(12) United States Patent
Xu et al.

(10) Patent No.: US 11,814,364 B2
(45) Date of Patent: Nov. 14, 2023

(54) PYRIDINE N-OXIDE DERIVATIVES USEFUL AS FACTOR XIA INHIBITORS

(71) Applicant: Janssen Pharmaceutica NV, Beerse (BE)

(72) Inventors: Guozhang Xu, Chesterbrook, PA (US); Boying Guo, Glenside, PA (US); Zhijie Liu, Paoli, PA (US); Jing Zhang, Wilmington, DE (US); Micheal D. Gaul, Apex, NC (US); Eugene B. Grant, Flemington, NJ (US); Mark J. Macielag, Gwynedd Valley, PA (US); Tianbao Lu, Churchville, PA (US); Tho V. Thieu, North Wales, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 17/696,926

(22) Filed: Mar. 17, 2022

(65) Prior Publication Data
US 2023/0091768 A1    Mar. 23, 2023

Related U.S. Application Data

(60) Provisional application No. 63/162,643, filed on Mar. 18, 2021, provisional application No. 63/162,641, filed on Mar. 18, 2021, provisional application No. 63/162,638, filed on Mar. 18, 2021, provisional application No. 63/162,645, filed on Mar. 18, 2021, provisional application No. 63/162,636, filed on Mar. 18, 2021.

(51) Int. Cl.
C07D 401/14    (2006.01)
C07D 417/14    (2006.01)
C07D 413/14    (2006.01)
C07D 405/14    (2006.01)

(52) U.S. Cl.
CPC ......... *C07D 401/14* (2013.01); *C07D 405/14* (2013.01); *C07D 413/14* (2013.01); *C07D 417/14* (2013.01)

(58) Field of Classification Search
CPC .. C07D 401/14; C07D 405/14; C07D 413/14; C07D 417/14
See application file for complete search history.

(56) References Cited

U.S. PATENT DOCUMENTS

| | | | |
|---|---|---|---|
| 4,845,079 A | 7/1989 | Luly et al. | |
| 4,885,292 A | 12/1989 | Ryono et al. | |
| 4,894,437 A | 1/1990 | TenBrink | |
| 4,980,283 A | 12/1990 | Huang et al. | |
| 5,034,512 A | 7/1991 | Hudspeth et al. | |
| 5,036,053 A | 7/1991 | Himmelsbach et al. | |
| 5,036,054 A | 7/1991 | Kaltenbronn et al. | |
| 5,055,466 A | 10/1991 | Weller, III et al. | |
| 5,063,207 A | 11/1991 | Doherty et al. | |
| 5,063,208 A | 11/1991 | Rosenberg et al. | |
| 5,064,965 A | 11/1991 | Ocain et al. | |
| 5,066,643 A | 11/1991 | Abeles et al. | |
| 5,071,837 A | 12/1991 | Doherty et al. | |
| 5,075,451 A | 12/1991 | Ocain et al. | |
| 5,089,471 A | 2/1992 | Hanson et al. | |
| 5,095,119 A | 3/1992 | Ocain et al. | |
| 5,098,924 A | 3/1992 | Poss | |
| 5,104,869 A | 4/1992 | Albright et al. | |
| 5,106,835 A | 4/1992 | Albright et al. | |
| 5,114,937 A | 5/1992 | Hamby et al. | |
| 5,116,835 A | 5/1992 | Rüger et al. | |
| 6,063,847 A | 5/2000 | Chackalamannil et al. | |
| 6,326,380 B1 | 12/2001 | Chackalamannil et al. | |
| 6,645,987 B2 | 11/2003 | Chackalamannil et al. | |
| 7,037,920 B2 | 5/2006 | Chackalamannil et al. | |
| 7,235,567 B2 | 6/2007 | Wu | |
| 7,304,078 B2 | 12/2007 | Chackalamannil et al. | |
| 2003/0022890 A1 | 1/2003 | Atwal et al. | |
| 2018/0079743 A1 | 3/2018 | Mertz et al. | |
| 2018/0194745 A1 | 7/2018 | Nuez et al. | |
| 2018/0339977 A1 | 11/2018 | Xu et al. | |

FOREIGN PATENT DOCUMENTS

| | | |
|---|---|---|
| EP | 1294714 B1 | 8/2007 |
| EP | 1495018 B1 | 3/2011 |
| WO | WO 1994/03479 A1 | 2/1994 |
| WO | WO 2001/40231 A1 | 6/2001 |
| WO | WO 2001/96330 A2 | 12/2001 |
| WO | WO 2015/011087 A1 | 1/2015 |
| WO | WO 2015/183709 A1 | 12/2015 |
| WO | WO 2016/015593 A1 | 2/2016 |
| WO | WO 2016/168098 A1 | 10/2016 |
| WO | WO 2017/005725 A1 | 1/2017 |
| WO | WO 2017/074832 A1 | 5/2017 |
| WO | WO 2017/095760 A1 | 6/2017 |
| WO | WO 2018/204661 A1 | 11/2018 |

OTHER PUBLICATIONS

QUAN et al., "Factor XIa Inhibitors as New Anticoagulants.", J. Med. Chem. 2018, pp. 7425-7447, vol. 61.
Gailani et al., "Intrinstic Pathway of Coagulation and Arterial Thrombosis.", *Arterioscler. Thromb. Vasc. Biol.*, 2007, pp. 2507-2513, vol. 27.
Hoffman, M., "A cell-based model of coagulation and the role of Factor VIIa.", Blood Reviews, 2003, S1-S5, vol. 17.

(Continued)

*Primary Examiner* — Michael Barker
*Assistant Examiner* — Jed A Kucharczk
(74) *Attorney, Agent, or Firm* — BakerHostetler

(57) ABSTRACT

The present invention is directed to pyridine N-oxide derivatives, stereoisomers, isotopologues, isotopomers and pharmaceutically acceptable salts thereof, pharmaceutical compositions containing said compounds and the use of said compounds in the treatment and/or prophylaxis of thromboembolic disorders, inflammatory disorders and diseases or conditions in which plasma kallikrein activity is implicated.

10 Claims, No Drawings

(56) References Cited

OTHER PUBLICATIONS

Chou, T., "Theoretical Basis, Experimental Design, and Computerized Simulation of Synergism and Antagonism in Drug Combination Studies.", Pharmacol Rev., 2006, pp. 621-681, vol. 58(3).
Howard et al., "Factor IXa Inhibitors as Novel Anticoagulants.", Arterioscler Thromb Vase Biol. 2007. pp. 722-727, vol. 27.
Bernatowicz et al., "Development of Potent Thrombin Receptor Antagonist Peptides.", Med. Chem., 1996, pp. 4879-4887, vol. 39.

PYRIDINE N-OXIDE DERIVATIVES USEFUL AS FACTOR XIa INHIBITORS

CROSS REFERENCE TO RELATED APPLICATIONS

This application claims the benefit of U.S. Provisional Patent Application No. 63/162,636, filed on Mar. 18, 2021, U.S. Provisional Patent Application No. 63/162,638, filed on Mar. 18, 2021, Provisional Patent Application No. 63/162,641, filed on Mar. 18, 2021, Provisional Patent Application No. 63/162,643, filed on Mar. 18, 2021, and Provisional Patent Application No. 63/162,645, filed on Mar. 18, 2021, which are incorporated by reference herein in their entirety.

FIELD OF THE INVENTION

The present invention is directed to pyridine N-oxide derivatives, stereoisomers, isotopologues, isotopomers and pharmaceutically acceptable salts thereof, pharmaceutical compositions containing said compounds, and the use of said compounds in the treatment and/or prophylaxis of thromboembolic disorders, inflammatory disorders and diseases or conditions in which plasma kallikrein activity is implicated.

BACKGROUND OF THE INVENTION

Thromboembolic diseases remain the leading cause of death in developed countries despite the availability of anticoagulants such as warfarin (COUMADIN®), heparin, low molecular weight heparins (LMWH), and synthetic pentasaccharides and antiplatelet agents such as aspirin and clopidogrel (PLAVIX®).

The oral anticoagulant warfarin inhibits the post-translational maturation of coagulation factors VII, IX, X and prothrombin, and has proven effective in both venous and arterial thrombosis. However, its usage is limited due to its narrow therapeutic index, slow onset of therapeutic effect, numerous dietary and drug interactions, and a need for monitoring and dose adjustment. Thus discovering and developing safe and efficacious oral anticoagulants for the prevention and treatment of a wide range of thromboembolic disorders has become increasingly important.

Factor XIa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel blocking circulation and inducing a heart attack or stroke. Thromboembolic disorders are the largest cause of mortality and disability in the industrialized world.

Blood clotting is a process of control of the bloodstream essential for the survival of mammals. The process of clotting, and the subsequent dissolution of the clot after wound healing has taken place, commences after vascular damage, and can be divided into four phases. The first phase, vasoconstriction or vasocontraction, can cause a decrease in blood loss in the damaged area. In the next phase, platelet activation by thrombin, platelets attach to the site of the vessel wall damage and form a platelet aggregate. In the third phase, formation of clotting complexes leads to massive formation of thrombin, which converts soluble fibrinogen to fibrin by cleavage of two small peptides. In the fourth phase, after wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting Factor X is activated. The activated Factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue damage or an injury is the result of the extrinsic pathway. Both pathways comprise a relatively large number of proteins, which are known as clotting factors. The intrinsic pathway requires the clotting Factors V, VIII, IX, X, XI and XII and also prekallikrein, high molecular weight kininogen, calcium ions and phospholipids from platelets.

Factor XIa, a plasma serine protease involved in the regulation of blood coagulation, is initiated in vivo by the binding of tissue Factor (TF) to factor VII (FVII) to generate Factor VIIa (FVIIa). The resulting TF:FVIIa complex activates Factor IX (FIX) and Factor X (FX) that leads to the production of Factor Xa (FXa). The generated FXa catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Gailani, D. et al., *Arterioscler Thromb. asc. Biol.*, 27:2507-2513 (2007)). The resulting burst of thrombin converts fibrinogen to fibrin that polymerizes to form the structural framework of a blood clot, and activates platelets, which are a key cellular component of coagulation (Hoffman, M., *Blood Reviews*, 17:S1-S5 (2003)). Therefore, Factor XIa plays a key role in propagating this amplification loop and is thus an attractive target for antithrombotic therapy.

In addition to stimulation via tissue factor, the coagulation system can be activated particularly on negatively charged surfaces, which include not only surface structures of foreign cells (e.g. bacteria) but also artificial surfaces such as vascular prostheses, stents and extracorporeal circulation. On the surface, initially Factor XII (FXII) is activated to Factor XIIa which subsequently activates Factor XI, attached to cell surfaces, to Factor XIa. This leads to further activation of the coagulation cascade as described above. In addition, Factor XIIa also activates bound plasma prokallikrein to plasma kallikrein (PK) which, in a potentiation loop, leads to further Factor XII activation, overall resulting in amplification of the initiation of the coagulation cascade. In addition, PK is an important bradykinin-releasing protease which leads to increased endothelial permeability. Further substrates that have been described are prorenin and prourokinase, whose activation may influence the regulatory processes of the renin-angiotensin system and fibrinolysis. The activation of PK is therefore an important link between coagulative and inflammatory processes.

OGAWA et al., in PCT Publication WO2017095760 A1, published 8 Jun. 2017 describe compounds which are selective Factor XIa inhibitors or dual inhibitors of Factor XIa and plasma kallilkrein.

XU, et al., in PCT Publication WO 2017074832 A1, published 4 May 2017, describe compounds which are selective Factor XIa inhibitors or dual inhibitors of Factor XIa and plasma kallikrein.

JIMENEZ NUNES et al., in PCT Publication WO 2017005725 A1, published 12 Jan. 2017 describe substituted oxopyridine derivatives and their use in the preparation of medicaments for the treatment and/or prophylaxis of cardiovascular diseases, preferably thrombotic or thromboembolic disorders, and or edemas, and also ophthalmic disorders.

MERTZ et al., in PCT Publication WO2016168098 A1, published 20 Oct. 2016 describe compounds which are selective Factor XIa inhibitors or dual inhibitors of Factor XIa and plasma kallilkrein.

LIU et al., in PCT Publication WO2016015593 A1, published 4 Feb. 2016 describe compounds which are selective Factor XIa inhibitors or dual inhibitors of Factor XIa and plasma kallilkrein.

LIU et al., in PCT Publication WO2015183709 A1, published 3 Dec. 2015 describe compounds which are selective Factor XIa inhibitors or dual inhibitors of Factor XIa and plasma kallilkrein.

ROHRIG et al., in PCT Publication WO2015011087 A1, published 29 Jan. 2015 describe substituted oxopyridine derivatives and their use in the preparation of medicaments for the treatment and/or prophylaxis of cardiovascular diseases, preferably thrombotic or thromboembolic disorders, and or edemas, and also ophthalmic disorders.

LELETI, M. R., et al., in PCT Publication WO2018204661 A1, published 8 Nov. 2018 describe compounds that inhibit at least one of the A2A and A2B adenosine receptors. Also described are the use of such compounds for the treatment of a diverse array of diseases, disorders, and conditions, including cancer and immune-related disorders that are mediated, at least in part, by the adenosine A2A and/or adenosine A2B receptor.

There remains a need for Factor XIa inhibitor compounds that have pharmacokinetic and pharmacodynamic properties suitable for use as human pharmaceuticals for the treatment and/or prophylaxis of a thromboembolic disorders.

SUMMARY OF THE INVENTION

The present invention is directed to compounds of formula (I)

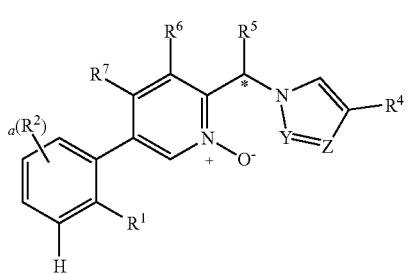

(I)

wherein $R^1$ is selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, nitro, —$NR^A R^B$, —C(O)—$C_{1-4}$alkyl, $C_{3-6}$cycloalkyl, phenyl and 5 to 6 membered heterocyclyl;

wherein the $C_{3-6}$cycloalkyl, phenyl or 5 to 6 membered heterocyclyl is optionally substituted with one or more substituents independently selected from the group consisting of halogen, hydroxy, cyano, $C_{1-4}$alkyl, fluorinated $C_{1-4}$alkyl, $C_{1-4}$alkoxy, fluorinated $C_{1-4}$alkoxy, —C(O)OH, —C(O)O—($C_{1-4}$alkyl), —$NR^A R^B$, —($C_{1-4}$alkyl)-$NR^A R^B$, $C_{3-7}$cycloalkyl and 5 to 6 membered heterocyclyl;

and wherein $R^A$ and $R^B$ are each independently selected from the group consisting of hydrogen and $C_{1-4}$alkyl;

a is an integer from 0 to 3;

each $R^2$ is independently selected from the group consisting of chloro, fluoro, methyl and methoxy;

Y is N and Z is $C(R^3)$, such that

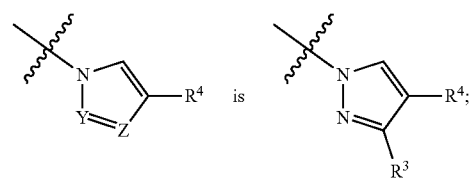

$R^3$ is selected from the group consisting of hydrogen, fluoro, chloro and methyl;

$R^4$ is selected from the group consisting of (a) carboxy;

(b) phenyl; wherein the phenyl is optionally substituted with one or more substituents independently selected from the group consisting of halogen, fluorinated $C_{1-2}$alkoxy, —C(O)OH, —C(O)—O—($C_{1-4}$alkyl), —$NR^C R^D$, —$C_{1-2}$alkyl-$NR^C R^D$, —C(O)—$NR^C R^D$, —$NR^D$—C(O)—($C_{1-2}$alkyl)-O—($C_{1-4}$alkyl), —$NR^D$—C(O)—O—($C_{1-2}$alkyl)-O—($C_{1-4}$alkyl), cyclopropyl, 1-carboxy-cycloprop-1-yl, 1-($C_{1-4}$alkoxy-carbonyl)-cycloprop-1-yl, pyrrolidin-2-yl-5-one, pyrrolidin-3-yl-2,5-dione, pyrrol-3-yl-2,5-dione, 1,2,3,4-tetrazol-1-yl, 1,2,3,4-tetrazol-5-yl, 1,2,4-oxadiazol-3-yl-5-one, oxazolidin-5-yl-2,4-dione, 1H-imidazol-5-yl-2,5-dione, thiazol-5-yl-2,4-dione, isoxazol-5-yl-3-ol, isothiazol-5-yl-3-ol, 3-chloro-4-hydroxy-phenyl, —C(O)—NH—CN, —C(O)—NH—$SO_2$—$CH_3$, —$SO_2$—NH—$CF_3$, and —$SO_2$—NH—$CF_2 CF_3$;

wherein $R^C$ is selected from the group consisting of hydrogen, $C_{1-4}$alkyl, cyclopropyl, 3-hydroxy-cycloprop-1-yl, —C(O)—$C_{1-4}$alkyl, —C(O)-cyclopropyl, —C(O)—O—$C_{1-4}$alkyl and —$SO_2$—$C_{1-4}$alkyl; and $R^D$ is selected from the group consisting of hydrogen and $C_{1-4}$alkyl;

(c) 5 membered heterocyclyl; wherein the 5 membered heterocyclyl contains at least one heteroatom selected from the group consisting of O, N and S; optionally contains 1 to 3 additional heteroatoms independently selected from the group consisting of O, N and S; wherein the 5 membered heterocyclyl is saturated, partially unsaturated, or aromatic;

wherein the 5 membered heterocyclyl is optionally substituted with one or more substituents independently selected from the group consisting of halogen, hydroxy, $C_{1-4}$alkyl, fluorinated $C_{1-4}$alkyl, $C_{1-4}$ alkoxy, fluorinated $C_{1-4}$alkoxy, $C_{3-7}$cycloalkyl, —C(O)OH, —C(O)—O—$C_{1-4}$alkyl, —$C_{1-2}$alkyl-C(O)—O—$C_{1-4}$alkyl, cyano, —$NR^E R^F$, —C(O)—$NR^E R^F$, pyrrolidin-2-yl-5-one, pyrrolidin-3-yl-2,5-dione, pyrrol-3-yl-2,5-dione, 1,2,3,4-tetrazol-1-yl, 1,2,3,4-tetrazol-5-yl, 1,2,4-oxadiazol-3-yl-5-one, oxazolidin-5-yl-2,4-dione, 1H-imidazol-5-yl-2,5-dione, thiazol-5-yl-2,4-dione, isoxazol-5-yl-3-ol, isothiazol-5-yl-3-ol, 3-chloro-4-hydroxy-phenyl, —C(O)—NH—CN, —C(O)—NH—$SO_2$—$CH_3$, —$SO_2$—NH—$CF_3$, and —$SO_2$—NH—$CF_2 CF_3$;

wherein $R^E$ is selected from the group consisting of hydrogen, $C_{1-4}$alkyl, cyclopropyl, 3-hydroxy-cycloprop-1-yl, —C(O)—$C_{1-4}$alkyl, —C(O)-cyclopropyl, —C(O)—O—$C_{1-4}$alkyl and —SO$_2$—$C_{1-4}$alkyl; and $R^F$ is selected from the group consisting of hydrogen and $C_{1-4}$alkyl;

(d) 6 membered heterocyclyl; wherein the 6 membered heterocyclyl contains at least one heteroatom selected from the group consisting of N, O and S; optionally contains 1 to 3 additional heteroatoms independently selected from the group consisting of O, N and S; wherein the 6 membered heterocyclyl is saturated, partially unsaturated, or aromatic; wherein the 6 membered heterocyclyl is bound through a carbon atom;

wherein the 6 membered heterocyclyl is optionally substituted with one or more substituents independently selected from the group consisting of halogen, hydroxy, oxo, $C_{1-4}$alkyl, fluorinated $C_{1-4}$alkyl, $C_{1-4}$ alkoxy, fluorinated $C_{1-4}$alkoxy, —$C_{1-2}$alkyl-O—$C_{1-4}$alkyl, $C_{3-7}$cycloalkyl, —C(O)OH, —C(O)—O—$C_{1-4}$alkyl, —$C_{1-2}$alkyl-C(O)—O—$C_{1-4}$alkyl, cyano, —NR$^G$R$^H$, —C(O)—NR$^G$R$^H$, pyrrolidin-2-yl-5-one, pyrrolidin-3-yl-2,5-dione, pyrrol-3-yl-2,5-dione, 1,2,3,4-tetrazol-1-yl, 1,2,3,4-tetrazol-5-yl, 1,2,4-oxadiazol-3-yl-5-one, oxazolidin-5-yl-2,4-dione, 1H-imidazol-5-yl-2,5-dione, thiazol-5-yl-2,4-dione, isoxazol-5-yl-3-ol, isothiazol-5-yl-3-ol, 3-chloro-4-hydroxy-phenyl, —C(O)—NH—CN, —C(O)—NH—SO$_2$—CH$_3$, —SO$_2$—NH—CF$_3$, and —SO$_2$—NH—CF$_2$CF$_3$;

wherein $R^G$ is selected from the group consisting of hydrogen, $C_{1-4}$alkyl, cyclopropyl, 3-hydroxy-cycloprop-1-yl, —C(O)—$C_{1-4}$alkyl, —C(O)-cyclopropyl, —C(O)—O—$C_{1-4}$alkyl and —SO$_2$—$C_{1-4}$alkyl; and $R^H$ is selected from the group consisting of hydrogen and $C_{1-4}$alkyl;

and wherein the 6 membered heterocyclyl contains a nitrogen ring atom, said nitrogen ring atom may be further optionally substituted with oxygen to form an N-oxide;

and (e) 9 to 10 membered bicyclic heterocyclyl; wherein the 9 to 10 membered bicyclic heterocyclyl contains at least one heteroatom selected from the group consisting of O, N and S; optionally contains one to four additional heteroatoms independently selected from the group consisting of O, N and S; wherein the 9 to 10 membered bicyclic heterocyclyl is saturated, partially unsaturated, partially aromatic, aromatic, bicyclic, fused, bridged or spiro-cyclic;

and wherein the 9 to 10 membered bicyclic heterocyclyl is optionally substituted with one or more substituents independently selected from the group consisting of halogen, hydroxy, oxo, $C_{1-4}$alkyl, fluorinated $C_{1-4}$alkyl, $C_{1-4}$alkoxy, fluorinated $C_{1-4}$alkoxy, cyano, —C(O)OH, —C(O)—O—$C_{1-4}$alkyl, NR$^J$R$^K$, and —C(O)—NR$^J$R$^K$, pyrrolidin-2-yl-5-one, pyrrolidin-3-yl-2,5-dione, pyrrol-3-yl-2,5-dione, 1,2,3,4-tetrazol-1-yl, 1,2,3,4-tetrazol-5-yl, 1,2,4-oxadiazol-3-yl-5-one, oxazolidin-5-yl-2,4-dione, 1H-imidazol-5-yl-2,5-dione, thiazol-5-yl-2,4-dione, isoxazol-5-yl-3-ol, isothiazol-5-yl-3-ol, 3-chloro-4-hydroxy-phenyl, —C(O)—NH—CN, —C(O)—NH—SO$_2$—CH$_3$, —SO$_2$—NH—CF$_3$, and —SO$_2$—NH—CF$_2$CF$_3$;

wherein $R^J$ and $R^K$ are each independently selected from the group consisting of hydrogen and $C_{1-4}$ alkyl;

$R^5$ is selected from the group consisting of (a) $C_{1-4}$alkyl; wherein the $C_{1-4}$alkyl is optionally substituted with one or more halogen; and further optionally substituted with a substituent selected from the group consisting of hydroxy, $C_{1-4}$alkoxy, fluorinated $C_{1-4}$alkoxy, —C(O)OH, —C(O)—O—($C_{1-4}$alkyl), —C(O)—O-(fluorinated $C_{1-4}$alkyl), —C(O)-(fluorinated $C_{1-4}$alkyl), and —C(O)—NR$^L$R$^M$; wherein R$^L$ and R$^M$ are each independently selected from the group consisting of hydrogen and $C_{1-2}$alkyl;

(b) —CH$_2$—$C_{3-8}$cycloalkyl or —CH$_2$-adamant-1-yl; wherein the $C_{3-8}$cycloalkyl is optionally substituted with one or more halogen or $C_{1-4}$alkyl; and further optionally substituted with a substituent selected from the group consisting of —C(O)OH, —C(O)—O—$C_{1-4}$alkyl, —C(O)-(5 to 6 membered saturated heterocyclyl), —C(O)-(isoindolin-2-yl), —C(O)-(azaspiro[2.4]heptan-5-yl), —C(O)-(carboxy substituted azaspiro[2.4]heptan-5-yl), —C(O)—(NR$^P$R$^Q$ substituted azaspiro[2.4]heptan-5-yl), phenyl, 1,1'-biphen-4-yl and —C(O)—NR$^P$R$^Q$;

wherein the —C(O)-(5 to 6 membered saturated heterocyclyl) substituent on the —CH$_2$—$C_{3-8}$cycloalkyl is further optionally substituted on the (5 to 6 membered heterocyclyl) with one or more substituents independently selected from the group consisting of halogen, hydroxy, $C_{1-4}$alkyl, fluorinated $C_{1-4}$alkyl, $C_{1-4}$ alkoxy, fluorinated $C_{1-4}$alkoxy, cyano, —C(O)OH, —C(O)—O—$C_{1-4}$alkyl, —NR$^P$R$^Q$, phenyl and $C_{3-8}$cycloalkyl;

wherein the phenyl substituent on the —CH$_2$—$C_{3-8}$cycloalkyl is further optionally substituted with one or more substituents independently selected form the group consisting of halogen, hydroxy, $C_{1-4}$alkyl, fluorinated $C_{1-4}$alkyl, $C_{1-4}$alkoxy, fluorinated $C_{1-4}$alkoxy, cyano, —NR$^P$R$^Q$, and $C_{3-8}$cycloalkyl;

and wherein R$^P$ and R$^Q$ are each independently selected from the group consisting of hydrogen and $C_{1-4}$alkyl;

(c) -L$^1$-(5 to 6 membered saturated heterocyclyl); wherein L$^1$ is selected from the group consisting of —CH$_2$— and —CH$_2$—C(O)—; wherein, when L$^1$ is —CH$_2$—C(O)—, then the (5 to 6 membered saturated heterocyclyl) is bound to the —C(O)— portion of L$^1$; and wherein the (5 to 6 membered saturated heterocyclyl) is optionally substituted with one to two oxo group;

(d) —$C_{1-2}$alkyl-phenyl; wherein the phenyl is optionally substituted with one or more substituents independently selected from the group consisting of halogen, hydroxy, $C_{1-4}$alkyl, fluorinated $C_{1-4}$alkyl, $C_{1-4}$ alkoxy, fluorinated $C_{1-4}$alkoxy, —OCH$_2$—C(O)—NR$^S$R$^T$, phenyl and phenoxy; and wherein R$^S$ and R$^T$ are each independently selected from the group consisting of hydrogen and $C_{1-4}$alkyl;

(e) 1,2,3-triazol-4-yl, 1,2,5-triazol-3-yl, —CH$_2$-1,2,3-triazol-4-yl and —CH$_2$-1,2,5-triazol-3-yl; wherein the 1,2,3-triazol-4-yl or 1,2,5-triazoly-3-yl, whether alone or as part of the substituent group is optionally substituted with a substituent selected from the group consisting of $C_{1-4}$alkyl, fluorinated $C_{1-4}$alkyl, phenyl and piperidinyl; wherein the piperidinyl is optionally substituted with —C(O)—$C_{1-4}$alkyl;

(f) —CH$_2$-(5 to 6 membered or 9 to 10 membered heterocyclyl); wherein the (5 to 6 membered or 9 to 10 membered heterocyclyl) is other than triazolyl;

wherein the (5 to 6 membered or 9 to 10 membered heterocyclyl) is optionally substituted with one or more substituents independently selected from the group consisting of halogen, hydroxy, oxo, $C_{1-4}$alkyl, fluorinated $C_{1-4}$alkyl, $C_{1-4}$alkoxy, fluorinated $C_{1-4}$alkoxy, cyano, —C(O)OH, —C(O)—O—$C_{1-4}$alkyl, —$C_{1-2}$alkyl-O—$C_{1-4}$ alkyl, —$C_{1-2}$alkyl-O-(fluorinated $C_{1-4}$alkyl), —C(O)—NR$^V$R$^W$, —C$_{1-2}$alkyl-C(O)—NR$^V$R$^W$, -(5 to 6 membered saturated heterocyclyl), —C(O)-(5 to 6 membered saturated heterocyclyl), —C(O)-(carboxy substituted 5 to 6 membered saturated heterocyclyl), —C$_{1-2}$alkyl-C(O)-(5 to 6 membered saturated heterocyclyl), phenyl and pyridinyl;
wherein the pyridinyl substituent on the —CH$_2$-(5 to 6 membered or 9 to 10 membered heterocyclyl) is further optionally substituted with one or more substituents independently selected from the group consisting of halogen and fluorinated C$_{1-4}$alkyl;
and wherein R$^V$ and R$^W$ are each independently selected from the group consisting of hydrogen and C$_{1-4}$alkyl;
and (g) —CH$_2$—NR$^8$R$^9$; wherein R$^8$ is selected from the group consisting of hydrogen and C$_{1-4}$alkyl; R$^9$ is selected from the group consisting of C$_{1-4}$alkyl, fluorinated C$_{1-4}$alkyl, C$_{1-4}$alkoxy, fluorinated C$_{1-4}$alkoxy, —C(O)—C$_{1-4}$alkyl, —C(O)—C$_{1-2}$alkyl-O—C$_{1-4}$alkyl, —C(O)-phenyl, —C(O)—C$_{1-2}$alkyl-phenyl, —C(O)—O—C$_{1-4}$alkyl, —C(O)—O— phenyl, —C(O)—O—C$_{1-2}$alkyl-phenyl, —C(O)—C$_{3-7}$cycloalkyl, —C(O)-(1-methyl-cycloprop-1-yl), —C(O)-(5 to 6 membered saturated heterocyclyl), —C(O)—C$_{1-2}$alkyl-C(O)-(5 to 6 membered saturated heterocyclyl), —O—C$_{1-2}$ alkyl-C(O)-(5 to 6 membered saturated heterocyclyl), —C(O)-(1-methyl-pyridinyl-one) and —C(O)—NR$^X$R$^Y$; and
wherein R$^X$ and R$^Y$ are each independently selected from the group consisting of hydrogen and C$_{1-4}$alkyl;
R$^6$ and R$^7$ are each independently selected from the group consisting of hydrogen, halogen, C$_{1-4}$alkyl and C$_{1-4}$alkoxy;
provided that at least one of R$^6$ or R$^7$ is hydrogen;
and stereoisomers, isotopomers, isotopologues and pharmaceutically acceptable salts thereof.

In certain embodiments, the present invention is directed to compounds of formula (I) wherein the R$^5$ substituent group is present in a stereoisomeric excess of the corresponding R-stereoisomer. In certain embodiments, the present invention is directed to compounds of formula (I) wherein the R$^5$ substituent group is present in a stereoisomeric excess of the corresponding S-stereoisomer.

The present invention is further directed to processes for the preparation of the compounds of formula (I). The present invention is further directed to a compound of formula (I) prepared according to any of the process(es) described herein.

Illustrative of the invention are pharmaceutical compositions comprising a pharmaceutically acceptable carrier and a compound of formula (I) as described herein. An illustration of the invention is a pharmaceutical composition made by mixing a compound of formula (I) as described herein and a pharmaceutically acceptable carrier. Illustrating the invention is a process for making a pharmaceutical composition comprising mixing a compound of formula (I) as described herein and a pharmaceutically acceptable carrier.

Exemplifying the invention are methods for the treatment and/or prophylaxis of thromboembolic disorders, inflammatory disorders or diseases or conditions in which plasma kallikrein activity is implicated, as described herein, comprising administering to a subject in need thereof a therapeutically effective amount of any of the compounds or pharmaceutical compositions described above.

Exemplifying the invention are methods or the treatment and/or prophylaxis of thromboembolic disorders, such as arterial cardiovascular thromboembolic disorders, venous cardiovascular thromboembolic disorders, arterial cerebrovascular thromboembolic disorders, and venous cerebrovascular thromboembolic disorders, comprising administering to a subject in need thereof a therapeutically effective amount of any of the compounds or pharmaceutical compositions described above. Examples of thromboembolic disorders include, but are not limited to, unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

DETAILED DESCRIPTION OF THE INVENTION

The present invention is directed to compounds of formula (I)

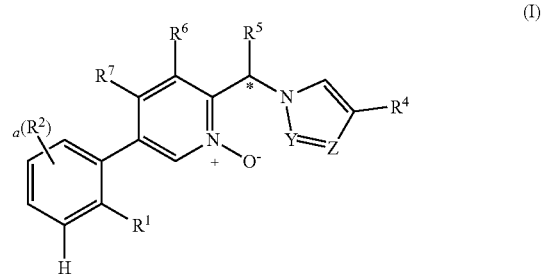

(I)

wherein a, R$^1$, R$^2$, Y, Z, R$^4$, R$^5$, R$^6$, R$^7$, etc. are as herein described; and stereoisomers, isotopologues, isotopomers, and pharmaceutically acceptable salts thereof. The compounds of the present invention are useful for the treatment and/or prophylaxis of thromboembolic disorders, inflammatory disorders and diseases or conditions in which plasma kallikrein activity is implicated. In certain embodiments, the present invention is directed to a compound of formula (I) which is a compound of formula (I-Q)

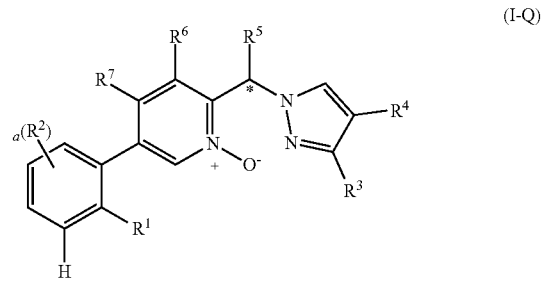

(I-Q)

wherein Y is N, Z is C(R$^3$) and R$^1$ is selected from the group consisting of halogen, hydroxy, C$_{1-4}$alkyl, fluorinated C$_{1-4}$alkyl, C$_{1-4}$alkoxy, fluorinated C$_{1-4}$alkoxy, cyano, nitro, —NR$^A$R$^B$, —C(O)—C$_{1-4}$alkyl.

In certain embodiments, the present invention is directed to a compound of formula (I) which is a compound of formula (I-PX)

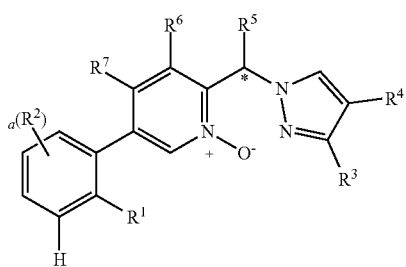

(I-PX)

wherein Y is N, Z is C(R³) and R⁴ is selected from the group consisting of (a) carboxy; and (b) phenyl; wherein the phenyl is optionally substituted with one or more substituents independently selected from the group consisting of halogen, fluorinated $C_{1-2}$alkoxy, —C(O)OH, —C(O)—O—($C_{1-4}$alkyl), —NR$^C$R$^D$, —$C_{1-2}$alkyl-NR$^C$R$^D$, —C(O)—NR$^C$R$^D$, —NR$^D$—C(O)—($C_{1-2}$alkyl)-O—($C_{1-4}$alkyl), —NR$^D$—C(O)—O—($C_{1-2}$alkyl)-O—($C_{1-4}$alkyl), cyclopropyl, 1-carboxy-cycloprop-1-yl, 1-($C_{1-4}$alkoxy-carbonyl)-cycloprop-1-yl, pyrrolidin-2-yl-5-one, pyrrolidin-3-yl-2,5-dione, pyrrol-3-yl-2,5-dione, 1,2,3,4-tetrazol-1-yl, 1,2,3,4-tetrazol-5-yl, 1,2,4-oxadiazol-3-yl-5-one, oxazolidin-5-yl-2,4-dione, 1H-imidazol-5-yl-2,5-dione, thiazol-5-yl-2,4-dione, isoxazol-5-yl-3-ol, isothiazol-5-yl-3-ol, 3-chloro-4-hydroxy-phenyl, —C(O)—NH—CN, —C(O)—NH—SO₂—CH₃, —SO₂—NH—CF₃, and —SO₂—NH—CF₂CF₃; wherein R$^C$ is selected from the group consisting of hydrogen, $C_{1-4}$alkyl, cyclopropyl, 3-hydroxy-cycloprop-1-yl, —C(O)—$C_{1-4}$alkyl, —C(O)-cyclopropyl, —C(O)—O—$C_{1-4}$alkyl and —SO₂—$C_{1-4}$alkyl; and R$^D$ is selected from the group consisting of hydrogen and $C_{1-4}$alkyl.

In certain embodiments, the present invention is directed to a compound of formula (I) which is a compound of formula (I-PY)

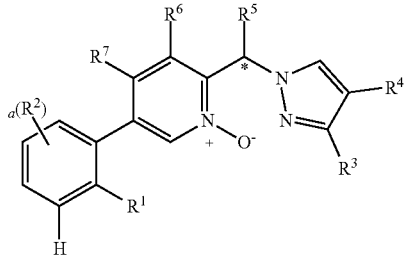

(I-PY)

wherein Y is N, Z is C(R³) and R⁴ is selected from the group consisting of (c) 5 membered heterocyclyl; wherein the 5 membered heterocyclyl contains at least one heteroatom selected from the group consisting of O, N and S; optionally contains 1 to 3 additional heteroatoms independently selected from the group consisting of O, N and S; wherein the 5 membered heterocyclyl is saturated, partially unsaturated, or aromatic; wherein the 5 membered heterocyclyl is optionally substituted with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, $C_{3-7}$cycloalkyl, —C(O)OH, —C(O)—O—$C_{1-4}$alkyl, cyano, —NR$^E$R$^F$, —C(O)—NR$^E$R$^F$, pyrrolidin-2-yl-5-one, pyrrolidin-3-yl-2,5-dione, pyrrol-3-yl-2,5-dione, 1,2,3,4-tetrazol-1-yl, 1,2,3,4-tetrazol-5-yl, 1,2,4-oxadiazol-3-yl-5-one, oxazolidin-5-yl-2,4-dione, 1H-imidazol-5-yl-2,5-dione, thiazol-5-yl-2,4-dione, isoxazol-5-yl-3-ol, isothiazol-5-yl-3-ol, 3-chloro-4-hydroxy-phenyl, —C(O)—NH—CN, —C(O)—NH—SO₂—CH₃, —SO₂—NH—CF₃, and —SO₂—NH—CF₂CF₃; wherein R$^E$ is selected from the group consisting of hydrogen, $C_{1-4}$alkyl, cyclopropyl, 3-hydroxy-cycloprop-1-yl, —C(O)—$C_{1-4}$alkyl, —C(O)-cyclopropyl, —C(O)—O—$C_{1-4}$alkyl and —SO₂—$C_{1-4}$alkyl; and R$^F$ is selected from the group consisting of hydrogen and $C_{1-4}$alkyl.

In certain embodiments, the present invention is directed to a compound of formula (I) which is a compound of formula (I-PZ)

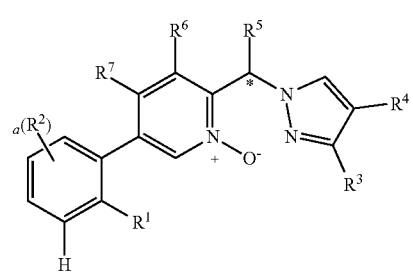

(I-PZ)

wherein Y is N, Z is C(R³) and R⁴ is selected from the group consisting of (d) 6 membered heterocyclyl; wherein the 6 membered heterocyclyl contains at least one heteroatom selected from the group consisting of N, O and S; optionally contains 1 to 3 additional heteroatoms independently selected from the group consisting of O, N and S; wherein the 6 membered heterocyclyl is saturated, partially unsaturated, or aromatic; wherein the 6 membered heterocyclyl is bound through a carbon atom; wherein the 6 membered heterocyclyl is optionally substituted with one or more substituents independently selected from the group consisting of halogen, hydroxy, oxo, $C_{1-4}$alkyl, fluorinated $C_{1-4}$alkyl, $C_{1-4}$alkoxy, fluorinated $C_{1-4}$alkoxy, —$C_{1-2}$alkyl-O—$C_{1-4}$alkyl, $C_{3-7}$cycloalkyl, —C(O)OH, —C(O)—O—$C_{1-4}$alkyl, cyano, —NR$^G$R$^H$, —C(O)—NR$^G$R$^H$, pyrrolidin-2-yl-5-one, pyrrolidin-3-yl-2,5-dione, pyrrol-3-yl-2,5-dione, 1,2,3,4-tetrazol-1-yl, 1,2,3,4-tetrazol-5-yl, 1,2,4-oxadiazol-3-yl-5-one, oxazolidin-5-yl-2,4-dione, 1H-imidazol-5-yl-2,5-dione, thiazol-5-yl-2,4-dione, isoxazol-5-yl-3-ol, isothiazol-5-yl-3-ol, 3-chloro-4-hydroxy-phenyl, —C(O)—NH—CN, —C(O)—NH—SO₂—CH₃, —SO₂—NH—CF₃, and —SO₂—NH—CF₂CF₃; wherein R$^G$ is selected from the group consisting of hydrogen, $C_{1-4}$alkyl, cyclopropyl, 3-hydroxy-cycloprop-1-yl, —C(O)—$C_{1-4}$alkyl, —C(O)-cyclopropyl, —C(O)—O—$C_{1-4}$alkyl and —SO₂—$C_{1-4}$alkyl; and R$^H$ is selected from the group consisting of hydrogen and $C_{1-4}$alkyl; and wherein the 6 membered heterocyclyl (preferably, 6 membered aromatic heterocyclyl) contains a nitrogen ring atom, said nitrogen ring atom may be further optionally substituted with oxygen to form an N-oxide.

In certain embodiments, the present invention is directed to a compound of formula (I) which is a compound of formula (I-PB)

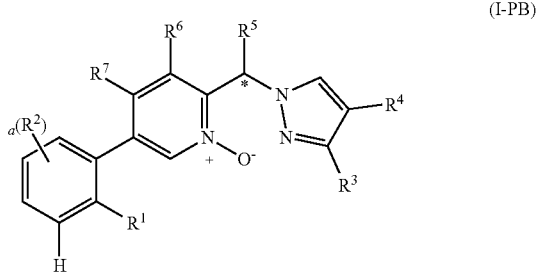

(I-PB)

wherein Y is N, Z is C(R³) and R⁴ is selected from the group consisting of (e) 9 to 10 membered bicyclic heterocyclyl; wherein the 9 to 10 membered bicyclic heterocyclyl contains at least one heteroatom selected from the group consisting of O, N and S; optionally contains one to four additional heteroatoms independently selected from the group consisting of O, N and S; wherein the 9 to 10 membered bicyclic heterocyclyl is saturated, partially unsaturated, partially aromatic, aromatic, bicyclic, fused, bridged or spiro-cyclic; and wherein the 9 to 10 membered bicyclic heterocyclyl is optionally substituted with one or more substituents independently selected from the group consisting of halogen, hydroxy, oxo, $C_{1-4}$alkyl, fluorinated $C_{1-4}$alkyl, $C_{1-4}$alkoxy, fluorinated $C_{1-4}$alkoxy, cyano, —C(O)OH, —C(O)—O—$C_{1-4}$alkyl, $NR^JR^K$, and —C(O)—$NR^JR^K$, pyrrolidin-2-yl-5-one, pyrrolidin-3-yl-2,5-dione, pyrrol-3-yl-2,5-dione, 1,2,3,4-tetrazol-1-yl, 1,2,3,4-tetrazol-5-yl, 1,2,4-oxadiazol-3-yl-5-one, oxazolidin-5-yl-2,4-dione, 1H-imidazol-5-yl-2,5-dione, thiazol-5-yl-2,4-dione, isoxazol-5-yl-3-ol, isothiazol-5-yl-3-ol, 3-chloro-4-hydroxy-phenyl, —C(O)—NH—CN, —C(O)—NH—SO₂—CH₃, —SO₂—NH—CF₃, and —SO₂—NH—CF₂CF₃; wherein $R^J$ and $R^K$ are each independently selected from the group consisting of hydrogen and $C_{1-4}$alkyl.

In certain embodiments, the present invention is directed to compounds of formula (I) wherein R¹ is selected from the group consisting of halogen, $C_{1-4}$alkyl, fluorinated $C_{1-4}$alkyl, $C_{1-4}$alkoxy, fluorinated $C_{1-4}$alkoxy, cyano, —$NR^AR^B$, —C(O)—$C_{1-4}$alkyl, and 5 to 6 membered heterocyclyl; wherein the 5 to 6 membered heterocyclyl is optionally substituted with one or more substituents independently selected from the group consisting of halogen, cyano, $C_{1-4}$alkyl, fluorinated $C_{1-4}$alkyl, $C_{1-4}$alkoxy, fluorinated $C_{1-4}$alkoxy, and $C_{3-7}$cycloalkyl; and wherein $R^A$ and $R^B$ are each independently selected from the group consisting of hydrogen and $C_{1-4}$alkyl. In certain embodiments, the present invention is directed to compounds of formula (I) wherein R¹ is selected from the group consisting of halogen, $C_{1-4}$alkyl, fluorinated $C_{1-4}$alkyl, $C_{1-4}$alkoxy, fluorinated $C_{1-4}$alkoxy, cyano, —$NR^AR^B$, and —C(O)—$C_{1-4}$alkyl; wherein $R^A$ and $R^B$ are each independently selected from the group consisting of hydrogen and $C_{1-4}$alkyl (preferably $C_{1-2}$alkyl).

In certain embodiments, the present invention is directed to compounds of formula (I) wherein R¹ is selected from the group consisting of 5 to 6 membered heterocyclyl; wherein the 5 to 6 membered heterocyclyl is optionally substituted with one or more substituents independently selected from the group consisting of halogen, cyano, fluorinated $C_{1-4}$alkyl, $C_{1-4}$alkoxy, and $C_{3-6}$cycloalkyl. In certain embodiments, the present invention is directed to compounds of formula (I) wherein R¹ is 5 to 6 membered heterocyclyl; wherein the 5 to 6 membered heterocyclyl is optionally substituted with a substituent selected from the group consisting of halogen, $C_{1-4}$alkyl, fluorinated $C_{1-4}$alkyl, and $C_{3-6}$cycloalkyl. In certain embodiments, the present invention is directed to compounds of formula (I) wherein R¹ is 5 to 6 membered heterocyclyl; wherein the 5 to 6 membered heterocyclyl is optionally substituted with one or more substituents independently selected from the group consisting of halogen, $C_{1-4}$alkyl and fluorinated $C_{1-4}$alkyl. In certain embodiments, the present invention is directed to compounds of formula (I) wherein R¹ is 5 membered heterocyclyl; wherein the 5 membered heterocyclyl is optionally substituted with fluorinated $C_{1-4}$alkyl.

In certain embodiments, the present invention is directed to compounds of formula (I) wherein R¹ is selected from the group consisting of fluoro, difluoromethyl, difluoromethoxy, cyano, amino, 2,2,2-trifluoroethoxy, methyl-carbonyl-, oxazol-5-yl, 1,2,3-triazol-1-yl, 4-chloro-1,2,3-triazol-1-yl, 4-bromo-1,2,3-triazol-1-yl, 4-cyano-1,2,3-triazol-1-yl, 4-(difluoromethoxy)-1,2,3-triazol-1-yl, 5-(difluoromethoxy)-1,2,3-triazol-1-yl, 4-(trifluoromethyl)-1,2,3-triazol-1-yl, 4-cyclopropyl-1,2,3-triazol-1-yl, and 1,2,3,4-tetrazol-1-yl.

In certain embodiments, the present invention is directed to compounds of formula (I) wherein R¹ is selected from the group consisting of fluoro, difluoromethyl, difluoromethoxy, 2,2,2-trifluoroethoxy, cyano, amino and methyl-carbonyl-. In certain embodiments, the present invention is directed to compounds of formula (I) wherein R¹ is selected from the group consisting of difluoromethyl, difluoromethoxy, 2,2,2-trifluoroethoxy, cyano, amino and methyl-carbonyl-. In certain embodiments, the present invention is directed to compounds of formula (I) wherein R¹ is selected from the group consisting of difluoromethyl, 2,2,2-trifluoroethoxy, cyano and methyl-carbonyl-.

In certain embodiments, the present invention is directed to compounds of formula (I) wherein R¹ is selected from the group consisting of 1,2,3-triazol-1-yl, 4-bromo-1,2,3-triazol-1-yl, 4-chloro-1,2,3-triazol-1-yl, 4-(trifluoro-methyl)-1,2,3-triazol-1-yl, 4-(difluoro-methoxy)-1,2,3-triazol-1-yl, 5-(difluoro-methoxy)-1,2,3-triazol-1-yl, 4-cyano-1,2,3-triazol-1-yl, 4-cyclopropyl-1,2,3-triazol-1-yl, oxazol-5-yl and 1,2,3,4-tetrazol-1-yl. In certain embodiments, the present invention is directed to compounds of formula (I) wherein R¹ is selected from the group consisting of 4-bromo-1,2,3-triazol-1-yl, 4-chloro-1,2,3-triazol-1-yl, 4-(trifluoromethyl)-1,2,3-triazol-1-yl, 4-(difluoro-methoxy)-1,2,3-triazol-1-yl, 5-(difluoro-methoxy)-1,2,3-triazol-1-yl, 4-cyano-1,2,3-triazol-1-yl, 4-cyclopropyl-1,2,3-triazol-1-yl, oxazol-5-yl and 1,2,3,4-tetrazol-1-yl. In certain embodiments, the present invention is directed to compounds of formula (I) wherein R¹ is selected from the group consisting of 4-bromo-1,2,3-triazol-1-yl, 4-chloro-1,2,3-triazol-1-yl, 4-(trifluoro-methyl)-1,2,3-triazol-1-yl, 4-(difluoromethoxy)-1,2,3-triazol-1-yl, 5-(difluoro-methoxy)-1,2,3-triazol-1-yl, 4-cyano-1,2,3-triazol-1-yl, and 1,2,3,4-tetrazol-1-yl. In certain embodiments, the present invention is directed to compounds of formula (I) wherein R¹ is selected from the group consisting of 4-chloro-1,2,3-triazol-1-yl, 4-(trifluoromethyl)-1,2,3-triazol-1-yl, 4-cyclopropyl-1,2,3-triazol-1-yl, oxazol-5-yl, and 1,2,3,4-tetrazol-1-yl. In certain embodiments, the present invention is directed to compounds of formula (I) wherein R¹ is selected from the group consisting of 4-bromo-1,2,3-triazol-1-yl, 4-chloro-1,2,3-triazol-1-yl, 4-cyano-1,2,3-triazol-1-yl, and 1,2,3,4-tetrazol-1-yl. In certain embodiments, the present invention is directed to compounds of formula (I) wherein R¹ is selected from the group consisting of 4-chloro-1,2,3-triazol-1-yl, 4-(trifluoromethyl)-1,2,3-triazol-1-yl, oxazol-5-yl, and 1,2,3,4-tetrazol-1-yl. In certain embodiments, the present invention is directed to compounds of formula (I) wherein R¹ is selected from the group consisting of 4-chloro-1,2,3-triazol-1-yl, 4-(trifluoro-methyl)-1,2,3-triazol-1-yl and 1,2,3,4-tetrazol-1-yl. In certain embodiments, the present invention is directed to compounds of formula (I) wherein R¹ is selected from the group consisting of 4-(trifluoro-methyl)-1,2,3-triazol-1-yl, and 1,2,3,4-tetrazol-1-yl. In certain embodiments, the present invention is directed to compounds of formula (I) wherein R¹ is selected from the group consisting of pyrazol-5-yl, oxazol-5-yl, 4-chloro-1,2,3-triazol-1-yl, 4-(trifluoro-methyl)-1,2,3-triazol-1-yl and 1,2,3,4-tetrazol-1-yl. In certain embodiments, the present invention is directed to compounds of formula (I) wherein R¹ is 1,2,3,4-tetrazol-1-yl;

In certain embodiments, the present invention is directed to compounds of formula (I), wherein R¹ is selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, nitro, —NR$^A$R$^B$, and —C(O)—$C_{1-4}$alkyl;

a is an integer from 0 to 3;
each R² is independently selected from the group consisting of chloro, fluoro, methyl and methoxy;
Y is N and Z is C(R³), such that

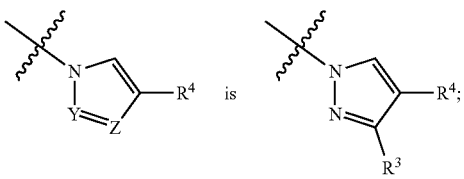 is

R³ is selected from the group consisting of hydrogen, fluoro, chloro and methyl;
R⁴ is selected from the group consisting of
(a) carboxy;
(b) phenyl; wherein the phenyl is optionally substituted with one or more substituents independently selected from the group consisting of halogen, fluorinated $C_{1-2}$alkoxy, —C(O)OH, —C(O)—O—($C_{1-4}$alkyl), —NR$^C$R$^D$, —$C_{1-2}$alkyl-NR$^C$R$^D$, —C(O)—NR$^C$R$^D$, —NR$^D$—C(O)—($C_{1-2}$alkyl)-O—($C_{1-4}$alkyl), —NR$^D$—C(O)—O—($C_{1-2}$alkyl)-O—($C_{1-4}$alkyl), cyclopropyl, 1-carboxy-cycloprop-1-yl, 1-($C_{1-4}$alkoxy-carbonyl)-cycloprop-1-yl, pyrrolidin-2-yl-5-one, pyrrolidin-3-yl-2,5-dione, pyrrol-3-yl-2,5-dione, 1,2,3,4-tetrazol-1-yl, 1,2,3,4-tetrazol-5-yl, 1,2,4-oxadiazol-3-yl-5-one, oxazolidin-5-yl-2,4-dione, 1H-imidazol-5-yl-2,5-dione, thiazol-5-yl-2,4-dione, isoxazol-5-yl-3-ol, isothiazol-5-yl-3-ol, 3-chloro-4-hydroxy-phenyl, —C(O)—NH—CN, —C(O)—NH—SO₂—CH₃, —SO₂—NH—CF₃, and —SO₂—NH—CF₂CF₃;
wherein R$^C$ is selected from the group consisting of hydrogen, $C_{1-4}$alkyl, cyclopropyl, 3-hydroxy-cycloprop-1-yl, —C(O)—$C_{1-4}$alkyl, —C(O)-cyclopropyl, —C(O)—O—$C_{1-4}$alkyl and —SO₂—$C_{1-4}$alkyl; and R$^D$ is selected from the group consisting of hydrogen and $C_{1-4}$alkyl;
(c) 5 membered heterocyclyl; wherein the 5 membered heterocyclyl contains at least one heteroatom selected from the group consisting of O, N and S; optionally contains 1 to 3 additional heteroatoms independently selected from the group consisting of O, N and S; wherein the 5 membered heterocyclyl is saturated, partially unsaturated, or aromatic;
and wherein the 5 membered heterocyclyl is optionally substituted with one or more substituents independently selected from the group consisting of halogen, hydroxy, $C_{1-4}$alkyl, fluorinated $C_{1-4}$alkyl, $C_{1-4}$ alkoxy, fluorinated $C_{1-4}$alkoxy, $C_{3-7}$cycloalkyl, —C(O)OH, —C(O)—O—$C_{1-4}$alkyl, —$C_{1-2}$alkyl-C(O)—O—$C_{1-4}$alkyl, cyano, —NR$^E$R$^F$, —C(O)—NR$^E$R$^F$, pyrrolidin-2-yl-5-one, pyrrolidin-3-yl-2,5-dione, pyrrol-3-yl-2,5-dione, 1,2,3,4-tetrazol-1-yl, 1,2,3,4-tetrazol-5-yl, 1,2,4-oxadiazol-3-yl-5-one, oxazolidin-5-yl-2,4-dione, 1H-imidazol-5-yl-2,5-dione, thiazol-5-yl-2,4-dione, isoxazol-5-yl-3-ol, isothiazol-5-yl-3-ol, 3-chloro-4-hydroxy-phenyl, —C(O)—NH—CN, —C(O)—NH—SO₂—CH₃, —SO₂—NH—CF₃, and —SO₂—NH—CF₂CF₃;
wherein R$^E$ is selected from the group consisting of hydrogen, $C_{1-4}$alkyl, cyclopropyl, 3-hydroxy-cycloprop-1-yl, —C(O)—$C_{1-4}$alkyl, —C(O)-cyclopropyl, —C(O)—O—$C_{1-4}$alkyl and —SO₂—$C_{1-4}$alkyl; and R$^F$ is selected from the group consisting of hydrogen and $C_{1-4}$alkyl;
(d) 6 membered heterocyclyl; wherein the 6 membered heterocyclyl contains at least one heteroatom selected from the group consisting of N, O and S; optionally contains 1 to 3 additional heteroatoms independently selected from the group consisting of O, N and S; wherein the 6 membered heterocyclyl is saturated, partially unsaturated, or aromatic; wherein the 6 membered heterocyclyl is bound through a carbon atom;
and wherein the 6 membered heterocyclyl is optionally substituted with one or more substituents independently selected from the group consisting of halogen, hydroxy, oxo, $C_{1-4}$alkyl, fluorinated $C_{1-4}$alkyl, $C_{1-4}$ alkoxy, fluorinated $C_{1-4}$alkoxy, —$C_{1-2}$alkyl-O—$C_{1-4}$alkyl, $C_{3-7}$cycloalkyl, —C(O)OH, —C(O)—O—$C_{1-4}$alkyl, —$C_{1-2}$alkyl-C(O)—O—$C_{1-4}$alkyl, cyano, —NR$^G$R$^H$, —C(O)—NR$^G$R$^H$, pyrrolidin-2-yl-5-one, pyrrolidin-3-yl-2,5-dione, pyrrol-3-yl-2,5-dione, 1,2,3,4-tetrazol-1-yl, 1,2,3,4-tetrazol-5-yl, 1,2,4-oxadiazol-3-yl-5-one, oxazolidin-5-yl-2,4-dione, 1H-imidazol-5-yl-2,5-dione, thiazol-5-yl-2,4-dione, isoxazol-5-yl-3-ol, isothiazol-5-yl-3-ol, 3-chloro-4-hydroxy-phenyl, —C(O)—NH—CN, —C(O)—NH—SO₂—CH₃, —SO₂—NH—CF₃, and —SO₂—NH—CF₂CF₃;
wherein R$^G$ is selected from the group consisting of hydrogen, $C_{1-4}$alkyl, cyclopropyl, 3-hydroxy-cycloprop-1-yl, —C(O)—$C_{1-4}$alkyl, —C(O)-cyclopropyl, —C(O)—O—$C_{1-4}$alkyl and —SO₂—$C_{1-4}$alkyl; and R$^H$ is selected from the group consisting of hydrogen and $C_{1-4}$alkyl;
and wherein the 6 membered heterocyclyl contains a nitrogen ring atom, said nitrogen ring atom may be further optionally substituted with oxygen to form an N-oxide;
and (e) 9 to 10 membered bicyclic heterocyclyl; wherein the 9 to 10 membered bicyclic heterocyclyl contains at least one heteroatom selected from the group consisting of O, N and S; optionally contains one to four additional heteroatoms independently selected from the group consisting of O, N and S; wherein the 9 to 10 membered bicyclic heterocyclyl is saturated, partially unsaturated, partially aromatic, aromatic, bicyclic, fused, bridged or spiro-cyclic;

and wherein the 9 to 10 membered bicyclic heterocyclyl is optionally substituted with one or more substituents independently selected from the group consisting of halogen, hydroxy, oxo, $C_{1-4}$alkyl, fluorinated $C_{1-4}$alkyl, $C_{1-4}$ alkoxy, fluorinated $C_{1-4}$alkoxy, cyano, —C(O)OH, —C(O)—O—$C_{1-4}$alkyl, —NR$^J$R$^K$, and —C(O)—NR$^J$R$^K$, pyrrolidin-2-yl-5-one, pyrrolidin-3-yl-2,5-dione, pyrrol-3-yl-2,5-dione, 1,2,3,4-tetrazol-1-yl, 1,2,3,4-tetrazol-5-yl, 1,2,4-oxadiazol-3-yl-5-one, oxazolidin-5-yl-2,4-dione, 1H-imidazol-5-yl-2,5-dione, thiazol-5-yl-2,4-dione, isoxazol-5-yl-3-ol, isothiazol-5-yl-3-ol, 3-chloro-4-hydroxy-phenyl, —C(O)—NH—CN, —C(O)—NH—SO$_2$—CH$_3$, —SO$_2$—NH—CF$_3$, and —SO$_2$—NH—CF$_2$CF$_3$; wherein R$^J$ and R$^K$ are each independently selected from the group consisting of hydrogen and $C_{1-4}$alkyl;

R$^5$ is selected from the group consisting of (a) $C_{1-4}$alkyl; wherein the $C_{1-4}$alkyl is optionally substituted with one or more halogen; and further optionally substituted with a substituent selected from the group consisting of hydroxy, $C_{1-4}$alkoxy, fluorinated $C_{1-4}$alkoxy, —C(O)OH, —C(O)—O—($C_{1-4}$alkyl), —C(O)—O-(fluorinated $C_{1-4}$alkyl), —C(O)-(fluorinated $C_{1-4}$alkyl), and —C(O)—NR$^L$R$^M$;

wherein R$^L$ and R$^M$ are each independently selected from the group consisting of hydrogen and $C_{1-2}$alkyl;

(b) —CH$_2$—$C_{3-8}$cycloalkyl or —CH$_2$-adamant-1-yl; wherein the $C_{3-8}$cycloalkyl is optionally substituted with one or more halogen or $C_{1-4}$alkyl; and further optionally substituted with a substituent selected from the group consisting of —C(O)OH, —C(O)—O—$C_{1-4}$ alkyl, —C(O)-(5 to 6 membered saturated heterocyclyl), —C(O)-(isoindolin-2-yl), —C(O)-(azaspiro[2.4]heptan-5-yl), —C(O)-(carboxy substituted azaspiro[2.4]heptan-5-yl), —C(O)—(NR$^P$R$^Q$ substituted azaspiro[2.4]heptan-5-yl), phenyl, 1,1'-biphen-4-yl and —C(O)—NR$^P$R$^Q$;

wherein the —C(O)-(5 to 6 membered saturated heterocyclyl) substituent on the —CH$_2$—$C_{3-8}$cycloalkyl is further optionally substituted on the (5 to 6 membered heterocyclyl) with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, —C(O)OH, —C(O)—O—$C_{1-4}$alkyl, —NR$^P$R$^Q$, phenyl and $C_{3-8}$cycloalkyl;

wherein the phenyl substituent on the —CH$_2$—$C_{3-8}$cycloalkyl is further optionally substituted with one or more substituents independently selected form the group consisting of halogen, hydroxy, $C_{1-4}$alkyl, fluorinated $C_{1-4}$ alkyl, $C_{1-4}$alkoxy, fluorinated $C_{1-4}$alkoxy, cyano, —NR$^P$R$^Q$, and $C_{3-8}$cycloalkyl;

and wherein R$^P$ and R$^Q$ are each independently selected from the group consisting of hydrogen and $C_{1-4}$alkyl;

(c) -L$^1$-(5 to 6 membered saturated heterocyclyl); wherein L$^1$ is selected from the group consisting of —CH$_2$— and —CH$_2$—C(O)—; wherein, when L$^1$ is —CH$_2$—C(O)—, then the (5 to 6 membered saturated heterocyclyl) is bound to the —C(O)— portion of L$^1$; - and wherein the (5 to 6 membered saturated heterocyclyl) is optionally substituted with one to two oxo group;

(d) —$C_{1-2}$alkyl-phenyl; wherein the phenyl is optionally substituted with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, —OCH$_2$—C(O)—NR$^S$R$^T$, phenyl and phenoxy; and wherein R$^S$ and R$^T$ are each independently selected from the group consisting of hydrogen and $C_{1-4}$alkyl;

(e) 1,2,3-triazol-4-yl, 1,2,5-triazol-3-yl, —CH$_2$-1,2,3-triazol-4-yl and —CH$_2$-1,2,5-triazol-3-yl; wherein the 1,2,3-triazol-4-yl or 1,2,5-triazoly-3-yl, whether alone or as part of the substituent group is optionally substituted with a substituent selected from the group consisting of $C_{1-4}$alkyl, fluorinated $C_{1-4}$alkyl, phenyl and piperidinyl;

wherein the piperidinyl is optionally substituted with —C(O)—$C_{1-4}$alkyl;

(f) —CH$_2$-(5 to 6 membered or 9 to 10 membered heterocyclyl); wherein the (5 to 6 membered or 9 to 10 membered heterocyclyl) is other than triazolyl;

wherein the (5 to 6 membered or 9 to 10 membered heterocyclyl) is optionally substituted with one or more substituents independently selected from the group consisting of halogen, hydroxy, oxo, $C_{1-4}$alkyl, fluorinated $C_{1-4}$alkyl, $C_{1-4}$alkoxy, fluorinated $C_{1-4}$alkoxy, cyano, —C(O)OH, —C(O)—O—$C_{1-4}$alkyl, —$C_{1-2}$alkyl-O—$C_{1-4}$alkyl, —$C_{1-2}$ alkyl-O-(fluorinated $C_{1-4}$alkyl), —C(O)—NR$^V$R$^W$, —$C_{1-2}$alkyl-C(O)—NR$^V$R$^W$, -(5 to 6 membered saturated heterocyclyl), —C(O)-(5 to 6 membered saturated heterocyclyl), —C(O)-(carboxy substituted 5 to 6 membered saturated heterocyclyl), —$C_{1-2}$alkyl-C(O)-(5 to 6 membered saturated heterocyclyl), phenyl and pyridinyl;

wherein the pyridinyl substituent on the —CH$_2$-(5 to 6 membered or 9 to 10 membered heterocyclyl) is further optionally substituted with one or more substituents independently selected from the group consisting of halogen and fluorinated $C_{1-4}$alkyl;

and wherein R$^V$ and R$^W$ are each independently selected from the group consisting of hydrogen and $C_{1-4}$alkyl;

and (g) —CH$_2$—NR$^8$R$^9$; wherein R$^8$ is selected from the group consisting of hydrogen and $C_{1-4}$alkyl; R$^9$ is selected from the group consisting of $C_{1-4}$alkyl, fluorinated $C_{1-4}$alkyl, $C_{1-4}$alkoxy, fluorinated $C_{1-4}$alkoxy, —C(O)—$C_{1-4}$alkyl, —C(O)—$C_{1-2}$alkyl-O—$C_{1-4}$alkyl, —C(O)-phenyl, —C(O)—$C_{1-2}$alkyl-phenyl, —C(O)—O—$C_{1-4}$alkyl, —C(O)—O-phenyl, —C(O)—O—$C_{1-2}$alkyl-phenyl, —C(O)—$C_{3-7}$cycloalkyl, —C(O)-(1-methyl-cycloprop-1-yl), —C(O)-(5 to 6 membered saturated heterocyclyl), —C(O)—$C_{1-2}$alkyl-C(O)-(5 to 6 membered saturated heterocyclyl), —O—$C_{1-2}$alkyl-C(O)-(5 to 6 membered saturated heterocyclyl), —C(O)-(1-methyl-pyridinyl-one) and —C(O)—NR$^X$R$^Y$; and wherein R$^X$ and R$^Y$ are each independently selected from the group consisting of hydrogen and $C_{1-4}$alkyl;

R$^6$ and R$^7$ are each independently selected from the group consisting of hydrogen, halogen, $C_{1-4}$alkyl and $C_{1-4}$alkoxy;

provided that at least one of R$^6$ or R$^7$ is hydrogen;

or a stereoisomer, isotopologue, isotopomer, or pharmaceutically acceptable salt or solvate thereof.

In certain embodiments, the present invention is directed to compounds of formula (I) wherein R$^1$ is selected from the group consisting of halogen, $C_{1-4}$alkyl, fluorinated $C_{1-4}$alkyl, $C_{1-4}$alkoxy, fluorinated $C_{1-4}$alkoxy, cyano, —NR$^A$R$^B$, and —C(O)—$C_{1-4}$alkyl; wherein R$^A$ and R$^B$ are each independently selected from the group consisting of hydrogen and $C_{1-4}$alkyl;

a is an integer from 1 to 2;

each R$^2$ is independently selected from the group consisting of chloro and fluoro;

Y is N and Z is C(R³), such that

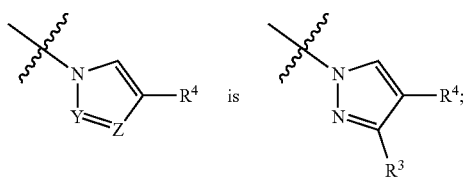 is

R³ is selected from the group consisting of hydrogen, and methyl;
R⁴ is selected from the group consisting of
(a) carboxy;
(b) phenyl; wherein the phenyl is optionally substituted with one to two substituents independently selected from the group consisting of halogen, fluorinated $C_{1-2}$alkoxy, —C(O)OH, —C(O)—O—($C_{1-4}$alkyl), —NR$^C$R$^D$, —$C_{1-2}$alkyl-NR$^C$R$^D$, —C(O)—NR$^C$R$^D$, —NR$^D$—C(O)—($C_{1-2}$alkyl)-O—($C_{1-4}$alkyl), —NR$^D$—C(O)—O—($C_{1-2}$alkyl)-O—($C_{1-4}$alkyl), cyclopropyl, 1-carboxy-cycloprop-1-yl, 1-($C_{1-4}$alkoxy-carbonyl)-cycloprop-1-yl, pyrrolidin-2-yl-5-one, 1,2,3,4-tetrazol-1-yl, 1,2,4-oxadiazol-3-yl-5-one and —C(O)—NH—SO₂—CH₃;
wherein R$^C$ is selected from the group consisting of hydrogen, cyclopropyl, 3-hydroxy-cycloprop-1-yl, —C(O)—$C_{1-4}$alkyl, —C(O)-cyclopropyl, —C(O)—O—$C_{1-4}$alkyl and —SO₂—$C_{1-4}$alkyl; and R$^D$ is selected from the group consisting of hydrogen and $C_{1-2}$alkyl;
(c) 5 membered heterocyclyl; wherein the 5 membered heterocyclyl contains at least one heteroatom selected from the group consisting of O, N and S; optionally contains 1 to 3 additional heteroatoms independently selected from the group consisting of O, N and S; wherein the 5 membered heterocyclyl is saturated, partially unsaturated, or aromatic;
wherein the 5 membered heterocyclyl is optionally substituted with one to two substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, $C_{3-7}$cycloalkyl, —C(O)OH, —C(O)—O—$C_{1-4}$alkyl, —$C_{1-2}$alkyl-C(O)—O—$C_{1-4}$alkyl, cyano, —NR$^E$R$^F$ and —C(O)—NR$^E$R$^F$; and wherein R$^E$ is selected from the group consisting of hydrogen, $C_{1-4}$alkyl, cyclopropyl, 3-hydroxy-cycloprop-1-yl, —C(O)—$C_{1-4}$alkyl, —C(O)-cyclopropyl, —C(O)—O—$C_{1-4}$alkyl and —SO₂—$C_{1-4}$alkyl; and R$^F$ is hydrogen and $C_{1-4}$alkyl;
(d) 6 membered heterocyclyl; wherein the 6 membered heterocyclyl contains at least one heteroatom selected from the group consisting of N, O and S; optionally contains 1 to 3 additional heteroatoms independently selected from the group consisting of O, N and S; wherein the 6 membered heterocyclyl is saturated, partially unsaturated, or aromatic; wherein the 6 membered heterocyclyl is bound through a carbon atom;
and wherein the 6 membered heterocyclyl is optionally substituted with one to two substituents independently selected from the group consisting of halogen, hydroxy, oxo, $C_{1-4}$alkyl, fluorinated $C_{1-4}$alkyl, $C_{1-4}$alkoxy, fluorinated $C_{1-4}$alkoxy, —$C_{1-2}$alkyl-O—$C_{1-4}$alkyl, $C_{3-7}$cycloalkyl, —C(O)OH, —C(O)—O—$C_{1-4}$alkyl, —$C_{1-2}$alkyl-C(O)—O—$C_{1-4}$ alkyl, cyano, —NR$^G$R$^H$, and —C(O)—NR$^G$R$^H$; wherein R$^G$ is selected from the group consisting of hydrogen, $C_{1-4}$ alkyl, cyclopropyl, 3-hydroxy-cycloprop-1-yl, —C(O)—$C_{1-4}$alkyl, —C(O)-cyclopropyl, —C(O)—O—$C_{1-4}$alkyl and —SO₂—$C_{1-4}$alkyl; and R$^H$ is hydrogen and $C_{1-4}$alkyl;
and wherein the 6 membered heterocyclyl contains a nitrogen ring atom, said nitrogen ring atom may be further optionally substituted with oxygen to form an N-oxide;
and (e) 9 to 10 membered bicyclic heterocyclyl; wherein the 9 to 10 membered bicyclic heterocyclyl contains at least one heteroatom selected from the group consisting of O, N and S; optionally contains one to four additional heteroatoms independently selected from the group consisting of O, N and S; wherein the 9 to 10 membered bicyclic heterocyclyl is saturated, partially unsaturated, partially aromatic, aromatic, bicyclic, fused, bridged or spiro-cyclic;
and wherein the 9 to 10 membered bicyclic heterocyclyl is optionally substituted with one to two substituents independently selected from the group consisting of halogen, hydroxy, oxo, $C_{1-4}$alkyl, fluorinated $C_{1-4}$alkyl, $C_{1-4}$ alkoxy, fluorinated $C_{1-4}$alkoxy, cyano, —C(O)OH, —C(O)—O—$C_{1-4}$alkyl, NR$^J$R$^K$, and —C(O)—NR$^J$R$^K$; wherein R$^J$ and R$^K$ are each hydrogen;
R⁵ is selected from the group consisting of
(a) $C_{1-4}$alkyl; wherein the $C_{1-4}$alkyl is optionally substituted with one or more halogen; and further optionally substituted with a substituent selected from the group consisting of hydroxy, $C_{1-4}$alkoxy, fluorinated $C_{1-4}$alkoxy, —C(O)OH, —C(O)—O—($C_{1-4}$alkyl), —C(O)—O-(fluorinated $C_{1-4}$alkyl), —C(O)-(fluorinated $C_{1-4}$alkyl), and —C(O)—NR$^L$R$^M$;
wherein R$^L$ and R$^M$ are each independently selected from the group consisting of hydrogen and $C_{1-2}$alkyl;
(b) —CH₂—$C_{3-8}$cycloalkyl or —CH₂-adamant-1-yl; wherein the $C_{3-8}$cycloalkyl is optionally substituted with one to two halogen or $C_{1-4}$alkyl; and further optionally substituted with a substituent selected from the group consisting of —C(O)OH, —C(O)—O—$C_{1-4}$ alkyl, —C(O)-(5 to 6 membered saturated heterocyclyl), —C(O)-(isoindolin-2-yl), —C(O)-(azaspiro[2.4]heptan-5-yl), —C(O)-(carboxy substituted azaspiro[2.4]heptan-5-yl), —C(O)—(NR$^P$R$^Q$ substituted azaspiro[2.4]heptan-5-yl), phenyl, 1,1'-biphen-4-yl and —C(O)—NR$^P$R$^Q$;
wherein the —C(O)-(5 to 6 membered saturated heterocyclyl) substituent on the —CH₂—$C_{3-8}$cycloalkyl is further optionally substituted on the (5 to 6 membered heterocyclyl) with one to two substituents independently selected from the group consisting of halogen, $C_{1-4}$alkyl, —C(O)OH, —C(O)—O—$C_{1-4}$alkyl, phenyl and $C_{3-8}$cycloalkyl;
wherein the phenyl substituent on the —CH₂—$C_{3-8}$cycloalkyl is further optionally substituted with $C_{1-4}$alkoxy;
and wherein R$^P$ and R$^Q$ are each independently selected from the group consisting of hydrogen and $C_{1-4}$alkyl;
(c) -L¹-(5 to 6 membered saturated heterocyclyl); wherein L¹ is selected from the group consisting of —CH₂— and —CH₂—C(O)—; wherein, when L¹ is —CH₂—C(O)—, then the (5 to 6 membered saturated heterocyclyl) is bound to the —C(O)— portion of L¹; and wherein the 5 to 6 membered saturated heterocyclyl is optionally substituted with one to two oxo group;
(d) —$C_{1-2}$alkyl-phenyl; wherein the phenyl is optionally substituted with one to two substituents independently selected from the group consisting of halogen, hydroxy, C$_{1-4}$alkyl, fluorinated C$_{1-4}$alkyl, C$_{1-4}$alkoxy, fluorinated C$_{1-4}$alkoxy, —OCH$_2$—C(O)—NR$^S$R$^T$, phenyl and phenoxy; and wherein R$^S$ and R$^T$ are each independently selected from the group consisting of hydrogen and C$_{1-2}$alkyl;
(e) 1,2,3-triazol-4-yl, 1,2,5-triazol-3-yl, —CH$_2$-1,2,3-triazol-4-yl and —CH$_2$-1,2,5-triazol-3-yl; wherein the 1,2,3-triazol-4-yl or 1,2,5-triazoly-3-yl, whether alone or as part of the substituent group is optionally substituted with a substituent selected from the group consisting of C$_{1-4}$alkyl, fluorinated C$_{1-4}$alkyl, phenyl and piperidinyl;
wherein the piperidinyl is optionally substituted with —C(O)—C$_{1-4}$alkyl;
(f) —CH$_2$-(5 to 6 membered or 9 to 10 membered heterocyclyl); wherein the (5 to 6 membered or 9 to 10 membered heterocyclyl) is other than triazolyl;
wherein the (5 to 6 membered or 9 to 10 membered heterocyclyl) is optionally substituted with one to two substituents independently selected from the group consisting of halogen, hydroxy, oxo, C$_{1-4}$alkyl, fluorinated C$_{1-4}$alkyl, C$_{1-4}$alkoxy, fluorinated C$_{1-4}$alkoxy, cyano, —C(O)OH, —C(O)—O—C$_{1-4}$alkyl, —C$_{1-2}$alkyl-O—C$_{1-4}$alkyl, —C$_{1-2}$ alkyl-O-(fluorinated C$_{1-4}$alkyl), —C(O)—NR$^V$R$^W$, —C$_{1-2}$alkyl-C(O)—NR$^V$R$^W$, -(5 to 6 membered saturated heterocyclyl), —C(O)-(5 to 6 membered saturated heterocyclyl), —C(O)-(carboxy substituted 5 to 6 membered saturated heterocyclyl), —C$_{1-2}$alkyl-C(O)-(5 to 6 membered saturated heterocyclyl), phenyl and pyridinyl;
wherein the pyridinyl substituent on the —CH$_2$-(5 to 6 membered or 9 to 10 membered heterocyclyl) is further optionally substituted with one to two substituents independently selected from the group consisting of halogen and fluorinated C$_{1-4}$alkyl;
and wherein R$^V$ and R$^W$ are each independently selected from the group consisting of hydrogen and C$_{1-4}$alkyl;
and (g) —CH$_2$—NR$^8$R$^9$; wherein R$^8$ is selected from the group consisting of hydrogen and C$_{1-2}$alkyl; R$^9$ is selected from the group consisting of C$_{1-4}$alkyl, fluorinated C$_{1-4}$alkyl, C$_{1-4}$alkoxy, fluorinated C$_{1-4}$alkoxy, —C(O)—C$_{1-4}$alkyl, —C(O)—C$_{1-2}$alkyl-O—C$_{1-4}$alkyl, —C(O)-phenyl, —C(O)—C$_{1-2}$alkyl-phenyl, —C(O)—O—C$_{1-4}$alkyl, —C(O)—O-phenyl, —C(O)—O—C$_{1-2}$alkyl-phenyl, —C(O)—C$_{3-7}$cycloalkyl, —C(O)-(1-methyl-cycloprop-1-yl), —C(O)-(5 to 6 membered saturated heterocyclyl), —C(O)—C$_{1-2}$alkyl-C(O)-(5 to 6 membered saturated heterocyclyl), —O—C$_{1-2}$alkyl-C(O)-(5 to 6 membered saturated heterocyclyl), —C(O)-(1-methyl-pyridinyl-one) and —C(O)—NR$^X$R$^Y$; and wherein R$^X$ and
R$^Y$ are each independently selected from the group consisting of hydrogen and C$_{1-2}$alkyl;
R$^6$ and R$^7$ are each independently selected from the group consisting of hydrogen, halogen, C$_{1-4}$alkyl and C$_{1-4}$alkoxy;
provided that at least one of R$^6$ or R$^7$ is hydrogen;
or a stereoisomer, isotopologue, isotopomer, or pharmaceutically acceptable salt or solvate thereof.

In certain embodiments, the present invention is directed to compounds of formula (I), wherein R$^1$ is selected from the group consisting of halogen, C$_{1-4}$alkyl, fluorinated C$_{1-4}$alkyl, C$_{1-4}$alkoxy, fluorinated C$_{1-4}$alkoxy, cyano, —NR$^A$R$^B$ and —C(O)—C$_{1-4}$alkyl; wherein R$^A$ and R$^B$ are each independently selected from the group consisting of hydrogen and C$_{1-2}$alkyl;
a is an integer from 1 to 2;
each R$^2$ is independently selected from the group consisting of chloro and fluoro;
Y is N and Z is C(R$^3$), such that

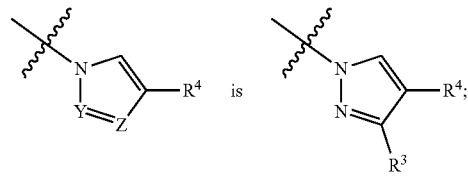

R$^3$ is hydrogen;
R$^4$ is selected from the group consisting of
(b) phenyl; wherein the phenyl is optionally substituted with one to two substituents independently selected from the group consisting of halogen, —C(O)OH, —NR$^C$R$^D$ and —C(O)—NR$^C$R$^D$; wherein R$^C$ is selected from the group consisting of hydrogen and —C(O)—O—C$_{1-4}$alkyl; and R$^D$ is hydrogen;
(c) 5 membered heterocyclyl; wherein the 5 membered heterocyclyl contains at least one N; optionally contains 1 to 3 additional N; wherein the 5 membered heterocyclyl is saturated, partially unsaturated, or aromatic; and wherein the 5 membered heterocyclyl is optionally substituted with one to two substituents independently selected from the group consisting of halogen, C$_{1-4}$alkyl, fluorinated C$_{1-4}$alkyl and —C(O)OH;
and (d) 6 membered heterocyclyl; wherein the 6 membered heterocyclyl contains at least one N; optionally contains 1 to 3 additional N; wherein the 6 membered heterocyclyl is saturated, partially unsaturated, or aromatic; wherein the 6 membered heterocyclyl is bound through a carbon atom; and wherein the 6 membered heterocyclyl is optionally substituted with one to two substituents independently selected from the group consisting of halogen, oxo, fluorinated C$_{1-4}$alkyl, —C(O)OH and —NR$^G$R$^H$; wherein R$^G$ and R$^H$ are each independently selected from the group consisting of hydrogen and C$_{1-4}$alkyl; and wherein the 6 membered heterocyclyl contains a nitrogen ring atom, said nitrogen ring atom may be further optionally substituted with oxygen to form an N-oxide;
R$^5$ is selected from the group consisting of
(a) C$_{1-4}$alkyl; wherein the C$_{1-4}$alkyl is optionally substituted with a substituent selected from the group consisting of C$_{1-4}$alkoxy and fluorinated C$_{1-4}$alkoxy;
(b) —CH$_2$—C$_{3-8}$cycloalkyl; wherein the C$_{3-6}$cycloalkyl is optionally substituted with a substituent selected from the group consisting of —C(O)-(5 to 6 membered saturated heterocyclyl) and —C(O)—NR$^P$R$^Q$; and wherein R$^P$ and R$^Q$ are each independently selected from the group consisting of hydrogen and C$_{1-4}$alkyl;
(c) -L$^1$-(5 to 6 membered saturated heterocyclyl); wherein L$^1$ is —CH$_2$—; and wherein the (5 to 6 membered saturated heterocyclyl) is optionally substituted with one to two oxo group;
(d) —C$_{1-2}$alkyl-phenyl; wherein the phenyl portion is optionally substituted with halogen;
and (f) —CH$_2$-(5 to 6 membered heterocyclyl); wherein the (5 to 6 membered heterocyclyl) is other than triazolyl; wherein the (5 to 6 membered heterocyclyl) is optionally substituted with one to two substituents independently selected from the group consisting of halogen, $C_{1-4}$alkyl, fluorinated $C_{1-4}$alkyl and —C(O)—NR$^V$R$^W$;

and wherein R$^V$ and R$^W$ are each independently selected from the group consisting of hydrogen and $C_{1-4}$alkyl;

R$^6$ is hydrogen;

R$^7$ is selected from the group consisting of hydrogen and $C_{1-4}$alkoxy; or a stereoisomer, isotopologue, isotopomer, or pharmaceutically acceptable salt or solvate thereof.

In certain embodiments, the present invention is directed to compounds of formula (I), wherein R$^1$ is selected from the group consisting of fluoro, difluoromethyl, difluoromethoxy, 2,2,2-trifluoroethoxy, cyano, amino and methyl-carbonyl-;

a is an integer from 1 to 2;

each R$^2$ is independently selected from the group consisting of 5-chloro and 6-fluoro;

Y is N and Z is C(R$^3$), such that

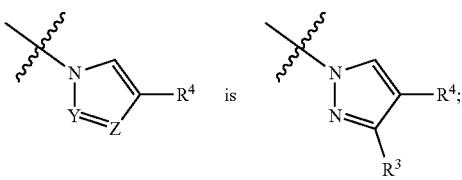

R$^3$ is hydrogen;

R$^4$ is selected from the group consisting of 4-carboxy-phenyl, 4-(amino-carbonyl)-phenyl, 4-(methoxy-carbonyl-amino)-phenyl, 3-fluoro-4-carboxy-phenyl, 3-fluoro-4-(amino-carbonyl)-phenyl, 2-fluoro-6-amino-pyridin-3-yl, 2-carboxy-pyridin-4-yl, 2-(trifluoro-methyl)-pyridin-4-yl, pyridin-4-yl-1-oxide, 5-carboxy-pyrrol-3-yl, 2-(trifluoro-methyl)-pyrimidin-4-yl, 1-methyl-pyrazol-5-yl, 1-methyl-pyridazin-4-yl-6-one, 1-methyl-1,2,3-triazol-5-yl, 1-methyl-4-fluoro-1,2,3-triazol-5-yl, 1-methyl-1,2,4-triazol-5-yl and 1-(difluoro-methyl)-1,2,4-triazol-5-yl;

R$^5$ is selected from the group consisting of
(a) ethyl, 2-methoxy-ethyl-, S-(2-methoxy-ethyl-), R-(2-methoxy-ethyl-), 2-(difluoro-methoxy)-ethyl-, R-(2-(difluoro-methoxy)-ethyl-), S-(2-(difluoro-methoxy)-ethyl-), R*-(2-(difluoro-methoxy)-ethyl-2,2-d2-), S*-(2-(difluoro-methoxy)-ethyl-2,2-d2-),
(b) cyclopropyl-methyl-, R*-(cyclopropyl-methyl-), S*-(cyclopropyl-methyl-), S-(cyclopropyl-methyl-), R-(cyclopropyl-methyl-), 2S*-(amino-carbonyl)-1S*-cyclopropyl-methyl-, 2R*-(piperidin-1-yl-carbonyl)-1S*-cyclopropyl-methyl-, 2S*-(piperidin-1-yl-carbonyl)-1S*-cyclopropyl-methyl-, R*-(2S*-(piperidin-1-yl-carbonyl)-cyclopropyl-methyl-), S*-(2R*-(piperidin-1-yl-carbonyl)-cyclopropyl-methyl-), S*-(2-(piperidin-1-yl-carbonyl)-cyclopropyl-methyl-),
(c) R*-(pyrrolidin-1-yl-2-one-methyl-), S*-(pyrrolidin-1-yl-2-one-methyl-),
(d) phenyl-methyl-, 4-fluoro-phenyl-methyl-, R*-(4-fluoro-phenyl-methyl-), S*-(4-fluoro-phenyl-methyl-),
(f) 4-fluoro-pyrazol-1-yl-methyl-, R*-(4-fluoro-pyrazol-1-yl-methyl-), S*-(4-fluoro-pyrazol-1-yl-methyl-), S*-(5-(amino-carbonyl)-pyrazol-1-yl-methyl-), R*-(5-(amino-carbonyl)-pyrazol-1-yl-methyl-), S*-(1-methyl-pyrazol-4-yl-methyl-), R*-(1-methyl-pyrazol-4-yl-methyl-), S-(1-methyl-pyrazol-3-yl)-methyl-), R-(1-methyl-pyrazol-3-yl)-methyl-), S-(1-methyl-pyrazol-3-yl-methyl-), R-(1-methyl-pyrazol-3-yl-methyl-), 1-(difluoro-methyl)-pyrazol-3-yl-methyl-, S*-(1-(difluoro-methyl)-pyrazol-3-yl-methyl-) and R*-(1-(difluoro-methyl)-pyrazol-3-yl-methyl-);

R$^6$ is hydrogen;

R$^7$ is selected from the group consisting of hydrogen and methoxy;

or a pharmaceutically acceptable salt or solvate thereof.

In certain embodiments, the present invention is directed to compounds of formula (I), wherein R$^1$ is selected from the group consisting of difluoromethyl, difluoromethoxy, 2,2,2-trifluoroethoxy, cyano, amino and methyl-carbonyl-;

a is an integer from 1 to 2;

each R$^2$ is independently selected from the group consisting of 5-chloro and 6-fluoro;

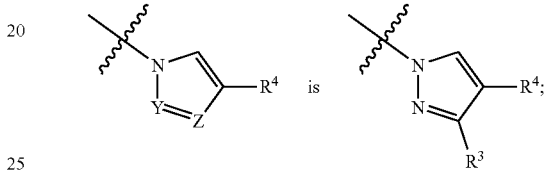

Y is N and Z is C(R$^3$), such that z is R$^3$

R$^3$ is hydrogen;

R$^4$ is selected from the group consisting of 4-carboxy-phenyl, 3-fluoro-4-carboxy-phenyl, 4-(amino-carbonyl)-phenyl, 3-fluoro-4-(amino-carbonyl)-phenyl, 5-carboxy-pyrrol-3-yl, 1-methyl-pyrazol-5-yl, pyridin-4-yl-1-oxide, 2-(trifluoro-methyl)-pyridin-4-yl, 2-fluoro-6-amino-pyridin-3-yl, 1-methyl-1,2,3-triazol-5-yl, 1-(difluoro-methyl)-1,2,4-triazol-5-yl and 1-methyl-4-fluoro-1,2,3-triazol-5-yl;

R$^5$ is selected from the group consisting of R-(2-methoxy-ethyl-), R-(2-(difluoro-methoxy)-ethyl-), phenyl-methyl-, 4-fluoro-phenyl-methyl-, S*-(4-fluoro-phenyl-methyl-), cyclopropyl-methyl-, R-(cyclopropyl-methyl-), S*-(cyclopropyl-methyl-), R*-(cyclopropyl-methyl-), R*-(2S*-(piperidin-1-yl-carbonyl)-cyclopropyl-methyl-), R*-(pyrrolidin-1-yl-2-one-methyl-), 4-fluoro-pyrazol-1-yl-methyl-, R*-(4-fluoro-pyrazol-1-yl-methyl-), S*-(5-(amino-carbonyl)-pyrazol-1-yl-methyl-), -(1-methyl-pyrazol-3-yl-methyl-), 1-(difluoro-methyl)-pyrazol-3-yl-methyl-, S*-(1-(difluoro-methyl)-pyrazol-3-yl-methyl-), R*-(1-(difluoro-methyl)-pyrazol-3-yl-methyl-) and R*-(1-methyl-pyrazol-4-yl-methyl-);

R$^6$ is hydrogen;

R$^7$ is selected from the group consisting of hydrogen and methoxy;

or a pharmaceutically acceptable salt or solvate thereof.

In certain embodiments, the present invention is directed to compounds of formula (I), wherein R$^1$ is selected from the group consisting of difluoromethyl, 2,2,2-trifluoroethoxy, cyano and methyl-carbonyl-;

a is an integer from 1 to 2;

each R$^2$ is independently selected from the group consisting of 5-chloro and 6-fluoro;

Y is N and Z is C(R³), such that

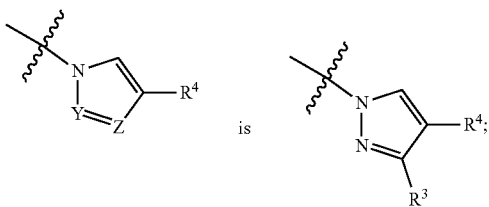

is

R³ is hydrogen;
R⁴ is selected from the group consisting of 4-carboxy-phenyl, 3-fluoro-4-carboxy-phenyl, 4-(amino-carbonyl)-phenyl, 3-fluoro-4-(amino-carbonyl)-phenyl, 5-carboxy-pyrrol-3-yl, pyridin-4-yl-1-oxide and 1-methyl-1,2,3-triazol-5-yl;
R⁵ is selected from the group consisting of R-(2-methoxy-ethyl-), R-(2-(difluoro-methoxy)-ethyl-), phenyl-methyl-, S*-(4-fluoro-phenyl-methyl-), cyclopropyl-methyl-, R-(cyclopropyl-methyl-), R*-(pyrrolidin-1-yl-2-one-methyl-), 4-fluoro-pyrazol-1-yl-methyl-, R-(1-methyl-pyrazol-3-yl-methyl-), 1-(difluoro-methyl)-pyrazol-3-yl-methyl-, S*-(1-(difluoro-methyl)-pyrazol-3-yl-methyl-), R*-(1-(difluoro-methyl)-pyrazol-3-yl-methyl-) and R*-(1-methyl-pyrazol-4-yl-methyl-);
R⁶ is hydrogen;
R⁷ is selected from the group consisting of hydrogen and methoxy;
or a pharmaceutically acceptable salt or solvate thereof.

In certain embodiments, the present invention is directed to compounds of formula (I), wherein R¹ is selected from the group consisting of difluoromethyl, 2,2,2-trifluoroethoxy and methyl-carbonyl-;
a is an integer from 1 to 2;
each R² is independently selected from the group consisting of 5-chloro and 6-fluoro;
Y is N and Z is C(R³), such that

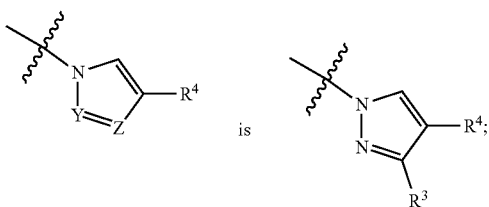

is

R³ is hydrogen;
R⁴ is selected from the group consisting of 4-carboxy-phenyl, 3-fluoro-4-carboxy-phenyl and 4-(amino-carbonyl)-phenyl;
R⁵ is selected from the group consisting of R-(2-(difluoro-methoxy)-ethyl-), phenyl-methyl-, R*-(pyrrolidin-1-yl-2-one-methyl-), 4-fluoro-pyrazol-1-yl-methyl-, R-(1-methyl-pyrazol-3-yl-methyl-), 1-(difluoro-methyl)-pyrazol-3-yl-methyl-, S*-(1-(difluoro-methyl)-pyrazol-3-yl-methyl-) and R*-(1-(difluoro-methyl)-pyrazol-3-yl-methyl-);
R⁶ is hydrogen;
R⁷ is selected from the group consisting of hydrogen and methoxy;
or a pharmaceutically acceptable salt or solvate thereof.

In certain embodiments, the present invention is directed to compounds of formula (I) wherein a is an integer from 1 to 2. In certain embodiments, the present invention is directed to compounds of formula (I) wherein a is 0. In certain embodiments, the present invention is directed to compounds of formula (I) wherein a is 1. In certain embodiments, the present invention is directed to compounds of formula (I) wherein a is 2. In certain embodiments, the present invention is directed to compounds of formula (I) wherein a is 3.

In certain embodiments, the present invention is directed to compounds of formula (I) wherein R² is selected from the group consisting of fluoro and chloro. In certain embodiments, the present invention is directed to compounds of formula (I) wherein R² is fluoro. In certain embodiments, the present invention is directed to compounds of formula (I) wherein R² is chloro.

In certain embodiments, the present invention is directed to compounds of formula (I) wherein each R² is independently selected from the group consisting of 4-chloro, 5-chloro, 4-fluoro, 5-fluoro and 6-fluoro. In certain embodiments, the present invention is directed to compounds of formula (I) wherein each R² is independently selected from the group consisting of 4-fluoro, 5-chloro and 6-fluoro. In certain embodiments, the present invention is directed to compounds of formula (I) wherein each R² is independently selected from the group consisting of 5-chloro and 6-fluoro. In certain embodiments, the present invention is directed to compounds of formula (I) wherein a is 2 and one R² is 5-chloro and one R² is 6-fluoro.

In certain embodiments, the present invention is directed to compounds of formula (I) wherein R³ is selected from the group consisting of hydrogen and methyl. In certain embodiments, the present invention is directed to compounds of formula (I) wherein R³ is hydrogen. In certain embodiments, the present invention is directed to compounds of formula (I) wherein R³ is methyl. In certain embodiments, the present invention is directed to compounds of formula (I) wherein R³ is selected from the group consisting of fluoro and chloro.

In certain embodiments, the present invention is directed to compounds of formula (I) wherein R⁴ is selected from any one or more (a) through (e), independently selected from any (a) through (e), as described in any of the embodiments herein.

In certain embodiments, the present invention is directed to compounds of formula (I) wherein R⁴ is selected from the group consisting of
(a) carboxy;
(b) phenyl; wherein the phenyl is optionally substituted with one to two substituents independently selected from the group consisting of halogen, fluorinated $C_{1-2}$alkoxy, —C(O)OH, —C(O)—O—($C_{1-4}$alkyl), —NR$^C$R$^D$, —$C_{1-2}$alkyl-NR$^C$R$^D$, —C(O)—NR$^C$R$^D$, —NR$^D$—C(O)—($C_{1-2}$alkyl)-O—($C_{1-4}$alkyl), —NR$^D$—C(O)—O—($C_{1-2}$alkyl)-O—($C_{1-4}$alkyl), cyclopropyl, 1-carboxy-cycloprop-1-yl, 1-($C_{1-4}$alkoxy-carbonyl)-cycloprop-1-yl, pyrrolidin-2-yl-5-one, 1,2,3,4-tetrazol-1-yl, 1,2,4-oxadiazol-3-yl-5-one and —C(O)—NH—SO₂—CH₃;
wherein R$^C$ is selected from the group consisting of hydrogen, cyclopropyl, 3-hydroxy-cycloprop-1-yl, —C(O)—$C_{1-4}$alkyl, —C(O)-cyclopropyl, —C(O)—O—$C_{1-4}$alkyl and —SO₂—$C_{1-4}$alkyl; and R$^D$ is selected from the group consisting of hydrogen and $C_{1-2}$alkyl;
(c) 5 membered heterocyclyl; wherein the 5 membered heterocyclyl contains at least one heteroatom selected from the group consisting of O, N and S; optionally contains 1 to 3 additional heteroatoms independently selected from the group consisting of O, N and S; wherein the 5 membered heterocyclyl is saturated, partially unsaturated, or aromatic;

wherein the 5 membered heterocyclyl is optionally substituted with one to two substituents independently selected from the group consisting of halogen, hydroxy, $C_{1-4}$alkyl, fluorinated $C_{1-4}$alkyl, $C_{1-4}$ alkoxy, fluorinated $C_{1-4}$alkoxy, $C_{3-7}$cycloalkyl, —C(O)OH, —C(O)—O—$C_{1-4}$alkyl, —$C_{1-2}$alkyl-C(O)—O—$C_{1-4}$ alkyl, cyano, —NR$^E$R$^F$ and —C(O)—NR$^E$R$^F$; and wherein R$^E$ is selected from the group consisting of hydrogen, $C_{1-4}$alkyl, cyclopropyl, 3-hydroxy-cycloprop-1-yl, —C(O)—$C_{1-4}$alkyl, —C(O)-cyclopropyl, —C(O)—O—$C_{1-4}$alkyl and —SO$_2$—$C_{1-4}$alkyl; and R$^F$ is hydrogen and $C_{1-4}$alkyl;

(d) 6 membered heterocyclyl; wherein the 6 membered heterocyclyl contains at least one heteroatom selected from the group consisting of N, O and S; optionally contains 1 to 3 additional heteroatoms independently selected from the group consisting of O, N and S; wherein the 6 membered heterocyclyl is saturated, partially unsaturated, or aromatic; wherein the 6 membered heterocyclyl is bound through a carbon atom;

and wherein the 6 membered heterocyclyl is optionally substituted with one to two substituents independently selected from the group consisting of halogen, hydroxy, oxo, $C_{1-4}$alkyl, fluorinated $C_{1-4}$alkyl, $C_{1-4}$ alkoxy, fluorinated $C_{1-4}$alkoxy, —$C_{1-2}$alkyl-O—$C_{1-4}$alkyl, $C_{3-7}$cycloalkyl, —C(O)OH, —C(O)—O—$C_{1-4}$alkyl, —$C_{1-2}$alkyl-C(O)—O—$C_{1-4}$alkyl, cyano, —NR$^G$R$^H$, and —C(O)—NR$^G$R$^H$; wherein R$^G$ is selected from the group consisting of hydrogen, $C_{1-4}$alkyl, cyclopropyl, 3-hydroxy-cycloprop-1-yl, —C(O)—$C_{1-4}$alkyl, —C(O)-cyclopropyl, —C(O)—O—$C_{1-4}$ alkyl and —SO$_2$—$C_{1-4}$alkyl; and R$^H$ is hydrogen and $C_{1-4}$alkyl;

and wherein the 6 membered heterocyclyl contains a nitrogen ring atom, said nitrogen ring atom may be further optionally substituted with oxygen to form an N-oxide;

and (e) 9 to 10 membered bicyclic heterocyclyl; wherein the 9 to 10 membered bicyclic heterocyclyl contains at least one heteroatom selected from the group consisting of O, N and S; optionally contains one to four additional heteroatoms independently selected from the group consisting of O, N and S; wherein the 9 to 10 membered bicyclic heterocyclyl is saturated, partially unsaturated, partially aromatic, aromatic, bicyclic, fused, bridged or spiro-cyclic;

and wherein the 9 to 10 membered bicyclic heterocyclyl is optionally substituted with one to two substituents independently selected from the group consisting of halogen, hydroxy, oxo, $C_{1-4}$alkyl, fluorinated $C_{1-4}$alkyl, $C_{1-4}$alkoxy, fluorinated $C_{1-4}$alkoxy, cyano, —C(O)OH, —C(O)—O—$C_{1-4}$alkyl, NR$^J$R$^K$, and —C(O)—NR$^J$R$^K$;

wherein R$^J$ and R$^K$ are each hydrogen; In certain embodiments, the present invention is directed to compounds of formula (I) wherein R$^4$ is selected from the group consisting of (b) phenyl; wherein the phenyl is optionally substituted with one to two substituents independently selected from the group consisting of halogen, —C(O)OH, —NR$^C$R$^D$ and —C(O)—NR$^C$R$^D$; wherein R$^C$ is selected from the group consisting of hydrogen and —C(O)—O—$C_{1-4}$alkyl; and R$^D$ is hydrogen; (c) 5 membered heterocyclyl; wherein the 5 membered heterocyclyl contains at least one N; optionally contains 1 to 3 additional N; wherein the 5 membered heterocyclyl is saturated, partially unsaturated, or aromatic; and wherein the 5 membered heterocyclyl is optionally substituted with one to two substituents independently selected from the group consisting of halogen, $C_{1-4}$alkyl, fluorinated $C_{1-4}$alkyl and —C(O)OH; and (d) 6 membered heterocyclyl; wherein the 6 membered heterocyclyl contains at least one N; optionally contains 1 to 3 additional N; wherein the 6 membered heterocyclyl is saturated, partially unsaturated, or aromatic; wherein the 6 membered heterocyclyl is bound through a carbon atom; and wherein the 6 membered heterocyclyl is optionally substituted with one to two substituents independently selected from the group consisting of halogen, oxo, fluorinated $C_{1-4}$alkyl, —C(O)OH and —NR$^G$R$^H$; wherein R$^G$ and R$^H$ are each independently selected from the group consisting of hydrogen and $C_{1-4}$alkyl; and wherein the 6 membered heterocyclyl contains a nitrogen ring atom, said nitrogen ring atom may be further optionally substituted with oxygen to form an N-oxide.

In certain embodiments, the present invention is directed to compounds of formula (I) wherein R$^4$ is carboxy.

In certain embodiments, the present invention is directed to compounds of formula (I) wherein R$^4$ is phenyl, wherein the phenyl is optionally substituted as described herein.

In certain embodiments, the present invention is directed to compounds of formula (I) wherein R$^4$ is selected from the group consisting of (a) carboxy; and (b) phenyl; wherein the phenyl is optionally substituted with one to two substituents independently selected from the group consisting of halogen, fluorinated $C_{1-2}$alkoxy, —C(O)OH, —C(O)—O—($C_{1-4}$ alkyl), —NR$^C$R$^D$, —$C_{1-2}$alkyl-NR$^C$R$^D$, —C(O)—NR$^C$R$^D$, —NR$^D$—C(O)—($C_{1-2}$ alkyl)-O—($C_{1-4}$alkyl), —NR$^D$—C(O)—O—($C_{1-2}$alkyl)-O—($C_{1-4}$alkyl), cyclopropyl, 1-carboxy-cycloprop-1-yl, 1-($C_{1-4}$ alkoxy-carbonyl)-cycloprop-1-yl, pyrrolidin-2-yl-5-one, 1,2,3,4-tetrazol-1-yl, 1,2,4-oxadiazol-3-yl-5-one and —C(O)—NH—SO$_2$—CH$_3$; wherein R$^C$ is selected from the group consisting of hydrogen, cyclopropyl, 3-hydroxy-cycloprop-1-yl, —C(O)—$C_{1-4}$ alkyl, —C(O)-cyclopropyl, —C(O)—O—$C_{1-4}$alkyl and —SO$_2$—$C_{1-4}$alkyl; and R$^D$ is selected from the group consisting of hydrogen and $C_{1-2}$alkyl.

In certain embodiments, the present invention is directed to compounds of formula (I) wherein R$^4$ is selected from the group consisting of (a) carboxy; and (b) phenyl; wherein the phenyl is optionally substituted with one or more substituents independently selected from the group consisting of halogen, fluorinated $C_{1-2}$alkoxy, —C(O)OH, —NR$^C$R$^D$, —$C_{1-2}$alkyl-NR$^C$R$^D$, —C(O)—NR$^C$R$^D$, —NR$^D$—C(O)—($C_{1-2}$alkyl)-O—($C_{1-4}$alkyl), —NR$^D$—C(O)—O—($C_{1-2}$alkyl)-O—($C_{1-4}$alkyl), 1-carboxy-cycloprop-1-yl, 1-($C_{1-4}$ alkoxy-carbonyl)-cycloprop-1-yl, pyrrolidin-3-yl-2,5-dione, 1,2,3,4-tetrazol-1-yl, 1,2,4-oxadiazol-3-yl-5-one, and —C(O)—NH—SO$_2$—CH$_3$; wherein R$^C$ is selected from the group consisting of hydrogen, cyclopropyl, —C(O)—$C_{1-4}$ alkyl, —C(O)—O—$C_{1-4}$alkyl and —SO$_2$—$C_{1-4}$ alkyl; and R$^D$ is selected from the group consisting of hydrogen and $C_{1-2}$alkyl.

In certain embodiments, the present invention is directed to compounds of formula (I) wherein R$^4$ is selected from the group consisting of phenyl, 4-fluoro-phenyl, 3-carboxy-phenyl, 4-carboxy-phenyl, 4-amino-phenyl, 4-(methyl-d$_3$-amino)-phenyl, 3-fluoro-4-(amino-carbonyl)-phenyl, 3-fluoro-4-carboxy-phenyl, 3-fluoro-4-(amino-carbonyl)-phenyl, 4-(amino-carbonyl)-phenyl, 3-fluoro-4-carboxy-phenyl, 4-trifluoro-methoxy-phenyl, 4-(methyl-carbonyl-amino)-phenyl, 4-(methoxy-carbonyl-amino)-phenyl, 4-(cyclopropyl-carbonyl-amino)-phenyl, 4-(1-amino-ethyl)-phenyl, 4-(cyclopropyl-amino-carbonyl)-phenyl, 4-(1-(methoxy-carbonyl-amino)-ethyl)-phenyl, 2-fluoro-6-(methyl-carbonyl-amino)-phenyl, 4-(methoxy-methyl-carbonyl-amino)-phenyl, 4-(2-methoxy-ethoxy-carbonyl-amino)-phenyl, 4-(methyl-sulfonyl-amino)-phenyl, 4-(methyl-sulfonyl-amino-carbonyl)-phenyl, 4-((1-methoxy-carbonyl)-cycloprop-1-yl)-phenyl, 4-(1-carboxy-cycloprop-1-yl)-phenyl, 4-(trans-3-hydroxy-cyclopropyl-amino-carbonyl)-phenyl, 4-(pyrrolidin-2-yl-5-one)-phenyl, 2-(1,2,3,4-tetrazol-1-yl)-5-chloro-phenyl, and 4-(1,2,4-oxadiazol-3-yl-5-one)-phenyl.

In certain embodiments, the present invention is directed to compounds of formula (I) wherein $R^4$ is 5 membered heterocyclyl, wherein the 5 membered heterocyclyl is optionally substituted as described herein.

In certain embodiments, the present invention is directed to compounds of formula (I) wherein $R^4$ is (c) 5 membered heterocyclyl; wherein the 5 membered heterocyclyl contains at least one heteroatom selected from the group consisting of O, N and S; optionally contains 1 to 3 additional heteroatoms independently selected from the group consisting of O, N and S; wherein the 5 membered heterocyclyl is saturated, partially unsaturated, or aromatic; wherein the 5 membered heterocyclyl is optionally substituted with one to two substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, $C_{3-7}$cycloalkyl, —C(O)OH, —C(O)—O—$C_{1-4}$alkyl, —$C_{1-2}$alkyl-C(O)—O—$C_{1-4}$ alkyl, cyano, —$NR^E R^F$ and —C(O)—$NR^E R^F$; and wherein $R^E$ is selected from the group consisting of hydrogen, $C_{1-4}$alkyl, cyclopropyl, 3-hydroxy-cycloprop-1-yl, —C(O)—$C_{1-4}$alkyl, —C(O)-cyclopropyl, —C(O)—O—$C_{1-4}$ alkyl and —$SO_2$—$C_{1-4}$alkyl; and $R^F$ is hydrogen and $C_{1-4}$alkyl.

In certain embodiments, the present invention is directed to compounds of formula (I) wherein $R^4$ is (c) 5 membered heterocyclyl; wherein the 5 membered heterocyclyl contains at least one heteroatom selected from the group consisting of O, N and S; optionally contains 1 to 3 additional heteroatoms independently selected from the group consisting of O, N and S; wherein the 5 membered heterocyclyl is saturated, partially unsaturated, or aromatic; and wherein the 5 membered heterocyclyl is optionally substituted with one to two substituents independently selected from the group consisting of halogen, hydroxy, $C_{1-4}$alkyl, fluorinated $C_{1-4}$alkyl, —$C_{1-2}$alkyl-C(O)—O—$C_{1-4}$alkyl, $C_{3-6}$cycloalkyl, cyano, —$NR^E R^F$, and —C(O)—$NR^E R^F$; wherein $R^E$ is selected from the group consisting of hydrogen and —C(O)-cyclopropyl; and $R^F$ is selected from the group consisting of hydrogen and $C_{1-4}$alkyl.

In certain embodiments, the present invention is directed to compounds of formula (I) wherein $R^4$ is selected from the group consisting of 5-carboxy-pyrrol-3-yl, 5-(amino-carbonyl)-thien-2-yl, 4-fluoro-5-(amino-carbonyl)-thien-3-yl, 3-methyl-5-(amino-carbonyl)-thien-2-yl, pyrazol-5-yl, 1-methyl-pyrazol-4-y, 1-methyl-pyrazol-5-yl, 1-(methoxy-carbonyl-methyl)-pyrazol-4-yl, 1-methyl-4-fluoro-pyrazol-5-yl, 1-methyl-4-cyano-pyrazol-5-yl, 1-(difluoro-methyl)-pyrazol-5-yl, 1-methyl-3-(trifluoro-methyl)-pyrazol-5-yl, 3-methyl-pyrazol-4-yl, 1-methyl-4-chloro-pyrazol-5-yl, 1-(methyl-d₃)-pyrazol-5-yl, 1-(difluoro-methyl)-pyrazol-3-yl, 1-(difluoro-methyl)-4-chloro-pyrazol-3-yl, 1-(difluoro-methyl)-4-chloro-pyrazol-5-yl, 1-(difluoro-methyl)-4-fluoro-pyrazol-5-yl, 1-(difluoro-methyl)-4-cyano-pyrazol-5-yl, 1-(difluoro-methyl)-4-cyano-pyrazol-3-yl, 1-methyl-4-hydroxy-pyrazol-5-yl, 1-(difluoro-methyl)-pyrazol-5-yl), 1-(trifluoro-methyl)-pyrazol-4-yl, 1-(difluoro-methyl)-3-hydroxy-pyrazol-4-yl, 3-chloro-pyrazol-4-yl, 1-(methyl-d₃)-4-(cyclopropyl-carbonyl-amino)-pyrazol-5-yl, 1-methyl-3-chloro-pyrazol-4-yl, 1-(methyl-d₃)-pyrazol-5-yl, imidazol-1-yl, 1-methyl-imidazol-5-yl, 2-methyl-imidazol-1-yl, 1-(difluoro-methyl)-imidazol-5-yl, 1-(difluoro-methyl)-4-chloro-imidazol-5-yl, 1-methyl-4-chloro-imidazol-5-yl, oxazol-5-yl, 3-methyl-isoxazol-4-yl, 1,3,4-oxadiazol-5-yl, 3-methyl-1,2,4-oxadiazol-5-yl, thiazol-5-yl, 4-methyl-thiazol-5-yl, 2-(difluoro-methyl)-thiazol-5-yl, 4-cyclopropyl-thiazol-5-yl, 4-(trifluoro-methyl)-thiazol-5-yl, 4-chloro-thiazol-5-yl, 2-amino-thaizol-5-yl, 2-(trifluoro-methyl)-4-methyl-thiazol-5-yl, 2-amino-4-chloro-thiazol-5-yl, isothiazol-4-yl, 1,2,4-thiadizol-5-yl, 2-(trifluoro-methyl)-1,3,4-thiadiazol-5-yl, 1,3,4-triazol-1-yl, 1-methyl-1,2,3-triazol-5-yl, 1-methyl-1,2,3-triazol-4-yl, 1-cyclopropyl-1,2,3-triazol-5-yl, 1-methyl-1,2,4-triazol-5-yl, 1-methyl-1,2,5-triazol-3-yl, 1-(difluoro-methyl)-4-chloro-1,2,5-triazol-3-yl, 1-(difluoro-methyl)-4-chloro-1,2,3-triazol-5-yl, 1-(difluoro-methyl)-5-chloro-1,2,3-triazol-4-yl, 1-(difluoro-methyl)-1,2,3-triazol-4-yl, 1-(difluoro-methyl)-1,2,3-triazol-5-yl, 1-(difluoro-methyl)-1,2,5-triazol-3-yl, 1-methyl-1,2,3-triazol-5-yl, 1-methyl-4-chloro-1,2,3-triazol-5-yl, 1-(difluoro-methyl)-1,2,5-triazol-3-yl, 1-(difluoro-methyl)-1,2,4-triazol-5-yl, 1-(difluoro-methyl)-1,3,4-triazol-2-yl, 1-methyl-5-fluoro-1,2,3-triazol-4-yl, 1-methyl-4-fluoro-1,2,3-triazol-5-yl, 1-(difluoro-methyl)-4-fluoro-1,2,5-triazol-3-yl, 1-(difluoro-methyl)-4-fluoro-1,2,3-triazol-5-yl, 1-(dilfuoro-methyl)-1,2,4-triazol-5-yl, 1-isopropyl-1,2,3-triazol-5-yl, 2-methyl-1,3,4-triazol-1-yl, 3-methyl-1,2,4-triazol-1-yl, and 1-methyl-1,2,3,4-tetrazol-5-yl.

In certain embodiments, the present invention is directed to compounds of formula (I) wherein $R^4$ is 6 membered heterocyclyl, wherein the 6 membered heterocyclyl is optionally substituted as described herein. In certain embodiments, $R^4$ is an optionally substituted 6 membered aromatic heterocyclyl, wherein the 6 membered heterocyclyl is bound through a carbon atom.

In certain embodiments, the present invention is directed to compounds of formula (I) wherein $R^4$ is (d) 6 membered heterocyclyl; wherein the 6 membered heterocyclyl contains at least one heteroatom selected from the group consisting of N, O and S; optionally contains 1 to 3 additional heteroatoms independently selected from the group consisting of O, N and S; wherein the 6 membered heterocyclyl is saturated, partially unsaturated, or aromatic; wherein the 6 membered heterocyclyl is bound through a carbon atom; and wherein the 6 membered heterocyclyl is optionally substituted with one to two substituents independently selected from the group consisting of halogen, hydroxy, oxo, $C_{1-4}$alkyl, fluorinated $C_{1-4}$alkyl, $C_{1-4}$ alkoxy, fluorinated $C_{1-4}$alkoxy, —$C_{1-2}$alkyl-O—$C_{1-4}$alkyl, $C_{3-7}$cycloalkyl, —C(O)OH, —C(O)—O—$C_{1-4}$alkyl, —$C_{1-2}$alkyl-C(O)—O—$C_{1-4}$alkyl, cyano, —$NR^G R^H$, and —C(O)—$NR^G R^H$; wherein $R^G$ is selected from the group consisting of hydrogen, $C_{1-4}$alkyl, cyclopropyl, 3-hydroxy-cycloprop-1-yl, —C(O)—$C_{1-4}$alkyl, —C(O)-cyclopropyl, —C(O)—O—$C_{1-4}$ alkyl and —$SO_2$—$C_{1-4}$alkyl; and $R^H$ is hydrogen and $C_{1-4}$alkyl; and wherein the 6 membered heterocyclyl contains a nitrogen ring atom, said nitrogen ring atom may be further optionally substituted with oxygen to form an N-oxide.

In certain embodiments, the present invention is directed to compounds of formula (I) wherein $R^4$ is (d) 6 membered heterocyclyl; wherein the 6 membered heterocyclyl contains at least one heteroatom selected from the group consisting of N, O and S; optionally contains 1 to 3 additional heteroatoms independently selected from the group consisting of O, N and S; wherein the 6 membered heterocyclyl is saturated, partially unsaturated, or aromatic; wherein the 6 membered heterocyclyl is bound through a carbon atom; and wherein the 6 membered heterocyclyl is optionally substituted with one to two substituents independently selected from the group consisting of halogen, oxo, $C_{1-4}$alkyl, fluorinated $C_{1-4}$alkyl, $C_{1-4}$alkoxy, fluorinated $C_{1-4}$alkoxy, —$C_{1-2}$alkyl-O—$C_{1-4}$alkyl, $C_{3-7}$cycloalkyl, —C(O)OH, —C(O)—O—$C_{1-4}$alkyl, cyano and —NR$^G$R$^H$; wherein R$^G$ is selected from the group consisting of hydrogen, $C_{1-4}$alkyl, —C(O)—$C_{1-4}$alkyl and —C(O)-cyclopropyl; and R$^H$ is selected from the group consisting of hydrogen and $C_{1-4}$alkyl; and wherein the 6 membered heterocyclyl contains a nitrogen ring atom, said nitrogen ring atom may be further optionally substituted with oxygen to form an N-oxide.

In certain embodiments, the present invention is directed to compounds of formula (I) wherein R$^4$ is selected from the group consisting of 1-(methoxy-carbonyl)-piperidin-4-yl, pyridin-2-yl, pyridin-4-yl, 3-fluoro-5-chloro-pyridin-4-yl, 2-(trifluoro-methyl)-5-(methyl-carbonyl-amino)-pyridin-4-yl, 2-(trifluoro-methyl)-pyridin-4-yl, 2-isopropyl-pyridin-4-yl, 2-t-butyl-pyridin-4-yl, 2-carboxy-pyridin-4-yl, 3-(trifluoro-methyl)-pyridin-4-yl, 2-chloro-6-amino-pyridin-3-yl, 2-fluoro-6-amino-pyridin-3-yl, 6-amino-pyridin-3-yl, 4-fluoro-6-amino-pyridin-3-yl, 5-fluoro-6-amino-pyridin-3-yl, 2-fluoro-5-methoxy-pyridin-3-yl, 6-fluoro-pyridin-3-yl, 3-fluoro-pyridin-4-yl, 2-methyl-6-amino-pyridin-3-yl, 2-fluoro-pyridin-4-yl, 2-(trifluoro-methyl)-pyridin-4-yl, 2-fluoro-4-(cyclopropyl-carbonyl-amino)-pyridin-3-yl, 2-methyl-pyridin-4-yl, 2-cyclopropyl-pyridin-4-yl, 2-cyano-pyridin-4-yl, 2-(difluoro-methoxy)-pyridin-4-yl, 2-(difluoro-methyl)-pyridin-4-yl, 1-methyl-pyridin-4-yl-2-one, 1-methyl-pyridin-3-yl-6-one, pyridin-3-yl-1-oxide, pyridin-4-yl-1-oxide, 6-amino-pyridin-3-yl-1-oxide, 2-methyl-6-amino-pyridin-3-yl-1-oxide, 3-fluoro-pyridin-4-yl-1-oxide, 2-cyano-pyridin-4-yl-1-oxide, 3-chloro-5-fluoro-pyridin-4-yl-1-oxide, 3-fluoro-5-chloro-pyridin-4-yl-1-oxide, 2-t-butyl-pyridin-4-yl-1-oxide, 2-isopropyl-pyridin-4-yl-1-oxide, 2-(trifluoro-methyl)-pyridin-4-yl-1-oxide, 2-(difluoro-methyl)-pyridin-4-yl-1-oxide, 2-methyl-pyridin-4-yl-1-oxide, 2,6-dimethyl-pyridin-4-yl-1-oxide, pyridazin-4-yl, pyridazin-4-yl-1-oxide, 1-methyl-pyridazin-4-yl-6-one, 1-isopropyl-pyridazin-4-yl-6-one, 1-(2-isopropyloxy-ethyl)-pyridazin-4-yl-6-one, 1-ethyl-pyridazin-4-yl-6-one, pyrimidin-4-yl, pyrimidin-5-yl, 2-(trifluoro-methyl)-pyrimidin-4-yl, 2-methyl-pyrimidin-4-yl, 6-(trifluoro-methyl)-pyrimidin-4-yl, 2-(methyl-amino)-pyrimidin-5-yl, pyrimidin-4-yl-1-oxide, 2-methyl-pyrimidin-4-yl-1-oxide, and 2-fluoro-6-amino-pyrazin-3-yl.

In certain embodiments, present invention is directed to compounds of formula (I), wherein R$^1$ is selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, nitro, —NR$^A$R$^B$, —C(O)—$C_{1-4}$alkyl, $C_{3-6}$cycloalkyl, phenyl and 5 to 6 membered heterocyclyl;
  wherein the $C_{3-6}$cycloalkyl, phenyl or 5 to 6 membered heterocyclyl is optionally substituted with one or more substituents independently selected from the group consisting of halogen, hydroxy, cyano, $C_{1-4}$alkyl, fluorinated $C_{1-4}$alkyl, $C_{1-4}$alkoxy, fluorinated $C_{1-4}$alkoxy, —C(O)OH, —C(O)O—($C_{1-4}$alkyl), —NR$^A$R$^B$, —($C_{1-4}$alkyl)-NR$^A$R$^B$, $C_{3-7}$cycloalkyl and 5 to 6 membered heterocyclyl; and wherein R$^A$ and R$^B$ are each independently selected from the group consisting of hydrogen and $C_{1-4}$alkyl;
a is an integer from 0 to 3;

each R$^2$ is independently selected from the group consisting of chloro, fluoro, methyl and methoxy;
Y is N and Z is C(R$^3$), such that

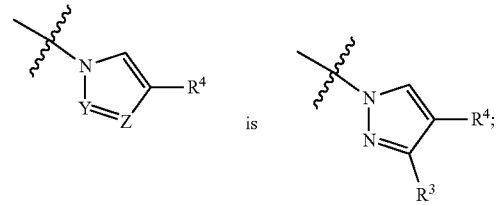

is

R$^3$ is selected from the group consisting of hydrogen, fluoro, chloro and methyl;
R$^4$ is 9 to 10 membered bicyclic heterocyclyl; wherein the 9 to 10 membered bicyclic heterocyclyl contains at least one heteroatom selected from the group consisting of O, N and S; optionally contains one to four additional heteroatoms independently selected from the group consisting of O, N and S; wherein the 9 to 10 membered bicyclic heterocyclyl is saturated, partially unsaturated, partially aromatic, aromatic, bicyclic, fused, bridged or spiro-cyclic;
and wherein the 9 to 10 membered bicyclic heterocyclyl is optionally substituted with one or more substituents independently selected from the group consisting of halogen, hydroxy, oxo, $C_{1-4}$alkyl, fluorinated $C_{1-4}$alkyl, $C_{1-4}$alkoxy, fluorinated $C_{1-4}$alkoxy, cyano, —C(O)OH, —C(O)—O—$C_{1-4}$alkyl, NR$^J$R$^K$, and —C(O)—NR$^J$R$^K$, pyrrolidin-2-yl-5-one, pyrrolidin-3-yl-2,5-dione, pyrrol-3-yl-2,5-dione, 1,2,3,4-tetrazol-1-yl, 1,2,3,4-tetrazol-5-yl, 1,2,4-oxadiazol-3-yl-5-one, oxazolidin-5-yl-2,4-dione, 1H-imidazol-5-yl-2,5-dione, thiazol-5-yl-2,4-dione, isoxazol-5-yl-3-ol, isothiazol-5-yl-3-ol, 3-chloro-4-hydroxy-phenyl, —C(O)—NH—CN, —C(O)—NH—SO$_2$—CH$_3$, —SO$_2$—NH—CF$_3$, and —SO$_2$—NH—CF$_2$CF$_3$; wherein R$^J$ and R$^K$ are each independently selected from the group consisting of hydrogen and $C_{1-4}$alkyl;
R$^5$ is selected from the group consisting of
(a) $C_{1-4}$alkyl; wherein the $C_{1-4}$alkyl is optionally substituted with one or more halogen, and further optionally substituted with a substituent selected from the group consisting of hydroxy, $C_{1-4}$alkoxy, fluorinated $C_{1-4}$alkoxy, —C(O)OH, —C(O)—O—($C_{1-4}$alkyl), —C(O)—O-(fluorinated $C_{1-4}$alkyl), —C(O)-(fluorinated $C_{1-4}$alkyl), and —C(O)—NR$^L$R$^M$; wherein R$^L$ and R$^M$ are each independently selected from the group consisting of hydrogen and $C_{1-2}$alkyl;
(b) —CH$_2$—$C_{3-8}$cycloalkyl or —CH$_2$-adamant-1-yl; wherein the $C_{3-8}$cycloalkyl is optionally substituted with one or more halogen or $C_{1-4}$alkyl; and further optionally substituted with a substituent selected from the group consisting of —C(O)OH, —C(O)—O—$C_{1-4}$ alkyl, —C(O)-(5 to 6 membered saturated heterocyclyl), —C(O)-(isoindolin-2-yl), —C(O)-(azaspiro[2.4]heptan-5-yl), —C(O)-(carboxy substituted azaspiro[2.4]heptan-5-yl), —C(O)—(NR$^P$R$^Q$ substituted azaspiro[2.4]heptan-5-yl), phenyl, 1,1'-biphen-4-yl and —C(O)—NR$^P$R$^Q$;
wherein the —C(O)-(5 to 6 membered saturated heterocyclyl) substituent on the —CH$_2$—$C_{3-8}$cycloalkyl is further optionally substituted on the (5 to 6 membered heterocyclyl) with one or more substituents independently selected from the group consisting of halogen, hydroxy, $C_{1-4}$alkyl, fluorinated $C_{1-4}$alkyl, $C_{1-4}$ alkoxy, fluorinated $C_{1-4}$alkoxy, cyano, —C(O)OH, —C(O)—O—$C_{1-4}$alkyl, —NR$^P$R$^Q$, phenyl and $C_{3-8}$cycloalkyl;

wherein the phenyl substituent on the —CH$_2$—$C_{3-8}$cycloalkyl is further optionally substituted with one or more substituents independently selected form the group consisting of halogen, hydroxy, $C_{1-4}$alkyl, fluorinated $C_{1-4}$alkyl, $C_{1-4}$alkoxy, fluorinated $C_{1-4}$alkoxy, cyano, —NR$^P$R$^Q$, and $C_{3-8}$cycloalkyl;

and wherein R$^P$ and R$^Q$ are each independently selected from the group consisting of hydrogen and $C_{1-4}$alkyl;

(c) -L$^1$-(5 to 6 membered saturated heterocyclyl); wherein L$^1$ is selected from the group consisting of —CH$_2$— and —CH$_2$—C(O)—; wherein, when L$^1$ is —CH$_2$—C(O)—, then the (5 to 6 membered saturated heterocyclyl) is bound to the —C(O)— portion of L$^1$; - and wherein the (5 to 6 membered saturated heterocyclyl) is optionally substituted with one to two oxo group;

(d) —$C_{1-2}$alkyl-phenyl; wherein the phenyl is optionally substituted with one or more substituents independently selected from the group consisting of halogen, hydroxy, $C_{1-4}$alkyl, fluorinated $C_{1-4}$alkyl, $C_{1-4}$ alkoxy, fluorinated $C_{1-4}$alkoxy, —OCH$_2$—C(O)—NR$^S$R$^T$, phenyl and phenoxy; and wherein R$^S$ and R$^T$ are each independently selected from the group consisting of hydrogen and $C_{1-4}$alkyl;

(e) 1,2,3-triazol-4-yl, 1,2,5-triazol-3-yl, —CH$_2$-1,2,3-triazol-4-yl and —CH$_2$-1,2,5-triazol-3-yl; wherein the 1,2,3-triazol-4-yl or 1,2,5-triazoly-3-yl, whether alone or as part of the substituent group is optionally substituted with a substituent selected from the group consisting of $C_{1-4}$alkyl, fluorinated $C_{1-4}$alkyl, phenyl and piperidinyl; wherein the piperidinyl is optionally substituted with —C(O)—$C_{1-4}$alkyl;

(f) —CH$_2$-(5 to 6 membered or 9 to 10 membered heterocyclyl); wherein the (5 to 6 membered or 9 to 10 membered heterocyclyl) is other than triazolyl;

wherein the (5 to 6 membered or 9 to 10 membered heterocyclyl) is optionally substituted with one or more substituents independently selected from the group consisting of halogen, hydroxy, oxo, $C_{1-4}$alkyl, fluorinated $C_{1-4}$alkyl, $C_{1-4}$alkoxy, fluorinated $C_{1-4}$alkoxy, cyano, —C(O)OH, —C(O)—O—$C_{1-4}$alkyl, —$C_{1-2}$alkyl-O—$C_{1-4}$ alkyl, —$C_{1-2}$alkyl-O-(fluorinated $C_{1-4}$alkyl), —C(O)—NR$^V$R$^W$, —$C_{1-2}$alkyl-C(O)—NR$^V$R$^W$, -(5 to 6 membered saturated heterocyclyl), —C(O)-(5 to 6 membered saturated heterocyclyl), —C(O)-(carboxy substituted 5 to 6 membered saturated heterocyclyl), —$C_{1-2}$alkyl-C(O)-(5 to 6 membered saturated heterocyclyl), phenyl and pyridinyl;

wherein the pyridinyl substituent on the —CH$_2$-(5 to 6 membered or 9 to 10 membered heterocyclyl) is further optionally substituted with one or more substituents independently selected from the group consisting of halogen and fluorinated $C_{1-4}$alkyl;

and wherein R$^V$ and R$^W$ are each independently selected from the group consisting of hydrogen and $C_{1-4}$alkyl;

and (g) —CH$_2$—NR$^8$R$^9$; wherein R$^8$ is selected from the group consisting of hydrogen and $C_{1-4}$alkyl; R$^9$ is selected from the group consisting of $C_{1-4}$alkyl, fluorinated $C_{1-4}$alkyl, $C_{1-4}$alkoxy, fluorinated $C_{1-4}$alkoxy, —C(O)—$C_{1-4}$alkyl, —C(O)—$C_{1-2}$alkyl-O—$C_{1-4}$alkyl, —C(O)-phenyl, —C(O)—$C_{1-2}$alkyl-phenyl, —C(O)—O—$C_{1-4}$alkyl, —C(O)—O— phenyl, —C(O)—O—$C_{1-2}$alkyl-phenyl, —C(O)—$C_{3-7}$cycloalkyl, —C(O)-(1-methyl-cycloprop-1-yl), —C(O)-(5 to 6 membered saturated heterocyclyl), —C(O)—$C_{1-2}$alkyl-C(O)-(5 to 6 membered saturated heterocyclyl), —O—$C_{1-2}$ alkyl-C(O)-(5 to 6 membered saturated heterocyclyl), —C(O)-(1-methyl-pyridinyl-one) and —C(O)—NR$^X$R$^Y$; and wherein R$^X$ and R$^Y$ are each independently selected from the group consisting of hydrogen and $C_{1-4}$alkyl;

R$^6$ and R$^7$ are each independently selected from the group consisting of hydrogen, halogen, $C_{1-4}$alkyl and $C_{1-4}$alkoxy;

provided that at least one of R$^6$ or R$^7$ is hydrogen;

or a stereoisomer, isotopologue, isotopomer, or pharmaceutically acceptable salt or solvate thereof.

In certain embodiments, present invention is directed to compounds of formula (I), wherein R$^1$ is selected from the group consisting of halogen, $C_{1-4}$alkyl, fluorinated $C_{1-4}$alkyl, $C_{1-4}$alkoxy, fluorinated $C_{1-4}$alkoxy, cyano, —NR$^A$R$^B$, —C(O)—$C_{1-4}$alkyl, and 5 to 6 membered heterocyclyl;

wherein the 5 to 6 membered heterocyclyl is optionally substituted with one or more substituents independently selected from the group consisting of halogen, cyano, $C_{1-4}$alkyl, fluorinated $C_{1-4}$alkyl, $C_{1-4}$alkoxy, fluorinated $C_{1-4}$alkoxy, and $C_{3-7}$cycloalkyl; and wherein R$^A$ and R$^B$ are each independently selected from the group consisting of hydrogen and $C_{1-4}$alkyl;

a is an integer from 1 to 2;

each R$^2$ is independently selected from the group consisting of chloro and fluoro;

Y is N and Z is C(R$^3$), such that

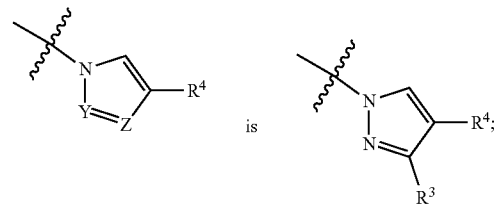

R$^3$ is selected from the group consisting of hydrogen, and methyl;

R$^4$ is 9 to 10 membered bicyclic heterocyclyl; wherein the 9 to 10 membered bicyclic heterocyclyl contains at least one heteroatom selected from the group consisting of O, N and S; optionally contains one to four additional heteroatoms independently selected from the group consisting of O, N and S; wherein the 9 to 10 membered bicyclic heterocyclyl is saturated, partially unsaturated, partially aromatic, aromatic, bicyclic, fused, bridged or spiro-cyclic;

and wherein the 9 to 10 membered bicyclic heterocyclyl is optionally substituted with one to two substituents independently selected from the group consisting of halogen, hydroxy, oxo, $C_{1-4}$alkyl, fluorinated $C_{1-4}$alkyl, $C_{1-4}$alkoxy, fluorinated $C_{1-4}$alkoxy, cyano, —C(O)OH, —C(O)—O—$C_{1-4}$alkyl, NR$^J$R$^K$, and —C(O)—NR$^J$R$^K$;

wherein R$^J$ and R$^K$ are each hydrogen;

R$^5$ is selected from the group consisting of (a) $C_{1-4}$alkyl; wherein the $C_{1-4}$alkyl is optionally substituted with one or more halogen, and further optionally substituted with a substituent selected from the group consisting of hydroxy, $C_{1-4}$alkoxy, fluorinated $C_{1-4}$alkoxy, —C(O)OH, —C(O)—O—($C_{1-4}$alkyl), —C(O)—O-(fluorinated $C_{1-4}$alkyl), —C(O)-(fluorinated $C_{1-4}$alkyl), and —C(O)—NR$^L$R$^M$; wherein R$^L$ and R$^M$ are each independently selected from the group consisting of hydrogen and $C_{1-2}$alkyl;

(b) —CH$_2$—C$_{3-8}$cycloalkyl or —CH$_2$-adamant-1-yl; wherein the C$_{3-8}$cycloalkyl is optionally substituted with one to two halogen or $C_{1-4}$alkyl; and further optionally substituted with a substituent selected from the group consisting of —C(O)OH, —C(O)—O—$C_{1-4}$alkyl, —C(O)-(5 to 6 membered saturated heterocyclyl), —C(O)-(isoindolin-2-yl), —C(O)-(azaspiro[2.4]heptan-5-yl), —C(O)-(carboxy substituted azaspiro[2.4]heptan-5-yl), —C(O)—(NR$^P$R$^Q$ substituted azaspiro[2.4]heptan-5-yl), phenyl, 1,1'-biphen-4-yl and —C(O)—NR$^P$R$^Q$;

wherein the —C(O)-(5 to 6 membered saturated heterocyclyl) substituent on the —CH$_2$—C$_{3-8}$cycloalkyl is further optionally substituted on the (5 to 6 membered heterocyclyl) with one to two substituents independently selected from the group consisting of halogen, $C_{1-4}$alkyl, —C(O)OH, —C(O)—O—$C_{1-4}$alkyl, phenyl and $C_{3-8}$cycloalkyl;

wherein the phenyl substituent on the —CH$_2$—C$_{3-8}$cycloalkyl is further optionally substituted with $C_{1-4}$alkoxy;

and wherein R$^P$ and R$^Q$ are each independently selected from the group consisting of hydrogen and $C_{1-4}$alkyl;

(c) -L$^1$-(5 to 6 membered saturated heterocyclyl); wherein L$^1$ is selected from the group consisting of —CH$_2$— and —CH$_2$—C(O)—; wherein, when L$^1$ is —CH$_2$—C(O)—, then the (5 to 6 membered saturated heterocyclyl) is bound to the —C(O)— portion of L$^1$; and wherein the (5 to 6 membered saturated heterocyclyl) is optionally substituted with one to two oxo group;

(d) —$C_{1-2}$alkyl-phenyl; wherein the phenyl is optionally substituted with one to two substituents independently selected from the group consisting of halogen, hydroxy, $C_{1-4}$alkyl, fluorinated $C_{1-4}$alkyl, $C_{1-4}$ alkoxy, fluorinated $C_{1-4}$alkoxy, —OCH$_2$—C(O)—NR$^S$R$^T$, phenyl and phenoxy; and wherein R$^S$ and R$^T$ are each independently selected from the group consisting of hydrogen and $C_{1-2}$alkyl;

(e) 1,2,3-triazol-4-yl, 1,2,5-triazol-3-yl, —CH$_2$-1,2,3-triazol-4-yl and —CH$_2$-1,2,5-triazol-3-yl; wherein the 1,2,3-triazol-4-yl or 1,2,5-triazoly-3-yl, whether alone or as part of the substituent group is optionally substituted with a substituent selected from the group consisting of $C_{1-4}$alkyl, fluorinated $C_{1-4}$alkyl, phenyl and piperidinyl; wherein the piperidinyl is optionally substituted with —C(O)—$C_{1-4}$alkyl;

(f) —CH$_2$-(5 to 6 membered or 9 to 10 membered heterocyclyl); wherein the (5 to 6 membered or 9 to 10 membered heterocyclyl) is other than triazolyl; wherein the (5 to 6 membered or 9 to 10 membered heterocyclyl) is optionally substituted with one to two substituents independently selected from the group consisting of halogen, hydroxy, oxo, $C_{1-4}$alkyl, fluorinated $C_{1-4}$alkyl, $C_{1-4}$alkoxy, fluorinated $C_{1-4}$alkoxy, cyano, —C(O)OH, —C(O)—O—$C_{1-4}$alkyl, —$C_{1-2}$alkyl-O—$C_{1-4}$ alkyl, —$C_{1-2}$alkyl-O-(fluorinated $C_{1-4}$alkyl), —C(O)—NR$^V$R$^W$, —$C_{1-2}$alkyl-C(O)—NR$^V$R$^W$, -(5 to 6 membered saturated heterocyclyl), —C(O)-(5 to 6 membered saturated heterocyclyl), —C(O)-(carboxy substituted 5 to 6 membered saturated heterocyclyl), —$C_{1-2}$alkyl-C(O)-(5 to 6 membered saturated heterocyclyl), phenyl and pyridinyl;

wherein the pyridinyl substituent on the —CH$_2$-(5 to 6 membered or 9 to 10 membered heterocyclyl) is further optionally substituted with one to two substituents independently selected from the group consisting of halogen and fluorinated $C_{1-4}$alkyl;

and wherein R$^V$ and R$^W$ are each independently selected from the group consisting of hydrogen and $C_{1-4}$alkyl;

and (g) —CH$_2$—NR$^8$R$^9$; wherein R$^8$ is selected from the group consisting of hydrogen and $C_{1-2}$alkyl; R$^9$ is selected from the group consisting of $C_{1-4}$alkyl, fluorinated $C_{1-4}$alkyl, $C_{1-4}$alkoxy, fluorinated $C_{1-4}$alkoxy, —C(O)—$C_{1-4}$alkyl, —C(O)—$C_{1-2}$alkyl-O—$C_{1-4}$alkyl, —C(O)-phenyl, —C(O)—$C_{1-2}$alkyl-phenyl, —C(O)—O—$C_{1-4}$alkyl, —C(O)—O— phenyl, —C(O)—O—$C_{1-2}$alkyl-phenyl, —C(O)—$C_{3-7}$cycloalkyl, —C(O)-(1-methyl-cycloprop-1-yl), —C(O)-(5 to 6 membered saturated heterocyclyl), —C(O)—$C_{1-2}$alkyl-C(O)-(5 to 6 membered saturated heterocyclyl), —O—$C_{1-2}$ alkyl-C(O)-(5 to 6 membered saturated heterocyclyl), —C(O)-(1-methyl-pyridinyl-one) and —C(O)—NR$^X$R$^Y$; and wherein R$^X$ and R$^Y$ are each independently selected from the group consisting of hydrogen and $C_{1-2}$alkyl;

R$^6$ and R$^7$ are each independently selected from the group consisting of hydrogen, halogen, $C_{1-4}$alkyl and $C_{1-4}$alkoxy;

provided that at least one of R$^6$ or R$^7$ is hydrogen;

or a stereoisomer, isotopologue, isotopomer, or pharmaceutically acceptable salt or solvate thereof.

In certain embodiments, present invention is directed to compounds of formula (I), wherein R$^1$ is 5 membered heterocyclyl; wherein the 5 membered heterocyclyl is optionally substituted with fluorinated $C_{1-4}$ alkyl;

a is an integer from 1 to 2;

each R$^2$ is independently selected from the group consisting of chloro and fluoro;

Y is N and Z is C(R$^3$), such that

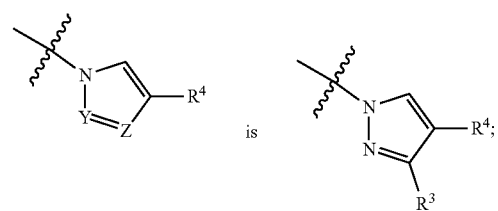

is

R$^3$ is hydrogen;

R$^4$ is 9 to 10 membered bicyclic heterocyclyl; wherein the 9 to 10 membered bicyclic heterocyclyl contains at least one heteroatom selected from the group consisting of O, N and S; optionally contains one to four additional heteroatoms independently selected from the group consisting of O, N and S; wherein the 9 to 10 membered bicyclic heterocyclyl is saturated, partially unsaturated, partially aromatic, aromatic, bicyclic, fused, bridged or spiro-cyclic; and wherein the 9 to 10 membered bicyclic heterocyclyl is optionally substituted with one to two substituents independently selected from the group consisting of halogen and $C_{1-4}$alkyl;

R$^5$ is selected from the group consisting of (a) $C_{1-4}$alkyl; wherein the $C_{1-4}$alkyl is optionally substituted with $C_{1-4}$alkoxy; and (b) —CH$_2$—$C_{3-8}$cycloalkyl;

R$^6$ is hydrogen;

R$^7$ is hydrogen;

or a stereoisomer, isotopologue, isotopomer, or pharmaceutically acceptable salt or solvate thereof.

In certain embodiments, present invention is directed to compounds of formula (I), wherein $R^1$ is selected from the group consisting of 1,2,3,4-tetrazol-1-yl and 4-(trifluoromethyl)-1,2,3-triazol-1-yl;

a is an integer from 1 to 2;

each $R^2$ is independently selected from the group consisting of 5-chloro and 6-fluoro;

Y is N and Z is $C(R^3)$, such that

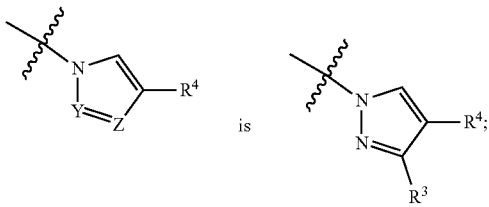

is $R^3$ is hydrogen;

$R^4$ is selected from the group consisting of 1-methyl-1H-indazol-5-yl, 2-methyl-indazol-5-yl, isoindol-4-yl-2-one, 2-methyl-isoindolin-5-yl-1-one, isobenzofuran-5-yl-1-one, 2-methyl-3,4-dihydroisoquinolin-6-yl-1-one, 2,2-difluoro-benzo[d][1,3]dioxol-5-yl and 2,3-dihydro-benzo[b][1,4]dioxin-6-yl;

$R^5$ is selected from the group consisting of 2-(difluoromethoxy)-ethyl- and cyclopropyl-methyl-;

$R^6$ is hydrogen;

$R^7$ is hydrogen;

or pharmaceutically acceptable salt or solvate thereof.

In certain embodiments, present invention is directed to compounds of formula (I), wherein $R^1$ is selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, nitro, —$NR^AR^B$, —C(O)—$C_{1-4}$alkyl, $C_{3-6}$cycloalkyl, phenyl and 5 to 6 membered heterocyclyl; wherein the $C_{3-6}$cycloalkyl, phenyl or 5 to 6 membered heterocyclyl is optionally substituted with one or more substituents independently selected from the group consisting of halogen, hydroxy, cyano, $C_{1-4}$alkyl, fluorinated $C_{1-4}$alkyl, $C_{1-4}$alkoxy, fluorinated $C_{1-4}$alkoxy, —C(O)OH, —C(O)O—($C_{1-4}$alkyl), —$NR^AR^B$, —($C_{1-4}$alkyl)-$NR^AR^B$, $C_{3-7}$cycloalkyl and 5 to 6 membered heterocyclyl; and wherein $R^A$ and $R^B$ are each independently selected from the group consisting of hydrogen and $C_{1-4}$alkyl;

a is an integer from 0 to 3;

each $R^2$ is independently selected from the group consisting of chloro, fluoro, methyl and methoxy;

Y is N and Z is $C(R^3)$, such that

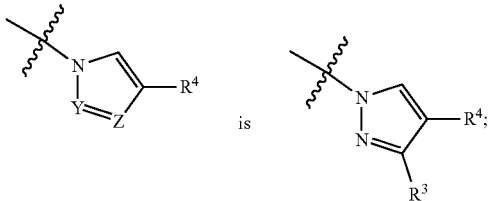

is $R^3$ is selected from the group consisting of hydrogen, fluoro, chloro and methyl;

$R^4$ is selected from the group consisting of
(a) carboxy; and
(b) phenyl; wherein the phenyl is optionally substituted with one or more substituents independently selected from the group consisting of halogen, fluorinated $C_{1-2}$alkoxy, —C(O)OH, —C(O)—O—($C_{1-4}$alkyl), —$NR^CR^D$, —$C_{1-2}$alkyl-$NR^CR^D$, —C(O)—$NR^CR^D$, —$NR^D$—C(O)—($C_{1-2}$alkyl)-O—($C_{1-4}$alkyl), —$NR^D$—C(O)—O—($C_{1-2}$alkyl)-O—($C_{1-4}$alkyl), cyclopropyl, 1-carboxy-cycloprop-1-yl, 1-($C_{1-4}$alkoxy-carbonyl)-cycloprop-1-yl, pyrrolidin-2-yl-5-one, pyrrolidin-3-yl-2,5-dione, pyrrol-3-yl-2,5-dione, 1,2,3,4-tetrazol-1-yl, 1,2,3,4-tetrazol-5-yl, 1,2,4-oxadiazol-3-yl-5-one, oxazolidin-5-yl-2,4-dione, 1H-imidazol-5-yl-2,5-dione, thiazol-5-yl-2,4-dione, isoxazol-5-yl-3-ol, isothiazol-5-yl-3-ol, 3-chloro-4-hydroxy-phenyl, —C(O)—NH—CN, —C(O)—NH—$SO_2$—$CH_3$, —$SO_2$—NH—$CF_3$, and —$SO_2$—NH—$CF_2CF_3$;

wherein $R^C$ is selected from the group consisting of hydrogen, $C_{1-4}$alkyl, cyclopropyl, 3-hydroxy-cycloprop-1-yl, —C(O)—$C_{1-4}$alkyl, —C(O)-cyclopropyl, —C(O)—O—$C_{1-4}$alkyl and —$SO_2$—$C_{1-4}$alkyl; and $R^D$ is selected from the group consisting of hydrogen and $C_{1-4}$alkyl;

$R^5$ is selected from the group consisting of
(a) $C_{1-4}$alkyl; wherein the $C_{1-4}$alkyl is optionally substituted with one or more halogen; and further optionally substituted with a substituent selected from the group consisting of hydroxy, $C_{1-4}$alkoxy, fluorinated $C_{1-4}$alkoxy, —C(O)OH, —C(O)—O—($C_{1-4}$alkyl), —C(O)—O-(fluorinated $C_{1-4}$alkyl), —C(O)-(fluorinated $C_{1-4}$alkyl), and —C(O)—$NR^LR^M$;

wherein $R^L$ and $R^M$ are each independently selected from the group consisting of hydrogen and $C_{1-2}$alkyl;

(b) —$CH_2$—$C_{3-8}$cycloalkyl or —$CH_2$-adamant-1-yl; wherein the $C_{3-8}$cycloalkyl is optionally substituted with one or more halogen or $C_{1-4}$alkyl; and further optionally substituted with a substituent selected from the group consisting of —C(O)OH, —C(O)—O—$C_{1-4}$alkyl, —C(O)-(5 to 6 membered saturated heterocyclyl), —C(O)-(isoindolin-2-yl), —C(O)-(azaspiro[2.4]heptan-5-yl), —C(O)-(carboxy substituted azaspiro[2.4]heptan-5-yl), —C(O)—($NR^PR^Q$ substituted azaspiro[2.4]heptan-5-yl), phenyl, 1,1'-biphen-4-yl and —C(O)—$NR^PR^Q$;

wherein the —C(O)-(5 to 6 membered saturated heterocyclyl) substituent on the —$CH_2$—$C_{3-8}$cycloalkyl is further optionally substituted on the (5 to 6 membered heterocyclyl) with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, —C(O)OH, —C(O)—O—$C_{1-4}$alkyl, —$NR^PR^Q$, phenyl and $C_{3-8}$cycloalkyl;

wherein the phenyl substituent on the —$CH_2$—$C_{3-8}$cycloalkyl is further optionally substituted with one or more substituents independently selected form the group consisting of halogen, hydroxy, $C_{1-4}$alkyl, fluorinated $C_{1-4}$alkyl, $C_{1-4}$alkoxy, fluorinated $C_{1-4}$alkoxy, cyano, —$NR^PR^Q$, and $C_{3-8}$cycloalkyl;

and wherein $R^P$ and $R^Q$ are each independently selected from the group consisting of hydrogen and $C_{1-4}$alkyl;

(c) -$L^1$-(5 to 6 membered saturated heterocyclyl); wherein $L^1$ is selected from the group consisting of —$CH_2$— and —$CH_2$—C(O)—; wherein, when $L^1$ is —$CH_2$—C(O)—, then the (5 to 6 membered saturated heterocyclyl) is bound to the —C(O)— portion of $L^1$; - and wherein the (5 to 6 membered saturated heterocyclyl) is optionally substituted with one to two oxo group;

(d) —$C_{1-2}$alkyl-phenyl; wherein the phenyl is optionally substituted with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, —$OCH_2$—C(O)—$NR^SR^T$, phenyl and phenoxy; and wherein $R^S$ and $R^T$ are each independently selected from the group consisting of hydrogen and $C_{1-4}$alkyl;

(e) 1,2,3-triazol-4-yl, 1,2,5-triazol-3-yl, —$CH_2$-1,2,3-triazol-4-yl and —$CH_2$-1,2,5-triazol-3-yl; wherein the 1,2,3-triazol-4-yl or 1,2,5-triazoly-3-yl, whether alone or as part of the substituent group is optionally substituted with a substituent selected from the group consisting of $C_{1-4}$alkyl, fluorinated $C_{1-4}$alkyl, phenyl and piperidinyl;

wherein the piperidinyl is optionally substituted with —C(O)—$C_{1-4}$alkyl;

(f) —$CH_2$-(5 to 6 membered or 9 to 10 membered heterocyclyl); wherein the (5 to 6 membered or 9 to 10 membered heterocyclyl) is other than triazolyl;

wherein the (5 to 6 membered or 9 to 10 membered heterocyclyl) is optionally substituted with one or more substituents independently selected from the group consisting of halogen, hydroxy, oxo, $C_{1-4}$alkyl, fluorinated $C_{1-4}$alkyl, $C_{1-4}$alkoxy, fluorinated $C_{1-4}$alkoxy, cyano, —C(O)OH, —C(O)—O—$C_{1-4}$alkyl, —$C_{1-2}$alkyl-O—$C_{1-4}$alkyl, —$C_{1-2}$ alkyl-O-(fluorinated $C_{1-4}$alkyl), —C(O)—$NR^VR^W$, —$C_{1-2}$alkyl-C(O)—$NR^VR^W$, -(5 to 6 membered saturated heterocyclyl), —C(O)-(5 to 6 membered saturated heterocyclyl), —C(O)-(carboxy substituted 5 to 6 membered saturated heterocyclyl), —$C_{1-2}$alkyl-C(O)-(5 to 6 membered saturated heterocyclyl), phenyl and pyridinyl;

wherein the pyridinyl substituent on the —$CH_2$-(5 to 6 membered or 9 to 10 membered heterocyclyl) is further optionally substituted with one or more substituents independently selected from the group consisting of halogen and fluorinated $C_{1-4}$alkyl;

and wherein $R^V$ and $R^W$ are each independently selected from the group consisting of hydrogen and $C_{1-4}$alkyl;

and (g) —$CH_2$—$NR^8R^9$; wherein $R^8$ is selected from the group consisting of hydrogen and $C_{1-4}$alkyl; $R^9$ is selected from the group consisting of $C_{1-4}$alkyl, fluorinated $C_{1-4}$alkyl, $C_{1-4}$alkoxy, fluorinated $C_{1-4}$alkoxy, —C(O)—$C_{1-4}$alkyl, —C(O)—$C_{1-2}$alkyl-O—$C_{1-4}$alkyl, —C(O)-phenyl, —C(O)—$C_{1-2}$alkyl-phenyl, —C(O)—O—$C_{1-4}$alkyl, —C(O)—O-phenyl, —C(O)—O—$C_{1-2}$alkyl-phenyl, —C(O)—$C_{3-7}$cycloalkyl, —C(O)-(1-methyl-cycloprop-1-yl), —C(O)-(5 to 6 membered saturated heterocyclyl), —C(O)—$C_{1-2}$alkyl-C(O)-(5 to 6 membered saturated heterocyclyl), —O—$C_{1-2}$alkyl-C(O)-(5 to 6 membered saturated heterocyclyl), —C(O)-(1-methyl-pyridinyl-one) and —C(O)—$NR^XR^Y$; and wherein $R^X$ and $R^Y$ are each independently selected from the group consisting of hydrogen and $C_{1-4}$alkyl;

$R^6$ and $R^7$ are each independently selected from the group consisting of hydrogen, halogen, $C_{1-4}$alkyl and $C_{1-4}$alkoxy;

provided that at least one of $R^6$ or $R^7$ is hydrogen;

or a stereoisomer, isotopologue, isotopomer, or pharmaceutically acceptable salt thereof.

In certain embodiments, present invention is directed to compounds of formula (I), wherein $R^1$ is selected from the group consisting of halogen, $C_{1-4}$alkyl, fluorinated $C_{1-4}$alkyl, $C_{1-4}$alkoxy, fluorinated $C_{1-4}$alkoxy, cyano, —$NR^AR^B$, —C(O)—$C_{1-4}$alkyl, and 5 to 6 membered heterocyclyl;

wherein the 5 to 6 membered heterocyclyl is optionally substituted with one or more substituents independently selected from the group consisting of halogen, cyano, $C_{1-4}$alkyl, fluorinated $C_{1-4}$alkyl, $C_{1-4}$alkoxy, fluorinated $C_{1-4}$alkoxy, and $C_{3-7}$cycloalkyl; and wherein $R^A$ and $R^B$ are each independently selected from the group consisting of hydrogen and $C_{1-4}$alkyl;

a is an integer from 1 to 2;

each $R^2$ is independently selected from the group consisting of chloro and fluoro;

Y is N and Z is $C(R^3)$, such that

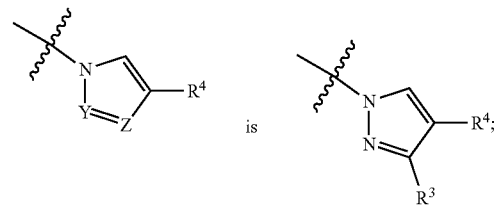

is $R^3$ is selected from the group consisting of hydrogen, and methyl;

$R^4$ is selected from the group consisting of (a) carboxy; and (b) phenyl; wherein the phenyl is optionally substituted with one to two substituents independently selected from the group consisting of halogen, fluorinated $C_{1-2}$alkoxy, —C(O)OH, —C(O)—O—($C_{1-4}$alkyl), —$NR^CR^D$, —$C_{1-2}$alkyl-$NR^CR^D$, —C(O)—$NR^CR^D$, —$NR^D$—C(O)—($C_{1-2}$alkyl)-O—($C_{1-4}$alkyl), —$NR^D$—C(O)—O—($C_{1-2}$alkyl)-O—($C_{1-4}$alkyl), cyclopropyl, 1-carboxy-cycloprop-1-yl, 1-($C_{1-4}$alkoxy-carbonyl)-cycloprop-1-yl, pyrrolidin-2-yl-5-one, 1,2,3,4-tetrazol-1-yl, 1,2,4-oxadiazol-3-yl-5-one and —C(O)—NH—$SO_2$—$CH_3$;

wherein $R^C$ is selected from the group consisting of hydrogen, cyclopropyl, 3-hydroxy-cycloprop-1-yl, —C(O)—$C_{1-4}$alkyl, —C(O)-cyclopropyl, —C(O)—O—$C_{1-4}$alkyl and —$SO_2$—$C_{1-4}$alkyl; and $R^D$ is selected from the group consisting of hydrogen and $C_{1-2}$alkyl;

$R^5$ is selected from the group consisting of (a) $C_{1-4}$alkyl; wherein the $C_{1-4}$alkyl is optionally substituted with one or more halogen; and further optionally substituted with a substituent selected from the group consisting of hydroxy, $C_{1-4}$alkoxy, fluorinated $C_{1-4}$alkoxy, —C(O)OH, —C(O)—O—($C_{1-4}$alkyl), —C(O)—O-(fluorinated $C_{1-4}$alkyl), —C(O)-(fluorinated $C_{1-4}$alkyl), and —C(O)—$NR^LR^M$;

wherein $R^L$ and $R^M$ are each independently selected from the group consisting of hydrogen and $C_{1-2}$alkyl;

(b) —$CH_2$—$C_{3-8}$cycloalkyl or —$CH_2$-adamant-1-yl; wherein the $C_{3-8}$cycloalkyl is optionally substituted with one to two halogen or $C_{1-4}$alkyl; and further optionally substituted with a substituent selected from the group consisting of —C(O)OH, —C(O)—O—$C_{1-4}$alkyl, —C(O)-(5 to 6 membered saturated heterocyclyl), —C(O)-(isoindolin-2-yl), —C(O)-(azaspiro[2.4]heptan-5-yl), —C(O)-(carboxy substituted azaspiro[2.4]heptan-5-yl), —C(O)—($NR^PR^Q$ substituted azaspiro[2.4]heptan-5-yl), phenyl, 1,1'-biphen-4-yl and —C(O)—$NR^PR^Q$;

wherein the —C(O)-(5 to 6 membered saturated heterocyclyl) substituent on the —$CH_2$—$C_{3-8}$cycloalkyl is further optionally substituted on the (5 to 6 membered heterocyclyl) with one to two substituents independently selected from the group consisting of halogen, $C_{1-4}$alkyl, —C(O)OH, —C(O)—O—$C_{1-4}$alkyl, phenyl and $C_{3-8}$cycloalkyl;
wherein the phenyl substituent on the —CH$_2$—$C_{3-8}$cycloalkyl is further optionally substituted with $C_{1-4}$alkoxy;
and wherein $R^P$ and $R^Q$ are each independently selected from the group consisting of hydrogen and $C_{1-4}$alkyl;
(c) -L$^1$-(5 to 6 membered saturated heterocyclyl); wherein L$^1$ is selected from the group consisting of —CH$_2$— and —CH$_2$—C(O)—; wherein, when L$^1$ is —CH$_2$—C(O)—, then the (5 to 6 membered saturated heterocyclyl) is bound to the —C(O)— portion of L$^1$; and wherein the (5 to 6 membered saturated heterocyclyl) is optionally substituted with one to two oxo group;
(d) —$C_{1-2}$alkyl-phenyl; wherein the phenyl is optionally substituted with one to two substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, —OCH$_2$—C(O)—NR$^S$R$^T$, phenyl and phenoxy; and wherein R$^S$ and R$^T$ are each independently selected from the group consisting of hydrogen and $C_{1-2}$alkyl;
(e) 1,2,3-triazol-4-yl, 1,2,5-triazol-3-yl, —CH$_2$-1,2,3-triazol-4-yl and —CH$_2$-1,2,5-triazol-3-yl; wherein the 1,2,3-triazol-4-yl or 1,2,5-triazoly-3-yl, whether alone or as part of the substituent group is optionally substituted with a substituent selected from the group consisting of $C_{1-4}$alkyl, fluorinated $C_{1-4}$alkyl, phenyl and piperidinyl;
wherein the piperidinyl is optionally substituted with —C(O)—$C_{1-4}$alkyl;
(f) —CH$_2$-(5 to 6 membered or 9 to 10 membered heterocyclyl); wherein the (5 to 6 membered or 9 to 10 membered heterocyclyl) is other than triazolyl;
wherein the (5 to 6 membered or 9 to 10 membered heterocyclyl) is optionally substituted with one to two substituents independently selected from the group consisting of halogen, hydroxy, oxo, $C_{1-4}$alkyl, fluorinated $C_{1-4}$alkyl, $C_{1-4}$alkoxy, fluorinated $C_{1-4}$alkoxy, cyano, —C(O)OH, —C(O)—O—$C_{1-4}$alkyl, —$C_{1-2}$alkyl-O—$C_{1-4}$alkyl, —$C_{1-2}$ alkyl-O-(fluorinated $C_{1-4}$alkyl), —C(O)—NR$^V$R$^W$, —$C_{1-2}$alkyl-C(O)—NR$^V$R$^W$, -(5 to 6 membered saturated heterocyclyl), —C(O)-(5 to 6 membered saturated heterocyclyl), —C(O)-(carboxy substituted 5 to 6 membered saturated heterocyclyl), —$C_{1-2}$alkyl-C(O)-(5 to 6 membered saturated heterocyclyl), phenyl and pyridinyl;
wherein the pyridinyl substituent on the —CH$_2$-(5 to 6 membered or 9 to 10 membered heterocyclyl) is further optionally substituted with one to two substituents independently selected from the group consisting of halogen and fluorinated $C_{1-4}$alkyl;
and wherein R$^V$ and R$^W$ are each independently selected from the group consisting of hydrogen and $C_{1-4}$alkyl;
and (g) —CH$_2$—NR$^8$R$^9$; wherein R$^8$ is selected from the group consisting of hydrogen and $C_{1-2}$alkyl; R$^9$ is selected from the group consisting of $C_{1-4}$alkyl, fluorinated $C_{1-4}$alkyl, $C_{1-4}$alkoxy, fluorinated $C_{1-4}$alkoxy, —C(O)—$C_{1-4}$alkyl, —C(O)—$C_{1-2}$alkyl-O—$C_{1-4}$alkyl, —C(O)-phenyl, —C(O)—$C_{1-2}$alkyl-phenyl, —C(O)—O—$C_{1-4}$alkyl, —C(O)—O-phenyl, —C(O)—O—$C_{1-2}$alkyl-phenyl, —C(O)—$C_{3-7}$cycloalkyl, —C(O)-(1-methyl-cycloprop-1-yl), —C(O)-(5 to 6 membered saturated heterocyclyl), —C(O)—$C_{1-2}$alkyl-C(O)-(5 to 6 membered saturated heterocyclyl), —O—$C_{1-2}$alkyl-C(O)-(5 to 6 membered saturated heterocyclyl), —C(O)-(1-methyl-pyridinyl-one) and —C(O)—NR$^X$R$^Y$; and wherein R$^X$ and R$^Y$ are each independently selected from the group consisting of hydrogen and $C_{1-2}$alkyl;
R$^6$ and R$^7$ are each independently selected from the group consisting of hydrogen, halogen, $C_{1-4}$alkyl and $C_{1-4}$alkoxy;
provided that at least one of R$^6$ or R$^7$ is hydrogen;
or a stereoisomer, isotopologue, isotopomer, or pharmaceutically acceptable salt or solvate thereof.
In certain embodiments, present invention is directed to compounds of formula (I), wherein R$^1$ is 5 to 6 membered heterocyclyl; wherein the 5 to 6 membered heterocyclyl is optionally substituted with one or more substituents independently selected from the group consisting of halogen, $C_{1-4}$alkyl and fluorinated $C_{1-4}$alkyl;
a is an integer from 1 to 2;
each R$^2$ is independently selected from the group consisting of chloro and fluoro; Y is N and Z is C(R$^3$), such that

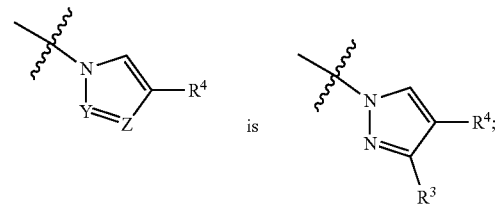

R$^3$ is hydrogen;
R$^4$ is selected from the group consisting of
(a) carboxy; and
(b) phenyl; wherein the phenyl is optionally substituted with one or more substituents independently selected from the group consisting of halogen, fluorinated $C_{1-2}$alkoxy, —C(O)OH, —NR$^C$R$^D$, —$C_{1-2}$alkyl-NR$^C$R$^D$, —C(O)—NR$^C$R$^D$, —NR$^D$—C(O)—($C_{1-2}$alkyl)-O—($C_{1-4}$alkyl), —NR$^D$—C(O)—O—($C_{1-2}$alkyl)-O—($C_{1-4}$alkyl), 1-carboxy-cycloprop-1-yl, 1-($C_{1-4}$alkoxy-carbonyl)-cycloprop-1-yl, pyrrolidin-3-yl-2,5-dione, 1,2,3,4-tetrazol-1-yl, 1,2,4-oxadiazol-3-yl-5-one, and —C(O)—NH—SO$_2$—CH$_3$;
wherein R$^C$ is selected from the group consisting of hydrogen, cyclopropyl, —C(O)—$C_{1-4}$alkyl, —C(O)—O—$C_{1-4}$alkyl and —SO$_2$—$C_{1-4}$alkyl; and R$^D$ is selected from the group consisting of hydrogen and $C_{1-2}$alkyl;
R$^5$ is selected from the group consisting of
(a) $C_{1-4}$alkyl; wherein the $C_{1-4}$alkyl is optionally substituted with a substituent selected from the group consisting of hydroxy, $C_{1-4}$alkoxy, fluorinated $C_{1-4}$alkoxy, —C(O)—O—($C_{1-4}$alkyl) and —C(O)—NR$^L$R$^M$; wherein R$^L$ and R$^M$ are each independently selected from the group consisting of hydrogen and $C_{1-2}$alkyl;
(b) —CH$_2$—$C_{3-8}$cycloalkyl or —CH$_2$-adamant-1-yl; wherein the $C_{3-6}$cycloalkyl is optionally substituted with one or more $C_{1-4}$alkyl; and further optionally substituted with a substituent selected from the group consisting of $C_{1-4}$ alkyl, —C(O)OH, —C(O)—O—$C_{1-4}$ alkyl, —C(O)-(5 to 6 membered saturated heterocyclyl), —C(O)-(isoindolin-2-yl), phenyl, 1,1'-biphen-4-yl and —C(O)—NR$^P$R$^Q$;

wherein the —C(O)-(5 to 6 membered saturated heterocyclyl) substituent on the —CH₂—C₃₋₈cycloalkyl is further optionally substituted on the (5 to 6 membered heterocyclyl) with one to two substituents independently selected from the group consisting of halogen, $C_{1-4}$alkyl, —C(O)OH, and phenyl;

wherein the phenyl substituent on the —CH₂—C₃₋₈cycloalkyl is further optionally substituted with $C_{1-4}$alkoxy;

and wherein $R^P$ and $R^Q$ are each independently selected from the group consisting of hydrogen and $C_{1-4}$alkyl;

(c) -L¹-(5 to 6 membered saturated heterocyclyl); wherein L¹ is selected from the group consisting of —CH₂— and —CH₂—C(O)—; wherein, when L¹ is —CH₂—C(O)—, then the (5 to 6 membered saturated heterocyclyl) is bound to the —C(O)— portion of L¹; and wherein the (5 to 6 membered saturated heterocyclyl) is optionally substituted with one to two oxo group;

(d) —$C_{1-2}$alkyl-phenyl; wherein the phenyl is optionally substituted with a substituent selected from the group consisting of halogen, hydroxy, $C_{1-4}$alkoxy, —OCH₂—C(O)—NR$^S$R$^T$, phenyl and phenoxy; and wherein R$^S$ and R$^T$ are each independently selected from the group consisting of hydrogen and $C_{1-2}$alkyl;

(e) 1,2,3-triazol-4-yl; wherein the 1,2,3-triazol-4-yl is optionally substituted with a substituent selected from the group consisting of $C_{1-4}$alkyl, phenyl and piperidinyl; wherein the piperidinyl is optionally substituted with —C(O)—$C_{1-2}$alkyl;

(f) —CH₂-(5 to 6 membered or 9 to 10 membered heterocyclyl); wherein the (5 to 6 membered or 9 to 10 heterocyclyl) is other than triazolyl;

wherein the (5 to 6 membered or 9 to 10 membered heterocyclyl) is optionally substituted with one or more substituents independently selected from the group consisting of halogen, oxo, $C_{1-4}$alkyl, fluorinated $C_{1-4}$alkyl, cyano, —C(O)OH, and —C(O)—NR$^V$R$^W$; wherein R$^V$ and R$^W$ are each independently selected from the group consisting of hydrogen and $C_{1-2}$alkyl; and (g) —CH₂—NR⁸R⁹; wherein R⁸ is $C_{1-2}$alkyl; R⁹ is —C(O)—O—$C_{1-4}$alkyl;

R⁶ and R⁷ are each independently selected from the group consisting of hydrogen, halogen and $C_{1-2}$alkoxy; provided that at least one of R⁶ or R⁷ is hydrogen;

or a stereoisomer, isotopologue, isotopomer, or pharmaceutically acceptable salt thereof.

In certain embodiments, present invention is directed to compounds of formula (I), wherein R¹ is selected from the group consisting of pyrazol-5-yl, oxazol-5-yl, 4-chloro-1,2,3-triazol-1-yl, 4-(trifluoro-methyl)-1,2,3-triazol-1-yl and 1,2,3,4-tetrazol-1-yl;

a is an integer from 1 to 2;

each R² is independently selected from the group consisting of 4-chloro, 5-chloro, 4-fluoro, 5-fluoro and 6-fluoro;

Y is N and Z is C(R³), such that

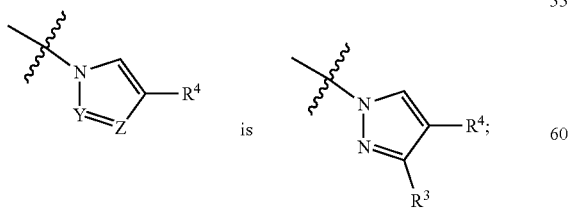

is

R³ is hydrogen;

R⁴ is selected from the group consisting of carboxy, phenyl, 4-fluoro-phenyl, 4-trifluoro-methoxy-phenyl, 3-carboxy-phenyl, 4-carboxy-phenyl, 3-fluoro-4-carboxy-phenyl, 4-amino-phenyl, 4-(methyl-d₃-amino)-phenyl, 4-(1-amino-ethyl)-phenyl, 4-(methyl-carbonyl-amino)-phenyl, 4-(methoxy-carbonyl-amino)-phenyl, 4-(methoxy-methyl-carbonyl-amino)-phenyl, 4-(2-methoxy-ethoxy-carbonyl-amino)-phenyl, 2-fluoro-6-(methyl-carbonyl-amino)-phenyl, 4-(1-(methoxy-carbonyl-amino)-ethyl)-phenyl, 4-(amino-carbonyl)-phenyl, 3-fluoro-4-(amino-carbonyl)-phenyl, 4-(cyclopropyl-amino-carbonyl)-phenyl, 4-(methyl-sulfonyl-amino)-phenyl, 4-(methyl-sulfonyl-amino-carbonyl)-phenyl, 4-(1-carboxy-cycloprop-1-yl)-phenyl, 4-((1-methoxy-carbonyl)-cycloprop-1-yl)-phenyl, 4-(pyrrolidin-2-yl-5-one)-phenyl), 2-(1,2,3,4-tetrazol-1-yl)-5-chloro-phenyl and 4-(1,2,4-oxadiazol-3-yl-5-one)-phenyl;

R⁵ is selected from the group consisting of
(a) isopropyloxy-methyl-, methoxy-carbonyl-methyl-, dimethyl-amino-carbonyl-methyl-, ethyl, R*-ethyl, S*-ethyl, R*-(2-hydroxy-ethyl-), S*-(2-hydroxy-ethyl-), 2-ethoxy-ethyl-, 2-(difluoro-methoxy)-ethyl-, S*-(2-(difluoro-methoxy)-ethyl-), R*-(2-(difluoro-methoxy)-ethyl-), R-(2-(difluoro-methoxy)-ethyl-), 2-methoxy-ethyl-, 2-(methoxy-d₃)-ethyl-, R-(2-methoxy-ethyl), R*-(2-methoxy-ethyl-), R-(2-(methoxy-d₃)-ethyl-), S*-(2-(methoxy-d₃)-ethyl-), R*-(2-isopropyloxy-ethyl), S*-(2-isopropyloxy-ethyl), 2-t-butoxy-ethyl-, S*-(2-(methoxy-d3)-ethyl-2,2-d₂-), R*-(2-(methoxy-d3)-ethyl-2,2-d2-), 2-(methyl-d₃)-ethyl-2,2-d₂-, n-propyl, R*-(n-propyl), S*-(n-propyl), S*-(2-methoxy-n-propyl-), R-(2-methoxy-n-propyl-), isobutyl, R-isobutyl, S*-isobutyl;

(b) cyclopropyl-methyl-, R*-(cyclopropyl-methyl-), R-(cyclopropyl-methyl-), S*-(cyclopropyl-methyl-), S-(cyclopropyl-methyl-), 2-methyl-cyclopropyl-methyl-, 2R*-carboxy-1S*-cyclopropyl-methyl-, 2S*-carboxy-1R*-cyclopropyl-methyl-, 2R*-carboxy-1R*-cyclopropyl-methyl-, 2S*-carboxy-1S*-cyclopropyl-methyl-, 2S*-(ethoxy-carbonyl)-1S*-cyclopropyl-methyl-, 2R*-(ethoxy-carbonyl)-1R*-cyclopropyl-methyl-, 2R*-(amino-carbonyl)-1S*-cyclopropyl-methyl-, 2S*-(amino-carbonyl)-1S*-cyclopropyl-methyl-, 2-(amino-carbonyl)-cyclopropyl-methyl-, 2-(1,1'-biphen-4-yl)-cyclopropyl-methyl, 2R*-(pyrrolidin-1-yl-carbonyl)-1S*-cyclopropyl-methyl-, 2S*-(pyrrolidin-1-yl-carbonyl)-1R*-cyclopropyl-methyl-, 2S*-(pyrrolidin-1-yl-carbonyl)-1S*-cyclopropyl-methyl-, 2R*-(pyrrolidin-1-yl-carbonyl)-1R*-cyclopropyl-methyl-, 2-(3-phenyl-pyrrolidin-1-yl-carbonyl)-cyclopropyl-methyl-, 2S*-(3-phenyl-pyrrolidin-1-yl-carbonyl)-1R*-cyclopropyl-methyl-, 2S*-(3-phenyl-pyrrolidin-1-yl-carbonyl)-1S*-cyclopropyl-methyl-, 2R*-(3-phenyl-pyrrolidin-1-yl-carbonyl)-1R*-cyclopropyl-methyl-, 2R*-(3-phenyl-pyrrolidin-1-yl-carbonyl)-1S*-cyclopropyl-methyl-, 2-(4,4-difluoro-piperidin-1-yl-carbonyl)-cyclopropyl-methyl-, 2-(piperidin-1-yl-carbonyl)-cyclopropyl-methyl-, 2S*-(piperidin-1-yl-carbonyl)-1R*-cyclopropyl-methyl-, 2R*-(piperidin-1-yl-carbonyl)-1R*-cyclopropyl-methyl-, 2R*-(piperidin-1-yl-carbonyl)-1S*-cyclopropyl-methyl-, 2S*-(piperidin-1-yl-carbonyl)-1S*-cyclopropyl-methyl-, 2S*-(4-carboxy-piperidin-1-yl-carbonyl)-1R*-cyclopropyl-methyl-, 2R*-(4-carboxy-piperidin-1-yl-carbonyl)-1R*-cyclopropyl-methyl-, 2S*-(3- carboxy-piperidin-1-yl-carbonyl)-1R*-cyclopropyl-methyl-, 2R*-(3-carboxy-piperidin-1-yl-carbonyl)-1R*-cyclopropyl-methyl-, 2R*-(piperazin-1-yl-carbonyl)-1S*-cyclopropyl-methyl-, 2R*-(morpholin-4-yl-carbonyl)-1R*-cyclopropyl-methyl-, 2S*-(morpholin-4-yl-carbonyl-methyl-, 2R*-(isoindolin-2-yl-carbonyl)-1S*cyclopropyl-methyl, 2S*-(isoindolin-2-yl-carbonyl)-1S*cyclopropyl-methyl, 2S*-(isoindolin-2-yl-carbonyl)-1R*cyclopropyl-methyl, 2R*-(isoindolin-2-yl-carbonyl)-1R*cyclopropyl-methyl, 2R*-(4-methoxy-phenyl)-1S*-cyclopropyl-methyl-, 2S*-(4-methoxy-phenyl)-1S*-cyclopropyl-methyl-, 2R*-(3-phenyl-pyrrolidin-1-yl-carbonyl)-1S*-cyclopropyl-methyl-, cyclobutyl-methyl-, 3,3-dimethyl-cyclobutyl-methyl-, cyclopentyl-methyl-, cyclohexyl-methyl-, 4-methyl-cyclohexyl-methyl-, 4,4-dimethyl-cyclohexyl-methyl-, adamantan-1-yl-methyl-;

(c) tetrahydrofuran-2-yl-methyl-, S*-(tetrahydrofuran-2-yl-methyl-), tetrahydropyran-2S*-yl-methyl-, tetrahydropyran-2R*-yl-methyl-, R*-(tetrahydropyran-2S*-yl-methyl-), S*-(tetrahydropyran-2S*-yl-methyl-), pyrrolidin-1-yl-carbonyl-methyl-, (pyrrolidin-1-yl-2-one)-methyl-, R*-((pyrrolidin-1-yl-2-one)-methyl-), S*-((pyrrolidin-1-yl-2-one)-methyl-), morpholin-4-yl-carbonyl-methyl-, piperazin-1-yl-carbonyl-methyl-;

(d) phenyl-methyl-, 4-chloro-phenyl-methyl-, R*-(4-chloro-phenyl-methyl-), S*-(4-chloro-phenyl-methyl-), 4-fluoro-phenyl-methyl-, 1R*-hydroxy-1-phenyl-methyl-, 1S*-hydroxy-1-phenyl-methyl-, 2-methoxy-phenyl-methyl-, R*-(3-methoxy-phenyl-methyl-), S*-(3-methoxy-phenyl-methyl-), 4-methoxy-phenyl-methyl-, 4-(amino-carbonyl-methoxy)-phenyl-methyl-, phenyl-ethyl-, 1,1'-biphen-4-yl-methyl-, 4-(phenoxy)-phenyl-methyl-;

(e) 1-methyl-1,2,3-triazol-4-yl, 1-phenyl-1,2,3-triazol-4-yl, 1-(piperidin-4-yl)-1,2,3-triazol-4-yl, 1-(1-methyl-carbonyl-piperidin-4-yl)-1,2,3-triazol-4-yl;

(f) pyrazol-1-yl-methyl-, R*-(pyrazol-1-yl-methyl-), S*-(pyrazol-1-yl-methyl-), 4-fluoro-pyrazol-1-yl-methyl-, 1-methyl-pyrazol-3-yl-methyl-, S-(1-methyl-pyrazol-3-yl-methyl-), R-(1-methyl-pyrazol-3-yl-methyl-), R*-(1-methyl-pyrazol-3-yl-methyl-), 4-(tert-butyl)-pyrazol-1-yl-methyl-, 1-(difluoro-methyl)-pyrazol-3-yl-methyl-, S*-(1-(difluoro-methyl)-pyrazol-3-yl-methyl-), R-(1-(difluoro-methyl)-pyrazol-3-yl-methyl-), R*-(1-(difluoro-methyl)-pyrazol-3-yl-methyl-), 3-carboxy-pyrazol-1-yl-methyl-, 3-(amino-carbonyl)-pyrazol-1-yl-methyl-, 4-cyano-pyrazol-1-yl-methyl-, isochroman-1-yl-methyl-, (pyridin-1-yl-2-one)-methyl-, oxazol-2-yl-methyl-, 1,2,4-oxadiazol-3-yl-methyl-, (5-methyl-1,3,4-oxadiazol-2-yl)-methyl-, thiazol-2-yl-methyl-, R*-(thiazol-2-yl-methyl-), S*-(thiazol-2-yl-methyl-);

and (g) N-methyl-N-(methoxy-carbonyl)-amino-methyl-;

$R^6$ is selected from the group consisting of hydrogen and fluoro;

$R^7$ is selected from the group consisting of hydrogen and methoxy;

provided that at least one of $R^6$ or $R^7$ is hydrogen;

or a pharmaceutically acceptable salt thereof.

In certain embodiments, present invention is directed to compounds of formula (I), wherein $R^1$ is selected from the group consisting of 4-chloro-1,2,3-triazol-1-yl, 4-(trifluoro-methyl)-1,2,3-triazol-1-yl and 1,2,3,4-tetrazol-1-yl;

a is an integer from 1 to 2;

each $R^2$ is independently selected from the group consisting of 4-fluoro, 5-chloro and 6-fluoro;

Y is N and Z is $C(R^3)$, such that

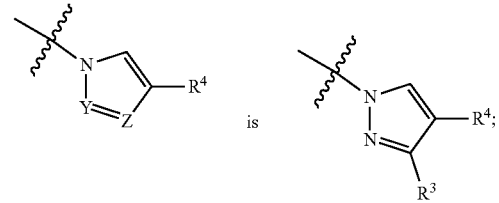

is $R^3$ is hydrogen;

$R^4$ is selected from the group consisting of phenyl, 4-fluoro-phenyl, 3-carboxy-phenyl, 4-carboxy-phenyl, 4-amino-phenyl, 4-(1-amino-ethyl)-phenyl, 4-(methyl-$d_3$-amino)-phenyl, 3-fluoro-4-carboxy-phenyl, 4-(amino-carbonyl)-phenyl, 3-fluoro-4-(amino-carbonyl)-phenyl, 4-(cyclopropyl-amino-carbonyl)-phenyl, 4-(methyl-carbonyl-amino)-phenyl, 4-(methoxy-carbonyl-amino)-phenyl, 2-fluoro-6-(methyl-carbonyl-amino)-phenyl, 4-(methoxy-methyl-carbonyl-amino)-phenyl, 4-(2-methoxy-ethoxy-carbonyl-amino)-phenyl, 4-(1-(methoxy-carbonyl-amino)-ethyl)-phenyl, 4-(methyl-sulfonyl-amino)-phenyl, 4-(methyl-sulfonyl-amino-carbonyl)-phenyl, 4-(1-carboxy-cycloprop-1-yl)-phenyl, 4-(pyrrolidin-2-yl-5-one)-phenyl), and 4-(1,2,4-oxadiazol-3-yl-5-one)-phenyl;

$R^5$ is selected from the group consisting of (a) isopropyloxy-methyl-, methoxy-carbonyl-methyl-, dimethyl-amino-carbonyl-methyl-, ethyl, R*-ethyl, S*-ethyl, S*-(2-hydroxy-ethyl-), 2-ethoxy-ethyl-, 2-(difluoro-methoxy)-ethyl-, S*-(2-(difluoro-methoxy)-ethyl-), R*-(2-(difluoro-methoxy)-ethyl-), R-(2-(difluoro-methoxy)-ethyl-), 2-methoxy-ethyl-, 2-(methoxy-$d_3$)-ethyl-, R-(2-methoxy-ethyl), R-(2-(methoxy-$d_3$)-ethyl-), S*-(2-(methoxy-d3)-ethyl-), S*-(2-isopropyloxy-ethyl), 2-t-butoxy-ethyl-, S*-(2-(methoxy-d3)-ethyl-2,2-d2-), 2-(methyl-$d_3$)-ethyl-2,2-$d_2$-, n-propyl, S*-(n-propyl), S*-(2-methoxy-n-propyl-), R-(2-methoxy-n-propyl-), isobutyl, S*-isobutyl;

cyclopropyl-methyl-, R-(cyclopropyl-methyl-), S*-(cyclopropyl-methyl-), 2-methyl-cyclopropyl-methyl-, 2R*-carboxy-1S*-cyclopropyl-methyl-, 2S*-carboxy-1R*-cyclopropyl-methyl-, 2R*-carboxy-1R*-cyclopropyl-methyl-, 2S*-carboxy-1S*-cyclopropyl-methyl-, 2S*-(ethoxy-carbonyl)-1S*-cyclopropyl-methyl-, 2R*-(ethoxy-carbonyl)-1R*-cyclopropyl-methyl-, 2R*-(amino-carbonyl)-1S*-cyclopropyl-methyl-, 2S*-(amino-carbonyl)-1S*-cyclopropyl-methyl-, 2-(amino-carbonyl)-cyclopropyl-methyl-, 2-(1,1'-biphen-4-yl)-cyclopropyl-methyl, 2R*-(pyrrolidin-1-yl-carbonyl)-1S*-cyclopropyl-methyl-, 2S*-(pyrrolidin-1-yl-carbonyl)-1S*-cyclopropyl-methyl-, 2R*-(pyrrolidin-1-yl-carbonyl)-1R*-cyclopropyl-methyl-, 2-(3-phenyl-pyrrolidin-1-yl-carbonyl)-cyclopropyl-methyl-, 2S*-(3-phenyl-pyrrolidin-1-yl-carbonyl)-1R*-cyclopropyl-methyl-, 2S*-(3-phenyl-pyrrolidin-1-yl-carbonyl)-1S*-cyclopropyl-methyl-, 2R*-(3-phenyl-pyrrolidin-1-yl-carbonyl)-1R*-cyclopropyl-methyl-, 2R*-(3-phenyl-pyrrolidin-1-yl-carbonyl)-1S*-cyclopropyl-methyl-, 2-(4,4-difluoro-piperidin-1-yl-carbonyl)-cyclopropyl-methyl-, 2-(piperidin-1-yl-carbonyl)-cyclopropyl-methyl-, 2S*-(piperidin-1-yl-carbonyl)-1R*-cyclopropyl-methyl-, 2R*-

(piperidin-1-yl-carbonyl)-1R*-cyclopropyl-methyl-, 2R*-(piperidin-1-yl-carbonyl)-1S*-cyclopropyl-methyl-, 2S*-(piperidin-1-yl-carbonyl)-1S*-cyclopropyl-methyl-, 2S*-(4-carboxy-piperidin-1-yl-carbonyl)-1R*-cyclopropyl-methyl-, 2R*-(4-carboxy-piperidin-1-yl-carbonyl)-1R*-cyclopropyl-methyl-, 2S*-(3-carboxy-piperidin-1-yl-carbonyl)-1R*-cyclopropyl-methyl-, 2R*-(3-carboxy-piperidin-1-yl-carbonyl)-1R*-cyclopropyl-methyl-, 2R*-(piperazin-1-yl-carbonyl)-1S*-cyclopropyl-methyl-, 2R*-(morpholin-4-yl-carbonyl)-1S*-cyclopropyl-methyl-, 2S*-(morpholin-4-yl-carbonyl)-1S*-cyclopropyl-methyl-, 2R*-(isoindolin-2-yl-carbonyl)-1S*cyclopropyl-methyl, 2S*-(isoindolin-2-yl-carbonyl)-1S*cyclopropyl-methyl, 2S*-(isoindolin-2-yl-carbonyl)-1R*cyclopropyl-methyl, 2R*-(isoindolin-2-yl-carbonyl)-1R*cyclopropyl-methyl, 2R*-(4-methoxy-phenyl)-1S*-cyclopropyl-methyl-, 2S*-(4-methoxy-phenyl)-1S*-cyclopropyl-methyl-, 2R*-(3-phenyl-pyrrolidin-1-yl-carbonyl)-1S*-cyclopropyl-methyl-, cyclobutyl-methyl-, 3,3-dimethyl-cyclobutyl-methyl-, cyclopentyl-methyl-, cyclohexyl-methyl-, 4-methyl-cyclohexyl-methyl-, 4,4-dimethyl-cyclohexyl-methyl-, adamantan-1-yl-methyl-;
(c) tetrahydrofuran-2-yl-methyl-, S*-(tetrahydrofuran-2-yl-methyl-), tetrahydropyran-2S*-yl-methyl-, tetrahydropyran-2R*-yl-methy, ethyl-), pyrrolidin-1-yl-carbonyl-methyl-, (pyrrolidin-1-yl-2-one)-methyl-, S*-((pyrrolidin-1-yl-2-one)-methyl-), morpholin-4-yl-carbonyl-methyl-, piperazin-1-yl-carbonyl-methyl-;
(d) phenyl-methyl-, 4-chloro-phenyl-methyl-, R*-(4-chloro-phenyl-methyl-), S*-(4-chloro-phenyl-methyl-), 4-fluoro-phenyl-methyl-, 1R*-hydroxy-1-phenyl-methyl-, 1S*-hydroxy-1-phenyl-methyl-, 2-methoxy-phenyl-methyl-, R*-(3-methoxy-phenyl-methyl-), S*-(3-methoxy-phenyl-methyl-), 4-methoxy-phenyl-methyl-, 4-(amino-carbonyl-methoxy)-phenyl-methyl-, phenyl-ethyl-, 1,1'-biphen-4-yl-methyl-, 4-(phenoxy)-phenyl-methyl-;
(e) 1-(1-methyl-carbonyl-piperidin-4-yl)-1,2,3-triazol-4-yl;
(f) pyrazol-1-yl-methyl-, R*-(pyrazol-1-yl-methyl-), S*-(pyrazol-1-yl-methyl-), 4-fluoro-pyrazol-1-yl-methyl-, 1-methyl-pyrazol-3-yl-methyl-, S-(1-methyl-pyrazol-3-yl-methyl-), R-(1-methyl-pyrazol-3-yl-methyl-), R*-(1-methyl-pyrazol-3-yl-methyl-), 4-(tert-butyl)-pyrazol-1-yl-methyl-, 1-(difluoro-methyl)-pyrazol-3-yl-methyl-, S*-(1-(difluoro-methyl)-pyrazol-3-yl-methyl-), R-(1-(difluoro-methyl)-pyrazol-3-yl-methyl-), R*-(1-(difluoro-methyl)-pyrazol-3-yl-methyl-), 4-cyano-pyrazol-1-yl-methyl-, isochroman-1-yl-methyl-, (pyridin-1-yl-2-one)-methyl-, oxazol-2-yl-methyl-, 1,2,4-oxadiazol-3-yl-methyl-, (5-methyl-1,3,4-oxadiazol-2-yl)-methyl-, thiazol-2-yl-methyl-, R*-(thiazol-2-yl-methyl-), S*-(thiazol-2-yl-methyl-);
and (g) N-methyl-N-(methoxy-carbonyl)-amino-methyl-;
R⁶ is selected from the group consisting of hydrogen and fluoro;
R⁷ is selected from the group consisting of hydrogen and methoxy;
provided that at least one of R⁶ or R⁷ is hydrogen;
or a pharmaceutically acceptable salt thereof.

In certain embodiments, present invention is directed to compounds of formula (I), wherein R¹ is selected from the group consisting of 4-chloro-1,2,3-triazol-1-yl, 4-(trifluoro-methyl)-1,2,3-triazol-1-yl and 1,2,3,4-tetrazol-1-yl;
a is an integer from 1 to 2;
each R² is independently selected from the group consisting of 5-chloro and 6-fluoro;
Y is N and Z is C(R³), such that

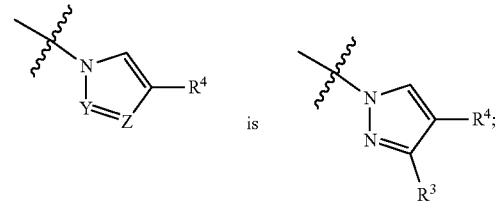

R³ is hydrogen;
R⁴ is selected from the group consisting of 3-carboxy-phenyl, 4-carboxy-phenyl, 4-(methyl-d₃-amino)-phenyl, 3-fluoro-4-carboxy-phenyl, 4-(amino-carbonyl)-phenyl, 3-fluoro-4-(amino-carbonyl)-phenyl, 4-(cyclopropyl-amino-carbonyl)-phenyl, 4-(methyl-carbonyl-amino)-phenyl, 4-(methoxy-carbonyl-amino)-phenyl, 2-fluoro-6-(methyl-carbonyl-amino)-phenyl, 4-(2-methoxy-ethoxy-carbonyl-amino)-phenyl, 4-(1-(methoxy-carbonyl-amino)-ethyl)-phenyl, 4-(methyl-sulfonyl-amino)-phenyl, 4-(methyl-sulfonyl-amino-carbonyl)-phenyl, 4-(pyrrolidin-2-yl-5-one)-phenyl), and 4-(1,2,4-oxadiazol-3-yl-5-one)-phenyl;
R⁵ is selected from the group consisting of
(a) isopropyloxy-methyl-, methoxy-carbonyl-methyl-, dimethyl-amino-carbonyl-methyl-, ethyl, R*-ethyl, S*-ethyl, S*-(2-hydroxy-ethyl-), 2-ethoxy-ethyl-, 2-(difluoro-methoxy)-ethyl-, S*-(2-(difluoro-methoxy)-ethyl-), R*-(2-(difluoro-methoxy)-ethyl-), R-(2-(difluoro-methoxy)-ethyl-), 2-methoxy-ethyl-, 2-(methoxy-d₃)-ethyl-), R-(2-methoxy-ethyl-), R-(2-(methoxy-d₃)-ethyl-), S*-(2-isopropyloxy-ethyl), 2-t-butoxy-ethyl-, S*-(2-(methoxy-d₃)-ethyl-2,2-d₂-), n-propyl, S*-(n-propyl), R-(2-methoxy-n-propyl-), S*-isobutyl;
(b) cyclopropyl-methyl-, R-(cyclopropyl-methyl-), S*-(cyclopropyl-methyl-), 2-methyl-cyclopropyl-methyl-, 2S*-(ethoxy-carbonyl)-1S*-cyclopropyl-methyl-, 2R*-(ethoxy-carbonyl)-1R*-cyclopropyl-methyl-, 2R*-(amino-carbonyl)-1S*-cyclopropyl-methyl-, 2S*-(amino-carbonyl)-1S*-cyclopropyl-methyl-, 2-(1,1'-biphen-4-yl)-cyclopropyl-methyl, 2S*-(pyrrolidin-1-yl-carbonyl)-1S*-cyclopropyl-methyl-, 2-(3-phenyl-pyrrolidin-1-yl-carbonyl)-cyclopropyl-methyl-, 2S*-(3-phenyl-pyrrolidin-1-yl-carbonyl)-1R*-cyclopropyl-methyl-, 2S*-(3-phenyl-pyrrolidin-1-yl-carbonyl)-1S*-cyclopropyl-methyl-, 2R*-(3-phenyl-pyrrolidin-1-yl-carbonyl)-1S*-cyclopropyl-methyl-, 2-(piperidin-1-yl-carbonyl)-cyclopropyl-methyl-, 2R*-(piperidin-1-yl-carbonyl)-1S*-cyclopropyl-methyl-, 2R*-(morpholin-4-yl-carbon yl-methyl-, 2S*-(isoindolin-2-yl-carbonyl)-1S*cyclopropyl-methyl, cyclobutyl-methyl-, 3,3-dimethyl-cyclobutyl-methyl-, cyclopentyl-methyl-, cyclohexyl-methyl-;
(c) tetrahydrofuran-2-yl-methyl-, S*-(tetrahydrofuran-2-yl-methyl-), tetrahydropyran-2S*-yl-methyl-, tetrahydropyran-2R*-yl-methyl-, S*-(tetrahydropyran-2S*-yl-methyl-), pyrrolidin-1-yl-carbonyl-methyl-, (pyrrolidin-1-yl-2-one)-methyl-, S*-((pyrrolidin-1-yl-2-one)-methyl-), morpholin-4-yl-carbonyl-methyl-;

(d) phenyl-methyl-, 4-chloro-phenyl-methyl-, R*-(4-chloro-phenyl-methyl-), S*-(4-chloro-phenyl-methyl-), 4-fluoro-phenyl-methyl-, 1R*-hydroxy-1-phenyl-methyl-, 1S*-hydroxy-1-phenyl-methyl-, 2-methoxy-phenyl-methyl-, R*-(3-methoxy-phenyl-methyl-), S*-(3-methoxy-phenyl-methyl-), 4-methoxy-phenyl-methyl-, 4-(amino-carbonyl-methoxy)-phenyl-methyl-, 1,1'-biphen-4-yl-methyl-, 4-(phenoxy)-phenyl-methyl-;

(f) pyrazol-1-yl-methyl-, R*-(pyrazol-1-yl-methyl-), S*-(pyrazol-1-yl-methyl-), 4-fluoro-pyrazol-1-yl-methyl-, 1-methyl-pyrazol-3-yl-methyl-, R-(1-methyl-pyrazol-3-yl-methyl-), R*-(1-methyl-pyrazol-3-yl-methyl-), 1-(difluoro-methyl)-pyrazol-3-yl-methyl-, S*-(1-(difluoro-methyl)-pyrazol-3-yl-methyl-), R-(1-(difluoro-methyl)-pyrazol-3-yl-methyl-), R*-(1-(difluoro-methyl)-pyrazol-3-yl-methyl-), isochroman-1-yl-methyl-, (pyridin-1-yl-2-one)-methyl-, oxazol-2-yl-methyl-, 1,2,4-oxadiazol-3-yl-methyl-, (5-methyl-1,3,4-oxadiazol-2-yl)-methyl-, thiazol-2-yl-methyl-, S*-(thiazol-2-yl-methyl-);

and (g) N-methyl-N-(methoxy-carbonyl)-amino-methyl-;

$R^6$ is selected from the group consisting of hydrogen and fluoro;

$R^7$ is selected from the group consisting of hydrogen and methoxy;

provided that at least one of $R^6$ or $R^7$ is hydrogen;

or a pharmaceutically acceptable salt thereof.

In certain embodiments, present invention is directed to compounds of formula (I), wherein $R^1$ is selected from the group consisting of 4-chloro-1,2,3-triazol-1-yl, 4-(trifluoromethyl)-1,2,3-triazol-1-yl and 1,2,3,4-tetrazol-1-yl;

a is an integer from 1 to 2;

each $R^2$ is independently selected from the group consisting of 5-chloro and 6-fluoro;

Y is N and Z is C($R^3$), such that

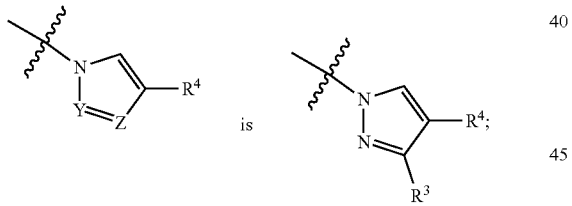

is $R^3$ is hydrogen;

$R^4$ is selected from the group consisting of 4-carboxy-phenyl, 3-fluoro-4-carboxy-phenyl, 4-(amino-carbonyl)-phenyl, 3-fluoro-4-(amino-carbonyl)-phenyl, 4-(methoxy-carbonyl-amino)-phenyl, and 4-(1,2,4-oxadiazol-3-yl-5-one)-phenyl;

$R^5$ is selected from the group consisting of (a) methoxy-carbonyl-methyl-, R*-ethyl, 2-ethoxy-ethyl-, 2-(difluoro-methoxy)-ethyl-, S*-(2-(difluoro-methoxy)-ethyl-), R*-(2-(difluoro-methoxy)-ethyl-), R-(2-(difluoro-methoxy)-ethyl-), R-(2-methoxy-ethyl-), R-(2-(methoxy-d₃)-ethyl-), S*-(2-isopropyloxy-ethyl), R-(2-methoxy-n-propyl-);

(b) cyclopropyl-methyl-, R-(cyclopropyl-methyl-), S*-(cyclopropyl-methyl-), 2-methyl-cyclopropyl-methyl-, 2-(3-phenyl-pyrrolidin-1-yl-carbonyl)-cyclopropyl-methyl-, 2R*-(3-phenyl-pyrrolidin-1-yl-carbonyl)-1S*-cyclopropyl-methyl-, 2-(piperidin-1-yl-carbonyl)-cyclopropyl-methyl-;

(c) tetrahydropyran-2S*-yl-methyl-, tetrahydropyran-2R*-yl-methyl-, S*-(tetrahydropyran-2S*-yl-methyl-), (pyrrolidin-1-yl-2-one)-methyl-, S*-((pyrrolidin-1-yl-2-one)-methyl-);

(d) phenyl-methyl-, 4-chloro-phenyl-methyl-, 4-fluoro-phenyl-methyl-, 1R*-hydroxy-1-phenyl-methyl-, S*-(3-methoxy-phenyl-methyl-), 4-methoxy-phenyl-methyl-, 4-(amino-carbonyl-methoxy)-phenyl-methyl-, 1,1'-biphen-4-yl-methyl-, 4-(phenoxy)-phenyl-methyl-;

(f) pyrazol-1-yl-methyl-, R*-(pyrazol-1-yl-methyl-), S*-(pyrazol-1-yl-methyl-), 4-fluoro-pyrazol-1-yl-methyl-, 1-methyl-pyrazol-3-yl-methyl-, R-(1-methyl-pyrazol-3-yl-methyl-), 1-(difluoro-methyl)-pyrazol-3-yl-methyl-, S*-(1-(difluoro-methyl)-pyrazol-3-yl-methyl-), R-(1-(difluoro-methyl)-pyrazol-3-yl-methyl-), R*-(1-(difluoro-methyl)-pyrazol-3-yl-methyl-), (pyridin-1-yl-2-one)-methyl-, oxazol-2-yl-methyl-, thiazol-2-yl-methyl-, S*-(thiazol-2-yl-methyl-);

and (g) N-methyl-N-(methoxy-carbonyl)-amino-methyl-;

$R^6$ is hydrogen;

$R^7$ is selected from the group consisting of hydrogen and methoxy;

or a pharmaceutically acceptable salt thereof.

In certain embodiments, present invention is directed to compounds of formula (I), wherein $R^1$ is selected from the group consisting of 4-chloro-1,2,3-triazol-1-yl, 4-(trifluoromethyl)-1,2,3-triazol-1-yl and 1,2,3,4-tetrazol-1-yl;

a is an integer from 1 to 2;

each $R^2$ is independently selected from the group consisting of 5-chloro and 6-fluoro;

Y is N and Z is C($R^3$), such that

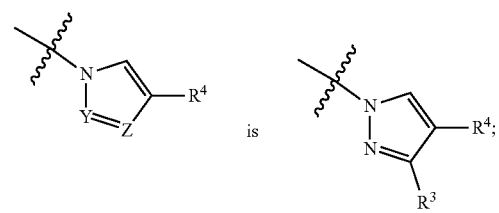

$R^3$ is hydrogen;

$R^4$ is selected from the group consisting of 4-carboxy-phenyl, 3-fluoro-4-carboxy-phenyl, 4-(amino-carbonyl)-phenyl, 3-fluoro-4-(amino-carbonyl)-phenyl, 4-(methoxy-carbonyl-amino)-phenyl, and 4-(1,2,4-oxadiazol-3-yl-5-one)-phenyl;

$R^5$ is selected from the group consisting of (a) methoxy-carbonyl-methyl-, 2-(difluoro-methoxy)-ethyl-, S*-(2-(difluoro-methoxy)-ethyl-), R*-(2-(difluoro-methoxy)-ethyl-), R-(2-(difluoro-methoxy)-ethyl-), R-(2-methoxy-ethyl-);

(b) cyclopropyl-methyl- and 2-(3-phenyl-pyrrolidin-1-yl-carbonyl)-cyclopropyl-methyl;

(c) S*-((pyrrolidin-1-yl-2-one)-methyl-);

(d) 4-chloro-phenyl-methyl-, 4-fluoro-phenyl-methyl-, 4-methoxy-phenyl-methyl-, 4-(amino-carbonyl-methoxy)-phenyl-methyl-;

and (f) R*-(pyrazol-1-yl-methyl-), R-(1-methyl-pyrazol-3-yl-methyl-), S*-(1-(difluoro-methyl)-pyrazol-3-yl-methyl-), R-(1-(difluoro-methyl)-pyrazol-3-yl-methyl-), R*-(1-(difluoro-methyl)-pyrazol-3-ylmethyl-), (pyridin-1-yl-2-one)-methyl-, oxazol-2-yl-methyl-, thiazol-2-yl-methyl-;

$R^6$ is hydrogen;

$R^7$ is hydrogen;

or a pharmaceutically acceptable salt thereof.

In certain embodiments, present invention is directed to compounds of formula (I), wherein $R^1$ is selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, nitro, —$NR^AR^B$, —C(O)—$C_{1-4}$alkyl, $C_{3-6}$cycloalkyl, phenyl and 5 to 6 membered heterocyclyl;

wherein the $C_{3-6}$cycloalkyl, phenyl or 5 to 6 membered heterocyclyl is optionally substituted with one or more substituents independently selected from the group consisting of halogen, hydroxy, cyano, $C_{1-4}$alkyl, fluorinated $C_{1-4}$alkyl, $C_{1-4}$alkoxy, fluorinated $C_{1-4}$alkoxy, —C(O)OH, —C(O)O—($C_{1-4}$alkyl), —$NR^AR^B$, —($C_{1-4}$ alkyl)-$NR^AR^B$, $C_{3-7}$cycloalkyl and 5 to 6 membered heterocyclyl; and wherein $R^A$ and $R^B$ are each independently selected from the group consisting of hydrogen and $C_{1-4}$alkyl;

a is an integer from 0 to 3;

each $R^2$ is independently selected from the group consisting of chloro, fluoro, methyl and methoxy;

Y is N and Z is C($R^3$), such that

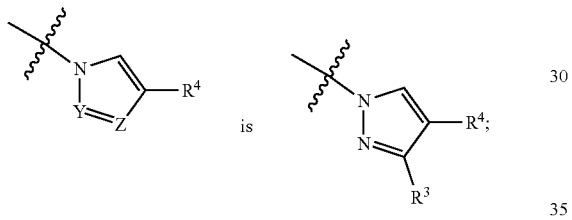

is $R^3$ is selected from the group consisting of hydrogen, fluoro, chloro and methyl;

$R^4$ is 6 membered heterocyclyl; wherein the 6 membered heterocyclyl contains at least one heteroatom selected from the group consisting of N, O and S; optionally contains 1 to 3 additional heteroatoms independently selected from the group consisting of O, N and S; wherein the 6 membered heterocyclyl is saturated, partially unsaturated, or aromatic; wherein the 6 membered heterocyclyl is bound through a carbon atom;

and wherein the 6 membered heterocyclyl is optionally substituted with one or more substituents independently selected from the group consisting of halogen, hydroxy, oxo, $C_{1-4}$alkyl, fluorinated $C_{1-4}$alkyl, $C_{1-4}$alkoxy, fluorinated $C_{1-4}$alkoxy, —$C_{1-2}$alkyl-O—$C_{1-4}$alkyl, $C_{3-7}$cycloalkyl, —C(O)OH, —C(O)—O—$C_{1-4}$alkyl, —$C_{1-2}$alkyl-C(O)—O—$C_{1-4}$alkyl, cyano, —$NR^GR^H$, —C(O)—$NR^GR^H$, pyrrolidin-2-yl-5-one, pyrrolidin-3-yl-2,5-dione, pyrrol-3-yl-2,5-dione, 1,2,3,4-tetrazol-1-yl, 1,2,3,4-tetrazol-5-yl, 1,2,4-oxadiazol-3-yl-5-one, oxazolidin-5-yl-2,4-dione, 1H-imidazol-5-yl-2,5-dione, thiazol-5-yl-2,4-dione, isoxazol-5-yl-3-ol, isothiazol-5-yl-3-ol, 3-chloro-4-hydroxy-phenyl, —C(O)—NH—CN, —C(O)—NH—SO$_2$—CH$_3$, —SO$_2$—NH—CF$_3$, and —SO$_2$—NH—CF$_2$CF$_3$;

wherein $R^G$ is selected from the group consisting of hydrogen, $C_{1-4}$alkyl, cyclopropyl, 3-hydroxy-cycloprop-1-yl, —C(O)—$C_{1-4}$alkyl, —C(O)-cyclopropyl, —C(O)—O—$C_{1-4}$alkyl and —SO$_2$—$C_{1-4}$alkyl; and $R^H$ is selected from the group consisting of hydrogen and $C_{1-4}$alkyl;

and wherein the 6 membered heterocyclyl contains a nitrogen ring atom, said nitrogen ring atom may be further optionally substituted with oxygen to form an N-oxide;

$R^5$ is selected from the group consisting of (a) $C_{1-4}$alkyl; wherein the $C_{1-4}$alkyl is optionally substituted with one or more halogen; and further optionally substituted with a substituent selected from the group consisting of hydroxy, $C_{1-4}$alkoxy, fluorinated $C_{1-4}$alkoxy, —C(O)OH, —C(O)—O—($C_{1-4}$alkyl), —C(O)—O-(fluorinated $C_{1-4}$alkyl), —C(O)-(fluorinated $C_{1-4}$alkyl), and —C(O)—$NR^LR^M$;

wherein $R^L$ and $R^M$ are each independently selected from the group consisting of hydrogen and $C_{1-2}$alkyl;

(b) —CH$_2$—$C_{3-8}$cycloalkyl or —CH$_2$-adamant-1-yl; wherein the $C_{3-8}$cycloalkyl is optionally substituted with one or more halogen or $C_{1-4}$alkyl; and further optionally substituted with a substituent selected from the group consisting of —C(O)OH, —C(O)—O—$C_{1-4}$alkyl, —C(O)-(5 to 6 membered saturated heterocyclyl), —C(O)-(isoindolin-2-yl), —C(O)-(azaspiro[2.4]heptan-5-yl), —C(O)-(carboxy substituted azaspiro[2.4]heptan-5-yl), —C(O)—($NR^PR^Q$ substituted azaspiro[2.4]heptan-5-yl), phenyl, 1,1'-biphen-4-yl and —C(O)—$NR^PR^Q$;

wherein the —C(O)-(5 to 6 membered saturated heterocyclyl) substituent on the —CH$_2$—$C_{3-8}$cycloalkyl is further optionally substituted on the (5 to 6 membered heterocyclyl) with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, —C(O)OH, —C(O)—O—$C_{1-4}$alkyl, —$NR^PR^Q$, phenyl and $C_{3-8}$cycloalkyl;

wherein the phenyl substituent on the —CH$_2$—$C_{3-8}$cycloalkyl is further optionally substituted with one or more substituents independently selected form the group consisting of halogen, hydroxy, $C_{1-4}$alkyl, fluorinated $C_{1-4}$ alkyl, $C_{1-4}$alkoxy, fluorinated $C_{1-4}$alkoxy, cyano, —$NR^PR^Q$, and $C_{3-8}$cycloalkyl;

and wherein $R^P$ and $R^Q$ are each independently selected from the group consisting of hydrogen and $C_{1-4}$alkyl;

(c) -$L^1$-(5 to 6 membered saturated heterocyclyl); wherein $L^1$ is selected from the group consisting of —CH$_2$— and —CH$_2$—C(O)—; wherein, when $L^1$ is —CH$_2$—C(O)—, then the (5 to 6 membered saturated heterocyclyl) is bound to the —C(O)— portion of $L^1$; - and wherein the (5 to 6 membered saturated heterocyclyl) is optionally substituted with one to two oxo group;

(d) —$C_{1-2}$alkyl-phenyl; wherein the phenyl is optionally substituted with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, —OCH$_2$—C(O)—$NR^SR^T$, phenyl and phenoxy; and wherein $R^S$ and $R^T$ are each independently selected from the group consisting of hydrogen and $C_{1-4}$alkyl;

(e) 1,2,3-triazol-4-yl, 1,2,5-triazol-3-yl, —CH$_2$-1,2,3-triazol-4-yl and —CH$_2$-1,2,5-triazol-3-yl; wherein the 1,2,3-triazol-4-yl or 1,2,5-triazoly-3-yl, whether alone or as part of the substituent group is optionally substituted with a substituent selected from the group consisting of $C_{1-4}$alkyl, fluorinated $C_{1-4}$alkyl, phenyl and piperidinyl;

wherein the piperidinyl is optionally substituted with —C(O)—$C_{1-4}$alkyl;

(f) —CH$_2$-(5 to 6 membered or 9 to 10 membered heterocyclyl); wherein the (5 to 6 membered or 9 to 10 membered heterocyclyl) is other than triazolyl;

wherein the (5 to 6 membered or 9 to 10 membered heterocyclyl) is optionally substituted with one or more substituents independently selected from the group consisting of halogen, hydroxy, oxo, C$_{1-4}$alkyl, fluorinated C$_{1-4}$alkyl, C$_{1-4}$alkoxy, fluorinated C$_{1-4}$alkoxy, cyano, —C(O)OH, —C(O)—O—C$_{1-4}$alkyl, —C$_{1-2}$alkyl-O—C$_{1-4}$alkyl, —C$_{1-2}$ alkyl-O-(fluorinated C$_{1-4}$alkyl), —C(O)—NR$^V$R$^W$, —C$_{1-2}$alkyl-C(O)—NR$^V$R$^W$, -(5 to 6 membered saturated heterocyclyl), —C(O)-(5 to 6 membered saturated heterocyclyl), —C(O)-(carboxy substituted 5 to 6 membered saturated heterocyclyl), —C$_{1-2}$alkyl-C(O)-(5 to 6 membered saturated heterocyclyl), phenyl and pyridinyl;

wherein the pyridinyl substituent on the —CH$_2$-(5 to 6 membered or 9 to 10 membered heterocyclyl) is further optionally substituted with one or more substituents independently selected from the group consisting of halogen and fluorinated C$_{1-4}$alkyl;

and wherein R$^V$ and R$^W$ are each independently selected from the group consisting of hydrogen and C$_{1-4}$alkyl;

and (g) —CH$_2$—NR$^8$R$^9$; wherein R$^8$ is selected from the group consisting of hydrogen and C$_{1-4}$alkyl; R$^9$ is selected from the group consisting of C$_{1-4}$alkyl, fluorinated C$_{1-4}$alkyl, C$_{1-4}$alkoxy, fluorinated C$_{1-4}$alkoxy, —C(O)—C$_{1-4}$alkyl, —C(O)—C$_{1-2}$alkyl-O—C$_{1-4}$alkyl, —C(O)-phenyl, —C(O)—C$_{1-2}$alkyl-phenyl, —C(O)—O—C$_{1-4}$alkyl, —C(O)—O-phenyl, —C(O)—O—C$_{1-2}$ alkyl-phenyl, —C(O)—C$_{3-7}$cycloalkyl, —C(O)-(1-methyl-cycloprop-1-yl), —C(O)-(5 to 6 membered saturated heterocyclyl), —C(O)—C$_{1-2}$alkyl-C(O)-(5 to 6 membered saturated heterocyclyl), —O—C$_{1-2}$alkyl-C(O)-(5 to 6 membered saturated heterocyclyl), —C(O)-(1-methyl-pyridinyl-one) and —C(O)—NR$^X$R$^Y$;

and wherein R$^X$ and R$^Y$ are each independently selected from the group consisting of hydrogen and C$_{1-4}$alkyl;

R$^6$ and R$^7$ are each independently selected from the group consisting of hydrogen, halogen, C$_{1-4}$alkyl and C$_{1-4}$alkoxy; provided that at least one of R$^6$ or R$^7$ is hydrogen; or a stereoisomer, isotopologue, isotopomer, or pharmaceutically acceptable salt or solvate thereof.

In certain embodiments, present invention is directed to compounds of formula (I), wherein R$^1$ is selected from the group consisting of halogen, C$_{1-4}$alkyl, fluorinated C$_{1-4}$alkyl, C$_{1-4}$alkoxy, fluorinated C$_{1-4}$alkoxy, cyano, —NR$^A$R$^B$, —C(O)—C$_{1-4}$alkyl, and 5 to 6 membered heterocyclyl;

wherein the 5 to 6 membered heterocyclyl is optionally substituted with one or more substituents independently selected from the group consisting of halogen, cyano, C$_{1-4}$alkyl, fluorinated C$_{1-4}$alkyl, C$_{1-4}$alkoxy, fluorinated C$_{1-4}$alkoxy, and C$_{3-7}$cycloalkyl; and wherein R$^A$ and R$^B$ are each independently selected from the group consisting of hydrogen and C$_{1-4}$alkyl;

a is an integer from 1 to 2;

each R$^2$ is independently selected from the group consisting of chloro and fluoro;

Y is N and Z is C(R$^3$), such that

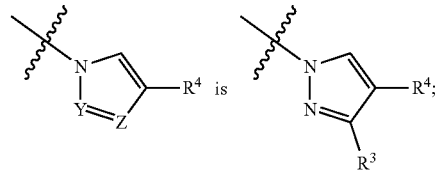

R$^3$ is selected from the group consisting of hydrogen, and methyl;

R$^4$ is 6 membered heterocyclyl; wherein the 6 membered heterocyclyl contains at least one heteroatom selected from the group consisting of N, O and S; optionally contains 1 to 3 additional heteroatoms independently selected from the group consisting of O, N and S; wherein the 6 membered heterocyclyl is saturated, partially unsaturated, or aromatic; wherein the 6 membered heterocyclyl is bound through a carbon atom;

and wherein the 6 membered heterocyclyl is optionally substituted with one to two substituents independently selected from the group consisting of halogen, hydroxy, oxo, C$_{1-4}$alkyl, fluorinated C$_{1-4}$alkyl, C$_{1-4}$alkoxy, fluorinated C$_{1-4}$alkoxy, —C$_{1-2}$alkyl-O—C$_{1-4}$alkyl, C$_{3-7}$cycloalkyl, —C(O)OH, —C(O)—O—C$_{1-4}$alkyl, —C$_{1-2}$alkyl-C(O)—O—C$_{1-4}$ alkyl, cyano, —NR$^G$R$^H$, and —C(O)—NR$^G$R$^H$;

wherein R$^G$ is selected from the group consisting of hydrogen, C$_{1-4}$alkyl, cyclopropyl, 3-hydroxy-cycloprop-1-yl, —C(O)—C$_{1-4}$alkyl, —C(O)-cyclopropyl, —C(O)—O—C$_{1-4}$alkyl and —SO$_2$—C$_{1-4}$alkyl; and R$^H$ is hydrogen and C$_{1-4}$alkyl;

and wherein the 6 membered heterocyclyl contains a nitrogen ring atom, said nitrogen ring atom may be further optionally substituted with oxygen to form an N-oxide;

R$^5$ is selected from the group consisting of (a) C$_{1-4}$alkyl; wherein the C$_{1-4}$alkyl is optionally substituted with one or more halogen; and further optionally substituted with a substituent selected from the group consisting of hydroxy, C$_{1-4}$alkoxy, fluorinated C$_{1-4}$alkoxy, —C(O)OH, —C(O)—O—(C$_{1-4}$alkyl), —C(O)—O-(fluorinated C$_{1-4}$alkyl), —C(O)-(fluorinated C$_{1-4}$alkyl), and —C(O)—NR$^L$R$^M$;

wherein R$^L$ and R$^M$ are each independently selected from the group consisting of hydrogen and C$_{1-2}$alkyl;

(b) —CH$_2$—C$_{3-8}$cycloalkyl or —CH$_2$-adamant-1-yl; wherein the C$_{3-8}$cycloalkyl is optionally substituted with one to two halogen or C$_{1-4}$alkyl; and further optionally substituted with a substituent selected from the group consisting of —C(O)OH, —C(O)—O—C$_{1-4}$ alkyl, —C(O)-(5 to 6 membered saturated heterocyclyl), —C(O)-(isoindolin-2-yl), —C(O)-(azaspiro[2.4] heptan-5-yl), —C(O)-(carboxy substituted azaspiro [2.4]heptan-5-yl), —C(O)—(NR$^P$R$^Q$ substituted azaspiro[2.4]heptan-5-yl), phenyl, 1,1'-biphen-4-yl and —C(O)—NR$^P$R$^Q$;

wherein the —C(O)-(5 to 6 membered saturated heterocyclyl) substituent on the —CH$_2$—C$_{3-8}$cycloalkyl is further optionally substituted on the (5 to 6 membered heterocyclyl) with one to two substituents independently selected from the group consisting of halogen, C$_{1-4}$alkyl, —C(O)OH, —C(O)—O—C$_{1-4}$alkyl, phenyl and C$_{3-8}$cycloalkyl;

wherein the phenyl substituent on the —CH$_2$—C$_{3-8}$cycloalkyl is further optionally substituted with C$_{1-4}$alkoxy;

and wherein $R^P$ and $R^Q$ are each independently selected from the group consisting of hydrogen and $C_{1-4}$alkyl;

(c) -$L^1$-(5 to 6 membered saturated heterocyclyl); wherein $L^1$ is selected from the group consisting of —$CH_2$— and —$CH_2$—C(O)—; wherein, when $L^1$ is —$CH_2$—C(O)—, then the (5 to 6 membered saturated heterocyclyl) is bound to the —C(O)— portion of $L^1$; and wherein the (5 to 6 membered saturated heterocyclyl) is optionally substituted with one to two oxo group;

(d) —$C_{1-2}$alkyl-phenyl; wherein the phenyl is optionally substituted with one to two substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, —$OCH_2$—C(O)—$NR^SR^T$, phenyl and phenoxy; and wherein $R^S$ and $R^T$ are each independently selected from the group consisting of hydrogen and $C_{1-2}$alkyl;

(e) 1,2,3-triazol-4-yl, 1,2,5-triazol-3-yl, —$CH_2$-1,2,3-triazol-4-yl and —$CH_2$-1,2,5-triazol-3-yl; wherein the 1,2,3-triazol-4-yl or 1,2,5-triazoly-3-yl, whether alone or as part of the substituent group is optionally substituted with a substituent selected from the group consisting of $C_{1-4}$alkyl, fluorinated $C_{1-4}$alkyl, phenyl and piperidinyl;

wherein the piperidinyl is optionally substituted with —C(O)—$C_{1-4}$alkyl;

(f) —$CH_2$-(5 to 6 membered or 9 to 10 membered heterocyclyl); wherein the (5 to 6 membered or 9 to 10 membered heterocyclyl) is other than triazolyl;

wherein the (5 to 6 membered or 9 to 10 membered heterocyclyl) is optionally substituted with one to two substituents independently selected from the group consisting of halogen, hydroxy, oxo, $C_{1-4}$alkyl, fluorinated $C_{1-4}$alkyl, $C_{1-4}$alkoxy, fluorinated $C_{1-4}$alkoxy, cyano, —C(O)OH, —C(O)—O—$C_{1-4}$alkyl, —$C_{1-2}$alkyl-O—$C_{1-4}$alkyl, —$C_{1-2}$ alkyl-O-(fluorinated $C_{1-4}$alkyl), —C(O)—$NR^VR^W$, —$C_{1-2}$alkyl-C(O)—$NR^VR^W$, -(5 to 6 membered saturated heterocyclyl), —C(O)-(5 to 6 membered saturated heterocyclyl), —C(O)-(carboxy substituted 5 to 6 membered saturated heterocyclyl), —$C_{1-2}$alkyl-C(O)-(5 to 6 membered saturated heterocyclyl), phenyl and pyridinyl;

wherein the pyridinyl substituent on the —$CH_2$-(5 to 6 membered or 9 to 10 membered heterocyclyl) is further optionally substituted with one to two substituents independently selected from the group consisting of halogen and fluorinated $C_{1-4}$alkyl;

and wherein $R^V$ and $R^W$ are each independently selected from the group consisting of hydrogen and $C_{1-4}$alkyl;

and (g) —$CH_2$—$NR^8R^9$; wherein $R^8$ is selected from the group consisting of hydrogen and $C_{1-2}$alkyl; $R^9$ is selected from the group consisting of $C_{1-4}$alkyl, fluorinated $C_{1-4}$alkyl, $C_{1-4}$alkoxy, fluorinated $C_{1-4}$alkoxy, —C(O)—$C_{1-4}$alkyl, —C(O)—$C_{1-2}$alkyl-O—$C_{1-4}$alkyl, —C(O)-phenyl, —C(O)—$C_{1-2}$alkyl-phenyl, —C(O)—O—$C_{1-4}$alkyl, —C(O)—O-phenyl, —C(O)—O—$C_{1-2}$alkyl-phenyl, —C(O)—$C_{3-7}$cycloalkyl, —C(O)-(1-methyl-cycloprop-1-yl), —C(O)-(5 to 6 membered saturated heterocyclyl), —C(O)—$C_{1-2}$alkyl-C(O)-(5 to 6 membered saturated heterocyclyl), —O—$C_{1-2}$alkyl-C(O)-(5 to 6 membered saturated heterocyclyl), —C(O)-(1-methyl-pyridinyl-one) and —C(O)—$NR^XR^Y$; and wherein $R^X$ and $R^Y$ are each independently selected from the group consisting of hydrogen and $C_{1-2}$alkyl;

$R^6$ and $R^7$ are each independently selected from the group consisting of hydrogen, halogen, $C_{1-4}$alkyl and $C_{1-4}$alkoxy; provided that at least one of $R^6$ or $R^7$ is hydrogen;

or a stereoisomer, isotopologue, isotopomer, or pharmaceutically acceptable salt or solvate thereof.

In certain embodiments, present invention is directed to compounds of formula (I), wherein $R^1$ is 5 to 6 membered heterocyclyl; wherein the 5 to 6 membered heterocyclyl is optionally substituted with a substituent selected from the group consisting of halogen, $C_{1-4}$alkyl, fluorinated $C_{1-4}$alkyl, and $C_{3-6}$cycloalkyl;

a is an integer from 1 to 2;

each $R^2$ is independently selected from the group consisting of chloro and fluoro;

Y is N and Z is $C(R^3)$, such that

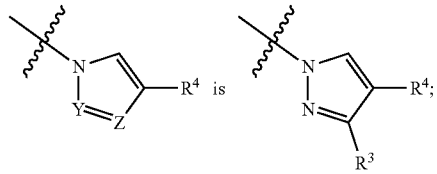

$R^3$ is selected from the group consisting of hydrogen and methyl;

$R^4$ is 6 membered heterocyclyl; wherein the 6 membered heterocyclyl contains at least one heteroatom selected from the group consisting of N, O and S; optionally contains 1 to 3 additional heteroatoms independently selected from the group consisting of O, N and S; wherein the 6 membered heterocyclyl is saturated, partially unsaturated, or aromatic; wherein the 6 membered heterocyclyl is bound through a carbon atom;

and wherein the 6 membered heterocyclyl is optionally substituted with one to two substituents independently selected from the group consisting of halogen, oxo, $C_{1-4}$alkyl, fluorinated $C_{1-4}$alkyl, $C_{1-4}$alkoxy, fluorinated $C_{1-4}$ alkoxy, —$C_{1-2}$alkyl-O—$C_{1-4}$alkyl, $C_{3-7}$cycloalkyl, —C(O)OH, —C(O)—O—$C_{1-4}$alkyl, cyano and —$NR^G R^H$; wherein $R^G$ is selected from the group consisting of hydrogen, $C_{1-4}$alkyl, —C(O)—$C_{1-4}$alkyl and —C(O)-cyclopropyl; and $R^H$ is selected from the group consisting of hydrogen and $C_{1-4}$alkyl;

and wherein the 6 membered heterocyclyl contains a nitrogen ring atom, said nitrogen ring atom may be further optionally substituted with oxygen to form an N-oxide;

$R^5$ is selected from the group consisting of (a) $C_{1-4}$alkyl; wherein the $C_{1-4}$alkyl is optionally substituted with a substituent selected from the group consisting of $C_{1-4}$alkoxy, fluorinated $C_{1-4}$alkoxy, —C(O)—O—($C_{1-4}$alkyl) and —C(O)-(fluorinated $C_{1-4}$alkyl);

(b) —$CH_2$—$C_{3-8}$cycloalkyl or —$CH_2$-adamant-1-yl; wherein the $C_{3-8}$cycloalkyl is optionally substituted with one or more halogen; and further optionally substituted with a substituent selected from the group consisting of —C(O)-(5 to 6 membered saturated heterocyclyl), —C(O)-(azaspiro[2.4]heptan-5-yl), —C(O)-(carboxy substituted azaspiro[2.4]heptan-5-yl), —C(O)—($NR^PR^Q$ substituted azaspiro[2.4]heptan-5-yl), and —C(O)—$NR^PR^Q$;

wherein the —C(O)-(5 to 6 membered saturated heterocyclyl) substituent on the —$CH_2$—$C_{3-8}$cycloalkyl is further optionally substituted on the (5 to 6 membered heterocyclyl) with a substituent selected from the group consisting of phenyl and $C_{3-8}$cycloalkyl;
and wherein $R^P$ and $R^Q$ are each independently selected from the group consisting of hydrogen and $C_{1-4}$alkyl;
(c) -$L^1$-(5 to 6 membered saturated heterocyclyl); wherein $L^1$ is —$CH_2$—; and wherein the 5 to 6 membered saturated heterocyclyl is optionally substituted with one to two oxo group;
(d) —$C_{1-2}$alkyl-phenyl; wherein the phenyl is optionally substituted with a substituent selected from the group consisting of halogen and $C_{1-4}$alkoxy;
(e) 1,2,3-triazol-4-yl, 1,2,5-triazoly-3-yl, —$CH_2$-1,2,3-triazol-4-yl and —$CH_2$-1,2,5-triazol-3-yl; wherein the 1,2,3-triazol-4-yl or 1,2,5-triazoly-3-yl, whether alone or as part of the substituent group is optionally substituted with a substituent selected from the group consisting of $C_{1-4}$alkyl, fluorinated $C_{1-4}$alkyl and phenyl;
(f) —$CH_2$-(5 to 6 membered or 9 to 10 membered heterocyclyl); wherein the 5 to 6 membered heterocyclyl is other than triazolyl;
wherein the (5 to 6 membered or 9 to 10 membered heterocyclyl) is optionally substituted with one to two substituents independently selected from the group consisting of halogen, oxo, $C_{1-4}$alkyl, fluorinated $C_{1-4}$alkyl, fluorinated $C_{1-4}$alkoxy, —C(O)OH, —$C_{1-2}$alkyl-O—$C_{1-4}$alkyl, —$C_{1-2}$alkyl-O-(fluorinated $C_{1-4}$alkyl), —C(O)—$NR^V R^W$, —$C_{1-2}$ alkyl-C(O)—$NR^V R^W$, -(5 to 6 membered saturated heterocyclyl), —C(O)-(5 to 6 membered saturated heterocyclyl), —C(O)-(carboxy substituted 5 to 6 membered saturated heterocyclyl), —$C_{1-2}$alkyl-C(O)-(5 to 6 membered saturated heterocyclyl), phenyl and pyridinyl;
wherein the pyridinyl substituent on the —$CH_2$-(5 to 6 membered or 9 to 10 membered heterocyclyl) is further optionally substituted halogen;
and wherein $R^V$ and $R^W$ are each independently selected from the group consisting of hydrogen and $C_{1-4}$alkyl;
and (g) —$CH_2$—$NR^8 R^9$; wherein $R^8$ is selected from the group consisting of hydrogen and $C_{1-2}$alkyl; $R^9$ is selected from the group consisting of fluorinated $C_{1-4}$alkoxy, —C(O)—$C_{1-4}$alkyl, —C(O)—$C_{1-2}$alkyl-O—$C_{1-4}$alkyl, —C(O)— phenyl, —C(O)—$C_{1-2}$alkyl-phenyl, —C(O)—O—$C_{1-4}$alkyl, —C(O)—O—$C_{1-2}$alkyl-phenyl, —C(O)—$C_{3-7}$cycloalkyl, —C(O)-(1-methyl-cycloprop-1-yl), —C(O)-(5 to 6 membered saturated heterocyclyl), —C(O)—$C_{1-2}$alkyl-C(O)-(5 to 6 membered saturated heterocyclyl), —O—$C_{1-2}$alkyl-C(O)-(5 to 6 membered saturated heterocyclyl), —C(O)-(1-methyl-pyridinyl-one) and —C(O)—$NR^X R^Y$; and wherein $R^X$ and $R^Y$ are each independently selected from the group consisting of hydrogen and $C_{1-2}$alkyl;
$R^6$ is selected from the group consisting of hydrogen and halogen;
$R^7$ is selected from the group consisting of hydrogen, halogen, $C_{1-2}$alkyl and $C_{1-4}$alkoxy;
provided that at least one of $R^6$ or $R^7$ is hydrogen;
or a stereoisomer, isotopologue, isotopomer, or pharmaceutically acceptable salt or solvate thereof.
In certain embodiments, present invention is directed to compounds of formula (I), wherein $R^1$ is selected from the group consisting of 4-chloro-1,2,3-triazol-1-yl, 4-(trifluoro-methyl)-1,2,3-triazol-1-yl, 4-cyclopropyl-1,2,3-triazol-1-yl, oxazol-5-yl, and 1,2,3,4-tetrazol-1-yl;
a is an integer from 1 to 2;

each $R^2$ is independently selected from the group consisting of 5-chloro and 6-fluoro;
Y is N and Z is C($R^3$), such that

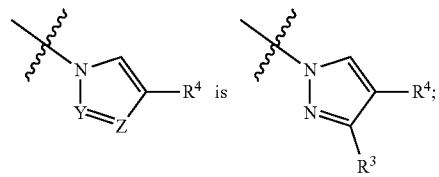

$R^3$ is selected from the group consisting of hydrogen and methyl;
$R^4$ is selected from the group consisting of 1-(methoxy-carbonyl)-piperidin-4-yl, 1-(methoxy-carbonyl)-piperidin-3-yl, 2-fluoro-6-amino-pyrazin-3-yl, pyridazin-4-yl, 1-ethyl-pyridazin-4-yl-6-one, 1-methyl-pyridazin-4-yl-6-one, 1-isopropyl-pyridazin-4-yl-6-one, 1-(2-isopropyloxy-ethyl)-pyridazin-4-yl-6-one, pyridazin-4-yl-1-oxide, pyridin-2-yl, 6-fluoro-pyridin-3-yl, 6-amino-pyridin-3-yl, 2-chloro-6-amino-pyridin-3-yl, 2-fluoro-6-amino-pyridin-3-yl, 2-methyl-6-amino-pyridin-3-yl, 5-fluoro-6-amino-pyridin-3-yl, 4-fluoro-6-amino-pyridin-3-yl, 2-fluoro-5-methoxy-pyridin-3-yl, 2-fluoro-4-(cyclopropyl-carbonyl-amino)-pyridin-3-yl, pyridin-4-yl, 2-fluoro-pyridin-4-yl, 3-fluoro-pyridin-4-yl, 2-methyl-pyridin-4-yl, 2-isopropyl-pyridin-4-yl, 2-t-butyl-pyridin-4-yl, 2-(trifluoro-methyl)-pyridin-4-yl, 2-cyano-pyridin-4-yl, 2-cyclopropyl-pyridin-4-yl, 2-(difluoro-methoxy)-pyridin-4-yl, 2-(difluoro-methyl)-pyridin-4-yl, 3-(trifluoro-methyl-pyridin-4-yl), 3-(trifluoro-methyl)-pyridin-4-yl, 3-fluoro-5-chloro-pyridin-4-yl, 2-(trifluoro-methyl)-5-(methyl-carbonyl-amino)-pyridin-4-yl, 1-methyl-pyridin-3-yl-6-one, 1-methyl-pyridin-4-yl-2-one, pyridin-3-yl-1-oxide, 6-amino-pyridin-3-yl-1-oxide, 2-methyl-6-amino-pyridin-3-yl-1-oxide, pyridin-4-yl-1-oxide, 3-fluoro-pyridin-4-yl-1-oxide, 2-(difluoro-methyl)-pyridin-4-yl-1-oxide, 2-methyl-pyridin-4-yl-1-oxide, 2-isopropyl-pyridin-4-yl-1-oxide, 2-t-butyl-pyridin-4-yl-1-oxide, 2-(trifluoro-methyl)-pyridin-4-yl-1-oxide, 2-cyano-pyridin-4-yl-1-oxide, 2,6-dimethyl-pyridin-4-yl-1-oxide, 3-fluoro-5-chloro-pyridin-4-yl-1-oxide, 3-chloro-5-fluoro-pyridin-4-yl-1-oxide, pyrimidin-4-yl, 2-methyl-pyrimidin-4-yl, pyrimidin-5-yl, 2-(trifluoro-methyl)-pyrimidin-4-yl, 6-(trifluoro-methyl)-pyrimidin-4-yl, 2-(methyl-amino)-pyrimidin-5-yl, pyrimidin-4-yl-1-oxide, and 2-methyl-pyrimidin-4-yl-1-oxide;
$R^5$ is selected from the group consisting of
(a) R*-ethyl, S*-ethyl, 2-methoxy-ethyl-, 2-(difluoro-methoxy)-ethyl-, R-(2-(difluoro-methoxy)-ethyl-), R*-(2-(difluoro-methoxy)-ethyl-), S*-(2-(difluoro-methoxy)-ethyl-), S-(2-(difluoro-methoxy)-ethyl-), 2-(difluoro-methyl-carbonyl)-methyl-, 2-trifluoro-methoxy-ethyl-, R*-(2-(methoxy-d3)-ethyl-), S*-(2-(methoxy-d3)-ethyl-), S*-(2-(difluoro-methoxy)-ethyl-2,2-$d_2$-), and R*-(2-(difluoro-methoxy)-ethyl-2,2-d2-);
(b) cyclopropyl-methyl-, S*-(cyclopropyl-methyl-), R*-(cyclopropyl-methyl-), R-(cyclopropyl-methyl-), S-(cyclopropyl-methyl-), 2-(amino-carbonyl)-cyclopropyl-methyl-, 2S*-(amino-carbonyl)-1S*-cyclopropyl-methyl-, 2R*-(amino-carbonyl)-1S*-cyclopropyl-methyl-, R*-(2S*-(amino-carbonyl)-1S*-cyclopropyl-methyl-), R*-(2S*-(amino-carbonyl)-1R*- cyclopropyl-methyl-), S*-(2R*-(amino-carbonyl)-1R*-cyclopropyl-methyl-), S*-(2R*-(amino-carbonyl)-1S*-cyclopropyl-methyl-), S*-(2S*-(amino-carbonyl)-1R*-cyclopropyl-methyl-), R*-(2R*-(amino-carbonyl)-1S*-cyclopropyl-methyl-), 2R*-(piperidin-1-yl-carbonyl)-1S*-cyclopropyl-methyl-, 2S*-(piperidin-1-yl-carbonyl)-1S*-cyclopropyl-methyl-, 2-(piperidin-1-yl-carbonyl)-cyclopropyl-methyl-, 2R*-(pyrrolidin-1-yl-carbonyl)-1S*-cyclopropyl-methyl-, 2S*-(pyrrolidin-1-yl-carbonyl)-1S*-cyclopropyl-methyl-, 2-(3-phenyl-pyrrolidin-1-yl-carbonyl)-cyclopropyl-methyl-, 2-(3-cyclopropyl-pyrrolidin-1-yl-carbonyl)-cyclopropyl-methyl-, 2-(7-amino-azaspiro[2.4]heptan-5-yl-carbonyl)-cyclopropyl-methyl-, 2-(7-carboxy-azaspiro[2.4]heptan-5-yl-carbonyl)-cyclopropyl-methyl-, and 2-(azaspiro[2.4]heptan-5-yl-carbonyl)-cyclopropyl-methyl-;
(c) tetrahydrofuran-2-yl-methyl-, R*-(pyrrolidin-1-yl-2-one-methyl-), R-(pyrrolidin-1-yl-2-one-methyl-), S*-(pyrrolidin-1-yl-2-one-methyl-), (pyrrolidin-1-yl-2-one)-methyl-, and (pyrrolidin-1yl-2,5-dione)-methyl-;
(d) phenyl-methyl-, 4-chloro-phenyl-methyl-, 4-fluoro-phenyl-methyl-, R*-(4-fluoro-phenyl-methyl-), S*-(4-fluoro-phenyl-methyl-), and 4-methoxy-phenyl-methyl-;
(e) 1-methyl-1,2,3-triazol-4-yl-methyl-, R-(1-methyl-1,2,3-triazol-4-yl-methyl), S-(1-methyl-1,2,3-triazol-4-yl-methyl), S-(1-(difluoro-methyl)-1,2,3-triazol-4-yl-methyl-), R-(1-(difluoro-methyl)-1,2,3-triazol-4-yl-methyl-), 1-methyl-1,2,5-triazol-3-yl-methyl-, 1-phenyl-1,2,5-triazol-3-yl-methyl-, R-(1-methyl-1,2,5-triazol-3-yl-methyl-), S-(1-methyl-1,2,5-triazol-3-yl-methyl-), S-(1-(difluoro-methyl)-1,2,5-triazol-3-yl-methyl-), and R-(1-(difluoro-methyl)-1,2,5-triazol-3-yl-methyl-);
(f) pyrazol-1-yl-methyl-, R*-(pyrazol-1-yl-methyl-), S*-(pyrazol-1-yl-methyl-), 4-fluoro-pyrazol-1-yl-methyl-, R*-(4-fluoro-pyrazol-1-yl-methyl-), S*-(4-fluoro-pyrazol-1-yl-methyl-), 1-methyl-pyrazol-3-yl-methyl-, 1-methyl-pyrazol-4-yl-methyl-, R-(1-methyl-pyrazol-3-yl-methyl-), S*-(1-methyl-pyrazol-3-yl-methyl-), S-(1-isopropyl-pyrazol-3-yl-methyl-), R-(1-isopropyl-pyrazol-3-yl-methyl-), 1-(difluoro-methyl)-pyrazol-3-yl-methyl-, S-(1-(difluoro-methyl)-pyrazol-1-yl-methyl-), R-(1-(difluoro-methyl)-pyrazol-1-yl-methyl-), R-(3-(difluoro-methoxy)-pyrazol-1-yl-methyl-), S-(3-(difluoro-methoxy)-pyrazol-1-yl)-methyl-), 3-(trifluoro-methyl)-pyrazol-1-yl-methyl-, 5-(trifluoro-methyl)-pyrazol-1-yl-methyl-, 4-(trifluoro-methyl)-pyrazol-1-yl-methyl-, S-(1-(2,2,2-trifluoro-ethyl)-pyrazol-1-yl-methyl-), R-(1-(2,2,2-trifluoro-ethyl)-pyrazol-1-yl-methyl-), 1-(2,2,2-trifluoroethyl)-4-fluoro-pyrazol-3-yl-methyl-, R*-(3-(methoxy-methyl)-pyrazol-1-yl-methyl-), S*-(3-(methoxy-methyl)-pyrazol-1-yl-methyl-), 3-(methoxy-methyl)-pyrazol-1-yl-methyl-, 5-(methoxy-methyl)-pyrazol-1-yl-methyl-, S*-(3-(difluoro-methoxy-methyl)-4-fluoro-pyrazol-1-yl-methyl-), R*-(3-(difluoro-methoxy-methyl)-4-fluoro-pyrazol-1-yl-methyl-), 3-carboxy-pyrazol-1-yl-methyl-, 3-(amino-carbonyl)-pyrazol-1-yl-methyl-, 4-(amino-carbonyl)-pyrazol-1-yl-methyl-, 3-(amino-carbonyl-methyl)-pyrazol-1-yl-methyl-, 5-(amino-carbonyl-methyl)-pyrazol-1-yl-methyl-, R*-(3-(amino-carbonyl)-pyrazol-1-yl-methyl-), R*-(3-(di-methyl-amino-carbonyl)-pyrazol-1-yl-methyl-), 4-(piperidin-1-yl-carbonyl)-pyrazol-1-yl-methyl-, R*-(4-(piperidin-1-yl-carbonyl)-pyrazol-1-yl-methyl-), S*-(4-(piperidin-1-yl-carbonyl)-pyrazol-1-yl-methyl-), 3-(piperidin-1-yl-carbonyl)-pyrazol-1-yl-methyl-, R*-(3-(piperidin-1-yl-carbonyl)-pyrazol-1-yl-methyl-), S*-(3-(piperidin-1-yl-carbonyl)-pyrazol-1-yl-methyl-, 4-(piperidin-1-yl-carbonyl-methyl)-pyrazol-1-yl-methyl-, 3-(4-carboxy-piperidin-1-yl-carbonyl)-pyrazol-1-yl-methyl-, 3-(tetrahydropyran-4-yl)-pyrazol-1-yl-methyl-, R*-(4-(pyridin-2-yl)-pyrazol-1-yl-methyl-), S*-(4-(pyridin-2-yl)-pyrazol-1-yl-methyl-), R*-((5-fluoro-pyridin-1-yl)-pyrazol-1-yl-methyl-), S*-((5-fluoro-pyridin-1-yl)-pyrazol-1-yl-methyl-), 3-phenyl-pyrazol-1-yl-methyl-, R-((3-methyl-imidazolidin-1-yl-2-one)-methyl-), S*-((3-methyl-imidazolidin-1-yl-2-one)-methyl-), (isoindolin-2-yl-1-one)-methyl-, R*-((oxazolidin-3-yl-2-one)-methyl-), S*-((oxazolidin-3-yl-2-one)-methyl-), (pyridin-1-yl-2-one)-methyl-, S*-(pyridin-1-yl-2-one)-methyl-), R*-(pyridin-1-yl-2-one)-methyl-), and 2,4,5,7-tetrahydropyrano[3,4-c]pyrazol-2-yl-methyl-;
and (g) (methoxy-carbonyl)-amino-methyl-, (cyclopropyl-carbonyl)-amino-methyl-, (1-methyl-cycloprop-1-yl-carbonyl)-amino-methyl-, (t-butoxy-carbonyl)-amino-methyl-, N-methyl-N-(methyl-carbonyl)-amino-methyl-, R*—(N-methyl-N-(methyl-carbonyl)-amino-methyl-), S*—(N-methyl-N-(methyl-carbonyl)-amino-methyl-), N-methyl-N-(isopropyl-carbonyl)-amino-methyl-, R*—(N-methyl-N-(isopropyl-carbonyl)-amino-methyl-), S*—(N-methyl-N-(isopropyl-carbonyl)-amino-methyl-), S*—(N-methyl-N-(t-butyl-carbonyl)-amino-methyl-), R*—(N-methyl-N-(t-butyl-carbonyl)-amino-methyl-), N-methyl-N-(t-butyl-carbonyl)-amino-methyl-, N-methyl-N-(methoxy-carbonyl)-amino-methyl-, R*—(N-methyl-N-(methoxy-carbonyl)-amino-methyl-), S*—(N-methyl-N-(methoxy-carbonyl)-amino-methyl-), R*—(N-methyl-N-(t-butoxy-carbonyl)-amino-methyl-), S*—(N-methyl-N-(t-butoxy-carbonyl)-amino-methyl-), N-methyl-N-(trifluoro-methoxy)-amino-methyl-, N-methyl-N-(methoxy-methyl-carbonyl)-amino-methyl-, N-methyl-N-(dimethyl-amino-carbonyl)-amino-methyl-, R*—(N-methyl-N-cyclopropyl-carbonyl)-amino-methyl-), S*—(N-methyl-N-(cyclopropyl-carbonyl)-amino-methyl-), N-methyl-N-(phenyl-carbonyl)-amino-methyl-, R*—(N-methyl-N-(phenyl-carbonyl)-amino-methyl-), S*—(N-methyl-N-(phenyl-carbonyl)-amino-methyl-), N-methyl-N-(benzyl-carbonyl)-amino-methyl-, N-methyl-N-(phenyl-ethyl-carbonyl)-amino-methyl-, S*—(N-methyl-N-(phenyl-ethyl-carbonyl)-amino-methyl-), R*—(N-methyl-N-(phenyl-ethyl-carbonyl)-amino-methyl-), R*—(N-methyl-N-(benzyloxy-carbonyl)-amino-methyl-), S*—(N-methyl-N-(benzyloxy-carbonyl)-amino-methyl-), N-methyl-N-(tetrahydropyran-4-yl-carbonyl)-amino-methyl-, N-methyl-N-(2-(piperidin-1-yl-carbonyl)-ethoxy))-amino-ethyl-, N-methyl-N-(piperidin-1-yl-carbonyl-methyl-carbonyl)-amino-methyl-, R*—(N-methyl-N-(2-(piperidin-1-yl-carbonyl)-ethyl-carbonyl)-amino-methyl-), S*—(N-methyl-N-(2-(piperidin-1-yl-carbonyl)-ethyl-carbonyl)-amino-methyl-), S*—(N-methyl-N-(1-methyl-pyridin-4-yl-2-one-carbonyl)-amino-methyl-), and R*—(N-methyl-N-(1-methyl-pyridin-4-yl-2-one-carbonyl)-amino-methyl-);
$R^6$ is selected from the group consisting of hydrogen and fluoro;

R⁷ is selected from the group consisting of hydrogen, chloro, methyl, methoxy, ethoxy and isopropyloxy;
provided that at least one of R⁶ or R⁷ is hydrogen;
or a pharmaceutically acceptable salt thereof.

In certain embodiments, present invention is directed to compounds of formula (I), wherein R¹ is selected from the group consisting of 4-chloro-1,2,3-triazol-1-yl, 4-(trifluoromethyl)-1,2,3-triazol-1-yl, oxazol-5-yl, and 1,2,3,4-tetrazol-1-yl;
a is an integer from 1 to 2;
each R² is independently selected from the group consisting of 5-chloro and 6-fluoro;
Y is N and Z is C(R³), such that

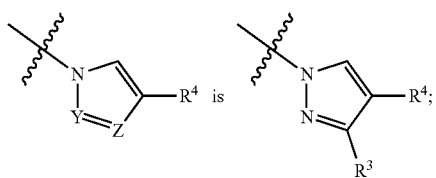

R³ is hydrogen;
R⁴ is selected from the group consisting of 1-(methoxy-carbonyl)-piperidin-4-yl, 1-(methoxy-carbonyl)-piperidin-3-yl, 2-fluoro-6-amino-pyrazin-3-yl, pyridazin-4-yl, 1-ethyl-pyridazin-4-yl-6-one, 1-methyl-pyridazin-4-yl-6-one, 1-isopropyl-pyridazin-4-yl-6-one pyridazin-4-yl-1-oxide, 6-fluoro-pyridin-3-yl, 6-amino-pyridin-3-yl, 2-chloro-6-amino-pyridin-3-yl, 2-fluoro-6-amino-pyridin-3-yl, 2-methyl-6-amino-pyridin-3-yl, 5-fluoro-6-amino-pyridin-3-yl, 2-fluoro-5-methoxy-pyridin-3-yl, pyridin-4-yl, 2-fluoro-pyridin-4-yl, 3-fluoro-pyridin-4-yl, 2-methyl-pyridin-4-yl, 2-isopropyl-pyridin-4-yl, 2-t-butyl-pyridin-4-yl, 2-(difluoro-methyl)-pyridin-4-yl, 2-(trifluoro-methyl)-pyridin-4-yl, 2-cyano-pyridin-4-yl, 2-cyclopropyl-pyridin-4-yl, 2-(difluoro-methoxy)-pyridin-4-yl, 2-(difluoro-methyl)-pyridin-4-yl, 3-(trifluoro-methyl)-pyridin-4-yl, 3-fluoro-5-chloro-pyridin-4-yl, 2-(trifluoro-methyl)-5-(methyl-carbonyl-amino)-pyridin-4-yl, 1-methyl-pyridin-3-yl-6-one, 1-methyl-pyridin-4-yl-2-one, pyridin-3-yl-1-oxide, 6-amino-pyridin-3-yl-1-oxide, 2-methyl-6-amino-pyridin-3-yl-1-oxide, pyridin-4-yl-1-oxide, 3-fluoro-pyridin-4-yl-1-oxide, 2-(difluoro-methyl)-pyridin-4-yl-1-oxide, 2-methyl-pyridin-4-yl-1-oxide, 2-isopropyl-pyridin-4-yl-1-oxide, 2-t-butyl-pyridin-4-yl-1-oxide, 2-(trifluoro-methyl)-pyridin-4-yl-1-oxide, 2-cyano-pyridin-4-yl-1-oxide, 2,6-dimethyl-pyridin-4-yl-1-oxide, 3-fluoro-5-chloro-pyridin-4-yl-1-oxide, 3-chloro-5-fluoro-pyridin-4-yl-1-oxide, pyrimidin-4-yl, 2-methyl-pyrimidin-4-yl, pyrimidin-5-yl, 2-(trifluoro-methyl)-pyrimidin-4-yl, 6-(trifluoro-methyl)-pyrimidin-4-yl, 2-(methyl-amino)-pyrimidin-5-yl, pyrimidin-4-yl-1-oxide, and 2-methyl-pyrimidin-4-yl-1-oxide;
R⁵ is selected from the group consisting of
(a) S*-ethyl, 2-methoxy-ethyl-, 2-(difluoro-methoxy)-ethyl-, R-(2-(difluoro-methoxy)-ethyl-), R*-(2-(difluoro-methoxy)-ethyl-), S*-(2-(difluoro-methoxy)-ethyl-), 2-(difluoro-methyl-carbonyl)-methyl-, 2-trifluoro-methoxy-ethyl-, R*-(2-(methoxy-d)ethyl-), and R*-(2-(difluoro-methoxy)-ethyl-2,2-d2-);
(b) cyclopropyl-methyl-, S*-(cyclopropyl-methyl-), R*-(cyclopropyl-methyl-), R-(cyclopropyl-methyl-), 2-(amino-carbonyl)-cyclopropyl-methyl-, 2S*-(amino-carbonyl)-1S*-cyclopropyl-methyl-, 2R*-(amino-carbonyl)-1S*-cyclopropyl-methyl-, R*-(2S*-(amino-carbonyl)-1S*-cyclopropyl-methyl-), S*-(2R*-(amino-carbonyl)-1R*-cyclopropyl-methyl-), S*-(2R*-(amino-carbonyl)-1S*-cyclopropyl-methyl-), S*-(2S*-(amino-carbonyl)-1R*-cyclopropyl-methyl-), R*-(2R*-(amino-carbonyl)-1S*-cyclopropyl-methyl-), 2R*-(piperidin-1-yl-carbonyl)-1S*-cyclopropyl-methyl-, 2-(piperidin-1-yl-carbonyl)-cyclopropyl-methyl-, 2R*-(pyrrolidin-1-yl-carbonyl)-1S*-cyclopropyl-methyl-, 2S*-(pyrrolidin-1-yl-carbonyl)-1S*-cyclopropyl-methyl-, 2-(3-phenyl-pyrrolidin-1-yl-carbonyl)-cyclopropyl-methyl-, 2-(3-cyclopropyl-pyrrolidin-1-yl-carbonyl)-cyclopropyl-methyl-, 2-(7-amino-azaspiro [2.4]heptan-5-yl-carbonyl)-cyclopropyl-methyl-, 2-(7-carboxy-azaspiro [2.4] heptan-5-yl-carbonyl)-cyclopropyl-methyl-, and 2-(azaspiro[2.4] heptan-5-yl-carbonyl)-cyclopropyl-methyl-;
(c) R*-(pyrrolidin-1-yl-2-one-methyl-), R-(pyrrolidin-1-yl-2-one-methyl-), S*-(pyrrolidin-1-yl-2-one-methyl-), (pyrrolidin-1-yl-2-one)-methyl-, and (pyrrolidin-1yl-2,5-dione)-methyl-;
(d) phenyl-methyl-, 4-chloro-phenyl-methyl-, 4-fluoro-phenyl-methyl-, R*-(4-fluoro-phenyl-methyl-), S*-(4-fluoro-phenyl-methyl-), and 4-methoxy-phenyl-methyl-;
(e) 1-methyl-1,2,3-triazol-4-yl-methyl-, R-(1-methyl-1,2,3-triazol-4-yl-methyl), R-(1-(difluoro-methyl)-1,2,3-triazol-4-yl-methyl-), 1-methyl-1,2,5-triazol-3-yl-methyl-, 1-phenyl-1,2,5-triazol-3-yl-methyl-, R-(1-methyl-1,2,5-triazol-3-yl-methyl-), and R-(1-(difluoro-methyl)-1,2,5-triazol-3-yl-methyl-);
(f) pyrazol-1-yl-methyl-, R*-(pyrazol-1-yl-methyl-), S*-(pyrazol-1-yl-methyl-), 4-fluoro-pyrazol-1-yl-methyl-, R*-(4-fluoro-pyrazol-1-yl-methyl-), S*-(4-fluoro-pyrazol-1-yl-methyl-), 1-methyl-pyrazol-3-yl-methyl-, 1-methyl-pyrazol-4-yl-methyl-, R-(1-methyl-pyrazol-3-yl-methyl-), S*-(1-methyl-pyrazol-3-yl-methyl-), R-(1-isopropyl-pyrazol-3-yl-methyl-), 1-(difluoro-methyl)-pyrazol-3-yl-methyl-, R-(1-(difluoro-methyl)-pyrazol-1-yl-methyl-), R-(3-(difluoro-methoxy)-pyrazol-1-yl-methyl-), S-(3-(difluoro-methoxy)-pyrazol-1-yl)-methyl-), 3-(trifluoro-methyl)-pyrazol-1-yl-methyl-, 5-(trifluoro-methyl)-pyrazol-1-yl-methyl-, 4-(trifluoro-methyl)-pyrazol-1-yl-methyl-, R-(1-(2,2,2-trifluoroethyl)-pyrazol-1-yl-methyl-), 1-(2,2,2-trifluoroethyl)-4-fluoro-pyrazol-3-yl-methyl-, R*-(3-(methoxy-methyl)-pyrazol-1-yl-methyl-), S*-(3-(methoxy-methyl)-pyrazol-1-yl-methyl-), 3-(methoxy-methyl)-pyrazol-1-yl-methyl-, 5-(methoxy-methyl)-pyrazol-1-yl-methyl-, S*-(3-(difluoro-methoxy-methyl)-4-fluoro-pyrazol-1-yl-methyl-), R*-(3-(difluoro-methoxy-methyl)-4-fluoro-pyrazol-1-yl-methyl-), 3-carboxy-pyrazol-1-yl-methyl-, 3-(amino-carbonyl)-pyrazol-1-yl-methyl-, 4-(amino-carbonyl)-pyrazol-1-yl-methyl-, 3-(amino-carbonyl-methyl)-pyrazol-1-yl-methyl-, 5-(amino-carbonyl-methyl)-pyrazol-1-yl-methyl-, R*-(3-(amino-carbonyl)-pyrazol-1-yl-methyl-), R*-(3-(dimethyl-amino-carbonyl)-pyrazol-1-yl-methyl-, 4-(piperidin-1-yl-carbonyl)-pyrazol-1-yl-methyl-, R*-(4-(piperidin-1-yl-carbonyl)-pyrazol-1-yl-methyl-), S*-(4-(piperidin-1-yl-carbonyl)-pyrazol-1-yl-methyl-), 3-(piperidin-1-yl-carbonyl)-pyrazol-1-yl-methyl-, R*-(3-(piperidin-1-yl-carbonyl)-pyrazol-1-yl-methyl-), 4-(piperidin-1-yl-carbonyl-methyl)-pyrazol-1-yl-methyl-, 3-(4-carboxypiperidin-1-yl-carbonyl)-pyrazol-1-yl-methyl-, 3-(tetrahydropyran-4-yl)-pyrazol-1-yl-methyl-, R-((3-methyl-imidazolidin-1-yl-2-one)-methyl-), (isoindolin-2-yl-1-one)-methyl-, R*-((oxazolidin-3-yl-2-one)-methyl-), S*-((oxazolidin-3-yl-2-one)-methyl-), (pyridin-1-yl-2-one)-methyl-, R*-(pyridin-1-yl-2-one)-methyl-), and 2,4,5,7-tetrahydropyrano[3,4-c]pyrazol-2-yl-methyl-;

and (g) (1-methyl-cycloprop-1-yl-carbonyl)-amino-methyl-, N-methyl-N-(methyl-carbonyl)-amino-methyl-, S*—(N-methyl-N-(methyl-carbonyl)-amino-methyl-), N-methyl-N-(isopropyl-carbonyl)-amino-methyl-, S*—(N-methyl-N-(isopropyl-carbonyl)-amino-methyl-), R*—(N-methyl-N-(t-butyl-carbonyl)-amino-methyl-), N-methyl-N-(t-butyl-carbonyl)-amino-methyl-, N-methyl-N-(methoxy-carbonyl)-amino-methyl-, S*—(N-methyl-N-(methoxy-carbonyl)-amino-methyl-), S*—(N-methyl-N-(t-butoxy-carbonyl)-amino-methyl-), N-methyl-N-(trifluoro-methoxy)-amino-methyl-, N-methyl-N-(methoxy-methyl-carbonyl)-amino-methyl-, N-methyl-N-(dimethyl-amino-carbonyl)-amino-methyl-, S*—(N-methyl-N-(cyclopropyl-carbonyl)-amino-methyl-), N-methyl-N-(phenyl-carbonyl)-amino-methyl-, R*—(N-methyl-N-(phenyl-carbonyl)-amino-methyl-), N-methyl-N-(benzyl-carbonyl)-amino-methyl-, N-methyl-N-(phenyl-ethyl-carbonyl)-amino-methyl-, S*—(N-methyl-N-(phenyl-ethyl-carbonyl)-amino-methyl-), R*—(N-methyl-N-(benzyloxy-carbonyl)-amino-methyl-), N-methyl-N-(tetrahydropyran-4-yl-carbonyl)-amino-methyl-, N-methyl-N-(2-(piperidin-1-yl-carbonyl)-ethoxy))-amino-ethyl-, N-methyl-N-(piperidin-1-yl-carbonyl-methyl-carbonyl)-amino-methyl-, S*—(N-methyl-N-(2-(piperidin-1-yl-carbonyl)-ethyl-carbonyl)-amino-methyl-), and R*—(N-methyl-N-(1-methyl-pyridin-4-yl-2-one-carbonyl)-amino-methyl-);

$R^6$ is hydrogen;
$R^7$ is selected from the group consisting of hydrogen, chloro, methyl, methoxy, ethoxy and isopropyloxy; or a pharmaceutically acceptable salt thereof.

In certain embodiments, present invention is directed to compounds of formula (I), wherein $R^1$ is selected from the group consisting of 4-chloro-1,2,3-triazol-1-yl, 4-(trifluoro-methyl)-1,2,3-triazol-1-yl, oxazol-5-yl, and 1,2,3,4-tetrazol-1-yl;

a is an integer from 1 to 2;
each $R^2$ is independently selected from the group consisting of 5-chloro and 6-fluoro;
Y is N and Z is C($R^3$), such that

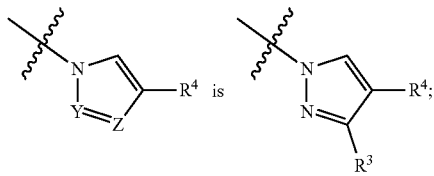

$R^3$ is hydrogen;
$R^4$ is selected from the group consisting of 2-fluoro-6-amino-pyrazin-3-yl, 1-ethyl-pyridazin-4-yl-6-one, 1-methyl-pyridazin-4-yl-6-one, 6-amino-pyridin-3-yl, 2-chloro-6-amino-pyridin-3-yl, 2-fluoro-6-amino-pyridin-3-yl, 2-methyl-6-amino-pyridin-3-yl, 5-fluoro-6-amino-pyridin-3-yl, pyridin-4-yl, 2-fluoro-pyridin-4-yl, 3-fluoro-pyridin-4-yl, 2-methyl-pyridin-4-yl, 2-isopropyl-pyridin-4-yl, 2-(difluoro-methyl)-pyridin-4-yl, 2-(trifluoro-methyl)-pyridin-4-yl, 2-cyano-pyridin-4-yl, 2-cyclopropyl-pyridin-4-yl, 2-(difluoro-methoxy)-pyridin-4-yl, 3-fluoro-5-chloro-pyridin-4-yl, 1-methyl-pyridin-4-yl-2-one, pyridin-3-yl-1-oxide, pyridin-4-yl-1-oxide, 3-fluoro-pyridin-4-yl-1-oxide, 2-(difluoro-methyl)-pyridin-4-yl-1-oxide, 2-methyl-pyridin-4-yl-1-oxide, 2-isopropyl-pyridin-4-yl-1-oxide, 3-fluoro-5-chloro-pyridin-4-yl-1-oxide, 3-chloro-5-fluoro-pyridin-4-yl-1-oxide, pyrimidin-4-yl, 2-(trifluoro-methyl)-pyrimidin-4-yl, 6-(trifluoro-methyl)-pyrimidin-4-yl, 2-(methyl-amino)-pyrimidin-5-yl, and pyrimidin-4-yl-1-oxide;

$R^5$ is selected from the group consisting of
(a) S*-ethyl, 2-(difluoro-methoxy)-ethyl-, R-(2-(difluoro-methoxy)-ethyl-), R*-(2-(difluoro-methoxy)-ethyl-), S*-(2-(difluoro-methoxy)-ethyl-), 2-(difluoro-methyl-carbonyl)-methyl-, 2-trifluoro-methoxy-ethyl-, R*-(2-(methoxy-$d_3$)-ethyl-), and R*-(2-(difluoro-methoxy)-ethyl-2,2-d2-);

(b) cyclopropyl-methyl-, S*-(cyclopropyl-methyl-), R*-(cyclopropyl-methyl-), R-(cyclopropyl-methyl-), 2-(amino-carbonyl)-cyclopropyl-methyl-, S*-(2R*-(amino-carbonyl)-1S*-cyclopropyl-methyl-), S*-(2S*-(amino-carbonyl)-1R*-cyclopropyl-methyl-), 2-(piperidin-1-yl-carbonyl)-cyclopropyl-methyl-, 2R*-(pyrrolidin-1-yl-carbonyl)-1S*-cyclopropyl-methyl-, 2-(3-phenyl-pyrrolidin-1-yl-carbonyl)-cyclopropyl-methyl-, 2-(3-cyclopropyl-pyrrolidin-1-yl-carbonyl)-cyclopropyl-methyl-, and 2-(7-carboxy-azaspiro[2.4]heptan-5-yl-carbonyl)-cyclopropyl-methyl-;

(c) R-(pyrrolidin-1-yl-2-one-methyl-), S*-(pyrrolidin-1-yl-2-one-methyl-), and (pyrrolidin-1-yl-2-one)-methyl-;

(d) phenyl-methyl-, 4-chloro-phenyl-methyl-, 4-fluoro-phenyl-methyl-, R*-(4-fluoro-phenyl-methyl-), S*-(4-fluoro-phenyl-methyl-), and 4-methoxy-phenyl-methyl-;

(e) R-(1-methyl-1,2,3-triazol-4-yl-methyl), R-(1-(difluoro-methyl)-1,2,3-triazol-4-yl-methyl-), 1-methyl-1,2,5-triazol-3-yl-methyl-, R-(1-methyl-1,2,5-triazol-3-yl-methyl-), and R-(1-(difluoro-methyl)-1,2,5-triazol-3-yl-methyl-);

(f) pyrazol-1-yl-methyl-, R*-(pyrazol-1-yl-methyl-), S*-(pyrazol-1-yl-methyl-), 4-fluoro-pyrazol-1-yl-methyl-, R*-(4-fluoro-pyrazol-1-yl-methyl-), S*-(4-fluoro-pyrazol-1-yl-methyl-), 1-methyl-pyrazol-3-yl-methyl-, 1-methyl-pyrazol-4-yl-methyl-, R-(1-methyl-pyrazol-3-yl-methyl-), R-(1-isopropyl-pyrazol-3-yl-methyl-), 1-(difluoro-methyl)-pyrazol-3-yl-methyl-, R-(1-(difluoro-methyl)-pyrazol-1-yl-methyl-), 3-(trifluoro-methyl)-pyrazol-1-yl-methyl-, 5-(trifluoro-methyl)-pyrazol-1-yl-methyl-, 4-(trifluoro-methyl)-pyrazol-1-yl-methyl-, R-(1-(2,2,2-trifluoroethyl)-pyrazol-1-yl-methyl-), R-(3-(difluoro-methoxy)-pyrazol-1-yl-methyl-), S*-(3-(methoxy-methyl)-pyrazol-1-yl-methyl-), 3-(methoxy-methyl)-pyrazol-1-yl-methyl-, 5-(methoxy-methyl)-pyrazol-1-yl-methyl-, S*-(3-(difluoro-methoxy-methyl)-4-fluoro-pyrazol-1-yl-methyl-), 3-carboxy-pyrazol-1-yl-methyl-, 3-(amino-carbonyl)-pyrazol-1-yl-methyl-, 4-(amino-carbonyl)-pyrazol-1-yl-methyl-, 3-(amino-carbonyl-methyl)-pyrazol-1-yl-methyl-, R*-(3-(dimethyl-amino-carbonyl)-pyrazol-1-yl-methyl-), 4-(piperidin-1-yl-carbonyl)-pyrazol-1-yl-methyl-, R*-(4-(piperidin-1-yl-carbonyl)-pyrazol-1-yl-methyl-), 3-(piperidin-1-ylcarbonyl)-pyrazol-1-yl-methyl-, R*-(3-(piperidin-1-yl-carbonyl)-pyrazol-1-yl-methyl-), 4-(piperidin-1-yl-carbonyl-methyl)-pyrazol-1-yl-methyl-, 3-(4-carboxy-piperidin-1-yl-carbonyl)-pyrazol-1-yl-methyl-, 3-(tetrahydropyran-4-yl)-pyrazol-1-yl-methyl-, R-((3-methyl-imidazolidin-1-yl-2-one)-methyl-), R*-((oxazolidin-3-yl-2-one)-methyl-), S*-((oxazolidin-3-yl-2-one)-methyl-), (pyridin-1-yl-2-one)-methyl-), R*-(pyridin-1-yl-2-one)-methyl-), and 2,4,5,7-tetrahydropyrano[3,4-c]pyrazol-2-yl-methyl-;

and (g) N-methyl-N-(methyl-carbonyl)-amino-methyl-, N-methyl-N-(isopropyl-carbonyl)-amino-methyl-, S*—(N-methyl-N-(isopropyl-carbonyl)-amino-methyl-), R*—(N-methyl-N-(t-butyl-carbonyl)-amino-methyl-), N-methyl-N-(t-butyl-carbonyl)-amino-methyl-, N-methyl-N-(methoxy-carbonyl)-amino-methyl-, S*—(N-methyl-N-(methoxy-carbonyl)-amino-methyl-), S*—(N-methyl-N-(t-butoxy-carbonyl)-amino-methyl-), N-methyl-N-(trifluoro-methoxy)-amino-methyl-, N-methyl-N-(dimethyl-amino-carbonyl)-amino-methyl-, N-methyl-N-(phenyl-carbonyl)-amino-methyl-, R*—(N-methyl-N-(phenyl-carbonyl)-amino-methyl-), N-methyl-N-(benzyl-carbonyl)-amino-methyl-, N-methyl-N-(phenyl-ethyl-carbonyl)-amino-methyl-, S*—(N-methyl-N-(phenyl-ethyl-carbonyl)-amino-methyl-), N-methyl-N-(2-(piperidin-1-yl-carbonyl)-ethoxy))-amino-ethyl-, N-methyl-N-(piperidin-1-yl-carbonyl-methyl-carbonyl)-amino-methyl-, and R*—(N-methyl-N-(1-methyl-pyridin-4-yl-2-one-carbonyl)-amino-methyl-);

$R^6$ is hydrogen;

$R^7$ is selected from the group consisting of hydrogen, chloro, methoxy, and ethoxy; or a pharmaceutically acceptable salt thereof.

In certain embodiments, present invention is directed to compounds of formula (I), wherein $R^1$ is selected from the group consisting of 4-(trifluoro-methyl)-1,2,3-triazol-1-yl, and 1,2,3,4-tetrazol-1-yl;

a is an integer from 1 to 2;

each $R^2$ is independently selected from the group consisting of 5-chloro and 6-fluoro;

Y is N and Z is $C(R^3)$, such that

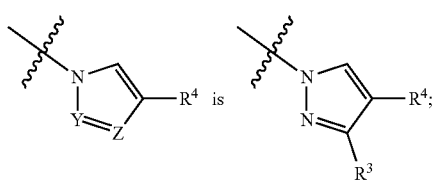

$R^3$ is hydrogen;

$R^4$ is selected from the group consisting of 1-methyl-pyridazin-4-yl-6-one, 2-chloro-6-amino-pyridin-3-yl, 2-fluoro-6-amino-pyridin-3-yl, 2-methyl-6-amino-pyridin-3-yl, pyridin-4-yl, 2-fluoro-pyridin-4-yl, 3-fluoro-pyridin-4-yl, 2-methyl-pyridin-4-yl, 2-(difluoro-methyl)-pyridin-4-yl, 2-(trifluoro-methyl)-pyridin-4-yl, 2-cyano-pyridin-4-yl, 2-cyclopropyl-pyridin-4-yl, 2-(difluoro-methoxy)-pyridin-4-yl, 3-fluoro-5-chloro-pyridin-4-yl, 1-methyl-pyridin-4-yl-2-one, pyridin-4-yl-1-oxide, 3-fluoro-pyridin-4-yl-1-oxide, 2-(difluoro-methyl)-pyridin-4-yl-1-oxide, 2-isopropyl-pyridin-4-yl-1-oxide, 3-chloro-5-fluoro-pyridin-4-yl-1-oxide, pyrimidin-4-yl, 2-(trifluoro-methyl)-pyrimidin-4-yl, and 2-(methyl-amino)-pyrimidin-5-yl;

$R^5$ is selected from the group consisting of
(a) 2-(difluoro-methoxy)-ethyl-, R-(2-(difluoro-methoxy)-ethyl-), R*-(2-(difluoro-methoxy)-ethyl-), S*-(2-(difluoro-methoxy)-ethyl-), and R*-(2-(difluoro-methoxy)-ethyl-2,2-$d_2$-);
(b) cyclopropyl-methyl-, S*-(cyclopropyl-methyl-), R*-(cyclopropyl-methyl-), 2-(amino-carbonyl)-cyclopropyl-methyl-, S*-(2R*-(amino-carbonyl)-1S*-cyclopropyl-methyl-), S*-(2S*-(amino-carbonyl)-1R*-cyclopropyl-methyl-), and 2-(piperidin-1-yl-carbonyl)-cyclopropyl-methyl-;
(c) R-(pyrrolidin-1-yl-2-one-methyl-), S*-(pyrrolidin-1-yl-2-one-methyl-), and (pyrrolidin-1-yl-2-one)-methyl-;
(d) 4-chloro-phenyl-methyl-, 4-fluoro-phenyl-methyl-, R*-(4-fluoro-phenyl-methyl-), S*-(4-fluoro-phenyl-methyl-), and 4-methoxy-phenyl-methyl-;
(e) R-(1-methyl-1,2,3-triazol-4-yl-methyl), R-(1-(difluoro-methyl)-1,2,3-triazol-4-yl-methyl-), and R-(1-methyl-1,2,5-triazol-3-yl-methyl-);
(f) pyrazol-1-yl-methyl-, R*-(pyrazol-1-yl-methyl-), S*-(pyrazol-1-yl-methyl-), 4-fluoro-pyrazol-1-yl-methyl-, R*-(4-fluoro-pyrazol-1-yl-methyl-), S*-(4-fluoro-pyrazol-1-yl-methyl-), 1-methyl-pyrazol-3-yl-methyl-, 1-methyl-pyrazol-4-yl-methyl-, R-(1-methyl-pyrazol-3-yl-methyl-), R-(1-isopropyl-pyrazol-3-yl-methyl-), 1-(difluoro-methyl)-pyrazol-3-yl-methyl-, R-(1-(difluoro-methyl)-pyrazol-1-yl-methyl-), 3-(trifluoro-methyl)-pyrazol-1-yl-methyl-, R-(1-(2,2,2-trifluoro-ethyl)-pyrazol-1-yl-methyl-), R-(3-(difluoro-methoxy)-pyrazol-1-yl-methyl-), S*-(3-(methoxy-methyl)-pyrazol-1-yl-methyl-), 3-(methoxy-methyl)-pyrazol-1-yl-methyl-, 3-(amino-carbonyl)-pyrazol-1-yl-methyl-, 4-(amino-carbonyl)-pyrazol-1-yl-methyl-, 3-(amino-carbonyl-methyl)-pyrazol-1-yl-methyl-, 4-(piperidin-1-yl-carbonyl)-pyrazol-1-yl-methyl-, 3-(piperidin-1-yl-carbonyl)-pyrazol-1-yl-methyl-, 4-(piperidin-1-yl-carbonyl-methyl)-pyrazol-1-yl-methyl-, 3-(4-carboxy-piperidin-1-yl-carbonyl)-pyrazol-1-yl-methyl-, R-((3-methyl-imidazolidin-1-yl-2-one)-methyl-), and 2,4,5,7-tetrahydropyrano[3,4-c]pyrazol-2-yl-methyl-;

and (g) N-methyl-N-(methyl-carbonyl)-amino-methyl-, S*—(N-methyl-N-(isopropyl-carbonyl)-amino-methyl-), R*—(N-methyl-N-(t-butyl-carbonyl)-amino-methyl-), N-methyl-N-(t-butyl-carbonyl)-amino-methyl-, S*—(N-methyl-N-(t-butoxy-carbonyl)-amino-methyl-), N-methyl-N-(phenyl-carbonyl)-amino-methyl-, N-methyl-N-(benzyl-carbonyl)-amino-methyl-, N-methyl-N-(phenyl-ethyl-carbonyl)-amino-methyl-, S*—(N-methyl-N-(phenyl-ethyl-carbonyl)-amino-methyl-), N-methyl-N-(2-piperidin-1-yl-carbonyl)-ethoxy))-amino-ethyl-, and R*—(N-methyl-N-(1-methyl-pyridin-4-yl-2-one-carbonyl)-amino-methyl-);

$R^6$ is hydrogen;

$R^7$ is selected from the group consisting of hydrogen, methoxy, and ethoxy; or a pharmaceutically acceptable salt thereof.

In certain embodiments, present invention is directed to compounds of formula (I), wherein $R^1$ is 1,2,3,4-tetrazol-1-yl;

a is 2;

one $R^2$ is 5-chloro and one $R^2$ is 6-fluoro;

Y is N and Z is C(R³), such that

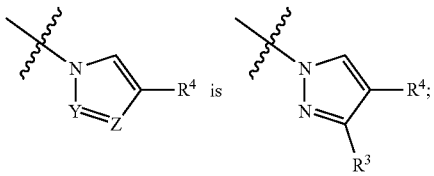

R³ is hydrogen;
R⁴ is selected from the group consisting of 2-chloro-6-amino-pyridin-3-yl, 2-fluoro-6-amino-pyridin-3-yl, 2-methyl-6-amino-pyridin-3-yl, pyridin-4-yl, 2-fluoro-pyridin-4-yl, 3-fluoro-pyridin-4-yl, 2-methyl-pyridin-4-yl, 2-(trifluoro-methyl)-pyridin-4-yl, 2-(difluoro-methyl)-pyridin-4-yl, 2-cyano-pyridin-4-yl, 3-fluoro-5-chloro-pyridin-4-yl, pyridin-4-yl-1-oxide, 3-fluoro-pyridin-4-yl-1-oxide, 2-(difluoro-methyl)-pyridin-4-yl-1-oxide, 2-isopropyl-pyridin-4-yl-1-oxide, and 2-(trifluoro-methyl)-pyrimidin-4-yl;
R⁵ is selected from the group consisting of
(a) 2-(difluoro-methoxy)-ethyl-, R-(2-(difluoro-methoxy)-ethyl-), R*-(2-(difluoro-methoxy)-ethyl-), and S*-(2-(difluoro-methoxy)-ethyl-);
(b) cyclopropyl-methyl- and R*-(cyclopropyl-methyl-);
(c) R-(pyrrolidin-1-yl-2-one-methyl-), S*-(pyrrolidin-1-yl-2-one-methyl-), and (pyrrolidin-1-yl-2-one)-methyl-;
(d) R*-(4-fluoro-phenyl-methyl-), and S*-(4-fluoro-phenyl-methyl-);
(e) R-(1-methyl-1,2,5-triazol-3-yl-methyl-);
(f) pyrazol-1-yl-methyl-, R*-(pyrazol-1-yl-methyl-), S*-(pyrazol-1-yl-methyl-), 4-fluoro-pyrazol-1-yl-methyl-, R*-(4-fluoro-pyrazol-1-yl-methyl-), S*-(4-fluoro-pyrazol-1-yl-methyl-), 1-methyl-pyrazol-3-yl-methyl-, 1-methyl-pyrazol-4-yl-methyl-, R-(1-methyl-pyrazol-3-yl-methyl-), R-(1-isopropyl-pyrazol-3-yl-methyl-), R-(1-(difluoro-methyl)-pyrazol-1-yl-methyl-), R-(1-(2,2,2-trifluoroethyl)-pyrazol-1-yl-methyl-), R-(3-(difluoro-methoxy)-pyrazol-1-yl-methyl-), S*-(3-(methoxy-methyl)-pyrazol-1-yl-methyl-), 3-(methoxy-methyl)-pyrazol-1-yl-methyl-, 3-(amino-carbonyl)-pyrazol-1-yl-methyl-, 3-(amino-carbonyl-methyl)-pyrazol-1-yl-methyl-, 3-(piperidin-1-yl-carbonyl)-pyrazol-1-yl-methyl-, 4-(piperidin-1-yl-carbonyl-methyl)-pyrazol-1-yl-methyl-, 3-(4-carboxy-piperidin-1-yl-carbonyl)-pyrazol-1-yl-methyl-, R-((3-methyl-imidazolidin-1-yl-2-one)-methyl-), and 2,4,5,7-tetrahydropyrano[3,4-c]pyrazol-2-yl-methyl-;
and (g) N-methyl-N-(phenyl-ethyl-carbonyl)-amino-methyl-, and R*—(N-methyl-N-(1-methyl-pyridin-4-yl-2-one-carbonyl)-amino-methyl-);
R⁶ is hydrogen;
R⁷ is selected from the group consisting of hydrogen, methoxy, and ethoxy;
or a pharmaceutically acceptable salt thereof.

In certain embodiments, present invention is directed to compounds of formula (I), wherein R¹ is 1,2,3,4-tetrazol-1-yl;
a is 2;
one R² is 5-chloro and one R² is 6-fluoro;

Y is N and Z is C(R³), such that

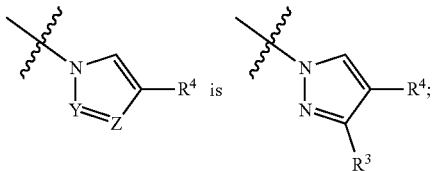

R³ is hydrogen;
R⁴ is selected from the group consisting of 2-fluoro-6-amino-pyridin-3-yl, 2-methyl-6-amino-pyridin-3-yl, pyridin-4-yl, 2-(trifluoro-methyl)-pyridin-4-yl, 3-fluoro-5-chloro-pyridin-4-yl, pyridin-4-yl-1-oxide, and 3-fluoro-pyridin-4-yl-1-oxide;
R⁵ is selected from the group consisting of
(a) R-(2-(difluoro-methoxy)-ethyl-), R*-(2-(difluoro-methoxy)-ethyl-), and S*-(2-(difluoro-methoxy)-ethyl-);
(b) cyclopropyl-methyl;
(c) R-(pyrrolidin-1-yl-2-one-methyl-);
(d) R*-(4-fluoro-phenyl-methyl-), and S*-(4-fluoro-phenyl-methyl-);
(f) pyrazol-1-yl-methyl-, R*-(pyrazol-1-yl-methyl-), 4-fluoro-pyrazol-1-yl-methyl-, R*-(4-fluoro-pyrazol-1-yl-methyl-), R-(1-methyl-pyrazol-3-yl-methyl-), R-(1-isopropyl-pyrazol-3-yl-methyl-), 3-(methoxy-methyl)-pyrazol-1-yl-methyl-, 3-(amino-carbonyl)-pyrazol-1-yl-methyl-, and 3-(4-carboxy-piperidin-1-yl-carbonyl)-pyrazol-1-yl-methyl-;
R⁶ is hydrogen;
R⁷ is selected from the group consisting of hydrogen, and ethoxy; or a pharmaceutically acceptable salt thereof.

In certain embodiments, the present invention is directed to compounds of formula (I) wherein R⁴ is 9 to 10 membered bicyclic heterocyclyl, wherein the 9 to 10 membered bicyclic heterocyclyl is optionally substituted as described herein.

In certain embodiments, the present invention is directed to compounds of formula (I) wherein R⁴ is (e) 9 to 10 membered bicyclic heterocyclyl; wherein the 9 to 10 membered bicyclic heterocyclyl contains at least one heteroatom selected from the group consisting of O, N and S; optionally contains one to four additional heteroatoms independently selected from the group consisting of O, N and S; wherein the 9 to 10 membered bicyclic heterocyclyl is saturated, partially unsaturated, partially aromatic, aromatic, bicyclic, fused, bridged or spiro-cyclic; and wherein the 9 to 10 membered bicyclic heterocyclyl is optionally substituted with one to two substituents independently selected from the group consisting of halogen, hydroxy, oxo, $C_{1-4}$alkyl, fluorinated $C_{1-4}$alkyl, $C_{1-4}$alkoxy, fluorinated $C_{1-4}$alkoxy, cyano, —C(O)OH, —C(O)—O—$C_{1-4}$alkyl, $NR^JR^K$, and —C(O)—$NR^JR^K$; wherein $R^J$ and $R^K$ are each hydrogen.

In certain embodiments, the present invention is directed to compounds of formula (I) wherein R⁴ is 9 to 10 membered bicyclic heterocyclyl; wherein the 9 to 10 membered bicyclic heterocyclyl contains at least one heteroatom selected from the group consisting of O, N and S; optionally contains one to four additional heteroatoms independently selected from the group consisting of O, N and S; wherein the 9 to 10 membered bicyclic heterocyclyl is saturated, partially unsaturated, partially aromatic, aromatic, bicyclic, fused, bridged or spiro-cyclic; and wherein the 9 to 10 membered bicyclic heterocyclyl is optionally substituted with one to two substituents independently selected from the group consisting of halogen and $C_{1-4}$alkyl.

In certain embodiments, the present invention is directed to compounds of formula (I) wherein R⁴ is selected from the group consisting of 1-methyl-1H-indazol-5-yl, 2-methyl-indazol-5-yl, isoindol-4-yl-2-one, 2-methyl-isoindolin-5-yl-1-one, 2-methyl-3,4-dihydroisoquinolin-6-yl-1-one, isobenzofuran-5-yl-1-one, 2,2-difluoro-benzo[d][1,3]dioxol-5-yl, and 2,3-dihydro-benzo[b][1,4]dioxin-6-yl.

In certain embodiments, the present invention is directed to compounds of formula (I) wherein R⁴ is selected from the group consisting of 4-carboxy-phenyl, 4-(amino-carbonyl)-phenyl, 4-(methoxy-carbonyl-amino)-phenyl, 3-fluoro-4-carboxy-phenyl, 3-fluoro-4-(amino-carbonyl)-phenyl, 2-fluoro-6-amino-pyridin-3-yl, 2-carboxy-pyridin-4-yl, 2-(trifluoro-methyl)-pyridin-4-yl, pyridin-4-yl-1-oxide, 5-carboxy-pyrrol-3-yl, 2-(trifluoro-methyl)-pyrimidin-4-yl, 1-methyl-pyrazol-5-yl, 1-methyl-pyridazin-4-yl-6-one, 1-methyl-1,2,3-triazol-5-yl, 1-methyl-4-fluoro-1,2,3-triazol-5-yl, 1-methyl-1,2,4-triazol-5-yl and 1-(difluoro-methyl)-1,2,4-triazol-5-yl. In certain embodiments, the present invention is directed to compounds of formula (I) wherein R⁴ is selected from the group consisting of 4-carboxy-phenyl, 3-fluoro-4-carboxy-phenyl, 4-(amino-carbonyl)-phenyl, 3-fluoro-4-(amino-carbonyl)-phenyl, 5-carboxy-pyrrol-3-yl, 1-methyl-pyrazol-5-yl, pyridin-4-yl-1-oxide, 2-(trifluoro-methyl)-pyridin-4-yl, 2-fluoro-6-amino-pyridin-3-yl, 1-methyl-1,2,3-triazol-5-yl, 1-(difluoro-methyl)-1,2,4-triazol-5-yl and 1-methyl-4-fluoro-1,2,3-triazol-5-yl. In certain embodiments, the present invention is directed to compounds of formula (I) wherein R⁴ is selected from the group consisting of 4-carboxy-phenyl, 3-fluoro-4-carboxy-phenyl, 4-(amino-carbonyl)-phenyl, 3-fluoro-4-(amino-carbonyl)-phenyl, 5-carboxy-pyrrol-3-yl, pyridin-4-yl-1-oxide and 1-methyl-1,2,3-triazol-5-yl. In certain embodiments, the present invention is directed to compounds of formula (I) wherein R⁴ is selected from the group consisting of 4-carboxy-phenyl, 3-fluoro-4-carboxy-phenyl and 4-(amino-carbonyl)-phenyl.

In certain embodiments, the present invention is directed to compounds of formula (I) wherein R⁴ is selected from the group consisting of carboxy, phenyl, 4-fluoro-phenyl, 4-trifluoro-methoxy-phenyl, 3-carboxy-phenyl, 4-carboxy-phenyl, 3-fluoro-4-carboxy-phenyl, 4-amino-phenyl, 4-(methyl-d₃-amino)-phenyl, 4-(1-amino-ethyl)-phenyl, 4-(methyl-carbonyl-amino)-phenyl, 4-(methoxy-carbonyl-amino)-phenyl, 4-(methoxy-methyl-carbonyl-amino)-phenyl, 4-(2-methoxy-ethoxy-carbonyl-amino)-phenyl, 2-fluoro-6-(methyl-carbonyl-amino)-phenyl, 4-(1-(methoxy-carbonyl-amino)-ethyl)-phenyl, 4-(amino-carbonyl)-phenyl, 3-fluoro-4-(amino-carbonyl)-phenyl, 4-(cyclopropyl-amino-carbonyl)-phenyl, 4-(methyl-sulfonyl-amino)-phenyl, 4-(methyl-sulfonyl-amino-carbonyl)-phenyl, 4-(1-carboxy-cycloprop-1-yl)-phenyl, 4-((1-methoxy-carbonyl)-cycloprop-1-yl)-phenyl, 4-(pyrrolidin-2-yl-5-one)-phenyl), 2-(1,2,3,4-tetrazol-1-yl)-5-chloro-phenyl and 4-(1,2,4-oxadiazol-3-yl-5-one)-phenyl. In certain embodiments, the present invention is directed to compounds of formula (I) wherein R⁴ is selected from the group consisting of phenyl, 4-fluoro-phenyl, 3-carboxy-phenyl, 4-carboxy-phenyl, 4-amino-phenyl, 4-(1-amino-ethyl)-phenyl, 4-(methyl-d₃-amino)-phenyl, 3-fluoro-4-carboxy-phenyl, 4-(amino-carbonyl)-phenyl, 3-fluoro-4-(amino-carbonyl)-phenyl, 4-(cyclopropyl-amino-carbonyl)-phenyl, 4-(methyl-carbonyl-amino)-phenyl, 4-(methoxy-carbonyl-amino)-phenyl, 2-fluoro-6-(methyl-carbonyl-amino)-phenyl, 4-(methoxy-methyl-carbonyl-amino)-phenyl, 4-(2-methoxy-ethoxy-carbonyl-amino)-phenyl, 4-(1-(methoxy-carbonyl-amino)-ethyl)-phenyl, 4-(methyl-sulfonyl-amino)-phenyl, 4-(methyl-sulfonyl-amino-carbonyl)-phenyl, 4-(1-carboxy-cycloprop-1-yl)-phenyl, 4-(pyrrolidin-2-yl-5-one)-phenyl), and 4-(1,2,4-oxadiazol-3-yl-5-one)-phenyl. In certain embodiments, the present invention is directed to compounds of formula (I) wherein R⁴ is selected from the group consisting of 3-carboxy-phenyl, 4-carboxy-phenyl, 4-(methyl-d₃-amino)-phenyl, 3-fluoro-4-carboxy-phenyl, 4-(amino-carbonyl)-phenyl, 3-fluoro-4-(amino-carbonyl)-phenyl, 4-(cyclopropyl-amino-carbonyl)-phenyl, 4-(methyl-carbonyl-amino)-phenyl, 4-(methoxy-carbonyl-amino)-phenyl, 2-fluoro-6-(methyl-carbonyl-amino)-phenyl, 4-(2-methoxy-ethoxy-carbonyl-amino)-phenyl, 4-(1-(methoxy-carbonyl-amino)-ethyl)-phenyl, 4-(methyl-sulfonyl-amino)-phenyl, 4-(methyl-sulfonyl-amino-carbonyl)-phenyl, 4-(pyrrolidin-2-yl-5-one)-phenyl), and 4-(1,2,4-oxadiazol-3-yl-5-one)-phenyl. In certain embodiments, the present invention is directed to compounds of formula (I) wherein R⁴ is selected from the group consisting of 4-carboxy-phenyl, 3-fluoro-4-carboxy-phenyl, 4-(amino-carbonyl)-phenyl, 3-fluoro-4-(amino-carbonyl)-phenyl, 4-(methoxy-carbonyl-amino)-phenyl, and 4-(1,2,4-oxadiazol-3-yl-5-one)-phenyl.

In certain embodiments, the present invention is directed to compounds of formula (I) wherein R⁴ is selected from the group consisting of 1-(difluoro-methyl)-pyrazol-3-yl, 1-(difluoro-methyl)-4-chloro-pyrazol-3-yl, 1-(difluoro-methyl)-4-cyano-pyrazol-3-yl, 3-chloro-pyrazol-4-yl, 1-methyl-pyrazol-4-yl, 3-methyl-pyrazol-4-yl, 1-methyl-3-chloro-pyrazol-4-yl, 1-(trifluoro-methyl)-pyrazol-4-yl, 1-(difluoro-methyl)-3-hydroxy-pyrazol-4-yl, 1-(methoxy-carbonyl-methyl)-pyrazol-4-yl, pyrazol-5-yl, 1-methyl-4-fluoro-pyrazol-5-yl, 1-methyl-pyrazol-5-yl, 1-methyl-4-cyano-pyrazol-5-yl, 1-(difluoro-methyl)-pyrazol-5-yl, 1-methyl-3-(trifluoro-methyl)-pyrazol-5-yl, 1-methyl-4-chloro-pyrazol-5-yl, 1-(methyl-d₃)-pyrazol-5-yl, 1-(difluoro-methyl)-4-chloro-pyrazol-5-yl, 1-(difluoro-methyl)-4-fluoro-pyrazol-5-yl, 1-(difluoro-methyl)-4-cyano-pyrazol-5-yl, 1-methyl-4-hydroxy-pyrazol-5-yl, 1-(difluoro-methyl)-pyrazol-5-yl), 1-(methyl-d₃)-4-(cyclopropyl-carbonyl-amino)-pyrazol-5-yl, thiazol-5-yl, 4-methyl-thiazol-5-yl, 4-cyclopropyl-thiazol-5-yl, 2-(difluoro-methyl)-thiazol-5-yl, 4-(trifluoro-methyl)-thiazol-5-yl, 4-chloro-thiazol-5-yl, 2-amino-thaizol-5-yl, 2-amino-4-chloro-thiazol-5-yl, 2-(trifluoro-methyl)-4-methyl-thiazol-5-yl, isothiazol-4-yl, 1,2,4-thiadizol-5-yl, 2-(trifluoro-methyl)-1,3,4-thiadiazol-5-yl, imidazol-1-yl, 2-methyl-imidazol-1-yl, 1-methyl-imidazol-5-yl, 1-(difluoro-methyl)-imidazol-5-yl, 1-(difluoro-methyl)-4-chloro-imidazol-5-yl, 1-methyl-4-chloro-imidazol-5-yl, oxazol-5-yl, 3-methyl-isoxazol-4-yl, 1,3,4-oxadiazol-5-yl, 3-methyl-1,2,4-oxadiazol-5-yl, 1-methyl-1,2,3-triazol-4-yl, 1-(difluoro-methyl)-1,2,3-triazol-4-yl, 1-(difluoro-methyl)-5-chloro-1,2,3-triazol-4-yl, 1-methyl-5-fluoro-1,2,3-triazol-4-yl, 1-methyl-1,2,3-triazol-5-yl, 1-methyl-4-chloro-1,2,3-triazol-5-yl, 1-cyclopropyl-1,2,3-triazol-5-yl, 1-(difluoro-methyl)-1,2,3-triazol-5-yl, 1-(difluoro-methyl)-4-chloro-1,2,3-triazol-5-yl, 1-methyl-4-fluoro-1,2,3-triazol-5-yl, 1-(difluoro-methyl)-4-fluoro-1,2,3-triazol-5-yl, 1-isopropyl-1,2,3-triazol-5-yl, 3-methyl-1,2,4-triazol-1-yl, 1-(difluoro-methyl)-1,2,4-triazol-5-yl, 1-methyl-1,2,4-triazol-5-yl, 1-methyl-1,2,5-triazol-3-yl, 1-(difluoro-methyl)-4-chloro-1,2,5-triazol-3-yl, 1-(difluoro-methyl)-1,2,5-triazol-3-yl, 1-(difluoro-methyl)-4-fluoro-1,2,5-triazol-3-yl, 1-(difluoro-methyl)-1,2,5-triazol-4-yl, 1,3,4-triazol-1-yl, 2-methyl-1,3,4-triazol-1-yl, 1-(difluoro-methyl)-1,3,4-triazol-2-yl, 1-methyl-1,2,3,4-tetrazol-5-yl, 5-(amino-carbonyl)-thien-2-yl, 3-methyl-5-(amino-carbonyl)-thien-2-yl, and 4-fluoro-5-(amino-carbonyl)-thien-3-yl. In certain embodiments, the present invention is directed to compounds of formula (I) wherein $R^4$ is selected from the group consisting of 1-(difluoro-methyl)-pyrazol-3-yl, 1-(difluoro-methyl)-4-chloro-pyrazol-3-yl, 3-chloro-pyrazol-4-yl, 1-methyl-pyrazol-4-yl, 1-methyl-3-chloro-pyrazol-4-yl, 1-(trifluoro-methyl)-pyrazol-4-yl, 1-(methoxy-carbonyl-methyl)-pyrazol-4-yl, pyrazol-5-yl, 1-methyl-4-fluoro-pyrazol-5-yl, 1-methyl-pyrazol-5-yl, 1-methyl-4-cyano-pyrazol-5-yl, 1-(difluoro-methyl)-pyrazol-5-yl, 1-methyl-3-(trifluoro-methyl)-pyrazol-5-yl, 1-methyl-4-chloro-pyrazol-5-yl, 1-(methyl-$d_3$)-pyrazol-5-yl, 1-(difluoro-methyl)-4-chloro-pyrazol-5-yl, 1-(difluoro-methyl)-4-fluoro-pyrazol-5-yl, 1-(difluoro-methyl)-4-cyano-pyrazol-5-yl, 1-methyl-4-hydroxy-pyrazol-5-yl, 1-(difluoro-methyl)-pyrazol-5-yl), 1-(methyl-$d_3$)-4-(cyclopropyl-carbonyl-amino)-pyrazol-5-yl, thiazol-5-yl, 4-methyl-thiazol-5-yl, 4-cyclopropyl-thiazol-5-yl, 2-(difluoro-methyl)-thiazol-5-yl, 4-(trifluoro-methyl)-thiazol-5-yl, 4-chloro-thiazol-5-yl, 2-amino-thaizol-5-yl, 2-amino-4-chloro-thiazol-5-yl, 2-(trifluoro-methyl)-4-methyl-thiazol-5-yl, isothiazol-4-yl, 1,2,4-thiadizol-5-yl, 2-(trifluoro-methyl)-1,3,4-thiadiazol-5-yl, imidazol-1-yl, 2-methyl-imidazol-1-yl, 1-methyl-imidazol-5-yl, 1-(difluoro-methyl)-imidazol-5-yl, 1-(difluoro-methyl)-4-chloro-imidazol-5-yl, 1-methyl-4-chloro-imidazol-5-yl, oxazol-5-yl, 3-methyl-isoxazol-4-yl, 1,3,4-oxadiazol-5-yl, 3-methyl-1,2,4-oxadiazol-5-yl, 1-methyl-1,2,3-triazol-4-yl, 1-(difluoro-methyl)-1,2,3-triazol-4-yl, 1-(difluoro-methyl)-5-chloro-1,2,3-triazol-4-yl, 1-methyl-5-fluoro-1,2,3-triazol-4-yl, 1-methyl-1,2,3-triazol-5-yl, 1-methyl-4-chloro-1,2,3-triazol-5-yl, 1-cyclopropyl-1,2,3-triazol-5-yl, 1-(difluoro-methyl)-1,2,3-triazol-5-yl, 1-(difluoro-methyl)-4-chloro-1,2,3-triazol-5-yl, 1-methyl-4-fluoro-1,2,3-triazol-5-yl, 1-isopropyl-1,2,3-triazol-5-yl, 3-methyl-1,2,4-triazol-1-yl, 1-(difluoro-methyl)-1,2,4-triazol-5-yl, 1-methyl-1,2,4-triazol-5-yl, 1-methyl-1,2,5-triazol-3-yl, 1-(difluoro-methyl)-1,2,5-triazol-3-yl, 1-(difluoro-methyl)-4-fluoro-1,2,5-triazol-3-yl, 1-(difluoro-methyl)-1,2,5-triazol-4-yl, 1,3,4-triazol-1-yl, 2-methyl-1,3,4-triazol-1-yl, 1-(difluoro-methyl)-1,3,4-triazol-2-yl, 1-methyl-1,2,3,4-tetrazol-5-yl, 5-(amino-carbonyl)-thien-2-yl, 3-methyl-5-(amino-carbonyl)-thien-2-yl, and 4-fluoro-5-(amino-carbonyl)-thien-3-yl. In certain embodiments, the present invention is directed to compounds of formula (I) wherein $R^4$ is selected from the group consisting of 1-(difluoro-methyl)-pyrazol-3-yl, 1-(difluoro-methyl)-4-chloro-pyrazol-3-yl, 3-chloro-pyrazol-4-yl, 1-methyl-3-chloro-pyrazol-4-yl, pyrazol-5-yl, 1-methyl-4-fluoro-pyrazol-5-yl, 1-methyl-pyrazol-5-yl, 1-methyl-4-cyano-pyrazol-5-yl, 1-(difluoro-methyl)-pyrazol-5-yl, 1-methyl-3-(trifluoro-methyl)-pyrazol-5-yl, 1-methyl-4-chloro-pyrazol-5-yl, 1-(methyl-$d_3$)-pyrazol-5-yl, 1-(difluoro-methyl)-4-chloro-pyrazol-5-yl, 1-(difluoro-methyl)-4-fluoro-pyrazol-5-yl, 1-methyl-4-hydroxy-pyrazol-5-yl, 4-methyl-thiazol-5-yl, 4-cyclopropyl-thiazol-5-yl, 2-(difluoro-methyl)-thiazol-5-yl, 4-(trifluoro-methyl)-thiazol-5-yl, 4-chloro-thiazol-5-yl, 2-amino-thaizol-5-yl, 2-amino-4-chloro-thiazol-5-yl, 2-(trifluoro-methyl)-4-methyl-thiazol-5-yl, 1,2,4-thiadizol-5-yl, imidazol-1-yl, 2-methyl-imidazol-1-yl, 1-methyl-imidazol-5-yl, 1-(difluoro-methyl)-imidazol-5-yl, 1-(difluoro-methyl)-4-chloro-imidazol-5-yl, 1-methyl-4-chloro-imidazol-5-yl, oxazol-5-yl, 3-methyl-isoxazol-4-yl, 1,3,4-oxadiazol-5-yl, 1-methyl-1,2,3-triazol-4-yl, 1-(difluoro-methyl)-1,2,3-triazol-4-yl, 1-(difluoro-methyl)-5-chloro-1,2,3-triazol-4-yl, 1-methyl-5-fluoro-1,2,3-triazol-4-yl, 1-methyl-1,2,3-triazol-5-yl, 1-methyl-4-chloro-1,2,3-triazol-5-yl, 1-cyclopropyl-1,2,3-triazol-5-yl, 1-(difluoro-methyl)-1,2,3-triazol-5-yl, 1-(difluoro-methyl)-4-chloro-1,2,3-triazol-5-yl, 1-methyl-4-fluoro-1,2,3-triazol-5-yl, 1-isopropyl-1,2,3-triazol-5-yl, 1-(difluoro-methyl)-1,2,4-triazol-5-yl, 1-methyl-1,2,4-triazol-5-yl, 1-(difluoro-methyl)-1,2,5-triazol-3-yl, 1-(difluoro-methyl)-4-fluoro-1,2,5-triazol-3-yl, 1-(difluoro-methyl)-1,2,5-triazol-4-yl, 1,3,4-triazol-1-yl, 2-methyl-1,3,4-triazol-1-yl, 1-(difluoro-methyl)-1,3,4-triazol-2-yl, 3-methyl-5-(amino-carbonyl)-thien-2-yl, and 4-fluoro-5-(amino-carbonyl)-thien-3-yl.

In certain embodiments, the present invention is directed to compounds of formula (I) wherein $R^4$ is selected from the group consisting of 1-(difluoro-methyl)-pyrazol-3-yl, 1-(difluoro-methyl)-4-chloro-pyrazol-3-yl, 3-chloro-pyrazol-4-yl, 1-methyl-3-chloro-pyrazol-4-yl, 1-methyl-4-fluoro-pyrazol-5-yl, 1-methyl-pyrazol-5-yl, 1-methyl-4-cyano-pyrazol-5-yl, 1-(difluoro-methyl)-pyrazol-5-yl, 1-methyl-3-(trifluoro-methyl)-pyrazol-5-yl, 1-(methyl-$d_3$)-pyrazol-5-yl, 1-(difluoro-methyl)-4-chloro-pyrazol-5-yl, 1-(difluoro-methyl)-4-fluoro-pyrazol-5-yl, 1-methyl-4-hydroxy-pyrazol-5-yl, 4-methyl-thiazol-5-yl, 4-(trifluoro-methyl)-thiazol-5-yl, 4-chloro-thiazol-5-yl, 2-amino-thaizol-5-yl, 2-amino-4-chloro-thiazol-5-yl, 1-methyl-imidazol-5-yl, 1-(difluoro-methyl)-imidazol-5-yl, 3-methyl-isoxazol-4-yl, 1-(difluoro-methyl)-1,2,3-triazol-4-yl, 1-(difluoro-methyl)-5-chloro-1,2,3-triazol-4-yl, 1-methyl-1,2,3-triazol-5-yl, 1-methyl-4-chloro-1,2,3-triazol-5-yl, 1-(difluoro-methyl)-1,2,3-triazol-5-yl, 1-methyl-4-fluoro-1,2,3-triazol-5-yl, 1-(difluoro-methyl)-4-chloro-1,2,3-triazol-5-yl, 1-(difluoro-methyl)-1,2,4-triazol-5-yl, 1-methyl-1,2,4-triazol-5-yl, 1-(difluoro-methyl)-1,2,5-triazol-3-yl, 1-(difluoro-methyl)-4-fluoro-1,2,5-triazol-3-yl, and 3-methyl-5-(amino-carbonyl)-thien-2-yl.

In certain embodiments, the present invention is directed to compounds of formula (I) wherein $R^4$ is selected from the group consisting of 3-chloro-pyrazol-4-yl, 1-methyl-3-chloro-pyrazol-4-yl, 1-methyl-4-fluoro-pyrazol-5-yl, 1-methyl-pyrazol-5-yl, 1-(difluoro-methyl)-pyrazol-5-yl, 1-(methyl-$d_3$)-pyrazol-5-yl, 1-(difluoro-methyl)-4-chloro-pyrazol-5-yl, 4-chloro-thiazol-5-yl, 2-amino-thaizol-5-yl 1-methyl-imidazol-5-yl, 1-(difluoro-methyl)-1,2,3-triazol-4-yl, 1-methyl-1,2,3-triazol-5-yl, 1-methyl-4-chloro-1,2,3-triazol-5-yl, 1-(difluoro-methyl)-1,2,3-triazol-5-yl, 1-methyl-4-fluoro-1,2,3-triazol-5-yl, 1-(difluoro-methyl)-4-chloro-1,2,3-triazol-5-yl, 1-(difluoro-methyl)-1,2,4-triazol-5-yl, and 1-methyl-1,2,4-triazol-5-yl.

In certain embodiments, the present invention is directed to compounds of formula (I) wherein $R^4$ is selected from the group consisting of 1-(methoxy-carbonyl)-piperidin-4-yl, 1-(methoxy-carbonyl)-piperidin-3-yl, 2-fluoro-6-amino-pyrazin-3-yl, pyridazin-4-yl, 1-ethyl-pyridazin-4-yl-6-one, 1-methyl-pyridazin-4-yl-6-one, 1-isopropyl-pyridazin-4-yl-6-one, 1-(2-isopropyloxy-ethyl)-pyridazin-4-yl-6-one, pyridazin-4-yl-1-oxide, pyridin-2-yl, 6-fluoro-pyridin-3-yl, 6-amino-pyridin-3-yl, 2-chloro-6-amino-pyridin-3-yl, 2-fluoro-6-amino-pyridin-3-yl, 2-methyl-6-amino-pyridin-3-yl, 5-fluoro-6-amino-pyridin-3-yl, 4-fluoro-6-amino-pyridin-3-yl, 2-fluoro-5-methoxy-pyridin-3-yl, 2-fluoro-4-(cyclopropyl-carbonyl-amino)-pyridin-3-yl, pyridin-4-yl, 2-fluoro-pyridin-4-yl, 3-fluoro-pyridin-4-yl, 2-methyl-pyridin-4-yl, 2-isopropyl-pyridin-4-yl, 2-t-butyl-pyridin-4-yl, 2-(trifluoro-methyl)-pyridin-4-yl, 2-cyano-pyridin-4-yl, 2-cyclopropyl-pyridin-4-yl, 2-(difluoro-methoxy)-pyridin-4-yl, 2-(difluoro-methyl)-pyridin-4-yl, 3-(trifluoro-methyl-pyridin-4-yl), 3-(trifluoro-methyl)-pyridin-4-yl, 3-fluoro-5-chloro-pyridin-4-yl, 2-(trifluoro-methyl)-5-(methyl-carbonyl-amino)-pyridin-4-yl, 1-methyl-pyridin-3-yl-6-one, 1-methyl-pyridin-4-yl-2-one, pyridin-3-yl-1-oxide, 6-amino-pyridin-3-yl-1-oxide, 2-methyl-6-amino-pyridin-3-yl-1-oxide, pyridin-4-yl-1-oxide, 3-fluoro-pyridin-4-yl-1-oxide, 2-(difluoro-methyl)-pyridin-4-yl-1-oxide, 2-methylpyridin-4-yl-1-oxide, 2-isopropyl-pyridin-4-yl-1-oxide, 2-t-butyl-pyridin-4-yl-1-oxide, 2-(trifluoro-methyl)-pyridin-4-yl-1-oxide, 2-cyano-pyridin-4-yl-1-oxide, 2,6-dimethyl-pyridin-4-yl-1-oxide, 3-fluoro-5-chloro-pyridin-4-yl-1-oxide, 3-chloro-5-fluoro-pyridin-4-yl-1-oxide, pyrimidin-4-yl, 2-methyl-pyrimidin-4-yl, pyrimidin-5-yl, 2-(trifluoro-methyl)-pyrimidin-4-yl, 6-(trifluoro-methyl)-pyrimidin-4-yl, 2-(methyl-amino)-pyrimidin-5-yl, pyrimidin-4-yl-1-oxide, and 2-methyl-pyrimidin-4-yl-1-oxide. In certain embodiments, the present invention is directed to compounds of formula (I) wherein $R^4$ is selected from the group consisting of 1-(methoxy-carbonyl)-piperidin-4-yl, 1-(methoxy-carbonyl)-piperidin-3-yl, 2-fluoro-6-amino-pyrazin-3-yl, pyridazin-4-yl, 1-ethyl-pyridazin-4-yl-6-one, 1-methyl-pyridazin-4-yl-6-one, 1-isopropyl-pyridazin-4-yl-6-one pyridazin-4-yl-1-oxide, 6-fluoro-pyridin-3-yl, 6-amino-pyridin-3-yl, 2-chloro-6-amino-pyridin-3-yl, 2-fluoro-6-amino-pyridin-3-yl, 2-methyl-6-amino-pyridin-3-yl, 5-fluoro-6-amino-pyridin-3-yl, 2-fluoro-5-methoxy-pyridin-3-yl, pyridin-4-yl, 2-fluoro-pyridin-4-yl, 3-fluoro-pyridin-4-yl, 2-methyl-pyridin-4-yl, 2-isopropyl-pyridin-4-yl, 2-t-butyl-pyridin-4-yl, 2-(difluoro-methyl)-pyridin-4-yl, 2-(trifluoro-methyl)-pyridin-4-yl, 2-cyano-pyridin-4-yl, 2-cyclopropyl-pyridin-4-yl, 2-(difluoro-methoxy)-pyridin-4-yl, 2-(difluoro-methyl)-pyridin-4-yl, 3-(trifluoro-methyl)-pyridin-4-yl, 3-fluoro-5-chloro-pyridin-4-yl, 2-(trifluoro-methyl)-5-(methyl-carbonyl-amino)-pyridin-4-yl, 1-methyl-pyridin-3-yl-6-one, 1-methyl-pyridin-4-yl-2-one, pyridin-3-yl-1-oxide, 6-amino-pyridin-3-yl-1-oxide, 2-methyl-6-amino-pyridin-3-yl-1-oxide, pyridin-4-yl-1-oxide, 3-fluoro-pyridin-4-yl-1-oxide, 2-(difluoro-methyl)-pyridin-4-yl-1-oxide, 2-methyl-pyridin-4-yl-1-oxide, 2-isopropyl-pyridin-4-yl-1-oxide, 2-t-butyl-pyridin-4-yl-1-oxide, 2-(trifluoro-methyl)-pyridin-4-yl-1-oxide, 2-cyano-pyridin-4-yl-1-oxide, 2,6-dimethyl-pyridin-4-yl-1-oxide, 3-fluoro-5-chloro-pyridin-4-yl-1-oxide, 3-chloro-5-fluoro-pyridin-4-yl-1-oxide, pyrimidin-4-yl, 2-methyl-pyrimidin-4-yl, pyrimidin-5-yl, 2-(trifluoro-methyl)-pyrimidin-4-yl, 6-(trifluoro-methyl)-pyrimidin-4-yl, 2-(methyl-amino)-pyrimidin-5-yl, pyrimidin-4-yl-1-oxide, and 2-methyl-pyrimidin-4-yl-1-oxide. In certain embodiments, the present invention is directed to compounds of formula (I) wherein $R^4$ is selected from the group consisting of 2-fluoro-6-amino-pyrazin-3-yl, 1-ethyl-pyridazin-4-yl-6-one, 1-methyl-pyridazin-4-yl-6-one, 6-amino-pyridin-3-yl, 2-chloro-6-amino-pyridin-3-yl, 2-fluoro-6-amino-pyridin-3-yl, 2-methyl-6-amino-pyridin-3-yl, 5-fluoro-6-amino-pyridin-3-yl, pyridin-4-yl, 2-fluoro-pyridin-4-yl, 3-fluoro-pyridin-4-yl, 2-methyl-pyridin-4-yl, 2-isopropyl-pyridin-4-yl, 2-(difluoro-methyl)-pyridin-4-yl, 2-(trifluoro-methyl)-pyridin-4-yl, 2-cyano-pyridin-4-yl, 2-cyclopropyl-pyridin-4-yl, 2-(difluoro-methoxy)-pyridin-4-yl, 3-fluoro-5-chloro-pyridin-4-yl, 1-methyl-pyridin-4-yl-2-one, pyridin-3-yl-1-oxide, pyridin-4-yl-1-oxide, 3-fluoro-pyridin-4-yl-1-oxide, 2-(difluoro-methyl)-pyridin-4-yl-1-oxide, 2-methyl-pyridin-4-yl-1-oxide, 2-isopropyl-pyridin-4-yl-1-oxide, 3-fluoro-5-chloro-pyridin-4-yl-1-oxide, 3-chloro-5-fluoro-pyridin-4-yl-1-oxide, pyrimidin-4-yl, 2-(trifluoro-methyl)-pyrimidin-4-yl, 6-(trifluoro-methyl)-pyrimidin-4-yl, 2-(methyl-amino)-pyrimidin-5-yl, and pyrimidin-4-yl-1-oxide.

In certain embodiments, the present invention is directed to compounds of formula (I) wherein $R^4$ is selected from the group consisting of 1-methyl-pyridazin-4-yl-6-one, 2-chloro-6-amino-pyridin-3-yl, 2-fluoro-6-amino-pyridin-3-yl, 2-methyl-6-amino-pyridin-3-yl, pyridin-4-yl, 2-fluoro-pyridin-4-yl, 3-fluoro-pyridin-4-yl, 2-methyl-pyridin-4-yl, 2-(difluoro-methyl)-pyridin-4-yl, 2-(trifluoro-methyl)-pyridin-din-4-yl, 2-cyano-pyridin-4-yl, 2-cyclopropyl-pyridin-4-yl, 2-(difluoro-methoxy)-pyridin-4-yl, 3-fluoro-5-chloro-pyridin-4-yl, 1-methyl-pyridin-4-yl-2-one, pyridin-4-yl-1-oxide, 3-fluoro-pyridin-4-yl-1-oxide, 2-(difluoro-methyl)-pyridin-4-yl-1-oxide, 2-isopropyl-pyridin-4-yl-1-oxide, 3-chloro-5-fluoro-pyridin-4-yl-1-oxide, pyrimidin-4-yl, 2-(trifluoro-methyl)-pyrimidin-4-yl, and 2-(methyl-amino)-pyrimidin-5-yl. In certain embodiments, the present invention is directed to compounds of formula (I) wherein $R^4$ is selected from the group consisting of 2-chloro-6-amino-pyridin-3-yl, 2-fluoro-6-amino-pyridin-3-yl, 2-methyl-6-amino-pyridin-3-yl, pyridin-4-yl, 2-fluoro-pyridin-4-yl, 3-fluoro-pyridin-4-yl, 2-methyl-pyridin-4-yl, 2-(trifluoro-methyl)-pyridin-4-yl, 2-(difluoro-methyl)-pyridin-4-yl, 2-cyano-pyridin-4-yl, 3-fluoro-5-chloro-pyridin-4-yl, pyridin-4-yl-1-oxide, 3-fluoro-pyridin-4-yl-1-oxide, 2-(difluoro-methyl)-pyridin-4-yl-1-oxide, 2-isopropyl-pyridin-4-yl-1-oxide, and 2-(trifluoro-methyl)-pyrimidin-4-yl. In certain embodiments, the present invention is directed to compounds of formula (I) wherein $R^4$ is selected from the group consisting of 2-fluoro-6-amino-pyridin-3-yl, 2-methyl-6-amino-pyridin-3-yl, pyridin-4-yl, 2-(trifluoro-methyl)-pyridin-4-yl, 3-fluoro-5-chloro-pyridin-4-yl, pyridin-4-yl-1-oxide, and 3-fluoro-pyridin-4-yl-1-oxide. In certain embodiments, the present invention is directed to compounds of formula (I) wherein $R^4$ is selected from the group consisting of 1-methyl-1H-indazol-5-yl, 2-methyl-indazol-5-yl, isoindol-4-yl-2-one, 2-methyl-isoindolin-5-yl-1-one, isobenzofuran-5-yl-1-one, 2-methyl-3,4-dihydroisoquinolin-6-yl-1-one, 2,2-difluoro-benzo[d][1,3]dioxol-5-yl and 2,3-dihydro-benzo[b][1,4]dioxin-6-yl.

In certain embodiments, the present invention is directed to compounds of formula (I) wherein $R^S$ is selected from any one or more of (a) through (g), independently selected from any (a) through (g) as described in any of the embodiments herein.

In certain embodiments, the present invention is directed to compounds of formula (I) wherein $R^5$ is selected from the group consisting of (a) $C_{1-4}$alkyl; wherein the $C_{1-4}$alkyl is optionally substituted with one or more halogen; and further optionally substituted with a substituent selected from the group consisting of hydroxy, $C_{1-4}$alkoxy, fluorinated $C_{1-4}$alkoxy, —C(O)OH, —C(O)—O—($C_{1-4}$alkyl), —C(O)—O-(fluorinated $C_{1-4}$alkyl), —C(O)-(fluorinated $C_{1-4}$alkyl), and —C(O)—$NR^LR^M$; wherein $R^L$ and $R^M$ are each independently selected from the group consisting of hydrogen and $C_{1-2}$alkyl;

(b) —$CH_2$—$C_{3-8}$cycloalkyl or —$CH_2$-adamant-1-yl; wherein the $C_{3-8}$cycloalkyl is optionally substituted with one to two halogen or $C_{1-4}$alkyl; and further optionally substituted with a substituent selected from the group consisting of —C(O)OH, —C(O)—O—$C_{1-4}$alkyl, —C(O)-(5 to 6 membered saturated heterocyclyl), —C(O)-(isoindolin-2-yl), —C(O)-(azaspiro[2.4]heptan-5-yl), —C(O)-(carboxy substituted azaspiro[2.4]heptan-5-yl), —C(O)—($NR^FR^Q$ substituted azaspiro[2.4]heptan-5-yl), phenyl, 1,1'-biphen-4-yl and —C(O)—$NR^FR^Q$; wherein the —C(O)-(5 to 6 membered saturated heterocyclyl) substituent on the —$CH_2$—$C_{3-8}$cycloalkyl is further optionally substituted on the (5 to 6 membered heterocyclyl) with one to two substituents independently selected from the group consisting of halogen, $C_{1-4}$alkyl, —C(O)OH, —C(O)—O—$C_{1-4}$alkyl, phenyl and $C_{3-8}$cycloalkyl; wherein the phenyl substituent on the —$CH_2$—$C_{3-8}$cycloalkyl is further optionally substituted with $C_{1-4}$alkoxy; and wherein $R^P$ and $R^Q$ are each independently selected from the group consisting of hydrogen and $C_{1-4}$alkyl;
(c) -$L^1$-(5 to 6 membered saturated heterocyclyl); wherein $L^1$ is selected from the group consisting of —$CH_2$— and —$CH_2$—C(O)—; wherein, when $L^1$ is —$CH_2$—C(O)—, then the (5 to 6 membered saturated heterocyclyl) is bound to the —C(O)— portion of $L^1$; and wherein the 5 to 6 membered saturated heterocyclyl is optionally substituted with one to two oxo group;
(d) —$C_{1-2}$alkyl-phenyl; wherein the phenyl is optionally substituted with one to two substituents independently selected from the group consisting of halogen, hydroxy, $C_{1-4}$alkyl, fluorinated $C_{1-4}$alkyl, $C_{1-4}$ alkoxy, fluorinated $C_{1-4}$alkoxy, —$OCH_2$—C(O)—$NR^SR^T$, phenyl and phenoxy; and wherein $R^S$ and $R^T$ are each independently selected from the group consisting of hydrogen and $C_{1-2}$alkyl;
(e) 1,2,3-triazol-4-yl, 1,2,5-triazol-3-yl, —$CH_2$-1,2,3-triazol-4-yl and —$CH_2$-1,2,5-triazol-3-yl; wherein the 1,2,3-triazol-4-yl or 1,2,5-triazoly-3-yl, whether alone or as part of the substituent group is optionally substituted with a substituent selected from the group consisting of $C_{1-4}$alkyl, fluorinated $C_{1-4}$alkyl, phenyl and piperidinyl; wherein the piperidinyl is optionally substituted with —C(O)—$C_{1-4}$alkyl;
(f) —$CH_2$-(5 to 6 membered or 9 to 10 membered heterocyclyl); wherein the (5 to 6 membered or 9 to 10 membered heterocyclyl) is other than triazolyl; wherein the (5 to 6 membered or 9 to 10 membered heterocyclyl) is optionally substituted with one to two substituents independently selected from the group consisting of halogen, hydroxy, oxo, $C_{1-4}$alkyl, fluorinated $C_{1-4}$alkyl, $C_{1-4}$alkoxy, fluorinated $C_{1-4}$alkoxy, cyano, —C(O)OH, —C(O)—O—$C_{1-4}$alkyl, —$C_{1-2}$alkyl-O—$C_{1-4}$alkyl, —$C_{1-2}$alkyl-O-(fluorinated $C_{1-4}$alkyl), —C(O)—$NR^VR^W$, —$C_{1-2}$alkyl-C(O)—$NR^VR^W$, -(5 to 6 membered saturated heterocyclyl), —C(O)-(5 to 6 membered saturated heterocyclyl), —C(O)-(carboxy substituted 5 to 6 membered saturated heterocyclyl), —$C_{1-2}$alkyl-C(O)-(5 to 6 membered saturated heterocyclyl), phenyl and pyridinyl; wherein the pyridinyl substituent on the —$CH_2$-(5 to 6 membered or 9 to 10 membered heterocyclyl) is further optionally substituted with one to two substituents independently selected from the group consisting of halogen and fluorinated $C_{1-4}$alkyl; and wherein $R^V$ and $R^W$ are each independently selected from the group consisting of hydrogen and $C_{1-4}$alkyl;
and (g) —$CH_2$—$NR^8R^9$; wherein $R^8$ is selected from the group consisting of hydrogen and $C_{1-2}$alkyl; $R^9$ is selected from the group consisting of $C_{1-4}$alkyl, fluorinated $C_{1-4}$alkyl, $C_{1-4}$alkoxy, fluorinated $C_{1-4}$alkoxy, —C(O)—$C_{1-4}$alkyl, —C(O)—$C_{1-2}$alkyl-O—$C_{1-4}$alkyl, —C(O)-phenyl, —C(O)—$C_{1-2}$alkyl-phenyl, —C(O)—O—$C_{1-4}$alkyl, —C(O)—O— phenyl, —C(O)—O—$C_{1-2}$alkyl-phenyl, —C(O)—$C_{3-7}$cycloalkyl, —C(O)-(1-methyl-cycloprop-1-yl), —C(O)-(5 to 6 membered saturated heterocyclyl), —C(O)—$C_{1-2}$alkyl-C(O)-(5 to 6 membered saturated heterocyclyl), —O—$C_{1-2}$ alkyl-C(O)-(5 to 6 membered saturated heterocyclyl), —C(O)-(1-methyl-pyridinyl-one) and —C(O)—$NR^XR^Y$; and
wherein $R^X$ and $R^Y$ are each independently selected from the group consisting of hydrogen and $C_{1-2}$alkyl; In certain embodiments, the present invention is directed to compounds of formula (I) wherein $R^S$ is selected from the group consisting of (a) $C_{1-4}$alkyl; wherein the $C_{1-4}$alkyl is optionally substituted with a substituent selected from the group consisting of $C_{1-4}$alkoxy, fluorinated $C_{1-4}$alkoxy, —C(O)—O—($C_{1-4}$alkyl) and —C(O)-(fluorinated $C_{1-4}$alkyl); (b) —$CH_2$—$C_{3-8}$cycloalkyl or —$CH_2$-adamant-1-yl; wherein the $C_{3-8}$cycloalkyl is optionally substituted with one or more halogen; and further optionally substituted with a substituent selected from the group consisting of —C(O)-(5 to 6 membered saturated heterocyclyl), —C(O)-(azaspiro[2.4]heptan-5-yl), —C(O)-(carboxy substituted azaspiro[2.4]heptan-5-yl), —C(O)—($NR^PR^Q$ substituted azaspiro[2.4]heptan-5-yl), and —C(O)—$NR^PR^Q$; wherein the —C(O)-(5 to 6 membered saturated heterocyclyl) substituent on the —$CH_2$—$C_{3-8}$cycloalkyl is further optionally substituted on the (5 to 6 membered heterocyclyl) with a substituent selected from the group consisting of phenyl and $C_{3-8}$cycloalkyl; and wherein $R^P$ and $R^Q$ are each independently selected from the group consisting of hydrogen and $C_{1-4}$alkyl; (c) -$L^1$-(5 to 6 membered saturated heterocyclyl); wherein $L^1$ is —$CH_2$—; and wherein the 5 to 6 membered saturated heterocyclyl is optionally substituted with one to two oxo group; (d) —$C_{1-2}$alkyl-phenyl; wherein the phenyl is optionally substituted with a substituent selected from the group consisting of halogen and $C_{1-4}$alkoxy; (e) 1,2,3-triazol-4-yl, 1,2,5-triazoly-3-yl, —$CH_2$-1,2,3-triazol-4-yl and —$CH_2$-1,2,5-triazol-3-yl; wherein the 1,2,3-triazol-4-yl or 1,2,5-triazoly-3-yl, whether alone or as part of the substituent group is optionally substituted with a substituent selected from the group consisting of $C_{1-4}$alkyl, fluorinated $C_{1-4}$alkyl and phenyl; (f) —$CH_2$-(5 to 6 membered or 9 to 10 membered heterocyclyl); wherein the 5 to 6 membered heterocyclyl is other than triazolyl; wherein the (5 to 6 membered or 9 to 10 membered heterocyclyl) is optionally substituted with one to two substituents independently selected from the group consisting of halogen, oxo, $C_{1-4}$alkyl, fluorinated $C_{1-4}$ alkyl, fluorinated $C_{1-4}$alkoxy, —C(O)OH, —$C_{1-2}$alkyl-O—$C_{1-4}$alkyl, —$C_{1-2}$alkyl-O-(fluorinated $C_{1-4}$alkyl), —C(O)—$NR^VR^W$, —$C_{1-2}$alkyl-C(O)—$NR^VR^W$, -(5 to 6 membered saturated heterocyclyl), —C(O)-(5 to 6 membered saturated heterocyclyl), —C(O)-(carboxy substituted 5 to 6 membered saturated heterocyclyl), —$C_{1-2}$alkyl-C(O)-(5 to 6 membered saturated heterocyclyl), phenyl and pyridinyl; wherein the pyridinyl substituent on the —$CH_2$-(5 to 6 membered or 9 to 10 membered heterocyclyl) is further optionally substituted halogen; and wherein $R^V$ and $R^W$ are each independently selected from the group consisting of hydrogen and $C_{1-4}$alkyl; and (g) —$CH_2$—$NR^8R^9$; wherein $R^8$ is selected from the group consisting of hydrogen and $C_{1-2}$alkyl; $R^9$ is selected from the group consisting of fluorinated $C_{1-4}$alkoxy, —C(O)—$C_{1-4}$alkyl, —C(O)—$C_{1-2}$alkyl-O—$C_{1-4}$alkyl, —C(O)-phenyl, —C(O)—$C_{1-2}$ alkyl-phenyl, —C(O)—O—$C_{1-4}$alkyl, —C(O)—O—$C_{1-2}$alkyl-phenyl, —C(O)—$C_{3-7}$cycloalkyl, —C(O)-(1-methyl-cycloprop-1-yl), —C(O)-(5 to 6 membered saturated heterocyclyl), —C(O)—$C_{1-2}$alkyl-C(O)-(5 to 6 membered saturated heterocyclyl), —O—$C_{1-2}$alkyl-C(O)-(5 to 6 membered saturated heterocyclyl), —C(O)-(1-methyl-pyridinyl-one) and —C(O)—$NR^XR^Y$; and wherein $R^X$ and $R^Y$ are each independently selected from the group consisting of hydrogen and $C_{1-2}$alkyl.

In certain embodiments, the present invention is directed to compounds of formula (I) wherein $R^S$ is selected from the group consisting of (a) $C_{1-4}$alkyl; wherein the $C_{1-4}$alkyl is optionally substituted with a substituent selected from the group consisting of hydroxy, $C_{1-4}$alkoxy, fluorinated $C_{1-4}$alkoxy, —C(O)—O—($C_{1-4}$alkyl) and —C(O)—NR$^L$R$^M$; wherein R$^L$ and R$^M$ are each independently selected from the group consisting of hydrogen and $C_{1-2}$alkyl; (b) —CH$_2$—C$_{3-6}$cycloalkyl or —CH$_2$-adamant-1-yl; wherein the C$_{3-6}$cycloalkyl is optionally substituted with one or more $C_{1-4}$alkyl; and further optionally substituted with a substituent selected from the group consisting of $C_{1-4}$alkyl, —C(O)OH, —C(O)—O—$C_{1-4}$alkyl, —C(O)-(5 to 6 membered saturated heterocyclyl), —C(O)-(isoindolin-2-yl), phenyl, 1,1'-biphen-4-yl and —C(O)—NR$^P$R$^Q$; wherein the —C(O)-(5 to 6 membered saturated heterocyclyl) substituent on the —CH$_2$—C$_{3-8}$cycloalkyl is further optionally substituted on the (5 to 6 membered heterocyclyl) with one to two substituents independently selected from the group consisting of halogen, $C_{1-4}$alkyl, —C(O)OH, and phenyl; wherein the phenyl substituent on the —CH$_2$—C$_{3-8}$cycloalkyl is further optionally substituted with $C_{1-4}$alkoxy; and wherein R$^P$ and R$^Q$ are each independently selected from the group consisting of hydrogen and $C_{1-4}$alkyl; (c) -L$^1$-(5 to 6 membered saturated heterocyclyl); wherein L$^1$ is selected from the group consisting of —CH$_2$— and —CH$_2$—C(O)—; wherein, when L$^1$ is —CH$_2$—C(O)—, then the (5 to 6 membered saturated heterocyclyl) is bound to the —C(O)— portion of L$^1$; and wherein the (5 to 6 membered saturated heterocyclyl) is optionally substituted with one to two oxo group; (d) —C$_{1-2}$alkyl-phenyl; wherein the phenyl is optionally substituted with a substituent selected from the group consisting of halogen, hydroxy, $C_{1-4}$alkoxy, —OCH$_2$—C(O)—NR$^S$R$^T$, phenyl and phenoxy; and wherein R$^S$ and R$^T$ are each independently selected from the group consisting of hydrogen and $C_{1-2}$alkyl; (e) 1,2,3-triazol-4-yl; wherein the 1,2,3-triazol-4-yl is optionally substituted with a substituent selected from the group consisting of $C_{1-4}$alkyl, phenyl and piperidinyl; wherein the piperidinyl is optionally substituted with —C(O)—C$_{1-2}$alkyl; (f) —CH$_2$-(5 to 6 membered or 9 to 10 membered heterocyclyl); wherein the (5 to 6 membered or 9 to 10 heterocyclyl) is other than triazolyl; wherein the (5 to 6 membered or 9 to 10 membered heterocyclyl) is optionally substituted with one or more substituents independently selected from the group consisting of halogen, oxo, $C_{1-4}$alkyl, fluorinated $C_{1-4}$alkyl, cyano, —C(O)OH, and —C(O)—NR$^V$R$^W$; wherein R$^V$ and R$^W$ are each independently selected from the group consisting of hydrogen and $C_{1-2}$alkyl; and (g) —CH$_2$—NR$^8$R$^9$; wherein R$^8$ is $C_{1-2}$alkyl; R$^9$ is —C(O)—O—$C_{1-4}$alkyl.

In certain embodiments, the present invention is directed to compounds of formula (I) wherein $R^5$ is selected from the group consisting of (a) $C_{1-4}$alkyl; wherein the $C_{1-4}$alkyl is optionally substituted with a substituent selected from the group consisting of $C_{1-4}$alkoxy and fluorinated $C_{1-4}$alkoxy; (b) —CH$_2$—C$_{3-8}$cycloalkyl; wherein the C$_{3-6}$cycloalkyl is optionally substituted with a substituent selected from the group consisting of —C(O)-(5 to 6 membered saturated heterocyclyl) and —C(O)—NR$^P$R$^Q$; and wherein R$^P$ and R$^Q$ are each independently selected from the group consisting of hydrogen and $C_{1-4}$alkyl; (c) -L$^1$-(5 to 6 membered saturated heterocyclyl); wherein L$^1$ is —CH$_2$—; and wherein the (5 to 6 membered saturated heterocyclyl) is optionally substituted with one to two oxo group; (d) —C$_{1-2}$alkyl-phenyl; wherein the phenyl portion is optionally substituted with halogen; and (f) —CH$_2$-(5 to 6 membered heterocyclyl); wherein the (5 to 6 membered heterocyclyl) is other than triazolyl; wherein the (5 to 6 membered heterocyclyl) is optionally substituted with one to two substituents independently selected from the group consisting of halogen, $C_{1-4}$ alkyl, fluorinated $C_{1-4}$alkyl and —C(O)—NR$^V$R$^W$; and wherein R$^V$ and R$^W$ are each independently selected from the group consisting of hydrogen and $C_{1-4}$alkyl.

In certain embodiments, the present invention is directed to compounds of formula (I) wherein $R^5$ is selected from the group consisting of (a) $C_{1-4}$alkyl; wherein the $C_{1-4}$alkyl is optionally substituted with one or more halogen, and further optionally substituted with a substituent selected from the group consisting of hydroxy, $C_{1-4}$alkoxy and fluorinated $C_{1-4}$alkoxy; (b) —CH$_2$—C$_{3-8}$cycloalkyl; wherein the C$_{3-6}$cycloalkyl is optionally substituted with one or more halogen, and further optionally substituted optionally substituted with $C_{1-4}$alkyl; (c) -L$^1$-(5 to 6 membered saturated heterocyclyl); wherein L$^1$ is —CH$_2$—; (d) —C$_{1-2}$alkyl-phenyl; wherein the phenyl is optionally substituted with one to two substituents independently selected from the group consisting of halogen and hydroxy; (e) 1,2,5-triazoly-3-yl; wherein the 1,2,5-triazoly-3-yl, is optionally substituted with a substituent selected from the group consisting of $C_{1-4}$alkyl, and phenyl; and (f) —CH$_2$-(5 to 6 membered heterocyclyl); wherein the (5 to 6 membered heterocyclyl) is other than triazolyl; wherein the (5 to 6 membered heterocyclyl) is optionally substituted with a substituent selected from the group consisting of halogen, fluorinated $C_{1-4}$alkyl, and fluorinated $C_{1-4}$alkoxy.

In certain embodiments, the present invention is directed to compounds of formula (I) wherein $R^5$ is selected from the group consisting of (a) $C_{1-4}$alkyl; wherein the $C_{1-4}$alkyl is optionally substituted with $C_{1-4}$ alkoxy; and (b) —CH$_2$—C$_{3-6}$cycloalkyl.

In certain embodiments, the present invention is directed to compounds of formula (I) wherein $R^5$ is $C_{1-4}$alkyl, wherein the $C_{1-4}$alkyl is optionally substituted as described herein.

In certain embodiments, the present invention is directed to compounds of formula (I) wherein $R^5$ is selected from the group consisting ethyl, R*-ethyl, S*-ethyl, n-propyl, R*-(n-propyl), S*-(n-propyl), 2-methoxy-ethyl-, 2-t-butoxy-ethyl-, R*-(2-methoxy-ethyl-), R-(2-methoxy-ethyl), 2-(methyl-d$_3$)-ethyl-2,2-d$_2$-, isobutyl, R*-isobutyl, S*-isobutyl, S-(2-methoxy-ethyl-), R-(2-methoxy-ethyl-), R-(2-hydroxy-ethyl-2,2-d$_2$-), S-(2-hydroxy-ethyl-2,2-d$_2$-), S-(2-(difluoro-methoxy)-ethyl-), R*-(2-(methoxy-d3)-ethyl-), S*-(2-(methoxy-d3)-ethyl-2,2-d2-), R*-(2-(methoxy-d$_3$)-ethyl-2,2-d$_2$-), 2-(difluoro-methoxy)-ethyl-, R*-(2-(difluoro-methoxy)-ethyl-2,2-d2-), S*-(2-(difluoro-methoxy)-ethyl-2,2-d$_2$-), 2-(2-(methyoxy-d$_3$)-ethyl-2,2-d$_2$-), 2-trifluoro-methoxy-ethyl-, R*-(2-trifluoro-methoxy-ethyl-), R-(2-trifluoro-methoxy-ethyl-), S-(2-(difluoro-methoxy)-ethyl-2,2-d$_2$-), R-(2-(difluoro-methoxy)-ethyl-2,2-d$_2$-), R-(3,3,3-trifluoro-n-propyl), S-(3,3,3-trifluoro-n-propyl), S-(2-hydroxy-ethyl-), R-(2-hydroxy-ethyl-), S-(2-t-butoxy-ethyl-), S*-(2-methoxy-ethyl), R-(2-t-butoxy-ethyl-), S-(2-methoxy-2-methyl-n-propyl-), R-(2-methoxy-2-methyl-n-propyl-), S-(2-hydroxy-2-methyl-n-propyl-), R-(2-hydroxy-2-methyl-n-propyl-), R-(2-(difluoro-methoxy)-ethyl-, R*-(2-hydroxy-ethyl-), S*-(2-hydroxy-ethyl-), 2-ethoxy-ethyl-, isopropyloxy-methyl-, R*-(2-isopropyloxy-ethyl), S*-(2-isopropyloxy-ethyl), R*-(2-(difluoro-methoxy)-ethyl-), R-(2-(difluoro-methoxy)-ethyl-), S*-(2-methoxy-n-propyl-), R-(2-methoxy-n-propyl-), methoxy-carbonyl-methyl-, 2-(difluoro-methyl-carbonyl)-methyl-, and dimethyl-amino-carbonyl-methyl-.

In certain embodiments, the present invention is directed to compounds of formula (I) wherein $R^5$ is —CH$_2$—C$_{3-8}$cycloalkyl (preferably —CH$_2$-cyclopropyl) or —CH$_2$-adamant-1-yl, wherein the —CH$_2$—C$_{3-8}$cycloalkyl is optionally substituted as described herein. In certain embodiments, the present invention is directed to compounds of formula (I) wherein $R^5$ is selected from the group consisting of —CH$_2$-cyclopropyl, wherein the —CH$_2$-cyclopropyl is optionally substituted as described herein.

In certain embodiments, the present invention is directed to compounds of formula (I) wherein $R^5$ is selected from the group consisting of cyclopropyl-methyl-, S-(cyclopropyl-methyl-), S*-(cyclopropyl-methyl-), R-(cyclopropyl-methyl-), R*-(cyclopropyl-methyl-), 2-methyl-cyclopropyl-methyl-, R-((2-methyl-cyclopropyl)-methyl-), S-((2-methyl-cyclopropyl)-methyl-), S*—(S*-(2-maethyl-cyclopropyl)-methyl-), R*—(S*-(2-methyl-cyclopropyl)-methyl-), R*—(R*-(2-methyl-cyclopropyl)-methyl-), R-(2,2-difluoro-cyclopropyl-methyl-), S-(2,2-difluoro-cyclopropyl-methyl-), 2R*-carboxy-1S*-cyclopropyl-methyl-, 2S*-carboxy-1R*-cyclopropyl-methyl-, 2S*-carboxy-1S*-cyclopropyl-methyl-, 2R*-carboxy-1R*-cyclopropyl-methyl-, 2S*-(ethoxy-carbonyl)-1S*-cyclopropyl-methyl-, 2R*-(ethoxy-carbonyl)-1R*-cyclopropyl-methyl-, —C(O)-isoindolin-2-yl, —C(O)-pyrrolidin-1-yl, 2R*-(piperidin-1-yl-carbonyl)-1R*-cyclopropyl-methyl-, 2S*-(piperidin-1-yl-carbonyl)-1S*-cyclopropyl-methyl-, 2-(piperidin-1-yl-carbonyl)-cyclopropyl-methyl-, 2S*-(piperidin-1-yl-carbonyl)-1R*-cyclopropyl-methyl-,2R*-(piperidin-1-yl-carbonyl)-1S*-cyclopropyl-methyl-, R*-(2S*-(piperidin-1-yl-carbonyl)-cyclopropyl-methyl-), S*-(2R*-(piperidin-1-yl-carbonyl)-cyclopropyl-methyl-), S*-(2-(piperidin-1-yl-carbonyl)-cyclopropyl-methyl-), 2-(4,4-difluoro-piperidin-1-yl-carbonyl)-cyclopropyl-methyl-, 2S*-(3-carboxy-piperidin-1-yl-carbonyl)-1R*-cyclopropyl-methyl-, 2R*-(3-carboxy-piperidin-1-yl-carbonyl)-1R*-cyclopropyl-methyl-, 2S*-(4-carboxy-piperidin-1-yl-carbonyl)-1R*-cyclopropyl-methyl-, 2R*-(4-carboxy-piperidin-1-yl-carbonyl)-1R*-cyclopropyl-methyl-, 2R*-(piperazin-1-yl-carbonyl)-1S*-cyclopropyl-methyl-, 2R*-(morpholin-4-yl-carbon yl-methyl-, 2S*-(morpholin-4-yl-carbon yl-methyl-, 2R*-(isoindolin-2-yl-carbonyl)-1S*cyclopropyl-methyl, 2S*-(isoindolin-2-yl-carbonyl)-1S*cyclopropyl-methyl, 2S*-(isoindolin-2-yl-carbonyl)-1R*cyclopropyl-methyl, 2R*-(isoindolin-2-yl-carbonyl)-1R*cyclopropyl-methyl, 2R*-(pyrrolidin-1-yl-carbonyl)-1S*-cyclopropyl-methyl-, 2S*-(pyrrolidin-1-yl-carbonyl)-1R*-cyclopropyl-methyl-, 2S*-(pyrrolidin-1-yl-carbonyl)-1S*-cyclopropyl-methyl-, 2R*-(pyrrolidin-1-yl-carbonyl)-1R*-cyclopropyl-methyl-, 2-(3-phenyl-pyrrolidin-1-yl-carbonyl)-cyclopropyl-methyl-, 2R*-(3-phenyl-pyrrolidin-1-yl-carbonyl)-1S*-cyclopropyl-methyl-, 2S*-(3-phenyl-pyrrolidin-1-yl-carbonyl)-1S*-cyclopropyl-methyl-, 2R*-(3-phenyl-pyrrolidin-1-yl-carbonyl)-1R*-cyclopropyl-methyl-, 2S*-(3-phenyl-pyrrolidin-1-yl-carbonyl)-1R*-cyclopropyl-methyl-, 2-(3-cyclopropyl-pyrrolidin-1-yl-carbonyl)-cyclopropyl-methyl-, 2S*-(4-methoxy-phenyl)-1S*-cyclopropyl-methyl-, 2R*-(4-methoxy-phenyl)-1S*-cyclopropyl-methyl-, 2-(1,1'-biphen-4-yl)-cyclopropyl-methyl, 2-(azaspiro[2.4]heptan-5-yl-carbonyl)-cyclopropyl-methyl-, 2-(7-carboxy-azaspiro[2.4]heptan-5-yl-carbonyl)-cyclopropyl-methyl-, 2-(7-amino-azaspiro[2.4]heptan-5-yl-carbonyl)-cyclopropyl-methyl-, 2-(amino-carbonyl)-cyclopropyl-methyl-, 2R*-(amino-carbonyl)-1S*-cyclopropyl-methyl-, 2S*-(amino-carbonyl)-1S*-cyclopropyl-methyl-, R*-(2S*-(amino-carbonyl)-1S*-cyclopropyl-methyl-), R*-(2S*-(amino-carbonyl)-1R*-cyclopropyl-methyl-), S*-(2R*-(amino-carbonyl)-1R*-cyclopropyl-methyl-), S*-(2R*-(amino-carbonyl)-1S*-cyclopropyl-methyl-), S*-(2S*-(amino-carbonyl)-1R*-cyclopropyl-methyl-), R*-(2R*-(amino-carbonyl)-1S*-cyclopropyl-methyl-), cyclobutyl-methyl-, R-(cyclobutyl-methyl-), S-(cyclobutyl-methyl-), 3,3-dimethyl-cyclobutyl-methyl-, cyclopentyl-methyl-, 4-methyl-cyclohexyl-methyl-, cyclohexyl-methyl-, 4,4-dimethyl-cyclohexyl-methyl- and adamantan-1-yl-methyl-.

In certain embodiments, the present invention is directed to compounds of formula (I) wherein $R^5$ is -L$^1$-(5 to 6 membered saturated heterocyclyl), wherein L$^1$ is selected from the group consisting of —CH$_2$— and —CH$_2$—C(O)—; wherein, when L$^1$ is —CH$_2$—C(O)—, then the (5 to 6 membered saturated heterocyclyl) is bound to the —C(O)— portion of L$^1$; and wherein the (5 to 6 membered saturated heterocyclyl) is optionally substituted as described herein.

In certain embodiments, the present invention is directed to compounds of formula (I) wherein $R^5$ is -L$^1$-(5 to 6 membered saturated heterocyclyl), wherein L$^1$ is —CH$_2$—. In certain embodiments, the present invention is directed to compounds of formula (I) wherein $R^5$ is -L$^1$-(5 to 6 membered saturated heterocyclyl), wherein L$^1$ is —CH$_2$—C(O)—. In certain embodiments of the present invention is directed to compounds of formula (I) wherein $R^5$ is -L$^1$-(5 to 6 membered saturated heterocyclyl); wherein the (5 to 6 membered saturated heterocyclyl) is selected from the group consisting of pyrrolidinyl, tetrahydrofuranyl, tetrahydropyranyl, piperazinyl and morpholinyl; and wherein the (5 to 6 membered saturated heterocyclyl) is further optionally substituted as described herein.

In certain embodiments, the present invention is directed to compounds of formula (I) wherein $R^5$ is selected from the group consisting of (pyrrolidin-1-yl-2-one)-methyl-, R*-((pyrrolidin-1-yl-2-one)-methyl-), S*-((pyrrolidin-1-yl-2-one)-methyl-), R*-(pyrrolidin-1-yl-2-one-methyl-), R-(pyrrolidin-1-yl-2-one-methyl-), S*-(pyrrolidin-1-yl-2-one-methyl-), pyrrolidin-1-yl-2-one-methyl-, (pyrrolidin-1yl-2,5-dione)-methyl-, tetrahydrofuran-2-yl-methyl-, S*-(tetrahydrofuran-2-yl-methyl-), R*-(tetrahydropyran-2S*-yl-methyl-), S*-(tetrahydropyran-2S*-yl-methyl-), tetrahydropyran-2R*-yl-methyl-, tetrahydropyran-2S*-yl-methyl-, morpholin-2-yl-methyl-, pyrrolidin-1-yl-carbonyl-methyl-, piperazin-1-yl-carbonyl-methyl- and morpholin-4-yl-carbonyl-methyl-.

In certain embodiments, the present invention is directed to compounds of formula (I) wherein $R^5$ is —C$_{1-2}$alkyl-phenyl, wherein the —C$_{1-2}$alkyl-phenyl is optionally substituted as described herein.

In certain embodiments, the present invention is directed to compounds of formula (I) wherein $R^5$ is selected from the group consisting of phenyl-methyl-, 1R*-hydroxy-1-phenyl-methyl-, 1S*-hydroxy-1-phenyl-methyl-, R*—(S*-(1-hydroxy-1-phenyl)-methyl-), S*—(S*-(1-hydroxy-1-phenyl)-methyl-), R*—(R*-(1-hydroxy-1-phenyl)-methyl-), S*—(R*-(1-hydroxy-1-phenyl)-methyl-), S—(S-(1-hydroxy-1-phenyl)-methyl-),S—(R-(1-hydroxy-1-phenyl)-methyl-), 4-fluoro-phenyl-methyl-, 4-chloro-phenyl-methyl-, R*-(4-chloro-phenyl-methyl-), S*-(4-chloro-phenyl-methyl-), 4-fluoro-phenyl-methyl-, R*-(4-fluoro-phenyl-methyl-), S*-(4-fluoro-phenyl-methyl-), R-(4-fluoro-phenyl-methyl-), S-(4-fluoro-phenyl-methyl-), S-(4-(difluoro-methyl)-phenyl-methyl-), R-(4-(difluoro-methyl)-phenyl-methyl-), 2-methoxy-phenyl-methyl-, 4-methoxy-phenyl-methyl-, R*-(3-methoxy-phenyl-methyl-), S*-(3-methoxy-phenylmethyl-), 4-(amino-carbonyl-methoxy)-phenyl-methyl-, 4-(phenoxy)-phenyl-methyl-, 1,1'-biphen-4-yl-methyl and phenyl-ethyl-.

In certain embodiments, the present invention is directed to compounds of formula (I) wherein $R^5$ is selected from the group consisting of 1,2,3-triazol-4-yl, 1,2,5-triazol-3-yl, —CH$_2$-1,2,3-triazol-4-yl or —CH$_2$-1,2,4-traizol-5-yl; wherein the 1,2,3-triazol-4-yl and 1,2,5-triazol-3-yl, whether alone or as part of the substituent group is optionally substituted as described herein.

In certain embodiments, the present invention is directed to compounds of formula (I) wherein $R^5$ is selected from the group consisting of 1-methyl-1,2,3-triazol-4-yl, 1-phenyl-1,2,3-triazol-4-yl, 1-methyl-1,2,5-triazol-3-yl, 1-phenyl-1,2,5-triazol-3-yl, 1-(piperidin-4-yl)-1,2,3-triazol-4-yl, 1-(1-methyl-carbonyl-piperidin-4-yl)-1,2,3-triazol-4-yl, 1-methyl-1,2,5-triazol-3-yl-methyl-, 1-methyl-1,2,3-triazol-4-yl-methyl-, 1-phenyl-1,2,5-triazol-3-yl-methyl-, R-(1-methyl-1,2,3-triazol-4-yl-methyl), S-(1-methyl-1,2,3-triazol-4-yl-methyl), S-(1-(difluoro-methyl)-1,2,5-triazol-3-yl-methyl-), R-(1-(difluoro-methyl)-1,2,5-triazol-3-yl-methyl-), S-(1-(difluoro-methyl)-1,2,3-triazol-4-yl-methyl-), R-(1-(difluoro-methyl)-1,2,3-triazol-4-yl-methyl-), R-(1-methyl-1,2,5-triazol-3-yl-methyl-), and S-(1-methyl-1,2,5-triazol-3-yl-methyl-).

In certain embodiments, the present invention is directed to compounds of formula (I) wherein $R^5$ is $C_{1-2}$alkyl-(5 to 6 membered or 9 to 10 membered heterocyclyl); wherein the (5 to 6 membered or 9 to 10 membered heterocyclyl) is other than triazolyl; and wherein the (5 to 6 membered or 9 to 10 membered heterocyclyl) is further optionally substituted as described herein.

In certain embodiments, the present invention is directed to compounds of formula (I) wherein $R^5$ is $C_{1-2}$alkyl-pyrazolyl; wherein the $C_{1-2}$alkyl-pyrazolyl is optionally substituted as described herein. In certain embodiments, the present invention is directed to compounds of formula (I) wherein $R^5$ is selected from the group consisting of —$C_{1-2}$alkyl-pyrazol-1-yl and —CH$_2$-pyrazol-3-yl; wherein the pyrazol-1-yl or pyrazol-3-yl is further optionally substituted as described herein.

In certain embodiments, the present invention is directed to compounds of formula (I) wherein $R^5$ is —CH$_2$-(5 to 6 membered or 9 to 10 membered heterocyclyl); wherein the (5 to 6 membered or 9 to 10 membered heterocyclyl) is other than triazolyl or pyrazolyl; and wherein the —CH$_2$-(5 to 6 membered or 9 to 10 membered heterocyclyl) is further optionally substituted as described herein. In certain embodiments, the present invention is directed to compounds of formula (I) wherein $R^5$ is —CH$_2$-(5 to 6 membered or 9 to 10 membered heterocyclyl) wherein the (5 to 6 membered or 9 to 10 membered heterocyclyl) is selected from the group consisting of pyridinyl, imidazolidinyl, oxazolyl, oxazolidinyl, isochromanyl, isoindolinyl, thiazolyl and 2,4,5,7-tetrahydropyrano[3,4-c]pyrazol-2-yl; and wherein the (5 to 6 membered or 9 to 10 membered heterocyclyl) is further optionally substituted as described herein.

In certain embodiments, the present invention is directed to compounds of formula (I) wherein $R^5$ is selected from the group consisting of pyrazol-1-yl-methyl-, R*-(pyrazol-1-yl-methyl-), S*-(pyrazol-1-yl-methyl-), S-(pyrazol-1-yl-methyl-), R-(pyrazol-1-yl-methyl-), 4-fluoro-pyrazol-1-yl-methyl-, S-(4-fluoro-pyrazol-1-yl-methyl-), R-(4-fluoro-pyrazol-1-yl-methyl-), R*-(4-fluoro-pyrazol-1-yl-methyl-), S*-(4-fluoro-pyrazol-1-yl-methyl-), 1-(difluoro-methyl)-pyrazol-3-yl-methyl-, R-(1-(difluoro-methyl)-pyrazol-3-yl-methyl-), S-(1-(difluoro-methyl)-pyrazol-3-yl-methyl-), S-(1-(difluoro-methyl)-pyrazol-1-yl-methyl-), R-(1-(difluoro-methyl)-pyrazol-1-yl-methyl-), R*-(1-(difluoro-methyl)-pyrazol-3-yl-methyl-), S*-(1-(difluoro-methyl)-pyrazol-3-yl-methyl-), R-(4-(difluoro-methoxy)-pyrazol-1-yl-methyl-), S-(4-(difluoro-methoxy)-pyrazol-1-yl-methyl-), S-(1-(2,2,2-trifluoroethyl)-pyrazol-1-yl-methyl-), R-(1-(2,2,2-trifluoroethyl)-pyrazol-1-yl-methyl-), 3-(trifluoro-methyl)-pyrazol-1-yl-methyl-, 5-(trifluoro-methyl)-pyrazol-1-yl-methyl-, 4-(trifluoro-methyl)-pyrazol-1-yl-methyl-, 1-methyl-pyrazol-4-yl-methyl-, S*-(1-methyl-pyrazol-4-yl-methyl-), R*-(1-methyl-pyrazol-4-yl-methyl-), 1-methyl-pyrazol-3-yl-methyl-, R-(1-methyl-pyrazol-3-yl-methyl-), R*-(1-methyl-pyrazol-3-yl-methyl-), S*-(1-methyl-pyrazol-3-yl-methyl-), S-(1-methyl-pyrazol-3-yl)-methyl-), S-(1-isopropyl-pyrazol-3-yl-methyl-), R-(1-isopropyl-pyrazol-3-yl-methyl-), 4-(tert-butyl)-pyrazol-1-yl-methyl-, 1-(2,2,2-trifluoroethyl)-4-fluoro-pyrazol-3-yl-methyl-, R-(3-(difluoro-methoxy)-pyrazol-1-yl-methyl-), S-(3-(difluoro-methoxy)-pyrazol-1-yl)-methyl-), 3-(methoxy-methyl)-pyrazol-1-yl-methyl-, 5-(methoxy-methyl)-pyrazol-1-yl-methyl-, R*-(3-(methoxy-methyl)-pyrazol-1-yl-methyl-), S*-(3-(methoxy-methyl)-pyrazol-1-yl-methyl-), S*-(3-(difluoro-methoxy-methyl)-4-fluoro-pyrazol-1-yl-methyl-), R*-(3-(difluoro-methoxy-methyl)-4-fluoro-pyrazol-1-yl-methyl-), 4-cyano-pyrazol-1-yl-methyl-, 3-carboxy-pyrazol-1-yl-methyl-, 3-(amino-carbonyl)-pyrazol-1-yl-methyl-, 4-(amino-carbonyl)-pyrazol-1-yl-methyl-, S*-(5-(amino-carbonyl)-pyrazol-1-yl-methyl-), R*-(5-(amino-carbonyl)-pyrazol-1-yl-methyl-), R*-(3-(amino-carbonyl)-pyrazol-1-yl-methyl-), R*-(3-(dimethyl-amino-carbonyl)-pyrazol-1-yl-methyl-), 3-(amino-carbonyl-methyl)-pyrazol-1-yl-methyl-, 5-(amino-carbonyl-methyl)-pyrazol-1-yl-methyl-, 3-(piperidin-1-yl-carbonyl)-pyrazol-1-yl-methyl-, R*-(3-(piperidin-1-yl-carbonyl)-pyrazol-1-yl-methyl-), S*-(3-(piperidin-1-yl-carbonyl)-pyrazol-1-yl-methyl-), 4-(piperidin-1-yl-carbonyl)-pyrazol-1-yl-methyl-, R*-(4-(piperidin-1-yl-carbonyl)-pyrazol-1-yl-methyl-), S*-(4-(piperidin-1-yl-carbonyl)-pyrazol-1-yl-methyl-), 3-(4-carboxy-piperidin-1-yl-carbonyl)-pyrazol-1-yl-methyl-, 4-(piperidin-1-yl-carbonyl-methyl)-pyrazol-1-yl-methyl-, 3-(tetrahydropyran-4-yl)-pyrazol-1-yl-methyl-, 3-phenyl-pyrazol-1-yl-methyl-, R*-(4-(pyridin-2-yl)-pyrazol-1-yl-methyl-), S*-(4-(pyridin-2-yl)-pyrazol-1-yl-methyl-), R*-((5-fluoro-pyridin-1-yl)-pyrazol-1-yl-methyl-), S*-((5-fluoro-pyridin-1-yl)-pyrazol-1-yl-methyl-), (pyridin-1-yl-2-one)-methyl-, S*-(pyridin-1-yl-2-one)-methyl-), R*-(pyridin-1-yl-2-one)-methyl-), 6-(trifluoro-methyl)-pyridin-3-yl, R-(6-(trifluoro-methyl)-pyridin-3-yl), S-(6-(trifluoro-methyl)-pyridin-3-yl), R-((3-methyl-imidazolidin-1-yl-2-one)-methyl-), S*-((3-methyl-imidazolidin-1-yl-2-one)-methyl-), oxazol-2-yl-methyl-, R*-((oxazolidin-3-yl-2-one)-methyl-), S*-((oxazolidin-3-yl-2-one)-methyl-), (5-methyl-1,3,4-oxadiazol-2-yl)-methyl-, 1,2,4-oxadiazol-3-yl-methyl-, 1,3,4-oxadiazol-2-yl-methyl-, isochroman-1-yl-methyl-, (isoindolin-2-yl-1-one)-methyl-, thiazol-2-yl-methyl-, R-(thiazol-2-yl-methyl-), S-(thiazol-2-yl-methyl-), R*-(thiazol-2-yl-methyl-), S*-(thiazol-2-yl-methyl-), and 2,4,5,7-tetrahydropyrano[3,4-c]pyrazol-2-yl-methyl-.

In certain embodiments, the present invention is directed to compounds of formula (I) wherein $R^5$ is selected from the group consisting of pyrazol-1-yl-methyl-, R*-(pyrazol-1-yl-methyl-), S*-(pyrazol-1-yl-methyl-), S-(pyrazol-1-yl-methyl-), R-(pyrazol-1-yl-methyl-), 4-fluoro-pyrazol-1-yl-methyl-, S-(4-fluoro-pyrazol-1-yl-methyl-), R-(4-fluoro-pyrazol-1-yl-methyl-), R*-(4-fluoro-pyrazol-1-yl-methyl-), S*-(4-fluoro-pyrazol-1-yl-methyl-), 1-(difluoro-methyl)- pyrazol-3-yl-methyl-, R-(1-(difluoro-methyl)-pyrazol-3-yl-methyl-), S-(1-(difluoro-methyl)-pyrazol-3-yl-methyl-), S-(1-(difluoro-methyl)-pyrazol-1-yl-methyl-), R-(1-(difluoro-methyl)-pyrazol-1-yl-methyl-), R*-(1-(difluoro-methyl)-pyrazol-3-yl-methyl-), S*-(1-(difluoro-methyl)-pyrazol-3-yl-methyl-), R-(4-(difluoro-methoxy)-pyrazol-1-yl-methyl-), S-(4-(difluoro-methoxy)-pyrazol-1-yl-methyl-), S-(1-(2,2,2-trifluoroethyl)-pyrazol-1-yl-methyl-), R-(1-(2,2,2-trifluoroethyl)-pyrazol-1-yl-methyl-), 3-(trifluoro-methyl)-pyrazol-1-yl-methyl-, 5-(trifluoro-methyl)-pyrazol-1-yl-methyl-, 4-(trifluoro-methyl)-pyrazol-1-yl-methyl-, 1-methyl-pyrazol-4-yl-methyl-, S*-(1-methyl-pyrazol-4-yl-methyl-), R*-(1-methyl-pyrazol-4-yl-methyl-), 1-methyl-pyrazol-3-yl-methyl-, R-(1-methyl-pyrazol-3-yl-methyl-), R*-(1-methyl-pyrazol-3-yl-methyl-), S*-(1-methyl-pyrazol-3-yl-methyl-), S-(1-methyl-pyrazol-3-yl)-methyl-), S-(1-isopropyl-pyrazol-3-yl-methyl-), R-(1-isopropyl-pyrazol-3-yl-methyl-), 4-(tert-butyl)-pyrazol-1-yl-methyl-, 1-(2,2,2-trifluoroethyl)-4-fluoro-pyrazol-3-yl-methyl-, R-(3-(difluoro-methoxy)-pyrazol-1-yl-methyl-), S-(3-(difluoro-methoxy)-pyrazol-1-yl)-methyl-), 3-(methoxy-methyl)-pyrazol-1-yl-methyl-, 5-(methoxy-methyl)-pyrazol-1-yl-methyl-, R*-(3-(methoxy-methyl)-pyrazol-1-yl-methyl-), S*-(3-(methoxy-methyl)-pyrazol-1-yl-methyl-), S*-(3-(difluoro-methoxy-methyl)-4-fluoro-pyrazol-1-yl-methyl-), R*-(3-(difluoro-methoxy-methyl)-4-fluoro-pyrazol-1-yl-methyl-), 4-cyano-pyrazol-1-yl-methyl-, 3-carboxy-pyrazol-1-yl-methyl-, 3-(amino-carbonyl)-pyrazol-1-yl-methyl-, 4-(amino-carbonyl)-pyrazol-1-yl-methyl-, S*-(5-(amino-carbonyl)-pyrazol-1-yl-methyl-), R*-(5-(amino-carbonyl)-pyrazol-1-yl-methyl-), R*-(3-(amino-carbonyl)-pyrazol-1-yl-methyl-), R*-(3-(dimethyl-amino-carbonyl)-pyrazol-1-yl-methyl-), 3-(amino-carbonyl-methyl)-pyrazol-1-yl-methyl-, 5-(amino-carbonyl-methyl)-pyrazol-1-yl-methyl-, 3-(piperidin-1-yl-carbonyl)-pyrazol-1-yl-methyl-, R*-(3-(piperidin-1-yl-carbonyl)-pyrazol-1-yl-methyl-), S*-(3-(piperidin-1-yl-carbonyl)-pyrazol-1-yl-methyl-), 4-(piperidin-1-yl-carbonyl)-pyrazol-1-yl-methyl-, R*-(4-(piperidin-1-yl-carbonyl)-pyrazol-1-yl-methyl-), S*-(4-(piperidin-1-yl-carbonyl)-pyrazol-1-yl-methyl-), 3-(4-carboxy-piperidin-1-yl-carbonyl)-pyrazol-1-yl-methyl-, 4-(piperidin-1-yl-carbonyl-methyl)-pyrazol-1-yl-methyl-, 3-(tetrahydropyran-4-yl)-pyrazol-1-yl-methyl-, 3-phenyl-pyrazol-1-yl-methyl-, R*-(4-(pyridin-2-yl)-pyrazol-1-yl-methyl-), S*-(4-(pyridin-2-yl)-pyrazol-1-yl-methyl-), R*-((5-fluoro-pyridin-1-yl)-pyrazol-1-yl-methyl-), and S*-((5-fluoro-pyridin-1-yl)-pyrazol-1-yl-methyl-).

In certain embodiments, the present invention is directed to compounds of formula (I) wherein $R^5$ is selected from the group consisting of (pyridin-1-yl-2-one)-methyl-, S*-(pyridin-1-yl-2-one)-methyl-), R*-(pyridin-1-yl-2-one)-methyl-), 6-(trifluoro-methyl)-pyridin-3-yl, R-(6-(trifluoro-methyl)-pyridin-3-yl), S-(6-(trifluoro-methyl)-pyridin-3-yl), R-((3-methyl-imidazolidin-1-yl-2-one)-methyl-), S*-((3-methyl-imidazolidin-1-yl-2-one)-methyl-), oxazol-2-yl-methyl-, R*-((oxazolidin-3-yl-2-one)-methyl-), S*-((oxazolidin-3-yl-2-one)-methyl-), (5-methyl-1,3,4-oxadiazol-2-yl)-methyl-, 1,2,4-oxadiazol-3-yl-methyl-, 1,3,4-oxadiazol-2-yl-methyl-, isochroman-1-yl-methyl-, (isoindolin-2-yl-1-one)-methyl-, thiazol-2-yl-methyl-, R-(thiazol-2-yl-methyl-), S-(thiazol-2-yl-methyl-), R*-(thiazol-2-yl-methyl-), S*-(thiazol-2-yl-methyl-), and 2,4,5,7-tetrahydropyrano[3,4-c]pyrazol-2-yl-methyl-.

In certain embodiments, the present invention is directed to compounds of formula (I) wherein $R^5$ is —CH$_2$—NR$^8$R$^9$; wherein $R^8$ and $R^9$ are as described herein.

In certain embodiments, the present invention is directed to compounds of formula (I) wherein $R^5$ is selected from the group consisting of (methoxy-carbonyl)-amino-methyl-, N-methyl-N-(phenyl-carbonyl)-amino-methyl-, N-methyl-N-(methoxy-carbonyl)-amino-methyl-, N-methyl-N-(methoxy-carbonyl)-amino-methyl-, N-methyl-N-(methyl-carbonyl)-amino-methyl-, N-methyl-N-(trifluoro-methoxy)-amino-methyl-, R*—(N-methyl-N-(methoxy-carbonyl)-amino-methyl-), S*—(N-methyl-N-(methoxy-carbonyl)-amino-methyl-), R*—(N-methyl-N-(methyl-carbonyl)-amino-methyl-), S*—(N-methyl-N-(methyl-carbonyl)-amino-methyl-), N-methyl-N-(isopropyl-carbonyl)-amino-methyl-, R*—(N-methyl-N-(isopropyl-carbonyl)-amino-methyl-), S*—(N-methyl-N-(isopropyl-carbonyl)-amino-methyl-), N-methyl-N-(t-butyl-carbonyl)-amino-methyl-, S*—(N-methyl-N-(t-butyl-carbonyl)-amino-methyl-), R*—(N-methyl-N-(t-butyl-carbonyl)-amino-methyl-), R*—(N-methyl-N-(t-butoxy-carbonyl)-amino-methyl-), S*—(N-methyl-N-(t-butoxy-carbonyl)-amino-methyl-), N-methyl-N-(methoxy-methyl-carbonyl)-amino-methyl-, (cyclopropyl-carbonyl)-amino-methyl-, (1-methyl-cycloprop-1-yl-carbonyl)-amino-methyl-, R*—(N-methyl-N-cyclopropyl-carbonyl)-amino-methyl-), S*—(N-methyl-N-(cyclopropyl-carbonyl)-amino-methyl-), R*—(N-methyl-N-(phenyl-carbonyl)-amino-methyl-), S*—(N-methyl-N-(phenyl-carbonyl)-amino-methyl-), N-methyl-N-(benzyl-carbonyl)-amino-methyl-, N-methyl-N-(phenyl-ethyl-carbonyl)-amino-methyl-, S*—(N-methyl-N-(phenyl-ethyl-carbonyl)-amino-methyl-), R*—(N-methyl-N-(phenyl-ethyl-carbonyl)-amino-methyl-), R*—(N-methyl-N-(benzyloxy-carbonyl)-amino-methyl-), S*—(N-methyl-N-(benzyloxy-carbonyl)-amino-methyl-), N-methyl-N-(tetrahydropyran-4-yl-carbonyl)-amino-methyl-, N-methyl-N-(piperidin-1-yl-carbonyl-methyl-carbonyl)-amino-methyl-, R*—(N-methyl-N-(2-(piperidin-1-yl-carbonyl)-ethyl-carbonyl)-amino-methyl-), S*—(N-methyl-N-(2-(piperidin-1-yl-carbonyl)-ethyl-carbonyl)-amino-methyl-), N-methyl-N-(2-(piperidin-1-yl-carbonyl)-ethoxy))-amino-ethyl-, S*—(N-methyl-N-(1-methyl-pyridin-4-yl-2-one-carbonyl)-amino-methyl-), R*—(N-methyl-N-(1-methyl-pyridin-4-yl-2-one-carbonyl)-amino-methyl-), and N-methyl-N-(dimethylamino-carbonyl)-amino-methyl-.

In certain embodiments, the present invention is directed to compounds of formula (I) wherein $R^5$ is selected from the group consisting of (a) ethyl, 2-methoxy-ethyl-, S-(2-methoxy-ethyl-), R-(2-methoxy-ethyl-), 2-(difluoro-methoxy)-ethyl-, R-(2-(difluoro-methoxy)-ethyl-), S-(2-(difluoro-methoxy)-ethyl-), R*-(2-(difluoro-methoxy)-ethyl-2,2-d2-), S*-(2-(difluoro-methoxy)-ethyl-2,2-d2-), (b) cyclopropyl-methyl-, R*-(cyclopropyl-methyl-), S*-(cyclopropyl-methyl-), S-(cyclopropyl-methyl-), R-(cyclopropyl-methyl-), 2S*-(amino-carbonyl)-1S*-cyclopropyl-methyl-, 2R*-(piperidin-1-yl-carbonyl)-1S*-cyclopropyl-methyl-, 2S*-(piperidin-1-yl-carbonyl)-1S*-cyclopropyl-methyl-, R*-(2S*-(piperidin-1-yl-carbonyl)-cyclopropyl-methyl-), S*-(2R*-(piperidin-1-yl-carbonyl)-cyclopropyl-methyl-), S*-(2-(piperidin-1-yl-carbonyl)-cyclopropyl-methyl-), (c) R*-(pyrrolidin-1-yl-2-one-methyl-), S*-(pyrrolidin-1-yl-2-one-methyl-), (d) phenyl-methyl-, 4-fluoro-phenyl-methyl-, R*-(4-fluoro-phenyl-methyl-), S*-(4-fluoro-phenyl-methyl-), (f) 4-fluoro-pyrazol-1-yl-methyl-, R*-(4-fluoro-pyrazol-1-yl-methyl-), S*-(4-fluoro-pyrazol-1-yl-methyl-), S*-(5-(amino-carbonyl)-pyrazol-1-yl-methyl-), R*-(5-(amino-carbonyl)-pyrazol-1-yl-methyl-), S*-(1-methyl-pyrazol-4-yl-methyl-), R*-(1-methyl-pyrazol-4-yl-methyl-), S-(1-methyl-pyrazol-3-yl)-methyl-), R-(1-methyl-pyrazol-3-yl)-methyl-), S-(1-methyl-pyrazol-3-yl-methyl-), R-(1- methyl-pyrazol-3-yl-methyl-), 1-(difluoro-methyl)-pyrazol-3-yl-methyl-, S*-(1-(difluoro-methyl)-pyrazol-3-yl-methyl-) and R*-(1-(difluoro-methyl)-pyrazol-3-yl-methyl-).

In certain embodiments, the present invention is directed to compounds of formula (I) wherein $R^5$ is selected from the group consisting of R-(2-methoxy-ethyl-), R-(2-(difluoro-methoxy)-ethyl-), phenyl-methyl-, 4-fluoro-phenyl-methyl-, S*-(4-fluoro-phenyl-methyl-), cyclopropyl-methyl-, R-(cyclopropyl-methyl-), S*-(cyclopropyl-methyl-), R*-(cyclopropyl-methyl-), R*-(2S*-(piperidin-1-yl-carbonyl)-cyclopropyl-methyl-), R*-(pyrrolidin-1-yl-2-one-methyl-), 4-fluoro-pyrazol-1-yl-methyl-, R*-(4-fluoro-pyrazol-1-yl-methyl-), S*-(5-(amino-carbonyl)-pyrazol-1-yl-methyl-), -(1-methyl-pyrazol-3-yl-methyl-), 1-(difluoro-methyl)-pyrazol-3-yl-methyl-, S*-(1-(difluoro-methyl)-pyrazol-3-yl-methyl-), R*-(1-(difluoro-methyl)-pyrazol-3-yl-methyl-) and R*-(1-methyl-pyrazol-4-yl-methyl-). In certain embodiments, the present invention is directed to compounds of formula (I) wherein $R^5$ is selected from the group consisting of R-(2-methoxy-ethyl-), R-(2-(difluoro-methoxy)-ethyl-), phenyl-methyl-, S*-(4-fluoro-phenyl-methyl-), cyclopropyl-methyl-, R-(cyclopropyl-methyl-), R*-(pyrrolidin-1-yl-2-one-methyl-), 4-fluoro-pyrazol-1-yl-methyl-, R-(1-methyl-pyrazol-3-yl-methyl-), 1-(difluoro-methyl)-pyrazol-3-yl-methyl-, S*-(1-(difluoro-methyl)-pyrazol-3-yl-methyl-), R*-(1-(difluoro-methyl)-pyrazol-3-yl-methyl-) and R*-(1-methyl-pyrazol-4-yl-methyl-). In certain embodiments, the present invention is directed to compounds of formula (I) wherein $R^5$ is selected from the group consisting of R-(2-(difluoro-methoxy)-ethyl-), phenyl-methyl-,R*-(pyrrolidin-1-yl-2-one-methyl-), 4-fluoro-pyrazol-1-yl-methyl-, R-(1-methyl-pyrazol-3-yl-methyl-), 1-(difluoro-methyl)-pyrazol-3-yl-methyl-, S*-(1-(difluoro-methyl)-pyrazol-3-yl-methyl-) and R*-(1-(difluoro-methyl)-pyrazol-3-yl-methyl-).

In certain embodiments, the present invention is directed to compounds of formula (I) wherein $R^5$ is selected from the group consisting of (a) isopropyloxy-methyl-, methoxy-carbonyl-methyl-, dimethyl-amino-carbonyl-methyl-, ethyl, R*-ethyl, S*-ethyl, R*-(2-hydroxy-ethyl-), S*-(2-hydroxy-ethyl-), 2-ethoxy-ethyl-, 2-(difluoro-methoxy)-ethyl-, S*-(2-(difluoro-methoxy)-ethyl-), R*-(2-(difluoro-methoxy)-ethyl-), R-(2-(difluoro-methoxy)-ethyl-), 2-methoxy-ethyl-, 2-(methoxy-d)-ethyl-, R-(2-methoxy-ethyl), R*-(2-methoxy-ethyl-), R-(2-(methoxy-d₃)-ethyl-), S*-(2-(methoxy-d₃)-ethyl-), R*-(2-isopropyloxy-ethyl), S*-(2-isopropyloxy-ethyl), 2-t-butoxy-ethyl-, S*-(2-(methoxy-d₃)-ethyl-2,2-d₂-), R*-(2-(methoxy-d₃)-ethyl-2,2-d₂-), 2-(methoxy-d₃)-ethyl-2,2-d₂-, n-propyl, R*-(n-propyl), S*-(n-propyl), S*-(2-methoxy-n-propyl-), R-(2-methoxy-n-propyl-), isobutyl, R-isobutyl, S*-isobutyl; (b) cyclopropyl-methyl-, R*-(cyclopropyl-methyl-), R-(cyclopropyl-methyl-), S*-(cyclopropyl-methyl-), S-(cyclopropyl-methyl-), 2-methyl-cyclopropyl-methyl-, 2R*-carboxy-1S*-cyclopropyl-methyl-, 2S*-carboxy-1R*-cyclopropyl-methyl-, 2R*-carboxy-1R*-cyclopropyl-methyl-, 2S*-carboxy-1S*-cyclopropyl-methyl-, 2S*-(ethoxy-carbonyl)-1S*-cyclopropyl-methyl-, 2R*-(ethoxy-carbonyl)-1R*-cyclopropyl-methyl-, 2R*-(amino-carbonyl)-1S*-cyclopropyl-methyl-, 2S*-(amino-carbonyl)-1S*-cyclopropyl-methyl-, 2-(amino-carbonyl)-cyclopropyl-methyl-, 2-(1,1'-biphen-4-yl)-cyclopropyl-methyl, 2R*-(pyrrolidin-1-yl-carbonyl)-1S*-cyclopropyl-methyl-, 2S*-(pyrrolidin-1-yl-carbonyl)-1R*-cyclopropyl-methyl-, 2S*-(pyrrolidin-1-yl-carbonyl)-1S*-cyclopropyl-methyl-, 2R*-(pyrrolidin-1-yl-carbonyl)-1R*-cyclopropyl-methyl-, 2-(3-phenyl-pyrrolidin-1-yl-carbonyl)-cyclopropyl-methyl-, 2S*-(3-phenyl-pyrrolidin-1-yl-carbonyl)-1R*-cyclopropyl-methyl-, 2S*-(3-phenyl-pyrrolidin-1-yl-carbonyl)-1S*-cyclopropyl-methyl-, 2R*-(3-phenyl-pyrrolidin-1-yl-carbonyl)-1R*-cyclopropyl-methyl-, 2R*-(3-phenyl-pyrrolidin-1-yl-carbonyl)-1S*-cyclopropyl-methyl-, 2-(4,4-difluoro-piperidin-1-yl-carbonyl)-cyclopropyl-methyl-, 2-(piperidin-1-yl-carbonyl)-cyclopropyl-methyl-, 2S*-(piperidin-1-yl-carbonyl)-1R*-cyclopropyl-methyl-, 2R*-(piperidin-1-yl-carbonyl)-1R*-cyclopropyl-methyl-, 2R*-(piperidin-1-yl-carbonyl)-1S*-cyclopropyl-methyl-, 2S*-(piperidin-1-yl-carbonyl)-1S*-cyclopropyl-methyl-, 2S*-(4-carboxy-piperidin-1-yl-carbonyl)-1R*-cyclopropyl-methyl-, 2R*-(4-carboxy-piperidin-1-yl-carbonyl)-1R*-cyclopropyl-methyl-, 2S*-(3-carboxy-piperidin-1-yl-carbonyl)-1R*-cyclopropyl-methyl-, 2R*-(3-carboxy-piperidin-1-yl-carbonyl)-1R*-cyclopropyl-methyl-, 2R*-(piperazin-1-yl-carbonyl)-1S*-cyclopropyl-methyl-, 2R*-(morpholin-4-yl-carbonyl)-1S*-cyclopropyl-methyl-, 2S*-(morpholin-4-yl-carbonyl)-1S*-cyclopropyl-methyl-, 2R*-(isoindolin-2-yl-carbonyl)-1S*cyclopropyl-methyl, 2S*-(isoindolin-2-yl-carbonyl)-1S*cyclopropyl-methyl, 2S*-(isoindolin-2-yl-carbonyl)-1R*cyclopropyl-methyl, 2R*-(isoindolin-2-yl-carbonyl)-1R*cyclopropyl-methyl, 2R*-(4-methoxy-phenyl)-1S*-cyclopropyl-methyl-, 2S*-(4-methoxy-phenyl)-1S*-cyclopropyl-methyl-, 2R*-(3-phenyl-pyrrolidin-1-yl-carbonyl)-1S*-cyclopropyl-methyl-, cyclobutyl-methyl-, 3,3-dimethyl-cyclobutyl-methyl-, cyclopentyl-methyl-, cyclohexyl-methyl-, 4-methyl-cyclohexyl-methyl-, 4,4-dimethyl-cyclohexyl-methyl-, adamantan-1-yl-methyl-; (c) tetrahydrofuran-2-yl-methyl-, S*-(tetrahydrofuran-2-yl-methyl-), tetrahydropyran-2S*-yl-methyl-, tetrahydropyran-2R*-yl-methyl-, R*-(tetrahydropyran-2S*-yl-methyl-), S*-(tetrahydropyran-2S*-yl-methyl-), pyrrolidin-1-yl-carbonyl-methyl-, (pyrrolidin-1-yl-2-one)-methyl-, R*-((pyrrolidin-1-yl-2-one)-methyl-), S*-((pyrrolidin-1-yl-2-one)-methyl-), morpholin-4-yl-carbonyl-methyl-, piperazin-1-yl-carbonyl-methyl-; (d) phenyl-methyl-, 4-chloro-phenyl-methyl-, R*-(4-chloro-phenyl-methyl-), S*-(4-chloro-phenyl-methyl-), 4-fluoro-phenyl-methyl-, 1R*-hydroxy-1-phenyl-methyl-, 1S*-hydroxy-1-phenyl-methyl-, 2-methoxy-phenyl-methyl-, R*-(3-methoxy-phenyl-methyl-), S*-(3-methoxy-phenyl-methyl-), 4-methoxy-phenyl-methyl-, 4-(amino-carbonyl-methoxy)-phenyl-methyl-, phenyl-ethyl-, 1,1'-biphen-4-yl-methyl-, 4-(phenoxy)-phenyl-methyl-; (e) 1-methyl-1,2,3-triazol-4-yl, 1-phenyl-1,2,3-triazol-4-yl, 1-(piperidin-4-yl)-1,2,3-triazol-4-yl, 1-(1-methyl-carbonyl-piperidin-4-yl)-1,2,3-triazol-4-yl; (f) pyrazol-1-yl-methyl-, R*-(pyrazol-1-yl-methyl-), S*-(pyrazol-1-yl-methyl-), 4-fluoro-pyrazol-1-yl-methyl-, 1-methyl-pyrazol-3-yl-methyl-, S-(1-methyl-pyrazol-3-yl-methyl-), R-(1-methyl-pyrazol-3-yl-methyl-), R*-(1-methyl-pyrazol-3-yl-methyl-), 4-(tert-butyl)-pyrazol-1-yl-methyl-, 1-(difluoro-methyl)-pyrazol-3-yl-methyl-, S*-(1-(difluoro-methyl)-pyrazol-3-yl-methyl-), R-(1-(difluoro-methyl)-pyrazol-3-yl-methyl-), R*-(1-(difluoro-methyl)-pyrazol-3-yl-methyl-), 3-carboxy-pyrazol-1-yl-methyl-, 3-(amino-carbonyl)-pyrazol-1-yl-methyl-, 4-cyano-pyrazol-1-yl-methyl-, isochroman-1-yl-methyl-, (pyridin-1-yl-2-one)-methyl-, oxazol-2-yl-methyl-, 1,2,4-oxadiazol-3-yl-methyl-, (5-methyl-1,3,4-oxadiazol-2-yl)-methyl-, thiazol-2-yl-methyl-, R*-(thiazol-2-yl-methyl-), S*-(thiazol-2-yl-methyl-); and (g) N-methyl-N-(methoxy-carbonyl)-amino-methyl-.

In certain embodiments, the present invention is directed to compounds of formula (I) wherein $R^S$ is selected from the group consisting of (a) isopropyloxy-methyl-, methoxycarbonyl-methyl-, dimethyl-amino-carbonyl-methyl-, ethyl, R*-ethyl, S*-ethyl, S*-(2-hydroxy-ethyl-), 2-ethoxy-ethyl-, 2-(difluoro-methoxy)-ethyl-, S*-(2-(difluoro-methoxy)-ethyl-), R*-(2-(difluoro-methoxy)-ethyl-), R-(2-(difluoro-methoxy)-ethyl-), 2-methoxy-ethyl-, 2-(methoxy-d$_3$)-ethyl-, R-(2-methoxy-ethyl), R-(2-(methoxy-d$_3$)-ethyl-), S*-(2-(methoxy-d$_3$)-ethyl-), S*-(2-isopropyloxy-ethyl), 2-t-butoxy-ethyl-, S*-(2-(methoxy-d$_3$)-ethyl-2,2-d2-), 2-(methyl-d$_3$)-ethyl-2,2-d$_2$-, n-propyl, S*-(n-propyl), S*-(2-methoxy-n-propyl-), R-(2-methoxy-n-propyl-), isobutyl, S*-isobutyl; (b) cyclopropyl-methyl-, R-(cyclopropyl-methyl-), S*-(cyclopropyl-methyl-), 2-methyl-cyclopropyl-methyl-, 2R*-carboxy-1S*-cyclopropyl-methyl-, 2S*-carboxy-1R*-cyclopropyl-methyl-, 2R*-carboxy-1R*-cyclopropyl-methyl-, 2S*-carboxy-1S*-cyclopropyl-methyl-, 2S*-(ethoxy-carbonyl)-1S*-cyclopropyl-methyl-, 2R*-(ethoxy-carbonyl)-1R*-cyclopropyl-methyl-, 2R*-(amino-carbonyl)-1S*-cyclopropyl-methyl-, 2S*-(amino-carbonyl)-1S*-cyclopropyl-methyl-, 2-(amino-carbonyl)-cyclopropyl-methyl-, 2-(1,1'-biphen-4-yl)-cyclopropyl-methyl, 2R*-(pyrrolidin-1-yl-carbonyl)-1S*-cyclopropyl-methyl-, 2S*-(pyrrolidin-1-yl-carbonyl)-1S*-cyclopropyl-methyl-, 2R*-(pyrrolidin-1-yl-carbonyl)-1R*-cyclopropyl-methyl-, 2-(3-phenyl-pyrrolidin-1-yl-carbonyl)-cyclopropyl-methyl-, 2S*-(3-phenyl-pyrrolidin-1-yl-carbonyl)-1R*-cyclopropyl-methyl-, 2S*-(3-phenyl-pyrrolidin-1-yl-carbonyl)-1S*-cyclopropyl-methyl-, 2R*-(3-phenyl-pyrrolidin-1-yl-carbonyl)-1R*-cyclopropyl-methyl-, 2R*-(3-phenyl-pyrrolidin-1-yl-carbonyl)-1S*-cyclopropyl-methyl-, 2-(4,4-difluoro-piperidin-1-yl-carbonyl)-cyclopropyl-methyl-, 2-(piperidin-1-yl-carbonyl)-cyclopropyl-methyl-, 2S*-(piperidin-1-yl-carbonyl)-1R*-cyclopropyl-methyl-, 2R*-(piperidin-1-yl-carbonyl)-1R*-cyclopropyl-methyl-, 2R*-(piperidin-1-yl-carbonyl)-1S*-cyclopropyl-methyl-, 2S*-(piperidin-1-yl-carbonyl)-1S*-cyclopropyl-methyl-, 2S*-(4-carboxy-piperidin-1-yl-carbonyl)-1R*-cyclopropyl-methyl-, 2R*-(4-carboxy-piperidin-1-yl-carbonyl)-1R*-cyclopropyl-methyl-, 2S*-(3-carboxy-piperidin-1-yl-carbonyl)-1R*-cyclopropyl-methyl-, 2R*-(3-carboxy-piperidin-1-yl-carbonyl)-1R*-cyclopropyl-methyl-, 2R*-(piperazin-1-yl-carbonyl)-1S*-cyclopropyl-methyl-, 2R*-(morpholin-4-yl-carbonyl)-1S*-cyclopropyl-methyl-, 2S*-(morpholin-4-yl-carbonyl)-1S*-cyclopropyl-methyl-, 2R*-(isoindolin-2-yl-carbonyl)-1S*cyclopropyl-methyl, 2S*-(isoindolin-2-yl-carbonyl)-1S*cyclopropyl-methyl, 2S*-(isoindolin-2-yl-carbonyl)-1R*cyclopropyl-methyl, 2R*-(isoindolin-2-yl-carbonyl)-1R*cyclopropyl-methyl, 2R*-(4-methoxy-phenyl)-1S*-cyclopropyl-methyl-, 2S*-(4-methoxy-phenyl)-1S*-cyclopropyl-methyl-, 2R*-(3-phenyl-pyrrolidin-1-yl-carbonyl)-1S*-cyclopropyl-methyl-, cyclobutyl-methyl-, 3,3-dimethyl-cyclobutyl-methyl-, cyclopentyl-methyl-, cyclohexyl-methyl-, 4-methyl-cyclohexyl-methyl-, 4,4-dimethyl-cyclohexyl-methyl-, adamantan-1-yl-methyl-; (c) tetrahydrofuran-2-yl-methyl-, S*-(tetrahydrofuran-2-yl-methyl-), tetrahydropyran-2S*-yl-methyl-, tetrahydropyran-2R*-yl-methyl-, S*-(tetrahydropyran-2S*-yl-methyl-), pyrrolidin-1-yl-carbonyl-methyl-, (pyrrolidin-1-yl-2-one)-methyl-, S*-((pyrrolidin-1-yl-2-one)-methyl-), morpholin-4-yl-carbonyl-methyl-, piperazin-1-yl-carbonyl-methyl-; (d) phenyl-methyl-, 4-chloro-phenyl-methyl-, R*-(4-chloro-phenyl-methyl-), S*-(4-chloro-phenyl-methyl-), 4-fluoro-phenyl-methyl-, 1R*-hydroxy-1-phenyl-methyl-, 1S*-hydroxy-1-phenyl-methyl-, 2-methoxy-phenyl-methyl-, R*-(3-methoxy-phenyl-methyl-), S*-(3-methoxy-phenyl-methyl-), 4-methoxy-phenyl-methyl-, 4-(amino-carbonyl-methoxy)-phenyl-methyl-, phenyl-ethyl-, 1,1'-biphen-4-yl-methyl-, 4-(phenoxy)-phenyl-methyl-; (e) 1-(1-methyl-carbonyl-piperidin-4-yl)-1,2,3-triazol-4-yl; (f) pyrazol-1-yl-methyl-, R*-(pyrazol-1-yl-methyl-), S*-(pyrazol-1-yl-methyl-), 4-fluoro-pyrazol-1-yl-methyl-, 1-methyl-pyrazol-3-yl-methyl-, S-(1-methyl-pyrazol-3-yl-methyl-), R-(1-methyl-pyrazol-3-yl-methyl-), R*-(1-methyl-pyrazol-3-yl-methyl-), 4-(tert-butyl)-pyrazol-1-yl-methyl-, 1-(difluoro-methyl)-pyrazol-3-yl-methyl-, S*-(1-(difluoro-methyl)-pyrazol-3-yl-methyl-), R-(1-(difluoro-methyl)-pyrazol-3-yl-methyl-), R*-(1-(difluoro-methyl)-pyrazol-3-yl-methyl-), 4-cyano-pyrazol-1-yl-methyl-, isochroman-1-yl-methyl-, (pyridin-1-yl-2-one)-methyl-, oxazol-2-yl-methyl-, 1,2,4-oxadiazol-3-yl-methyl-, (5-methyl-1,3,4-oxadiazol-2-yl)-methyl-, thiazol-2-yl-methyl-, R*-(thiazol-2-yl-methyl-), S*-(thiazol-2-yl-methyl-); and (g) N-methyl-N-(methoxy-carbonyl)-amino-methyl-.

In certain embodiments, the present invention is directed to compounds of formula (I) wherein $R^S$ is selected from the group consisting of (a) isopropyloxy-methyl-, methoxy-carbonyl-methyl-, dimethyl-amino-carbonyl-methyl-, ethyl, R*-ethyl, S*-ethyl, S*-(2-hydroxy-ethyl-), 2-ethoxy-ethyl-, 2-(difluoro-methoxy)-ethyl-, S*-(2-(difluoro-methoxy)-ethyl-), R*-(2-(difluoro-methoxy)-ethyl-), R-(2-(difluoro-methoxy)-ethyl-), 2-methoxy-ethyl-, 2-(methoxy-d$_3$)-ethyl-, R-(2-methoxy-ethyl-), R-(2-(methoxy-d$_3$)-ethyl-), S*-(2-isopropyloxy-ethyl), 2-t-butoxy-ethyl-, S*-(2-(methoxy-d$_3$)-ethyl-2,2-d$_2$-), n-propyl, S*-(n-propyl), R-(2-methoxy-n-propyl-), S*-isobutyl; (b) cyclopropyl-methyl-, R-(cyclopropyl-methyl-), S*-(cyclopropyl-methyl-), 2-methyl-cyclopropyl-methyl-, 2S*-(ethoxy-carbonyl)-1S*-cyclopropyl-methyl-, 2R*-(ethoxy-carbonyl)-1R*-cyclopropyl-methyl-, 2R*-(amino-carbonyl)-1S*-cyclopropyl-methyl-, 2S*-(amino-carbonyl)-1S*-cyclopropyl-methyl-, 2-(1,1'-biphen-4-yl)-cyclopropyl-methyl, 2S*-(pyrrolidin-1-yl-carbonyl)-1S*-cyclopropyl-methyl-, 2-(3-phenyl-pyrrolidin-1-yl-carbonyl)-cyclopropyl-methyl-, 2S*-(3-phenyl-pyrrolidin-1-yl-carbonyl)-1R*-cyclopropyl-methyl-, 2S*-(3-phenyl-pyrrolidin-1-yl-carbonyl)-1S*-cyclopropyl-methyl-, 2R*-(3-phenyl-pyrrolidin-1-yl-carbonyl)-1S*-cyclopropyl-methyl-, 2-(piperidin-1-yl-carbonyl)-cyclopropyl-methyl-, 2R*-(piperidin-1-yl-carbonyl)-1S*-cyclopropyl-methyl-, 2R*-(morpholin-4-yl-carbonyl-methyl-, 2S*-(isoindolin-2-yl-carbonyl)-1S*cyclopropyl-methyl, cyclobutyl-methyl-, 3,3-dimethyl-cyclobutyl-methyl-, cyclopentyl-methyl-, cyclohexyl-methyl-; (c) tetrahydrofuran-2-yl-methyl-, S*-(tetrahydrofuran-2-yl-methyl-), tetrahydropyran-2S*-yl-methyl-, tetrahydropyran-2R*-yl-methyl-, S*-(tetrahydropyran-2S*-yl-methyl-), pyrrolidin-1-yl-carbonyl-methyl-, (pyrrolidin-1-yl-2-one)-methyl-, S*-((pyrrolidin-1-yl-2-one)-methyl-), morpholin-4-yl-carbonyl-methyl-; (d) phenyl-methyl-, 4-chloro-phenyl-methyl-, R*-(4-chloro-phenyl-methyl-), S*-(4-chloro-phenyl-methyl-), 4-fluoro-phenyl-methyl-, 1R*-hydroxy-1-phenyl-methyl-, 1S*-hydroxy-1-phenyl-methyl-, 2-methoxy-phenyl-methyl-, R*-(3-methoxy-phenyl-methyl-), S*-(3-methoxy-phenyl-methyl-), 4-methoxy-phenyl-methyl-, 4-(amino-carbonyl-methoxy)-phenyl-methyl-, 1,1'-biphen-4-yl-methyl-, 4-(phenoxy)-phenyl-methyl-; (f) pyrazol-1-yl-methyl-, R*-(pyrazol-1-yl-methyl-), S*-(pyrazol-1-yl-methyl-), 4-fluoro-pyrazol-1-yl-methyl-, 1-methyl-pyrazol-3-yl-methyl-, R-(1-methyl-pyrazol-3-yl-methyl-), R*-(1-methyl-pyrazol-3-yl-methyl-), 1-(difluoro-methyl)-pyrazol-3-yl-methyl-, S*-(1-(difluoro-methyl)-pyrazol-3-yl-methyl-), R-(1-(difluoro-methyl)-pyrazol-3-yl-methyl-), R*-(1-(difluoro-methyl)-pyrazol-3-yl-methyl-), isochroman-1-yl-methyl-, (pyridin-1-yl-2-one)-methyl-, oxazol-2-yl-methyl-, 1,2,4-oxadiazol-3-yl-methyl-, (5-methyl-1,3,4- oxadiazol-2-yl)-methyl-, thiazol-2-yl-methyl-, S*-(thiazol-2-yl-methyl-); and (g) N-methyl-N-(methoxy-carbonyl)-amino-methyl-.

In certain embodiments, the present invention is directed to compounds of formula (I) wherein $R^S$ is selected from the group consisting of (a) methoxy-carbonyl-methyl-, R*-ethyl, 2-ethoxy-ethyl, 2-(difluoro-methoxy)-ethyl-, S*-(2-(difluoro-methoxy)-ethyl-), R*-(2-(difluoro-methoxy)-ethyl-), R-(2-(difluoro-methoxy)-ethyl-), R-(2-methoxy-ethyl-), R-(2-(methoxy-d)-ethyl-), S*-(2-isopropyloxy-ethyl), R-(2-methoxy-n-propyl-); (b) cyclopropyl-methyl-, R-(cyclopropyl-methyl-), S*-(cyclopropyl-methyl-), 2-methyl-cyclopropyl-methyl-, 2-(3-phenyl-pyrrolidin-1-yl-carbonyl)-cyclopropyl-methyl-, 2R*-(3-phenyl-pyrrolidin-1-yl-carbonyl)-1S*-cyclopropyl-methyl-, 2-(piperidin-1-yl-carbonyl)-cyclopropyl-methyl-; (c) tetrahydropyran-2S*-yl-methyl-, tetrahydropyran-2R*-yl-methyl, ethyl-), (pyrrolidin-1-yl-2-one)-methyl-, S*-((pyrrolidin-1-yl-2-one)-methyl-); (d) phenyl-methyl-, 4-chloro-phenyl-methyl-, 4-fluoro-phenyl-methyl-, 1R*-hydroxy-1-phenyl-methyl-, S*-(3-methoxy-phenyl-methyl-), 4-methoxy-phenyl-methyl-, 4-(amino-carbonyl-methoxy)-phenyl-methyl-, 1,1'-biphen-4-yl-methyl-, 4-(phenoxy)-phenyl-methyl-; (f) pyrazol-1-yl-methyl-, R*-(pyrazol-1-yl-methyl-), S*-(pyrazol-1-yl-methyl-), 4-fluoro-pyrazol-1-yl-methyl-, 1-methyl-pyrazol-3-yl-methyl-, R-(1-methyl-pyrazol-3-yl-methyl-), 1-(difluoro-methyl)-pyrazol-3-yl-methyl-, S*-(1-(difluoro-methyl)-pyrazol-3-yl-methyl-), R-(1-(difluoro-methyl)-pyrazol-3-yl-methyl-), R*-(1-(difluoro-methyl)-pyrazol-3-yl-methyl-), (pyridin-1-yl-2-one)-methyl-, oxazol-2-yl-methyl-, thiazol-2-yl-methyl-, S*-(thiazol-2-yl-methyl-); and (g) N-methyl-N-(methoxy-carbonyl)-amino-methyl-.

In certain embodiments, the present invention is directed to compounds of formula (I) wherein $R^S$ is selected from the group consisting of (a) methoxy-carbonyl-methyl-, 2-(difluoro-methoxy)-ethyl-, S*-(2-(difluoro-methoxy)-ethyl-), R*-(2-(difluoro-methoxy)-ethyl-), R-(2-(difluoro-methoxy)-ethyl-), R-(2-methoxy-ethyl-); (b) cyclopropyl-methyl- and 2-(3-phenyl-pyrrolidin-1-yl-carbonyl)-cyclopropyl-methyl; (c) S*-((pyrrolidin-1-yl-2-one)-methyl-); (d) 4-chloro-phenyl-methyl-, 4-fluoro-phenyl-methyl-, 4-methoxy-phenyl-methyl-, 4-(amino-carbonyl-methoxy)-phenyl-methyl-; (f) R*-(pyrazol-1-yl-methyl-), R-(1-methyl-pyrazol-3-yl-methyl-), S*-(1-(difluoro-methyl)-pyrazol-3-yl-methyl-), R-(1-(difluoro-methyl)-pyrazol-3-yl-methyl-), R*-(1-(difluoro-methyl)-pyrazol-3-yl-methyl-), (pyridin-1-yl-2-one)-methyl-, oxazol-2-yl-methyl- and thiazol-2-yl-methyl-.

In certain embodiments, the present invention is directed to compounds of formula (I) wherein $R^5$ is selected from the group consisting of (a) R*-ethyl, S*-ethyl, *-(2-hydroxy-ethyl-), S*-(2-hydroxy-ethyl-), S-(2-hydroxy-ethyl-), R-(2-hydroxy-ethyl-), S-(2-methoxy-ethyl-), R-(2-methoxy-ethyl-), S*-(2-methoxy-ethyl), R*-(2-methoxy-ethyl-), 2-(difluoro-methoxy)-ethyl-, S-(2-(difluoro-methoxy)-ethyl-), R-(2-(difluoro-methoxy)-ethyl-), S*-(2-(difluoro-methoxy)-ethyl-), R*-(2-(difluoro-methoxy)-ethyl-), R-(2-trifluoro-methoxy-ethyl-), S-(2-t-butoxy-ethyl-), R-(2-t-butoxy-ethyl-), 2-(2-(methyoxy-$d_3$)-ethyl-2,2-$d_2$-), R-(2-hydroxy-ethyl-2,2-$d_2$-), S-(2-hydroxy-ethyl-2,2-$d_2$-), R*-(2-(methoxy-d)-ethyl-2,2-$d_2$-), S-(2-(difluoro-methoxy)-ethyl-2,2-$d_2$-), R-(2-(difluoro-methoxy)-ethyl-2,2-$d_2$-), S-(2-methoxy-2-methyl-n-propyl-), R-(2-methoxy-2-methyl-n-propyl-), S-(2-hydroxy-2-methyl-n-propyl-), R-(2-hydroxy-2-methyl-n-propyl-), R-(3,3,3-trifluoro-n-propyl), S-(3,3,3-trifluoro-n-propyl); (b) cyclopropyl-methyl-, S-(cyclopropyl-methyl-), R-(cyclopropyl-methyl-), R*-(cyclopropyl-methyl-), S*-(cyclopropyl-methyl-), R-(2,2-difluoro-cyclopropyl-methyl-), S-(2,2-difluoro-cyclopropyl-methyl-), R-(cyclobutyl-methyl-), S-(cyclobutyl-methyl-), R-((2-methyl-cyclopropyl)-methyl-), S-((2-methyl-cyclopropyl)-methyl-), S*—(S*-(2-methyl-cyclopropyl)-methyl-), R*—(S*-(2-methyl-cyclopropyl)-methyl-), R*—(R*-(2-methyl-cyclopropyl)-methyl-); (c) morpholin-2-yl-methyl-; (d) R-(4-fluoro-phenyl-methyl-), S-(4-fluoro-phenyl-methyl-), R*-(4-fluoro-phenyl-methyl-), S*-(4-fluoro-phenyl-methyl-), S-(4-(difluoro-methyl)-phenyl-methyl-), R-(4-(difluoro-methyl)-phenyl-methyl-), S—(S-(1-hydroxy-1-phenyl)-methyl-), S—(R-(1-hydroxy-1-phenyl)-methyl-), R*—(R*-(1-hydroxy-1-phenyl)-methyl-), S*—(R*-(1-hydroxy-1-phenyl)-methyl-), R*—(S*-(1-hydroxy-1-phenyl)-methyl-), S*—(S*-(1-hydroxy-1-phenyl)-methyl-); (e) 1-methyl-1,2,5-triazol-3-yl, 1-phenyl-1,2,5-triazol-3-yl; (f) S*-(pyrazol-1-yl-methyl-), R*-(pyrazol-1-yl-methyl-), S-(pyrazol-1-yl-methyl-), R-(pyrazol-1-yl-methyl-), S-(4-fluoro-pyrazol-1-yl-methyl-), S*-(4-fluoro-pyrazol-1-yl-methyl-), R-(4-fluoro-pyrazol-1-yl-methyl-), R-(4-(difluoro-methoxy)-pyrazol-1-yl-methyl-), S-(4-(difluoro-methoxy)-pyrazol-1-yl-methyl-), R-(1-(difluoro-methyl)-pyrazol-3-yl-methyl-), S-(1-(difluoro-methyl)-pyrazol-3-yl-methyl-), R*-(1-(difluoro-methyl)-pyrazol-3-yl-methyl-), S*-(1-(difluoro-methyl)-pyrazol-3-yl-methyl-), R-(thiazol-2-yl-methyl-), S-(thiazol-2-yl-methyl-), 6-(trifluoro-methyl)-pyridin-3-yl-methyl-, R-(6-(trifluoro-methyl)-pyridin-3-yl-methyl-), S-(6-(trifluoro-methyl)-pyridin-3-yl-methyl-), oxazol-2-yl-methyl-, and 1,3,4-oxadiazol-2-yl-methyl- In certain embodiments, the present invention is directed to compounds of formula (I) wherein $R^5$ is selected from the group consisting of (a) R*-ethyl, S*-ethyl, R-(2-hydroxy-ethyl-), R-(2-methoxy-ethyl-), R*-(2-methoxy-ethyl-), 2-(difluoro-methoxy)-ethyl-, S-(2-(difluoro-methoxy)-ethyl-), R-(2-(difluoro-methoxy)-ethyl-), S*-(2-(difluoro-methoxy)-ethyl-), R*-(2-(difluoro-methoxy)-ethyl-), R-(2-trifluoro-methoxy-ethyl-), R-(2-t-butoxy-ethyl-), 2-(2-(methyoxy-$d_3$)-ethyl-2,2-$d_2$-), R-(2-hydroxy-ethyl-2,2-$d_2$-), S*-(2-(methoxy-$d_3$)-ethyl-2,2-d2-), R*-(2-(methoxy-$d_3$)-ethyl-2,2-$d_2$-), S-(2-(difluoro-methoxy)-ethyl-2,2-$d_2$-), R-(2-(difluoro-methoxy)-ethyl-2,2-$d_2$-), R-(2-methoxy-2-methyl-n-propyl-), R-(2-hydroxy-2-methyl-n-propyl-), R-(3,3,3-trifluoro-n-propyl); (b) cyclopropyl-methyl-, S-(cyclopropyl-methyl-), R-(cyclopropyl-methyl-), R*-(cyclopropyl-methyl-), S*-(cyclopropyl-methyl-), R-(2,2-difluoro-cyclopropyl-methyl-), R-(cyclobutyl-methyl-), R-((2-methyl-cyclopropyl)-methyl-), S*—(S*-(2-methyl-cyclopropyl)-methyl-), R*—(R*-(2-methyl-cyclopropyl)-methyl-); (c) morpholin-2-yl-methyl-; (d) R-(4-fluoro-phenyl-methyl-), S-(4-fluoro-phenyl-methyl-), R*-(4-fluoro-phenyl-methyl-), S*-(4-fluoro-phenyl-methyl-), R-(4-(difluoro-methyl)-phenyl-methyl-), S—(S-(1-hydroxy-1-phenyl)-methyl-), S—(R-(1-hydroxy-1-phenyl)-methyl-), R*—(R*-(1-hydroxy-1-phenyl)-methyl-), S*—(R*-(1-hydroxy-1-phenyl)-methyl-), S*—(S*-(1-hydroxy-1-phenyl)-methyl-); (e) 1-methyl-1,2,5-triazol-3-yl, 1-phenyl-1,2,5-triazol-3-yl; (f) S*-(pyrazol-1-yl-methyl-), R-(pyrazol-1-yl-methyl-), S-(4-fluoro-pyrazol-1-yl-methyl-), S*-(4-fluoro-pyrazol-1-yl-methyl-), R-(4-fluoro-pyrazol-1-yl-methyl-), R-(4-(difluoro-methoxy)-pyrazol-1-yl-methyl-), R-(1-(difluoro-methyl)-pyrazol-3-yl-methyl-), S-(1-(difluoro-methyl)-pyrazol-3-yl-methyl-), S*-(1-(difluoro-methyl)-pyrazol-3-yl-methyl-), R-(thiazol-2-yl-methyl-), S-(thiazol-2-yl-methyl-), 6-(trifluoro-methyl)-pyridin-3-yl-methyl-, R-(6-(trifluoro-methyl)-pyridin-3-yl-methyl-), oxazol-2-yl-methyl-, and 1,3,4-oxadiazol-2-yl-methyl-.

In certain embodiments, the present invention is directed to compounds of formula (I) wherein $R^5$ is selected from the group consisting of (a) R*-ethyl, S*-ethyl, R-(2-hydroxy-ethyl-), R-(2-methoxy-ethyl-), R*-(2-methoxy-ethyl-), 2-(difluoro-methoxy)-ethyl-, S-(2-(difluoro-methoxy)-ethyl-), R-(2-(difluoro-methoxy)-ethyl-), S*-(2-(difluoro-methoxy)-ethyl-), R*-(2-(difluoro-methoxy)-ethyl-), R-(2-trifluoro-methoxy-ethyl-), R-(2-t-butoxy-ethyl-), 2-(2-(methyoxy-d$_3$)-ethyl-2,2-d$_2$-), S*-(2-(methoxy-d$_3$)-ethyl-2,2-d$_2$-), R*-(2-(methoxy-d$_3$)-ethyl-2,2-d2-), R-(2-(difluoro-methoxy)-ethyl-2,2-d$_2$-), R-(2-methoxy-2-methyl-n-propyl-); (b) cyclopropyl-methyl-, S-(cyclopropyl-methyl-), R-(cyclopropyl-methyl-), R*-(cyclopropyl-methyl-), S*-(cyclopropyl-methyl-), R-(2,2-difluoro-cyclopropyl-methyl-), R-(cyclobutyl-methyl-), R-((2-methyl-cyclopropyl)-methyl-), S*—(S*-(2-methyl-cyclopropyl)-methyl-), R*—(R*-(2-methyl-cyclopropyl)-methyl-); (c) morpholin-2-yl-methyl-; (d) R-(4-fluoro-phenyl-methyl-), R-(4-(difluoro-methyl)-phenyl-methyl-), S—(S-(1-hydroxy-1-phenyl)-methyl-), S—(R-(1-hydroxy-1-phenyl)-methyl-), S*—(R*-(1-hydroxy-1-phenyl)-methyl-), S*—(S*-(1-hydroxy-1-phenyl)-methyl-); (e) 1-methyl-1,2,5-triazol-3-yl, 1-phenyl-1,2,5-triazol-3-yl; (f) S*-(pyrazol-1-yl-methyl-), R-(pyrazol-1-yl-methyl-), S*-(4-fluoro-pyrazol-1-yl-methyl-), R-(4-fluoro-pyrazol-1-yl-methyl-), R-(1-(difluoro-methyl)-pyrazol-3-yl-methyl-), S*-(1-(difluoro-methyl)-pyrazol-3-yl-methyl-), R-(thiazol-2-yl-methyl-), 6-(trifluoro-methyl)-pyridin-3-yl-methyl-, R-(6-(trifluoro-methyl)-pyridin-3-yl-methyl-), oxazol-2-yl-methyl-, and 1,3,4-oxadiazol-2-yl-methyl-.

In certain embodiments, the present invention is directed to compounds of formula (I) wherein $R^5$ is selected from the group consisting of (a) R-(2-methoxy-ethyl-), 2-(difluoro-methoxy)-ethyl-, R-(2-(difluoro-methoxy)-ethyl-), S*-(2-(difluoro-methoxy)-ethyl-), R-(2-t-butoxy-ethyl-), S*-(2-(methoxy-d$_3$)-ethyl-2,2-d$_2$-), R-(2-(difluoro-methoxy)-ethyl-2,2-d$_2$-); (b) cyclopropyl-methyl-, R-(cyclopropyl-methyl-), R*-(cyclopropyl-methyl-), S*-(cyclopropyl-methyl-), R-(cyclobutyl-methyl-), R-((2-methyl-cyclopropyl)-methyl-), S*—(S*-(2-methyl-cyclopropyl)-methyl-); (d) R-(4-fluoro-phenyl-methyl-), R-(4-(difluoro-methyl)-phenyl-methyl-), S—(S-(1-hydroxy-1-phenyl)-methyl-), S—(R-(1-hydroxy-1-phenyl)-methyl-), S*—(S*-(1-hydroxy-1-phenyl)-methyl-); (e) 1-methyl-1,2,5-triazol-3-yl; (f) S*-(pyrazol-1-yl-methyl-), S*-(4-fluoro-pyrazol-1-yl-methyl-), R-(4-fluoro-pyrazol-1-yl-methyl-), R-(1-(difluoro-methyl)-pyrazol-3-yl-methyl-), S*-(1-(difluoro-methyl)-pyrazol-3-yl-methyl-), R-(thiazol-2-yl-methyl-), R-(6-(trifluoro-methyl)-pyridin-3-yl-methyl-) and oxazol-2-yl-methyl-.

In certain embodiments, the present invention is directed to compounds of formula (I) wherein $R^5$ is selected from the group consisting of (a) R-(2-methoxy-ethyl-), R-(2-(difluoro-methoxy)-ethyl-), R-(2-(difluoro-methoxy)-ethyl-2,2-d$_2$-); (b) cyclopropyl-methyl-, R-(cyclopropyl-methyl-), S*-(cyclopropyl-methyl-); (d) R-(4-fluoro-phenyl-methyl-), S—(R-(1-hydroxy-1-phenyl)-methyl-); (f) R-(4-fluoro-pyrazol-1-yl-methyl-), R-(1-(difluoro-methyl)-pyrazol-3-yl-methyl-), and R-(thiazol-2-yl-methyl-).

In certain embodiments, the present invention is directed to compounds of formula (I) wherein $R^5$ is selected from the group consisting of (a) R*-ethyl, S*-ethyl, 2-methoxy-ethyl-, 2-(difluoro-methoxy)-ethyl-, R-(2-(difluoro-methoxy)-ethyl-), R*-(2-(difluoro-methoxy)-ethyl-), S*-(2-(difluoro-methoxy)-ethyl-), S-(2-(difluoro-methoxy)-ethyl-), 2-(difluoro-methyl-carbonyl)-methyl-, 2-trifluoro-methoxy-ethyl-, R*-(2-(methoxy-d$_3$)-ethyl-), S*-(2-(methoxy-d$_3$)-ethyl-), S*-(2-(difluoro-methoxy)-ethyl-2,2-d$_2$-), and R*-(2-(difluoro-methoxy)-ethyl-2,2-d2-); (b) cyclopropyl-methyl-, S*-(cyclopropyl-methyl-), R*-(cyclopropyl-methyl-), R-(cyclopropyl-methyl-), S-(cyclopropyl-methyl-), 2-(amino-carbonyl)-cyclopropyl-methyl-, 2S*-(amino-carbonyl)-1S*-cyclopropyl-methyl-, 2R*-(amino-carbonyl)-1S*-cyclopropyl-methyl-, R*-(2S*-(amino-carbonyl)-1S*-cyclopropyl-methyl-), R*-(2S*-(amino-carbonyl)-1R*-cyclopropyl-methyl-), S*-(2R*-(amino-carbonyl)-1R*-cyclopropyl-methyl-), S*-(2R*-(amino-carbonyl)-1S*-cyclopropyl-methyl-), S*-(2S*-(amino-carbonyl)-1R*-cyclopropyl-methyl-), R*-(2R*-(amino-carbonyl)-1S*-cyclopropyl-methyl-), 2R*-(piperidin-1-yl-carbonyl)-1S*-cyclopropyl-methyl-, 2S*-(piperidin-1-yl-carbonyl)-1S*-cyclopropyl-methyl-, 2-(piperidin-1-yl-carbonyl)-cyclopropyl-methyl-, 2R*-(pyrrolidin-1-yl-carbonyl)-1S*-cyclopropyl-methyl-, 2S*-(pyrrolidin-1-yl-carbonyl)-1S*-cyclopropyl-methyl-, 2-(3-phenyl-pyrrolidin-1-yl-carbonyl)-cyclopropyl-methyl-, 2-(3-cyclopropyl-pyrrolidin-1-yl-carbonyl)-cyclopropyl-methyl-, 2-(7-amino-azaspiro [2.4]heptan-5-yl-carbonyl)-cyclopropyl-methyl-, 2-(7-carboxy-azaspiro [2.4]heptan-5-yl-carbonyl)-cyclopropyl-methyl-, and 2-(azaspiro[2.4]heptan-5-yl-carbonyl)-cyclopropyl-methyl-; (c) tetrahydro-furan-2-yl-methyl-, R*-(pyrrolidin-1-yl-2-one-methyl-), R-(pyrrolidin-1-yl-2-one-methyl-), S*-(pyrrolidin-1-yl-2-one-methyl-), (pyrrolidin-1-yl-2-one)-methyl-, and (pyrrolidin-1yl-2,5-dione)-methyl-; (d) phenyl-methyl-, 4-chloro-phenyl-methyl-, 4-fluoro-phenyl-methyl-, R*-(4-fluoro-phenyl-methyl-), S*-(4-fluoro-phenyl-methyl-), and 4-methoxy-phenyl-methyl-; (e) 1-methyl-1,2,3-triazol-4-yl-methyl-, R-(1-methyl-1,2,3-triazol-4-yl-methyl), S-(1-methyl-1,2,3-triazol-4-yl-methyl), S-(1-(difluoro-methyl)-1,2,3-triazol-4-yl-methyl-), R-(1-(difluoro-methyl)-1,2,3-triazol-4-yl-methyl-), 1-methyl-1,2,5-triazol-3-yl-methyl-, 1-phenyl-1,2,5-triazol-3-yl-methyl-, R-(1-methyl-1,2,5-triazol-3-yl-methyl-), S-(1-methyl-1,2,5-triazol-3-yl-methyl-), S-(1-(difluoro-methyl)-1,2,5-triazol-3-yl-methyl-), and R-(1-(difluoro-methyl)-1,2,5-triazol-3-yl-methyl-); (f) pyrazol-1-yl-methyl-, R*-(pyrazol-1-yl-methyl-), S*-(pyrazol-1-yl-methyl-), 4-fluoro-pyrazol-1-yl-methyl-, R*-(4-fluoro-pyrazol-1-yl-methyl-), S*-(4-fluoro-pyrazol-1-yl-methyl-), 1-methyl-pyrazol-3-yl-methyl-, 1-methyl-pyrazol-4-yl-methyl-, R-(1-methyl-pyrazol-3-yl-methyl-), S*-(1-methyl-pyrazol-3-yl-methyl-), S-(1-isopropyl-pyrazol-3-yl-methyl-), R-(1-isopropyl-pyrazol-3-yl-methyl-), 1-(difluoro-methyl)-pyrazol-3-yl-methyl-, S-(1-(difluoro-methyl)-pyrazol-1-yl-methyl-), R-(1-(difluoro-methyl)-pyrazol-1-yl-methyl-), R-(3-(difluoro-methoxy)-pyrazol-1-yl-methyl-), S-(3-(difluoro-methoxy)-pyrazol-1-yl)-methyl-), 3-(trifluoro-methyl)-pyrazol-1-yl-methyl-, 5-(trifluoro-methyl)-pyrazol-1-yl-methyl-, 4-(trifluoro-methyl)-pyrazol-1-yl-methyl-, S-(1-(2,2,2-trifluoroethyl)-pyrazol-1-yl-methyl-), R-(1-(2,2,2-trifluoroethyl)-pyrazol-1-yl-methyl-), 1-(2,2,2-trifluoroethyl)-4-fluoro-pyrazol-3-yl-methyl-, R*-(3-(methoxy-methyl)-pyrazol-1-yl-methyl-), S*-(3-(methoxy-methyl)-pyrazol-1-yl-methyl-), 3-(methoxy-methyl)-pyrazol-1-yl-methyl-, 5-(methoxy-methyl)-pyrazol-1-yl-methyl-, S*-(3-(difluoro-methoxy-methyl)-4-fluoro-pyrazol-1-yl-methyl-), R*-(3-(difluoro-methoxy-methyl)-4-fluoro-pyrazol-1-yl-methyl-), 3-carboxy-pyrazol-1-yl-methyl-, 3-(amino-carbonyl)-pyrazol-1-yl-methyl-, 4-(amino-carbonyl)-pyrazol-1-yl-methyl-, 3-(amino-carbonyl-methyl)-pyrazol-1-yl-methyl-, 5-(amino-carbonyl-methyl)-pyrazol-1-yl-methyl-, R*-(3-(amino-carbonyl-methyl)-pyrazol-1-yl-methyl-), R*-(3-(dimethyl-amino-carbonyl)-pyrazol-1-yl-methyl-), 4-(piperidin-1-ylcarbonyl)-pyrazol-1-yl-methyl-, R*-(4-(piperidin-1-yl-carbonyl)-pyrazol-1-yl-methyl-), S*-(4-(piperidin-1-yl-carbonyl)-pyrazol-1-yl-methyl-), 3-(piperidin-1-yl-carbonyl)-pyrazol-1-yl-methyl-, R*-(3-(piperidin-1-yl-carbonyl)-pyrazol-1-yl-methyl-), S*-(3-(piperidin-1-yl-carbonyl)-pyrazol-1-yl-methyl-, 4-(piperidin-1-yl-carbonyl-methyl)-pyrazol-1-yl-methyl-, 3-(4-carboxy-piperidin-1-yl-carbonyl)-pyrazol-1-yl-methyl-, 3-(tetrahydropyran-4-yl)-pyrazol-1-yl-methyl-, R*-(4-(pyridin-2-yl)-pyrazol-1-yl-methyl-), S*-(4-(pyridin-2-yl)-pyrazol-1-yl-methyl-), R*-((5-fluoro-pyridin-1-yl)-pyrazol-1-yl-methyl-), S*-((5-fluoro-pyridin-1-yl)-pyrazol-1-yl-methyl-), 3-phenyl-pyrazol-1-yl-methyl-, R-((3-methyl-imidazolidin-1-yl-2-one)-methyl-), S*-((3-methyl-imidazolidin-1-yl-2-one)-methyl-), (isoindolin-2-yl-1-one)-methyl-, R*-((oxazolidin-3-yl-2-one)-methyl-), S*-((oxazolidin-3-yl-2-one)-methyl-), (pyridin-1-yl-2-one)-methyl-, S*-(pyridin-1-yl-2-one)-methyl-), R*-(pyridin-1-yl-2-one)-methyl-), and 2,4,5,7-tetrahydropyrano[3,4-c]pyrazol-2-yl-methyl-; and (g) (methoxy-carbonyl)-amino-methyl-, (cyclopropyl-carbonyl)-amino-methyl-, (1-methyl-cycloprop-1-yl-carbonyl)-amino-methyl-, (t-butoxy-carbonyl)-amino-methyl-, N-methyl-N-(methyl-carbonyl)-amino-methyl-, R*—(N-methyl-N-(methyl-carbonyl)-amino-methyl-), S*—(N-methyl-N-(methyl-carbonyl)-amino-methyl-), N-methyl-N-(isopropyl-carbonyl)-amino-methyl-, R*—(N-methyl-N-(isopropyl-carbonyl)-amino-methyl-), S*—(N-methyl-N-(isopropyl-carbonyl)-amino-methyl-), S*—(N-methyl-N-(t-butyl-carbonyl)-amino-methyl-), R*—(N-methyl-N-(t-butyl-carbonyl)-amino-methyl-), N-methyl-N-(t-butyl-carbonyl)-amino-methyl-, N-methyl-N-(methoxy-carbonyl)-amino-methyl-, R*—(N-methyl-N-(methoxy-carbonyl)-amino-methyl-), S*—(N-methyl-N-(methoxy-carbonyl)-amino-methyl-), R*—(N-methyl-N-(t-butoxy-carbonyl)-amino-methyl-), S*—(N-methyl-N-(t-butoxy-carbonyl)-amino-methyl-), N-methyl-N-(trifluoro-methoxy)-amino-methyl-, N-methyl-N-(methoxy-methyl-carbonyl)-amino-methyl-, N-methyl-N-(dimethyl-amino-carbonyl)-amino-methyl-, R*—(N-methyl-N-cyclopropyl-carbonyl)-amino-methyl-), S*—(N-methyl-N-(cyclopropyl-carbonyl)-amino-methyl-), N-methyl-N-(phenyl-carbonyl)-amino-methyl-, R*—(N-methyl-N-(phenyl-carbonyl)-amino-methyl-), S*—(N-methyl-N-(phenyl-carbonyl)-amino-methyl-), N-methyl-N-(benzyl-carbonyl)-amino-methyl-, N-methyl-N-(phenyl-ethyl-carbonyl)-amino-methyl-, S*—(N-methyl-N-(phenyl-ethyl-carbonyl)-amino-methyl-), R*—(N-methyl-N-(phenyl-ethyl-carbonyl)-amino-methyl-), R*—(N-methyl-N-(benzyloxy-carbonyl)-amino-methyl-), S*—(N-methyl-N-(benzyloxy-carbonyl)-amino-methyl-), N-methyl-N-(tetrahydropyran-4-yl-carbonyl)-amino-methyl-, N-methyl-N-(2-(piperidin-1-yl-carbonyl)-ethoxy))-amino-ethyl-, N-methyl-N-(piperidin-1-yl-carbonyl-methyl-carbonyl)-amino-methyl-, R*—(N-methyl-N-(2-(piperidin-1-yl-carbonyl)-ethyl-carbonyl)-amino-methyl-), S*—(N-methyl-N-(2-(piperidin-1-yl-carbonyl)-ethyl-carbonyl)-amino-methyl-), S*—(N-methyl-N-(1-methyl-pyridin-4-yl-2-one-carbonyl)-amino-methyl-), and R*—(N-methyl-N-(1-methyl-pyridin-4-yl-2-one-carbonyl)-amino-methyl-).

In certain embodiments, the present invention is directed to compounds of formula (I) wherein $R^S$ is selected from the group consisting of (a) S*-ethyl, 2-methoxy-ethyl-, 2-(difluoro-methoxy)-ethyl-, R-(2-(difluoro-methoxy)-ethyl-), R*-(2-(difluoro-methoxy)-ethyl-), S*-(2-(difluoro-methoxy)-ethyl-, 2-(difluoro-methyl-carbonyl)-methyl-, 2-trifluoro-methoxy-ethyl-, R*-(2-(methoxy-d$_3$)-ethyl-), and R*-(2-(difluoro-methoxy)-ethyl-2,2-d$_2$-); (b) cyclopropyl-methyl-, S*-(cyclopropyl-methyl-), R*-(cyclopropyl-methyl-), R-(cyclopropyl-methyl-), 2-(amino-carbonyl)-cyclopropyl-methyl-, 2S*-(amino-carbonyl)-1S*-cyclopropyl-methyl-, 2R*-(amino-carbonyl)-1S*-cyclopropyl-methyl-, R*-(2S*-(amino-carbonyl)-1S*-cyclopropyl-methyl-), S*-(2R*-(amino-carbonyl)-1R*-cyclopropyl-methyl-), S*-(2R*-(amino-carbonyl)-1S*-cyclopropyl-methyl-), S*-(2S*-(amino-carbonyl)-1R*-cyclopropyl-methyl-), R*-(2R*-(amino-carbonyl)-1S*-cyclopropyl-methyl-), 2R*-(piperidin-1-yl-carbonyl)-1S*-cyclopropyl-methyl-, 2-(piperidin-1-yl-carbonyl)-cyclopropyl-methyl-, 2R*-(pyrrolidin-1-yl-carbonyl)-1S*-cyclopropyl-methyl-, 2S*-(pyrrolidin-1-yl-carbonyl)-1S*-cyclopropyl-methyl-, 2-(3-phenyl-pyrrolidin-1-yl-carbonyl)-cyclopropyl-methyl-, 2-(3-cyclopropyl-pyrrolidin-1-yl-carbonyl)-cyclopropyl-methyl-, 2-(7-amino-azaspiro [2.4]heptan-5-yl-carbonyl)-cyclopropyl-methyl-, 2-(7-carboxy-azaspiro [2.4]heptan-5-yl-carbonyl)-cyclopropyl-methyl-, and 2-(azaspiro[2.4]heptan-5-yl-carbonyl)-cyclopropyl-methyl-; (c) R*-(pyrrolidin-1-yl-2-one-methyl-), R-(pyrrolidin-1-yl-2-one-methyl-), S*-(pyrrolidin-1-yl-2-one-methyl-), (pyrrolidin-1-yl-2-one)-methyl-, and (pyrrolidin-1yl-2,5-dione)-methyl-; (d) phenyl-methyl-, 4-chloro-phenyl-methyl-, 4-fluoro-phenyl-methyl-, R*-(4-fluoro-phenyl-methyl-), S*-(4-fluoro-phenyl-methyl-), and 4-methoxy-phenyl-methyl-; (e) 1-methyl-1,2,3-triazol-4-yl-methyl-, R-(1-methyl-1,2,3-triazol-4-yl-methyl), R-(1-(difluoro-methyl)-1,2,3-triazol-4-yl-methyl-), 1-methyl-1,2,5-triazol-3-yl-methyl-, 1-phenyl-1,2,5-triazol-3-yl-methyl-, R-(1-methyl-1,2,5-triazol-3-yl-methyl-), and R-(1-(difluoro-methyl)-1,2,5-triazol-3-yl-methyl-); (f) pyrazol-1-yl-methyl-, R*-(pyrazol-1-yl-methyl-), S*-(pyrazol-1-yl-methyl-), 4-fluoro-pyrazol-1-yl-methyl-, R*-(4-fluoro-pyrazol-1-yl-methyl-), S*-(4-fluoro-pyrazol-1-yl-methyl-), 1-methyl-pyrazol-3-yl-methyl-, 1-methyl-pyrazol-4-yl-methyl-, R-(1-methyl-pyrazol-3-yl-methyl-), S*-(1-methyl-pyrazol-3-yl-methyl-), R-(1-isopropyl-pyrazol-3-yl-methyl-), 1-(difluoro-methyl)-pyrazol-3-yl-methyl-, R-(1-(difluoro-methyl)-pyrazol-1-yl-methyl-), R-(3-(difluoro-methoxy)-pyrazol-1-yl-methyl-), S-(3-(difluoro-methoxy)-pyrazol-1-yl)-methyl-, 3-(trifluoro-methyl)-pyrazol-1-yl-methyl-, 5-(trifluoro-methyl)-pyrazol-1-yl-methyl-, 4-(trifluoro-methyl)-pyrazol-1-yl-methyl-, R-(1-(2,2,2-trifluoroethyl)-pyrazol-1-yl-methyl-), 1-(2,2,2-trifluoroethyl)-4-fluoro-pyrazol-3-yl-methyl-, R*-(3-(methoxy-methyl)-pyrazol-1-yl-methyl-), S*-(3-(methoxy-methyl)-pyrazol-1-yl-methyl-), 3-(methoxy-methyl)-pyrazol-1-yl-methyl-, 5-(methoxy-methyl)-pyrazol-1-yl-methyl-, S*-(3-(difluoro-methoxy-methyl)-4-fluoro-pyrazol-1-yl-methyl-), R*-(3-(difluoro-methoxy-methyl)-4-fluoro-pyrazol-1-yl-methyl-), 3-carboxy-pyrazol-1-yl-methyl-, 3-(amino-carbonyl)-pyrazol-1-yl-methyl-, 4-(amino-carbonyl)-pyrazol-1-yl-methyl-, 3-(amino-carbonyl-methyl)-pyrazol-1-yl-methyl-, 5-(amino-carbonyl-methyl)-pyrazol-1-yl-methyl-, R*-(3-(amino-carbonyl)-pyrazol-1-yl-methyl-), R*-(3-(dimethyl-amino-carbonyl)-pyrazol-1-yl-methyl-), 4-(piperidin-1-yl-carbonyl)-pyrazol-1-yl-methyl-, R*-(4-(piperidin-1-yl-carbonyl)-pyrazol-1-yl-methyl-), S*-(4-(piperidin-1-yl-carbonyl)-pyrazol-1-yl-methyl-), 3-(piperidin-1-yl-carbonyl)-pyrazol-1-yl-methyl-, R*-(3-(piperidin-1-yl-carbonyl)-pyrazol-1-yl-methyl-), 4-(piperidin-1-yl-carbonyl-methyl)-pyrazol-1-yl-methyl-, 3-(4-carboxy-piperidin-1-yl-carbonyl)-pyrazol-1-yl-methyl-, 3-(tetrahydropyran-4-yl)-pyrazol-1-yl-methyl-, R-((3-methyl-imidazolidin-1-yl-2-one)-methyl-), (isoindolin-2-yl-1-one)-methyl-, R*-((oxazolidin-3-yl-2-one)-methyl-), S*-((oxazolidin-3-yl-2-one)-methyl-), (pyridin-1-yl-2-one)-methyl-, R*-(pyridin-1-yl-2-one)-methyl-), and 2,4,5,7- tetrahydropyrano[3,4-c]pyrazol-2-yl-methyl-; and (g) (1-methyl-cycloprop-1-yl-carbonyl)-amino-methyl-, N-methyl-N-(methyl-carbonyl)-amino-methyl-, S*—(N-methyl-N-(methyl-carbonyl)-amino-methyl-), N-methyl-N-(isopropyl-carbonyl)-amino-methyl-, S*—(N-methyl-N-(isopropyl-carbonyl)-amino-methyl-), R*—(N-methyl-N-(t-butyl-carbonyl)-amino-methyl-), N-methyl-N-(t-butyl-carbonyl)-amino-methyl-, N-methyl-N-(methoxy-carbonyl)-amino-methyl-, S*—(N-methyl-N-(methoxy-carbonyl)-amino-methyl-), S*—(N-methyl-N-(t-butoxy-carbonyl)-amino-methyl-), N-methyl-N-(trifluoro-methoxy)-amino-methyl-, N-methyl-N-(methoxy-methyl-carbonyl)-amino-methyl-, N-methyl-N-(dimethyl-amino-carbonyl)-amino-methyl-, S*—(N-methyl-N-(cyclopropyl-carbonyl)-amino-methyl-), N-methyl-N-(phenyl-carbonyl)-amino-methyl-, R*—(N-methyl-N-(phenyl-carbonyl)-amino-methyl-), N-methyl-N-(benzyl-carbonyl)-amino-methyl-, N-methyl-N-(phenyl-ethyl-carbonyl)-amino-methyl-, S*—(N-methyl-N-(phenyl-ethyl-carbonyl)-amino-methyl-), R*—(N-methyl-N-(benzyloxy-carbonyl)-amino-methyl-), N-methyl-N-(tetrahydropyran-4-yl-carbonyl)-amino-methyl-, N-methyl-N-(2-(piperidin-1-yl-carbonyl)-ethoxy))-amino-ethyl-, N-methyl-N-(piperidin-1-yl-carbonyl-methyl-carbonyl)-amino-methyl-, S*—(N-methyl-N-(2-(piperidin-1-yl-carbonyl)-ethyl-carbonyl)-amino-methyl-), and R*—(N-methyl-N-(1-methyl-pyridin-4-yl-2-one-carbonyl)-amino-methyl-).

In certain embodiments, the present invention is directed to compounds of formula (I) wherein $R^5$ is selected from the group consisting of (a) S*-ethyl, 2-(difluoro-methoxy)-ethyl-, R-(2-(difluoro-methoxy)-ethyl-), R*-(2-(difluoro-methoxy)-ethyl-), S*-(2-(difluoro-methoxy)-ethyl-), 2-(difluoro-methyl-carbonyl)-methyl-, 2-trifluoro-methoxy-ethyl-, R*-(2-(methoxy-d₃)-ethyl-), and R*-(2-(difluoro-methoxy)-ethyl-2,2-d₂-); (b) cyclopropyl-methyl-, S*-(cyclopropyl-methyl-), R*-(cyclopropyl-methyl-), R-(cyclopropyl-methyl-), 2-(amino-carbonyl)-cyclopropyl-methyl-, S*-(2R*-(amino-carbonyl)-1S*-cyclopropyl-methyl-), S*-(2S*-(amino-carbonyl)-1R*-cyclopropyl-methyl-), 2-(piperidin-1-yl-carbonyl)-cyclopropyl-methyl-, 2R*-(pyrrolidin-1-yl-carbonyl)-1S*-cyclopropyl-methyl-, 2-(3-phenyl-pyrrolidin-1-yl-carbonyl)-cyclopropyl-methyl-, 2-(3-cyclopropyl-pyrrolidin-1-yl-carbonyl)-cyclopropyl-methyl-, and 2-(7-carboxy-azaspiro [2.4]heptan-5-yl-carbonyl)-cyclopropyl-methyl-; (c) R-(pyrrolidin-1-yl-2-one-methyl-), S*-(pyrrolidin-1-yl-2-one-methyl-), and (pyrrolidin-1-yl-2-one)-methyl-; (d) phenyl-methyl-, 4-chloro-phenyl-methyl-, 4-fluoro-phenyl-methyl-, R*-(4-fluoro-phenyl-methyl-), S*-(4-fluoro-phenyl-methyl-), and 4-methoxy-phenyl-methyl-; (e) R-(1-methyl-1,2,3-triazol-4-yl-methyl), R-(1-(difluoro-methyl)-1,2,3-triazol-4-yl-methyl-), 1-methyl-1,2,5-triazol-3-yl-methyl-, R-(1-methyl-1,2,5-triazol-3-yl-methyl-), and R-(1-(difluoro-methyl)-1,2,5-triazol-3-yl-methyl-); (f) pyrazol-1-yl-methyl-, R*-(pyrazol-1-yl-methyl-), S*-(pyrazol-1-yl-methyl-), 4-fluoro-pyrazol-1-yl-methyl-, R*-(4-fluoro-pyrazol-1-yl-methyl-), S*-(4-fluoro-pyrazol-1-yl-methyl-), 1-methyl-pyrazol-3-yl-methyl-, 1-methyl-pyrazol-4-yl-methyl-, R-(1-methyl-pyrazol-3-yl-methyl-), R-(1-isopropyl-pyrazol-3-yl-methyl-), 1-(difluoro-methyl)-pyrazol-3-yl-methyl-, R-(1-(difluoro-methyl)-pyrazol-1-yl-methyl-), 3-(trifluoro-methyl)-pyrazol-1-yl-methyl-, 5-(trifluoro-methyl)-pyrazol-1-yl-methyl-, 4-(trifluoro-methyl)-pyrazol-1-yl-methyl-, R-(1-(2,2,2-trifluoroethyl)-pyrazol-1-yl-methyl-), R-(3-(difluoro-methoxy)-pyrazol-1-yl-methyl-), S*-(3-(methoxy-methyl)-pyrazol-1-yl-methyl-), 3-(methoxy-methyl)-pyrazol-1-yl-methyl-, 5-(methoxy-methyl)-pyrazol-1-yl-methyl-, S*-(3-(difluoro-methoxy-methyl)-4-fluoro-pyrazol-1-yl-methyl-), 3-carboxy-pyrazol-1-yl-methyl-, 3-(amino-carbonyl)-pyrazol-1-yl-methyl-, 4-(amino-carbonyl)-pyrazol-1-yl-methyl-, 3-(amino-carbonyl-methyl)-pyrazol-1-yl-methyl-, R*-(3-(dimethyl-amino-carbonyl)-pyrazol-1-yl-methyl-), 4-(piperidin-1-yl-carbonyl)-pyrazol-1-yl-methyl-, R*-(4-(piperidin-1-yl-carbonyl)-pyrazol-1-yl-methyl-), 3-(piperidin-1-yl-carbonyl)-pyrazol-1-yl-methyl-, R*-(3-(piperidin-1-yl-carbonyl)-pyrazol-1-yl-methyl-), 4-(piperidin-1-yl-carbonyl-methyl)-pyrazol-1-yl-methyl-, 3-(4-carboxy-piperidin-1-yl-carbonyl)-pyrazol-1-yl-methyl-, 3-(tetrahydropyran-4-yl)-pyrazol-1-yl-methyl-, R-((3-methyl-imidazolidin-1-yl-2-one)-methyl-), R*-((oxazolidin-3-yl-2-one)-methyl-), S*-((oxazolidin-3-yl-2-one)-methyl-), (pyridin-1-yl-2-one)-methyl-, R*-(pyridin-1-yl-2-one)-methyl-), and 2,4,5,7-tetrahydropyrano[3,4-c]pyrazol-2-yl-methyl-; and (g) N-methyl-N-(methyl-carbonyl)-amino-methyl-, N-methyl-N-(isopropyl-carbonyl)-amino-methyl-, S*—(N-methyl-N-(isopropyl-carbonyl)-amino-methyl-), R*—(N-methyl-N-(t-butyl-carbonyl)-amino-methyl-), N-methyl-N-(t-butyl-carbonyl)-amino-methyl-, N-methyl-N-(methoxy-carbonyl)-amino-methyl-, S*—(N-methyl-N-(methoxy-carbonyl)-amino-methyl-), S*—(N-methyl-N-(t-butoxy-carbonyl)-amino-methyl-), N-methyl-N-(trifluoro-methoxy)-amino-methyl-, N-methyl-N-(dimethyl-amino-carbonyl)-amino-methyl-, N-methyl-N-(phenyl-carbonyl)-amino-methyl-, R*—(N-methyl-N-(phenyl-carbonyl)-amino-methyl-), N-methyl-N-(benzyl-carbonyl)-amino-methyl-, N-methyl-N-(phenyl-ethyl-carbonyl)-amino-methyl-, S*—(N-methyl-N-(phenyl-ethyl-carbonyl)-amino-methyl-), N-methyl-N-(2-(piperidin-1-yl-carbonyl)-ethoxy))-amino-ethyl-, N-methyl-N-(piperidin-1-yl-carbonyl-methyl-carbonyl)-amino-methyl-, and R*—(N-methyl-N-(1-methyl-pyridin-4-yl-2-one-carbonyl)-amino-methyl-).

In certain embodiments, the present invention is directed to compounds of formula (I) wherein $R^S$ is selected from the group consisting of (a) 2-(difluoro-methoxy)-ethyl-, R-(2-(difluoro-methoxy)-ethyl-), R*-(2-(difluoro-methoxy)-ethyl-), S*-(2-(difluoro-methoxy)-ethyl-), and R*-(2-(difluoro-methoxy)-ethyl-2,2-dr); (b) cyclopropyl-methyl-, S*-(cyclopropyl-methyl-), R*-(cyclopropyl-methyl-), 2-(amino-carbonyl)-cyclopropyl-methyl-, S*-(2R*-(amino-carbonyl)-1S*-cyclopropyl-methyl-), S*-(2S*-(amino-carbonyl)-1R*-cyclopropyl-methyl-), and 2-(piperidin-1-yl-carbonyl)-cyclopropyl-methyl-; (c) R-(pyrrolidin-1-yl-2-one-methyl-), S*-(pyrrolidin-1-yl-2-one-methyl-), and (pyrrolidin-1-yl-2-one)-methyl-; (d) 4-chloro-phenyl-methyl-, 4-fluoro-phenyl-methyl-, R*-(4-fluoro-phenyl-methyl-), S*-(4-fluoro-phenyl-methyl-), and 4-methoxy-phenyl-methyl-; (e) R-(1-methyl-1,2,3-triazol-4-yl-methyl), R-(1-(difluoro-methyl)-1,2,3-triazol-4-yl-methyl-), and R-(1-methyl-1,2,5-triazol-3-yl-methyl-); (f) pyrazol-1-yl-methyl-, R*-(pyrazol-1-yl-methyl-), S*-(pyrazol-1-yl-methyl-), 4-fluoro-pyrazol-1-yl-methyl-, R*-(4-fluoro-pyrazol-1-yl-methyl-), S*-(4-fluoro-pyrazol-1-yl-methyl-), 1-methyl-pyrazol-3-yl-methyl-, 1-methyl-pyrazol-4-yl-methyl-, R-(1-methyl-pyrazol-3-yl-methyl-), R-(1-isopropyl-pyrazol-3-yl-methyl-), 1-(difluoro-methyl)-pyrazol-3-yl-methyl-, R-(1-(difluoro-methyl)-pyrazol-1-yl-methyl-), 3-(trifluoro-methyl)-pyrazol-1-yl-methyl-, R-(1-(2,2,2-trifluoroethyl)-pyrazol-1-yl-methyl-), R-(3-(difluoro-methoxy)-pyrazol-1-yl-methyl-), S*-(3-(methoxy-methyl)-pyrazol-1-yl-methyl-), 3-(methoxy-methyl)-pyrazol-1-yl-methyl-, 3-(amino-carbonyl)-pyrazol-1-yl-methyl-, 4-(amino-carbonyl)-pyrazol-1-yl-methyl-, 3-(amino-carbonyl-methyl)-pyrazol-1-yl-methyl-, 4-(piperidin-1-yl-carbonyl)-pyrazol-1-yl-methyl-, 3-(piperidin-1-yl-carbonyl)-pyrazol-1-yl-methyl-, 4-(piperidin-1-yl-carbonyl-methyl)-pyrazol-1-yl-methyl-, 3-(4-carboxy-piperidin-1-yl-carbonyl)-pyrazol-1-yl-methyl-, R-((3-methyl-imidazolidin-1-yl-2-one)-methyl-), and 2,4,5,7-tetrahydropyrano[3,4-c]pyrazol-2-yl-methyl-; and (g) N-methyl-N-(methyl-carbonyl)-amino-methyl-, S*—(N-methyl-N-(isopropyl-carbonyl)-amino-methyl-), R*—(N-methyl-N-(t-butyl-carbonyl)-amino-methyl-), N-methyl-N-(t-butyl-carbonyl)-amino-methyl-, S*—(N-methyl-N-(t-butoxy-carbonyl)-amino-methyl-), N-methyl-N-(phenyl-carbonyl)-amino-methyl-, N-methyl-N-(benzyl-carbonyl)-amino-methyl-, N-methyl-N-(phenyl-ethyl-carbonyl)-amino-methyl-, S*—(N-methyl-N-(phenyl-ethyl-carbonyl)-amino-methyl-), N-methyl-N-(2-(piperidin-1-yl-carbonyl)-ethoxy))-amino-ethyl-, and R*—(N-methyl-N-(1-methyl-pyridin-4-yl-2-one-carbonyl)-amino-methyl-).

In certain embodiments, the present invention is directed to compounds of formula (I) wherein $R^S$ is selected from the group consisting of (a) 2-(difluoro-methoxy)-ethyl-, R-(2-(difluoro-methoxy)-ethyl-), R*-(2-(difluoro-methoxy)-ethyl-), and S*-(2-(difluoro-methoxy)-ethyl-); (b) cyclopropyl-methyl- and R*-(cyclopropyl-methyl-); (c) R-(pyrrolidin-1-yl-2-one-methyl-), S*-(pyrrolidin-1-yl-2-one-methyl-), and (pyrrolidin-1-yl-2-one)-methyl-; (d) R*-(4-fluoro-phenyl-methyl-), and S*-(4-fluoro-phenyl-methyl-); (e) R-(1-methyl-1,2,5-triazol-3-yl-methyl-); (f) pyrazol-1-yl-methyl-, R*-(pyrazol-1-yl-methyl-), S*-(pyrazol-1-yl-methyl-), 4-fluoro-pyrazol-1-yl-methyl-, R*-(4-fluoro-pyrazol-1-yl-methyl-), S*-(4-fluoro-pyrazol-1-yl-methyl-), 1-methyl-pyrazol-3-yl-methyl-, 1-methyl-pyrazol-4-yl-methyl-, R-(1-methyl-pyrazol-3-yl-methyl-), R-(1-isopropyl-pyrazol-3-yl-methyl-), R-(1-(difluoro-methyl)-pyrazol-1-yl-methyl-), R-(1-(2,2,2-trifluoroethyl)-pyrazol-1-yl-methyl-), R-(3-(difluoro-methoxy)-pyrazol-1-yl-methyl-), S*-(3-(methoxy-methyl)-pyrazol-1-yl-methyl-), 3-(methoxy-methyl)-pyrazol-1-yl-methyl-, 3-(amino-carbonyl)-pyrazol-1-yl-methyl-, 3-(amino-carbonyl-methyl)-pyrazol-1-yl-methyl-, 3-(piperidin-1-yl-carbonyl)-pyrazol-1-yl-methyl-, 4-(piperidin-1-yl-carbonyl-methyl)-pyrazol-1-yl-methyl-, 3-(4-carboxy-piperidin-1-yl-carbonyl)-pyrazol-1-yl-methyl-, R-((3-methyl-imidazolidin-1-yl-2-one)-methyl-), 2,4,5,7-tetrahydropyrano[3,4-c]pyrazol-2-yl-methyl-; and (g) N-methyl-N-(phenyl-ethyl-carbonyl)-amino-methyl-, and R*—(N-methyl-N-(1-methyl-pyridin-4-yl-2-one-carbonyl)-amino-methyl-).

In certain embodiments, the present invention is directed to compounds of formula (I) wherein $R^S$ is selected from the group consisting of (a) R-(2-(difluoro-methoxy)-ethyl-), R*-(2-(difluoro-methoxy)-ethyl-), and S*-(2-(difluoro-methoxy)-ethyl-); (b) cyclopropyl-methyl; (c) R-(pyrrolidin-1-yl-2-one-methyl-); (d) R*-(4-fluoro-phenyl-methyl-), and S*-(4-fluoro-phenyl-methyl-); (f) pyrazol-1-yl-methyl-, R*-(pyrazol-1-yl-methyl-), 4-fluoro-pyrazol-1-yl-methyl-, R*-(4-fluoro-pyrazol-1-yl-methyl-), R-(1-methyl-pyrazol-3-yl-methyl-), R-(1-isopropyl-pyrazol-3-yl-methyl-), 3-(methoxy-methyl)-pyrazol-1-yl-methyl-, 3-(amino-carbonyl)-pyrazol-1-yl-methyl-, and 3-(4-carboxy-piperidin-1-yl-carbonyl)-pyrazol-1-yl-methyl-. In certain embodiments, the present invention is directed to compounds of formula (I) wherein $R^S$ is selected from the group consisting of 2-(difluoro-methoxy)-ethyl- and cyclopropyl-methyl-.

In certain embodiments, the present invention is directed to compounds of formula (I) wherein $R^6$ and $R^7$ are each independently selected from the group consisting of hydrogen, halogen, $C_{1-4}$alkyl and $C_{1-4}$alkoxy; provided that at least one of $R^6$ or $R^7$ is hydrogen.

In certain embodiments, the present invention is directed to compounds of formula (I) wherein $R^6$ and $R^7$ are each independently selected from the group consisting of hydrogen, halogen and $C_{1-2}$alkoxy; provided that at least one of $R^6$ or $R^7$ is hydrogen.

In certain embodiments, the present invention is directed to compounds of formula (I) wherein $R^6$ and $R^7$ are each independently selected from the group consisting of hydrogen, chloro, fluoro, methoxy, ethoxy, and iso-propyloxy; provided that at least one of $R^6$ or $R^7$ is hydrogen.

In certain embodiments, the present invention is directed to compounds of formula (I) wherein $R^6$ is selected from the group consisting of hydrogen and halogen. In certain embodiments, the present invention is directed to compounds of formula (I) wherein $R^6$ is selected from the group consisting of hydrogen and fluoro.

In certain embodiments, the present invention is directed to compounds of formula (I) wherein $R^6$ is hydrogen.

In certain embodiments, the present invention is directed to compounds of formula (I) wherein $R^6$ is selected from the group consisting of fluoro and chloro. In certain embodiments, the present invention is directed to compounds of formula (I) wherein $R^6$ is fluoro.

In certain embodiments, the present invention is directed to compounds of formula (I) wherein $R^7$ is selected from the group consisting of hydrogen, halogen, $C_{1-4}$alkyl (preferably $C_{1-2}$alkyl) and $C_{1-4}$alkoxy. In certain embodiments, the present invention is directed to compounds of formula (I) wherein $R^7$ is selected from the group consisting of hydrogen, halogen and $C_{1-2}$alkoxy. In certain embodiments, the present invention is directed to compounds of formula (I) wherein $R^7$ is selected from the group consisting of hydrogen and $C_{1-4}$alkoxy.

In certain embodiments, the present invention is directed to compounds of formula (I) wherein $R^7$ is selected from the group consisting of hydrogen, chloro, methyl, methoxy, ethoxy and isopropyloxy. In certain embodiments, the present invention is directed to compounds of formula (I) wherein $R^7$ is selected from the group consisting of hydrogen, chloro, methoxy and ethoxy. $R^7$ is selected from the group consisting of hydrogen, chloro, methoxy, and ethoxy. In certain embodiments, the present invention is directed to compounds of formula (I) wherein $R^7$ is hydrogen. In certain embodiments, the present invention is directed to compounds of formula (I) wherein $R^7$ is chloro. In certain embodiments, the present invention is directed to compounds of formula (I) wherein $R^7$ is methyl. In certain embodiments, the present invention is directed to compounds of formula (I) wherein $R^7$ is selected from the group consisting of methoxy, ethoxy and isopropyloxy. In certain embodiments, the present invention is directed to compounds of formula (I) wherein $R^7$ is selected from the group consisting of hydrogen, methoxy and ethoxy. In certain embodiments, the present invention is directed to compounds of formula (I) wherein $R^7$ is selected from the group consisting of hydrogen and methoxy. In certain embodiments, the present invention is directed to compounds of formula (I) wherein $R^7$ is selected from the group consisting of hydrogen, and ethoxy. In certain embodiments, the present invention is directed to compounds of formula (I) wherein $R^7$ is methoxy. In certain embodiments, the present invention is directed to compounds of formula (I) wherein $R^7$ is ethoxy.

In certain embodiments, the present invention is directed to compounds of formula (I) wherein $R^7$ is hydrogen.

The compounds of the present invention are useful for the treatment and/or prophylaxis of thromboembolic disorders, inflammatory disorders and diseases or conditions in which plasma kallikrein activity is implicated.

In certain embodiments, the present invention is directed to methods for the treatment and/or prophylaxis of a thromboembolic disorder comprising administering to a patient in need of such treatment and/or prophylaxis a therapeutically effective amount of a least one of the compounds of the present invention, or a stereoisomer, isotopologue, isotopomer or pharmaceutically acceptable salt or solvate thereof.

As used herein, the term "thromboembolic disorders" includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In certain embodiments, the term "thromboembolic disorders" includes acute coronary syndrome, stroke, deep vein thrombosis, and pulmonary embolism. In certain embodiments, the "thromboembolic disorders" include hereditary angioedema (HAE) and diabetic macular edema (DME).

In certain embodiments, the present invention is directed to methods for the treatment and/or prophylaxis of an inflammatory disorder comprising: administering to a patient in need of such treatment and/or prophylaxis a therapeutically effective amount of at least one of the compounds of the present invention or a stereoisomer, isotopologue, isotopomer or pharmaceutically acceptable salt or solvate thereof.

Examples of the inflammatory disorders include, but are not limited to, sepsis, acute respiratory distress syndrome, and systemic inflammatory response syndrome.

In certain embodiments, the present invention is directed to methods for the treatment and/or prophylaxis of a disease or condition in which plasma kallikrein activity is implicated, comprising administering to a patient in need of such treatment and/or prophylaxis a therapeutically effective amount of at least one of the compounds of the present invention or a stereoisomer, isotopologue, isotopomer or pharmaceutically acceptable salt or solvate thereof. The diseases or conditions in which plasma kallikrein activity is implicated include, but are not limited to, impaired visual acuity, diabetic retinopathy, diabetic macular edema, hereditary angioedema, diabetes, pancreatitis, nephropathy, cardiomyopathy, neuropathy, inflammatory bowel disease, arthritis, inflammation, septic shock, hypotension, cancer, adult respiratory distress syndrome, disseminated intravascular coagulation, and cardiopulmonary bypass surgery.

In certain embodiments, the present invention provides a method for the primary prophylaxis of a thromboembolic disorder. In certain embodiments, the present invention provides a method for the primary prophylaxis of a thromboembolic disorder wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In certain embodiments, the present invention provides a method for the secondary prophylaxis of a thromboembolic disorder. In certain embodiments, the present invention provides a method for the secondary prophylaxis of a thromboembolic disorder. wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

In certain embodiments of the present invention, the compound of formula (I) may be administered in combination with one or more anticoagulant, anti-thrombin agent, anti-platelet agent, fibrinolytic, hypolipidemic agent, antihypertensive agent, and/or anti-ischemic agent. Suitable examples include, but are not limited to warfarin, heparin, aprotinin, a synthetic pentasaccharide, a boroarginine derivative, a boropeptide, heparin, hirudin, argatroban, a thromboxane-A2-receptor antagonist, a thromboxane-A2-synthetase inhibitor, a PDE-III inhibitor, a PDE V inhibitor, an ADP receptor antagonist, an antagonist of the purinergic receptor P2Y1, an antagonist of the purinergic receptor P2Y12, tissue plasminogen activator and modified forms thereof, anistreplase, urokinase, streptokinase, tenecteplase, lanoteplase, a PAI-I inhibitor, an alpha-2-antiplasmin inhibitor, an anisoylated plasminogen streptokinase activator complex, a HMG-CoA reductase inhibitor, a squalene synthetase inhibitor, a fibrate, a bile acid sequestrant, an ACAT inhibitor, a MTP inhibitor, a lipooxygenase inhibitor, a cholesterol absorption inhibitor, a cholesterol ester transfer protein inhibitor, an alpha adrenergic blocker, a beta adrenergic blocker, a calcium channel blocker, a diuretic, a renin inhibitor, an angiotensin-converting enzyme inhibitor, an angiotensin-II-receptor antagonist, an ET receptor antagonist, a Dual ET/A11 antagonist, a neutral endopeptidase inhibitor, a vasopeptidase inhibitor, a Class I agent, a Class agent, a Class III agent, a Class IV agent, an IAch inhibitor, an IKur inhibitor and a cardiac glycoside.

In certain embodiments, the present invention is directed to compounds of formula (I) wherein the stereocenter denoted with the "*" is present as a racemic mixture. In certain embodiments, the present invention is directed to compounds of formula (I) wherein the stereocenter denoted with the "*" is present in an enantiomeric excess of the R-enantiomer. In certain embodiments, the present invention is directed to compounds of formula (I) wherein the stereocenter denoted with the "*" is present in an enantiomeric excess of the S-enantiomer.

In certain embodiments, the present invention is directed to compounds of formula (I) is present in an enantiomeric excess of one of the R- or S-enantiomers (at the stereocenter denoted with the "*"). In certain embodiments of the present invention, the compound of formula (I) is present in an enantiomeric excess of one of the R- or S-enantiomers (at the stereocenter denoted with the "*") of about 55%, about 60%, about 65%, about 70%, about 75%, about 80%, about 85%, about 90%, about 91%, about 92%, about 93%, about 94%, about 95%, about 96%, about 97%, about 98% or about 99%. Preferably the compound of formula (I) is present in an enantiomeric excess of one of the R- or S-enantiomers (at the stereocenter denoted with the "*") of greater than or equal to about 80%, preferably greater than or equal to about 90%, more preferably greater than or equal to about 93%, more preferably greater than or equal to about 95%, more preferably greater than or equal to about 97%, more preferably greater than or equal to about 98%, more preferably greater than or equal to about 99%.

Additional embodiments of the present invention include those wherein the substituents selected for one or more of the variables defined herein (i.e. a, Y, Z, $R^1$, $R^2$, $R^3$, $R^4$, $R^5$, $R^6$, $R^7$, etc.) are independently selected to be any individual substituent or any subset of substituents selected from the complete list as defined herein. Additional embodiments of the present invention include those wherein the substituents selected for one or more of the variables defined herein (i.e. a, Y, Z, $R^1$, $R^2$, $R^3$, $R^4$, $R^5$, $R^6$, $R^7$, etc.) are independently selected to correspond to any of the embodiments as defined herein.

In additional embodiments, the present invention is directed to any single compound or subset of compounds selected from the representative compounds listed in Tables 1-5, below.

Representative compounds of the present invention are as listed in Tables 1-5, below. Unless otherwise noted, the position of $R^2$ group(s) as listed in the Table below will follow the following numbering scheme:

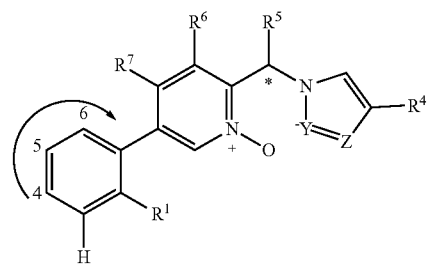

such that the $R^1$ substituted phenyl is bound to the rest of the compound of formula (I) through the 1-position, $R^1$ is bound to the phenyl at the 2-position and any $R^2$ substituents are bound at the 4-, 5- and/or 6-positions.

Unless otherwise noted, wherein a stereogenic center is present in a listed compound, the compound was prepared as a mixture of stereo-configurations. Wherein a stereo-center is designated as part of the substituent group, the S*- or *S- and R*- or *R-designations are intended to indicate that although the substituent group was present in an enantiomeric excess of one stereo-configuration, the exact stereo-configuration of the center was not determined. The designations S- and R- are intended to indicate that substituent group was present in an enantiomeric excess of the corresponding S- or R-stereo-configuration.

TABLE 1

Representative Compounds of Formula (I-Q)

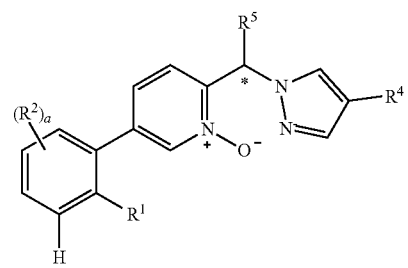

| ID No. | $R^1$ | $(R^2)_a$ | $R^5$ | $R^4$ |
|---|---|---|---|---|
| Q1 | cyano | 5-chloro | 4-fluoro-phenyl-methyl- | 4-(methoxy-carbonyl-amino)-phenyl |
| Q2 | 2,2,2-trifluoro-ethoxy | 5-chloro | 4-fluoro-phenyl-methyl- | 4-carboxy-phenyl |
| Q3 | 2,2,2-trifluoroethoxy | 5-chloro | cyclopropyl-methyl- | 4-(methoxy-carbonyl-amino)-phenyl |
| Q4 | 2,2,2-trifluoro-ethoxy | 5-chloro, 6-fluoro | phenyl-methyl- | 4-carboxy-phenyl |
| Q5 | 2,2,2-trifluoro-ethoxy | 5-chloro, 6-fluoro | 2-methoxy-ethyl- | 4-carboxy-phenyl |
| Q7 | 2,2,2-trifluoro-ethoxy | 5-chloro, 6-fluoro | 2R*-(piperidin-1-yl-carbonyl)-1S*-cyclopropyl-methyl- | 4-carboxy-phenyl |

TABLE 1-continued

Representative Compounds of Formula (I-Q)

| ID No. | R¹ | (R²)ₐ | R⁵ | R⁴ |
|---|---|---|---|---|
| Q8 | 2,2,2-trifluoro-ethoxy | 5-chloro, 6-fluoro | 2S*-(piperidin-1-yl-carbonyl)-1S*-cyclopropyl-methyl- | 4-carboxy-phenyl |
| Q11 | fluoro | 5-chloro, 6-fluoro | 2S*-(amino-carbonyl)-1S*-cyclopropyl-methyl- | 4-(methoxy-carbonyl-amino)-phenyl |
| Q12 | difluoro-methyl | 5-chloro, 6-fluoro | R*-(cyclopropyl-methyl-) | 4-carboxy-phenyl |
| Q13 | difluoro-methyl | 5-chloro, 6-fluoro | S*-(cyclopropyl-methyl-) | 4-carboxy-phenyl |
| Q14 | difluoro-methyl | 5-chloro, 6-fluoro | R*-(pyrrolidin-1-yl-2-one-methyl-) | 4-carboxy-phenyl |
| Q15 | difluoro-methyl | 5-chloro, 6-fluoro | S*-(pyrrolidin-1-yl-2-one-methyl-) | 4-carboxy-phenyl |
| Q16 | difluoro-methyl | 5-chloro, 6-fluoro | cyclopropyl-methyl- | 4-carboxy-phenyl |
| Q17 | difluoro-methoxy | 5-chloro, 6-fluoro | R*-(4-fluoro-phenyl-methyl-) | pyridin-4-yl-1-oxide |
| Q18 | difluoro-methyl | 5-chloro, 6-fluoro | S*-(4-fluoro-phenyl-methyl-) | pyridin-4-yl-1-oxide |
| Q19 | difluoro-methoxy | 5-chloro, 6-fluoro | S*-(4-fluoro-phenyl-methyl-) | pyridin-4-yl-1-oxide |
| Q20 | difluoro-methyl | 5-chloro, 6-fluoro | R*-(4-fluoro-phenyl-methyl-) | pyridin-4-yl-1-oxide |
| Q21 | difluoro-methoxy | 5-chloro, 6-fluoro | cyclopropyl-methyl- | 2-carboxy-pyridin-4-yl |
| Q22 | difluoro-methyl | 5-chloro, 6-fluoro | R*-(4-fluoro-pyrazol-1-yl-methyl-) | 2-(trifluoro-methyl)-pyridin-4-yl |
| Q23 | difluoro-methyl | 5-chloro, 6-fluoro | S*-(4-fluoro-pyrazol-1-yl-methyl-) | 2-(trifluoro-methyl)-pyridin-4-yl |
| Q24 | difluoro-methyl | 5-chloro, 6-fluoro | cyclopropyl-methyl- | 5-carboxy-pyrrol-3-yl |
| Q25 | difluoro-methyl | 5-chloro, 6-fluoro | R*-(4-fluoro-pyrazol-1-yl-methyl-) | 2-fluoro-6-amino-pyridin-3-yl |
| Q26 | difluoro-methyl | 5-chloro, 6-fluoro | S*-(4-fluoro-pyrazol-1-yl-methyl-) | 2-fluoro-6-amino-pyridin-3-yl |
| Q27 | difluoro-methyl | 5-chloro, 6-fluoro | S*-(5-(amino-carbonyl)-pyrazol-1-yl-methyl-) | 2-(trifluoro-methyl)-pyridin-4-yl |
| Q28 | difluoro-methyl | 5-chloro, 6-fluoro | R*-(5-(amino-carbonyl)-pyrazol-1-yl-methyl-) | 2-(trifluoro-methyl)-pyridin-4-yl |
| Q29 | difluoro-methyl | 5-chloro, 6-fluoro | 2-(difluoro-methoxy)-ethyl- | 2-(trifluoro-methyl)-pyrimidin-4-yl |
| Q30 | difluoro-methyl | 5-chloro, 6-fluoro | 4-fluoro-pyrazol-1-yl-methyl- | 1-methyl-pyrazol-5-yl |
| Q31 | difluoro-methyl | 5-chloro, 6-fluoro | 4-fluoro-pyrazol-1-yl-methyl- | 4-carboxy-phenyl |
| Q32 | difluoro-methyl | 5-chloro, 6-fluoro | 4-fluoro-pyrazol-1-yl-methyl- | 4-carboxy-phenyl |
| Q33 | difluoro-methyl | 5-chloro, 6-fluoro | S-(2-methoxy-ethyl-) | 4-carboxy-phenyl |
| Q34 | difluoro-methyl | 5-chloro, 6-fluoro | R-(2-methoxy-ethyl-) | 4-carboxy-phenyl |
| Q35 | difluoro-methyl | 5-chloro, 6-fluoro | R-(2-(difluoro-methoxy)-ethyl-) | 4-carboxy-phenyl |
| Q36 | difluoro-methyl | 5-chloro, 6-fluoro | S-(2-(difluoro-methoxy)-ethyl-) | 4-carboxy-phenyl |
| Q37 | difluoro-methyl | 5-chloro, 6-fluoro | R*-(2S*-(piperidin-1-yl-carbonyl)-cyclopropyl-methyl-) | 4-(amino-carbonyl)-phenyl |
| Q38 | difluoro-methyl | 5-chloro, 6-fluoro | S*-(2R*-(piperidin-1-yl-carbonyl)-cyclopropyl-methyl-) | 4-carboxy-phenyl |
| Q39 | difluoro-methyl | 5-chloro, 6-fluoro | R*-(2S*-(piperidin-1-yl-carbonyl)-cyclopropyl-methyl-) | 4-carboxy-phenyl |
| Q40 | difluoro-methyl | 5-chloro, 6-fluoro | S*-(2-(piperidin-1-yl-carbonyl)-cyclopropyl-methyl-) | 4-(amino-carbonyl)-phenyl |
| Q41 | difluoro-methyl | 5-chloro, 6-fluoro | S*-(1-methyl-pyrazol-4-yl-methyl-) | 1-methyl-1,2,3-triazol-5-yl |
| Q42 | difluoro-methyl | 5-chloro, 6-fluoro | R*-(1-methyl-pyrazol-4-yl-methyl-) | 1-methyl-1,2,3-triazol-5-yl |
| Q43 | amino | 5-chloro, 6-fluoro | S-(2-(difluoro-methoxy)-ethyl-) | 1-methyl-1,2,3-triazol-5-yl |

TABLE 1-continued

Representative Compounds of Formula (I-Q)

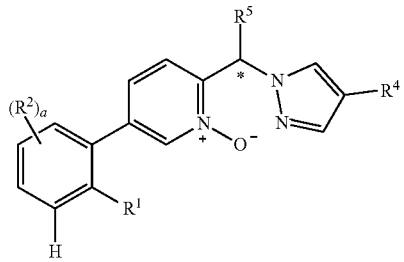

| ID No. | R¹ | (R²)$_a$ | R⁵ | R⁴ |
| --- | --- | --- | --- | --- |
| Q44 | amino | 5-chloro, 6-fluoro | R-(2-(difluoro-methoxy)-ethyl-) | 1-methyl-1,2,3-triazol-5-yl |
| Q45 | amino | 5-chloro, 6-fluoro | R-(2-(difluoro-methoxy)-ethyl-) | 1-methyl-1,2,4-triazol-5-yl |
| Q46 | cyano | 5-chloro | S-(1-methyl-pyrazol-3-yl-methyl-) | 4-carboxy-phenyl |
| Q47 | cyano | 5-chloro | R-(1-methyl-pyrazol-3-yl-methyl-) | 4-carboxy-phenyl |
| Q48 | difluoro-methyl | 5-chloro, 6-fluoro | S-(1-methyl-pyrazol-3-yl-methyl-) | 4-carboxy-phenyl |
| Q49 | difluoro-methyl | 5-chloro, 6-fluoro | R-(1-methyl-pyrazol-3-yl-methyl-) | 4-carboxy-phenyl |
| Q52 | cyano | 5-chloro | R*-(2-(difluoro-methoxy)-ethyl-2,2-d2-) | 1-(difluoro-methyl)-1,2,4-triazol-5-yl |
| Q53 | cyano | 5-chloro | S*-(2-(difluoro-methoxy)-ethyl-2,2-d2-) | 1-(difluoro-methyl)-1,2,4-triazol-5-yl |
| Q57 | 2,2,2-trifluoro-ethoxy | 5-chloro | S-(1-methyl-pyrazol-3-yl-methyl-) | 4-carboxy-phenyl |
| Q58 | 2,2,2-trifluoro-ethoxy | 5-chloro | R-(1-methyl-pyrazol-3-yl-methyl-) | 4-carboxy-phenyl |
| Q64 | difluoro-methyl | 5-chloro, 6-fluoro | S*-(1-(difluoro-methyl)-pyrazol-3-yl-methyl-) | 3-fluoro-4-carboxy-phenyl |
| Q65 | difluoro-methyl | 5-chloro, 6-fluoro | R*-(1-(difluoro-methyl)-pyrazol-3-yl-methyl-) | 3-fluoro-4-carboxy-phenyl |
| Q66 | difluoro-methyl | 5-chloro, 6-fluoro | R*-(1-(difluoro-methyl)-pyrazol-3-yl-methyl-) | 3-fluoro-4-(amino-carbonyl)-phenyl |
| Q67 | difluoro-methyl | 5-chloro, 6-fluoro | S*-(1-(difluoro-methyl)-pyrazol-3-yl-methyl-) | 3-fluoro-4-(amino-carbonyl)-phenyl |
| Q68 | difluoro-methyl | 5-chloro, 6-fluoro | R*-(1-(difluoro-methyl)-pyrazol-3-yl-methyl-) | 4-(amino-carbonyl)-phenyl |
| Q69 | difluoro-methyl | 5-chloro, 6-fluoro | S*-(1-(difluoro-methyl)-pyrazol-3-yl-methyl-) | 4-(amino-carbonyl)-phenyl |
| Q70 | difluoro-methyl | 5-chloro, 6-fluoro | R*-(1-(difluoro-methyl)-pyrazol-3-yl-methyl-) | 4-carboxy-phenyl |
| Q71 | difluoro-methyl | 5-chloro, 6-fluoro | S*-(1-(difluoro-methyl)-pyrazol-3-yl-methyl-) | 4-carboxy-phenyl |
| Q72 | difluoro-methoxy | 5-chloro, 6-fluoro | R*-(1-(difluoro-methyl)-pyrazol-3-yl-methyl-) | 3-fluoro-4-(amino-carbonyl)-phenyl |
| Q73 | difluoro-methoxy | 5-chloro, 6-fluoro | S*-(1-(difluoro-methyl)-pyrazol-3-yl-methyl-) | 3-fluoro-4-(amino-carbonyl)-phenyl |

TABLE 2

Representative Compounds of Formula (I-Q)

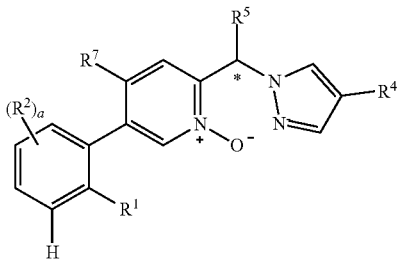

| ID No. | R¹ | (R²)$_a$ | R⁵ | R⁴ | R⁷ |
|---|---|---|---|---|---|
| Q6 | 2,2,2-trifluoro-ethoxy | 5-chloro, 6-fluoro | phenyl-methyl- | 4-carboxy-phenyl | methoxy |
| Q9 | cyano | 5-chloro, 6-fluoro | R*-(cyclopropyl-methyl-) | 1-methyl-pyridazin-4-yl-6-one | methoxy |
| Q10 | cyano | 5-chloro, 6-fluoro | S*-(cyclopropyl-methyl-) | 1-methyl-pyridazin-4-yl-6-one | methoxy |
| Q50 | cyano | 5-chloro | S-(cyclopropyl-methyl-) | 4-carboxy-phenyl | methoxy |
| Q51 | cyano | 5-chloro | R-(cyclopropyl-methyl-) | 4-carboxy-phenyl | methoxy |
| Q54 | cyano | 5-chloro | ethyl | 1-(difluoro-methyl)-1,2,4-triazol-5-yl | methoxy |
| Q55 | cyano | 5-chloro, 6-fluoro | S-(cyclopropyl-methyl-) | 1-(difluoro-methyl)-1,2,4-triazol-5-yl | methoxy |
| Q56 | cyano | 5-chloro, 6-fluoro | R-(cyclopropyl-methyl-) | 1-(difluoro-methyl)-1,2,4-triazol-5-yl | methoxy |
| Q59 | cyano | 5-chloro | cyclopropyl-methyl- | 3-fluoro-4-(amino-carbonyl)-phenyl | methoxy |
| Q60 | cyano | 5-chloro | R*-(cyclopropyl-methyl-) | 1-methyl-1,2,4-triazol-5-yl | methoxy |
| Q61 | cyano | 5-chloro | S*-(cyclopropyl-methyl-) | 1-methyl-1,2,4-triazol-5-yl | methoxy |
| Q62 | cyano | 5-chloro | R*-(cyclopropyl-methyl-) | 1-methyl-4-fluoro-1,2,3-triazol-5-yl | methoxy |
| Q63 | cyano | 5-chloro | S*-(cyclopropyl-methyl-) | 1-methyl-4-fluoro-1,2,3-triazol-5-yl | methoxy |
| Q74 | difluoro-methyl | 5-chloro, 6-fluoro | 1-(difluoro-methyl)-pyrazol-3-yl-methyl- | 3-fluoro-4-carboxy-phenyl | methoxy |
| Q75 | difluoro-methyl | 5-chloro, 6-fluoro | 1-(difluoro-methyl)-pyrazol-3-yl-methyl- | 3-fluoro-4-(amino-carbonyl)-phenyl | methoxy |
| Q76 | methyl-carbonyl- | 5-chloro | R*-(1-(difluoro-methyl)-pyrazol-3-yl-methyl-) | 3-fluoro-4-carboxy-phenyl | methoxy |
| Q77 | methyl-carbonyl- | 5-chloro | R*-(1-(difluoro-methyl)-pyrazol-3-yl-methyl-) | 3-fluoro-4-(amino-carbonyl)-phenyl | methoxy |
| Q78 | methyl-carbonyl- | 5-chloro | S*-(1-(difluoro-methyl)-pyrazol-3-yl-methyl-) | 3-fluoro-4-(amino-carbonyl)-phenyl | methoxy |

TABLE 3

Representative Compounds of Formula (I)

(I-PX)

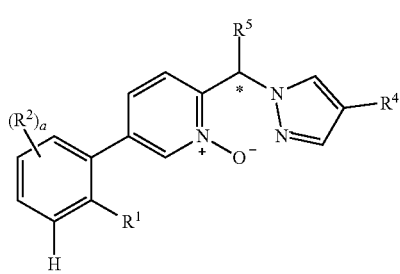

| ID No. | R¹ | (R²)$_a$ | R⁵ | R4 |
|---|---|---|---|---|
| P1 | 1,2,3,4-tetrazol-1-yl | 5-chloro | cyclopropyl-methyl- | 4-carboxy-phenyl |
| P2 | 1,2,3,4-tetrazol-1-yl | 5-chloro | cyclopropyl-methyl- | 4-(methoxy-carbonyl-amino)-phenyl |

TABLE 3-continued

Representative Compounds of Formula (I)

| | | | | |
|---|---|---|---|---|
| P3 | 1,2,3,4-tetrazol-1-yl | 5-chloro | cyclopropyl-methyl- | 3-carboxy-phenyl |
| P4 | 4-chloro-1,2,3-triazol-1-yl | 5-chloro | cyclopropyl-methyl- | 4-carboxy-phenyl |
| P5 | 1,2,3,4-tetrazol-1-yl | 5-chloro | S-(cyclopropyl-methyl-) | 4-carboxy-phenyl |
| P6 | 1,2,3,4-tetrazol-1-yl | 5-chloro | R-(cyclopropyl-methyl-) | 4-carboxy-phenyl |
| P7 | 1,2,3,4-tetrazol-1-yl | 5-chloro | 4-fluoro-phenyl-methyl- | 4-carboxy-phenyl |
| P8 | 1,2,3,4-tetrazol-1-yl | 5-chloro | 2-t-butoxy-ethyl- | 4-carboxy-phenyl |
| P9 | 1,2,3,4-tetrazol-1-yl | 5-chloro, 6-fluoro | cyclopropyl-methyl- | 4-carboxy-phenyl |
| P10 | pyrazol-5-yl | 5-chloro | cyclopropyl-methyl- | 4-(methoxy-carbonyl-amino)-phenyl |
| P13 | 1,2,3,4-tetrazol-1-yl | 5-chloro | cyclopropyl-methyl- | 3-carboxy-phenyl |
| P14 | 4-chloro-1,2,3-triazol-1-yl | 5-chloro | cyclopropyl-methyl- | 4-(methoxy-carbonyl-amino)-phenyl |
| P17 | 1,2,3,4-tetrazol-1-yl | 5-chloro, 6-fluoro | cyclopropyl-methyl- | 4-(methoxy-carbonyl-amino)-phenyl |
| P18 | 1,2,3,4-tetrazol-1-yl | 5-chloro | cyclopropyl-methyl- | 4-(methyl-sulfonyl-amino-carbonyl)-phenyl |
| P21 | 1,2,3,4-tetrazol-1-yl | 5-chloro, 6-fluoro | cyclopropyl-methyl- | 4-amino-phenyl |
| P22 | 1,2,3,4-tetrazol-1-yl | 5-chloro | 4-fluoro-phenyl-methyl- | 4-fluoro-phenyl |
| P23 | 1,2,3,4-tetrazol-1-yl | 5-chloro, 6-fluoro | cyclopropyl-methyl- | 4-(methyl-carbonyl-amino)-phenyl |
| P26 | 1,2,3,4-tetrazol-1-yl | 5-chloro | 1-phenyl-1,2,3-triazol-4-yl | 4-carboxy-phenyl |
| P27 | 1,2,3,4-tetrazol-1-yl | 5-chloro, 6-fluoro | R*-(cyclopropyl-methyl-) | 4-(methoxy-carbonyl-amino)-phenyl |
| P28 | 1,2,3,4-tetrazol-1-yl | 5-chloro, 6-fluoro | R-(cyclopropyl-methyl-) | 4-(methoxy-carbonyl-amino)-phenyl |
| P31 | 1,2,3,4-tetrazol-1-yl | 5-chloro | 1-methyl-1,2,3-triazol-4-yl | 4-carboxy-phenyl |
| P32 | 1,2,3,4-tetrazol-1-yl | 5-chloro | 1-methyl-1,2,3-triazol-4-yl | 3-carboxy-phenyl |
| P33 | 1,2,3,4-tetrazol-1-yl | 5-chloro, 6-fluoro | 1-methyl-1,2,3-triazol-4-yl | 4-carboxy-phenyl |
| P34 | 1,2,3,4-tetrazol-1-yl | 5-chloro | cyclopropyl-methyl- | 4-(methoxy-carbonyl-amino)-phenyl |
| P35 | 1,2,3,4-tetrazol-1-yl | 5-chloro, 6-fluoro | 1-phenyl-1,2,3-triazol-4-yl | 4-carboxy-phenyl |
| P38 | 1,2,3,4-tetrazol-1-yl | 5-chloro, 6-fluoro | 2-methoxy-ethyl- | 4-(methoxy-carbonyl-amino)-phenyl |
| P39 | 1,2,3,4-tetrazol-1-yl | 5-chloro | phenyl-methyl- | 4-(methoxy-carbonyl-amino)-phenyl |
| P40 | 1,2,3,4-tetrazol-1-yl | 4-chloro | cyclopropyl-methyl- | 4-(methoxy-carbonyl-amino)-phenyl |
| P41 | 1,2,3,4-tetrazol-1-yl | 4,5-dichloro | cyclopropyl-methyl- | 4-(methoxy-carbonyl-amino)-phenyl |
| P42 | 1,2,3,4-tetrazol-1-yl | 5-chloro | R*-(cyclopropyl-methyl-) | 4-(methoxy-carbonyl-amino)-phenyl |
| P43 | 1,2,3,4-tetrazol-1-yl | 5-chloro | S*-(cyclopropyl-methyl-) | 4-(methoxy-carbonyl-amino)-phenyl |
| P44 | 1,2,3,4-tetrazol-1-yl | 5-chloro, 4-fluoro | 2-methoxy-ethyl- | 4-(methoxy-carbonyl-amino)-phenyl |
| P46 | 1,2,3,4-tetrazol-1-yl | 5-chloro, 4-fluoro | phenyl-methyl- | 4-(methoxy-carbonyl-amino)-phenyl |
| P47 | 1,2,3,4-tetrazol-1-yl | 5-chloro | phenyl-methyl- | 4-(1-amino-ethyl)-phenyl |
| P51 | 1,2,3,4-tetrazol-1-yl | 5-chloro | 1-(piperidin-4-yl)-1,2,3-triazol-4-yl | 4-carboxy-phenyl |
| P52 | 1,2,3,4-tetrazol-1-yl | 5-chloro, 6-fluoro | 1-(piperidin-4-yl)-1,2,3-triazol-4-yl | 4-carboxy-phenyl |
| P53 | 1,2,3,4-tetrazol-1-yl | 5-chloro | 1-(1-methyl-carbonyl-piperidin-4-yl)-1,2,3-triazol-4-yl | 4-carboxy-phenyl |
| P54 | 1,2,3,4-tetrazol-1-yl | 5-chloro, 6-fluoro | 1-(1-methyl-carbonyl-piperidin-4-yl)-1,2,3-triazol-4-yl | 4-carboxy-phenyl |
| P55 | 1,2,3,4-tetrazol-1-yl | 5-chloro | 4-fluoro-phenyl-methyl- | 4-(cyclopropyl-amino-carbonyl)-phenyl |
| P56 | 1,2,3,4-tetrazol-1-yl | 4-chloro, 6-fluoro | cyclopropyl-methyl- | 4-(methoxy-carbonyl-amino)-phenyl |
| P57 | 1,2,3,4-tetrazol-1-yl | 5-chloro | 4-chloro-phenyl-methyl- | 4-carboxy-phenyl |
| P58 | 1,2,3,4-tetrazol-1-yl | 5-chloro | phenyl-methyl- | 4-(1-(methoxy-carbonyl-amino)-ethyl)-phenyl |
| P60 | 1,2,3,4-tetrazol-1-yl | 4-chloro, 5-fluoro | cyclopropyl-methyl- | 4-(methoxy-carbonyl-amino)-phenyl |
| P61 | 1,2,3,4-tetrazol-1-yl | 5-chloro | 2-(1,1'-biphen-4-yl)-cyclopropyl-methyl | 4-carboxy-phenyl |
| P62 | 1,2,3,4-tetrazol-1-yl | 5-chloro | 1,1'-biphen-4-yl-methyl- | 4-carboxy-phenyl |
| P64 | 1,2,3,4-tetrazol-1-yl | 5-chloro | 4-methoxy-phenyl-methyl- | 4-carboxy-phenyl |
| P65 | 1,2,3,4-tetrazol-1-yl | 5-chloro | phenyl-ethyl- | 4-carboxy-phenyl |

TABLE 3-continued

Representative Compounds of Formula (I)

| | | | | |
|---|---|---|---|---|
| P67 | 1,2,3,4-tetrazol-1-yl | 5-chloro | 2S*-(ethoxy-carbonyl)-1S*-cyclopropyl-methyl- | 4-carboxy-phenyl |
| P68 | 1,2,3,4-tetrazol-1-yl | 5-chloro | 2R*-(ethoxy-carbonyl)-1R*-cyclopropyl-methyl- | 4-carboxy-phenyl |
| P69 | 1,2,3,4-tetrazol-1-yl | 5-chloro | 2S*-carboxy-1S*-cyclopropyl-methyl- | 4-carboxy-phenyl |
| P70 | 1,2,3,4-tetrazol-1-yl | 5-chloro | 2R*-carboxy-1R*-cyclopropyl-methyl- | 4-carboxy-phenyl |
| P71 | 1,2,3,4-tetrazol-1-yl | 5-chloro, 6-fluoro | phenyl-methyl- | 4-(methoxy-carbonyl-amino)-phenyl |
| P72 | 1,2,3,4-tetrazol-1-yl | 5-chloro | 2R*-(piperidin-1-yl-carbonyl)-1R*-cyclopropyl-methyl- | 4-carboxy-phenyl |
| P73 | 1,2,3,4-tetrazol-1-yl | 5-chloro | 2S*-(piperidin-1-yl-carbonyl)-1S*-cyclopropyl-methyl- | 4-carboxy-phenyl |
| P74 | 1,2,3,4-tetrazol-1-yl | 5-chloro | 2R*-(piperazin-1-yl-carbonyl)-1S*-cyclopropyl-methyl- | 4-carboxy-phenyl |
| P76 | 1,2,3,4-tetrazol-1-yl | 5-chloro, 6-fluoro | phenyl-methyl- | 4-(methyl-sulfonyl-amino)-phenyl |
| P77 | 1,2,3,4-tetrazol-1-yl | 5-chloro, 6-fluoro | tetrahydropyran-2R*-yl-methyl- | 4-(cyclopropyl-amino-carbonyl)-phenyl |
| P78 | 1,2,3,4-tetrazol-1-yl | 5-chloro | 2R*-(piperidin-1-yl-carbonyl)-1S*-cyclopropyl-methyl- | 4-carboxy-phenyl |
| P79 | 1,2,3,4-tetrazol-1-yl | 5-chloro | 2S*-(piperidin-1-yl-carbonyl)-1S*-cyclopropyl-methyl- | 4-carboxy-phenyl |
| P80 | 1,2,3,4-tetrazol-1-yl | 5-chloro, 6-fluoro | tetrahydropyran-2S*-yl-methyl- | 4-(cyclopropyl-amino-carbonyl)-phenyl |
| P81 | 1,2,3,4-tetrazol-1-yl | 5-chloro | 2R*-(morpholin-4-yl-carbonyl)-1S*-cyclopropyl-methyl- | 4-carboxy-phenyl |
| P82 | 1,2,3,4-tetrazol-1-yl | 5-chloro | 2S*-(morpholin-4-yl-carbonyl)-1S*-cyclopropyl-methyl- | 4-carboxy-phenyl |
| P83 | 1,2,3,4-tetrazol-1-yl | 5-chloro, 6-fluoro | R*-(2-methoxy-ethyl-) | 4-(methoxy-carbonyl-amino)-phenyl |
| P84 | 1,2,3,4-tetrazol-1-yl | 5-chloro, 6-fluoro | R-(2-methoxy-ethyl) | 4-(methoxy-carbonyl-amino)-phenyl |
| P86 | 1,2,3,4-tetrazol-1-yl | 5-chloro | 4-methoxy-phenyl-methyl- | 4-(cyclopropyl-amino-carbonyl)-phenyl |
| P87 | 1,2,3,4-tetrazol-1-yl | 5-chloro | 1,1'-biphen-4-yl-methyl- | 4-(cyclopropyl-amino-carbonyl)-phenyl |
| P88 | 1,2,3,4-tetrazol-1-yl | 5-chloro | cyclopropyl-methyl- | 4-((1-methoxy-carbonyl)-cycloprop-1-yl)-phenyl |
| P89 | 1,2,3,4-tetrazol-1-yl | 5-chloro | cyclopropyl-methyl- | 4-(1-carboxy-cycloprop-1-yl)-phenyl |
| P90 | 1,2,3,4-tetrazol-1-yl | 5-chloro | piperazin-1-yl-carbonyl-methyl- | 4-carboxy-phenyl |
| P91 | 1,2,3,4-tetrazol-1-yl | 5-chloro | morpholin-4-yl-carbonyl-methyl- | 4-carboxy-phenyl |
| P92 | 1,2,3,4-tetrazol-1-yl | 5-chloro | 4-chloro-phenyl-methyl- | 4-(methoxy-carbonyl-amino)-phenyl |
| P94 | 1,2,3,4-tetrazol-1-yl | 5-chloro, 6-fluoro | 4-chloro-phenyl-methyl- | 4-(methoxy-carbonyl-amino)-phenyl |
| P95 | 1,2,3,4-tetrazol-1-yl | 5-chloro | 2R*-(isoindolin-2-yl-carbonyl)-1S*cyclopropyl-methyl | 4-carboxy-phenyl |
| P96 | 1,2,3,4-tetrazol-1-yl | 5-chloro | 2S*-(isoindolin-2-yl-carbonyl)-1S*cyclopropyl-methyl | 4-carboxy-phenyl |
| P97 | 1,2,3,4-tetrazol-1-yl | 5-chloro | 2S*-(isoindolin-2-yl-carbonyl)-1R*cyclopropyl-methyl | 4-carboxy-phenyl |
| P98 | 1,2,3,4-tetrazol-1-yl | 5-chloro | 2R*-(isoindolin-2-yl-carbonyl)-1R*cyclopropyl-methyl | 4-carboxy-phenyl |
| P99 | 1,2,3,4-tetrazol-1-yl | 5-chloro | 2R*-(3-phenyl-pyrrolidin-1-yl-carbonyl)-1S*-cyclopropyl-methyl- | 4-carboxy-phenyl |
| P100 | 1,2,3,4-tetrazol-1-yl | 5-chloro | 2S*-(3-phenyl-pyrrolidin-1-yl-carbonyl)-1S*-cyclopropyl-methyl- | 4-carboxy-phenyl |
| P101 | 1,2,3,4-tetrazol-1-yl | 5-chloro | 2R*-(3-phenyl-pyrrolidin-1-yl-carbonyl)-1R*-cyclopropyl-methyl- | 4-carboxy-phenyl |

TABLE 3-continued

Representative Compounds of Formula (I)

| | | | | |
|---|---|---|---|---|
| P102 | 1,2,3,4-tetrazol-1-yl | 5-chloro, 6-fluoro | cyclohexyl-methyl- | 4-(methoxy-carbonyl-amino)-phenyl |
| P104 | 1,2,3,4-tetrazol-1-yl | 5-chloro | 2R*-(pyrrolidin-1-yl-carbonyl)-1S*-cyclopropyl-methyl- | 4-carboxy-phenyl |
| P105 | 1,2,3,4-tetrazol-1-yl | 5-chloro | 2S*-(pyrrolidin-1-yl-carbonyl)-1R*-cyclopropyl-methyl- | 4-carboxy-phenyl |
| P106 | 1,2,3,4-tetrazol-1-yl | 5-chloro | 2S*-(pyrrolidin-1-yl-carbonyl)-1S*-cyclopropyl-methyl- | 4-carboxy-phenyl |
| P107 | 1,2,3,4-tetrazol-1-yl | 5-chloro | 2R*-(pyrrolidin-1-yl-carbonyl)-1R*-cyclopropyl-methyl- | 4-carboxy-phenyl |
| P109 | 1,2,3,4-tetrazol-1-yl | 5-chloro, 6-fluoro | cyclobutyl-methyl- | 4-(methoxy-carbonyl-amino)-phenyl |
| P110 | 1,2,3,4-tetrazol-1-yl | 5-chloro, 6-fluoro | cyclopentyl-methyl- | 4-(methoxy-carbonyl-amino)-phenyl |
| P113 | 1,2,3,4-tetrazol-1-yl | 5-chloro | 2R*-(amino-carbonyl)-1S*-cyclopropyl-methyl- | 4-carboxy-phenyl |
| P114 | 1,2,3,4-tetrazol-1-yl | 5-chloro | 2S*-(amino-carbonyl)-1S*-cyclopropyl-methyl- | 4-carboxy-phenyl |
| P115 | 1,2,3,4-tetrazol-1-yl | 5-chloro, 6-fluoro | tetrahydropyran-2S*-yl-methyl- | 4-(methoxy-carbonyl-amino)-phenyl |
| P117 | 1,2,3,4-tetrazol-1-yl | 5-chloro, 6-fluoro | 4-fluoro-phenyl-methyl- | 4-(methoxy-carbonyl-amino)-phenyl |
| P118 | 1,2,3,4-tetrazol-1-yl | 5-chloro | 1R*-hydroxy-1-phenyl-methyl- | 4-carboxy-phenyl |
| P119 | 1,2,3,4-tetrazol-1-yl | 5-chloro | 1S*-hydroxy-1-phenyl-methyl- | 4-carboxy-phenyl |
| P120 | 1,2,3,4-tetrazol-1-yl | 5-chloro, 6-fluoro | adamantan-1-yl-methyl- | 4-(methoxy-carbonyl-amino)-phenyl |
| P121 | 1,2,3,4-tetrazol-1-yl | 5-chloro, 6-fluoro | 4-fluoro-phenyl-methyl- | 4-(pyrrolidin-2-yl-5-one)-phenyl) |
| P122 | 1,2,3,4-tetrazol-1-yl | 5-chloro, 6-fluoro | 4,4-dimethyl-cyclohexyl-methyl- | 4-(methoxy-carbonyl-amino)-phenyl |
| P123 | 1,2,3,4-tetrazol-1-yl | 5-chloro | 2-(4,4-difluoro-piperidin-1-yl-carbonyl)-cyclopropyl-methyl- | 4-(methoxy-carbonyl-amino)-phenyl |
| P125 | 1,2,3,4-tetrazol-1-yl | 5-chloro, 6-fluoro | 4-fluoro-phenyl-methyl- | 4-(cyclopropyl-amino-carbonyl)-phenyl |
| P126 | 1,2,3,4-tetrazol-1-yl | 5-chloro, 6-fluoro | 3,3-dimethyl-cyclobutyl-methyl- | 4-(methoxy-carbonyl-amino)-phenyl |
| P127 | 1,2,3,4-tetrazol-1-yl | 5-chloro, 6-fluoro | tetrahydropyran-2R*-yl-methyl- | 4-(methoxy-carbonyl-amino)-phenyl |
| P128 | 1,2,3,4-tetrazol-1-yl | 5-chloro | isochroman-1-yl-methyl- | 4-carboxy-phenyl |
| P129 | 1,2,3,4-tetrazol-1-yl | 5-chloro, 6-fluoro | 4-methyl-cyclohexyl-methyl- | 4-(methoxy-carbonyl-amino)-phenyl |
| P131 | 1,2,3,4-tetrazol-1-yl | 5-chloro, 6-fluoro | cyclopropyl-methyl- | 4-(methoxy-methyl-carbonyl-amino)-phenyl |
| P135 | 1,2,3,4-tetrazol-1-yl | 5-chloro, 6-fluoro | 4-methoxy-phenyl-methyl- | 4-(cyclopropyl-amino-carbonyl)-phenyl |
| P136 | oxazol-5-yl | 5-chloro, 6-fluoro | 4-fluoro-phenyl-methyl- | 4-(cyclopropyl-amino-carbonyl)-phenyl |
| P138 | 1,2,3,4-tetrazol-1-yl | 5-chloro | 4-(amino-carbonyl-methoxy)-phenyl-methyl- | 4-carboxy-phenyl |
| P141 | 1,2,3,4-tetrazol-1-yl | 5-chloro, 6-fluoro | cyclopropyl-methyl- | 4-(2-methoxy-ethoxy-carbonyl-amino)-phenyl |
| P142 | 1,2,3,4-tetrazol-1-yl | 5-chloro, 6-fluoro | tetrahydropyran-2R*-yl-methyl- | 4-(cyclopropyl-amino-carbonyl)-phenyl |
| P143 | 1,2,3,4-tetrazol-1-yl | 5-chloro, 6-fluoro | tetrahydropyran-2R*-yl-methyl- | 4-(cyclopropyl-amino-carbonyl)-phenyl |
| P147 | 1,2,3,4-tetrazol-1-yl | 5-chloro | 4-(phenoxy)-phenyl-methyl- | 4-carboxy-phenyl |
| P150 | 1,2,3,4-tetrazol-1-yl | 5-chloro | 4-chloro-phenyl-methyl- | 4-trifluoro-methoxy-phenyl |
| P152 | 1,2,3,4-tetrazol-1-yl | 5-chloro | 4-chloro-phenyl-methyl- | 2-(1,2,3,4-tetrazol-1-yl)-5-chloro-phenyl |
| P153 | 1,2,3,4-tetrazol-1-yl | 5-chloro, 6-fluoro | Ethyl | 4-(methoxy-carbonyl-amino)-phenyl |
| P154 | 1,2,3,4-tetrazol-1-yl | 5-chloro, 6-fluoro | R*-ethyl | 4-(methoxy-carbonyl-amino)-phenyl |
| P155 | 1,2,3,4-tetrazol-1-yl | 5-chloro, 6-fluoro | S*-ethyl | 4-(methoxy-carbonyl-amino)-phenyl |
| P156 | 1,2,3,4-tetrazol-1-yl | 5-chloro, 6-fluoro | n-propyl | 4-(methoxy-carbonyl-amino)-phenyl |
| P157 | 1,2,3,4-tetrazol-1-yl | 5-chloro, 6-fluoro | R*-(n-propyl) | 4-(methoxy-carbonyl-amino)-phenyl |
| P158 | 1,2,3,4-tetrazol-1-yl | 5-chloro, 6-fluoro | S*-(n-propyl) | 4-(methoxy-carbonyl-amino)-phenyl |

TABLE 3-continued

Representative Compounds of Formula (I)

| P159 | 1,2,3,4-tetrazol-1-yl | 5-chloro, 6-fluoro | R*-(4-chloro-phenyl-methyl-) | 4-(methoxy-carbonyl-amino)-phenyl |
|---|---|---|---|---|
| P160 | 1,2,3,4-tetrazol-1-yl | 5-chloro, 6-fluoro | S*-(4-chloro-phenyl-methyl-) | 4-(methoxy-carbonyl-amino)-phenyl |
| P163 | 1,2,3,4-tetrazol-1-yl | 5-chloro | (pyrrolidin-1-yl-2-one)-methyl- | 4-carboxy-phenyl |
| P164 | 1,2,3,4-tetrazol-1-yl | 5-chloro, 6-fluoro | 2-methoxy-phenyl-methyl- | 4-(methoxy-carbonyl-amino)-phenyl |
| P168 | 1,2,3,4-tetrazol-1-yl | 5-chloro, 6-fluoro | 2-(piperidin-1-yl-carbonyl)-cyclopropyl-methyl- | 4-carboxy-phenyl |
| P169 | 1,2,3,4-tetrazol-1-yl | 5-chloro, 6-fluoro | 2-(piperidin-1-yl-carbonyl)-cyclopropyl-methyl- | 4-carboxy-phenyl |
| P175 | 1,2,3,4-tetrazol-1-yl | 5-chloro, 6-fluoro | 2-(3-phenyl-pyrrolidin-1-yl-carbonyl)-cyclopropyl-methyl- | 4-carboxy-phenyl |
| P176 | 1,2,3,4-tetrazol-1-yl | 5-chloro, 6-fluoro | 2-(3-phenyl-pyrrolidin-1-yl-carbonyl)-cyclopropyl-methyl- | 4-carboxy-phenyl |
| P179 | 1,2,3,4-tetrazol-1-yl | 5-chloro, 6-fluoro | Isobutyl | 4-(methoxy-carbonyl-amino)-phenyl |
| P180 | 1,2,3,4-tetrazol-1-yl | 5-chloro, 6-fluoro | R*-isobutyl | 4-(methoxy-carbonyl-amino)-phenyl |
| P181 | 1,2,3,4-tetrazol-1-yl | 5-chloro, 6-fluoro | S*-isobutyl | 4-(methoxy-carbonyl-amino)-phenyl |
| P191 | 1,2,3,4-tetrazol-1-yl | 5-chloro, 6-fluoro | R*-(2-isopropyloxy-ethyl) | 4-(methoxy-carbonyl-amino)-phenyl |
| P192 | 1,2,3,4-tetrazol-1-yl | 5-chloro, 6-fluoro | S*-(2-isopropyloxy-ethyl) | 4-(methoxy-carbonyl-amino)-phenyl |
| P195 | 1,2,3,4-tetrazol-1-yl | 5-chloro, 6-fluoro | 2S*-(3-phenyl-pyrrolidin-1-yl-carbonyl)-1R*-cyclopropyl-methyl- | phenyl |
| P196 | 1,2,3,4-tetrazol-1-yl | 5-chloro, 6-fluoro | 2R*-(3-phenyl-pyrrolidin-1-yl-carbonyl)-1R*-cyclopropyl-methyl- | phenyl |
| P197 | 1,2,3,4-tetrazol-1-yl | 5-chloro, 6-fluoro | 2S*-(piperidin-1-yl-carbonyl)-1R*-cyclopropyl-methyl- | phenyl |
| P198 | 1,2,3,4-tetrazol-1-yl | 5-chloro, 6-fluoro | 2R*-(piperidin-1-yl-carbonyl)-1R*-cyclopropyl-methyl- | phenyl |
| P202 | 1,2,3,4-tetrazol-1-yl | 5-chloro, 6-fluoro | S*-(tetrahydrofuran-2-yl-methyl-) | 4-(methoxy-carbonyl-amino)-phenyl |
| P203 | 1,2,3,4-tetrazol-1-yl | 5-chloro, 6-fluoro | tetrahydrofuran-2-yl-methyl- | 4-(methoxy-carbonyl-amino)-phenyl |
| P204 | 1,2,3,4-tetrazol-1-yl | 5-chloro, 6-fluoro | 2-ethoxy-ethyl- | 4-(methoxy-carbonyl-amino)-phenyl |
| P206 | 1,2,3,4-tetrazol-1-yl | 5-chloro, 6-fluoro | R*-(3-methoxy-phenyl-methyl-) | 4-(methoxy-carbonyl-amino)-phenyl |
| P207 | 1,2,3,4-tetrazol-1-yl | 5-chloro, 6-fluoro | S*-(3-methoxy-phenyl-methyl-) | 4-(methoxy-carbonyl-amino)-phenyl |
| P208 | 1,2,3,4-tetrazol-1-yl | 5-chloro, 6-fluoro | 2R*-carboxy-1S*-cyclopropyl-methyl- | phenyl |
| P209 | 1,2,3,4-tetrazol-1-yl | 5-chloro, 6-fluoro | 2S*-carboxy-1R*-cyclopropyl-methyl- | phenyl |
| P213 | 1,2,3,4-tetrazol-1-yl | 5-chloro, 6-fluoro | 2S*-(4-carboxy-piperidin-1-yl-carbonyl)-1R*-cyclopropyl-methyl- | phenyl |
| P214 | 1,2,3,4-tetrazol-1-yl | 5-chloro, 6-fluoro | pyrazol-1-yl-methyl- | 4-(methoxy-carbonyl-amino)-phenyl |
| P215 | 1,2,3,4-tetrazol-1-yl | 5-chloro, 6-fluoro | 2R*-(4-carboxy-piperidin-1-yl-carbonyl)-1R*-cyclopropyl-methyl- | phenyl |
| P217 | 1,2,3,4-tetrazol-1-yl | 5-chloro, 6-fluoro | R*-(2-hydroxy-ethyl-) | 4-(methoxy-carbonyl-amino)-phenyl |
| P218 | 1,2,3,4-tetrazol-1-yl | 5-chloro, 6-fluoro | S*-(2-hydroxy-ethyl-) | 4-(methoxy-carbonyl-amino)-phenyl |
| P219 | 1,2,3,4-tetrazol-1-yl | 5-chloro, 6-fluoro | R*-(tetrahydropyran-2S*-yl-methyl-) | 4-(methoxy-carbonyl-amino)-phenyl |
| P220 | 1,2,3,4-tetrazol-1-yl | 5-chloro, 6-fluoro | S*-(tetrahydropyran-2S*-yl-methyl-) | 4-(methoxy-carbonyl-amino)-phenyl |
| P221 | 1,2,3,4-tetrazol-1-yl | 5-chloro, 6-fluoro | 2S*-(3-phenyl-piperidin-1-yl-carbonyl)-1R*-cyclopropyl-methyl- | 4-(methoxy-carbonyl-amino)-phenyl |
| P222 | 1,2,3,4-tetrazol-1-yl | 5-chloro, 6-fluoro | 2S*-(3-phenyl-piperidin-1-yl-carbonyl)-1S*-cyclopropyl-methyl- | 4-(methoxy-carbonyl-amino)-phenyl |

TABLE 3-continued

Representative Compounds of Formula (I)

| | | | | |
|---|---|---|---|---|
| P223 | 1,2,3,4-tetrazol-1-yl | 5-chloro, 6-fluoro | 2S*-(3-carboxy-piperidin-1-yl-carbonyl)-1R*-cyclopropyl-methyl- | phenyl |
| P224 | 1,2,3,4-tetrazol-1-yl | 5-chloro, 6-fluoro | 2R*-(3-carboxy-piperidin-1-yl-carbonyl)-1R*-cyclopropyl-methyl- | phenyl |
| P225 | 1,2,3,4-tetrazol-1-yl | 5-chloro, 6-fluoro | R*-(2-(difluoro-methoxy)-ethyl-) | 4-(methoxy-carbonyl-amino)-phenyl |
| P226 | 1,2,3,4-tetrazol-1-yl | 5-chloro, 6-fluoro | R-(2-(difluoro-methoxy)-ethyl-) | 4-(methoxy-carbonyl-amino)-phenyl |
| P227 | 1,2,3,4-tetrazol-1-yl | 5-chloro, 6-fluoro | 2-methyl-cyclopropyl-methyl- | 4-carboxy-phenyl |
| P228 | 1,2,3,4-tetrazol-1-yl | 5-chloro, 6-fluoro | S*-(2-methoxy-n-propyl-) | 4-(methoxy-carbonyl-amino)-phenyl |
| P229 | 1,2,3,4-tetrazol-1-yl | 5-chloro, 6-fluoro | isopropyloxy-methyl- | 4-(methoxy-carbonyl-amino)-phenyl |
| P230 | 1,2,3,4-tetrazol-1-yl | 5-chloro, 6-fluoro | R-(2-methoxy-n-propyl-) | 4-(methoxy-carbonyl-amino)-phenyl |
| P231 | 1,2,3,4-tetrazol-1-yl | 5-chloro, 6-fluoro | 2R*-(piperidin-1-yl-carbonyl)-1S*-cyclopropyl-methyl- | 4-(methoxy-carbonyl-amino)-phenyl |
| P232 | 1,2,3,4-tetrazol-1-yl | 5-chloro, 6-fluoro | 2S*-(piperidin-1-yl-carbonyl)-1S*-cyclopropyl-methyl- | 4-(methoxy-carbonyl-amino)-phenyl |
| P239 | 1,2,3,4-tetrazol-1-yl | 5-chloro | 2R*-(4-methoxy-phenyl)-1S*-cyclopropyl-methyl- | 4-carboxy-phenyl |
| P240 | 1,2,3,4-tetrazol-1-yl | 5-chloro | 2S*-(4-methoxy-phenyl)-1S*-cyclopropyl-methyl- | 4-carboxy-phenyl |
| P245 | 1,2,3,4-tetrazol-1-yl | 5-chloro, 6-fluoro | 2R*-carboxy-1S*-cyclopropyl-methyl- | 4-(methoxy-carbonyl-amino)-phenyl |
| P246 | 1,2,3,4-tetrazol-1-yl | 5-chloro, 6-fluoro | 2S*-carboxy-1S*-cyclopropyl-methyl- | 4-(methoxy-carbonyl-amino)-phenyl |
| P249 | 1,2,3,4-tetrazol-1-yl | 5-chloro, 6-fluoro | 2-(amino-carbonyl)-cyclopropyl-methyl- | 4-(methoxy-carbonyl-amino)-phenyl |
| P272 | 1,2,3,4-tetrazol-1-yl | 5-chloro, 6-fluoro | R*-(pyrazol-1-yl-methyl-) | 4-(methoxy-carbonyl-amino)-phenyl |
| P273 | 1,2,3,4-tetrazol-1-yl | 5-chloro, 6-fluoro | S*-(pyrazol-1-yl-methyl-) | 4-(methoxy-carbonyl-amino)-phenyl |
| P277 | 1,2,3,4-tetrazol-1-yl | 5-chloro, 6-fluoro | 4-fluoro-pyrazol-1-yl-methyl- | 4-(methoxy-carbonyl-amino)-phenyl |
| P278 | 1,2,3,4-tetrazol-1-yl | 5-chloro, 6-fluoro | 2-(methoxy-$d_3$)-ethyl- | 4-(methyl-$d_3$-amino)-phenyl |
| P289 | 1,2,3,4-tetrazol-1-yl | 5-chloro, 6-fluoro | R-(2-(methoxy-$d_3$)-ethyl-) | 4-(methoxy-carbonyl-amino)-phenyl |
| P290 | 1,2,3,4-tetrazol-1-yl | 5-chloro, 6-fluoro | S*-(2-(methoxy-$d_3$)-ethyl-) | 4-(methoxy-carbonyl-amino)-phenyl |
| P305 | 1,2,3,4-tetrazol-1-yl | 5-chloro, 6-fluoro | (pyridin-1-yl-2-one)-methyl- | 4-(methoxy-carbonyl-amino)-phenyl |
| P327 | 1,2,3,4-tetrazol-1-yl | 5-chloro, 6-fluoro | 1-methyl-pyrazol-3-yl-methyl- | 4-(methoxy-carbonyl-amino)-phenyl |
| P328 | 1,2,3,4-tetrazol-1-yl | 5-chloro, 6-fluoro | R-(1-methyl-pyrazol-3-yl-methyl-) | 4-(methoxy-carbonyl-amino)-phenyl |
| P329 | 1,2,3,4-tetrazol-1-yl | 5-chloro, 6-fluoro | R*-(1-methyl-pyrazol-3-yl-methyl-) | 4-(methoxy-carbonyl-amino)-phenyl |
| P330 | 1,2,3,4-tetrazol-1-yl | 5-chloro, 6-fluoro | R-(1-methyl-pyrazol-3-yl-methyl-) | 4-(methoxy-carbonyl-amino)-phenyl |
| P445 | 1,2,3,4-tetrazol-1-yl | 5-chloro, 6-fluoro | 3-carboxy-pyrazol-1-yl-methyl- | 4-(methoxy-carbonyl-amino)-phenyl |
| P446 | 1,2,3,4-tetrazol-1-yl | 5-chloro, 6-fluoro | 3-(amino-carbonyl)-pyrazol-1-yl-methyl- | 4-(methoxy-carbonyl-amino)-phenyl |
| P476 | 1,2,3,4-tetrazol-1-yl | 5-chloro, 6-fluoro | N-methyl-N-(methoxy-carbonyl)-amino-methyl- | 4-(methoxy-carbonyl-amino)-phenyl |
| P621 | 1,2,3,4-tetrazol-1-yl | 5-chloro, 6-fluoro | cyclopropyl-methyl- | carboxy |
| P838 | 4-(trifluoro-methyl)-1,2,3-triazol-1-yl | 5-chloro, 6-fluoro | 2-(difluoro-methoxy)-ethyl- | 4-carboxy-phenyl |
| P844 | 4-(trifluoro-methyl)-1,2,3-triazol-1-yl | 5-chloro, 6-fluoro | 2-(difluoro-methoxy)-ethyl- | 3-fluoro-4-(amino-carbonyl)-phenyl |
| P854 | 4-(trifluoro-methyl)-1,2,3-triazol-1-yl | 5-chloro, 6-fluoro | S-(1-methyl-pyrazol-3-yl-methyl-) | 4-carboxy-phenyl |
| P855 | 4-(trifluoro-methyl)-1,2,3-triazol-1-yl | 5-chloro, 6-fluoro | R-(1-methyl-pyrazol-3-yl-methyl-) | 4-carboxy-phenyl |
| P858 | 4-(trifluoro-methyl)-1,2,3-triazol-1-yl | 5-chloro, 6-fluoro | R-(2-(difluoro-methoxy)-ethyl-) | 4-carboxy-phenyl |
| P859 | 4-(trifluoro-methyl)-1,2,3-triazol-1-yl | 5-chloro | R-(2-(difluoro-methoxy)-ethyl-) | 3-fluoro-4-(amino-carbonyl)-phenyl |
| P860 | 4-(trifluoro-methyl)-1,2,3-triazol-1-yl | 5-chloro, 6-fluoro | R-(2-(difluoro-methoxy)-ethyl-) | 3-fluoro-4-(amino-carbonyl)-phenyl |

TABLE 3-continued

Representative Compounds of Formula (I)

| | | | | |
|---|---|---|---|---|
| P867 | 4-(trifluoro-methyl)-1,2,3-triazol-1-yl | 5-chloro, 6-fluoro | S*-ethyl | 3-fluoro-4-(amino-carbonyl)-phenyl |
| P868 | 4-(trifluoro-methyl)-1,2,3-triazol-1-yl | 5-chloro, 6-fluoro | R*-ethyl | 3-fluoro-4-(amino-carbonyl)-phenyl |
| P871 | 4-(trifluoro-methyl)-1,2,3-triazol-1-yl | 5-chloro, 6-fluoro | 2-(difluoro-methoxy)-ethyl- | 3-fluoro-4-carboxy-phenyl |
| P872 | 4-(trifluoro-methyl)-1,2,3-triazol-1-yl | 5-chloro, 6-fluoro | 1-(difluoro-methyl)-pyrazol-3-yl-methyl- | 3-fluoro-4-carboxy-phenyl |
| P873 | 4-(trifluoro-methyl)-1,2,3-triazol-1-yl | 5-chloro, 6-fluoro | R-(cyclopropyl-methyl-) | 3-fluoro-4-(amino-carbonyl)-phenyl |
| P875 | 4-chloro-1,2,3-triazol-1-yl | 5-chloro, 6-fluoro | R*-(2-(difluoro-methoxy)-ethyl-) | 3-fluoro-4-(amino-carbonyl)-phenyl |
| P876 | 4-chloro-1,2,3-triazol-1-yl | 5-chloro, 6-fluoro | S*-(2-(difluoro-methoxy)-ethyl-) | 3-fluoro-4-(amino-carbonyl)-phenyl |
| P879 | 4-(trifluoro-methyl)-1,2,3-triazol-1-yl | 5-chloro, 6-fluoro | dimethyl-amino-carbonyl-methyl- | 3-fluoro-4-carboxy-phenyl |
| P880 | 4-chloro-1,2,3-triazol-1-yl | 5-chloro, 6-fluoro | R*-(2-(difluoro-methoxy)-ethyl-) | 3-fluoro-4-carboxy-phenyl |
| P881 | 4-chloro-1,2,3-triazol-1-yl | 5-chloro, 6-fluoro | S*-(2-(difluoro-methoxy)-ethyl-) | 3-fluoro-4-carboxy-phenyl |
| P882 | 4-(trifluoro-methyl)-1,2,3-triazol-1-yl | 5-chloro, 6-fluoro | R*-ethyl | 3-fluoro-4-(amino-carbonyl)-phenyl |
| P883 | 4-(trifluoro-methyl)-1,2,3-triazol-1-yl | 5-chloro, 6-fluoro | S*-ethyl | 3-fluoro-4-(amino-carbonyl)-phenyl |
| P884 | 4-(trifluoro-methyl)-1,2,3-triazol-1-yl | 5-chloro, 6-fluoro | dimethyl-amino-carbonyl-methyl- | 3-fluoro-4-(amino-carbonyl)-phenyl |
| P886 | 4-(trifluoro-methyl)-1,2,3-triazol-1-yl | 5-chloro, 6-fluoro | S*-(2-(difluoro-methoxy)-ethyl-) | 3-fluoro-4-carboxy-phenyl |
| P887 | 4-(trifluoro-methyl)-1,2,3-triazol-1-yl | 5-chloro, 6-fluoro | R*-(2-(difluoro-methoxy)-ethyl-) | 3-fluoro-4-carboxy-phenyl |
| P888 | 4-(trifluoro-methyl)-1,2,3-triazol-1-yl | 5-chloro, 6-fluoro | R*-(cyclopropyl-methyl-) | 3-fluoro-4-(amino-carbonyl)-phenyl |
| P889 | 4-(trifluoro-methyl)-1,2,3-triazol-1-yl | 5-chloro, 6-fluoro | S*-(cyclopropyl-methyl-) | 3-fluoro-4-(amino-carbonyl)-phenyl |
| P890 | 4-(trifluoro-methyl)-1,2,3-triazol-1-yl | 5-chloro, 6-fluoro | methoxy-carbonyl-methyl- | 3-fluoro-4-carboxy-phenyl |
| P891 | 4-(trifluoro-methyl)-1,2,3-triazol-1-yl | 5-chloro, 6-fluoro | S*-(1-(difluoro-methyl)-pyrazol-3-yl-methyl-) | 3-fluoro-4-(amino-carbonyl)-phenyl |
| P892 | 4-(trifluoro-methyl)-1,2,3-triazol-1-yl | 5-chloro, 6-fluoro | R-(1-(difluoro-methyl)-pyrazol-3-yl-methyl-) | 3-fluoro-4-(amino-carbonyl)-phenyl |
| P893 | 4-chloro-1,2,3-triazol-1-yl | 5-chloro, 6-fluoro | R*-(1-(difluoro-methyl)-pyrazol-3-yl-methyl-) | 3-fluoro-4-(amino-carbonyl)-phenyl |
| P894 | 4-chloro-1,2,3-triazol-1-yl | 5-chloro, 6-fluoro | R-(1-(difluoro-methyl)-pyrazol-3-yl-methyl-) | 3-fluoro-4-(amino-carbonyl)-phenyl |
| P895 | 4-chloro-1,2,3-triazol-1-yl | 5-chloro, 6-fluoro | R*-(2-(difluoro-methoxy)-ethyl-) | 4-(amino-carbonyl)-phenyl |
| P896 | 4-chloro-1,2,3-triazol-1-yl | 5-chloro, 6-fluoro | S*-(2-(difluoro-methoxy)-ethyl-) | 4-(amino-carbonyl)-phenyl |
| P897 | 4-chloro-1,2,3-triazol-1-yl | 5-chloro, 6-fluoro | R*-(1-(difluoro-methyl)-pyrazol-3-yl-methyl-) | 4-carboxy-phenyl |
| P898 | 4-chloro-1,2,3-triazol-1-yl | 5-chloro, 6-fluoro | S*-(1-(difluoro-methyl)-pyrazol-3-yl-methyl-) | 4-carboxy-phenyl |
| P899 | 4-(trifluoro-methyl)-1,2,3-triazol-1-yl | 5-chloro, 6-fluoro | R*-(1-(difluoro-methyl)-pyrazol-3-yl-methyl-) | 4-carboxy-phenyl |
| P900 | 4-(trifluoro-methyl)-1,2,3-triazol-1-yl | 5-chloro, 6-fluoro | S*-(1-(difluoro-methyl)-pyrazol-3-yl-methyl-) | 4-carboxy-phenyl |
| P901 | 4-(trifluoro-methyl)-1,2,3-triazol-1-yl | 5-chloro, 6-fluoro | pyrrolidin-1-yl-carbonyl-methyl- | 3-fluoro-4-carboxy-phenyl |
| P902 | 4-(trifluoro-methyl)-1,2,3-triazol-1-yl | 5-chloro, 6-fluoro | pyrrolidin-1-yl-carbonyl-methyl- | 3-fluoro-4-(amino-carbonyl)-phenyl |
| P905 | 4-(trifluoro-methyl)-1,2,3-triazol-1-yl | 5-chloro | S*-(1-(difluoro-methyl)-pyrazol-3-yl-methyl-) | 3-fluoro-4-(amino-carbonyl)-phenyl |
| P906 | 4-(trifluoro-methyl)-1,2,3-triazol-1-yl | 5-chloro, 6-fluoro | R*-(1-(difluoro-methyl)-pyrazol-3-yl-methyl-) | 3-fluoro-4-(amino-carbonyl)-phenyl |
| P907 | 4-(trifluoro-methyl)-1,2,3-triazol-1-yl | 5-chloro, 6-fluoro | R*-(1-(difluoro-methyl)-pyrazol-3-yl-methyl-) | 4-(amino-carbonyl)-phenyl |
| P908 | 4-(trifluoro-methyl)-1,2,3-triazol-1-yl | 5-chloro, 6-fluoro | S*-(1-(difluoro-methyl)-pyrazol-3-yl-methyl-) | 4-(amino-carbonyl)-phenyl |
| P909 | 4-(trifluoro-methyl)-1,2,3-triazol-1-yl | 5-chloro, 6-fluoro | oxazol-2-yl-methyl- | 3-fluoro-4-(amino-carbonyl)-phenyl |
| P910 | 4-chloro-1,2,3-triazol-1-yl | 5-chloro, 6-fluoro | R*-(1-(difluoro-methyl)-pyrazol-3-yl-methyl-) | 4-(amino-carbonyl)-phenyl |
| P911 | 4-chloro-1,2,3-triazol-1-yl | 5-chloro, 6-fluoro | S*-(1-(difluoro-methyl)-pyrazol-3-yl-methyl-) | 4-(amino-carbonyl)-phenyl |
| P912 | 4-(trifluoro-methyl)-1,2,3-triazol-1-yl | 5-chloro, 6-fluoro | oxazol-2-yl-methyl- | 3-fluoro-4-carboxy-phenyl |
| P913 | 4-(trifluoro-methyl)-1,2,3-triazol-1-yl | 5-chloro, 6-fluoro | S*-(2-(methoxy-$d_3$)-ethyl-2,2-$d_2$-) | 3-fluoro-4-(amino-carbonyl)-phenyl |

TABLE 3-continued

Representative Compounds of Formula (I)

| P914 | 4-(trifluoro-methyl)-1,2,3-triazol-1-yl | 5-chloro, 6-fluoro | R*-(2-(methoxy-d₃)-ethyl-2,2-d₂-) | 3-fluoro-4-(amino-carbonyl)-phenyl |
|---|---|---|---|---|
| P915 | 4-(trifluoro-methyl)-1,2,3-triazol-1-yl | 5-chloro, 6-fluoro | 1,2,4-oxadiazol-3-yl-methyl- | 3-fluoro-4-(amino-carbonyl)-phenyl |
| P926 | 4-chloro-1,2,3-triazol-1-yl | 5-chloro, 6-fluoro | 2-(methyl-d₃)-ethyl-2,2-d₂- | 3-fluoro-4-(amino-carbonyl)-phenyl |
| P927 | 4-(trifluoro-methyl)-1,2,3-triazol-1-yl | 5-chloro, 6-fluoro | (5-methyl-1,3,4-oxadiazol-2-yl)-methyl- | 3-fluoro-4-(amino-carbonyl)-phenyl |
| P928 | 1,2,3,4-tetrazol-1-yl | 5-chloro, 6-fluoro | R*-(2-(difluoro-methoxy)-ethyl-) | 3-fluoro-4-(amino-carbonyl)-phenyl |
| P929 | 1,2,3,4-tetrazol-1-yl | 5-chloro, 6-fluoro | S*-(2-(difluoro-methoxy)-ethyl-) | 3-fluoro-4-(amino-carbonyl)-phenyl |
| P930 | 4-(trifluoro-methyl)-1,2,3-triazol-1-yl | 5-chloro, 6-fluoro | R*-(1-(difluoro-methyl)-pyrazol-3-yl-methyl-) | 3-fluoro-4-carboxy-phenyl |
| P931 | 4-(trifluoro-methyl)-1,2,3-triazol-1-yl | 5-chloro, 6-fluoro | S*-(1-(difluoro-methyl)-pyrazol-3-yl-methyl-) | 3-fluoro-4-carboxy-phenyl |
| P932 | 1,2,3,4-tetrazol-1-yl | 5-chloro, 6-fluoro | S*-(1-(difluoro-methyl)-pyrazol-3-yl-methyl-) | 3-fluoro-4-(amino-carbonyl)-phenyl |
| P933 | 1,2,3,4-tetrazol-1-yl | 5-chloro, 6-fluoro | R*-(1-(difluoro-methyl)-pyrazol-3-yl-methyl-) | 3-fluoro-4-(amino-carbonyl)-phenyl |
| P936 | 4-(trifluoro-methyl)-1,2,3-triazol-1-yl | 5-chloro, 6-fluoro | R*-((pyrrolidin-1-yl-2-one)-methyl-) | 3-fluoro-4-(amino-carbonyl)-phenyl |
| P937 | 4-(trifluoro-methyl)-1,2,3-triazol-1-yl | 5-chloro, 6-fluoro | S*-((pyrrolidin-1-yl-2-one)-methyl-) | 3-fluoro-4-(amino-carbonyl)-phenyl |
| P941 | 4-(trifluoro-methyl)-1,2,3-triazol-1-yl | 5-chloro, 6-fluoro | thiazol-2-yl-methyl- | 3-fluoro-4-carboxy-phenyl |
| P942 | 4-(trifluoro-methyl)-1,2,3-triazol-1-yl | 5-chloro, 6-fluoro | R*-(thiazol-2-yl-methyl-) | 3-fluoro-4-(amino-carbonyl)-phenyl |
| P943 | 4-(trifluoro-methyl)-1,2,3-triazol-1-yl | 5-chloro, 6-fluoro | S*-(thiazol-2-yl-methyl-) | 3-fluoro-4-(amino-carbonyl)-phenyl |
| P946 | 1,2,3,4-tetrazol-1-yl | 5-chloro, 6-fluoro | R*-(cyclopropyl-methyl-) | 3-fluoro-4-(amino-carbonyl)-phenyl |
| P947 | 1,2,3,4-tetrazol-1-yl | 5-chloro, 6-fluoro | S*-(cyclopropyl-methyl-) | 3-fluoro-4-(amino-carbonyl)-phenyl |
| P948 | 4-(trifluoro-methyl)-1,2,3-triazol-1-yl | 5-chloro, 6-fluoro | pyrazol-1-yl-methyl- | 3-fluoro-4-(amino-carbonyl)-phenyl |
| P949 | 1,2,3,4-tetrazol-1-yl | 5-chloro, 6-fluoro | S*-ethyl | 3-fluoro-4-(amino-carbonyl)-phenyl |
| P950 | 1,2,3,4-tetrazol-1-yl | 5-chloro, 6-fluoro | R*-ethyl | 3-fluoro-4-(amino-carbonyl)-phenyl |
| P951 | 4-(trifluoro-methyl)-1,2,3-triazol-1-yl | 5-chloro, 6-fluoro | 4-(tert-butyl)-pyrazol-1-yl-methyl- | 3-fluoro-4-(amino-carbonyl)-phenyl |
| P952 | 4-(trifluoro-methyl)-1,2,3-triazol-1-yl | 5-chloro, 6-fluoro | 1-(difluoro-methyl)-pyrazol-3-yl-methyl- | 3-fluoro-4-(amino-carbonyl)-phenyl |
| P955 | 4-(trifluoro-methyl)-1,2,3-triazol-1-yl | 5-chloro, 6-fluoro | 4-cyano-pyrazol-1-yl-methyl- | 3-fluoro-4-(amino-carbonyl)-phenyl |

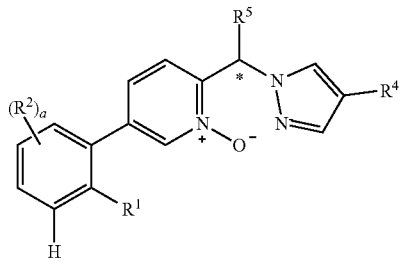

(I-PY)

| ID No. | R¹ | (R²)ₐ | R⁵ | R⁴ |
|---|---|---|---|---|
| P288 | 1,2,3,4-tetrazol-1-yl | 5-chloro, 6-fluoro | cyclopropyl-methyl- | 1-methyl-pyrazol-4-y |
| P389 | 1,2,3,4-tetrazol-1-yl | 5-chloro, 6-fluoro | cyclopropyl-methyl- | 1-methyl-pyrazol-5-yl |
| P390 | 1,2,3,4-tetrazol-1-yl | 5-chloro, 6-fluoro | cyclopropyl-methyl- | 1-(methoxy-carbonyl-methyl)-pyrazol-4-yl |
| P455 | 1,2,3,4-tetrazol-1-yl | 5-chloro, 6-fluoro | cyclopropyl-methyl- | oxazol-5-yl |
| P456 | 1,2,3,4-tetrazol-1-yl | 5-chloro, 6-fluoro | cyclopropyl-methyl- | isothiazol-4-yl |
| P457 | 1,2,3,4-tetrazol-1-yl | 5-chloro, 6-fluoro | cyclopropyl-methyl- | 1-methyl-imidazol-5-yl |
| P460 | 1,2,3,4-tetrazol-1-yl | 5-chloro, 6-fluoro | cyclopropyl-methyl- | 1-methyl-1,2,3-triazol-5-yl |

TABLE 3-continued

Representative Compounds of Formula (I)

| | | | | |
|---|---|---|---|---|
| P467 | 1,2,3,4-tetrazol-1-yl | 5-chloro, 6-fluoro | cyclopropyl-methyl- | pyrazol-5-yl |
| P478 | 1,2,3,4-tetrazol-1-yl | 5-chloro, 6-fluoro | cyclopropyl-methyl- | 1-methyl-4-fluoro-pyrazol-5-yl |
| P481 | 1,2,3,4-tetrazol-1-yl | 5-chloro, 6-fluoro | cyclopropyl-methyl- | 1-methyl-pyrazol-5-yl |
| P484 | 1,2,3,4-tetrazol-1-yl | 5-chloro, 6-fluoro | cyclopropyl-methyl- | thiazol-5-yl |
| P487 | 1,2,3,4-tetrazol-1-yl | 5-chloro, 6-fluoro | 2-(difluoro-methoxy)-ethyl- | 1-methyl-pyrazol-5-yl |
| P488 | 1,2,3,4-tetrazol-1-yl | 5-chloro, 6-fluoro | cyclopropyl-methyl- | 4-methyl-thiazol-5-yl |
| P493 | 1,2,3,4-tetrazol-1-yl | 5-chloro, 6-fluoro | S-(4-fluoro-pyrazol-1-yl-methyl-) | thiazol-5-yl |
| P494 | 1,2,3,4-tetrazol-1-yl | 5-chloro, 6-fluoro | R-(cyclopropyl-methyl-) | 1-methyl-1,2,3-triazol-4-yl |
| P495 | 1,2,3,4-tetrazol-1-yl | 5-chloro, 6-fluoro | R-(cyclopropyl-methyl-) | 1-methyl-imidazol-5-yl |
| P496 | 1,2,3,4-tetrazol-1-yl | 5-chloro, 6-fluoro | S-(cyclopropyl-methyl-) | 1-methyl-1,2,3-triazol-4-yl |
| P497 | 1,2,3,4-tetrazol-1-yl | 5-chloro, 6-fluoro | R-(cyclopropyl-methyl-) | oxazol-5-yl |
| P498 | 1,2,3,4-tetrazol-1-yl | 5-chloro, 6-fluoro | R*-(cyclopropyl-methyl-) | 1-methyl-imidazol-5-yl |
| P499 | 1,2,3,4-tetrazol-1-yl | 5-chloro, 6-fluoro | R*-(cyclopropyl-methyl-) | oxazol-5-yl |
| P501 | 1,2,3,4-tetrazol-1-yl | 5-chloro, 6-fluoro | S*-(4-fluoro-pyrazol-1-yl-methyl-) | 1-methyl-pyrazol-5-yl |
| P502 | 1,2,3,4-tetrazol-1-yl | 5-chloro, 6-fluoro | R-(4-fluoro-pyrazol-1-yl-methyl-) | 1-methyl-imidazol-5-yl |
| P503 | 1,2,3,4-tetrazol-1-yl | 5-chloro, 6-fluoro | R-(4-fluoro-pyrazol-1-yl-methyl-) | 1-methyl-pyrazol-5-yl |
| P504 | 1,2,3,4-tetrazol-1-yl | 5-chloro, 6-fluoro | S*-(4-fluoro-pyrazol-1-yl-methyl-) | 1-methyl-imidazol-5-yl |
| P505 | 1,2,3,4-tetrazol-1-yl | 5-chloro, 6-fluoro | R-(cyclopropyl-methyl-) | 3-methyl-isoxazol-4-yl |
| P506 | 1,2,3,4-tetrazol-1-yl | 5-chloro, 6-fluoro | R-(cyclopropyl-methyl-) | 3-methyl-isoxazol-4-yl |
| P507 | 1,2,3,4-tetrazol-1-yl | 5-chloro, 6-fluoro | R*-(cyclopropyl-methyl-) | 1-methyl-1,2,3-triazol-5-yl |
| P508 | 1,2,3,4-tetrazol-1-yl | 5-chloro, 6-fluoro | R-(cyclopropyl-methyl-) | 1-methyl-1,2,3-triazol-5-yl |
| P509 | 1,2,3,4-tetrazol-1-yl | 5-chloro, 6-fluoro | S-(2-methoxy-ethyl-) | 1-methyl-1,2,3-triazol-5-yl |
| P510 | 1,2,3,4-tetrazol-1-yl | 5-chloro, 6-fluoro | R-(2-methoxy-ethyl-) | 1-methyl-1,2,3-triazol-5-yl |
| P511 | 1,2,3,4-tetrazol-1-yl | 5-chloro, 6-fluoro | S*-(cyclopropyl-methyl-) | 1-methyl-1,2,3-triazol-5-yl |
| P519 | 1,2,3,4-tetrazol-1-yl | 5-chloro, 6-fluoro | S-(2-methoxy-ethyl-) | 1,3,4-triazol-1-yl |
| P520 | 1,2,3,4-tetrazol-1-yl | 5-chloro, 6-fluoro | R-(2-methoxy-ethyl-) | 1,3,4-triazol-1-yl |
| P521 | 1,2,3,4-tetrazol-1-yl | 5-chloro, 6-fluoro | cyclopropyl-methyl- | 1-methyl-4-cyano-pyrazol-5-yl |
| P524 | 1,2,3,4-tetrazol-1-yl | 5-chloro, 6-fluoro | cyclopropyl-methyl- | 1-cyclopropyl-1,2,3-triazol-5-yl |
| P525 | 1,2,3,4-tetrazol-1-yl | 5-chloro, 6-fluoro | cyclopropyl-methyl- | 1,2,4-thiadizol-5-yl |
| P526 | 1,2,3,4-tetrazol-1-yl | 5-chloro, 6-fluoro | cyclopropyl-methyl- | 1-methyl-1,2,4-triazol-5-yl |
| P527 | 1,2,3,4-tetrazol-1-yl | 5-chloro, 6-fluoro | R*-(2-methoxy-ethyl-) | imidazol-1-yl |
| P528 | 1,2,3,4-tetrazol-1-yl | 5-chloro, 6-fluoro | S-(2-methoxy-ethyl-) | imidazol-1-yl |
| P529 | 1,2,3,4-tetrazol-1-yl | 5-chloro, 6-fluoro | S-(2-(difluoro-methoxy)-ethyl-) | 1-methyl-1,2,3-triazol-5-yl |
| P530 | 1,2,3,4-tetrazol-1-yl | 5-chloro, 6-fluoro | R-(2-(difluoro-methoxy)-ethyl-) | 1-methyl-1,2,3-triazol-5-yl |
| P531 | 1,2,3,4-tetrazol-1-yl | 5-chloro, 6-fluoro | R-(2-methoxy-ethyl-) | 2-(difluoro-methyl)-thiazol-5-yl |
| P532 | 1,2,3,4-tetrazol-1-yl | 5-chloro, 6-fluoro | S-(2-methoxy-ethyl-) | 2-(difluoro-methyl)-thiazol-5-yl |
| P535 | 1,2,3,4-tetrazol-1-yl | 5-chloro, 6-fluoro | cyclopropyl-methyl- | 4-cyclopropyl-thiazol-5-yl |
| P536 | 4-chloro-1,2,3-triazol-1-yl | 5-chloro, 6-fluoro | S-(4-fluoro-pyrazol-1-yl-methyl-) | 1-methyl-1,2,3-triazol-5-yl |
| P537 | 4-chloro-1,2,3-triazol-1-yl | 5-chloro, 6-fluoro | R-(4-fluoro-pyrazol-1-yl-methyl-) | 1-methyl-1,2,3-triazol-5-yl |

TABLE 3-continued

Representative Compounds of Formula (I)

| P538 | 1,2,3,4-tetrazol-1-yl | 5-chloro, 6-fluoro | R-(4-fluoro-phenyl-methyl-) | 1-methyl-1,2,3-triazol-5-yl |
| --- | --- | --- | --- | --- |
| P539 | 1,2,3,4-tetrazol-1-yl | 5-chloro, 6-fluoro | S-(4-fluoro-phenyl-methyl-) | 1-methyl-1,2,3-triazol-5-yl |
| P540 | 1,2,3,4-tetrazol-1-yl | 5-chloro, 6-fluoro | cyclopropyl-methyl- | 4-(trifluoro-methyl)-thiazol-5-yl |
| P541 | 1,2,3,4-tetrazol-1-yl | 5-chloro, 6-fluoro | cyclopropyl-methyl- | 1-methyl-1,2,3,4-tetrazol-5-yl |
| P542 | 1,2,3,4-tetrazol-1-yl | 5-chloro, 6-fluoro | cyclopropyl-methyl- | 1-(difluoro-methyl)-pyrazol-5-yl |
| P543 | 1,2,3,4-tetrazol-1-yl | 5-chloro, 6-fluoro | cyclopropyl-methyl- | 2-(trifluoro-methyl)-1,3,4-thiadiazol-5-yl |
| P544 | 4-chloro-1,2,3-triazol-1-yl | 5-chloro, 6-fluoro | R-(2-methoxy-ethyl-) | 1-methyl-1,2,3-triazol-5-yl |
| P545 | 1,2,3,4-tetrazol-1-yl | 5-chloro, 6-fluoro | R-(cyclopropyl-methyl-) | 1,3,4-oxadiazol-5-yl |
| P546 | 4-chloro-1,2,3-triazol-1-yl | 5-chloro, 6-fluoro | S-(2-methoxy-ethyl-) | 1-methyl-imidazol-5-yl |
| P547 | 1,2,3,4-tetrazol-1-yl | 5-chloro, 6-fluoro | S-(cyclopropyl-methyl-) | 1,3,4-oxadiazol-5-yl |
| P548 | 1,2,3,4-tetrazol-1-yl | 5-chloro, 6-fluoro | cyclopropyl-methyl- | 1-methyl-3-(trifluoro-methyl)-pyrazol-5-yl |
| P549 | 1,2,3,4-tetrazol-1-yl | 5-chloro, 6-fluoro | S-(2-(difluoro-methoxy)-ethyl-) | 1-methyl-1,2,4-triazol-5-yl |
| P550 | 1,2,3,4-tetrazol-1-yl | 5-chloro, 6-fluoro | R-(2-(difluoro-methoxy)-ethyl- | 1-methyl-1,2,4-triazol-5-yl |
| P553 | 1,2,3,4-tetrazol-1-yl | 5-chloro, 6-fluoro | cyclopropyl-methyl- | 3-methyl-pyrazol-4-yl |
| P554 | 1,2,3,4-tetrazol-1-yl | 5-chloro, 6-fluoro | cyclopropyl-methyl- | 1-methyl-1,2,5-triazol-3-yl |
| P555 | 1,2,3,4-tetrazol-1-yl | 5-chloro, 6-fluoro | cyclopropyl-methyl- | 1-methyl-4-chloro-pyrazol-5-yl |
| P556 | 1,2,3,4-tetrazol-1-yl | 5-chloro, 6-fluoro | R-(2-(difluoro-methoxy)-ethyl-) | 1-(methyl-$d_3$)-pyrazol-5-yl |
| P557 | 1,2,3,4-tetrazol-1-yl | 5-chloro, 6-fluoro | S-(2-(difluoro-methoxy)-ethyl-) | 1-(methyl-$d_3$)-pyrazol-5-yl |
| P558 | 1,2,3,4-tetrazol-1-yl | 5-chloro, 6-fluoro | S-(2-methoxy-ethyl-) | 1-(difluoro-methyl)-pyrazol-3-yl |
| P559 | 1,2,3,4-tetrazol-1-yl | 5-chloro, 6-fluoro | S-(2-methoxy-ethyl-) | 1-(difluoro-methyl)-pyrazol-5-yl |
| P560 | 1,2,3,4-tetrazol-1-yl | 5-chloro, 6-fluoro | R-(2-methoxy-ethyl-) | 1-(difluoro-methyl)-pyrazol-3-yl |
| P561 | 1,2,3,4-tetrazol-1-yl | 5-chloro, 6-fluoro | R-(2-methoxy-ethyl-) | 1-(difluoro-methyl)-pyrazol-5-yl |
| P562 | 1,2,3,4-tetrazol-1-yl | 5-chloro, 6-fluoro | S-(2-(difluoro-methoxy)-ethyl-) | 1-(difluoro-methyl)-pyrazol-5-yl |
| P563 | 1,2,3,4-tetrazol-1-yl | 5-chloro, 6-fluoro | R-(2-(difluoro-methoxy)-ethyl-) | 1-(difluoro-methyl)-pyrazol-3-yl |
| P564 | 1,2,3,4-tetrazol-1-yl | 5-chloro, 6-fluoro | R-(2-(difluoro-methoxy)-ethyl-) | 1-(difluoro-methyl)-pyrazol-5-yl |
| P565 | 1,2,3,4-tetrazol-1-yl | 5-chloro, 6-fluoro | S-(2-(difluoro-methoxy)-ethyl-) | 1-(difluoro-methyl)-pyrazol-3-yl |
| P566 | 1,2,3,4-tetrazol-1-yl | 5-chloro, 6-fluoro | S-(4-fluoro-phenyl-methyl-) | 1-(difluoro-methyl)-pyrazol-5-yl |
| P567 | 1,2,3,4-tetrazol-1-yl | 5-chloro, 6-fluoro | S-(4-fluoro-phenyl-methyl-) | 1-(difluoro-methyl)-pyrazol-3-yl |
| P568 | 1,2,3,4-tetrazol-1-yl | 5-chloro, 6-fluoro | R-(4-fluoro-phenyl-methyl-) | 1-(difluoro-methyl)-pyrazol-5-yl |
| P569 | 1,2,3,4-tetrazol-1-yl | 5-chloro, 6-fluoro | R-(4-fluoro-phenyl-methyl-) | 1-(difluoro-methyl)-pyrazol-3-yl |
| P572 | 1,2,3,4-tetrazol-1-yl | 5-chloro, 6-fluoro | R-(2-(difluoro-methoxy)-ethyl- | 1-(difluoro-methyl)-4-chloro-pyrazol-3-yl |
| P573 | 1,2,3,4-tetrazol-1-yl | 5-chloro, 6-fluoro | S-(2-(difluoro-methoxy)-ethyl-) | 1-(difluoro-methyl)-4-chloro-pyrazol-3-yl |
| P574 | 1,2,3,4-tetrazol-1-yl | 5-chloro, 6-fluoro | R-(2-(difluoro-methoxy)-ethyl-) | 1-(difluoro-methyl)-4-chloro-pyrazol-5-yl |
| P575 | 1,2,3,4-tetrazol-1-yl | 5-chloro, 6-fluoro | S*-(2-(difluoro-methoxy)-ethyl-) | 1-(difluoro-methyl)-4-chloro-pyrazol-5-yl |
| P576 | 1,2,3,4-tetrazol-1-yl | 5-chloro, 6-fluoro | R-(2-methoxy-ethyl-) | 1-(difluoro-methyl)-4-chloro-pyrazol-3-yl |
| P577 | 1,2,3,4-tetrazol-1-yl | 5-chloro, 6-fluoro | S-(2-methoxy-ethyl-) | 1-(difluoro-methyl)-4-chloro-pyrazol-3-yl |
| P578 | 1,2,3,4-tetrazol-1-yl | 5-chloro, 6-fluoro | R-(cyclopropyl-methyl-) | 1-(difluoro-methyl)-4-chloro-pyrazol-5-yl |
| P579 | 1,2,3,4-tetrazol-1-yl | 5-chloro, 6-fluoro | S-(2-(difluoro-methoxy)-ethyl-) | 4-(trifluoro-methyl)-thiazol-5-yl |
| P580 | 1,2,3,4-tetrazol-1-yl | 5-chloro, 6-fluoro | R-(2-(difluoro-methoxy)-ethyl-) | 4-(trifluoro-methyl)-thiazol-5-yl |

TABLE 3-continued

Representative Compounds of Formula (I)

| | | | | |
|---|---|---|---|---|
| P582 | 1,2,3,4-tetrazol-1-yl | 5-chloro, 6-fluoro | R-(2-(difluoro-methoxy)-ethyl-) | 4-chloro-thiazol-5-yl |
| P584 | 1,2,3,4-tetrazol-1-yl | 5-chloro, 6-fluoro | S-(2-(difluoro-methoxy)-ethyl-) | 4-chloro-thiazol-5-yl |
| P585 | 1,2,3,4-tetrazol-1-yl | 5-chloro, 6-fluoro | S-(cyclopropyl-methyl-) | 1-(difluoro-methyl)-pyrazol-5-yl |
| P586 | 1,2,3,4-tetrazol-1-yl | 5-chloro, 6-fluoro | R-(cyclopropyl-methyl-) | 1-(difluoro-methyl)-4-chloro-pyrazol-5-yl |
| P587 | 1,2,3,4-tetrazol-1-yl | 5-chloro, 6-fluoro | S-(cyclopropyl-methyl-) | 1-(difluoro-methyl)-4-chloro-pyrazol-5-yl |
| P588 | 1,2,3,4-tetrazol-1-yl | 5-chloro, 6-fluoro | R-(cyclopropyl-methyl-) | 1-(difluoro-methyl)-4-chloro-1,2,5-triazol-3-yl |
| P589 | 1,2,3,4-tetrazol-1-yl | 5-chloro, 6-fluoro | R*-(4-fluoro-phenyl-methyl-) | 1-(difluoro-methyl)-4-chloro-1,2,3-triazol-5-yl |
| P590 | 1,2,3,4-tetrazol-1-yl | 5-chloro, 6-fluoro | R-(cyclopropyl-methyl-) | 1-(difluoro-methyl)-4-chloro-1,2,3-triazol-5-yl |
| P591 | 1,2,3,4-tetrazol-1-yl | 5-chloro, 6-fluoro | S-(4-fluoro-phenyl-methyl-) | 1-(difluoro-methyl)-5-chloro-1,2,3-triazol-4-yl |
| P592 | 1,2,3,4-tetrazol-1-yl | 5-chloro, 6-fluoro | R-(4-fluoro-phenyl-methyl-) | 1-(difluoro-methyl)-4-chloro-1,2,5-triazol-3-yl |
| P593 | 1,2,3,4-tetrazol-1-yl | 5-chloro, 6-fluoro | S-(cyclopropyl-methyl-) | 1-(difluoro-methyl)-1,2,3-triazol-4-yl |
| P594 | 1,2,3,4-tetrazol-1-yl | 5-chloro, 6-fluoro | R-(cyclopropyl-methyl-) | 1-(difluoro-methyl)-1,2,3-triazol-4-yl |
| P595 | 1,2,3,4-tetrazol-1-yl | 5-chloro, 6-fluoro | R-(cyclopropyl-methyl-) | 1-(difluoro-methyl)-1,2,3-triazol-5-yl |
| P596 | 1,2,3,4-tetrazol-1-yl | 5-chloro, 6-fluoro | R-(4-fluoro-phenyl-methyl-) | 1-(difluoro-methyl)-1,2,5-triazol-3-yl |
| P597 | 1,2,3,4-tetrazol-1-yl | 5-chloro, 6-fluoro | S-(4-fluoro-phenyl-methyl-) | 1-(difluoro-methyl)-1,2,3-triazol-4-yl |
| P598 | 1,2,3,4-tetrazol-1-yl | 5-chloro, 6-fluoro | S*-(4-fluoro-phenyl-methyl-) | 1-(difluoro-methyl)-1,2,5-triazol-3-yl |
| P599 | 1,2,3,4-tetrazol-1-yl | 5-chloro, 6-fluoro | R-(4-fluoro-phenyl-methyl-) | 1-(difluoro-methyl)-1,2,3-triazol-5-yl |
| P600 | 1,2,3,4-tetrazol-1-yl | 5-chloro, 6-fluoro | R-(4-fluoro-phenyl-methyl-) | 1-(difluoro-methyl)-1,2,3-triazol-4-yl |
| P601 | 1,2,3,4-tetrazol-1-yl | 5-chloro, 6-fluoro | S-(cyclopropyl-methyl-) | 1-(difluoro-methyl)-1,2,3-triazol-5-yl |
| P602 | 1,2,3,4-tetrazol-1-yl | 5-chloro, 6-fluoro | S-(4-fluoro-phenyl-methyl-) | 1-(difluoro-methyl)-1,2,3-triazol-5-yl |
| P603 | 1,2,3,4-tetrazol-1-yl | 5-chloro, 6-fluoro | S-(cyclopropyl-methyl-) | 1-(difluoro-methyl)-1,2,5-triazol-3-yl |
| P604 | 1,2,3,4-tetrazol-1-yl | 5-chloro, 6-fluoro | R-(cyclopropyl-methyl-) | 1-(difluoro-methyl)-5-chloro-1,2,3-triazol-4-yl |
| P605 | 1,2,3,4-tetrazol-1-yl | 5-chloro, 6-fluoro | R-(4-fluoro-phenyl-methyl-) | 1-(difluoro-methyl)-4-chloro-1,2,3-triazol-5-yl |
| P606 | 1,2,3,4-tetrazol-1-yl | 5-chloro, 6-fluoro | R-(cyclopropyl-methyl-) | 1-(difluoro-methyl)-1,2,5-triazol-3-yl |
| P607 | 1,2,3,4-tetrazol-1-yl | 5-chloro, 6-fluoro | S-(cyclopropyl-methyl-) | 1-(difluoro-methyl)-5-chloro-1,2,3-triazol-4-yl |
| P608 | 1,2,3,4-tetrazol-1-yl | 5-chloro, 6-fluoro | S-(4-fluoro-phenyl-methyl-) | 1-(difluoro-methyl)-4-chloro-1,2,5-triazol-3-yl |
| P609 | 1,2,3,4-tetrazol-1-yl | 5-chloro, 6-fluoro | S-(cyclopropyl-methyl-) | 1-(difluoro-methyl)-4-chloro-1,2,5-triazol-3-yl |
| P610 | 1,2,3,4-tetrazol-1-yl | 5-chloro, 6-fluoro | R-(4-fluoro-phenyl-methyl-) | 1-(difluoro-methyl)-5-chloro-1,2,3-triazol-4-yl |
| P611 | 1,2,3,4-tetrazol-1-yl | 5-chloro, 6-fluoro | S-(cyclopropyl-methyl-) | 1-(difluoro-methyl)-4-chloro-1,2,3-triazol-5-yl |
| P612 | 1,2,3,4-tetrazol-1-yl | 5-chloro, 6-fluoro | cyclopropyl-methyl- | 3-methyl-1,2,4-oxadiazol-5-yl |
| P613 | 1,2,3,4-tetrazol-1-yl | 5-chloro, 6-fluoro | S-(cyclopropyl-methyl-) | 2-amino-thaizol-5-yl |
| P614 | 1,2,3,4-tetrazol-1-yl | 5-chloro, 6-fluoro | R-(cyclopropyl-methyl-) | 2-amino-thaizol-5-yl |
| P615 | 4-(difluoro-methoxy)-1,2,3-triazol-1-yl | 5-chloro, 6-fluoro | S-(2-methoxy-ethyl-) | 1-methyl-1,2,3-triazol-5-yl |
| P616 | 4-(difluoro-methoxy)-1,2,3-triazol-1-yl | 5-chloro, 6-fluoro | R-(2-methoxy-ethyl-) | 1-methyl-1,2,3-triazol-5-yl |
| P617 | 4-chloro-1,2,3-triazol-1-yl | 5-chloro, 6-fluoro | S-(4-fluoro-phenyl-methyl-) | 1-methyl-1,2,3-triazol-5-yl |
| P618 | 4-chloro-1,2,3-triazol-1-yl | 5-chloro, 6-fluoro | R-(4-fluoro-phenyl-methyl-) | 1-methyl-1,2,3-triazol-5-yl |
| P619 | 1,2,3,4-tetrazol-1-yl | 5-chloro, 6-fluoro | R-(2-methoxy-ethyl-) | 1-methyl-3-(trifluoro-methyl)-pyrazol-5-yl |
| P620 | 1,2,3,4-tetrazol-1-yl | 5-chloro, 6-fluoro | S-(2-methoxy-ethyl-) | 1-methyl-3-(trifluoro-methyl)-pyrazol-5-yl |

TABLE 3-continued

Representative Compounds of Formula (I)

| | | | | |
|---|---|---|---|---|
| P622 | 1,2,3,4-tetrazol-1-yl | 5-chloro, 6-fluoro | S-(2-methoxy-ethyl-) | 1-(difluoro-methyl)-4-chloro-pyrazol-5-yl |
| P623 | 1,2,3,4-tetrazol-1-yl | 5-chloro, 6-fluoro | R-(2-methoxy-ethyl-) | 1-(difluoro-methyl)-4-chloro-pyrazol-5-yl |
| P624 | 1,2,3,4-tetrazol-1-yl | 5-chloro, 6-fluoro | cyclopropyl-methyl- | 2-amino-4-chloro-thiazol-5-yl |
| P625 | 4-chloro-1,2,3-triazol-1-yl | 5-chloro, 6-fluoro | S-(2-methoxy-ethyl-) | 1-(difluoro-methyl)-4-fluoro-pyrazol-5-yl |
| P626 | 4-chloro-1,2,3-triazol-1-yl | 5-chloro, 6-fluoro | R-(2-methoxy-ethyl-) | 1-(difluoro-methyl)-4-fluoro-pyrazol-5-yl |
| P627 | 1,2,3,4-tetrazol-1-yl | 5-chloro, 6-fluoro | S-(cyclopropyl-methyl-) | 1-(difluoro-methyl)-4-fluoro-pyrazol-5-yl |
| P628 | 1,2,3,4-tetrazol-1-yl | 5-chloro, 6-fluoro | R-(cyclopropyl-methyl-) | 1-(difluoro-methyl)-4-fluoro-pyrazol-5-yl |
| P629 | 4-chloro-1,2,3-triazol-1-yl | 5-chloro, 6-fluoro | S-(4-fluoro-phenyl-methyl-) | 1-methyl-4-cyano-pyrazol-5-yl |
| P630 | 4-chloro-1,2,3-triazol-1-yl | 5-chloro, 6-fluoro | R-(4-fluoro-phenyl-methyl-) | 1-methyl-4-cyano-pyrazol-5-yl |
| P631 | 4-chloro-1,2,3-triazol-1-yl | 5-chloro, 6-fluoro | R-(4-fluoro-pyrazol-1-yl-methyl-) | 1-(difluoro-methyl)-4-fluoro-pyrazol-5-yl |
| P632 | 4-(difluoro-methoxy)-1,2,3-triazol-1-yl | 5-chloro, 6-fluoro | S-(4-fluoro-phenyl-methyl-) | 1-methyl-1,2,3-triazol-5-yl |
| P633 | 4-chloro-1,2,3-triazol-1-yl | 5-chloro, 6-fluoro | S-(2-(difluoro-methoxy)-ethyl-) | 1-methyl-1,2,3-triazol-5-yl |
| P634 | 4-chloro-1,2,3-triazol-1-yl | 5-chloro, 6-fluoro | S-(4-fluoro-pyrazol-1-yl-methyl-) | 1-(difluoro-methyl)-4-fluoro-pyrazol-5-yl |
| P635 | 4-(difluoro-methoxy)-1,2,3-triazol-1-yl | 5-chloro, 6-fluoro | R-(4-fluoro-phenyl-methyl-) | 1-methyl-1,2,3-triazol-5-yl |
| P636 | 4-chloro-1,2,3-triazol-1-yl | 5-chloro, 6-fluoro | R-(2-(difluoro-methoxy)-ethyl-) | 1-methyl-1,2,3-triazol-5-yl |
| P637 | 1,2,3,4-tetrazol-1-yl | 5-chloro, 6-fluoro | S-(2-t-butoxy-ethyl-) | 1-(difluoro-methyl)-pyrazol-5-yl |
| P638 | 4-chloro-1,2,3-triazol-1-yl | 5-chloro, 6-fluoro | S*-(2-methoxy-ethyl) | 1-methyl-4-chloro-1,2,3-triazol-5-yl |
| P639 | 4-chloro-1,2,3-triazol-1-yl | 5-chloro, 6-fluoro | R-(2-methoxy-ethyl-) | 1-methyl-4-chloro-1,2,3-triazol-5-yl |
| P640 | 1,2,3,4-tetrazol-1-yl | 5-chloro, 6-fluoro | R-(2-t-butoxy-ethyl-) | 1-(difluoro-methyl)-pyrazol-5-yl |
| P641 | 4-chloro-1,2,3-triazol-1-yl | 5-chloro, 6-fluoro | S-(4-fluoro-pyrazol-1-yl-methyl-) | 1-(difluoro-methyl)-pyrazol-5-yl |
| P642 | 1,2,3,4-tetrazol-1-yl | 5-chloro, 6-fluoro | S-(2-methoxy-2-methyl-n-propyl-) | 1-(difluoro-methyl)-pyrazol-5-yl |
| P643 | 4-chloro-1,2,3-triazol-1-yl | 5-chloro, 6-fluoro | R-(4-fluoro-pyrazol-1-yl-methyl-) | 1-(difluoro-methyl)-pyrazol-5-yl |
| P644 | 1,2,3,4-tetrazol-1-yl | 5-chloro, 6-fluoro | S*-(4-fluoro-pyrazol-1-yl-methyl-) | 1-(difluoro-methyl)-pyrazol-5-yl |
| P645 | 1,2,3,4-tetrazol-1-yl | 5-chloro, 6-fluoro | S-(4-fluoro-pyrazol-1-yl-methyl-) | 1-(difluoro-methyl)-pyrazol-5-yl |
| P646 | 1,2,3,4-tetrazol-1-yl | 5-chloro, 6-fluoro | R-(2-methoxy-2-methyl-n-propyl-) | 1-(difluoro-methyl)-pyrazol-5-yl |
| P647 | 1,2,3,4-tetrazol-1-yl | 5-chloro, 6-fluoro | S-(2-hydroxy-2-methyl-n-propyl-) | 1-(difluoro-methyl)-pyrazol-5-yl |
| P648 | 1,2,3,4-tetrazol-1-yl | 5-chloro, 6-fluoro | R-(2-hydroxy-2-methyl-n-propyl-) | 1-(difluoro-methyl)-pyrazol-5-yl |
| P649 | 1,2,3,4-tetrazol-1-yl | 5-chloro, 6-fluoro | S-(2-hydroxy-ethyl-) | 1-(difluoro-methyl)-pyrazol-5-yl |
| P650 | 1,2,3,4-tetrazol-1-yl | 5-chloro, 6-fluoro | R-(2-hydroxy-ethyl-) | 1-(difluoro-methyl)-pyrazol-5-yl |
| P653 | 1,2,3,4-tetrazol-1-yl | 5-chloro, 6-fluoro | R-(2,2-difluoro-cyclopropyl-methyl-) | 1-(difluoro-methyl)-1,2,3-triazol-4-yl |
| P654 | 1,2,3,4-tetrazol-1-yl | 5-chloro, 6-fluoro | S-(2,2-difluoro-cyclopropyl-methyl-) | 1-(difluoro-methyl)-1,2,3-triazol-4-yl |
| P655 | 4-chloro-1,2,3-triazol-1-yl | 5-chloro, 6-fluoro | R-(4-(difluoro-methoxy)-pyrazol-1-yl-methyl-) | 1-(difluoro-methyl)-1,2,3-triazol-4-yl |
| P656 | 4-chloro-1,2,3-triazol-1-yl | 5-chloro, 6-fluoro | S-(4-(difluoro-methoxy)-pyrazol-1-yl-methyl-) | 1-(difluoro-methyl)-1,2,3-triazol-4-yl |
| P657 | 1,2,3,4-tetrazol-1-yl | 5-chloro, 6-fluoro | R-(cyclobutyl-methyl-) | 1-(difluoro-methyl)-1,2,3-triazol-4-yl |
| P658 | 1,2,3,4-tetrazol-1-yl | 5-chloro, 6-fluoro | S-(cyclobutyl-methyl-) | 1-(difluoro-methyl)-1,2,3-triazol-4-yl |
| P659 | 1,2,3,4-tetrazol-1-yl | 5-chloro, 6-fluoro | S*-(2-(difluoro-methoxy)-ethyl-) | 1-(difluoro-methyl)-1,2,3-triazol-4-yl |
| P660 | 1,2,3,4-tetrazol-1-yl | 5-chloro, 6-fluoro | R*-(2-(difluoro-methoxy)-ethyl-) | 1-(difluoro-methyl)-1,2,3-triazol-4-yl |
| P661 | 1,2,3,4-tetrazol-1-yl | 5-chloro, 6-fluoro | R*-(cyclopropyl-methyl-) | 1-(difluoro-methyl)-4-cyano-pyrazol-5-yl |

TABLE 3-continued

Representative Compounds of Formula (I)

| ID | Col1 | Col2 | Col3 | Col4 |
|---|---|---|---|---|
| P662 | 1,2,3,4-tetrazol-1-yl | 5-chloro, 6-fluoro | cyclopropyl-methyl- | 1-(difluoro-methyl)-4-cyano-pyrazol-3-yl |
| P663 | 1,2,3,4-tetrazol-1-yl | 5-chloro, 6-fluoro | S*-(cyclopropyl-methyl-) | 1-(difluoro-methyl)-4-cyano-pyrazol-5-yl |
| P664 | 4-chloro-1,2,3-triazol-1-yl | 5-chloro, 6-fluoro | S*-(pyrazol-1-yl-methyl-) | 1-(difluoro-methyl)-1,2,3-triazol-4-yl |
| P665 | 4-chloro-1,2,3-triazol-1-yl | 5-chloro, 6-fluoro | R*-(pyrazol-1-yl-methyl-) | 1-(difluoro-methyl)-1,2,3-triazol-4-yl |
| P666 | 4-chloro-1,2,3-triazol-1-yl | 5-chloro, 6-fluoro | R-(2-(difluoro-methoxy)-ethyl-) | 1-(difluoro-methyl)-1,2,5-triazol-3-yl |
| P667 | 4-chloro-1,2,3-triazol-1-yl | 5-chloro, 6-fluoro | S-(2-(difluoro-methoxy)-ethyl-) | 1-(difluoro-methyl)-1,2,3-triazol-5-yl |
| P668 | 4-chloro-1,2,3-triazol-1-yl | 5-chloro, 6-fluoro | R-(2-(difluoro-methoxy)-ethyl-) | 1-(difluoro-methyl)-1,2,3-triazol-5-yl |
| P669 | 1,2,3,4-tetrazol-1-yl | 5-chloro, 6-fluoro | S-(cyclopropyl-methyl-) | 1-methyl-4-hydroxy-pyrazol-5-yl |
| P670 | 4-chloro-1,2,3-triazol-1-yl | 5-chloro, 6-fluoro | S-(2-(difluoro-methoxy)-ethyl-) | 1-(difluoro-methyl)-1,2,5-triazol-3-yl |
| P671 | 1,2,3,4-tetrazol-1-yl | 5-chloro, 6-fluoro | S-(2-methoxy-ethyl-) | 1-(difluoro-methyl)-1,2,3-triazol-5-yl |
| P672 | 1,2,3,4-tetrazol-1-yl | 5-chloro, 6-fluoro | S-(2-(difluoro-methoxy)-ethyl-) | 1-(difluoro-methyl)-1,2,3-triazol-5-yl |
| P673 | 1,2,3,4-tetrazol-1-yl | 5-chloro, 6-fluoro | R-(cyclopropyl-methyl-) | 1-methyl-4-hydroxy-pyrazol-5-yl |
| P674 | 1,2,3,4-tetrazol-1-yl | 5-chloro, 6-fluoro | R-(2-(difluoro-methoxy)-ethyl-) | 1-(difluoro-methyl)-1,2,5-triazol-3-yl |
| P675 | 1,2,3,4-tetrazol-1-yl | 5-chloro, 6-fluoro | R-(2-methoxy-ethyl-) | 1-(difluoro-methyl)-1,2,5-triazol-3-yl |
| P676 | 1,2,3,4-tetrazol-1-yl | 5-chloro, 6-fluoro | R-(2-(difluoro-methoxy)-ethyl-) | 1-(difluoro-methyl)-1,2,3-triazol-5-yl |
| P677 | 1,2,3,4-tetrazol-1-yl | 5-chloro, 6-fluoro | S-(2-(difluoro-methoxy)-ethyl-) | 1-(difluoro-methyl)-1,2,5-triazol-3-yl |
| P678 | 4-chloro-1,2,3-triazol-1-yl | 5-chloro, 6-fluoro | S-(2-(difluoro-methoxy)-ethyl-) | 1-(difluoro-methyl)-1,2,3-triazol-4-yl |
| P679 | 4-chloro-1,2,3-triazol-1-yl | 5-chloro, 6-fluoro | R-(2-(difluoro-methoxy)-ethyl-) | 1-(difluoro-methyl)-1,2,3-triazol-4-yl |
| P680 | 4-chloro-1,2,3-triazol-1-yl | 5-chloro, 6-fluoro | R-(2-(difluoro-methoxy)-ethyl-) | 1-methyl-4-fluoro-pyrazol-5-yl |
| P681 | 4-chloro-1,2,3-triazol-1-yl | 5-chloro, 6-fluoro | S-(2-(difluoro-methoxy)-ethyl-) | 1-methyl-4-fluoro-pyrazol-5-yl |
| P682 | 4-chloro-1,2,3-triazol-1-yl | 5-chloro, 6-fluoro | S-(pyrazol-1-yl-methyl-) | 1-(difluoro-methyl)-1,2,5-triazol-3-yl |
| P683 | 4-chloro-1,2,3-triazol-1-yl | 5-chloro, 6-fluoro | R-(2-(difluoro-methoxy)-ethyl-) | 1-(difluoro-methyl)-1,2,4-triazol-5-yl |
| P684 | 4-chloro-1,2,3-triazol-1-yl | 5-chloro, 6-fluoro | S-(pyrazol-1-yl-methyl-) | 1-(difluoro-methyl)-1,2,3-triazol-5-yl |
| P685 | 4-chloro-1,2,3-triazol-1-yl | 5-chloro, 6-fluoro | R-(pyrazol-1-yl-methyl-) | 1-(difluoro-methyl)-1,2,3-triazol-5-yl |
| P686 | 1,2,3,4-tetrazol-1-yl | 5-chloro, 6-fluoro | S-(2-methoxy-ethyl-) | 1-(difluoro-methyl)-1,2,5-triazol-3-yl |
| P687 | 4-chloro-1,2,3-triazol-1-yl | 5-chloro, 6-fluoro | S-(2-(difluoro-methoxy)-ethyl-) | 1-(difluoro-methyl)-1,2,4-triazol-5-yl |
| P688 | 1,2,3,4-tetrazol-1-yl | 5-chloro, 6-fluoro | R-(2-methoxy-ethyl-) | 1-(difluoro-methyl)-1,2,3-triazol-4-yl |
| P689 | 1,2,3,4-tetrazol-1-yl | 5-chloro, 6-fluoro | S-(2-methoxy-ethyl-) | 1-(difluoro-methyl)-1,2,3-triazol-4-yl |
| P690 | 1,2,3,4-tetrazol-1-yl | 5-chloro, 6-fluoro | R-(2-methoxy-ethyl-) | 1-(difluoro-methyl)-1,2,3-triazol-5-yl |
| P691 | 4-chloro-1,2,3-triazol-1-yl | 5-chloro, 6-fluoro | R-(pyrazol-1-yl-methyl-) | 1-(difluoro-methyl)-1,2,5-triazol-3-yl |
| P692 | 4-chloro-1,2,3-triazol-1-yl | 5-chloro, 6-fluoro | R-(2-(difluoro-methoxy)-ethyl-) | 1-(difluoro-methyl)-1,3,4-triazol-2-yl |
| P693 | 4-chloro-1,2,3-triazol-1-yl | 5-chloro, 6-fluoro | S-(2-(difluoro-methoxy)-ethyl-) | 1-(difluoro-methyl)-1,3,4-triazol-2-yl |
| P696 | 1,2,3,4-tetrazol-1-yl | 5-chloro, 6-fluoro | 1-methyl-1,2,5-triazol-3-yl | 1-(difluoro-methyl)-pyrazol-5-yl) |
| P697 | 1,2,3,4-tetrazol-1-yl | 5-chloro, 6-fluoro | 1-phenyl-1,2,5-triazol-3-yl | 1-(difluoro-methyl)-pyrazol-5-yl |
| P699 | 1,2,3,4-tetrazol-1-yl | 5-chloro, 6-fluoro | R-(3,3,3-trifluoro-n-propyl) | 1-(difluoro-methyl)-1,2,3-triazol-4-yl |
| P700 | 1,2,3,4-tetrazol-1-yl | 5-chloro, 6-fluoro | S-(3,3,3-trifluoro-n-propyl) | 1-(difluoro-methyl)-1,2,3-triazol-4-yl |
| P701 | 1,2,3,4-tetrazol-1-yl | 5-chloro, 6-fluoro | S-(2-(difluoro-methoxy)-ethyl-) | 1-(difluoro-methyl)-1,2,4-triazol-5-yl |
| P702 | 1,2,3,4-tetrazol-1-yl | 5-chloro, 6-fluoro | R-(2-(difluoro-methoxy)-ethyl-) | 1-(difluoro-methyl)-1,2,4-triazol-5-yl |
| P705 | 4-chloro-1,2,3-triazol-1-yl | 5-chloro, 6-fluoro | R-(2-(difluoro-methoxy)-ethyl-) | 1-methyl-5-fluoro-1,2,3-triazol-4-yl |

TABLE 3-continued

Representative Compounds of Formula (I)

| | | | | |
|---|---|---|---|---|
| P706 | 4-chloro-1,2,3-triazol-1-yl | 5-chloro, 6-fluoro | S-(2-(difluoro-methoxy)-ethyl-) | 1-methyl-5-fluoro-1,2,3-triazol-4-yl |
| P708 | 1,2,3,4-tetrazol-1-yl | 5-chloro, 6-fluoro | cyclopropyl-methyl- | 1-(trifluoro-methyl)-pyrazol-4-yl |
| P709 | 1,2,3,4-tetrazol-1-yl | 5-chloro, 6-fluoro | cyclopropyl-methyl- | 1-(difluoro-methyl)-3-hydroxy-pyrazol-4-yl |
| P713 | 1,2,3,4-tetrazol-1-yl | 5-chloro, 6-fluoro | S-(S-(1-hydroxy-1-phenyl)-methyl-) | 1-(difluoro-methyl)-pyrazol-5-yl |
| P714 | 1,2,3,4-tetrazol-1-yl | 5-chloro, 6-fluoro | R-(2-(difluoro-methoxy)-ethyl-) | 1-(difluoro-methyl)-4-chloro-1,2,3-triazol-5-yl |
| P716 | 1,2,3,4-tetrazol-1-yl | 5-chloro, 6-fluoro | S-(R-(1-hydroxy-1-phenyl)-methyl-) | 1-(difluoro-methyl)-pyrazol-5-yl |
| P717 | 1,2,3,4-tetrazol-1-yl | 5-chloro, 6-fluoro | S-(2-(difluoro-methoxy)-ethyl-) | 1-(difluoro-methyl)-4-chloro-1,2,3-triazol-5-yl |
| P718 | 1,2,3,4-tetrazol-1-yl | 5-chloro, 6-fluoro | R-(thiazol-2-yl-methyl-) | 1-(difluoro-methyl)-pyrazol-5-yl |
| P719 | 1,2,3,4-tetrazol-1-yl | 5-chloro, 6-fluoro | R*-(R*-(1-hydroxy-1-phenyl)-methyl-) | 1-(difluoro-methyl)-pyrazol-5-yl |
| P720 | 4-chloro-1,2,3-triazol-1-yl | 5-chloro, 6-fluoro | S-(2-(difluoro-methoxy)-ethyl-) | 1-methyl-1,2,4-triazol-5-yl |
| P721 | 1,2,3,4-tetrazol-1-yl | 5-chloro, 6-fluoro | S*-(R*-(1-hydroxy-1-phenyl)-methyl-) | 1-(difluoro-methyl)-pyrazol-5-yl |
| P722 | 4-chloro-1,2,3-triazol-1-yl | 5-chloro, 6-fluoro | R-(2-(difluoro-methoxy)-ethyl-) | 1-methyl-1,2,4-triazol-5-yl |
| P723 | 1,2,3,4-tetrazol-1-yl | 5-chloro, 6-fluoro | S-(thiazol-2-yl-methyl-) | 1-(difluoro-methyl)-pyrazol-5-yl |
| P724 | 1,2,3,4-tetrazol-1-yl | 5-chloro, 6-fluoro | R-(2-(difluoro-methoxy)-ethyl-) | 1-methyl-4-fluoro-1,2,3-triazol-5-yl |
| P725 | 1,2,3,4-tetrazol-1-yl | 5-chloro, 6-fluoro | S-(2-(difluoro-methoxy)-ethyl-) | 1-methyl-4-chloro-1,2,3-triazol-5-yl |
| P726 | 1,2,3,4-tetrazol-1-yl | 5-chloro, 6-fluoro | R-(2-(difluoro-methoxy)-ethyl-) | 1-methyl-4-chloro-1,2,3-triazol-5-yl |
| P727 | 1,2,3,4-tetrazol-1-yl | 5-chloro, 6-fluoro | S-(2-(difluoro-methoxy)-ethyl-) | 1-methyl-4-fluoro-1,2,3-triazol-5-yl |
| P728 | 4-chloro-1,2,3-triazol-1-yl | 5-chloro, 6-fluoro | R*-(S*-(1-hydroxy-1-phenyl)-methyl-) | 1-(difluoro-methyl)-pyrazol-5-yl |
| P729 | 4-chloro-1,2,3-triazol-1-yl | 5-chloro, 6-fluoro | S*-(R*-(1-hydroxy-1-phenyl)-methyl-) | 1-(difluoro-methyl)-pyrazol-5-yl |
| P730 | 1,2,3,4-tetrazol-1-yl | 5-chloro, 6-fluoro | S-(4-(difluoro-methyl)-phenyl-methyl-) | 1-(difluoro-methyl)-1,2,3-triazol-5-yl |
| P731 | 1,2,3,4-tetrazol-1-yl | 5-chloro, 6-fluoro | R-(4-(difluoro-methyl)-phenyl-methyl-) | 1-(difluoro-methyl)-1,2,3-triazol-5-yl |
| P732 | 4-chloro-1,2,3-triazol-1-yl | 5-chloro, 6-fluoro | S*-(S*-(1-hydroxy-1-phenyl)-methyl-) | 1-(difluoro-methyl)-pyrazol-5-yl |
| P733 | 4-chloro-1,2,3-triazol-1-yl | 5-chloro, 6-fluoro | R*-(R*-(1-hydroxy-1-phenyl)-methyl-) | 1-(difluoro-methyl)-pyrazol-5-yl |
| P734 | 1,2,3,4-tetrazol-1-yl | 5-chloro, 6-fluoro | R-(1-(difluoro-methyl)-pyrazol-3-yl-methyl-) | 1-(difluoro-methyl)-pyrazol-5-yl |
| P735 | 1,2,3,4-tetrazol-1-yl | 5-chloro, 6-fluoro | S-(1-(difluoro-methyl)-pyrazol-3-yl-methyl-) | 1-(difluoro-methyl)-pyrazol-5-yl |
| P743 | 1,2,3,4-tetrazol-1-yl | 5-chloro, 6-fluoro | S-(cyclopropyl-methyl-) | 1-methyl-4-fluoro-1,2,3-triazol-5-yl |
| P744 | 1,2,3,4-tetrazol-1-yl | 5-chloro, 6-fluoro | R-(cyclopropyl-methyl-) | 1-methyl-4-fluoro-1,2,3-triazol-5-yl |
| P745 | 4-chloro-1,2,3-triazol-1-yl | 5-chloro, 6-fluoro | R*-(2-(difluoro-methoxy)-ethyl-) | 1-methyl-4-hydroxy-pyrazol-5-yl |
| P747 | 4-chloro-1,2,3-triazol-1-yl | 5-chloro, 6-fluoro | R-(2-(difluoro-methoxy)-ethyl-) | 1-methyl-4-hydroxy-pyrazol-5-yl |
| P749 | 1,2,3,4-tetrazol-1-yl | 5-chloro, 6-fluoro | R-(2-(difluoro-methoxy)-ethyl-) | 1-methyl-4-fluoro-1,2,3-triazol-5-yl |
| P750 | 1,2,3,4-tetrazol-1-yl | 5-chloro, 6-fluoro | R-(2-(difluoro-methoxy)-ethyl-) | 1-(difluoro-methyl)-4-fluoro-1,2,5-triazol-3-yl |
| P751 | 1,2,3,4-tetrazol-1-yl | 5-chloro, 6-fluoro | S-(2-(difluoro-methoxy)-ethyl-) | 1-(difluoro-methyl)-4-fluoro-1,2,3-triazol-5-yl |
| P752 | 1,2,3,4-tetrazol-1-yl | 5-chloro, 6-fluoro | R*-(2-(difluoro-methoxy)-ethyl-) | 1-(difluoro-methyl)-4-fluoro-1,2,5-triazol-3-yl |
| P753 | 1,2,3,4-tetrazol-1-yl | 5-chloro, 6-fluoro | 6-(trifluoro-methyl)-pyridin-3-yl-methyl- | 1-(difluoro-methyl)-pyrazol-5-yl |
| P754 | 4-(trifluoro-methyl)-1,2,3-triazol-1-yl | 5-chloro, 6-fluoro | R-(2-(difluoro-methoxy)-ethyl-) | 1-methyl-4-fluoro-1,2,3-triazol-5-yl |
| P755 | 4-(trifluoro-methyl)-1,2,3-triazol-1-yl | 5-chloro, 6-fluoro | S-(2-(difluoro-methoxy)-ethyl-) | 1-methyl-4-fluoro-1,2,3-triazol-5-yl |
| P756 | 4-(trifluoro-methyl)-1,2,3-triazol-1-yl | 5-chloro, 6-fluoro | S-(2-(difluoro-methoxy)-ethyl-) | 1-methyl-1,2,3-triazol-5-yl |
| P757 | 4-(trifluoro-methyl)-1,2,3-triazol-1-yl | 5-chloro, 6-fluoro | R-(2-(difluoro-methoxy)-ethyl-) | 1-methyl-1,2,4-triazol-5-yl |
| P758 | 4-(trifluoro-methyl)-1,2,3-triazol-1-yl | 5-chloro, 6-fluoro | S-(2-(difluoro-methoxy)-ethyl-) | 1-methyl-1,2,3-triazol-4-yl |

TABLE 3-continued

Representative Compounds of Formula (I)

| | | | | |
|---|---|---|---|---|
| P759 | 4-(trifluoro-methyl)-1,2,3-triazol-1-yl | 5-chloro, 6-fluoro | S-(2-(difluoro-methoxy)-ethyl-) | 1-methyl-1,2,4-triazol-5-yl |
| P760 | 4-(trifluoro-methyl)-1,2,3-triazol-1-yl | 5-chloro, 6-fluoro | R-(2-(difluoro-methoxy)-ethyl-) | 1-methyl-1,2,3-triazol-4-yl |
| P761 | 4-(trifluoro-methyl)-1,2,3-triazol-1-yl | 5-chloro, 6-fluoro | R-(2-(difluoro-methoxy)-ethyl-) | 1-methyl-1,2,3-triazol-5-yl |
| P762 | 1,2,3,4-tetrazol-1-yl | 5-chloro, 6-fluoro | R-(cyclopropyl-methyl-) | 1-(difluoro-methyl)-1,2,4-triazol-5-yl |
| P763 | 1,2,3,4-tetrazol-1-yl | 5-chloro, 6-fluoro | S-(cyclopropyl-methyl-) | 1-(difluoro-methyl)-1,2,4-triazol-5-yl |
| P764 | 1,2,3,4-tetrazol-1-yl | 5-chloro, 6-fluoro | S*-(S*-(2-methyl-cyclopropyl)-methyl-) | 1-(difluoro-methyl)-1,2,4-triazol-5-yl |
| P765 | 1,2,3,4-tetrazol-1-yl | 5-chloro, 6-fluoro | R*-(S*-(2-methyl-cyclopropyl)-methyl-) | 1-(difluoro-methyl)-1,2,4-triazol-5-yl |
| P766 | 1,2,3,4-tetrazol-1-yl | 5-chloro, 6-fluoro | R*-(R*-(2-methyl-cyclopropyl)-methyl-) | 1-(difluoro-methyl)-1,2,4-triazol-5-yl |
| P767 | 1,2,3,4-tetrazol-1-yl | 5-chloro, 6-fluoro | R*-(R*-(2-methyl-cyclopropyl)-methyl-) | 1-(difluoro-methyl)-1,2,4-triazol-5-yl |
| P768 | 1,2,3,4-tetrazol-1-yl | 5-chloro, 6-fluoro | R-((2-methyl-cyclopropyl)-methyl-) | 1-methyl-4-fluoro-1,2,3-triazol-5-yl |
| P769 | 1,2,3,4-tetrazol-1-yl | 5-chloro, 6-fluoro | S-((2-methyl-cyclopropyl)-methyl-) | 1-methyl-4-fluoro-1,2,3-triazol-5-yl |
| P770 | 1,2,3,4-tetrazol-1-yl | 5-chloro, 6-fluoro | S-(2-(difluoro-methoxy)-ethyl-) | 1-(difluoro-methyl)-imidazol-5-yl |
| P771 | 1,2,3,4-tetrazol-1-yl | 5-chloro, 6-fluoro | R-(2-(difluoro-methoxy)-ethyl-) | 1-(difluoro-methyl)-imidazol-5-yl |
| P772 | 4-chloro-1,2,3-triazol-1-yl | 5-chloro, 6-fluoro | R-(6-(trifluoro-methyl)-pyridin-3-yl-methyl-) | 1-methyl-1,2,3-triazol-5-yl |
| P773 | 4-chloro-1,2,3-triazol-1-yl | 5-chloro, 6-fluoro | S-(6-(trifluoro-methyl)-pyridin-3-yl-methyl-) | 1-methyl-1,2,3-triazol-5-yl |
| P774 | 1,2,3,4-tetrazol-1-yl | 5-chloro, 6-fluoro | 6-(trifluoro-methyl)-pyridin-3-yl-methyl- | 1-methyl-pyrazol-5-yl |
| P777 | 1,2,3,4-tetrazol-1-yl | 5-chloro, 6-fluoro | R-(6-(trifluoro-methyl)-pyridin-3-yl-methyl-) | 1-(difluoro-methyl)-pyrazol-5-yl |
| P778 | 1,2,3,4-tetrazol-1-yl | 5-chloro, 6-fluoro | S-(6-(trifluoro-methyl)-pyridin-3-yl-methyl-) | 1-(difluoro-methyl)-pyrazol-5-yl |
| P779 | 1,2,3,4-tetrazol-1-yl | 5-chloro, 6-fluoro | S-(6-(trifluoro-methyl)-pyridin-3-yl-methyl-) | 1-methyl-4-fluoro-1,2,3-triazol-5-yl |
| P780 | 1,2,3,4-tetrazol-1-yl | 5-chloro, 6-fluoro | R-(6-(trifluoro-methyl)-pyridin-3-yl-methyl-) | 1-methyl-4-fluoro-1,2,3-triazol-5-yl |
| P781 | 4-cyclopropyl-1,2,3-triazol-1-yl | 5-chloro, 6-fluoro | R-(2-(difluoro-methoxy)-ethyl-) | 1-methyl-1,2,4-triazol-5-yl |
| P782 | 4-cyclopropyl-1,2,3-triazol-1-yl | 5-chloro, 6-fluoro | S-(2-(difluoro-methoxy)-ethyl-) | 1-methyl-1,2,4-triazol-5-yl |
| P783 | 1,2,3,4-tetrazol-1-yl | 5-chloro, 6-fluoro | R-(6-(trifluoro-methyl)-pyridin-3-yl-methyl-) | 1-(difluoro-methyl)-1,2,4-triazol-5-yl |
| P784 | 1,2,3,4-tetrazol-1-yl | 5-chloro, 6-fluoro | S-(6-(trifluoro-methyl)-pyridin-3-yl-methyl-) | 1-(difluoro-methyl)-1,2,4-triazol-5-yl |
| P785 | 1,2,3,4-tetrazol-1-yl | 5-chloro, 6-fluoro | R-(6-(trifluoro-methyl)-pyridin-3-yl-methyl-) | 1-(difluoro-methyl)-imidazol-5-yl |
| P786 | 1,2,3,4-tetrazol-1-yl | 5-chloro, 6-fluoro | S-(6-(trifluoro-methyl)-pyridin-3-yl-methyl-) | 1-(difluoro-methyl)-imidazol-5-yl |
| P787 | 4-bromo-1,2,3-triazol-1-yl | 5-chloro, 6-fluoro | S-(2-(difluoro-methoxy)-ethyl-) | 1-(difluoro-methyl)-1,2,4-triazol-5-yl |
| P788 | 4-bromo-1,2,3-triazol-1-yl | 5-chloro, 6-fluoro | R-(2-(difluoro-methoxy)-ethyl-) | 1-(difluoro-methyl)-1,2,4-triazol-5-yl |
| P789 | 4-cyano-1,2,3-triazol-1-yl | 5-chloro, 6-fluoro | S-(2-(difluoro-methoxy)-ethyl-) | 1-(difluoro-methyl)-1,2,4-triazol-5-yl |
| P790 | 4-cyano-1,2,3-triazol-1-yl | 5-chloro, 6-fluoro | R-(2-(difluoro-methoxy)-ethyl-) | 1-(difluoro-methyl)-1,2,4-triazol-5-yl |
| P791 | 4-(trifluoro-methyl)-1,2,3-triazol-1-yl | 5-chloro, 6-fluoro | S-(1-(difluoro-methyl)-pyrazol-3-yl-methyl-) | 1-methyl-1,2,3-triazol-5-yl |
| P792 | 4-(trifluoro-methyl)-1,2,3-triazol-1-yl | 5-chloro, 6-fluoro | R-(1-(difluoro-methyl)-pyrazol-3-yl-methyl-) | 1-methyl-1,2,3-triazol-5-yl |
| P793 | 4-chloro-1,2,3-triazol-1-yl | 5-chloro, 6-fluoro | S-(1-(difluoro-methyl)-pyrazol-3-yl-methyl-) | 1-methyl-1,2,4-triazol-5-yl |
| P794 | 4-chloro-1,2,3-triazol-1-yl | 5-chloro, 6-fluoro | R-(1-(difluoro-methyl)-pyrazol-3-yl-methyl-) | 1-methyl-1,2,4-triazol-5-yl |
| P795 | 4-chloro-1,2,3-triazol-1-yl | 5-chloro, 6-fluoro | R-(1-(difluoro-methyl)-pyrazol-3-yl-methyl-) | 1-methyl-4-fluoro-1,2,3-triazol-5-yl |
| P796 | 4-chloro-1,2,3-triazol-1-yl | 5-chloro, 6-fluoro | S-(1-(difluoro-methyl)-pyrazol-3-yl-methyl-) | 1-methyl-4-fluoro-1,2,3-triazol-5-yl |
| P797 | 4-chloro-1,2,3-triazol-1-yl | 5-chloro, 6-fluoro | R-(1-(difluoro-methyl)-pyrazol-3-yl-methyl-) | 1-methyl-4-fluoro-1,2,3-triazol-5-yl |
| P798 | 4-chloro-1,2,3-triazol-1-yl | 5-chloro, 6-fluoro | S-(1-(difluoro-methyl)-pyrazol-3-yl-methyl-) | 1-methyl-4-fluoro-1,2,3-triazol-5-yl |

TABLE 3-continued

Representative Compounds of Formula (I)

| | | | | |
|---|---|---|---|---|
| P799 | 4-(difluoro-methoxy)-1,2,3-triazol-1-yl | 5-chloro, 6-fluoro | S-(2-(difluoro-methoxy)-ethyl-) | 1-methyl-1,2,4-triazol-5-yl |
| P800 | 5-(difluoro-methoxy)-1,2,3-triazol-1-yl | 5-chloro, 6-fluoro | S*-(2-(difluoro-methoxy)-ethyl-) | 1-methyl-1,2,4-triazol-5-yl |
| P801 | 4-(difluoro-methoxy)-1,2,3-triazol-1-yl | 5-chloro, 6-fluoro | R-(2-(difluoro-methoxy)-ethyl-) | 1-methyl-1,2,4-triazol-5-yl |
| P802 | 5-(difluoro-methoxy)-1,2,3-triazol-1-yl | 5-chloro, 6-fluoro | R*-(2-(difluoro-methoxy)-ethyl-) | 1-methyl-1,2,4-triazol-5-yl |
| P803 | 4-(trifluoro-methyl)-1,2,3-triazol-1-yl | 5-chloro, 6-fluoro | 2-(difluoro-methoxy)-ethyl- | 1-isopropyl-1,2,3-triazol-5-yl |
| P804 | 1,2,3-triazol-1-yl | 5-chloro, 6-fluoro | S*-(2-(difluoro-methoxy)-ethyl-) | 1-(difluoro-methyl)-1,2,4-triazol-5-yl |
| P805 | 4-(trifluoro-methyl)-1,2,3-triazol-1-yl | 5-chloro | R-(2-(difluoro-methoxy)-ethyl-) | 1-methyl-1,2,4-triazol-5-yl |
| P806 | 1,2,3-triazol-1-yl | 5-chloro, 6-fluoro | R*-(2-(difluoro-methoxy)-ethyl-) | 1-(difluoro-methyl)-1,2,4-triazol-5-yl |
| P807 | 4-(trifluoro-methyl)-1,2,3-triazol-1-yl | 5-chloro | S-(2-(difluoro-methoxy)-ethyl-) | 1-methyl-1,2,4-triazol-5-yl |
| P808 | 1,2,3,4-tetrazol-1-yl | 5-chloro, 6-fluoro | S*-(2-(difluoro-methoxy)-ethyl-) | 1-(difluoro-methyl)-1,2,4-triazol-5-yl |
| P809 | 4-chloro-1,2,3-triazol-1-yl | 5-chloro, 6-fluoro | R*-(2-(difluoro-methoxy)-ethyl-) | 1-(methyl-$d_3$)-4-(cyclopropyl-carbonyl-amino)-pyrazol-5-yl |
| P810 | 4-chloro-1,2,3-triazol-1-yl | 5-chloro, 6-fluoro | S*-(2-(difluoro-methoxy)-ethyl-) | 1-(methyl-$d_3$)-4-(cyclopropyl-carbonyl-amino)-pyrazol-5-yl |
| P811 | 4-(trifluoro-methyl)-1,2,3-triazol-1-yl | 5-chloro, 6-fluoro | R*-(2-hydroxy-ethyl-) | 1-methyl-1,2,4-triazol-5-yl |
| P812 | 4-(trifluoro-methyl)-1,2,3-triazol-1-yl | 5-chloro, 6-fluoro | S*-(2-hydroxy-ethyl-) | 1-methyl-1,2,4-triazol-5-yl |
| P813 | 4-(trifluoro-methyl)-1,2,3-triazol-1-yl | 5-chloro, 6-fluoro | S*-(2-(difluoro-methoxy)-ethyl-) | 1-methyl-1,2,4-triazol-5-yl |
| P814 | 4-(trifluoro-methyl)-1,2,3-triazol-1-yl | 5-chloro, 6-fluoro | R*-(2-(difluoro-methoxy)-ethyl-) | 1-methyl-1,2,4-triazol-5-yl |
| P815 | 4-(trifluoro-methyl)-1,2,3-triazol-1-yl | 5-chloro, 6-fluoro | S-(1-(difluoro-methyl)-pyrazol-3-yl-methyl-) | 1-methyl-1,2,4-triazol-5-yl |
| P816 | 4-(trifluoro-methyl)-1,2,3-triazol-1-yl | 5-chloro, 6-fluoro | R-(1-(difluoro-methyl)-pyrazol-3-yl-methyl-) | 1-methyl-1,2,4-triazol-5-yl |
| P817 | 4-cyano-1,2,3-triazol-1-yl | 5-chloro, 6-fluoro | R-(2-(difluoro-methoxy)-ethyl-) | 1-(difluoro-methyl)-1,2,3-triazol-5-yl |
| P818 | 4-cyano-1,2,3-triazol-1-yl | 5-chloro, 6-fluoro | S-(2-(difluoro-methoxy)-ethyl-) | 1-(difluoro-methyl)-1,2,3-triazol-5-yl |
| P819 | 4-(trifluoro-methyl)-1,2,3-triazol-1-yl | 5-chloro, 6-fluoro | S-(2-(difluoro-methoxy)-ethyl-2,2-$d_2$-) | 1-methyl-1,2,4-triazol-5-yl |
| P820 | 4-(trifluoro-methyl)-1,2,3-triazol-1-yl | 5-chloro, 6-fluoro | R-(2-(difluoro-methoxy)-ethyl-2,2-$d_2$-) | 1-methyl-1,2,4-triazol-5-yl |
| P821 | 4-(trifluoro-methyl)-1,2,3-triazol-1-yl | 5-chloro, 6-fluoro | R-(2-(difluoro-methoxy)-ethyl-2,2-$d_2$-) | 2-methyl-1,3,4-triazol-1-yl |
| P822 | 4-(trifluoro-methyl)-1,2,3-triazol-1-yl | 5-chloro, 6-fluoro | S-(2-(difluoro-methoxy)-ethyl-) | 2-methyl-1,3,4-triazol-1-yl |
| P823 | 4-(trifluoro-methyl)-1,2,3-triazol-1-yl | 5-chloro, 6-fluoro | R-(2-(difluoro-methoxy)-ethyl-) | 3-methyl-1,2,4-triazol-1-yl |
| P824 | 4-(trifluoro-methyl)-1,2,3-triazol-1-yl | 5-chloro, 6-fluoro | S-(2-(difluoro-methoxy)-ethyl-) | 3-methyl-1,2,4-triazol-1-yl |
| P825 | 4-(difluoro-methoxy)-1,2,3-triazol-1-yl | 5-chloro, 6-fluoro | S*-(2-(difluoro-methoxy)-ethyl-) | 3-methyl-1,2,4-triazol-1-yl |
| P826 | 4-(difluoro-methoxy)-1,2,3-triazol-1-yl | 5-chloro, 6-fluoro | S*-(2-(difluoro-methoxy)-ethyl-) | 2-methyl-imidazol-1-yl |
| P827 | 4-(difluoro-methoxy)-1,2,3-triazol-1-yl | 5-chloro, 6-fluoro | R*-(2-(difluoro-methoxy)-ethyl-) | 3-methyl-1,2,4-triazol-1-yl |
| P828 | 4-(difluoro-methoxy)-1,2,3-triazol-1-yl | 5-chloro, 6-fluoro | R*-(2-(difluoro-methoxy)-ethyl-) | 2-methyl-imidazol-1-yl |
| P829 | 4-(difluoro-methoxy)-1,2,3-triazol-1-yl | 5-chloro, 6-fluoro | R*-(2-(difluoro-methoxy)-ethyl-) | 2-methyl-1,3,4-triazol-1-yl |
| P830 | 4-(difluoro-methoxy)-1,2,3-triazol-1-yl | 5-chloro, 6-fluoro | S*-(2-(difluoro-methoxy)-ethyl-) | 2-methyl-1,3,4-triazol-1-yl |

TABLE 3-continued

Representative Compounds of Formula (I)

| | | | |
|---|---|---|---|
| P831 | 4-(trifluoro-methyl)-1,2,3-triazol-1-yl | 5-chloro, 6-fluoro | R*-(2-(difluoro-methoxy)-ethyl-) | 1-(methyl-d$_3$)-4-(cyclopropyl-carbonyl-amino)-pyrazol-5-yl |
| P832 | 4-(trifluoro-methyl)-1,2,3-triazol-1-yl | 5-chloro, 6-fluoro | S*-(2-(difluoro-methoxy)-ethyl-) | 1-(methyl-d$_3$)-4-(cyclopropyl-carbonyl-amino)-pyrazol-5-yl |
| P834 | 4-(trifluoro-methyl)-1,2,3-triazol-1-yl | 5-chloro, 6-fluoro | R-(2-(difluoro-methoxy)-ethyl-2,2-d$_2$-) | 1-methyl-1,2,4-triazol-5-yl |
| P835 | 4-(trifluoro-methyl)-1,2,3-triazol-1-yl | 5-chloro, 6-fluoro | S-(2-(difluoro-methoxy)-ethyl-2,2-d$_2$-) | 1-methyl-1,2,4-triazol-5-yl |
| P836 | 4-(trifluoro-methyl)-1,2,3-triazol-1-yl | 5-chloro, 6-fluoro | R*-(1-(difluoro-methyl)-pyrazol-3-yl-methyl-) | 1-(difluoro-methyl)-1,2,4-triazol-5-yl |
| P837 | 4-(trifluoro-methyl)-1,2,3-triazol-1-yl | 5-chloro, 6-fluoro | S*-(1-(difluoro-methyl)-pyrazol-3-yl-methyl-) | 1-(difluoro-methyl)-1,2,4-triazol-5-yl |
| P839 | 4-(trifluoro-methyl)-1,2,3-triazol-1-yl | 5-chloro, 6-fluoro | R*-(2-trifluoro-methoxy-ethyl-) | 1-methyl-1,2,4-triazol-5-yl |
| P840 | 4-(trifluoro-methyl)-1,2,3-triazol-1-yl | 5-chloro, 6-fluoro | R-(2-trifluoro-methoxy-ethyl-) | 1-methyl-1,2,4-triazol-5-yl |
| P843 | 1,2,3,4-tetrazol-1-yl | 5-chloro, 6-fluoro | S*-(2-(difluoro-methoxy)-ethyl-) | 1-(difluoro-methyl)-4-chloro-imidazol-5-yl |
| P845 | oxazol-5-yl | 5-chloro, 6-fluoro | R*-(2-(difluoro-methoxy)-ethyl-) | 1-methyl-4-fluoro-1,2,3-triazol-5-yl |
| P846 | oxazol-5-yl | 5-chloro, 6-fluoro | R-(2-(difluoro-methoxy)-ethyl-) | 1-methyl-4-fluoro-1,2,3-triazol-5-yl |
| P847 | 1,2,3,4-tetrazol-1-yl | 5-chloro, 6-fluoro | S-(cyclopropyl-methyl-) | 1-methyl-4-chloro-imidazol-5-yl |
| P848 | 1,2,3,4-tetrazol-1-yl | 5-chloro, 6-fluoro | R-(cyclopropyl-methyl-) | 1-methyl-4-chloro-imidazol-5-yl |
| P849 | 1,2,3,4-tetrazol-1-yl | 5-chloro, 6-fluoro | S-(2-(difluoro-methoxy)-ethyl-2,2-d$_2$-) | 1-methyl-3-chloro-pyrazol-4-yl |
| P850 | 1,2,3,4-tetrazol-1-yl | 5-chloro, 6-fluoro | R-(2-(difluoro-methoxy)-ethyl-2,2-d$_2$-) | 1-methyl-3-chloro-pyrazol-4-yl |
| P851 | 4-cyano-1,2,3-triazol-1-yl | 5-chloro, 6-fluoro | S-(1-(difluoro-methyl)-pyrazol-3-yl-methyl-) | 1-methyl-3-chloro-pyrazol-4-yl |
| P852 | 4-cyano-1,2,3-triazol-1-yl | 5-chloro, 6-fluoro | R-(1-(difluoro-methyl)-pyrazol-3-yl-methyl-) | 1-methyl-3-chloro-pyrazol-4-yl |
| P853 | 4-(trifluoro-methyl)-1,2,3-triazol-1-yl | 5-chloro, 6-fluoro | 2-(2-(methyoxy-d$_3$)-ethyl-2,2-d$_2$-) | 1-(difluoro-methyl)-pyrazol-5-yl |
| P856 | 4-cyano-1,2,3-triazol-1-yl | 5-chloro, 6-fluoro | R-(2-hydroxy-ethyl-2,2-d$_2$-) | 1-(difluoro-methyl)-1,2,4-triazol-5-yl |
| P857 | 4-cyano-1,2,3-triazol-1-yl | 5-chloro, 6-fluoro | S-(2-hydroxy-ethyl-2,2-d$_2$-) | 1-(difluoro-methyl)-1,2,4-triazol-5-yl |
| P863 | 4-(trifluoro-methyl)-1,2,3-triazol-1-yl | 5-chloro, 6-fluoro | S*-(2-(methoxy-d$_3$)-ethyl-2,2-d$_2$-) | 1-methyl-1,2,4-triazol-5-yl |
| P864 | 4-(trifluoro-methyl)-1,2,3-triazol-1-yl | 5-chloro, 6-fluoro | R*-(2-(methoxy-d$_3$)-ethyl-2,2-d$_2$-) | 1-methyl-1,2,4-triazol-5-yl |
| P869 | 1,2,3,4-tetrazol-1-yl | 5-chloro, 6-fluoro | S*-(2-(methoxy-d$_3$)-ethyl-2,2-d$_2$-) | 1-(difluoro-methyl)-pyrazol-5-yl |
| P870 | 1,2,3,4-tetrazol-1-yl | 5-chloro, 6-fluoro | R*-(2-(methoxy-d$_3$)-ethyl-2,2-d$_2$-) | 1-(difluoro-methyl)-pyrazol-5-yl |
| P874 | 4-(trifluoro-methyl)-1,2,3-triazol-1-yl | 5-chloro, 6-fluoro | cyclopropyl-methyl- | 1-methyl-1,2,4-triazol-5-yl |
| P903 | 4-(trifluoro-methyl)-1,2,3-triazol-1-yl | 5-chloro, 6-fluoro | 2-(difluoro-methoxy)-ethyl- | 4-(1,2,4-oxadiazol-3-yl-5-one)-phenyl |
| P904 | 4-(trifluoro-methyl)-1,2,3-triazol-1-yl | 5-chloro, 6-fluoro | cyclopropyl-methyl- | 5-(amino-carbonyl)-thien-2-yl |
| P920 | 4-chloro-1,2,3-triazol-1-yl | 5-chloro, 6-fluoro | S*-(1-(difluoro-methyl)-pyrazol-3-yl-methyl-) | 1-methyl-4-fluoro-1,2,3-triazol-5-yl |
| P925 | 4-(trifluoro-methyl)-1,2,3-triazol-1-yl | 5-chloro, 6-fluoro | oxazol-2-yl-methyl- | 1-methyl-1,2,4-triazol-5-yl |
| P934 | 4-(trifluoro-methyl)-1,2,3-triazol-1-yl | 5-chloro, 6-fluoro | morpholin-2-yl-methyl- | 1-methyl-1,2,4-triazol-5-yl |
| P935 | 4-(trifluoro-methyl)-1,2,3-triazol-1-yl | 5-chloro, 6-fluoro | 1,3,4-oxadiazol-2-yl-methyl- | 1-methyl-1,2,4-triazol-5-yl |
| P938 | 1,2,3,4-tetrazol-1-yl | 5-chloro, 6-fluoro | cyclopropyl-methyl- | 3-chloro-pyrazol-4-yl |
| P953 | 1,2,3,4-tetrazol-1-yl | 5-chloro, 6-fluoro | S*-(cyclopropyl-methyl-) | 4-fluoro-5-(amino-carbonyl)-thien-3-yl |
| P954 | 1,2,3,4-tetrazol-1-yl | 5-chloro, 6-fluoro | R*-(cyclopropyl-methyl-) | 4-fluoro-5-(amino-carbonyl)-thien-3-yl |
| P956 | 4-(trifluoro-methyl)-1,2,3-triazol-1-yl | 5-chloro, 6-fluoro | R*-(cyclopropyl-methyl-) | 3-methyl-5-(amino-carbonyl)-thien-2-yl |
| P957 | 4-(trifluoro-methyl)-1,2,3-triazol-1-yl | 5-chloro, 6-fluoro | S*-(cyclopropyl-methyl-) | 3-methyl-5-(amino-carbonyl)-thien-2-yl |
| P960 | 1,2,3,4-tetrazol-1-yl | 5-chloro, 6-fluoro | cyclopropyl-methyl- | 3-methyl-5-(amino-carbonyl)-thien-2-yl |

TABLE 3-continued

Representative Compounds of Formula (I)

| | | | | |
|---|---|---|---|---|
| P961 | 1,2,3,4-tetrazol-1-yl | 5-chloro, 6-fluoro | R*-(cyclopropyl-methyl-) | 2-(trifluoro-methyl)-4-methyl-thiazol-5-yl |
| P962 | 1,2,3,4-tetrazol-1-yl | 5-chloro, 6-fluoro | S*-(cyclopropyl-methyl-) | 2-(trifluoro-methyl)-4-methyl-thiazol-5-yl |

(I-PZ)

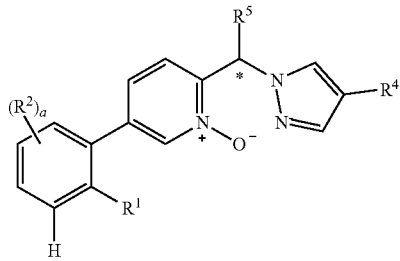

| ID No. | $R^1$ | $(R^2)_a$ | $R^5$ | $R^4$ |
|---|---|---|---|---|
| P19 | 1,2,3,4-tetrazol-1-yl | 5-chloro | cyclopropyl-methyl- | 2-chloro-6-amino-pyridin-3-yl |
| P20 | 1,2,3,4-tetrazol-1-yl | 5-chloro, 6-fluoro | cyclopropyl-methyl- | 2-fluoro-6-amino-pyridin-3-yl |
| P24 | 1,2,3,4-tetrazol-1-yl | 5-chloro, 6-fluoro | cyclopropyl-methyl- | 6-amino-pyridin-3-yl |
| P25 | 1,2,3,4-tetrazol-1-yl | 5-chloro, 6-fluoro | cyclopropyl-methyl- | 6-amino-pyridin-3-yl-1-oxide |
| P29 | 1,2,3,4-tetrazol-1-yl | 5-chloro, 6-fluoro | cyclopropyl-methyl- | 4-fluoro-6-amino-pyridin-3-yl |
| P36 | 1,2,3,4-tetrazol-1-yl | 5-chloro, 6-fluoro | R-(cyclopropyl-methyl-) | 2-fluoro-6-amino-pyridin-3-yl |
| P37 | 1,2,3,4-tetrazol-1-yl | 5-chloro, 6-fluoro | S-(cyclopropyl-methyl-) | 2-fluoro-6-amino-pyridin-3-yl |
| P45 | 1,2,3,4-tetrazol-1-yl | 5-chloro | phenyl-methyl- | 2-fluoro-6-amino-pyridin-3-yl |
| P48 | 1,2,3,4-tetrazol-1-yl | 5-chloro | R*-(cyclopropyl-methyl-) | 2-chloro-6-amino-pyridin-3-yl |
| P49 | 1,2,3,4-tetrazol-1-yl | 5-chloro | S*-(cyclopropyl-methyl-) | 2-chloro-6-amino-pyridin-3-yl |
| P50 | 1,2,3,4-tetrazol-1-yl | 5-chloro | phenyl-methyl- | 2-chloro-6-amino-pyridin-3-yl |
| P75 | 1,2,3,4-tetrazol-1-yl | 5-chloro, 6-fluoro | cyclopropyl-methyl- | 2-fluoro-5-methoxy-pyridin-3-yl |
| P103 | 1,2,3,4-tetrazol-1-yl | 5-chloro | cyclopropyl-methyl- | 1-isopropyl-pyridazin-4-yl-6-one |
| P108 | 1,2,3,4-tetrazol-1-yl | 5-chloro, 6-fluoro | cyclopropyl-methyl- | 1-(methoxy-carbonyl)-piperidin-3-yl |
| P111 | 1,2,3,4-tetrazol-1-yl | 5-chloro | cyclopropyl-methyl- | 1-(2-isopropyloxy-ethyl)-pyridazin-4-yl-6-one |
| P112 | 1,2,3,4-tetrazol-1-yl | 5-chloro | cyclopropyl-methyl- | 1-ethyl-pyridazin-4-yl-6-one |
| P116 | 1,2,3,4-tetrazol-1-yl | 5-chloro, 6-fluoro | 4-fluoro-phenyl-methyl- | 1-methyl-pyridazin-4-yl-6-one |
| P124 | 1,2,3,4-tetrazol-1-yl | 5-chloro | cyclopropyl-methyl- | 1-methyl-pyridazin-4-yl-6-one |
| P132 | 1,2,3,4-tetrazol-1-yl | 5-chloro, 6-fluoro | cyclopropyl-methyl- | 1-methyl-pyridazin-4-yl-6-one |
| P134 | 1,2,3,4-tetrazol-1-yl | 5-chloro, 6-fluoro | 4-methoxy-phenyl-methyl- | 1-methyl-pyridin-4-yl-2-one |
| P140 | 1,2,3,4-tetrazol-1-yl | 5-chloro, 6-fluoro | cyclopropyl-methyl- | 1-methyl-pyridin-4-yl-2-one |
| P144 | 1,2,3,4-tetrazol-1-yl | 5-chloro, 6-fluoro | cyclopropyl-methyl- | 1-methyl-pyridin-4-yl-2-one |
| P148 | oxazol-5-yl | 5-chloro, 6-fluoro | 4-fluoro-phenyl-methyl- | 2-fluoro-4-(cyclopropyl-carbonyl-amino)-pyridin-3-yl |
| P151 | 1,2,3,4-tetrazol-1-yl | 5-chloro | 4-chloro-phenyl-methyl- | pyridin-3-yl-1-oxide |
| P162 | 1,2,3,4-tetrazol-1-yl | 5-chloro, 6-fluoro | 4-chloro-phenyl-methyl- | 5-fluoro-6-amino-pyridin-3-yl |
| P166 | 1,2,3,4-tetrazol-1-yl | 5-chloro, 6-fluoro | 2-methoxy-ethyl- | 1-(methoxy-carbonyl)-piperidin-4-yl |
| P167 | 1,2,3,4-tetrazol-1-yl | 5-chloro, 6-fluoro | cyclopropyl-methyl- | 1-(methoxy-carbonyl)-piperidin-4-yl |
| P171 | 1,2,3,4-tetrazol-1-yl | 5-chloro | 4-chloro-phenyl-methyl- | pyridin-4-yl |
| P172 | 1,2,3,4-tetrazol-1-yl | 5-chloro | 4-chloro-phenyl-methyl- | pyridin-4-yl-1-oxide |
| P173 | 1,2,3,4-tetrazol-1-yl | 5-chloro | 4-chloro-phenyl-methyl- | 6-fluoro-pyridin-3-yl |
| P174 | 1,2,3,4-tetrazol-1-yl | 5-chloro | 4-chloro-phenyl-methyl- | 3-fluoro-pyridin-4-yl |

TABLE 3-continued

Representative Compounds of Formula (I)

| | | | | |
|---|---|---|---|---|
| P177 | 1,2,3,4-tetrazol-1-yl | 5-chloro, 6-fluoro | S*-(cyclopropyl-methyl-) | 2-chloro-6-amino-pyridin-3-yl |
| P178 | 1,2,3,4-tetrazol-1-yl | 5-chloro, 6-fluoro | R*-(cyclopropyl-methyl-) | 2-chloro-6-amino-pyridin-3-yl |
| P183 | 1,2,3,4-tetrazol-1-yl | 5-chloro, 6-fluoro | cyclopropyl-methyl- | 2-methyl-6-amino-pyridin-3-yl |
| P184 | 1,2,3,4-tetrazol-1-yl | 5-chloro, 6-fluoro | cyclopropyl-methyl- | 2-methyl-6-amino-pyridin-3-yl-1-oxide |
| P185 | 1,2,3,4-tetrazol-1-yl | 5-chloro, 6-fluoro | tetrahydrofuran-2-yl-methyl- | pyridin-4-yl-1-oxide |
| P186 | 1,2,3,4-tetrazol-1-yl | 5-chloro, 6-fluoro | tetrahydrofuran-2-yl-methyl- | pyridin-4-yl |
| P187 | 1,2,3,4-tetrazol-1-yl | 5-chloro, 6-fluoro | cyclopropyl-methyl- | pyridin-4-yl |
| P188 | 1,2,3,4-tetrazol-1-yl | 5-chloro, 6-fluoro | cyclopropyl-methyl- | pyrimidin-5-yl |
| P193 | 1,2,3,4-tetrazol-1-yl | 5-chloro, 6-fluoro | S*-(cyclopropyl-methyl-) | 5-fluoro-6-amino-pyridin-3-yl |
| P194 | 1,2,3,4-tetrazol-1-yl | 5-chloro, 6-fluoro | R*-(cyclopropyl-methyl-) | 5-fluoro-6-amino-pyridin-3-yl |
| P199 | 1,2,3,4-tetrazol-1-yl | 5-chloro, 6-fluoro | 2R*-(piperidin-1-yl-carbonyl)-1S*-cyclopropyl-methyl- | 1-methyl-pyridazin-4-yl-6-one |
| P200 | 1,2,3,4-tetrazol-1-yl | 5-chloro, 6-fluoro | 2S*-(piperidin-1-yl-carbonyl)-1S*-cyclopropyl-methyl- | 1-methyl-pyridazin-4-yl-6-one |
| P201 | 1,2,3,4-tetrazol-1-yl | 5-chloro, 6-fluoro | 2-(amino-carbonyl)-cyclopropyl-methyl- | 2-fluoro-6-amino-pyridin-3-yl |
| P210 | 1,2,3,4-tetrazol-1-yl | 5-chloro | 4-chloro-phenyl-methyl- | 2-fluoro-pyridin-4-yl |
| P211 | 1,2,3,4-tetrazol-1-yl | 5-chloro, 6-fluoro | R*-ethyl | pyridin-4-yl |
| P212 | 1,2,3,4-tetrazol-1-yl | 5-chloro, 6-fluoro | S*-ethyl | pyridin-4-yl |
| P216 | 1,2,3,4-tetrazol-1-yl | 5-chloro, 6-fluoro | cyclopropyl-methyl- | 1-methyl-pyridin-3-yl-6-one |
| P233 | 1,2,3,4-tetrazol-1-yl | 5-chloro, 6-fluoro | R*-ethyl | pyridin-4-yl-1-oxide |
| P234 | 1,2,3,4-tetrazol-1-yl | 5-chloro, 6-fluoro | S*-ethyl | pyridin-4-yl-1-oxide |
| P235 | 1,2,3,4-tetrazol-1-yl | 5-chloro, 6-fluoro | R*-(4-fluoro-phenyl-methyl-) | pyridin-4-yl |
| P236 | 1,2,3,4-tetrazol-1-yl | 5-chloro, 6-fluoro | S*-(4-fluoro-phenyl-methyl-) | pyridin-4-yl |
| P237 | 1,2,3,4-tetrazol-1-yl | 5-chloro, 6-fluoro | R*-(4-fluoro-phenyl-methyl-) | pyridin-4-yl-1-oxide |
| P238 | 1,2,3,4-tetrazol-1-yl | 5-chloro, 6-fluoro | S*-(4-fluoro-phenyl-methyl-) | pyridin-4-yl-1-oxide |
| P241 | 1,2,3,4-tetrazol-1-yl | 5-chloro, 6-fluoro | R*-(pyrrolidin-1-yl-2-one-methyl-) | pyridin-4-yl |
| P242 | 1,2,3,4-tetrazol-1-yl | 5-chloro, 6-fluoro | R-(pyrrolidin-1-yl-2-one-methyl-) | pyridin-4-yl |
| P243 | 1,2,3,4-tetrazol-1-yl | 5-chloro, 6-fluoro | R*-(pyrrolidin-1-yl-2-one-methyl-) | pyridin-4-yl-1-oxide |
| P244 | 1,2,3,4-tetrazol-1-yl | 5-chloro, 6-fluoro | S*-(pyrrolidin-1-yl-2-one-methyl-) | pyridin-4-yl-1-oxide |
| P250 | 1,2,3,4-tetrazol-1-yl | 5-chloro | 4-chloro-phenyl-methyl- | 2-(trifluoro-methyl)-pyridin-4-yl |
| P252 | 1,2,3,4-tetrazol-1-yl | 5-chloro, 6-fluoro | 2-(piperidin-1-yl-carbonyl)-cyclopropyl-methyl- | pyridin-4-yl |
| P253 | 1,2,3,4-tetrazol-1-yl | 5-chloro, 6-fluoro | 2-(3-phenyl-pyrrolidin-1-yl-carbonyl)-cyclopropyl-methyl- | pyridin-4-yl |
| P254 | 1,2,3,4-tetrazol-1-yl | 5-chloro, 6-fluoro | 2-(3-cyclopropyl-pyrrolidin-1-yl-carbonyl)-cyclopropyl-methyl- | pyridin-4-yl |
| P255 | 1,2,3,4-tetrazol-1-yl | 5-chloro, 6-fluoro | 2-(azaspiro[2.4]hepatn-5-yl-carbonyl)-cyclopropyl-methyl- | pyridin-4-yl |
| P256 | 1,2,3,4-tetrazol-1-yl | 5-chloro, 6-fluoro | pyrazol-1-yl-methyl- | 2-fluoro-6-amino-pyridin-3-yl |
| P257 | 1,2,3,4-tetrazol-1-yl | 5-chloro, 6-fluoro | pyrrolidin-1-yl-2-one-methyl- | 2-fluoro-pyridin-4-yl |
| P258 | 1,2,3,4-tetrazol-1-yl | 5-chloro, 6-fluoro | R*-(cyclopropyl-methyl-) | pyrimidin-4-yl |
| P259 | 1,2,3,4-tetrazol-1-yl | 5-chloro, 6-fluoro | S*-(cyclopropyl-methyl-) | pyrimidin-4-yl |
| P260 | 1,2,3,4-tetrazol-1-yl | 5-chloro, 6-fluoro | 2-(amino-carbonyl)-cyclopropyl-methyl- | pyridin-4-yl |

TABLE 3-continued

Representative Compounds of Formula (I)

| | | | | |
|---|---|---|---|---|
| P261 | 1,2,3,4-tetrazol-1-yl | 5-chloro, 6-fluoro | R*-(cyclopropyl-methyl-) | pyridin-4-yl |
| P262 | 1,2,3,4-tetrazol-1-yl | 5-chloro, 6-fluoro | S*-(cyclopropyl-methyl-) | pyridin-4-yl |
| P263 | 1,2,3,4-tetrazol-1-yl | 5-chloro, 6-fluoro | R*-(cyclopropyl-methyl-) | 2-fluoro-pyridin-4-yl |
| P264 | 1,2,3,4-tetrazol-1-yl | 5-chloro, 6-fluoro | S*-(cyclopropyl-methyl-) | 2-fluoro-pyridin-4-yl |
| P266 | 1,2,3,4-tetrazol-1-yl | 5-chloro, 6-fluoro | 2R*-(pyrrolidin-1-yl-carbonyl)-1S*-cyclopropyl-methyl- | pyridin-4-yl |
| P267 | 1,2,3,4-tetrazol-1-yl | 5-chloro, 6-fluoro | 2S*-(pyrrolidin-1-yl-carbonyl)-1S*-cyclopropyl-methyl- | pyridin-4-yl |
| P268 | 1,2,3,4-tetrazol-1-yl | 5-chloro, 6-fluoro | 2-(piperidin-1-yl-carbonyl)-cyclopropyl-methyl- | pyridin-4-yl-1-oxide |
| P269 | 1,2,3,4-tetrazol-1-yl | 5-chloro, 6-fluoro | pyrazol-1-yl-methyl- | pyridin-4-yl |
| P270 | 1,2,3,4-tetrazol-1-yl | 5-chloro, 6-fluoro | 3-phenyl-pyrazol-1-yl-methyl- | pyridin-4-yl |
| P274 | 1,2,3,4-tetrazol-1-yl | 5-chloro, 6-fluoro | 2-(7-amino-azaspiro[2.4]heptan-5-yl-carbonyl)-cyclopropyl-methyl- | pyridin-4-yl |
| P275 | 1,2,3,4-tetrazol-1-yl | 5-chloro, 6-fluoro | 4-fluoro-pyrazol-1-yl-methyl- | 2-(trifluoro-methyl)-pyridin-4-yl |
| P276 | 1,2,3,4-tetrazol-1-yl | 5-chloro, 6-fluoro | 4-fluoro-pyrazol-1-yl-methyl- | pyridin-4-yl |
| P279 | 1,2,3,4-tetrazol-1-yl | 5-chloro, 6-fluoro | R*-(cyclopropyl-methyl-) | pyridin-4-yl-1-oxide |
| P280 | 1,2,3,4-tetrazol-1-yl | 5-chloro, 6-fluoro | S*-(cyclopropyl-methyl-) | pyridin-4-yl-1-oxide |
| P281 | 1,2,3,4-tetrazol-1-yl | 5-chloro, 6-fluoro | 4-fluoro-pyrazol-1-yl-methyl- | 2-fluoro-6-amino-pyridin-3-yl |
| P282 | 1,2,3,4-tetrazol-1-yl | 5-chloro, 6-fluoro | 2S*-(amino-carbonyl)-1S*-cyclopropyl-methyl- | pyridin-4-yl-1-oxide |
| P283 | 1,2,3,4-tetrazol-1-yl | 5-chloro, 6-fluoro | 2R*-(amino-carbonyl)-1S*-cyclopropyl-methyl- | pyridin-4-yl-1-oxide |
| P285 | 1,2,3,4-tetrazol-1-yl | 5-chloro, 6-fluoro | pyrazol-1-yl-methyl- | 2-methyl-pyridin-4-yl |
| P286 | 1,2,3,4-tetrazol-1-yl | 5-chloro | pyrazol-1-yl-methyl- | 2-cyclopropyl-pyridin-4-yl |
| P287 | 1,2,3,4-tetrazol-1-yl | 5-chloro, 6-fluoro | 2-(7-carboxy-azaspiro[2.4]heptan-5-yl-carbonyl)-cyclopropyl-methyl- | pyridin-4-yl |
| P291 | 1,2,3,4-tetrazol-1-yl | 5-chloro, 6-fluoro | 4-(piperidin-1-yl-carbonyl)-pyrazol-1-yl-methyl- | pyridin-4-yl |
| P292 | 1,2,3,4-tetrazol-1-yl | 5-chloro, 6-fluoro | 4-(piperidin-1-yl-carbonyl)-pyrazol-1-yl-methyl- | pyridin-4-yl-1-oxide |
| P293 | 1,2,3,4-tetrazol-1-yl | 5-chloro | (isoindolin-2-yl-1-one)-methyl- | pyridin-4-yl |
| P294 | 1,2,3,4-tetrazol-1-yl | 5-chloro, 6-fluoro | cyclopropyl-methyl- | 2-cyano-pyridin-4-yl |
| P295 | 1,2,3,4-tetrazol-1-yl | 5-chloro, 6-fluoro | cyclopropyl-methyl- | 2-(trifluoro-methyl)-pyrimidin-4-yl |
| P296 | 1,2,3,4-tetrazol-1-yl | 5-chloro, 6-fluoro | N-methyl-N-(phenyl-carbonyl)-amino-methyl- | pyridin-4-yl |
| P297 | 1,2,3,4-tetrazol-1-yl | 5-chloro, 6-fluoro | R*-(2-(difluoro-methoxy)-ethyl-) | 2-fluoro-6-amino-pyridin-3-yl |
| P298 | 1,2,3,4-tetrazol-1-yl | 5-chloro, 6-fluoro | S*-(2-(difluoro-methoxy)-ethyl-) | 2-fluoro-6-amino-pyridin-3-yl |
| P299 | 1,2,3,4-tetrazol-1-yl | 5-chloro, 6-fluoro | N-methyl-N-(benzyl-carbonyl)-amino-methyl- | pyridin-4-yl |
| P300 | 1,2,3,4-tetrazol-1-yl | 5-chloro | (t-butoxy-carbonyl)-amino-methyl- | 2-fluoro-pyridin-4-yl |
| P301 | 1,2,3,4-tetrazol-1-yl | 5-chloro | (methoxy-carbonyl)-amino-methyl- | 2-fluoro-pyridin-4-yl |
| P302 | 1,2,3,4-tetrazol-1-yl | 5-chloro, 6-fluoro | N-methyl-N-(methyl-carbonyl)-amino-methyl- | pyridin-4-yl |
| P303 | 1,2,3,4-tetrazol-1-yl | 5-chloro, 6-fluoro | N-methyl-N-(methoxy-carbonyl)-amino-methyl- | pyridin-4-yl |
| P304 | 1,2,3,4-tetrazol-1-yl | 5-chloro | (cyclopropyl-carbonyl)-amino-methyl- | 2-fluoro-pyridin-4-yl |
| P306 | 1,2,3,4-tetrazol-1-yl | 5-chloro, 6-fluoro | S*-(2-(difluoro-methoxy)-ethyl-) | 3-fluoro-pyridin-4-yl-1-oxide |
| P307 | 1,2,3,4-tetrazol-1-yl | 5-chloro, 6-fluoro | 2-(difluoro-methoxy)-ethyl- | 2-methyl-pyridin-4-yl |
| P308 | 1,2,3,4-tetrazol-1-yl | 5-chloro, 6-fluoro | R*-(2-(difluoro-methoxy)-ethyl-) | 3-fluoro-pyridin-4-yl-1-oxide |

TABLE 3-continued

Representative Compounds of Formula (I)

| | | | | |
|---|---|---|---|---|
| P309 | 1,2,3,4-tetrazol-1-yl | 5-chloro, 6-fluoro | pyrazol-1-yl-methyl- | 2-fluoro-pyridin-4-yl |
| P310 | 1,2,3,4-tetrazol-1-yl | 5-chloro, 6-fluoro | pyrazol-1-yl-methyl- | 2-methyl-pyridin-4-yl |
| P311 | 1,2,3,4-tetrazol-1-yl | 5-chloro, 6-fluoro | N-methyl-N-(2-(piperidin-1-yl-carbonyl)-ethoxy))-amino-ethyl- | pyridin-4-yl |
| P312 | 1,2,3,4-tetrazol-1-yl | 5-chloro, 6-fluoro | N-methyl-N-(phenyl-ethyl-carbonyl)-amino-methyl- | pyridin-4-yl |
| P313 | 1,2,3,4-tetrazol-1-yl | 5-chloro, 6-fluoro | cyclopropyl-methyl- | 2-(difluoro-methoxy)-pyridin-4-yl |
| P314 | 1,2,3,4-tetrazol-1-yl | 5-chloro, 6-fluoro | R*-(pyrazol-1-yl-methyl-) | 2-fluoro-6-amino-pyridin-3-yl |
| P315 | 1,2,3,4-tetrazol-1-yl | 5-chloro, 6-fluoro | S*-(pyrazol-1-yl-methyl-) | 2-fluoro-6-amino-pyridin-3-yl |
| P316 | 1,2,3,4-tetrazol-1-yl | 5-chloro, 6-fluoro | 3-(trifluoro-methyl)-pyrazol-1-yl-methyl- | pyridin-4-yl |
| P317 | 1,2,3,4-tetrazol-1-yl | 5-chloro, 6-fluoro | 5-(trifluoro-methyl)-pyrazol-1-yl-methyl- | pyridin-4-yl |
| P318 | 1,2,3,4-tetrazol-1-yl | 5-chloro, 6-fluoro | pyrazol-1-yl-methyl- | 2-(difluoro-methyl)-pyridin-4-yl |
| P319 | 1,2,3,4-tetrazol-1-yl | 5-chloro, 6-fluoro | pyrazol-1-yl-methyl- | pyrimidin-4-yl |
| P320 | 1,2,3,4-tetrazol-1-yl | 5-chloro, 6-fluoro | pyrazol-1-yl-methyl- | pyrimidin-4-yl-1-oxide |
| P321 | 1,2,3,4-tetrazol-1-yl | 5-chloro | 4-(trifluoro-methyl)-pyrazol-1-yl-methyl- | 2-fluoro-pyridin-4-yl |
| P322 | 1,2,3,4-tetrazol-1-yl | 5-chloro, 6-fluoro | N-methyl-N-(piperidin-1-yl-carbonyl-methyl-carbonyl)-amino-methyl- | pyridin-4-yl |
| P323 | 1,2,3,4-tetrazol-1-yl | 5-chloro, 6-fluoro | N-methyl-N-(trifluoro-methoxy)-amino-methyl- | pyridin-4-yl |
| P324 | 1,2,3,4-tetrazol-1-yl | 5-chloro | (pyrrolidin-1yl-2,5-dione)-methyl- | 2-fluoro-pyridin-4-yl |
| P325 | 1,2,3,4-tetrazol-1-yl | 5-chloro, 6-fluoro | 2-(difluoro-methyl-carbonyl)-methyl- | pyrimidin-4-yl-1-oxide |
| P331 | 1,2,3,4-tetrazol-1-yl | 5-chloro, 6-fluoro | 4-(trifluoro-methyl)-pyrazol-1-yl-methyl- | 2-fluoro-pyridin-4-yl |
| P332 | 1,2,3,4-tetrazol-1-yl | 5-chloro, 6-fluoro | 4-fluoro-pyrazol-1-yl-methyl- | 2-(trifluoro-methyl)-pyridin-4-yl |
| P333 | 1,2,3,4-tetrazol-1-yl | 5-chloro, 6-fluoro | 4-fluoro-pyrazol-1-yl-methyl- | 2-(trifluoro-methyl)-pyridin-4-yl |
| P334 | 1,2,3,4-tetrazol-1-yl | 5-chloro, 6-fluoro | S*-(pyrazol-1-yl-methyl-) | 2-(difluoro-methyl)-pyridin-4-yl-1-oxide |
| P335 | 1,2,3,4-tetrazol-1-yl | 5-chloro, 6-fluoro | R*-(2S*-(amino-carbonyl)-1S*-cyclopropyl-methyl-) | 2-fluoro-6-amino-pyridin-3-yl |
| P336 | 1,2,3,4-tetrazol-1-yl | 5-chloro, 6-fluoro | R*-(2S*-(amino-carbonyl)-1R*-cyclopropyl-methyl-) | 2-fluoro-6-amino-pyridin-3-yl |
| P337 | 1,2,3,4-tetrazol-1-yl | 5-chloro, 6-fluoro | S*-(2R*-(amino-carbonyl)-1R*-cyclopropyl-methyl-) | 2-fluoro-6-amino-pyridin-3-yl |
| P338 | 1,2,3,4-tetrazol-1-yl | 5-chloro, 6-fluoro | S*-(2R*-(amino-carbonyl)-1S*-cyclopropyl-methyl-) | 2-fluoro-6-amino-pyridin-3-yl |
| P339 | 1,2,3,4-tetrazol-1-yl | 5-chloro, 6-fluoro | R*-(pyrazol-1-yl-methyl-) | 2-(difluoro-methyl)-pyridin-4-yl-1-oxide |
| P340 | 1,2,3,4-tetrazol-1-yl | 5-chloro, 6-fluoro | S*-(2S*-(amino-carbonyl)-1R*-cyclopropyl-methyl-) | 2-fluoro-6-amino-pyridin-3-yl |
| P341 | 1,2,3,4-tetrazol-1-yl | 5-chloro, 6-fluoro | R*-(2R*-(amino-carbonyl)-1S*-cyclopropyl-methyl-) | 2-fluoro-6-amino-pyridin-3-yl |
| P342 | 1,2,3,4-tetrazol-1-yl | 5-chloro, 6-fluoro | R-(2-(difluoro-methoxy)-ethyl-) | 2-methyl-6-amino-pyridin-3-yl |
| P343 | 1,2,3,4-tetrazol-1-yl | 5-chloro, 6-fluoro | R*-(2-(difluoro-methoxy)-ethyl-) | 2-methyl-6-amino-pyridin-3-yl |
| P344 | 1,2,3,4-tetrazol-1-yl | 5-chloro, 6-fluoro | N-methyl-N-(phenyl-carbonyl)-amino-methyl- | pyridin-4-yl-1-oxide |
| P345 | 1,2,3,4-tetrazol-1-yl | 5-chloro, 6-fluoro | N-methyl-N-(benzyl-carbonyl)-amino-methyl- | pyridin-4-yl-1-oxide |
| P346 | 1,2,3,4-tetrazol-1-yl | 5-chloro, 6-fluoro | 5-(trifluoro-methyl)-pyrazol-1-yl-methyl- | 2-fluoro-pyridin-4-yl |
| P347 | 1,2,3,4-tetrazol-1-yl | 5-chloro | (1-methyl-cycloprop-1-yl-carbonyl)-amino-methyl- | 2-fluoro-pyridin-4-yl |
| P348 | 1,2,3,4-tetrazol-1-yl | 5-chloro, 6-fluoro | pyrazol-1-yl-methyl- | pyridin-4-yl-1-oxide |
| P349 | 1,2,3,4-tetrazol-1-yl | 5-chloro, 6-fluoro | S*-(N-methyl-N-(phenyl-ethyl-carbonyl)-amino-methyl-) | pyridin-4-yl-1-oxide |
| P350 | 1,2,3,4-tetrazol-1-yl | 5-chloro, 6-fluoro | R*-(N-methyl-N-(phenyl-ethyl-carbonyl)-amino-methyl-) | pyridin-4-yl-1-oxide |

TABLE 3-continued

Representative Compounds of Formula (I)

| | | | | |
|---|---|---|---|---|
| P351 | 1,2,3,4-tetrazol-1-yl | 5-chloro, 6-fluoro | N-methyl-N-(methyl-carbonyl)-amino-methyl- | pyridin-4-yl-1-oxide |
| P352 | 1,2,3,4-tetrazol-1-yl | 5-chloro, 6-fluoro | 4-fluoro-pyrazol-1-yl-methyl- | 2-fluoro-pyridin-4-yl |
| P353 | 1,2,3,4-tetrazol-1-yl | 5-chloro, 6-fluoro | R*-(N-methyl-N-(t-butoxy-carbonyl)-amino-methyl-) | 2-fluoro-pyridin-4-yl |
| P354 | 1,2,3,4-tetrazol-1-yl | 5-chloro, 6-fluoro | S*-(N-methyl-N-(t-butoxy-carbonyl)-amino-methyl-) | 2-fluoro-pyridin-4-yl |
| P355 | 1,2,3,4-tetrazol-1-yl | 5-chloro, 6-fluoro | R*-(N-methyl-N-(methoxy-carbonyl)-amino-methyl-) | 2-fluoro-pyridin-4-yl |
| P356 | 1,2,3,4-tetrazol-1-yl | 5-chloro, 6-fluoro | S*-(N-methyl-N-(methoxy-carbonyl)-amino-methyl-) | 2-fluoro-pyridin-4-yl |
| P357 | 1,2,3,4-tetrazol-1-yl | 5-chloro, 6-fluoro | 3-(trifluoro-methyl)-pyrazol-1-yl-methyl- | 2-fluoro-pyridin-4-yl |
| P358 | 1,2,3,4-tetrazol-1-yl | 5-chloro, 6-fluoro | (pyridin-1-yl-2-one)-methyl- | 2-(trifluoro-methyl)-pyridin-4-yl |
| P359 | 1,2,3,4-tetrazol-1-yl | 5-chloro, 6-fluoro | 1-methyl-pyrazol-3-yl-methyl- | 2-cyano-pyridin-4-yl |
| P360 | 1,2,3,4-tetrazol-1-yl | 5-chloro, 6-fluoro | 4-fluoro-pyrazol-1-yl-methyl- | pyridin-4-yl-1-oxide |
| P361 | 1,2,3,4-tetrazol-1-yl | 5-chloro, 6-fluoro | R*-(pyrrolidin-1-yl-2-one-methyl-) | 2-(difluoro-methyl)-pyridin-4-yl-1-oxide |
| P362 | 1,2,3,4-tetrazol-1-yl | 5-chloro, 6-fluoro | S*-(pyrrolidin-1-yl-2-one-methyl-) | 2-(difluoro-methyl)-pyridin-4-yl-1-oxide |
| P363 | 1,2,3,4-tetrazol-1-yl | 5-chloro, 6-fluoro | R*-(pyrrolidin-1-yl-2-one-methyl-) | 2-(trifluoro-methyl)-pyridin-4-yl |
| P364 | 1,2,3,4-tetrazol-1-yl | 5-chloro, 6-fluoro | S*-(pyrrolidin-1-yl-2-one-methyl-) | 2-(trifluoro-methyl)-pyridin-4-yl |
| P365 | 1,2,3,4-tetrazol-1-yl | 5-chloro, 6-fluoro | pyrrolidin-1-yl-2-one-methyl- | 2-(difluoro-methyl)-pyridin-4-yl-1-oxide |
| P366 | 1,2,3,4-tetrazol-1-yl | 5-chloro, 6-fluoro | 2-trifluoro-methoxy-ethyl- | pyrimidin-4-yl |
| P367 | 1,2,3,4-tetrazol-1-yl | 5-chloro, 6-fluoro | 2-(difluoro-methoxy)-ethyl- | pyrimidin-4-yl |
| P368 | 1,2,3,4-tetrazol-1-yl | 5-chloro, 6-fluoro | cyclopropyl-methyl- | 2-methyl-pyrimidin-4-yl |
| P369 | 1,2,3,4-tetrazol-1-yl | 5-chloro, 6-fluoro | cyclopropyl-methyl- | 2-methyl-pyrimidin-4-yl-1-oxide |
| P370 | 1,2,3,4-tetrazol-1-yl | 5-chloro, 6-fluoro | S*-(pyridin-1-yl-2-one)-methyl- | 2-(difluoro-methyl)-pyridin-4-yl-1-oxide |
| P371 | 1,2,3,4-tetrazol-1-yl | 5-chloro, 6-fluoro | S*-(pyridin-1-yl-2-one)-methyl- | 2-(difluoro-methyl)-pyridin-4-yl |
| P372 | 1,2,3,4-tetrazol-1-yl | 5-chloro, 6-fluoro | R*-(pyridin-1-yl-2-one)-methyl- | 2-(difluoro-methyl)-pyridin-4-yl |
| P373 | 1,2,3,4-tetrazol-1-yl | 5-chloro, 6-fluoro | R*-(pyridin-1-yl-2-one)-methyl- | 2-(difluoro-methyl)-pyridin-4-yl-1-oxide |
| P375 | 1,2,3,4-tetrazol-1-yl | 5-chloro, 6-fluoro | R*-(N-methyl-N-(benzyloxy-carbonyl)-amino-methyl-) | 2-(trifluoro-methyl)-pyridin-4-yl |
| P376 | 1,2,3,4-tetrazol-1-yl | 5-chloro, 6-fluoro | S*-(N-methyl-N-(benzyloxy-carbonyl)-amino-methyl-) | 2-(trifluoro-methyl)-pyridin-4-yl |
| P377 | 1,2,3,4-tetrazol-1-yl | 5-chloro, 6-fluoro | R-(1-methyl-pyrazol-3-yl-methyl-) | 2-(trifluoro-methyl)-pyridin-4-yl |
| P378 | 1,2,3,4-tetrazol-1-yl | 5-chloro, 6-fluoro | S*-(1-methyl-pyrazol-3-yl-methyl-) | 2-(trifluoro-methyl)-pyridin-4-yl |
| P379 | 1,2,3,4-tetrazol-1-yl | 5-chloro, 6-fluoro | cyclopropyl-methyl- | 2-(trifluoro-methyl)-pyridin-4-yl-1-oxide |
| P380 | 1,2,3,4-tetrazol-1-yl | 5-chloro, 6-fluoro | cyclopropyl-methyl- | 3-(trifluoro-methyl)-pyridin-4-yl |
| P381 | 1,2,3,4-tetrazol-1-yl | 5-chloro, 6-fluoro | S*-(N-methyl-N-(methoxy-carbonyl)-amino-methyl-) | 2-(trifluoro-methyl)-pyridin-4-yl |
| P382 | 1,2,3,4-tetrazol-1-yl | 5-chloro, 6-fluoro | S*-(pyrrolidin-1-yl-2-one methyl-) | 2-fluoro-pyridin-4-yl |
| P383 | 1,2,3,4-tetrazol-1-yl | 5-chloro, 6-fluoro | R*-(N-methyl-N-(methoxy-carbonyl)-amino-methyl-) | 2-(trifluoro-methyl)-pyridin-4-yl |
| P384 | 1,2,3,4-tetrazol-1-yl | 5-chloro, 6-fluoro | R*-(pyrrolidin-1-yl-2-one methyl-) | 2-fluoro-pyridin-4-yl |
| P385 | 1,2,3,4-tetrazol-1-yl | 5-chloro, 6-fluoro | 2-(difluoro-methoxy)-ethyl- | 3-fluoro-pyridin-4-yl |
| P386 | 1,2,3,4-tetrazol-1-yl | 5-chloro, 6-fluoro | R*-(2-(methoxy-d$_3$)-ethyl-) | 2-(trifluoro-methyl)-pyridin-4-yl |
| P387 | 1,2,3,4-tetrazol-1-yl | 5-chloro, 6-fluoro | S*-(2-(methoxy-d$_3$)-ethyl-) | 2-(trifluoro-methyl)-pyridin-4-yl |
| P388 | 1,2,3,4-tetrazol-1-yl | 5-chloro | 2,4,5,7-tetrahydropyrano[3,4-c]pyrazol-2-yl-methyl- | 2-(trifluoro-methyl)-pyridin-4-yl |
| P391 | 1,2,3,4-tetrazol-1-yl | 5-chloro, 6-fluoro | R*-(N-methyl-N-(methoxy-carbonyl)-amino-methyl-) | 2-(difluoro-methyl)-pyridin-4-yl |

TABLE 3-continued

Representative Compounds of Formula (I)

| P392 | 1,2,3,4-tetrazol-1-yl | 5-chloro, 6-fluoro | S*-(N-methyl-N-(methoxy-carbonyl)-amino-methyl-) | 2-(difluoro-methyl)-pyridin-4-yl-1-oxide |
| --- | --- | --- | --- | --- |
| P393 | 1,2,3,4-tetrazol-1-yl | 5-chloro, 6-fluoro | 4-fluoro-pyrazol-1-yl-methyl- | 2-isopropyl-pyridin-4-yl |
| P394 | 1,2,3,4-tetrazol-1-yl | 5-chloro, 6-fluoro | S*-(N-methyl-N-(methoxy-carbonyl)-amino-methyl-) | 2-(difluoro-methyl)-pyridin-4-yl |
| P395 | 1,2,3,4-tetrazol-1-yl | 5-chloro, 6-fluoro | 4-fluoro-pyrazol-1-yl-methyl- | 2-t-butyl-pyridin-4-yl |
| P396 | 1,2,3,4-tetrazol-1-yl | 5-chloro, 6-fluoro | R*-(N-methyl-N-(methoxy-carbonyl)-amino-methyl-) | 2-(difluoro-methyl)-pyridin-4-yl-1-oxide |
| P397 | 1,2,3,4-tetrazol-1-yl | 5-chloro, 6-fluoro | cyclopropyl-methyl- | pyridazin-4-yl |
| P398 | 1,2,3,4-tetrazol-1-yl | 5-chloro, 6-fluoro | cyclopropyl-methyl- | pyridazin-4-yl-1-oxide |
| P399 | 1,2,3,4-tetrazol-1-yl | 5-chloro, 6-fluoro | R*-(N-methyl-N-(2-(piperidin-1-yl-carbonyl)-ethyl-carbonyl)-amino-methyl-) | 2-(trifluoro-methyl)-pyridin-4-yl |
| P400 | 1,2,3,4-tetrazol-1-yl | 5-chloro, 6-fluoro | S*-(N-methyl-N-(2-(piperidin-1-yl-carbonyl)-ethyl-carbonyl)-amino-methyl-) | 2-(trifluoro-methyl)-pyridin-4-yl |
| P401 | 1,2,3,4-tetrazol-1-yl | 5-chloro, 6-fluoro | R*-(2-(difluoro-methoxy)-ethyl-) | 2-(trifluoro-methyl)-pyrimidin-4-yl |
| P402 | 1,2,3,4-tetrazol-1-yl | 5-chloro, 6-fluoro | S*-(2-(difluoro-methoxy)-ethyl-) | 2-(trifluoro-methyl)-pyrimidin-4-yl |
| P403 | 1,2,3,4-tetrazol-1-yl | 5-chloro, 6-fluoro | R*-(N-methyl-N-(methyl-carbonyl)-amino-methyl-) | 2-(trifluoro-methyl)-pyridin-4-yl |
| P404 | 1,2,3,4-tetrazol-1-yl | 5-chloro, 6-fluoro | S*-(N-methyl-N-(methyl-carbonyl)-amino-methyl-) | 2-(trifluoro-methyl)-pyridin-4-yl |
| P405 | 1,2,3,4-tetrazol-1-yl | 5-chloro, 6-fluoro | R*-(4-fluoro-pyrazol-1-yl-methyl-) | 2-(difluoro-methyl)-pyridin-4-yl-1-oxide |
| P406 | 1,2,3,4-tetrazol-1-yl | 5-chloro, 6-fluoro | S*-(4-fluoro-pyrazol-1-yl-methyl-) | 2-(difluoro-methyl)-pyridin-4-yl-1-oxide |
| P407 | 1,2,3,4-tetrazol-1-yl | 5-chloro, 6-fluoro | N-methyl-N-(tetrahydropyran-4-yl-carbonyl)-amino-methyl- | 2-(trifluoro-methyl)-pyridin-4-yl |
| P408 | 1,2,3,4-tetrazol-1-yl | 5-chloro, 6-fluoro | 1-methyl-pyrazol-4-yl-methyl- | 2-cyano-pyridin-4-yl |
| P409 | 1,2,3,4-tetrazol-1-yl | 5-chloro, 6-fluoro | R*-(N-methyl-N-(phenyl-carbonyl)-amino-methyl-) | 2-(trifluoro-methyl)-pyridin-4-yl |
| P410 | 1,2,3,4-tetrazol-1-yl | 5-chloro, 6-fluoro | S*-(N-methyl-N-(phenyl-carbonyl)-amino-methyl-) | 2-(trifluoro-methyl)-pyridin-4-yl |
| P411 | 1,2,3,4-tetrazol-1-yl | 5-chloro, 6-fluoro | R*-(4-(piperidin-1-yl-carbonyl)-pyrazol-1-yl-methyl-) | 2-(trifluoro-methyl)-pyridin-4-yl |
| P412 | 1,2,3,4-tetrazol-1-yl | 5-chloro, 6-fluoro | S*-(4-(piperidin-1-yl-carbonyl)-pyrazol-1-yl-methyl-) | 2-(trifluoro-methyl)-pyridin-4-yl |
| P413 | 1,2,3,4-tetrazol-1-yl | 5-chloro, 6-fluoro | R*-(4-fluoro-pyrazol-1-yl-methyl-) | 2-isopropyl-pyridin-4-yl-1-oxide |
| P414 | 1,2,3,4-tetrazol-1-yl | 5-chloro, 6-fluoro | S*-(4-fluoro-pyrazol-1-yl-methyl-) | 2-isopropyl-pyridin-4-yl-1-oxide |
| P415 | 1,2,3,4-tetrazol-1-yl | 5-chloro, 6-fluoro | 2-(difluoro-methoxy)-ethyl- | 1-methyl-pyridazin-4-yl-6-one |
| P416 | 1,2,3,4-tetrazol-1-yl | 5-chloro, 6-fluoro | R*-(4-fluoro-pyrazol-1-yl-methyl-) | 2-fluoro-6-amino-pyridin-3-yl |
| P417 | 1,2,3,4-tetrazol-1-yl | 5-chloro, 6-fluoro | S*-(4-fluoro-pyrazol-1-yl-methyl-) | 2-fluoro-6-amino-pyridin-3-yl |
| P418 | 1,2,3,4-tetrazol-1-yl | 5-chloro, 6-fluoro | N-methyl-N-(isopropyl-carbonyl)-amino-methyl- | 2-fluoro-pyridin-4-yl |
| P419 | 1,2,3,4-tetrazol-1-yl | 5-chloro, 6-fluoro | 3-(tetrahydropyran-4-yl)-pyrazol-1-yl-methyl- | 2-(trifluoro-methyl)-pyridin-4-yl |
| P420 | 1,2,3,4-tetrazol-1-yl | 5-chloro, 6-fluoro | R*-(N-methyl-N-(isopropyl-carbonyl)-amino-methyl-) | 2-(trifluoro-methyl)-pyridin-4-yl |
| P421 | 1,2,3,4-tetrazol-1-yl | 5-chloro, 6-fluoro | S*-(N-methyl-N-(isopropyl-carbonyl)-amino-methyl-) | 2-(trifluoro-methyl)-pyridin-4-yl |
| P422 | 1,2,3,4-tetrazol-1-yl | 5-chloro, 6-fluoro | S*-(N-methyl-N-(t-butyl-carbonyl)-amino-methyl-) | 2-(trifluoro-methyl)-pyridin-4-yl |
| P423 | 1,2,3,4-tetrazol-1-yl | 5-chloro, 6-fluoro | R*-(N-methyl-N-(phenyl-carbonyl)-amino-methyl-) | 2-(trifluoro-methyl)-pyridin-4-yl |
| P424 | 1,2,3,4-tetrazol-1-yl | 5-chloro, 6-fluoro | N-methyl-N-(phenyl-carbonyl)-amino-methyl- | 2-fluoro-pyridin-4-yl |
| P425 | 1,2,3,4-tetrazol-1-yl | 5-chloro, 6-fluoro | R*-(N-methyl-N-cyclopropyl-carbonyl)-amino-methyl-) | 2-(trifluoro-methyl)-pyridin-4-yl |
| P426 | 1,2,3,4-tetrazol-1-yl | 5-chloro, 6-fluoro | N-methyl-N-(t-butyl-carbonyl)-amino-methyl- | 2-fluoro-pyridin-4-yl |

TABLE 3-continued

Representative Compounds of Formula (I)

| | | | | |
|---|---|---|---|---|
| P427 | 1,2,3,4-tetrazol-1-yl | 5-chloro, 6-fluoro | N-methyl-N-(methoxy-methyl-carbonyl)-amino-methyl- | 2-(trifluoro-methyl)-pyridin-4-yl |
| P428 | 1,2,3,4-tetrazol-1-yl | 5-chloro, 6-fluoro | S*-(N-methyl-N-(cyclopropyl-carbonyl)-amino-methyl-) | 2-(trifluoro-methyl)-pyridin-4-yl |
| P429 | 1,2,3,4-tetrazol-1-yl | 5-chloro, 6-fluoro | S*-(4-(piperidin-1-yl-carbonyl)-pyrazol-1-yl-methyl-) | 2-fluoro-6-amino-pyridin-3-yl |
| P430 | 1,2,3,4-tetrazol-1-yl | 5-chloro, 6-fluoro | R*-((oxazolidin-3-yl-2-one)-methyl-) | 2-(trifluoro-methyl)-pyridin-4-yl |
| P431 | 1,2,3,4-tetrazol-1-yl | 5-chloro, 6-fluoro | S*-((oxazolidin-3-yl-2-one)-methyl-) | 2-(trifluoro-methyl)-pyridin-4-yl |
| P432 | 1,2,3,4-tetrazol-1-yl | 5-chloro, 6-fluoro | R-((3-methyl-imidazolidin-1-yl-2-one)methyl-) | 2-(trifluoro-methyl)-pyridin-4-yl |
| P433 | 1,2,3,4-tetrazol-1-yl | 5-chloro, 6-fluoro | S*4(3-methyl-imidazolidin-1-yl-2-one)-methyl-) | 2-(trifluoro-methyl)-pyridin-4-yl |
| P434 | 1,2,3,4-tetrazol-1-yl | 5-chloro, 6-fluoro | S*-(N-methyl-N-(1-methyl-pyridin-4-yl-2-one-carbonyl)-amino-methyl-) | 2-(trifluoro-methyl)-pyridin-4-yl |
| P435 | 1,2,3,4-tetrazol-1-yl | 5-chloro, 6-fluoro | R*-(N-methyl-N-(1-methyl-pyridin-4-yl-2-one-carbonyl)-amino-methyl-) | 2-(trifluoro-methyl)-pyridin-4-yl |
| P436 | 1,2,3,4-tetrazol-1-yl | 5-chloro, 6-fluoro | 4-fluoro-pyrazol-1-yl-methyl- | 2-t-butyl-pyridin-4-yl-1-oxide |
| P437 | 1,2,3,4-tetrazol-1-yl | 5-chloro, 6-fluoro | N-methyl-N-(dimethylamino-carbonyl)-amino-methyl- | 2-(trifluoro-methyl)-pyridin-4-yl |
| P438 | 1,2,3,4-tetrazol-1-yl | 5-chloro, 6-fluoro | R*-((oxazolidin-3-yl-2-one)-methyl-) | 2-cyano-pyridin-4-yl |
| P439 | 1,2,3,4-tetrazol-1-yl | 5-chloro, 6-fluoro | S*-((oxazolidin-3-yl-2-one)-methyl-) | 2-cyano-pyridin-4-yl |
| P440 | 1,2,3,4-tetrazol-1-yl | 5-chloro, 6-fluoro | R*-(3-(methoxy-methyl)-pyrazol-1-yl-methyl-) | 2-(trifluoro-methyl)-pyridin-4-yl |
| P441 | 1,2,3,4-tetrazol-1-yl | 5-chloro, 6-fluoro | S*-(3-(methoxy-methyl)-pyrazol-1-yl-methyl-) | 2-(trifluoro-methyl)-pyridin-4-yl |
| P442 | 1,2,3,4-tetrazol-1-yl | 5-chloro, 6-fluoro | 3-carboxy-pyrazol-1-yl-methyl- | pyridin-4-yl |
| P443 | 1,2,3,4-tetrazol-1-yl | 5-chloro, 6-fluoro | 3-(amino-carbonyl)-pyrazol-1-yl-methyl- | pyridin-4-yl |
| P444 | 1,2,3,4-tetrazol-1-yl | 5-chloro, 6-fluoro | 3-(4-carboxy-piperidin-1-yl-carbonyl)-pyrazol-1-yl-methyl- | pyridin-4-yl |
| P447 | 1,2,3,4-tetrazol-1-yl | 5-chloro, 6-fluoro | 3-(piperidin-1-yl-carbonyl)-pyrazol-1-yl-methyl- | pyridin-4-yl-1-oxide |
| P448 | 1,2,3,4-tetrazol-1-yl | 5-chloro, 6-fluoro | R*-(3-(amino-carbonyl)-pyrazol-1-yl-methyl-) | 2-(trifluoro-methyl)-pyridin-4-yl |
| P449 | 1,2,3,4-tetrazol-1-yl | 5-chloro, 6-fluoro | R*-(3-(piperidin-1-yl carbonyl)-pyrazol-1-yl-methyl-) | 2-(trifluoro-methyl)-pyridin-4-yl |
| P450 | 1,2,3,4-tetrazol-1-yl | 5-chloro, 6-fluoro | S*-(3-(piperidin-1-yl carbonyl)-pyrazol-1-yl-methyl-) | 2-(trifluoro-methyl)-pyridin-4-yl |
| P451 | 1,2,3,4-tetrazol-1-yl | 5-chloro, 6-fluoro | R*-(3-(dimethyl-amino-carbonyl)-pyrazol-1-yl-methyl-) | 2-(trifluoro-methyl)-pyridin-4-yl |
| P452 | 1,2,3,4-tetrazol-1-yl | 5-chloro, 6-fluoro | 1-methyl-pyrazol-4-yl-methyl- | 2-(trifluoro-methyl)-pyridin-4-yl |
| P453 | 1,2,3,4-tetrazol-1-yl | 5-chloro, 6-fluoro | S*-(4-fluoro-pyrazol-1-yl methyl-) | 2-cyano-pyridin-4-yl |
| P454 | 1,2,3,4-tetrazol-1-yl | 5-chloro, 6-fluoro | R*-(4-fluoro-pyrazol-1-yl methyl-) | 2-cyano-pyridin-4-yl |
| P458 | 1,2,3,4-tetrazol-1-yl | 5-chloro, 6-fluoro | 2-(difluoro-methoxy)-ethyl- | 2-cyano-pyridin-4-yl |
| P459 | 1,2,3,4-tetrazol-1-yl | 5-chloro, 6-fluoro | (pyridin-1-yl-2-one)-methyl- | 2-cyano-pyridin-4-yl |
| P461 | 1,2,3,4-tetrazol-1-yl | 5-chloro, 6-fluoro | (pyrrolidin-1-yl-2-one)-methyl- | 2-cyano-pyridin-4-yl |
| P462 | 1,2,3,4-tetrazol-1-yl | 5-chloro, 6-fluoro | 2-(difluoro-methoxy)-ethyl- | 2-(trifluoro-methyl)-pyridin-4-yl |
| P463 | 1,2,3,4-tetrazol-1-yl | 5-chloro, 6-fluoro | 2,4,5,7-tetrahydropyrano[3,4-c]pyrazol-2-yl-methyl- | 2-(trifluoro-methyl)-pyridin-4-yl |
| P464 | 1,2,3,4-tetrazol-1-yl | 5-chloro, 6-fluoro | 5-(methoxy-methyl)-pyrazol-1-yl-methyl- | 2-(trifluoro-methyl)-pyridin-4-yl |
| P465 | 1,2,3,4-tetrazol-1-yl | 5-chloro, 6-fluoro | 2,4,5,7-tetrahydropyrano[3,4-c]pyrazol-2-yl-methyl- | 2-(trifluoro-methyl)-pyridin-4-yl |

TABLE 3-continued

Representative Compounds of Formula (I)

| P466 | 1,2,3,4-tetrazol-1-yl | 5-chloro, 6-fluoro | pyrrolidin-1-yl-2-one-methyl- | 2-cyano-pyridin-4-yl-1-oxide |
| P468 | 1,2,3,4-tetrazol-1-yl | 5-chloro, 6-fluoro | 4-fluoro-pyrazol-1-yl-methyl- | 6-(trifluoro-methyl)-pyrimidin-4-yl |
| P469 | 1,2,3,4-tetrazol-1-yl | 5-chloro, 6-fluoro | 4-fluoro-pyrazol-1-yl-methyl- | 2-(trifluoro-methyl)-pyrimidin-4-yl |
| P470 | 1,2,3,4-tetrazol-1-yl | 5-chloro, 6-fluoro | 5-(amino-carbonyl-methyl)-pyrazol-1-yl-methyl- | 2-(trifluoro-methyl)-pyridin-4-yl |
| P471 | 1,2,3,4-tetrazol-1-yl | 5-chloro, 6-fluoro | 4-(piperidin-1-yl-carbonyl-methyl)-pyrazol-1-yl-methyl- | 2-fluoro-6-amino-pyridin-3-yl |
| P472 | 1,2,3,4-tetrazol-1-yl | 5-chloro, 6-fluoro | 4-fluoro-pyrazol-1-yl-methyl- | 2-methyl-pyridin-4-yl-1-oxide |
| P473 | 1,2,3,4-tetrazol-1-yl | 5-chloro, 6-fluoro | 4-(piperidin-1-yl-carbonyl-methyl)-pyrazol-1-yl-methyl- | 2-(trifluoro-methyl)-pyridin-4-yl |
| P474 | 1,2,3,4-tetrazol-1-yl | 5-chloro, 6-fluoro | 4-fluoro-pyrazol-1-yl-methyl- | 2-methyl-pyridin-4-yl |
| P475 | 1,2,3,4-tetrazol-1-yl | 5-chloro, 6-fluoro | 4-(piperidin-1-yl-carbonyl-methyl)-pyrazol-1-yl-methyl- | 2-(trifluoro-methyl)-pyridin-4-yl |
| P477 | 1,2,3,4-tetrazol-1-yl | 5-chloro, 6-fluoro | 4-fluoro-pyrazol-1-yl-methyl- | 2,6-dimethyl-pyridin-4-yl-1-oxide |
| P479 | 4-chloro-1,2,3-triazol-1-yl | 5-chloro, 6-fluoro | 4-fluoro-pyrazol-1-yl-methyl- | 2-(trifluoro-methyl)-pyridin-4-yl |
| P480 | 4-chloro-1,2,3-triazol-1-yl | 5-chloro, 6-fluoro | R*-(4-fluoro-pyrazol-1-yl-methyl-) | 2-(trifluoro-methyl)-pyridin-4-yl |
| P482 | 1,2,3,4-tetrazol-1-yl | 5-chloro, 6-fluoro | N-methyl-N-(methoxy-carbonyl)-amino-methyl- | 2-fluoro-6-amino-pyridin-3-yl |
| P483 | 1,2,3,4-tetrazol-1-yl | 5-chloro, 6-fluoro | 4-(amino-carbonyl)-pyrazol-1-yl-methyl- | 2-(trifluoro-methyl)-pyridin-4-yl |
| P485 | 4-cyclopropyl-1,2,3-triazol-1-yl | 5-chloro, 6-fluoro | 4-fluoro-pyrazol-1-yl-methyl- | 2-(trifluoro-methyl)-pyridin-4-yl |
| P486 | 1,2,3,4-tetrazol-1-yl | 5-chloro, 6-fluoro | 3-(amino-carbonyl-methyl)-pyrazol-1-yl-methyl- | 2-(trifluoro-methyl)-pyridin-4-yl |
| P489 | 1,2,3,4-tetrazol-1-yl | 5-chloro, 6-fluoro | 5-(methoxy-methyl)-pyrazol-1-yl-methyl- | 2-fluoro-6-amino-pyridin-3-yl |
| P492 | 1,2,3,4-tetrazol-1-yl | 5-chloro, 6-fluoro | 3-(methoxy-methyl)-pyrazol-1-yl-methyl- | 2-fluoro-6-amino-pyridin-3-yl |
| P500 | 1,2,3,4-tetrazol-1-yl | 5-chloro, 6-fluoro | 4-fluoro-pyrazol-1-yl-methyl- | 2-cyclopropyl-pyridin-4-yl |
| P513 | 1,2,3,4-tetrazol-1-yl | 5-chloro, 6-fluoro | R*-(pyrazol-1-yl-methyl-) | 2-(trifluoro-methyl)-pyridin-4-yl |
| P514 | 1,2,3,4-tetrazol-1-yl | 5-chloro, 6-fluoro | S*-(pyrazol-1-yl-methyl-) | 2-(trifluoro-methyl)-pyridin-4-yl |
| P515 | 1,2,3,4-tetrazol-1-yl | 5-chloro, 6-fluoro | R*-(4-pyridin-2-yl)-pyrazol 1-yl-methyl-) | pyridin-2-yl |
| P516 | 1,2,3,4-tetrazol-1-yl | 5-chloro, 6-fluoro | S*-(4-pyridin-2-yl)-pyrazol 1-yl-methyl-) | pyridin-2-yl |
| P517 | 1,2,3,4-tetrazol-1-yl | 5-chloro, 6-fluoro | cyclopropyl-methyl- | 3-fluoro-5-chloro-pyridin-4-yl |
| P518 | 1,2,3,4-tetrazol-1-yl | 5-chloro, 6-fluoro | cyclopropyl-methyl- | 3-fluoro-5-chloro-pyridin-4-yl-1-oxide |
| P522 | 1,2,3,4-tetrazol-1-yl | 5-chloro, 6-fluoro | R*-((5-fluoro-pyridin-1-yl)-pyrazol-1-yl-methyl-) | 2-(trifluoro-methyl)-pyridin-4-yl |
| P523 | 1,2,3,4-tetrazol-1-yl | 5-chloro, 6-fluoro | S*-((5-fluoro-pyridin-1-yl)-pyrazol-1-yl-methyl-) | 2-(trifluoro-methyl)-pyridin-4-yl |
| P533 | 1,2,3,4-tetrazol-1-yl | 5-chloro, 6-fluoro | R-(3-(difluoro-methoxy)-pyrazol-1-yl-methyl-) | 2-(trifluoro-methyl)-pyridin-4-yl |
| P534 | 1,2,3,4-tetrazol-1-yl | 5-chloro, 6-fluoro | S-(3-(difluoro-methoxy)-pyrazol-1-yl)-methyl-) | 2-(trifluoro-methyl)-pyridin-4-yl |
| P551 | 1,2,3,4-tetrazol-1-yl | 5-chloro, 6-fluoro | S-(2-(difluoro-methoxy)-ethyl-) | 2-(methyl-amino)-pyrimidin-5-yl |
| P552 | 1,2,3,4-tetrazol-1-yl | 5-chloro, 6-fluoro | R-(2-(difluoro-methoxy)-ethyl-) | 2-(methyl-amino)-pyrimidin-5-yl |
| P570 | 1,2,3,4-tetrazol-1-yl | 5-chloro, 6-fluoro | S*-(3-(difluoro-methoxy-methyl)-4-fluoro-pyrazol-1-yl-methyl-) | 2-(trifluoro-methyl)-pyridin-4-yl |
| P571 | 1,2,3,4-tetrazol-1-yl | 5-chloro, 6-fluoro | R*-(3-(difluoro-methoxy-methyl)-4-fluoro-pyrazol-1-yl-methyl-) | 2-(trifluoro-methyl)-pyridin-4-yl |
| P581 | 1,2,3,4-tetrazol-1-yl | 5-chloro, 6-fluoro | S-(2-(difluoro-methoxy)-ethyl-) | 3-fluoro-5-chloro-pyridin-4-yl |
| P583 | 1,2,3,4-tetrazol-1-yl | 5-chloro, 6-fluoro | R-(2-(difluoro-methoxy)-ethyl-) | 3-fluoro-5-chloro-pyridin-4-yl |
| P651 | 1,2,3,4-tetrazol-1-yl | 5-chloro, 6-fluoro | S-(1-isopropyl-pyrazol-3-yl-methyl-) | 2-(trifluoro-methyl)-pyridin-4-yl |
| P652 | 1,2,3,4-tetrazol-1-yl | 5-chloro, 6-fluoro | R-(1-isopropyl-pyrazol-3-yl-methyl-) | 2-(trifluoro-methyl)-pyridin-4-yl |
| P694 | 1,2,3,4-tetrazol-1-yl | 5-chloro, 6-fluoro | 1-methyl-1,2,5-triazol-3-yl-methyl- | 2-(trifluoro-methyl)-pyridin-4-yl |

TABLE 3-continued

Representative Compounds of Formula (I)

| | | | | |
|---|---|---|---|---|
| P695 | 1,2,3,4-tetrazol-1-yl | 5-chloro, 6-fluoro | 1-methyl-1,2,3-triazol-4-yl-methyl- | 2-(trifluoro-methyl)-pyridin-4-yl |
| P698 | 1,2,3,4-tetrazol-1-yl | 5-chloro, 6-fluoro | 1-phenyl-1,2,5-triazol-3-yl-methyl- | 2-(trifluoro-methyl)-pyridin-4-yl |
| P703 | 1,2,3,4-tetrazol-1-yl | 5-chloro, 6-fluoro | 1-(difluoro-methyl)-pyrazol-3-yl-methyl- | 2-(trifluoro-methyl)-pyridin-4-yl |
| P704 | 1,2,3,4-tetrazol-1-yl | 5-chloro, 6-fluoro | R-(1-methyl-1,2,5-triazol-3-yl-methyl-) | 2-(trifluoro-methyl)-pyridin-4-yl |
| P707 | 1,2,3,4-tetrazol-1-yl | 5-chloro, 6-fluoro | S-(1-methyl-1,2,5-triazol-3-yl-methyl-) | 2-(trifluoro-methyl)-pyridin-4-yl |
| P710 | 1,2,3,4-tetrazol-1-yl | 5-chloro, 6-fluoro | S-(1-(2,2,2-trifluoroethyl)-pyrazol-1-yl-methyl-) | 2-(trifluoro-methyl)-pyridin-4-yl |
| P711 | 1,2,3,4-tetrazol-1-yl | 5-chloro, 6-fluoro | R-(1-(2,2,2-trifluoroethyl)-pyrazol-1-yl-methyl-) | 2-(trifluoro-methyl)-pyridin-4-yl |
| P712 | 4-chloro-1,2,3-triazol-1-yl | 5-chloro, 6-fluoro | R-(1-methyl-1,2,5-triazol-3-yl-methyl-) | 2-(trifluoro-methyl)-pyridin-4-yl |
| P715 | 4-chloro-1,2,3-triazol-1-yl | 5-chloro, 6-fluoro | S-(1-methyl-1,2,5-triazol-3-yl-methyl-) | 2-(trifluoro-methyl)-pyridin-4-yl |
| P736 | 1,2,3,4-tetrazol-1-yl | 5-chloro, 6-fluoro | R-(1-methyl-1,2,3-triazol-4-yl-methyl) | 2-(trifluoro-methyl)-pyridin-4-yl |
| P737 | 1,2,3,4-tetrazol-1-yl | 5-chloro, 6-fluoro | S-(1-methyl-1,2,3-triazol-4-yl-methyl) | 2-(trifluoro-methyl)-pyridin-4-yl |
| P738 | 4-chloro-1,2,3-triazol-1-yl | 5-chloro, 6-fluoro | S-(1-methyl-1,2,3-triazol-4-yl-methyl) | 2-(trifluoro-methyl)-pyridin-4-yl |
| P739 | 4-chloro-1,2,3-triazol-1-yl | 5-chloro, 6-fluoro | R-(1-methyl-1,2,3-triazol-4-yl-methyl) | 2-(trifluoro-methyl)-pyridin-4-yl |
| P740 | 1,2,3,4-tetrazol-1-yl | 5-chloro, 6-fluoro | S-(1-(difluoro-methyl)-1,2,5-triazol-3-yl-methyl-) | 2-(trifluoro-methyl)-pyridin-4-yl |
| P741 | 1,2,3,4-tetrazol-1-yl | 5-chloro, 6-fluoro | 1-(2,2,2-trifluoroethyl)-4-fluoro-pyrazol-3-yl-methyl- | 2-(trifluoro-methyl)-pyridin-4-yl |
| P742 | 1,2,3,4-tetrazol-1-yl | 5-chloro, 6-fluoro | R-(1-(difluoro-methy-1,2,5-triazol-3-yl-methyl-) | 2-(trifluoro-methyl)-pyridin-4-yl |
| P746 | 1,2,3,4-tetrazol-1-yl | 5-chloro, 6-fluoro | S-(1-(difluoro-methyl)-1,2,3-triazol-4-yl-methyl-) | 2-(trifluoro-methyl)-pyridin-4-yl |
| P748 | 1,2,3,4-tetrazol-1-yl | 5-chloro, 6-fluoro | R-(1-(difluoro-methyl)-1,2,3-triazol-4-yl-methyl-) | 2-(trifluoro-methyl)-pyridin-4-yl |
| P775 | 1,2,3,4-tetrazol-1-yl | 5-chloro, 6-fluoro | S-(1-(difluoro-methyl)-pyrazol-1-yl-methyl-) | 2-(trifluoro-methyl)-pyridin-4-yl |
| P776 | 1,2,3,4-tetrazol-1-yl | 5-chloro, 6-fluoro | R-(1-(difluoro-methyl)-pyrazol-1-yl-methyl-) | 2-(trifluoro-methyl)-pyridin-4-yl |
| P833 | 4-(trifluoro-methyl)-1,2,3-triazol-1-yl | 5-chloro, 6-fluoro | S*-(2-(difluoro-methoxy)-ethyl-) | 2-fluoro-6-amino-pyrazin-3-yl |
| P841 | 1,2,3,4-tetrazol-1-yl | 5-chloro, 6-fluoro | S*-(cyclopropyl-methyl-) | 2-(trifluoro-methyl)-5-(methyl-carbonyl-amino)-pyridin-4-yl |
| P842 | 1,2,3,4-tetrazol-1-yl | 5-chloro, 6-fluoro | R*-(cyclopropyl-methyl-) | 2-(trifluoro-methyl)-5-(methyl-carbonyl-amino)-pyridin-4-yl |
| P861 | 1,2,3,4-tetrazol-1-yl | 5-chloro, 6-fluoro | cyclopropyl-methyl- | 3-chloro-5-fluoro-pyridin-4-yl-1-oxide |
| P862 | 1,2,3,4-tetrazol-1-yl | 5-chloro, 6-fluoro | S*-(cyclopropyl-methyl-) | 3-chloro-5-fluoro-pyridin-4-yl-1-oxide |
| P865 | 4-(trifluoro-methyl)-1,2,3-triazol-1-yl | 5-chloro, 6-fluoro | S*-(2-(difluoro-methoxy)-ethyl-2,2-d$_2$-) | 3-fluoro-pyridin-4-yl-1-oxide |
| P866 | 4-(trifluoro-methyl)-1,2,3-triazol-1-yl | 5-chloro, 6-fluoro | R*-(2-(difluoro-methoxy)-ethyl-2,2-d$_2$-) | 3-fluoro-pyridin-4-yl-1-oxide |

(I-PB)

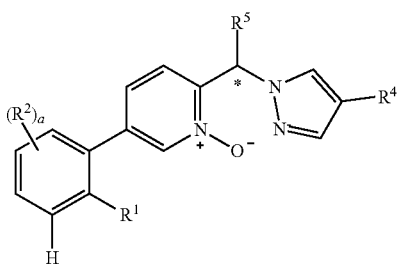

| ID No. | $R^1$ | $(R^2)_a$ | $R^5$ | $R^4$ |
|---|---|---|---|---|
| P12 | 1,2,3,4-tetrazol-1-yl | 5-chloro | cyclopropyl-methyl- | 2-methyl-isoindolin-5-yl-1-one |
| P15 | 1,2,3,4-tetrazol-1-yl | 5-chloro | cyclopropyl-methyl- | 2-methyl-3,4-dihydroisoquinolin-6-yl-1-one |

TABLE 3-continued

Representative Compounds of Formula (1)

| | | | | |
|---|---|---|---|---|
| P16 | 1,2,3,4-tetrazol-1-yl | 5-chloro | cyclopropyl-methyl- | isobenzofuran-5-yl-1-one |
| P265 | 1,2,3,4-tetrazol-1-yl | 5-chloro, 6-fluoro | cyclopropyl-methyl- | 1-methyl-1H-indazol-5-yl |
| P271 | 1,2,3,4-tetrazol-1-yl | 5-chloro, 6-fluoro | cyclopropyl-methyl- | 2,3-dihydro-benzo[b][1,4]dioxin-6-yl |
| P284 | 1,2,3,4-tetrazol-1-yl | 5-chloro, 6-fluoro | cyclopropyl-methyl- | 2,2-difluoro-benzo[d][1,3]dioxo1-5-yl |
| P326 | 1,2,3,4-tetrazol-1-yl | 5-chloro, 6-fluoro | cyclopropyl-methyl- | 2-methyl-indazol-5-yl |
| P885 | 4-(trifluoro-methyl)-1,2,3-triazol-1-yl | 5-chloro, 6-fluoro | 2-(difluoro-methoxy)-ethyl- | isoindo1-4-yl-2-one |

TABLE 4

Representative Compounds of Formula (I)

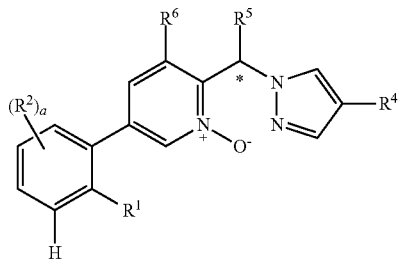

(I-PX)

| ID No. | R¹ | (R²)ₐ | R⁵ | R⁴ | R⁶ |
|---|---|---|---|---|---|
| P11 | 1,2,3,4-tetrazol-1-yl | 5-chloro | cyclopropyl-methyl- | 3-carboxy-phenyl | fluoro |
| P30 | 1,2,3,4-tetrazol-1-yl | 5-chloro, 6-fluoro | cyclopropyl-methyl- | 4-(methoxy-carbonyl-amino)-phenyl | fluoro |

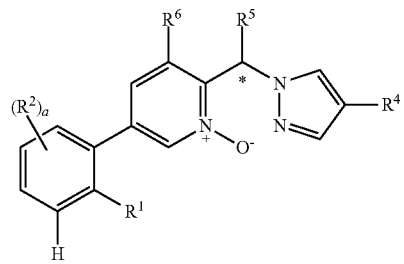

(I-PZ)

| ID No. | R¹ | (R²)ₐ | R⁵ | R⁴ | R⁶ |
|---|---|---|---|---|---|
| P59 | 1,2,3,4-tetrazol-1-yl | 5-chloro | phenyl-methyl- | 2-fluoro-6-amino-pyridin | fluoro |

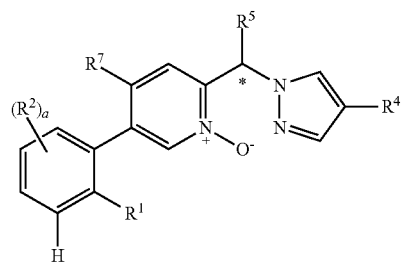

(I-PX)

| ID No. | R¹ | (R²)ₐ | R⁵ | R⁴ | R⁷ |
|---|---|---|---|---|---|
| P63 | 1,2,3,4-tetrazol-1-yl | 5-chloro, 6-fluoromethyl- | cyclopropyl-methoxy | 2-fluoro-6-(methyl-carbonyl-amino)-phenyl | methoxy |
| P93 | 1,2,3,4-tetrazol-1-yl | 5-chloro, 6-fluoro | cyclopropyl-methyl- | 4-(methoxy-carbonyl-amino)-phenyl | methoxy |
| P877 | 4-(trifluoro-methyl)-1,2,3-triazol-1-yl | 5-chloro | R*-ethyl | 3-fluoro-4-(amino-carbonyl)-phenyl | methoxy |
| P878 | 4-(trifluoro-methyl)-1,2,3-triazol-1-yl | 5-chloro | S*-ethyl | 3-fluoro-4-(amino-carbonyl)-phenyl | methoxy |

TABLE 4-continued

Representative Compounds of Formula (I)

(I-PY)

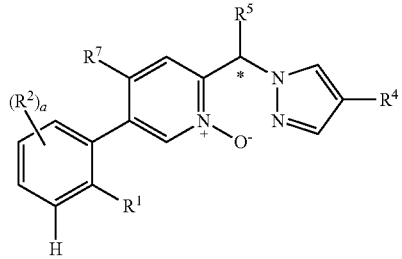

| ID No. | R¹ | (R²)ₐ | R⁵ | R⁴ | R⁷ |
|---|---|---|---|---|---|
| P490 | 1,2,3,4-tetrazol-1-yl | 5-chloro, 6-fluoro | S-(cyclopropyl-methyl-) | 1-methyl-pyrazol-5-yl | methoxy |
| P491 | 1,2,3,4-tetrazol-1-yl | 5-chloro, 6-fluoro | R-(cyclopropyl-methyl-) | 1-methyl-pyrazol-5-yl | methoxy |
| P512 | 1,2,3,4-tetrazol-1-yl | 5-chloro, 6-fluoro | R*-(cyclopropyl-methyl-) | 1-methyl-1,2, 3-triazol-5-yl | chloro |
| P916 | 1,2,3, 4-tetrazol-1-yl | 5-chloro | R*-(cyclopropyl-methyl-) | 1-(difluoro-methyl)-1,2,4-triazol-5-yl | methoxy |
| P917 | 1,2,3, 4-tetrazol-1-yl | 5-chloro | S*-(cyclopropyl-methyl-) | 1-(difluoro-methyl)-1,2,4-triazol-5-yl | methoxy |
| P918 | 4-(trifluoro-methyl)-1,2,3-triazol-1-yl | 5-chloro | R*-(cyclopropyl-methyl-) | 1-methyl-1,2,4-triazol-5-yl | methoxy |
| P919 | 4-(trifluoro-methyl)-1,2,3-triazol-1-yl | 5-chloro | S*-(cyclopropyl-methyl-) | 1-methyl-1,2,4-triazol-5-yl | methoxy |
| P921 | 4-(trifluoro-methyl)-1,2,3- triazol-1-yl | 5-chloro | R*-ethyl | 1-methyl-1,2,4-triazol-5yl- | methoxy |
| P922 | 4-(trifluoro-methyl)-1,2,3- triazol-1-yl | 5-chloro | S*-ethyl | 1-methyl-1,2,4-triazol-5-yl | methoxy |
| P923 | 4-(trifluoro-methyl)-1,2,3-triazol-1-yl | 5-chloro | R*-ethyl | 1-(difluoro-methyl)-1,2,4-triazol-5-yl | methoxy |
| P924 | 4-(trifluoro-methyl)-1,2,3-triazol-1-yl | 5-chloro | S*-ethyl | 1-(difluoro-methyl)-1,2,4-triazol-5-yl | methoxy |
| P939 | 4-(trifluoro-methyl)-1,2,3-triazol-1-yl | 5-chloro | R*-(cyclopropyl-methyl-) | 1-(difluoro-methyl)-1,2,4-triazol-5-yl | methoxy |
| P940 | 4-(trifluoro-methyl)-1,2,3-triazol-1-yl | 5-chloro | S*-(cyclopropyl-methyl-) | 1-(difluoro-methyl)-1,2,4-triazol-5-yl | methoxy |
| P944 | 4-(trifluoro-methyl)-1,2,3-triazol-1-yl | 5-chloro | R*-(cyclopropyl-methyl-) | 1-methyl-1,2,4-triazol-5-yl | ethoxy |
| P945 | 4-(trifluoro-methyl)-1,2,3-triazol-1-yl | 5-chloro | S*-(cyclopropyl-methyl-) | 1-methyl-1,2,4-triazol-5-yl | ethoxy |
| P958 | 4-(trifluoro-methyl)-1,2,3-triazol-1-yl | 5-chloro | R*-(cyclopropyl-methyl-) | 3-methyl-5-(amino-carbonyl)-thien-2-yl | methoxy |
| P959 | 4-(trifluoro-methyl)-1,2,3-triazol-1-yl | 5-chloro | S*-(cyclopropyl-methyl-) | 3-methyl-5-(amino-carbonyl)-thien-2-yl | methoxy |

(I-PZ)

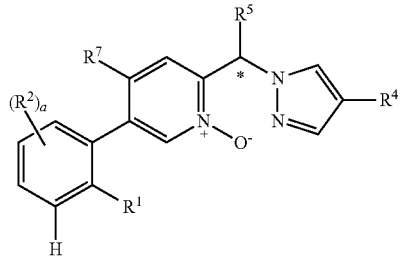

| ID No. | R¹ | (R²)ₐ | R⁵ | R⁴ | R⁷ |
|---|---|---|---|---|---|
| P66 | 1,2,3,4-tetrazol-1-yl | 5-chloro, 6-fluoro | cyclopropyl-methyl- | 1-methyl-pyridazin-4-yl-6-one | methoxy |
| P85 | 1,2,3,4-tetrazol-1-yl | 5-chloro, 6-fluoro | cyclopropyl-methyl- | 2-fluoro-6-amino-pyridin-3-yl | methoxy |
| P130 | 1,2,3,4-tetrazol-1-yl | 5-chloro, 6-fluoro | cyclopropyl-methyl- | 1-methyl-pyridazin-4-yl-6-one | methyl |
| P133 | 1,2,3,4-tetrazol-1-yl | 5-chloro, 6-fluoro | cyclopropyl-methyl- | 1-methyl-pyridazin-4-yl-6-one | methyl |
| P137 | 1,2,3,4-tetrazol-1-yl | 5-chloro, 6-fluoro | cyclopropyl-methyl- | 1-methyl-pyridazin-4-yl-6-one | ethoxy |
| P139 | 1,2,3,4-tetrazol-1-yl | 5-chloro, 6-fluoro | cyclopropyl-methyl- | 1-methyl-pyridazin-4-yl-6-one | chloro |
| P145 | 1,2,3,4-tetrazol-1-yl | 5-chloro, 6-fluoro | cyclopropyl-methyl- | 1-methyl-pyridazin-4-yl-6-one | chloro |
| P146 | 1,2,3,4-tetrazol-1-yl | 5-chloro, 6-fluoro | cyclopropyl-methyl- | 1-methyl-pyridazin-4-yl-6-one | iso-propyl-oxy |
| P149 | 1,2,3,4-tetrazol-1-yl | 5-chloro, 6-fluoro | cyclopropyl-methyl- | 1-methyl-pyridazin-4-yl-6-one | iso-propyl-oxy |
| P161 | 1,2,3,4-tetrazol-1-yl | 5-chloro, 6-fluoro | cyclopropyl-methyl- | 1-isopropyl-pyridazin-4-yl-6-one | methoxy |
| P165 | 1,2,3,4-tetrazol-1-yl | 5-chloro, 6-fluoro | cyclopropyl-methyl- | 1-methyl-pyridazin-4-yl-2-one | methoxy |
| P170 | 1,2,3,4-tetrazol-1-yl | 5-chloro, 6-fluoro | cyclopropyl-methyl- | 1-ethyl-pyridazin-4-yl-6-one | methoxy |
| P182 | oxazol-5-yl | 5-chloro, 6-fluoro | cyclopropyl-methyl- | 2-fluoro-6-amino-pyridin-3-yl | methoxy |
| P189 | 1,2,3,4-tetrazol-1-yl | 5-chloro, 6-fluoro | R*-(cyclopropyl-methyl-) | 1-methyl-pyridazin-4-yl-6-one | chloro |
| P190 | 1,2,3,4-tetrazol-1-yl | 5-chloro, 6-fluoro | S*-(cyclopropyl-methyl-) | 1-methyl-pyridazin-4-yl-6-one | chloro |
| P205 | oxazol-5-yl | 5-chloro, 6-fluoro | cyclopropyl-methyl- | 1-methyl-pyridazin-4-yl-6-one | methoxy |
| P247 | 1,2,3,4-tetrazol-1-yl | 5-chloro, 6-fluoro | 2-(amino-carbonyl)-cyclopropyl-methyl- | 2-methyl-6-amino-pyridin-3-yl | methoxy |
| P248 | 1,2,3,4-tetrazol-1-yl | 5-chloro, 6-fluoro | 2-(piperidin-1-yl-carbonyl)-cyclopropyl-methyl- | 2-methyl-6-amino-pyridin-3-yl | methoxy |
| P251 | 1,2,3,4-tetrazol-1-yl | 5-chloro, 6-fluoro | cyclopropyl-methyl- | pyridin-4-yl | ethoxy |

TABLE 5

Representative Compounds of Formula (I-PZ)

| ID No. | R¹ | (R²)ₐ | R⁵ | R⁴ |
|---|---|---|---|---|
| P374 | 1,2,3,4-tetrazol-1-yl | 5-chloro,6-fluoro | cyclopropyl-methyl- | 2-(trifluoro-methyl)-pyridin-4-yl |

In another embodiment, the present invention is directed to a compound of formula (H)

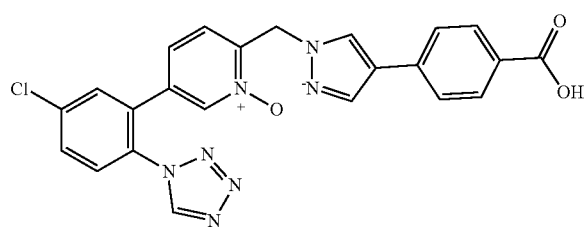

also known as 4-[1-[[5-[5-chloro-2-(tetrazol-1-yl)phenyl]-1-oxido-pyridin-1-ium-2-yl]methyl]pyrazol-4-yl]benzoic acid, and stereoisomers, isotopologues, isotopomers, pharmaceutically acceptable salts and solvates thereof.

In certain embodiments, the present invention is directed to a compound independently selected from the group consisting of
methyl N-[4-[1-[(1R)-1-[5-[3-chloro-2-fluoro-6-(tetrazol-1-yl)phenyl]-1-oxido-pyridin-1-ium-2-yl]-2-cyclopropyl-ethyl]pyrazol-4-yl]phenyl]carbamate;
methyl N-[4-[1-[(1R)-1-[5-[3-chloro-2-fluoro-6-(tetrazol-1-yl)phenyl]-1-oxido-pyridin-1-ium-2-yl]-3-methoxy-propyl]pyrazol-4-yl]phenyl]carbamate;
methyl N-[4-[1-[(1R)-1-[5-[3-chloro-2-fluoro-6-(tetrazol-1-yl)phenyl]-1-oxido-pyridin-1-ium-2-yl]-3-(difluoromethoxy)propyl]pyrazol-4-yl]phenyl]carbamate;
5-[3-chloro-2-fluoro-6-(tetrazol-1-yl)phenyl]-2-[(1R)-3-(difluoromethoxy)-1-[4-(3-methyltriazol-4-yl)pyrazol-1-yl]propyl]-1-oxido-pyridin-1-ium;
5-[3-chloro-6-(4-chlorotriazol-1-yl)-2-fluoro-phenyl]-2-[(1R)-3-(difluoromethoxy)-1-[4-(3-methyltriazol-4-yl)pyrazol-1-yl]propyl]-1-oxido-pyridin-1-ium;
5-[3-chloro-2-fluoro-6-(tetrazol-1-yl)phenyl]-2-[(1R)-3-(difluoromethoxy)-1-[4-[3-(difluoromethyl)triazol-4-yl]pyrazol-1-yl]propyl]-1-oxido-pyridin-1-ium;
5-[3-chloro-6-(4-chlorotriazol-1-yl)-2-fluoro-phenyl]-2-[(1R)-3-(difluoromethoxy)-1-[4-(5-fluoro-3-methyl-triazol-4-yl)pyrazol-1-yl]propyl]-1-oxido-pyridin-1-ium;
5-[3-chloro-6-(4-chlorotriazol-1-yl)-2-fluoro-phenyl]-2-[(1R)-3-(difluoromethoxy)-1-[4-[2-(difluoromethyl)-1,2,4-triazol-3-yl]pyrazol-1-yl]propyl]-1-oxido-pyridin-1-ium;
5-[3-chloro-6-(4-chlorotriazol-1-yl)-2-fluoro-phenyl]-2-[(1R)-3-(difluoromethoxy)-1-[4-(2-methyl-1,2,4-triazol-3-yl)pyrazol-1-yl]propyl]-1-oxido-pyridin-1-ium;
5-[3-chloro-2-fluoro-6-(tetrazol-1-yl)phenyl]-2-[(1R)-2-cyclopropyl-1-[4-(5-fluoro-3-methyl-triazol-4-yl)pyrazol-1-yl]ethyl]-1-oxido-pyridin-1-ium;
5-[3-chloro-2-fluoro-6-[4-(trifluoromethyl)triazol-1-yl]phenyl]-2-[(1R)-3-(difluoromethoxy)-1-[4-(2-methyl-1,2,4-triazol-3-yl)pyrazol-1-yl]propyl]-1-oxido-pyridin-1-ium;
5-[3-chloro-6-(4-chlorotriazol-1-yl)-2-fluoro-phenyl]-2-[(1R)-2-[1-(difluoromethyl)pyrazol-3-yl]-1-[4-(2-methyl-1,2,4-triazol-3-yl)pyrazol-1-yl]ethyl]-1-oxido-pyridin-1-ium;
5-[3-chloro-6-(4-chlorotriazol-1-yl)-2-fluoro-phenyl]-2-[(1R)-2-[1-(difluoromethyl)pyrazol-3-yl]-1-[4-(5-fluoro-3-methyl-triazol-4-yl)pyrazol-1-yl]ethyl]-1-oxido-pyridin-1-ium;
4-[1-[(1R)-1-[5-[3-chloro-2-fluoro-6-[4-(trifluoromethyl)triazol-1-yl]phenyl]-1-oxido-pyridin-1-ium-2-yl]-3-(difluoromethoxy)propyl]pyrazol-4-yl]-2-fluoro-benzamide;
(R*)-4-[1-[1-[5-[3-chloro-6-(4-chlorotriazol-1-yl)-2-fluoro-phenyl]-1-oxido-pyridin-1-ium-2-yl]-3-(difluoromethoxy)propyl]pyrazol-4-yl]-2-fluoro-benzamide;
4-[1-[(1R)-1-[5-[3-chloro-2-fluoro-6-[4-(trifluoromethyl)triazol-1-yl]phenyl]-1-oxido-pyridin-1-ium-2-yl]-2-[1-(difluoromethyl)pyrazol-3-yl]ethyl]pyrazol-4-yl]-2-fluoro-benzamide;
4-[1-[(1R)-1-[5-[3-chloro-6-(4-chlorotriazol-1-yl)-2-fluoro-phenyl]-1-oxido-pyridin-1-ium-2-yl]-2-[1-(difluoromethyl)pyrazol-3-yl]ethyl]pyrazol-4-yl]-2-fluoro-benzamide;
and stereoisomers, tautomers, isotopomers, isotopologues and pharmaceutically acceptable salts thereof.

In certain embodiments, the present invention is directed to a compound independently selected from the group consisting of
5-[3-chloro-6-(4-chlorotriazol-1-yl)-2-fluoro-phenyl]-2-[(1R)-3-(difluoromethoxy)-1-[4-(3-methyltriazol-4-yl)pyrazol-1-yl]propyl]-1-oxido-pyridin-1-ium;
5-[3-chloro-6-(4-chlorotriazol-1-yl)-2-fluoro-phenyl]-2-[(1R)-3-(difluoromethoxy)-1-[4-(2-methyl-1,2,4-triazol-3-yl)pyrazol-1-yl]propyl]-1-oxido-pyridin-1-ium;
5-[3-chloro-2-fluoro-6-[4-(trifluoromethyl)triazol-1-yl]phenyl]-2-[(1R)-3-(difluoromethoxy)-1-[4-(2-methyl-1,2,4-triazol-3-yl)pyrazol-1-yl]propyl]-1-oxido-pyridin-1-ium;
4-[1-[(1R)-1-[5-[3-chloro-2-fluoro-6-[4-(trifluoromethyl)triazol-1-yl]phenyl]-1-oxido-pyridin-1-ium-2-yl]-2-[1-(difluoromethyl)pyrazol-3-yl]ethyl]pyrazol-4-yl]-2-fluoro-benzamide;
4-[1-[(1R)-1-[5-[3-chloro-6-(4-chlorotriazol-1-yl)-2-fluoro-phenyl]-1-oxido-pyridin-1-ium-2-yl]-2-[1-(difluoromethyl)pyrazol-3-yl]ethyl]pyrazol-4-yl]-2-fluoro-benzamide;
and pharmaceutically acceptable salts thereof.

In certain embodiments, the present invention is directed to a compound independently selected from the group consisting of
methyl N-[4-[1-[(1R)-1-[5-[3-chloro-2-fluoro-6-(tetrazol-1-yl)phenyl]-1-oxido-pyridin-1-ium-2-yl]-2-cyclopropyl-ethyl]pyrazol-4-yl]phenyl]carbamate;
methyl N-[4-[1-[(1R)-1-[5-[3-chloro-2-fluoro-6-(tetrazol-1-yl)phenyl]-1-oxido-pyridin-1-ium-2-yl]-3-methoxy-propyl]pyrazol-4-yl]phenyl]carbamate;
methyl N-[4-[1-[(1R)-1-[5-[3-chloro-2-fluoro-6-(tetrazol-1-yl)phenyl]-1-oxido-pyridin-1-ium-2-yl]-3-(difluoromethoxy)propyl]pyrazol-4-yl]phenyl]carbamate;
4-[1-[(1R)-1-[5-[3-chloro-2-fluoro-6-[4-(trifluoromethyl)triazol-1-yl]phenyl]-1-oxido-pyridin-1-ium-2-yl]-3-(difluoromethoxy)propyl]pyrazol-4-yl]-2-fluoro-benzamide;

(R*)-4-[1-[1-[5-[3-chloro-6-(4-chlorotriazol-1-yl)-2-fluoro-phenyl]-1-oxido-pyridin-1-ium-2-yl]-3-(difluoromethoxy)propyl]pyrazol-4-yl]-2-fluoro-benzamide;

4-[1-[(1R)-1-[5-[3-chloro-2-fluoro-6-[4-(trifluoromethyl)triazol-1-yl]phenyl]-1-oxido-pyridin-1-ium-2-yl]-2-[1-(difluoromethyl)pyrazol-3-yl]ethyl]pyrazol-4-yl]-2-fluoro-benzamide;

4-[1-[(1R)-1-[5-[3-chloro-6-(4-chlorotriazol-1-yl)-2-fluoro-phenyl]-1-oxido-pyridin-1-ium-2-yl]-2-[1-(difluoromethyl)pyrazol-3-yl]ethyl]pyrazol-4-yl]-2-fluoro-benzamide;

and pharmaceutically acceptable salts thereof.

In certain embodiments, the present invention is directed to a compound independently selected from the group consisting of 5-[3-chloro-2-fluoro-6-(tetrazol-1-yl)phenyl]-2-[(1R)-3-(difluoromethoxy)-1-[4-(3-methyltriazol-4-yl)pyrazol-1-yl]propyl]-1-oxido-pyridin-1-ium;

5-[3-chloro-6-(4-chlorotriazol-1-yl)-2-fluoro-phenyl]-2-[(1R)-3-(difluoromethoxy)-1-[4-(3-methyltriazol-4-yl)pyrazol-1-yl]propyl]-1-oxido-pyridin-1-ium;

5-[3-chloro-2-fluoro-6-(tetrazol-1-yl)phenyl]-2-[(1R)-3-(difluoromethoxy)-1-[4-[3-(difluoromethyl)triazol-4-yl]pyrazol-1-yl]propyl]-1-oxido-pyridin-1-ium;

5-[3-chloro-6-(4-chlorotriazol-1-yl)-2-fluoro-phenyl]-2-[(1R)-3-(difluoromethoxy)-1-[4-(5-fluoro-3-methyl-triazol-4-yl)pyrazol-1-yl]propyl]-1-oxido-pyridin-1-ium;

5-[3-chloro-6-(4-chlorotriazol-1-yl)-2-fluoro-phenyl]-2-[(1R)-3-(difluoromethoxy)-1-[4-[2-(difluoromethyl)-1,2,4-triazol-3-yl]pyrazol-1-yl]propyl]-1-oxido-pyridin-1-ium;

5-[3-chloro-6-(4-chlorotriazol-1-yl)-2-fluoro-phenyl]-2-[(1R)-3-(difluoromethoxy)-1-[4-(2-methyl-1,2,4-triazol-3-yl)pyrazol-1-yl]propyl]-1-oxido-pyridin-1-ium;

5-[3-chloro-2-fluoro-6-(tetrazol-1-yl)phenyl]-2-[(1R)-2-cyclopropyl-1-[4-(5-fluoro-3-methyl-triazol-4-yl)pyrazol-1-yl]ethyl]-1-oxido-pyridin-1-ium;

5-[3-chloro-2-fluoro-6-[4-(trifluoromethyl)triazol-1-yl]phenyl]-2-[(1R)-3-(difluoromethoxy)-1-[4-(2-methyl-1,2,4-triazol-3-yl)pyrazol-1-yl]propyl]-1-oxido-pyridin-1-ium;

5-[3-chloro-6-(4-chlorotriazol-1-yl)-2-fluoro-phenyl]-2-[(1R)-2-[1-(difluoromethyl)pyrazol-3-yl]-1-[4-(2-methyl-1,2,4-triazol-3-yl)pyrazol-1-yl]ethyl]-1-oxido-pyridin-1-ium;

5-[3-chloro-6-(4-chlorotriazol-1-yl)-2-fluoro-phenyl]-2-[(1R)-2-[1-(difluoromethyl)pyrazol-3-yl]-1-[4-(5-fluoro-3-methyl-triazol-4-yl)pyrazol-1-yl]ethyl]-1-oxido-pyridin-1-ium;

and pharmaceutically acceptable salts thereof.

Definitions

As used herein, unless otherwise noted, "halogen" shall mean chloro, bromo, fluoro and iodo, preferably bromo, fluoro or chloro.

As used herein, unless otherwise noted, the term "oxo" shall mean s functional group of the structure =O (i.e. a substituent oxygen atom connected to another atom by a double bond).

As used herein, unless otherwise noted, the term "$C_{X-Y}$alkyl" wherein X and Y are integers, whether used alone or as part of a substituent group, include straight and branched chains containing between X and Y carbon atoms. For example, $C_{1-4}$alkyl radicals include straight and branched chains of between 1 and 4 carbon atoms, including methyl, ethyl, propyl, isopropyl, butyl, isobutyl, sec-butyl and t-butyl.

One skilled in the art will recognize that the terms "—($C_{X-Y}$alkyl)-" and "—$C_{X-Y}$alkyl-" wherein X and Y are integers, shall denote any $C_{X-Y}$alkyl carbon chain as herein defined, wherein said $C_{X-Y}$alkyl chain is divalent and is further bound through two points of attachment, preferably through two terminal carbon atoms.

As used herein, unless otherwise noted, the term "fluorinated $C_{X-Y}$alkyl" shall mean any $C_{X-Y}$alkyl group as defined above substituted with at least one fluorine atom, preferably one to three fluorine atoms. In an example, "fluorinated $C_{1-4}$alkyl" include, but are not limited to, —$CH_2F$, —$CF_2H$, —$CF_3$, —$CH_2$—$CF_3$, —$CF_2$—$CF_2$—$CF_2$—$CF_3$, and the like.

As used herein, unless otherwise noted, "$C_{X-Y}$alkoxy" wherein X and Y are integers, shall mean an oxygen ether radical of the above described straight or branched chain $C_{X-Y}$alkyl groups containing between X and Y carbon atoms. For example, $C_{1-4}$alkoxy shall include methoxy, ethoxy, n-propoxy, isopropoxy, n-butyloxy, iso-butyloxy, sec-butyloxy and tert-butyloxy.

As used herein, unless otherwise noted, the term "fluorinated $C_{X-Y}$alkoxy" shall mean any $C_{X-Y}$alkoxy group as defined above substituted with at least one fluorine atom, preferably one to three fluorine atoms. For example, "fluorinated $C_{1-4}$alkoxy" include, but are not limited, —$OCH_2F$, —$OCF_2H$, —$OCF_3$, —$OCH_2$—$CF_3$, —$OCF_2$—$CF_2$—$CF_2$—$CF_3$, and the like.

As used herein, unless otherwise noted, the term "$C_{X-Y}$cycloalkyl", wherein X and Y are integers, shall mean any stable X- to Y-membered monocyclic, bicyclic, polycyclic, bridged or spiro-cyclic saturated ring system, preferably a monocyclic, bicyclic, bridged or spiro-cyclic saturated ring system. For example, the term "$C_{3-8}$cycloalkyl" includes, but is not limited to cyclopropyl, cyclobutyl, cyclopentyl, cyclohexyl, cycloheptyl, bicyclo[2.2.1]hept-2-yl, cyclooctyl, bicyclo[2.2.2]octan-2-yl, and the like.

As used herein, unless otherwise noted, the term "heterocyclyl" shall denote any monocyclic, saturated, partially unsaturated or aromatic ring structure containing at least one heteroatom selected from the group consisting of O, N and S, optionally containing one to three additional heteroatoms independently selected from the group consisting of O, N and S; or any saturated, partially unsaturated, partially aromatic or aromatic bicyclic, fused, bridged or spiro-cyclic ring system containing at least one heteroatom selected from the group consisting of O, N and S, optionally containing one to four additional heteroatoms independently selected from the group consisting of O, N and S. Unless otherwise noted, the heterocyclyl group may be attached at any heteroatom or carbon atom of the ring such that the result is a stable structure. Suitable examples include, but are not limited to, pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 2,3-dihydrobenzofuryl, 2,3-dihydrobenzo[b][1,4]dioxinyl, benzo[d][1,3]dioxolyl, and the like.

As used herein, unless otherwise noted, the term "5 to 6 membered heterocyclyl" shall denote any monocyclic, saturated, partially unsaturated or aromatic heterocyclyl group as described above, wherein the 5 to 6 membered heterocyclyl contains 5 to 6 ring atoms. Unless otherwise noted, the 5 to 6 membered heterocyclyl may be attached at any heteroatom or carbon atom of the ring such that the result is a stable structure. Suitable examples include, but are not limited to furyl, thiophenyl, pyrrolyl, pyrrolidinyl, oxazolyl, thiazolyl, isoxazolyl, pyrazolyl, imidazolyl, triazolyl, isothiazolyl, dioxolanyl, pyrazolidinyl, thiadiazolyl, pyranyl, pyridinyl, dioxanyl, morpholinyl, dithianyl, thiomorpholinyl, pyridazinyl, pyrimidinyl, pyrazinyl, piperidinyl, piperazinyl, triazinyl, oxazinyl, isoxazinyl, oxathiazinyl, and the like.

As used herein, unless otherwise noted, the term "5 membered heterocyclyl" shall denote heterocyclyl group as described above, wherein the heterocyclyl contains 5 ring atoms. Unless otherwise noted, the 5 membered heterocyclyl may be attached at any heteroatom or carbon atom of the ring such that the result is a stable structure. Suitable examples include, but are not limited to furyl, thiophenyl, pyrrolyl, pyrrolidinyl, oxazolyl, thiazolyl, isoxazolyl, pyrazolyl, imidazolyl, triazolyl, isothiazolyl, dioxolanyl, pyrazolidinyl, thiadiazolyl, and the like.

As used herein, unless otherwise noted, the term "6 membered heterocyclyl" shall denote any heterocyclyl group as described above, wherein the heterocyclyl contains 6 ring atoms. Unless otherwise noted, the 6 membered heterocyclyl may be attached at any heteroatom or carbon atom of the ring such that the result is a stable structure. Suitable examples include, but are not limited to pyranyl, pyridinyl, dioxanyl, morpholinyl, dithianyl, thiomorpholinyl, pyridazinyl, pyrimidinyl, pyrazinyl, piperidinyl, piperazinyl, triazinyl, oxazinyl, isoxazinyl, oxathiazinyl, and the like.

As used herein, unless otherwise noted, the term "5 to 6 membered saturated heterocyclyl" shall denote any heterocyclyl group as described above, wherein the heterocyclyl contains 5 to 6 ring atoms and wherein the heterocyclyl ring structure is saturated (i.e. wherein the ring structure does not contain any double bonds). Unless otherwise noted, the 5 to 6 membered saturated heterocyclyl may be attached at any heteroatom or carbon atom of the ring such that the result is a stable structure. Suitable examples include, but are not limited to pyrrolidinyl, dioxolanyl, imidazolidinyl, pyrazolidinyl, piperidinyl, piperazinyl, morpholinyl, thiomorpholinyl, dithianyl, trithianyl, and the like.

As used herein, unless otherwise noted, the term "9 to 10 membered heterocyclyl" shall mean any heterocyclyl group as described above, wherein the heteocyclyl contains 9 to 10 ring system atoms. Unless otherwise noted, the 9 to 10 membered heterocyclyl may be attached at any heteroatom or carbon atom of the ring such that the result is a stable structure. Suitable examples include, but are not limited to indolenyl, indolyl, isoindolyl, indolizinyl, indolinyl, benzofuryl, benzothiophenyl, indazolyl, benzimidazolyl, benzthiazolyl, purinyl, quinolinyl, isoquinolinyl, quinolizinyl, quinazolinyl, cinnolinyl, phthalazinyl, quinoxalinyl, naphthyridinyl, pteridinyl, quinuclidinyl, thionaphthenyl, isobenzazolyl, pyrano[3,4-b]pyrrolyl, anthranyl, benzopyranyl, chromenyl, coumarinyl, benzopyronyl, and the like.

As used herein, unless otherwise noted, the term "5 to 6 membered or 9 to 10 membered heterocyclyl" shall denote any monocyclic, saturated, partially unsaturated or aromatic ring structure containing 5 to 6 ring atoms, further containing at least one heteroatom selected from the group consisting of O, N and S, and optionally containing one to three additional heteroatoms independently selected from the group consisting of O, N and S; or any saturated, partially unsaturated, partially aromatic or aromatic bicyclic, fused, bridged or spiro-cyclic ring system containing 9 to 10 ring atoms, further containing at least one heteroatom selected from the group consisting of O, N and S, and optionally containing one to four additional heteroatoms independently selected from the group consisting of O, N and S. Unless otherwise noted, the 5 to 6 membered of 9 to 10 membered heterocyclyl group may be attached at any heteroatom or carbon atom of the ring such that the result is a stable structure. Suitable examples include but are not limited to pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 2,3-dihydrobenzofury, 2,3-dihydrobenzo[b][1,4]dioxinyl, benzo[d][1,3]dioxolyl, and the like.

When a particular group is "substituted" (e.g. $C_{X-Y}$alkyl, $C_{X-Y}$alkoxy, $C_{X-Y}$cycloalkyl, heterocyclyl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at a diastereomeric excess of greater than or equal to about 80%, more preferably, at a diastereomeric excess of greater than or equal to about 90%, more preferably still, at a diastereomeric excess of greater than or equal to about 95%, more preferably still, at a diastereomeric excess of greater than or equal to about 98%, most preferably, at a diastereomeric excess of greater than or equal to about 99%.

In certain embodiments, the present invention is directed to compounds of formula (I) in an enantiomeric excess of one of the R- or S-enantiomers (at the stereocenter denoted with the "*"). In certain embodiments of the present invention, the compound of formula (I) is present in an enantiomeric excess of one of the R- or S-enantiomers (at the stereocenter denoted with the "*") of about 55%, about 60%, about 65%, about 70%, about 75%, about 80%, about 85%, about 90%, about 91%, about 92%, about 93%, about 94%, about 95%, about 96%, about 97%, about 98% or about 99%. Preferably the compound of formula (I) is present in an enantiomeric excess of one of the R- or S-enantiomers (at the stereocenter denoted with the "*") of greater than or equal to about 80%, preferably greater than or equal to about 90%, more preferably greater than or equal to about 93%, more preferably greater than or equal to about 95%, more preferably greater than or equal to about 97%, more preferably greater than or equal to about 98%, more preferably greater than or equal to about 99%.

In certain embodiments, the present invention is directed to compounds of formula (I) in a diastereomeric or stereoisomeric excess of one of the possible diastereomers or stereoisomers. In certain embodiments of the present invention, the compound of formula (I) is present in a diastereomeric or stereoisomeric excess of one of the possible diastereomers or stereoisomers, of about 55%, about 60%, about 65%, about 70%, about 75%, about 80%, about 85%, about 90%, about 91%, about 92%, about 93%, about 94%, about 95%, about 96%, about 97%, about 98% or about 99%. Preferably, the compound of formula (I) is present in a diastereomeric or stereoisomeric excess of one of the possible diastereomers or stereoisomers of greater than or equal to about 80%, preferably greater than or equal to about 90%, more preferably greater than or equal to about 93%, more preferably greater than or equal to about 95%, more preferably greater than or equal to about 97%, more preferably greater than or equal to about 98%, more preferably greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

As used herein, unless otherwise noted, the term "isotopologues" shall mean molecules that differ only in their isotopic composition. More particularly, an isotopologue of a molecule differs from the parent molecule in that it contains at least one atom which is an isotope (i.e. has a different number of neutrons from its parent atom).

For example, isotopologues of water include, but are not limited to, "light water" (HOH or $H_2O$), "semi-heavy water" with the deuterium isotope in equal proportion to protium (HDO or $^1H^2HO$), "heavy water" with two deuterium isotopes of hydrogen per molecule ($d_2O$ or $^2H_2O$), "super-heavy water" or tritiated water ($T_2O$ or $^3H_2O$), where the hydrogen atoms are replaced with tritium ($^3H$) isotopes, two heavy-oxygen water isotopologues ($H_2^{18}O$ and $H_2^{17}O$) and isotopologues where the hydrogen and oxygen atoms may each independently be replaced by isotopes, for example the doubly labeled water isotopologue $d_2^{18}O$.

It is intended that within the scope of the present invention, any one or more element(s), in particular when mentioned in relation to a compound of formula (I), shall comprise all isotopes and isotopic mixtures of said element(s), either naturally occurring or synthetically produced, either with natural abundance or in an isotopically enriched form. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. Radiolabelled compounds of formula (I) may comprise one or more radioactive isotope(s) selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^3H$, $^{11}C$ and $^{18}F$.

As used herein, unless otherwise noted, the term "isotopomer" shall mean isomers with isotopic atoms, having the same number of each isotope of each element but differing in their position. Isotopomers include both constitutional isomers and stereoisomers solely based on isotopic location. For example, $CH_3CHDCH_3$ and $CH_3CH_2CH_2D$ are a pair of constitutional isotopomers of n-propane; whereas (R)—$CH_3CHDOH$ and (S)—$CH_3CHDOH$ or (Z)—$CH_3CH$=$CHD$ and (E)-$CH_3CH$=$CHD$ are examples of isotopic stereoisomers of ethanol and n-propene, respectively.

It is further intended that the present invention includes the compounds described herein, including all isomers thereof (including, but not limited to stereoisomers, enantiomers, diastereomers, tautomers, isotopologues, isotopomers, and the like).

Under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl" substituent refers to a group of the formula

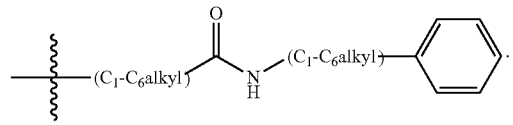

Abbreviations used in the specification, particularly the Schemes and Examples, are as listed in the Table A, below:

TABLE A

| | Abbreviations |
|---|---|
| Ac = | Acetyl (i.e. —C(O)CH₃) |
| AcOH = | Acetic Acid |
| ACN or MeCN = | Acetonitrile |
| ADDP = | 1,1'-(Azodicarbonyl)dipiperidine |
| Boc or BOC = | tert-Butoxyloxycarbonyl (i.e. —C(O)—O—C(CH₃)₃) |
| Boc₂O = | di-tert-butyl decarbonate |
| BPO = | Benzoyl peroxide |
| BSA = | Bovine Serum Albumin |
| CDI = | 1,1'-Carbonyldiimidazole |
| CHAPS = | 3-[(3-cholamidopropyl)dimethylammonio]-1-propanesulfonate |
| Cu(OAc)₂ = | Cupric Acetate |
| Cu(OTf)₂ = | Copper Triflate or Copper(II) trifluoromethane-sulfonate |
| DAST = | Diethylaminosulfur trifluoride |
| DBU = | 1,8-Diazabicyclo[5.4.0]undec-7-ene |
| DCM = | Dichloromethane |
| DCE = | 1,2-Dichloroethane |
| DEA = | Diethylamine |
| Dess Martin (reagent) or DMP = | Dess-Martin periodinane (also known as 1,1,1-Tris(acetyloxy)-1,1-dihydro-1,2-benziodoxol-3-(1H)-one) |
| DIAD = | Diisopropylazodicarboxylate |
| DIEA or DIPEA = | Disiopropyl Ethyl Amine |
| DMA or DMAc = | N,N-dimethylacetamide |
| DMAP = | Dimethylaminopyridine |
| DME (biological context) = | Diabetic Macular Edema |
| DME (examples, schemes) = | Dimethoxyethane |
| DMF = | N,N-Dimethylformamide |
| DMSO = | Dimethylsulfoxide |

TABLE A-continued

| Abbreviations | |
|---|---|
| dba = | Dibenzylideneacetone |
| dppf = | 1,1'-Bis(diphenylphosphino)ferrocene |
| dtbpy = | 4,4'-di-tert-Butyl-2,2'-bipyridine |
| EA or EtOAc = | Ethyl Acetate |
| EDC = | 1-Ethyl-3-(3-dimethylaminopropyl)carbodiimide |
| ee = | Enantiomeric Excess |
| (EP) = | indicates End Point Read (assay) |
| ES or ESI = | Electrospray ionization |
| Et = | Ethyl |
| Et$_2$O = | Diethyl Ether |
| Et$_3$N or TEA = | Triethylamine |
| FXIa = | Factor XIa |
| HAE = | Hereditary Angioedema |
| HATU = | Hexafluorophosphate azabenzotriazole tetramethyl uranium |
| Hex = | Hexanes |
| HFIP = | Hexafluoroisopropanol |
| HOAc = | Acetic Acid |
| HPLC = | High Performance Liquid Chromatography |
| IPA = | Isopropylamine |
| i-PrMgCl = | Isopropyl Magensium Chloride |
| i-PrMgCl•LiCl = | Isopropyl Magensium Chloride Lithium Chloride Complex |
| i-PrOH = | Isopropanol |
| [Ir(OMe)(COD)]$_2$ = | bis(1,5-cyclooctadiene)di-μ-methoxydiiridium(I) |
| KIN = | Indicates Kinetic Read (assay) |
| KOAc = | Potassium Acetate |
| LC-MS or LC/MS = | Liquid chromatography-mass spectrometry |
| LDA = | Lithium Diisopropylamide |
| LiBEt$_3$ = | Lithium Triethylborohydride |
| LiHMDS or LHMDS = | Lithium bis(trimethylsilyl)amide |
| LiN(SiMe$_3$)$_2$ = | Lithium bis(trimethylsilyl)amide |
| m-CPBA = | meta-chloroperbenzoic acid |
| Me = | Methyl |
| MeOH = | Methanol |
| 2-Me—THF = | 2-Methyl-tetrahydrofuran |
| Me = | Methyl |
| MeOH = | Methanol |
| MOM = | Methoxy methyl |
| Ms or mesyl = | Methylsulfonyl (i.e. —SO$_2$—CH$_3$) |
| MsCl = | Mesylchloride |
| MTBE or MtBE = | Methyl tert-butylether |
| NBS = | N-bromosuccinimide |
| NCS = | N-chlorosuccinimide |
| NaOAc = | Sodium Acetate |
| n-BuLi = | n-ButylLithium |
| NCS = | N-Chlorosuccinimide |
| NMR = | Nuclear Magnetic Resonance |
| OMS or mesylate = | Methanesulfonate (i.e. —O—SO$_2$—CH$_3$) |
| OTf or triflate = | Trifluoromethanesulfonyl (i.e. —O—SO$_-$—CF$_3$) |
| OTs or tosylate = | p-Toluenesulfonate (i.e. —O—SO$_2$-(p-methylphenyl)) |
| Pd(dppf)Cl$_2$ or PdCl$_2$(dppf) = | [1,1'-Bis(diphenylphosphino)ferrocene] Palladium (II) Dichloride |
| PdCl$_2$(PPh$_3$)$_2$ or Pd(PPh$_3$)$_2$Cl$_2$ | Bis(triphenylphosphine)palladium (II) Dichloride |
| Pd$_2$(dba)$_3$ = | Tris(dibenzylideneacetone)dipalladium(0) |
| Pd(PPh$_3$)$_4$ = | Tetrakis(triphenylphosphine)palladium(0) |
| PE = | Petroleum ether |
| Ph = | Phenyl |
| PK = | Plasma Kallikrein |
| PPh$_3$ = | Triphenylphosphine |
| ReMeO$_3$ or MeReO$_3$ = | Methyl trioxorhenium (VII) |
| RFU = | Relative Fluorescence Unit |
| sat. = | Saturated |
| t-BuOLi = | Lithium tert-butoxide |
| t-BuONa = | Sodium tert-butoxide |
| t-BuOH = | tert-Butylalcohol |
| TBAF = | Tetra-n-butylammonium fluoride |
| TBAI | Tetra-n-butylammonium iodide |
| TBS = | tert-Butyldimethylsilyl |
| TBSCl = | tert-Butyldimethylsilyl chloride |
| TEA = | Triethylamine |
| Tf or triflyl = | Trifluoromethylsulfonyl (i.e. —SO$_2$—CF$_3$) |
| TFA = | Trifluoroacetic acid |
| THF = | Tetrahydrofuran |
| THP = | Tetrahydropyranyl |
| TLC = | Thin Layer Chromatography |
| TMS = | Trimethysilyl |
| TMSCF$_2$Br = | Bromodifluoromethyl)trimethylsilane |
| TMSN$_3$ = | Trimethylsilylazide |
| Tris (buffer) = | 2-Amino-2-(hydroxymethyl)-1,3-propanediol |
| Ts or tosyl = | —SO$_2$-(p-methylphenyl) |
| wt % or wt % = | Weight Percent |
| Xphos-Pd G3 = | (2-Dicyclohexylphosphino-2',4',6'-triisopropyl-1,1'-biphenyl) [2-(2'-amino-1,1'-biphenyl)]palladium(II) methanesulfonate |

As used herein, unless otherwise noted, the term "isolated form" shall mean that the compound is present in a form which is separate from any solid mixture with another compound(s), solvent system or biological environment. In an embodiment of the present invention, the compound of formula (I) is present in an isolated form.

As used herein, unless otherwise noted, the term "substantially pure form" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment of the present invention, the compound of formula (I) is present as a substantially pure form.

As used herein, unless otherwise noted, the term "substantially free of a corresponding salt form(s)" when used to described the compound of formula (I) shall mean that mole percent of the corresponding salt form(s) in the isolated base of formula (I) is less than about 5 mole percent, preferably less than about 2 mole percent, more preferably, less than about 0.5 mole percent, most preferably less than about 0.1 mole percent.

In an embodiment of the present invention, the compound of formula (I) is present in a form which is substantially free of corresponding salt form(s).

As used herein, unless otherwise noted, the terms "treating", "treatment" and the like, shall include the management and care of a subject or patient, preferably a mammal, more preferably a human, for the purpose of combating a disease, condition, or disorder and includes the administration of a compound of the present invention to prevent the onset of the symptoms or complications, alleviate the symptoms or complications, slow the progression of the disease or disorder, or eliminate the disease, condition, or disorder. The terms "treating" or "treatment" further include: (a) inhibiting the disease-state, i.e., arresting its development; and/or (b) relieving the disease-state, i.e., causing regression of the disease state.

As used herein, "prophylaxis" is the protective treatment of a disease state to reduce and/or minimize the risk and/or reduction in the risk of recurrence of a disease state by administering to a patient a therapeutically effective amount of at least one of the compounds of the present invention or a stereoisomer, isotopologue, isotopomer, a pharmaceutically acceptable salt, or a solvate thereof. Patients may be selected for prophylaxis therapy based on factors that are known to increase risk of suffering a clinical disease state compared to the general population. For prophylaxis treatment, conditions of the clinical disease state may or may not be presented yet. "Prophylaxis" treatment can be divided into (a) primary prophylaxis and (b) secondary prophylaxis. Primary prophylaxis is defined as treatment to reduce or minimize the risk of a disease state in a patient that has not yet presented with a clinical disease state, whereas secondary prophylaxis is defined as minimizing or reducing the risk of a recurrence or second occurrence of the same or similar clinical disease state.

As used herein, "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population.

As used herein, "risk reduction" covers therapies that lower the incidence of development of a clinical disease state. As such, primary and secondary prevention therapies are examples of risk reduction.

One skilled in the art will recognize that wherein the present invention is directed to methods of prophylaxis, the subject in need thereof (i.e. a subject in need of prophylaxis) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prophylaxis or prophylactic treatment) as a consequence of the subject's medical history, including, but not limited to, family history, pre-disposition, co-existing (comorbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

As used herein, the term "composition" is intended to encompass a product comprising the specified ingredients in the specified amounts, as well as any product which results, directly or indirectly, from combinations of the specified ingredients in the specified amounts.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

The compounds of the present invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds is preferably, but not necessarily, a synergistic combination. Synergy, for example, may occur when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently or consecutively to the mammal being treated. When administered in combination each component may be administered at the same time or sequentially in any order at different points in time. Thus, each component may be administered separately but sufficiently closely in time so as to provide the desired therapeutic effect.

One or more additional pharmacologically active agents may be administered in combination with the compounds of the invention. The additional active agent (or agents) is intended to mean a pharmaceutically active agent (or agents) that is active in the body, including pro-drugs that convert to pharmaceutically active form after administration, which is different from the compound of formula (I), and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of formula (I) in a single dosage formulation (a fixed dose drug combination), or may be administered to the patient in one or more separate dosage formulations which allows for concurrent or sequential administration of the active agents (co-administration of the separate active agents).

Examples of additional active agents which may be employed include but are not limited to angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin receptor antagonists also known as angiotensin receptor blockers or ARBs (e.g., losartan i.e., COZAAR®, valsartan, candesartan, olmesartan, telmesartan, eprosartan, irbesartan and any of these drugs used in combination with hydrochlorothiazide such as HYZAAR®); diuretics, e.g. hydrochlorothiazide (HCTZ); potassium sparing diuretics such as amiloride HCl, spironolactone, epleranone, triamterene, each with or without HCTZ; neutral endopeptidase inhibitors (e.g., thiorphan and phosphoramidon); aldosterone antagonists; aldosterone synthase inhibitors; renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643); enalkrein; RO 42-5892; A 65317; CP 80794; ES 1005; ES 8891; SQ 34017; aliskiren (2(S),4(S),5(S),7(S)—

N-(2-carbamoyl-2-methylpropyl)-5-amino-4-hydroxy-2,7-diisopropyl-8-[4-methoxy-3-(3-methoxypropoxy)-phenyl]-octanamide hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholytics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant (TREDAPTIVE®) and/or with an HMG-CoA reductase inhibitor; niacin in immediate-release or controlled release forms, and particularly niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; or with other drugs beneficial for the prevention or the treatment of the above-mentioned diseases including but not limited to diazoxide; and including the free-acid, free-base, and pharmaceutically acceptable salt forms of the above active agents where chemically possible. Compounds which can be alternatively or additionally administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Anticoagulant agents (or coagulation inhibitory agents) that may be used in combination with the compounds of this invention include warfarin, heparin (either unfractionated heparin or any commercially available low molecular weight heparin, for example enoxaparin and dalteparin), aprotinin, synthetic pentasaccharide inhibitors of Factor Xa such as fondaparinux and idraparinux, direct Factor Xa inhibitors such as rivaroxaban, apixaban, betrixaban, edoxaban, otamixaban, direct acting thrombin inhibitors including hirudin, dabigatran, argatroban, ximelagatran, melagatran, lepirudin, desirudin, and bivalirudin, as well as other factor VIIa inhibitors, VIIIa inhibitors, IXa inhibitors, Xa inhibitors, XIa inhibitors, fibrinogen receptor antagonists (including abciximab, eptifibatide and tirofiban), TAFI inibitors, and others known in the art. Factor IXa inhibitors include synthetic active-site blocked competitive inhibitors, oral inhibitors and RNA aptamers. These are described in Howard, E L, Becker K C, Rusconi, C P, Becker R C. "Factor IXa Inhibitors as Novel Anticoagulents", Arterioscler. Thromb. Vasc. Biol., 2007, pp 722-727, Vol. 27.

The term "anti-platelet agents" or "platelet inhibitory agents", as used herein, denotes agents that inhibit platelet function, for example, by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicylic acid or ASA), and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, phosphodiesterase-III (PDE-III) inhibitors (e.g., dipyridamole, cilostazol), and PDE V inhibitors (such as sildenafil), and pharmaceutically acceptable salts or prodrugs thereof.

The term "anti-platelet agents" or "platelet inhibitory agents", as used herein, is also intended to include ADP (adenosine diphosphate) receptor antagonists, preferable antagonists of the purinergic receptors P2Y1 and P2Y12 with P2Y12 being even more preferred. Preferred P2Y12 receptor antagonists include ticlopidine, prasugrel, clopidogrel, elinogrel, ticagrelor and cangrelor, including pharmaceutically acceptable salts or prodrugs thereof. Clopidogrel is an even more preferred agent. Ticlopidine and clopidogrel are also preferred compounds since they are known to be gentle on the gastro-intestinal tract in use. The compounds of the present invention may also be dosed in combination with aprotinin.

The term "thrombin inhibitors" or "anti-thrombin agents", as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin), endothelial cell activation, inflammatory reactions, and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, dabigatran and argatroban, including pharmaceutically acceptable salts and prodrugs thereof. Boroarginine derivatives and boropeptides include N-acetyl and peptide derivatives of boronic acid, such as C-terminal alpha-aminoboronic acid derivatives of lysine, ornithine, arginine, homoarginine and corresponding isothiouronium analogs thereof. The term "hirudin", as used herein, includes suitable derivatives or analogs of hirudin, referred to herein as hirulogs, such as disulfatohirudin.

The term "thrombin receptor antagonists", also known as protease activated receptor (PAR) antagonists or PAR-1 antagonists, are useful in the treatment of thrombotic, inflammatory, atherosclerotic and fibroproliferative disorders, as well as other disorders in which thrombin and its receptor play a pathological role. Thrombin receptor antagonist peptides have been identified based on structure-activity studies involving substitutions of amino acids on thrombin receptors. In Bernatowicz et al, J Med. Chem., vol. 39, pp. 4879-4887 (1996), tetra- and pentapeptides are disclosed as being potent thrombin receptor antagonists, for example N-trans-cinnamoyl-p-fluoroPhe-p-guanidinoPhe-Leu-Arg-$NH_2$ and N-trans-cinnamoyl-p-fluoroPhe-p-guanidinoPhe-Leu-Arg-Arg-$NH_2$. Peptide thrombin receptor antagonists are also disclosed in WO 94/03479. Substituted tricyclic thrombin receptor antagonists are disclosed in U.S. Pat. Nos. 6,063,847, 6,326,380 and WO 01/96330. Other thrombin receptor antagonists include those disclosed in U.S. Pat. Nos. 7,304,078; 7,235,567; 7,037,920; 6,645,987; and EP Patent Nos. EP1495018 and EP1294714.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, PAI-I inhibitors (i.e., inactivators of tissue plasminogen activator inhibitors), alpha-2-antiplasmin inhibitors, and anisoylated plasminogen streptokinase activator complexes, including pharmaceutically acceptable salts or prodrugs thereof. The term anistreplase, as used herein, refers to anisoylated plasminogen streptokinase activator complexes. The term urokinase, as used herein, is intended to denote both dual and single chain urokinase, the latter also being referred to herein as prourokinase. Examples of suitable anti-arrhythmic agents for use in combination with the present compounds include: Class I agents (such as propafenone); Class II agents (such as carvedilol and propranolol); Class III agents (such as sotalol, dofetilide, aminodarone, azimilide and ibutilide); Class IV agents (such as ditiazem and verapamil); IAch inhibitors, and IKur inhibitors (e.g., compounds such as those disclosed in WO01/40231).

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems.

One skilled in the art will recognize that wherein a reaction step of the present invention may be carried out in a variety of solvents or solvent systems, said reaction step may also be carried out in a mixture of the suitable solvents or solvent systems.

One skilled in the art will further recognize that the reaction or process step(s) as herein described are allowed to proceed for a sufficient period of time until the reaction is complete, as determined by any method known to one skilled in the art, for example, chromatography (e.g. HPLC). In this context a "completed reaction or process step" shall mean that the reaction mixture contains a significantly diminished amount of the starting material(s)/reagent(s) and a significantly reduced amount of the desired product(s), as compared to the amounts of each present at the beginning of the reaction.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

Examples of suitable solvents, bases, reaction temperatures, and other reaction parameters and components are provided in the detailed descriptions which follow herein. One skilled in the art will recognize that the listing of said examples is not intended, and should not be construed, as limiting in any way the invention set forth in the claims which follow thereafter.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

As used herein, unless otherwise noted, the term "oxygen protecting group" shall mean a group which may be attached to an oxygen atom to protect said oxygen atom from participating in a reaction and which may be readily removed following the reaction. Suitable oxygen protecting groups include, but are not limited to, acetyl, benzoyl, t-butyl-dimethylsilyl, trimethylsilyl (TMS), MOM, THP, and the like. Other suitable oxygen protecting groups may be found in texts such as T. W. Greene & P. G. M. Wuts, Protective Groups in Organic Synthesis, John Wiley & Sons, 1991.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows $$[(Rmoles-Smoles)/(Rmoles+Smoles)] \times 100\%$$

where Rmoles and Smoles are the R and S mole fractions in the mixture such that Rmoles+Smoles=1. The enantiomeric excess may alternatively be calculated from the specific rotations of the desired enantiomer and the prepared mixture as follows:

$$ee=([\alpha-obs]/[\alpha-max]) \times 100.$$

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts". Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, ( )-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

General Synthesis Schemes

Compounds of formula (I) of the present invention may be prepared as described in the general synthesis schemes and Examples which follow hereinafter, selecting and substituting suitable reagents and conditions, as would be well within the skill of persons versed in the art. Additionally, the preparation of any starting materials used in the schemes and synthesis examples which follow hereinafter is similarly well within the skill of persons versed in the art.

Compounds of formula (I) wherein Y is N and Z is C(R³) may be prepared as described in Scheme 1, below.

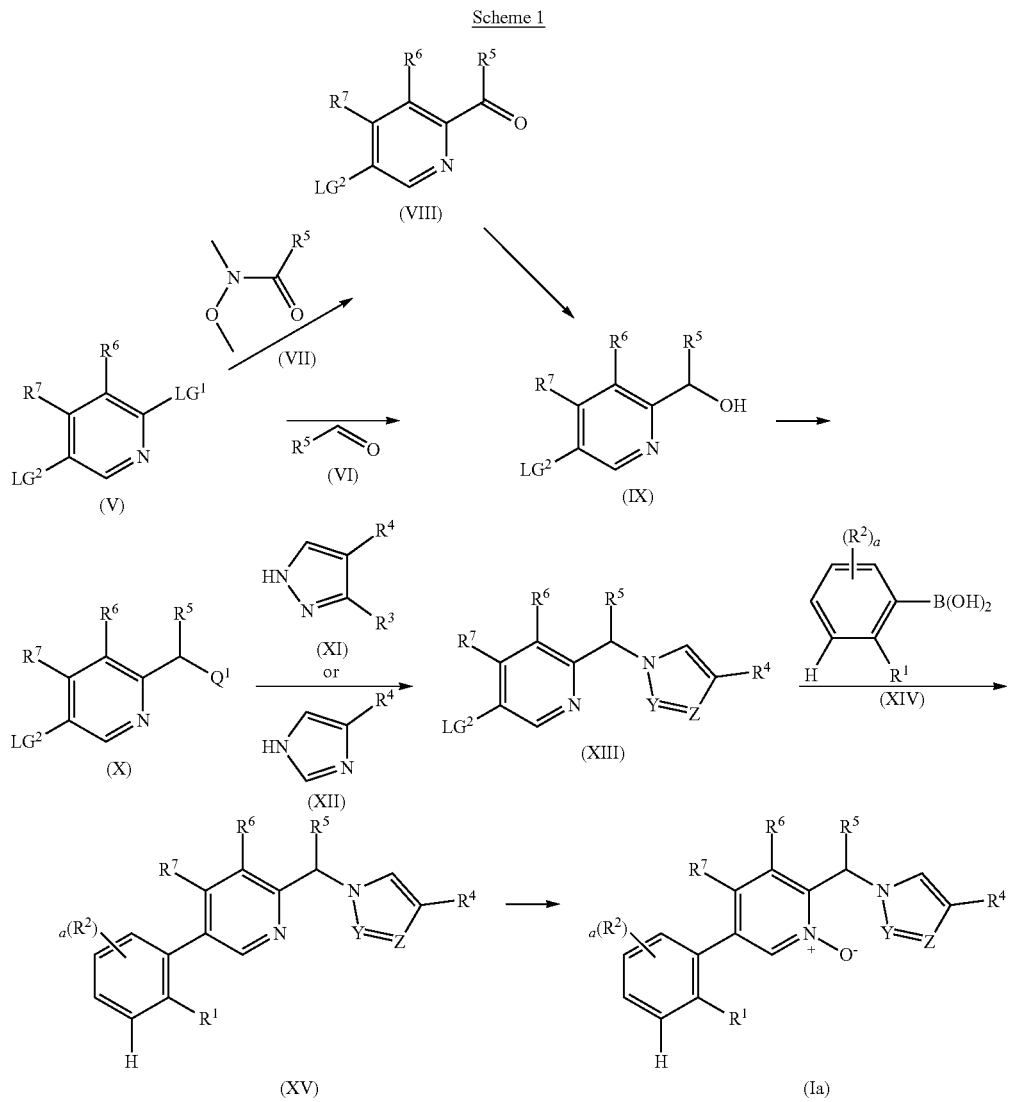

Scheme 1

Accordingly, a suitably substituted compound of formula (V), wherein LG¹ is a suitably selected leaving group such as Br, I, and the like, LG² is a second suitably selected leaving group such as Br, Cl, OTf, and the like, is reacted sequentially with a suitably selected reagent such as n-BuLi, i-PrMgCl.LiCl, and the like; and a suitably substituted compound of formula (VI), a known compound or compound prepared by known methods; in a suitably selected solvent such as THF, Et₂O, toluene, and the like; preferably at about −78° C.; to yield the corresponding compound of formula (IX).

Alternatively, the compound of formula (V) is reacted sequentially with a suitably selected reagents such as n-BuLi, i-PrMgCl and the like; and a suitably substituted compound of formula (VII), a known compound or compound prepared by known methods; in a suitably selected solvent such as THF, Et₂O, heptanes, and the like; preferably at about −78° C.; to yield the corresponding compound of formula (VIII). The compound of formula (VIII) is then reacted with a suitably selected reducing agent such as NaBH₄, LiAlH₄, LiBEt₃, and the like; in a suitably selected solvent such as methanol, i-PrOH, THF, and the like; preferably at a temperature in the range of from about −15° C. to about 20° C. (for example, at about 0° C.); to yield the corresponding compound of formula (IX).

The compound of formula (IX) is protected according to known methods, to yield the corresponding compound of formula (X), wherein Q¹ is —OPG¹ and PG¹ is the corresponding oxygen protecting group such as mesyl, tosyl, and the like. For example, the compound of formula (IX) may be reacted with mesyl chloride or mesyl anhydride, in the presence of an organic amine such as TEA, pyridine, and the like, in a suitably selected solvent such as DCM, and the like, preferably at a temperature of about 20° C. (about room temperature), to yield the corresponding compound of formula (X) wherein Q¹ is —O-mesyl (PG¹ is mesyl). Alternatively, the compound of formula (IX) is reacted with a suitably selected chlorinating agent such as SO₂Cl, POCl₃, and the like; in a suitably selected solvent such as DCM, DCE, and the like; to yield the corresponding compound of formula (X) wherein the Q¹ is —Cl.

The compound of formula (X) is reacted with a suitably substituted pyrazole, a compound of formula (XI), a known compound or compound prepared by known methods or a suitably substituted imidazole, a compound of formula (XII), a known compound or compound prepared by known methods; in the presence of a suitably selected base such as Cs$_2$CO$_3$, K$_2$CO$_3$, DIEA, DBU, and the like; in a suitably selected solvent such as acetonitrile, DMF, 1,4-dioxane, and the like; to yield the corresponding compound of formula (XIII).

The compound of formula (XIII) is reacted with a suitably substituted compound of formula (XIV), a known compound or compound prepared by known methods; in the presence of a suitably selected catalyst such as Pd(PPh$_3$)$_4$, PdCl$_2$(dppf), Pd$_2$(dba)$_3$, and the like; in the presence of a suitably selected base such as K$_2$CO$_3$, Cs$_2$CO$_3$, K$_3$PO$_4$, and the like; in a suitably selected solvent such as 1,4-dioxane, DMF, toluene, and the like; to yield the corresponding compound of formula (XV).

The compound of formula (XV) is reacted with a suitably selected oxidizing agent such as a mixture of hydrogen peroxide and ReMeO$_3$ (methyltrioxorhenium), and the like; in a suitably selected solvent such as DMF, MeOH, THF, and the like; to yield the corresponding compound of formula (Ia).

Compounds of formula (I), wherein Y is N, Z is C(R$^3$) and wherein R$^1$ is a N-bound substituted ring structure such as 1,2,3,4-tetrazol-1-yl, may alternatively be prepared as described in Scheme 2, below.

Scheme 2

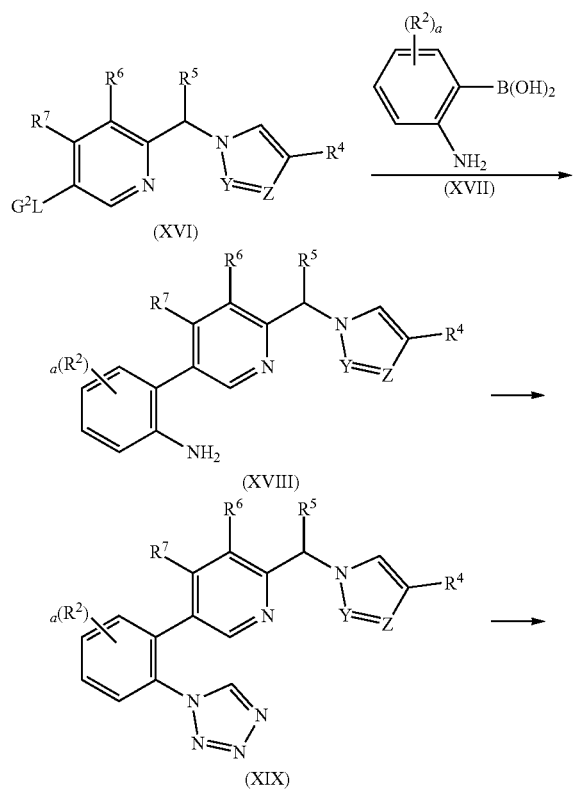

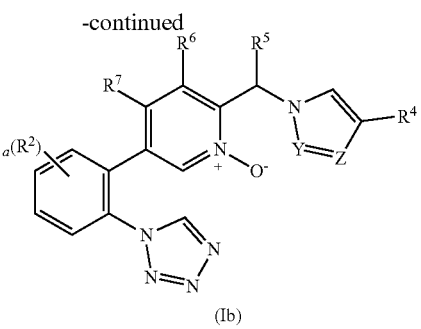

Accordingly, a suitably substituted compound of formula (XVI), prepared for example as described in Scheme 1, above, is reacted with a suitably substituted compound of formula (XVII), a known compound or compound prepared by known methods; in the presence of a suitably selected catalyst such as Pd(PPh$_3$)$_4$, PdCl$_2$(PPh$_3$)$_2$, PdCl$_2$(dppf), and the like; in the presence of a suitably selected base such as K$_2$CO$_3$, Cs$_2$CO$_3$, and the like; in a suitably selected solvent such as 1,4-dioxane, DMF, toluene, and the like; to yield the corresponding compound of formula (XVIII).

The compound of formula (XVIII) is reacted with a suitably selected source of azides such as TMSN$_3$, NaN$_3$, and the like; in the presence of trimethoxymethyl in acetic acid, with heating (for example to a temperature in the range of from about 45° C. to about 100° C.), preferably in a flow chemistry reactor; to yield the corresponding compound of formula (XIX).

The compound of formula (XIX) is reacted with a suitably selected oxidizing agent such as a mixture of hydrogen peroxide and ReMeO$_3$ (methyltrioxorhenium), and the like; in a suitably selected solvent such as DMF, MeOH, 1,4-dioxane, and the like; to yield the corresponding compound of formula (Ib).

One skilled in the art will recognize that compounds of formula (I) wherein R$^1$ is a nitrogen bound ring structure (other than 1,2,3,4-tetrazol-1-yl exemplified above) may be similarly prepared, by reacting a suitably substituted compound of formula (XVIII) with a suitably selected reagent, to effect the desired ring closure at the terminal NH$_2$ group, according to known methods, as would be readily recognized by those skilled in the art.

Certain compounds of formula (I) wherein Y is N and Z is C(R$^3$) may alternatively be prepared as described in Scheme 3, below.

Scheme 3

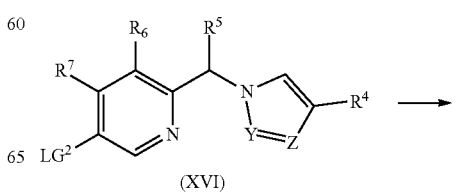

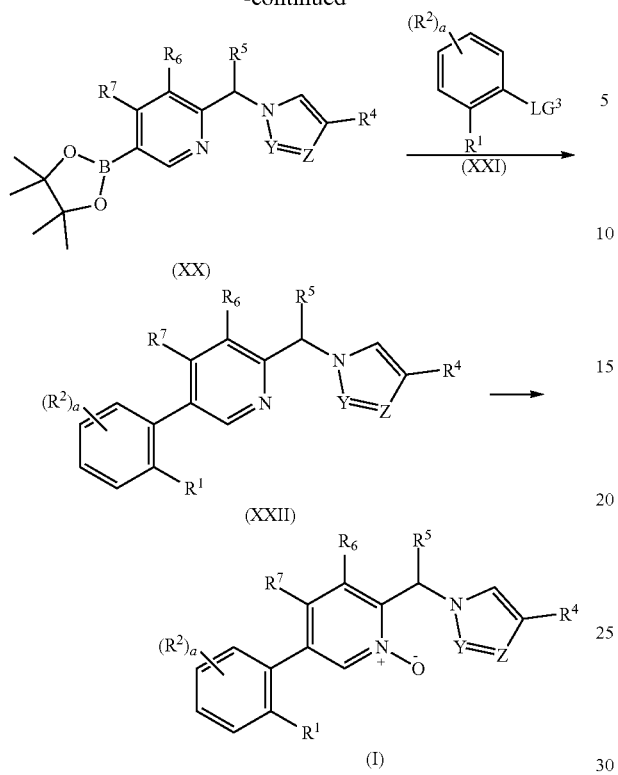

(XX)

(XXII)

(I)

Accordingly, a suitably substituted compound of formula (XVI), prepared for example as described in Scheme 1 above, is reacted with 4,4,4',4',5,5,5',5'-octamethyl-2,2'-bi(1,3,2-dioxaborolane), a known compound; in the presence of a suitable selected catalyst such as $PdCl_2$(dppf), $PdCl_2$($PPh_3$)$_2$, Pd(dba)$_3$, and the like; in the presence of a suitably selected agent such as KOAc, NaOAc, NaHCO$_3$, and the like; in a suitable selected solvent such as DMSO, THF, 1,4-dioxane, and the like; to yield the corresponding compound of formula (XX).

The compound of formula (XX) is reacted with a suitably substituted compound of formula (XXI), wherein $LG^3$ is a suitably selected leaving group such as Br, I, OTf, and the like, a known compound or compound prepared by known methods; in the presence of a suitably selected base such as $K_2CO_3$, NaHCO$_3$, $K_3PO_4$, and the like; in the presence of a suitably selected catalyst such as Pd(PPh$_3$)$_2$, Pd$_2$(dba)$_3$, PdCl$_2$(dppf), and the like; in a suitably selected solvent such as DMF, 1,4-dioxane, toluene, and the like; to yield the corresponding compound of formula (XXII).

The compound of formula (XXII) is reacted with a suitably selected oxidizing agent such as a mixture of hydrogen peroxide and ReMeO$_3$ (methyltrioxorhenium), and the like; in a suitably selected solvent such as DMF, MeOH, 1,4-dioxane, and the like; to yield the corresponding compound of formula (I).

Certain compounds of formula (VIII), more particularly, compounds of formula (VIII) wherein $R^5$ is selected from the group consisting of —(CH$_2$)—$R^Y$; wherein $R^Y$ is for example a ring structure, may alternatively be prepared as described in Scheme 4, below.

Scheme 4

Accordingly, a suitably substituted compound of formula (XXIII), wherein $LG^2$ is a second suitably selected leaving group such as Br, Cl, OTf, and the like, and wherein $LG^4$ is a suitably selected leaving group such as Br, Cl, OTs, and the like, a known compound or compound prepared by known methods, is reacted with a suitably substituted compound of formula (XXIV), a known compound or compound prepared by known methods; neat or in a suitably selected solvent such as DMF, DMSO, and the like; preferably at an elevated temperature, for example at about 80° C.; to yield the corresponding compound of formula (XXV).

The compound of formula (XXV) is reacted with a suitably selected reducing agent such as NaBH$_4$, LiAlH$_4$, and the like; in a suitably selected solvent such as methanol, i-PrOH, DMF, and the like; preferably at a temperature in the range of from about −15° C. to about 20° C. (for example, at about 0° C.); to yield the corresponding compound of formula (VIIIa).

Compounds of formula (IX) wherein $R^5$ is —CH$_2$-(2-ethoxy-carbonyl-cycloprop-1-yl) may alternatively be prepared as described in Scheme 5, below.

Scheme 5

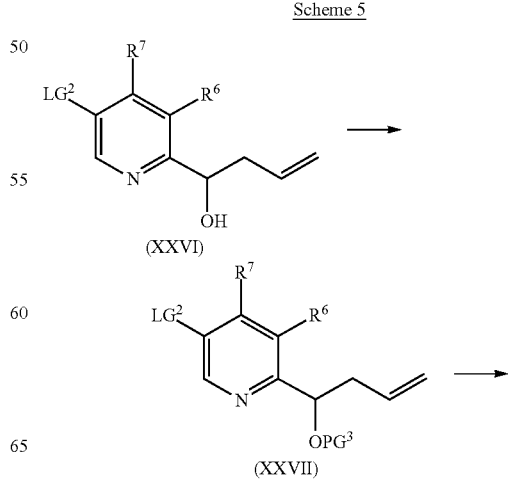

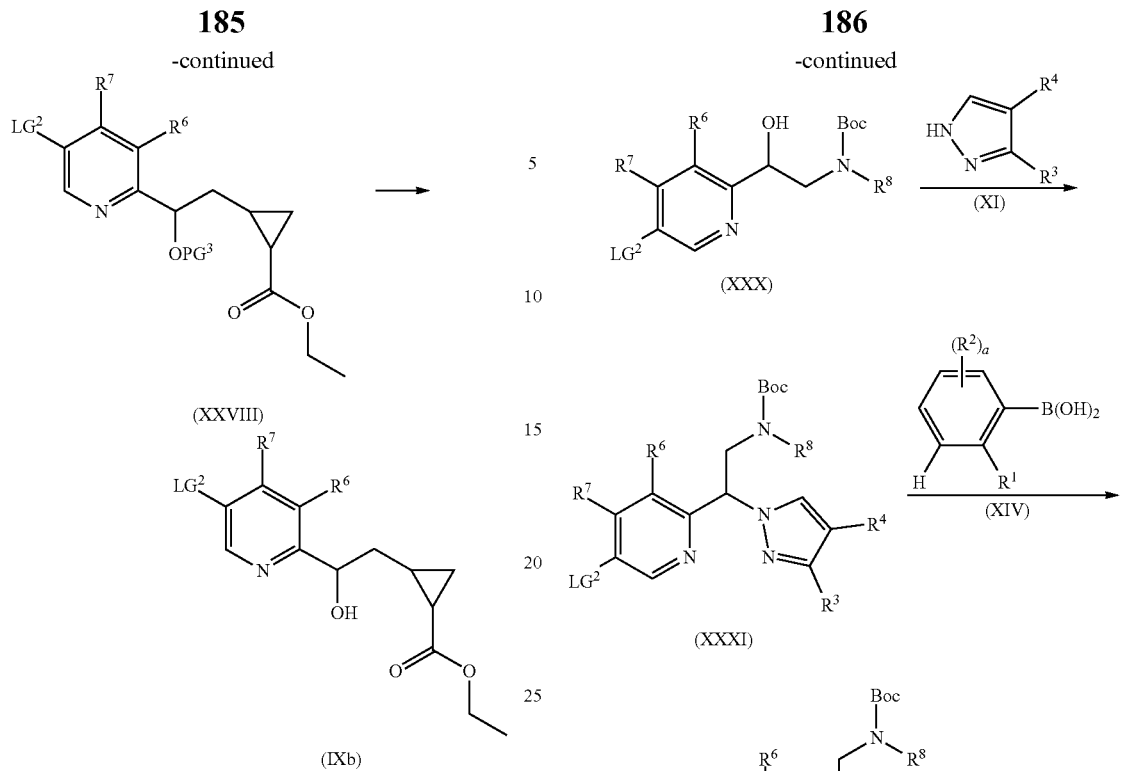

Accordingly, a suitably substituted compound of formula (XXVI), wherein LG² is a suitably selected leaving group such as Br, OTf, I, and the like, a known compound or compound prepared by known methods, is reacted under suitably selected oxygen protecting conditions; to yield the corresponding compound of formula (XXVII), wherein PG² is the corresponding oxygen protecting group. For example, the compound of formula (XXVI) may be reacted with TBSCl and imidazole, in a solvent such as DMF, to yield the corresponding compound of formula (XXVII), wherein PG² is TBS.

The compound of formula (XXVII) is reacted with ethyl 2-diazoacetate, a known compound; in the presence of a suitably selected catalyst such as $Cu(OTf)_2$, and the like; in a solvent such as hexafluoroisopropanol (HFIP); to yield the corresponding compound of formula (XXVIII).

The compound of formula (XXVIII) is de-protected, according to known methods, to yield the corresponding compound of formula (VIIIb). For example, wherein PG² is TBS, the compound of formula (XXVIII) may be reacted with TBAF, in a solvent such as THF; to yield the corresponding compound of formula (VIIIb).

Compounds of formula (I) wherein Y is N and Z is C(R³), and wherein R⁵ is —CH₂—NR⁸R⁹, may alternatively be prepared as described in Scheme 6, below.

Scheme 6

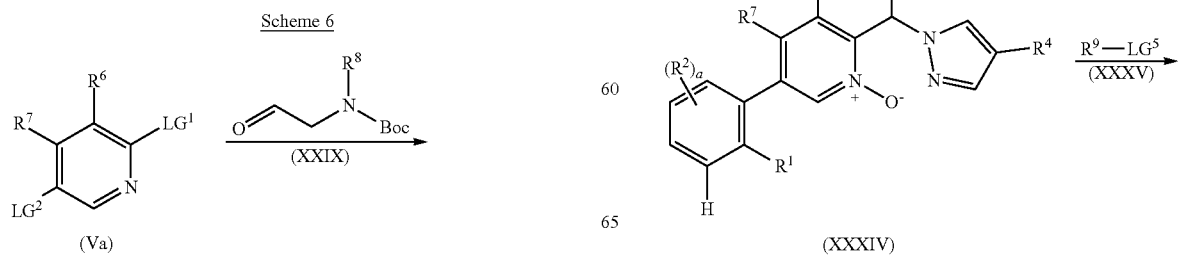

-continued

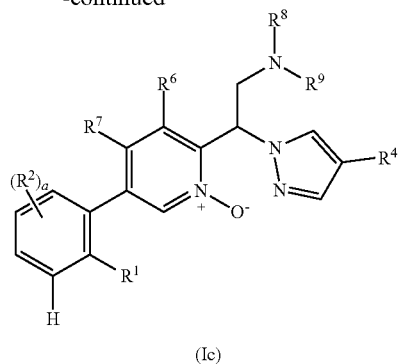

(Ic)

Accordingly, a suitably substituted compound of formula (Va), wherein $LG^1$ is a suitably selected first leaving group such as Br, I, and the like, wherein $LG^2$ is a suitably selected second leaving group such as Br, Cl, and the like, and wherein $LG^1$ and $LG^2$ are selected such that $LG^1$ is selectively reacted with a suitably selected agent such as n-BuLi, i-PrMgCl, and the like; and then reacted with a suitably substituted compound of formula (XXIX), a known compound or compound prepared by known methods (for example, tert-butyl methyl(2-oxoethyl)carbamate or other alternately protected derivative thereof), a known compound; in a suitably selected solvent such as toluene, THF, $Et_2O$, and the like; to yield the corresponding compound of formula (XXX).

The compound of formula (XXX) is reacted with a suitably substituted pyrazole, a compound of formula (XI), a known compound or compound prepared by known methods; in the presence of for example, a mixture of DIAD and $PPh_3$; in a suitably selected solvent such as THF, DCM, and the like; to yield the corresponding compound of formula (XXXI). One skilled in the art will recognize that as described above, the coupling of the suitably substituted pyrazole substituent may be effected using the 1-step process (i.e. according to Mitsunobu reaction conditions) described herein, or the 2-step process as described in more detail the Schemes above, to yield the corresponding compound of formula (XXXI).

The compound of formula (XXXI) is reacted with a suitably substituted compound of formula (XIV), a known compound or compound prepared by known methods; in the presence of a suitably selected catalyst such as $Pd(PPh_3)_4$, $PdCl_2(PPh_3)_2$, $PdCl_2(dppf)$, and the like; in the presence of a suitably selected base such as $K_2CO_3$, $K_3PO_4$, $NaHCO_3$, and the like; in a suitably selected solvent such as 1,4-dioxane, toluene, DMF, and the like; to yield the corresponding compound of formula (XXXII).

The compound of formula (XXXII) is reacted with a suitably selected oxidizing agent such as a mixture of hydrogen peroxide and $ReMeO_3$ (methyltrioxorhenium), and the like; in a suitably selected solvent such as DMF, MeOH, i-PrOH, and the like; to yield the corresponding compound of formula (XXXIII).

The compound of formula (XXXIII) is reacted with to remove the Boc (or alternate) protecting group according to known methods, for example by reacting with an acid such as HCl, in a suitably solvent such as 1,4-dioxane; to yield the corresponding compound of formula (XXXIV).

The compound of formula (XXXIV) is reacted with a suitably substituted compound of formula (XXXV), wherein $LG^5$ is a suitably selected leaving group such as Cl, OMs, OTs, and the like; in the presence of a suitably selected base such as TEA, DIPEA, pyridine, and the like; in a suitably selected solvent such as DCM, DMF, acetonitrile, and the like; to yield the corresponding compound of formula (Ic).

Compounds of formula (I) Y is N, Z is $C(R^3)$ and wherein $R^5$ is optionally substituted 1,2,3-triazol-4-yl may alternatively be prepared as described in Scheme 7, below.

Scheme 7

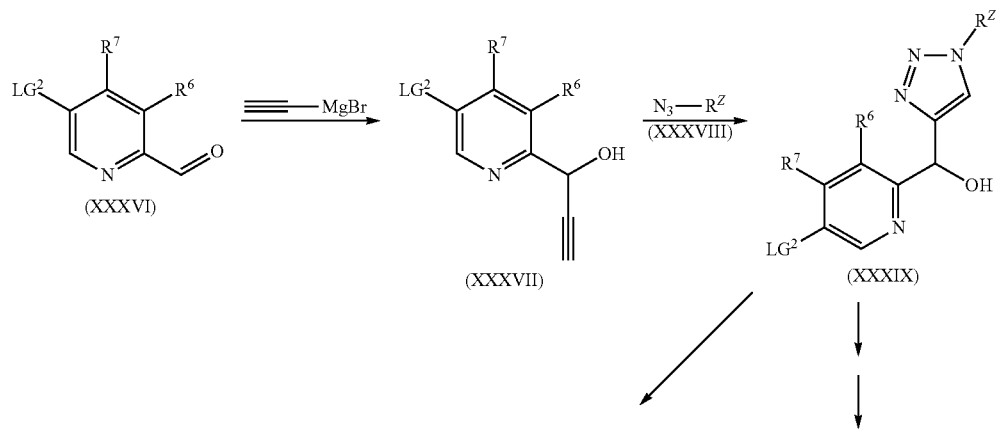

-continued

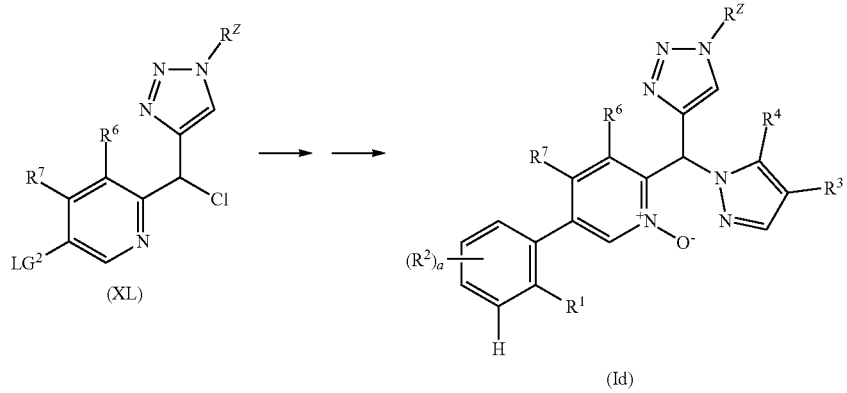

(XL) → (Id)

Accordingly, a suitably substituted compound of formula (XXXVI), wherein $LG^2$ is a suitably selected leaving group such as Br, Cl, and the like, a known compound or compound prepared by known methods, is reacted with a ethynylmagnesium bromide (or alternate reactive ethynyl compound as would be readily recognized by those skilled in the art), a known compound or compound prepared by known methods, in a suitably selected anhydrous solvent such as THF, $Et_2O$, 2-Me-THF, and the like; preferably at a reduced temperature, for example at about −78° C.; to yield the corresponding compound of formula (XXXVII).

The compound of formula (XXXVII) is reacted with a suitably substituted compound of formula (XXXVIII), wherein $R^Z$ is hydrogen or an optional substituent on the 1,2,4-triazol-4-yl as described herein (for example $C_{1-4}$alkyl, fluorinated $C_{1-4}$alkyl, phenyl, etc.), a known compound or compound prepared by known methods; in the presence of a suitably selected catalyst such as $Cu(OAc)_2$, $CuSO_4$, CuI, and the like; in the presence of a suitable selected agent such as sodium L-ascorbate, and the like; in a suitably selected solvent mixture such as t-butanol/water, DCM/water, and the like; to yield the corresponding compound of formula (XXXIX).

The compound of formula (XXXIX) is then reacted as described herein, to yield the corresponding compound of formula (Id). For example, the compound of formula (XXXIX) may be substituted for the compound of formula (IX) in Scheme 1, and reacted as described therein, to yield the corresponding compound of formula (Id).

Alternatively, the compound of formula (XXXIX) is reacted with a suitably selected source of chloride such as $SOCl_2$, and the like; to yield the corresponding compound of formula (XL). The compound of formula (XL) is then reacted as described herein, to yield the corresponding compound of formula (Id). For example, the compound of formula (XL) may be substituted for the compound of formula (XI) in Scheme 1, and reacted as described therein, to yield the corresponding compound of formula (Id).

Compounds of formula (XIII), particularly compounds of formula (XIII) wherein Y is N, Z is $C(R^3)$ and wherein $R^4$ is an optionally substituted 5 membered heterocyclyl may be prepared, for example, as described in Scheme 8, below.

Scheme 8

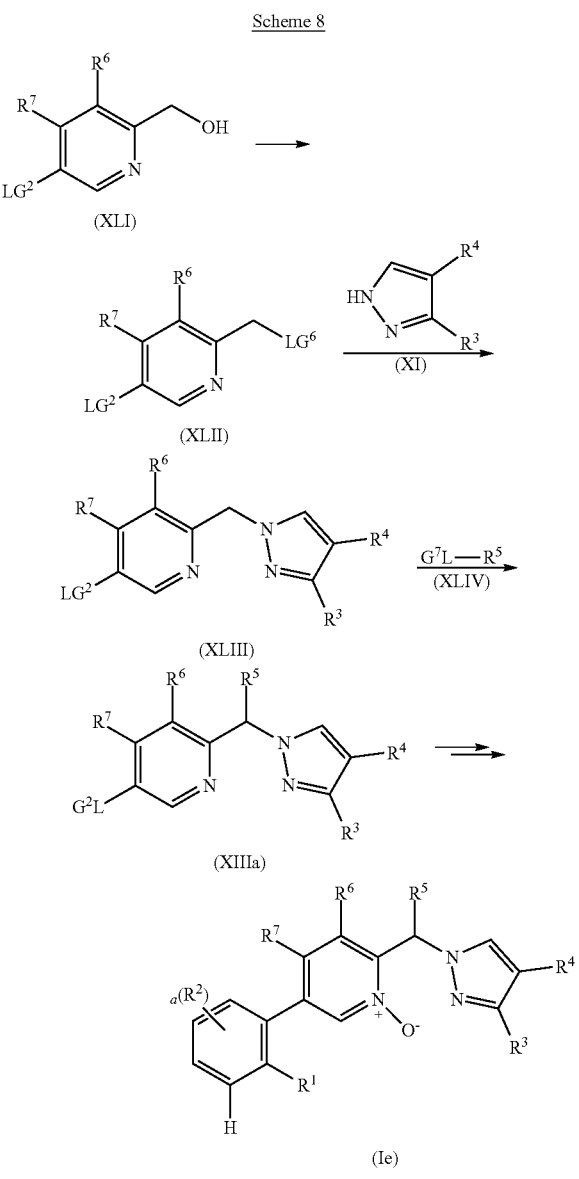

Accordingly, a suitably substituted compound of formula (XLI), wherein $LG^2$ is a suitably selected leaving group such as Br, Cl, and the like, a known compound or compound prepared by known methods, is reacted to convert the terminal OH group to a suitable leaving group, $LG^6$, wherein $LG^6$ is for example OMs, OTf, Cl, Br, and the like, according to known methods, to yield the corresponding compound of formula (XLII).

The compound of formula (XLII) is reacted with a suitably substituted compound of formula (XI), a known compound or compound prepared by known methods; in the presence of a suitably selected base such as $Cs_2CO_3$, NaH, $K_2CO_3$, DIEA, and the like; in a suitably selected solvent such as acetonitrile, DMF, DMSO, and the like; to yield the corresponding compound of formula (XLIII).

The compound of formula (XLIII) is reacted with a suitably substituted compound of formula (XLIV), wherein $LG^7$ is a suitably selected leaving group such as Cl, Br, OMs, and the like, a known compound or compound prepared by known methods; in the presence of a suitably selected base such as LDA, NaH, $LiN(SiMe_3)_2$, and the like; in a suitably selected solvent such as THF, DMF, $Et_2O$, and the like; to yield the corresponding compound of formula (XIIIa).

The compound of formula (XIIIa) is then substituted for the corresponding compound in Schemes 1-3 above (for example, for the compound of formula (XIII) in Scheme 1), and reacted as described therein, to yield the corresponding compound of formula (Ie).

Compounds of formula (XI) may be prepared, for example, as described in Scheme 9, below.

Scheme 9

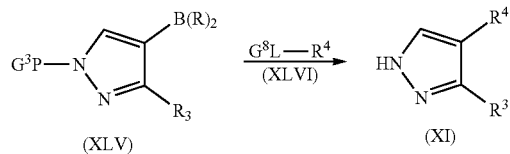

Accordingly, a suitably substituted compound of formula (XLV), wherein $PG^3$ is a suitably selected nitrogen protecting group such as Boc, tetrahydropyran (THP), and the like, and wherein $B(R)_2$ is for example $B(OH)_2$, $B(OCH_3)_2$,

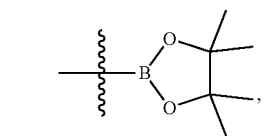 [SMILES: *B1OC(C)(C)C(C)(C)O1]

and the like; a known compound or compound prepared by known methods, is reacted with a suitably substituted compound of formula (XLVI), wherein $LG^8$ is a suitably selected leaving group such as Br, OTf, I, and the like; under Suzuki coupling conditions, for example, in the presence of a suitably selected base such as $K_2CO_3$, $K_3PO_4$, $Cs_2CO_3$, and the like; in the presence of a suitably selected catalyst such as $Pd(PPh_3)_4$, $PdCl_2(PPh_3)_2$, $Pd_2(dba)_3$, and the like; in a suitably selected solvent such as 1,4-dioxane, toluene, THF, and the like; to yield the corresponding compound of formula (XI).

One skilled in the art will recognize that various substituent groups (for example $R^1$, $R^2$, $R^3$, $R^4$, $R^5$, etc.) may be protected prior to any reaction step described above, and then de-protected at a later step in the synthesis, as would be desirable or necessary, according to methods well known to those skilled in the art.

Pharmaceutical Compositions

The present invention further comprises pharmaceutical compositions containing a compound of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus, for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg to about 1000 mg or any amount or range therein, and may be given at a dosage of from about 0.05 mg/day to about 1000 mg/day, or any amount or range therein, about 0.1 mg/day to about 500 mg/day, or any amount or range therein, preferably from about 1 mg/day to about 300 mg/day, or any amount or range therein.

The dosages, however, may be varied depending upon the requirement of the patients, the severity of the condition being treated and the compound being employed. The use of either daily administration or post-periodic dosing may be employed.

Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid pre-formulation composition containing a homogeneous mixture of a compound of the present invention, or a pharmaceutically acceptable salt thereof. When referring to these pre-formulation compositions as homogeneous, it is meant that the active ingredient is dispersed evenly throughout the composition so that the composition may be readily subdivided into equally effective dosage forms such as tablets, pills and capsules. This solid pre-formulation composition is then subdivided into unit dosage forms of the type described above containing from about 0.01 mg to about 1,000 mg, or any amount or range therein, of the active ingredient of the present invention. The tablets or pills of the novel composition can be coated or otherwise compounded to provide a dosage form yielding the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of the treatment and/or prophylaxis of thromboembolic disorders described in the present invention may also be carried out using a pharmaceutical composition comprising any of the compounds as defined herein and a pharmaceutically acceptable carrier. The pharmaceutical composition may contain between about 0.01 mg and about 1000 mg of the compound, or any amount or range therein, preferably from about 0.05 mg to about 300 mg of the compound, or any amount or range therein, more preferably from about 0.1 mg to about 100 mg of the compound, or any amount or range therein, more preferably from about 0.1 mg to about 50 mg of the compound, or any amount or range therein; and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms may include suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in The Handbook of Pharmaceutical Excipients, published by the American Pharmaceutical Association and the Pharmaceutical Society of Great Britain. Methods of formulating pharmaceutical compositions have been described in numerous publications such as Pharmaceutical Dosage Forms: Tablets, Second Edition, Revised and Expanded, Volumes 1-3, edited by Lieberman et al; Pharmaceutical Dosage Forms: Parenteral Medications, Volumes 1-2, edited by Avis et al; and Pharmaceutical Dosage Forms: Disperse Systems, Volumes 1-2, edited by Lieberman et al; published by Marcel Dekker, Inc.

Compounds of the present invention may be administered in any of the foregoing compositions and according to dosage regimens established in the art whenever treatment or prophylaxis of thromboembolic disorders, inflammatory disorders or diseases or conditions in which plasma kallikrein activity is implicated is required.

The daily dosage of the products may be varied over a wide range from about 0.01 mg to about 1,000 mg per adult human per day, or any amount or range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug may be ordinarily supplied at a dosage level of from about 0.005 mg/kg to about 10 mg/kg of body weight per day, or any amount or range therein. Preferably, the range is from about 0.01 to about 5.0 mg/kg of body weight per day, or any amount or range therein, more preferably, from about 0.1 to about 1.0 mg/kg of body weight per day, or any amount or range therein, more preferably, from about 0.1 to about 0.5 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

The following Examples are set forth to aid in the understanding of the invention and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

EXAMPLES

Synthesis Examples

Example A: Intermediate 1

3-Bromo-5,6,7,8-tetrahydroquinolin-8-yl methanesulfonate

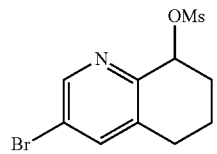 [SMILES: CS(=O)(=O)OC1CCCc2cc(Br)cnc21]

Step 1. 3-Bromo-5,6,7,8-tetrahydroquinoline 1-oxide

To a solution of 3-bromo-5,6,7,8-tetrahydroquinoline (1.0 g, 4.72 mmol, 1.00 equiv) in DMF (10 mL) was added $H_2O_2$ (2.67 g, 23.6 mmol, 5.00 equiv) and $ReMeO_3$ (0.59 g, 2.36 mmol, 0.50 equiv). The resulting mixture was stirred at room temperature for 5 h. The mixture was purified by reverse-phase chromatography (C18, 330 g, $CH_3CN/H_2O$ (0.05% TFA)=10%-70%) to yield the title compound as a yellow oil. (ESI, m/z): 228.0 [M+H]$^+$.

Step 2. 3-Bromo-5,6,7,8-tetrahydroquinolin-8-yl acetate

A solution of 3-bromo-5,6,7,8-tetrahydroquinoline 1-oxide (0.95 g, 4.17 mmol, 1.00 equiv) in acetic anhydride (5 mL) was heated at 55° C. with stirring for 5 h. The reaction mixture was concentrated under reduced pressure and the residue was purified by silica gel chromatography (0-50% EtOAc/petroleum ether) to yield the title compound as a yellow oil. (ESI, m/z): 270.0 [M+H]$^+$.

Step 3. 3-Bromo-5,6,7,8-tetrahydroquinolin-8-ol

To a solution of 3-bromo-5,6,7,8-tetrahydroquinolin-8-yl acetate (0.90 g, 3.332 mmol, 1.00 equiv) in MeOH (20 mL) was added $K_2CO_3$ (2.763 g, 19.991 mmol, 6.0 equiv). The resulting mixture was stirred at room temperature for 5 h, filtered, the filter cake was washed with methanol (20 mL), and the resulting mixture was concentrated to yield the title compound as a yellow solid. (ES, m/z): 228.0 [M+H]$^+$.

Step 4. 3-Bromo-5,6,7,8-tetrahydroquinolin-8-yl methanesulfonate

To a solution of 3-bromo-5,6,7,8-tetrahydroquinolin-8-ol (800 mg, 3.51 mmol, 1.00 equiv) in DCM (20 mL) was added TEA (1.5 g, 10.5 mmol, 3.00 equiv) and methanesulfonyl chloride (600 mg, 5.25 mmol, 1.50 equiv). The resulting mixture was stirred at room temperature for 5 h. The reaction was concentrated. The residue was purified by silica gel chromatography (0-60% EtOAc/petroleum ether) to yield the title compound as a yellow solid. (ES, m/z): 307.9 [M+H]$^+$.

Example B: Intermediate 2

3-Bromo-7-chloro-6,7-dihydro-5H-cyclopenta[b]pyridine

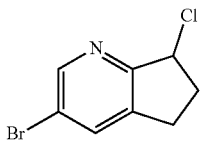 [SMILES: ClC1CCc2cc(Br)cnc21]

To a solution of 3-bromo-6,7-dihydro-5H-cyclopenta[b]pyridin-7-ol (400 mg, 1.87 mmol, 1.00 equiv) in $CH_2Cl_2$ (5 mL) was added methanesulfonyl chloride (428.1 mg, 3.74 mmol, 2.00 equiv) and triethylamine (378.2 mg, 3.74 mmol, 2.00 equiv). The resulting mixture was stirred at room temperature overnight. The reaction was quenched with $H_2O$ (3 mL). The resulting mixture was extracted with ethyl acetate (3×10 mL). The organic layers were combined, dried over $Na_2SO_4$, filtered and concentrated. The resulting residue was purified by silica gel chromatography (0~40% ethyl acetate/petroleum ether) to yield 3-bromo-7-chloro-6,7-dihydro-5H-cyclopenta[b] pyridine as a brown solid. (ES, m/z): 232.0[M+H]$^+$.

Example C: Intermediate 3

4-Chloro-2-(4,4,5,5-tetramethyl-1,3,2-dioxaborolan-2-yl)aniline

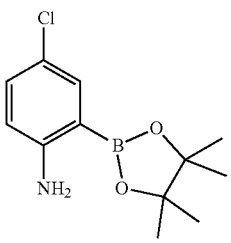 [SMILES: CC1(C)OB(c2cc(Cl)ccc2N)OC1(C)C]

Into a 100-mL three-necked round-bottom flask purged and maintained with an inert atmosphere of nitrogen, was added a solution of 2-bromo-4-chlorobenzenamine (10 g, 48.43 mmol, 1.00 equiv) in DMSO (30 mL), followed by 4,4,5,5-tetramethyl-2-(4,4,5,5-tetramethyl-1,3,2-dioxaborolan-2-yl)-1,3,2-dioxaborolane (18.5 g, 72.9 mmol, 1.50 equiv), potassium acetate (12.2 g, 124.4 mmol, 2.57 equiv) and Pd(dppf)Cl$_2$ (1.1 g, 1.50 mmol, 0.03 equiv). The resulting reaction mixture was stirred overnight at 80° C. in an oil bath. It was concentrated under vacuum. The residue was applied onto a silica gel column with ethyl acetate/petroleum ether (1:50) to yield 4-chloro-2-(4,4,5,5-tetramethyl-1,3,2-dioxaborolan-2-yl)benzenamine as a white solid. LC-MS (ES, m/z): 254 [M+H]$^+$; H-NMR (400 MHz, CDCl$_3$, ppm): 1.51 (s, 12H), 6.53 (d, J=6.6 Hz, 1H), 7.15 (m, 1H), 7.73 (m, 1H).

Example D: Intermediate 4

(6-Amino-3-chloro-2-fluorophenyl)boronic acid

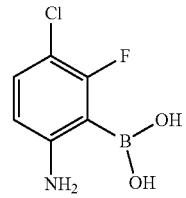

Step 1. N-(4-Chloro-3-fluorophenyl)-2,2,2-trifluoroacetamide

To a solution of 4-chloro-3-fluoroaniline (100 g, 0.69 mol) in ethyl ether (1 L) was added sodium carbonate (127.4 g, 1.2 mol). The resulting mixture was cooled to −10° C., and then trifluoroacetic anhydride (116.2 g, 0.82 mol) was added. The resulting mixture was stirred at room temperature overnight. One liter of petroleum ether was added to the reaction mixture. The resulting mixture was filtered and the filtrate was washed with water, saturated sodium bicarbonate solution, brine and then dried over anhydrous sodium sulfate, filtered and concentrated to yield the N-(4-chloro-3-fluorophenyl)-2,2,2-trifluoroacetamide as a white solid. TLC: R$_f$=0.5 (EA/PE=1:3)

Step 2. (6-Amino-3-chloro-2-fluorophenyl)boronic acid

To a solution of N-(4-chloro-3-fluorophenyl)-2,2,2-trifluoroacetamide (30 g, 124.2 mmol) in THF (300 mL) was added n-butyl lithium (99.4 mL, 248.4 mmol, 2.5 M in hexane) under nitrogen at −78° C. After stirring for 1 h, tri-isopropyl borate (63.0 mL, 273 mmol) was added. After stirring for 1 h, the resulting mixture was maintained under nitrogen and recovered to room temperature for 1 h. To the resulting mixture was then add HCl solution (1 M) at 0° C. The resulting mixture was maintained under nitrogen and stirred at room temperature overnight. To the reaction mixture was added brine (400 mL), and then the mixture was extracted with EA (300 mL×3). The organic layers were combined, dried over anhydrous sodium sulfate, filtered, and concentrated to yield a nearly saturated solution. PE (600 mL) was added to the mixture. After stirring 1 h, the mixture was filtered to yield (6-amino-3-chloro-2-fluorophenyl)boronic acid as a white solid. LC/MS: mass calculated. for $C_6H_6BClFNO_2$: 189.0, measured: 190.1 [M+H]$^+$.

Example E: Intermediate 5

4-Chloro-1-(4-chloro-2-(trimethylstannyl)phenyl)-1H-1,2,3-triazole

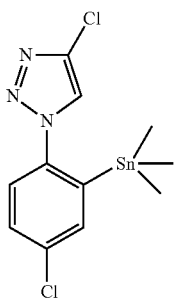 [SMILES: [CH3][Sn]([CH3])([CH3])[c]1cc(Cl)ccc1-n1cc(Cl)nn1]

Step 1. 1-Azido-2-bromo-4-chlorobenzene

To a solution of 2-bromo-4-chlorobenzenamine (5.0 g, 24.22 mmol, 1.00 equiv) in CH$_3$CN (200 mL) was added tert-butyl nitrite (3.7 g, 36.9 mmol, 1.50 equiv) and TMSN$_3$ (4.2 g, 36.455 mmol, 1.50 equiv). The resulting mixture was stirred at 0° C. for 20 min then room temperature for another 2 h. The reaction was quenched with H$_2$O (50 mL). The resulting mixture was extracted with EtOAc (3×100 mL). The organic layers were combined, dried over Na$_2$SO$_4$, filtered and concentrated. The residue was purified by silica gel chromatography (0~40% EtOAc/petroleum ether) to yield 1-azido-2-bromo-4-chlorobenzene as a brown solid.

Step 2. 1-(2-Bromo-4-chlorophenyl)-4-(tributylstannyl)-1H-1,2,3-triazole

To a solution of 1-azido-2-bromo-4-chlorobenzene (3.5 g, 15.1 mmol, 1.00 equiv) in toluene (40 mL) was added tributyl(ethynyl)stannane (9.5 g, 30.2 mmol, 2.00 equiv). The resulting mixture was stirred at 110° C. for 8 h under N$_2$. The reaction was quenched with H$_2$O (40 mL). The resulting mixture was extracted with EtOAc (3×50 mL). The organic layers were combined, dried over Na$_2$SO$_4$, filtered, and concentrated.

The residue was purified by silica gel chromatography (0-10% EtOAc/petroleum ether) to yield 1-(2-bromo-4-chlorophenyl)-4-(tributylstannyl)-1H-1,2,3-triazole as a brown oil. LC-MS: (ES, m/z): 548.2[M+H]$^+$.

Step 3. 1-(2-Bromo-4-chlorophenyl)-4-chloro-1H-1,2,3-triazole

To a solution of 1-(2-bromo-4-chlorophenyl)-4-(tributylstannyl)-1H-1,2,3-triazole (8 g, 14.6 mmol, 1.00 equiv) in CH$_3$CN (80 mL) was added 1-(5-bromopyridin-2-yl)-2-cyclopropylethyl methanesulfonate (2.9 g, 21.7 mmol, 1.50 equiv). The resulting mixture was stirred at 90° C. for 24 h. The reaction was quenched with H$_2$O (40 mL). The resulting mixture was extracted with EtOAc (3×50 mL). The organic layers were combined, dried over Na$_2$SO$_4$, filtered and concentrated. The residue was purified by silica gel chromatography (0-10% EtOAc/petroleum ether) to yield 1-(2-bromo-4-chlorophenyl)-4-chloro-1H-1,2,3-triazole as a light brown solid. LC-MS: (ES, m/z): 291.9 [M+H]$^+$.

Step 4. 4-Chloro-1-(4-chloro-2-(trimethylstannyl)phenyl)-1H-1,2,3-triazole

To a solution of 1-(2-bromo-4-chlorophenyl)-4-chloro-1H-1,2,3-triazole (1.4 g, 4.78 mmol, 1.00 equiv) in toluene (15 mL) was added 1,1,1,2,2,2-hexamethyldistannane (4.7 g, 14.3 mmol, 3.00 equiv) and Pd(PPh$_3$)$_4$ (276.1 mg, 0.24 mmol, 0.05 equiv). The resulting mixture was stirred at 120° C. for 24 h. The reaction was quenched with H$_2$O (20 mL). The resulting mixture was extracted with EtOAc (3×30 mL). The organic layers were combined, dried over Na$_2$SO$_4$, filtered and concentrated. The residue was purified by silica gel chromatography (0-10% EtOAc/petroleum ether) to yield 4-chloro-1-(4-chloro-2-(trimethylstannyl)phenyl)-1H-1,2,3-triazole as a light yellow oil. LC-MS: (ES, m/z): 378.1 [M+H]$^+$.

Example F: Intermediate 6

1-(5-Bromopyridin-2-yl)-3-((tert-butyldimethylsilyl)oxy)propyl methanesulfonate

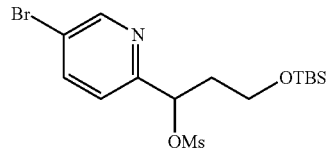 [SMILES: CC(C)(C)[Si](C)(C)OCCC(OS(C)(=O)=O)c1ccc(Br)cn1]

Step 1. 1-(5-Bromopyridin-2-yl)-3-((tert-butyldimethylsilyl)oxy)propan-1-ol

To a mixture of 2,5-dibromopyridine (1.5 g, 6.3 mmol, 1.0 equiv) in toluene (15 mL) at −70° C. under N$_2$, with n-butyllithium (2.7 mL, 6.65 mmol, 1.05 equiv) added dropwise for 30 min, was then added 3-(tert-butyldimethylsilyloxy)propanal (1.31 g, 6.97 mmol, 1.1 equiv) in THF. The reaction was stirred at −70° C. for 1 h. Saturated NH$_4$Cl was added, the mixture was extracted with EA. The combined extracts were washed with water, saturated brine and dried over anhydrous Na$_2$SO$_4$, then concentrated and the resulting residue purified by chromatography on EA/PE (1-30%) to yield 1-(5-bromopyridin-2-yl)-3-(tert-butyldimethylsilyloxy)propan-1-ol as a yellow oil. LC/MS: mass calculated, for C$_{1-4}$H$_{24}$BrNO$_2$Si: 346.335, measured: 346.10 [M+H]$^+$.

Step 2. 1-(5-Bromopyridin-2-yl)-3-((tert-butyldimethylsilyl)oxy)propyl methanesulfonate To a mixture of 1-(5-bromopyridin-2-yl)-3-(tert-butyldimethylsilyloxy)propan-1-ol (1.3 g, 3.75 mmol, 1.0 equiv) in DCM (15 mL) with triethylamine (1.04 mL, 7.51 mmol, 2.0 equiv) was added methanesulfonyl chloride (0.35 mL, 4.5 mmol, 1.2 equiv). The resulting mixture was stirred at room temperature for 2 h. Water was added, the mixture was extracted with EA. The combined extracts were washed with water, saturated brine, and dried over anhydrous Na$_2$SO$_4$. The resulting mixture was concentrated and purified by chromatography on EA/PE (1-15%) to yield 1-(5-bromopyridin-2-yl)-3-(tert-butyldimethylsilyloxy)propyl methanesulfonate as a yellow oil. LC/MS: mass calculated, for C$_{15}$H$_{26}$BrNO$_4$SSi: 424.426, measured: 425.90 [M+H]$^+$.

Example G: Intermediate 7

1-(5-Bromopyridin-2-yl)-2-(4-fluorophenyl)ethyl methanesulfonate

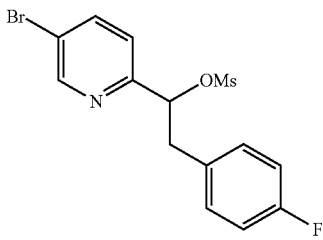 [SMILES: CS(=O)(=O)OC(Cc1ccc(F)cc1)c1ccc(Br)cn1]

Step 1. (4-Fluorobenzyl)magnesium bromide

To a mixture of Mg (1.1 g, 48.4 mmol, 4.5 equiv) and 1,2-dibromoethane (202 mg, 1.08 mmol, 0.1 equiv) in THF (15 mL) was added 1-(bromomethyl)-4-fluorobenzene (2.0 mL, 16.1 mmol, 1.5 equiv) at 0° C. for 30 min under nitrogen. To the reaction mixture was then added to a solution of 5-bromopicolinaldehyde (2 g, 10.8 mmol, 1.0 equiv) in THF (15 mL) under $N_2$. The reaction was stirred at −70° C. for 1 h. Saturated $NH_4Cl$ was added, the mixture was extracted with EA. The combined extracts were washed with water, saturated brine, and dried over anhydrous $Na_2SO_4$. The resulting mixture was concentrated and the residue purified with silica gel column with EA/PE (1-25%) to yield 1-(5-bromopyridin-2-yl)-2-(4-fluorophenyl)ethanol as a yellow solid. LC/MS: mass calculated, for $C_{13}H_{11}BrFNO$: 296.14, measured: 295.9 $[M+H]^+$.

Step 2. 1-(5-Bromopyridin-2-yl)-2-(4-fluorophenyl)ethan-1-ol

To a mixture of 1-(5-bromopyridin-2-yl)-2-(4-fluorophenyl)ethanol (1.0 g, 3.38 mmol, 1.0 equiv) in DCM (10 mL) with triethylamine (0.94 mL, 6.75 mmol, 2.0 equiv) was added methanesulfonyl chloride (0.31 mL, 4.15 mmol, 1.2 equiv). The reaction was stirred at room temperature for 1 h. Water was added, and the mixture was extracted with DCM. The combined extracts were washed with water, saturated brine, and dried over anhydrous $Na_2SO_4$. The resulting mixture was concentrated and purified by chromatography on EA/PE (1-25%) to yield 1-(5-bromopyridin-2-yl)-2-(4-fluorophenyl)ethyl methanesulfonate as a yellow solid. LC/MS: mass calculated, for $C_{14}H_{13}BrFNO_3S$: 374.225, measured: 375.95 $[M+H]^+$.

Step 3. 1-(5-Bromopyridin-2-yl)-2-(4-fluorophenyl)ethyl methanesulfonate

To a mixture of 1-(5-bromopyridin-2-yl)-2-(4-fluorophenyl)ethyl methanesulfonate (750 mg, 2.00 mmol, 1.0 equiv) and sodium hydride (979.5 mg, 3.0 mmol, 1.5 equiv) in $CH_3CN$ (10 mL) was added tert-butyl 4-(1H-pyrazol-4-yl)benzoate (587.5 mg, 2.41 mmol, 1.2 equiv). The resulting mixture was stirred at 0° C. for 4 h. Water was added, and the mixture was extracted with EA. The combined extracts were washed with water, saturated brine, and dried over anhydrous $Na_2SO_4$. The resulting mixture was concentrated and then purified by chromatography on EA/PE (1-40%) to yield tert-butyl 4-(1-(1-(5-bromopyridin-2-yl)-2-(4-fluorophenyl)ethyl)-1H-pyrazol-4-yl)benzoate as a yellow oil. LC/MS: mass calculated, for $C_{27}H_{25}BrFN_3O_2$: 522.409, measured: 524.15 $[M+H]^+$.

Example H: Intermediate 8

1-(5-Bromo-3-fluoropyridin-2-yl)-2-cyclopropyl-ethyl methanesulfonate

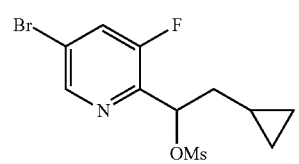 [SMILES: CS(=O)(=O)OC(CC1CC1)c1ncc(Br)cc1F]

Step 1. 2-Cyclopropyl-N-methoxy-N-methylacetamide

To a mixture of 2-cyclopropylacetic acid (15 g, 149.8 mmol, 1.0 equiv) in DCM (200 mL) were added CDI (26.7 g, 164.8 mmol, 1.1 equiv) in portions and N,O-dimethylhydroxylamine hydrochloride (16.1 g, 164.8 mmol, 1.1 equiv). The reaction was stirred at room temperature for 4 h. Water was added, and the resulting mixture was extracted with EA. The combined extracts were washed with water, saturated brine, and dried over anhydrous $Na_2SO_4$. The resulting mixture was concentrated to yield methoxy(methyl)amino 2-cyclopropylacetate as a yellow oil. $^1H$ NMR (300 MHz, Chloroform-d) δ 3.67 (s, 3H), 3.20 (s, 3H), 2.36 (d, J=7.0 Hz, 2H), 1.18-1.00 (m, 1H), 0.62-0.44 (m, 2H), 0.17 (dt, J=6.1, 4.6 Hz, 2H).

Step 2. 1-(5-Bromo-3-fluoropyridin-2-yl)-2-cyclopropylethan-1-one

To a solution of 2,5-dibromo-3-fluoropyridine (1 g, 3.9 mmol, 1.00 equiv) in toluene (10 mL) was added n-BuLi (1.6 mL, 4.12 mmol, 1.05 equiv) and 2-cyclopropyl-N-methoxy-N-methylacetamide (618.0 mg, 4.32 mmol, 1.10 equiv) at −78° C. The resulting mixture was stirred at −78° C. for 2 h. The reaction was quenched with $H_2O$ (10 mL). The resulting mixture was extracted with EtOAc (3×20 mL). The organic layers were combined, dried over $Na_2SO_4$, filtered and concentrated. The residue was purified by silica gel chromatography (0~30% EtOAc/petroleum ether) to yield 1-(5-bromo-3-fluoropyridine-2-yl)-2-cyclopropylethanone as light yellow oil.

Step 3. 1-(5-Bromo-3-fluoropyridin-2-yl)-2-cyclopropylethan-1-ol

To a solution of 1-(5-bromo-3-fluoropyridin-2-yl)-2-cyclopropylethanone (600 mg, 2.33 mmol, 1.00 equiv) in $CH_3OH$ (6 mL) was added $NaBH_4$ (175.9 mg, 4.65 mmol, 2.00 equiv) at 0° C. The resulting mixture was stirred at 0° C. for 2 h. The reaction was quenched with ice water (5 mL). The resulting mixture was extracted with EtOAc (3×10 mL). The organic layers were combined, dried over $Na_2SO_4$, filtered and concentrated. The residue was purified by silica gel chromatography (0~30% EtOAc/petroleum ether) to yield 1-(5-bromo-3-fluoropyridin-2-yl)-2-cyclopropylethanol as a light yellow oil. LC-MS: (ES, m/z): 260.1$[M+H]^+$.

Step 4. 1-(5-Bromo-3-fluoropyridin-2-yl)-2-cyclopropylethyl methanesulfonate To a solution of 1-(5-bromo-3-fluoropyridin-2-yl)-2-cyclopropylethanol (490 mg, 1.88 mmol, 1.00 equiv) in CH₂Cl₂ (5 mL) was added triethylamine (381.3 mg, 3.77 mmol, 2.00 equiv) and MsCl (431.6 mg, 3.77 mmol, 2.00 equiv) at 0° C. The resulting mixture was stirred at room temperature for 2 h. The reaction was quenched with H₂O (5 mL). The resulting mixture was extracted with EtOAc (3×10 mL). The organic layers were combined, dried over Na₂SO₄, filtered and concentrated. The residue was purified by silica gel chromatography (0~30% EtOAc/petroleum ether) to yield 1-(5-bromo-3-fluoropyridin-2-yl)-2-cyclopropylethyl methanesulfonate as a light yellow oil. LC-MS: (ES, m/z): 338.1 [M+H]⁺.

Example I: Intermediate 9

1-(5-Bromo-3-methylpyridin-2-yl)-2-cyclopropylethyl methanesulfonate

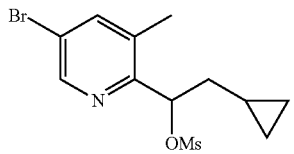 [SMILES: Cc1cc(Br)cnc1C(CC1CC1)OS(C)(=O)=O]

The title compound was prepared according to the procedure described in 1-(5-bromo-3-fluoropyridin-2-yl)-2-cyclopropylethyl methanesulfonate (Intermediate 8, Example H), substituting 2,5-dibromo-3-methylpyridine for 2,5-dibromo-3-fluoropyridine in Step 2.

Example J: Intermediate 10

1-(5-Bromo-4-methoxypyridin-2-yl)-2-cyclopropylethyl methanesulfonate

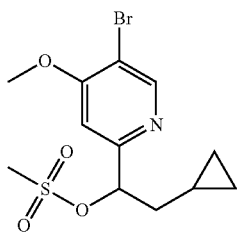 [SMILES: COc1cc(C(CC2CC2)OS(C)(=O)=O)ncc1Br]

Step 1. 1-(5-Bromo-4-methoxypyridin-2-yl)-2-cyclopropylethan-1-one

To a solution of 2, 5-dibromo-4-methoxypyridine (2.0 g, 11.2 mmol, 1.00 equiv) in toluene (30 mL) under nitrogen was added n-butyllithium (4.9 mL, 12.4 mmol, 2.50 M in THF, 1.10 equiv) at −78° C. and the solution was stirred for 1 h at this temperature. To the resulting solution was then added a solution of 2-cyclopropyl-N-methoxy-N-methylacetamide (1.93 g, 13.5 mmol, 1.20 equiv) in toluene (5 mL) at −78° C. and the resulting mixture was maintained stirring for 2 h at −78° C. The resulting solution was quenched with sat. NH₄Cl (aqueous) and extracted with ethyl acetate twice. The combined organic layer was washed with brine, dried over Na₂SO₄ and concentrated. The residue was purified by silica gel chromatography (0-50% EtOAc/petroleum ether) to yield 1-(5-bromo-4-methoxypyridin-2-yl)-2-cyclopropylethanone as a white solid. LC-MS: (ES, m/z): 270.0, 272.0 [M+H, M+H+2]⁺.

Step 2. 1-(5-Bromo-4-methoxypyridin-2-yl)-2-cyclopropylethan-1-ol

To a solution of 1-(5-bromo-4-methoxypyridin-2-yl)-2-cyclopropylethanone (270 mg, 1.00 mmol, 1.00 equiv) in methanol (5 mL) was added sodium borohydride (45 mg, 1.12 mmol, 1.20 equiv) at 0° C. and the resulting solution was stirred for 1 h at room temperature. The reaction was quenched with water and extracted with EtOAc twice. The combined organic layers were washed with water and brine. The organic layer was dried over Na₂SO₄ and concentrated. The residue was purified by silica gel chromatography (0-50% EtOAc/petroleum ether) to yield 1-(5-bromo-4-methoxypyridin-2-yl)-2-cyclopropylethanol as colorless oil. LC-MS: (ES, m/z): 272.0, 274.0 [M+H, M+H+2]⁺.

Step 3. 1-(5-Bromo-4-methoxypyridin-2-yl)-2-cyclopropylethyl methanesulfonate To a mixture of 1-(5-bromo-4-methoxypyridin-2-yl)-2-cyclopropylethan-1-ol (240 mg, 0.88 mmol, 1.00 equiv) and triethylamine (267.7 mg, 2.65 mmol, 3.00 equiv) in DCM (3 mL) was added methanesulfonyl chloride (121.2 mg, 1.06 mmol, 1.20 equiv) at 0° C. and the resulting solution was stirred for 2 h at room temperature. The reaction was washed with water and brine. The organic layer was dried over Na₂SO₄ and concentrated. The residue was purified by silica gel chromatography (0-50% EtOAc/petroleum ether) to yield 1-(5-bromo-4-methoxypyridin-2-yl)-2-cyclopropylethyl methanesulfonate as a colorless oil. LC-MS: (ES, m/z): 349.9, 351.9 [M+H, M+H+2]⁺.

Example K: Intermediate 11

1-(5-Bromopyridin-2-yl)-3-methoxypropyl methanesulfonate

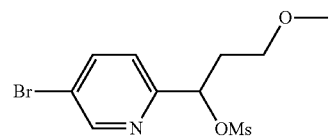 [SMILES: COCCC(OS(C)(=O)=O)c1ccc(Br)cn1]

The title compound was prepared according to the procedure described in 1-(5-bromo-3-fluoropyridin-2-yl)-2-cyclopropylethyl methanesulfonate (Intermediate 8, Example H), substituting 2,5-dibromo-pyridine for 2,5-dibromo-3-fluoropyridine in Step 2.

Example L: Intermediate 12

1-(5-Bromopyridin-2-yl)-2-phenylethyl methanesulfonate

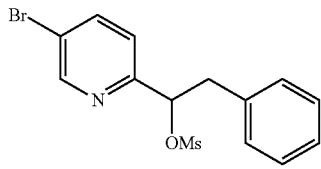 [SMILES: CS(=O)(=O)OC(Cc1ccccc1)c1ccc(Br)cn1]

Step 1. 1-(5-Bromopyridin-2-yl)-2-phenylethan-1-ol

To a solution of 2,5-dibromopyridine (10.0 g, 42.2 mmol, 1.00 equiv.) in toluene (100 mL) was added n-butyllithium (18.5 mL, 2.5 M THE solution, 46.3 mmol, 1.10 equiv.) at −78° C., and then after 1 h, 2-phenylacetaldehyde was added (6.1 g, 50.8 mmol). The resulting mixture was stirred at −78° C. for 2 h. The reaction was quenched with saturated aqueous solution of NH$_4$Cl (100 mL). The resulting mixture was extracted with CH$_2$Cl$_2$ (3×100 mL) and the organic layers were combined and concentrated to yield 1-(5-bromopyridin-2-yl)-2-phenylethanol as a yellow solid. LC-MS: (ES, m/z): 278.0 [M+H]$^+$.

Step 2. 1-(5-Bromopyridin-2-yl)-2-phenylethyl methanesulfonate

To a solution of 1-(5-bromopyridin-2-yl)-2-phenylethanol (9.7 g, 34.9 mmol, 1.00 equiv.) in CH$_2$Cl$_2$ (100 mL) was added pyridine (8.3 g, 104.99 mmol, 3.00 equiv.) and MsCl (8.0 g, 69.8 mmol, 2.00 equiv.).

The resulting mixture was stirred at room temperature for overnight, then quenched with H$_2$O (100 mL. The resulting mixture was extracted with CH$_2$Cl$_2$ (3×100 mL). The organic layers were combined, dried over Na$_2$SO$_4$, filtered and concentrated. The residue was purified by silica gel chromatography (0-30% EA/PE) to yield 1-(5-bromopyridin-2-yl)-2-phenylethyl methanesulfonate as a yellow solid. LC-MS: (ES, m/z): 356.0[M+H]$^+$.

Example M: Intermediate 13

1-(5-Bromo-3-fluoropyridin-2-yl)-2-phenylethyl methanesulfonate

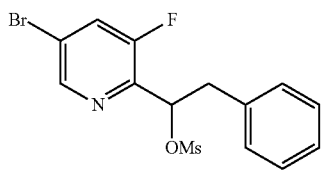 [SMILES: CS(=O)(=O)OC(Cc1ccccc1)c1ncc(Br)cc1F]

The title compound was prepared according to the procedure described in Example H, substituting 2,5-dibromo-3-fluoropyridine for 2,5-dibromopyridine in 1-(5-bromopyridin-2-yl)-2-phenylethyl methanesulfonate (Intermediate 12).

Example N: Intermediate 14

1-(5-Bromopyridin-2-yl)-2-((R)-tetrahydro-2H-pyran-2-yl)ethyl methanesulfonate

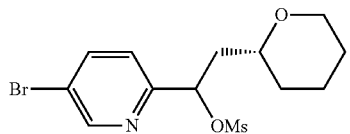 [SMILES: CS(=O)(=O)OC(C[C@H]1CCCCO1)c1ccc(Br)cn1]

The title compound was prepared according to the procedure described in 1-(5-bromo-3-fluoropyridin-2-yl)-2-cyclopropylethyl methanesulfonate (Example H, Intermediate 8) substituting 2-(tetrahydro-2H-pyran-2-yl)acetic acid for 2-cyclopropylacetic acid in Step 1.

Example 1: 2-(1-(4-(4-Carboxyphenyl)-1H-pyrazol-1-yl)-2-cyclopropylethyl)-5-(5-chloro-2-(1H-tetrazol-1-yl)phenyl)pyridine 1-oxide

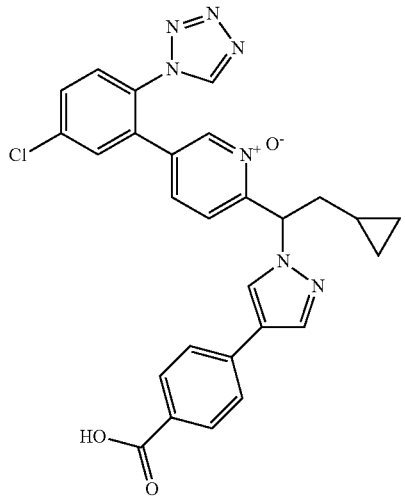

Step 1: tert-Butyl 4-(1-(1-(5-(2-amino-5-chlorophenyl)pyridin-2-yl)-2-cyclopropylethyl)-1H-pyrazol-4-yl)benzoate A round bottom flask was charged with tert-butyl 4-(1-(1-(5-bromopyridin-2-yl)-2-cyclopropylethyl)-1H-pyrazol-4-yl)benzoate (700 mg, 1.49 mmol, 1.0 eq.). To the flask was then added 1,4-dioxane (10 ml) and H$_2$O (2 mL), followed by 4-chloro-2-(4,4,5,5-tetramethyl-1,3,2-dioxaborolan-2-yl)benzenamine (758 mg, 3.0 mmol, 2.0 eq.), K$_2$CO$_3$ (620 mg, 4.5 mmol, 3.0 eq.), and Pd(PPh$_3$)$_4$ (86 mg, 0.08 mmol, 0.05 eq.). The flask was evacuated and maintained under N$_2$. The mixture was stirred at 100° C. for 2 h under N$_2$, cooled to room temperature, quenched with H$_2$O and extracted with EtOAc. The organic layer was washed with brine, dried over Na$_2$SO$_4$, filtered and concentrated. The resulting residue was purified by silica gel chromatography (0→5% CH$_3$OH/CH$_2$Cl$_2$) to yield tert-butyl 4-(1-(1-(5-(2-amino-5-chlorophenyl)pyridin-2-yl)-2-cyclopropylethyl)-1H-pyrazol-4-yl)

benzoate as a light yellow solid. LC/MS: mass calculated for $C_{30}H_{31}ClN_4O_2$: 514.21, measured (ESI, m/z): 515.30 $[M+H]^+$.

Step 2. 4-(1-(1-(5-(2-Amino-5-chlorophenyl)pyridin-2-yl)-2-cyclopropylethyl)-1H-pyrazol-4-yl)benzoic acid To a solution of tert-butyl 4-(1-(1-(5-(2-amino-5-chlorophenyl)pyridin-2-yl)-2-cyclopropylethyl)-1H-pyrazol-4-yl) benzoate (700 mg, 1.36 mmol, 1.0 eq.) in $CH_2Cl_2$ (7 mL) was added TFA (1.8 mL). The resulting mixture was stirred at room temperature for 2 h, then concentrated to yield 4-(1-(1-(5-(2-amino-5-chlorophenyl)pyridin-2-yl)-2-cyclopropylethyl)-1H-pyrazol-4-yl)benzoic acid as a brown solid, which was used in the next step without further purification. LC/MS: mass calculated for $C_{26}H_{23}ClN_4O_2$: 458.15, measured (ESI, m/z): 459.25 $[M+H]^+$.

Step 3. 4-(1-(1-(5-(5-chloro-2-(1H-tetrazol-1-yl)phenyl)pyridin-2-yl)-2-cyclopropylethyl)-1H-pyrazol-4-yl)benzoic acid $TMSN_3$ (879 mg, 7.6 mmol) and trimethoxymethane (1.6 g, 15.3 mmol) were added sequentially to a solution of 4-(1-(1-(5-(2-amino-5-chlorophenyl)pyridin-2-yl)-2-cyclopropylethyl)-1H-pyrazol-4-yl)benzoic acid (700 mg from step 2) in acetic acid (14 mL). The resulting mixture was stirred at room temperature overnight.

The reaction was quenched with $H_2O$. The resulting mixture was extracted with EtOAc. The organic layers were combined, dried over $Na_2SO_4$, filtered and concentrated. The residue was purified by reverse phase column chromatography on C18 (0-*40% $CH_3CN/H_2O$) to yield 4-(1-(1-(5-(5-chloro-2-(1H-tetrazol-1-yl)phenyl)pyridin-2-yl)-2-cyclopropylethyl)-1H-pyrazol-4-yl)benzoic acid as an off-white solid. LC/MS: mass calculated for $C_{27}H_{22}ClN_7O_2$: 511.15, measured (ESI, m/z): 511.95 $[M+H]^+$.

Step 4. 2-(1-(4-(4-Carboxyphenyl)-1H-pyrazol-1-yl)-2-cyclopropylethyl)-5-(5-chloro-2-(1H-tetrazol-1-yl)phenyl)pyridine 1-oxide To a solution of 4-(1-(1-(5-(5-chloro-2-(1H-tetrazol-1-yl)phenyl)pyridin-2-yl)-2-cyclopropylethyl)-1H-pyrazol-4-yl) benzoic acid (100 mg, 0.20 mmol, 1.0 eq.) in $CH_3OH$ (2.5 mL) was added methyltrioxorhenium (VII) (24 mg, 0.10 mmol, 0.5 eq.) and $H_2O_2$ (111 mg, 0.98 mmol, 5.0 eq.). The resulting mixture was stirred at room temperature for 2 h, then quenched with $NaHSO_3$. The resulting mixture was extracted with EtOAc. The organic layer was washed with brine, dried over $Na_2SO_4$, filtered and concentrated.

The resulting residue was purified by reverse phase chromatography on C18 column (0→50% $CH_3CN/H_2O$) to yield 2-(1-(4-(4-carboxyphenyl)-1H-pyrazol-1-yl)-2-cyclopropylethyl)-5-(5-chloro-2-(1H-tetrazol-1-yl)phenyl)pyridine 1-oxide as a white solid.

LC/MS: mass calculated for $C_{27}H_{22}ClN_7O_3$: 527.15, measured (ES, m/z): 528.25 $[M+H]^+$. $^1H$ NMR (300 MHz, DMSO-$d_6$) δ 9.68 (s, 1H), 8.65 (s, 1H), 8.29 (s, 1H), 8.12 (s, 1H), 7.84-7.97 (m, 3H), 7.78-7.90 (m, 2H), 7.70-7.76 (m, 2H), 7.22 (d, J=8.3 Hz, 1H), 6.96 (d, J=8.3, 1H), 6.10 (dd, J=9.8, 4.2 Hz, 1H), 2.33-2.42 (m, 1H), 1.84-1.92 (m, 1H), 0.56-0.64 (m, 1H), 0.29-0.40 (m, 2H), 0.11-0.17 (m, 1H), 0.01-0.06 (m, 1H).

Example 2: 5-(5-Chloro-2-(1H-tetrazol-1-yl)phenyl)-2-(2-cyclopropyl-1-(4-(4-((methoxycarbonyl) amino)phenyl)-1H-pyrazol-1-yl)ethyl)pyridine 1-oxide

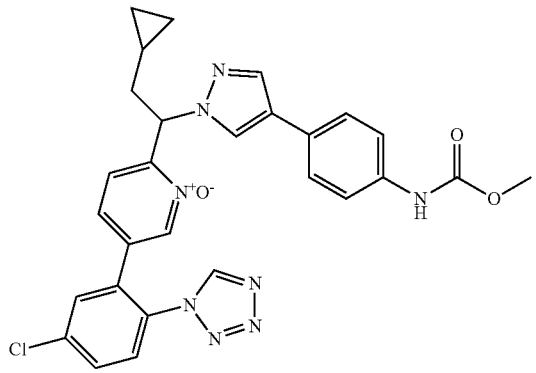

Step 1: Methyl 4-bromophenylcarbamate

To a solution of 4-bromobenzenamine (2 g, 11.63 mmol, 1.0 equiv) in $CH_2Cl_2$ (20 mL) was added pyridine (2.7 g, 34.13 mmol, 3.0 equiv) and $ClCOOCH_3$ (1.3 g, 13.75 mmol, 1.2 equiv). The resulting mixture was stirred at room temperature for 2 h. The reaction was quenched with $H_2O$. The resulting mixture was extracted with EtOAc. The organic layers were combined, dried over $Na_2SO_4$, filtered and concentrated. The resulting residue was purified by silica gel chromatography (0→10% EtOAc/petroleum ether) to yield methyl 4-bromophenylcarbamate as a white solid. LC/MS: mass calculated for $C_8H_8BrNO_2$: 228.97, measured (ES, m/z): 230.10 $[M+H]^+$.

Step 2: Methyl 4-(1H-pyrazol-4-yl)phenylcarbamate

To a solution of methyl 4-bromophenylcarbamate (2.5 g, 10.87 mmol, 1.0 equiv) in 1,4-dioxane/$H_2O$ (25 mL/5 mL) was added tert-butyl 4-(4,4,5,5-tetramethyl-1,3,2-dioxaborolan-2-yl)-1H-pyrazole-1-carboxylate (4.8 g, 16.32 mmol, 1.5 equiv), $K_2CO_3$ (4.5 g, 32.56 mmol, 3.0 equiv) and $Pd(PPh_3)_4$ (0.6 g, 0.52 mmol, 0.05 equiv). The resulting mixture was stirred at 100° C. overnight under $N_2$. The reaction was quenched with $H_2O$.

The resulting mixture was extracted with EtOAc. The organic layers were combined, dried over $Na_2SO_4$, filtered and concentrated. The resulting residue was purified by silica gel chromatography (0→10% $CH_3OH/CH_2Cl_2$) to yield methyl 4-(1H-pyrazol-4-yl)phenylcarbamate as a light brown solid. LC/MS: mass calculated for $C_{11}H_{11}N_3O_2$: 217.09, measured (ES, m/z): 218.20 $[M+H]^+$.

Step 3: Methyl 4-(1-(1-(5-bromopyridin-2-yl)-2-cyclopropylethyl)-1H-pyrazol-4-yl)phenylcarbamate A mixture of 1-(5-bromopyridin-2-yl)-3-methoxypropyl methanesulfonate (1.0 g, 3.1 mmol, 1.0 eq.), methyl 4-(1H-pyrazol-4-yl)phenylcarbamate (746 mg, 3.4 mmol, 1.10 eq.) and cesium carbonate (2.5 g, 7.8 mmol, 2.50 eq.) in acetonitrile (10 mL) was stirred at 70° C. overnight. The reaction was diluted with water and extracted with EtOAc twice. The combined organic layer was washed with brine, dried over $Na_2SO_4$ and concentrated. The resulting residue was purified by silica gel chromatography (0-30% EtOAc/petroleum ether) to yield methyl 4-(1-(1-(5-bromopyridin-2-yl)-2-cyclopropylethyl)-1H-pyrazol-4-yl)phenylcarbamate as a white solid. LC/MS (ESI, m/z): mass calculated. for $C_{21}H_{21}BrN_4O_2$: 440.1, measured: 441.1, 443.1 [M+H, M+H+2]$^+$.

Step 4: Methyl 4-(1-(1-(5-(2-amino-5-chlorophenyl) pyridin-2-yl)-2-cyclopropylethyl)-1H-pyrazol-4-yl) phenylcarbamate To a 50 ml round bottom flask containing methyl (4-(1-(1-(5-bromopyridin-2-yl)-2-cyclopropylethyl)-1H-pyrazol-4-yl)phenyl)carbamate (400 mg, 0.91 mmol) in 1,4-dioxane and $H_2O$ (6.6 ml) was added 4-chloro-2-(4,4,5,5-tetramethyl-1,3,2-dioxaborolan-2-yl)benzenamine (459.6 mg, 1.8 mmol), $K_2CO_3$ (375.8 mg, 2.72 mmol), and Pd(PPh$_3$)$_4$ (52.4 mg, 0.05 mmol). The flask was evacuated and refilled with $N_2$. The mixture was stirred at 100° C. for 2 h, diluted with $H_2O$ (10 mL) and extracted with EtOAc (3×20 mL). The organic layer was washed with brine, dried over $Na_2SO_4$, filtered, and concentrated under reduced pressure. The resulting residue was purified by silica gel chromatograph (0-5% $CH_3OH/CH_2Cl_2$) to yield methyl 4-(1-(1-(5-(2-amino-5-chlorophenyl)pyridin-2-yl)-2-cyclopropylethyl)-1H-pyrazol-4-yl)phenylcarbamate as a light yellow solid. LC/MS (ESI, m/z): mass calculated. for $C_{27}H_{26}ClN_5O_2$: 487.2, measured: 488.2[M+H]$^+$.

Step 5: Methyl 4-(1-(1-(5-(5-chloro-2-(1H-tetrazol-1-yl)phenyl)pyridin-2-yl)-2-cyclopropylethyl)-1H-pyrazol-4-yl)phenylcarbamate TMSN$_3$ (413.2 mg, 3.587 mmol) and trimethoxymethane (761.1 mg, 7.2 mmol) were added sequentially to a solution of methyl 4-(1-(1-(5-(2-amino-5-chlorophenyl)pyridin-2-yl)-2-cyclopropylethyl)-1H-pyrazol-4-yl)phenylcarbamate (350 mg, 0.72 mmol) in acetic acid (15 ml). The resulting mixture was stirred at room temperature overnight, then diluted with $H_2O$ (10 mL) and extracted with EtOAc (3×15 mL). The organic layers were combined, dried over $Na_2SO_4$, filtered and concentrated. The residue was purified by reverse phase chromatography on C18 column (0~40% $CH_3CN/H_2O$) to yield methyl 4-(1-(1-(5-(5-chloro-2-(1H-tetrazol-1-yl)phenyl)pyridin-2-yl)-2-cyclopropylethyl)-1H-pyrazol-4-yl)phenylcarbamate as a yellow solid. LC/MS (ESI, m/z): mass calculated. for $C_{28}H_{25}ClN_8O_2$: 540.2, measured: 541.4[M+H]$^+$.

Step 6: 5-(5-Chloro-2-(1H-tetrazol-1-yl)phenyl)-2-(2-cyclopropyl-1-(4-(4-(methoxycarbonylamino) phenyl)-1H-pyrazol-1-yl)ethyl)pyridine 1-oxide Methyl 4-(1-(1-(5-(5-chloro-2-(1H-tetrazol-1-yl)phenyl) pyridin-2-yl)-2-cyclopropylethyl)-1H-pyrazol-4-yl)phenyl-carbamate (250 mg, 0.46 mmol, 1.0 eq.) was dissolved in $CH_3OH$ (6 mL). To the resulting mixture was then added methyltrioxorhenium (VII) (57.6 mg, 0.23 mmol, 0.5 eq.) followed by $H_2O_2$ (30% solution, 262 mg, 2.31 mmol, 5.0 eq.). The resulting mixture was stirred at room temperature for 2 h, quenched with NaHSO$_3$ (5 ml, 10% aqueous). and extracted with EtOAc (3×10 mL). The combined organic layer was washed with brine, dried over $Na_2SO_4$, filtered and concentrated. The resulting residue was purified by C18 column chromatography (0→50% $CH_3CN/H_2O$) to yield 5-(5-chloro-2-(1H-tetrazol-1-yl)phenyl)-2-(2-cyclopropyl-1-(4-(4-(methoxycarbonylamino)phenyl)-1H-pyrazol-1-yl) ethyl)pyridine 1-oxide as a white solid.

HPLC purity (method B): 99.2%, retention time=1.567 min; LC/MS: mass calculated for $C_{28}H_{25}ClN_8O_3$: 556.17, measured (ES, m/z): 557.25 [M+H]$^+$. $^1$H NMR (300 MHz, DMSO-d$_6$) δ 9.68 (s, 1H), 9.63 (s, 1H), 8.40 (s, 1H), 8.28 (d, J=1.7 Hz, 1H), 7.94 (s, 1H), 7.88-7.91 (m, 1H), 7.82-7.85 (m, 2H), 7.52 (d, J=8.7 Hz, 2H), 7.44 (d, J=8.6 Hz, 2H), 7.17 (d, J=8.3 Hz, 1H), 6.96 (d, J=8.3 Hz, 1H), 6.06 (dd, J=9.8, 4.2 Hz, 1H), 3.67 (s, 3H), 2.30-2.45 (m, 1H), 1.80-1.91 (m, 1H), 0.56-0.67 (m, 1H), 0.30-0.40 (m, 2H), 0.09-0.16 (m, 1H), 0.00-0.06 (m, 1H).

Example 3: 2-(1-(4-(3-Carboxyphenyl)-1H-pyrazol-1-yl)-2-cyclopropylethyl)-5-(5-chloro-2-(1H-tetrazol-1-yl)phenyl)pyridine 1-oxide

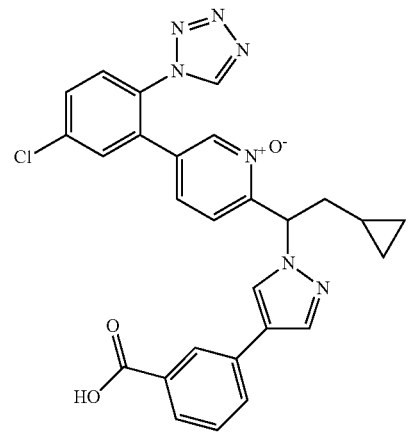

LC/MS: mass calculated. for $C_{27}H_{22}ClN_7O_3$: 527.15; measured (ES, m/z): 528.25 [M+H]$^+$. $^1$H NMR (300 MHz, DMSO-d$_6$) δ 9.67 (s, 1H), 8.63 (s, 1H), 8.28 (d, J=1.7 Hz, 1H), 8.15 (s, 1H), 8.08 (s, 1H), 7.81-7.93 (m, 4H), 7.74-7.80 (m, 1H), 7.49 (t, J=7.8 Hz, 1H), 7.19 (d, J=8.3 Hz, 1H), 6.95 (d, J=8.3, 1H), 6.09 (dd, J=9.9, 4.3 Hz, 1H), 2.32-2.42 (m, 1H), 1.83-1.92 (m, 1H), 0.50-0.70 (m, 1H), 0.27-0.41 (m, 2H), 0.07-0.17 (m, 1H), 0.00-0.06 (m, 1H).

Example 4: 2-(1-(4-(4-Carboxyphenyl)-1H-pyrazol-1-yl)-2-cyclopropylethyl)-5-(5-chloro-2-(4-chloro-1H-1,2,3-triazol-1-yl)phenyl)pyridine 1-oxide

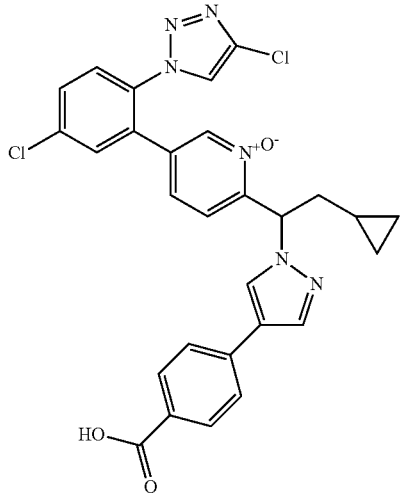

LC/MS: mass calculated for $C_{28}H_{22}Cl_2N_6O_3$: 560.11, measured (ES, m/z): 561.25 [M+H]$^+$. $^1$H NMR (300 MHz, DMSO-d$_6$) δ 8.69 (s, 1H), 8.64 (s, 1H), 8.25 (d, J=1.7 Hz, 1H), 8.12 (s, 1H), 7.89-7.97 (m, 2H), 7.87 (d, J=2.2 Hz, 1H), 7.70-7.85 (m, 4H), 7.26 (d, J=8.3 Hz, 1H), 6.98 (d, J=8.3 Hz, 1H), 6.12 (dd, J=9.8, 4.5 Hz, 1H), 2.25-2.46 (m, 1H), 1.81-2.00 (m, 1H), 0.50-0.70 (m, 1H), 0.31-0.40 (m, 2H), 0.11-0.16 (m, 1H), 0.00-0.08 (m, 1H).

Example 5: (S)-2-(1-(4-(4-Carboxyphenyl)-1H-pyrazol-1-yl)-2-cyclopropylethyl)-5-(5-chloro-2-(1H-tetrazol-1-yl)phenyl)pyridine 1-oxide

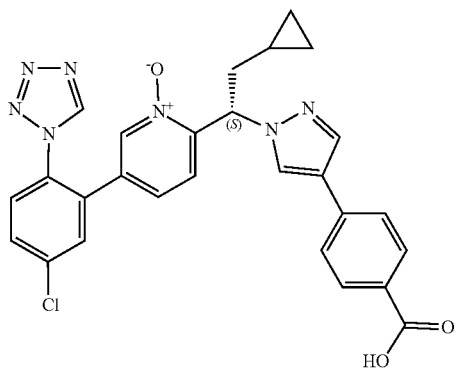

LC/MS: mass calculated for $C_{27}H_{22}ClN_7O_3$: 527.15, measured (ES, m/z): 528.20 [M+H]$^+$. $^1$H NMR (300 MHz, DMSO-d$_6$) δ 9.68 (s, 1H), 8.64 (s, 1H), 8.29 (d, J=1.7 Hz, 1H), 8.12 (s, 1H), 7.88-7.96 (m, 3H), 7.82-7.86 (m, 2H), 7.70-7.79 (m, 2H), 7.22 (d, J=8.3 Hz, 1H), 6.96 (d, J=8.3 Hz, 1H), 6.10 (dd, J=9.9, 4.2 Hz, 1H), 2.24-2.45 (m, 1H), 1.78-1.98 (m, 1H), 0.52-0.74 (m, 1H), 0.24-0.47 (m, 2H), 0.08-0.23 (m, 1H), 0.01-0.07 (m, 1H).

Example 6: (R)-2-(1-(4-(4-Carboxyphenyl)-1H-pyrazol-1-yl)-2-cyclopropylethyl)-5-(5-chloro-2-(1H-tetrazol-1-yl)phenyl)pyridine 1-oxide

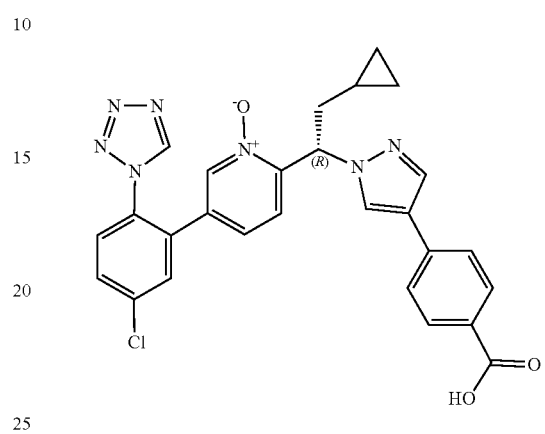

LC/MS: mass calculated for $C_{27}H_{22}ClN_7O_3$: 527.15, measured (ES, m/z): 528.20 [M+H]$^+$. $^1$H NMR (300 MHz, DMSO-d$_6$) δ 9.68 (s, 1H), 8.65 (s, 1H), 8.29 (d, J=1.7 Hz, 1H), 8.12 (s, 1H), 7.84-7.97 (m, 3H), 7.78-7.90 (m, 2H), 7.70-7.76 (m, 2H), 7.22 (d, J=8.3 Hz, 1H), 6.96 (dd, J=8.3, 1.8 Hz, 1H), 6.10 (dd, J=9.7, 4.3 Hz, 1H), 2.30-2.46 (m, 1H), 1.84-1.91 (m, 1H), 0.56-0.64 (m, 1H), 0.30-0.41 (m, 2H), 0.09-0.17 (m, 1H), 0.00-0.06 (m, 1H).

Example 7: 2-(1-(4-(4-Carboxyphenyl)-1H-pyrazol-1-yl)-2-(4-fluorophenyl)ethyl)-5-(5-chloro-2-(1H-tetrazol-1-yl)phenyl)pyridine 1-oxide

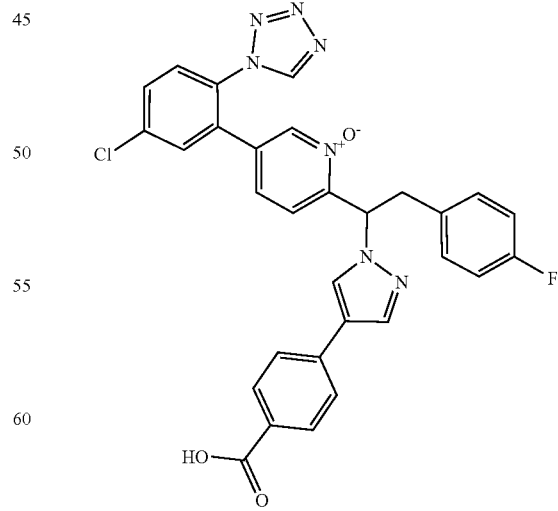

LC/MS: mass calculated for $C_{30}H_{21}ClFN_7O_3$: 581.14, measured (ES, m/z): 582.25 [M+H]$^+$.

Example 8: 2-(3-(tert-Butoxy)-1-(4-(4-carboxyphenyl)-1H-pyrazol-1-yl)propyl)-5-(5-chloro-2-(1H-tetrazol-1-yl)phenyl)pyridine 1-oxide

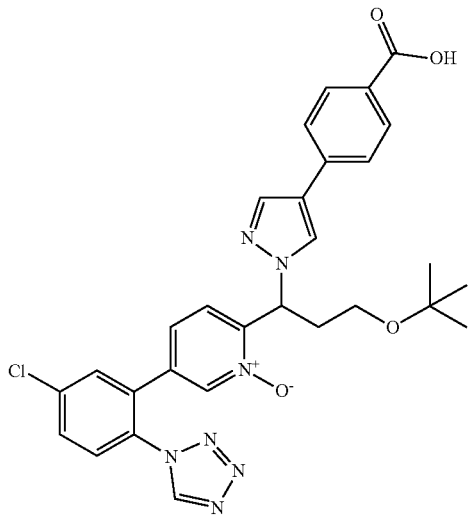 [SMILES: CC(C)(C)OCCC(c1ccc(-c2cc(Cl)ccc2-n2cnnn2)c[n+]1[O-])n1cc(-c2ccc(C(=O)O)cc2)cn1]

To a mixture of 4-(1-(3-tert-butoxy-1-(5-(5-chloro-2-(1H-tetrazol-1-yl)phenyl)pyridin-2-yl)propyl)-1H-pyrazol-4-yl)benzoic acid (150 mg, 0.269 mmol, 1.0 equiv) in MeOH (2 mL) with $H_2O_2$ (0.040 mL, 1.344 mmol, 5.0 equiv) was added methyltrioxorhenium (33.498 mg, 0.134 mmol, 0.5 quiv). The resulting mixture was stirred at room temperature for 1 h. The mixture was concentrated and the residue obtained was purified by reverse phase chromatography on C18 (80 g, MeCN/$H_2O$ (0.05% $CF_3COOH$): 0>>>45%) to yield 2-(3-tert-butoxy-1-(4-(4-carboxyphenyl)-1H-pyrazol-1-yl)propyl)-5-(5-chloro-2-(1H-tetrazol-1-yl)phenyl)pyridine 1-oxide as a white solid.

LC/MS: mass calculated for $C_{29}H_{28}ClN_7O_4$: 573.19, measured (ES, m/z): 573.9 $[M+H]^+$.

Example 9: 5-(5-Chloro-2-(1H-pyrazol-5-yl)phenyl)-2-(2-cyclopropyl-1-(4-(4-((methoxycarbonyl)amino)phenyl)-1H-pyrazol-1-yl)ethyl)pyridine 1-oxide

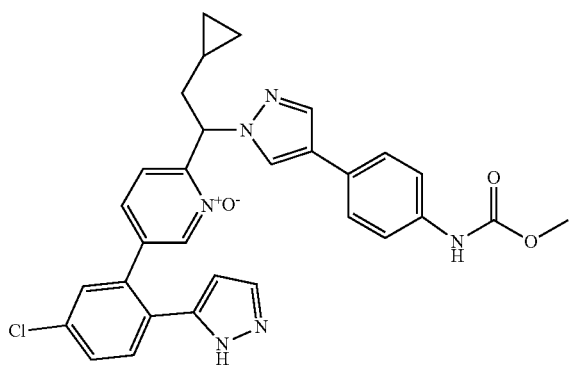

LC/MS: mass calculated for $C_{30}H_{27}ClN_6O_3$: 554.18; measured (ES, m/z): 554.90 $[M+H]^+$. $^1$H NMR (400 MHz, DMSO-$d_6$) δ 9.63 (s, 1H), 8.43 (s, 1H), 8.15 (d, J=1.6 Hz, 1H), 7.97 (s, 1H), 7.69 (d, J=8.3 Hz, 1H), 7.62 (d, J=2.2 Hz, 1H), 7.50-7.60 (m, 4H), 7.45 (d, J=8.4 Hz, 2H), 7.17-7.24 (m, 1H), 7.09-7.16 (m, 1H), 6.12 (dd, J=10.0, 4.1 Hz, 1H), 5.96 (d, J=2.2 Hz, 1H), 3.67 (s, 3H), 2.31-2.47 (m, 1H), 1.83-1.95 (m, 1H), 0.57-0.71 (m, 1H), 0.28-0.48 (m, 2H), 0.12-0.24 (m, 1H), 0.03-0.11 (m, 1H).

Example 10: 2-(1-(4-(3-Carboxyphenyl)-1H-pyrazol-1-yl)-2-cyclopropylethyl)-5-(5-chloro-2-(1H-tetrazol-1-yl)phenyl)-3-fluoropyridine 1-oxide

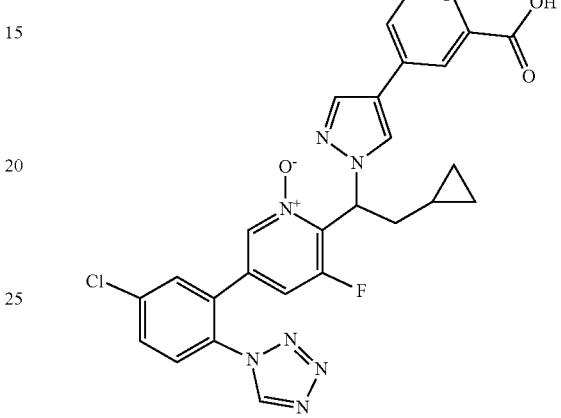

LC/MS: mass calculated for $C_{27}H_{21}ClFN_7O_3$: 545.14, measured (ES, m/z): 546.20 $[M+H]^+$. $^1$H NMR (300 MHz, DMSO-$d_6$) δ 9.71 (s, 1H), 8.49 (s, 1H), 8.20 (s, 1H), 8.12 (s, 1H), 7.96 (d, J=2.0 Hz, 1H), 7.89-7.97 (m, 1H), 7.82-7.89 (m, 2H), 7.70-7.80 (m, 2H), 7.40 (t, J=7.7 Hz, 1H), 7.21 (d, J=9.6 Hz, 1H), 6.26 (t, J=7.8 Hz, 1H), 2.52-2.62 (m, 1H), 2.14-2.35 (m, 1H), 0.51-0.77 (m, 1H), 0.22-0.46 (m, 2H), 0.04-0.17 (m, 1H), −0.10-0.00 (m, 1H). $^{19}$F NMR (282 MHz, DMSO-$d_6$) δ −119.50.

Example 11: 5-(5-Chloro-2-(1H-tetrazol-1-yl)phenyl)-2-(2-cyclopropyl-1-(4-(2-methyl-1-oxoisoindolin-5-yl)-1H-pyrazol-1-yl)ethyl)pyridine 1-oxide

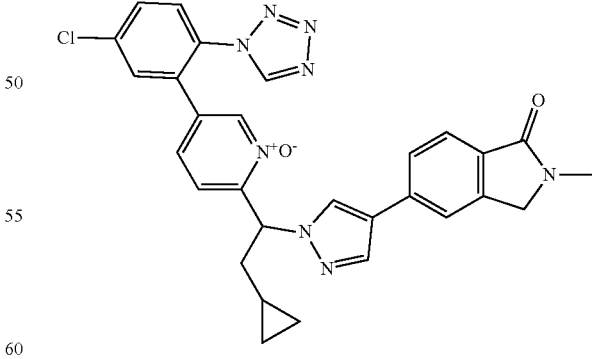

LC-MS: mass calculated for $C_{29}H_{25}ClN_8O_2$: 552.2, measured (ES, m/z): 553.2 $[M+H]^+$. $^1$H NMR (400 MHz, CD$_3$OD) δ ppm 0.07 (tt, J=8.72, 4.67 Hz, 1H) 0.18-0.28 (m, 1H) 0.35-0.51 (m, 2 h) 0.67-0.77 (m, 1H) 1.94-2.05 (m, 1H) 2.46-2.57 (m, 1H) 3.20 (s, 3H) 4.51 (s, 2 h) 6.18-6.30 (m, 1H) 7.08-7.22 (m, 1H) 7.38-7.47 (m, 1H) 7.68-7.74 (m, 3H)

7.75-7.81 (m, 3H) 8.04-8.12 (m, 1H) 8.21-8.31 (m, 1H) 8.39-8.50 (m, 1H) 9.38 (s, 1H).

Example 12: 5-(5-Chloro-2-(4-chloro-1H-1,2,3-triazol-1-yl)phenyl)-2-(2-cyclopropyl-1-(4-(4-((methoxycarbonyl)amino)phenyl)-1H-pyrazol-1-yl)ethyl)pyridine 1-oxide

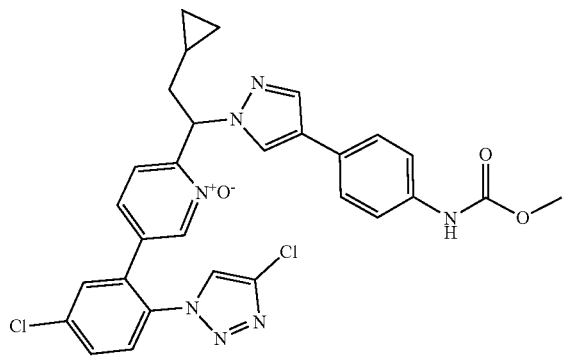

LC/MS: mass calculated for $C_{29}H_{25}Cl_2N_7O_3$: 589.1; measured (ES, m/z): 590.30 [M+H]$^+$. $^1$H NMR (400 MHz, DMSO-d$_6$) δ 9.64 (s, 1H), 8.69 (s, 1H), 8.40 (s, 1H), 8.24 (d, J=1.7 Hz, 1H), 7.94 (s, 1H), 7.87 (d, J=2.3 Hz, 1H), 7.79-7.83 (m, 1H), 7.76 (d, J=8.5 Hz, 1H), 7.49-7.56 (m, 2H), 7.44 (d, J=8.5 Hz, 2H), 7.20 (d, J=8.3 Hz, 1H), 6.97 (dd, J=8.3 Hz, 1H), 6.02-6.14 (m, 1H), 3.67 (s, 3H), 2.30-2.45 (m, 1H), 1.80-1.96 (m, 1H), 0.52-0.68 (m, 1H), 0.24-0.47 (m, 2H), 0.08-0.19 (m, 1H), 0.01-0.06 (m, 1H).

Example 13: 5-(5-Chloro-2-(1H-tetrazol-1-yl)phenyl)-2-(2-cyclopropyl-1-(4-(2-methyl-1-oxo-1,2,3,4-tetrahydroisoquinolin-6-yl)-1H-pyrazol-1-yl)ethyl)pyridine 1-oxide

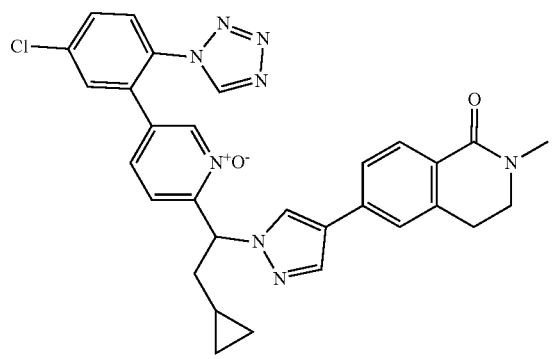

LC-MS: mass calculated for $C_{30}H_{27}ClN_8O_2$: 566.2, measured (ES, m/z): 567.3 [M+H]$^+$. $^1$H NMR (400 MHz, CD$_3$OD) δ ppm 0.01-0.12 (m, 1H) 0.16-0.26 (m, 1H) 0.34-0.51 (m, 2 h) 0.64-0.76 (m, 1H) 1.88-2.05 (m, 1H) 2.41-2.57 (m, 1H) 3.05 (t, J=6.82 Hz, 2 h) 3.14 (s, 3H) 3.57-3.69 (m, 2 h) 6.16-6.28 (m, 1H) 7.13-7.22 (m, 1H) 7.40 (d, J=8.08 Hz, 1H) 7.49 (s, 1H) 7.56 (d, J=8.08 Hz, 1H) 7.65-7.73 (m, 1H) 7.74-7.81 (m, 2 h) 7.90 (d, J=8.08 Hz, 1H) 8.02 (s, 1H) 8.25 (s, 1H) 8.36 (s, 1H) 9.37 (s, 1H).

Example 14: 5-(5-Chloro-2-(1H-tetrazol-1-yl)phenyl)-2-(2-cyclopropyl-1-(4-(1-oxo-1,3-dihydroisobenzofuran-5-yl)-1H-pyrazol-1-yl)ethyl)pyridine 1-oxide

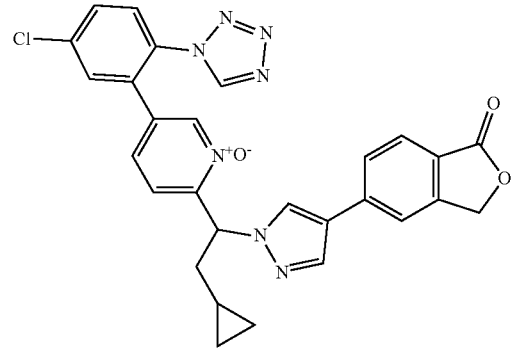

LC/MS: mass calculated for $C_{28}H_{22}ClN_7O_3$: 539.2, measured (ES, m/z): 540.2 [M+H]$^+$. $^1$H NMR (400 MHz, CD$_3$OD) δ ppm 0.02-0.12 (m, 1H) 0.16-0.26 (m, 1H) 0.34-0.51 (m, 2 h) 0.62-0.79 (m, 1H) 1.96-2.08 (m, 1H) 2.44-2.55 (m, 1H) 5.39 (s, 2 h) 6.19-6.27 (m, 1H) 7.13-7.21 (m, 1H) 7.42-7.48 (m, 1H) 7.68-7.81 (m, 3H) 7.81-7.87 (m, 3H) 8.10 (s, 1H) 8.26 (s, 1H) 8.47 (s, 1H) 9.38 (s, 1H).

Example 15: 5-(3-Chloro-2-fluoro-6-(1H-tetrazol-1-yl)phenyl)-2-(2-cyclopropyl-1-(4-(4-(methoxycarbonylamino)phenyl)-1H-pyrazol-1-yl)ethyl)pyridine 1-oxide

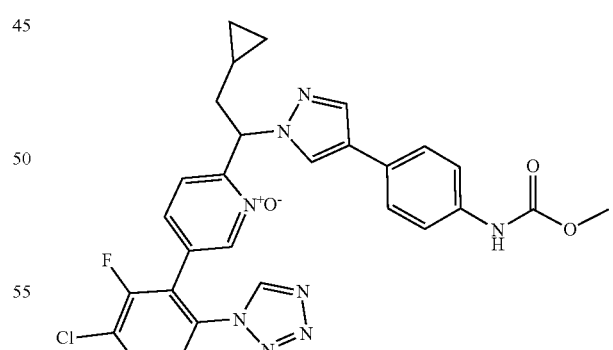

LC/MS: mass calculated for $C_{28}H_{24}ClFN_8O_3$: 574.16, measured (ES, m/z): 575.30 [M+H]$^+$. $^1$H NMR (300 MHz, DMSO-d$_6$) δ 9.66 (d, J=13.9 Hz, 2H), 8.41 (d, J=1.0 Hz, 2H), 8.09-8.03 (m, 1H), 7.95 (s, 1H), 7.77-7.74 (m, 1H), 7.58-7.40 (m, 4H), 7.26-7.10 (m, 2H), 6.08-6.04 (m, 1H), 3.67 (s, 3H), 2.43-2.33 (m, 1H), 1.93-1.78 (m, 1H), 0.62 (s, 1H), 0.38-0.30 (m 2 h), 0.13-0.02 (m, 2H). $^{19}$F NMR (282 MHz, DMSO-d$_6$) d −74.69, −112.77.

Example 16: 5-(5-Chloro-2-(1H-tetrazol-1-yl)phenyl)-2-(2-(2-cyclopropyl-1-(4-(4-(methylsulfonylcarbamoyl)phenyl)-1H-pyrazol-1-yl)ethyl)pyridine 1-oxide

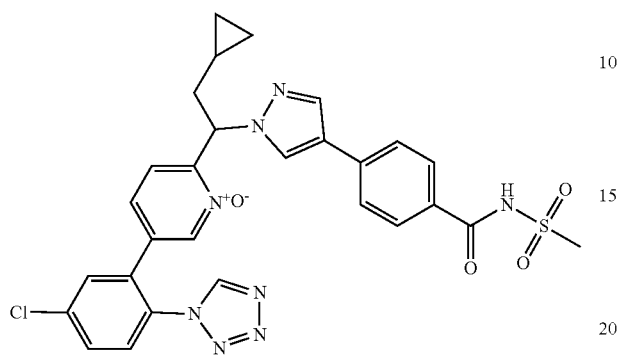

LC/MS: mass calculated for $C_{28}H_{25}ClN_8O_4S$: 604.14, measured (ES, m/z): 605.20 [M+H]$^+$. $^1$H NMR (300 MHz, DMSO-d$_6$) δ 9.68 (s, 1H), 8.54 (s, 1H), 8.27 (s, 1H), 8.05 (s, 1H), 7.87-7.95 (m, 3H), 7.80-7.86 (m, 2H), 7.54-7.61 (m, 2H), 7.16 (d, J=8.3 Hz, 1H), 6.96 (d, J=8.7 Hz, 1H), 5.88-6.35 (m, 1H), 2.85 (s, 3H), 2.23-2.48 (m, 1H), 1.77-1.96 (m, 1H), 0.51-0.73 (m, 1H), 0.25-0.50 (m, 2H), 0.09-0.20 (m, 1H), 0.01-0.08 (m, 1H).

Example 17: 2-(1-(4-(6-Amino-2-chloropyridin-3-yl)-1H-pyrazol-1-yl)-2-cyclopropylethyl)-5-(5-chloro-2-(1H-tetrazol-1-yl)phenyl)pyridine 1-oxide

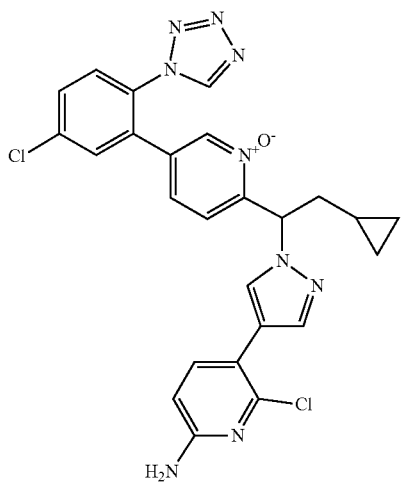

LC/MS: mass calculated for $C_{25}H_{21}Cl_2N_9O$: 533.12, measured (ES, m/z): 533.75 [M+H]$^+$. $^1$H NMR (300 MHz, DMSO-d$_6$) δ 9.68 (s, 1H), 8.29-8.26 (m, 2H), 7.90 (d, J=2.0 Hz, 1H), 7.79-7.88 (m, 3H), 7.63 (d, J=8.4 Hz, 1H), 7.22 (d, J=8.3 Hz, 1H), 6.97 (d, J=8.3 Hz, 1H), 6.46 (d, J=8.4 Hz, 1H), 6.09 (dd, J=9.8, 4.3 Hz, 1H), 2.21-2.43 (m, 1H), 1.80-1.97 (m, 1H), 0.50-0.69 (m, 1H), 0.23-0.47 (m, 2H), 0.06-0.21 (m, 1H), −0.09-0.00 (m, 1H).

Example 18: 2-(1-(4-(6-Amino-2-fluoropyridin-3-yl)-1H-pyrazol-1-yl)-2-cyclopropylethyl)-5-(3-chloro-2-fluoro-6-(1H-tetrazol-1-yl)phenyl)pyridine 1-oxide

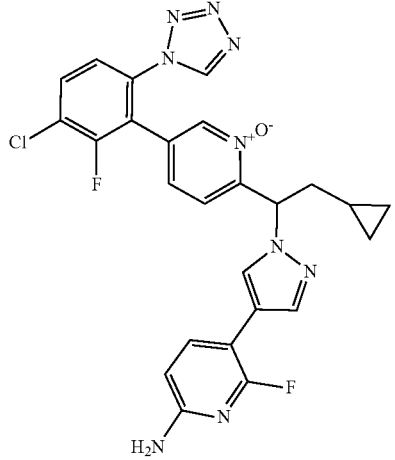

LC/MS: mass calculated for $C_{25}H_{20}ClF_2N_9O$: 535.14; measured (ES, m/z): 536.20 [M+H]$^+$. $^1$H NMR (400 MHz, DMSO-d$_6$) δ 9.68 (s, 1H), 8.40 (s, 1H), 8.24 (s, 1H), 8.05 (t, J=7.6 Hz, 1H), 7.77-7.86 (m, 2H), 7.75 (d, J=8.8 Hz, 1H), 7.21 (d, J=8.3 Hz, 1H), 7.14 (d, J=8.3 Hz, 1H), 6.36 (d, J=8.2 Hz, 1H), 6.07 (dd, J=9.8, 4.3 Hz, 1H), 2.29-2.43 (m, 1H), 1.77-1.94 (m, 1H), 0.52-0.65 (m, 1H), 0.22-0.40 (m, 2H), −0.05-0.03 (m, 1H). $^{19}$F NMR (376 MHz, DMSO-d$_6$) δ −71.42, −74.56, −112.77.

Example 19: 2-(1-(4-(4-Aminophenyl)-1H-pyrazol-1-yl)-2-cyclopropylethyl)-5-(3-chloro-2-fluoro-6-(1H-tetrazol-1-yl)phenyl)pyridine 1-oxide

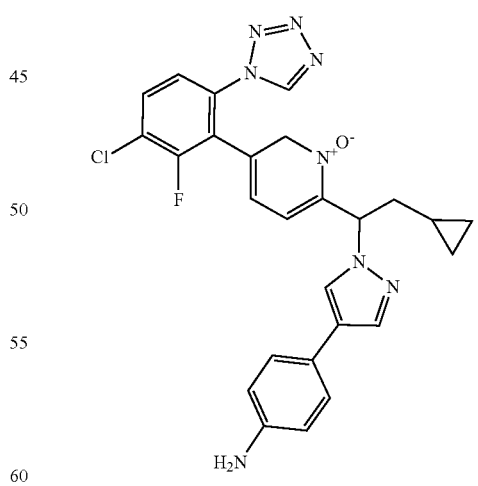

LC/MS: mass calculated for $C_{26}H_{22}ClFN_8O$: 516.16, measured (ES, m/z): 517.25 [M+H]$^+$. $^1$H NMR (400 MHz, DMSO-d$_6$) δ 9.68 (s, 1H), 8.43 (s, 1H), 9.38 (s, 1H), 8.06 (t, J=8.0 Hz, 1H), 7.97 (s, 1H), 7.75 (d, J=8.7 Hz, 1H), 7.59 (s, 1H), 7.55 (s, 1H), 7.24 (d, J=8.3 Hz, 1H), 7.15 (d, J=8.2 Hz, 1H), 7.05-7.09 (m, 2H), 6.06 (dd, J=9.8, 4.2 Hz, 1H), 2.28-2.44 (m, 1H), 1.77-1.95 (m, 1H), 0.51-0.67 (m, 1H), 0.24-0.45 (m, 2H), 0.07-0.17 (m, 1H), −0.02-0.05 (m, 1H). ¹⁹F NMR (376 MHz, DMSO-d₆) δ −74.20, −112.79.

Example 20: 5-(5-Chloro-2-(1H-tetrazol-1-yl)phenyl)-2-(2-(4-fluorophenyl)-1-(4-(4-fluorophenyl)-1H-pyrazol-1-yl)ethyl)pyridine 1-oxide

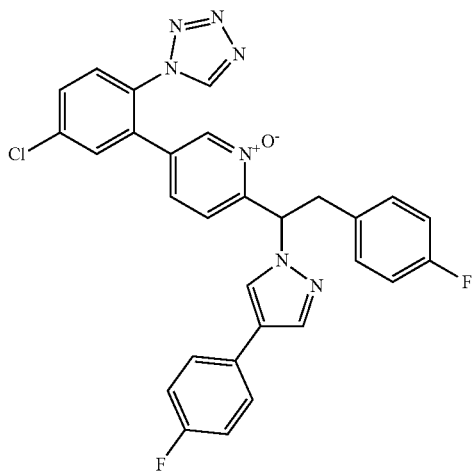

LC/MS: mass calculated for C₂₉H₂₀ClF₂N₇O: 555.14, measured (ES, m/z): 555.80 [M+H]⁺. ¹H NMR (300 MHz, DMSO-d₆) δ 9.69 (s, 1H), 8.35 (dd, J=4.1, 1.2 Hz, 2H), 8.01 (s, 1H), 7.92 (dd, J=2.0, 0.8 Hz, 1H), 7.80-7.89 (m, 2H), 7.53-7.63 (m, 2H), 7.12-7.28 (m, 5H), 6.95-7.12 (m, 3H), 6.18 (dd, J=9.9, 4.4 Hz, 1H), 3.41-3.67 (m, 2H).

Example 21: 2-(1-(4-(4-Acetamidophenyl)-1H-pyrazol-1-yl)-2-cyclopropylethyl)-5-(3-chloro-2-fluoro-6-(1H-tetrazol-1-yl)phenyl)pyridine 1-oxide

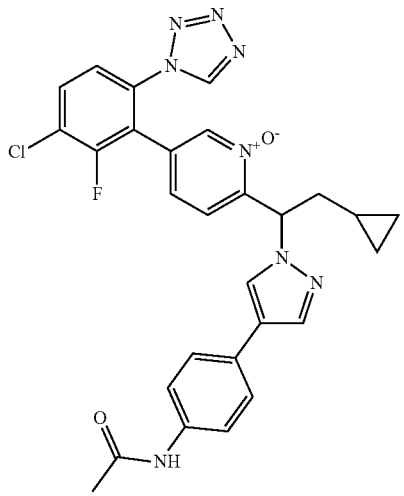

LC/MS: mass calculated for C₂₈H₂₄ClFN₈O₂: 558.17, measured (ES, m/z): 559.20 [M+H]⁺. ¹H NMR (400 MHz, DMSO-d₆) δ 9.92 (s, 1H), 9.68 (s, 1H), 8.37-8.46 (m, 2H), 8.05 (t, J=8.0 Hz 1H), 7.96 (s, 1H), 7.75 (d, J=8.7 Hz, 1H), 7.50-7.59 (m, 4H), 7.17-7.24 (m, 1H), 7.10-7.16 (m, 1H), 6.06 (dd, J=9.8, 4.2 Hz, 1H), 2.28-2.45 (m, 1H), 2.04 (s, 3H), 1.79-1.93 (m, 1H), 0.54-0.69 (m, 1H), 0.24-0.45 (m, 2H), 0.07-0.18 (m, 1H), −0.01-0.06 (m, 1H). ¹⁹F NMR: (376 MHz, DMSO-d₆): δ −74.70, −112.77.

Example 22: 5-(5-Chloro-2-cyanophenyl)-2-(2-(4-fluorophenyl)-1-(4-(4-((methoxycarbonyl)amino)phenyl)-1H-pyrazol-1-yl)ethyl)pyridine 1-oxide

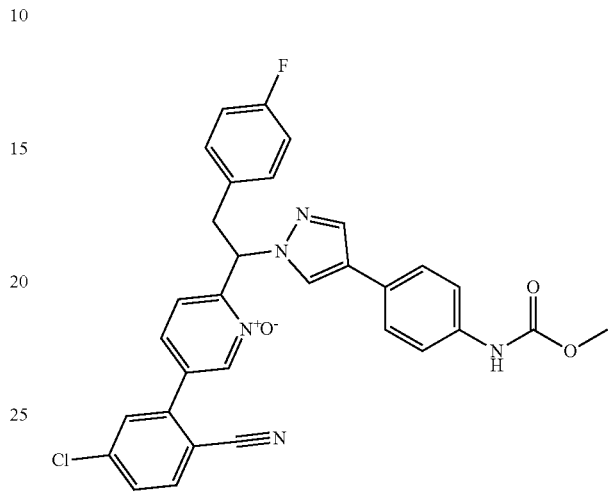

LC/MS: mass calculated for C₃₁H₂₃ClFN₅O₃: 567.15, measured (ES, m/z): 568.05 [M+H]⁺. ¹H NMR (300 MHz, DMSO-d₆) δ 9.63 (s, 1H), 8.72 (s, Hz, 1H), 8.31 (s, 1H), 8.06 (d, J=8.4 Hz, 1H), 8.00 (s, 1H), 7.90 (d, J=2.1 Hz, 1H), 7.78 (d, J=8.4 Hz, 1H), 7.63 (d, J=8.3 Hz, 1H), 7.37-7.54 (m, 5H), 7.21-7.34 (m, 2H), 7.02-7.18 (m, 2H), 6.28 (dd, J=10.1, 4.2 Hz, 1H), 3.66 (s, 3H), 3.49-3.65 (m, 2H). ¹⁹F NMR (282 MHz, DMSO-d₆) δ −73.99, −116.23.

Example 23: 2-(1-(4-(4-Carboxyphenyl)-1H-pyrazol-1-yl)-2-(4-fluorophenyl)ethyl)-5-(5-chloro-2-(2,2,2-trifluoroethoxy)phenyl)pyridine 1-oxide

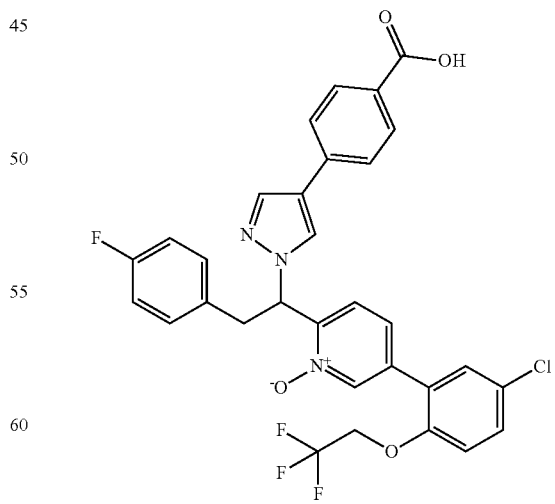

LC/MS: mass calculated for C₃₁H₂₂ClF₄N₃O₄: 611.12, measured (ES, m/z): 612.00 [M+H]⁺. ¹H NMR (400 MHz, DMSO-d₆) δ 12.84 (br, 1H), 8.53 (s, 2H), 8.16 (s, 1H), 7.91

(d, J=8.4 Hz, 2H), 7.69 (d, J=8.4 Hz, 2H), 747-7.63 (m, 3H), 7.43 (d, J=8.4 Hz, 1H), 7.21-7.37 (m, 3H), 7.08 (t, J=8.9 Hz, 2H), 6.31 (dd, J=10.0, 4.5 Hz, 1H), 4.81-4.89 (m, 2H), 3.54-3.74 (m, 2H). $^{19}$F NMR (282 MHz, DMSO-d$_6$) δ −72.39, −73.60, −116.17.

Example 24: 5-(5-Chloro-2-(2,2,2-trifluoroethoxy)phenyl)-2-(2-cyclopropyl-1-(4-(4-((methoxycarbonyl)amino)phenyl)-1H-pyrazol-1-yl)ethyl)pyridine 1-oxide

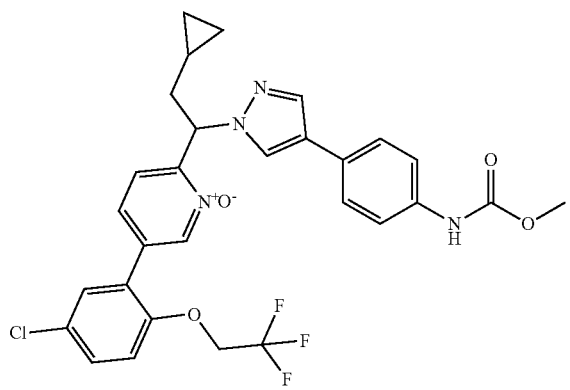

LC/MS: mass calculated for C$_{29}$H$_{26}$ClF$_3$N$_4$O$_4$: 586.16, measured (ES, m/z): 587.10 [M+H]$^+$. $^1$H NMR (300 MHz, DMSO-d$_6$) δ 9.64 (s, 1H), 8.46 (d, J=8.4 Hz, 2H), 7.97 (s, 1H), 7.50-7.60 (m, 4H), 7.41-7.49 (m, 3H), 7.23-7.39 (m, 2H), 6.14 (dd, J=9.9, 4.1 Hz, 1H), 4.81-4.89 (m, 2H), 3.67 (s, 3H), 2.37-2.49 (m, 1H), 1.84-2.02 (m, 1H), 0.52-0.79 (m, 1H), 0.28-0.51 (m, 2H), 0.13-0.26 (m, 1H), 0.01-0.12 (m, 1H).

Example 25: 2-(1-(4-(6-Aminopyridin-3-yl)-1H-pyrazol-1-yl)-2-cyclopropylethyl)-5-(3-Chloro-2-fluoro-6-(1H-tetrazol-1-yl)phenyl)pyridine 1-oxide

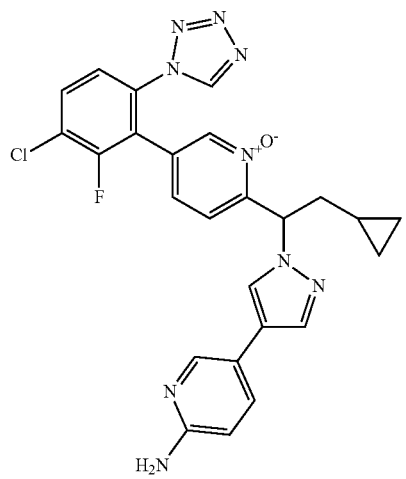

LC/MS: mass calculated for C$_{25}$H$_{21}$ClFN$_9$O: 517.15, measured (ES, m/z): 518.10 [M+H]$^+$. $^1$H NMR (300 MHz, DMSO-d$_6$) δ 9.68 (s, 1H), 8.40 (s, 1H), 8.33 (s, 1H), 8.20 (d, J=2.4 Hz, 1H), 8.06 (t, J=8.7 Hz, 1H), 7.89 (s, 1H), 7.75 (d, J=8.7 Hz, 1H), 7.60 (dd, J=8.5, 2.5 Hz, 1H), 7.41-7.23 (m, 2H), 6.46 (d, J=8.5 Hz, 1H), 5.97-6.10 (m, 1H), 5.87 (s, 2H), 2.23-2.45 (m, 1H), 1.72-1.97 (m, 1H), 0.73-0.96 (m, 1H), 0.48-0.72 (m, 1H), 0.20-0.48 (m, 2H), 0.06-0.18 (m, 1H).

Example 26: 2-Amino-5-(1-(1-(5-(3-Chloro-2-fluoro-6-(1H-tetrazol-1-yl)phenyl)-1-oxidopyridin-2-yl)-2-cyclopropylethyl)-1H-pyrazol-4-yl)pyridine 1-oxide

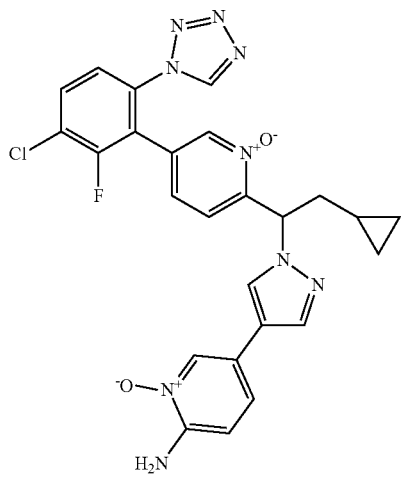

LC/MS: mass calculated for C25H21ClFN9O2: 533.15, measured (ES, m/z): 534.10 [M+H]$^+$. $^1$H NMR (300 MHz, DMSO-d$_6$) δ 9.68 (s, 1H), 8.37-8.52 (m, 3H), 8.06 (t, J=9.0 Hz, 1H), 7.99 (s, 1H), 7.75 (d, J=8.7 Hz, 1H), 7.39 (d, J=8.5 Hz, 1H), 7.09-7.27 (m, 2H), 6.82 (d, J=8.6 Hz, 1H), 6.74 (s, 2H), 6.05 (dd, J=9.7, 4.3 Hz, 1H), 2.13-2.43 (m, 1H), 1.73-1.96 (m, 1H), 0.73-0.95 (m, 1H), 0.47-0.72 (m, 1H), 0.23-0.44 (m, 2H), 0.05-0.19 (m, 1H).

Example 27: 2-((4-(4-Carboxyphenyl)-1H-pyrazol-1-yl)(1-phenyl-1H-1,2,3-triazol-4-yl)methyl)-5-(5-chloro-2-(1H-tetrazol-1-yl)phenyl)pyridine 1-oxide

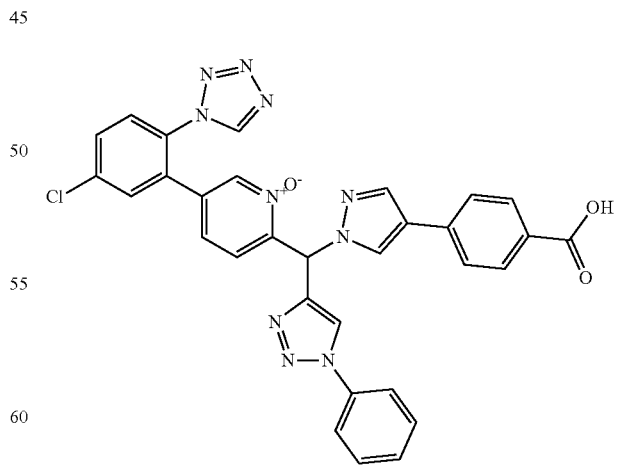

LC/MS: mass calculated for C$_{31}$H$_{21}$ClN$_{10}$O: 616.15, measured (ES, m/z): 617.1 [M+H]$^+$. $^1$H NMR (300 MHz, DMSO-d$_6$) δ 9.70 (s, 1H), 8.84 (s, 1H), 8.49 (s, 1H), 8.36 (d, J=1.6 Hz, 1H), 8.17 (s, 1H), 7.87-7.98 (m, 5H), 7.80-7.87

(m, 2H), 7.71-7.80 (m, 2H), 7.61 (t, J=7.5 Hz, 2H), 7.46-7.57 (m, 2H), 7.10 (d, J=8.3 Hz, 1H), 6.98-7.07 (m, 1H).

Example 28: (R*)-5-(3-Chloro-2-fluoro-6-(1H-tetrazol-1-yl)phenyl)-2-(2-cyclopropyl-1-(4-(4-((methoxycarbonyl)amino)phenyl)-1H-pyrazol-1-yl)ethyl)pyridine 1-oxide

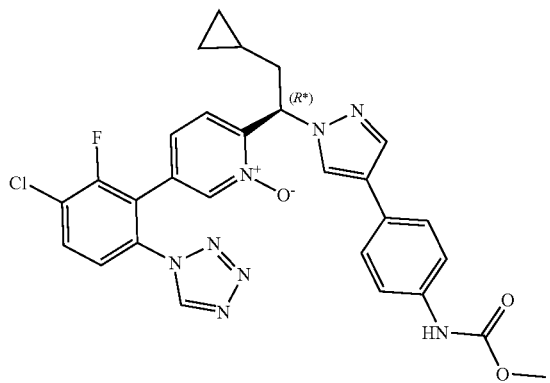

To a solution of methyl 4-(1-(1-(5-(3-chloro-2-fluoro-6-(1H-tetrazol-1-yl)phenyl)pyridin-2-yl)-2-cyclopropylethyl)-1H-pyrazol-4-yl)phenylcarbamate (230 mg, 0.41 mmol, 1.0 equiv.) in $CH_3OH$ (6 mL) was added methyltrioxorhenium (VII) (51 mg, 0.21 mmol, 0.5 equiv.) and $H_2O_2$ (233 mg, 2.06 mmol, 5.0 equiv.). The resulting mixture was stirred at room temperature for 2 h. The reaction was quenched with $NaHSO_3$ (4 mL, 10% aqueous). The resulting mixture was extracted with EtOAc. The organic layers were combined, dried over $Na_2SO_4$, filtered and concentrated. The resulting residue was purified by C18 reverse phase chromatography (0→50% $CH_3CN/H_2O$) to yield 5-(3-chloro-2-fluoro-6-(1H-tetrazol-1-yl)phenyl)-2-(2-cyclopropyl-1-(4-(4-(methoxycarbonylamino)phenyl)-1H-pyrazol-1-yl)ethyl)pyridine 1-oxide as a white solid. The racemic mixture was separated by prep-Chiral-HPLC separation with the following conditions: column, chiralpak IB4. 6*250 mm, 5 um HPLC Chiral-A (IB) 001IB00CE-LA026; mobile phase, (Method: (MeOH (0.1% TFA): DCM=50%: 50%; Total Run Time (min), 30; Detector, UV 254 nm. The collected fractions were combined and concentrated under vacuum to yield (R*)-5-(3-chloro-2-fluoro-6-(1H-tetrazol-1-yl)phenyl)-2-(2-cyclopropyl-1-(4-(4-(methoxycarbonylamino)phenyl)-1H-pyrazol-1-yl)ethyl)pyridine 1-oxide as a white solid.

LC/MS: mass calculated for $C_{28}H_{24}ClFN_8O_3$, 574.16; measured (ES, m/z): 574.75 [M+H]$^+$. $^1$H NMR (400 MHz, DMSO-$d_6$) δ 9.69 (s, 1H), 9.64 (s, 1H), 8.41 (s, 2H), 8.06 (t, J=8.2 Hz, 1H), 7.96 (s, 1H), 7.76 (d, J=8.2 Hz, 1H), 7.53 (d, J=8.4 Hz, 2H), 7.45 (d, J=8.4 Hz, 2H), 7.22 (d, J=8.3 Hz, 1H), 7.15 (d, J=8.4 Hz, 1H), 6.07 (dd, J=9.9, 4.2 Hz, 1H), 3.68 (s, 3H), 2.34-2.42 (m, 1H), 1.82-1.90 (m, 1H), 0.58-0.65 (m, 1H), 0.29-0.39 (m, 2H), 0.10-0.15 (m, 1H), 0.00-0.05 (m, 1H). $^{19}$F NMR (376 MHz, DMSO-$d_6$) δ −74.72, −112.76.

Example 29: (R)-5-(3-Chloro-2-fluoro-6-(1H-tetrazol-1-yl)phenyl)-2-(2-cyclopropyl-1-(4-(4-((methoxycarbonyl)amino)phenyl)-1H-pyrazol-1-yl)ethyl)pyridine 1-oxide

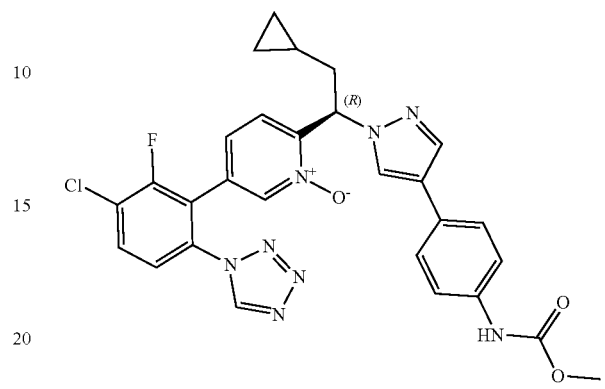

To a solution of methyl 4-(1-(1-(5-(3-chloro-2-fluoro-6-(1H-tetrazol-1-yl)phenyl)pyridin-2-yl)-2-cyclopropylethyl)-1H-pyrazol-4-yl)phenylcarbamate (230 mg, 0.41 mmol, 1.0 equiv.) in $CH_3OH$ (6 mL) was added methyltrioxorhenium (VII) (51 mg, 0.21 mmol, 0.5 equiv.) and $H_2O_2$ (233 mg, 2.06 mmol, 5.0 equiv.). The resulting mixture was stirred at room temperature for 2 h. The reaction was quenched with $NaHSO_3$ (4 mL, 10% aqueous). The resulting mixture was extracted with EtOAc (3×20 mL). The organic layers were combined, dried over $Na_2SO_4$, filtered and concentrated. The resulting residue was purified by C18 reverse phase chromatography (0→50% $CH_3CN/H_2O$) to yield 5-(3-chloro-2-fluoro-6-(1H-tetrazol-1-yl)phenyl)-2-(2-cyclopropyl-1-(4-(4-(methoxycarbonylamino)phenyl)-1H-pyrazol-1-yl)ethyl)pyridine 1-oxide as a white solid. The racemic mixture was separated by Prep-Chiral-HPLC separation with the following conditions: column, chiralpak IB4. 6*250 mm, 5 um HPLC Chiral-A (IB) 001IB00CE-LA026; mobile phase, (Method: (MeOH (0.1% TFA): DCM=50%: 50%; Total Run Time (min), 30; Detector, UV 254 nm. The collected fractions were combined and concentrated under vacuum. To yield (R)-5-(3-chloro-2-fluoro-6-(1H-tetrazol-1-yl)phenyl)-2-(2-cyclopropyl-1-(4-(4-(methoxycarbonylamino)phenyl)-1H-pyrazol-1-yl)ethyl)pyridine 1-oxide as a white solid.

LC/MS: mass calculated for $C_{28}H_{24}ClFN_8O_3$, 574.16; measured (ES, m/z): 574.75 [M+H]$^+$. $^1$H NMR (400 MHz, DMSO-$d_6$) δ 9.69 (s, 1H), 9.64 (s, 1H), 8.41 (s, 2H), 8.06 (t, J=8.2 Hz, 1H), 7.96 (s, 1H), 7.76 (d, J=8.2 Hz, 1H), 7.53 (d, J=8.4 Hz, 2H), 7.45 (d, J=8.4 Hz, 2H), 7.22 (d, J=8.3 Hz, 1H), 7.15 (d, J=8.4 Hz, 1H), 6.07 (dd, J=9.9, 4.2 Hz, 1H), 3.68 (s, 3H), 2.34-2.42 (m, 1H), 1.82-1.90 (m, 1H), 0.58-0.65 (m, 1H), 0.29-0.39 (m, 2H), 0.10-0.15 (m, 1H), 0.00-0.05 (m, 1H). $^{19}$F NMR (300 MHz, DMSO-$d_6$) δ −74.73, −112.78.

Example 30: 2-(1-(4-(6-Amino-4-fluoropyridin-3-yl)-1H-pyrazol-1-yl)-2-cyclopropylethyl)-5-(3-Chloro-2-fluoro-6-(1H-tetrazol-1-yl)phenyl)pyridine 1-oxide

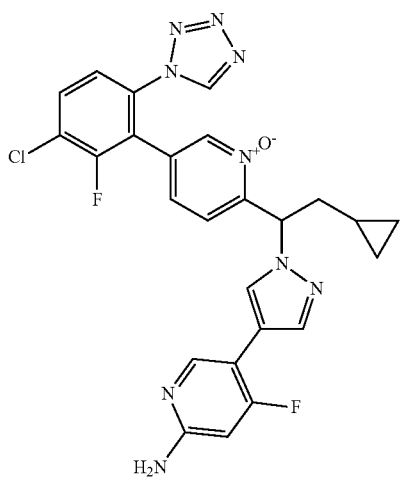

LC/MS: mass calculated for $C_{25}H_{20}ClF_2N_9O$, 535.14, measured (ES, m/z): 536.25 [M+H]⁺. ¹H NMR (300 MHz, DMSO-d₆) δ 9.60 (s, 1H), 8.60 (d, J=7.3 Hz, 1H), 8.36 (s, 2H), 8.02 (t, J=8.1 Hz, 1H), 7.93 (s, 1H), 7.75 (d, J=8.7 Hz, 1H), 7.59-7.71 (m, 1H), 7.09-7.32 (m, 2H), 6.74 (d, J=10.7 Hz, 1H), 5.53-5.70 (m, 1H), 2.21-2.44 (m, 1H), 1.88-2.09 (m, 1H), 0.41-0.61 (m, 1H), 0.17-0.40 (in, 2H), −0.10-0.12 (in, 2H).

Example 31: 5-(3-Chloro-2-fluoro-6-(1H-tetrazol-1-yl)phenyl)-2-(2-cyclopropyl-1-(4-(4-(methoxycarbonylamino)phenyl)-1H-pyrazol-1-yl)ethyl)-3-fluoropyridine 1-oxide

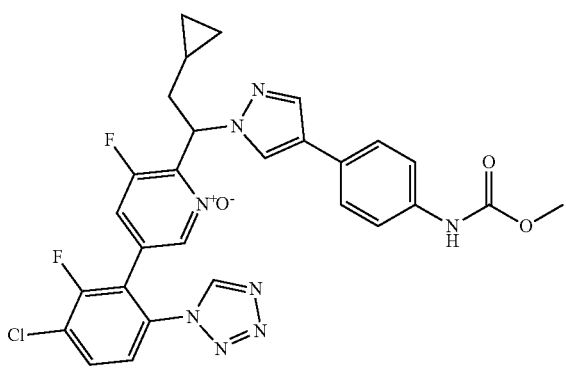

LC/MS: mass calculated for $C_{23}H_{16}ClF_2N_9O$: 592.15; measured (ES, m/z): 592.75 [M+H]⁺. ¹H NMR (400 MHz, DMSO-d₆) δ 9.72 (s, 1H), 9.62 (s, 1H), 8.34 (d, J=11.3 Hz, 2H), 8.14-8.05 (m, 1H), 7.84-7.74 (m, 2H), 7.60-7.48 (m, 2H), 7.47-7.38 (m, 3H), 6.25 (t, J=7.8 Hz, 1H), 3.67 (s, 3H), 2.57-2.51 (m, 1H), 2.19 (dt, J=14.6, 8.3 Hz, 1H), 0.72-0.60 (m, 1H), 0.44-0.23 (m, 2H), 0.14-0.03 (m, 1H), −0.07 (dt, J=9.5, 4.6 Hz, 1H). ¹⁹F NMR (376 MHz, DMSO-d₆) d −74.39 (d, J=3.7 Hz), −112.36, −119.13.

Example 32: 2-((4-(4-Carboxyphenyl)-1H-pyrazol-1-yl)(1-methyl-1H-1,2,3-triazol-4-yl)methyl)-5-(5-chloro-2-(1H-tetrazol-1-yl)phenyl)pyridine 1-oxide

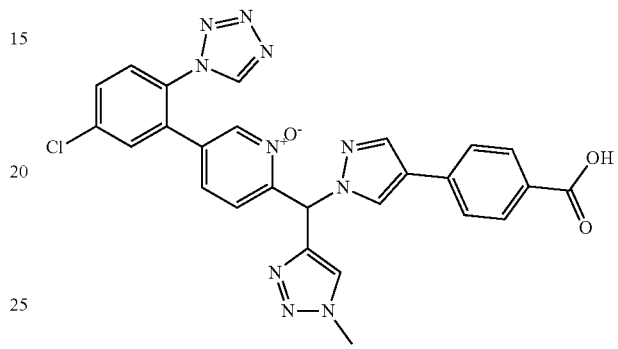

LC/MS: mass calculated for $C_{26}H_{19}ClN_{10}O_3$: 554.13, measured (ES, m/z): 554.7 [M+H]⁺. ¹H NMR (300 MHz, DMSO-d₆) δ 9.70 (s, 1H), 8.42 (s, 1H), 8.33 (s, 1H), 8.11 (d, J=10.1 Hz, 2H), 7.87-7.96 (m, 3H), 7.80-7.87 (m, 2H), 7.72 (d, J=8.2 Hz, 2H), 7.42 (s, 1H), 7.05-7.12 (m, 1H), 6.95-7.03 (m, 1H), 4.06 (s, 3H).

Example 33: 2-((4-(3-Carboxyphenyl)-1H-pyrazol-1-yl)(1-methyl-1H-1,2,3-triazol-4-yl)methyl)-5-(5-chloro-2-(1H-tetrazol-1-yl)phenyl)pyridine 1-oxide

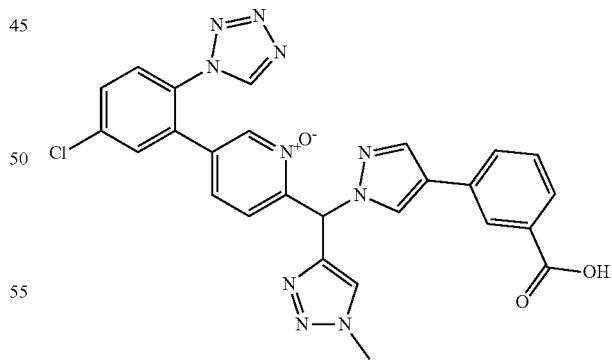

LC/MS: mass calculated for $C_{26}H_{19}ClN_{10}O_3$: 554.13, measured (ES, m/z): 555.0 [M+H]⁺. ¹H NMR (300 MHz, DMSO-d₆) δ 9.70 (s, 1H), 8.40 (s, 1H), 8.33 (s, 1H), 8.04-8.14 (m, 3H), 7.98-7.94 (m, 1H), 7.73-7.89 (m, 4H), 7.48 (t, J=7.8 Hz, 1H), 7.42 (s, 1H), 7.09 (d, J=8.3 Hz, 1H), 6.93-7.03 (m, 1H), 4.05 (s, 3H).

227

Example 34: 2-((4-(4-Carboxyphenyl)-1H-pyrazol-1-yl)(1-methyl-1H-1,2,3-triazol-4-yl)methyl)-5-(3-Chloro-2-fluoro-6-(1H-tetrazol-1-yl)phenyl)pyridine 1-oxide

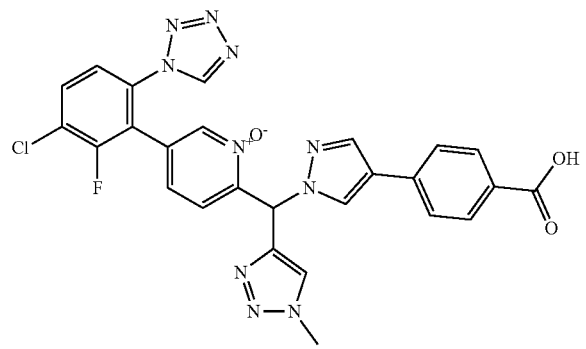

LC/MS: mass calculated for $C_{26}H_{18}ClFN_{10}O_3$: 572.12; measured (ES, m/z): 573.00 [M+H]$^+$. $^1$H NMR (300 MHz, DMSO-d$_6$) δ 9.70 (s, 1H), 8.45 (s, 1H), 8.41 (s, 1H), 8.02-8.17 (m, 3H), 7.87-7.93 (m, 2H), 7.66-7.79 (m, 3H), 7.41 (s, 1H), 7.17-7.24 (m, 1H), 7.08-7.16 (m, 1H), 4.06 (s, 3H). $^{19}$F NMR (282 MHz, DMSO-d$_6$) δ −112.59.

Example 35: 2-((4-(4-Carboxyphenyl)-1H-pyrazol-1-yl)(1-phenyl-1H-1,2,3-triazol-4-yl)methyl)-5-(3-Chloro-2-fluoro-6-(1H-tetrazol-1-yl)phenyl)pyridine 1-oxide

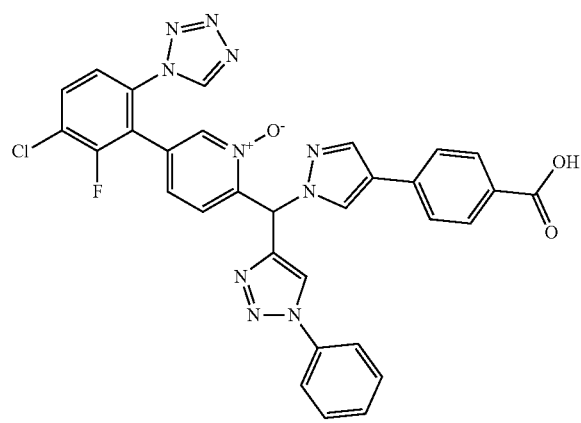 [SMILES: O=C(O)c1ccc(-c2cnn(C(c3cn(-c4ccccc4)nn3)c3ccc(-c4c(-n5cnnn5)ccc(Cl)c4F)c[n+]3[O-])c2)cc1]

LC/MS: mass calculated for $C_{31}H_{20}ClFN_{10}O_3$: 634.14, measured (ES, m/z): 635.05 [M+H]$^+$. $^1$H NMR (300 MHz, DMSO-d$_6$) δ 9.71 (s, 1H), 8.87 (s, 1H), 8.44-8.52 (m, 2H), 8.18 (s, 1H), 8.07 (t, J=8.1 Hz, 1H), 7.86-7.99 (m, 4H), 7.71-7.82 (m, 3H), 7.61-7.68 (m, 2H), 7.47-7.56 (m, 2H), 7.20-7.28 (m, 1H), 7.11-7.19 (m, 1H), 2.54 (s, 3H). $^{19}$F NMR (282 MHz, DMSO-d$_6$) δ −112.50.

228

Example 36: (S)-2-(1-(4-(6-Amino-2-fluoropyridin-3-yl)-1H-pyrazol-1-yl)-2-cyclopropylethyl)-5-(3-Chloro-2-fluoro-6-(1H-tetrazol-1-yl)phenyl)pyridine 1-oxide

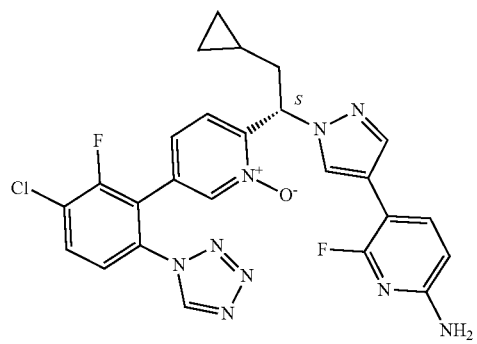

Step 1. N-(6-Fluoro-5-(1H-pyrazol-4-yl)pyridin-2-yl)acetamide

The mixture of N-(6-fluoro-5-iodopyridin-2-yl)acetamide (3.0 g, 10.713 mmol, 1.00 equiv), tert-butyl 4-(4,4,5,5-tetramethyl-1,3,2-dioxaborolan-2-yl)-1H-pyrazole-1-carboxylate (6.302 g, 21.426 mmol, 2.00 equiv), potassium carbonate (4.442 g, 32.138 mmol, 3.00 equiv) and Pd(PPh$_3$)$_4$ (1.238 g, 1.071 mmol, 0.10 equiv) in DMF (30 mL) and water (5 mL) was stirred overnight at 90° C. The reaction was concentrated and purified by silica gel chromatography (0-10% MeOH/DCM) to yield N-(6-fluoro-5-(1H-pyrazol-4-yl)pyridin-2-yl)acetamide as a light yellow solid (1.7 g, 72.065% yield). LC/MS: mass calculated for $C_{10}H_9FN_4O$: 220.1, measured: 221.1 [M+H]$^+$.

Step 2. N-(5-(1-(1-(5-Bromopyridin-2-yl)-2-cyclopropylethyl)-1H-pyrazol-4-yl)-6-fluoropyridin-2-yl)acetamide To a solution of N-(6-fluoro-5-(1H-pyrazol-4-yl)pyridin-2-yl)acetamide (400 mg, 1.817 mmol) in CH$_3$CN (5 mL) was added 1-(5-bromopyridin-2-yl)-2-cyclopropylethyl methanesulfonate (528.8 mg, 1.651 mmol,) and Cs$_2$CO$_3$ (1.1 g, 3.376 mmol). The resulting mixture was stirred at 80° C. for 2 h. The reaction was quenched with H$_2$O (20 mL). The resulting mixture was extracted with EtOAc (3×30 mL). The organic layers were combined, dried over Na$_2$SO$_4$, filtered and concentrated. The residue obtained was purified by silica gel chromatography (0-30% EtOAc/petroleum ether) to yield N-(5-(1-(1-(5-bromopyridin-2-yl)-2-cyclopropylethyl)-1H-pyrazol-4-yl)-6-fluoropyridin-2-yl)acetamide as a light yellow solid (330 mg, 44.9% yield). LC/MS: mass calculated for $C_{20}H_{19}BrFN_5O$: 443.1, measured: 444.2 [M+H]$^+$.

Step 3. N-(5-(1-(1-(5-(6-Amino-3-chloro-2-fluorophenyl)pyridin-2-yl)-2-cyclopropylethyl)-1H-pyrazol-4-yl)-6-fluoropyridin-2-yl)acetamide To a solution of N-(5-(1-(1-(5-bromopyridin-2-yl)-2-cyclopropylethyl)-1H-pyrazol-4-yl)-6-fluoropyridin-2-yl)acetamide (330 mg, 0.743 mmol) in 1,4-dioxane/H$_2$O (5.5 ml) was added 6-amino-3-chloro-2-fluorophenylboronic acid (351.7 mg, 1.114 mmol), K$_2$CO$_3$ (308.0 mg, 2.228 mmol)

and Pd(PPh$_3$)$_4$ (43.0 mg, 0.037 mmol). The resulting mixture was stirred at 100° C. for 2 h. The reaction was quenched with H2O (10 mL). The resulting mixture was extracted with EtOAc (3×20 mL). The organic layers were combined, dried over Na$_2$SO$_4$, filtered and concentrated. The residue obtained was purified by silica gel chromatography (0-10% CH$_3$OH/CH$_2$Cl$_2$) to yield N-(5-(1-(1-(5-(6-amino-3-chloro-2-fluorophenyl)pyridin-2-yl)-2-cyclopropylethyl)-1H-pyrazol-4-yl)-6-fluoropyridin-2-yl)acetamide as a light brown solid (350 mg, 92.5% yield). LC/MS: mass calculated for C$_{26}$H$_{23}$ClF$_2$N$_6$O: 508.2, measured: 509.1 [M+H]$^+$.

Step 4. N-(5-(1-(1-(5-(3-Chloro-2-fluoro-6-(1H-tetrazol-1-yl)phenyl)pyridin-2-yl)-2-cyclopropylethyl)-1H-pyrazol-4-yl)-6-fluoropyridin-2-yl)acetamide To a solution of N-(5-(1-(1-(5-(6-amino-3-chloro-2-fluorophenyl)pyridin-2-yl)-2-cyclopropylethyl)-1H-pyrazol-4-yl)-6-fluoropyridin-2-yl)acetamide (350 mg, 0.688 mmol) in acetic acid (12 ml) was added TMSN$_3$ (396.1 mg, 3.438 mmol) and trimethoxymethane (729.8 mg, 6.877 mmol). The resulting mixture was stirred at rt for overnight. The reaction was quenched with H$_2$O (20 mL). The resulting mixture was extracted with EtOAc (3×25 mL). The organic layers were combined, dried over Na$_2$SO$_4$, filtered and concentrated. The residue obtained was purified by C18 chromatography (0~60% CH$_3$CN/H$_2$O) to yield N-(5-(1-(1-(5-(3-chloro-2-fluoro-6-(1H-tetrazol-1-yl)phenyl)pyridin-2-yl)-2-cyclopropylethyl)-1H-pyrazol-4-yl)-6-fluoropyridin-2-yl)acetamide as light yellow solid (300 mg, 356% yield), LC/MS: mass calculated for C$_{27}$H$_{22}$ClF$_2$N$_9$O: 561.2, measured: 562.3 [M+H]$^+$.

Step 5. 2-(1-(4-(6-Acetamido-2-fluoropyridin-3-yl)-1H-pyrazol-1-yl)-2-cyclopropylethyl)-5-(3-chloro-2-fluoro-6-(1H-tetrazol-1-yl)phenyl)pyridine 1-oxide To a solution of N-(5-(1-(1-(5-(3-chloro-2-fluoro-6-(1H-tetrazol-1-yl)phenyl)pyridin-2-yl)-2-cyclopropylethyl)-1H-pyrazol-4-yl)-6-fluoropyridin-2-yl)acetamide (5 mg, 0.009 mmol) in CH$_3$OH (0.5 mL) was added methyltrioxorhenium (VII) (1.1 mg, 0.004 mmol) and H$_2$O$_2$ (5.0 mg, 0.044 mmol,). The resulting mixture was stirred at rt for 2 h. The reaction worked well based on LC/MS. LC/MS: mass calculated for C$_{27}$H$_{22}$ClF$_2$N$_9$O$_2$: 577.2, measured: 578.3 [M+H]$^+$.

Step 6. 2-(1-(4-(6-Amino-2-fluoropyridin-3-yl)-1H-pyrazol-1-yl)-2-cyclopropylethyl)-5-(3-chloro-2-fluoro-6-(1H-tetrazol-1-yl)phenyl)pyridine 1-oxide To a solution of 2-(1-(4-(6-acetamido-2-fluoropyridin-3-yl)-1H-pyrazol-1-yl)-2-cyclopropylethyl)-5-(3-chloro-2-fluoro-6-(1H-tetrazol-1-yl)phenyl)pyridine 1-oxide (120 mg, 0.208 mmol) in THF (2.2 ml) was added HCl (2.4 mL, 2 M). The resulting mixture was stirred at 60° C. for 2 h. The reaction was quenched with H$_2$O (10 mL). The resulting mixture was extracted with EtOAc (3×15 mL). The organic layers were combined, dried over Na$_2$SO$_4$, filtered and concentrated. The residue obtained was purified by C18 chromatography (0~50% CH$_3$CN/H$_2$O) to yield 2-(1-(4-(6-amino-2-fluoropyridin-3-yl)-1H-pyrazol-1-yl)-2-cyclopropylethyl)-5-(3-chloro-2-fluoro-6-(1H-tetrazol-1-yl)phenyl)pyridine 1-oxide as a yellow solid, LC/MS: mass calculated for C$_{25}$H$_{20}$ClF$_2$N$_9$O: 535.14, measured: 535.70 [M+H]$^+$. The racemic mixture was separated by prep-Chiral-HPLC separation. The collected fractions were combined and concentrated under vacuum. This resulted in (S)-2-(1-(4-(6-amino-2-fluoropyridin-3-yl)-1H-pyrazol-1-yl)-2-cyclopropylethyl)-5-(3-chloro-2-fluoro-6-(1H-tetrazol-1-yl)phenyl)pyridine 1-oxide (14.8 mg, 10.2%) as an off-white solid.

LC/MS: mass calculated for C$_{25}$H$_{20}$ClF$_2$N$_9$O: 535.14, measured (ES, m/z): 535.70 [M+H]$^+$. $^1$H NMR (400 MHz, DMSO-d$_6$) δ 9.69 (s, 1H), 8.41 (s, 1H), 8.24 (s, 1H), 8.06 (t, J=8.8 Hz, 1H), 7.71-7.88 (m, 3H), 7.22 (d, J=8.3 Hz, 1H), 7.10-7.17 (m, 1H), 6.37 (d, J=8.2 Hz, 1H), 6.00-6.15 (m, 1H), 2.30-2.43 (m, 1H), 1.79-1.93 (m, 1H), 0.50-0.67 (m, 1H), 0.22-0.41 (m, 2H), 0.07-0.18 (m, 1H), −0.06-0.05 (m, 1H). $^{19}$F NMR (376 MHz, DMSO-d$_6$) δ −71.41, −74.76, −112.78.

Example 37: (R)-2-(1-(4-(6-amino-2-fluoropyridin-3-yl)-1H-pyrazol-1-yl)-2-cyclopropylethyl)-5-(3-Chloro-2-fluoro-6-(1H-tetrazol-1-yl)phenyl)pyridine 1-oxide

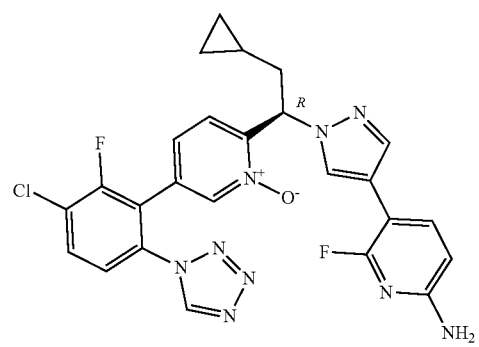

LC/MS: mass calculated for C$_{25}$H$_{20}$ClF$_2$N$_9$O: 535.14, measured (ES, m/z): 535.75 [M+H]$^+$. $^1$H NMR (400 MHz, DMSO-d$_6$) δ 9.69 (s, 1H), 8.41 (s, 1H), 8.24 (s, 1H), 8.06 (t, J=8.8 Hz, 1H), 7.71-7.88 (m, 3H), 7.22 (d, J=8.3 Hz, 1H), 7.10-7.17 (m, 1H), 6.37 (d, J=8.2 Hz, 1H), 6.00-6.15 (m, 1H), 2.30-2.43 (m, 1H), 1.79-1.99 (m, 1H), 0.50-0.66 (m, 1H), 0.22-0.40 (m, 2H), 0.07-0.17 (m, 1H), −0.04-0.04 (m, 1H). $^{19}$F NMR (376 MHz, DMSO-d$_6$) δ −71.42, −74.74, −112.77.

Example 38: 5-(3-Chloro-2-fluoro-6-(1H-tetrazol-1-yl)phenyl)-2-(3-methoxy-1-(4-(4-((methoxycarbonyl)amino)phenyl)-1H-pyrazol-1-yl)propyl)pyridine 1-oxide

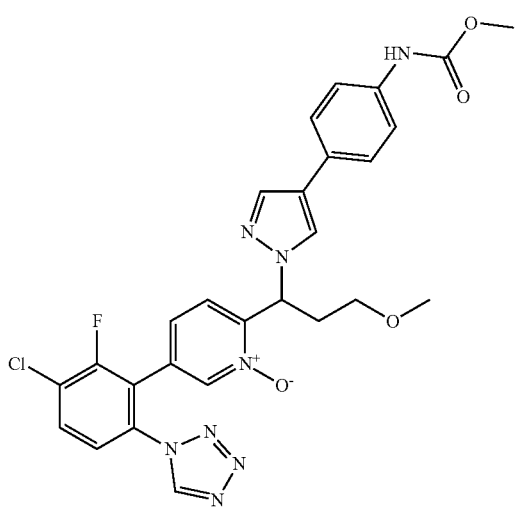 [SMILES: COCCC(c1ccc(-c2c(-n3cnnn3)ccc(Cl)c2F)c[n+]1[O-])n1cc(-c2ccc(NC(=O)OC)cc2)cn1]

LC/MS: mass calculated for $C_{27}H_{24}ClFN_8O_4$: 578.16, measured (ES, m/z): 579.2 [M+H]$^+$. $^1$H NMR (300 MHz, Chloroform-d) δ 8.65 (s, 1H), 8.39 (s, 1H), 7.87 (d, J=2.7 Hz, 2H), 7.79 (t, J=8.4 Hz, 1H), 7.54 (d, J=8.3 Hz, 1H), 7.33-7.50 (m, 5H), 7.06 (d, J=8.3 Hz, 1H), 6.69 (s, 1H), 6.28-6.42 (m, 1H), 3.81 (s, 3H), 3.40-3.54 (m, 1H), 3.32 (s, 3H), 3.17-3.29 (m, 1H), 2.47-2.71 (m, 2H).

Example 39: 5-(5-Chloro-2-(1H-tetrazol-1-yl)phenyl)-2-(1-(4-(4-((methoxycarbonyl)amino)phenyl)-1H-pyrazol-1-yl)-2-phenylethyl)pyridine 1-oxide

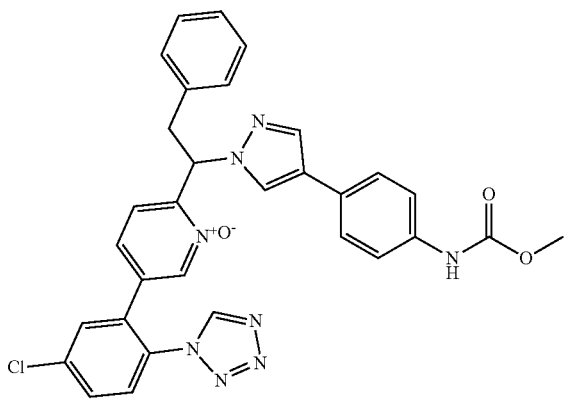

LC/MS: mass calculated for $C_{31}H_{25}ClN_8O_3$: 592.17, measured (ES, m/z): 593.20 [M+H]$^+$. $^1$H NMR (400 MHz, DMSO-d$_6$) δ 9.69 (s, 1H), 9.63 (s, 1H), 8.36 (s, 1H), 8.27 (s, 1H), 7.95 (s, 1H), 7.92 (d, J=2.1 Hz, 1H), 7.81-7.89 (m, 2H), 7.36-7.51 (m, 4H), 7.10-7.29 (m, 6H), 7.96-6.99 (m, 1H), 6.20 (dd, J=10.1, 4.2 Hz, 1H), 3.66 (s, 3H), 3.45-3.62 (m, 2H).

Example 40: 5-(4-Chloro-2-(1H-tetrazol-1-yl)phenyl)-2-(2-cyclopropyl-1-(4-(4-((methoxycarbonyl)amino)phenyl)-1H-pyrazol-1-yl)ethyl)pyridine 1-oxide

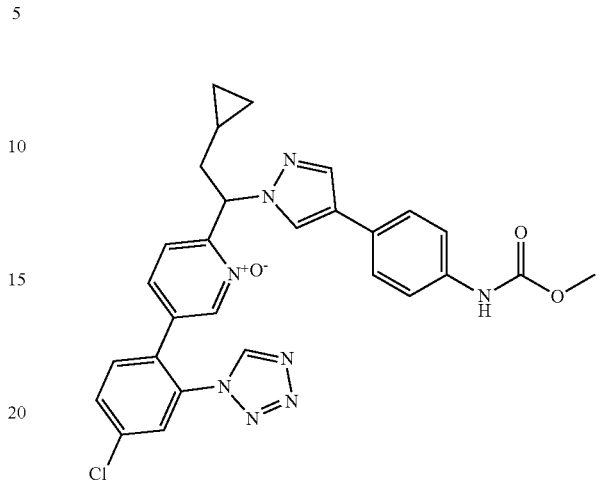

LC/MS: mass calculated for $C_{28}H_{25}ClN_8O_3$: 556.17, measured (ES, m/z): 557.20 [M+H]$^+$. $^1$H NMR (300 MHz, DMSO-d$_6$) δ 9.72 (s, 1H), 9.63 (s, 1H), 8.39 (s, 1H), 8.22 (d, J=1.7 Hz, 1H), 8.03 (d, J=2.1 Hz, 1H), 7.93 (s, 1H), 7.87 (d, J=8.4 Hz, 1H), 7.76 (d, J=8.4 Hz, 1H), 7.51 (d, J=8.7 Hz, 2H), 7.43 (d, J=8.7 Hz, 2H), 7.16 (d, J=8.3 Hz, 1H), 6.94 (d, J=8.3 Hz, 1H), 6.05 (dd, J=9.8, 4.2 Hz, 1H), 3.66 (s, 3H), 2.31-2.44 (m, 1H), 1.75-1.93 (m, 1H), 0.50-68 (m, 1H), 0.22-0.47 (m, 2H), 0.06-0.17 (m, 1H), 0.01-0.05 (m, 1H).

Example 41: 2-(2-Cyclopropyl-1-(4-(4-((methoxycarbonyl)amino)phenyl)-1H-pyrazol-1-yl)ethyl)-5-(4,5-dichloro-2-(1H-tetrazol-1-yl)phenyl)pyridine 1-oxide

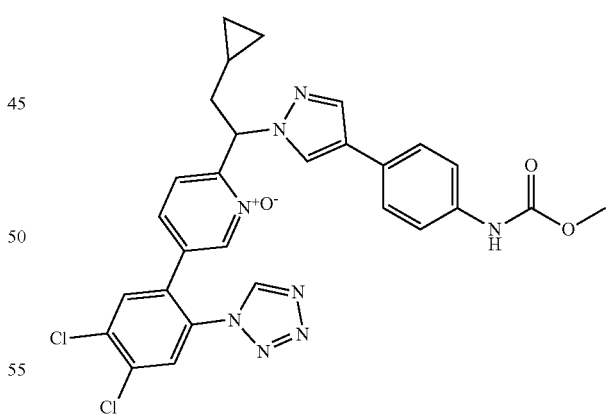

LC/MS: mass calculated for $C_{28}H_{24}Cl_2N_8O_3$: 590.13, measured (ES, m/z): 591.15 [M+H]$^+$. $^1$H NMR (300 MHz, DMSO-d$_6$) δ 9.71 (s, 1H), 9.63 (s, 1H), 8.39 (s, 1H), 8.29 (d, J=1.7 Hz, 1H), 8.26 (s, 1H), 8.12 (s, 1H), 7.93 (s, 1H), 7.47-7.57 (m, 2H), 7.38-7.46 (m, 2H), 7.17 (d, J=8.3 Hz, 1H), 6.95 (d, J=8.3 Hz, 1H), 6.06 (dd, J=9.8, 4.2 Hz, 1H), 3.66 (s, 3H), 2.22-2.43 (m, 1H), 1.74-1.93 (m, 1H), 0.50-0.72 (m, 1H), 0.23-0.44 (m, 2H), 0.08-0.19 (m, 1H), 0.00-0.06 (m, 1H).

Example 42: (R*)-5-(5-Chloro-2-(1H-tetrazol-1-yl)phenyl)-2-(2-cyclopropyl-1-(4-(4-((methoxycarbonyl)amino)phenyl)-1H-pyrazol-1-yl)ethyl)pyridine 1-oxide

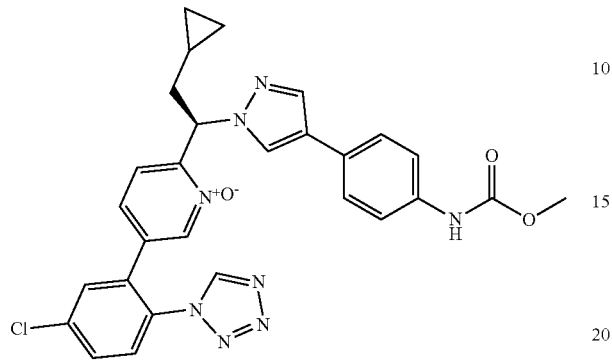

LC/MS: mass calculated for $C_{28}H_{25}ClN_8O_3$: 556.17, measured (ES, m/z): 556.80 [M+H]$^+$. $^1$H NMR (400 MHz, DMSO-$d_6$) δ 9.68 (s, 1H), 9.64 (s, 1H), 8.40 (s, 1H), 8.28 (d, J=1.7 Hz, 1H), 7.94 (s, 1H), 7.90 (d, J=2.1 Hz, 1H), 7.80-7.87 (m, 2H), 7.49-7.57 (m, 2H), 7.40-7.46 (m, 2H), 7.16 (d, J=8.4 Hz, 1H), 6.96 (d, J=8.3 Hz, 1H), 6.06 (dd, J=9.8, 4.3 Hz, 1H), 3.67 (s, 3H), 2.29-2.44 (m, 1H), 1.79-1.90 (m, 1H), 0.52-0.65 (m, 1H), 0.27-0.44 (m, 2H), 0.08-0.19 (m, 1H), 0.00-0.08 (m, 1H).

Example 43: (S*)-5-(5-Chloro-2-(1H-tetrazol-1-yl)phenyl)-2-(2-cyclopropyl-1-(4-(4-((methoxycarbonyl)amino)phenyl)-1H-pyrazol-1-yl)ethyl)pyridine 1-oxide

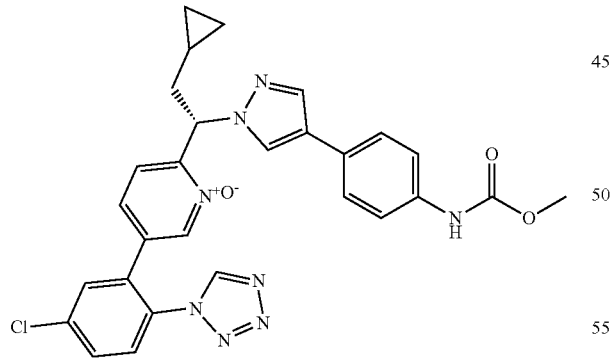

LC/MS: mass calculated for $C_{28}H_{25}ClN_8O_3$: 556.17, measured (ES, m/z): 556.80 [M+H]$^+$. $^1$H NMR (400 MHz, DMSO-$d_6$) δ 9.68 (s, 1H), 9.64 (s, 1H), 8.40 (s, 1H), 8.28 (d, J=1.7 Hz, 1H), 7.94 (s, 1H), 7.90 (d, J=2.1 Hz, 1H), 7.79-7.87 (m, 2H), 7.48-7.56 (m, 2H), 7.44 (d, J=8.5 Hz, 2H), 7.16 (d, J=8.4 Hz, 1H), 6.96 (d, J=8.3 Hz, 1H), 6.06 (dd, J=9.8, 4.3 Hz, 1H), 3.67 (s, 3H), 2.26-2.44 (m, 1H), 1.77-1.96 (m, 1H), 0.54-0.70 (m, 1H), 0.25-0.43 (m, 2H), 0.08-0.21 (m, 1H), 0.00-0.07 (m, 1H).

Example 44: 5-(5-Chloro-4-fluoro-2-(1H-tetrazol-1-yl)phenyl)-2-(3-methoxy-1-(4-(4-((methoxycarbonyl)amino)phenyl)-1H-pyrazol-1-yl)propyl)pyridine 1-oxide

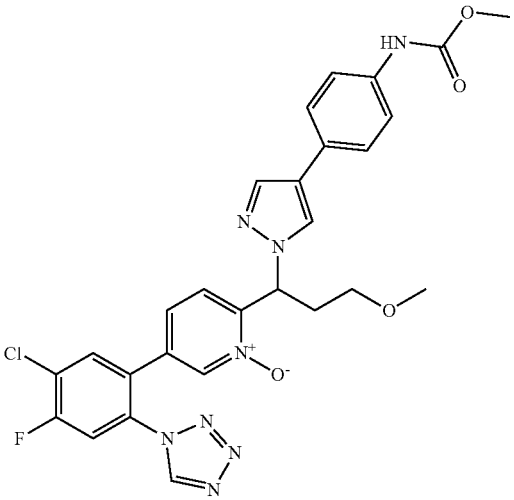 [SMILES: COCCC(c1ccc(-c2cc(Cl)c(F)cc2-n2cnnn2)c[n+]1[O-])n1cc(-c2ccc(NC(=O)OC)cc2)cn1]

LC/MS: mass calculated for $C_{27}H_{24}ClFN_8O_4$: 578.16, measured (ES, m/z): 578.80 [M+H]$^+$. $^1$H NMR (300 MHz, Chloroform-d) δ 8.55 (s, 1H), 8.26 (s, 1H), 7.83 (d, J=5.8 Hz, 2H), 7.62 (d, J=7.2 Hz, 1H), 7.33-7.56 (m, 6H), 6.80 (d, J=8.3 Hz, 1H), 6.64 (s, 1H), 6.22-6.40 (m, 1H), 3.78 (s, 3H), 3.38-3.53 (m, 1H), 3.30 (s, 3H), 3.12-3.27 (m, 1H), 2.47-2.66 (m, 2H). $^{19}$F NMR (282 MHz, Chloroform-d) δ −75.81, −108.49.

Example 45: 2-(1-(4-(6-Amino-2-fluoropyridin-3-yl)-1H-pyrazol-1-yl)-2-phenylethyl)-5-(5-chloro-2-(1H-tetrazol-1-yl)phenyl)pyridine 1-oxide

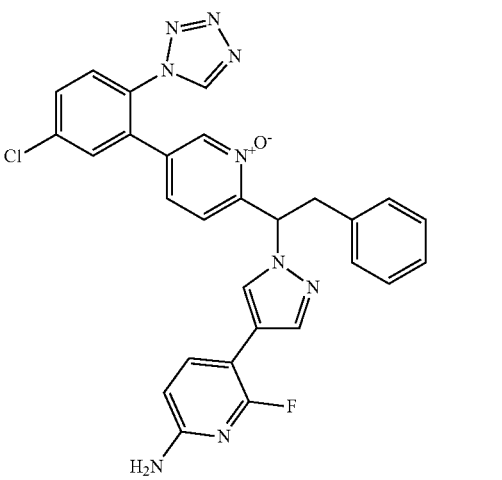

LC/MS: mass calculated for $C_{28}H_{21}ClFN_9O$: 553.15, measured (ES, m/z): 554.05 [M+H]$^+$. $^1$H NMR (400 MHz, DMSO-$d_6$) δ 9.69 (s, 1H), 8.35 (s, 1H), 8.09 (s, 1H), 7.92 (s, 1H), 7.81-7.88 (m, 3H), 7.70-7.78 (m, 1H), 7.10-7.31 (m, 6H), 6.98 (d, J=8.3 Hz, 1H), 6.34 (d, J=8.3 Hz, 1H), 6.23

(dd, J=9.9, 4.4 Hz, 1H), 3.43-3.68 (m, 2H). $^{19}$F NMR (376 MHz, DMSO-d$_6$) δ −71.34, −74.75.

Example 46: 5-(5-Chloro-4-fluoro-2-(1H-tetrazol-1-yl)phenyl)-2-(1-(4-(4-((methoxycarbonyl)amino)phenyl)-1H-pyrazol-1-yl)-2-phenylethyl)pyridine 1-oxide

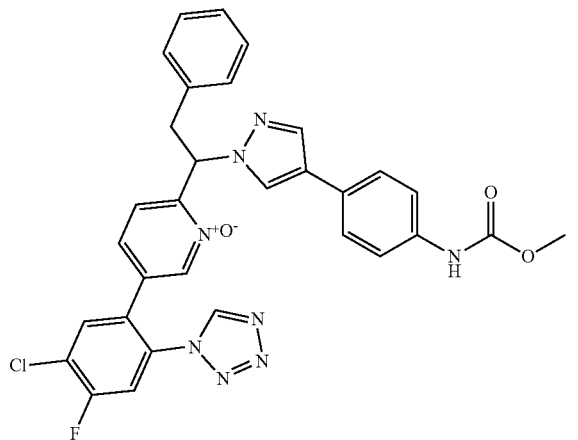

LC/MS: mass calculated for C$_{31}$H$_{24}$ClFN$_8$O$_3$: 610.16; measured (ES, m/z): 610.75 [M+H]$^+$. $^1$H NMR (400 MHz, DMSO-d$_6$) δ 9.70 (s, 1H), 9.62 (s, 1H), 8.36 (s, 1H), 8.26 (s, 1H), 8.10-8.14 (m, 2H), 7.94 (s, 1H), 7.38-7.47 (m, 4H), 7.11-7.29 (m, 6H), 6.97 (d, J=8.3 Hz, 1H), 6.20 (dd, J=10.0, 4.2 Hz, 1H), 3.65 (s, 3H), 3.43-3.63 (m, 2H). $^{19}$F NMR (376 MHz, DMSO-d$_6$) δ −74.59, −112.76.

Example 47: 2-(1-(4-(4-(1-Aminoethyl)phenyl)-1H-pyrazol-1-yl)-2-phenylethyl)-5-(5-chloro-2-(1H-tetrazol-1-yl)phenyl)pyridine 1-oxide

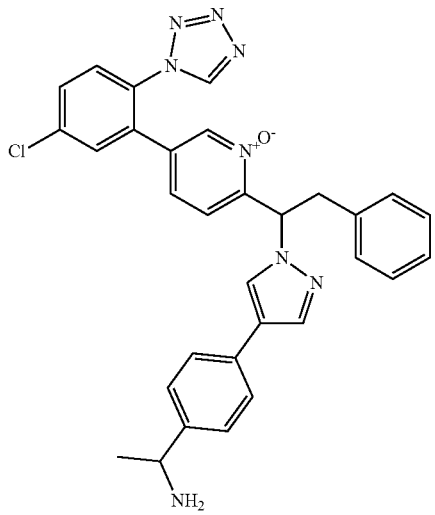

LC/MS: mass calculated for C$_{31}$H$_{27}$ClN$_8$O: 562.20; measured (ES, m/z): 563.25 [M+H]$^+$. $^1$H NMR (300 MHz, DMSO-d$_6$) δ 9.68 (s, 1H), 8.32-8.38 (m, 2H), 8.10-8.24 (m, 3H), 8.04 (s, 1H), 7.88-7.93 (m, 1H), 7.76-7.87 (m, 2H), 7.60 (d, J=8.2 Hz, 2H), 7.42 (d, J=8.2 Hz, 2H), 7.28 (d, J=8.4 Hz, 1H), 7.10-7.19 (m, 5H), 6.98 (d, J=8.3 Hz, 1H), 6.12-6.33 (m, 1H), 4.27-4.50 (m, 1H), 3.51-3.56 (m, 2H), 1.47 (d, J=6.7 Hz, 3H). $^{19}$F NMR (282 MHz, DMSO-d$_6$) δ −73.76.

Example 48: (R*)-2-(1-(4-(6-Amino-2-chloropyridin-3-yl)-1H-pyrazol-1-yl)-2-cyclopropylethyl)-5-(5-chloro-2-(1H-tetrazol-1-yl)phenyl)pyridine 1-oxide

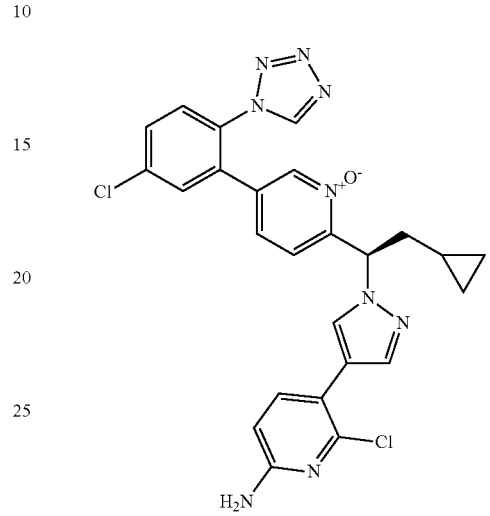

LC/MS: mass calculated for C$_{25}$H$_{21}$Cl$_2$N$_9$O: 533.12, measured (ES, m/z): 534.05 [M+H]$^+$. $^1$H NMR (400 MHz, DMSO-d$_6$) δ 9.68 (s, 1H), 8.23-8.33 (m, 2H), 7.90 (d, J=2.1 Hz, 1H), 7.80-7.88 (m, 3H), 7.63 (d, J=8.4 Hz, 1H), 7.22 (d, J=8.3 Hz, 1H), 6.97 (d, J=8.3 Hz, 1H), 6.46 (d, J=8.3 Hz, 1H), 6.37 (br, 2H), 6.09 (dd, J=9.9, 4.4 Hz, 1H), 2.23-2.44 (m, 1H), 1.79-1.97 (m, 1H), 0.51-0.66 (m, 1H), 0.23-0.46 (m, 2H), 0.06-0.16 (m, 1H), −0.07-0.06 (m, 1H).

Example 49: (S*)-2-(1-(4-(6-Amino-2-chloropyridin-3-yl)-1H-pyrazol-1-yl)-2-cyclopropylethyl)-5-(5-chloro-2-(1H-tetrazol-1-yl)phenyl)pyridine 1-oxide

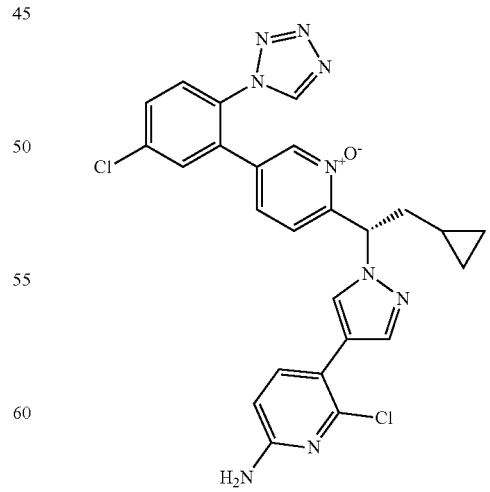

LC/MS: mass calculated for C$_{25}$H$_{21}$Cl$_2$N$_9$O: 533.12, measured (ES, m/z): 534.05 [M+H]$^+$. $^1$H NMR (400 MHz, DMSO-d$_6$) δ 9.68 (s, 1H), 8.23-8.33 (m, 2H), 7.90 (d, J=2.1

Hz, 1H), 7.80-7.88 (m, 3H), 7.63 (d, J=8.3 Hz, 1H), 7.22 (d, J=8.4 Hz, 1H), 6.97 (d, J=8.3 Hz, 1H), 6.46 (d, J=8.3 Hz, 1H), 6.36 (br, 2H), 6.09 (dd, J=9.8, 4.4 Hz, 1H), 2.25-2.40 (m, 1H), 1.79-1.96 (m, 1H), 0.51-0.66 (m, 1H), 0.23-0.46 (m, 2H), 0.06-0.16 (m, 1H), −0.07-0.06 (m, 1H).

Example 50: 2-(1-(4-(6-Amino-5-fluoropyridin-3-yl)-1H-pyrazol-1-yl)-2-phenylethyl)-5-(chloro-2-(1H-tetrazol-1-yl)phenyl)pyridine 1-oxide

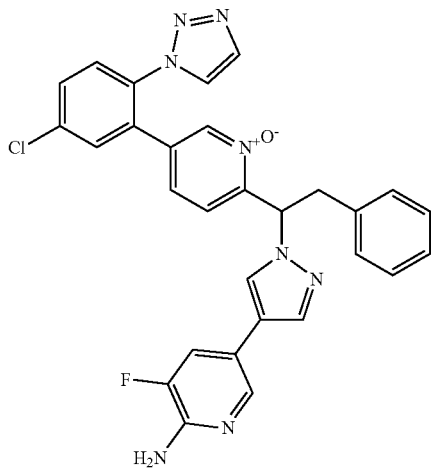

LC/MS: mass calculated for $C_{28}H_{21}ClFN_9O$: 553.15; measured (ES, m/z): 553.80 [M+H]+. $^1$H NMR (300 MHz, DMSO-$d_6$) δ 9.70 (s, 1H), 8.29-8.40 (m, 2H), 8.03 (s, 2H), 7.78-7.96 (m, 4H), 7.10-7.35 (m, 6H), 6.99 (d, J=8.3 Hz, 1H), 6.19 (dd, J=9.9, 4.5 Hz, 1H), 3.43-3.65 (m, 2H).

Example 51: 2-((4-(4-Carboxyphenyl)-1H-pyrazol-1-yl)(1-(piperidin-4-yl)-1H-1,2,3-triazol-4-yl)methyl)-5-(5-chloro-2-(1H-tetrazol-1-yl)phenyl)pyridine 1-oxide

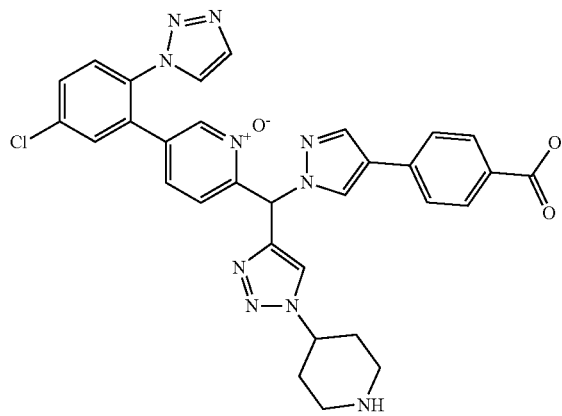

LC/MS: mass calculated for $C_{30}H_{28}ClN_{11}O_3$: 623.19; measured (ES, m/z): 624.10 [M+H]+. $^1$H NMR (300 MHz, DMSO-$d_6$) δ 9.70 (s, 1H), 8.60-8.86 (m, 1H), 8.31-8.51 (m, 3H), 8.25 (s, 1H), 8.14 (s, 1H), 7.83-7.96 (m, 5H), 7.73 (d, J=8.3 Hz, 2H), 7.46 (s, 1H), 7.12 (d, J=8.4 Hz, 1H), 6.95-7.04 (m, 1H), 4.66-5.01 (m, 1H), 3.34-3.56 (m, 2H), 2.97-3.21 (m, 2H), 2.25-2.40 (m, 2H), 2.04-2.24 (m, 2H). $^{19}$F NMR (282 MHz, DMSO-$d_6$) δ −74.06.

Example 52: 2-((4-(4-Carboxyphenyl)-1H-pyrazol-1-yl)(1-(piperidin-4-yl)-1H-1,2,3-triazol-4-yl)methyl)-5-(3-chloro-2-fluoro-6-(1H-tetrazol-1-yl)phenyl)pyridine 1-oxide

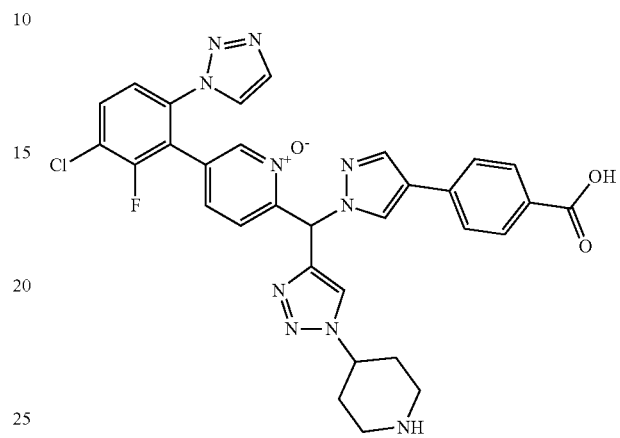

LC/MS: mass calculated for $C_{30}H_{25}ClFN_{11}O_3$: 641.18, measured (ES, m/z): 642.1 [M+H]+. $^1$H NMR (300 MHz, DMSO-$d_6$) δ 9.71 (s, 1H), 8.71 (s, 1H), 8.44 (d, J=6.6 Hz, 2H), 8.25 (s, 1H), 8.14 (s, 1H), 8.01-8.11 (m, 1H), 7.90-7.94 (m, 2H), 7.67-7.81 (m, 3H), 7.45 (s, 1H), 7.13-7.25 (m, 2H), 4.71-4.99 (m, 1H), 3.31-3.55 (m, 2H), 2.92-3.25 (m, 2H), 2.26-2.40 (m, 2H), 2.01-2.25 (m, 2H). $^{19}$F NMR (282 MHz, DMSO-$d_6$) δ −73.99, −112.61.

Example 53: 2-((1-(1-Acetylpiperidin-4-yl)-1H-1,2,3-triazol-4-yl)(4-(4-Carboxyphenyl)-1H-pyrazol-1-yl)methyl)-5-(5-chloro-2-(1H-tetrazol-1-yl)phenyl)pyridine 1-oxide

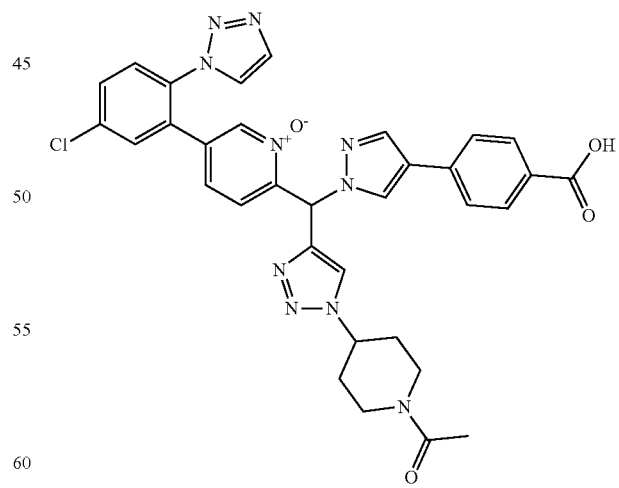

LC/MS: mass calculated for $C_{32}H_{28}ClN_{11}O_4$: 665.2; measured (ES, m/z): 666.00 [M+H]+. $^1$H NMR (300 MHz, DMSO-$d_6$) δ 9.70 (s, 1H), 8.42 (s, 1H), 8.34 (d, J=1.6 Hz, 1H), 8.23 (s, 1H), 8.12 (s, 1H), 7.82-7.96 (m, 5H), 7.72 (d, J=8.4 Hz, 2H), 7.44 (s, 1H), 7.12 (d, J=8.3 Hz, 1H), 6.99 (d, J=9.2 Hz, 1H), 4.72-4.90 (m, 1H), 4.36-4.52 (m, 1H), 3.81-3.98 (m, 1H), 3.11-3.33 (m, 1H), 2.62-2.85 (m, 1H), 2.04-2.23 (m, 2H), 2.03 (s, 3H), 1.69-1.99 (m, 2H).

Example 54: 2-((1-(1-Acetylpiperidin-4-yl)-1H-1,2,3-triazol-4-yl)(4-(4-Carboxyphenyl)-1H-pyrazol-1-yl)methyl)-5-(3-chloro-2-fluoro-6-(1H-tetrazol-1-yl)phenyl)pyridine 1-oxide

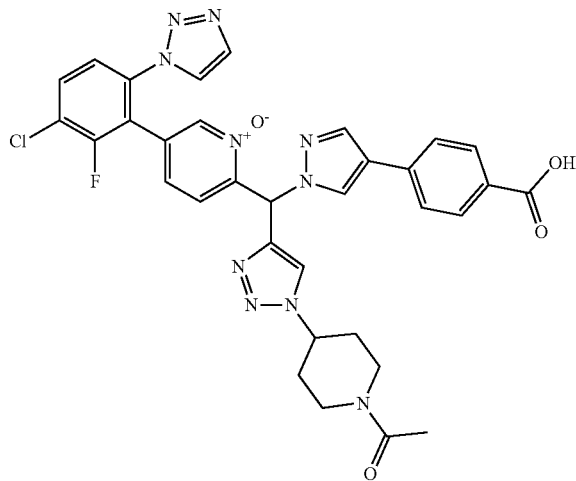

LC/MS: mass calculated for $C_{32}H_{27}ClFN_{11}O_4$: 683.2, measured (ES, m/z): 684.20 [M+H]$^+$. $^1$H NMR (300 MHz, DMSO-d$_6$) δ 9.70 (s, 1H), 8.40-8.45 (m, 2H), 8.22 (s, 1H), 8.13 (s, 1H), 8.01-8.11 (m, 1H), 7.91 (d, J=8.3 Hz, 2H), 7.67-7.81 (m, 3H), 7.43 (s, 1H), 7.14-7.21 (m, 2H), 4.70-4.92 (m, 1H), 4.37-4.58 (m, 1H), 3.85-4.01 (m, 1H), 3.12-3.30 (m, 1H), 2.62-2.83 (m, 1H), 2.06-2.29 (m, 2H), 2.03 (s, 3H), 1.88-2.00 (m, 1H), 1.61-1.87 (m, 1H).

Example 55: 5-(5-Chloro-2-(1H-tetrazol-1-yl)phenyl)-2-(1-(4-(4-(cyclopropylcarbamoyl)phenyl)-1H-pyrazol-1-yl)-2-(4-fluorophenyl)ethyl)pyridine 1-oxide

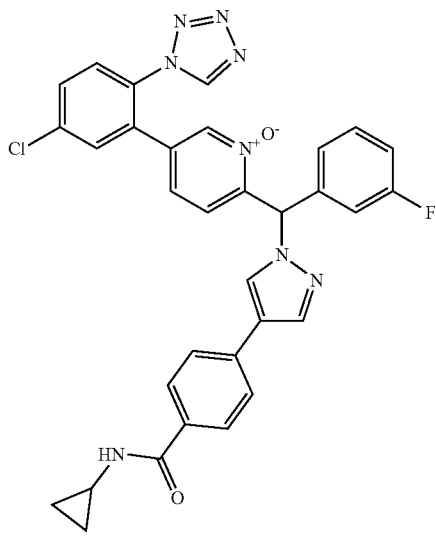

LC/MS: mass calculated for $C_{33}H_{26}ClFN_8O_2$: 620.2, measured (ES, m/z): 621.3 [M+H]$^+$. $^1$H NMR (400 MHz, CD$_3$OD) δ ppm 0.58-0.67 (m, 2H), 0.76-0.85 (m, 2H), 2.77-2.89 (m, 1H), 3.54-3.71 (m, 2H), 6.22-6.30 (m, 1H), 6.94 (t, J=8.84 Hz, 2H), 7.19 (br d, J=8.08 Hz, 3H), 7.48-7.53 (m, 1H), 7.55-7.61 (m, 2H), 7.77 (s, 5H), 8.00-8.05 (m, 1H), 8.06-8.11 (m, 1H), 8.27-8.34 (m, 1H), 9.38 (s, 1H).

Example 56: 5-(4-Chloro-2-fluoro-6-(1H-tetrazol-1-yl)phenyl)-2-(2-cyclopropyl-1-(4-(4-((methoxycarbonyl)amino)phenyl)-1H-pyrazol-1-yl)ethyl)pyridine 1-oxide

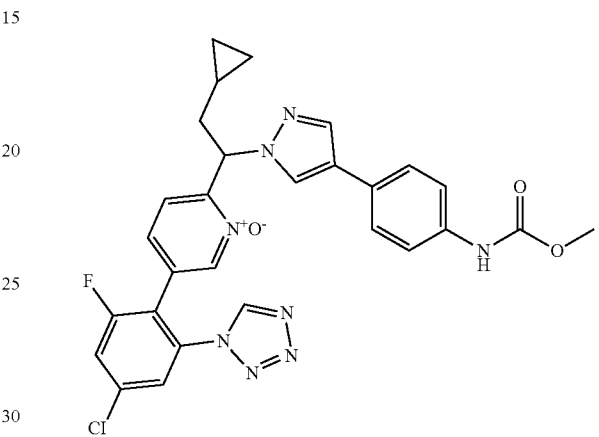

LC/MS: mass calculated for $C_{28}H_{24}ClFN_8O_3$: 574.16, measured (ES, m/z): 575.15 [M+H]$^+$. $^1$H NMR (300 MHz, DMSO-d$_6$) δ 9.71 (s, 1H), 9.63 (s, 1H), 8.32-8.46 (m, 2H), 8.04 (d, J=9.2 Hz, 1H), 7.92-8.00 (m, 2H), 7.39-7.58 (m, 4H), 7.20 (d, J=8.3 Hz, 1H), 7.07-7.14 (m, 1H), 6.05 (dd, J=9.8, 4.2 Hz, 1H), 3.66 (s, 3H), 2.27-2.45 (m, 1H), 1.75-1.94 (m, 1H), 0.53-0.71 (m, 1H), 0.25-0.46 (m, 2H), 0.06-0.19 (m, 1H), −0.01-0.05 (m, 1H).

Example 57: 2-(1-(4-(4-Carboxyphenyl)-1H-pyrazol-1-yl)-2-(4-chlorophenyl)ethyl)-5-(5-chloro-2-(1H-tetrazol-1-yl)phenyl)pyridine 1-oxide

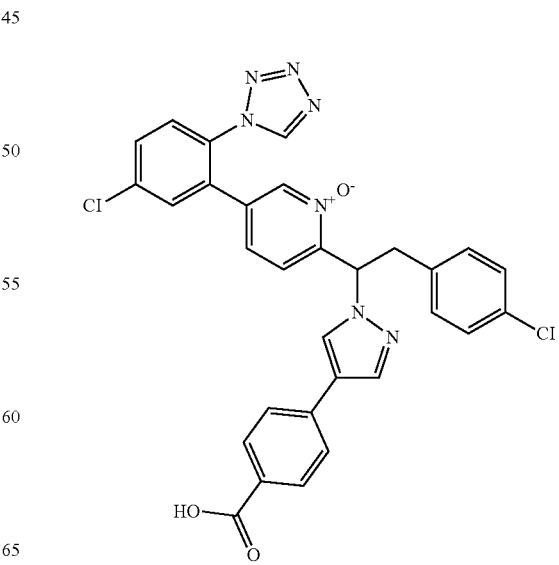

LC/MS: mass calculated for $C_{30}H_{21}Cl_2N_7O_3$: 597.1, measured (ES, m/z): 598.0 [M+H]$^+$. $^1$H 7.78-7.98 (m, 5H), 7.67 (d, J=8.2 Hz, 2H), 7.13-7.37 (m, 5H), 6.99 (dd, J=8.3, 1.7 Hz, 1H), 6.22 (dd, J=10.1, 4.5 Hz, 1H), 3.38-3.79 (m, 2H).

Example 58: 5-(5-Chloro-2-(1H-tetrazol-1-yl)phenyl)-2-(1-(4-(4-(1-((methoxycarbonyl)amino)ethyl)phenyl)-1H-pyrazol-1-yl)-2-phenylethyl)pyridine 1-oxide

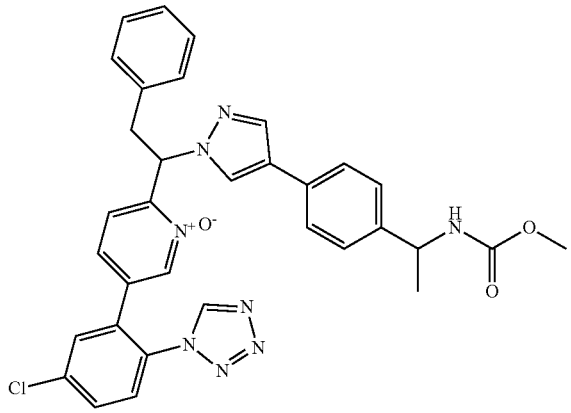

LC/MS: mass calculated for $C_{33}H_{29}ClN_8O_3$: 620.2, measured (ES, m/z): 621.0 [M+H]$^+$. $^1$H NMR (300 MHz, CD$_3$OD) δ 9.38 (s, 1H), 8.30 (s, 1H), 7.94 (d, J=8.9 Hz, 2H), 7.75-7.82 (m, 2H), 7.71 (d, J=9.2 Hz, 1H), 7.50 (d, J=8.3 Hz, 1H), 7.43 (d, J=7.9 Hz, 2H), 7.27 (d, J=8.1 Hz, 2H), 7.12-7.24 (m, 6H), 6.20-6.36 (m, 1H), 4.58-4.77 (m, 1H), 3.61 (s, 5H), 1.42 (d, J=7.0 Hz, 3H).

Example 59: 2-(1-(4-(6-Amino-2-fluoropyridin-3-yl)-1H-pyrazol-1-yl)-2-phenylethyl)-5-(5-chloro-2-(1H-tetrazol-1-yl)phenyl)-3-fluoropyridine 1-oxide

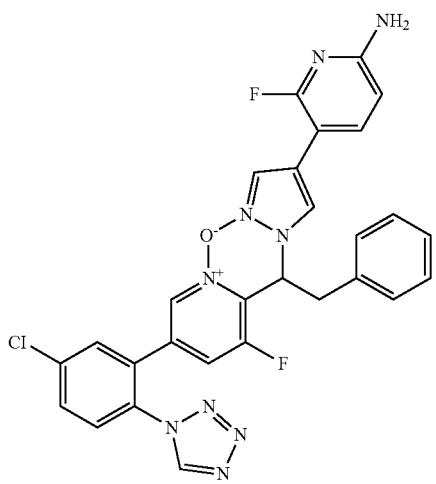

LC/MS: mass calculated for $C_{28}H_{20}ClF_2N_9O$: 571.14, measured (ES, m/z): 571.95 [M+H]$^+$. $^1$H NMR (300 MHz, DMSO-d$_6$) δ 9.66 (s, 1H), 8.07-8.22 (m, 2H), 7.65-7.97 (m, 5H), 7.08-7.36 (m, 6H), 6.27-6.43 (m, 2H), 3.78 (d, J=8.2 Hz, 2H). $^{19}$F NMR (282 MHz, DMSO-d$_6$) δ −71.61, −74.67, −118.86.

Example 60: 2-((4-(4-Carboxyphenyl)-1H-pyrazol-1-yl)methyl)-5-(5-chloro-2-(1H-tetrazol-1-yl)phenyl)pyridine 1-oxide

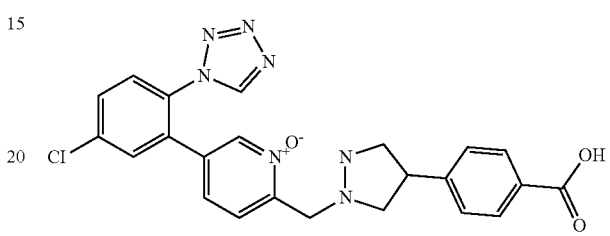

LC/MS: mass calculated for $C_{23}H_{16}ClN_7O_3$: 473.10, measured (ES, m/z): 474.00 [M+H]$^+$. $^1$H NMR (300 MHz, DMSO-d$_6$) δ 12.84 (br, 1H), 9.69 (s, 1H), 8.48 (s, 1H), 8.34 (d, J=1.7 Hz, 1H), 8.11 (s, 1H), 7.79-7.97 (m, 5H), 7.72 (d, J=8.3 Hz, 2H), 6.92-7.00 (m, 1H), 6.78 (d, J=8.2 Hz, 1H), 5.51 (s, 2H).

Example 61: 5-(4-Chloro-5-fluoro-2-(1H-tetrazol-1-yl)phenyl)-2-(2-cyclopropyl-1-(4-(4-((methoxycarbonyl)amino)phenyl)-1H-pyrazol-1-yl)ethyl)pyridine 1-oxide

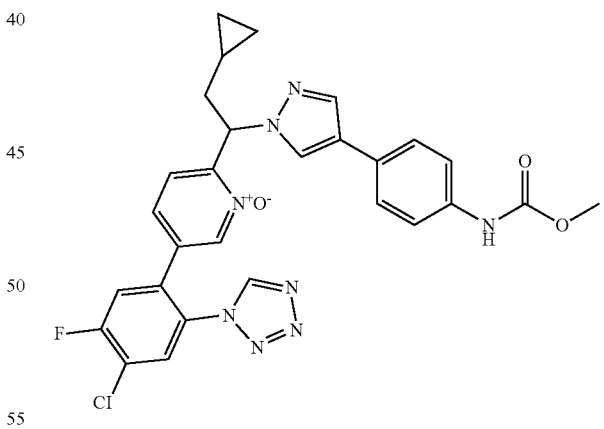

LC/MS: mass calculated for $C_{28}H_{24}ClFN_8O$: 574.16, measured (ES, m/z): 575.15 [M+H]$^+$. $^1$H NMR (300 MHz, DMSO-d$_6$) δ 9.67 (s, 1H), 9.61 (s, 1H), 8.36 (s, 1H), 8.17-8.30 (m, 2H), 7.88-7.97 (m, 2H), 7.45-7.54 (m, 2H), 7.37-7.45 (m, 2H), 7.16 (d, J=8.3 Hz, 1H), 6.91 (d, J=8.3 Hz, 1H), 6.03 (dd, J=9.8, 4.3 Hz, 1H), 3.64 (s, 3H), 2.26-2.42 (m, 1H), 1.75-1.88 (m, 1H), 0.55-0.61 (m, 1H), 0.26-0.39 (m, 2H), 0.06-0.15 (m, 1H), −0.04-0.05 (m, 1H). $^{19}$F NMR (282 MHz, DMSO-d$_6$) δ −74.41, −112.04.

Example 62: 2-(2-(2-([1,1'-Biphenyl]-4-yl)cyclopropyl)-1-(4-(4-carboxyphenyl)-1H-pyrazol-1-yl)ethyl)-5-(5-chloro-2-(1H-tetrazol-1-yl)phenyl)pyridine 1-oxide

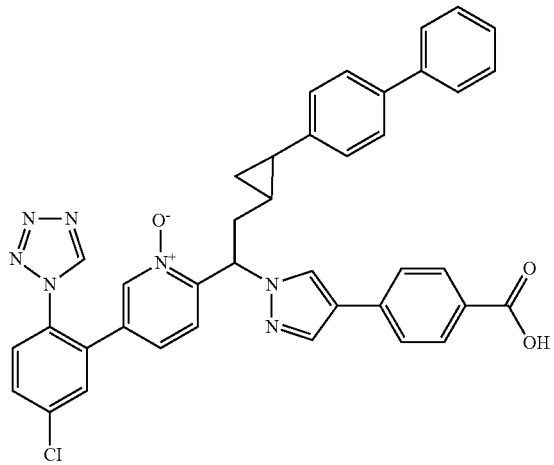

LC/MS: mass calculated for $C_{39}H_{30}ClN_7O_3$: 679.2, measured (ES, m/z): 680 [M]+. $^1$H NMR (400 MHz, CD$_3$OD) δ ppm 0.74-0.98 (m, 2H), 1.11-1.17 (m, 1H), 1.24-1.32 (m, 1H), 1.35-1.49 (m, 1H), 2.27-2.42 (m, 1H), 2.43-2.56 (m, 1H), 2.68-2.79 (m, 1H), 6.21-6.33 (m, 1H), 6.74-6.87 (m, 1H), 7.03-7.11 (m, 2H), 7.11-7.29 (m, 5H), 7.29-7.86 (m, 6H), 7.87-8.29 (m, 5H), 9.37 (s, 1H).

Example 63: 2-(2-([1,1'-Biphenyl]-4-yl)-1-(4-(4-Carboxyphenyl)-1H-pyrazol-1-yl)ethyl)-5-(5-chloro-2-(1H-tetrazol-1-yl)phenyl)pyridine 1-oxide

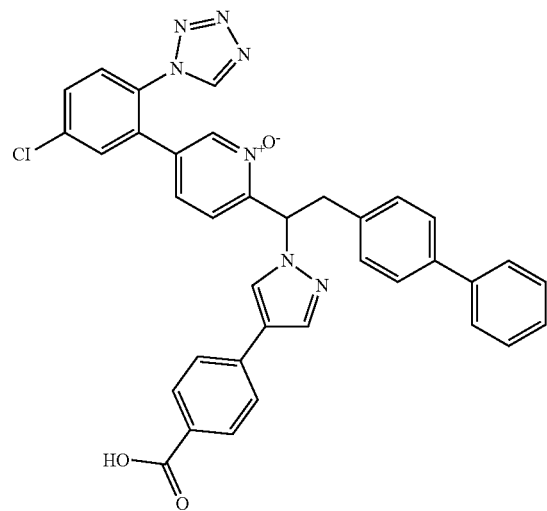

LC/MS: mass calculated for $C_{36}H_{26}ClN_7O_3$: 639.18, measured (ES, m/z): 640.15 [M+H]$^+$. $^1$H NMR (300 MHz, DMSO-d$_6$) δ 12.81 (s, 1H), 9.68 (s, 1H), 8.55 (s, 1H), 8.36 (d, J=1.7 Hz, 1H), 8.13 (s, 1H), 7.77-7.94 (m, 5H), 7.49-7.71 (m, 6H), 7.35-7.45 (m, 2H), 7.18-7.34 (m, 4H) 6.98 (d, J=8.3 Hz, 1H), 6.28 (dd, J=9.6, 4.5 Hz, 1H), 3.49-3.71 (m, 2H).

Example 64: 2-(1-(4-(6-Acetamido-2-fluoropyridin-3-yl)-1H-pyrazol-1-yl)-2-cyclopropylethyl)-5-(3-Chloro-2-fluoro-6-(1H-tetrazol-1-yl)phenyl)-4-methoxypyridine 1-oxide

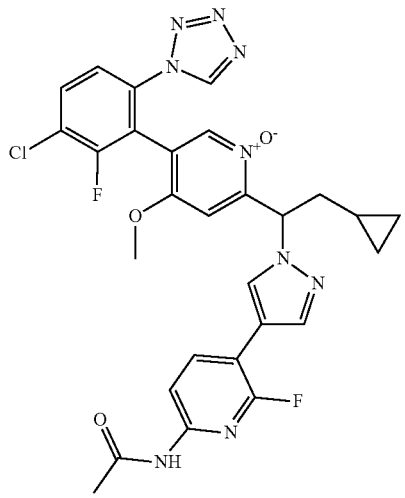

LC/MS: mass calculated for $C_{28}H_{24}ClF_2N_9O_3$: 607.17, measured (ES, m/z): 608.15 [M+H]$^+$. $^1$H NMR (300 MHz, DMSO-d$_6$) δ 10.65 (d, J=2.9 Hz, 1H), 9.71 (d, J=7.3 Hz, 1H), 8.34-8.48 (m, 2H), 8.17-8.29 (m, 1H), 7.93-8.09 (m, 3H), 7.68-7.79 (m, 1H), 6.91-7.09 (m, 1H), 6.11-6.18 (m, 1H), 3.70 (s, 3H), 2.31-2.45 (m, 1H), 2.07 (s, 3H), 1.87-2.02 (m, 1H), 0.51-0.63 (m, 1H), 0.24-0.39 (m, 2H), 0.04-0.16 (m, 1H), −0.08-0.01 (m, 1H). $^{19}$F NMR (282 MHz, Chloroform-d) δ −65.73, −65.78, −69.92, −106.93, −107.06.

Example 65: 2-(1-(4-(4-Carboxyphenyl)-1H-pyrazol-1-yl)-2-(4-methoxyphenyl)ethyl)-5-(5-chloro-2-(1H-tetrazol-1-yl)phenyl)pyridine 1-oxide

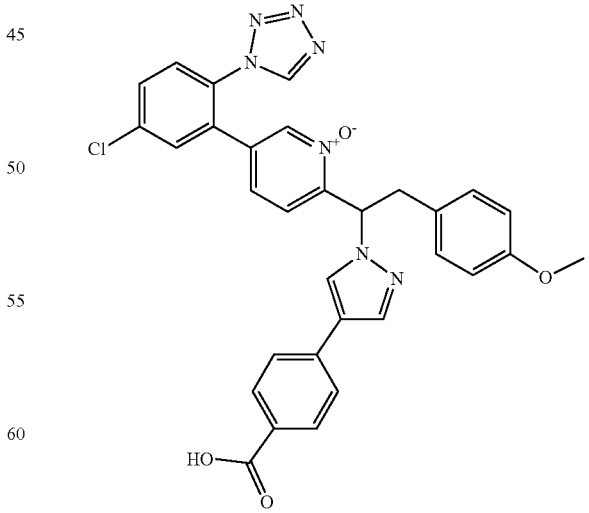

LC/MS: mass calculated for $C_{31}H_{24}ClN_7O_4$: 593.16, measured (ES, m/z): 594.20 [M+H]$^+$. $^1$H NMR (300 MHz, DMSO-d$_6$) δ 9.69 (s, 1H), 8.50 (s, 1H), 8.35 (s, 1H), 8.13 (s, 1H), 7.80-7.96 (m, 5H), 7.62-7.72 (m, 2H), 7.28 (d, J=8.3 Hz, 1H), 7.15 (dd, J=9.1, 7.3 Hz, 1H), 6.99 (d, J=8.3 Hz, 1H), 6.69-6.80 (m, 3H), 6.22 (dd, J=9.1, 4.4 Hz, 1H), 3.64 (s, 3H), 3.42-3.63 (m, 2H).

Example 66: 2-(1-(4-(4-Carboxyphenyl)-1H-pyrazol-1-yl)-3-phenylpropyl)-5-(5-chloro-2-(1H-tetrazol-1-yl)phenyl)pyridine 1-oxide

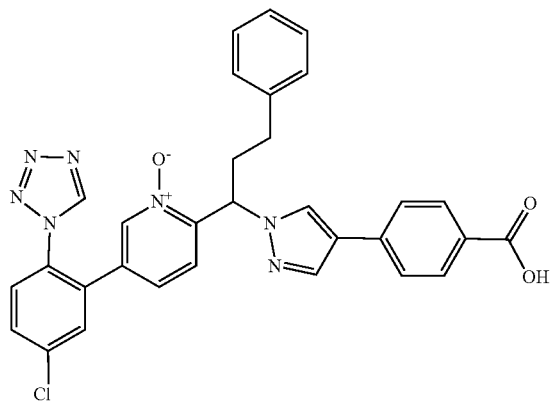

Step 1:
1-(5-Bromopyridin-2-yl)-3-phenylpropan-1-ol

To a mixture of 4-bromopicolinaldehyde in THF (30 mL) under nitrogen was added phenethylmagnesium chloride solution (6.45 mL, 6.45 mmol) at −78° C. The resulting mixture was stirred at −78° C. for 2 h. The reaction was quenched with aqueous NH$_4$Cl (50 mL) and extracted with EtOAc (2×25 mL).

The combined organic layer was washed with brine (1×25 mL), dried over Na$_2$SO$_4$ and concentrated in vacuo. The residue was purified by silica gel chromatography (0-50% EtOAc/petroleum ether) to yield 1-(5-bromopyridin-2-yl)-3-phenylpropan-1-ol as a light-yellow oil, which was used in the next step without further purification.

Step 2: 1-(5-Bromopyridin-2-yl)-3-phenylpropyl methanesulfonate

To a mixture of 1-(5-bromopyridin-2-yl)-3-phenylpropan-1-ol (510 mg, 1.75 mmol) in DCM (10 mL) with triethylamine (0.49 mL, 2.00 mmol) was added methanesulfonyl chloride (0.162 mL, 1.20 mmol). The reaction was stirred at room temperature for 1 h. Water was added, and the mixture was extracted with DCM. The combined extracts were washed with water, saturated brine and dried over anhydrous Na$_2$SO$_4$. The resulting mixture was concentrated and purified by chromatography on EA/PE (1-25%) to yield 2-(2-([1,1'-biphenyl]-4-yl)cyclopropyl)-1-(5-bromopyridin-2-yl)ethyl methanesulfonate as a yellow solid, which was used in the next step without further purification.

Step 3: tert-Butyl 4-(1-(1-(5-bromopyridin-2-yl)-2-(4-fluorophenyl)ethyl)-1H-pyrazol-4-yl)benzoate To a mixture of 2-(2-([1,1'-biphenyl]-4-yl)cyclopropyl)-1-(5-bromopyridin-2-yl)ethyl methanesulfonate (852.9 mg, 2.30 mmol) and cesium carbonate (900 mg, 2.76 mmol) in CH$_3$CN (10 mL) was added tert-butyl 4-(1H-pyrazol-4-yl)benzoate (732 mg, 2.99 mmol). The resulting mixture was stirred at 80° C. for 4 h. Water was added, and the mixture was extracted with EA. The combined extracts were washed with water, saturated brine and dried over anhydrous Na$_2$SO$_4$. The resulting mixture was concentrated and purified by flash column chromatography on silica gel with EA/PE (1-40%) to yield tert-butyl 4-(1-(1-(5-bromopyridin-2-yl)-2-(4-fluorophenyl)ethyl)-1H-pyrazol-4-yl)benzoate as a yellow oil. LC/MS: mass calculated for C$_{28}$H$_{28}$BrN$_3$O$_2$: 517.1, measured (ES, m/z): 519.1 [M+H+2]$^+$.

Step 4: 2-(1-(4-(4-Carboxyphenyl)-1H-pyrazol-1-yl)-3-phenylpropyl)-5-(5-chloro-2-(1H-tetrazol-1-yl)phenyl)pyridine 1-oxide To a solution of 4-(1-(1-(5-(5-chloro-2-(1H-tetrazol-1-yl)phenyl)pyridin-2-yl)-3-phenylpropyl)-1H-pyrazol-4-yl)benzoic acid (167.6 mg, 0.3 mmol) in CH$_3$OH (6 mL) was added MeReO$_3$ (37.2 mg, 0.15 mmol) and H$_2$O$_2$ (30%, 169 mg, 1.49 mmol) The resulting mixture was stirred at room temperature for 12 h. The resulting residue was concentrated in vacuo and purified by C18 chromatography (0~50% CH$_3$CN/H$_2$O) to yield 2-(1-(4-(4-Carboxyphenyl)-1H-pyrazol-1-yl)-3-phenylpropyl)-5-(5-chloro-2-(1H-tetrazol-1-yl)phenyl)pyridine 1-oxide as a white solid.

LC/MS: mass calculated for C$_{31}$H$_{24}$ClN$_7$O$_3$: 577.2, measured (ES, m/z): 578 [M]$^+$. $^1$H NMR (400 MHz, CD$_3$OD) δ ppm 2.45-2.79 (m, 4H), 5.99-6.21 (m, 1H), 7.06-7.29 (m, 6H), 7.31-7.42 (m, 2H), 7.63-7.82 (m, 4H), 7.94-8.13 (m, 4H), 8.17-8.37 (m, 2H), 9.28-9.42 (m, 1H).

Example 67: 5-(3-Chloro-2-fluoro-6-(1H-tetrazol-1-yl)phenyl)-2-(2-cyclopropyl-1-(4-(1-methyl-6-oxo-1,6-dihydropyridazin-4-yl)-1H-pyrazol-1-yl)ethyl)-4-methoxypyridine 1-oxide

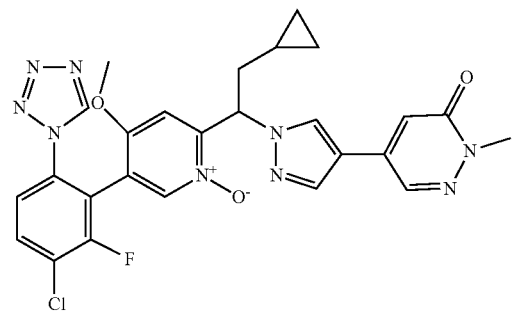 [SMILES: COc1cc(C(CC2CC2)n2cc(-c3cnn(C)c(=O)c3)cn2)[n+]([O-])cc1-c1c(-n2cnnn2)ccc(Cl)c1F]

LC/MS: mass calculated for C$_{26}$H$_{23}$ClFN$_9$O$_3$: 563.16, measured (ES, m/z): 564 [M+H]$^+$. $^1$H NMR (300 MHz, DMSO-d$_6$) δ 9.74 (d, J=6.7 Hz, 1H), 8.82 (s, 1H), 8.41 (d, J=3.7 Hz, 1H), 8.22-8.32 (m, 2 h), 8.00-8.12 (m, 1H), 7.70-7.81 (m, 1H), 7.11-7.18 (m, 1H), 7.01-7.04 (m, 2H), 6.01-6.26 (m, 1H), 3.63 (d, J=3.1 Hz, 3H), 3.58 (d, J=2.0 Hz, 3H), 2.4-2.46 (m, 1H), 1.78-2.07 (m, 1H), 0.46-0.67 (m, 1H), 0.24-0.45 (m, 2H), 0.06-0.23 (m, 1H), −0.09-0.05 (m, 1H). $^{19}$F NMR (282 MHz, DMSO-d$_6$) δ −74.80, −111.71.

Example 68: 2-(1-(4-(4-Carboxyphenyl)-1H-pyrazol-1-yl)-2-((1S*,2S*)-2-(ethoxycarbonyl)cyclopropyl)ethyl)-5-(5-chloro-2-(1H-tetrazol-1-yl)phenyl)pyridine 1-oxide

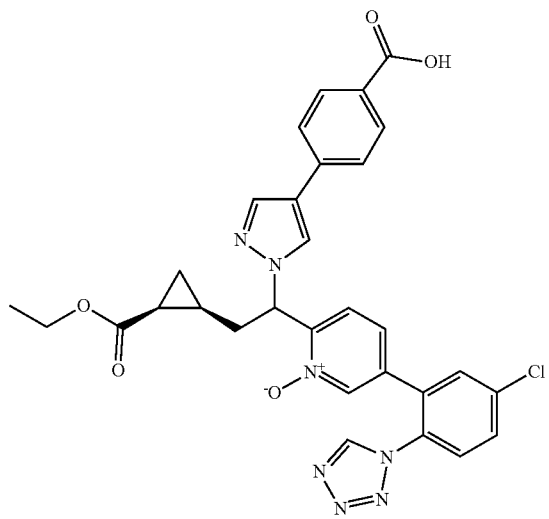

LC/MS: mass calculated for $C_{30}H_{26}ClN_7O_5$: 599.17; measured (ES, m/z): 600.05 [M+H]$^+$. $^1$H NMR (300 MHz, DMSO-d$_6$) δ 9.69 (s, 1H), 8.61 (s, 1H), 8.31 (d, J=1.8 Hz, 1H), 8.14 (s, 1H), 7.89-7.97 (m, 3H), 7.80-7.87 (m, 2H), 7.70-7.78 (m, 2H), 7.25 (d, J=8.3 Hz, 1H), 6.96 (d, J=8.3 Hz, 1H), 6.13 (dd, J=9.7, 4.6 Hz, 1H), 3.96-4.13 (m, 2H), 2.29-2.35 (m, 1H), 1.63-1.76 (m, 1H), 0.99-1.27 (m, 6H), 0.80-0.88 (m, 1H).

Example 69: 2-(1-(4-(4-Carboxyphenyl)-1H-pyrazol-1-yl)-2-((1S*,2R*)-2-(ethoxycarbonyl)cyclopropyl)ethyl)-5-(5-chloro-2-(1H-tetrazol-1-yl)phenyl)pyridine 1-oxide

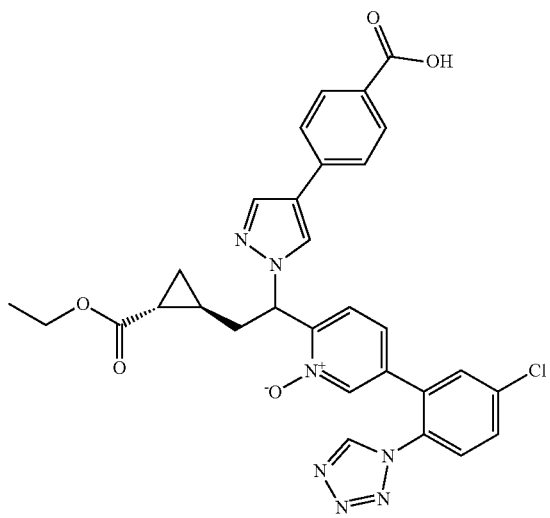

LC/MS: mass calculated for $C_{30}H_{26}ClN_7O_5$: 599.17; measured (ES, m/z): 600.05 [M+H]$^+$. $^1$H NMR (300 MHz, DMSO-d$_6$) δ 9.69 (s, 1H), 8.62 (s, 1H), 8.30 (d, J=1.7 Hz, 1H), 8.14 (s, 1H), 7.86-7.97 (m, 3H), 7.78-7.86 (d, J=2.8 Hz, 2H), 7.70-7.78 (m, 2H), 7.28 (d, J=8.3 Hz, 1H), 6.99 (d, J=8.3 Hz, 1H), 6.11 (dd, J=10.4, 3.8 Hz, 1H), 3.77-3.95 (m, 2H), 2.25-2.42 (m, 1H), 2.05-2.18 (m, 1H), 1.26-1.33 (m, 1H), 1.07-1.24 (m, 1H), 0.88-1.03 (m, 4H), 0.75-0.84 (m, 1H).

Example 70: 2-(2-((1S*,2S*)-2-Carboxycyclopropyl)-1-(4-(4-Carboxyphenyl)-1H-pyrazol-1-yl)ethyl)-5-(5-chloro-2-(1H-tetrazol-1-yl)phenyl)pyridine 1-oxide

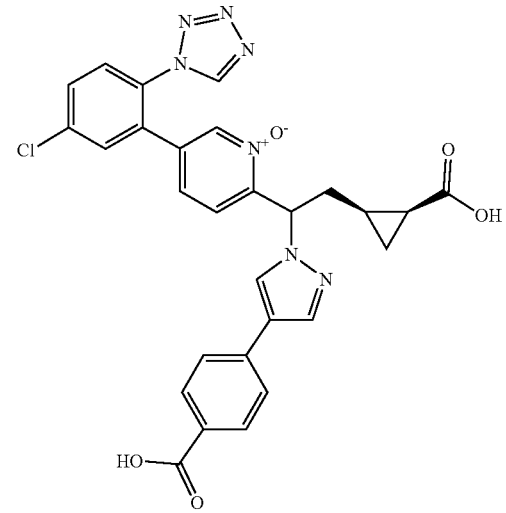

LC/MS: mass calculated for $C_{28}H_{22}ClN_7O_5$: 571.14, measured (ES, m/z): 572.05 [M+H]$^+$. $^1$H NMR (400 MHz, DMSO-d$_6$) δ 9.66-9.71 (m, 1H), 8.55-8.65 (m, 1H), 8.28-8.33 (m, 1H), 8.10-8.16 (m, 1H), 7.88-7.96 (m, 3H), 7.79-7.88 (m, 2H), 7.70-7.77 (m, 2H), 7.18-7.29 (m, 1H), 6.91-7.01 (m, 1H), 6.05-6.18 (m, 1H), 2.53-2.57 (m, 1H), 2.24-2.35 (m, 1H), 1.57-1.67 (m, 1H), 1.23-1.32 (m, 1H), 0.94-1.05 (m, 1H), 0.77-0.93 (m, 1H).

Example 71: 2-(2-((1S*,2R*)-2-Carboxycyclopropyl)-1-(4-(4-carboxyphenyl)-1H-pyrazol-1-yl)ethyl)-5-(5-chloro-2-(1H-tetrazol-1-yl)phenyl)pyridine 1-oxide

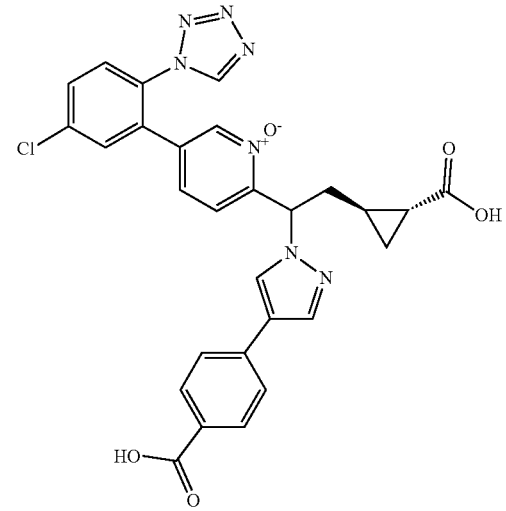

LC/MS: mass calculated for $C_{28}H_{22}ClN_7O_5$: 571.14, measured (ES, m/z): 572.00 [M+H]$^+$. $^1$H NMR (300 MHz, DMSO-d$_6$) δ 9.68 (s, 1H), 8.64 (s, 1H), 8.30 (d, J=1.7 Hz, 1H), 8.14 (s, 1H), 7.80-7.97 (m, 5H), 7.70-7.78 (m, 2H), 7.21 (d, J=8.3 Hz, 1H), 6.93-7.02 (m, 1H), 6.10 (dd, J=9.7, 4.2 Hz, 1H), 2.53-2.57 (m, 1H), 1.95-2.03 (m, 1H), 1.21-1.36 (m, 1H), 1.11-1.18 (m, 1H), 0.85-0.95 (m, 1H), 0.73-0.80 (m, 1H).

Example 72: 5-(3-Chloro-2-fluoro-6-(1H-tetrazol-1-yl)phenyl)-2-(1-(4-(4-((methoxycarbonyl)amino)phenyl)-1H-pyrazol-1-yl)-2-phenylethyl)pyridine 1-oxide

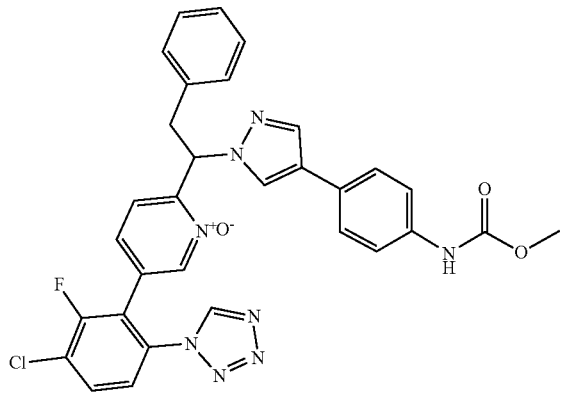

LC/MS: mass calculated for $C_{31}H_{24}ClFN_8O_3$: 610.16, measured (ES, m/z): 611.10 [M+H]$^+$. $^1$H NMR (400 MHz, DMSO-d$_6$) δ 9.70 (s, 1H), 9.64 (s, 1H), 8.48 (s, 1H), 8.27 (s, 1H), 8.02-8.11 (m, 1H), 7.96 (s, 1H), 7.75-7.77 (m, 1H), 7.40-7.46 (m, 4H), 7.16-7.27 (m, 7H), 6.18-6.21 (m, 1H), 3.66 (s, 3H), 3.50-3.60 (m, 2H). $^{19}$F NMR (400 MHz, DMSO-d$_6$) δ −74.56, −112.70.

Example 73: 2-(1-(4-(4-Carboxyphenyl)-1H-pyrazol-1-yl)-2-((1R*,2R*)-2-(piperazine-1-carbonyl)cyclopropyl)ethyl)-5-(5-chloro-2-(1H-tetrazol-1-yl)phenyl)pyridine 1-oxide

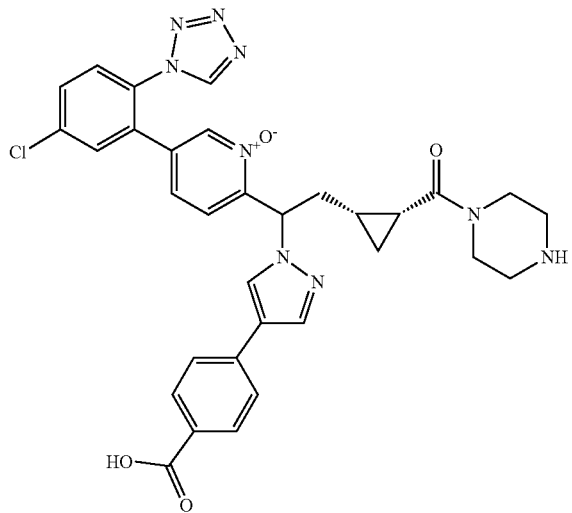

LC/MS: mass calculated for $C_{32}H_{30}ClN_9O_4$: 639.21, measured (ES, m/z): 640.10 [M+H]$^+$. $^1$H NMR (400 MHz, DMSO-d$_6$) δ 9.69 (s, 1H), 8.77-8.87 (m, 2H), 8.56-8.63 (m, 1H), 8.24-8.31 (m, 1H), 7.90-7.96 (m, 2H), 7.87-7.90 (m, 1H), 7.79-7.86 (m, 2H), 7.70-7.78 (m, 2H), 7.20 (d, J=8.3 Hz, 1H), 7.02 (dd, J=8.3, 1.7 Hz, 1H), 6.06 (dd, J=10.2, 3.5 Hz, 1H), 3.87-3.96 (m, 2H), 3.50-3.71 (m, 2H), 3.00-3.18 (m, 4H), 2.34-2.45 (m, 1H), 2.07-2.20 (m, 1H), 1.88-1.98 (m, 1H), 1.03-1.15 (m, 1H), 0.81-0.89 (m, 1H), 0.52-0.57 (m, 1H). $^{19}$F NMR (376 MHz, DMSO-d$_6$) δ −73.46.

Example 74: 2-(1-(4-(4-Carboxyphenyl)-1H-pyrazol-1-yl)-2-((1S*,2S*)-2-(piperazine-1-carbonyl)cyclopropyl)ethyl)-5-(5-chloro-2-(1H-tetrazol-1-yl)phenyl)pyridine 1-oxide

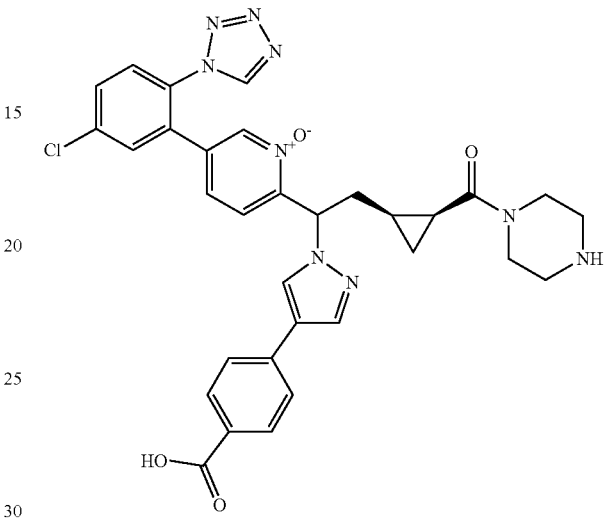

LC/MS: mass calculated for $C_{32}H_{30}ClN_9O_4$: 639.21, measured (ES, m/z): 640.10 [M+H]$^+$. $^1$H NMR (400 MHz, DMSO-d$_6$) δ 9.69 (s, 1H), 8.82-8.95 (m, 2H), 8.58 (s, 1H), 8.30 (d, J=1.7 Hz, 1H), 8.12 (s, 1H), 7.88-7.95 (m, 3H), 7.79-7.88 (m, 2H), 7.70-7.77 (m, 2H), 7.27 (d, J=8.3 Hz, 1H), 6.96 (d, J=8.3 Hz, 1H), 6.11 (dd, J=9.2, 5.6 Hz, 1H), 3.84-3.95 (m, 1H), 3.68-3.80 (m, 2H), 3.54-3.63 (m, 1H), 3.12-3.21 (m, 2H), 3.03-3.11 (m, 2H), 2.38-2.45 (m, 1H), 1.93-2.08 (m, 2H), 0.90-1.02 (m, 2H), 0.81-0.89 (m, 1H). $^{19}$F NMR (376 MHz, DMSO-d$_6$) δ −73.54.

Example 75: 2-(1-(4-(4-Carboxyphenyl)-1H-pyrazol-1-yl)-2-((1S*,2R*)-2-(piperazine-1-carbonyl)cyclopropyl)ethyl)-5-(5-chloro-2-(1H-tetrazol-1-yl)phenyl)pyridine 1-oxide

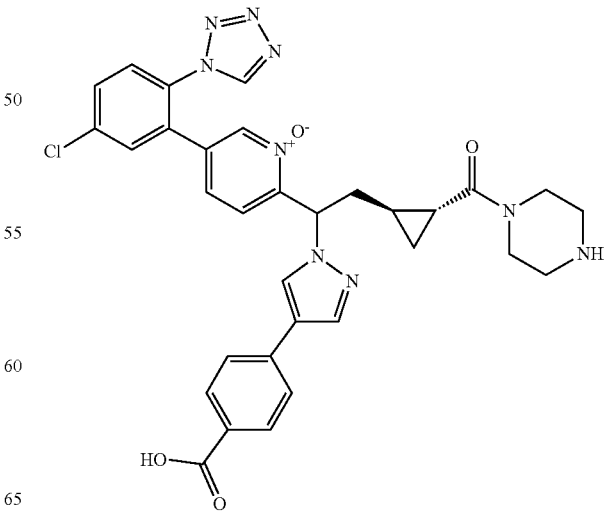

LC/MS: mass calculated for $C_{32}H_{30}ClN_9O_4$: 639.21, measured (ES, m/z): 640.10 [M+H]$^+$. $^1$H NMR (400 MHz, DMSO-d$_6$) δ 12.70-13.10 (m, 1H), 9.68 (s, 1H), 8.72-8.96 (m, 2H), 8.61 (s, 1H), 8.29 (d, J=1.7 Hz, 1H), 8.15 (s, 1H), 7.90-7.96 (m, 2H), 7.79-7.90 (m, 3H), 7.70-7.76 (m, 2H), 7.20 (d, J=8.3 Hz, 1H), 6.99 (dd, J=8.3 Hz, 1H), 6.11 (dd, J=10.1, 4.3 Hz, 1H), 3.70-3.81 (m, 2H), 3.53-3.70 (m, 2H), 2.90-3.11 (m, 4H), 2.42-2.50 (m, 1H), 1.99-2.10 (m, 1H), 1.76-1.84 (m, 1H), 1.06-1.15 (m, 1H), 0.86-0.94 (m, 1H), 0.68-0.77 (m, 1H). $^{19}$F NMR (376 MHz, DMSO-d$_6$) δ −73.35.

Example 76: 5-(3-Chloro-2-fluoro-6-(1H-tetrazol-1-yl)phenyl)-2-(2-cyclopropyl-1-(4-(2-fluoro-6-methoxypyridin-3-yl)-1H-pyrazol-1-yl)ethyl)pyridine 1-oxide

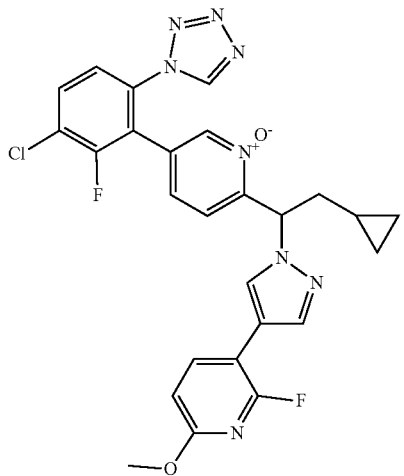

LC/MS: mass calculated for $C_{26}H_{21}ClF_2N_8O_2$: 550.14; measured (ES, m/z): 551.15 [M+H]$^+$. $^1$H NMR (400 MHz, DMSO-d$_6$) δ 9.68 (s, 1H), 8.38-8.45 (m, 2H), 8.15-8.23 (m, 1H), 8.05 (t, J=8.2 Hz, 1H), 7.99 (s, 1H), 7.75 (d, J=8.8 Hz, 1H), 7.28 (d, J=8.3 Hz, 1H), 7.15 (d, J=8.3 Hz, 1H), 6.83 (d, J=8.5 Hz, 1H), 6.11 (dd, J=9.8, 4.3 Hz, 1H), 3.85 (s, 3H), 2.30-2.42 (m, 1H), 1.85-1.96 (m, 1H), 0.54-0.65 (m, 1H), 0.24-0.41 (m, 2H), 0.07-0.16 (m, 1H), −0.05-0.00 (m, 1H).

Example 77: 5-(3-Chloro-2-fluoro-6-(1H-tetrazol-1-yl)phenyl)-2-(1-(4-(4-(methylsulfonamido)phenyl)-1H-pyrazol-1-yl)-2-phenylethyl)pyridine 1-oxide

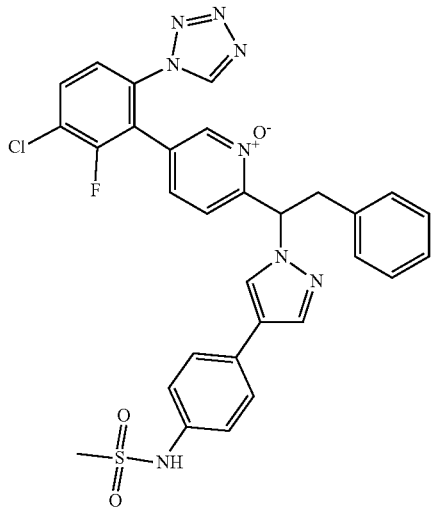

LC/MS: mass calculated for $C_{30}H_{24}ClFN_8O_3S$: 630.1, measured (ES, m/z): 631.0 [M+H]$^+$. $^1$H NMR (300 MHz, DMSO-d$_6$) δ 9.68 (s, 1H), 9.65 (s, 1H), 8.47 (s, 1H), 8.28 (s, 1H), 8.01-8.09 (m, 1H), 7.96 (s, 1H), 7.74 (d, J=8.7 Hz, 1H) 7.44-7.53 (m, 2H), 7.05-7.29 (m, 9H), 6.18 (dd, J=9.8, 4.4 Hz, 1H), 3.44-3.64 (m, 2H), 2.94 (s, 3H). $^{19}$F NMR (282 MHz, DMSO-d$_6$) δ −74.13, −112.69.

Example 78: 5-(3-Chloro-2-fluoro-6-(1H-tetrazol-1-yl)phenyl)-2-(1-(4-(4-(cyclopropanecarboxamido)phenyl)-1H-pyrazol-1-yl)-2-((R*)tetrahydro-2H-pyran-2-yl)ethyl)pyridine 1-oxide

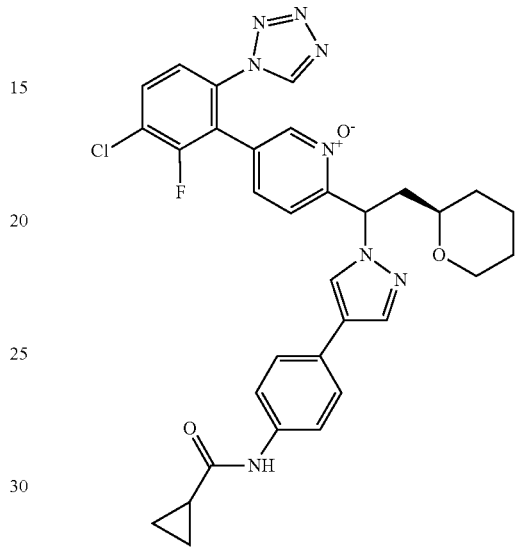

LC/MS: mass calculated for $C_{32}H_{30}ClFN_8O_3$: 628.12, measured (ES, m/z): 629.20 [M+H]$^+$. $^1$H NMR (400 MHz, DMSO-d$_6$) δ 10.18 (s, 1H), 9.67 (s, 1H), 8.28-8.41 (m, 2H), 8.01-8.09 (m, 1H), 7.91 (s, 1H), 7.72-7.80 (m, 1H), 7.54-7.62 (m, 2H), 7.47-7.53 (m, 2H), 7.29-7.36 (m, 1H), 7.16 (dd, J=8.3, 1.6 Hz, 1H), 6.13 (t, J=7.2 Hz, 1H), 3.69-3.83 (m, 1H), 3.11-3.23 (m, 1H), 3.01-3.10 (m, 1H), 2.27-2.44 (m, 2H), 1.64-1.83 (m, 3H), 1.28-1.49 (m, 2H), 1.09-1.27 (m, 1H), 0.73-0.86 (m, 4H).

Example 79: 2-(1-(4-(4-Carboxyphenyl)-1H-pyrazol-1-yl)-2-((1S*,2R*)-2-(piperidine-1-carbonyl)cyclopropyl)ethyl)-5-(5-chloro-2-(1H-tetrazol-1-yl)phenyl)pyridine 1-oxide

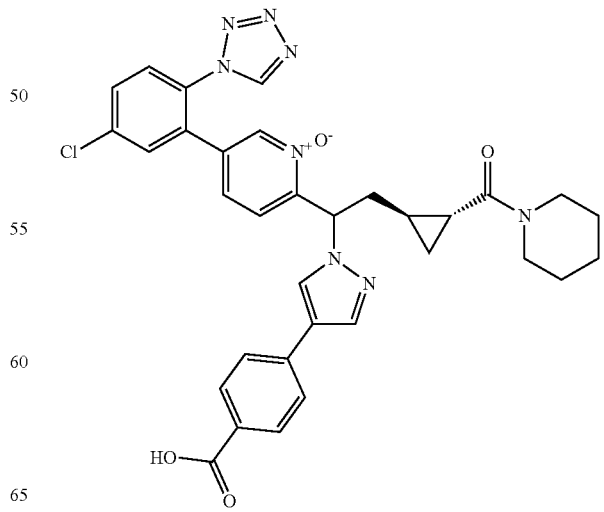

LC/MS: mass calculated for $C_{33}H_{31}ClN_8O_4$ 638.22, measured (ES, m/z): 639.10 [M+H]$^+$. $^1$H NMR (400 MHz, DMSO-d$_6$) δ 9.68 (s, 1H), 8.61 (s, 1H), 8.29 (d, J=1.7 Hz, 1H), 8.14 (s, 1H), 7.87-7.96 (m, 3H), 7.78-7.95 (m, 2H), 7.70-7.77 (m, 2H), 7.21 (d, J=8.3 Hz, 1H), 6.97 (dd, J=8.3, 1.7 Hz, 1H), 6.08 (dd, J=10.5, 3.8 Hz, 1H), 3.37-3.46 (m, 1H), 3.27-3.37 (m, 2H), 3.12-3.22 (m, 1H), 2.36-2.47 (m, 1H), 2.01-2.12 (m, 1H), 1.64-1.72 (m, 1H), 1.46-1.55 (m, 1H), 1.32-1.42 (m, 3H), 1.20-1.30 (m, 2H), 1.05-1.15 (m, 1H), 0.77-0.86 (m, 1H), 0.59-0.68 (m, 1H).

Example 80: 2-(1-(4-(4-Carboxyphenyl)-1H-pyrazol-1-yl)-2-((1S*,2S*)-2-(piperidine-1-carbonyl)cyclopropyl)ethyl)-5-(5-chloro-2-(1H-tetrazol-1-yl)phenyl)pyridine 1-oxide

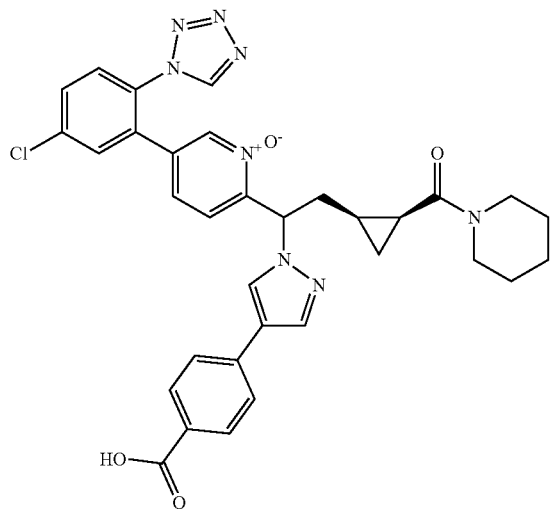

LC/MS: mass calculated for $C_{33}H_{31}ClN_8O_4$: 638.22; measured (ES, m/z): 639.25 [M+H]$^+$. $^1$H NMR (400 MHz, DMSO-d$_6$) δ 9.67 (s, 1H), 8.59 (s, 1H), 8.30 (d, J=1.7 Hz, 1H), 8.12 (s, 1H), 7.88-7.95 (m, 3H), 7.78-7.88 (m, 2H), 7.70-7.77 (m, 2H), 7.26 (d, J=8.3 Hz, 1H), 6.93 (d, J=8.3 Hz, 1H), 6.11 (dd, J=9.6, 5.2 Hz, 1H), 3.31-3.41 (m, 4H), 2.37-2.46 (m, 1H), 1.83-2.01 (m, 2H), 1.55-1.62 (m, 2H), 1.48-1.54 (m, 2H), 1.37-1.43 (m, 2H), 0.85-0.97 (m, 2H), 0.73-0.81 (m, 1H).

Example 81: 2-(1-(4-(4-Carboxyphenyl)-1H-pyrazol-1-yl)-2-phenylethyl)-5-(3-chloro-2-fluoro-6-(2,2,2-trifluoroethoxy)phenyl)pyridine 1-oxide

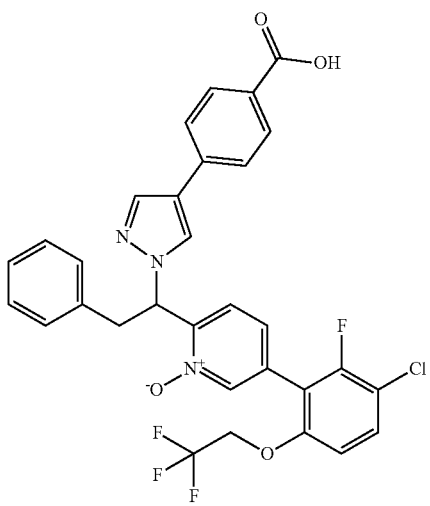

LC/MS: mass calculated for $C_{31}H_{22}ClF_4N_3O_4$: 611.12, measured (ES, m/z): 612.1[M+H]$^+$. $^1$H NMR (300 MHz, DMSO-d$_6$) δ 8.55 (s, 1H), 8.51 (s, 1H), 7.84-7.97 (m, 2H), 7.63-7.82 (m, 3H), 7.44 (d, J=1.0 Hz, 2H), 7.07-7.34 (m, 6H), 6.25-6.42 (m, 1H), 4.77-4.98 (m, 2H), 3.57-3.77 (m, 2H). $^{19}$F NMR (282 MHz, DMSO-d$_6$) δ −72.46, −115.56.

Example 82: 2-(1-(4-(4-Carboxyphenyl)-1H-pyrazol-1-yl)-3-methoxypropyl)-5-(3-chloro-2-fluoro-6-(2,2,2-trifluoroethoxy)phenyl)pyridine 1-oxide

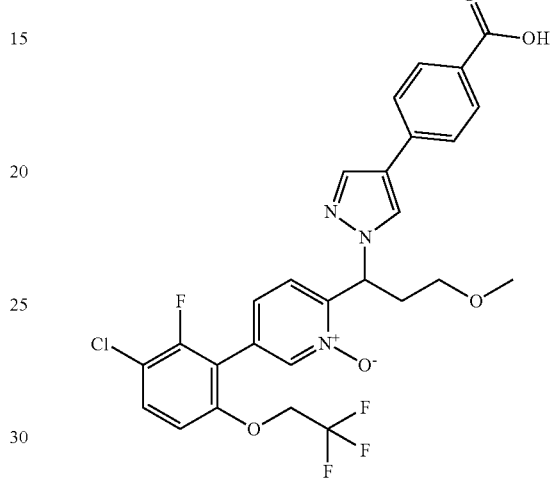

LC/MS: mass calculated for $C_{27}H_{22}ClF_4N_3O_5$: 579.12, measured (ES, m/z): 580.1[M+H]$^+$. $^1$H NMR (300 MHz, DMSO-d$_6$) δ 8.64 (s, 1H), 8.47 (s, 1H), 8.17 (s, 1H), 7.87-7.99 (m, 2H), 7.65-7.83 (m, 3H), 7.34-7.47 (m, 2H), 7.22 (d, J=9.2 Hz, 1H), 6.17-6.36 (m, 1H), 4.87 (q, J=8.8 Hz, 2H), 3.31-3.39 (m, 1H), 3.16-3.30 (m, 4H), 2.52-2.64 (m, 2H). $^{19}$F NMR (282 MHz, DMSO-d$_6$) δ −72.49, −115.56.

Example 83: 5-(3-Chloro-2-fluoro-6-(1H-tetrazol-1-yl)phenyl)-2-(1-(4-(4-(cyclopropanecarboxamido)phenyl)-1H-pyrazol-1-yl)-2-((S*)-tetrahydro-2H-pyran-2-yl)ethyl)pyridine 1-oxide

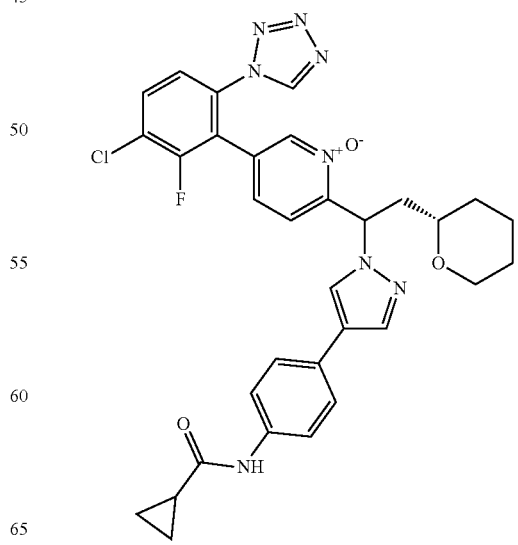

LC/MS: mass calculated for $C_{32}H_{30}ClFN_8O_3$: 628.21, measured (ES, m/z): 629.20 [M+H]$^+$. $^1$H NMR (300 MHz, DMSO-d$_6$) δ 10.18 (s, 1H), 9.66 (s, 1H), 8.39 (s, 1H), 8.33 (s, 1H), 7.98-8.08 (m, 1H), 7.95 (s, 1H), 7.73 (d, J=8.7, Hz, 1H), 7.47-7.64 (m, 4H), 7.20 (d, J=8.3 Hz, 1H), 7.11 (dd, J=8.3, 1.6 Hz, 1H), 6.22 (dd, J=11.0, 3.5 Hz, 1H), 3.85-3.89 (m, 1H), 3.09-3.20 (m, 1H), 2.84-2.97 (m, 1H), 2.29-2.43 (m, 1H), 2.11-2.26 (m, 1H), 1.68-1.82 (m, 2H), 1.35-1.51 (m, 4H), 1.14-1.28 (m, 1H), 0.69-0.83 (m, 4H).

Example 84: 2-(1-(4-(4-Carboxyphenyl)-1H-pyrazol-1-yl)-2-((1S*,2R*)-2-(morpholine-4-carbonyl)cyclopropyl)ethyl)-5-(5-chloro-2-(1H-tetrazol-1-yl)phenyl)pyridine 1-oxide

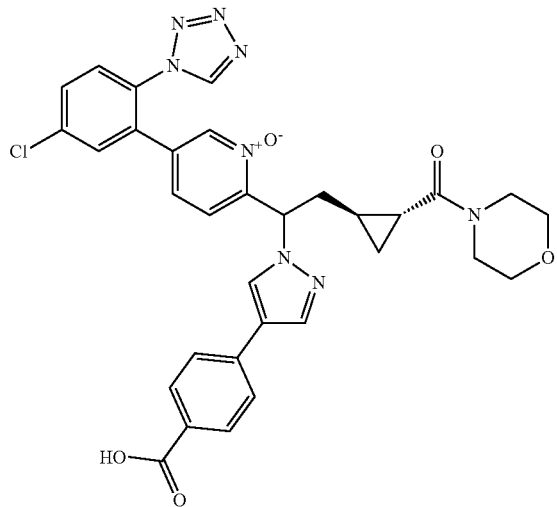

LC/MS: mass calculated for $C_{32}H_{29}ClN_8O$: 640.19, measured (ES, m/z): 641.05 [M+H]$^+$. $^1$H NMR (400 MHz, DMSO-d$_6$) δ 9.68 (s, 1H), 8.62 (s, 1H), 8.30 (d, J=1.7 Hz, 1H), 8.15 (s, 1H), 7.90-7.96 (m, 2H), 7.87-7.90 (m, 1H), 7.78-7.87 (m, 2H), 7.71-7.77 (m, 2H), 7.20 (d, J=8.3 Hz, 1H), 6.97 (dd, J=8.3 Hz, 1H), 6.09 (dd, J=10.5, 3.8 Hz, 1H), 3.16-3.50 (m, 8H), 2.33-2.45 (m, 1H), 2.05-2.16 (m, 1H), 1.63-1.72 (m, 1H), 1.10-1.20 (m, 1H), 0.83-0.90 (m, 1H), 0.63-0.70 (m, 1H).

Example 85: 2-(1-(4-(4-Carboxyphenyl)-1H-pyrazol-1-yl)-2-((1S*,2S*)-2-(morpholine-4-carbonyl)cyclopropyl)ethyl)-5-(5-chloro-2-(1H-tetrazol-1-yl)phenyl)pyridine 1-oxide

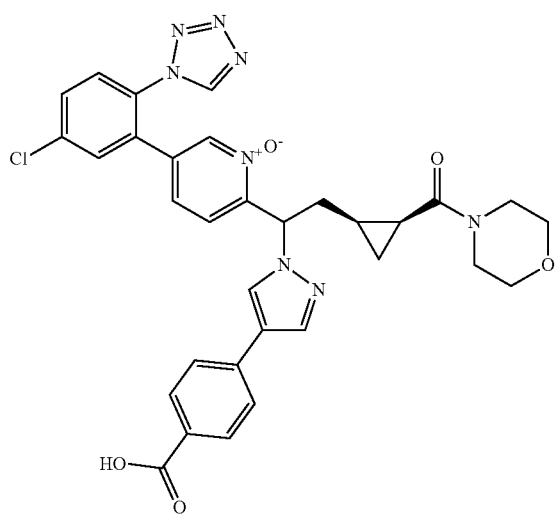

LC/MS: mass calculated for $C_{32}H_{29}ClN_8O$: 640.19, measured (ES, m/z): 254 nm $^1$H NMR (400 MHz, DMSO-d$_6$) δ 9.68 (s, 1H), 8.57-8.65 (m, 1H), 8.30 (d, J=1.8 Hz, 1H), 8.06-8.11 (m, 1H), 7.88-7.99 (m, 3H), 7.80-7.87 (m, 2H), 7.69-7.78 (m, 2H), 7.42-7.53 (m, 1H), 7.15-7.31 (m, 1H), 6.90-7.02 (m, 1H), 6.11 (dd, J=9.4, 5.3 Hz, 1H), 3.50-3.65 (m, 6H), 3.38-3.346 (m, 2H), 2.34-2.44 (m, 1H), 2.05-2.14 (m, 1H), 1.93-2.04 (m, 1H), 1.04-1.14 (m, 1H), 0.90-0.96 (m, 1H), 0.77-0.88 (m, 1H).

Example 86: (R*)-5-(3-Chloro-2-fluoro-6-(1H-tetrazol-1-yl)phenyl)-2-(3-methoxy-1-(4-(4-((methoxycarbonyl)amino)phenyl)-1H-pyrazol-1-yl)propyl)pyridine 1-oxide

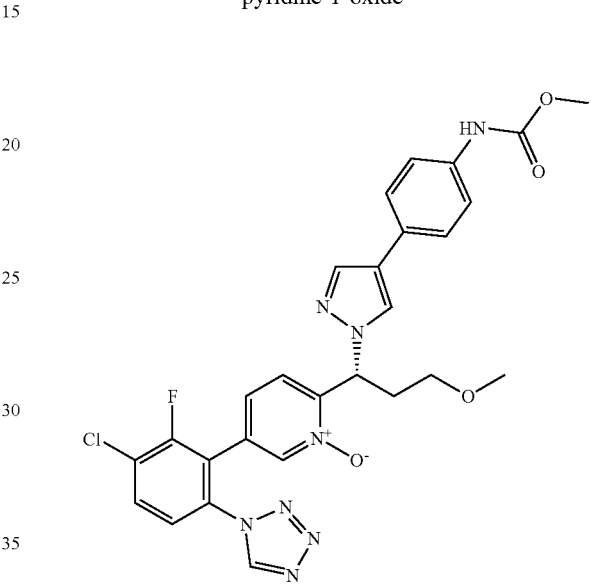

LC/MS: mass calculated for $C_{27}H_{24}ClFN_8O_4$: 578.16, measured (ES, m/z): 579.10 [M+H]$^+$. $^1$H NMR (300 MHz, Chloroform-d) δ 8.55 (s, 1H), 8.24 (s, 1H), 7.80-7.91 (m, 2H), 7.74 (t, J=7.9 Hz, 1H), 7.34-7.43 (m, 6H), 6.85-6.94 (m, 1H), 6.69 (s, 1H), 6.25-6.35 (m, 1H), 3.78 (s, 3H), 3.41-3.49 (m, 1H), 3.30 (s, 3H), 3.19-3.25 (m, 1H), 2.53-2.64 (m, 2H). $^{19}$F NMR (282 MHz, Chloroform-d) δ −75.82, −109.72.

Example 87: (R)-5-(3-Chloro-2-fluoro-6-(1H-tetrazol-1-yl)phenyl)-2-(3-methoxy-1-(4-(4-((methoxycarbonyl)amino)phenyl)-1H-pyrazol-1-yl)propyl)pyridine 1-oxide

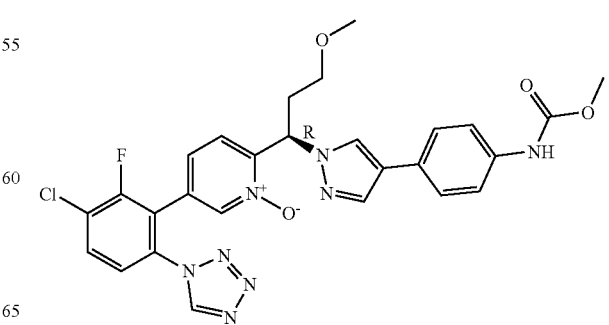

Step 1: N,3-Dimethoxy-N-methylpropanamide

To a solution of 3-methoxypropanoic acid (5.0 g, 48.0 mmol, 1.0 equiv.) in DCM (100 mL) was added di(1H-imidazol-1-yl)methanone (8.6 g, 52.8 mmol, 1.1 equiv.) at room temperature and the solution was stirred for 0.5 h. To the solution was then added N, O-dimethylhydroxylamine hydrochloride (5.2 g, 52.8 mmol, 1.1 equiv.) and the resulting mixture was stirred at room temperature overnight. The reaction was quenched with 1N HCL and extracted with DCM twice. The combined organic layer was washed with saturated aqueous NaHCO$_3$ and brine, dried over anhydrous Na$_2$SO$_4$ and concentrated to yield N,3-dimethoxy-N-methylpropanamide as a colorless oil. $^1$H NMR (300 MHz, CDCl$_3$): δ 3.66-3.74 (m, 5H), 3.37 (s, 3H), 3.20 (s, 3H), 2.72 (t, J=6.5 Hz, 2H).

Step 2: 1-(5-Bromopyridin-2-yl)-3-methoxypropan-1-one

To a solution of 2,5-dibromopyridine (2.0 g, 8.4 mmol, 1.0 equiv.) in toluene (20 mL) under nitrogen was added n-butyllithium (3.5 mL, 8.9 mmol, 2.50 M in THF, 1.05 equiv.) at −78° C. and the solution was stirred for 1 h at this temperature. To the solution was then added a solution of N,3-dimethoxy-N-methylpropanamide (1.4 g, 9.3 mmol, 1.1 equiv.) in toluene (10 mL) at −78° C. and the resulting mixture was stirred −78° C. for 2 h. The reaction was quenched with saturated NH$_4$Cl solution and extracted with ethyl acetate twice. The combined organic layer was washed with brine, dried over Na$_2$SO$_4$ and concentrated. The residue was purified by silica gel chromatography (0→50% EA/petroleum ether) to yield 1-(5-bromopyridin-2-yl)-3-methoxypropan-1-one as a white solid. LC/MS: mass calculated for C$_9$H$_{10}$BrNO$_2$: 242.99, measured (ES, m/z): 244.05, 246.05 [M+H, M+H+2]$^+$.

Step 3: 1-(5-Bromopyridin-2-yl)-3-methoxypropan-1-ol

To a solution of 1-(5-bromopyridin-2-yl)-3-methoxypropan-1-one (1.1 g, 4.51 mmol, 1.0 equiv.) in CH$_3$OH (10 mL) was added sodium borohydride (205 mg, 5.41 mmol, 1.2 equiv.) in portions at 0° C. and the resulting mixture was stirred at room temperature for 1 h. The reaction was quenched with water, and the mixture extracted with ethyl acetate twice. The combined organic layers were washed with water and brine.

The organic layer was dried over Na$_2$SO$_4$ and concentrated. The residue was purified by silica gel chromatography (0→50% EA/petroleum ether) to yield 1-(5-bromopyridin-2-yl)-3-methoxypropan-1-ol as a colorless oil. LC/MS: mass calculated for C$_9$H$_{12}$BrNO$_2$: 245.01, measured (ES, m/z): 246.10, 248.10 [M+H, M+H+2]$^+$.

Step 4: 1-(5-Bromopyridin-2-yl)-3-methoxypropyl methanesulfonate

To a mixture of 1-(5-bromopyridin-2-yl)-3-methoxypropan-1-ol (940 mg, 3.82 mmol, 1.0 equiv.) and triethylamine (1.16 g, 11.5 mmol, 3.0 equiv.) in DCM (10 mL) was added methanesulfonyl chloride (525 mg, 4.58 mmol, 1.2 equiv.) at 0° C. and the resulting mixture was stirred at room temperature for 2 h. The reaction was washed with water and brine. The organic layer was dried over Na$_2$SO$_4$ and concentrated. The residue was purified by silica gel chromatography (0→50% EA/petroleum ether) to yield 1-(5-bromopyridin-2-yl)-3-methoxypropyl methanesulfonate as a light yellow solid. LC/MS: mass calculated for C$_{10}$H$_{14}$BrNO$_4$S: 322.98, measured (ES, m/z): 324.05, 326.05 [M+H, M+H+2]$^+$.

Step 5: Methyl (4-(1-(1-(5-bromopyridin-2-yl)-3-methoxypropyl)-1H-pyrazol-4-yl)phenyl)carbamate A mixture of 1-(5-bromopyridin-2-yl)-3-methoxypropyl methanesulfonate (500 mg, 1.54 mmol, 1.0 equiv.), methyl 4-(1H-pyrazol-4-yl)phenylcarbamate (368 mg, 1.70 mmol, 1.1 equiv.) and cesium carbonate (753 mg, 2.31 mmol, 1.5 equiv.) in acetonitrile (10 mL) was stirred at 100° C. for 4 h. The reaction was diluted with water, and the mixture extracted with ethyl acetate twice. The combined organic layers were washed with brine, dried over Na$_2$SO$_4$ and concentrated. The residue was purified by silica gel chromatography (0→30% EA/petroleum ether) to yield methyl 4-(1-(1-(5-bromopyridin-2-yl)-3-methoxypropyl)-1H-pyrazol-4-yl)phenylcarbamate as a light yellow solid. LC/MS: mass calculated for C$_{20}$H$_{21}$BrN$_4$O$_3$: 444.08, measured (ES, m/z): 445.00, 447.00 [M+H, M+H+2]$^+$.

Step 6: Methyl (4-(1-(1-(5-(6-amino-3-chloro-2-fluorophenyl)pyridin-2-yl)-3-methoxypropyl)-1H-pyrazol-4-yl)phenyl)carbamate A mixture of methyl 4-(1-(1-(5-bromopyridin-2-yl)-3-methoxypropyl)-1H-pyrazol-4-yl)phenylcarbamate (200 mg, 0.45 mmol, 1.0 equiv.), 6-amino-3-chloro-2-fluorophenylboronic acid (170 mg, 0.90 mmol, 2.0 equiv.), potassium carbonate (186 mg, 1.35 mmol, 3.0 equiv.) and Pd(PPh$_3$)$_4$ (52 mg, 0.045 mmol, 0.1 equiv.) in 1,4-dioxane (3 mL) and water (1 mL) was stirred at 90° C. overnight. After cooling to room temperature, the reaction was quenched with H$_2$O and extracted with ethyl acetate twice. The combined organic layers were washed with brine, dried over Na$_2$SO$_4$ and concentrated. The residue was purified by silica gel chromatography (0→50% EA/petroleum ether) to yield methyl 4-(1-(1-(5-(6-amino-3-chloro-2-fluorophenyl)pyridin-2-yl)-3-methoxypropyl)-1H-pyrazol-4-yl)phenylcarbamate as a light yellow oil. LC/MS: mass calculated for C$_{26}$H$_{25}$ClFN$_5$O$_3$: 509.16, measured (ES, m/z): 510.20 [M+H]$^+$.

Step 7: Methyl (4-(1-(1-(5-(3-chloro-2-fluoro-6-(1H-tetrazol-1-yl)phenyl) pyridin-2-yl)-3-methoxypropyl)-1H-pyrazol-4-yl)phenyl)carbamate A mixture of methyl 4-(1-(1-(5-(6-amino-3-chloro-2-fluorophenyl)pyridin-2-yl)-3-methoxypropyl)-1H-pyrazol-4-yl)phenylcarbamate (200 mg, 0.39 mmol, 1.0 equiv.), azidotrimethylsilane (0.5 mL), and trimethoxymethane (0.5 mL) in acetic acid glacial (1 mL) was stirred at room temperature overnight. The mixture was then concentrated and the residue was purified by reverse phase chromatography on C18 (80 g, MeCN/H$_2$O (0.05% CF$_3$COOH): 0→45%) to yield methyl (4-(1-(1-(5-(3-chloro-2-fluoro-6-(1H-tetrazol-1-yl)phenyl)pyridin-2-yl)-3-methoxypropyl)-1H-pyrazol-4-yl)phenyl)carbamate as a white solid. LC/MS: mass calculated for C$_{27}$H$_{24}$ClFN$_8$O$_3$: 562.16, measured (ES, m/z): 563.25 [M+H]$^+$.

Step 8: (R)-5-(3-Chloro-2-fluoro-6-(1H-tetrazol-1-yl)phenyl)-2-(3-methoxy-1-(4-(4-((methoxycarbonyl)amino)phenyl)-1H-pyrazol-1-yl)propyl)pyridine 1-oxide A mixture of methyl (4-(1-(1-(5-(3-chloro-2-fluoro-6-(1H-tetrazol-1-yl)phenyl) pyridin-2-yl)-3-methoxypropyl)-

1H-pyrazol-4-yl)phenyl)carbamate (450 mg, 0.80 mmol, 1.0 equiv.), methyl trioxorhenium (VII) (100 mg, 0.40 mmol, 0.5 equiv.) and hydrogen peroxide (0.40 mL, 4.00 mmol, 30 wt %, 5.0 equiv.) in CH₃OH (5 mL) was stirred at room temperature for 1 h. DMF (2 mL) was added to the mixture, which was then stirred for another hour. The reaction was purified by reverse phase chromatography on C18 (80 g, MeCN/H₂O (0.05% CF₃COOH): 0→45%) to yield 5-(3-chloro-2-fluoro-6-(1H-tetrazol-1-yl)phenyl)-2-(3-methoxy-1-(4-(4-((methoxycarbonyl)amino)phenyl)-1H-pyrazol-1-yl)propyl)pyridine 1-oxide as a white solid. The racemic product was purified by SFC to yield (R)-5-(3-chloro-2-fluoro-6-(1H-tetrazol-1-yl)phenyl)-2-(3-methoxy-1-(4-(4-((methoxycarbonyl)amino)phenyl)-1H-pyrazol-1-yl)propyl) pyridine 1-oxide as a white solid.

LC/MS: mass calculated for $C_{27}H_{24}ClFN_8O_4$: 578.16, measured (ES, m/z): 579.10 [M+H]⁺. ¹H NMR (300 MHz, CDCl₃): δ 8.57 (s, 1H), 8.24 (s, 1H), 7.80-7.91 (m, 2H), 7.72-7.77 (m, 1H), 7.34-7.49 (m, 6H), 6.82-6.93 (m, 1H), 6.73 (s, 1H), 6.24-6.36 (m, 1H), 3.78 (s, 3H), 3.41-3.49 (m, 1H), 3.30 (s, 3H), 3.18-3.26 (m, 1H), 2.52-2.65 (m, 2H). ¹⁹F NMR (282 MHz, CDCl₃): δ −75.58, −109.75.

Example 88: 2-(1-(4-(6-Amino-2-fluoropyridin-3-yl)-1H-pyrazol-1-yl)-2-cyclopropylethyl)-5-(3-Chloro-2-fluoro-6-(1H-tetrazol-1-yl)phenyl)-4-methoxypyridine 1-oxide LC/MS: mass calculated for $C_{26}H_{22}ClF_2N_9O_2$: 565.16, measured (ES, m/z): 566.2 [M+H]⁺. ¹H NMR (300 MHz, Chloroform-d) δ 8.75-8.88 (m, 1H), 8.48 (d, J=9.6 Hz, 1H), 7.89-7.99 (m, 2H), 7.64-7.85 (m, 2H), 7.42-7.51 (m, 1H), 7.22-7.33 (m, 1H), 6.37-6.48 (m, 1H), 6.12-6.36 (m, 1H), 3.60 (s, 3H), 2.53-2.70 (m, 1H), 1.78-2.02 (m, 1H), 0.41-0.52 (m, 2H), 0.18-0.32 (m, 1H), 0.04-0.15 (m, 2H). ¹⁹F NMR (282 MHz, Chloroform-d) δ −70.96, −75.80, −109.57.

Example 89: 5-(5-Chloro-2-(1H-tetrazol-1-yl)phenyl)-2-(1-(4-(4-(cyclopropylcarbamoyl)phenyl)-1H-pyrazol-1-yl)-2-(4-methoxyphenyl)ethyl)pyridine 1-oxide

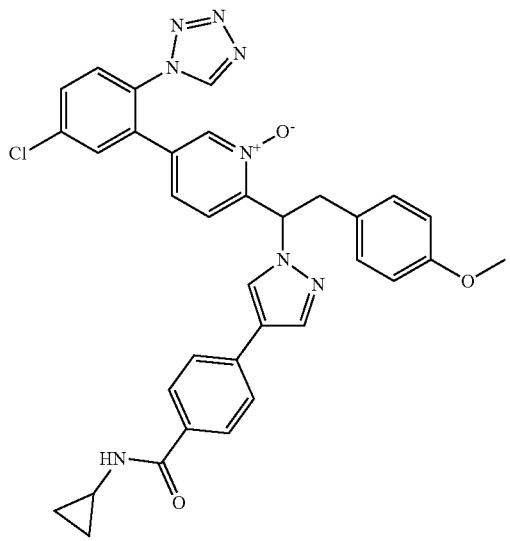 [SMILES: COc1ccc(CC(c2ccc(-c3cc(Cl)ccc3-n3cnnn3)c[n+]2[O-])n2cc(-c3ccc(C(=O)NC4CC4)cc3)cn2)cc1]

LC/MS: mass calculated for $C_{34}H_{29}ClN_8O_3$: 632.2, measured (ES, m/z): 633.3 [M+H]⁺. ¹H NMR (400 MHz, CD₃OD) δ ppm 0.59-0.67 (m, 2 h) 0.76-0.84 (m, 2 h) 2.80-2.88 (m, 1H) 3.51-3.64 (m, 2 h) 3.66 (s, 3H) 6.27 (dd, J=10.36, 3.79 Hz, 1H) 6.64-6.83 (m, 3H) 7.08-7.21 (m, 2 h) 7.55 (d, J=8.08 Hz, 3H) 7.67-7.84 (m, 5H) 8.04 (d, J=19.71 Hz, 2 h) 8.26-8.37 (m, 1H) 9.37 (s, 1H).

Example 90: 2-(2-([1,1'-Biphenyl]-4-yl)-1-(4-(4-(cyclopropylcarbamoyl)phenyl)-1H-pyrazol-1-yl)ethyl)-5-(5-chloro-2-(1H-tetrazol-1-yl)phenyl)pyridine 1-oxide

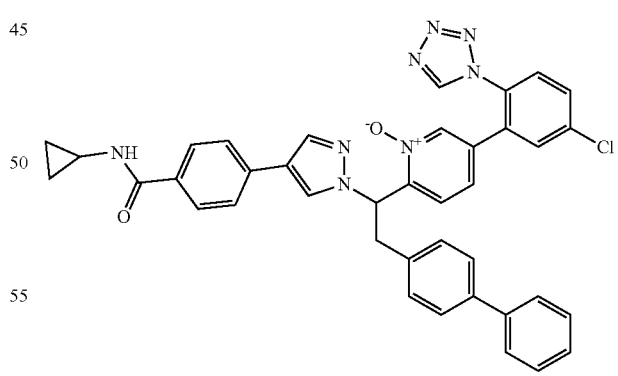

LC/MS: mass calculated for $C_{39}H_{31}ClN_8O_2$: 678.2, measured (ES, m/z): 679.3 [M+H]⁺. ¹H NMR (400 MHz, CD₃OD) δ ppm 0.58-0.67 (m, 2 h) 0.76-0.84 (m, 2 h) 2.75-2.91 (m, 1H) 3.59-3.79 (m, 2 h) 6.31-6.41 (m, 1H) 7.14-7.21 (m, 1H) 7.24-7.30 (m, 3H) 7.33-7.41 (m, 2 h) 7.47 (d, J=8.08 Hz, 2 h) 7.51-7.60 (m, 5H) 7.67-7.83 (m, 5H) 8.00-8.07 (m, 1H) 8.10-8.18 (m, 1H) 8.27-8.37 (m, 1H) 9.38 (s, 1H).

Example 91: 5-(5-Chloro-2-(1H-tetrazol-1-yl)phenyl)-2-(2-cyclopropyl-1-(4-(4-(1-(methoxycarbonyl)cyclopropyl)phenyl)-1H-pyrazol-1-yl)ethyl)pyridine 1-oxide

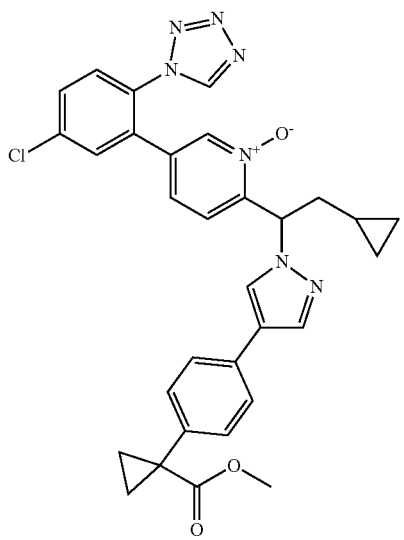 [SMILES: COC(=O)C1(c2ccc(-c3cnn(C(CC4CC4)c4ccc(-c5cc(Cl)ccc5-n5cnnn5)c[n+]4[O-])c3)cc2)CC1]

LC/MS: mass calculated for $C_{31}H_{28}ClN_7O_3$: 581.2, measured (ES, m/z): 582.3 [M+H]⁺. ¹H NMR (CD₃OD) δ 9.36 (s, 1H), 8.17-8.32 (m, 2H), 7.89-8.00 (m, 1H), 7.77 (s, 2H), 7.66-7.72 (m, 1H), 7.50 (d, J=8.1 Hz, 2H), 7.29-7.41 (m, 3H), 7.05-7.18 (m, 1H), 6.21 (br s, 1H), 3.60 (s, 3H), 2.46 (br d, J=6.1 Hz, 1H), 1.91-1.99 (m, 1H), 1.49-1.60 (m, 2H), 1.14-1.23 (m, 2H), 0.69 (br s, 1H), 0.41 (ddd, J=16.5, 8.2, 4.5 Hz, 2H), 0.16-0.25 (m, 1H), 0.05 (br d, J=4.5 Hz, 1H).

Example 92: 2-(1-(4-(4-(1-Carboxycyclopropyl)phenyl)-1H-pyrazol-1-yl)-2-cyclopropylethyl)-5-(5-chloro-2-(1H-tetrazol-1-yl)phenyl)pyridine 1-oxide

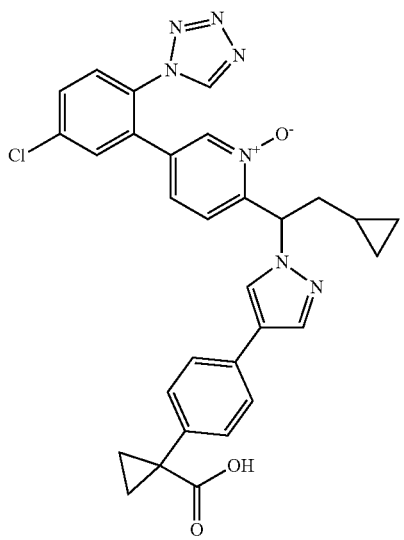 [SMILES: O=C(O)C1(c2ccc(-c3cnn(C(CC4CC4)c4ccc(-c5cc(Cl)ccc5-n5cnnn5)c[n+]4[O-])c3)cc2)CC1]

LC/MS: mass calculated for $C_{30}H_{26}ClN_7O_3$: 567.2, measured (ES, m/z): 568.2 [M+H]⁺. ¹H NMR (CD₃OD) δ 9.28 (s, 1H), 8.18 (br s, 2H), 7.79-7.93 (m, 1H), 7.68 (s, 2H), 7.63 (s, 1H), 7.42 (d, J=8.1 Hz, 2H), 7.22-7.35 (m, 3H), 7.00-7.15 (m, 1H), 6.02-6.28 (m, 1H), 2.31-2.51 (m, 1H), 1.85-1.94 (m, 1H), 1.46-1.53 (m, 2H), 1.05-1.18 (m, 2H), 0.55-0.72 (m, 1H), 0.28-0.46 (m, 2H), 0.08-0.20 (m, 1H), −0.10-0.05 (m, 1H).

Example 93: 2-(1-(4-(4-carboxyphenyl)-1H-pyrazol-1-yl)-3-oxo-3-(piperazin-1-yl)propyl)-5-(5-chloro-2-(1H-tetrazol-1-yl)phenyl)pyridine 1-oxide

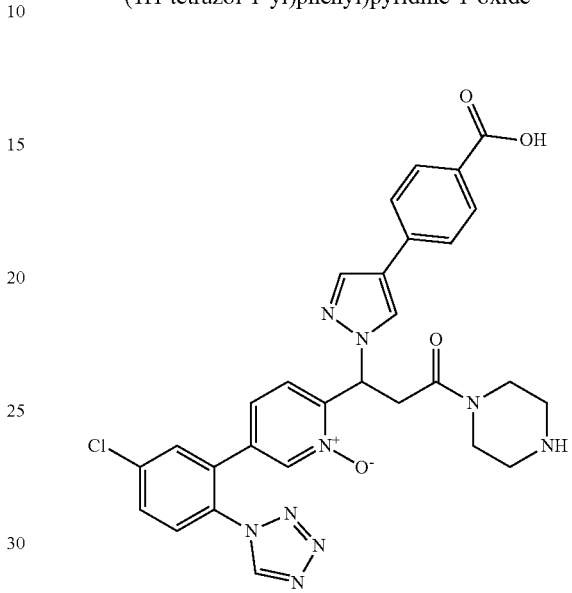

LC/MS: mass calculated for $C_{29}H_{26}ClN_9O_4$: 699.23, measured (ES, m/z): 600.10 [M+H]⁺. ¹H NMR (300 MHz, DMSO-d₆) δ 9.70 (s, 1H), 8.72-8.78 (m, 1H), 8.56 (s, 1H), 8.36 (s, 1H), 8.11 (s, 1H), 7.78-7.97 (m, 5H), 7.73 (d, J=8.2 Hz, 2H), 6.95-7.02 (m, 2H), 6.41-6.49 (m, 1H), 3.53-3.81 (m, 6H), 2.99-3.17 (m, 4H). ¹⁹F NMR (282 MHz, DMSO-d₆) δ −73.63.

Example 94: 2-(1-(4-(4-Carboxyphenyl)-1H-pyrazol-1-yl)-3-morpholino-3-oxopropyl)-5-(5-chloro-2-(1H-tetrazol-1-yl)phenyl)pyridine 1-oxide

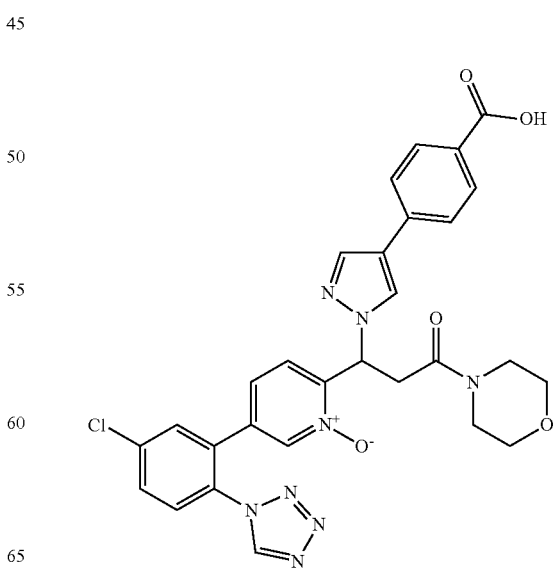

LC/MS: mass calculated for C₂₉H₂₅ClN₈O₅: 600.16, measured (ES, m/z): 601.10 [M+H]⁺. ¹H NMR (300 MHz, DMSO-d₆) δ 9.69 (s, 1H), 8.54 (s, 1H), 8.35 (s, 1H), 8.10 (s, 1H), 7.79-7.97 (m, 5H), 7.68-7.77 (m, 2H), 6.93-7.05 (m, 2H), 6.45 (dd, J=9.4, 3.8 Hz, 1H), 3.54-3.80 (m, 8H), 3.21-3.35 (m, 2H).

Example 95: 5-(5-Chloro-2-(1H-tetrazol-1-yl)phenyl)-2-(2-(4-chlorophenyl)-1-(4-(4-((methoxycarbonyl)amino)phenyl)-1H-pyrazol-1-yl)ethyl)pyridine 1-oxide

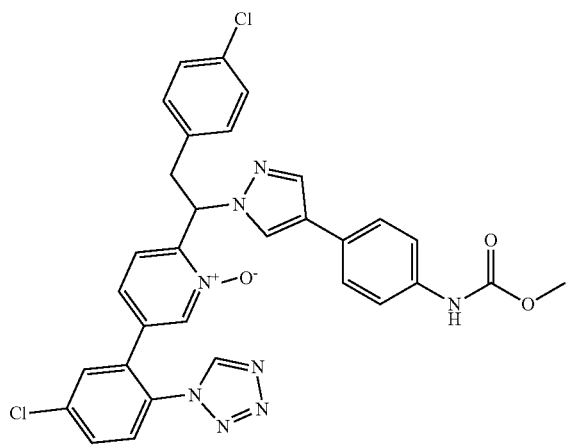 [SMILES: COC(=O)Nc1ccc(-c2cnn(C(Cc3ccc(Cl)cc3)c3ccc(-c4cc(Cl)ccc4-n4cnnn4)c[n+]3[O-])c2)cc1]

LC/MS: mass calculated for C₃₁H₂₄Cl₂N₈O₃: 626.13, measured (ES, m/z): 627.10 [M+H]⁺. ¹H NMR (300 MHz, Chloroform-d) δ 8.61 (s, 1H), 8.35 (s, 1H), 7.90 (s, 1H), 7.70 (d, J=8.5 Hz, 1H), 7.48-7.62 (m, 4H), 7.26-7.41 (m, 4H), 7.15-7.26 (m, 2H), 7.05-7.14 (m, 2H), 6.94 (d, J=8.2 Hz, 1H), 6.69 (s, 1H), 6.16 (d, J=9.3 Hz, 1H), 3.80 (s, 3H), 3.63-3.76 (m, 1H), 3.44-3.54 (m, 1H).

Example 96: 2-(1-(4-(4-Carboxyphenyl)-1H-pyrazol-1-yl)-2-phenylethyl)-5-(3-Chloro-2-fluoro-6-(2,2,2-trifluoroethoxy)phenyl)-4-methoxypyridine 1-oxide

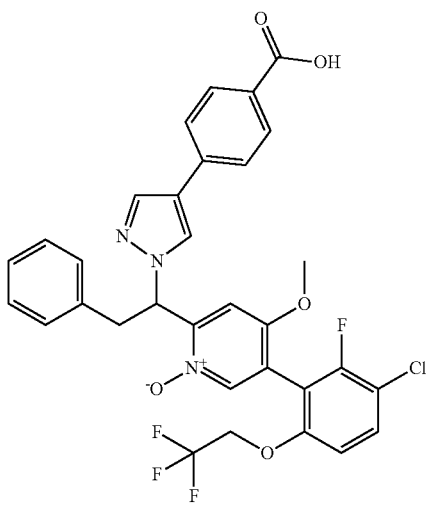

LC/MS: mass calculated for C₃₂H₂₄ClF₄N₃O₅: 641.13, measured (ES, m/z): 642.20 [M+H]⁺. 1H NMR (300 MHz, Chloroform-d) δ 8.41 (d, J=7.4 Hz, 1H), 8.00-8.05 (m, 3H), 7.80 (s, 1H), 7.45-7.57 (m, 4H), 7.16-7.32 (m, 5H), 6.79 (d, J=9.0 Hz, 1H), 6.45-6.60 (m, 1H), 4.30-4.44 (m, 2H), 3.92 (s, 3H), 3.79-3.89 (m, 1H), 3.62-3.72 (m, 1H). 19F NMR (282 MHz, Chloroform-d) δ −73.76, −75.92, −110.75.

Example 97: 5-(3-Chloro-2-fluoro-6-(1H-tetrazol-1-yl)phenyl)-2-(2-cyclopropyl-1-(4-(4-((methoxycarbonyl)amino)phenyl)-1H-pyrazol-1-yl)ethyl)-4-methoxypyridine 1-oxide

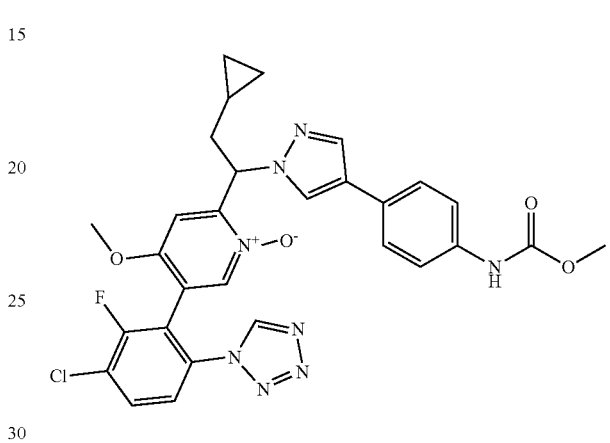

LC/MS: mass calculated for C₂₉H₂₈ClFN₈O₄: 604.17, measured (ES, m/z): 605.15 [M+H]⁺. ¹H NMR (300 MHz, Chloroform-d) δ 8.61 (d, J=17.5 Hz, 1H), 8.20 (s, 1H), 7.72-7.94 (m, 3H), 7.37-7.54 (m, 5H), 7.04-7.17 (m, 1H), 6.75 (s, 1H), 6.08-6.41 (m, 1H), 3.77-3.85 (m, 3H), 3.51-3.70 (m, 3H), 2.49-2.63 (m, 1H), 2.19-2.38 (m, 1H), 0.64-0.74 (m, 1H), 0.38-0.52 (m, 2H), 0.21-0.33 (m, 1H), 0.06-0.14 (m, 1H).

Example 98: 5-(3-Chloro-2-fluoro-6-(1H-tetrazol-1-yl)phenyl)-2-(2-(4-chlorophenyl)-1-(4-(4-((methoxycarbonyl)amino)phenyl)-1H-pyrazol-1-yl)ethyl)pyridine 1-oxide

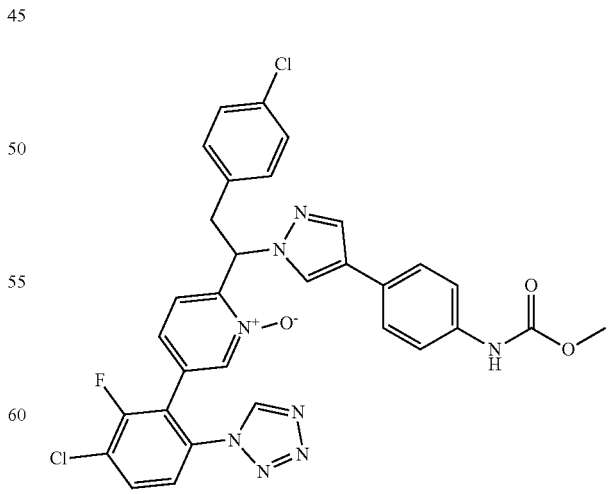

LC/MS: mass calculated for C₃₁H₂₃Cl₂FN₈O₃: 644.10, measured (ES, m/z): 645.10 [M+H]⁺. ¹H NMR (300 MHz, CD₃OD) δ 9.39 (s, 1H), 8.41 (s, 1H), 7.86-7.99 (m, 3H), 7.61 (d, J=8.7 Hz, 1H), 7.49 (d, J=8.4 Hz, 1H), 7.38-7.44 (m, 4H), 7.13-7.35 (m, 5H), 6.25 (dd, J=9.8, 4.5 Hz, 1H), 3.74 (s, 3H), 3.54-3.79 (m, 2H). $^{19}$F NMR (282 MHz, CD$_3$OD) δ −76.85, −77.69, −113.62.

Example 99: 2-(1-(4-(4-Carboxyphenyl)-1H-pyrazol-1-yl)-2-((1S*,2R*)-2-(isoindoline-2-carbonyl)cyclopropyl)ethyl)-5-(5-chloro-2-(1H-tetrazol-1-yl)phenyl)pyridine 1-oxide

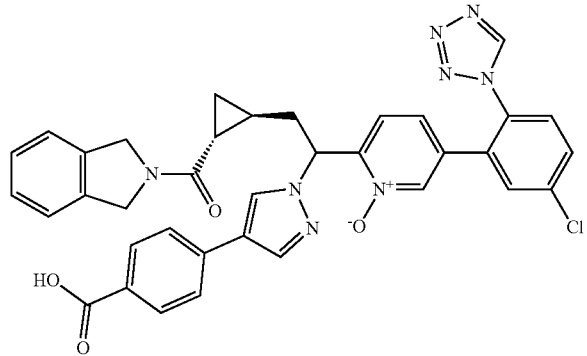

LC/MS: mass calculated for C$_{36}$H$_{29}$ClN$_8$O$_4$: 672.20, measured (ES, m/z): 673.10 [M+H]$^+$. $^1$H NMR (400 MHz, DMSO-d$_6$) δ 9.70 (s, 1H), 8.62 (s, 1H), 8.31 (d, J=1.7 Hz, 1H), 8.15 (s, 1H), 7.90 (d, J=2.0 Hz, 1H), 7.80-7.88 (m, 2H), 7.75-7.80 (m, 2H), 7.59-7.66 (m, 2H), 7.28 (d, J=8.3 Hz, 1H), 7.10-7.25 (m, 4H), 6.99 (dd, J=8.3, 1.8 Hz, 1H), 6.12 (dd, J=10.6, 3.7 Hz, 1H), 4.79 (d, J=14.4 Hz, 1H), 4.65 (d, J=13.5 Hz, 1H), 4.48 (d, J=16.3 Hz, 1H), 4.33-4.42 (m, 1H), 2.32-2.44 (m, 1H), 2.16-2.25 (m, 1H), 1.44-1.53 (m, 1H), 1.19-1.30 (m, 1H), 0.89-0.97 (m, 1H), 0.71-0.79 (m, 1H).

Example 100: 2-(1-(4-(4-Carboxyphenyl)-1H-pyrazol-1-yl)-2-((1S*,2S*)-2-(isoindoline-2-carbonyl)cyclopropyl)ethyl)-5-(5-chloro-2-(1H-tetrazol-1-yl)phenyl)pyridine 1-oxide

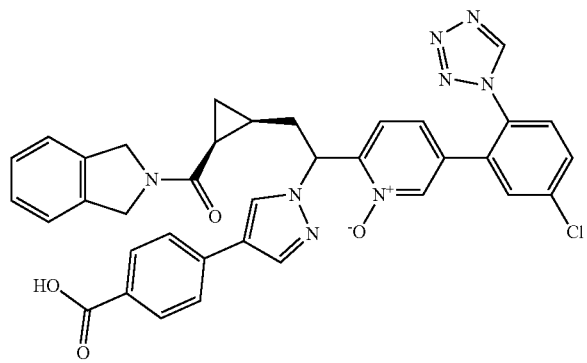

LC/MS: mass calculated for C$_{36}$H$_{29}$ClN$_8$O$_4$: 672.20, measured (ES, m/z): 673.10 [M+H]$^+$. $^1$H NMR (400 MHz, DMSO-d$_6$) δ 9.68 (s, 1H), 8.57 (s, 1H), 8.30 (d, J=1.8 Hz, 1H), 7.69-7.98 (m, 6H), 7.56-7.68 (m, 2H), 7.17-7.47 (m, 6H), 6.90-7.00 (m, 1H), 6.13 (dd, J=9.8, 4.9 Hz, 1H), 4.92 (d, J=13.9 Hz, 1H), 4.45-4.72 (m, 3H), 2.13-2.24 (m, 1H), 1.88-1.98 (m, 1H), 1.04-1.26 (m, 1H), 0.81-0.98 (m, 2H).

Example 101: 2-(1-(4-(4-Carboxyphenyl)-1H-pyrazol-1-yl)-2-((1R*,2S*)-2-(isoindoline-2-carbonyl)cyclopropyl)ethyl)-5-(5-chloro-2-(1H-tetrazol-1-yl)phenyl)pyridine 1-oxide

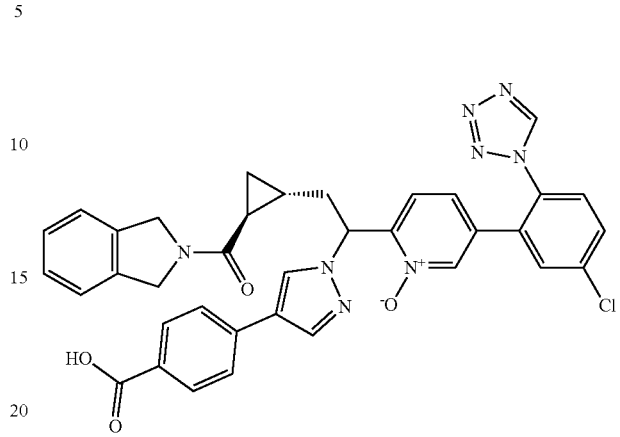

LC/MS: mass calculated for C$_{36}$H$_{29}$ClN$_8$O$_4$: 672.20, measured (ES, m/z): 673.10 [M+H]$^+$. $^1$H NMR (400 MHz, DMSO-d$_6$) δ 9.70 (s, 1H), 8.60 (s, 1H), 8.32 (d, J=1.7 Hz, 1H), 8.13 (s, 1H), 7.84-7.98 (m, 3H), 7.77-7.84 (m, 2H), 7.66-7.73 (m, 2H), 7.24-7.40 (m, 4H), 7.22 (d, J=8.3 Hz, 1H), 6.96-7.04 (m, 1H), 6.10 (dd, J=10.1, 3.7 Hz, 1H), 4.98-5.11 (m, 2H), 4.60 (s, 2H), 2.42-2.51 (m, 1H), 2.11-2.22 (m, 1H), 1.79-1.88 (m, 1H), 1.11-1.20 (m, 1H), 0.87-0.96 (m, 1H), 0.59-0.68 (m, 1H).

Example 102: 2-(1-(4-(4-Carboxyphenyl)-1H-pyrazol-1-yl)-2-((1R*,2R*)-2-(isoindoline-2-carbonyl)cyclopropyl)ethyl)-5-(5-chloro-2-(1H-tetrazol-1-yl)phenyl)pyridine 1-oxide

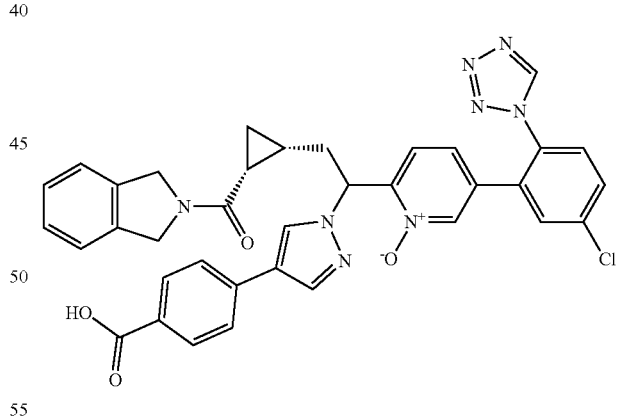

LC/MS: mass calculated for C$_{36}$H$_{29}$ClN$_8$O$_4$: 672.20, measured (ES, m/z): 673.10 [M+H]$^+$. $^1$H NMR (400 MHz, DMSO-d$_6$) δ 9.66 (s, 1H), 8.62 (s, 1H), 8.23-8.34 (m, 1H), 8.11 (s, 1H), 7.87-7.96 (m, 2H), 7.77-7.86 (m, 3H), 7.67-7.77 (m, 2H), 7.28-7.41 (m, 5H), 6.88 (d, J=8.3 Hz, 1H), 6.02 (dd, J=10.0, 4.7 Hz, 1H), 5.05 (d, J=13.7 Hz, 1H), 4.96 (d, J=14.1 Hz, 1H), 4.78 (d, J=16.0 Hz, 1H), 4.63 (d, J=16.3 Hz, 1H), 2.36-2.45 (m, 1H), 2.22-2.32 (m, 1H), 1.91-2.01 (m, 1H), 1.22-1.26 (m, 1H), 1.11-1.21 (m, 1H), 0.73-0.88 (m, 1H).

Example 103: 2-(1-(4-(4-Carboxyphenyl)-1H-pyrazol-1-yl)-2-((1S*,2R*)-2-(3-phenylpyrrolidine-1-carbonyl)cyclopropyl)ethyl)-5-(5-chloro-2-(1H-tetrazol-1-yl)phenyl)pyridine 1-oxide

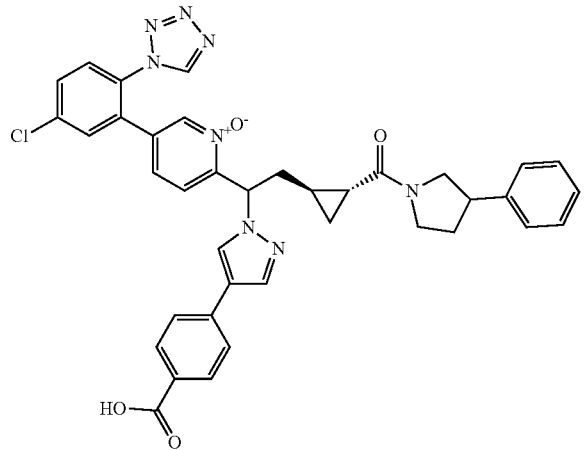

LC/MS: mass calculated for $C_{38}H_{33}ClN_8O_4$: 700.23, measured (ES, m/z): 701.10 [M+H]$^+$. $^1$H NMR (400 MHz, DMSO-$d_6$) δ 12.90 (s, 1H) 9.70 (d, J=5.5 Hz, 1H), 8.52-8.69 (m, 1H), 8.26-8.37 (m, 1H), 8.20 (s, 1H), 7.88-7.99 (m, 3H), 7.81-7.86 (m, 2H), 7.66-7.79 (m, 2H), 7.39-7.43 (m, 1H), 7.15-7.33 (m, 4H), 7.05-7.14 (m, 1H), 6.95-7.04 (m, 1H), 6.04-6.13 (m, 1H), 3.63-3.76 (m, 1H), 3.19-3.60 (m, 3H), 3.03-3.17 (m, 1H), 2.11-2.30 (m, 2H), 1.95-2.25 (m, 1H), 1.37-1.91 (m, 1H), 1.10-1.33 (m, 1H), 0.76-0.90 (m, 1H), 0.63-0.66 (m, 1H).

Example 104: 2-(1-(4-(4-Carboxyphenyl)-1H-pyrazol-1-yl)-2-((1S*,2S*)-2-(3-phenylpyrrolidine-1-carbonyl)cyclopropyl)ethyl)-5-(5-chloro-2-(1H-tetrazol-1-yl)phenyl)pyridine 1-oxide

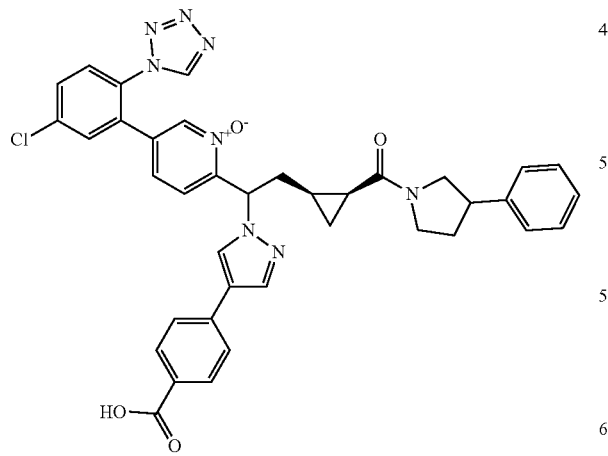

LC/MS: mass calculated for $C_{38}H_{33}ClN_8O_4$: 700.23, measured (ES, m/z): 701.10 [M+H]$^+$. $^1$H NMR (400 MHz, DMSO-$d_6$) δ 9.66-9.73 (m, 1H), 8.54-8.65 (m, 1H), 8.25-8.34 (m, 1H), 8.07-8.17 (m, 1H), 7.81-7.92 (m, 3H), 7.80-7.91 (m, 2H), 7.70-7.78 (m, 2H), 7.22-7.40 (m, 5H), 7.08-7.20 (m, 1H), 6.85-6.96 (m, 1H), 6.01-6.12 (m, 1H), 4.05-4.27 (m, 1H), 3.65-3.90 (m, 2H), 3.21-3.42 (m, 1H), 3.05-3.11 (m, 1H), 2.31-2.44 (m, 1H), 2.05-2.21 (m, 2H), 1.82-1.93 (m, 1H), 1.70-1.74 (m, 1H), 1.05-1.12 (m, 1H), 1.72-1.81 (m, 1H), 1.52-1.59 (m, 1H).

Example 105: 2-(1-(4-(4-Carboxyphenyl)-1H-pyrazol-1-yl)-2-((1R*,2R*)-2-(3-phenylpyrrolidine-1-carbonyl)cyclopropyl)ethyl)-5-(5-chloro-2-(1H-tetrazol-1-yl)phenyl)pyridine 1-oxide

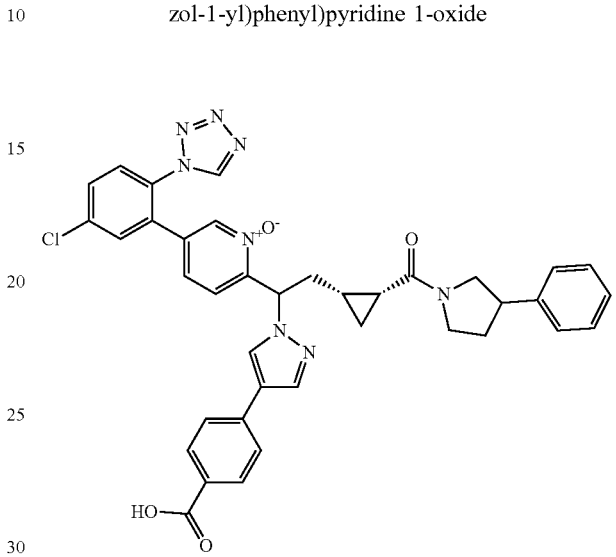

LC/MS: mass calculated for $C_{38}H_{33}ClN_8O_4$: 700.23, measured (ES, m/z): 701.10 [M+H]$^+$. $^1$H NMR (400 MHz, DMSO-$d_6$) δ 9.72 (s, 1H), 8.53-8.65 (m, 1H), 8.30-8.39 (m, 1H), 8.07-8.17 (m, 1H), 7.85-7.98 (m, 3H), 7.69-7.82 (m, 4H), 7.14-7.48 (m, 6H), 6.91-7.04 (m, 1H), 6.00-6.15 (m, 1H), 4.05-4.12 (m, 1H), 3.65-3.94 (m, 3H), 3.10-3.25 (m, 2H), 2.00-2.41 (m, 3H), 1.80-1.95 (m, 1H), 1.01-1.15 (m, 1H), 0.71-0.85 (m, 2H).

Example 106: 5-(3-Chloro-2-fluoro-6-(1H-tetrazol-1-yl)phenyl)-2-(2-cyclohexyl-1-(4-(4-((methoxycarbonyl)amino)phenyl)-1H-pyrazol-1-yl)ethyl)pyridine 1-oxide

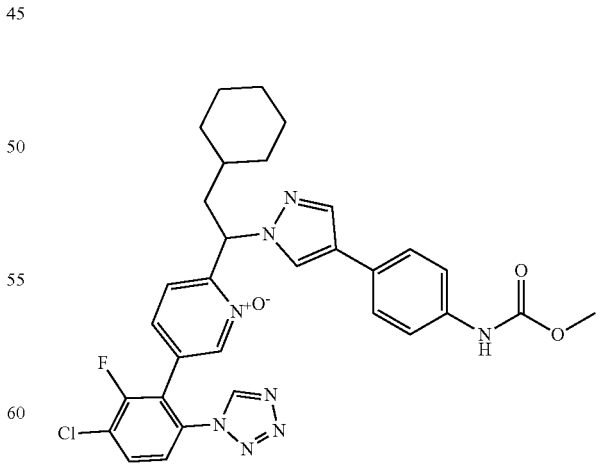

LC/MS: mass calculated for $C_{31}H_{30}ClFN_8O_3$: 616.21, measured (ES, m/z): 617.25 [M+H]$^+$. $^1$H NMR (300 MHz, DMSO-$d_6$) δ 9.68 (s, 1H), 9.65 (s, 1H), 8.41 (s, 2H), 8.06 (t, J=8.7 Hz, 1H), 7.95 (s, 1H), 7.75 (d, J=8.7 Hz, 1H), 7.50-7.53 (m, 2H), 7.71-7.44 (m, 2H), 7.06-7.19 (m, 2H), 6.03-6.24 (m, 1H), 3.66 (s, 3H), 2.12-2.32 (m, 1H), 1.91-2.05 (m, 1H), 1.78-1.91 (m, 1H), 1.63-1.74 (m, 1H), 1.45-1.62 (m, 3H), 0.82-1.22 (m, 6H). $^{19}$F NMR (282 MHz, DMSO-$d_6$) δ −74.60, −112.77.

Example 107: 5-(5-Chloro-2-(1H-tetrazol-1-yl)phenyl)-2-(2-cyclopropyl-1-(4-(1-isopropyl-6-oxo-1,6-dihydropyridazin-4-yl)-1H-pyrazol-1-yl)ethyl)pyridine 1-oxide

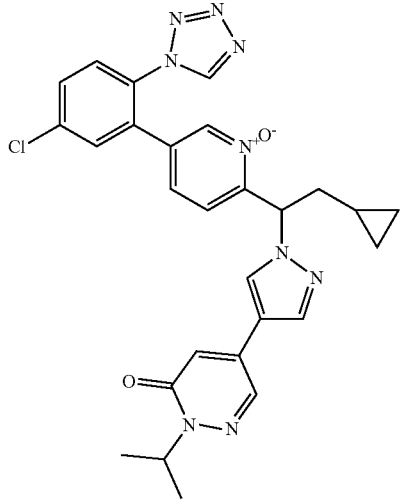

LC/MS: mass calculated for $C_{27}H_{26}ClN_9O_2$: 543.2, measured (ES, m/z): 544.2 [M+H]$^+$. $^1$H NMR (CD$_3$OD) δ 9.37 (s, 1H), 8.59 (s, 1H), 8.33 (d, J=2.0 Hz, 1H), 8.26 (s, 1H), 8.13 (s, 1H), 7.74-7.82 (m, 2H), 7.67-7.73 (m, 1H), 7.47 (d, J=8.6 Hz, 1H), 7.17 (d, J=8.1 Hz, 1H), 7.06 (d, J=2.0 Hz, 1H), 6.23 (dd, J=10.1, 4.0 Hz, 1H), 5.24 (quin, J=6.7 Hz, 1H), 2.38-2.52 (m, 1H), 1.96-2.03 (m, 1H), 1.37 (d, J=6.6 Hz, 6H), 0.60-0.72 (m, 1H), 0.33-0.50 (m, 2H), 0.18 (dq, J=9.2, 4.7 Hz, 1H), 0.00-0.08 (m, 1H).

Example 108: 2-(1-(4-(4-Carboxyphenyl)-1H-pyrazol-1-yl)-2-((1S*,2R*)-2-(pyrrolidine-1-carbonyl)cyclopropyl)ethyl)-5-(5-chloro-2-(1H-tetrazol-1-yl)phenyl)pyridine 1-oxide

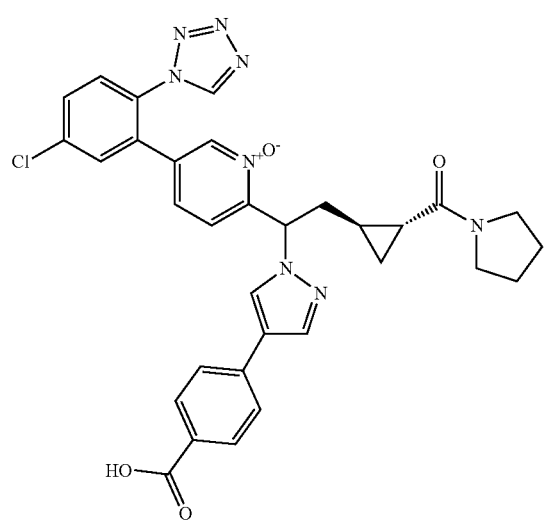

LC/MS: mass calculated for $C_{32}H_{29}ClN_8O_4$: 624.20, measured (ES, m/z): 625.10 [M+H]$^+$. $^1$H NMR (400 MHz, DMSO-$d_6$) δ 9.69 (s, 1H), 8.60 (s, 1H), 8.30 (s, 1H), 8.15 (s, 1H), 7.87-7.95 (m, 3H), 7.80-7.87 (m, 2H), 7.63-7.79 (m, 2H), 7.29 (d, J=8.4 Hz, 1H), 6.98 (dd, J=8.3 Hz, 1H), 6.07 (dd, J=10.5, 3.7 Hz, 1H), 3.28-3.40 (m, 1H), 3.15-3.26 (m, 1H), 2.97-3.15 (m, 2H), 2.24-2.38 (m, 1H), 2.08-2.21 (m, 1H), 1.66-1.78 (m, 1H), 1.53-1.65 (m, 2H), 1.26-1.45 (m, 2H), 1.11-1.22 (m, 1H), 0.75-0.86 (m, 1H), 0.58-0.68 (m, 1H).

Example 109: 2-(1-(4-(4-Carboxyphenyl)-1H-pyrazol-1-yl)-2-((1R*,2S*)-2-(pyrrolidine-1-carbonyl)cyclopropyl)ethyl)-5-(5-chloro-2-(1H-tetrazol-1-yl)phenyl)pyridine 1-oxide

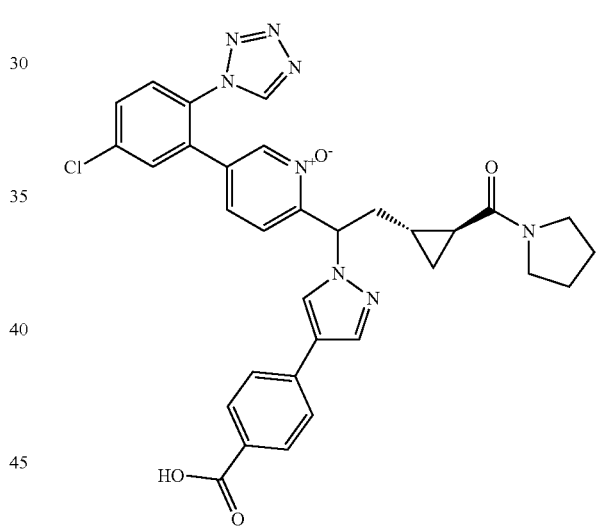

LC/MS: mass calculated for $C_{32}H_{29}ClN_8O_4$: 624.20, measured (ES, m/z): 625.10 [M+H]$^+$. $^1$H NMR (400 MHz, DMSO-$d_6$) δ 9.69 (s, 1H), 8.60 (s, 1H), 8.30 (s, 1H), 8.13 (s, 1H), 7.87-7.95 (m, 3H), 7.79-7.87 (m, 2H), 7.68-7.77 (m, 2H), 7.16 (d, J=8.3 Hz, 1H), 6.99 (dd, J=8.3 Hz, 1H), 6.05 (dd, J=10.0, 3.7 Hz, 1H), 3.47-3.70 (m, 2H), 3.12-3.28 (m, 2H), 2.33-2.46 (m, 1H), 2.03-2.16 (m, 1H), 1.85-1.98 (m, 2H), 1.64-1.83 (m, 3H), 1.01-1.15 (m, 1H), 0.74-0.86 (m, 1H), 0.48-0.60 (m, 1H).

Example 110: 2-(1-(4-(4-Carboxyphenyl)-1H-pyrazol-1-yl)-2-((1S*,2S*)-2-(pyrrolidine-1-carbonyl)cyclopropyl)ethyl)-5-(5-chloro-2-(1H-tetrazol-1-yl)phenyl)pyridine 1-oxide

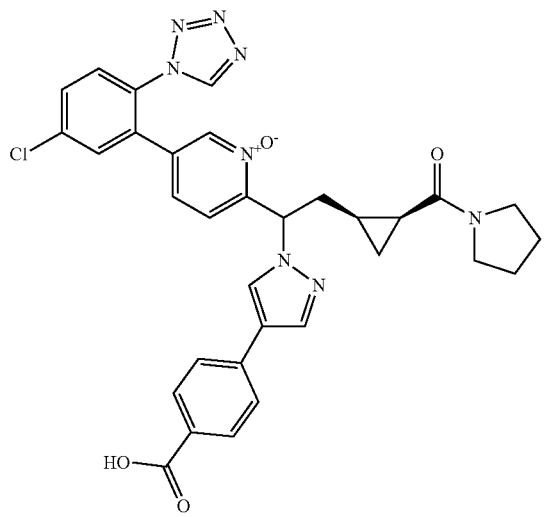

LC/MS: mass calculated for $C_{32}H_{29}ClN_8O_4$: 624.20, measured (ES, m/z): 625.05 [M+H]$^+$. $^1$H NMR (400 MHz, DMSO-d$_6$) δ 9.68 (s, 1H), 8.56 (s, 1H), 8.30 (s, 1H), 8.09 (s, 1H), 7.87-7.96 (m, 3H), 7.78-7.88 (m, 2H), 7.69-7.78 (m, 2H), 7.30 (d, J=8.3 Hz, 1H), 6.91-6.98 (m, 1H), 6.09 (dd, J=9.5, 5.3 Hz, 1H), 3.44-3.56 (m, 1H), 3.12-3.30 (m, 3H), 2.35-2.47 (m, 1H), 2.09-2.23 (m, 1H), 1.63-1.91 (m, 5H), 0.94-1.09 (m, 1H), 0.74-0.91 (m, 2H).

Example 111: 2-(1-(4-(4-Carboxyphenyl)-1H-pyrazol-1-yl)-2-((1R*,2R*)-2-(pyrrolidine-1-carbonyl)cyclopropyl)ethyl)-5-(5-chloro-2-(1H-tetrazol-1-yl)phenyl)pyridine 1-oxide

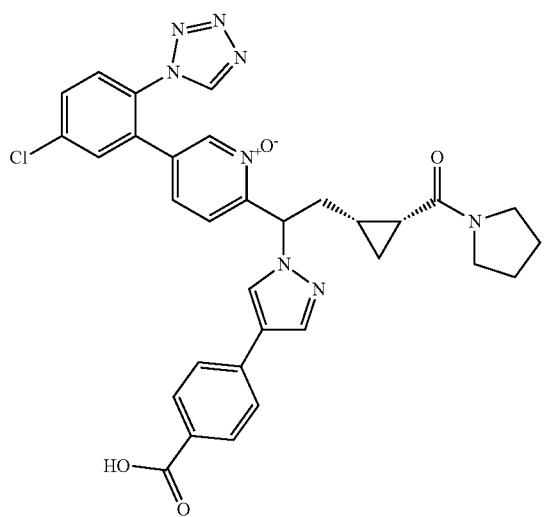

LC/MS: mass calculated for $C_{32}H_{29}ClN_8O_4$: 624.20, measured (ES, m/z): 625.05 [M+H]$^+$. $^1$H NMR (400 MHz, DMSO-d$_6$) δ 9.68 (s, 1H), 8.57 (s, 1H), 8.30 (s, 1H), 8.11 (s, 1H), 7.87-7.95 (m, 3H), 7.79-7.87 (m, 2H), 7.71-7.77 (m, 2H), 7.35 (d, J=8.3 Hz, 1H), 6.89-7.00 (m, 1H), 5.98 (dd, J=10.5, 4.3 Hz, 1H), 3.47-3.70 (m, 3H), 3.17-3.30 (m, 1H), 2.37-2.48 (m, 1H), 2.03-2.16 (m, 1H), 1.89-2.02 (m, 2H), 1.69-1.88 (m, 3H), 0.96-1.11 (m, 1H), 0.71-0.78 (m, 1H), 0.62-0.70 (m, 1H).

Example 112: 5-(3-Chloro-2-fluoro-6-(1H-tetrazol-1-yl)phenyl)-2-(2-cyclopropyl-1-(4-(1-(methoxycarbonyl)piperidin-3-yl)-1H-pyrazol-1-yl)ethyl)pyridine 1-oxide

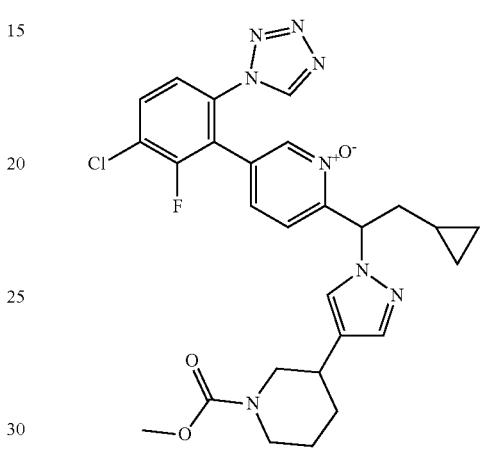

LC/MS: mass calculated for $C_{27}H_{28}ClFN_8O_3$: 566.2, measured (ES, m/z): 567.0 [M+H]$^+$. $^1$H NMR (300 MHz, DMSO-d$_6$) δ 9.68 (s, 1H), 8.37 (s, 1H), 8.39 (s, 1H), 8.06 (d, J=8.7 Hz, 1H), 7.89 (s, 1H), 7.75 (d, J=8.7 Hz, 1H), 7.47 (s, 1H), 7.13 (s, 2H), 5.99 (dd, J=9.6, 4.2 Hz, 1H), 3.96-4.10 (m, 1H), 3.81-3.95 (m, 1H), 3.59 (s, 3H), 2.69-2.96 (m, 2H), 2.53-2.66 (m, 1H), 2.18-2.34 (m, 1H), 1.91-2.04 (m, 1H), 1.75-1.90 (m, 1H), 1.59-1.72 (m, 1H), 1.35-1.56 (m, 2H), 0.44-0.62 (m, 1H), 0.18-0.40 (m, 2H), 0.02-0.13 (m, 1H), −0.14-0.00 (m, 1H). $^{19}$F NMR (282 MHz, DMSO-d$_6$) δ −74.95, −112.78.

Example 113: 5-(3-Chloro-2-fluoro-6-(1H-tetrazol-1-yl)phenyl)-2-(2-cyclobutyl-1-(4-(4-((methoxycarbonyl)amino)phenyl)-1H-pyrazol-1-yl)ethyl)pyridine 1-oxide

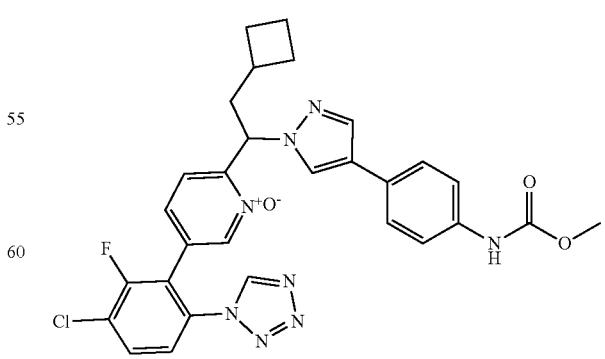

LC/MS: mass calculated for $C_{29}H_{26}ClFN_8O$: 588.2, measured (ES, m/z): 589.1 [M+H]$^+$. $^1$H NMR (300 MHz, Chloroform-d) δ 8.62 (s, 1H), 8.34 (s, 1H), 7.86 (s, 1H), 7.74-7.84 (m, 2H), 7.51 (d, J=8.3 Hz, 1H), 7.34-7.48 (m, 5H), 7.01 (d, J=8.3 Hz, 1H), 6.72 (s, 1H), 5.97-6.08 (m, 1H), 3.80 (s, 3H), 2.47-2.66 (m, 1H), 2.16-2.36 (m, 2H), 2.01-2.13 (m, 1H), 1.77-1.99 (m, 4H), 1.57-1.75 (m, 1H). $^{19}$F NMR (282 MHz, Chloroform-d) δ −75.81, −109.82.

Example 114: 5-(3-Chloro-2-fluoro-6-(1H-tetrazol-1-yl)phenyl)-2-(2-cyclopentyl-1-(4-(4-((methoxycarbonyl)amino)phenyl)-1H-pyrazol-1-yl)ethyl)pyridine 1-oxide

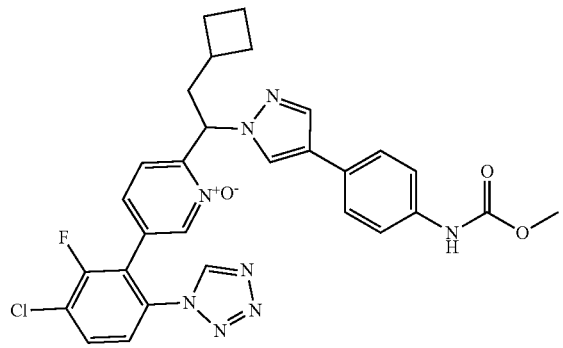

LC/MS: mass calculated for $C_{30}H_{28}ClFN_8O_3$: 602.2, measured (ES, m/z): 603.0 [M+H]$^+$. $^1$H NMR (300 MHz, DMSO-d$_6$) δ 9.67 (s, 1H), 9.65 (s, 1H), 8.41 (s, 2H), 8.01-8.10 (m, 1H), 7.95 (s, 1H), 7.75 (d, J=8.7 Hz, 1H), 7.52 (d, J=8.7 Hz, 2H), 7.44 (d, J=8.7 Hz, 2H), 7.23 (d, J=8.3 Hz, 1H), 7.15 (d, J=8.3 Hz, 1H), 6.02 (dd, J=10.6, 3.8 Hz, 1H), 3.66 (s, 3H), 2.28-2.46 (m, 1H), 1.93-2.13 (m, 1H), 1.68-1.86 (m, 1H), 1.23-1.66 (m, 7H), 0.95-1.15 (m, 1H). $^{19}$F NMR (282 MHz, DMSO-d$_6$) δ −74.14, −112.77.

Example 115: 5-(5-Chloro-2-(1H-tetrazol-1-yl)phenyl)-2-(2-cyclopropyl-1-(4-(1-(2-isopropoxyethyl)-6-oxo-1,6-dihydropyridazin-4-yl)-1H-pyrazol-1-yl)ethyl)pyridine 1-oxide

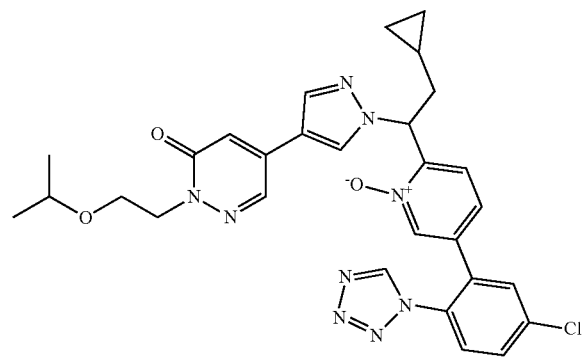

LC/MS: mass calculated for $C_{29}H_{30}ClN_9O_3$: 587.2, measured (ES, m/z): 588.3 [M+H]$^+$. $^1$H NMR (CD$_3$OD) δ 9.38 (s, 1H), 8.60 (s, 1H), 8.22-8.33 (m, 2H), 8.13 (s, 1H), 7.75-7.81 (m, 2H), 7.67-7.73 (m, 1H), 7.47 (d, J=8.1 Hz, 1H), 7.16 (br d, J=8.1 Hz, 1H), 7.08 (d, J=2.0 Hz, 1H), 6.14-6.32 (m, 1H), 4.30 (t, J=5.6 Hz, 2H), 3.83 (t, J=5.8 Hz, 2H), 3.62 (dt, J=12.1, 6.1 Hz, 1H), 2.37-2.53 (m, 1H), 1.97-2.07 (m, 1H), 1.09 (d, J=6.1 Hz, 6H), 0.65 (br d, J=6.1 Hz, 1H), 0.34-0.49 (m, 2H), 0.18 (dq, J=9.2, 4.7 Hz, 1H), 0.01-0.07 (m, 1H).

Example 116: 5-(5-Chloro-2-(1H-tetrazol-1-yl)phenyl)-2-(2-cyclopropyl-1-(4-(1-ethyl-6-oxo-1,6-dihydropyridazin-4-yl)-1H-pyrazol-1-yl)ethyl)pyridine 1-oxide

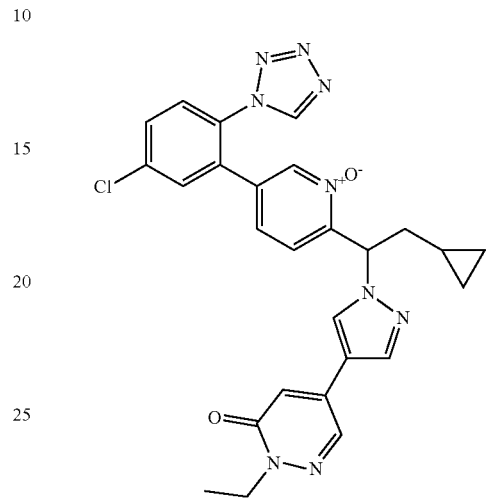

LC/MS: mass calculated for $C_{26}H_{24}ClN_9O_2$: 529.2, measured (ES, m/z): 530.3 [M+H]$^+$. $^1$H NMR (CD$_3$OD) δ 9.38 (s, 1H), 8.60 (br s, 1H), 8.23-8.35 (m, 2H), 8.12 (s, 1H), 7.75-7.81 (m, 2H), 7.68-7.73 (m, 1H), 7.47 (d, J=8.1 Hz, 1H), 7.16 (br d, J=7.6 Hz, 1H), 7.08 (d, J=1.5 Hz, 1H), 6.23 (br d, J=6.6 Hz, 1H), 4.20 (q, J=7.1 Hz, 2H), 2.37-2.50 (m, 1H), 1.97-2.03 (m, 1H), 1.36 (t, J=7.3 Hz, 3H), 0.60-0.73 (m, 1H), 0.33-0.50 (m, 2H), 0.14-0.23 (m, 1H), 0.00-0.07 (m, 1H).

Example 117: 2-(2-((1S*,2R*)-2-Carbamoylcyclopropyl)-1-(4-(4-Carboxyphenyl)-1H-pyrazol-1-yl)ethyl)-5-(5-chloro-2-(1H-tetrazol-1-yl)phenyl)pyridine 1-oxide

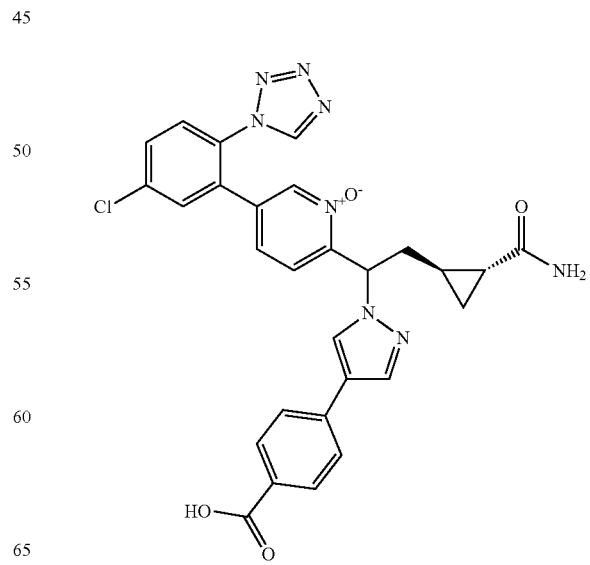

LC/MS: mass calculated for $C_{28}H_{23}ClN_8O_4$: 570.15, measured (ES, m/z): 571.05 [M+H]$^+$. $^1$H NMR (400 MHz, DMSO-d$_6$) δ 9.69 (s, 1H), 8.63 (s, 1H), 8.30 (d, J=1.7 Hz, 1H), 8.14 (s, 1H), 7.88-7.95 (m, 3H), 7.80-7.88 (m, 2H), 7.72-7.78 (m, 2H), 7.37 (s, 1H), 7.20 (d, J=8.3 Hz, 1H), 6.96 (d, J=8.3 Hz, 1H), 6.72 (s, 1H), 6.07 (dd, J=10.1, 4.3 Hz, 1H), 2.55-2.65 (m, 1H), 1.77-1.89 (m, 1H), 1.32-1.41 (m, 1H), 0.92-1.04 (m, 1H), 0.72-0.82 (m, 1H), 0.55-0.68 (m, 1H).

Example 118: 2-(2-((1S*,2S*)-2-Carbamoylcyclopropyl)-1-(4-(4-Carboxyphenyl)-1H-pyrazol-1-yl)ethyl)-5-(5-chloro-2-(1H-tetrazol-1-yl)phenyl)pyridine 1-oxide

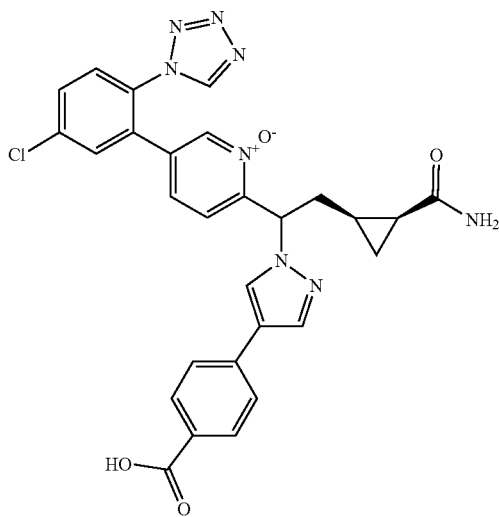

LC/MS: mass calculated for $C_{28}H_{23}ClN_8O_4$: 570.15, measured (ES, m/z): 571.05 [M+H]$^+$. $^1$H NMR (400 MHz, DMSO-d$_6$) δ 9.69 (s, 1H), 8.52-8.59 (m, 1H), 8.28-8.32 (m, 1H), 8.08-8.13 (m, 1H), 7.90-7.91 (m, 3H), 7.82-7.84 (m, 2H), 7.72-7.75 (m, 2H), 7.46-7.61 (m, 1H), 7.20-7.29 (m, 1H), 6.93-7.00 (m, 1H), 6.75-6.88 (m, 1H), 6.05-6.13 (m, 1H), 2.29-2.39 (m, 1H), 2.02-2.09 (m, 1H), 1.44-1.57 (m, 1H), 0.83-1.00 (m, 1H), 0.66-0.77 (m, 1H), 0.43-0.63 (m, 1H).

Example 119: 5-(3-Chloro-2-fluoro-6-(1H-tetrazol-1-yl)phenyl)-2-(1-(4-(4-((methoxycarbonyl)amino)phenyl)-1H-pyrazol-1-yl)-2-((S*)-tetrahydro-2H-pyran-2-yl)ethyl)pyridine 1-oxide

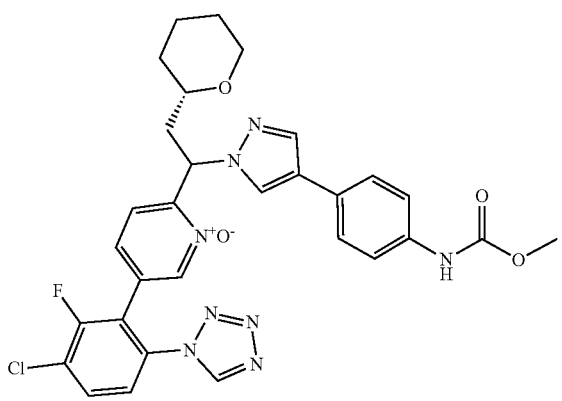

Step 1: N-methoxy-N-methyl-2-(tetrahydro-2H-pyran-2-yl)acetamide

To a solution of 2-(tetrahydro-2H-pyran-2-yl)acetic acid (500 mg, 3.47 mmol, 1.0 equiv.) in DCM (20 mL) was added N,O-dimethylhydroxylamine hydrochloride (408 mg, 4.17 mmol, 1.2 equiv.), EDC.HCl (999 mg, 5.21 mmol, 1.5 equiv.), DMAP (423 mg, 3.47 mmol, 1.0 equiv.) and DIEA (1343 mg, 10.41 mmol, 3.0 equiv.). The resulting mixture was stirred at room temperature overnight. The resulting mixture was washed with 1N HCl and extracted with DCM (3×20 mL). The organic layers were combined, dried over Na$_2$SO$_4$, filtered and concentrated to yield N-methoxy-N-methyl-2-(tetrahydro-2H-pyran-2-yl)acetamide as light yellow oil. $^1$H NMR (400 MHz, Chloroform-d): δ 3.90-3.97 (m, 1H), 3.74-3.85 (m, 1H), 3.68 (s, 3H), 3.40-3.49 (m, 1H), 3.17 (s, 3H), 2.76 (dd, J=15.5, 7.6 Hz, 1H), 2.36 (dd, J=15.3, 5.2 Hz, 1H), 1.76-1.87 (m, 1H), 1.62-1.72 (m, 1H), 1.43-1.57 (m, 3H), 1.23-1.37 (m, 1H).

Step 2: 1-(5-Bromopyridin-2-yl)-2-(tetrahydro-2H-pyran-2-yl)ethan-1-one n-Butyllithium (2.5 M in hexane, 1.3 mL, 3.20 mmol, 1.2 equiv.) was added dropwise to a stirred solution of 2,5-dibromopyridine (759 mg, 3.20 mmol, 1.2 equiv.) in toluene (15 mL) under nitrogen at −78° C. The mixture was stirred at −78° C. for 2 h. Then N-methoxy-N-methyl-2-(tetrahydro-2H-pyran-2-yl)acetamide (500 mg, 2.67 mmol, 1.0 equiv.) in toluene (5 mL) was added dropwise and the mixture was stirred at −78° C. for 1 h. The mixture was quenched with sat. aqueous NH$_4$Cl and allowed to warm to room temperature. The organic layer was separated, washed with brine, dried Na$_2$SO$_4$, filtered and concentrated under vacuum. The resulting residue was purified by silica gel chromatography (0→100% ethyl acetate/petroleum ether) to yield 1-(5-bromopyridin-2-yl)-2-(tetrahydro-2H-pyran-2-yl)ethan-1-one as a light yellow solid. LC/MS: mass calculated for $C_{12}H_{14}BrNO_2$: 283.02, measured (ES, m/z): 284.00, 286.00 [M+H, M+H+2]$^+$.

Step 3: 1-(5-Bromopyridin-2-yl)-2-(tetrahydro-2H-pyran-2-yl)ethan-1-ol

To a solution of 1-(5-bromopyridin-2-yl)-2-(tetrahydro-2H-pyran-2-yl)ethan-1-one (413 mg, 1.45 mmol, 1.0 equiv.) in CH$_3$OH (10 mL) was added NaBH$_4$ (66 mg, 1.74 mmol, 1.2 equiv.) at 0° C. The resulting mixture was stirred at room temperature. overnight. The mixture was quenched with water. The resulting mixture was extracted with ethyl acetate (3×20 mL). The organic layers were combined, dried over Na$_2$SO$_4$, filtered and concentrated to yield 1-(5-bromopyridin-2-yl)-2-(tetrahydro-2H-pyran-2-yl)ethan-1-ol as a white solid. LC/MS: mass calculated for $C_{12}H_{16}BrNO_2$: 285.04, measured (ES, m/z): 286.00, 288.00 [M+H, M+H+2]$^+$.

Step 4: 1-(5-Bromopyridin-2-yl)-2-((R*)tetrahydro-2H-pyran-2-yl)ethyl methanesulfonate To a solution of 1-(5-bromopyridin-2-yl)-2-(tetrahydro-2H-pyran-2-yl)ethan-1-ol (400 mg, 1.40 mmol, 1.0 equiv.) in dichloromethane (20 mL) was added methanesulfonyl chloride (320 mg, 2.80 mmol, 2.0 equiv.), triethyl amine (424 mg, 4.20 mmol, 3.0 equiv.). The resulting mixture was stirred at room temperature for 3 h. The resulting mixture was extracted with ethyl acetate (3×10 mL). The organic layers were combined, dried over sodium sulfate, filtered, and concentrated. The resulting residue was purified by silica gel chromatography (0→50% ethyl acetate/petroleum ether) to yield 1-(5-bromopyridin-2-yl)-2-((R*)tetrahydro-2H-pyran-2-yl)ethyl methanesulfonate as a light yellow solid. LC/MS: mass calculated for $C_{13}H_{18}BrNO_4S$: 363.01, measured (ES, m/z): 363.95, 365.95 [M+H, M+H+2]$^+$.

Step 5: Methyl (4-(1-(1-(5-bromopyridin-2-yl)-2-((S*)-tetrahydro-2H-pyran-2-yl)ethyl)-1H-pyrazol-4-yl)phenyl)carbamate To a solution of 1-(5-bromopyridin-2-yl)-2-((R*)tetrahydro-2H-pyran-2-yl)ethyl methanesulfonate (284 mg, 0.78 mmol, 1.0 equiv.) in acetonitrile (10 mL) was added methyl 4-(1H-pyrazol-4-yl)phenylcarbamate (254 mg, 1.17 mmol, 1.5 equiv.) and $Cs_2CO_3$ (508 mg, 1.56 mmol, 2.0 equiv.). The resulting mixture was stirred at 70° C. for 3 h. The reaction was quenched with $H_2O$ (10 mL). The resulting mixture was extracted with ethyl acetate (3×20 mL). The organic layers were combined, dried over $Na_2SO_4$, filtered and concentrated. The resulting residue was purified by silica gel chromatography (0→50% ethyl acetate/petroleum ether) to yield methyl (4-(1-(1-(5-bromopyridin-2-yl)-2-((S*)-tetrahydro-2H-pyran-2-yl)ethyl)-1H-pyrazol-4-yl)phenyl)carbamate as a light yellow solid. LC/MS: mass calculated for $C_{23}H_{25}BrN_4O_3$: 484.11, measured (ES, m/z): 485.00, 487.00 [M+H, M+H+2]$^+$.

Step 6: Methyl (4-(1-(1-(5-(6-amino-3-chloro-2-fluorophenyl)pyridin-2-yl)-2-((S*)-tetrahydro-2H-pyran-2-yl)ethyl)-1H-pyrazol-4-yl)phenyl)carbamate To a solution of methyl (4-(1-(1-(5-bromopyridin-2-yl)-2-((S*)-tetrahydro-2H-pyran-2-yl)ethyl)-1H-pyrazol-4-yl)phenyl)carbamate (120 mg, 0.25 mmol, 1.0 equiv.) in 1,4-dioxane/$H_2O$ (12 mL) was added 6-amino-3-chloro-2-fluorophenylboronic acid (94 mg, 0.49 mmol, 2.0 equiv.), $K_2CO_3$ (114 mg, 0.74 mmol, 3.0 equiv.) and Pd(PPh$_3$)$_4$ (28 mg, 0.025 mmol, 0.1 equiv.) under $N_2$. The resulting mixture was stirred at 80° C. for 2 h. The reaction was quenched with $H_2O$ (10 mL). The resulting mixture was extracted with ethyl acetate (3×30 mL). The organic layers were combined, dried over $Na_2SO_4$, filtered and concentrated. The resulting residue was purified by silica gel chromatography (0→100% ethyl acetate/petroleum ether) to yield methyl (4-(1-(1-(5-(6-amino-3-chloro-2-fluorophenyl)pyridin-2-yl)-2-((S*)-tetrahydro-2H-pyran-2-yl)ethyl)-1H-pyrazol-4-yl)phenyl) carbamate as a light yellow solid. LC/MS: mass calculated for $C_{29}H_{29}ClFN_5O_3$: 549.19, measured (ES, m/z): 550.25 [M+H]$^+$.

Step 7: Methyl (4-(1-(1-(5-(3-chloro-2-fluoro-6-(1H-tetrazol-1-yl)phenyl)pyridin-2-yl)-2-((S*)-tetrahydro-2H-pyran-2-yl)ethyl)-1H-pyrazol-4-yl)phenyl) carbamate To a solution of methyl (4-(1-(1-(5-(6-amino-3-chloro-2-fluorophenyl)pyridin-2-yl)-2-((S*)-tetrahydro-2H-pyran-2-yl)ethyl)-1H-pyrazol-4-yl)phenyl)carbamate (185 mg, 0.34 mmol, 1.0 equiv.) in acetic acid (5 mL) was added TMSN$_3$ (193.8 mg, 1.68 mmol, 5.0 equiv.) and trimethoxymethane (356 mg, 3.36 mmol, 10.0 equiv.). The resulting mixture was stirred at room temperature overnight. The resulting mixture was extracted with EtOAc (3×10 mL). The organic layers were combined, dried over $Na_2SO_4$, filtered and concentrated. The resulting residue was purified by C18 chromatography (0→50% $CH_3CN/H_2O$) to yield methyl (4-(1-(1-(5-(3-chloro-2-fluoro-6-(1H-tetrazol-1-yl)phenyl)pyridin-2-yl)-2-((S*)-tetrahydro-2H-pyran-2-yl)ethyl)-1H-pyrazol-4-yl)phenyl)carbamate. LC/MS: mass calculated for $C_{30}H_{28}ClFN_8O_3$: 602.20, measured (ES, m/z): 603.20 [M+H]$^+$.

Step 8: 5-(3-Chloro-2-fluoro-6-(1H-tetrazol-1-yl) phenyl)-2-(1-(4-(4-((methoxycarbonyl)amino)phenyl)-1H-pyrazol-1-yl)-2-((S*)-tetrahydro-2H-pyran-2-yl)ethyl)pyridine 1-oxide A mixture of methyl (4-(1-(1-(5-(3-chloro-2-fluoro-6-(1H-tetrazol-1-yl)phenyl)pyridin-2-yl)-2-((S*)-tetrahydro-2H-pyran-2-yl)ethyl)-1H-pyrazol-4-yl)phenyl)carbamate (350 mg, 0.58 mmol, 1.0 equiv.), methyl trioxorhenium (VII) (72 mg, 0.29 mmol, 0.5 equiv.) and hydrogen peroxide (0.29 mL, 2.90 mmol, 30 wt %, 5.0 equiv.) in $CH_3OH$ (5 mL) was stirred at room temperature for 1 h. The reaction was purified by reverse phase chromatography on C18 (80 g, MeCN/$H_2O$ (0.05% $CF_3COOH$): 0→45%) to yield 5-(3-chloro-2-fluoro-6-(1H-tetrazol-1-yl)phenyl)-2-(1-(4-(4-((methoxycarbonyl)amino)phenyl)-1H-pyrazol-1-yl)-2-((S*)-tetrahydro-2H-pyran-2-yl)ethyl)pyridine 1-oxide as a white solid.

LC/MS: mass calculated for $C_{30}H_{28}ClFN_8O_4$: 618.19; measured (ES, m/z): 619.10 [M+H]$^+$. $^1$H NMR (400 MHz, CDCl$_3$): δ 8.68 (s, 1H), 8.41 (s, 1H), 7.74-7.92 (m, 3H), 7.34-7.59 (m, 6H), 7.05-7.11 (m, 1H), 6.69 (s, 1H), 6.30-6.36 (m, 1H), 3.78-3.89 (m, 4H), 3.18-3.34 (m, 2H), 2.45-2.62 (m, 2H), 1.78-1.83 (m, 1H), 1.62-1.70 (m, 1H), 1.17-1.59 (m, 4H). $^{19}$F NMR (376 MHz, CDCl$_3$): δ −75.81, −109.93.

Example 120: 5-(3-Chloro-2-fluoro-6-(1H-tetrazol-1-yl)phenyl)-2-(2-(4-fluorophenyl)-1-(4-(1-methyl-6-oxo-1,6-dihydropyridazin)-1H-pyrazol-1-yl)ethyl) pyridine 1-oxide

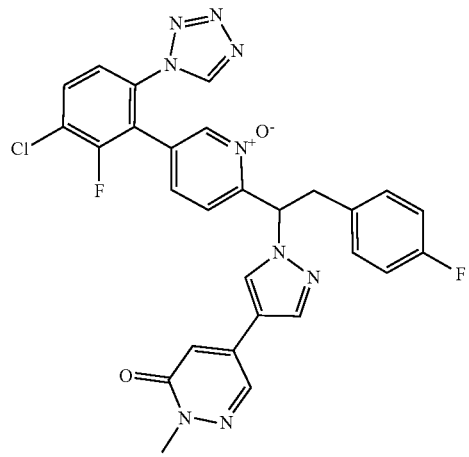

LC/MS: mass calculated for $C_{28}H_{20}ClF_2N_9O_2$: 587.13; measured (ES, m/z): 588.0 [M+H]$^+$. $^1$H NMR (300 MHz, Chloroform-d) δ 8.62 (s, 1H), 8.31 (s, 1H), 7.95 (s, 1H), 7.84 (d, J=2.1 Hz, 1H), 7.78 (t, J=8.7 Hz, 1H), 7.70 (s, 1H), 7.65 (d, J=8.3 Hz, 1H), 7.41 (d, J=8.7 Hz, 1H), 7.00-7.12 (m, 3H), 6.86-6.98 (m, 3H), 6.19 (d, J=10.3 Hz, 1H), 3.78 (s, 3H), 3.61-3.68 (m, 1H), 3.42-3.51 (m, 1H). $^{19}$F NMR (282 MHz, Chloroform-d) δ −75.87, −109.75, −114.91.

Example 121: 5-(3-Chloro-2-fluoro-6-(1H-tetrazol-1-yl)phenyl)-2-(2-(4-fluorophenyl)-1-(4-(4-((methoxycarbonyl)amino)phenyl)-1H-pyrazol-1-yl)ethyl)pyridine 1-oxide

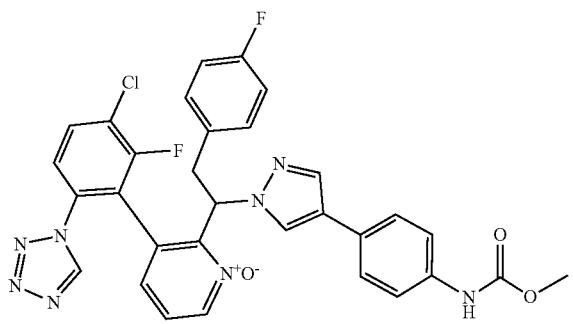

LC/MS: mass calculated for C₃₁H₂₃ClF₂N₈O₃: 628.15, measured (ES, m/z): 629.1 [M+H]⁺. ¹H NMR (300 MHz, Chloroform-d) δ 8.61 (s, 1H), 8.36 (s, 1H), 7.90 (s, 1H), 7.77 (t, J=7.3 Hz, 1H), 7.60 (d, J=8.3 Hz, 1H), 7.51 (s, 1H), 7.40 (d, J=8.7 Hz, 1H), 7.34 (s, 4H), 7.02-7.15 (m, 3H), 6.89-6.91 (m, 2H), 6.65 (s, 1H), 6.13 (d, J=10.3 Hz, 1H), 3.71-3.81 (m, 3H), 3.62-3.73 (m, 1H), 3.42-3.51 (m, 1H). ¹⁹F NMR (282 MHz, Chloroform-d) δ −75.79, −109.83, −115.48.

Example 122: 2-((1R*,2R*)-1-(4-(4-Carboxyphenyl)-1H-pyrazol-1-yl)-2-hydroxy-2-phenylethyl)-5-(5-chloro-2-(1H-tetrazol-1-yl)phenyl)pyridine 1-oxide

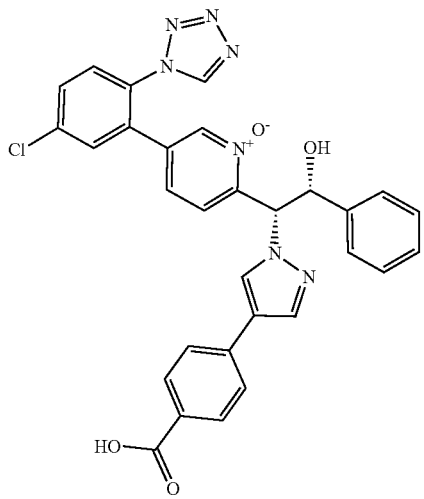

LC/MS: mass calculated for C₃₀H₂₂ClN₇O₄: 579.14, measured (ES, m/z): 580.05 [M+H]⁺. ¹H NMR (400 MHz, DMSO-d₆) δ 9.73 (s, 1H), 8.29 (d, J=1.8 Hz, 1H), 8.04-8.10 (m, 1H), 7.89-8.04 (m, 3H), 7.79-7.91 (m, 4H), 7.52-7.60 (m, 2H), 7.13-7.29 (m, 5H), 7.08 (d, J=8.3 Hz, 1H), 6.25 (d, J=9.7 Hz, 1H), 5.51 (d, J=9.7 Hz, 1H).

Example 123: 2-((1R*,2S*)-1-(4-(4-Carboxyphenyl)-1H-pyrazol-1-yl)-2-hydroxy-2-phenylethyl)-5-(5-chloro-2-(1H-tetrazol-1-yl)phenyl)pyridine 1-oxide

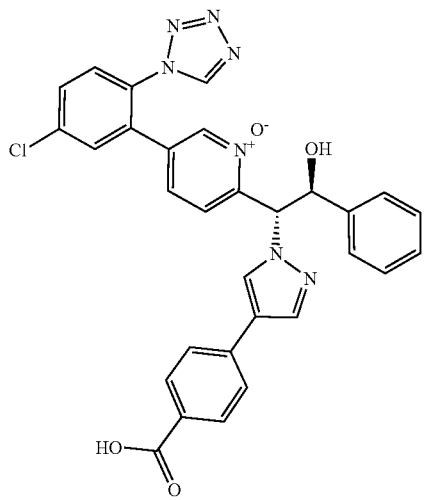

LC/MS: mass calculated for C₃₀H₂₂ClN₇O₄: 579.14, measured (ES, m/z): 580.05 [M+H]⁺. ¹H NMR (300 MHz, DMSO-d₆) δ 9.60 (s, 1H), 8.66 (s, 1H), 8.24 (s, 1H), 8.01 (s, 1H), 7.87-7.97 (m, 2H), 7.75-7.88 (m, 3H), 7.68-7.81 (m, 2H), 7.52 (d, J=8.3 Hz, 1H), 7.29-7.39 (m, 2H), 7.14-7.32 (m, 3H), 6.88 (d, J=8.3 Hz, 1H), 6.42 (d, J=6.8 Hz, 1H), 5.58 (d, J=6.9 Hz, 1H).

Example 124: 2-(2-((3r,5r,7r)-Adamantan-1-yl)-1-(4-(4-((methoxycarbonyl)amino)phenyl)-1H-pyrazol-1-yl)ethyl)-5-(3-Chloro-2-fluoro-6-(1H-tetrazol-1-yl)phenyl)pyridine 1-oxide

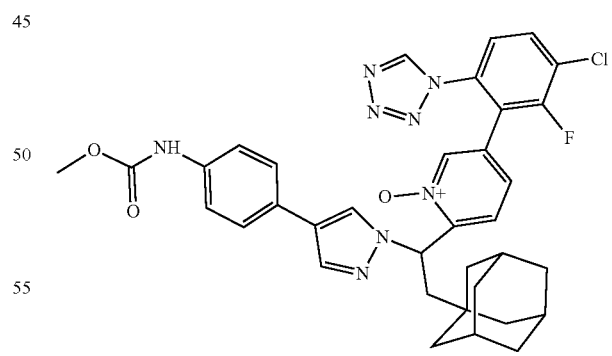

LC/MS: mass calculated for C₃₅H₃₄ClFN₈O₃: 668.24, measured (ES, m/z): 669.10 [M+H]⁺. ¹H NMR (300 MHz, Chloroform-d) δ 8.63 (s, 1H), 8.38 (s, 1H), 7.71-7.88 (m, 3H), 7.35-7.49 (m, 6H), 7.04 (d, J=8.3 Hz, 1H), 6.65 (s, 1H), 6.36 (d, J=9.1 Hz, 1H), 3.78 (s, 3H), 2.41-2.55 (m, 1H), 1.88-1.94 (m, 3H), 1.72-1.83 (m, 1H), 1.49-1.70 (m, 9H), 1.33-1.43 (m, 3H). ¹⁹F NMR (282 MHz, Chloroform-d) δ −75.79, −109.91.

Example 125: 5-(3-Chloro-2-fluoro-6-(1H-tetrazol-1-yl)phenyl)-2-(2-(4-fluorophenyl)-1-(4-(4-(5-oxopyrrolidin-2-yl)phenyl)-1H-pyrazol-1-yl)ethyl)pyridine 1-oxide

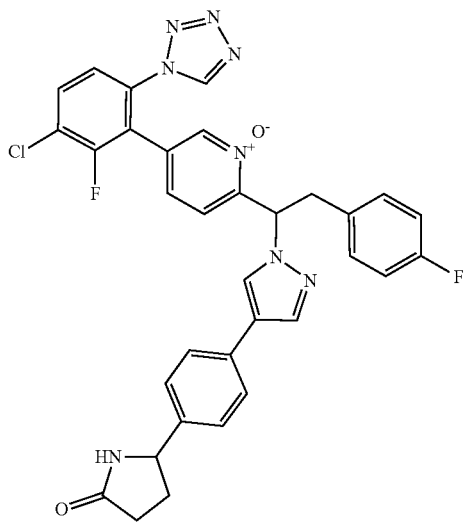

LC/MS: mass calculated for $C_{33}H_{25}ClF_2N_8O_2$: 638.17, measured (ES, m/z): 639.1 [M+H]$^+$. $^1$H NMR (300 MHz, Chloroform-d) δ 8.64 (s, 1H), 8.33 (s, 1H), 7.93 (s, 1H), 7.79 (t, J=8.0 Hz, 1H), 7.52-7.63 (m, 2H), 7.40-7.46 (m, 3H), 7.24-7.31 (m, 2H), 7.09-7.12 (m, 2H), 7.00 (d, J=8.3 Hz, 1H), 6.91 (t, J=8.4 Hz, 2H), 6.51 (s, 1H), 6.14 (d, J=10.2 Hz, 1H), 4.79 (t, J=7.0 Hz, 1H), 3.60-3.73 (m, 2H), 2.40-2.70 (m, 3H), 1.91-2.01 (m, 1H). $^{19}$F NMR (282 MHz, Chloroform-d) δ −75.97, −109.83, −115.57.

Example 126: 5-(3-Chloro-2-fluoro-6-(1H-tetrazol-1-yl)phenyl)-2-(2-(4,4-dimethylcyclohexyl)-1-(4-(4-((methoxycarbonyl)amino)phenyl)-1H-pyrazol-1-yl)ethyl)pyridine 1-oxide

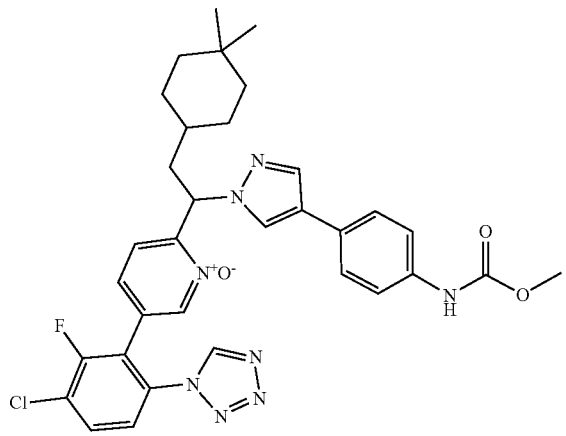

LC/MS: mass calculated for $C_{33}H_{34}ClFN_8O_3$: 644.21, measured (ES, m/z): 645.25 [M+H]$^+$. $^1$H NMR (300 MHz, DMSO-d$_6$) δ 9.66 (s, 1H), 9.63 (s, 1H), 8.36-8.42 (m, 2H), 7.98-8.09 (m, 1H), 7.93 (s, 1H), 7.73 (dd, J=8.7, 1.6 Hz, 1H), 7.38-7.54 (m, 4H), 7.09-7.19 (m, 2H), 6.07-6.16 (m, 1H), 3.64 (s, 3H), 2.20-2.26 (m, 1H), 1.94-2.01 (m, 1H), 1.64-1.70 (m, 1H), 1.31-1.37 (m, 3H), 0.98-1.26 (m, 5H), 0.78-0.85 (m, 6H).

Example 127: 5-(5-Chloro-2-(1H-tetrazol-1-yl)phenyl)-2-(2-(2-(4,4-difluoropiperidine-1-carbonyl)cyclopropyl)-1-(4-(4-((methoxycarbonyl)amino)phenyl)-1H-pyrazol-1-yl)ethyl)pyridine 1-oxide

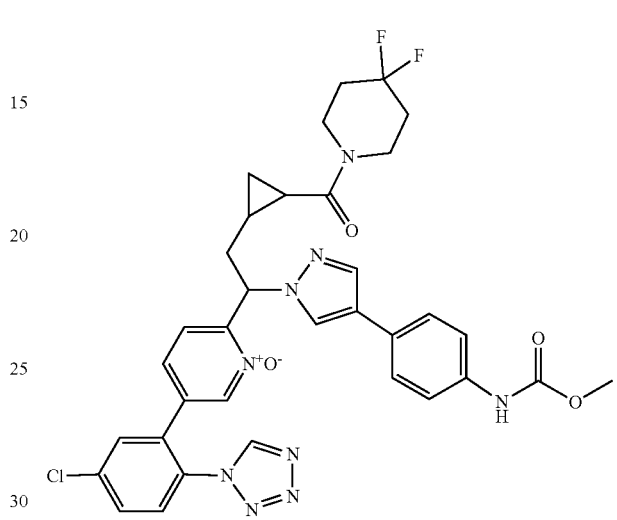

LC/MS: mass calculated for $C_{34}H_{32}ClF_2N_9O_4$: 703.2, measured (ES, m/z): 704 [M]+. $^1$H NMR (400 MHz, CD$_3$OD) δ ppm 0.70-0.88 (m, 1H), 0.90-1.03 (m, 1H), 1.35-1.56 (m, 2H), 1.56-1.94 (m, 4H), 2.18-2.46 (m, 2H), 3.43-3.63 (m, 4H), 3.68-3.78 (m, 4H), 6.13-6.26 (m, 1H), 7.12-7.21 (m, 1H), 7.37-7.54 (m, 4H), 7.67-7.74 (m, 1H), 7.74-7.82 (m, 2H), 7.89-7.99 (m, 1H), 8.14-8.21 (m, 1H), 8.22-8.33 (m, 1H), 9.18-9.29 (m, 1H), 9.29-9.44 (m, 1H).

Example 128: 5-(5-Chloro-2-(1H-tetrazol-1-yl)phenyl)-2-(2-cyclopropyl-1-(4-(1-methyl-6-oxo-1,6-dihydropyridazin-4-yl)-1H-pyrazol-1-yl)ethyl)pyridine 1-oxide

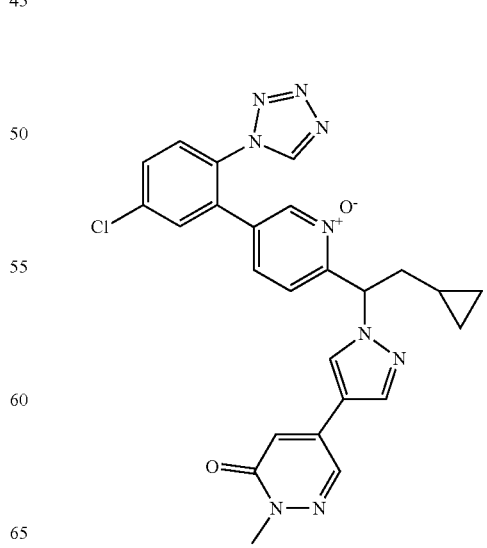

LC/MS: mass calculated for $C_{25}H_{22}ClN_9O_2$: 515.2, measured (ES, m/z): 516.2 [M+H]$^+$. $^1$H NMR (400 MHz, CD$_3$OD) δ 9.37 (s, 1H), 8.59 (s, 1H), 8.25 (s, 2H), 8.12 (s, 1H), 7.74-7.81 (m, 2H), 7.67-7.72 (m, 1H), 7.41-7.54 (m, 1H), 7.16 (br d, J=8.08 Hz, 1H), 7.08 (d, J=2.02 Hz, 1H), 6.23 (br dd, J=4.04, 9.60 Hz, 1H), 3.76 (s, 3H), 2.38-2.56 (m, 1H), 1.94-2.07 (m, 1H), 0.65 (br d, J=6.06 Hz, 1H), 0.33-0.52 (m, 2H), 0.15-0.25 (m, 1H), 0.02-0.08 (m, 1H).

Example 129: 5-(3-Chloro-2-fluoro-6-(1H-tetrazol-1-yl)phenyl)-2-(1-(4-(4-(cyclopropylcarbamoyl)phenyl)-1H-pyrazol-1-yl)-2-(4-fluorophenyl)ethyl)pyridine 1-oxide

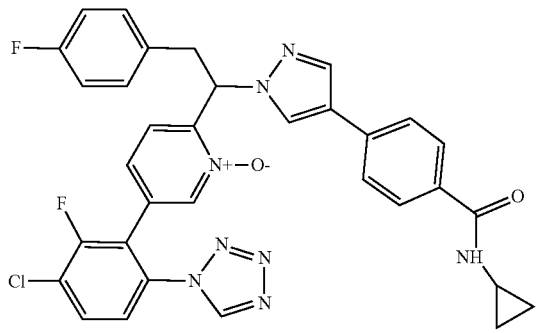 [SMILES: O=C(NC1CC1)c1ccc(-c2cnn(C(Cc3ccc(F)cc3)c3ccc(-c4c(-n5cnnn5)ccc(Cl)c4F)c[n+]3[O-])c2)cc1]

LC/MS: mass calculated for $C_{33}H_{25}ClF_2N_8O_2$: 638.17, measured (ES, m/z): 639.2 [M+H]$^+$. $^1$H NMR (300 MHz, Chloroform-d) δ 8.64 (s, 1H), 8.34 (s, 1H), 7.95 (s, 1H), 7.77 (t, J=8.7 Hz, 1H), 7.65-7.72 (m, 2H), 7.59-7.61 (m, 2H), 7.36-7.47 (m, 3H), 7.01-7.09 (m, 3H), 6.85-6.91 (m, 2H), 6.37 (s, 1H), 6.08-6.20 (m, 1H), 3.68 (t, J=13.6 Hz, 1H), 3.48 (dd, J=13.4, 3.2 Hz, 1H), 2.82-2.92 (m, 1H), 0.82-0.91 (m, 2H), 0.57-0.67 (m, 2H). $^{19}$F NMR (282 MHz, Chloroform-d) δ −75.83, −109.89, −115.33.

Example 130: 5-(3-Chloro-2-fluoro-6-(1H-tetrazol-1-yl)phenyl)-2-(2-(3,3-dimethylcyclobutyl)-1-(4-(4-((methoxycarbonyl)amino)phenyl)-1H-pyrazol-1-yl)ethyl)pyridine 1-oxide

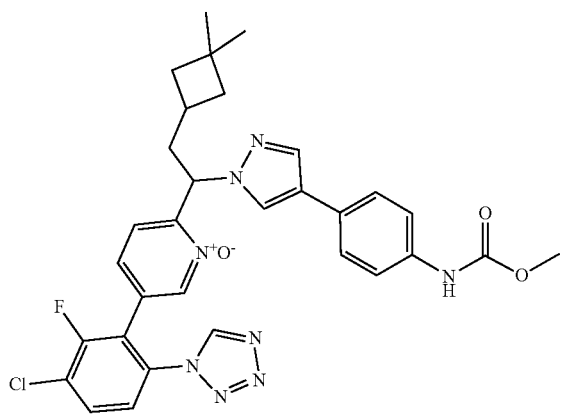

LC/MS: mass calculated for $C_{31}H_{30}ClFN_8O_3$: 616.2, measured (ES, m/z): 617.0 [M+H]$^+$. $^1$H NMR (300 MHz, DMSO-d$_6$) δ 9.67 (s, 1H), 9.63 (s, 1H), 8.39 (d, J=1.5 Hz, 1H), 8.33 (s, 1H), 8.04 (t, J=8.7 Hz, 1H), 7.92 (s, 1H), 7.73 (d, J=8.7 Hz, 1H), 7.50 (d, J=8.7 Hz, 2H), 7.40-7.42 (m, 2H), 7.21 (d, J=8.3 Hz, 1H), 7.12 (d, J=8.2 Hz, 1H), 5.88 (dd, J=9.9, 3.7 Hz, 1H), 3.65 (s, 3H), 2.35-2.45 (m, 1H), 2.01-2.20 (m, 2H), 1.71-1.79 (m, 1H), 1.51-1.58 (m, 1H), 1.46-1.50 (m, 1H), 1.27-1.40 (m, 1H), 0.95-1.12 (m, 6H). $^{19}$F NMR (376 MHz, DMSO-d$_6$) δ −112.79, −218.44.

Example 131: 5-(3-Chloro-2-fluoro-6-(1H-tetrazol-1-yl)phenyl)-2-(1-(4-(4-(methoxycarbonylamino)phenyl)-1H-pyrazol-1-yl)-2-((R*)tetrahydro-2H-pyran-2-yl)ethyl)pyridine 1-oxide

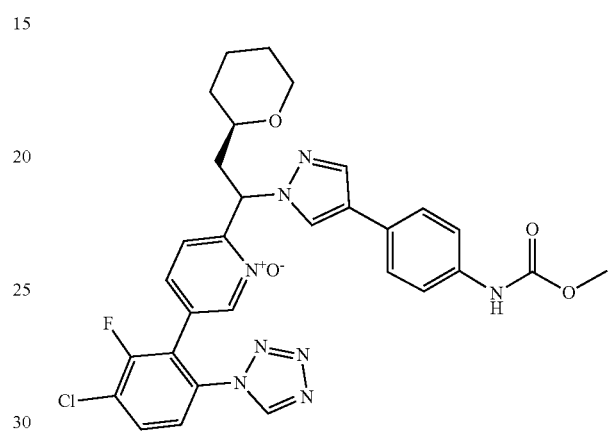

LC/MS: mass calculated for $C_{30}H_{28}ClFN_8O_4$: 618.19, measured (ES, m/z): 619.25 [M+H]$^+$. $^1$H NMR (400 MHz, CD$_3$OD) δ 9.39 (s, 1H), 8.37 (d, J=1.5 Hz, 1H), 8.16 (s, 1H), 7.86-7.98 (m, 2H), 7.62 (d, J=8.7 Hz, 1H), 7.44-7.53 (m, 5H), 7.29 (d, J=8.4 Hz, 1H), 6.45 (dd, J=11.1, 3.7 Hz, 1H), 3.97 (d, J=11.4 Hz, 1H), 3.23-3.29 (m, 1H), 2.92-3.03 (m, 1H), 2.47-2.56 (m, 1H), 2.31-2.41 (m, 1H), 1.72-1.82 (m, 1H), 1.43-1.63 (m, 4H), 1.29-1.40 (m, 1H).

Example 132: 2-(1-(4-(4-Carboxyphenyl)-1H-pyrazol-1-yl)-2-(isochroman-1-yl)ethyl)-5-(5-chloro-2-(1H-tetrazol-1-yl)phenyl)pyridine 1-oxide

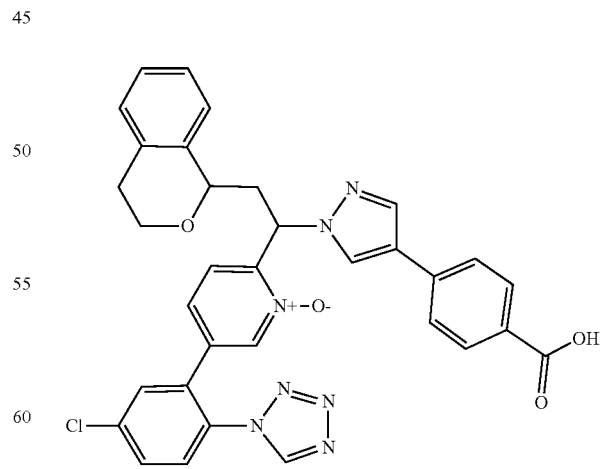

LC/MS: mass calculated for $C_{33}H_{28}ClN_7O_4$: 619.17, measured (ES, m/z): 620.25 [M+H]$^+$. $^1$H NMR (400 MHz, DMSO-d$_6$) δ 9.66 (s, 1H), 8.72 (s, 1H), 8.29 (d, J=1.7 Hz, 1H), 8.21 (s, 1H), 7.90-7.96 (m, 2H), 7.85-7.89 (m, 1H), 7.74-7.88 (m, 4H), 7.08-7.20 (m, 5H), 6.91-6.99 (m, 1H), 6.41 (dd, J=11.3, 3.2 Hz, 1H), 4.33-4.41 (m, 1H), 4.06-4.16 (m, 1H), 3.68-3.73 (m, 1H), 2.86-2.96 (m, 1H), 2.77-2.86 (m, 1H), 2.67-2.75 (m, 1H), 2.51-2.59 (m, 1H).

Example 133: 5-(3-Chloro-2-fluoro-6-(1H-tetrazol-1-yl)phenyl)-2-(1-(4-(4-((methoxycarbonyl)amino)phenyl)-1H-pyrazol-1-yl)-2-(4-methylcyclohexyl)ethyl)pyridine 1-oxide

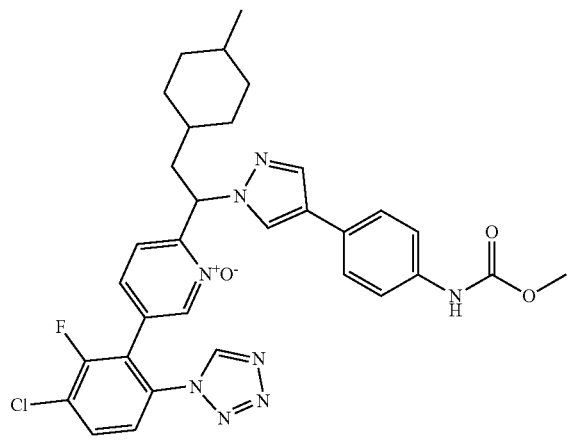

LC/MS: mass calculated for C₃₂H₃₂ClFN₈O₃: 630.23, measured (ES, m/z): 631.25 [M+H]⁺. ¹H NMR (300 MHz, DMSO-d₆) δ 9.67 (d, J=2.3 Hz, 1H), 9.63 (s, 1H), 8.36-8.45 (m, 2H), 7.98-8.10 (m, 1H), 7.94 (d, J=2.5 Hz, 1H), 7.68-7.78 (m, 1H), 7.46-1.55 (m, 2H), 7.42 (d, J=8.5 Hz, 2H), 7.07-7.18 (m, 2H), 6.00-6.16 (m, 1H), 3.65 (s, 3H), 2.08-2.31 (m, 2H), 1.82-1.96 (m, 1H), 1.42-1.63 (m, 3H), 1.25-1.41 (m, 4H), 0.94-1.04 (m, 1H), 0.82-0.91 (m, 1H), 0.70-0.82 (m, 3H). ¹⁹F NMR (282 MHz, DMSO-d₆) δ −74.76, −112.76.

Example 134: 5-(3-Chloro-2-fluoro-6-(1H-tetrazol-1-yl)phenyl)-2-(2-cyclopropyl-1-(4-(1-methyl-6-oxo-1,6-dihydropyridazin-4-yl)-1H-pyrazol-1-yl)ethyl)-4-methylpyridine 1-oxide

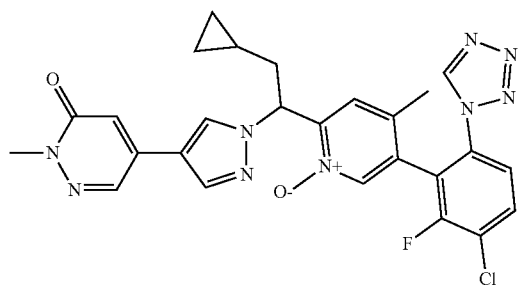 [SMILES: Cc1cc(C(CC2CC2)n2cc(-c3cnn(C)c(=O)c3)cn2)[n+]([O-])cc1-c1c(-n2cnnn2)ccc(Cl)c1F]

LC/MS: mass calculated for C₂₆H₂₃ClFN₉O₂: 547.16, measured (ES, m/z): 548.15 [M+H]⁺. ¹H NMR (400 MHz, DMSO-d₆) δ 9.71 (s, 1H), 8.80 (s, 1H), 8.29 (d, J=2.2 Hz, 1H), 8.27 (s, 1H), 8.25 (s, 1H), 8.05-8.14 (m, 1H), 7.79 (d, J=8.7 Hz, 1H), 7.36 (s, 1H), 7.15 (d, J=2.2 Hz, 1H), 6.02 (dd, J=10.0, 4.4 Hz, 1H), 3.64 (s, 3H), 2.31-2.37 (m, 1H), 1.98 (s, 3H), 1.89-1.95 (m, 1H), 0.50-0.56 (m, 1H), 0.29-0.39 (m, 2H), 0.09-0.14 (m, 1H), −0.06-0.00 (m, 1H). ¹⁹F NMR (376 MHz, DMSO-d₆) δ −74.96, −112.16.

Example 135: 5-(3-Chloro-2-fluoro-6-(1H-tetrazol-1-yl)phenyl)-2-(2-cyclopropyl-1-(4-(4-(2-methoxyacetamido)phenyl)-1H-pyrazol-1-yl)ethyl)pyridine 1-oxide

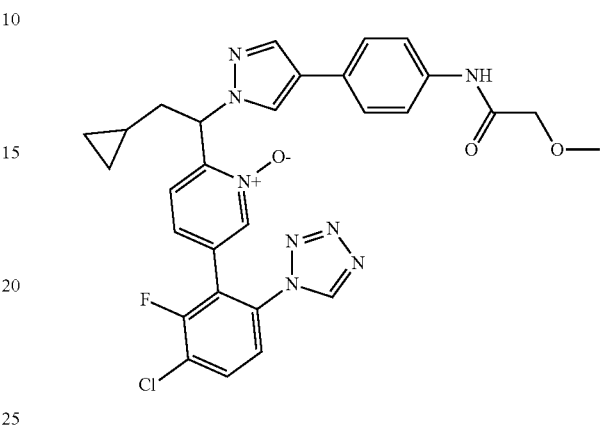

LC/MS: mass calculated for C₂₉H₂₆ClFN₈O₃: 588.18, measured (ES, m/z): 589.1 [M+H]⁺. ¹H NMR (300 MHz, DMSO-d₆) δ 9.77 (s, 1H), 9.69 (s, 1H), 8.45 (s, 1H), 8.42 (s, 1H), 8.03-8.09 (m, 1H), 7.99 (s, 1H), 7.76 (d, J=8.7 Hz, 1H), 7.66-7.69 (m, 2H), 7.54-7.57 (m, 2H), 7.20-7.23 (m, 1H), 7.13-7.16 (m, 1H), 6.03-6.08 (m, 1H), 4.00 (s, 2H), 3.38 (s, 3H), 2.35-2.43 (m, 1H), 1.81-1.91 (m, 1H), 0.60-0.66 (m, 1H), 0.30-0.41 (m, 2H), 0.09-0.14 (m, 1H), 0.00-0.06 (m, 1H). ¹⁹F NMR (282 MHz, DMSO-d₆) δ −74.90, −112.79.

Example 136: 5-(3-Chloro-2-fluoro-6-(1H-tetrazol-1-yl)phenyl)-2-(2-cyclopropyl-1-(4-(1-methyl-6-oxo-1,6-dihydropyridazin-4-yl)-1H-pyrazol-1-yl)ethyl)pyridine 1-oxide

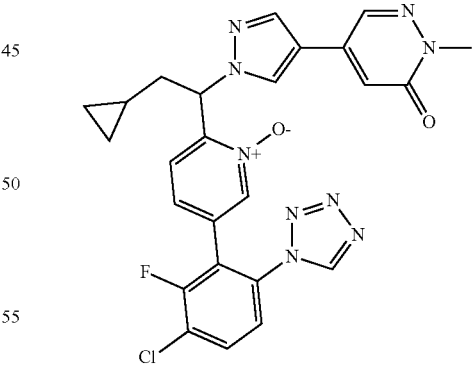

LC/MS: mass calculated for C₂₅H₂₁ClFN₉O₂: 533.14, measured (ES, m/z): 534.1 [M+H]⁺. ¹H NMR (300 MHz, DMSO-d₆) δ 9.70 (s, 1H), 8.84 (s, 1H), 8.43 (s, 1H), 8.29 (d, J=2.2 Hz, 1H), 8.26 (s, 1H), 8.07 (d, J=8.7 Hz, 1H), 7.76 (d, J=8.7 Hz, 1H), 7.33 (d, J=8.3 Hz, 1H), 7.15-7.18 (m, 2H), 6.08 (dd, J=9.8, 4.4 Hz, 1H), 3.64 (s, 3H), 2.30-2.40 (m, 1H), 1.84-1.95 (m, 1H), 0.53-0.61 (m, 1H), 0.28-0.41 (m, 2H), 0.08-0.16 (m, 1H), −0.06-0.00 (m, 1H). ¹⁹F NMR (282 MHz, DMSO-d₆) δ −74.52, −112.76.

Example 137: 5-(3-Chloro-2-fluoro-6-(1H-tetrazol-1-yl)phenyl)-2-(2-cyclopropyl-1-(4-(1-methyl-6-oxo-1,6-dihydropyridazin-4-yl)-1H-pyrazol-1-yl)ethyl)-4-methylpyridine 1-oxide

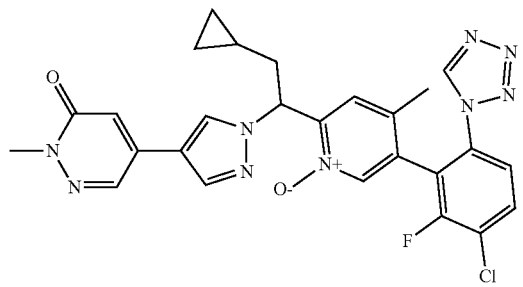 [SMILES: Cc1cc(C(CC2CC2)n2cc(-c3cnn(C)c(=O)c3)cn2)[n+]([O-])cc1-c1c(-n2cnnn2)ccc(Cl)c1F]

LC/MS: mass calculated for $C_{26}H_{23}ClFN_9O_2$: 547.16, measured (ES, m/z): 548.10 [M+H]$^+$. $^1$H NMR (400 MHz, DMSO-d$_6$) δ 9.74 (s, 1H), 8.80 (s, 1H), 8.29 (d, J=2.2 Hz, 1H), 8.27 (s, 1H), 8.23 (s, 1H), 8.07-8.12 (m, 1H), 7.81 (d, J=8.7 Hz, 1H), 7.36 (s, 1H), 7.15 (d, J=2.2 Hz, 1H), 6.10 (dd, J=9.6, 4.8 Hz, 1H), 3.63 (s, 3H), 2.32-2.39 (m, 1H), 1.99 (s, 3H), 1.83-1.89 (m, 1H), 0.50-0.57 (m, 1H), 0.26-0.37 (m, 2H), 0.06-0.11 (m, 1H), −0.07-0.00 (m, 1H). $^{19}$F NMR (376 MHz, DMSO-d$_6$) δ −74.98, −112.19.

Example 138: 5-(3-Chloro-2-fluoro-6-(1H-tetrazol-1-yl)phenyl)-2-(2-(4-methoxyphenyl)-1-(4-(1-methyl-2-oxo-1,2-dihydropyridin-4-yl)-1H-pyrazol-1-yl)ethyl)pyridine 1-oxide

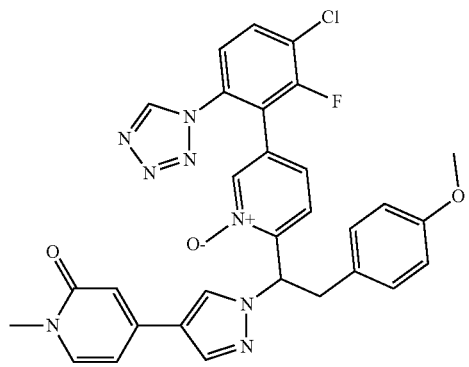 [SMILES: COc1ccc(CC(c2ccc(-c3c(-n4cnnn4)ccc(Cl)c3F)c[n+]2[O-])n2cc(-c3ccn(C)c(=O)c3)cn2)cc1]

LC/MS: mass calculated for $C_{30}H_{24}ClFN_8O_3$: 598.16, measured (ES, m/z): 599.20 [M+H]$^+$. $^1$H NMR (400 MHz, DMSO-d$_6$) δ 9.70 (s, 1H), 8.50 (s, 1H), 8.48 (s, 1H), 8.12 (s, 1H), 8.05-8.09 (m, 1H), 7.77 (d, J=8.8 Hz, 1H), 7.66 (d, J=7.0 Hz, 1H), 7.32 (d, J=8.3 Hz, 1H), 7.11-7.22 (m, 1H), 7.03-7.10 (m, 2H), 6.75-6.86 (m, 2H), 6.60 (s, 1H), 6.45 (d, J=7.1 Hz, 1H), 6.14 (dd, J=9.6, 4.8 Hz, 1H), 3.68 (s, 3H), 3.39-3.55 (m, 2H), 3.39 (s, 3H).

Example 139: 5-(3-Chloro-2-fluoro-6-(1H-tetrazol-1-yl)phenyl)-2-(1-(4-(4-(cyclopropylcarbamoyl)phenyl)-1H-pyrazol-1-yl)-2-(4-methoxyphenyl)ethyl)pyridine 1-oxide

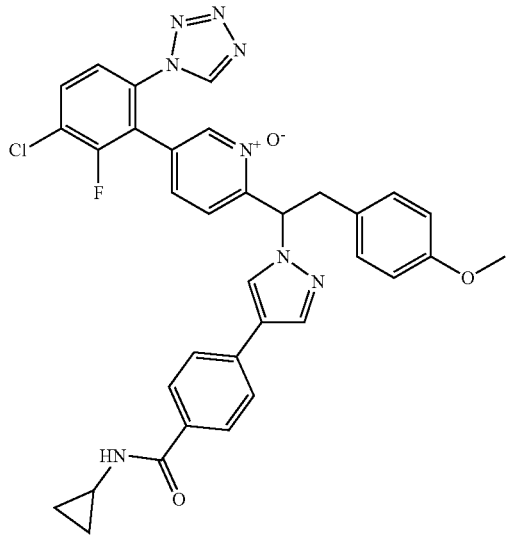

LC/MS: mass calculated for $C_{34}H_{28}ClFN_8O_3$: 650.19, measured (ES, m/z): 651.25 [M+H]$^+$. $^1$H NMR (400 MHz, DMSO-d$_6$) δ 9.70 (s, 1H), 8.43-8.59 (m, 2H), 8.40 (d, J=4.2 Hz, 1H), 7.93-8.23 (m, 2H), 7.69-7.86 (m, 3H), 7.56-7.70 (m, 2H), 7.31 (d, J=8.3 Hz, 1H), 7.19 (d, J=8.3 Hz, 1H), 7.04-7.13 (m, 2H), 6.70-6.90 (m, 2H), 6.16 (dd, J=9.9, 4.5 Hz, 1H), 3.68 (s, 3H), 3.35-3.57 (m, 2H), 2.79-2.88 (m, 1H), 0.66-0.74 (m, 2H), 0.47-0.62 (m, 2H).

Example 140: 5-(3-Chloro-2-fluoro-6-(oxazol-5-yl)phenyl)-2-(1-(4-(4-(cyclopropylcarbamoyl)phenyl)-1H-pyrazol-1-yl)-2-(4-fluorophenyl)ethyl)pyridine 1-oxide

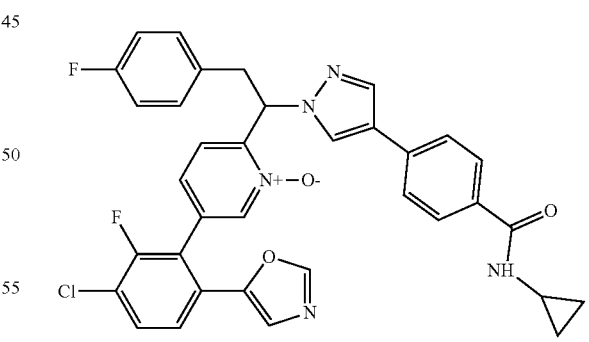

LC/MS: mass calculated for $C_{35}H_{26}ClF_2N_5O_3$: 637.16, measured (ES, m/z): 638 [M+H]$^+$. $^1$H NMR (300 MHz, DMSO-d$_6$) δ 8.52 (d, J=1.6 Hz, 1H), 8.49 (s, 1H), 8.33-8.42 (m, 2H), 8.13 (s, 1H), 7.77-7.85 (m, 3H), 7.61-7.68 (m, 3H), 7.46 (d, J=8.3 Hz, 1H), 7.37 (d, J=8.3 Hz, 1H), 7.21-7.27 (m, 2H), 7.04-7.11 (m, 2H), 6.66 (s, 1H), 6.26-6.32 (m, 1H), 3.62-3.67 (m, 2H), 2.76-2.84 (m, 1H), 0.64-0.70 (m, 2H), 0.53-0.57 (m, 2H). $^{19}$F NMR (282 MHz, DMSO-d$_6$) δ −74.83, −114.99, −116.08.

Example 141: 5-(3-Chloro-2-fluoro-6-(1H-tetrazol-1-yl)phenyl)-2-(2-cyclopropyl-1-(4-(1-methyl-6-oxo-1,6-dihydropyridazin-4-yl)-1H-pyrazol-1-yl)ethyl)-4-ethoxypyridine 1-oxide

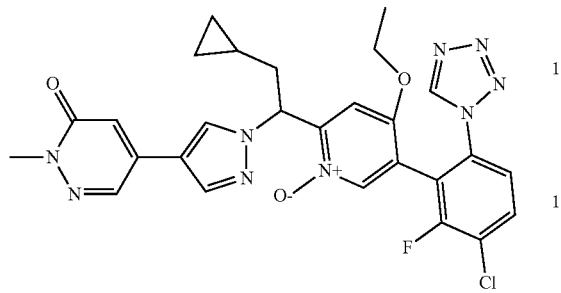

LC/MS: mass calculated for $C_{27}H_{25}ClFN_9O_3$: 577.17, measured (ES, m/z): 578.2 [M+H]$^+$. $^1$H NMR (300 MHz, CD$_3$OD) δ 9.45 (s, 1H), 8.61 (s, 1H), 8.43 (s, 1H), 8.27 (d, J=4.8 Hz, 1H), 8.18 (d, J=7.9 Hz, 1H), 7.92 (t, J=7.6 Hz, 1H), 7.63-7.68 (m, 1H), 7.06-7.24 (m, 2H), 6.21-6.38 (m, 1H), 3.83-4.12 (m, 2H), 3.77 (d, J=3.6 Hz, 3H), 2.43-2.59 (m, 1H), 1.98-2.12 (m, 1H), 1.11-1.21 (m, 3H), 0.65-0.71 (m, 1H), 0.34-0.50 (m, 2H), 0.13-0.25 (m, 1H), 0.02-0.10 (m, 1H). 19F NMR (282 MHz, CD$_3$OD) δ −77.66-112.69.

Example 142: 2-(2-(4-(2-Amino-2-oxoethoxy)phenyl)-1-(4-(4-Carboxyphenyl)-1H-pyrazol-1-yl)ethyl)-5-(5-chloro-2-(1H-tetrazol-1-yl)phenyl)pyridine 1-oxide

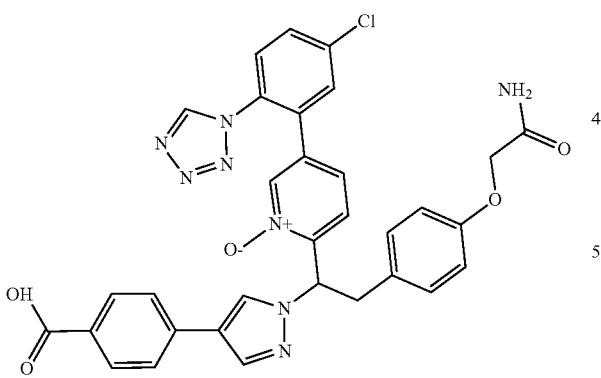

LC/MS: mass calculated for $C_{32}H_{25}ClN_8O_5$: 636.16, measured (ES, m/z): 637.15[M+H]$^+$. $^1$H NMR (400 MHz, DMSO-d$_6$) δ 9.69 (s, 1H), 8.52 (s, 1H), 8.36 (s, 1H), 8.13 (s, 1H), 7.89-7.92 (m, 3H), 7.82-7.87 (m, 2H), 7.72-7.65 (m, 2H), 7.47 (s, 1H), 7.35 (s, 1H), 7.24 (d, J=8.4 Hz, 1H), 7.09-7.16 (m, 2H), 6.98 (d, J=8.2 Hz, 1H), 6.79-6.86 (m, 2H), 6.19 (dd, J=9.9, 4.4 Hz, 1H), 4.34 (s, 2H), 3.43-3.50 (m, 2H).

Example 143: 4-Chloro-5-(3-Chloro-2-fluoro-6-(1H-tetrazol-1-yl)phenyl)-2-(2-cyclopropyl-1-(4-(1-methyl-6-oxo-1,6-dihydropyridazin-4-yl)-1H-pyrazol-1-yl)ethyl)pyridine 1-oxide

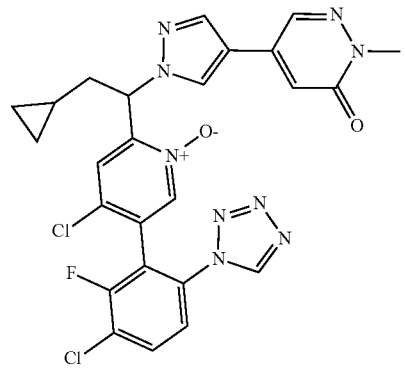 [SMILES: Cn1ncc(-c2cnn(C(CC3CC3)c3cc(Cl)c(-c4c(-n5cnnn5)ccc(Cl)c4F)c[n+]3[O-])c2)cc1=O]

LC/MS: mass calculated for $C_{25}H_{20}Cl_2FN_9O_2$: 567.11, measured (ES, m/z): 567.95 [M+H]$^+$. $^1$H NMR (400 MHz, DMSO-d$_6$) δ 9.83 (s, 1H), 8.82 (s, 1H), 8.61 (s, 1H), 8.29 (d, J=2.2 Hz, 1H), 8.27 (s, 1H), 8.14-8.18 (m, 1H), 7.84 (d, J=8.8 Hz, 1H), 7.67 (s, 1H), 7.16 (d, J=2.2 Hz, 1H), 6.01 (dd, J=9.9, 4.6 Hz, 1H), 3.64 (s, 3H), 2.31-2.40 (m, 1H), 1.90-1.98 (m, 1H), 0.49-0.57 (m, 1H), 0.29-0.41 (m, 2H), 0.09-0.14 (m, 1H), −0.07-0.00 (m, 1H), $^{19}$F NMR (376 MHz, DMSO-d$_6$) δ −111.42.

Example 144: 5-(3-Chloro-2-fluoro-6-(1H-tetrazol-1-yl)phenyl)-2-(2-cyclopropyl-1-(4-(1-methyl-2-oxo-1,2-dihydropyridin-4-yl)-1H-pyrazol-1-yl)ethyl)-4-(hydroxymethyl)pyridine 1-oxide

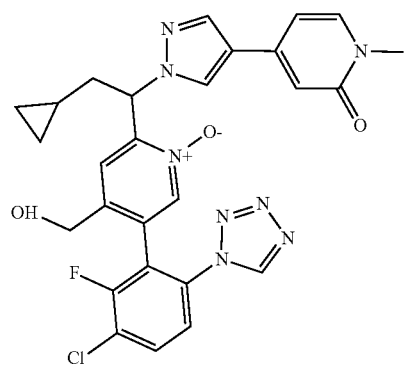 [SMILES: Cn1ccc(-c2cnn(C(CC3CC3)c3cc(CO)c(-c4c(-n5cnnn5)ccc(Cl)c4F)c[n+]3[O-])c2)cc1=O]

LC/MS: mass calculated for $C_{27}H_{24}ClFN_8O_3$: 562.16, measured (ES, m/z): 563.05 [M+H]$^+$. $^1$H NMR (400 MHz, DMSO-d$_6$) δ 9.67 (s, 1H), 8.68 (s, 1H), 8.28 (s, 1H), 8.16 (s, 1H), 8.08 (t, J=8.7 Hz, 1H), 7.77 (d, J=8.8 Hz, 1H), 7.68 (d, J=7.1 Hz, 1H), 7.42 (s, 1H), 6.67 (d, J=2.0 Hz, 1H), 6.53 (d, J=7.0 Hz, 1H), 6.05 (dd, J=10.0, 4.0 Hz, 1H), 5.48 (t, J=5.6 Hz, 1H), 4.04-4.18 (m, 2H), 3.40 (s, 3H), 2.30-2.38 (m, 1H), 1.88-1.94 (m, 1H), 0.53-0.62 (m, 1H), 0.29-0.39 (m, 2H), 0.11-0.15 (m, 1H), −0.04-0.00 (m, 1H). $^{19}$F NMR (376 MHz, DMSO-d$_6$) δ −111.62.

Example 145: 5-(3-Chloro-2-fluoro-6-(1H-tetrazol-1-yl)phenyl)-2-(2-cyclopropyl-1-(4-(4-(((2-methoxyethoxy)carbonyl)amino)phenyl)-1H-pyrazol-1-yl)ethyl)pyridine 1-oxide

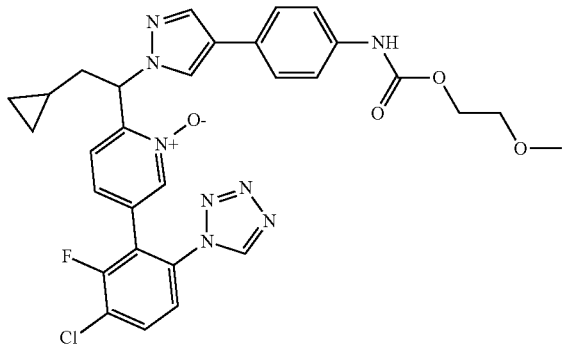 [SMILES: COCCOC(=O)Nc1ccc(-c2cnn(C(CC3CC3)c3ccc(-c4c(-n5cnnn5)ccc(Cl)c4F)c[n+]3[O-])c2)cc1]

LC/MS: mass calculated for $C_{30}H_{28}ClFN_8O_4$: 618.19, measured (ES, m/z): 619.0 [M+H]$^+$. $^1$H NMR (400 MHz, DMSO-d$_6$) δ 9.75 (s, 1H), 9.68 (s, 1H), 8.41 (s, 2H), 8.06 (t, J=7.8 Hz, 1H), 7.96 (s, 1H), 7.76 (dd, J=8.7 Hz, 1H), 7.53 (d, J=8.7 Hz, 2H), 7.46 (d, J=8.5 Hz, 2H), 7.25-7.11 (m, 2H), 6.06 (dd, J=9.7, 4.2 Hz, 1H), 4.25-4.17 (m, 2H), 3.61-3.54 (m, 2H), 3.30 (s, 3H), 2.32-2.41 (m, 1H), 1.79-1.90 (m, 1H), 0.58-0.65 (m, 1H), 0.25-0.41 (m, 2H), 0.01-0.15 (m, 2 h). $^{19}$F NMR (376 MHz, DMSO-d$_6$) δ −73.2, −75.36, −74.66, −112.78.

Example 146: 5-(3-Chloro-2-fluoro-6-(1H-tetrazol-1-yl)phenyl)-2-(1-(4-(4-(cyclopropylcarbamoyl)phenyl)-1H-pyrazol-1-yl)-2-((R*)-tetrahydro-2H-pyran-2-yl)ethyl)pyridine 1-oxide

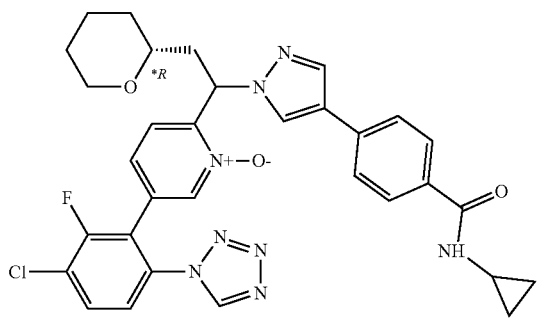 [SMILES: O=C(NC1CC1)c1ccc(-c2cnn(C(C[C@H]3CCCCO3)c3ccc(-c4c(-n5cnnn5)ccc(Cl)c4F)c[n+]3[O-])c2)cc1]

LC/MS: mass calculated for $C_{32}H_{30}ClFN_8O_3$: 628.21, measured (ES, m/z): 629.25 [M+H]$^+$. $^1$H NMR (400 MHz, Chloroform-d) δ 8.67 (s, 1H), 8.41 (s, 1H), 8.01 (s, 1H), 7.93 (s, 1H), 7.74-7.81 (m, 3H), 7.66 (d, J=8.3 Hz, 1H), 7.55-7.58 (m, 2H), 7.43 (d, J=8.6 Hz, 1H), 7.09 (d, J=8.4 Hz, 1H), 6.50 (d, J=10.6 Hz, 1H), 6.36 (s, 1H), 3.99 (d, J=11.3 Hz, 1H), 3.18-3.27 (m, 2H), 2.92-2.97 (m, 1H), 2.51-2.58 (m, 1H), 2.28-2.34 (m, 1H), 1.78-1.82 (m, 1H), 1.53-1.59 (m, 2H), 1.26-1.47 (m, 3H), 0.89-0.92 (m, 2H), 0.65-0.68 (m, 2 h).

Example 147: 5-(3-Chloro-2-fluoro-6-(1H-tetrazol-1-yl)phenyl)-2-(1-(4-(4-(cyclopropylcarbamoyl)phenyl)-1H-pyrazol-1-yl)-2-((S*)-tetrahydro-2H-pyran-2-yl)ethyl)pyridine 1-oxide

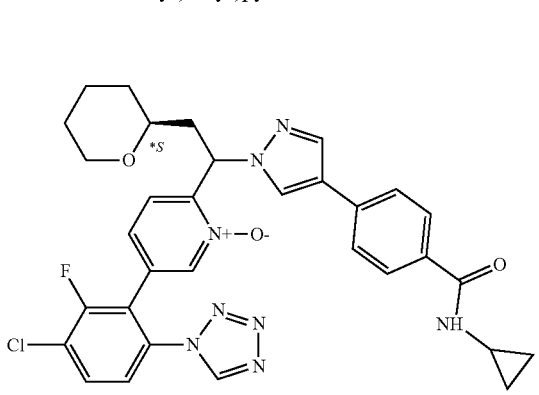

LC/MS: mass calculated for $C_{32}H_{30}ClFN_8O_3$: 628.21, measured (ES, m/z): 629.25 [M+H]$^+$. $^1$H NMR (400 MHz, Chloroform-d) δ 8.61 (s, 1H), 8.28 (s, 1H), 8.00 (s, 1H), 7.90 (s, 1H), 7.72-7.80 (m, 3H), 7.52-7.57 (m, 2H), 7.48 (d, J=8.4 Hz, 1H), 7.42 (d, J=8.6 Hz, 1H), 6.98 (d, J=8.4 Hz, 1H), 6.29-6.36 (m, 2H), 3.87 (d, J=11.3 Hz, 1H), 3.24-3.29 (m, 2H), 2.89-2.96 (m, 1H), 2.56-2.62 (m, 1H), 2.47-2.52 (m, 1H), 1.81-1.86 (m, 1H), 1.64-1.71 (m, 1H), 1.46-1.56 (m, 3H), 1.28-1.38 (m, 1H), 0.88-0.92 (m, 2H), 0.64-0.68 (m, 2 h).

Example 148: 5-(3-Chloro-2-fluoro-6-(1H-tetrazol-1-yl)phenyl)-2-(2-cyclopropyl-1-(4-(1-methyl-2-oxo-1,2-dihydropyridin-4-yl)-1H-pyrazol-1-yl)ethyl)-4-(hydroxymethyl)pyridine 1-oxide

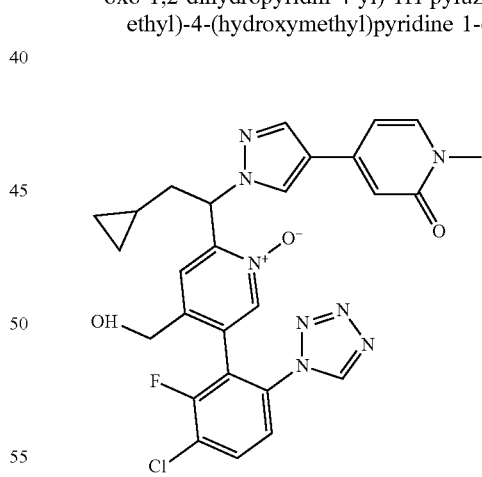

LC/MS: mass calculated for $C_{27}H_{24}ClFN_8O_3$: 562.16, measured (ES, m/z): 563.05 [M+H]$^+$. $^1$H NMR (400 MHz, DMSO-d$_6$) δ 9.68 (s, 1H), 8.66 (s, 1H), 8.29 (s, 1H), 8.13 (s, 1H), 8.07 (t, J=8.7 Hz, 1H), 7.77 (d, J=8.7 Hz, 1H), 7.67 (d, J=7.1 Hz, 1H), 7.40 (s, 1H), 6.66 (d, J=2.0 Hz, 1H), 6.53 (d, J=7.1 Hz, 1H), 6.12 (dd, J=9.7, 4.5 Hz, 1H), 5.49 (t, J=5.6 Hz, 1H), 4.04-4.19 (m, 2H), 3.39 (s, 3H), 2.31-2.39 (m, 1H), 1.81-1.87 (m, 1H), 0.54-0.61 (m, 1H), 0.26-0.36 (m, 2H), 0.05-0.10 (m, 1H), −0.07-0.00 (m, 1H). $^{19}$F NMR (376 MHz, DMSO-d$_6$) δ −73.43, −111.57.

Example 149: 4-Chloro-5-(3-chloro-2-fluoro-6-(1H-tetrazol-1-yl)phenyl)-2-(2-cyclopropyl-1-(4-(1-methyl-6-oxo-1,6-dihydropyridazin-4-yl)-1H-pyrazol-1-yl)ethyl)pyridine 1-oxide

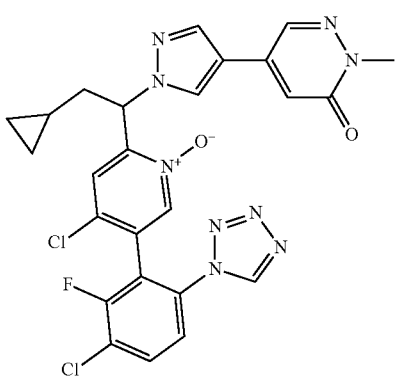 [SMILES: Cn1ncc(-c2cnn(C(CC3CC3)c3cc(Cl)c(-c4c(-n5cnnn5)ccc(Cl)c4F)c[n+]3[O-])c2)cc1=O]

LC/MS: mass calculated for $C_{25}H_{20}Cl_2FN_9O_2$: 567.11, measured (ES, m/z): 567.95 [M+H]$^+$. $^1$H NMR (400 MHz, DMSO-d$_6$) δ 9.85 (s, 1H), 8.81 (s, 1H), 8.61 (s, 1H), 8.28 (d, J=2.2 Hz, 1H), 8.25 (s, 1H), 8.16 (t, J=8.3 Hz, 1H), 7.85 (d, J=8.8 Hz, 1H), 7.65 (s, 1H), 7.15 (d, J=2.2 Hz, 1H), 6.08 (dd, J=9.7, 4.9 Hz, 1H), 3.63 (s, 3H), 2.33-2.41 (m, 1H), 1.87-1.93 (m, 1H), 0.51-0.57 (m, 1H), 0.27-0.39 (m, 2H), 0.07-0.12 (m, 1H), −0.07-0.00 (m, 1H). $^{19}$F NMR (376 MHz, DMSO-d$_6$) δ −73.42, 111.46.

Example 150: 5-(3-Chloro-2-fluoro-6-(1H-tetrazol-1-yl)phenyl)-2-(2-cyclopropyl-1-(4-(1-methyl-6-oxo-1,6-dihydropyridazin-4-yl)-1H-pyrazol-1-yl)ethyl)-4-isopropoxypyridine 1-oxide

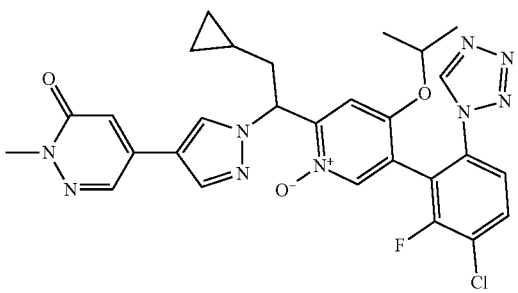 [SMILES: CC(C)Oc1cc(C(CC2CC2)n2cc(-c3cnn(C)c(=O)c3)cn2)[n+]([O-])cc1-c1c(-n2cnnn2)ccc(Cl)c1F]

LC/MS: mass calculated for $C_{28}H_{27}ClFN_9O_3$: 591.19, measured (ES, m/z): 592.1 [M+H]$^+$. $^1$H NMR (300 MHz, CD$_3$OD) δ 9.44 (s, 1H), 8.62 (s, 1H), 8.44 (s, 1H), 8.25-8.28 (m, 1H), 8.18 (s, 1H), 7.83-7.98 (m, 1H), 7.60-7.65 (m, 1H), 7.19 (s, 1H), 7.10-7.12 (m, 1H), 6.24-6.31 (m, 1H), 4.52-4.60 (m, 1H), 3.77 (s, 3H), 1.20 (d, J=6.0 Hz, 3H), 0.94 (d, J=6.0 Hz, 3H), 0.62-0.71 (m, 1H), 0.39-0.47 (m, 2H), 0.17-0.24 (m, 1H), 0.03-0.11 (m, 1H). $^{19}$F NMR (282 MHz, CD$_3$OD) δ −77.65, −112.59.

Example 151: 2-(1-(4-(4-Carboxyphenyl)-1H-pyrazol-1-yl)-2-(4-phenoxyphenyl)ethyl)-5-(5-chloro-2-(1H-tetrazol-1-yl)phenyl)pyridine 1-oxide

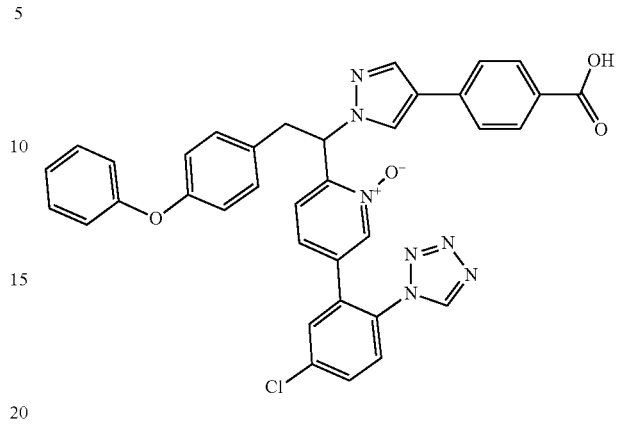

LC/MS: mass calculated for $C_{36}H_{26}ClN_7O_4$: 655.17, measured (ES, m/z): 656.20[M+H]$^+$. $^1$H NMR (400 MHz, DMSO-d$_6$) δ 9.70 (s, 1H), 8.49 (s, 1H), 8.37 (s, 1H), 8.13 (s, 1H), 7.87-7.96 (m, 3H), 7.80-7.90 (m, 2H), 7.66-7.70 (m, 2H), 7.27-7.37 (m, 3H), 7.16-7.23 (m, 2H), 7.05-7.13 (m, 1H), 7.00 (d, J=8.3 Hz, 1H), 6.85-6.96 (m, 4H), 6.22 (dd, J=10.0, 4.5 Hz, 1H), 3.46-3.60 (m, 2H).

Example 152: 5-(3-Chloro-2-fluoro-6-(oxazol-5-yl)phenyl)-2-(1-(4-(6-(cyclopropanecarboxamido)-2-fluoropyridin-3-yl)-1H-pyrazol-1-yl)-2-(4-fluorophenyl)ethyl)pyridine 1-oxide

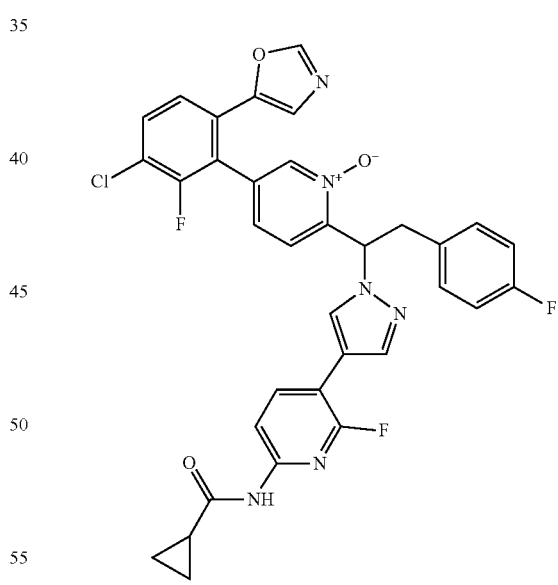

LC/MS: mass calculated for $C_{34}H_{24}ClF_3N_6O_3$: 656.15, measured (ES, m/z): 657 [M+H]$^+$. $^1$H NMR (300 MHz, DMSO-d$_6$) δ 10.97 (s, 1H), 8.52 (d, J=1.6 Hz, 1H), 8.39 (s, 1H), 8.34 (d, J=2.0 Hz, 1H), 8.19 (t, J=8.3 Hz, 1H), 8.06 (d, J=1.5 Hz, 1H), 7.97 (d, J=8.3 Hz, 1H), 7.83 (t, J=7.5 Hz, 1H), 7.66 (d, J=8.6 Hz, 1H), 7.47 (d, J=8.3 Hz, 1H), 7.36 (d, J=8.2 Hz, 1H), 7.25 (t, J=5.6 Hz, 2H), 7.07 (t, J=8.9 Hz, 2H), 6.65 (s, 1H), 6.34 (t, J=7.3 Hz, 1H), 3.61-3.75 (m, 2H), 1.91-2.91 (m, 1H), 0.72-0.85 (m, 4H). $^{19}$F NMR (376 MHz, DMSO-d$_6$) δ −70.47, −74.78, −114.99, −116.09.

Example 153: 5-(3-Chloro-2-fluoro-6-(1H-tetrazol-1-yl)phenyl)-2-(2-cyclopropyl-1-(4-(1-methyl-6-oxo-1,6-dihydropyridazin-4-yl)-1H-pyrazol-1-yl)ethyl)-4-isopropoxypyridine 1-oxide

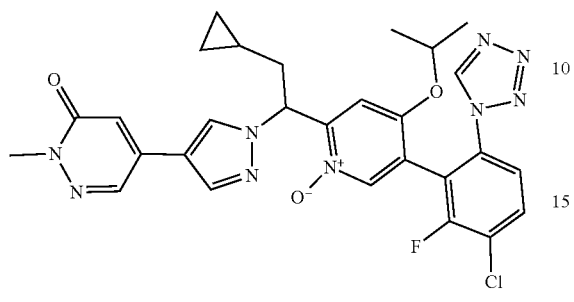

LC/MS: mass calculated for $C_{28}H_{27}ClFN_9O_3$: 591.19, measured (ES, m/z): 592.1 [M+H]+. $^1$H NMR (300 MHz, CD$_3$OD) δ 9.47 (s, 1H), 8.62 (s, 1H), 8.44 (s, 1H), 8.27 (d, J=4.3 Hz, 1H), 8.18 (d, J=6.8 Hz, 1H), 7.91 (t, J=7.6 Hz, 1H), 7.66-7.61 (m, 1H), 7.18 (d, J=8.3 Hz, 1H), 7.11 (d, J=5.4 Hz, 1H), 6.33 (dd, J=9.9, 4.8 Hz, 1H), 4.48-4.62 (m, 1H), 3.71-3.79 (m, 3H), 2.45-2.58 (m, 1H), 1.99-2.14 (m, 1H), 1.11-1.22 (m, 3H), 0.89-1.05 (m, 3H), 0.62-0.72 (m, 1H), 0.41-0.49 (m, 2H), 0.13-0.26 (m, 1H), 0.02-0.12 (m, 1H). $^{19}$F NMR (282 MHz, CD$_3$OD) δ −77.66, −112.59.

Example 154: 5-(5-Chloro-2-(1H-tetrazol-1-yl)phenyl)-2-(2-(4-chlorophenyl)-1-(4-(4-(trifluoromethoxy)phenyl)-1H-pyrazol-1-yl)ethyl)pyridine 1-oxide

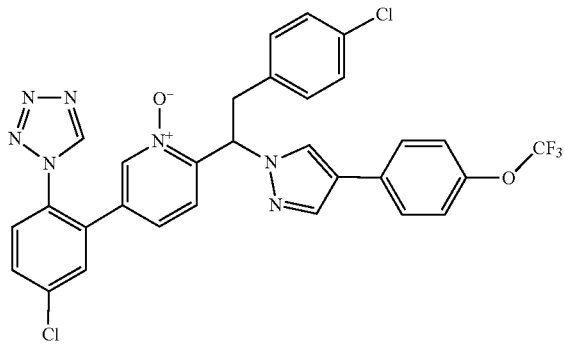 [SMILES: [O-][n+]1cc(-c2cc(Cl)ccc2-n2cnnn2)ccc1C(Cc1ccc(Cl)cc1)n1cc(-c2ccc(OC(F)(F)F)cc2)cn1]

LC/MS: mass calculated for $C_{30}H_{20}Cl_2F_3N_7O_2$: 637.1, measured (ES, m/z): 639.2 [M+H+2]+. $^1$H NMR (400 MHz, CD$_3$OD) δ ppm 3.52-3.72 (m, 3H), 6.17-6.34 (m, 2H), 7.15-7.25 (m, 4H), 7.49 (d, J=8.3 Hz, 1H), 7.54-7.61 (m, 2H), 7.67-7.76 (m, 2H), 7.76-7.82 (m, 1H), 7.97 (s, 1H), 8.04 (s, 1H), 8.22-8.38 (m, 2H), 9.38 (s, 1H).

Example 155: 5-(5-Chloro-2-(1H-tetrazol-1-yl)phenyl)-2-(2-(4-chlorophenyl)-1-(4-(1-oxidopyridin-3-yl)-1H-pyrazol-1-yl)ethyl)pyridine 1-oxide

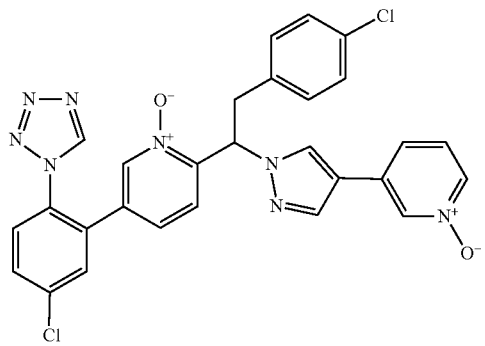 [SMILES: [O-][n+]1cccc(-c2cnn(C(Cc3ccc(Cl)cc3)c3ccc(-c4cc(Cl)ccc4-n4cnnn4)c[n+]3[O-])c2)c1]

LC/MS: mass calculated for $C_{28}H_{20}Cl_2N_8O_2$: 570.1, measured (ES, m/z): 571.2 [M]+. $^1$H NMR (400 MHz, CD$_3$OD) δ ppm 3.42-3.53 (m, 1H), 3.53-3.71 (m, 1H), 6.29 (dd, J=10.3, 4.4 Hz, 1H), 7.09-7.29 (m, 2H), 7.49-7.61 (m, 2H), 7.68-7.76 (m, 1H), 7.76-7.82 (m, 2H), 8.03-8.18 (m, 4H), 8.18-8.27 (m, 2H), 8.31 (d, J=1.5 Hz, 2H), 8.58 (bs, 1H), 9.38 (s, 1H).

Example 156: 5-(5-Chloro-2-(1H-tetrazol-1-yl)phenyl)-2-(1-(4-(5-chloro-2-(1H-tetrazol-1-yl)phenyl)-1H-pyrazol-1-yl)-2-(4-chlorophenyl)ethyl)pyridine 1-oxide

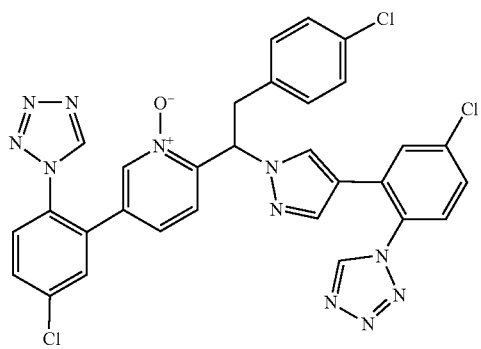 [SMILES: [O-][n+]1cc(-c2cc(Cl)ccc2-n2cnnn2)ccc1C(Cc1ccc(Cl)cc1)n1cc(-c2cc(Cl)ccc2-n2cnnn2)cn1]

LC/MS: mass calculated for $C_{30}H_{20}Cl_3N_{11}O$: 655.1, measured (ES, m/z): 656.3 [M]+. $^1$H NMR (400 MHz, CD$_3$OD) δ ppm 3.43-3.62 (m, 2H), 7.00-7.11 (m, 3H), 7.16-7.22 (m, 2H), 7.25 (d, J=8.3 Hz, 2H), 7.37-7.47 (m, 2H), 7.47-7.57 (m, 2H), 7.66 (d, J=2.0 Hz, 2H), 7.69-7.74 (m, 1H), 7.75-7.85 (m, 1H), 8.28 (s, 1H), 9.16 (s, 1H), 9.39 (s, 1H).

Example 157: 5-(3-Chloro-2-fluoro-6-(1H-tetrazol-1-yl)phenyl)-2-(1-(4-(4-(methoxycarbonylamino)phenyl)-1H-pyrazol-1-yl)propyl)pyridine 1-oxide

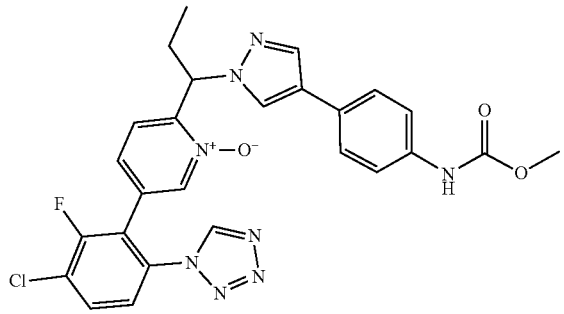 [SMILES: CCC(c1ccc(-c2c(-n3cnnn3)ccc(Cl)c2F)c[n+]1[O-])n1cc(-c2ccc(NC(=O)OC)cc2)cn1]

LC/MS: mass calculated for $C_{26}H_{22}ClFN_8O_3$: 548.14, measured (ES, m/z): 549.05 [M+H]$^+$. $^1$H NMR (300 MHz, DMSO-d$_6$) δ 9.67 (s, 1H), 9.63 (s, 1H), 8.41 (s, 1H), 8.34 (s, 1H), 8.04 (t, J=8.7 Hz, 1H), 7.93 (s, 1H), 7.74 (d, J=8.7 Hz, 1H), 7.48-7.51 (m, 2H), 7.41-7.44 (m, 2H), 7.19-7.22 (m, 1H), 7.11-7.15 (m, 1H), 5.85 (dd, J=9.2, 5.4 Hz, 1H), 3.65 (s, 3H), 2.14-2.26 (m, 2H), 0.83 (t, J=7.2 Hz, 3H). $^{19}$F NMR (300 MHz, DMSO-d$_6$) δ −112.75.

Example 158: (R*)-5-(3-Chloro-2-fluoro-6-(1H-tetrazol-1-yl)phenyl)-2-(1-(4-(4-(methoxycarbonylamino)phenyl)-1H-pyrazol-1-yl)propyl)pyridine 1-oxide

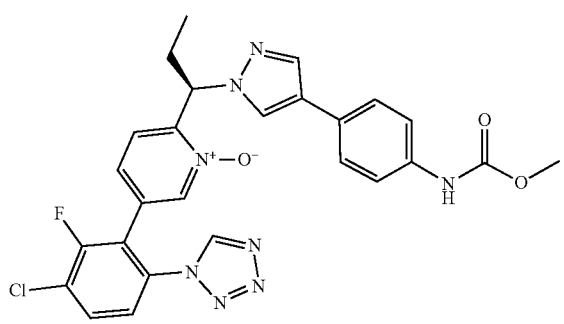 [SMILES: CC[C@H](c1ccc(-c2c(-n3cnnn3)ccc(Cl)c2F)c[n+]1[O-])n1cc(-c2ccc(NC(=O)OC)cc2)cn1]

LC/MS: mass calculated for $C_{26}H_{22}ClFN_8O_3$: 548.14, measured (ES, m/z): 549.05 [M+H]$^+$. $^1$H NMR (300 MHz, DMSO-d$_6$) δ 9.67 (s, 1H), 9.63 (s, 1H), 8.41 (s, 1H), 8.34 (s, 1H), 8.04 (t, J=8.7 Hz, 1H), 7.93 (s, 1H), 7.74 (d, J=8.7 Hz, 1H), 7.48-7.51 (m, 2H), 7.41-7.44 (m, 2H), 7.19-7.22 (m, 1H), 7.11-7.15 (m, 1H), 5.85 (dd, J=9.2, 5.4 Hz, 1H), 3.65 (s, 3H), 2.14-2.26 (m, 2H), 0.83 (t, J=7.2 Hz, 3H). $^{19}$F NMR (300 MHz, DMSO-d$_6$) δ −112.75.

Example 159: (S*)-5-(3-Chloro-2-fluoro-6-(1H-tetrazol-1-yl)phenyl)-2-(1-(4-(4-(methoxycarbonylamino)phenyl)-1H-pyrazol-1-yl)butyl)pyridine 1-oxide

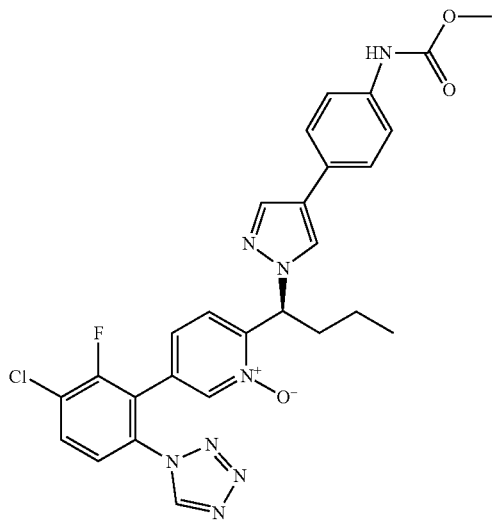 [SMILES: CCC[C@@H](c1ccc(-c2c(-n3cnnn3)ccc(Cl)c2F)c[n+]1[O-])n1cc(-c2ccc(NC(=O)OC)cc2)cn1]

LC/MS: mass calculated for $C_{28}H_{22}ClFN_8O_3$: 548.14, measured (ES, m/z): 549.05 [M+H]$^+$. $^1$H NMR (300 MHz, DMSO-d$_6$) δ 9.67 (s, 1H), 9.63 (s, 1H), 8.41 (s, 1H), 8.34 (s, 1H), 8.04 (t, J=8.7 Hz, 1H), 7.93 (s, 1H), 7.74 (d, J=8.7 Hz, 1H), 7.48-7.51 (m, 2H), 7.41-7.44 (m, 2H), 7.19-7.22 (m, 1H), 7.11-7.15 (m, 1H), 5.85 (dd, J=9.2, 5.4 Hz, 1H), 3.65 (s, 3H), 2.14-2.26 (m, 2H), 0.83 (t, J=7.2 Hz, 3H). $^{19}$F NMR (300 MHz, DMSO-d$_6$) δ −112.75.

Example 160: 5-(3-Chloro-2-fluoro-6-(1H-tetrazol-1-yl)phenyl)-2-(1-(4-(4-(methoxycarbonylamino)phenyl)-1H-pyrazol-1-yl)butyl)pyridine 1-oxide

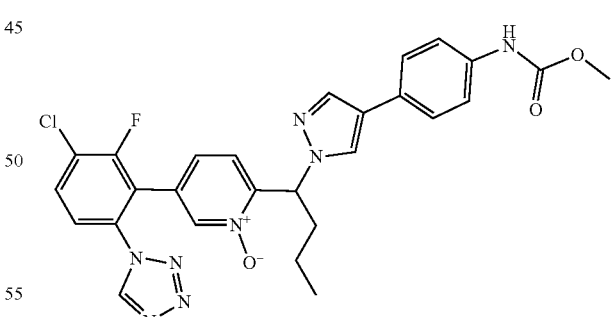

LC/MS: mass calculated for $C_{27}H_{24}ClFN_8O_3$: 562.16, measured (ES, m/z): 563.10 [M+H]$^+$. $^1$H NMR (300 MHz, DMSO-d$_6$) δ 9.67 (s, 1H), 9.63 (s, 1H), 8.40 (s, 1H), 8.36 (s, 1H), 8.04 (t, J=8.7 Hz, 1H), 7.92 (s, 1H), 7.73 (d, J=8.7 Hz, 1H), 7.48-7.51 (m, 2H), 7.41-7.44 (m, 2H), 7.19-7.22 (m, 1H), 7.11-7.15 (m, 1H), 5.97 (dd, J=10.4, 4.2 Hz, 1H), 3.65 (s, 3H), 2.15-2.28 (m, 1H), 2.02-2.12 (m, 1H), 1.15-1.24 (m, 2H), 0.88 (t, J=7.3 Hz, 3H). $^{19}$F NMR (300 MHz, DMSO-d$_6$) δ −112.76.

Example 161: (R*)-5-(3-Chloro-2-fluoro-6-(1H-tetrazol-1-yl)phenyl)-2-(1-(4-(4-(methoxycarbonylamino)phenyl)-1H-pyrazol-1-yl)butyl)pyridine 1-oxide

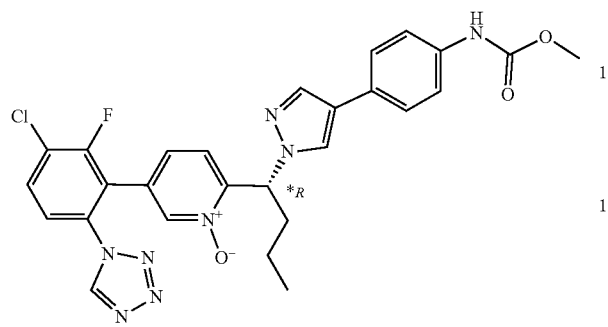

LC/MS: mass calculated for $C_{27}H_{24}ClFN_8O_3$: 562.16, measured (ES, m/z): 563.10 [M+H]$^+$. $^1$H NMR (300 MHz, DMSO-d$_6$) δ 9.67 (s, 1H), 9.63 (s, 1H), 8.40 (s, 1H), 8.36 (s, 1H), 8.04 (t, J=8.7 Hz, 1H), 7.92 (s, 1H), 7.73 (d, J=8.7 Hz, 1H), 7.48-7.51 (m, 2H), 7.41-7.44 (m, 2H), 7.19-7.22 (m, 1H), 7.11-7.15 (m, 1H), 5.97 (dd, J=10.4, 4.2 Hz, 1H), 3.65 (s, 3H), 2.15-2.28 (m, 1H), 2.02-2.12 (m, 1H), 1.15-1.24 (m, 2H), 0.88 (t, J=7.3 Hz, 3H). $^{19}$F NMR (300 MHz, DMSO-d$_6$) δ −112.76.

Example 162: (S*)-5-(3-Chloro-2-fluoro-6-(1H-tetrazol-1-yl)phenyl)-2-(1-(4-(4-(methoxycarbonylamino)phenyl)-1H-pyrazol-1-yl)butyl)pyridine 1-oxide

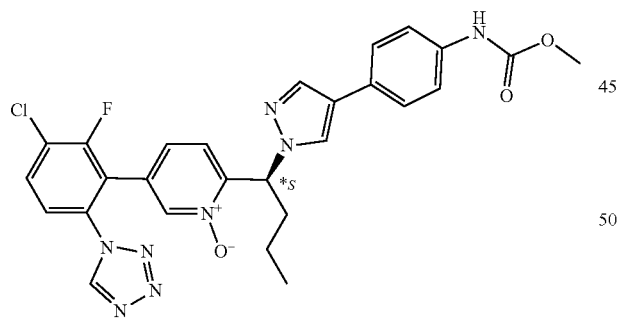

LC/MS: mass calculated for $C_{27}H_{24}ClFN_8O_3$: 562.16, measured (ES, m/z): 563.15 [M+H]$^+$. $^1$H NMR (300 MHz, DMSO-d$_6$) δ 9.67 (s, 1H), 9.63 (s, 1H), 8.40 (s, 1H), 8.36 (s, 1H), 8.04 (t, J=8.7 Hz, 1H), 7.92 (s, 1H), 7.73 (d, J=8.7 Hz, 1H), 7.48-7.51 (m, 2H), 7.41-7.44 (m, 2H), 7.19-7.22 (m, 1H), 7.11-7.15 (m, 1H), 5.97 (dd, J=10.4, 4.2 Hz, 1H), 3.65 (s, 3H), 2.15-2.28 (m, 1H), 2.02-2.12 (m, 1H), 1.15-1.24 (m, 2H), 0.88 (t, J=7.3 Hz, 3H). $^{19}$F NMR (300 MHz, DMSO-d$_6$) δ −112.76.

Example 163: (R*)-5-(3-Chloro-2-fluoro-6-(1H-tetrazol-1-yl)phenyl)-2-(2-(4-chlorophenyl)-1-(4-(4-((methoxycarbonyl)amino)phenyl)-1H-pyrazol-1-yl)ethyl)pyridine 1-oxide

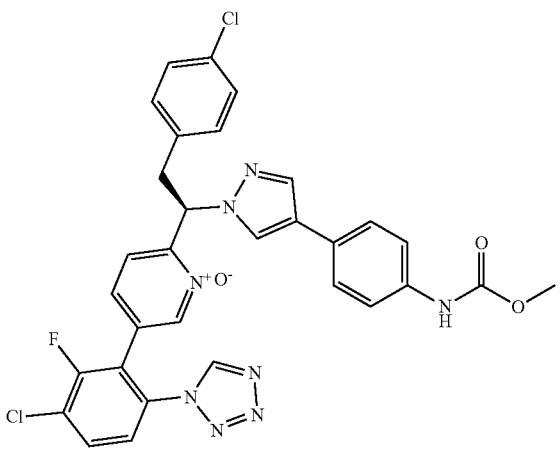

LC/MS: mass calculated for $C_{31}H_{23}Cl_2FN_8O_3$: 644.1, measured (ES, m/z): 645.0 [M+H]$^+$. $^1$H NMR (300 MHz, CD$_3$OD) δ 9.37 (s, 1H), 8.39 (s, 1H), 7.85-7.98 (m, 3H), 7.60 (d, J=8.7 Hz, 1H), 7.47 (d, J=8.3 Hz, 1H), 7.40 (s, 4H), 7.25-7.33 (m, 1H), 7.15-7.23 (m, 4H), 6.23 (dd, J=9.8, 4.5 Hz, 1H), 3.72 (s, 3H), 3.52-3.73 (m, 2H).

Example 164: (S*)-5-(3-Chloro-2-fluoro-6-(1H-tetrazol-1-yl)phenyl)-2-(2-(4-chlorophenyl)-1-(4-(4-((methoxycarbonyl)amino)phenyl)-1H-pyrazol-1-yl)ethyl)pyridine 1-oxide

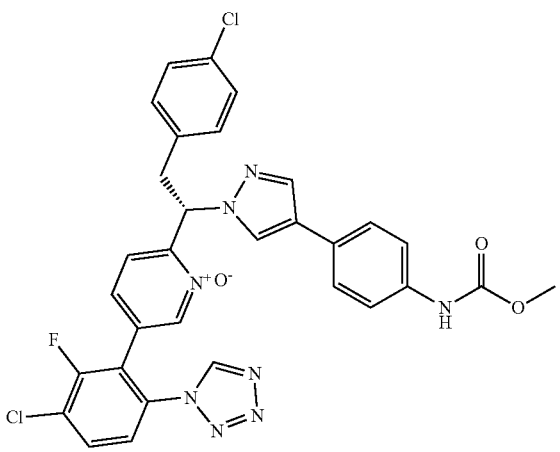

LC/MS: mass calculated for $C_{31}H_{23}Cl_2FN_8O_3$: 644.1, measured (ES, m/z): 645.0 [M+H]$^+$. $^1$H NMR (300 MHz, CD$_3$OD) δ 9.37 (s, 1H), 8.39 (s, 1H), 7.85-7.98 (m, 3H), 7.60 (d, J=8.7 Hz, 1H), 7.47 (d, J=8.3 Hz, 1H), 7.40 (s, 4H), 7.25-7.33 (m, 1H), 7.15-7.23 (m, 4H), 6.23 (dd, J=9.8, 4.5 Hz, 1H), 3.72 (s, 3H), 3.52-3.73 (m, 2H).

Example 165: 5-(3-Chloro-2-fluoro-6-(1H-tetrazol-1-yl)phenyl)-2-(2-cyclopropyl-1-(4-(1-isopropyl-6-oxo-1,6-dihydropyridazin-4-yl)-1H-pyrazol-1-yl)ethyl)-4-methoxypyridine 1-oxide

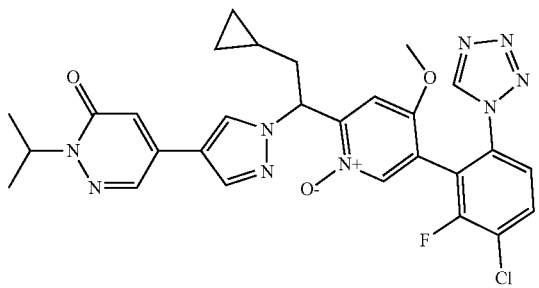 [SMILES: COc1cc(C(CC2CC2)n2cc(-c3cnn(C(C)C)c(=O)c3)cn2)[n+]([O-])cc1-c1c(-n2cnnn2)ccc(Cl)c1F]

LC/MS: mass calculated for $C_{28}H_{27}ClFN_9O_3$: 591.19, measured (ES, m/z): 592.2 [M+H]$^+$. $^1$H NMR (300 MHz, CD$_3$OD) δ 9.4-9.48 (m, 1H), 8.62 (s, 1H), 8.44 (s, 1H), 8.32-8.34 (m, 1H), 8.16-8.19 (m, 1H), 7.88-7.95 (m, 1H), 7.59-7.65 (m, 1H), 7.23-7.26 (m, 1H), 7.06-7.09 (m, 1H), 6.23-6.33 (m, 1H), 5.18-5.27 (m, 1H), 3.70 (s, 3H), 2.46-2.56 (m, 1H), 2.00-2.11 (m, 1H), 1.35-1.38 (m, 6H), 0.64-0.73 (m, 1H), 0.38-0.51 (m, 2H), 0.16-0.22 (m, 1H), 0.00-0.09 (m, 1H). $^{19}$F NMR (282 MHz, CD$_3$OD) δ −112.65.

Example 166: 2-(1-(4-(6-Amino-5-fluoropyridin-3-yl)-1H-pyrazol-1-yl)-2-(4-chlorophenyl)ethyl)-5-(3-chloro-2-fluoro-6-(1H-tetrazol-1-yl)phenyl)pyridine 1-oxide

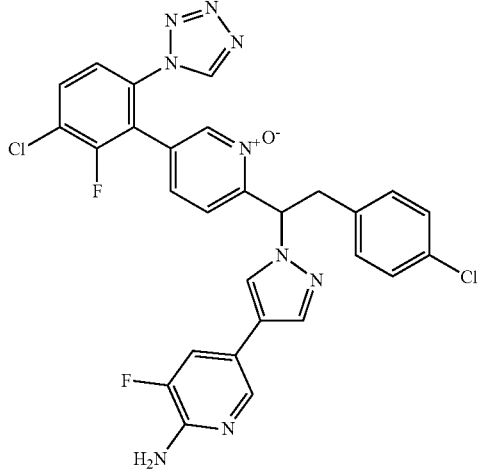

LC/MS: mass calculated for $C_{28}H_{19}Cl_2F_2N_9O$: 605.10, measured (ES, m/z): 606.1 [M+H]$^+$. $^1$H NMR (400 MHz, DMSO-d$_6$) δ 9.70 (s, 1H), 8.47 (s, 1H), 8.02-8.12 (m, 2H), 7.86 (s, 1H), 7.71-7.77 (m, 2H), 7.22-7.33 (m, 3H), 7.16-7.20 (m, 3H), 6.34 (d, J=8.5 Hz, 1H), 6.21 (dd, J=10.0, 4.4 Hz, 1H), 3.50-3.62 (m, 2H). $^{19}$F NMR (376 MHz, DMSO-d$_6$) δ −71.29, −74.89, −112.71.

Example 167: 2-(1-(4-(4-Carboxyphenyl)-1H-pyrazol-1-yl)-2-(2-oxopyrrolidin-1-yl)ethyl)-5-(5-chloro-2-(1H-tetrazol-1-yl)phenyl)pyridine 1-oxide

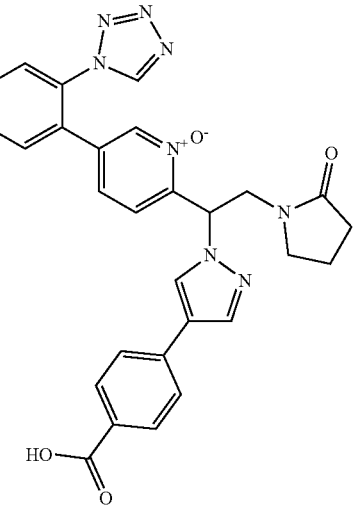

LC/MS: mass calculated for $C_{28}H_{23}ClN_8O_4$: 570.15, measured (ES, m/z): 571.1 [M+H]$^+$. $^1$H NMR (400 MHz, DMSO-d$_6$) δ 9.69 (s, 1H), 8.60 (s, 1H), 8.33 (s, 1H), 8.10 (s, 1H), 7.88-7.96 (m, 3H), 7.80-7.90 (m, 2H), 7.69-7.76 (m, 2H), 7.50 (d, J=8.3 Hz, 1H), 7.01 (d, J=8.3 Hz, 1H), 6.33 (dd, J=9.0, 5.9 Hz, 1H), 3.94-4.10 (m, 2H), 3.21-3.25 (m, 1H), 2.85-2.90 (m, 1H), 2.07-2.12 (m, 2H), 1.81-1.92 (m, 2H).

Example 168: 5-(3-Chloro-2-fluoro-6-(1H-tetrazol-1-yl)phenyl)-2-(1-(4-(4-((methoxycarbonyl)amino)phenyl)-1H-pyrazol-1-yl)-2-(2-methoxyphenyl)ethyl)pyridine 1-oxide

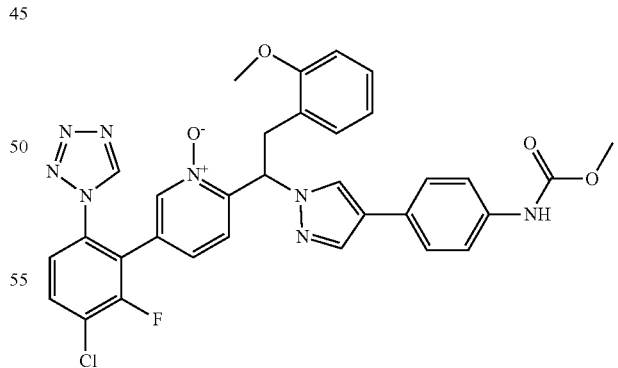

LC/MS: mass calculated for $C_{32}H_{28}ClFN_8O_4$: 640.2, measured (ES, m/z): 641.3 [M]+. $^1$H NMR (400 MHz, CD$_3$OD) δ ppm 3.72 (s, 3H), 3.85 (s, 3H), 6.67-6.84 (m, 3H), 6.84-7.00 (m, 3H), 7.06-7.28 (m, 3H), 7.38 (s, 6H), 7.55-7.66 (m, 3H), 7.66-7.75 (m, 2H), 7.77-7.84 (m, 1H), 7.85-7.97 (m, 3H), 8.34 (s, 2H), 9.36 (s, 1H).

Example 169: 5-(3-Chloro-2-fluoro-6-(1H-tetrazol-1-yl)phenyl)-2-(2-(2-cyclopropyl-1-(4-(1-methyl-2-oxo-1,2-dihydropyridin-4-yl)-1H-pyrazol-1-yl)ethyl)-4-methoxypyridine 1-oxide

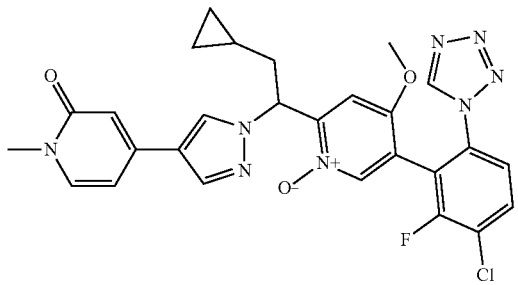

LC/MS: mass calculated for C$_{27}$H$_{24}$ClFN$_8$O$_3$: 562.2, measured (ES, m/z): 563.2 [M+H]$^+$. $^1$H NMR (300 MHz, DMSO-d$_6$) δ 9.70-9.73 (m, 1H), 8.63 (s, 1H), 8.36-8.38 (m, 1H), 8.01-8.11 (m, 2H), 7.70-7.80 (m, 1H), 7.763-7.67 (m, 1H), 6.96-7.03 (m, 1H), 6.62-6.64 (m, 1H), 6.48-6.54 (m, 1H), 6.03-6.16 (m, 1H), 3.53 (s, 3H), 3.37 (s, 3H), 2.27-2.39 (m, 1H), 1.88-1.96 (m, 1H), 0.49-0.59 (m, 1H), 0.24-0.38 (m, 2H), 0.06-0.12 (m, 1H), −0.08-0.00 (m, 1H). $^{19}$F NMR (282 MHz, DMSO-d$_6$) δ −73.44, −111.71, −111.82.

Example 170: 5-(3-Chloro-2-fluoro-6-(1H-tetrazol-1-yl)phenyl)-2-(3-methoxy-1-(4-(1-(methoxycarbonyl)piperidin-4-yl)-1H-pyrazol-1-yl)propyl)pyridine 1-oxide

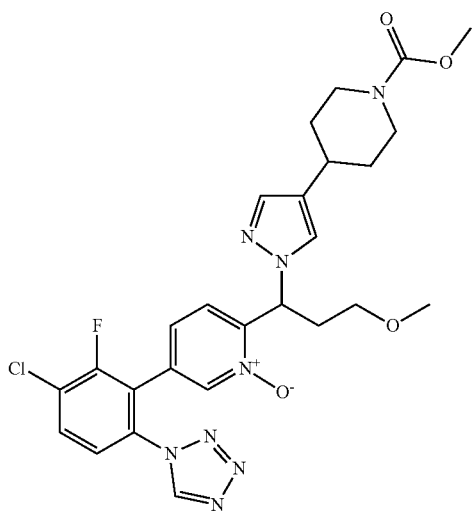 [SMILES: COCCC(c1ccc(-c2c(-n3cnnn3)ccc(Cl)c2F)c[n+]1[O-])n1cc(C2CCN(C(=O)OC)CC2)cn1]

LC/MS: mass calculated for C$_{26}$H$_{28}$ClFN$_8$O$_4$: 570.19, measured (ES, m/z): 571 [M+H]$^+$. $^1$H NMR (300 MHz, DMSO-d$_6$) δ 9.67 (s, 1H), 8.39 (s, 1H), 7.98-8.01 (m, 1H), 7.79 (s, 1H), 7.68 (s, 1H), 7.45 (s, 1H), 7.12 (s, 2H), 6.03 (dd, J=9.7, 4.7 Hz, 1H), 3.95-4.02 (m, 2H), 3.60 (s, 3H), 3.21-3.27 (m, 1H), 3.14 (s, 3H), 3.00-3.08 (m, 1H), 2.81-2.91 (m, 2H), 2.61-2.69 (m, 1H), 2.33-2.39 (m, 2H), 2.82-2.87 (m, 2H), 1.33-1.39 (m, 2H). $^{19}$F NMR (282 MHz, DMSO-d$_6$) δ −112.74.

Example 171: 5-(3-Chloro-2-fluoro-6-(1H-tetrazol-1-yl)phenyl)-2-(2-cyclopropyl-1-(4-(1-(methoxycarbonyl)piperidin-4-yl)-1H-pyrazol-1-yl)ethyl)pyridine 1-oxide

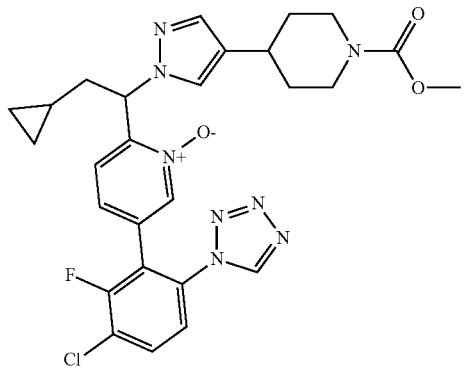 [SMILES: COC(=O)N1CCC(c2cnn(C(CC3CC3)c3ccc(-c4c(-n5cnnn5)ccc(Cl)c4F)c[n+]3[O-])c2)CC1]

LC/MS: mass calculated for C$_{27}$H$_{28}$ClFN$_8$O$_3$: 566.19, measured (ES, m/z): 567 [M+H]$^+$. $^1$H NMR (300 MHz, DMSO-d$_6$) δ 9.66 (s, 1H), 8.37 (s, 1H), 8.04 (t, J=8.7 Hz, 1H), 7.83 (s, 1H), 7.73 (d, J=8.7 Hz, 1H), 7.44 (s, 1H), 7.11 (d, J=1.1 Hz, 2H), 5.96 (dd, J=9.6, 4.2 Hz, 1H), 3.96-3.98 (m, 2H), 3.57 (s, 3H), 2.81-2.89 (m, 2H), 2.57-2.71 (m, 1H), 2.18-2.25 (m, 1H), 1.71-1.89 (m, 3H), 1.31-1.39 (m, 2H), 0.51-0.56 (m, 1H), 0.21-0.29 (m, 2H), 0.00-0.15 (m, 1H), −0.08-0.00 (m, 1H). $^{19}$F NMR (282 MHz, DMSO-d$_6$) δ −74.95, −112.80.

Example 172: 2-((R*)-1-(4-(4-Carboxyphenyl)-1H-pyrazol-1-yl)-2-(2-(piperidine-1-carbonyl)cyclopropyl)ethyl)-5-(3-chloro-2-fluoro-6-(1H-tetrazol-1-yl)phenyl)pyridine 1-oxide

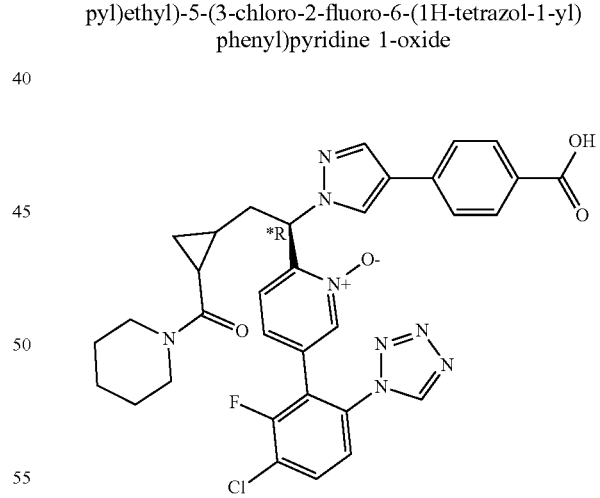

LC/MS: mass calculated for C$_{33}$H$_{30}$ClFN$_8$O$_4$: 656.20, measured (ES, m/z): 657.10 [M+H]$^+$. $^1$H NMR (300 MHz, DMSO-d$_6$) δ 9.69 (s, 1H), 8.63 (s, 1H), 8.44 (s, 1H), 8.16 (s, 1H), 8.06 (d, J=8.7 Hz, 1H), 7.91-7.94 (m, 2H), 7.77-7.73 (m, 3H), 7.26 (d, J=8.3 Hz, 1H), 7.16 (d, J=8.3 Hz, 1H), 6.07 (dd, J=10.4, 3.7 Hz, 1H), 3.27-3.46 (m, 3H), 3.15-3.23 (m, 1H), 2.40-2.47 (m, 1H), 2.01-2.11 (m, 1H), 1.66-1.74 (m, 1H), 1.22-1.52 (m, 6H), 1.07-1.15 (m, 1H), 0.78-0.85 (m, 1H), 0.59-0.66 (m, 1H). $^{19}$F NMR (282 MHz, DMSO-d$_6$) δ −74.66, −112.77.

Example 173: 2-((S*)-1-(4-(4-Carboxyphenyl)-1H-pyrazol-1-yl)-2-(2-(piperidine-1-carbonyl)cyclopropyl)ethyl)-5-(3-Chloro-2-fluoro-6-(1H-tetrazol-1-yl)phenyl)pyridine 1-oxide

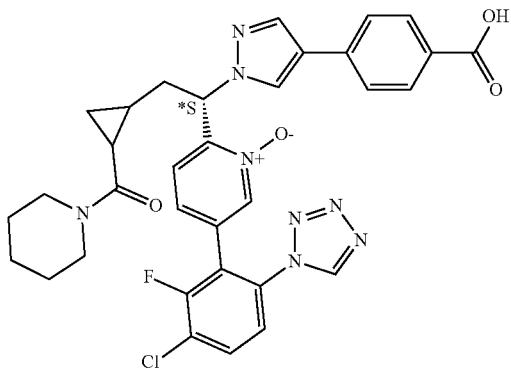 [SMILES: O=C(O)c1ccc(-c2cnn([C@@H](CC3CC3C(=O)N3CCCCC3)c3ccc(-c4c(-n5cnnn5)ccc(Cl)c4F)c[n+]3[O-])c2)cc1]

LC/MS: mass calculated for $C_{33}H_{30}ClFN_8O_4$: 656.20, measured (ES, m/z): 657.10 [M+H]$^+$. $^1$H NMR (300 MHz, DMSO-d$_6$) δ 9.69 (s, 1H), 8.63 (s, 1H), 8.44 (s, 1H), 8.16 (s, 1H), 8.06 (d, J=8.7 Hz, 1H), 7.91-7.94 (m, 2H), 7.77-7.73 (m, 3H), 7.26 (d, J=8.3 Hz, 1H), 7.16 (d, J=8.3 Hz, 1H), 6.07 (dd, J=10.4, 3.7 Hz, 1H), 3.27-3.46 (m, 3H), 3.15-3.23 (m, 1H), 2.40-2.47 (m, 1H), 2.01-2.11 (m, 1H), 1.66-1.74 (m, 1H), 1.22-1.52 (m, 6H), 1.07-1.15 (m, 1H), 0.78-0.85 (m, 1H), 0.59-0.66 (m, 1H). $^{19}$F NMR (282 MHz, DMSO-d$_6$) δ −74.65, −112.77.

Example 174: 2-(1-(4-(4-Carboxyphenyl)-1H-pyrazol-1-yl)-2-((1S*,2R*)-2-(piperidine-1-carbonyl)cyclopropyl)ethyl)-5-(3-chloro-2-fluoro-6-(2,22-trifluoroethoxy)phenyl)pyridine 1-oxide

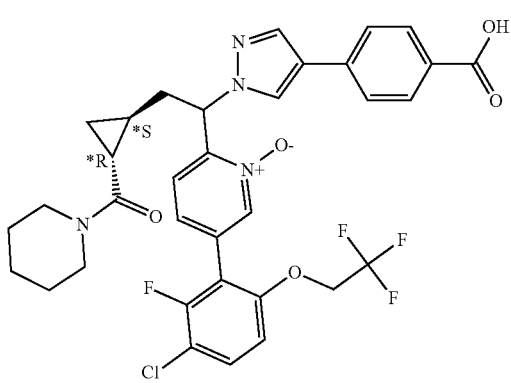 [SMILES: O=C(O)c1ccc(-c2cnn(C(C[C@@H]3C[C@H]3C(=O)N3CCCCC3)c3ccc(-c4c(OCC(F)(F)F)ccc(Cl)c4F)c[n+]3[O-])c2)cc1]

LC/MS: mass calculated for $C_{34}H_{31}ClF_4N_4O_5$: 686.19, measured (ES, m/z): 687.10 [M+H]$^+$. $^1$H NMR (300 MHz, DMSO-d$_6$) δ 8.68 (s, 1H), 8.47 (s, 1H), 8.19 (s, 1H), 7.89-7.98 (m, 2H), 7.67-7.81 (m, 3H), 7.32-7.46 (m, 2H), 7.17-7.29 (m, 1H), 6.16 (dd, J=10.4, 3.7 Hz, 1H), 4.81-4.90 (m, 2H), 3.28-3.44 (m, 3H), 3.14-2.24 (m, 1H), 2.41-2.48 (m, 1H), 2.13-2.22 (m, 1H), 1.69-1.75 (m, 1H), 1.12-1.46 (m, 7H), 0.81-0.87 (m, 1H), 0.66-0.74 (m, 1H). $^{19}$F NMR (282 MHz, DMSO-d$_6$) δ −72.48, −74.64, −115.61.

Example 175: 2-(1-(4-(4-Carboxyphenyl)-1H-pyrazol-1-yl)-2-((1S*,2S*)-2-(piperidine-1-carbonyl)cyclopropyl)ethyl)-5-(3-chloro-2-fluoro-6-(2,2,2-trifluoroethoxy)phenyl)pyridine 1-oxide

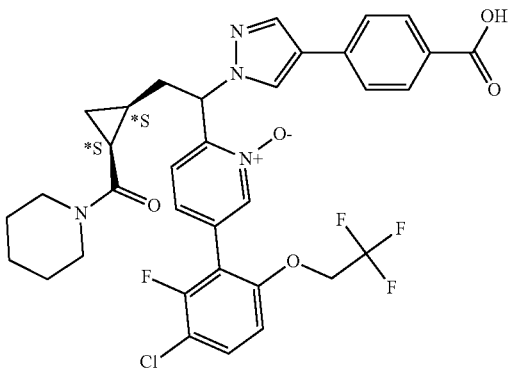 [SMILES: O=C(O)c1ccc(-c2cnn(C(C[C@@H]3C[C@@H]3C(=O)N3CCCCC3)c3ccc(-c4c(OCC(F)(F)F)ccc(Cl)c4F)c[n+]3[O-])c2)cc1]

LC/MS: mass calculated for $C_{34}H_{31}ClF_4N_4O_5$: 686.19, measured (ES, m/z): 687.10 [M+H]$^+$. $^1$H NMR (300 MHz, DMSO-d$_6$) δ 8.68 (s, 1H), 8.47 (s, 1H), 8.19 (s, 1H), 7.89-7.98 (m, 2H), 7.67-7.81 (m, 3H), 7.32-7.46 (m, 2H), 7.17-7.29 (m, 1H), 6.16 (dd, J=10.4, 3.7 Hz, 1H), 4.81-4.90 (m, 2H), 3.28-3.44 (m, 3H), 3.14-2.24 (m, 1H), 2.41-2.48 (m, 1H), 2.13-2.22 (m, 1H), 1.69-1.75 (m, 1H), 1.12-1.46 (m, 7H), 0.81-0.87 (m, 1H), 0.66-0.74 (m, 1H). $^{19}$F NMR (282 MHz, DMSO-d$_6$) δ −72.50, −74.42, −115.55.

Example 176: 5-(3-Chloro-2-fluoro-6-(1H-tetrazol-1-yl)phenyl)-2-(2-cyclopropyl-1-(4-(1-ethyl-6-oxo-1,6-dihydropyridazin-4-yl)-1H-pyrazol-1-yl)ethyl)-4-methoxypyridine 1-oxide

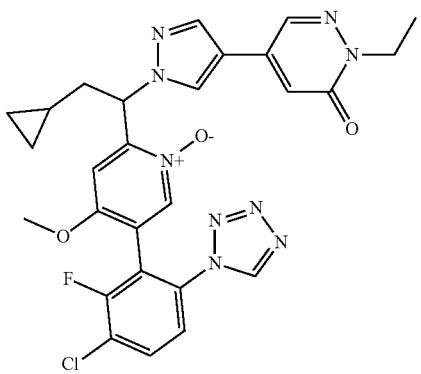 [SMILES: CCn1ncc(-c2cnn(C(CC3CC3)c3cc(OC)c(-c4c(-n5cnnn5)ccc(Cl)c4F)c[n+]3[O-])c2)cc1=O]

LC/MS: mass calculated for $C_{27}H_{25}ClFN_9O_3$: 577.17, measured (ES, m/z): 578 [M+H]$^+$. $^1$H NMR (300 MHz, Chloroform-d) δ 8.85-8.88 (m, 1H), 8.42-8.44 (m, 1H), 8.16-8.18 (m, 1H), 7.93-8.11 (m, 2H), 7.76-7.81 (m, 1H), 7.43-7.46 (m, 1H), 7.31-7.33 (m, 1H), 7.07-7.13 (m, 1H), 6.22-6.37 (m, 1H), 4.20-4.30 (m, 2H), 3.66-3.67 (m, 3H), 2.50-2.61 (m, 1H), 1.88-2.02 (m, 1H), 1.36-1.43 (m, 3H), 0.57-0.63 (m, 1H), 0.36-0.50 (m, 2H), 0.16-0.22 (m, 1H), 0.03-0.10 (m, 1H). $^{19}$F NMR (282 MHz, Chloroform-d) δ −75.87, −109.31, −109.44.

Example 177: 5-(5-Chloro-2-(1H-tetrazol-1-yl)phenyl)-2-(2-(4-chlorophenyl)-1-(4-(pyridin-4-yl)-1H-pyrazol-1-yl)ethyl)pyridine 1-oxide

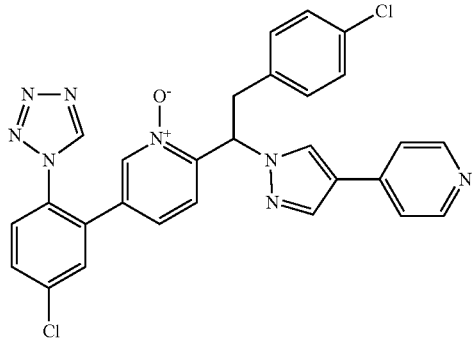 [SMILES: [O-][n+]1cc(-c2cc(Cl)ccc2-n2cnnn2)ccc1C(Cc1ccc(Cl)cc1)n1cc(-c2ccncc2)cn1]

LC/MS: mass calculated for $C_{28}H_{20}Cl_2N_8O$: 554.1, measured (ES, m/z): 555.2 [M+H]$^+$. $^1$H NMR (400 MHz, CD$_3$OD) δ ppm 3.56-3.66 (m, 1H), 3.72 (dd, J=13.7, 10.8 Hz, 1H), 6.33 (dd, J=10.8, 3.9 Hz, 1H), 7.13-7.18 (m, 2H), 7.18-7.26 (m, 2H), 7.68-7.75 (m, 3H), 7.75-7.83 (m, 3H), 8.12 (d, J=6.8 Hz, 1H), 8.29-8.33 (m, 1H), 8.36 (s, 1H), 8.52-8.58 (m, 2H), 8.62 (d, J=6.8 Hz, 1H), 9.39 (s, 1H). LC/MS: mass calculated for $C_{28}H_{20}Cl_2N_8O$: 554.1, measured (ES, m/z): 555.2 [M+H]$^+$.

Example 178: 5-(5-Chloro-2-(1H-tetrazol-1-yl)phenyl)-2-(2-(4-chlorophenyl)-1-(4-(1-oxidopyridin-4-yl)-1H-pyrazol-1-yl)ethyl)pyridine 1-oxide

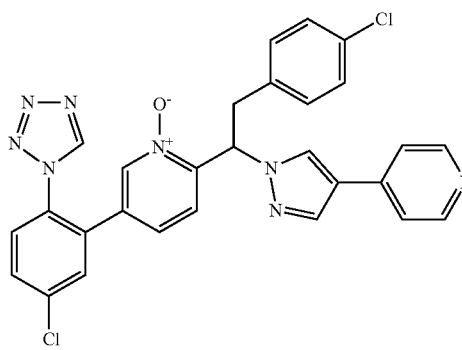

LC/MS: mass calculated for $C_{28}H_{20}Cl_2N_8O_2$: 570.1, measured (ES, m/z): 571.2 [M+H]$^+$. $^1$H NMR (400 MHz, CD$_3$OD) δ ppm 3.54-3.72 (m, 2H), 6.27 (bd, J=4.4 Hz, 1H), 7.13-7.18 (m, 7H), 7.58 (d, J=8.3 Hz, 1H), 7.75-7.83 (m, 6H), 8.14 (s, 1H), 8.31 (s, 1H), 9.38 (s, 1H).

Example 179: 5-(5-Chloro-2-(1H-tetrazol-1-yl)phenyl)-2-(2-(4-chlorophenyl)-1-(4-(2-fluoropyridin-4-yl)-1H-pyrazol-1-yl)ethyl)pyridine 1-oxide

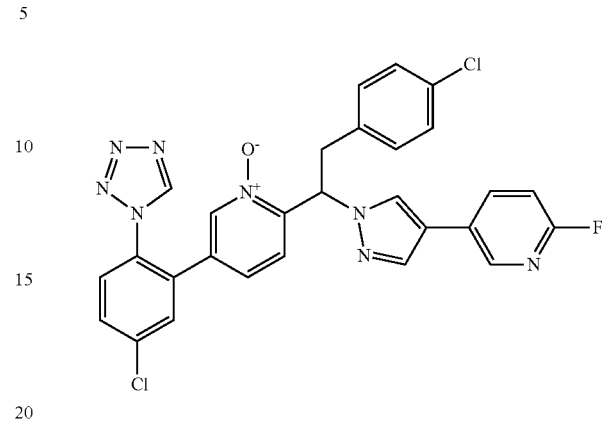

LC/MS: mass calculated for $C_{28}H_{19}Cl_2FN_8O$: 572.1, measured (ES, m/z): 573.2 [M]$^+$. $^1$H NMR (400 MHz, CD$_3$OD) δ ppm 3.53-3.71 (m, 2H), 6.16-6.38 (m, 1H), 7.04 (d, J=8.3, 1H), 7.15-7.19 (m, 2H), 7.19-7.24 (m, 2H), 7.51 (d, J=8.8 Hz, 1H), 7.69-7.74 (m, 2H), 7.75-7.83 (m, 2H), 7.98-8.07 (m, 2H), 8.07-8.12 (m, 2H), 8.34 (d, J=2.4 Hz, 1H), 9.38 (s, 1H).

Example 180: 5-(5-Chloro-2-(1H-tetrazol-1-yl)phenyl)-2-(2-(4-chlorophenyl)-1-(4-(3-fluoropyridin-4-yl)-1H-pyrazol-1-yl)ethyl)pyridine 1-oxide

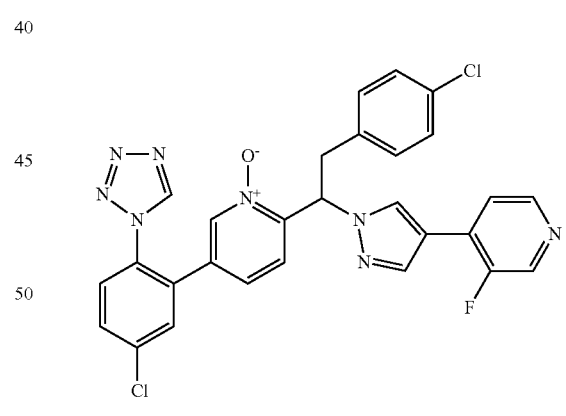

LC/MS: mass calculated for $C_{28}H_{19}Cl_2FN_8O$: 572.1, measured (ES, m/z): 573.2 [M+H]$^+$. $^1$H NMR (400 MHz, CD$_3$OD) δ ppm 3.52-3.73 (m, 2H), 6.21-6.36 (m, 1H), 7.14-7.19 (m, 2H), 7.19-7.24 (m, 2H), 7.55 (d, J=8.3 Hz, 1H), 7.69-7.75 (m, 2H), 7.75-7.83 (m, 4H), 8.05-8.12 (m, 2H), 8.15 (s, 1H), 8.29 (d, J=8.8 Hz, 1H), 9.38 (s, 1H).

Example 181: 2-((R*)-1-(4-(4-Carboxyphenyl)-1H-pyrazol-1-yl)-2-(2-(3-phenylpyrrolidine-1-carbonyl)cyclopropyl)ethyl)-5-(3-chloro-2-fluoro-6-(1H-tetrazol-1-yl)phenyl)pyridine 1-oxide

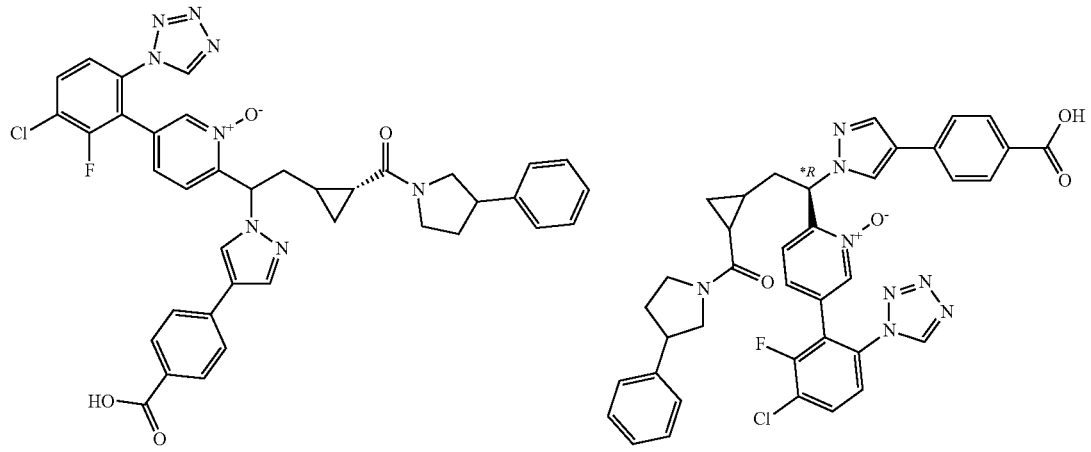 [SMILES: O=C(O)c1ccc(-c2cnn(C(CC3C[C@H]3C(=O)N3CCC(c4ccccc4)C3)c3ccc(-c4c(-n5cnnn5)ccc(Cl)c4F)c[n+]3[O-])c2)cc1 ; O=C(O)c1ccc(-c2cnn([C@H](CC3CC3C(=O)N3CCC(c4ccccc4)C3)c3ccc(-c4c(-n5cnnn5)ccc(Cl)c4F)c[n+]3[O-])c2)cc1]

LC/MS: mass calculated for $C_{38}H_{32}ClFN_8O_4$: 718.22, measured (ES, m/z): 719.10 [M+H]$^+$. $^1$H NMR (400 MHz, DMSO-d$_6$) δ 9.67-9.69 (m, 1H), 8.56-8.62 (m, 1H), 8.40-8.42 (m, 1H), 8.14-8.18 (m, 1H), 8.03-8.07 (m, 1H), 7.89-7.96 (m, 2H), 7.65-7.76 (m, 3H), 7.02-7.47 (m, 7H), 6.05-6.11 (m, 1H), 3.36-3.92 (m, 3H), 2.93-3.21 (m, 2H), 2.12-2.33 (m, 1H), 1.92-2.09 (m, 1H), 1.38-1.58 (m, 1H), 1.15-1.32 (m, 3H), 0.77-0.87 (m, 1H), 0.62-0.68 (m, 1H). $^{19}$F NMR (376 MHz, DMSO-d$_6$) δ −112.74.

Example 182: 2-((S*)-1-(4-(4-Carboxyphenyl)-1H-pyrazol-1-yl)-2-(2-(3-phenylpyrrolidine-1-carbonyl)cyclopropyl)ethyl)-5-(3-chloro-2-fluoro-6-(1H-tetrazol-1-yl)phenyl)pyridine 1-oxide

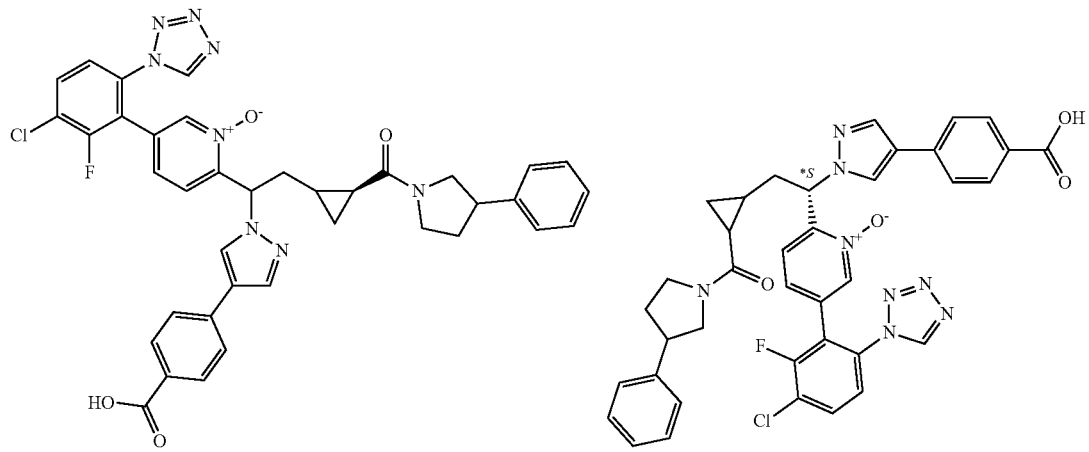 [SMILES: O=C(O)c1ccc(-c2cnn(C(CC3C[C@@H]3C(=O)N3CCC(c4ccccc4)C3)c3ccc(-c4c(-n5cnnn5)ccc(Cl)c4F)c[n+]3[O-])c2)cc1 ; O=C(O)c1ccc(-c2cnn([C@@H](CC3CC3C(=O)N3CCC(c4ccccc4)C3)c3ccc(-c4c(-n5cnnn5)ccc(Cl)c4F)c[n+]3[O-])c2)cc1]

LC/MS: mass calculated for $C_{38}H_{32}ClFN_8O_4$: 718.22, measured (ES, m/z): 719.10 [M+H]$^+$. $^1$H NMR (400 MHz, DMSO-d$_6$) δ 9.67-9.69 (m, 1H), 8.56-8.62 (m, 1H), 8.40-8.42 (m, 1H), 8.14-8.18 (m, 1H), 8.03-8.07 (m, 1H), 7.89-7.96 (m, 2H), 7.65-7.76 (m, 3H), 7.02-7.47 (m, 7H), 6.05-6.11 (m, 1H), 3.36-3.92 (m, 3H), 2.93-3.21 (m, 2H), 2.12-2.33 (m, 1H), 1.92-2.09 (m, 1H), 1.38-1.58 (m, 1H), 1.15-1.32 (m, 3H), 0.77-0.87 (m, 1H), 0.62-0.68 (m, 1H). $^{19}$F NMR (376 MHz, DMSO-d$_6$) δ −112.74.

Example 183: (S*)-2-(1-(4-(6-Amino-2-chloropyridin-3-yl)-1H-pyrazol-1-yl)-2-cyclopropylethyl)-5-(3-chloro-2-fluoro-6-(1H-tetrazol-1-yl)phenyl)pyridine 1-oxide

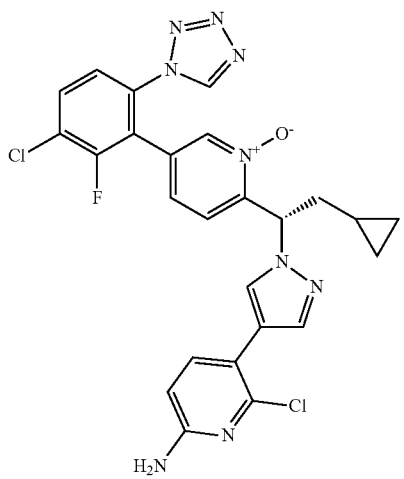 [SMILES: Nc1ccc(-c2cnn([C@@H](CC3CC3)c3ccc(-c4c(-n5cnnn5)ccc(Cl)c4F)c[n+]3[O-])c2)c(Cl)n1]

LC/MS: mass calculated for $C_{25}H_{20}Cl_2FN_9O$: 551.1, measured (ES, m/z): 552.2 [M+H]$^+$. $^1$H NMR (400 MHz, DMSO-d$_6$) δ 9.69 (s, 1H), 8.41 (s, 1H), 8.30 (s, 1H), 8.06 (t, J=8.7 Hz, 1H), 7.85 (s, 1H), 7.76 (d, J=8.7 Hz, 1H), 7.64 (d, J=8.4 Hz, 1H), 7.26 (d, J=8.3 Hz, 1H), 7.16 (d, J=8.3 Hz, 1H), 6.45 (d, J=8.4 Hz, 1H), 6.38 (s, 2H), 6.08 (dd, J=9.8, 4.3 Hz, 1H), 2.30-2.37 (m, 1H), 1.84-1.93 (m, 1H), 0.57-0.61 (m, 1H), 0.28-0.38 (m, 2H), 0.08-0.13 (m, 1H), −0.05-0.00 (m, 1H). $^{19}$F NMR (376 MHz, DMSO-d$_6$) δ −73.51, −112.76.

Example 184: (R*)-2-(1-(4-(6-Amino-2-chloropyridin-3-yl)-1H-pyrazol-1-yl)-2-cyclopropylethyl)-5-(3-chloro-2-fluoro-6-(1H-tetrazol-1-yl)phenyl)pyridine 1-oxide

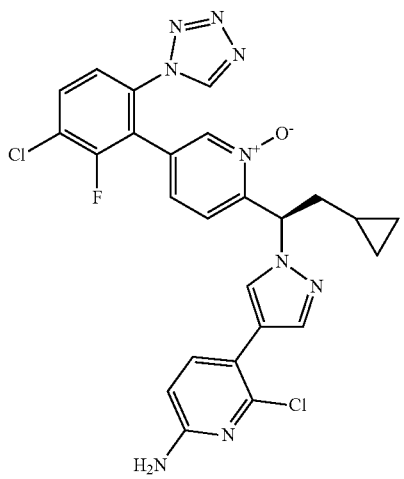 [SMILES: Nc1ccc(-c2cnn([C@H](CC3CC3)c3ccc(-c4c(-n5cnnn5)ccc(Cl)c4F)c[n+]3[O-])c2)c(Cl)n1]

LC/MS: mass calculated for $C_{25}H_{20}Cl_2FN_9O$: 551.1, measured (ES, m/z): 552.0 [M+H]$^+$. $^1$H NMR (400 MHz, DMSO-d$_6$) δ 9.69 (s, 1H), 8.41 (s, 1H), 8.30 (s, 1H), 8.06 (t, J=8.7 Hz, 1H), 7.85 (s, 1H), 7.76 (d, J=8.7 Hz, 1H), 7.64 (d, J=8.4 Hz, 1H), 7.26 (d, J=8.3 Hz, 1H), 7.16 (d, J=8.3 Hz, 1H), 6.45 (d, J=8.4 Hz, 1H), 6.38 (s, 2H), 6.08 (dd, J=9.8, 4.3 Hz, 1H), 2.30-2.37 (m, 1H), 1.84-1.93 (m, 1H), 0.57-0.61 (m, 1H), 0.28-0.38 (m, 2H), 0.08-0.13 (m, 1H), −0.05-0.00 (m, 1H).

Example 185: 5-(3-Chloro-2-fluoro-6-(1H-tetrazol-1-yl)phenyl)-2-(1-(4-(4-(methoxycarbonylamino)phenyl)-1H-pyrazol-1-yl)-3-methylbutyl)pyridine 1-oxide

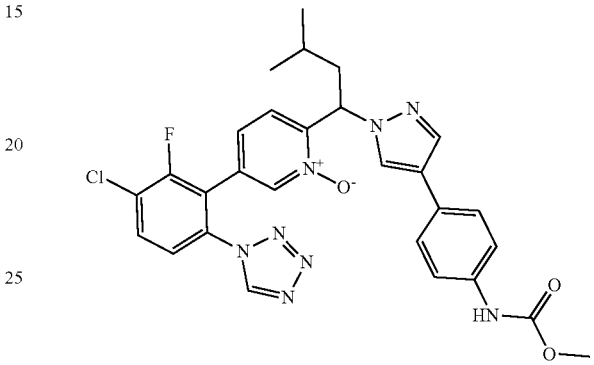

LC/MS: mass calculated for $C_{28}H_{26}ClFN_8O_3$: 576.18, measured (ES, m/z): 577.10 [M+H]$^+$. $^1$H NMR (300 MHz, DMSO-d$_6$) δ 9.66 (s, 1H), 9.61 (s, 1H), 8.39 (t, J=1.7 Hz, 2H), 8.03 (dd, J=8.7, 7.7 Hz, 1H), 7.93 (s, 1H), 7.73 (dd, J=8.7, 1.6 Hz, 1H), 7.50 (d, J=8.8 Hz, 2H), 7.42 (d, J=8.7 Hz, 2H), 7.19 (d, J=8.3 Hz, 1H), 7.16-7.08 (m, 1H), 6.08 (dd, J=10.6, 3.8 Hz, 1H), 3.65 (s, 3H), 2.24 (s, 1H), 1.90 (s, 1H), 1.35 (s, 1H), 0.95 (d, J=6.5 Hz, 3H), 0.84 (d, J=6.6 Hz, 3H). 19F NMR (300 MHz, DMSO-d$_6$) d −74.64, −112.75.

Example 186: (R*)-5-(3-Chloro-2-fluoro-6-(1H-tetrazol-1-yl)phenyl)-2-(1-(4-(4-(methoxycarbonylamino)phenyl)-1H-pyrazol-1-yl)-3-methylbutyl)pyridine 1-oxide

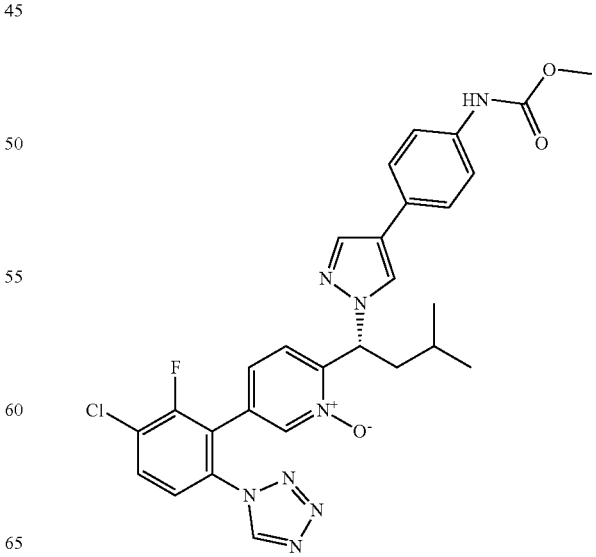

LC/MS: mass calculated for $C_{28}H_{26}ClFN_8O_3$: 576.18, measured (ES, m/z): 577.10 [M+H]+. $^1$H NMR (300 MHz, DMSO-$d_6$) δ 9.66 (s, 1H), 9.61 (s, 1H), 8.40 (s, 2H), 8.04 (t, J=8.7 Hz, 1H), 7.93 (s, 1H), 7.73 (d, J=8.7 Hz, 1H), 7.48-7.51 (m, 2H), 7.40-7.44 (m, 2H), 7.19 (d, J=8.3 Hz, 1H), 7.12 (d, J=8.3 Hz, 1H), 6.08 (dd, J=10.6, 3.8 Hz, 1H), 3.64 (s, 3H), 2.18-2.28 (m, 1H), 1.81-1.83 (m, 1H), 1.21-1.47 (m, 1H), 0.95 (d, J=6.6 Hz, 3H), 0.84 (d, J=6.6 Hz, 3H). $^{19}$F NMR (300 MHz, DMSO-$d_6$) δ −74.03, −112.75.

Example 187: (S*)-5-(3-Chloro-2-fluoro-6-(1H-tetrazol-1-yl)phenyl)-2-(1-(4-(4-(methoxycarbonylamino)phenyl)-1H-pyrazol-1-yl)-3-methylbutyl)pyridine 1-oxide

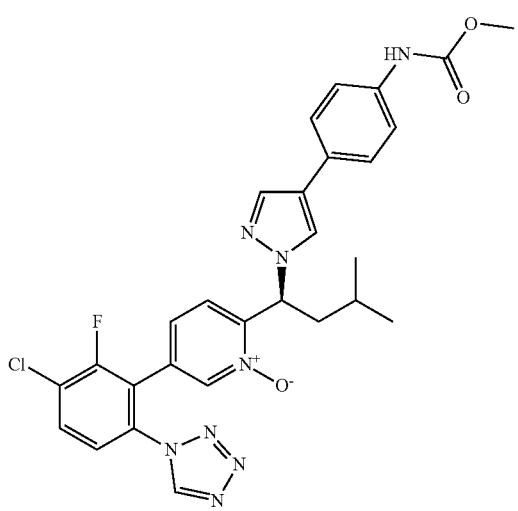 [SMILES: COC(=O)Nc1ccc(-c2cnn([C@@H](CC(C)C)c3ccc(-c4c(-n5cnnn5)ccc(Cl)c4F)c[n+]3[O-])c2)cc1]

LC/MS: mass calculated for $C_{28}H_{26}ClFN_8O_3$: 576.18, measured (ES, m/z): 577.10 [M+H]+. $^1$H NMR (300 MHz, DMSO-$d_6$) δ 9.66 (s, 1H), 9.61 (s, 1H), 8.40 (s, 2H), 8.04 (t, J=8.7 Hz, 1H), 7.93 (s, 1H), 7.73 (d, J=8.7 Hz, 1H), 7.48-7.51 (m, 2H), 7.40-7.44 (m, 2H), 7.19 (d, J=8.3 Hz, 1H), 7.12 (d, J=8.3 Hz, 1H), 6.08 (dd, J=10.6, 3.8 Hz, 1H), 3.64 (s, 3H), 2.18-2.28 (m, 1H), 1.81-1.83 (m, 1H), 1.21-1.47 (m, 1H), 0.95 (d, J=6.6 Hz, 3H), 0.84 (d, J=6.6 Hz, 3H). $^{19}$F NMR (300 MHz, DMSO-$d_6$) δ −74.17, −112.75.

Example 188: 2-(1-(4-(6-Amino-2-fluoropyridin-3-yl)-1H-pyrazol-1-yl)-2-cyclopropylethyl)-5-(3-chloro-2-fluoro-6-(oxazol-5-yl)phenyl)-4-methoxypyridine 1-oxide

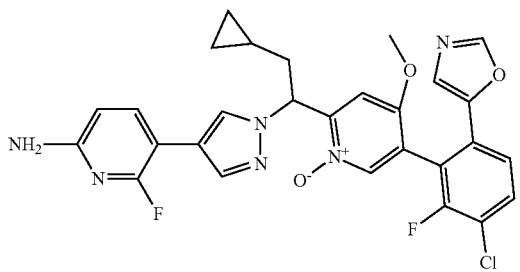 [SMILES: COc1cc(C(CC2CC2)n2cc(-c3ccc(N)nc3F)cn2)[n+]([O-])cc1-c1c(-c2cnco2)ccc(Cl)c1F]

LC/MS: mass calculated for $C_{28}H_{23}ClF_2N_6O_3$: 564.14, measured (ES, m/z): 565.2 [M+H]+. $^1$H NMR (300 MHz, DMSO-$d_6$) δ 8.36-8.44 (m, 2H), 8.27-8.33 (m, 1H), 7.79-7.96 (m, 3H), 7.63-7.73 (m, 1H), 7.19-7.22 (m, 1H), 6.86 (s, 1H), 6.76 (s, 1H), 6.35-6.44 (m, 1H), 6.14-6.29 (m, 1H), 3.69 (s, 3H), 2.37-2.48 (m, 1H), 2.00-2.12 (m, 1H), 0.59-0.71 (m, 1H), 0.29-0.48 (m, 2H), 0.14-0.24 (m, 1H), 0.03-0.10 (m, 1H). $^{19}$F NMR (282 MHz, DMSO-$d_6$) δ −71.41, −74.81, −114.45.

Example 189: 2-(1-(4-(6-Amino-2-methylpyridin-3-yl)-1H-pyrazol-1-yl)-2-cyclopropylethyl)-5-(3-chloro-2-fluoro-6-(1H-tetrazol-1-yl)phenyl)pyridine 1-oxide

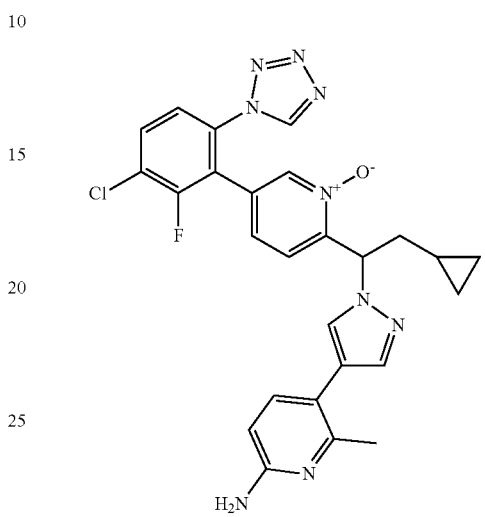

LC/MS: mass calculated for $C_{26}H_{23}ClFN_9O$: 531.2, measured (ES, m/z): 532.1 [M+H]+. $^1$H NMR (400 MHz, DMSO-$d_6$) δ 13.61 (s, 1H), 9.70 (s, 1H), 8.43 (s, 1H), 8.34 (s, 1H), 8.03-8.11 (m, 1H), 8.00 (d, J=9.1 Hz, 1H), 7.84 (s, 1H), 7.76 (d, J=8.7 Hz, 1H), 7.67 (s, 2H), 7.33 (d, J=8.3 Hz, 1H), 7.17 (d, J=8.3 Hz, 1H), 6.86 (d, J=9.1 Hz, 1H), 6.12 (dd, J=9.8, 4.3 Hz, 1H), 2.50 (s, 3H), 2.29-2.36 (m, 1H), 1.88-1.97 (m, 1H), 0.56-0.61 (m, 1H), 0.27-0.37 (m, 2H), 0.10-0.15 (m, 1H), −0.08-0.00 (m, 1H). $^{19}$F NMR (376 MHz, DMSO-$d_6$) δ −73.62, −112.79.

Example 190: 6-Amino-3-(1-(1-(5-(3-Chloro-2-fluoro-6-(1H-tetrazol-1-yl)phenyl)-1-oxidopyridin-2-yl)-2-cyclopropylethyl)-1H-pyrazol-4-yl)-2-methylpyridine 1-oxide

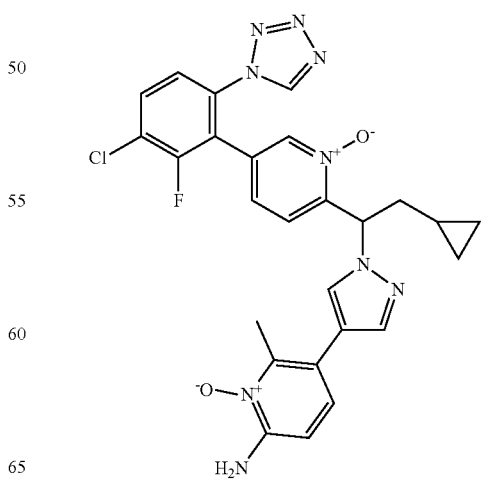

LC/MS: mass calculated for C₂₆H₂₃ClFN₉O₂: 547.2, measured (ES, m/z): 548.3 [M+H]⁺. ¹H NMR (400 MHz, DMSO-d₆) δ 9.70 (s, 1H), 8.43 (s, 1H), 8.25 (s, 1H), 8.02-8.11 (m, 1H), 7.72-7.80 (m, 2H), 7.29-7.32 (m, 2H), 7.15-7.18 (m, 3H), 6.80 (d, J=8.8 Hz, 1H), 6.10 (dd, J=9.8, 4.3 Hz, 1H), 2.48 (s, 3H), 2.27-2.34 (m, 1H), 1.87-1.94 (m, 1H), 0.57-0.63 (m, 1H), 0.28-0.38 (m, 2H), 0.09-0.12 (m, 1H), −0.06-0.00 (m, 1H). ¹⁹F NMR (376 MHz, DMSO-d₆) δ −73.59, −112.76.

Example 191: 5-(3-Chloro-2-fluoro-6-(1H-tetrazol-1-yl)phenyl)-2-(1-(4-(1-oxidopyridin-4-yl)-1H-pyrazol-1-yl)-2-(tetrahydrofuran-2-yl)ethyl)pyridine 1-oxide

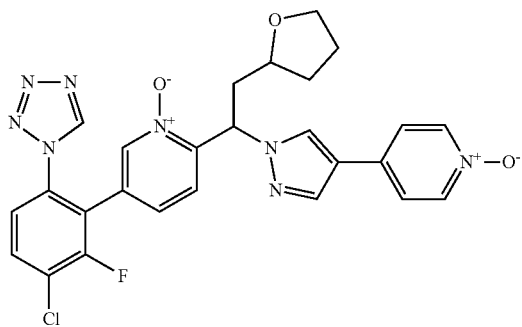 [SMILES: [O-][n+]1ccc(-c2cnn(C(CC3CCCO3)c3ccc(-c4c(-n5cnnn5)ccc(Cl)c4F)c[n+]3[O-])c2)cc1]

LC/MS: mass calculated for C₂₆H₂₂ClFN₈O₃: 548.1, measured (ES, m/z): 549.2 [M]⁺. ¹H NMR (400 MHz, CD₃OD) δ ppm 1.49-1.64 (m, 4H), 1.83-1.90 (m, 3H), 1.90-2.02 (m, 5H), 2.33-2.45 (m, 3H), 2.68 (bd, J=10.8 Hz, 4H), 3.11-3.15 (m, 4H), 3.40-3.55 (m, 2H), 3.56-3.80 (m, 6H), 3.80-3.95 (m, 4H), 5.74-5.84 (m, 7H), 7.25 (bd, J=7.8 Hz, 4H), 7.49-7.68 (m, 9H), 7.83-7.90 (m, 4H), 8.05 (bs, 3H), 8.11 (bs, 4H), 8.27-8.31 (m, 9H), 8.34 (bs, 1H), 8.50 (bs, 1H), 9.21-9.27 (m, 1H).

Example 192: 5-(3-Chloro-2-fluoro-6-(1H-tetrazol-1-yl)phenyl)-2-(1-(4-(pyridin-4-yl)-1H-pyrazol-1-yl)-2-(tetrahydrofuran-2-yl)ethyl)pyridine 1-oxide

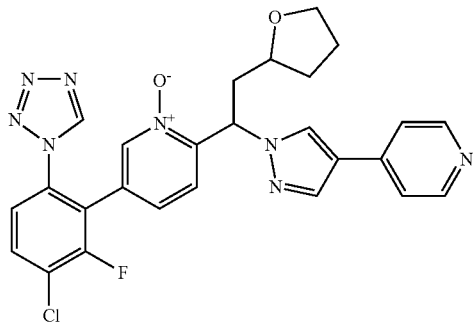 [SMILES: [O-][n+]1cc(-c2c(-n3cnnn3)ccc(Cl)c2F)ccc1C(CC1CCCO1)n1cc(-c2ccncc2)cn1]

LC/MS: mass calculated for C₂₈H₂₂ClFN₈O₂: 532.2, measured (ES, m/z): 533.3 [M+H]⁺. ¹H NMR (400 MHz, CD₃OD) δ ppm 1.52-1.63 (m, 2H), 1.81-2.05 (m, 3H), 2.32-2.45 (m, 2H), 2.46-2.59 (m, 1H), 2.59-2.77 (m, 2H), 3.42-3.53 (m, 2H), 3.54-3.78 (m, 3H), 3.79-3.94 (m, 2H), 5.72-5.86 (m, 1H), 7.34 (bd, J=7.3 Hz, 2H), 7.42-7.53 (m, 1H), 7.53-7.69 (m, 3H), 7.76-7.98 (m, 3H), 8.16 (bs, 2H), 8.23-8.29 (m, 1H), 8.30-8.38 (m, 2H), 8.64 (bs, 2H), 8.69-8.82 (m, 2H), 9.23-9.28 (m, 1H).

Example 193: 5-(3-Chloro-2-fluoro-6-(1H-tetrazol-1-yl)phenyl)-2-(2-cyclopropyl-1-(4-(pyridin-4-yl)-1H-pyrazol-1-yl)ethyl)pyridine 1-oxide

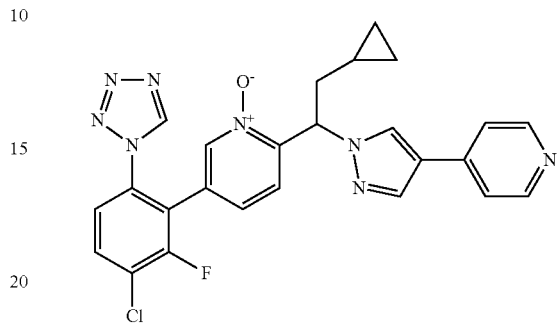

LC/MS: mass calculated for C₂₅H₂₀ClFN₈O: 502.1, measured (ES, m/z): 503.3 [M+H]⁺. ¹H NMR (400 MHz, CD₃OD) δ ppm 0.01-0.25 (m, 2H), 0.30-0.53 (m, 2H), 0.66 (bs, 1H), 1.96-2.13 (m, 2H), 2.37-2.58 (m, 1H), 6.24-6.30 (m, 1H), 7.61 (bdd, J=8.8, 2.0 Hz, 1H), 7.84-8.03 (m, 2H), 8.05-8.15 (m, 2H), 8.27 (bs, 1H), 8.34-8.40 (m, 2H), 8.62 (bd, J=5.9 Hz, 1H), 8.72-8.89 (m, 1H), 9.39 (s, 1H).

Example 194: 5-(3-Chloro-2-fluoro-6-(1H-tetrazol-1-yl)phenyl)-2-(2-cyclopropyl-1-(4-(pyrimidin-5-yl)-1H-pyrazol-1-yl)ethyl)pyridine 1-oxide

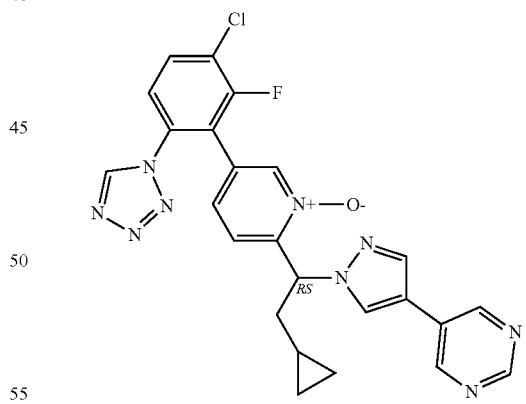

LC/MS: mass calculated for C₂₄H₁₉ClFN₉O: 503.1, measured (ES, m/z): 504.1 [M+H]⁺. ¹H NMR (400 MHz, CD₃OD) δ ppm 0.02-0.11 (m, 1H) 0.14-0.27 (m, 1H) 0.34-0.52 (m, 2 h) 0.65-0.78 (m, 1H) 1.98-2.05 (m, 1H) 2.45-2.59 (m, 1H) 6.22-6.33 (m, 1H) 7.22-7.34 (m, 1H) 7.50 (d, J=8.31 Hz, 1H) 7.60 (dd, J=8.56, 1.71 Hz, 1H) 7.91 (dd, J=8.56, 7.58 Hz, 1H) 8.09-8.19 (m, 1H) 8.33-8.41 (m, 1H) 8.49-8.59 (m, 1H) 8.91-9.22 (m, 3H) 9.36-9.41 (m, 1H).

Example 195: 4-Chloro-5-(3-chloro-2-fluoro-6-(1H-tetrazol-1-yl)phenyl)-2-((R*)-2-cyclopropyl-1-(4-(1-methyl-6-oxo-1,6-dihydropyridazin-4-yl)-1H-pyrazol-1-yl)ethyl)pyridine 1-oxide

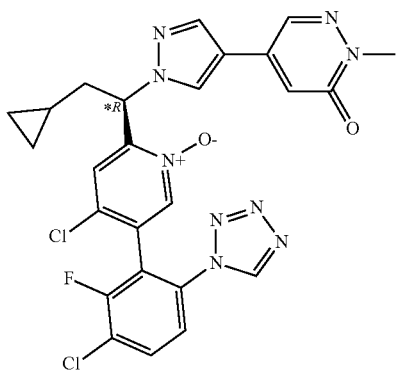

LC/MS: mass calculated for $C_{25}H_{20}Cl_2FN_9O_2$: 567.11, measured (ES, m/z): 568.00 [M+H]$^+$. $^1$H NMR (400 MHz, DMSO-d$_6$) δ 9.82 (s, 1H), 8.81 (s, 1H), 8.60 (s, 1H), 8.29 (d, J=2.2 Hz, 1H), 8.26 (s, 1H), 8.15 (d, J=8.7 Hz, 1H), 7.84 (d, J=8.7 Hz, 1H), 7.67 (s, 1H), 7.15 (d, J=2.2 Hz, 1H), 6.01 (dd, J=9.9, 4.6 Hz, 1H), 3.64 (s, 3H), 2.32-2.41 (m, 1H), 1.90-2.05 (m, 1H), 0.51-0.56 (m, 1H), 0.30-0.38 (m, 2H), 0.05-0.13 (m, 1H), -0.07-0.00 (m, 1H). $^{19}$F NMR (376 MHz, DMSO-d$_6$) δ -111.41.

Example 196: 4-Chloro-5-(3-chloro-2-fluoro-6-(1H-tetrazol-1-yl)phenyl)-2-((S*)-2-cyclopropyl-1-(4-(1-methyl-6-oxo-1,6-dihydropyridazin-4-yl)-1H-pyrazol-1-yl)ethyl)pyridine 1-oxide

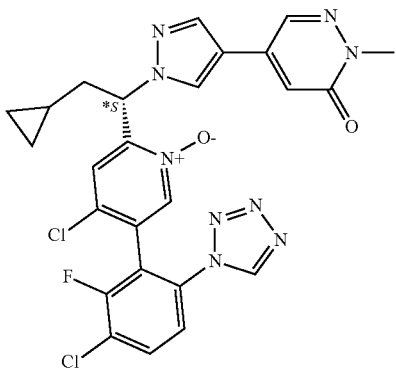

LC/MS: mass calculated for $C_{25}H_{20}Cl_2FN_9O_2$: 567.11, measured (ES, m/z): 567.95 [M+H]$^+$. $^1$H NMR (400 MHz, DMSO-d$_6$) δ 9.82 (s, 1H), 8.81 (s, 1H), 8.60 (s, 1H), 8.29 (d, J=2.2 Hz, 1H), 8.26 (s, 1H), 8.15 (d, J=8.7 Hz, 1H), 7.84 (d, J=8.7 Hz, 1H), 7.67 (s, 1H), 7.15 (d, J=2.2 Hz, 1H), 6.01 (dd, J=9.9, 4.6 Hz, 1H), 3.64 (s, 3H), 2.32-2.41 (m, 1H), 1.90-2.05 (m, 1H), 0.51-0.56 (m, 1H), 0.30-0.38 (m, 2H), 0.05-0.13 (m, 1H), -0.07-0.00 (m, 1H). $^{19}$F NMR (376 MHz, DMSO-d$_6$) δ -111.39.

Example 197: (R*)-5-(3-Chloro-2-fluoro-6-(1H-tetrazol-1-yl)phenyl)-2-(3-isopropoxy-1-(4-(4-(methoxycarbonylamino)phenyl)-1H-pyrazol-1-yl)propyl)pyridine 1-oxide

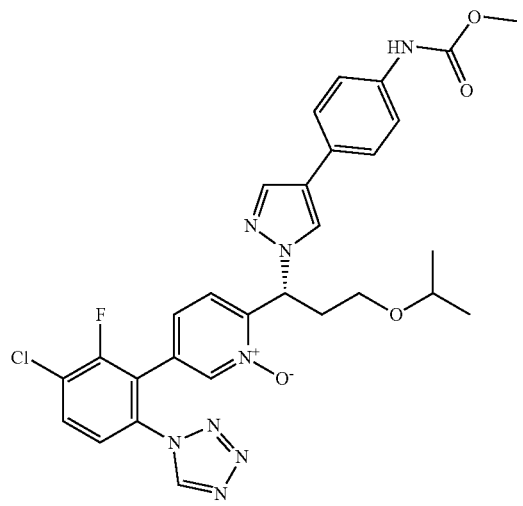 [SMILES: COC(=O)Nc1ccc(-c2cnn([C@H](CCOC(C)C)c3ccc(-c4c(-n5cnnn5)ccc(Cl)c4F)c[n+]3[O-])c2)cc1]

LC/MS: mass calculated for $C_{29}H_{28}ClFN_8O_4$: 606.19, measured (ES, m/z): 607.05 [M+H]$^+$. $^1$H NMR (400 MHz, DMSO-d$_6$) δ 9.67 (s, 1H), 9.62 (s, 1H), 8.40 (s, 1H), 8.31 (s, 1H), 8.05 (t, J=8.7 Hz, 1H), 7.94 (s, 1H), 7.75 (d, J=8.8 Hz, 1H), 7.47-7.55 (m, 2H), 7.42-7.45 (m, 2H), 7.29 (d, J=8.3 Hz, 1H), 7.16 (d, J=8.3 Hz, 1H), 6.15 (t, J=7.3 Hz, 1H), 3.66 (s, 3H), 3.31-3.47 (m, 2H), 3.14-3.20 (m, 1H), 2.39-2.44 (m, 2H), 1.01 (dd, J=9.2, 6.1 Hz, 6H). $^{19}$F NMR (376 MHz, DMSO-d$_6$) δ -112.73.

Example 198: (S*)-5-(3-Chloro-2-fluoro-6-(1H-tetrazol-1-yl)phenyl)-2-(3-isopropoxy-1-(4-(4-(methoxycarbonylamino)phenyl)-1H-pyrazol-1-yl)propyl)pyridine 1-oxide

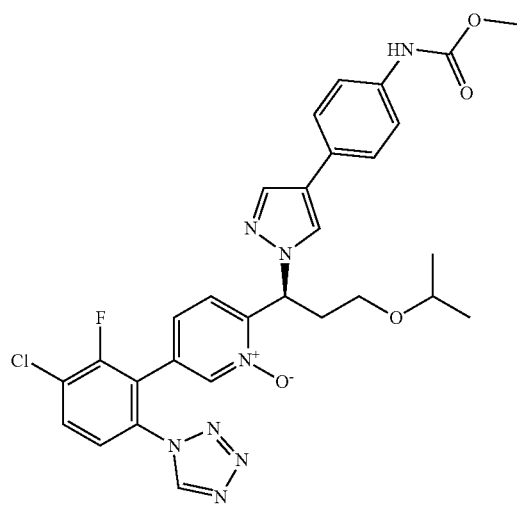 [SMILES: COC(=O)Nc1ccc(-c2cnn([C@@H](CCOC(C)C)c3ccc(-c4c(-n5cnnn5)ccc(Cl)c4F)c[n+]3[O-])c2)cc1]

LC/MS: mass calculated for $C_{29}H_{28}ClFN_8O_4$: 606.19, measured (ES, m/z): 607.05 [M+H]$^+$. $^1$H NMR (400 MHz, DMSO-$d_6$) δ 9.67 (s, 1H), 9.62 (s, 1H), 8.40 (s, 1H), 8.31 (s, 1H), 8.05 (t, J=8.7 Hz, 1H), 7.94 (s, 1H), 7.75 (d, J=8.8 Hz, 1H), 7.47-7.55 (m, 2H), 7.42-7.45 (m, 2H), 7.29 (d, J=8.3 Hz, 1H), 7.16 (d, J=8.3 Hz, 1H), 6.15 (t, J=7.3 Hz, 1H), 3.66 (s, 3H), 3.31-3.47 (m, 2H), 3.14-3.20 (m, 1H), 2.39-2.44 (m, 2H), 1.01 (dd, J=9.2, 6.1 Hz, 6H). $^{19}$F NMR (376 MHz, DMSO-$d_6$) δ −112.72.

Example 199: (S*)-2-(1-(4-(6-Amino-5-fluoropyridin-3-yl)-1H-pyrazol-1-yl)-2-cyclopropylethyl)-5-(3-chloro-2-fluoro-6-(1H-tetrazol-1-yl)phenyl)pyridine 1-oxide

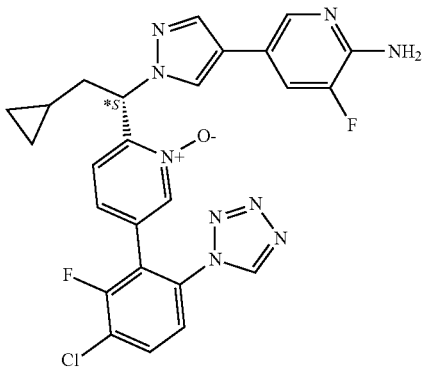

LC/MS: mass calculated for $C_{25}H_{20}ClF_2N_9O$: 535.1, measured (ES, m/z): 536.3 [M+H]$^+$. $^1$H NMR (400 MHz, DMSO-$d_6$) δ 9.69 (s, 1H), 8.44 (s, 1H), 8.41 (s, 1H), 8.11-8.02 (m, 2H), 7.98 (s, 1H), 7.73-7.77 (m, 2H), 7.21 (d, J=8.2 Hz, 1H), 7.14 (d, J=8.2 Hz, 1H), 6.04 (dd, J=9.6, 4.3 Hz, 1H), 2.34-2.43 (m, 1H), 1.79-1.87 (m, 1H), 0.58-0.64 (m, 1H), 0.29-0.37 (m, 2H), 0.09-0.14 (m, 1H), 0.00-0.04 (m, 1H). $^{19}$F NMR (376 MHz, DMSO-$d_6$) δ −73.97, −112.79.

Example 200: (R*)-2-(1-(4-(6-Amino-5-fluoropyridin-3-yl)-1H-pyrazol-1-yl)-2-cyclopropylethyl)-5-(3-chloro-2-fluoro-6-(1H-tetrazol-1-yl)phenyl)pyridine 1-oxide

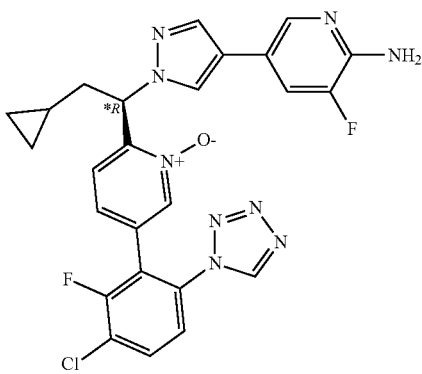

Step 1. N-(5-(1-(1-(5-Bromopyridin-2-yl)-2-cyclopropylethyl)-1H-pyrazol-4-yl)-3-fluoropyridin-2-yl)acetamide To a solution of N-(3-fluoro-5-(1H-pyrazol-4-yl)pyridin-2-yl)acetamide (prepared via Suzuki coupling of 5-bromo-3-fluoropyridin-2-amine and tert-butyl 4-(4,4,5,5-tetramethyl-1,3,2-dioxaborolan-2-yl)-1H-pyrazole-1-carboxylate) (250 mg, 1.135 mmol, 1.00 equiv) in CH$_3$CN (10 mL) was added 1-(5-bromopyridin-2-yl)-2-cyclopropylethyl methanesulfonate (363.532 mg, 1.135 mmol, 1.00 equiv) and Cs$_2$CO$_3$ (739.817 mg, 2.271 mmol, 2.00 equiv). The resulting mixture was stirred at 80° C. for 5 h. The reaction was concentrated. The residue obtained was purified by silica gel chromatography (0-100% EtOAc/petroleum ether) to yield TM as a yellow solid (240 mg, 47.579% yield). LC/MS: mass calculated for $C_{20}H_{19}BrFN_5O$: 444.3, measured: 444.1 [M+H]$^+$.

Step 2. N-(5-(1-(1-(5-(6-Amino-3-chloro-2-fluorophenyl)pyridin-2-yl)-2-cyclopropylethyl)-1H-pyrazol-4-yl)-3-fluoropyridin-2-yl)acetamide To a solution of N-(5-(1-(1-(5-bromopyridin-2-yl)-2-cyclopropylethyl)-1H-pyrazol-4-yl)-3-fluoropyridin-2-yl)acetamide (9.643 mg, 0.022 mmol, 1.00 equiv) in 1,4-dioxane (0.5 mL) and H$_2$O (0.1 mL) was added 4-chloro-3-fluoro-2-(4,4,5,5-tetramethyl-1,3,2-dioxaborolan-2-yl)benzenamine (7.072 mg, 0.026 mmol, 1.20 equiv), K$_2$CO$_3$ (8.999 mg, 0.065 mmol, 3.00 equiv) and Pd(PPh$_3$)$_4$ (2.508 mg, 0.002 mmol, 0.10 equiv). The resulting mixture was stirred at 85° C. for 5 h. LC/MS: mass calculated for $C_{26}H_{23}ClF_2N_6O$: 509.0, measured: 509.1 [M+H]$^+$.

Step 3. N-(5-(1-(1-(5-(3-Chloro-2-fluoro-6-(1H-tetrazol-1-yl)phenyl)pyridin-2-yl)-2-cyclopropylethyl)-1H-pyrazol-4-yl)-3-fluoropyridin-2-yl)acetamide To a solution of N-(5-(1-(1-(5-(6-amino-3-chloro-2-fluorophenyl)pyridin-2-yl)-2-cyclopropylethyl)-1H-pyrazol-4-yl)-3-fluoropyridin-2-yl)acetamide (160 mg, 0.314 mmol, 1.00 equiv) in AcOH (5 mL) was added trimethoxymethane (500.419 mg, 4.716 mmol, 15.00 equiv) and TMSN$_3$ (362.186 mg, 3.144 mmol, 10.00 equiv). The resulting mixture was stirred at rt for 6 h. The mixture was purified by reverse-phase chromatography (C18, 330 g, CH$_3$CN/H$_2$O (0.05% TFA)=10%-70%), this resulted in 145 mg (82.074% yield) of target molecule as a yellow solid. LC/MS: mass calculated for $C_{27}H_{22}ClF_2N_9O$: 562.0, measured: 562.1 [M+H]$^+$.

Step 4. 2-(1-(4-(6-Acetamido-5-fluoropyridin-3-yl)-1H-pyrazol-1-yl)-2-cyclopropylethyl)-5-(3-chloro-2-fluoro-6-(1H-tetrazol-1-yl)phenyl)pyridine 1-oxide To a solution of N-(5-(1-(1-(5-(3-chloro-2-fluoro-6-(1H-tetrazol-1-yl)phenyl)pyridin-2-yl)-2-cyclopropylethyl)-1H-pyrazol-4-yl)-3-fluoropyridin-2-yl)acetamide (9.824 mg, 0.017 mmol, 1.00 equiv) in DMF (1 mL) was added H$_2$O$_2$ (9.911 mg, 0.087 mmol, 5.00 equiv) and ReMeO$_3$ (2.179 mg, 0.009 mmol, 0.50 equiv). The resulting mixture was stirred at rt for 5 h. The mixture was purified by reverse-phase chromatography (C18, 330 g, CH$_3$CN/H$_2$O (0.05% TFA)=10%-70%), this resulted in 9.0 mg (16.9% yield) of the desired product as a white solid. LC/MS: mass calculated for $C_{27}H_{22}ClF_2N_9O_2$. 0.57C2HF3O2: 643.0, measured: 578.2 [M+H]$^+$.

Step 5. (R*)-2-(1-(4-(6-Amino-5-fluoropyridin-3-yl)-1H-pyrazol-1-yl)-2-cyclopropylethyl)-5-(3-chloro-2-fluoro-6-(1H-tetrazol-1-yl)phenyl)pyridine 1-oxide The mixture of 2-(1-(4-(6-acetamido-5-fluoropyridin-3-yl)-1H-pyrazol-1-yl)-2-cyclopropylethyl)-5-(3-chloro-2- fluoro-6-(1H-tetrazol-1-yl)phenyl)pyridine 1-oxide (44 mg, 0.076 mmol, 1.00 equiv), HCl (1.0 mL, 2.0 M) and tetrahydrofuran (5.0 mL) was stirred at 60° C. for 4 h. The reaction was concentrated under reduced pressure and the residue was diluted with water. The solution was adjusted to pH 7 and extracted with EA twice. The combined organic was concentrated and the residue was purified by reverse phase chromatography on C18 (40 g, MeCN/H$_2$O (0.05% CF$_3$COOH): 0>>>40%) to yield 2-(1-(4-(6-amino-5-fluoropyridin-3-yl)-1H-pyrazol-1-yl)-2-cyclopropylethyl)-5-(3-chloro-2-fluoro-6-(1H-tetrazol-1-yl)phenyl)pyridine 1-oxide as a white solid. LC/MS: mass calculated for C$_{25}$H$_{20}$ClF$_2$N$_9$O: 536.0, measured: 536.1 [M+H]$^+$.

Step 6: (R*)-2-(1-(4-(6-amino-5-fluoropyridin-3-yl)-1H-pyrazol-1-yl)-2-cyclopropylethyl)-5-(3-chloro-2-fluoro-6-(1H-tetrazol-1-yl)phenyl)pyridine 1-oxide 2-(1-(4-(6-Amino-5-fluoropyridin-3-yl)-1H-pyrazol-1-yl)-2-cyclopropylethyl)-5-(3-chloro-2-fluoro-6-(1H-tetrazol-1-yl)phenyl)pyridine 1-oxide (30 mg, 0.056 mmol) was purified by preparative chiral HPLC with the following conditions: column, CHIRALPAK IE-3 Size: 0.46*10 cm; 3 um; mobile phase, MtBE (0.1% DEA):EtOH=70:30; Total Run Time (min), 15 min; Detector, UV 254 nm to yield (S*)-2-(1-(4-(6-amino-5-fluoropyridin-3-yl)-1H-pyrazol-1-yl)-2-cyclopropylethyl)-5-(3-chloro-2-fluoro-6-(1H-tetrazol-1-yl)phenyl)pyridine 1-oxide as an off-white solid and (R*)-2-(1-(4-(6-amino-5-fluoropyridin-3-yl)-1H-pyrazol-1-yl)-2-cyclopropylethyl)-5-(3-chloro-2-fluoro-6-(1H-tetrazol-1-yl)phenyl)pyridine 1-oxide as a white solid.

LC/MS: mass calculated for C$_{25}$H$_{20}$ClF$_2$N$_9$O: 535.1, measured (ES, m/z): 536.2 [M+H]$^+$. $^1$H NMR (400 MHz, DMSO-d$_6$) δ 9.69 (s, 1H), 8.41-8.43 (m, 2H), 8.02-8.11 (m, 2H), 7.97 (s, 1H), 7.68-7.76 (m, 2H), 7.20 (d, J=8.3 Hz, 1H), 7.14 (d, J=8.3 Hz, 1H), 6.30 (s, 2H), 6.04 (dd, J=10.0, 4.2 Hz, 1H), 2.33-2.42 (m, 1H), 1.77-1.86 (m, 1H), 0.57-0.63 (m, 1H), 0.31-0.37 (m, 2H), 0.08-0.15 (m, 1H), 0.00-0.03 (m, 1H). $^{19}$F NMR (376 MHz, DMSO-d$_6$) δ −73.67, −112.78.

Example 201: 5-(3-Chloro-2-fluoro-6-(1H-tetrazol-1-yl)phenyl)-2-(1-(4-phenyl-1H-pyrazol-1-yl)-2-((1R*,2S*)-2-(piperidine-1-carbonyl)cyclopropyl)ethyl)pyridine 1-oxide

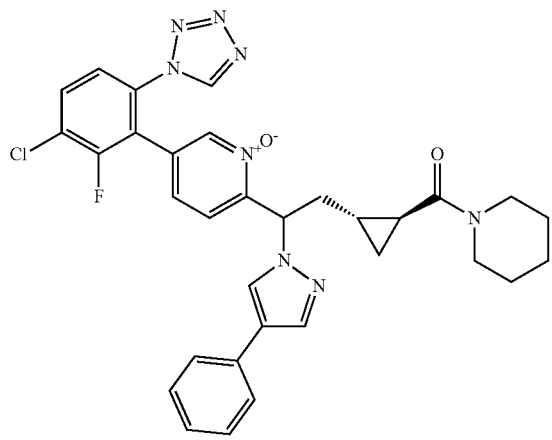

LC/MS: mass calculated for C$_{37}$H$_{32}$ClFN$_8$O$_2$: 674.23, measured (ES, m/z): 675.1 [M+H]$^+$. $^1$H NMR (300 MHz, DMSO-d$_6$) δ 9.67 (d, J=3.5 Hz, 1H), 8.40-8.52 (m, 2H), 7.92-8.11 (m, 2H), 7.71-7.77 (m, 1H), 7.49-7.67 (m, 2H), 7.04-7.42 (m, 10H), 6.05 (dd, J=7.5, 4.5 Hz, 1H), 2.53-3.95 (m, 5H), 1.28-2.38 (m, 4H), 1.10-1.35 (m, 2H), 1.75-1.84 (m, 1H), 1.60-1.64 (m, 1H). $^{19}$F NMR (282 MHz, DMSO-d$_6$) δ −74.68, −112.76 (d, J=5.0 Hz), −218.56.

Example 202: 5-(3-Chloro-2-fluoro-6-(1H-tetrazol-1-yl)phenyl)-2-(1-(4-phenyl-1H-pyrazol-1-yl)-2-((1R*,2R*)-2-(piperidine-1-carbonyl)cyclopropyl)ethyl)pyridine 1-oxide

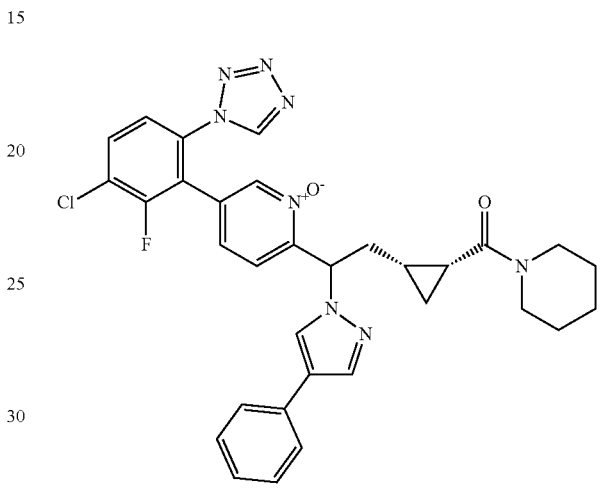

LC/MS: mass calculated for C$_{37}$H$_{32}$ClFN$_8$O$_2$: 674.23, measured (ES, m/z): 675.1 [M+H]$^+$. $^1$H NMR (300 MHz, DMSO-d$_6$) δ 9.66 (d, J=4.3 Hz, 1H), 8.36-8.49 (m, 2H), 7.98-8.08 (m, 2H), 7.71-7.74 (m, 1H), 7.53-7.64 (m, 2H), 7.06-7.42 (m, 10H), 5.98-6.08 (m, 1H), 3.81-4.17 (m, 3H), 3.08-3.38 (m, 2H), 1.90-2.35 (m, 4H), 1.70-1.74 (m, 1H), 1.04-1.18 (m, 1H), 0.76-0.88 (m, 1H), 0.48-0.56 (m, 1H). $^{19}$F NMR (282 MHz, DMSO-d$_6$) δ −74.31, −112.78.

Example 203: 5-(3-Chloro-2-fluoro-6-(1H-tetrazol-1-yl)phenyl)-2-(1-(4-phenyl-1H-pyrazol-1-yl)-2-((1R*,2S*)-2-(piperidine-1-carbonyl)cyclopropyl)ethyl)pyridine 1-oxide

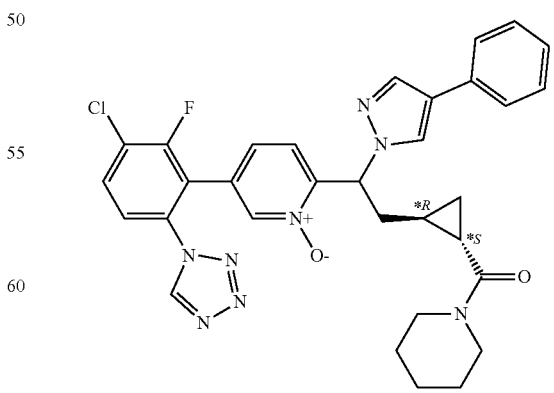

LC/MS: mass calculated for C$_{32}$H$_{30}$ClFN$_8$O$_2$: 612.21, measured (ES, m/z): 613.0 [M+H]$^+$. $^1$H NMR (300 MHz, DMSO-d$_6$) δ 9.66 (s, 1H), 8.47 (s, 1H), 8.41 (s, 1H), 7.98-8.09 (m, 2H), 7.73 (d, J=8.7 Hz, 1H), 7.54-7.64 (m, 2H), 7.31-7.37 (m, 2H), 7.09-7.27 (m, 3H), 6.03 (dd, J=10.4, 3.7 Hz, 1H), 3.25-3.45 (m, 3H), 3.11-3.21 (m, 1H), 2.36-2.43 (m, 1H), 1.98-2.06 (m, 1H), 1.65-1.70 (m, 1H), 1.21-1.54 (m, 6 H), 1.03-1.11 (m, 1H), 0.77-0.83 (m, 1H), 0.58-0.63 (m, 1H). $^{19}$F NMR (282 MHz, DMSO-d$_6$) δ −74.85, 112.77.

Example 204: 5-(3-Chloro-2-fluoro-6-(1H-tetrazol-1-yl)phenyl)-2-(1-(4-phenyl-1H-pyrazol-1-yl)-2-((1R*,2R*)-2-(piperidine-1-carbonyl)cyclopropyl)ethyl)pyridine 1-oxide

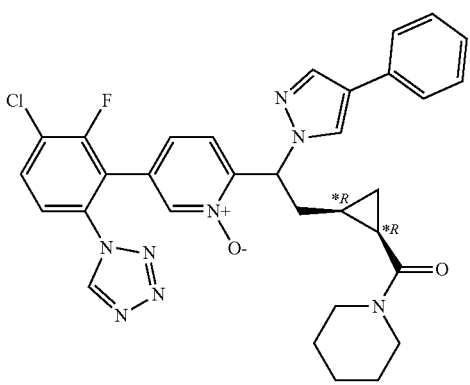

LC/MS: mass calculated for C$_{32}$H$_{30}$ClFN$_8$O$_2$: 612.21, measured (ES, m/z): 613.0 [M+H]$^+$. $^1$H NMR (300 MHz, DMSO-d$_6$) δ 9.67 (s, 1H), 8.43 (s, 1H), 8.39 (s, 1H), 7.97-8.09 (m, 2H), 7.73 (d, J=8.7 Hz, 1H), 7.54-7.63 (m, 2H), 7.24-7.40 (m, 3H), 7.06-7.24 (m, 2H), 6.08 (dd, J=9.4, 5.3 Hz, 1H), 3.52-3.62 (m, 1H), 3.42-3.48 (m, 1H), 3.28-3.38 (m, 1H), 3.32-3.42 (m, 1H), 1.83-1.96 (m, 2H), 1.33-1.59 (m, 6H), 0.90-0.97 (m, 1H), 0.82-0.88 (m, 1H), 0.68-0.75 (m, 1H).

Example 205: 5-(3-Chloro-6-cyano-2-fluorophenyl)-2-((R*)-2-cyclopropyl-1-(4-(1-methyl-6-oxo-1,6-dihydropyridazin-4-yl)-1H-pyrazol-1-yl)ethyl)-4-methoxypyridine 1-oxide

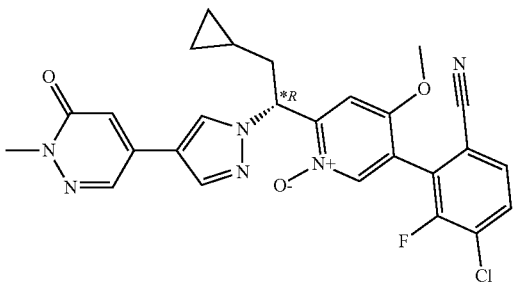

LC/MS: mass calculated for C$_{28}$H$_{22}$ClFN$_8$O$_3$: 520.14, measured (ES, m/z): 521.10 [M+H]$^+$. $^1$H NMR (300 MHz, DMSO-d$_6$) δ 8.85 (d, J=3.6 Hz, 1H), 8.55 (s, 1H), 8.23-8.33 (m, 2H), 7.85-8.00 (m, 2H), 7.26 (d, J=3.7 Hz, 1H), 7.14 (d, J=2.2 Hz, 1H), 6.15-6.23 (m, 1H), 3.82 (s, 3H), 3.62 (s, 3H), 2.45-2.51 (m, 1H), 1.95-2.05 (m, 1H), 0.54-0.63 (m, 1H), 0.31-0.44 (m, 2H), 0.15-0.19 (m, 1H), 0.00-0.05 (m, 1H).

Example 206: 5-(3-Chloro-6-cyano-2-fluorophenyl)-2-((S*)-2-cyclopropyl-1-(4-(1-methyl-6-oxo-1,6-dihydropyridazin-4-yl)-1H-pyrazol-1-yl)ethyl)-4-methoxypyridine 1-oxide

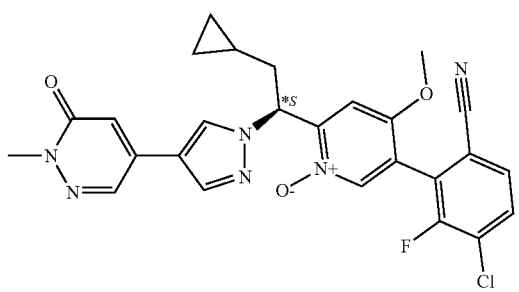

LC/MS: mass calculated for C$_{28}$H$_{22}$ClFN$_8$O$_3$: 520.14, measured (ES, m/z): 521.15 [M+H]$^+$. $^1$H NMR (300 MHz, DMSO-d$_6$) δ 8.85 (d, J=3.6 Hz, 1H), 8.55 (s, 1H), 8.23-8.33 (m, 2H), 7.85-8.00 (m, 2H), 7.26 (d, J=3.7 Hz, 1H), 7.14 (d, J=2.2 Hz, 1H), 6.15-6.23 (m, 1H), 3.82 (s, 3H), 3.62 (s, 3H), 2.45-2.51 (m, 1H), 1.95-2.05 (m, 1H), 0.54-0.63 (m, 1H), 0.31-0.44 (m, 2H), 0.15-0.19 (m, 1H), 0.00-0.05 (m, 1H).

Example 207: 5-(3-Chloro-2-fluoro-6-(1H-tetrazol-1-yl)phenyl)-2-(1-(4-(1-methyl-6-oxo-1,6-dihydropyridazin-4-yl)-1H-pyrazol-1-yl)-2-((1S*,2R*)-2-(piperidine-1-carbonyl)cyclopropyl)ethyl)pyridine 1-oxide

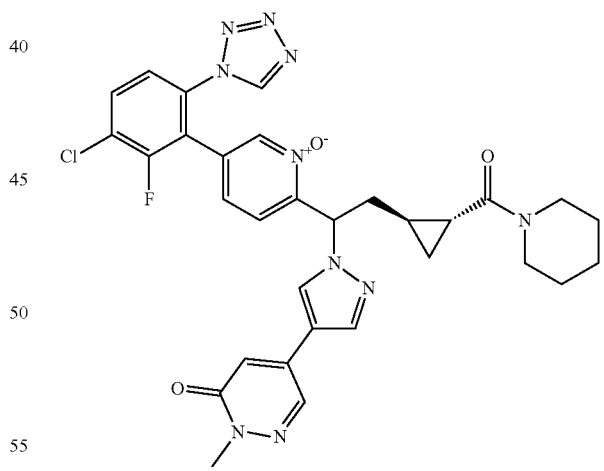

LC/MS: mass calculated for C$_{31}$H$_{30}$ClFN$_{10}$O$_3$: 644.21, measured (ES, m/z): 645.10 [M+H]$^+$. $^1$H NMR (400 MHz, DMSO-d$_6$) δ 9.68 (s, 1H), 8.80 (s, 1H), 8.43 (s, 1H), 8.24-8.30 (m, 2H), 8.06 (t, J=8.7 Hz, 1H), 7.75 (d, J=8.7 Hz, 1H), 7.33 (d, J=8.3 Hz, 1H), 7.12-7.24 (m, 2H), 6.06 (dd, J=10.5, 4.0 Hz, 1H), 3.64 (s, 3H), 3.29-3.55 (m, 3H), 3.24 (s, 1H), 2.38-2.44 (m, 1H), 1.95-2.03 (m, 1H), 1.63-1.68 (m, 1H), 1.20-1.58 (m, 6H), 1.01-1.05 (m, 1H), 0.72-0.81 (m, 1H), 0.58-0.67 (m, 1H). $^{19}$F NMR (376 MHz, DMSO-d$_6$) δ −72.83−−76.72, −112.75.

Example 208: 5-(3-Chloro-2-fluoro-6-(1H-tetrazol-1-yl)phenyl)-2-(1-(4-(1-methyl-6-oxo-1,6-dihydropyridazin-4-yl)-1H-pyrazol-1-yl)-2-((1S*,2S*)-2-(piperidine-1-carbonyl)cyclopropyl)ethyl)pyridine 1-oxide

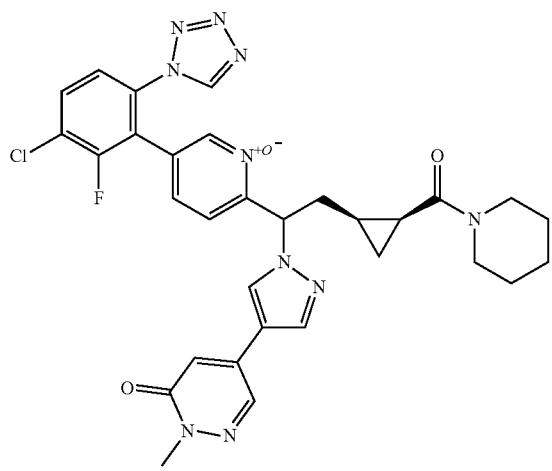

LC/MS: mass calculated for $C_{31}H_{30}ClFN_{10}O_3$: 644.21, measured (ES, m/z): 645.10 [M+H]$^+$. $^1$H NMR (400 MHz, DMSO-d$_6$) δ 9.68 (s, 1H), 8.76 (d, J=5.1 Hz, 1H), 8.43 (d, J=8.2 Hz, 1H), 8.23-8.31 (m, 2H), 8.05 (t, J=8.8 Hz, 1H), 7.75 (d, J=8.7 Hz, 1H), 7.33 (d, J=8.3 Hz, 1H), 7.11-7.24 (m, 2H), 6.07 (dd, J=9.8, 4.6 Hz, 1H), 3.61-3.63 (m, 4H), 3.44-3.49 (m, 1H), 3.31-3.39 (m, 2H), 2.31-2.38 (m, 1H), 1.92-2.05 (m, 2H), 1.40-1.62 (m, 4H), 0.81-1.15 (m, 3H). $^{19}$F NMR (376 MHz, DMSO-d$_6$) δ −74.92, −112.70.

Example 209: 2-(1-(4-(6-Amino-2-fluoropyridin-3-yl)-1H-pyrazol-1-yl)-2-(2-carbamoylcyclopropyl)ethyl)-5-(3-Chloro-2-fluoro-6-(1H-tetrazol-1-yl)phenyl)pyridine 1-oxide

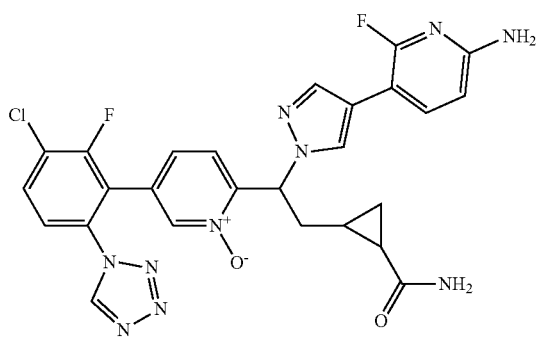 [SMILES: NC(=O)C1CC1CC(c1ccc(-c2c(-n3cnnn3)ccc(Cl)c2F)c[n+]1[O-])n1cc(-c2ccc(N)nc2F)cn1]

LC/MS: mass calculated for $C_{28}H_{21}ClF_2N_{10}O_2$: 578.15, measured (ES, m/z): 579.05 [M+H]$^+$. $^1$H NMR (400 MHz, DMSO-d$_6$) δ 9.68 (s, 1H), 8.40 (s, 1H), 8.16-8.23 (m, 1H), 8.05 (t, J=8.2 Hz, 1H), 7.73-7.85 (m, 3H), 7.33-7.36 (m, 1H), 7.21 (d, J=8.3 Hz, 1H), 7.07-7.18 (m, 1H), 6.69 (s, 1H), 6.34-6.38 (m, 1H), 6.02-6.09 (m, 1H), 2.55-2.64 (m, 1H), 2.30-2.42 (m, 1H), 1.73-1.81 (m, 1H), 1.56-1.61 (m, 1H), 1.33-1.38 (m, 1H), 0.91-0.96 (m, 1H), 0.71-0.78 (m, 1H), 0.56-0.60 (m, 1H).

Example 210: 5-(3-Chloro-2-fluoro-6-(1H-tetrazol-1-yl)phenyl)-2-((1S*)-1-(4-(4-((methoxycarbonyl)amino)phenyl)-1H-pyrazol-1-yl)-2-(tetrahydrofuran-2-yl)ethyl)pyridine 1-oxide

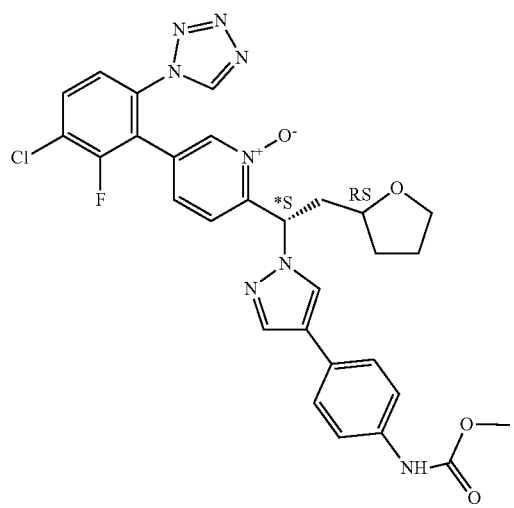 [SMILES: COC(=O)Nc1ccc(-c2cnn([C@@H](CC3CCCO3)c3ccc(-c4c(-n5cnnn5)ccc(Cl)c4F)c[n+]3[O-])c2)cc1]

LC/MS: mass calculated for $C_{29}H_{26}ClFN_8O_4$: 604.17, measured (ES, m/z): 605.3 [M+H]$^+$.

Example 211: 5-(3-Chloro-2-fluoro-6-(1H-tetrazol-1-yl)phenyl)-2-(1-(4-(4-((methoxycarbonyl)amino)phenyl)-1H-pyrazol-1-yl)-2-(tetrahydrofuran-2-yl)ethyl)pyridine 1-oxide

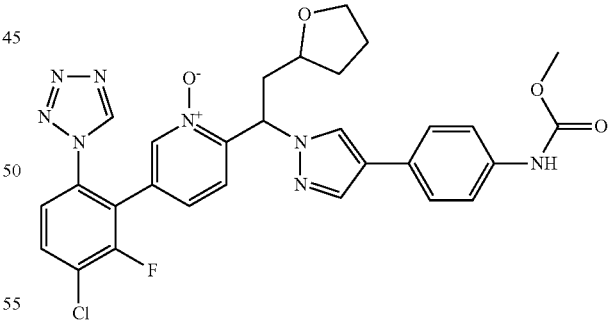

LC/MS: mass calculated for $C_{29}H_{28}ClFN_8O_4$: 604.2, measured (ES, m/z): 605.3 [M+H]$^+$. $^1$H NMR (400 MHz, CD$_3$OD) δ ppm 1.57 (bs, 3H), 1.72-1.80 (m, 1H), 1.82-2.03 (m, 4H), 2.30-2.42 (m, 2H), 2.42-2.54 (m, 2H), 2.54-2.61 (m, 1H), 2.66 (bd, J=6.4 Hz, 3H), 3.62-3.85 (m, 5H), 3.85-3.98 (m, 6H), 6.21 (bs, 3H), 6.29-6.46 (m, 5H), 7.27 (bd, J=8.3 Hz, 3H), 7.35-7.46 (m, 5H), 7.49 (bd, J=8.8 Hz, 3H), 7.60 (bd, J=8.3 Hz, 5H), 7.87-7.94 (m, 3H), 8.17 (bd, J=8.3 Hz, 3H), 8.36 (s, 4H), 9.12-9.33 (m, 3H), 9.37 (d, J=1.5 Hz, 1H).

Example 212: 5-(3-Chloro-2-fluoro-6-(1H-tetrazol-1-yl)phenyl)-2-(3-ethoxy-1-(4-(4-((methoxycarbonyl)amino)phenyl)-1H-pyrazol-1-yl)propyl)pyridine 1-oxide

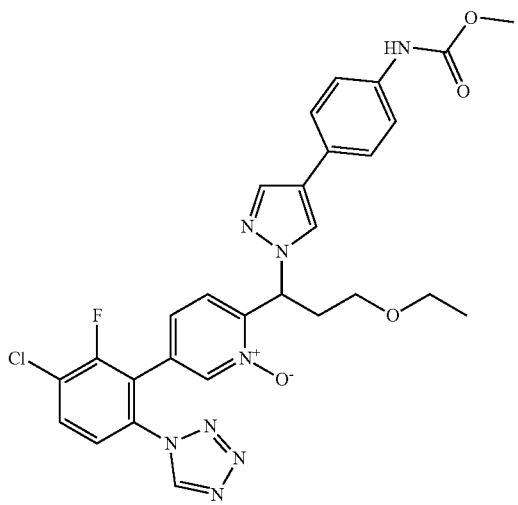 [SMILES: CCOCCC(c1ccc(-c2c(-n3cnnn3)ccc(Cl)c2F)c[n+]1[O-])n1cc(-c2ccc(NC(=O)OC)cc2)cn1]

Step 1: 1-(5-Bromopyridin-2-yl)-3-((tert-butyldimethylsilyl)oxy)propan-1-ol

To a solution of 2,5-dibromopyridine (6.0 g, 25.3 mmol, 1.0 equiv.) in toluene (90 mL) under nitrogen was added n-butyllithium (11.1 mL, 27.9 mmol, 2.5 M in THF, 1.1 equiv.) at −78° C. and the solution was stirred for 1 h at this temperature. To the solution was then added a solution of 3-((tert-butyldimethylsilyl)oxy)propanal (5.7 g, 30.4 mmol, 1.2 equiv.) in toluene (10 mL) at −78° C. and the resulting mixture was stirred at −78° C. for 2 h. The reaction was quenched with NH$_4$Cl (aq.) and extracted with ethyl acetate twice. The combined organic layer was washed with brine, dried over Na$_2$SO$_4$ and concentrated. The residue was purified by silica gel chromatography (0→50% ethyl acetate/petroleum ether) to yield 1-(5-bromopyridin-2-yl)-3-((tert-butyldimethylsilyl)oxy)propan-1-ol as a light yellow oil.

Step 2: 1-(5-Bromopyridin-2-yl)-3-((tert-butyldimethylsilyl)oxy)propyl methanesulfonate To a mixture of 1-(5-bromopyridin-2-yl)-3-((tert-butyldimethylsilyl)oxy)propan-1-ol (4.2 g, 12.1 mmol, 1.0 equiv.) and triethylamine (3.7 g, 36.4 mmol, 3.0 equiv.) in DCM (50 mL) was added methanesulfonyl chloride (1.7 g, 14.6 mmol, 1.2 equiv.) at 0° C. and the solution was stirred at room temperature for 2 h. The mixture was washed with water and brine. The organic layer was dried over Na$_2$SO$_4$ and concentrated. The residue was purified by silica gel chromatography (0→50% ethyl acetate/petroleum ether) to yield 1-(5-bromopyridin-2-yl)-3-((tert-butyldimethylsilyl)oxy)propyl methanesulfonate as a light yellow oil. LC/MS: mass calculated for C$_{15}$H$_{26}$BrNO$_4$SSi: 423.05, measured (ES, m/z): 423.95, 425.95 [M+H, M+H+2]$^+$.

Step 3: Methyl (4-(1-(1-(5-bromopyridin-2-yl)-3-((tert-butyldimethylsilyl)oxy)propyl)-1H-pyrazol-4-yl)phenyl)carbamate A mixture of 1-(5-bromopyridin-2-yl)-3-((tert-butyldimethylsilyl)oxy)propyl methanesulfonate (2.0 g, 4.7 mmol, 1.0 equiv.), methyl (4-(1H-pyrazol-4-yl)phenyl)carbamate (1.2 g, 5.7 mmol, 1.2 equiv.) and cesium carbonate (1.7 g, 5.2 mmol, 1.1 equiv.) in acetonitrile (30 mL) was stirred at 90° C. overnight. The mixture was diluted with water, and the mixture extracted with ethyl acetate twice. The combined organic layers were washed with brine, dried over Na$_2$SO$_4$ and concentrated. The residue was purified by silica gel chromatography (0→50% ethyl acetate/petroleum ether) to yield methyl (4-(1-(1-(5-bromopyridin-2-yl)-3-((tert-butyldimethylsilyl)oxy)propyl)-1H-pyrazol-4-yl)phenyl)carbamate as a white solid. LC/MS: mass calculated for C$_{25}$H$_{33}$BrN$_4$O$_3$Si: 544.15, measured (ES, m/z): 545.05, 547.05 [M+H, M+H+2]$^+$.

Step 4: Methyl (4-(1-(1-(5-bromopyridin-2-yl)-3-hydroxypropyl)-1H-pyrazol-4-yl)phenyl)carbamate To a solution of methyl (4-(1-(1-(5-bromopyridin-2-yl)-3-((tert-butyldimethylsilyl)oxy)propyl)-1H-pyrazol-4-yl)phenyl)carbamate (600 mg, 1.10 mmol, 1.0 equiv.) in THF (10 mL) was added tetrabutylammonium fluoride (1.65 mL, 1.65 mmol, 1.5 equiv, 1 M in THF) and the resulting mixture was stirred at room temperature for 1 h. The mixture was diluted with water, and the mixture extracted with ethyl acetate twice. The combined organic layers were washed with brine, dried over Na$_2$SO$_4$ and concentrated. The residue was purified by silica gel chromatography (0→50% ethyl acetate/petroleum ether) to yield methyl (4-(1-(1-(5-bromopyridin-2-yl)-3-hydroxypropyl)-1H-pyrazol-4-yl)phenyl)carbamate as a white solid. LC/MS: mass calculated for C$_{19}$H$_{19}$BrN$_4$O$_3$: 430.06, measured (ES, m/z): 430.95, 432.95 [M+H, M+H+2]$^+$.

Step 5: Methyl (4-(1-(1-(5-bromopyridin-2-yl)-3-ethoxypropyl)-1H-pyrazol-4-yl)phenyl)carbamate A mixture of methyl (4-(1-(1-(5-bromopyridin-2-yl)-3-hydroxypropyl)-1H-pyrazol-4-yl)phenyl)carbamate (200 mg, 0.46 mmol, 1.0 equiv.), silver oxide (537 mg, 2.32 mmol, 5.0 equiv.) and iodoethane (362 mg, 2.32 mmol, 5.0 equiv.) in acetonitrile (5 mL) was stirred at 50° C. overnight. After filtration, the filtrate was concentrated and the residue was purified by silica gel chromatography (0→50% ethyl acetate/petroleum ether) and then by reverse phase chromatography on C18 (80 g, MeCN/H$_2$O (0.05% CF$_3$COOH): 0→45%) to yield methyl (4-(1-(1-(5-bromopyridin-2-yl)-3-ethoxypropyl)-1H-pyrazol-4-yl)phenyl)carbamate as a light yellow solid. LC/MS: mass calculated for C$_{21}$H$_{23}$BrN$_4$O$_3$: 458.10, measured (ES, m/z): 459.00, 461.00 [M+H, M+H+2]$^+$.

Step 6: Methyl (4-(1-(1-(5-(6-amino-3-chloro-2-fluorophenyl)pyridin-2-yl)-3-ethoxypropyl)-1H-pyrazol-4-yl)phenyl)carbamate A mixture of methyl (4-(1-(1-(5-bromopyridin-2-yl)-3-ethoxypropyl)-1H-pyrazol-4-yl)phenyl)carbamate (120 mg, 0.26 mmol, 1.0 equiv.), 6-amino-3-chloro-2-fluorophenylboronic acid (74 mg, 0.39 mmol, 1.5 equiv.), potassium carbonate (108 mg, 0.78 mmol, 3.0 equiv.) and Pd(PPh$_3$)$_4$ (30 mg, 0.026 mmol, 0.1 equiv.) in 1,4-dioxane (2 mL) and water (0.5 mL) was stirred at 90° C. overnight. After cooling to room temperature, the reaction was quenched with H$_2$O and extracted with ethyl acetate twice. The combined organic layers were washed with brine, dried over Na$_2$SO$_4$ and concentrated. The residue was purified by silica gel chromatography (0→50% ethyl acetate/petroleum ether) to yield methyl (4-(1-(1-(5-(6-amino-3-chloro-2-fluorophenyl)pyridin-2-yl)-3-ethoxypropyl)-1H-pyrazol-4-yl)phenyl)carbamate as a light yellow solid. LC/MS: mass calculated for $C_{27}H_{27}ClFN_5O_3$: 523.18, measured (ES, m/z): 524.05 $[M+H]^+$.

Step 7: Methyl (4-(1-(1-(5-(3-chloro-2-fluoro-6-(1H-tetrazol-1-yl)phenyl)pyridin-2-yl)-3-ethoxypropyl)-1H-pyrazol-4-yl)phenyl)carbamate A mixture of methyl (4-(1-(1-(5-(6-amino-3-chloro-2-fluorophenyl)pyridin-2-yl)-3-ethoxypropyl)-1H-pyrazol-4-yl)phenyl)carbamate (110 mg, 0.21 mmol, 1.0 equiv.), azidotrimethylsilane (1.0 mL) and trimethoxymethane (1.0 mL) in acetic acid glacial (1 mL) was stirred at room temperature overnight. The mixture was concentrated and the residue was purified by reverse phase chromatography on C18 (80 g, MeCN/H$_2$O (0.05% CF$_3$COOH): 0→45%) to yield methyl (4-(1-(1-(5-(3-chloro-2-fluoro-6-(1H-tetrazol-1-yl)phenyl)pyridin-2-yl)-3-ethoxypropyl)-1H-pyrazol-4-yl)phenyl)carbamate as a light yellow solid. LC/MS: mass calculated for $C_{28}H_{28}ClFN_8O_3$: 576.18, measured (ES, m/z): 577.15 $[M+H]^+$.

Step 8: 5-(3-Chloro-2-fluoro-6-(1H-tetrazol-1-yl)phenyl)-2-(3-ethoxy-1-(4-(4-((methoxycarbonyl)amino)phenyl)-1H-pyrazol-1-yl)propyl)pyridine 1-oxide A mixture of methyl (4-(1-(1-(5-(3-chloro-2-fluoro-6-(1H-tetrazol-1-yl)phenyl)pyridin-2-yl)-3-ethoxypropyl)-1H-pyrazol-4-yl)phenyl)carbamate (80 mg, 0.14 mmol, 1.0 equiv.), methyl trioxorhenium (VII) (17 mg, 0.069 mmol, 0.5 equiv.) and hydrogen peroxide (0.07 mL, 0.69 mmol, 30 wt %, 5.0 equiv.) in CH$_3$OH (1.0 mL) was stirred at room temperature for 2 h. The reaction was purified by reverse phase chromatography on C18 (80 g, MeCN/H$_2$O (0.05% CF$_3$COOH): 0→45%) to yield 5-(3-chloro-2-fluoro-6-(1H-tetrazol-1-yl)phenyl)-2-(3-ethoxy-1-(4-(4-((methoxycarbonyl)amino)phenyl)-1H-pyrazol-1-yl)propyl)pyridine 1-oxide as a white solid.

LC/MS: mass calculated for $C_{28}H_{26}ClFN_8O_4$: 592.2, measured (ES, m/z): 593.1 $[M+H]^+$. $^1$H NMR (400 MHz, DMSO-d$_6$): δ 9.68 (s, 1H), 9.63 (s, 1H), 8.41 (s, 1H), 8.33 (s, 1H), 8.06 (t, J=8.2 Hz, 1H), 7.95 (s, 1H), 7.73-7.76 (m, 1H), 7.41-7.56 (m, 4H), 7.14-7.28 (m, 2H), 6.14 (t, J=7.3 Hz, 1H), 3.67 (s, 3H), 3.28-3.46 (m, 3H), 3.18-3.26 (m, 1H), 2.40-2.49 (m, 2H), 1.06 (t, J=7.0 Hz, 3H). $^{19}$F NMR (376 MHz, DMSO-d$_6$): δ −73.74, −112.73.

Example 213: 5-(3-Chloro-2-fluoro-6-(oxazol-5-yl)phenyl)-2-(2-cyclopropyl-1-(4-(1-methyl-6-oxo-1,6-dihydropyridazin-4-yl)-1H-pyrazol-1-yl)ethyl)-4-methoxypyridine 1-oxide

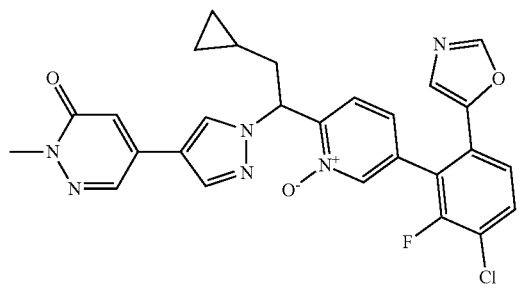 [SMILES: Cn1ncc(-c2cnn(C(CC3CC3)c3ccc(-c4c(-c5cnco5)ccc(Cl)c4F)c[n+]3[O-])c2)cc1=O]

LC/MS: mass calculated for $C_{28}H_{24}ClFN_8O_4$: 562.15, measured (ES, m/z): 563.05 $[M+H]^+$. H NMR (300 MHz, DMSO-d$_6$) δ 8.87 (d, J=6.3 Hz, 1H), 8.25-8.42 (m, 4H), 7.77-7.89 (m, 1H), 7.63-7.73 (m, 1H), 7.19-7.28 (m, 1H), 7.12-7.19 (m, 1H), 6.71-6.85 (m, 1H), 6.12-6.31 (m, 1H), 3.68 (dd, J=19.2, 2.1 Hz, 6H), 1.97-2.11 (m, 2H), 0.63 (s, 1H), 0.31-0.49 (m, 2H), 0.19 (s, 1H), 0.08 (s, 1H).

Example 214: (R*)-5-(3-Chloro-2-fluoro-6-(1H-tetrazol-1-yl)phenyl)-2-(1-(4-(4-(methoxycarbonylamino)phenyl)-1H-pyrazol-1-yl)-2-(3-methoxyphenyl)ethyl)pyridine 1-oxide

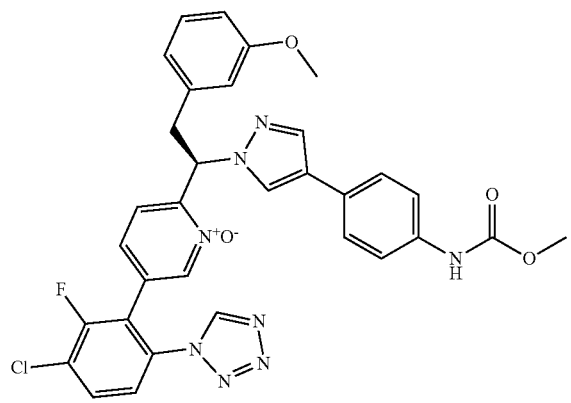

LC/MS: mass calculated for $C_{32}H_{28}ClFN_8O_4$: 640.17, measured (ES, m/z): 641.20 $[M+H]^+$. H NMR (300 MHz, DMSO-d$_6$) δ 9.69 (s, 1H), 9.62 (s, 1H), 8.47 (d, J=1.5 Hz, 1H), 8.26 (s, 1H), 8.02-8.12 (m, 1H), 7.96 (s, 1H), 7.76 (dd, J=8.7, 1.5 Hz, 1H), 7.36-7.51 (m, 4H), 7.27 (d, J=8.3 Hz, 1H), 7.08-7.23 (m, 2H), 6.68-6.79 (m, 3H), 6.11-6.23 (m, 1H), 3.65 (d, J=4.3 Hz, 6H), 3.41-3.61 (m, 2H). $^{19}$F NMR (282 MHz, DMSO-d$_6$) δ −74.54-112.69.

Example 215: (S*)-5-(3-Chloro-2-fluoro-6-(1H-tetrazol-1-yl)phenyl)-2-(1-(4-(4-((methoxycarbonyl)amino)phenyl)-1H-pyrazol-1-yl)-2-(3-methoxyphenyl)ethyl)pyridine 1-oxide

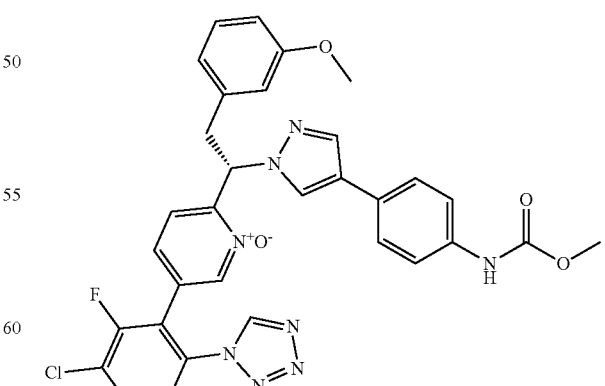

LC/MS: mass calculated for $C_{32}H_{26}ClFN_8O_4$: 640.17, measured (ES, m/z): 641.10 $[M+H]^+$. $^1$H NMR (300 MHz, DMSO-d$_6$) δ 9.69 (s, 1H), 9.62 (s, 1H), 8.47 (s, 1H), 8.26 (s, 1H), 8.06 (t, J=8.7 Hz, 1H), 7.96 (s, 1H), 7.76 (d, J=8.7 Hz, 1H), 7.36-7.50 (m, 4H), 7.26 (d, J=8.3 Hz, 1H), 7.10-7.15 (m, 2H), 6.70-6.79 (m, 3H), 6.15-6.21 (m, 1H), 3.66 (s, 3H), 3.65 (s, 3H), 3.44-3.58 (m, 2H). $^{19}$F NMR (282 MHz, DMSO-d$_6$) δ −74.45-112.70.

Example 216: 2-(2-((1S*,2R*)-2-Carboxycyclopropyl)-1-(4-phenyl-1H-pyrazol-1-yl)ethyl)-5-(3-Chloro-2-fluoro-6-(1H-tetrazol-1-yl)phenyl)pyridine 1-oxide

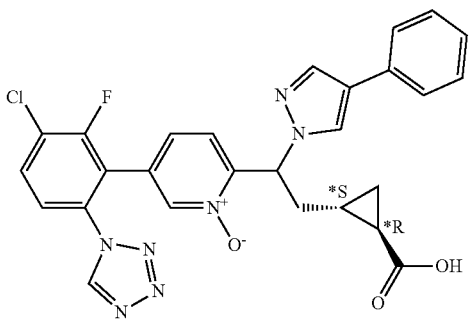 [SMILES: O=C(O)[C@@H]1C[C@H]1CC(c1ccc(-c2c(-n3cnnn3)ccc(Cl)c2F)c[n+]1[O-])n1cc(-c2ccccc2)cn1]

LC/MS: mass calculated for C$_{27}$H$_{21}$ClFN$_7$O$_3$: 545.1, measured (ES, m/z): 546.2 [M+H]$^+$. $^1$H NMR (300 MHz, DMSO-d$_6$) δ 9.67 (s, 1H), 8.46 (s, 1H), 8.41 (s, 1H), 7.97-8.01 (m, 2H), 7.73 (d, J=8.7 Hz, 1H), 7.54-7.63 (m, 2H), 7.30-7.35 (m, 2H), 7.25 (s, 1H), 7.12-7.20 (m, 2H), 5.97-6.16 (m, 1H), 2.51-2.54 (m, 1H), 2.23-2.33 (m, 1H), 1.53-1.62 (m, 1H), 0.88-1.02 (m, 2H), 0.73-0.78 (m, 1H). $^{19}$F NMR (282 MHz, DMSO-d$_6$) δ −74.17, −112.70.

Example 217: 2-(2-((1R*,2S*)-2-Carboxycyclopropyl)-1-(4-phenyl-1H-pyrazol-1-yl)ethyl)-5-(3-Chloro-2-fluoro-6-(1H-tetrazol-1-yl)phenyl)pyridine 1-oxide

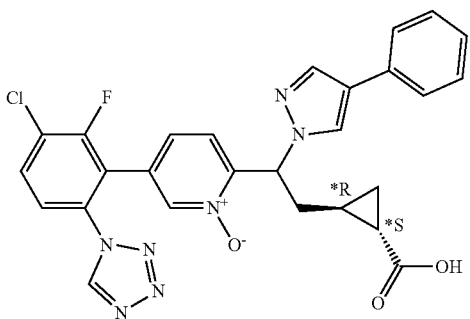 [SMILES: O=C(O)[C@H]1C[C@@H]1CC(c1ccc(-c2c(-n3cnnn3)ccc(Cl)c2F)c[n+]1[O-])n1cc(-c2ccccc2)cn1]

LC/MS: mass calculated for C$_{27}$H$_{21}$ClFN$_7$O$_3$: 545.1, measured (ES, m/z): 546.15 [M+H]$^+$. $^1$H NMR (300 MHz, DMSO-d$_6$) δ 9.66 (s, 1H), 8.48 (s, 1H), 8.40 (s, 1H), 7.97-8.10 (m, 2H), 7.73 (dd, J=8.7, 1.6 Hz, 1H), 7.54-7.64 (m, 2H), 7.33-7.43 (m, 2H), 7.04-7.27 (m, 3H), 6.04-7.13 (m, 1H), 2.53-2.65 (m, 1H), 1.88-2.00 (m, 1H), 1.29-1.40 (m, 1H), 1.05-1.20 (m, 1H), 0.0.82-0.95 (m, 1H), 0.70-0.80 (m, 1H). 19F NMR (282 MHz, DMSO-d$_6$) d −74.83, −112.70.

Example 218: 5-(5-Chloro-2-(1H-tetrazol-1-yl)phenyl)-2-(2-(4-chlorophenyl)-1-(4-(2-fluoropyridin-4-yl)-1H-pyrazol-1-yl)ethyl)pyridine 1-oxide

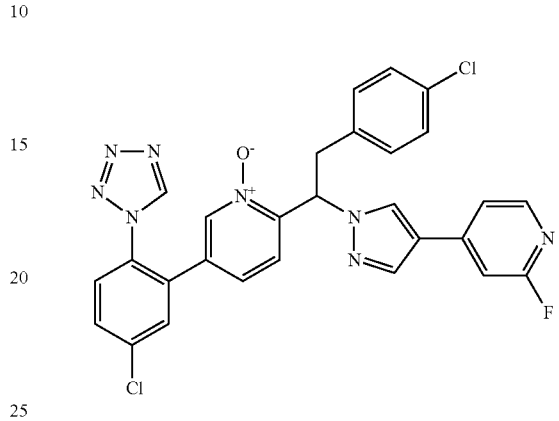

LC/MS: mass calculated for C$_{28}$H$_{19}$Cl$_2$FN$_8$O: 572.1, measured (ES, m/z): 573.2 [M+H]$^+$. $^1$H NMR (400 MHz, CD$_3$OD) δ ppm 3.53-3.73 (m, 2H), 6.30 (bd, J=3.9 Hz, 1H), 7.14-7.19 (m, 2H), 7.19-7.24 (m, 2H), 7.37-7.48 (m, 4H), 7.54 (s, 1H), 7.70-7.74 (m, 2H), 7.75-7.82 (m, 2H), 8.15 (s, 1H), 8.28 (s, 1H), 9.38 (s, 1H).

Example 219: (R*)-5-(3-Chloro-2-fluoro-6-(1H-tetrazol-1-yl)phenyl)-2-(1-(4-(pyridin-4-yl)-1H-pyrazol-1-yl)propyl)pyridine 1-oxide

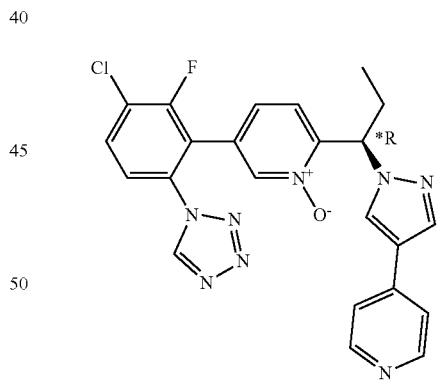

LC/MS: mass calculated for C$_{23}$H$_{18}$ClFN$_8$O: 476.12, measured (ES, m/z): 477.00 [M+H]$^+$. H NMR (400 MHz, DMSO-d$_6$) δ 9.69 (s, 1H), 8.80 (s, 1H), 8.56-8.62 (m, 2H), 8.43 (d, J=1.6 Hz, 1H), 8.27 (s, 1H), 8.02-8.13 (m, 1H), 7.71-7.82 (m, 3H), 7.35 (d, J=8.3 Hz, 1H), 7.18 (dd, J=8.3, 1.6 Hz, 1H), 5.89-5.96 (m, 1H), 2.12-2.32 (m, 2H), 0.84 (t, J=7.2 Hz, 3H). $^{19}$F NMR (376 MHz, DMSO-d$_6$) δ −73.88, −112.72.

Example 220: (S*)-5-(3-Chloro-2-fluoro-6-(1H-tetrazol-1-yl)phenyl)-2-(1-(4-(pyridin-4-yl)-1H-pyrazol-1-yl)propyl)pyridine 1-oxide

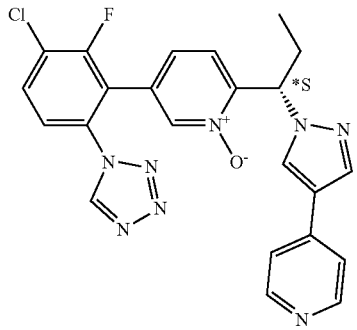 [SMILES: CC[C@@H](c1ccc(-c2c(-n3cnnn3)ccc(Cl)c2F)c[n+]1[O-])n1cc(-c2ccncc2)cn1]

LC/MS: mass calculated for $C_{23}H_{18}ClFN_8O$: 476.12, measured (ES, m/z): 477.00 [M+H]$^+$. H NMR (400 MHz, DMSO-d$_6$) δ 9.69 (s, 1H), 8.84 (s, 1H), 8.59-8.65 (m, 2H), 8.43 (d, J=1.5 Hz, 1H), 8.30 (s, 1H), 8.02-8.10 (m, 1H), 7.81-7.88 (m, 2H), 7.76 (dd, J=8.7, 1.5 Hz, 1H), 7.37 (d, J=8.3 Hz, 1H), 7.18 (dd, J=8.2, 1.6 Hz, 1H), 5.91-5.98 (m, 1H), 2.17-2.31 (m, 2H), 0.84 (t, J=7.2 Hz, 3H). $^{19}$F NMR (376 MHz, DMSO-de) δ −73.89, −112.72.

Example 221: 2-(2-((1R*,2S*)-2-(4-Carboxypiperidine-1-carbonyl)cyclopropyl)-1-(4-phenyl-1H-pyrazol-1-yl)ethyl)-5-(3-chloro-2-fluoro-6-(1H-tetrazol-1-yl)phenyl)pyridine 1-oxide

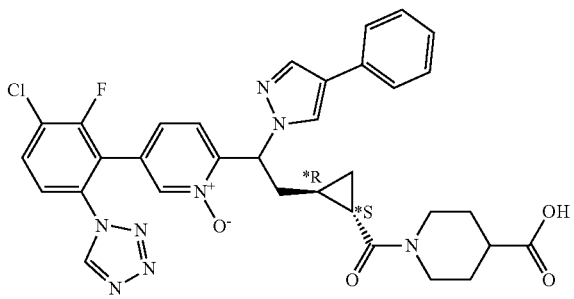 [SMILES: O=C(O)C1CCN(C(=O)[C@H]2C[C@@H]2CC(c2ccc(-c3c(-n4cnnn4)ccc(Cl)c3F)c[n+]2[O-])n2cc(-c3ccccc3)cn2)CC1]

LC/MS: mass calculated for $C_{33}H_{30}ClFN_8O_4$: 656.20, measured (ES, m/z): 657.10 [M+H]$^+$. H NMR (300 MHz, DMSO-d$_6$) δ 9.68 (s, 1H), 8.47-8.51 (m, 1H), 8.40 (d, J=1.4 Hz, 1H), 7.97-8.10 (m, 2H), 7.73 (dd, J=8.7, 1.6 Hz, 1H), 7.54-7.63 (m, 2H), 7.31-7.42 (m, 2H), 7.04-7.28 (m, 3H), 6.04 (dd, J=10.5, 3.6 Hz, 1H), 3.96 (d, J=36.8 Hz, 2H), 2.82-3.31 (m, 1H), 2.58-2.74 (m, 1H), 2.23-2.52 (m, 2H), 1.95-2.11 (m, 1H), 1.73 (d, J=20.8 Hz, 3H), 1.15-1.49 (m, 2H), 1.06 (s, 1H), 0.81 (s, 1H), 0.55-0.69 (m, 1H). $^{19}$F NMR (282 MHz, DMSO-d$_6$) δ −74.81, −112.77.

Example 222: 5-(3-Chloro-2-fluoro-6-(1H-tetrazol-1-yl)phenyl)-2-(1-(4-(4-((methoxycarbonyl)amino)phenyl)-1H-pyrazol-1-yl)-2-(1H-pyrazol-1-yl)ethyl)pyridine 1-oxide

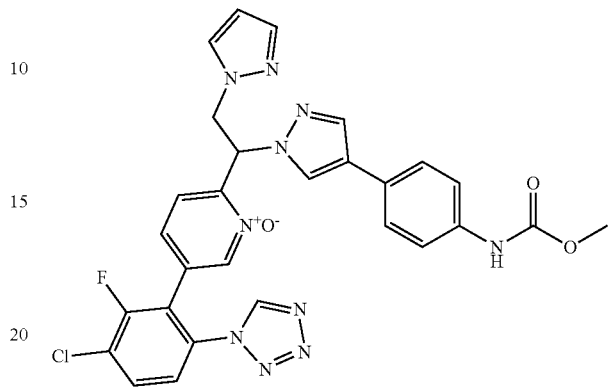

LC/MS: mass calculated for $C_{28}H_{22}ClFN_{10}O_3$: 600.15, measured (ES, m/z): 601.00 [M+H]$^+$. H NMR (400 MHz, DMSO-d$_6$) δ 9.69 (s, 1H), 9.65 (s, 1H), 8.47-8.54 (m, 1H), 8.22 (s, 1H), 8.07-8.11 (m, 1H), 7.98 (s, 1H), 7.77 (dd, J=8.7, 1.5 Hz, 1H), 7.39-7.49 (m, 6H), 7.31 (d, J=8.3 Hz, 1H), 7.20 (dd, J=8.3, 1.6 Hz, 1H), 6.52 (dd, J=9.5, 4.5 Hz, 1H), 6.04-6.15 (m, 1H), 5.02-5.13 (m, 1H), 4.90-4.99 (m, 1H), 3.66 (s, 3H). $^{19}$F NMR (376 MHz, DMSO-d$_6$) δ −74.87, −112.63.

Example 223: 2-(2-((1R*,2R*)-2-(4-Carboxypiperidine-1-carbonyl)cyclopropyl)-1-(4-phenyl-1H-pyrazol-1-yl)ethyl)-5-(3-chloro-2-fluoro-6-(1H-tetrazol-1-yl)phenyl)pyridine 1-oxide

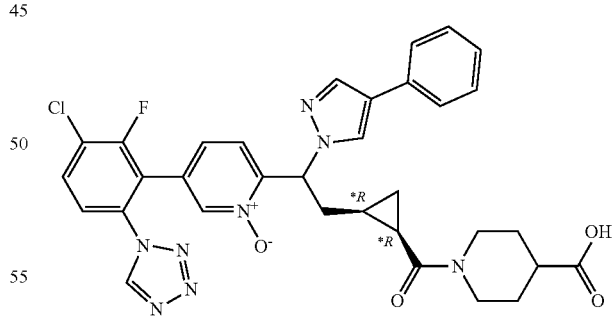

LC/MS: mass calculated for $C_{33}H_{30}ClFN_8O_4$: 656.20, measured (ES, m/z): 657.10 [M+H]$^+$. $^1$H NMR (300 MHz, DMSO-d$_6$) d 9.67 (s, 1H), 8.35-8.52 (m, 2H), 7.97-8.10 (m, 2H), 7.73 (dd, J=8.7, 1.5 Hz, 1H), 7.53-7.63 (m, 2H), 7.04-7.40 (m, 5H), 5.94-6.11 (m, 1H), 4.00-4.30 (m, 2H), 3.00-3.40 (m, 1H), 2.61-2.83 (m, 1H), 2.30-2.50 (m, 2H), 1.74-2.02 (m, 4H), 1.20-1.70 (m, 2H), 0.91-1.10 (m, 1H), 0.45-0.87 (m, 2 h). 19F NMR (282 MHz, DMSO-d$_6$) d −74.70, −112.69.

Example 224: 5-(3-Chloro-2-fluoro-6-(1H-tetrazol-1-yl)phenyl)-2-(2-cyclopropyl-1-(4-(1-methyl-6-oxo-1,6-dihydropyridin-3-yl)-1H-pyrazol-1-yl)ethyl)pyridine 1-oxide

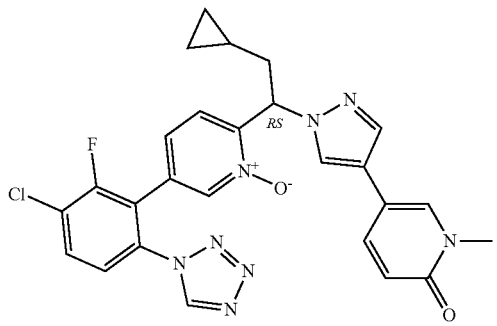 [SMILES: Cn1cc(-c2cnn(C(CC3CC3)c3ccc(-c4c(-n5cnnn5)ccc(Cl)c4F)c[n+]3[O-])c2)ccc1=O]

LC/MS: mass calculated for $C_{26}H_{22}ClFN_8O_2$: 532.2, measured (ES, m/z): 533.3 [M+H]$^+$. $^1$H NMR (400 MHz, CD$_3$OD) δ ppm 0.02-0.12 (m, 1H) 0.16-0.26 (m, 1H) 0.34-0.50 (m, 2 h) 0.65-0.76 (m, 1H) 1.94-2.02 (m, 1H) 2.43-2.57 (m, 1H) 3.59-3.67 (m, 3H) 6.14-6.27 (m, 1H) 6.59-6.67 (m, 1H) 7.23-7.34 (m, 1H) 7.41 (d, J=8.08 Hz, 1H) 7.60 (br d, J=9.09 Hz, 1H) 7.80-7.95 (m, 3H) 7.99 (s, 1H) 8.18 (s, 1H) 8.36 (s, 1H) 9.35-9.41 (m, 1H).

Example 225: (R*)-5-(3-Chloro-2-fluoro-6-(1H-tetrazol-1-yl)phenyl)-2-(3-hydroxy-1-(4-(4-((methoxycarbonyl)amino)phenyl)-1H-pyrazol-1-yl)propyl)pyridine 1-oxide

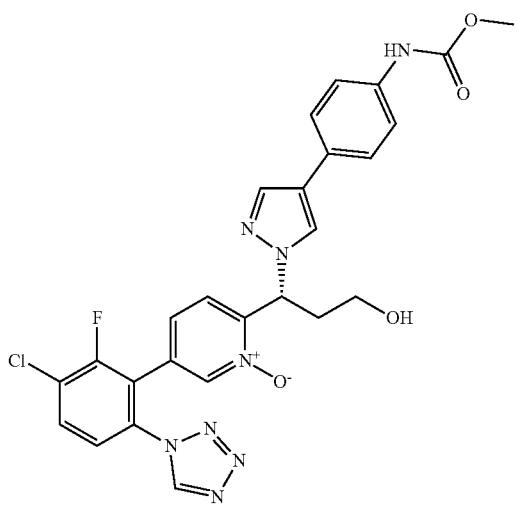 [SMILES: COC(=O)Nc1ccc(-c2cnn([C@H](CCO)c3ccc(-c4c(-n5cnnn5)ccc(Cl)c4F)c[n+]3[O-])c2)cc1]

LC/MS: mass calculated for $C_{26}H_{22}ClFN_8O_4$: 54.14, measured (ES, m/z): 565.15 [M+H]$^+$. $^1$H NMR (300 MHz, DMSO-d$_6$) δ 9.69 (s, 1H), 9.64 (s, 1H), 8.42 (s, 1H), 8.31 (s, 1H), 8.06 (t, J=8.2 Hz, 1H), 7.93 (s, 1H), 7.76 (dd, J=8.7, 1.6 Hz, 1H), 7.42-7.57 (m, 4H), 7.11-7.34 (m, 2H), 6.07-6.20 (m, 1H), 4.70 (t, J=5.1 Hz, 1H), 3.67 (s, 3H), 3.38-3.40 (m, 1H), 3.14-3.30 (m, 1H), 2.23-2.47 (m, 2H).

Example 226: (S*)-5-(3-Chloro-2-fluoro-6-(1H-tetrazol-1-yl)phenyl)-2-(3-hydroxy-1-(4-(4-((methoxycarbonyl)amino)phenyl)-1H-pyrazol-1-yl)propyl)pyridine 1-oxide

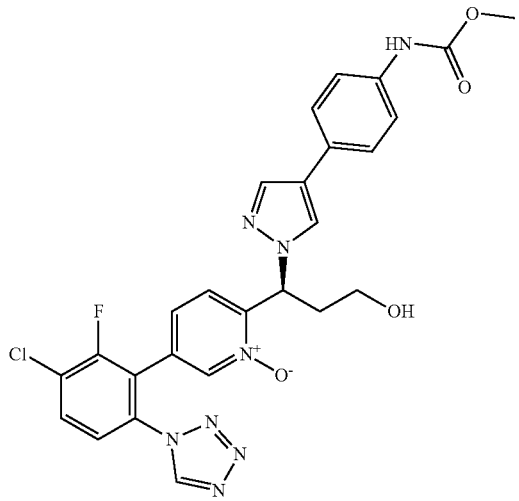 [SMILES: COC(=O)Nc1ccc(-c2cnn([C@@H](CCO)c3ccc(-c4c(-n5cnnn5)ccc(Cl)c4F)c[n+]3[O-])c2)cc1]

LC/MS: mass calculated for $C_{26}H_{22}ClFN_8O_4$: 564.14, measured (ES, m/z): 565.20 [M+H]$^+$. $^1$H NMR (300 MHz, DMSO-d$_6$) δ 9.66 (d, J=15.7 Hz, 2H), 8.42 (s, 1H), 8.31 (s, 1H), 8.00-8.12 (m, 1H), 7.94 (s, 1H), 7.76 (d, J=8.7 Hz, 1H), 7.39-7.65 (m, 4H), 7.08-7.37 (m, 2H), 6.19 (d, J=9.0 Hz, 1H), 4.70 (t, J=5.1 Hz, 1H), 3.67 (s, 3H), 3.38-3.42 (m, 1H), 3.14-3.30 (m, 1H), 2.23-2.45 (m, 2H). $^{19}$F NMR (300 MHz, DMSO-d$_6$) δ −112.71.

Example 227: 5-(3-Chloro-2-fluoro-6-(1H-tetrazol-1-yl)phenyl)-2-((R*)-1-(4-(4-((methoxycarbonyl)amino)phenyl)-1H-pyrazol-1-yl)-2-((S*)-tetrahydro-2H-pyran-2-yl)ethyl)pyridine 1-oxide

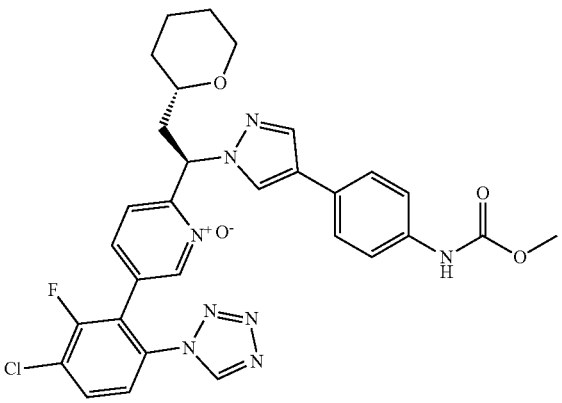

LC/MS: mass calculated for $C_{30}H_{28}ClFN_8O_4$: 618.2, measured (ES, m/z): 619.1 [M+H]$^+$. $^1$H NMR (300 MHz, DMSO-d$_6$) δ 9.69 (s, 1H), 9.63 (s, 1H), 8.40 (d, J=1.5 Hz, 1H), 8.32 (s, 1H), 8.02-8.11 (m, 1H), 7.91 (s, 1H), 7.76 (dd, J=8.7, 1.6 Hz, 1H), 7.49-7.55 (m, 2H), 7.39-7.48 (m, 2H), 7.34 (d, J=8.3 Hz, 1H), 7.16 (dd, J=8.4, 1.6 Hz, 1H), 6.07-7.17 (m, 1H), 3.77 (d, J=11.6 Hz, 1H), 3.67 (s, 3H), 3.01-3.25 (m, 2H), 2.25-2.42 (m, 2H), 1.73 (t, J=11.9 Hz, 2H), 1.40 (s, 3H), 1.15-1.23 (m, 1H). $^{19}$F NMR (282 MHz, DMSO-$d_6$) δ -74.44, -112.72.

Example 228: 5-(3-Chloro-2-fluoro-6-(1H-tetrazol-1-yl)phenyl)-2-((S*)-1-(4-(4-((methoxycarbonyl)amino)phenyl)-1H-pyrazol-1-yl)-2-((S*)-tetrahydro-2H-pyran-2-yl)ethyl)pyridine 1-oxide

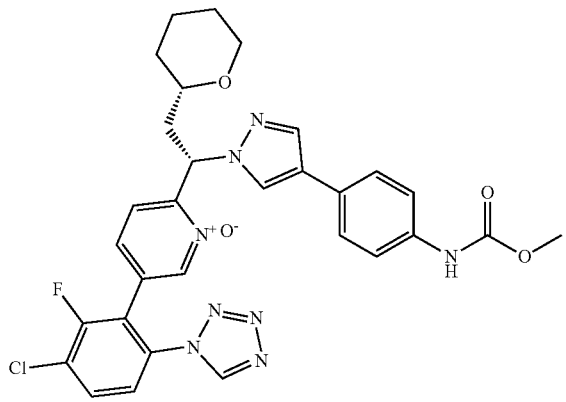

Step 1: N-Methoxy-N-methyl-2-(tetrahydro-2H-pyran-2-yl)acetamide

To a solution of 2-(tetrahydro-2H-pyran-2-yl)acetic acid (500 mg, 3.47 mmol, 1.0 equiv.) in DCM (20 mL) was added N,O-dimethylhydroxylamine hydrochloride (408 mg, 4.17 mmol, 1.2 equiv.), EDC.HCl (999 mg, 5.21 mmol, 1.5 equiv.), DMAP (423 mg, 3.47 mmol, 1.0 equiv.) and DIEA (1343 mg, 10.41 mmol, 3.0 equiv.). The resulting mixture was stirred at room temperature overnight. The resulting mixture was washed with 1N HCl and extracted with DCM (3×20 mL). The organic layers were combined, dried over Na$_2$SO$_4$, filtered and concentrated to yield N-methoxy-N-methyl-2-(tetrahydro-2H-pyran-2-yl)acetamide as a light yellow oil. $^1$H NMR (400 MHz, Chloroform-d): δ 3.90-3.97 (m, 1H), 3.74-3.85 (m, 1H), 3.68 (s, 3H), 3.40-3.49 (m, 1H), 3.17 (s, 3H), 2.76 (dd, J=15.5, 7.6 Hz, 1H), 2.36 (dd, J=15.3, 5.2 Hz, 1H), 1.76-1.87 (m, 1H), 1.62-1.72 (m, 1H), 1.43-1.57 (m, 3H), 1.23-1.37 (m, 1H).

Step 2: 1-(5-Bromopyridin-2-yl)-2-(tetrahydro-2H-pyran-2-yl)ethan-1-one n-Butyllithium (2.5 M in hexanes, 1.3 mL, 3.20 mmol, 1.2 equiv.) was added dropwise to a stirred solution of 2,5-dibromopyridine (759 mg, 3.20 mmol, 1.2 equiv.) in toluene (15 mL) under nitrogen at -78° C. The mixture was stirred at -78° C. for 2 h. Then N-methoxy-N-methyl-2-(tetrahydro-2H-pyran-2-yl)acetamide (500 mg, 2.67 mmol, 1.0 equiv.) in toluene (5 mL) was added dropwise and the mixture was stirred at -78° C. for 1 h. The mixture was quenched with sat. aqueous NH$_4$Cl, then allowed to warm to room temperature. The organic layer was separated, washed with brine, dried Na$_2$SO$_4$, filtered and concentrated under vacuum. The resulting residue was purified by silica gel chromatography (0→100% ethyl acetate/petroleum ether) to yield 1-(5-bromopyridin-2-yl)-2-(tetrahydro-2H-pyran-2-yl)ethan-1-one as a light yellow solid. LC/MS: mass calculated for $C_{12}H_{14}BrNO_2$: 283.02, measured (ES, m/z): 284.00, 286.00 [M+H, M+H+2]$^+$.

Step 3: 1-(5-Bromopyridin-2-yl)-2-(tetrahydro-2H-pyran-2-yl)ethan-1-ol

To a solution of 1-(5-bromopyridin-2-yl)-2-(tetrahydro-2H-pyran-2-yl)ethan-1-one (413 mg, 1.45 mmol, 1.0 equiv.) in CH$_3$OH (10 mL) was added NaBH$_4$ (66 mg, 1.74 mmol, 1.2 equiv.) at 0° C. The resulting mixture was stirred at room temperature overnight. The reaction was quenched with water. The resulting mixture was extracted with ethyl acetate (3×20 mL). The organic layers were combined, dried over Na$_2$SO$_4$, filtered, and concentrated to yield 1-(5-bromopyridin-2-yl)-2-(tetrahydro-2H-pyran-2-yl)ethan-1-ol as a white solid. LC/MS: mass calculated for $C_{12}H_{16}BrNO_2$: 285.04, measured (ES, m/z): 286.00, 288.00 [M+H, M+H+2]$^+$.

Step 4: 1-(5-Bromopyridin-2-yl)-2-((R*)tetrahydro-2H-pyran-2-yl)ethyl methanesulfonate To a solution of 1-(5-bromopyridin-2-yl)-2-(tetrahydro-2H-pyran-2-yl)ethan-1-ol (400 mg, 1.40 mmol, 1.0 equiv.) in DCM (20 mL) was added methanesulfonyl chloride (320 mg, 2.80 mmol, 2.0 equiv.), Et$_3$N (424 mg, 4.20 mmol, 3.0 equiv.). The resulting mixture was stirred at room temperature for 3 h. The resulting mixture was extracted with ethyl acetate (3×10 mL). The organic layers were combined, dried over Na$_2$SO$_4$, filtered and concentrated. The resulting residue was purified by silica gel chromatography (0→50% ethyl acetate/petroleum ether) to yield 1-(5-bromopyridin-2-yl)-2-((R*)-2H-pyran-2-yl)ethyl methanesulfonate as a light yellow solid. LC/MS: mass calculated for $C_{13}H_{18}BrNO_4S$: 363.01, measured (ES, m/z): 363.95, 365.95 [M+H, M+H+2]$^+$.

Step 5: Methyl (4-(1-(1-(5-bromopyridin-2-yl)-2-((S*)-tetrahydro-2H-pyran-2-yl)ethyl)-1H-pyrazol-4-yl)phenyl)carbamate To a solution of 1-(5-bromopyridin-2-yl)-2-((R*)tetrahydro-2H-pyran-2-yl)ethyl methanesulfonate (284 mg, 0.78 mmol, 1.0 equiv.) in ACN (10 mL) was added methyl 4-(1H-pyrazol-4-yl)phenylcarbamate (254 mg, 1.17 mmol, 1.5 equiv.) and Cs$_2$CO$_3$ (508 mg, 1.56 mmol, 2.0 equiv.). The resulting mixture was stirred at 70° C. for 3 h. The reaction was quenched with H$_2$O (10 mL). The resulting mixture was extracted with ethyl acetate (3×20 mL). The organic layers were combined, dried over Na$_2$SO$_4$, filtered and concentrated. The resulting residue was purified by silica gel chromatography (0→50% ethyl acetate/petroleum ether) to yield methyl (4-(1-(1-(5-bromopyridin-2-yl)-2-((S*)-tetrahydro-2H-pyran-2-yl)ethyl)-1H-pyrazol-4-yl)phenyl)carbamate as a light yellow solid. LC/MS: mass calculated for $C_{23}H_{25}BrN_4O_3$: 484.11, measured (ES, m/z): 485.00, 487.00 [M+H, M+H+2]$^+$.

Step 6: Methyl (4-(1-(1-(5-(6-amino-3-chloro-2-fluorophenyl)pyridin-2-yl)-2-((S*)-tetrahydro-2H-pyran-2-yl)ethyl)-1H-pyrazol-4-yl)phenyl)carbamate To a solution of methyl (4-(1-(1-(5-bromopyridin-2-yl)-2-((S*)-tetrahydro-2H-pyran-2-yl)ethyl)-1H-pyrazol-4-yl)phenyl)carbamate (120 mg, 0.25 mmol, 1.0 equiv.) in 1,4-dioxane/H$_2$O (12 mL) was added 6-amino-3-chloro-2-fluorophenylboronic acid (94 mg, 0.49 mmol, 2.0 equiv.), K$_2$CO$_3$ (114 mg, 0.74 mmol, 3.0 equiv.) and Pd(PPh$_3$)$_4$ (28 mg, 0.025 mmol, 0.1 equiv.) under $N_2$. The resulting mixture was stirred at 80° C. for 2 h. The reaction was quenched with $H_2O$ (10 mL). The resulting mixture was extracted with ethyl acetate (3×30 mL). The organic layers were combined, dried over $Na_2SO_4$, filtered and concentrated. The resulting residue was purified by silica gel chromatography (0→100% ethyl acetate/petroleum ether) to yield methyl (4-(1-(1-(5-(6-amino-3-chloro-2-fluorophenyl)pyridin-2-yl)-2-((S*)-tetrahydro-2H-pyran-2-yl)ethyl)-1H-pyrazol-4-yl)phenyl) carbamate as a light yellow solid. LC/MS: mass calculated for $C_{29}H_{29}ClFN_5O_3$: 549.19, measured (ES, m/z): 550.25 $[M+H]^+$.

Step 7: Methyl (4-(1-(1-(5-(3-chloro-2-fluoro-6-(1H-tetrazol-1-yl)phenyl)pyridin-2-yl)-2-((S*)-tetrahydro-2H-pyran-2-yl)ethyl)-1H-pyrazol-4-yl)phenyl) carbamate To a solution of methyl (4-(1-(1-(5-(6-amino-3-chloro-2-fluorophenyl)pyridin-2-yl)-2-((S*)-tetrahydro-2H-pyran-2-yl)ethyl)-1H-pyrazol-4-yl)phenyl)carbamate (185 mg, 0.34 mmol, 1.0 equiv.) in acetic acid (5 mL) was added $TMSN_3$ (193.8 mg, 1.68 mmol, 5.0 equiv.) and trimethoxymethane (356 mg, 3.36 mmol, 10.0 equiv.). The resulting mixture was stirred at room temperature overnight. The resulting mixture was extracted with EtOAc (3×10 mL). The organic layers were combined, dried over $Na_2SO_4$, filtered and concentrated. The resulting residue was purified by C18 chromatography (0→50% $CH_3CN/H_2O$) to yield methyl (4-(1-(1-(5-(3-chloro-2-fluoro-6-(1H-tetrazol-1-yl)phenyl)pyridin-2-yl)-2-((S*)-tetrahydro-2H-pyran-2-yl)ethyl)-1H-pyrazol-4-yl)phenyl)carbamate. LC/MS: mass calculated for $C_{30}H_{28}ClFN_8O_3$: 602.20, measured (ES, m/z): 603.20 $[M+H]^+$.

Step 8: 5-(3-Chloro-2-fluoro-6-(1H-tetrazol-1-yl)phenyl)-2-((S*)-1-(4-(4-((methoxycarbonyl)amino)phenyl)-1H-pyrazol-1-yl)-2-((S*)-tetrahydro-2H-pyran-2-yl)ethyl)pyridine 1-oxide A mixture of methyl (4-(1-(1-(5-(3-chloro-2-fluoro-6-(1H-tetrazol-1-yl)phenyl)pyridin-2-yl)-2-((S*)-tetrahydro-2H-pyran-2-yl)ethyl)-1H-pyrazol-4-yl)phenyl)carbamate (350 mg, 0.58 mmol, 1.0 equiv.), methyl trioxorhenium (VII) (72 mg, 0.29 mmol, 0.5 equiv.) and hydrogen peroxide (0.29 mL, 2.90 mmol, 30%, 5.0 equiv.) in $CH_3OH$ (5 mL) was stirred at room temperature for 1 h. The reaction was purified by reverse phase chromatography on C18 (80 g, MeCN/$H_2O$ (0.05% $CF_3COOH$): 0→45%) to yield 5-(3-chloro-2-fluoro-6-(1H-tetrazol-1-yl)phenyl)-2-(1-(4-(4-((methoxycarbonyl)amino)phenyl)-1H-pyrazol-1-yl)-2-((S*)-tetrahydro-2H-pyran-2-yl)ethyl)pyridine 1-oxide as a white solid. 20 mg of the product was then further purified with Prep-Chiral-HPLC to yield 5-(3-chloro-2-fluoro-6-(1H-tetrazol-1-yl)phenyl)-2-((S*)-1-(4-(4-((methoxycarbonyl)amino)phenyl)-1H-pyrazol-1-yl)-2-((S*)-tetrahydro-2H-pyran-2-yl)ethyl)pyridine 1-oxide as a white solid.
LC/MS: mass calculated for $C_{30}H_{28}ClFN_8O_4$: 618.2, measured (ES, m/z): 619.1 $[M+H]^+$. $^1H$ NMR (300 MHz, DMSO-$d_6$): δ 9.69 (s, 1H), 9.63 (s, 1H), 8.40 (s, 1H), 8.32 (s, 1H), 8.01-8.10 (m, 1H), 7.91 (s, 1H), 7.74-7.77 (m, 1H), 7.40-7.55 (m, 4H), 7.26-7.37 (m, 1H), 7.08-7.19 (m, 1H), 6.13 (t, J=7.2 Hz, 1H), 3.72-3.80 (m, 1H), 3.67 (s, 3H), 3.04-3.20 (m, 2H), 2.26-2.46 (m, 2H), 1.66-1.79 (m, 2H), 1.35-1.45 (m, 3H), 1.12-1.27 (m, 1H). $^{19}F$ NMR (282 MHz, DMSO-$d_6$): δ −73.78, −112.73.

Example 229: 5-(3-Chloro-2-fluoro-6-(1H-tetrazol-1-yl)phenyl)-2-(1-(4-(4-((methoxycarbonyl)amino)phenyl)-1H-pyrazol-1-yl)-2-((1R*,2S*)-2-(3-phenylpyrrolidine-1-carbonyl)cyclopropyl)ethyl) pyridine 1-oxide

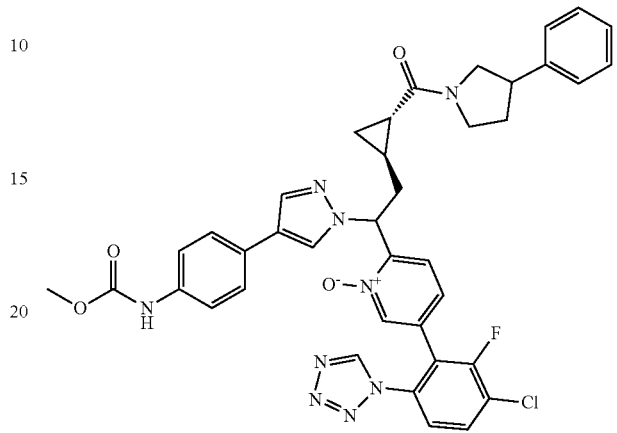

LC/MS: mass calculated for $C_{39}H_{35}ClFN_9O_4$: 747.24, measured (ES, m/z): 748.10 $[M+H]^+$. $^1H$ NMR (300 MHz, DMSO-$d_6$) δ 9.61-9.78 (m, 2H), 8.31-8.48 (m, 2H), 7.87-8.12 (m, 2H), 7.71-7.82 (m, 1H), 7.46-7.53 (m, 4H), 7.04-7.42 (m, 7H), 5.72-6.12 (m, 1H), 3.82-3.87 (m, 1H), 3.76 (s, 3H), 3.08-3.57 (m, 4H), 1.51-2.40 (m, 4H), 1.11-1.48 (m, 2H), 0.52-1.08 (m, 2H).

Example 230: 5-(3-Chloro-2-fluoro-6-(1H-tetrazol-1-yl)phenyl)-2-(1-(4-(4-((methoxycarbonyl)amino)phenyl)-1H-pyrazol-1-yl)-2-((1S*,2S*)-2-(3-phenylpyrrolidine-1-carbonyl)cyclopropyl)ethyl) pyridine 1-oxide

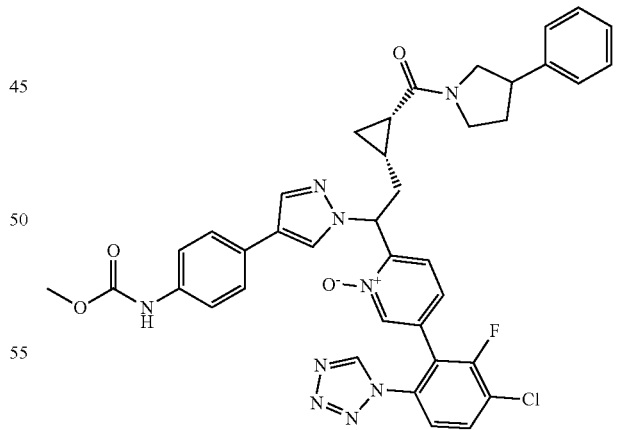

LC/MS: mass calculated for $C_{39}H_{35}ClFN_9O_4$: 747.24, measured (ES, m/z): 748.10 $[M+H]^+$. H NMR (300 MHz, DMSO-$d_6$) δ 9.61-9.84 (m, 2H), 8.28-8.49 (m, 2H), 8.02-8.13 (m, 1H), 7.90-8.00 (m, 1H), 7.71-7.81 (m, 1H), 7.45-7.59 (m, 3H), 7.03-7.41 (m, 7H), 5.79-6.18 (m, 1H), 3.78-4.25 (m, 2H), 3.76 (s, 3H), 3.08-3.45 (m, 2H), 2.31-2.41 (m, 1H), 2.01-2.28 (m, 2H), 1.65-1.99 (m, 2H), 0.98-1.15 (m, 1H), 0.45-0.99 (m, 2H).

Example 231: 2-(2-((1R*,2S*)-2-(3-Carboxypiperidine-1-carbonyl)cyclopropyl)-1-(4-phenyl-1H-pyrazol-1-yl)ethyl)-5-(3-chloro-2-fluoro-6-(1H-tetrazol-1-yl)phenyl)pyridine 1-oxide

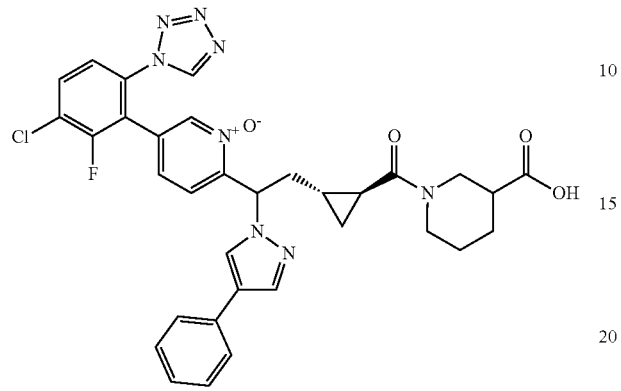

LC/MS: mass calculated for $C_{33}H_{30}ClFN_8O_4$: 656.20, measured (ES, m/z): 657.10 [M+H]$^+$. $^1$H NMR (300 MHz, DMSO-d$_6$) δ 9.66 (s, 1H), 8.46 (d, J=4.4 Hz, 1H), 8.40 (d, J=1.5 Hz, 1H), 8.00-8.12 (m, 2H), 7.73 (dd, J=8.7, 1.6 Hz, 1H), 7.54-7.63 (m, 2H), 7.30-7.50 (m, 2H), 7.11-7.26 (m, 3H), 6.00-6.10 (m, 1H), 3.47-4.38 (m, 2H), 2.56-3.41 (m, 2H), 1.65-2.45 (m, 5H), 1.18-1.64 (m, 3H), 1.00-1.19 (m, 1H), 0.73-0.92 (m, 1H), 0.58-0.71 (m, 1H). $^{19}$F NMR (282 MHz, DMSO-d$_6$) d −74.92, −112.76.

Example 232: 2-(2-((1R*,2R*)-2-(3-Carboxypiperidine-1-carbonyl)cyclopropyl)-1-(4-phenyl-1H-pyrazol-1-yl)ethyl)-5-(3-chloro-2-fluoro-6-(1H-tetrazol-1-yl)phenyl)pyridine 1-oxide

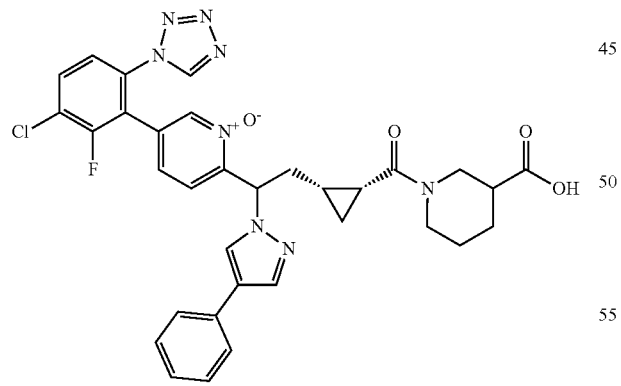

LC/MS: mass calculated for $C_{33}H_{30}ClFN_8O_4$: 656.20, measured (ES, m/z): 657.1 [M+H]$^+$. $^1$H NMR (300 MHz, DMSO-d$_6$) δ 9.67 (d, J=1.2 Hz, 1H), 8.39-8.51 (m, 2H), 7.96-8.11 (m, 2H), 7.73 (dd, J=8.7, 1.5 Hz, 1H), 7.53-7.63 (m, 2H), 7.07-7.41 (m, 5H), 5.95-6.16 (m, 1H), 2.65-4.48 (m, 4H), 2.12-2.43 (m, 2H), 1.86-2.12 (m, 3H), 1.13-1.78 (m, 3H), 0.41-1.10 (m, 3H). $^{19}$F NMR (282 MHz, DMSO-d$_6$) δ −74.78, −112.70.

Example 233: (R*)-5-(3-Chloro-2-fluoro-6-(1H-tetrazol-1-yl)phenyl)-2-(3-(difluoromethoxy)-1-(4-(4-((methoxycarbonyl)amino)phenyl)-1H-pyrazol-1-yl)propyl)pyridine 1-oxide

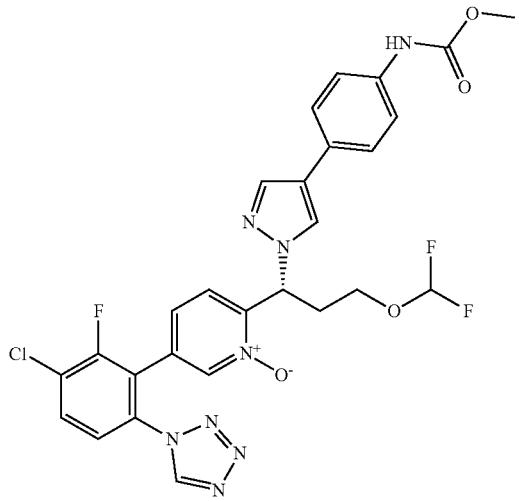 [SMILES: COC(=O)Nc1ccc(-c2cnn([C@H](CCOC(F)F)c3ccc(-c4c(-n5cnnn5)ccc(Cl)c4F)c[n+]3[O-])c2)cc1]

LC/MS: mass calculated for $C_{27}H_{22}ClF_3N_8O_4$: 614.14, measured (ES, m/z): 615.1 [M+H]$^+$. $^1$H NMR (300 MHz, DMSO-d$_6$) δ 9.68 (s, 1H), 9.64 (s, 1H), 8.44 (s, 1H), 8.34 (s, 1H), 8.06 (dd, J=8.7, 7.8 Hz, 1H), 7.99 (s, 1H), 7.76 (dd, J=8.7, 1.6 Hz, 1H), 7.42-7.56 (m, 4H), 7.19 (d, J=1.1 Hz, 2H), 6.31-6.89 (m, 1H), 6.15 (dd, J=9.8, 4.8 Hz, 1H), 3.80-3.91 (m, 1H), 3.65-3.72 (m, 4H), 2.54-2.65 (m, 2H). $^{19}$F NMR (282 MHz, DMSO-d$_6$) δ −73.41, −83.20, −112.68.

Example 234: (R)-5-(3-Chloro-2-fluoro-6-(1H-tetrazol-1-yl)phenyl)-2-(3-(difluoromethoxy)-1-(4-(4-((methoxycarbonyl)amino)phenyl)-1H-pyrazol-1-yl)propyl)pyridine 1-oxide

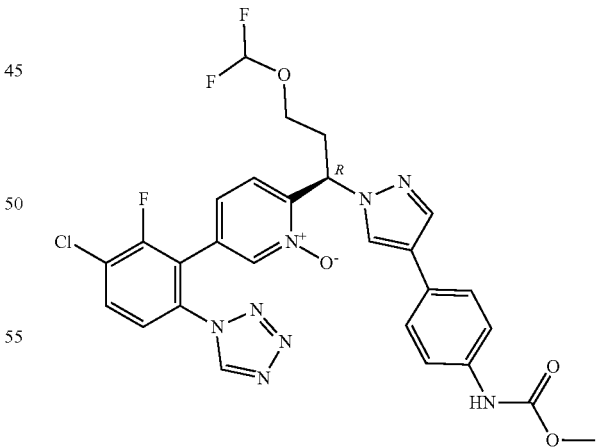

Step 1: Methyl (4-(1-(1-(5-bromopyridin-2-yl)-3-(difluoromethoxy)propyl)-1H-pyrazol-4-yl)phenyl)carbamate Methyl (4-(1-(1-(5-bromopyridin-2-yl)-3-hydroxypropyl)-1H-pyrazol-4-yl)phenyl)carbamate (200 mg, 0.46 mmol, 1.0 equiv.) was dissolved in acetonitrile (2 mL), and cuprous iodide (18 mg, 0.09 mmol, 0.2 equiv.) was added. The mixture was heated to 50° C. under nitrogen atmosphere, and a solution of 2-(fluorosulfonyl)difluoro acetic acid (124 mg, 0.70 mmol, 1.5 equiv.) in acetonitrile (1 mL) was added dropwise.

The reaction mixture was heated for an additional 30 min at 50° C. The reaction was diluted with water, and the mixture extracted with ethyl acetate twice. The combined organic layers were washed with brine, dried over $Na_2SO_4$ and concentrated. The residue was purified by silica gel chromatography (0→50% ethyl acetate/petroleum ether) to yield methyl (4-(1-(1-(5-bromopyridin-2-yl)-3-(difluoromethoxy)propyl)-1H-pyrazol-4-yl)phenyl)carbamate as a light yellow solid. LC/MS: mass calculated for $C_{20}H_{19}BrF_2N_4O_3$: 480.06, measured (ES, m/z): 481.05, 483.05 [M+H, M+H+2]$^+$.

Step 2: Methyl (4-(1-(1-(5-(6-amino-3-chloro-2-fluorophenyl)pyridin-2-yl)-3-(difluoromethoxy)propyl)-1H-pyrazol-4-yl)phenyl)carbamate A mixture of methyl (4-(1-(1-(5-bromopyridin-2-yl)-3-(difluoromethoxy)propyl)-1H-pyrazol-4-yl)phenyl)carbamate (110 mg, 0.23 mmol, 1.0 equiv.), 6-amino-3-chloro-2-fluorophenylboronic acid (87 mg, 0.46 mmol, 2.0 equiv.), potassium carbonate (95 mg, 0.69 mmol, 3.0 equiv.) and $Pd(PPh_3)_4$ (26 mg, 0.023 mmol, 0.1 equiv.) in 1,4-dioxane (2 mL) and water (0.5 mL) was stirred at 90° C. overnight. After cooling to room temperature, the reaction was quenched with $H_2O$ and extracted with ethyl acetate twice. The combined organic layers were washed with brine, dried over $Na_2SO_4$ and concentrated. The residue was purified by silica gel chromatography (0→50% ethyl acetate/petroleum ether) to yield methyl (4-(1-(1-(5-(6-amino-3-chloro-2-fluorophenyl)pyridin-2-yl)-3-(difluoromethoxy)propyl)-1H-pyrazol-4-yl)phenyl)carbamate as a light yellow solid. LC/MS: mass calculated for $C_{26}H_{23}ClF_3N_5O_3$: 545.14, measured (ES, m/z): 546.25 [M+H]$^+$.

Step 3: Methyl (4-(1-(1-(5-(3-chloro-2-fluoro-6-(1H-tetrazol-1-yl)phenyl)pyridin-2-yl)-3-(difluoromethoxy)propyl)-1H-pyrazol-4-yl)phenyl)carbamate A mixture of methyl (4-(1-(1-(5-(6-amino-3-chloro-2-fluorophenyl)pyridin-2-yl)-3-(difluoromethoxy)propyl)-1H-pyrazol-4-yl)phenyl)carbamate (100 mg, 0.18 mmol, 1.0 equiv.), azidotrimethylsilane (1 mL) and trimethoxymethane (1 mL) in acetic acid glacial (1 mL) was stirred at room temperature overnight. The mixture was concentrated and the residue was purified by reverse phase chromatography on C18 (80 g, MeCN/$H_2O$ (0.05% $CF_3COOH$): 0→45%) to yield methyl (4-(1-(1-(5-(3-chloro-2-fluoro-6-(1H-tetrazol-1-yl)phenyl)pyridin-2-yl)-3-(difluoromethoxy)propyl)-1H-pyrazol-4-yl)phenyl)carbamate as a light yellow solid. LC/MS: mass calculated for $C_{27}H_{22}ClF_3N_8O_3$: 598.15, measured (ES, m/z): 599.00 [M+H]$^+$.

Step 4: (R)-5-(3-Chloro-2-fluoro-6-(1H-tetrazol-1-yl)phenyl)-2-(3-(difluoromethoxy)-1-(4-(4-((methoxycarbonyl)amino)phenyl)-1H-pyrazol-1-yl)propyl)pyridine 1-oxide A mixture of methyl (4-(1-(1-(5-(3-chloro-2-fluoro-6-(1H-tetrazol-1-yl)phenyl)pyridin-2-yl)-3-(difluoromethoxy)propyl)-1H-pyrazol-4-yl)phenyl)carbamate (120 mg, 0.20 mmol, 1.0 equiv.), methyl trioxorhenium (VII) (25 mg, 0.10 mmol) and hydrogen peroxide (0.10 mL, 1.00 mmol, 30 wt %, 5.0 equiv.) in $CH_3OH$ (2.0 mL) was stirred at room temperature for 1 h. The reaction was purified by reverse phase chromatography on C18 (80 g, MeCN/$H_2O$ (0.05% $CF_3COOH$): 0→45%) and then Prep-Chiral HPLC to yield (R)-5-(3-chloro-2-fluoro-6-(1H-tetrazol-1-yl)phenyl)-2-(3-(difluoromethoxy)-1-(4-(4-((methoxycarbonyl)amino)phenyl)-1H-pyrazol-1-yl)propyl)pyridine 1-oxide as a white solid.

LC/MS: mass calculated for $C_{27}H_{22}ClF_3N_8O_4$: 614.1, measured (ES, m/z): 615.2 [M+H]$^+$. $^1$H NMR (300 MHz. DMSO-$d_6$): δ 9.68 (s, 1H), 9.63 (s, 1H), 8.44 (s, 1H), 8.34 (s, 1H), 8.06 (t, J=8.3 Hz, 1H), 8.00 (s, 1H), 7.76 (d, J=9.0 Hz, 1H), 7.42-7.57 (m, 4H), 7.07-7.30 (m, 2H), 6.64 (t, J=75.8 Hz, 1H), 6.11-6.19 (m, 1H), 3.81-3.89 (m, 1H), 3.62-3.75 (m, 4H), 2.55-2.66 (m, 2H).

Example 235: 2-(1-(4-(4-Carboxyphenyl)-1H-pyrazol-1-yl)-2-(2-methylcyclopropyl)ethyl)-5-(3-chloro-2-fluoro-6-(1H-tetrazol-1-yl)phenyl)pyridine 1-oxide

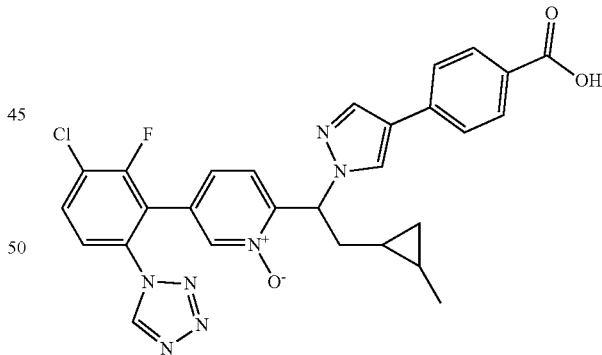

LC/MS: mass calculated for $C_{28}H_{23}ClFN_7O_3$: 559.15, measured (ES, m/z): 560.25[M+H]$^+$. H NMR (400 MHz, DMSO-$d_6$) δ 12.82 (brs, 1H), 9.68 (d, J=1.3 Hz, 1H), 8.64 (d, J=5.6 Hz, 1H), 8.41 (dd, J=5.3, 1.6 Hz, 1H), 8.12 (d, J=5.0 Hz, 1H), 8.05 (dd, J=8.7, 7.7 Hz, 1H), 7.88-7.96 (m, 2H), 7.71-7.82 (m, 3H), 7.28-7.36 (m, 1H), 7.11-7.16 (m, 1H), 6.09-6.12 (m, 1H), 3.32-3.75 (m, 1H), 2.20-2.41 (m, 1H), 1.85-2.01 (m, 1H), 0.75-1.12 (m, 3H), 0.41-0.62 (m, 1H), 0.12-0.34 (m, 2H), 0.05-0.11 (m, 1H). $^{19}$F NMR (376 MHz, DMSO) δ −73.78, −112.75.

Example 236: 5-(3-Chloro-2-fluoro-6-(1H-tetrazol-1-yl)phenyl)-2-((1S*)-3-methoxy-1-(4-(4-((methoxycarbonyl)amino)phenyl)-1H-pyrazol-1-yl)butyl)pyridine 1-oxide

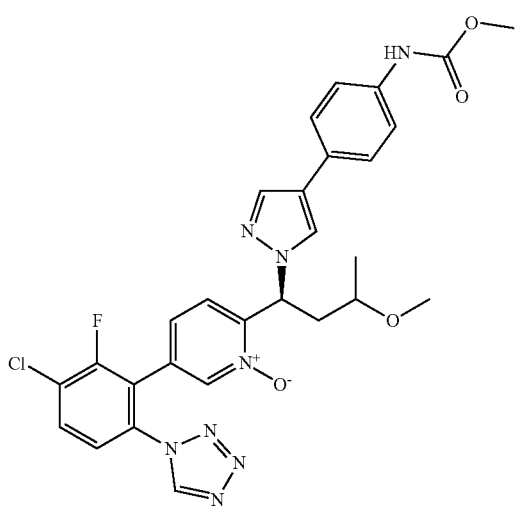 [SMILES: COC(=O)Nc1ccc(-c2cnn([C@@H](CC(C)OC)c3ccc(-c4c(-n5cnnn5)ccc(Cl)c4F)c[n+]3[O-])c2)cc1]

LC/MS: mass calculated for $C_{28}H_{26}ClFN_8O_4$: 592.2, measured (ES, m/z): 593.0 [M+H]+. $^1$H NMR (300 MHz, DMSO-$d_6$) δ 9.64 (d, J=14.4 Hz, 2H), 8.33-8.41 (m, 2H), 7.98-8.08 (m, 1H), 7.94 (s, 1H), 7.68-7.78 (m, 1H), 7.40-7.54 (m, 4H), 7.25 (d, J=8.3 Hz, 1H), 7.12 (d, J=8.6 Hz, 1H), 6.21 (d, J=7.2 Hz, 1H), 3.65 (s, 3H), 3.12 (s, 3H), 2.88-3.05 (m, 1H), 2.35 (t, J=11.7 Hz, 1H), 2.23 (d, J=10.8 Hz, 1H), 1.04 (d, J=6.1 Hz, 3H). $^{19}$F NMR (282 MHz, DMSO-$d_6$) δ −73.40, −112.74.

Example 237: 5-(3-Chloro-2-fluoro-6-(1H-tetrazol-1-yl)phenyl)-2-(2-isopropoxy-1-(4-(4-((methoxycarbonyl)amino)phenyl)-1H-pyrazol-1-yl)ethyl)pyridine 1-oxide

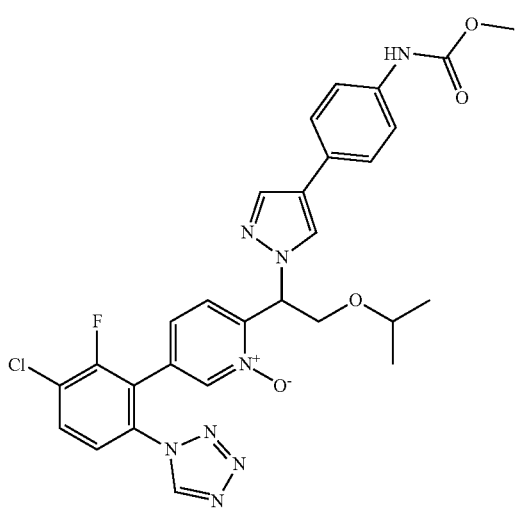 [SMILES: COC(=O)Nc1ccc(-c2cnn(C(COC(C)C)c3ccc(-c4c(-n5cnnn5)ccc(Cl)c4F)c[n+]3[O-])c2)cc1]

LC/MS: mass calculated for $C_{28}H_{26}ClFN_8O_4$: 592.2, measured (ES, m/z): 593.05 [M+H]+. $^1$H NMR (300 MHz, DMSO-$d_6$) δ 9.68 (s, 1H), 9.64 (s, 1H), 8.44 (s, 1H), 8.33 (s, 1H), 8.04 (dd, J=8.7, 7.8 Hz, 1H), 7.92 (s, 1H), 7.73 (dd, J=8.7, 1.6 Hz, 1H), 7.38-7.55 (m, 4H), 7.10-7.20 (m, 2H), 6.09-6.20 (m, 1H), 3.99-4.19 (m, 2H), 3.67 (s, 3H), 3.54-3.63 (m, 1H), 0.92-1.10 (m, 6H). 19F NMR (282 MHz, DMSO-$d_6$) d −74.66, −112.73.

Example 238: 5-(3-Chloro-2-fluoro-6-(1H-tetrazol-1-yl)phenyl)-2-((1R)-3-methoxy-1-(4-(4-((methoxycarbonyl)amino)phenyl)-1H-pyrazol-1-yl)butyl)pyridine 1-oxide

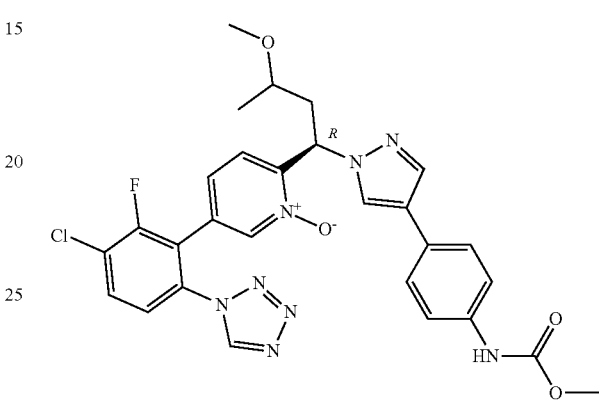

LC/MS: mass calculated for $C_{28}H_{26}ClFN_8O_4$: 592.2, measured (ES, m/z): 593.05 [M+H]+. $^1$H NMR (300 MHz, DMSO-$d_6$) δ 9.60-9.72 (m, 2H), 8.40 (s, 1H), 8.34 (s, 1H), 8.04 (t, J=8.2 Hz, 1H), 7.94 (s, 1H), 7.67-7.78 (m, 1H), 7.49-7.58 (m, 2H), 7.40-7.49 (m, 2H), 7.23-7.31 (m, 1H), 7.10-7.17 (m, 1H), 6.18-6.28 (m, 1H), 3.65 (s, 3H), 3.12 (s, 3H), 2.91-3.04 (m, 1H), 2.15-2.45 (m, 2H), 1.04 (d, J=6.1 Hz, 3H). 19F NMR (282 MHz, DMSO-$d_6$) d −112.74.

Example 239: 5-(3-Chloro-2-fluoro-6-(1H-tetrazol-1-yl)phenyl)-2-(1-(4-(4-((methoxycarbonyl)amino)phenyl)-1H-pyrazol-1-yl)-2-((1S*,2R*)-2-(piperidine-1-carbonyl)cyclopropyl)ethyl)pyridine 1-oxide

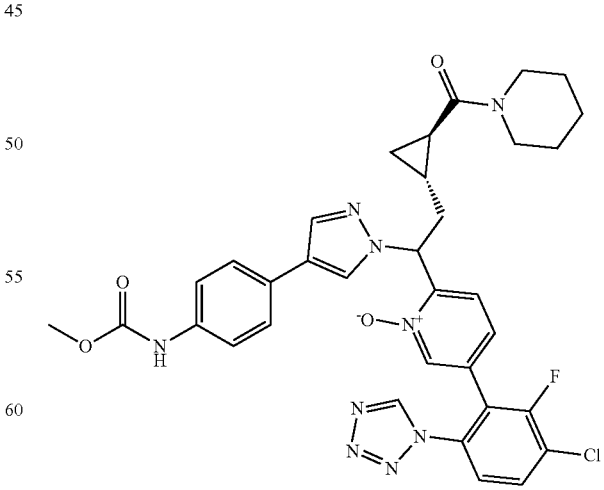

LC/MS: mass calculated for $C_{34}H_{33}ClFN_9O_4$: 685.23, measured (ES, m/z): 686.10 [M+H]+. H NMR (300 MHz, DMSO-$d_6$) δ 9.58-9.70 (m, 2H), 8.31-8.46 (m, 2H), 7.90-

8.12 (m, 2H), 7.73 (dd, J=8.7, 1.5 Hz, 1H), 7.38-7.59 (m, 4H), 7.09-7.32 (m, 2H), 5.93-6.12 (m, 1H), 3.65 (s, 3H), 3.31-3.39 (m, 2H), 3.15-3.22 (m, 1H), 2.35-2.43 (m, 1H), 1.95-2.09 (m, 1H), 1.70-1.94 (m, 1H), 1.21-1.65 (m, 6H), 1.00-1.12 (m, 1H), 0.75-0.89 (m, 1H), 0.55-0.65 (m, 1H). $^{19}$F NMR (282 MHz, DMSO-$d_6$) δ −73.41, −112.76.

Example 240: 5-(3-Chloro-2-fluoro-6-(1H-tetrazol-1-yl)phenyl)-2-(1-(4-(4-((methoxycarbonyl)amino)phenyl)-1H-pyrazol-1-yl)-2-((1S*,2S*)-2-(piperidine-1-carbonyl)cyclopropyl)ethyl)pyridine 1-oxide

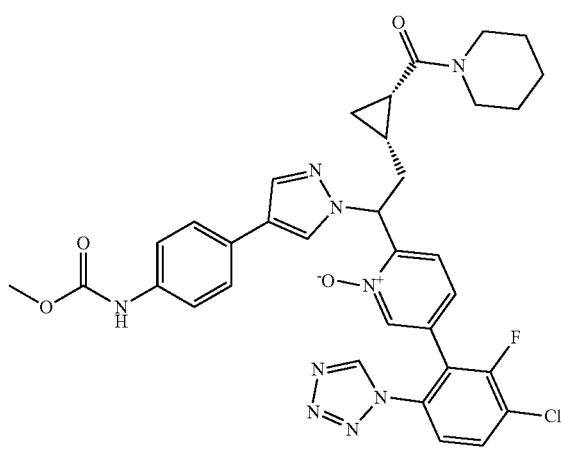

LC/MS: mass calculated for $C_{34}H_{33}ClFN_9O_4$: 685.23, measured (ES, m/z): 686.10 [M+H]$^+$. $^1$H NMR (300 MHz, DMSO-$d_6$) δ 9.59-9.70 (m, 2H), 8.29-8.44 (m, 2H), 7.98-8.07 (m, 1H), 7.95 (d, J=6.1 Hz, 1H), 7.73 (dd, J=8.7, 1.5 Hz, 1H), 7.41-7.55 (m, 4H), 7.08-7.28 (m, 2H), 5.93-6.07 (m, 1H), 3.65 (s, 3H), 3.32-3.43 (m, 1H), 3.19-3.31 (m, 1H), 2.31-2.45 (m, 1H), 1.93-2.11 (m, 1H), 1.61-1.72 (m, 1H), 1.21-1.60 (m, 6H), 1.05-1.12 (m, 1H), 0.75-0.85 (m, 1H), 0.55-0.65 (m, 1H). $^{19}$F NMR (282 MHz, DMSO-$d_6$) δ −73.41, −112.77.

Example 241: (R*)-5-(3-Chloro-2-fluoro-6-(1H-tetrazol-1-yl)phenyl)-2-(1-(4-(1-oxidopyridin-4-yl)-1H-pyrazol-1-yl)propyl)pyridine 1-oxide

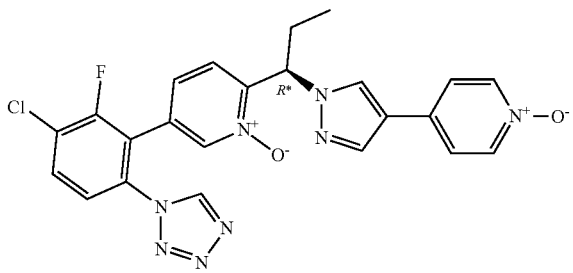 [SMILES: CC[C@H](c1ccc(-c2c(-n3cnnn3)ccc(Cl)c2F)c[n+]1[O-])n1cc(-c2cc[n+]([O-])cc2)cn1]

LC/MS: mass calculated for $C_{23}H_{18}ClFN_8O_2$: 492.12, measured (ES, m/z): 493.20 [M+H]$^+$. $^1$H NMR (400 MHz, DMSO-$d_6$) δ 9.68 (s, 1H), 8.65 (s, 1H), 8.42 (d, J=1.6 Hz, 1H), 8.18-8.24 (m, 2H), 8.15 (s, 1H), 8.01-8.11 (m, 1H), 7.75 (dd, J=8.7, 1.5 Hz, 1H), 7.63-7.71 (m, 2H), 7.30 (d, J=8.3 Hz, 1H), 7.17 (dd, J=8.3, 1.7 Hz, 1H), 5.90 (dd, J=9.6, 5.0 Hz, 1H), 2.11-2.39 (m, 2H), 0.84 (t, J=7.2 Hz, 3H). $^{19}$F NMR (376 MHz, DMSO-$d_6$) δ −73.88, −112.72.

Example 242: (S*)-5-(3-Chloro-2-fluoro-6-(1H-tetrazol-1-yl)phenyl)-2-(1-(4-(1-oxidopyridin-4-yl)-1H-pyrazol-1-yl)propyl)pyridine 1-oxide

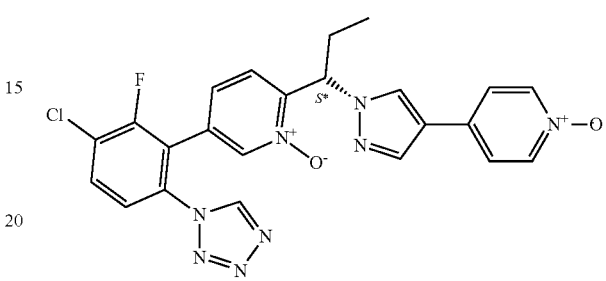

LC/MS: mass calculated for $C_{23}H_{18}ClFN_8O_2$: 492.12, measured (ES, m/z): 493.00 [M+H]$^+$. $^1$H NMR (400 MHz, DMSO-$d_6$) δ 9.68 (s, 1H), 8.65 (s, 1H), 8.42 (d, J=1.6 Hz, 1H), 8.17-8.24 (m, 2H), 8.15 (s, 1H), 7.98-8.09 (m, 1H), 7.75-7.83 (m, 1H), 7.63-7.70 (m, 2H), 7.30 (d, J=8.3 Hz, 1H), 7.17 (dd, J=8.3, 1.7 Hz, 1H), 5.90 (dd, J=9.6, 5.0 Hz, 1H), 2.12-2.28 (m, 2H), 0.84 (t, J=7.2 Hz, 3H). $^{19}$F NMR (376 MHz, DMSO-$d_6$) δ −73.89, −112.72.

Example 243: (R*)-5-(3-Chloro-2-fluoro-6-(1H-tetrazol-1-yl)phenyl)-2-(2-(4-fluorophenyl)-1-(4-(pyridin-4-yl)-1H-pyrazol-1-yl)ethyl)pyridine 1-oxide

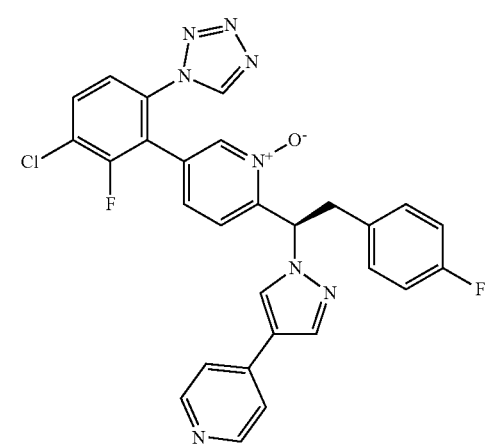 [SMILES: [O-][n+]1cc(-c2c(-n3cnnn3)ccc(Cl)c2F)ccc1[C@@H](Cc1ccc(F)cc1)n1cc(-c2ccncc2)cn1]

LC/MS: mass calculated for $C_{28}H_{19}ClF_2N_8O$: 556.13, measured (ES, m/z): 557.00 [M+H]$^+$. $^1$H NMR (400 MHz, DMSO-$d_6$) δ 9.69 (s, 1H), 8.57 (s, 1H), 8.44-8.52 (m, 3H), 8.21 (s, 1H), 8.02-8.11 (m, 1H), 7.76 (dd, J=8.7, 1.5 Hz, 1H), 7.52-7.59 (m, 2H), 7.39 (d, J=8.3 Hz, 1H), 7.11-7.29 (m, 3H), 6.99-7.10 (m, 2H), 6.21 (dd, J=10.0, 4.6 Hz, 1H), 3.43-3.79 (m, 2H). $^{19}$F NMR (376 MHz, DMSO-$d_6$) δ −116.07, −112.68.

Example 244: (S*)-5-(3-Chloro-2-fluoro-6-(1H-tetrazol-1-yl)phenyl)-2-(2-(4-fluorophenyl)-1-(4-(pyridin-4-yl)-1H-pyrazol-1-yl)ethyl)pyridine 1-oxide

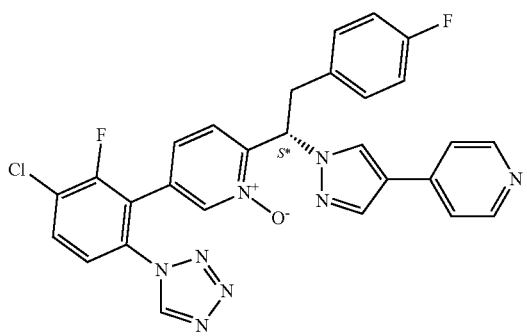 [SMILES: [O-][n+]1cc(-c2c(-n3cnnn3)ccc(Cl)c2F)ccc1[C@H](Cc1ccc(F)cc1)n1cc(-c2ccncc2)cn1]

LC/MS: mass calculated for $C_{28}H_{19}ClF_2N_8O$: 556.13, measured (ES, m/z): 557.05 [M+H]$^+$. $^1$H NMR (400 MHz, DMSO-d$_6$) δ 9.69 (s, 1H), 8.58 (s, 1H), 8.44-8.55 (m, 3H), 8.22 (s, 1H), 8.02-8.11 (m, 1H), 7.76 (dd, J=8.7, 1.5 Hz, 1H), 7.56-7.62 (m, 2H), 7.40 (d, J=8.3 Hz, 1H), 7.13-7.25 (m, 3H), 7.01-7.10 (m, 2H), 6.15-6.25 (m, 1H), 3.44-3.70 (m, 2H).

Example 245: (R*)-5-(3-Chloro-2-fluoro-6-(1H-tetrazol-1-yl)phenyl)-2-(2-(4-fluorophenyl)-1-(4-(1-oxidopyridin-4-yl)-1H-pyrazol-1-yl)ethyl)pyridine 1-oxide

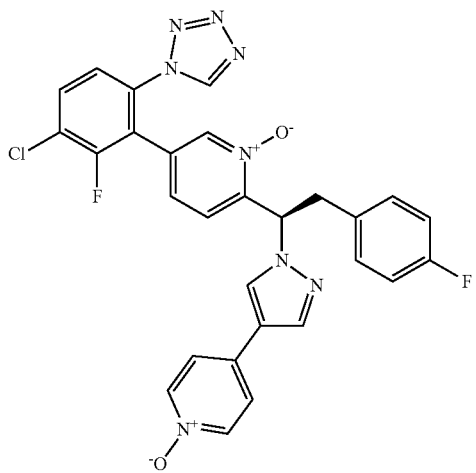

LC/MS: mass calculated for $C_{28}H_{19}ClF_2N_8O_2$: 572.13, measured (ES, m/z): 573.00 [M+H]$^+$. $^1$H NMR (400 MHz, DMSO-d$_6$) δ 9.69 (s, 1H), 8.44-8.54 (m, 2H), 8.17 (d, J=7.5 Hz, 3H), 8.01-8.08 (m, 1H), 7.76 (dd, J=8.7, 1.5 Hz, 1H), 7.55-7.63 (m, 2H), 7.37 (d, J=8.3 Hz, 1H), 7.14-7.25 (m, 3H), 7.01-7.11 (m, 2H), 6.19 (dd, J=9.9, 4.5 Hz, 1H), 3.46-3.64 (m, 2H). $^{19}$F NMR (376 MHz, DMSO-d$_6$) δ −112.44, −116.03.

Example 246: (S*)-5-(3-Chloro-2-fluoro-6-(1H-tetrazol-1-yl)phenyl)-2-(2-(4-fluorophenyl)-1-(4-(1-oxidopyridin-4-yl)-1H-pyrazol-1-yl)ethyl)pyridine 1-oxide

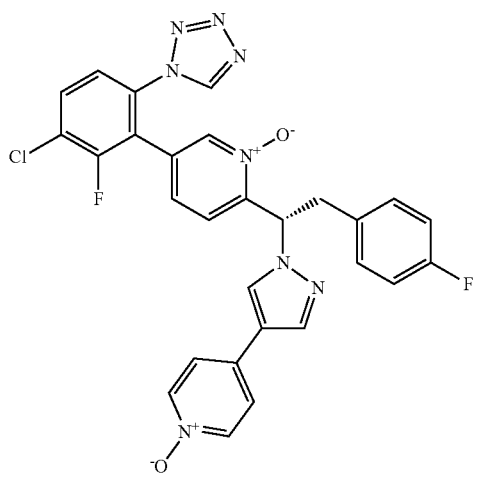

LC/MS: mass calculated for $C_{28}H_{19}ClF_2N_8O$: 572.13, measured (ES, m/z): 573.00 [M+H]$^+$. $^1$H NMR (400 MHz, DMSO-d$_6$) δ 9.69 (s, 1H), 8.44-8.54 (m, 2H), 8.17 (d, J=7.4 Hz, 3H), 8.01-8.11 (m, 1H), 7.76 (dd, J=8.8, 1.5 Hz, 1H), 7.56-7.63 (m, 2H), 7.37 (d, J=8.3 Hz, 1H), 7.13-7.25 (m, 3H), 7.01-7.11 (m, 2H), 6.19 (dd, J=9.9, 4.6 Hz, 1H), 3.42-3.70 (m, 2H). $^{19}$F NMR (376 MHz, DMSO-d$_6$) δ −112.69, −116.05.

Example 247: 2-(1-(4-(4-Carboxyphenyl)-1H-pyrazol-1-yl)-2-((1S*,2R*)-2-(4-methoxyphenyl)cyclopropyl)ethyl)-5-(5-chloro-2-(1H-tetrazol-1-yl)phenyl)pyridine 1-oxide

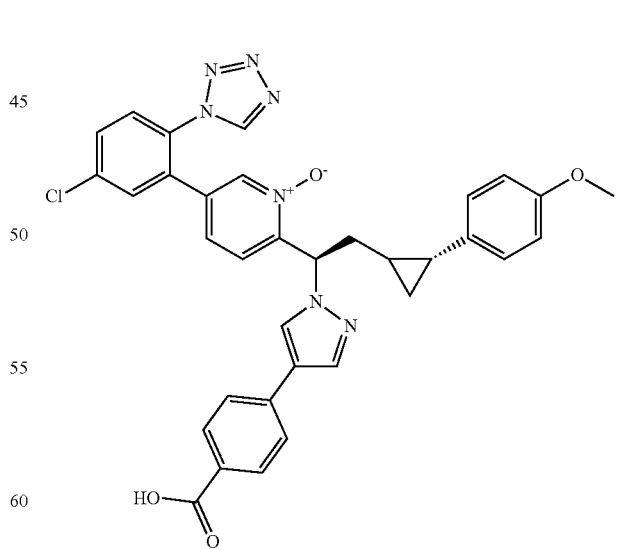

LC/MS: mass calculated for $C_{34}H_{28}ClN_7O_4$: 633.19, measured (ES, m/z): 634.20[M+H]$^+$. $^1$H NMR (400 MHz, DMSO-d$_6$) δ 9.68 (s, 1H), 8.58 (s, 1H), 8.29 (d, J=1.7 Hz, 1H), 8.13 (s, 1H), 7.78-7.95 (m, 5H), 7.64-7.74 (m, 2H), 7.21 (d, J=8.4 Hz, 1H), 6.96 (dd, J=8.3, 1.7 Hz, 1H), 6.71-6.79 (m, 2H), 6.60-6.68 (m, 2H), 6.12 (dd, J=10.1, 3.8 Hz, 1H), 3.62 (s, 3H), 2.39-2.44 (m, 1H), 2.11-2.18 (m, 1H), 1.49-1.53 (m, 1H), 0.88-0.92 (m, 1H), 0.71-0.78 (m, 2H).

Example 248: 2-(1-(4-(4-Carboxyphenyl)-1H-pyrazol-1-yl)-2-((1S*,2S*)-2-(4-methoxyphenyl)cyclopropyl)ethyl)-5-(5-chloro-2-(1H-tetrazol-1-yl)phenyl)pyridine 1-oxide

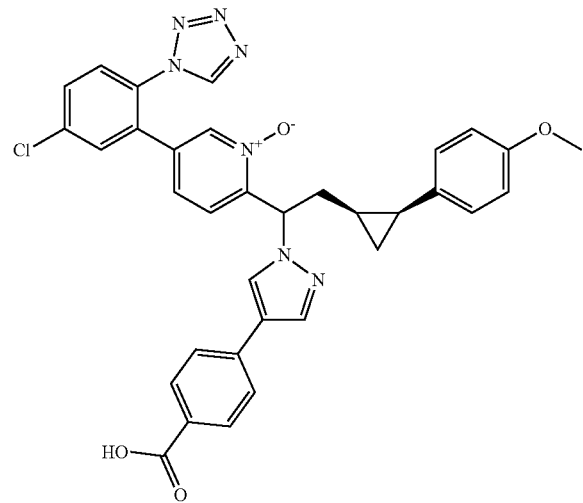 [SMILES: COc1ccc([C@H]2C[C@H]2CC(c2ccc(-c3cc(Cl)ccc3-n3cnnn3)c[n+]2[O-])n2cc(-c3ccc(C(=O)O)cc3)cn2)cc1]

LC/MS: mass calculated for $C_{34}H_{28}ClN_7O_4$: 633.19, measured (ES, m/z): 634.20 [M+H]$^+$. $^1$H NMR (400 MHz, DMSO-d$_6$) δ 12.82 (s, 1H), 9.68 (s, 1H), 8.51 (s, 1H), 8.28 (d, J=1.7 Hz, 1H), 8.09 (s, 1H), 7.78-7.93 (m, 5H), 7.61-7.68 (m, 2H), 7.25 (d, J=8.3 Hz, 1H), 6.97 (dd, J=8.3, 1.8 Hz, 1H), 6.88-6.96 (m, 2H), 6.72-6.80 (m, 2H), 6.10-6.20 (m, 1H), 3.67 (s, 3H), 2.46-2.53 (m, 1H), 2.05-2.17 (m, 1H), 1.70-1.81 (m, 1H), 0.65-0.82 (m, 3H).

Example 249: (R*)-5-(3-Chloro-2-fluoro-6-(1H-tetrazol-1-yl)phenyl)-2-(2-(2-oxopyrrolidin-1-yl)-1-(4-(pyridin-4-yl)-1H-pyrazol-1-yl)ethyl)pyridine 1-oxide

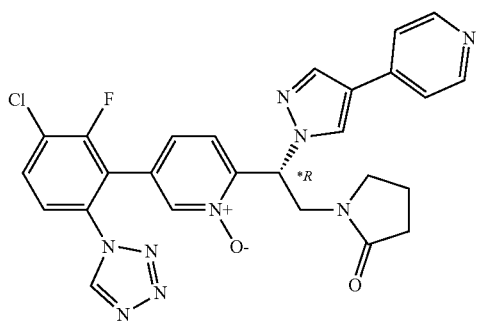 [SMILES: O=C1CCCN1C[C@H](c1ccc(-c2c(-n3cnnn3)ccc(Cl)c2F)c[n+]1[O-])n1cc(-c2ccncc2)cn1]

LC/MS: mass calculated for $C_{26}H_{21}ClFN_9O_2$: 545.15, measured (ES, m/z): 546.2 [M+H]$^+$. $^1$H NMR (400 MHz, DMSO-d$_6$) δ 9.68 (s, 1H), 8.72 (s, 1H), 8.44-8.55 (m, 3H), 8.19 (s, 1H), 9.98-8.09 (m, 1H), 7.77-7.81 (m, 1H), 7.56-7.70 (m, 3H), 7.18-7.26 (m, 1H), 6.28-6.34 (m, 1H), 3.95-4.11 (m, 2H), 3.21-3.29 (m, 1H), 2.85-2.94 (m, 1H), 2.05-2.19 (m, 2H), 1.79-1.85 (m, 2 h). $^{19}$F NMR (376 MHz, DMSO-d$_6$) δ −112.67, −115.30.

Example 250: (R)-5-(3-Chloro-2-fluoro-6-(1H-tetrazol-1-yl)phenyl)-2-(2-(2-oxopyrrolidin-1-yl)-1-(4-(pyridin-4-yl)-1H-pyrazol-1-yl)ethyl)pyridine 1-oxide

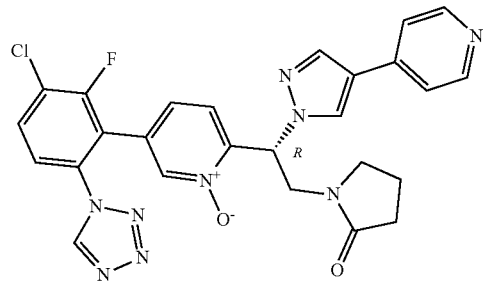

LC/MS: mass calculated for $C_{26}H_{21}ClFN_9O_2$: 545.15, measured (ES, m/z): 546.1 [M+H]$^+$. $^1$H NMR (400 MHz, DMSO-d$_6$) δ 9.69 (s, 1H), 8.71 (s, 1H), 8.51 (d, J=5.1 Hz, 2H), 8.46 (s, 1H), 8.18 (s, 1H), 9.98-8.08 (m, 1H), 7.77 (d, J=8.7 Hz, 1H), 7.55-7.63 (m, 3H), 7.22 (d, J=8.4 Hz, 1H), 6.28-6.39 (m, 1H), 3.99-4.11 (m, 2H), 3.19-3.25 (m, 1H), 2.89-2.98 (m, 1H), 2.09-2.14 (m, 2H), 1.71-1.89 (m, 2H). $^{19}$F NMR (376 MHz, DMSO-d$_6$) δ −112.67, −73.40.

Example 251: (R*)-5-(3-Chloro-2-fluoro-6-(1H-tetrazol-1-yl)phenyl)-2-(1-(4-(1-oxidopyridin-4-yl)-1H-pyrazol-1-yl)-2-(2-oxopyrrolidin-1-yl)ethyl)pyridine 1-oxide

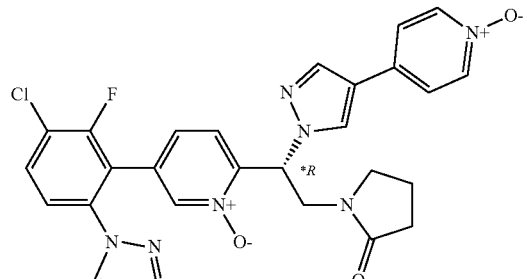

LC/MS: mass calculated for $C_{26}H_{21}ClFN_9O_3$: 561.14, measured (ES, m/z): 561.9 [M+H]$^+$. $^1$H NMR (400 MHz, DMSO-d$_6$) δ 9.69 (s, 1H), 8.64 (s, 1H), 8.41-8.47 (m, 1H), 8.10-8.22 (m, 3H), 8.02-8.08 (m, 1H), 7.77 (dd, J=8.7, 1.5 Hz, 1H), 7.61-7.69 (m, 2H), 7.58 (d, J=8.3 Hz, 1H), 7.21 (dd, J=8.2, 1.7 Hz, 1H), 6.28-6.36 (m, 1H), 3.94-4.10 (m, 2H), 3.18-3.22 (m, 1H), 2.86-2.94 (m, 1H), 2.09-2.16 (m, 2H), 1.78-1.85 (m, 2 h). $^{19}$F NMR (376 MHz, DMSO-d$_6$) δ −112.68, −73.41.

Example 252: (S*)-5-(3-Chloro-2-fluoro-6-(1H-tetrazol-1-yl)phenyl)-2-(1-(4-(1-oxidopyridin-4-yl)-1H-pyrazol-1-yl)-2-(2-oxopyrrolidin-1-yl)ethyl)pyridine 1-oxide

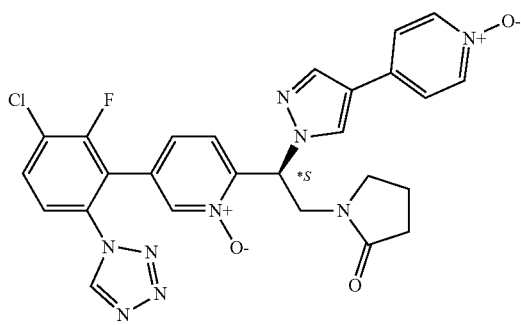 [SMILES: O=C1CCCN1C[C@@H](c1ccc(-c2c(-n3cnnn3)ccc(Cl)c2F)c[n+]1[O-])n1cc(-c2cc[n+]([O-])cc2)cn1]

LC/MS: mass calculated for $C_{26}H_{21}ClFN_9O_3$: 561.14, measured (ES, m/z): 561.9 [M+H]$^+$. $^1$H NMR (400 MHz, DMSO-d$_6$) δ 9.69 (s, 1H), 8.64 (s, 1H), 8.41-8.46 (m, 1H), 8.02-8.24 (m, 4H), 7.77 (dd, J=8.7, 1.5 Hz, 1H), 7.55-7.70 (m, 3H), 7.22 (dd, J=8.2, 1.6 Hz, 1H), 6.28-6.34 (m, 1H), 3.94-4.10 (m, 2H), 3.23-3.32 (m, 1H), 2.85-2.94 (m, 1H), 2.04-2.22 (m, 2H), 1.76-1.87 (m, 2H). $^{19}$F NMR (376 MHz, DMSO-d$_6$) δ −112.68, −73.41.

Example 253: 2-(2-((1S*,2R*)-2-Carboxycyclopropyl)-1-(4-(4-((methoxycarbonyl)amino)phenyl)-1H-pyrazol-1-yl)ethyl)-5-(3-chloro-2-fluoro-6-(1H-tetrazol-1-yl)phenyl)pyridine 1-oxide

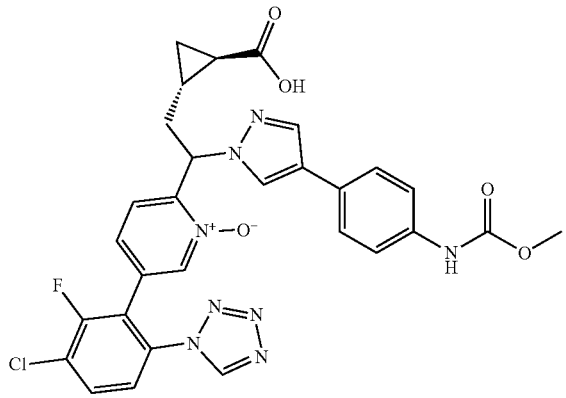 [SMILES: COC(=O)Nc1ccc(-c2cnn(C(C[C@@H]3C[C@H]3C(=O)O)c3ccc(-c4c(-n5cnnn5)ccc(Cl)c4F)c[n+]3[O-])c2)cc1]

LC/MS: mass calculated for $C_{29}H_{24}ClFN_8O_5$: 618.15, measured (ES, m/z): 619.05 [M+H]$^+$. $^1$H NMR (400 MHz, DMSO-d$_6$) δ 11.97 (brs, 1H), 9.68 (s, 1H), 9.66 (s, 1H), 8.35-8.49 (m, 2H), 8.05 (dd, J=8.7, 7.7 Hz, 1H), 7.97 (s, 1H), 7.71-7.81 (m, 1H), 7.41-7.55 (m, 4H), 7.22 (d, J=8.3 Hz, 1H), 7.15 (dd, J=8.3, 1.7 Hz, 1H), 6.05 (dd, J=10.2, 4.1 Hz, 1H), 3.66 (s, 3H), 2.52-2.60 (m, 1H), 1.89-1.95 (m, 1H), 1.30-1.37 (m, 1H), 1.09-1.15 (m, 1H), 0.82-0.94 (m, 1H), 0.70-0.80 (m, 1H). $^{19}$F NMR (376 MHz, DMSO-d$_6$) δ −114.90, −112.70, −73.48.

Example 254: 2-(2-((1S*,2S*)-2-Carboxycyclopropyl)-1-(4-(4-((methoxycarbonyl)amino)phenyl)-1H-pyrazol-1-yl)ethyl)-5-(3-chloro-2-fluoro-6-(1H-tetrazol-1-yl)phenyl)pyridine 1-oxide

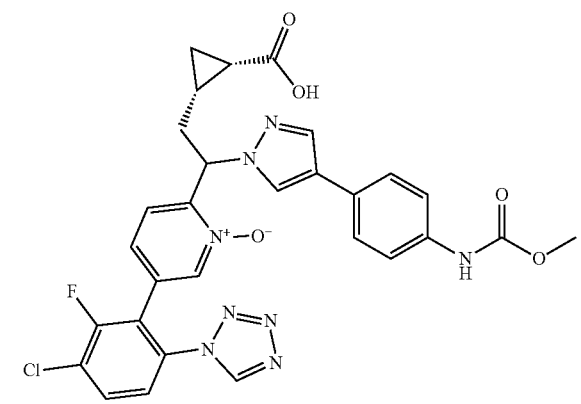 [SMILES: COC(=O)Nc1ccc(-c2cnn(C(C[C@@H]3C[C@@H]3C(=O)O)c3ccc(-c4c(-n5cnnn5)ccc(Cl)c4F)c[n+]3[O-])c2)cc1]

LC/MS: mass calculated for $C_{29}H_{24}ClFN_8O_5$: 618.15, measured (ES, m/z): 618.85 [M+H]$^+$. $^1$H NMR (400 MHz, DMSO-d$_6$) δ 12.09 (s, 1H), 9.69 (d, J=3.5 Hz, 1H), 9.64 (s, 1H), 8.35-8.43 (m, 2H), 7.95-8.08 (m, 2H), 7.74-7.76 (m, 1H), 7.43-7.53 (m, 4H), 7.14-7.28 (m, 2H), 6.01-6.13 (m, 1H), 3.67 (s, 3H), 2.52-2.60 (m, 1H), 1.89-1.95 (m, 1H), 1.30-1.37 (m, 1H), 1.09-1.15 (m, 1H), 0.82-0.94 (m, 1H), 0.70-0.80 (m, 1H). $^{19}$F NMR (376 MHz, DMSO-d$_6$) δ −112.69, −73.65.

Example 255: 2-(2-((1S*,2S*)-2-Carbamoylcyclopropyl)-1-(4-(4-((methoxycarbonyl)amino)phenyl)-1H-pyrazol-1-yl)ethyl)-5-(3-chloro-2,6-difluorophenyl)pyridine 1-oxide

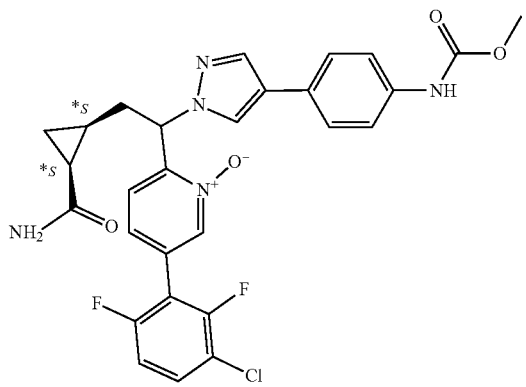 [SMILES: COC(=O)Nc1ccc(-c2cnn(C(C[C@@H]3C[C@@H]3C(N)=O)c3ccc(-c4c(F)ccc(Cl)c4F)c[n+]3[O-])c2)cc1]

LC/MS: mass calculated for $C_{28}H_{24}ClF_2N_5O_4$: 567.15, measured (ES, m/z): 568.05 [M+H]$^+$. $^1$H NMR (300 MHz, DMSO-d$_6$) δ 9.64 (s, 1H), 8.56 (d, J=8.9 Hz, 1H), 8.35 (d, J=16.2 Hz, 1H), 7.92 (d, J=12.9 Hz, 1H), 7.73-7.80 (m, 1H), 7.37-7.74 (m, 8H), 6.85-6.78 (m, 1H), 6.11-6.16 (m, 1H), 3.66 (s, 3H), 2.55-2.72 (m, 1H), 2.21-2.39 (m, 1H), 1.54-1.66 (m, 1H), 0.62-1.11 (m, 3H). $^{19}$F NMR (282 MHz, DMSO-d$_6$) δ −114.41, −73.41.

Example 256: 2-(1-(4-(6-Amino-2-fluoropyridin-3-yl)-1H-pyrazol-1-yl)-2-(2-carbamoylcyclopropyl)ethyl)-5-(3-chloro-2-fluoro-6-(1H-tetrazol-1-yl)phenyl)-4-methoxypyridine 1-oxide

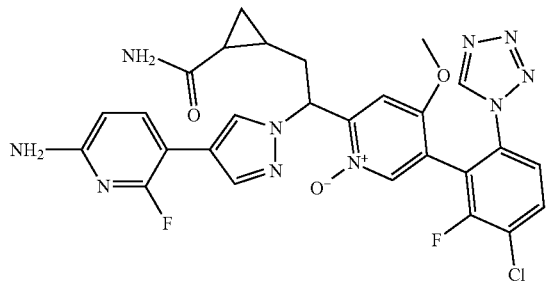 [SMILES: COc1cc(C(CC2CC2C(N)=O)n2cc(-c3ccc(N)nc3F)cn2)[n+]([O-])cc1-c1c(-n2cnnn2)ccc(Cl)c1F]

LC/MS: mass calculated for $C_{27}H_{23}ClF_2N_{10}O_3$: 608.15, measured (ES, m/z): 609.1 [M+H]$^+$. $^1$H NMR (400 MHz, DMSO-d$_6$) δ 9.70-9.79 (m, 1H), 8.41 (t, J=5.2 Hz, 1H), 8.21 (d, J=22.6 Hz, 1H), 7.98-8.08 (m, 1H), 7.72-7.92 (m, 3H), 7.24 (d, J=9.2 Hz, 1H), 7.09 (d, J=6.2 Hz, 1H), 6.85-7.00 (m, 1H), 6.73 (s, 1H), 6.36 (t, J=7.2 Hz, 1H), 6.12 (s, 1H), 3.55 (d, J=9.2 Hz, 3H), 1.71 (d, J=86.4 Hz, 1H), 1.36 (s, 1H), 0.91 (s, 1H), 0.76 (s, 2H), 0.60 (s, 1H). $^{19}$F NMR (376 MHz, DMSO-d$_6$) δ −71.42, −74.37, −74.36, −111.59, −111.78.

Example 257: 2-(1-(4-(6-Amino-2-fluoropyridin-3-yl)-1H-pyrazol-1-yl)-2-(2-(piperidine-1-carbonyl)cyclopropyl)ethyl)-5-(3-chloro-2-fluoro-6-(1H-tetrazol-1-yl)phenyl)-4-methoxypyridine 1-oxide

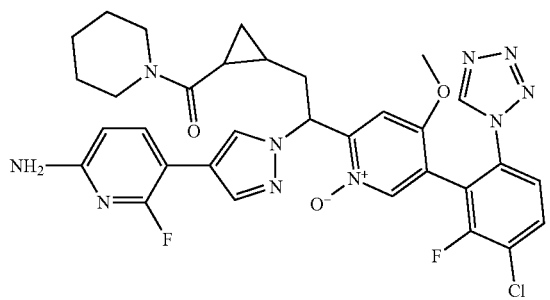 [SMILES: COc1cc(C(CC2CC2C(=O)N2CCCCC2)n2cc(-c3ccc(N)nc3F)cn2)[n+]([O-])cc1-c1c(-n2cnnn2)ccc(Cl)c1F]

LC/MS: mass calculated for $C_{32}H_{31}ClF_2N_{10}O_3$: 676.22, measured (ES, m/z): 677.1 [M+H]$^+$. $^1$H NMR (400 MHz, DMSO-d$_6$) δ 9.74 (d, J=11.9 Hz, 1H), 8.42 (d, J=4.4 Hz, 1H), 8.20-8.26 (m, 1H), 8.06 (t, J=8.2 Hz, 1H), 7.90 (d, J=12.3 Hz, 1H), 7.7-7.87 (m, 2H), 6.90-7.02 (m, 1H), 6.31-6.38 (m, 1H), 6.04-6.17 (m, 1H), 3.53 (s, 3H), 3.35 (s, 3H), 3.15-3.21 (m, 1H), 1.96-2.05 (m, 1H), 1.63-1.73 (m, 1H), 1.12-1.52 (m, 7H), 1.08-1.12 (m, 1H), 0.81 (s, 1H), 0.63 (s, 1H). $^{19}$F NMR (376 MHz, DMSO-d$_6$) δ −71.29, −74.44, −111.71.

Example 258: 2-(2-(2-Carbamoylcyclopropyl)-1-(4-(4-((methoxycarbonyl)amino)phenyl)-1H-pyrazol-1-yl)ethyl)-5-(3-chloro-2-fluoro-6-(1H-tetrazol-1-yl)phenyl)pyridine 1-oxide

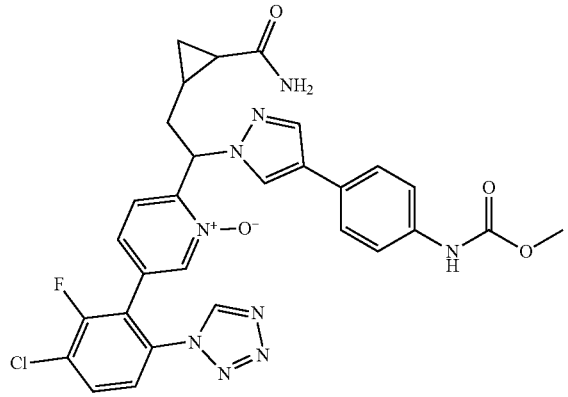 [SMILES: COC(=O)Nc1ccc(-c2cnn(C(CC3CC3C(N)=O)c3ccc(-c4c(-n5cnnn5)ccc(Cl)c4F)c[n+]3[O-])c2)cc1]

LC/MS: mass calculated for $C_{29}H_{25}ClFN_9O_4$: 617.17, measured (ES, m/z): 618.1 [M+H]$^+$. $^1$H NMR (300 MHz, DMSO-d$_6$) δ 9.59-9.69 (m, 2H), 8.28-8.42 (m, 2H), 7.93-8.06 (m, 2H), 7.73 (dd, J=8.7, 1.6 Hz, 1H), 7.49-7.55 (m, 2H), 7.41-7.46 (m, 2H), 7.34-7.37 (m, 1H), 7.18-7.25 (m, 2H), 6.69 (s, 1H), 6.01 (dd, J=10.2, 4.2 Hz, 1H), 3.65 (s, 3H), 2.55-2.65 (m, 1H), 1.69-2.12 (m, 1H), 1.31-1.51 (m, 1H), 0.96-1.11 (m, 1H), 0.61-0.89 (m, 1H), 0.39-0.58 (m, 1H). $^{19}$F NMR (282 MHz, DMSO-d$_6$) δ −73.47, −112.72.

Example 259: 5-(5-Chloro-2-(1H-tetrazol-1-yl)phenyl)-2-(2-(4-chlorophenyl)-1-(4-(2-(trifluoromethyl)pyridin-4-yl)-1H-pyrazol-1-yl)ethyl)pyridine 1-oxide

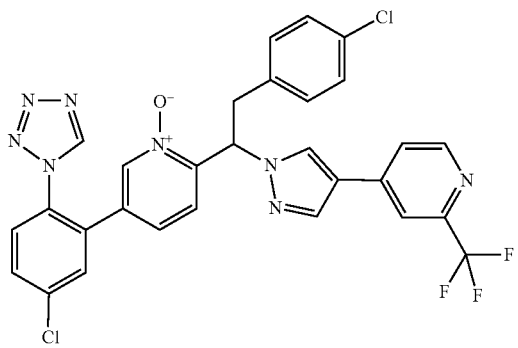 [SMILES: [O-][n+]1cc(-c2cc(Cl)ccc2-n2cnnn2)ccc1C(Cc1ccc(Cl)cc1)n1cc(-c2ccnc(C(F)(F)F)c2)cn1]

LC/MS: mass calculated for $C_{29}H_{19}Cl_2F_3N_8O$: 622.1, measured (ES, m/z): 623.3 [M]$^+$. $^1$H NMR (400 MHz, CD$_3$OD) δ ppm 3.55-3.73 (m, 2H), 6.24-6.36 (m, 1H), 7.10-7.28 (m, 2H), 7.48-7.67 (m, 2H), 7.67-7.86 (m, 2H), 7.88-8.00 (m, 4H), 8.15-8.28 (m, 2H), 8.31 (d, J=1.5 Hz, 1H), 8.37 (s, 1H), 8.57 (d, J=5.4 Hz, 1H), 9.38 (s, 1H).

Example 260: 5-(3-Chloro-2-fluoro-6-(1H-tetrazol-1-yl)phenyl)-2-(2-cyclopropyl-1-(4-(pyridin-4-yl)-1H-pyrazol-1-yl)ethyl)-4-ethoxypyridine 1-oxide

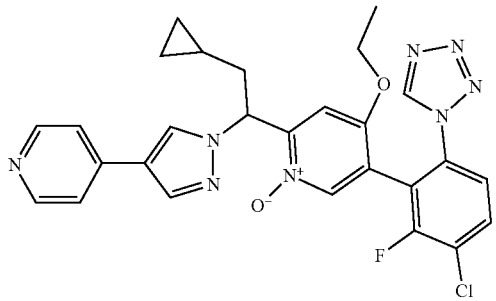 [SMILES: CCOc1cc(C(CC2CC2)n2cc(-c3ccncc3)cn2)[n+]([O-])cc1-c1c(-n2cnnn2)ccc(Cl)c1F]

LC/MS: mass calculated for C₂₇H₂₄ClFN₈O₂: 546.17, measured (ES, m/z): 547.1 [M+H]⁺. ¹H NMR (400 MHz, DMSO-d₆) δ 9.75 (d, J=7.6 Hz, 1H), 9.03 (d, J=5.2 Hz, 1H), 8.71-8.82 (m, 2H), 8.42 (dd, J=8.1, 3.7 Hz, 2H), 8.01-8.18 (m, 3H), 7.70-7.82 (m, 1H), 6.91-7.26 (m, 1H), 6.12-6.25 (m, 1H), 3.90-4.03 (m, 1H), 3.72-3.81 (m, 1H), 2.37-2.46 (m, 1H), 1.97-2.11 (m, 1H), 1.05 (t, J=6.9 Hz, 3H), 0.59 (s, 1H), 0.30-0.42 (m, 2H), 0.14 (d, J=6.0 Hz, 1H), 0.01 (s, 1H). ¹⁹F NMR (376 MHz, DMSO-d₆) δ −73.86, −111.71.

Example 261: 5-(3-Chloro-2-fluoro-6-(1H-tetrazol-1-yl)phenyl)-2-(2-(2-(piperidine-1-carbonyl)cyclopropyl)-1-(4-(pyridin-4-yl)-1H-pyrazol-1-yl)ethyl)pyridine 1-oxide

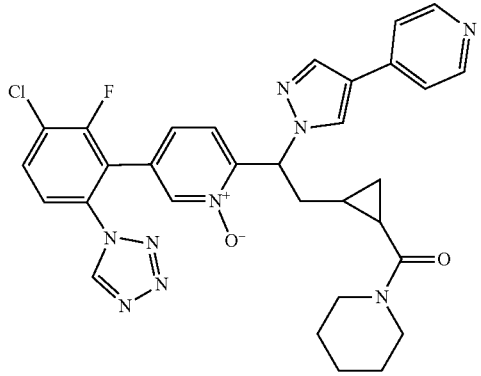 [SMILES: O=C(C1CC1CC(c1ccc(-c2c(-n3cnnn3)ccc(Cl)c2F)c[n+]1[O-])n1cc(-c2ccncc2)cn1)N1CCCCC1]

LC/MS: mass calculated for C₃₁H₂₉ClFN₉O₂: 613.21, measured (ES, m/z): 614.10 [M+H]⁺. ¹H NMR (400 MHz, DMSO-d₆) δ 9.69 (s, 1H), 9.07 (s, 1H), 8.79 (d, J=6.2 Hz, 2H), 8.41-8.50 (m, 2H), 8.15-8.21 (m, 2H), 7.98-8.09 (m, 1H), 7.75 (dd, J=8.7, 1.5 Hz, 1H), 7.44 (d, J=8.3 Hz, 1H), 6.98-7.25 (m, 1H), 6.11 (dd, J=10.6, 4.0 Hz, 1H), 3.11-3.51 (m, 4H), 2.49 (s, 1H), 2.02-2.12 (m, 1H), 1.67-1.73 (m, 1H), 1.19-1.59 (m, 6H), 1.06 (s, 1H), 0.78-0.82 (m, 1H), 0.61-0.69 (m, 1H). ¹⁹F NMR (376 MHz, DMSO-d₆) δ −74.15, −112.77.

Example 262: 5-(3-Chloro-2-fluoro-6-(1H-tetrazol-1-yl)phenyl)-2-(2-(2-(3-phenylpyrrolidine-1-carbonyl)cyclopropyl)-1-(4-(pyridin-4-yl)-1H-pyrazol-1-yl)ethyl)pyridine 1-oxide

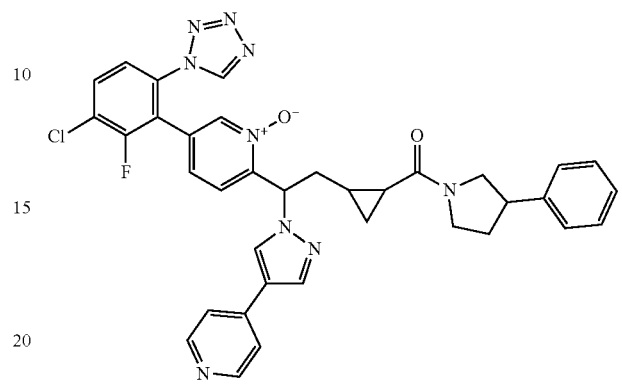

LC/MS: mass calculated for C₃₆H₃₁ClFN₉O₂: 675.23, measured (ES, m/z): 676.10 [M+H]⁺. ¹H NMR (400 MHz, DMSO-d₆) δ 9.69 (dd, J=4.6, 1.2 Hz, 1H), 9.01-9.12 (m, 1H), 8.75-8.81 (m, 2H), 8.50 (d, J=7.3 Hz, 1H), 8.43 (d, J=5.4 Hz, 1H), 8.00-8.25 (m, 3H), 7.75 (dd, J=8.9, 3.2 Hz, 1H), 7.41-7.58 (m, 1H), 7.05-7.32 (m, 7H), 6.09-6.17 (m, 1H), 3.69-4.03 (m, 1H), 3.44-3.55 (m, 1H), 3.25-3.41 (m, 1H), 2.79-3.24 (m, 2H), 2.35-2.45 (m, 1H), 2.00-2.21 (m, 2H), 1.58-1.98 (m, 1H), 1.39-1.51 (m, 1H), 0.79-0.91 (m, 1H), 0.70 (s, 1H). ¹⁹F NMR (376 MHz, DMSO-d₆) δ −74.20, −112.76.

Example 263: 5-(3-Chloro-2-fluoro-6-(1H-tetrazol-1-yl)phenyl)-2-(2-(2-(3-cyclopropylpyrrolidine-1-carbonyl)cyclopropyl)-1-(4-(pyridin-4-yl)-1H-pyrazol-1-yl)ethyl)pyridine 1-oxide

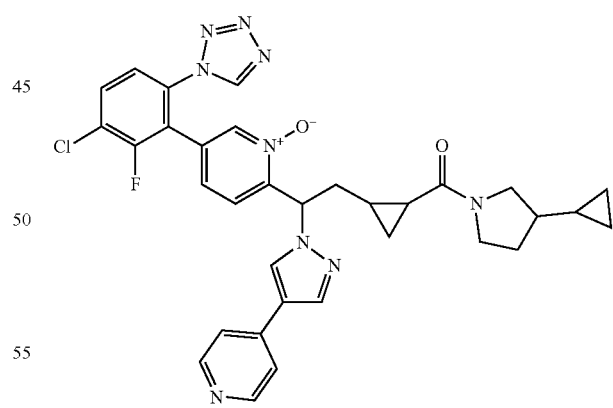

LC/MS: mass calculated for C₃₃H₃₁ClFN₉O₂: 639.23, measured (ES, m/z): 640.10 [M+H]⁺. ¹H NMR (400 MHz, DMSO-d₆) δ 9.69 (d, J=0.9 Hz, 1H), 8.99-9.13 (m, 1H), 8.76-8.85 (m, 2H), 8.49 (dd, J=6.0, 2.7 Hz, 1H), 8.39-8.42 (m, 1H), 8.15-8.25 (m, 2H), 7.98-8.09 (m, 1H), 7.76 (dd, J=8.7, 1.5 Hz, 1H), 7.40-7.58 (m, 1H), 6.99-7.21 (m, 1H), 6.11 (d, J=10.4 Hz, 1H), 3.47-3.63 (m, 1H), 3.25-3.39 (m, 1H), 3.19-3.21 (m, 1H), 2.86-3.07 (m, 1H), 2.68-2.82 (m, 1H), 2.31-2.42 (m, 1H), 2.14 (d, J=14.4 Hz, 1H), 1.71-1.89

(m, 1H), 1.30-1.63 (m, 2H), 0.92-1.27 (m, 2H), 0.65-0.88 (m, 1H), 0.61-0.69 (m, 1H), 0.25-0.39 (m, 2H), 0.08-0.19 (m, 2H). $^{19}$F NMR (376 MHz, DMSO-d$_6$) δ −74.35, −112.76.

Example 264: 2-(2-(2-(5-Azaspiro[2.4]heptane-5-carbonyl)cyclopropyl)-1-(4-(pyridin-4-yl)-1H-pyrazol-1-yl)ethyl)-5-(3-chloro-2-fluoro-6-(1H-tetrazol-1-yl)phenyl)pyridine 1-oxide

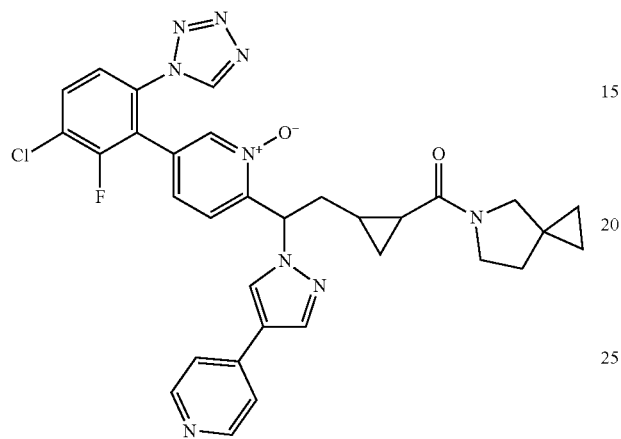

LC/MS: mass calculated for C$_{32}$H$_{29}$ClFN$_9$O$_2$: 625.21, measured (ES, m/z): 626.10 [M+H]$^+$. $^1$H NMR (400 MHz, DMSO-d$_6$) δ 9.69 (d, J=1.4 Hz, 1H), 9.07 (d, J=5.8 Hz, 1H), 8.72-8.87 (m, 2H), 8.34-8.58 (m, 2H), 8.12-8.21 (m, 2H), 7.98-8.08 (m, 1H), 7.76 (d, J=8.7 Hz, 1H), 7.39-7.49 (m, 1H), 6.95-7.25 (m, 1H), 6.07-6.18 (m, 1H), 3.35-3.61 (m, 1H), 2.89-3.31 (m, 3H), 2.38-2.42 (m, 1H), 2.05-2.15 (m, 1H), 1.67-1.79 (m, 1H), 1.37-1.49 (m, 1H), 1.19-1.26 (m, 1H), 1.13 (s, 1H), 0.82 (d, J=5.2 Hz, 1H), 0.59-0.69 (m, 1H), 0.39-0.51 (m, 3H), 0.21-0.29 (m, 1H). $^{19}$F NMR (376 MHz, DMSO-d$_6$) δ −74.11, −112.75.

Example 265: 2-(1-(4-(6-Amino-2-fluoropyridin-3-yl)-1H-pyrazol-1-yl)-2-(1H-pyrazol-1-yl)ethyl)-5-(3-chloro-2-fluoro-6-(1H-tetrazol-1-yl)phenyl)pyridine 1-oxide

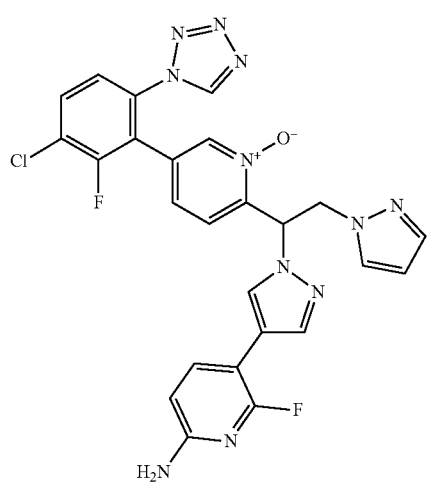 [SMILES: Nc1ccc(-c2cnn(C(Cn3cccn3)c3ccc(-c4c(-n5cnnn5)ccc(Cl)c4F)c[n+]3[O-])c2)c(F)n1]

LC/MS: mass calculated for C$_{25}$H$_{18}$ClF$_2$N$_{11}$O: 561.14, measured (ES, m/z): 562.0 [M+H]$^+$. $^1$H NMR (300 MHz, DMSO-d$_6$) δ 9.69 (s, 1H), 8.51 (s, 1H), 8.02-8.14 (m, 2H), 7.88 (s, 1H), 7.69-7.82 (m, 2H), 7.43 (d, J=8.2 Hz, 2H), 7.29 (d, J=8.4 Hz, 1H), 7.20 (d, J=8.5 Hz, 1H), 6.48-6.58 (m, 1H), 6.35-6.38 (m, 1H), 6.12 (t, J=2.0 Hz, 1H), 4.91-5.13 (m, 2H). $^{19}$F NMR (282 MHz, DMSO-d$_6$) δ −71.28, −112.63.

Example 266: 5-(3-Chloro-2-fluoro-6-(1H-tetrazol-1-yl)phenyl)-2-(1-(4-(2-fluoropyridin-4-yl)-1H-pyrazol-1-yl)-2-(2-oxopyrrolidin-1-yl)ethyl)pyridine 1-oxide

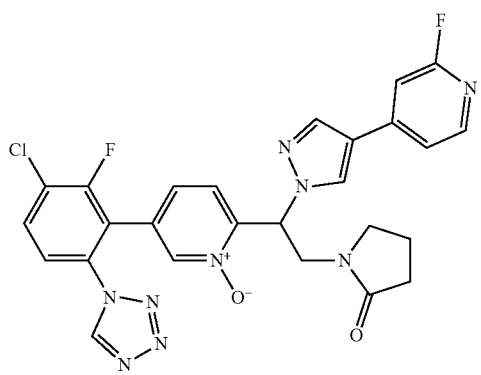 [SMILES: O=C1CCCN1CC(c1ccc(-c2c(-n3cnnn3)ccc(Cl)c2F)c[n+]1[O-])n1cc(-c2ccnc(F)c2)cn1]

LC/MS: mass calculated for C$_{26}$H$_{20}$ClF$_2$N$_9$O$_2$: 563.13, measured (ES, m/z): 564.05 [M+H]$^+$. $^1$H NMR (400 MHz, DMSO-d$_6$) δ 9.68 (s, 1H), 8.78 (s, 1H), 8.46 (d, J=1.5 Hz, 1H), 8.24 (s, 1H), 8.18 (d, J=5.3 Hz, 1H), 8.02-8.11 (m, 1H), 7.76 (dd, J=8.8, 1.5 Hz, 1H), 7.55-7.65 (m, 2H), 7.43 (s, 1H), 7.22 (dd, J=8.3, 1.7 Hz, 1H), 6.28-6.38 (m, 1H), 3.95-4.11 (m, 2H), 3.25-3.35 (m, 1H), 2.88-2.97 (m, 1H), 2.05-2.18 (m, 2H), 1.72-1.90 (m, 2 h). $^{19}$F NMR (376 MHz, DMSO) d −69.19, −73.82, −112.67.

Example 267: (R*)-5-(3-Chloro-2-fluoro-6-(1H-tetrazol-1-yl)phenyl)-2-(2-cyclopropyl-1-(4-(pyrimidin-4-yl)-1H-pyrazol-1-yl)ethyl)pyridine 1-oxide

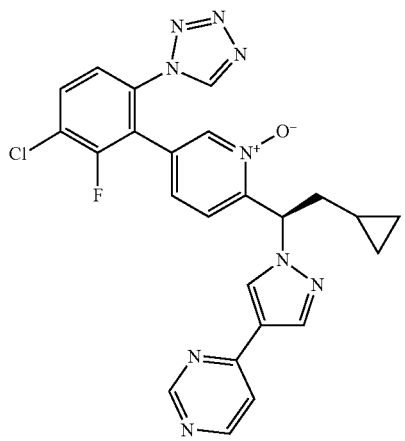 [SMILES: [O-][n+]1cc(-c2c(-n3cnnn3)ccc(Cl)c2F)ccc1[C@@H](CC1CC1)n1cc(-c2ccncn2)cn1]

LC/MS: mass calculated for C$_{24}$H$_{19}$ClFN$_9$O: 503.1, measured (ES, m/z): 504.00 [M+H]$^+$. $^1$H NMR (300 MHz, DMSO-d$_6$) δ 9.67 (s, 1H), 9.07 (s, 1H), 8.84 (s, 1H), 8.71 (d, J=5.4 Hz, 1H), 8.36-8.44 (m, 1H), 8.26 (s, 1H), 8.01-8.06 (m, 1H), 7.68-7.84 (m, 2H), 7.31-7.37 (m, 1H), 7.12-7.18 (m, 1H), 6.06-6.17 (m, 1H), 2.29-2.34 (m, 1H), 1.89-1.98 (m, 1H), 0.50-0.62 (m, 1H), 0.23-0.39 (m, 2H), 0.06-0.13 (m, 1H), 0.01-0.14 (m, 1H). $^{19}$F NMR (282 MHz, DMSO-$d_6$) δ −74.99, −112.75.

Example 268: (S*)-5-(3-Chloro-2-fluoro-6-(1H-tetrazol-1-yl)phenyl)-2-(2-cyclopropyl-1-(4-(pyrimidin-4-yl)-1H-pyrazol-1-yl)ethyl)pyridine 1-oxide

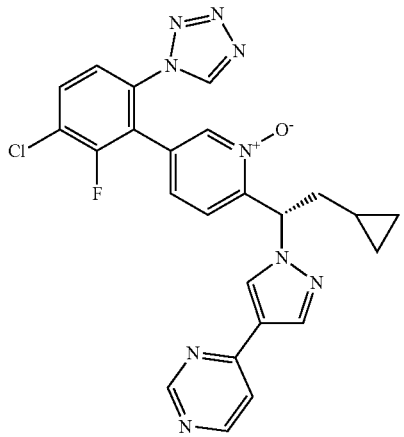 [SMILES: [O-][n+]1cc(-c2c(-n3cnnn3)ccc(Cl)c2F)ccc1[C@H](CC1CC1)n1cc(-c2ccncn2)cn1]

LC/MS: mass calculated for $C_{24}H_{19}ClFN_9O$: 503.1, measured (ES, m/z): 504.05 [M+H]$^+$. $^1$H NMR (300 MHz, DMSO-$d_6$) δ 9.59 (s, 1H), 8.97 (s, 1H), 8.69 (s, 1H), 8.53-8.57 (m, 1H), 8.32-8.40 (m, 1H), 8.12 (s, 1H), 7.98-8.03 (m, 1H), 7.81-7.85 (m, 1H), 7.70-7.79 (m, 1H), 7.60-7.69 (m, 1H), 7.22-7.30 (m, 1H), 5.59-5.71 (m, 1H), 2.33-2.43 (m, 1H), 1.93-2.02 (m, 1H), 0.43-0.52 (m, 1H), 0.24-0.35 (m, 2H), 0.01-0.09 (m, 2H). $^{19}$F NMR (282 MHz, DMSO-$d_6$) δ −74.95, −113.45.

Example 269: 2-(2-(2-Carbamoylcyclopropyl)-1-(4-(pyridin-4-yl)-1H-pyrazol-1-yl)ethyl)-5-(3-chloro-2-fluoro-6-(1H-tetrazol-1-yl)phenyl)pyridine 1-oxide

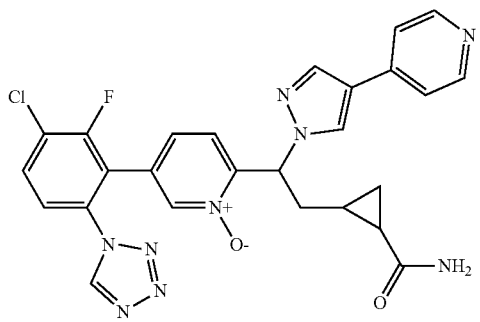 [SMILES: NC(=O)C1CC1CC(c1ccc(-c2c(-n3cnnn3)ccc(Cl)c2F)c[n+]1[O-])n1cc(-c2ccncc2)cn1]

LC/MS: mass calculated for $C_{26}H_{21}ClFN_9O_2$: 545.15, measured (ES, m/z): 546.05 [M+H]$^+$. $^1$H NMR (300 MHz, DMSO-$d_6$) δ 9.71 (s, 1H), 9.07 (s, 1H), 8.78 (d, J=6.1 Hz, 2H), 8.44 (s, 2H), 8.02-8.19 (m, 3H), 7.77 (dd, J=8.7, 1.6 Hz, 1H), 7.47 (d, J=8.3 Hz, 1H), 7.33 (d, J=14.7 Hz, 1H), 7.10-7.20 (m, 1H), 6.69 (s, 1H), 6.04-6.15 (m, 1H), 2.54-2.69 (m, 1H), 1.78-1.92 (m, 1H), 1.22-1.37 (m, 1H), 0.92 (s, 1H), 0.71-0.80 (m, 1H), 0.55-0.65 (m, 1H). $^{19}$F NMR (282 MHz, DMSO-$d_6$) δ −73.89, −112.71.

Example 270: (R*)-5-(3-Chloro-2-fluoro-6-(1H-tetrazol-1-yl)phenyl)-2-(2-cyclopropyl-1-(4-(pyridin-4-yl)-1H-pyrazol-1-yl)ethyl)pyridine 1-oxide

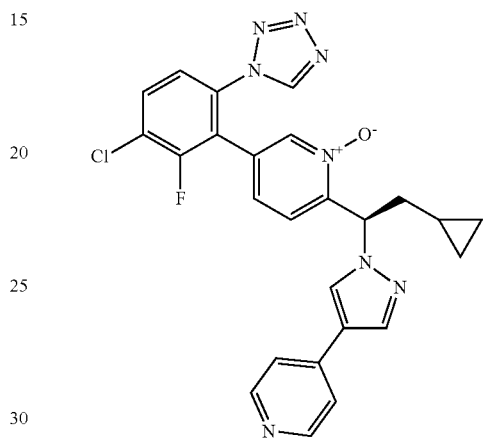

To a solution of 5-(3-chloro-2-fluoro-6-(1H-tetrazol-1-yl)phenyl)-2-(2-cyclopropyl-1-(4-(pyridin-4-yl)-1H-pyrazol-1-yl)ethyl)pyridine (300 mg, 0.616 mmol) in MeOH (3 mL) was added methyltrioxorhenium (76.779 mg, 0.308 mmol) and hydrogen peroxide (0.618 mL, 6.161 mmol, 30%). The resulting mixture was stirred at 30° C. for 1 h. The residue obtained was purified by C18 chromatography ((80 g, CH3CN/H2O (0.05% CF3COOH)): 0>>>60%) to yield 5-(3-chloro-2-fluoro-6-(1H-tetrazol-1-yl)phenyl)-2-(2-cyclopropyl-1-(4-(pyridin-4-yl)-1H-pyrazol-1-yl)ethyl)pyridine 1-oxide as a white solid (150 mg), which was purified by Prep-Chiral-HPLC. The collected fractions were combined and concentrated under vacuum. This resulted in (R*)-5-(3-chloro-2-fluoro-6-(1H-tetrazol-1-yl)phenyl)-2-(2-cyclopropyl-1-(4-(pyridin-4-yl)-1H-pyrazol-1-yl)ethyl) pyridine 1-oxide (27.5 mg, 8.504%) as a white solid and (S*)-5-(3-chloro-2-fluoro-6-(1H-tetrazol-1-yl)phenyl)-2-(2-cyclopropyl-1-(4-(pyridin-4-yl)-1H-pyrazol-1-yl)ethyl) pyridine 1-oxide as a white solid.

LC/MS: mass calculated for $C_{25}H_{20}ClFN_8O$: 502.14, measured (ES, m/z): 503.05 [M+H]$^+$. $^1$H NMR (300 MHz, DMSO-$d_6$) δ 9.67 (s, 1H), 8.81 (s, 1H), 8.50-8.59 (m, 2H), 8.40 (d, J=1.5 Hz, 1H), 8.23 (s, 1H), 8.01-8.12 (m, 1H), 7.65-7.82 (m, 3H), 7.28-7.35 (m, 1H), 7.10-7.21 (m, 1H), 6.08-6.14 (m, 1H), 2.31-2.41 (m, 1H), 1.84-1.93 (m, 1H), 0.51-0.62 (m, 1H), 0.24-0.39 (m, 2H), 0.15-0.21 (m, 1H), 0.01-0.10 (m, 2H). $^{19}$F NMR (282 MHz, DMSO-$d_6$) δ −73.46, −112.77.

Example 271: (S*)-5-(3-Chloro-2-fluoro-6-(1H-tetrazol-1-yl)phenyl)-2-(2-cyclopropyl-1-(4-(pyridin-4-yl)-1H-pyrazol-1-yl)ethyl)pyridine 1-oxide

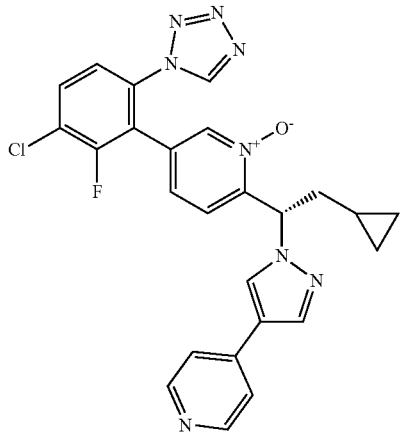 [SMILES: [O-][n+]1cc(-c2c(-n3cnnn3)ccc(Cl)c2F)ccc1[C@H](CC1CC1)n1cc(-c2ccncc2)cn1]

LC/MS: mass calculated for $C_{25}H_{20}ClFN_8O$: 502.14, measured (ES, m/z): 503.05 [M+H]$^+$. $^1$H NMR (300 MHz, DMSO-d$_6$) δ 9.67 (s, 1H), 8.79 (s, 1H), 8.48-8.57 (m, 2H), 8.40 (d, J=1.6 Hz, 1H), 8.22 (s, 1H), 8.01-8.12 (m, 1H), 7.64-7.79 (m, 3H), 7.28-7.36 (m, 1H), 7.10-7.21 (m, 1H), 6.03-6.15 (m, 1H), 2.32-2.41 (m, 1H), 1.85-1.93 (m, 1H), 0.52-0.62 (m, 1H), 0.21-0.39 (m, 2H), 0.01-0.15 (m, 2H). $^{19}$F NMR (282 MHz, DMSO-d$_6$) δ −73.45, −112.77.

Example 272: (R*)-5-(3-Chloro-2-fluoro-6-(1H-tetrazol-1-yl)phenyl)-2-(2-cyclopropyl-1-(4-(2-fluoropyridin-4-yl)-1H-pyrazol-1-yl)ethyl)pyridine 1-oxide

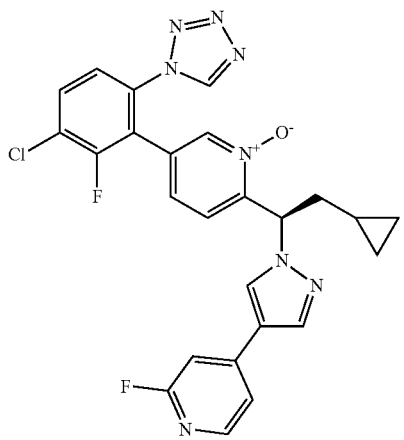 [SMILES: [O-][n+]1cc(-c2c(-n3cnnn3)ccc(Cl)c2F)ccc1[C@@H](CC1CC1)n1cc(-c2ccnc(F)c2)cn1]

LC/MS: mass calculated for $C_{25}H_{19}ClF_2N_8O$: 520.13, measured (ES, m/z): 521.05 [M+H]$^+$. $^1$H NMR (300 MHz, DMSO-d$_6$) δ 9.67 (s, 1H), 8.82 (s, 1H), 8.41 (s, 1H), 8.25 (s, 1H), 8.15 (d, J=5.3 Hz, 1H), 7.99-8.08 (m, 1H), 7.73 (dd, J=8.7, 1.6 Hz, 1H), 7.55-7.61 (m, 1H), 7.43 (s, 1H), 7.25-7.34 (m, 1H), 7.14 (dd, J=8.3, 1.6 Hz, 1H), 6.01-6.13 (m, 1H), 2.31-2.41 (m, 1H), 1.83-1.92 (m, 1H), 0.52-0.62 (m, 1H), 0.25-0.40 (m, 2H), 0.01-0.18 (m, 2H). $^{19}$F NMR (282 MHz, DMSO-d$_6$) δ −69.24, −112.75.

Example 273: (S*)-5-(3-Chloro-2-fluoro-6-(1H-tetrazol-1-yl)phenyl)-2-(2-cyclopropyl-1-(4-(2-fluoropyridin-4-yl)-1H-pyrazol-1-yl)ethyl)pyridine 1-oxide

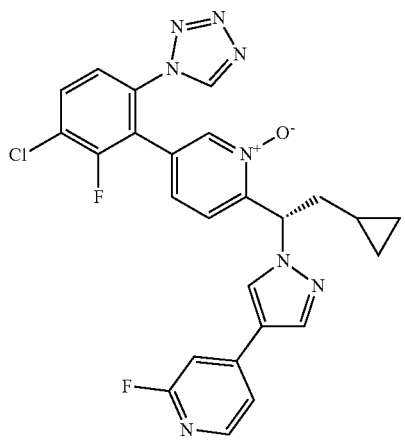 [SMILES: [O-][n+]1cc(-c2c(-n3cnnn3)ccc(Cl)c2F)ccc1[C@H](CC1CC1)n1cc(-c2ccnc(F)c2)cn1]

LC/MS: mass calculated for $C_{25}H_{19}ClF_2N_8O$: 520.13, measured (ES, m/z): 521.00 [M+H]$^+$. $^1$H NMR (300 MHz, DMSO-d$_6$) δ 9.67 (s, 1H), 8.82 (s, 1H), 8.40 (s, 1H), 8.25 (s, 1H), 8.15 (d, J=5.3 Hz, 1H), 7.99-8.08 (m, 1H), 7.73 (dd, J=8.7, 1.6 Hz, 1H), 7.55-7.61 (m, 1H), 7.43 (s, 1H), 7.29 (d, J=8.3 Hz, 1H), 7.14 (dd, J=8.3, 1.6 Hz, 1H), 6.02-6.12 (m, 1H), 2.31-2.41 (m, 1H), 1.83-1.92 (m, 1H), 0.52-0.62 (m, 1H), 0.25-0.40 (m, 2H), 0.10-0.16 (m, 1H), 0.06-0.10 (m, 1H). $^{19}$F NMR (282 MHz, DMSO-d$_6$) δ −69.24, −112.75.

Example 274: 5-(3-Chloro-2-fluoro-6-(1H-tetrazol-1-yl)phenyl)-2-(2-cyclopropyl-1-(4-(1-methyl-1H-indazol-5-yl)-1H-pyrazol-1-yl)ethyl)pyridine 1-oxide

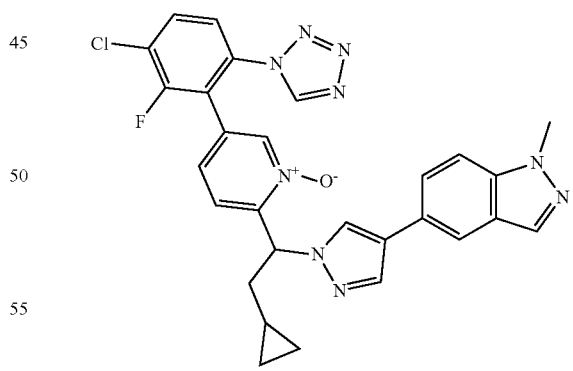

LC/MS: mass calculated for $C_{28}H_{23}ClFN_9O$: 555.17, measured (ES, m/z): 556.2 [M+H]$^+$. $^1$H NMR (400 MHz, CD$_3$OD) δ ppm 0.06-0.14 (m, 1H) 0.18-0.27 (m, 1H) 0.38-0.50 (m, 3H) 0.69-0.83 (m, 1H) 1.97-2.03 (m, 1H) 2.53 (br d, J=8.31 Hz, 1H) 4.06 (s, 3H) 6.22-6.43 (m, 1H) 7.11-7.28 (m, 1H) 7.41-7.49 (m, 1H) 7.51-7.62 (m, 3H) 7.69 (d, J=8.80 Hz, 1H) 7.88-8.02 (m, 4H) 8.26-8.40 (m, 1H) 9.43 (s, 1H).

Example 275: 5-(3-Chloro-2-fluoro-6-(1H-tetrazol-1-yl)phenyl)-2-(1-(4-(pyridin-4-yl)-1H-pyrazol-1-yl)-2-((1S*,2R*)-2-(pyrrolidine-1-carbonyl)cyclopropyl)ethyl)pyridine 1-oxide

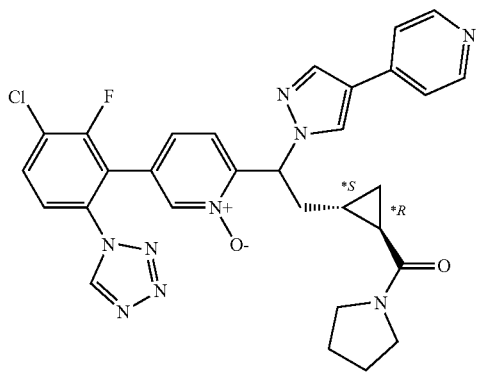 [SMILES: O=C([C@@H]1C[C@H]1CC(c1ccc(-c2c(-n3cnnn3)ccc(Cl)c2F)c[n+]1[O-])n1cc(-c2ccncc2)cn1)N1CCCC1]

LC/MS: mass calculated for $C_{30}H_{27}ClFN_9O_2$: 599.20, measured (ES, m/z): 600.10 [M+H]$^+$. $^1$H NMR (400 MHz, DMSO-d$_6$) δ 9.69 (s, 1H), 8.93-9.06 (m, 1H), 8.76 (s, 2H), 8.37-8.49 (m, 2H), 8.13 (d, J=5.7 Hz, 2H), 7.98-8.08 (m, 1H), 7.76 (dd, J=8.8, 1.5 Hz, 1H), 7.42-7.56 (m, 1H), 7.15-7.28 (m, 1H), 5.98-6.22 (m, 1H), 2.95-3.99 (m, 4H), 2.35-2.48 (m, 1H), 2.05-2.34 (m, 1H), 1.31-2.01 (m, 5H), 0.99-1.15 (m, 1H), 0.76-0.89 (m, 1H), 0.62-0.72 (m, 1H). $^{19}$F NMR (376 MHz, DMSO-d$_6$) δ −74.05, −112.75.

Example 276: 5-(3-Chloro-2-fluoro-6-(1H-tetrazol-1-yl)phenyl)-2-(1-(4-(pyridin-4-yl)-1H-pyrazol-1-yl)-2-((1S*,2S*)-2-(pyrrolidine-1-carbonyl)cyclopropyl)ethyl)pyridine 1-oxide

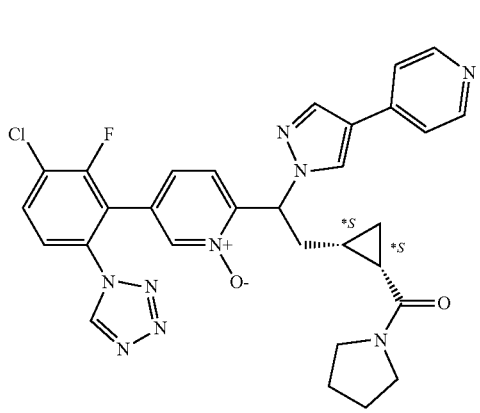 [SMILES: O=C([C@H]1C[C@H]1CC(c1ccc(-c2c(-n3cnnn3)ccc(Cl)c2F)c[n+]1[O-])n1cc(-c2ccncc2)cn1)N1CCCC1]

LC/MS: mass calculated for $C_{30}H_{27}ClFN_9O_2$: 599.20, measured (ES, m/z): 600.10 [M+H]$^+$. $^1$H NMR (400 MHz, DMSO-d$_6$) δ 9.69 (s, 1H), 9.01 (s, 1H), 8.75 (d, J=6.0 Hz, 2H), 8.41-8.47 (m, 2H), 8.00-8.15 (m, 3H), 7.75 (dd, J=8.7, 1.6 Hz, 1H), 7.36 (d, J=8.3 Hz, 1H), 7.11-7.28 (m, 1H), 6.09 (dd, J=10.2, 3.7 Hz, 1H), 3.56-3.68 (m, 2H), 3.22 (t, J=6.8 Hz, 2H), 2.34-2.43 (m, 1H), 2.12-2.21 (m, 1H), 1.88-1.96 (m, 2H), 1.66-1.83 (m, 3H), 1.08 (s, 1H), 0.72-0.82 (m, 1H), 0.39-0.50 (m, 1H). $^{19}$F NMR (376 MHz, DMSO-d$_6$) δ −73.92, −112.75.

Example 277: 5-(3-Chloro-2-fluoro-6-(1H-tetrazol-1-yl)phenyl)-2-(1-(4-(1-oxidopyridin-4-yl)-1H-pyrazol-1-yl)-2-(2-(piperidine-1-carbonyl)cyclopropyl)ethyl)pyridine 1-oxide

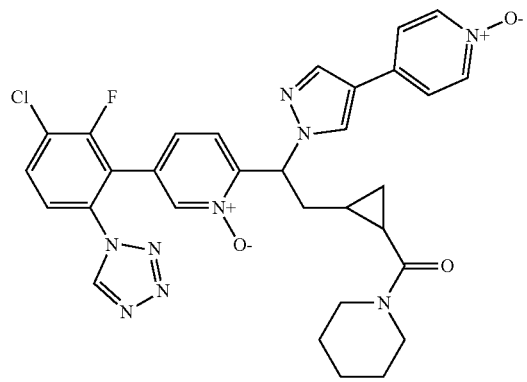 [SMILES: O=C(C1CC1CC(c1ccc(-c2c(-n3cnnn3)ccc(Cl)c2F)c[n+]1[O-])n1cc(-c2cc[n+]([O-])cc2)cn1)N1CCCCC1]

LC/MS: mass calculated for $C_{31}H_{29}ClFN_9O_3$: 629.21, measured (ES, m/z): 630.10 [M+H]$^+$. $^1$H NMR (300 MHz, DMSO-d$_6$) δ 9.67 (s, 1H), 8.60-8.70 (m, 1H), 8.41 (s, 1H), 8.10-8.21 (m, 3H), 8.04 (dd, J=8.7, 7.7 Hz, 1H), 7.73 (dd, J=8.7, 1.6 Hz, 1H), 7.60-7.70 (m, 2H), 7.25-7.40 (m, 1H), 7.10-7.24 (m, 1H), 5.95-6.15 (m, 1H), 3.31-3.67 (m, 3H), 3.10-3.28 (m, 1H), 2.32-2.49 (m, 1H), 1.83-2.11 (m, 2H), 1.20-1.70 (m, 6H), 1.00-1.17 (m, 1H), 0.41-0.85 (m, 2H). $^{19}$F NMR (282 MHz, DMSO-d$_6$) d −112.77.

Example 278: 2-(2-(1H-Pyrazol-1-yl)-1-(4-(pyridin-4-yl)-1H-pyrazol-1-yl)ethyl)-5-(3-chloro-2-fluoro-6-(1H-tetrazol-1-yl)phenyl)pyridine 1-oxide

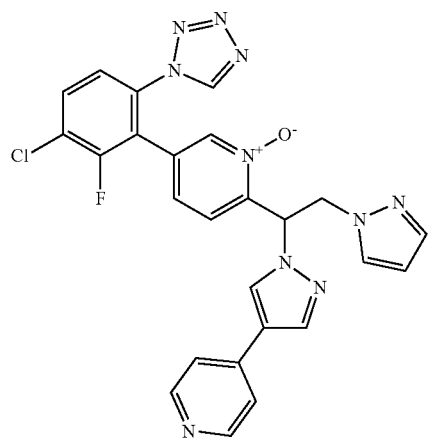 [SMILES: [O-][n+]1cc(-c2c(-n3cnnn3)ccc(Cl)c2F)ccc1C(Cn1cccn1)n1cc(-c2ccncc2)cn1]

LC/MS: mass calculated for $C_{25}H_{18}ClFN_{10}O$: 528.1, measured (ES, m/z): 529.05 [M+H]$^+$. $^1$H NMR (400 MHz, DMSO-d$_6$) δ 9.70 (s, 1H), 8.86 (s, 1H), 8.77 (d, J=6.3 Hz, 2H), 8.44-8.53 (m, 2H), 8.14 (d, J=6.2 Hz, 2H), 8.04-8.11 (m, 1H), 7.77 (dd, J=8.9, 1.4 Hz, 1H), 7.61 (d, J=8.3 Hz, 1H), 7.53 (d, J=2.2 Hz, 1H), 7.42 (d, J=1.7 Hz, 1H), 7.26 (dd, J=8.4, 1.6 Hz, 1H), 6.51-6.62 (m, 1H), 6.19-6.18 (m, 1H), 5.08-5.18 (m, 1H), 4.92-5.07 (m, 1H). $^{19}$F NMR (376 MHz, DMSO-d$_6$) δ −74.30, −112.64.

Example 279: 5-(3-Chloro-2-fluoro-6-(1H-tetrazol-1-yl)phenyl)-2-(2-(3-phenyl-1H-pyrazol-1-yl)-1-(4-(pyridin-4-yl)-1H-pyrazol-1-yl)ethyl)pyridine 1-oxide

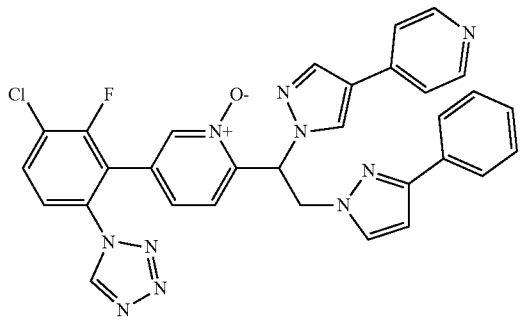 [SMILES: [O-][n+]1cc(-c2c(-n3cnnn3)ccc(Cl)c2F)ccc1C(Cn1ccc(-c2ccccc2)n1)n1cc(-c2ccncc2)cn1]

LC/MS: mass calculated for C$_{31}$H$_{22}$ClFN$_{10}$O: 604.16, measured (ES, m/z): 605.15 [M+H]$^+$. $^1$H NMR (400 MHz, DMSO-d$_6$) δ 9.63 (s, 1H), 8.66 (s, 1H), 8.48 (d, J=2.2 Hz, 1H), 8.31 (d, J=7.0 Hz, 2H), 8.18 (s, 1H), 8.01-8.09 (m, 1H), 7.66-7.80 (m, 6H), 7.49 (d, J=2.3 Hz, 1H), 7.31-7.39 (m, 2H), 7.20-7.30 (m, 2H), 6.57 (d, J=2.3 Hz, 1H), 6.14-6.22 (m, 1H), 5.12-5.21 (m, 1H), 5.01-5.11 (m, 1H). $^{19}$F NMR (376 MHz, DMSO-d$_6$) δ -74.61, -113.36.

Example 280: 5-(3-Chloro-2-fluoro-6-(1H-tetrazol-1-yl)phenyl)-2-(2-cyclopropyl-1-(4-(2,3-dihydrobenzo[b][1,4]dioxin-6-yl)-1H-pyrazol-1-yl)ethyl)pyridine 1-oxide

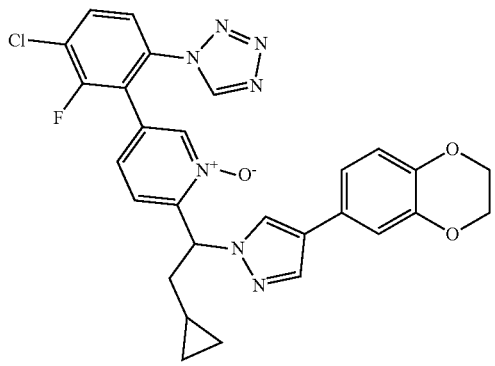 [SMILES: [O-][n+]1cc(-c2c(-n3cnnn3)ccc(Cl)c2F)ccc1C(CC1CC1)n1cc(-c2ccc3c(c2)OCCO3)cn1]

LC/MS: mass calculated for C$_{28}$H$_{23}$ClFN$_7$O$_3$: 559.2, measured (ES, m/z): 560.3 [M+H]$^+$. $^1$H NMR (400 MHz, CD$_3$OD) δ ppm 0.06-0.12 (m, 1H), 0.14-0.24 (m, 1H), 0.36-0.49 (m, 2H), 0.66-0.77 (m, 1H), 1.95-1.99 (m, 1H), 2.44-2.56 (m, 1H), 4.22-4.28 (m, 4H), 6.10-6.33 (m, 1H), 6.81 (d, J=8.31 Hz, 1H), 6.99-7.09 (m, 2H), 7.20-7.30 (m, 1H), 7.38 (br d, J=8.31 Hz, 1H), 7.58-7.65 (m, 1H), 7.91 (dd, J=8.80, 7.83 Hz, 2H), 8.09-8.25 (m, 1H), 8.29-8.40 (m, 1H), 9.37 (s, 1H).

Example 281: (R*)-5-(3-Chloro-2-fluoro-6-(1H-tetrazol-1-yl)phenyl)-2-(1-(4-(4-((methoxycarbonyl)amino)phenyl)-1H-pyrazol-1-yl)-2-(1H-pyrazol-1-yl)ethyl)pyridine 1-oxide

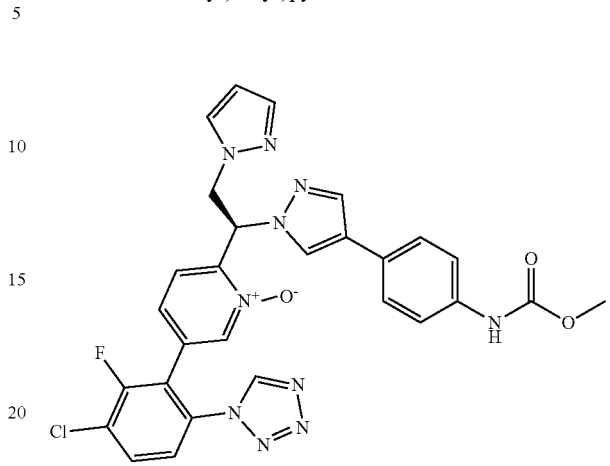

LC/MS: mass calculated for C$_{28}$H$_{22}$ClFN$_{10}$O$_3$: 600.15, measured (ES, m/z): 601.00 [M+H]$^+$. $^1$H NMR (400 MHz, DMSO-d$_6$) δ 9.59-9.71 (m, 2H), 8.51 (s, 1H), 8.21 (s, 1H), 7.98-8.09 (M, 1H), 7.98 (s, 1H), 7.76 (dd, J=8.7, 1.5 Hz, 1H), 7.39-7.49 (m, 6H), 7.27-7.32 (m, 1H), 7.12-7.21 (m, 1H), 6.46-6.55 (m, 1H), 6.06-6.12 (m, 1H), 4.86-5.13 (m, 2H), 3.66 (s, 3H). $^{19}$F NMR (376 MHz, DMSO-d$_6$) δ -112.62.

Example 282: (S*)-5-(3-Chloro-2-fluoro-6-(1H-tetrazol-1-yl)phenyl)-2-(1-(4-(4-((methoxycarbonyl)amino)phenyl)-1H-pyrazol-1-yl)-2-(1H-pyrazol-1-yl)ethyl)pyridine 1-oxide

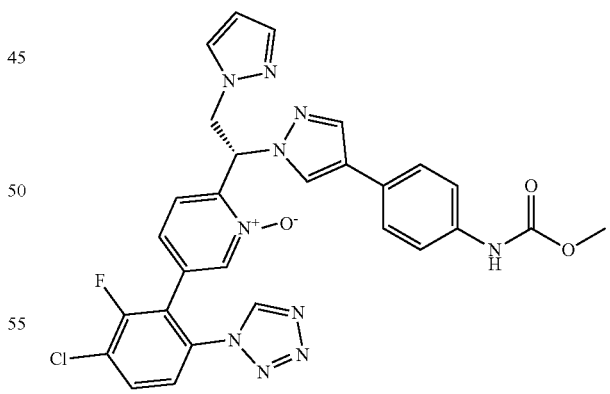

LC/MS: mass calculated for C$_{28}$H$_{22}$ClFN$_{10}$O$_3$: 600.15, measured (ES, m/z): 601.00 [M+H]$^+$. $^1$H NMR (400 MHz, DMSO-d$_6$) δ 9.62-9.79 (m, 2H), 8.51 (d, J=1.5 Hz, 1H), 8.21 (s, 1H), 8.07 (dd, J=8.7, 7.8 Hz, 1H), 7.98 (s, 1H), 7.76 (dd, J=8.7, 1.5 Hz, 1H), 7.39-7.56 (m, 6H), 7.29-7.36 (m, 1H), 7.16-7.23 (m, 1H), 6.45-4.66 (m, 1H), 6.08-6.17 (m, 1H), 4.87-5.13 (m, 2H), 3.66 (s, 3H). $^{19}$F NMR (376 MHz, DMSO-d$_6$) δ -112.62.

Example 283: 2-(2-(2-(7-amino-5-azaspiro[2.4]heptane-5-carbonyl)cyclopropyl)-1-(4-(pyridin-4-yl)-1H-pyrazol-1-yl)ethyl)-5-(3-Chloro-2-fluoro-6-(1H-tetrazol-1-yl)phenyl)pyridine 1-oxide

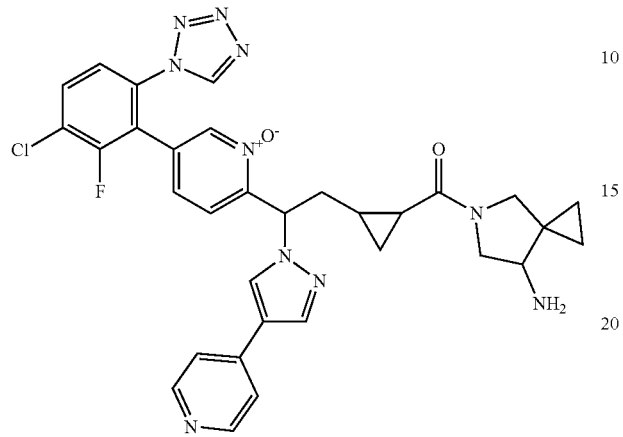

LC/MS: mass calculated for $C_{32}H_{30}ClFN_{10}O_2$: 640.22, measured (ES, m/z): 641.10 [M+H]+. $^1$H NMR (400 MHz, DMSO-$d_6$) δ 9.68-9.73 (m, 1H), 8.96-9.11 (m, 1H), 8.74-8.83 (m, 2H), 8.39-8.51 (m, 2H), 7.97-8.31 (m, 5H), 7.74-7.79 (m, 1H), 7.29-7.50 (m, 1H), 7.16-7.26 (m, 1H), 6.05-6.20 (m, 1H), 3.51-4.26 (m, 3H), 2.97-3.52 (m, 2H), 2.17-2.49 (m, 2H), 1.36-1.99 (m, 1H), 0.96-1.20 (m, 2H), 0.35-0.94 (m, 5H). $^{19}$F NMR (376 MHz, DMSO-$d_6$) δ −74.04, −112.78.

Example 284: 5-(3-Chloro-2-fluoro-6-(1H-tetrazol-1-yl)phenyl)-2-(2-(4-fluoro-1H-pyrazol-1-yl)-1-(4-(2-(trifluoromethyl)pyridin-4-yl)-1H-pyrazol-1-yl)ethyl)pyridine 1-oxide

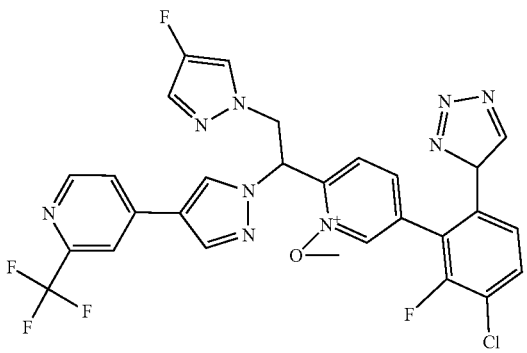 [SMILES: CO[n+]1cc(-c2c(C3C=NN=N3)ccc(Cl)c2F)ccc1C(Cn1cc(F)cn1)n1cc(-c2ccnc(C(F)(F)F)c2)cn1]

LC/MS: mass calculated for $C_{26}H_{16}ClF_5N_{10}O$: 614.11, measured (ES, m/z): 615.10[M+H]+. $^1$H NMR (400 MHz, DMSO-$d_6$) δ 9.69 (s, 1H), 8.75 (s, 1H), 8.67 (d, J=5.2 Hz, 1H), 8.52 (d, J=1.5 Hz, 1H), 8.39 (s, 1H), 8.03-8.13 (m, 2H), 7.88 (dd, J=5.2, 1.5 Hz, 1H), 7.70-7.77 (m, 1H), 7.69 (d, J=4.6 Hz, 1H), 7.42-7.55 (m, 2H), 7.23 (dd, J=8.3, 1.6 Hz, 1H), 6.46-6.59 (m, 1H), 4.85-5.13 (m, 2H). $^{19}$F NMR (376 MHz, DMSO-$d_6$) δ −66.54, −75.01, −112.50, −177.74.

Example 285: 5-(3-Chloro-2-fluoro-6-(1H-tetrazol-1-yl)phenyl)-2-(2-(4-fluoro-1H-pyrazol-1-yl)-1-(4-(pyridin-4-yl)-1H-pyrazol-1-yl)ethyl)pyridine 1-oxide

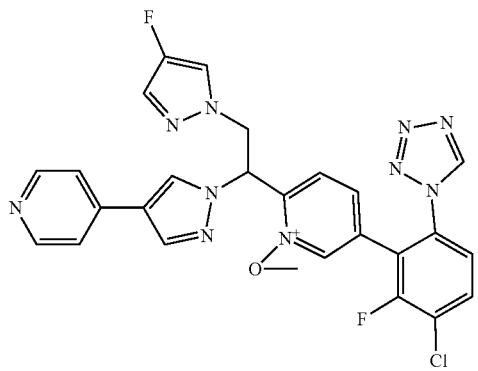 [SMILES: CO[n+]1cc(-c2c(-n3cnnn3)ccc(Cl)c2F)ccc1C(Cn1cc(F)cn1)n1cc(-c2ccncc2)cn1]

LC/MS: mass calculated for $C_{25}H_{17}ClF_2N_{10}O$: 546.12, measured (ES, m/z): 547.25[M+H]+. $^1$H NMR (400 MHz, DMSO-$d_6$) δ 9.71 (s, 1H), 8.87 (s, 1H), 8.74-8.85 (m, 2H), 8.45-8.57 (m, 2H), 8.04-8.22 (m, 3H), 7.70-7.81 (m, 2H), 7.59 (d, J=8.3 Hz, 1H), 7.45 (d, J=4.2 Hz, 1H), 7.27 (dd, J=8.3, 1.6 Hz, 1H), 6.53-6.60 (m, 1H), 4.83-5.17 (m, 2H). $^{19}$F NMR (376 MHz, DMSO-$d_6$) δ −74.15, −112.64, −177.60.

Example 286: 5-(3-Chloro-2-fluoro-6-(1H-tetrazol-1-yl)phenyl)-2-(2-(4-fluoro-1H-pyrazol-1-yl)-1-(4-(4-((methoxycarbonyl)amino)phenyl)-1H-pyrazol-1-yl)ethyl)pyridine 1-oxide

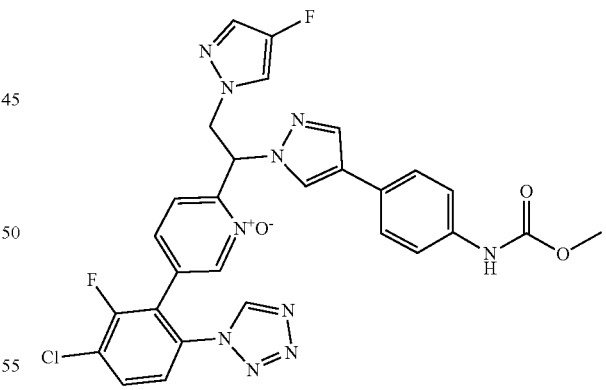

LC/MS: mass calculated for $C_{28}H_{21}ClF_2N_{10}O_3$: 618.14, measured (ES, m/z): 619.15[M+H]+. $^1$H NMR (400 MHz, DMSO-$d_6$) δ 9.60-9.69 (m, 2H), 8.51 (d, J=1.6 Hz, 1H), 8.23 (s, 1H), 7.98-8.09 (m, 1H), 8.00 (s, 1H), 7.76 (dd, J=8.7, 1.5 Hz, 1H), 7.62 (d, J=4.6 Hz, 1H), 7.40-7.49 (m, 5H), 7.26-7.32 (m, 1H), 7.15-7.25 (m, 1H), 6.50 (dd, J=9.5, 4.5 Hz, 1H), 4.82-5.06 (m, 2H), 3.66 (s, 3H). $^{19}$F NMR (376 MHz, DMSO-$d_6$) δ −74.33, −112.67, −177.92.

Example 287: 5-(3-Chloro-2-fluoro-6-(1H-tetrazol-1-yl)phenyl)-2-(3-(methoxy-d3)-1-(4-(4-((methyl-d3)amino)phenyl)-1H-pyrazol-1-yl)propyl)pyridine 1-oxide

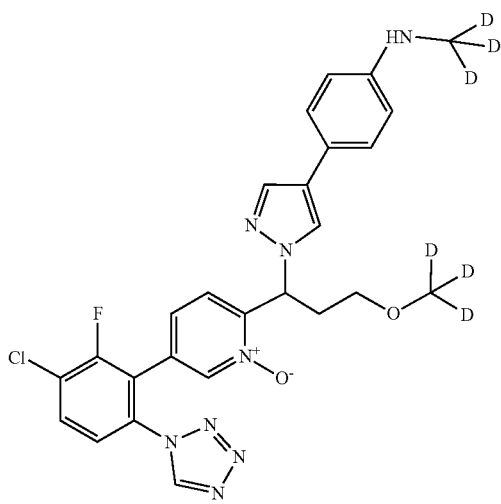 [SMILES: [2H]C([2H])([2H])Nc1ccc(-c2cnn(C(CCOC([2H])([2H])[2H])c3ccc(-c4c(-n5cnnn5)ccc(Cl)c4F)c[n+]3[O-])c2)cc1]

LC/MS: mass calculated for $C_{28}H_{18}ClD_6FN_8O_2$: 540.2, measured (ES, m/z): 541.2 [M+H]+, $^1$H NMR (300 MHz, DMSO-d$_6$) d 9.69 (s, 1H), 8.39-8.49 (m, 1H), 8.32 (s, 1H), 8.06 (dd, J=8.7, 7.8 Hz, 1H), 7.94 (s, 1H), 7.76 (dd, J=8.7, 1.6 Hz, 1H), 7.47-7.59 (m, 2H), 7.08-7.34 (m, 2H), 6.94 (d, J=8.2 Hz, 2H), 6.14 (dd, J=8.9, 5.6 Hz, 1H), 3.13-3.37 (m, 2H), 2.39-2.50 (m, 2 h). $^{19}$F NMR (282 MHz, DMSO-d$_6$) d −74.61, −112.71.

Example 288A: (R*)-5-(3-Chloro-2-fluoro-6-(1H-tetrazol-1-yl)phenyl)-2-(2-cyclopropyl-1-(4-(1-oxidopyridin-4-yl)-1H-pyrazol-1-yl)ethyl)pyridine 1-oxide

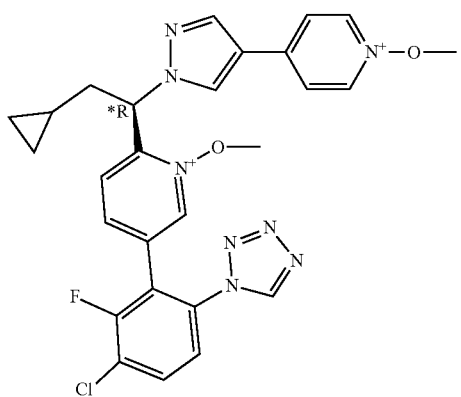 [SMILES: CO[n+]1ccc(-c2cnn([C@H](CC3CC3)c3ccc(-c4c(-n5cnnn5)ccc(Cl)c4F)c[n+]3OC)c2)cc1]

LC/MS: mass calculated for $C_{25}H_{20}ClFN_8O_2$; 518.14, measured (ES, m/z): 519.05 [M+H]+. $^1$H NMR (300 MHz, DMSO-d$_6$) δ 9.69 (s, 1H), 8.71 (s, 1H), 8.42 (s, 1H), 8.13-8.26 (m, 3H), 7.99-8.10 (m, 1H), 7.74-7.80 (m, 1H), 7.62-7.72 (m, 2H), 7.23-7.31 (m, 1H), 7.10-7.19 (m, 1H), 6.08 (dd, J=9.9, 4.3 Hz, 1H), 2.34-2.43 (m, 1H), 1.84-1.92 (m, 1H), 0.56-0.64 (m, 1H), 0.27-0.41 (m, 2H), 0.08-0.16 (m, 1H), 0.01-0.03 (m, 1H). $^{19}$F NMR (282 MHz, DMSO-d$_6$) δ −112.76.

Example 288B: (S*)-5-(3-Chloro-2-fluoro-6-(1H-tetrazol-1-yl)phenyl)-2-(2-cyclopropyl-1-(4-(1-oxidopyridin-4-yl)-1H-pyrazol-1-yl)ethyl)pyridine 1-oxide

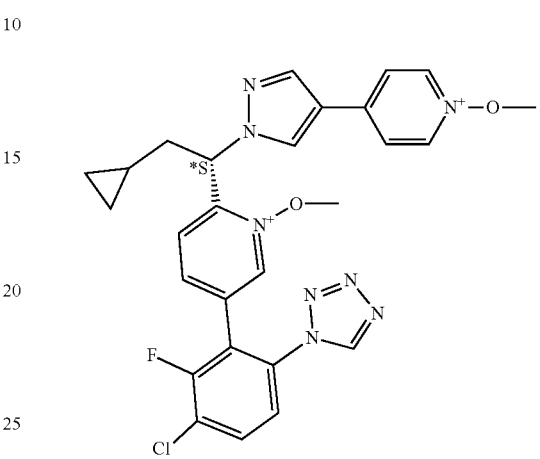

LC/MS: mass calculated for $C_{25}H_{20}ClFN_8O_2$: 518.13, measured (ES, m/z): 519.05 [M+H]+. $^1$H NMR (300 MHz, DMSO-d$_6$) δ 9.69 (s, 1H), 8.70 (s, 1H), 8.42 (s, 1H), 8.12-8.24 (m, 3H), 7.99-8.10 (m, 1H), 7.72-7.82 (m, 1H), 7.61-7.71 (m, 2H), 7.24-7.31 (m, 1H), 7.11-7.19 (m, 1H), 6.08 (dd, J=9.8, 4.3 Hz, 1H), 2.33-2.42 (m, 1H), 1.82-1.93 (m, 1H), 0.56-0.65 (m, 1H), 0.27-0.42 (m, 2H), 0.08-0.17 (m, 1H), 0.01-0.03 (m, 1H). $^{19}$F NMR (282 MHz, DMSO-d$_6$) δ −112.76.

Example 289: 2-(1-(4-(6-Amino-2-fluoropyridin-3-yl)-1H-pyrazol-1-yl)-2-(4-fluoro-1H-pyrazol-1-yl)ethyl)-5-(3-Chloro-2-fluoro-6-(1H-tetrazol-1-yl)phenyl)pyridine 1-oxide

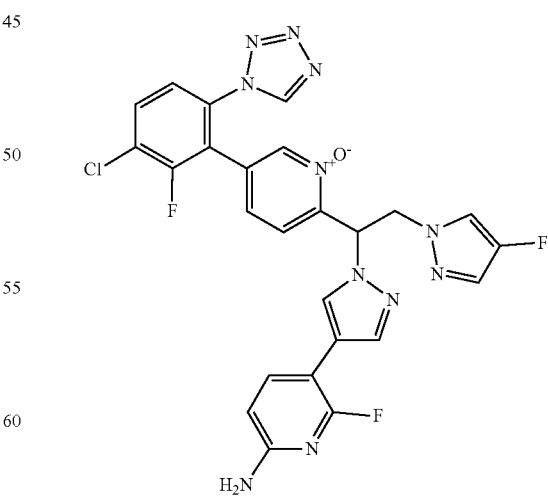

LC/MS: mass calculated for $C_{25}H_{17}ClF_3NO_{11}$: 579.12, measured (ES, m/z): 580.05[M+H]+. $^1$H NMR (400 MHz, DMSO-d$_6$) δ 9.67-9.71 (m, 1H), 8.49-8.53 (m, 1H), 8.01-

8.11 (m, 2H), 7.90 (s, 1H), 7.72-7.80 (m, 2H), 7.61 (d, J=4.6 Hz, 1H), 7.45 (d, J=4.2 Hz, 1H), 7.25-7.31 (m, 1H), 7.17-7.23 (m, 1H), 6.51 (dd, J=9.5, 4.5 Hz, 1H), 6.35 (dd, J=8.2, 2.0 Hz, 1H), 4.78-5.07 (m, 2H). $^{19}$F NMR (376 MHz, DMSO-d$_6$) δ −71.69, −74.68, −112.63, −177.91.

Example 290: 2-(2-((1S*,2S*)-2-Carbamoylcyclopropyl)-1-(4-(1-oxidopyridin-4-yl)-1H-pyrazol-1-yl)ethyl)-5-(3-chloro-2-fluoro-6-(1H-tetrazol-1-yl)phenyl)pyridine 1-oxide

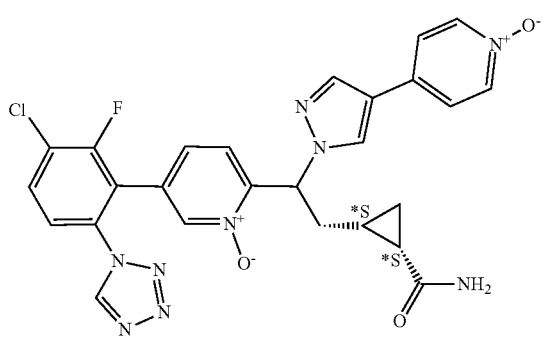

LC/MS: mass calculated for C$_{26}$H$_{21}$ClFN$_9$O$_3$: 561.14, measured (ES, m/z): 562.10 [M+H]$^+$. $^1$H NMR (300 MHz, DMSO-d$_6$) δ 9.69 (s, 1H), 8.59-8.68 (m, 1H), 8.42 (s, 1H), 8.13-8.23 (m, 3H), 8.02-8.11 (m, 1H), 7.76 (dd, J=8.7, 1.6 Hz, 1H), 7.59-7.70 (m, 2H), 7.53 (s, 1H), 7.22-7.27 (m, 1H), 7.14-7.20 (m, 1H), 6.74 (s, 1H), 6.05 (dd, J=10.4, 3.7 Hz, 1H), 2.28-2.40 (m, 1H), 2.00-2.14 (m, 1H), 1.45-4.53 (m, 1H), 0.92-1.03 (m, 1H), 0.62-0.79 (m, 1H), 0.34-0.56 (m, 1H). $^{19}$F NMR (282 MHz, DMSO-d$_6$) δ −112.71.

Example 291: 2-(2-((1S*,2R*)-2-Carbamoylcyclopropyl)-1-(4-(1-oxidopyridin-4-yl)-1H-pyrazol-1-yl)ethyl)-5-(3-chloro-2-fluoro-6-(1H-tetrazol-1-yl)phenyl)pyridine 1-oxide

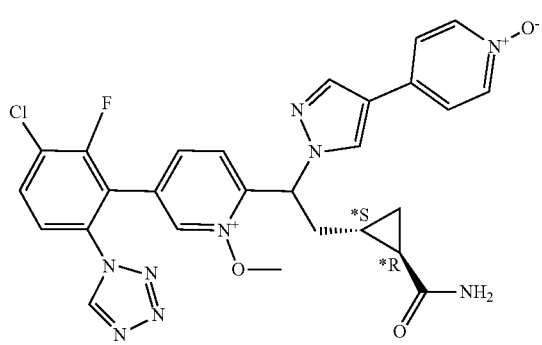 [SMILES: CO[n+]1cc(-c2c(-n3cnnn3)ccc(Cl)c2F)ccc1C(C[C@@H]1C[C@H]1C(N)=O)n1cc(-c2cc[n+]([O-])cc2)cn1]

LC/MS: mass calculated for C$_{26}$H$_{21}$ClFN$_9$O$_3$: 561.14, measured (ES, m/z): 562.30 [M+H]$^+$. $^1$H NMR (300 MHz, DMSO-d$_6$) δ 9.69 (s, 1H), 8.56-8.66 (m, 1H), 8.36-8.46 (m, 1H), 8.00-8.22 (m, 4H), 7.76 (dd, J=8.7, 1.6 Hz, 1H), 7.62-7.71 (m, 2H), 7.35-7.60 (m, 2H), 7.10-7.22 (m, 1H), 6.75-6.91 (m, 1H), 5.89-6.18 (m, 1H), 2.18-2.49 (m, 2H), 1.52-1.70 (m, 1H), 0.52-0.93 (m, 3H). $^{19}$F NMR (282 MHz, DMSO-d$_6$) δ −112.68.

Example 292: 5-(3-Chloro-2-fluoro-6-(1H-tetrazol-1-yl)phenyl)-2-(2-cyclopropyl-1-(4-(2,2-difluorobenzo[d][1,3]dioxol-5-yl)-1H-pyrazol-1-yl)ethyl)pyridine 1-oxide

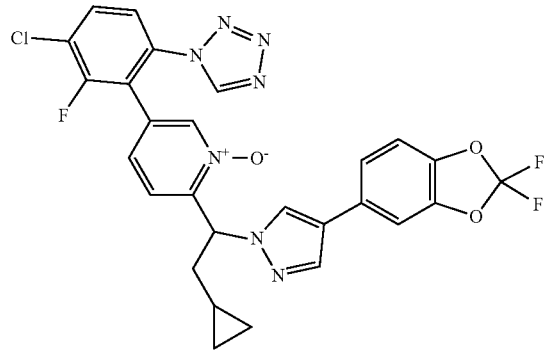 [SMILES: [O-][n+]1cc(-c2c(-n3cnnn3)ccc(Cl)c2F)ccc1C(CC1CC1)n1cc(-c2ccc3c(c2)OC(F)(F)O3)cn1]

LC/MS: mass calculated for C$_{27}$H$_{19}$ClF$_3$N$_7$O$_3$: 581.1, measured (ES, m/z): 582.2 [M+H]$^+$. $^1$H NMR (400 MHz, CD$_3$OD) δ ppm −0.05-0.04 (m, 1H) 0.08-0.18 (m, 1H) 0.28-0.42 (m, 2 h) 0.58-0.70 (m, 1H) 1.88-1.95 (m, 1H) 2.37-2.48 (m, 1H) 6.09-6.20 (m, 1H) 7.09-7.13 (m, 1H) 7.16-7.23 (m, 1H) 7.29-7.41 (m, 3H) 7.53 (dd, J=8.80, 1.47 Hz, 1H) 7.80-7.86 (m, 1H) 7.87-7.92 (m, 1H) 8.18-8.26 (m, 1H) 8.27-8.33 (m, 1H) 9.31 (s, 1H).

Example 293: 5-(3-Chloro-2-fluoro-6-(1H-tetrazol-1-yl)phenyl)-2-(1-(4-(2-methylpyridin-4-yl)-1H-pyrazol-1-yl)-2-(1H-pyrazol-1-yl)ethyl)pyridine 1-oxide

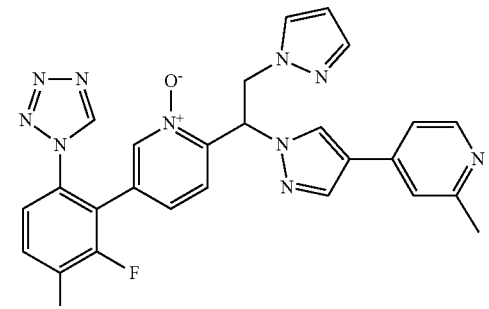

LC/MS: mass calculated for C$_{26}$H$_{20}$ClFN$_{10}$O: 542.1, measured (ES, m/z): 543.3 [M+H]$^+$. $^1$H NMR (400 MHz, CD$_3$OD) δ ppm 5.09 (bdd, J=14.2, 4.4 Hz, 2H), 5.14-5.29 (m, 7H), 6.11-6.19 (m, 3H), 6.70 (bdd, J=9.8, 4.4 Hz, 1H), 7.32 (bd, J=8.8 Hz, 3H), 7.45 (bdd, J=8.1, 2.2 Hz, 7H), 7.62 (bdd, J=8.6, 1.7 Hz, 6H), 7.65-7.73 (m, 8H), 7.88-7.96 (m, 12H), 7.97-8.01 (m, 4H), 8.03-8.10 (m, 11H), 8.33 (s, 6H), 8.42-8.45 (m, 4H), 9.39 (s, 1H).

Example 294: 5-(5-Chloro-2-(1H-tetrazol-1-yl)phenyl)-2-(1-(4-(2-cyclopropylpyridin-4-yl)-1H-pyrazol-1-yl)-2-(H-pyrazol-1-yl)ethyl)pyridine 1-oxide

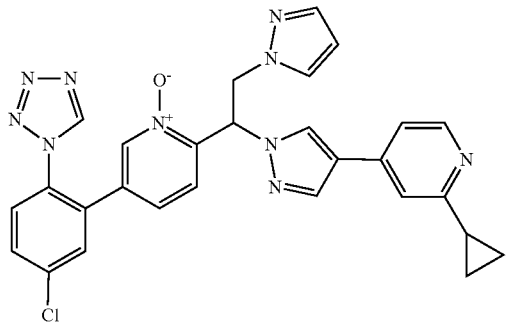 [SMILES: [O-][n+]1cc(-c2cc(Cl)ccc2-n2cnnn2)ccc1C(Cn1cccn1)n1cc(-c2ccnc(C3CC3)c2)cn1]

LC/MS: mass calculated for $C_{28}H_{23}ClN_{10}O$: 550.2, measured (ES, m/z): 551.3 [M+H]$^+$. $^1$H NMR (400 MHz, CD$_3$OD) δ ppm 1.21-1.47 (m, 5H), 2.19-2.35 (m, 3H), 5.01-5.12 (m, 2H), 5.20 (dd, J=13.9, 10.0 Hz, 1H), 6.15 (bt, J=2.0 Hz, 1H), 6.68 (d, J=9.8 Hz, 1H), 7.20 (d, J=8.3 Hz, 1H), 7.40-7.48 (m, 1H), 7.64 (d, J=8.3 Hz, 1H), 7.68-7.75 (m, 1H), 7.76-7.83 (m, 1H), 7.86 (d, J=6.6 Hz, 1H), 8.32-8.36 (m, 1H), 8.38 (d, J=6.4 Hz, 1H), 8.55 (s, 1H), 9.39 (s, 1H).

Example 295: 2-(2-(2-(7-Carboxy-5-azaspiro[2.4]heptane-5-carbonyl)cyclopropyl)-1-(4-(pyridin-4-yl)-1H-pyrazol-1-yl)ethyl)-5-(3-chloro-2-fluoro-6-(1H-tetrazol-1-yl)phenyl)pyridine 1-oxide

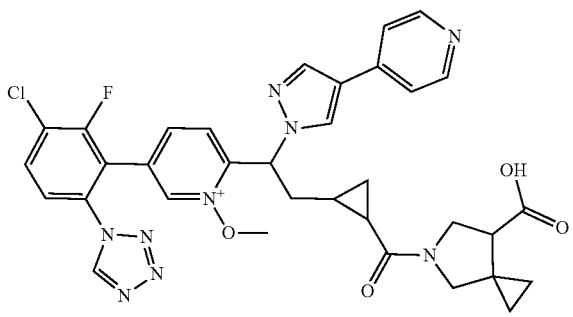 [SMILES: CO[n+]1cc(-c2c(-n3cnnn3)ccc(Cl)c2F)ccc1C(CC1CC1C(=O)N1CC(C(=O)O)C2(CC2)C1)n1cc(-c2ccncc2)cn1]

LC/MS: mass calculated for $C_{33}H_{29}ClFN_9O_4$: 669.20, measured (ES, m/z): 670.20 [M+H]$^+$. $^1$H NMR (300 MHz, DMSO-d$_6$) δ 9.70 (s, 1H), 8.98-9.12 (m, 1H), 8.72-8.86 (m, 2H), 8.38-8.54 (m, 2H), 8.10-8.18 (m, 2H), 8.03-8.09 (m, 1H), 7.76 (d, J=8.7 Hz, 1H), 7.35-7.56 (m, 1H), 7.14-7.23 (m, 1H), 6.00-6.19 (m, 1H), 4.12-4.23 (m, 1H) 3.40-4.02 (m, 4H), 3.08-3.32 (m, 1H), 1.41-2.33 (m, 1H), 1.18-1.23 (m, 1H), 0.36-1.16 (m, 8H).

Example 296: 5-(3-Chloro-2-fluoro-6-(1H-tetrazol-1-yl)phenyl)-2-(2-cyclopropyl-1-(1'-methyl-1H,1'H-[4,4'-bipyrazol]-1-yl)ethyl)pyridine 1-oxide

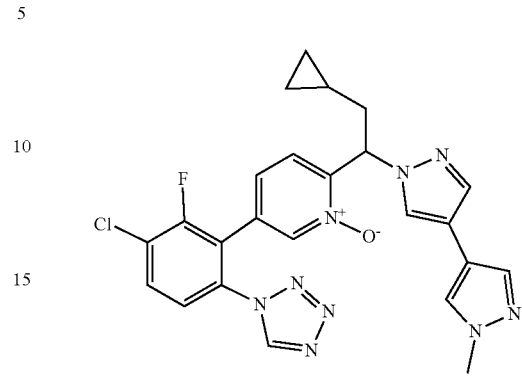

To 1-(1-(5-(3-Chloro-2-fluoro-6-(1H-tetrazol-1-yl)phenyl)pyridin-2-yl)-2-cyclopropylethyl)-1'-methyl-1H,1'H-4,4'-bipyrazole (35 mg, 0.07 mmol) in HOAc (2.5 mL) was added MeReO$_3$ (8.9 mg, 0.04 mmol), followed by 30% H$_2$O$_2$ (122 mg, 1.07 mmol) and the resulting mixture was stirred at room temperature for 1 h.

The solvent was removed under reduced pressure and the residue was dissolved in MeOH, which was subjected to Gilson HPLC purification to yield 5-(3-Chloro-2-fluoro-6-(1H-tetrazol-1-yl)phenyl)-2-(2-cyclopropyl-1-(1'-methyl-1H,1'H-[4,4'-bipyrazol]-1-yl)ethyl)pyridine 1-oxide as a white solid.

LC/MS: mass calculated for $C_{24}H_{21}ClFN_9O$: 505.2, measured (ES, m/z) 506.2 [M+H]$^+$. $^1$H NMR (400 MHz, CD$_3$OD) δ ppm 0.03-0.11 (m, 1H) 0.16-0.25 (m, 1H) 0.35-0.49 (m, 2 h) 0.65-0.75 (m, 1H) 1.89-2.00 (m, 1H) 2.49 (ddd, J=13.94, 10.03, 5.87 Hz, 1H) 3.88-3.91 (m, 3H) 6.12-6.21 (m, 1H) 7.24-7.30 (m, 1H) 7.33-7.39 (m, 1H) 7.58-7.63 (m, 1H) 7.66 (s, 1H) 7.78 (d, J=9.78 Hz, 2 h) 7.91 (dd, J=8.80, 7.83 Hz, 1H) 8.06 (s, 1H) 8.35 (s, 1H) 9.38 (s, 1H).

Example 297: (R)-5-(3-Chloro-2-fluoro-6-(1H-tetrazol-1-yl)phenyl)-2-(3-(methoxy-d3)-1-(4-(4-((methoxycarbonyl)amino)phenyl)-1H-pyrazol-1-yl)propyl)pyridine 1-oxide

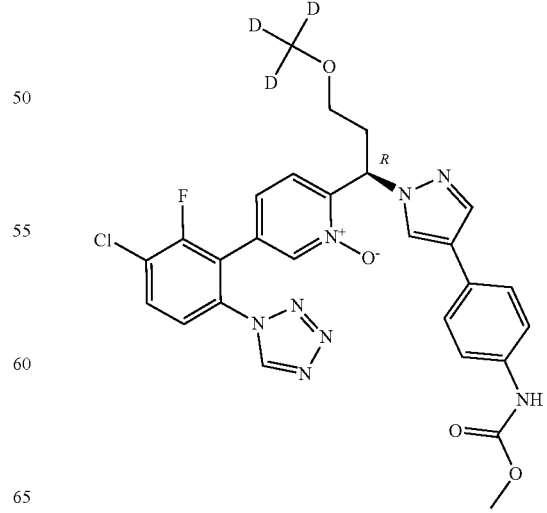

Step 1: 5-Bromo-2-(1-(4-iodo-1H-pyrazol-1-yl)-3-(methoxy-d3)propyl)pyridine

A mixture of 3-(5-bromopyridin-2-yl)-3-(4-iodo-1H-pyrazol-1-yl)propan-1-ol (500 mg, 1.23 mmol, 1.0 equiv.), silver oxide (1.42 g, 6.13 mmol, 5.0 equiv.) and iodomethane-d₃ (888 mg, 6.13 mmol, 5.0 equiv.) in acetonitrile (8 mL) was stirred at 50° C. overnight. After filtration, the filtrate was concentrated. The residue was purified by silica gel chromatography (0→50% ethyl acetate/petroleum ether) to yield 5-bromo-2-(1-(4-iodo-1H-pyrazol-1-yl)-3-(methoxy-d₃)propyl)pyridine as a light yellow solid. LC/MS: mass calculated for $C_{12}H_{10}D_3BrIN_3O$: 423.95, measured (ES, m/z): 424.90, 426.90 [M+H, M+H+2]⁺.

Step 2: Methyl (4-(1-(1-(5-bromopyridin-2-yl)-3-(methoxy-d₃)propyl)-1H-pyrazol-4-yl)phenyl)carbamate A mixture of 5-bromo-2-(1-(4-iodo-1H-pyrazol-1-yl)-3-(methoxy-d₃)propyl)pyridine (350 mg, 0.82 mmol, 1.0 equiv.), methyl (4-(4,4,5,5-tetramethyl-1,3,2-dioxaborolan-2-yl)phenyl)carbamate (228 mg, 0.82 mmol, 1.0 equiv.), potassium phosphate (524 mg, 2.47 mmol, 3.0 equiv.) and Pd(PPh₃)₄ (95 mg, 0.08 mmol, 0.1 equiv.) in 1,4-dioxane (6 mL) and water (2 mL) was stirred at 90° C. overnight. After cooling to room temperature, the reaction was quenched with H₂O and extracted with ethyl acetate twice. The combined organic layers were washed with brine, dried over Na₂SO₄ and concentrated. The residue was purified by silica gel chromatography (0→50% ethyl acetate/petroleum ether) to yield methyl (4-(1-(1-(5-bromopyridin-2-yl)-3-(methoxy-d₃)propyl)-1H-pyrazol-4-yl)phenyl)carbamate as a light yellow solid. LC/MS: mass calculated for $C_{20}H_{18}D3BrN_4O_3$: 447.10, measured (ES, m/z): 448.05, 450.05 [M+H, M+H+2]⁺.

Step 3: Methyl (4-(1-(1-(5-(6-amino-3-chloro-2-fluorophenyl)pyridin-2-yl)-3-(methoxy-d₃)propyl)-1H-pyrazol-4-yl)phenyl)carbamate A mixture of methyl (4-(1-(1-(5-bromopyridin-2-yl)-3-(methoxy-d₃)propyl)-1H-pyrazol-4-yl)phenyl)carbamate (150 mg, 0.34 mmol, 1.0 equiv.), 6-amino-3-chloro-2-fluorophenylboronic acid (95 mg, 0.50 mmol, 1.5 equiv.), potassium carbonate (139 mg, 1.00 mmol, 3.0 equiv.) and Pd(PPh₃)₄ (39 mg, 0.03 mmol, 0.1 equiv.) in 1,4-dioxane (4 mL) and water (1 mL) was stirred at 90° C. overnight. After cooling to room temperature, the reaction was quenched with H₂O and extracted with ethyl acetate twice. The combined organic layers were washed with brine, dried over Na₂SO₄ and concentrated. The residue was purified by silica gel chromatography (0→50% ethyl acetate/petroleum ether) to yield methyl (4-(1-(1-(5-(6-amino-3-chloro-2-fluorophenyl)pyridin-2-yl)-3-(methoxy-d₃)propyl)-1H-pyrazol-4-yl)phenyl)carbamate as a light yellow solid. LC/MS: mass calculated for $C_{26}H_{22}D3ClFN_5O_3$: 512.18, measured (ES, m/z): 513.20 [M+H]⁺.

Step 4: Methyl (4-(1-(1-(5-(3-chloro-2-fluoro-6-(1H-tetrazol-1-yl)phenyl)pyridin-2-yl)-3-(methoxy-d₃)propyl)-1H-pyrazol-4-yl)phenyl)carbamate A mixture of methyl (4-(1-(1-(5-(6-amino-3-chloro-2-fluorophenyl)pyridin-2-yl)-3-(methoxy-d₃)propyl)-1H-pyrazol-4-yl)phenyl)carbamate (150 mg, 0.29 mmol, 1.0 equiv.), azidotrimethylsilane (1 mL) and trimethoxymethane (1 mL) in acetic acid glacial (2 mL) was stirred at room temperature overnight. The mixture was concentrated and the residue was purified by reverse phase chromatography on C18 (80 g, MeCN/H₂O (0.05% CF₃COOH): 0→45%) to yield methyl (4-(1-(1-(5-(3-chloro-2-fluoro-6-(1H-tetrazol-1-yl)phenyl)pyridin-2-yl)-3-(methoxy-d₃)propyl)-1H-pyrazol-4-yl)phenyl)carbamate as a light yellow solid. LC/MS: mass calculated for $C_{27}H_{21}D3ClFN_8O_3$: 565.18, measured (ES, m/z): 566.20 [M+H]⁺.

Step 5: (R)-5-(3-Chloro-2-fluoro-6-(1H-tetrazol-1-yl)phenyl)-2-(3-(methoxy-d₃)-1-(4-(4-((methoxycarbonyl)amino)phenyl)-1H-pyrazol-1-yl)propyl)pyridine 1-oxide A mixture of methyl (4-(1-(1-(5-(3-chloro-2-fluoro-6-(1H-tetrazol-1-yl)phenyl)pyridin-2-yl)-3-(methoxy-d₃)propyl)-1H-pyrazol-4-yl)phenyl)carbamate (100 mg, 0.18 mmol, 1.0 equiv.), methyl trioxorhenium (VII) (22 mg, 0.09 mmol, 0.5 equiv.) and hydrogen peroxide (0.09 mL, 0.88 mmol, 30 wt %, 5.0 equiv.) in CH₃OH (2.0 mL) was stirred at room temperature for 1 h. The reaction was purified by reverse phase chromatography on C18 (80 g, MeCN/H₂O (0.05% CF₃COOH): 0→45%) and then Prep-Chiral HPLC to yield (R*)-5-(3-chloro-2-fluoro-6-(1H-tetrazol-1-yl)phenyl)-2-(3-(methoxy-d₃)-1-(4-(4-((methoxycarbonyl)amino)phenyl)-1H-pyrazol-1-yl)propyl)pyridine 1-oxide as a white solid.

LC/MS: mass calculated for $C_{27}H_{21}ClD_3FN_8O_4$: 581.17, measured (ES, m/z): 582.2[M+H]⁺. ¹H NMR (300 MHz, DMSO-d₆): δ 9.69 (s, 1H), 9.64 (s, 1H), 8.42 (s, 1H), 8.34 (s, 1H), 8.02-8.10 (m, 1H), 7.96 (s, 1H), 7.74-7.78 (m, 1H), 7.41-7.55 (m, 4H), 7.20-7.25 (m, 1H), 7.12-7.19 (m, 1H), 6.10-6.18 (m, 1H), 3.67 (s, 3H), 3.26-3.32 (m, 1H), 3.14-3.23 (m, 1H), 2.41-2.50 (m, 2H). ¹⁹F NMR (282 MHz, DMSO-d₆): δ −73.42, −112.71.

Example 298: (S*)-5-(3-Chloro-2-fluoro-6-(1H-tetrazol-1-yl)phenyl)-2-(3-(methoxy-d₃)-1-(4-(4-((methoxycarbonyl)amino)phenyl)-1H-pyrazol-1-yl)propyl)pyridine 1-oxide

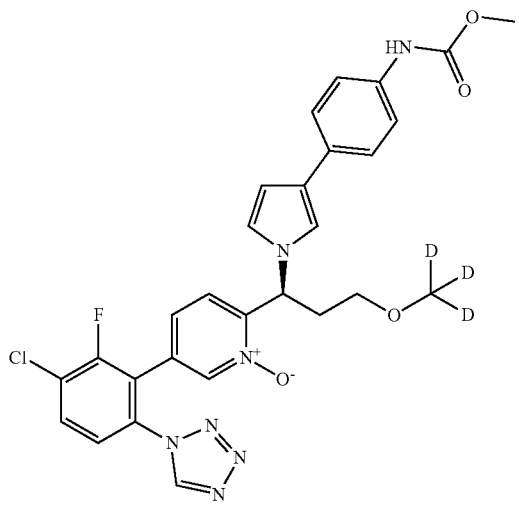 [SMILES: [2H]C([2H])([2H])OCC[C@@H](c1ccc(-c2c(-n3cnnn3)ccc(Cl)c2F)c[n+]1[O-])n1ccc(-c2ccc(NC(=O)OC)cc2)c1]

Step 1: 5-Bromo-2-(1-(4-iodo-1H-pyrazol-1-yl)-3-(methoxy-d3)propyl)pyridine

A mixture of 3-(5-bromopyridin-2-yl)-3-(4-iodo-1H-pyrazol-1-yl)propan-1-ol (500 mg, 1.23 mmol, 1.0 equiv.), silver oxide (1.42 g, 6.13 mmol, 5.0 equiv.) and iodomethane-d$_3$ (888 mg, 6.13 mmol, 5.0 equiv.) in acetonitrile (8 mL) was stirred at 50° C. overnight. After filtration, the filtrate was concentrated. The residue was purified by silica gel chromatography (0→50% ethyl acetate/petroleum ether) to yield 5-bromo-2-(1-(4-iodo-1H-pyrazol-1-yl)-3-(methoxy-d$_3$)propyl)pyridine as a light yellow solid. LC/MS: mass calculated for $C_{12}H_{10}D_3BrIN_3O$: 423.95, measured (ES, m/z): 424.90, 426.90 [M+H, M+H+2]$^+$.

Step 2: Methyl (4-(1-(1-(5-bromopyridin-2-yl)-3-(methoxy-d$_3$)propyl)-1H-pyrazol-4-yl)phenyl)carbamate A mixture of 5-bromo-2-(1-(4-iodo-1H-pyrazol-1-yl)-3-(methoxy-d$_3$)propyl)pyridine (350 mg, 0.82 mmol, 1.0 equiv.), methyl (4-(4,4,5,5-tetramethyl-1,3,2-dioxaborolan-2-yl)phenyl)carbamate (228 mg, 0.82 mmol, 1.0 equiv.), potassium phosphate (524 mg, 2.47 mmol, 3.0 equiv.) and Pd(PPh$_3$)$_4$ (95 mg, 0.08 mmol, 0.1 equiv.) in 1,4-dioxane (6 mL) and water (2 mL) was stirred at 90° C. overnight. After cooling to room temperature, the reaction was quenched with H$_2$O and extracted with ethyl acetate twice. The combined organic layers were washed with brine, dried over Na$_2$SO$_4$ and concentrated. The residue was purified by silica gel chromatography (0→50% ethyl acetate/petroleum ether) to yield methyl (4-(1-(1-(5-bromopyridin-2-yl)-3-(methoxy-d$_3$)propyl)-1H-pyrazol-4-yl)phenyl)carbamate as a light yellow solid. LC/MS: mass calculated for $C_{20}H_{18}D_3BrN_4O_3$: 447.10, measured (ES, m/z): 448.05, 450.05 [M+H, M+H+2]$^+$.

Step 3: Methyl (4-(1-(1-(5-(6-amino-3-chloro-2-fluorophenyl)pyridin-2-yl)-3-(methoxy-d$_3$)propyl)-1H-pyrazol-4-yl)phenyl)carbamate A mixture of methyl (4-(1-(1-(5-bromopyridin-2-yl)-3-(methoxy-d$_3$)propyl)-1H-pyrazol-4-yl)phenyl)carbamate (150 mg, 0.34 mmol, 1.0 equiv.), 6-amino-3-chloro-2-fluorophenylboronic acid (95 mg, 0.50 mmol, 1.5 equiv.), potassium carbonate (139 mg, 1.00 mmol, 3.0 equiv.) and Pd(PPh$_3$)$_4$ (39 mg, 0.03 mmol, 0.1 equiv.) in 1,4-dioxane (4 mL) and water (1 mL) was stirred at 90° C. overnight. After cooling to room temperature, the reaction was quenched with H$_2$O and extracted with ethyl acetate twice. The combined organic layers were washed with brine, dried over Na$_2$SO$_4$ and concentrated. The residue was purified by silica gel chromatography (0→50% ethyl acetate/petroleum ether) to yield methyl (4-(1-(1-(5-(6-amino-3-chloro-2-fluorophenyl)pyridin-2-yl)-3-(methoxy-d$_3$)propyl)-1H-pyrazol-4-yl)phenyl)carbamate as a light yellow solid. LC/MS: mass calculated for $C_{26}H_{22}D3ClFN_5O_3$: 512.18, measured (ES, m/z): 513.20 [M+H]$^+$.

Step 4: Methyl (4-(1-(1-(5-(3-chloro-2-fluoro-6-(1H-tetrazol-1-yl)phenyl)pyridin-2-yl)-3-(methoxy-d$_3$)propyl)-1H-pyrazol-4-yl)phenyl)carbamate A mixture of methyl (4-(1-(1-(5-(6-amino-3-chloro-2-fluorophenyl)pyridin-2-yl)-3-(methoxy-d$_3$)propyl)-1H-pyrazol-4-yl)phenyl)carbamate (150 mg, 0.29 mmol, 1.0 equiv.), azidotrimethylsilane (1 mL) and trimethoxymethane (1 mL) in acetic acid glacial (2 mL) was stirred at room temperature overnight. The mixture was concentrated and the residue was purified by reverse phase chromatography on C18 (80 g, MeCN/H$_2$O (0.05% CF$_3$COOH): 0→45%) to yield methyl (4-(1-(1-(5-(3-chloro-2-fluoro-6-(1H-tetrazol-1-yl)phenyl)pyridin-2-yl)-3-(methoxy-d$_3$)propyl)-1H-pyrazol-4-yl)phenyl)carbamate as a light yellow solid. LC/MS: mass calculated for $C_{27}H_{21}D3ClFN_8O_3$: 565.18, measured (ES, m/z): 566.20 [M+H]$^+$.

Step 5: (S*)-5-(3-Chloro-2-fluoro-6-(1H-tetrazol-1-yl)phenyl)-2-(3-(methoxy-d$_3$)-1-(4-(4-((methoxycarbonyl)amino)phenyl)-1H-pyrazol-1-yl)propyl)pyridine 1-oxide A mixture of methyl (4-(1-(1-(5-(3-chloro-2-fluoro-6-(1H-tetrazol-1-yl)phenyl)pyridin-2-yl)-3-(methoxy-d$_3$)propyl)-1H-pyrazol-4-yl)phenyl)carbamate (100 mg, 0.18 mmol, 1.0 equiv.), methyl trioxorhenium (VII) (22 mg, 0.09 mmol, 0.5 equiv.) and hydrogen peroxide (0.09 mL, 0.88 mmol, 30 wt %, 5.0 equiv.) in CH$_3$OH (2.0 mL) was stirred at room temperature for 1 h. The reaction was purified by reverse phase chromatography on C18 (80 g, MeCN/H$_2$O (0.05% CF$_3$COOH): 0→45%) and then Prep-Chiral HPLC to yield (S*)-5-(3-chloro-2-fluoro-6-(1H-tetrazol-1-yl)phenyl)-2-(3-(methoxy-d$_3$)-1-(4-(4-((methoxycarbonyl)amino)phenyl)-1H-pyrazol-1-yl)propyl)pyridine 1-oxide as a white solid.

LC/MS: mass calculated for $C_{27}H_{21}ClD_3FN_8O_4$: 581.18, measured (ES, m/z): 582.2[M+H]$^+$. $^1$H NMR (300 MHz, DMSO-d$_6$): δ 9.69 (s, 1H), 9.64 (s, 1H), 8.42 (s, 1H), 8.34 (s, 1H), 8.01-8.11 (m, 1H), 7.96 (s, 1H), 7.74-7.78 (m, 1H), 7.42-7.55 (m, 4H), 7.14-7.25 (m, 2H), 6.10-6.17 (m, 1H), 3.67 (s, 3H), 3.27-3.31 (m, 1H), 3.15-3.24 (m, 1H), 2.41-2.50 (m, 2H). $^{19}$F NMR (282 MHz, DMSO-d$_6$): δ −73.41, −112.71.

Example 299: 5-(3-Chloro-2-fluoro-6-(1H-tetrazol-1-yl)phenyl)-2-(2-(4-(piperidine-1-carbonyl)-1H-pyrazol-1-yl)-1-(4-(pyridin-4-yl)-1H-pyrazol-1-yl)ethyl)pyridine 1-oxide

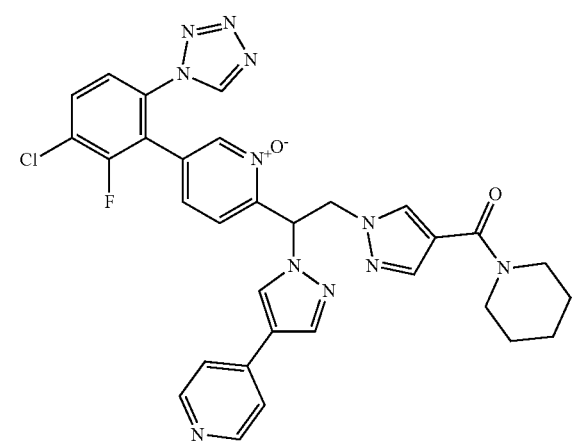

LC/MS: mass calculated for $C_{31}H_{27}ClFN_{11}O_2$: 639.20, measured (ES, m/z): 640.15 [M+H]$^+$. $^1$H NMR (400 MHz, DMSO-d$_6$) δ 9.71 (s, 1H), 8.80 (s, 1H), 8.72 (d, J=6.0 Hz, 2H), 8.53 (s, 1H), 8.45 (s, 1H), 8.04-8.11 (m, 1H), 7.98-8.03 (m, 2H), 7.74-7.81 (m, 2H), 7.53-7.61 (m, 2H), 7.27 (d, J=8.8 Hz, 1H), 6.52-6.60 (m, 1H), 5.08-5.15 (m, 1H), 4.98-5.07 (m, 1H), 3.28-3.40 (m, 4H), 1.50-1.58 (m, 2H), 1.38 (s, 4H). $^{19}$F NMR (376 MHz, DMSO-d$_6$) δ −73.88, −112.63.

Example 300: 5-(3-Chloro-2-fluoro-6-(1H-tetrazol-1-yl)phenyl)-2-(1-(4-(1-oxidopyridin-4-yl)-1H-pyrazol-1-yl)-2-(4-(piperidine-1-carbonyl)-1H-pyrazol-1-yl)ethyl)pyridine 1-oxide

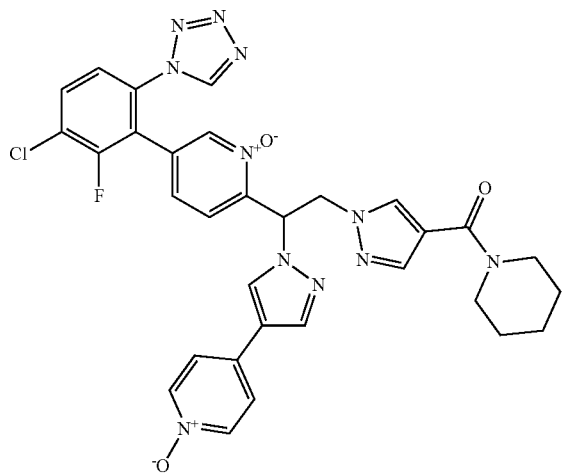

LC/MS: mass calculated for C$_{31}$H$_{27}$ClFN$_{11}$O$_3$: 655.19, measured (ES, m/z): 656.30 [M+H]$^+$. $^1$H NMR (400 MHz, DMSO-d$_6$) δ 9.70 (s, 1H), 8.53 (d, J=2.5 Hz, 2H), 8.22-8.31 (m, 3H), 8.04-8.12 (m, 1H), 7.61-7.81 (m, 5H), 7.48 (d, J=8.3 Hz, 1H), 7.24 (dd, J=8.4, 1.6 Hz, 1H), 6.53 (dd, J=9.8, 4.5 Hz, 1H), 4.95-5.13 (m, 2H), 3.37 (s, 4H), 1.50-1.60 (m, 2H), 1.38 (s, 4H). $^{19}$F NMR (376 MHz, DMSO-d$_6$) δ −74.51, −112.62.

Example 301: 5-(5-Chloro-2-(1H-tetrazol-1-yl)phenyl)-2-(2-(1-oxoisoindolin-2-yl)-1-(4-(pyridin-4-yl)-1H-pyrazol-1-yl)ethyl)pyridine 1-oxide

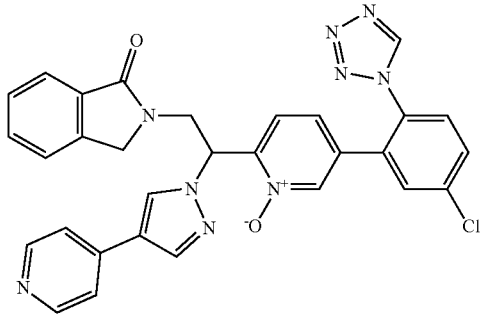

LC/MS: mass calculated for C$_{26}$H$_{19}$ClFN$_9$O: 527.16, measured (ES, m/z): 576.3 [M+H]$^+$.

Example 302: 5-(3-Chloro-2-fluoro-6-(1H-tetrazol-1-yl)phenyl)-2-(1-(4-(2-cyanopyridin-4-yl)-1H-pyrazol-1-yl)-2-cyclopropylethyl)pyridine 1-oxide

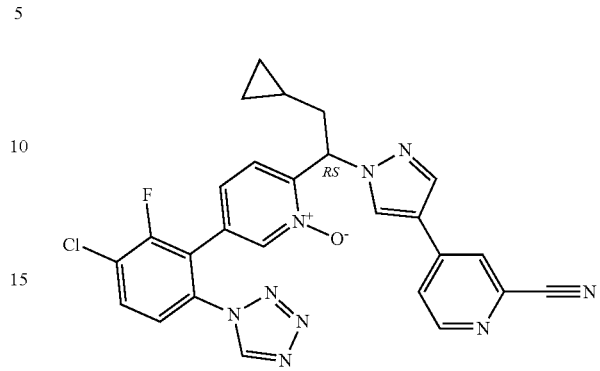

LC/MS: mass calculated for C$_{26}$H$_{19}$ClFN$_9$O: 527.1, measured (ES, m/z): 528.2 [M+H]$^+$. $^1$H NMR (400 MHz, CD$_3$OD) δ ppm 0.01-0.08 (m, 1H) 0.15-0.24 (m, 1H) 0.35-0.48 (m, 2H) 0.62-0.74 (m, 1H) 1.99-2.05 (m, 1H) 2.43-2.53 (m, 1H) 6.22-6.28 (m, 1H) 7.26-7.32 (m, 1H) 7.50-7.54 (m, 1H) 7.59-7.63 (m, 1H) 7.85-7.88 (m, 1H) 7.88-7.89 (m, 1H) 7.89-7.94 (m, 1H) 8.15 (d, J=1.47 Hz, 1H) 8.20 (s, 1H) 8.35-8.38 (m, 1H) 8.58-8.61 (m, 1H) 8.62-8.64 (m, 1H) 9.38 (s, 1H).

Example 303: 5-(3-Chloro-2-fluoro-6-(1H-tetrazol-1-yl)phenyl)-2-(2-cyclopropyl-1-(4-(2-(trifluoromethyl)pyrimidin-4-yl)-1H-pyrazol-1-yl)ethyl)pyridine 1-oxide

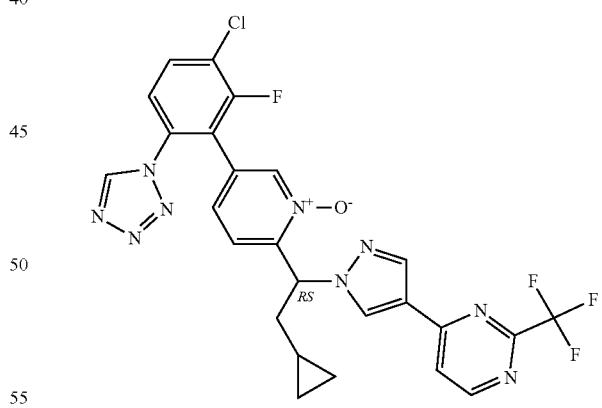

LC/MS: mass calculated for C$_{25}$H$_{18}$ClF$_4$N$_9$O: 571.1, measured (ES, m/z): 572.3 [M+H]$^+$. $^1$H NMR (400 MHz, CD$_3$OD) δ ppm 0.01-0.07 (m, 1H) 0.15-0.23 (m, 1H) 0.33-0.50 (m, 2H) 0.63-0.74 (m, 1H) 2.03-2.09 (m, 1H) 2.43-2.53 (m, 1H) 6.24-6.30 (m, 1H) 7.27-7.33 (m, 1H) 7.55-7.59 (m, 1H) 7.59-7.63 (m, 1H) 7.87-7.90 (m, 1H) 7.90-7.94 (m, 1H) 8.30 (s, 1H) 8.36 (s, 1H) 8.76 (s, 1H) 8.79-8.82 (m, 1H) 9.38 (s, 1H).

Example 304: 5-(3-Chloro-2-fluoro-6-(1H-tetrazol-1-yl)phenyl)-2-(2-(N-methylbenzamido)-1-(4-(pyridin-4-yl)-1H-pyrazol-1-yl)ethyl)pyridine 1-oxide

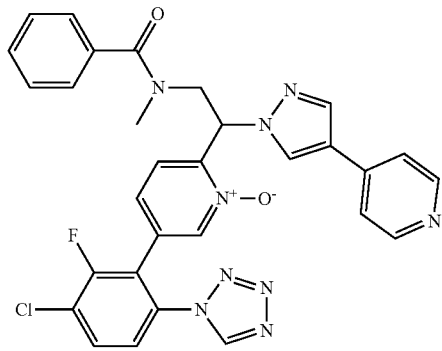 [SMILES: CN(CC(c1ccc(-c2c(-n3cnnn3)ccc(Cl)c2F)c[n+]1[O-])n1cc(-c2ccncc2)cn1)C(=O)c1ccccc1]

LC/MS: mass calculated for $C_{30}H_{23}ClFN_9O_2$: 595.16, measured (ES, m/z): 596.15 [M+H]$^+$. $^1$H NMR (300 MHz, DMSO-d$_6$) δ 9.69 (s, 1H), 8.75-8.88 (m, 1H), 8.44-8.54 (m, 3H), 8.16 (s, 1H), 8.05 (t, J=8.2 Hz, 1H), 7.70-7.85 (m, 2H), 7.55-7.67 (m, 2H), 7.32-7.50 (m, 3H), 7.00-7.31 (m, 3H), 6.40-6.60 (m, 1H), 4.15-4.45 (m, 2H), 2.62-3.15 (m, 3H). 19F NMR (282 MHz, DMSO-d$_6$) d −73.41, −112.66.

Example 305: (R*)-2-(1-(4-(6-Amino-2-fluoropyridin-3-yl)-1H-pyrazol-1-yl)-3-(difluoromethoxy)propyl)-5-(3-chloro-2-fluoro-6-(1H-tetrazol-1-yl)phenyl)pyridine 1-oxide

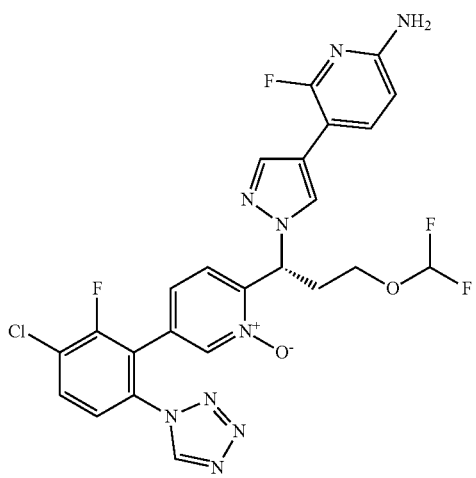 [SMILES: Nc1ccc(-c2cnn([C@H](CCOC(F)F)c3ccc(-c4c(-n5cnnn5)ccc(Cl)c4F)c[n+]3[O-])c2)c(F)n1]

LC/MS: mass calculated for $C_{24}H_{18}ClF_4N_9O_2$: 575.12, measured (ES, m/z): 576.20 [M+H]$^+$. $^1$H NMR (300 MHz, DMSO-d$_6$) δ 9.69 (s, 1H), 8.45 (s, 1H), 8.16-8.22 (m, 1H), 8.02-8.12 (m, 1H), 7.88-7.93 (m, 1H), 7.70-7.80 (m, 2H), 7.12-7.25 (m, 2H), 6.30-6.95 (m, 2H), 6.10-6.20 (m, 1H), 3.76-3.87 (m, 2H), 2.54-2.80 (m, 2H). $^{19}$F NMR (282 MHz, DMSO-d$_6$) δ −71.32, −74.49, −83.25, −112.69.

Example 306: (S*)-2-(1-(4-(6-Amino-2-fluoropyridin-3-yl)-1H-pyrazol-1-yl)-3-(difluoromethoxy)propyl)-5-(3-chloro-2-fluoro-6-(1H-tetrazol-1-yl)phenyl)pyridine 1-oxide

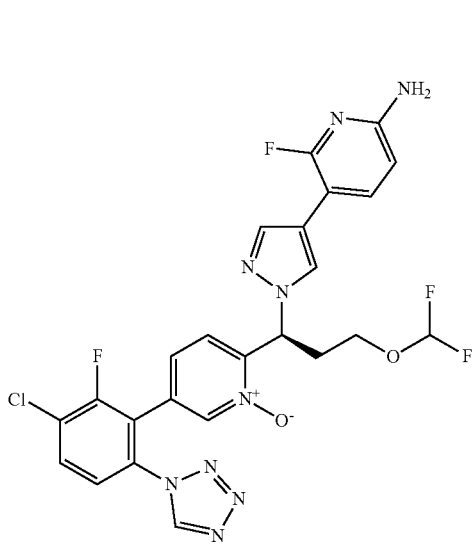 [SMILES: Nc1ccc(-c2cnn([C@@H](CCOC(F)F)c3ccc(-c4c(-n5cnnn5)ccc(Cl)c4F)c[n+]3[O-])c2)c(F)n1]

LC/MS: mass calculated for $C_{24}H_{18}ClF_4N_9O_2$: 575.12, measured (ES, m/z): 576.10 [M+H]$^+$. $^1$H NMR (300 MHz, DMSO-d$_6$) δ 9.69 (s, 1H), 8.44 (s, 1H), 8.18 (d, J=1.8 Hz, 1H), 8.02-8.10 (m, 1H), 7.90 (d, J=1.6 Hz, 1H), 7.72-7.85 (m, 2H), 7.13-7.24 (m, 2H), 6.60-6.80 (m, 1H), 6.31-6.40 (m, 3H), 6.08-6.18 (m, 1H), 3.78-3.88 (m, 1H), 3.50-3.60 (m, 1H), 2.65-2.72 (m, 2H).

Example 307: 5-(3-Chloro-2-fluoro-6-(1H-tetrazol-1-yl)phenyl)-2-(2-(N-methyl-2-phenylacetamido)-1-(4-(pyridin-4-yl)-1H-pyrazol-1-yl)ethyl)pyridine 1-oxide

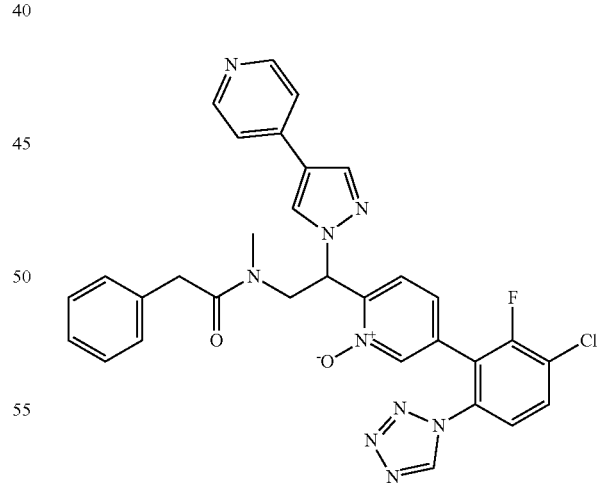

LC/MS: mass calculated for $C_{31}H_{25}ClFN_9O_2$: 609.18, measured (ES, m/z): 610.15 [M+H]$^+$. $^1$H NMR (300 MHz, DMSO-d$_6$) δ 9.68 (d, J=8.9 Hz, 1H), 8.55-8.84 (m, 3H), 8.38-8.52 (m, 2H), 7.99-8.15 (m, 1H), 7.57-7.77 (m, 4H), 7.11-7.28 (m, 4H), 7.02-7.09 (m, 2H), 6.31 (dd, J=9.5, 4.8 Hz, 1H), 4.27 (m, 1H), 3.98-4.11 (m, 1H), 3.50-3.74 (m, 2H), 2.75 (d, J=8.8 Hz, 3H). $^{19}$F NMR (282 MHz, DMSO-d$_6$) d −73.49, −112.61, −112.67.

Example 308: 2-(2-((tert-Butoxycarbonyl)amino)-1-(4-(2-fluoropyridin-4-yl)-1H-pyrazol-1-yl)ethyl)-5-(5-chloro-2-(1H-tetrazol-1-yl)phenyl)pyridine 1-oxide

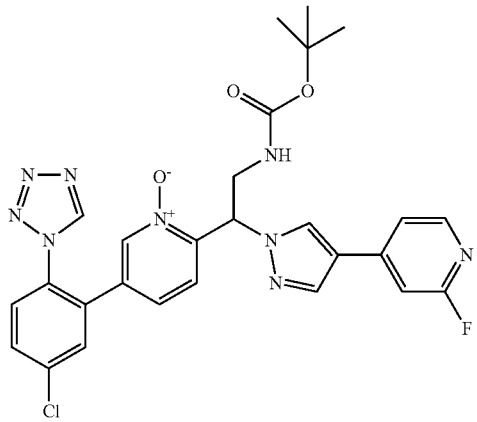 [SMILES: CC(C)(C)OC(=O)NCC(c1ccc(-c2cc(Cl)ccc2-n2cnnn2)c[n+]1[O-])n1cc(-c2ccnc(F)c2)cn1]

LC/MS: mass calculated for $C_{27}H_{25}ClFN_9O_3$: 577.2, measured (ES, m/z): 578.3 [M+H]$^+$. $^1$H NMR (400 MHz, CD$_3$OD) δ ppm 1.35 (s, 9H), 3.86-4.07 (m, 3H), 6.32 (dd, J=8.1, 5.6 Hz, 1H), 7.17 (dd, J=8.3, 1.5 Hz, 1H), 7.29 (s, 1H), 7.39-7.59 (m, 2H), 7.68-7.74 (m, 1H), 7.74-7.81 (m, 2H), 8.04-8.20 (m, 2H), 8.28 (d, J=1.5 Hz, 1H), 8.49 (s, 1H), 9.38 (s, 1H).

Example 309: 5-(5-Chloro-2-(1H-tetrazol-1-yl)phenyl)-2-(1-(4-(2-fluoropyridin-4-yl)-1H-pyrazol-1-yl)-2-((methoxycarbonyl)amino)ethyl)pyridine 1-oxide

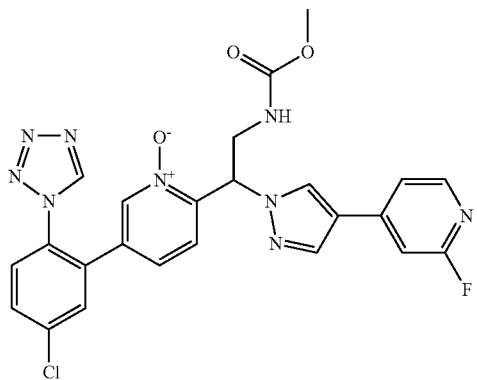 [SMILES: COC(=O)NCC(c1ccc(-c2cc(Cl)ccc2-n2cnnn2)c[n+]1[O-])n1cc(-c2ccnc(F)c2)cn1]

LC/MS: mass calculated for $C_{24}H_{19}ClFN_9O_3$: 535.1, measured (ES, m/z): 536.3 [M+H]$^+$. $^1$H NMR (400 MHz, CD$_3$OD) δ ppm 3.59 (s, 3H), 3.91-4.20 (m, 2H), 6.35 (bdd, J=7.8, 5.9 Hz, 1H), 7.10-7.23 (m, 1H), 7.29 (s, 1H), 7.43-7.48 (m, 2H), 7.49-7.54 (m, 1H), 7.68-7.74 (m, 1H), 7.74-7.83 (m, 2H), 8.03-8.21 (m, 2H), 8.29 (d, J=1.5 Hz, 1H), 8.49 (s, 1H), 9.36 (s, 1H). $^{19}$F NMR (282 MHz, DMSO-d$_6$) δ −73.49, −112.61.

Example 310: 5-(3-Chloro-2-fluoro-6-(1H-tetrazol-1-yl)phenyl)-2-(2-(N-methylacetamido)-1-(4-(pyridin-4-yl)-1H-pyrazol-1-yl)ethyl)pyridine 1-oxide

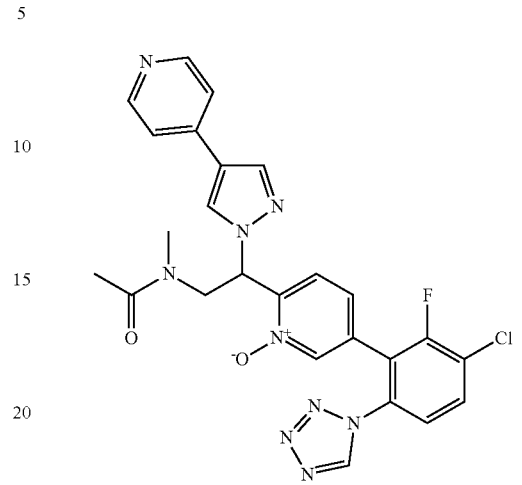

LC/MS: mass calculated for $C_{25}H_{21}ClFN_9O_2$: 533.14, measured (ES, m/z): 534.10 [M+H]$^+$. $^1$H NMR (300 MHz, DMSO-d$_6$) δ 9.60-9.68 (m, 1H), 8.75 (d, J=5.7 Hz, 1H), 8.49-8.70 (m, 2H), 8.38-8.48 (m, 1H), 8.22-8.38 (s, 1H), 8.00 (t, J=8.2 Hz, 1H), 7.80-7.85 (m, 2H), 7.62-7.78 (m, 2H), 7.21-7.39 (m, 2H), 6.23-6.38 (m, 1H), 4.05-4.43 (m, 2H), 2.70-2.85 (m, 3H), 1.80-2.00 (m, 3H). 19F NMR (282 MHz, DMSO-d$_6$) d −73.80, −112.76.

Example 311: 5-(3-Chloro-2-fluoro-6-(1H-tetrazol-1-yl)phenyl)-2-(2-((methoxycarbonyl)(methyl)amino)-1-(4-(pyridin-4-yl)-1H-pyrazol-1-yl)ethyl)pyridine 1-oxide

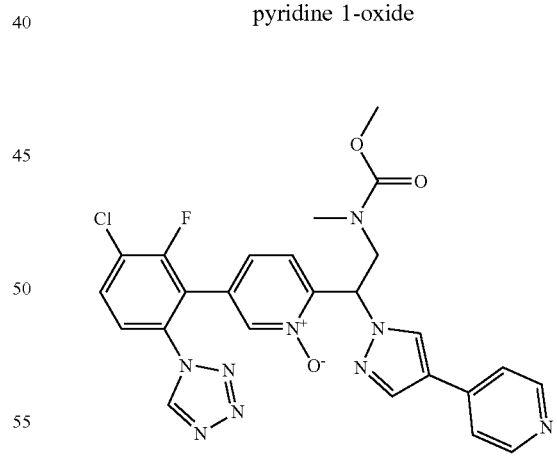

LC/MS: mass calculated for $C_{25}H_{21}ClFN_9O_3$: 549.1, measured (ES, m/z): 550.25 [M+H]$^+$. $^1$H NMR (300 MHz, DMSO-d$_6$) δ 9.59 (s, 1H), 8.91 (s, 1H), 8.63-8.76 (m, 2H), 8.32-8.50 (m, 2H), 8.15-8.25 (m, 2H), 7.96 (t, J=8.2 Hz, 1H), 7.61-7.75 (m, 2H), 7.25 (dd, J=8.3, 1.7 Hz, 1H), 6.18-6.39 (m, 1H), 4.07-4.30 (m, 1H), 3.96-4.07 (m, 1H), 3.32-3.62 (m, 3H), 2.60-2.80 (m, 3H). 19F NMR (282 MHz, DMSO-d$_6$) d −74.06, −112.80.

Example 312: 5-(5-Chloro-2-(1H-tetrazol-1-yl)phenyl)-2-(2-(cyclopropanecarboxamido)-1-(4-(2-fluoropyridin-4-yl)-1H-pyrazol-1-yl)ethyl)pyridine 1-oxide

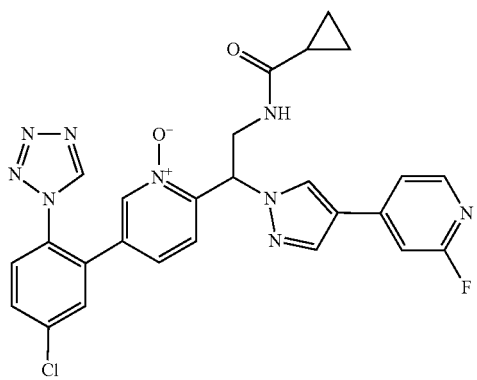 [SMILES: O=C(NCC(c1ccc(-c2cc(Cl)ccc2-n2cnnn2)c[n+]1[O-])n1cc(-c2ccnc(F)c2)cn1)C1CC1]

LC/MS: mass calculated for $C_{26}H_{21}ClFN_9O_2$: 545.1, measured (ES, m/z): 546.2 [M+H]$^+$. $^1$H NMR (400 MHz, CD$_3$OD) δ ppm 0.63-0.85 (m, 4H), 1.44-1.53 (m, 1H), 4.04-4.22 (m, 2H), 6.37 (dd, J=8.3, 5.4 Hz, 1H), 7.16 (dd, J=8.3, 1.5 Hz, 1H), 7.24-7.35 (m, 2H), 7.39-7.60 (m, 4H), 7.67-7.75 (m, 1H), 7.75-7.82 (m, 1H), 8.05-8.20 (m, 1H), 8.28 (d, J=1.5 Hz, 1H), 8.49 (s, 1H), 9.37 (s, 1H).

Example 313: 5-(3-Chloro-2-fluoro-6-(1H-tetrazol-1-yl)phenyl)-2-(1-(4-(4-((methoxycarbonyl)amino)phenyl)-1H-pyrazol-1-yl)-2-(2-oxopyridin-1(2H)-yl)ethyl)pyridine 1-oxide

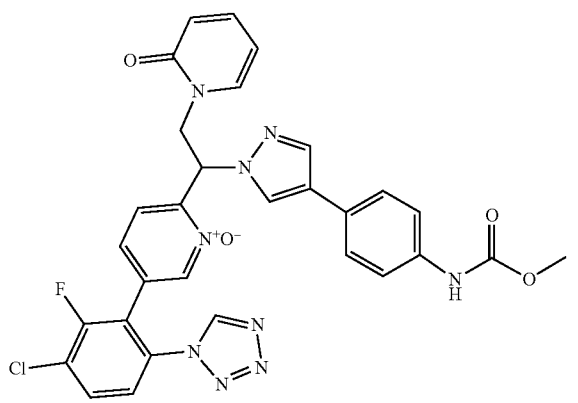

LC/MS: mass calculated for $C_{30}H_{23}ClFN_9O_4$: 627.2, measured (ES, m/z): 628.15 [M+H]$^+$. $^1$H NMR (300 MHz, DMSO-d$_6$) δ 9.67 (s, 1H), 9.61 (s, 1H), 8.44 (d, J=1.5 Hz, 1H), 8.13 (s, 1H), 8.01-8.10 (m, 1H), 7.91 (s, 1H), 7.64-7.79 (m, 2H), 7.33-7.48 (m, 4H), 7.27-7.38 (m, 1H), 7.21 (dd, J=8.3, 1.6 Hz, 1H), 7.16 (d, J=6.0 Hz, 1H), 6.45-6.55 (m, 1H), 6.36 (d, J=9.1 Hz, 1H), 5.98-6.08 (m, 1H), 4.62-4.75 (m, 2H), 3.64 (s, 3H).

Example 314: (S*)-5-(3-Chloro-2-fluoro-6-(1H-tetrazol-1-yl)phenyl)-2-(3-(difluoromethoxy)-1-(4-(3-fluoro-1-oxidopyridin-4-yl)-1H-pyrazol-1-yl)propyl)pyridine 1-oxide

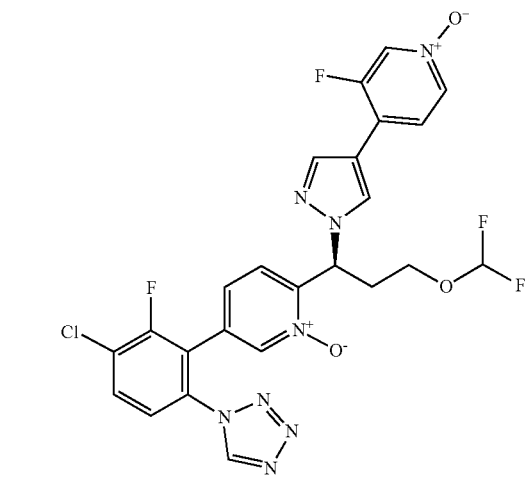 [SMILES: [O-][n+]1ccc(-c2cnn([C@@H](CCOC(F)F)c3ccc(-c4c(-n5cnnn5)ccc(Cl)c4F)c[n+]3[O-])c2)c(F)c1]

LC/MS: mass calculated for $C_{24}H_{17}ClF_4NaO_3$: 576.10, measured (ES, m/z): 577.05 [M+H]$^+$. $^1$H NMR (300 MHz, DMSO-d$_6$) δ 9.70 (s, 1H), 8.52-8.61 (m, 2H), 8.47 (s, 1H), 8.14-8.21 (m, 2H), 8.04-8.12 (m, 1H), 7.72-7.88 (m, 2H), 7.27-7.36 (m, 1H), 7.16-7.24 (m, 1H), 6.32-6.91 (m, 1H), 6.19-6.28 (m, 1H), 3.83 (s, 1H), 3.70 (s, 1H), 2.55-2.75 (m, 2H). $^{19}$F NMR (282 MHz, DMSO-d$_6$) δ −83.28, −112.66, −124.00.

Example 315: 5-(3-Chloro-2-fluoro-6-(1H-tetrazol-1-yl)phenyl)-2-(3-(difluoromethoxy)-1-(4-(2-methylpyridin-4-yl)-1H-pyrazol-1-yl)propyl)pyridine 1-oxide

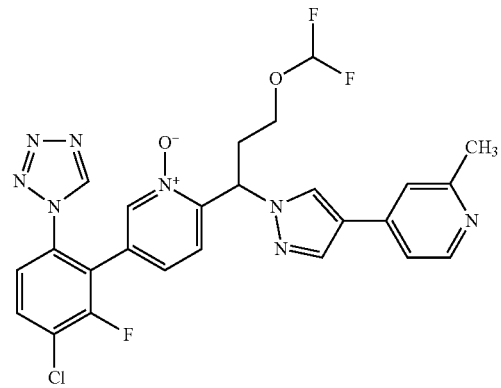 [SMILES: Cc1cc(-c2cnn(C(CCOC(F)F)c3ccc(-c4c(-n5cnnn5)ccc(Cl)c4F)c[n+]3[O-])c2)ccn1]

LC/MS: mass calculated for $C_{25}H_{20}ClF_3N_8O_2$: 556.13, measured (ES, m/z): 557.10[M+H]$^+$. $^1$H NMR (400 MHz, DMSO-d$_6$) δ 9.70 (s, 1H), 9.00 (s, 1H), 8.69 (d, J=6.3 Hz, 1H), 8.44-8.49 (m, 2H), 8.13-8.17 (m, 1H), 8.02-8.11 (m, 2H), 7.77 (dd, J=8.7, 1.5 Hz, 1H), 7.47 (d, J=8.3 Hz, 1H), 7.22 (dd, J=8.3, 1.7 Hz, 1H), 6.42-6.86 (m, 1H), 6.20-6.27 (m, 1H), 3.81-3.92 (m, 1H), 3.60-3.73 (m, 1H), 2.64-2.74 (m, 4H), 2.54-2.63 (m, 1H). $^{19}$F NMR (376 MHz, DMSO-d$_6$) δ −73.96, −83.33, −112.68.

Example 316: (R*)-5-(3-Chloro-2-fluoro-6-(1H-tetrazol-1-yl)phenyl)-2-(3-(difluoromethoxy)-1-(4-(3-fluoro-1-oxidopyridin-4-yl)-1H-pyrazol-1-yl)propyl)pyridine 1-oxide

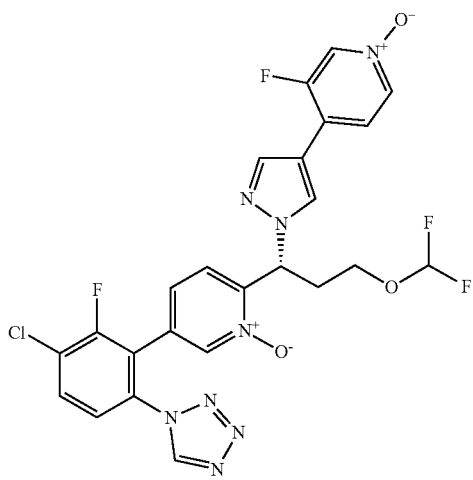 [SMILES: [O-][n+]1ccc(-c2cnn([C@H](CCOC(F)F)c3ccc(-c4c(-n5cnnn5)ccc(Cl)c4F)c[n+]3[O-])c2)c(F)c1]

LC/MS: mass calculated for $C_{24}H_{17}ClF_4N_8O_3$: 576.10, measured (ES, m/z): 577.15 [M+H]$^+$. $^1$H NMR (300 MHz, DMSO-d$_6$) δ 9.67 (s, 1H), 8.52-8.60 (m, 2H), 8.43 (s, 1H), 8.09-8.19 (m, 2H), 8.04 (dd, J=8.7, 7.7 Hz, 1H), 7.69-7.85 (m, 2H), 7.28 (d, J=8.3 Hz, 1H), 7.12-7.21 (m, 1H), 6.61 (t, J=75.7 Hz, 1H), 6.18-6.28 (m, 1H), 3.77-3.90 (m, 1H), 3.61-3.75 (m, 1H), 2.54-2.72 (m, 2H).

Example 317: 5-(3-Chloro-2-fluoro-6-(1H-tetrazol-1-yl)phenyl)-2-(1-(4-(2-fluoropyridin-4-yl)-1H-pyrazol-1-yl)-2-(1H-pyrazol-1-yl)ethyl)pyridine 1-oxide

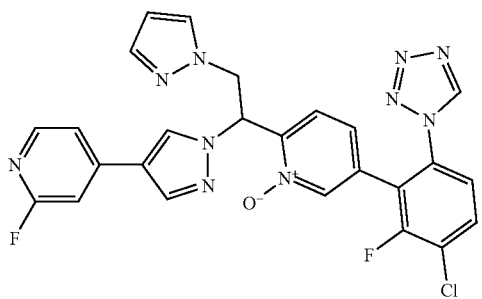 [SMILES: [O-][n+]1cc(-c2c(-n3cnnn3)ccc(Cl)c2F)ccc1C(Cn1cccn1)n1cc(-c2ccnc(F)c2)cn1]

LC/MS: mass calculated for $C_{25}H_{17}ClF_2N_{10}O$: 546.1, measured (ES, m/z): 547.10[M+H]$^+$. $^1$H NMR (400 MHz, DMSO-d$_6$) δ 9.69 (s, 1H), 8.60 (s, 1H), 8.52 (d, J=1.6 Hz, 1H), 8.29 (s, 1H), 8.16 (d, J=5.3 Hz, 1H), 8.03-8.12 (m, 1H), 7.77 (dd, J=8.7, 1.5 Hz, 1H), 7.44-7.56 (m, 3H), 7.35-7.43 (m, 2H), 7.22 (dd, J=8.3, 1.7 Hz, 1H), 6.48-4.56 (m, 1H), 6.09-6.13 (m, 1H), 4.93-5.14 (m, 2H). $^{19}$F NMR (376 MHz, DMSO-d$_6$) δ -69.15, -74.91, -112.61.

Example 318: 5-(3-Chloro-2-fluoro-6-(1H-tetrazol-1-yl)phenyl)-2-(1-(4-(2-methylpyridin-4-yl)-1H-pyrazol-1-yl)-2-(1H-pyrazol-1-yl)ethyl)pyridine 1-oxide

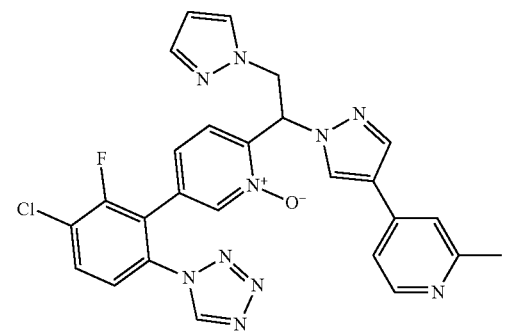 [SMILES: Cc1cc(-c2cnn(C(Cn3cccn3)c3ccc(-c4c(-n5cnnn5)ccc(Cl)c4F)c[n+]3[O-])c2)ccn1]

LC/MS: mass calculated for $C_{26}H_{20}ClFN_{10}O$: 542.1, measured (ES, m/z): 543.25 [M+H]$^+$. $^1$H NMR (400 MHz, DMSO-d$_6$) δ 9.70 (s, 1H), 8.81 (s, 1H), 8.68 (d, J=6.4 Hz, 1H), 8.52 (s, 1H), 8.44 (s, 1H), 8.04-8.14 (m, 2H), 8.00 (dd, J=6.4, 1.9 Hz, 1H), 7.77 (dd, J=8.7, 1.5 Hz, 1H), 7.63 (d, J=8.3 Hz, 1H), 7.53 (d, J=2.3 Hz, 1H), 7.42 (d, J=1.9 Hz, 1H), 7.27 (dd, J=8.3, 1.7 Hz, 1H), 6.54-6.62 (m, 1H), 6.13 (t, J=2.1 Hz, 1H), 5.08-5.20 (m, 1H), 4.96-5.04 (m, 1H), 2.65 (s, 3H). $^{19}$F NMR (376 MHz, DMSO-d$_6$) δ -74.53, -112.63.

Example 319: 5-(3-Chloro-2-fluoro-6-(1H-tetrazol-1-yl)phenyl)-2-(2-(N-methyl-4-oxo-4-(piperidin-1-yl)butanamido)-1-(4-(pyridin-4-yl)-1H-pyrazol-1-yl)ethyl)pyridine 1-oxide

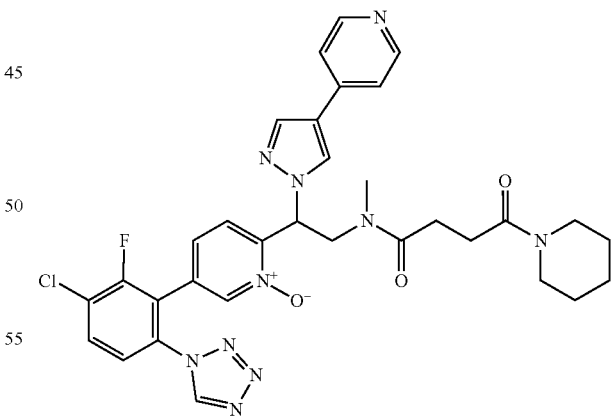

LC/MS: mass calculated for $C_{32}H_{32}ClFN_{10}O_3$: 658.2, measured (ES, m/z): 659.35 [M+H]$^+$. $^1$H NMR (300 MHz, DMSO-d$_6$) δ 9.52-9.56 (m, 1H), 8.28-8.58 (m, 4H), 8.09-8.21 (m, 1H), 7.92 (t, J=8.2 Hz, 1H), 7.49-7.69 (m, 4H), 7.17-7.28 (m, 1H), 6.14-6.37 (m, 1H), 4.07-4.26 (m, 1H), 3.87-3.98 (m, 1H), 3.20-3.51 (m, 4H), 2.55-3.78 (m, 4H), 2.20-2.45 (m, 3H), 1.42-1.54 (m, 2H), 1.27-1.41 (m, 4H). $^{19}$F NMR (282 MHz, DMSO-d$_6$) δ -73.86, -112.76.

Example 320: 5-(3-Chloro-2-fluoro-6-(1H-tetrazol-1-yl)phenyl)-2-(2-(N-methyl-3-phenylpropanamido)-1-(4-(pyridin-4-yl)-1H-pyrazol-1-yl)ethyl)pyridine 1-oxide

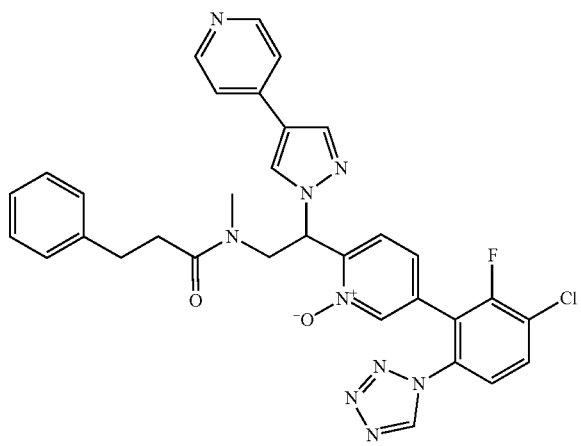

LC/MS: mass calculated for $C_{32}H_{27}ClFN_9O_2$: 623.2, measured (ES, m/z): 624.25 [M+H]$^+$. $^1$H NMR (300 MHz, DMSO-d$_6$) δ 9.68 (s, 1H), 8.63 (d, J=12.2 Hz, 1H), 8.40-8.53 (m, 3H), 8.11-8.28 (m, 1H), 8.01-8.13 (m, 1H), 7.70-7.78 (m, 1H), 7.53-7.69 (m, 3H), 7.07-7.26 (m, 6H), 6.18-6.35 (m, 1H), 3.84-4.35 (m, 2H), 2.53-2.78 (m, 6H), 2.43-2.25 (m, 1H). $^{19}$F NMR (282 MHz, DMSO-d$_6$) δ −73.45, −112.64.

Example 321: 5-(3-Chloro-2-fluoro-6-(1H-tetrazol-1-yl)phenyl)-2-(2-cyclopropyl-1-(4-(2-(difluoromethoxy)pyridin-4-yl)-1H-pyrazol-1-yl)ethyl)pyridine 1-oxide

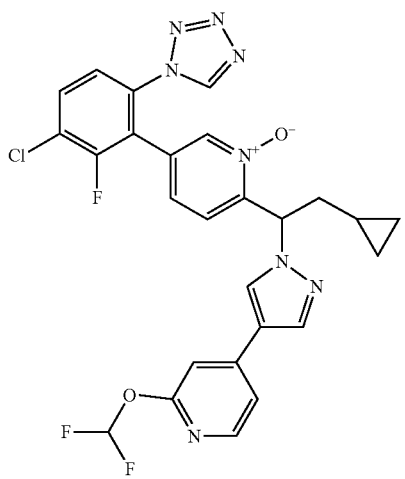

LC/MS: mass calculated for $C_{26}H_{20}ClF_3N_8O_2$: 568.1, measured (ES, m/z): 569.2 [M+H]$^+$. $^1$H NMR (400 MHz, CD$_3$OD) δ 9.34-9.42 (m, 1H), 8.54 (s, 1H), 8.36 (s, 1H), 8.05-8.17 (m, 2H), 7.83-7.94 (m, 1H), 7.52-7.74 (m, 2H), 7.49 (d, J=8.31 Hz, 1H), 7.34-7.42 (m, 1H), 7.27 (br d, J=7.83 Hz, 1H), 7.19 (d, J=0.98 Hz, 1H), 6.24 (br dd, J=3.67, 9.54 Hz, 1H), 2.41-2.60 (m, 1H), 1.95-2.04 (m, 1H), 0.63-0.77 (m, 1H), 0.34-0.49 (m, 2H), 0.14-0.25 (m, 1H), 0.01-0.09 (m, 1H).

Example 322: (R*)-2-(1-(4-(6-Amino-2-fluoropyridin-3-yl)-1H-pyrazol-1-yl)-2-(1H-pyrazol-1-yl)ethyl)-5-(3-chloro-2-fluoro-6-(1H-tetrazol-1-yl)phenyl)pyridine 1-oxide

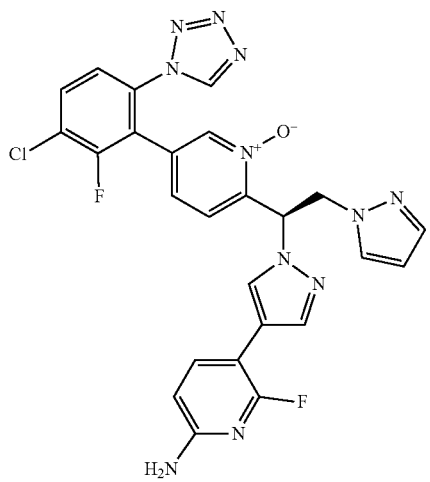

LC/MS: mass calculated for $C_{25}H_{18}ClF_2N_{11}O$: 561.1, measured (ES, m/z): 562.10 [M+H]$^+$. $^1$H NMR (400 MHz, DMSO-d$_6$) δ 9.69 (s, 1H), 8.50 (s, 1H), 8.02-8.12 (m, 2H), 7.88 (s, 1H), 7.71-7.80 (m, 2H), 7.43 (dd, J=10.4, 2.1 Hz, 2H), 7.22-7.30 (m, 1H), 7.12-7.19 (m, 1H), 6.48-6.56 (m, 1H), 6.36-6.45 (m, 3H), 6.12 (t, J=2.0 Hz, 1H), 4.86-5.13 (m, 2H). $^{19}$F NMR (376 MHz, DMSO-d$_6$) δ −71.27, −112.62.

Example 323: (S*)-2-(1-(4-(6-Amino-2-fluoropyridin-3-yl)-1H-pyrazol-1-yl)-2-(1H-pyrazol-1-yl)ethyl)-5-(3-chloro-2-fluoro-6-(1H-tetrazol-1-yl)phenyl)pyridine 1-oxide

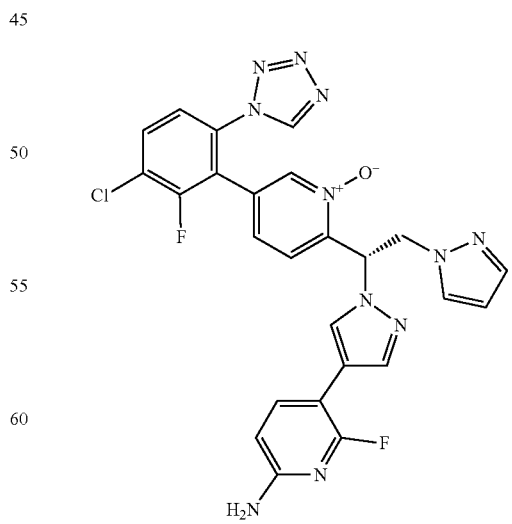

LC/MS: mass calculated for $C_{25}H_{18}ClF_2NO_{11}$: 561.1, measured (ES, m/z): 562.05 [M+H]$^+$. $^1$H NMR (400 MHz, DMSO-d$_6$) δ 9.69 (s, 1H), 8.50 (d, J=1.6 Hz, 1H), 8.02-8.12 (m, 2H), 7.88 (d, J=1.6 Hz, 1H), 7.71-7.80 (m, 2H), 7.37-7.44 (m, 2H), 7.22-7.29 (m, 1H), 7.12-7.21 (m, 1H), 6.49-6.57 (m, 1H), 6.30-6.38 (m, 3H), 6.12 (t, J=2.1 Hz, 1H), 4.84-5.14 (m, 2H). $^{19}$F NMR (376 MHz, DMSO-d$_6$) δ −71.27, −112.62.

Example 324: 5-(3-Chloro-2-fluoro-6-(1H-tetrazol-1-yl)phenyl)-2-(1-(4-(pyridin-4-yl)-1H-pyrazol-1-yl)-2-(3-(trifluoromethyl)-1H-pyrazol-1-yl)ethyl)pyridine 1-oxide

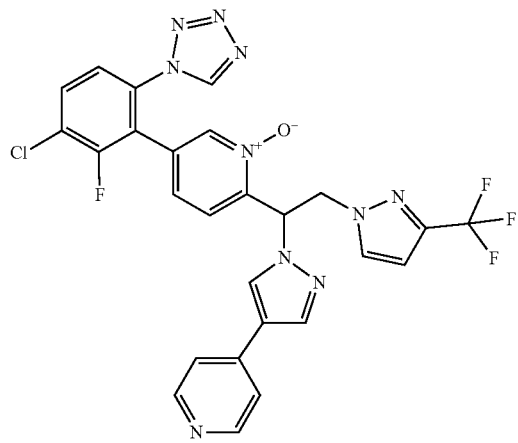

LC/MS: mass calculated for C$_{26}$H$_{17}$ClF$_4$N$_{10}$O: 596.1, measured (ES, m/z): 597.05 [M+H]$^+$. $^1$H NMR (400 MHz, DMSO-d$_6$) δ 9.68 (s, 1H), 8.53-8.60 (m, 3H), 8.34 (s, 1H), 8.17 (s, 1H), 8.09 (t, J=8.2 Hz, 1H), 7.90 (s, 1H), 7.75-7.80 (m, 1H), 7.65-7.74 (m, 2H), 7.16-7.27 (m, 2H), 6.93-6.98 (m, 1H), 6.72-6.79 (m, 1H), 5.10-5.20 (m, 1H), 4.99 (dd, J=13.8, 3.9 Hz, 1H). $^{19}$F NMR (376 MHz, DMSO-d$_6$) δ −58.61, −73.51, −112.66.

Example 325: 5-(3-Chloro-2-fluoro-6-(1H-tetrazol-1-yl)phenyl)-2-(1-(4-(pyridin-4-yl)-1H-pyrazol-1-yl)-2-(5-(trifluoromethyl)-1H-pyrazol-1-yl)ethyl)pyridine 1-oxide

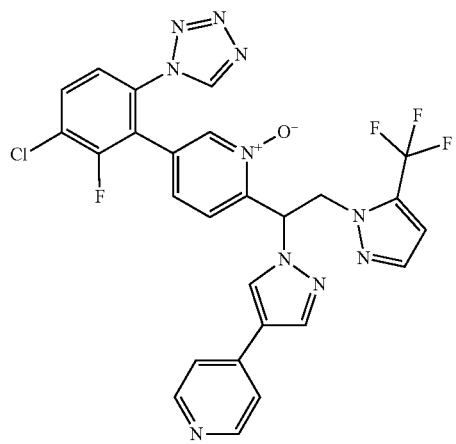

LC/MS: mass calculated for C$_{26}$H$_{17}$ClF$_4$N$_{10}$O: 596.1, measured (ES, m/z): 597.15 [M+H]$^+$. $^1$H NMR (400 MHz, DMSO-d$_6$) δ 9.70 (s, 1H), 8.53-8.62 (m, 1H), 8.49 (d, J=5.3 Hz, 2H), 8.19 (s, 1H), 8.00-8.12 (m, 3H), 7.77 (dd, J=8.7, 1.5 Hz, 1H), 7.41-7.51 (m, 3H), 7.26 (dd, J=8.3, 1.7 Hz, 1H), 6.63-6.72 (m, 2H), 5.01-5.16 (m, 2H). $^{19}$F NMR (376 MHz, DMSO-d$_6$) δ −71.32, −74.49, −112.69.

Example 326: 5-(3-Chloro-2-fluoro-6-(1H-tetrazol-1-yl)phenyl)-2-(1-(4-(2-(difluoromethyl)pyridin-4-yl)-1H-pyrazol-1-yl)-2-(1H-pyrazol-1-yl)ethyl)pyridine 1-oxide

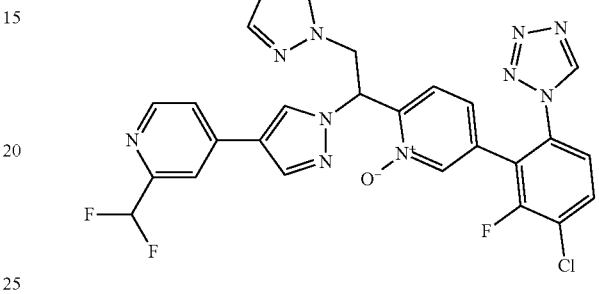

LC/MS: mass calculated for C$_{26}$H$_{18}$ClF$_3$N$_{10}$O: 578.1, measured (ES, m/z): 579.1 [M+H]$^+$. $^1$H NMR (400 MHz, DMSO-d$_6$) δ 9.62 (s, 1H), 8.70 (s, 1H), 8.47 (d, J=2.2 Hz, 1H), 8.35 (d, J=6.8 Hz, 1H), 8.22 (s, 1H), 8.05-8.12 (m, 1H), 7.93 (d, J=2.7 Hz, 1H), 7.73-7.81 (m, 2H), 7.38-7.51 (m, 3H), 7.17-7.23 (m, 1H), 6.52-6.58 (m, 1H), 6.07-6.15 (m, 1H), 4.93-5.21 (m, 2 h). $^{19}$F NMR (376 MHz, DMSO-d$_6$) δ −75.12, −112.63, −115.43.

Example 327: 2-(2-(1H-Pyrazol-1-yl)-1-(4-(pyrimidin-4-yl)-1H-pyrazol-1-yl)ethyl)-5-(3-chloro-2-fluoro-6-(1H-tetrazol-1-yl)phenyl)pyridine 1-oxide

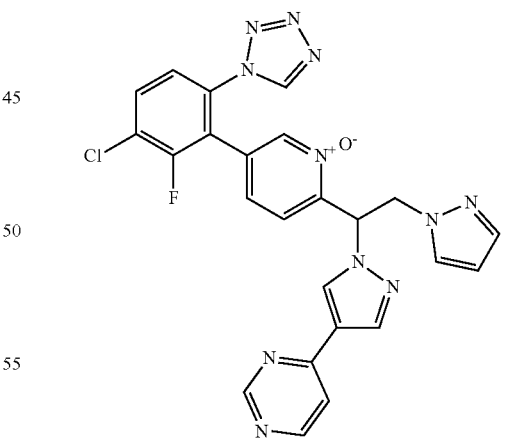

LC/MS: mass calculated for C$_{24}$H$_{17}$ClFN$_{11}$O: 529.1, measured (ES, m/z): 530.1 [M+H]$^+$. $^1$H NMR (400 MHz, DMSO-d$_6$) δ 9.62 (s, 1H), 8.99 (s, 1H), 8.59 (s, 1H), 8.55-8.57 (m, 1H), 8.48 (d, J=2.2 Hz, 1H), 8.16 (s, 1H), 8.00-8.09 (m, 1H), 7.77-7.82 (m, 2H), 7.69 (dd, J=8.2, 2.3 Hz, 1H), 7.43 (dd, J=6.2, 2.1 Hz, 2H), 7.19 (d, J=8.2 Hz, 1H), 6.18-6.22 (m, 1H), 6.09-6.11 (m, 1H), 4.98-5.22 (m, 2H). $^{19}$F NMR (376 MHz, DMSO-d$_6$) δ −74.98, −113.38.

Example 328: 4-(1-(1-(5-(3-Chloro-2-fluoro-6-(1H-tetrazol-1-yl)phenyl)-1-oxidopyridin-2-yl)-2-(1H-pyrazol-1-yl)ethyl)-1H-pyrazol-4-yl)pyrimidine 1-oxide

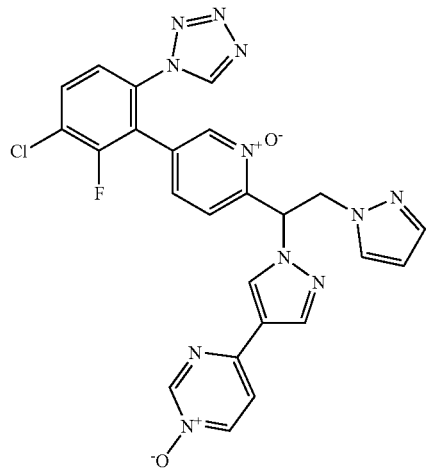

LC/MS: mass calculated for $C_{24}H_{17}ClFN_{11}O_2$: 545.1, measured (ES, m/z): 546.1 [M+H]+. $^1$H NMR (400 MHz, DMSO-$d_6$) δ 9.69 (s, 1H), 8.95-9.01 (m, 3H), 8.49-8.59 (m, 3H), 8.21 (s, 1H), 8.03-8.11 (m, 1H), 7.73-7.81 (m, 2H), 7.50 (d, J=2.3 Hz, 1H), 7.38-7.42 (m, J=5.1, 3.2 Hz, 2H), 7.22 (dd, J=8.3, 1.7 Hz, 1H), 6.52-6.61 (m, 1H), 6.12-6.13 (m, 1H), 5.05-5.17 (m, 1H), 4.94-5.02 (m, 1H). $^{19}$F NMR (376 MHz, DMSO-$d_6$) δ −74.95, −112.61.

Example 329: 5-(5-Chloro-2-(1H-tetrazol-1-yl)phenyl)-2-(1-(4-(2-fluoropyridin-4-yl)-1H-pyrazol-1-yl)-2-(4-(trifluoromethyl)-1H-pyrazol-1-yl)ethyl)pyridine 1-oxide

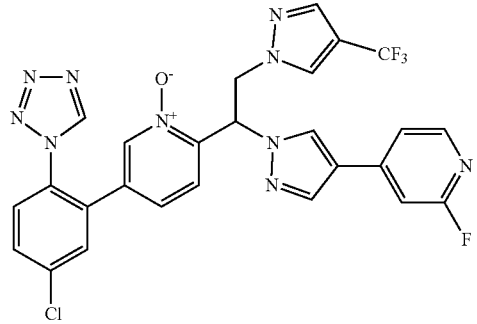 [SMILES: [O-][n+]1cc(-c2cc(Cl)ccc2-n2cnnn2)ccc1C(Cn1cc(C(F)(F)F)cn1)n1cc(-c2ccnc(F)c2)cn1]

LC/MS: mass calculated for $C_{26}H_{17}ClF_4N_{10}O$: 596.1, measured (ES, m/z): 597.3 [M+H]+. $^1$H NMR (400 MHz, CD$_3$OD) δ ppm 5.07-5.14 (m, 2H), 5.21 (dd, J=13.7, 9.8 Hz, 1H), 6.69 (dd, J=9.8, 3.9 Hz, 1H), 7.18 (d, J=8.3, 1H), 7.41-7.46 (m, 2H), 7.49 (d, J=8.3 Hz, 1H), 7.75-7.83 (m, 2H), 7.90 (s, 1H), 8.08-8.12 (m, 2H), 8.18 (s, 8.28 (s, 1H), 8.35 (d, J=1.5 Hz, 1H), 9.38 (s, 1H).

Example 330: 5-(3-Chloro-2-fluoro-6-(1H-tetrazol-1-yl)phenyl)-2-(2-(N-methyl-3-oxo-3-(piperidin-1-yl)propanamido)-1-(4-(pyridin-4-yl)-1H-pyrazol-1-yl)ethyl)pyridine 1-oxide

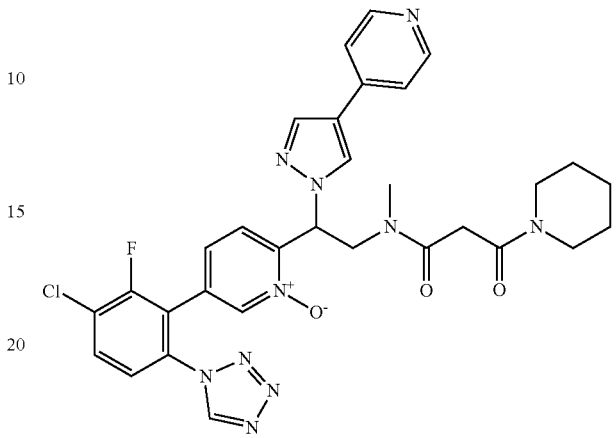

LC/MS: mass calculated for $C_{31}H_{30}ClFN_{10}O_3$: 644.2, measured (ES, m/z): 645.20 [M+H]+. $^1$H NMR (300 MHz, DMSO-$d_6$) δ 9.65-9.75 (m, 1H), 8.93-9.10 (m, 1H), 8.72-8.80 (m, 2H), 8.35-8.57 (m, 2H), 8.00-8.18 (m, 3H), 7.54-7.78 (m, 2H), 7.19-7.31 (m, 1H), 6.22-6.36 (m, 1H), 4.13-4.39 (m, 1H), 3.89-4.09 (m, 1H), 3.35-3.45 (m, 4H), 3.15-3.22 (m, 1H), 3.05-3.12 (m, 1H), 2.70-2.85 (m, 3H), 1.45-1.60 (m, 2H), 1.30-1.45 (m, 4H). $^{19}$F NMR (282 MHz, DMSO-$d_6$) d −74.15, −112.62.

Example 331: 5-(3-Chloro-2-fluoro-6-(1H-tetrazol-1-yl)phenyl)-2-(1-(4-(pyridin-4-yl)-1H-pyrazol-1-yl)-2-(2,2,2-trifluoro-N-methylacetamido)ethyl)pyridine 1-oxide

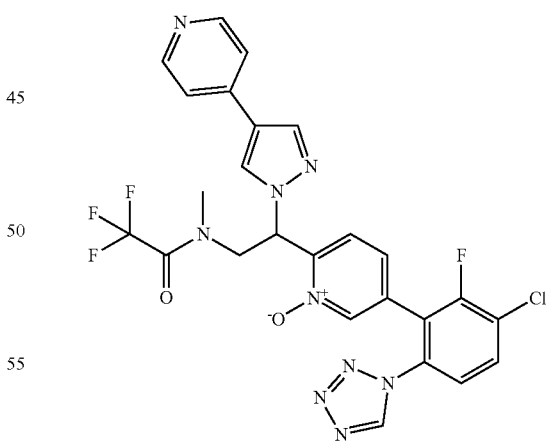

LC/MS: mass calculated for $C_{25}H_{18}ClF_4NO_2$: 587.1, measured (ES, m/z): 588.1 [M+H]+. $^1$H NMR (300 MHz, DMSO-$d_6$) δ 9.69 (s, 1H), 9.07 (s, 1H), 8.77 (d, J=6.4 Hz, 2H), 8.40-8.51 (m, 2H), 8.14 (d, J=6.2 Hz, 2H), 8.06-8.13 (m, 1H), 7.71-7.80 (m, 2H), 7.28 (dd, J=8.3, 1.6 Hz, 1H), 6.40 (dd, J=10.1, 4.6 Hz, 1H), 4.45-4.56 (m, 1H), 4.09 (dd, J=13.5, 4.6 Hz, 1H), 2.93-3.01 (m, 3H). $^{19}$F NMR (282 MHz, DMSO-$d_6$) δ −67.48, −69.22, −74.18, −112.67.

397

Example 332: 4-(1-(1-(5-(3-Chloro-2-fluoro-6-(1H-tetrazol-1-yl)phenyl)-1-oxidopyridin-2-yl)-3-(difluoromethoxy)propyl)-1H-pyrazol-4-yl)pyrimidine 1-oxide

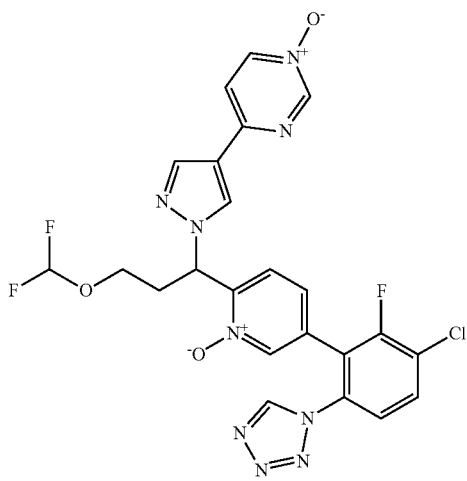

LC/MS: mass calculated for $C_{23}H_{17}ClF_3N_9O_3$: 559.1, measured (ES, m/z): 560.10 [M+H]$^+$. $^1$H NMR (400 MHz, DMSO-$d_6$) δ 9.62 (s, 1H), 8.60-8.99 (m, 1H), 8.18-8.52 (m, 3H), 7.66-8.04 (m, 3H), 7.33-7.41 (m, 1H), 7.20 (d, J=8.3 Hz, 1H), 6.35-6.79 (m, 1H), 6.10-6.24 (m, 1H), 3.79-3.81 (m, 2H), 2.53-2.67 (m, 2H). $^{19}$F NMR (376 MHz, DMSO-$d_6$) d −73.95, −83.20, −112.77.

Example 333: (R*)-2-(1-(4-(4-Carboxyphenyl)-1H-pyrazol-1-yl)-2-cyclopropylethyl)-5-(3-chloro-6-(difluoromethyl)-2-fluorophenyl)pyridine 1-oxide

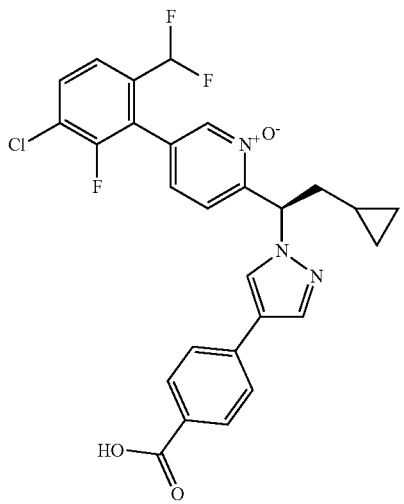

LC/MS: mass calculated for $C_{27}H_{21}ClF_3N_3O_3$: 527.1, measured (ES, m/z): 528.10 [M+H]$^+$. $^1$H NMR (300 MHz, DMSO-$d_6$) δ 12.76 (s, 1H), 8.69 (s, 1H), 8.47 (s, 1H), 8.15 (s, 1H), 7.81-7.96 (m, 3H), 7.75-7.82 (m, 2H), 7.59 (d, J=8.4 Hz, 1H), 7.31-7.43 (m, 2H), 6.87 (t, J=53.9 Hz, 1H), 6.13-6.23 (m, 1H), 2.40-2.50 (m, 1H), 1.88-2.02 (m, 1H), 0.60-0.72 (m, 1H), 0.24-0.47 (m, 2H), 0.13-0.25 (m, 1H), 0.03-0.12 (m, 1H).

Example 334: (S*)-2-(1-(4-(4-Carboxyphenyl)-1H-pyrazol-1-yl)-2-cyclopropylethyl)-5-(3-chloro-6-(difluoromethyl)-2-fluorophenyl)pyridine 1-oxide

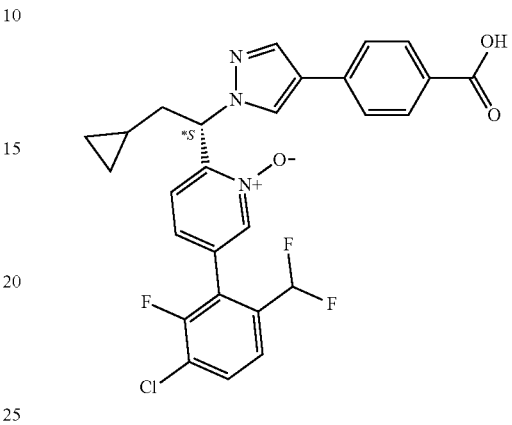

LC/MS: mass calculated for $C_{27}H_{21}ClF_3N_3O_3$: 527.1, measured (ES, m/z): 528.1 [M+H]$^+$. $^1$H NMR (300 MHz, DMSO-$d_6$) δ 12.83 (bs, 1H), 8.69 (s, 1H), 8.47 (s, 1H), 8.15 (s, 1H), 7.81-7.96 (m, 3H), 7.75 (d, J=8.3 Hz, 2H), 7.59 (d, J=8.5 Hz, 1H), 7.31-7.43 (m, 2H), 6.87 (s, 1H), 6.12-6.21 (m, 1H), 2.48-2.49 (m, 1H), 1.95-1.99 (m, 1H), 0.66-0.67 (m, 1H), 0.36-0.37 (m, 2H), 0.17-0.18 (m, 1H), 0.01-0.03 (m, 1H).

Example 335: 5-(3-Chloro-2-fluoro-6-(1H-tetrazol-1-yl)phenyl)-2-(2-cyclopropyl-1-(4-(2-methyl-2H-indazol-5-yl)-1H-pyrazol-1-yl)ethyl)pyridine 1-oxide

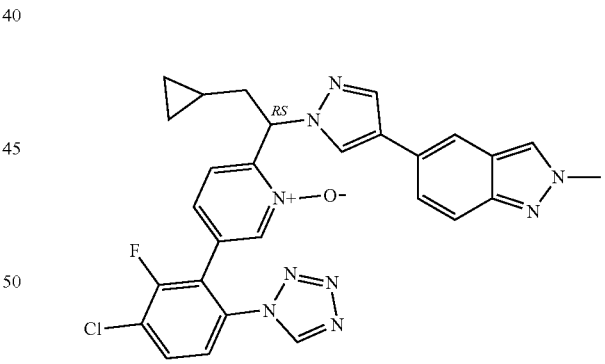

To 5-(1-(1-(5-(3-Chloro-2-fluoro-6-(1H-tetrazol-1-yl)phenyl)pyridin-2-yl)-2-cyclopropylethyl)-1H-pyrazol-4-yl)-2-methyl-2H-indazole (32.5 mg, 0.06 mmol) in DCM (5 mL) was added meta-chloroperbenzoic acid (m-CPBA) (54 mg, 0.24 mmol) and the resulting mixture was stirred at room temperature for 2 h. The reaction mixture was concentrated under reduced pressure and the residue was purified by Gilson HPLC to yield the title compound as a yellow solid.

LC/MS: mass calculated for $C_{28}H_{23}ClFN_9O$: 555.2, measured (ES, m/z): 556.2 [M+H]$^+$. $^1$H NMR (400 MHz, CD$_3$OD) δ 9.37 (s, 1H), 8.25-8.44 (m, 2H), 8.20 (s, 1H), 8.00 (br s, 1H), 7.85-7.94 (m, 2H), 7.55-7.64 (m, 3H), 7.42

(br d, J=8.59 Hz, 1H), 7.14-7.32 (m, 1H), 6.23 (br d, J=5.56 Hz, 1H), 4.21 (s, 3H), 2.45-2.64 (m, 1H), 1.94-2.07 (m, 1H), 0.73 (br s, 1H), 0.34-0.55 (m, 2H), 0.17-0.29 (m, 1H), 0.09 (br d, J=4.55 Hz, 1H).

Example 336: (R*)-5-(3-Chloro-2-fluoro-6-(1H-tetrazol-1-yl)phenyl)-2-(1-(4-(4-((methoxycarbonyl)amino)phenyl)-1H-pyrazol-1-yl)-2-(1-methyl-1H-pyrazol-3-yl)ethyl)pyridine 1-oxide

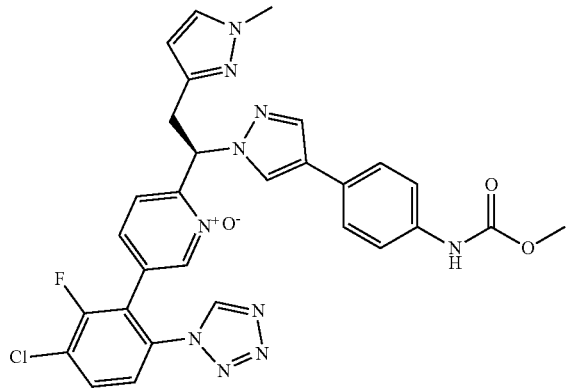

Step 1: N-methoxy-N-methyl-2-(1-methyl-1H-pyrazol-3-yl)acetamide

To a solution of 2-(1-methyl-1H-pyrazol-3-yl)acetic acid (1.0 g, 7.1 mmol, 1.0 equiv.) in DCM (10 mL) was added di(1H-imidazol-1-yl)methanone (1.7 g, 10.7 mmol, 1.5 equiv.) at room temperature and the solution was stirred for 0.5 h. To the solution was then added N,O-dimethylhydroxylamine hydrochloride (835 mg, 8.6 mmol, 1.2 equiv.) and the mixture was stirred at room temperature overnight. The reaction was quenched with water, and the mixture extracted with DCM twice. The combined organic layer was washed with 1N HCl, saturated aqueous NaHCO$_3$ and brine, dried over anhydrous Na$_2$SO$_4$ and concentrated to yield N-methoxy-N-methyl-2-(1-methyl-1H-pyrazol-3-yl)acetamide as a colorless oil. $^1$H NMR (300 MHz, Chloroform-d): δ 7.30 (d, J=2.2 Hz, 1H), 6.23 (d, J=2.2 Hz, 1H), 3.87 (s, 3H), 3.83 (s, 2H), 3.71 (s, 3H), 3.22 (s, 3H).

Step 2: 1-(5-Bromopyridin-2-yl)-2-(1-methyl-1H-pyrazol-3-yl)ethan-1-one

To a solution of 2,5-dibromopyridine (830 mg, 3.50 mmol, 1.0 equiv.) in toluene (10 mL) under nitrogen was added n-butyllithium (1.5 mL, 3.68 mmol, 2.50 M in THF, 1.05 equiv.) at −78° C. and the solution was stirred for 1H at this temperature. To the solution was then added the solution of N-methoxy-N-methyl-2-(1-methyl-1H-pyrazol-3-yl)acetamide (642 mg, 3.50 mmol, 1.0 equiv.) in toluene (5 mL) at −78° C. and the mixture was allowed to stirred at −78° C. for 2 h. The reaction was quenched with sat. NH$_4$Cl (aq.) and extracted with ethyl acetate twice. The combined organic layer was washed with brine, dried over Na$_2$SO$_4$ and concentrated. The residue was purified by silica gel chromatography (0→50% ethyl acetate/petroleum ether) to yield 1-(5-bromopyridin-2-yl)-2-(1-methyl-1H-pyrazol-3-yl)ethan-1-one as a light yellow oil. LC/MS: mass calculated for C$_{11}$H$_{10}$BrN$_3$O: 279.00, measured (ES, m/z): 279.95, 281.95 [M+H, M+H+2]$^+$.

Step 3: 1-(5-Bromopyridin-2-yl)-2-(1-methyl-1H-pyrazol-3-yl)ethan-1-ol

To a solution of 1-(5-bromopyridin-2-yl)-2-(1-methyl-1H-pyrazol-3-yl)ethan-1-one (330 mg, 1.18 mmol, 1.0 equiv.) in ethanol (10 mL) was added NaBH$_4$ (53 mg, 1.41 mmol, 1.2 equiv.) and the solution was stirred at room temperature for 2 h. The reaction was quenched with water, and the mixture extracted with ethyl acetate twice. The combined organic layers were washed with brine, dried over Na$_2$SO$_4$ and concentrated. The residue was purified by silica gel chromatography (0→50% ethyl acetate/petroleum ether) to yield 1-(5-bromopyridin-2-yl)-2-(1-methyl-1H-pyrazol-3-yl)ethan-1-ol as a light yellow solid. LC/MS: mass calculated for C$_{11}$H$_{12}$BrN$_3$O: 281.02, measured (ES, m/z): 282.00, 284.00 [M+H, M+H+2]$^+$.

Step 4: 1-(5-Bromopyridin-2-yl)-2-(1-methyl-1H-pyrazol-3-yl)ethyl methanesulfonate To a mixture of 1-(5-bromopyridin-2-yl)-2-(1-methyl-1H-pyrazol-3-yl)ethan-1-ol (330 mg, 1.17 mmol, 1.0 equiv.) and triethylamine (296 mg, 2.92 mmol, 2.5 equiv.) in DCM (5 mL) was added methanesulfonyl chloride (201 mg, 1.75 mmol, 1.2 equiv.) at 0° C. and the solution was stirred at room temperature for 2 h. The reaction mixture was concentrated and purified by silica gel chromatography (0→50% ethyl acetate/petroleum ether) to yield 1-(5-bromopyridin-2-yl)-2-(1-methyl-1H-pyrazol-3-yl)ethyl methanesulfonate a light yellow oil. LC/MS: mass calculated for C$_{12}$H$_{14}$BrN$_3$O$_3$S: 358.99, measured (ES, m/z): 359.95, 361.95 [M+H, M+H+2]$^+$.

Step 5: Methyl (4-(1-(1-(5-bromopyridin-2-yl)-2-(1-methyl-1H-pyrazol-3-yl)ethyl)-1H-pyrazol-4-yl)phenyl)carbamate A mixture of 1-(5-bromopyridin-2-yl)-2-(1-methyl-1H-pyrazol-3-yl)ethyl methanesulfonate (340 mg, 0.94 mmol, 1.0 equiv.), methyl (4-(1H-pyrazol-4-yl)phenyl)carbamate (246 mg, 1.13 mmol, 1.2 equiv.) and cesium carbonate (308 mg, 0.94 mmol, 1.0 equiv.) in acetonitrile (8 mL) was stirred at 90° C. for 4 h. The reaction was diluted with water, and the mixture extracted with ethyl acetate twice. The combined organic layers were washed with brine, dried over Na$_2$SO$_4$ and concentrated. The residue was purified by silica gel chromatography (0→50% ethyl acetate/petroleum ether) to yield methyl (4-(1-(1-(5-bromopyridin-2-yl)-2-(1-methyl-1H-pyrazol-3-yl)ethyl)-1H-pyrazol-4-yl)phenyl)carbamate as a light yellow solid. LC/MS: mass calculated for C$_{22}$H$_{21}$BrN$_6$O$_2$: 480.09, measured (ES, m/z): 481.00, 483.00 [M+H, M+H+2]$^+$.

Step 6: Methyl (4-(1-(1-(5-(6-amino-3-chloro-2-fluorophenyl)pyridin-2-yl)-2-(1-methyl-1H-pyrazol-3-yl)ethyl)-1H-pyrazol-4-yl)phenyl)carbamate A mixture of methyl (4-(1-(1-(5-bromopyridin-2-yl)-2-(1-methyl-1H-pyrazol-3-yl)ethyl)-1H-pyrazol-4-yl)phenyl) carbamate (260 mg, 0.54 mmol, 1.0 equiv.), 6-amino-3-chloro-2-fluorophenylboronic acid (153 mg, 0.81 mmol, 1.5 equiv.), potassium carbonate (224 mg, 1.62 mmol, 3.0 equiv.) and Pd(PPh$_3$)$_4$ (62 mg, 0.054 mmol, 0.1 equiv.) in 1,4-dioxane (5 mL) and water (1 mL) was stirred at 90° C. for 4 h. After cooling to room temperature, the reaction was quenched with H₂O and extracted with ethyl acetate twice. The combined organic layers were washed with brine, dried over Na₂SO₄ and concentrated. The residue was purified by silica gel chromatography (0→10% MeOH/DCM) to yield methyl (4-(1-(1-(5-(6-amino-3-chloro-2-fluorophenyl)pyridin-2-yl)-2-(1-methyl-1H-pyrazol-3-yl)ethyl)-1H-pyrazol-4-yl)phenyl)carbamate as a light yellow solid. LC/MS: mass calculated for $C_{28}H_{25}ClFN_7O_2$: 545.17, measured (ES, m/z): 546.10 [M+H]⁺.

Step 7: Methyl (4-(1-(1-(5-(3-chloro-2-fluoro-6-(1H-tetrazol-1-yl)phenyl)pyridin-2-yl)-2-(1-methyl-1H-pyrazol-3-yl)ethyl)-1H-pyrazol-4-yl)phenyl)carbamate A mixture of methyl (4-(1-(1-(5-(6-amino-3-chloro-2-fluorophenyl)pyridin-2-yl)-2-(1-methyl-1H-pyrazol-3-yl)ethyl)-1H-pyrazol-4-yl)phenyl)carbamate (230 mg, 0.42 mmol, 1.0 equiv.), azidotrimethylsilane (0.5 mL) and trimethoxymethane (0.5 mL) in acetic acid glacial (1 mL) was stirred at room temperature overnight. The mixture was then concentrated and the residue was purified by reverse phase chromatography on C18 (80 g, MeCN/H₂O (0.05% CF₃COOH): 0→45%) to yield methyl (4-(1-(1-(5-(3-chloro-2-fluoro-6-(1H-tetrazol-1-yl)phenyl)pyridin-2-yl)-2-(1-methyl-1H-pyrazol-3-yl)ethyl)-1H-pyrazol-4-yl)phenyl)carbamate as a light yellow solid. LC/MS: mass calculated for $C_{29}H_{24}ClFN_{10}O_2$: 598.18, measured (ES, m/z): 599.15 [M+H]⁺.

Step 8: (R*)-5-(3-Chloro-2-fluoro-6-(1H-tetrazol-1-yl)phenyl)-2-(1-(4-(4-((methoxycarbonyl)amino)phenyl)-1H-pyrazol-1-yl)-2-(1-methyl-1H-pyrazol-3-yl)ethyl)pyridine 1-oxide A mixture of methyl (4-(1-(1-(5-(3-chloro-2-fluoro-6-(1H-tetrazol-1-yl)phenyl)pyridin-2-yl)-2-(1-methyl-1H-pyrazol-3-yl)ethyl)-1H-pyrazol-4-yl)phenyl)carbamate (170 mg, 0.28 mmol, 1.0 equiv.) and 3-chloroperoxybenzoic acid (147 mg, 0.85 mmol, 3.0 equiv.) in DCM (3 mL) was stirred at room temperature for 2 h. The solution was purified by reverse phase chromatography on C18 (80 g, MeCN/H₂O (0.05% NH₄HCO₃): 0→45%) to yield 50 mg of 5-(3-chloro-2-fluoro-6-(1H-tetrazol-1-yl)phenyl)-2-(1-(4-(4-((methoxycarbonyl)amino)phenyl)-1H-pyrazol-1-yl)-2-(1-methyl-1H-pyrazol-3-yl)ethyl)pyridine 1-oxide as off-white solid. The racemic product was purified by Chiral HPLC to yield (R*)-5-(3-chloro-2-fluoro-6-(1H-tetrazol-1-yl)phenyl)-2-(1-(4-(4-((methoxycarbonyl)amino)phenyl)-1H-pyrazol-1-yl)-2-(1-methyl-1H-pyrazol-3-yl)ethyl)pyridine 1-oxide as a white solid.

LC/MS: mass calculated for $C_{29}H_{24}ClFN_{10}O_3$: 614.2 measured (ES, m/z): 615.2 [M+H]⁺. ¹H NMR (400 MHz, DMSO-d₆): δ 9.69 (s, 1H), 9.64 (s, 1H), 8.45 (s, 1H), 8.33 (s, 1H), 8.07 (t, J=8.4 Hz, 1H), 7.93 (s, 1H), 7.74-7.78 (m, 1H), 7.40-7.52 (m, 5H), 7.15-7.25 (m, 2H), 6.28 (t, J=7.3 Hz, 1H), 5.76 (d, J=2.2 Hz, 1H), 3.73 (s, 3H), 3.67 (s, 3H), 3.50-3.52 (m, 2H).

Example 337: (R)-5-(3-Chloro-2-fluoro-6-(1H-tetrazol-1-yl)phenyl)-2-(1-(4-(4-((methoxycarbonyl)amino)phenyl)-1H-pyrazol-1-yl)-2-(1-methyl-1H-pyrazol-3-yl)ethyl)pyridine 1-oxide

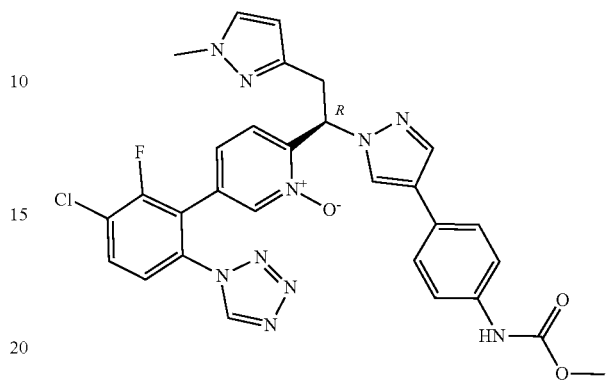

Step 1: N-Methoxy-N-methyl-2-(1-methyl-1H-pyrazol-3-yl)acetamide

To a solution of 2-(1-methyl-1H-pyrazol-3-yl)acetic acid (1.0 g, 7.1 mmol, 1.0 equiv.) in DCM (10 mL) was added CDI (1.7 g, 10.7 mmol, 1.5 equiv.) at room temperature and the solution was stirred for 0.5 h. To the solution was then added N,O-dimethylhydroxylamine hydrochloride (835 mg, 8.6 mmol, 1.2 equiv.) and the mixture was stirred at room temperature overnight. The reaction was quenched with water, and the mixture extracted with DCM twice. The combined organic layer was washed with 1N HCl, saturated aqueous NaHCO₃ and brine, dried over anhydrous Na₂SO₄ and concentrated to yield N-methoxy-N-methyl-2-(1-methyl-1H-pyrazol-3-yl)acetamide as a colorless oil. ¹H NMR (300 MHz, Chloroform-d): δ 7.30 (d, J=2.2 Hz, 1H), 6.23 (d, J=2.2 Hz, 1H), 3.87 (s, 3H), 3.83 (s, 2H), 3.71 (s, 3H), 3.22 (s, 3H).

Step 2: 1-(5-Bromopyridin-2-yl)-2-(1-methyl-1H-pyrazol-3-yl)ethan-1-one

To a solution of 2,5-dibromopyridine (830 mg, 3.50 mmol, 1.0 equiv.) in toluene (10 mL) under nitrogen was added n-butyllithium (1.5 mL, 3.68 mmol, 2.50 M in THF, 1.05 equiv.) at −78° C. and the solution was stirred for 1 h at this temperature. To the solution was then added the solution of N-methoxy-N-methyl-2-(1-methyl-1H-pyrazol-3-yl)acetamide (642 mg, 3.50 mmol, 1.0 equiv.) in toluene (5 mL) at −78° C. and the solution was allowed to stirred at −78° C. for 2 h. The reaction was quenched with sat. NH₄Cl (aq.) and extracted with ethyl acetate twice. The combined organic layer was washed with brine, dried over Na₂SO₄ and concentrated. The residue was purified by silica gel chromatography (0→50% ethyl acetate/petroleum ether) to yield 1-(5-bromopyridin-2-yl)-2-(1-methyl-1H-pyrazol-3-yl)ethan-1-one as a light yellow oil. LC/MS: mass calculated for $C_{11}H_{10}BrN_3O$: 279.00, measured (ES, m/z): 279.95, 281.95 [M+H, M+H+2]⁺.

Step 3: 1-(5-Bromopyridin-2-yl)-2-(1-methyl-1H-pyrazol-3-yl)ethan-1-ol

To a solution of 1-(5-bromopyridin-2-yl)-2-(1-methyl-1H-pyrazol-3-yl)ethan-1-one (330 mg, 1.18 mmol, 1.0 equiv.) in ethanol (10 mL) was added NaBH$_4$ (53 mg, 1.41 mmol, 1.2 equiv.) and the solution was stirred at room temperature for 2 h. The reaction was quenched with water, and the mixture extracted with ethyl acetate twice. The combined organic layers were washed with brine, dried over Na$_2$SO$_4$ and concentrated. The residue was purified by silica gel chromatography (0→50% ethyl acetate/petroleum ether) to yield 1-(5-bromopyridin-2-yl)-2-(1-methyl-1H-pyrazol-3-yl)ethan-1-ol as a light yellow solid. LC/MS: mass calculated for C$_{11}$H$_{12}$BrN$_3$O: 281.02, measured (ES, m/z): 282.00, 284.00 [M+H, M+H+2]$^+$.

Step 4: 1-(5-Bromopyridin-2-yl)-2-(1-methyl-1H-pyrazol-3-yl)ethyl methanesulfonate To a mixture of 1-(5-bromopyridin-2-yl)-2-(1-methyl-1H-pyrazol-3-yl)ethan-1-ol (330 mg, 1.17 mmol, 1.0 equiv.) and triethylamine (296 mg, 2.92 mmol, 2.5 equiv.) in DCM (5 mL) was added methanesulfonyl chloride (201 mg, 1.75 mmol, 1.2 equiv.) at 0° C. and the solution was stirred at room temperature for 2 h. The reaction was concentrated and purified by silica gel chromatography (0→50% ethyl acetate/petroleum ether) to yield 1-(5-bromopyridin-2-yl)-2-(1-methyl-1H-pyrazol-3-yl)ethyl methanesulfonate a light yellow oil. LC/MS: mass calculated for C$_{12}$H$_{14}$BrN$_3$O$_3$S: 358.99, measured (ES, m/z): 359.95, 361.95 [M+H, M+H+2]$^+$.

Step 5: Methyl (4-(1-(1-(5-bromopyridin-2-yl)-2-(1-methyl-1H-pyrazol-3-yl)ethyl)-1H-pyrazol-4-yl)phenyl)carbamate A mixture of 1-(5-bromopyridin-2-yl)-2-(1-methyl-1H-pyrazol-3-yl)ethyl methanesulfonate (340 mg, 0.94 mmol, 1.0 equiv.), methyl (4-(1H-pyrazol-4-yl)phenyl)carbamate (246 mg, 1.13 mmol, 1.2 equiv.) and cesium carbonate (308 mg, 0.94 mmol, 1.0 equiv.) in acetonitrile (8 mL) was stirred at 90° C. for 4 h. The reaction was diluted with water, and the mixture extracted with ethyl acetate twice. The combined organic layers were washed with brine, dried over Na$_2$SO$_4$ and concentrated. The residue was purified by silica gel chromatography (0→50% ethyl acetate/petroleum ether) to yield methyl (4-(1-(1-(5-bromopyridin-2-yl)-2-(1-methyl-1H-pyrazol-3-yl)ethyl)-1H-pyrazol-4-yl)phenyl)carbamate as a light yellow solid. LC/MS: mass calculated for C$_{22}$H$_{21}$BrN$_6$O$_2$: 480.09, measured (ES, m/z): 481.00, 483.00 [M+H, M+H+2]$^+$.

Step 6: Methyl (4-(1-(1-(5-(6-amino-3-chloro-2-fluorophenyl)pyridin-2-yl)-2-(1-methyl-1H-pyrazol-3-yl)ethyl)-1H-pyrazol-4-yl)phenyl)carbamate A mixture of methyl (4-(1-(1-(5-bromopyridin-2-yl)-2-(1-methyl-1H-pyrazol-3-yl)ethyl)-1H-pyrazol-4-yl)phenyl) carbamate (260 mg, 0.54 mmol, 1.0 equiv.), 6-amino-3-chloro-2-fluorophenylboronic acid (153 mg, 0.81 mmol, 1.5 equiv.), potassium carbonate (224 mg, 1.62 mmol, 3.0 equiv.) and Pd(PPh$_3$)$_4$ (62 mg, 0.054 mmol, 0.1 equiv.) in 1,4-dioxane (5 mL) and water (1 mL) was stirred at 90° C. for 4 h. After cooling to room temperature, the reaction was quenched with H$_2$O and extracted with ethyl acetate twice. The combined organic layers were washed with brine, dried over Na$_2$SO$_4$ and concentrated. The residue was purified by silica gel chromatography (0→10% MeOH/DCM) to yield methyl (4-(1-(1-(5-(6-amino-3-chloro-2-fluorophenyl)pyridin-2-yl)-2-(1-methyl-1H-pyrazol-3-yl)ethyl)-1H-pyrazol-4-yl)phenyl)carbamate as a light yellow solid. LC/MS: mass calculated for C$_{28}$H$_{25}$ClFN$_7$O$_2$: 545.17, measured (ES, m/z): 546.10 [M+H]$^+$.

Step 7: Methyl (4-(1-(1-(5-(3-chloro-2-fluoro-6-(1H-tetrazol-1-yl)phenyl)pyridin-2-yl)-2-(1-methyl-1H-pyrazol-3-yl)ethyl)-1H-pyrazol-4-yl)phenyl) carbamate A mixture of methyl (4-(1-(1-(5-(6-amino-3-chloro-2-fluorophenyl)pyridin-2-yl)-2-(1-methyl-1H-pyrazol-3-yl) ethyl)-1H-pyrazol-4-yl)phenyl)carbamate (230 mg, 0.42 mmol, 1.0 equiv.), azidotrimethylsilane (0.5 mL) and trimethoxymethane (0.5 mL) in acetic acid glacial (1 mL) was stirred at room temperature overnight. The mixture was concentrated and the residue was purified by reverse phase chromatography on C18 (80 g, MeCN/H$_2$O (0.05% CF$_3$COOH): 0→45%) to yield methyl (4-(1-(1-(5-(3-chloro-2-fluoro-6-(1H-tetrazol-1-yl)phenyl)pyridin-2-yl)-2-(1-methyl-1H-pyrazol-3-yl)ethyl)-1H-pyrazol-4-yl)phenyl) carbamate as a light yellow solid. LC/MS: mass calculated for C$_{29}$H$_{24}$ClFN$_{10}$O$_2$: 598.18, measured (ES, m/z): 599.15 [M+H]$^+$.

Step 8: (R)-5-(3-Chloro-2-fluoro-6-(1H-tetrazol-1-yl)phenyl)-2-(1-(4-(4-((methoxycarbonyl)amino) phenyl)-1H-pyrazol-1-yl)-2-(1-methyl-1H-pyrazol-3-yl)ethyl)pyridine 1-oxide A mixture of methyl (4-(1-(1-(5-(3-chloro-2-fluoro-6-(1H-tetrazol-1-yl)phenyl)pyridin-2-yl)-2-(1-methyl-1H-pyrazol-3-yl)ethyl)-1H-pyrazol-4-yl)phenyl)carbamate (170 mg, 0.28 mmol, 1.0 equiv.) and 3-chloroperoxybenzoic acid (147 mg, 0.85 mmol, 3.0 equiv.) in DCM (3 mL) was stirred at room temperature for 2 h. The solution was purified by reverse phase chromatography on C18 (80 g, MeCN/H$_2$O (0.05% NH$_4$HCO$_3$): 0→45%) to yield 50 mg of 5-(3-chloro-2-fluoro-6-(1H-tetrazol-1-yl)phenyl)-2-(1-(4-(4-((methoxycarbonyl)amino)phenyl)-1H-pyrazol-1-yl)-2-(1-methyl-1H-pyrazol-3-yl)ethyl)pyridine 1-oxide as off-white solid. The racemic product was purified by Chiral HPLC to yield (S*)-5-(3-chloro-2-fluoro-6-(1H-tetrazol-1-yl)phenyl)-2-(1-(4-(4-((methoxycarbonyl)amino)phenyl)-1H-pyrazol-1-yl)-2-(1-methyl-1H-pyrazol-3-yl)ethyl)pyridine 1-oxide as a white solid.

LC/MS: mass calculated for C$_{29}$H$_{24}$ClFN$_{10}$O$_3$: 614.2 measured (ES, m/z): 615.2 [M+H]$^+$. $^1$H NMR (400 MHz, DMSO-d$_6$): δ 9.69 (s, 1H), 9.64 (s, 1H), 8.45 (d, J=1.6 Hz, 1H), 8.33 (s, 1H), 8.02-8.11 (m, 1H), 7.93 (s, 1H), 7.73-7.78 (m, 1H), 7.40-7.52 (m, 5H), 7.14-7.25 (m, 2H), 6.28 (t, J=7.3 Hz, 1H), 5.76 (d, J=2.2 Hz, 1H), 3.73 (s, 3H), 3.67 (s, 3H), 3.49-3.52 (m, 2H).

Example 338: (R*)-5-(3-Chloro-2-fluoro-6-(1H-tetrazol-1-yl)phenyl)-2-(1-(4-(4-((methoxycarbonyl)amino)phenyl)-1H-pyrazol-1-yl)-2-(1-methyl-1H-pyrazol-4-yl)ethyl)pyridine 1-oxide

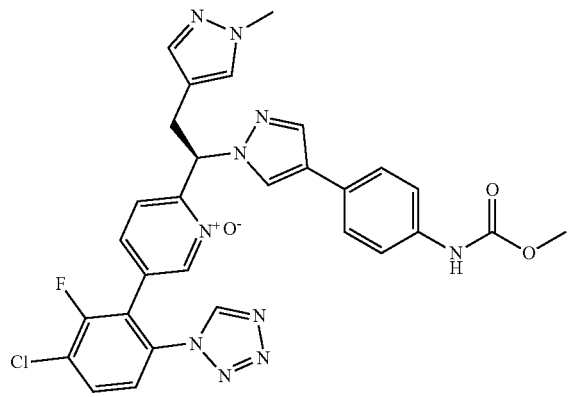

LC/MS: mass calculated for $C_{29}H_{24}ClFN_{10}O_3$: 614.17, measured (ES, m/z): 615.20 [M+H]$^+$. $^1$H NMR (400 MHz, DMSO-d$_6$) δ 9.69 (s, 1H), 9.63 (s, 1H), 8.45 (d, J=1.5 Hz, 1H), 8.30 (s, 1H), 8.04-8.06 (m, 1H), 7.97 (s, 1H), 7.76 (dd, J=8.7, 1.5 Hz, 1H), 7.49 (d, J=8.8 Hz, 2H), 7.43 (d, J=8.5 Hz, 2H), 7.27 (d, J=8.3 Hz, 2H), 7.16 (dd, J=8.4, 1.6 Hz, 1H), 7.01 (s, 1H), 6.04 (dd, J=9.4, 5.1 Hz, 1H), 3.71 (s, 3H), 3.66 (s, 3H), 3.33-3.41 (m, 2H).

Example 339: (R)-5-(3-Chloro-2-fluoro-6-(1H-tetrazol-1-yl)phenyl)-2-(1-(4-(4-((methoxycarbonyl)amino)phenyl)-1H-pyrazol-1-yl)-2-(1-methyl-1H-pyrazol-4-yl)ethyl)pyridine 1-oxide

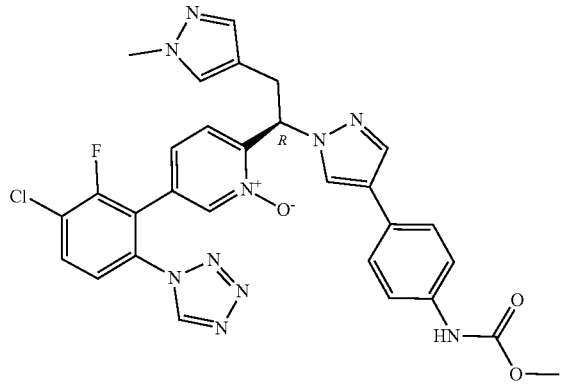

LC/MS: mass calculated for $C_{29}H_{24}ClFN_{10}O_3$: 614.17, measured (ES, m/z): 615.20 [M+H]$^+$. $^1$H NMR (400 MHz, DMSO-d$_6$) δ 9.68 (s, 1H), 9.62 (s, 1H), 8.44 (s, 1H), 8.29 (s, 1H), 8.01-8.10 (m, 1H), 7.96 (s, 1H), 7.75 (dd, J=8.6, 1.6 Hz, 1H), 7.40-7.52 (m, 4H), 7.27 (d, J=7.6 Hz, 2H), 7.16 (dd, J=8.1, 1.7 Hz, 1H), 7.01 (s, 1H), 6.04 (dd, J=9.4, 5.2 Hz, 1H), 3.71 (s, 3H), 3.66 (s, 3H), 3.32-3.46 (m, 2H).

Example 340: 5-(3-Chloro-2-fluoro-6-(1H-tetrazol-1-yl)phenyl)-2-(1-(4-(2-fluoropyridin-4-yl)-1H-pyrazol-1-yl)-2-(4-(trifluoromethyl)-1H-pyrazol-1-yl)ethyl)pyridine 1-oxide

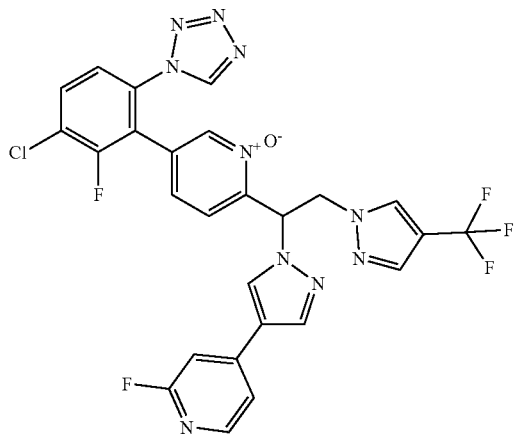

LC/MS: mass calculated for $C_{26}H_{16}ClF_5N_{10}O$: 614.1, measured (ES, m/z): 615.10 [M+H]$^+$. $^1$H NMR (400 MHz, DMSO-d$_6$) δ 9.70 (s, 1H), 8.61 (s, 1H), 8.54 (d, J=1.7 Hz, 1H), 8.31 (s, 1H), 8.13-8.21 (m, 2H), 8.08-8.09 (m, 1H), 7.87 (s, 1H), 7.77 (dd, J=8.8, 1.5 Hz, 1H), 7.52-7.53 (m, 1H), 7.44 (d, J=8.3 Hz, 1H), 7.38 (s, 1H), 7.24 (dd, J=8.3, 1.6 Hz, 1H), 6.60-6.62 (m, 1H), 5.16-5.17 (m, 1H), 5.06 (dd, J=13.9, 4.5 Hz, 1H). $^{19}$F NMR (376 MHz, DMSO-d$_6$) δ −54.67, −69.15, −74.70, −112.64.

Example 341: (R*)-5-(3-Chloro-2-fluoro-6-(1H-tetrazol-1-yl)phenyl)-2-(2-(4-fluoro-1H-pyrazol-1-yl)-1-(4-(2-(trifluoromethyl)pyridin-4-yl)-1H-pyrazol-1-yl)ethyl)pyridine 1-oxide

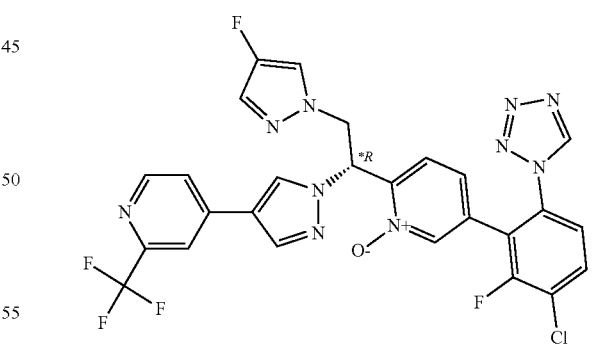

LC/MS: mass calculated for $C_{26}H_{16}ClF_5N_{10}O$: 614.1, measured (ES, m/z): 615.20 [M+H]$^+$. $^1$H NMR (400 MHz, DMSO-d$_6$) δ 9.69 (s, 1H), 8.75 (s, 1H), 8.67 (d, J=5.2 Hz, 1H), 8.51 (d, J=1.6 Hz, 1H), 8.38 (s, 1H), 8.03-8.13 (m, 2H), 7.88 (dd, J=5.2, 1.6 Hz, 1H), 7.77 (dd, J=8.7, 1.5 Hz, 1H), 7.69 (d, J=4.6 Hz, 1H), 7.42-7.50 (m, 2H), 7.23 (dd, J=8.3, 1.6 Hz, 1H), 6.54 (dd, J=9.7, 4.5 Hz, 1H), 5.01-5.02 (m, 1H), 4.91 (dd, J=13.8, 4.6 Hz, 1H). $^{19}$F NMR (376 MHz, DMSO-d$_6$) δ −66.54, −112.61, −177.77.

Example 342: (S*)-5-(3-Chloro-2-fluoro-6-(1H-tetrazol-1-yl)phenyl)-2-(2-(4-fluoro-1H-pyrazol-1-yl)-1-(4-(2-(trifluoromethyl)pyridin 4-yl)-1H-pyrazol-1-yl)ethyl)pyridine 1-oxide

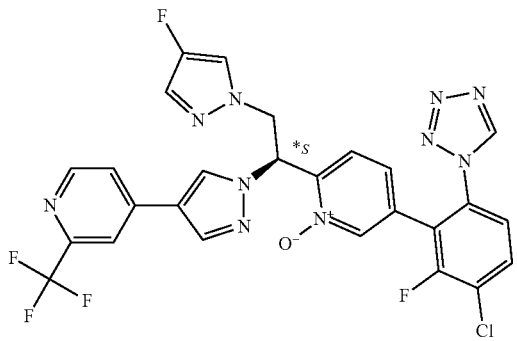 [SMILES: [O-][n+]1cc(-c2c(-n3cnnn3)ccc(Cl)c2F)ccc1[C@H](Cn1cc(F)cn1)n1cc(-c2ccnc(C(F)(F)F)c2)cn1]

LC/MS: mass calculated for C$_{26}$H$_{16}$ClF$_5$N$_{10}$O: 614.1, measured (ES, m/z): 615.20 [M+H]$^+$. $^1$H NMR (400 MHz, DMSO-d$_6$) δ 9.67 (s, 1H), 8.72 (s, 1H), 8.66 (d, J=5.1 Hz, 1H), 8.50 (s, 1H), 8.37 (s, 1H), 8.06 (dd, J=16.1, 7.8 Hz, 2H), 7.87 (d, J=5.6 Hz, 1H), 7.75 (dd, J=8.7, 1.5 Hz, 1H), 7.68 (d, J=4.5 Hz, 1H), 7.42-7.50 (m, 2H), 7.23 (dd, J=8.4, 1.7 Hz, 1H), 6.53 (dd, J=9.6, 4.6 Hz, 1H), 5.00 (dd, J=13.9, 9.7 Hz, 1H), 4.90 (dd, J=13.9, 4.6 Hz, 1H). $^{19}$F NMR (376 MHz, DMSO-d$_6$) δ −66.54, −112.61, −177.77.

Example 343: (S*)-4-(1-(1-(5-(3-Chloro-2-fluoro-6-(1H-tetrazol-1-yl)phenyl)-1-oxidopyridin-2-yl)-2-(1H-pyrazol-1-yl)ethyl)-1H-pyrazol-4-yl)-2-(difluoromethyl)pyridine 1-oxide

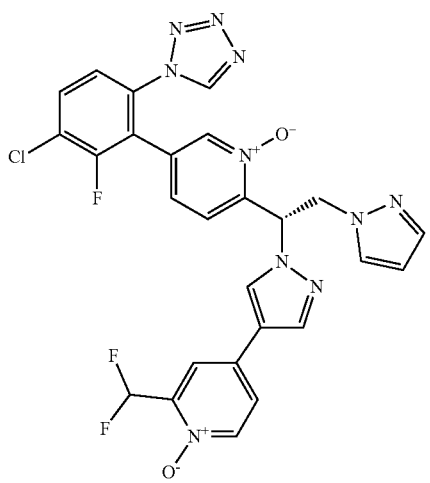

LC/MS: mass calculated for C$_{26}$H$_{18}$ClF$_3$N$_{10}$O$_2$: 594.1, measured (ES, m/z): 595.1 [M+H]$^+$. $^1$H NMR (400 MHz, DMSO-d$_6$) δ 9.69 (s, 1H), 8.45-8.69 (m, 2H), 8.34 (d, J=6.8 Hz, 1H), 8.29 (s, 1H), 8.08-8.09 (m, 1H), 7.94 (d, J=2.7 Hz, 1H), 7.77-7.79 (m, 2H), 7.05-7.54 (m, 5H), 6.54-6.55 (m, 1H), 6.13-6.14 (m, 1H), 4.91-5.23 (m, 2H). $^{19}$F NMR (376 MHz, DMSO-d$_6$) δ −112.61, −122.81.

Example 344: (R*)-2-(1-(4-(4-Carboxyphenyl)-1H-pyrazol-1-yl)-2-(2-oxopyrrolidin-1-yl)ethyl)-5-(3-chloro-6-(difluoromethyl)-2-fluorophenyl)pyridine 1-oxide

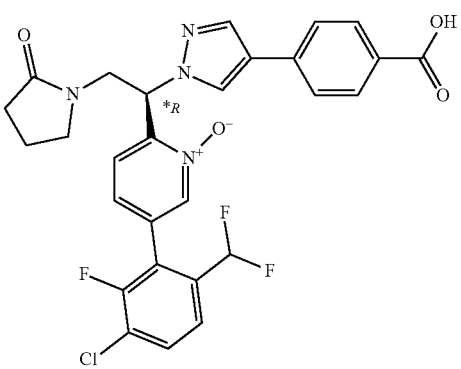 [SMILES: O=C(O)c1ccc(-c2cnn([C@H](CN3CCCC3=O)c3ccc(-c4c(C(F)F)ccc(Cl)c4F)c[n+]3[O-])c2)cc1]

LC/MS: mass calculated for C$_{28}$H$_{22}$ClF$_3$N$_4$O$_4$: 570.1, measured (ES, m/z): 571.15 [M+H]$^+$. $^1$H NMR (300 MHz, DMSO-d$_6$) δ 12.90 (brs, 1H), 8.51-8.69 (m, 2H), 8.15 (s, 1H), 7.85-8.00 (m, 3H), 7.67-7.81 (m, 3H), 7.63 (d, J=8.6 Hz, 1H), 7.44 (d, J=8.3 Hz, 1H), 6.90 (t, J=53.8 Hz, 1H), 6.36-6.45 (m, 1H), 3.99-4.25 (m, 2H), 3.31-3.44 (m, 1H), 2.89-3.05 (m, 1H), 2.11-2.25 (m, 2H), 1.73-1.95 (m, 2 h). $^{19}$F NMR (282 MHz, DMSO-d$_6$) d −109.80, −115.23.

Example 345: (S*)-2-(1-(4-(4-Carboxyphenyl)-1H-pyrazol-1-yl)-2-(2-oxopyrrolidin-1-yl)ethyl)-5-(3-chloro-6-(difluoromethyl)-2-fluorophenyl)pyridine 1-oxide

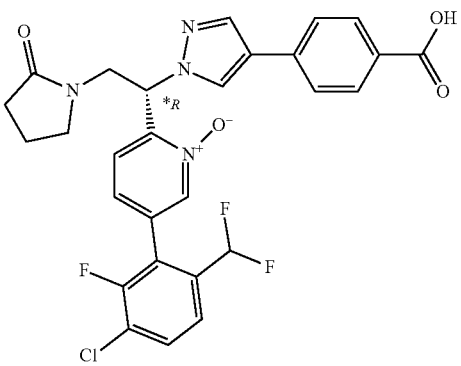 [SMILES: O=C(O)c1ccc(-c2cnn([C@@H](CN3CCCC3=O)c3ccc(-c4c(C(F)F)ccc(Cl)c4F)c[n+]3[O-])c2)cc1]

LC/MS: mass calculated for C$_{28}$H$_{22}$ClF$_3$N$_4$O$_4$: 570.1, measured (ES, m/z): 571.1 [M+H]$^+$. $^1$H NMR (300 MHz, DMSO-d$_6$) δ 12.87 (s, 1H), 8.48-8.70 (m, 2H), 8.15 (s, 1H), 7.86-7.98 (m, 3H), 7.66-7.79 (m, 3H), 7.63 (d, J=8.6 Hz, 1H), 7.44 (d, J=8.0 Hz, 1H), 6.72-7.12 (m, 1H), 6.40-6.42 (m, 1H), 3.99-4.24 (m, 2H), 3.36-3.44 (m, 1H), 2.91-3.06 (m, 1H), 2.09-2.24 (m, 2H), 1.70-1.93 (m, 2 h). $^{19}$F NMR (282 MHz, DMSO-d$_6$) δ −109.80, −115.23.

Example 346: 2-(1-(4-(2-Carboxypyridin-4-yl)-1H-pyrazol-1-yl)-2-cyclopropylethyl)-5-(3-chloro-6-(difluoromethyl)-2-fluorophenyl)pyridine 1-oxide

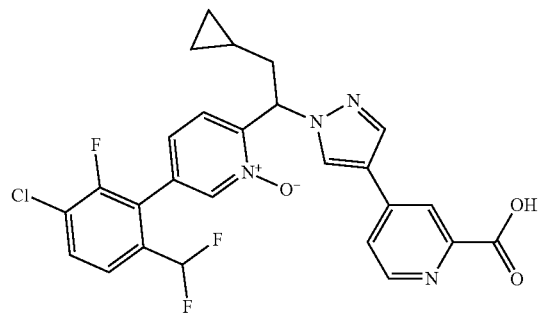 [SMILES: O=C(O)c1cc(-c2cnn(C(CC3CC3)c3ccc(-c4c(C(F)F)ccc(Cl)c4F)c[n+]3[O-])c2)ccn1]

LC/MS: mass calculated for $C_{26}H_{20}ClF_3N_4O_3$: 528.12, measured (ES, m/z): 529.1 [M+H]$^+$. $^1$H NMR (300 MHz, DMSO-d$_6$) δ 8.98 (s, 1H), 8.63 (d, J=5.3 Hz, 1H), 8.48 (s, 1H), 8.26-8.37 (m, 2H), 7.82-7.94 (m, 2H), 7.59 (d, J=8.5 Hz, 1H), 7.43 (d, J=8.2 Hz, 1H), 7.36-7.37 (m, 1H), 6.72-7.11 (m, 1H), 6.18 (dd, J=10.1, 4.1 Hz, 1H), 2.48-2.49 (m, 1H), 1.95-2.02 (m, 1H), 0.64-0.65 (m, 1H), 0.29-0.45 (m, 2H), 0.18-0.19 (m, 1H), 0.05-0.06 (m, 1H). $^{19}$F NMR (282 MHz, DMSO-d$_6$) δ −74.33, −115.29.

Example 347: 2-((R*)-1-(4-(6-Amino-2-fluoropyridin-3-yl)-1H-pyrazol-1-yl)-2-((1S*,2S*)-2-carbamoylcyclopropyl)ethyl)-5-(3-chloro-2-fluoro-6-(1H-tetrazol-1-yl)phenyl)pyridine 1-oxide

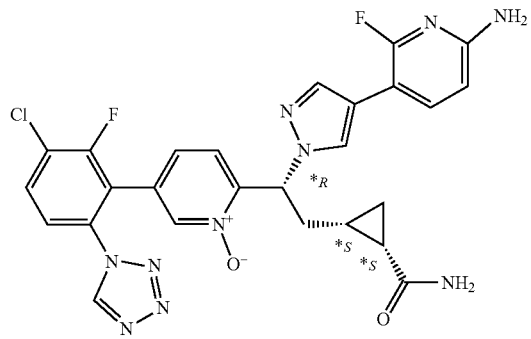 [SMILES: NC(=O)[C@H]1C[C@H]1C[C@H](c1ccc(-c2c(-n3cnnn3)ccc(Cl)c2F)c[n+]1[O-])n1cc(-c2ccc(N)nc2F)cn1]

LC/MS: mass calculated for $C_{26}H_{21}ClF_2N_{10}O_2$: 578.2, measured (ES, m/z): 579.1 [M+H]$^+$. $^1$H NMR (400 MHz, DMSO-d$_6$) δ 9.69 (s, 1H), 8.21-8.42 (m, 2H), 8.06-8.08 (m, 1H), 7.68-7.88 (m, 3H), 7.36 (s, 1H), 7.22 (d, J=8.3 Hz, 1H), 7.15 (dd, J=8.3, 1.7 Hz, 1H), 6.72 (s, 1H), 6.25-6.40 (m, 3H), 6.04-6.06 (m, 1H), 2.63-2.66 (m, 1H), 1.73-1.84 (m, 1H), 1.37-1.38 (m, 1H), 0.94 (s, 1H), 0.75-0.76 (m, 1H), 0.59-0.61 (m, 1H).

Example 348: 2-((R*)-1-(4-(6-Amino-2-fluoropyridin-3-yl)-1H-pyrazol-1-yl)-2-((1R*,2S*)-2-carbamoylcyclopropyl)ethyl)-5-(3-chloro-2-fluoro-6-(1H-tetrazol-1-yl)phenyl)pyridine 1-oxide

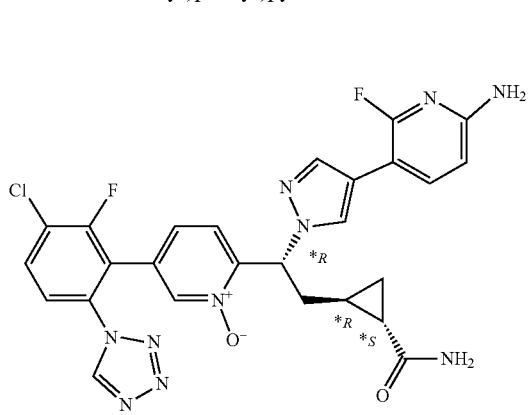

LC/MS: mass calculated for $C_{26}H_{21}ClF_2N_{10}O_2$: 578.2, measured (ES, m/z): 579.2 [M+H]$^+$. $^1$H NMR (400 MHz, DMSO-d$_6$) δ 9.69 (s, 1H), 8.41 (s, 1H), 8.19 (d, J=1.8 Hz, 1H), 8.06-8.07 (m, 1H), 7.86 (s, 1H), 7.73-7.81 (m, 2H), 7.52 (s, 1H), 7.18-7.21 (m, 2H), 6.72 (s, 1H), 6.27-6.42 (m, 3H), 6.04 (dd, J=10.4, 3.7 Hz, 1H), 2.35-2.37 (m, 1H), 2.04-2.06 (m, 1H), 1.46-1.48 (m, 1H), 0.98-0.99 (m, 1H), 0.67-0.74 (m, 1H), 0.42-0.43 (m, 1H).

Example 349: 2-((S*)-1-(4-(6-Amino-2-fluoropyridin-3-yl)-1H-pyrazol-1-yl)-2-((1R*,2R*)-2-carbamoylcyclopropyl)ethyl)-5-(3-chloro-2-fluoro-6-(1H-tetrazol-1-yl)phenyl)pyridine 1-oxide

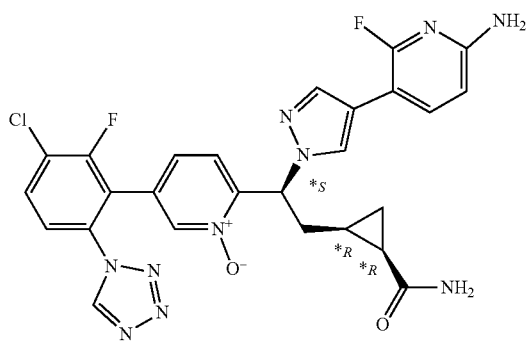 [SMILES: NC(=O)[C@@H]1C[C@@H]1C[C@@H](c1ccc(-c2c(-n3cnnn3)ccc(Cl)c2F)c[n+]1[O-])n1cc(-c2ccc(N)nc2F)cn1]

LC/MS: mass calculated for $C_{26}H_{21}ClF_2N_{10}O_2$: 578.2, measured (ES, m/z): 579.2 [M+H]$^+$. $^1$H NMR (400 MHz, DMSO-d$_6$) δ 9.69 (s, 1H), 8.41 (d, J=1.7 Hz, 1H), 8.17 (d, J=1.6 Hz, 1H), 8.06-8.07 (m, 1H), 7.72-7.89 (m, 3H), 7.52 (s, 1H), 7.32-7.45 (m, 1H), 7.10-7.22 (m, 1H), 6.80 (s, 1H), 6.36 (dd, J=8.3, 2.1 Hz, 1H), 6.31 (d, J=4.6 Hz, 2H), 6.10-6.13 (m, 1H), 2.28-2.39 (m, 1H), 1.59-1.61 (m, 1H), 1.25 (s, 2H), 1.12 (s, 1H), 0.72-0.89 (m, 1H).

Example 350: 2-((S*)-1-(4-(6-Amino-2-fluoropyridin-3-yl)-1H-pyrazol-1-yl)-2-((1S*,2R*)-2-carbamoylcyclopropyl)ethyl)-5-(3-chloro-2-fluoro-6-(1H-tetrazol-1-yl)phenyl)pyridine 1-oxide

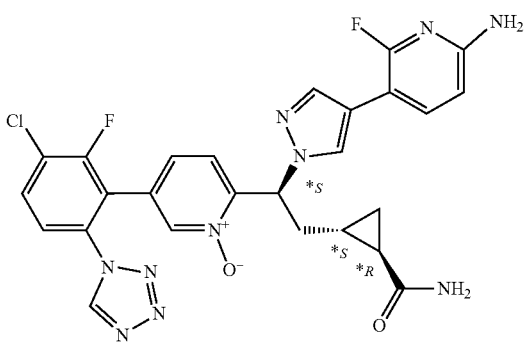 [SMILES: NC(=O)[C@@H]1C[C@H]1C[C@@H](c1ccc(-c2c(-n3cnnn3)ccc(Cl)c2F)c[n+]1[O-])n1cc(-c2ccc(N)nc2F)cn1]

LC/MS: mass calculated for $C_{26}H_{21}ClF_2N_{10}O_2$: 578.2, measured (ES, m/z): 579.1 [M+H]$^+$. $^1$H NMR (400 MHz, DMSO-d$_6$) δ 9.69 (s, 1H), 8.41 (s, 1H), 8.19 (d, J=1.8 Hz, 1H), 8.06-8.07 (m, 1H), 7.67-7.88 (m, 3H), 7.53 (s, 1H), 7.13-7.24 (m, 2H), 6.71-6.75 (m, 1H), 6.25-6.42 (m, 3H), 6.04-6.06 (m, 1H), 2.30-2.40 (m, 1H), 2.00-2.09 (m, 1H), 1.47-1.48 (m, 1H), 0.98 (s, 1H), 0.71-0.72 (m, 1H), 0.38-0.47 (m, 1H).

Example 351: (R*)-4-(1-(1-(5-(3-Chloro-2-fluoro-6-(1H-tetrazol-1-yl)phenyl)-1-oxidopyridin-2-yl)-2-(1H-pyrazol-1-yl)ethyl)-1H-pyrazol-4-yl)-2-(difluoromethyl)pyridine 1-oxide

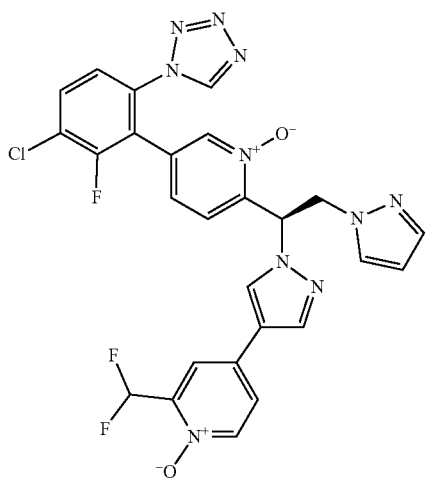

LC/MS: mass calculated for $C_{26}H_{18}ClF_3N_{10}O_2$: 594.1, measured (ES, m/z): 595.1 [M+H]$^+$. $^1$H NMR (400 MHz, DMSO-d$_6$) δ 9.69 (s, 1H), 8.48-8.68 (m, 2H), 8.34 (d, J=6.9 Hz, 1H), 8.29 (s, 1H), 8.08-8.09 (m, 1H), 7.94 (d, J=2.7 Hz, 1H), 7.77-7.78 (m, 2H), 6.92-7.56 (m, 5H), 6.54-6.55 (m, 1H), 6.13-6.14 (m, 1H), 4.82-5.20 (m, 2H). $^{19}$F NMR (376 MHz, DMSO-d$_6$) δ −73.66, −112.61, −122.81.

Example 352: 2-((S*)-1-(4-(6-Amino-2-fluoropyridin-3-yl)-1H-pyrazol-1-yl)-2-((1R*,2S*)-2-carbamoylcyclopropyl)ethyl)-5-(3-chloro-2-fluoro-6-(1H-tetrazol-1-yl)phenyl)pyridine 1-oxide

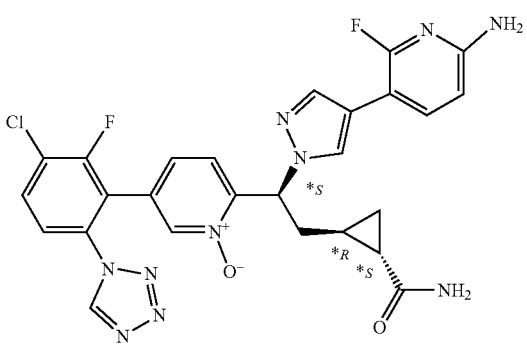 [SMILES: NC(=O)[C@H]1C[C@@H]1C[C@@H](c1ccc(-c2c(-n3cnnn3)ccc(Cl)c2F)c[n+]1[O-])n1cc(-c2ccc(N)nc2F)cn1]

LC/MS: mass calculated for $C_{26}H_{21}ClF_2N_{10}O_2$: 578.2, measured (ES, m/z): 579.1 [M+H]$^+$. $^1$H NMR (400 MHz, DMSO-d$_6$) δ 9.69 (s, 1H), 8.41 (s, 1H), 8.24 (s, 1H), 8.06-8.07 (m, 1H), 7.59-7.92 (m, 3H), 7.36 (s, 1H), 7.22 (d, J=8.3 Hz, 1H), 7.12-7.18 (m, 1H), 6.72 (s, 1H), 6.25-6.40 (m, 3H), 6.04-6.05 (m, 1H), 2.55-2.66 (m, 1H), 1.78-1.79 (m, 1H), 1.37-1.38 (m, 1H), 0.94 (s, 1H), 0.75-0.76 (m, 1H), 0.60-0.61 (m, 1H).

Example 353: 2-((R*)-1-(4-(6-Amino-2-fluoropyridin-3-yl)-1H-pyrazol-1-yl)-2-((1S*,2R*)-2-carbamoylcyclopropyl)ethyl)-5-(3-chloro-2-fluoro-6-(1H-tetrazol-1-yl)phenyl)pyridine 1-oxide

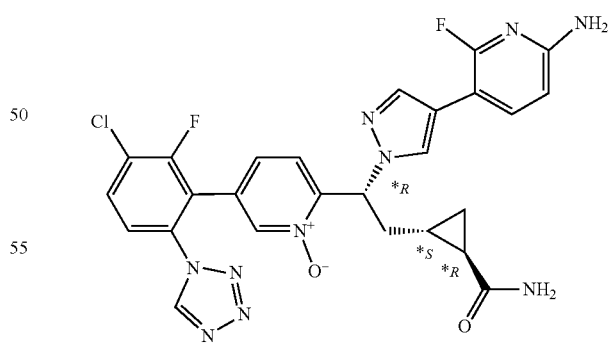

LC/MS: mass calculated for $C_{26}H_{21}ClF_2N_{10}O_2$: 578.2, measured (ES, m/z): 579.1 [M+H]$^+$. $^1$H NMR (400 MHz, DMSO-d$_6$) δ 9.70 (s, 1H), 8.42 (d, J=1.7 Hz, 1H), 8.18 (s, 1H), 8.06-8.07 (m, 1H), 7.72-7.89 (m, 3H), 7.54 (s, 1H), 7.35 (d, J=8.2 Hz, 1H), 7.14 (dd, J=8.3, 1.7 Hz, 1H), 6.82 (s, 1H), 6.29-6.40 (m, 3H), 6.09-6.11 (m, 1H), 2.41-2.42 (m, 1H), 1.59-1.61 (m, 1H), 1.24 (s, 2H), 0.68-0.90 (m, 3H).

Example 354: (R)-2-(1-(4-(6-Amino-2-methylpyridin-3-yl)-1H-pyrazol-1-yl)-3-(difluoromethoxy)propyl)-5-(3-chloro-2-fluoro-6-(1H-tetrazol-1-yl)phenyl)pyridine 1-oxide

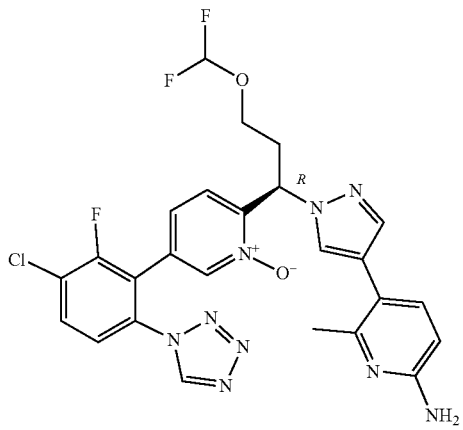

LC/MS: mass calculated for $C_{25}H_{21}ClF_3N_9O_2$: 571.2, measured (ES, m/z): 572.2 [M+H]$^+$. $^1$H NMR (300 MHz, DMSO-d$_6$) δ 9.69 (s, 1H), 8.46 (d, J=1.4 Hz, 1H), 8.15 (s, 1H), 8.07-8.09 (m, 1H), 7.71-7.83 (m, 2H), 7.62-7.64 (m, 1H), 7.25-7.27 (m, 1H), 7.18 (dd, J=8.3, 1.6 Hz, 1H), 6.34-6.93 (m, 3H), 6.18 (dd, J=9.8, 4.6 Hz, 1H), 3.80-3.90 (m, 1H), 3.69 (s, 1H), 2.61-2.63 (m, 2H), 2.40 (s, 3H). $^{19}$F NMR (282 MHz, DMSO-d$_6$) δ −73.44, −83.29, −112.68.

Example 355: (R*)-2-(1-(4-(6-Amino-2-methylpyridin-3-yl)-1H-pyrazol-1-yl)-3-(difluoromethoxy)propyl)-5-(3-chloro-2-fluoro-6-(1H-tetrazol-1-yl)phenyl)pyridine 1-oxide

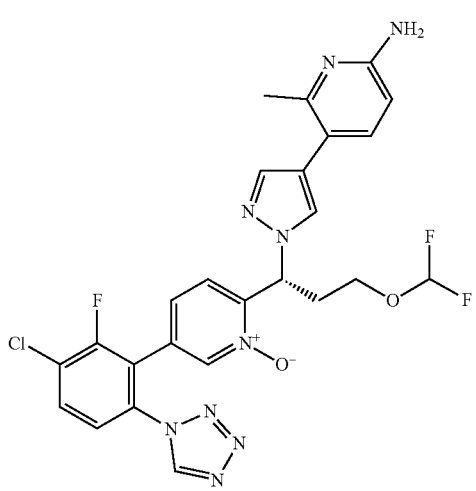 [SMILES: Cc1nc(N)ccc1-c1cnn([C@H](CCOC(F)F)c2ccc(-c3c(-n4cnnn4)ccc(Cl)c3F)c[n+]2[O-])c1]

LC/MS: mass calculated for $C_{25}H_{21}ClF_3N_9O_2$: 571.2, measured (ES, m/z): 572.2 [M+H]$^+$. $^1$H NMR (300 MHz, DMSO-d$_6$) δ 9.69 (s, 1H), 8.46 (d, J=1.4 Hz, 1H), 8.23 (s, 1H), 8.01-8.13 (m, 1H), 7.70-7.92 (m, 3H), 7.28 (d, J=8.3 Hz, 1H), 7.19 (dd, J=8.2, 1.6 Hz, 1H), 6.31-6.91 (m, 2H), 6.20-6.22 (m, 1H), 3.80-3.90 (m, 1H), 3.67-3.68 (m, 1H), 2.59-2.60 (m, 2H), 2.46 (s, 3H). $^{19}$F NMR (282 MHz, DMSO-d$_6$) δ −73.47, −83.31, −112.69.

Example 356: 5-(3-Chloro-2-fluoro-6-(1H-tetrazol-1-yl)phenyl)-2-(2-(N-methylbenzamido)-1-(4-(1-oxidopyridin-4-yl)-1H-pyrazol-1-yl)ethyl)pyridine 1-oxide

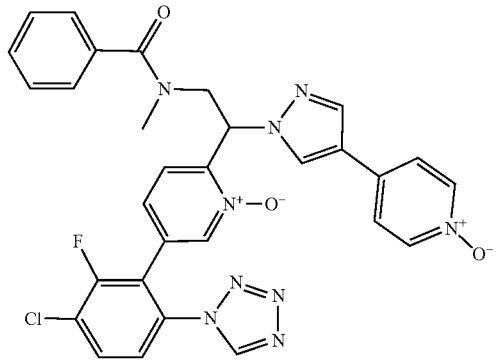 [SMILES: CN(CC(c1ccc(-c2c(-n3cnnn3)ccc(Cl)c2F)c[n+]1[O-])n1cc(-c2cc[n+]([O-])cc2)cn1)C(=O)c1ccccc1]

LC/MS: mass calculated for $C_{30}H_{23}ClFN_9O_3$: 611.15, measured (ES, m/z): 612.15 [M+H]$^+$. $^1$H NMR (400 MHz, DMSO-d$_6$) δ 9.70 (s, 1H), 8.84 (s, 1H), 8.48 (s, 1H), 8.30-8.39 (m, 2H), 8.20 (s, 1H), 8.07-8.09 (m, 1H), 7.77 (d, J=11.2 Hz, 4H), 7.41 (d, J=6.3 Hz, 3H), 7.23 (s, 2H), 7.04 (d, J=51.1 Hz, 1H), 6.51 (s, 1H), 4.29-4.32 (m, 2H), 2.87-3.05 (m, 3H).

Example 357: 5-(3-Chloro-2-fluoro-6-(1H-tetrazol-1-yl)phenyl)-2-(2-(N-methyl-2-phenylacetamido)-1-(4-(1-oxidopyridin-4-yl)-1H-pyrazol-1-yl)ethyl)pyridine 1-oxide

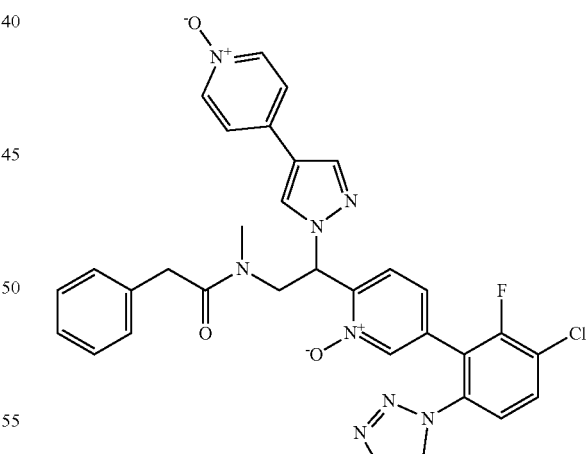

LC/MS: mass calculated for $C_{31}H_{25}ClFN_9O_3$: 625.18, measured (ES, m/z): 626.15 [M+H]$^+$. $^1$H NMR (400 MHz, DMSO-d$_6$) δ 9.69 (d, J=12.1 Hz, 1H), 8.67 (d, J=70.1 Hz, 1H), 8.49 (d, J=30.8 Hz, 1H), 8.33-8.39 (m, 2H), 8.15 (s, 1H), 8.07-8.09 (m, 1H), 7.71-7.80 (m, 3H), 7.58-7.67 (m, 1H), 7.13-7.30 (m, 4H), 6.93-7.12 (m, 2H), 6.31-6.33 (m, 1H), 4.28-4.36 (m, 1H), 3.95-4.11 (m, 1H), 3.49-3.80 (m, 2H), 2.77 (d, J=10.3 Hz, 3H).

Example 358: 5-(3-Chloro-2-fluoro-6-(1H-tetrazol-1-yl)phenyl)-2-(1-(4-(2-fluoropyridin-4-yl)-1H-pyrazol-1-yl)-2-(5-(trifluoromethyl)-1H-pyrazol-1-yl)ethyl)pyridine 1-oxide

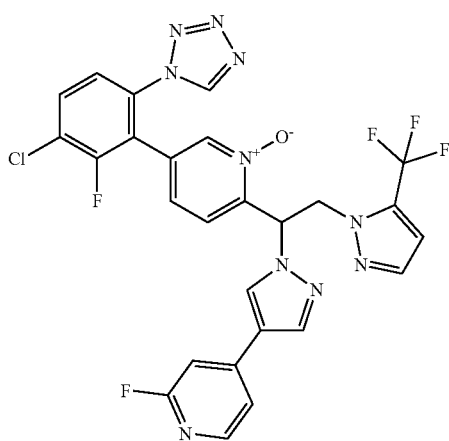 [SMILES: [O-][n+]1cc(-c2c(-n3cnnn3)ccc(Cl)c2F)ccc1C(Cn1nccc1C(F)(F)F)n1cc(-c2ccnc(F)c2)cn1]

LC/MS: mass calculated for $C_{26}H_{16}ClF_5N_{10}O$: 614.11, measured (ES, m/z): 615.15 [M+H]$^+$. $^1$H NMR (400 MHz, DMSO-d$_6$) δ 9.70 (s, 1H), 8.62 (s, 1H), 8.55 (d, J=1.6 Hz, 1H), 8.32 (s, 1H), 8.16 (d, J=5.3 Hz, 1H), 8.08 (dd, J=8.7, 7.7 Hz, 1H), 7.71-7.81 (m, 2H), 7.50-7.55 (m, 1H), 7.46 (d, J=8.3 Hz, 1H), 7.38 (s, 1H), 7.25 (dd, J=8.3, 1.6 Hz, 1H), 6.62 (d, J=2.4 Hz, 1H), 6.50-6.60 (m, 1H), 5.16-5.28 (m, 1H), 5.05-5.15 (m, 1H). $^{19}$F NMR (376 MHz, DMSO-d$_6$) d −60.37, −69.13, −74.89, −74.95, −112.61.

Example 359: 5-(5-Chloro-2-(1H-tetrazol-1-yl)phenyl)-2-(1-(4-(2-fluoropyridin-4-yl)-1H-pyrazol-1-yl)-2-(1-methylcyclopropane-1-carboxamido)ethyl)pyridine 1-oxide

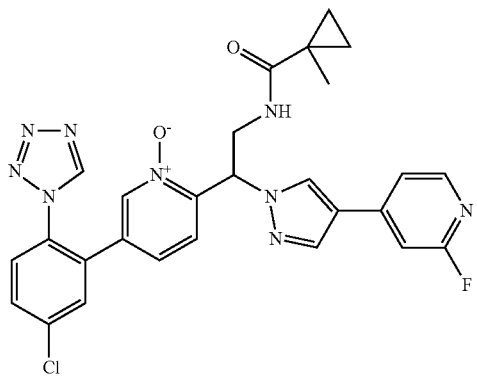 [SMILES: CC1(C(=O)NCC(c2ccc(-c3cc(Cl)ccc3-n3cnnn3)c[n+]2[O-])n2cc(-c3ccnc(F)c3)cn2)CC1]

LC/MS: mass calculated for $C_{27}H_{23}ClFN_9O_2$: 559.2, measured (ES, m/z): 560.3 [M+H]$^+$. $^1$H NMR (400 MHz, CD$_3$OD) δ ppm 0.46-0.64 (m, 2H), 0.87-1.06 (m, 2H), 1.21 (s, 3H), 3.97-4.15 (m, 2H), 4.20 (dd, J=13.7, 7.8 Hz, 1H), 6.45 (dd, J=7.8, 5.9 Hz, 1H), 7.17 (d, J=8.3, 1H), 7.24-7.34 (m, 2H), 7.49-7.54 (m, 2H), 7.54-7.59 (m, 1H), 7.61-7.74 (m, 1H), 7.74-7.83 (m, 1H), 8.01-8.24 (m, 1H), 8.29 (d, J=1.5 Hz, 1H), 8.47 (s, 1H), 9.38 (s, 1H).

Example 360: 5-(3-Chloro-2-fluoro-6-(1H-tetrazol-1-yl)phenyl)-2-(1-(4-(1-oxidopyridin-4-yl)-1H-pyrazol-1-yl)-2-(1H-pyrazol-1-yl)ethyl)pyridine 1-oxide

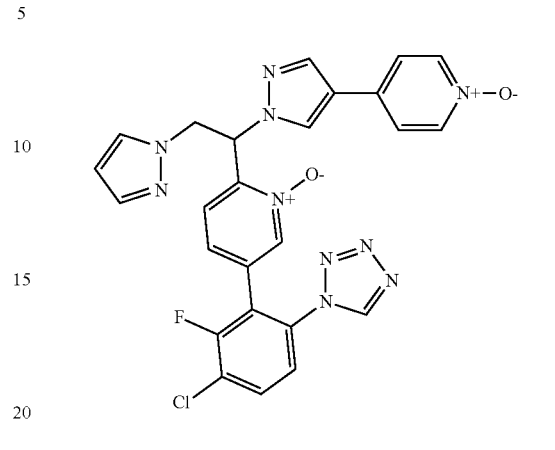

LC/MS: mass calculated for $C_{25}H_{18}ClFN_{10}O_2$: 544.1, measured (ES, m/z): 545.2 [M+H]$^+$. $^1$H NMR (400 MHz, DMSO-d$_6$) δ 9.69 (s, 1H), 8.49-8.58 (m, 2H), 8.17-8.39 (m, 2H), 8.08-8.09 (m, 1H), 7.64-7.82 (m, 3H), 7.38-7.55 (m, 3H), 7.22 (d, J=8.3 Hz, 1H), 6.55-6.56 (m, 1H), 6.13-6.14 (m, 1H), 5.08-5.09 (m, 1H), 4.97 (dd, J=13.9, 4.5 Hz, 1H). $^{19}$F NMR (376 MHz, DMSO-d$_6$) δ −74.65, −112.62.

Example 361: (S*)-5-(3-Chloro-2-fluoro-6-(1H-tetrazol-1-yl)phenyl)-2-(2-(N-methyl-3-phenylpropanamido)-1-(4-(1-oxidopyridin-4-yl)-1H-pyrazol-1-yl)ethyl)pyridine 1-oxide

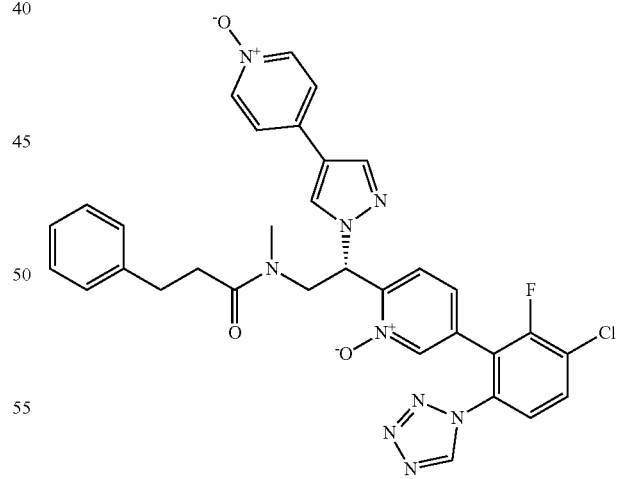

LC/MS: mass calculated for $C_{32}H_{27}ClFN_9O_3$: 639.19, measured (ES, m/z): 640.25 [M+H]$^+$. $^1$H NMR (300 MHz, DMSO-d$_6$) δ 9.69 (s, 1H), 8.58 (d, J=8.3 Hz, 1H), 8.39-8.52 (m, 1H), 8.00-8.27 (m, 4H), 7.76-7.78 (m, 1H), 7.51-7.69 (m, 3H), 7.19-7.31 (m, 6H), 6.16-6.41 (m, 1H), 3.83-4.40 (m, 2H), 2.62-2.84 (m, 6H), 2.55-2.56 (m, 1H).

Example 362: (R*)-5-(3-Chloro-2-fluoro-6-(1H-tetrazol-1-yl)phenyl)-2-(2-(N-methyl-3-phenylpropanamido)-1-(4-(1-oxidopyridin-4-yl)-1H-pyrazol-1-yl)ethyl)pyridine 1-oxide

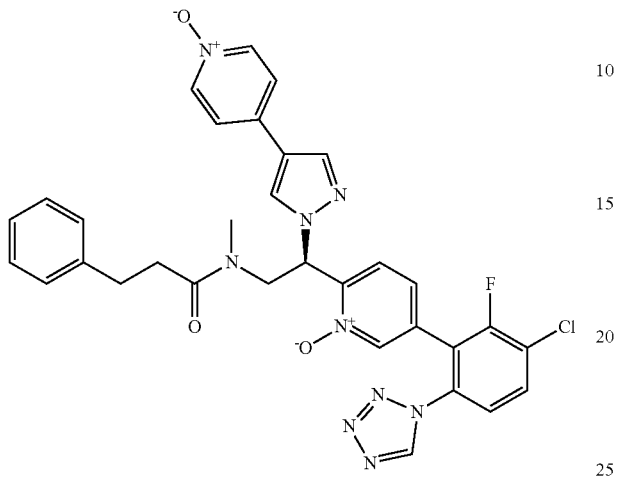

LC/MS: mass calculated for C₃₂H₂₇ClFN₉O₃: 639.19, measured (ES, m/z): 640.25 [M+H]⁺. ¹H NMR (300 MHz, DMSO-d₆) δ 9.69 (s, 1H), 8.58 (d, J=8.3 Hz, 1H), 8.47 (d, J=14.7 Hz, 1H), 8.00-8.25 (m, 4H), 7.76-7.78 (m, 1H), 7.52-7.69 (m, 3H), 7.10-7.31 (m, 6H), 6.11-6.42 (m, 1H), 3.79-4.43 (m, 2H), 2.75-2.77 (m, 5H), 2.55-2.56 (m, 2H).

Example 363: (S*)-5-(3-Chloro-2-fluoro-6-(1H-tetrazol-1-yl)phenyl)-2-(2-(N-methyl-3-phenylpropanamido)-1-(4-(1-oxidopyridin-4-yl)-1H-pyrazol-1-yl)ethyl)pyridine 1-oxide

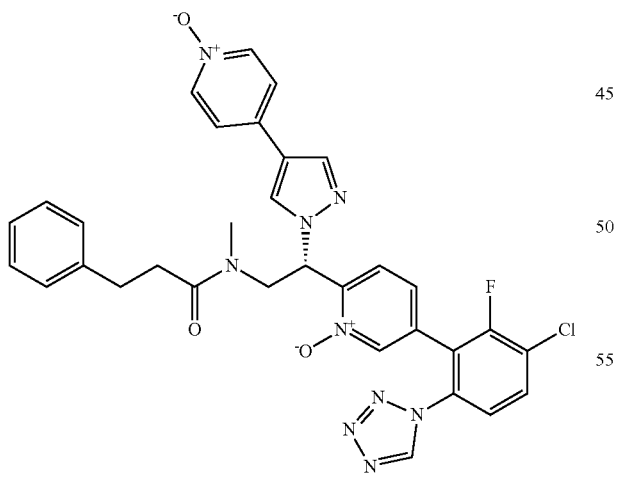

LC/MS: mass calculated for C₂₅H₂₁ClFN₉O₃: 549.14 measured (ES, m/z): 550.20 [M+H]⁺. ¹H NMR (300 MHz, DMSO-d₆) δ 9.69 (d, J=3.9 Hz, 1H), 8.63 (d, J=12.9 Hz, 1H), 8.40-8.55 (m, 1H), 8.02-8.28 (m, 4H), 7.53-7.82 (m, 4H), 7.23-7.24 (m, 1H), 6.19-6.38 (m, 1H), 3.78-4.44 (m, 2H), 2.74 (s, 3H), 1.92 (d, J=9.3 Hz, 3H).

Example 364: 5-(3-Chloro-2-fluoro-6-(1H-tetrazol-1-yl)phenyl)-2-(2-(4-fluoro-1H-pyrazol-1-yl)-1-(4-(2-fluoropyridin-4-yl)-1H-pyrazol-1-yl)ethyl)pyridine 1-oxide

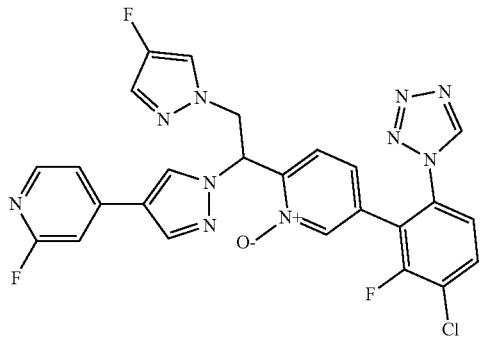 [SMILES: [O-][n+]1cc(-c2c(-n3cnnn3)ccc(Cl)c2F)ccc1C(Cn1cc(F)cn1)n1cc(-c2ccnc(F)c2)cn1]

LC/MS: mass calculated for C₂₅H₁₆ClF₃N₁₀O: 564.11, measured (ES, m/z): 565.10 [M+H]⁺. ¹H NMR (300 MHz, DMSO-d₆) δ 9.67 (s, 1H), 8.60 (s, 1H), 8.49 (d, J=1.3 Hz, 1H), 8.27 (s, 1H), 8.14 (d, J=5.3 Hz, 1H), 8.05 (dd, J=8.7, 7.8 Hz, 1H), 7.74 (dd, J=8.7, 1.6 Hz, 1H), 7.62-7.70 (m, 1H), 7.50-7.59 (m, 1H), 7.40-7.53 (m, 2H), 7.37 (s, 1H), 7.16-7.26 (m, 1H), 6.48-6.58 (m, 1H), 4.77-5.07 (m, 2H). ¹⁹F NMR (282 MHz, DMSO-d₆) d −69.14, −75.24, −112.62, −177.79.

Example 365: (R*)-5-(3-Chloro-6-(difluoromethoxy)-2-fluorophenyl)-2-(2-(4-fluorophenyl)-1-(4-(1-oxidopyridin-4-yl)-1H-pyrazol-1-yl)ethyl)pyridine 1-oxide

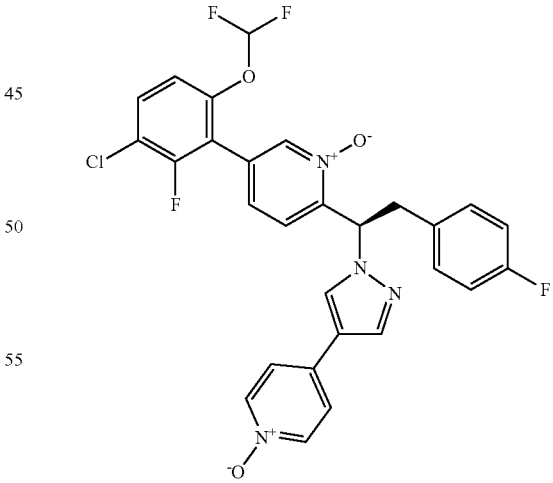

LC/MS: mass calculated for C₂₈H₁₉ClF₄N₄O₃: 570.10, measured (ES, m/z): 571.15 [M+H]⁺. ¹H NMR (400 MHz, DMSO-d₆) δ 8.56 (d, J=6.2 Hz, 2H), 8.12-8.21 (m, 3H), 7.81-7.82 (m, 1H), 7.56-7.63 (m, 2H), 7.39-7.55 (m, 2H), 7.25-7.26 (m, 4H), 7.03-7.13 (m, 2H), 6.27-6.28 (m, 1H), 3.52-3.78 (m, 2H).

Example 366: (S*)-5-(3-Chloro-6-(difluoromethyl)-2-fluorophenyl)-2-(2-(4-fluorophenyl)-1-(4-(1-oxidopyridin-4-yl)-1H-pyrazol-1-yl)ethyl)pyridine 1-oxide

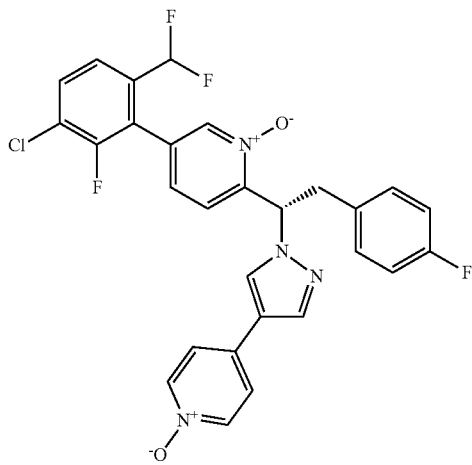

LC/MS: mass calculated for C$_{28}$H$_{19}$ClF$_4$N$_4$O$_2$: 554.11, measured (ES, m/z): 555.10 [M+H]$^+$. $^1$H NMR (400 MHz, DMSO-d$_6$) δ 8.56 (dd, J=5.9, 1.2 Hz, 2H), 8.12-8.22 (m, 3H), 7.89-7.90 (m, 1H), 7.56-7.65 (m, 3H), 7.36-7.50 (m, 2H), 7.21-7.29 (m, 2H), 7.01-7.14 (m, 2H), 6.78-7.02 (m, 1H), 6.26 (dd, J=10.3, 4.0 Hz, 1H), 3.50-3.79 (m, 2H).

Example 367: (S*)-5-(3-Chloro-6-(difluoromethoxy)-2-fluorophenyl)-2-(2-(4-fluorophenyl)-1-(4-(1-oxidopyridin-4-yl)-1H-pyrazol-1-yl)ethyl)pyridine 1-oxide

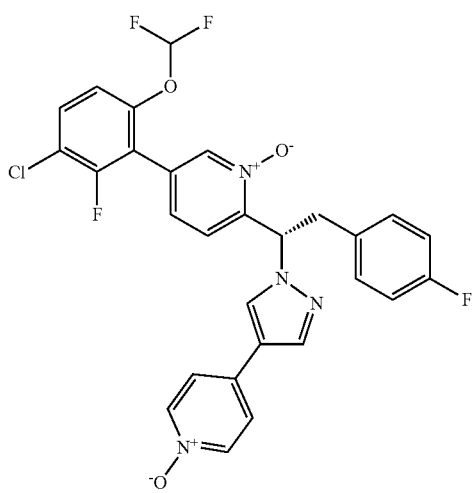

LC/MS: mass calculated C$_{28}$H$_{19}$ClF$_4$N$_4$O$_3$: 570.11, measured (ES, m/z): 571.15 [M+H]$^+$. $^1$H NMR (400 MHz, DMSO-d$_6$) δ 8.56 (d, J=6.1 Hz, 2H), 8.12-8.21 (m, 3H), 7.81-7.82 (m, 1H), 7.56-7.63 (m, 2H), 7.42-7.54 (m, 2H), 7.25-7.26 (m, 4H), 7.03-7.13 (m, 2H), 6.27 (dd, J=10.3, 4.2 Hz, 1H), 3.51-3.71 (m, 2H).

Example 368: (R*)-5-(3-Chloro-6-(difluoromethyl)-2-fluorophenyl)-2-(2-(4-fluorophenyl)-1-(4-(1-oxidopyridin-4-yl)-1H-pyrazol-1-yl)ethyl)pyridine 1-oxide

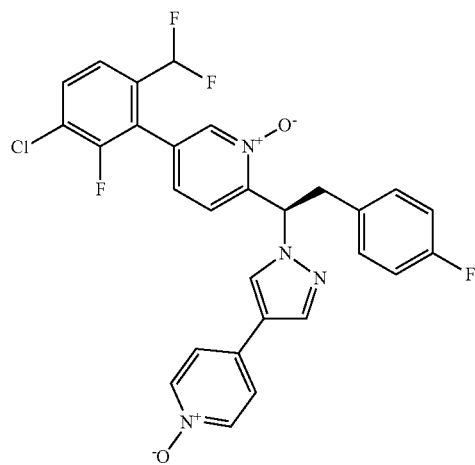

LC/MS: mass calculated C$_{28}$H$_{19}$ClF$_4$N$_4$O$_2$: 554.11, measured (ES, m/z): 555.10 [M+H]$^+$. $^1$H NMR (400 MHz, DMSO-d$_6$) δ 8.56 (dd, J=5.6, 1.1 Hz, 2H), 8.12-8.22 (m, 3H), 7.85-7.94 (m, 1H), 7.56-7.65 (m, 3H), 7.33-7.54 (m, 2H), 7.20-7.29 (m, 2H), 7.01-7.13 (m, 2H), 6.78-7.02 (m, 1H), 6.27 (dd, J=10.4, 4.0 Hz, 1H), 3.43-3.78 (m, 2H).

Example 369: (R*)-2-(2-((tert-Butoxycarbonyl)(methyl)amino)-1-(4-(2-fluoropyridin-4-yl)-1H-pyrazol-1-yl)ethyl)-5-(3-chloro-2-fluoro-6-(1H-tetrazol-1-yl)phenyl)pyridine 1-oxide

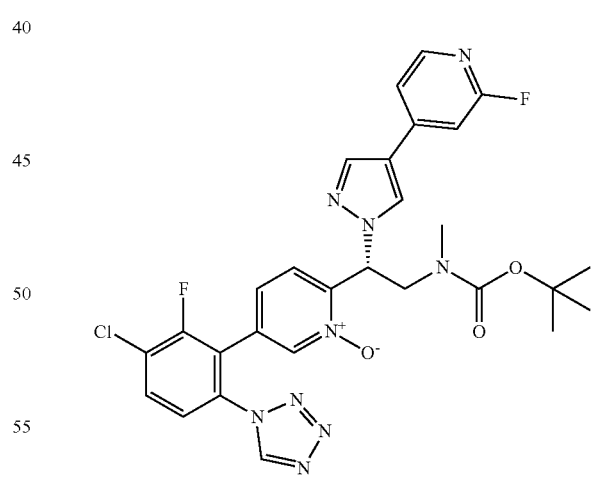

LC/MS: mass calculated for C$_{28}$H$_{26}$ClF$_2$N$_9$O$_3$: 609.2, measured (ES, m/z): 610.20 [M+H]$^+$. $^1$H NMR (300 MHz, DMSO-d$_6$) d 9.68 (s, 1H), 8.72 (s, 1H), 8.44 (d, J=1.6 Hz, 1H), 8.20-8.35 (m, 1H), 8.12-8.20 (m, 1H), 8.05 (dd, J=8.7, 7.7 Hz, 1H), 7.74 (dd, J=8.7, 1.6 Hz, 1H), 7.65 (d, J=8.3 Hz, 1H), 7.57 (d, J=5.4 Hz, 1H), 7.42 (s, 1H), 7.17-7.26 (m, 1H), 6.22-6.38 (m, 1H), 3.76-4.19 (m, 2H), 2.60-2.80 (m, 3H), 1.27 (s, 9H). $^{19}$F NMR (282 MHz, DMSO-d$_6$) d −69.24, −112.66.

Example 370: (S*)-2-(2-((tert-Butoxycarbonyl)(methyl)amino)-1-(4-(2-fluoropyridin-4-yl)-1H-pyrazol-1-yl)ethyl)-5-(3-chloro-2-fluoro-6-(1H-tetrazol-1-yl)phenyl)pyridine 1-oxide

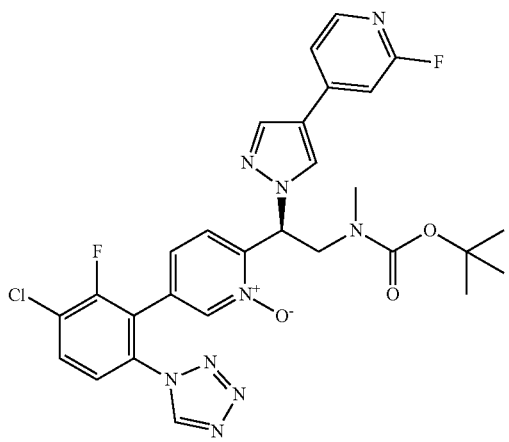 [SMILES: CN(C[C@@H](c1ccc(-c2c(-n3cnnn3)ccc(Cl)c2F)c[n+]1[O-])n1cc(-c2ccnc(F)c2)cn1)C(=O)OC(C)(C)C]

LC/MS: mass calculated for $C_{28}H_{26}ClF_2N_9O_3$: 609.2, measured (ES, m/z): 610.20 [M+H]$^+$. $^1$H NMR (300 MHz, DMSO-d$_6$) d 9.68 (s, 1H), 8.72 (s, 1H), 8.44 (d, J=1.5 Hz, 1H), 8.18-8.32 (m, 1H), 8.16 (d, J=5.3 Hz, 1H), 7.99-8.11 (m, 1H), 7.74 (dd, J=8.7, 1.6 Hz, 1H), 7.65 (d, J=8.2 Hz, 1H), 7.57 (d, J=5.3 Hz, 1H), 7.42 (s, 1H), 7.22 (d, J=8.4 Hz, 1H), 6.20-6.38 (m, 1H), 3.73-4.23 (m, 2H), 2.60-2.80 (m, 3H), 1.27 (s, 9H). $^{19}$F NMR (282 MHz, DMSO-d$_6$) d −69.23, −112.66.

Example 371: (R*)-5-(3-Chloro-2-fluoro-6-(1H-tetrazol-1-yl)phenyl)-2-(1-(4-(2-fluoropyridin-4-yl)-1H-pyrazol-1-yl)-2-((methoxycarbonyl)(methyl)amino)ethyl)pyridine 1-oxide

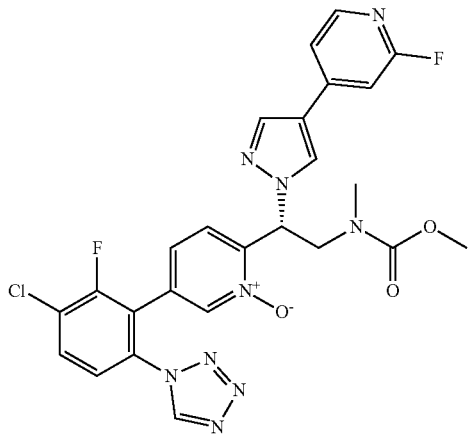 [SMILES: COC(=O)N(C)C[C@H](c1ccc(-c2c(-n3cnnn3)ccc(Cl)c2F)c[n+]1[O-])n1cc(-c2ccnc(F)c2)cn1]

LC/MS: mass calculated for $C_{25}H_{20}ClF_2N_9O_3$: 567.1, measured (ES, m/z): 568.10 [M+H]$^+$. $^1$H NMR (300 MHz, DMSO-d$_6$) d 9.68 (s, 1H), 8.75 (s, 1H), 8.45 (d, J=1.4 Hz, 1H), 8.23 (s, 1H), 8.16 (d, J=5.3 Hz, 1H), 8.05 (dd, J=8.7, 7.7 Hz, 1H), 7.75 (dd, J=8.7, 1.6 Hz, 1H), 7.66 (d, J=8.5 Hz, 1H), 7.57 (d, J=5.4 Hz, 1H), 7.42 (s, 1H), 7.20 (d, J=8.0 Hz, 1H), 6.20-6.40 (m, 1H), 3.85-4.20 (m, 2H), 3.35-3.62 (m, 3H), 2.60-2.80 (m, 3H). $^{19}$F NMR (282 MHz, DMSO-d$_6$) d −69.20, −112.67.

Example 372: (S*)-5-(3-Chloro-2-fluoro-6-(1H-tetrazol-1-yl)phenyl)-2-(1-(4-(2-fluoropyridin-4-yl)-1H-pyrazol-1-yl)-2-((methoxycarbonyl)(methyl)amino)ethyl)pyridine 1-oxide

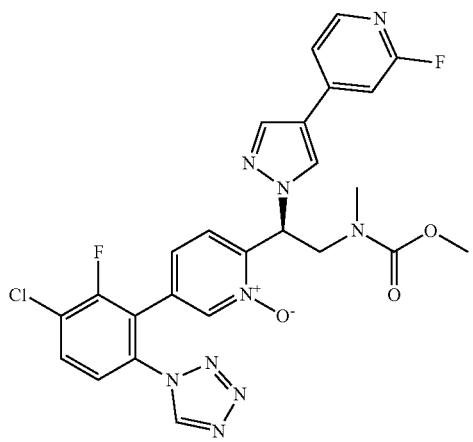 [SMILES: COC(=O)N(C)C[C@@H](c1ccc(-c2c(-n3cnnn3)ccc(Cl)c2F)c[n+]1[O-])n1cc(-c2ccnc(F)c2)cn1]

LC/MS: mass calculated for $C_{25}H_{20}ClF_2N_9O_3$: 567.1, measured (ES, m/z): 568.10 [M+H]$^+$. $^1$H NMR (300 MHz, DMSO-d$_6$) δ 9.68 (s, 1H), 8.75 (s, 1H), 8.45 (s, 1H), 8.23 (s, 1H), 8.16 (d, J=5.4 Hz, 1H), 8.00-8.11 (m, 1H), 7.73-7.78 (m, 1H), 7.62-7.70 (m, 1H), 7.54-7.59 (m, 1H), 7.41 (s, 1H), 7.18-7.24 (m, 1H), 6.20-6.34 (m, 1H), 3.75-4.25 (m, 2H), 3.38-3.47 (m, 3H), 2.68 (d, J=12.8 Hz, 3H). $^{19}$F NMR (282 MHz, DMSO-d$_6$) δ −69.20, −112.67.

Example 373: 5-(3-Chloro-2-fluoro-6-(1H-tetrazol-1-yl)phenyl)-2-(1-(4-(2-fluoropyridin-4-yl)-1H-pyrazol-1-yl)-2-(3-(trifluoromethyl)-1H-pyrazol-1-yl)ethyl)pyridine 1-oxide

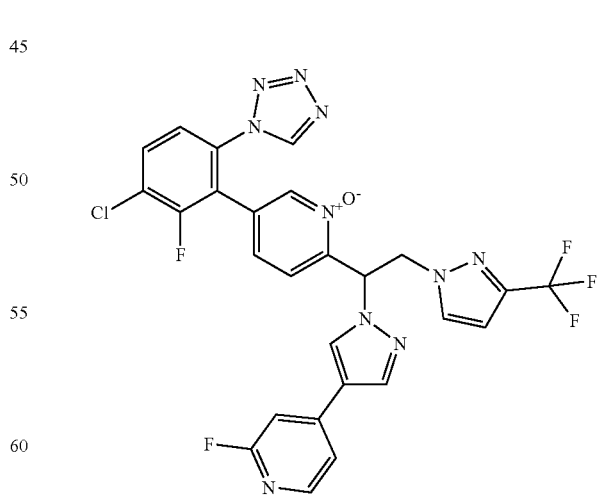

LC/MS: mass calculated for $C_{26}H_{16}ClF_5N_{10}O$: 614.11, measured (ES, m/z): 615.15[M+H]$^+$. $^1$H NMR (300 MHz, DMSO-d$_6$) δ 9.69 (s, 1H), 8.61 (s, 1H), 8.52 (d, J=1.5 Hz, 1H), 8.25 (s, 1H), 8.15 (d, J=5.3 Hz, 1H), 8.08-8.09 (m, 1H), 7.77 (dd, J=8.8, 1.6 Hz, 1H), 7.66 (d, J=1.9 Hz, 1H), 7.47-7.56 (m, 2H), 7.38 (s, 1H), 7.24 (dd, J=8.3, 1.7 Hz, 1H), 6.79-6.95 (m, 2H), 5.18-5.20 (m, 1H), 5.05 (dd, J=13.8, 4.5 Hz, 1H). $^{19}$F NMR (282 MHz, DMSO-$d_6$) δ –57.82, –69.12, –74.59, –112.59.

Example 374: 5-(3-Chloro-2-fluoro-6-(1H-tetrazol-1-yl)phenyl)-2-(2-(2-oxopyridin-1(2H)-yl)-1-(4-(2-(trifluoromethyl)pyridin-4-yl)-1H-pyrazol-1-yl)ethyl)pyridine 1-oxide

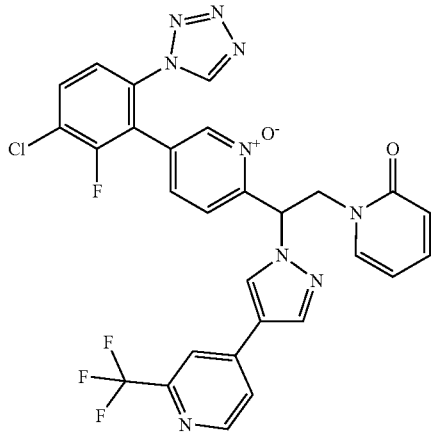

LC/MS: mass calculated for $C_{28}H_{18}ClF_4N_9O_2$: 623.12, measured (ES, m/z): 624.10 [M+H]$^+$. $^1$H NMR (400 MHz, DMSO-$d_6$) δ 9.70 (s, 1H), 8.75 (s, 1H), 8.65 (d, J=5.1 Hz, 1H), 8.48 (d, J=1.6 Hz, 1H), 8.35 (s, 1H), 8.04-8.14 (m, 2H), 7.85-7.90 (m, 1H), 7.74-7.83 (m, 2H), 7.32-7.40 (m, 1H), 7.24-7.30 (m, 1H), 7.13-7.19 (m, 1H), 6.53 (t, J=7.4 Hz, 1H), 6.39 (d, J=9.0 Hz, 1H), 6.00-6.08 (m, 1H), 4.76 (d, J=7.4 Hz, 2H). $^{19}$F NMR (376 MHz, DMSO-$d_6$) δ –66.51, –74.78, –112.58.

Example 375: 5-(3-Chloro-2-fluoro-6-(1H-tetrazol-1-yl)phenyl)-2-(1-(4-(2-cyanopyridin-4-yl)-1H-pyrazol-1-yl)-2-(1-methyl-1H-pyrazol-3-yl)ethyl)pyridine 1-oxide

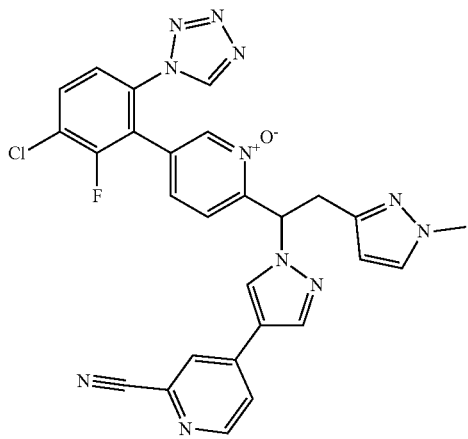

LC/MS: mass calculated for $C_{27}H_{19}ClFN_{11}O$: 567.14, measured (ES, m/z): 568.10 [M+H]$^+$. $^1$H NMR (400 MHz, DMSO-$d_6$) δ 9.69 (s, 1H), 8.80 (s, 1H), 8.65 (d, J=5.2 Hz, 1H), 8.46 (d, J=1.6 Hz, 1H), 8.27-8.35 (m, 2H), 8.03-8.11 (m, 1H), 7.89-7.93 (m, 1H), 7.74-7.78 (m, 1H), 7.47 (d, J=2.2 Hz, 1H), 7.37-7.41 (m, 1H), 7.15-7.20 (m, 1H), 6.33 (t, J=7.5 Hz, 1H), 5.81 (d, J=2.2 Hz, 1H), 3.73 (s, 3H), 3.53 (d, J=7.5 Hz, 2H). $^{19}$F NMR (376 MHz, DMSO-$d_6$) δ –74.54, –112.67.

Example 376: 5-(3-Chloro-2-fluoro-6-(1H-tetrazol-1-yl)phenyl)-2-(2-(4-fluoro-1H-pyrazol-1-yl)-1-(4-(1-oxidopyridin-4-yl)-1H-pyrazol-1-yl)ethyl)pyridine 1-oxide

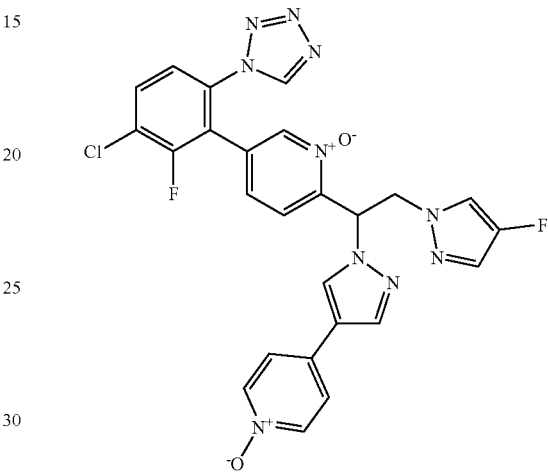

LC/MS: mass calculated for $C_{25}H_{17}ClF_2N_{10}O_2$: 562.12, measured (ES, m/z): 563.10 [M+H]$^+$. $^1$H NMR (400 MHz, DMSO-$d_6$) δ 9.69 (s, 1H), 8.47-8.54 (m, 2H), 8.13-8.27 (m, 3H), 8.04-8.10 (m, 1H), 7.73-7.79 (m, 1H), 7.63-7.70 (m, 1H), 7.56-7.63 (m, 2H), 7.43-7.48 (m, 1H), 7.38-7.42 (m, 1H), 7.19-7.24 (m, 1H), 7.49-7.54 (m, 1H), 4.83-5.07 (m, 2H). $^{19}$F NMR (376 MHz, DMSO-$d_6$) δ –112.62, –177.79.

Example 377: (R*)-4-(1-(1-(5-(3-Chloro-2-fluoro-6-(1H-tetrazol-1-yl)phenyl)-1-oxidopyridin-2-yl)-2-(2-oxopyrrolidin-1-yl)ethyl)-1H-pyrazol-4-yl)-2-(difluoromethyl)pyridine 1-oxide

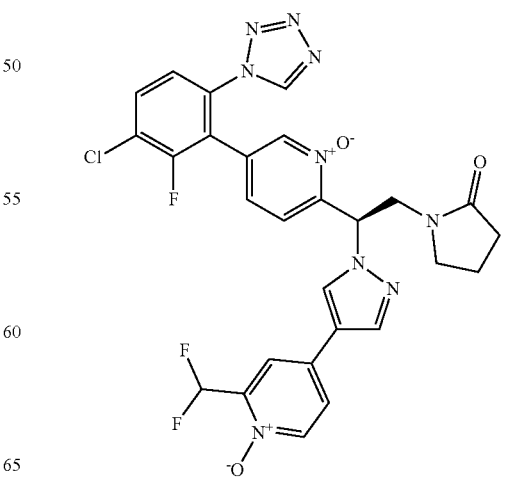

LC/MS: mass calculated for $C_{27}H_{21}ClF_3N_9O_3$: 611.14, measured (ES, m/z): 612.05 [M+H]$^+$. $^1$H NMR (400 MHz, DMSO-d$_6$) δ 9.57 (s, 1H), 8.66 (s, 1H), 8.35-8.40 (m, 1H), 8.28 (d, J=6.8 Hz, 1H), 8.17 (s, 1H), 7.92-8.01 (m, 2H), 7.85-7.89 (m, 1H), 7.58-7.70 (m, 2H), 6.98-7.32 (m, 2H), 6.31-6.38 (m, 1H), 3.97-4.10 (m, 2H), 3.29-3.38 (m, 1H), 2.88-2.99 (m, 1H), 2.15-2.22 (m, 2H), 1.78-1.91 (m, 2H). $^{19}$F NMR (376 MHz, DMSO-d$_6$) δ −112.66, −122.78.

Example 378: (S*)-4-(1-(1-(5-(3-Chloro-2-fluoro-6-(1H-tetrazol-1-yl)phenyl)-1-oxidopyridin-2-yl)-2-(2-oxopyrrolidin-1-yl)ethyl)-1H-pyrazol-4-yl)-2-(difluoromethyl)pyridine 1-oxide

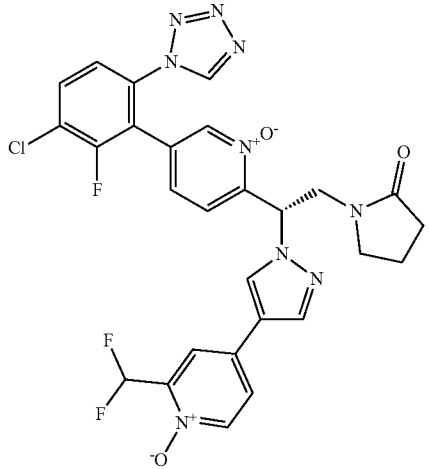

LC/MS: mass calculated for $C_{27}H_{21}ClF_3N_9O_3$: 611.14, measured (ES, m/z): 612.1 [M+H]$^+$. $^1$H NMR (400 MHz, DMSO-d$_6$) δ 9.57 (s, 1H), 8.65 (s, 1H), 8.36 (d, J=1.3 Hz, 1H), 8.28 (d, J=6.9 Hz, 1H), 8.17 (s, 1H), 7.92-8.00 (m, 2H), 7.81 (dd, J=6.8, 2.6 Hz, 1H), 7.58-7.69 (m, 2H), 6.98-7.34 (m, 2H), 6.26-6.34 (m, 1H), 4.01-4.12 (m, 2H), 3.28-3.29 (m, 1H), 2.91-2.99 (m, 1H), 2.14-2.21 (m, 2H), 1.83-1.85 (m, 2H). $^{19}$F NMR (376 MHz, DMSO-d$_6$) δ −112.66, −122.78.

Example 379A: (R*)-5-(3-Chloro-2-fluoro-6-(1H-tetrazol-1-yl)phenyl)-2-(2-(2-oxopyrrolidin-1-yl)-1-(4-(2-(trifluoromethyl)pyridin-4-yl)-1H-pyrazol-1-yl)ethyl)pyridine 1-oxide

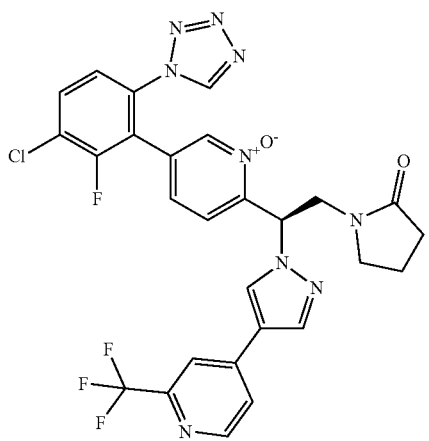

LC/MS: mass calculated for $C_{27}H_{20}ClF_4N_9O_2$: 613.1, measured (ES, m/z): 614.1 [M+H]$^+$. $^1$H NMR (400 MHz, DMSO-d$_6$) δ 9.69 (s, 1H), 8.91 (s, 1H), 8.69 (d, J=5.2 Hz, 1H), 8.47 (d, J=1.6 Hz, 1H), 8.34 (s, 1H), 8.15-8.16 (m, 1H), 8.07-8.09 (m, 1H), 7.93 (dd, J=5.4, 1.7 Hz, 1H), 7.77 (dd, J=8.7, 1.5 Hz, 1H), 7.63 (d, J=8.3 Hz, 1H), 7.23 (dd, J=8.3, 1.7 Hz, 1H), 6.34-6.36 (m, 1H), 4.04-4.11 (m, 2H), 3.30-3.32 (m, 1H), 2.89-3.01 (m, 1H), 2.05-2.23 (m, 2H), 1.83-1.86 (m, 2H). $^{19}$F NMR (376 MHz, DMSO-d$_6$) δ −66.51, −112.66.

Example 379B: (S*)-5-(3-Chloro-2-fluoro-6-(1H-tetrazol-1-yl)phenyl)-2-(2-(2-oxopyrrolidin-1-yl)-1-(4-(2-(trifluoromethyl)pyridin-4-yl)-1H-pyrazol-1-yl)ethyl)pyridine 1-oxide

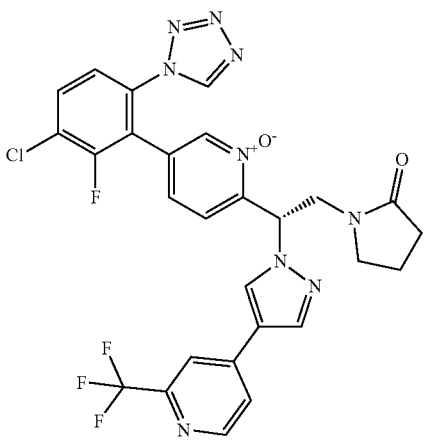

LC/MS: mass calculated for $C_{27}H_{20}ClF_4N_9O_2$: 613.1, measured (ES, m/z): 614.1 [M+H]$^+$. $^1$H NMR (400 MHz, DMSO-d$_6$) δ 9.69 (s, 1H), 8.91 (s, 1H), 8.69 (d, J=5.2 Hz, 1H), 8.47 (d, J=1.6 Hz, 1H), 8.34 (s, 1H), 8.15 (d, J=1.7 Hz, 1H), 8.07-8.09 (m, 1H), 7.93 (dd, J=5.2, 1.7 Hz, 1H), 7.77 (dd, J=8.7, 1.5 Hz, 1H), 7.63 (d, J=8.3 Hz, 1H), 7.23 (dd, J=8.3, 1.7 Hz, 1H), 6.34-6.36 (m, 1H), 4.04-4.09 (m, 2H), 3.30-3.33 (m, 1H), 2.89-2.99 (m, 1H), 2.05-2.21 (m, 2H), 1.82-1.91 (m, 2H). $^{19}$F NMR (376 MHz, DMSO-d$_6$) δ −66.51, −112.66.

Example 380: 5-(3-Chloro-2-fluoro-6-(1H-tetrazol-1-yl)phenyl)-2-(1-(4-(2-(difluoromethyl)pyridin-4-yl)-1H-pyrazol-1-yl)-2-(2-oxopyrrolidin-1-yl)ethyl)pyridine 1-oxide

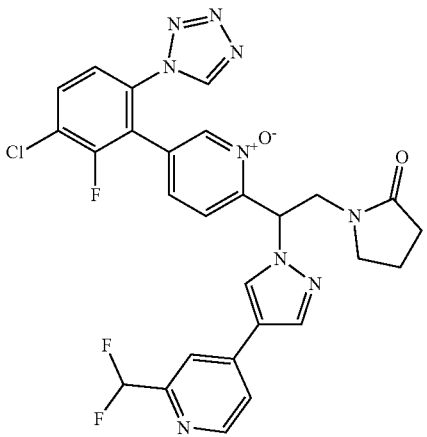

LC/MS: mass calculated for $C_{27}H_{21}ClF_3N_9O_2$: 595.15, measured (ES, m/z): MH+: 596.1 [M+H]$^+$. $^1$H NMR (400 MHz, DMSO-d$_6$) δ 9.69 (s, 1H), 8.85 (s, 1H), 8.61 (d, J=5.2 Hz, 1H), 8.46 (d, J=1.6 Hz, 1H), 8.28 (s, 1H), 8.07-8.09 (m, 1H), 7.93 (d, J=1.5 Hz, 1H), 7.73-7.82 (m, 2H), 7.61 (d, J=8.3 Hz, 1H), 7.22 (dd, J=8.2, 1.7 Hz, 1H), 6.81-7.06 (m, 1H), 6.34-6.36 (m, 1H), 3.94-4.17 (m, 2H), 3.21-3.31 (m, 1H), 2.90-2.98 (m, 1H), 2.06-2.21 (m, 2H), 1.82-1.91 (m, 2H). $^{19}$F NMR (376 MHz, DMSO-d$_6$) δ −73.47, −112.67, −115.37.

Example 381: 2-(3-(tert-Butoxy)-1-(4-(pyrimidin-4-yl)-1H-pyrazol-1-yl)propyl)-5-(3-Chloro-2-fluoro-6-(1H-tetrazol-1-yl)phenyl)pyridine 1-oxide

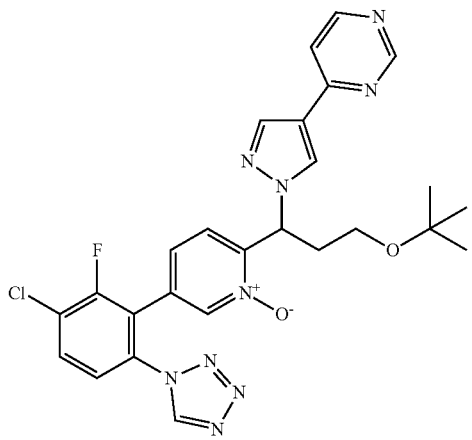 [SMILES: CC(C)(C)OCCC(c1ccc(-c2c(-n3cnnn3)ccc(Cl)c2F)c[n+]1[O-])n1cc(-c2ccncn2)cn1]

LC/MS: mass calculated for $C_{26}H_{25}ClFN_9O_2$: 549.2, measured (ES, m/z): 550.1 [M+H]$^+$. $^1$H NMR (300 MHz, DMSO-d$_6$) δ 9.69 (s, 1H), 9.07 (d, J=1.3 Hz, 1H), 8.67-8.79 (m, 2H), 8.42 (s, 1H), 8.25 (s, 1H), 8.06-8.08 (m, 1H), 7.71-7.83 (m, 2H), 7.45 (d, J=8.3 Hz, 1H), 7.14-7.23 (m, 1H), 6.18-6.29 (m, 1H), 3.26-3.35 (m, 1H), 3.15-3.16 (m, 1H), 2.44-2.45 (m, 2H), 1.02 (s, 9H). $^{19}$F NMR (282 MHz, DMSO-d$_6$) δ −73.57, −112.71.

Example 382: 5-(3-Chloro-2-fluoro-6-(1H-tetrazol-1-yl)phenyl)-2-(3-(difluoromethoxy)-1-(4-(pyrimidin-4-yl)-1H-pyrazol-1-yl)propyl)pyridine 1-oxide

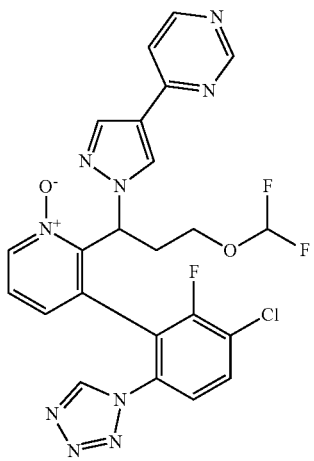 [SMILES: [O-][n+]1cccc(Cc2c(-n3cnnn3)ccc(Cl)c2F)c1C(CCOC(F)F)n1cc(-c2ccncn2)cn1]

LC/MS: mass calculated for $C_{23}H_{17}ClF_3NO_2$: 543.11, measured (ES, m/z): 544.1 [M+H]$^+$. $^1$H NMR (400 MHz, DMSO-d$_6$) δ 9.68 (s, 1H), 9.07 (d, J=1.4 Hz, 1H), 8.77 (s, 1H), 8.72 (d, J=5.4 Hz, 1H), 8.45 (d, J=1.6 Hz, 1H), 8.31 (s, 1H), 8.01-8.10 (m, 1H), 7.72-7.81 (m, 2H), 7.33 (d, J=8.2 Hz, 1H), 7.19 (dd, J=8.3, 1.7 Hz, 1H), 6.41-6.83 (m, 1H), 6.23 (dd, J=10.3, 4.3 Hz, 1H), 3.57-3.95 (m, 2H), 2.57-2.77 (m, 2H). $^{19}$F NMR (376 MHz, DMSO-d$_6$) δ −74.20, −83.28, −112.66.

Example 383: 5-(3-Chloro-2-fluoro-6-(1H-tetrazol-1-yl)phenyl)-2-(2-cyclopropyl-1-(4-(2-methylpyrimidin-4-yl)-1H-pyrazol-1-yl)ethyl)pyridine 1-oxide

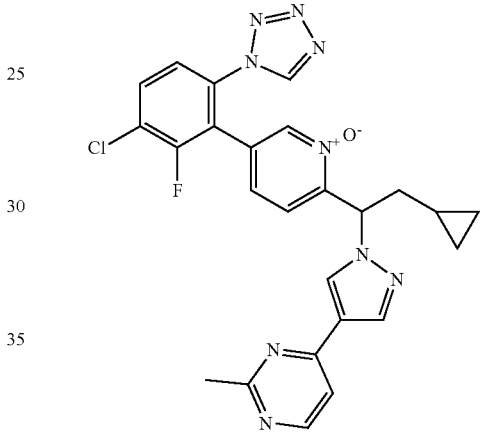

To a solution of 4-(1-(1-(5-(3-Chloro-2-fluoro-6-(1H-tetrazol-1-yl)phenyl)pyridin-2-yl)-2-cyclopropylethyl)-1H-pyrazol-4-yl)-2-methylpyrimidine (67.6 mg, 0.14 mmol) in DCM (4 mL) was added m-CPBA (45.3 mg, 0.20 mmol) and the reaction mixture was stirred at room temperature for 2 h. It was then quenched with sodium thiosulfate solution and the solvent was removed under reduced pressure. The residue was purified by Gilson HPLC to yield 5-(3-chloro-2-fluoro-6-(1H-tetrazol-1-yl)phenyl)-2-(2-cyclopropyl-1-(4-(2-methylpyrimidin-4-yl)-1H-pyrazol-1-yl)ethyl)pyridine 1-oxide as a white solid.

LC/MS: mass calculated for $C_{25}H_{21}ClFN_9O$: 517.2, measured (ES, m/z): 518.3 [M+H]$^+$. $^1$H NMR (400 MHz, CD$_3$OD) δ 9.39 (s, 1H), 8.88 (s, 1H), 8.65-8.74 (m, 1H), 8.37 (bd, J=3.42 Hz, 2H), 7.84-7.97 (m, 2H), 7.57-7.68 (m, 2H), 7.24-7.35 (m, 1H), 6.18-6.35 (m, 1H), 2.80 (s, 3H), 2.41-2.55 (m, 1H), 2.03-2.16 (m, 1H), 0.60-0.74 (m, 1H), 0.35-0.48 (m, 2H), 0.15-0.23 (m, 1H), 0.00-0.06 (m, 1H).

Example 384: 4-(1-(1-(5-(3-Chloro-2-fluoro-6-(1H-tetrazol-1-yl)phenyl)-1-oxidopyridin-2-yl)-2-cyclopropylethyl)-1H-pyrazol-4-yl)-2-methylpyrimidine 1-oxide

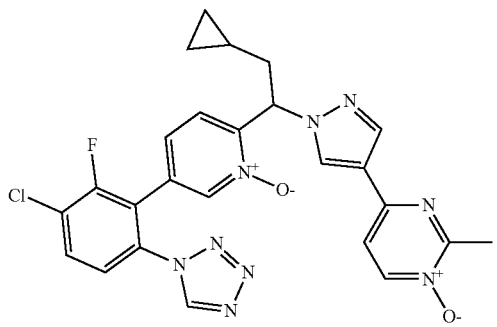 [SMILES: Cc1nc(-c2cnn(C(CC3CC3)c3ccc(-c4c(-n5cnnn5)ccc(Cl)c4F)c[n+]3[O-])c2)cc[n+]1[O-]]

The title compound was prepared as a white solid. LC/MS: mass calculated for $C_{25}H_{21}ClFN_9O_2$: 533.2, measured 534.3 [M+H]$^+$. $^1$H NMR (400 MHz, CD$_3$OD) δ 9.38 (s, 1H), 8.60-8.68 (m, 1H), 8.45-8.54 (m, 1H), 8.32-8.39 (m, 1H), 8.22 (s, 1H), 7.86-7.96 (m, 1H), 7.71-7.77 (m, 1H), 7.58-7.64 (m, 1H), 7.50-7.56 (m, 1H), 7.18-7.35 (m, 1H), 6.20-6.36 (m, 1H), 2.73 (s, 3H), 2.44-2.55 (m, 1H), 1.98-2.11 (m, 1H), 0.62-0.75 (m, 1H), 0.32-0.48 (m, 2H), 0.13-0.25 (m, 1H), 0.00-0.06 (m, 1H).

Example 385: (S*)-5-(3-Chloro-2-fluoro-6-(1H-tetrazol-1-yl)phenyl)-2-(1-(4-(2-(difluoromethyl)pyridin-4-yl)-1H-pyrazol-1-yl)-2-(2-oxopyridin-1(2H)-yl)ethyl)pyridine 1-oxide

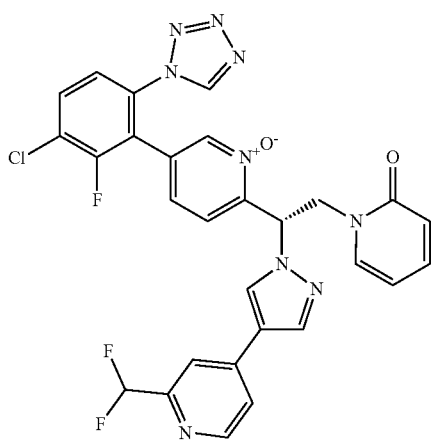

LC/MS: mass calculated for $C_{28}H_{19}ClF_3N_9O_3$ 621.957; measured (ES, m/z): 622.10 [M+H]$^+$. $^1$H NMR (300 MHz, DMSO-d$_6$) δ 9.67 (s, 1H), 8.62 (s, 1H), 8.45 (d, J=1.4 Hz, 1H), 8.30 (d, J=6.8 Hz, 1H), 8.23 (s, 1H), 8.05 (dd, J=8.7, 7.8 Hz, 1H), 7.94 (d, J=2.6 Hz, 1H), 7.70-7.82 (m, 3H), 7.18-7.40 (m, 3H), 7.14 (dd, J=7.1, 2.0 Hz, 1H), 6.48-6.49 (m, 1H), 6.33-6.42 (m, 1H), 6.03-6.05 (m, 1H), 4.73 (d, J=7.4 Hz, 2H). $^{19}$F NMR (282 MHz, DMSO-d$_6$) δ −73.48, −112.61, −122.80.

Example 386: (S*)-4-(1-(1-(5-(3-Chloro-2-fluoro-6-(1H-tetrazol-1-yl)phenyl)pyridin-2-yl)-2-(2-oxopyridin-1(2H)-yl)ethyl)-1H-pyrazol-4-yl)-2-(difluoromethyl)pyridine 1-oxide

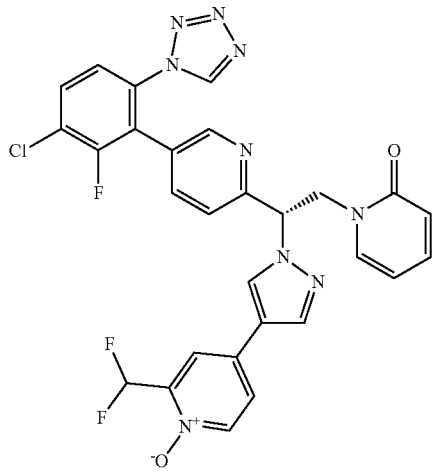

LC/MS: mass calculated for $C_{28}H_{19}ClF_3N_9O_2$: 605.13, measured (ES, m/z): 606.25 [M+H]$^+$. $^1$H NMR (300 MHz, DMSO-d$_6$) δ 9.61 (s, 1H), 8.70 (s, 1H), 8.45 (d, J=2.2 Hz, 1H), 8.33 (d, J=6.8 Hz, 1H), 8.24 (s, 1H), 7.98-8.03 (m, 1H), 7.92 (d, J=2.6 Hz, 1H), 7.69-7.75 (m, 3H), 7.28-7.42 (m, 1H), 7.14-7.24 (m, 3H), 6.33-6.43 (m, 1H), 5.95-6.08 (m, 2H), 4.94 (dd, J=13.3, 4.9 Hz, 1H), 4.50-4.70 (m, 1H). $^{19}$F NMR (282 MHz, DMSO-d$_6$) δ −113.40, −122.85.

Example 387: (R*)-5-(3-Chloro-2-fluoro-6-(1H-tetrazol-1-yl)phenyl)-2-(1-(4-(2-(difluoromethyl)pyridin-4-yl)-1H-pyrazol-1-yl)-2-(2-oxopyridin-1(2H)-yl)ethyl)pyridine 1-oxide

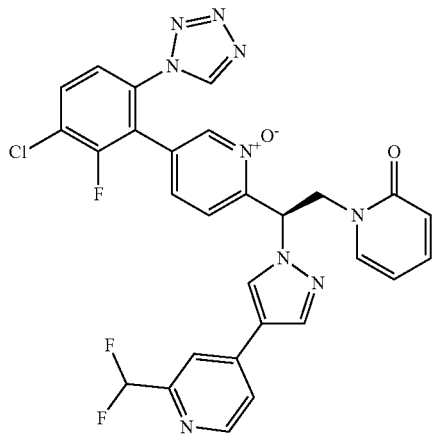

LC/MS: mass calculated for $C_{28}H_{19}ClF_3N_9O_2$: 605.13, measured (ES, m/z): 606.20 [M+H]$^+$. $^1$H NMR (300 MHz, DMSO-d$_6$) δ 9.61 (s, 1H), 8.71 (s, 1H), 8.41-8.48 (m, 1H), 8.33 (d, J=6.8 Hz, 1H), 8.24 (s, 1H), 8.00-8.05 (m, 1H), 7.92 (d, J=2.6 Hz, 1H), 7.64-7.80 (m, 3H), 7.28-7.42 (m, 1H), 7.13-7.24 (m, 3H), 6.38 (d, J=8.9 Hz, 1H), 5.95-6.10 (m, 2H), 4.94 (dd, J=13.4, 4.8 Hz, 1H), 4.50-4.70 (m, 1H). $^{19}$F NMR (282 MHz, DMSO-d$_6$) δ −113.40, −122.84.

Example 388: (R*)-4-(1-(1-(5-(3-Chloro-2-fluoro-6-(1H-tetrazol-1-yl)phenyl)pyridin-2-yl)-2-(2-oxopyridin-1(2H)-yl)ethyl)-1H-pyrazol-4-yl)-2-(difluoromethyl)pyridine 1-oxide

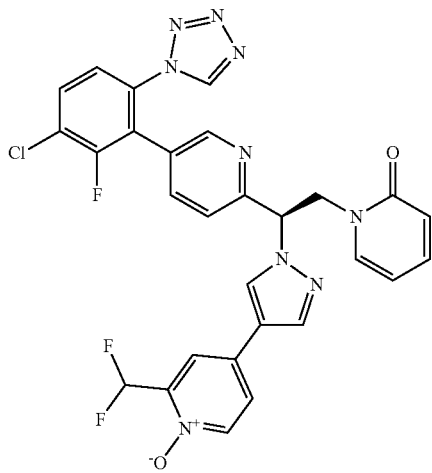

LC/MS: mass calculated for C$_{28}$H$_{19}$ClF$_3$N$_9$O$_3$: 621.13, measured (ES, m/z): 622.10 [M+H]$^+$. $^1$H NMR (300 MHz, DMSO-d$_6$) δ 9.67 (s, 1H), 8.62 (s, 1H), 8.45 (d, J=1.5 Hz, 1H), 8.30 (d, J=6.8 Hz, 1H), 8.23 (s, 1H), 7.99-8.11 (m, 1H), 7.94 (d, J=2.6 Hz, 1H), 7.70-7.82 (m, 3H), 7.18-7.40 (m, 3H), 7.05-7.17 (m, 1H), 6.42-6.57 (m, 1H), 6.37 (d, J=9.1 Hz, 1H), 5.99-6.05 (m, 1H), 4.73 (d, J=7.4 Hz, 2H). $^{19}$F NMR (282 MHz, DMSO-d$_6$) δ −112.61, −122.80.

Example 389: 5-(3-Chloro-2-fluoro-6-(1H-tetrazol-1-yl)phenyl)-2-(2-cyclopropyl-1-(3-methyl-4-(2-(trifluoromethyl)pyridin-4-yl)-1H-pyrazol-1-yl)ethyl)pyridine 1-oxide

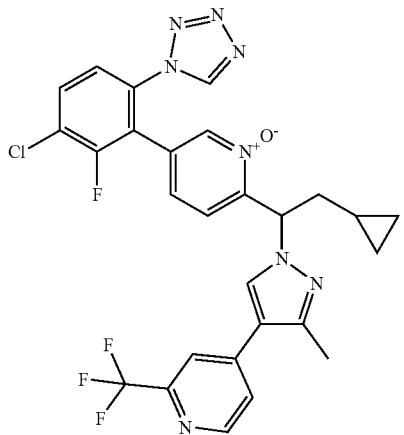

To a solution of 4-(1-(1-(5-(3-chloro-2-fluoro-6-(1H-tetrazol-1-yl)phenyl)pyridin-2-yl)-2-cyclopropylethyl)-3-methyl-1H-pyrazol-4-yl)-2-(trifluoromethyl)pyridine (132 mg, 0.23 mmol) in DCM (3 mL) was added m-CPBA (156 mg, 0.7 mol) and the reaction mixture was stirred at room temperature for 2 h. The solvent was removed under reduced pressure and the residue was purified by Gilson HPLC to yield 5-(3-chloro-2-fluoro-6-(1H-tetrazol-1-yl)phenyl)-2-(2-cyclopropyl-1-(3-methyl-4-(2-(trifluoromethyl)pyridin-4-yl)-1H-pyrazol-1-yl)ethyl)pyridine 1-oxide as a white solid.

LC/MS: mass calculated for C$_{27}$H$_{21}$ClF$_4$N$_8$O: 584.2, measured (ES, m/z): 585.2 [M+H]$^+$. $^1$H NMR (400 MHz, CD$_3$OD) δ 9.39 (s, 1H), 8.62-8.70 (m, 1H), 8.48 (s, 1H), 8.37 (d, J=0.98 Hz, 1H), 7.84-7.97 (m, 2H), 7.71-7.80 (m, 1H), 7.49-7.69 (m, 2H), 7.23-7.39 (m, 1H), 6.10-6.33 (m, 1H), 2.49 (s, 4H), 1.95-2.01 (m, 1H), 0.58-0.75 (m, 1H), 0.35-0.52 (m, 2H), 0.12-0.24 (m, 1H), 0.00 (s, 1H).

Example 390: 2-(1-(4-(2-Carboxypyridin-4-yl)-1H-pyrazol-1-yl)-2-cyclopropylethyl)-5-(3-chloro-6-(difluoromethoxy)-2-fluorophenyl)pyridine 1-oxide

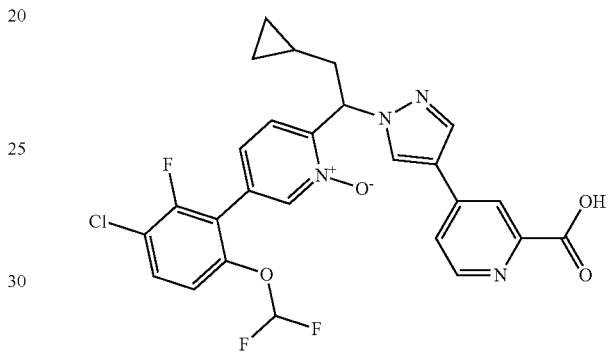

LC/MS: mass calculated for C$_{26}$H$_{20}$ClF$_3$N$_4$O$_4$: 544.11, measured (ES, m/z): 545.2 [M+H]$^+$. $^1$H NMR (300 MHz, DMSO-d$_6$) δ 8.95 (s, 1H), 8.60 (s, 1H), 8.52 (s, 1H), 8.20-8.28 (m, 2H), 7.75-7.90 (m, 2H), 7.00-7.51 (m, 4H), 6.19 (dd, J=10.0, 4.1 Hz, 3H), 2.70-2.72 (m, 1H), 1.90-2.10 (m, 1H), 0.55-0.66 (m, 1H), 0.30-0.50 (m, 2H), 0.12-0.21 (m, 1H), 0.02-0.06 (m, 1H). $^{19}$F NMR (282 MHz, DMSO-d$_6$) δ −82.63, −113.89.

Example 391: (R*)-2-(2-(((Benzyloxy)carbonyl)(methyl)amino)-1-(4-(2-(trifluoromethyl)pyridin-4-yl)-1H-pyrazol-1-yl)ethyl)-5-(3-chloro-2-fluoro-6-(1H-tetrazol-1-yl)phenyl)pyridine 1-oxide

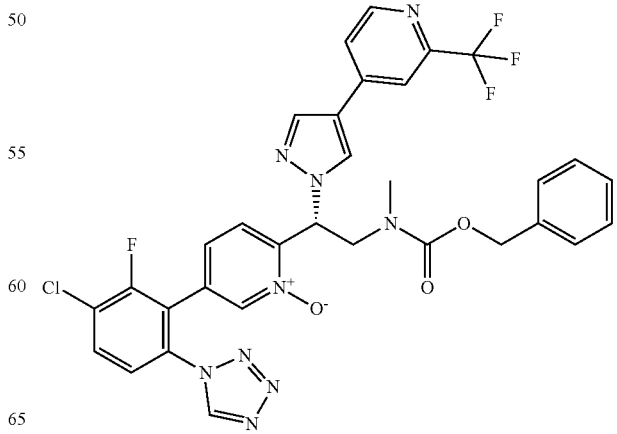

LC/MS: mass calculated for $C_{32}H_{24}ClF_4N_9O_3$: 693.16, measured (ES, m/z): 694.15 [M+H]$^+$. $^1$H NMR (300 MHz, DMSO-d$_6$) δ 9.68 (s, 1H), 8.79-8.91 (m, 1H), 8.66 (d, J=5.2 Hz, 1H), 8.46 (s, 1H), 8.28-8.35 (m, 1H), 7.99-8.15 (m, 2H), 7.82-7.95 (m, 1H), 7.72-7.80 (m, 1H), 7.60-7.70 (m, 1H), 7.19-7.32 (m, 6H), 6.29-6.40 (m, 1H), 4.85-5.04 (m, 2H), 4.18-4.38 (m, 1H), 3.90-4.01 (m, 1H), 2.73 (s, 3H). $^{19}$F NMR (282 MHz, DMSO-d$_6$) δ −66.53, −112.64.

Example 392: (S*)-2-(2-(((Benzyloxy)carbonyl)(methyl)amino)-1-(4-(2-(trifluoromethyl)pyridin-4-yl)-1H-pyrazol-1-yl)ethyl)-5-(3-chloro-2-fluoro-6-(1H-tetrazol-1-yl)phenyl)pyridine 1-oxide

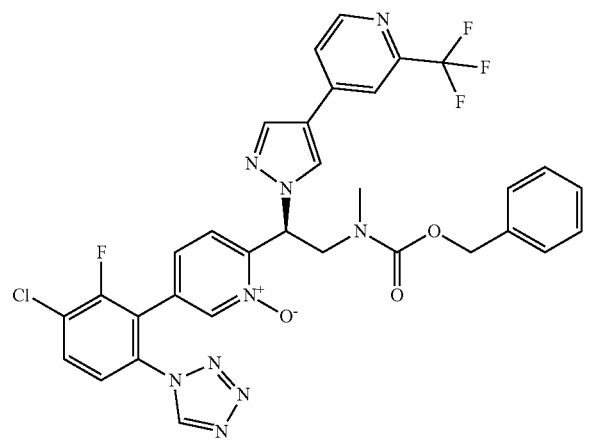 [SMILES: CN(C[C@@H](c1ccc(-c2c(-n3cnnn3)ccc(Cl)c2F)c[n+]1[O-])n1cc(-c2ccnc(C(F)(F)F)c2)cn1)C(=O)OCc1ccccc1]

LC/MS: mass calculated for $C_{32}H_{24}ClF_4N_9O_3$: 693.16, measured (ES, m/z): 694.1 [M+H]$^+$. $^1$H NMR (300 MHz, DMSO-d$_6$) δ 9.68 (s, 1H), 8.76-8.93 (m, 1H), 8.66 (d, J=5.2 Hz, 1H), 8.46 (s, 1H), 8.29 (d, J=11.2 Hz, 1H), 7.99-8.15 (m, 2H), 7.83-7.92 (m, 1H), 7.75 (dd, J=8.7, 1.5 Hz, 1H), 7.60-7.70 (m, 1H), 7.14-7.38 (m, 6H), 6.33 (s, 1H), 4.87-5.01 (m, 2H), 4.15-4.35 (m, 1H), 3.90-4.02 (m, 1H), 2.73 (s, 3H). $^{19}$F NMR (282 MHz, DMSO-d$_6$) δ −66.53, −112.64.

Example 393: (R)-5-(3-Chloro-2-fluoro-6-(1H-tetrazol-1-yl)phenyl)-2-(2-(1-methyl-1H-pyrazol-3-yl)-1-(4-(2-(trifluoromethyl)pyridin-4-yl)-1H-pyrazol-1-yl)ethyl)pyridine 1-oxide

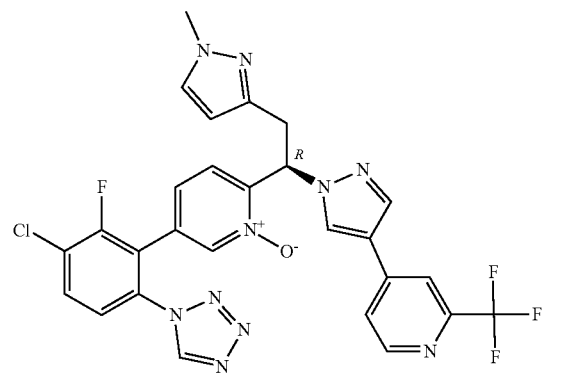

LC/MS: mass calculated for $C_{27}H_{19}ClF_4N_{10}O$: 610.14, measured (ES, m/z): 611.1 [M+H]$^+$. $^1$H NMR (300 MHz, DMSO-d$_6$) δ 9.69 (s, 1H), 8.85 (s, 1H), 8.65 (d, J=5.1 Hz, 1H), 8.42-8.50 (m, 1H), 8.31 (s, 1H), 8.01-8.12 (m, 2H), 7.88 (dd, J=5.0, 1.7 Hz, 1H), 7.74 (dd, J=8.7, 1.6 Hz, 1H), 7.45 (d, J=2.1 Hz, 1H), 7.36 (d, J=8.3 Hz, 1H), 7.16 (dd, J=8.3, 1.7 Hz, 1H), 6.25-6.40 (m, 1H), 5.78 (d, J=2.2 Hz, 1H), 3.71 (s, 3H), 3.52 (d, J=7.5 Hz, 2H). $^{19}$F NMR (282 MHz, DMSO-d$_6$) δ −66.53, −112.68.

Example 394: (S*)-5-(3-Chloro-2-fluoro-6-(1H-tetrazol-1-yl)phenyl)-2-(2-(1-methyl-1H-pyrazol-3-yl)-1-(4-(2-(trifluoromethyl)pyridin-4-yl)-1H-pyrazol-1-yl)ethyl)pyridine 1-oxide

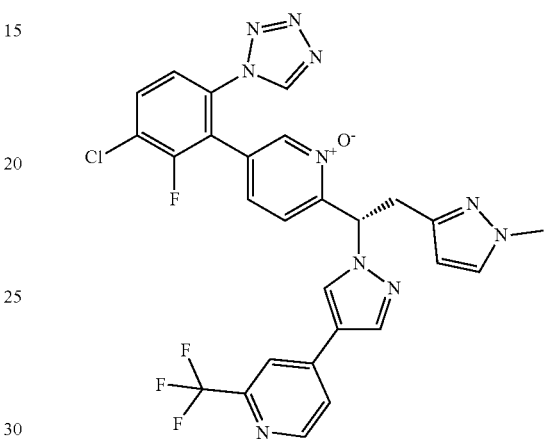

LC/MS: mass calculated for $C_{27}H_{19}ClF_4N_{10}O$: 610.14, measured (ES, m/z): 611.10 [M+H]$^+$. $^1$H NMR (300 MHz, DMSO-d$_6$) δ 9.67 (s, 1H), 8.85 (s, 1H), 8.65 (d, J=5.2 Hz, 1H), 8.41-8.48 (m, 1H), 8.31 (s, 1H), 8.01-8.12 (m, 2H), 7.86-7.92 (m, 1H), 7.72-7.80 (m, 1H), 7.45 (d, J=2.1 Hz, 1H), 7.35-7.40 (m, 1H), 7.15-7.21 (m, 1H), 6.31 (t, J=7.4 Hz, 1H), 5.78 (d, J=2.2 Hz, 1H), 3.71 (s, 3H), 3.52 (d, J=7.6 Hz, 2H). $^{19}$F NMR (282 MHz, DMSO-d$_6$) δ −66.53, −112.68.

Example 395: 5-(3-Chloro-2-fluoro-6-(1H-tetrazol-1-yl)phenyl)-2-(2-cyclopropyl-1-(4-(1-oxido-3-(trifluoromethyl)pyridin-4-yl)-1H-pyrazol-1-yl)ethyl)pyridine 1-oxide

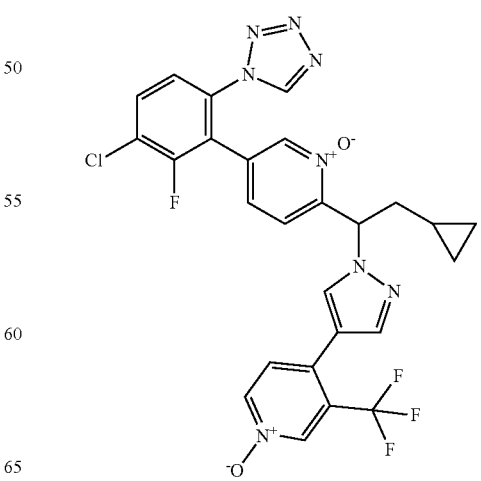

To a solution of 5-(3-chloro-2-fluoro-6-(1H-tetrazol-1-yl)phenyl)-2-(2-cyclopropyl-1-(4-(3-(trifluoromethyl)pyridin-4-yl)-1H-pyrazol-1-yl)ethyl)pyridine (65 mg, 0.12 mmol) in MeOH (3 mL) was added m-CPBA (131.3 mg, 0.59 mmol) and the reaction mixture was stirred at room temperature for 16 h. The mixture was subjected to Gilson HPLC directly to yield 5-(3-Chloro-2-fluoro-6-(1H-tetrazol-1-yl)phenyl)-2-(2-cyclopropyl-1-(4-(1-oxido-3-(trifluoromethyl)pyridin-4-yl)-1H-pyrazol-1-yl)ethyl)pyridine 1-oxide as a white solid.

LC/MS: mass calculated for $C_{26}H_{19}ClF_4N_8O_2$: 586.1, measured (ES, m/z): 587.3 [M+H]$^+$. $^1$H NMR (400 MHz, CD$_3$OD) δ 9.39 (s, 1H), 8.67-8.71 (m, 1H), 8.46-8.51 (m, 1H), 8.35-8.40 (m, 1H), 8.31 (s, 1H), 7.89 (s, 2H), 7.74-7.80 (m, 1H), 7.55-7.64 (m, 2H), 7.31 (dd, J=1.96, 8.31 Hz, 1H), 6.25 (dd, J=3.91, 10.27 Hz, 1H), 2.39-2.51 (m, 1H), 2.03 (s, 1H), 0.60-0.73 (m, 1H), 0.32-0.49 (m, 2H), 0.13-0.24 (m, 1H), −0.03-0.03 (m, 1H).

Example 396: 5-(3-Chloro-2-fluoro-6-(1H-tetrazol-1-yl)phenyl)-2-(2-cyclopropyl-1-(4-(3-(trifluoromethyl)pyridin-4-yl)-1H-pyrazol-1-yl)ethyl)pyridine 1-oxide

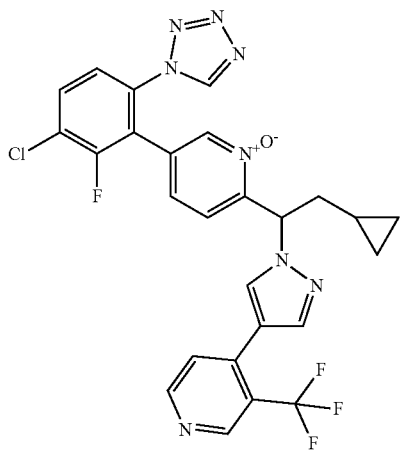

To a solution of 5-(3-chloro-2-fluoro-6-(1H-tetrazol-1-yl)phenyl)-2-(2-cyclopropyl-1-(4-(3-(trifluoromethyl)pyridin-4-yl)-1H-pyrazol-1-yl)ethyl)pyridine (55 mg, 0.1 mmol) in MeOH (1.6 mL) was added MeReO$_3$ 912.4 mg, 0.05 mmol), followed by 30% H$_2$O$_2$ (169 mg, 1.49 mmol) and the resulting mixture was stirred at room temperature for 1 h. The reaction mixture was subjected to Gilson HPLC to yield 5-(3-chloro-2-fluoro-6-(1H-tetrazol-1-yl)phenyl)-2-(2-cyclopropyl-1-(4-(3-(trifluoromethyl)pyridin-4-yl)-1H-pyrazol-1-yl)ethyl)pyridine 1-oxide as a white solid.

LC/MS: mass calculated for $C_{26}H_{19}ClF_4N_8O$: 570.1, measured (ES, m/z): 571.2 [M+H]$^+$. $^1$H NMR (400 MHz, CD$_3$OD) δ 9.39 (s, 1H), 8.93-9.00 (m, 1H), 8.71-8.82 (m, 1H), 8.39 (s, 2H), 7.88-7.98 (m, 2H), 7.81 (d, J=5.38 Hz, 1H), 7.57-7.64 (m, 2H), 7.32 (dd, J=1.47, 8.31 Hz, 1H), 6.26 (dd, J=3.91, 10.27 Hz, 1H), 2.44 (m, 2H), 1.99-2.13 (m, 1H), 0.60-0.73 (m, 1H), 0.33-0.50 (m, 2H), 0.19 (dt, J=5.14, 9.17 Hz, 1H), −0.03-0.04 (m, 1H).

Example 397: (S*)-5-(3-Chloro-2-fluoro-6-(1H-tetrazol-1-yl)phenyl)-2-(2-((methoxycarbonyl)(methyl)amino)-1-(4-(2-(trifluoromethyl)pyridin-4-yl)-1H-pyrazol-1-yl)ethyl)pyridine 1-oxide

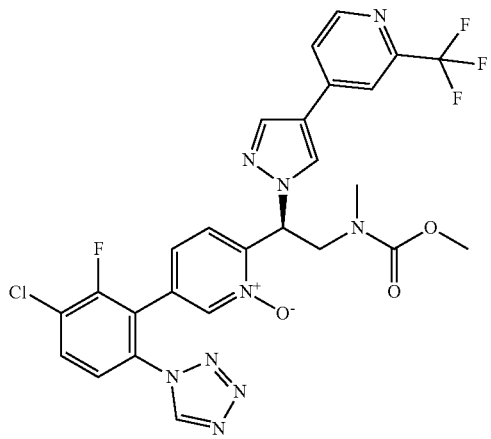 [SMILES: COC(=O)N(C)C[C@@H](c1ccc(-c2c(-n3cnnn3)ccc(Cl)c2F)c[n+]1[O-])n1cc(-c2ccnc(C(F)(F)F)c2)cn1]

LC/MS: mass calculated for $C_{26}H_{20}ClF_4N_9O_3$: 617.13, measured (ES, m/z): 618.1 [M+H]$^+$. $^1$H NMR (300 MHz, DMSO-d$_6$) δ 9.69 (s, 1H), 8.89 (s, 1H), 8.66 (d, J=5.2 Hz, 1H), 8.46 (s, 1H), 8.33 (s, 1H), 8.13 (s, 1H), 8.00-8.08 (m, 1H), 7.91 (d, J=5.2 Hz, 1H), 7.75 (dd, J=8.7, 1.6 Hz, 1H), 7.67 (d, J=8.3 Hz, 1H), 7.16-7.27 (m, 1H), 6.20-6.40 (m, 1H), 4.08-4.25 (m, 1H), 3.80-4.05 (m, 1H), 3.53 (s, 3H), 2.60-2.83 (m, 3H). $^{19}$F NMR (282 MHz, DMSO-d$_6$) δ −66.52, −112.68.

Example 398: (S*)-5-(3-Chloro-2-fluoro-6-(1H-tetrazol-1-yl)phenyl)-2-(1-(4-(2-fluoropyridin-4-yl)-1H-pyrazol-1-yl)-2-(2-oxopyrrolidin-1-yl)ethyl)pyridine 1-oxide

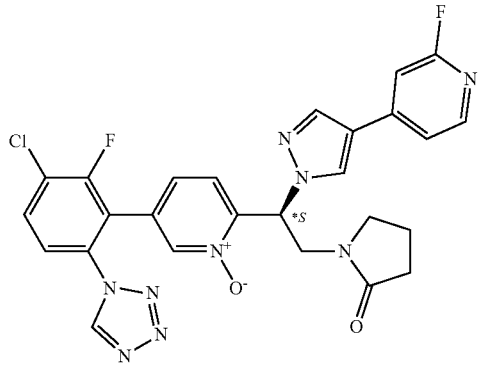 [SMILES: O=C1CCCN1C[C@@H](c1ccc(-c2c(-n3cnnn3)ccc(Cl)c2F)c[n+]1[O-])n1cc(-c2ccnc(F)c2)cn1]

LC/MS: mass calculated for $C_{26}H_{20}ClF_2N_9O$: 563.14, measured (ES, m/z): 564.1 [M+H]$^+$. $^1$H NMR (400 MHz, DMSO-d$_6$) δ 9.69 (s, 1H), 8.79 (s, 1H), 8.47 (d, J=1.6 Hz, 1H), 8.25 (s, 1H), 8.18 (d, J=5.3 Hz, 1H), 8.03-8.10 (m, 1H), 7.77 (dd, J=8.7, 1.5 Hz, 1H), 7.55-7.65 (m, 2H), 7.44 (s, 1H), 7.22 (dd, J=8.2, 1.7 Hz, 1H), 6.26-6.37 (m, 1H), 3.93-4.09 (m, 2H), 3.25-3.35 (m, 1H), 2.87-2.97 (m, 1H), 2.05-2.23 (m, 2H), 1.70-1.90 (m, 2H). $^{19}$F NMR (376 MHz, DMSO-d$_6$) δ −69.19, −112.67.

Example 399: (R*)-5-(3-Chloro-2-fluoro-6-(1H-tetrazol-1-yl)phenyl)-2-(2-((methoxycarbonyl)(methyl)amino)-1-(4-(2-(trifluoromethyl)pyridin-4-yl)-1H-pyrazol-1-yl)ethyl)pyridine 1-oxide

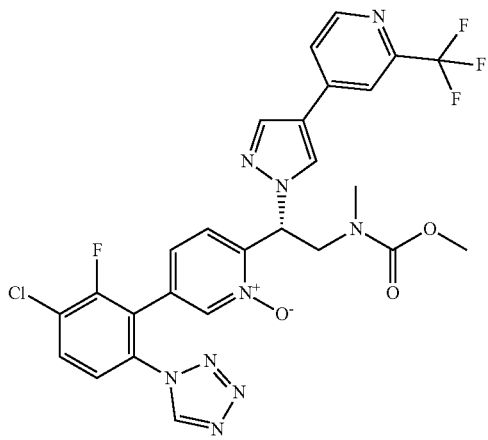 [SMILES: COC(=O)N(C)C[C@H](c1ccc(-c2c(-n3cnnn3)ccc(Cl)c2F)c[n+]1[O-])n1cc(-c2ccnc(C(F)(F)F)c2)cn1]

LC/MS: mass calculated for $C_{26}H_{20}ClF_4N_9O_3$: 617.13, measured (ES, m/z): 618.1 [M+H]$^+$. $^1$H NMR (300 MHz, DMSO-$d_6$) δ 9.69 (s, 1H), 8.89 (s, 1H), 8.66 (d, J=5.2 Hz, 1H), 8.46 (s, 1H), 8.33 (s, 1H), 8.13 (s, 1H), 8.00-8.11 (m, 1H), 7.91 (d, J=5.3 Hz, 1H), 7.75 (dd, J=8.7, 1.6 Hz, 1H), 7.67 (d, J=8.3 Hz, 1H), 7.21 (d, J=8.4 Hz, 1H), 6.20-6.40 (m, 1H), 4.08-4.20 (m, 1H), 3.80-3.95 (m, 1H), 3.50-3.56 (m, 3H), 2.66 (d, J=13.0 Hz, 3H). $^{19}$F NMR (282 MHz, DMSO-$d_6$) δ −66.51, −112.68.

Example 400: (R*) 5-(3-Chloro-2-fluoro-6-(1H-tetrazol-1-yl)phenyl)-2-(1-(4-(2-fluoropyridin-4-yl)-1H-pyrazol-1-yl)-2-(2-oxopyrrolidin-1-yl)ethyl)pyridine 1-oxide

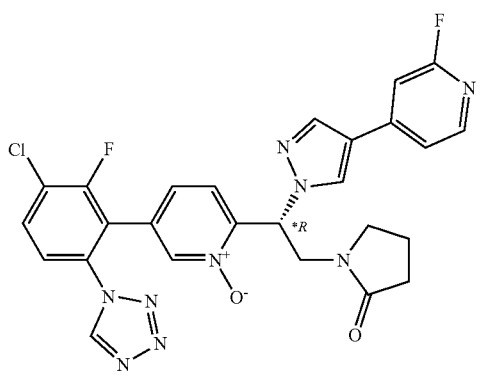 [SMILES: O=C1CCCN1C[C@H](c1ccc(-c2c(-n3cnnn3)ccc(Cl)c2F)c[n+]1[O-])n1cc(-c2ccnc(F)c2)cn1]

LC/MS: mass calculated for $C_{26}H_{20}ClF_2N_9O$: 563.1, measured (ES, m/z): 564.2 [M+H]$^+$. $^1$H NMR (400 MHz, DMSO-$d_6$) δ 9.69 (s, 1H), 8.79 (s, 1H), 8.47 (d, J=1.6 Hz, 1H), 8.25 (s, 1H), 8.18 (d, J=5.3 Hz, 1H), 8.00-8.09 (m, 1H), 7.77 (dd, J=8.7, 1.5 Hz, 1H), 7.55-7.65 (m, 2H), 7.44 (s, 1H), 7.22 (dd, J=8.3, 1.7 Hz, 1H), 6.28-6.34 (m, 1H), 3.90-4.10 (m, 2H), 3.25-3.35 (m, 1H), 2.87-2.98 (m, 1H), 2.05-2.23 (m, 2H), 1.71-1.89 (m, 2 h). $^{19}$F NMR (376 MHz, DMSO-$d_6$) δ −69.19, −112.67.

Example 401: 5-(3-Chloro-2-fluoro-6-(1H-tetrazol-1-yl)phenyl)-2-(3-(difluoromethoxy)-1-(4-(3-fluoropyridin-4-yl)-1H-pyrazol-1-yl)propyl)pyridine 1-oxide

Step 1: 5-Bromo-2-(3-(difluoromethoxy)-1-(4-(3-fluoropyridin-4-yl)-1H-pyrazol-1-yl)propyl)pyridine A mixture of 5-bromo-2-(3-(difluoromethoxy)-1-(4-iodo-1H-pyrazol-1-yl)propyl)pyridine (450 mg, 0.98 mmol, 1.0 equiv.), (3-fluoropyridin-4-yl)boronic acid (138 mg, 0.98 mmol, 1.0 equiv.), potassium phosphate (626 mg, 2.95 mmol, 3.0 equiv.) and Pd(PPh$_3$)$_4$ (114 mg, 0.10 mmol, 0.1 equiv.) in 1,4-dioxane (6 mL) and water (2 mL) was stirred at 90° C. overnight. The resulting mixture was cooled to room temperature, the reaction was quenched with H$_2$O and extracted with ethyl acetate twice. The combined organic layers were washed with brine, dried over Na$_2$SO$_4$ and concentrated. The residue was purified by silica gel chromatography (0→50% ethyl acetate/petroleum ether) to yield 5-bromo-2-(3-(difluoromethoxy)-1-(4-(3-fluoropyridin-4-yl)-1H-pyrazol-1-yl)propyl)pyridine as a light yellow solid. LC/MS: mass calculated for $C_{17}H_{14}BrF_3N_4O$: 426.03, measured (ES, m/z): 426.95, 428.95 [M+H, M+H+2]$^+$.

Step 2: 4-Chloro-2-(6-(3-(difluoromethoxy)-1-(4-(3-fluoropyridin-4-yl)-1H-pyrazol-1-yl)propyl)pyridin-3-yl)-3-fluoroaniline A mixture of 5-bromo-2-(3-(difluoromethoxy)-1-(4-(3-fluoropyridin-4-yl)-1H-pyrazol-1-yl)propyl)pyridine (110 mg, 0.26 mmol, 1.0 equiv.), 6-amino-3-chloro-2-fluorophenylboronic acid (73 mg, 0.39 mmol, 1.509 equiv.), potassium carbonate (107 mg, 0.77 mmol, 3.0 equiv.) and Pd(PPh$_3$)$_4$ (30 mg, 0.026 mmol, 0.1 equiv.) in 1,4-dioxane (3 mL) and water (1 mL) was stirred at 90° C. overnight. The resulting mixture was cooled to room temperature, the reaction was quenched with H$_2$O and extracted with ethyl acetate twice. The combined organic layers were washed with brine, dried over Na$_2$SO$_4$ and concentrated.

The residue was purified by silica gel chromatography (0→50% ethyl acetate/petroleum ether) to yield 4-chloro-2-(6-(3-(difluoromethoxy)-1-(4-(3-fluoropyridin-4-yl)-1H-pyrazol-1-yl)propyl)pyridin-3-yl)-3-fluoroaniline as a light yellow solid. LC/MS: mass calculated for $C_{23}H_{18}ClF_4N_5O$: 491.11, measured (ES, m/z): 492.15 [M+H]$^+$.

Step 3: 5-(3-Chloro-2-fluoro-6-(1H-tetrazol-1-yl)phenyl)-2-(3-(difluoromethoxy)-1-(4-(3-fluoropyridin-4-yl)-1H-pyrazol-1-yl)propyl)pyridine A mixture of 4-chloro-2-(6-(3-(difluoromethoxy)-1-(4-(3-fluoropyridin-4-yl)-1H-pyrazol-1-yl)propyl)pyridin-3-yl)-3-fluoroaniline (110 mg, 0.22 mmol, 1.0 equiv.), aidotrimethylsilane (0.5 mL) and trimethoxymethane (0.5 mL) in acetic acid glacial (1 mL) was stirred at room temperature overnight. The mixture was concentrated and the residue was purified by reverse phase chromatography on C18 (80 g, MeCN/H$_2$O (0.05% CF$_3$COOH): 0→45%) to yield 5-(3-chloro-2-fluoro-6-(1H-tetrazol-1-yl)phenyl)-2-(3-(difluoromethoxy)-1-(4-(3-fluoropyridin-4-yl)-1H-pyrazol-1-yl)propyl)pyridine as a light yellow solid. LC/MS: mass calculated for C$_{24}$H$_{17}$ClF$_4$N$_8$O: 544.14, measured (ES, m/z): 545.10 [M+H]$^+$.

Step 5: 5-(3-Chloro-2-fluoro-6-(1H-tetrazol-1-yl)phenyl)-2-(3-(difluoromethoxy)-1-(4-(3-fluoropyridin-4-yl)-1H-pyrazol-1-yl)propyl)pyridine 1-oxide A mixture of 5-(3-chloro-2-fluoro-6-(1H-tetrazol-1-yl)phenyl)-2-(3-(difluoromethoxy)-1-(4-(3-fluoropyridin-4-yl)-1H-pyrazol-1-yl)propyl)pyridine (50 mg, 0.09 mmol, 1.0 equiv.), methyl trioxorhenium (VII) (11 mg, 0.05 mmol, 0.5 equiv.) and hydrogen peroxide (0.046 mL, 0.46 mmol, 30 wt %, 5.0 equiv.) in CH$_3$OH (1.0 mL) was stirred at room temperature for 2 h. The reaction was purified by reverse phase chromatography on C18 (80 g, MeCN/H$_2$O (0.05% CF$_3$COOH): 0→45%) to yield 5-(3-chloro-2-fluoro-6-(1H-tetrazol-1-yl)phenyl)-2-(3-(difluoromethoxy)-1-(4-(3-fluoropyridin-4-yl)-1H-pyrazol-1-yl)propyl)pyridine 1-oxide as a white solid.

LC/MS: mass calculated for C$_{24}$H$_{17}$ClF$_4$N$_8$O$_2$: 560.11, measured (ES, m/z): 561.0 [M+H]$^+$. $^1$H NMR (300 MHz, DMSO-d$_6$): δ 9.70 (s, 1H), 8.62-8.71 (m, 2H), 8.40-8.50 (m, 2H), 8.28 (s, 1H), 8.02-8.10 (m, 1H), 7.89 (t, J=6.1 Hz, 1H), 7.76 (dd, J=8.7, 1.6 Hz, 1H), 7.18-7.38 (m, 2H), 6.64 (t, J=75.7 Hz, 1H), 6.23-6.29 (m, 1H), 3.79-3.89 (m, 1H), 3.61-3.75 (m, 1H), 2.54-2.70 (m, 2H). $^{19}$F NMR (282 MHz, DMSO-d$_6$): δ −74.79, −83.35, −112.68, −129.03.

Example 402: (R*)-5-(3-Chloro-2-fluoro-6-(1H-tetrazol-1-yl)phenyl)-2-(3-(methoxy-d3)-1-(4-(2-(trifluoromethyl)pyridin-4-yl)-1H-pyrazol-1-yl)propyl)pyridine 1-oxide

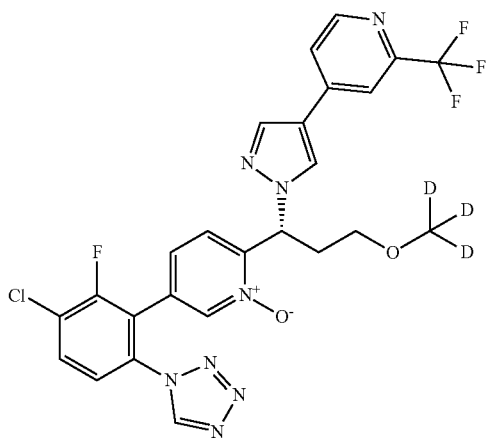 [SMILES: [2H]C([2H])([2H])OCC[C@H](c1ccc(-c2c(-n3cnnn3)ccc(Cl)c2F)c[n+]1[O-])n1cc(-c2ccnc(C(F)(F)F)c2)cn1]

Step 1: 4-(1-(1-(5-Bromopyridin-2-yl)-3-((tert-butyldimethylsilyl)oxy)propyl)-1H-pyrazol-4-yl)-2-(trifluoromethyl)pyridine 4-(1H-pyrazol-4-yl)-2-(trifluoromethyl)pyridine (603 mg, 2.83 mmol, 1.0 equiv.) and cesium carbonate (2.8 g, 8.49 mmol, 3.0 equiv.) were dissolved in CH$_3$CN (10.0 mL) and stirred at room temperature for 0.5 h. The solution of 1-(5-bromopyridin-2-yl)-3-((tert-butyldimethylsilyl)oxy)propyl methanesulfonate (1.2 g, 2.83 mmol, 1.0 equiv.) in 8.0 mL CH$_3$CN was then added, the reaction mixture stirred for another 3 h at 70° C. The resulting mixture was diluted with EA (100 mL) and water (50 mL), the organic extracts were washed with water (50 mL twice) and then dried over anhydrous Na$_2$SO$_4$, filtered and concentrated under reduced pressure. The residue was purified by normal phase chromatography (mobile phase: DCM/MeOH, 0-*20%) to yield 4-(1-(1-(5-bromopyridin-2-yl)-3-((tert-butyldimethylsilyl)oxy)propyl)-1H-pyrazol-4-yl)-2-(trifluoromethyl)pyridine as a yellow oil. LC/MS: mass calculated for C$_{23}$H$_{28}$BrF$_3$N$_4$OSi: 540.12, measured (ES, m/z): 541.05 [M+H]$^+$.

Step 2: 3-(5-Bromopyridin-2-yl)-3-(4-(2-(trifluoromethyl)pyridin-4-yl)-1H-pyrazol-1-yl)propan-1-ol 4-(1-(1-(5-bromopyridin-2-yl)-3-((tert-butyldimethylsilyl)oxy)propyl)-1H-pyrazol-4-yl)-2-(trifluoromethyl)pyridine (1.2 g, 2.23 mmol, 1.0 equiv.) was dissolved in THF (20 mL) and then tetrabutylammonium fluoride (1.7 g, 6.7 mmol, 3.0 equiv.) added to the mixture stirred at room temperature for 5 h. The solvent was removed under reduced pressure; the mixture was diluted with EA (100 mL) and washed by water (50 mL) three times. The combined organic layers were dried by anhydrous Na$_2$SO$_4$. The resulting residue was purified by silica gel column (mobile phase: DCM/MeOH, 0→10%) to yield 3-(5-bromopyridin-2-yl)-3-(4-(2-(trifluoromethyl)pyridin-4-yl)-1H-pyrazol-1-yl)propan-1-ol as a yellow oil. LC/MS: mass calculated for C$_{17}$H$_{14}$BrF$_3$N$_4$O: 426.03, measured (ES, m/z): 428.95 [M+H+2]$^+$

Step 3: 4-(1-(1-(5-bromopyridin-2-yl)-3-(methoxy-d3)propyl)-1H-pyrazol-4-yl)-2-(trifluoromethyl)pyridine To the solution of 3-(5-bromopyridin-2-yl)-3-(4-(2-(trifluoromethyl)pyridin-4-yl)-1H-pyrazol-1-yl)propan-1-ol (830.0 mg, 1.94 mmol, 1.0 equiv.) and silver oxide (2251.0 mg, 9.70 mmol, 5.0 equiv.) in CHCl$_3$ (10 mL) and iodomethane-D$_3$ (1.4 g, 9.70 mmol, 5.0 equiv.) was added. The reaction mixture was stirred for 6 h at 50° C. The reaction mixture was then diluted with DCM 100 mL) and washed by water (50 mL) three times, and the organic layer dried by anhydrous Na$_2$SO$_4$. The solvent was removed and the residue was purified by normal phase chromatography (mobile phase: DCM/MeOH, 0→10%) to yield 4-(1-(1-(5-bromopyridin-2-yl)-3-(methoxy-d3)propyl)-1H-pyrazol-4-yl)-2-(trifluoromethyl)pyridine as a yellow solid.

LC/MS: mass calculated for C$_{11}$H$_{13}$D3BrF$_3$N$_4$O: 443.06, measured (ES, m/z): 446.05 [M+H+2]$^+$

Step 4: 4-chloro-3-fluoro-2-(6-(3-(methoxy-d3)-1-(4-(2-(trifluoromethyl)pyridin-4-yl)-1H-pyrazol-1-yl)propyl)pyridin-3-yl)aniline 4-(1-(1-(5-bromopyridin-2-yl)-3-(methoxy-d3)propyl)-1H-pyrazol-4-yl)-2-(trifluoromethyl)pyridine (600.0 mg, 1.35 mmol, 1.0 equiv.), (6-amino-3-chloro-2-fluorophenyl) boronic acid (281.3 mg, 1.48 mmol, 1.1 equiv.), tetrakis (triphenylphosphine)palladium(156.1 mg, 0.14 mmol, 0.1 equiv.) and potassium carbonate (279.9 mg, 2.03 mmol, 1.5 equiv.) were dissolved in 1,4-dioxane (8.0 mL) and water (8.0 mL) under $N_2$ and the reaction mixture was stirred at 90° C. for 4 h. The mixture was then diluted with EA (100 mL) and water (50 mL), the organic extracts were washed with water (50 mL) two times and then dried over anhydrous $Na_2SO_4$, filtered and concentrated under reduced pressure. The residue was purified by normal phase chromatography (mobile phase: DCM/MeOH, 0→10%) to yield 4-chloro-3-fluoro-2-(6-(3-(methoxy-d3)-1-(4-(2-(trifluoromethyl)pyridin-4-yl)-1H-pyrazol-1-yl)propyl)pyridin-3-yl)aniline as a yellow solid. LC/MS: mass calculated for $C_{24}H_{17}D3ClF_4N_5O$: 508.15, measured (ES, m/z): 509.15 $[M+H]^+$ Step 5: 4-(1-(1-(5-(3-chloro-2-fluoro-6-(1H-tetrazol-1-yl)phenyl)pyridin-2-yl)-3-(methoxy-d3)propyl)-1H-pyrazol-4-yl)-2-(trifluoromethyl)pyridine 4-chloro-3-fluoro-2-(6-(3-(methoxy-d3)-1-(4-(2-(trifluoromethyl)pyridin-4-yl)-1H-pyrazol-1-yl)propyl)pyridin-3-yl)aniline (400.0 mg, 0.79 mmol, 1.0 equiv.), azidotrimethylsilane (543.3 mg, 4.72 mmol, 6.0 equiv.) and trimethoxymethane (2 mL) were dissolved in acetic acid glacial (2.5 mL). The reaction mixture was stirred at 30° C. overnight. The solvent was removed under reduced pressure and the resulting residue was purified by chromatography on C18 (80 g, MeCN/$H_2O$ (0.05% $CF_3COOH$): 0→46%) to yield 4-(1-(1-(5-(3-chloro-2-fluoro-6-(1H-tetrazol-1-yl)phenyl)pyridin-2-yl)-3-(methoxy-d3)propyl)-1H-pyrazol-4-yl)-2-(trifluoromethyl)pyridine as a white solid. LC/MS: mass calculated for $C_{25}H_{16}D3ClF_4N_8O$: 561.15, measured (ES, m/z): 562.10 $[M+H]^+$ Step 6: (R*)-5-(3-chloro-2-fluoro-6-(1H-tetrazol-1-yl)phenyl)-2-(3-(methoxy-d3)-1-(4-(2-(trifluoromethyl)pyridin-4-yl)-1H-pyrazol-1-yl)propyl)pyridine 1-oxide 4-(1-(1-(5-(3-chloro-2-fluoro-6-(1H-tetrazol-1-yl)phenyl)pyridin-2-yl)-3-(methoxy-d3)propyl)-1H-pyrazol-4-yl)-2-(trifluoromethyl)pyridine (150.0 mg, 0.27 mmol, 1.0 equiv.), 3-chloroperoxybenzoic acid (230.3 mg, 1.34 mmol, 5.0 equiv.) were dissolved in EA (5.0 mL) and stirred at room temperature for 2 h. Sodium bicarbonate and sodium thiosulfate were added to the mixture, and the mixture was then diluted with EA (100 mL) and water (50 mL), the organic extracts were washed with water (50 mL) two times and then dried over anhydrous $Na_2SO_4$, filtered and concentrated under reduced pressure. The resulting residue was purified by chromatography on C18 (80 g, MeCN/$H_2O$ (0.05% $CF_3COOH$): 0→60%) and prep-chiral-HPLC. The collected fractions were combined and concentrated under vacuum to yield (R*)-5-(3-chloro-2-fluoro-6-(1H-tetrazol-1-yl)phenyl)-2-(3-(methoxy-d3)-1-(4-(2-(trifluoromethyl) pyridin-4-yl)-1H-pyrazol-1-yl)propyl)pyridine 1-oxide as a white solid.
LC/MS: mass calculated for $C_{25}H_{16}ClD_3F_4N_8O_2$: 577.14, measured (ES, m/z): 578.15 $^1$H NMR (300 MHz, DMSO-$d_6$) δ 9.68 (s, 1H), 8.89 (s, 1H), 8.66 (d, J=5.2 Hz, 1H), 8.43 (s, 1H), 8.35 (s, 1H), 8.15 (s, 1H), 8.00-8.08 (m, 1H), 7.92 (d, J=4.9 Hz, 1H), 7.70-7.76 (m, 1H), 7.32 (d, J=8.3 Hz, 1H), 7.15 (d, J=7.7 Hz, 1H), 6.16 (t, J=7.3 Hz, 1H), 3.08-3.22 (m, 2H), 2.40-2.47 (m, 2H). $^{19}$F NMR (282 MHz, DMSO-$d_6$) δ −66.50, −112.71.

Example 403: (S*)-5-(3-Chloro-2-fluoro-6-(1H-tetrazol-1-yl)phenyl)-2-(3-(methoxy-d3)-1-(4-(2-(trifluoromethyl)pyridin-4-yl)-1H-pyrazol-1-yl)propyl)pyridine 1-oxide

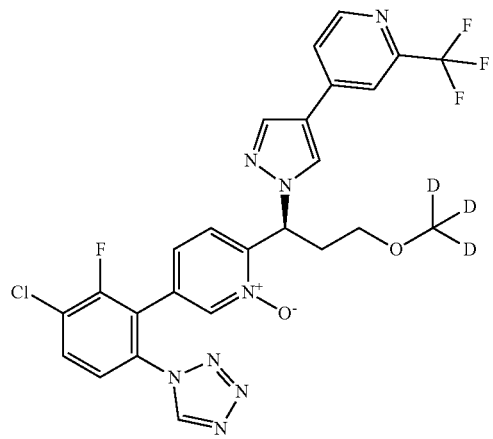 [SMILES: [2H]C([2H])([2H])OCC[C@@H](c1ccc(-c2c(-n3cnnn3)ccc(Cl)c2F)c[n+]1[O-])n1cc(-c2ccnc(C(F)(F)F)c2)cn1]

LC/MS: mass calculated for $C_{25}H_{18}ClD_3F_4N_8O_2$: 577.14, measured (ES, m/z): 578.15 $[M+H]^+$. $^1$H NMR (300 MHz, DMSO-$d_6$) δ 9.68 (s, 1H), 8.89 (s, 1H), 8.66 (d, J=5.2 Hz, 1H), 8.43 (s, 1H), 8.35 (s, 1H), 8.15 (d, J=1.2 Hz, 1H), 8.00-8.08 (m, 1H), 7.88-7.94 (m, 1H), 7.74 (dd, J=8.7, 1.6 Hz, 1H), 7.32 (d, J=8.3 Hz, 1H), 7.15 (d, J=8.9 Hz, 1H), 6.10-6.20 (m, 1H), 3.10-3.32 (m, 2H), 2.40-2.47 (m, 2H). $^{19}$F NMR (282 MHz, DMSO-$d_6$) δ −66.51, −112.69.

Example 404: 5-(5-Chloro-2-(1H-tetrazol-1-yl)phenyl)-2-(2-(4,5-dihydropyrano[3,4-c]pyrazol-2(7H)-yl)-1-(4-(2-(trifluoromethyl)pyridin-4-yl)-1H-pyrazol-1-yl)ethyl)pyridine 1-oxide

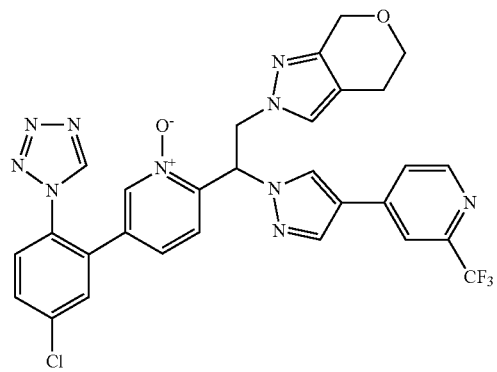 [SMILES: [O-][n+]1cc(-c2cc(Cl)ccc2-n2cnnn2)ccc1C(Cn1cc2c(n1)COCC2)n1cc(-c2ccnc(C(F)(F)F)c2)cn1]

LC/MS: mass calculated for $C_{29}H_{22}ClF_3N_{10}O_2$: 634.2, measured (ES, m/z): 635.3 $[M+H]^+$. $^1$H NMR (400 MHz, CD$_3$OD) δ ppm 2.50 (bs, 2H), 2.52-2.57 (m, 1H), 3.58-3.70 (m, 1H), 3.70-3.83 (m, 1H), 4.57-4.69 (m, 2H), 4.96-5.10 (m, 2H), 6.58-6.67 (m, 1H), 7.12-7.23 (m, 2H), 7.26-7.33 (m, 1H), 7.55 (d, J=8.3 Hz, 1H), 7.69-7.75 (m, 1H), 7.75-

7.82 (m, 2H), 7.96 (d, J=7.3 Hz, 1H), 8.19-8.25 (m, 1H), 8.29-8.34 (m, 1H), 8.59 (d, J=4.9 Hz, 1H), 9.38 (s, 1H).

Example 405: 5-(3-Chloro-2-fluoro-6-(1H-tetrazol-1-yl)phenyl)-2-(2-cyclopropyl-1-(2-methyl-1'H,2H-[3,4'-bipyrazol]-1'-yl)ethyl)pyridine 1-oxide

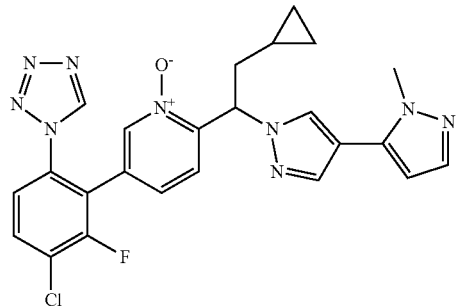 [SMILES: Cn1nccc1-c1cnn(C(CC2CC2)c2ccc(-c3c(-n4cnnn4)ccc(Cl)c3F)c[n+]2[O-])c1]

To a mixture of 1'-(1-(5-(3-Chloro-2-fluoro-6-(1H-tetrazol-1-yl)phenyl)pyridin-2-yl)-2-cyclopropylethyl)-2-methyl-1'H,2H-3,4'-bipyrazole (32 mg, 0.07 mmol) in MeOH (1 mL) was added MeReO$_3$ (8.1 mg, 0.03 mmol), followed by 30% H$_2$O$_2$ (111 mg, 0.98 mmol). The resulting mixture was stirred at room temperature for 1 h. The reaction mixture was subjected to Gilson HPLC to yield 5-(3-Chloro-2-fluoro-6-(1H-tetrazol-1-yl)phenyl)-2-(2-cyclopropyl-1-(2-methyl-1'H,2H-[3,4'-bipyrazol]-1'-yl)ethyl)pyridine 1-oxide as a white solid.

LC/MS: mass calculated for $C_{24}H_{21}ClFN_9O$: 505.2, measured (ES, m/z): 506.3 [M+H]$^+$. $^1$H NMR (400 MHz, CD$_3$OD) δ 9.39 (s, 1H), 8.37 (s, 1H), 8.28 (s, 1H), 7.89-7.96 (m, 1H), 7.88 (s, 1H), 7.62 (s, 1H), 7.48-7.54 (m, 2H), 7.30 (s, 1H), 6.45 (d, J=1.96 Hz, 1H), 6.25 (dd, J=4.16, 10.03 Hz, 1H), 3.89-3.97 (m, 3H), 2.42-2.53 (m, 1H), 1.99-2.08 (m, 1H), 0.64-0.75 (m, 1H), 0.37-0.49 (m, 2H), 0.19 (dt, J=4.65, 9.17 Hz, 1H), 0.01-0.06 (m, 1H).

Example 406: 5-(3-chloro-2-fluoro-6-(1H-tetrazol-1-yl)phenyl)-2-(2-cyclopropyl-1-(1'-(2-methoxy-2-oxoethyl)-1H,1'H-[4,4'-bipyrazol]-1-yl)ethyl)pyridine 1-oxide

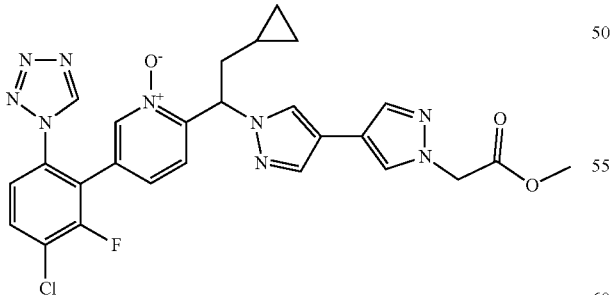

LC/MS: mass calculated for $C_{26}H_{23}ClFN_9O_3$: 563.2, measured (ES, m/z): 564.2 [M+H]$^+$. $^1$H NMR (400 MHz, CD$_3$OD) δ 9.38 (s, 1H), 8.35 (s, 1H), 8.10 (s, 1H), 7.88-7.95 (m, 1H), 7.86 (s, 1H), 7.79 (s, 1H), 7.73 (s, 1H), 7.57-7.62 (m, 1H), 7.34 (s, 1H), 7.24-7.30 (m, 1H), 6.18 (dd, J=3.91, 10.27 Hz, 1H), 5.02 (s, 2H), 3.73-3.79 (m, 3H), 2.43-2.55 (m, 1H), 1.94-2.00 (m, 1H), 0.65-0.77 (m, 1H), 0.37-0.47 (m, 2H), 0.17-0.25 (m, 1H), 0.04-0.10 (m, 1H).

Example 407: (R*) 5-(3-Chloro-2-fluoro-6-(1H-tetrazol-1-yl)phenyl)-2-(1-(4-(2-(difluoromethyl)pyridin-4-yl)-1H-pyrazol-1-yl)-2-((methoxycarbonyl)(methyl)amino)ethyl)pyridine 1-oxide trifluoroacetic acid

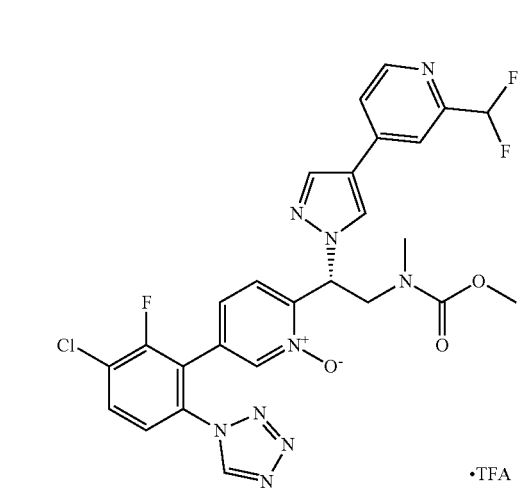 [SMILES: COC(=O)N(C)C[C@H](c1ccc(-c2c(-n3cnnn3)ccc(Cl)c2F)c[n+]1[O-])n1cc(-c2ccnc(C(F)F)c2)cn1]

LC/MS: mass calculated for $C_{26}H_{21}ClF_3N_9O_3$: 599.1, measured (ES, m/z): 600.1 [M+H]$^+$. $^1$H NMR (400 MHz, DMSO-d$_6$) δ 9.46 (s, 1H), 8.58 (s, 1H), 8.33 (s, 1H), 8.26 (d, J=6.9 Hz, 1H), 8.14 (s, 1H), 7.96 (s, 1H), 7.85-7.94 (m, 1H), 7.78-7.83 (m, 1H), 7.56-7.70 (m, 2H), 7.35 (d, J=8.1 Hz, 1H), 7.15 (t, J=53.2 Hz, 1H), 5.77 (t, J=7.5 Hz, 1H), 4.00-4.08 (m, 2H), 3.40-3.52 (m, 3H), 2.58 (s, 3H). $^{19}$F NMR (376 MHz, CD$_3$OD) δ −76.98, −114.23, −125.09.

Example 408: (S*)-4-(1-(1-(5-(3-Chloro-2-fluoro-6-(1H-tetrazol-1-yl)phenyl)-1-oxidopyridin-2-yl)-2-((methoxycarbonyl)(methyl)amino)ethyl)-1H-pyrazol-4-yl)-2-(difluoromethyl)pyridine 1-oxide

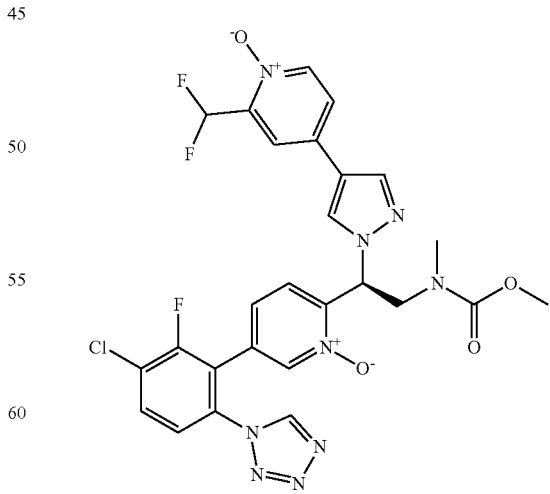

LC/MS: mass calculated for $C_{26}H_{21}ClF_3N_9O_4$: 615.1, measured (ES, m/z): 616.1 [M+H]$^+$. $^1$H NMR (400 MHz, DMSO-d$_6$) δ 9.70 (s, 1H), 8.80 (s, 1H), 8.47 (d, J=1.6 Hz, 1H), 8.37 (d, J=6.8 Hz, 1H), 8.25 (s, 1H), 8.03-8.10 (m, 1H), 8.00 (d, J=2.6 Hz, 1H), 7.84 (dd, J=6.8, 2.7 Hz, 1H), 7.77 (dd, J=8.7, 1.5 Hz, 1H), 7.67 (s, 1H), 7.07-7.41 (m, 2H), 6.26-6.31 (m, 1H), 4.03-4.20 (m, 1H), 3.85-4.02 (m, 1H), 3.55-3.62 (m, 3H), 2.60-2.80 (m, 3H). $^{19}$F NMR (376 MHz, DMSO-$d_6$) δ −112.67, −122.79.

Example 409: 5-(3-Chloro-2-fluoro-6-(1H-tetrazol-1-yl)phenyl)-2-(2-(4-fluoro-1H-pyrazol-1-yl)-1-(4-(2-isopropylpyridin-4-yl)-1H-pyrazol-1-yl)ethyl)pyridine 1-oxide trifluoroacetic acid

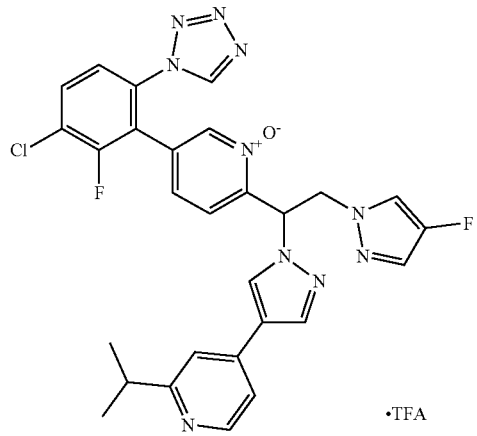

LC/MS: mass calculated for $C_{28}H_{23}ClF_2N_{10}O$: 588.15, measured (ES, m/z): 589.15 [M+H]$^+$. $^1$H NMR (400 MHz, DMSO-$d_6$) δ 9.69 (s, 1H), 8.90 (s, 1H), 8.65 (d, J=6.3 Hz, 1H), 8.48-8.54 (m, 2H), 8.04-8.13 (m, 2H), 7.93-8.04 (m, 1H), 7.70-7.80 (m, 2H), 7.59 (d, J=8.3 Hz, 1H), 7.45 (d, J=4.2 Hz, 1H), 7.26 (dd, J=8.3, 1.7 Hz, 1H), 6.50-6.59 (m, 1H), 5.00-5.09 (m, 1H), 4.88-4.99 (m, 1H), 3.15-3.24 (m, 1H), 1.30-1.38 (m, 6H). $^{19}$F NMR (376 MHz, DMSO-$d_6$) δ −74.21, −112.66, −177.61.

Example 410: (S*)-5-(3-Chloro-2-fluoro-6-(1H-tetrazol-1-yl)phenyl)-2-(1-(4-(2-(difluoromethyl)pyridin-4-yl)-1H-pyrazol-1-yl)-2-((methoxycarbonyl)(methyl)amino)ethyl)pyridine 1-oxide trifluoroacetic acid

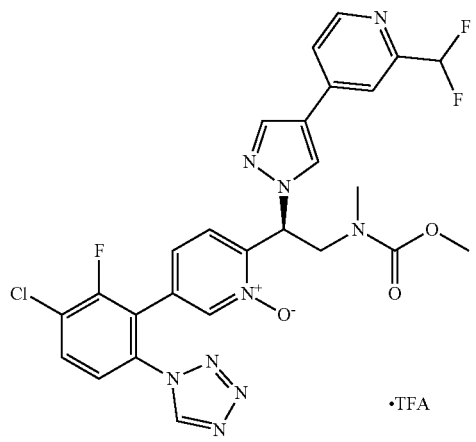 [SMILES: COC(=O)N(C)C[C@@H](c1ccc(-c2c(-n3cnnn3)ccc(Cl)c2F)c[n+]1[O-])n1cc(-c2ccnc(C(F)F)c2)cn1]

LC/MS: mass calculated for $C_{26}H_{21}ClF_3N_9O_3$: 599.1, measured (ES, m/z): 600.1 [M+H]$^+$. $^1$H NMR (400 MHz, DMSO-$d_6$) δ 9.51 (s, 1H), 8.62 (s, 1H), 8.36 (s, 1H), 8.27 (d, J=6.9 Hz, 1H), 8.16 (s, 1H), 7.88-8.00 (m, 2H), 7.81 (d, J=8.1 Hz, 1H), 7.62-7.69 (m, 2H), 7.03-7.34 (m, 2H), 5.78 (t, J=7.5 Hz, 1H), 4.03-4.12 (m, 2H), 3.40-5.58 (m, 3H), 2.58 (s, 3H). $^{19}$F NMR (376 MHz, DMSO-$d_6$) δ −73.42, −113.44, −122.79.

Example 411: 2-(1-(4-(2-(tert-Butyl)pyridin-4-yl)-1H-pyrazol-1-yl)-2-(4-fluoro-1H-pyrazol-1-yl)ethyl)-5-(3-chloro-2-fluoro-6-(1H-tetrazol-1-yl)phenyl)pyridine 1-oxide trifluoroacetic acid

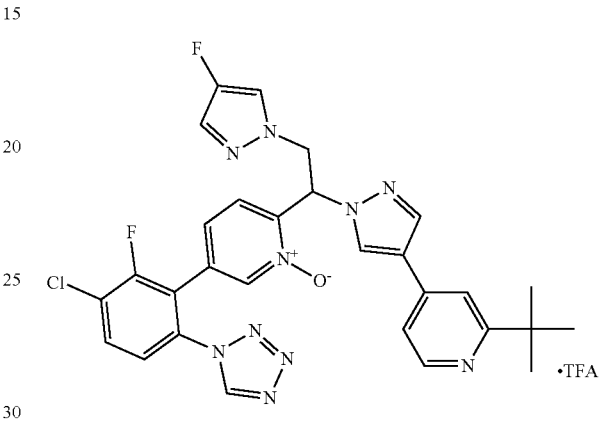

LC/MS: mass calculated for $C_{29}H_{25}ClF_2N_{10}O$: 602.2, measured (ES, m/z): 603.2 [M+H]$^+$. $^1$H NMR (400 MHz, DMSO-$d_6$) δ 9.69 (s, 1H), 8.94 (s, 1H), 8.61 (d, J=6.1 Hz, 1H), 8.52 (s, 2H), 8.03-8.10 (m, 1H), 7.90-8.00 (m, 2H), 7.77 (dd, J=8.7, 1.5 Hz, 1H), 7.72 (d, J=4.6 Hz, 1H), 7.56 (d, J=8.3 Hz, 1H), 7.45 (d, J=4.2 Hz, 1H), 7.26 (dd, J=8.1, 1.7 Hz, 1H), 6.50-6.58 (m, 1H), 5.00-5.07 (m, 1H), 4.87-4.97 (m, 1H), 1.43 (s, 9H). $^{19}$F NMR (376 MHz, DMSO-$d_6$) δ −74.33, −112.66, −177.65.

Example 412: (R*)-4-(1-(1-(5-(3-Chloro-2-fluoro-6-(1H-tetrazol-1-yl)phenyl)-1-oxidopyridin-2-yl)-2-((methoxycarbonyl)(methyl)amino)ethyl)-1H-pyrazol-4-yl)-2-(difluoromethyl)pyridine 1-oxide

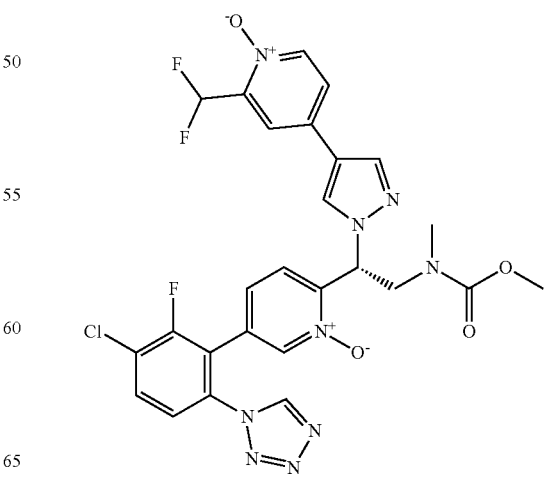

LC/MS: mass calculated for $C_{26}H_{21}ClF_3N_9O_4$: 615.1, measured (ES, m/z): 616.10 [M+H]$^+$. $^1$H NMR (400 MHz, DMSO-d$_6$) δ 9.70 (s, 1H), 8.79 (s, 1H), 8.47 (d, J=1.6 Hz, 1H), 8.35-8.40 (m, 1H), 8.25 (s, 1H), 8.05-8.11 (m, 1H), 8.00 (d, J=2.6 Hz, 1H), 7.81-7.88 (m, 1H), 7.75-7.80 (m, 1H), 7.63-7.70 (m, 1H), 7.11-7.40 (m, 2H), 6.23-6.35 (m, 1H), 3.89-4.21 (m, 2H), 3.35-3.59 (m, 3H), 2.65-2.72 (m, 3H). $^{19}$F NMR (376 MHz, DMSO-d$_6$) δ −112.67, −122.78.

Example 413: 5-(3-Chloro-2-fluoro-6-(1H-tetrazol-1-yl)phenyl)-2-(2-cyclopropyl-1-(4-(pyridazin-4-yl)-1H-pyrazol-1-yl)ethyl)pyridine 1-oxide

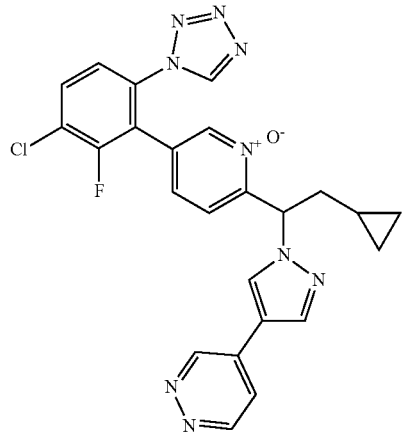

To a solution of 4-(1-(1-(5-(3-chloro-2-fluoro-6-(1H-tetrazol-1-yl)phenyl)pyridin-2-yl)-2-cyclopropylethyl)-1H-pyrazol-4-yl)pyridazine (76.9 mg, 0.16 mmol) in MeOH (3 mL) was added m-CPBA (176.6 mg, 0.79 mmol) and the reaction mixture was stirred at room temperature for 16 h. The mixture was subjected to Gilson HPLC directly to yield 5-(3-chloro-2-fluoro-6-(1H-tetrazol-1-yl)phenyl)-2-(2-cyclopropyl-1-(4-(pyridazin-4-yl)-1H-pyrazol-1-yl)ethyl)pyridine 1-oxide as a white solid.

LC/MS: mass calculated for $C_{24}H_{19}ClFN_9O$: 503.4, measured (ES, m/z): 504.2 [M+H]$^+$. $^1$H NMR (400 MHz, CD$_3$OD) δ 9.25 (s, 1H), 8.94 (d, J=2.45 Hz, 1H), 8.55 (s, 1H), 8.31-8.39 (m, 2H), 8.07-8.14 (m, 2H), 7.87 (dd, J=7.58, 8.56 Hz, 1H), 7.55-7.66 (m, 2H), 7.35 (d, J=8.31 Hz, 1H), 5.57-5.69 (m, 1H), 2.40-2.53 (m, 1H), 2.10 (t, J=7.09 Hz, 1H), 0.52-0.67 (m, 1H), 0.40 (br dd, J=1.96, 6.36 Hz, 2H), 0.01-0.14 (m, 2H).

Example 414: 4-(1-(1-(5-(3-Chloro-2-fluoro-6-(1H-tetrazol-1-yl)phenyl)-1-oxidopyridin-2-yl)-2-cyclopropylethyl)-1H-pyrazol-4-yl)pyridazine 1-oxide

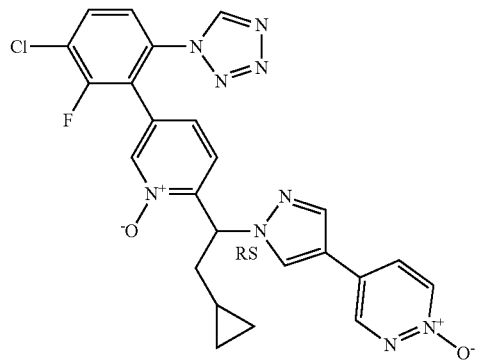

LC/MS: mass calculated for $C_{24}H_{19}ClFN_9O_2$: 519.1, measured (ES, m/z): 520 [M+H]$^+$. $^1$H NMR (400 MHz, CD$_3$OD) δ 9.38 (s, 1H), 8.57-8.98 (m, 2H), 8.32-8.55 (m, 2H), 8.11-8.24 (m, 1H), 7.85-7.97 (m, 1H), 7.47-7.65 (m, 3H), 7.29 (br d, J=8.31 Hz, 1H), 6.16-6.34 (m, 1H), 2.40-2.57 (m, 1H), 1.96-2.11 (m, 1H), 0.59-0.77 (m, 1H), 0.34-0.51 (m, 2H), 0.15-0.23 (m, 1H), 0.00-0.07 (m, 2H).

Example 415: (R*)-5-(3-Chloro-2-fluoro-6-(1H-tetrazol-1-yl)phenyl)-2-(2-(N-methyl-4-oxo-4-(piperidin-1-yl)butanamido)-1-(4-(2-(trifluoromethyl)pyridin-4-yl)-1H-pyrazol-1-yl)ethyl)pyridine 1-oxide

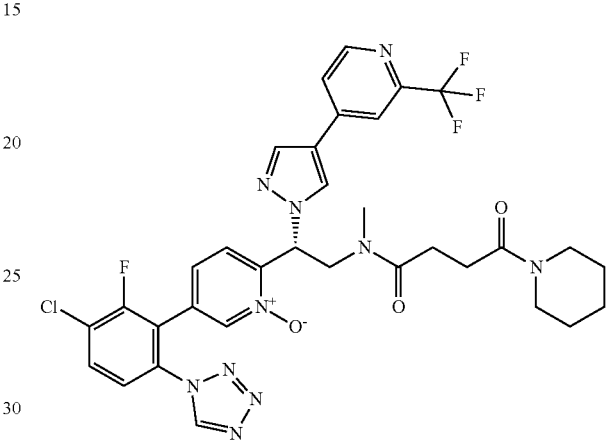

LC/MS: mass calculated for $C_{33}H_{31}ClF_4N_{10}O_3$: 726.2, measured (ES, m/z): 727.2 [M+H]$^+$. $^1$H NMR (300 MHz, DMSO-d$_6$) δ 9.68 (d, J=1.5 Hz, 1H), 8.80-8.90 (m, 1H), 8.60-8.70 (m, 1H), 8.40-8.47 (m, 1H), 8.02-8.29 (m, 3H), 7.83-7.94 (m, 1H), 7.62-7.80 (m, 2H), 7.17-7.26 (m, 1H), 6.19-6.40 (m, 1H), 3.93-4.40 (m, 2H), 3.34-3.47 (m, 3H), 2.60-2.72 (m, 3H), 2.48-2.52 (m, 2H), 2.27-2.45 (m, 3H), 1.33-1.59 (m, 6H). $^{19}$F NMR (282 MHz, DMSO-d$_6$) δ −66.58, −112.63.

Example 416: (S*)-5-(3-Chloro-2-fluoro-6-(1H-tetrazol-1-yl)phenyl)-2-(2-(N-methyl-4-oxo-4-(piperidin-1-yl)butanamido)-1-(4-(2-(trifluoromethyl)pyridin-4-yl)-1H-pyrazol-1-yl)ethyl)pyridine 1-oxide

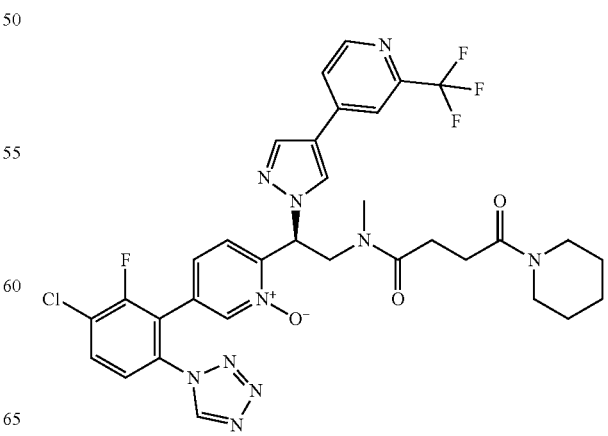

LC/MS: mass calculated for $C_{33}H_{31}ClF_4N_{10}O_3$: 726.2, measured (ES, m/z): 727.2 [M+H]$^+$. $^1$H NMR (300 MHz, DMSO-d$_6$) δ 9.68 (d, J=1.6 Hz, 1H), 8.80-8.90 (m, 1H), 8.62-8.69 (m, 1H), 8.26-8.49 (m, 2H), 8.02-8.18 (m, 2H), 7.86-7.91 (m, 1H), 7.62-7.80 (m, 2H), 7.18-7.27 (m, 1H), 6.18-6.40 (m, 1H), 3.91-4.30 (m, 2H), 3.38-3.42 (m, 3H), 2.60-2.72 (m, 4H), 2.15-2.45 (m, 2H), 1.20-1.59 (m, 8H). $^{19}$F NMR (282 MHz, DMSO-d$_6$) δ −66.58, −112.65.

Example 417: (R*)-5-(3-Chloro-2-fluoro-6-(1H-tetrazol-1-yl)phenyl)-2-(3-(difluoromethoxy)-1-(4-(2-(trifluoromethyl)pyrimidin-4-yl)-1H-pyrazol-1-yl)propyl)pyridine 1-oxide

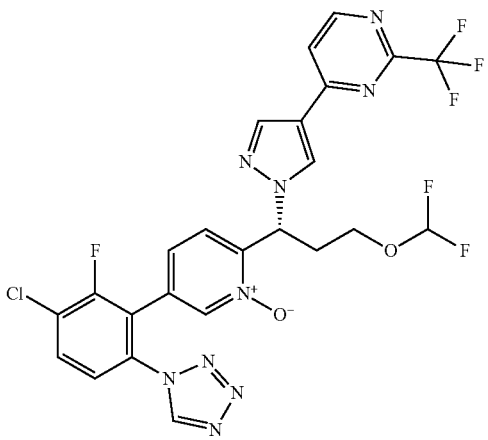 [SMILES: [O-][n+]1cc(-c2c(-n3cnnn3)ccc(Cl)c2F)ccc1[C@@H](CCOC(F)F)n1cc(-c2ccnc(C(F)(F)F)n2)cn1]

Step 1: 4-(1-(1-(5-Bromopyridin-2-yl)-3-((tert-butyldimethylsilyl)oxy)propyl)-1H-pyrazol-4-yl)-2-(trifluoromethyl)pyrimidine To a solution of 4-(1H-pyrazol-4-yl)-2-(trifluoromethyl)pyrimidine (1.0 g, 4.67 mmol, 1.1 equiv.) in CH$_3$CN (8 mL) was added Cs$_2$CO$_3$ (1.4 g, 4.25 mmol, 1.0 equiv.) under N$_2$. The reaction mixture was stirred for 0.5 h, then a solution of 1-(5-bromopyridin-2-yl)-3-((tert-butyldimethylsilyl)oxy) propyl methanesulfonate (1.8 g, 4.25 mmol, 1.0 equiv.) was added. The reaction mixture was stirred for 4 h at 90° C., then cooled to room temperature and quenched with water, extracted with EA, washed with brine, dried over Na$_2$SO$_4$ and concentrated under vacuum. The residue was purified by silica gel chromatography with EA/PE (0→66%) to yield 4-(1-(1-(5-bromopyridin-2-yl)-3-((tert-butyldimethylsilyl) oxy) propyl)-1H-pyrazol-4-yl)-2-(trifluoromethyl) pyrimidine as yellow oil. LC/MS: mass calculated for $C_{22}H_{27}BrF_3N_5OSi$: 541.11, measured (ES, m/z): 542.10, 544.15 [M+H, M+H+2]$^+$.

Step 2: 3-(5-Bromopyridin-2-yl)-3-(4-(2-(trifluoromethyl)pyrimidin-4-yl)-1H-pyrazol-1-yl)propan-1-ol To a solution of 4-(1-(1-(5-bromopyridin-2-yl)-3-((tert-butyldimethylsilyl)oxy)propyl)-1H-pyrazol-4-yl)-2-(trifluoromethyl)pyrimidine (1.5 g, 2.78 mmol, 1.0 equiv.) in THF (25 mL) was added TBAF (3.3 ml, 3.34 mmol, 1.2 equiv.). The reaction mixture was stirred for 2 h at room temperature, then quenched with water, extracted with EA, washed with brine, dried over Na$_2$SO$_4$ and concentrated under vacuum. The residue was purified by silica gel chromatography with EA/PE (0→100%) to yield 3-(5-bromopyridin-2-yl)-3-(4-(2-(trifluoromethyl) pyrimidin-4-yl)-1H-pyrazol-1-yl) propan-1-ol as yellow oil. LC/MS: mass calculated for $C_{16}H_{13}BrF_3N_5O$: 427.03, measured (ES, m/z): 428.00, 429.95 [M+H, M+H+2]$^+$.

Step 3: 4-(1-(1-(5-Bromopyridin-2-yl)-3-(difluoromethoxy)propyl)-1H-pyrazol-4-yl)-2-(trifluoromethyl)pyrimidine To a solution of 3-(5-bromopyridin-2-yl)-3-(4-(2-(trifluoromethyl)pyrimidin-4-yl)-1H-pyrazol-1-yl)propan-1-ol (0.79 g, 1.83 mmol, 1.0 equiv.) in CH$_3$CN (10 mL) was added CuI (0.14 g, 0.73 mmol, 0.4 equiv.) under N$_2$, then a solution of 2,2-difluoro-2-(fluorosulfonyl)acetic acid (0.49 g, 2.75 mmol, 2.0 equiv.) in CH$_3$CN (5 mL) was added. The reaction mixture was stirred for 0.5 h at 50° C., then cooled to room temperature and quenched with water, extracted with EA, washed with brine, dried over Na$_2$SO$_4$, and concentrated under vacuum. The residue was purified by silica gel chromatography with EA/PE (0→66%) to yield 4-(1-(1-(5-bromopyridin-2-yl)-3-(difluoromethoxy)propyl)-1H-pyrazol-4-yl)-2-(trifluoromethyl)pyrimidine as yellow oil. LC/MS: mass calculated for $C_{17}H_{13}BrF_5N_5O$: 477.02, measured (ES, m/z): 478.00, 480.00 [M+H, M+H+2]$^+$.

Step 4: 4-Chloro-2-(6-(3-(difluoromethoxy)-1-(4-(2-(trifluoromethyl)pyrimidin-4-yl)-1H-pyrazol-1-yl)propyl)pyridin-3-yl)-3-fluoroaniline To a solution of 4-(1-(1-(5-bromopyridin-2-yl)-3-(difluoromethoxy)propyl)-1H-pyrazol-4-yl)-2-(trifluoromethyl) pyrimidine (0.40 g, 0.84 mmol, 1.0 equiv.) and (6-amino-3-chloro-2-fluorophenyl)boronic acid (0.24 g, 1.27 mol, 1.5 equiv.) in 1,4-dioxane (8 mL) and water (2 mL) was added Pd(PPh$_3$)$_4$ (97 mg, 0.01 mmol, 0.1 equiv) and K$_2$CO$_3$ (0.35 g, 2.52 mmol, 3.0 equiv.) under N$_2$. The reaction mixture was stirred for 4 h at 90° C., then cooled to room temperature and quenched with water, extracted with EA, washed with brine, dried over Na$_2$SO$_4$ and concentrated under vacuum. The residue was purified by silica gel chromatography with EA/PE (0→66%) to yield 4-chloro-2-(6-(3-(difluoromethoxy)-1-(4-(2-(trifluoromethyl)pyrimidin-4-yl)-1H-pyrazol-1-yl)propyl)pyridin-3-yl)-3-fluoroaniline as yellow oil. LC/MS: mass calculated for $C_{23}H_{17}ClF_6N_6O$: 542.11, measured (ES, m/z): 543.10 [M+H]$^+$.

Step 5: 4-(1-(1-(5-(3-Chloro-2-fluoro-6-(1H-tetrazol-1-yl)phenyl)pyridin-2-yl)-3-(difluoromethoxy)propyl)-1H-pyrazol-4-yl)-2-(trifluoromethyl)pyrimidine To a solution of 4-chloro-2-(6-(3-(difluoromethoxy)-1-(4-(2-(trifluoromethyl)pyrimidin-4-yl)-1H-pyrazol-1-yl)propyl)pyridin-3-yl)-3-fluoroaniline (0.30 g, 0.55 mmol, 1.0 equiv.) and TMSN$_3$ (0.96 g, 8.29 mmol, 15.0 equiv.) in CH$_3$COOH (3 mL) was added trimethoxymethane (0.88 g, 8.29 mmol, 15.0 equiv.) under N$_2$. The reaction mixture was stirred for 15 h at room temperature, then concentrated under vacuum. The mixture was purified by reverse-phase chromatography (C18, 330 g, CH$_3$CN/H$_2$O (0.05% TFA)= 10%→70%) to yield 4-(1-(1-(5-(3-chloro-2-fluoro-6-(2H-pentazol-2-yl)phenyl)pyridin-2-yl)-3-(difluoromethoxy) propyl)-1H-pyrazol-4-yl)-2-(trifluoromethyl)pyrimidine as yellow oil. LC/MS: mass calculated for $C_{24}H_{16}ClF_6N_9O$: 595.11, measured (ES, m/z): 618.10 [M+Na]$^+$.

Step 6: (R)-5-(3-Chloro-2-fluoro-6-(1H-tetrazol-1-yl)phenyl)-2-(3-(difluoromethoxy)-1-(4-(2-(trifluoromethyl)pyrimidin-4-yl)-1H-pyrazol-1-yl)propyl)pyridine 1-oxide To a solution of 4-(1-(1-(5-(3-chloro-2-fluoro-6-(1H-tetrazol-1-yl)phenyl)pyridin-2-yl)-3-(difluoromethoxy)propyl)-1H-pyrazol-4-yl)-2-(trifluoromethyl)pyrimidine (0.13 g, 0.22 mmol, 1.0 equiv.) in MeOH (6 mL) and with ReMeO$_3$ (0.03 g, 0.11 mmol, 0.5 equiv.) and H$_2$O$_2$ (0.07 g, 2.18 mmol, 10.0 equiv.) was added under N$_2$. The reaction mixture was stirred 3 h at room temperature, then concentrated under vacuum. The mixture was purified by reverse-phase chromatography (C18, 330 g, CH$_3$CN/H$_2$O (0.05% TFA)=10%→70%) to yield 5-(3-chloro-2-fluoro-6-(1H-tetrazol-1-yl)phenyl)-2-(3-(difluoromethoxy)-1-(4-(2-(trifluoromethyl)pyrimidin-4-yl)-1H-pyrazol-1-yl)propyl)pyridine 1-oxide as a yellow oil. 80 mg of resulting residue was further purified by Prep-Chiral-HPLC. The collected fractions were combined and concentrated under vacuum to yield (R)-5-(3-chloro-2-fluoro-6-(1H-tetrazol-1-yl) phenyl)-2-(3-(difluoromethoxy)-1-(4-(2-(trifluoromethyl)pyrimidin-4-yl)-1H-pyrazol-1-yl)propyl)pyridine 1-oxide.

LC/MS: mass calculated for $C_{24}H_{16}ClF_6N_9O_2$: 611.10, measured (ES, m/z): 612.15 [M+H]$^+$. $^1$H NMR (300 MHz, CD$_3$OD): δ9.40 (s, 1H), 8.83 (d, J=5.4 Hz, 1H), 8.74 (s, 1H), 8.41 (s, 1H), 8.35 (s, 1H), 7.86-8.00 (m, 2H), 7.54-7.68 (m, 2H), 7.33 (d, J=8.3 Hz, 1H), 6.42 (dd, J=10.3, 4.5 Hz, 1H), 6.38 (t, J=75.0 Hz, 1H), 3.96-4.10 (m, 1H), 3.69-3.96 (m, 1H), 2.64-2.90 (m, 2H). $^{19}$F NMR (282 MHz, CD$_3$OD): δ −72.26, −86.21, −113.69.

Example 418: (S*)-5-(3-Chloro-2-fluoro-6-(1H-tetrazol-1-yl)phenyl)-2-(3-(difluoromethoxy)-1-(4-(2-(trifluoromethyl)pyrimidin-4-yl)-1H-pyrazol-1-yl)propyl)pyridine 1-oxide

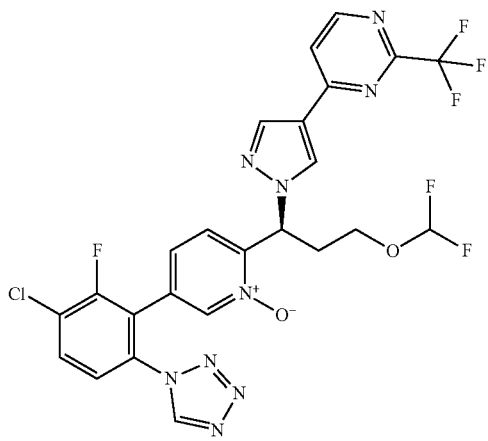 [SMILES: [O-][n+]1cc(-c2c(-n3cnnn3)ccc(Cl)c2F)ccc1[C@H](CCOC(F)F)n1cc(-c2ccnc(C(F)(F)F)n2)cn1]

LC/MS: mass calculated for $C_{24}H_{16}ClF_6N_9O_2$: 611.1, measured (ES, m/z): 612.05 [M+H]$^+$. $^1$H NMR (300 MHz, CD$_3$OD) δ 9.40 (s, 1H), 8.83 (d, J=5.4 Hz, 1H), 8.74 (s, 1H), 8.32-8.43 (m, 2H), 7.86-8.00 (m, 2H), 7.54-7.68 (m, 2H), 7.29-7.35 (m, 1H), 6.01-6.66 (m, 2H), 3.91-4.01 (m, 1H), 3.67-3.80 (m, 1H), 2.60-2.86 (m, 2H). $^{19}$F NMR (282 MHz, CD$_3$OD) δ −72.26, −86.22, −113.69.

Example 419: (R*)-5-(3-Chloro-2-fluoro-6-(1H-tetrazol-1-yl)phenyl)-2-(2-(N-methylacetamido)-1-(4-(2-(trifluoromethyl)pyridin-4-yl)-1H-pyrazol-1-yl)ethyl)pyridine 1-oxide

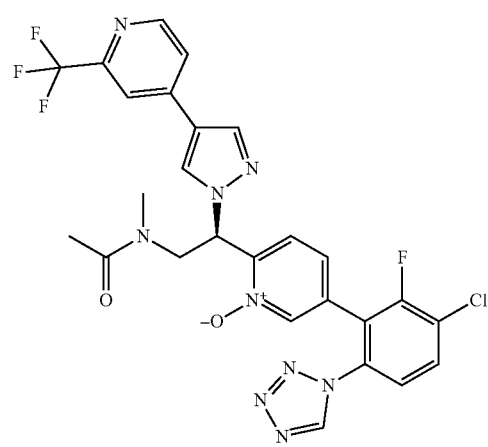

LC/MS: mass calculated for $C_{26}H_{20}ClF_4N_9O_2$: 601.1, measured (ES, m/z): 602.0 [M+H]$^+$. $^1$H NMR (300 MHz, DMSO-d$_6$) δ 9.69 (d, J=4.0 Hz, 1H), 8.89 (d, J=10.0 Hz, 1H), 8.62-8.69 m, 1H), 8.29-8.51 (m, 2H), 8.00-8.18 (m, 2H), 7.85-7.96 (m, 1H), 7.61-7.78 (m, 2H), 7.18-7.28 (m, 1H), 6.20-6.32 (m, 1H), 3.84-4.35 (m, 2H), 2.70-2.80 (m, 3H), 1.80-1.98 (m, 3H). $^{19}$F NMR (282 MHz, DMSO-d$_6$) δ −66.50, −112.65.

Example 420: (S*)-5-(3-Chloro-2-fluoro-6-(1H-tetrazol-1-yl)phenyl)-2-(2-(N-methylacetamido)-1-(4-(2-(trifluoromethyl)pyridin-4-yl)-1H-pyrazol-1-yl)ethyl)pyridine 1-oxide

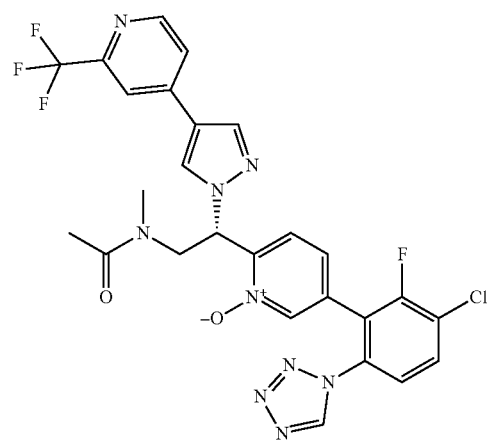

LC/MS: mass calculated for $C_{26}H_{20}ClF_4N_9O_2$: 601.1, measured (ES, m/z): 602.0 [M+H]$^+$. $^1$H NMR (300 MHz, DMSO-d$_6$) δ 9.69 (d, J=3.9 Hz, 1H), 8.89 (d, J=10.0 Hz, 1H), 8.60-8.70 (m, 1H), 8.28-8.52 (m, 2H), 8.00-8.18 (m, 2H), 7.85-7.96 (m, 1H), 7.75 (dd, J=8.7, 1.5 Hz, 1H), 7.60-7.68 (m, 1H), 7.16-7.28 (m, 1H), 6.20-6.32 (m, 1H), 3.88-4.31 (m, 2H), 2.72 (d, J=6.7 Hz, 3H), 1.80-1.92 (m, 3H). $^{19}$F NMR (282 MHz, DMSO-d$_6$) δ −66.53, −112.64.

Example 421: (R*)-4-(1-(1-(5-(3-Chloro-2-fluoro-6-(1H-tetrazol-1-yl)phenyl)-1-oxidopyridin-2-yl)-2-(4-fluoro-1H-pyrazol-1-yl)ethyl)-1H-pyrazol-4-yl)-2-(difluoromethyl)pyridine 1-oxide

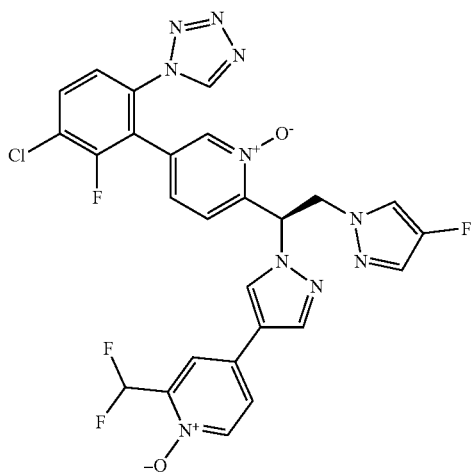

LC/MS: mass calculated for $C_{26}H_{17}ClF_4N_{10}O_2$: 612.1, measured (ES, m/z): 613.1 [M+H]$^+$. $^1$H NMR (400 MHz, DMSO-d$_6$) δ 9.69 (s, 1H), 8.65 (d, J=0.7 Hz, 1H), 8.51 (d, J=1.6 Hz, 1H), 8.35 (d, J=6.9 Hz, 1H), 8.30 (s, 1H), 8.02-8.09 (m, 1H), 7.95 (d, J=2.6 Hz, 1H), 7.76-7.82 (m, 2H), 7.69 (dd, J=4.6, 0.8 Hz, 1H), 7.10-7.48 (m, 4H), 6.44-6.56 (m, 1H), 4.97-5.02 (m, 1H), 4.84-4.92 (m, 1H). $^{19}$F NMR (376 MHz, DMSO-d$_6$) δ −112.62, −122.81, −177.76.

Example 422: (S*)-4-(1-(1-(5-(3-Chloro-2-fluoro-6-(1H-tetrazol-1-yl)phenyl)-1-oxidopyridin-2-yl)-2-(4-fluoro-1H-pyrazol-1-yl)ethyl)-1H-pyrazol-4-yl)-2-(difluoromethyl)pyridine 1-oxide

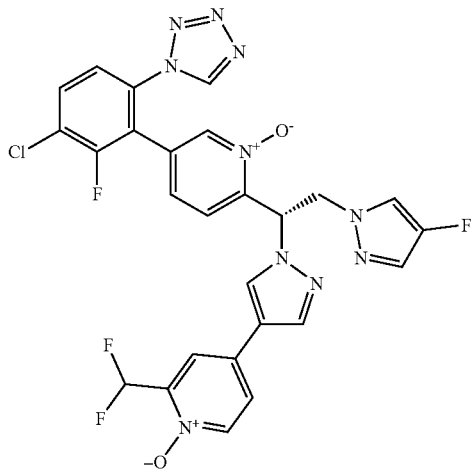

LC/MS: mass calculated for $C_{26}H_{17}ClF_4N_{10}O_2$: 612.1, measured (ES, m/z): 613.1 [M+H]$^+$. $^1$H NMR (400 MHz, DMSO-d$_6$) δ 9.69 (s, 1H), 8.65 (s, 1H), 8.51 (s, 1H), 8.35 (d, J=6.8 Hz, 1H), 8.30 (s, 1H), 8.07 (t, J=8.2 Hz, 1H), 7.95 (d, J=2.6 Hz, 1H), 7.73-7.83 (m, 2H), 7.69 (d, J=4.6 Hz, 1H), 7.16-7.50 (m, 4H), 6.48-6.54 (m, 1H), 4.85-5.04 (m, 2H). $^{19}$F NMR (376 MHz, DMSO-d$_6$) δ −112.62, −122.81, −177.76.

Example 423: 5-(3-Chloro-2-fluoro-6-(1H-tetrazol-1-yl)phenyl)-2-(2-(N-methyltetrahydro-2H-pyran-4-carboxamido)-1-(4-(2-(trifluoromethyl)pyridin-4-yl)-1H-pyrazol-1-yl)ethyl)pyridine 1-oxide

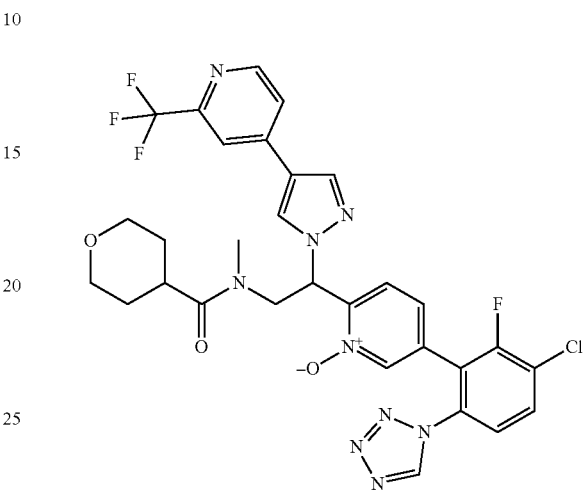

LC/MS: mass calculated for $C_{30}H_{26}ClF_4N_9O_3$: 671.2, measured (ES, m/z): 672.1 [M+H]$^+$. $^1$H NMR (300 MHz, DMSO-d$_6$) δ 9.48 (s, 1H), 8.60-8.80 (m, 2H), 8.13-8.36 (m, 2H), 7.88-8.01 (m, 3H), 7.59-7.69 (m, 2H), 7.16-7.27 (m, 1H), 6.14-6.32 (m, 1H), 3.90-4.40 (m, 2H), 3.60-3.72 (m, 2H), 3.25-3.35 (m, 2H), 2.70-2.85 (m, 4H), 1.42-1.56 (m, 4H). $^{19}$F NMR (282 MHz, DMSO-d$_6$) δ −66.54, −74.63, −112.71.

Example 424: 5-(3-Chloro-2-fluoro-6-(1H-tetrazol-1-yl)phenyl)-2-(1-(4-(2-cyanopyridin-4-yl)-1H-pyrazol-1-yl)-2-(1-methyl-1H-pyrazol-4-yl)ethyl)pyridine 1-oxide trifluoroacetic acid

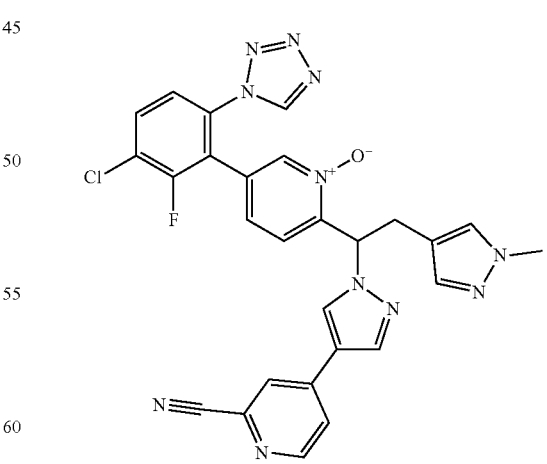

LC/MS: mass calculated for $C_{27}H_{19}ClFN_{11}O \cdot C_{27}H_{19}ClFN_{11}O$: 567.96, measured (ES, m/z): 568.2 [M+H]$^+$. $^1$H NMR (300 MHz, DMSO-d$_6$) δ 9.68 (s, 1H), 8.75 (s, 1H), 8.63 (dd, J=5.3, 0.8 Hz, 1H), 8.45 (s, 1H), 8.31 (d, J=1.7 Hz, 2H), 8.00-8.07 (m, 1H), 7.90 (dd, J=5.3, 1.8 Hz, 1H), 7.74 (dd, J=8.7, 1.6 Hz, 1H), 7.41 (d, J=8.3 Hz, 1H), 7.29 (s, 1H), 7.12-7.19 (m, 1H), 7.00 (s, 1H), 6.00-6.08 (m, 1H), 3.69 (s, 3H), 3.30-3.48 (m, 2H). $^{19}$F NMR (282 MHz, DMSO-$d_6$) δ −74.74, −112.70.

Example 425: (R*)-5-(3-Chloro-2-fluoro-6-(1H-tetrazol-1-yl)phenyl)-2-(2-(N-methylbenzamido)-1-(4-(2-(trifluoromethyl)pyridin-4-yl)-1H-pyrazol-1-yl)ethyl)pyridine 1-oxide

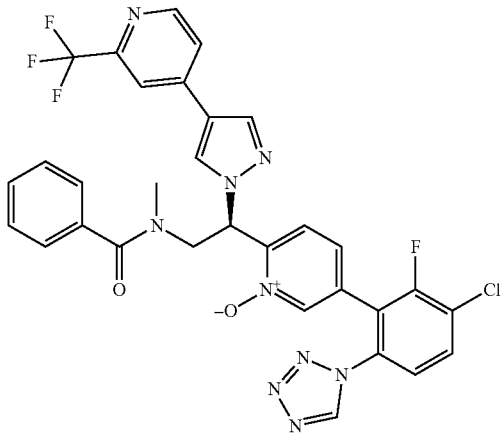

LC/MS: mass calculated for $C_{31}H_{22}ClF_4N_9O_2$: 663.2, measured (ES, m/z): 664.1 [M+H]$^+$. $^1$H NMR (300 MHz, DMSO-$d_6$) δ 9.69 (s, 1H), 9.02 (s, 1H), 8.67 (d, J=5.2 Hz, 1H), 8.48 (s, 1H), 8.32 (s, 1H), 8.02-8.20 (m, 2H), 7.72-7.96 (m, 3H), 7.19-7.43 (m, 6H), 6.40-6.51 (m, 1H), 4.11-4.42 (m, 2H), 2.90-3.10 (m, 1H), 2.69 (s, 2H). $^{19}$F NMR (282 MHz, DMSO-$d_6$) δ −66.51, −112.65.

Example 426: (S*)-5-(3-Chloro-2-fluoro-6-(1H-tetrazol-1-yl)phenyl)-2-(2-(N-methylbenzamido)-1-(4-(2-(trifluoromethyl)pyridin-4-yl)-1H-pyrazol-1-yl)ethyl)pyridine 1-oxide trifluoroacetic acid

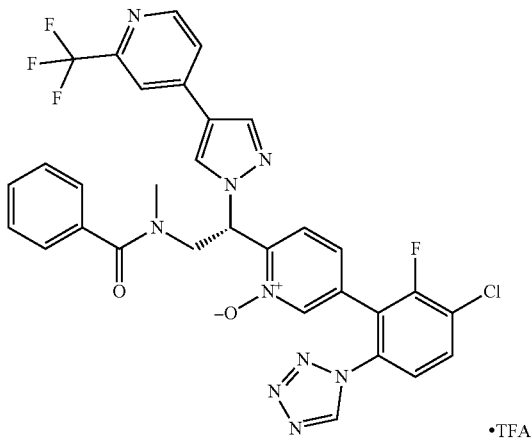

LC/MS: mass calculated for $C_{31}H_{22}ClF_4N_9O_2$: 663.2, measured (ES, m/z): 664.1 [M+H]$^+$. $^1$H NMR (300 MHz, DMSO-$d_6$) δ 9.69 (s, 1H), 9.01 (s, 1H), 8.67 (d, J=5.2 Hz, 1H), 8.47 (s, 1H), 8.10-8.34 (m, 2H), 8.00-8.07 (m, 1H), 7.92 (s, 1H), 7.70-7.82 (m, 2H), 7.31-7.41 (m, 3H), 7.00-7.26 (m, 3H), 6.28-6.52 (m, 1H), 3.90-4.40 (m, 2H), 2.90-3.10 (m, 1H), 2.69 (s, 2H). $^{19}$F NMR (282 MHz, DMSO-$d_6$) δ (ppm) −66.51, −74.22, −112.66.

Example 427: (R*)-5-(3-Chloro-2-fluoro-6-(1H-tetrazol-1-yl)phenyl)-2-(2-(4-(piperidine-1-carbonyl)-1H-pyrazol-1-yl)-1-(4-(2-(trifluoromethyl)pyridin-4-yl)-1H-pyrazol-1-yl)ethyl)pyridine 1-oxide

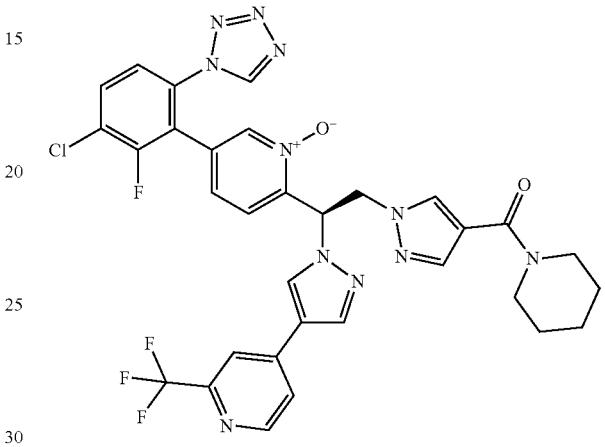

LC/MS: mass calculated for $C_{32}H_{26}ClF_4N_{11}O_2$: 707.2, measured (ES, m/z): 708.3 [M+H]$^+$. $^1$H NMR (300 MHz, DMSO-$d_6$) δ 9.64 (s, 1H), 8.58-8.64 (m, 2H), 8.48 (s, 1H), 8.35 (s, 1H), 7.96-8.08 (m, 2H), 7.82 (d, J=5.1 Hz, 1H), 7.64-7.76 (m, 2H), 7.59 (s, 1H), 7.53 (d, J=8.4 Hz, 1H), 7.23 (d, J=7.7 Hz, 1H), 6.45-6.56 (m, 1H), 4.91-5.14 (m, 2H), 3.30 (brs, 4H), 1.20-1.50 (m, 6H).

Example 428: (S*)-5-(3-Chloro-2-fluoro-6-(1H-tetrazol-1-yl)phenyl)-2-(2-(4-(piperidine-1-carbonyl)-1H-pyrazol-1-yl)-1-(4-(2-(trifluoromethyl)pyridin-4-yl)-1H-pyrazol-1-yl)ethyl)pyridine 1-oxide

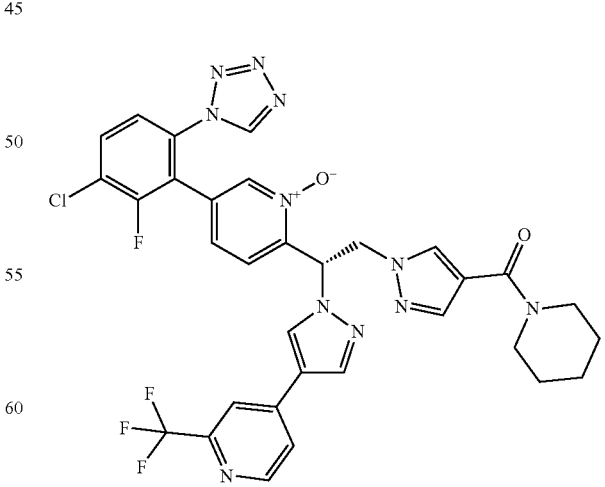

LC/MS: mass calculated for $C_{32}H_{26}ClF_4N_{11}O_2$: 707.2, measured (ES, m/z): 708.25 [M+H]$^+$. $^1$H NMR (300 MHz, DMSO-$d_6$) δ 9.65 (s, 1H), 8.59-8.69 (m, 2H), 8.49 (s, 1H), 8.36 (s, 1H), 7.97-8.09 (m, 2H), 7.83 (d, J=5.2 Hz, 1H), 7.65-7.77 (m, 2H), 7.59 (s, 1H), 7.52 (d, J=8.3 Hz, 1H), 7.23 (d, J=8.3 Hz, 1H), 6.45-6.58 (m, 1H), 4.87-5.15 (m, 2H), 3.31 (s, 4H), 1.05-1.58 (m, 6H).

Example 429: (R*)-4-(1-(1-(5-(3-Chloro-2-fluoro-6-(1H-tetrazol-1-yl)phenyl)-1-oxidopyridin-2-yl)-2-(4-fluoro-1H-pyrazol-1-yl)ethyl)-1H-pyrazol-4-yl)-2-isopropylpyridine 1-oxide

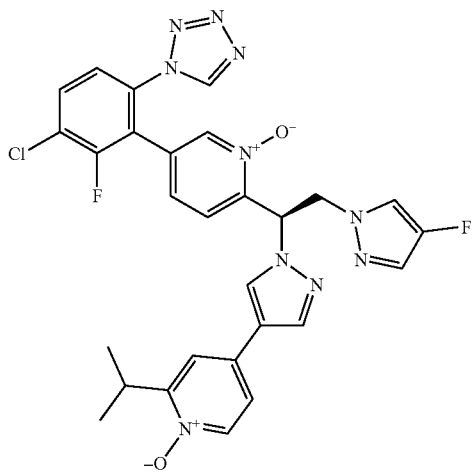

LC/MS: mass calculated for $C_{28}H_{23}ClF_2N_{10}O_2$: 604.2, measured (ES, m/z): 605.2 [M+H]$^+$. $^1$H NMR (300 MHz, DMSO-d$_6$) δ 9.69 (s, 1H), 8.53 (d, J=7.3 Hz, 2H), 8.14-8.25 (m, 2H), 8.00-8.09 (m, 1H), 7.77 (dd, J=8.8, 1.5 Hz, 1H), 7.67 (d, J=4.6 Hz, 1H), 7.55 (d, J=2.6 Hz, 1H), 7.43-7.51 (m, 2H), 7.39 (d, J=8.3 Hz, 1H), 7.22 (dd, J=8.2, 1.7 Hz, 1H), 6.43-6.57 (m, 1H), 4.80-5.05 (m, 2H), 3.52-3.63 (m, 1H), 1.18-1.27 (m, 6H). $^{19}$F NMR (282 MHz, DMSO-d$_6$) δ −177.80, −112.65.

Example 430: (S*)-4-(1-(1-(5-(3-Chloro-2-fluoro-6-(1H-tetrazol-1-yl)phenyl)-1-oxidopyridin-2-yl)-2-(4-fluoro-1H-pyrazol-1-yl)ethyl)-1H-pyrazol-4-yl)-2-isopropylpyridine 1-oxide

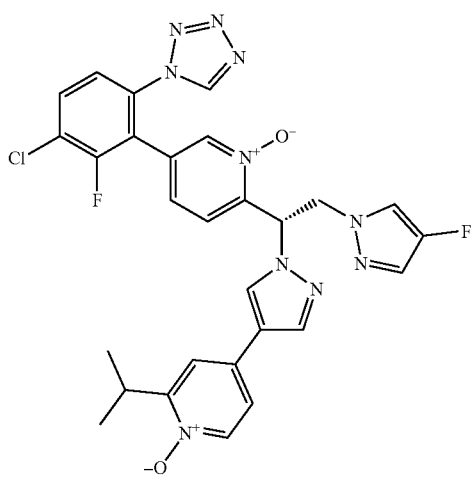

LC/MS: mass calculated for $C_{28}H_{23}ClF_2N_{10}O_2$: 604.17, measured (ES, m/z): 605.25[M+H]$^+$. $^1$H NMR (300 MHz, DMSO-d$_6$) δ 9.69 (s, 1H), 8.53 (d, J=7.3 Hz, 2H), 8.14-8.25 (m, 2H), 8.00-8.09 (m, 1H), 7.77 (dd, J=8.8, 1.5 Hz, 1H), 7.67 (d, J=4.6 Hz, 1H), 7.55 (d, J=2.6 Hz, 1H), 7.43-7.51 (m, 2H), 7.39 (d, J=8.3 Hz, 1H), 7.22 (dd, J=8.2, 1.7 Hz, 1H), 6.45-6.58 (m, 1H), 4.80-5.10 (m, 2H), 3.52-3.63 (m, 1H), 1.24 (d, J=6.8 Hz, 6H). $^{19}$F NMR (282 MHz, DMSO-d$_6$) δ −177.80, −112.65.

Example 431: 5-(3-Chloro-2-fluoro-6-(1H-tetrazol-1-yl)phenyl)-2-(3-(difluoromethoxy)-1-(4-(1-methyl-6-oxo-1,6-dihydropyridazin-4-yl)-1H-pyrazol-1-yl)propyl)pyridine 1-oxide trifluoroacetic acid

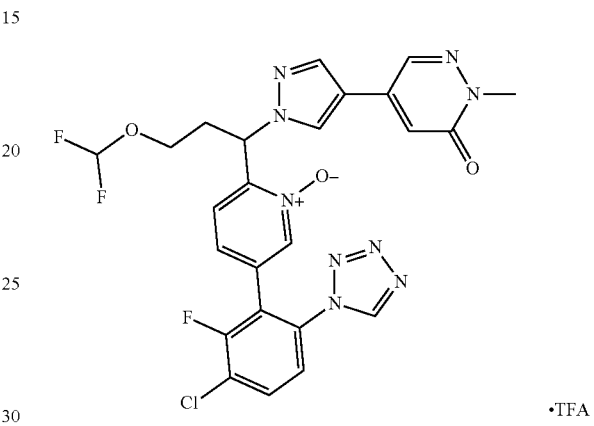

·TFA

LC/MS: mass calculated for $C_{24}H_{19}ClF_3N_9O_3$: 573.13, measured (ES, m/z): 574.1 [M+H]$^+$. $^1$H NMR (400 MHz, DMSO-d$_6$) δ 9.69 (s, 1H), 8.77 (s, 1H), 8.46 (d, J=1.6 Hz, 1H), 8.25-8.31 (m, 2H), 8.06 (dd, J=8.7, 7.8 Hz, 1H), 7.76 (dd, J=8.7, 1.5 Hz, 1H), 7.34 (d, J=8.3 Hz, 1H), 7.19 (dd, J=8.3, 1.7 Hz, 1H), 7.15 (d, J=2.2 Hz, 1H), 6.63 (t, J=75.7 Hz, 1H), 6.13-6.21 (m 1H), 3.80-3.87 (m, 1H), 3.62-3.71 (m, 1H), 3.63 (s, 3H), 2.60-2.80 (m, 2H). $^{19}$F NMR (376 MHz, DMSO-d$_6$) δ −74.82, −83.27, −83.28, −112.71.

Example 432: (R*)-2-(1-(4-(6-Amino-2-fluoropyridin-3-yl)-1H-pyrazol-1-yl)-2-(4-fluoro-1H-pyrazol-1-yl)ethyl)-5-(3-chloro-2-fluoro-6-(1H-tetrazol-1-yl)phenyl)pyridine 1-oxide

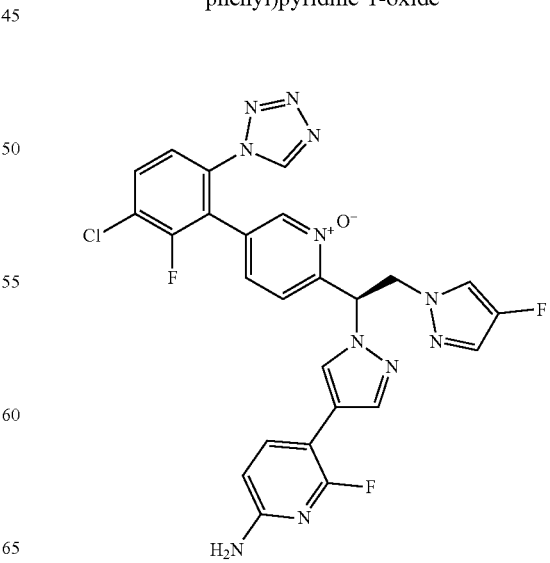

LC/MS: mass calculated for $C_{25}H_{17}ClF_3NO_{11}$: 579.1, measured (ES, m/z): 580.2 [M+H]$^+$. $^1$H NMR (400 MHz, DMSO-d$_6$) δ 9.68 (d, J=3.6 Hz, 1H), 8.48-8.54 (m, 1H), 8.00-8.11 (m, 2H), 7.89 (d, J=1.5 Hz, 1H), 7.70-7.81 (m, 2H), 7.58-7.70 (m, 1H), 7.44 (dd, J=4.3, 0.8 Hz, 1H), 7.16-7.33 (m, 2H), 6.51 (dd, J=9.5, 4.5 Hz, 1H), 6.25-6.44 (m, 3H), 5.09-5.84 (m, 2H).

Example 433: (S*)-2-(1-(4-(6-Amino-2-fluoropyridin-3-yl)-1H-pyrazol-1-yl)-2-(4-fluoro-1H-pyrazol-1-yl)ethyl)-5-(3-chloro-2-fluoro-6-(1H-tetrazol-1-yl)phenyl)pyridine 1-oxide LC/MS: mass calculated for $C_{27}H_{24}ClF_2N_9O_2$: 579.17, measured (ES, m/z): 580.1 [M+H]$^+$. $^1$H NMR (300 MHz, DMSO-d$_6$) δ 9.68 (d, J=1.4 Hz, 1H), 8.70-8.80 (m, 1H), 8.40-8.45 (m, 1H), 8.13-8.32 (m, 2H), 7.99-8.07 (m, 1H), 7.62-7.77 (m, 2H), 7.50-7.60 (m, 1H), 7.35-7.43 (m, 1H), 7.16-7.27 (m, 1H), 6.16-6.35 (m, 1H), 3.92-4.37 (m, 2H), 2.67-2.89 (m, 4H), 0.66-0.95 (m, 6H). $^{19}$F NMR (282 MHz, DMSO-d$_6$) δ −69.13, −74.65, −112.68.

Example 435: (R*)-5-(3-Chloro-6-(difluoromethyl)-2-fluorophenyl)-2-(2-(4-fluoro-1H-pyrazol-1-yl)-1-(4-(2-(trifluoromethyl)pyridin-4-yl)-1H-pyrazol-1-yl)ethyl)pyridine 1-oxide

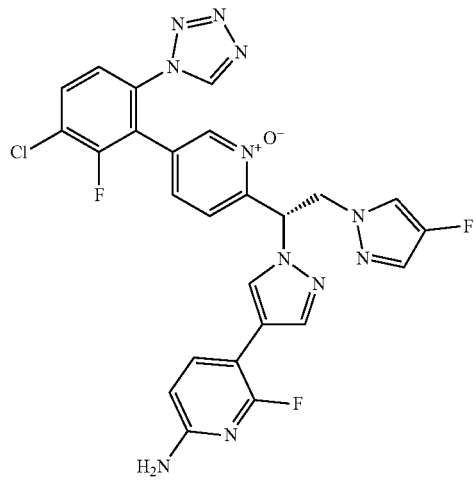

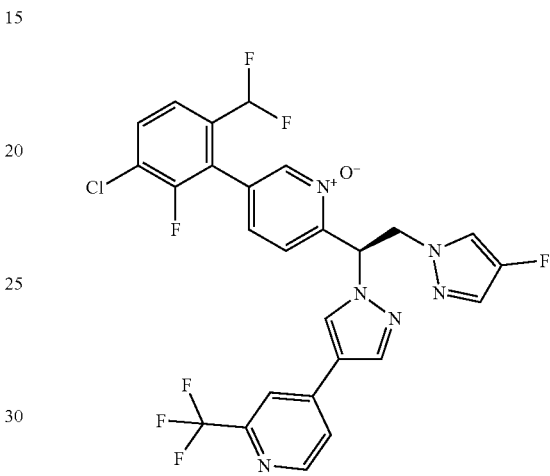

LC/MS: mass calculated for $C_{25}H_{17}ClF_3N_{11}O$: 579.1, measured (ES, m/z): 580.2 [M+H]$^+$. $^1$H NMR (400 MHz, DMSO-d$_6$) δ 9.68 (s, 1H), 8.48-8.53 (m, 1H), 8.02-8.11 (m, 2H), 7.89 (d, J=1.5 Hz, 1H), 7.72-7.81 (m, 2H), 7.61 (dd, J=4.7, 0.9 Hz, 1H), 7.44 (dd, J=4.2, 0.8 Hz, 1H), 7.28 (d, J=8.3 Hz, 1H), 7.20 (dd, J=8.3, 1.6 Hz, 1H), 6.51 (dd, J=9.4, 4.6 Hz, 1H), 6.35 (d, J=8.1 Hz, 3H), 4.78-5.04 (m, 2H).

Example 434: 5-(3-Chloro-2-fluoro-6-(1H-tetrazol-1-yl)phenyl)-2-(1-(4-(2-fluoropyridin-4-yl)-1H-pyrazol-1-yl)-2-(N-methylisobutyramido)ethyl)pyridine 1-oxide trifluoroacetic acid LC/MS: mass calculated for $C_{26}H_{16}ClF_7N_6O$: 596.1, measured (ES, m/z): 597.05 [M+H]$^+$. $^1$H NMR (400 MHz, DMSO-d$_6$) δ 8.82 (s, 1H), 8.68 (d, J=5.2 Hz, 1H), 8.59 (d, J=1.6 Hz, 1H), 8.43 (s, 1H), 8.11-8.14 (m, 1H), 7.87-7.95 (m, 2H), 7.72 (dd, J=4.6, 0.9 Hz, 1H), 7.56-7.65 (m, 2H), 7.42-7.52 (m, 2H), 6.72-7.05 (m, 1H), 6.58-6.68 (m, 1H), 5.01-5.15 (m, 1H), 4.88-5.00 (m, 1H). $^{19}$F NMR (376 MHz, DMSO-d$_6$) δ −66.50, −115.19, −177.82.

Example 436: (S*)-5-(3-Chloro-6-(difluoromethyl)-2-fluorophenyl)-2-(2-(4-fluoro-1H-pyrazol-1-yl)-1-(4-(2-(trifluoromethyl)pyridin-4-yl)-1H-pyrazol-1-yl)ethyl)pyridine 1-oxide

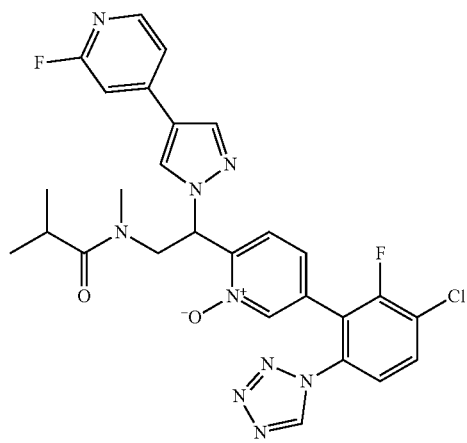

·TFA

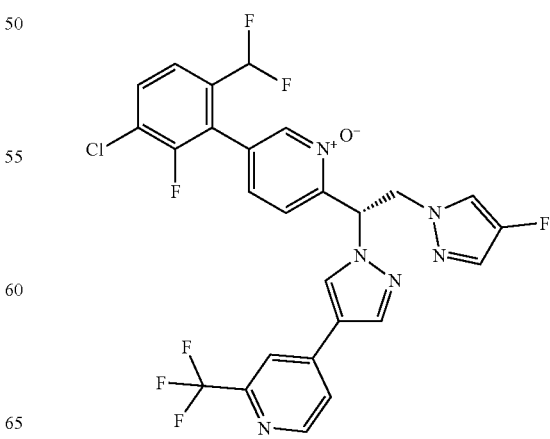

LC/MS: mass calculated for $C_{26}H_{16}ClF_7N_6O$: 596.1, measured (ES, m/z): 597.1 [M+H]+. $^1$H NMR (400 MHz, DMSO-d$_6$) δ 8.82 (s, 1H), 8.68 (d, J=5.2 Hz, 1H), 8.59 (d, J=1.6 Hz, 1H), 8.43 (s, 1H), 8.11-8.14 (m, 1H), 7.86-7.95 (m, 2H), 7.72 (dd, J=4.7, 0.9 Hz, 1H), 7.60-7.70 (m, 2H), 7.42-7.52 (m, 2H), 6.89 (t, J=53.9 Hz, 1H), 6.64 (dd, J=9.9, 4.3 Hz, 1H), 5.00-5.14 (m, 1H), 4.92-4.99 (m, 1H). $^{19}$F NMR (376 MHz, DMSO-d$_6$) δ −66.53, −115.19, −177.82.

Example 437: 5-(5-Chloro-2-(1H-tetrazol-1-yl)phenyl)-2-(2-(3-(tetrahydro-2H-pyran-4-yl)-1H-pyrazol-1-yl)-1-(4-(2-(trifluoromethyl)pyridin-4-yl)-1H-pyrazol-1-yl)ethyl)pyridine 1-oxide

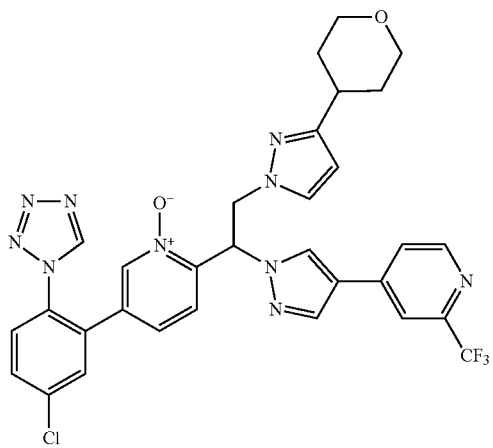 [SMILES: [O-][n+]1cc(-c2cc(Cl)ccc2-n2cnnn2)ccc1C(Cn1ccc(C2CCOCC2)n1)n1cc(-c2ccnc(C(F)(F)F)c2)cn1]

LC/MS: mass calculated for $C_{31}H_{26}ClF_3N_{10}O_2$: 662.2, measured (ES, m/z): 663.6 [M]+. $^1$H NMR (400 MHz, CD$_3$OD) δ ppm 9.37 (d, J=5.9 Hz, 1H), 8.57-8.64 (m, 1H), 8.49-8.56 (m, 1H), 8.32 (br s, 1H), 8.14-8.19 (m, 1H), 7.97-8.00 (m, 2H), 7.75-7.82 (m, 2H), 7.70-7.75 (m, 2H), 7.63-7.69 (m, 2H), 7.63-7.69 (m, 2H), 7.20 (br d, J=7.3 Hz, 1H), 6.48-6.69 (m, 2H), 4.44-4.72 (m, 1H), 4.29-4.44 (m, 1H), 3.79-3.99 (m, 1H), 3.36-3.51 (m, 2H), 2.64-2.79 (m, 1H), 1.58-1.84 (m, 4H).

Example 438: 2-(1-(4-(5-Carboxy-1H-pyrrol-3-yl)-1H-pyrazol-1-yl)-2-cyclopropylethyl)-5-(3-chloro-6-(difluoromethyl)-2-fluorophenyl)pyridine 1-oxide

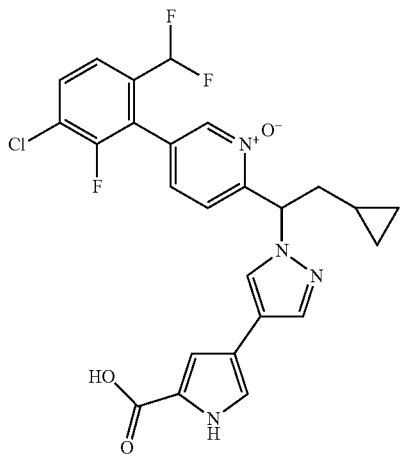

LC/MS: mass calculated for $C_{25}H_{20}ClF_3N_4O_3$: 516.11, measured (ES, m/z): 517.15 [M+H]+. $^1$H NMR (400 MHz, CD$_3$OD) δ 8.43 (s, 1H), 8.11 (s, 1H), 7.69-7.84 (m, 2H), 7.59 (d, J=8.5 Hz, 1H), 7.50 (d, J=2.3 Hz, 2H), 7.20 (d, J=1.7 Hz, 1H), 7.04 (d, J=1.7 Hz, 1H), 6.66 (t, J=54.2 Hz, 1H), 6.26 (dd, J=10.4, 3.9 Hz, 1H), 2.50-2.61 (m, 1H), 1.90-2.08 (m, 1H), 0.72-0.83 (m, 1H), 0.38-0.42 (m, 2H), 0.20-0.30 (m, 1H), 0.08-0.16 (m, 1H).

Example 439: (R*)-5-(3-Chloro-2-fluoro-6-(1H-tetrazol-1-yl)phenyl)-2-(2-(N-methylisobutyramido)-1-(4-(2-(trifluoromethyl)pyridin-4-yl)-1H-pyrazol-1-yl)ethyl)pyridine 1-oxide

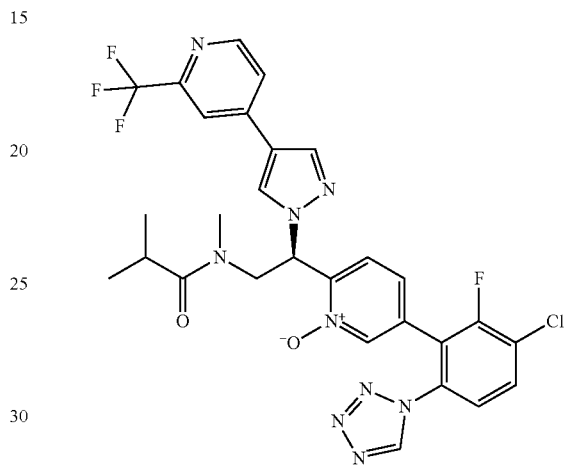

LC/MS: mass calculated for $C_{28}H_{24}ClF_4N_9O_2$: 629.17, measured (ES, m/z): 630.15 [M+H]+. $^1$H NMR (300 MHz, DMSO-d$_6$) δ 9.70 (d, J=1.4 Hz, 1H), 8.80-8.90 (m, 1H), 8.63-8.70 (m, 1H), 8.23-8.58 (m, 2H), 8.01-8.17 (m, 2H), 7.88-7.95 (m, 1H), 7.64-7.81 (m, 2H), 7.18-7.26 (m, 1H), 6.10-6.61 (m, 1H), 3.89-4.53 (m, 2H), 2.67-2.87 (m, 4H), 0.65-1.00 (m, 6H). $^{19}$F NMR (282 MHz, DMSO-d$_6$) δ −66.53, −112.67.

Example 440: (S*)-5-(3-Chloro-2-fluoro-6-(1H-tetrazol-1-yl)phenyl)-2-(2-(N-methylisobutyramido)-1-(4-(2-(trifluoromethyl)pyridin-4-yl)-1H-pyrazol-1-yl)ethyl)pyridine 1-oxide

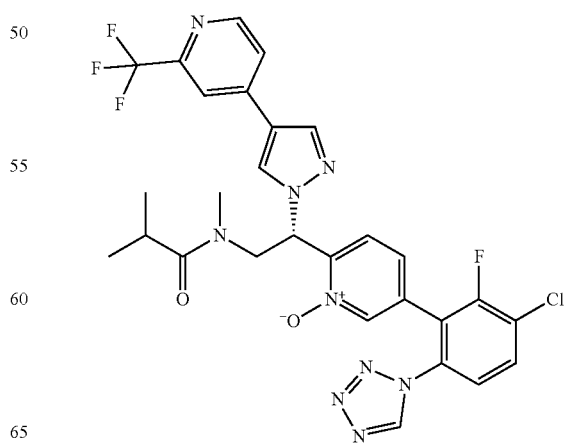

LC/MS: mass calculated for $C_{28}H_{24}ClF_4N_9O_2$: 629.17, measured (ES, m/z): 630.15 [M+H]$^+$. $^1$H NMR (300 MHz, DMSO-d$_6$) δ 9.70 (d, J=1.4 Hz, 1H), 8.80-8.90 (m, 1H), 8.63-8.70 (m, 1H), 8.24-8.56 (m, 2H), 8.01-8.17 (m, 2H), 7.87-7.94 (m, 1H), 7.64-7.81 (m, 2H), 7.18-7.28 (m, 1H), 6.16-6.47 (m, 1H), 3.89-4.47 (m, 2H), 2.67-2.97 (m, 4H), 0.64-1.02 (m, 6H). $^{19}$F NMR (282 MHz, DMSO-d$_6$) δ −66.53, −112.67.

Example 441: (S*)-5-(3-Chloro-2-fluoro-6-(1H-tetrazol-1-yl)phenyl)-2-(2-(N-methylpivalamido)-1-(4-(2-(trifluoromethyl)pyridin-4-yl)-1H-pyrazol-1-yl)ethyl)pyridine 1-oxide

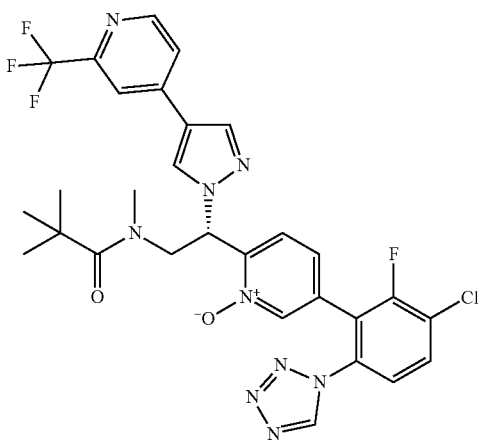

LC/MS: mass calculated for $C_{29}H_{26}ClF_4N_9O_2$: 643.18, measured (ES, m/z): 644.20 [M+H]$^+$. $^1$H NMR (300 MHz, DMSO-d$_6$) δ 9.71 (s, 1H), 8.87 (s, 1H), 8.67 (d, J=5.2 Hz, 1H), 8.45 (d, J=1.4 Hz, 1H), 8.32 (s, 1H), 8.16 (s, 1H), 8.00-8.09 (m, 1H), 7.90-7.98 (m, 1H), 7.72-7.83 (m, 2H), 7.19-7.30 (m, 1H), 6.30-6.38 (m, 1H), 3.94-4.22 (m, 2H), 2.79 (s, 3H), 1.11 (s, 9H). $^{19}$F NMR (282 MHz, DMSO-d$_6$) δ −66.53, −112.69.

Example 442: (R*)-5-(3-Chloro-2-fluoro-6-(1H-tetrazol-1-yl)phenyl)-2-(2-(N-methylpivalamido)-1-(4-(2-(trifluoromethyl)pyridin-4-yl)-1H-pyrazol-1-yl)ethyl)pyridine 1-oxide

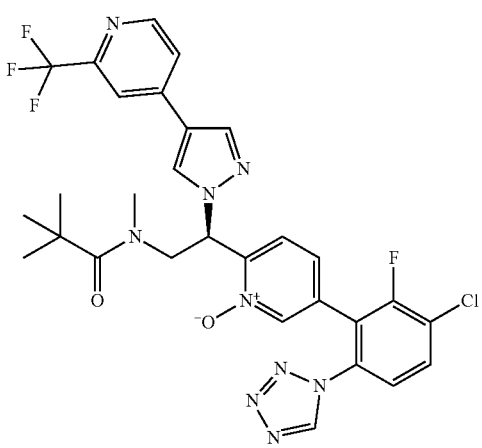

LC/MS: mass calculated for $C_{29}H_{26}ClF_4N_9O_2$: 643.18, measured (ES, m/z): 644.15 [M+H]$^+$. $^1$H NMR (400 MHz, DMSO-d$_6$) δ 9.70 (s, 1H), 8.87 (s, 1H), 8.66 (d, J=5.1 Hz, 1H), 8.44 (d, J=1.4 Hz, 1H), 8.31 (s, 1H), 8.15 (s, 1H), 8.02-8.09 (m, 1H), 7.93 (d, J=5.5 Hz, 1H), 7.70-7.79 (m, 2H), 7.21-7.27 (m, 1H), 6.30-6.39 (m, 1H), 3.90-4.21 (m, 2H), 2.78 (s, 3H), 1.11 (s, 9H). $^{19}$F NMR (376 MHz, DMSO-d$_6$) δ −66.53, −112.68.

Example 443: 5-(3-Chloro-2-fluoro-6-(1H-tetrazol-1-yl)phenyl)-2-(1-(4-(2-fluoropyridin-4-yl)-1H-pyrazol-1-yl)-2-(N-methylbenzamido)ethyl)pyridine 1-oxide trifluoroacetic acid

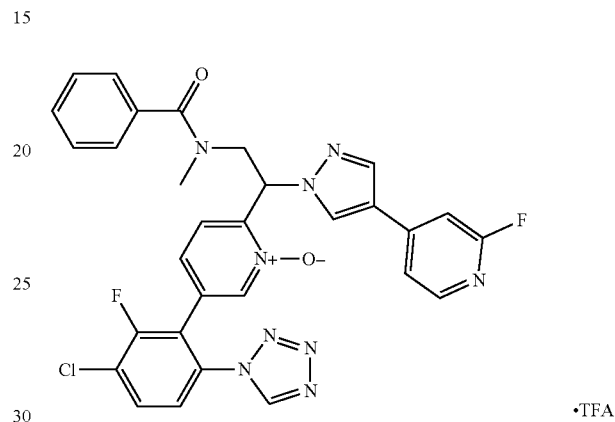

LC/MS: mass calculated for $C_{30}H_{22}ClF_2N_9O_2$: 613.2, measured (ES, m/z): 614.15 [M+H]$^+$. $^1$H NMR (300 MHz, DMSO-d$_6$) δ 9.68 (s, 1H), 8.88 (s, 1H), 8.47 (s, 1H), 8.14-8.27 (m, 2H), 8.05 (t, J=8.3 Hz, 1H), 7.69-7.82 (m, 2H), 7.59 (s, 1H), 7.16-7.46 (m, 7H), 6.30-6.56 (m, 1H), 4.10-4.32 (m, 2H), 3.03 (s, 1H), 2.68 (s, 2H). $^{19}$F NMR (282 MHz, DMSO-d$_6$) δ −69.18, −74.65, −112.65.

Example 444: (R*)-5-(3-Chloro-2-fluoro-6-(1H-tetrazol-1-yl)phenyl)-2-(2-(N-methylcyclopropanecarboxamido)-1-(4-(2-(trifluoromethyl)pyridin-4-yl)-1H-pyrazol-1-yl)ethyl)pyridine 1-oxide

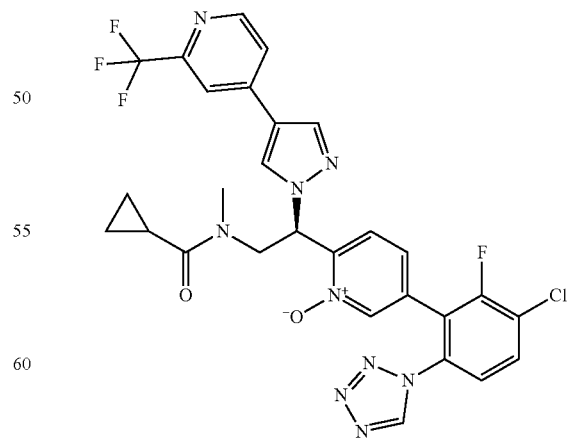

LC/MS: mass calculated for $C_{28}H_{22}ClF_4N_9O_2$: 627.15, measured (ES, m/z): 628.15 [M+H]$^+$. $^1$H NMR (300 MHz, DMSO-d$_6$) δ 9.65-9.71 (m, 1H), 8.86 (d, J=15.7 Hz, 1H), 8.66 (t, J=4.9 Hz, 1H), 8.25-8.50 (m, 2H), 8.01-8.15 (m, 2H), 7.85-7.95 (m, 1H), 7.59-7.79 (m, 2H), 7.15-7.29 (m, 1H), 6.21-6.35 (m, 1H), 4.02-4.52 (m, 2H), 2.65-2.95 (m, 3H), 1.69-2.12 (m, 1H), 0.65-0.89 (m, 3H), 0.38-0.64 (m, 1H). $^{19}$F NMR (282 MHz, DMSO-d$_6$) δ −66.52, −112.64.

Example 445: 5-(3-Chloro-2-fluoro-6-(1H-tetrazol-1-yl)phenyl)-2-(1-(4-(2-fluoropyridin-4-yl)-1H-pyrazol-1-yl)-2-(N-methylpivalamido)ethyl)pyridine 1-oxide

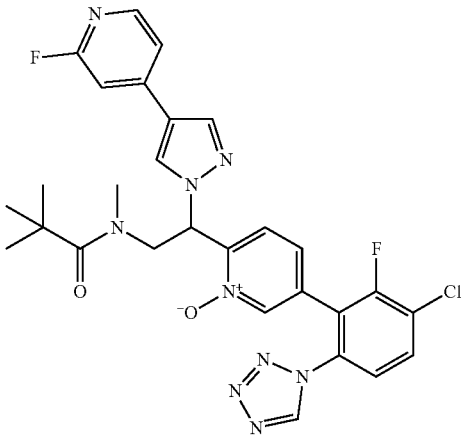

LC/MS: mass calculated for C$_{28}$H$_{26}$ClF$_2$N$_9$O$_2$: 593.19, measured (ES, m/z): 594.1 [M+H]$^+$. $^1$H NMR (300 MHz, DMSO-d$_6$) δ 9.68 (s, 1H), 8.72 (s, 1H), 8.43 (d, J=1.6 Hz, 1H), 8.20 (s, 1H), 8.14 (d, J=5.3 Hz, 1H), 8.00-8.08 (m, 1H), 7.65-7.81 (m, 2H), 7.55-7.59 (m, 1H), 7.42 (s, 1H), 7.22 (dd, J=8.2, 1.7 Hz, 1H), 6.27-6.38 (m, 1H), 4.08-4.19 (m, 1H), 3.88-3.93 (m, 1H), 2.75 (s, 3H), 1.09 (s, 9H). $^{19}$F NMR (282 MHz, DMSO-d$_6$) δ −69.16, −112.69.

Example 446: 5-(3-Chloro-2-fluoro-6-(1H-tetrazol-1-yl)phenyl)-2-(2-(2-methoxy-N-methylacetamido)-1-(4-(2-(trifluoromethyl)pyridin-4-yl)-1H-pyrazol-1-yl)ethyl)pyridine 1-oxide trifluoroacetic acid

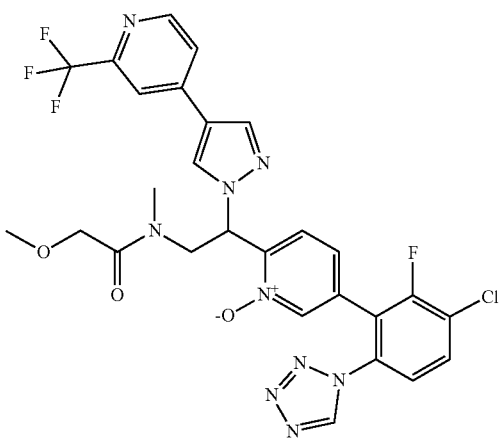

LC/MS: mass calculated for C$_{27}$H$_{22}$ClF$_4$N$_9$O$_3$: 631.15, measured (ES, m/z): 632.15 [M+H]$^+$. $^1$H NMR (300 MHz, DMSO-d$_6$) δ 9.65-9.72 (m, 1H), 8.01-9.95 (m, 1H), 8.61-8.71 (m, 1H), 8.28-8.50 (m, 2H), 8.02-8.15 (m, 2H), 7.81-7.97 (m, 1H), 7.56-7.77 (m, 2H), 7.23 (t, J=7.7 Hz, 1H), 6.19-6.39 (m, 1H), 3.73-4.27 (m, 4H), 3.09-3.23 (m, 3H), 2.79-2.80 (m, 3H). $^{19}$F NMR (282 MHz, DMSO-d$_6$) δ −66.56, −74.71, −112.66.

Example 447: (S*)-5-(3-Chloro-2-fluoro-6-(1H-tetrazol-1-yl)phenyl)-2-(2-(N-methylcyclopropanecarboxamido)-1-(4-(2-(trifluoromethyl)pyridin-4-yl)-1H-pyrazol-1-yl)ethyl)pyridine 1-oxide

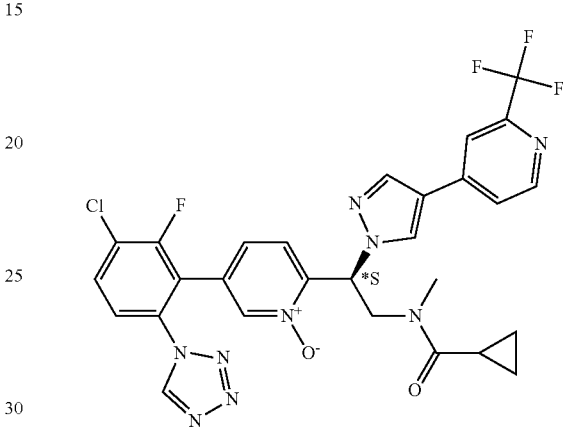

LC/MS: mass calculated for C$_{28}$H$_{22}$ClF$_4$N$_9$O$_2$: 627.15, measured (ES, m/z): 628.10 [M+H]$^+$. $^1$H NMR (300 MHz, DMSO-d$_6$) δ 9.68 (s, 1H), 8.86 (d, J=15.3 Hz, 1H), 8.66 (t, J=4.9 Hz, 1H), 8.27-8.51 (m, 2H), 8.00-8.16 (m, 2H), 7.90 (s, 1H), 7.59-7.79 (m, 2H), 7.12-7.25 (m, 1H), 6.10-6.23 (m, 1H), 3.97-4.54 (m, 2H), 2.90 (s, 1H), 2.71 (s, 2H), 1.10-1.24 (m, 1H), 0.42-0.74 (m, 4H). $^{19}$F NMR (282 MHz, DMSO-d$_6$) δ −66.52, −112.67.

Example 448: (S*)-2-(1-(4-(6-acetamido-2-fluoropyridin-3-yl)-1H-pyrazol-1-yl)-2-(4-(piperidine-1-carbonyl)-1H-pyrazol-1-yl)ethyl)-5-(3-chloro-2-fluoro-6-(1H-tetrazol-1-yl)phenyl)pyridine 1-oxide

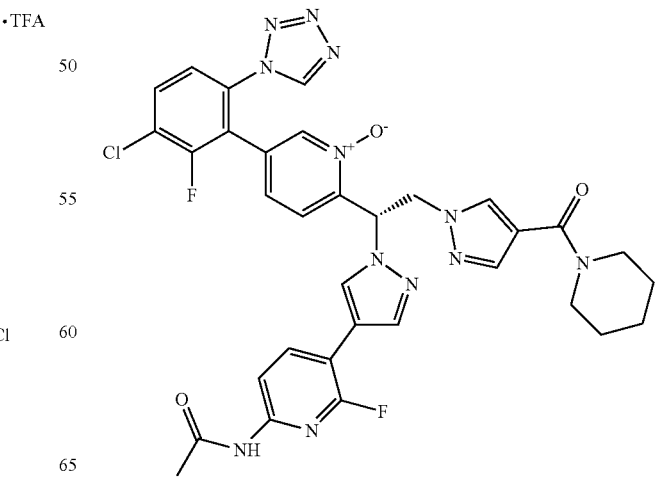

LC/MS: mass calculated for $C_{31}H_{27}ClF_2N_{12}O_2$: 672.20, measured (ES, m/z): 673.20 [M+H]$^+$. $^1$H NMR (300 MHz, CD$_3$OD) δ 9.38 (s, 1H), 8.42 (s, 1H), 7.85-7.98 (m, 2H), 7.82 (s, 1H), 7.51-7.77 (m, 5H), 7.30 (d, J=8.0 Hz, 1H), 6.57-6.79 (m, 1H), 6.41 (d, J=7.5 Hz, 1H), 5.05-5.14 (m, 2H), 3.38-3.64 (m, 4H), 1.37-1.67 (m, 6H).

Example 449: (R*)-5-(3-Chloro-2-fluoro-6-(1H-tetrazol-1-yl)phenyl)-2-(2-(2-oxooxazolidin-3-yl)-1-(4-(2-(trifluoromethyl)pyridin-4-yl)-1H-pyrazol-1-yl)ethyl)pyridine 1-oxide

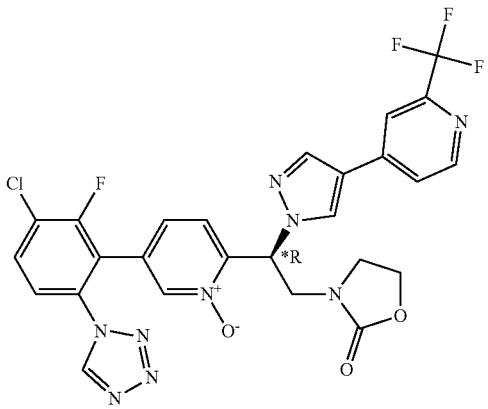 [SMILES: O=C1OCCN1C[C@@H](c1ccc(-c2c(-n3cnnn3)ccc(Cl)c2F)c[n+]1[O-])n1cc(-c2ccnc(C(F)(F)F)c2)cn1]

LC/MS: mass calculated for $C_{26}H_{18}ClF_4N_9O_3$: 615.12, measured (ES, m/z): 616.10 [M+H]$^+$. $^1$H NMR (300 MHz, DMSO-d$_6$) δ 9.66 (s, 1H), 8.90 (s, 1H), 8.67 (d, J=5.2 Hz, 1H), 8.46 (s, 1H), 8.35 (s, 1H), 8.00-8.15 (m, 2H), 7.90 (d, J=5.4 Hz, 1H), 7.69-7.79 (m, 1H), 7.54 (d, J=8.3 Hz, 1H), 7.16-7.27 (m, 1H), 6.22-6.38 (m, 1H), 4.21-4.05 (m, 3H), 3.85-4.99 (m, 1H), 3.60-3.68 (m, 1H), 3.11-3.21 (m, 1H). $^{19}$F NMR (282 MHz, DMSO-d$_6$) δ −66.53, −112.63.

Example 450: (S*)-5-(3-Chloro-2-fluoro-6-(1H-tetrazol-1-yl)phenyl)-2-(2-(2-oxooxazolidin-3-yl)-1-(4-(2-(trifluoromethyl)pyridin-4-yl)-1H-pyrazol-1-yl)ethyl)pyridine 1-oxide

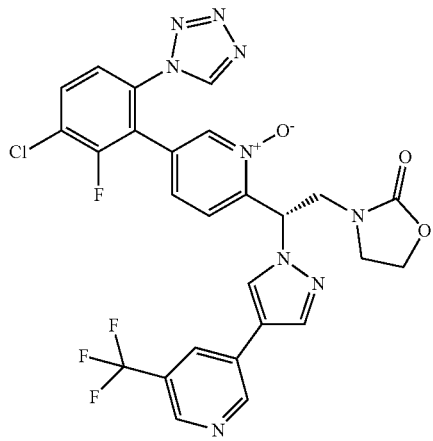 [SMILES: O=C1OCCN1C[C@@H](c1ccc(-c2c(-n3cnnn3)ccc(Cl)c2F)c[n+]1[O-])n1cc(-c2cncc(C(F)(F)F)c2)cn1]

LC/MS: mass calculated for $C_{26}H_{18}ClF_4N_9O_3$: 615.12, measured (ES, m/z): 616.10 [M+H]$^+$. $^1$H NMR (300 MHz, DMSO-d$_6$) δ 9.66 (s, 1H), 8.87-8.93 (m, 1H), 8.67 (d, J=5.2 Hz, 1H), 8.46 (d, J=1.5 Hz, 1H), 8.35 (s, 1H), 8.00-8.17 (m, 1H), 7.85-7.94 (m, 1H), 7.70-7.78 (m, 1H), 7.54 (d, J=8.3 Hz, 1H), 7.18-7.28 (m, 1H), 6.24-6.34 (m, 1H), 4.21-4.04 (m, 3H), 3.86-3.97 (m, 1H), 3.54-3.59 (m, 1H), 3.11-3.22 (m, 2H). $^{19}$F NMR (282 MHz, DMSO-d$_6$) δ −66.53, −112.63.

Example 451: (R)-5-(3-Chloro-2-fluoro-6-(1H-tetrazol-1-yl)phenyl)-2-(2-(3-methyl-2-oxo-2,3-dihydro-1H-imidazol-1-yl)-1-(4-(2-(trifluoromethyl)pyridin-4-yl)-1H-pyrazol-1-yl)ethyl)pyridine 1-oxide

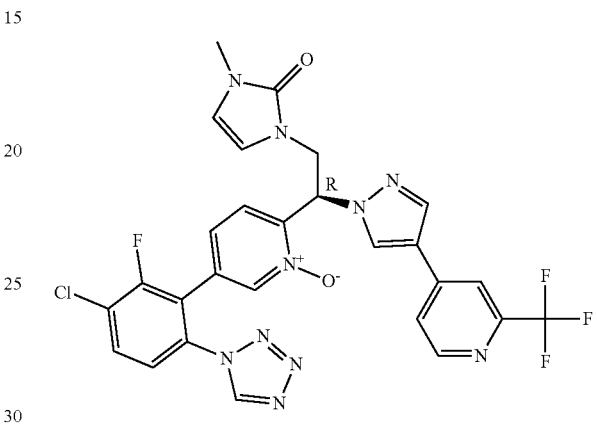

Step 1: tert-Butyl (2-(5-bromopyridin-2-yl)-2-hydroxyethyl)carbamate

To the solution of 2,5-dibromopyridine (10.0 g, 42.21 mmol, 1.1 equiv.) in 110 mL toluene was added n-butyllithium (16.1 mL, 40.30 mmol, 1.05 equiv, 2.5 M in hexane) at −78° C. and stirred for 1 h. tert-Butyl (2-oxoethyl)carbamate (6.1 g, 38.38 mmol, 1.0 equiv.) was then added to the solution and the mixture was stirred for 2 h at room temperature. The reaction was quenched by ammonium chloride solution (50 mL) and the organic layer washed by brine (40 mL) three times, the organic layer dried by anhydrous Na$_2$SO$_4$. The solvent was removed and the residue was purified by silica gel column chromatography (0→30% EA/PE) to yield tert-butyl (2-(5-bromopyridin-2-yl)-2-hydroxyethyl)carbamate as a yellow solid. LC/MS: mass calculated for $C_{12}H_{17}BrN_2O_3$: 316.04, measured (ES, m/z): 317.00 [M+H]$^+$.

Step 2: tert-Butyl (2-(5-bromopyridin-2-yl)-2-(4-iodo-1H-pyrazol-1-yl)ethyl)carbamate To the solution of tert-butyl (2-(5-bromopyridin-2-yl)-2-hydroxyethyl)carbamate (2.0 g, 6.31 mmol, 1.0 equiv.) and ADDP (3.2 g, 12.61 mmol, 2.0 equiv.) in DCM (30 mL) was added PBu$_3$ (2.6 g, 12.61 mmol, 2.0 equiv.) and 4-iodo-1H-pyrazole (1.3 g, 6.93 mmol, 1.1 equiv.) at 0° C. The reaction mixture was stirred at room temperature for 2 h. The reaction mixture was diluted with EA (50 mL) and washed with water (50 mL) three times and the organic layer dried by anhydrous Na$_2$SO$_4$. The solvent was removed, and the residue was purified by silica gel column chromatography (0→30% EA/PE) to yield tert-butyl (2-(5-bromopyridin-2-yl)-2-(4-iodo-1H-pyrazol-1-yl)ethyl)carbamate as a yellow solid.

LC/MS: mass calculated for $C_{15}H_{18}BrIN_4O_2$: 491.97, measured (ES, m/z): 393.00 [M+H–Boc]$^+$.

Step 3: tert-Butyl (2-(5-bromopyridin-2-yl)-2-(4-(2-(trifluoromethyl)pyridin-4-yl)-1H-pyrazol-1-yl) ethyl)carbamate tert-Butyl (2-(5-bromopyridin-2-yl)-2-(4-iodo-1H-pyrazol-1-yl)ethyl)carbamate (900.0 mg, 1.83 mmol, 1.0 equiv.), 4-(4,4,5,5-tetramethyl-1,3,2-dioxaborolan-2-yl)-2-(trifluoromethyl)pyridine (473.4 mg, 1.73 mmol, 0.95 equiv.), 1,1'-bis(diphenylphosphino)ferrocene]dichloropalladium (II)(133.5 mg, 0.18 mmol, 0.1 equiv.) and potassium phosphate (1.9 g, 9.12 mmol, 5.0 equiv.) were dissolved in 1,4-dioxane (15 mL) and $H_2O$ (1.5 mL) under $N_2$. The reaction mixture was stirred at 70° C. for 4 h and diluted with EA (100 mL) and water (50 mL), the organic extracts were washed with water (50 mL) two times and then dried over anhydrous $Na_2SO_4$, filtered and concentrated under reduced pressure. The residue was purified by normal phase chromatography (mobile phase: DCM/MeOH, 0→12%) to yield tert-butyl (2-(5-bromopyridin-2-yl)-2-(4-(2-(trifluoromethyl)pyridin-4-yl)-1H-pyrazol-1-yl)ethyl)carbamate as a yellow solid (74.9% yield). LC/MS: mass calculated for $C_{21}H_{21}BrF_3N_5O_2$: 511.08, measured (ES, m/z): 536.10 [M+Na+2]$^+$.

Step 4: tert-Butyl (2-(5-(6-amino-3-chloro-2-fluorophenyl)pyridin-2-yl)-2-(4-(2-(trifluoromethyl)pyridin-4-yl)-1H-pyrazol-1-yl)ethyl)carbamate tert-Butyl (2-(5-bromopyridin-2-yl)-2-(4-(2-(trifluoromethyl)pyridin-4-yl)-1H-pyrazol-1-yl)ethyl)carbamate (700.0 mg, 1.37 mmol, 1.0 equiv.), (6-amino-3-chloro-2-fluorophenyl)boronic acid (284.6 mg, 1.50 mmol, 1.1 equiv.), tetrakis (triphenylphosphine)palladium(157.9 mg, 0.14 mmol, 0.1 equiv.) and $K_2CO_3$ (870.1 mg, 4.10 mmol, 3.0 equiv.) were dissolved in 1,4-dioxane (10 mL) and water (2.0 mL) under $N_2$ and the reaction mixture was stirred at 90° C. for 4 h. The mixture was diluted with EA (100 mL) and water (50 mL), the organic extracts were washed with water (50 mL) two times and then dried over anhydrous $Na_2SO_4$, filtered, and concentrated under reduced pressure. The residue was purified by normal phase chromatography (mobile phase: MeOH/DCM, 0-*20%) to yield tert-butyl (2-(5-(6-amino-3-chloro-2-fluorophenyl)pyridin-2-yl)-2-(4-(2-(trifluoromethyl)pyridin-4-yl)-1H-pyrazol-1-yl)ethyl)carbamat as a yellow solid. LC/MS: mass calculated for $C_{27}H_{25}ClF_4N_6O_2$: 576.17, measured (ES, m/z): 577.10 [M+H]$^+$.

Step 5: tert-Butyl (2-(5-(3-chloro-2-fluoro-6-(1H-tetrazol-1-yl)phenyl)pyridin-2-yl)-2-(4-(2-(trifluoromethyl)pyridin-4-yl)-1H-pyrazol-1-yl)ethyl)carbamate tert-Butyl (2-(5-(6-amino-3-chloro-2-fluorophenyl)pyridin-2-yl)-2-(4-(2-(trifluoromethyl)pyridin-4-yl)-1H-pyrazol-1-yl)ethyl)carbamate (816.9 mg, 1.42 mmol, 1.0 equiv.), azidotrimethylsilane (815.6 mg, 7.08 mmol, 5.0 equiv.) and trimethoxymethane (1.5 g, 14.20 mmol, 10.0 equiv.) were dissolved in acetic acid glacial (5 mL). The reaction mixture was stirred at 30° C. overnight. Following this the solvent was removed under reduced pressure to yield tert-butyl (2-(5-(3-chloro-2-fluoro-6-(1H-tetrazol-1-yl)phenyl)pyridin-2-yl)-2-(4-(2-(trifluoromethyl)pyridin-4-yl)-1H-pyrazol-1-yl)ethyl)carbamate as a yellow solid, and used in the next step without further purification. LC/MS: mass calculated for $C_{28}H_{24}ClF_4N_9O_2$: 629.17, measured (ES, m/z): 630.15 [M+H]$^+$.

Step 6: 2-(2-((tert-Butoxycarbonyl)amino)-1-(4-(2-(trifluoromethyl)pyridin-4-yl)-1H-pyrazol-1-yl) ethyl)-5-(3-chloro-2-fluoro-6-(1H-tetrazol-1-yl)phenyl)pyridine 1-oxide tert-Butyl (2-(5-(3-chloro-2-fluoro-6-(1H-tetrazol-1-yl) phenyl)pyridin-2-yl)-2-(4-(2-(trifluoromethyl)pyridin-4-yl)-1H-pyrazol-1-yl)ethyl)carbamate (630.0 mg, 1.0 mmol, 1.0 equiv.), methyltrioxorhenium (VII) (124.6 mg, 0.5 equiv., 0.5 equiv.) were dissolved in methanol (10.0 mL) and then hydrogen peroxide (170.1 mg, 5.0 mmol, 5.0 equiv, 30 wt. %) was added at room temperature, and the mixture stirred for 3 h. EA (100 mL) was added and the mixture washed with water (50 mL) and brine, then dried over anhydrous $Na_2SO_4$, filtered, and concentrated under reduced pressure. The residue was purified by chromatography on C18 (80 g, MeCN/$H_2O$ (0.05% $CF_3COOH$): 0→60%) to yield 2-(2-((tert-butoxycarbonyl)amino)-1-(4-(2-(trifluoromethyl)pyridin-4-yl)-1H-pyrazol-1-yl)ethyl)-5-(3-chloro-2-fluoro-6-(1H-tetrazol-1-yl)phenyl)pyridine 1-oxide as a yellow solid. LC/MS: mass calculated for $C_{28}H_{24}ClF_4N_9O_3$: 645.16, measured (ES, m/z): 646.15 [M+H]$^+$.

Step 7: 2-(2-Amino-1-(4-(2-(trifluoromethyl)pyridin-4-yl)-1H-pyrazol-1-yl)ethyl)-5-(3-chloro-2-fluoro-6-(1H-tetrazol-1-yl)phenyl)pyridine 1-oxide 2-(2-((tert-Butoxycarbonyl)amino)-1-(4-(2-(trifluoromethyl)pyridin-4-yl)-1H-pyrazol-1-yl)ethyl)-5-(3-chloro-2-fluoro-6-(1H-tetrazol-1-yl)phenyl)pyridine 1-oxide (536 mg, 0.83 mmol, 1.0 equiv.) was dissolved in DCM (10 mL) and then trifluoroacetic acid (283.8 mg, 2.49 mmol, 3.0 equiv.) was added to the mixture, and the resulting solution was stirred at room temperature overnight. The pH value of the solvent was adjusted to 9 by sodium bicarbonate solution. DCM (100 mL) was added and the mixture washed with water (50 mL) three times, and the organic layer dried by anhydrous $Na_2SO_4$. The solvent was removed under reduced pressure and the resulting residue was purified by chromatography on C18 (80 g, MeCN/$H_2O$ (0.05% $CF_3COOH$): 0→30%) to yield 2-(2-amino-1-(4-(2-(trifluoromethyl)pyridin-4-yl)-1H-pyrazol-1-yl)ethyl)-5-(3-chloro-2-fluoro-6-(1H-tetrazol-1-yl)phenyl)pyridine 1-oxide as a white solid. LC/MS: mass calculated for $C_{23}H_{16}ClF_4N_9O$: 545.11, measured (ES, m/z): 568.10 [M+Na]$^+$.

Step 8: (R)-5-(3-Chloro-2-fluoro-6-(1H-tetrazol-1-yl)phenyl)-2-(2-(3-methyl-2-oxo-2,3-dihydro-1H-imidazol-1-yl)-1-(4-(2-(trifluoromethyl)pyridin-4-yl)-1H-pyrazol-1-yl)ethyl)pyridine 1-oxide A mixture of 2-(2-amino-1-(4-(2-(trifluoromethyl)pyridin-4-yl)-1H-pyrazol-1-yl)ethyl)-5-(3-chloro-2-fluoro-6-(1H-tetrazol-1-yl)phenyl)pyridine 1-oxide (100.0 mg, 0.18 mmol, 1.0 equiv.) and N,N'-disuccinimidyl carbonate (93.8 mg, 0.36 mmol, 2.0 equiv.) in DMF (5 mL) was stirred overnight at room temperature. A solution of 2,2-dimethoxy-N-methylethan-1-amine (54.5 mg, 0.46 mmol, 2.5 equiv.) in DMF (5 mL) was added to the solution and the mixture was stirred for 4 h at room temperature. The reaction mixture was diluted with water, and the mixture extracted with ethyl acetate twice. The combined organic layers were washed with water and brine, dried over anhydrous $Na_2SO_4$ and concentrated. The residue was stirred with 3M HCl for 2 h at room temperature. The mixture was adjusted to pH=8 by sodium bicarbonate and then extracted with ethyl acetate twice. The combined organic layers were washed with brine, dried over anhydrous $Na_2SO_4$ and concentrated. The residue was purified by chromatography on C18 (80 g, $MeCN/H_2O$ (0.05% $CF_3COOH$): 0→60%) and prep-chiral-HPLC. The collected fractions were combined and concentrated under vacuum. To yield (R)-5-(3-chloro-2-fluoro-6-(1H-tetrazol-1-yl)phenyl)-2-(2-(3-methyl-2-oxo-2,3-dihydro-1H-imidazol-1-yl)-1-(4-(2-(trifluoromethyl)pyridin-4-yl)-1H-pyrazol-1-yl)ethyl)pyridine 1-oxide as a white solid.

LC/MS: mass calculated for $C_{27}H_{19}ClF_4N_{10}O_2$: 626.13, measured (ES, m/z): 627.15 [M+H]$^+$. $^1$H NMR (300 MHz, DMSO-$d_6$) δ 9.66 (s, 1H), 8.79 (s, 1H), 8.65 (d, J=5.1 Hz, 1H), 8.45 (s, 1H), 8.33 (s, 1H), 8.04-8.10 (m, 2H), 7.84-7.92 (m, 1H), 7.72-7.80 (m, 1H), 7.60 (d, J=8.3 Hz, 1H), 7.15-7.24 (m, 1H), 6.30-6.40 (m, 2H), 6.08 (d, J=3.0 Hz, 1H), 4.30-4.50 (m, 2H), 3.04 (s, 3H). $^{19}$F NMR (282 MHz, DMSO-$d_6$) δ −66.52, −112.63.

Example 452: (S*)-5-(3-Chloro-2-fluoro-6-(1H-tetrazol-1-yl)phenyl)-2-(2-(3-methyl-2-oxo-2,3-dihydro-1H-imidazol-1-yl)-1-(4-(2-(trifluoromethyl)pyridin-4-yl)-1H-pyrazol-1-yl)ethyl)pyridine 1-oxide

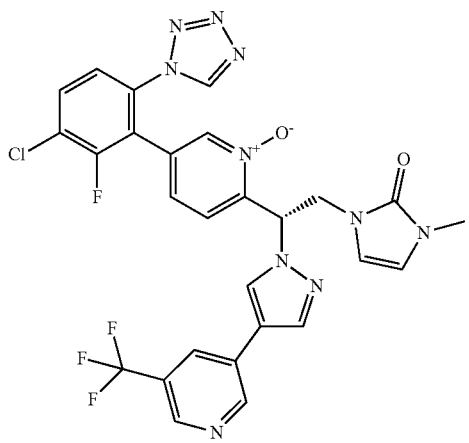 [SMILES: Cn1ccn(C[C@@H](c2ccc(-c3c(-n4cnnn4)ccc(Cl)c3F)c[n+]2[O-])n2cc(-c3cncc(C(F)(F)F)c3)cn2)c1=O]

LC/MS: mass calculated for $C_{27}H_{19}ClF_4N_{10}O_2$: 626.13, measured (ES, m/z): 627.10 [M+H]$^+$. $^1$H NMR (300 MHz, DMSO-$d_6$) δ 9.65 (s, 1H), 8.79 (s, 1H), 8.65 (d, J=5.2 Hz, 1H), 8.45 (d, J=1.5 Hz, 1H), 8.33 (s, 1H), 7.79-8.29 (m, 2H), 7.84-7.92 (m, 1H), 7.68-7.81 (m, 1H), 7.60 (d, J=8.3 Hz, 1H), 7.12-7.29 (m, 1H), 6.30-6.40 (m, 2H), 6.08 (d, J=2.9 Hz, 1H), 4.28-4.50 (m, 2H), 3.04 (s, 3H). $^{19}$F NMR (282 MHz, DMSO-$d_6$) δ −66.52, −112.64.

Example 453: (S*)-5-(3-Chloro-2-fluoro-6-(1H-tetrazol-1-yl)phenyl)-2-(2-(N,1-dimethyl-2-oxo-1,2-dihydropyridine-4-carboxamido)-1-(4-(2-(trifluoromethyl)pyridin-4-yl)-1H-pyrazol-1-yl)ethyl)pyridine 1-oxide

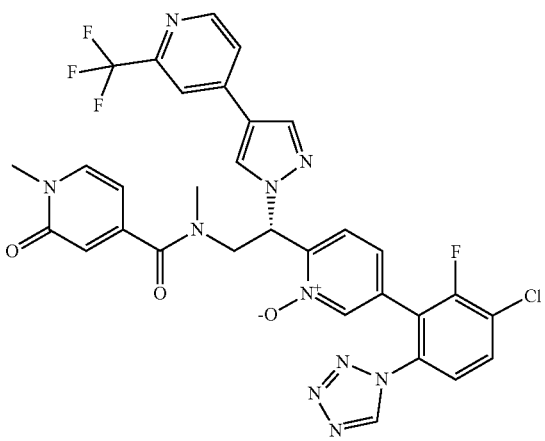

LC/MS: mass calculated for $C_{31}H_{23}ClF_4N_{10}O_3$: 694.16, measured (ES, m/z): 695.15 [M+H]$^+$. $^1$H NMR (400 MHz, DMSO-$d_6$) δ 9.68 (d, J=4.5 Hz, 1H), 8.78-9.10 (m, 1H), 8.60-8.78 (m, 1H), 8.41-8.22 (m, 1H), 8.00-8.39 (m, 3H), 7.85-7.98 (m, 1H), 7.59-7.81 (m, 3H), 7.13-7.42 (m, 1H), 6.25-6.54 (m, 1H), 5.75-6.21 (m, 2H), 3.91-4.49 (m, 2H), 3.38-3.43 (m, 3H), 2.65-3.06 (m, 3H). $^{19}$F NMR (376 MHz, DMSO-$d_6$) δ −66.51, −73.45, −112.63.

Example 454: (R*)-5-(3-Chloro-2-fluoro-6-(1H-tetrazol-1-yl)phenyl)-2-(2-(N,1-dimethyl-2-oxo-1,2-dihydropyridine-4-carboxamido)-1-(4-(2-(trifluoromethyl)pyridin-4-yl)-1H-pyrazol-1-yl)ethyl)pyridine 1-oxide trifluoroacetic acid

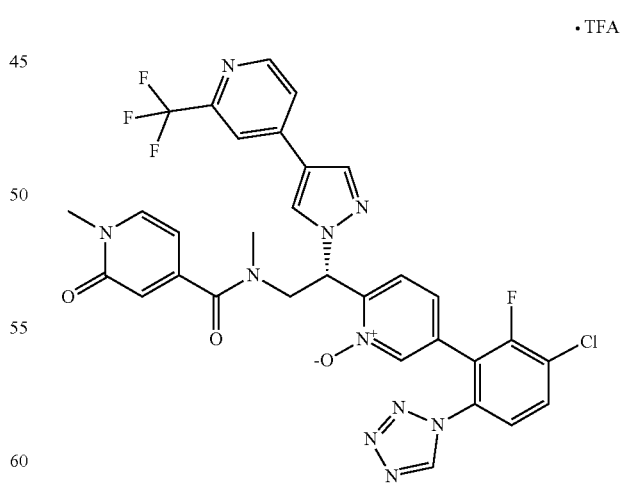

LC/MS: mass calculated for $C_{31}H_{23}ClF_4N_{10}O_3$: 694.16, measured (ES, m/z): 695.25 [M+H]$^+$. $^1$H NMR (400 MHz, DMSO-$d_6$) δ 9.68 (d, J=4.6 Hz, 1H), 8.80-9.12 (m, 1H), 8.60-8.79 (m, 1H), 8.41-8.59 (m, 1H), 8.20-8.30 (m, 1H), 8.00-8.19 (m, 2H), 7.85-7.99 (m, 1H), 7.59-7.83 (m, 2H), 7.12-7.40 (m, 1H), 5.76-6.50 (m, 3H), 4.29-4.43 (m, 1H), 4.11-4.18 (m, 1H), 3.94-4.05 (m, 1H), 3.35-3.48 (m, 3H), 3.01 (s, 1H), 2.70 (s, 2H). $^{19}$F NMR (376 MHz, DMSO-$d_6$) δ −66.51, −74.73, −112.64.

Example 455: 2-(tert-Butyl)-4-(1-(1-(5-(3-chloro-2-fluoro-6-(1H-tetrazol-1-yl)phenyl)-1-oxidopyridin-2-yl)-2-(4-fluoro-1H-pyrazol-1-yl)ethyl)-1H-pyrazol-4-yl)pyridine 1-oxide trifluoroacetic acid

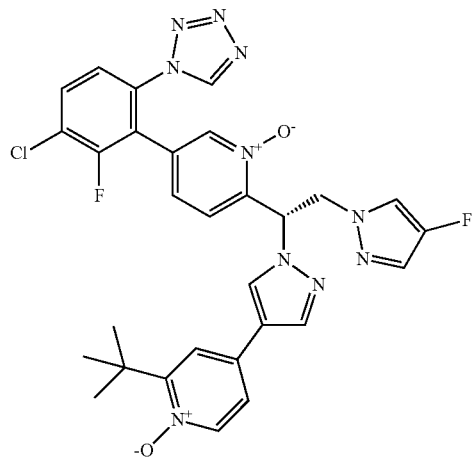

LC/MS: mass calculated for $C_{29}H_{25}ClF_2N_{10}O_2$: 618.18, measured (ES, m/z): 619.20 [M+H]$^+$. $^1$H NMR (300 MHz, DMSO-$d_6$) δ 9.69 (s, 1H), 8.48-8.59 (m, 2H), 8.21 (s, 1H), 8.11-8.19 (m, 1H), 8.00-8.19 (m, 1H), 7.87-7.93 (m, 1H), 7.65-7.79 (m, 2H), 7.41-7.60 (m, 2H), 7.28-7.40 (m, 1H), 7.19-7.28 (m, 1H), 6.47-6.58 (m, 1H), 4.81-5.07 (m, 2H), 1.58 (s, 9H). $^{19}$F NMR (282 MHz, DMSO-$d_6$) δ −74.14, −112.65, −177.81.

Example 456: 5-(3-Chloro-2-fluoro-6-(1H-tetrazol-1-yl)phenyl)-2-(1-(4-(2-(trifluoromethyl)pyridin-4-yl)-1H-pyrazol-1-yl)-2-(1,3,3-trimethylureido)ethyl)pyridine 1-oxide trifluoroacetic acid

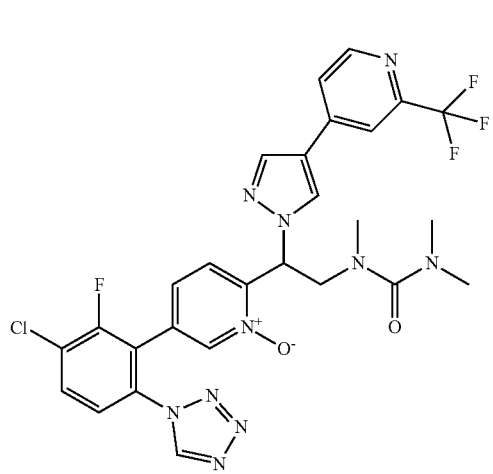

LC/MS: mass calculated for $C_{27}H_{23}ClF_4N_{10}O_2$: 630.16, measured (ES, m/z): 631.10 [M+H]$^+$. $^1$H NMR (300 MHz, CD$_3$OD) δ 9.41 (s, 1H), 8.58-8.67 (m, 2H), 8.41 (s, 1H), 8.22 (s, 1H), 8.04 (s, 1H), 7.90-7.79 (m, 1H), 7.86 (d, J=5.3 Hz, 1H), 7.70 (d, J=8.3 Hz, 1H), 7.59-7.68 (m, 1H), 7.26-7.40 (m, 1H), 6.50-6.61 (m, 1H), 4.20-4.35 (m, 1H), 4.01-4.15 (m, 1H), 2.91 (s, 3H), 2.69 (s, 6H). $^{19}$F NMR (282 MHz, CD$_3$OD) δ −69.53, −77.19, −113.69.

Example 457: (R*)-2-(1-(4-(6-Amino-2-fluoropyridin-3-yl)-1H-pyrazol-1-yl)-2-(4-fluoro-1H-pyrazol-1-yl)ethyl)-5-(3-chloro-6-(difluoromethyl)-2-fluorophenyl)pyridine 1-oxide

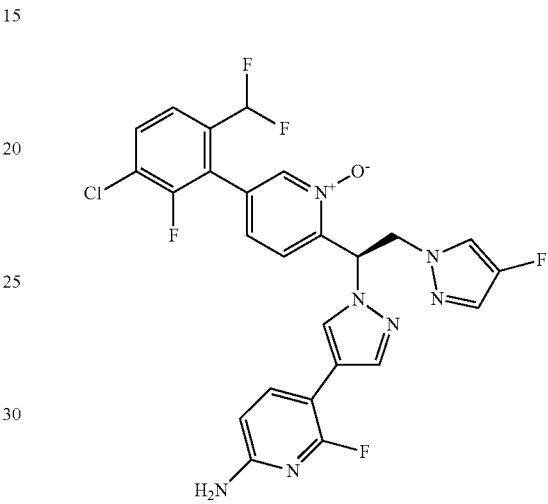

LC/MS: mass calculated for $C_{25}H_{17}ClF_5N_7O$: 561.11, measured (ES, m/z): 562.05 [M+H]$^+$. $^1$H NMR (400 MHz, CD$_3$OD) δ 8.51 (s, 1H), 7.99-8.05 (m, 2H), 7.84-7.92 (m, 1H), 7.77-7.84 (m, 1H), 7.58-7.67 (m, 2H), 7.50-7.57 (m, 1H), 7.47 (d, J=4.5 Hz, 1H), 7.38 (d, J=4.0 Hz, 1H), 6.47-6.87 (m, 3H), 5.04-5.20 (m, 2H).

Example 458: (S*)-2-(1-(4-(6-Amino-2-fluoropyridin-3-yl)-1H-pyrazol-1-yl)-2-(4-fluoro-1H-pyrazol-1-yl)ethyl)-5-(3-chloro-6-(difluoromethyl)-2-fluorophenyl)pyridine 1-oxide

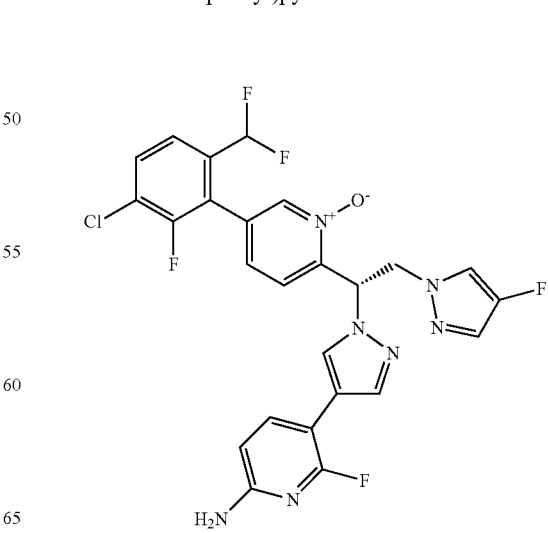

LC/MS: mass calculated for $C_{25}H_{17}ClF_5N_7O$: 561.11, measured (ES, m/z): 562.10 [M+H]$^+$. $^1$H NMR (300 MHz, CD$_3$OD) δ 8.50 (s, 1H), 8.00 (s, 2H), 7.75-7.80 (m, 2H), 7.61 (d, J=8.3 Hz, 2H), 7.50-7.56 (m, 1H), 7.47 (d, J=4.6 Hz, 1H), 7.38 (d, J=4.0 Hz, 1H), 6.65-6.75 (m, 1H), 6.47-6.55 (m, 1H), 5.06-5.21 (m, 2 h), 4.90-4.92 (m, 1H).

Example 459: (R*)-5-(3-Chloro-2-fluoro-6-(1H-tetrazol-1-yl)phenyl)-2-(1-(4-(2-cyanopyridin-4-yl)-1H-pyrazol-1-yl)-2-(2-oxooxazolidin-3-yl)ethyl)pyridine 1-oxide

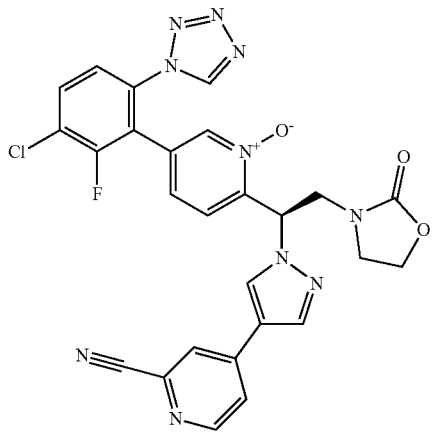 [SMILES: N#Cc1cc(-c2cnn([C@H](CN3CCOC3=O)c3ccc(-c4c(-n5cnnn5)ccc(Cl)c4F)c[n+]3[O-])c2)ccn1]

LC/MS: mass calculated for $C_{26}H_{18}ClFN_{10}O_3$: 572.12, measured (ES, m/z): 573.15 [M+H]$^+$. $^1$H NMR (300 MHz, DMSO-d$_6$) δ 9.67 (s, 1H), 8.84 (s, 1H), 8.60-8.70 (m, 1H), 8.45 (d, J=1.4 Hz, 1H), 8.31 (s, 2H), 8.00-8.11 (m, 1H), 7.86-7.96 (m, 1H), 7.70-7.80 (m, 1H), 7.55 (d, J=8.3 Hz, 1H), 7.15-7.27 (m, 1H), 6.21-6.36 (m, 1H), 4.01-4.23 (m, 3H), 4.84-4.96 (m, 1H), 3.49-3.61 (m, 1H), 3.12-3.20 (m, 1H). $^{19}$F NMR (282 MHz, DMSO-d$_6$) δ −112.62.

Example 460: (S*)-5-(3-Chloro-2-fluoro-6-(1H-tetrazol-1-yl)phenyl)-2-(1-(4-(2-cyanopyridin-4-yl)-1H-pyrazol-1-yl)-2-(2-oxooxazolidin-3-yl)ethyl)pyridine 1-oxide

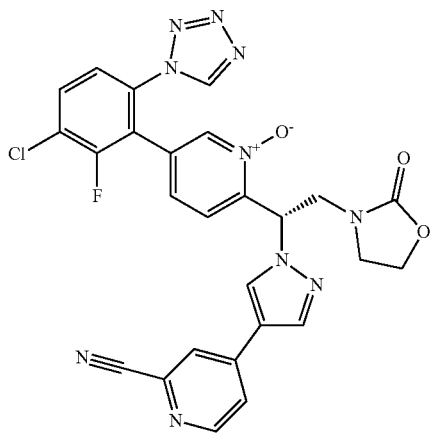 [SMILES: N#Cc1cc(-c2cnn([C@@H](CN3CCOC3=O)c3ccc(-c4c(-n5cnnn5)ccc(Cl)c4F)c[n+]3[O-])c2)ccn1]

LC/MS: mass calculated for $C_{26}H_{18}ClFN_{10}O_3$: 572.12, measured (ES, m/z): 573.15 [M+H]$^+$. $^1$H NMR (300 MHz, DMSO-d$_6$) δ 9.67 (s, 1H), 8.84 (s, 1H), 8.65 (dd, J=5.2, 0.8 Hz, 1H), 8.45 (d, J=1.4 Hz, 1H), 8.31 (d, J=1.9 Hz, 2H), 8.00-8.11 (m, 1H), 7.86-7.98 (m, 1H), 7.74 (dd, J=8.7, 1.6 Hz, 1H), 7.55 (d, J=8.3 Hz, 1H), 7.21 (dd, J=8.3, 1.7 Hz, 1H), 6.22-6.36 (m, 1H), 4.03-4.23 (m, 3H), 3.83-3.99 (m, 1H), 3.51-3.59 (m, 1H), 3.15-3.20 (m, 1H). $^{19}$F NMR (282 MHz, DMSO-d$_6$) δ −112.63.

Example 461: (R*)-5-(3-Chloro-2-fluoro-6-(1H-tetrazol-1-yl)phenyl)-2-(2-(3-(methoxymethyl)-1H-pyrazol-1-yl)-1-(4-(2-(trifluoromethyl)pyridin-4-yl)-1H-pyrazol-1-yl)ethyl)pyridine 1-oxide

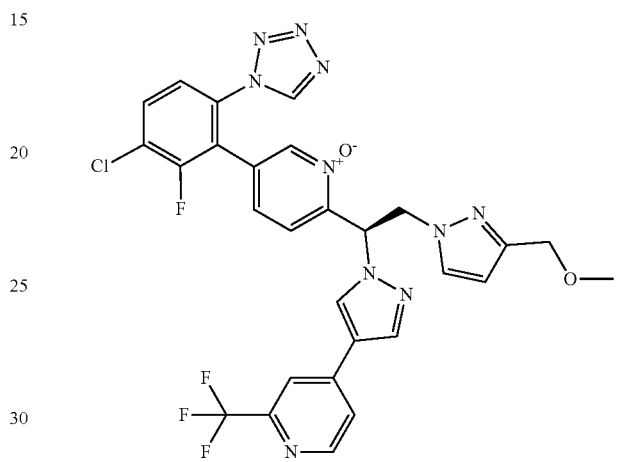

LC/MS: mass calculated for $C_{28}H_{21}ClF_4N_{10}O_2$: 640.15, measured (ES, m/z): 641.15 [M+H]$^+$. $^1$H NMR (300 MHz, DMSO-d$_6$) δ 9.67 (s, 1H), 8.70 (s, 1H), 8.64 (d, J=5.1 Hz, 1H), 8.50 (s, 1H), 8.35 (s, 1H), 7.99-8.11 (m, 2H), 7.83 (d, J=5.0 Hz, 1H), 7.74 (dd, J=8.7, 1.6 Hz, 1H), 7.40-7.52 (m, 2H), 7.16-7.25 (m, 1H), 6.49-6.70 (m, 1H), 6.06 (d, J=2.2 Hz, 1H), 4.86-5.09 (m, 2H), 4.25 (s, 2H), 3.11 (s, 3H). $^{19}$F NMR (282 MHz, DMSO-d$_6$) δ −66.56, −112.62.

Example 462: (R)-5-(3-Chloro-2-fluoro-6-(1H-tetrazol-1-yl)phenyl)-2-(2-(3-(methoxymethyl)-1H-pyrazol-1-yl)-1-(4-(2-(trifluoromethyl)pyridin-4-yl)-1H-pyrazol-1-yl)ethyl)pyridine 1-oxide

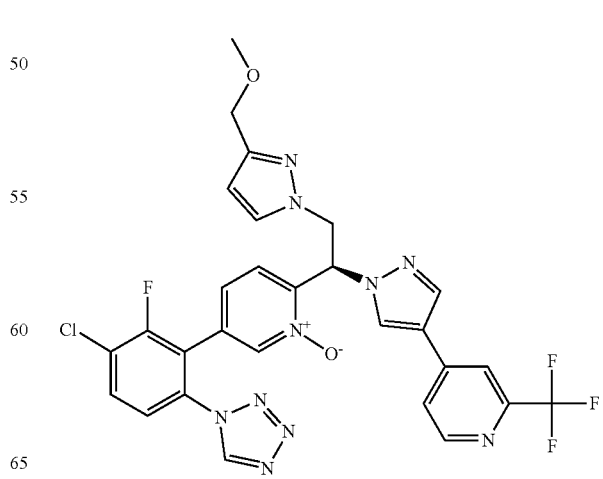

LC/MS: mass calculated for $C_{28}H_{21}ClF_4N_{10}O_2$: 640.15, measured (ES, m/z): 641.15 [M+H]⁺. ¹H NMR (300 MHz, DMSO-d₆) δ 9.67 (s, 1H), 8.70 (s, 1H), 8.64 (d, J=5.2 Hz, 1H), 8.50 (s, 1H), 8.35 (s, 1H), 7.99-8.11 (m, 2H), 7.83 (d, J=5.1 Hz, 1H), 7.74 (dd, J=8.7, 1.6 Hz, 1H), 7.40-7.52 (m, 2H), 7.17-7.23 (m, 1H), 6.49-6.58 (m, 1H), 6.06 (d, J=2.3 Hz, 1H), 4.84-5.07 (m, 2H), 4.25 (s, 2H), 3.11 (s, 3H). ¹⁹F NMR (282 MHz, DMSO-d₆) δ −66.56, −112.60.

Example 463: 2-(2-(3-Carboxy-1H-pyrazol-1-yl)-1-(4-(pyridin-4-yl)-1H-pyrazol-1-yl)ethyl)-5-(3-chloro-2-fluoro-6-(1H-tetrazol-1-yl)phenyl)pyridine 1-oxide trifluoroacetic acid

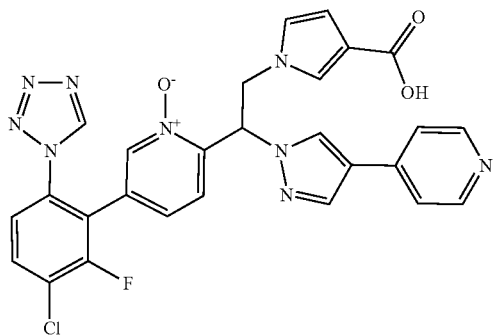 [SMILES: O=C(O)c1ccn(CC(c2ccc(-c3c(-n4cnnn4)ccc(Cl)c3F)c[n+]2[O-])n2cc(-c3ccncc3)cn2)c1]

LC/MS: mass calculated for $C_{28}H_{18}ClFN_{10}O_3$: 572.12, measured (ES, m/z): 573.05 [M+H]⁺. ¹H NMR (300 MHz, DMSO-d₆) δ 9.69 (s, 1H), 8.86 (s, 1H), 8.74 (d, J=6.4 Hz, 2H), 8.53 (s, 1H), 8.47 (s, 1H), 8.00-8.14 (m, 3H), 7.75 (dd, J=8.7, 1.6 Hz, 1H), 7.51-7.61 (m, 2H), 7.25 (d, J=8.2 Hz, 1H), 6.52-6.65 (m, 2H), 5.13-5.27 (m, 1H), 5.05 (dd, J=13.7, 4.3 Hz, 1H). ¹⁹F NMR (282 MHz, DMSO-d₆) δ −74.19, −112.59.

Example 464: 2-(2-(3-Carbamoyl-1H-pyrazol-1-yl)-1-(4-(pyridin-4-yl)-1H-pyrazol-1-yl)ethyl)-5-(3-chloro-2-fluoro-6-(1H-tetrazol-1-yl)phenyl)pyridine 1-oxide trifluoroacetic acid

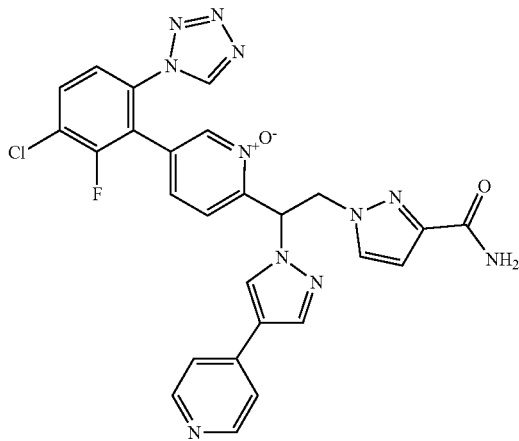

LC/MS: mass calculated for $C_{26}H_{19}ClFN_{11}O_2$: 571.14, measured (ES, m/z): 572.20 [M+H]⁺. ¹H NMR (300 MHz, DMSO-d₆) δ 9.70 (s, 1H), 8.83 (s, 1H), 8.68-8.80 (m, 2H), 8.48-8.55 (m, 1H), 8.43 (s, 1H), 7.98-8.12 (m, 3H), 7.76 (dd, J=8.7, 1.5 Hz, 1H), 7.60 (d, J=8.3 Hz, 1H), 7.54 (d, J=2.4 Hz, 1H), 7.34 (s, 1H), 7.20-7.36 (m, 2H), 6.59-6.71 (m, 1H), 6.48 (d, J=2.3 Hz, 1H), 5.51-5.30 (m, 1H), 4.95-5.10 (m, 1H). ¹⁹F NMR (282 MHz, DMSO-d₆) δ −73.94, −112.62.

Example 465: 2-(2-(3-(4-Carboxypiperidine-1-carbonyl)-1H-pyrazol-1-yl)-1-(4-(pyridin-4-yl)-1H-pyrazol-1-yl)ethyl)-5-(3-chloro-2-fluoro-6-(1H-tetrazol-1-yl)phenyl)pyridine 1-oxide

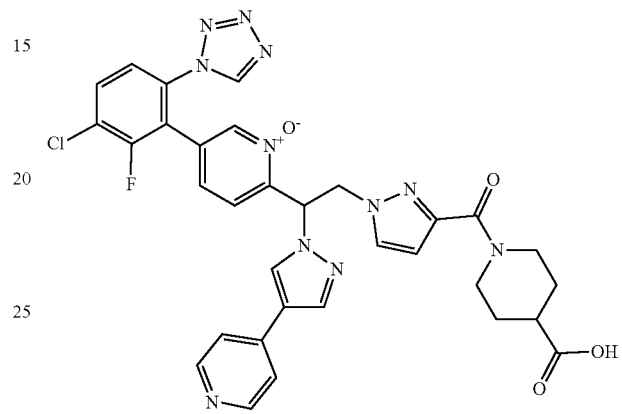

LC/MS: mass calculated for $C_{32}H_{27}ClFN_{11}O_4$: 683.19, measured (ES, m/z): 684.20 [M+H]⁺. ¹H NMR (300 MHz, DMSO-d₆) δ 9.69 (s, 1H), 8.84 (d, J=5.9 Hz, 1H), 8.67-8.76 (m, 2H), 8.42-8.54 (m, 2H), 8.00-8.12 (m, 3H), 7.75 (dd, J=8.7, 1.5 Hz, 1H), 7.70 (d, J=2.3 Hz, 1H), 7.62 (d, J=8.3 Hz, 1H), 7.26 (dd, J=8.3, 1.6 Hz, 1H), 6.49-6.62 (m, 1H), 6.38-6.48 (m, 1H), 4.97-5.22 (m, 2H), 3.98-4.27 (m, 2H), 2.75-3.04 (m, 2H), 2.32-2.46 (m, 1H), 1.71-1.90 (m, 1H), 1.51-1.70 (m, 1H), 1.28-1.42 (m, 2H). ¹⁹F NMR (282 MHz, DMSO-d₆) δ −74.07, −112.65.

Example 466: 2-(2-(3-Carboxy-1H-pyrazol-1-yl)-1-(4-(4-((methoxycarbonyl)amino)phenyl)-1H-pyrazol-1-yl)ethyl)-5-(3-chloro-2-fluoro-6-(1H-tetrazol-1-yl)phenyl)pyridine 1-oxide

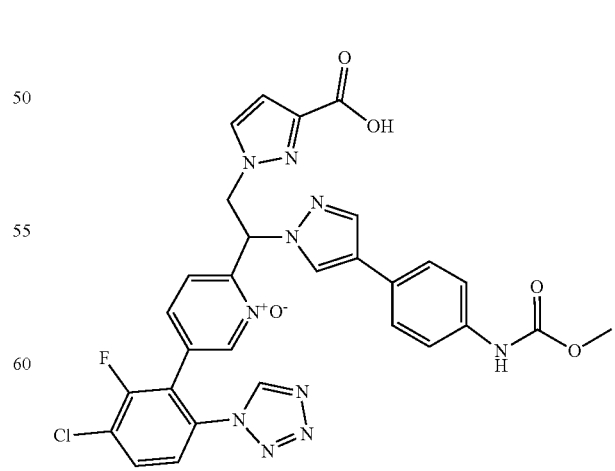

LC/MS: mass calculated for $C_{29}H_{22}ClFN_{10}O_5$: 644.14, measured (ES, m/z): 645.20 [M+H]⁺. ¹H NMR (300 MHz, DMSO-d$_6$) δ 9.67 (s, 1H), 9.60 (s, 1H), 8.50 (s, 1H), 8.00-8.11 (m, 1H), 7.84 (d, J=2.3 Hz, 1H), 7.70-7.82 (m, 3H), 7.32-7.44 (m, 4H), 7.29 (d, J=8.5 Hz, 1H), 7.21 (d, J=7.9 Hz, 1H), 6.47-6.60 (m, 2H), 4.92-5.05 (m, 2H), 3.64 (s, 3H).

Example 467: 2-(2-(3-Carbamoyl-1H-pyrazol-1-yl)-1-(4-(4-((methoxycarbonyl)amino)phenyl)-1H-pyrazol-1-yl)ethyl)-5-(3-chloro-2-fluoro-6-(1H-tetrazol-1-yl)phenyl)pyridine 1-oxide trifluoroacetic acid

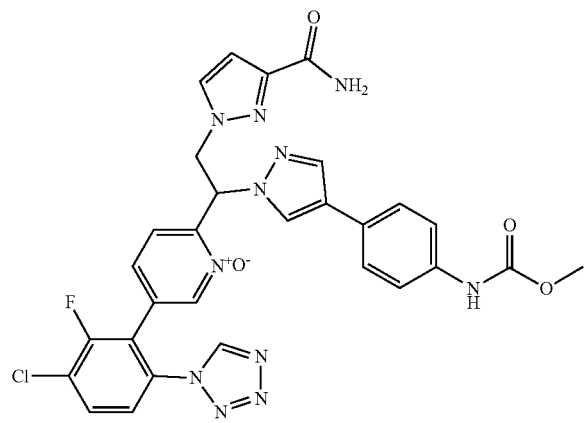

LC/MS: mass calculated for C$_{29}$H$_{23}$ClFN$_{11}$O$_4$: 643.16, measured (ES, m/z): 644.20 [M+H]$^+$. $^1$H NMR (400 MHz, DMSO-d$_6$) δ 9.70 (s, 1H), 9.63 (s, 1H), 8.47 (s, 1H), 8.04-8.13 (m, 1H), 7.89-7.96 (m, 2H), 7.74-7.81 (m, 2H), 7.68 (s, 1H), 7.40-7.46 (m, 2H), 7.32-7.39 (m, 3H), 7.21 (s, 2H), 6.55-6.65 (m, 2H), 4.90-5.12 (m, 2H), 3.66 (s, 3H). $^{19}$F NMR (376 MHz, DMSO-d$_6$) δ −73.41, −112.61.

Example 468: 5-(3-Chloro-2-fluoro-6-(1H-tetrazol-1-yl)phenyl)-2-(1-(4-(1-oxidopyridin-4-yl)-1H-pyrazol-1-yl)-2-(3-(piperidine-1-carbonyl)-1H-pyrazol-1-yl)ethyl)pyridine 1-oxide

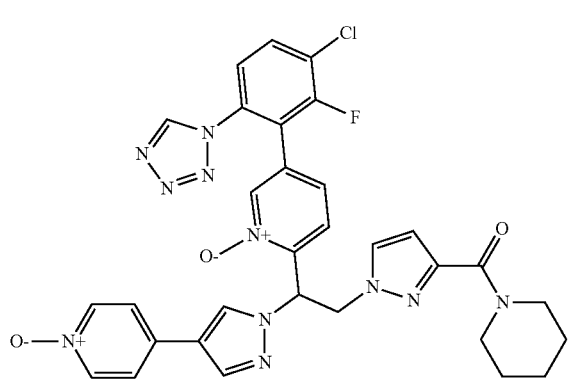 [SMILES: O=C(c1ccn(CC(c2ccc(-c3c(-n4cnnn4)ccc(Cl)c3F)c[n+]2[O-])n2cc(-c3cc[n+]([O-])cc3)cn2)n1)N1CCCCC1]

LC/MS: mass calculated for C$_{31}$H$_{27}$ClFN$_{11}$O$_3$: 655.20, measured (ES, m/z): 656.20 [M+H]$^+$. $^1$H NMR (300 MHz, DMSO-d$_6$) δ 9.67 (s, 1H), 8.43-8.58 (m, 2H), 8.10-8.18 (m, 3H), 8.02-8.10 (m, 1H), 7.70-7.79 (m, 1H), 7.62 (d, J=2.4 Hz, 1H), 7.56 (d, J=7.1 Hz, 2H), 7.45 (d, J=8.4 Hz, 1H), 7.22 (d, J=8.8 Hz, 1H), 6.45-6.56 (m, 1H), 6.37 (d, J=2.3 Hz, 1H), 4.92-5.16 (m, 2H), 3.41-3.60 (m, 4H), 1.40-1.62 (m, 4H), 1.20-1.39 (m, 2H). $^{19}$F NMR (282 MHz, DMSO-d$_6$) δ −112.63.

Example 469: (R*)-2-(2-(3-Carbamoyl-1H-pyrazol-1-yl)-1-(4-(2-(trifluoromethyl)pyridin-4-yl)-1H-pyrazol-1-yl)ethyl)-5-(3-chloro-2-fluoro-6-(1H-tetrazol-1-yl)phenyl)pyridine 1-oxide

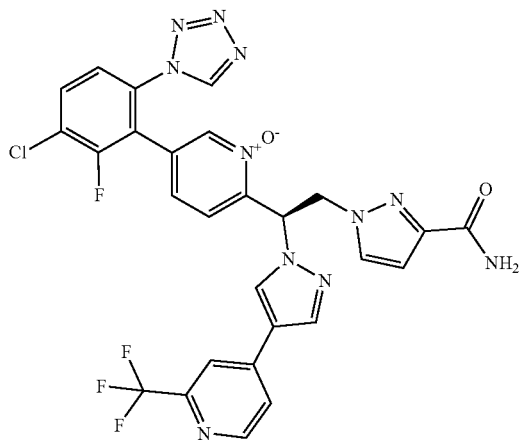

LC/MS: mass calculated for C$_{27}$H$_{18}$ClF$_4$N$_{11}$O$_2$: 639.13, measured (ES, m/z): 640.05 [M+H]$^+$. $^1$H NMR (300 MHz, DMSO-d$_6$) δ 9.71 (s, 1H), 8.77 (s, 1H), 8.66 (d, J=5.2 Hz, 1H), 8.54 (s, 1H), 8.39 (s, 1H), 8.03-8.14 (m, 2H), 7.86 (d, J=5.2 Hz, 1H), 7.78 (dd, J=8.7, 1.6 Hz, 1H), 7.48-7.56 (m, 2H), 7.39 (s, 1H), 7.20-7.30 (m, 2H), 6.59-6.70 (m, 1H), 6.49 (d, J=2.3 Hz, 1H), 5.10-5.24 (m, 1H), 4.94-5.09 (m, 1H). $^{19}$F NMR (282 MHz, DMSO-d$_6$) δ −66.53, −112.61.

Example 470: (R*)-5-(3-Chloro-2-fluoro-6-(1H-tetrazol-1-yl)phenyl)-2-(2-(3-(piperidine-1-carbonyl)-1H-pyrazol-1-yl)-1-(4-(2-(trifluoromethyl)pyridin-4-yl)-1H-pyrazol-1-yl)ethyl)pyridine 1-oxide

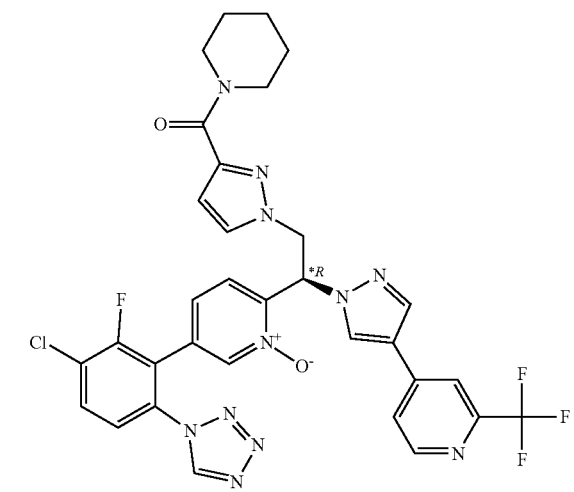 [SMILES: O=C(c1ccn(C[C@H](c2ccc(-c3c(-n4cnnn4)ccc(Cl)c3F)c[n+]2[O-])n2cc(-c3ccnc(C(F)(F)F)c3)cn2)n1)N1CCCCC1]

LC/MS: mass calculated for C$_{32}$H$_{26}$ClF$_4$N$_{11}$O$_2$: 707.19, measured (ES, m/z): 708.15 [M+H]$^+$. $^1$H NMR (300 MHz, DMSO-$d_6$) δ 9.68 (s, 1H), 8.73 (s, 1H), 8.64 (d, J=5.2 Hz, 1H), 8.51 (d, J=1.5 Hz, 1H), 8.35 (s, 1H), 8.00-8.11 (m, 2H), 7.84 (dd, J=5.3, 1.6 Hz, 1H), 7.75 (dd, J=8.7, 1.6 Hz, 1H), 7.65 (d, J=2.3 Hz, 1H), 7.53 (d, J=8.3 Hz, 1H), 7.23 (dd, J=8.2, 1.6 Hz, 1H), 6.50-6.69 (m, 1H), 6.37 (d, J=2.3 Hz, 1H), 4.96-5.17 (m, 2H), 3.29-3.52 (s, 4H), 1.32-4.57 (m, 4H), 1.13-1.30 (m, 2H). $^{19}$F NMR (282 MHz, DMSO-$d_6$) δ −66.59, −112.63.

Example 471: (R*)-5-(3-Chloro-2-fluoro-6-(1H-tetrazol-1-yl)phenyl)-2-(2-(3-(piperidine-1-carbonyl)-1H-pyrazol-1-yl)-1-(4-(2-(trifluoromethyl)pyridin-4-yl)-1H-pyrazol-1-yl)ethyl)pyridine 1-oxide trifluoroacetic acid

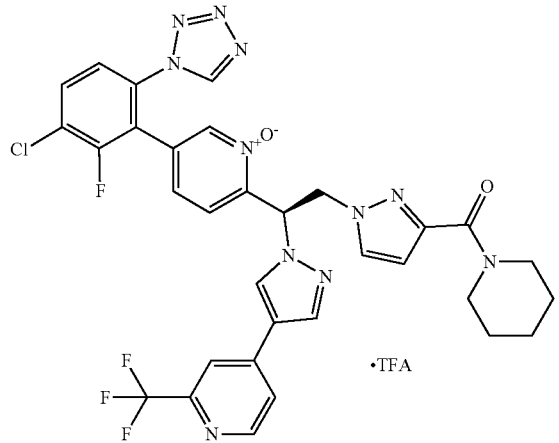

LC/MS: mass calculated for $C_{32}H_{26}ClF_4N_{11}O_2$: 707.19, measured (ES, m/z): 708.20 [M+H]$^+$. $^1$H NMR (300 MHz, DMSO-$d_6$) δ 9.55 (s, 1H), 8.51-8.61 (m, 2H), 8.39 (d, J=1.6 Hz, 1H), 8.23 (s, 1H), 7.95-7.98 (m, 1H), 7.88-7.93 (m, 1H), 7.76 (dd, J=5.2, 1.6 Hz, 1H), 7.57-7.66 (m, 2H), 7.53 (d, J=8.3 Hz, 1H), 7.23 (dd, J=8.3, 1.6 Hz, 1H), 6.46-6.58 (m, 1H), 6.34 (d, J=2.3 Hz, 1H), 4.92-5.11 (m, 2H), 3.28-3.45 (m, 4H), 1.29-1.51 (m, 4H), 1.08-1.22 (m, 2H). $^{19}$F NMR (282 MHz, DMSO-$d_6$) δ −66.60, −73.60, −112.65.

Example 472: (R*)-5-(3-Chloro-2-fluoro-6-(1H-tetrazol-1-yl)phenyl)-2-(2-(3-(dimethylcarbamoyl)-1H-pyrazol-1-yl)-1-(4-(2-(trifluoromethyl)pyridin-4-yl)-1H-pyrazol-1-yl)ethyl)pyridine 1-oxide

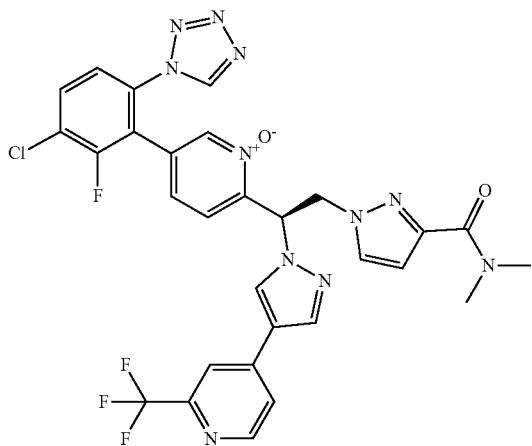

LC/MS: mass calculated for $C_{29}H_{22}ClF_4N_{11}O_2$: 667.16, measured (ES, m/z): 668.15 [M+H]$^+$. $^1$H NMR (300 MHz, DMSO-$d_6$) δ 9.68 (s, 1H), 8.75 (s, 1H), 8.64 (d, J=5.2 Hz, 1H), 8.50 (d, J=1.5 Hz, 1H), 8.35 (s, 1H), 8.00-8.11 (m, 2H), 7.84 (dd, J=5.0, 1.6 Hz, 1H), 7.75 (dd, J=8.7, 1.6 Hz, 1H), 7.61 (d, J=2.4 Hz, 1H), 7.52 (d, J=8.3 Hz, 1H), 7.23 (dd, J=8.3, 1.6 Hz, 1H), 6.49-6.61 (m, 1H), 6.39 (d, J=2.3 Hz, 1H), 4.97-5.18 (m, 2H), 3.00 (s, 3H), 2.88 (s, 3H). $^{19}$F NMR (282 MHz, DMSO-$d_6$) δ −66.54, −112.65.

Example 473: 5-(3-Chloro-2-fluoro-6-(1H-tetrazol-1-yl)phenyl)-2-(2-(1-methyl-1H-pyrazol-4-yl)-1-(4-(2-(trifluoromethyl)pyridin-4-yl)-1H-pyrazol-1-yl)ethyl)pyridine 1-oxide

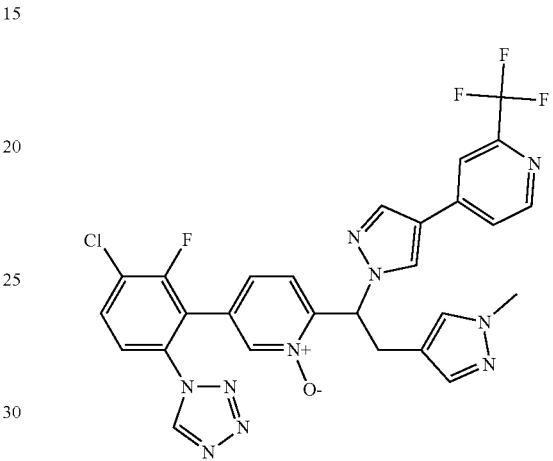

LC/MS: mass calculated for $C_{27}H_{19}ClF_4N_{10}O$: 610.14, measured (ES, m/z): 611.10 [M+H]$^+$. $^1$H NMR (300 MHz, DMSO-$d_6$) δ 9.67 (s, 1H), 8.80 (s, 1H), 8.65 (d, J=5.1 Hz, 1H), 8.44 (d, J=1.6 Hz, 1H), 8.34 (s, 1H), 8.10 (d, J=1.6 Hz, 1H), 7.98-8.08 (m, 1H), 7.88 (dd, J=5.1, 1.6 Hz, 1H), 7.74 (dd, J=8.7, 1.5 Hz, 1H), 7.40 (d, J=8.3 Hz, 1H), 7.28 (s, 1H), 7.16 (dd, J=8.3, 1.6 Hz, 1H), 7.01 (s, 1H), 6.00-6.12 (m, 1H), 3.69 (s, 2H), 3.29-3.41 (m, 3H). $^{19}$F NMR (282 MHz, DMSO-$d_6$) δ −66.53, −74.58, −112.72.

Example 474: (S*)-5-(3-Chloro-2-fluoro-6-(1H-tetrazol-1-yl)phenyl)-2-(1-(4-(2-cyanopyridin-4-yl)-1H-pyrazol-1-yl)-2-(4-fluoro-1H-pyrazol-1-yl)ethyl)pyridine 1-oxide

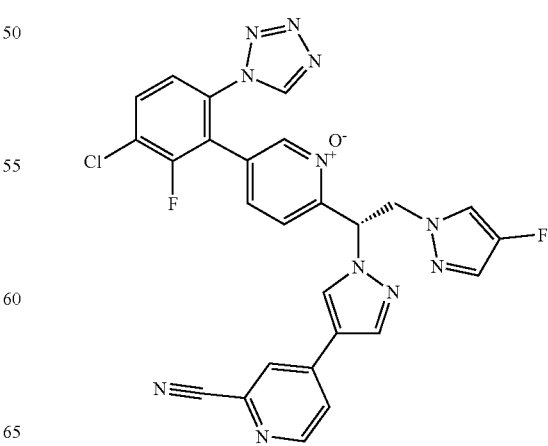

LC/MS: mass calculated for $C_{26}H_{16}ClF_2NO_{11}$: 571.12, measured (ES, m/z): 572.10 [M+H]$^+$. $^1$H NMR (300 MHz, DMSO-d$_6$) δ 9.66 (s, 1H), 8.55-8.86 (m, 2H), 8.49 (s, 1H), 8.24-8.41 (m, 2H), 7.99-8.11 (m, 1H), 7.87 (dd, J=5.2, 1.8 Hz, 1H), 7.74 (dd, J=8.7, 1.6 Hz, 1H), 7.67 (dd, J=4.6, 0.8 Hz, 1H), 7.38-7.51 (m, 2H), 7.21 (dd, J=8.3, 1.7 Hz, 1H), 6.42-6.59 (m, 1H), 4.82-5.06 (m, 2H). $^{19}$F NMR (282 MHz, DMSO-d$_6$) δ −112.62, −177.69.

Example 475: (R*)-5-(3-Chloro-2-fluoro-6-(1H-tetrazol-1-yl)phenyl)-2-(1-(4-(2-cyanopyridin-4-yl)-1H-pyrazol-1-yl)-2-(4-fluoro-1H-pyrazol-1-yl)ethyl)pyridine 1-oxide

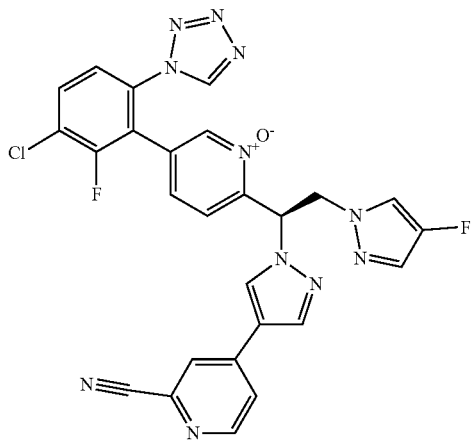

LC/MS: mass calculated for $C_{2H}H_{16}ClF_2N_{11}O$: 571.12, measured (ES, m/z): 572.10 [M+H]$^+$. $^1$H NMR (300 MHz, DMSO-d$_6$) δ 9.66 (s, 1H), 8.58-8.68 (m, 2H), 8.49 (d, J=1.6 Hz, 1H), 8.24-8.35 (m, 2H), 7.99-8.10 (m, 1H), 7.87 (dd, J=5.2, 1.8 Hz, 1H), 7.65-7.76 (m, 2H), 7.38-7.51 (m, 2H), 7.21 (dd, J=8.3, 1.7 Hz, 1H), 6.45-6.61 (m, 1H), 4.84-5.03 (m, 2H). $^{19}$F NMR (282 MHz, DMSO-d$_6$) δ −112.62, −177.70.

Example 476: (S*)-2-(2-(3-Carbamoyl-1H-pyrazol-1-yl)-1-(4-(2-(trifluoromethyl)pyridin-4-yl)-1H-pyrazol-1-yl)ethyl)-5-(3-chloro-6-(difluoromethyl)-2-fluorophenyl)pyridine 1-oxide

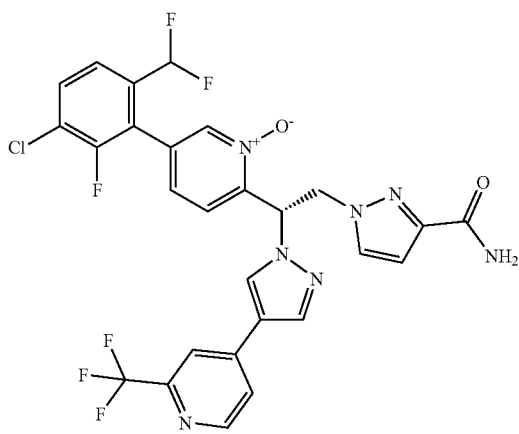 [SMILES: NC(=O)c1ccn(C[C@@H](c2ccc(-c3c(C(F)F)ccc(Cl)c3F)c[n+]2[O-])n2cc(-c3ccnc(C(F)(F)F)c3)cn2)n1]

LC/MS: mass calculated for $C_{27}H_{18}ClF_6N_7O_2$: 621.1, measured (ES, m/z): 622.15 [M+H]$^+$. $^1$H NMR (300 MHz, DMSO-d$_6$) δ 8.53-8.67 (m, 2H), 8.47 (s, 1H), 8.29 (s, 1H), 8.00 (d, J=1.6 Hz, 1H), 7.74-7.87 (m, 2H), 7.64 (d, J=8.3 Hz, 1H), 7.52-7.61 (m, 2H), 7.46 (dd, J=8.3, 1.6 Hz, 1H), 6.86 (d, J=54.0 Hz, 1H), 6.69 (dd, J=10.0, 4.4 Hz, 1H), 6.50 (d, J=2.3 Hz, 1H), 5.16-5.22 (m, 1H), 5.04 (dd, J=13.9, 4.4 Hz, 1H). $^{19}$F NMR (282 MHz, DMSO-d$_6$) δ −66.55, −74.46, −115.18.

Example 477: (R*)-2-(2-(3-Carbamoyl-1H-pyrazol-1-yl)-1-(4-(2-(trifluoromethyl)pyridin-4-yl)-1H-pyrazol-1-yl)ethyl)-5-(3-chloro-6-(difluoromethyl)-2-fluorophenyl)pyridine 1-oxide

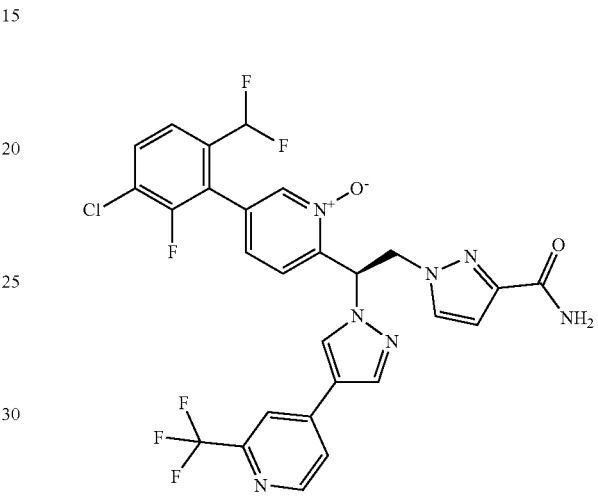

LC/MS: mass calculated for $C_{27}H_{18}ClF_6N_7O_2$: 621.11, measured (ES, m/z): 622.10 [M+H]$^+$. $^1$H NMR (300 MHz, DMSO-d$_6$) δ 8.81 (s, 1H), 8.65 (d, J=5.2 Hz, 1H), 8.58 (d, J=1.6 Hz, 1H), 8.41 (s, 1H), 8.08 (d, J=1.4 Hz, 1H), 7.81-7.94 (m, 2H), 7.54-7.66 (m, 3H), 7.45 (dd, J=8.2, 1.6 Hz, 1H), 7.36 (s, 1H), 7.24 (s, 1H), 6.66-6.93 (m, 2H), 6.50 (d, J=2.3 Hz, 1H), 5.02-5.28 (m, 2H). $^{19}$F NMR (282 MHz, DMSO-d$_6$) δ −66.54, −115.17.

Example 479: 5-(3-Chloro-2-fluoro-6-(1H-tetrazol-1-yl)phenyl)-2-(2-cyclopropyl-1-(4-(oxazol-5-yl)-1H-pyrazol-1-yl)ethyl)pyridine 1-oxide

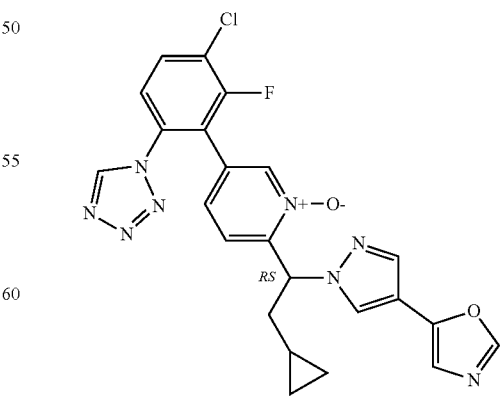

LC/MS: mass calculated for $C_{23}H_{18}ClFN_8O_2$: 492.1, measured (ES, m/z): 493.1 [M+H]$^+$. $^1$H NMR (400 MHz, CD₃OD) δ 9.38 (s, 1H), 8.28-8.42 (m, 2H), 8.15-8.27 (m, 1H), 7.91 (bs, 2H), 7.56-7.64 (m, 1H), 7.42-7.52 (m, 1H), 7.17-7.41 (m, 2H), 6.17-6.31 (m, 1H), 2.42-2.55 (m, 1H), 1.95-2.06 (m, 1H), 0.60-0.74 (m, 1H), 0.34-0.50 (m, 2H), 0.19 (bd, J=4.55 Hz, 1H), 0.03 (bd, J=4.04 Hz, 1H).

Example 480: 5-(3-Chloro-2-fluoro-6-(1H-tetrazol-1-yl)phenyl)-2-(2-cyclopropyl-1-(4-(isothiazol-4-yl)-1H-pyrazol-1-yl)ethyl)pyridine 1-oxide

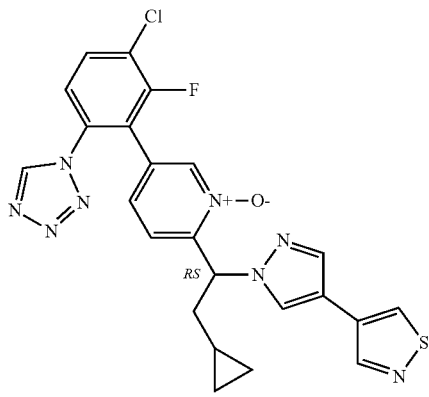 [SMILES: [O-][n+]1cc(-c2c(-n3cnnn3)ccc(Cl)c2F)ccc1C(CC1CC1)n1cc(-c2cnsc2)cn1]

LC/MS: mass calculated for C₂₃H₁₈ClFN₈OS: 508.1, measured (ES, m/z): 509.1 [M+H]⁺. ¹H NMR (400 MHz, CD₃OD) δ 9.38 (s, 1H), 8.86-9.01 (m, 1H), 8.71-8.85 (m, 1H), 8.25-8.47 (m, 2H), 7.96-8.06 (m, 1H), 7.91 (s, 1H), 7.60 (br d, J=8.59 Hz, 1H), 7.44 (br s, 1H), 7.16-7.32 (m, 1H), 6.15-6.32 (m, 1H), 2.42-2.58 (m, 1H), 1.94-2.05 (m, 1H), 0.64-0.78 (m, 1H), 0.36-0.50 (m, 2H), 0.16-0.25 (m, 1H), 0.02-0.11 (m, 1H).

Example 481: 5-(3-Chloro-2-fluoro-6-(1H-tetrazol-1-yl)phenyl)-2-(2-cyclopropyl-1-(4-(1-methyl-1H-imidazol-5-yl)-1H-pyrazol-1-yl)ethyl)pyridine 1-oxide

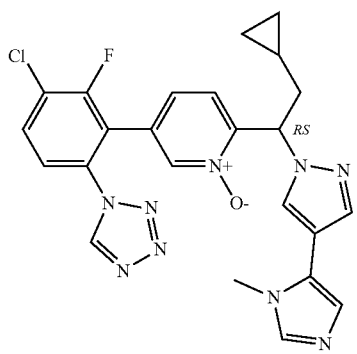 [SMILES: Cn1cncc1-c1cnn(C(CC2CC2)c2ccc(-c3c(-n4cnnn4)ccc(Cl)c3F)c[n+]2[O-])c1]

LC/MS: mass calculated for C₂₄H₂₁ClFN₉O: 505.2, measured (ES, m/z): 506.1 [M+H]⁺. ¹H NMR (400 MHz, CD₃OD) δ ppm) 9.40 (s, 1H), 8.91-8.96 (m, 1H), 8.38 (s, 2H), 7.86-7.97 (m, 2H), 7.58-7.72 (m, 3H), 7.28-7.37 (m, 1H), 6.27 (br dd, J=10.27, 3.91 Hz, 1H), 3.93 (s, 3H), 2.41-2.54 (m, 1H), 2.02-2.13 (m, 1H), 0.63-0.73 (m, 1H), 0.34-0.49 (m, 2H), 0.15-0.22 (m, 1H), 0.00-0.06 (m, 1H).

Example 482: 5-(3-Chloro-2-fluoro-6-(1H-tetrazol-1-yl)phenyl)-2-(1-(4-(2-cyanopyridin-4-yl)-1H-pyrazol-1-yl)-3-(difluoromethoxy)propyl)pyridine 1-oxide trifluoroacetic acid

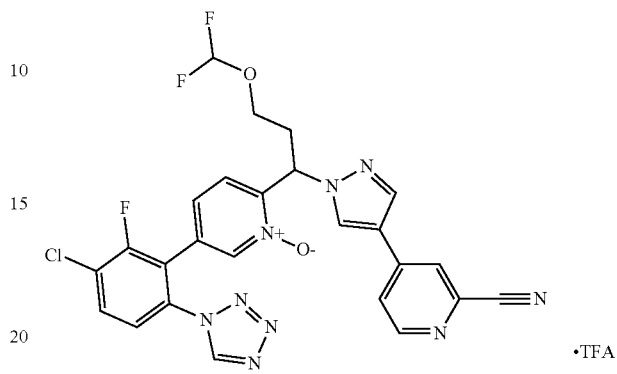

LC/MS: mass calculated for C₂₅H₁₇ClF₃N₉O₂: 567.11, measured (ES, m/z): 568.10 [M+H]⁺. ¹H NMR (300 MHz, DMSO-d₆) δ 9.66 (s, 1H), 8.81 (s, 1H), 8.64 (d, J=5.2 Hz, 1H), 8.43 (d, J=1.6 Hz, 1H), 8.32 (d, J=2.7 Hz, 2H), 7.97-8.09 (m, 1H), 7.92 (dd, J=5.2, 1.8 Hz, 1H), 7.73 (dd, J=8.7, 1.5 Hz, 1H), 7.34 (d, J=8.3 Hz, 1H), 7.18 (dd, J=8.3, 1.6 Hz, 1H), 6.61 (t, J=75.7 Hz, 1H), 6.12-6.27 (m, 1H), 3.51-3.72 (m, 2H), 2.59 (m, 2 h). ¹⁹F NMR (282 MHz, DMSO-d₆) δ −75.03, −83.25, −112.67.

Example 483: 5-(3-Chloro-2-fluoro-6-(1H-tetrazol-1-yl)phenyl)-2-(1-(4-(2-cyanopyridin-4-yl)-1H-pyrazol-1-yl)-2-(2-oxopyridin-1(2H)-yl)ethyl)pyridine 1-oxide

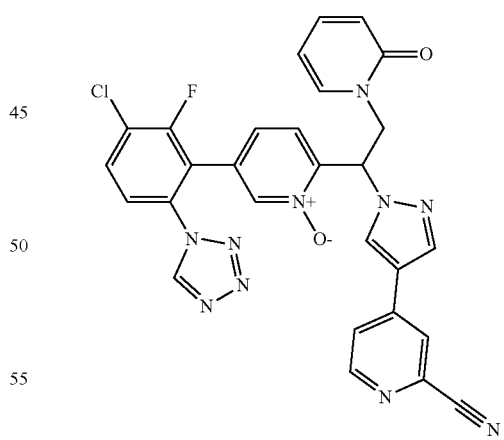

LC/MS: mass calculated for C₂₈H₁₈ClFN₁₀O₂: 580.13, measured (ES, m/z): 581.10 [M+H]⁺. ¹H NMR (400 MHz, DMSO-d₆) δ 9.69 (s, 1H), 8.67 (s, 1H), 8.62 (d, J=5.2 Hz, 1H), 8.47 (d, J=1.7 Hz, 1H), 8.30 (s, 2H), 8.11-8.02 (m, 1H), 7.89 (dd, J=5.2, 1.8 Hz, 1H), 7.83-7.73 (m, 2H), 7.32-7.40 (m, 1H), 7.26 (dd, J=8.2, 1.7 Hz, 1H), 7.16 (dd, J=7.0, 2.0 Hz, 1H), 6.48-6.59 (m, 1H), 6.39 (d, J=9.2 Hz, 1H), 5.99-6.07 (m, 1H), 4.72-4.49 (m, 2H).

Example 484: 5-(3-Chloro-2-fluoro-6-(1H-tetrazol-1-yl)phenyl)-2-(2-cyclopropyl-1-(4-(1-methyl-1H-1,2,3-triazol-5-yl)-1H-pyrazol-1-yl)ethyl)pyridine 1-oxide

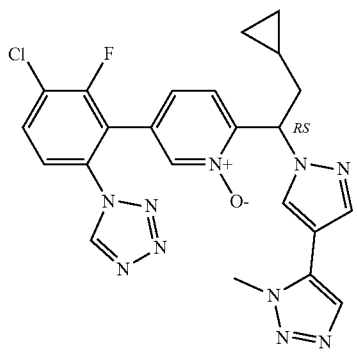 [SMILES: Cn1nncc1-c1cnn(C(CC2CC2)c2ccc(-c3c(-n4cnnn4)ccc(Cl)c3F)c[n+]2[O-])c1]

LC/MS: mass calculated for $C_{23}H_{20}ClFN_{10}O$: 506.2, measured (ES, m/z): 507.2 [M+H]$^+$. $^1$H NMR (400 MHz, CD$_3$OD) δ. 9.39 (s, 1H), 8.38 (d, J=10.76 Hz, 2H), 7.88-7.98 (m, 3H), 7.59-7.64 (m, 1H), 7.54 (d, J=8.31 Hz, 1H), 7.29 (d, J=8.31 Hz, 1H), 6.27 (dd, J=10.03, 4.16 Hz, 1H), 4.15 (s, 3H), 2.48 ((m, 1H), 2.00-2.10 (m, 1H), 0.62-0.76 (m, 1H), 0.34-0.50 (m, 2H), 0.19 (m, 1H), 0.02-0.07 (m, 1H).

Example 485: 5-(3-Chloro-2-fluoro-6-(1H-tetrazol-1-yl)phenyl)-2-(1-(4-(2-cyanopyridin-4-yl)-1H-pyrazol-1-yl)-2-(2-oxopyrrolidin-1-yl)ethyl)pyridine 1-oxide trifluoroacetic acid

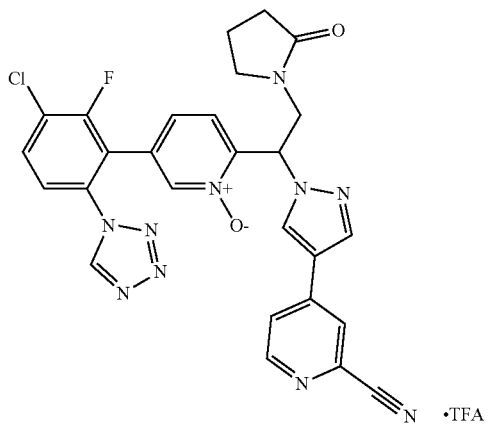 [SMILES: N#Cc1cc(-c2cnn(C(CN3CCCC3=O)c3ccc(-c4c(-n5cnnn5)ccc(Cl)c4F)c[n+]3[O-])c2)ccn1]

LC/MS: mass calculated for $C_{27}H_{20}ClFN_{10}O_2$: 570.14, measured (ES, m/z): 571.10 [M+H]$^+$. $^1$H NMR (400 MHz, DMSO-d$_6$) δ 9.68 (s, 1H), 8.83 (s, 1H), 8.65 (d, J=5.2 Hz, 1H), 8.45 (s, 1H), 8.22-8.39 (m, 2H), 8.00-8.12 (m, 1H), 7.93 (d, J=5.2 Hz, 1H), 7.76 (d, J=8.7 Hz, 1H), 7.63 (d, J=8.2 Hz, 1H), 7.22 (d, J=8.3 Hz, 1H), 6.22-6.41 (m, 1H), 3.91-4.12 (m, 2H), 3.19-3.40 (m, 1H), 2.81-3.02 (m, 1H), 2.01-2.24 (m, 2H), 1.69-1.92 (m, 2H). $^{19}$F NMR (376 MHz, DMSO-d$_6$) δ −75.00, −112.67.

Example 486: 5-(3-Chloro-2-fluoro-6-(1H-tetrazol-1-yl)phenyl)-2-(3-(difluoromethoxy)-1-(4-(2-(trifluoromethyl)pyridin-4-yl)-1H-pyrazol-1-yl)propyl)pyridine 1-oxide trifluoroacetic acid

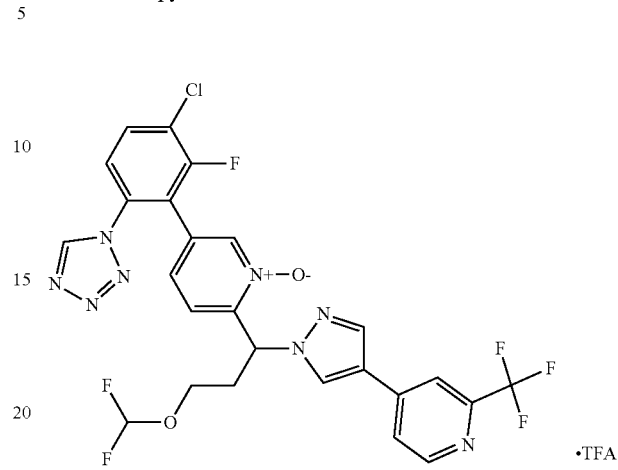

LC/MS: mass calculated for $C_{25}H_{17}ClF_6N_8O_2$: 610.11, measured (ES, m/z): 611.00 [M+H]$^+$. $^1$H NMR (300 MHz, DMSO-d$_6$) δ 9.67 (s, 1H), 8.88 (s, 1H), 8.67 (d, J=5.2 Hz, 1H), 8.41-8.52 (m, 2H), 8.10-8.17 (m, 1H), 8.04-8.06 (m, 1H), 7.91 (dd, J=5.2, 1.6 Hz, 1H), 7.74 (dd, J=8.7, 1.5 Hz, 1H), 7.31 (d, J=8.3 Hz, 1H), 7.17 (dd, J=7.9, 1.3 Hz, 1H), 6.37-6.85 (m, 1H), 6.19-6.23 (m, 1H), 3.61-3.90 (m, 2H), 2.59 (s, 2H). $^{19}$F NMR (282 MHz, DMSO-d$_6$) δ −66.54, −74.84, −83.28, −112.68.

Example 487: 5-(3-Chloro-2-fluoro-6-(1H-tetrazol-1-yl)phenyl)-2-(2-(4,5-dihydropyrano[3,4-c]pyrazol-2(7H)-yl)-1-(4-(2-(trifluoromethyl)pyridin-4-yl)-1H-pyrazol-1-yl)ethyl)pyridine 1-oxide trifluoroacetic acid

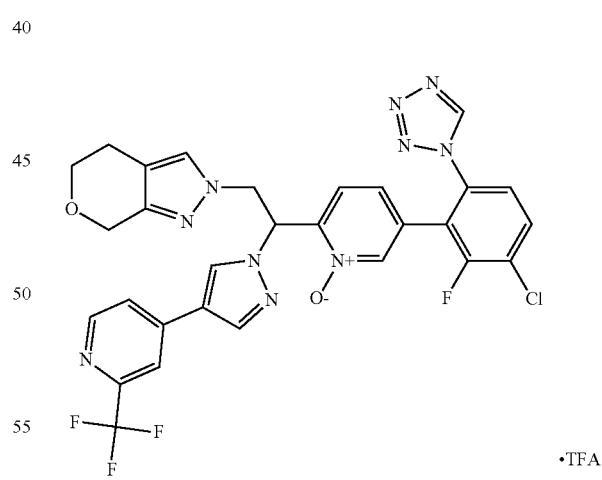

LC/MS: mass calculated for $C_{29}H_{21}ClF_4N_{10}O_2$: 652.15, measured (ES, m/z): 653.20 [M+H]$^+$. $^1$H NMR (300 MHz, DMSO-d$_6$) δ 9.66 (s, 1H), 8.75 (s, 1H), 8.65 (d, J=5.3 Hz, 1H), 8.49 (s, 1H), 8.36 (s, 1H), 7.99-8.11 (m, 2H), 7.86 (d, J=5.2 Hz, 1H), 7.74 (dd, J=8.8, 1.6 Hz, 1H), 7.42 (d, J=8.3 Hz, 1H), 7.27 (s, 1H), 7.18 (d, J=7.8 Hz, 1H), 6.46-6.59 (m, 1H), 4.81-5.04 (m, 2H), 4.44-4.61 (m, 2H), 3.62-3.71 (m, 2H), 2.39-2.46 (m, 2H). $^{19}$F NMR (282 MHz, DMSO-d$_6$) δ −66.48, −74.67f, −112.64.

Example 488: 5-(3-Chloro-2-fluoro-6-(1H-tetrazol-1-yl)phenyl)-2-(2-(5-(methoxymethyl)-1H-pyrazol-1-yl)-1-(4-(2-(trifluoromethyl)pyridin-4-yl)-1H-pyrazol-1-yl)ethyl)pyridine 1-oxide trifluoroacetic acid

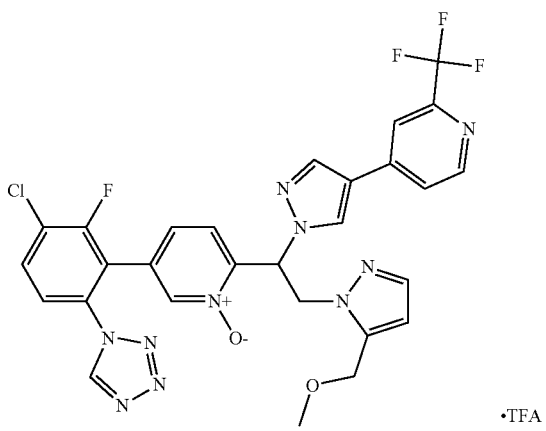 [SMILES: COCc1ccnn1CC(c1ccc(-c2c(-n3cnnn3)ccc(Cl)c2F)c[n+]1[O-])n1cc(-c2ccnc(C(F)(F)F)c2)cn1]

LC/MS: mass calculated for $C_{28}H_{21}ClF_4N_{10}O_2$: 640.2, measured (ES, m/z): 641.1 [M+H]$^+$. $^1$H NMR (400 MHz, DMSO-d$_6$) δ 9.68 (s, 1H), 8.62-8.71 (m, 2H), 8.51 (d, J=1.6 Hz, 1H), 8.35 (s, 1H), 8.03-8.11 (m, 2H), 7.85 (dd, J=5.2, 1.7 Hz, 1H), 7.76 (dd, J=8.7, 1.5 Hz, 1H), 7.48 (d, J=8.3 Hz, 1H), 7.36 (d, J=1.8 Hz, 1H), 7.22 (dd, J=8.3, 1.7 Hz, 1H), 6.66 (dd, J=9.7, 4.4 Hz, 1H), 6.16 (d, J=1.8 Hz, 1H), 5.03 (dd, J=14.0, 9.8 Hz, 1H), 4.89 (dd, J=14.0, 4.4 Hz, 1H), 4.44 (d, J=12.6 Hz, 1H), 4.39 (d, J=12.6 Hz, 1H), 3.24 (s, 3H). $^{19}$F NMR (376 MHz, DMSO-d$_6$) δ −66.54, −74.58, −112.61.

Example 489: 5-(3-Chloro-2-fluoro-6-(1H-tetrazol-1-yl)phenyl)-2-(2-(4,7-dihydropyrano[3,4-c]pyrazol-1(5H)-yl)-1-(4-(2-(trifluoromethyl)pyridin-4-yl)-1H-pyrazol-1-yl)ethyl)pyridine 1-oxide trifluoroacetic acid

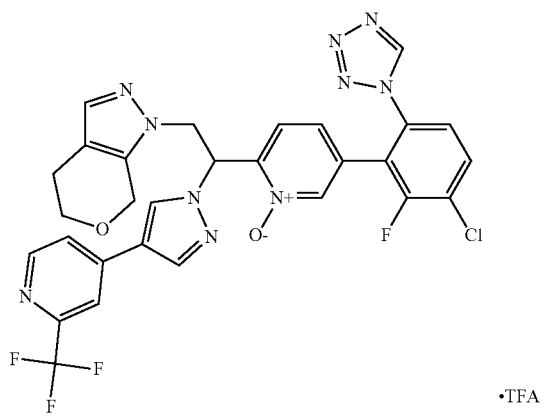 [SMILES: [O-][n+]1cc(-c2c(-n3cnnn3)ccc(Cl)c2F)ccc1C(Cn1ncc2c1COCC2)n1cc(-c2ccnc(C(F)(F)F)c2)cn1]

LC/MS: mass calculated for $C_{29}H_{21}ClF_4N_{10}O_2$: 652.15, measured (ES, m/z): 653.20 [M+H]$^+$. $^1$H NMR (400 MHz, DMSO-d$_6$) δ 9.68 (s, 1H), 8.63-8.72 (m, 2H), 8.53 (d, J=1.6 Hz, 1H), 8.39 (s, 1H), 8.03-8.11 (m, 2H), 7.85 (d, J=4.9 Hz, 1H), 7.76 (dd, J=8.7, 1.5 Hz, 1H), 7.41 (d, J=8.3 Hz, 1H), 7.19-7.28 (m, 2H), 6.46-6.58 (m, 1H), 4.80-4.91 (m, 1H), 4.68-4.79 (m, 2H), 4.41 (d, J=14.6 Hz, 1H), 3.61-3.74 (m, 1H), 3.49-3.57 (m, 1H), 2.29-2.44 (m, 2H). $^{19}$F NMR (376 MHz, DMSO-d$_6$) −66.55, −73.71, −112.63.

Example 490: 5-(3-Chloro-2-fluoro-6-(1H-tetrazol-1-yl)phenyl)-2-(1-(4-(2-cyanopyridin-4-yl)-1H-pyrazol-1-yl)-2-(2-oxopyrrolidin-1-yl)ethyl)pyridine 1-oxide trifluoroacetic acid

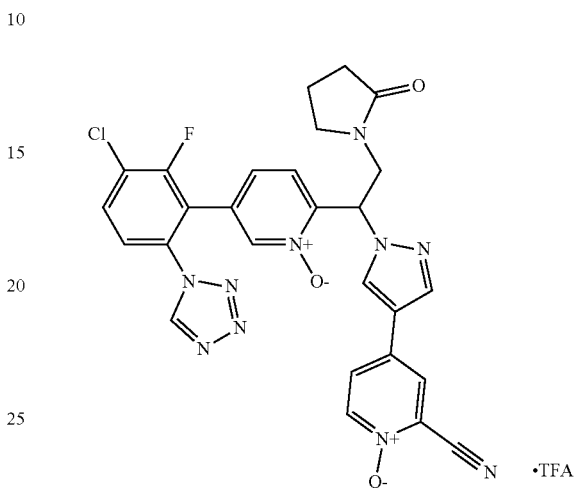

LC/MS: mass calculated for $C_{27}H_{20}ClFN_{10}O_3$: 586.14, measured (ES, m/z): 587.10 [M+H]$^+$. $^1$H NMR (400 MHz, DMSO-d$_6$) δ 9.64 (s, 1H), 8.65 (s, 1H), 8.35-8.44 (m, 3H), 8.16 (s, 1H), 7.98-8.07 (m, 1H), 7.89 (dd, J=7.0, 2.7 Hz, 1H), 7.72 (dd, J=8.7, 1.5 Hz, 1H), 7.61 (d, J=8.3 Hz, 1H), 7.19-7.25 (m, 1H), 6.25-6.33 (m, 1H), 3.93-4.09 (m, 2H), 3.22-3.33 (m, 1H), 2.81-2.99 (m, 1H), 2.06-2.21 (m, 2H), 1.69-1.91 (m, 2 h). $^{19}$F NMR (376 MHz, DMSO-d$_6$) δ −74.42, −112.74.

Example 491: 2-(1-(1'H,2H-[3,4'-Bipyrazol]-1'-yl)-2-cyclopropylethyl)-5-(3-chloro-2-fluoro-6-(1H-tetrazol-1-yl)phenyl)pyridine 1-oxide

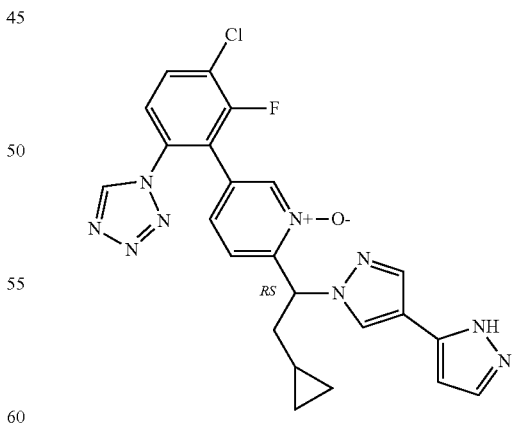

LC/MS: mass calculated for $C_{23}H_{19}ClFN_9O$: 491.1, measured (ES, m/z): 492.1 [M+H]$^+$. $^1$H NMR (400 MHz, CD$_3$OD) δ ppm 0.02-0.10 (m, 1H) 0.15-0.25 (m, 1H) 0.35-0.50 (m, 2 h) 0.62-0.78 (m, 1H) 1.96-2.07 (m, 1H) 2.43-2.55 (m, 1H) 6.19-6.29 (m, 1H) 6.64-6.74 (m, 1H) 7.26-7.34 (m, 1H) 7.48 (d, J=8.31 Hz, 1H) 7.60 (dd, J=8.56, 1.71 Hz, 1H) 7.79-7.86 (m, 1H) 7.88-7.94 (m, 1H) 7.97 (s, 1H) 8.34 (br d, J=12.72 Hz, 2 h) 9.36-9.42 (m, 1H).

Example 492: 5-(3-Chloro-2-fluoro-6-(1H-tetrazol-1-yl)phenyl)-2-(2-(4-fluoro-1H-pyrazol-1-yl)-1-(4-(6-(trifluoromethyl)pyrimidin-4-yl)-1H-pyrazol-1-yl)ethyl)pyridine 1-oxide

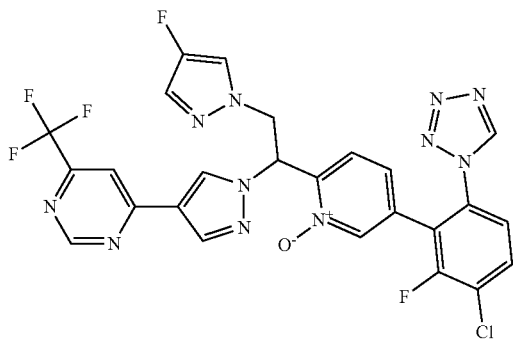 [SMILES: [O-][n+]1cc(-c2c(-n3cnnn3)ccc(Cl)c2F)ccc1C(Cn1cc(F)cn1)n1cc(-c2cc(C(F)(F)F)ncn2)cn1]

LC/MS: mass calculated for $C_{25}H_{15}ClF_5N_{11}O$: 615.11, measured (ES, m/z): 616.10 [M+H]$^+$. $^1$H NMR (400 MHz, DMSO-d$_6$) δ 9.68 (s, 1H), 9.26 (s, 1H), 8.81 (s, 1H), 8.51 (s, 1H), 8.44 (s, 1H), 8.29 (s, 1H), 8.00-8.12 (m, 1H), 7.76 (d, J=8.7 Hz, 1H), 7.71 (d, J=4.6 Hz, 1H), 7.49 (d, J=8.3 Hz, 1H), 7.44 (d, J=4.1 Hz, 1H), 7.23 (dd, J=8.3, 1.6 Hz, 1H), 6.51-6.63 (m, 1H), 4.88-5.11 (m, 2 h). $^{19}$F NMR (376 MHz, DMSO-d$_6$) δ −68.75, −74.42, −112.63, −177.62.

Example 493: 5-(3-Chloro-2-fluoro-6-(1H-tetrazol-1-yl)phenyl)-2-(2-(4-fluoro-1H-pyrazol-1-yl)-1-(4-(2-(trifluoromethyl)pyrimidin-4-yl)-1H-pyrazol-1-yl)ethyl)pyridine 1-oxide

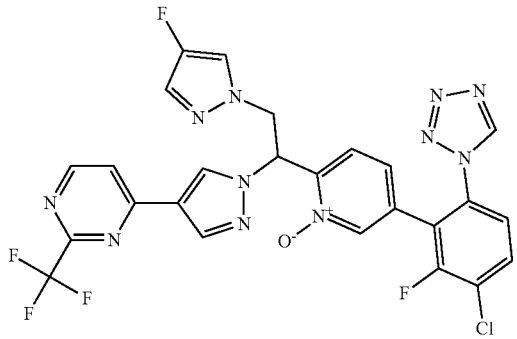 [SMILES: [O-][n+]1cc(-c2c(-n3cnnn3)ccc(Cl)c2F)ccc1C(Cn1cc(F)cn1)n1cc(-c2ccnc(C(F)(F)F)n2)cn1]

LC/MS: mass calculated for $C_{25}H_{15}ClF_5N_{11}O$: 615.11, measured (ES, m/z): 616.10 [M+H]$^+$. $^1$H NMR (400 MHz, DMSO-d$_6$) δ 9.68 (s, 1H), 8.93 (d, J=5.4 Hz, 1H), 8.74 (s, 1H), 8.51 (d, J=1.6 Hz, 1H), 8.36 (s, 1H), 7.97-8.11 (m, 2H), 7.69-7.81 (m, 2H), 7.40-7.50 (m, 2H), 7.23 (dd, J=8.3, 1.7 Hz, 1H), 6.51-6.64 (m, 1H), 4.88-5.12 (m, 2 h). $^{19}$F NMR (376 MHz, DMSO-d$_6$) δ −69.36, −74.58, −112.63, −177.63.

Example 494: 2-(2-(5-(2-Amino-2-oxoethyl)-1H-pyrazol-1-yl)-1-(4-(2-(trifluoromethyl)pyridin-4-yl)-1H-pyrazol-1-yl)ethyl)-5-(3-chloro-2-fluoro-6-(1H-tetrazol-1-yl)phenyl)pyridine 1-oxide

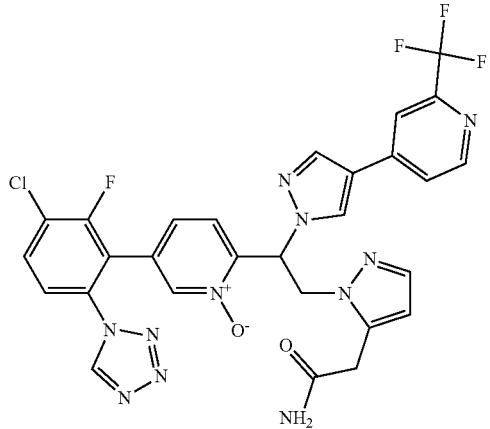 [SMILES: NC(=O)Cc1ccnn1CC(c1ccc(-c2c(-n3cnnn3)ccc(Cl)c2F)c[n+]1[O-])n1cc(-c2ccnc(C(F)(F)F)c2)cn1]

LC/MS: mass calculated for $C_{28}H_{20}ClF_4N_1O_2$: 653.14, measured (ES, m/z): 654.20 [M+H]$^+$. $^1$H NMR (300 MHz, DMSO-d$_6$) δ 9.67 (s, 1H), 8.69 (s, 1H), 8.64 (d, J=5.3 Hz, 1H), 8.50 (s, 1H), 8.33 (s, 1H), 7.99-8.11 (m, 2H), 7.83 (d, J=5.3 Hz, 1H), 7.74 (dd, J=8.7, 1.5 Hz, 1H), 7.52 (s, 1H), 7.40 (d, J=8.4 Hz, 1H), 7.28 (d, J=1.8 Hz, 1H), 7.19 (d, J=8.1 Hz, 1H), 7.02 (s, 1H), 6.59-6.71 (m, 1H), 5.97 (d, J=1.8 Hz, 1H), 4.79-5.05 (m, 2H), 3.52 (s, 2H).

Example 495: 2-(1-(4-(6-Amino-2-fluoropyridin-3-yl)-1H-pyrazol-1-yl)-2-(4-(2-oxo-2-(piperidin-1-yl)ethyl)-1H-pyrazol-1-yl)ethyl)-5-3-chloro-2-fluoro-6-(1H-tetrazol-1-yl)phenyl)pyridine 1-oxide

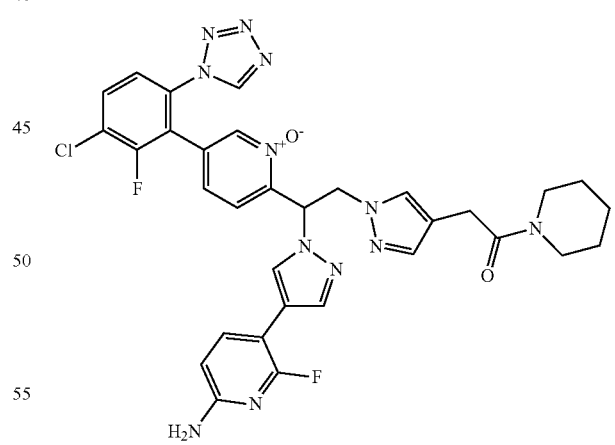

LC/MS: mass calculated for $C_{32}H_{29}ClF_2N_{12}O_2$: 686.12, measured (ES, m/z): 687.20 [M+H]$^+$. $^1$H NMR (400 MHz, DMSO-d$_6$) δ 9.69 (s, 1H), 8.51 (d, J=1.6 Hz, 1H), 8.03-8.11 (m, 2H), 7.89 (d, J=1.6 Hz, 1H), 7.72-7.81 (m, 2H), 7.11-7.34 (m, 4H), 6.48-6.53 (m, 1H), 6.30-6.37 (m, 1H), 4.95-5.09 (m, 2H), 4.84-4.93 (m, 1H), 3.38 (s, 2H), 3.23-3.34 (m, 2H), 3.11-3.22 (m, 2H), 1.24-1.42 (m, 4H), 1.08-1.21 (m, 2H). $^{19}$F NMR (376 MHz, DMSO-d$_6$) δ −71.10, −74.85, −112.62.

Example 496: 4-(1-(1-(5-(3-Chloro-2-fluoro-6-(1H-tetrazol-1-yl)phenyl)-1-oxidopyridin-2-yl)-2-(4-fluoro-1H-pyrazol-1-yl)ethyl)-1H-pyrazol-4-yl)-2-methylpyridine 1-oxide

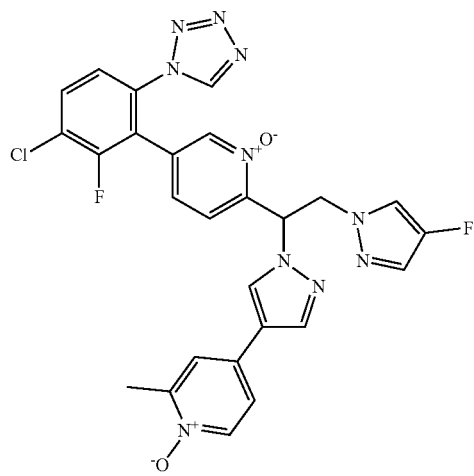

LC/MS: mass calculated for C$_{26}$H$_{19}$ClF$_2$N$_{10}$O$_2$: 576.13, measured (ES, m/z): 577.10 [M+H]$^+$. $^1$H NMR (400 MHz, DMSO-d$_6$) δ 9.69 (s, 1H), 8.51 (s, 2H), 8.31-8.39 (m, 1H), 8.23-8.18 (m, 1H), 8.01-8.15 (m, 1H), 7.80-7.89 (m, 1H), 7.77 (dd, J=8.7, 1.5 Hz, 1H), 7.68 (d, J=4.6 Hz, 1H), 7.53-7.61 (m, 1H), 7.45 (d, J=4.3 Hz, 2H), 7.20-7.27 (m, 1H), 6.48-6.59 (m, 1H), 4.80-5.07 (m, 2H), 2.38-2.44 (m, 3H). $^{19}$F NMR (376 MHz, DMSO-d$_6$) δ −74.66, −112.65, −177.75.

Example 497: 5-(3-Chloro-2-fluoro-6-(1H-tetrazol-1-yl)phenyl)-2-(2-(4-(2-oxo-2-(piperidin-1-yl)ethyl)-1H-pyrazol-1-yl)-1-(4-(2-(trifluoromethyl)pyridin-4-yl)-1H-pyrazol-1-yl)ethyl)pyridine 1-oxide

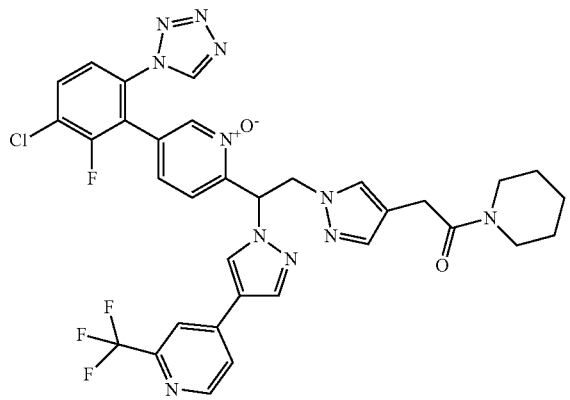

LC/MS: mass calculated for C$_{33}$H$_{28}$ClF$_4$NO$_{112}$: 721.21, measured (ES, m/z): 722.15 [M+H]$^+$. $^1$H NMR (400 MHz, DMSO-d$_6$) δ 9.69 (s, 1H), 8.75 (s, 1H), 8.67 (d, J=5.2 Hz, 1H), 8.52 (d, J=1.6 Hz, 1H), 8.39 (s, 1H), 8.03-8.13 (m, 2H), 7.88 (dd, J=5.2, 1.7 Hz, 1H), 7.77 (dd, J=8.7, 1.5 Hz, 1H), 7.45 (d, J=8.3 Hz, 1H), 7.34 (s, 1H), 7.28 (s, 1H), 7.22 (dd, J=8.3, 1.7 Hz, 1H), 6.50-6.61 (m, 1H), 4.99-5.11 (m, 1H), 4.84-4.96 (m, 1H), 3.37 (s, 2H), 3.21-3.31 (m, 2H), 3.12-3.19 (m, 2H), 1.22-1.32 (m, 4H), 1.05-1.19 (m, 2H). $^{19}$F NMR (376 MHz, DMSO-d$_6$) δ −66.58, −74.73, −112.60.

Example 498: 5-(3-Chloro-2-fluoro-6-(1H-tetrazol-1-yl)phenyl)-2-(2-(4-fluoro-1H-pyrazol-1-yl)-1-(4-(2-methylpyridin-4-yl)-1H-pyrazol-1-yl)ethyl)pyridine 1-oxide

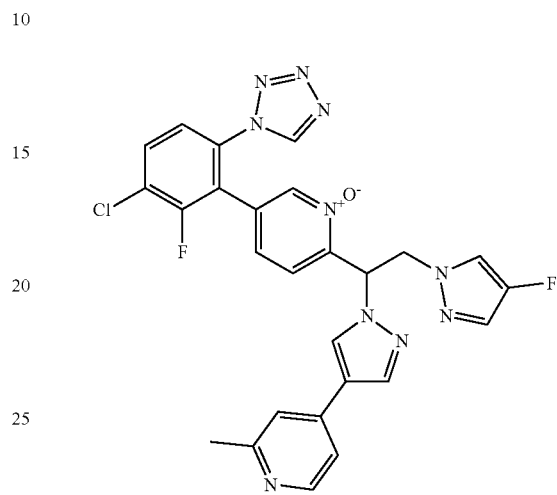

LC/MS: mass calculated for C$_{26}$H$_{19}$ClF$_2$N$_{10}$O: 560.14, measured (ES, m/z): 561.10 [M+H]$^+$. $^1$H NMR (400 MHz, DMSO-d$_6$) δ 9.70 (s, 1H), 8.81 (s, 1H), 8.67 (d, J=6.3 Hz, 1H), 8.52 (d, J=1.6 Hz, 1H), 8.44 (s, 1H), 8.04-8.13 (m, 2H), 7.98 (d, J=6.4 Hz, 1H), 7.77 (dd, J=8.7, 1.5 Hz, 1H), 7.73 (d, J=4.6 Hz, 1H), 7.61 (d, J=8.3 Hz, 1H), 7.44 (d, J=4.1 Hz, 1H), 7.27 (dd, J=8.3, 1.6 Hz, 1H), 6.49-6.60 (m, 1H), 4.99-5.08 (m, 1H), 4.89-4.98 (m, 1H), 2.65 (s, 3H). $^{19}$F NMR (376 MHz, DMSO-d$_6$) δ −73.98, −112.64, −177.60.

Example 499: 5-(3-Chloro-2-fluoro-6-(1H-tetrazol-1-yl)phenyl)-2-(2-(5-(2-oxo-2-(piperidin-1-yl)ethyl)-1H-pyrazol-1-yl)-1-(4-(2-(trifluoromethyl)pyridin-4-yl)-1H-pyrazol-1-yl)ethyl)pyridine 1-oxide

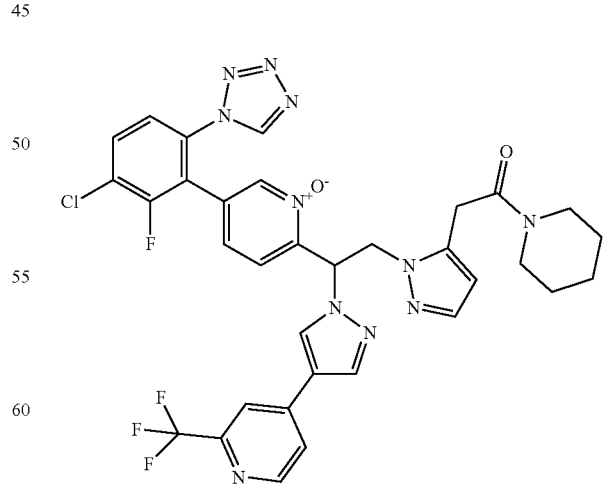

LC/MS: mass calculated for C$_{33}$H$_{28}$ClF$_4$N$_{11}$O$_2$: 721.21, measured (ES, m/z): 722.20 [M+H]$^+$. $^1$H NMR (300 MHz, DMSO-d$_6$) δ 9.68 (s, 1H), 8.71 (s, 1H), 8.64 (d, J=5.2 Hz, 1H), 8.50 (d, J=1.6 Hz, 1H), 8.36 (s, 1H), 8.00-8.11 (m, 2H), 7.84 (dd, J=5.2, 1.6 Hz, 1H), 7.74 (dd, J=8.7, 1.6 Hz, 1H), 7.38 (d, J=8.3 Hz, 1H), 7.30 (d, J=1.8 Hz, 1H), 7.20 (dd, J=8.3, 1.7 Hz, 1H), 6.58-6.69 (m, 1H), 5.93 (d, J=1.8 Hz, 1H), 4.89-5.06 (m, 1H), 4.69-4.85 (m, 1H), 3.65-3.84 (m, 2H), 3.39-3.43 (m, 2H), 3.29-3.35 (m, 2H), 1.49-1.60 (m, 2H), 1.31-1.48 (m, 4H). $^{19}$F NMR (282 MHz, DMSO-$d_6$) δ −66.55, −74.29, −112.61.

Example 500: 5-(3-Chloro-2-fluoro-6-(1H-tetrazol-1-yl)phenyl)-2-(2-((methoxycarbonyl)(methyl)amino)-1-(4-(4-((methoxycarbonyl)amino)phenyl)-1H-pyrazol-1-yl)ethyl)pyridine 1-oxide

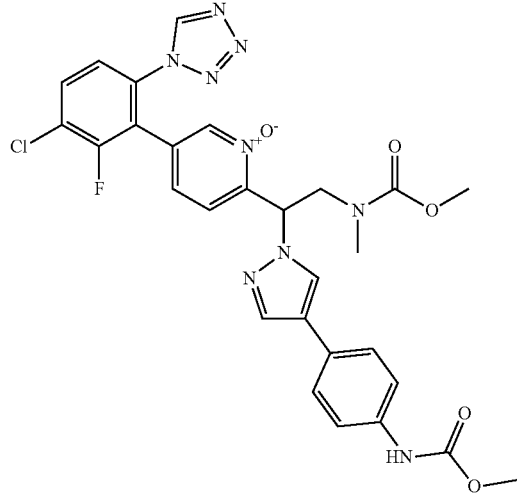

LC/MS: mass calculated for $C_{28}H_{25}ClFN_9O_5$: 621.17, measured (ES, m/z): 622.15 [M+H]$^+$. $^1$H NMR (400 MHz, CD$_3$OD) δ 9.39 (d, J=8.1 Hz, 1H), 8.40 (d, J=7.5 Hz, 1H), 8.19 (d, J=11.3 Hz, 1H), 7.87-7.98 (m, 2H), 7.57-7.80 (m, 2H), 7.39-7.54 (m, 4H), 7.32 (s, 1H), 6.31-6.53 (m, 1H), 4.02-4.44 (m, 2H), 3.76 (s, 3H), 3.54-3.70 (m, 3H), 2.85 (s, 3H). $^{19}$F NMR (376 MHz, DMSO-$d_6$) δ −74.66, −112.69.

Example 501: 4-(1-(1-(5-(3-Chloro-2-fluoro-6-(1H-tetrazol-1-yl)phenyl)-1-oxidopyridin-2-yl)-2-(4-fluoro-1H-pyrazol-1-yl)ethyl)-1H-pyrazol-4-yl)-2,6-dimethylpyridine 1-oxide

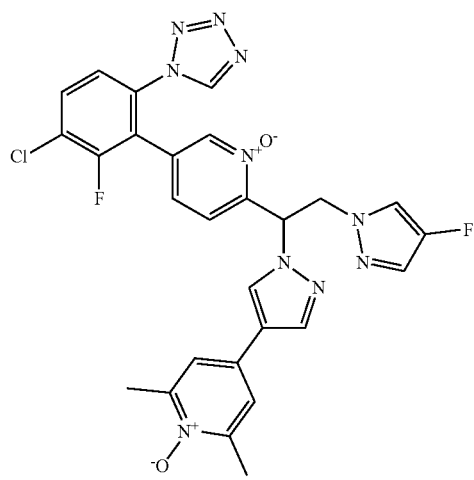

LC/MS: mass calculated for $C_{27}H_{21}ClF_2N_{10}O_2$: 590.15, measured (ES, m/z): 591.15 [M+H]$^+$. $^1$H NMR (300 MHz, DMSO-$d_6$) δ 9.69 (s, 1H), 8.51 (d, J=1.4 Hz, 1H), 8.39 (d, J=0.8 Hz, 1H), 8.02-8.15 (m, 2H), 7.77 (dd, J=8.7, 1.6 Hz, 1H), 7.66 (dd, J=4.6, 0.9 Hz, 1H), 7.60 (s, 2H), 7.38-7.49 (m, 2H), 7.23 (dd, J=8.2, 1.6 Hz, 1H), 6.46-6.58 (m, 1H), 4.76-5.14 (m, 2H), 2.36 (s, 6H). $^{19}$F NMR (282 MHz, DMSO-$d_6$) δ −112.63, −177.79.

Example 502: 5-(3-Chloro-2-fluoro-6-(1H-tetrazol-1-yl)phenyl)-2-(2-cyclopropyl-1-(4-fluoro-2-methyl-1'H,2H-[3,4'-bipyrazol]-1'-yl)ethyl)pyridine 1-oxide

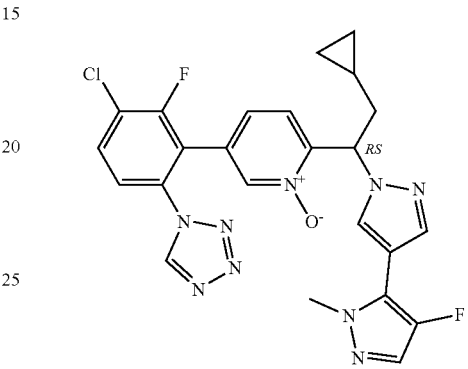

LC/MS: mass calculated for $C_{24}H_{20}ClF_2N_9O$: 523.1, measured (ES, m/z): 524.3 [M+H]$^+$. $^1$H NMR (400 MHz, CD$_3$OD) δ 9.38 (s, 1H), 8.28-8.40 (m, 2H), 7.90 (dd, J=7.34, 1.47 Hz, 2H), 7.59-7.64 (m, 1H), 7.54 (d, J=8.31 Hz, 1H), 7.39 (d, J=4.40 Hz, 1H), 7.26-7.32 (m, 1H), 6.28 (br dd, J=10.03, 3.67 Hz, 1H), 3.89 (s, 3H), 2.42-2.52 (m, 1H), 2.02-2.08 (m, 1H), 0.64-0.75 (m, 1H), 0.34-0.50 (m, 2H), 0.15-0.24 (m, 1H), −0.01-0.05 (m, 1H).

Example 503: (S*)-5-(3-Chloro-6-(4-chloro-1H-1,2,3-triazol-1-yl)-2-fluorophenyl)-2-(2-(4-fluoro-1H-pyrazol-1-yl)-1-(4-(2-(trifluoromethyl)pyridin-4-yl)-1H-pyrazol-1-yl)ethyl)pyridine 1-oxide

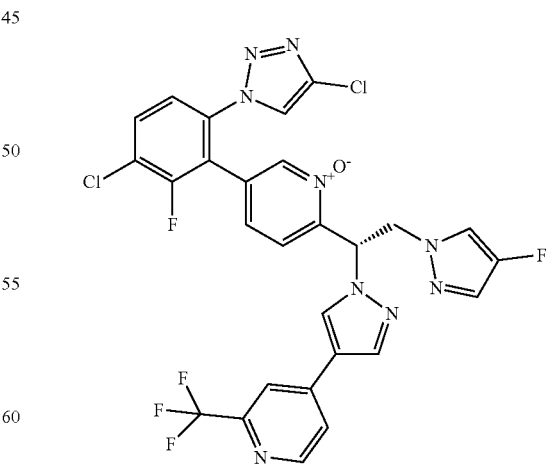

LC/MS: mass calculated for $C_{27}H_{16}Cl_2F_5N_9O$: 647.08, measured (ES, m/z): 648.05 [M+H]$^+$. $^1$H NMR (400 MHz, CD$_3$OD) δ 8.62 (d, J=5.2 Hz, 1H), 8.38-8.45 (m, 2H), 8.32 (s, 1H), 8.27 (s, 1H), 7.97-8.02 (m, 1H), 7.90 (dd, J=8.7, 7.6

Hz, 1H), 7.81 (dd, J=5.3, 1.7 Hz, 1H), 7.54-7.62 (m, 2H), 7.49 (dd, J=4.6, 0.8 Hz, 1H), 7.30-7.39 (m, 2H), 6.62-6.71 (m, 1H), 4.99-5.15 (m, 2H). $^{19}$F NMR (376 MHz, CD$_3$OD) δ −69.30, −114.09, −179.51.

Example 504: (R*)-5-(3-Chloro-6-(4-chloro-1H-1,2,3-triazol-1-yl)-2-fluorophenyl)-2-(2-(4-fluoro-1H-pyrazol-1-yl)-1-(4-(2-(trifluoromethyl)pyridin-4-yl)-1H-pyrazol-1-yl)ethyl)pyridine 1-oxide

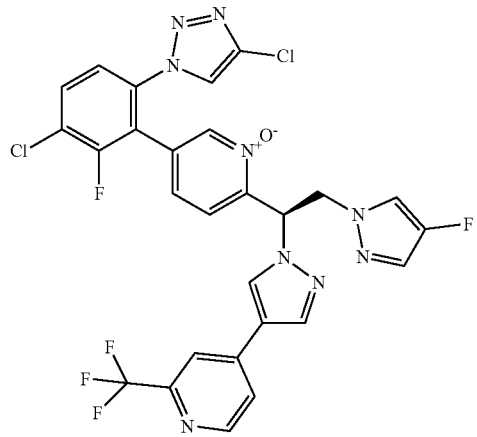

LC/MS: mass calculated for C$_{27}$H$_{16}$Cl$_2$F$_5$N$_9$O: 647.08, measured (ES, m/z): 648.05 [M+H]$^+$. $^1$H NMR (400 MHz, CD$_3$OD) δ 8.62 (d, J=5.2 Hz, 1H), 8.39-8.46 (m, 2H), 8.32 (s, 1H), 8.27 (s, 1H), 8.00 (d, J=1.7 Hz, 1H), 7.90 (dd, J=8.7, 7.6 Hz, 1H), 7.78-7.84 (m, 1H), 7.54-7.62 (m, 2H), 7.49 (dd, J=4.5, 0.8 Hz, 1H), 7.30-7.39 (m, 2H), 6.69 (dd, J=9.4, 4.4 Hz, 1H), 5.11 (dd, J=14.0, 9.5 Hz, 1H), 5.03 (dd, J=14.0, 4.5 Hz, 1H). $^{19}$F NMR (376 MHz, CD$_3$OD) δ −69.53, −179.50.

Example 505: 2-(1-(4-(6-Amino-2-fluoropyridin-3-yl)-1H-pyrazol-1-yl)-2-((methoxycarbonyl)(methyl)amino)ethyl)-5-(3-chloro-2-fluoro-6-(1H-tetrazol-1-yl)phenyl)pyridine 1-oxide

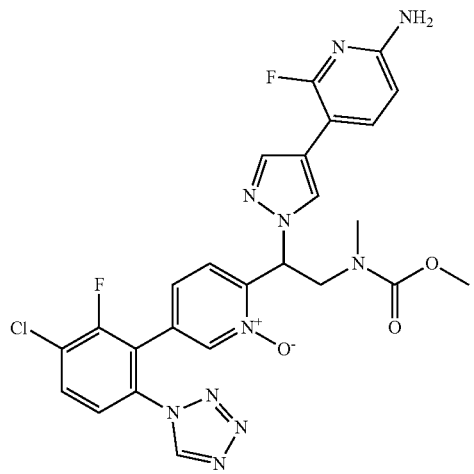 [SMILES: COC(=O)N(C)CC(c1ccc(-c2c(-n3cnnn3)ccc(Cl)c2F)c[n+]1[O-])n1cc(-c2ccc(N)nc2F)cn1]

LC/MS: mass calculated for C$_{25}$H$_{21}$ClF$_2$N$_{10}$O$_3$: 582.15, measured (ES, m/z): 583.10 [M+H]$^+$. $^1$H NMR (400 MHz, CD$_3$OD) δ 9.40 (s, 1H), 8.40 (d, J=7.3 Hz, 1H), 8.12 (s, 1H), 7.86-8.01 (m, 2H), 7.75-7.84 (m, 1H), 7.56-7.74 (m, 2H), 7.32 (d, J=8.3 Hz, 1H), 6.40-6.53 (m, 2H), 4.01-4.36 (m, 2H), 3.53-3.71 (m, 3H), 2.76-2.87 (m, 3H). $^{19}$F NMR (376 MHz, CD$_3$OD) δ −74.12, −77.28, −113.65.

Example 506: 2-(2-(4-Carbamoyl-1H-pyrazol-1-yl)-1-(4-(2-(trifluoromethyl)pyridin-4-yl)-1H-pyrazol-1-yl)ethyl)-5-(3-chloro-2-fluoro-6-(1H-tetrazol-1-yl)phenyl)pyridine 1-oxide

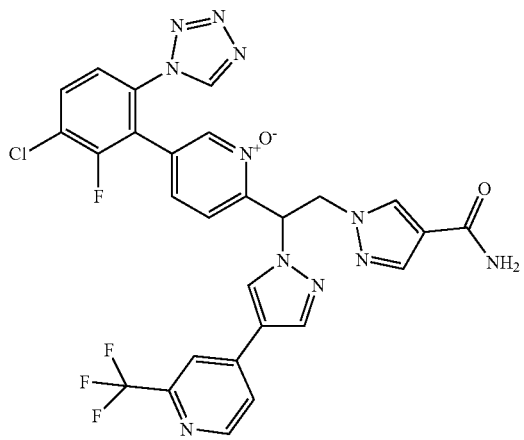

LC/MS: mass calculated for C$_{27}$H$_{18}$ClF$_4$N$_{11}$O$_2$: 639.13, measured (ES, m/z): 640.10 [M+H]$^+$. $^1$H NMR (300 MHz, DMSO-d$_6$) δ 9.70 (s, 1H), 8.76 (s, 1H), 8.66 (d, J=5.2 Hz, 1H), 8.55 (d, J=1.3 Hz, 1H), 8.40 (s, 1H), 8.02-8.13 (m, 2H), 7.98 (s, 1H), 7.72-7.91 (m, 3H), 7.49-7.60 (m, 1H), 7.41 (d, J=8.3 Hz, 1H), 7.23 (dd, J=8.3, 1.7 Hz, 1H), 6.91-7.05 (m, 1H), 6.53-6.62 (m, 1H), 5.06-5.19 (m, 1H), 4.90-5.01 (m, 1H). $^{19}$F NMR (282 MHz, DMSO-d$_6$) δ −66.53, −74.07, −112.60.

Example 507: 5-(3-Chloro-6-(difluoromethyl)-2-fluorophenyl)-2-(3-(difluoromethoxy)-1-(4-(2-(trifluoromethyl)pyrimidin-4-yl)-1H-pyrazol-1-yl)propyl)pyridine 1-oxide

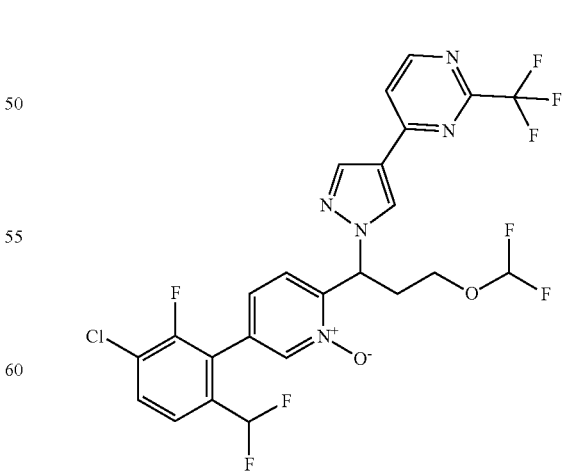

LC/MS: mass calculated for C$_{24}$H$_{16}$ClF$_8$N$_5$O$_2$: 593.09, measured (ES, m/z): 594.05 [M+H]$^+$. $^1$H NMR (300 MHz, DMSO-d$_6$) δ 8.91-9.02 (m, 2H), 8.53 (d, J=1.6 Hz, 1H), 8.43 (s, 1H), 8.10 (d, J=5.4 Hz, 1H), 7.84-7.96 (m, 1H), 7.62 (d, J=8.5 Hz, 1H), 7.52 (d, J=8.4 Hz, 1H), 7.42 (dd, J=8.3, 1.6 Hz, 1H), 6.40-7.11 (m, 2H), 6.30-6.40 (m, 1H), 3.70-3.95 (m, 2H), 2.63-2.86 (m, 2H). $^{19}$F NMR (282 MHz, DMSO-d$_6$) δ −69.34, −74.07, −83.21, −115.24.

Example 508: 5-(3-chloro-6-(difluoromethyl)-2-fluorophenyl)-2-(2-(4-fluoro-1H-pyrazol-1-yl)-1-(2-methyl-1'H,2H-[3,4'-bipyrazol]-1'-yl)ethyl)pyridine 1-oxide

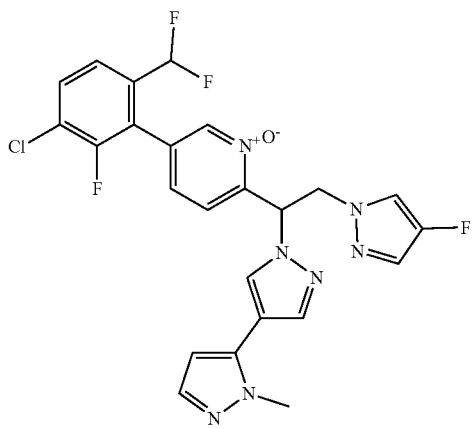

LC/MS: mass calculated for C$_{24}$H$_{18}$ClF$_4$N$_7$O: 531.12, measured (ES, m/z): 532.15 [M+H]$^+$. $^1$H NMR (400 MHz, DMSO-d$_6$) δ 8.60 (d, J=1.6 Hz, 1H), 8.30 (s, 1H), 7.97 (s, 1H), 7.88-7.94 (m, 1H), 7.60-7.67 (m, 2H), 7.56 (d, J=8.3 Hz, 1H), 7.51-7.59 (m, 1H), 7.41-7.48 (m, 1H), 7.39 (d, J=1.9 Hz, 1H), 6.74-7.07 (m, 1H), 6.58-6.69 (m, 1H), 6.39 (d, J=2.0 Hz, 1H), 4.91-5.10 (m, 2H), 3.83 (s, 3H). $^{19}$F NMR (376 MHz, DMSO-d$_6$) δ −74.56, −115.20, −177.95.

Example 509: 5-(3-Chloro-2-fluoro-6-(1H-tetrazol-1-yl)phenyl)-2-(2-cyclopropyl-1-(4-(thiazol-5-yl)-1H-pyrazol-1-yl)ethyl)pyridine 1-oxide

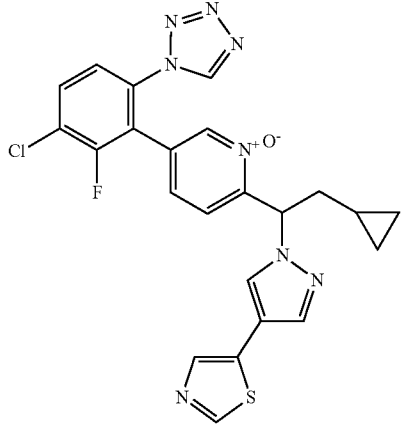

To a solution of 5-(1-(1-(5-(3-chloro-2-fluoro-6-(1H-tetrazol-1-yl)phenyl)pyridin-2-yl)-2-cyclopropylethyl)-1H-pyrazol-4-yl)thiazole (11 mg, 0.022 mmol) in MeOH was added MeReO$_3$ (4 mg, 0.016 mmol), followed by 30% H$_2$O$_2$ (50 uL) and the reaction mixture was stirred at room temperature for 2 h. It was subjected to Gilson HPLC purification to yield 5-(3-chloro-2-fluoro-6-(1H-tetrazol-1-yl)phenyl)-2-(2-cyclopropyl-1-(4-(thiazol-5-yl)-1H-pyrazol-1-yl)ethyl)pyridine 1-oxide as a white solid.

LC/MS: mass calculated for C$_{23}$H$_{18}$ClFN$_8$OS: 508.1, measured (ES, m/z): 509.1 [M+H]$^+$. $^1$H NMR (400 MHz, CD$_3$OD) δ 9.38 (d, J=2.93 Hz, 1H), 8.23-8.42 (m, 2H), 7.85-8.07 (m, 2H), 7.43-7.74 (m, 2H), 7.13-7.38 (m, 2H), 6.35-6.55 (m, 1H), 6.12-6.35 (m, 1H), 4.94-4.97 (m, 1H), 2.39-2.53 (m, 1H), 1.94 (s, 1H), 0.59-0.74 (m, 1H), 0.32-0.49 (m, 2H), 0.15-0.27 (m, 1H), −0.04-0.08 (m, 1H).

Example 510: 5-(3-Chloro-6-(4-cyclopropyl-1H-1,2,3-triazol-1-yl)-2-fluorophenyl)-2-(2-(4-fluoro-1H-pyrazol-1-yl)-1-(4-(2-(trifluoromethyl)pyridin-4-yl)-1H-pyrazol-1-yl)ethyl)pyridine 1-oxide

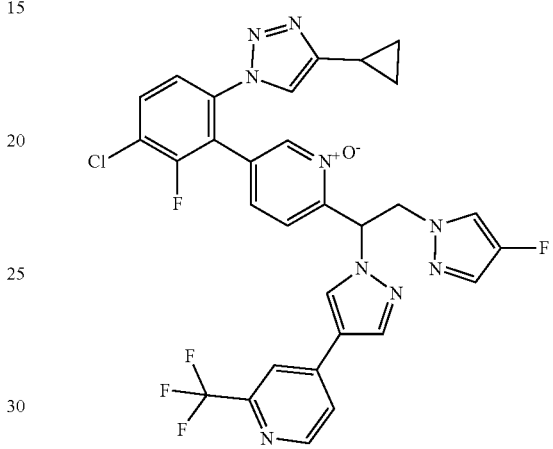

LC/MS: mass calculated for C$_{30}$H$_{21}$ClF$_5$N$_9$O: 653.15, measured (ES, m/z): 654.15 [M+H]$^+$. $^1$H NMR (300 MHz, CD$_3$OD) δ 8.60 (d, J=5.2 Hz, 1H), 8.42 (d, J=0.8 Hz, 1H), 8.31-8.39 (m, 1H), 8.26 (s, 1H), 7.95-8.01 (m, 1H), 7.75-7.92 (m, 3H), 7.43-7.61 (m, 3H), 7.35 (dd, J=4.1, 0.8 Hz, 1H), 7.22-7.31 (m, 1H), 6.61-6.73 (m, 1H), 4.94-5.18 (m, 2H), 1.81-1.99 (m, 1H), 0.81-0.97 (m, 2H), 0.62-0.74 (m, 2H). $^{19}$F NMR (282 MHz, CD$_3$OD) δ −69.52, −77.75, −114.56, −179.51.

Example 511: 2-(2-(3-(2-Amino-2-oxoethyl)-1H-pyrazol-1-yl)-1-(4-(2-(trifluoromethyl)pyridin-4-yl)-1H-pyrazol-1-yl)ethyl)-5-(3-chloro-2-fluoro-6-(1H-tetrazol-1-yl)phenyl)pyridine 1-oxide

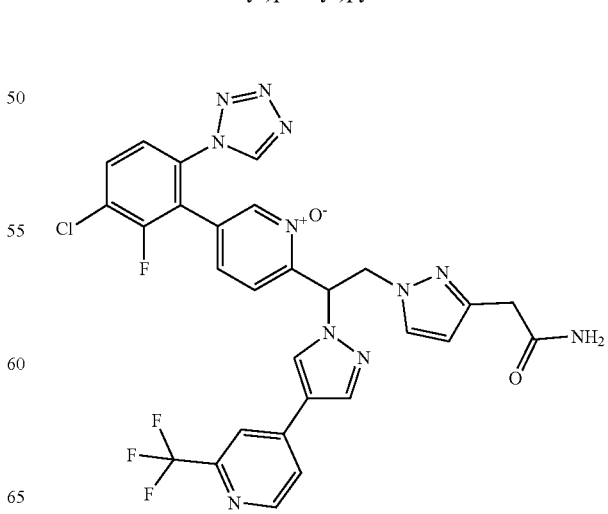

LC/MS: mass calculated for $C_{28}H_{20}ClF_4N_{11}O_2$: 653.14, measured (ES, m/z): 654.15 [M+H]$^+$. $^1$H NMR (400 MHz, DMSO-d$_6$) δ 9.70 (s, 1H), 8.63-8.70 (m, 2H), 8.52 (d, J=1.6 Hz, 1H), 8.37 (s, 1H), 8.04-8.12 (m, 2H), 7.86 (dd, J=5.1, 1.7 Hz, 1H), 7.77 (dd, J=8.7, 1.5 Hz, 1H), 7.48 (d, J=8.4 Hz, 1H), 7.27-7.40 (m, 2H), 7.23 (dd, J=8.2, 1.7 Hz, 1H), 6.89 (s, 1H), 6.55 (dd, J=9.8, 4.5 Hz, 1H), 5.99 (d, J=2.2 Hz, 1H), 5.00 (dd, J=13.9, 9.8 Hz, 1H), 4.90 (dd, J=13.8, 4.5 Hz, 1H), 3.32 (s, 2H). $^{19}$F NMR (376 MHz, DMSO-d$_6$) δ −66.51, −74.51, −112.60.

Example 512: 5-(3-chloro-2-fluoro-6-(1H-tetrazol-1-yl)phenyl)-2-(3-(difluoromethoxy)-1-(2-methyl-1'H,2H-[3,4'-bipyrazol]-1'-yl)propyl)pyridine 1-oxide

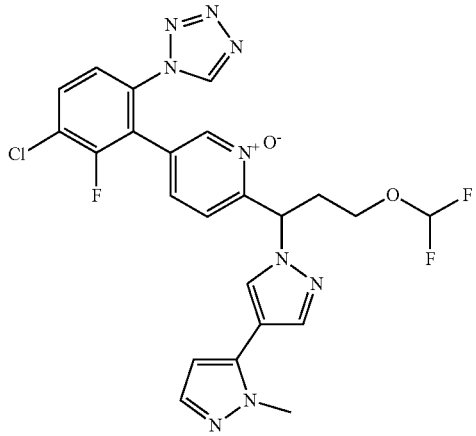

Step 1: 1-(5-Bromopyridin-2-yl)-3-((tert-butyldimethylsilyl)oxy)propan-1-ol

To a solution of 2,5-dibromopyridine (22.9 g, 96.54 mmol, 1.0 equiv) in toluene (150 mL) was add n-BuLi (46 mL, 115.85 mmol, 1.2 equiv) at −78° C. under N$_2$, after 1H was add 3-((tert-butyldimethylsilyl)oxy)propanal (20.0 g, 106.19 mmol, 1.1 equiv) in toluene (50 mL) to the mixture slowly at −78° C., then the reaction mixture was stirred 2 h at −78° C. To the reaction mixture was added NH$_4$Cl (aq.) and extracted with ethyl acetate. The combined organic layers were washed with brine, dried over Na$_2$SO$_4$ and concentrated. The residue was purified by silica gel chromatography (0→40% EA/PE) to yield 1-(5-bromopyridin-2-yl)-3-((tert-butyldimethylsilyl)oxy)propan-1-ol as a yellow solid. LC/MS: mass calculated for $C_{14}H_{24}BrNO_2Si$: 345.08, measured (ES, m/z): 346.34 [M+H]$^+$.

Step 2: 1-(5-Bromopyridin-2-yl)-3-((tert-butyldimethylsilyl)oxy)propyl methanesulfonate To a solution of 1-(5-bromopyridin-2-yl)-3-((tert-butyldimethylsilyl)oxy)propan-1-ol (5.0 g, 14.44 mmol, 1.0 equiv) in CH$_2$Cl$_2$ (50 mL) was added triethylamine (4 mL, 28.87 mmol, 2.0 equiv) and methanesulfonic anhydride (3.8 g, 21.66 mmol, 1.5 equiv) at 0° C., then warmed to room temperature, and stirred for 4 h. To the reaction was added water and the mixture extracted with CH$_2$Cl$_2$. The combined organic layers were washed with brine, dried over Na$_2$SO$_4$ and concentrated. The residue was purified by silica gel chromatography (0-*40% EA/PE) to yield 1-(5-bromopyridin-2-yl)-3-((tert-butyldimethylsilyl)oxy)propyl methanesulfonate as a yellow solid. LC/MS: mass calculated for $C_{15}H_{26}BrNO_4SSi$: 423.05, measured (ES, m/z): 424.43 [M+H]$^+$.

Step 3: 1'-(1-(5-Bromopyridin-2-yl)-3-((tert-butyldimethylsilyl)oxy)propyl)-2-methyl-1'H,2H-3,4'-bipyrazole A mixture of 1-(5-bromopyridin-2-yl)-3-((tert-butyldimethylsilyl)oxy)propyl methanesulfonate (800 mg, 1.89 mmol, 1.0 equiv), 2-methyl-1'H,2H-3,4'-bipyrazole (335 mg, 2.26 mmol, 1.2 equiv) and Cs$_2$CO$_3$ (1.2 g, 3.77 mmol, 2.0 equiv) in acetonitrile (10 mL) was stirred at 85° C. for 2 h. To the reaction mixture was added water and the mixture extracted with ethyl acetate, the organic layer was washed with brine and dried over anhydrous Na$_2$SO$_4$. The combined organic layers were washed with brine, dried over Na$_2$SO$_4$ and concentrated. The residue was purified by silica gel chromatography (0→40% EA/PE) to yield 1'-(1-(5-bromopyridin-2-yl)-3-((tert-butyldimethylsilyl)oxy)propyl)-2-methyl-1'H,2H-3,4'-bipyrazole as a yellow solid. LC/MS: mass calculated for $C_{21}H_{30}BrN_5OSi$: 475.14, measured (ES, m/z): 476.49 [M+H]$^+$.

Step 4: 3-(5-Bromopyridin-2-yl)-3-(2-methyl-1'H,2H-[3,4'-bipyrazol]-1'-yl)propan-1-ol The mixture of 1'-(1-(5-bromopyridin-2-yl)-3-((tert-butyldimethylsilyl)oxy)propyl)-2-methyl-1'H,2H-3,4'-bipyrazole (800 mg, 1.68 mmol, 1.0 equiv) and TBAF (878 mg, 3.36 mmol, 2.0 equiv) in THF (10 mL) was stirred at room temperature for 2 h. To the reaction mixture was added water and the mixture extracted with ethyl acetate. The combined organic layers were washed with brine, dried over Na$_2$SO$_4$ and concentrated. The residue was purified by silica gel chromatography (0→40% EA/PE) to yield 3-(5-bromopyridin-2-yl)-3-(2-methyl-1'H,2H-[3,4'-bipyrazol]-1'-yl)propan-1-ol as a yellow solid. LC/MS: mass calculated for $C_{15}H_{16}BrN_5O$: 361.05, measured (ES, m/z): 362.23 [M+H]$^+$.

Step 5: 1'-(1-(5-Bromopyridin-2-yl)-3-(difluoromethoxy)propyl)-2-methyl-1'H,2H-3,4'-bipyrazole To a mixture of 3-(5-bromopyridin-2-yl)-3-(2-methyl-1'H,2H-[3,4'-bipyrazol]-1'-yl)propan-1-ol (600 mg, 1.66 mmol, 1.0 equiv) and cuprous iodide (63 mg, 0.33 mmol, 0.2 equiv) in acetonitrile (8 mL) was added 2-(fluorosulfonyl)difluoroacetic acid (442 mg, 2.49 mmol, 1.5 equiv) in acetonitrile (2 mL) at 50° C. under N$_2$. The reaction mixture was stirred at 50° C. for 30 min. To the reaction mixture was added water and the mixture extracted with ethyl acetate. The combined organic layers were washed with brine, dried over Na$_2$SO$_4$ and concentrated. The residue was purified by silica gel chromatography (0→40% EA/PE) to yield 1'-(1-(5-bromopyridin-2-yl)-3-(difluoromethoxy)propyl)-2-methyl-1'H,2H-3,4'-bipyrazole as a yellow solid. LC/MS: mass calculated for $C_{16}H_{16}BrF_2N_5O$: 411.05, measured (ES, m/z): 412.24 [M+H]$^+$.

Step 6: 4-Chloro-2-(6-(3-(difluoromethoxy)-1-(2-methyl-1'H,2H-[3,4'-bipyrazol]-1'-yl)propyl)pyridin-3-yl)-3-fluoroaniline A mixture of 1'-(1-(5-bromopyridin-2-yl)-3-(difluoromethoxy)propyl)-2-methyl-1'H,2H-3,4'-bipyrazole (390 mg, 0.95 mmol, 1.0 equiv), (6-amino-3-chloro-2-fluorophenyl)boronic acid (358 mg, 1.89 mmol, 2.0 equiv), $K_2CO_3$ (654 mg, 4.73 mmol, 5.0 equiv) and $Pd(PPh_3)_4$ (109 mg, 0.10 mmol, 0.1 equiv) in 1,4-dioxane (4 mL) and water (1 mL) was stirred at 80° C. under $N_2$ overnight. To the reaction mixture was added water and the mixture extracted with ethyl acetate. The combined organic layers were washed with brine, dried over $Na_2SO_4$ and concentrated. The residue was purified by silica gel chromatography (0→40% EA/PE) to yield 4-chloro-2-(6-(3-(difluoromethoxy)-1-(2-methyl-1'H,2H-[3,4'-bipyrazol]-1'-yl)propyl)pyridin-3-yl)-3-fluoroaniline as a yellow solid. LC/MS: mass calculated for $C_{22}H_{20}ClF_3N_6O$: 476.13, measured (ES, m/z): 477.14 $[M+H]^+$ Step 7: 1'-(1-(5-(3-Chloro-2-fluoro-6-(1H-tetrazol-1-yl)phenyl)pyridin-2-yl)-3-(difluoromethoxy)propyl)-2-methyl-1'H,2H-3,4'-bipyrazole A mixture of 4-chloro-2-(6-(3-(difluoromethoxy)-1-(2-methyl-1'H,2H-[3,4'-bipyrazol]-1'-yl)propyl)pyridin-3-yl)-3-fluoroaniline (400 mg, 0.84 mmol, 1.0 equiv), azidotrimethylsilane (2 mL) and trimethoxymethane (2 mL) in acetic acid (3 mL) was stirred at room temperature overnight. The reaction was concentrated and purified by reverse phase chromatography on C18 (80 g, MeCN/$H_2O$ (0.05% $CF_3COOH$): 0→55%) to yield 1'-(1-(5-(3-chloro-2-fluoro-6-(1H-tetrazol-1-yl)phenyl)pyridin-2-yl)-3-(difluoromethoxy)propyl)-2-methyl-1'H,2H-3,4'-bipyrazole as a yellow solid. LC/MS: mass calculated for $C_{23}H_{19}ClF_3N_9O$: 529.14, measured (ES, m/z): 530.14 $[M+H]^+$ Step 8: 5-(3-Chloro-2-fluoro-6-(1H-tetrazol-1-yl)phenyl)-2-(3-(difluoromethoxy)-1-(2-methyl-1'H,2H-[3,4'-bipyrazol]-1'-yl)propyl)pyridine 1-oxide A mixture of 1'-(1-(5-(3-chloro-2-fluoro-6-(1H-tetrazol-1-yl)phenyl)pyridin-2-yl)-3-(difluoromethoxy)propyl)-2-methyl-1'H,2H-3,4'-bipyrazole (100 mg, 0.19 mmol, 1.0 equiv), 3-chloroperoxybenzoic acid (130 mg, 0.76 mmol, 4.0 equiv) in ethyl acetate (2 mL) was stirred at room temperature for 2 h. The resulting mixture was purified by reverse phase chromatography on C18 (80 g, MeCN/$H_2O$ (0.05% $CF_3COOH$): 0→55%) to yield 5-(3-chloro-2-fluoro-6-(1H-tetrazol-1-yl)phenyl)-2-(3-(difluoromethoxy)-1-(2-methyl-1'H,2H-[3,4'-bipyrazol]-1'-yl)propyl)pyridine 1-oxide as a white solid.

LC/MS: mass calculated for $C_{23}H_{19}ClF_3N_9O_2$: 545.13, measured (ES, m/z): 546.05 $[M+H]^+$. $^1H$ NMR (300 MHz, DMSO-$d_6$) δ 9.67 (s, 1H), 8.44 (d, J=1.5 Hz, 1H), 8.37 (s, 1H), 8.04 (t, J=8.7 Hz, 1H), 7.92 (s, 1H), 7.74 (d, J=8.7 Hz, 1H), 7.37 (d, J=1.9 Hz, 1H), 7.23-7.27 (m, 1H), 7.15-7.18 (m, 1H), 6.61 (t, J=78.0 Hz, 1H), 6.40 (d, J=1.9 Hz, 1H), 6.19 (dd, J=9.8, 4.7 Hz, 1H), 3.86 (s, 3H), 3.79-3.83 (m, 1H), 3.61-3.69 (m, 1H), 2.52-2.65 (m, 2H). $^{19}F$ NMR (282 MHz, DMSO-$d_6$) δ −74.67, −83.31, −112.70.

Example 513: 5-(3-Chloro-2-fluoro-6-(1H-tetrazol-1-yl)phenyl)-2-(2-cyclopropyl-1-(4-(4-methylthiazol-5-yl)-1H-pyrazol-1-yl)ethyl)pyridine 1-oxide

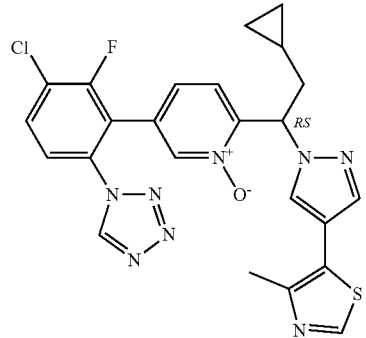 [SMILES: Cc1ncsc1-c1cnn(C(CC2CC2)c2ccc(-c3c(-n4cnnn4)ccc(Cl)c3F)c[n+]2[O-])c1]

Step 1: 5-Bromo-2-(2-cyclopropyl-1-(4-iodo-1H-pyrazol-1-yl)ethyl)pyridine

To a mixture of 1-(5-bromopyridin-2-yl)-2-cyclopropylethyl methanesulfonate (540 mg, 1.7 mmol), 4-iodo-1H-pyrazole (360 mg, 1.86 mmol), and $Cs_2CO_3$ (824 mg, 2.5 mmol) was added $CH_3CN$ (8 mL) and the reaction mixture was stirred at 85° C. for 3 h. The precipitate was filtered off and the solvent was removed under reduced pressure. The residue was purified by flash column chromatography on silica gel (EtOAc/heptane: 0-30%) to yield 5-bromo-2-(2-cyclopropyl-1-(4-iodo-1H-pyrazol-1-yl)ethyl)pyridine as a colorless oil. LC/MS: mass calculated for $C_{13}H_{13}BrIN_3$: 418.071, measured: 417.95 $[M+H]^+$.

Step 2: 5-(1-(1-(5-Bromopyridin-2-yl)-2-cyclopropylethyl)-1H-pyrazol-4-yl)-4-methylthiazole To a microwave vial was added 5-bromo-2-(2-cyclopropyl-1-(4-iodo-1H-pyrazol-1-yl)ethyl)pyridine (58 mg, 0.14 mmol), 4-methyl-5-(4,4,5,5-tetramethyl-1,3,2-dioxaborolan-2-yl)thiazole (40.6 mg, 0.18 mmol), $Pd(PPh_3)_4$ (8 mg, 0.007 mmol), $K_2CO_3$ (0.11 mL, 2M) and 1,4-dioxane (4 ml). The vial was sealed and the mixture was evacuated and refilled with argon, then heated at 130° C. for 65 mins. The reaction was cooled to room temperature and the solvent was removed under reduced pressure. The residue was used in the next step reaction directly (without further purification). LC/MS: mass calculated for $C_{17}H_{17}BrN_4S$: 388.0, measured: 389.1 $[M+H]^+$.

Step 3: 4-Chloro-2-(6-(2-cyclopropyl-1-(4-(4-methylthiazol-5-yl)-1H-pyrazol-1-yl)ethyl)pyridin-3-yl)-3-fluoroaniline To a mixture of 5-(1-(1-(5-bromopyridin-2-yl)-2-cyclopropylethyl)-1H-pyrazol-4-yl)-4-methylthiazole (54 mg, 0.139 mmol), 4-chloro-3-fluoro-2-(4,4,5,5-tetramethyl-1,3,2-dioxaborolan-2-yl)aniline (37.7 mg, 0.139 mmol) and $Pd(PPh_3)_4$ (8.01 mg, 0.0069 mmol) in 1,4-dioxane (4 mL) was added aqueous $K_2CO_3$ (0.139 mL, 2 M) and the reaction mixture was heated at 130° C. for 65 mins. The reaction mixture was concentrated and the residue was purified by prep HPLC to yield 4-chloro-2-(6-(2-cyclopropyl-1-(4-(4-methylthiazol-5-yl)-1H-pyrazol-1-yl)ethyl)pyridin-3-yl)-3- fluoroaniline as a yellow solid. LC/MS: mass calculated for $C_{23}H_{21}ClFN_5S$: 453.1, measured: 454.1 $[M+H]^+$.

Step 4: 5-(1-(1-(5-(3-Chloro-2-fluoro-6-(1H-tetrazol-1-yl)phenyl)pyridin-2-yl)-2-cyclopropylethyl)-1H-pyrazol-4-yl)-4-methylthiazole To 4-chloro-2-(6-(2-cyclopropyl-1-(4-(4-methylthiazol-5-yl)-1H-pyrazol-1-yl)ethyl)pyridin-3-yl)-3-fluoroaniline (21.7 mg, 0.048 mmol) in HOAc (4 mL) was added trimethoxymethane (50.7 mg, 0.48 mmol), followed by $NaN_3$ (31 mg, 0.48 mmol) and the resulting mixture was stirred at 80° C. for 2 h. Upon the completion of the reaction, the solvent was removed under reduced pressure and the residue was dissolved in MeOH and purified by prep HPLC to yield 5-(1-(1-(5-(3-chloro-2-fluoro-6-(1H-tetrazol-1-yl)phenyl)pyridin-2-yl)-2-cyclopropylethyl)-1H-pyrazol-4-yl)-4-methylthiazole as a colorless film. LC/MS: mass calculated for $C_{24}H_{20}ClFN_8S$: 506.1, measured: 507.2 $[M+H]^+$.

Step 5: 5-(3-Chloro-2-fluoro-6-(1H-tetrazol-1-yl)phenyl)-2-(2-cyclopropyl-1-(4-(4-methylthiazol-5-yl)-1H-pyrazol-1-yl)ethyl)pyridine 1-oxide To a solution of 5-(1-(1-(5-(3-chloro-2-fluoro-6-(1H-tetrazol-1-yl)phenyl)pyridin-2-yl)-2-cyclopropylethyl)-1H-pyrazol-4-yl)-4-methylthiazole in MeOH (2.5 ml) was added $MeReO_3$, followed by 30% $H_2O_2$ (130 μL) and the reaction mixture was stirred at room temperature for 2 h. The resulting mixture was then subjected to Gilson HPLC purification to yield 5-(3-chloro-2-fluoro-6-(1H-tetrazol-1-yl)phenyl)-2-(2-cyclopropyl-1-(4-(4-methylthiazol-5-yl)-1H-pyrazol-1-yl)ethyl)pyridine 1-oxide as a white solid. LC/MS: mass calculated for $C_{24}H_{20}ClFN_8OS$: 522.1, measured (ES, m/z): 523.2 $[M+H]^+$. $^1H$ NMR (400 MHz, CD3OD) δ ppm −0.01-0.05 (m, 1H) 0.15-0.22 (m, 1H) 0.34-0.49 (m, 2 h) 0.61-0.73 (m, 1H) 2.01-2.09 (m, 1H) 2.39-2.51 (m, 4H) 6.23-6.28 (m, 1H) 7.30 (dd, J=8.31, 1.47 Hz, 1H) 7.56 (d, J=8.31 Hz, 1H) 7.59-7.63 (m, 1H) 7.88-7.97 (m, 2 h) 8.36-8.40 (m, 1H) 8.80-8.88 (m, 1H) 9.39 (s, 1H).

Example 514: 2-(1-(4-(6-Amino-2-fluoropyridin-3-yl)-1H-pyrazol-1-yl)-2-(5-(methoxymethyl)-1H-pyrazol-1-yl)ethyl)-5-(3-chloro-2-fluoro-6-(1H-tetrazol-1-yl)phenyl)pyridine 1-oxide

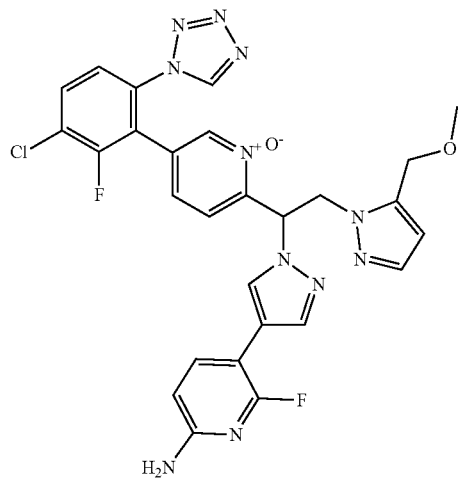

LC/MS: mass calculated for $C_{27}H_{22}ClF_2N_{11}O_2$: 605.16, measured (ES, m/z): 606.10 $[M+H]^+$. $^1H$ NMR (400 MHz, DMSO-$d_6$) δ 9.69 (s, 1H), 8.50 (d, J=1.6 Hz, 1H), 8.02-8.21 (m 1H), 7.98 (d, J=1.8 Hz, 1H), 7.85 (d, J=1.2 Hz, 1H), 7.69-7.80 (m, 2H), 7.31-7.39 (m, 2H), 7.20 (dd, J=8.3, 1.6 Hz, 1H), 6.60-6.68 (m, 1H), 6.30-6.39 (m, 1H), 6.16 (d, J=1.8 Hz, 1H), 4.92-5.06 (m, 1H), 4.81-4.91 (m, 1H), 4.34-4.51 (m, 2H), 3.24 (s, 3H). $^{19}F$ NMR (376 MHz, DMSO-$d_6$) δ −71.32, −74.63, −112.63.

Example 515: 5-(3-chloro-2-fluoro-6-(1H-tetrazol-1-yl)phenyl)-2-((S)-2-cyclopropyl-1-(2-methyl-1'H,2H-[3,4'-bipyrazol]-1'-yl)ethyl)-4-methoxypyridine 1-oxide

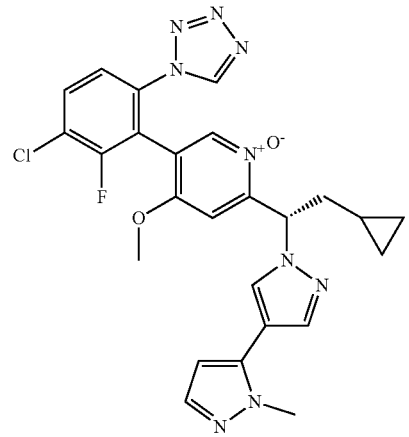

Step 1: 1'-(1-(5-Chloro-4-methoxypyridin-2-yl)-2-cyclopropylethyl)-2-methyl-1'H,2H-3,4'-bipyrazole A mixture of cesium carbonate (940 mg, 2.88 mmol, 1.1 equiv.) and 2-methyl-1'H,2H-3,4'-bipyrazole (465 mg, 3.14 mmol, 1.2 equiv.) in acetonitrile (10.0 mL) was stirred for 15 min at room temperature. 1-(5-Chloro-4-methoxypyridin-2-yl)-2-cyclopropylethyl methanesulfonate (800 mg, 2.62 mmol, 1.0 equiv.) was added and the solution was stirred for 3H at 90° C. The solution was diluted with $H_2O$, extracted with ethyl acetate twice. The combined organic layers were washed with brine, dried over $Na_2SO_4$, concentrated and purified by reverse phase chromatography on C18 (80 g, MeCN/$H_2O$ (0.05% $CF_3COOH$): 0→45%) to yield 1'-(1-(5-chloro-4-methoxypyridin-2-yl)-2-cyclopropylethyl)-2-methyl-1'H,2H-3,4'-bipyrazole as a light yellow oil. LC/MS: mass calculated for $C_{18}H_{20}ClN_5O$: 357.14, measured (ES, m/z): 358.05 $[M+H]^+$.

Step 2: (6-(2-Cyclopropyl-1-(2-methyl-1'H,2H-[3,4'-bipyrazol]-1'-yl)ethyl)-4-methoxypyridin-3-yl)boronic acid A mixture of 1'-(1-(5-chloro-4-methoxypyridin-2-yl)-2-cyclopropylethyl)-2-methyl-1'H,2H-3,4'-bipyrazole (935 mg, 2.61 mmol, 1.0 equiv.), 4,4,4',4',5,5,5',5'-octamethyl-2,2'-bi(1,3,2-dioxaborolane) (10.0 g, 39.19 mmol, 15.0 equiv.), Xphos-Pd G3 (442 mg, 0.52 mmol, 0.2 equiv.) and potassium acetate (3.8 g, 39.19 mmol, 15.0 equiv.) in 1,4-dioxane (10.0 mL) was stirred for 2 h at 80° C. The mixture was diluted with $H_2O$, extracted with ethyl acetate twice. The combined organic layers were washed with brine, dried over Na$_2$SO$_4$ and concentrated to yield (6-(2-cyclopropyl-1-(2-methyl-1'H, 2 h-[3,4'-bipyrazol]-1'-yl)ethyl)-4-methoxypyridin-3-yl)boronic acid as light yellow oil. LC/MS: mass calculated for C$_{18}$H$_{22}$BN$_5$O$_3$: 367.18, measured (ES, m/z): 368.15 [M+H]$^+$.

Step 3: 4-Chloro-2-(6-(2-cyclopropyl-1-(2-methyl-1'H,2H-[3,4'-bipyrazol]-1'-yl)ethyl)-4-methoxypyridin-3-yl)-3-fluoroaniline A mixture of (6-(2-cyclopropyl-1-(2-methyl-1'H,2H-[3,4'-bipyrazol]-1'-yl)ethyl)-4-methoxypyridin-3-yl)boronic acid (3.0 g, resulting), 4-chloro-3-fluoro-2-iodoaniline (471 mg, 1.74 mmol), Pd(PPh$_3$)$_4$ (100 mg, 0.09 mmol), potassium carbanate (360 mg, 2.61 mmol) in 1,4-dioxane (10.0 mL) and water (2.0 mL) was refluxed at 90° C. under N$_2$ for 2 h. The mixture was diluted with H$_2$O, extracted with ethyl acetate twice. The combined organic layers were washed with brine, dried over Na$_2$SO$_4$, concentrated and purified by silica gel chromatography (0→8%, MeOH/DCM) to yield 4-chloro-2-(6-(2-cyclopropyl-1-(2-methyl-1'H,2H-[3,4'-bipyrazol]-1'-yl)ethyl)-4-methoxypyridin-3-yl)-3-fluoroaniline as light yellow solid. LC/MS: mass calculated for C$_{24}$H$_{24}$ClFN$_6$O: 466.17, measured (ES, m/z): 467.15 [M+H]$^+$.

Step 4: 1'-(1-(5-(3-Chloro-2-fluoro-6-(1H-tetrazol-1-yl)phenyl)-4-methoxypyridin-2-yl)-2-cyclopropylethyl)-2-methyl-1'H,2H-3,4'-bipyrazole A mixture of 4-chloro-2-(6-(2-cyclopropyl-1-(2-methyl-1'H,2H-[3,4'-bipyrazol]-1'-yl)ethyl)-4-methoxypyridin-3-yl)-3-fluoroaniline (320 mg, 0.68 mmol, 1.0 equiv.), trimethoxymethane (1 mL), azidotrimethylsilane (1 mL) and acetic acid (1 mL) was stirred overnight at room temperature, then concentrated under vacuum. The residue was purified by reverse phase chromatography on C18 (0→55% MeCN/H$_2$O (0.05% CF$_3$COOH)) to yield 1'-(1-(5-(3-chloro-2-fluoro-6-(1H-tetrazol-1-yl)phenyl)-4-methoxypyridin-2-yl)-2-cyclopropylethyl)-2-methyl-1'H,2H-3,4'-bipyrazole as a white solid. LC/MS: mass calculated for C$_{25}$H$_{23}$ClFN$_9$O: 519.17, measured (ES, m/z): 520.15 [M+H]$^+$.

Step 5: 5-(3-Chloro-2-fluoro-6-(1H-tetrazol-1-yl)phenyl)-2-((S)-2-cyclopropyl-1-(2-methyl-1'H,2H-[3,4'-bipyrazol]-1'-yl)ethyl)-4-methoxypyridine 1-oxide A mixture of 1'-(1-(5-(3-chloro-2-fluoro-6-(1H-tetrazol-1-yl)phenyl)-4-methoxypyridin-2-yl)-2-cyclopropylethyl)-2-methyl-1'H,2H-3,4'-bipyrazole (280 mg, 0.54 mmol, 1.0 equiv.) and 3-chlorobenzoperoxoic acid (465 mg, 2.69 mmol, 5.0 equiv.) in ethyl acetate (3 mL) was stirred for 1H at room temperature. The solution was purified by reverse phase chromatography on C18 (80 g, MeCN/H$_2$O (0.05% CF$_3$COOH): 0→45%) to yield 5-(3-chloro-2-fluoro-6-(1H-tetrazol-1-yl)phenyl)-2-(2-cyclopropyl-1-(2-methyl-1'H,2H-[3,4'-bipyrazol]-1'-yl)ethyl)-4-methoxypyridine 1-oxide as a white solid. 45 mg of the racemic product was separated by Chiral-HPLC to yield 5-(3-chloro-2-fluoro-6-(1H-tetrazol-1-yl)phenyl)-2-((S*)-2-cyclopropyl-1-(2-methyl-1'H,2H-[3,4'-bipyrazol]-1'-yl)ethyl)-4-methoxypyridine 1-oxide.

LC/MS: mass calculated for C$_{25}$H$_{23}$ClFN$_9$O$_2$: 535.16, measured (ES, m/z): 536.10 [M+H]$^+$. $^1$H NMR (300 MHz, CD$_3$OD) δ 9.51-9.39 (m, 1H), 8.37 (s, 1H), 8.28 (d, J=3.4 Hz, 1H), 7.84-7.97 (m, 2H), 7.56-7.65 (m, 1H), 7.40-7.47 (m, 1H), 7.20 (d, J=4.1 Hz, 1H), 6.37-6.46 (m, 1H), 6.20-6.36 (m, 1H), 3.94 (d, J=4.0 Hz, 3H), 3.69 (d, J=1.3 Hz, 3H), 2.41-2.57 (m, 1H), 1.97-2.12 (m, 1H), 0.59-0.75 (m, 1H), 0.31-0.50 (m, 2H), 0.13-0.27 (m, 1H), 0.01-0.10 (m, 1H).

Example 516: 5-(3-chloro-2-fluoro-6-(1H-tetrazol-1-yl)phenyl)-2-((R)-2-cyclopropyl-1-(2-methyl-1'H, 2H-[3,4'-bipyrazol]-1'-yl)ethyl)-4-methoxypyridine 1-oxide

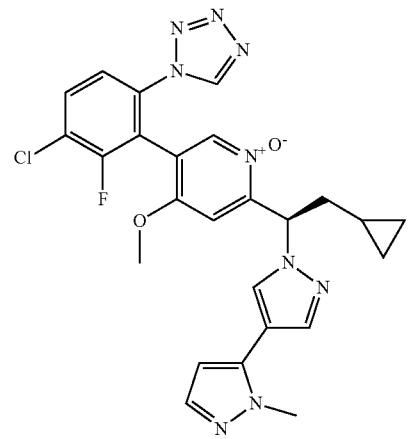

LC/MS: mass calculated for C$_{25}$H$_{23}$ClFN$_9$O$_2$: 535.16, measured (ES, m/z): 536.10 [M+H]$^+$. $^1$H NMR (300 MHz, CD$_3$OD) δ 9.38-9.50 (m, 1H), 8.37 (s, 1H), 8.28 (d, J=3.4 Hz, 1H), 7.82-7.97 (m, 2H), 7.54-7.65 (m, 1H), 7.39-7.47 (m, 1H), 7.20 (d, J=4.2 Hz, 1H), 6.36-6.44 (m, 1H), 6.20-6.34 (m, 1H), 3.94 (d, J=4.1 Hz, 3H), 3.69 (d, J=1.2 Hz, 3H), 2.42-2.58 (m, 1H), 1.93-2.11 (m, 1H), 0.59-0.74 (m, 1H), 0.32-0.50 (m, 2H), 0.11-0.25 (m, 1H), −0.02-0.10 (m, 1H).

Example 517: 2-(1-(4-(6-Amino-2-fluoropyridin-3-yl)-1H-pyrazol-1-yl)-2-(3-(methoxymethyl)-1H-pyrazol-1-yl)ethyl)-5-(3-chloro-2-fluoro-6-(1H-tetrazol-1-yl)phenyl)pyridine 1-oxide

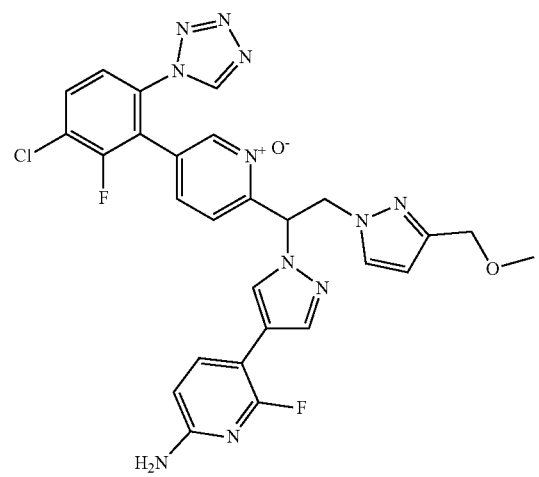

LC/MS: mass calculated for $C_{27}H_{22}ClF_2N_{11}O_2$: 605.16, measured (ES, m/z): 606.25 [M+H]+. $^1$H NMR (400 MHz, DMSO-$d_6$) δ 9.70 (s, 1H), 8.51 (d, J=1.4 Hz, 1H), 8.02-8.12 (m, 2H), 7.88 (s, 1H), 7.70-7.80 (m, 2H), 7.39 (d, J=2.3 Hz, 1H), 7.30 (d, J=8.3 Hz, 1H), 7.20 (dd, J=8.4, 1.6 Hz, 1H), 6.47-6.58 (m, 1H), 6.29-6.38 (m, 1H), 6.08 (d, J=2.3 Hz, 1H), 4.96-5.05 (m, 1H), 4.87-4.95 (m, 1H), 4.28 (s, 2H), 3.15 (s, 3H). $^{19}$F NMR (376 MHz, DMSO-$d_6$) δ −71.30, −74.39, −112.63.

Example 518: (S*)-2-(1-(4-(4-Carboxyphenyl)-1H-pyrazol-1-yl)-2-(4-fluoro-1H-pyrazol-1-yl)ethyl)-5-(3-chloro-6-(difluoromethyl)-2-fluorophenyl)pyridine 1-oxide

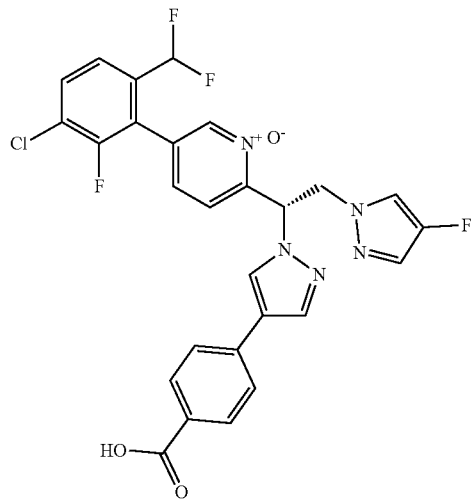

LC/MS: mass calculated for $C_{27}H_{18}ClF_4N_5O_3$: 571.10, measured (ES, m/z): 594.10 [M+Na]+. $^1$H NMR (300 MHz, DMSO-$d_6$) δ 12.86 (s, 1H), 8.58 (s, 1H), 8.52 (s, 1H), 8.21 (s, 1H), 7.90-7.93 (m, 3H), 7.65-7.75 (m, 3H), 7.62 (d, J=8.6 Hz, 1H), 7.38-7.52 (m, 3H), 6.72-7.03 (m, 1H), 6.62 (dd, J=9.5, 4.4 Hz, 1H), 4.90-5.13 (m, 2H). $^{19}$F NMR (282 MHz, DMSO-$d_6$) δ −73.40, −115.20, −177.89.

Example 519: (S)-5-(3-Chloro-2-fluoro-6-(1H-tetrazol-1-yl)phenyl)-2-(2-(4-fluoro-1H-pyrazol-1-yl)-1-(4-(thiazol-5-yl)-1H-pyrazol-1-yl)ethyl)pyridine 1-oxide

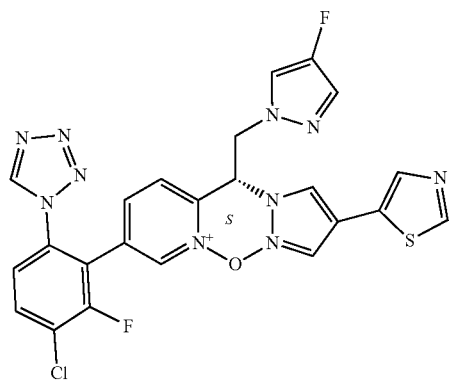

LC/MS: mass calculated for $C_{23}H_{15}ClF_2N_{10}OS$: 552.08, measured (ES, m/z): 575.05[M+Na]+. $^1$H NMR (300 MHz, DMSO-$d_6$) δ 9.67 (s, 1H), 8.93 (d, J=0.8 Hz, 1H), 8.49 (s, 1H), 8.26 (s, 1H), 7.99-8.11 (m, 2H), 7.96 (s, 1H), 7.72-7.80 (m, 1H), 7.64 (d, J=4.6 Hz, 1H), 7.47-7.39 (m, 1H), 7.32-7.40 (m, 1H), 7.24-7.15 (m, 1H), 6.47-6.54 (m, 1H), 5.02-4.81 (m, 2 h). $^{19}$F NMR (282 MHz, DMSO-$d_6$) δ −112.64, −177.82.

Example 520: (R)-5-(3-Chloro-2-fluoro-6-(1H-tetrazol-1-yl)phenyl)-2-(2-cyclopropyl-1-(4-(1-methyl-1H-1,2,3-triazol-4-yl)-1H-pyrazol-1-yl)ethyl)pyridine 1-oxide

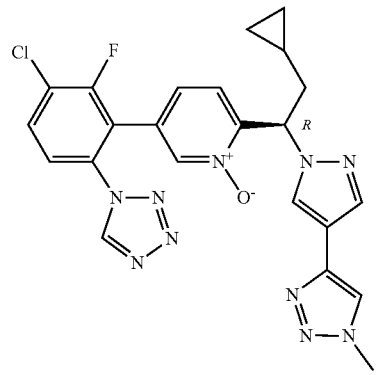

LC/MS: mass calculated for $C_{23}H_{20}ClFN_{10}O$: 506.15, measured (ES, m/z): 507.10 [M+H]+. $^1$H NMR (300 MHz, DMSO-$d_6$) δ 9.68 (s, 1H), 8.29-8.44 (m, 2H), 8.19 (s, 1H), 8.06 (dd, J=8.7, 7.8 Hz, 1H), 7.90 (d, J=0.7 Hz, 1H), 7.75 (dd, J=8.7, 1.6 Hz, 1H), 7.25 (d, J=8.3 Hz, 1H), 7.15 (dd, J=8.3, 1.6 Hz, 1H), 6.05-6.15 (m, 1H), 4.06 (s, 3H), 2.30-2.42 (m, 1H), 1.85-2.00 (m, 1H), 1.50-1.70 (m, 1H), 0.22-0.42 (m, 2H), 0.05-0.18 (m, 1H), −0.08-0.03 (m, 1H). $^{19}$F NMR (282 MHz, DMSO-$d_6$) δ −112.76.

Example 522: (R)-5-(3-Chloro-2-fluoro-6-(1H-tetrazol-1-yl)phenyl)-2-(2-cyclopropyl-1-(4-(1-methyl-1H-imidazol-5-yl)-1H-pyrazol-1-yl)ethyl)pyridine 1-oxide

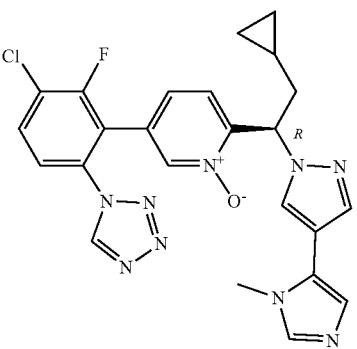

Step 1: 4-(1-Methyl-1H-imidazol-5-yl)-1H-pyrazole

5-Bromo-1-methyl-1H-imidazole (10.0 g, 62.11 mmol, 1.0 equiv.), tert-butyl 4-(4,4,5,5-tetramethyl-1,3,2-dioxaborolan-2-yl)-1H-pyrazole-1-carboxylate (21.9 g, 74.53 mmol, 1.2 equiv.), $K_2CO_3$ (25.7 g, 186.34 mmol, 3.0 equiv) and $Pd(PPh_3)_4$ (7.2 g, 6.21 mmol, 0.1 equiv.) were dissolved in DMF (50.0 mL) and $H_2O$ (10.0 mL). The flask was evacuated and flushed three times with nitrogen and the mixture was stirred for 17.0 h at 100° C. under an atmosphere of nitrogen. The solvent was removed by distillation under vacuum. The resulting was diluted with water (60.0 mL), then extracted with EA. Organic phase was dried under vacuum to yield 4-(1-methyl-1H-imidazol-5-yl)-1H-pyrazole as a yellow solid. LC/MS: mass calculated for $C_7H_8N_4$: 148.07, measured (ES, m/z): 149.05 $[M+H]^+$.

Step 2: 5-Bromo-2-(2-cyclopropyl-1-(4-(1-methyl-1H-imidazol-5-yl)-1H-pyrazol-1-yl)ethyl)pyridine 4-(1-Methyl-1H-imidazol-5-yl)-1H-pyrazole (1.1 g, 7.50 mmol, 1.0 equiv.) and $Cs_2CO_3$ (2.0 g, 6.25 mmol, 1.0 equiv.) were dissolved in $CH_3CN$ (15.0 mL). The mixture was stirred at room temperature for 1.0 h. Then 1-(5-bromopyridin-2-yl)-2-cyclopropylethyl methanesulfonate (2.0 g, 6.25 mmol, 1.0 equiv.) was added into the mixture and the mixture was heated to 80° C. for 2.0 h with $N_2$. The solvent was removed under reduced pressure. The residue was applied onto a silica gel column with EA to yield 5-bromo-2-(2-cyclopropyl-1-(4-(1-methyl-1H-imidazol-5-yl)-1H-pyrazol-1-yl)ethyl)pyridine light as a brown oil. LC/MS: mass calculated for $C_{17}H_{18}BrN_5$: 371.07, measured (ES, m/z): 374.00 $[M+H+2]^+$.

Step 3: 4-Chloro-2-(6-(2-cyclopropyl-1-(4-(1-methyl-1H-imidazol-5-yl)-1H-pyrazol-1-yl)ethyl)pyridin-3-yl)-3-fluoroaniline 5-Bromo-2-(2-cyclopropyl-1-(4-(1-methyl-1H-imidazol-5-yl)-1H-pyrazol-1-yl)ethyl)pyridine (1.0 g, 2.69 mmol, 1.0 equiv.), (6-amino-3-chloro-2-fluorophenyl)boronic acid (1.0 g, 5.37 mmol, 2.0 equiv.), $K_2CO_3$ (1.1 g, 8.06 mmol, 3.0 equiv.) and $Pd(PPh_3)_4$ (310.5 mg, 0.27 mmol, 0.1 equiv.) were dissolved in 1,4-dioxane (5.0 mL) and $H_2O$ (1.0 mL). The flask was evacuated and flushed three times with nitrogen and the mixture was stirred 17.0 h at 100° C. under an atmosphere of nitrogen, then concentrated under reduced pressure. The residue was applied onto a silica gel column with MeOH/DCM (1:5) to yield 4-chloro-2-(6-(2-cyclopropyl-1-(4-(1-methyl-1H-imidazol-5-yl)-1H-pyrazol-1-yl)ethyl)pyridin-3-yl)-3-fluoroaniline as a light yellow oil. LC/MS: mass calculated for $C_{23}H_{22}ClFN_6$: 436.16, measured (ES, m/z): 437.15 $[M+H]^+$.

Step 4: 5-(3-Chloro-2-fluoro-6-(1H-tetrazol-1-yl)phenyl)-2-(2-cyclopropyl-1-(4-(1-methyl-1H-imidazol-5-yl)-1H-pyrazol-1-yl)ethyl)pyridine 4-Chloro-2-(6-(2-cyclopropyl-1-(4-(1-methyl-1H-imidazol-5-yl)-1H-pyrazol-1-yl)ethyl)pyridin-3-yl)-3-fluoroaniline (300.0 mg, 0.69 mmol, 1.0 equiv.) was dissolved in azidotrimethylsilane (3.0 mL), trimethoxymethane (3.0 mL) and AcOH (3.0 mL). The mixture was stirred at room temperature for 17.0 h. The solvent was removed under vacuum. The residue was purified by chromatography on C18 (80 g, MeCN/$H_2O$ (0.05% $CF_3COOH$): 0→60%) to yield 5-(3-chloro-2-fluoro-6-(1H-tetrazol-1-yl)phenyl)-2-(2-cyclopropyl-1-(4-(1-methyl-1H-imidazol-5-yl)-1H-pyrazol-1-yl)ethyl)pyridine as a yellow oil. LC/MS: mass calculated for $C_{24}H_{21}ClFN_9$: 489.16, measured (ES, m/z): 490.10 $[M+H]^+$.

Step 5: (R)-5-(3-chloro-2-fluoro-6-(1H-tetrazol-1-yl)phenyl)-2-(2-cyclopropyl-1-(4-(1-methyl-1H-imidazol-5-yl)-1H-pyrazol-1-yl)ethyl)pyridine 1-oxide 5-(3-Chloro-2-fluoro-6-(1H-tetrazol-1-yl)phenyl)-2-(2-cyclopropyl-1-(4-(1-methyl-1H-imidazol-5-yl)-1H-pyrazol-1-yl)ethyl)pyridine (100.0 mg, 0.20 mmol, 1.0 equiv.) and m-CPBA (10.0 mg, 0.06 mmol, 0.3 equiv.) were dissolved in EA (3.0 mL). The mixture was stirred at room temperature for 17 h, then the solvent was removed under vacuum and the residue was purified by chromatography on C18 (80 g, MeCN/$H_2O$ (0.05% $CF_3COOH$): 0→60%) and prep-chiral-HPLC. The collected fractions were combined and concentrated under vacuum to yield (R)-5-(3-chloro-2-fluoro-6-(1H-tetrazol-1-yl)phenyl)-2-(2-cyclopropyl-1-(4-(1-methyl-1H-imidazol-5-yl)-1H-pyrazol-1-yl)ethyl)pyridine 1-oxide as an off-white solid.

LC/MS: mass calculated for $C_{24}H_{21}ClFN_9O$: 505.15, measured (ES, m/z): 506.10 $[M+H]^+$. $^1H$ NMR (300 MHz, $CD_3OD$) δ 9.40 (s, 1H), 8.35-8.42 (m, 1H), 8.19 (d, J=0.8 Hz, 1H), 7.85-7.94 (m, 1H), 7.82 (s, 1H), 7.58-7.70 (m, 2H), 7.50 (d, J=8.3 Hz, 1H), 7.28-7.34 (m, 1H), 7.08 (s, 1H), 6.20-6.32 (m, 1H), 3.75 (s, 3H), 2.40-2.52 (m, 1H), 1.96-2.11 (m, 1H), 0.62-0.80 (m, 1H), 0.34-0.54 (m, 2H), 0.15-0.25 (m, 1H), 0.02-0.15 (m, 1H). $^{19}F$ NMR (376 MHz, $CD_3OD$) δ −113.36.

Example 523: (S)-5-(3-Chloro-2-fluoro-6-(1H-tetrazol-1-yl)phenyl)-2-(2-cyclopropyl-1-(4-(1-methyl-1H-1,2,3-triazol-4-yl)-1H-pyrazol-1-yl)ethyl)pyridine 1-oxide

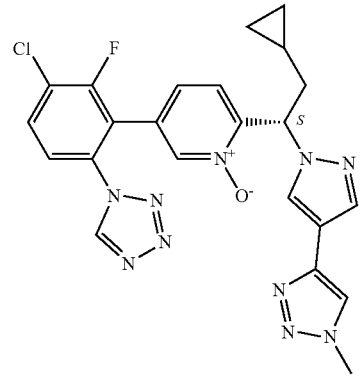

LC/MS: mass calculated for $C_{23}H_{20}ClFN_{10}O$: 506.15, measured (ES, m/z): 507.10 $[M+H]^+$. $^1H$ NMR (300 MHz, DMSO-$d_6$) δ 9.68 (s, 1H), 8.29-8.44 (m, 2H), 8.19 (s, 1H), 8.06 (dd, J=8.7, 7.8 Hz, 1H), 7.90 (d, J=0.7 Hz, 1H), 7.75 (dd, J=8.7, 1.6 Hz, 1H), 7.25 (d, J=8.3 Hz, 1H), 7.15 (dd, J=8.3, 1.6 Hz, 1H), 6.05-6.15 (m, 1H), 4.06 (s, 3H), 2.30-2.42 (m, 1H), 1.85-2.00 (m, 1H), 1.50-1.70 (m, 1H), 0.22-0.42 (m, 2H), 0.05-0.18 (m, 1H), −0.08-0.03 (m, 1H). $^{19}F$ NMR (282 MHz, DMSO-$d_6$) δ −112.76.

Example 524: (R)-5-(3-Chloro-2-fluoro-6-(1H-tetrazol-1-yl)phenyl)-2-(2-cyclopropyl-1-(4-(oxazol-5-yl)-1H-pyrazol-1-yl)ethyl)pyridine 1-oxide

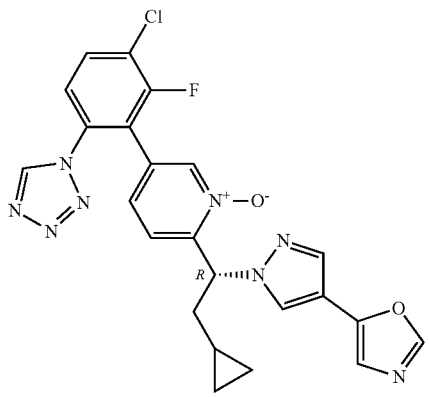

Step 1: 1-(1-(5-Bromopyridin-2-yl)-2-cyclopropylethyl)-1H-pyrazole-4-carbaldehyde 1H-pyrazole-4-carbaldehyde (600.2 mg, 6.25 mmol, 1.0 equiv.) and $Cs_2CO_3$ (2.0 g, 6.25 mmol, 1.0 equiv.) were dissolved in $CH_3CN$ (15.0 mL). The mixture was stirred at r.t for 1.0 h. Then 1-(5-bromopyridin-2-yl)-2-cyclopropylethyl methanesulfonate (2.0 g, 6.25 mmol, 1.0 equiv.) was added into the mixture. The flask was evacuated and flushed three times with nitrogen, followed by flushing with nitrogen and heated to 80° C. for 2.0 h. The residue was diluted with water (50.0 mL). The mixture was extracted with ethyl acetate (3×40 mL). The organic layers were combined, washed with brine, dried over $Na_2SO_4$ and concentrated under vacuum to yield 1-(1-(5-bromopyridin-2-yl)-2-cyclopropylethyl)-1H-pyrazole-4-carbaldehyde as a yellow oil. LC/MS: mass calculated for $C_{14}H_{14}BrN_3O$: 319.03, measured (ES, m/z): 319.95 $[M+H]^+$.

Step 2: 5-(1-(1-(5-Bromopyridin-2-yl)-2-cyclopropylethyl)-1H-pyrazol-4-yl)oxazole 1-(1-(5-Bromopyridin-2-yl)-2-cyclopropylethyl)-1H-pyrazole-4-carbaldehyde (1.0 g, 3.12 mmol, 1.0 equiv.), tosylmethyl isocyanide (609.8 mg, 3.12 mmol, 1.0 equiv.) and $K_2CO_3$ (431.7 mg, 3.12 mmol, 1.0 equiv.) were dissolved in MeOH (10.0 mL). The mixture was heated to 90° C. for 2 h. The solvent was removed by distillation under vacuum. The residue was applied onto a silica gel column with ethyl acetate to yield 5-(1-(1-(5-bromopyridin-2-yl)-2-cyclopropylethyl)-1H-pyrazol-4-yl)oxazole as a yellow oil. LC/MS: mass calculated for $C_{16}H_{15}BrN_4O$: 358.04, measured (ES, m/z): 361.05 $[M+H+2]^+$.

Step 3: 4-Chloro-2-(6-(2-cyclopropyl-1-(4-(oxazol-5-yl)-1H-pyrazol-1-yl)ethyl)pyridin-3-yl)-3-fluoroaniline 5-(1-(1-(5-Bromopyridin-2-yl)-2-cyclopropylethyl)-1H-pyrazol-4-yl)oxazole (400.0 mg, 1.11 mmol, 1.0 equiv.), (6-amino-3-chloro-2-fluorophenyl)boronic acid (421.8 mg, 2.23 mmol, 2.0 equiv.), $K_2CO_3$ (307.8 mg, 2.23 mmol, 2.0 equiv.) and $Pd(PPh_3)_4$ (128.7 mg, 0.11 mmol, 0.1 equiv.) were dissolved in 1,4-dioxane (5.0 mL) and $H_2O$ (1.0 mL). The flask was evacuated and flushed three times with nitrogen and the mixture was stirred 2.0 h at 100° C. under an atmosphere of nitrogen. The solvent was removed by distillation under vacuum. The residue was applied onto a silica gel column with MeOH/DCM (1:5) to yield 4-chloro-2-(6-(2-cyclopropyl-1-(4-(oxazol-5-yl)-1H-pyrazol-1-yl)ethyl)pyridin-3-yl)-3-fluoroaniline as a yellow oil. LC/MS: mass calculated for $C_{22}H_{19}ClFN_5O$: 423.13, measured (ES, m/z): 424.05 $[M+H]^+$.

Step 4: 5-(1-(1-(5-(3-Chloro-2-fluoro-6-(1H-tetrazol-1-yl)phenyl)pyridin-2-yl)-2-cyclopropylethyl)-1H-pyrazol-4-yl)oxazole 4-chloro-2-(6-(2-cyclopropyl-1-(4-(oxazol-5-yl)-1H-pyrazol-1-yl)ethyl)pyridin-3-yl)-3-fluoroaniline (500.0 mg, 1.18 mmol, 1.0 equiv.) was dissolved in azidotrimethylsilane (5.0 mL), trimethoxymethane (5.0 mL) and AcOH (5.0 mL). The mixture was stirred at room temperature for 17.0 h. The solvent was removed under vacuum. Following this the reaction mixture was purified by chromatography on C18 (80 g, $MeCN/H_2O$ (0.05% $CF_3COOH$): 0→60%) to yield 5-(1-(1-(5-(3-chloro-2-fluoro-6-(1H-tetrazol-1-yl)phenyl)pyridin-2-yl)-2-cyclopropylethyl)-1H-pyrazol-4-yl)oxazole as a light yellow oil. LC/MS: mass calculated for $C_{23}H_{18}ClFN_8O$: 476.13, measured (ES, m/z): 477.00 $[M+H]^+$.

Step 5: (R)-5-(3-Chloro-2-fluoro-6-(1H-tetrazol-1-yl)phenyl)-2-(2-cyclopropyl-1-(4-(oxazol-5-yl)-1H-pyrazol-1-yl)ethyl)pyridine 1-oxide 5-(1-(1-(5-(3-Chloro-2-fluoro-6-(1H-tetrazol-1-yl)phenyl)pyridin-2-yl)-2-cyclopropylethyl)-1H-pyrazol-4-yl)oxazole (100.0 mg, 0.21 mmol, 1.0 equiv.) and m-CPBA (10.0 mg, 0.06 mmol, 0.3 equiv.) were dissolved in EA (3.0 mL). The mixture was stirred at room temperature for 17.0 h. The reaction mixture was purified by chromatography on C18 (80 g, $MeCN/H_2O$ (0.05% $CF_3COOH$): 0→60%) and prep-chiral-HPLC. The collected fractions were combined and concentrated under vacuum to yield (R)-5-(3-chloro-2-fluoro-6-(1H-tetrazol-1-yl)phenyl)-2-(2-cyclopropyl-1-(4-(oxazol-5-yl)-1H-pyrazol-1-yl)ethyl)pyridine 1-oxide as an off-white solid.

LC/MS: mass calculated for $C_{23}H_{18}ClFN_8O_2$: 492.12, measured (ES, m/z): 493.10 $[M+H]^+$. $^1H$ NMR (300 MHz, $CD_3OD$) δ 9.39 (s, 1H), 8.28-8.41 (m, 2H), 8.18 (s, 1H), 7.87-7.99 (m, 2H), 7.58-7.64 (m, 1H), 7.49 (d, J=8.3 Hz, 1H), 7.24-7.35 (m, 2H), 6.19-6.28 (m, 1H), 2.38-2.52 (m, 1H), 1.95-2.07 (m, 1H), 0.62-0.78 (m, 1H), 0.31-0.51 (m, 2H), 0.10-0.21 (m, 1H), 0.03-0.08 (m, 1H). $^{19}F$ NMR (282 MHz, $CD_3OD$) δ −113.70.

Example 525: (R*)-5-(3-Chloro-2-fluoro-6-(1H-tetrazol-1-yl)phenyl)-2-(2-cyclopropyl-1-(4-(1-methyl-1H-imidazol-5-yl)-1H-pyrazol-1-yl)ethyl)pyridine 1-oxide

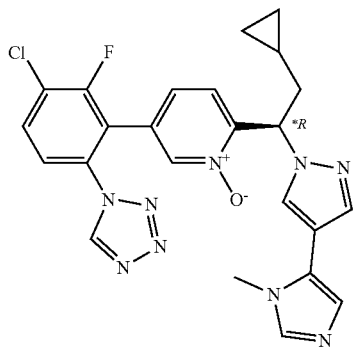

LC/MS: mass calculated for $C_{24}H_{21}ClFN_9O$: 505.1, measured (ES, m/z): 506.10 [M+H]$^+$. $^1$H NMR (300 MHz, CD$_3$OD) δ 9.40 (s, 1H), 8.42-8.35 (m, 1H), 8.19 (d, J=0.8 Hz, 1H), 7.93 (dd, J=8.7, 7.6 Hz, 1H), 7.82 (s, 1H), 7.58-7.70 (m, 2H), 7.50 (d, J=8.3 Hz, 1H), 7.31 (dd, J=8.3, 1.7 Hz, 1H), 7.08 (s, 1H), 6.20-6.30 (m, 1H), 3.75 (s, 3H), 2.40-2.57 (m, 1H), 1.96-2.11 (m, 1H), 0.62-0.80 (m, 1H), 0.34-0.54 (m, 2H), 0.11-0.26 (m, 1H), 0.01-0.10 (m, 1H). $^{19}$F NMR (282 MHz, CD$_3$OD) δ −113.72.

Example 526: (R*)-5-(3-Chloro-2-fluoro-6-(1H-tetrazol-1-yl)phenyl)-2-(2-cyclopropyl-1-(4-(oxazol-5-yl)-1H-pyrazol-1-yl)ethyl)pyridine 1-oxide

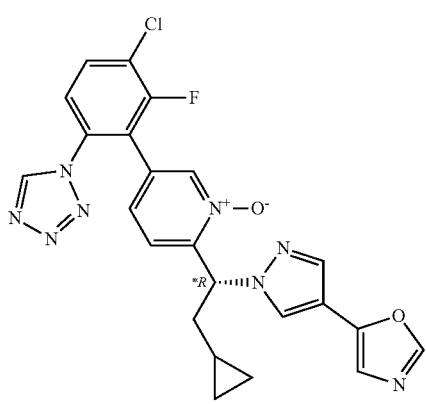

LC/MS: mass calculated for $C_{23}H_{18}ClFN_8O$: 492.12, measured (ES, m/z): 493.10 [M+H]$^+$. $^1$H NMR (300 MHz, CD$_3$OD) δ 9.39 (s, 1H), 8.29 (s, 1H), 8.35 (s, 1H), 8.18 (s, 1H), 7.87-7.99 (m, 2H), 7.62 (dd, J=8.7, 1.7 Hz, 1H), 7.49 (d, J=8.3 Hz, 1H), 7.24-7.35 (m, 2H), 6.20-6.30 (m, 1H), 2.40-2.55 (m, 1H), 1.92-2.10 (m, 1H), 0.60-0.80 (m, 1H), 0.33-0.54 (m, 2H), 0.13-0.26 (m, 1H), 0.00-0.10 (m, 1H). $^{19}$F NMR (282 MHz, CD$_3$OD) δ −113.70.

Example 527: (R*)-2-(1-(4-(4-Carboxyphenyl)-1H-pyrazol-1-yl)-2-(4-fluoro-1H-pyrazol-1-yl)ethyl)-5-(3-chloro-6-(difluoromethyl)-2-fluorophenyl)pyridine 1-oxide

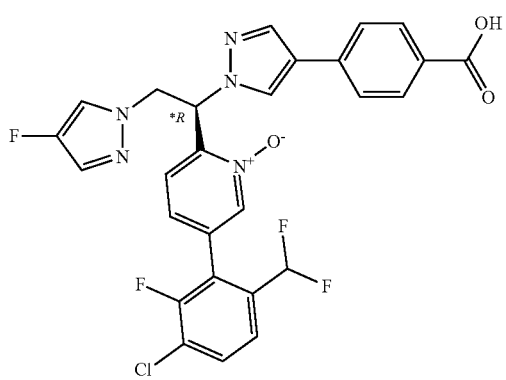 [SMILES: O=C(O)c1ccc(-c2cnn([C@H](Cn3cc(F)cn3)c3ccc(-c4c(C(F)F)ccc(Cl)c4F)c[n+]3[O-])c2)cc1]

LC/MS: mass calculated for $C_{27}H_{18}ClF_4N_5O_3$: 571.10, measured (ES, m/z): 572.10 [M+H]$^+$. $^1$H NMR (300 MHz, DMSO-d$_6$) δ 12.86 (s, 1H), 8.45-8.65 (m, 2H), 8.21 (s, 1H), 7.82-7.98 (m, 3H), 7.59-7.74 (m, 4H), 7.38-7.52 (m, 3H), 6.89 (t, J=53.9 Hz, 1H), 6.57-6.67 (m, 1H), 4.90-5.13 (m, 2H). $^{19}$F NMR (282 MHz, DMSO-d$_6$) δ −109.00, −115.20, −177.89.

Example 528: 5-(3-Chloro-2-fluoro-6-(1H-tetrazol-1-yl)phenyl)-2-(1-(4-(2,6-dimethylpyridin-4-yl)-1H-pyrazol-1-yl)-2-(4-fluoro-1H-pyrazol-1-yl)ethyl)pyridine 1-oxide

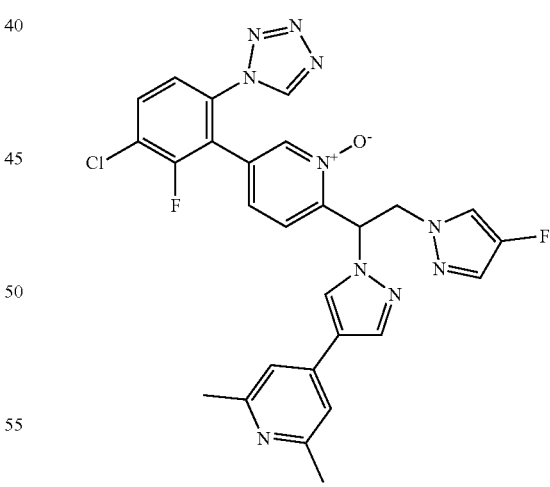

LC/MS: mass calculated for $C_{28}H_{21}ClF_2N_{10}O$: 586.15, measured (ES, m/z): 587.15[M+H]$^+$. $^1$H NMR (300 MHz, DMSO-d$_6$) δ 9.69 (s, 1H), 8.71 (s, 1H), 8.42-8.58 (m, 2H), 8.36 (s, 1H), 8.07 (t, J=8.2 Hz, 1H), 7.59-7.83 (m, 4H), 7.52 (d, J=8.2 Hz, 1H), 7.44 (d, J=4.2 Hz, 1H), 7.20-7.30 (m, 1H), 6.47-6.56 (m, 1H), 4.88-5.05 (m, 2H), 2.10-2.22 (m, 1H), 1.00-1.20 (m, 4H). $^{19}$F NMR (282 MHz, DMSO-d$_6$) δ −73.67, −112.66, −177.68.

Example 529: (S)-2-(1-(4-(4-Carboxyphenyl)-1H-pyrazol-1-yl)-3-methoxypropyl)-5-(3-chloro-6-(difluoromethyl)-2-fluorophenyl)pyridine 1-oxide

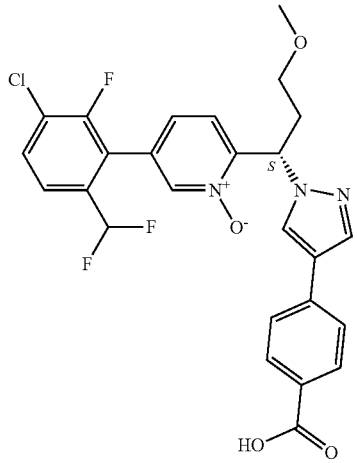

LC/MS: mass calculated for $C_{26}H_{21}ClF_3N_3O_4$: 531.1, measured (ES, m/z): 532.05 [M+H]$^+$. $^1$H NMR (300 MHz, DMSO-$d_6$) δ 12.85 (s, 1H), 8.64 (s, 1H), 8.51 (s, 1H), 8.18 (s, 1H), 7.84-7.98 (m, 3H), 7.77 (d, J=8.4 Hz, 2H), 7.62 (d, J=8.5 Hz, 1H), 7.34-7.47 (m, 2H), 6.89 (t, J=54.0 Hz, 1H), 6.21-6.32 (m, 1H), 3.35-3.43 (m, 1H), 3.19-3.29 (m, 4H), 2.53-2.61 (m, 2 h). $^{19}$F NMR (282 MHz, DMSO-$d_6$) δ −109.80, −115.26.

Example 530: (R)-2-(1-(4-(4-Carboxyphenyl)-1H-pyrazol-1-yl)-3-methoxypropyl)-5-(3-chloro-6-(difluoromethyl)-2-fluorophenyl)pyridine 1-oxide

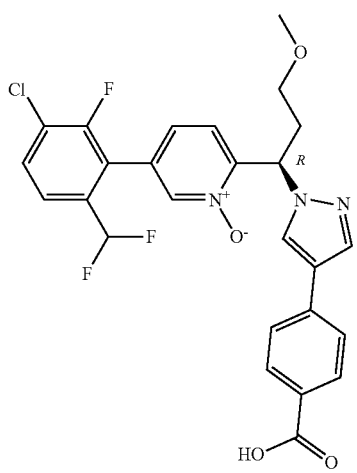

LC/MS: mass calculated for $C_{26}H_{21}ClF_3N_3O_4$: 531.1, measured (ES, m/z): 532.1 [M+H]$^+$. $^1$H NMR (300 MHz, DMSO-$d_6$) δ 12.85 (brs, 1H), 8.64 (s, 1H), 8.51 (d, J=1.4 Hz, 1H), 8.18 (s, 1H), 7.84-7.98 (m, 3H), 7.77 (d, J=8.4 Hz, 2H), 7.62 (d, J=8.5 Hz, 1H), 7.34-7.47 (m, 2H), 6.69-7.08 (m, 1H), 6.21-6.32 (m, 1H), 3.33 (s, 1H), 3.17-3.41 (m, 4H), 2.57-2.62 (m, 2H). $^{19}$F NMR (282 MHz, DMSO-$d_6$) δ −73.39, −115.28.

Example 531: (S*)-5-(3-Chloro-2-fluoro-6-(1H-tetrazol-1-yl)phenyl)-2-(2-(4-fluoro-1H-pyrazol-1-yl)-1-(4-(1-methyl-1H-imidazol-5-yl)-1H-pyrazol-1-yl)ethyl)pyridine 1-oxide

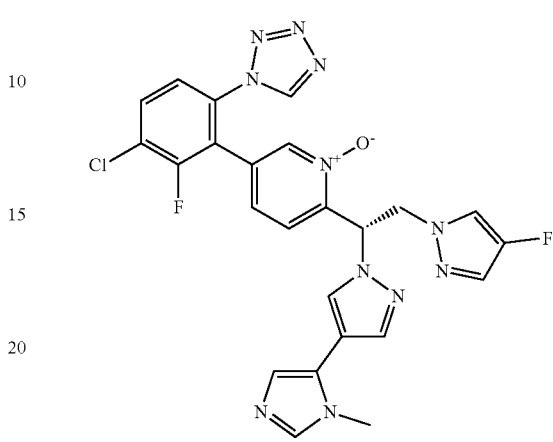

LC/MS: mass calculated for $C_{24}H_{18}ClF_2NO_{11}$: 549.14, measured (ES, m/z): 572.10 [M+Na]$^+$. $^1$H NMR (300 MHz, DMSO-$d_6$) δ 9.69 (s, 1H), 8.52 (s, 1H), 8.22 (s, 1H), 8.07 (dd, J=8.7, 7.7 Hz, 1H), 7.91 (s, 1H), 7.76 (dd, J=8.8, 1.6 Hz, 1H), 7.61 (d, J=4.5 Hz, 1H), 7.33-7.50 (m, 3H), 7.17-7.26 (m, 1H), 6.48-6.58 (m, 1H), 6.36 (d, J=1.9 Hz, 1H), 4.82-5.03 (m, 2H), 3.80 (s, 3H). $^{19}$F NMR (282 MHz, DMSO-$d_6$) δ −73.40, −112.63, −177.92.

Example 532: (R)-5-(3-Chloro-2-fluoro-6-(1H-tetrazol-1-yl)phenyl)-2-(2-(4-fluoro-1H-pyrazol-1-yl)-1-(2-methyl-1'H,2H-[3,4'-bipyrazol]-1'-yl)ethyl)pyridine 1-oxide

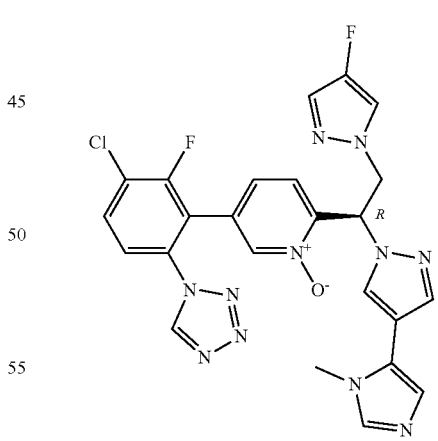

LC/MS: mass calculated for C24H18ClF2N11O: 549.1, measured (ES, m/z): 550.2 [M+H]$^+$. $^1$H NMR (300 MHz, DMSO-d6) δ 9.69 (s, 1H), 8.52 (d, J=1.4 Hz, 1H), 8.14-8.01 (m, 2H), 7.84 (s, 1H), 7.76 (dd, J=8.7, 1.5 Hz, 1H), 7.62-7.55 (m, 2H), 7.49-7.42 (m, 1H), 7.39 (d, J=8.3 Hz, 1H), 7.25-7.16 (m, 1H), 6.97 (d, J=1.2 Hz, 1H), 6.51 (dd, J=9.3, 4.7 Hz, 1H), 5.02-4.81 (m, 2H), 3.58 (s, 3H). $^{19}$F NMR (282 MHz, DMSO-d6) δ −112.64, −177.98.

Example 533: (R)-5-(3-Chloro-2-fluoro-6-(1H-tetrazol-1-yl)phenyl)-2-(2-(4-fluoro-1H-pyrazol-1-yl)-1-(4-(1-methyl-1H-imidazol-5-yl)-1H-pyrazol-1-yl)ethyl)pyridine 1-oxide

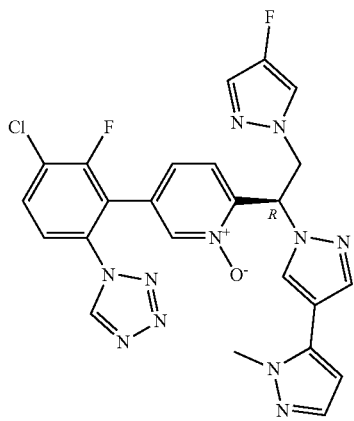

LC/MS: mass calculated for $C_{24}H_{18}ClF_2N_{11}O$: 549.14, measured (ES, m/z): 550.10 [M+H]$^+$. $^1$H NMR (300 MHz, DMSO-d$_6$) δ 9.69 (s, 1H), 8.52 (s, 1H), 8.22 (s, 1H), 8.07 (dd, J=8.7, 7.8 Hz, 1H), 7.91 (s, 1H), 7.76 (dd, J=8.8, 1.6 Hz, 1H), 7.61 (d, J=4.6 Hz, 1H), 7.33-7.49 (m, 3H), 6.87-7.28 (m, 2H), 6.48-6.58 (m, 1H), 6.36 (d, J=1.9 Hz, 1H), 4.82-5.03 (m, 2H), 3.80 (s, 3H). $^{19}$F NMR (282 MHz, DMSO-d$_6$) δ −73.50, −112.64, −177.92.

Example 534: (S*)-5-(3-Chloro-2-fluoro-6-(1H-tetrazol-1-yl)phenyl)-2-(2-(4-fluoro-1H-pyrazol-1-yl)-1-(4-(1-methyl-1H-imidazol-5-yl)-1H-pyrazol-1-yl)ethyl)pyridine 1-oxide

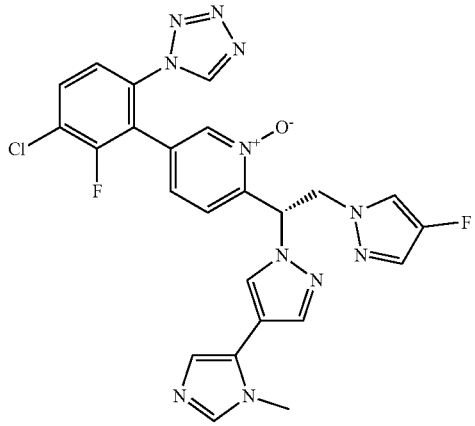 [SMILES: Cn1cncc1-c1cnn([C@@H](Cn2cc(F)cn2)c2ccc(-c3c(-n4cnnn4)ccc(Cl)c3F)c[n+]2[O-])c1]

LC/MS: mass calculated for $C_{24}H_{18}ClF_2N_{11}O$: 549.14, measured (ES, m/z): 550.15 [M+H]$^+$. $^1$H NMR (300 MHz, DMSO-d$_6$) δ 9.69 (s, 1H), 8.52 (d, J=1.5 Hz, 1H), 8.01-8.14 (m, 2H), 7.84 (s, 1H), 7.76 (dd, J=8.7, 1.6 Hz, 1H), 7.55-7.65 (m, 2H), 7.45 (d, J=4.1 Hz, 1H), 7.39 (d, J=8.3 Hz, 1H), 7.16-7.25 (m, 1H), 6.97 (d, J=1.1 Hz, 1H), 6.47-6.57 (m, 1H), 4.81-5.02 (m, 2H), 3.58 (s, 3H). $^{19}$F NMR (282 MHz, DMSO-d$_6$) δ −112.64, −177.98.

Example 535: (R*)-5-(3-Chloro-2-fluoro-6-(1H-tetrazol-1-yl)phenyl)-2-(2-cyclopropyl-1-(4-(3-methylisoxazol-4-yl)-1H-pyrazol-1-yl)ethyl)pyridine 1-oxide

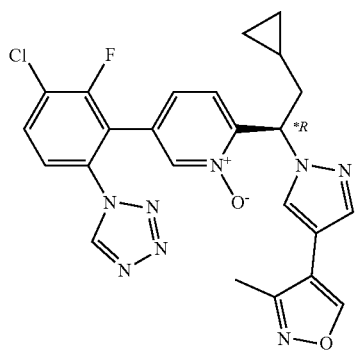

LC/MS: mass calculated for $C_{24}H_{20}ClFN_8O_2$: 506.14, measured (ES, m/z): 507.20 [M+H]$^+$. $^1$H NMR (400 MHz, DMSO-d$_6$) δ 9.69 (s, 1H), 9.03 (s, 1H), 8.42 (s, 1H), 8.34 (s, 1H), 8.08 (t, J=8.2 Hz, 1H), 7.85 (s, 1H), 7.75 (d, J=8.8 Hz, 1H), 7.25 (d, J=8.3 Hz, 1H), 7.15 (d, J=8.3 Hz, 1H), 6.07-6.17 (m, 1H), 2.30-2.42 (m, 4H), 1.85-1.93 (m, 1H), 0.55-0.65 (m, 1H), 0.25-0.45 (m, 2H), 0.08-0.16 (m, 1H), −0.08-0.05 (m, 1H). $^{19}$F NMR (376 MHz, DMSO-d$_6$) δ −112.77.

Example 536: (R)-5-(3-Chloro-2-fluoro-6-(1H-tetrazol-1-yl)phenyl)-2-(2-cyclopropyl-1-(4-(3-methylisoxazol-4-yl)-1H-pyrazol-1-yl)ethyl)pyridine 1-oxide

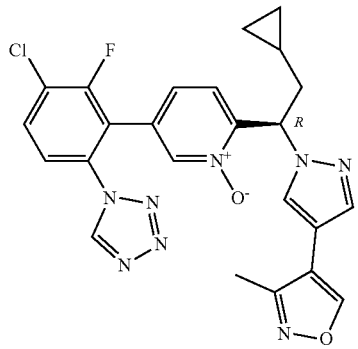

Step 1: 4-(1-(1-(5-Bromopyridin-2-yl)-2-cyclopropylethyl)-1H-pyrazol-4-yl)-3-methylisoxazole A mixture of 5-bromo-2-(2-cyclopropyl-1-(4-iodo-1H-pyrazol-1-yl)ethyl)pyridine (430 mg, 1.03 mmol, 1.0 equiv.), 3-methyl-4-(4,4,5,5-tetramethyl-1,3,2-dioxaborolan-2-yl)isoxazole (237 mg, 1.13 mmol, 1.1 equiv.), Pd(dppf)Cl$_2$·CH$_2$Cl$_2$ (78 mg, 0.1 mmol, 0.1 equiv.) and potassium carbonate (426 mg, 3.09 mmol, 3.0 equiv.) in 1,4-dioxane (10 mL) and water (2 mL) was stirred at 100° C. for 2 h under nitrogen atmosphere. After cooling to room temperature, the reaction was quenched with water, and the mixture extracted with ethyl acetate twice. The combined organic layers were washed with brine, dried over sodium sulfate and concentrated. The residue was purified by silica gel chromatography (0→50% ethyl acetate/petroleum ether) to yield 4-(1-(1-(5-bromopyridin-2-yl)-2-cyclopropylethyl)-1H-pyrazol-4-yl)-3-methylisoxazole as a light yellow oil. LC/MS: mass calculated for $C_{17}H_{17}BrN_4O$: 372.06, measured (ES, m/z): 373.00, 375.00 [M+H, M+H+2]$^+$.

Step 2: 4-Chloro-2-(6-(2-cyclopropyl-1-(4-(3-methylisoxazol-4-yl)-1H-pyrazol-1-yl)ethyl)pyridin-3-yl)-3-fluoroaniline To a mixture of 4-(1-(1-(5-bromopyridin-2-yl)-2-cyclopropylethyl)-1H-pyrazol-4-yl)-3-methylisoxazole (190 mg, 0.51 mmol, 1.0 equiv.), 6-amino-3-chloro-2-fluorophenylboronic acid (145 mg, 0.76 mmol, 1.5 equiv.) and potassium carbonate (211 mg, 1.53 mmol, 3.0 equiv.) in 1,4-dioxane (5 mL) and water (1 mL) was added tetrakis(triphenylphosphine)palladium(0) (59 mg, 0.05 mmol, 0.1 equiv.) and the mixture was stirred at 90° C. for 2 h. After cooling to room temperature, the reaction was quenched with water, and the mixture extracted with ethyl acetate twice. The combined organic layers were washed with brine, dried over anhydrous sodium sulfate and concentrated. The residue was purified by silica gel chromatography (0→80% ethyl acetate/petroleum ether) to yield 4-chloro-2-(6-(2-cyclopropyl-1-(4-(3-methylisoxazol-4-yl)-1H-pyrazol-1-yl)ethyl)pyridin-3-yl)-3-fluoroaniline as a light yellow solid. LC/MS: mass calculated for $C_{23}H_{21}ClFN_5O$: 437.14, measured (ES, m/z): 438.10 [M+H]$^+$.

Step 3: 4-(1-(1-(5-(3-Chloro-2-fluoro-6-(1H-tetrazol-1-yl)phenyl)pyridin-2-yl)-2-cyclopropylethyl)-1H-pyrazol-4-yl)-3-methylisoxazole A mixture of 4-chloro-2-(6-(2-cyclopropyl-1-(4-(3-methylisoxazol-4-yl)-1H-pyrazol-1-yl)ethyl)pyridin-3-yl)-3-fluoroaniline (220 mg, 0.50 mmol, 1.0 equiv.), azidotrimethylsilane (1.0 mL), and trimethoxymethane (1.0 mL) in acetic acid glacial (1.0 mL) was stirred at room temperature overnight. The mixture was concentrated and the residue was purified by reverse phase chromatography on C18 (80 g, MeCN/H$_2$O (0.05% CF$_3$COOH): 0→50%) to yield 4-(1-(1-(5-(3-chloro-2-fluoro-6-(1H-tetrazol-1-yl)phenyl)pyridin-2-yl)-2-cyclopropylethyl)-1H-pyrazol-4-yl)-3-methylisoxazole as a light yellow solid. LC/MS: mass calculated for $C_{24}H_{20}ClFN_8O$: 490.14, measured (ES, m/z): 491.10 [M+H]$^+$.

Step 4: (R)-5-(3-Chloro-2-fluoro-6-(1H-tetrazol-1-yl)phenyl)-2-(2-cyclopropyl-1-(4-(3-methylisoxazol-4-yl)-1H-pyrazol-1-yl)ethyl)pyridine 1-oxide A mixture of 4-(1-(1-(5-(3-chloro-2-fluoro-6-(1H-tetrazol-1-yl)phenyl)pyridin-2-yl)-2-cyclopropylethyl)-1H-pyrazol-4-yl)-3-methylisoxazole (200 mg, 0.41 mmol, 1.0 equiv.), methyl trioxorhenium (VII) (51 mg, 0.20 mmol, 0.5 equiv.) and hydrogen peroxide (0.20 mL, 2.31 mmol, 30 wt %, 5.0 equiv.) in CH$_3$OH (2.0 mL) was stirred at room temperature for 1H. The reaction was purified by reverse phase chromatography on C18 (80 g, MeCN/H$_2$O (0.05% CF$_3$COOH): 0→45%) and then Chiral HPLC to yield (S*)-5-(3-chloro-2-fluoro-6-(1H-tetrazol-1-yl)phenyl)-2-(2-cyclopropyl-1-(4-(3-methylisoxazol-4-yl)-1H-pyrazol-1-yl)ethyl)pyridine 1-oxide as a white solid.

LC/MS: mass calculated for $C_{24}H_{20}ClFN_8O_2$: 506.14, measured (ES, m/z): 507.2 [M+H]$^+$. $^1$H NMR (400 MHz, DMSO-d$_6$): δ9.69 (s, 1H), 9.04 (s, 1H), 8.42 (s, 1H), 8.35 (s, 1H), 8.06 (t, J=8.2 Hz, 1H), 7.85 (s, 1H), 7.72-7.78 (m, 1H), 7.22-7.29 (m, 1H), 7.12-7.19 (m, 1H), 6.08-6.12 (m, 1H), 2.31-2.37 (m, 4H), 1.85-1.92 (m, 1H), 0.56-0.63 (m, 1H), 0.27-0.39 (m, 2H), 0.08-0.14 (m, 1H), 0.03--0.06 (m, 1H). $^{19}$FNMR (376 MHz, DMSO-d$_6$): δ -112.77.

Example 537: (R*)-5-(3-Chloro-2-fluoro-6-(1H-tetrazol-1-yl)phenyl)-2-(2-cyclopropyl-1-(4-(1-methyl-1H-1,2,3-triazol-5-yl)-1H-pyrazol-1-yl)ethyl) pyridine 1-oxide

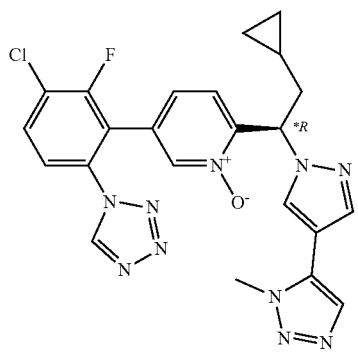

LC/MS: mass calculated for $C_{23}H_{20}ClFN_{10}O$: 506.15, measured (ES, m/z): 507.15 [M+H]$^+$. $^1$H NMR (400 MHz, CD$_3$OD) δ 9.40 (s, 1H), 8.36-8.43 (m, 2H), 7.89-8.03 (m, 2H), 7.86 (s, 1H), 7.63 (dd, J=8.7, 1.7 Hz, 1H), 7.56 (d, J=8.3 Hz, 1H), 7.32 (dd, J=8.4, 1.7 Hz, 1H), 6.25-6.31 (m, 1H), 4.17 (s, 3H), 2.42-2.53 (m, 1H), 2.00-2.12 (m, 1H), 0.62-0.75 (m, 1H), 0.35-0.50 (m, 2H), 0.12-0.25 (m, 1H), 0.03-0.10 (m, 1H). $^{19}$F NMR (376 MHz, CD$_3$OD) δ -113.76.

Example 538: (R)-5-(3-Chloro-2-fluoro-6-(1H-tetrazol-1-yl)phenyl)-2-(2-cyclopropyl-1-(4-(1-methyl-1H-1,2,3-triazol-5-yl)-1H-pyrazol-1-yl)ethyl)pyridine 1-oxide

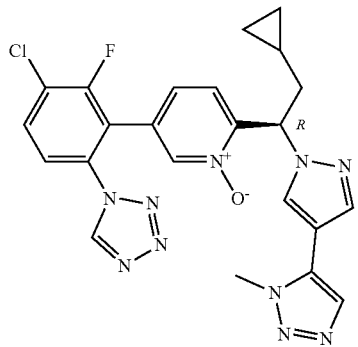

Step 1: 5-Iodo-1-methyl-1H-1,2,3-triazole

1-Methyl-1H-1,2,3-triazole (5.0 g, 60.17 mmol, 1.0 equiv.) was dissolved in THE (100.0 mL). The flask was evacuated and flushed three times with nitrogen, followed by flushing with nitrogen. Then the mixture was cooled to −78° C. and at this temperature, n-BuLi (7.19 mL, 66.19 mmol, 1.1 equiv, 2.5 M in hexane) was added into the mixture slowly. The mixture was then stirred at this temperature for 40 minutes. Then $I_2$ (16.8 g, 66.19 mmol, 1.1 equiv. dissolved in about 40.0 mL THF) was added into the mixture slowly. The mixture was stirred at this temperature for 2.0 h. The reaction was then quenched by the addition of $NH_4Cl$ saturated aqueous solution (100 mL). The resulting solution was extracted with ethyl acetate (3×80 mL). The organic layers were combined, washed with brine, dried, and concentrated under vacuum to yield 5-iodo-1-methyl-1H-1, 2,3-triazo as a light yellow solid. LC/MS: mass calculated for $C_3H_{41}N_3$: 208.94, measured (ES, m/z): 210.05 $[M+H]^+$.

Step 2: 1-Methyl-5-(1H-pyrazol-4-yl)-1H-1,2,3-triazole

5-Iodo-1-methyl-1H-1,2,3-triazole (6.0 g, 28.71 mmol, 1.0 equiv.), tert-butyl 4-(4,4,5,5-tetramethyl-1,3,2-dioxaborolan-2-yl)-1H-pyrazole-1-carboxylate (12.7 g, 43.07 mmol, 1.5 equiv.), $K_2CO_3$ (11.9 g, 86.13 mmol, 3.0 equiv.) and $Pd(PPh_3)_4$ (3.3 g, 2.87 mmol, 0.1 equiv.) were dissolved in DMF (30.0 mL) and $H_2O$ (6.0 mL). The flask was evacuated and flushed three times with nitrogen and the mixture was stirred 17 h at 100° C. under an atmosphere of nitrogen. The solvent was removed by distillation under vacuum. The residue was applied onto a silica gel column with ethyl acetate/petroleum ether (1:1) to yield 1-methyl-5-(1H-pyrazol-4-yl)-1H-1,2,3-triazole as a light yellow solid (58.9% yield). LC/MS: mass calculated for $C_6H_7N_5$: 149.07, measured (ES, m/z): 150.20 $[M+H]^+$.

Step 3: 5-Bromo-2-(2-cyclopropyl-1-(4-(1-methyl-1H-1,2,3-triazol-5-yl)-1H-pyrazol-1-yl)ethyl)pyridine 1-Methyl-5-(1H-pyrazol-4-yl)-1H-1,2,3-triazole (465.8 mg, 3.12 mmol, 1.0 equiv.) and $Cs_2CO_3$ (1.0 g, 3.12 mmol, 1.0 equiv.) were dissolved in $CH_3CN$ (15.0 mL). The mixture was stirred at room temperature for 1.0 h. Then 1-(5-bromopyridin-2-yl)-2-cyclopropylethyl methanesulfonate (1.0 g, 3.12 mmol, 1.0 equiv.) was added into the mixture and the mixture was heated to 80° C. for 2.0 h with $N_2$. The residue was diluted with water then extracted with 3×40 mL of ethyl acetate. The organic layers were combined, washed with brine, dried and concentrated under vacuum to yield 5-bromo-2-(2-cyclopropyl-1-(4-(1-methyl-1H-1,2,3-triazol-5-yl)-1H-pyrazol-1-yl)ethyl)pyridine as a yellow oil. LC/MS: mass calculated for $C_{16}H_{17}BrN_6$: 372.07, measured (ES, m/z): 375.15 $[M+H+2]^+$.

Step 4: 4-Chloro-2-(6-(2-cyclopropyl-1-(4-(1-methyl-1H-1,2,3-triazol-5-yl)-1H-pyrazol-1-yl)ethyl) pyridin-3yl)-3-fluoroaniline 5-Bromo-2-(2-cyclopropyl-1-(4-(1-methyl-1H-1,2,3-triazol-5-yl)-1H-pyrazol-1-yl)ethyl)pyridine (1.0 g, 2.68 mmol, 1.0 equiv.), (6-amino-3-chloro-2-fluorophenyl)boronic acid (1.0 g, 5.36 mmol, 2.0 equiv.), $K_2CO_3$ (1.1 g, 8.04 mmol, 3.0 equiv.) and $Pd(PPh_3)_4$ (309.7 mg, 0.27 mmol, 0.1 equiv.) were dissolved in 1,4-dioxane (10.0 mL) and $H_2O$ (2.0 mL). The flask was evacuated and flushed three times with nitrogen and the mixture was stirred 5.0 h at 100° C. under an atmosphere of nitrogen. The solvent was removed by distillation under vacuum. The residue was applied onto a silica gel column with MeOH/DCM (1:5) to yield 4-chloro-2-(6-(2-cyclopropyl-1-(4-(1-methyl-1H-1,2,3-triazol-5-yl)-1H-pyrazol-1-yl)ethyl)pyridin-3-yl)-3-fluoroaniline as a light brown solid. LC/MS: mass calculated for $C_{22}H_{21}ClFN_7$: 437.15, measured (ES, m/z): 438.05 $[M+H]^+$.

Step 5: 5-(3-Chloro-2-fluoro-6-(1H-tetrazol-1-yl) phenyl)-2-(2-cyclopropyl-1-(4-(1-methyl-1H-1,2,3-triazol-5-yl)-1H-pyrazol-1-yl)ethyl)pyridine 4-Chloro-2-(6-(2-cyclopropyl-1-(4-(1-methyl-1H-1,2,3-triazol-5-yl)-1H-pyrazol-1-yl)ethyl)pyridin-3-yl)-3-fluoroaniline (1.2 g, 2.74 mmol, 1.0 equiv.) was dissolved in azidotrimethylsilane (9.0 mL), trimethoxymethane (9.0 mL) and acetic acid (9.0 mL). The mixture was stirred at room temperature for 17.0 h.

The solvent was removed by distillation under vacuum. The reaction mixture was purified by chromatography on C18 (80 g, $MeCN/H_2O$ (0.05% $CF_3COOH$): 0→60%) to yield 5-(3-chloro-2-fluoro-6-(1H-tetrazol-1-yl)phenyl)-2-(2-cyclopropyl-1-(4-(1-methyl-1H-1,2,3-triazol-5-yl)-1H-pyrazol-1-yl)ethyl)pyridine as a yellow solid. LC/MS: mass calculated for $C_{23}H_{20}ClFN_{10}$: 490.15, measured (ES, m/z): 491.10 $[M+H]^+$.

Step 6: (R)-5-(3-Chloro-2-fluoro-6-(1H-tetrazol-1-yl)phenyl)-2-(2-cyclopropyl-1-(4-(1-methyl-1H-1,2,3-triazol-5-yl)-1H-pyrazol-1-yl)ethyl)pyridine 1-oxide 5-(3-Chloro-2-fluoro-6-(1H-tetrazol-1-yl)phenyl)-2-(2-cyclopropyl-1-(4-(1-methyl-1H-1,2,3-triazol-5-yl)-1H-pyrazol-1-yl)ethyl)pyridine (200.0 mg, 0.41 mmol, 1.0 equiv.) and methyltrioxorhenium (VII) (10.0 mg, 0.04 mmol, 0.1 equiv.) were dissolved in MeOH (3.0 mL). Then $H_2O_2$ (1.0 mL, 30 wt %) was added into the mixture. The mixture was stirred at room temperature for 2.0 h. The reaction mixture was purified by chromatography on C18 (80 g, $MeCN/H_2O$ (0.05% $CF_3COOH$): 0→60%) and prep-chiral-HPLC. The collected fractions were combined and concentrated under vacuum. to yield (R)-5-(3-chloro-2-fluoro-6-(1H-tetrazol-1-yl)phenyl)-2-(2-cyclopropyl-1-(4-(1-methyl-1H-1,2,3-triazol-5-yl)-1H-pyrazol-1-yl)ethyl) pyridine 1-oxide as an off-white solid.

LC/MS: mass calculated for $C_{23}H_{20}ClFN_{10}O$: 506.15, measured (ES, m/z): 507.15 $[M+H]^+$. $^1$H NMR (400 MHz, $CD_3OD$) δ 9.40 (s, 1H), 8.37-8.43 (m, 2H), 7.89-7.99 (m, 2H), 7.86 (s, 1H), 7.60-7.64 (m, 1H), 7.56 (d, J=8.3 Hz, 1H), 7.33-7.40 (m, 1H), 6.20-6.30 (m, 1H), 4.17 (s, 3H), 2.40-2.52 (m, 1H), 2.00-2.11 (m, 1H), 0.71 (t, J=7.0 Hz, 1H), 0.38-0.50 (m, 2H), 0.14-0.24 (m, 1H), 0.04-0.10 (m, 1H). $^{19}$F NMR (376 MHz, $CD_3OD$) δ −113.76.

Example 539: (S)-5-(3-Chloro-2-fluoro-6-(1H-tetrazol-1-yl)phenyl)-2-(3-methoxy-1-(4-(1-methyl-1H-1,2,3-triazol-5-yl)-1H-pyrazol-1-yl)propyl)pyridine 1-oxide

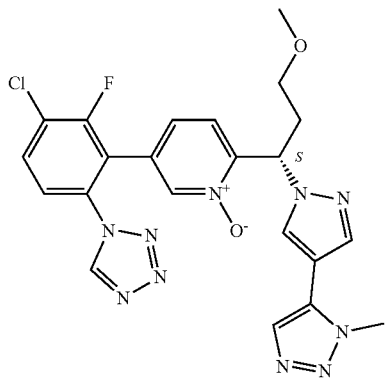

LC/MS: mass calculated for $C_{22}H_{20}ClFN_{10}O_2$: 510.14, measured (ES, m/z): 511.20 [M+H]$^+$. $^1$H NMR (300 MHz, DMSO-d$_6$) δ 9.63 (s, 1H), 8.45 (d, J=0.8 Hz, 1H), 8.38 (s, 1H), 7.94-8.04 (m, 2H), 7.88 (s, 1H), 7.69 (dd, J=8.7, 1.6 Hz, 1H), 7.33 (d, J=8.3 Hz, 1H), 7.16 (dd, J=8.4, 1.6 Hz, 1H), 6.17 (t, J=7.3 Hz, 1H), 4.06 (s, 3H), 3.25-3.38 (m, 1H), 3.10-3.23 (m, 4H), 2.48-2.53 (m, 2 h). $^{19}$F NMR (376 MHz, DMSO-d$_6$) δ −73.50, −112.71.

Example 540: (R-5-(3-Chloro-2-fluoro-6-(1H-tetrazol-1-yl)phenyl)-2-(3-methoxy-1-(4-(1-methyl-1H-1,2,3-triazol-5-yl)-1H-pyrazol-1-yl)propyl)pyridine 1-oxide

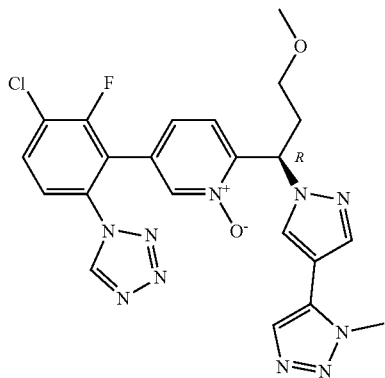

Step 1: 5-Iodo-1-methyl-1H-1,2,3-triazole

A round bottom flask was filled with 1-methyl-1H-1,2,3-triazole (5.0 g, 60.2 mmol, 1.0 eq.) and THF (100.0 mL). The flask was evacuated and flushed three times with nitrogen. The mixture was cooled to −78° C. and at this temperature, n-BuLi (7.19 mL, 66.2 mmol, 1.1 eq, 2.5 M in hexane) was added into the mixture slowly. The mixture was stirred at this temperature for 40 minutes. Then I$_2$ (16.8 g, 66.19 mmol, 1.1 equiv. dissolved in about 40.0 mL THF) was added into the mixture slowly. The mixture was stirred at this temperature for 2.0 h. The reaction was then quenched by the addition of NH$_4$Cl saturated aqueous solution (100 mL). The resulting solution was extracted with ethyl acetate (3×80 mL). The organic layers were combined, washed with brine, dried, and concentrated under vacuum to yield 5-iodo-1-methyl-1H-1,2,3-triazole as a light yellow solid. LC/MS: mass calculated for $C_3H_4IN_3$: 208.94, measured (ES, m/z): 210.05 [M+H]$^+$.

Step 2: 1-Methyl-5-(1H-pyrazol-4-yl)-1H-1,2,3-triazole

5-Iodo-1-methyl-1H-1,2,3-triazole (6.0 g, 28.7 mmol, 1.0 eq.), tert-butyl 4-(4,4,5,5-tetramethyl-1,3,2-dioxaborolan-2-yl)-1H-pyrazole-1-carboxylate (12.7 g, 43.1 mmol, 1.5 eq.), K$_2$CO$_3$ (11.9 g, 86.1 mmol, 3.0 eq.) and Pd(PPh$_3$)$_4$ (3.3 g, 2.87 mmol, 0.1 eq.) were dissolved in DMF (30.0 mL) and H$_2$O (6.0 mL). The flask was evacuated and flushed three times with nitrogen, and the mixture was stirred for 17 h at 100° C. under an atmosphere of nitrogen. The solvent was removed by distillation under vacuum. The residue was applied onto a silica gel column with ethyl acetate/petroleum ether (1:1) to yield 1-methyl-5-(1H-pyrazol-4-yl)-1H-1,2,3-triazole as a light yellow solid. LC/MS: mass calculated for $C_6H_7N_5$: 149.07, measured (ES, m/z): 150.20 [M+H]$^+$.

Step 3: 1-(5-Bromopyridin-2-yl)-3-methoxypropan-1-one

To a solution of 2,5-dibromopyridine (5.0 g, 21.1 mmol, 1.00 eq.) in toluene (50 mL) under nitrogen was added n-butyllithium (8.9 mL, 22.2 mmol, 2.50 M in THF, 1.05 eq.) at −78° C. and the mixture was stirred for 1 h at this temperature. To the solution above was then added the solution of N,3-dimethoxy-N-methylpropanamide (3.42 g, 23.2 mmol, 1.10 eq.) in toluene (10 mL) at −78° C. and the resulting mixture was stirred for 2 h at −78° C., then quenched with sat. NH$_4$Cl aqueous and extracted with ethyl acetate twice. The combined organic layer was washed with brine, dried over Na$_2$SO$_4$ and concentrated. The residue was purified by silica gel chromatography (0-50% EtOAc/petroleum ether) to yield 1-(5-bromopyridin-2-yl)-3-methoxypropan-1-one as a white solid. LC/MS: mass calculated for $C_9H_{10}BrNO_2$: 243.0, measured: 244.0, 246.0 [M+H, M+H+2]$^+$.

Step 4: 1-(5-Bromopyridin-2-yl)-3-methoxypropan-1-ol

To a solution of 1-(5-bromopyridin-2-yl)-3-methoxypropan-1-one (6.2 g, 25.4 mmol, 1.00 eq.) in methanol (10 mL) was added sodium borohydride (1.2 g, 30.5 mmol, 1.20 eq.) in portions at 0° C., and the mixture was stirred for 1 h at room temperature. The reaction was quenched with water and extracted with EtOAc twice. The combined organic layer was washed with water and brine. The organic layer was dried over Na$_2$SO$_4$ and concentrated to yield 1-(5-bromopyridin-2-yl)-3-methoxypropan-1-ol as a yellow oil. LC/MS: mass calculated for $C_9H_{12}BrNO_2$: 245.0, measured: 246.0, 248.0 [M+H, M+H+2]$^+$.

Step 5: 1-(5-Bromopyridin-2-yl)-3-methoxypropyl methanesulfonate

To a mixture of 1-(5-bromopyridin-2-yl)-3-methoxypropan-1-ol (2.2 g, 8.9 mmol, 1.00 eq.) and triethylamine (2.7 g, 26.8 mmol, 3.00 eq.) in DCM (30 mL) was added methanesulfonyl chloride (1.23 g, 10.7 mmol, 1.20 eq.) at 0°

C. and the solution was stirred for 2 h at room temperature. The reaction was washed with water and brine. The organic layer was dried over $Na_2SO_4$ and concentrated. The residue was purified by silica gel chromatography (0-50% EtOAc/petroleum ether) to yield 1-(5-bromopyridin-2-yl)-3-methoxypropyl methanesulfonate as a light yellow solid. LC/MS: mass calculated for $C_{10}H_{14}BrNO_4S$: 323.0, measured: 324.0, 326.0 [M+H, M+H+2]$^+$.

Step 6: 5-Bromo-2-(3-methoxy-1-(4-(1-methyl-1H-1,2,3-triazol-5-yl)-1H-pyrazol-1-yl)propyl)pyridine 1-Methyl-5-(1H-pyrazol-4-yl)-1H-1,2,3-triazole (230.0 mg, 1.54 mmol, 1.0 eq.) and $Cs_2CO_3$ (502.5 mg, 1.54 mmol, 1.0 eq.) were dissolved in $CH_3CN$ (15.0 mL). The mixture was stirred at room temperature for 1.0 h. Then 1-(5-bromopyridin-2-yl)-3-methoxypropyl methanesulfonate (500.0 mg, 1.54 mmol, 1.0 eq.) was added and the resulting mixture was heated to 80° C. for 2.0 h with $N_2$. The solvent was removed under vacuum. The residue was applied onto a silica gel column with ethyl acetate/petroleum ether (1:1) to yield 5-bromo-2-(3-methoxy-1-(4-(1-methyl-1H-1,2,3-triazol-5-yl)-1H-pyrazol-1-yl)propyl)pyridine as a yellow oil. LC/MS: mass calculated for $C_{15}H_{17}BrN_6O$: 376.06, measured (ES, m/z): 379.10 [M+H+2].

Step 7: 4-Chloro-3-fluoro-2-(6-(3-methoxy-1-(4-(1-methyl-1H-1,2,3-triazol-5-yl)-1H-pyrazol-1-yl)propyl)pyridin-3-yl)aniline 5-Bromo-2-(3-methoxy-1-(4-(1-methyl-1H-1,2,3-triazol-5-yl)-1H-pyrazol-1-yl)propyl)pyridine (360.0 mg, 0.95 mmol, 1.0 eq.), (6-amino-3-chloro-2-fluorophenyl)boronic acid (361.4 mg, 1.90 mmol, 2.0 eq.), $K_2CO_3$ (395.6 mg, 2.81 mmol, 3.0 eq.) and $Pd(PPh_3)_4$ (110.3 mg, 0.09 mmol, 0.1 eq.) were dissolved in 1,4-dioxane (10.0 mL) and $H_2O$ (2.0 mL). The flask was evacuated and flushed three times with nitrogen, and the mixture was stirred 2.0 h at 100° C. under an atmosphere of nitrogen. The solvent was removed by distillation under vacuum. The residue was applied onto a silica gel column with MeOH/DCM (1:5) to yield 4-chloro-3-fluoro-2-(6-(3-methoxy-1-(4-(1-methyl-1H-1,2,3-triazol-5-yl)-1H-pyrazol-1-yl)propyl)pyridin-3-yl)aniline as a light brown solid. LC/MS: mass calculated for $C_{21}H_{21}ClFN_7O$: 441.15, measured (ES, m/z): 442.00 [M+H]$^+$.

Step 8: 5-(3-Chloro-2-fluoro-6-(1H-tetrazol-1-yl)phenyl)-2-(3-methoxy-1-(4-(1-methyl-1H-1,2,3-triazol-5-yl)-1H-pyrazol-1-yl)propyl)pyridine 4-Chloro-3-fluoro-2-(6-(3-methoxy-1-(4-(1-methyl-1H-1,2,3-triazol-5-yl)-1H-pyrazol-1-yl)propyl)pyridin-3-yl)aniline (360.0 mg, 0.815 mmol, 1.0 eq.) was dissolved in azidotrimethylsilane (4.0 mL), trimethoxymethane (4.0 mL) and AcOH (4.0 mL). The mixture was stirred at room temperature for 17.0 h. The solvent was removed under vacuum. The reaction mixture was purified by chromatography on C18 (80 g, MeCN/$H_2O$ (0.05% $CF_3COOH$): 0→60%) to yield 5-(3-chloro-2-fluoro-6-(1H-tetrazol-1-yl)phenyl)-2-(3-methoxy-1-(4-(1-methyl-1H-1,2,3-triazol-5-yl)-1H-pyrazol-1-yl)propyl)pyridine as a brown solid. LC/MS: mass calculated for $C_{22}H_{20}ClFN_{10}O$: 494.15, measured (ES, m/z): 495.20 [M+H]$^+$.

Step 9: (R)-5-(3-Chloro-2-fluoro-6-(1H-tetrazol-1-yl)phenyl)-2-(3-methoxy-1-(4-(1-methyl-1H-1,2,3-triazol-5-yl)-1H-pyrazol-1-yl)propyl)pyridine 1-oxide 5-(3-Chloro-2-fluoro-6-(1H-tetrazol-1-yl)phenyl)-2-(3-methoxy-1-(4-(1-methyl-1H-1,2,3-triazol-5-yl)-1H-pyrazol-1-yl)propyl)pyridine (200.0 mg, 0.40 mmol, 1.0 eq.) and methyltrioxorhenium (VII) (8.0 mg, 0.03 mmol, 0.08 eq.) were dissolved in MeOH (3.0 mL). Then $H_2O_2$ (1.0 mL, 30 wt %) was added into the mixture. The mixture was stirred at room temperature for 2.0 h. The reaction mixture was purified by chromatography on C18 (80 g, MeCN/$H_2O$ (0.05% $CF_3COOH$): 0→60%) and prep-chiral-HPLC. The collected fractions were combined and concentrated under vacuum to yield (R)-5-(3-chloro-2-fluoro-6-(1H-tetrazol-1-yl)phenyl)-2-(3-methoxy-1-(4-(1-methyl-1H-1,2,3-triazol-5-yl)-1H-pyrazol-1-yl)propyl)pyridine 1-oxide as an off-white solid.

HPLC purity (method A): 99.2%, retention time=1.400 min. LC/MS: mass calculated for $C_{22}H_{20}ClFN_{10}O_2$: 510.14, measured (ES, m/z): 511.20[M+H]$^+$. $^1$H NMR (300 MHz, DMSO-$d_6$) δ 9.62 (s, 1H), 8.44 (d, J=0.8 Hz, 1H), 8.38 (s, 1H), 7.93-8.04 (m, 2H), 7.88 (s, 1H), 7.70-7.80 (m, 1H), 7.34 (d, J=8.3 Hz, 1H), 7.12-7.22 (m, 1H), 6.17 (t, J=7.3 Hz, 1H), 4.06 (s, 3H), 3.25-3.34 (m, 1H), 3.11-3.15 (m, 4H), 2.48-2.54 (m, 2H). $^{19}$F NMR (376 MHz, DMSO-$d_6$) δ −112.71.

Example 541: (R)-2-(1-(4-(4-Carboxyphenyl)-1H-pyrazol-1-yl)-3-(difluoromethoxy)propyl)-5-(3-chloro-6-(difluoromethyl)-2-fluorophenyl)pyridine 1-oxide

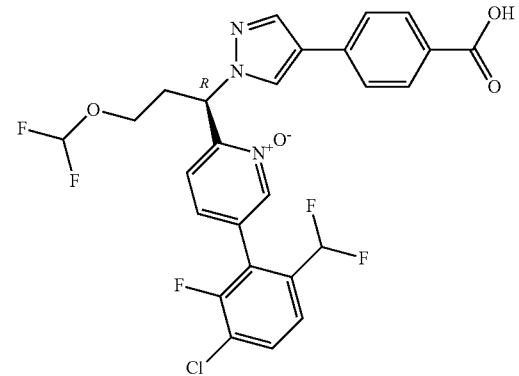

LC/MS: mass calculated for $C_{27}H_{19}ClF_5N_3O_4$:567.10, measured (ES, m/z): 568.05 [M+H]$^+$. $^1$H NMR (400 MHz, DMSO-$d_6$) δ 8.64 (s, 1H), 8.53 (s, 1H), 8.21 (s, 1H), 7.87-7.96 (m, 3H), 7.72-7.82 (m, 2H), 7.62 (d, J=8.5 Hz, 1H), 7.40 (s, 2H), 6.48-7.04 (m, 2H), 6.23-6.35 (m, 1H), 3.88-3.98 (m, 1H), 3.70-3.80 (m, 1H), 2.60-2.80 (m, 2H). $^{19}$F NMR (376 MHz, DMSO-$d_6$) δ −83.15, −109.93, −115.26.

Example 542: (S)-2-(1-(4-(4-Carboxyphenyl)-1H-pyrazol-1-yl)-3-(difluoromethoxy)propyl)-5-(3-chloro-6-(difluoromethyl)-2-fluorophenyl)pyridine 1-oxide

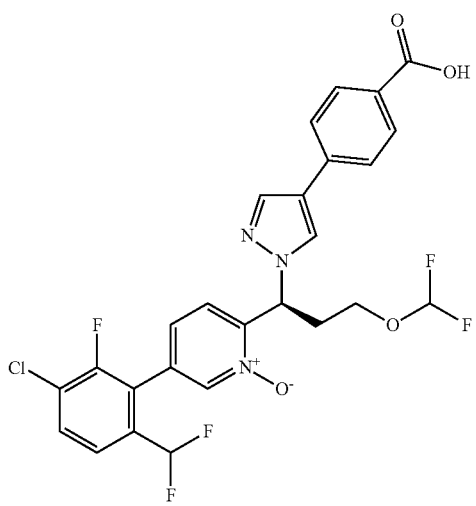 [SMILES: O=C(O)c1ccc(-c2cnn([C@@H](CCOC(F)F)c3ccc(-c4c(C(F)F)ccc(Cl)c4F)c[n+]3[O-])c2)cc1]

LC/MS: mass calculated for $C_{26}H_{19}ClF_5N_3O_4$:567.10, measured (ES, m/z): 568.05 [M+H]$^+$. $^1$H NMR (400 MHz, DMSO-d$_6$) δ 12.84 (brs, 1H), 8.64 (s, 1H), 8.53 (s, 1H), 8.21 (s, 1H), 7.87-7.96 (m, 3H), 7.76 (d, J=8.3 Hz, 2H), 7.62 (d, J=8.5 Hz, 1H), 7.40 (s, 2H), 6.48-7.04 (m, 2H), 6.23-6.35 (m, 1H), 3.88-3.98 (m, 1H), 3.70-3.80 (m, 1H), 2.60-2.80 (m, 2H). $^{19}$F NMR (376 MHz, DMSO-d$_6$) δ −83.15, −110.68, −115.26.

Example 543: 4-Chloro-5-(3-chloro-2-fluoro-6-(1H-tetrazol-1-yl)phenyl)-2-((S*)-2-cyclopropyl-1-(4-(3-methyl-3H-1,2,3-triazol-4-yl)-1H-pyrazol-1-yl)ethyl)pyridine 1-oxide

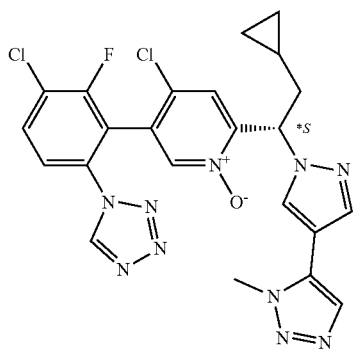

LC/MS: mass calculated for $C_{23}H_{19}Cl_2FN_{10}O$: 540.11, measured (ES, m/z): 541.10 [M+H]$^+$. $^1$H NMR (400 MHz, DMSO-d$_6$) δ 9.76 (s, 1H), 8.61 (s, 1H), 8.11 (t, J=8.2 Hz, 1H), 7.99 (s, 1H), 7.91 (d, J=7.8 Hz, 1H), 7.78-7.88 (m, 2H), 7.35 (d, J=7.9 Hz, 1H), 5.70-5.78 (m, 1H), 3.91 (s, 3H), 2.33-2.45 (m, 1H), 1.96-2.08 (m, 1H), 0.45-0.58 (m, 1H), 0.22-0.40 (m, 2H), −0.05-0.10 (m, 2 h). $^{19}$F NMR (376 MHz, DMSO-d$_6$) δ −111.96.

Example 544: 4-Chloro-5-(3-chloro-2-fluoro-6-(1H-tetrazol-1-yl)phenyl)-2-((R*)-2-cyclopropyl-1-(4-(3-methyl-3H-1,2,3-triazol-4-yl)-1H-pyrazol-1-yl)ethyl)pyridine 1-oxide

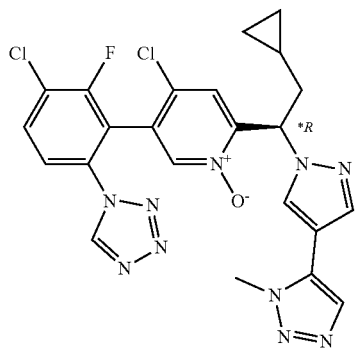

LC/MS: mass calculated for $C_{23}H_{19}Cl_2FN_{10}O$: 540.11, measured (ES, m/z): 541.15 [M+H]$^+$. $^1$H NMR (400 MHz, DMSO-d$_6$) δ 9.76 (s, 1H), 8.61 (s, 1H), 8.11 (t, J=8.3 Hz, 1H), 8.00 (d, J=5.0 Hz, 1H), 7.90 (dd, J=7.9, 3.6 Hz, 1H), 7.79-7.87 (m, 2H), 7.30-7.38 (m, 1H), 5.65-5.78 (m, 1H), 3.91 (s, 3H), 2.30-2.42 (m, 1H), 1.96-2.08 (m, 1H), 0.45-0.58 (m, 1H), 0.22-0.40 (m, 2H), −0.05-0.10 (m, 2 h). $^{19}$F NMR (376 MHz, DMSO-d$_6$) δ −112.00.

Example 545: (R*)-2-(2-(1H-Pyrazol-1-yl)-1-(4-(2-(trifluoromethyl)pyridin-4-yl)-1H-pyrazol-1-yl)ethyl)-5-(3-chloro-2-fluoro-6-(1H-tetrazol-1-yl)phenyl)pyridine 1-oxide

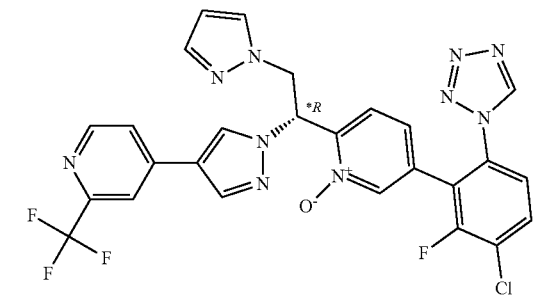 [SMILES: [O-][n+]1cc(-c2c(-n3cnnn3)ccc(Cl)c2F)ccc1[C@@H](Cn1cccn1)n1cc(-c2ccnc(C(F)(F)F)c2)cn1]

LC/MS: mass calculated for $C_{26}H_{17}ClF_4N_{10}O$: 596.12, measured (ES, m/z): 597.15 [M+H]$^+$. $^1$H NMR (400 MHz, DMSO-d$_6$) δ 9.69 (s, 1H), 8.73 (s, 1H), 8.66 (d, J=5.1 Hz, 1H), 8.52 (d, J=1.6 Hz, 1H), 8.37 (s, 1H), 8.03-8.12 (m, 2H), 7.87 (dd, J=5.2, 1.7 Hz, 1H), 7.77 (dd, J=8.7, 1.5 Hz, 1H), 7.45-7.53 (m, 2H), 7.42 (d, J=1.8 Hz, 1H), 7.22 (dd, J=8.3, 1.7 Hz, 1H), 6.52-6.60 (m, 1H), 6.10-6.15 (m, 1H), 4.93-5.15 (m, 2 h). $^{19}$F NMR (376 MHz, DMSO-d$_6$) δ −66.54, −112.65.

Example 546: (S*)-2-(2-(1H-Pyrazol-1-yl)-1-(4-(2-(trifluoromethyl)pyridin-4-yl)-1H-pyrazol-1-yl)ethyl)-5-(3-chloro-2-fluoro-6-(1H-tetrazol-1-yl)phenyl)pyridine 1-oxide

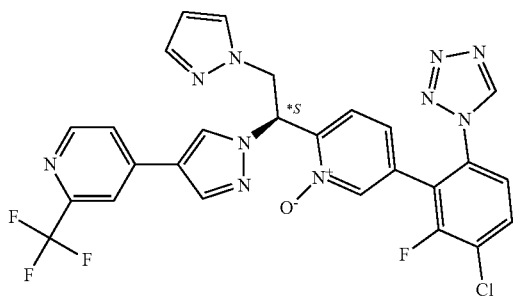 [SMILES: [O-][n+]1cc(-c2c(-n3cnnn3)ccc(Cl)c2F)ccc1[C@H](Cn1cccn1)n1cc(-c2ccnc(C(F)(F)F)c2)cn1]

LC/MS: mass calculated for $C_{26}H_{17}ClF_4N_{10}O$: 596.12, measured (ES, m/z): 597.15 [M+H]$^+$. $^1$H NMR (400 MHz, DMSO-d$_6$) δ 9.69 (s, 1H), 8.73 (s, 1H), 8.66 (d, J=5.1 Hz, 1H), 8.52 (d, J=1.7 Hz, 1H), 8.37 (s, 1H), 8.03-8.12 (m, 2H), 7.87 (dd, J=5.2, 1.6 Hz, 1H), 7.77 (dd, J=8.7, 1.6 Hz, 1H), 7.45-7.53 (m, 2H), 7.42 (d, J=1.9 Hz, 1H), 7.23 (dd, J=8.2, 1.7 Hz, 1H), 6.52-6.60 (m, 1H), 6.10-6.15 (m, 1H), 4.93-5.15 (m, 2H). $^{19}$F NMR (376 MHz, DMSO-d$_6$) δ −66.54, −112.60.

Example 547: (R*)-5-(3-Chloro-2-fluoro-6-(1H-tetrazol-1-yl)phenyl)-2-(2-(4-fluoro-1H-pyrazol-1-yl)-1-(4-(1-methyl-1H-imidazol-5-yl)-1H-pyrazol-1-yl)ethyl)pyridine 1-oxide

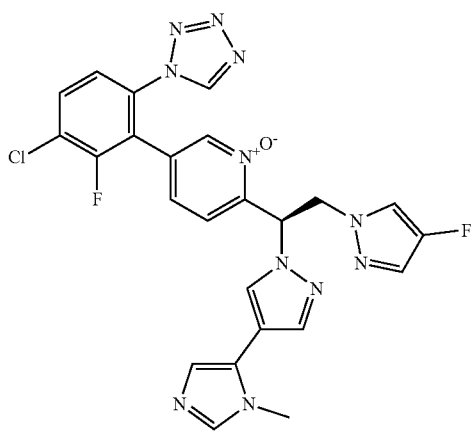

LC/MS: mass calculated for $C_{31}H_{20}ClF_4N_{11}O$: 673.15, measured (ES, m/z): 674.20 [M+H]$^+$. $^1$H NMR (300 MHz, DMSO-d$_6$) δ 8.48 (s, 1H), 7.78 (d, J=5.2 Hz, 1H), 7.60-7.70 (m, 2H), 7.44-7.55 (m, 2H), 7.40 (s, 1H), 7.05-7.18 (m, 2H), 6.93-7.01 (m, 1H), 6.71-6.90 (m, 4H), 6.56-6.67 (m, 1H), 6.47-6.56 (m, 2H), 5.47 (t, J=7.4 Hz, 1H), 4.49 (d, J=7.4 Hz, 2H). $^{19}$F NMR (282 MHz, DMSO-d$_6$) δ −70.32, −115.04.

Example 548: (S*)-5-(3-Chloro-2-fluoro-6-(1H-tetrazol-1-yl)phenyl)-2-(2-(4-fluoro-1H-pyrazol-1-yl)-1-(4-(1-methyl-1H-imidazol-5-yl)-1H-pyrazol-1-yl)ethyl)pyridine 1-oxide

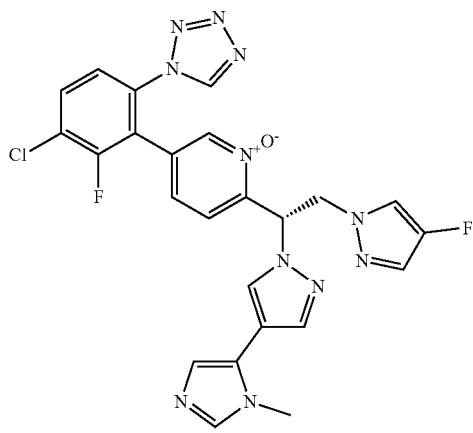

LC/MS: mass calculated for $C_{31}H_{20}ClF_4N_{11}O$: 673.15, measured (ES, m/z): 674.15 [M+H]$^+$. $^1$H NMR (300 MHz, DMSO-d$_6$) δ 8.48 (s, 1H), 7.78 (d, J=5.2 Hz, 1H), 7.60-7.70 (m, 2H), 7.37-7.58 (m, 3H), 7.03-7.22 (m, 2H), 6.97 (d, J=5.1 Hz, 1H), 6.69-6.92 (m, 4H), 6.56-6.67 (m, 1H), 6.47-6.56 (m, 2H), 5.47 (t, J=7.5 Hz, 1H), 4.49 (d, J=7.4 Hz, 2H). $^{19}$F NMR (282 MHz, DMSO-d$_6$) δ −70.32, −115.05.

Example 549: 5-(3-Chloro-2-fluoro-6-(1H-tetrazol-1-yl)phenyl)-2-(1-(4-(3-chloro-5-fluoropyridin-4-yl)-1H-pyrazol-1-yl)-2-cyclopropylethyl)pyridine 1-oxide

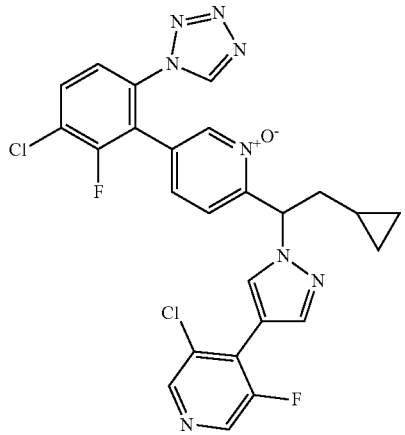

Step 1. 4-(1-(1-(5-Bromopyridin-2-yl)-2-cyclopropylethyl)-1H-pyrazol-4-yl)-3-chloro-5-fluoropyridine A mixture of 1-(5-bromopyridin-2-yl)-2-cyclopropylethyl methanesulfonate (350 mg, 1.1 mmol), 3-chloro-5-fluoro-4-(1H-pyrazol-4-yl)pyridine (216 mg, 1.1 mmol) and Cs$_2$CO$_3$ (427.4 mg, 1.3 mmol) in ACN (4 ml) was stirred at 80° C. for 16 h. The precipitate was filtered off and the filtrate was concentrated. The residue was purified by Gilson HPLC to yield a colorless film (138 mg, 30%).

Step 2. 4-Chloro-2-(6-(1-(4-(3-chloro-5-fluoropyridin-4-yl)-1H-pyrazol-1-yl)-2-cyclopropylethyl)pyridin-3-yl)-3-fluoroaniline To a mixture of 4-(1-(1-(5-bromopyridin-2-yl)-2-cyclopropylethyl)-1H-pyrazol-4-yl)-3-chloro-5-fluoropyridine (138 mg, 0.33 mmol), (6-amino-3-chloro-2-fluorophenyl) boronic acid, and Pd(PPh$_3$)$_4$ (19 mg, 0.02 mmol) in 1,4-dioxane (4 ml) was added aqueous K$_2$CO$_3$ (0.33 ml, 2 M) and the reaction mixture was heated at 130° C. for 65 mins. It was concentrated and the residue was purified by Gilson HPLC to yield a colorless film (86.3 mg, 54.2%).

Step 3. 3-Chloro-4-(1-(1-(5-(3-chloro-2-fluoro-6-(1H-tetrazol-1-yl)phenyl)pyridin-2-yl)-2-cyclopropylethyl)-1H-pyrazol-4-yl)-5-fluoropyridine To 4-chloro-2-(6-(1-(4-(3-chloro-5-fluoropyridin-4-yl)-1H-pyrazol-1-yl)-2-cyclopropylethyl)pyridin-3-yl)-3-fluoroaniline (86.3 mg, 0.18 mmol) in HOAc (3 ml) was added trimethoxymethane (188 mg, 1.77 mmol), followed by NaN$_3$ (115.4 mg, 1.77 mmol) and the resulting mixture was stirred at 80° C. for 2 h. The solvent was removed under reduced pressure and the residue was dissolved in MeOH and purified by Gilson HPLC to yield a white solid (78 mg, 81.5%).

Step 4. 5-(3-Chloro-2-fluoro-6-(1H-tetrazol-1-yl) phenyl)-2-(1-(4-(3-chloro-5-fluoropyridin-4-yl)-1H-pyrazol-1-yl)-2-cyclopropylethyl)pyridine 1-oxide To a solution of 3-chloro-4-(1-(1-(5-(3-chloro-2-fluoro-6-(1H-tetrazol-1-yl)phenyl)pyridin-2-yl)-2-cyclopropylethyl)-1H-pyrazol-4-yl)-5-fluoropyridine (45 mg, 0.08 mmol) in MeOH was added MeReO$_3$ (6.3 g, 0.03 mmol), followed by 30% H$_2$O$_2$ (189.2 mg, 1.7 mmol) and the reaction mixture was stirred at room temperature for 2 h. The resulting mixture was then subjected to Gilson HPLC purification to yield the 5-(3-chloro-2-fluoro-6-(1H-tetrazol-1-yl)phenyl)-2-(1-(4-(3-chloro-5-fluoropyridin-4-yl)-1H-pyrazol-1-yl)-2-cyclopropylethyl)pyridine 1-oxide as a white solid.

LC/MS: mass calculated for C$_{25}$H$_{18}$Cl$_2$F$_2$N$_8$O: 554.1, measured (ES, m/z): 555.2 [M+H]$^+$. $^1$H NMR (400 MHz, CD$_3$OD) δ ppm 0.02 (br d, J=4.40 Hz, 1H), 0.16-0.24 (m, 1H), 0.35-0.51 (m, 2H), 0.62-0.76 (m, 1H), 2.01-2.14 (m, 1H), 2.41-2.52 (m, 1H), 6.30 (br d, J=7.34 Hz, 1H), 7.30 (br d, J=8.31 Hz, 1H), 7.51-7.66 (m, 2H), 7.88-7.97 (m, 1H), 8.10-8.17 (m, 1H), 8.37 (s, 1H), 8.50 (br d, J=12.72 Hz, 2H), 8.58 (s, 1H), 9.35-9.43 (m, 1H).

Example 550: 3-Chloro-4-(1-(1-(5-(3-chloro-2-fluoro-6-(1H-tetrazol-1-yl)phenyl)-1-oxidopyridin-2-yl)-2-cyclopropylethyl)-1H-pyrazol-4-yl)-5-fluoropyridine 1-oxide

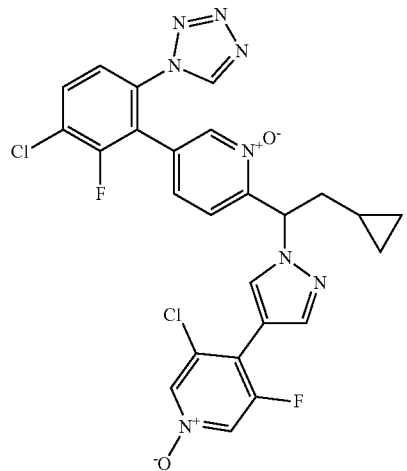

3-Chloro-4-(1-(1-(5-(3-Chloro-2-fluoro-6-(1H-tetrazol-1-yl)phenyl)-1-oxidopyridin-2-yl)-2-cyclopropylethyl)-1H-pyrazol-4-yl)-5-fluoropyridine 1-oxide was prepared as a white solid.

LC/MS: mass calculated for C$_{25}$H$_{18}$Cl$_2$F$_2$N$_8$O$_2$: 570.1, measured (ES, m/z): 571.1 [M+H]$^+$. $^1$H NMR (400 MHz, CD$_3$OD) δ ppm 9.35-9.43 (m, 1H), 8.58 (s, 1H), 8.50 (br d, J=12.72 Hz, 2H), 8.37 (s, 1H), 8.10-8.17 (m, 1H), 7.88-7.97 (m, 1H), 7.51-7.66 (m, 2H), 7.30 (br d, J=8.31 Hz, 1H), 6.30 (br d, J=7.34 Hz, 1H), 2.41-2.52 (m, 1H), 2.01-2.14 (m, 1H), 2.01-2.14 (m, 1H), 0.62-0.76 (m, 1H), 0.35-0.51 (m, 2H), 0.16-0.24 (m, 1H), 0.02 (br d, J=4.40 Hz, 1H).

Example 551: (S)-2-(1-(4-(4H-1,2,4-Triazol-4-yl)-1H-pyrazol-1-yl)-3-methoxypropyl)-5-(3-chloro-2-fluoro-6-(1H-tetrazol-1-yl)phenyl)pyridine 1-oxide

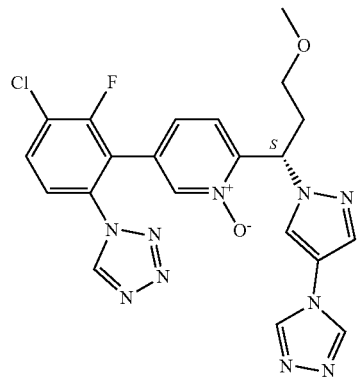

LC/MS: mass calculated for C$_{21}$H$_{18}$ClFN$_{10}$O$_2$: 496.13, measured (ES, m/z): 497.05 [M+H]$^+$. $^1$H NMR (400 MHz, DMSO-d$_6$) δ 9.70 (s, 1H), 8.99 (s, 1H), 8.55 (s, 1H), 8.44 (d, J=1.6 Hz, 1H), 8.17 (s, 1H), 8.02-8.11 (m, 2H), 7.76 (dd, J=8.7, 1.6 Hz, 1H), 7.34 (d, J=8.3 Hz, 1H), 7.18 (dd, J=8.3, 1.7 Hz, 1H), 6.12-6.20 (m, 1H), 3.28-3.35 (m, 1H), 3.14-3.27 (m, 4H), 2.43-2.52 (m, 2H). $^{19}$F NMR (376 MHz, DMSO-$d_6$) δ −112.69.

Example 552: (R)-2-(1-(4-(4H-1,2,4-Triazol-4-yl)-1H-pyrazol-1-yl)-3-methoxypropyl)-5-(3-chloro-2-fluoro-6-(1H-tetrazol-1-yl)phenyl)pyridine 1-oxide

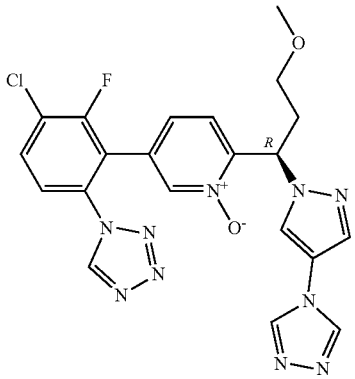

Step 1: 4-(1-(Tetrahydro-2H-pyran-2-yl)-1H-pyrazol-4-yl)-4H-1,2,4-triazole

A mixture of 4-iodo-1-(tetrahydro-2H-pyran-2-yl)-1H-pyrazole (3.0 g, 10.79 mmol, 1.0 equiv.), 4H-1,2,4-triazole (1.1 g, 16.18 mmol, 1.5 equiv.), cupric acetate (0.2 g, 1.08 mmol, 0.1 equiv.) and cesium carbonate (7 g, 21.57 mmol, 2.0 equiv.) in N,N-dimethylformamide (30 mL) was refluxed at 120° C. under nitrogen for 24 h. The mixture was diluted with water, extracted with ethyl acetate twice and washed with water twice. The combined organic layers was washed with brine, dried over $Na_2SO_4$, concentrated and purified by silica gel chromatography (0→8%, DCM/MeOH) to yield 4-(1-(tetrahydro-2H-pyran-2-yl)-1H-pyrazol-4-yl)-4H-1,2,4-triazole as a light yellow oil. LC/MS: mass calculated for $C_{10}H_{13}N_5O$: 219.11, measured (ES, m/z): 220.20 [M+H]$^+$ Step 2: 4-(1H-pyrazol-4-yl)-4H-1,2,4-triazole A mixture of 4-(1-(tetrahydro-2H-pyran-2-yl)-1H-pyrazol-4-yl)-4H-1,2,4-triazole (1.75 g, 7.9 mmol, 1.0 equiv.) and HCl (17.5 mL, 4.0 M in 1,4-dioxane) was stirred for 0.5 h at room temperature. The mixture was diluted with water, then adjusted to pH 7-8 with sodium bicarbonate. The solid was filtered out. The filtrate was concentrated under vacuum to yield 4-(1H-pyrazol-4-yl)-4H-1,2,4-triazole as a light yellow solid. LC/MS: mass calculated for $C_5H_5N_5$: 135.05, measured (ES, m/z): 136.05 [M+H]$^+$.

Step 3: 2-(1-(4-(4H-1,2,4-Triazol-4-yl)-1H-pyrazol-1-yl)-3-methoxypropyl)-5-bromopyridine A mixture of cesium carbonate (660 mg, 2.04 mmol, 1.1 equiv.) and 4-(1H-pyrazol-4-yl)-4H-1,2,4-triazole (330 mg, 2.41 mmol, 1.3 equiv.) in acetonitrile (10 mL) was stirred for 15 min at room temperature. 1-(5-bromopyridin-2-yl)-3-methoxypropyl methanesulfonate (600 mg, 1.85 mmol, 1.0 equiv.) was added and the solution was stirred for 3 h at 90° C. The solution was diluted with $H_2O$ and extracted with ethyl acetate twice. The combined organic layers were washed with brine, dried over $Na_2SO_4$, concentrated and purified by silica gel chromatography (0→8%, MeOH/DCM) to yield 2-(1-(4-(4H-1,2,4-triazol-4-yl)-1H-pyrazol-1-yl)-3-methoxypropyl)-5-bromopyridine as a light yellow oil. LC/MS: mass calculated for $C_{14}H_{15}BrN_6O$: 362.05, measured (ES, m/z): 363.15 [M+H]$^+$.

Step 4: 2-(6-(1-(4-(4H-1,2,4-Triazol-4-yl)-1H-pyrazol-1-yl)-3-methoxypropyl)pyridin-3-yl)-4-chloro-3-fluoroaniline A mixture of 2-(1-(4-(4H-1,2,4-triazol-4-yl)-1H-pyrazol-1-yl)-3-methoxypropyl)-5-bromopyridine (520 mg, 1.42 mmol, 1.0 equiv.), (6-amino-3-chloro-2-fluorophenyl)boronic acid (540 mg, 2.84 mmol, 2.0 equiv.), Pd(PPh$_3$)$_4$ (330 mg, 0.28 mmol, 0.2 equiv.), potassium carbonate (1.2 g, 8.51 mmol, 6.0 equiv.) in 1,4-dioxane (6 mL) and water (1.5 mL) was refluxed at 90° C. under $N_2$ for 2 h. The mixture was diluted with water, and the mixture extracted with ethyl acetate twice. The combined organic layers was washed with brine, dried over $Na_2SO_4$, concentrated and purified by silica gel chromatography (0→10%, MeOH/DCM) to yield 2-(6-(1-(4-(4H-1,2,4-triazol-4-yl)-1H-pyrazol-1-yl)-3-methoxypropyl)pyridin-3-yl)-4-chloro-3-fluoroaniline as a light yellow oil. LC/MS: mass calculated for $C_{20}H_{19}ClFN_7O$: 427.13, measured (ES, m/z): 428.15 [M+H]$^+$.

Step 5: 2-(1-(4-(4H-1,2,4-Triazol-4-yl)-1H-pyrazol-1-yl)-3-methoxypropyl)-5-(3-chloro-2-fluoro-6-(1H-tetrazol-1-yl)phenyl)pyridine A mixture of 2-(6-(1-(4-(4H-1,2,4-triazol-4-yl)-1H-pyrazol-1-yl)-3-methoxypropyl)pyridin-3-yl)-4-chloro-3-fluoroaniline (560 mg, 1.31 mmol, 1.0 equiv.), trimethoxymethane (3 mL), azidotrimethylsilane (3 mL) and acetic acid (3 mL) was stirred overnight at room temperature. The reaction was purified by reverse phase chromatography on C18 (80 g, MeCN/H$_2$O (0.05% CF$_3$COOH): 0→45%) to yield 2-(1-(4-(4H-1,2,4-triazol-4-yl)-1H-pyrazol-1-yl)-3-methoxypropyl)-5-(3-chloro-2-fluoro-6-(1H-tetrazol-1-yl)phenyl)pyridine as a white solid.

LC/MS: mass calculated for $C_{21}H_{18}ClFN_{10}O$: 480.13, measured (ES, m/z): 481.25 [M+H]$^+$.

Step 6: (R)-2-(1-(4-(4H-1,2,4-Triazol-4-yl)-1H-pyrazol-1-yl)-3-methoxypropyl)-5-(3-chloro-2-fluoro-6-(1H-tetrazol-1-yl)phenyl)pyridine 1-oxide A mixture of 2-(1-(4-(4H-1,2,4-triazol-4-yl)-1H-pyrazol-1-yl)-3-methoxypropyl)-5-(3-chloro-2-fluoro-6-(1H-tetrazol-1-yl)phenyl)pyridine (350 mg, 0.73 mmol, 1.0 equiv.), hydrogen peroxide (0.74 mL, 7.28 mmol, 10.0 equiv.) and methyltrioxorhenium (36 mg, 0.15 mmol, 0.2 equiv.) in CH$_3$OH (4 mL) was stirred for 3 h at room temperature. The mixture was purified by reverse phase chromatography on C18 (80 g, MeCN/H$_2$O (0.05% CF$_3$COOH): 0→45%) to yield 2-(1-(4-(4H-1,2,4-triazol-4-yl)-1H-pyrazol-1-yl)-3-methoxypropyl)-5-(3-chloro-2-fluoro-6-(1H-tetrazol-1-yl)phenyl)pyridine 1-oxide The racemic product was separated by chiral-HPLC to yield (R)-2-(1-(4-(4H-1,2,4-triazol-4-yl)-1H-pyrazol-1-yl)-3-methoxypropyl)-5-(3-chloro-2-fluoro-6-(1H-tetrazol-1-yl)phenyl)pyridine 1-oxide as a light yellow solid.

LC/MS: mass calculated for $C_{21}H_{18}ClFN_{10}O_2$: 496.13, measured (ES, m/z): 497.05 [M+H]$^+$. $^1$H NMR (400 MHz, DMSO-$d_6$): δ 9.58 (s, 1H), 8.91 (s, 1H), 8.43 (d, J=0.7 Hz, 1H), 8.34 (d, J=1.6 Hz, 1H), 8.14 (s, 1H), 7.91-8.01 (m, 2H), 7.67-7.79 (m, 1H), 7.41 (d, J=8.3 Hz, 1H), 7.22-7.30 (m, 1H), 6.14 (t, J=7.4 Hz, 1H), 3.30-3.42 (m, 1H), 3.11-3.22 (m, 1H), 3.16 (s, 3H), 2.41-2.50 (m, 2H). $^{19}$F NMR (376 MHz, DMSO-d$_6$): δ −73.80, −112.80.

Example 553: 5-(3-Chloro-2-fluoro-6-(1H-tetrazol-1-yl)phenyl)-2-(1-(4-cyano-2-methyl-1'H,2H-[3,4'-bipyrazol]-1'-yl)-2-cyclopropylethyl)pyridine 1-oxide

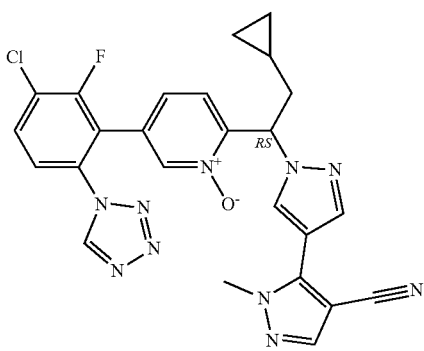 [SMILES: Cn1ncc(C#N)c1-c1cnn(C(CC2CC2)c2ccc(-c3c(-n4cnnn4)ccc(Cl)c3F)c[n+]2[O-])c1]

LC/MS: mass calculated for C$_{25}$H$_{20}$ClFN$_{10}$O: 530.1; measured (ES, m/z): 531.2 [M+H]$^+$. $^1$H NMR (400 MHz, CD$_3$OD) δ ppm −0.05-0.04 (m, 1H) 0.14-0.23 (m, 1H) 0.35-0.51 (m, 2 h) 0.63-0.75 (m, 1H) 2.04-2.13 (m, 1H) 2.39-2.50 (m, 1H) 3.95-4.00 (m, 3H) 6.26-6.39 (m, 1H) 7.25-7.33 (m, 1H) 7.58-7.66 (m, 2 h) 7.86-7.87 (m, 1H) 7.88-7.96 (m, 1H) 8.04 (br s, 1H) 8.28-8.61 (m, 2 h) 9.39 (s, 1H).

Example 554: (R*)-5-(3-Chloro-2-fluoro-6-(1H-tetrazol-1-yl)phenyl)-2-(2-(3-(5-fluoropyridin-2-yl)-1H-pyrazol-1-yl)-1-(4-(2-(trifluoromethyl)pyridin-4-yl)-1H-pyrazol-1-yl)ethyl)pyridine 1-oxide

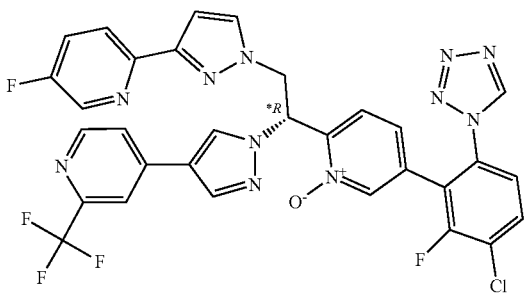 [SMILES: [O-][n+]1cc(-c2c(-n3cnnn3)ccc(Cl)c2F)ccc1[C@@H](Cn1ccc(-c2ccc(F)cn2)n1)n1cc(-c2ccnc(C(F)(F)F)c2)cn1]

LC/MS: mass calculated for C$_{31}$H$_{19}$ClF$_5$N$_{11}$O: 691.14, measured (ES, m/z): 692.10 [M+H]$^+$. $^1$H NMR (400 MHz, DMSO-d$_6$) δ 9.63 (s, 1H), 8.80 (s, 1H), 8.66 (d, J=5.2 Hz, 1H), 8.56 (dd, J=5.0, 2.4 Hz, 1H), 8.49 (d, J=2.2 Hz, 1H), 8.33 (s, 1H), 8.01-8.12 (m, 3H), 7.85 (d, J=5.1 Hz, 1H), 7.77 (d, J=8.7 Hz, 1H), 7.72 (dd, J=8.1, 2.3 Hz, 1H), 7.63 (d, J=2.4 Hz, 1H), 7.31-7.42 (m, 1H), 7.20-7.30 (m, 2H), 6.18-6.30 (m, 1H), 5.12-5.31 (m, 2 h). $^{19}$F NMR (376 MHz, DMSO-d$_6$) δ −66.57, −113.38, −124.96.

Example 555: (S*)-5-(3-Chloro-2-fluoro-6-(1H-tetrazol-1-yl)phenyl)-2-(2-(3-(5-fluoropyridin-2-yl)-1H-pyrazol-1-yl)-1-(4-(2-(trifluoromethyl)pyridin-4-yl)-1H-pyrazol-1-yl)ethyl)pyridine 1-oxide

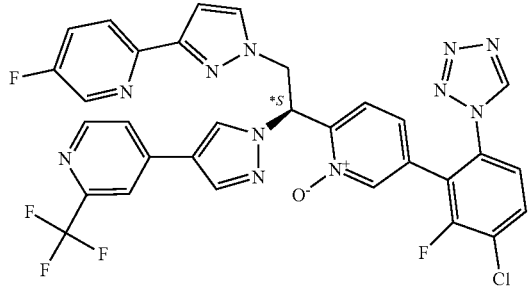 [SMILES: [O-][n+]1cc(-c2c(-n3cnnn3)ccc(Cl)c2F)ccc1[C@H](Cn1ccc(-c2ccc(F)cn2)n1)n1cc(-c2ccnc(C(F)(F)F)c2)cn1]

LC/MS: mass calculated for C$_{31}$H$_{19}$ClF$_5$N$_{11}$O: 691.14, measured (ES, m/z): 692.10 [M+H]$^+$. $^1$H NMR (400 MHz, DMSO-d$_6$) δ 9.63 (s, 1H), 8.80 (s, 1H), 8.66 (d, J=5.2 Hz, 1H), 8.56 (dd, J=4.9, 2.4 Hz, 1H), 8.49 (d, J=2.2 Hz, 1H), 8.33 (s, 1H), 8.01-8.12 (m, 3H), 7.85 (dd, J=5.1, 1.7 Hz, 1H), 7.77 (dd, J=8.7, 1.5 Hz, 1H), 7.72 (dd, J=8.2, 2.3 Hz, 1H), 7.63 (d, J=2.4 Hz, 1H), 7.31-7.42 (m, 1H), 7.21-7.30 (m, 2H), 6.18-6.30 (m, 1H), 5.12-5.31 (m, 2 h). $^{19}$F NMR (376 MHz, DMSO-d$_6$) δ −66.57, −113.38, −124.96.

Example 556: 2-((1R*)-1-(4-(4-Carbamoylphenyl)-1H-pyrazol-1-yl)-2-((2S*)-2-(piperidine-1-carbonyl)cyclopropyl)ethyl)-5-(3-chloro-6-(difluoromethyl)-2-fluorophenyl)pyridine 1-oxide

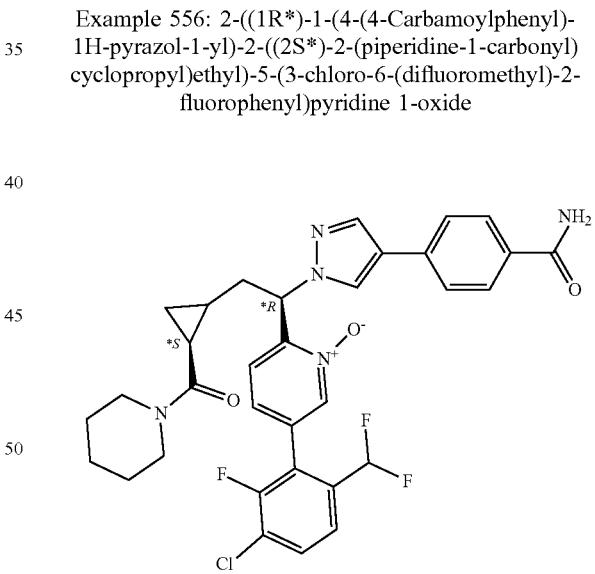

LC/MS: mass calculated for C$_{33}$H$_{31}$ClF$_3$N$_5$O$_3$: 637.2, measured (ES, m/z): 638.30 [M+H]$^+$. $^1$H NMR (400 MHz, CD$_3$OD) δ 8.39-8.48 (m, 2H), 8.11 (s, 1H), 7.87-7.96 (m, 2H), 7.74-7.81 (m, 1H), 7.66-7.74 (m, 3H), 7.60 (d, J=8.5 Hz, 1H), 7.50-7.56 (m, 1H), 6.67 (t, J=54.1 Hz, 1H), 6.27-6.35 (m, 1H), 3.40-3.52 (m, 2H), 3.32-3.36 (m, 1H), 3.05-3.19 (m, 1H), 2.46-2.58 (m, 1H), 2.32-2.45 (m, 1H), 1.20-1.65 (m, 7H), 0.95-1.05 (m, 1H), 0.78-0.86 (m, 1H). $^{19}$F NMR (376 MHz, CD$_3$OD) δ −110.64, −116.71.

Example 557: 2-((1S*)-1-(4-(4-Carbamoylphenyl)-1H-pyrazol-1-yl)-2-((2R*)-2-(piperidine-1-carbonyl)cyclopropyl)ethyl)-5-(3-chloro-6-(difluoromethyl)-2-fluorophenyl)pyridine 1-oxide

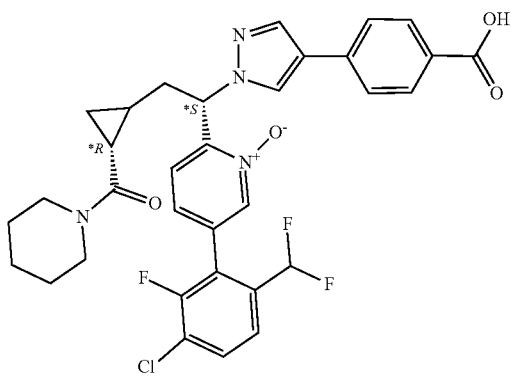 [SMILES: O=C(O)c1ccc(-c2cnn([C@@H](CC3C[C@H]3C(=O)N3CCCCC3)c3ccc(-c4c(C(F)F)ccc(Cl)c4F)c[n+]3[O-])c2)cc1]

LC/MS: mass calculated for $C_{33}H_{30}ClF_3N_4O_4$: 638.2, measured (ES, m/z): 639.15 [M+H]$^+$. $^1$H NMR (400 MHz, DMSO-$d_6$) δ 8.47 (s, 1H), 8.41 (s, 1H), 8.09 (s, 1H), 7.80-7.90 (m, 3H), 7.65 (d, J=8.0 Hz, 2H), 7.58 (d, J=8.5 Hz, 1H), 7.44 (s, 1H), 6.82 (t, J=67.0 Hz, 1H), 6.10-6.20 (m, 1H), 3.60-3.70 (m, 2H), 3.32-3.40 (m, 2H), 2.10-2.20 (m, 1H), 1.90-2.00 (m, 1H), 1.50-1.59 (m, 5H), 1.30-1.38 (s, 3H), 0.80-0.90 (m, 1H), 1.00-1.09 (m, 1H), 0.50-0.59 (m, 1H). $^{19}$F NMR (376 MHz, DMSO-$d_6$) δ −115.43.

Example 558: 2-((1R)-1-(4-(4-Carboxyphenyl)-1H-pyrazol-1-yl)-2-((2S)-2-(piperidine-1-carbonyl)cyclopropyl)ethyl)-5-(3-chloro-6-(difluoromethyl)-2-fluorophenyl)pyridine 1-oxide

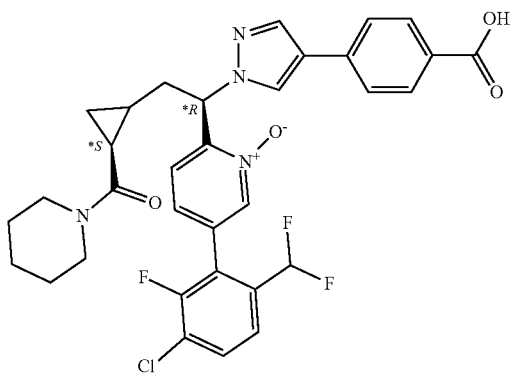 [SMILES: O=C(O)c1ccc(-c2cnn([C@H](CC3C[C@@H]3C(=O)N3CCCCC3)c3ccc(-c4c(C(F)F)ccc(Cl)c4F)c[n+]3[O-])c2)cc1]

LC/MS: mass calculated for $C_{33}H_{30}ClF_3N_4O_4$: 638.2, measured (ES, m/z): 639.15 [M+H]$^+$. $^1$H NMR (400 MHz, DMSO-$d_6$) δ 8.54 (s, 1H), 8.44 (s, 1H), 8.16 (s, 1H), 7.90-8.00 (m, 2H), 7.87 (t, J=7.9 Hz, 1H), 7.70-7.78 (m, 2H), 7.57-7.67 (m, 2H), 7.46-7.53 (m, 1H), 6.82 (t, J=54.0 Hz, 1H), 6.19 (t, J=7.2 Hz, 1H), 3.33-3.45 (m, 1H), 3.21-3.33 (m, 2H), 3.00-3.15 (m, 1H), 2.30-2.38 (m, 2H), 1.45-1.60 (m, 2H), 1.05-1.40 (m, 5H), 0.80-0.90 (m, 1H), 0.70-0.80 (m, 1H). $^{19}$F NMR (376 MHz, DMSO-$d_6$) δ −115.29.

Example 559: 2-((1S)-1-(4-(4-Carbamoylphenyl)-1H-pyrazol-1-yl)-2-(2-(piperidine-1-carbonyl)cyclopropyl)ethyl)-5-(3-chloro-6-(difluoromethyl)-2-fluorophenyl)pyridine 1-oxide

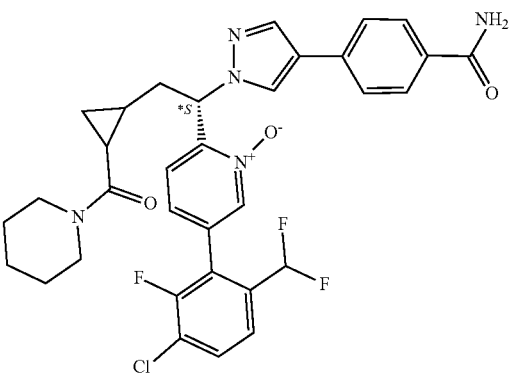 [SMILES: NC(=O)c1ccc(-c2cnn([C@@H](CC3CC3C(=O)N3CCCCC3)c3ccc(-c4c(C(F)F)ccc(Cl)c4F)c[n+]3[O-])c2)cc1]

LC/MS: mass calculated for $C_{33}H_{31}ClF_3N_5O_3$: 637.2, measured (ES, m/z): 638.30 [M+H]$^+$. $^1$H NMR (400 MHz, CD$_3$OD) δ 8.40-8.49 (m, 2H), 8.05-8.15 (m, 1H), 7.86-7.93 (m, 2H), 7.79 (t, J=7.8 Hz, 1H), 7.65-7.73 (m, 3H), 7.60 (d, J=8.5 Hz, 1H), 7.48-7.56 (m, 1H), 6.67 (t, J=54.1 Hz, 1H), 6.21-6.35 (m, 1H), 3.75-3.85 (m, 1H), 3.40-3.60 (m, 2H), 3.05-3.18 (m, 1H), 2.45-2.80 (m, 1H), 2.15-2.45 (m, 1H), 1.65-1.80 (m, 1H), 1.20-1.63 (m, 6H), 0.94-1.10 (m, 1H), 0.70-0.88 (m, 1H). $^{19}$F NMR (376 MHz, CD$_3$OD) δ −110.69, −116.71.

Example 560: 5-(3-Chloro-2-fluoro-6-(1H-tetrazol-1-yl)phenyl)-2-(2-cyclopropyl-1-(4-(1-cyclopropyl-1H-1,2,3-triazol-5-yl)-1H-pyrazol-1-yl)ethyl)pyridine 1-oxide

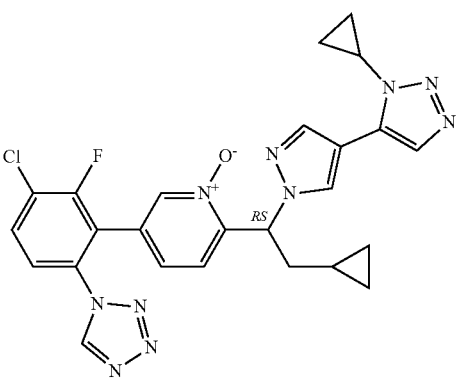 [SMILES: [O-][n+]1cc(-c2c(-n3cnnn3)ccc(Cl)c2F)ccc1C(CC1CC1)n1cc(-c2cnnn2C2CC2)cn1]

LC/MS: mass calculated for $C_{25}H_{22}ClFN_{10}O$: 532.2, measured (ES, m/z): 533.1 [M+H]$^+$. $^1$H NMR (400 MHz, CD$_3$OD) δ 9.39 (s, 1H), 8.49 (s, 1H), 8.38 (s, 1H), 8.06 (s, 1H), 7.85-7.97 (m, 2H), 7.61 (dd, J=1.96, 8.80 Hz, 1H), 7.55 (d, J=8.31 Hz, 1H), 7.30 (d, J=8.31 Hz, 1H), 6.28 (dd, J=4.16, 10.03 Hz, 1H), 3.78-3.88 (m, 1H), 2.39-2.58 (m, 1H), 2.04 (ddd, J=4.16, 7.83, 13.94 Hz, 1H), 1.25-1.34 (m, 4H), 0.63-0.80 (m, 1H), 0.34-0.51 (m, 2H), 0.13-0.24 (m, 1H), −0.03-0.08 (m, 1H).

Example 561: 2-(1-(4-(1,2,4-Thiadiazol-5-yl)-1H-pyrazol-1-yl)-2-cyclopropylethyl)-5-(3-chloro-2-fluoro-6-(1H-tetrazol-1-yl)phenyl)pyridine 1-oxide

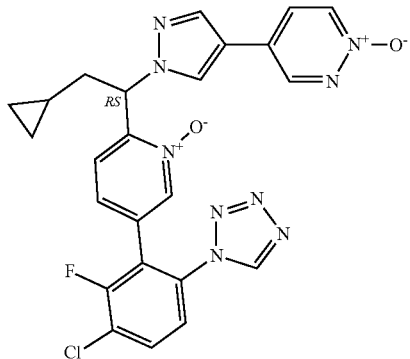 [SMILES: [O-][n+]1ccc(-c2cnn(C(CC3CC3)c3ccc(-c4c(-n5cnnn5)ccc(Cl)c4F)c[n+]3[O-])c2)cn1]

LC/MS: mass calculated for $C_{22}H_{17}ClFN_9OS$: 509.1, measured (ES, m/z): 510.1 $[M+H]^+$. $^1H$ NMR (400 MHz, CD$_3$OD) δ 9.38 (s, 1H), 8.62-8.73 (m, 1H), 7.84-8.60 (m, 4H), 7.51-7.70 (m, 2H), 7.26-7.34 (m, 1H), 6.18-6.37 (m, 1H), 2.33-2.56 (m, 1H), 1.98-2.15 (m, 1H), 0.54-0.81 (m, 1H), 0.44 (br d, J=4.40 Hz, 2H), 0.14-0.25 (m, 1H), −0.10-0.07 (m, 1H).

Example 562: 5-(3-Chloro-2-fluoro-6-(1H-tetrazol-1-yl)phenyl)-2-(2-cyclopropyl-1-(4-(1-methyl-1H-1,2,4-triazol-5-yl)-1H-pyrazol-1-yl)ethyl)pyridine 1-oxide

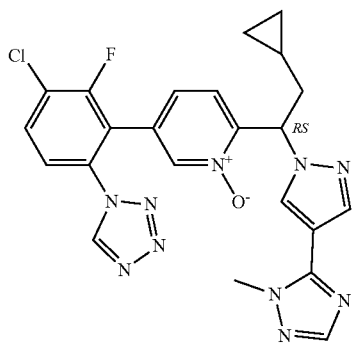

LC/MS: mass calculated for $C_{23}H_{20}ClFN_{10}O$: 506.2, measured (ES, m/z): 507.2 $[M+H]^+$. $^1H$ NMR (400 MHz, CD$_3$OD) δ 9.40 (s, 1H), 8.64-8.74 (m, 1H), 8.37-8.44 (m, 1H), 8.28-8.35 (m, 1H), 8.14 (s, 1H), 7.88-7.99 (m, 1H), 7.64 (br d, J=8.31 Hz, 2H), 7.22-7.40 (m, 1H), 6.24-6.37 (m, 1H), 4.10 (s, 3H), 2.41-2.60 (m, 1H), 2.04-2.20 (m, 1H), 0.63-0.77 (m, 1H), 0.34-0.50 (m, 2H), 0.16-0.24 (m, 1H), 0.00 (s, 1H).

Example 563: (R*)-2-(1-(4-(1H-Imidazol-1-yl)-1H-pyrazol-1-yl)-3-methoxypropyl)-5-(3-chloro-2-fluoro-6-(1H-tetrazol-1-yl)phenyl)pyridine 1-oxide

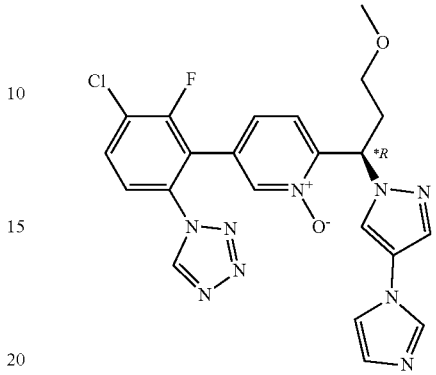

Step 1: 4-(1H-Imidazol-1-yl)-1-(tetrahydro-2H-pyran-2-yl)-1H-pyrazole

To a solution of 4-iodo-1-(tetrahydro-2H-pyran-2-yl)-1H-pyrazole (3.0 g, 10.71 mmol, 1.0 equiv.) in N,N-dimethylformamide (20 mL) was added 1H-imidazole (1.1 g, 16.07 mmol, 1.5 equiv.), cupric acetate (194 mg, 1.07 mmol, 1.0 equiv.) and cesium carbonate (7 mg, 21.42 mmol, 2.0 equiv.). The mixture was refluxed at 110° C. overnight. The resulting mixture was quenched with water (100 mL). The resulting mixture was then extracted with EA (3×100 mL). The organic layers were combined, washed with water (3×100 mL), dried over Na$_2$SO$_4$ and concentrated. The resulting residue was purified by silica gel chromatography (0%→10% MeOH/DCM) to yield 4-(1H-imidazol-1-yl)-1-(tetrahydro-2H-pyran-2-yl)-1H-pyrazole as a yellow oil. LC/MS: mass calculated for $C_{11}H_{14}N_4O$: 218.12, measured (ES, m/z): 219.05 $[M+H]^+$.

Step 2: 4-(1H-Imidazol-1-yl)-1H-pyrazole 4-(1H-imidazol-1-yl)-1-(tetrahydro-2H-pyran-2-yl)-1H-pyrazole (1.8 g, 8.25 mmol, 1.0 equiv.) was added in the solvent hydrogen chloride (1,4-dioxane), The resulting mixture was then stirred at room temperature for 3 h. The mixture was concentrated, diluted with water, then adjusted to pH 8-9 with sodium bicarbonate and concentrated. The resulting solid was diluted with DCM/MeOH (V/V=10:1), filtered out to yield 4-(1H-imidazol-1-yl)-1H-pyrazole as a white solid. LC/MS: mass calculated for $C_6H_6N_4$:134.06, measured (ES, m/z): 135.00 $[M+H]^+$.

Step 3: 2-(1-(4-(1H-Imidazol-1-yl)-1H-pyrazol-1-yl)-3-methoxypropyl)-5-bromopyridine To a solution of 4-(1H-imidazol-1-yl)-1H-pyrazole (252 mg, 1.88 mmol, 1.2 equiv.) in acetonitrile (5 mL) was added cesium carbonate (473 mg, 1.44 mmol, 1.0 equiv.), The resulting mixture was then stirred at room temperature for 20 min and 1-(5-bromopyridin-2-yl)-3-methoxypropyl methanesulfonate (468 mg, 1.44 mmol, 1.0 equiv.) was added. Then the mixture was refluxed for 1 h. The resulting mixture was extracted with EA (3×20 mL). The organic layers were combined, dried over Na$_2$SO$_4$ and concentrated.

Then the residue was purified by silica gel chromatography (0%→10%, DCM/MeOH) to yield 2-(1-(4-(1H-imidazol-1-yl)-1H-pyrazol-1-yl)-3-methoxypropyl)-5-bromopyridine as a yellow oil. LC/MS: mass calculated for $C_{15}H_{16}BrN_5O$: 361.05, measured (ES, m/z): 363.95 [M+H+2]$^+$.

Step 4: 2-(6-(1-(4-(1H-Imidazol-1-yl)-1H-pyrazol-1-yl)-3-methoxypropyl)pyridine-3-yl)-4-chloro-3-fluoroaniline A mixture of 2-(1-(4-(1H-imidazol-1-yl)-1H-pyrazol-1-yl)-3-methoxypropyl)-5-bromopyridine (300 mg, 0.83 mmol, 1.0 equiv.), 6-amino-3-chloro-2-fluorophenylboronic acid (392 mg, 2.07 mmol, 2.5 equiv.), Pd(pph$_3$)$_4$ (48 mg, 0.04 mmol, 0.05 equiv.), potassium carbonate (401 mg, 2.90 mmol, 3.5 equiv.) in 1,4-dioxane/water (V/V=5:1, 6 mL) was refluxed at 90° C. under $N_2$ for 2 h. The reaction was quenched by water (10 mL), then extracted with EA (3×20 mL). The organic layers were combined, washed with brine, dried over $Na_2SO_4$ and concentrated. The residue was purified by silica gel chromatography (0%→10%, DCM/MeOH) to yield 2-(6-(1-(4-(1H-imidazol-1-yl)-1H-pyrazol-1-yl)-3-methoxypropyl)pyridin-3-yl)-4-chloro-3-fluoroaniline as a yellow oil. LC/MS: mass calculated for $C_{21}H_{20}ClFN_6O$: 426.14, measured (ES, m/z): 427.10 [M+H]$^+$.

Step 5: 2-(1-(4-(1H-Imidazol-1-yl)-1H-pyrazol-1-yl)-3-methoxypropyl)-5-(3-chloro-2-fluoro-6-(1H-tetrazol-1-yl)phenyl)pyridine A mixture of 2-(6-(1-(4-(1H-imidazol-1-yl)-1H-pyrazol-1-yl)-3-methoxypropyl)pyridin-3-yl)-4-chloro-3-fluoroaniline (292 mg, 1.71 mmol, 1 equiv.), trimethoxymethane (1 mL), TMSN$_3$ (1 mL) and acetic acid (3 mL) was stirred overnight at room temperature. The reaction was purified by reverse phase chromatography on C18 (0%→55% MeCN/H$_2$O (0.05% CF$_3$COOH)) to yield 2-(1-(4-(1H-imidazol-1-yl)-1H-pyrazol-1-yl)-3-methoxypropyl)-5-(3-chloro-2-fluoro-6-(1H-tetrazol-1-yl)phenyl)pyridine as a light yellow solid. LC/MS: mass calculated for $C_{22}H_{19}ClFN_9O$: 479.14, measured (ES, m/z): 480.25[M+H]$^+$.

Step 6: (R*)-2-(1-(4-(1H-Imidazol-1-yl)-1H-pyrazol-1-yl)-3-methoxypropyl)-5-(3-chloro-2-fluoro-6-(1H-tetrazol-1-yl)phenyl)pyridine 1-oxide A mixture of 2-(1-(4-(1H-imidazol-1-yl)-1H-pyrazol-1-yl)-3-methoxypropyl)-5-(3-chloro-2-fluoro-6-(1H-tetrazol-1-yl)phenyl)pyridine (200 mg, 0.42 mmol, 1.0 equiv.), methyltrioxorhenium (52 mg, 0.21 mmol, 0.2 equiv.) and hydrogen peroxide (0.2 mL, 30 wt %) in CH$_3$OH (1 mL) was stirred for 1H at room temperature. The mixture was purified by reverse phase chromatography on C18 (80 g, MeCN/H$_2$O (0.05% CF$_3$COOH)) to yield 2-(1-(4-(1H-imidazol-1-yl)-1H-pyrazol-1-yl)-3-methoxypropyl)-5-(3-chloro-2-fluoro-6-(1H-tetrazol-1-yl)phenyl)pyridine 1-oxide as a white solid. The racemic product was separated by chiral-HPLC to yield (R*)-2-(1-(4-(1H-imidazol-1-yl)-1H-pyrazol-1-yl)-3-methoxypropyl)-5-(3-chloro-2-fluoro-6-(1H-tetrazol-1-yl)phenyl)pyridine 1- as a white solid.
LC/MS: mass calculated for $C_{22}H_{19}ClFN_9O_2$: 495.13, measured (ES, m/z): 496.10 [M+H]$^+$. $^1$H NMR (300 MHz, DMSO-d$_6$) δ 9.69 (s, 1H), 8.50 (s, 1H), 8.44 (s, 1H), 8.15 (s, 1H), 8.06 (t, J=8.2 Hz, 1H), 8.00 (s, 1H), 7.76 (d, J=8.9 Hz, 1H), 7.59 (s, 1H), 7.32 (d, J=8.2 Hz, 1H), 7.17 (d, J=8.3 Hz, 1H), 7.10 (s, 1H), 6.10-6.15 (m, 1H), 3.25-3.47 (m, 2H), 3.20 (s, 3H), 2.50-2.60 (m, 2H). $^{19}$F-NMR (282 MHz, DMSO-d$_6$) δ −112.70.

Example 564: (S)-2-(1-(4-(1H-imidazol-1-yl)-1H-pyrazol-1-yl)-3-methoxypropyl)-5-(3-chloro-2-fluoro-6-(1H-tetrazol-1-yl)phenyl)pyridine 1-oxide

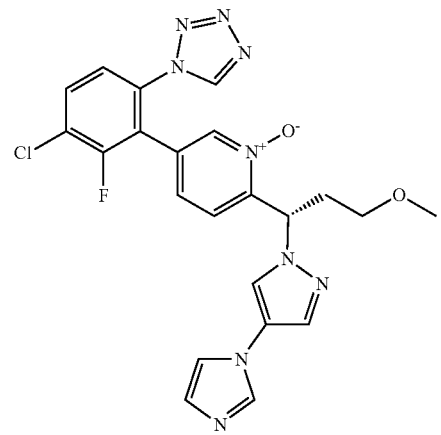 [SMILES: COCC[C@@H](c1ccc(-c2c(-n3cnnn3)ccc(Cl)c2F)c[n+]1[O-])n1cc(-n2ccnc2)cn1]

LC/MS: mass calculated for $C_{22}H_{19}ClFN_9O_2$: 495.13, measured (ES, m/z): 496.10 [M+H]$^+$. $^1$H NMR (300 MHz, DMSO-d$_6$) δ 9.69 (s, 1H), 8.41-8.55 (m, 2H), 7.97-8.22 (m, 3H), 7.57-7.80 (m, 2H), 7.09-7.38 (m, 3H), 6.08-6.12 (m, 1H), 3.26-3.35 (m, 2H), 3.16-3.20 (m, 3H), 2.50-2.60 (m, 2H).

Example 565: (S)-5-(3-chloro-2-fluoro-6-(1H-tetrazol-1-yl)phenyl)-2-(3-(difluoromethoxy)-1-(4-(1-methyl-1H-1,2,3-triazol-5-yl)-1H-pyrazol-1-yl)propyl)pyridine 1-oxide

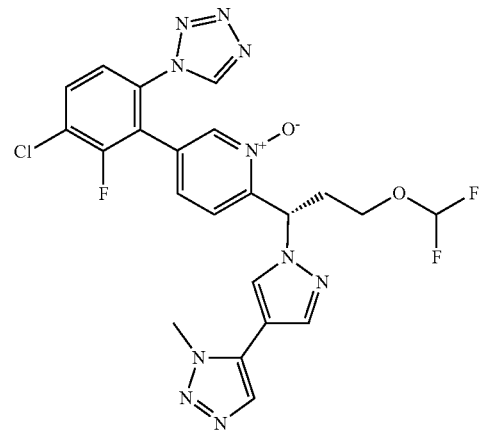 [SMILES: Cn1nncc1-c1cnn([C@@H](CCOC(F)F)c2ccc(-c3c(-n4cnnn4)ccc(Cl)c3F)c[n+]2[O-])c1]

LC/MS: mass calculated for $C_{22}H_{18}ClF_3N_{10}O_2$: 546.13, measured (ES, m/z): 547.10 [M+H]$^+$. $^1$H NMR (400 MHz, DMSO-d$_6$) δ 9.70 (s, 1H), 8.46-8.57 (m, 2H), 8.03-8.12 (m, 2H), 7.91 (s, 1H), 7.77 (dd, J=8.7, 1.5 Hz, 1H), 7.32 (d, J=8.3 Hz, 1H), 7.19 (dd, J=8.2, 1.7 Hz, 1H), 6.64 (t, J=75.7 Hz, 1H), 6.20-6.28 (m, 1H), 4.10 (s, 3H), 3.80-3.90 (m, 1H), 3.62-3.73 (m, 1H), 2.53-2.70 (m, 2H). $^{19}$F NMR (376 MHz, DMSO-d$_6$) δ −83.30, −112.67.

Example 566: (R)-5-(3-Chloro-2-fluoro-6-(1H-tetrazol-1-yl)phenyl)-2-(3-(difluoromethoxy)-1-(4-(1-methyl-1H-1,2,3-triazol-5-yl)-1H-pyrazol-1-yl)propyl)pyridine 1-oxide

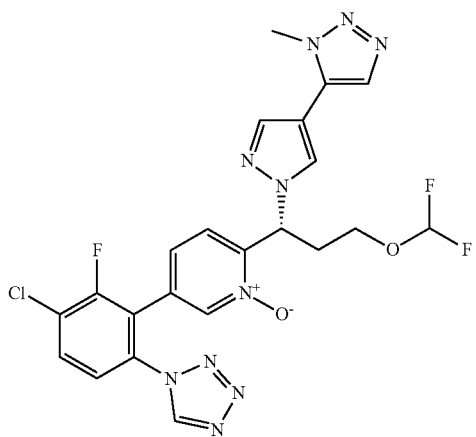 [SMILES: Cn1nncc1-c1cnn([C@H](CCOC(F)F)c2ccc(-c3c(-n4cnnn4)ccc(Cl)c3F)c[n+]2[O-])c1]

Step 1: 1-(5-Bromopyridin-2-yl)-3-((tert-butyldimethylsilyl)oxy)propan-1-ol To a solution of 2,5-dibromopyridine (34.3 g, 144.81 mmol, 1.0 equiv.) in toluene (200 mL) was add n-BuLi (69.5 mL, 173.77 mmol, 1.2 equiv) at −78° C. under $N_2$, after 1 h was add 3-((tert-butyldimethylsilyl)oxy)propanal (30.0 g, 159.29 mmol, 1.1 equiv.) in toluene (100 mL) to the mixture slowly at −78° C., then the reaction mixture was stirred 2 hours at −78° C. The reaction mixture was added $NH_4Cl$ (aq.) and extracted with ethyl acetate, the organic layer was washed with brine and dried over anhydrous $Na_2SO_4$ and concentrated. The residue was purified by silica gel chromatography (0→40% EA/PE) to yield 1-(5-bromopyridin-2-yl)-3-((tert-butyldimethylsilyl)oxy)propan-1-ol as a yellow liquid. LC/MS: mass calculated for $C_{14}H_{24}BrNO_2Si$: 345.08, measured (ES, m/z): 346.05 $[M+H]^+$.

Step 2: 1-(5-Bromopyridin-2-yl)-3-((tert-butyldimethylsilyl)oxy)propyl methanesulfonate To a solution of 1-(5-bromopyridin-2-yl)-3-((tert-butyldimethylsilyl)oxy)propan-1-ol (15.0 g, 43.31 mmol, 1.0 equiv.) in DCM (100 mL) was added triethylamine (12.0 ml, 86.62 mmol, 2.0 equiv.) and methanesulfonic anhydride (11.3 g, 64.97 mmol, 1.5 equiv) at 0° C., then warmed to room temperature the and stirred for 4 h. The reaction was added water, and the mixture extracted with DCM, the organic layer was washed with brine and dried over anhydrous $Na_2SO_4$ and concentrated. The residue was purified by silica gel chromatography (0→40% EA/PE) to yield 1-(5-bromopyridin-2-yl)-3-((tert-butyldimethylsilyl)oxy)propyl methanesulfonate as a yellow solid. LC/MS: mass calculated for $C_{15}H_{26}BrNO_4SSi$: 423.05, measured (ES, m/z): 423.95 $[M+H]^+$.

Step 3: 5-Bromo-2-(3-((tert-butyldimethylsilyl)oxy)-1-(4-iodo-1H-pyrazol-1-yl)propyl)pyridine The mixture of 1-(5-bromopyridin-2-yl)-3-((tert-butyldimethylsilyl)oxy)propyl methanesulfonate (10.0 g, 23.56 mmol, 1.0 equiv.), 4-iodo-1H-pyrazole (5.5 g, 28.27 mmol, 1.2 equiv.) and $Cs_2CO_3$ (15.4 g, 47.12 mmol, 2.0 equiv.) in acetonitrile (80 mL) was stirred at 85° C. for 2 h. To the reaction mixture was added water, and the mixture extracted with ethyl acetate, the organic layer was washed with brine and dried over anhydrous $Na_2SO_4$ and concentrated. The residue was purified by silica gel chromatography (0→40% EA/PE) to yield 5-bromo-2-(3-((tert-butyldimethylsilyl)oxy)-1-(4-iodo-1H-pyrazol-1-yl)propyl)pyridine as a yellow solid. LC/MS: mass calculated for $C_{17}H_{25}BrIN_3OSi$: 521.00, measured (ES, m/z): 522.10 $[M+H]^+$.

Step 4: 3-(5-Bromopyridin-2-yl)-3-(4-iodo-1H-pyrazol-1-yl)propan-1-ol

The mixture of 5-bromo-2-(3-((tert-butyldimethylsilyl)oxy)-1-(4-iodo-1H-pyrazol-1-yl)propyl)pyridine (11.0 g, 21.06 mmol, 1.0 equiv.) and TBAF (11.5 mL, 42.12 mmol, 2.0 equiv.) in THF (100 mL) was stirred at room temperature for 2 h. To the reaction mixture was added water, and the mixture extracted with ethyl acetate, the organic layer was washed with brine and dried over anhydrous $Na_2SO_4$ and concentrated. The residue was purified by silica gel chromatography (0→40% EA/PE) to yield 3-(5-bromopyridin-2-yl)-3-(4-iodo-1H-pyrazol-1-yl)propan-1-ol as a yellow solid. LC/MS: mass calculated for $C_{11}H_{11}BrIN_3O$: 406.91, measured (ES, m/z): 407.95 $[M+H]^+$.

Step 5: 5-Bromo-2-(3-(difluoromethoxy)-1-(4-iodo-1H-pyrazol-1-yl)propyl)pyridine To a mixture of 3-(5-bromopyridin-2-yl)-3-(4-iodo-1H-pyrazol-1-yl)propan-1-ol (6.4 g, 15.68 mmol, 1.0 equiv.) and cuprous iodide (597 mg, 3.14 mmol, 0.2 equiv.) in acetonitrile (50 mL) was added 2-(fluorosulfonyl)difluoroacetic acid (4.2 g, 23.53 mmol, 1.5 equiv.) in acetonitrile (10 mL) at 50° C. under $N_2$. The reaction mixture was stirred at 50° C. for 30 min. To the reaction mixture was added water, and the mixture extracted with ethyl acetate, the organic layer was washed with brine and dried over anhydrous $Na_2SO_4$ and concentrated. The residue was purified by silica gel chromatography (0→40% EA/PE) to yield 5-bromo-2-(3-(difluoromethoxy)-1-(4-iodo-1H-pyrazol-1-yl)propyl)pyridine as a yellow solid. LC/MS: mass calculated for $C_{12}H_{11}BrF_2IN_3O$: 456.91, measured (ES, m/z): 457.65 $[M+H]^+$.

Step 6: 5-Bromo-2-(3-(difluoromethoxy)-1-(4-(1-methyl-1H-1,2,3-triazol-5-yl)-1H-pyrazol-1-yl)propyl)pyridine The mixture of 5-bromo-2-(3-(difluoromethoxy)-1-(4-iodo-1H-pyrazol-1-yl)propyl)pyridine (1.0 g, 2.18 mmol, 1.0 equiv.), 1-methyl-5-(4,4,5,5-tetramethyl-1,3,2-dioxaborolan-2-yl)-1H-1,2,3-triazole (502 mg, 2.40 mmol, 1.1 equiv.), $K_2CO_3$ (1.5 g, 10.92 mmol, 5.0 equiv.) and Pd(dppf)$Cl_2$ (159 mg, 0.22 mmol, 0.1 equiv.) in 1,4-dioxane (10 mL) and water (2 mL) was stirred at 90° C. under $N_2$ for 2 h. To the reaction mixture was added water, and the mixture extracted with ethyl acetate, the organic layer was washed with brine and dried over anhydrous $Na_2SO_4$ and concentrated. The residue was purified by silica gel chromatography (0→40% EA/PE) to yield 5-bromo-2-(3-(difluoromethoxy)-1-(4-(1-methyl-1H-1,2,3-triazol-5-yl)-1H-pyrazol-1-yl)propyl)pyridine as a yellow solid. LC/MS: mass calculated for $C_{15}H_{15}BrF_2N_6O$: 412.05, measured (ES, m/z): 413.00 $[M+H]^+$.

Step 7: 4-Chloro-2-(6-(3-(difluoromethoxy)-1-(4-(1-methyl-1H-1,2,3-triazol-5-yl)-1H-pyrazol-1-yl)propyl)pyridin-3-yl)-3-fluoroaniline To a mixture of 5-bromo-2-(3-(difluoromethoxy)-1-(4-(1-methyl-1H-1,2,3-triazol-5-yl)-1H-pyrazol-1-yl)propyl)pyridine (290 mg, 0.70 mmol, 1.0 equiv.), 6-amino-3-chloro-2-fluorophenylboronic acid (199 mg, 1.05 mmol, 1.5 equiv.) and potassium carbonate (291 mg, 2.10 mmol, 3.0 equiv.) in 1,4-dioxane (5 mL) and water (1 mL) was added Pd(PPh$_3$)$_4$ (81 mg, 0.07 mmol, 0.1 equiv.) and the mixture was stirred for 2 h at 90° C. under N$_2$. After cooling to room temperature, the reaction was quenched with water, and the mixture extracted with EtOAc twice. The combined organic layers were washed with brine, dried over anhydrous sodium sulfate, and concentrated. The residue was purified by silica gel chromatography (0→80% EA/PE) to yield 4-chloro-2-(6-(3-(difluoromethoxy)-1-(4-(1-methyl-1H-1,2,3-triazol-5-yl)-1H-pyrazol-1-yl)propyl)pyridin-3-yl)-3-fluoroaniline as a light yellow solid. LC/MS: mass calculated for C$_{21}$H$_{19}$ClF$_3$N$_7$O: 477.13, measured (ES, m/z): 478.10 [M+H]$^+$.

Step 8: 5-(3-Chloro-2-fluoro-6-(1H-tetrazol-1-yl)phenyl)-2-(3-(difluoromethoxy)-1-(4-(1-methyl-1H-1,2,3-triazol-5-yl)-1H-pyrazol-1-yl)propyl)pyridine A mixture of 4-chloro-2-(6-(3-(difluoromethoxy)-1-(4-(1-methyl-1H-1,2,3-triazol-5-yl)-1H-pyrazol-1-yl)propyl)pyridin-3-yl)-3-fluoroaniline (0.26 g, 0.54 mmol, 1.0 equiv.), azidotrimethylsilane (1.0 mL), trimethoxymethane (1.0 mL) in acetic acid glacial (1.0 mL) was stirred overnight at room temperature. The solution was purified by reverse phase chromatography on C18 (80 g, MeCN/H$_2$O (0.05% CF$_3$COOH): 0→50%) to yield 5-(3-chloro-2-fluoro-6-(1H-tetrazol-1-yl)phenyl)-2-(3-(difluoromethoxy)-1-(4-(1-methyl-1H-1,2,3-triazol-5-yl)-1H-pyrazol-1-yl)propyl)pyridine as a light yellow solid. LC/MS: mass calculated for C$_{22}$H$_{18}$ClF$_3$N$_{10}$O: 530.13, measured (ES, m/z): 531.10 [M+H]$^+$.

Step 9: (R)-5-(3-Chloro-2-fluoro-6-(1H-tetrazol-1-yl)phenyl)-2-(3-(difluoromethoxy)-1-(4-(1-methyl-1H-1,2,3-triazol-5-yl)-1H-pyrazol-1-yl)propyl)pyridine 1-oxide The compound of 5-(3-chloro-2-fluoro-6-(1H-tetrazol-1-yl)phenyl)-2-(3-(difluoromethoxy)-1-(4-(1-methyl-1H-1,2,3-triazol-5-yl)-1H-pyrazol-1-yl)propyl)pyridine 1-oxide (60 mg) was separated by Prep-Chiral-HPLC to yield (R)-5-(3-chloro-2-fluoro-6-(1H-tetrazol-1-yl)phenyl)-2-(3-(difluoromethoxy)-1-(4-(1-methyl-1H-1,2,3-triazol-5-yl)-1H-pyrazol-1-yl)propyl)pyridine 1-oxide as a white solid.

LC/MS: mass calculated for C$_{22}$H$_{18}$ClF$_3$N$_{10}$O$_2$: 546.13, measured (ES, m/z): 547.05 [M+H]$^+$. $^1$H NMR (400 MHz, DMSO-d$_6$) δ 9.70 (s, 1H), 8.55 (s, 1H), 8.48 (s, 1H), 8.03-8.12 (m, 2H), 7.91 (s, 1H), 7.77 (d, J=8.7 Hz, 1H), 7.32 (d, J=8.2 Hz, 1H), 7.19 (d, J=8.2, Hz, 1H), 6.64 (t, J=75.7 Hz, 1H), 6.24 (dd, J=10.1, 4.4 Hz, 1H), 4.10 (s, 3H), 3.83-3.88 (m, 1H), 3.65-3.71 (m, 1H), 2.57-2.68 (m, 2H). $^{19}$F NMR (376 MHz, DMSO-d$_6$) δ −83.29, −112.67.

Alternative Synthesis Method

Step 1: 1-(5-Bromopyridin-2-yl)-3-((tert-butyldimethylsilyl)oxy)propan-1-ol n-Butyllithium (56.5 g, 882.3 mmol, 1.1 eq., 2.5 M) was slowly added to a solution of 2,5-dibromopyridine (190 g, 802.1 mol, 1.0 eq.) in toluene (1500 mL) at −78° C. under N$_2$ and the mixture was stirred for 1 h under N$_2$. Then 3-((tert-butyldimethylsilyl)oxy)propanal (166.2 g, 882.3 mmol, 1.1 eq.) was added and the mixture was stirred for 1 h. The reaction was then quenched with saturated ammonium chloride aqueous solution and extracted with EtOAc twice. The combined organic layer was washed with brine, dried over Na$_2$SO$_4$, concentrated under reduced pressure and purified by silica gel chromatography (0-20% EtOAc/petroleum ether) to yield 1-(5-bromopyridin-2-yl)-3-((tert-butyldimethylsilyl)oxy)propan-1-ol as a yellow oil. LC/MS: mass calculated for C$_{14}$H$_{24}$BrNO$_2$Si: 345.08, measured: 346.15 [M+H]$^+$.

Step 2: 5-Bromo-2-(3-((tert-butyldimethylsilyl)oxy)-1-((tetrahydro-2H-pyran-2-yl)oxy)propyl)pyridine To a solution of 1-(5-bromopyridin-2-yl)-3-((tert-butyldimethylsilyl)oxy)propan-1-ol (145 g, 418.7 mmol, 1 eq.) and 3,4-dihydro-2H-pyran (105.7 g, 1256.1 mmol, 3.0 eq.) in DCM (1500 mL) was added TsOH (7.21 g, 41.9 mmol, 0.1 eq.). The reaction mixture was stirred at 70° C. for 1 h, then quenched with NaHCO$_3$, extracted with EtOAc. The combined organic layer was washed with brine, dried over Na$_2$SO$_4$ and concentrated under vacuum to yield 5-bromo-2-(3-((tert-butyldimethylsilyl)oxy)-1-((tetrahydro-2H-pyran-2-yl)oxy)propyl)pyridine. LC/MS: mass calculated for C$_{19}$H$_{32}$BrNO$_3$Si: 429.13, measured: 430.25[M+H]$^+$.

Step 3: 3-(5-Bromopyridin-2-yl)-3-(tetrahydro-2H-pyran-2-yloxy)propan-1-ol

To a solution of 5-bromo-2-(3-((tert-butyldimethylsilyl)oxy)-1-((tetrahydro-2H-pyran-2-yl)oxy)propyl)pyridine (130 g, 302.0 mmol, 1.0 eq.) in tetrahydrofuran (1500 mL), triethylamine trihydrofluoride (97.4 g, 604.0 mmol, 2.0 eq.) was added. The reaction was stirred for 2.5 h at 70° C., then diluted with water and extracted with EtOAc three times. The combined organic layer was washed with brine, dried over Na$_2$SO$_4$, and concentrated under vacuum. The residue was purified by silica gel chromatography with EA/PE (0-30%) to yield 3-(5-bromopyridin-2-yl)-3-(tetrahydro-2H-pyran-2-yloxy)propan-1-ol as yellow oil. LC/MS: mass calculated for C$_{13}$H$_{18}$BrNO$_3$: 315.05, measured: 316.05 [M+H]$^+$.

Step 4: 5-Bromo-2-(3-(difluoromethoxy)-1-((tetrahydro-2H-pyran-2-yl)oxy)propyl)pyridine To a solution of 3-(5-bromopyridin-2-yl)-3-((tetrahydro-2H-pyran-2-yl)oxy)propan-1-ol (67 g, 211.9 mmol, 1 eq.) in acetonitrile (800 mL) was added cuprous iodide (8.1 g, 42.4 mmol, 0.2 eq.). To the resulting mixture was then slowly added 2-(fluorosulfonyl)difluoroacetic acid (56.6 g, 317.8 mmol, 1.5 eq.) over 1 h at 50° C. in N$_2$. The reaction was quenched with water and extracted with EtOAc three times. The combined organic layer was washed with brine, dried over Na$_2$SO$_4$, and concentrated under vacuum. The residue was purified by silica gel chromatography with EtOAc/petroleum ether (0-20%) to yield 5-bromo-2-(3-(difluoromethoxy)-1-((tetrahydro-2H-pyran-2-yl)oxy)propyl)pyridine as yellow oil. LC/MS: mass calculated for C$_{14}$H$_{18}$BrF$_2$NO$_3$: 365.04, measured: 366.15 [M+H]$^+$.

Step 5: 1-(5-Bromopyridin-2-yl)-3-(difluoromethoxy)propan-1-ol

To a mixture of 5-bromo-2-(3-(difluoromethoxy)-1-((tetrahydro-2H-pyran-2-yl)oxy)propyl)pyridine (48 g, 131.1 mmol, 1.00 eq.) in DCM (1 L) was added TFA (200 mL) dropwise with stirring at 0° C. The reaction was stirred at room temperature for 1 h, then concentrated to yield 1-(5-bromopyridin-2-yl)-3-(difluoromethoxy)propan-1-ol as a brown oil. LC/MS: mass calculated for $C_9H_{10}BrF_2NO_2$: 280.99, measured: 281.95, 283.95 [M+H, M+H+2]$^+$.

Step 6: 1-(5-Bromopyridin-2-yl)-3-(difluoromethoxy)propyl methanesulfonate

To a mixture of 1-(5-bromopyridin-2-yl)-3-(difluoromethoxy)propan-1-ol (45 g, 159.5 mmol, 1 eq.) and triethylamine (80.7 g, 794.6 mmol, 5 eq.) in DCM (1000 mL) was added methanesulfonic anhydride (55.6 g, 319.1 mmol, 2 eq.) at 0° C. and the solution was stirred for 2 h at room temperature, then diluted with $H_2O$ and extracted with DCM twice. The combined organic layer was washed with brine, dried over $Na_2SO_4$, concentrated and purified by silica gel chromatography (0-30% EtOAc/petroleum ether) to yield 1-(5-bromopyridin-2-yl)-3-(difluoromethoxy)propyl methanesulfonate as a light yellow solid. LC/MS: mass calculated for $C_{10}H_{12}BrF_2NO_4S$: 359, measured: 360.05 [M+H]$^+$.

Step 7: 5-Bromo-2-(3-(difluoromethoxy)-1-(4-(1-methyl-1H-1,2,3-triazol-5-yl)-1H-pyrazol-1-yl)propyl)pyridine A mixture of 1-methyl-5-(1H-pyrazol-4-yl)-1H-1,2,3-triazole (2.961 g, 19.9 mmol, 1.1 eq.) and cesium carbonate (6.5 g, 19.9 mmol, 1.1 eq.) in acetonitrile (60 mL) was stirred for 15 min at room temperature. 1-(5-Bromopyridin-2-yl)-3-(difluoromethoxy)propyl methanesulfonate (6.5 g, 18.0 mmol, 1 eq.) was added and the solution was stirred for 3 h at 90° C., then diluted with $H_2O$, and extracted with EtOAc twice. The combined organic layer was washed with brine, dried over $Na_2SO_4$, concentrated and purified by silica gel chromatography (0-50% EtOAc/petroleum ether) to yield 5-bromo-2-(3-(difluoromethoxy)-1-(4-(1-methyl-1H-1,2,3-triazol-5-yl)-1H-pyrazol-1-yl)propyl)pyridine as a light yellow oil. LC/MS: mass calculated for $C_{15}H_{15}BrF_2N_6O$: 412, measured: 413.15 [M+H]$^+$.

Step 8: 4-Chloro-2-(6-(3-(difluoromethoxy)-1-(4-(1-methyl-1H-1,2,3-triazol-5-yl)-1H-pyrazol-1-yl)propyl)pyridin-3-yl)-3-fluoroaniline To a mixture of 5-bromo-2-(3-(difluoromethoxy)-1-(4-(1-methyl-1H-1,2,3-triazol-5-yl)-1H-pyrazol-1-yl)propyl)pyridine (290 mg, 0.70 mmol, 1.0 eq.), 6-amino-3-chloro-2-fluorophenylboronic acid (199 mg, 1.05 mmol, 1.5 eq.) and potassium carbonate (291 mg, 2.10 mmol, 3.0 eq.) in 1,4-dioxane (5 mL) and water (1 mL) was added Pd(PPh$_3$)$_4$ (81 mg, 0.07 mmol, 0.1 eq.) and the resulting mixture was stirred for 2 h at 90° C. under $N_2$. After cooling to room temperature, the mixture was diluted with water and extracted with EtOAc twice. The combined organic layer was washed with brine, dried over anhydrous sodium sulfate, and concentrated. The residue was purified by silica gel chromatography (0→80% EA/PE) to yield 4-chloro-2-(6-(3-(difluoromethoxy)-1-(4-(1-methyl-1H-1,2,3-triazol-5-yl)-1H-pyrazol-1-yl)propyl)pyridin-3-yl)-3-fluoroaniline as a light yellow solid. LC/MS: mass calculated for $C_{21}H_{19}ClF_3N_7O$: 477.13, measured: (ES, m/z): 478.10 [M+H]$^+$.

Step 9: 5-(3-Chloro-2-fluoro-6-(1H-tetrazol-1-yl)phenyl)-2-(3-(difluoromethoxy)-1-(4-(1-methyl-1H-1,2,3-triazol-5-yl)-1H-pyrazol-1-yl)propyl)pyridine A mixture of 4-chloro-2-(6-(3-(difluoromethoxy)-1-(4-(1-methyl-1H-1,2,3-triazol-5-yl)-1H-pyrazol-1-yl)propyl)pyridin-3-yl)-3-fluoroaniline (0.26 g, 0.54 mmol, 1.0 eq.), azidotrimethylsilane (1.0 mL), trimethoxymethane (1.0 mL) in acetic acid glacial (1.0 mL) was stirred overnight at room temperature. The solution was purified by reverse phase chromatography on C18 (80 g, MeCN/H$_2$O (0.05% CF$_3$COOH): 0→50%) to yield 5-(3-chloro-2-fluoro-6-(1H-tetrazol-1-yl)phenyl)-2-(3-(difluoromethoxy)-1-(4-(1-methyl-1H-1,2,3-triazol-5-yl)-1H-pyrazol-1-yl)propyl)pyridine as a light yellow solid. LC/MS: mass calculated for $C_{22}H_{18}ClF_3N_{10}O$: 530.13, measured (ESI, m/z): 531.10 [M+H]$^+$.

Step 10: (R)-5-(3-Chloro-2-fluoro-6-(1H-tetrazol-1-yl)phenyl)-2-(3-(difluoromethoxy)-1-(4-(1-methyl-1H-1,2,3-triazol-5-yl)-1H-pyrazol-1-yl)propyl)pyridine 1-oxide A racemic mixture of 5-(3-chloro-2-fluoro-6-(1H-tetrazol-1-yl)phenyl)-2-(3-(difluoromethoxy)-1-(4-(1-methyl-1H-1,2,3-triazol-5-yl)-1H-pyrazol-1-yl)propyl)pyridine 1-oxide (60 mg) was separated by prep-chiral-HPLC to yield (R)-5-(3-chloro-2-fluoro-6-(1H-tetrazol-1-yl)phenyl)-2-(3-(difluoromethoxy)-1-(4-(1-methyl-1H-1,2,3-triazol-5-yl)-1H-pyrazol-1-yl)propyl)pyridine 1-oxide as a white solid.

HPLC purity (method A): 99.8%, retention time=1.202 min. LC/MS: mass calculated for $C_{22}H_{18}ClF_3N_{10}O_2$: 546.13, measured (ES, m/z): 547.05 [M+H]$^+$. $^1$H NMR (400 MHz, DMSO-d$_6$) δ 9.70 (s, 1H), 8.55 (s, 1H), 8.48 (s, 1H), 8.03-8.12 (m, 2H), 7.91 (s, 1H), 7.77 (d, J=8.7 Hz, 1H), 7.32 (d, J=8.2 Hz, 1H), 7.19 (d, J=8.2, Hz, 1H), 6.64 (t, J=75.7 Hz, 1H), 6.24 (dd, J=10.1, 4.4 Hz, 1H), 4.10 (s, 3H), 3.83-3.88 (m, 1H), 3.65-3.71 (m, 1H), 2.57-2.68 (m, 2H). $^{19}$F NMR (376 MHz, DMSO-d$_6$) δ −83.29, −112.67.

Example 567: (S*)-5-(3-Chloro-6-(difluoromethyl)-2-fluorophenyl)-2-(1-(4-(1-methyl-1H-1,2,3-triazol-5-yl)-1H-pyrazol-1-yl)-2-(1-methyl-1H-pyrazol-4-yl)ethyl)pyridine 1-oxide

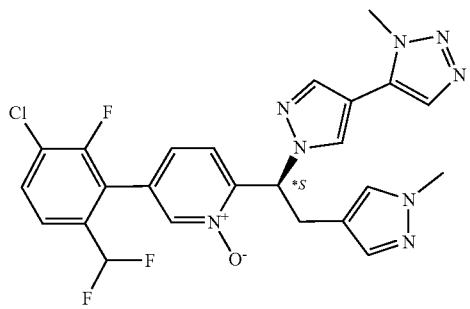 [SMILES: Cn1cc(C[C@@H](c2ccc(-c3c(C(F)F)ccc(Cl)c3F)c[n+]2[O-])n2cc(-c3cnnn3C)cn2)cn1]

LC/MS: mass calculated for $C_{24}H_{20}ClF_3N_8O$: 528.14, measured (ES, m/z): 529.10 [M+H]$^+$. $^1$H NMR (300 MHz, DMSO-d$_6$) δ 8.51 (d, J=6.6 Hz, 2H), 8.04 (s, 1H), 7.84-7.94 (m, 2H), 7.62 (d, J=8.6 Hz, 1H), 7.53 (d, J=8.3 Hz, 1H), 7.41 (d, J=8.0 Hz, 1H), 7.35 (s, 1H), 6.69-7.10 (m, 2H), 6.10-6.22 (m, 1H), 3.62 (s, 3H), 3.80-3.90 (m, 1H), 4.07 (s, 3H), 3.30-3.35 (m, 2H).

Example 568: (R*)-5-(3-Chloro-6-(difluoromethyl)-2-fluorophenyl)-2-(1-(4-(1-methyl-1H-1,2,3-triazol-5-yl)-1H-pyrazol-1-yl)-2-(1-methyl-1H-pyrazol-4-yl)ethyl)pyridine 1-oxide

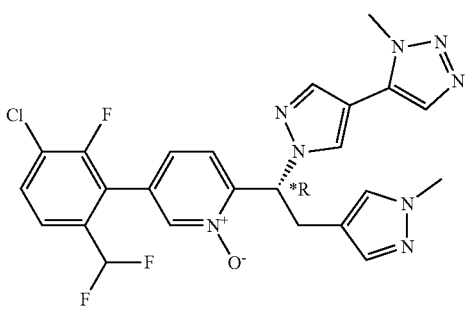 [SMILES: Cn1cc(C[C@H](c2ccc(-c3c(C(F)F)ccc(Cl)c3F)c[n+]2[O-])n2cc(-c3cnnn3C)cn2)cn1]

LC/MS: mass calculated for $C_{24}H_{20}ClF_3N_8O$: 528.14, measured (ES, m/z): 529.10 [M+H]$^+$. $^1$H NMR (300 MHz, DMSO-d$_6$) δ 8.51 (d, J=6.5 Hz, 2H), 8.04 (s, 1H), 7.83-7.95 (m, 2H), 7.61 (d, J=8.5 Hz, 1H), 7.53 (d, J=8.3 Hz, 1H), 7.41 (d, J=8.3 Hz, 1H), 7.35 (s, 1H), 6.67-7.13 (m, 2H), 6.12-6.22 (m, 1H), 4.07 (s, 3H), 3.71 (s, 3H), 3.33-3.36 (m, 2H).

Example 569: (R)-5-(3-Chloro-2-fluoro-6-(1H-tetrazol-1-yl)phenyl)-2-(1-(4-(2-(difluoromethyl)thiazol-5-yl)-1H-pyrazol-1-yl)-3-methoxypropyl)pyridine 1-oxide

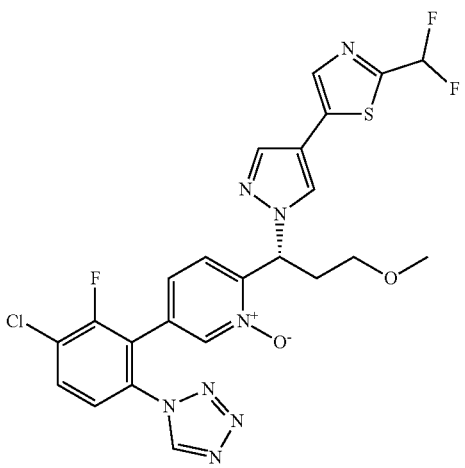 [SMILES: COCC[C@H](c1ccc(-c2c(-n3cnnn3)ccc(Cl)c2F)c[n+]1[O-])n1cc(-c2cnc(C(F)F)s2)cn1]

Step 1:
2-(Difluoromethyl)-5-(1H-pyrazol-4-yl)thiazole

To a solution of 5-bromo-2-(difluoromethyl)thiazole (500 mg, 2.34 mmol, 1.0 equiv.) in DMF (20 mL) and H$_2$O (2 mL) was added tert-butyl 4-(4,4,5,5-tetramethyl-1,3,2-dioxaborolan-2-yl)-1H-pyrazole-1-carboxylate (1.0 g, 3.50 mmol, 1.5 equiv.), K$_2$CO$_3$ (0.97 g, 7.01 mmol, 3.0 equiv.) and Pd(PPh$_3$)$_4$ (270 mg, 0.23 mmol, 0.1 equiv.). The resulting mixture was maintained under nitrogen and stirred at 85° C. for 14 h. After cooling to room temperature, the reaction was quenched with water (80 mL). The resulting mixture was extracted with ethyl acetate (3×30 mL). The organic layers were combined, dried over anhydrous sodium sulfate, filtered and concentrated. The resulting residue was purified by silica gel chromatography (0→5% MeOH/DCM) to yield 2-(difluoromethyl)-5-(1H-pyrazol-4-yl)thiazole as a yellow solid. LC/MS: mass calculated for $C_7H_5F_2N_3S$: 201.02, measured (ES, m/z): 202.0 [M+H]$^+$.

Step 2: 5-(1-(1-(5-Bromopyridin-2-yl)-3-methoxypropyl)-1H-pyrazol-4-yl)-2-(difluoromethyl)thiazole To a solution of 1-(5-bromopyridin-2-yl)-3-methoxypropyl methanesulfonate (400 mg, 1.23 mmol, 1.0 equiv.) in ACN (20 mL) was added Cs$_2$CO$_3$ (442 mg, 1.36 mmol, 1.1 equiv.) and 2-(difluoromethyl)-5-(1H-pyrazol-4-yl)thiazole (248 mg, 1.23 mmol, 1.0 equiv.) and stirred at 80° C. for 2 h. After cooling to room temperature, the reaction was quenched with water. The resulting mixture was extracted with ethyl acetate. The organic layers were combined, dried over anhydrous sodium sulfate, filtered and concentrated to yield 5-(1-(1-(5-bromopyridin-2-yl)-3-methoxypropyl)-1H-pyrazol-4-yl)-2-(difluoromethyl)thiazole as a yellow oil (451 mg, 85.1% yield). LC/MS: mass calculated for $C_{16}H_{15}BrF_2N_4OS$: 428.01, measured (ES, m/z): 428.95, 430.95 [M+H, M+H+2]$^+$.

Step 3: 4-Chloro-2-(6-(1-(4-(2-(difluoromethyl)thiazol-5-yl)-1H-pyrazol-1-yl)-3-methoxypropyl)pyridin-3-yl)-3-fluoroaniline To a solution of 5-(1-(1-(5-bromopyridin-2-yl)-3-methoxypropyl)-1H-pyrazol-4-yl)-2-(difluoromethyl)thiazole (451 mg, 1.05 mmol, 1.0 equiv.) in 1,4-dioxane (20 mL) and H$_2$O (1 mL) was added (6-amino-3-chloro-2-fluorophenyl)boronic acid (398 mg, 2.10 mmol, 2.0 equiv.), K$_2$CO$_3$ (436 mg, 3.15 mmol, 3.0 equiv.) and Pd(PPh$_3$)$_4$ (121 mg, 0.11 mmol, 0.1 equiv.). The resulting mixture was maintained under nitrogen and stirred at 75° C. for 2 h. After cooling to room temperature, the reaction was quenched with water. The resulting mixture was extracted with ethyl acetate. The organic layers were combined, dried over anhydrous sodium sulfate, filtered and concentrated. The resulting residue was purified by silica gel chromatography (0→7% MeOH/DCM) to yield 4-chloro-2-(6-(1-(4-(2-(difluoromethyl)thiazol-5-yl)-1H-pyrazol-1-yl)-3-methoxypropyl)pyridin-3-yl)-3-fluoroaniline as a yellow oil. LC/MS: mass calculated for $C_{22}H_{19}ClF_3N_5OS$: 493.10, measured (ES, m/z): 494.00 [M+H]$^+$.

Step 4: 5-(1-(1-(5-(3-Chloro-2-fluoro-6-(1H-tetrazol-1-yl)phenyl)pyridin-2-yl)-3-methoxypropyl)-1H-pyrazol-4-yl)-2-(difluoromethyl)thiazole To a solution of 4-chloro-2-(6-(1-(4-(2-(difluoromethyl)thiazol-5-yl)-1H-pyrazol-1-yl)-3-methoxypropyl)pyridin-3-yl)-3-fluoroaniline (576 mg, 1.17 mmol, 1.0 equiv.) in AcOH (3 mL) was added trimethoxymethane (2 mL) and TMSN$_3$ (2 mL). The resulting mixture was stirred at room temperature. for 14 h. The reaction was purified by reverse phase chromatography on C18 (80 g, 5%→60%, MeCN/H$_2$O) to yield 5-(1-(1-(5-(3-chloro-2-fluoro-6-(1H-tetrazol-1-yl)phenyl)pyridin-2-yl)-3-methoxypropyl)-1H-pyrazol-4-yl)-2-(difluoromethyl)thiazole as a yellow oil. LC/MS: mass calculated for $C_{23}H_{18}ClF_3NOS$: 546.10, measured (ES, m/z): 547.15 [M+H]$^+$.

Step 5: (R)-5-(3-Chloro-2-fluoro-6-(1H-tetrazol-1-yl)phenyl)-2-(1-(4-(2-(difluoromethyl)thiazol-5-yl)-1H-pyrazol-1-yl)-3-methoxypropyl)pyridine 1-oxide To a solution of 5-(1-(1-(5-(3-chloro-2-fluoro-6-(1H-tetrazol-1-yl)phenyl)pyridin-2-yl)-3-methoxypropyl)-1H- pyrazol-4-yl)-2-(difluoromethyl)thiazole (150 mg, 0.27 mmol, 1.0 equiv.) in MeOH (5 mL) was added Methyltrioxorhenium (34 mg, 0.137 mmol, 0.5 eq) and $H_2O_2$ (0.138 mL, 1.371 mmol, 5 eq). The resulting mixture was stirred at room temperature. for 2 h. The reaction was purified by reverse phase chromatography on $C_{18}$ (120 g, 5%-55%, MeCN/$H_2O$) and Chiral HPLC to yield (R)-5-(3-chloro-2-fluoro-6-(1H-tetrazol-1-yl)phenyl)-2-(1-(4-(2-(difluoromethyl)thiazol-5-yl)-1H-pyrazol-1-yl)-3-methoxypropyl)pyridine 1-oxide as a white solid.

LC/MS: mass calculated for $C_{23}H_{18}ClF_3N_8O_2S$: 562.19, measured (ES, m/z): 563.20 [M+H]$^+$. $^1$H NMR (300 MHz, DMSO-$d_6$) δ 9.69 (s, 1H), 8.54 (s, 1H), 8.43 (s, 1H), 8.18 (s, 1H), 8.00-8.12 (m, 2H), 7.76 (d, J=8.8 Hz, 1H), 7.35 (t, J=51.0 Hz, 1H), 7.33 (d, J=3.7 Hz, 1H), 7.16-7.19 (m, 1H), 6.17 (t, J=7.4 Hz, 1H), 3.27-3.38 (m, 1H), 3.13-3.20 (m, 4H), 2.41-2.46 (m, 2H). $^{19}$F NMR (282 MHz, DMSO-$d_6$) δ −108.70, −112.69.

Example 570: (S)-5-(3-Chloro-2-fluoro-6-(1H-tetrazol-1-yl)phenyl)-2-(1-(4-(2-(difluoromethyl)thiazol-5-yl)-1H-pyrazol-1-yl)-3-methoxypropyl)pyridine 1-oxide

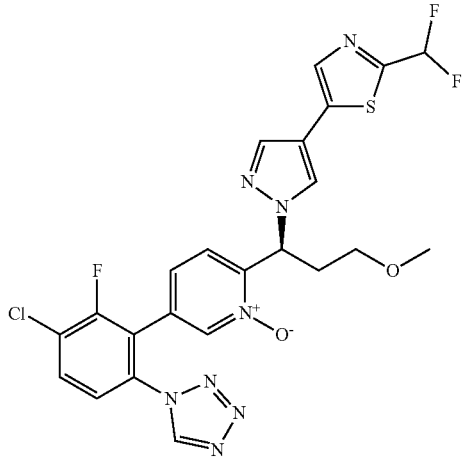 [SMILES: COCC[C@@H](c1ccc(-c2c(-n3cnnn3)ccc(Cl)c2F)c[n+]1[O-])n1cc(-c2cnc(C(F)F)s2)cn1]

LC/MS: mass calculated for $C_{23}H_{18}ClF_3N_8O_2S$: 562.19, measured (ES, m/z): 563.20 [M+H]$^+$. $^1$H NMR (300 MHz, DMSO-$d_6$) δ 9.69 (s, 1H), 8.54 (s, 1H), 8.40-8.47 (m, 1H), 8.18 (d, J=1.3 Hz, 1H), 8.07 (dd, J=8.7, 7.8 Hz, 1H), 8.03 (s, 1H), 7.76 (dd, J=8.7, 1.6 Hz, 1H), 7.06-7.59 (m, 3H), 6.11-6.22 (m, 1H), 3.26-3.32 (m, 1H), 3.20 (s, 3H), 3.10-3.20 (m, 1H), 2.40-2.50 (m, 2H). $^{19}$F NMR (282 MHz, DMSO-$d_6$) δ −108.69, −112.69.

Example 571: (R)-5-(3-Chloro-2-fluoro-6-(1H-tetrazol-1-yl)phenyl)-2-(2-(3-(((difluoromethoxy)methyl)-1H-pyrazol-1-yl)-1-(4-(2-(trifluoromethyl)pyridin-4-yl)-1H-pyrazol-1yl)ethyl)pyridine 1-oxide

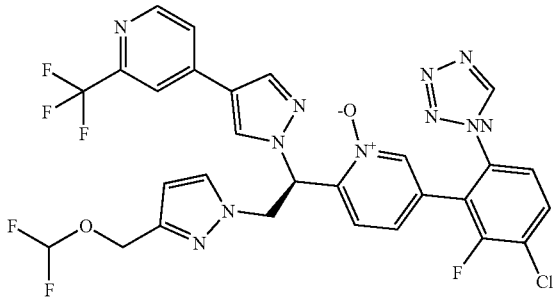

LC/MS: mass calculated for $C_{28}H_{19}ClF_3N_{10}O_2$: 676.13, measured (ES, m/z): 699.05 [M+Na]$^+$. $^1$H NMR (400 MHz, DMSO-$d_6$) δ 9.69 (s, 1H), 8.72 (s, 1H), 8.66 (d, J=5.2 Hz, 1H), 8.53 (d, J=1.6 Hz, 1H), 8.38 (s, 1H), 8.05-8.11 (m, 2H), 7.85 (dd, J=5.1, 1.7 Hz, 1H), 7.77 (dd, J=8.7, 1.5 Hz, 1H), 7.44-7.52 (m, 2H), 7.23 (dd, J=8.3, 1.6 Hz, 1H), 6.46-6.69 (m, 2H), 6.19 (d, J=2.3 Hz, 1H), 4.91-5.17 (m, 1H), 4.79 (s, 2H). $^{19}$F NMR (376 MHz, DMSO-$d_6$) δ −66.58, −82.59, −112.61.

Example 572: (S)-5-(3-Chloro-2-fluoro-6-(1H-tetrazol-1-yl)phenyl)-2-(2-(3-((difluoromethoxy)methyl)-1H-pyrazol-1-yl)-1-(4-(2-(trifluoromethyl)pyridin-4-yl)-1H-pyrazol-1yl)ethyl)pyridine 1-oxide

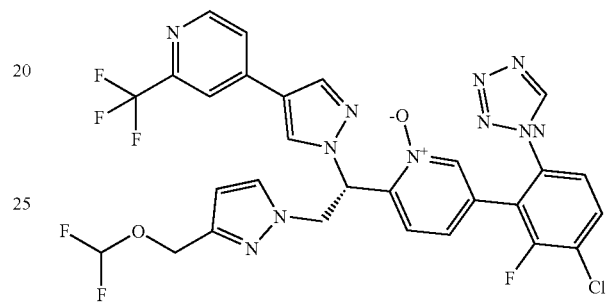

LC/MS: mass calculated for $C_{28}H_{19}ClF_6N_{10}O_2$: 676.13, measured (ES, m/z): 699.10 [M+Na]$^+$. $^1$H NMR (400 MHz, DMSO-$d_6$) δ 9.69 (s, 1H), 8.72 (s, 1H), 8.66 (d, J=5.2 Hz, 1H), 8.53 (d, J=1.6 Hz, 1H), 8.38 (s, 1H), 8.05-8.20 (m, 2H), 7.82-7.88 (m, 1H), 7.77 (dd, J=8.7, 1.5 Hz, 1H), 7.44-7.52 (m, 2H), 7.23 (dd, J=8.2, 1.7 Hz, 1H), 6.47-6.89 (m, 2H), 6.19 (d, J=2.3 Hz, 1H), 4.94-5.18 (m, 2H), 4.78 (s, 2 h). $^{19}$F NMR (376 MHz, DMSO-$d_6$) δ −66.58, −82.59, −112.62.

Example 573: 5-(3-Chloro-2-fluoro-6-(1H-tetrazol-1-yl)phenyl)-2-(2-cyclopropyl-1-(4-(4-cyclopropylthiazol-5-yl)-1H-pyrazol-1-yl)ethyl)pyridine 1-oxide

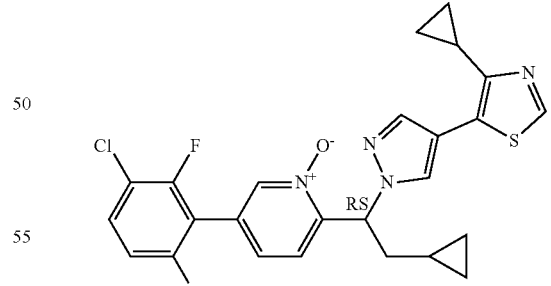

LC/MS: mass calculated for $C_{26}H_{22}ClFN_8OS$: 548.1, measured (ES, m/z): 549.2 [M+H]$^+$. $^1$H NMR (400 MHz, CD$_3$OD) δ ppm 0.02-0.08 (m, 1H) 0.16-0.25 (m, 1H) 0.34-0.51 (m, 2 h) 0.65-0.76 (m, 1H) 0.89-0.95 (m, 2 h) 1.03 (dt, J=8.31, 3.18 Hz, 2 h) 1.99-2.07 (m, 1H) 2.08-2.20 (m, 1H) 2.47 (ddd, J=13.82, 10.15, 6.36 Hz, 1H) 6.24 (dd, J=10.03, 4.16 Hz, 1H) 7.30 (dd, J=8.31, 1.47 Hz, 1H) 7.51 (d, J=8.31 Hz, 1H) 7.61 (dd, J=8.56, 1.71 Hz, 1H) 7.86 (s, 1H) 7.89-7.96 (m, 1H) 8.26 (s, 1H) 8.37 (s, 1H) 8.85 (s, 1H) 9.38 (s, 1H).

Example 574: (S)-5-(3-Chloro-6-(4-chloro-1H-1,2,3-triazol-1-yl)-2-fluorophenyl)-2-(2-(4-fluoro-1H-pyrazol-1-yl)-1-(4-(1-methyl-1H-1,2,3-triazol-5-yl)-1H-pyrazol-1-yl)ethyl)pyridine 1-oxide

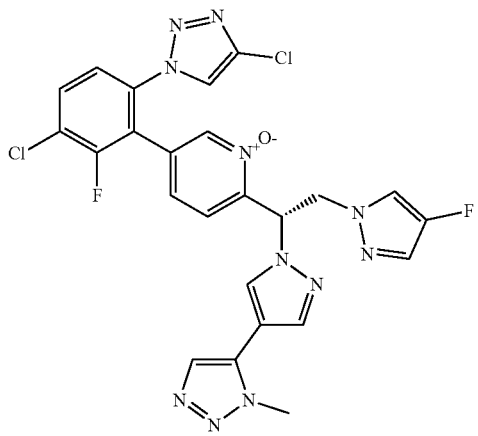

LC/MS: mass calculated for $C_{24}H_{17}Cl_2F_2N_{11}O$: 583.10, measured (ES, m/z): 584.15 [M+H]$^+$. $^1$H NMR (400 MHz, DMSO-d$_6$) δ 8.69 (s, 1H), 8.49 (d, J=1.4 Hz, 1H), 8.38 (s, 1H), 7.99-8.08 (m, 2H), 7.86 (s, 1H), 7.64-7.73 (m, 2H), 7.43-7.52 (m, 2H), 7.21 (dd, J=8.3, 1.6 Hz, 1H), 6.53-6.61 (m, 1H), 4.88-5.05 (m, 2H), 4.03 (s, 3H). $^{19}$F NMR (376 MHz, DMSO-d$_6$) δ −112.88, −177.81.

Example 575: (R)-5-(3-Chloro-6-(4-chloro-1H-1,2,3-triazol-1-yl)-2-fluorophenyl)-2-(2-(4-fluoro-1H-pyrazol-1-yl)-1-(4-(1-methyl-1H-1,2,3-triazol-5-yl)-1H-pyrazol-1-yl)ethyl)pyridine 1-oxide

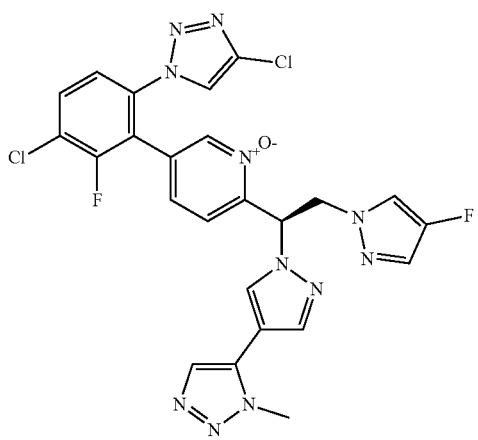

Step 1: 1-(5-Bromopyridin-2-yl)-2-(4-fluoro-1H-pyrazol-1-yl)ethan-1-one

A mixture of 2-bromo-1-(5-bromopyridin-2-yl)ethan-1-one (8.5 g, 30.5 mmol, 1.0 eq.) and 4-fluoro-1H-pyrazole (4 g, 46.5 mmol, 1.5 eq) in DMF (2 mL) was stirred 0.5 h at 80° C. under N$_2$, then quenched with water, extracted with DCM, washed with brine, dried over Na$_2$SO$_4$, and concentrated under vacuum. The reaction mixture was stirred 0.5 h at 80° C., then quenched with water, extracted with DCM, washed with brine, dried over Na$_2$SO$_4$, and concentrated under vacuum. The residue was purified by silica gel chromatography with EtOAc/petroleum ether (0-66%) to yield 1-(5-bromopyridin-2-yl)-2-(4-fluoro-1H-pyrazol-1-yl)ethan-1-one as yellow solid. LC/MS: mass calculated for $C_{10}H_7BrFN_3O$: 282.98, measured: 285.9 [M+H]$^+$.

Step 2: 1-(5-Bromopyridin-2-yl)-2-(4-fluoro-1H-pyrazol-1-yl)ethan-1-ol 1-(5-bromopyridin-2-yl)-2-(4-fluoro-1H-pyrazol-1-yl)ethan-1-one (10 g, 35.2 mmol) was dissolved in MeOH (15 mL). The mixture was charged with N$_2$. The mixture was then cooled to 0° C. and stirred at this temperature about 10 min. NaBH$_4$ (3.3 g, 86.8 mmol) was added into the mixture in three portions over 15 mins. The mixture was stirred at this temperature for 2.5 h. The reaction was concentrated and the residue was used in next step without further purification.

Step 3: 1-(5-Bromopyridin-2-yl)-2-(4-fluoro-1H-pyrazol-1-yl)ethyl methanesulfonate To a solution of 1-(5-bromopyridin-2-yl)-2-(4-fluoro-1H-pyrazol-1-yl)ethan-1-ol (12 g, 41.9 mmol, 1 eq) in DCM (100 mL) was added Et$_3$N (12.7 g, 15.8 mol, 3 eq) and methanesulfonic anhydride (14.6 g, 83.9 mmol, 2 eq) under N$_2$. The reaction mixture was stirred 4 h at room temperature, then extracted with DCM, washed with brine, dried over Na$_2$SO$_4$, and concentrated under vacuum. The residue was purified by silica gel chromatography with EtOAc/petroleum ether (0-66%) to yield 1-(5-bromopyridin-2-yl)-2-(4-fluoro-1H-pyrazol-1-yl)ethyl methanesulfonate as a yellow solid. LC/MS: mass calculated for $C_{11}H_{11}BrFN_3O_3S$: 362.97, measured: 365.9 [M+H]$^+$.

Step 4: 5-Bromo-2-(2-(4-fluoro-1H-pyrazol-1-yl)-1-(4-(1-methyl-1H-1,2,3-triazol-5-yl)-1H-pyrazol-1-yl)ethyl)pyridine 1-Methyl-5-(1H-pyrazol-4-yl)-1H-1,2,3-triazole (122.9 mg, 0.82 mmol, 1.0 equiv.) and Cs$_2$CO$_3$ (268.4 mg, 0.82 mmol, 1.0 equiv.) were dissolved in CH$_3$CN (15.0 mL). The mixture was stirred at room temperature for 1.0 h. Then 1-(5-bromopyridin-2-yl)-2-(4-fluoro-1H-pyrazol-1-yl)ethyl methanesulfonate (300.0 mg, 0.82 mmol, 1.0 equiv.) was added into the mixture and the mixture was heated to 80° C. for 2.0 h under N$_2$. The solvent was removed by distillation under vacuum. The residue was applied onto a silica gel column with MeOH/DCM (1:10) to yield 5-bromo-2-(2-(4-fluoro-1H-pyrazol-1-yl)-1-(4-(1-methyl-1H-1,2,3-triazol-5-yl)-1H-pyrazol-1-yl)ethyl)pyridine as an off-white solid. LC/MS: mass calculated for $C_{24}H_{17}Cl_2F_2N_{11}O$: 583.10, measured (ES, m/z): 584.15[M+H]$^+$. $^1$H NMR (400 MHz, DMSO-d$_6$) δ 8.69 (s, 1H), 8.49 (d, J=1.4 Hz, 1H), 8.38 (s, 1H), 7.99-8.08 (m, 2H), 7.86 (s, 1H), 7.73-7.64 (m, 2H), 7.43-7.52 (m, 2H), 7.15-7.23 (m, 1H), 6.55-6.67 (m, 1H), 4.85-5.04 (m, 2H), 4.03 (s, 3H). $^{19}$F NMR (376 MHz, DMSO-d$_6$) δ −112.88, −177.81.

Step 5: (6-(2-(4-Fluoro-1H-pyrazol-1-yl)-1-(4-(1-methyl-1H-1,2,3-triazol-5-yl)-1H-pyrazol-1-yl)ethyl)pyridin-3-yl)boronic acid 5-Bromo-2-(2-(4-fluoro-1H-pyrazol-1-yl)-1-(4-(1-methyl-1H-1,2,3-triazol-5-yl)-1H-pyrazol-1-yl)ethyl)pyridine (150.0 mg, 0.36 mmol, 1.0 equiv.), 4,4,4',4',5,5,5',5'-octamethyl-2,2'-bi(1,3,2-dioxaborolane) (273.8 mg, 1.08 mmol, 3.0 equiv.), K$_2$CO$_3$ (105.8 mg, 1.08 mmol, 3.0 equiv.) and Pd(dppf)Cl$_2$ (29.4 mg, 0.04 mmol, 0.1 equiv.) were dissolved in 1,4-dioxane (10.0 mL). The mixture was charged with N$_2$ and then heated to 100° C. for 4.0 h. The resulting solution was diluted with water (50 mL), then extracted with EA (10 mL×3). The organic layers were combined, washed with brine (50 mL*1), dried and concentrated under vacuum to yield (6-(2-(4-fluoro-1H-pyrazol-1-yl)-1-(4-(1-methyl-1H-1,2,3-triazol-5-yl)-1H-pyrazol-1-yl)ethyl)pyridin-3-yl)boronic acid as a brown oil. LC/MS: mass calculated for C$_{16}$H$_{16}$BFN$_8$O$_2$: 382.15, measured (ES, m/z): 383.05 [M+H]$^+$.

Step 6: 5-(3-Chloro-6-(4-chloro-1H-1,2,3-triazol-1-yl)-2-fluorophenyl)-2-(2-(4-fluoro-1H-pyrazol-1-yl)-1-(4-(1-methyl-1H-1,2,3-triazol-5-yl)-1H-pyrazol-1-yl)ethyl)pyridine (6-(2-(4-Fluoro-1H-pyrazol-1-yl)-1-(4-(1-methyl-1H-1,2,3-triazol-5-yl)-1H-pyrazol-1-yl)ethyl)pyridin-3-yl)boronic acid (120.0 mg, 0.31 mmol, 1.0 equiv.), 4-chloro-1-(4-chloro-3-fluoro-2-iodophenyl)-1H-1,2,3-triazole (168.6 mg, 0.47 mmol, 1.5 equiv.), Pd(PPh$_3$)$_4$ (36.3 mg, 0.03 mmol, 0.1 equiv.) and K$_2$CO$_3$ (130.2 mg, 0.94 mmol, 3.0 equiv.) were dissolved in 1,4-dioxane (10.0 mL) and H$_2$O (2.0 mL). The flask was evacuated and flushed three times with nitrogen and the mixture was stirred 4.0 h at 100° C. under an atmosphere of nitrogen. The resulting solution was diluted with water (50 mL), then extracted with EA (20.0 mL×3). The organic layers were combined, washed with brine (50.0 mL×1), dried and concentrated under vacuum. The residue was applied onto a silica gel column with ethyl acetate/petroleum ether (1:1) to yield 5-(3-chloro-6-(4-chloro-1H-1,2,3-triazol-1-yl)-2-fluorophenyl)-2-(2-(4-fluoro-1H-pyrazol-1-yl)-1-(4-(1-methyl-1H-1,2,3-triazol-5-yl)-1H-pyrazol-1-yl)ethyl)pyridine as a light yellow oil. LC/MS: mass calculated for C$_{24}$H$_{17}$Cl$_2$F$_2$N$_{11}$: 567.10, measured (ES, m/z): 568.20 [M+H]$^+$.

Step 7: (R)-5-(3-Chloro-6-(4-chloro-1H-1,2,3-triazol-1-yl)-2-fluorophenyl)-2-(2-(4-fluoro-1H-pyrazol-1-yl)-1-(4-(1-methyl-1H-1,2,3-triazol-5-yl)-1H-pyrazol-1-yl)ethyl)pyridine 1-oxide 5-(3-Chloro-6-(4-chloro-1H-1,2,3-triazol-1-yl)-2-fluorophenyl)-2-(2-(4-fluoro-1H-pyrazol-1-yl)-1-(4-(1-methyl-1H-1,2,3-triazol-5-yl)-1H-pyrazol-1-yl)ethyl)pyridine (100.0 mg, 0.18 mmol, 1.0 equiv.), ReMeO$_3$ (8.0 mg, 0.03 mmol, 0.2 equiv.) and H$_2$O$_2$ (1.0 mL, 30 wt %) were dissolved in DMF (2.0 mL) and stirred at room temperature for 2.0 h. The reaction mixture was then purified by chromatography on C18 (80 g, MeCN/H$_2$O (0.05% CF$_3$COOH): 0→60%) and prep-chiral-HPLC. The collected fractions were combined and concentrated under vacuum to yield (R)-5-(3-chloro-6-(4-chloro-1H-1,2,3-triazol-1-yl)-2-fluorophenyl)-2-(2-(4-fluoro-1H-pyrazol-1-yl)-1-(4-(1-methyl-1H-1,2,3-triazol-5-yl)-1H-pyrazol-1-yl)ethyl)pyridine 1-oxide as an off-white solid.

HPLC purity (method B): 99.6%, retention time=1.316 min. LC/MS: mass calculated for C$_{24}$H$_{17}$Cl$_2$F$_2$N$_{11}$O: 583.10, measured (ES, m/z): 584.15 [M+H]$^+$. $^1$H NMR (400 MHz, DMSO-d$_6$) δ 8.69 (s, 1H), 8.49 (d, J=1.4 Hz, 1H), 8.38 (s, 1H), 7.99-8.08 (m, 2H), 7.86 (s, 1H), 7.73-7.64 (m, 2H), 7.43-7.52 (m, 2H), 7.15-7.23 (m, 1H), 6.55-6.67 (m, 1H), 4.85-5.04 (m, 2H), 4.03 (s, 3H). $^{19}$F NMR (376 MHz, DMSO) δ −112.88, −177.81.

Example 576: (R)-5-(3-Chloro-2-fluoro-6-(1H-tetrazol-1-yl)phenyl)-2-(2-(4-fluorophenyl)-1-(4-(1-methyl-1H-1,2,3-triazol-5-yl)-1H-pyrazol-1-yl)ethyl)pyridine 1-oxide

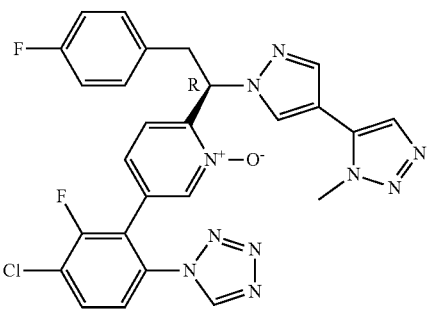

Step 1: 1-(5-Bromopyridin-2-yl)-2-(4-fluorophenyl)ethan-1-ol

To a solution of 2,5-dibromopyridine (5.0 g, 21.1 mmol, 1.00 eq.) in toluene (75 mL) under nitrogen was added n-butyllithium (9.3 mL, 23.2 mmol, 2.50 M in THF, 1.05 eq.) at −78° C. and the solution was stirred for 1 h at this temperature. To the resulting solution was then added a solution of 2-(4-fluorophenyl)acetaldehyde (3.1 g, 11.2 mmol, 1.10 eq.) in toluene (25 mL) at −78° C. and the resulting mixture was stirred for 2 h at −78° C., quenched with sat. NH$_4$Cl (aq.) and extracted with ethyl acetate twice. The combined organic layer was washed with brine, dried over Na$_2$SO$_4$ and concentrated. The residue was purified by silica gel chromatography (0-50% EtOAc/petroleum ether) to yield 1-(5-bromopyridin-2-yl)-2-(4-fluorophenyl)ethan-1-ol as a light red solid. LC/MS: mass calculated for C$_{13}$H$_{11}$BrFNO: 295.0, measured: 296.0, 298.0 [M+H, M+H+2]$^+$.

Step 2: 1-(5-Bromopyridin-2-yl)-2-(4-fluorophenyl)ethyl methanesulfonate

To a mixture of 1-(5-bromopyridin-2-yl)-2-(4-fluorophenyl)ethan-1-ol (5.1 g, 17.2 mmol, 1.00 eq.) and triethylamine (5.23 g, 51.7 mmol, 3.00 eq.) in DCM (50 mL) was added methanesulfonyl chloride (2.4 g, 20.7 mmol, 1.20 eq.) at 0° C. and the solution was stirred for 1 h at room temperature, then diluted with water and washed with brine. The organic layer was dried over Na$_2$SO$_4$ and concentrated. The residue was purified by silica gel chromatography (0-50% EtOAc/petroleum ether) to yield 1-(5-bromopyridin-2-yl)-2-(4-fluorophenyl)ethyl methanesulfonate as a

Step 3: 5-Bromo-2-(2-(4-fluorophenyl)-1-(4-(1-methyl-1H-1,2,3-triazol-5-yl)-1H-pyrazol-1-yl)ethyl)pyridine A mixture of cesium carbonate (876 mg, 2.67 mmol, 1.0 eq.) and 1-methyl-5-(1H-pyrazol-4-yl)-1H-1,2,3-triazole (438 mg, 2.94 mmol, 1.1 eq.) in acetonitrile (3 mL) was stirred for 15 min at room temperature. 1-(5-Bromopyridin-2-yl)-2-(4-fluorophenyl)ethyl methanesulfonate (1.0 g, 2.67 mmol, 1.0 eq.) was added and the solution was stirred for 3 h at 70° C. The solution was diluted with $H_2O$, extracted with ethyl acetate twice. The combined organic layers were washed with brine, dried over $Na_2SO_4$, concentrated and purified by silica gel chromatography (0%→8%, DCM/MeOH) to yield 2-(1-(4-(4H-1,2,4-triazol-4-yl)-1H-pyrazol-1-yl)-3-methoxypropyl)-5-bromopyridine as a light yellow oil. LC/MS: mass calculated for $C_{19}H_{16}BrFN_6$:426.06, measured (ES, m/z): 427.10 [M+H]$^+$.

Step 4: 4-Chloro-3-fluoro-2-(6-(2-(4-fluorophenyl)-1-(4-(1-methyl-1H-1,2,3-triazol-5-yl)-1H-pyrazol-1-yl)ethyl)pyridin-3-yl)aniline A mixture of 5-bromo-2-(2-(4-fluorophenyl)-1-(4-(1-methyl-1H-1,2,3-triazol-5-yl)-1H-pyrazol-1-yl)ethyl)pyridine (1.0 g, 2.40 mmol, 1.0 eq.), 6-amino-3-chloro-2-fluorophenylboronic acid (1.1 g, 6.0 mmol, 2.5 eq.), Pd(PPh$_3$)$_4$ (138 mg, 0.12 mmol, 0.05 eq.), potassium carbonate (1.2 g, 8.39 mmol, 3.5 eq.) in 1,4-dioxane/water (V/V=5:1, 6 mL) was refluxed at 90° C. under $N_2$ for 2 h. The reaction was quenched by water (10 mL), then extracted with EA (3×20 mL). The organic layers were combined, washed with brine, dried over $Na_2SO_4$ and concentrated. The residue was purified by silica gel chromatography (0%→10%, MeOH/DCM) to yield 4-chloro-3-fluoro-2-(6-(2-(4-fluorophenyl)-1-(4-(1-methyl-1H-1,2,3-triazol-5-yl)-1H-pyrazol-1-yl)ethyl)pyridin-3-yl)aniline as a yellow oil. LC/MS: mass calculated for $C_{19}H_{16}BrFN_6$:491.14, measured (ES, m/z): 492.10 [M+H]$^+$.

Step 5: 5-(3-Chloro-2-fluoro-6-(1H-tetrazol-1-yl)phenyl)-2-(2-(4-fluorophenyl)-1-(4-(1-methyl-1H-1,2,3-triazol-5-yl)-1H-pyrazol-1-yl)ethyl)pyridine A mixture of 4-chloro-3-fluoro-2-(6-(2-(4-fluorophenyl)-1-(4-(1-methyl-1H-1,2,3-triazol-5-yl)-1H-pyrazol-1-yl)ethyl)pyridin-3-yl)aniline (900 mg, 1.83 mmol, 1.0 eq.), TMSN$_3$ (2 mL), azidotrimethylsilane (2 mL) and acetic acid (2 mL) was stirred overnight at 45° C. The resulting mixture was concentrated and purified by reverse phase chromatography on C18 (0%→55% MeCN/H$_2$O (0.05% CF$_3$COOH)) to yield 5-(3-chloro-2-fluoro-6-(1H-tetrazol-1-yl)phenyl)-2-(2-(4-fluorophenyl)-1-(4-(1-methyl-1H-1,2,3-triazol-5-yl)-1H-pyrazol-1-yl)ethyl)pyridine as a light yellow solid. LC/MS: mass calculated for $C_{26}H_{19}ClF_2N_{10}$: 544.15, measured (ES, m/z): (ES, m/z) 545.10 [M+H]$^+$.

Step 6: (R)-5-(3-Chloro-2-fluoro-6-(1H-tetrazol-1-yl)phenyl)-2-(2-(4-fluorophenyl)-1-(4-(1-methyl-1H-1,2,3-triazol-5-yl)-1H-pyrazol-1-yl)ethyl)pyridine 1-oxide A mixture of 5-(3-chloro-2-fluoro-6-(1H-tetrazol-1-yl)phenyl)-2-(2-(4-fluorophenyl)-1-(4-(1-methyl-1H-1,2,3-triazol-5-yl)-1H-pyrazol-1-yl)ethyl)pyridine (300 mg, 0.55 mmol, 1.0 eq.), methyltrioxorhenium (68.6 mg, 0.28 mmol, 0.5 eq.) and hydrogen peroxide (0.5 mL, 30 wt %) in CH$_3$OH (3 mL) was stirred for 3 h at room temperature. The resulting mixture was purified by reverse phase chromatography on C18 (MeCN/H$_2$O (0.05% CF$_3$COOH)) to yield 5-(3-chloro-2-fluoro-6-(1H-tetrazol-1-yl)phenyl)-2-(2-(4-fluorophenyl)-1-(4-(1-methyl-1H-1,2,3-triazol-5-yl)-1H-pyrazol-1-yl)ethyl)pyridine 1-oxide as a light yellow solid. The racemic product was separated by chiral-HPLC to yield (R)-5-(3-chloro-2-fluoro-6-(1H-tetrazol-1-yl)phenyl)-2-(2-(4-fluorophenyl)-1-(4-(1-methyl-1H-1,2,3-triazol-5-yl)-1H-pyrazol-1-yl)ethyl)pyridine 1-oxide as an off-white solid. HPLC purity (method A): 100%, retention time=1.289 min. LC/MS: mass calculated for $C_{26}H_{19}ClF_2N_{10}O$: 560.14, measured (ES, m/z): 561.10[M+H]$^+$. $^1$H NMR: (300 MHz, DMSO-d$_6$) δ 9.70 (s, 1H), 8.48 (s, 1H), 8.37 (s, 1H), 7.98-8.09 (m, 1H), 7.98 (s, 1H), 7.83 (s, 1H), 7.74-7.78 (m, 1H), 7.45 (d, J=8.3 Hz, 1H), 7.11-7.25 (m, 3H), 7.03-7.09 (m, 2H), 6.21-6.26 (m, 1H), 3.99 (s, 3H), 3.46-3.66 (m, 2H). $^{19}$F-NMR: (282 MHz, DMSO-d$_6$) δ −112.69, −116.07.

Example 577: (S)-5-(3-Chloro-2-fluoro-6-(1H-tetrazol-1-yl)phenyl)-2-(2-(4-fluorophenyl)-1-(4-(1-methyl-1H-1,2,3-triazol-5-yl)-1H-pyrazol-1-yl)ethyl)pyridine 1-oxide

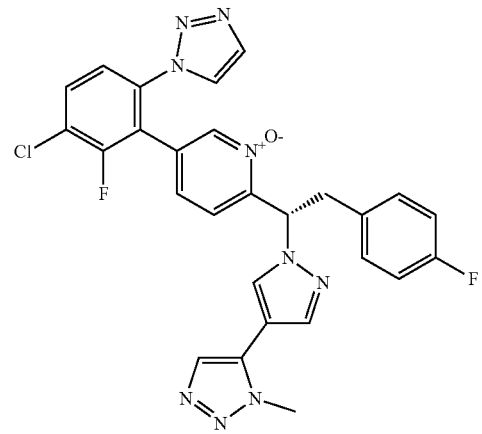

LC/MS: mass calculated for $C_{26}H_{19}ClF_2N_{10}O$: 560.14, measured (ES, m/z): 561.15 [M+H]$^+$. $^1$H NMR (300 MHz, DMSO-d$_6$) δ 9.70 (s, 1H), 8.48 (d, J=1.5 Hz, 1H), 8.37 (s, 1H), 8.02-8.09 (m, 1H), 7.98 (s, 1H), 7.83 (s, 1H), 7.76 (dd, J=8.7, 1.6 Hz, 1H), 7.45 (d, J=8.3 Hz, 1H), 7.11-7.24 (m, 3H), 6.96-7.08 (m, 2H), 6.15-6.26 (m, 1H), 3.99 (s, 3H), 3.45-3.66 (m, 2H). $^{19}$F NMR (282 MHz, DMSO-d$_6$) δ −112.69, −116.07.

Example 578: 5-(3-Chloro-2-fluoro-6-(1H-tetrazol-1-yl)phenyl)-2-(2-cyclopropyl-1-(4-(4-(trifluoromethyl)thiazol-5-yl)-1H-pyrazol-1-yl)ethyl)pyridine 1-oxide

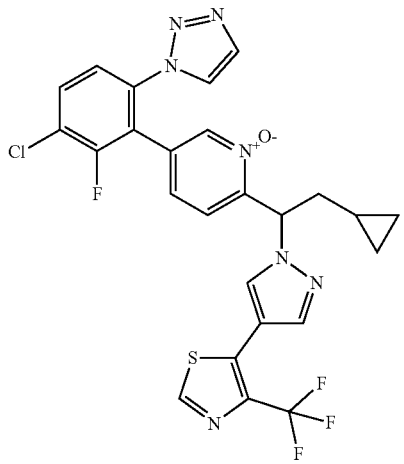

LC/MS: mass calculated for C₂₄H₁₇ClF₄N₈OS: 576.1, measured (ES, m/z): 577.2 [M+H]⁺. ¹H NMR (400 MHz, CD₃OD) δ 9.38 (s, 1H), 8.97 (s, 1H), 8.36 (s, 1H), 8.27 (s, 1H), 7.91 (s, 1H), 7.80 (s, 1H), 7.53-7.65 (m, 2H), 7.30 (br d, J=8.59 Hz, 1H), 6.23 (br d, J=7.58 Hz, 1H), 2.38-2.48 (m, 1H), 2.01-2.08 (m, 1H), 0.61-0.74 (m, 1H), 0.33-0.49 (m, 2H), 0.17 (br d, J=4.55 Hz, 1H).

Example 579: 5-(3-Chloro-2-fluoro-6-(1H-tetrazol-1-yl)phenyl)-2-(2-cyclopropyl-1-(4-(1-methyl-1H-tetrazol-5-yl)-1H-pyrazol-1-yl)ethyl)pyridine 1-oxide

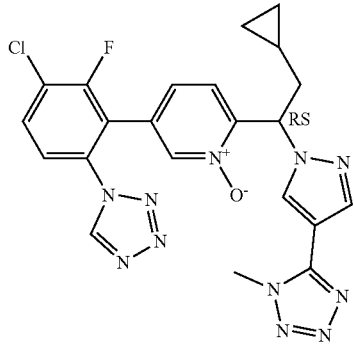 [SMILES: Cn1nnnc1-c1cnn(C(CC2CC2)c2ccc(-c3c(-n4cnnn4)ccc(Cl)c3F)c[n+]2[O-])c1]

LC/MS: mass calculated for C₂₂H₁₉ClFN₁O: 507.1, measured (ES, m/z): 508.2 [M+H]⁺. ¹H NMR (400 MHz, CD₃OD) δ 9.38 (s, 1H), 8.67 (s, 1H), 8.37 (s, 1H), 8.17 (s, 1H), 7.86-7.96 (m, 1H), 7.60 (br d, J=8.59 Hz, 2H), 7.30 (br d, J=8.08 Hz, 1H), 6.32 (br d, J=6.57 Hz, 1H), 4.22 (s, 3H), 2.43-2.71 (m, 1H), 1.99-2.19 (m, 1H), 0.67 (br d, J=4.55 Hz, 1H), 0.26-0.52 (m, 2H), 0.15-0.24 (m, 1H), −0.02-0.07 (m, 1H).

Example 580: 5-(3-Chloro-2-fluoro-6-(1H-tetrazol-1-yl)phenyl)-2-(2-cyclopropyl-1-(2-(difluoromethyl)-1'H,2H-[3,4'-bipyrazol]-1'-yl)ethyl)pyridine 1-oxide

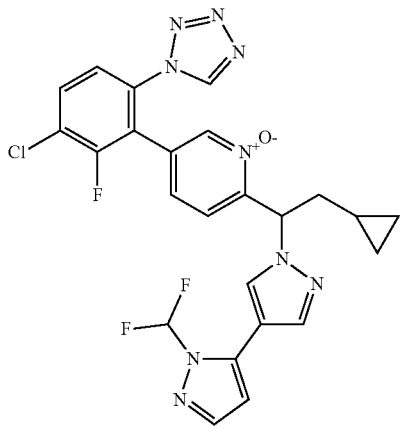

LC/MS: mass calculated for C₂₄H₁₉ClF₃N₉O C₂₄H₁₉ClF₃N₉O, 541.1, measured (ES, m/z): 542.3 [M+H]⁺. ¹H NMR (400 MHz, CD₃OD) δ 9.38 (s, 1H), 8.37 (s, 1H), 8.26 (s, 1H), 7.91 (br t, J=8.08 Hz, 1H), 7.85 (s, 1H), 7.68 (s, 1H), 7.53-7.63 (m, 2H), 7.27-7.35 (m, 1H), 6.55-6.62 (m, 1H), 6.24 (br dd, J=3.28, 9.85 Hz, 1H), 3.28-3.33 (m, 1H), 2.39-2.52 (m, 1H), 2.01-2.09 (m, 1H), 0.60-0.73 (m, 1H), 0.34-0.51 (m, 2H), 0.14-0.23 (m, 1H), −0.04-0.07 (m, 1H).

Example 581: 5-(3-Chloro-2-fluoro-6-(1H-tetrazol-1-yl)phenyl)-2-(2-cyclopropyl-1-(4-(5-(trifluoromethyl)-1,3,4-thiadiazol-2-yl)-1H-pyrazol-1-yl)ethyl)pyridine 1-oxide

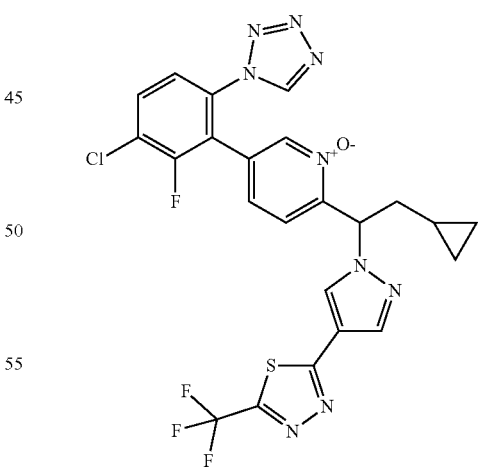

LC/MS: mass calculated for C₂₃H₁₆ClF₄N₉OS: 577.1, measured (ES, m/z): 578.1 [M+H]⁺. ¹H NMR (400 MHz, CD₃OD) δ ppm 9.38 (s, 1H), 8.74 (s, 1H), 8.37 (s, 1H), 8.20 (s, 1H), 7.86-7.96 (m, 1H), 7.56-7.66 (m, 2H), 7.30 (dd, J=8.31, 1.47 Hz, 1H) 6.23-6.35 (m, 1H), 2.42-2.54 (m, 1H), 2.02-2.12 (m, 1H), 0.63-0.75 (m, 1H), 0.34-0.50 (m, 2H), 0.13-0.23 (m, 1H), −0.06-0.07 (m, 1H).

Example 582: (R)-5-(3-Chloro-6-(4-chloro-1H-1,2,3-triazol-1-yl)-2-fluorophenyl)-2-(3-methoxy-1-(4-(1-methyl-1H-1,2,3-triazol-5-yl)-1H-pyrazol-1-yl)propyl)pyridine 1-oxide

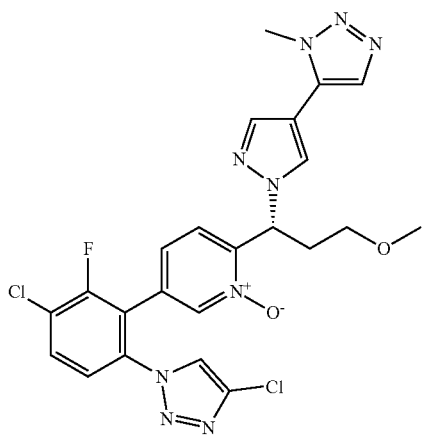 [SMILES: COCC[C@H](c1ccc(-c2c(-n3cc(Cl)nn3)ccc(Cl)c2F)c[n+]1[O-])n1cc(-c2cnnn2C)cn1]

Step 1:
1-(5-Bromopyridin-2-yl)-3-methoxypropan-1-one

To a solution of 2,5-dibromopyridine (10 g, 42.2 mmol, 1.00 eq.) in toluene (100 mL) under nitrogen was added n-butyllithium (17.73 mL, 44.3 mmol, 2.50 M in THF, 1.05 eq.) at −78° C. and the solution was stirred for 1 h at this temperature. To the solution was then added the solution of N,3-dimethoxy-N-methylpropanamide (6.8 g, 46.4 mmol, 1.10 eq.) in toluene (20 mL) at −78° C. and the solution was allowed to stirred for 2 h at −78° C. The solution was quenched with sat. NH$_4$Cl aqueous solution and extracted with EtOAc twice. The combined organic layer was washed with brine, dried over Na$_2$SO$_4$ and concentrated. The residue was purified by silica gel chromatography (0-50% EtOAc/petroleum ether) to yield 1-(5-bromopyridin-2-yl)-3-methoxypropan-1-one as a light yellow solid. LC/MS: mass calculated for $C_9H_{10}BrNO_2$: 243.0, measured: 244.0, 246.0 [M+H, M+H+2]$^+$.

Step 2:
1-(5-Bromopyridin-2-yl)-3-methoxypropan-1-ol

To a solution of 1-(5-bromopyridin-2-yl)-3-methoxypropan-1-one (6.2 g, 25.4 mmol, 1.00 eq.) in methanol (10 mL) was added sodium borohydride (1.2 g, 30.5 mmol, 1.20 eq.) in portions at 0° C. and the solution was stirred for 1 h at room temperature. The reaction was quenched with water and extracted with EtOAc twice. The combined organic layers were washed with water and brine. The organic layer was dried over Na$_2$SO$_4$ and concentrated to yield 1-(5-bromopyridin-2-yl)-3-methoxypropan-1-ol as yellow oil. LC/MS: mass calculated for $C_9H_{12}BrNO_2$: 245.0, measured: 246.0, 248.0 [M+H, M+H+2]$^+$.

Step 3: 1-(5-Bromopyridin-2-yl)-3-methoxypropyl methanesulfonate

To a mixture of 1-(5-bromopyridin-2-yl)-3-methoxypropan-1-ol (5.9 g, 24.0 mmol, 1.00 eq.) and triethylamine (7.3 g, 71.9 mmol, 3.00 eq.) in DCM (60 mL) was added methanesulfonyl chloride (3.3 g, 28.8 mmol, 1.20 eq.) at 0° C. and the solution was stirred for 2 h at room temperature. The reaction was washed with water and brine. The organic layer was dried over Na$_2$SO$_4$ and concentrated. The residue was purified by silica gel chromatography (0-50% EtOAc/petroleum ether) to yield 1-(5-bromopyridin-2-yl)-3-methoxypropyl methanesulfonate as a yellow solid. LC/MS: mass calculated for $C_{10}H_{14}BrNO_4S$: 323.0, measured: 324.0, 326.0 [M+H, M+H+2]$^+$.

Step 4: 5-Bromo-2-(3-methoxy-1-(4-(1-methyl-1H-1,2,3-triazol-5-yl)-1H-pyrazol-1-yl)propyl)pyridine A mixture of 1-methyl-5-(1H-pyrazol-4-yl)-1H-1,2,3-triazole (1 g, 6.7 mmol, 1 eq.) and cesium carbonate (2.40 g, 7.4 mmol, 1.1 eq.) in acetonitrile (10 mL) was stirred for 15 min at room temperature. 1-(5-Bromopyridin-2-yl)-3-methoxypropyl methanesulfonate (2.2 g, 6.7 mmol, 1 eq.) was added and the solution was stirred for 3 h at 90° C. The solution was diluted with H$_2$O, extracted with ethyl acetate twice. The combined organic layers was washed with brine, dried over Na$_2$SO$_4$, concentrated and purified by silica gel chromatography (0-50% EtOAc/petroleum ether) to yield 5-bromo-2-(3-methoxy-1-(4-(1-methyl-1H-1,2,3-triazol-5-yl)-1H-pyrazol-1-yl)propyl)pyridine as a light yellow oil. LC/MS: mass calculated for $C_{15}H_{17}BrN_6O$: 376, measured: 376.95 [M+H]$^+$.

Step 5: (6-(3-Methoxy-1-(4-(1-methyl-1H-1,2,3-triazol-5-yl)-1H-pyrazol-1-yl)propyl)pyridin-3-yl)boronic acid A mixture of 5-bromo-2-(3-methoxy-1-(4-(1-methyl-1H-1,2,3-triazol-5-yl)-1H-pyrazol-1-yl)propyl)pyridine (0.5 g, 1.3 mmol, 1.0 eq), 4,4,4',4',5,5,5',5'-octamethyl-2,2'-bi(1,3,2-dioxaborolane) (0.67 g, 2.7 mmol, 2 eq), Pd(dppf)Cl$_2$ (0.097 g, 0.13 mmol, 0.1 eq.), K$_2$CO$_3$ (0.39 g, 3.98 mmol, 3 eq.) in 1,4-dioxane (5 mL) was heated at reflux at 90° C. under N$_2$ for 2 h. The mixture was diluted with H$_2$O, extracted with ethyl acetate twice. The combined organic layers was washed with brine, dried over Na$_2$SO$_4$, concentrated to yield (6-(3-methoxy-1-(4-(1-methyl-1H-1,2,3-triazol-5-yl)-1H-pyrazol-1-yl)propyl)pyridin-3-yl)boronic acid. LC/MS: mass calculated for $C_{15}H_{19}BN_6O_3$: 342, measured: 343.05 [M+H]$^+$.

Step 6: 1-Azido-4-chloro-3-fluoro-2-iodobenzene

4-Chloro-3-fluoro-2-iodoaniline (2.0 g, 7.4 mmol) was dissolved in CH$_3$CN (10 mL). Then azidotrimethylsilane (1.5 mL) and tert-butyl nitrite (1.3 mL) were added into the mixture dropwise. The mixture was stirred at room temperature for 17 h. The solvent was removed under reduced pressure. The residue was applied onto a silica gel column with ethyl acetate/petroleum ether (1:10) to yield 1-azido-4-chloro-3-fluoro-2-iodobenzene as a brown solid.

Step 7: 1-(4-Chloro-3-fluoro-2-iodophenyl)-4-(tributylstannyl)-1H-1,2,3-triazole To a solution of 1-azido-4-chloro-3-fluoro-2-iodobenzene (1.83 g, 6.15 mmol, 1 eq) in toluene (10 mL) was added tributyl(ethynyl)stannane (5.340 mL, 17.9 mmol, 3 eq) at room temperature, the reaction was then stirred overnight at 100° C. under N$_2$ atmosphere. The resulting solution was concentrated under vacuum and applied onto a silica gel column with ethyl acetate/petroleum ether (1:9) to yield 1-(4-chloro-3-fluoro-2-iodophenyl)-4-(tributylstannyl)-1H-1,2,3-triazole as a white solid. LC/MS: mass calculated for $C_{20}H_{30}ClFIN_3Sn$: 613, measured: 614 [M+H]$^+$.

Step 8: 4-Chloro-1-(4-chloro-3-fluoro-2-iodophenyl)-1H-1,2,3-triazole

To 1-(4-Chloro-3-fluoro-2-iodophenyl)-4-(tributylstannyl)-1H-1,2,3-triazole (10 g, 16.3 mmol, 1.0 eq) in CH$_3$CN (100 mL) was added NCS (2.18 g, 16.3 mmol, 1 eq). The resulting mixture was stirred at 80° C. for 4 h and concentrated under reduced pressure. The residue was applied onto a silica gel column to yield 4-chloro-1-(4-chloro-3-fluoro-2-iodophenyl)-1H-1,2,3-triazole. LC/MS: mass calculated for $C_8H_3Cl_2FIN_3$: 356.87, measured: 357.10 [M+H]$^+$.

Step 9: 5-(3-Chloro-6-(4-chloro-1H-1,2,3-triazol-1-yl)-2-fluorophenyl)-2-(3-methoxy-1-(4-(1-methyl-1H-1,2,3-triazol-5-yl)-1H-pyrazol-1-yl)propyl)pyridine (6-(3-Methoxy-1-(4-(1-methyl-1H-1,2,3-triazol-5-yl)-1H-pyrazol-1-yl)propyl)pyridin-3-yl)boronic acid (120.0 mg, 0.35 mmol, 1.0 eq.), 4-chloro-1-(4-chloro-3-fluoro-2-iodophenyl)-1H-1,2,3-triazole (188.3 mg, 0.53 mmol, 1.5 eq.), Pd(PPh$_3$)$_4$ (40.5 mg, 0.035 mmol, 0.1 eq.) and K$_2$CO$_3$ (145.4 mg, 1.05 mmol, 3.0 eq.) were dissolved in 1,4-dioxane (10.0 mL) and H$_2$O (2.0 mL). The flask was evacuated and flushed three times with nitrogen and the mixture was stirred 40 h at 100° C. under an atmosphere of nitrogen. The resulting solution was diluted with water (50 mL), then extracted with EtOAc (3×20.0 mL). The organic layer was washed with brine (50.0 mL), dried and concentrated under vacuum. The residue was applied onto a silica gel column with ethyl acetate/petroleum ether (1:1) to yield 5-(3-chloro-6-(4-chloro-1H-1,2,3-triazol-1-yl)-2-fluorophenyl)-2-(3-methoxy-1-(4-(1-methyl-1H-1,2,3-triazol-5-yl)-1H-pyrazol-1-yl)propyl)pyridine as a light yellow oil.

Step 10: (R)-5-(3-Chloro-6-(4-chloro-1H-1,2,3-triazol-1-yl)-2-fluorophenyl)-2-(3-methoxy-1-(4-(1-methyl-1H-1,2,3-triazol-5-yl)-1H-pyrazol-1-yl)propyl)pyridine 1-oxide 5-(3-Chloro-6-(4-chloro-1H-1,2,3-triazol-1-yl)-2-fluorophenyl)-2-(3-methoxy-1-(4-(1-methyl-1H-1,2,3-triazol-5-yl)-1H-pyrazol-1-yl)propyl)pyridine (100.0 mg, 0.19 mmol, 1.0 eq.), MeReO$_3$ (8.0 mg, 0.032 mmol, 0.17 eq.) and H$_2$O$_2$ (1.0 mL) were dissolved in DMF (2.0 mL) and the resulting mixture was stirred at room temperature for 2 h. The reaction mixture was purified by chromatography on C18 (80 g, MeCN/H$_2$O (0.05% CF$_3$COOH): 0>>>60%) and prep-chiral-HPLC. The collected fractions were combined and concentrated under vacuum to yield (R)-5-(3-chloro-6-(4-chloro-1H-1,2,3-triazol-1-yl)-2-fluorophenyl)-2-(3-methoxy-1-(4-(1-methyl-1H-1,2,3-triazol-5-yl)-1H-pyrazol-1-yl)propyl)pyridine 1-oxide as an off-white solid.

HPLC purity (method A): 99.9%, retention time=1.427 min. LC/MS: mass calculated for $C_{23}H_{20}Cl_2FN_9O_2$: 543.11, measured (ES, m/z): 544.00 [M+H]$^+$. $^1$H NMR (400 MHz, CD$_3$OD) δ 8.30-8.39 (m, 2H), 7.97 (s, 1H), 7.84-7.94 (m, 2H), 7.54-7.63 (m, 2H), 7.34 (dd, J=8.4, 1.6 Hz, 1H), 6.35-6.45 (m, 1H), 4.17 (s, 3H), 3.40-3.51 (m, 1H), 3.32 (s, 3H), 3.22-3.29 (m, 1H), 2.60-2.70 (m, 2H). $^{19}$F NMR (376 MHz, CD$_3$OD) δ −114.18.

Example 583: (R)-2-(1-(4-(1,3,4-Oxadiazol-2-yl)-1H-pyrazol-1-yl)-2-cyclopropylethyl)-5-(3-chloro-2-fluoro-6-(1H-tetrazol-1-yl)phenyl)pyridine 1-oxide

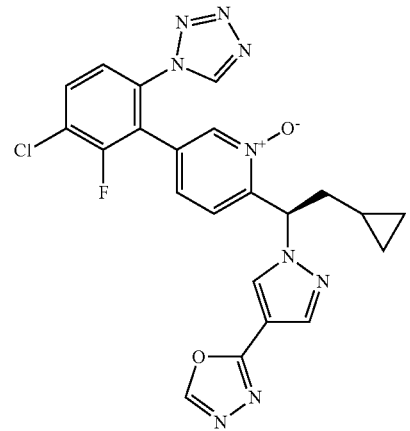 [SMILES: [O-][n+]1cc(-c2c(-n3cnnn3)ccc(Cl)c2F)ccc1[C@@H](CC1CC1)n1cc(-c2nnco2)cn1]

LC/MS: mass calculated for $C_{22}H_{17}ClFN_9O_2$: 493.12, measured (ES, m/z): 494.05 [M+H]$^+$. $^1$H NMR (400 MHz, CD$_3$OD) δ 9.39 (s, 1H), 8.94 (s, 1H), 8.67 (s, 1H), 8.35-8.40 (m, 1H), 8.17 (s, 1H), 7.93 (dd, J=8.7, 7.6 Hz, 1H), 7.56-7.66 (m, 2H), 7.32 (dd, J=8.3, 1.7 Hz, 1H), 6.21-6.33 (m, 1H), 2.40-2.53 (m, 1H), 2.00-2.12 (m, 1H), 0.60-0.73 (m, 1H), 0.34-0.52 (m, 2H), 0.14-0.24 (m, 1H), 0.00-0.06 (m, 1H). $^{19}$F NMR (376 MHz, CD$_3$OD) δ −113.72.

Example 584: (S)-5-(3-Chloro-6-(4-chloro-1H-1,2,3-triazol-1-yl)-2-fluorophenyl)-2-(3-methoxy-1-(4-(1-methyl-1H-1,2,3-triazol-5-yl)-1H-pyrazol-1-yl)propyl)pyridine 1-oxide

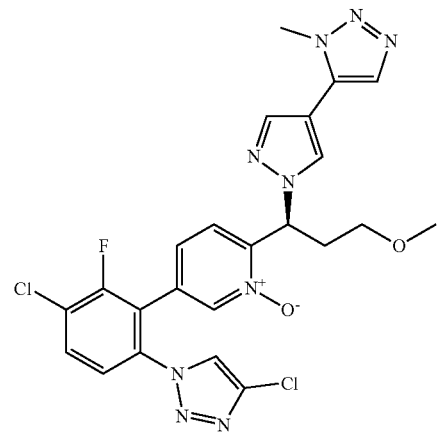 [SMILES: COCC[C@@H](c1ccc(-c2c(-n3cc(Cl)nn3)ccc(Cl)c2F)c[n+]1[O-])n1cc(-c2cnnn2C)cn1]

LC/MS: mass calculated for $C_{23}H_{20}Cl_2FN_9O_2$: 543.11, measured (ES, m/z): 544.05 [M+H]$^+$. $^1$H NMR (400 MHz, CD$_3$OD) δ 8.30-8.39 (m, 3H), 7.97 (s, 1H), 7.94-7.84 (m, 2H), 7.54-7.63 (m, 2H), 7.34 (dd, J=8.4, 1.6 Hz, 1H), 6.36-6.46 (m, 1H), 4.17 (s, 3H), 3.40-3.50 (m, 1H), 3.32 (s, 3H), 2.21-3.29 (m, 1H), 1.60-1.70 (m, 2H). $^{19}$F NMR (376 MHz, CD$_3$OD) δ −114.18.

Example 585: (S)-2-(1-(4-(1,3,4-Oxadiazol-2-yl)-1H-pyrazol-1-yl)-2-cyclopropylethyl)-5-(3-chloro-2-fluoro-6-(1H-tetrazol-1-yl)phenyl)pyridine 1-oxide

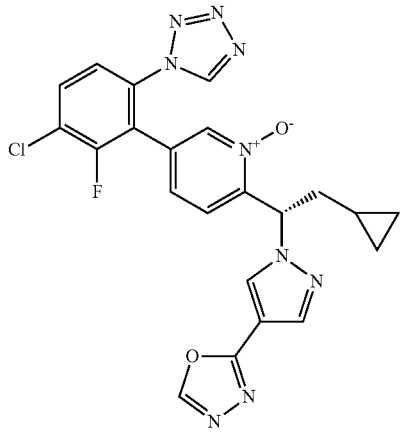 [SMILES: [O-][n+]1cc(-c2c(-n3cnnn3)ccc(Cl)c2F)ccc1[C@H](CC1CC1)n1cc(-c2nnco2)cn1]

LC/MS: mass calculated for $C_{22}H_{17}ClFN_9O_2$: 493.12, measured (ES, m/z): 494.05 [M+H]$^+$. $^1$H NMR (400 MHz, CD$_3$OD) δ 9.39 (s, 1H), 8.94 (s, 1H), 8.67 (s, 1H), 8.32-8.39 (m, 1H), 8.17 (s, 1H), 7.93 (dd, J=8.7, 7.6 Hz, 1H), 7.56-7.66 (m, 2H), 7.32 (dd, J=8.3, 1.7 Hz, 1H), 6.25-6.35 (m, 1H), 2.40-2.53 (m, 1H), 2.00-2.10 (m, 1H), 0.60-0.73 (m, 1H), 0.34-0.52 (m, 2H), 0.14-0.24 (m, 1H), 0.00-0.06 (m, 1H). $^{19}$F NMR (376 MHz, CD$_3$OD) δ −113.73.

Example 586: 5-(3-Chloro-2-fluoro-6-(1H-tetrazol-1-yl)phenyl)-2-(2-cyclopropyl-1-(2-methyl-5-(trifluoromethyl)-1'H,2H-[3,4'-bipyrazol]-1'-yl)ethyl)pyridine 1-oxide

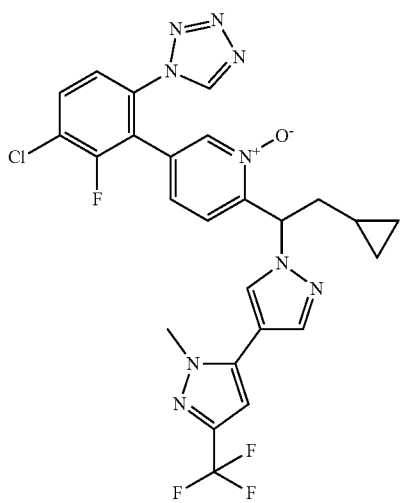 [SMILES: Cn1nc(C(F)(F)F)cc1-c1cnn(C(CC2CC2)c2ccc(-c3c(-n4cnnn4)ccc(Cl)c3F)c[n+]2[O-])c1]

LC/MS: mass calculated for $C_{25}H_{20}ClF_4N_9O$: 573.1, measured (ES, m/z): 574.2 [M+H]$^+$. $^1$H NMR (400 MHz, CD$_3$OD) δ ppm 0.01-0.08 (m, 1H) 0.15-0.22 (m, 1H) 0.34-0.50 (m, 2 h) 0.64-0.76 (m, 1H) 2.03 (s, 1H) 2.43-2.51 (m, 1H) 3.99 (s, 3H) 6.22-6.30 (m, 1H) 6.73 (s, 1H) 7.29 (d, J=8.31 Hz, 1H) 7.53 (d, J=8.31 Hz, 1H) 7.58-7.64 (m, 1H) 7.86-7.95 (m, 2 h) 8.33 (s, 1H) 8.37 (s, 1H) 9.39 (s, 1H).

Example 587: (S)-5-(3-Chloro-2-fluoro-6-(1H-tetrazol-1-yl)phenyl)-2-(3-(difluoromethoxy)-1-(4-(1-methyl-1H-1,2,4-triazol-5-yl)-1H-pyrazol-1-yl)propyl)pyridine 1-oxide

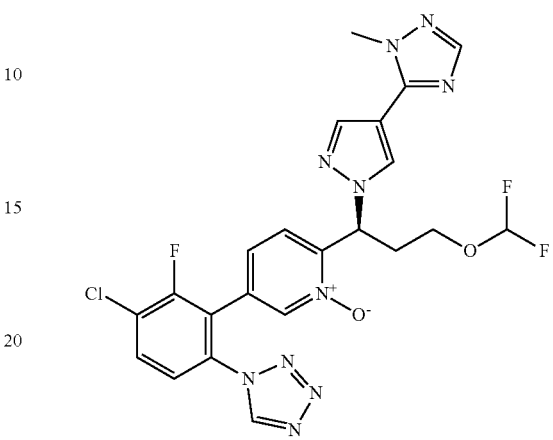

LC/MS: mass calculated for $C_{22}H_{18}ClF_3N_{10}O_2$: 546.13, measured (ES, m/z): 547.10 [M+H]$^+$. $^1$H NMR (400 MHz, DMSO-d$_6$) δ 9.69 (s, 1H), 8.62 (s, 1H), 8.47 (d, J=1.6 Hz, 1H), 8.03-8.13 (m, 2H), 7.90 (s, 1H), 7.76 (dd, J=8.7, 1.5 Hz, 1H), 7.30 (d, J=8.3 Hz, 1H), 7.19 (dd, J=8.3, 1.6 Hz, 1H), 6.64 (t, J=75.7 Hz, 1H), 6.21-6.30 (m, 1H), 3.97 (s, 3H), 3.80-3.90 (m, 1H), 3.65-3.76 (m, 1H), 2.56-2.73 (m, 2H). $^{19}$F NMR (376 MHz, DMSO-d$_6$) δ −83.31, −112.67.

Example 588: (R)-5-(3-Chloro-2-fluoro-6-(1H-tetrazol-1-yl)phenyl)-2-(3-(difluoromethoxy)-1-(4-(1-methyl-1H-1,2,4-triazol-5-yl)-1H-pyrazol-1-yl)propyl)pyridine 1-oxide

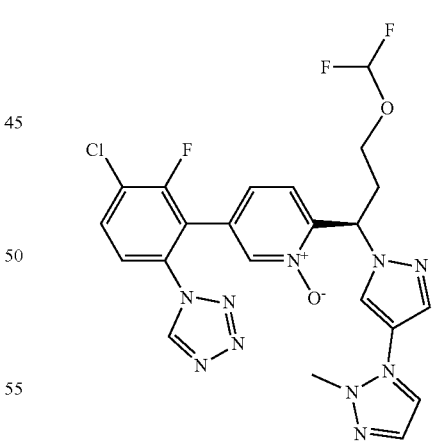

Step 1: 5-Bromo-2-(3-((tert-butyldimethylsilyl)oxy)-1-((tetrahydro-2H-pyran-2-yl)oxy)propyl)pyridine A mixture of 1-(5-bromopyridin-2-yl)-3-((tert-butyldimethylsilyl)oxy)propan-1-ol (12.1 g, 34.9 mmol, 1.0 equiv.), 4-methylbenzenesulfonic acid (0.60 g, 3.49 mmol, 0.1 equiv.) and 3,4-Dihydro-2H-pyran (8.8 g, 104.8 mmol, 3.0 equiv.) in dichloromethane (120 mL) was stirred for 1 h at 70° C. The pH value of the solution was adjusted to ~6-7 with sodium bicarbonate. The resulting solution was extracted with dichloromethane. The organic layers were combined, washed with sodium carbonate (aq.) and brine, dried and concentrated under vacuum to the residue of 5-bromo-2-(3-((tert-butyldimethylsilyl)oxy)-1-((tetrahydro-2H-pyran-2-yl)oxy)propyl)pyridine as a light yellow oil. LC/MS: mass calculated for $C_{19}H_{32}BrNO_3Si$: 429.13, measured (ES, m/z): 454.00 $[M+Na]^+$.

Step 2: 3-(5-Bromopyridin-2-yl)-3-((tetrahydro-2H-pyran-2-yl)oxy)propan-1-ol

A mixture of 5-bromo-2-(3-((tert-butyldimethylsilyl)oxy)-1-((tetrahydro-2H-pyran-2-yl) oxy)propyl)pyridine (13.5 g, 31.36 mmol, 1.0 equiv.) and tetrabutylammonium fluoride (47.0 mL, 1.0 M in THF) was stirred for 1 h at room temperature. The mixture was diluted with $H_2O$, extracted with ethyl acetate twice. The combined organic layers were washed with brine, dried over $Na_2SO_4$, concentrated and purified by silica gel chromatography (0→50% EA/PE) to yield 3-(5-bromopyridin-2-yl)-3-((tetrahydro-2H-pyran-2-yl) oxy)propan-1-ol as a light yellow oil. LC/MS: mass calculated for $C_{13}H_{18}BrNO_3$: 315.05, measured (ES, m/z): 315.95 $[M+H]^+$.

Step 3: 1-(5-Bromopyridin-2-yl)-3-(difluoromethoxy)propan-1-ol

To a solution of 3-(5-bromopyridin-2-yl)-3-((tetrahydro-2H-pyran-2-yl)oxy)propan-1-ol (4.0 g, 12.7 mmol, 1.0 equiv.) in acetonitrile (40.0 mL) added cuprous iodide (0.48 g, 2.53 mmol, 0.2 equiv.). The mixture was heated to 50° C. under nitrogen atmosphere, and a solution of 2,2-difluoro-2-(fluorosulfonyl)acetic acid (1.96 mL, 1.5 equiv.) in acetonitrile (2 mL) was added dropwise. The mixture was heated for an additional 30 min at 50° C. The resulting solution was extracted with dichloromethane. The combined organic layers was washed with brine, dried over $Na_2SO_4$, concentrated and purified by silica gel chromatography (0→50% EtOAc/petroleum ether) to yield 1-(5-bromopyridin-2-yl)-3-(difluoromethoxy)propan-1-ol as a light yellow oil. LC/MS: mass calculated for $C_9H_{10}BrF_2NO_2$: 280.99, measured (ES, m/z): 282.00, 283.90 $[M+H, M+H+2]^+$.

Step 4: 1-(5-Bromopyridin-2-yl)-3-(difluoromethoxy)propyl methanesulfonate

To a mixture of 1-(5-bromopyridin-2-yl)-3-(difluoromethoxy)propan-1-ol (1.0 g, 3.5 mmol, 1.0 equiv.) and triethylamine (2.46 mL, 1.7 mmol, 5.0 equiv.) in DCM (10.0 mL) was added methanesulfonic anhydride (1.24 g, 7.1 mmol, 2.0 equiv.) at 0° C. and the solution was stirred for 2 h at room temperature. The mixture was diluted with $H_2O$, extracted with DCM twice. The combined organic layers was washed with brine, dried over $Na_2SO_4$, concentrated and purified by silica gel chromatography (0→50% EtOAc/petroleum ether) to yield 1-(5-bromopyridin-2-yl)-3-(difluoromethoxy)propyl methanesulfonate as a light yellow solid. LC/MS: mass calculated for $C_{10}H_{12}BrF_2NO_4S$: 358.96, measured (ES, m/z): 360.00, 361.90 $[M+H, M+H+2]^+$.

Step 5: 5-Bromo-2-(3-(difluoromethoxy)-1-(4-(1-methyl-1H-1,2,4-triazol-5-yl)-1H-pyrazol-1-yl)propyl)pyridine A mixture of 1-methyl-5-(1H-pyrazol-4-yl)-1H-1,2,4-triazole (0.25 g, 1.67 mmol, 1.2 equiv.) and cesium carbonate (0.50 g, 1.53 mmol, 1.1 equiv.) in acetonitrile (5.0 mL) was stirred for 15 min at room temperature. 1-(5-Bromopyridin-2-yl)-3-(difluoromethoxy)propyl methanesulfonate (0.50 g, 1.39 mmol, 1.0 equiv.) was added and the solution was stirred for 3 h at 90° C. The solution was diluted with $H_2O$, extracted with ethyl acetate twice. The combined organic layers was washed with brine, dried over $Na_2SO_4$, concentrated and purified by silica gel chromatography (0→50% EtOAc/petroleum ether) to yield 5-bromo-2-(3-(difluoromethoxy)-1-(4-(1-methyl-1H-1,2,4-triazol-5-yl)-1H-pyrazol-1-yl)propyl)pyridine as a light yellow oil. LC/MS: mass calculated for $C_{15}H_{15}BrF_2N_6O$: 412.05, measured (ES, m/z): 412.95 $[M+H]^+$.

Step 6: 4-Chloro-2-(6-(3-(difluoromethoxy)-1-(4-(1-methyl-1H-1,2,4-triazol-5-yl)-1H-pyrazol-1-yl)propyl)pyridin-3-yl)-3-fluoroaniline A mixture of 5-bromo-2-(3-(difluoromethoxy)-1-(4-(1-methyl-1H-1,2,4-triazol-5-yl)-1H-pyrazol-1-yl)propyl)pyridine (0.43 g, 1.04 mmol, 1.0 equiv.), (6-amino-3-chloro-2-fluorophenyl)boronic acid (0.39 g, 2.08 mmol, 2.0 equiv.), $Pd(PPh_3)_4$ (0.24 g, 0.21 mmol, 0.2 equiv.), potassium carbonate (0.86 g, 6.24 mmol, 6.0 equiv.) in 1,4-dioxane (6 mL) and water (1.5 mL) was refluxed at 90° C. under $N_2$ for 2 h. The mixture was diluted with $H_2O$, extracted with ethyl acetate twice. The combined organic layers was washed with brine, dried over $Na_2SO_4$, concentrated and purified by silica gel chromatography (0→8%, MeOH/DCM) to yield 4-chloro-2-(6-(3-(difluoromethoxy)-1-(4-(1-methyl-1H-1,2,4-triazol-5-yl)-1H-pyrazol-1-yl)propyl)pyridin-3-yl)-3-fluoroaniline as a light yellow oil. LC/MS: mass calculated for $C_{21}H_{19}ClF_3N_7O$: 477.13, measured (ES, m/z): 478.10 $[M+H]^+$.

Step 7: 5-(3-Chloro-2-fluoro-6-(1H-tetrazol-1-yl)phenyl)-2-(3-(difluoromethoxy)-1-(4-(1-methyl-1H-1,2,4-triazol-5-yl)-1H-pyrazol-1-yl)propyl)pyridine A mixture of 4-chloro-2-(6-(3-(difluoromethoxy)-1-(4-(1-methyl-1H-1,2,4-triazol-5-yl)-1H-pyrazol-1-yl)propyl)pyridin-3-yl)-3-fluoroaniline (0.31 g, 0.65 mmol, 1.0 equiv.), trimethoxymethane (1 mL), azidotrimethylsilane (1 mL) and acetic acid (1 mL) was stirred overnight at room temperature. The reaction was purified by reverse phase chromatography on C18 (80 g, $MeCN/H_2O$ (0.05% $CF_3COOH$): 0→45%) to yield 5-(3-chloro-2-fluoro-6-(1H-tetrazol-1-yl)phenyl)-2-(3-(difluoromethoxy)-1-(4-(1-methyl-1H-1,2,4-triazol-5-yl)-1H-pyrazol-1-yl)propyl)pyridine as a light yellow oil. LC/MS: mass calculated for $C_{22}H_{18}ClF_3N_{10}O$: 530.13, measured (ES, m/z): 531.25 $[M+H]^+$.

Step 8: (R)-5-(3-Chloro-2-fluoro-6-(1H-tetrazol-1-yl)phenyl)-2-(3-(difluoromethoxy)-1-(4-(1-methyl-1H-1,2,4-triazol-5-yl)-1H-pyrazol-1-yl)propyl)pyridine 1-oxide A mixture of 5-(3-chloro-2-fluoro-6-(1H-tetrazol-1-yl)phenyl)-2-(3-(difluoromethoxy)-1-(4-(1-methyl-1H-1,2,4-triazol-5-yl)-1H-pyrazol-1-yl)propyl)pyridine (0.17 g, 0.32 mmol, 1.0 equiv.), hydrogen peroxide (30 wt %, 0.36 mL, 3.20 mmol, 10.0 equiv.) and methyltrioxorhenium (16 mg, 0.06 mmol, 0.2 equiv.) in $CH_3OH$ (2 mL) was stirred for 3 h at room temperature. The mixture was purified by reverse phase chromatography on C18 (80 g, $MeCN/H_2O$ (0.05% $CF_3COOH$): 0→45%) to yield 5-(3-chloro-2-fluoro-6-(1H-tetrazol-1-yl)phenyl)-2-(3-(difluoromethoxy)-1-(4-(1- methyl-1H-1,2,4-triazol-5-yl)-1H-pyrazol-1-yl)propyl)pyridine 1-oxide. The racemic product was separated by chiral-HPLC to yield (R)-5-(3-chloro-2-fluoro-6-(1H-tetrazol-1-yl)phenyl)-2-(3-(difluoromethoxy)-1-(4-(1-methyl-1H-1,2,4-triazol-5-yl)-1H-pyrazol-1-yl)propyl)pyridine 1-oxide as an oyster white solid.

LC/MS: mass calculated for $C_{22}H_{18}ClF_3N_{10}O_2$: 546.13, measured (ES, m/z): 547.10 [M+H]$^+$. $^1$H NMR (400 MHz, DMSO-$d_6$): δ 9.69 (s, 1H), 8.62 (s, 1H), 8.47 (d, J=1.6 Hz, 1H), 8.03-8.13 (m, 2H), 7.90 (s, 1H), 7.72-7.82 (m, 1H), 7.30 (d, J=8.3 Hz, 1H), 7.15-7.22 (m, 1H), 6.64 (t, J=75.7 Hz, 1H), 6.21-6.31 (m, 1H), 3.97 (s, 3H), 3.83-3.92 (m, 1H), 3.65-3.77 (m, 1H), 2.56-2.73 (m, 2H). $^{19}$F NMR (376 MHz, DMSO-$d_6$): δ −83.32, −112.68.

Example 589: (S)-5-(3-Chloro-2-fluoro-6-(1H-tetrazol-1-yl)phenyl)-2-(3-(difluoromethoxy)-1-(4-(2-(methylamino)pyrimidin-5-yl)-1H-pyrazol-1-yl)propyl)pyridine 1-oxide

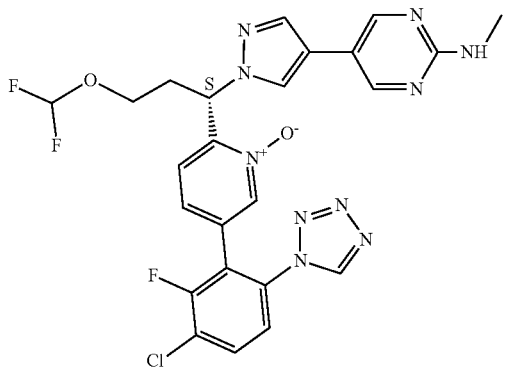

LC/MS: mass calculated for $C_{24}H_{20}ClF_3N_{10}O_2$: 572.14, measured (ES, m/z): 573.25 [M+H]$^+$. $^1$H NMR (300 MHz, DMSO-$d_6$) δ 9.59 (s, 1H), 8.58 (s, 2H), 8.34 (d, J=13.4 Hz, 2H), 7.90-8.02 (m, 2H), 7.66 (dd, J=8.7, 1.5 Hz, 1H), 7.15-7.31 (m, 2H), 6.53 (t, J=75.7 Hz, 1H), 6.10-6.16 (m, 1H), 3.60-7.64 (m, 4H), 2.81 (s, 3H). $^{19}$F NMR (282 MHz, DMSO-$d_6$) δ −83.11, −112.80.

Example 590: (R)-5-(3-Chloro-2-fluoro-6-(1H-tetrazol-1-yl)phenyl)-2-(3-(difluoromethoxy)-1-(4-(2-(methylamino)pyrimidin-5-yl)-1H-pyrazol-1-yl)propyl)pyridine 1-oxide

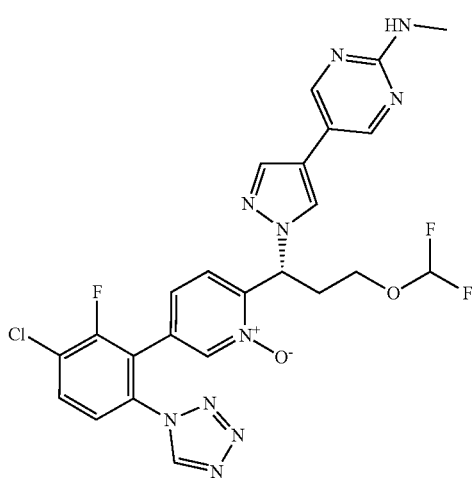 [SMILES: CNc1ncc(-c2cnn([C@H](CCOC(F)F)c3ccc(-c4c(-n5cnnn5)ccc(Cl)c4F)c[n+]3[O-])c2)cn1]

LC/MS: mass calculated for $C_{24}H_{20}ClF_3N_{10}O_2$: 572.14, measured (ES, m/z): 573.25 [M+H]$^+$. $^1$H NMR (300 MHz, DMSO-$d_6$) δ 9.64 (s, 1H), 8.54 (s, 2H), 8.42 (s, 1H), 8.32 (s, 1H), 7.96-8.07 (m, 2H), 7.72 (dd, J=8.7, 1.5 Hz, 1H), 7.17-7.32 (m, 2H), 6.59 (t, J=75.7 Hz, 1H), 6.12-6.25 (m, 1H), 3.82-3.92 (m, 1H), 3.55-3.76 (m, 3H), 2.82 (s, 3H). $^{19}$F NMR (282 MHz, DMSO-$d_6$) δ −83.12, −112.79.

Example 591: 5-(3-Chloro-2-fluoro-6-(1H-tetrazol-1-yl)phenyl)-2-(2-cyclopropyl-1-(3'-methyl-1H,1'H-[4,4'-bipyrazol]-1-yl)ethyl)pyridine 1-oxide

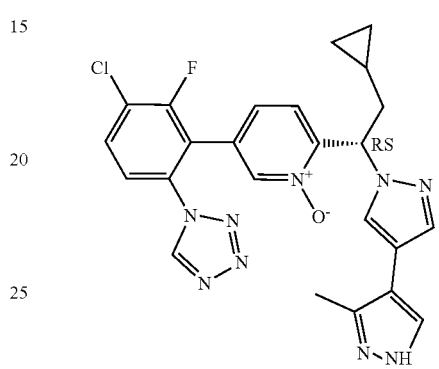

LC/MS: mass calculated for $C_{24}H_{21}ClFN_9O$: 505.2, measured (ES, m/z): 506.1 [M+H]$^+$. $^1$H NMR (400 MHz, CD$_3$OD) 5 ppm −0.07−−0.01 (m, 1H) 0.11-0.21 (m, 1H) 0.34-0.41 (m, 1H) 0.43-0.54 (m, 2 h) 1.83-1.92 (m, 1H) 2.30-2.41 (m, 1H) 5.96-6.09 (m, 1H) 7.26 (s, 1H) 7.31 (d, J=8.80 Hz, 1H) 7.47 (dd, J=8.80, 1.47 Hz, 1H) 7.64-7.76 (m, 3H) 8.54 (d, J=1.47 Hz, 1H) 9.30 (s, 1H).

Example 592: 5-(3-Chloro-2-fluoro-6-(1H-tetrazol-1-yl)phenyl)-2-(2-cyclopropyl-1-(4-(2-methyl-2H-1,2,3-triazol-4-yl)-1H-pyrazol-1-yl)ethyl)pyridine 1-oxide

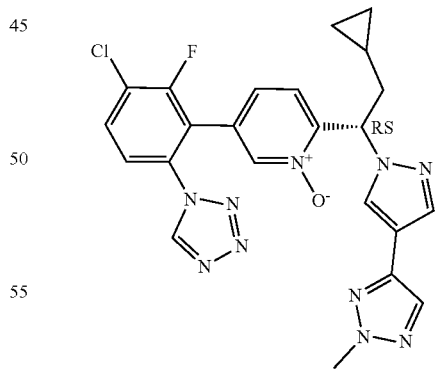

LC/MS: mass calculated for $C_{23}H_{20}ClFN_{10}O$: 506.2, measured (ES, m/z): 507.1 [M+H]$^+$. $^1$H NMR (400 MHz, CD$_3$OD) δ 9.38 (s, 1H), 8.35 (s, 1H), 8.26 (s, 1H), 8.08 (s, 1H), 7.88-7.97 (m, 2H), 7.57-7.65 (m, 1H), 7.44 (d, J=8.31 Hz, 1H), 7.21-7.32 (m, 1H), 6.19-6.26 (m, 1H), 4.13 (s, 3H), 2.42-2.57 (m, 1H), 1.90-2.04 (m, 1H), 0.65-0.77 (m, 1H), 0.41 (br s, 2H), 0.20 (br d, J=4.89 Hz, 1H), 0.03-0.10 (m, 1H).

Example 593: 5-(3-Chloro-2-fluoro-6-(1H-tetrazol-1-yl)phenyl)-2-(1-(4-chloro-2-methyl-1'H,2H-[3,4'-bipyrazol]-1'-yl)-2-cyclopropylethyl)pyridine 1-oxide

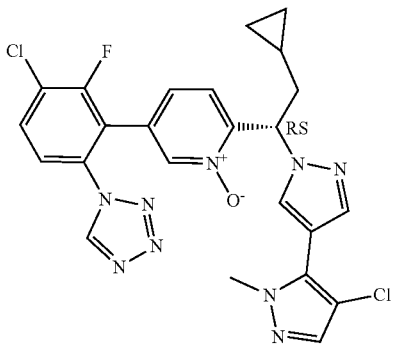

LC/MS: mass calculated for $C_{24}H_{20}Cl_2FN_9O$: 539.1, measured (ES, m/z): 540.2 [M+H]$^+$. $^1$H NMR (400 MHz, CD$_3$OD) δ 9.38 (s, 1H), 8.36 (d, J=14.67 Hz, 2H), 7.83-7.98 (m, 2H), 7.52-7.67 (m, 2H), 7.48 (s, 1H), 7.30 (d, J=7.83 Hz, 1H), 6.28 (dd, J=4.16, 10.03 Hz, 1H), 3.89 (s, 3H), 2.37-2.54 (m, 1H), 2.04-2.13 (m, 1H), 0.60-0.82 (m, 1H), 0.41 (m, 2H), 0.18 (dd, J=4.40, 9.29 Hz, 1H), −0.01-0.05 (m, 1H).

Example 594: (R)-5-(3-chloro-2-fluoro-6-(1H-tetrazol-1-yl)phenyl)-2-(3-(difluoromethoxy)-1-(2-(methyl-d3)-1'H,2H-[3,4'-bipyrazol]-1'-yl)propyl)pyridine 1-oxide

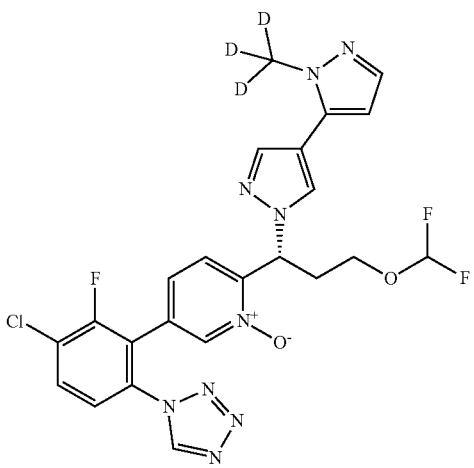 [SMILES: [2H]C([2H])([2H])n1nccc1-c1cnn([C@H](CCOC(F)F)c2ccc(-c3c(-n4cnnn4)ccc(Cl)c3F)c[n+]2[O-])c1]

Step 1: 5-Iodo-1-(methyl-d$_3$)-1H-pyrazole

The mixture of 5-iodo-1H-pyrazole (10.0 g, 51.55 mmol, 1.0 equiv.), iodomethane-d$_3$ (14.9 g, 103.11 mmol, 2.0 equiv.) and K$_2$CO$_3$ (21.4 g, 154.66 mmol, 3.0 equiv.) in DMF (100 mL) was stirred at room temperature overnight. To the reaction mixture was added water, and the mixture extracted with ethyl acetate, the organic layer was washed with water and dried over anhydrous Na$_2$SO$_4$. The resulting mixture was concentrated to yield 5-iodo-1-(methyl-d3)-1H-pyrazole as a yellow solid. LC/MS: mass calculated for $C_4H_2D_3IN_2$: 210.97, measured (ES, m/z): 211.95 [M+H]$^+$.

Step 2: 2-(Methyl-d$_3$)-1'H,2H-3,4'-bipyrazole

The mixture of 5-iodo-1-(methyl-d3)-1H-pyrazole (4.0 g, 18.96 mmol, 1.0 equiv.), tert-butyl 4-(4,4,5,5-tetramethyl-1,3,2-dioxaborolan-2-yl)-1H-pyrazole-1-carboxylate (8.4 g, 28.43 mmol, 1.5 equiv.), K$_2$CO$_3$ (7.9 g, 56.87 mmol, 3.0 equiv.) and Pd(PPh$_3$)$_4$ (2.2 g, 1.89 mmol, 0.1 equiv.) in DMF (40 mL) and water (8 mL) was stirred at 90° C. for 3 hours under N$_2$. The reaction mixture was concentrated. The residue was purified by silica gel chromatography (0→20% MeOH/DCM) to yield 2-(methyl-d$_3$)-1'H,2H-3,4'-bipyrazole as a white solid. LC/MS: mass calculated for $C_7H_5D_3N_4$: 151.09, measured (ES, m/z): 152.05 [M+H]$^+$.

Step 3: 1'-(1-(5-Bromopyridin-2-yl)-3-(difluoromethoxy)propyl)-2-(methyl-d$_3$)-1'H,2H-3,4'-bipyrazole The mixture of 1-(5-bromopyridin-2-yl)-3-(difluoromethoxy)propyl methanesulfonate (400 mg, 1.11 mmol, 1.0 equiv.), 2-(methyl-d3)-1'H,2H-3,4'-bipyrazole (201 mg, 1.33 mmol, 1.2 equiv.) and Cs$_2$CO$_3$ (724 mg, 2.22 mmol, 2.0 equiv.) in Acetonitrile (5 mL) was stirred at 90° C. for 2 h. To the reaction mixture was added water, and the mixture extracted with ethyl acetate, the organic layer was washed with brine and dried over anhydrous Na$_2$SO$_4$. The resulting mixture was concentrated and purified by silica gel chromatography (0→40% EA/PE) to yield 1'-(1-(5-bromopyridin-2-yl)-3-(difluoromethoxy)propyl)-2-(methyl-d3)-1'H,2H-3,4'-bipyrazole as a yellow solid. LC/MS: mass calculated for $C_{16}H_{13}D_3BrF_2N_5O$: 414.07, measured (ES, m/z): 414.95 [M+H]$^+$.

Step 4: 4-Chloro-2-(6-(3-(difluoromethoxy)-1-(2-(methyl-d$_3$)-1'H,2H-[3,4'-bipyrazol]-1'-yl)propyl)pyridin-3-yl)-3-fluoroaniline The mixture of 1'-(1-(5-bromopyridin-2-yl)-3-(difluoromethoxy)propyl)-2-(methyl-d3)-1'H,2H-3,4'-bipyrazole (450 mg, 1.08 mmol, 1.0 equiv.), (6-amino-3-chloro-2-fluorophenyl)boronic acid (410 mg, 2.16 mmol, 2.0 equiv.), K$_2$CO$_3$ (749 mg, 5.42 mmol, 5.0 equiv.) and Pd(PPh$_3$)$_4$ (125 mg, 0.11 mmol, 0.1 equiv.) in 1,4-dioxane (5 mL) and water (1 mL) was stirred at 90° C. under N$_2$ overnight. To the reaction mixture was added water, and the mixture extracted with ethyl acetate, the organic layer was washed with brine and dried over anhydrous Na$_2$SO$_4$. The resulting mixture was concentrated and purified by silica gel chromatography (0→40% EA/PE) to yield 4-chloro-2-(6-(3-(difluoromethoxy)-1-(2-(methyl-d$_3$)-1'H,2H-[3,4'-bipyrazol]-1'-yl)propyl)pyridin-3-yl)-3-fluoroaniline as a yellow solid. LC/MS: mass calculated for $C_{22}H_{17}D_3ClF_3N_6O$: 479.15, measured (ES, m/z): 480.05 [M+H]$^+$.

Step 5: 1'-(1-(5-(3-Chloro-2-fluoro-6-(1H-tetrazol-1-yl)phenyl)pyridin-2-yl)-3-(difluoromethoxy)propyl)-2-(methyl-d$_3$)-1'H,2H-3,4'-bipyrazole The mixture of 4-chloro-2-(6-(3-(difluoromethoxy)-1-(2-(methyl-d3)-1'H,2H-[3,4'-bipyrazol]-1'-yl)propyl)pyridin-3-yl)-3-fluoroaniline (450 mg, 0.94 mmol, 1.0 equiv.), azidotrimethylsilane (2 mL) and trimethoxymethane (2 mL) in acetic acid (3 mL) was stirred at room temperature overnight. The solution was purified by reverse phase chromatography on C18 (80 g, MeCN/H$_2$O (0.05% CF$_3$COOH): 0→55%) to yield 1'-(1-(5-(3-chloro-2-fluoro-6-(1H-tetrazol-1-yl)phenyl)pyridin-2-yl)-3-(difluoromethoxy)propyl)-2-(methyl-d$_3$)-1'H,2H-3,4'-bipyrazole as a yellow solid. LC/MS: mass calculated for C$_{23}$H$_{16}$D$_3$ClF$_3$N$_9$O: 532.15, measured (ES, m/z): 533.20 [M+H]$^+$.

Step 6 (R)-5-(3-Cloro-2-fluoro-6-(1H-tetrazol-1-yl)phenyl)-2-(3-(difluoromethoxy)-1-(2-(methyl-d3)-1'H,2H-[3,4'-bipyrazol]-1'-yl)propyl)pyridine 1-oxide The mixture of 1'-(1-(5-(3-chloro-2-fluoro-6-(1H-tetrazol-1-yl)phenyl)pyridin-2-yl)-3-(difluoromethoxy)propyl)-2-(methyl-d3)-1'H,2H-3,4'-bipyrazole (450 mg, 0.84 mmol, 1.0 equiv, 3-chloroperoxybenzoic acid (583 mg, 3.38 mol, 4.0 equiv. in DCM (3 mL) was stirred at room temperature for 2 h. The solution was purified by reverse phase chromatography on C18 (80 g, MeCN/H$_2$O (0.05% CF$_3$COOH): 0→55%) to yield 5-(3-chloro-2-fluoro-6-(1H-tetrazol-1-yl)phenyl)-2-(3-(difluoromethoxy)-1-(2-(methyl-d3)-1'H,2H-[3,4'-bipyrazol]-1'-yl)propyl)pyridine 1-oxide. The compound 5-(3-chloro-2-fluoro-6-(1H-tetrazol-1-yl)phenyl)-2-(3-(difluoromethoxy)-1-(2-(methyl-d3)-1'H,2H-[3,4'-bipyrazol]-1'-yl)propyl)pyridine 1-oxide (120 mg) was separated by Prep-Chiral-HPLC to yield (R)-5-(3-chloro-2-fluoro-6-(1H-tetrazol-1-yl)phenyl)-2-(3-(difluoromethoxy)-1-(2-(methyl-d$_3$)-1'H,2H-[3,4'-bipyrazol]-1'-yl)propyl)pyridine 1-oxide as a white solid.

LC/MS: mass calculated for C$_{23}$H$_{16}$ClD$_3$F$_3$N$_9$O$_2$: 548.1, measured (ES, m/z): 549.1[M+H]$^+$. $^1$H NMR (300 MHz, DMSO-d$_6$) δ 9.58 (s, 1H), 8.36 (s, 1H), 8.28 (s, 1H), 7.95 (t, J=8.2 Hz, 1H), 7.89 (s, 1H), 7.65 (d, J=8.7 Hz, 1H), 7.26-7.39 (m, 2H), 7.16-7.19 (m, 1H), 6.52 (t, J=75.0 Hz, 1H), 6.39 (s, 1H), 6.15-6.20 (m, 1H), 3.58-3.66 (m, 2H), 2.51-2.63 (m, 2H). $^{19}$F NMR (282 MHz, DMSO-d$_6$) δ −83.22, −112.78.

Example 595: (S)-5-(3-Chloro-2-fluoro-6-(1H-tetrazol-1-yl)phenyl)-2-(3-(difluoromethoxy)-1-(2-(methyl-d3)-1'H,2H-[3,4'-bipyrazol]-1'-yl)propyl)pyridine 1-oxide

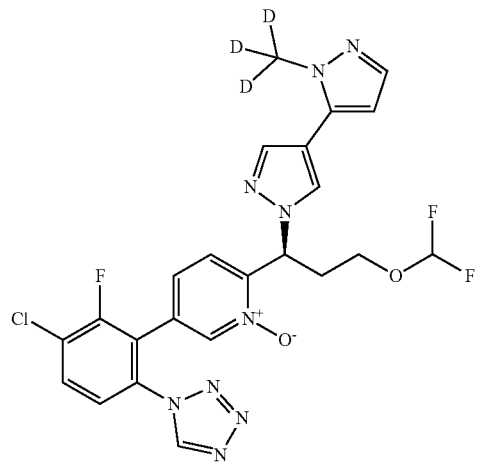 [SMILES: [2H]C([2H])([2H])n1nccc1-c1cnn([C@@H](CCOC(F)F)c2ccc(-c3c(-n4cnnn4)ccc(Cl)c3F)c[n+]2[O-])c1]

LC/MS: mass calculated for C$_{23}$H$_{16}$ClD$_3$F$_3$N$_9$O$_2$: 548.1, measured (ES, m/z): 549.10 [M+H]$^+$. $^1$H NMR (300 MHz, DMSO-d$_6$) δ 9.63 (s, 1H), 8.42 (s, 1H), 8.33 (s, 1H) 7.93-8.06 (m, 2H), 7.70 (dd, J=8.7, 1.6 Hz, 1H), 7.30-7.50 (m, 2H), 7.24 (dd, J=8.3, 1.7 Hz, 1H), 6.30-6.88 (m, 2H), 6.18-6.28 (m, 1H), 3.80-3.88 (m, 1H), 3.60-3.78 (m, 1H), 2.60-2.71 (m, 2H). $^{19}$F NMR (282 MHz, DMSO-d$_6$) δ −83.21, −112.79.

Example 596: (S)-5-(3-Chloro-2-fluoro-6-(1H-tetrazol-1-yl)phenyl)-2-(1-(2-(difluoromethyl)-1'H,2H-[3,4'-bipyrazol]-1'-yl)-3-methoxypropyl)pyridine 1-oxide

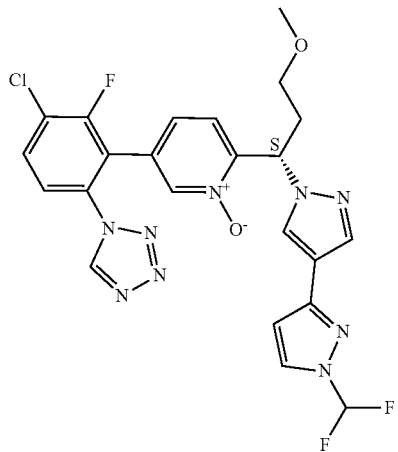

LC/MS: mass calculated for C$_{23}$H$_{19}$ClF$_3$N$_9$O$_2$: 545.13, measured (ES, m/z): 546.10 [M+H]$^+$. $^1$H NMR (300 MHz, DMSO-d$_6$) δ 9.66 (s, 1H), 8.36-8.50 (m, 2H), 8.20 (d, J=2.7 Hz, 1H), 8.01-8.10 (m, 1H), 7.56-8.00 (m, 3H), 7.10-7.30 (m, 2H), 6.77 (d, J=2.7 Hz, 1H), 6.10-6.20 (m, 1H), 3.25-3.31 (m, 1H), 3.11-3.23 (m, 4H), 2.38-2.50 (m, 2H). $^{19}$F NMR (282 MHz, DMSO-d$_6$) δ −93.91, −112.71.

Example 597: (S)-5-(3-chloro-2-fluoro-6-(1H-tetrazol-1-yl)phenyl)-2-(1-(2-(difluoromethyl)-1'H,2H-[3,4'-bipyrazol]-1'-yl)-3-methoxypropyl)pyridine 1-oxide

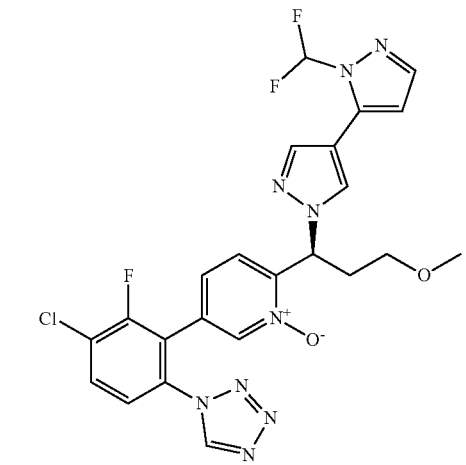 [SMILES: COCC[C@@H](c1ccc(-c2c(-n3cnnn3)ccc(Cl)c2F)c[n+]1[O-])n1cc(-c2ccnn2C(F)F)cn1]

LC/MS: mass calculated for C$_{23}$H$_{19}$ClF$_3$N$_9$O$_2$: 545.13, measured (ES, m/z): 568.05 [M+Na]$^+$. $^1$H NMR (300 MHz, DMSO-$d_6$) δ 9.67 (s, 1H), 8.32-8.49 (m, 2H), 7.63-8.07 (m, 5H), 7.35 (d, J=8.3 Hz, 1H), 7.12-7.21 (m, 1H), 6.67 (d, J=1.7 Hz, 1H), 6.12-6.22 (m, 1H), 3.25-3.29 (m, 1H), 3.08-3.17 (m, 4H), 2.42-2.45 (m, 2H). $^{19}$F NMR (282 MHz, DMSO-$d_6$) δ −93.56, −112.70.

Example 598: (R)-5-(3-chloro-2-fluoro-6-(1H-tetrazol-1-yl)phenyl)-2-(1-(1'-(difluoromethyl)-1H,1'H-[4,4'-bipyrazol]-1-yl)-3-methoxypropyl)pyridine 1-oxide

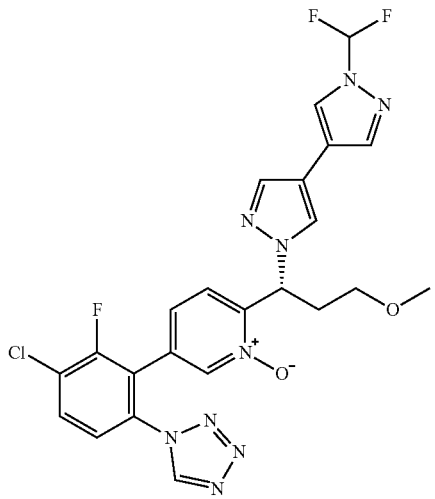 [SMILES: COCC[C@H](c1ccc(-c2c(-n3cnnn3)ccc(Cl)c2F)c[n+]1[O-])n1cc(-c2cnn(C(F)F)c2)cn1]

Step 1: Mixture of 1-(Difluoromethyl)-5-iodo-1H-pyrazole and 1-(difluoromethyl)-3-iodo-1H-pyrazole A mixture of 5-iodo-1H-pyrazole (10.0 g, 551.55 mmol, 1.0 equiv.), sodium 2-chloro-2,2-difluoroacetate (31.4 g, 61.86 mmol, 1.2 equiv.) and cesium carbonate (33.8 g, 103.11 mmol, 2.0 equiv.) in N,N-dimethylformamide (100 mL) was stirred at 90° C. under $N_2$ atmosphere for 3H. Then the reaction was diluted with EA (100 mL), then filtered the solid cesium carbonate. The organic was added water (500 mL), then extracted with EA (3×300 mL). The organic layers were combined, washed with water (300 mL), dried over $Na_2SO_4$ and concentrated to yield a mixture 1-(difluoromethyl)-5-iodo-1H-pyrazole and 1-(difluoromethyl)-5-iodo-1H-pyrazole as a light yellow oil. LC/MS: mass calculated for $C_4H_3F_2IN_2$: 243.93, measured (ES, m/z): 244.95 [M+H]$^+$.

Step 2: Mixture of 2-(difluoromethyl)-1'H,2H-3,4'-bipyrazole and 1-(difluoromethyl)-1H,1'H-3,4'-bipyrazole To a solution of 1-(difluoromethyl)-5-iodo-1H-pyrazole (two isomers mixture, 5.4 g, 21.93 mmol, 1.0 equiv.) in DMF/water (V/V=4:1, 50 mL) was added tert-butyl 4-(4,4,5,5-tetramethyl-1,3,2-dioxaborolan-2-yl)-1H-pyrazole-1-carboxylate (9.7 g, 32.89 mmol, 1.5 equiv.), $K_2CO_3$ (9.1 g, 65.78 mmol, 2.0 equiv.) and Pd(PPh$_3$)$_4$ (2.5 g, 2.19 mmol, 0.1 equiv.). Then the mixture was stirred at 90° C. for 2 h. The reaction was diluted with EA (50 mL), The resulting mixture was then filtered to remove insolubilized $K_2CO_3$. The resulting mixture was diluted with water (300 mL), extracted with EA (3×300 mL). The organic layers were combined, washed with water (300 mL), dried over $Na_2SO_4$ and concentrated. The residue was purified by silica gel chromatography (0%→60%, EA/PE) to yield a mixture of 2-(difluoromethyl)-1'H,2H-3,4'-bipyrazole and 1-(difluoromethyl)-1H,1'H-3,4'-bipyrazole and 1-(difluoromethyl)-1H,1'H-3,4'-bipyrazole as a light yellow solid. LC/MS: mass calculated for $C_7H_6F_2N_4$: 184.06, measured (ES, m/z): 185.05[M+H]$^+$.

Step 3: Mixture of 1'-(1-(5-bromopyridin-2-yl)-3-methoxypropyl)-2-(difluoromethyl)-1'H,2H-3,4'-bipyrazole and 1'-(1-(5-bromopyridin-2-yl)-3-methoxypropyl)-1-(difluoromethyl)-1H,1'H-3,4'-bipyrazole A mixture of cesium carbonate (322 mg, 0.99 mmol, 1.0 equiv.) and two isomers mixture 2-(difluoromethyl)-1'H,2H-3,4'-bipyrazole (182 mg, 0.99 mmol, 1.0 equiv.) in acetonitrile (3 mL) was stirred for 15 min at room temperature. 1-(5-bromopyridin-2-yl)-3-(trifluoromethoxy)propyl methanesulfonate (320 mg, 0.99 mmol, 1.0 equiv.) was added and the solution was stirred for 2.5 h at 90° C. The resulting mixture was diluted with EA (10 mL), filtered to remove the insolubilized salt, diluted with water, and the mixture extracted with EA (3×10 mL). The organic layers were combined, washed with water (300 mL), dried over $Na_2SO_4$ and concentrated. The residue was purified by silica gel chromatography (0%→60%, EA/PE) to yield a mixture of 1'-(1-(5-bromopyridin-2-yl)-3-methoxypropyl)-2-(difluoromethyl)-1'H,2H-3,4'-bipyrazole and 1'-(1-(5-bromopyridin-2-yl)-3-methoxypropyl)-1-(difluoromethyl)-1H,1'H-3,4'-bipyrazole. LC/MS: mass calculated for $C_{16}H_{16}BrF_2N_5O$: 411.05, measured (ES, m/z): 412.00 [M+H]$^+$.

Step 4: Mixture of 4-chloro-2-(6-(1-(2-(difluoromethyl)-1'H,2H-[3,4'-bipyrazol]-1'-yl)-3-methoxypropyl)pyridin-3-yl)-3-fluoroaniline and 4-chloro-2-(6-(1-(1-(difluoromethyl)-1H,1'H-[3,4'-bipyrazol]-1'-yl)-3-methoxypropyl)pyridin-3-yl)-3-fluoroaniline A mixture of 1'-(1-(5-bromopyridin-2-yl)-3-methoxypropyl)-2-(difluoromethyl)-1'H,2H-3,4'-bipyrazole (325 mg, 0.79 mmol, 1.0 equiv.), 6-amino-3-chloro-2-fluorophenylboronic acid (224 mg, 1.18 mmol, 1.5 equiv.), Pd(PPh$_3$)$_4$ (91 mg, 0.08 mmol, 0.1 equiv.) and $K_2CO_3$ (109 mg, 0.79 mmol, 2.0 equiv.) in 1,4-dioxane/water (V/V=4:1, 3 mL) was refluxed at 90° C. under $N_2$ for 3H. The resulting mixture was diluted with EA (10 mL), filtered to remove the insolubilized salt, diluted with water (10 mL) and extracted with EA (3×10 mL). The organic layers were combined, washed with water (20 mL), dried over $Na_2SO_4$ and concentrated. The residue was purified by silica gel chromatography (0%→30%, EA/PE) to yield 4-chloro-2-(6-(1-(2-(difluoromethyl)-1'H,2H-[3,4'-bipyrazol]-1'-yl)-3-methoxypropyl)pyridin-3-yl)-3-fluoroaniline and 4-chloro-2-(6-(1-(1-(difluoromethyl)-1H,1'H-[3,4'-bipyrazol]-1'-yl)-3-methoxypropyl)pyridin-3-yl)-3-fluoroaniline. LC/MS: mass calculated for $C_{22}H_{20}ClF_3N_6O$: 476.13, measured (ES, m/z): 477.10 [M+H]$^+$.

Step 5: Mixture of 1'-(1-(5-(3-chloro-2-fluoro-6-(1H-tetrazol-1-yl)phenyl)pyridin-2-yl)-3-methoxypropyl)-2-(difluoromethyl)-1'H,2H-3,4'-bipyrazole and 1'-(1-(5-(3-chloro-2-fluoro-6-(1H-tetrazol-1-yl)phenyl)pyridin-2-yl)-3-methoxypropyl)-1-(difluoromethyl)-1H,1'H-3,4'-bipyrazole A mixture of 4-chloro-2-(6-(1-(2-(difluoromethyl)-1'H,2H-[3,4'-bipyrazol]-1'-yl)-3-methoxypropyl)pyridin-3-yl)-

3-fluoroaniline (300 mg, 0.62 mmol, 1.0 equiv.), trimethoxymethane (2 mL) azidotrimethylsilane (2 mL) and acetic acid (2 mL) was stirred overnight at 25° C. The reaction was purified by reverse chromatography on C18 (0%→55% MeCN/H$_2$O (0.05% CF$_3$COOH)) to yield 1'-(1-(5-(3-chloro-2-fluoro-6-(1H-tetrazol-1-yl)phenyl)pyridin-2-yl)-3-methoxypropyl)-2-(difluoromethyl)-1'H,2H-3,4'-bipyrazole and 1'-(1-(5-(3-chloro-2-fluoro-6-(1H-tetrazol-1-yl)phenyl)pyridin-2-yl)-3-methoxypropyl)-1-(difluoromethyl)-1H,1'H-3,4'-bipyrazole as a light yellow solid. LC/MS: mass calculated for C$_{23}$H$_{19}$ClF$_3$N$_9$O: 529.14, measured (ES, m/z): 530.05 [M+H]$^+$.

Step 6: (R)-5-(3-Chloro-2-fluoro-6-(1H-tetrazol-1-yl)phenyl)-2-(1-(1-(difluoromethyl)-1H,1'H-[3,4'-bipyrazol]-1'-yl)-3-methoxypropyl)pyridine 1-oxide A mixture of 1'-(1-(5-(3-chloro-2-fluoro-6-(1H-tetrazol-1-yl)phenyl)pyridin-2-yl)-3-methoxypropyl)-2-(difluoromethyl)-1'H,2H-3,4'-bipyrazole (100 mg, 0.19 mmol, 1.0 equiv.) and 1'-(1-(5-(3-chloro-2-fluoro-6-(1H-tetrazol-1-yl)phenyl)pyridin-2-yl)-3-methoxypropyl)-1-(difluoromethyl)-1H,1'H-3,4'-bipyrazole (100 mg, 0.19 mmol, 1.0 equiv.), methyltrioxorhenium (24 mg, 0.09 mmol, 0.5 equiv.), hydrogen peroxide (0.5 mL) in CH$_3$OH (2 mL) was stirred for 3 h at room temperature. The resulting mixture was purified by reverse phase chromatography on C18 (MeCN/H$_2$O (0.05% CF$_3$COOH)) to yield a mixture 5-(3-chloro-2-fluoro-6-(1H-tetrazol-1-yl)phenyl)-2-(1-(2-(difluoromethyl)-1'H,2H-[3,4'-bipyrazol]-1'-yl)-3-methoxypropyl)pyridine 1-oxide and 5-(3-chloro-2-fluoro-6-(1H-tetrazol-1-yl)phenyl)-2-(1-(1-(difluoromethyl)-1H,1'H-[3,4'-bipyrazol]-1'-yl)-3-methoxypropyl)pyridine 1-oxide as a white solid. The racemic product was separated by chiral-HPLC to yield (R)-5-(3-chloro-2-fluoro-6-(1H-tetrazol-1-yl)phenyl)-2-(1-(1-(difluoromethyl)-1H,1'H-[3,4'-bipyrazol]-1'-yl)-3-methoxypropyl)pyridine 1-oxide as a white solid.

LC/MS: mass calculated for C$_{23}$H$_{19}$ClF$_3$N$_9$O$_2$: 545.13, measured (ES, m/z): 568.10 [M+Na]+. $^1$H NMR (300 MHz, DMSO-d$_6$) δ 9.66 (s, 1H), 8.40 (s, 2H), 8.20 (d, J=2.7 Hz, 1H), 8.03-8.08 (m, 1H), 7.95 (d, J=5.8 Hz, 1H), 7.54-7.79 (m, 2H), 7.09-7.27 (m, 2H), 6.75 (d, J=2.7 Hz, 1H), 6.14-6.18 (m, 1H), 3.27-3.30 (m, 1H), 3.13-3.19 (m, 4H), 2.39-2.48 (m, 2H). $^{19}$F-NMR (282 MHz, DMSO-d$_6$) δ -93.91, -112.71.

Example 599: (R)-5-(3-chloro-2-fluoro-6-(1H-tetrazol-1-yl)phenyl)-2-(1-(2-(difluoromethyl)-1'H,2H-[3,4'-bipyrazol]-1'-yl)-3-methoxypropyl)pyridine 1-oxide

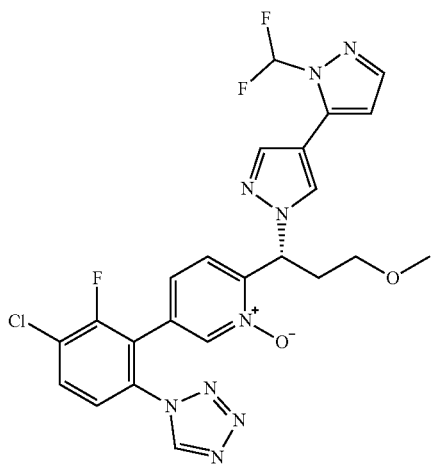 [SMILES: COCC[C@H](c1ccc(-c2c(-n3cnnn3)ccc(Cl)c2F)c[n+]1[O-])n1cc(-c2ccnn2C(F)F)cn1]

Step 1: Mixture of 1-(difluoromethyl)-5-iodo-1H-pyrazole and 1-(difluoromethyl)-3-iodo-1H-pyrazole A mixture of 5-iodo-1H-pyrazole (10.0 g, 551.55 mmol, 1.0 equiv.), sodium 2-chloro-2,2-difluoroacetate (31.4 g, 61.86 mmol, 1.2 equiv.) and cesium carbonate (33.8 g, 103.11 mmol, 2.0 equiv.) in N,N-dimethylformamide (100 mL) was stirred at 90° C. under N$_2$ atmosphere for 3 h. Then the reaction was diluted with EA (100 mL), then filtered the solid cesium carbonate. The organic was added water (500 mL), then extracted with EA (3×300 mL). The organic layers were combined, washed with water (300 mL), dried over Na$_2$SO$_4$ and concentrated to yield a mixture 1-(difluoromethyl)-5-iodo-1H-pyrazole and 1-(difluoromethyl)-5-iodo-1H-pyrazole as light yellow oil. LC/MS: mass calculated for C$_4$H$_3$F$_2$IN$_2$:243.93, measured (ES, m/z): 244.95 [M+H]$^+$.

Step 2: Mixture of 2-(difluoromethyl)-1'H,2H-3,4'-bipyrazole and 1-(difluoromethyl)-1H,1'H-3,4'-bipyrazole To a solution of 1-(difluoromethyl)-5-iodo-1H-pyrazole (two isomers mixture, 5.4 g, 21.93 mmol, 1.0 equiv.) in DMF/water (V/V=4:1, 50 mL) was added tert-butyl 4-(4,4,5,5-tetramethyl-1,3,2-dioxaborolan-2-yl)-1H-pyrazole-1-carboxylate (9.7 g, 32.89 mmol, 1.5 equiv.), K$_2$CO$_3$ (9.1 g, 65.78 mmol, 2.0 equiv.) and Pd(PPh$_3$)$_4$ (2.5 g, 2.19 mmol, 0.1 equiv.). Then the mixture was stirred at 90° C. for 2 h. The reaction was diluted with EA (50 mL). The resulting mixture was then filtered to remove insolubilized K$_2$CO$_3$. The resulting mixture was diluted with water (300 mL), extracted with EA (3×300 mL). The organic layers were combined, washed with water (300 mL), dried over Na$_2$SO$_4$ and concentrated. The residue was purified by silica gel chromatography (0%→60%, EA/PE) to yield a mixture of 2-(difluoromethyl)-1'H,2H-3,4'-bipyrazole and 1-(difluoromethyl)-1H,1'H-3,4'-bipyrazole and 1-(difluoromethyl)-1H,1'H-3,4'-bipyrazole as a light yellow solid. LC/MS: mass calculated for C$_7$H$_6$F$_2$N$_4$: 184.06, measured (ES, m/z): 185.05 [M+H]$^+$.

Step 3: Mixture of 1'-(1-(5-bromopyridin-2-yl)-3-methoxypropyl)-2-(difluoromethyl)-1'H,2H-3,4'-bipyrazole and 1'-(1-(5-bromopyridin-2-yl)-3-methoxypropyl)-1-(difluoromethyl)-1H,1'H-3,4'-bipyrazole A mixture of cesium carbonate (322 mg, 0.99 mmol, 1.0 equiv.) and two isomers mixture 2-(difluoromethyl)-1'H,2H-3,4'-bipyrazole (182 mg, 0.99 mmol, 1.0 equiv.) in acetonitrile (3 mL) was stirred for 15 min at room temperature. 1-(5-bromopyridin-2-yl)-3-(trifluoromethoxy)propyl methanesulfonate (320 mg, 0.99 mmol, 1.0 equiv.) was added and the solution was stirred for 2.5 h at 90° C. The resulting mixture was diluted with EA (10 mL), filtered to remove the insolubilized salt, diluted with water, and the mixture extracted with EA (3×10 mL). The organic layers were combined, washed with water (300 mL), dried over Na$_2$SO$_4$ and concentrated. The residue was purified by silica gel chromatography (0%→60%, EA/PE) to yield a mixture of 1'-(1-(5-bromopyridin-2-yl)-3-methoxypropyl)-2-(difluoromethyl)-1'H,2H-3,4'-bipyrazole and 1'-(1-(5-bromopyridin-2-yl)-3-methoxypropyl)-1-(difluoromethyl)-1H,1'H-3,4'-. LC/MS: mass calculated for C$_{16}$H$_{16}$BrF$_2$N$_5$O: 411.05, measured (ES, m/z): 412.00 [M+H]$^+$.

Step 4: Mixture of 4-chloro-2-(6-(1-(2-(difluoromethyl)-1'H,2H-[3,4'-bipyrazol]-1'-yl)-3-methoxypropyl)pyridin-3-yl)-3-fluoroaniline and 4-chloro-2-(6-(1-(1-(difluoromethyl)-1H,1'H-[3,4'-bipyrazol]-1'-yl)-3-methoxypropyl)pyridin-3-yl)-3-fluoroaniline A mixture of 1'-(1-(5-bromopyridin-2-yl)-3-methoxypropyl)-2-(difluoromethyl)-1'H,2H-3,4'-bipyrazole (325 mg, 0.79 mmol, 1.0 equiv.), 6-amino-3-chloro-2-fluorophenylboronic acid (224 mg, 1.18 mmol, 1.5 equiv.), Pd(PPh$_3$)$_4$ (91 mg, 0.08 mmol, 0.1 equiv.) and K$_2$CO$_3$ (109 mg, 0.79 mmol, 2.0 equiv.) in 1,4-dioxane/water (V/V=4:1, 3 mL) was refluxed at 90° C. under N$_2$ for 3H. The resulting mixture was diluted with EA (10 mL), filtered to remove the insolubilized salt, diluted with water (10 mL) and extracted with EA (3×10 mL). The organic layers were combined, washed with water (20 mL), dried over Na$_2$SO$_4$ and concentrated. The residue was purified by silica gel chromatography (0%→30%, EA/PE) to yield 4-chloro-2-(6-(1-(2-(difluoromethyl)-1'H,2H-[3,4'-bipyrazol]-1'-yl)-3-methoxypropyl)pyridin-3-yl)-3-fluoroaniline and 4-chloro-2-(6-(1-(1-(difluoromethyl)-1H,1'H-[3,4'-bipyrazol]-1'-yl)-3-methoxypropyl)pyridin-3-yl)-3-fluoroaniline. LC/MS: mass calculated for C$_{22}$H$_{20}$ClF$_3$N$_6$O: 476.13, measured (ES, m/z): 477.10 [M+H]$^+$.

Step 5: Mixture of 1'-(1-(5-(3-chloro-2-fluoro-6-(1H-tetrazol-1-yl)phenyl) pyridin-2-yl)-3-methoxypropyl)-2-(difluoromethyl)-1'H,2H-3,4'-bipyrazole and 1'-(1-(5-(3-chloro-2-fluoro-6-(1H-tetrazol-1-yl)phenyl)pyridin-2-yl)-3-methoxypropyl)-1-(difluoromethyl)-1H,1'H-3,4'-bipyrazole A mixture of 4-chloro-2-(6-(1-(2-(difluoromethyl)-1'H,2H-[3,4'-bipyrazol]-1'-yl)-3-methoxypropyl)pyridin-3-yl)-3-fluoroaniline (300 mg, 0.62 mmol, 1.0 equiv.), trimethoxymethane (2 mL) azidotrimethylsilane (2 mL) and acetic acid (2 mL) was stirred overnight at 25° C. The reaction was purified by reverse chromatography on C18 (0%→55% MeCN/H$_2$O (0.05% CF$_3$COOH)) to yield 1'-(1-(5-(3-chloro-2-fluoro-6-(1H-tetrazol-1-yl)phenyl)pyridin-2-yl)-3-methoxypropyl)-2-(difluoromethyl)-1'H,2H-3,4'-bipyrazole and 1'-(1-(5-(3-chloro-2-fluoro-6-(1H-tetrazol-1-yl)phenyl)pyridin-2-yl)-3-methoxypropyl)-1-(difluoromethyl)-1H,1'H-3,4'-bipyrazole as a light yellow solid. LC/MS: mass calculated for C$_{23}$H$_{19}$ClF$_3$N$_9$O: 529.14, measured (ES, m/z): 530.05 [M+H]$^+$.

Step 6: (R)-5-(3-Chloro-2-fluoro-6-(1H-tetrazol-1-yl)phenyl)-2-(1-(2-(difluoromethyl)-1'H,2H-[3,4'-bipyrazol]-1'-yl)-3-methoxypropyl)pyridine 1-oxide A mixture of 1'-(1-(5-(3-chloro-2-fluoro-6-(1H-tetrazol-1-yl)phenyl)pyridin-2-yl)-3-methoxypropyl)-2-(difluoromethyl)-1'H,2H-3,4'-bipyrazole (100 mg, 0.19 mmol, 1.0 equiv.) and 1'-(1-(5-(3-chloro-2-fluoro-6-(1H-tetrazol-1-yl)phenyl)pyridin-2-yl)-3-methoxypropyl)-1-(difluoromethyl)-1H,1'H-3,4'-bipyrazole (100 mg, 0.19 mmol, 1.0 equiv.), methyltrioxorhenium (24 mg, 0.09 mmol, 0.5 equiv.), hydrogen peroxide (0.5 mL, 30 wt %) in CH$_3$OH (2 mL) was stirred for 3 h at room temperature. The resulting mixture was purified by reverse phase chromatography on C18 (MeCN/H$_2$O (0.05% CF$_3$COOH)) to yield a mixture 5-(3-chloro-2-fluoro-6-(1H-tetrazol-1-yl)phenyl)-2-(1-(2-(difluoromethyl)-1'H,2H-[3,4'-bipyrazol]-1'-yl)-3-methoxypropyl)pyridine 1-oxide and 5-(3-chloro-2-fluoro-6-(1H-tetrazol-1-yl)phenyl)-2-(1-(1-(difluoromethyl)-1H,1'H-[3,4'-bipyrazol]-1'-yl)-3-methoxypropyl)pyridine 1-oxide as a white solid. The racemic product was separated by chiral-HPLC to yield (R)-5-(3-chloro-2-fluoro-6-(1H-tetrazol-1-yl)phenyl)-2-(1-(2-(difluoromethyl)-1'H,2H-[3,4'-bipyrazol]-1'-yl)-3-methoxypropyl)pyridine 1-oxide as a white solid.

LC/MS: mass calculated for C$_{23}$H$_{19}$ClF$_3$N$_9$O$_2$: 545.13, measured (ES, m/z): 568.10 [M+Na]$^+$. $^1$H NMR (300 MHz, DMSO-d$_6$) δ 9.67 (s, 1H), 8.44 (s, 1H), 8.37 (s, 1H), 8.04-8.09 (m, 1H), 7.60-8.01 (m, 4H), 7.11-7.39 (m, 2H), 6.67 (d, J=1.8 Hz, 1H), 6.17-6.22 (m, 1H), 3.06-3.29 (m, 5H), 2.38-2.50 (m, 2H). $^{19}$F-NMR (282 MHz, DMSO-d$_6$) δ −93.58, −112.69.

Example 600: (S)-5-(3-chloro-2-fluoro-6-(1H-tetrazol-1-yl)phenyl)-2-(3-(difluoromethoxy)-1-(2-(difluoromethyl)-1'H,2H-[3,4'-bipyrazol]-1'-yl)propyl)pyridine 1-oxide

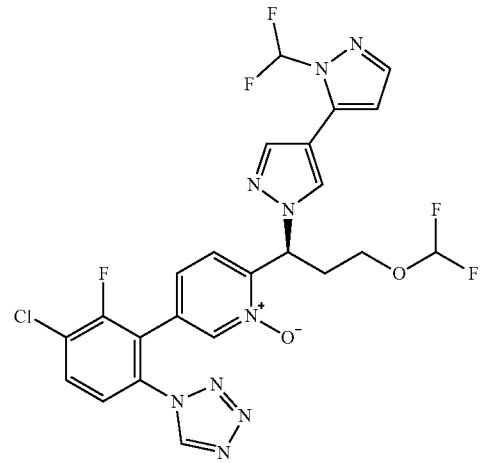 [SMILES: [O-][n+]1cc(-c2c(-n3cnnn3)ccc(Cl)c2F)ccc1[C@H](CCOC(F)F)n1cc(-c2ccnn2C(F)F)cn1]

LC/MS: mass calculated for C$_{23}$H$_{17}$ClF$_5$N$_9$O$_2$: 581.11, measured (ES, m/z): 582.00 [M+H]$^+$. $^1$H NMR (400 MHz, DMSO-d$_6$) δ 9.68 (s, 1H), 8.36-8.50 (m, 2H), 8.22 (d, J=2.7 Hz, 1H), 7.60-8.11 (m, 4H), 7.13-7.40 (m, 2H), 6.44-6.85 (m, 2H), 6.13-6.28 (m, 1H), 3.80-3.91 (m, 1H), 3.60-3.77 (m, 1H), 2.55-2.75 (m, 2H). $^{19}$F NMR (376 MHz, DMSO-d$_6$) δ −83.26, −93.93, −112.69.

Example 601: (R)-5-(3-chloro-2-fluoro-6-(1H-tetrazol-1-yl)phenyl)-2-(3-(difluoromethoxy)-1-(1-(difluoromethyl)-1H,1'H-[3,4'-bipyrazol]-1'-yl)propyl)pyridine 1-oxide

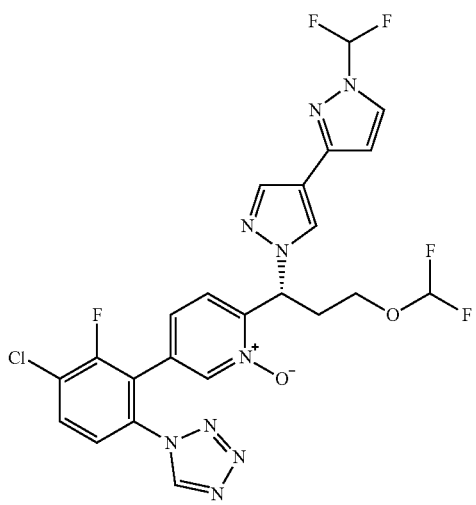 [SMILES: [O-][n+]1cc(-c2c(-n3cnnn3)ccc(Cl)c2F)ccc1[C@@H](CCOC(F)F)n1cc(-c2ccn(C(F)F)n2)cn1]

Step 1: 1-(5-Bromopyridin-2-yl)-3-((tert-butyldimethylsilyl)oxy)propan-1-ol

To a solution of 2,5-dibromopyridine (35 g, 147.8 mmol, 1.0 equiv.) in tetrahydrofuran (350 mL) was added n-butyllithium (65 mL, 162.5 mmol, 1.1 equiv.) after the temperature was dropped to −70° C. and stirred for 1H under $N_2$. Then 3-((tert-butyldimethylsilyl)oxy)propanal (33 mL, 155.1 mmol, 1.1 equiv.) was added and stirred for additional 1 h. The reaction was then quenched by ammonia chloride saturated solution, extracted with ethyl acetate twice. The combined organic layers were washed with brine, dried over $Na_2SO_4$ and purified by silica gel chromatography (0→50% EtOAc/petroleum ether) to yield 1-(5-bromopyridin-2-yl)-3-((tert-butyldimethylsilyl)oxy)propan-1-ol as light yellow oil. LC/MS: mass calculated for $C_{14}H_{24}BrNO_2Si$: 345.08, measured (ES, m/z): 347.95 [M+H+2]$^+$.

Step 2: 5-Bromo-2-(3-((tert-butyldimethylsilyl)oxy)-1-((tetrahydro-2H-pyran-2-yl)oxy)propyl)pyridine A mixture of 1-(5-bromopyridin-2-yl)-3-((tert-butyldimethylsilyl)oxy)propan-1-ol (15 g, 43.3 mmol, 1.0 equiv.), 4-methylbenzenesulfonic acid (750 mg, 4.33 mmol, 0.1 equiv.) and 3,4-dihydro-2H-pyran (10.9 g, 129.9 mmol, 3.0 equiv.) in dichloromethane (150 mL) was stirred for 1 h at 70° C. The resulting solution was diluted with water and the pH value of the solution was adjusted to ~6-7 with $NaHCO_3$. The resulting solution was extracted with dichloromethane. The organic layers were combined, washed with sodium carbonate (aq.) and brine, dried and concentrated under vacuum to yield 5-bromo-2-(3-((tert-butyldimethylsilyl)oxy)-1-((tetrahydro-2H-pyran-2-yl)oxy)propyl)pyridine as a light yellow oil. LC/MS: mass calculated for $C_{19}H_{32}BrNO_3Si$: 429.13, measured (ES, m/z): 430.45 [M+H]$^+$.

Step 3: 3-(5-Bromopyridin-2-yl)-3-((tetrahydro-2H-pyran-2-yl)oxy)propan-1-ol

A mixture of 5-bromo-2-(3-((tert-butyldimethylsilyl)oxy)-1-((tetrahydro-2H-pyran-2-yl)oxy)propyl)pyridine (17.7 g, 41.1 mmol, 1.0 equiv.) and tetrabutylammonium fluoride (61.7 mL, 1.0 M in THF) was stirred for 1 h at room temperature. The mixture was diluted with $H_2O$, extracted with ethyl acetate twice. The combined organic layers were washed with brine, dried over $Na_2SO_4$, concentrated and purified by silica gel chromatography (0→50% EA/PE) to yield 3-(5-bromopyridin-2-yl)-3-((tetrahydro-2H-pyran-2-yl)oxy)propan-1-ol as a light yellow oil. LC/MS: mass calculated for $C_{13}H_{18}BrNO_3$: 315.05, measured (ES, m/z): 316.20, 317.95 [M+H, M+H+2]$^+$.

Step 4: 5-Bromo-2-(3-(difluoromethoxy)-1-((tetrahydro-2H-pyran-2-yl)oxy)propyl)pyridine To a solution of 3-(5-bromopyridin-2-yl)-3-((tetrahydro-2H-pyran-2-yl)oxy)propan-1-ol (4.0 g, 12.7 mmol, 1.0 equiv.) in acetonitrile (40 mL) was added cuprous iodide (0.48 g, 2.53 mmol, 0.2 equiv.). The mixture was heated to 50° C. under nitrogen atmosphere, and a solution of 2,2-difluoro-2-(fluorosulfonyl)acetic acid (2.0 mL, 1.5 equiv.) in acetonitrile (2 mL) was added dropwise. The mixture was heated for an additional 30 min at 50° C. The resulting solution was extracted with dichloromethane. The combined organic layers was washed with brine, dried over $Na_2SO_4$, concentrated and purified by silica gel chromatography (0→50% EtOAc/petroleum ether) to yield 5-bromo-2-(3-(difluoromethoxy)-1-((tetrahydro-2H-pyran-2-yl)oxy)propyl)pyridine as a light yellow oil. LC/MS: mass calculated for $C_{14}H_{18}BrF_2NO_3$: 365.04, measured (ES, m/z): 366.20, 368.10 [M+H, M+H+2]$^+$.

Step 5: 1-(5-Bromopyridin-2-yl)-3-(difluoromethoxy)propan-1-ol

To the solution of 5-bromo-2-(3-(difluoromethoxy)-1-((tetrahydro-2H-pyran-2-yl)oxy)propyl)pyridine (4.4 g, 12.0 mmol, 1.0 equiv.) in DCM (50 mL) was added trifluoroacetic acid (5 mL) and the mixture was stirred for 1 h at room temperature. The reaction solution was concentrated under vacuum to yield 1-(5-bromopyridin-2-yl)-3-(difluoromethoxy)propan-1-ol as dark yellow oil. LC/MS: mass calculated for $C_9H_{10}BrF_2NO_2$: 280.99, measured (ES, m/z): 282.10, 284.05 [M+H, M+H+2]$^+$.

Step 6: 1-(5-Bromopyridin-2-yl)-3-(difluoromethoxy)propyl methanesulfonate

To a mixture of 1-(5-bromopyridin-2-yl)-3-(difluoromethoxy)propan-1-ol (4.0 g, 14.2 mmol, 1.0 equiv.) and triethylamine (10 mL, 71.0 mmol, 5 equiv.) in DCM (40 mL) was added methanesulfonic anhydride (5.0 g, 28.4 mmol, 2.0 equiv.) at 0° C. and the solution was stirred for 2 h at room temperature. The mixture was diluted with $H_2O$, extracted with DCM twice. The combined organic layers were washed with brine, dried over $Na_2SO_4$, concentrated and purified by silica gel chromatography (0→50% EtOAc/petroleum ether) to yield 1-(5-bromopyridin-2-yl)-3-(difluoromethoxy)propyl methanesulfonate as a light yellow solid. LC/MS: mass calculated for $C_{10}H_{12}BrF_2NO_4S$: 358.96, measured (ES, m/z): 360, 361.90 [M+H, M+H+2]$^+$.

Step 7: The mixture of 1'-(1-(5-bromopyridin-2-yl)-3-(difluoromethoxy)propyl)-2-(difluoromethyl)-1'H,2H-3,4'-bipyrazole and 1'-(1-(5-bromopyridin-2-yl)-3-(difluoromethoxy)propyl)-1-(difluoromethyl)-1H,1'H-3,4'-bipyrazole To a solution of the mixture of 2-(difluoromethyl)-1'H,2H-3,4'-bipyrazole and 1-(difluoromethyl)-1H,1'H-3,4'-bipyrazole (0.61 g, 3.33 mmol, 1.2 equiv.) in acetonitrile (8.0 mL) was added cesium carbonate (1.0 g, 3.05 mmol, 1.1 equiv.) and the solution was stirred for 15 min at room temperature. 1-(5-Bromopyridin-2-yl)-3-(difluoromethoxy) propyl methanesulfonate (1.0 g, 2.78 mmol, 1.0 equiv.) was added and the solution was stirred for another 3 h at 90° C. The solution was diluted with H₂O, extracted with ethyl acetate twice. The combined organic layers was washed with brine, dried over Na₂SO₄, concentrated and purified by silica gel chromatography (0→50% EtOAc/petroleum ether) to yield a mixture of 1'-(1-(5-bromopyridin-2-yl)-3-(difluoromethoxy)propyl)-2-(difluoromethyl)-1'H,2H-3,4'-bipyrazole and 1'-(1-(5-bromopyridin-2-yl)-3-(difluoromethoxy)propyl)-1-(difluoromethyl)-1H,1'H-3,4'-bipyrazole as a light yellow oil. LC/MS: mass calculated for $C_{16}H_{14}BrF_4N_5O$: 447.03, measured (ES, m/z): 448.10 [M+H]⁺.

Step 8: The mixture of 4-chloro-2-(6-(3-(difluoromethoxy)-1-(2-(difluoromethyl)-1'H,2H-[3,4'-bipyrazol]-1'-yl)propyl)pyridin-3-yl)-3-fluoroaniline and 4-chloro-2-(6-(3-(difluoromethoxy)-1-(1-(difluoromethyl)-1H,1'H-[3,4'-bipyrazol]-1'-yl)propyl) pyridin-3-yl)-3-fluoroaniline To a solution of the mixture of 1'-(1-(5-bromopyridin-2-yl)-3-(difluoromethoxy)propyl)-2-(difluoromethyl)-1'H,2H-3,4'-bipyrazole and 1'-(1-(5-bromopyridin-2-yl)-3-(difluoromethoxy)propyl)-1-(difluoromethyl)-1H,1'H-3,4'-bipyrazole (1.1 g, 2.5 mmol, 1.0 equiv.) in 1,4-dioxane (10 mL) and water (2 mL) was added (6-amino-3-chloro-2-fluorophenyl)boronic acid (0.96 g, 5.1 mmol, 2.0 equiv.), Pd(PPh₃)₄ (0.59 g, 0.51 mmol, 0.2 equiv.), K₂CO₃ (2.1 g, 15.3 mmol, 6.0 equiv.) and the solution was refluxed at 90° C. under N₂ for 2 h. The mixture was diluted with H₂O, extracted with ethyl acetate twice. The combined organic layers were washed with brine, dried over Na₂SO₄, concentrated and purified by silica gel chromatography (0→80%, EtOAc/petroleum ether) to yield a mixture of 4-chloro-2-(6-(3-(difluoromethoxy)-1-(2-(difluoromethyl)-1'H,2H-[3,4'-bipyrazol]-1'-yl)propyl)pyridin-3-yl)-3-fluoroaniline and 4-chloro-2-(6-(3-(difluoromethoxy)-1-(1-(difluoromethyl)-1H,1'H-[3,4'-bipyrazol]-1'-yl)propyl)pyridin-3-yl)-3-fluoroaniline as a light yellow oil. LC/MS: mass calculated for $C_{22}H_{18}ClF_5N_6O$: 512.12, measured (ES, m/z): 513.05 [M+H]⁺.

Step 9: The mixture of 1'-(1-(5-(3-chloro-2-fluoro-6-(1H-tetrazol-1-yl)phenyl)pyridin-2-yl)-3-(difluoromethoxy)propyl)-2-(difluoromethyl)-1'H,2H-3,4'-bipyrazole and 1'-(1-(5-(3-chloro-2-fluoro-6-(1H-tetrazol-1-yl)phenyl)pyridin-2-yl)-3-(difluoromethoxy)propyl)-1-(difluoromethyl)-1H,1'H-3,4'-bipyrazole To a solution of the mixture of 4-chloro-2-(6-(3-(difluoromethoxy)-1-(2-(difluoromethyl)-1'H,2H-[3,4'-bipyrazol]-1'-yl)propyl)pyridin-3-yl)-3-fluoroaniline and 4-chloro-2-(6-(3-(difluoromethoxy)-1-(1-(difluoromethyl)-1H,1'H-[3,4'-bipyrazol]-1'-yl)propyl)pyridin-3-yl)-3-fluoroaniline (1.1 g, 2.1 mmol, 1.0 equiv.) in acetic acid (3 mL) was added trimethoxymethane (3 mL), azidotrimethylsilane (3 mL) and the solution was stirred overnight at room temperature. The reaction was purified by reverse phase chromatography on C18 (80 g, MeCN/H₂O (0.05% CF₃COOH): 0→45%) to yield a mixture of 1'-(1-(5-(3-chloro-2-fluoro-6-(1H-tetrazol-1-yl)phenyl)pyridin-2-yl)-3-(difluoromethoxy)propyl)-2-(difluoromethyl)-1'H,2H-3,4'-bipyrazole and 1'-(1-(5-(3-chloro-2-fluoro-6-(1H-tetrazol-1-yl)phenyl)pyridin-2-yl)-3-(difluoromethoxy)propyl)-1-(difluoromethyl)-1H,1'H-3,4'-bipyrazole as a light yellow solid. LC/MS: mass calculated for $C_{23}H_{17}ClF_5N_9O$: 565.12, measured (ES, m/z): 566.05 [M+H]⁺.

Step 10: (R)-5-(3-Chloro-2-fluoro-6-(1H-tetrazol-1-yl)phenyl)-2-(3-(difluoromethoxy)-1-(1-(difluoromethyl)-1H,1'H-[3,4'-bipyrazol]-1'-yl)propyl)pyridine 1-oxide To a solution of the mixture of 1'-(1-(5-(3-chloro-2-fluoro-6-(1H-tetrazol-1-yl)phenyl)pyridin-2-yl)-3-(difluoromethoxy)propyl)-2-(difluoromethyl)-1'H,2H-3,4'-bipyrazole and 1'-(1-(5-(3-chloro-2-fluoro-6-(1H-tetrazol-1-yl)phenyl)pyridin-2-yl)-3-(difluoromethoxy)propyl)-1-(difluoromethyl)-1H,1'H-3,4'-bipyrazole (0.5 g, 0.88 mmol, 1.0 equiv.) in CH₃OH (5 mL) was added hydrogen peroxide (30 wt %, 1.0 mL, 8.84 mmol, 10.0 equiv.) and methyltrioxorhenium (45 mg, 0.18 mmol, 0.2 equiv.) and the solution was stirred for 1 h at room temperature. The mixture was purified by reverse phase chromatography on C18 (80 g, MeCN/H₂O (0.05% CF₃COOH): 0→45%) to yield a mixture of 5-(3-chloro-2-fluoro-6-(1H-tetrazol-1-yl)phenyl)-2-(3-(difluoromethoxy)-1-(1-(difluoromethyl)-1H,1'H-[3,4'-bipyrazol]-1'-yl)propyl)pyridine 1-oxide and 5-(3-chloro-2-fluoro-6-(1H-tetrazol-1-yl)phenyl)-2-(3-(difluoromethoxy)-1-(2-(difluoromethyl)-1'H,2H-[3,4'-bipyrazol]-1'-yl)propyl) pyridine 1-oxide. The racemic product was separated by Chiral-HPLC to yield (R)-5-(3-chloro-2-fluoro-6-(1H-tetrazol-1-yl)phenyl)-2-(3-(difluoromethoxy)-1-(1-(difluoromethyl)-1H,1'H-[3,4'-bipyrazol]-1'-yl)propyl)pyridine 1-oxide as a white solid.

LC/MS: mass calculated for $C_{23}H_{17}ClF_5N_9O_2$: 581.11, measured (ES, m/z): 582.15 [M+H]⁺. ¹H NMR: (400 MHz, DMSO-d₆): δ 9.70 (s, 1H), 8.46 (d, J=1.6 Hz, 1H), 8.40 (s, 1H), 8.07 (t, J=8.2 Hz, 1H), 7.66-7.98 (m, 4H), 7.34 (d, J=8.3 Hz, 1H), 7.15-7.25 (m, 1H), 6.43-6.84 (m, 2H), 6.17-6.27 (m, 1H), 3.78-3.88 (m, 1H), 3.62-3.73 (m, 1H), 2.53-2.68 (m, 2H). ¹⁹F NMR (376 MHz, DMSO-d₆): δ −83.36, −93.65, −112.66.

Example 602: (R)-5-(3-chloro-2-fluoro-6-(1H-tetrazol-1-yl)phenyl)-2-(3-(difluoromethoxy)-1-(2-(difluoromethyl)-1'H,2H-[3,4'-bipyrazol]-1'-yl)propyl) pyridine 1-oxide

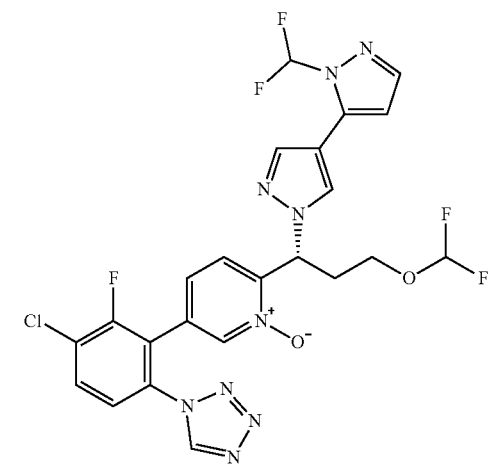 [SMILES: [O-][n+]1cc(-c2c(-n3cnnn3)ccc(Cl)c2F)ccc1[C@@H](CCOC(F)F)n1cc(-c2ccnn2C(F)F)cn1]

Step 1: 1-(5-Bromopyridin-2-yl)-3-((tert-butyldimethylsilyl)oxy)propan-1-ol

To a solution of 2,5-dibromopyridine (35 g, 147.8 mmol, 1.0 equiv.) in tetrahydrofuran (350 mL) was added n-butyllithium (65 mL, 162.5 mmol, 1.1 equiv.) after the temperature was dropped to −70° C. and stirred for 1 h under $N_2$. Then 3-((tert-butyldimethylsilyl)oxy)propanal (33 mL, 155.1 mmol, 1.1 equiv.) was added and stirred for additional 1 h. The reaction was then quenched by ammonia chloride saturated solution, extracted with ethyl acetate twice. The combined organic layers were washed with brine, dried over $Na_2SO_4$ and purified by silica gel chromatography (0→50% EtOAc/petroleum ether) to yield 1-(5-bromopyridin-2-yl)-3-((tert-butyldimethylsilyl)oxy)propan-1-ol as light yellow oil. LC/MS: mass calculated for $C_{14}H_{24}BrNO_2Si$: 345.08, measured (ES, m/z): 347.95 [M+H+2]$^+$.

Step 2: 5-Bromo-2-(3-((tert-butyldimethylsilyl)oxy)-1-((tetrahydro-2H-pyran-2-yl)oxy)propyl)pyridine A mixture of 1-(5-bromopyridin-2-yl)-3-((tert-butyldimethylsilyl)oxy)propan-1-ol (15 g, 43.3 mmol, 1.0 equiv.), 4-methylbenzenesulfonic acid (750 mg, 4.33 mmol, 0.1 equiv.) and 3,4-dihydro-2H-pyran (10.9 g, 129.9 mmol, 3.0 equiv.) in dichloromethane (150 mL) was stirred for 1 h at 70° C. The resulting solution was diluted with water and the pH value of the solution was adjusted to ~6-7 with $NaHCO_3$. The resulting solution was extracted with dichloromethane. The organic layers were combined, washed with sodium carbonate (aq.) and brine, dried and concentrated under vacuum to yield 5-bromo-2-(3-((tert-butyldimethylsilyl)oxy)-1-((tetrahydro-2H-pyran-2-yl)oxy)propyl)pyridine as a light yellow oil. LC/MS: mass calculated for $C_{19}H_{32}BrNO_3Si$: 429.13, measured (ES, m/z): 430.45 [M+H]$^+$.

Step 3: 3-(5-Bromopyridin-2-yl)-3-((tetrahydro-2H-pyran-2-yl)oxy)propan-1-ol A mixture of 5-bromo-2-(3-((tert-butyldimethylsilyl)oxy)-1-((tetrahydro-2H-pyran-2-yl)oxy)propyl)pyridine (17.7 g, 41.1 mmol, 1.0 equiv.) and tetrabutylammonium fluoride (61.7 mL, 1.0 M in THF) was stirred for 1 h at room temperature. The mixture was diluted with $H_2O$, extracted with ethyl acetate twice. The combined organic layers were washed with brine, dried over $Na_2SO_4$, concentrated and purified by silica gel chromatography (0→50% EA/PE) to yield 3-(5-bromopyridin-2-yl)-3-((tetrahydro-2H-pyran-2-yl)oxy)propan-1-ol as a light yellow oil. LC/MS: mass calculated for $C_{13}H_{18}BrNO_3$: 315.05, measured (ES, m/z): 316.20, 317.95 [M+H, M+H+2]$^+$.

Step 4: 5-Bromo-2-(3-(difluoromethoxy)-1-((tetrahydro-2H-pyran-2-yl)oxy)propyl)pyridine To a solution of 3-(5-bromopyridin-2-yl)-3-((tetrahydro-2H-pyran-2-yl)oxy)propan-1-ol (4.0 g, 12.7 mmol, 1.0 equiv.) in acetonitrile (40 mL) was added cuprous iodide (0.48 g, 2.53 mmol, 0.2 equiv.). The mixture was heated to 50° C. under nitrogen atmosphere, and a solution of 2,2-difluoro-2-(fluorosulfonyl)acetic acid (2.0 mL, 1.5 equiv.) in acetonitrile (2 mL) was added dropwise. The mixture was heated for an additional 30 min at 50° C. The resulting solution was extracted with dichloromethane. The combined organic layers was washed with brine, dried over $Na_2SO_4$, concentrated and purified by silica gel chromatography (0→50% EtOAc/petroleum ether) to yield 5-bromo-2-(3-(difluoromethoxy)-1-((tetrahydro-2H-pyran-2-yl)oxy)propyl)pyridine as a light yellow oil. LC/MS: mass calculated for $C_{14}H_{18}BrF_2NO_3$: 365.04, measured (ES, m/z): 366.20, 368.10 [M+H, M+H+2]$^+$.

Step 5: 1-(5-Bromopyridin-2-yl)-3-(difluoromethoxy)propan-1-ol

To the solution of 5-bromo-2-(3-(difluoromethoxy)-1-((tetrahydro-2H-pyran-2-yl)oxy)propyl)pyridine (4.4 g, 12.0 mmol, 1.0 equiv.) in DCM (50 mL) was added trifluoroacetic acid (5 mL) and the mixture was stirred for 1 h at room temperature. The reaction solution was concentrated under vacuum to yield 1-(5-bromopyridin-2-yl)-3-(difluoromethoxy)propan-1-ol as dark yellow oil. LC/MS: mass calculated for $C_9H_{10}BrF_2NO_2$: 280.99, measured (ES, m/z): 282.10, 284.05 [M+H, M+H+2]$^+$.

Step 6: 1-(5-Bromopyridin-2-yl)-3-(difluoromethoxy)propyl methanesulfonate

To a mixture of 1-(5-bromopyridin-2-yl)-3-(difluoromethoxy)propan-1-ol (4.0 g, 14.2 mmol, 1.0 equiv.) and triethylamine (10 mL, 71.0 mmol, 5 equiv.) in DCM (40 mL) was added methanesulfonic anhydride (5.0 g, 28.4 mmol, 2.0 equiv.) at 0° C. and the solution was stirred for 2 h at room temperature. The mixture was diluted with $H_2O$, extracted with DCM twice. The combined organic layers were washed with brine, dried over $Na_2SO_4$, concentrated and purified by silica gel chromatography (0→50% EtOAc/petroleum ether) to yield 1-(5-bromopyridin-2-yl)-3-(difluoromethoxy)propyl methanesulfonate as a light yellow solid. LC/MS: mass calculated for $C_{10}H_{12}BrF_2NO_4S$: 358.96, measured (ES, m/z): 360, 361.90 [M+H, M+H+2]$^+$.

Step 7: The mixture of 1'-(1-(5-bromopyridin-2-yl)-3-(difluoromethoxy)propyl)-2-(difluoromethyl)-1'H,2H-3,4'-bipyrazole and 1'-(1-(5-bromopyridin-2-yl)-3-(difluoromethoxy)propyl)-1-(difluoromethyl)-1H,1'H-3,4'-bipyrazole To a solution of the mixture of 2-(difluoromethyl)-1'H,2H-3,4'-bipyrazole and 1-(difluoromethyl)-1H,1'H-3,4'-bipyrazole (0.61 g, 3.33 mmol, 1.2 equiv.) in acetonitrile (8.0 mL) was added cesium carbonate (1.0 g, 3.05 mmol, 1.1 equiv.) and the solution was stirred for 15 min at room temperature. 1-(5-Bromopyridin-2-yl)-3-(difluoromethoxy)propyl methanesulfonate (1.0 g, 2.78 mmol, 1.0 equiv.) was added and the solution was stirred for another 3 h at 90° C. The solution was diluted with $H_2O$, extracted with ethyl acetate twice. The combined organic layers was washed with brine, dried over $Na_2SO_4$, concentrated and purified by silica gel chromatography (0→50% EtOAc/petroleum ether) to yield a mixture of 1'-(1-(5-bromopyridin-2-yl)-3-(difluoromethoxy)propyl)-2-(difluoromethyl)-1'H,2H-3,4'-bipyrazole and 1'-(1-(5-bromopyridin-2-yl)-3-(difluoromethoxy)propyl)-1-(difluoromethyl)-1H,1'H-3,4'-bipyrazole as a light yellow oil. LC/MS: mass calculated for $C_{16}H_{14}BrF_4N_5O$: 447.03, measured (ES, m/z): 448.10 [M+H]$^+$.

Step 8: The mixture of 4-chloro-2-(6-(3-(difluoromethoxy)-1-(2-(difluoromethyl)-1'H,2H-[3,4'-bipyrazol]-1'-yl)propyl)pyridin-3-yl)-3-fluoroaniline and 4-chloro-2-(6-(3-(difluoromethoxy)-1-(1-(difluoromethyl)-1H,1'H-[3,4'-bipyrazol]-1'-yl)propyl)pyridin-3-yl)-3-fluoroaniline To a solution of the mixture of 1'-(1-(5-bromopyridin-2-yl)-3-(difluoromethoxy)propyl)-2-(difluoromethyl)-1'H,2H-

3,4'-bipyrazole and 1'-(1-(5-bromopyridin-2-yl)-3-(difluoromethoxy)propyl)-1-(difluoromethyl)-1H,1'H-3,4'-bipyrazole and 1'-(1-(5-bromopyridin-2-yl)-3-(difluoromethoxy)propyl)-1-(difluoromethyl)-1H,1'H-3,4'-bipyrazole (1.1 g, 2.5 mmol, 1.0 equiv.) in 1,4-dioxane (10 mL) and water (2 mL) was added (6-amino-3-chloro-2-fluorophenyl)boronic acid (0.96 g, 5.1 mmol, 2.0 equiv.), Pd(PPh$_3$)$_4$ (0.59 g, 0.51 mmol, 0.2 equiv.), K$_2$CO$_3$ (2.1 g, 15.3 mmol, 6.0 equiv.) and the solution was refluxed at 90° C. under N$_2$ for 2 h. The mixture was diluted with H$_2$O, extracted with ethyl acetate twice. The combined organic layers were washed with brine, dried over Na$_2$SO$_4$, concentrated and purified by silica gel chromatography (0→80%, EtOAc/petroleum ether) to yield a mixture of 4-chloro-2-(6-(3-(difluoromethoxy)-1-(2-(difluoromethyl)-1'H,2H-[3,4'-bipyrazol]-1'-yl)propyl)pyridin-3-yl)-3-fluoroaniline and 4-chloro-2-(6-(3-(difluoromethoxy)-1-(1-(difluoromethyl)-1H,1'H-[3,4'-bipyrazol]-1'-yl)propyl)pyridin-3-yl)-3-fluoroaniline as a light yellow oil. LC/MS: mass calculated for C$_{22}$H$_{18}$ClF$_5$N$_6$O: 512.12, measured (ES, m/z): 513.05 [M+H]$^+$.

Step 9: The mixture of 1'-(1-(5-(3-chloro-2-fluoro-6-(1H-tetrazol-1-yl) phenyl)pyridin-2-yl)-3-(difluoromethoxy)propyl)-2-(difluoromethyl)-1'H,2H-3,4'-bipyrazole and 1'-(1-(5-(3-chloro-2-fluoro-6-(1H-tetrazol-1-yl)phenyl)pyridin-2-yl)-3-(difluoromethoxy)propyl)-1-(difluoromethyl)-1H, 1'H-3,4'-bipyrazole To a solution of the mixture of 4-chloro-2-(6-(3-(difluoromethoxy)-1-(2-(difluoromethyl)-1'H,2H-[3,4'-bipyrazol]-1'-yl)propyl)pyridin-3-yl)-3-fluoroaniline and 4-chloro-2-(6-(3-(difluoromethoxy)-1-(1-(difluoromethyl)-1H,1'H-[3,4'-bipyrazol]-1'-yl) propyl)pyridin-3-yl)-3-fluoroaniline (1.1 g, 2.1 mmol, 1.0 equiv.) in acetic acid (3 mL) was added trimethoxymethane (3 mL), azidotrimethylsilane (3 mL) and the solution was stirred overnight at room temperature. The reaction was purified by reverse phase chromatography on C18 (80 g, MeCN/H$_2$O (0.05% CF$_3$COOH): 0→45%) to yield a mixture of 1'-(1-(5-(3-chloro-2-fluoro-6-(1H-tetrazol-1-yl)phenyl)pyridin-2-yl)-3-(difluoromethoxy)propyl)-2-(difluoromethyl)-1'H,2H-3,4'-bipyrazole and 1'-(1-(5-(3-chloro-2-fluoro-6-(1H-tetrazol-1-yl)phenyl)pyridin-2-yl)-3-(difluoromethoxy)propyl)-1-(difluoromethyl)-1H,1'H-3,4'-bipyrazole as a light yellow solid. LC/MS: mass calculated for C$_{23}$H$_{17}$ClF$_5$N$_9$O: 565.12, measured (ES, m/z): 566.05 [M+H]$^+$.

Step 10: (R)-5-(3-Chloro-2-fluoro-6-(1H-tetrazol-1-yl)phenyl)-2-(3-(difluoromethoxy)-1-(2-(difluoromethyl)-1'H,2H-[3,4'-bipyrazol]-1'-yl)propyl)pyridine 1-oxide To a solution of the mixture of 1'-(1-(5-(3-chloro-2-fluoro-6-(1H-tetrazol-1-yl) phenyl)pyridin-2-yl)-3-(difluoromethoxy)propyl)-2-(difluoromethyl)-1'H,2H-3,4'-bipyrazole and 1'-(1-(5-(3-chloro-2-fluoro-6-(1H-tetrazol-1-yl)phenyl)pyridin-2-yl)-3-(difluoromethoxy)propyl)-1-(difluoromethyl)-1H,1'H-3,4'-bipyrazole (0.5 g, 0.88 mmol, 1.0 equiv.) in CH$_3$OH (5 mL) was added hydrogen peroxide (1.0 mL, 8.84 mmol, 10.0 equiv.) and methyltrioxorhenium (45 mg, 0.18 mmol, 0.2 equiv.) and the solution was stirred for 1 h at room temperature. The mixture was purified by reverse phase chromatography on C18 (80 g, MeCN/H$_2$O (0.05% CF$_3$COOH): 0→45%) to yield a mixture of 5-(3-chloro-2-fluoro-6-(1H-tetrazol-1-yl)phenyl)-2-(3-(difluoromethoxy)-1-(1-(difluoromethyl)-1H,1'H-[3,4'-bipyrazol]-1'-yl)propyl)pyridine 1-oxide and 5-(3-chloro-2-fluoro-6-(1H-tetrazol-1-yl)phenyl)-2-(3-(difluoromethoxy)-1-(2-(difluoromethyl)-1'H,2H-[3,4'-bipyrazol]-1'-yl)propyl) pyridine 1-oxide. The racemic product was separated by Chiral-HPLC to yield (R)-5-(3-chloro-2-fluoro-6-(1H-tetrazol-1-yl)phenyl)-2-(3-(difluoromethoxy)-1-(2-(difluoromethyl)-1'H,2H-[3,4'-bipyrazol]-1'-yl)propyl)pyridine 1-oxide as a light yellow solid.

LC/MS: mass calculated for C$_{23}$H$_{17}$ClF$_5$N$_9$O$_2$: 581.11, measured (ES, m/z): 582.00 [M+H]$^+$. $^1$H NMR (400 MHz, DMSO-d$_6$): δ 9.68 (s, 1H), 8.35-8.55 (m, 2H), 8.22 (d, J=2.7 Hz, 1H), 8.06 (t, J=8.2 Hz, 1H), 8.00 (s, 1H), 7.57-7.96 (m, 2H), 7.11-7.30 (m, 2H), 6.41-6.86 (m, 2H), 6.10-6.27 (m, 1H), 3.76-3.90 (m, 1H), 3.62-3.75 (, 1H), 2.56-2.74 (m, 2H). $^{19}$F NMR (376 MHz, DMSO-d$_6$): δ −83.26, −93.93, −112.68.

Example 603: (S)-5-(3-chloro-2-fluoro-6-(1H-tetrazol-1-yl)phenyl)-2-(3-(difluoromethoxy)-1-(1-(difluoromethyl)-1H,1'H-[3,4'-bipyrazol]-1'-yl)propyl) pyridine 1-oxide

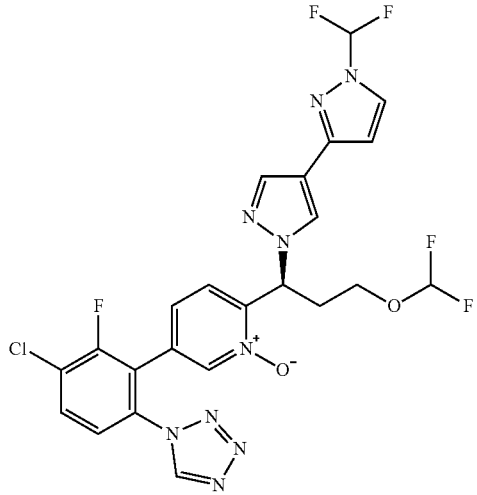 [SMILES: [O-][n+]1cc(-c2c(-n3cnnn3)ccc(Cl)c2F)ccc1[C@H](CCOC(F)F)n1cc(-c2ccn(C(F)F)n2)cn1]

LC/MS: mass calculated for C$_{23}$H$_{17}$ClF$_5$N$_9$O$_2$: 581.11, measured (ES, m/z): 604.00 [M+Na]$^+$. $^1$H NMR (400 MHz, DMSO-d$_6$) δ 9.70 (s, 1H), 8.47 (d, J=1.6 Hz, 1H), 8.40 (s, 1H), 8.07 (t, J=8.2 Hz, 1H), 7.65-8.00 (m, 4H), 7.34 (d, J=8.3 Hz, 1H), 7.20 (dd, J=8.3, 1.7 Hz, 1H), 6.40-6.87 (m, 2H), 6.18-6.27 (m, 1H), 3.80-3.90 (m, 1H), 3.61-3.73 (m, 1H), 2.54-2.70 (m, 2H). $^{19}$F NMR (376 MHz, DMSO-d$_6$) δ −83.36, −93.65, −112.66.

Example 604: (S)-5-(3-chloro-2-fluoro-6-(1H-tetrazol-1-yl)phenyl)-2-(1-(2-(difluoromethyl)-1'H,2H-[3,4'-bipyrazol]-1'-yl)-2-(4-fluorophenyl)ethyl)pyridine 1-oxide

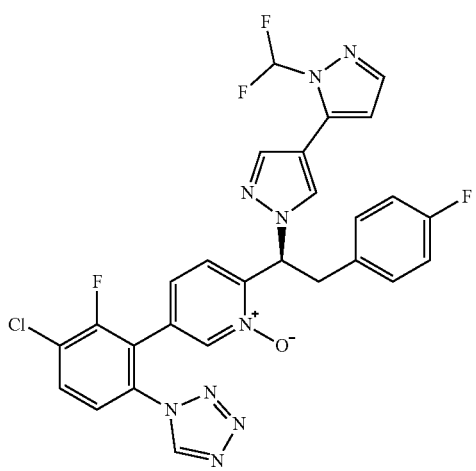 [SMILES: [O-][n+]1cc(-c2c(-n3cnnn3)ccc(Cl)c2F)ccc1[C@H](Cc1ccc(F)cc1)n1cc(-c2ccnn2C(F)F)cn1]

Step 1: The mixture of 1'-(1-(5-bromopyridin-2-yl)-2-(4-fluorophenyl) ethyl)-2-(difluoromethyl)-1'H,2H-3,4'-bipyrazole and 1'-(1-(5-bromopyridin-2-yl)-2-(4-fluorophenyl)ethyl)-1-(difluoromethyl)-1H,1'H-3,4'-bipyrazole To a solution of the mixture of 2-(difluoromethyl)-1'H,2H-3,4'-bipyrazole and 1-(difluoromethyl)-1H,1'H-3,4'-bipyrazole (0.59 g, 3.21 mmol, 1.2 equiv.) in acetonitrile (10 mL) was added cesium carbonate (0.96 g, 2.94 mmol, 1.1 equiv.) and the solution was stirred for 15 min at room temperature. 1-(5-Bromopyridin-2-yl)-2-(4-fluorophenyl)ethyl methanesulfonate (1.0 g, 2.67 mmol, 1.0 equiv.) was added and the solution was stirred for another 3 h at 90° C. The solution was diluted with water, extracted with ethyl acetate twice. The combined organic layers were washed with brine, dried over sodium sulfate, concentrated and purified by silica gel chromatography (0→50% EtOAc/petroleum ether) to yield a mixture of 1'-(1-(5-bromopyridin-2-yl)-2-(4-fluorophenyl)ethyl)-2-(difluoromethyl)-1'H,2H-3,4'-bipyrazole and 1'-(1-(5-bromopyridin-2-yl)-2-(4-fluorophenyl)ethyl)-1-(difluoromethyl)-1H,1'H-3,4'-bipyrazole as a light yellow oil. LC/MS: mass calculated for $C_{20}H_{15}BrF_3N_5$: 461.05, measured (ES, m/z): 462.27, 464.05 $[M+H, M+H+2]^+$.

Step 2: The mixture of 4-chloro-2-(6-(1-(2-(difluoromethyl)-1'H,2H-[3,4'-bipyrazol]-1'-yl)-2-(4-fluorophenyl)ethyl)pyridin-3-yl)-3-fluoroaniline and 4-chloro-2-(6-(1-(1-(difluoromethyl)-1H,1'H-[3,4'-bipyrazol]-1'-yl)-2-(4-fluorophenyl)ethyl)pyridin-3-yl)-3-fluoroaniline To a solution of the mixture of 1'-(1-(5-bromopyridin-2-yl)-2-(4-fluorophenyl)ethyl)-2-(difluoromethyl)-1'H,2H-3,4'-bipyrazole and 1'-(1-(5-bromopyridin-2-yl)-2-(4-fluorophenyl)ethyl)-1-(difluoromethyl)-1H,1'H-3,4'-bipyrazole (1.0 g, 2.16 mmol, 1.0 equiv.) in 1,4-dioxane (10.0 mL) and water (2.0 mL) was added (6-amino-3-chloro-2-fluorophenyl)boronic acid (0.82 g, 4.33 mmol, 2.0 equiv.), $Pd(PPh_3)_4$ (0.50 g, 0.43 mmol, 0.2 equiv.), $K_2CO_3$ (1.8 g, 12.98 mmol, 6.0 equiv.) and the solution was refluxed at 90° C. under $N_2$ for 2 h. The mixture was diluted with $H_2O$, extracted with ethyl acetate twice. The combined organic layers were washed with brine, dried over $Na_2SO_4$, concentrated and purified by silica gel chromatography (0→80%, EtOAc/petroleum ether) to yield a mixture of 4-chloro-2-(6-(1-(2-(difluoromethyl)-1'H,2H-[3,4'-bipyrazol]-1'-yl)-2-(4-fluorophenyl)ethyl) pyridin-3-yl)-3-fluoroaniline and 4-chloro-2-(6-(1-(1-(difluoromethyl)-1H,1'H-[3,4'-bipyrazol]-1'-yl)-2-(4-fluorophenyl)ethyl)pyridin-3-yl)-3-fluoroaniline as a light yellow solid. LC/MS: mass calculated for $C_{26}H_{19}ClF_4N_6$: 526.13, measured (ES, m/z): 527.10 $[M+H]^+$.

Step 3: The mixture of 1'-(1-(5-(3-chloro-2-fluoro-6-(1H-tetrazol-1-yl) phenyl)pyridin-2-yl)-2-(4-fluorophenyl)ethyl)-2-(difluoromethyl)-1'H,2H-3,4'-bipyrazole and 1'-(1-(5-(3-chloro-2-fluoro-6-(1H-tetrazol-1-yl)phenyl)pyridin-2-yl)-2-(4-fluorophenyl)ethyl)-1-(difluoromethyl)-1H,1'H-3,4'-bipyrazole To a solution of the mixture of 4-chloro-2-(6-(1-(2-(difluoromethyl)-1'H,2H-[3,4'-bipyrazol]-1'-yl)-2-(4-fluorophenyl)ethyl)pyridin-3-yl)-3-fluoroaniline and 4-chloro-2-(6-(1-(1-(difluoromethyl)-1H,1'H-[3,4'-bipyrazol]-1'-yl)-2-(4-fluorophenyl)ethyl)pyridin-3-yl)-3-fluoroaniline (1.0 g, 2.01 mmol, 1.0 equiv.) in acetic acid (3.0 mL) was added trimethoxymethane (3.0 mL), azidotrimethylsilane (3.0 mL) and the solution was stirred overnight at room temperature. The reaction was purified by reverse phase chromatography on C18 (80 g, $MeCN/H_2O$ (0.05% $CF_3COOH$): 0→45%) to yield a mixture of 1'-(1-(5-(3-chloro-2-fluoro-6-(1H-tetrazol-1-yl)phenyl)pyridin-2-yl)-2-(4-fluorophenyl)ethyl)-2-(difluoromethyl)-1'H,2H-3,4'-bipyrazole and 1'-(1-(5-(3-chloro-2-fluoro-6-(1H-tetrazol-1-yl)phenyl)pyridin-2-yl)-2-(4-fluorophenyl)ethyl)-1-(difluoromethyl)-1H,1'H-3,4'-bipyrazole as a light yellow solid. LC/MS: mass calculated for $C_{27}H_{18}ClF_4N_9$: 579.13, measured (ES, m/z): 580.05 $[M+H]^+$.

Step 4: (S)-5-(3-Chloro-2-fluoro-6-(1H-tetrazol-1-yl)phenyl)-2-(1-(2-(difluoromethyl)-1'H,2H-[3,4'-bipyrazol]-1'-yl)-2-(4-fluorophenyl)ethyl)pyridine 1-oxide To a solution of the mixture of 1'-(1-(5-(3-chloro-2-fluoro-6-(1H-tetrazol-1-yl)phenyl)pyridin-2-yl)-2-(4-fluorophenyl)ethyl)-2-(difluoromethyl)-1'H,2H-3,4'-bipyrazole and 1'-(1-(5-(3-chloro-2-fluoro-6-(1H-tetrazol-1-yl)phenyl)pyridin-2-yl)-2-(4-fluorophenyl)ethyl)-1-(difluoromethyl)-1H,1'H-3,4'-bipyrazole (0.50 g, 0.86 mmol, 1.0 equiv.) in $CH_3OH$ (5 mL) was added hydrogen peroxide (30 wt. %, 0.98 mL, 8.62 mmol, 20.0 equiv.) and methyltrioxorhenium (43 mg, 0.17 mmol, 0.4 equiv.) and the solution was stirred for 1 h at room temperature. The mixture was purified by reverse phase chromatography on C18 (80 g, $MeCN/H_2O$ (0.05% $CF_3COOH$): 0→45%) to yield a mixture of 5-(3-chloro-2-fluoro-6-(1H-tetrazol-1-yl)phenyl)-2-(1-(2-(difluoromethyl)-1'H,2H-[3,4'-bipyrazol]-1'-yl)-2-(4-fluorophenyl)ethyl)pyridine 1-oxide and 5-(3-chloro-2-fluoro-6-(1H-tetrazol-1-yl)phenyl)-2-(1-(1-(difluoromethyl)-1H, 1'H-[3,4'-bipyrazol]-1'-yl)-2-(4-fluorophenyl)ethyl)pyridine 1-oxide. The racemic product was separated by Chiral-HPLC to yield (S)-5-(3-chloro-2-fluoro-6-(1H-tetrazol-1-yl)

phenyl)-2-(1-(2-(difluoromethyl)-1'H,2H-[3,4'-bipyrazol]-1'-yl)-2-(4-fluorophenyl)ethyl)pyridine 1-oxide as a white solid.

$^1$H NMR (400 MHz, DMSO-d$_6$): δ 9.71 (s, 1H), 8.48 (d, J=1.6 Hz, 1H), 8.21 (s, 1H), 8.07 (t, J=8.2 Hz, 1H), 7.88 (s, 1H), 7.52-7.86 (m, 3H), 7.49 (d, J=8.3 Hz, 1H), 7.20-7.24 (m, 1H), 7.11-7.19 (m, 2H), 7.00-7.10 (m, 2H), 6.61 (d, J=1.7 Hz, 1H), 6.20-6.28 (m, 1H), 3.50-3.65 (m, 2H). $^{19}$F NMR (376 MHz, DMSO-d$_6$): δ −93.64, −112.69, −116.14.

Example 605: (S)-5-(3-chloro-2-fluoro-6-(1H-tetrazol-1-yl)phenyl)-2-(1-(1-(difluoromethyl)-1H,1'H-[3,4'-bipyrazol]-1'-yl)-2-(4-fluorophenyl)ethyl)pyridine 1-oxide

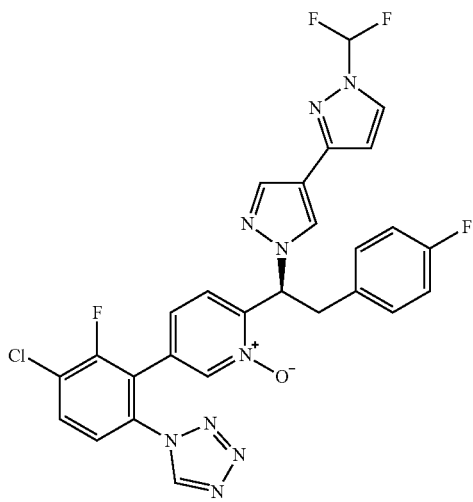 [SMILES: [O-][n+]1cc(-c2c(-n3cnnn3)ccc(Cl)c2F)ccc1[C@H](Cc1ccc(F)cc1)n1cc(-c2ccn(C(F)F)n2)cn1]

LC/MS: mass calculated for C$_{27}$H$_{18}$ClF$_4$N$_9$O: 595.13, measured (ES, m/z): 596.05 [M+H]$^+$. $^1$H NMR (400 MHz, DMSO-d$_6$) δ 9.70 (s, 1H), 8.47 (d, J=1.6 Hz, 1H), 8.31 (s, 1H), 8.19 (d, J=2.7 Hz, 1H), 8.07 (t, J=8.2 Hz, 1H), 7.97 (s, 1H), 7.60-7.93 (m, 2H), 7.33 (d, J=8.3 Hz, 1H), 7.15-7.27 (m, 3H), 7.01-7.11 (m, 2H), 6.71 (d, J=2.7 Hz, 1H), 6.15-6.28 (m, 1H), 3.45-3.69 (m, 2H). $^{19}$F NMR (376 MHz, DMSO-d$_6$) δ −93.92, −112.70, −116.20.

Example 606: (R)-5-(3-Chloro-2-fluoro-6-(1H-tetrazol-1-yl)phenyl)-2-(1-(2-(difluoromethyl)-1'H,2H-[3,4'-bipyrazol]-1'-yl)-2-(4-fluorophenyl)ethyl)pyridine 1-oxide

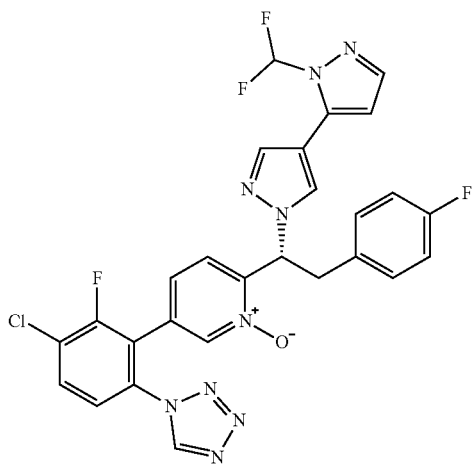 [SMILES: [O-][n+]1cc(-c2c(-n3cnnn3)ccc(Cl)c2F)ccc1[C@@H](Cc1ccc(F)cc1)n1cc(-c2ccnn2C(F)F)cn1]

Step 1: The mixture of 1'-(1-(5-bromopyridin-2-yl)-2-(4-fluorophenyl)ethyl)-2-(difluoromethyl)-1'H,2H-3,4'-bipyrazole and 1'-(1-(5-bromopyridin-2-yl)-2-(4-fluorophenyl)ethyl)-1-(difluoromethyl)-1H,1'H-3,4'-bipyrazole To a solution of the mixture of 2-(difluoromethyl)-1'H,2H-3,4'-bipyrazole and 1-(difluoromethyl)-1H,1'H-3,4'-bipyrazole (0.59 g, 3.21 mmol, 1.2 equiv.) in acetonitrile (10 mL) was added cesium carbonate (0.96 g, 2.94 mmol, 1.1 equiv.) and the solution was stirred for 15 min at room temperature. 1-(5-Bromopyridin-2-yl)-2-(4-fluorophenyl)ethyl methanesulfonate (1.0 g, 2.67 mmol, 1.0 equiv.) was added and the solution was stirred for another 3 h at 90° C. The solution was diluted with H$_2$O, extracted with ethyl acetate twice. The combined organic layers were washed with brine, dried over Na$_2$SO$_4$, concentrated and purified by silica gel chromatography (0→50% EtOAc/petroleum ether) to yield a mixture of 1'-(1-(5-bromopyridin-2-yl)-2-(4-fluorophenyl)ethyl)-2-(difluoromethyl)-1'H,2H-3,4'-bipyrazole and 1'-(1-(5-bromopyridin-2-yl)-2-(4-fluorophenyl)ethyl)-1-(difluoromethyl)-1H,1'H-3,4'-bipyrazole as a light yellow oil. LC/MS: mass calculated for C$_{20}$H$_{15}$BrF$_3$N$_5$: 461.05, measured (ES, m/z): 462.27, 464.05 [M+H, M+H+2]$^+$.

Step 2: The mixture of 4-chloro-2-(6-(1-(2-(difluoromethyl)-1'H,2H-[3,4'-bipyrazol]-1'-yl)-2-(4-fluorophenyl)ethyl)pyridin-3-yl)-3-fluoroaniline and 4-chloro-2-(6-(1-(1-(difluoromethyl)-1H,1'H-[3,4'-bipyrazol]-1'-yl)-2-(4-fluorophenyl)ethyl)pyridin-3-yl)-3-fluoroaniline To a solution of the mixture of 1'-(1-(5-bromopyridin-2-yl)-2-(4-fluorophenyl)ethyl)-2-(difluoromethyl)-1'H,2H-3,4'-bipyrazole and 1'-(1-(5-bromopyridin-2-yl)-2-(4-fluorophenyl)ethyl)-1-(difluoromethyl)-1H,1'H-3,4'-bipyrazole (1.0 g, 2.16 mmol, 1.0 equiv.) in 1,4-dioxane (10.0 mL) and water (2.0 mL) was added (6-amino-3-chloro-2-fluorophenyl)boronic acid (0.82 g, 4.33 mmol, 2.0 equiv.), Pd(PPh$_3$)$_4$ (0.50 g, 0.43 mmol, 0.2 equiv.), K$_2$CO$_3$ (1.8 g, 12.98 mmol, 6.0 equiv.) and the solution was refluxed at 90° C. under N$_2$ for 2 h. The mixture was diluted with H$_2$O, extracted with ethyl acetate twice. The combined organic layers were washed with brine, dried over Na$_2$SO$_4$, concentrated and purified by silica gel chromatography (0→80%, EtOAc/petroleum ether) to yield a mixture of 4-chloro-2-(6-(1-(2-(difluoromethyl)-1'H,2H-[3,4'-bipyrazol]-1'-yl)-2-(4-fluorophenyl)ethyl)pyridin-3-yl)-3-fluoroaniline and 4-chloro-2-(6-(1-(1-(difluoromethyl)-1H,1'H-[3,4'-bipyrazol]-1'-yl)-2-(4-fluorophenyl)ethyl)pyridin-3-yl)-3-fluoroaniline as a light yellow solid. LC/MS: mass calculated for C$_{26}$H$_{19}$ClF$_4$N$_6$: 526.13, measured (ES, m/z): 527.10 [M+H]$^+$.

Step 3: Mixture of 1'-(1-(5-(3-chloro-2-fluoro-6-(1H-tetrazol-1-yl)phenyl)pyridin-2-yl)-2-(4-fluorophenyl)ethyl)-2-(difluoromethyl)-1'H,2H-3,4'-bipyrazole and 1'-(1-(5-(3-chloro-2-fluoro-6-(1H-tetrazol-1-yl) phenyl)pyridin-2-yl)-2-(4-fluorophenyl)ethyl)-1-(difluoromethyl)-1H,1'H-3,4'-bipyrazole To a solution of the mixture of 4-chloro-2-(6-(1-(2-(difluoromethyl)-1'H,2H-[3,4'-bipyrazol]-1'-yl)-2-(4-fluorophenyl)ethyl)pyridin-3-yl)-3-fluoroaniline and 4-chloro-2-(6-(1-(1-(difluoromethyl)-1H,1'H-[3,4'-bipyrazol]-1'-yl)-2-(4-fluorophenyl)ethyl)pyridin-3-yl)-3-fluoroaniline (1.0 g, 2.01 mmol, 1.0 equiv.) in acetic acid (3.0 mL) was added trimethoxymethane (3.0 mL), azidotrimethylsilane (3.0 mL) and the solution was stirred overnight at room temperature.

The reaction was purified by reverse phase chromatography on C18 (80 g, MeCN/H$_2$O (0.05% CF$_3$COOH): 0→45%) to yield a mixture of 1'-(1-(5-(3-chloro-2-fluoro-6-(1H-tetrazol-1-yl) phenyl)pyridin-2-yl)-2-(4-fluorophenyl)ethyl)-2-(difluoromethyl)-1'H,2H-3,4'-bipyrazole and 1'-(1-(5-(3-chloro-2-fluoro-6-(1H-tetrazol-1-yl)phenyl)pyridin-2-yl)-2-(4-fluorophenyl)ethyl)-1-(difluoromethyl)-1H,1'H-3,4'-bipyrazole as a light yellow solid. LC/MS: mass calculated for C$_{27}$H$_{18}$ClF$_4$N$_9$: 579.13, measured (ES, m/z): 580.05 [M+H]$^+$.

Step 4: (R)-5-(3-Chloro-2-fluoro-6-(1H-tetrazol-1-yl)phenyl)-2-(1-(2-(difluoromethyl)-1'H,2H-[3,4'-bipyrazol]-1'-yl)-2-(4-fluorophenyl)ethyl)pyridine 1-oxide To a solution of the mixture of 1'-(1-(5-(3-chloro-2-fluoro-6-(1H-tetrazol-1-yl)phenyl)pyridin-2-yl)-2-(4-fluorophenyl)ethyl)-2-(difluoromethyl)-1'H,2H-3,4'-bipyrazole and 1'-(1-(5-(3-chloro-2-fluoro-6-(1H-tetrazol-1-yl)phenyl)pyridin-2-yl)-2-(4-fluorophenyl)ethyl)-1-(difluoromethyl)-1H,1'H-3,4'-bipyrazole (0.50 g, 0.86 mmol, 1.0 equiv.) in CH$_3$OH (5 mL) was added hydrogen peroxide (30 wt %, 0.98 mL, 8.62 mmol, 20.0 equiv.) and methyltrioxorhenium (43 mg, 0.17 mmol, 0.4 equiv.) and the solution was stirred for 1 h at room temperature. The mixture was purified by reverse phase chromatography on C18 (80 g, MeCN/H$_2$O (0.05% CF$_3$COOH): 0→45%) to yield a mixture of 5-(3-chloro-2-fluoro-6-(1H-tetrazol-1-yl)phenyl)-2-(1-(2-(difluoromethyl)-1'H,2H-[3,4'-bipyrazol]-1'-yl)-2-(4-fluorophenyl)ethyl)pyridine 1-oxide and 5-(3-chloro-2-fluoro-6-(1H-tetrazol-1-yl)phenyl)-2-(1-(1-(difluoromethyl)-1H,1'H-[3,4'-bipyrazol]-1'-yl)-2-(4-fluorophenyl)ethyl)pyridine 1-oxide. The racemic product was separated by Chiral-HPLC to yield (R)-5-(3-chloro-2-fluoro-6-(1H-tetrazol-1-yl)phenyl)-2-(1-(2-(difluoromethyl)-1'H,2H-[3,4'-bipyrazol]-1'-yl)-2-(4-fluorophenyl)ethyl)pyridine 1-oxide as a white solid.
$^1$H NMR (400 MHz, DMSO-d$_6$): δ 9.71 (s, 1H), 8.48 (d, J=1.7 Hz, 1H), 8.22 (s, 1H), 8.07 (t, J=8.2 Hz, 1H), 7.89 (s, 1H), 7.55-7.87 (m, 3H), 7.50 (d, J=8.3 Hz, 1H), 7.20-7.27 (m, 1H), 7.12-7.19 (m, 2H), 7.00-7.10 (m, 2H), 6.62 (d, J=1.8 Hz, 1H), 6.18-6.30 (m, 1H), 3.48-3.68 (m, 2H). $^{19}$F NMR (376 MHz, DMSO-d$_6$): δ −93.63, −112.68, −116.12.

Example 607: (R)-5-(3-Chloro-2-fluoro-6-(1H-tetrazol-1-yl)phenyl)-2-(1-(1-(difluoromethyl)-$^1$H,1'H-[3,4'-bipyrazol]-1'-yl)-2-(4-fluorophenyl)ethyl)pyridine 1-oxide

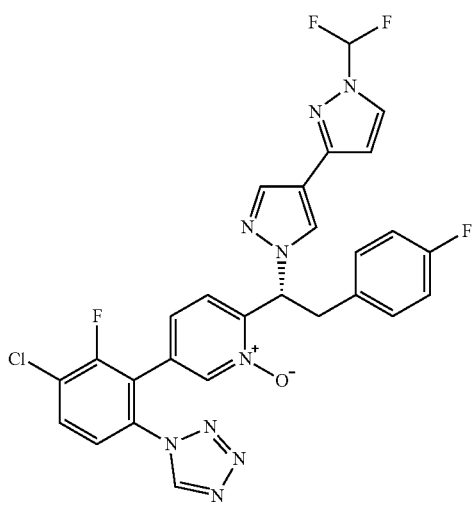 [SMILES: [O-][n+]1cc(-c2c(-n3cnnn3)ccc(Cl)c2F)ccc1[C@@H](Cc1ccc(F)cc1)n1cc(-c2ccn(C(F)F)n2)cn1]

Step 1: The mixture of 1'-(1-(5-bromopyridin-2-yl)-2-(4-fluorophenyl)ethyl)-2-(difluoromethyl)-1'H,2H-3,4'-bipyrazole and 1'-(1-(5-bromopyridin-2-yl)-2-(4-fluorophenyl)ethyl)-1-(difluoromethyl)-1H,1'H-3,4'-bipyrazole To a solution of the mixture of 2-(difluoromethyl)-1'H,2H-3,4'-bipyrazole and 1-(difluoromethyl)-1H,1'H-3,4'-bipyrazole (0.59 g, 3.21 mmol, 1.2 equiv.) in acetonitrile (10 mL) was added cesium carbonate (0.96 g, 2.94 mmol, 1.1 equiv.) and the solution was stirred for 15 min at room temperature. 1-(5-Bromopyridin-2-yl)-2-(4-fluorophenyl) ethyl methanesulfonate (1.0 g, 2.67 mmol, 1.0 equiv.) was added and the solution was stirred for another 3 h at 90° C. The solution was diluted with water, extracted with ethyl acetate twice. The combined organic layers were washed with brine, dried over Na$_2$SO$_4$, concentrated and purified by silica gel chromatography (0→50% EtOAc/petroleum ether) to yield a mixture of 1'-(1-(5-bromopyridin-2-yl)-2-(4-fluorophenyl)ethyl)-2-(difluoromethyl)-1'H,2H-3,4'-bipyrazole and 1'-(1-(5-bromopyridin-2-yl)-2-(4-fluorophenyl)ethyl)-1-(difluoromethyl)-1H,1'H-3,4'-bipyrazole as a light yellow oil. LC/MS: mass calculated for C$_{20}$H$_{15}$BrF$_3$N$_5$: 461.05, measured (ES, m/z): 462.27, 464.05 [M+H, M+H+2]$^+$.

Step 2: The mixture of 4-chloro-2-(6-(1-(2-(difluoromethyl)-1'H,2H-[3,4'-bipyrazol]-1'-yl)-2-(4-fluorophenyl)ethyl)pyridin-3-yl)-3-fluoroaniline and 4-chloro-2-(6-(1-(1-(difluoromethyl)-1H,1'H-[3,4'-bipyrazol]-1'-yl)-2-(4-fluorophenyl)ethyl)pyridin-3-yl)-3-fluoroaniline To a solution of the mixture of 1'-(1-(5-bromopyridin-2-yl)-2-(4-fluorophenyl)ethyl)-2-(difluoromethyl)-1'H,2H-3,4'-bipyrazole and 1'-(1-(5-bromopyridin-2-yl)-2-(4-fluorophenyl)ethyl)-1-(difluoromethyl)-1H,1'H-3,4'-bipyrazole (1.0 g, 2.16 mmol, 1.0 equiv.) in 1,4-dioxane (10.0 mL) and water (2.0 mL) was added (6-amino-3-chloro-2-fluorophenyl)boronic acid (0.82 g, 4.33 mmol, 2.0 equiv.), Pd(PPh$_3$)$_4$ (0.50 g, 0.43 mmol, 0.2 equiv.), K$_2$CO$_3$ (1.8 g, 12.98 mmol, 6.0 equiv.) and the solution was refluxed at 90° C. under N$_2$ for 2 h. The mixture was diluted with H$_2$O, extracted with ethyl acetate twice. The combined organic layers were washed with brine, dried over Na$_2$SO$_4$, concentrated and purified by silica gel chromatography (0→80%, EtOAc/petroleum ether) to yield a mixture of 4-chloro-2-(6-(1-(2-(difluoromethyl)-1'H,2H-[3,4'-bipyrazol]-1'-yl)-2-(4-fluorophenyl)ethyl)pyridin-3-yl)-3-fluoroaniline and 4-chloro-2-(6-(1-(1-(difluoromethyl)-1H,1'H-[3,4'-bipyrazol]-1'-yl)-2-(4-fluorophenyl)ethyl)pyridin-3-yl)-3-fluoroaniline as a light yellow solid. LC/MS: mass calculated for C$_{26}$H$_{19}$ClF$_4$N$_6$: 526.13, measured (ES, m/z): 527.10 [M+H]$^+$.

Step 3: The mixture of 1'-(1-(5-(3-chloro-2-fluoro-6-(1H-tetrazol-1-yl)phenyl)pyridin-2-yl)-2-(4-fluorophenyl)ethyl)-2-(difluoromethyl)-1'H,2H-3,4'-bipyrazole and 1'-(1-(5-(3-chloro-2-fluoro-6-(1H-tetrazol-1-yl)phenyl)pyridin-2-yl)-2-(4-fluorophenyl)ethyl)-1-(difluoromethyl)-1H,1'H-3,4'-bipyrazole To a solution of the mixture of 4-chloro-2-(6-(1-(2-(difluoromethyl)-1'H,2H-[3,4'-bipyrazol]-1'-yl)-2-(4-fluorophenyl)ethyl)pyridin-3-yl)-3-fluoroaniline and 4-chloro-2-(6-(1-(1-(difluoromethyl)-1H,1'H-[3,4'-bipyrazol]-1'-yl)-2-(4-fluorophenyl)ethyl)pyridin-3-yl)-3-fluoroaniline (1.0 g, 2.01 mmol, 1.0 equiv.) in acetic acid (3.0 mL) was added trimethoxymethane (3.0 mL), azidotrimethylsilane (3.0 mL) and the solution was stirred overnight at room temperature. The reaction was purified by reverse phase chromatography on C18 (80 g, MeCN/H$_2$O (0.05% CF$_3$COOH): 0→45%) to yield a mixture of 1'-(1-(5-(3-chloro-2-fluoro-6-(1H-tetrazol-1-yl)phenyl)pyridin-2-yl)-2-(4-fluorophenyl)ethyl)-2-(difluoromethyl)-1'H,2H-3,4'-bipyrazole and 1'-(1-(5-(3-chloro-2-fluoro-6-(1H-tetrazol-1-yl)phenyl)pyridin-2-yl)-2-(4-fluorophenyl)ethyl)-1-(difluoromethyl)-1H,1'H-3,4'-bipyrazole as a light yellow solid. LC/MS: mass calculated for C$_{27}$H$_{18}$ClF$_4$N$_9$: 579.13, measured (ES, m/z): 580.05 [M+H]$^+$.

Step 4: (R)-5-(3-Chloro-2-fluoro-6-(1H-tetrazol-1-yl)phenyl)-2-(1-(1-(difluoromethyl)-1H,1'H-[3,4'-bipyrazol]-1'-yl)-2-(4-fluorophenyl)ethyl)pyridine 1-oxide To a solution of the mixture of 1'-(1-(5-(3-chloro-2-fluoro-6-(1H-tetrazol-1-yl)phenyl)pyridin-2-yl)-2-(4-fluorophenyl)ethyl)-2-(difluoromethyl)-1'H,2H-3,4'-bipyrazole and 1'-(1-(5-(3-chloro-2-fluoro-6-(1H-tetrazol-1-yl)phenyl)pyridin-2-yl)-2-(4-fluorophenyl)ethyl)-1-(difluoromethyl)-1H,1'H-3,4'-bipyrazole (0.50 g, 0.86 mmol, 1.0 equiv.) in CH$_3$OH (5.0 mL) was added hydrogen peroxide (30 wt %, 0.98 mL, 8.62 mmol, 20.0 equiv.) and methyltrioxorhenium (43 mg, 0.17 mmol, 0.4 equiv.) and the solution was stirred for 1H at room temperature. The mixture was purified by reverse phase chromatography on C18 (80 g, MeCN/H$_2$O (0.05% CF$_3$COOH): 0→45%) to yield a mixture of 5-(3-chloro-2-fluoro-6-(1H-tetrazol-1-yl)phenyl)-2-(1-(2-(difluoromethyl)-1'H,2H-[3,4'-bipyrazol]-1'-yl)-2-(4-fluorophenyl)ethyl)pyridine 1-oxide and 5-(3-chloro-2-fluoro-6-(1H-tetrazol-1-yl)phenyl)-2-(1-(1-(difluoromethyl)-1H,1'H-[3,4'-bipyrazol]-1'-yl)-2-(4-fluorophenyl)ethyl)pyridine 1-oxide. The racemic product was separated by Chiral-HPLC to yield (R)-5-(3-chloro-2-fluoro-6-(1H-tetrazol-1-yl)phenyl)-2-(1-(1-(difluoromethyl)-1H,1'H-[3,4'-bipyrazol]-1'-yl)-2-(4-fluorophenyl)ethyl)pyridine 1-oxide as a white solid.

LC/MS: mass calculated for C$_{27}$H$_{18}$ClF$_4$N$_9$O: 595.13, measured (ES, m/z): 596.05 [M+H]$^+$. $^1$H NMR (400 MHz, DMSO-d$_6$): δ 9.70 (s, 1H), 8.47 (d, J=1.6 Hz, 1H), 8.32 (s, 1H), 8.19 (d, J=2.7 Hz, 1H), 8.07 (t, J=8.2 Hz, 1H), 7.97 (s, 1H), 7.69-7.91 (m, 2H), 7.33 (d, J=8.3 Hz, 1H), 7.15-7.23 (m, 3H), 7.02-7.11 (m, 2H), 6.71 (d, J=2.7 Hz, 1H), 6.15-6.28 (m, 1H), 3.66-3.47 (m, 2H). $^{19}$F NMR (376 MHz, DMSO-d$_6$): δ −93.92, −112.69, −116.14.

Example 608: (S*)-5-(3-Chloro-2-fluoro-6-(1H-tetrazol-1-yl)phenyl)-2-(2-(3-((difluoromethoxy)methyl)-4-fluoro-1H-pyrazol-1-yl)-1-(4-(2-(trifluoromethyl)pyridin-4-yl)-1H-pyrazol-1-yl)ethyl) pyridine 1-oxide

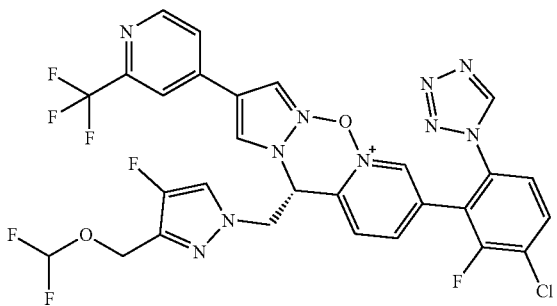

LC/MS: mass calculated for C$_{28}$H$_{18}$ClF$_7$N$_{10}$O$_2$: 694.12, measured (ES, m/z): 695.00 [M+H]$^+$. $^1$H NMR (400 MHz, DMSO-d$_6$) δ 9.69 (s, 1H), 8.73 (s, 1H), 8.67 (d, J=5.2 Hz, 1H), 8.53 (d, J=1.6 Hz, 1H), 8.39 (s, 1H), 8.03-8.12 (m, 2H), 7.87 (dd, J=5.2, 1.6 Hz, 1H), 7.70-7.80 (m, 2H), 7.46 (d, J=8.3 Hz, 1H), 7.23 (dd, J=8.2, 1.6 Hz, 1H), 6.45-6.89 (m, 2H), 4.89-5.06 (m, 2H), 4.80 (s, 2H). $^{19}$F NMR (376 MHz, DMSO-de) δ −66.57, −83.22, −112.63, −176.86.

Example 609: (R*)-5-(3-Chloro-2-fluoro-6-(1H-tetrazol-1-yl)phenyl)-2-(2-(3-((difluoromethoxy)methyl)-4-fluoro-1H-pyrazol-1-yl)-1-(4-(2-(trifluoromethyl)pyridin-4-yl)-1H-pyrazol-1-yl)ethyl) pyridine 1-oxide

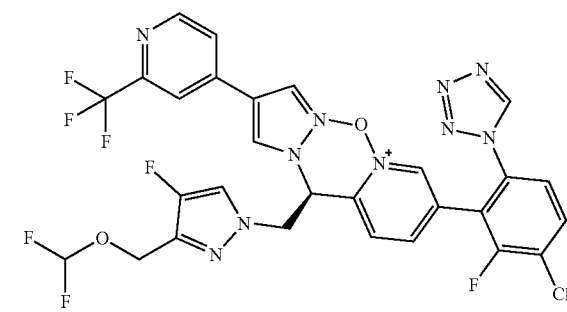

LC/MS: mass calculated for C$_{28}$H$_{18}$ClF$_7$N$_{10}$O$_2$: 694.12, measured (ES, m/z): 695.00 [M+H]$^+$. $^1$H NMR (400 MHz, DMSO-d$_6$) δ 9.55 (s, 1H), 8.61 (d, J=5.2 Hz, 1H), 8.48 (s, 1H), 8.40 (s, 1H), 8.26 (s, 1H), 7.91-8.01 (m, 2H), 7.79 (d, J=5.1 Hz, 1H), 7.59-7.69 (m, 2H), 7.52 (d, J=8.4 Hz, 1H), 7.20-7.26 (m, 1H), 6.27-6.77 (m, 2H), 4.83-5.01 (m, 2H), 4.75 (s, 2H). $^{19}$F NMR (376 MHz, DMSO-d$_6$) δ −66.64, −82.91, −112.73, −176.48.

Example 610: (R)-2-(1-(4-chloro-1-(difluoromethyl)-1H,1'H-[3,4'-bipyrazol]-1'-yl)-3-(difluoromethoxy)propyl)-5-(3-chloro-2-fluoro-6-(1H-tetrazol-1-yl)phenyl)pyridine 1-oxide

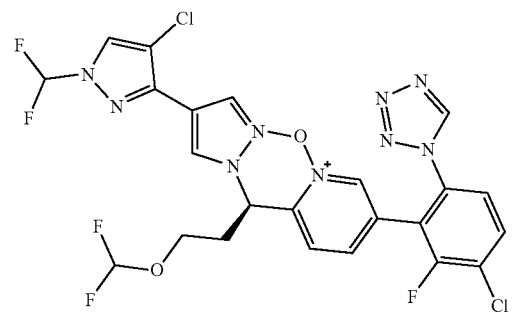

Step 1: 4-Chloro-1'-(1-(5-(3-chloro-2-fluoro-6-(1H-tetrazol-1-yl)phenyl)pyridin-2-yl)-3-(difluoromethoxy)propyl)-2-(difluoromethyl)-1'H,2H-3,4'-bipyrazole and 4-chloro-1'-(1-(5-(3-chloro-2-fluoro-6-(1H-tetrazol-1-yl)phenyl)pyridin-2-yl)-3-(difluoromethoxy)propyl)-1-(difluoromethyl)-1H,1'H-3,4'-bipyrazole A mixture of 1'-(1-(5-(3-chloro-2-fluoro-6-(1H-tetrazol-1-yl)phenyl)pyridin-2-yl)-3-(difluoromethoxy)propyl)-2-

(difluoromethyl)-1'H,2H-3,4'-bipyrazole and 1'-(1-(5-(3-chloro-2-fluoro-6-(1H-tetrazol-1-yl)phenyl)pyridin-2-yl)-3-(difluoromethoxy)propyl)-1-(difluoromethyl)-1H,1'H-3,4'-bipyrazole (0.2 g, 0.35 mmol, 1.0 equiv.), 1-chloropyrrolidine-2,5-dione (47 mg, 0.35 mmol, 1.0 equiv.) in DMF (2 mL) was stirred for overnight at 60° C. The mixture was purified by reverse phase chromatography on C18 (80 g, MeCN/H2O (0.05% CF3COOH): 0→45%) to yield a mixture of 4-chloro-1'-(1-(5-(3-chloro-2-fluoro-6-(1H-tetrazol-1-yl)phenyl)pyridine-2-yl)-3-(difluoromethoxy)propyl)-2-(difluoromethyl)-1'H,2H-3,4'-bipyrazole and 4-chloro-1'-(1-(5-(3-chloro-2-fluoro-6-(1H-tetrazol-1-yl)phenyl)pyridin-2-yl)-3-(difluoromethoxy)propyl)-1-(difluoromethyl)-1H,1'H-3,4'-bipyrazole as a white solid. LC/MS: mass calculated for $C_{23}H_{16}Cl_2F_5N_9O$: 599.08, measured (ES, m/z): 621.95 [M+Na]$^+$.

Step 2: (R)-2-(1-(4-Chloro-2-(difluoromethyl)-1'H,2H-[3,4'-bipyrazol]-1'-yl)-3-(difluoromethoxy)propyl)-5-(3-chloro-2-fluoro-6-(1H-tetrazol-1-yl)phenyl)pyridine-1-oxide A mixture of 4-chloro-1'-(1-(5-(3-chloro-2-fluoro-6-(1H-tetrazol-1-yl)phenyl)pyridin-2-yl)-3-(difluoromethoxy)propyl)-2-(difluoromethyl)-1'H,2H-3,4'-bipyrazole and 4-chloro-1'-(1-(5-(3-chloro-2-fluoro-6-(1H-tetrazol-1-yl)phenyl)pyridin-2-yl)-3-(difluoromethoxy)propyl)-1-(difluoromethyl)-1H,1'H-3,4'-bipyrazole (180 mg, 0.30 mmol, 1.0 equiv.), hydrogen peroxide (30 wt %, 0.34 mL, 3.0 mmol, 10.0 equiv.) and methyltrioxorhenium (15 mg, 0.06 mmol, 0.2 equiv.) in CH$_3$OH (2 mL) was stirred for 1 h at room temperature. The mixture was purified by reverse phase chromatography on C18 (80 g, MeCN/H$_2$O (0.05% CF$_3$COOH): 0→45%) to yield a mixture of 2-(1-(4-chloro-2-(difluoromethyl)-1'H,2H-[3,4'-bipyrazol]-1'-yl)-3-(difluoromethoxy)propyl)-5-(3-chloro-2-fluoro-6-(1H-tetrazol-1-yl)phenyl)pyridine 1-oxide and 2-(1-(4-chloro-1-(difluoromethyl)-1H,1'H-[3,4'-bipyrazol]-1'-yl)-3-(difluoromethoxy)propyl)-5-(3-chloro-2-fluoro-6-(1H-tetrazol-1-yl)phenyl)pyridine 1-oxide. The racemic product was separated by Chiral-HPLC to yield (R)-2-(1-(4-chloro-2-(difluoromethyl)-1'H,2H-[3,4'-bipyrazol]-1'-yl)-3-(difluoromethoxy)propyl)-5-(3-chloro-2-fluoro-6-(1H-tetrazol-1-yl)phenyl)pyridine 1-oxide as a white solid.

LC/MS: mass calculated for $C_{23}H_{16}Cl_2F_5N_9O_2$: 615.07, measured (ES, m/z): 615.95 [M+H]$^+$. $^1$H NMR (400 MHz, DMSO-d$_6$): δ 9.70 (s, 1H), 8.44-8.50 (m, 2H), 8.02-8.12 (m, 2H), 7.94 (s, 1H), 7.60-7.92 (m, 2H), 7.36 (d, J=8.3 Hz, 1H), 7.17-7.26 (m, 1H), 6.62 (t, J=75.6 Hz, 1H), 6.20-6.31 (m, 1H), 3.80-3.90 (m, 1H), 3.62-3.75 (m, 1H), 2.55-2.71 (m, 2H). $^{19}$F NMR (376 MHz, DMSO-d$_6$): δ −83.43, −94.21, −112.64.

Example 611: ((S)-2-(1-(4-chloro-1-(difluoromethyl)-1H,1'H-[3,4'-bipyrazol]-1'-yl)-3-(difluoromethoxy)propyl)-5-(3-chloro-2-fluoro-6-(1H-tetrazol-1-yl)phenyl)pyridine 1-oxide

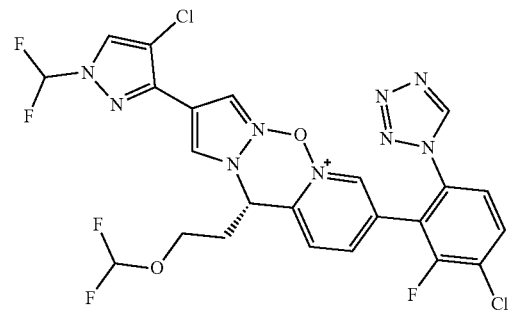

LC/MS: mass calculated for $C_{23}H_{16}Cl_2F_5N_9O_2$: 615.07, measured (ES, m/z): 616.00 [M+H]$^+$. $^1$H NMR (400 MHz, DMSO-d$_6$) δ 9.69 (s, 1H), 8.63 (s, 1H), 8.53 (s, 1H), 8.45 (d, J=1.6 Hz, 1H), 8.02-8.11 (m, 2H), 7.70-7.97 (m, 2H), 7.27 (d, J=8.3 Hz, 1H), 7.18 (dd, J=8.2, 1.6 Hz, 1H), 6.63 (t, J=76.0 Hz, 1H), 6.20-6.29 (m, 1H), 3.80-3.88 (m, 1H), 3.62-3.72 (m, 1H), 2.56-2.74 (m, 2H). $^{19}$F NMR (376 MHz, DMSO-d$_6$) δ −83.31, −94.92, −112.72.

Example 612: (R)-2-(1-(4-chloro-2-(difluoromethyl)-1'H,2H-[3,4'-bipyrazol]-1'-yl)-3-(difluoromethoxy)propyl)-5-(3-chloro-2-fluoro-6-(1H-tetrazol-1-yl)phenyl)pyridine 1-oxide

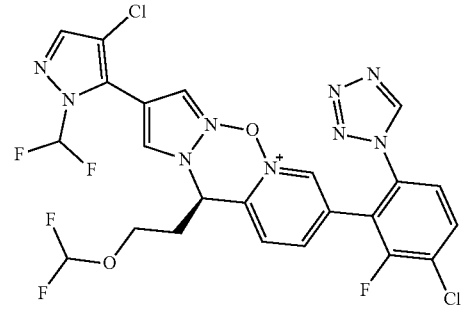

Step 1: 4-Chloro-1'-(1-(5-(3-chloro-2-fluoro-6-(1H-tetrazol-1-yl)phenyl) pyridin-2-yl)-3-(difluoromethoxy)propyl)-2-(difluoromethyl)-1'H,2H-3,4'-bipyrazole and 4-chloro-1'-(1-(5-(3-chloro-2-fluoro-6-(1H-tetrazol-1-yl) phenyl)pyridin-2-yl)-3-(difluoromethoxy)propyl)-1-(difluoromethyl)-1H,1'H-3,4'-bipyrazole A mixture of 1'-(1-(5-(3-chloro-2-fluoro-6-(1H-tetrazol-1-yl)phenyl)pyridin-2-yl)-3-(difluoromethoxy)propyl)-2-(difluoromethyl)-1'H,2H-3,4'-bipyrazole and 1'-(1-(5-(3-chloro-2-fluoro-6-(1H-tetrazol-1-yl)phenyl)pyridin-2-yl)-3-(difluoromethoxy)propyl)-1-(difluoromethyl)-1H,1'H-3,4'-bipyrazole (0.2 g, 0.35 mmol, 1.0 equiv.), 1-chloropyrrolidine-2,5-dione (47 mg, 0.35 mmol, 1.0 equiv.) in DMF (2 mL) was stirred for overnight at 60° C. The mixture was purified by reverse phase chromatography on C18 (80 g, MeCN/H₂O (0.05% CF₃COOH): 0→45%) to yield a mixture of 4-chloro-1'-(1-(5-(3-chloro-2-fluoro-6-(1H-tetrazol-1-yl)phenyl)pyridin-2-yl)-3-(difluoromethoxy)propyl)-2-(difluoromethyl)-1'H,2H-3,4'-bipyrazole and 4-chloro-1'-(1-(5-(3-chloro-2-fluoro-6-(1H-tetrazol-1-yl)phenyl)pyridin-2-yl)-3-(difluoromethoxy)propyl)-1-(difluoromethyl)-1H,1'H-3,4'-bipyrazole as a white solid. LC/MS: mass calculated for C₂₃H₁₆Cl₂F₅N₉O: 599.08, measured (ES, m/z): 621.95 [M+Na]⁺.

Step 2: (R)-2-(1-(4-Chloro-2-(difluoromethyl)-1'H,2H-[3,4'-bipyrazol]-1'-yl)-3-(difluoromethoxy)propyl)-5-(3-chloro-2-fluoro-6-(1H-tetrazol-1-yl)phenyl)pyridine 1-oxide A mixture of 4-chloro-1'-(1-(5-(3-chloro-2-fluoro-6-(1H-tetrazol-1-yl)phenyl) pyridin-2-yl)-3-(difluoromethoxy)propyl)-2-(difluoromethyl)-1'H,2H-3,4'-bipyrazole and 4-chloro-1'-(1-(5-(3-chloro-2-fluoro-6-(1H-tetrazol-1-yl) phenyl)pyridin-2-yl)-3-(difluoromethoxy)propyl)-1-(difluoromethyl)-1H,1'H-3,4'-bipyrazole (180 mg, 0.30 mmol, 1.0 equiv.), hydrogen peroxide (30 wt %, 0.34 mL, 3.0 mmol, 10.0 equiv.) and methyltrioxorhenium (15 mg, 0.06 mmol, 0.2 equiv.) in CH₃OH (2 mL) was stirred for 1 h at room temperature. The mixture was purified by reverse phase chromatography on C18 (80 g, MeCN/H₂O (0.05% CF₃COOH): 0→45%) to yield a mixture of 2-(1-(4-chloro-2-(difluoromethyl)-1'H,2H-[3,4'-bipyrazol]-1'-yl)-3-(difluoromethoxy)propyl)-5-(3-chloro-2-fluoro-6-(1H-tetrazol-1-yl)phenyl)pyridine 1-oxide and 2-(1-(4-chloro-1-(difluoromethyl)-1H,1'H-[3,4'-bipyrazol]-1'-yl)-3-(difluoromethoxy)propyl)-5-(3-chloro-2-fluoro-6-(1H-tetrazol-1-yl)phenyl)pyridine 1-oxide. The racemic product was separated by Chiral-HPLC to yield (R)-2-(1-(4-chloro-2-(difluoromethyl)-1'H,2H-[3,4'-bipyrazol]-1'-yl)-3-(difluoromethoxy)propyl)-5-(3-chloro-2-fluoro-6-(1H-tetrazol-1-yl)phenyl)pyridine 1-oxide as a white solid.

LC/MS: mass calculated for C₂₃H₁₆Cl₂F₅N₉O₂: 615.07, measured (ES, m/z): 616.00 [M+H]⁺. ¹H NMR (400 MHz, DMSO-d₆): δ 9.69 (s, 1H), 8.63 (s, 1H), 8.53 (s, 1H), 8.45 (d, J=1.6 Hz, 1H), 8.02-8.11 (m, 2H), 7.60-7.97 (m, 2H), 7.27 (d, J=8.3 Hz, 1H), 7.15-7.22 (m, 1H), 6.63 (t, J=75.6 Hz, 1H), 6.20-6.30 (m, 1H), 3.79-3.89 (m, 1H), 3.62-3.75 (m, 1H), 2.56-2.70 (m, 2H).

Example 613: ((S)-2-(1-(4-chloro-2-(difluoromethyl)-1'H,2H-[3,4'-bipyrazol]-1'-yl)-3-(difluoromethoxy)propyl)-5-(3-chloro-2-fluoro-6-(1H-tetrazol-1-yl)phenyl)pyridine 1-oxide

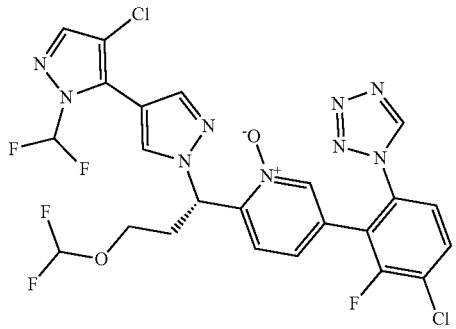

LC/MS: mass calculated for C₂₃H₁₆Cl₂F₅N₉O₂: 615.07, measured (ES, m/z): 616.00 [M+H]⁺. ¹H NMR (400 MHz, DMSO-d₆) δ 9.70 (s, 1H), 8.50-8.44 (m, 2H), 8.02-8.12 (m, 2H), 7.90-7.95 (m, 1H), 7.73-7.80 (m, 2H), 7.36 (d, J=8.3 Hz, 1H), 7.21 (dd, J=8.3, 1.7 Hz, 1H), 6.62 (t, J=75.6 Hz, 1H), 6.20-6.29 (m, 1H), 3.80-3.88 (m, 1H), 3.63-3.70 (m, 1H), 2.55-2.72 (m, 2 h). ¹⁹F NMR (376 MHz, DMSO-d₆) δ −83.43, −94.22, −112.64.

Example 614: (R)-2-(1-(4-chloro-1-(difluoromethyl)-1H,1'H-[3,4'-bipyrazol]-1'-yl)-3-methoxypropyl)-5-(3-chloro-2-fluoro-6-(1H-tetrazol-1-yl)phenyl)pyridine 1-oxide

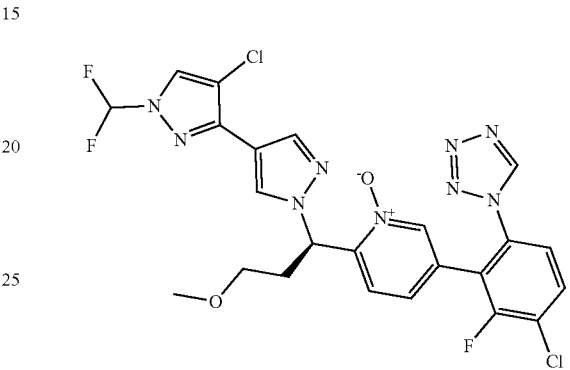

LC/MS: mass calculated for C₂₃H₁₈Cl₂F₃N₉O₂: 579.09, measured (ES, m/z): 580.00 [M+H]⁺. ¹H NMR (300 MHz, DMSO-d₆) δ 9.65 (s, 1H), 8.59 (s, 1H), 8.40-8.53 (m, 2H), 8.00-8.10 (m, 2H), 7.56-7.99 (m, 2H), 7.29 (d, J=8.3 Hz, 1H), 7.15 (d, J=8.3 Hz, 1H), 6.17-6.28 (m, 1H), 3.25-3.35 (m, 1H), 3.10-3.23 (m, 4H), 2.53-2.58 (m, 1H), 2.45-2.49 (m, 1H). ¹⁹F NMR (282 MHz, DMSO-d₆) δ −73.97, −94.90, −112.73.

Example 615: (S)-2-(1-(4-chloro-1-(difluoromethyl)-1H,1'H-[3,4'-bipyrazol]-1'-yl)-3-methoxypropyl)-5-(3-chloro-2-fluoro-6-(1H-tetrazol-1-yl)phenyl)pyridine 1-oxide

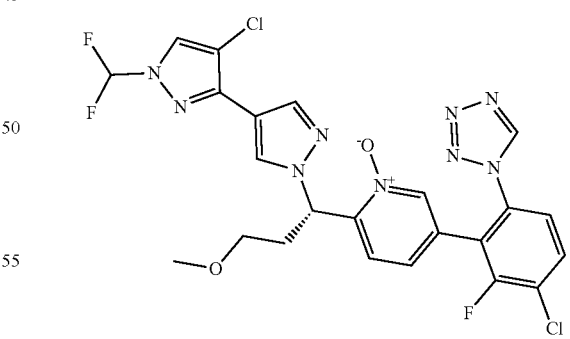

LC/MS: mass calculated for C₂₃H₁₈Cl₂F₃N₉O₂: 579.09, measured (ES, m/z): 580.00 [M+H]⁺. ¹H NMR (300 MHz, DMSO-d₆) δ 9.65 (s, 1H), 8.59 (s, 1H), 8.40-8.51 (m, 2H), 8.00-8.10 (m, 2H), 7.56-7.99 (m, 2H), 7.29 (d, J=8.3 Hz, 1H), 7.15 (d, J=8.3 Hz, 1H), 6.17-6.28 (m, 1H), 3.25-3.35 (m, 1H), 3.10-3.23 (m, 4H), 2.53-2.58 (m, 1H), 2.45-2.49 (m, 1H). ¹⁹F NMR (282 MHz, DMSO-d₆) δ −73.84, −94.91, −112.73.

Example 616: (R)-5-(3-chloro-2-fluoro-6-(1H-tetrazol-1-yl)phenyl)-2-(2-cyclopropyl-1-(2-(difluoromethyl)-1'H,2H-[3,4'-bipyrazol]-1'-yl)ethyl)pyridine 1-oxide

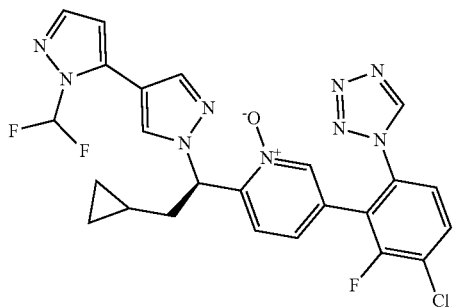

Step 1: 1'-(1-(5-Bromopyridin-2-yl)-2-cyclopropylethyl)-2-(difluoromethyl)-1'H,2H-3,4'-bipyrazole A mixture of cesium carbonate (509 mg, 1.56 mmol, 1.0 equiv.) and 2-(difluoromethyl)-1'H,2H-3,4'-bipyrazole (288 mg, 1.56 mmol, 1.0 equiv.) in acetonitrile (3 mL) was stirred for 15 min at room temperature. 1-(5-bromopyridin-2-yl)-2-cyclopropylethyl methanesulfonate (500 mg, 1.56 mmol, 1.0 equiv.) was added and the solution was stirred for 2.5 h at 70° C. The resulting mixture was diluted with water, extracted with EA (3×5 mL). Then the organic layers were combined, washed with brine, dried over $Na_2SO_4$ and concentrated. The residue was purified by silica gel chromatography (EA/PE, 0%→50%) to yield 1'-(1-(5-bromopyridin-2-yl)-2-cyclopropylethyl)-2-(difluoromethyl)-1'H,2H-3,4'-bipyrazole as a yellow oil. LC/MS: mass calculated for $C_{17}H_{16}BrF_2N_5$: 407.06, measured (ES, m/z): 408.00[M+H]$^+$.

Step 2: 4-Chloro-2-(6-(2-cyclopropyl-1-(2-(difluoromethyl)-1'H,2H-[3,4'-bipyrazol]-1'-yl)ethyl)pyridin-3-yl)-3-fluoroaniline A mixture of 1'-(1-(5-bromopyridin-2-yl)-2-cyclopropylethyl)-2-(difluoromethyl)-1'H,2H-3,4'-bipyrazole (360 mg, 0.89 mmol, 1.0 equiv.), 6-amino-3-chloro-2-fluorophenylboronic acid (251 mg, 1.3 mmol, 1.5 equiv.), Pd(PPh$_3$)$_4$ (102 mg, 0.09 mmol, 0.1 equiv.) and $K_2CO_3$ (366 mg, 2.65 mmol, 3.0 equiv.) in 1,4-dioxane/water (V/V=4:1, 3 mL) was refluxed at 90° C. under $N_2$ for 3 h. The resulting mixture was diluted with water, and the mixture extracted with EA (3×5 mL). The organic layers were combined, washed with water (5 mL), dried over $Na_2SO_4$ and concentrated. The residue was purified by silica gel chromatography (0%→10%, DCM/MeOH) to yield 4-chloro-2-(6-(2-cyclopropyl-1-(2-(difluoromethyl)-1'H,2H-[3,4'-bipyrazol]-1'-yl)ethyl)pyridin-3-yl)-3-fluoroaniline as a yellow oil. LC/MS: mass calculated for $C_{23}H_{20}ClF_3N_6$: 472.14, measured (ES, m/z): 473.10[M+H]$^+$.

Step 3: 1'-(1-(5-(3-Chloro-2-fluoro-6-(1H-tetrazol-1-yl)phenyl)pyridin-2-yl)-2-cyclopropylethyl)-2-(difluoromethyl)-1'H,2H-3,4'-bipyrazole A mixture of 4-chloro-2-(6-(2-cyclopropyl-1-(2-(difluoromethyl)-1'H,2H-[3,4'-bipyrazol]-1'-yl)ethyl)pyridin-3-yl)-3-fluoroaniline (373 mg, 0.79 mmol, 1.0 equiv.), trimethoxymethane (2 mL), azidotrimethylsilane (2 mL) and acetic acid (2 mL) was stirred overnight at 25° C. The reaction was purified by reverse chromatography on C18 (0%→55% MeCN/H$_2$O (0.05% CF$_3$COOH)) to yield 1'-(1-(5-(3-chloro-2-fluoro-6-(1H-tetrazol-1-yl)phenyl)pyridin-2-yl)-2-cyclopropylethyl)-2-(difluoromethyl)-1'H,2H-3,4'-bipyrazole as a light yellow solid.

Step 4: (R)-5-(3-Chloro-2-fluoro-6-(1H-tetrazol-1-yl)phenyl)-2-(2-cyclopropyl-1-(2-(difluoromethyl)-1'H,2H-[3,4'-bipyrazol]-1'-yl)ethyl)pyridine 1-oxide A mixture of 1'-(1-(5-(3-chloro-2-fluoro-6-(1H-tetrazol-1-yl)phenyl)pyridin-2-yl)-2-cyclopropylethyl)-2-(difluoromethyl)-1'H,2H-3,4'-bipyrazole (100 mg, 0.19 mmol, 1.0 equiv.), methyltrioxorhenium (24 mg, 0.01 mmol, 0.5 equiv.) and hydrogen peroxide (0.5 mL) in CH$_3$OH (2 mL) was stirred for 2 h at room temperature. The resulting mixture was purified by reverse phase chromatography on C18 (MeCN/H$_2$O (0.05% CF$_3$COOH)) to yield 5-(3-chloro-2-fluoro-6-(1H-tetrazol-1-yl)phenyl)-2-(2-cyclopropyl-1-(2-(difluoromethyl)-1'H,2H-[3,4'-bipyrazol]-1'-yl)ethyl)pyridine 1-oxide as an off-white solid. The racemic product was separated by chiral-HPLC to yield (R)-5-(3-chloro-2-fluoro-6-(1H-tetrazol-1-yl)phenyl)-2-(2-cyclopropyl-1-(2-(difluoromethyl)-1'H,2H-[3,4'-bipyrazol]-1'-yl)ethyl)pyridine 1-oxide as an off-white solid.

LC/MS: mass calculated for $C_{24}H_{19}ClF_3N_9O$: 541.14, measured (ES, m/z): 542.10 [M+H]$^+$. $^1$H NMR (300 MHz, DMSO-d$_6$) δ 9.67 (s, 1H), 8.41 (d, J=6.3 Hz, 2H), 7.97-8.10 (m, 1H), 7.58-7.90 (m, 4H), 7.34 (d, J=8.3 Hz, 1H), 7.15 (d, J=8.1 Hz, 1H), 6.66 (d, J=1.7 Hz, 1H), 6.14-6.19 (m, 1H), 2.30-2.40 (m, 1H), 1.86-1.98 (m, 1H), 0.38-0.63 (m, 1H), 0.18-0.43 (m, 2H), 0.03-0.14 (m, 1H), −0.12--0.02 (m, 1H). $^{19}$F-NMR (282 MHz, DMSO-d$_6$) δ −93.56, −112.75.

Example 617: (S)-5-(3-Chloro-2-fluoro-6-(1H-tetrazol-1-yl)phenyl)-2-(3-(difluoromethoxy)-1-(4-(4-(trifluoromethyl)thiazol-5-yl)-1H-pyrazol-1-yl)propyl)pyridine 1-oxide

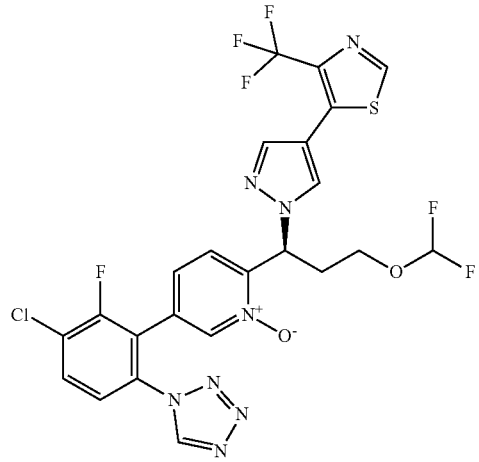 [SMILES: [O-][n+]1cc(-c2c(-n3cnnn3)ccc(Cl)c2F)ccc1[C@H](CCOC(F)F)n1cc(-c2scnc2C(F)(F)F)cn1]

Step 1:
5-(1H-Pyrazol-4-yl)-4-(trifluoromethyl)thiazole

A mixture of 5-bromo-4-(trifluoromethyl)thiazole (200 mg, 0.86 mmol, 1.0 equiv.), 1-Boc-pyrazole-4-boronic acid pinacol ester (507 mg, 1.72 mmol, 2.0 equiv.), Pd(PPh$_3$)$_4$ (100 mg, 0.09 mmol, 0.1 equiv.), potassium carbonate (357 mg, 2.59 mmol, 3.0 equiv.) in DMF (2 mL) and water (0.5 mL) was stirred at 90° C. under nitrogen for 2 h. The solution was diluted with H$_2$O, extracted with ethyl acetate twice. The combined organic layers was washed with brine, dried over Na$_2$SO$_4$, concentrated, and purified by silica gel chromatography (0→10% MeOH/DCM) to yield 5-(1H-pyrazol-4-yl)-4-(trifluoromethyl)thiazole as light yellow oil. LC/MS: mass calculated for C$_7$H$_4$F$_3$N$_3$S: 219.01 measured (ES, m/z): 219.95 [M+H]$^+$ Step 2: 5-(1-(1-(5-Bromopyridin-2-yl)-3-(difluoromethoxy)propyl)-1H-pyrazol-4-yl)-4-(trifluoromethyl)thiazole A mixture of 5-(1H-pyrazol-4-yl)-4-(trifluoromethyl)thiazole (160 mg, 0.73 mmol, 1.2 equiv.) and cesium carbonate (218 mg, 0.67 mmol, 1.1 equiv.) in acetonitrile (2 mL) was stirred for 15 min at room temperature. 1-(5-Bromopyridin-2-yl)-3-(difluoromethoxy)propyl methanesulfonate (219 mg, 0.61 mmol, 1.0 equiv.) was added and the solution was stirred for 3 h at 90° C. The solution was diluted with H$_2$O, extracted with ethyl acetate twice. The combined organic layers was washed with brine, dried over Na$_2$SO$_4$, concentrated and purified by silica gel chromatography (0→50% EA/PE) to yield 5-(1-(1-(5-bromopyridin-2-yl)-3-(difluoromethoxy)propyl)-1H-pyrazol-4-yl)-4-(trifluoromethyl)thiazole as light yellow oil. LC/MS: mass calculated for C$_{16}$H$_{12}$BrF$_5$N$_4$OS: 481.98, measured (ES, m/z): 482.90 [M+H]$^+$.

Step 3: 4-Chloro-2-(6-(3-(difluoromethoxy)-1-(4-(4-(trifluoromethyl)thiazol-5-yl)-1H-pyrazol-1-yl)propyl)pyridin-3-yl)-3-fluoroaniline A mixture of 5-(1-(1-(5-bromopyridin-2-yl)-3-(difluoromethoxy)propyl)-1H-pyrazol-4-yl)-4-(trifluoromethyl)thiazole (270 mg, 0.56 mmol, 1.0 equiv.), (6-amino-3-chloro-2-fluorophenyl)boronic acid (212 mg, 1.12 mmol, 2.0 equiv.), Pd(PPh$_3$)$_4$ (129 mg, 0.11 mmol, 0.2 equiv.), K$_2$CO$_3$ (463 mg, 3.35 mmol, 6.0 equiv.) in 1,4-dioxane (4 mL) and water (1 mL) was stirred at 90° C. under N$_2$ for 2 h. The mixture was diluted with water, extracted with ethyl acetate twice. The combined organic layers was washed with brine, dried over Na$_2$SO$_4$, concentrated and purified by silica gel chromatography (0→8% MeOH/DCM) to yield 4-chloro-2-(6-(3-(difluoromethoxy)-1-(4-(4-(trifluoromethyl)thiazol-5-yl)-1H-pyrazol-1-yl)propyl)pyridin-3-yl)-3-fluoroaniline as light yellow oil. LC/MS: mass calculated for C$_{22}$H$_{16}$ClF$_6$N$_5$OS: 547.07, measured (ES, m/z): 548.00 [M+H]$^+$.

Step 4: 5-(1-(1-(5-(3-Chloro-2-fluoro-6-(1H-tetrazol-1-yl)phenyl)pyridin-2-yl)-3-(difluoromethoxy)propyl)-1H-pyrazol-4-yl)-4-(trifluoromethyl)thiazole A mixture of 4-chloro-2-(6-(3-(difluoromethoxy)-1-(4-(4-(trifluoromethyl)thiazol-5-yl)-1H-pyrazol-1-yl)propyl)pyridin-3-yl)-3-fluoroaniline (146 mg, 0.27 mmol, 1.0 equiv.), trimethoxymethane (1 mL), azidotrimethylsilane (1 mL) and acetic acid (1 mL) was stirred overnight at room temperature, then concentrated under vacuum. The residue was purified by reverse phase chromatography on C18 (0→45%, MeCN/H$_2$O (0.05% CF$_3$COOH)) to yield 5-(1-(1-(5-(3-chloro-2-fluoro-6-(5H-1l4-tetrazol-1-yl)phenyl)pyridin-2-yl)-3-(difluoromethoxy)propyl)-1H-pyrazol-4-yl)-4-(trifluoromethyl)thiazole as light yellow oil. LC/MS: mass calculated for C$_{23}$H$_{15}$ClF$_6$N$_8$OS: 600.07, measured (ES, m/z): 622.95 [M+Na]$^+$.

Step 5: (S)-5-(3-Chloro-2-fluoro-6-(1H-tetrazol-1-yl)phenyl)-2-(3-(difluoromethoxy)-1-(4-(4-(trifluoromethyl)thiazol-5-yl)-1H-pyrazol-1-yl)propyl)pyridine 1-oxide A mixture of 5-(1-(1-(5-(3-chloro-2-fluoro-6-(1H-tetrazol-1-yl)phenyl)pyridin-2-yl)-3-(difluoromethoxy)propyl)-1H-pyrazol-4-yl)-4-(trifluoromethyl)thiazole (100 mg, 0.17 mmol, 1.0 equiv.), hydrogen peroxide (30 wt %, 0.19 mL, 1.66 mmol, 10.0 equiv.) and methyltrioxorhenium (8 mg, 0.033 mmol, 0.2 equiv.) in CH$_3$OH (1 mL) was stirred for 1 h at room temperature. The mixture was purified by reverse phase chromatography on C18 (0→45%, MeCN/H$_2$O (0.05% CF$_3$COOH)) to yield 5-(3-chloro-2-fluoro-6-(1H-tetrazol-1-yl)phenyl)-2-(3-(difluoromethoxy)-1-(4-(4-(trifluoromethyl)thiazol-5-yl)-1H-pyrazol-1-yl)propyl)pyridine 1-oxide. The racemic product was separated by Chiral-HPLC to yield (S)-5-(3-chloro-2-fluoro-6-(1H-tetrazol-1-yl)phenyl)-2-(3-(difluoromethoxy)-1-(4-(4-(trifluoromethyl)thiazol-5-yl)-1H-pyrazol-1-yl)propyl)pyridine 1-oxide as a white solid.

LC/MS: mass calculated for C$_{23}$H$_{15}$ClF$_6$N$_8$O$_2$S: 616.06, measured (ES, m/z): 616.95 [M+H]$^+$. $^1$H NMR (400 MHz, DMSO-d$_6$): δ 9.69 (s, 1H), 9.17 (s, 1H), 8.47 (d, J=1.6 Hz, 1H), 8.39 (s, 1H), 8.02-8.11 (m, 1H), 7.86 (s, 1H), 7.72-7.80 (m, 1H), 7.34 (d, J=8.3 Hz, 1H), 7.18-7.25 (m, 1H), 6.62 (t, J=76.0 Hz, 1H), 6.18-6.26 (m, 1H), 3.79-3.89 (m, 1H), 3.60-3.70 (m, 1H), 2.55-2.70 (m, 2H).

Example 618: (R)-5-(3-Chloro-2-fluoro-6-(1H-tetrazol-1-yl)phenyl)-2-(3-(difluoromethoxy)-1-(4-(4-(trifluoromethyl)thiazol-5-yl)-1H-pyrazol-1-yl)propyl)pyridine 1-oxide

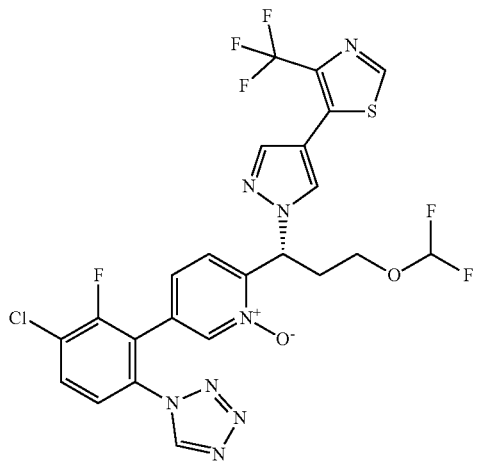 [SMILES: [O-][n+]1cc(-c2c(-n3cnnn3)ccc(Cl)c2F)ccc1[C@@H](CCOC(F)F)n1cc(-c2scnc2C(F)(F)F)cn1]

LC/MS: mass calculated for C$_{23}$H$_{15}$ClF$_6$N$_8$O$_2$S: 616.06, measured (ES, m/z): 616.95 [M+H]$^+$. $^1$H NMR (400 MHz, DMSO-d$_6$): δ 9.69 (s, 1H), 9.17 (s, 1H), 8.47 (d, J=1.6 Hz, 1H), 8.39 (s, 1H), 8.01-8.11 (m, 1H), 7.86 (s, 1H), 7.72-7.80 (m, 1H), 7.34 (d, J=8.3 Hz, 1H), 7.17-7.26 (m, 1H), 6.62 (t, J=75.6 Hz, 1H), 6.20-6.28 (m, 1H), 3.79-3.89 (m, 1H), 3.61-3.71 (m, 1H), 2.55-2.70 (m, 2H).

Example 619: (S)-5-(3-Chloro-2-fluoro-6-(1H-tetrazol-1-yl)phenyl)-2-(1-(4-(2-chloro-6-fluorophenyl)-1H-pyrazol-1-yl)-3-(difluoromethoxy)propyl)pyridine 1-oxide

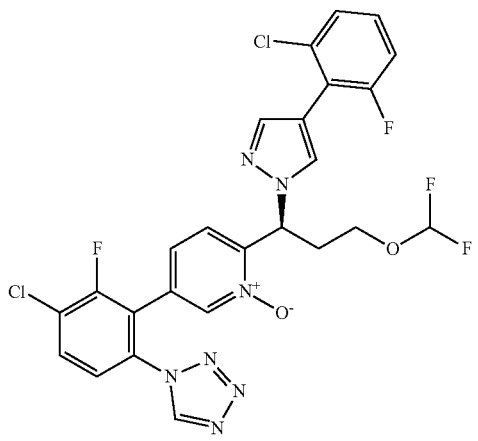 [SMILES: [O-][n+]1cc(-c2c(-n3cnnn3)ccc(Cl)c2F)ccc1[C@H](CCOC(F)F)n1cc(-c2c(F)cccc2Cl)cn1]

LC/MS: mass calculated for $C_{24}H_{16}Cl_2F_4N_8O_2$: 594.07, measured (ES, m/z): 616.95 [M+Na]$^+$. $^1$H NMR (300 MHz, DMSO-$d_6$) δ 9.67 (s, 1H), 8.55-8.64 (m, 3H), 8.44 (d, J=1.5 Hz, 1H), 7.99-8.15 (m, 2H), 7.74 (dd, J=8.8, 1.6 Hz, 1H), 7.35 (d, J=8.3 Hz, 1H), 7.19 (d, J=8.1 Hz, 1H), 6.32-6.91 (m, 1H), 6.22-6.38 (m, 1H), 3.52-3.92 (m, 2H), 2.59-2.67 (m, 2H). $^{19}$F NMR (282 MHz, DMSO-$d_6$) δ −83.41, −112.65, −126.21.

Example 620: (R)-5-(3-Chloro-2-fluoro-6-(1H-tetrazol-1-yl)phenyl)-2-(1-(4-(4-chlorothiazol-5-yl)-1H-pyrazol-1-yl)-3-(difluoromethoxy)propyl)pyridine 1-oxide

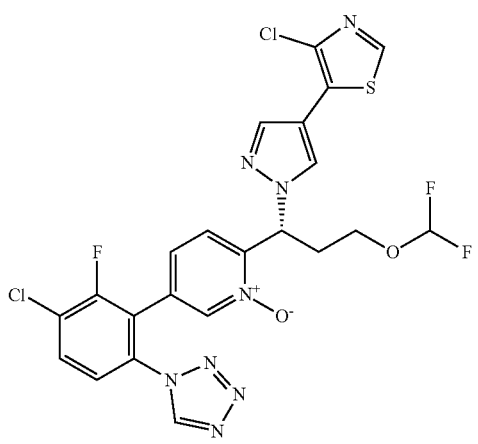 [SMILES: [O-][n+]1cc(-c2c(-n3cnnn3)ccc(Cl)c2F)ccc1[C@@H](CCOC(F)F)n1cc(-c2scnc2Cl)cn1]

Step 1: 2,5-Dibromo-4-chlorothiazole

To a 100 mL round-bottomed flask was added 2,4-dichlorothiazole (5.0 g, 32.5 mmol, 1.0 equiv.) and glacial acetic acid (10.0 mL). The resulting solution was treated slowly dropwise via addition funnel with Br$_2$ (2.5 mL, 48.7 mmol, 1.5 equiv.) over 5 minutes. The mixture was stirred at 90° C. for 3 Hours. After cooling, the mixture was basified with solid sodium carbonate, first, then 5% sodium carbonate (aq). The overall mixture was extracted with ethyl acetate (3×100 mL), and the combined organic layers were washed with 5% sodium carbonate, dried, and concentrated to yield 2,5-dibromo-4-chlorothiazole as a light yellow oil. LC/MS: mass calculated for $C_3Br_2ClNS$: 274.78, measured (ES, m/z): 275.75, 277.75 [M+H, M+H+2]$^+$.

Step 2: 5-Bromo-4-chloro-N-(4-methoxybenzyl) thiazol-2-amine

A mixture of 2,5-dibromo-4-chlorothiazole (5.0 g, 18.0 mmol, 1.0 equiv.) and (4-methoxyphenyl)methanamine (2.5 g, 18.0 mmol, 1.0 equiv.) in 1,4-dioxane (75 mL) was stirred at 80° C. for 4 h and the mixture was concentrated. The residue was diluted with water, and the mixture extracted with ethyl acetate three times. The combined organic layers were washed with sodium bicarbonate solution and brine, dried over anhydrous sodium sulfate and concentrated. The residue was purified by silica gel chromatography (0→50% ethyl acetate/petroleum ether) to yield 5-bromo-4-chloro-N-(4-methoxybenzyl)thiazol-2-amine as a yellow solid. LC/MS: mass calculated for $C_{11}H_{10}BrClN_2OS$: 331.94, measured (ES, m/z): 332.90, 334.90 [M+H, M+H+2]$^+$.

Step 3: tert-Butyl (5-bromo-4-chlorothiazol-2-yl)(4-methoxybenzyl)carbamate

A mixture of 5-bromo-4-chloro-N-(4-methoxybenzyl)thiazol-2-amine (4.7 g, 14.1 mmol, 1.0 equiv.), Boc$_2$O (4.6 g, 21.1 mmol, 1.5 equiv.), triethylamine (4.3 g, 42.3 mmol, 3.0 equiv.) and DMAP (172 mg, 1.4 mmol, 0.1 equiv.) in tetrahydrofuran (50 mL) was stirred at room temperature overnight. The reaction was quenched with water, and the mixture extracted with ethyl acetate twice. The combined organic layers were washed with brine, dried over anhydrous sodium sulfate and concentrated. The residue was purified by silica gel chromatography (0→50% ethyl acetate/petroleum ether) to yield tert-butyl (5-bromo-4-chlorothiazol-2-yl)(4-methoxybenzyl)carbamate as an off-white solid. LC/MS: mass calculated for $C_{16}H_{18}BrClN_2O_3S$: 431.99, measured (ES, m/z): 376.85, 378.90 [M−t−Bu+H, M−t−Bu+H+2]$^+$.

Step 4: tert-Butyl (4-chloro-5-(1H-pyrazol-4-yl)thiazol-2-yl)(4-methoxybenzyl)carbamate A mixture of tert-butyl (5-bromo-4-chlorothiazol-2-yl)(4-methoxybenzyl)carbamate (2.5 g, 5.8 mmol, 1.0 equiv.), tert-butyl 4-(4,4,5,5-tetramethyl-1,3,2-dioxaborolan-2-yl)-1H-pyrazole-1-carboxylate (3.4 g, 11.5 mmol, 2.0 equiv.), potassium carbonate (2.4 g, 17.3 mmol, 3.0 equiv.) and tetrakis(triphenylphosphine)palladium (666 mg, 0.58 mmol, 0.1 equiv.) in DMF (30 mL) and water (5 mL) was stirred at 90° C. for 4 h. After cooling to room temperature, the reaction was quenched with water, and the mixture extracted with ethyl acetate twice. The combined organic layers were washed with brine, dried over anhydrous sodium sulfate and concentrated. The residue was purified by silica gel chromatography (0→50% ethyl acetate/petroleum ether) to yield tert-butyl (4-chloro-5-(1H-pyrazol-4-yl)thiazol-2-yl)(4-methoxybenzyl)carbamate as a light yellow solid. LC/MS: mass calculated for $C_{19}H_{21}ClN_4O_3S$: 420.10, measured (ES, m/z): 421.10 [M+H]$^+$.

Step 5: tert-Butyl (5-(1-(1-(5-bromopyridin-2-yl)-3-(difluoromethoxy)propyl)-1H-pyrazol-4-yl)-4-chlorothiazol-2-yl)(4-methoxybenzyl)carbamate A mixture of 1-(5-bromopyridin-2-yl)-3-(difluoromethoxy)propyl methanesulfonate (325 mg, 0.90 mmol, 1.0 equiv.), tert-butyl (4-chloro-5-(1H-pyrazol-4-yl)thiazol-2-yl)(4-methoxybenzyl)carbamate (380 mg, 0.90 mmol, 1.0 equiv.) and cesium carbonate (294 mg, 0.90 mmol, 1.0 equiv.) in acetonitrile (5 mL) was stirred at 90° C. for 4 h. The reaction was diluted with water, and the mixture extracted with ethyl acetate twice. The combined organic layers were washed with brine, dried over sodium sulfate and concentrated. The residue was purified by silica gel chromatography (0→80% ethyl acetate/petroleum ether) to yield tert-butyl (5-(1-(1-(5-bromopyridin-2-yl)-3-(difluoromethoxy)propyl)-1H-pyrazol-4-yl)-4-chlorothiazol-2-yl)(4-methoxybenzyl)carbamate as a light yellow solid. LC/MS: mass calculated for $C_{28}H_{29}BrClF_2N_5O_4S$: 683.08, measured (ES, m/z): 684.15, 686.15 [M+H, M+H+2]$^+$.

Step 6: 5-(1-(1-(5-Bromopyridin-2-yl)-3-(difluoromethoxy)propyl)-1H-pyrazol-4-yl)-4-chlorothiazol-2-amine A mixture of tert-butyl (5-(1-(1-(5-bromopyridin-2-yl)-3-(difluoromethoxy)propyl)-1H-pyrazol-4-yl)-4-chlorothiazol-2-yl)(4-methoxybenzyl)carbamate (430 mg, 0.63 mmol, 1.0 equiv.) in trifluoroacetic acid (5.0 mL) was stirred at 45° C. for 2 h. The solution was concentrated and diluted with DCM. The solution was washed with aqueous sodium bicarbonate solution and brine, dried over anhydrous sodium sulfate and concentrated. The residue was purified by silica gel chromatography (0→80% ethyl acetate/petroleum ether) to yield 5-(1-(1-(5-bromopyridin-2-yl)-3-(difluoromethoxy)propyl)-1H-pyrazol-4-yl)-4-chlorothiazol-2-amine as a light yellow oil. LC/MS: mass calculated for $C_{15}H_{13}BrClF_2N_5OS$: 462.97, measured (ES, m/z): 464.00, 466.00 [M+H, M+H+2]$^+$.

Step 7: 5-(1-(1-(5-Bromopyridin-2-yl)-3-(difluoromethoxy)propyl)-1H-pyrazol-4-yl)-4-chlorothiazole 5-(1-(1-(5-Bromopyridin-2-yl)-3-(difluoromethoxy)propyl)-1H-pyrazol-4-yl)-4-chlorothiazol-2-amine (100 mg, 0.22 mmol, 1.0 equiv.) was dissolved in 2.0 mL THF and tert-butyl-nitrite (44 mg, 0.43 mmol, 2.0 equiv.) was added. The reaction mixture was stirred at 60° C. for 2 h. The solution was concentrated and the residue was purified by silica gel chromatography (0→80% ethyl acetate/petroleum ether) to yield 5-(1-(1-(5-bromopyridin-2-yl)-3-(difluoromethoxy)propyl)-1H-pyrazol-4-yl)-4-chlorothiazole as a light yellow solid. LC/MS: mass calculated for $C_{15}H_{12}BrClF_2N_4OS$: 447.96, measured (ES, m/z): 448.90, 450.90 [M+H, M+H+2]$^+$.

Step 8: 4-Chloro-2-(6-(1-(4-(4-chlorothiazol-5-yl)-1H-pyrazol-1-yl)-3-(difluoromethoxy)propyl)pyridin-3-yl)-3-fluoroaniline To a mixture of 5-(1-(1-(5-bromopyridin-2-yl)-3-(difluoromethoxy)propyl)-1H-pyrazol-4-yl)-4-chlorothiazole (70 mg, 0.16 mmol, 1.0 equiv.), 6-amino-3-chloro-2-fluorophenylboronic acid (44 mg, 0.23 mmol, 1.5 equiv.) and potassium carbonate (65 mg, 0.47 mmol, 3.0 equiv.) in 1,4-dioxane (2 mL) and water (0.5 mL) was added tetrakis(triphenylphosphine)palladium(0) (18 mg, 0.016 mmol, 0.1 equiv.) and the mixture was stirred at 90° C. for 2 h. After cooling to room temperature, the reaction was quenched with water, and the mixture extracted with ethyl acetate twice. The combined organic layers were washed with brine, dried over anhydrous sodium sulfate and concentrated. The residue was purified by Prep-TLC (10% MeOH/DCM) to yield 4-chloro-2-(6-(1-(4-(4-chlorothiazol-5-yl)-1H-pyrazol-1-yl)-3-(difluoromethoxy)propyl)pyridin-3-yl)-3-fluoroaniline as a light yellow solid. LC/MS: mass calculated for $C_{21}H_{16}Cl_2F_3N_5OS$: 513.04, measured (ES, m/z): 514.10, 516.10 [M+H, M+H+2]$^+$.

Step 9: 4-Chloro-5-(1-(1-(5-(3-chloro-2-fluoro-6-(1H-tetrazol-1-yl)phenyl)pyridin-2-yl)-3-(difluoromethoxy)propyl)-1H-pyrazol-4-yl)thiazole A mixture of 4-chloro-2-(6-(1-(4-(4-chlorothiazol-5-yl)-1H-pyrazol-1-yl)-3-(difluoromethoxy)propyl)pyridin-3-yl)-3-fluoroaniline (50 mg, 0.10 mmol, 1.0 equiv.), azidotrimethylsilane (0.5 mL) and trimethoxymethane (0.5 mL) in acetic acid glacial (0.5 mL) was stirred at room temperature overnight. The mixture was concentrated and the residue was purified by reverse phase chromatography on C18 (80 g, MeCN/H$_2$O (0.05% CF$_3$COOH): 0→50%) to yield 4-chloro-5-(1-(1-(5-(3-chloro-2-fluoro-6-(1H-tetrazol-1-yl)phenyl)pyridin-2-yl)-3-(difluoromethoxy)propyl)-1H-pyrazol-4-yl)thiazole as a light yellow solid. LC/MS: mass calculated for $C_{22}H_{15}Cl_2F_3N_8OS$: 566.04, measured (ES, m/z): 567.00 [M+H]$^+$.

Step 10: (R)-5-(3-Chloro-2-fluoro-6-(1H-tetrazol-1-yl)phenyl)-2-(1-(4-(4-chlorothiazol-5-yl)-1H-pyrazol-1-yl)-3-(difluoromethoxy)propyl)pyridine 1-oxide A mixture of 4-chloro-5-(1-(1-(5-(3-chloro-2-fluoro-6-(1H-tetrazol-1-yl)phenyl)pyridin-2-yl)-3-(difluoromethoxy)propyl)-1H-pyrazol-4-yl)thiazole (50 mg, 0.09 mmol, 1.0 equiv.), methyl trioxorhenium (VII) (11 mg, 0.04 mmol, 0.5 equiv.) and hydrogen peroxide (0.04 mL, 0.44 mmol, 30 wt %, 5.0 equiv.) in CH$_3$OH (0.5 mL) was stirred at room temperature for 1 h. The reaction was purified by reverse phase chromatography on C18 (80 g, MeCN/H$_2$O (0.05% CF$_3$COOH): 0→45%) and then Prep-HPLC to yield (R)-5-(3-chloro-2-fluoro-6-(1H-tetrazol-1-yl)phenyl)-2-(1-(4-(4-chlorothiazol-5-yl)-1H-pyrazol-1-yl)-3-(difluoromethoxy)propyl)pyridine 1-oxide as a white solid.

LC/MS: mass calculated for $C_{22}H_{15}Cl_2F_3N_8O_2S$: 582.04, measured (ES, m/z): 583.0 [M+H]$^+$. $^1$H NMR (300 MHz, DMSO-d$_6$): δ 9.70 (s, 1H), 9.04 (s, 1H), 8.53 (s, 1H), 8.47 (s, 1H), 8.02-8.14 (m, 2H), 7.73-7.82 (m, 1H), 7.19-7.35 (m, 2H), 6.64 (t, J=75.7 Hz, 1H), 6.20-6.27 (m, 1H), 3.79-3.90 (m, 1H), 3.64-3.76 (m, 1H), 2.55-2.69 (m, 2H). $^{19}$F-NMR (DMSO, 282 MHz-d6): 5-83.29, −112.65.

Example 621: (R)-5-(3-Chloro-2-fluoro-6-(1H-tetrazol-1-yl)phenyl)-2-(1-(4-(2-chloro-6-fluorophenyl)-1H-pyrazol-1-yl)-3-(difluoromethoxy)propyl)pyridine 1-oxide

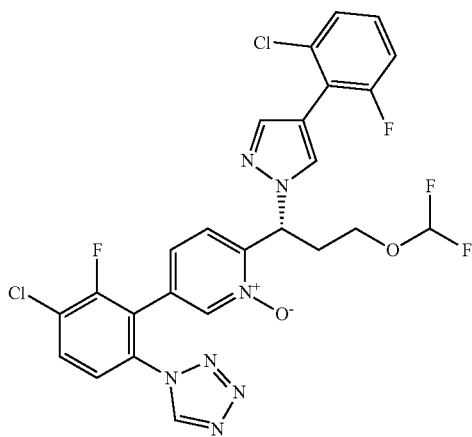 [SMILES: [O-][n+]1cc(-c2c(-n3cnnn3)ccc(Cl)c2F)ccc1[C@@H](CCOC(F)F)n1cc(-c2c(F)cccc2Cl)cn1]

Step 1: 3-Chloro-5-fluoro-4-iodopyridine

To a solution of 3-chloro-5-fluoropyridine (5.0 g, 38.01 mmol, 1.0 equiv.) in dry THF (45 mL) was added n-butyllithium (16.7 mL, 2.5 M, 41.81 mmol, 1.1 equiv.) at −78° C. under $N_2$ atmosphere, and the reaction mixture was stirred at this temperature for 30 min. Then iodine (11.0 g, 41.81 mmol, 1.1 mmol) in dry THF (10 mL) was added and the mixture stirred for a further 3 h. The resulting mixture was quenched by water (30 mL), extracted with EA (3×40 mL). The organic layers were combined, washed with brine, dried over $Na_2SO_4$. The resulting residue was purified by silica gel chromatography (0%→20%, EA/PE) to yield 3-chloro-5-fluoro-4- as an off-white solid. LC/MS: mass calculated for $C_5H_2ClFIN$: 256.89, measured (ES, m/z): 257.85 [M+H]$^+$.

Step 2: 3-Chloro-5-fluoro-4-(1H-pyrazol-4-yl)pyridine

To a solution of 3-chloro-5-fluoro-4-iodopyridine (2.0 g, 7.77 mmol, 1.0 equiv.) in 1,4-dioxane/water (25 mL) was added tert-butyl 4-(4,4,5,5-tetramethyl-1,3,2-dioxaborolan-2-yl)-1H-pyrazole-1-carboxylate (3.4 g, 11.66 mmol, 1.5 equiv.), $K_2CO_3$ (3.2 g, 23.31 mmol, 3.0 equiv.) and $Pd(PPh_3)_4$ (0.9 g, 0.78 mmol, 0.1 equiv.). Then the mixture was stirred at 90° C. for 2 h. The resulting mixture was diluted with water (100 mL), extracted with EA (3×100 mL). The organic layers were combined, washed with brine, dried over $Na_2SO_4$ and concentrated. The resulting residue was purified by silica gel chromatography (EA/PE, 0%→50%) to yield 3-chloro-5-fluoro-4-(1H-pyrazol-4-yl)pyridine as a yellow solid. LC/MS: mass calculated for $C_8H_5ClFN_3$: 197.02, measured (ES, m/z): 198.00 [M+H]$^+$.

Step 3: 4-(1-(1-(5-Bromopyridin-2-yl)-3-(difluoromethoxy)propyl)-1H-pyrazol-4-yl)-3-chloro-5-fluoropyridine A mixture of cesium carbonate (296 mg, 0.91 mmol, 1.0 equiv.) and 3-chloro-5-fluoro-4-(1H-pyrazol-4-yl)pyridine (179 mg, 0.91 mmol, 1.0 equiv.) in acetonitrile (2 mL) was stirred for 15 min at room temperature. 1-(5-Bromopyridin-2-yl)-3-(difluoromethoxy)propyl methanesulfonate (327 mg, 0.91 mmol, 1.0 equiv.) was added and the solution was stirred for 2.5 h at 70° C. The resulting mixture was diluted with water, extracted with EA (3×5 mL). Then the organic layers were combined, washed with brine, dried over $Na_2SO_4$ and concentrated. The residue was purified by silica gel chromatography (EA/PE, 0%→50%) to yield 4-(1-(1-(5-bromopyridin-2-yl)-3-(difluoromethoxy)propyl)-1H-pyrazol-4-yl)-3-chloro-5-fluoropyridine as a yellow oil. LC/MS: mass calculated for $C_{17}H_{13}BrClF_3N_4O$:459.99, measured (ES, m/z): 461.66 [M+H]$^+$.

Step 4: 4-Chloro-2-(6-(1-(4-(3-chloro-5-fluoropyridin-4-yl)-1H-pyrazol-1-yl)-3-(difluoromethoxy)propyl)pyridin-3-yl)-3-fluoroaniline A mixture of 4-(1-(1-(5-bromopyridin-2-yl)-3-(difluoromethoxy)propyl)-1H-pyrazol-4-yl)-3-chloro-5-fluoropyridine (330 mg, 0.72 mmol, 1.0 equiv.), 6-amino-3-chloro-2-fluorophenylboronic acid (203 mg, 1.07 mmol, 1.5 equiv.), $Pd(PPh_3)_4$ (83 mg, 0.07 mmol, 0.1 equiv.) and $K_2CO_3$ (296 mg, 2.14 mmol, 3.0 equiv.) in 1,4-dioxane/water (V/V=4:1.3 mL) was refluxed at 90° C. under $N_2$ for 3 h. The resulting mixture was diluted with water, and the mixture extracted with EA (3×5 mL). The organic layers were combined, washed with water (5 mL), dried over $Na_2SO_4$ and concentrated. The residue was purified by silica gel chromatography (0%→10%, DCM/MeOH) to yield 4-chloro-2-(6-(1-(4-(3-chloro-5-fluoropyridin-4-yl)-1H-pyrazol-1-yl)-3-(difluoromethoxy)propyl)pyridin-3-yl)-3-fluoroaniline as a yellow oil. LC/MS: mass calculated for $C_{23}H_{17}Cl_2F_4N_5O$: 525.07, measured (ES, m/z):526.05 [M+H]$^+$.

Step 5: 3-Chloro-4-(1-(1-(5-(3-chloro-2-fluoro-6-(1H-tetrazol-1-yl)phenyl)pyridin-2-yl)-3-(difluoromethoxy)propyl)-1H-pyrazol-4-yl)-5-fluoropyridine A mixture of 4-chloro-2-(6-(1-(4-(2-chloro-6-fluorophenyl)-1H-pyrazol-1-yl)-3-(difluoromethoxy)propyl)pyridin-3-yl)-3-fluoroaniline (349 mg, 0.68 mmol, 1.0 equiv.), trimethoxymethane (2 mL), $TMSN_3$ (2 mL) and acetic acid (2 mL) was stirred overnight at 25° C. The reaction was purified by reverse chromatography on C18 (0%→55% MeCN/$H_2O$ (0.05% $CF_3COOH$)) to yield 3-chloro-4-(1-(1-(5-(3-chloro-2-fluoro-6-(1H-tetrazol-1-yl)phenyl)pyridin-2-yl)-3-(difluoromethoxy)propyl)-1H-pyrazol-4-yl)-5-fluoropyridine as a yellow oil. LC/MS: mass calculated for $C_{24}H_{16}Cl_2F_4N_8O$: 578.08, measured (ES, m/z): 579.05 [M+H]$^+$.

Step 6: (R)-5-(3-Chloro-2-fluoro-6-(1H-tetrazol-1-yl)phenyl)-2-(1-(4-(3-chloro-5-fluoropyridin-4-yl)-1H-pyrazol-1-yl)-3-(difluoromethoxy)propyl)pyridine 1-oxide A mixture of 3-chloro-4-(1-(1-(5-(3-chloro-2-fluoro-6-(1H-tetrazol-1-yl)phenyl)pyridine-2-yl)-3-(difluoromethoxy)propyl)-1H-pyrazol-4-yl)-5-fluoropyridine (200 mg, 0.35 mmol, 1.0 equiv.) and 3-chlorobenzoperoxoic acid (298 mg, 1.73 mmol, 5.0 equiv.) in ethyl acetate (1 mL) was stirred for 1 h at room temperature. The resulting mixture was purified by reverse phase chromatography on C18 (MeCN/$H_2O$ (0.05% $CF_3COOH$)) to yield a mixture of 5-(3-chloro-2-fluoro-6-(1H-tetrazol-1-yl)phenyl)-2-(1-(4-

(2-chloro-6-fluorophenyl)-1H-pyrazol-1-yl)-3-(difluoromethoxy)propyl)pyridine 1-oxide as a white solid. The racemic product was separated by chiral-HPLC to yield (R)-5-(3-chloro-2-fluoro-6-(1H-tetrazol-1-yl)phenyl)-2-(1-(4-(2-chloro-6-fluorophenyl)-1H-pyrazol-1-yl)-3-(difluoromethoxy)propyl)pyridine 1-oxide as a white solid.

LC/MS: mass calculated for $C_{24}H_{16}Cl_2F_4N_8O_2$: 594.07, measured (ES, m/z): 616.95 [M+Na]$^+$. $^1$H NMR (300 MHz, DMSO-d$_6$) δ 9.67 (s, 1H), 8.55-8.64 (m, 3H), 8.44 (d, J=1.5 Hz, 1H), 7.99-8.15 (m, 2H), 7.74-7.78 (m, 1H), 7.35 (d, J=8.3 Hz, 1H), 7.19-7.22 (m, 1H), 6.32-6.89 (m, 1H), 6.22-6.38 (m, 1H), 3.52-3.92 (m, 2H), 2.62-2.71 (m, 2H). $^{19}$F-NMR (282 MHz, DMSO-d$_6$) δ −83.41, −112.65, −126.21.

Example 622: (S)-5-(3-Chloro-2-fluoro-6-(1H-tetrazol-1-yl)phenyl)-2-(1-(4-(4-chlorothiazol-5-yl)-1H-pyrazol-1-yl)-3-(difluoromethoxy)propyl)pyridine 1-oxide

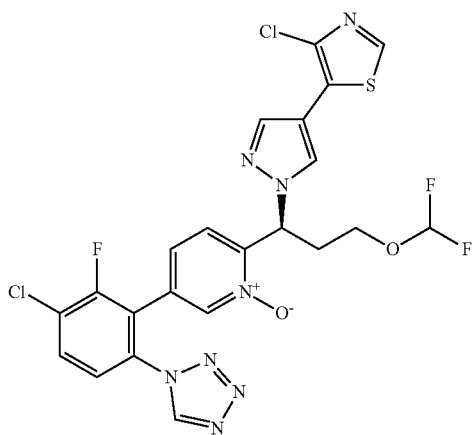 [SMILES: [O-][n+]1cc(-c2c(-n3cnnn3)ccc(Cl)c2F)ccc1[C@H](CCOC(F)F)n1cc(-c2scnc2Cl)cn1]

Step 1: 2,5-Dibromo-4-chlorothiazole

To a 100 mL round-bottomed flask was added 2,4-dichlorothiazole (5.0 g, 32.5 mmol, 1.0 equiv.) and glacial AcOH (10.0 mL). The resulting solution was treated slowly dropwise via addition funnel with Br$_2$ (2.5 mL, 48.7 mmol, 1.5 equiv.) over 5 minutes. The mixture was stirred at 90° C. for 3 hours. After cooling, the mixture was basified with solid sodium carbonate, first, then 5% sodium carbonate (aq). The overall mixture was extracted with ethyl acetate (3×100 mL), and the combined organic layers were washed with 5% sodium carbonate, dried, and concentrated to yield 2,5-dibromo-4-chlorothiazole as a light yellow oil. LC/MS: mass calculated for $C_3Br_2ClNS$: 274.78, measured (ES, m/z): 275.75, 277.75 [M+H, M+H+2]$^+$.

Step 2: 5-Bromo-4-chloro-N-(4-methoxybenzyl) thiazol-2-amine

A mixture of 2,5-dibromo-4-chlorothiazole (5.0 g, 18.0 mmol, 1.0 equiv.) and (4-methoxyphenyl)methanamine (2.5 g, 18.0 mmol, 1.0 equiv.) in 1,4-dioxane (75 mL) was stirred at 80° C. for 4 h and the mixture was concentrated. The residue was diluted with water, and the mixture extracted with ethyl acetate three times. The combined organic layers were washed with sodium bicarbonate solution and brine, dried over anhydrous sodium sulfate and concentrated. The residue was purified by silica gel chromatography (0→50% ethyl acetate/petroleum ether) to yield 5-bromo-4-chloro-N-(4-methoxybenzyl)thiazol-2-amine as a yellow solid. LC/MS: mass calculated for $C_{11}H_{10}BrClN_2OS$: 331.94, measured (ES, m/z): 332.90, 334.90 [M+H, M+H+2]$^+$.

Step 3: tert-Butyl (5-bromo-4-chlorothiazol-2-yl)(4-methoxybenzyl)carbamate

A mixture of 5-bromo-4-chloro-N-(4-methoxybenzyl)thiazol-2-amine (4.7 g, 14.1 mmol, 1.0 equiv.), Boc$_2$O (4.6 g, 21.1 mmol, 1.5 equiv.), triethylamine (4.3 g, 42.3 mmol, 3.0 equiv.) and DMAP (172 mg, 1.4 mmol, 0.1 equiv.) in tetrahydrofuran (50 mL) was stirred at room temperature overnight. The reaction was quenched with water, and the mixture extracted with ethyl acetate twice. The combined organic layers were washed with brine, dried over anhydrous sodium sulfate and concentrated. The residue was purified by silica gel chromatography (0→50% ethyl acetate/petroleum ether) to yield tert-butyl (5-bromo-4-chlorothiazol-2-yl)(4-methoxybenzyl)carbamate as an off-white solid. LC/MS: mass calculated for $C_{16}H_{18}BrClN_2O_3S$: 431.99, measured (ES, m/z): 376.85, 378.90 [M−t−Bu+H, M−t−Bu+H+2]$^+$.

Step 4: tert-Butyl (4-chloro-5-(1H-pyrazol-4-yl)thiazol-2-yl)(4-methoxybenzyl)carbamate A mixture of tert-butyl (5-bromo-4-chlorothiazol-2-yl)(4-methoxybenzyl)carbamate (2.5 g, 5.8 mmol, 1.0 equiv.), tert-butyl 4-(4,4,5,5-tetramethyl-1,3,2-dioxaborolan-2-yl)-1H-pyrazole-1-carboxylate (3.4 g, 11.5 mmol, 2.0 equiv.), potassium carbonate (2.4 g, 17.3 mmol, 3.0 equiv.) and tetrakis(triphenylphosphine)palladium (666 mg, 0.58 mmol, 0.1 equiv.) in DMF (30 mL) and water (5 mL) was stirred at 90° C. for 4 h. After cooling to room temperature, the reaction was quenched with water, and the mixture extracted with ethyl acetate twice. The combined organic layers were washed with brine, dried over anhydrous sodium sulfate and concentrated. The residue was purified by silica gel chromatography (0→50% ethyl acetate/petroleum ether) to yield tert-butyl (4-chloro-5-(1H-pyrazol-4-yl)thiazol-2-yl)(4-methoxybenzyl)carbamate as a light yellow. LC/MS: mass calculated for $C_{19}H_{21}ClN_4O_3S$: 420.10, measured (ES, m/z): 421.10 [M+H]$^+$.

Step 5: tert-Butyl (5-(1-(1-(5-bromopyridin-2-yl)-3-(difluoromethoxy)propyl)-1H-pyrazol-4-yl)-4-chlorothiazol-2-yl)(4-methoxybenzyl)carbamate A mixture of 1-(5-bromopyridin-2-yl)-3-(difluoromethoxy)propyl methanesulfonate (325 mg, 0.90 mmol, 1.0 equiv.), tert-butyl (4-chloro-5-(1H-pyrazol-4-yl)thiazol-2-yl)(4-methoxybenzyl)carbamate (380 mg, 0.90 mmol, 1.0 equiv.) and cesium carbonate (294 mg, 0.90 mmol, 1.0 equiv.) in acetonitrile (5 mL) was stirred at 90° C. for 4 h. The reaction was diluted with water, and the mixture extracted with ethyl acetate twice. The combined organic layers were washed with brine, dried over sodium sulfate and concentrated. The residue was purified by silica gel chromatography (0→80% ethyl acetate/petroleum ether) to yield tert-butyl (5-(1-(1-(5-bromopyridin-2-yl)-3-(difluoromethoxy)propyl)-1H-pyrazol-4-yl)-4-chlorothiazol-2-yl)(4-methoxybenzyl)carbamate as a light yellow solid.

LC/MS: mass calculated for $C_{28}H_{29}BrClF_2N_5O_4S$: 683.08, measured (ES, m/z): 684.15, 686.15 [M+H, M+H+2]$^+$.

Step 6: 5-(1-(1-(5-Bromopyridin-2-yl)-3-(difluoromethoxy)propyl)-1H-pyrazol-4-yl)-4-chlorothiazol-2-amine A mixture of tert-butyl (5-(1-(1-(5-bromopyridin-2-yl)-3-(difluoromethoxy)propyl)-1H-pyrazol-4-yl)-4-chlorothiazol-2-yl)(4-methoxybenzyl)carbamate (430 mg, 0.63 mmol, 1.0 equiv.) in trifluoroacetic acid (5.0 mL) was stirred at 45° C. for 2 h. The solution was concentrated and diluted with DCM. The solution was washed with aqueous sodium bicarbonate solution and brine, dried over anhydrous sodium sulfate and concentrated. The residue was purified by silica gel chromatography (0→80% ethyl acetate/petroleum ether) to yield 5-(1-(1-(5-bromopyridin-2-yl)-3-(difluoromethoxy)propyl)-1H-pyrazol-4-yl)-4-chlorothiazol-2-amine as a light yellow oil. LC/MS: mass calculated for $C_{15}H_{13}BrClF_2N_5OS$: 462.97, measured (ES, m/z): 464.00, 466.00 [M+H, M+H+2]$^+$.

Step 7: 5-(1-(1-(5-Bromopyridin-2-yl)-3-(difluoromethoxy)propyl)-1H-pyrazol-4-yl)-4-chlorothiazole 5-(1-(1-(5-Bromopyridin-2-yl)-3-(difluoromethoxy)propyl)-1H-pyrazol-4-yl)-4-chlorothiazol-2-amine (100 mg, 0.22 mmol, 1.0 equiv.) was dissolved in 2.0 mL THF and tert-butyl-nitrite (44 mg, 0.43 mmol, 2.0 equiv.) was added. The reaction mixture was stirred at 60° C. for 2 h. The solution was concentrated and the residue was purified by silica gel chromatography (0→80% ethyl acetate/petroleum ether) to yield 5-(1-(1-(5-bromopyridin-2-yl)-3-(difluoromethoxy)propyl)-1H-pyrazol-4-yl)-4-chlorothiazole as a light yellow solid. LC/MS: mass calculated for $C_{15}H_{12}BrClF_2N_4OS$: 447.96, measured (ES, m/z): 448.90, 450.90 [M+H, M+H+2]$^+$.

Step 8: 4-Chloro-2-(6-(1-(4-(4-chlorothiazol-5-yl)-1H-pyrazol-1-yl)-3-(difluoromethoxy)propyl)pyridin-3-yl)-3-fluoroaniline To a mixture of 5-(1-(1-(5-bromopyridin-2-yl)-3-(difluoromethoxy)propyl)-1H-pyrazol-4-yl)-4-chlorothiazole (70 mg, 0.16 mmol, 1.0 equiv.), 6-amino-3-chloro-2-fluorophenylboronic acid (44 mg, 0.23 mmol, 1.5 equiv.) and potassium carbonate (65 mg, 0.47 mmol, 3.0 equiv.) in 1,4-dioxane (2 mL) and water (0.5 mL) was added tetrakis(triphenylphosphine)palladium(0) (18 mg, 0.016 mmol, 0.1 equiv.) and the mixture was stirred at 90° C. for 2 h. After cooling to room temperature, the reaction was quenched with water, and the mixture extracted with ethyl acetate twice. The combined organic layers were washed with brine, dried over anhydrous sodium sulfate, and concentrated. The residue was purified by Prep-TLC (10% MeOH/DCM) to yield 4-chloro-2-(6-(1-(4-(4-chlorothiazol-5-yl)-1H-pyrazol-1-yl)-3-(difluoromethoxy)propyl)pyridin-3-yl)-3-fluoroaniline as a light yellow solid. LC/MS: mass calculated for $C_{21}H_{16}Cl_2F_3N_5OS$: 513.04, measured (ES, m/z): 514.10, 516.10 [M+H, M+H+2]$^+$.

Step 9: 4-Chloro-5-(1-(1-(5-(3-chloro-2-fluoro-6-(1H-tetrazol-1-yl)phenyl)pyridin-2-yl)-3-(difluoromethoxy)propyl)-1H-pyrazol-4-yl)thiazole A mixture of 4-chloro-2-(6-(1-(4-(4-chlorothiazol-5-yl)-1H-pyrazol-1-yl)-3-(difluoromethoxy)propyl)pyridin-3-yl)-3-fluoroaniline (50 mg, 0.10 mmol, 1.0 equiv.), azidotrimethylsilane (0.5 mL) and trimethoxymethane (0.5 mL) in acetic acid glacial (0.5 mL) was stirred at room temperature overnight. The mixture was concentrated and the residue was purified by reverse phase chromatography on C18 (80 g, MeCN/H$_2$O (0.05% CF$_3$COOH): 0→50%) to yield 4-chloro-5-(1-(1-(5-(3-chloro-2-fluoro-6-(1H-tetrazol-1-yl)phenyl)pyridin-2-yl)-3-(difluoromethoxy)propyl)-1H-pyrazol-4-yl)thiazole as a light yellow solid. LC/MS: mass calculated for $C_{22}H_{15}Cl_2F_3N_8OS$: 566.04, measured (ES, m/z): 567.00 [M+H]$^+$.

Step 10: (S)-5-(3-Chloro-2-fluoro-6-(1H-tetrazol-1-yl)phenyl)-2-(1-(4-(4-chlorothiazol-5-yl)-1H-pyrazol-1-yl)-3-(difluoromethoxy)propyl)pyridine 1-oxide A mixture of 4-chloro-5-(1-(1-(5-(3-chloro-2-fluoro-6-(1H-tetrazol-1-yl)phenyl)pyridin-2-yl)-3-(difluoromethoxy)propyl)-1H-pyrazol-4-yl)thiazole (50 mg, 0.09 mmol, 1.0 equiv.), methyl trioxorhenium (VII) (11 mg, 0.04 mmol, 0.5 equiv.) and hydrogen peroxide (0.04 mL, 0.44 mmol, 30 wt %, 5.0 equiv.) in CH$_3$OH (0.5 mL) was stirred at room temperature for 1 h. The reaction was purified by reverse phase chromatography on C18 (80 g, MeCN/H$_2$O (0.05% CF$_3$COOH): 0→45%) and then Prep-HPLC to yield (S)-5-(3-chloro-2-fluoro-6-(1H-tetrazol-1-yl)phenyl)-2-(1-(4-(4-chlorothiazol-5-yl)-1H-pyrazol-1-yl)-3-(difluoromethoxy)propyl)pyridine 1-oxide as a white solid.

LC/MS: mass calculated for $C_{22}H_{15}Cl_2F_3N_8O_2S$: 582.04, measured (ES, m/z): 583.0 [M+H]$^+$. $^1$H NMR (DMSO, 300 MHz-d6): δ 9.69 (s, 1H), 9.03 (s, 1H), 8.53 (s, 1H), 8.46 (s, 1H), 8.05-8.09 (m, 2H), 7.77 (d, J=8.5 Hz, 1H), 7.20-7.35 (m, 2H), 6.64 (t, J=75.8 Hz, 1H), 6.20-6.27 (m, 1H), 3.79-3.90 (m, 1H), 3.64-3.76 (m, 1H), 2.55-2.69 (m, 2H). $^{19}$F-NMR (DMSO, 282 MHz-d6): δ −73.53, −83.25, −112.68.

Example 623: (S)-5-(3-Chloro-2-fluoro-6-(1H-tetrazol-1-yl)phenyl)-2-(2-cyclopropyl-1-(2-(difluoromethyl)-1'H,2H-[3,4'-bipyrazol]-1'-yl)ethyl)pyridine 1-oxide

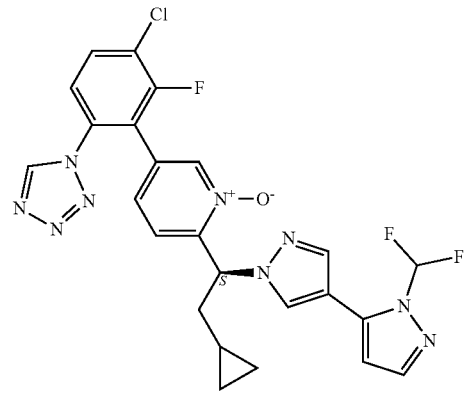

LC/MS: mass calculated for $C_{24}H_{19}ClF_3N_9O$: 541.14, measured (ES, m/z): 542.10[M+H]$^+$. $^1$H NMR (300 MHz, DMSO-d$_6$) δ 9.72 (s, 1H), 8.41-8.52 (m, 2H), 7.58-8.21 (m, 5H), 7.34 (d, J=8.3 Hz, 1H), 7.15 (dd, J=8.2, 1.6 Hz, 1H), 6.66 (d, J=1.7 Hz, 1H), 6.11 (dd, J=9.7, 4.4 Hz, 1H), 2.22-2.38 (m, 1H), 1.89-2.08 (m, 1H), 0.46-0.63 (m, 1H), 0.19-0.43 (m, 2H), 0.03-0.21 (m, 1H), −0.05-0.08 (m, 1H). $^{19}$F NMR (282 MHz, DMSO-d$_6$) δ −93.56, −112.80.

Example 624: (R)-2-(1-(4-chloro-2-(difluoromethyl)-1'H,2H-[3,4'-bipyrazol]-1'-yl)-2-cyclopropylethyl)-5-(3-chloro-2-fluoro-6-(1H-tetrazol-1-yl)phenyl)pyridine 1-oxide

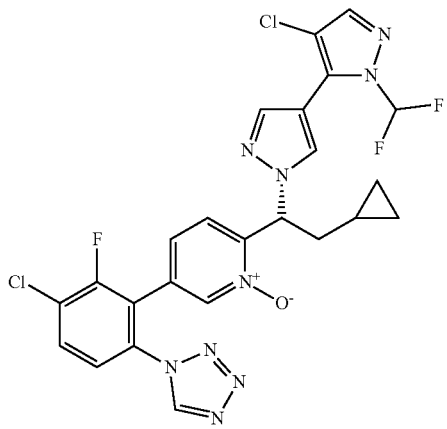

Step 1: 4-Chloro-1'-(1-(5-(3-chloro-2-fluoro-6-(1H-tetrazol-1-yl)phenyl)pyridin-2-yl)-2-cyclopropylethyl)-2-(difluoromethyl)-1'H,2H-3,4'-bipyrazole To a solution of 1'-(1-(5-(3-chloro-2-fluoro-6-(1H-tetrazol-1-yl) phenyl)pyridin-2-yl)-2-cyclopropylethyl)-2-(difluoromethyl)-1'H,2H-3,4'-bipyrazole (100 mg, 0.19 mmol, 1.0 equiv.) in N,N-dimethylformamide (1 mL) was added 1-chloropyrrolidine-2,5-dione (25 mg, 0.19 mmol, 1.0 equiv.). Then the mixture was stirred at 60° C. for 2 h. The resulting mixture was purified by reverse C18 chromatography (0%→55% MeCN/H$_2$O, 0.05% CF$_3$COOH) to yield 4-chloro-1'-(1-(5-(3-chloro-2-fluoro-6-(1H-tetrazol-1-yl) phenyl)pyridin-2-yl)-2-cyclopropylethyl)-2-(difluoromethyl)-1'H,2H-3,4'-bipyrazole as a white solid. LC/MS: mass calculated for C$_{24}$H$_{18}$Cl$_2$F$_3$N$_9$:559.10, measured (ES, m/z): 560.00 [M+H]$^+$.

Step 2: (R)-2-(1-(4-chloro-2-(difluoromethyl)-1'H,2H-[3,4'-bipyrazol]-1'-yl)-2-cyclopropylethyl)-5-(3-chloro-2-fluoro-6-(1H-tetrazol-1-yl)phenyl)pyridine 1-oxide A mixture of 4-chloro-1'-(1-(5-(3-chloro-2-fluoro-6-(1H-tetrazol-1-yl)phenyl)pyridine-2-yl)-2-cyclopropylethyl)-2-(difluoromethyl)-1'H,2H-3,4'-bipyrazole (102 mg, 0.18 mmol, 1.0 equiv.), methyltrioxorhenium (23 mg, 0.09 mmol, 0.5 equiv.) and hydrogen peroxide (0.6 mL) in CH$_3$OH (2 mL) was stirred for 4 h at room temperature. The resulting mixture was purified by reverse phase chromatography on C18 (MeCN/H$_2$O (0.05% CF$_3$COOH)) to yield 2-(1-(4-chloro-2-(difluoromethyl)-1'H,2H-[3,4'-bipyrazol]-1'-yl)-2-cyclopropylethyl)-5-(3-chloro-2-fluoro-6-(1H-tetrazol-1-yl) phenyl)pyridine 1-oxide as a white solid. The racemic product was separated by chiral-HPLC to yield (R)-2-(1-(4-chloro-2-(difluoromethyl)-1'H,2H-[3,4'-bipyrazol]-1'-yl)-2-cyclopropylethyl)-5-(3-chloro-2-fluoro-6-(1H-tetrazol-1-yl) phenyl)pyridine 1-oxide as a white solid.

LC/MS: mass calculated for C$_{24}$H$_{18}$Cl$_2$F$_3$N$_9$O: 575.10, measured (ES, m/z): 576.00 [M+H]$^+$. $^1$H NMR (300 MHz, DMSO-d$_6$) δ 9.67 (s, 1H), 8.48 (s, 1H), 8.41 (s, 1H), 7.97-8.10 (m, 2H), 7.54-7.97 (m, 3H), 7.38 (d, J=8.3 Hz, 1H), 7.17 (d, J=8.3 Hz, 1H), 6.15-6.19 (m, 1H), 2.21-2.31 (m, 1H), 1.94-2.02 (m, 1H), 0.53-0.62 (m, 1H), 0.24-0.36 (m, 2H), 0.04-0.11 (m, 1H), −0.12--0.08 (m, 1H). $^{19}$F-NMR (282 MHz, DMSO-d$_6$) δ −94.10, −112.72.

Example 625: (S)-2-(1-(4-chloro-2-(difluoromethyl)-1'H,2H-[3,4'-bipyrazol]-1'-yl)-2-cyclopropylethyl)-5-(3-chloro-2-fluoro-6-(1H-tetrazol-1-yl)phenyl)pyridine 1-oxide

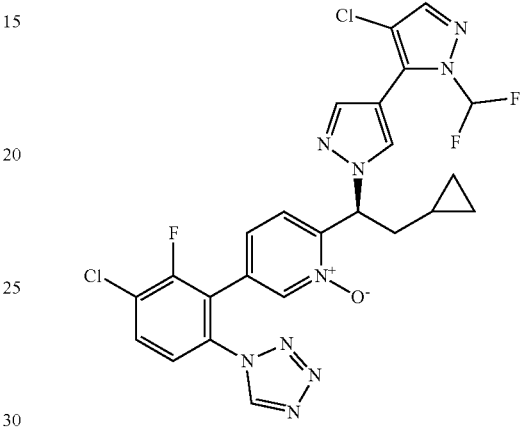

Step 1: 4-Chloro-1'-(1-(5-(3-chloro-2-fluoro-6-(1H-tetrazol-1-yl)phenyl)pyridine-2-yl)-2-cyclopropylethyl)-2-(difluoromethyl)-1'H,2H-3,4'-bipyrazole To a solution of 1'-(1-(5-(3-chloro-2-fluoro-6-(1H-tetrazol-1-yl)phenyl)pyridin-2-yl)-2-cyclopropylethyl)-2-(difluoromethyl)-1'H,2H-3,4'-bipyrazole (100 mg, 0.19 mmol, 1.0 equiv.) in N,N-dimethylformamide (1 mL) was added 1-chloropyrrolidine-2,5-dione (25 mg, 0.19 mmol, 1.0 equiv.). Then the mixture was stirred at 60° C. for 2 h. The resulting mixture was purified by reverse C18 chromatography (0%→55% MeCN/H$_2$O, 0.05% CF$_3$COOH) to yield 4-chloro-1'-(1-(5-(3-chloro-2-fluoro-6-(1H-tetrazol-1-yl) phenyl)pyridin-2-yl)-2-cyclopropylethyl)-2-(difluoromethyl)-1'H,2H-3,4'-bipyrazole as a white solid. LC/MS: mass calculated for C$_{24}$H$_{18}$Cl$_2$F$_3$N$_9$: 559.10, measured (ES, m/z): 560.00 [M+H]$^+$ Step 2: (S)-2-(1-(4-Chloro-2-(difluoromethyl)-1'H,2H-[3,4'-bipyrazol]-1'-yl)-2-cyclopropylethyl)-5-(3-chloro-2-fluoro-6-(1H-tetrazol-1-yl)phenyl)pyridine 1-oxide A mixture of 4-chloro-1'-(1-(5-(3-chloro-2-fluoro-6-(1H-tetrazol-1-yl)phenyl)pyridin-2-yl)-2-cyclopropylethyl)-2-(difluoromethyl)-1'H,2H-3,4'-bipyrazole (102 mg, 0.18 mmol, 1.0 equiv.), methyltrioxorhenium (23 mg, 0.09 mmol, 0.5 equiv.) and hydrogen peroxide (0.6 ml, 30 wt %) in CH$_3$OH (2 mL) was stirred for 4 h at room temperature. The resulting mixture was purified by reverse phase chromatography on C18 (MeCN/H$_2$O (0.05% CF$_3$COOH)) to yield 2-(1-(4-chloro-2-(difluoromethyl)-1'H,2H-[3,4'-bipyrazol]-1'-yl)-2-cyclopropylethyl)-5-(3-chloro-2-fluoro-6-(1H-tetrazol-1-yl)phenyl)pyridine 1-oxide as a white solid. The racemic product was separated by chiral-HPLC to yield (S)-2-(1-(4-chloro-2-(difluoromethyl)-1'H,2H-[3,4'-bipyrazol]-1'-yl)-2-cyclopropylethyl)-5-(3-chloro-2-fluoro-6-(1H-tetrazol-1-yl)phenyl)pyridine 1-oxide as a white solid.

LC/MS: mass calculated for $C_{24}H_{18}Cl_2F_3N_9O$: 575.10, measured (ES, m/z): 576.00 [M+H]$^+$. $^1$H NMR: (300 MHz, DMSO-d$_6$) δ 9.67 (s, 1H), 8.49 (s, 1H), 8.41 (d, J=1.5 Hz, 1H), 7.99-8.10 (m, 2H), 7.55-7.97 (m, 3H), 7.38 (d, J=8.3 Hz, 1H), 7.16-7.18 (m, 1H), 6.15-6.19 (m, 1H), 2.21-2.31 (m, 1H), 1.93-2.02 (m, 1H), 0.54-0.62 (m, 1H), 0.22-0.40 (m, 2H), 0.06-0.10 (m, 1H), −0.12→0.06 (m, 1H). $^{19}$F-NMR: (282 MHz, DMSO-d$_6$) δ −94.10, −112.72.

Example 626: (R)-2-(1-(4-(5-Chloro-2-(difluoromethyl)-2H-1,2,3-triazol-4-yl)-1H-pyrazol-1-yl)-2-cyclopropylethyl)-5-(3-chloro-2-fluoro-6-(1H-tetrazol-1-yl)phenyl)pyridine 1-oxide

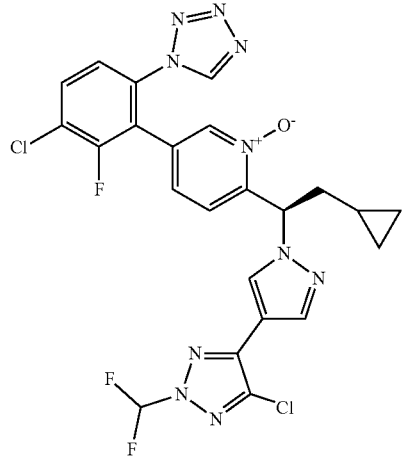 [SMILES: [O-][n+]1cc(-c2c(-n3cnnn3)ccc(Cl)c2F)ccc1[C@@H](CC1CC1)n1cc(-c2nn(C(F)F)nc2Cl)cn1]

LC/MS: mass calculated for $C_{23}H_{17}Cl_2F_3N_{10}O$: 576.09, measured (ES, m/z): 577.05 [M+H]$^+$. $^1$H NMR (400 MHz, DMSO-d$_6$) δ 9.69 (s, 1H), 8.53 (s, 1H), 8.41 (d, J=1.6 Hz, 1H), 7.98-8.37 (m, 3H), 7.76 (dd, J=8.7, 1.5 Hz, 1H), 7.52 (d, J=8.3 Hz, 1H), 7.21 (dd, J=8.3, 1.7 Hz, 1H), 6.20-6.30 (m, 1H), 2.20-2.33 (m, 1H), 1.90-2.00 (m, 1H), 0.54-0.61 (m, 1H), 0.23-0.45 (m, 2H), 0.10-0.20 (m, 1H), −0.20--0.10 (m, 1H). $^{19}$F NMR (376 MHz, DMSO-d$_6$) −96.79, −112.70.

Example 627A: (R*)-2-(1-(4-(5-Chloro-1-(difluoromethyl)-1H-1,2,3-triazol-4-yl)-1H-pyrazol-1-yl)-2-(4-fluorophenyl)ethyl)-5-(3-chloro-2-fluoro-6-(1H-tetrazol-1-yl)phenyl)pyridine 1-oxide

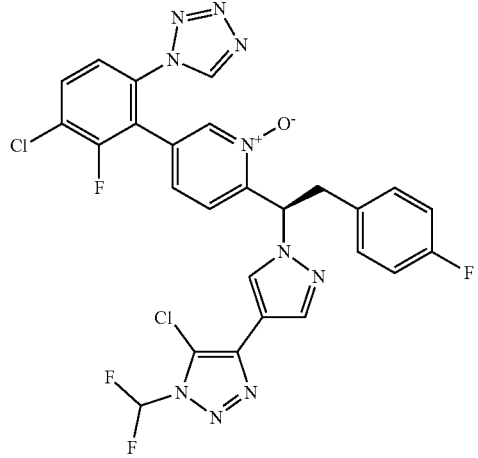 [SMILES: [O-][n+]1cc(-c2c(-n3cnnn3)ccc(Cl)c2F)ccc1[C@@H](Cc1ccc(F)cc1)n1cc(-c2nnn(C(F)F)c2Cl)cn1]

LC/MS: mass calculated for $C_{26}H_{16}Cl_2F_4N_{10}O$: 630.08, measured (ES, m/z): 631.05 [M+H]$^+$. $^1$H NMR (400 MHz, DMSO-d$_6$) δ 9.71 (s, 1H), 8.49 (d, J=1.6 Hz, 1H), 8.01-8.38 (m, 3H), 7.99 (s, 1H), 7.77 (dd, J=8.7, 1.5 Hz, 1H), 7.58 (d, J=8.3 Hz, 1H), 7.24 (dd, J=8.2, 1.7 Hz, 1H), 7.11-7.19 (m, 2H), 6.99-7.10 (m, 2H), 6.28-6.38 (m, 1H), 3.56 (d, J=7.5 Hz, 2H). $^{19}$F NMR (376 MHz, DMSO-d$_6$) −97.58, −112.65, −116.11.

Example 627B: (R)-2-(1-(4-(4-Chloro-1-(difluoromethyl)-1H-1,2,3-triazol-5-yl)-1H-pyrazol-1-yl)-2-cyclopropylethyl)-5-(3-chloro-2-fluoro-6-(1H-tetrazol-1-yl)phenyl)pyridine 1-oxide

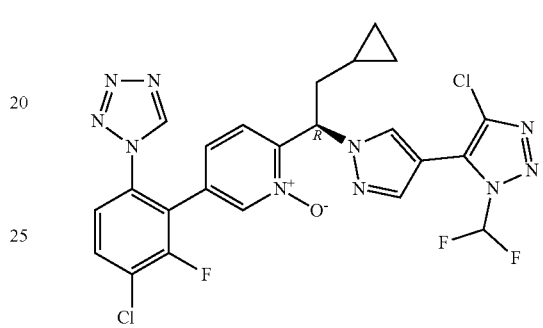

LC/MS: mass calculated for $C_{23}H_{17}Cl_2F_3N_{10}O$: 576.09, measured (ES, m/z): 577.00 [M+H]$^+$. $^1$H NMR (400 MHz, DMSO-d$_6$) δ 9.69 (s, 1H), 8.99 (s, 1H), 8.15-8.47 (m, 2H), 8.14 (s, 1H), 8.03-8.11 (m, 1H), 7.76 (dd, J=8.7, 1.5 Hz, 1H), 7.50 (d, J=8.3 Hz, 1H), 7.21 (dd, J=8.3, 1.7 Hz, 1H), 6.21-6.30 (m, 1H), 2.22-2.33 (m, 1H), 1.90-2.00 (m, 1H), 0.52-0.66 (m, 1H), 0.34-0.44 (m, 1H), 0.23-0.34 (m, 1H), 0.10-0.20 (m, 1H), −0.20--0.10 (m, 1H). $^{19}$F NMR (376 MHz, DMSO-d$_6$) −96.22, −112.71.

Example 628: (S)-2-(1-(4-(5-Chloro-1-(difluoromethyl)-1H-1,2,3-triazol-4-yl)-1H-pyrazol-1-yl)-2-(4-fluorophenyl)ethyl)-5-(3-chloro-2-fluoro-6-(1H-tetrazol-1-yl)phenyl)pyridine 1-oxide

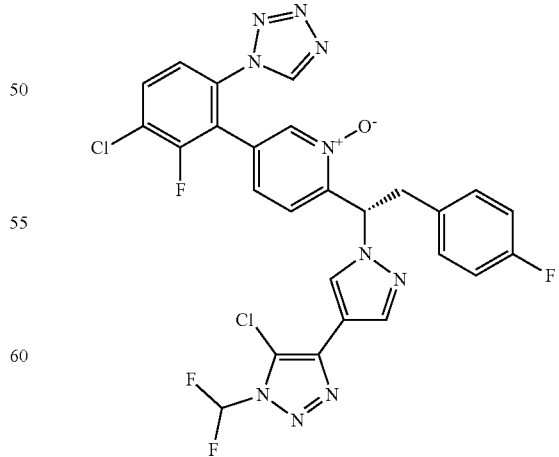

LC/MS: mass calculated for $C_{26}H_{16}Cl_2F_4N_{10}O$: 630.08, measured (ES, m/z): 631.05 [M+H]$^+$. $^1$H NMR (400 MHz, DMSO-$d_6$) δ 9.72 (s, 1H), 8.87 (s, 1H), 8.02-8.49 (m, 4H), 7.70-7.82 (m, 2H), 7.28 (dd, J=8.2, 1.7 Hz, 1H), 7.00-7.14 (m, 4H), 6.22-6.33 (m, 1H), 3.44-3.70 (m, 2H). $^{19}$F NMR (376 MHz, DMSO-$d_6$) −95.96, −112.56, 115.77.

Example 629: (R)-2-(1-(4-(5-Chloro-2-(difluoromethyl)-2H-1,2,3-triazol-4-yl)-1H-pyrazol-1-yl)-2-(4-fluorophenyl)ethyl)-5-(3-chloro-2-fluoro-6-(1H-tetrazol-1-yl)phenyl)pyridine 1-oxide

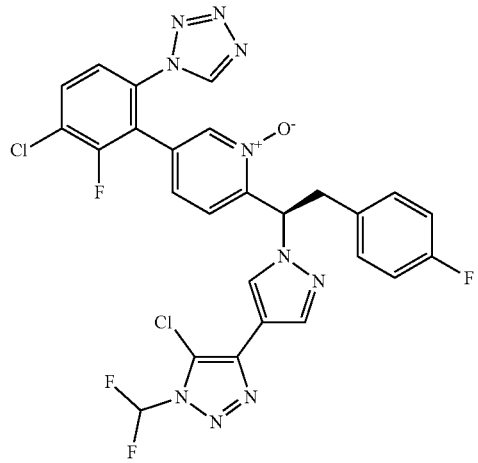 [SMILES: [O-][n+]1cc(-c2c(-n3cnnn3)ccc(Cl)c2F)ccc1[C@@H](Cc1ccc(F)cc1)n1cc(-c2nnn(C(F)F)c2Cl)cn1]

LC/MS: mass calculated for $C_{26}H_{16}Cl_2F_4N_{10}O$: 630.08, measured (ES, m/z): 631.05 [M+H]$^+$. $^1$H NMR (400 MHz, DMSO-$d_6$) δ 9.71 (s, 1H), 8.40-8.46 (m, 2H), 7.99-8.32 (m, 3H), 7.72-7.82 (m, 2H), 7.28 (dd, J=8.3, 1.7 Hz, 1H), 7.00-7.13 (m, 4H), 6.24-6.33 (m, 1H), 3.40-3.66 (m, 2H). $^{19}$F (376 MHZ, DMSO-$d_6$) −96.81, −112.66, −115.75.

Example 630: (S)-5-(3-chloro-2-fluoro-6-(1H-tetrazol-1-yl)phenyl)-2-(2-cyclopropyl-1-(4-(1-(difluoromethyl)-1H-1,2,3-triazol-4-yl)-1H-pyrazol-1-yl)ethyl)pyridine 1-oxide

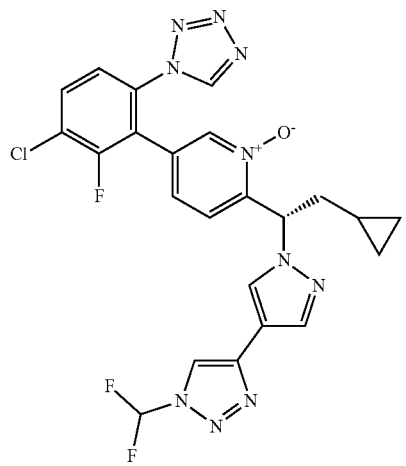 [SMILES: [O-][n+]1cc(-c2c(-n3cnnn3)ccc(Cl)c2F)ccc1[C@H](CC1CC1)n1cc(-c2cn(C(F)F)nn2)cn1]

LC/MS: mass calculated for $C_{23}H_{18}ClF_3N_{10}O$: 542.13, measured (ES, m/z): 543.05 [M+H]$^+$. $^1$H NMR (400 MHz, DMSO-$d_6$) δ 9.70 (s, 1H), 8.58 (s, 1H), 8.20-8.50 (m, 2H), 8.18 (s, 1H), 8.07 (dd, J=8.7, 7.8 Hz, 1H), 7.99 (s, 1H), 7.76 (dd, J=8.7, 1.5 Hz, 1H), 7.40 (d, J=8.3 Hz, 1H), 7.18 (dd, J=8.3, 1.7 Hz, 1H), 6.10-6.20 (m, 1H), 2.26-2.38 (m, 1H), 1.90-2.02 (m, 1H), 0.50-0.65 (m, 1H), 0.25-0.42 (m, 2H), 0.08-0.18 (m, 1H), −0.10--0.01 (m, 1H). $^{19}$F NMR (376 MHz, DMSO-$d_6$) −97.06, −112.74.

Example 631: (R)-5-(3-chloro-2-fluoro-6-(1H-tetrazol-1-yl)phenyl)-2-(2-cyclopropyl-1-(4-(1-(difluoromethyl)-1H-1,2,3-triazol-4-yl)-1H-pyrazol-1-yl)ethyl)pyridine 1-oxide

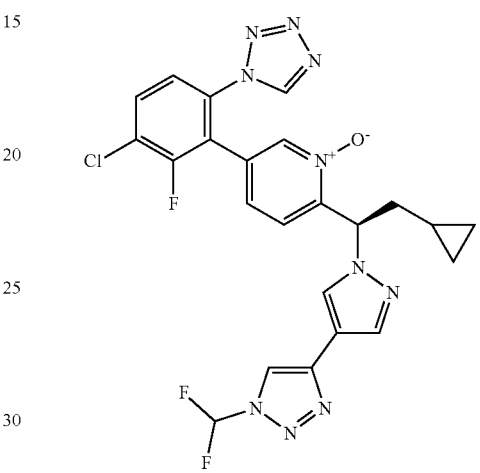

Step 1: 2-(1-(4-(1H-1,2,3-Triazol-5-yl)-1H-pyrazol-1-yl)-2-cyclopropylethyl)-5-bromopyridine To a stirred solution of 5-bromo-2-(2-(2-cyclopropyl-1-(4-ethynyl-1H-pyrazol-1-yl)ethyl)pyridine (1.5 g, 4.7 mmol, 1.0 equiv.) and azidotrimethylsilane (5.5 g, 47.4 mmol, 10.0 equiv.) in DMA (30 mL) was added CuSO$_4$.5H$_2$O (0.36 g, 1.42 mmol, 0.3 equiv.) and sodium ascorbate (0.28 g, 1.42 mmol, 0.3 equiv.). The mixture was stirred at 35° C. for 16 h, quenched with water, and extracted with ethyl acetate twice. The combined organic layers were dried over anhydrous sodium sulfate and concentrated under vacuum. The residue was applied onto a silica gel column (0→100% EA/PE) to yield 2-(1-(4-(1H-1,2,3-triazol-5-yl)-1H-pyrazol-1-yl)-2-cyclopropylethyl)-5-bromopyridine as a light yellow solid. LC/MS: mass calculated for $C_{15}H_{15}BrN_6$: 358.05, measured (ES, m/z): 359.05, 361.05 [M+H, M+H+2]$^+$.

Step 2: 5-Bromo-2-(2-cyclopropyl-1-(4-(1-(difluoromethyl)-1H-1,2,3-triazol-5-yl)-1H-pyrazol-1-yl)ethyl)pyridine, 5-bromo-2-(2-cyclopropyl-1-(4-(2-(difluoromethyl)-2H-1,2,3-triazol-4-yl)-1H-pyrazol-1-yl)ethyl)pyridine and 5-bromo-2-cyclopropyl-1-(4-(2-(difluoromethyl)-2H-1,2,3-triazol-4-yl)-1H-pyrazol-1-yl)ethyl)pyridine A solution of 2-(1-(4-(1H-1,2,3-triazol-5-yl)-1H-pyrazol-1-yl)-2-cyclopropylethyl)-5-bromopyridine (1.0 g, 2.8 mmol, 1.0 equiv.), sodium 2-chloro-2,2-difluoroacetate (0.64 g, 4.18 mmol, 1.5 equiv.) and cesium carbonate (2.7 g, 8.4 mmol, 3.0 equiv.) in DMA (30 mL) under nitrogen atmosphere was stirred for 1H at 70° C. After the mixture was cooled to room temperature, water (50 mL) was added.

The resulting mixture was extracted with ethyl acetate twice. The organic layers were combined, dried over anhydrous sodium sulfate, filtered and concentrated. The resulting residue was purified by silica gel chromatography (0→20% EA/PE) to yield a mixture of 5-bromo-2-(2-cyclopropyl-1-(4-(1-(difluoromethyl)-1H-1,2,3-triazol-5-yl)-1H-pyrazol-1-yl)ethyl)pyridine, 5-bromo-2-(2-cyclopropyl-1-(4-(1-(difluoromethyl)-1H-1,2,3-triazol-4-yl)-1H-pyrazol-1-yl)ethyl)pyridine and 5-bromo-2-(2-cyclopropyl-1-(4-(2-(difluoromethyl)-2H-1,2,3-triazol-4-yl)-1H-pyrazol-1-yl)ethyl)pyridine as colorless oil. LC/MS: mass calculated for $C_{16}H_{15}BrF_2N_6$: 408.05, measured (ES, m/z): 409.05, 410.05 $[M+H, M+H+2]^+$.

Step 3: 4-Chloro-2-(6-(2-cyclopropyl-1-(4-(1-(difluoromethyl)-1H-1,2,3-triazol-5-yl)-1H-pyrazol-1-yl)ethyl)pyridin-3-yl)-3-fluoroaniline, 4-chloro-2-(6-(2-cyclopropyl-1-(4-(1-(difluoromethyl)-1H-1,2,3-triazol-4-yl)-1H-pyrazol-1-yl)ethyl)pyridin-3-yl)-3-fluoroaniline and 4-chloro-2-(6-(2-cyclopropyl-1-(4-(2-(difluoromethyl)-2H-1,2,3-triazol-4-yl)-1H-pyrazol-1-yl)ethyl)pyridin-3-yl)-3-fluoroaniline To a solution of the mixture of 5-bromo-2-(2-cyclopropyl-1-(4-(1-(difluoromethyl)-1H-1,2,3-triazol-5-yl)-1H-pyrazol-1-yl)ethyl)pyridine, 5-bromo-2-(2-cyclopropyl-1-(4-(1-(difluoromethyl)-1H-1,2,3-triazol-4-yl)-1H-pyrazol-1-yl)ethyl)pyridine and 5-bromo-2-(2-cyclopropyl-1-(4-(2-(difluoromethyl)-2H-1,2,3-triazol-4-yl)-1H-pyrazol-1-yl)ethyl)pyridine (1.0 g, 2.44 mmol, 1.0 equiv.) in 1,4-dioxane (13 mL) and water (1 mL) was added (6-amino-3-chloro-2-fluorophenyl)boronic acid (833 mg, 4.40 mmol, 1.8 equiv.) tetrakis(triphenylphosphine)palladium (282 mg, 0.24 mmol, 0.1 equiv.) and potassium carbonate (1.0 g, 7.33 mmol, 3.0 equiv.). The reaction mixture was stirred at 100° C. for 2 h, then quenched with water, and extracted with ethyl acetate twice. The combined organic layers were dried over anhydrous sodium sulfate and concentrated under vacuum. The residue was applied onto a silica gel column (0→100% EA/PE) to yield a mixture of 4-chloro-2-(6-(2-cyclopropyl-1-(4-(1-(difluoromethyl)-1H-1,2,3-triazol-5-yl)-1H-pyrazol-1-yl)ethyl)pyridin-3-yl)-3-fluoroaniline, 4-chloro-2-(6-(2-cyclopropyl-1-(4-(1-(difluoromethyl)-1H-1,2,3-triazol-4-yl)-1H-pyrazol-1-yl)ethyl)pyridin-3-yl)-3-fluoroaniline and 4-chloro-2-(6-(2-cyclopropyl-1-(4-(2-(difluoromethyl)-2H-1,2,3-triazol-4-yl)-1H-pyrazol-1-yl)ethyl)pyridin-3-yl)-3-fluoroaniline as light yellow oil. LC/MS: mass calculated for $C_{22}H_{19}ClF_3N_7$: 473.13, measured (ES, m/z): 474.20 $[M+H]^+$.

Step 4: 5-(3-Chloro-2-fluoro-6-(1H-tetrazol-1-yl)phenyl)-2-(2-cyclopropyl-1-(4-(2-(difluoromethyl)-2H-1,2,3-triazol-4-yl)-1H-pyrazol-1-yl)ethyl)pyridine, the mixture of 5-(3-chloro-2-fluoro-6-(1H-tetrazol-1-yl)phenyl)-2-(2-cyclopropyl-1-(4-(1-(difluoromethyl)-1H-1,2,3-triazol-5-yl)-1H-pyrazol-1-yl)ethyl)pyridine and 5-(3-chloro-2-fluoro-6-(1H-tetrazol-1-yl)phenyl)-2-(2-cyclopropyl-1-(4-(1-(difluoromethyl)-1H-1,2,3-triazol-4-yl)-1H-pyrazol-1-yl)ethyl)pyridine To a solution of the mixture of 4-chloro-2-(6-(2-cyclopropyl-1-(4-(1-(difluoromethyl)-1H-1,2,3-triazol-5-yl)-1H-pyrazol-1-yl)ethyl)pyridin-3-yl)-3-fluoroaniline, 4-chloro-2-(6-(2-cyclopropyl-1-(4-(1-(difluoromethyl)-1H-1,2,3-triazol-4-yl)-1H-pyrazol-1-yl)ethyl)pyridin-3-yl)-3-fluoroaniline and 4-chloro-2-(6-(2-cyclopropyl-1-(4-(2-(difluoromethyl)-2H-1,2,3-triazol-4-yl)-1H-pyrazol-1-yl)ethyl)pyridin-3-yl)-3-fluoroaniline (1.0 g, 2.11 mmol, 1.0 equiv.) in acetic acid (15 mL) was added trimethoxymethane (2.2 g, 21.1 mmol, 10.0 equiv.) and $TMSN_3$ (2.4 g, 21.1 mmol, 10.0 equiv.). The resulting mixture was stirred overnight at room temperature, then concentrated under vacuum. The residue was purified by reverse column chromatography on C18 (120 g, MeCN/$H_2O$ (0.05% $CF_3COOH$): 5→80%) to yield 5-(3-chloro-2-fluoro-6-(1H-tetrazol-1-yl)phenyl)-2-(2-cyclopropyl-1-(4-(2-(difluoromethyl)-2H-1,2,3-triazol-4-yl)-1H-pyrazol-1-yl)ethyl)pyridine as a light yellow solid, and a mixture of 5-(3-chloro-2-fluoro-6-(1H-tetrazol-1-yl)phenyl)-2-(2-cyclopropyl-1-(4-(1-(difluoromethyl)-1H-1,2,3-triazol-5-yl)-1H-pyrazol-1-yl)ethyl)pyridine and 5-(3-chloro-2-fluoro-6-(1H-tetrazol-1-yl)phenyl)-2-(2-cyclopropyl-1-(4-(1-(difluoromethyl)-1H-1,2,3-triazol-4-yl)-1H-pyrazol-1-yl)ethyl)pyridine as an light yellow solid. LC/MS: mass calculated for $C_{23}H_{18}ClF_3N_{10}$: 526.14, measured (ES, m/z): 527.20 $[M+H]^+$.

Step 5: (R)-5-(3-Chloro-2-fluoro-6-(1H-tetrazol-1-yl)phenyl)-2-(2-cyclopropyl-1-(4-(1-(difluoromethyl)-1H-1,2,3-triazol-5-yl)-1H-pyrazol-1-yl)ethyl)pyridine 1-oxide A solution of the mixture of 5-(3-chloro-2-fluoro-6-(1H-tetrazol-1-yl)phenyl)-2-(2-cyclopropyl-1-(4-(1-(difluoromethyl)-1H-1,2,3-triazol-5-yl)-1H-pyrazol-1-yl)ethyl)pyridine and 5-(3-chloro-2-fluoro-6-(1H-tetrazol-1-yl)phenyl)-2-(2-cyclopropyl-1-(4-(1-(difluoromethyl)-1H-1,2,3-triazol-4-yl)-1H-pyrazol-1-yl)ethyl)pyridine (350 mg, 0.66 mmol, 1.0 equiv.), methylrhenium (VII) trioxide (33 mg, 0.13 mmol, 0.2 equiv.) and hydrogen peroxide (30 wt %, 753 mg, 6.64 mmol, 10.0 equiv.) in $CH_3OH$ (5 mL) was stirred for 1 h at room temperature. The reaction mixture was purified by reverse column chromatography on C18 (80 g, MeCN/$H_2O$ (0.05% $CF_3COOH$): 5→80%) to yield 5-(3-chloro-2-fluoro-6-(1H-tetrazol-1-yl)phenyl)-2-(2-cyclopropyl-1-(4-(1-(difluoromethyl)-1H-1,2,3-triazol-5-yl)-1H-pyrazol-1-yl)ethyl)pyridine 1-oxide as an off-white solid, which was purified by Prep-Chiral-HPLC with MtBE(0.1% DEA)MeOH=50:50 to yield (R)-5-(3-chloro-2-fluoro-6-(1H-tetrazol-1-yl)phenyl)-2-(2-cyclopropyl-1-(4-(1-(difluoromethyl)-1H-1,2,3-triazol-5-yl)-1H-pyrazol-1-yl)ethyl)pyridine 1-oxide as an off-white solid.

LC/MS: mass calculated for $C_{23}H_{18}ClF_3N_{10}O$: 542.13, measured (ES, m/z): 543.10 $[M+H]^+$. $^1H$ NMR (400 MHz, DMSO-$d_6$): δ 9.70 (s, 1H), 8.90 (s, 1H), 8.58 (s, 1H), 8.20-8.51 (m, 2H), 8.02-8.11 (m, 1H), 7.99 (s, 1H), 7.71-7.80 (m, 1H), 7.40 (d, J=8.3 Hz, 1H), 7.11-7.20 (m, 1H), 6.06-6.18 (m, 1H), 2.30-2.43 (m, 1H), 1.88-1.98 (m, 1H), 0.53-0.68 (m, 1H), 0.23-0.41 (m, 2H), 0.08-0.17 (m, 1H), −0.05-0.00 (m, $^1H$).

Example 632: ((R)-5-(3-chloro-2-fluoro-6-(1H-tetrazol-1-yl)phenyl)-2-(2-cyclopropyl-1-(4-(1-(difluoromethyl)-1H-1,2,3-triazol-5-yl)-1H-pyrazol-1-yl)ethyl)pyridine 1-oxide

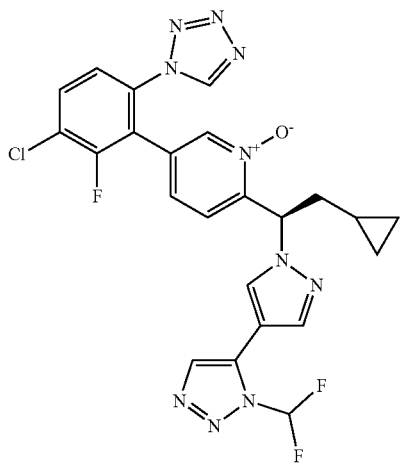 [SMILES: [O-][n+]1cc(-c2c(-n3cnnn3)ccc(Cl)c2F)ccc1[C@@H](CC1CC1)n1cc(-c2cnnn2C(F)F)cn1]

Step 1: 2-(1-(4-(1H-1,2,3-Triazol-5-yl)-1H-pyrazol-1-yl)-2-cyclopropylethyl)-5-bromopyridine To a stirred solution of 5-bromo-2-(2-cyclopropyl-1-(4-ethynyl-1H-pyrazol-1-yl)ethyl)pyridine (1.5 g, 4.7 mmol, 1.0 equiv.) and azidotrimethylsilane (5.5 g, 47.4 mmol, 10.0 equiv.) in DMAc (30 mL) was added $CuSO_4·5H_2O$ (0.36 g, 1.42 mmol, 0.3 equiv.) and sodium ascorbate (0.28 g, 1.42 mmol, 0.3 equiv.). The mixture was stirred at 35° C. for 16 h, then quenched with water, and extracted with ethyl acetate twice. The combined organic layers were dried over anhydrous sodium sulfate and concentrated under vacuum. The residue was applied onto a silica gel column (0→100% EA/PE) to yield 2-(1-(4-(1H-1,2,3-triazol-5-yl)-1H-pyrazol-1-yl)-2-cyclopropylethyl)-5-bromopyridine as a light yellow solid. LC/MS: mass calculated for $C_{15}H_{15}BrN_6$: 358.05, measured (ES, m/z): 359.05, 361.05 $[M+H, M+H+2]^+$.

Step 2: 5-Bromo-2-(2-cyclopropyl-1-(4-(1-(difluoromethyl)-1H-1,2,3-triazol-5-yl)-1H-pyrazol-1-yl)ethyl)pyridine, 5-bromo-2-(2-cyclopropyl-1-(4-(2-(difluoromethyl)-2H-1,2,3-triazol-4-yl)-1H-pyrazol-1-yl)ethyl)pyridine and 5-bromo-2-(2-cyclopropyl-1-(4-(2-(difluoromethyl)-2H-1,2,3-triazol-4-yl)-1H-pyrazol-1-yl)ethyl)pyridine A solution of 2-(1-(4-(1H-1,2,3-triazol-5-yl)-1H-pyrazol-1-yl)-2-cyclopropylethyl)-5-bromopyridine (1.0 g, 2.8 mmol, 1.0 equiv.), sodium 2-chloro-2,2-difluoroacetate (0.64 g, 4.18 mmol, 1.5 equiv.) and cesium carbonate (2.7 g, 8.4 mmol, 3.0 equiv.) in DMA (30 mL) under nitrogen atmosphere was stirred for 1H at 70° C. After the mixture was cooled to room temperature, water (50 mL) was added. The resulting mixture was extracted with ethyl acetate twice. The organic layers were combined, dried over anhydrous sodium sulfate, filtered and concentrated. The resulting residue was purified by silica gel chromatography (0→20% EA/PE) to yield a mixture of 5-bromo-2-(2-cyclopropyl-1-(4-(1-(difluoromethyl)-1H-1,2,3-triazol-5-yl)-1H-pyrazol-1-yl)ethyl)pyridine, 5-bromo-2-(2-cyclopropyl-1-(4-(1-(difluoromethyl)-1H-1,2,3-triazol-4-yl)-1H-pyrazol-1-yl)ethyl)pyridine and 5-bromo-2-(2-cyclopropyl-1-(4-(2-(difluoromethyl)-2H-1,2,3-triazol-4-yl)-1H-pyrazol-1-yl)ethyl)pyridine as colorless oil. LC/MS: mass calculated for $C_{16}H_{15}BrF_2N_6$: 408.05, measured (ES, m/z): 409.05, 410.05 $[M+H, M+H+2]^+$.

Step 3: 4-Chloro-2-(6-(2-cyclopropyl-1-(4-(1-(difluoromethyl)-1H-1,2,3-triazol-5-yl)-1H-pyrazol-1-yl)ethyl)pyridin-3-yl)-3-fluoroaniline, 4-chloro-2-(6-(2-cyclopropyl-1-(4-(1-(difluoromethyl)-1H-1,2,3-triazol-4-yl)-1H-pyrazol-1-yl)ethyl)pyridin-3-yl)-3-fluoroaniline and 4-chloro-2-(6-(2-cyclopropyl-1-(4-(2-(difluoromethyl)-2H-1,2,3-triazol-4-yl)-1H-pyrazol-1-yl)ethyl)pyridin-3-yl)-3-fluoroaniline To a solution of the mixture of 5-bromo-2-(2-cyclopropyl-1-(4-(1-(difluoromethyl)-1H-1,2,3-triazol-5-yl)-1H-pyrazol-1-yl)ethyl)pyridine, 5-bromo-2-(2-cyclopropyl-1-(4-(1-(difluoromethyl)-1H-1,2,3-triazol-4-yl)-1H-pyrazol-1-yl)ethyl)pyridine and 5-bromo-2-(2-cyclopropyl-1-(4-(2-(difluoromethyl)-2H-1,2,3-triazol-4-yl)-1H-pyrazol-1-yl)ethyl)pyridine (1.0 g, 2.44 mmol, 1.0 equiv.) in 1,4-dioxane (13 mL) and water (1 mL) was added (6-amino-3-chloro-2-fluorophenyl)boronic acid (833 mg, 4.40 mmol, 1.8 equiv.) tetrakis(triphenylphosphine)palladium (282 mg, 0.24 mmol, 0.1 equiv.) and potassium carbonate (1.0 g, 7.33 mmol, 3.0 equiv.). The reaction mixture was stirred at 100° C. for 2 h, then quenched with water, and extracted with ethyl acetate twice. The combined organic layers were dried over anhydrous sodium sulfate and concentrated under vacuum. The residue was applied onto a silica gel column (0→100% EA/PE) to yield a mixture of 4-chloro-2-(6-(2-cyclopropyl-1-(4-(1-(difluoromethyl)-1H-1,2,3-triazol-5-yl)-1H-pyrazol-1-yl)ethyl)pyridin-3-yl)-3-fluoroaniline, 4-chloro-2-(6-(2-cyclopropyl-1-(4-(1-(difluoromethyl)-1H-1,2,3-triazol-4-yl)-1H-pyrazol-1-yl)ethyl)pyridin-3-yl)-3-fluoroaniline and 4-chloro-2-(6-(2-cyclopropyl-1-(4-(2-(difluoromethyl)-2H-1,2,3-triazol-4-yl)-1H-pyrazol-1-yl)ethyl)pyridin-3-yl)-3-fluoroaniline as light yellow oil. LC/MS: mass calculated for $C_{22}H_{19}ClF_3N_7$: 473.13, measured (ES, m/z): 474.20 $[M+H]+$.

Step 4: 5-(3-Chloro-2-fluoro-6-(1H-tetrazol-1-yl)phenyl)-2-(2-cyclopropyl-1-(4-(2-(difluoromethyl)-2H-1,2,3-triazol-4-yl)-1H-pyrazol-1-yl)ethyl)pyridine, the mixture of 5-(3-chloro-2-fluoro-6-(1H-tetrazol-1-yl)phenyl)-2-(2-cyclopropyl-1-(4-(1-(difluoromethyl)-1H-1,2,3-triazol-5-yl)-1H-pyrazol-1-yl)ethyl)pyridine and 5-(3-chloro-2-fluoro-6-(1H-tetrazol-1-yl)phenyl)-2-(2-cyclopropyl-1-(4-(1-(difluoromethyl)-1H-1,2,3-triazol-4-yl)-1H-pyrazol-1-yl)ethyl)pyridine To a solution of the mixture of 4-chloro-2-(6-(2-cyclopropyl-1-(4-(1-(difluoromethyl)-1H-1,2,3-triazol-5-yl)-1H-pyrazol-1-yl)ethyl)pyridin-3-yl)-3-fluoroaniline, 4-chloro-2-(6-(2-cyclopropyl-1-(4-(1-(difluoromethyl)-1H-1,2,3-triazol-4-yl)-1H-pyrazol-1-yl)ethyl)pyridin-3-yl)-3-fluoroaniline and 4-chloro-2-(6-(2-cyclopropyl-1-(4-(2-(difluoromethyl)-2H-1,2,3-triazol-4-yl)-1H-pyrazol-1-yl)ethyl)pyridin-3-yl)-3-fluoroaniline (1.0 g, 2.11 mmol, 1.0 equiv.) in acetic acid (15 mL) was added trimethoxymethane (2.2 g, 21.1 mmol, 10.0 equiv.) and $TMSN_3$ (2.4 g, 21.1 mmol, 10.0 equiv.). The resulting mixture was stirred overnight at room temperature, then concentrated under vacuum. The residue was purified by reverse column chromatography on C18 (120 g, $MeCN/H_2O$ (0.05% $CF_3COOH$): 5→80%) to yield 5-(3-chloro-2-fluoro-6-(1H-tetrazol-1-yl)phenyl)-2-(2-cyclopropyl-1-(4-(2-(difluoromethyl)-2H-1,2,3-triazol-4-yl)-1H-pyrazol-1-yl)ethyl)pyridine as a light yellow solid, and a mixture of 5-(3-chloro-2-fluoro-6-(1H-tetrazol-1-yl)

phenyl)-2-(2-cyclopropyl-1-(4-(1-(difluoromethyl)-1H-1,2,3-triazol-5-yl)-1H-pyrazol-1-yl)ethyl)pyridine and 5-(3-chloro-2-fluoro-6-(1H-tetrazol-1-yl)phenyl)-2-(2-cyclopropyl-1-(4-(1-(difluoromethyl)-1H-1,2,3-triazol-4-yl)-1H-pyrazol-1-yl)ethyl)pyridine as an light yellow solid. LC/MS: mass calculated for $C_{23}H_{18}ClF_3N_{10}$: 526.14, measured (ES, m/z): 527.20 [M+H]$^+$.

Step 5: (R)-5-(3-Chloro-2-fluoro-6-(1H-tetrazol-1-yl)phenyl)-2-(2-cyclopropyl-1-(4-(1-(difluoromethyl)-1H-1,2,3-triazol-4-yl)-1H-pyrazol-1-yl)ethyl)pyridine 1-oxide A solution of the mixture of 5-(3-chloro-2-fluoro-6-(1H-tetrazol-1-yl)phenyl)-2-(2-cyclopropyl-1-(4-(1-(difluoromethyl)-1H-1,2,3-triazol-5-yl)-1H-pyrazol-1-yl)ethyl)pyridine and 5-(3-chloro-2-fluoro-6-(1H-tetrazol-1-yl)phenyl)-2-(2-cyclopropyl-1-(4-(1-(difluoromethyl)-1H-1,2,3-triazol-4-yl)-1H-pyrazol-1-yl)ethyl)pyridine (350 mg, 0.66 mmol, 1.0 equiv.), methylrhenium (VII) trioxide (33 mg, 0.13 mmol, 0.2 equiv.) and hydrogen peroxide (30 wt %, 753 mg, 6.64 mmol, 10.0 equiv.) in $CH_3OH$ (5 mL) was stirred for 1 h at room temperature. The reaction mixture was purified by reverse column chromatography on C18 (80 g, MeCN/$H_2O$ (0.05% $CF_3COOH$): 5→80%) to yield 5-(3-chloro-2-fluoro-6-(1H-tetrazol-1-yl)phenyl)-2-(1-(4-(1-(difluoromethyl)-1H-1,2,3-triazol-4-yl)-1H-pyrazol-1-yl)-2-(4-fluorophenyl)ethyl)pyridine 1-oxide as an off-white solid, which was purified by Prep-Chiral-HPLC with MtBE(0.1% DEA)MeOH=50:50 to yield (R)-5-(3-chloro-2-fluoro-6-(1H-tetrazol-1-yl)phenyl)-2-(2-cyclopropyl-1-(4-(1-(difluoromethyl)-1H-1,2,3-triazol-4-yl)-1H-pyrazol-1-yl)ethyl)pyridine 1-oxide.

LC/MS: mass calculated for $C_{23}H_{17}ClF_3N_{10}O$: 542.13, measured (ES, m/z): 543.05 [M+H]$^+$. $^1$H NMR (400 MHz, DMSO-$d_6$): δ 9.69 (s, $^1$H), 8.58 (s, $^1$H), 8.20-8.50 (m, 2H), 8.18 (s, $^1$H), 8.01-8.12 (m, $^1$H), 7.99 (s, $^1$H), 7.70-7.81 (m, $^1$H), 7.40 (d, J=8.3 Hz, $^1$H), 7.12-7.22 (m, $^1$H), 6.10-6.22 (m, $^1$H), 2.26-2.38 (m, $^1$H), 1.90-2.02 (m, $^1$H), 0.50-0.65 (m, $^1$H), 0.23-0.41 (m, 2H), 0.05-0.17 (m, $^1$H), −0.11-−0.01 (m, $^1$H).

Example 633: (R)-5-(3-Chloro-2-fluoro-6-(1H-tetrazol-1-yl)phenyl)-2-(1-(4-(2-(difluoromethyl)-2H-1,2,3-triazol-4-yl)-1H-pyrazol-1-yl)-2-(4-fluorophenyl)ethyl)pyridine 1-oxide

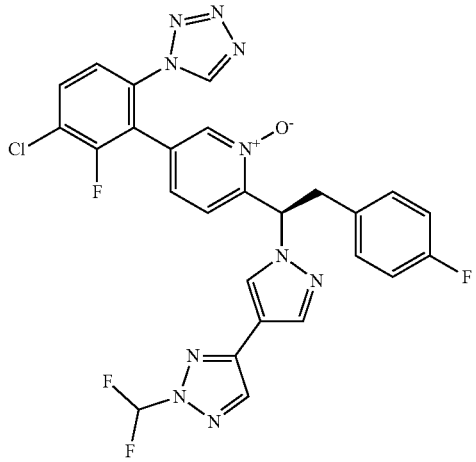 [SMILES: [O-][n+]1cc(-c2c(-n3cnnn3)ccc(Cl)c2F)ccc1[C@@H](Cc1ccc(F)cc1)n1cc(-c2cnn(C(F)F)n2)cn1]

LC/MS: mass calculated for $C_{26}H_{17}ClF_4N_{10}O$: 596.12, measured (ES, m/z): 597.25 [M+H]$^+$ $^1$H NMR (400 MHz, DMSO-$d_6$) δ 9.70 (s, 1H), 8.41-8.52 (m, 2H), 8.38 (s, 1H), 7.92-8.29 (m, 3H), 7.77 (dd, J=8.7, 1.5 Hz, 1H), 7.40 (d, J=8.3 Hz, 1H), 7.15-7.25 (m, 3H), 7.01-7.11 (m, 2H), 6.25 (dd, J=10.0, 4.6 Hz, 1H), 3.51-3.66 (m, 2H). $^{19}$F NMR (376 MHz, DMSO-$d_6$) δ −96.70, −112.71, −112.75.

Example 634: (S)-5-(3-Chloro-2-fluoro-6-(1H-tetrazol-1-yl)phenyl)-2-(1-(4-(1-(difluoromethyl)-1H-1,2,3-triazol-4-yl)-1H-pyrazol-1-yl)-2-(4-fluorophenyl)ethyl)pyridine 1-oxide

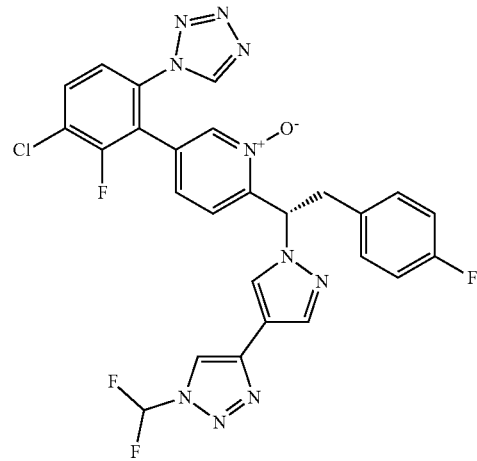 [SMILES: [O-][n+]1cc(-c2c(-n3cnnn3)ccc(Cl)c2F)ccc1[C@H](Cc1ccc(F)cc1)n1cc(-c2cn(C(F)F)nn2)cn1]

LC/MS: mass calculated for $C_{26}H_{17}ClF_4N_{10}O$: 596.12, measured (ES, m/z): 597.05 [M+H]$^+$. $^1$H NMR (400 MHz, DMSO-$d_6$) δ 9.70 (s, 1H), 8.85 (s, 1H), 8.48 (d, J=1.6 Hz, 1H), 8.11-8.43 (m, 2H), 8.07 (dd, J=8.7, 7.8 Hz, 1H), 8.02 (s, 1H), 7.77 (dd, J=8.7, 1.5 Hz, 1H), 7.38 (d, J=8.3 Hz, 1H), 7.14-7.24 (m, 3H), 7.01-7.10 (m, 2H), 6.20-6.30 (m, 1H), 3.50-3.68 (m, 2H). $^{19}$F NMR (376 MHZ, DMSO-$d_6$) −97.71, −112.70, −116.13.

Example 635: (S*)-5-(3-Chloro-2-fluoro-6-(1H-tetrazol-1-yl)phenyl)-2-(1-(4-(2-(difluoromethyl)-2H-1,2,3-triazol-4-yl)-1H-pyrazol-1-yl)-2-(4-fluorophenyl)ethyl)pyridine 1-oxide

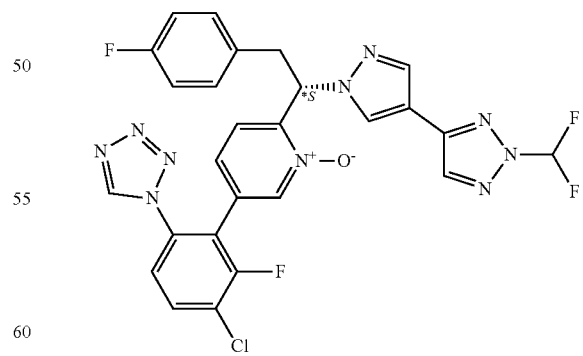

LC/MS: mass calculated for $C_{26}H_{17}ClF_4N_{10}O$: 596.12, measured (ES, m/z): 597.25 [M+H]$^+$. $^1$H NMR (400 MHz, DMSO-$d_6$) δ 9.70 (s, 1H), 8.42-8.50 (m, 2H), 8.38 (s, 1H), 7.94-8.28 (m, 3H), 7.77 (dd, J=8.7, 1.5 Hz, 1H), 7.40 (d, J=8.3 Hz, 1H), 7.13-7.22 (m, 3H), 7.01-7.11 (m, 2H), 6.25

(dd, J=9.9, 4.6 Hz, 1H), 3.49-3.66 (m, 2H). $^{19}$F NMR (376 MHz, DMSO-d$_6$) δ −96.49, −112.70, −116.08.

Example 636: (R)-5-(3-Chloro-2-fluoro-6-(1H-tetrazol-1-yl)phenyl)-2-(1-(4-(1-(difluoromethyl)-1H-1,2,3-triazol-5-yl)-1H-pyrazol-1-yl)-2-(4-fluorophenyl)ethyl)pyridine 1-oxide

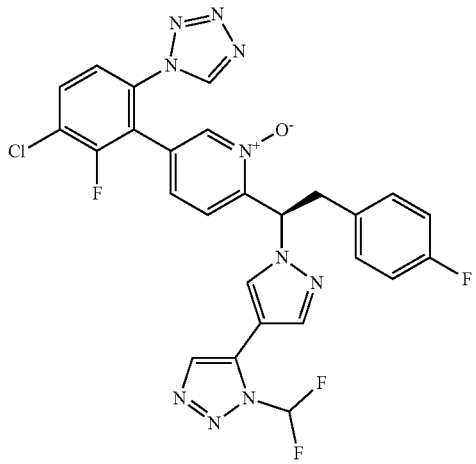 [SMILES: [O-][n+]1cc(-c2c(-n3cnnn3)ccc(Cl)c2F)ccc1[C@@H](Cc1ccc(F)cc1)n1cc(-c2cnnn2C(F)F)cn1]

Step 1: 5-Bromo-2-(1-(4-ethynyl-1H-pyrazol-1-yl)-2-(4-fluorophenyl)ethyl)pyridine To a solution of 4-ethynyl-1H-pyrazole (0.8 g, 8.7 mmol, 1.0 equiv.) in acetonitrile (40 mL) was cesium carbonate (2.8 g, 8.7 mmol, 1.0 equiv.). After the reaction mixture was stirred at room temperature 30 min, 1-(5-bromopyridin-2-yl)-2-(4-fluorophenyl)ethyl methanesulfonate (3.6 g, 8.7 mmol, 2.0 equiv.) was added. The mixture stirred for 2 h at 80° C. The mixture was concentrated and purified by silica gel chromatography (0→20% EA/PE) to yield 5-bromo-2-(1-(4-ethynyl-1H-pyrazol-1-yl)-2-(4-fluorophenyl)ethyl)pyridine as light yellow oil. LC/MS: mass calculated for $C_{18}H_{13}BrFN_3$: 369.03, measured (ES, m/z): 369.95, 371.95 [M+H, M+H+2]$^+$.

Step 2: 2-(1-(4-(1H-1,2,3-Triazol-5-yl)-1H-pyrazol-1-yl)-2-(4-fluorophenyl)ethyl)-5-bromopyridine To a solution of 5-bromo-2-(1-(4-ethynyl-1H-pyrazol-1-yl)-2-(4-fluorophenyl)ethyl)pyridine (2.5 g, 6.8 mmol, 1.0 equiv.) and trimethoxymethane (3.9 g, 33.8 mmol, 5.0 equiv.) in N,N-dimethylacetamide (20 mL) was added CuSO$_4$.5H$_2$O (0.5 g, 2.03 mmol, 0.3 equiv.) and sodium ascorbate (0.4 g, 2.03 mmol, 0.3 equiv.), and the mixture was stirred at 35° C. for 16 h. The mixture was diluted with water, and the mixture extracted with EtOAc twice. The combined organic layers were washed with brine, dried over MgSO$_4$, filtered, and evaporated. The residue was purified by silica gel chromatography (0→20% EA/PE) to yield 2-(1-(4-(1H-1,2,3-triazol-5-yl)-1H-pyrazol-1-yl)-2-(4-fluorophenyl)ethyl)-5-bromopyridine as a colorless solid. LC/MS: mass calculated for $C_{18}H_{14}BrFN_6$: 412.05, measured (ES, m/z): 413.05, 415.05 [M+H, M+H+2]$^+$.

Step 3: 5-Bromo-2-(1-(4-(2-(difluoromethyl)-2H-1,2,3-triazol-4-yl)-1H-pyrazol-1-yl)-2-(4-fluorophenyl)ethyl)pyridine, the mixture of the 5-bromo-2-(1-(4-(1-(difluoromethyl)-1H-1,2,3-triazol-5-yl)-1H-pyrazol-1-yl)-2-(4-fluorophenyl)ethyl)pyridine and 5-bromo-2-(1-(4-(1-(difluoromethyl)-1H-1,2,3-triazol-4-yl)-1H-pyrazol-1-yl)-2-(4-fluorophenyl)ethyl)pyridine A mixture of 2-(1-(4-(1H-1,2,3-triazol-5-yl)-1H-pyrazol-1-yl)-2-(4-fluorophenyl)ethyl)-5-bromopyridine (2.0 g, 4.84 mmol, 1.0 equiv.), sodium 2-chloro-2,2-difluoroacetate (1.1 g, 7.26 mmol, 1.5 equiv.) and cesium carbonate (4.7 g, 14.52 mmol, 3.0 equiv.) in DMF (20 mL) under nitrogen atmosphere was stirred 1 h at 70° C. After the mixture was cooled to room temperature, the reaction was quenched with water. The resulting mixture was extracted with ethyl acetate. The organic layers were combined, dried over anhydrous sodium sulfate, filtered and concentrated. The resulting residue was purified by silica gel chromatography (0→20% EA/PE) to yield 5-bromo-2-(1-(4-(2-(difluoromethyl)-2H-1,2,3-triazol-4-yl)-1H-pyrazol-1-yl)-2-(4-fluorophenyl)ethyl)pyridine as light yellow oil, and a mixture of 5-bromo-2-(1-(4-(1-(difluoromethyl)-1H-1,2,3-triazol-5-yl)-1H-pyrazol-1-yl)-2-(4-fluorophenyl)ethyl)pyridine and 5-bromo-2-(1-(4-(1-(difluoromethyl)-1H-1,2,3-triazol-4-yl)-1H-pyrazol-1-yl)-2-(4-fluorophenyl)ethyl)pyridine as light yellow oil. LC/MS: mass calculated for $C_{19}H_{14}BrF_3N_6$: 462.04, measured (ES, m/z): 463.05, 465.05 [M+H, M+H+2]$^+$.

Step 4: 4-Chloro-2-(6-(1-(4-(1-(difluoromethyl)-1H-1,2,3-triazol-5-yl)-1H-pyrazol-1-yl)-2-(4-fluorophenyl)ethyl)pyridin-3-yl)-3-fluoroaniline and 4-chloro-2-(6-(1-(4-(1-(difluoromethyl)-1H-1,2,3-triazol-4-yl)-1H-pyrazol-1-yl)-2-(4-fluorophenyl)ethyl)pyridin-3-yl)-3-fluoroaniline To a solution of the mixture of 5-bromo-2-(1-(4-(1-(difluoromethyl)-1H-1,2,3-triazol-5-yl)-1H-pyrazol-1-yl)-2-(4-fluorophenyl)ethyl)pyridine and 5-bromo-2-(1-(4-(1-(difluoromethyl)-1H-1,2,3-triazol-4-yl)-1H-pyrazol-1-yl)-2-(4-fluorophenyl)ethyl)pyridine (1.6 g, 3.45 mmol, 1.0 equiv.) in 1,4-dioxane (20 mL) and water (2 mL) was added (6-amino-3-chloro-2-fluorophenyl)boronic acid (1.3 g, 6.91 mmol, 2.0 equiv.), tetrakis(triphenylphosphine)palladium (399 mg, 0.35 mmol, 0.1 equiv.) and potassium carbonate (1.4 g, 10.4 mmol, 3.0 equiv.). The reaction mixture was stirred at 100° C. for 2 h under N$_2$, then quenched with water. The resulting mixture was extracted with ethyl acetate. The combined organic layers were dried over anhydrous sodium sulfate and concentrated under vacuum. The residue was applied onto a silica gel column (0→100% EA/PE) to yield a mixture of 4-chloro-2-(6-(1-(4-(1-(difluoromethyl)-1H-1,2,3-triazol-5-yl)-1H-pyrazol-1-yl)-2-(4-fluorophenyl)ethyl)pyridin-3-yl)-3-fluoroaniline and 4-chloro-2-(6-(1-(4-(1-(difluoromethyl)-1H-1,2,3-triazol-4-yl)-1H-pyrazol-1-yl)-2-(4-fluorophenyl)ethyl)pyridin-3-yl)-

3-fluoroaniline as a grey solid. LC/MS: mass calculated for $C_{25}H_{18}ClF_4N_7$: 527.12, measured (ES, m/z): 528.20 [M+H]$^+$.

Step 5: 5-(3-Chloro-2-fluoro-6-(1H-tetrazol-1-yl)phenyl)-2-(1-(4-(2-(difluoromethyl)-2H-1,2,3-triazol-4-yl)-1H-pyrazol-1-yl)-2-(4-fluorophenyl)ethyl)pyridine To a solution of the mixture of 4-chloro-2-(6-(1-(4-(1-(difluoromethyl)-1H-1,2,3-triazol-5-yl)-1H-pyrazol-1-yl)-2-(4-fluorophenyl)ethyl)pyridin-3-yl)-3-fluoroaniline and 4-chloro-2-(6-(1-(4-(1-(difluoromethyl)-1H-1,2,3-triazol-4-yl)-1H-pyrazol-1-yl)-2-(4-fluorophenyl)ethyl)pyridin-3-yl)-3-fluoroaniline (1.6 g, 3.0 mmol, 1.0 equiv.) in acetic acid (15 mL) was added trimethoxymethane (3.2 g, 30.3 mmol, 10.0 equiv.), and TMSN$_3$ (3.5 g, 30.3 mmol, 10.0 equiv.). The resulting mixture was stirred overnight at room temperature, then concentrated under vacuum. The residue was purified by reverse column chromatography on C18 (5→80%, MeCN/H$_2$O (0.05% CF$_3$COOH)) to yield a mixture of 5-(3-chloro-2-fluoro-6-(1H-tetrazol-1-yl)phenyl)-2-(1-(4-(1-(difluoromethyl)-1H-1,2,3-triazol-5-yl)-1H-pyrazol-1-yl)-2-(4-fluorophenyl)ethyl)pyridine and 5-(3-chloro-2-fluoro-6-(1H-tetrazol-1-yl)phenyl)-2-(1-(4-(1-(difluoromethyl)-1H-1,2,3-triazol-4-yl)-1H-pyrazol-1-yl)-2-(4-fluorophenyl)ethyl)pyridine as an off-white solid. LC/MS: mass calculated for $C_{26}H_{17}ClF_4N_{10}$: 580.13, measured (ES, m/z): 581.20 [M+H]$^+$.

Step 6: (R)-5-(3-Chloro-2-fluoro-6-(1H-tetrazol-1-yl)phenyl)-2-(1-(4-(1-(difluoromethyl)-1H-1,2,3-triazol-5-yl)-1H-pyrazol-1-yl)-2-(4-fluorophenyl)ethyl)pyridine 1-oxide To a solution of the mixture of 5-(3-chloro-2-fluoro-6-(1H-tetrazol-1-yl)phenyl)-2-(1-(4-(1-(difluoromethyl)-1H-1,2,3-triazol-5-yl)-1H-pyrazol-1-yl)-2-(4-fluorophenyl)ethyl)pyridine and 5-(3-chloro-2-fluoro-6-(1H-tetrazol-1-yl)phenyl)-2-(1-(4-(1-(difluoromethyl)-1H-1,2,3-triazol-4-yl)-1H-pyrazol-1-yl)-2-(4-fluorophenyl)ethyl)pyridine (500 mg, 0.86 mmol, 1.0 equiv.) in CH$_3$OH (8 mL) was added methylrhenium (VII) trioxide (43 mg, 0.17 mmol, 0.2 eq) and hydrogen peroxide (30 wt %, 976 mg, 8.61 mmol, 10.0 equiv.). The mixture was stirred for 1 h at room temperature, then purified by reverse column chromatography on C18 (5→80%, MeCN/H$_2$O (0.05% CF$_3$COOH)) to yield 5-(3-chloro-2-fluoro-6-(1H-tetrazol-1-yl)phenyl)-2-(1-(4-(1-(difluoromethyl)-1H-1,2,3-triazol-5-yl)-1H-pyrazol-1-yl)-2-(4-fluorophenyl)ethyl)pyridine 1-oxide as an off-white solid, which was purified by Prep-Chiral-HPLC with MtBE(0.1% DEA):MeOH=50:50 to yield (R)-5-(3-chloro-2-fluoro-6-(1H-tetrazol-1-yl)phenyl)-2-(1-(4-(1-(difluoromethyl)-1H-1,2,3-triazol-5-yl)-1H-pyrazol-1-yl)-2-(4-fluorophenyl)ethyl)pyridine 1-oxide as an off-white solid.

LC/MS: mass calculated for $C_{26}H_{17}ClF_4N_{10}O$: 596.12, measured (ES, m/z): 597.05 [M+H]$^+$. $^1$H NMR (400 MHz, DMSO-d$_6$): δ 9.71 (s, 1H), 8.48 (d, J=1.6 Hz, 1H), 8.13-8.42 (m, 2H), 8.12 (s, 1H), 8.03-8.11 (m, 1H), 8.00 (s, 1H), 7.73-7.80 (m, 1H), 7.53 (d, J=8.3 Hz, 1H), 7.19-7.24 (m, 1H), 7.12-7.19 (m, 2H), 6.99-7.10 (m, 2H), 6.20-6.31 (m, 1H), 3.45-3.82 (m, 2H).

Example 637: (R)-5-(3-Chloro-2-fluoro-6-(1H-tetrazol-1-yl)phenyl)-2-(1-(4-(1-(difluoromethyl)-1H-1,2,3-triazol-4-yl)-1H-pyrazol-1-yl)-2-(4-fluorophenyl)ethyl)pyridine 1-oxide

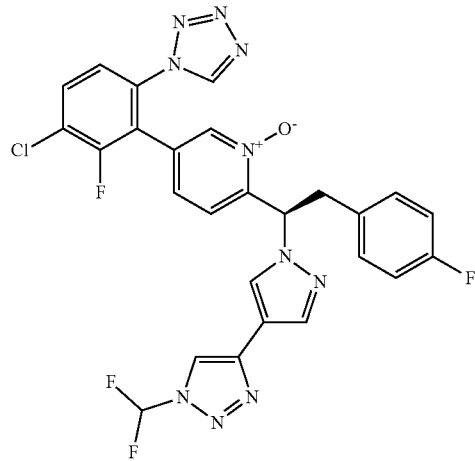 [SMILES: [O-][n+]1cc(-c2c(-n3cnnn3)ccc(Cl)c2F)ccc1[C@@H](Cc1ccc(F)cc1)n1cc(-c2cn(C(F)F)nn2)cn1]

Step 1: 5-Bromo-2-(1-(4-ethynyl-1H-pyrazol-1-yl)-2-(4-fluorophenyl)ethyl)pyridine To a solution of 4-ethynyl-1H-pyrazole (0.8 g, 8.7 mmol, 1.0 equiv.) in acetonitrile (40 mL) was cesium carbonate (2.8 g, 8.7 mmol, 1.0 equiv.). After the reaction mixture was stirred at room temperature 30 min, 1-(5-bromopyridin-2-yl)-2-(4-fluorophenyl)ethyl methanesulfonate (3.6 g, 8.7 mmol, 2.0 equiv.) was added. The mixture stirred for 2 h at 80° C. The mixture was concentrated and purified by silica gel chromatography (0→20% EA/PE) to yield 5-bromo-2-(1-(4-ethynyl-1H-pyrazol-1-yl)-2-(4-fluorophenyl)ethyl)pyridine as light yellow oil. LC/MS: mass calculated for $C_{18}H_{13}BrFN_3$: 369.03, measured (ES, m/z): 369.95, 371.95 [M+H, M+H+2]$^+$.

Step 2: 2-(1-(4-(1H-1,2,3-triazol-5-yl)-1H-pyrazol-1-yl)-2-(4-fluorophenyl)ethyl)-5-bromopyridine To a solution of 5-bromo-2-(1-(4-ethynyl-1H-pyrazol-1-yl)-2-(4-fluorophenyl)ethyl)pyridine (2.5 g, 6.8 mmol, 1.0 equiv.) and trimethoxymethane (3.9 g, 33.8 mmol, 5.0 equiv.) in N,N-dimethylacetamide (20 mL) was added CuSO$_4$.5H$_2$O (0.5 g, 2.03 mmol, 0.3 equiv.) and sodium ascorbate (0.4 g, 2.03 mmol, 0.3 equiv.), and the mixture was stirred at 35° C. for 16 h. The mixture was diluted with water, and the mixture extracted with EtOAc twice. The combined organic layers were washed with brine, dried over MgSO$_4$, filtered, and evaporated. The residue was purified by silica gel chromatography (0→20% EA/PE) to yield 2-(1-(4-(1H-1,2,3-triazol-5-yl)-1H-pyrazol-1-yl)-2-(4-fluorophenyl)ethyl)-5-bromopyridine as a colorless solid. LC/MS: mass calculated for $C_{18}H_{14}BrFN_6$: 412.05, measured (ES, m/z): 413.05, 415.05 [M+H, M+H+2]$^+$.

Step 3: 5-Bromo-2-(1-(4-(2-(difluoromethyl)-2H-1, 2,3-triazol-4-yl)-1H-pyrazol-1-yl)-2-(4-fluorophenyl)ethyl)pyridine, the mixture of the 5-bromo-2-(1-(4-(1-(difluoromethyl)-1H-1,2,3-triazol-5-yl)-1H-pyrazol-1-yl)-2-(4-fluorophenyl)ethyl)pyridine and 5-bromo-2-(1-(4-(1-(difluoromethyl)-1H-1,2,3-triazol-4-yl)-1H-pyrazol-1-yl)-2-(4-fluorophenyl)ethyl)pyridine A mixture of 2-(1-(4-(1H-1,2,3-triazol-5-yl)-1H-pyrazol-1-yl)-2-(4-fluorophenyl)ethyl)-5-bromopyridine (2.0 g, 4.84 mmol, 1.0 equiv.), sodium 2-chloro-2,2-difluoroacetate (1.1 g, 7.26 mmol, 1.5 equiv.) and cesium carbonate (4.7 g, 14.52 mmol, 3.0 equiv.) in DMF (20 mL) under nitrogen atmosphere was stirred 1H at 70° C. After the mixture was cooled to room temperature, the reaction was quenched with water. The resulting mixture was extracted with ethyl acetate. The organic layers were combined, dried over anhydrous sodium sulfate, filtered and concentrated. The resulting residue was purified by silica gel chromatography (0→20% EA/PE) to yield 5-bromo-2-(1-(4-(2-(difluoromethyl)-2H-1,2,3-triazol-4-yl)-1H-pyrazol-1-yl)-2-(4-fluorophenyl)ethyl)pyridine as light yellow oil, and a mixture of 5-bromo-2-(1-(4-(1-(difluoromethyl)-1H-1,2,3-triazol-5-yl)-1H-pyrazol-1-yl)-2-(4-fluorophenyl)ethyl)pyridine and 5-bromo-2-(1-(4-(1-(difluoromethyl)-1H-1,2,3-triazol-4-yl)-1H-pyrazol-1-yl)-2-(4-fluorophenyl)ethyl)pyridine as light yellow oil. LC/MS: mass calculated for $C_{19}H_{14}BrF_3N_6$: 462.04, measured (ES, m/z): 463.05, 465.05 [M+H, M+H+2]$^+$.

Step 4: 4-Chloro-2-(6-(1-(4-(1-(difluoromethyl)-1H-1,2,3-triazol-5-yl)-1H-pyrazol-1-yl)-2-(4-fluorophenyl)ethyl)pyridin-3-yl)-3-fluoroaniline and 4-chloro-2-(6-(1-(4-(1-(difluoromethyl)-1H-1,2,3-triazol-4-yl)-1H-pyrazol-1-yl)-2-(4-fluorophenyl)ethyl)pyridin-3-yl)-3-fluoroaniline To a solution of the mixture of 5-bromo-2-(1-(4-(1-(difluoromethyl)-1H-1,2,3-triazol-5-yl)-1H-pyrazol-1-yl)-2-(4-fluorophenyl)ethyl)pyridine and 5-bromo-2-(1-(4-(1-(difluoromethyl)-1H-1,2,3-triazol-4-yl)-1H-pyrazol-1-yl)-2-(4-fluorophenyl)ethyl)pyridine (1.6 g, 3.45 mmol, 1.0 equiv.) in 1,4-dioxane (20 mL) and water (2 mL) was added (6-amino-3-chloro-2-fluorophenyl)boronic acid (1.3 g, 6.91 mmol, 2.0 equiv.), tetrakis(triphenylphosphine)palladium (399 mg, 0.35 mmol, 0.1 equiv.) and potassium carbonate (1.4 g, 10.4 mmol, 3.0 equiv.). The reaction mixture was stirred at 100° C. for 2 h under N$_2$, then quenched with water. The resulting mixture was extracted with ethyl acetate. The combined organic layers were dried over anhydrous sodium sulfate and concentrated under vacuum. The residue was applied onto a silica gel column (0→100% EA/PE) to yield a mixture of 4-chloro-2-(6-(1-(4-(1-(difluoromethyl)-1H-1,2,3-triazol-5-yl)-1H-pyrazol-1-yl)-2-(4-fluorophenyl)ethyl)pyridin-3-yl)-3-fluoroaniline and 4-chloro-2-(6-(1-(4-(1-(difluoromethyl)-1H-1,2,3-triazol-4-yl)-1H-pyrazol-1-yl)-2-(4-fluorophenyl)ethyl)pyridin-3-yl)-3-fluoroaniline as a grey solid. LC/MS: mass calculated for $C_{25}H_{18}ClF_4N_7$: 527.12, measured (ES, m/z): 528.20 [M+H]$^+$.

Step 5: 5-(3-Chloro-2-fluoro-6-(1H-tetrazol-1-yl)phenyl)-2-(1-(4-(2-(difluoromethyl)-2H-1,2,3-triazol-4-yl)-1H-pyrazol-1-yl)-2-(4-fluorophenyl)ethyl)pyridine To a solution of the mixture of 4-chloro-2-(6-(1-(4-(1-(difluoromethyl)-1H-1,2,3-triazol-5-yl)-1H-pyrazol-1-yl)-2-(4-fluorophenyl)ethyl)pyridin-3-yl)-3-fluoroaniline and 4-chloro-2-(6-(1-(4-(1-(difluoromethyl)-1H-1,2,3-triazol-4-yl)-1H-pyrazol-1-yl)-2-(4-fluorophenyl)ethyl)pyridin-3-yl)-3-fluoroaniline (1.6 g, 3.0 mmol, 1.0 equiv.) in acetic acid (15 mL) was added trimethoxymethane (3.2 g, 30.3 mmol, 10.0 equiv.), and azidotrimethylsilane (3.5 g, 30.3 mmol, 10.0 equiv.). The resulting mixture was stirred overnight at room temperature, then concentrated under vacuum. The residue was purified by reverse column chromatography on C18 (5→80%, MeCN/H$_2$O (0.05% CF$_3$COOH)) to yield a mixture of 5-(3-chloro-2-fluoro-6-(1H-tetrazol-1-yl)phenyl)-2-(1-(4-(1-(difluoromethyl)-1H-1,2,3-triazol-5-yl)-1H-pyrazol-1-yl)-2-(4-fluorophenyl)ethyl)pyridine and 5-(3-chloro-2-fluoro-6-(1H-tetrazol-1-yl)phenyl)-2-(1-(4-(1-(difluoromethyl)-1H-1,2,3-triazol-4-yl)-1H-pyrazol-1-yl)-2-(4-fluorophenyl)ethyl)pyridine as an off-white solid. LC/MS: mass calculated for $C_{2H}H_{17}ClF_4N_{10}$: 580.13, measured (ES, m/z): 581.20 [M+H]$^+$.

Step 6: (R)-5-(3-Chloro-2-fluoro-6-(1H-tetrazol-1-yl)phenyl)-2-(1-(4-(1-(difluoromethyl)-1H-1,2,3-triazol-4-yl)-1H-pyrazol-1-yl)-2-(4-fluorophenyl)ethyl)pyridine 1-oxide To a solution of the mixture of 5-(3-chloro-2-fluoro-6-(1H-tetrazol-1-yl)phenyl)-2-(1-(4-(1-(difluoromethyl)-1H-1,2,3-triazol-5-yl)-1H-pyrazol-1-yl)-2-(4-fluorophenyl)ethyl)pyridine and 5-(3-chloro-2-fluoro-6-(1H-tetrazol-1-yl)phenyl)-2-(1-(4-(1-(difluoromethyl)-1H-1,2,3-triazol-4-yl)-1H-pyrazol-1-yl)-2-(4-fluorophenyl)ethyl)pyridine (500 mg, 0.86 mmol, 1.0 equiv.) in CH$_3$OH (8 mL) was added methylrhenium (VII) trioxide (43 mg, 0.17 mmol, 0.2 eq) and hydrogen peroxide (30 wt %, 976 mg, 8.61 mmol, 10.0 equiv.). The mixture was stirred for 1 h at room temperature, then purified by reverse column chromatography on C18 (5→80%, MeCN/H$_2$O (0.05% CF$_3$COOH)) to yield 5-(3-chloro-2-fluoro-6-(1H-tetrazol-1-yl)phenyl)-2-(1-(4-(1-(difluoromethyl)-1H-1,2,3-triazol-4-yl)-1H-pyrazol-1-yl)-2-(4-fluorophenyl)ethyl)pyridine 1-oxide as an off-white solid, which was purified by Prep-Chiral-HPLC with MtBE(0.1% DEA):MeOH=50:50 to yield (R)-5-(3-chloro-2-fluoro-6-(1H-tetrazol-1-yl)phenyl)-2-(1-(4-(1-(difluoromethyl)-1H-1,2,3-triazol-4-yl)-1H-pyrazol-1-yl)-2-(4-fluorophenyl)ethyl)pyridine 1-oxide as an off-white solid.

LC/MS: mass calculated for $C_{26}H_{17}ClF_4N_{10}O$: 596.12, measured (ES, m/z): 597.05 [M+H]$^+$. $^1$H NMR (400 MHz, DMSO-d$_6$): δ9.70 (s, 1H), 8.85 (s, 1H), 8.48 (d, J=1.6 Hz, 1H), 8.11-8.43 (m, 2H), 8.03-8.10 (m, 1H), 8.02 (s, 1H), 7.72-7.82 (m, 1H), 7.38 (d, J=8.3 Hz, 1H), 7.14-7.24 (m, 3H), 7.01-7.11 (m, 2H), 6.20-6.30 (m, 1H), 3.50-3.68 (m, 2H).

Example 638: (S)-5-(3-Chloro-2-fluoro-6-(1H-tetrazol-1-yl)phenyl)-2-(1-(4-(1-(difluoromethyl)-1H-imidazol-4-yl)-1H-pyrazol-1-yl)-2-(4-fluorophenyl)ethyl)pyridine 1-oxide

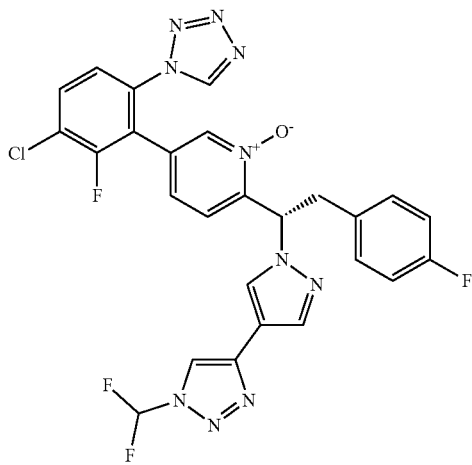 [SMILES: [O-][n+]1cc(-c2c(-n3cnnn3)ccc(Cl)c2F)ccc1[C@H](Cc1ccc(F)cc1)n1cc(-c2cn(C(F)F)nn2)cn1]

LC/MS: mass calculated for $C_{23}H_{18}ClF_3N_{10}O$: 542.13, measured (ES, m/z): 543.10 [M+H]$^+$. $^1$H NMR (400 MHz, DMSO-d$_6$) δ 9.69 (s, 1H), 8.90 (s, 1H), 8.52 (s, 1H), 8.12-8.46 (m, 2H), 8.05-8.13 (m, 1H), 8.01 (s, 1H), 7.76 (dd, J=8.7, 1.5 Hz, 1H), 7.29 (d, J=8.3 Hz, 1H), 7.16 (dd, J=8.2, 1.7 Hz, 1H), 6.12 (dd, J=9.9, 4.3 Hz, 1H), 2.29-2.41 (m, 1H), 2.08 (s, 1H), 1.85-1.94 (m, 1H), 0.55-0.67 (m, 1H), 0.25-0.33 (m, 2H), 0.09-0.19 (m, 1H), −0.05-0.00 (m, 1H). $^{19}$F NMR (376 MHz, DMSO-d$_6$) δ −96.22, −112.76.

Example 639: (S)-5-(3-Chloro-2-fluoro-6-(1H-tetrazol-1-yl)phenyl)-2-(1-(4-(1-(difluoromethyl)-1H-1,2,3-triazol-5-yl)-1H-pyrazol-1-yl)-2-(4-fluorophenyl)ethyl)pyridine 1-oxide

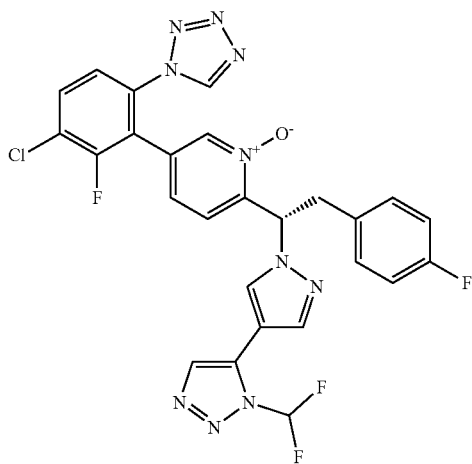 [SMILES: [O-][n+]1cc(-c2c(-n3cnnn3)ccc(Cl)c2F)ccc1[C@H](Cc1ccc(F)cc1)n1cc(-c2cnnn2C(F)F)cn1]

LC/MS: mass calculated for $C_{26}H_{17}ClF_4N_{10}O$: 596.12, measured (ES, m/z): 597.25 [M+H]$^+$. $^1$H NMR (400 MHz, DMSO-d$_6$) δ 9.71 (s, 1H), 8.48 (d, J=1.6 Hz, 1H), 8.12-8.43 (m, 2H), 8.12 (s, 1H), 8.08 (dd, J=8.7, 7.7 Hz, 1H), 8.00 (s, 1H), 7.77 (dd, J=8.7, 1.5 Hz, 1H), 7.53 (d, J=8.3 Hz, 1H), 7.22 (dd, J=8.3, 1.7 Hz, 1H), 7.11-7.20 (m, 2H), 6.99-7.10 (m, 2H), 6.22-6.32 (m, 1H), 3.45-3.68 (m, 2H). $^{19}$F NMR (376 MHZ, DMSO-d$_6$) −97.19, −112.68, −116.08.

Example 640: (S)-5-(3-Chloro-2-fluoro-6-(1H-tetrazol-1-yl)phenyl)-2-(2-cyclopropyl-1-(4-(2-(difluoromethyl)-2H-1,2,3-triazol-4-yl)-1H-pyrazol-1-yl)ethyl)pyridine 1-oxide

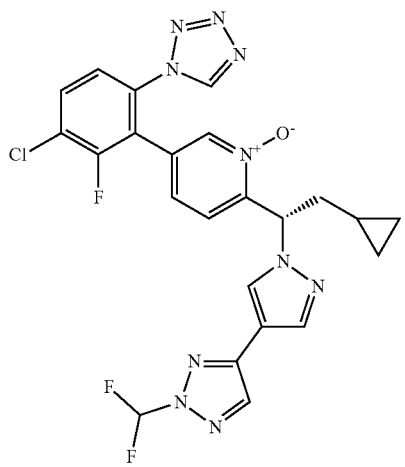 [SMILES: [O-][n+]1cc(-c2c(-n3cnnn3)ccc(Cl)c2F)ccc1[C@H](CC1CC1)n1cc(-c2cnn(C(F)F)n2)cn1]

LC/MS: mass calculated for $C_{23}H_{18}ClF_3N_{10}O$:542.13, measured (ES, m/z): 543.10 [M+H]$^+$. $^1$H NMR (400 MHz, DMSO-d$_6$) δ 9.69 (s, 1H), 8.64 (s, 1H), 8.40-8.49 (m, 2H), 7.95-8.31 (m, 3H), 7.76 (dd, J=8.7, 1.5 Hz, 1H), 7.31 (d, J=8.3 Hz, 1H), 7.16 (dd, J=8.3, 1.7 Hz, 1H), 6.09-6.18 (m, 1H), 2.33-2.43 (m, 1H), 1.88-1.99 (m, 1H), 0.55-0.65 (m, 1H), 0.27-0.40 (m, 2H), 0.08-0.17 (m, 1H), −0.07-0.00 (m, 1H). $^{19}$F NMR (376 MHz, DMSO-d$_6$) −96.67, −112.76.

Example 641: (R)-2-(1-(4-(4-Chloro-1-(difluoromethyl)-1H-1,2,3-triazol-5-yl)-1H-pyrazol-1-yl)-2-cyclopropylethyl)-5-(3-chloro-2-fluoro-6-(1H-tetrazol-1-yl)phenyl)pyridine 1-oxide

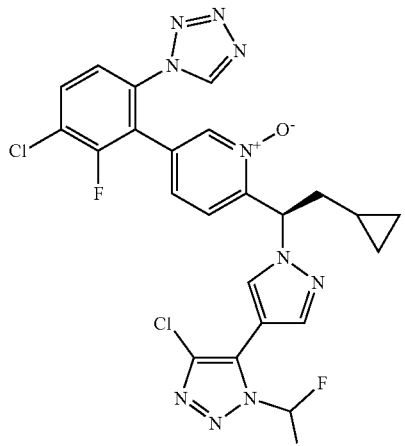

Step 1: 2-(1-(4-(4-Chloro-1-(difluoromethyl)-1H-1,2,3-triazol-5-yl)-1H-pyrazol-1-yl)-2-cyclopropylethyl)-5-(3-chloro-2-fluoro-6-(1H-tetrazol-1-yl)phenyl)pyridine and 2-(1-(4-(5-chloro-1-(difluoromethyl)-1H-1,2,3-triazol-4-yl)-1H-pyrazol-1-yl)-2-cyclopropylethyl)-5-(3-chloro-2-fluoro-6-(1H-tetrazol-1-yl)phenyl)pyridine To a solution of the mixture of 5-(3-chloro-2-fluoro-6-(1H-tetrazol-1-yl)phenyl)-2-(2-cyclopropyl-1-(4-(1-(difluoromethyl)-1H-1,2,3-triazol-5-yl)-1H-pyrazol-1-yl)ethyl)pyridine and 5-(3-chloro-2-fluoro-6-(1H-tetrazol-1-yl)phenyl)-2-(2-cyclopropyl-1-(4-(1-(difluoromethyl)-1H-1,2,3-triazol-4-yl)-1H-pyrazol-1-yl)ethyl)pyridine (200 mg, 0.38 mmol, 1.0 equiv.) in N,N-dimethylformamide (5 mL) was added NCS (253 mg, 1.90 mmol, 5.0 equiv.). The reaction mixture was stirred 5 h at room temperature, then purified by reverse column chromatography on C18 (120 g, MeCN/H$_2$O (0.05% CF$_3$COOH): 5→80%) to yield a mixture of 2-(1-(4-(4-chloro-1-(difluoromethyl)-1H-1,2,3-triazol-5-yl)-1H-pyrazol-1-yl)-2-cyclopropylethyl)-5-(3-chloro-2-fluoro-6-(1H-tetrazol-1-yl)phenyl)pyridine and 2-(1-(4-(5-chloro-1-(difluoromethyl)-1H-1,2,3-triazol-4-yl)-1H-pyrazol-1-yl)-2-cyclopropylethyl)-5-(3-chloro-2-fluoro-6-(1H-tetrazol-1-yl)phenyl)pyridine as a red solid. LC/MS: mass calculated for C$_{23}$H$_{17}$Cl$_2$F$_3$N$_{10}$: 560.10, measured (ES, m/z): 561.20 [M+H]$^+$.

Step 2: (R)-2-(1-(4-(5-Chloro-1-(difluoromethyl)-1H-1,2,3-triazol-4-yl)-1H-pyrazol-1-yl)-2-cyclopropylethyl)-5-(3-chloro-2-fluoro-6-(1H-tetrazol-1-yl)phenyl)pyridine 1-oxide A solution of the mixture of 2-(1-(4-(4-chloro-1-(difluoromethyl)-1H-1,2,3-triazol-5-yl)-1H-pyrazol-1-yl)-2-cyclopropylethyl)-5-(3-chloro-2-fluoro-6-(1H-tetrazol-1-yl)phenyl)pyridine and 2-(1-(4-(5-chloro-1-(difluoromethyl)-1H-1,2,3-triazol-4-yl)-1H-pyrazol-1-yl)-2-cyclopropylethyl)-5-(3-chloro-2-fluoro-6-(1H-tetrazol-1-yl)phenyl)pyridine (120 mg, 0.21 mmol, 1.0 equiv.), methylrhenium (VII) trioxide (11 mg, 0.04 mmol, 0.2 equiv.) and hydrogen peroxide (30 wt %, 242 mg, 2.14 mmol, 10.0 equiv.) in CH$_3$OH (3 mL) was stirred 1H at room temperature. The mixture was purified by reverse column chromatography on C18 (120 g, MeCN/H$_2$O (0.05% CF$_3$COOH): 5→80%) to yield 2-(1-(4-(4-chloro-1-(difluoromethyl)-1H-1,2,3-triazol-5-yl)-1H-pyrazol-1-yl)-2-cyclopropylethyl)-5-(3-chloro-2-fluoro-6-(1H-tetrazol-1-yl)phenyl)pyridine 1-oxide an off-white solid and 2-(1-(4-(5-chloro-1-(difluoromethyl)-1H-1,2,3-triazol-4-yl)-1H-pyrazol-1-yl)-2-cyclopropylethyl)-5-(3-chloro-2-fluoro-6-(1H-tetrazol-1-yl)phenyl)pyridine 1-oxide as an off-white solid. 2-(1-(4-(5-Chloro-1-(difluoromethyl)-1H-1,2,3-triazol-4-yl)-1H-pyrazol-1-yl)-2-cyclopropylethyl)-5-(3-chloro-2-fluoro-6-(1H-tetrazol-1-yl)phenyl)pyridine 1-oxide was purified by Prep-Chiral-HPLC with MtBE(0.1% DEA):EtOH=50:50 to yield (R)-2-(1-(4-(5-Chloro-1-(difluoromethyl)-1H-1,2,3-triazol-4-yl)-1H-pyrazol-1-yl)-2-cyclopropylethyl)-5-(3-chloro-2-fluoro-6-(1H-tetrazol-1-yl)phenyl)pyridine 1-oxide as an off-white solid.

LC/MS: mass calculated for C$_{23}$H$_{17}$Cl$_2$F$_3$N$_{10}$O: 576.10, measured (ES, m/z): 577.05 [M+H]$^+$. $^1$H NMR (400 MHz, DMSO-d$_6$): δ9.70 (s, 1H), 8.64 (s, 1H), 8.14-8.48 (m, 2H), 8.02-8.11 (m, 1H), 8.00 (s, 1H), 7.70-7.81 (m, 1H), 7.44 (d, J=8.3 Hz, 1H), 7.14-7.25 (m, 1H), 6.15-6.28 (m, 1H), 2.20-2.32 (m, 1H), 1.97-2.10 (m, 1H), 0.50-0.65 (m, 1H), 0.22-0.41 (m, 2H), 0.05-0.17 (m, 1H), −0.05--0.15 (m, 1H).

Example 642: (R)-2-(1-(4-(4-Chloro-1-(difluoromethyl)-1H-1,2,3-triazol-5-yl)-1H-pyrazol-1-yl)-2-(4-fluorophenyl)ethyl)-5-(3-chloro-2-fluoro-6-(1H-tetrazol-1-yl)phenyl)pyridine 1-oxide

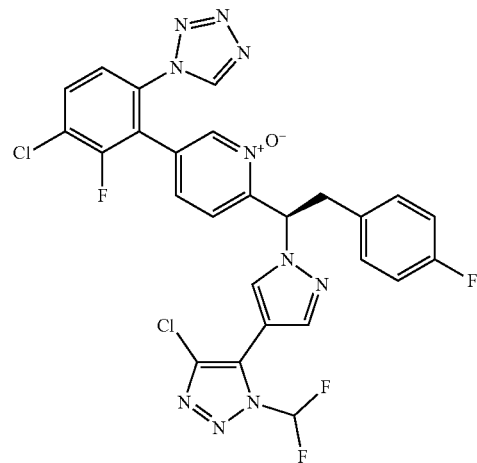

Step 1: 2-(1-(4-(5-Chloro-1-(difluoromethyl)-1H-1,2,3-triazol-4-yl)-1H-pyrazol-1-yl)-2-(4-fluorophenyl)ethyl)-5-(3-chloro-2-fluoro-6-(1H-tetrazol-1-yl)phenyl)pyridine and 2-(1-(4-(4-chloro-1-(difluoromethyl)-1H-1,2,3-triazol-5-yl)-1H-pyrazol-1-yl)-2-(4-fluorophenyl)ethyl)-5-(3-chloro-2-fluoro-6-(1H-tetrazol-1-yl)phenyl)pyridine To a solution of the mixture of 5-(3-chloro-2-fluoro-6-(1H-tetrazol-1-yl)phenyl)-2-(1-(4-(1-(difluoromethyl)-1H-1,2,3-triazol-5-yl)-1H-pyrazol-1-yl)-2-(4-fluorophenyl)ethyl)pyridine and 5-(3-chloro-2-fluoro-6-(1H-tetrazol-1-yl)phenyl)-2-(1-(4-(1-(difluoromethyl)-1H-1,2,3-triazol-5-yl)-1H-pyrazol-1-yl)-2-(4-fluorophenyl)ethyl)pyridine (300 mg, 0.52 mmol, 1.0 equiv.) in N,N-dimethylformamide (10 mL) was added NCS (345 mg, 2.58 mmol, 5.0 equiv.). The reaction mixture was stirred 5 h at room temperature, then purified by reverse column chromatography on C18 (5→80%, MeCN/H$_2$O (0.05% CF$_3$COOH)) to yield a mixture of 2-(1-(4-(5-chloro-1-(difluoromethyl)-1H-1,2,3-triazol-4-yl)-1H-pyrazol-1-yl)-2-(4-fluorophenyl)ethyl)-5-(3-chloro-2-fluoro-6-(1H-tetrazol-1-yl)phenyl)pyridine and 2-(1-(4-(4-chloro-1-(difluoromethyl)-1H-1,2,3-triazol-5-yl)-1H-pyrazol-1-yl)-2-(4-fluorophenyl)ethyl)-5-(3-chloro-2-fluoro-6-(1H-tetrazol-1-yl)phenyl)pyridine as a yellow solid. LC/MS: mass calculated for C$_{26}$H$_{16}$Cl$_2$F$_4$N$_{10}$: 614.09, measured (ES, m/z): 615.15 [M+H]$^+$.

Step 2: (R)-2-(1-(4-(4-Chloro-1-(difluoromethyl)-1H-1,2,3-triazol-5-yl)-1H-pyrazol-1-yl)-2-(4-fluorophenyl)ethyl)-5-(3-chloro-2-fluoro-6-(1H-tetrazol-1-yl)phenyl)pyridine 1-oxide A solution of the mixture of 2-(1-(4-(5-chloro-1-(difluoromethyl)-1H-1,2,3-triazol-4-yl)-1H-pyrazol-1-yl)-2-(4-fluorophenyl)ethyl)-5-(3-chloro-2-fluoro-6-(1H-tetrazol-1-yl)phenyl)pyridine and 2-(1-(4-(4-chloro-1-

(difluoromethyl)-1H-1,2,3-triazol-5-yl)-1H-pyrazol-1-yl)-2-(4-fluorophenyl)ethyl)-5-(3-chloro-2-fluoro-6-(1H-tetrazol-1-yl)phenyl)pyridine (230 mg, 0.37 mmol, 1.0 equiv.), methylrhenium (VII) trioxide (18 mg, 0.08 mmol, 0.2 equiv.) and hydrogen peroxide (30 wt %, 423 mg, 3.74 mmol, 10.0 equiv.) in CH$_3$OH (5 mL) was stirred 1 h at room temperature. The mixture was purified by reverse column chromatography on C18 (5→80%, MeCN/H$_2$O (0.05% CF$_3$COOH) to yield 2-(1-(4-(4-chloro-1-(difluoromethyl)-1H-1,2,3-triazol-5-yl)-1H-pyrazol-1-yl)-2-(4-fluorophenyl)ethyl)-5-(3-chloro-2-fluoro-6-(1H-tetrazol-1-yl)phenyl)pyridine 1-oxide as an off-white solid, which was purified by Prep-Chiral-HPLC with MtBE(0.1% DEA)MeOH=50:50 to yield (R)-2-(1-(4-(4-Chloro-1-(difluoromethyl)-1H-1,2,3-triazol-5-yl)-1H-pyrazol-1-yl)-2-(4-fluorophenyl)ethyl)-5-(3-chloro-2-fluoro-6-(1H-tetrazol-1-yl)phenyl)pyridine 1-oxide as an light yellow solid.

LC/MS: mass calculated for C$_{26}$H$_{16}$Cl$_2$F$_4$N$_{10}$O: 630.08, measured (ES, m/z): 631.05 [M+H]$^+$. $^1$H NMR (400 MHz, DMSO-d$_6$): 9.71 (s, 1H), 8.49 (d, J=1.6 Hz, 1H), 8.02-8.41 (m, 3H), 7.99 (s, 1H), 7.71-7.82 (m, 1H), 7.58 (d, J=8.3 Hz, 1H), 7.20-7.30 (m, 1H), 7.11-7.19 (m, 2H), 6.99-7.13 (m, 2H), 6.33 (t, J=7.4 Hz, 1H), 3.57 (d, J=7.5 Hz, 2H).

Example 643: (R)-5-(3-Chloro-2-fluoro-6-(1H-tetrazol-1-yl)phenyl)-2-(2-cyclopropyl-1-(4-(2-(difluoromethyl)-2H-1,2,3-triazol-4-yl)-1H-pyrazol-1-yl)ethyl)pyridine 1-oxide

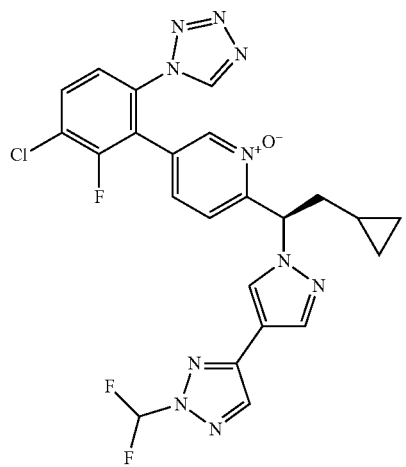

Step 1: 2-(1-(4-(1H-1,2,3-Triazol-5-yl)-1H-pyrazol-1-yl)-2-cyclopropylethyl)-5-bromopyridine To a stirred solution of 5-bromo-2-(2-cyclopropyl-1-(4-ethynyl-1H-pyrazol-1-yl)ethyl)pyridine (1.5 g, 4.7 mmol, 1.0 equiv.) and azidotrimethylsilane (5.5 g, 47.4 mmol, 10.0 equiv.) in N,N-dimethylacetamide (30 mL) was added CuSO$_4$.5H$_2$O (0.36 g, 1.42 mmol, 0.3 equiv.) and sodium ascorbate (0.28 g, 1.42 mmol, 0.3 equiv.). The mixture was stirred at 35° C. for 16 h, then quenched with water, and extracted with ethyl acetate twice. The combined organic layers were dried over anhydrous sodium sulfate and concentrated under vacuum. The residue was applied onto a silica gel column (0→100% EA/PE) to yield 2-(1-(4-(1H-1,2,3-triazol-5-yl)-1H-pyrazol-1-yl)-2-cyclopropylethyl)-5-bromopyridine as a light yellow solid. LC/MS: mass calculated for C$_{15}$H$_{15}$BrN$_6$: 358.05, measured (ES, m/z): 359.05, 361.05 [M+H, M+H+2]$^+$.

Step 2: 5-Bromo-2-(2-cyclopropyl-1-(4-(1-(difluoromethyl)-1H-1,2,3-triazol-5-yl)-1H-pyrazol-1-yl)ethyl)pyridine, 5-bromo-2-(2-cyclopropyl-1-(4-(2-(difluoromethyl)-2H-1,2,3-triazol-4-yl)-1H-pyrazol-1-yl)ethyl)pyridine and 5-bromo-2-(2-cyclopropyl-1-(4-(2-(difluoromethyl)-2H-1,2,3-triazol-4-yl)-1H-pyrazol-1-yl)ethyl)pyridine A solution of 2-(1-(4-(1H-1,2,3-triazol-5-yl)-1H-pyrazol-1-yl)-2-cyclopropylethyl)-5-bromopyridine (1.0 g, 2.8 mmol, 1.0 equiv.), sodium 2-chloro-2,2-difluoroacetate (0.64 g, 4.18 mmol, 1.5 equiv.) and cesium carbonate (2.7 g, 8.4 mmol, 3.0 equiv.) in N,N-dimethylacetamide (30 mL) under nitrogen atmosphere was stirred for 1 h at 70° C. After the mixture was cooled to room temperature, water (50 mL) was added. The resulting mixture was extracted with ethyl acetate twice. The organic layers were combined, dried over anhydrous sodium sulfate, filtered, and concentrated. The resulting residue was purified by silica gel chromatography (0→20% EA/PE) to yield a mixture of 5-bromo-2-(2-cyclopropyl-1-(4-(1-(difluoromethyl)-1H-1,2,3-triazol-5-yl)-1H-pyrazol-1-yl)ethyl)pyridine, 5-bromo-2-(2-cyclopropyl-1-(4-(1-(difluoromethyl)-1H-1,2,3-triazol-4-yl)-1H-pyrazol-1-yl)ethyl)pyridine and 5-bromo-2-(2-cyclopropyl-1-(4-(2-(difluoromethyl)-2H-1,2,3-triazol-4-yl)-1H-pyrazol-1-yl)ethyl)pyridine as colorless oil. LC/MS: mass calculated for C$_{16}$H$_{15}$BrF$_2$N$_6$: 408.05, measured (ES, m/z): 409.05, 410.05 [M+H, M+H+2]$^+$.

Step 3: 4-Chloro-2-(6-(2-cyclopropyl-1-(4-(1-(difluoromethyl)-1H-1,2,3-triazol-5-yl)-1H-pyrazol-1-yl)ethyl)pyridin-3-yl)-3-fluoroaniline, 4-chloro-2-(6-(2-cyclopropyl-1-(4-(1-(difluoromethyl)-1H-1,2,3-triazol-4-yl)-1H-pyrazol-1-yl)ethyl)pyridin-3-yl)-3-fluoroaniline and 4-chloro-2-(6-(2-cyclopropyl-1-(4-(2-(difluoromethyl)-2H-1,2,3-triazol-4-yl)-1H-pyrazol-1-yl)ethyl)pyridin-3-yl)-3-fluoroaniline To a solution of the mixture of 5-bromo-2-(2-cyclopropyl-1-(4-(1-(difluoromethyl)-1H-1,2,3-triazol-5-yl)-1H-pyrazol-1-yl)ethyl)pyridine, 5-bromo-2-(2-cyclopropyl-1-(4-(1-(difluoromethyl)-1H-1,2,3-triazol-4-yl)-1H-pyrazol-1-yl)ethyl)pyridine and 5-bromo-2-(2-cyclopropyl-1-(4-(2-(difluoromethyl)-2H-1,2,3-triazol-4-yl)-1H-pyrazol-1-yl)ethyl)pyridine (1.0 g, 2.44 mmol, 1.0 equiv.) in 1,4-dioxane (13 mL) and water (1 mL) was added (6-amino-3-chloro-2-fluorophenyl)boronic acid (833 mg, 4.40 mmol, 1.8 equiv.) tetrakis(triphenylphosphine)palladium (282 mg, 0.24 mmol, 0.1 equiv.) and potassium carbonate (1.0 g, 7.33 mmol, 3.0 equiv.). The reaction mixture was stirred at 100° C. for 2 h, then quenched with water, and extracted with ethyl acetate twice. The combined organic layers were dried over anhydrous sodium sulfate and concentrated under vacuum. The residue was applied onto a silica gel column (0→100% EA/PE) to yield a mixture of 4-chloro-2-(6-(2-cyclopropyl-1-(4-(1-(difluoromethyl)-1H-1,2,3-triazol-5-yl)-1H-pyrazol-1-yl)ethyl)pyridin-3-yl)-3-fluoroaniline, 4-chloro-2-(6-(2-cyclopropyl-1-(4-(1-(difluoromethyl)-1H-1,2,3-triazol-4-yl)-1H-pyrazol-1-yl)ethyl)pyridin-3-yl)-3-fluoroaniline and 4-chloro-2-(6-(2-cyclopropyl-1-(4-(2-(difluoromethyl)-2H-1,2,3-triazol-4-yl)-1H-pyrazol-1-yl)ethyl)

pyridin-3-yl)-3-fluoroaniline as light yellow oil. LC/MS: mass calculated for $C_{22}H_{19}ClF_3N_7$: 473.13, measured (ES, m/z): 474.20 [M+H]+.

Step 4: 5-(3-Chloro-2-fluoro-6-(1H-tetrazol-1-yl)phenyl)-2-(2-cyclopropyl-1-(4-(2-(difluoromethyl)-2H-1,2,3-triazol-4-yl)-1H-pyrazol-1-yl)ethyl)pyridine, the mixture of 5-(3-chloro-2-fluoro-6-(1H-tetrazol-1-yl)phenyl)-2-(2-cyclopropyl-1-(4-(1-(difluoromethyl)-1H-1,2,3-triazol-5-yl)-1H-pyrazol-1-yl)ethyl)pyridine and 5-(3-chloro-2-fluoro-6-(1H-tetrazol-1-yl)phenyl)-2-(2-cyclopropyl-1-(4-(1-(difluoromethyl)-1H-1,2,3-triazol-4-yl)-1H-pyrazol-1-yl)ethyl)pyridine To a solution of the mixture of 4-chloro-2-(6-(2-cyclopropyl-1-(4-(1-(difluoromethyl)-1H-1,2,3-triazol-5-yl)-1H-pyrazol-1-yl)ethyl)pyridin-3-yl)-3-fluoroaniline, 4-chloro-2-(6-(2-cyclopropyl-1-(4-(1-(difluoromethyl)-1H-1,2,3-triazol-4-yl)-1H-pyrazol-1-yl)ethyl)pyridin-3-yl)-3-fluoroaniline and 4-chloro-2-(6-(2-cyclopropyl-1-(4-(2-(difluoromethyl)-2H-1,2,3-triazol-4-yl)-1H-pyrazol-1-yl)ethyl)pyridin-3-yl)-3-fluoroaniline (1.0 g, 2.11 mmol, 1.0 equiv.) in acetic acid (15 mL) was added trimethoxymethane (2.2 g, 21.1 mmol, 10.0 equiv.) and azidotrimethylsilane (2.4 g, 21.1 mmol, 10.0 equiv.). The resulting mixture was stirred overnight at room temperature, then concentrated under vacuum. The residue was purified by reverse column chromatography on C18 (120 g, MeCN/$H_2O$ (0.05% $CF_3COOH$): 5→80%) to yield 5-(3-chloro-2-fluoro-6-(1H-tetrazol-1-yl)phenyl)-2-(2-cyclopropyl-1-(4-(2-(difluoromethyl)-2H-1,2,3-triazol-4-yl)-1H-pyrazol-1-yl)ethyl)pyridine as a light yellow solid, and a mixture of 5-(3-chloro-2-fluoro-6-(1H-tetrazol-1-yl)phenyl)-2-(2-cyclopropyl-1-(4-(1-(difluoromethyl)-1H-1,2,3-triazol-5-yl)-1H-pyrazol-1-yl)ethyl)pyridine and 5-(3-chloro-2-fluoro-6-(1H-tetrazol-1-yl)phenyl)-2-(2-cyclopropyl-1-(4-(1-(difluoromethyl)-1H-1,2,3-triazol-4-yl)-1H-pyrazol-1-yl)ethyl)pyridine as an light yellow solid. LC/MS: mass calculated for $C_{23}H_{18}ClF_3N_{10}$: 526.14, measured (ES, m/z): 527.20 [M+H]+.

Step 5: (R)-5-(3-Chloro-2-fluoro-6-(1H-tetrazol-1-yl)phenyl)-2-(2-cyclopropyl-1-(4-(2-(difluoromethyl)-2H-1,2,3-triazol-4-yl)-1H-pyrazol-1-yl)ethyl)pyridine 1-oxide A solution of 5-(3-chloro-2-fluoro-6-(1H-tetrazol-1-yl)phenyl)-2-(2-cyclopropyl-1-(4-(2-(difluoromethyl)-2H-1,2,3-triazol-4-yl)-1H-pyrazol-1-yl)ethyl)pyridine (120 mg, 0.23 mmol, 1.0 equiv.), methylrhenium (VII) trioxide (11 mg, 0.05 mmol, 0.2 equiv.) and hydrogen peroxide (30 wt %, 258 mg, 2.23 mmol, 10.0 equiv.) in $CH_3OH$ (2 mL) was stirred 1 h at room temperature. The mixture was purified by reverse column chromatography on C18 (120 g, MeCN/$H_2O$ (0.05% $CF_3COOH$): 5→80%) to yield 5-(3-chloro-2-fluoro-6-(1H-tetrazol-1-yl)phenyl)-2-(2-cyclopropyl-1-(4-(2-(difluoromethyl)-2H-1,2,3-triazol-4-yl)-1H-pyrazol-1-yl)ethyl)pyridine 1-oxide as an off-white solid. The racemic mixture was purified by Prep-Chiral-HPLC with MtBE(0.1% DEA): EtOH=50:50 to yield (R)-5-(3-Chloro-2-fluoro-6-(1H-tetrazol-1-yl)phenyl)-2-(2-cyclopropyl-1-(4-(2-(difluoromethyl)-2H-1,2,3-triazol-4-yl)-1H-pyrazol-1-yl)ethyl)pyridine 1-oxide.

LC/MS: mass calculated for $C_{23}H_{18}ClF_3N_{10}O$: 542.13, measured (ES, m/z): 543.10 [M+H]+. $^1$H NMR (400 MHz, DMSO-$d_6$): δ 9.69 (s, 1H), 8.63 (s, 1H), 8.40-8.46 (m, 2H), 7.94-8.32 (m, 3H), 7.71-7.80 (m, 1H), 7.31 (d, J=8.3 Hz, 1H), 7.12-7.20 (m, 1H), 6.08-6.16 (m, 1H), 2.33-2.43 (m, 1H), 1.88-2.00 (m, 1H), 0.52-0.65 (m, 1H), 0.27-0.40 (m, 2H), 0.08-0.18 (m, 1H), −0.08-0.00 (m, 1H)

Example 644: (S)-2-(1-(4-(5-Chloro-1-(difluoromethyl)-1H-1,2,3-triazol-4-yl)-1H-pyrazol-1-yl)-2-cyclopropylethyl)-5-(3-chloro-2-fluoro-6-(1H-tetrazol-1-yl)phenyl)pyridine 1-oxide

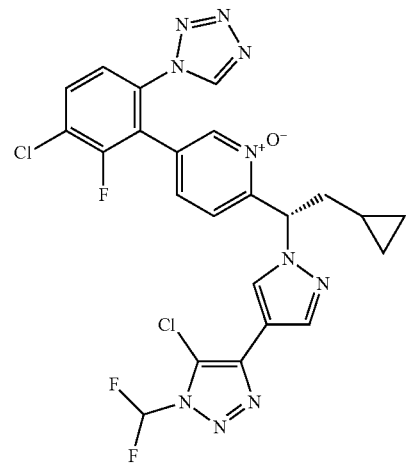

LC/MS: mass calculated for $C_{23}H_{17}Cl_2F_3N_{10}O$: 576.10, measured (ES, m/z): 577.05 [M+H]+. $^1$H NMR (400 MHz, DMSO-$d_6$) δ 9.70 (s, 1H), 8.63 (s, 1H), 8.15-8.46 (m, 2H), 8.04-8.08 (m, 1H), 8.00 (s, 1H), 7.74-7.77 (m, 1H), 7.42-7.44 (m, 1H), 7.18-7.20 (m, 1H), 6.19-6.23 (m, 1H), 2.22-2.50 (m, 1H), 2.07-1.98 (m, 1H), 0.50-0.67 (m, 1H), 0.20-0.40 (m, 2H), 0.05-0.15 (m, 1H), −0.15-−0.05 (m, 1H). $^{19}$F NMR (376 MHz, DMSO-$d_6$) δ −97.49, −112.71.

Example 645: (S)-2-(1-(4-(5-Chloro-2-(difluoromethyl)-2H-1,2,3-triazol-4-yl)-1H-pyrazol-1-yl)-2-(4-fluorophenyl)ethyl)-5-(3-chloro-2-fluoro-6-(1H-tetrazol-1-yl)phenyl)pyridine 1-oxide

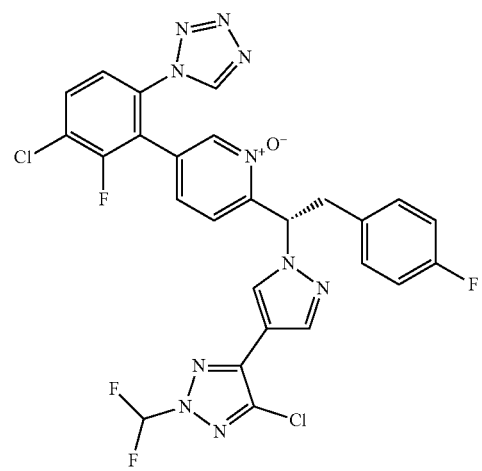

LC/MS: mass calculated for $C_{26}H_{16}Cl_2F_4N_{10}O$: 630.08, measured (ES, m/z): 631.05 [M+H]+. $^1$H NMR (400 MHz, DMSO-d$_6$) δ 9.71 (s, 1H), 8.43 (d, J=6.8 Hz, 2H), 7.98-8.31 (m, 3H), 7.76-7.78 (m, 2H), 7.26-7.28 (m, 1H), 7.00-7.14 (m, 4H), 6.25-6.29 (m, 1H), 3.44-3.72 (m, 2H). $^{19}$F NMR (376 MHZ, DMSO-d$_6$) δ −96.60, −112.59, −115.74.

Example 646: (S)-2-(1-(4-(5-Chloro-2-(difluoromethyl)-2H-1,2,3-triazol-4-yl)-1H-pyrazol-1-yl)-2-cyclopropylethyl)-5-(3-chloro-2-fluoro-6-(1H-tetrazol-1-yl)phenyl)pyridine 1-oxide

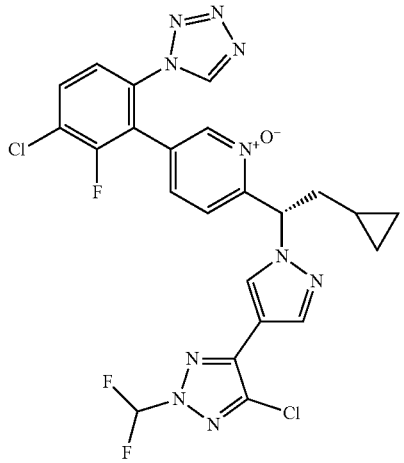

LC/MS: mass calculated for C$_{23}$H$_{17}$Cl$_2$F$_3$N$_{10}$O: 576.10, measured (ES, m/z): 577.05 [M+H]$^+$. $^1$H NMR (400 MHz, DMSO-d$_6$) δ 9.69 (s, 1H), 8.53 (s, 1H), 8.40 (m, 1H), 8.01-8.36 (m, 3H), 7.76 (dd, J=8.7, 1.5 Hz, 1H), 7.52 (d, J=8.3 Hz, 1H), 7.21 (dd, J=8.3, 1.7 Hz, 1H), 6.23-6.27 (m, 1H), 2.23-2.30 (m, 1H), 1.93-1.99 (m, 1H), 0.50-0.60 (m, 2H), 0.21-0.42 (m, 1H), 0.10-0.20 (m, 1H), −0.20-−0.10 (m, 1H). $^{19}$F NMR (376 MHz, DMSO-d$_6$) δ −97.17, −112.70.

Example 647: (R)-2-(1-(4-(5-Chloro-1-(difluoromethyl)-1H-1,2,3-triazol-4-yl)-1H-pyrazol-1-yl)-2-(4-fluorophenyl)ethyl)-5-(3-chloro-2-fluoro-6-(1H-tetrazol-1-yl)phenyl)pyridine 1-oxide

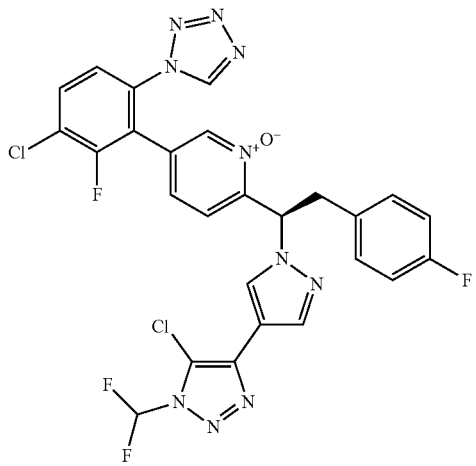

LC/MS: mass calculated for C$_{26}$H$_{16}$Cl$_2$F$_4$N$_{10}$O: 630.08, measured (ES, m/z): 631.05 [M+H]$^+$. $^1$H NMR (400 MHz, DMSO-d$_6$) δ 9.72 (s, 1H), 8.87 (s, 1H), 8.05-8.43 (m, 4H), 7.73-7.78 (m, 2H), 7.28 (dd, J=8.3, 1.7 Hz, 1H), 7.01-7.10 (m, 4H), 6.25-6.29 (m, 1H), 3.37-3.75 (m, 2H). $^{19}$F NMR (376 MHz, DMSO-d$_6$) δ −96.56, −112.65, −115.83.

Example 648: (S)-2-(1-(4-(4-Chloro-1-(difluoromethyl)-1H-1,2,3-triazol-5-yl)-1H-pyrazol-1-yl)-2-cyclopropylethyl)-5-(3-chloro-2-fluoro-6-(1H-tetrazol-1-yl)phenyl)pyridine 1-oxide

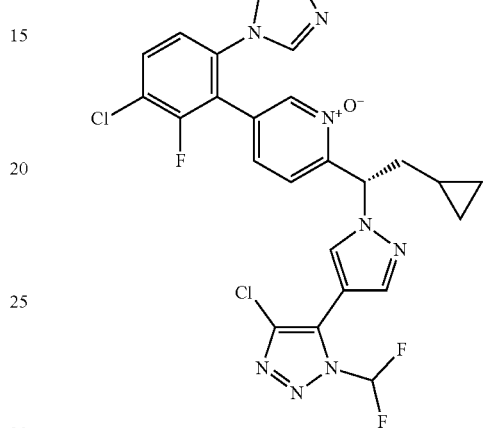

Step 1: 2-(1-(4-(4-Chloro-1-(difluoromethyl)-1H-1,2,3-triazol-5-yl)-1H-pyrazol-1-yl)-2-cyclopropylethyl)-5-(3-chloro-2-fluoro-6-(1H-tetrazol-1-yl)phenyl)pyridine and 2-(1-(4-(5-chloro-1-(difluoromethyl)-1H-1,2,3-triazol-4-yl)-1H-pyrazol-1-yl)-2-cyclopropylethyl)-5-(3-chloro-2-fluoro-6-(1H-tetrazol-1-yl)phenyl)pyridine To a solution of the mixture of 5-(3-chloro-2-fluoro-6-(1H-tetrazol-1-yl)phenyl)-2-(2-cyclopropyl-1-(4-(1-(difluoromethyl)-1H-1,2,3-triazol-5-yl)-1H-pyrazol-1-yl)ethyl)pyridine and 5-(3-chloro-2-fluoro-6-(1H-tetrazol-1-yl)phenyl)-2-(2-cyclopropyl-1-(4-(1-(difluoromethyl)-1H-1,2,3-triazol-4-yl)-1H-pyrazol-1-yl)ethyl)pyridine (200 mg, 0.38 mmol, 1.0 equiv.) in N,N-dimethylformamide (5 mL) was added N-chlorosuccinimide (253 mg, 1.90 mmol, 5.0 equiv.). The reaction mixture was stirred 5 h at room temperature, then purified by reverse column chromatography on C18 (120 g, MeCN/H$_2$O (0.05% CF$_3$COOH): 5→80%) to yield a mixture of 2-(1-(4-(4-chloro-1-(difluoromethyl)-1H-1,2,3-triazol-5-yl)-1H-pyrazol-1-yl)-2-cyclopropylethyl)-5-(3-chloro-2-fluoro-6-(1H-tetrazol-1-yl)phenyl)pyridine and 2-(1-(4-(5-chloro-1-(difluoromethyl)-1H-1,2,3-triazol-4-yl)-1H-pyrazol-1-yl)-2-cyclopropylethyl)-5-(3-chloro-2-fluoro-6-(1H-tetrazol-1-yl)phenyl)pyridine as a red solid. LC/MS: mass calculated for C$_{23}$H$_{17}$Cl$_2$F$_3$N$_{10}$: 560.10, measured (ES, m/z): 561.20 [M+H]$^+$.

Step 2: (S)-2-(1-(4-(4-Chloro-1-(difluoromethyl)-1H-1,2,3-triazol-5-yl)-1H-pyrazol-1-yl)-2-cyclopropylethyl)-5-(3-chloro-2-fluoro-6-(1H-tetrazol-1-yl)phenyl)pyridine 1-oxide A solution of the mixture of 2-(1-(4-(4-chloro-1-(difluoromethyl)-1H-1,2,3-triazol-5-yl)-1H-pyrazol-1-yl)-2-cyclopropylethyl)-5-(3-chloro-2-fluoro-6-(1H-tetrazol-1-yl)phenyl)pyridine and 2-(1-(4-(5-chloro-1-(difluoromethyl)-1H-1,2,3-triazol-4-yl)-1H-pyrazol-1-yl)-2-cyclopropylethyl)-5-(3-chloro-2-fluoro-6-(1H-tetrazol-1-yl)phenyl)pyridine (120 mg, 0.21 mmol, 1.0 equiv.), methylrhenium (VII) trioxide (11 mg, 0.04 mmol, 0.2 equiv.) and hydrogen peroxide (30 wt %, 242 mg, 2.14 mmol, 10.0 equiv.) in CH₃OH (3 mL) was stirred 1 h at room temperature. The mixture was purified by reverse column chromatography on C18 (120 g, MeCN/H₂O (0.05% CF₃COOH): 5→80%) to yield 2-(1-(4-(4-chloro-1-(difluoromethyl)-1H-1,2,3-triazol-5-yl)-1H-pyrazol-1-yl)-2-cyclopropylethyl)-5-(3-chloro-2-fluoro-6-(1H-tetrazol-1-yl)phenyl)pyridine 1-oxide an off-white solid and 2-(1-(4-(5-chloro-1-(difluoromethyl)-1H-1,2,3-triazol-4-yl)-1H-pyrazol-1-yl)-2-cyclopropylethyl)-5-(3-chloro-2-fluoro-6-(1H-tetrazol-1-yl)phenyl)pyridine 1-oxide as an off-white solid. 2-(1-(4-(4-Chloro-1-(difluoromethyl)-1H-1,2,3-triazol-5-yl)-1H-pyrazol-1-yl)-2-cyclopropylethyl)-5-(3-chloro-2-fluoro-6-(1H-tetrazol-1-yl)phenyl)pyridine 1-oxide was purified by Prep-Chiral-HPLC with MtBE(0.1% DEA)MeOH=50:50 to yield (S)-2-(1-(4-(4-chloro-1-(difluoromethyl)-1H-1,2,3-triazol-5-yl)-1H-pyrazol-1-yl)-2-cyclopropylethyl)-5-(3-chloro-2-fluoro-6-(1H-tetrazol-1-yl)phenyl)pyridine 1-oxide as a light yellow solid.

LC/MS: mass calculated for $C_{23}H_{17}Cl_2F_3N_{10}O$: 576.10, measured (ES, m/z): 577.05 [M+H]⁺. ¹H NMR (400 MHz, DMSO-d₆): δ9.69 (s, 1H), 8.99 (s, 1H), 8.15-8.47 (m, 2H), 8.14 (s, 1H), 8.03-8.11 (m, 1H), 7.71-7.81 (m, 1H), 7.50 (d, J=8.3 Hz, 1H), 7.16-7.27 (m, 1H), 6.20-6.30 (m, 1H), 2.22-2.33 (m, 1H), 1.90-2.02 (m, 1H), 0.50-0.65 (m, 1H), 0.34-0.44 (m, 1H), 0.25-0.33 (m, 1H), 0.12-0.20 (m, 1H), −0.20−−0.10 (m, ¹H).

Example 649: 5-(3-Chloro-2-fluoro-6-(1H-tetrazol-1-yl)phenyl)-2-(2-cyclopropyl-1-(4-(3-methyl-1,2,4-oxadiazol-5-yl)-1H-pyrazol-1-yl)ethyl)pyridine 1-oxide

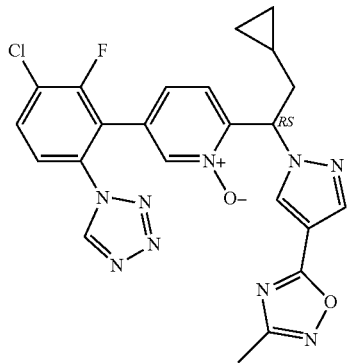 [SMILES: Cc1noc(-c2cnn(C(CC3CC3)c3ccc(-c4c(-n5cnnn5)ccc(Cl)c4F)c[n+]3[O-])c2)n1]

LC/MS: mass calculated for $C_{23}H_{19}ClFN_9O_2$: 507.1, measured (ES, m/z): 508.2 [M+H]⁺. ¹H NMR (400 MHz, CD₃OD) δ 9.38 (s, 1H), 8.69 (s, 1H), 8.36 (s, 1H), 8.15 (s, 1H), 7.86-7.98 (m, 1H), 7.59 (br d, J=7.58 Hz, 2H), 7.30 (br d, J=8.59 Hz, 1H), 6.28 (b dd, J=3.28, 9.85 Hz, 1H), 2.43-2.53 (m, 1H), 2.39 (s, 3H), 2.03-2.12 (m, 1H), 0.65 (bd, J=6.06 Hz, 1H), 0.33-0.51 (m, 2H), 0.14-0.24 (m, 1H), 0.00 (m, 1H).

Example 650: (S)-2-(1-(4-(2-Aminothiazol-5-yl)-1H-pyrazol-1-yl)-2-cyclopropylethyl)-5-(3-chloro-2-fluoro-6-(1H-tetrazol-1-yl)phenyl)pyridine 1-oxide

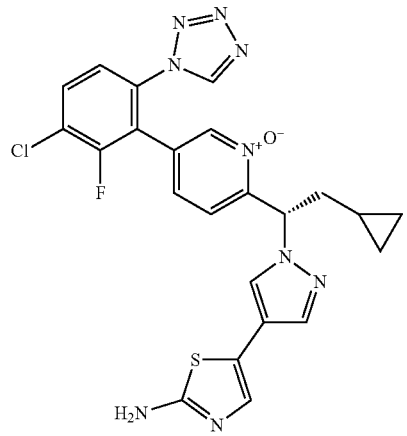

LC/MS: mass calculated for $C_{23}H_{19}ClFN_9OS$: 523.11, measured (ES, m/z): 524.1 [M+H]⁺. ¹H NMR (300 MHz, DMSO-d₆) δ 9.68 (s, 1H), 8.40 (s, 1H), 8.14 (s, 1H), 8.06 (dd, J=8.7, 7.8 Hz, 1H), 7.68-7.80 (m, 2H), 7.10-7.24 (m, 2H), 7.08 (s, 1H), 6.91 (s, 2H), 6.00-6.04 (m, 1H), 2.28-2.42 (m, 1H), 1.70-2.00 (m, 1H), 0.50-0.55 (m, 1H), 0.20-0.40 (m, 2H), 0.05-0.19 (m, 2H).

Example 651: (R)-2-(1-(4-(2-Aminothiazol-5-yl)-1H-pyrazol-1-yl)-2-cyclopropylethyl)-5-(3-chloro-2-fluoro-6-(1H-tetrazol-1-yl)phenyl)pyridine 1-oxide

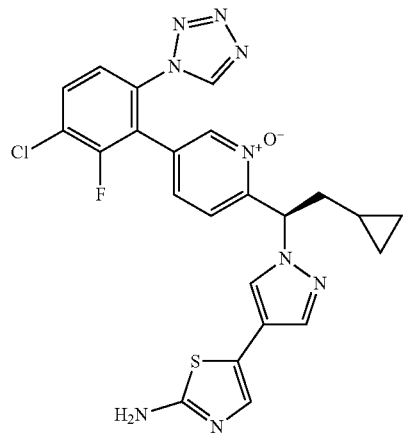

Step 1: tert-Butyl (5-(1H-pyrazol-4-yl)thiazol-2-yl)(4-methoxybenzyl)carbamate

To a solution of tert-butyl (5-bromothiazol-2-yl)(4-methoxybenzyl)carbamate (2.5 g, 6.26 mmol, 1.0 equiv.) in DMF (35 mL) and H₂O (6 mL) was added tert-butyl 4-(4,4,5,5-tetramethyl-1,3,2-dioxaborolan-2-yl)-1H-pyrazole-1-carboxylate (3.7 g, 12.52 mmol, 2.0 equiv.), K₂CO₃ (2.6 g, 18.78 mmol, 3.0 equiv.) and Pd(PPh₃)₄ (0.72 g, 0.62 mmol, 0.1 equiv.). The resulting mixture was maintained under nitrogen and stirred at 90° C. for 2 h. After cooling to room temperature, the reaction was quenched with water (200 mL). The resulting mixture was extracted with ethyl acetate (3×40 mL). The organic layers were combined, dried over anhydrous sodium sulfate, filtered, and concentrated. The resulting residue was purified by silica gel chromatography (0→70% EA/PE) to yield tert-butyl (5-(1H-pyrazol-4-yl)thiazol-2-yl)(4-methoxybenzyl)carbamate as a light pink solid. LC/MS: mass calculated for $C_{19}H_{22}N_4O_3S$: 386.14, measured (ES, m/z): 387.05 [M+H]$^+$.

Step 2: tert-Butyl (5-(1-(1-(5-bromopyridin-2-yl)-2-cyclopropylethyl)-1H-pyrazol-4-yl)thiazol-2-yl)(4-methoxybenzyl)carbamate To a solution of tert-butyl (5-(1H-pyrazol-4-yl)thiazol-2-yl)(4-methoxybenzyl)carbamate (700 mg, 1.81 mmol, 1.0 equiv.) in ACN (20 mL) was added $Cs_2CO_3$ (885 mg, 2.72 mmol, 1.5 equiv.) at room temperature. for 0.5 h. To the resulting mixture was added 1-(6-bromopyridin-3-yl)-2-cyclopropylethyl methanesulfonate (870 mg, 2.72 mmol, 1.5 equiv.). The resulting mixture was stirred at 80° C. for 2 h. The reaction was quenched with water (50 mL). The resulting mixture was extracted with ethyl acetate (3×20 mL). The organic layers were combined, dried over anhydrous sodium sulfate, filtered and concentrated. The resulting residue was purified by silica gel chromatography (0→40% EA/PE) to yield tert-butyl (5-(1-(1-(5-bromopyridin-2-yl)-2-cyclopropylethyl)-1H-pyrazol-4-yl)thiazol-2-yl)(4-methoxybenzyl)carbamate as a red brown oil. LC/MS: mass calculated for $C_{29}H_{32}BrN_5O_3S$: 609.14, measured (ES, m/z): 610.05, 612.05 [M+H, M+H+2]$^+$.

Step 3: tert-Butyl (5-(1-(1-(5-(6-amino-3-chloro-2-fluorophenyl)pyridin-2-yl)-2-cyclopropylethyl)-1H-pyrazol-4-yl)thiazol-2-yl)(4-methoxybenzyl)carbamate To a solution of tert-butyl (5-(1-(1-(5-bromopyridin-2-yl)-2-cyclopropylethyl)-1H-pyrazol-4-yl)thiazol-2-yl)(4-methoxybenzyl)carbamate (867 mg, 1.42 mmol, 1.0 equiv.) in 1,4-dioxane (25 mL) and $H_2O$ (2 mL) was added (6-amino-3-chloro-2-fluorophenyl)boronic acid (403 mg, 2.13 mmol, 1.5 equiv.), $K_2CO_3$ (589 mg, 4.26 mmol, 3.0 equiv.) and Pd(PPh$_3$)$_4$ (164 mg, 0.14 mmol, 0.1 equiv.). The resulting mixture was maintained under nitrogen and stirred at 90° C. for 2 h. After cooling to room temperature, the reaction was quenched with water (50 mL). The resulting mixture was extracted with ethyl acetate (3×25 mL). The organic layers were combined, dried over anhydrous sodium sulfate, filtered and concentrated. The resulting residue was purified by silica gel chromatography (0→50% EA/PE) to yield tert-butyl (5-(1-(1-(5-(6-amino-3-chloro-2-fluorophenyl)pyridin-2-yl)-2-cyclopropylethyl)-1H-pyrazol-4-yl)thiazol-2-yl)(4-methoxybenzyl)carbamate as a light yellow solid. LC/MS: mass calculated for $C_{35}H_{36}ClFN_6O_3S$: 674.22, measured (ES, m/z): 675.10 [M+H]$^+$.

Step 4: tert-Butyl (5-(1-(1-(5-(3-chloro-2-fluoro-6-(1H-tetrazol-1-yl)phenyl)pyridin-2-yl)-2-cyclopropylethyl)-1H-pyrazol-4-yl)thiazol-2-yl)(4-methoxybenzyl)carbamate To a solution of tert-butyl (5-(1-(1-(5-(6-amino-3-chloro-2-fluorophenyl)pyridin-2-yl)-2-cyclopropylethyl)-1H-pyrazol-4-yl)thiazol-2-yl)(4-methoxybenzyl)carbamate (500 mg, 0.74 mmol, 1.0 equiv.) in AcOH (3 mL) was added trimethoxymethane (2 mL) and TMSN$_3$ (2 mL). The resulting mixture was stirred at room temperature for 14 h. The reaction was purified by reverse phase chromatography on C18 (120 g, 5%→100%, MeCN/H$_2$O) to yield tert-butyl (5-(1-(1-(5-(3-chloro-2-fluoro-6-(1H-tetrazol-1-yl)phenyl)pyridin-2-yl)-2-cyclopropylethyl)-1H-pyrazol-4-yl)thiazol-2-yl)(4-methoxybenzyl)carbamate as a light yellow solid. LC/MS: mass calculated for $C_{36}H_{35}ClFN_9O_3S$: 727.23, measured (ES, m/z): 728.15 [M+H]$^+$.

Step 5: 5-(3-Chloro-2-fluoro-6-(1H-tetrazol-1-yl)phenyl)-2-(2-cyclopropyl-1-(4-(2-((4-methoxybenzyl)amino)thiazol-5-yl)-1H-pyrazol-1-yl)ethyl)pyridine 1-oxide To a solution of tert-butyl (5-(1-(1-(5-(3-chloro-2-fluoro-6-(1H-tetrazol-1-yl)phenyl)pyridin-2-yl)-2-cyclopropylethyl)-1H-pyrazol-4-yl)thiazol-2-yl)(4-methoxybenzyl)carbamate (200 mg, 0.28 mmol, 1.0 equiv.) in peroxyacetic acid (5 mL) was stirred at room temperature. for 14 h. The resulting residue was purified by reverse phase chromatography on C18 (80 g, 5%→50%, MeCN/H$_2$O) to yield 5-(3-chloro-2-fluoro-6-(1H-tetrazol-1-yl)phenyl)-2-(2-cyclopropyl-1-(4-(2-((4-methoxybenzyl)amino)thiazol-5-yl)-1H-pyrazol-1-yl)ethyl)pyridine 1-oxide as a yellow oil. LC/MS: mass calculated for $C_{31}H_{27}ClFN_9O_2S$: 643.17, measured (ES, m/z): 644.05 [M+H]$^+$.

Step 6: (R)-2-(1-(4-(2-Aminothiazol-5-yl)-1H-pyrazol-1-yl)-2-cyclopropylethyl)-5-(3-chloro-2-fluoro-6-(1H-tetrazol-1-yl)phenyl)pyridine 1-oxide To a solution of 5-(3-chloro-2-fluoro-6-(1H-tetrazol-1-yl)phenyl)-2-(2-cyclopropyl-1-(4-(2-((4-methoxybenzyl)amino)thiazol-5-yl)-1H-pyrazol-1-yl)ethyl)pyridine 1-oxide (100 mg, 0.16 mmol, 1.0 equiv.) TFA (4 mL) was stirred at 50° C. for 3 h. After cooling to room temperature, the reaction was purified by reverse phase chromatography on C$_{18}$ (120 g, 5%-*45%, MeCN/H$_2$O (0.05% CF$_3$COOH)) and Chiral HPLC to yield (R)-2-(1-(4-(2-aminothiazol-5-yl)-1H-pyrazol-1-yl)-2-cyclopropylethyl)-5-(3-chloro-2-fluoro-6-(1H-tetrazol-1-yl)phenyl)pyridine 1-oxide as a white solid LC/MS: mass calculated for $C_{23}H_{19}ClFN_9OS$: 523.11, measured (ES, m/z): 524.10 [M+H]$^+$. $^1$H NMR (300 MHz, DMSO-d$_6$) δ 9.68 (s, 1H), 8.40 (s, 1H), 8.15 (s, 1H), 8.06 (t, J=8.7 Hz, 1H), 7.75 (d, J=8.7 Hz, 1H), 7.71 (s, 1H), 7.12-7.21 (m, 2H), 7.09 (s, 1H), 6.98 (s, 2H), 6.03 (dd, J=9.8, 4.3 Hz, 1H), 2.27-2.38 (m, 1H), 1.79-1.88 (m, 1H), 0.54-0.63 (m, 1H), 0.27-0.37 (m, 2H), 0.06-0.14 (m, 1H), 0.00-0.04 (m, 1H). $^{19}$F NMR (282 MHz, DMSO-d$_6$) δ −112.73.

Example 652: (S)-5-(3-Chloro-6-(difluoromethyl)-2-fluorophenyl)-2-(3-methoxy-1-(4-(1-methyl-1H-1,2,3-triazol-5-yl)-1H-pyrazol-1-yl)propyl)pyridine 1-oxide

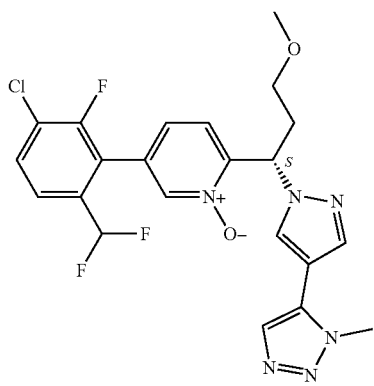

LC/MS: mass calculated for $C_{22}H_{20}ClF_3N_6O_2$: 492.13, measured (ES, m/z): 493.05 [M+H]$^+$. $^1$H NMR (400 MHz, DMSO-d$_6$) δ 8.59 (s, 1H), 8.52 (d, J=1.7 Hz, 1H), 8.06 (s, 1H), 7.86-7.94 (m, 2H), 7.62 (d, J=8.5 Hz, 1H), 7.48 (d, J=8.2 Hz, 1H), 7.40 (dd, J=8.2, 1.7 Hz, 1H), 6.90 (t, J=53.8 Hz, 1H), 6.27-6.35 (m, 1H), 4.12 (s, 3H), 3.32-3.40 (m, 1H), 3.18-3.26 (m, 4H), 2.52-2.64 (m, 2H). $^{19}$F NMR (376 MHz, DMSO-d$_6$) δ −106.90--112.99, −115.25.

Example 653: (R)-5-(3-Chloro-6-(difluoromethyl)-2-fluorophenyl)-2-(3-methoxy-1-(4-(1-methyl-1H-1,2,3-triazol-5-yl)-1H-pyrazol-1-yl)propyl)pyridine 1-oxide

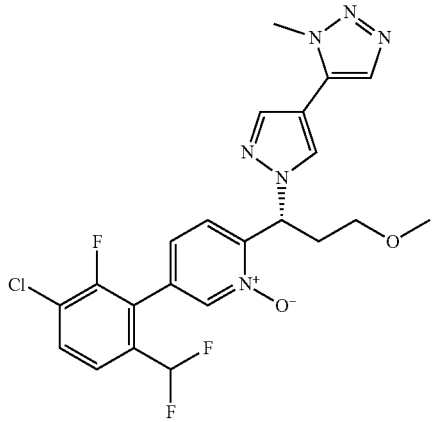 [SMILES: COCC[C@H](c1ccc(-c2c(C(F)F)ccc(Cl)c2F)c[n+]1[O-])n1cc(-c2cnnn2C)cn1]

Step 1: (6-(3-Methoxy-1-(4-(1-methyl-1H-1,2,3-triazol-5-yl)-1H-pyrazol-1-yl)propyl)pyridin-3-yl)boronic acid A mixture of 5-bromo-2-(3-methoxy-1-(4-(1-methyl-1H-1,2,3-triazol-5-yl)-1H-pyrazol-1-yl)propyl)pyridine (0.50 g, 1.33 mmol, 1.0 equiv.), 4,4,4',4',5,5,5',5'-octamethyl-2,2'-bi(1,3,2-dioxaborolane) (0.67 g, 2.65 mmol, 2.0 equiv.), Pd(dppf)Cl$_2$ (97 mg, 0.13 mmol, 0.1 equiv.), K$_2$CO$_3$ (0.39 g, 3.98 mmol, 3.0 equiv.) in 1,4-dioxane (5 mL) was refluxed at 90° C. under N$_2$ for 2 h. The mixture was diluted with water, extracted with ethyl acetate twice. The combined organic layers were washed with brine, dried over Na$_2$SO$_4$, concentrated to yield (6-(3-methoxy-1-(4-(1-methyl-1H-1,2,3-triazol-5-yl)-1H-pyrazol-1-yl)propyl)pyridin-3-yl)boronic acid. LC/MS: mass calculated for $C_{15}H_{19}BN_6O_3$: 342.16, measured (ES, m/z): 343.05 [M+H]$^+$.

Step 2: 5-(3-Chloro-6-(difluoromethyl)-2-fluorophenyl)-2-(3-methoxy-1-(4-(1-methyl-1H-1,2,3-triazol-5-yl)-1H-pyrazol-1-yl)propyl)pyridine A mixture of (6-(3-methoxy-1-(4-(1-methyl-1H-1,2,3-triazol-5-yl)-1H-pyrazol-1-yl)propyl)pyridin-3-yl)boronic acid (1.1 g, resulting), 2-bromo-4-chloro-1-(difluoromethyl)-3-fluorobenzene (0.56 g, 2.14 mmol), Pd(PPh$_3$)$_4$ (0.50 g, 0.43 mmol), K$_2$CO$_3$ (1.8 g, 12.86 mmol) in 1,4-dioxane (10 mL) and water (2 mL) was refluxed at 90° C. under N$_2$ for 2 h. The mixture was diluted with H$_2$O, extracted with ethyl acetate twice. The combined organic layers was washed with brine, dried over Na$_2$SO$_4$, concentrated and purified by silica gel chromatography (0→10%, MeOH/DCM) to yield 5-(3-chloro-6-(difluoromethyl)-2-fluorophenyl)-2-(3-methoxy-1-(4-(1-methyl-1H-1,2,3-triazol-5-yl)-1H-pyrazol-1-yl)propyl)pyridine as a light yellow oil. LC/MS: mass calculated for $C_{22}H_{20}ClF_3N_6O$: 476.13, measured (ES, m/z): 477.05 [M+H]$^+$.

Step 3: (R)-5-(3-Chloro-6-(difluoromethyl)-2-fluorophenyl)-2-(3-methoxy-1-(4-(1-methyl-1H-1,2,3-triazol-5-yl)-1H-pyrazol-1-yl)propyl)pyridine 1-oxide A mixture of 5-(3-chloro-6-(difluoromethyl)-2-fluorophenyl)-2-(3-methoxy-1-(4-(1-methyl-1H-1,2,3-triazol-5-yl)-1H-pyrazol-1-yl)propyl)pyridine (0.20 g, 0.42 mmol, 1.0 equiv.), hydrogen peroxide (30 wt %, 0.48 mL, 4.19 mmol, 10.0 equiv.) and methyltrioxorhenium (21 mg, 0.084 mmol, 0.2 equiv.) in CH$_3$OH (0.5 mL) was stirred for 1 h at room temperature. The mixture was purified by reverse phase chromatography on C18 (80 g, MeCN/H$_2$O (0.05% CF$_3$COOH): 0→45%) and Prep-Chiral-HPLC to yield (R)-5-(3-chloro-6-(difluoromethyl)-2-fluorophenyl)-2-(3-methoxy-1-(4-(1-methyl-1H-1,2,3-triazol-5-yl)-1H-pyrazol-1-yl)propyl)pyridine 1-oxide as a white solid.

LC/MS: mass calculated for $C_{22}H_{20}ClF_3N_6O_2$: 492.13, measured (ES, m/z): 493.05 [M+H]$^+$. $^1$H NMR (400 MHz, DMSO-d$_6$): δ 8.59 (s, 1H), 8.52 (d, J=1.6 Hz, 1H), 8.06 (s, 1H), 7.84-7.94 (m, 2H), 7.62 (d, J=8.5 Hz, 1H), 7.48 (d, J=8.2 Hz, 1H), 7.35-7.45 (m, 1H), 6.90 (t, J=53.8 Hz, 1H), 6.31 (t, J=7.3 Hz, 1H), 4.12 (s, 3H), 3.33-3.43 (m, 1H), 3.18-3.26 (m, 4H), 2.52-2.64 (m, 2H). $^{19}$F NMR (376 MHz, DMSO-d$_6$): −108.53, −109.92, −115.25.

Example 654: (S)-5-(3-Chloro-6-(4-chloro-1H-1,2,3-triazol-1-yl)-2-fluorophenyl)-2-(2-(4-fluorophenyl)-1-(4-(1-methyl-1H-1,23-triazol-5-yl)-1H-pyrazol-1-ylethyl)pyridine 1-oxide

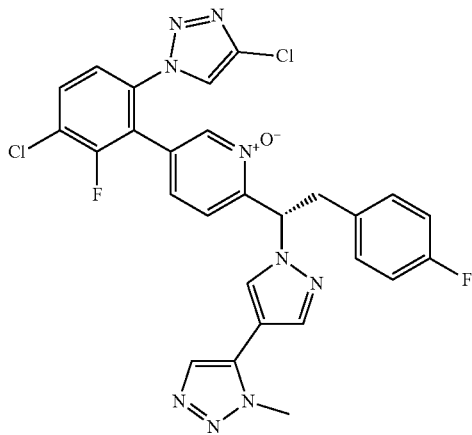

LC/MS: mass calculated for $C_{27}H_{19}Cl_2F_2N_9O$: 593.1, measured (ES, m/z): 594.2 [M+H]$^+$. $^1$H NMR (400 MHz, DMSO-$d_6$) δ 8.54-8.60 (m, 1H), 8.36 (s, 1H), 8.29 (d, J=2.9 Hz, 1H), 7.90-7.98 (m, 2H), 7.82 (s, 1H), 7.61 (dd, J=8.7, 1.6 Hz, 1H), 7.53 (d, J=8.3 Hz, 1H), 7.22 (dd, J=8.3, 1.7 Hz, 1H), 7.12-7.20 (m, 2H), 6.98-7.08 (m, 2H), 6.29-6.31 (m, 1H), 3.97 (s, 3H), 3.51-3.58 (m, 2H). $^{19}$F NMR (376 MHz, DMSO-$d_6$) δ -110.59--118.46 (m).

Example 655: (R)-5-(3-Chloro-6-(4-chloro-1H-1,2,3-triazol-1-yl)-2-fluorophenyl)-2-(2-(4-fluorophenyl)-1-(4-(1-methyl-1H-1,2,3-triazol-5-yl)-1H-pyrazol-1-yl)ethyl)pyridine 1-oxide

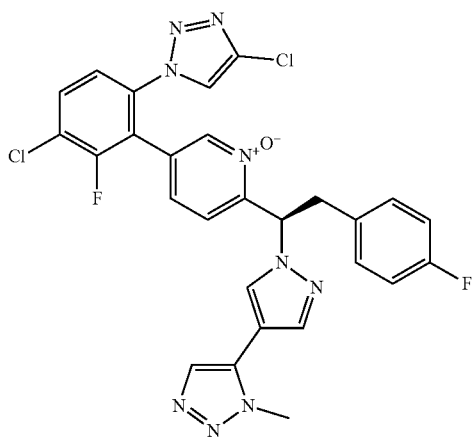

Step 1: 1-(5-Bromopyridin-2-yl)-2-(4-fluorophenyl)ethan-1-ol

To a solution of 2,5-dibromopyridine (15.6 g, 65.81 mmol, 1.0 equiv.) in toluene (120 mL) was add n-BuLi (31.5 mL, 78.97 mmol, 1.2 equiv.) at -78° C. under $N_2$, after 1 hour was add 2-(4-fluorophenyl)acetaldehyde (10.0 g, 72.39 mmol, 1.1 equiv.) in toluene (30 mL) to the mixture slowly at -78° C. under $N_2$, then the reaction mixture was stirred 2 hours at -78° C. under $N_2$. The reaction mixture was added NH$_4$Cl (aq.) and extracted with ethyl acetate, the organic layer was washed with brine and dried over anhydrous Na$_2$SO$_4$. The resulting mixture was then concentrated and purified by silica gel chromatography (0→40% EA/PE) to yield 1-(5-bromopyridin-2-yl)-2-(4-fluorophenyl)ethan-1-ol as a yellow solid. LC/MS: mass calculated for $C_{13}H_{11}BrFNO$: 295.00, measured (ES, m/z): 295.85 [M+H]$^+$.

Step 2: 1-(5-Bromopyridin-2-yl)-2-(4-fluorophenyl)ethyl methanesulfonate

To a solution of 1-(5-bromopyridin-2-yl)-2-(4-fluorophenyl)ethan-1-ol (10.0 g, 33.77 mmol, 1.0 equiv.) in DCM (100 mL) was added triethylamine (9.4 ml, 67.54 mmol, 2.0 equiv.) and methanesulfonic anhydride (8.8 g, 50.65 mmol, 1.5 equiv.) at 0° C., then warmed to room temperature and stirred for 4 h. The reaction was added water, and the mixture extracted with DCM, the organic layer was washed with brine and dried over anhydrous Na$_2$SO$_4$. Concentrated and purified by silica gel chromatography (0→40% EA/PE) to yield 1-(5-bromopyridin-2-yl)-2-(4-fluorophenyl)ethyl methanesulfonate as a yellow solid. LC/MS: mass calculated for $C_{14}H_{13}BrFNO_3S$: 372.98, measured (ES, m/z): 373.90 [M+H]$^+$.

Step 3: 5-Bromo-2-(2-(4-fluorophenyl)-1-(4-(1-methyl-1H-1,2,3-triazol-5-yl)-1H-pyrazol-1-yl)ethyl)pyridine The mixture of 1-(5-bromopyridin-2-yl)-2-(4-fluorophenyl)ethyl methanesulfonate (1.2 g, 3.21 mmol, 1.0 equiv.), 1-methyl-5-(1H-pyrazol-4-yl)-1H-1,2,3-triazole (574 mg, 3.85 mmol, 1.2 equiv.) and Cs$_2$CO$_3$ (2.1 g, 6.41 mmol, 2.0 equiv.) in acetonitrile (15 mL) was stirred at 90° C. for 3 h. To the reaction mixture was added water, and the mixture extracted with ethyl acetate, the organic layer was washed with brine and dried over anhydrous Na$_2$SO$_4$. The resulting mixture was concentrated and purified by silica gel chromatography (0→40% EA/PE) to yield 5-bromo-2-(2-(4-fluorophenyl)-1-(4-(1-methyl-1H-1,2,3-triazol-5-yl)-1H-pyrazol-1-yl)ethyl)pyridine as a yellow solid. LC/MS: mass calculated for $C_{19}H_{16}BrFN_6$: 426.06, measured (ES, m/z): 426.90 [M+H]$^+$.

Step 4: (6-(2-(4-Fluorophenyl)-1-(4-(1-methyl-1H-1,2,3-triazol-5-yl)-1H-pyrazol-1-yl)ethyl)pyridin-3-yl)boronic acid The mixture of 5-bromo-2-(2-(4-fluorophenyl)-1-(4-(1-methyl-1H-1,2,3-triazol-5-yl)-1H-pyrazol-1-yl)ethyl)pyridine (1.2 g, 2.81 mmol, 1.0 equiv.), KOAc (689 mg, 7.02 mmol, 2.5 equiv.), 4,4,4',4',5,5,5',5'-octamethyl-2,2'-bi(1,3,2-dioxaborolane) (1.4 g, 5.61 mmol, 2.0 equiv.) and Pd(dppf)Cl$_2$ (205 mg, 0.28 mmol, 0.1 equiv.) in 1,4-dioxane (15 mL) was stirred at 90° C. for 2 h under N$_2$. To the reaction mixture was added water, and the mixture extracted with ethyl acetate, the organic layer was washed with brine and dried over anhydrous Na$_2$SO$_4$. The resulting mixture was then concentrated to yield 6-(2-(4-fluorophenyl)-1-(4-(1-methyl-1H-1,2,3-triazol-5-yl)-1H-pyrazol-1-yl)ethyl)pyridin-3-yl)boronic acid as a yellow solid. LC/MS: mass calculated for $C_{19}H_{18}BFN_6O_2$: 392.16, measured (ES, m/z): 393.05 [M+H]$^+$.

Step 5: 5-(3-Chloro-6-(4-chloro-1H-1,2,3-triazol-1-yl)-2-fluorophenyl)-2-(2-(4-fluorophenyl)-1-(4-(1-methyl-1H-1,2,3-triazol-5-yl)-1H-pyrazol-1-yl)ethyl)pyridine The mixture of (6-(2-(4-fluorophenyl)-1-(4-(1-methyl-1H-1,2,3-triazol-5-yl)-1H-pyrazol-1-yl)ethyl)pyridin-3-yl)boronic acid (600 mg, 1.53 mmol, 1.0 equiv.), 4-chloro-1-(4-chloro-3-fluoro-2-iodophenyl)-1H-1,2,3-triazole (821 mg, 2.29 mmol, 1.5 equiv.), $K_2CO_3$ (1.1 g, 7.64 mmol, 5.0 equiv.) and $Pd(PPh_3)_4$ (177 mg, 0.15 mmol, 0.1 equiv.) in 1,4-dioxane (10 mL) and water (2 mL) was stirred at 90° C. for 2 h under $N_2$. To the reaction mixture was added water, and the mixture extracted with ethyl acetate, the organic layer was washed with brine and dried over anhydrous $Na_2SO_4$. The resulting mixture was then concentrated and purified by silica gel chromatography (0→40% EA/PE) to yield 5-(3-chloro-6-(4-chloro-1H-1,2,3-triazol-1-yl)-2-fluorophenyl)-2-(2-(4-fluorophenyl)-1-(4-(1-methyl-1H-1,2,3-triazol-5-yl)-1H-pyrazol-1-yl)ethyl)pyridine as a yellow solid. LC/MS: mass calculated for $C_{27}H_{19}Cl_2F_2N_9$: 577.11, measured (ES, m/z): 578.00 $[M+H]^+$.

Step 6: (R)-5-(3-chloro-6-(4-chloro-1H-1,2,3-triazol-1-yl)-2-fluorophenyl)-2-(2-(4-fluorophenyl)-1-(4-(1-methyl-1H-1,2,3-triazol-5-yl)-1H-pyrazol-1-yl)ethyl)pyridine 1-oxide The mixture of 5-(3-chloro-6-(4-chloro-1H-1,2,3-triazol-1-yl)-2-fluorophenyl)-2-(2-(4-fluorophenyl)-1-(4-(1-methyl-1H-1,2,3-triazol-5-yl)-1H-pyrazol-1-yl)ethyl)pyridine (200 mg, 0.35 mmol, 1.0 equiv.), methyltrioxorhenium (43.09 mg, 0.17 mmol, 0.5 equiv.) and hydrogen peroxide (196 mg, 1.73 mmol, 5.0 equiv, 30%) in $CH_3OH$ (2 mL) was stirred at room temperature for 2 h. The solution was purified by reverse phase chromatography on C18 (80 g, $MeCN/H_2O$ (0.05% $CF_3COOH$): 0→55%) to yield 5-(3-chloro-6-(4-chloro-1H-1,2,3-triazol-1-yl)-2-fluorophenyl)-2-(2-(4-fluorophenyl)-1-(4-(1-methyl-1H-1,2,3-triazol-5-yl)-1H-pyrazol-1-yl)ethyl)pyridine 1-oxide. The compound of 5-(3-chloro-6-(4-chloro-1H-1,2,3-triazol-1-yl)-2-fluorophenyl)-2-(2-(4-fluorophenyl)-1-(4-(1-methyl-1H-1,2,3-triazol-5-yl)-1H-pyrazol-1-yl)ethyl)pyridine 1-oxide was separated by Prep-Chiral-HPLC to yield (R)-5-(3-chloro-6-(4-chloro-1H-1,2,3-triazol-1-yl)-2-fluorophenyl)-2-(2-(4-fluorophenyl)-1-(4-(1-methyl-1H-1,2,3-triazol-5-yl)-1H-pyrazol-1-yl)ethyl)pyridine 1-oxide as a white solid.

LC/MS: mass calculated for $C_{27}H_{19}Cl_2F_2N_9O$: 593.1, measured (ES, m/z): 594.2 $[M+H]^+$. $^1H$ NMR (400 MHz, DMSO-$d_6$) δ 8.56-8.59 (m, 1H), 8.37 (s, 1H), 8.29 (s, 1H), 7.89-7.98 (m, 2H), 7.82 (s, 1H), 7.59-7.63 (m, 1H), 7.51-7.54 (m, 1H), 7.11-7.26 (m, 3H), 7.02 (t, J=8.2 Hz, 2H), 6.24-6.29 (m, 1H), 3.97 (s, 3H), 3.46-3.63 (m, 2H). $^{19}F$ NMR (376 MHz, DMSO-$d_6$) δ –113.10, –115.78.

Example 656: (R)-5-(3-Chloro-2-fluoro-6-(1H-tetrazol-1-yl)phenyl)-2-(3-methoxy-1-(2-methyl-5-(trifluoromethyl)-1'H,2H-[3,4'-bipyrazol]-1'-yl)propyl)pyridine 1-oxide

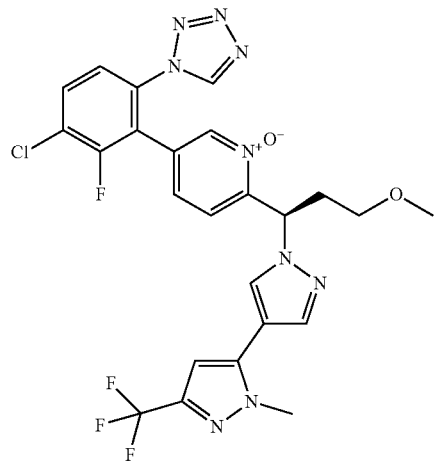

LC/MS: mass calculated for $C_{24}H_{20}ClF_4N_9O_2$: 577.13, measured (ES, m/z): 578.2 $[M+H]^+$. $^1H$ NMR (400 MHz, DMSO-$d_6$) δ 9.63 (s, 1H), 8.42 (s, 1H), 8.37-8.39 (m, 1H), 7.95-8.04 (m, 2H), 7.69 (dd, J=8.7, 1.5 Hz, 1H), 7.37 (d, J=8.3 Hz, 1H), 7.20 (dd, J=8.4, 1.6 Hz, 1H), 6.91 (s, 1H), 6.19-6.23 (m, 1H), 3.95 (s, 3H), 3.30-3.32 (m, 1H), 3.16-3.18 (m, 4H), 2.45-2.47 (m, 2H). $^{19}F$ NMR (376 MHz, DMSO-$d_6$) δ –60.50, –73.71, –112.82.

Example 657: (S)-5-(3-Chloro-2-fluoro-6-(1H-tetrazol-1-yl)phenyl)-2-(3-methoxy-1-(2-methyl-5-(trifluoromethyl)-1'H,2H-[3,4'-bipyrazol]-1'-yl)propyl)pyridine 1-oxide

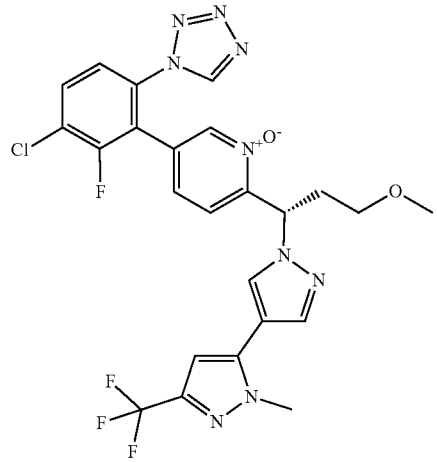

LC/MS: mass calculated for $C_{24}H_{20}ClF_4N_9O_2$: 577.13, measured (ES, m/z): 578.2 $[M+H]^+$. $^1H$ NMR (400 MHz, DMSO-$d_6$) δ 9.70 (s, 1H), 8.51 (s, 1H), 8.45 (s, 1H), 8.04-8.08 (m, 1H), 8.02 (s, 1H), 7.77 (d, J=8.7 Hz, 1H), 7.34 (d, J=8.3 Hz, 1H), 7.18 (d, J=8.3 Hz, 1H), 6.94 (s, 1H), 6.18-6.22 (m, 1H), 3.99 (s, 3H), 3.31-3.33 (m, 1H), 3.19-

3.21 (m, 4H), 2.47-2.49 (m, 2H). $^{19}$F NMR (376 MHz, DMSO-d$_6$) δ −60.50, −73.65, −112.80.

Example 658: 2-(1-(4-Carboxy-1H-pyrazol-1-yl)-2-cyclopropylethyl)-5-(3-Chloro-2-fluoro-6-(1H-tetrazol-1-yl)phenyl)pyridine 1-oxide

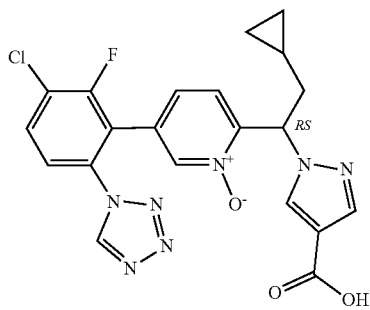 [SMILES: O=C(O)c1cnn(C(CC2CC2)c2ccc(-c3c(-n4cnnn4)ccc(Cl)c3F)c[n+]2[O-])c1]

LC/MS: mass calculated for C$_{21}$H$_{17}$ClFN$_7$O$_3$: 469.1, measured (ES, m/z): 470.2 [M+H]$^+$. $^1$H NMR (400 MHz, CD$_3$OD) δ 9.38 (s, 1H), 8.29-8.48 (m, 2H), 7.84-8.03 (m, 2H), 7.43-7.70 (m, 2H), 7.28 (br d, J=7.58 Hz, 1H), 6.09-6.40 (m, 1H), 2.42 (br d, J=6.06 Hz, 1H), 1.90-2.21 (m, 1H), 0.63 (br d, J=5.05 Hz, 1H), 0.32-0.53 (m, 2H), 0.17 (br d, J=4.04 Hz, 1H), 0.00 (s, 1H).

Example 659: (S)-2-(1-(4-Chloro-2-(difluoromethyl)-1'H,2H-[3,4'-bipyrazol]-1'-yl)-3-methoxypropyl)-5-(3-chloro-2-fluoro-6-(1H-tetrazol-1-yl)phenyl)pyridine 1-oxide

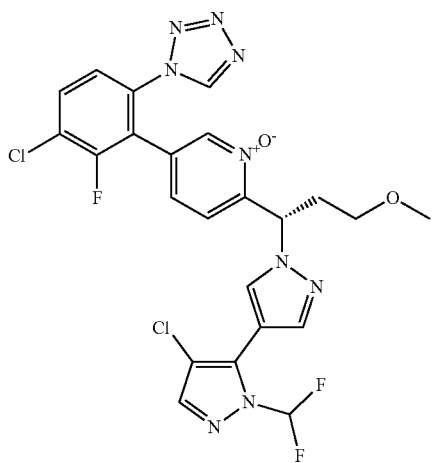

LC/MS: mass calculated for C$_{23}$H$_{18}$Cl$_2$F$_3$N$_9$O$_2$: 579.09, measured (ES, m/z): 580.2 [M+H]$^+$. $^1$H NMR (300 MHz, DMSO-d$_6$) δ 9.69 (s, 1H), 8.42-8.44 (m, 2H), 8.01-8.12 (m, 2H), 7.58-7.99 (m, 3H), 7.39-7.42 (m, 1H), 7.19-7.39 (m, 1H), 6.20-6.27 (m, 1H), 3.27-3.36 (m, 1H), 3.06-3.20 (m, 4H), 2.44-2.57 (m, 2 h). $^{19}$F NMR (282 MHz, DMSO-d$_6$) δ −73.65, −94.00, −94.11, −112.68.

Example 660: (R)-2-(1-(4-Chloro-2-(difluoromethyl)-1'H,2H-[3,4'-bipyrazol]-1'-yl)-3-methoxypropyl)-5-(3-chloro-2-fluoro-6-(1H-tetrazol-1-yl)phenyl)pyridine 1-oxide

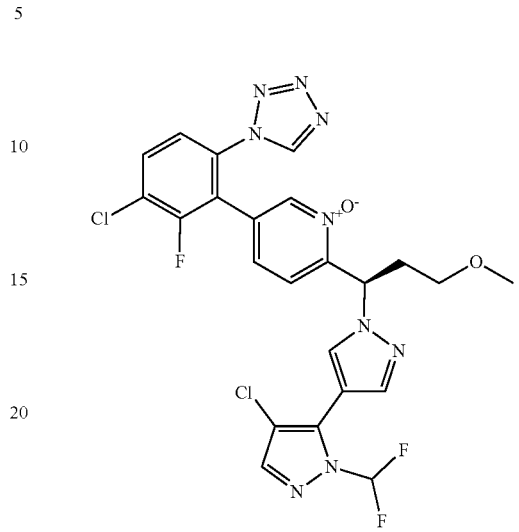

Step 1: 1'-(1-(5-Bromopyridin-2-yl)-3-methoxypropyl)-2-(difluoromethyl)-1'H,2H-3,4'-bipyrazole A mixture of 1-(5-bromopyridin-2-yl)-3-methoxypropyl methanesulfonate (1.5 g, 4.6 mmol, 1.0 equiv.), 2-(difluoromethyl)-1'H,2H-3,4'-bipyrazole (937 mg, 5.1 mmol, 1.1 equiv.) and cesium carbonate (1.7 g, 5.1 mmol, 1.1 equiv.) in acetonitrile (20 mL) was stirred at 90° C. for 4 h. The reaction was diluted with water, and the mixture extracted with ethyl acetate twice. The combined organic layers were washed with brine, dried over anhydrous sodium sulfate and concentrated. The residue was purified by silica gel chromatography (0→80% ethyl acetate/petroleum ether) to yield 1'-(1-(5-bromopyridin-2-yl)-3-methoxypropyl)-2-(difluoromethyl)-1'H,2H-3,4'-bipyrazole as a light yellow oil. LC/MS: mass calculated for C$_{16}$H$_{16}$BrF$_2$N$_5$O: 411.05, measured (ES, m/z): 412.05, 414.05 [M+H, M+H+2]$^+$.

Step 2: 1'-(1-(5-Bromopyridin-2-yl)-3-methoxypropyl)-4-chloro-2-(difluoromethyl)-1'H,2H-3,4'-bipyrazole A mixture of 1'-(1-(5-bromopyridin-2-yl)-3-methoxypropyl)-2-(difluoromethyl)-1'H,2H-3,4'-bipyrazole (500 mg, 1.21 mmol, 1.0 equiv.) and N-chlorosuccinimide (243 mg, 1.82 mmol, 1.5 equiv.) in DMF (5 mL) was stirred at 60° C. for 2 h. The solution was diluted withe water, and the mixture extracted with ethyl acetate twice. The combined organic layers were washed with water, brine, dried over anhydrous sodium sulfate and concentrated. The residue was purified by silica gel chromatography (0→80% ethyl acetate/petroleum ether) to yield 1'-(1-(5-bromopyridin-2-yl)-3-methoxypropyl)-4-chloro-2-(difluoromethyl)-1'H,2H-3,4'-bipyrazole as a light yellow oil. LC/MS: mass calculated for C$_{16}$H$_{15}$BrClF$_2$N$_5$O: 445.01, measured (ES, m/z): 445.90, 447.90 [M+H, M+H+2]$^+$.

Step 3: 4-Chloro-2-(6-(1-(4-chloro-2-(difluoromethyl)-1'H,2H-[3,4'-bipyrazol]-1'-yl)-3-methoxypropyl)pyridin-3-yl)-3-fluoroaniline To a mixture of 1'-(1-(5-bromopyridin-2-yl)-3-methoxypropyl)-4-chloro-2-(difluoromethyl)-1'H,2H-3,4'-bipyrazole (370 mg, 0.83 mmol, 1.0 equiv.), 6-amino-3-chloro-2-fluorophenylboronic acid (235 mg, 1.24 mmol, 1.5 equiv.) and potassium carbonate (343 mg, 2.49 mmol, 3.0 equiv.) in 1,4-dioxane (4 mL) and water (1 mL) was added tetrakis(triphenylphosphine)palladium(0) (96 mg, 0.08 mmol, 0.1 equiv.) and the mixture was stirred at 90° C. for 2 h. After cooling to room temperature, the reaction was quenched with water, and the mixture extracted with ethyl acetate twice. The combined organic layers were washed with brine, dried over anhydrous sodium sulfate and concentrated. The residue was purified silica gel chromatography (0→10% MeOH/DCM) to yield 4-chloro-2-(6-(1-(4-chloro-2-(difluoromethyl)-1'H,2H-[3,4'-bipyrazol]-1'-yl)-3-methoxypropyl)pyridin-3-yl)-3-fluoroaniline as a light yellow solid. LC/MS: mass calculated for $C_{22}H_{19}Cl_2F_3N_6O$: 510.09, measured (ES, m/z): 511.15 [M+H]$^+$.

Step 4: 4-Chloro-1'-(1-(5-(3-chloro-2-fluoro-6-(1H-tetrazol-1-yl)phenyl)pyridin-2-yl)-3-methoxypropyl)-2-(difluoromethyl)-1'H,2H-3,4'-bipyrazole A mixture of 4-chloro-2-(6-(1-(4-chloro-2-(difluoromethyl)-1'H,2H-[3,4'-bipyrazol]-1'-yl)-3-methoxypropyl)pyridin-3-yl)-3-fluoroaniline (400 mg, 0.78 mmol, 1.0 equiv.), azidotrimethylsilane (1 mL) and trimethoxymethane (1 mL) in acetic acid glacial (1 mL) was stirred at room temperature overnight. The mixture was concentrated and the residue was purified by reverse phase chromatography on C18 (80 g, MeCN/H$_2$O (0.05% CF$_3$COOH): 0→50%) to yield 4-chloro-1'-(1-(5-(3-chloro-2-fluoro-6-(1H-tetrazol-1-yl)phenyl)pyridin-2-yl)-3-methoxypropyl)-2-(difluoromethyl)-1'H,2H-3,4'-bipyrazole as alight yellow solid.

LC/MS: mass calculated for $C_{23}H_{18}Cl_2F_3N_9O$: 563.10, measured (ES, m/z): 564.05 [M+H]$^+$.

Step 5: (R)-2-(1-(4-Chloro-2-(difluoromethyl)-1'H,2H-[3,4'-bipyrazol]-1'-yl)-3-methoxypropyl)-5-(3-chloro-2-fluoro-6-(1H-tetrazol-1-yl)phenyl)pyridine 1-oxide A mixture of 4-chloro-1'-(1-(5-(3-chloro-2-fluoro-6-(1H-tetrazol-1-yl)phenyl)pyridin-2-yl)-3-methoxypropyl)-2-(difluoromethyl)-1'H,2H-3,4'-bipyrazole (300 mg, 0.53 mmol, 1.0 equiv.), methyl trioxorhenium (VII) (66 mg, 0.27 mmol, 0.5 equiv.) and hydrogen peroxide (0.27 mL, 2.66 mmol, 30 wt %, 5.0 equiv.) in CH$_3$OH (2.0 mL) was stirred at room temperature for 1 h. The reaction was purified by reverse phase chromatography on C18 (80 g, MeCN/H$_2$O (0.05% CF$_3$COOH): 0→45%) and then Prep-HPLC to yield (R)-2-(1-(4-chloro-2-(difluoromethyl)-1'H,2H-[3,4'-bipyrazol]-1'-yl)-3-methoxypropyl)-5-(3-chloro-2-fluoro-6-(1H-tetrazol-1-yl)phenyl)pyridine 1-oxide as a white solid.

LC/MS: mass calculated for $C_{23}H_{18}Cl_2F_3N_9O_2$: 579.09, measured (ES, m/z): 580.2 [M+H]$^+$. $^1$H NMR (300 MHz, DMSO-d$_6$): δ 9.69 (s, 1H), 8.42-8.44 (m, 2H), 8.01-8.13 (m, 2H), 7.52-8.00 (m, 3H), 7.40-7.43 (m, 1H), 7.20-7.24 (m, 1H), 6.25 (t, J=7.3 Hz, 1H), 3.28-3.37 (m, 1H), 3.10-3.20 (m, 4H), 2.42-2.59 (m, 2H). $^{19}$F-NMR (282 MHz, DMSO-d$_6$): δ −73.60, −94.10, −112.69.

Example 661: 2-(1-(4-(2-Amino-4-chlorothiazol-5-yl)-1H-pyrazol-1-yl)-2-cyclopropylethyl)-5-(3-chloro-2-fluoro-6-(1H-tetrazol-1-yl)phenyl)pyridine 1-oxide

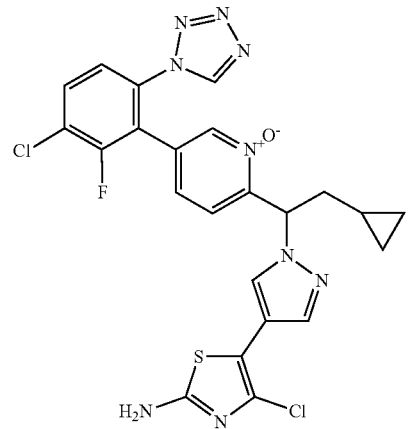

LC/MS: mass calculated for $C_{23}H_{18}Cl_2FN_9OS$: 557.07, measured (ES, m/z): 558.15 [M+H]$^+$. $^1$H NMR (300 MHz, DMSO-d$_6$) δ 9.69 (s, 1H), 8.41 (d, J=1.5 Hz, 1H), 8.26 (s, 1H), 8.06 (dd, J=8.7, 7.8 Hz, 1H), 7.75-7.80 (m, 2H), 7.21-7.48 (m, 3H), 7.06-7.20 (m, 1H), 6.05-6.10 (m, 1H), 2.27-2.40 (m, 1H), 1.83-1.98 (m, 1H), 0.58-0.65 (m, 1H), 0.25-0.40 (m, 2H), 0.06-0.15 (m, 1H), −0.08-0.00 (m, 1H). $^{19}$F NMR (282 MHz, DMSO-d$_6$) δ −74.05 (d, J=14.3 Hz), −112.76.

Example 662: (S)-5-(3-Chloro-6-(4-chloro-1H-1,2,3-triazol-1-yl)-2-fluorophenyl)-2-(1-(2-(difluoromethyl)-4-fluoro-1'H,2H-[3,4'-bipyrazol]-1'-yl)-3-methoxypropyl)pyridine 1-oxide

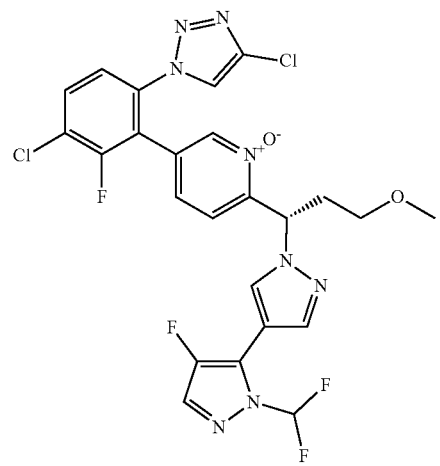

LC/MS: mass calculated for $C_{24}H_{18}Cl_2F_4N_8O_2$: 596.09, measured (ES, m/z): 619.00 [M+Na]$^+$. $^1$H NMR (400 MHz, DMSO-d$_6$) δ 8.68 (s, 1H), 8.37-8.44 (m, 2H), 8.00-8.06 (m, 2H), 7.66-7.97 (m, 3H), 7.42 (d, J=8.3 Hz, 1H), 7.18 (dd, J=8.3, 1.7 Hz, 1H), 6.23-6.27 (m, 1H), 3.21-3.31 (m, 1H), 3.19 (s, 3H), 3.09-3.22 (m, 1H), 2.44-2.66 (m, 2 h). $^{19}$F NMR (376 MHz, DMSO-d$_6$) δ −94.09, −94.15, −112.95, −171.24.

Example 663: (R)-5-(3-Chloro-6-(4-chloro-1H-1,2, 3-triazol-1-yl)-2-fluorophenyl)-2-(1-(2-(difluoromethyl)-4-fluoro-1'H,2H-[3,4'-bipyrazol]-1'-yl)-3-methoxypropyl)pyridine 1-oxide

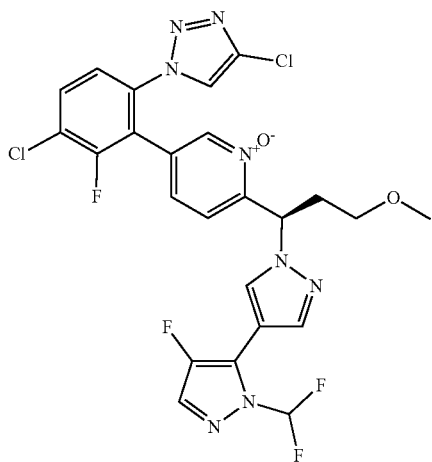

Step 1: 1'-(1-(5-Bromopyridin-2-yl)-3-methoxypropyl)-2-(difluoromethyl)-4-fluoro-1'H,2H-3,4'-bipyrazole A mixture of 1'-(1-(5-bromopyridin-2-yl)-3-methoxypropyl)-2-(difluoromethyl)-1'H,2H-3,4'-bipyrazole (1.0 g, 2.4 mmol, 1.0 equiv.) and 1-Chloromethyl-4-fluoro-1,4-diazoniabicyclo[2.2.2]octane bis(tetrafluoroborate) (also known as Selectfluor™, 1.3 g, 3.6 mmol, 1.5 equiv.) in acetonitrile (10 mL) was stirred for 2 h at 60° C. The reaction was quenched with water, and the mixture extracted with ethyl acetate twice. The combined organic layers were washed with brine, dried over anhydrous sodium sulfate and concentrated. The residue was purified silica gel chromatography (0→50% EA/PE) to yield 1'-(1-(5-bromopyridin-2-yl)-3-methoxypropyl)-2-(difluoromethyl)-4-fluoro-1'H,2H-3, 4'-bipyrazole as a light yellow solid. LC/MS: mass calculated for C$_{16}$H$_{15}$BrF$_3$N$_5$O: 429.04, measured (ES, m/z): 430.00, 432.00 [M+H, M+H+2]$^+$.

Step 2: (6-(1-(2-(Difluoromethyl)-4-fluoro-1'H,2H-[3,4'-bipyrazol]-1'-yl)-3-methoxypropyl)pyridin-3-yl)boronic acid A mixture of 1'-(1-(5-bromopyridin-2-yl)-3-methoxypropyl)-2-(difluoromethyl)-4-fluoro-1'H,2H-3,4'-bipyrazole (260 mg, 0.60 mmol, 1.0 equiv.), 4,4,4',4',5,5,5',5'-octamethyl-2,2'-bi(1,3,2-dioxaborolane) (307 mg, 1.21 mmol, 2.0 equiv.), Pd(dppf)Cl$_2$ (44 mg, 0.06 mmol, 0.1 equiv.), potassium carbonate (178 mg, 1.81 mmol, 3.0 equiv.) in 1,4-dioxane (3 mL) was stirred at 90° C. under N$_2$ for 2 h. The mixture was diluted with H$_2$O, extracted with ethyl acetate twice. The combined organic layers were washed with brine, dried over Na$_2$SO$_4$, concentrated to yield (6-(1-(2-(difluoromethyl)-4-fluoro-1'H,2H-[3,4'-bipyrazol]-1'-yl)-3-methoxypropyl)pyridin-3-yl)boronic acid. LC/MS: mass calculated for C$_{16}$H$_{17}$BF$_3$N$_5$O$_3$: 395.14, measured (ES, m/z): 396.05 [M+H]$^+$.

Step 3: 1'-(1-(5-(3-Chloro-6-(4-chloro-1H-1,2,3-triazol-1-yl)-2-fluorophenyl)pyridin-2-yl)-3-methoxypropyl)-2-(difluoromethyl)-4-fluoro-1'H, 2H-3,4'-bipyrazole A mixture of (6-(1-(2-(difluoromethyl)-4-fluoro-1'H,2H-[3,4'-bipyrazol]-1'-yl)-3-methoxypropyl)pyridin-3-yl)boronic acid (0.23 g, 0.58 mmol, 1.0 equiv.), 4-chloro-1-(4-chloro-3-fluoro-2-iodophenyl)-1H-1,2,3-triazole (313 mg, 0.87 mmol, 1.5 equiv.), Pd(PPh$_3$)$_4$ (135 mg, 0.12 mmol, 0.2 equiv.), K$_2$CO$_3$ (483 mg, 3.49 mmol, 6.0 equiv.) in 1,4-dioxane (4 mL) and water (1 mL) was refluxed at 90° C. under N$_2$ for 2 h. The mixture was diluted with H$_2$O, extracted with ethyl acetate twice. The combined organic layers were washed with brine, dried over Na$_2$SO$_4$, concentrated and purified by silica gel chromatography (0→8%, MeOH/DCM) to yield 1'-(1-(5-(3-chloro-6-(4-chloro-1H-1,2,3-triazol-1-yl)-2-fluorophenyl)pyridin-2-yl)-3-methoxypropyl)-2-(difluoromethyl)-4-fluoro-1'H,2H-3,4'-bipyrazole as a light yellow oil. LC/MS: mass calculated for C$_{24}$H$_{18}$Cl$_2$F$_4$N$_8$O: 580.09, measured (ES, m/z): 581.00 [M+H]$^+$.

Step 4: (R)-5-(3-Chloro-6-(4-chloro-1H-1,2,3-triazol-1-yl)-2-fluorophenyl)-2-(1-(2-(difluoromethyl)-4-fluoro-1'H,2H-[3,4'-bipyrazol]-1'-yl)-3-methoxypropyl)pyridine 1-oxide A mixture of 1'-(1-(5-(3-chloro-6-(4-chloro-1H-1,2,3-triazol-1-yl)-2-fluorophenyl)pyridin-2-yl)-3-methoxypropyl)-2-(difluoromethyl)-4-fluoro-1'H,2H-3,4'-bipyrazole (260 mg, 0.45 mmol, 1.0 equiv.), hydrogen peroxide (30 wt %, 0.51 mL, 4.47 mmol, 10.0 equiv.) and methyltrioxorhenium (22 mg, 0.09 mmol, 0.2 equiv.) in CH$_3$OH (3 mL) was stirred for 1 h at room temperature. The mixture was purified by reverse phase chromatography on C18 (80 g, MeCN/H$_2$O (0.05% CF$_3$COOH): 0→45%) to yield 5-(3-chloro-6-(4-chloro-1H-1,2,3-triazol-1-yl)-2-fluorophenyl)-2-(1-(2-(difluoromethyl)-4-fluoro-1'H,2H-[3,4'-bipyrazol]-1'-yl)-3-methoxypropyl)pyridine 1-oxide. The racemic product was separated by Chiral-HPLC to yield (R)-5-(3-chloro-6-(4-chloro-1H-1,2,3-triazol-1-yl)-2-fluorophenyl)-2-(1-(2-(difluoromethyl)-4-fluoro-1'H,2H-[3,4'-bipyrazol]-1'-yl)-3-methoxypropyl)pyridine 1-oxide as a white solid.

LC/MS: mass calculated for C$_{24}$H$_{18}$Cl$_2$F$_4$N$_8$O$_2$: 596.09, measured (ES, m/z): 619.00 [M+Na]$^+$. $^1$H NMR (400 MHz, DMSO-d$_6$): δ 8.68 (s, 1H), 8.37-8.44 (m, 2H), 7.99-8.09 (m, 2H), 7.66-7.98 (m, 3H), 7.42 (d, J=8.3 Hz, 1H), 7.15-7.25 (m, 1H), 6.20-6.30 (m, 1H), 3.26-3.34 (m, 1H), 3.19 (s, 3H), 3.09-3.18 (m, 1H), 2.44-2.56 (m, 2H).

Example 664: (S)-5-(3-Chloro-2-fluoro-6-(1H-tetrazol-1-yl)phenyl)-2-(2-cyclopropyl-1-(2-(difluoromethyl)-4-fluoro-1'H,2H-[3,4'-bipyrazol]-1'-yl)ethyl) pyridine 1-oxide

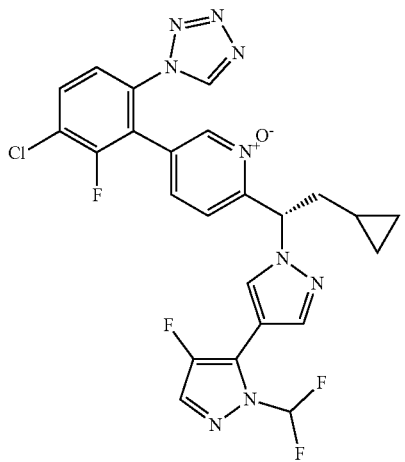

LC/MS: mass calculated for $C_{24}H_{18}ClF_4N_9O$: 559.13, measured (ES, m/z): 582.05 [M+Na]$^+$. $^1$H NMR (300 MHz, DMSO-d$_6$) δ 9.68 (s, 1H), 8.42-8.45 (m, 2H), 7.58-8.12 (m, 5H), 7.38 (d, J=8.3 Hz, 1H), 7.18 (dd, J=8.2, 1.7 Hz, 1H), 6.15-6.19 (m, 1H), 2.21-2.37 (m, 1H), 1.91-2.06 (m, 1H), 0.53-0.63 (m, 1H), 0.22-0.39 (m, 2H), 0.06-0.14 (m, 1H), −0.14−−0.12 (m, 1H). $^{19}$F NMR (282 MHz, DMSO-d$_6$) δ −94.13 (d, J=3.5 Hz), −112.73, −171.37.

Example 665: (R)-5-(3-Chloro-2-fluoro-6-(1H-tetrazol-1-yl)phenyl)-2-(2-cyclopropyl-1-(2-(difluoromethyl)-4-fluoro-1'H,2H-[3,4'-bipyrazol]-1'-yl)ethyl) pyridine 1-oxide

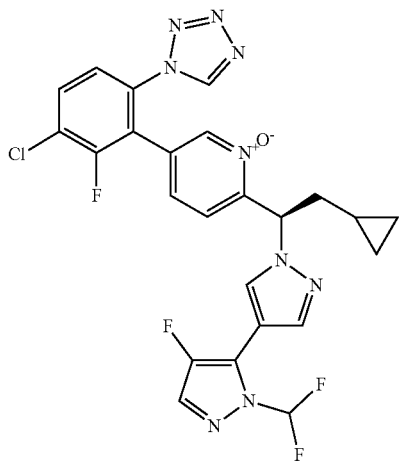

Step 1: 1'-(1-(5-Bromopyridin-2-yl)-2-cyclopropylethyl)-2-(difluoromethyl)-1'H,2H-3,4'-bipyrazole A mixture of cesium carbonate (508.8 mg, 1.6 mmol, 1.0 equiv.) and 2-(difluoromethyl)-1'H,2H-3,4'-bipyrazole (287.5 mg, 1.6 mmol, 1.0 equiv.) in acetonitrile (3.0 mL) was stirred for 15 min at room temperature. 1-(5-Bromopyridin-2-yl)-2-cyclopropylethyl methanesulfonate (500.0 mg, 1.6 mmol, 1.0 equiv.) was added and the solution was stirred for 2.5 h at 70° C. The resulting mixture was diluted with water, extracted with EA (3×50 mL). Then the organic layers were combined, washed with brine, dried over Na$_2$SO$_4$ and concentrated. The residue was purified by silica gel chromatography (PE/EA, 0%→50%) to yield 1'-(1-(5-bromopyridin-2-yl)-2-cyclopropylethyl)-2-(difluoromethyl)-1'H,2H-3,4'-bipyrazole as a yellow oil. LC/MS: mass calculated For $C_{17}H_{16}BrF_2N_5$: 407.06, measured (ES, m/z): 408.00 [M+H]$^+$.

Step 2: 4-Chloro-2-(6-(2-cyclopropyl-1-(2-(difluoromethyl)-1'H,2H-[3,4'-bipyrazol]-1'-yl)ethyl)pyridin-3-yl)-3-fluoroaniline A mixture of 1'-(1-(5-bromopyridin-2-yl)-2-cyclopropylethyl)-2-(difluoromethyl)-1'H,2H-3,4'-bipyrazole (370.0 mg, 0.91 mmol, 1.0 equiv.), 6-amino-3-chloro-2-fluorophenylboronic acid (257.5 mg, 1.36 mmol, 1.5 equiv.), Pd(PPh$_3$)$_4$ (104.7 mg, 0.091 mmol, 0.1 equiv.) and K$_2$CO$_3$ (375.8 mg, 2.70 mmol, 3.0 equiv.) in 1,4-dioxane/water (V/V=4:1, 30 mL) was refluxed at 90° C. under N$_2$ for 3H. The resulting mixture was diluted with water, and the mixture extracted with EA (3×15 mL). The organic layers were combined, washed with water (5 mL), dried over Na$_2$SO$_4$ and concentrated. The residue was purified by silica gel chromatography (0%→10%, DCM/MeOH) to yield 4-chloro-2-(6-(2-cyclopropyl-1-(2-(difluoromethyl)-1'H,2H-[3,4'-bipyrazol]-1'-yl)ethyl)pyridin-3-yl)-3-fluoroaniline as a yellow oil. LC/MS: mass calculated For $C_{23}H_{20}ClF_3N_6$: 472.14, measured (ES, m/z): 473.05 [M+H]$^+$.

Step 3: 1'-(1-(5-(3-Chloro-2-fluoro-6-(1H-tetrazol-1-yl)phenyl)pyridin-2-yl)-2-cyclopropylethyl)-2-(difluoromethyl)-1'H,2H-3,4'-bipyrazole A mixture of 4-chloro-2-(6-(2-cyclopropyl-1-(2-(difluoromethyl)-1'H,2H-[3,4'-bipyrazol]-1'-yl)ethyl)pyridin-3-yl)-3-fluoroaniline (300.0 mg, 0.63 mmol, 1.0 equiv.), trimethoxymethane (2.0 mL), azidotrimethylsilane (2.0 mL) and acetic acid (2.0 mL) was stirred overnight at 25° C. The reaction was purified by reverse chromatography on C18 (0→55% MeCN/H$_2$O (0.05% CF$_3$COOH)) to yield 1'-(1-(5-(3-chloro-2-fluoro-6-(1H-tetrazol-1-yl)phenyl)pyridin-2-yl)-2-cyclopropylethyl)-2-(difluoromethyl)-1'H,2H-3,4'-bipyrazole. LC/MS: mass calculated For $C_{24}H_{19}ClF_3N_9$: 525.14, measured (ES, m/z): 526.10 [M+H]$^+$.

Step 4: 1'-(1-(5-(3-Chloro-2-fluoro-6-(1H-tetrazol-1-yl)phenyl)pyridin-2-yl)-2-cyclopropylethyl)-2-(difluoromethyl)-4-fluoro-1'H,2H-3,4'-bipyrazole A mixture of 1'-(1-(5-(3-chloro-2-fluoro-6-(1H-tetrazol-1-yl)phenyl) pyridin-2-yl)-2-cyclopropylethyl)-2-(difluoromethyl)-1'H,2H-3,4'-bipyrazole (150.0 mg, 0.29 mmol, 1.0 equiv.) and Selectfluor™ (202.1 mg, 0.57 mmol, 2.0 equiv.) in acetonitrile (2.0 mL) was stirred at 60° C. The resulting mixture was purified by reverse phase chromatography on C18 (MeCN/H$_2$O (0.05% CF$_3$COOH)) to yield 1'-(1-(5-(3-chloro-2-fluoro-6-(1H-tetrazol-1-yl)phenyl)pyridin-2-yl)-2-cyclopropylethyl)-2-(difluoromethyl)-4-fluoro-1'H,2H-3,4'-bipyrazole as a brown solid. LC/MS: mass calculated For $C_{24}H_{18}ClF_4N_9$: 543.13, measured (ES, m/z): 544.10 [M+H]$^+$.

Step 5: (R)-5-(3-Chloro-2-fluoro-6-(1H-tetrazol-1-yl)phenyl)-2-(2-cyclopropyl-1-(2-(difluoromethyl)-4-fluoro-1'H,2H-[3,4'-bipyrazol]-1'-yl)ethyl)pyridine 1-oxide A mixture of 1'-(1-(5-(3-chloro-2-fluoro-6-(1H-tetrazol-1-yl)phenyl)pyridin-2-yl)-2-cyclopropylethyl)-2-(difluoromethyl)-4-fluoro-1'H,2H-3,4'-bipyrazole (60.0 mg, 0.11 mmol, 1.0 equiv.), methyltrioxorhenium (13.7 mg, 0.055 mmol, 0.5 equiv.) and hydrogen peroxide (0.2 mL, 30 wt. %) in CH$_3$OH (0.5 mL) was stirred for 2 h at room temperature. The resulting mixture was purified by reverse phase chromatography on C18 (MeCN/H$_2$O (0.05% CF$_3$COOH)) to yield a mixture of 5-(3-chloro-2-fluoro-6-(1H-tetrazol-1-yl)phenyl)-2-(2-cyclopropyl-1-(2-(difluoromethyl)-4-fluoro-1'H,2H-[3,4'-bipyrazol]-1'-yl)ethyl)pyridine 1-oxide as white solid. The racemic product was separated by chiral-HPLC to yield (R)-5-(3-chloro-2-fluoro-6-(1H-tetrazol-1-yl)phenyl)-2-(2-cyclopropyl-1-(2-(difluoromethyl)-4-fluoro-1'H,2H-[3,4'-bipyrazol]-1'-yl)ethyl)pyridine 1-oxide as a white solid.

LC/MS: mass calculated for C$_{24}$H$_{18}$ClF$_4$N$_9$O: 559.13, measured (ES, m/z): 582.05 [M+Na]$^+$. $^1$H NMR (300 MHz, DMSO-d$_6$) δ 9.68 (s, 1H), 8.44 (d, J=11.4 Hz, 2H), 7.57-8.13 (m, 5H), 7.38 (d, J=8.3 Hz, 1H), 7.10-7.20 (m, 1H), 6.10-6.20 (m, 1H), 2.24-2.34 (m, 1H), 1.94-2.07 (m, 1H), 0.53-0.63 (m, 1H), 0.22-0.39 (m, 2H), 0.06-0.14 (m, 1H), −0.04-−0.12 (m, 1H). $^{19}$F-NMR (282 MHz, DMSO-d$_6$) δ −93.94, −112.72, −171.38.

Example 666: (S)-5-(3-Chloro-6-(4-chloro-1H-1,2,3-triazol-1-yl)-2-fluorophenyl)-2-(1-(4-cyano-2-methyl-1'H,2H-[3,4'-bipyrazol]-1'-yl)-2-(4-fluorophenyl)ethyl)pyridine 1-oxide

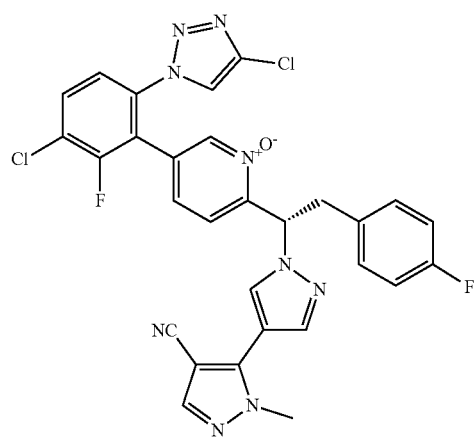

LC/MS: mass calculated for C$_{29}$H$_{19}$Cl$_2$F$_2$N$_9$O: 617.11, measured (ES, m/z): 618.00 [M+H]$^+$. $^1$H NMR (400 MHz, DMSO-d$_6$) δ 8.71 (s, 1H), 8.44-8.46 (m, 2H), 8.01-8.05 (m, 3H), 7.70 (dd, J=8.7, 1.5 Hz, 1H), 7.61 (d, J=8.3 Hz, 1H), 7.15-7.26 (m, 3H), 7.03-7.08 (m, 2H), 6.31-6.34 (m, 1H), 3.83 (s, 3H), 3.54-3.63 (m, 2H). $^{19}$F NMR (376 MHz, DMSO-d$_6$) δ −112.89, −115.96, −218.49.

Example 667: (R)-5-(3-Chloro-6-(4-chloro-1H-1,2,3-triazol-1-yl)-2-fluorophenyl)-2-(1-(4-cyano-2-methyl-1'H,2H-[3,4'-bipyrazol]-1'-yl)-2-(4-fluorophenyl)ethyl)pyridine 1-oxide

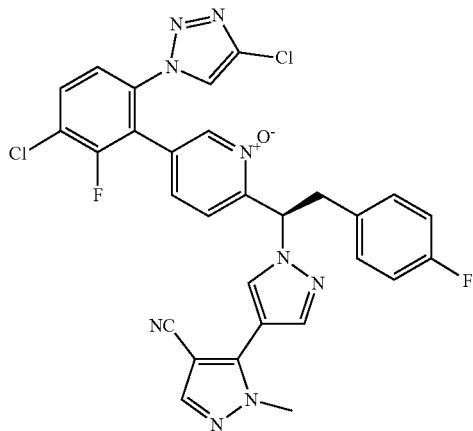

Step 1: 4-Ethynyl-2-methyl-1'H,2H-3,4'-bipyrazole

A mixture of 5-bromo-4-ethynyl-1-methyl-1H-pyrazole (1.0 g, 5.41 mmol, 1.0 equiv.), 1-Boc-pyrazole-4-boronic acid pinacol ester (3.2 g, 10.81 mmol, 2.0 equiv.), Pd(PPh$_3$)$_4$ (0.63 g, 0.54 mmol, 0.1 equiv.), K$_2$CO$_3$ (2.2 g, 16.21 mmol, 3.0 equiv.) in N,N-dimethylformamide (10 mL) and water (2 mL) was refluxed at 90° C. under N$_2$ for 2 h. The mixture was diluted with H$_2$O, extracted with ethyl acetate twice. The combined organic layers were washed with brine, dried over Na$_2$SO$_4$, concentrated, and purified by silica gel chromatography (0→10% MeOH/DCM) to yield 4-ethynyl-2-methyl-1'H,2H-3,4'-bipyrazole as a light yellow solid. LC/MS: mass calculated for C$_8$H$_7$N$_5$: 173.07, measured (ES, m/z): 174.10 [M+H]$^+$.

Step 2: 1'-(1-(5-Bromopyridin-2-yl)-2-(4-fluorophenyl)ethyl)-2-methyl-1'H,2H-[3,4'-bipyrazole]-4-carbonitrile A mixture of 2-methyl-1'H,2H-[3,4'-bipyrazole]-4-carbonitrile (0.30 g, 1.73 mmol, 1.2 equiv.) and cesium carbonate (0.52 g, 1.59 mmol, 1.1 equiv.) in acetonitrile (5 mL) was stirred for 15 min at room temperature. 1-(5-Bromopyridin-2-yl)-2-(4-fluorophenyl)ethyl methanesulfonate (0.54 g, 1.44 mmol, 1.0 equiv.) was added and the resulting mixture was stirred at 90° C. for 2 h. The solution was diluted with water, extracted with ethyl acetate twice. The combined organic layers were washed with brine, dried over Na$_2$SO$_4$, concentrated and purified by silica gel chromatography (0→80% EtOAc/petroleum ether) to yield 1'-(1-(5-bromopyridin-2-yl)-2-(4-fluorophenyl)ethyl)-2-methyl-1'H,2H-[3,4'-bipyrazole]-4-carbonitrile as a light yellow oil. LC/MS: mass calculated for C$_{21}$H$_{16}$BrFN$_6$: 450.06, measured (ES, m/z): 450.95, 452.95 [M+H, M+H+2]$^+$.

Step 3: (6-(1-(4-Cyano-2-methyl-1'H,2H-[3,4'-bipyrazol]-1'-yl)-2-(4-fluorophenyl)ethyl)pyridin-3-yl)boronic A mixture of 1'-(1-(5-bromopyridin-2-yl)-2-(4-fluorophenyl)ethyl)-2-methyl-1'H,2H-[3,4'-bipyrazole]-4-carbonitrile (0.60 g, 1.33 mmol, 1.0 equiv.), 4,4,4',4',5,5,5',5'-octamethyl-2,2'-bi(1,3,2-dioxaborolane) (0.68 g, 2.66 mmol, 2.0 equiv.), Pd(dppf)Cl$_2$ (0.097 g, 0.13 mmol, 0.1 equiv.), K$_2$CO$_3$ (0.39 g, 3.99 mmol, 3.0 equiv.) in 1,4-dioxane (6 mL) was refluxed at 90° C. under N$_2$ for 2 h. The mixture was diluted with H$_2$O, extracted with ethyl acetate twice. The combined organic layers was washed with brine, dried over Na$_2$SO$_4$, concentrated to yield (6-(1-(4-cyano-2-methyl-1'H,2H-[3,4'-bipyrazol]-1'-yl)-2-(4-fluorophenyl)ethyl)pyridin-3-yl)boronic acid. LC/MS: mass calculated for C$_{21}$H$_{18}$BFN$_6$O$_2$: 416.16, measured (ES, m/z): 417.05 [M+H]$^+$.

Step 4: 1'-(1-(5-(3-Chloro-6-(4-chloro-1H-1,2,3-triazol-1-yl)-2-fluorophenyl)pyridin-2-yl)-2-(4-fluorophenyl)ethyl)-2-methyl-1'H,2H-[3,4'-bipyrazole]-4-carbonitrile A mixture of (6-(1-(4-cyano-2-methyl-1'H,2H-[3,4'-bipyrazol]-1'-yl)-2-(4-fluorophenyl)ethyl)pyridin-3-yl)boronic acid (0.65 g, resulting), 4-chloro-1-(4-chloro-3-fluoro-2-iodophenyl)-1H-1,2,3-triazole (0.32 g, 0.90 mmol), Pd(PPh$_3$)$_4$ (0.14 g, 0.12 mmol), K$_2$CO$_3$ (0.50 g, 3.60 mmol) in 1,4-dioxane (4 mL) and water (1 mL) was refluxed at 90° C. under N$_2$ for 2 h. The mixture was diluted with H$_2$O, extracted with ethyl acetate twice. The combined organic layers was washed with brine, dried over Na$_2$SO$_4$, concentrated and purified by silica gel chromatography (0→8%, MeOH/DCM) to yield 1'-(1-(5-(3-chloro-6-(4-chloro-1H-1,2,3-triazol-1-yl)-2-fluorophenyl)pyridin-2-yl)-2-(4-fluorophenyl)ethyl)-2-methyl-1'H,2H-[3,4'-bipyrazole]-4-carbonitrile as a light yellow oil. LC/MS: mass calculated for C$_{29}$H$_{19}$Cl$_2$F$_2$N$_9$: 601.11, measured (ES, m/z): 624.00 [M+Na]$^+$.

Step 5: (S*)-5-(3-Chloro-6-(4-chloro-1H-1,2,3-triazol-1-yl)-2-fluorophenyl)-2-(1-(4-cyano-2-methyl-1'H,2H-[3,4'-bipyrazol]-1'-yl)-2-(4-fluorophenyl)ethyl)pyridine 1-oxide A mixture of 1'-(1-(5-(3-chloro-6-(4-chloro-1H-1,2,3-triazol-1-yl)-2-fluorophenyl)pyridin-2-yl)-2-(4-fluorophenyl)ethyl)-2-methyl-1'H,2H-[3,4'-bipyrazole]-4-carbonitrile (0.30 g, 0.50 mmol, 1.0 equiv.), hydrogen peroxide (30 wt %, 0.57 mL, 4.98 mmol, 10.0 equiv.) and methyltrioxorhenium (0.025 g, 0.10 mmol, 0.2 equiv.) in CH$_3$OH (3 mL) was stirred for 1 h at room temperature. The mixture was purified by reverse phase chromatography on C18 (80 g, MeCN/H$_2$O (0.05% CF$_3$COOH): 0→45%) and Prep-Chiral-HPLC to yield (R)-5-(3-chloro-6-(4-chloro-1H-1,2,3-triazol-1-yl)-2-fluorophenyl)-2-(1-(4-cyano-2-methyl-1'H,2H-[3,4'-bipyrazol]-1'-yl)-2-(4-fluorophenyl)ethyl)pyridine 1-oxide as a white solid.

LC/MS: mass calculated for C$_{29}$H$_{19}$Cl$_2$F$_2$N$_9$O: 617.11, measured (ES, m/z): 618.00 [M+H]$^+$. $^1$H NMR (400 MHz, DMSO-d$_6$) δ 8.71 (s, 1H), 8.42-8.49 (m, 2H), 7.99-8.07 (m, 3H), 7.66-7.75 (m, 3H), 7.61 (d, J=8.2 Hz, 1H), 7.14-7.26 (m, 3H), 7.01-7.11 (m, 2H), 6.28-6.40 (m, 1H), 3.83 (s, 3H), 3.52-3.66 (m, 2H).

Example 668: (R)-5-(3-Chloro-6-(4-chloro-1H-1,2,3-triazol-1-yl)-2-fluorophenyl)-2-(1-(2-(difluoromethyl)-4-fluoro-1'H,2H-[3,4'-bipyrazol]-1'-yl)-2-(4-fluoro-1H-pyrazol-1-yl)ethyl)pyridine 1-oxide

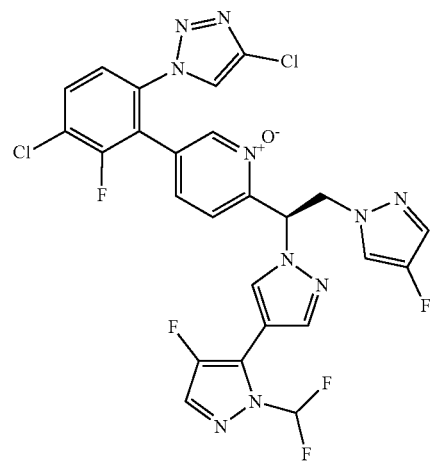

LC/MS: mass calculated for C$_{25}$H$_{15}$Cl$_2$F$_5$N$_{10}$O: 636.07, measured (ES, m/z): 637.05 [M+H]$^+$. $^1$H NMR (400 MHz, DMSO-d$_6$) δ 8.68 (s, 1H), 8.49 (d, J=1.6 Hz, 1H), 8.23 (s, 1H), 7.97-8.08 (m, 2H), 7.90 (s, 1H), 7.59-7.77 (m, 3H), 7.51 (d, J=8.3 Hz, 1H), 7.44 (d, J=4.1 Hz, 1H), 7.23 (dd, J=8.3, 1.7 Hz, 1H), 6.59-6.63 (m, 1H), 4.93-5.00 (m, 2H). $^{19}$F NMR (376 MHz, DMSO-d$_6$) δ −94.18 (d, J=44.3 Hz), −112.87, −171.13, −177.85.

Example 669: (S)-5-(3-Chloro-6-(difluoromethyl)-2-fluorophenyl)-2-(2-(4-fluorophenyl)-1-(4-(1-methyl-1H-1,2,3-triazol-5-yl)-1H-pyrazol-1-yl)ethyl)pyridine 1-oxide

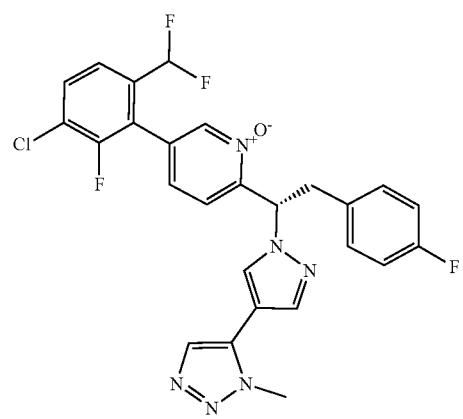

LC/MS: mass calculated for C$_{26}$H$_{19}$ClF$_4$N$_6$O: 542.12, measured (ES, m/z): 543.1 [M+H]$^+$. $^1$H NMR (400 MHz, DMSO-d$_6$) δ 8.56 (d, J=1.6 Hz, 1H), 8.45 (s, 1H), 8.05 (s, 1H), 7.88-7.92 (m, 1H), 7.85 (s, 1H), 7.63 (d, J=8.5 Hz, 1H), 7.57 (d, J=8.3 Hz, 1H), 7.44 (dd, J=8.2, 1.6 Hz, 1H), 7.18-7.28 (m, 2H), 6.77-7.12 (m, 3H), 6.31-6.34 (m, 1H), 4.02 (s, 3H), 3.57-3.72 (m, 2H). $^{19}$F NMR (376 MHz, DMSO-d$_6$) δ −109.36, −115.64.

Example 670: (S)-5-(3-Chloro-6-(4-chloro-1H-1,2,3-triazol-1-yl)-2-fluorophenyl)-2-(3-(difluoromethoxy)-1-(4-(1-methyl-1H-1,2,3-triazol-5-yl)-1H-pyrazol-1-yl)propyl)pyridine 1-oxide

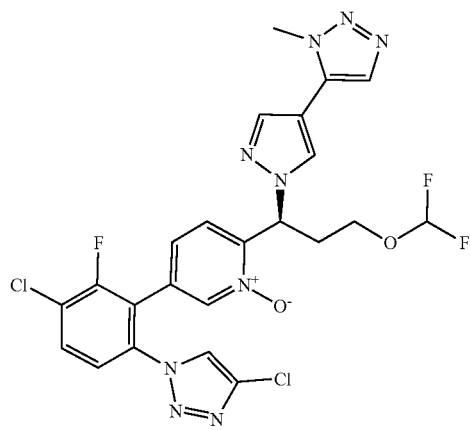 [SMILES: Cn1nncc1-c1cnn([C@@H](CCOC(F)F)c2ccc(-c3c(-n4cc(Cl)nn4)ccc(Cl)c3F)c[n+]2[O-])c1]

LC/MS: mass calculated for $C_{23}H_{18}Cl_2F_3N_9O_2$: 579.09, measured (ES, m/z): 580.05 [M+H]$^+$. $^1$H NMR (400 MHz, DMSO-d$_6$) δ 8.68 (s, 1H), 8.54 (s, 1H), 8.43 (d, J=1.6 Hz, 1H), 7.99-8.07 (m, 2H), 7.90 (s, 1H), 7.69 (dd, J=8.8, 1.5 Hz, 1H), 7.34 (d, J=8.3 Hz, 1H), 7.18 (dd, J=8.2, 1.7 Hz, 1H), 6.64 (t, J=75.7 Hz, 1H), 6.24-6.27 (m, 1H), 4.10 (s, 3H), 3.83-3.88 (m, 1H), 3.65-3.75 (m, 1H), 2.53-2.73 (m, 2H). $^{19}$F NMR (376 MHz, DMSO-d$_6$) δ −83.27, −112.92.

Example 671: (S)-5-(3-Chloro-6-(4-chloro-1H-1,2,3-triazol-1-yl)-2-fluorophenyl)-2-(1-(2-(difluoromethyl)-4-fluoro-1'H,2H-[3,4'-bipyrazol]-1'-yl)-2-(4-fluoro-1H-pyrazol-1-yl)ethyl)pyridine 1-oxide

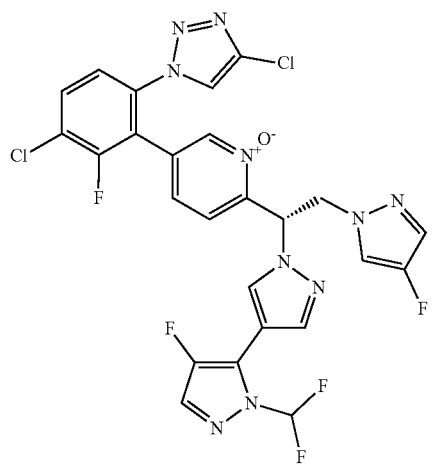

LC/MS: mass calculated for $C_{25}H_{15}Cl_2F_5N_{10}O$: 636.07, measured (ES, m/z): 637.10 [M+H]$^+$. $^1$H NMR (400 MHz, DMSO-d$_6$) δ 8.68 (s, 1H), 8.49 (d, J=1.6 Hz, 1H), 8.23 (s, 1H), 7.97-8.08 (m, 2H), 7.90 (s, 1H), 7.60-7.76 (m, 3H), 7.51 (d, J=8.3 Hz, 1H), 7.44 (d, J=4.2 Hz, 1H), 7.23 (dd, J=8.2, 1.7 Hz, 1H), 6.61 (dd, J=8.7, 5.6 Hz, 1H), 4.87-5.05 (m, 2H). $^{19}$F NMR (376 MHz, DMSO-d$_6$) δ −90.93, −112.87, −171.14, −177.86.

Example 672: (R)-5-(3-Chloro-6-(difluoromethyl)-2-fluorophenyl)-2-(2-(4-fluorophenyl)-1-(4-(1-methyl-1H-1,2,3-triazol-5-yl)-1H-pyrazol-1-yl)ethyl)pyridine 1-oxide

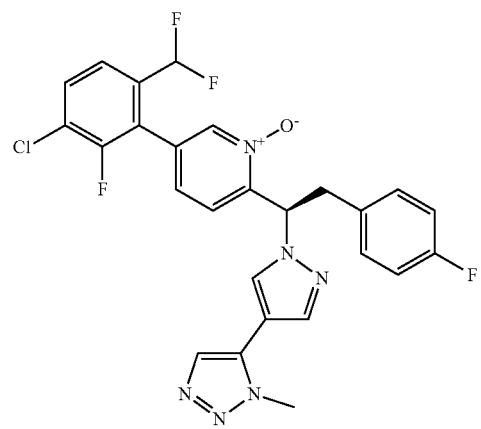 [SMILES: Cn1nncc1-c1cnn([C@H](Cc2ccc(F)cc2)c2ccc(-c3c(C(F)F)ccc(Cl)c3F)c[n+]2[O-])c1]

LC/MS: mass calculated for $C_{26}H_{19}ClF_4N_6O$: 542.12, measured (ES, m/z): 543.1 [M+H]$^+$. $^1$H NMR (400 MHz, DMSO-d$_6$) δ 8.56 (d, J=1.6 Hz, 1H), 8.45 (s, 1H), 8.05 (s, 1H), 7.88-7.92 (m, 1H), 7.85 (s, 1H), 7.63 (d, J=8.6 Hz, 1H), 7.57 (d, J=8.2 Hz, 1H), 7.44 (dd, J=8.2, 1.6 Hz, 1H), 7.19-7.27 (m, 2H), 6.77-7.13 (m, 3H), 6.31-6.34 (m, 1H), 4.02 (s, 3H), 3.58-3.72 (m, 2H). $^{19}$F NMR (376 MHz, DMSO-d$_6$) δ −109.37, −115.64.

Example 673: (R)-5-(3-Chloro-6-(4-chloro-1H-1,2,3-triazol-1-yl)-2-fluorophenyl)-2-(3-(difluoromethoxy)-1-(4-(1-methyl-1H-1,2,3-triazol-5-yl)-1H-pyrazol-1-yl)propyl)pyridine 1-oxide

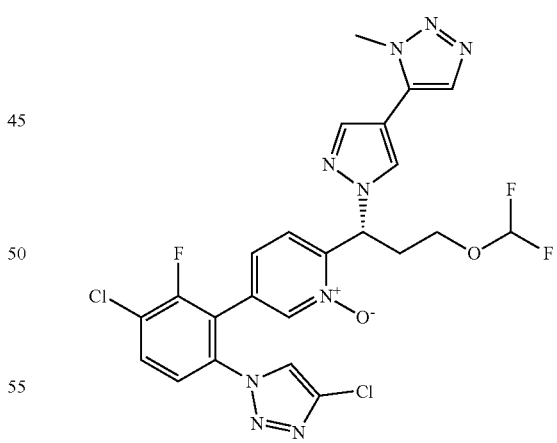

Step 1. 1-(5-Bromopyridin-2-yl)-3-((tert-butyldimethylsilyl)oxy)propan-1-ol

To a solution of 2,5-dibromopyridine (28 g, 118.197 mol, 1.0 equiv) in toluene (450 mL), n-butyllithium (49.643 mL, 124.107 mmol, 1.05 equiv, 2.5 M) was dropped in at −78° C. in N$_2$ and stirred for 1 h under N$_2$. Then 3-((tert-butyldimethylsilyl)oxy)-N-methoxy-N,3-dimethylbutanamide (26.713 g, 141.837 mmol, 1.2 equiv) was added and stirred for another 1 h. The reaction was then quenched by the addition of saturated ammonium chloride aqueous solution and extracted with ethyl acetate twice. The combined organic layers was washed with brine, dried over $Na_2SO_4$, concentrated under reduced pressure and the residue was purified by silica gel chromatography (0-20% EtOAc/petroleum ether) to yield 1-(5-bromopyridin-2-yl)-3-((tert-butyldimethylsilyl)oxy)propan-1-ol (26 g, 63.514% yield) as a yellow oil. LC/MS: mass calculated for $C_{14}H_{24}BrNO_2Si$: 345.08, measured: 346.15 $[M+H]^+$.

Step 2. 5-Bromo-2-(3-((tert-butyldimethylsilyl)oxy)-1-((tetrahydro-2H-pyran-2-yl)oxy)propyl)pyridine To a solution of 1-(5-bromopyridin-2-yl)-3-((tert-butyldimethylsilyl)oxy)propan-1-ol (145 g, 418.670 mmol, 1 equiv) and 3,4-dihydro-2H-pyran (105.651 g, 1256.09 mmol, 3.0 equiv) in DCM (1500 mL) was added 3-((tert-butyldimethylsilyl)oxy)propanal (7.210 g, 41.867 mmol, 0.1 equiv). The reaction mixture was stirred at 70° C. for 1 h, then the reaction mixture was quenched with $NaHCO_3$, extracted with EA. The combined organic layers was washed with brine, dried over $Na_2SO_4$ and concentrated under vacuum to yield 5-bromo-2-(3-((tert-butyldimethylsilyl)oxy)-1-((tetrahydro-2H-pyran-2-yl)oxy)propyl)pyridine (130 g). LC/MS: mass calculated for $C_{19}H_{32}BrNO_3Si$: 429.13, measured: 430.25 $[M+H]^+$.

Step 3. 3-(5-Bromopyridin-2-yl)-3-(tetrahydro-2H-pyran-2-yloxy)propan-1-ol

To a solution of 5-bromo-2-(3-((tert-butyldimethylsilyl)oxy)-1-((tetrahydro-2H-pyran-2-yl)oxy)propyl)pyridine (130 g, 302.008 mmol, 1.0 equiv) in tetrahydrofuran (1500 mL), triethylamine trihydrofluoride (97.374 g, 604.016 mmol, 2.0 equiv) was added. The reaction was stirred for 2.5 h at 70° C. The reaction was quenched with water and extracted with EA three times. The combined organic layers were washed with brine, dried over $Na_2SO_4$ and concentrated under vacuum. The residue was purified by silica gel chromatography with EA/PE (0-30%) to give 3-(5-bromopyridin-2-yl)-3-(tetrahydro-2H-pyran-2-yloxy)propan-1-ol as yellow oil (70 g, 73.304% yield). LC/MS: mass calculated for $C_{13}H_{18}BrNO_3$: 315.05, measured: 316.05 [M+H]+.

Step 4. 5-Bromo-2-(3-(difluoromethoxy)-1-((tetrahydro-2H-pyran-2-yl)oxy)propyl)pyridine To a solution of 3-(5-bromopyridin-2-yl)-3-((tetrahydro-2H-pyran-2-yl)oxy)propan-1-ol (67 g, 211.897 mmol, 1 equiv) in acetonitrile (800 mL) was added cuprous iodide (8.071 g, 42.379 mmol, 0.2 equiv). then dropwise added 2-(fluorosulfonyl)difluoroacetic acid (56.604 g, 317.846 mmol, 1.5 equiv) for 1 h at 50° C. in $N_2$. The reaction was quenched with water and extracted with EA three times. The combined organic layers were washed with brine, dried over $Na_2SO_4$ and concentrated under vacuum. The residue was purified by silica gel chromatography with EA/PE (0-20%) gave 5-bromo-2-(3-(difluoromethoxy)-1-((tetrahydro-2H-pyran-2-yl)oxy)propyl)pyridine as yellow oil (50 g, 64.436% yield). LC/MS: mass calculated for $C_{14}H_{18}BrF_2NO_3$: 365.04, measured: 366.15 $[M+H]^+$.

Step 5. 1-(5-Bromopyridin-2-yl)-3-(difluoromethoxy)propan-1-ol

To a solution of 5-bromo-2-(3-(difluoromethoxy)-1-((tetrahydro-2H-pyran-2-yl)oxy)propyl)pyridine (49 g, 133.807 mmol, 1 equiv) in dichloromethane (500 mL) was added trifluoroacetic acid (1500 mL). The reaction mixture was stirred at rt for 3 h, The reaction was quenched with water and concentrated under vacuum. The product 1-(5-bromopyridin-2-yl)-3-(difluoromethoxy)propan-1-ol as a brown oil (35 g, 92.728% yield). LC/MS: mass calculated for $C_9H_{10}BrF_2NO_2$: 280.99, measured: 282.05 $[M+H]^+$.

Step 6. 1-(5-Bromopyridin-2-yl)-3-(difluoromethoxy)propyl methanesulfonate

To a mixture of 1-(5-bromopyridin-2-yl)-3-(difluoromethoxy)propan-1-ol (45 g, 159.528 mmol, 1 equiv.) and triethylamine (80.715 g, 794.640 mmol, 5 equiv.) in DCM (1000 mL) was added Methanesulfonic anhydride (55.578 g, 319.056 mmol, 2 equiv.) at 0° C. and the solution was stirred for 2 h at room temperature. The mixture was diluted with $H_2O$, extracted with DCM twice. The combined organic layers were washed with brine, dried over $Na_2SO_4$, concentrated and purified by silica gel chromatography (0-30% EtOAc/petroleum ether) to yield 1-(5-bromopyridin-2-yl)-3-(difluoromethoxy)propyl methanesulfonate as a light yellow solid (34 g, 59.174% yield). LC/MS: mass calculated for $C_{10}H_{12}BrF_2NO_4S$: 359, measured: 360.05 $[M+H]^+$.

Step 7. 5-Bromo-2-(3-(difluoromethoxy)-1-(4-(1-methyl-1H-1,2,3-triazol-5-yl)-1H-pyrazol-1-yl)propyl)pyridine A mixture of 1-methyl-5-(1H-pyrazol-4-yl)-1H-1,2,3-triazole (2.961 g, 19.852 mmol, 1.1 equiv.) and cesium carbonate (6.468 g, 19.852 mmol, 1.1 equiv.) in acetonitrile (60 mL) was stirred for 15 min at room temperature. 1-(5-bromopyridin-2-yl)-3-(difluoromethoxy)propyl methanesulfonate (6.5 g, 18.047 mmol, 1 equiv.) was added and the solution was stirred for 3 h at 90° C. The solution was diluted with $H_2O$, extracted with ethyl acetate twice. The combined organic layers was washed with brine, dried over $Na_2SO_4$, concentrated and the residue was purified by silica gel chromatography (0→50% EtOAc/petroleum ether) to yield 5-bromo-2-(3-(difluoromethoxy)-1-(4-(1-methyl-1H-1,2,3-triazol-5-yl)-1H-pyrazol-1-yl)propyl)pyridine as a light yellow oil (6.6 g, 88.503% yield). LC/MS: mass calculated for $C_{15}H_{15}BrF_2N_6O$: 412, measured: 413.15 $[M+H]^+$.

Step 8. (6-(3-(Difluoromethoxy)-1-(4-(1-methyl-1H-1,2,3-triazol-5-yl)-1H-pyrazol-1-yl)propyl)pyridin-3-yl)boronic acid A mixture of 5-bromo-2-(3-(difluoromethoxy)-1-(4-(1-methyl-1H-1,2,3-triazol-5-yl)-1H-pyrazol-1-yl)propyl)pyridine (6.6 g, 15.972 mmol, 1 equiv.), 4,4,4',4',5,5,5',5'-octamethyl-2,2'-bi(1,3,2-dioxaborolane) (8.112 g, 31.944 mmol, 2 equiv.), Pd(dppf)$Cl_2$ (1.169 g, 1.597 mmol, 0.1 equiv.) and KOAc (0.584 g, 5.953 mmol, 3 equiv.) in 1,4-dioxane (60 mL) was stirred for 2 h at 90° C. in a nitrogen atmosphere. The mixture was diluted with $H_2O$, extracted with ethyl acetate twice. The combined organic layers was washed with brine, dried over $Na_2SO_4$ and concentrated to yield (6-(3-(difluoromethoxy)-1-(4-(1- methyl-1H-1,2,3-triazol-5-yl)-1H-pyrazol-1-yl)propyl)pyridin-3-yl)boronic acid as deep yellow oil (6 g).

Step 9. 5-(3-Chloro-6-(4-chloro-1H-1,2,3-triazol-1-yl)-2-fluorophenyl)-2-(3-(difluoromethoxy)-1-(4-(1-methyl-1H-1,2,3-triazol-5-yl)-1H-pyrazol-1-yl)propyl)pyridine A mixture of (6-(3-(difluoromethoxy)-1-(4-(1-methyl-1H-1,2,3-triazol-5-yl)-1H-pyrazol-1-yl)propyl)pyridin-3-yl)boronic acid (0.75 g, 1.983 mmol, 1 equiv), 4-chloro-1-(4-chloro-3-fluoro-2-iodophenyl)-1H-1,2,3-triazole (0.852 g, 2.380 mmol, 1.2 equiv), Pd(PPh$_3$)$_4$ (0.458 g, 0.397 mmol, 0.2 equiv), K$_2$CO$_3$ (1.645 g, 11.900 mmol, 6 equiv) in 1,4-dioxane (10 ml) and water (2 ml) was refluxed at 90° C. under N$_2$ for 2 h. The mixture was diluted with H$_2$O, extracted with ethyl acetate twice. The combined organic layers was washed with brine, dried over Na$_2$SO$_4$, concentrated and purified by silica gel chromatography (0→8%, MeOH/DCM) to yield 5-(3-chloro-6-(4-chloro-1H-1,2,3-triazol-1-yl)-2-fluorophenyl)-2-(3-(difluoromethoxy)-1-(4-(1-methyl-1H-1,2,3-triazol-5-yl)-1H-pyrazol-1-yl)propyl)pyridine as a yellow solid (1.1 g, 98.274% yield). LC/MS: mass calculated for C$_{23}$H$_{18}$Cl$_2$F$_3$N$_9$O: 563, measured: 564.05 [M+H]$^+$.

Step 10. (R)-5-(3-Chloro-6-(4-chloro-1H-1,2,3-triazol-1-yl)-2-fluorophenyl)-2-(3-(difluoromethoxy)-1-(4-(1-methyl-1H-1,2,3-triazol-5-yl)-1H-pyrazol-1-yl)propyl)pyridine 1-oxide A mixture of 5-(3-chloro-6-(4-chloro-1H-1,2,3-triazol-1-yl)-2-fluorophenyl)-2-(3-(difluoromethoxy)-1-(4-(1-methyl-1H-1,2,3-triazol-5-yl)-1H-pyrazol-1-yl)propyl)pyridine (1.1 g, 1.949 mmol, 1 equiv.), hydrogen peroxide (2.210 mL, 19.491 mmol, 10 equiv.) and methyltrioxorhenium (0.097 g, 0.390 mmol, 0.2 equiv.) in methanol (10 mL) was stirred for 1 h at room temperature. The mixture was purified by revers phase chromatography on C18 (80 g, MeCN/H$_2$O (0.05% CF$_3$COOH): 0>>>45%) to yield 5-(3-chloro-6-(4-chloro-1H-1,2,3-triazol-1-yl)-2-fluorophenyl)-2-(3-(difluoromethoxy)-1-(4-(1-methyl-1H-1,2,3-triazol-5-yl)-1H-pyrazol-1-yl)propyl)pyridine 1-oxide. The racemic product was separated by Chiral-HPLC to yield (R)-5-(3-chloro-6-(4-chloro-1H-1,2,3-triazol-1-yl)-2-fluorophenyl)-2-(3-(difluoromethoxy)-1-(4-(1-methyl-1H-1,2,3-triazol-5-yl)-1H-pyrazol-1-yl)propyl)pyridine 1-oxide (215.6 mg, 19.034% yield) as a white solid.

LC/MS: mass calculated for C$_{23}$H$_{18}$Cl$_2$F$_3$N$_9$O$_2$: 579.09, measured (ES, m/z): 580.05 [M+H]$^+$. $^1$H NMR (400 MHz, DMSO-d$_6$) δ 8.68 (s, 1H), 8.54 (s, 1H), 8.43 (s, 1H), 7.99-8.07 (m, 2H), 7.90 (s, 1H), 7.69 (dd, J=8.7, 1.5 Hz, 1H), 7.34 (d, J=8.3 Hz, 1H), 7.18 (dd, J=8.3, 1.7 Hz, 1H), 6.64 (t, J=75.7 Hz, 1H), 6.26 (dd, J=10.0, 4.6 Hz, 1H), 4.10 (s, 3H), 3.82-3.91 (m, 1H), 3.65-3.77 (m, 1H), 2.56-2.72 (m, 2H). $^{19}$F NMR (376 MHz, DMSO-d$_6$) δ −83.27, −112.92.

Example 674: (S)-2-(3-(tert-Butoxy)-1-(2-(difluoromethyl)-1'H,2H-[3,4'-bipyrazol]-1'-yl)propyl)-5-(3-chloro-2-fluoro-6-(1H-tetrazol-1-yl)phenyl)pyridine 1-oxide

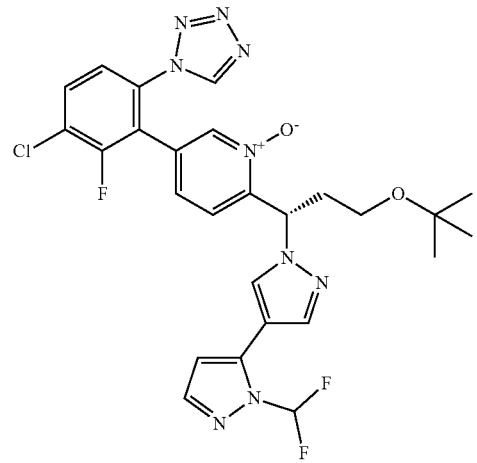 [SMILES: CC(C)(C)OCC[C@@H](c1ccc(-c2c(-n3cnnn3)ccc(Cl)c2F)c[n+]1[O-])n1cc(-c2ccnn2C(F)F)cn1]

LC/MS: mass calculated for C$_{26}$H$_{25}$ClF$_3$N$_9$O$_2$: 587.18, measured (ES, m/z): 610.10 [M+Na]$^+$. $^1$H NMR (300 MHz, DMSO-d$_6$) δ 9.68 (s, 1H), 8.42 (d, J=1.5 Hz, 1H), 8.35 (s, 1H), 7.62-8.11 (m, 5H), 7.45 (d, J=8.3 Hz, 1H), 7.19 (dd, J=8.2, 1.7 Hz, 1H), 6.67 (d, J=1.7 Hz, 1H), 6.19-6.24 (m, 1H), 3.25-3.30 (m, 1H), 3.10-3.16 (m, 1H), 2.37-2.46 (m, 2H), 1.02 (s, 9H). $^{19}$F NMR (282 MHz, DMSO-d$_6$) δ −93.57, −93.64, −112.70.

Example 675: (S*)-2-(1-(4-(4-Chloro-1-methyl-1H-1,2,3-triazol-5-yl)-1H-pyrazol-1-yl)-3-methoxypropyl)-5-(3-chloro-6-(4-chloro-1H-1,2,3-triazol-1-yl)-2-fluorophenyl)pyridine 1-oxide

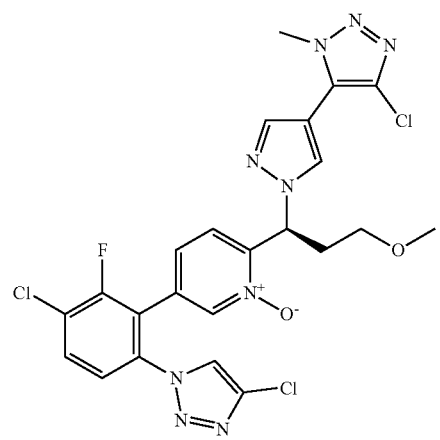 [SMILES: COCC[C@@H](c1ccc(-c2c(-n3cc(Cl)nn3)ccc(Cl)c2F)c[n+]1[O-])n1cc(-c2c(Cl)nnn2C)cn1]

LC/MS: mass calculated for C$_{23}$H$_{19}$Cl$_3$FN$_9$O$_2$: 577.07, measured (ES, m/z): 578.00 [M+H]$^+$. $^1$H NMR (400 MHz, DMSO-d$_6$) δ 8.69 (s, 1H), 8.58 (d, J=0.8 Hz, 1H), 8.42 (d, J=1.6 Hz, 1H), 7.99-8.09 (m, 2H), 7.70 (dd, J=8.7, 1.5 Hz, 1H), 7.42 (d, J=8.3 Hz, 1H), 7.15-7.25 (m, 1H), 6.25-6.29 (m, 1H), 4.12 (s, 3H), 3.27-3.36 (m, 1H), 3.20 (s, 3H), 3.12-3.18 (m, 1H), 2.46-2.50 (m, 2H). $^{19}$F NMR (376 MHz, DMSO-d$_6$) δ −73.56, −112.95.

Example 676: (R)-2-(1-(4-(4-Chloro-1-methyl-1H-1,2,3-triazol-5-yl)-1H-pyrazol-1-yl)-3-methoxypropyl)-5-(3-chloro-6-(4-chloro-1H-1,2,3-triazol-1-yl)-2-fluorophenyl)pyridine 1-oxide

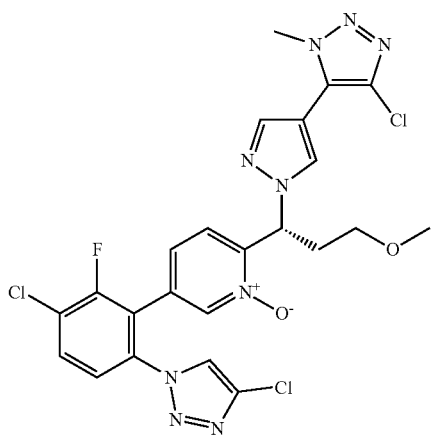 [SMILES: COCC[C@H](c1ccc(-c2c(-n3cc(Cl)nn3)ccc(Cl)c2F)c[n+]1[O-])n1cc(-c2c(Cl)nnn2C)cn1]

Step 1: 1-Methyl-5-(1H-pyrazol-4-yl)-1H-1,2,3-triazole

A mixture of 5-bromo-4-(trifluoromethyl)thiazole (3.8 g, 18.2 mmol, 1.0 equiv.), 1-Boc-pyrazole-4-boronic acid pinacol ester (10.7 g, 36.4 mmol, 2.0 equiv.), Pd(PPh$_3$)$_4$ (2.1 g, 1.8 mmol, 0.1 equiv.), K$_2$CO$_3$ (7.5 g, 54.5 mmol, 3.0 equiv.) in DMF (40 mL) and water (8 mL) was stirred at 90° C. under N$_2$ for 2 h. The solution was diluted with H$_2$O, extracted with ethyl acetate twice. The combined organic layers were washed with brine, dried over Na$_2$SO$_4$, concentrated and purified by silica gel chromatography (0→10% MeOH/DCM) to yield 1-methyl-5-(1H-pyrazol-4-yl)-1H-1,2,3-triazole as a light yellow solid. LC/MS: mass calculated for C$_6$H$_7$N$_5$: 149.07 measured (ES, m/z): 150.10 [M+H]$^+$.

Step 2: 5-Bromo-2-(3-methoxy-1-(4-(1-methyl-1H-1,2,3-triazol-5-yl)-1H-pyrazol-1-yl)propyl)pyridine A mixture of 1-methyl-5-(1H-pyrazol-4-yl)-1H-1,2,3-triazole (1.0 g, 6.7 mmol, 1.0 equiv.) and cesium carbonate (2.4 g, 7.4 mmol, 1.1 equiv.) in acetonitrile (10 mL) was stirred for 15 min at room temperature. 1-(5-Bromopyridin-2-yl)-3-methoxypropyl methanesulfonate (2.2 g, 6.7 mmol, 1.0 equiv.) was added and the mixture was stirred for 3 h at 90° C. The mixture was diluted with H$_2$O, extracted with ethyl acetate twice. The combined organic layers were washed with brine, dried over Na$_2$SO$_4$, concentrated and purified by silica gel chromatography (0→50% EA/PE) to yield 5-bromo-2-(3-methoxy-1-(4-(1-methyl-1H-1,2,3-triazol-5-yl)-1H-pyrazol-1-yl)propyl)pyridine as light yellow oil. LC/MS: mass calculated for C$_{15}$H$_{17}$BrN$_6$O: 376.06, measured (ES, m/z): 376.95 [M+H]$^+$.

Step 3: 5-Bromo-2-(1-(4-(4-chloro-1-methyl-1H-1,2,3-triazol-5-yl)-1H-pyrazol-1-yl)-3-methoxypropyl)pyridine A mixture of 5-bromo-2-(3-methoxy-1-(4-(1-methyl-1H-1,2,3-triazol-5-yl)-1H-pyrazol-1-yl)propyl)pyridine (0.5 g, 1.3 mmol, 1 equiv.), 1-chloropyrrolidine-2,5-dione (1.1 g, 4.0 mmol, 3.0 equiv.) in DMF (5 mL) was stirred for 48 h at room temperature. The mixture was diluted with H$_2$O, extracted with ethyl acetate twice. The combined organic layers were washed with brine, dried over Na$_2$SO$_4$, concentrated and purified by silica gel chromatography (0→80%, EA/PE) to yield 5-bromo-2-(1-(4-(4-chloro-1-methyl-1H-1,2,3-triazol-5-yl)-1H-pyrazol-1-yl)-3-methoxypropyl)pyridine as light yellow oil. LC/MS: mass calculated for C$_{15}$H$_{16}$BrClN$_6$O: 410.13, measured (ES, m/z): 410.95, 412.95 [M+H, M+2+H]$^+$.

Step 4: (6-(1-(4-(4-Chloro-1-methyl-1H-1,2,3-triazol-5-yl)-1H-pyrazol-1-yl)-3-methoxypropyl)pyridin-3-yl)boronic acid A mixture of 5-bromo-2-(1-(4-(4-chloro-1-methyl-1H-1,2,3-triazol-5-yl)-1H-pyrazol-1-yl)-3-methoxypropyl)pyridine (0.5 g, 1.2 mmol, 1 equiv.), 4,4,4',4',5,5,5',5'-octamethyl-2,2'-bi(1,3,2-dioxaborolane) (0.6 g, 2.4 mmol, 2.0 equiv.), Pd(dppf)Cl$_2$ (89 mg, 0.12 mmol, 0.1 equiv.), K$_2$CO$_3$ (0.36 g, 3.6 mmol, 3.0 equiv.) in 1,4-dioxane (5 mL) was refluxed at 90° C. under N$_2$ for 2 h. The mixture was diluted with H$_2$O, extracted with ethyl acetate twice. The combined organic layers was washed with brine, dried over Na$_2$SO$_4$, concentrated to yield (6-(1-(4-(4-chloro-1-methyl-1H-1,2,3-triazol-5-yl)-1H-pyrazol-1-yl)-3-methoxypropyl)pyridin-3-yl)boronic acid. LC/MS: mass calculated for C$_{15}$H$_{18}$BClN$_6$O$_3$: 376.12, measured (ES, m/z): 377.05 [M+H]$^+$.

Step 5: 2-(1-(4-(4-Chloro-1-methyl-1H-1,2,3-triazol-5-yl)-1H-pyrazol-1-yl)-3-methoxypropyl)-5-(3-chloro-6-(4-chloro-1H-1,2,3-triazol-1-yl)-2-fluorophenyl)pyridine A mixture of (6-(1-(4-(4-chloro-1-methyl-1H-1,2,3-triazol-5-yl)-1H-pyrazol-1-yl)-3-methoxypropyl)pyridin-3-yl)boronic acid (200 mg, 0.53 mmol, 1.0 equiv.), 4-chloro-1-(4-chloro-3-fluoro-2-iodophenyl)-1H-1,2,3-triazole (285 mg, 0.80 mmol, 1.5 equiv.), Pd(PPh$_3$)$_4$ (123 mg, 0.11 mmol, 0.2 equiv.), K$_2$CO$_3$ (440 mg, 3.19 mmol, 6.0 equiv.) in 1,4-dioxane (4 mL) and water (1 mL) was stirred at 90° C. under N$_2$ for 2 h. The mixture was diluted with H$_2$O, extracted with ethyl acetate twice. The combined organic layers were washed with brine, dried over Na$_2$SO$_4$, concentrated and purified by silica gel chromatography (0→8%, MeOH/DCM) to yield 2-(1-(4-(4-chloro-1-methyl-1H-1,2,3-triazol-5-yl)-1H-pyrazol-1-yl)-3-methoxypropyl)-5-(3-chloro-6-(4-chloro-1H-1,2,3-triazol-1-yl)-2-fluorophenyl)pyridine as light yellow oil. LC/MS: mass calculated for C$_{23}$H$_{19}$Cl$_3$FN$_9$O: 561.08, measured (ES, m/z): 564.00 [M+H]$^+$.

Step 6: (R)-2-(1-(4-(4-Chloro-1-methyl-1H-1,2,3-triazol-5-yl)-1H-pyrazol-1-yl)-3-methoxypropyl)-5-(3-chloro-6-(4-chloro-1H-1,2,3-triazol-1-yl)-2-fluorophenyl)pyridine 1-oxide A mixture of 2-(1-(4-(4-chloro-1-methyl-1H-1,2,3-triazol-5-yl)-1H-pyrazol-1-yl)-3-methoxypropyl)-5-(3-chloro-6-(4-chloro-1H-1,2,3-triazol-1-yl)-2-fluorophenyl)pyridine (200 mg, 0.36 mmol, 1.0 equiv.), hydrogen peroxide (30 wt %, 0.40 mL, 3.6 mmol, 10.0 equiv.) and methyltrioxorhenium (18 mg, 0.07 mmol, 0.2 equiv.) in CH$_3$OH (2 mL) was stirred for 1 h at room temperature. The mixture was purified by reverse phase chromatography on C18 (80 g, MeCN/H$_2$O (0.05% CF$_3$COOH): 0→45%) to yield 2-(1-(4-(4-chloro-1- methyl-1H-1,2,3-triazol-5-yl)-1H-pyrazol-1-yl)-3-methoxypropyl)-5-(3-chloro-6-(4-chloro-1H-1,2,3-triazol-1-yl)-2-fluorophenyl)pyridine 1-oxide. The racemic product was separated by Chiral-HPLC to yield (R)-2-(1-(4-(4-chloro-1-methyl-1H-1,2,3-triazol-5-yl)-1H-pyrazol-1-yl)-3-methoxypropyl)-5-(3-chloro-6-(4-chloro-1H-1,2,3-triazol-1-yl)-2-fluorophenyl)pyridine 1-oxide as a white solid.

LC/MS: mass calculated for $C_{23}H_{19}Cl_3FN_9O_2$: 577.07, measured (ES, m/z): 578.00 [M+H]$^+$. $^1$H NMR (400 MHz, DMSO-d$_6$): δ 8.69 (s, 1H), 8.58 (d, J=0.7 Hz, 1H), 8.39-8.44 (m, 1H), 7.99-8.09 (m, 2H), 7.65-7.75 (m, 1H), 7.42 (d, J=8.3 Hz, 1H), 7.15-7.22 (m, 1H), 6.28 (t, J=7.3 Hz, 1H), 4.12 (s, 3H), 3.27-3.35 (m, 1H), 3.20 (s, 3H), 3.12-3.19 (m, 1H), 2.46-2.50 (m, 2H).

Example 677: (R)-2-(3-(tert-Butoxy)-1-(2-(difluoromethyl)-1'H,2H-[3,4'-bipyrazol]-1'-yl)propyl)-5-(3-chloro-2-fluoro-6-(1H-tetrazol-1-yl)phenyl)pyridine 1-oxide

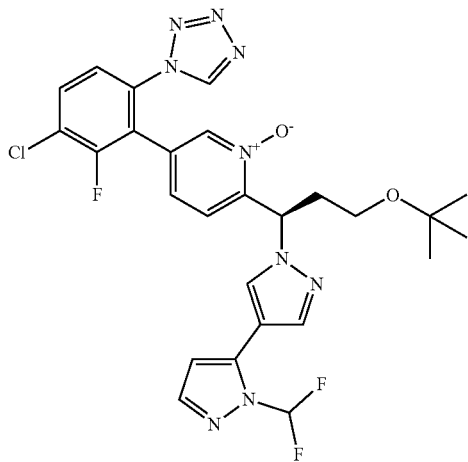 [SMILES: CC(C)(C)OCC[C@H](c1ccc(-c2c(-n3cnnn3)ccc(Cl)c2F)c[n+]1[O-])n1cc(-c2ccnn2C(F)F)cn1]

Step 1:
3-(tert-butoxy)-N-methoxy-N-methylpropanamide

To a solution of 3-(tert-butoxy)propanoic acid (1.0 g, 6.84 mmol, 1.0 equiv.) in DCM (15 mL) was added CDI (1.7 g, 10.26 mmol, 1.5 equiv.) slowly, then the mixture was stirred at room temperature for 10 min. After that, N,O-dimethylhydroxylamine hydrogen chloride (1.0 g, 10.26 mmol, 1.5 equiv.) was added to the mixture was stirred at room temperature overnight. The reaction was quenched with 1N HCl and extracted with DCM twice. The combined organic layer was washed with saturated aqueous NaHCO$_3$ and brine, dried over anhydrous Na$_2$SO$_4$ and concentrated to yield 3-(tert-butoxy)-N-methoxy-N-methylpropanamide as a light yellow oil which was used in the next step without purified. LC/MS: mass calculated for $C_9H_{19}NO_3$: 189.14, measured (ES, m/z): 190.15 [M+H]$^+$.

Step 2: 1-(5-Bromopyridin-2-yl)-3-(tert-butoxy)propan-1-one

To a solution of 2,5-dibromopyridine (1.4 g, 5.76 mmol, 1.0 equiv.) in toluene (15 mL) was added n-butyllithium (2.5 mL, 6.33 mmol, 1.1 equiv, 2.5 M in hexane) at −78° C., and then the mixture was stirred at this temperature for 1 h. Then 3-(tert-butoxy)-N-methoxy-N-methylpropanamide (1.2 g, 6.34 mmol, 1.1 equiv.) was added and the mixture stirred at this temperature for 1 h. The resulting mixture was quenched by saturated aqueous NH$_4$Cl (30 mL) and extracted with EA (3×30 mL). The organic layers were combined, washed with brine, dried over Na$_2$SO$_4$ and concentrated. The residue was purified by (0%→25%, EA/PE) to yield 1-(5-bromopyridin-2-yl)-3-(tert-butoxy)propan-1-one as a light yellow oil. LC/MS: mass calculated for $C_{12}H_{16}BrNO_2$: 285.04, measured (ES, m/z): 286.00 [M+H]$^+$.

Step 3: 1-(5-Bromopyridin-2-yl)-3-(tert-butoxy)propan-1-ol

To a solution of 1-(5-bromopyridin-2-yl)-3-(tert-butoxy)propan-1-one (473 mg, 1.65 mmol, 1.0 equiv.) in CH$_3$OH (3 mL) was added NaBH$_4$ (125 mg, 3.31 mmol, 2.0 equiv.) in several portions at 0° C. Then the mixture was stirred at room temperature for 2 h. The resulting mixture was quenched by water (10 mL) and extract with EA (3×10 mL). Then the organic layers were combined, washed with brine, dried over Na$_2$SO$_4$, and concentrated to yield 1-(5-bromopyridin-2-yl)-3-(tert-butoxy)propan-1-ol as a light yellow oil. LC/MS: mass calculated for $C_{13}H_{20}BrNO_4S$: 365.03, measured (ES, m/z): 368.00 [M+H+2]$^+$.

Step 4: 1-(5-Bromopyridin-2-yl)-3-(tert-butoxy)propyl methanesulfonate

To a solution of 1-(5-bromopyridin-2-yl)-3-(tert-butoxy)propan-1-ol (433 mg, 1.50 mmol, 1.0 equiv.) in chloromethane (3 mL) was added triethylamine (608 mg, 6.01 mmol, 4.0 equiv.) under 0° C., followed by methanesulfonic anhydride (523 mg, 3.01 mmol, 2.0 equiv.). The resulting mixture was stirred at room temperature for 2 h. The reaction was quenched by water (10 mL), extracted with EA (3×10 mL). The organic layers were combined, washed with brine, dried over Na$_2$SO$_4$ and concentrated. The residue was purified by silica gel chromatography (EA/PE, 0%→35%) to yield 1-(5-bromopyridin-2-yl)-3-(tert-butoxy)propyl methanesulfonate as a light yellow oil.

Step 5: 1'-(1-(5-Bromopyridin-2-yl)-3-(tert-butoxy)propyl)-2-(difluoromethyl)-1'H,2H-3,4'-bipyrazole A mixture of cesium carbonate (398 mg, 1.22 mmol, 1.0 equiv.) and 2-(difluoromethyl)-1'H,2H-3,4'-bipyrazole (225 mg, 1.22 mmol, 1.0 equiv.) in acetonitrile (3 mL) was stirred for 15 min at room temperature. 1-(5-bromopyridin-2-yl)-3-(tert-butoxy)propyl methanesulfonate (447 mg, 1.22 mmol, 1.0 equiv.) was added and the solution was stirred for 2.5 h at 70° C. The resulting mixture was diluted with water, extracted with EA (3×5 mL). The organic layers were combined, washed with brine, dried over Na$_2$SO$_4$ and concentrated. The residue was purified by silica gel chromatography (EA/PE, 0%→50%) to yield 1'-(1-(5-bromopyridin-2-yl)-3-(tert-butoxy)propyl)-2-(difluoromethyl)-1'H,2H-3,4'-bipyrazole as a yellow oil. LC/MS: mass calculated for $C_{19}H_{22}BrF_2N_5O$: 453.10, measured (ES, m/z): 455.95 [M+H+2]$^+$.

Step 6: 2-(6-(3-(tert-Butoxy)-1-(2-(difluoromethyl)-1'H,2H-[3,4'-bipyrazol]-1'-yl)propyl)pyridin-3-yl)-4-chloro-3-fluoroaniline A mixture of 1'-(1-(5-bromopyridin-2-yl)-3-(tert-butoxy)propyl)-2-(difluoromethyl)-1'H,2H-3,4'-bipyrazole (448 mg, 0.99 mmol, 1.0 equiv.), 6-amino-3-chloro-2-fluorophenylboronic acid (280 mg, 1.48 mmol, 1.5 equiv.), Pd(PPh$_3$)$_4$ (114 mg, 0.10 mmol, 0.1 equiv.) and K$_2$CO$_3$ (409 mg, 2.96 mmol, 3.0 equiv.) in 1,4-dioxane/water (V/V=4:1, 3 mL) was refluxed at 90° C. under N$_2$ for 3 h. The resulting mixture was diluted with water, and the mixture extracted with EA (3×5 mL). The organic layers were combined, washed with water (5 mL), dried over Na$_2$SO$_4$ and concentrated. The residue was purified by silica gel chromatography (0%→80%, EA/PE) to yield 2-(6-(3-(tert-butoxy)-1-(2-(difluoromethyl)-1'H,2H-[3,4'-bipyrazol]-1'-yl)propyl)pyridin-3-yl)-4-chloro-3-fluoroaniline as a light yellow solid. LC/MS: mass calculated for C$_{25}$H$_{26}$ClF$_3$N$_6$O: 518.18, measured (ES, m/z): 519.25 [M+H]$^+$.

Step 7:1'-(3-(tert-Butoxy)-1-(5-(3-chloro-2-fluoro-6-(1H-tetrazol-1-yl)phenyl)pyridin-2-yl)propyl)-2-(difluoromethyl)-1'H,2H-3,4'-bipyrazole A mixture of 2-(6-(3-(tert-butoxy)-1-(2-(difluoromethyl)-1'H,2H-[3,4'-bipyrazol]-1'-yl)propyl)pyridin-3-yl)-4-chloro-3-fluoroaniline (295 mg, 0.57 mmol, 1.0 equiv.), trimethoxymethane (2 mL), azidotrimethylsilane (2 mL) and acetic acid (2 mL) was stirred overnight at 30° C. The reaction was purified by reverse chromatography on C18 (0%→55% MeCN/H$_2$O (0.05% CF$_3$COOH)) to yield 1'-(3-(tert-butoxy)-1-(5-(3-chloro-2-fluoro-6-(1H-tetrazol-1-yl)phenyl)pyridin-2-yl)propyl)-2-(difluoromethyl)-1'H,2H-3,4'-bipyrazole as a light yellow solid. LC/MS: mass calculated for C$_{26}$H$_{25}$ClF$_3$N$_9$O: 571.18, measured (ES, m/z): 572.25 [M+H]$^+$.

Step 8: (R)-2-(3-(tert-Butoxy)-1-(2-(difluoromethyl)-1'H,2H-[3,4'-bipyrazol]-1'-yl)propyl)-5-(3-chloro-2-fluoro-6-(1H-tetrazol-1-yl)phenyl)pyridine 1-oxide A mixture of 1'-(3-(tert-butoxy)-1-(5-(3-chloro-2-fluoro-6-(1H-tetrazol-1-yl)phenyl)pyridin-2-yl)propyl)-2-(difluoromethyl)-1'H,2H-3,4'-bipyrazole (195 mg, 0.34 mmol, 1.0 equiv.), methyltrioxorhenium (42 mg, 0.17 mmol, 0.5 equiv.) and hydrogen peroxide (0.5 mL, 30 wt %) in CH$_3$OH (1.5 mL) was stirred for 2 h at room temperature. The resulting mixture was purified by reverse phase chromatography on C18 (MeCN/H$_2$O (0.05% CF$_3$COOH)) to yield 2-(3-(tert-butoxy)-1-(2-(difluoromethyl)-1'H,2H-[3,4'-bipyrazol]-1'-yl)propyl)-5-(3-chloro-2-fluoro-6-(1H-tetrazol-1-yl)phenyl)pyridine 1-oxide. The racemic product was separated by chiral-HPLC to yield (R)-2-(3-(tert-butoxy)-1-(2-(difluoromethyl)-1'H,2H-[3,4'-bipyrazol]-1'-yl)propyl)-5-(3-chloro-2-fluoro-6-(1H-tetrazol-1-yl)phenyl)pyridine 1-oxide as a white solid.

LC/MS: mass calculated for C$_{26}$H$_{25}$ClF$_3$N$_9$O$_2$: 587.18, measured (ES, m/z): 610.10 [M+Na]$^+$. $^1$H NMR (300 MHz, DMSO-d$_6$) δ 9.68 (s, 1H), 8.42 (d, J=1.5 Hz, 1H), 8.35 (s, 1H), 7.61-8.11 (m, 5H), 7.45 (d, J=8.3 Hz, 1H), 7.19-7.20 (m, 1H), 6.67 (d, J=1.7 Hz, 1H), 6.20-6.25 (m, 1H), 3.25-3.29 (m, 1H), 3.07-3.19 (m, 1H), 2.39-2.46 (m, 2H), 1.02 (s, 9H). $^{19}$F-NMR (282 MHz, DMSO-d$_6$) δ −93.57, −93.64, −112.70.

Example 678: (S)-5-(3-Chloro-6-(4-chloro-1H-1,2,3-triazol-1-yl)-2-fluorophenyl)-2-(1-(2-(difluoromethyl)-1'H,2H-[3,4'-bipyrazol]-1'-yl)-2-(4-fluoro-1H-pyrazol-1-yl)ethyl)pyridine 1-oxide

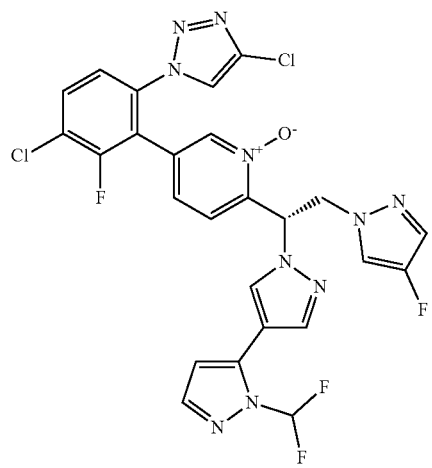 [SMILES: [O-][n+]1cc(-c2c(-n3cc(Cl)nn3)ccc(Cl)c2F)ccc1[C@H](Cn1cc(F)cn1)n1cc(-c2ccnn2C(F)F)cn1]

LC/MS: mass calculated for C$_{25}$H$_{16}$Cl$_2$F$_4$N$_{10}$O 618.08, measured (ES, m/z): 619.0 [M+H]$^+$. $^1$H NMR (400 MHz, DMSO-d$_6$) δ 8.67 (s, 1H), 8.48 (s, 1H), 8.21 (s, 1H), 8.03 (dd, J=8.7, 7.8 Hz, 1H), 7.58-7.95 (m, 5H), 7.49 (d, J=8.3 Hz, 1H), 7.44 (d, J=4.1 Hz, 1H), 7.21 (dd, J=8.3, 1.7 Hz, 1H), 6.64 (d, J=1.7 Hz, 1H), 6.54-6.63 (m, 1H), 4.87-5.02 (m, 2H). $^{19}$F NMR (376 MHz, DMSO-d$_6$) δ −93.64, −93.69, −112.87, −177.87.

Example 679: (S)-5-(3-Chloro-2-fluoro-6-(1H-tetrazol-1-yl)phenyl)-2-(1-(2-(difluoromethyl)-1'H,2H-[3,4'-bipyrazol]-1'-yl)-3-methoxy-3-methylbutyl)pyridine 1-oxide

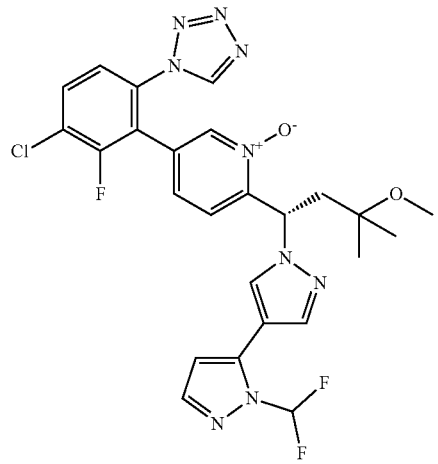 [SMILES: COC(C)(C)C[C@@H](c1ccc(-c2c(-n3cnnn3)ccc(Cl)c2F)c[n+]1[O-])n1cc(-c2ccnn2C(F)F)cn1]

LC/MS: mass calculated for C$_{25}$H$_{23}$ClF$_3$N$_9$O$_2$: 573.16, measured (ES, m/z): 574.1 [M+H]$^+$. $^1$H NMR (400 MHz, DMSO-d$_6$) δ 9.69 (s, 1H), 8.40-8.45 (m, 2H), 8.06 (dd, J=8.7, 7.7 Hz, 1H), 7.67-7.98 (m, 4H), 7.43 (d, J=8.3 Hz, 1H), 7.16 (dd, J=8.4, 1.7 Hz, 1H), 6.68 (d, J=1.7 Hz, 1H), 6.30-6.33 (m, 1H), 3.02 (s, 3H), 2.52-2.60 (m, 1H), 2.32 (dd, J=14.5, 4.2 Hz, 1H), 1.03 (s, 3H), 0.97 (s, 3H). ¹⁹F NMR (376 MHz, DMSO-d₆) δ −93.53, −112.73.

Example 680: (R)-5-(3-Chloro-6-(4-chloro-1H-1,2,3-triazol-1-yl)-2-fluorophenyl)-2-(1-(2-(difluoromethyl)-1'H,2H-[3,4'-bipyrazol]-1'-yl)-2-(4-fluoro-1H-pyrazol-1-yl)ethyl)pyridine 1-oxide

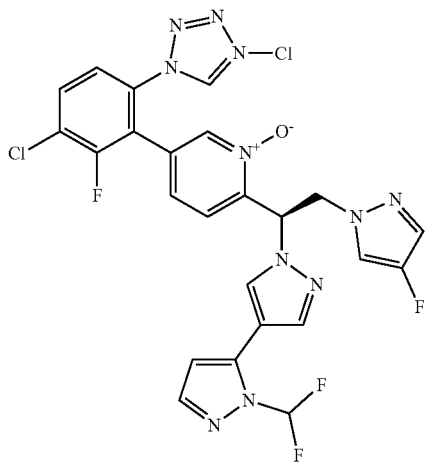

LC/MS: mass calculated for $C_{25}H_{16}Cl_2F_4N_{10}O$: 618.08, measured (ES, m/z): 619.0 [M+H]⁺. ¹H NMR (400 MHz, DMSO-d₆) δ 8.67 (s, 1H), 8.48 (s, 1H), 8.21 (s, 1H), 8.03 (dd, J=8.7, 7.7 Hz, 1H), 7.58-7.94 (m, 5H), 7.49 (d, J=8.3 Hz, 1H), 7.41-7.46 (m, 1H), 7.21 (dd, J=8.2, 1.7 Hz, 1H), 6.64 (d, J=1.7 Hz, 1H), 6.49-6.61 (m, 1H), 4.87-5.02 (m, 2H). ¹⁹F NMR (376 MHz, DMSO-d₆) δ −93.64, −93.69, −112.87, −177.87.

Example 681: (S*)-5-(3-Chloro-2-fluoro-6-(1H-tetrazol-1-yl)phenyl)-2-(1-(2-(difluoromethyl)-1'H,2H-[3,4'-bipyrazol]-1'-yl)-2-(4-fluoro-1H-pyrazol-1-yl)ethyl)pyridine 1-oxide

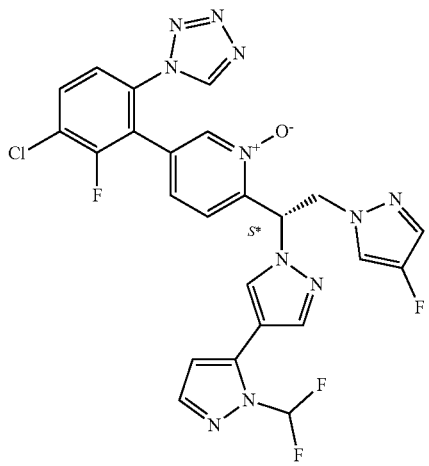 [SMILES: [O-][n+]1cc(-c2c(-n3cnnn3)ccc(Cl)c2F)ccc1[C@H](Cn1cc(F)cn1)n1cc(-c2ccnn2C(F)F)cn1]

LC/MS: mass calculated for $C_{24}H_{16}ClF_4NO_{11}$: 585.12, measured (ES, m/z): 608.05 [M+Na]⁺. ¹H NMR (400 MHz, DMSO-d₆) δ 9.68 (s, 1H), 8.51 (d, J=1.6 Hz, 1H), 8.20 (s, 1H), 8.07 (dd, J=8.7, 7.8 Hz, 1H), 7.57-7.95 (m, 5H), 7.40-7.49 (m, 2H), 7.23 (dd, J=8.3, 1.7 Hz, 1H), 6.64 (d, J=1.7 Hz, 1H), 6.51-6.56 (m, 1H), 4.86-5.01 (m, 2 h). ¹⁹F NMR (376 MHz, DMSO-d₆) δ −93.63, −93.71, −112.61, −177.90.

Example 682: (S)-5-(3-Chloro-2-fluoro-6-(1H-tetrazol-1-yl)phenyl)-2-(1-(2-(difluoromethyl)-1'H,2H-[3,4'-bipyrazol]-1'-yl)-2-(4-fluoro-1H-pyrazol-1-yl)ethyl)pyridine 1-oxide

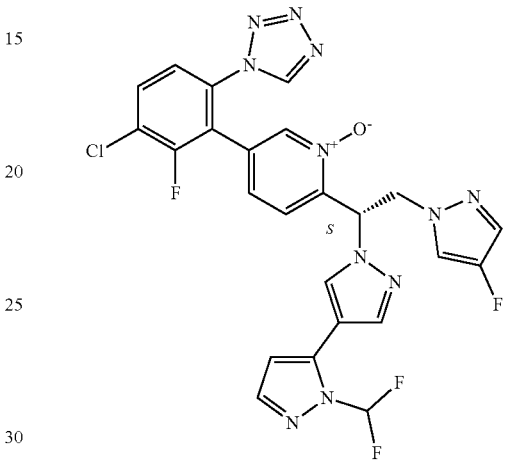

LC/MS: mass calculated for $C_{24}H_{16}ClF_4N_{11}O$: 585.12, measured (ES, m/z): 608.05 [M+Na]⁺. ¹H NMR (400 MHz, DMSO-d₆) δ 9.68 (s, 1H), 8.51 (d, J=1.6 Hz, 1H), 8.20 (s, 1H), 8.07 (dd, J=8.7, 7.8 Hz, 1H), 7.55-7.97 (m, 5H), 7.39-7.50 (m, 2H), 7.22 (dd, J=8.3, 1.7 Hz, 1H), 6.64 (d, J=1.8 Hz, 1H), 6.51-6.55 (m, 1H), 4.85-5.01 (m, 2 h). ¹⁹F NMR (376 MHz, DMSO-d₆) δ −93.63, −93.71, −112.62, −177.90.

Example 683: (R)-5-(3-Chloro-2-fluoro-6-(1H-tetrazol-1-yl)phenyl)-2-(1-(2-(difluoromethyl)-1'H,2H-[3,4'-bipyrazol]-1'-yl)-3-methoxy-3-methylbutyl)pyridine 1-oxide

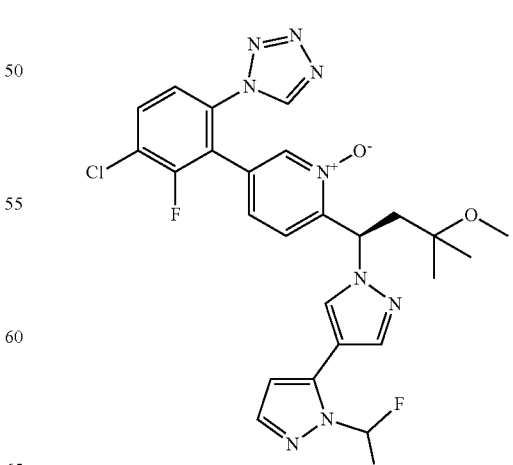

Step 1: N,3-Dimethoxy-N,3-dimethylbutanamide

To a solution of 2-Methoxy-2-methylpropanecarboxylic acid (1.0 g, 7.56 mmol, 1.0 equiv.) in DCM (12 mL) was added CDI (1.8 g, 11.35 mmol, 2.0 equiv.) at room temperature under $N_2$. The mixture was stirred at room temperature for 1 h. Then N-methoxymethanamine hydrochloride (812 mg, 8.32 mmol, 1.1 equiv.) was added. The mixture was stirred at room temperature overnight. To the reaction mixture was added water, and the mixture extracted with DCM, the organic layer was washed with $NaHCO_3$ (aq.), brine and dried over anhydrous $Na_2SO_4$. Concentrated to yield N,3-dimethoxy-N,3-dimethylbutanamide as a yellow solid.

Step 2: 1-(5-Bromopyridin-2-yl)-3-methoxy-3-methylbutan-1-one

To a solution of 2,5-dibromopyridine (608 mg, 2.57 mmol, 1.0 equiv.) in toluene (5 mL) was add n-BuLi (1.1 ml, 2.82 mmol, 1.1 equiv.) at −78° C. under $N_2$. After 1 h to the mixture was add N,3-dimethoxy-N,3-dimethylbutanamide (540 mg, 3.08 mmol, 1.2 equiv.) in toluene (3 mL) and the mixture slowly at −78° C. under $N_2$. The reaction mixture was stirred 2 h at −78° C. To the reaction mixture was added $NH_4Cl$ (aq.) and the mixture extracted with ethyl acetate, the organic layer was washed with brine and dried over anhydrous $Na_2SO_4$. The resulting mixture was concentrated and purified silica gel chromatography (0→40% EA/PE) to yield 1-(5-bromopyridin-2-yl)-3-methoxy-3-methylbutan-1-one as a yellow solid. LC/MS: mass calculated for $C_{11}H_{14}BrNO_2$: 271.02, measured (ES, m/z): 272.00 [M+H]$^+$.

Step 3: 1-(5-Bromopyridin-2-yl)-3-methoxy-3-methylbutan-1-ol

To a solution of 1-(5-bromopyridin-2-yl)-3-methoxy-3-methylbutan-1-one (250 mg, 0.92 mmol, 1.0 equiv.) in $CH_3OH$ (3 mL) was added $NaBH_4$ (42 mg, 1.10 mmol, 1.2 equiv.) slowly at 0° C., then warmed to room temperature and stirred for 1 h. To the reaction mixture was added water, and the mixture extracted with ethyl acetate, the organic layer was washed with brine and dried over anhydrous $Na_2SO_4$. The resulting mixture was concentrated to yield 1-(5-bromopyridin-2-yl)-3-methoxy-3-methylbutan-1-ol as a yellow solid. LC/MS: mass calculated for $C_{11}H_{16}BrNO_2$: 273.04, measured (ES, m/z): 274.00 [M+H]$^+$.

Step 4: 1-(5-Bromopyridin-2-yl)-3-methoxy-3-methylbutyl methanesulfonate

To a solution of 1-(5-bromopyridin-2-yl)-3-methoxy-3-methylbutan-1-ol (240 mg, 0.87 mmol, 1.0 equiv) in DCM (5 mL) was added triethylamine (0.2 mL, 1.75 mmol, 2.0 equiv.) and methanesulfonic anhydride (229 mg, 1.31 mmol, 1.5 equiv.) at 0° C., then warmed to room temperature the and stirred for 4 h. To the reaction was added water, and the mixture extracted with DCM, the organic layer was washed with brine and dried over anhydrous $Na_2SO_4$. The resulting mixture was concentrated and purified by silica gel chromatography (0→40% EA/PE) to yield 1-(5-bromopyridin-2-yl)-3-methoxy-3-methylbutyl methanesulfonate as a yellow solid. LC/MS: mass calculated for $C_{12}H_{18}BrNO_4S$: 351.01, measured (ES, m/z): 351.95 [M+H]$^+$.

Step 5: 1'-(1-(5-Bromopyridin-2-yl)-3-methoxy-3-methylbutyl)-2-(difluoromethyl)-1'H,2H-3,4'-bipyrazole The mixture of 1-(5-bromopyridin-2-yl)-3-methoxy-3-methylbutyl methanesulfonate (170 mg, 0.48 mmol, 1.0 equiv.), 2-(difluoromethyl)-1'H,2H-3,4'-bipyrazole (107 mg, 0.58 mmol, 1.2 equiv.) and $Cs_2CO_3$ (314 mg, 0.96 mmol, 2.0 equiv.) in acetonitrile (5 mL) was stirred at 90° C. for 3 h. To the reaction mixture was added water, and the mixture extracted with ethyl acetate, the organic layer was washed with brine and dried over anhydrous $Na_2SO_4$. The resulting mixture was concentrated and purified silica gel chromatography (0→40% EA/PE) to yield 1'-(1-(5-bromopyridin-2-yl)-3-methoxy-3-methylbutyl)-2-(difluoromethyl)-1'H,2H-3,4'-bipyrazole as a yellow solid. LC/MS: mass calculated for $C_{18}H_{20}BrF_2N_5O$: 439.08, measured (ES, m/z): 439.95 [M+H]$^+$.

Step 6: 4-Chloro-2-(6-(1-(2-(difluoromethyl)-1'H,2H-[3,4'-bipyrazol]-1'-yl)-3-methoxy-3-methylbutyl)pyridin-3-yl)-3-fluoroaniline The mixture of 1'-(1-(5-bromopyridin-2-yl)-3-methoxy-3-methylbutyl)-2-(difluoromethyl)-1'H,2H-3,4'-bipyrazole (170 mg, 0.39 mmol, 1.0 equiv.), (6-amino-3-chloro-2-fluorophenyl)boronic acid (146 mg, 0.77 mmol, 2.0 equiv.), $K_2CO_3$ (267 mg, 1.93 mmol, 5.0 equiv.) and $Pd(PPh_3)_4$ (45 mg, 0.039 mmol, 0.1 equiv.) in 1,4-dioxane (4 mL) and water (1 mL) was stirred at 90° C. under $N_2$ overnight. To the reaction mixture was added water, and the mixture extracted with ethyl acetate, the organic layer was washed with brine and dried over anhydrous $Na_2SO_4$. The resulting mixture was concentrated and purified by silica gel chromatography (0→40% EA/PE) to yield 4-chloro-2-(6-(1-(2-(difluoromethyl)-1'H,2H-[3,4'-bipyrazol]-1'-yl)-3-methoxy-3-methylbutyl)pyridin-3-yl)-3-fluoroaniline as a yellow solid.

Step 7: 1'-(1-(5-(3-chloro-2-fluoro-6-(1H-tetrazol-1-yl)phenyl)pyridin-2-yl)-3-methoxy-3-methylbutyl)-2-(difluoromethyl)-1'H,2H-3,4'-bipyrazole The mixture of 4-chloro-2-(6-(1-(2-(difluoromethyl)-1'H, 2H-[3,4'-bipyrazol]-1'-yl)-3-methoxy-3-methylbutyl)pyridin-3-yl)-3-fluoroaniline (170 mg, 0.34 mmol, 1.0 equiv), azidotrimethylsilane (2 mL) and trimethoxymethane (2 mL) in acetic acid (3 mL) was stirred at room temperature overnight. The reaction was concentrated and purified by reverse phase chromatography on C18 (80 g, MeCN/$H_2O$ (0.05% $CF_3COOH$): 0→55%) to yield 1'-(1-(5-(3-chloro-2-fluoro-6-(1H-tetrazol-1-yl)phenyl)pyridin-2-yl)-3-methoxy- 3-methylbutyl)-2-(difluoromethyl)-1'H,2H-3,4'-bipyrazole as a yellow solid. LC/MS: mass calculated for $C_{25}H_{23}ClF_3N_9O$: 557.17, measured (ES, m/z): 558.15 [M+H]$^+$.

Step 8: (R)-5-(3-chloro-2-fluoro-6-(1H-tetrazol-1-yl)phenyl)-2-(1-(2-(difluoromethyl)-1'H,2H-[3,4'-bipyrazol]-1'-yl)-3-methoxy-3-methylbutyl)pyridine 1-oxide The mixture of 1'-(1-(5-(3-chloro-2-fluoro-6-(1H-tetrazol-1-yl)phenyl)pyridin-2-yl)-3-methoxy-3-methylbutyl)-2-(difluoromethyl)-1'H,2H-3,4'-bipyrazole (150 mg, 0.269 mmol, 1.0 equiv), methyltrioxorhenium (33.503 mg, 0.134 mmol, 0.5 equiv) and hydrogen peroxide (152.407 mg, 1.344 mmol, 5.0 equiv, 30%) in CH$_3$OH (2 mL) was stirred at room temperature for 2 h. The reaction was purified by reverse phase chromatography on C18 (80 g, MeCN/H2O (0.05% CF3COOH): 0>55%) to yield 5-(3-chloro-2-fluoro-6-(1H-tetrazol-1-yl)phenyl)-2-(1-(2-(difluoromethyl)-1'H,2H-[3,4'-bipyrazol]-1'-yl)-3-methoxy-3-methylbutyl)pyridine 1-oxide. The compound, 5-(3-chloro-2-fluoro-6-(1H-tetrazol-1-yl)phenyl)-2-(1-(2-(difluoromethyl)-1'H,2H-[3,4'-bipyrazol]-1'-yl)-3-methoxy-3-methylbutyl)pyridine 1-oxide (80 mg) was separated by Prep-Chiral-HPLC to yield (R)-5-(3-chloro-2-fluoro-6-(1H-tetrazol-1-yl)phenyl)-2-(1-(2-(difluoromethyl)-1'H,2H-[3,4'-bipyrazol]-1'-yl)-3-methoxy-3-methylbutyl)pyridine 1-oxide as a white solid.

LC/MS: mass calculated for $C_{25}H_{23}ClF_3N_9O_2$: 573.16, measured (ES, m/z): 574.10 [M+H]$^+$. $^1$H NMR (400 MHz, DMSO-d$_6$) δ 9.69 (s, 1H), 8.40-8.45 (m, 2H), 8.06 (t, J=8.8 Hz, 1H), 7.88 (s, 1H), 7.83 (t, J=56.0 Hz, 1H), 7.75-7.77 (m, 2H), 7.44 (d, J=8.3 Hz, 1H), 7.17 (d, J=8.3 Hz, 1H), 6.68 (d, J=1.7 Hz, 1H), 6.32 (dd, J=8.7, 4.1 Hz, 1H), 3.02 (s, 3H), 2.52-2.60 (m, 1H), 2.30-2.35 (m, 1H), 1.03 (s, 3H), 0.97 (s, 3H). $^{19}$F NMR (376 MHz, DMSO-d$_6$) δ −93.53, −112.73.

Example 684: (S)-5-(3-Chloro-2-fluoro-6-(1H-tetrazol-1-yl)phenyl)-2-(1-(2-(difluoromethyl)-1'H,2H-[3,4'-bipyrazol]-1'-yl)-3-hydroxy-3-methylbutyl)pyridine 1-oxide

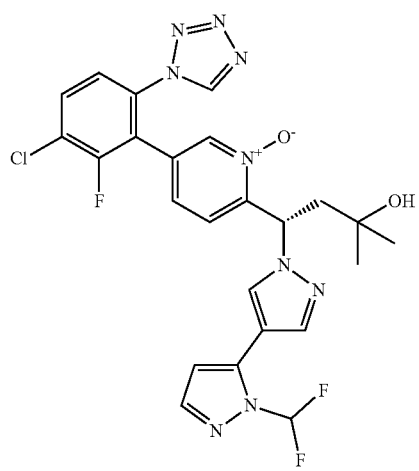 [SMILES: CC(C)(O)C[C@@H](c1ccc(-c2c(-n3cnnn3)ccc(Cl)c2F)c[n+]1[O-])n1cc(-c2ccnn2C(F)F)cn1]

LC/MS: mass calculated for $C_{24}H_{21}ClF_3N_9O_2$: 559.15, measured (ES, m/z): 560.10 [M+H]$^+$. $^1$H NMR (400 MHz, DMSO-d$_6$) δ 9.69 (s, 1H), 8.39-8.46 (m, 2H), 8.04-8.08 (m, 1H), 7.67-7.99 (m, 4H), 7.43 (d, J=8.3 Hz, 1H), 7.18 (dd, J=8.3, 1.7 Hz, 1H), 6.69 (d, J=1.7 Hz, 1H), 6.34-6.38 (m, 1H), 4.53 (s, 1H), 2.50-2.59 (m, 1H), 2.16 (dd, J=14.2, 3.8 Hz, 1H), 0.96 (d, J=5.9 Hz, 6H). $^{19}$F NMR (376 MHz, DMSO-d$_6$) δ −93.58 (d, J=5.0 Hz), −112.75.

Example 685: (R)-5-(3-Chloro-2-fluoro-6-(1H-tetrazol-1-yl)phenyl)-2-(1-(2-(difluoromethyl)-1'H,2H-[3,4'-bipyrazol]-1'-yl)-3-hydroxy-3-methylbutyl)pyridine 1-oxide

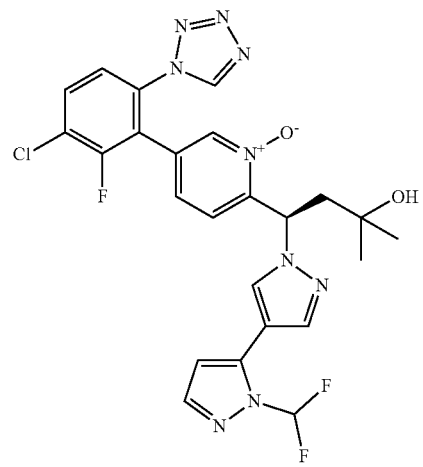 [SMILES: CC(C)(O)C[C@H](c1ccc(-c2c(-n3cnnn3)ccc(Cl)c2F)c[n+]1[O-])n1cc(-c2ccnn2C(F)F)cn1]

Step 1: Benzyl 3-hydroxy-3-methylbutanoate

To a solution of 3-hydroxy-3-methylbutyric acid (3.2 g, 31.83 mmol, 1.0 equiv.) and benzyl alcohol (4.1 g, 38.19 mmol, 1.2 equiv.) in DCM (10 mL) was added 4-dimethylaminopyridine (0.78 g, 6.39 mmol, 0.2 equiv.) and the solution was stirred at 0° C. Then N,N'-dicyclohexylcarbodiimide (9.9 g, 47.99 mmol, 1.5 equiv.) was added and the mixture stirred at room temperature overnight. The precipitated insoluble matter was removed by filtration, and the filtrate was concentrated and purified by silica gel column chromatography (0→70% EA/PE) to yield benzyl 3-hydroxy-3-methylbutanoate as pale yellow oil. $^1$H NMR (400 MHz, Chloroform-d) δ 7.38 (s, 3H), 7.30-7.35 (m, 2H), 5.18 (s, 2H), 3.57 (s, 1H), 2.56 (s, 2H), 1.30 (s, 6H).

Step 2: Benzyl 3-((tert-butyldimethylsilyl)oxy)-3-methylbutanoate

To a solution of benzyl 3-hydroxy-3-methylbutyrate (5.1 g, 24.49 mmol, 1.0 equiv.) in DCM (50 mL) was added 2,6-lutidine (5.3 g, 48.98 mmol, 2.0 equiv.) and the solution was stirred at 0° C. Then trifluoromethanesulfonic acid tert-butyldimethylsilyl ester (5.6 mL, 24.49 mmol, 1.0 equiv.) was added dropwise, and the mixture stirred for 1 h at 0° C. The resulting mixture was stirred for 2 h at room temperature. The reaction mixture was diluted with ethyl acetate, washed with water, aqueous saturated ammonium chloride solution and aqueous saturated sodium chloride solution, then dried over Na$_2$SO$_4$, concentrated and purified by silica gel chromatography (0→60%, EA/PE) to yield benzyl 3-((tert-butyldimethylsilyl)oxy)-3-methylbutanoate as a colorless oil. LC/MS: mass calculated for $C_{18}H_{30}O_3Si$: 322.20, measured (ES, m/z): 323.15 [M+H]$^+$.

Step 3: 3-((tert-Butyldimethylsilyl)oxy)-3-methylbutanoic acid

Benzyl 3-(t-butyldimethylsilyloxy)-3-methylbutyrate (5.4 g, 16.59 mmol, 1.0 equiv.) was dissolved in ethyl acetate (60 mL), and 10% palladium-carbon (1.1 g) was added for hydrogenation with $H_2$ under atmospheric pressure. After 40 minutes stirring, the reaction was stopped, and the catalyst was removed by filtration. The filtrate was concentrated under vacuum to yield the 3-((tert-butyldimethylsilyl)oxy)-3-methylbutanoic acid as a colorless oil. $^1$H NMR (400 MHz, Chloroform-d) δ 11.28 (s, 1H), δ 2.51 (s, 2H), 1.40 (s, 6H), 0.87 (s, 9H), 0.19-0.00 (m, 6H).

Step 4: 3-((tert-Butyldimethylsilyl)oxy)-N-methoxy-N,3-dimethylbutanamide

To a solution of 3-((tert-butyldimethylsilyl)oxy)-3-methylbutanoic acid (0.68 g, 2.66 mmol, 1.0 equiv.) in DCM (20 mL) was added 1,1'-carbonyldiimidazole (2.1 g, 12.91 mmol, 1.5 equiv.) and was stirred for 15 min at room temperature. N,O-dimethylhydroxylamine hydrochloride (1.1 g, 12.91 mmol, 1.5 equiv.) was added and the mixture was stirred at room temperature overnight. The solution was diluted with $H_2O$ and extracted with DCM twice. The combined organic layers were washed with 0.5 M hydrochloric acid and brine, dried over $Na_2SO_4$ and concentrated to yield 3-((tert-butyldimethylsilyl)oxy)-N-methoxy-N,3-dimethylbutanamide as a light yellow oil. $^1$H NMR (400 MHz, Chloroform-d) δ 3.66 (s, 3H), 3.14 (s, 3H), 1.45 (s, 2H), 1.37 (s, 6H), 0.83 (s, 9H), 0.07 (s, 6H).

Step 5: 1-(5-Bromopyridin-2-yl)-3-((tert-butyldimethylsilyl)oxy)-3-methylbutan-1-one To a solution of 2,5-dibromopyridine (1.6 g, 6.92 mmol, 1.0 equiv.) in toluene (20 mL) added n-butyllithium (3.0 mL, 7.61 mmol, 1.1 equiv.) at the temperature was dropped at −70° C. and the mixture stirred for 1 h under $N_2$. Then 3-((tert-butyldimethylsilyl)oxy)-N-methoxy-N,3-dimethylbutanamide (2.0 g, 7.26 mmol, 1.0 equiv.) was added and the mixture stirred for additional 1 h. The reaction was quenched with saturated ammonium chloride aqueous solution and extracted with ethyl acetate twice. The combined organic layers were washed with brine, dried over $Na_2SO_4$, concentrated and purified by silica gel chromatography (0→20% EtOAc/petroleum ether) to yield 1-(5-bromopyridin-2-yl)-3-((tert-butyldimethylsilyl)oxy)-3-methylbutan-1-one as a light yellow oil. LC/MS: mass calculated for $C_{16}H_{26}BrNO_2Si$: 371.09, measured (ES, m/z): 372.00, 374.00 [M+H, M+H+2]$^+$.

Step 6: 1-(5-Bromopyridin-2-yl)-3-((tert-butyldimethylsilyl)oxy)-3-methylbutan-1-ol To a solution of 1-(5-bromopyridin-2-yl)-3-((tert-butyldimethylsilyl)oxy)-3-methylbutan-1-one (1.2 g, 3.22 mmol, 1.0 equiv.) in $CH_3OH$ (12 mL) was added $NaBH_4$ (0.18 g, 4.83 mmol, 1.5 equiv.) at 0° C. The mixture was stirred at r.t for 2 h. The reaction was quenched with water and then extracted with ethyl acetate twice. The combined layers were washed with brine, dried over $Na_2SO_4$, concentrated and purified by silica gel chromatography (0→30%, EA/PE) to yield 1-(5-bromopyridin-2-yl)-3-((tert-butyldimethylsilyl)oxy)-3-methylbutan-1-ol as a light yellow oil. LC/MS: mass calculated for $C_{16}H_{28}BrNO_2Si$: 373.11, measured (ES, m/z): 374.00, 376.00 [M+H, M+H+2]$^+$.

Step 7: 1-(5-Bromopyridin-2-yl)-3-((tert-butyldimethylsilyl)oxy)-3-methylbutyl methanesulfonate To a mixture of 1-(5-bromopyridin-2-yl)-3-((tert-butyldimethylsilyl)oxy)-3-methylbutan-1-ol (0.52 g, 1.39 mmol, 1.0 equiv.) and triethylamine (0.97 mL, 6.95 mmol, 5.0 equiv.) in DCM (6 mL) was added methanesulfonic anhydride (0.48 g, 2.78 mmol, 2.0 equiv.) at 0° C. and the solution stirred for 2 h at room temperature. The mixture was diluted with $H_2O$, extracted with DCM twice. The combined organic layers were washed with brine, dried over $Na_2SO_4$, concentrated and purified by silica gel chromatography (0→30%, EA/PE) to yield 1-(5-bromopyridin-2-yl)-3-((tert-butyldimethylsilyl)oxy)-3-methylbutyl methanesulfonate a light yellow oil. LC/MS: mass calculated for $C_{17}H_{30}BrNO_4SSi$: 451.08, measured (ES, m/z): 452.05, 454.05 [M+H, M+H+2]$^+$.

Step 8: 1'-(1-(5-Bromopyridin-2-yl)-3-((tert-butyldimethylsilyl)oxy)-3-methylbutyl)-2-(difluoromethyl)-1'H,2H-3,4'-bipyrazole A mixture of 2-(difluoromethyl)-1'H,2H-3,4'-bipyrazole (0.21 g, 1.14 mmol, 1.2 equiv.) and cesium carbonate (0.34 g, 1.05 mmol, 1.1 equiv.) in acetonitrile (5 mL) was stirred for 15 min at room temperature. 1-(5-Bromopyridin-2-yl)-3-((tert-butyldimethylsilyl)oxy)-3-methylbutyl methanesulfonate (0.43 g, 0.95 mmol, 1.0 equiv.) was added and the solution was stirred for 3 h at 90° C. The solution was diluted with $H_2O$, extracted with ethyl acetate twice. The combined organic layers were washed with brine, dried over $Na_2SO_4$, concentrated and purified by silica gel chromatography (0→10% MeOH/DCM) to yield 1'-(1-(5-bromopyridin-2-yl)-3-((tert-butyldimethylsilyl)oxy)-3-methylbutyl)-2-(difluoromethyl)-1'H,2H-3,4'-bipyrazole as a light yellow oil. LC/MS: mass calculated for $C_{23}H_{32}BrF_2N_5OSi$: 539.15, measured (ES, m/z): 540.15, 542.15 [M+H, M+H+2]$^+$.

Step 9: 2-(6-(3-((tert-Butyldimethylsilyl)oxy)-1-(2-(difluoromethyl)-1'H,2H-[3,4'-bipyrazol]-1'-yl)-3-methylbutyl)pyridin-3-yl)-4-chloro-3-fluoroaniline A mixture of 1'-(1-(5-bromopyridin-2-yl)-3-((tert-butyldimethylsilyl)oxy)-3-methylbutyl)-2-(difluoromethyl)-1'H,2H-3,4'-bipyrazole (0.23 g, 0.43 mmol, 1.0 equiv.), (6-amino-3-chloro-2-fluorophenyl)boronic acid (0.16 g, 0.85 mmol, 2.0 equiv.), $Pd(PPh_3)_4$ (0.098 g, 0.085 mmol, 0.2 equiv.), $K_2CO_3$ (0.35 g, 2.55 mmol, 6.0 equiv.) in 1,4-dioxane (4 mL) and water (1 mL) was refluxed at 90° C. under $N_2$ for 2 h. The mixture was diluted with $H_2O$, then extracted with ethyl acetate twice. The combined organic layers were washed with brine, dried over $Na_2SO_4$, concentrated and purified by silica gel chromatography (0→8%, MeOH/DCM) to yield 2-(6-(3-((tert-butyldimethylsilyl)oxy)-1-(2-(difluoromethyl)-1'H,2H-[3,4'-bipyrazol]-1'-yl)-3-methylbutyl)pyridin-3-yl)-4-chloro-3-fluoroaniline as a light yellow oil. LC/MS: mass calculated for $C_{29}H_{36}ClF_3N_6OSi$: 604.24, measured (ES, m/z): 605.20 [M+H]$^+$.

Step 10: 1'-(3-((tert-Butyldimethylsilyl)oxy)-1-(5-(3-chloro-2-fluoro-6-(1H-tetrazol-1-yl)phenyl)pyridin-2-yl)-3-methylbutyl)-2-(difluoromethyl)-1'H,2H-3,4'-bipyrazole A mixture of 2-(6-(3-((tert-butyldimethylsilyl)oxy)-1-(2-(difluoromethyl)-1'H,2H-[3,4'-bipyrazol]-1'-yl)-3-methylbutyl)pyridin-3-yl)-4-chloro-3-fluoroaniline (0.20 g, 0.33 mmol, 1.0 equiv.), trimethoxymethane (2 mL), azidotrimethylsilane (2 mL) and acetic acid (2 mL) was stirred overnight at room temperature. The mixture was concentrated under vacuum and purified by reverse phase chromatography on C18 (80 g, MeCN/H$_2$O (0.05% CF$_3$COOH): 0→45%) to yield 1'-(3-((tert-butyldimethylsilyl)oxy)-1-(5-(3-chloro-2-fluoro-6-(1H-tetrazol-1-yl)phenyl)pyridin-2-yl)-3-methylbutyl)-2-(difluoromethyl)-1'H,2H-3,4'-bipyrazole as an yellow solid. LC/MS: mass calculated for C$_{30}$H$_{35}$ClF$_3$N$_9$OSi: 657.24, measured (ES, m/z): 658.15 [M+H]$^+$.

Step 11: 2-(3-((tert-Butyldimethylsilyl)oxy)-1-(2-(difluoromethyl)-1'H,2H-[3,4'-bipyrazol]-1'-yl)-3-methylbutyl)-5-(3-chloro-2-fluoro-6-(1H-tetrazol-1-yl)phenyl)pyridine 1-oxide A mixture of 1'-(3-((tert-butyldimethylsilyl)oxy)-1-(5-(3-chloro-2-fluoro-6-(1H-tetrazol-1-yl)phenyl)pyridin-2-yl)-3-methylbutyl)-2-(difluoromethyl)-1'H,2H-3,4'-bipyrazole (0.12 g, 0.18 mmol, 1.0 equiv.) and 3-chlorobenzoperoxoic acid (0.16 g, 0.91 mmol, 5.0 equiv.) in ethyl acetate (2 mL) was then stirred for 1 h at room temperature. The mixture was purified by reverse phase chromatography on C18 (80 g, MeCN/H$_2$O (0.05% CF$_3$COOH): 0→45%) to yield 2-(3-((tert-butyldimethylsilyl)oxy)-1-(2-(difluoromethyl)-1'H,2H-[3,4'-bipyrazol]-1'-yl)-3-methylbutyl)-5-(3-chloro-2-fluoro-6-(1H-tetrazol-1-yl)phenyl)pyridine 1-oxide as a light yellow solid. LC/MS: mass calculated for C$_{30}$H$_{35}$ClF$_3$N$_9$O$_2$Si: 673.23, measured (ES, m/z): 696.10 [M+H]$^+$.

Step 12: (R)-5-(3-Chloro-2-fluoro-6-(1H-tetrazol-1-yl)phenyl)-2-(1-(2-(difluoromethyl)-1'H,2H-[3,4'-bipyrazol]-1'-yl)-3-hydroxy-3-methylbutyl)pyridine 1-oxide A mixture of 2-(3-((tert-butyldimethylsilyl)oxy)-1-(2-(difluoromethyl)-1'H,2H-[3,4'-bipyrazol]-1'-yl)-3-methylbutyl)-5-(3-chloro-2-fluoro-6-(1H-tetrazol-1-yl)phenyl)pyridine 1-oxide (0.10 g, 0.15 mmol, 1.0 equiv.) and trifluoroacetic acid (0.5 mL) in DCM (1.5 mL) was stirred for 1 h at room temperature. The mixture was diluted with H$_2$O, then extracted with ethyl acetate twice. The combined organic layers was washed with brine, dried over Na$_2$SO$_4$, concentrated and purified by reverse phase chromatography on C18 (80 g, MeCN/H$_2$O (0.05% CF$_3$COOH): 0→45%) and Prep-Chiral-HPLC to yield (R)-5-(3-chloro-2-fluoro-6-(1H-tetrazol-1-yl)phenyl)-2-(1-(2-(difluoromethyl)-1'H,2H-[3,4'-bipyrazol]-1'-yl)-3-hydroxy-3-methylbutyl)pyridine 1-oxide as a white solid.

LC/MS: mass calculated for C$_{24}$H$_{21}$ClF$_3$N$_9$O$_2$: 559.15, measured (ES, m/z): 560.10 [M+H]$^+$. $^1$H NMR (400 MHz, DMSO-d$_6$): δ 9.70 (s, 1H), 8.40-8.46 (m, 2H), 8.02-8.11 (m, 1H), 7.67-7.99 (m, 4H), 7.43 (d, J=8.3 Hz, 1H), 7.14-7.23 (m, 1H), 6.69 (d, J=1.7 Hz, 1H), 6.30-6.41 (m, 1H), 4.53 (s, 1H), 2.52-2.63 (m, 1H), 2.10-2.22 (m, 1H), 0.96 (d, J=5.9 Hz, 6H). $^{19}$F NMR (376 MHz, DMSO-d$_6$): δ -93.59, -112.75.

Example 686: (S)-5-(3-Chloro-2-fluoro-6-(1H-tetrazol-1-yl)phenyl)-2-(1-(2-(difluoromethyl)-1'H,2H-[3,4'-bipyrazol]-1'-yl)-3-methoxypropyl)pyridine 1-oxide

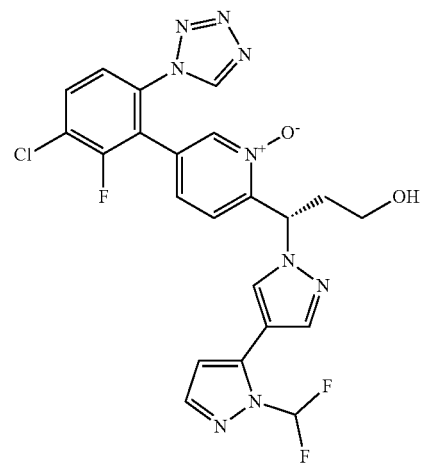 [SMILES: [O-][n+]1cc(-c2c(-n3cnnn3)ccc(Cl)c2F)ccc1[C@H](CCO)n1cc(-c2ccnn2C(F)F)cn1]

LC/MS: mass calculated for C$_{22}$H$_{17}$ClF$_3$N$_9$O$_2$: 531.11, measured (ES, m/z): 532.05 [M+H]$^+$. $^1$H NMR (300 MHz, DMSO-d$_6$) δ 9.70 (s, 1H), 8.44 (d, J=1.5 Hz, 1H), 8.36 (s, 1H), 7.62-8.11 (m, 5H), 7.40 (d, J=8.3 Hz, 1H), 7.18 (dd, J=8.3, 1.7 Hz, 1H), 6.69 (d, J=1.7 Hz, 1H), 6.22-6.26 (m, 1H), 4.73 (t, J=5.2 Hz, 1H), 3.33-3.45 (m, 1H), 3.18-3.28 (m, 1H), 2.22-2.47 (m, 2H). $^{19}$F NMR (282 MHz, DMSO-d$_6$) δ -93.61 (d, J=9.7 Hz), -112.69, -218.34.

Example 687: (R)-5-(3-Chloro-2-fluoro-6-(1H-tetrazol-1-yl)phenyl)-2-(1-(2-(difluoromethyl)-1'H,2H-[3,4'-bipyrazol]-1'-yl)-3-hydroxypropyl)pyridine 1-oxide

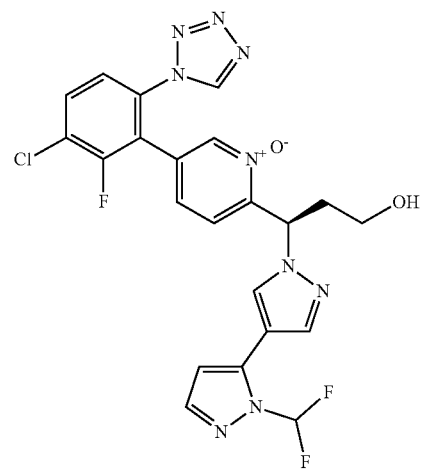

A mixture of 1'-(3-((tert-butyldimethylsilyl)oxy)-1-(5-(3-chloro-2-fluoro-6-(1H-tetrazol-1-yl)phenyl)pyridin-2-yl)propyl)-2-(difluoromethyl)-1'H,2H-3,4'-bipyrazole (150 mg, 0.24 mmol, 1.0 equiv.), methyltrioxorhenium (30 mg, 0.12 mmol, 0.5 equiv.) and hydrogen peroxide (0.5 mL, 30 wt %) in CH₃OH (1 mL) was stirred for 3 h at room temperature. The resulting mixture was purified by reverse phase chromatography on C18 (MeCN/H₂O (0.05% CF₃COOH)) to yield 5-(3-chloro-2-fluoro-6-(1H-tetrazol-1-yl)phenyl)-2-(1-(2-(difluoromethyl)-1'H,2H-[3,4'-bipyrazol]-1'-yl)-3-hydroxypropyl)pyridine 1-oxide as a white solid. The racemic product was separated by chiral-HPLC to yield (R*)-5-(3-chloro-2-fluoro-6-(1H-tetrazol-1-yl)phenyl)-2-(1-(2-(difluoromethyl)-1'H,2H-[3,4'-bipyrazol]-1'-yl)-3-hydroxypropyl)pyridine 1-oxide as a white solid.

LC/MS: mass calculated for $C_{22}H_{17}ClF_3N_9O_2$: 531.11, measured (ES, m/z): 532.05 [M+H]⁺. ¹H NMR (300 MHz, DMSO-$d_6$) δ 9.70 (s, 1H), 8.44 (d, J=1.5 Hz, 1H), 8.36 (s, 1H), 7.61-8.12 (m, 5H), 7.40 (d, J=8.3 Hz, 1H), 7.17-7.20 (m, 1H), 6.69 (d, J=1.8 Hz, 1H), 6.23-6.28 (m, 1H), 4.73 (t, J=5.2 Hz, 1H), 3.33-3.45 (m, 1H), 3.18-3.28 (m, 1H), 2.24-2.47 (m, 2H). ¹⁹F-NMR (282 MHz, DMSO-$d_6$) δ −93.61, −112.69.

Example 688: (S)-5-(3-Chloro-2-fluoro-6-(1H-tetrazol-1-yl)phenyl)-2-(2-(1-isopropyl-1H-pyrazol-3-yl)-1-(4-(2-(trifluoromethyl)pyridin-4-yl)-1H-pyrazol-1-yl)ethyl)pyridine 1-oxide

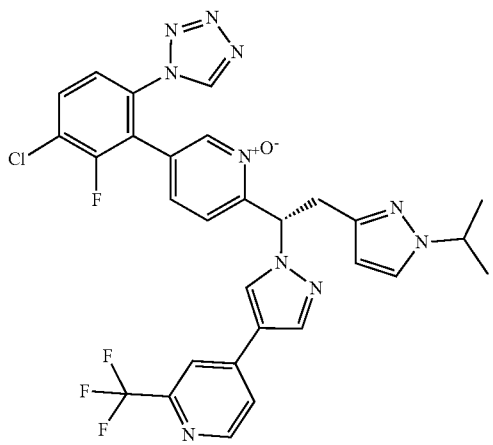

LC/MS: mass calculated for $C_{29}H_{23}ClF_4N_{10}O$: 638.17, measured (ES, m/z): 639.2 [M+H]⁺. ¹H NMR (400 MHz, DMSO-$d_6$) δ 9.69 (s, 1H), 8.82 (s, 1H), 8.66 (d, J=5.2 Hz, 1H), 8.45 (s, 1H), 8.31 (s, 1H), 8.02-8.12 (m, 2H), 7.88 (d, J=5.4 Hz, 1H), 7.76 (dd, J=8.8, 1.5 Hz, 1H), 7.53 (d, J=2.3 Hz, 1H), 7.42-7.48 (m, 1H), 7.16-7.24 (m, 1H), 6.34 (t, J=7.5 Hz, 1H), 5.79 (d, J=2.3 Hz, 1H), 4.31-4.37 (m, 1H), 3.54 (d, J=7.6 Hz, 2H), 1.30 (d, J=6.4 Hz, 6H). ¹⁹F NMR (376 MHz, DMSO-$d_6$) δ −66.55, −112.69.

Example 689: (R)-5-(3-Chloro-2-fluoro-6-(1H-tetrazol-1-yl)phenyl)-2-(2-(1-isopropyl-1H-pyrazol-3-yl)-1-(4-(2-(trifluoromethyl)pyridin-4-yl)-1H-pyrazol-1-yl)ethyl)pyridine 1-oxide

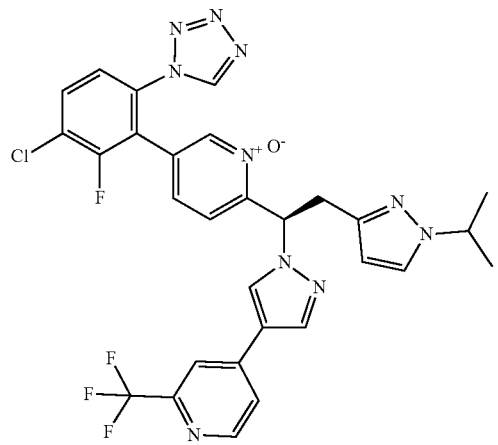

LC/MS: mass calculated for $C_{29}H_{23}ClF_4N_{10}O$: 638.17, measured (ES, m/z): 639.1 [M+H]⁺. ¹H NMR (400 MHz, DMSO-$d_6$) δ 9.69 (s, 1H), 8.82 (s, 1H), 8.64-8.69 (m, 1H), 8.45 (d, J=1.6 Hz, 1H), 8.31 (s, 1H), 8.02-8.12 (m, 2H), 7.88 (dd, J=5.1, 1.7 Hz, 1H), 7.73-7.79 (m, 1H), 7.53 (d, J=2.2 Hz, 1H), 7.43-7.48 (m, 1H), 7.19 (dd, J=8.3, 1.6 Hz, 1H), 6.34 (t, J=7.5 Hz, 1H), 5.79 (d, J=2.3 Hz, 1H), 4.35-4.43 (m, 1H), 3.51-3.57 (m, 2H), 1.31 (d, J=6.4 Hz, 6H). ¹⁹F NMR (376 MHz, DMSO-$d_6$) δ −66.55, −112.69.

Example 690: (R)-5-(3-Chloro-2-fluoro-6-(1H-tetrazol-1-yl)phenyl)-2-((S*)-2-(2,2-difluorocyclopropyl)-1-(4-(1-(difluoromethyl)-1H-1,2,3-triazol-4-yl)-1H-pyrazol-1-yl)ethyl)pyridine 1-oxide

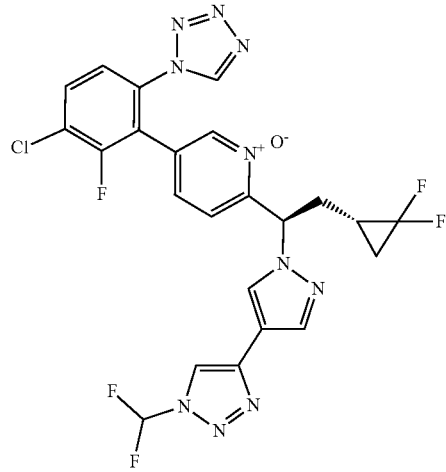

Step 1: 2-(2,2-Difluorocyclopropyl)-N-methoxy-N-methylacetamide

To a solution of 2-(2,2-difluorocyclopropyl)acetic acid (1.0 g, 7.4 mmol, 1.0 equiv.) in DCM (10 mL) was added 1,1'-carbonyldiimidazole (1.8 g, 11.0 mmol, 1.5 equiv.) and the solution was stirred for 15 min at room temperature. Then N,O-dimethylhydroxylamine hydrochloride (0.92 g, 11.0 mmol, 1.5 equiv.) was added and the mixture stirred at room temperature overnight. The mixture was diluted with $H_2O$, extracted with DCM twice. The combined layers were washed with hydrochloric acid (pH=3~4), saturated sodium bicarbonate and brine twice respectively, dried over $Na_2SO_4$ and concentrated to yield 2-(2,2-difluorocyclopropyl)-N-methoxy-N-methylacetamide as a light yellow oil. $^1H$ NMR (400 MHz, Chloroform-d) δ 3.69 (s, 3H), 3.21 (s, 3H), 2.72 (dd, J=17.1, 6.7 Hz, 1H), 2.47-2.59 (m, 1H), 1.93 (m, 1H), 1.54 (m, 1H), 1.04 (m, 1H).

Step 2: 1-(5-Bromopyridin-2-yl)-2-(2,2-difluorocyclopropyl)ethan-1-one

To a solution of 2,5-dibromopyridine (1.1 g, 4.7 mmol, 1.0 equiv.) in toluene (10 mL) added n-butyllithium (2.1 mL, 5.2 mmol, 1.1 equiv.) after the temperature was dropped to −70° C. and stirred for 1 h under $N_2$. Then 2-(2,2-difluorocyclopropyl)-N-methoxy-N-methylacetamide (0.88 g, 4.9 mmol, 1.1 equiv.) was added and the mixture stirred for additional 1H. The reaction was then quenched with the addition of saturated ammonium chloride aqueous solution and extracted with ethyl acetate twice. The combined organic layers were washed with brine, dried over $Na_2SO_4$, concentrated and purified by silica gel chromatography (0→30% EtOAc/petroleum ether) to yield 1-(5-bromopyridin-2-yl)-2-(2,2-difluorocyclopropyl)ethan-1-one as a light yellow oil. LC/MS: mass calculated for $C_{10}H_8BrF_2NO$: 274.98, measured (ES, m/z): 276.90, 277.90 $[M+H, M+H+2]^+$.

Step 3: 1-(5-Bromopyridin-2-yl)-2-(2,2-difluorocyclopropyl)ethan-1-ol

To a solution of 1-(5-bromopyridin-2-yl)-2-(2,2-difluorocyclopropyl)ethan-1-one (0.82 g, 2.97 mmol, 1.0 equiv.) in $CH_3OH$ (10 mL) was added $NaBH_4$ (0.17 g, 4.46 mmol, 1.5 equiv.) at 0° C. The mixture was stirred at room temperature for 2 h. The reaction was quenched with water and then extracted with ethyl acetate twice. The combined layers were washed with brine, dried over $Na_2SO_4$ and concentrated to yield 1-(5-bromopyridin-2-yl)-2-(2,2-difluorocyclopropyl)ethan-1-ol as a light yellow oil. LC/MS: mass calculated for $C_{10}H_{10}BrF_2NO$: 276.99, measured (ES, m/z): 278.05, 279.05 $[M+H, M+H+2]^+$.

Step 4: 1-(5-Bromopyridin-2-yl)-2-(2,2-difluorocyclopropyl)ethyl methanesulfonate To a mixture of 1-(5-bromopyridin-2-yl)-2-(2,2-difluorocyclopropyl)ethan-1-ol (0.78 g, 2.81 mmol, 1.0 equiv.) and triethylamine (1.95 mL, 14.02 mmol, 5.0 equiv.) in DCM (10 mL) was added methanesulfonic anhydride (0.98 g, 5.61 mmol, 2.0 equiv.) at 0° C. and the solution was stirred for 2 h at room temperature. The mixture was diluted with $H_2O$, extracted with DCM twice. The combined organic layers were washed with brine, dried over $Na_2SO_4$, concentrated and purified by silica gel chromatography (0→50% EA/PE) to yield 1-(5-bromopyridin-2-yl)-2-(2,2-difluorocyclopropyl)ethyl methanesulfonate as a light yellow oil. LC/MS: mass calculated for $C_{11}H_{12}BrF_2NO_3S$: 354.97, measured (ES, m/z): 355.85, 357.85 $[M+H, M+H+2]^+$.

Step 5: 5-Bromo-2-(2-(2,2-difluorocyclopropyl)-1-(4-(1-(difluoromethyl)-1H-1,2,3-triazol-4-yl)-1H-pyrazol-1-yl)ethyl)pyridine A mixture of 1-(difluoromethyl)-4-(1H-pyrazol-4-yl)-1H-1,2,3-triazole (0.10 g, 0.54 mmol, 1.0 equiv.) and cesium carbonate (0.19 g, 0.59 mmol, 1.1 equiv.) in acetonitrile (3 mL) was stirred for 15 min at room temperature. 1-(5-Bromopyridin-2-yl)-2-(2,2-difluorocyclopropyl)ethyl methanesulfonate (0.10 g, 0.54 mmol, 1.0 equiv.) was added and the solution was stirred for 3 h at 90° C. The mixture was diluted with $H_2O$, extracted with DCM twice. The combined organic layers were washed with brine, dried over $Na_2SO_4$, concentrated and purified by silica gel chromatography (0→60% EA/PE) to yield 5-bromo-2-(2-(2,2-difluorocyclopropyl)-1-(4-(1-(difluoromethyl)-1H-1,2,3-triazol-4-yl)-1H-pyrazol-1-yl)ethyl)pyridine as a light yellow oil. LC/MS: mass calculated for $C_{16}H_{13}BrF_4N_6$: 444.03, measured (ES, m/z): 445.15, 447.15 $[M+H, M+H+2]^+$.

Step 6: 4-Chloro-2-(6-(2-(2,2-difluorocyclopropyl)-1-(4-(1-(difluoromethyl)-1H-1,2,3-triazol-4-yl)-1H-pyrazol-1-yl)ethyl)pyridin-3-yl)-3-fluoroaniline A mixture of 5-bromo-2-(2-(2,2-difluorocyclopropyl)-1-(4-(1-(difluoromethyl)-1H-1,2,3-triazol-4-yl)-1H-pyrazol-1-yl)ethyl)pyridine (0.24 g, 0.54 mmol, 1.0 equiv.), (6-amino-3-chloro-2-fluorophenyl)boronic acid (0.15 g, 0.81 mmol, 1.5 equiv.), $Pd(PPh_3)_4$ (0.13 g, 0.11 mmol, 0.2 equiv.), $K_2CO_3$ (0.45 g, 3.23 mmol, 6.0 equiv.) in 1,4-dioxane (4 mL) and water (1 mL) was refluxed at 90° C. under $N_2$ for 2 h. The mixture was diluted with $H_2O$, extracted with ethyl acetate twice. The combined organic layers were washed with brine, dried over $Na_2SO_4$, concentrated and purified by silica gel chromatography (0→5%, MeOH/DCM) to yield 4-chloro-2-(6-(2-(2,2-difluorocyclopropyl)-1-(4-(1-(difluoromethyl)-1H-1,2,3-triazol-4-yl)-1H-pyrazol-1-yl)ethyl)pyridin-3-yl)-3-fluoroaniline as a light yellow oil. LC/MS: mass calculated for $C_{22}H_{17}ClF_5N_7$: 509.12, measured (ES, m/z): 510.25 $[M+H]^+$.

Step 7: 5-(3-Chloro-2-fluoro-6-(4H-1,2,4-triazol-4-yl)phenyl)-2-(2-(2,2-difluorocyclopropyl)-1-(4-(1-(difluoromethyl)-1H-1,2,3-triazol-4-yl)-1H-pyrazol-1-yl)ethyl)pyridine A mixture of 2-(6-(3-((tert-butyldimethylsilyl)oxy)-1-(2-(difluoromethyl)-1'H,2H-[3,4'-bipyrazol]-1'-yl)-3-methylbutyl)pyridin-3-yl)-4-chloro-3-fluoroaniline (100 mg, 0.20 mmol, 1.0 equiv.), trimethoxymethane (0.2 mL), azidotrimethylsilane (0.2 mL) and acetic acid (0.2 mL) was stirred overnight at room temperature. The reaction mixture was purified by reverse phase chromatography on C18 (80 g, $MeCN/H_2O$ (0.05% $CF_3COOH$): 0→45%) to yield 5-(3-chloro-2-fluoro-6-(1H-tetrazol-1-yl)phenyl)-2-(2-(2,2-difluorocyclopropyl)-1-(4-(1-(difluoromethyl)-1H-1,2,3-triazol-4-yl)-1H-pyrazol-1-yl)ethyl)pyridine as a light yellow solid. LC/MS: mass calculated for $C_{24}H_{17}ClF_5N_9$: 561.91, measured (ES, m/z): 563.20 [M+H]$^+$.

Step 8: 5-(3-Chloro-2-fluoro-6-(1H-tetrazol-1-yl)phenyl)-2-((1S*)-2-(2,2-difluorocyclopropyl)-1-(4-(1-(difluoromethyl)-1H-1,2,3-triazol-4-yl)-1H-pyrazol-1-yl)ethyl)pyridine 1-oxide A mixture of 5-(3-chloro-2-fluoro-6-(1H-tetrazol-1-yl)phenyl)-2-(2-(2,2-difluorocyclopropyl)-1-(4-(1-(difluoromethyl)-1H-1,2,3-triazol-4-yl)-1H-pyrazol-1-yl)ethyl)pyridine (50 mg, 0.09 mmol, 1.0 equiv.), hydrogen peroxide (30 wt %, 0.10 mL, 0.89 mmol, 10.0 equiv.) and methyltrioxorhenium (5 mg, 0.02 mmol, 0.2 equiv.) in $CH_3OH$ (1 mL) was stirred for 1 h at room temperature. The mixture was purified by reverse phase chromatography on C18 (80 g, MeCN/H$_2$O (0.05% CF$_3$COOH): 0→45%) and Prep-Chiral-HPLC to yield (R)-5-(3-chloro-2-fluoro-6-(1H-tetrazol-1-yl)phenyl)-2-((1S*)-2-(2,2-difluorocyclopropyl)-1-(4-(1-(difluoromethyl)-1H-1,2,3-triazol-4-yl)-1H-pyrazol-1-yl)ethyl)pyridine 1-oxide as a white solid.

LC/MS: mass calculated for $C_{23}H_{16}ClF_5N_{10}O$: 578.11, measured (ES, m/z): 579.00 [M+H]$^+$. $^1$H NMR (400 MHz, DMSO-d$_6$): δ 9.69 (s, 1H), 8.92 (s, 1H), 8.51 (s, 1H), 8.15-8.46 (m, 2H), 8.02-8.11 (m, 2H), 7.70-7.80 (m, 1H), 7.33 (d, J=8.3 Hz, 1H), 7.15-7.23 (m, 1H), 6.15-6.26 (m, 1H), 2.37-2.48 (m, 2H), 1.55-1.70 (m, 1H), 1.28-1.42 (m, 1H), 0.80-0.90 (m, 1H). $^{19}$F NMR (376 MHz, DMSO-d$_6$): δ −96.23, −112.73, −127.30, −127.72, −141.54, −141.95.

Example 691: (S)-5-(3-Chloro-2-fluoro-6-(1H-tetrazol-1-yl)phenyl)-2-((R*)-2-(2,2-difluorocyclopropyl)-1-(4-(1-(difluoromethyl)-1H-1,2,3-triazol-4-yl)-1H-pyrazol-1-yl)ethyl)pyridine 1-oxide

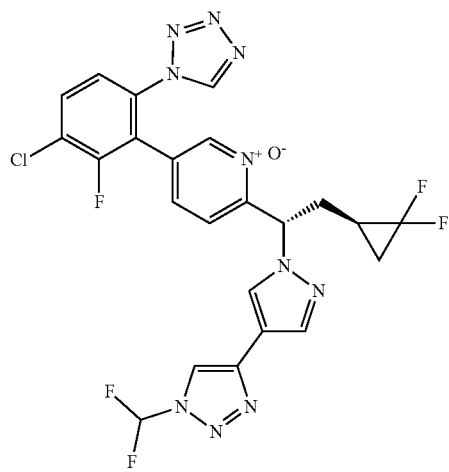

LC/MS: mass calculated for $C_{23}H_{16}ClF_5N_{10}O$: 578.11, measured (ES, m/z): 579.05 [M+H]$^+$. $^1$H NMR (400 MHz, DMSO-d$_6$) δ 9.69 (s, 1H), 8.92 (s, 1H), 8.51 (s, 1H), 8.14-8.47 (m, 2H), 7.94-8.11 (m, 2H), 7.76 (dd, J=8.7, 1.5 Hz, 1H), 7.33 (d, J=8.3 Hz, 1H), 7.18 (dd, J=8.2, 1.7 Hz, 1H), 6.18-6.22 (m, 1H), 2.34-2.50 (m, 2H), 1.60-1.66 (m, 1H), 1.29-1.41 (m, 1H), 0.81-0.88 (m, 1H). $^{19}$F NMR (376 MHz, DMSO-d$_6$) δ −96.23, −112.71, −127.32, −127.72, −141.55, −141.95.

Example 692: (R)-5-(3-Chloro-6-(4-chloro-1H-1,2,3-triazol-1-yl)-2-fluorophenyl)-2-(1-(4-(1-(difluoromethyl)-1H-1,2,3-triazol-4-yl)-1H-pyrazol-1-yl)-2-(4-(difluoromethyl)-1H-pyrazol-1-yl)ethyl)pyridine 1-oxide

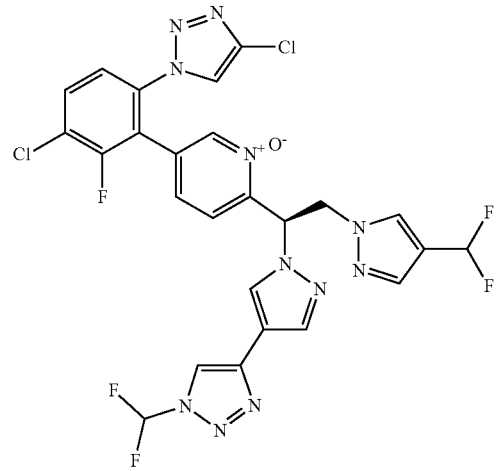

LC/MS: mass calculated for $C_{25}H_{16}Cl_2F_5N_{11}O$: 651.08, measured (ES, m/z): 651.95 [M+H]$^+$. $^1$H NMR (400 MHz, DMSO-d$_6$) δ 8.87 (s, 1H), 8.69 (s, 1H), 8.50 (d, J=1.6 Hz, 1H), 8.11-8.45 (m, 2H), 7.99-8.08 (m, 2H), 7.90 (d, J=1.9 Hz, 1H), 7.65-7.73 (m, 2H), 7.37 (d, J=8.3 Hz, 1H), 7.22 (dd, J=8.2, 1.7 Hz, 1H), 6.94 (t, J=56.1 Hz, 1H), 6.62-6.66 (m, 1H), 5.02-5.18 (m, 2H). $^{19}$F NMR (376 MHz, DMSO-d$_6$) δ −96.20, −96.26, −104.95, −105.05, −112.72, −112.86.

Example 693: (S)-5-(3-Chloro-6-(4-chloro-1H-1,2,3-triazol-1-yl)-2-fluorophenyl)-2-(1-(4-(1-(difluoromethyl)-1H-1,2,3-triazol-4-yl)-1H-pyrazol-1-yl)-2-(4-(difluoromethyl)-1H-pyrazol-1-yl)ethyl)pyridine 1-oxide

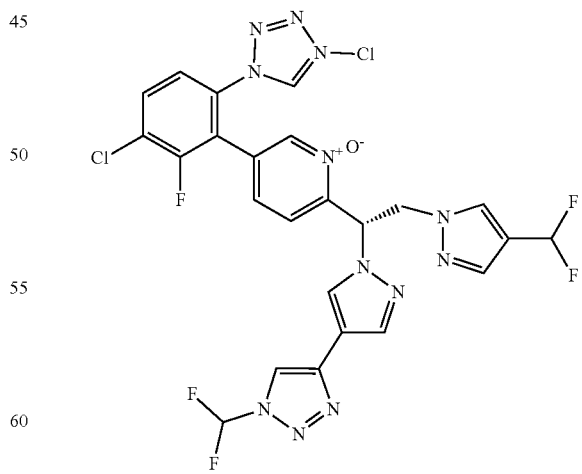

LC/MS: mass calculated for $C_{25}H_{16}Cl_2F_5N_{11}O$: 651.08, measured (ES, m/z): 651.95 [M+H]$^+$. $^1$H NMR (400 MHz, DMSO-d$_6$) δ 8.87 (s, 1H), 8.69 (s, 1H), 8.50 (d, J=1.6 Hz, 1H), 8.10-8.47 (m, 2H), 7.99-8.08 (m, 2H), 7.90 (d, J=1.7

Hz, 1H), 7.65-7.73 (m, 2H), 7.37 (d, J=8.3 Hz, 1H), 7.22 (dd, J=8.3, 1.6 Hz, 1H), 6.94 (t, J=56.1 Hz, 1H), 6.62-6.66 (m, 1H), 5.02-5.18 (m, 2H). $^{19}$F NMR (376 MHz, DMSO-d$_6$) δ −96.18, −96.26, −105.05, −112.86, −112.86, −218.50.

Example 694: (R)-(3-Chloro-2-fluoro-6-(1H-tetrazol-1-yl)phenyl)-2-(2-cyclobutyl-1-(4-(1-(difluoromethyl)-1H-1,2,3-triazol-4-yl)-1H-pyrazol-1-yl)ethyl)pyridine 1-oxide

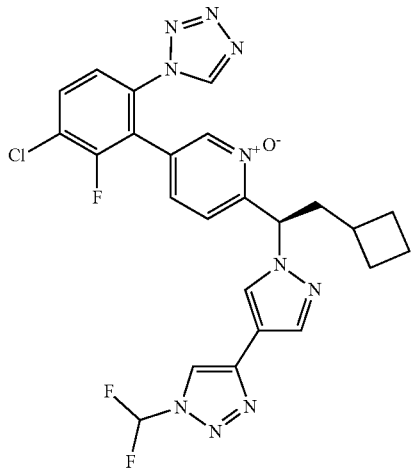

LC/MS: mass calculated for C$_{24}$H$_{20}$ClF$_3$N$_{10}$O: 556.15, measured (ES, m/z): 579.00 [M+Na]$^+$. $^1$H NMR (400 MHz, DMSO-d$_6$) δ 9.69 (s, 1H), 8.89 (s, 1H), 8.14-8.48 (m, 3H), 8.06 (dd, J=8.7, 7.7 Hz, 1H), 7.99 (s, 1H), 7.76 (dd, J=8.7, 1.5 Hz, 1H), 7.32 (d, J=8.3 Hz, 1H), 7.16 (dd, J=8.3, 1.7 Hz, 1H), 5.97 (dd, J=10.3, 4.1 Hz, 1H), 2.40-2.47 (m, 1H), 2.19-2.26 (m, 1H), 2.06-2.12 (m, 1H), 1.95-2.00 (m, 1H), 1.72-1.85 (m, 4H), 1.50-1.59 (m, 1H). $^{19}$F NMR (376 MHz, DMSO-d$_6$) δ −96.22, −112.75.

Example 695: (S)-5-(3-Chloro-2-fluoro-6-(1H-tetrazol-1-yl)phenyl)-2-(2-cyclobutyl-1-(4-(1-(difluoromethyl)-1H-1,2,3-triazol-4-yl)-1H-pyrazol-1-yl)ethyl)pyridine 1-oxide

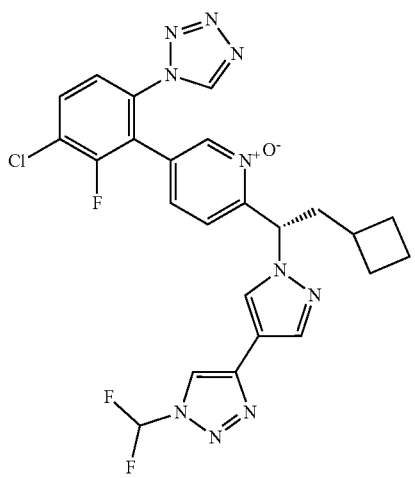

LC/MS: mass calculated for C$_{24}$H$_{20}$ClF$_3$N$_{10}$O: 556.15, measured (ES, m/z): 579.00 [M+Na]$^+$. $^1$H NMR (400 MHz, DMSO-d$_6$) δ 9.69 (s, 1H), 8.89 (s, 1H), 8.13-8.48 (m, 3H), 8.06 (dd, J=8.7, 7.8 Hz, 1H), 7.99 (s, 1H), 7.76 (dd, J=8.8, 1.5 Hz, 1H), 7.32 (d, J=8.3 Hz, 1H), 7.16 (dd, J=8.3, 1.7 Hz, 1H), 5.94-5.98 (m, 1H), 2.40-2.47 (m, 1H), 2.19-2.35 (m, 1H), 2.08-2.12 (m, 1H), 1.95-1.99 (m, 1H), 1.69-1.83 (m, 4H), 1.50-1.59 (m, 1H). $^{19}$F NMR (376 MHz, DMSO-d$_6$) δ −73.68, −96.22, −112.74.

Example 696: (S*)-5-(3-Chloro-2-fluoro-6-(1H-tetrazol-1-yl)phenyl)-2-(3-(difluoromethoxy)-1-(4-(1-(difluoromethyl)-1H-1,2,3-triazol-4-yl)-1H-pyrazol-1-yl)propyl)pyridine 1-oxide

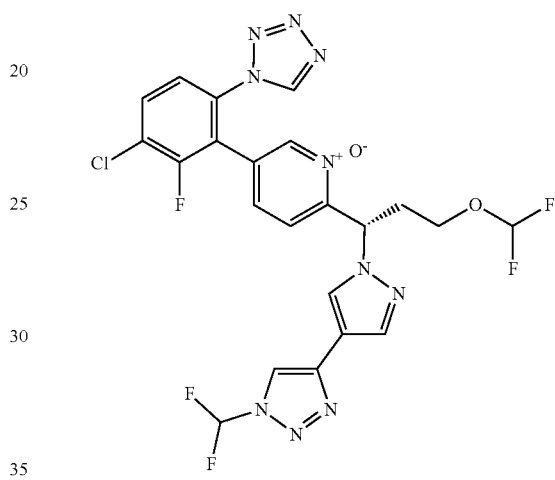

Step 1: 5-Bromo-2-(3-(difluoromethoxy)-1-(4-(1-(difluoromethyl)-1H-1,2,3-triazol-5-yl)-1H-pyrazol-1-yl)propyl)pyridine A mixture of cesium carbonate (437 mg, 1.34 mmol, 1.0 equiv.) and 1-(difluoromethyl)-4-(1H-pyrazol-4-yl)-1H-1,2,3-triazole (248 mg, 1.34 mmol, 1.0 equiv.) in acetonitrile (5 mL) was stirred for 15 min at room temperature. 1-(5-bromopyridin-2-yl)-3-(difluoromethoxy)propyl methanesulfonate (483 mg, 1.34 mmol, 1.0 equiv.) was added and the solution was stirred for 2.5 h at 90° C. The resulting mixture was diluted with water, extracted with EA (3×10 mL). Then the organic layers were combined, washed with brine, dried over Na$_2$SO$_4$ and concentrated. The residue was purified by silica gel chromatography (EA/PE, 0%→80%) to yield 5-bromo-2-(3-(difluoromethoxy)-1-(4-(1-(difluoromethyl)-1H-1,2,3-triazol-4-yl)-1H-pyrazol-1-yl)propyl)pyridine as a colorless oil. LC/MS: mass calculated for C$_{15}$H$_{13}$BrF$_4$N$_6$O: 448.03, measured (ES, m/z): 450.95 [M+H+2]$^+$.

Step 2: 4-Chloro-2-(6-(3-(difluoromethoxy)-1-(4-(1-(difluoromethyl)-1H-1,2,3-triazol-5-yl)-1H-pyrazol-1-yl)propyl)pyridin-3-yl)-3-fluoroaniline A mixture of 5-bromo-2-(3-(difluoromethoxy)-1-(4-(1-(difluoromethyl)-1H-1,2,3-triazol-4-yl)-1H-pyrazol-1-yl)propyl)pyridine (150 mg, 0.33 mmol, 1.0 equiv.), 6-amino-3-chloro-2-fluorophenylboronic acid (95 mg, 0.5 mmol, 1.5 equiv.), Pd(PPh$_3$)$_4$ (39 mg, 0.03 mmol, 0.1 equiv.) and K$_2$CO$_3$ (138 mg, 1.0 mmol, 3.0 equiv.) in 1,4-dioxane/water (V/V=5:1, 6 mL) was refluxed at 90° C. under $N_2$ for 3 h. The resulting mixture was diluted with water, and the mixture extracted with EA (3×15 mL). The organic layers were combined, washed with brine (5 mL), dried over $Na_2SO_4$ and concentrated. The residue was purified by silica gel chromatography (0%→80%, EA/PE) to yield 4-chloro-2-(6-(3-(difluoromethoxy)-1-(4-(1-(difluoromethyl)-1H-1,2,3-triazol-4-yl)-1H-pyrazol-1-yl)propyl)pyridin-3-yl)-3-fluoroaniline as a light yellow oil. LC/MS: mass calculated for $C_{21}H_{17}ClF_5N_7O$: 513.11, measured (ES, m/z): 514.00 $[M+H]^+$.

Step 3: 5-(3-Chloro-2-fluoro-6-(1H-tetrazol-1-yl)phenyl)-2-(3-(difluoromethoxy)-1-(4-(1-(difluoromethyl)-1H-1,2,3-triazol-5-yl)-1H-pyrazol-1-yl)propyl)pyridine A mixture of 4-chloro-2-(6-(3-(difluoromethoxy)-1-(4-(1-(difluoromethyl)-1H-1,2,3-triazol-4-yl)-1H-pyrazol-1-yl)propyl)pyridin-3-yl)-3-fluoroaniline (128 mg, 0.25 mmol, 1.0 equiv.), trimethoxymethane (2 mL), azidotrimethylsilane (2 mL) and acetic acid (2 mL) was stirred overnight at 30° C. The reaction was purified by reverse chromatography on C18 (0→55% MeCN/$H_2O$ (0.05% $CF_3COOH$)) to yield 5-(3-chloro-2-fluoro-6-(1H-tetrazol-1-yl)phenyl)-2-(3-(difluoromethoxy)-1-(4-(1-(difluoromethyl)-1H-1,2,3-triazol-5-yl)-1H-pyrazol-1-yl)propyl)pyridine as a light yellow solid. LC/MS: mass calculated for $C_{22}H_{16}ClF_5N_{10}O$: 566.11, measured (ES, m/z): 567.00 $[M+H]^+$.

Step 4: (S*)-5-(3-Chloro-2-fluoro-6-(1H-tetrazol-1-yl)phenyl)-2-(3-(difluoromethoxy)-1-(4-(1-(difluoromethyl)-1H-1,2,3-triazol-5-yl)-1H-pyrazol-1-yl)propyl)pyridine 1-oxide A mixture of 5-(3-chloro-2-fluoro-6-(1H-tetrazol-1-yl)phenyl)-2-(3-(difluoromethoxy)-1-(4-(1-(difluoromethyl)-1H-1,2,3-triazol-4-yl)-1H-pyrazol-1-yl)propyl)pyridine (128.2 mg, 0.23 mmol, 1.0 equiv.), methyltrioxorhenium (28.9 mg, 0.11 mmol, 0.5 equiv.) and hydrogen peroxide (0.5 mL, 30 wt %) in $CH_3OH$ (2 mL) was stirred for 3 h at room temperature. The resulting mixture was purified by reverse phase chromatography on C18 (MeCN/$H_2O$ (0.05% $CF_3COOH$)) to yield 5-(3-chloro-2-fluoro-6-(1H-tetrazol-1-yl)phenyl)-2-(3-(difluoromethoxy)-1-(4-(1-(difluoromethyl)-1H-1,2,3-triazol-4-yl)-1H-pyrazol-1-yl)propyl)pyridine 1-oxide as a white solid. The racemic product was separated by chiral-HPLC to yield (S*)-5-(3-chloro-2-fluoro-6-(1H-tetrazol-1-yl)phenyl)-2-(3-(difluoromethoxy)-1-(4-(1-(difluoromethyl)-1H-1,2,3-triazol-4-yl)-1H-pyrazol-1-yl)propyl)pyridine 1-oxide as a white solid.

LC/MS: mass calculated for $C_{22}H_{16}ClF_5N_{10}O_2$: 582.11, measured (ES, m/z): 583.00 $[M+H]^+$. $^1H$ NMR: (400 MHz, DMSO-$d_6$) δ 9.69 (s, 1H), 8.91 (s, 1H), 7.99-8.46 (m, 5H), 7.74-7.77 (m, 1H), 7.27 (d, J=8.3 Hz, 1H), 7.17-7.19 (m, 1H), 6.64 (t, J=75.7 Hz, 4H), 6.20-6.23 (m, 1H), 3.81-3.86 (m, 1H), 3.64-3.74 (m, 1H), 2.55-2.71 (m, 2H). $^{19}F$-NMR (376 MHz, DMSO-$d_6$) δ −83.28, −96.24, −112.68.

Example 697: (R*)-5-(3-Chloro-2-fluoro-6-(1H-tetrazol-1-yl)phenyl)-2-(3-(difluoromethoxy)-1-(4-(1-(difluoromethyl)-1H-1,2,3-triazol-4-yl)-1H-pyrazol-1-yl)propyl)pyridine 1-oxide

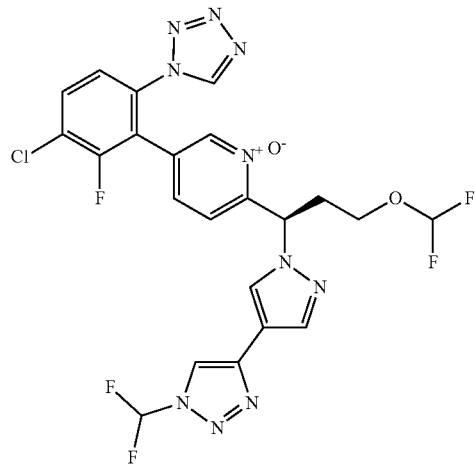

LC/MS: mass calculated for $C_{22}H_{16}ClF_5N_{10}O_2$: 582.11, measured (ES, m/z): 583.00 $[M+H]^+$. $^1H$ NMR (400 MHz, DMSO-$d_6$) δ 9.69 (s, 1H), 8.91 (s, 1H), 8.44-8.45 (m, 2H), 8.02-8.34 (m, 3H), 7.76 (dd, J=8.7, 1.5 Hz, 1H), 7.27 (d, J=8.3 Hz, 1H), 7.16-7.19 (m, 1H), 6.64 (t, J=75.7 Hz, 1H), 6.19-6.23 (m, 1H), 3.81-3.86 (m, 1H), 3.64-3.74 (m, 1H), 2.56-2.71 (m, 2H). $^{19}F$ NMR (376 MHz, DMSO-$d_6$) δ −83.28, −96.24, −112.68.

Example 698: (R*)-5-(3-Chloro-2-fluoro-6-(1H-tetrazol-1-yl)phenyl)-2-(1-(4-cyano-2-(difluoromethyl)-1'H,2H-[3,4'-bipyrazol]-1'-yl)-2-cyclopropylethyl)pyridine 1-oxide

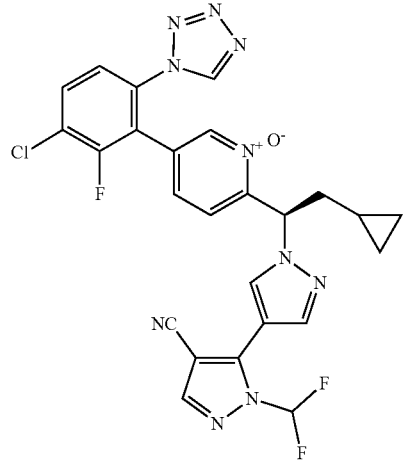

LC/MS: mass calculated for $C_{25}H_{18}ClF_3N_{10}O$: 566.13, measured (ES, m/z): 567.05 $[M+H]^+$. $^1H$ NMR (300 MHz, DMSO-$d_6$) δ 9.70 (s, 1H), 8.67 (s, 1H), 8.40-8.48 (m, 2H), 7.70-8.13 (m, 4H), 7.48 (d, J=8.3 Hz, 1H), 7.21 (dd, J=8.2, 1.7 Hz, 1H), 6.19-6.24 (m, 1H), 2.23-2.31 (m, 1H), 1.97-2.08 (m, 1H), 0.55-0.64 (m, 1H), 0.27-0.38 (m, 2H), 0.09-

0.15 (m, 1H), −0.12−−0.06 (m, 1H). ¹⁹F NMR (282 MHz, DMSO-$d_6$) δ −95.41, −112.69.

Example 699: 5-(3-Chloro-2-fluoro-6-(1H-tetrazol-1-yl)phenyl)-2-(1-(4-cyano-1-(difluoromethyl)-1H,1'H-[3,4'-bipyrazol]-1'-yl)-2-cyclopropylethyl)pyridine 1-oxide

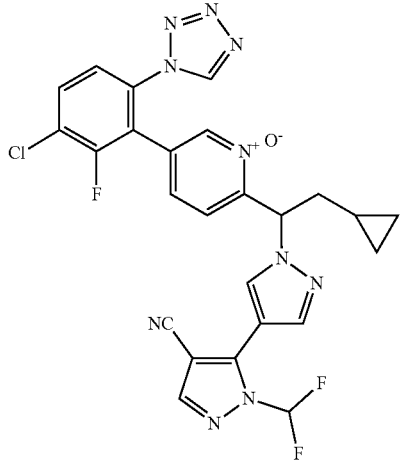

LC/MS: mass calculated for $C_{25}H_{18}ClF_3N_{10}O$: 566.13, measured (ES, m/z): 567.05 [M+H]⁺. ¹H NMR (300 MHz, DMSO-$d_6$) δ 9.69 (s, 1H), 8.66 (s, 1H), 8.59 (d, J=0.8 Hz, 1H), 8.42 (s, 1H), 7.70-8.13 (m, 4H), 7.46 (d, J=8.3 Hz, 1H), 7.15-7.28 (m, 1H), 6.17-6.26 (m, 1H), 2.22-2.32 (m, 1H), 1.95-2.06 (m, 1H), 0.55-0.62 (m, 1H), 0.24-0.39 (m, 2H), 0.07-0.13 (m, 1H), −0.12−−0.06 (m, 1H). ¹⁹F NMR (282 MHz, DMSO-$d_6$) δ −96.39, −112.73.

Example 700: (S*)-5-(3-Chloro-2-fluoro-6-(1H-tetrazol-1-yl)phenyl)-2-(1-(4-cyano-2-(difluoromethyl)-1'H,2H-[3,4'-bipyrazol]-1'-yl)-2-cyclopropylethyl)pyridine 1-oxide

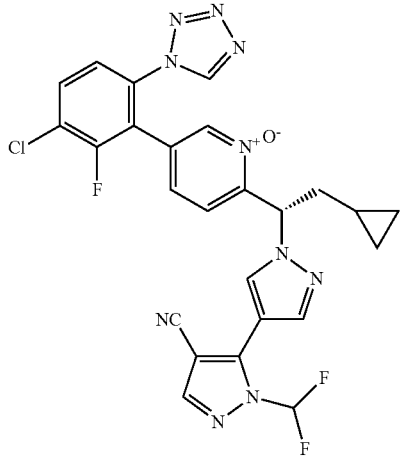

Step 1: 2-(Difluoromethyl)-1'-(tetrahydro-2H-pyran-2-yl)-1'H,2H-3,4'-bipyrazole

To a solution of 1-(difluoromethyl)-5-iodo-1H-pyrazole (6.7 g, 27.46 mmol, 1.0 equiv.) in 1,4-dioxane/water (60.0 mL) was added tert-butyl 4-(4,4,5,5-tetramethyl-1,3,2-dioxaborolan-2-yl)-1H-pyrazole-1-carboxylate (11.5 g, 41.19 mmol, 1.5 equiv.), $K_2CO_3$ (7.6 g, 54.92 mmol, 2.0 equiv.) and Pd(PPh₃)₄ (3.2 g, 2.75 mmol, 0.1 equiv.). Then the mixture was stirred at 90° C. for 2 h. The resulting mixture was diluted with EA (100 mL), filtered to remove the salt and water (300 mL) was added. Then extracted with EA (3×300 mL). The organic layers were combined, washed with brine (100 mL), dried over $Na_2SO_4$ and concentrated. The residue was purified by silica gel chromatography (0%→50%, PE/EA) to yield 2-(difluoromethyl)-1'-(tetrahydro-2H-pyran-2-yl)-1'H,2H-3,4'-bipyrazole as a yellow oil. LC/MS: mass calculated For $C_{12}H_{14}F_2N_4O$: 268.11, measured (ES, m/z): 269.05 [M+H]⁺.

Step 2: 4-Bromo-2-(difluoromethyl)-1'-(tetrahydro-2H-pyran-2-yl)-1'H,2H-3,4'-bipyrazole A mixture of 2-(difluoromethyl)-1'-(tetrahydro-2H-pyran-2-yl)-1'H,2H-3,4'-bipyrazole (2.0 g, 7.46 mmol, 1.0 equiv.) and 1-bromopyrrolidine-2,5-dione (2.0 g, 11.18 mmol, 1.5 equiv.) in DMF (15.0 mL) stirred at 30° C. for 2 h. The resulting mixture was diluted with water, and the mixture extracted with EA (3×30 mL). The organic layers were combined, washed with brine (30 mL), dried over $Na_2SO_4$ and concentrated. The residue was purified by silica gel chromatography (0%→30%, PE/EA) to yield 4-bromo-2-(difluoromethyl)-1'-(tetrahydro-2H-pyran-2-yl)-1'H,2H-3,4'-bipyrazole as a yellow oil. LC/MS: mass calculated For $C_{12}H_{13}BrF_2N_4O$: 346.02, measured (ES, m/z): 346.90 [M+H]⁺.

Step 3: 2-(Difluoromethyl)-1'H,2H-[3,4'-bipyrazole]-4-carbonitrile

A mixture of 2-(difluoromethyl)-1'-(tetrahydro-2H-pyran-2-yl)-1'H,2H-3,4'-bipyrazole (2.1 g, 6.05 mmol, 1.0 equiv.), zinc cyanide (2.1 g, 18.15 mmol, 3.0 equiv.), zinc (0.06 g, 0.91 mmol, 0.15 equiv.), Pd₂(dba)₃CHCl₃ (313.1 mg, 0.30 mmol, 0.05 equiv.) and P(t-Bu)₃$_H$BF₄ (351.0 mg, 1.21 mmol, 0.2 equiv.) in N,N-dimethylacetamide (15 mL) was stirred at 130° C. at 6 h. The resulting mixture was extracted with EA (3×50 mL). Then the organic layers were combined, washed with water (5×100 mL) and brine, dried over $Na_2SO_4$ and concentrated. The resulting residue was purified by (0%→80%, PE/EA) to yield 2-(difluoromethyl)-1'H,2H-[3,4'-bipyrazole]-4-carbonitrile as a light yellow oil. LC/MS: mass calculated For $C_8H_5F_2N_5$:209.05, measured (ES, m/z): 210.05 [M+H]⁺.

Step 4: 1'-(1-(5-Bromopyridin-2-yl)-2-cyclopropylethyl)-2-(difluoromethyl)-1'H,2H-[3,4'-bipyrazole]-4-carbonitrile A mixture of cesium carbonate (396.8 mg, 1.22 mmol, 0.6 equiv.) and 2-(difluoromethyl)-1'H,2H-[3,4'-bipyrazole]-4-carbonitrile (509.5 mg, 2.44 mmol, 1.0 equiv. two isomers mixture) in acetonitrile (5.0 mL) was stirred for 15 min at room temperature. 1-(5-bromopyridin-2-yl)-2-cyclopropylethyl methanesulfonate (650.0 mg, 2.03 mmol, 1.0 equiv.) was added and the solution was stirred for 3H at 70° C. The resulting mixture was extracted with EA (3×15.mL). Then the organic layers were combined, washed with brine, dried over $Na_2SO_4$ and concentrated. The resulting residue was purified by silica gel chromatography (0%→50%, PE/EA) to yield 1'-(1-(5-bromopyridin-2-yl)-2-cyclopropylethyl)-2-(difluoromethyl)-1'H,2H-[3,4'-bipyrazole]-4-carbonitrile as a yellow oil. LC/MS: mass calculated For $C_{18}H_{15}BrF_2N_6$: 432.05, measured (ES, m/z): 435.00 [M+H+2]$^+$.

Step 5: 1'-(1-(5-(6-Amino-3-chloro-2-fluorophenyl) pyridin-2-yl)-2-cyclopropylethyl)-2-(difluoromethyl)-1'H,2H-[3,4'-bipyrazole]-4-carbonitrile A mixture of 1'-(1-(5-bromopyridin-2-yl)-2-cyclopropylethyl)-2-(difluoromethyl)-1'H,2H-[3,4'-bipyrazole]-4-carbonitrile (572.0 mg, 1.26 mmol, 1.0 equiv.), 6-amino-3-chloro-2-fluorophenylboronic acid (357.7 mg, 1.89 mmol, 1.5 equiv.), Pd(PPh$_3$)$_4$ (145.5 mg, 0.13 mmol, 0.1 equiv.) and K$_2$CO$_3$ (522.0 mg, 3.78 mmol, 3.0 equiv.) in 1,4-dioxane/water (V/V=5:1, 6.0 mL) was refluxed at 90° C. under N$_2$ for 3 h. The resulting mixture was diluted with water, and the mixture extracted with EA (3×15 mL). The organic layers were combined, washed with brine (5 mL), dried over Na$_2$SO$_4$ and concentrated. The residue was purified by silica gel chromatography (0%→80%, PE/EA) to yield 1'-(1-(5-(6-amino-3-chloro-2-fluorophenyl)pyridin-2-yl)-2-cyclopropylethyl)-2-(difluoromethyl)-1'H,2H-[3,4'-bipyrazole]-4-carbonitrile as a yellow oil. LC/MS: mass calculated For $C_{24}H_{19}ClF_3N_7$: 497.13, measured (ES, m/z): 498.05 [M+H]$^+$.

Step 6: 1'-(1-(5-(3-Chloro-2-fluoro-6-(1H-tetrazol-1-yl)phenyl)pyridin-2-yl)-2-cyclopropylethyl)-2-(difluoromethyl)-1'H,2H-[3,4'-bipyrazole]-4-carbonitrile A mixture of 1'-(1-(5-(6-amino-3-chloro-2-fluorophenyl) pyridin-2-yl)-2-cyclopropylethyl)-2-(difluoromethyl)-1'H,2H-[3,4'-bipyrazole]-4-carbonitrile (492.0 mg, 0.99 mmol, 1.0 equiv.), trimethoxymethane (2.0 mL), azidotrimethylsilane (2.0 mL) and acetic acid (2.0 mL) was stirred overnight at 30° C. The reaction was purified by reverse chromatography on C18 (0→55% MeCN/H$_2$O (0.05% CF$_3$COOH)) to yield 1'-(1-(5-(3-chloro-2-fluoro-6-(1H-tetrazol-1-yl)phenyl)pyridin-2-yl)-2-cyclopropylethyl)-2-(difluoromethyl)-1'H,2H-[3,4'-bipyrazole]-4-carbonitrile as a light yellow solid. LC/MS: mass calculated for $C_{25}H_{18}ClF_3N_{10}$: 550.14, measured (ES, m/z): 573.05 [M+Na]$^+$.

Step 7: (S*)-5-(3-Chloro-2-fluoro-6-(1H-tetrazol-1-yl)phenyl)-2-(1-(4-cyano-2-(difluoromethyl)-1'H,2H-[3,4'-bipyrazol]-1'-yl)-2-cyclopropylethyl)pyridine 1-oxide A mixture of 1'-(1-(5-(3-chloro-2-fluoro-6-(1H-tetrazol-1-yl)phenyl)pyridin-2-yl)-2-cyclopropylethyl)-2-(difluoromethyl)-1'H,2H-[3,4'-bipyrazole]-4-carbonitrile (480.0 mg, 0.87 mmol, 1.0 equiv.), methyltrioxorhenium (108.6 mg, 0.44 mmol, 0.5 equiv.) and hydrogen peroxide (1.0 mL, 30 wt. %) in CH$_3$OH (5.0 mL) was stirred for 2 h at room temperature. The resulting mixture was purified by reverse phase chromatography on C18 (MeCN/H$_2$O (0.05% CF$_3$COOH)) to yield a mixture 5-(3-chloro-2-fluoro-6-(1H-tetrazol-1-yl)phenyl)-2-(1-(4-cyano-2-(difluoromethyl)-1'H,2H-[3,4'-bipyrazol]-1'-yl)-2-cyclopropylethyl)pyridine 1-oxide and 5-(3-chloro-2-fluoro-6-(1H-tetrazol-1-yl)phenyl)-2-(1-(4-cyano-1-(difluoromethyl)-1H,1'H-[3,4'-bipyrazol]-1'-yl)-2-cyclopropylethyl)pyridine 1-oxide as a white solid. The racemic product was separated by chiral-HPLC to yield (S*)-5-(3-chloro-2-fluoro-6-(1H-tetrazol-1-yl)phenyl)-2-(1-(4-cyano-2-(difluoromethyl)-1'H,2H-[3,4'-bipyrazol]-1'-yl)-2-cyclopropylethyl)pyridine 1-oxide as a white solid.

LC/MS: mass calculated for $C_{25}H_{18}ClF_3N_{10}O$: 566.13, measured (ES, m/z): 567.05 [M+H]$^+$. $^1$H NMR (300 MHz, DMSO-d$_6$) δ 9.70 (s, 1H), 8.66 (s, 1H), 8.40-8.44 (m, 2H), 7.70-8.13 (m, 4H), 7.47 (d, J=8.3 Hz, 1H), 7.18-7.23 (m, 1H), 6.15-6.28 (m, 1H), 2.20-2.33 (m, 1H), 1.99-2.06 (m, 1H), 0.55-0.62 (m, 1H), 0.27-0.38 (m, 2H), 0.09-0.13 (m, 1H), −0.06--0.11 (m, 1H). $^{19}$F-NMR (282 MHz, DMSO-d$_6$) δ −74.04, −95.50, −112.60.

Example 701: (S*)-5-(3-Chloro-6-(4-chloro-1H-1,2,3-triazol-1-yl)-2-fluorophenyl)-2-(1-(4-(1-(difluoromethyl)-1H-1,2,3-triazol-4-yl)-1H-pyrazol-1-yl)-2-(1H-pyrazol-1-yl)ethyl)pyridine 1-oxide

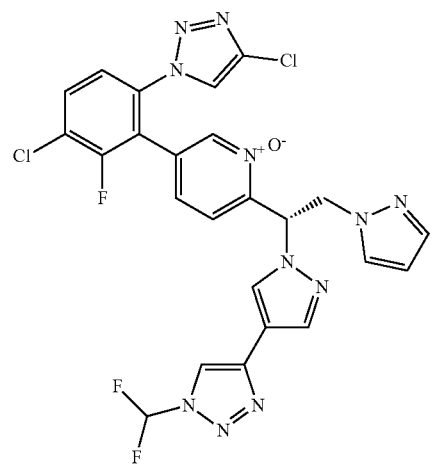

LC/MS: mass calculated for $C_{24}H_{16}Cl_2F_3N_{11}O$: 601.09, measured (ES, m/z): 601.95 [M+H]$^+$. $^1$H NMR (300 MHz, DMSO-d$_6$) δ 8.84 (s, 1H), 8.64 (s, 1H), 8.47-7.95 (m, 5H), 7.67 (dd, J=8.7, 1.6 Hz, 1H), 7.51-7.39 (m, 3H), 7.25-7.16 (m, 1H), 6.59 (dd, J=9.2, 4.9 Hz, 1H), 6.13 (t, J=2.1 Hz, 1H), 5.16-4.94 (m, 2H). $^{19}$F NMR (282 MHz, DMSO-d$_6$) d −73.65, −96.24, −112.94.

Example 702: (R*)-5-(3-Chloro-6-(4-chloro-1H-1,2,3-triazol-1-yl)-2-fluorophenyl)-2-(1-(4-(1-(difluoromethyl)-1H-1,2,3-triazol-4-yl)-1H-pyrazol-1-yl)-2-(1H-pyrazol-1-yl)ethyl)pyridine 1-oxide

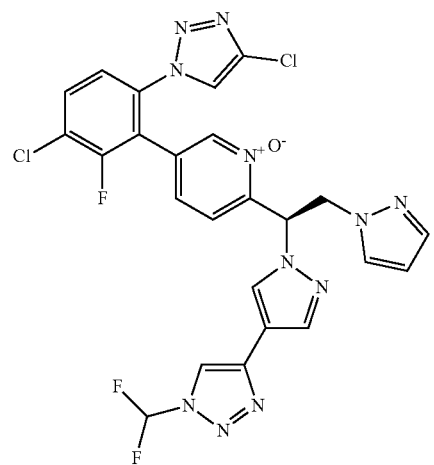

LC/MS: mass calculated for $C_{24}H_{16}Cl_2F_3N_{11}O$: 601.09, measured (ES, m/z): 601.95 [M+H]+. 1H NMR (300 MHz, DMSO-$d_6$) δ 8.86 (s, 1H), 8.68 (s, 1H), 7.97-8.54 (m, 5H), 7.69 (dd, J=8.7, 1.6 Hz, 1H), 7.49 (d, J=2.3 Hz, 1H), 7.41-7.43 (m, 2H), 7.20 (dd, J=8.6, 1.5 Hz, 1H), 6.51-6.62 (m, 1H), 6.13 (t, J=2.1 Hz, 1H), 4.98-5.14 (m, 2H). 19F NMR (282 MHz, DMSO-$d_6$) δ −96.26, −112.87.

Example 703: (R)-5-(3-Chloro-6-(4-chloro-1H-1,2,3-triazol-1-yl)-2-fluorophenyl)-2-(3-(difluoromethoxy)-1-(4-(2-(difluoromethyl)-2H-1,2,3-triazol-4-yl)-1H-pyrazol-1-yl)propyl)pyridine 1-oxide

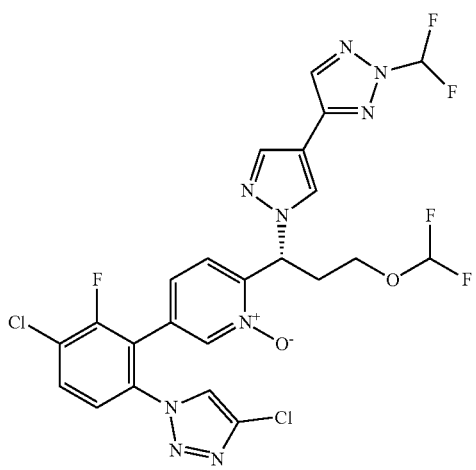 [SMILES: [O-][n+]1cc(-c2c(-n3cc(Cl)nn3)ccc(Cl)c2F)ccc1[C@@H](CCOC(F)F)n1cc(-c2cnn(C(F)F)n2)cn1]

Step 1: (6-(3-(Difluoromethoxy)-1-(4-(2-(difluoromethyl)-2H-1,2,3-triazol-4-yl)-1H-pyrazol-1-yl)propyl)pyridin-3-yl)boronic acid A mixture of 5-bromo-2-(3-(difluoromethoxy)-1-(4-(2-(difluoromethyl)-2H-1,2,3-triazol-4-yl)-1H-pyrazol-1-yl)propyl)pyridine (200 mg, 0.45 mmol, 1.0 equiv.), 4,4,4',4',5,5,5',5'-octamethyl-2,2'-bi(1,3,2-dioxaborolane) (226 mg, 0.89 mmol, 2.0 equiv.), Pd(dppf)Cl$_2$ (32 mg, 0.05 mmol, 0.1 equiv.) and KOAc (131 mg, 1.34 mmol, 3.0 equiv.) in 1,4-dioxane (4 mL) was stirred for 2 h at 80° C. The resulting mixture was diluted with water, extracted with EA (3×15 mL). Then the organic layers were combined, washed with brine, dried over Na$_2$SO$_4$ and concentrated to yield (6-(3-(difluoromethoxy)-1-(4-(2-(difluoromethyl)-2H-1,2,3-triazol-4-yl)-1H-pyrazol-1-yl)propyl)pyridin-3-yl)boronic acid as a black oil. LC/MS: mass calculated for $C_{15}H_{15}BF_4N_6O_3$: 414.12, measured (ES, m/z): 415.10 [M+H]+.

Step 2: 5-(3-Chloro-6-(4-chloro-1H-1,2,3-triazol-1-yl)-2-fluorophenyl)-2-(3-(difluoromethoxy)-1-(4-(2-(difluoromethyl)-2H-1,2,3-triazol-4-yl)-1H-pyrazol-1-yl)propyl)pyridine A mixture of 4-chloro-1-(4-chloro-3-fluoro-2-iodophenyl)-1H-1,2,3-triazole (162 mg, 0.45 mmol, 1.0 equiv.), (6-(3-(difluoromethoxy)-1-(4-(2-(difluoromethyl)-2H-1,2,3-triazol-4-yl)-1H-pyrazol-1-yl)propyl)pyridin-3-yl)boronic acid (187 mg, 0.45 mmol, 1.0 equiv.), Pd(PPh$_3$)$_4$ (52 mg, 0.05 mmol, 0.1 equiv.) and K$_2$CO$_3$ (187 mg, 1.36 mmol, 3.0 equiv.) in 1,4-dioxane/water (V/V=4:1, 3 mL) was refluxed at 90° C. under N$_2$ for 3H. The resulting mixture was diluted with water, and the mixture extracted with EA (3×15 mL). The organic layers were combined, washed with brine (5 mL), dried over Na$_2$SO$_4$ and concentrated. The residue was purified by silica gel chromatography (0%→80%, EA/PE) to yield 5-(3-chloro-6-(4-chloro-1H-1,2,3-triazol-1-yl)-2-fluorophenyl)-2-(3-(difluoromethoxy)-1-(4-(2-(difluoromethyl)-2H-1,2,3-triazol-4-yl)-1H-pyrazol-1-yl)propyl)pyridine as a light yellow solid. LC/MS: mass calculated for $C_{23}H_{16}Cl_2F_5N_9O$: 599.08, measured (ES, m/z): 621.90 [M+Na]+.

Step 3: (R)-5-(3-Chloro-6-(4-chloro-1H-1,2,3-triazol-1-yl)-2-fluorophenyl)-2-(3-(difluoromethoxy)-1-(4-(2-(difluoromethyl)-2H-1,2,3-triazol-4-yl)-1H-pyrazol-1-yl)propyl)pyridine 1-oxide A mixture of 5-(3-chloro-6-(4-chloro-1H-1,2,3-triazol-1-yl)-2-fluorophenyl)-2-(3-(difluoromethoxy)-1-(4-(2-(difluoromethyl)-2H-1,2,3-triazol-4-yl)-1H-pyrazol-1-yl)propyl)pyridine (115 mg, 0.19 mmol, 0.5 equiv.), methyltrioxorhenium (24 mg, 0.09 mmol, 0.5 equiv.) and hydrogen peroxide (0.5 mL, 30 wt %) in CH$_3$OH (2 mL) was stirred for 3H at room temperature. The resulting mixture was purified by reverse phase chromatography on C18 (MeCN/H$_2$O (0.05% CF$_3$COOH)) to yield 5-(3-chloro-6-(4-chloro-1H-1,2,3-triazol-1-yl)-2-fluorophenyl)-2-(3-(difluoromethoxy)-1-(4-(2-(difluoromethyl)-2H-1,2,3-triazol-4-yl)-1H-pyrazol-1-yl)propyl)pyridine 1-oxide (100 mg) as a white solid. The racemic product was separated by chiral-HPLC to yield (R)-5-(3-chloro-6-(4-chloro-1H-1,2,3-triazol-1-yl)-2-fluorophenyl)-2-(3-(difluoromethoxy)-1-(4-(2-(difluoromethyl)-2H-1,2,3-triazol-4-yl)-1H-pyrazol-1-yl)propyl)pyridine 1-oxide as a white solid.

LC/MS: mass calculated for $C_{23}H_{16}Cl_2F_5N_9O_2$: 615.07, measured (ES, m/z): 615.95 [M+H]+. 1H NMR (400 MHz, DMSO-$d_6$) δ 8.67 (s, 1H), 8.58 (d, J=0.7 Hz, 1H), 7.97-8.47 (m, 5H), 7.66-7.72 (m, 1H), 7.32 (d, J=8.3 Hz, 1H), 7.15-7.20 (m, 1H), 6.40-6.85 (m, 1H), 6.20-6.30 (m, 1H), 3.82-3.87 (m, 1H), 3.67-3.73 (m, 1H), 2.58-2.73 (m, 2H). 19F-NMR (376 MHz, DMSO-$d_6$) δ −83.29, −96.70, −112.94.

Example 704: (S)-5-(3-Chloro-6-(4-chloro-1H-1,2,3-triazol-1-yl)-2-fluorophenyl)-2-(3-(difluoromethoxy)-1-(4-(1-(difluoromethyl)-1H-1,2,3-triazol-5-yl)-1H-pyrazol-1-yl)propyl)pyridine 1-oxide

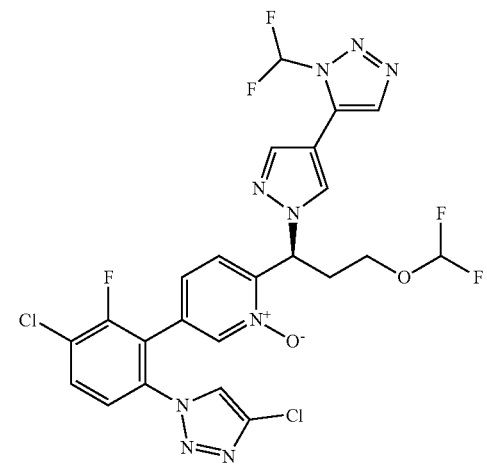 [SMILES: [O-][n+]1cc(-c2c(-n3cc(Cl)nn3)ccc(Cl)c2F)ccc1[C@H](CCOC(F)F)n1cc(-c2cnnn2C(F)F)cn1]

LC/MS: mass calculated for $C_{23}H_{16}Cl_2F_5N_9O_2$: 615.07, measured (ES, m/z): 615.95 [M+H]$^+$. $^1$H NMR (400 MHz, DMSO-d$_6$) δ 8.68 (s, 1H), 8.16-8.59 (m, 4H), 7.99-8.07 (m, 2H), 7.70 (dd, J=8.7, 1.5 Hz, 1H), 7.41 (d, J=8.3 Hz, 1H), 7.20 (dd, J=8.2, 1.7 Hz, 1H), 6.63 (t, J=75.7 Hz, 1H), 6.27 (dd, J=10.0, 4.5 Hz, 1H), 3.81-3.91 (m, 1H), 3.63-3.79 (m, 1H), 2.55-2.73 (m, 2H). $^{19}$F NMR (376 MHz, DMSO-d$_6$) δ −83.42, −97.14, −112.93.

Example 705: (R)-5-(3-Chloro-6-(4-chloro-1H-1,2,3-triazol-1-yl)-2-fluorophenyl)-2-(3-(difluoromethoxy)-1-(4-(1-(difluoromethyl)-1H-1,2,3-triazol-5-yl)-1H-pyrazol-1-yl)propyl)pyridine 1-oxide

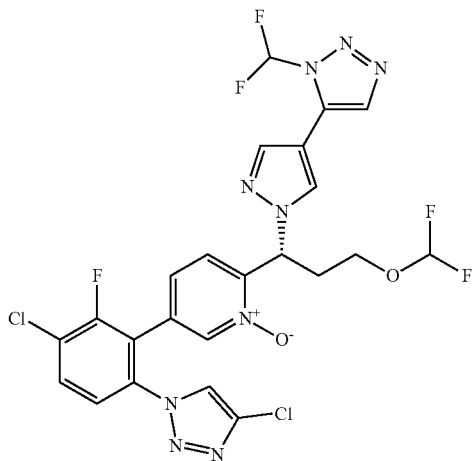 [SMILES: [O-][n+]1cc(-c2c(-n3cc(Cl)nn3)ccc(Cl)c2F)ccc1[C@@H](CCOC(F)F)n1cc(-c2cnnn2C(F)F)cn1]

Step 1: 1-(Difluoromethyl)-5-iodo-1H-1,2,3-triazole

Isopropylmagnesium chloride (35.5 ml, 46.2 mmol, 1.1 eq.) was slowly added to a solution of 1-(difluoromethyl)-1H-1,2,3-triazole (5 g, 42.0 mmol, 1.0 eq.) in THF (40 mL) at −78° C. under N$_2$. After 1 h, I$_2$ (11.7 g, 46.2 mmol, 1.1 eq.) in THF (10 ml) was added to the mixture and the reaction was warmed to room temperature and stirred for 1 h. The reaction mixture was diluted with NH$_4$Cl and extracted with EtOAc. The organic layer was washed with brine and dried over anhydrous Na$_2$SO$_4$, filtered, concentrated, and purified by flash column chromatography on silica gel with EtOAc/petroleum ether (1-40%) to yield 1-(difluoromethyl)-5-iodo-1H-1,2,3-triazole as a yellow solid. LC/MS: mass calculated for $C_3H_2F_2IN_3$: 245, measured: 246 [M+H]$^+$.

Step 2: 1-(Difluoromethyl)-5-(1H-pyrazol-4-yl)-1H-1,2,3-triazole

To a solution of 1-(difluoromethyl)-5-iodo-1H-1,2,3-triazole (1 g, 4.1 mmol, 1.0 eq) and tert-butyl 4-(4,4,5,5-tetramethyl-1,3,2-dioxaborolan-2-yl)-1H-pyrazole-1-carboxylate (1.8 g, 6.1 mmol, 1.5 eq.) in 1,4-dioxane (15 mL) and water (3 mL) was added potassium carbonate (2.3 g, 16.3 mmol, 4 eq) and Pd(PPh$_3$)$_4$ (0.24 g, 0.20 mmol, 0.05 eq) under N$_2$. The reaction mixture was stirred for 2 h at 90° C., then quenched with water, extracted with EtOAc, dried over Na$_2$SO$_4$, and concentrated under vacuum. The residue was purified by silica gel chromatography with MeOH/DCM (0-10%) to yield 1-(difluoromethyl)-5-(1H-pyrazol-4-yl)-1H-1,2,3-triazole. LC/MS: mass calculated for $C_6H_5F_2N_5$: 185.05, measured: 186.1 [M+H]$^+$.

Step 3: 5-Bromo-2-(3-(difluoromethoxy)-1-(4-(1-(difluoromethyl)-1H-1,2,3-triazol-5-yl)-1H-pyrazol-1-yl)propyl)pyridine To a solution of 1-(difluoromethyl)-5-(1H-pyrazol-4-yl)-1H-1,2,3-triazole (0.14 g, 0.76 mmol, 1.0 eq.) in ACN (10 mL) was added cesium carbonate (0.25 g, 0.76 mmol, 1.0 eq). After the reaction mixture was stirred for 1 h at room temperature. 1-(5-Bromopyridin-2-yl)-3-(difluoromethoxy) propyl methanesulfonate (0.30 g, 0.83 mmol, 1.1 equiv) was then added. The reaction mixture was stirred for 2 h at 80° C., then cooled to rt and filtered through a pad of CELITE. The filtrate was concentrated under vacuum. The resulting residue was purified by silica gel chromatography with EtOAc/petroleum ether (0-60%) to yield 5-bromo-2-(3-(difluoromethoxy)-1-(4-(1-(difluoromethyl)-1H-1,2,3-triazol-5-yl)-1H-pyrazol-1-yl)propyl)pyridine as light brown oil. LC/MS (ESI, m/z): mass calculated for $C_{15}H_{13}BrF_4N_6O$: 448.03, measured: 449.0 [M+H]$^+$, 451.0 [M+2+H]$^+$.

Step 4: (6-(3-(Difluoromethoxy)-1-(4-(1-(difluoromethyl)-1H-1,2,3-triazol-5-yl)-1H-pyrazol-1-yl)propyl)pyridin-3-yl)boronic acid A mixture of 5-bromo-2-(3-(difluoromethoxy)-1-(4-(1-(difluoromethyl)-1H-1,2,3-triazol-5-yl)-1H-pyrazol-1-yl) propyl)pyridine (200.0 mg, 0.45 mmol, 1.0 equiv.), 4,4,4',4',5,5,5',5'-octamethyl-2,2'-bi(1,3,2-dioxaborolane) (226.1 mg, 0.89 mmol, 2.0 equiv.), Pd(dppf)Cl$_2$ (32.5 mg, 0.05 mmol, 0.1 equiv.) and KOAc (131.1 mg, 1.34 mmol, 3.0 equiv.) in 1,4-dioxane (4 mL) was stirred for 2 h at 80° C. The resulting mixture was diluted with water, extracted with EA (3×15 mL). Then the organic layers were combined, washed with brine, dried over Na$_2$SO$_4$ and concentrated to yield (6-(3-(difluoromethoxy)-1-(4-(1-(difluoromethyl)-1H-1,2,3-triazol-5-yl)-1H-pyrazol-1-yl)propyl)pyridin-3-yl)boronic acid as a black oil. LC/MS: mass calculated for $C_{15}H_{15}BF_4N_6O_3$: 414.12, measured (ES, m/z): 415.05 [M+H]$^+$.

Step 5: 5-(3-Chloro-6-(4-chloro-1H-1,2,3-triazol-1-yl)-2-fluorophenyl)-2-(3-(difluoromethoxy)-1-(4-(1-(difluoromethyl)-1H-1,2,3-triazol-5-yl)-1H-pyrazol-1-yl)propyl)pyridine A mixture of 4-chloro-1-(4-chloro-3-fluoro-2-iodophenyl)-1H-1,2,3-triazole (147.0 mg, 0.41 mmol, 1.0 equiv.), (6-(3-(difluoromethoxy)-1-(4-(1-(difluoromethyl)-1H-1,2,3-triazol-5-yl)-1H-pyrazol-1-yl)propyl)pyridin-3-yl)boronic acid (170.1 mg, 0.41 mmol, 1.0 equiv.), Pd(PPh$_3$)$_4$ (47.4 mg, 0.04 mmol, 0.1 equiv.) and K$_2$CO$_3$ (170.3 mg, 1.23 mmol, 3.0 equiv.) in 1,4-dioxane/water (V/V=4:1, 3 mL) was refluxed at 90° C. under N$_2$ for 3 h. The resulting mixture was diluted with water, and the mixture extracted with EA (3×15 mL). The organic layers were combined, washed with brine (5 mL), dried over Na$_2$SO$_4$ and concentrated. The residue was purified by silica gel chromatography (0%→80%, EA/PE) to yield 5-(3-chloro-6-(4-chloro-1H-1,2,3-triazol-1-yl)-2-fluorophenyl)-2-(3-(difluoromethoxy)-1-(4-(1-(difluoromethyl)-1H-1,2,3-triazol-5-yl)-1H-pyrazol-1-yl)propyl)pyridine as a light yellow solid. LC/MS: mass calculated for $C_{23}H_{16}Cl_2F_5N_9O$: 599.08, measured (ES, m/z): 600.90 [M+H]$^+$.

Step 6: (R)-5-(3-Chloro-6-(4-chloro-1H-1,2,3-triazol-1-yl)-2-fluorophenyl)-2-(3-(difluoromethoxy)-1-(4-(1-(difluoromethyl)-1H-1,2,3-triazol-5-yl)-1H-pyrazol-1-yl)propyl)pyridine 1-oxide A mixture of 5-(3-chloro-2-fluoro-6-(1H-tetrazol-1-yl)phenyl)-2-(3-(difluoromethoxy)-1-(4-(2-(difluoromethyl)-2H-1,2,3-triazol-4-yl)-1H-pyrazol-1-yl)propyl)pyridine (110.0 mg, 0.18 mmol, 1.0 equiv.), methyltrioxorhenium (22.8 mg, 0.09 mmol, 0.5 equiv.) and hydrogen peroxide (0.5 mL, 30 wt %) in CH$_3$OH (2 mL) was stirred for 3 h at room temperature. The resulting mixture was purified by reverse phase chromatography on C18 (MeCN/H$_2$O (0.05% CF$_3$COOH)) to yield 5-(3-chloro-6-(4-chloro-1H-1,2,3-triazol-1-yl)-2-fluorophenyl)-2-(3-(difluoromethoxy)-1-(4-(1-(difluoromethyl)-1H-1,2,3-triazol-5-yl)-1H-pyrazol-1-yl)propyl)pyridine 1-oxide (100.0 mg) as a white solid. The racemic product was separated by chiral-HPLC to yield (R)-5-(3-chloro-6-(4-chloro-1H-1,2,3-triazol-1-yl)-2-fluorophenyl)-2-(3-(difluoromethoxy)-1-(4-(1-(difluoromethyl)-1H-1,2,3-triazol-5-yl)-1H-pyrazol-1-yl)propyl)pyridine 1-oxide as a white solid.

LC/MS: mass calculated for C$_{23}$H$_{16}$Cl$_2$F$_5$N$_9$O$_2$: 615.07, measured (ES, m/z): 615.95 [M+H]$^+$. $^1$H NMR (400 MHz, DMSO-d$_6$) δ 8.68 (s, 1H), 8.14-8.55 (m, 4H), 7.97-8.07 (m, 2H), 7.68-7.74 (m, 1H), 7.41 (d, J=8.3 Hz, 1H), 7.14-7.25 (m, 1H), 6.40-6.80 (m, 1H), 6.20-6.31 (m, 1H), 3.80-3.90 (m, 1H), 3.60-3.72 (m, 1H), 2.56-2.71 (m, 2H). $^{19}$F-NMR (376 MHz, DMSO-d$_6$) δ −83.42, −97.14, −112.93.

Example 706: (S)-5-(3-Chloro-2-fluoro-6-(1H-tetrazol-1-yl)phenyl)-2-(2-cyclopropyl-1-(4-hydroxy-2-methyl-1'H,2H-[3,4'-bipyrazol]-1'-yl)ethyl)pyridine 1-oxide

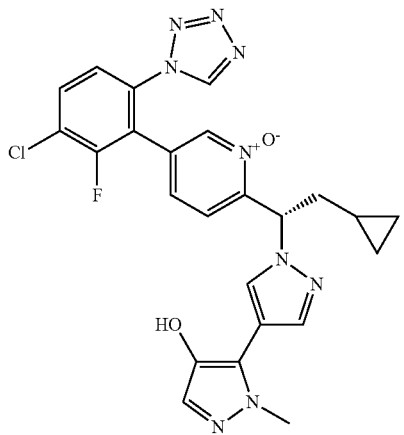

LC/MS: mass calculated for C$_{24}$H$_{21}$ClFN$_9$O$_2$: 521.15, measured (ES, m/z): 522.3 [M+H]$^+$. $^1$H NMR (400 MHz, DMSO-d$_6$) δ 9.69 (s, 1H), 8.54 (s, 1H), 8.42 (d, J=1.6 Hz, 1H), 8.33 (d, J=0.8 Hz, 1H), 8.07 (dd, J=8.7, 7.7 Hz, 1H), 7.90 (s, 1H), 7.76 (dd, J=8.7, 1.5 Hz, 1H), 7.28 (d, J=8.3 Hz, 1H), 7.16 (dd, J=8.2, 1.7 Hz, 1H), 7.02 (s, 1H), 6.10-6.14 (m, 1H), 3.80 (s, 3H), 2.30-2.42 (m, 1H), 1.86-1.96 (m, 1H), 0.57-0.66 (m, 1H), 0.26-0.41 (m, 2H), 0.06-0.17 (m, 1H), −0.08-0.03 (m, 1H). $^{19}$F NMR (376 MHz, DMSO-d$_6$) δ −73.41, −112.76.

Example 707: (S)-5-(3-Chloro-6-(4-chloro-1H-1,2,3-triazol-1-yl)-2-fluorophenyl)-2-(3-(difluoromethoxy)-1-(4-(2-(difluoromethyl)-2H-1,2,3-triazol-4-yl)-1H-pyrazol-1-yl)propyl)pyridine 1-oxide

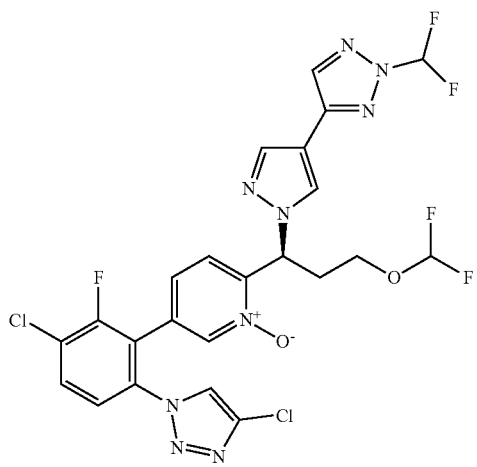 [SMILES: [O-][n+]1cc(-c2c(-n3cc(Cl)nn3)ccc(Cl)c2F)ccc1[C@H](CCOC(F)F)n1cc(-c2cnn(C(F)F)n2)cn1]

LC/MS: mass calculated for C$_{23}$H$_{16}$Cl$_2$F$_5$N$_9$O$_2$: 615.07, measured (ES, m/z): 615.95 [M+H]$^+$. $^1$H NMR (400 MHz, DMSO-d$_6$) δ 8.68 (s, 1H), 8.58 (s, 1H), 7.98-8.47 (m, 5H), 7.69 (dd, J=8.7, 1.5 Hz, 1H), 7.33 (d, J=8.3 Hz, 1H), 7.18 (dd, J=8.3, 1.7 Hz, 1H), 6.64 (t, J=75.7 Hz, 1H), 6.22-6.26 (m, 1H), 3.82-3.88 (m, 1H), 3.67-3.73 (m, 1H), 2.59-2.72 (m, 2H). $^{19}$F NMR (376 MHz, DMSO-d$_6$) δ −83.29, −96.70, −112.94.

Example 708: (S)-5-(3-Chloro-2-fluoro-6-(1H-tetrazol-1-yl)phenyl)-2-(1-(4-(1-(difluoromethyl)-1H-1,2,3-triazol-5-yl)-1H-pyrazol-1-yl)-3-methoxypropyl)pyridine 1-oxide

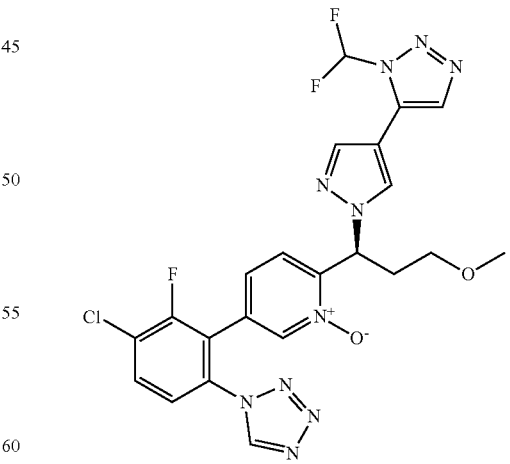

LC/MS: mass calculated for C$_{22}$H$_{18}$ClF$_3$N$_{10}$O$_2$: 546.13, measured (ES, m/z): 547.05 [M+H]$^+$. $^1$H NMR (300 MHz, DMSO-d$_6$) δ 9.69 (s, 1H), 8.58 (d, J=0.7 Hz, 1H), 8.30-8.48 (m, 2H), 7.91-8.15 (m, 3H), 7.76 (dd, J=8.7, 1.6 Hz, 1H), 7.33 (d, J=8.3 Hz, 1H), 7.17 (dd, J=8.3, 1.7 Hz, 1H), 6.17-6.22 (m, 1H), 3.30-3.32 (m, 1H), 3.18-3.20 (m, 4H), 2.51-2.53 (m, 2H). $^{19}$F NMR (282 MHz, DMSO-$d_6$) δ −96.69, −112.70.

Example 709: (S)-5-(3-Chloro-2-fluoro-6-(1H-tetrazol-1-yl)phenyl)-2-(3-(difluoromethoxy)-1-(4-(1-(difluoromethyl)-1H-1,2,3-triazol-5-yl)-1H-pyrazol-1-yl)propyl)pyridine 1-oxide

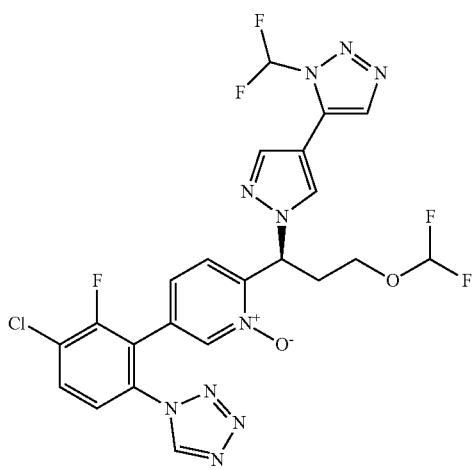 [SMILES: [O-][n+]1cc(-c2c(-n3cnnn3)ccc(Cl)c2F)ccc1[C@H](CCOC(F)F)n1cc(-c2cnnn2C(F)F)cn1]

LC/MS: mass calculated for $C_{22}H_{16}ClF_5N_{10}O_2$: 582.11, measured (ES, m/z): 605.00 [M+Na]$^+$. $^1$H NMR (300 MHz, DMSO-$d_6$) δ 9.67 (s, 1H), 7.97-8.53 (m, 6H), 7.74 (dd, J=8.8, 1.6 Hz, 1H), 7.36 (d, J=8.3 Hz, 1H), 7.18 (dd, J=8.3, 1.7 Hz, 1H), 6.60 (t, J=75.7 Hz, 1H), 6.22-6.27 (m, 1H), 3.52-3.86 (m, 2H), 2.58-2.64 (m, 2H). $^{19}$F NMR (282 MHz, DMSO-$d_6$) δ −83.41, −97.13, −112.66.

Example 710: (R)-5-(3-Chloro-2-fluoro-6-(1H-tetrazol-1-yl)phenyl)-2-(2-cyclopropyl-1-(4-hydroxy-2-methyl-1'H,2H-[3,4'-bipyrazol]-1'-yl)ethyl)pyridine 1-oxide

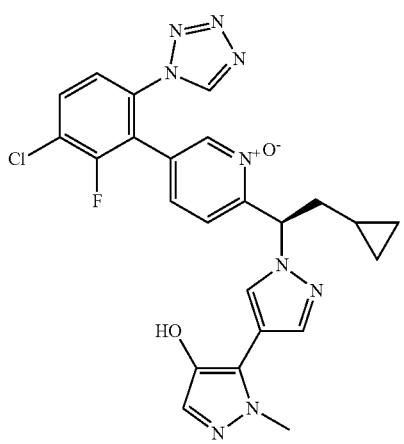

Step 1:
5-Iodo-4-(methoxymethoxy)-1-methyl-1H-pyrazole

To a solution of 4-(methoxymethoxy)-1-methyl-1H-pyrazole (460 mg, 3.24 mmol, 1.0 equiv.) in tetrahydrofuran (10 mL) under nitrogen was added n-butyllithium (1.4 mL, 3.56 mmol, 2.50 M in THF, 1.1 equiv.) at −78° C. and the solution was stirred for 1H at this temperature. To the solution was then added the solution of I$_2$ (986 mg, 3.88 mmol, 1.2 equiv.) in tetrahydrofuran (5 mL) at −78° C. and the solution was allowed to warm to room temperature for 2 h. The reaction was quenched with sat. NH$_4$Cl solution and extracted with ethyl acetate twice. The combined organic layer was washed with brine, dried over Na$_2$SO$_4$ and concentrated. The residue was purified by silica gel chromatography (0→50% ethyl acetate/petroleum ether) to yield 5-iodo-4-(methoxymethoxy)-1-methyl-1H-pyrazole as a white solid. LC/MS: mass calculated for $C_6H_9IN_2O_2$: 267.97, measured (ES, m/z): 268.90 [M+H]$^+$.

Step 2: 4-(Methoxymethoxy)-2-methyl-1'H,2H-3,4'-bipyrazole

A mixture of 5-iodo-4-(methoxymethoxy)-1-methyl-1H-pyrazole (680 mg, 2.54 mmol, 1.0 equiv.), tert-butyl 4-(4,4,5,5-tetramethyl-1,3,2-dioxaborolan-2-yl)-1H-pyrazole-1-carboxylate (1.49 g, 5.07 mmol, 2.0 equiv.), potassium carbonate (1.05 g, 7.61 mmol, 3.0 equiv.) and tetrakis(triphenylphosphine)palladium (293 mg, 0.25 mmol, 0.1 equiv.) in DMF (10 mL) and water (2.0 mL) was stirred at 90° C. for 2 h. After cooling to room temperature, the reaction was quenched with water and then extracted with ethyl acetate twice. The combined organic layers were washed with brine, dried over anhydrous sodium sulfate and concentrated. The residue was purified by silica gel chromatography (0→10% MeOH/DCM) to yield 4-(methoxymethoxy)-2-methyl-1'H,2H-3,4'-bipyrazole as a white solid. LC/MS: mass calculated for $C_9H_{12}N_4O_2$: 208.10, measured (ES, m/z): 209.05 [M+H]$^+$.

Step 3: 1'-(1-(5-Bromopyridin-2-yl)-2-cyclopropylethyl)-4-(methoxymethoxy)-2-methyl-1'H,2H-3,4'-bipyrazole A mixture of 1-(5-bromopyridin-2-yl)-2-cyclopropylethyl methanesulfonate (280 mg, 0.87 mmol, 1.0 equiv.), 4-(methoxymethoxy)-2-methyl-1'H,2H-3,4'-bipyrazole (200 mg, 0.96 mmol, 1.1 equiv.) and cesium carbonate (313 mg, 0.96 mmol, 1.1 equiv.) in acetonitrile (10 mL) was stirred at 90° C. for 4 h. The reaction was diluted with water and then extracted with ethyl acetate twice. The combined organic layers were washed with brine, dried over Na$_2$SO$_4$ and concentrated. The residue was purified by silica gel chromatography (0→10% MeOH/DCM) to yield 1'-(1-(5-bromopyridin-2-yl)-2-cyclopropylethyl)-4-(methoxymethoxy)-2-methyl-1'H,2H-3,4'-bipyrazole as a light yellow solid. LC/MS: mass calculated for $C_{19}H_{22}BrN_5O_2$: 431.10, measured (ES, m/z): 432.10, 434.10 [M+H, M+H+2]$^+$.

Step 4: 4-Chloro-2-(6-(2-cyclopropyl-1-(4-(methoxymethoxy)-2-methyl-1'H,2H-[3,4'-bipyrazol]-1'-yl)ethyl)pyridin-3-yl)-3-fluoroaniline To a mixture of 1'-(1-(5-bromopyridin-2-yl)-2-cyclopropylethyl)-4-(methoxymethoxy)-2-methyl-1'H,2H-3,4'-bipyrazole (350 mg, 0.81 mmol, 1.0 equiv.), 6-amino-3-chloro-2-fluorophenylboronic acid (230 mg, 1.21 mmol, 1.5 equiv.) and potassium carbonate (336 mg, 2.43 mmol, 3.0 equiv.) in 1,4-dioxane (10 mL) and water (2 mL) was added tetrakis(triphenylphosphine)palladium(0) (94 mg, 0.08 mmol, 0.1 equiv.) and the mixture stirred at 90° C. for 2 h. After cooling to room temperature, the reaction was quenched with water and then extracted with ethyl acetate twice. The combined organic layers were washed with brine, dried over anhydrous sodium sulfate and concentrated. The residue was purified silica gel chromatography (0→10% MeOH/DCM) to yield 4-chloro-2-(6-(2-cyclopropyl-1-(4-(methoxymethoxy)-2-methyl-1'H,2H-[3,4'-bipyrazol]-1'-yl)ethyl)pyridin-3-yl)-3-fluoroaniline as a light yellow solid. LC/MS: mass calculated for $C_{25}H_{26}ClFN_6O_2$: 496.18, measured (ES, m/z): 497.10 $[M+H]^+$.

Step 5: 1'-(1-(5-(3-Chloro-2-fluoro-6-(1H-tetrazol-1-yl)phenyl)pyridin-2-yl)-2-cyclopropylethyl)-4-(methoxymethoxy)-2-methyl-1'H,2H-3,4'-bipyrazole A mixture of 4-chloro-2-(6-(2-cyclopropyl-1-(4-(methoxymethoxy)-2-methyl-1'H,2H-[3,4'-bipyrazol]-1'-yl)ethyl)pyridin-3-yl)-3-fluoroaniline (350 mg, 0.70 mmol, 1.0 equiv.), azidotrimethylsilane (1 mL) and trimethoxymethane (1 mL) in acetic acid glacial (1 mL) was stirred at room temperature overnight. The mixture was concentrated and the residue was purified by reverse phase chromatography on C18 (80 g, MeCN/H2O (0.05% CF3COOH): 0→50%) to yield 1'-(1-(5-(3-chloro-2-fluoro-6-(1H-tetrazol-1-yl)phenyl)pyridin-2-yl)-2-cyclopropylethyl)-4-(methoxymethoxy)-2-methyl-1'H,2H-3,4'-bipyrazole as alight yellow solid. LC/MS: mass calculated for $C_{26}H_{25}ClFN_9O_2$: 549.18, measured (ES, m/z): 550.15 $[M+H]^+$.

Step 6: 5-(3-Chloro-2-fluoro-6-(1H-tetrazol-1-yl)phenyl)-2-(2-cyclopropyl-1-(4-(methoxymethoxy)-2-methyl-1'H,2H-[3,4'-bipyrazol]-1'-yl)ethyl)pyridine 1-oxide A mixture of 1'-(1-(5-(3-chloro-2-fluoro-6-(1H-tetrazol-1-yl)phenyl)pyridin-2-yl)-2-cyclopropylethyl)-4-(methoxymethoxy)-2-methyl-1'H,2H-3,4'-bipyrazole (200 mg, 0.36 mmol, 1.0 equiv.) and 3-chloroperoxybenzoic acid (314 mg, 1.81 mmol, 5.0 equiv.) in ethyl acetate (5 mL) was stirred at room temperature for 1 h. The reaction was purified by reverse phase chromatography on C18 (80 g, MeCN/H2O (0.05% CF3COOH): 0→45%) to yield 5-(3-chloro-2-fluoro-6-(1H-tetrazol-1-yl)phenyl)-2-(2-cyclopropyl-1-(4-(methoxymethoxy)-2-methyl-1'H,2H-[3,4'-bipyrazol]-1'-yl)ethyl)pyridine 1-oxide as a light yellow solid. LC/MS: mass calculated for $C_{26}H_{25}ClFN_9O_3$: 565.18, measured (ES, m/z): 566.25 $[M+H]^+$.

Step 7: (R)-5-(3-chloro-2-fluoro-6-(1H-tetrazol-1-yl)phenyl)-2-(2-cyclopropyl-1-(4-hydroxy-2-methyl-1'H,2H-[3,4'-bipyrazol]-1'-yl)ethyl)pyridine 1-oxide To a solution of 5-(3-chloro-2-fluoro-6-(1H-tetrazol-1-yl)phenyl)-2-(2-cyclopropyl-1-(4-(methoxymethoxy)-2-methyl-1'H,2H-[3,4'-bipyrazol]-1'-yl)ethyl)pyridine 1-oxide (150 mg, 0.27 mmol, 1.0 equiv.) in DCM (2 mL) was added trifluoroacetic acid (1 mL) and the solution was stirred at room temperature for 3 h. The solution was concentrated and the residue was purified by reverse phase chromatography on C18 (80 g, MeCN/H2O (0.05% CF3COOH): 0→50%) and Prep-Chiral-HPLC to yield (R)-5-(3-chloro-2-fluoro-6-(1H-tetrazol-1-yl)phenyl)-2-(2-cyclopropyl-1-(4-hydroxy-2-methyl-1'H,2H-[3,4'-bipyrazol]-1'-yl)ethyl)pyridine 1-oxide as a white solid.

LC/MS: mass calculated for $C_{24}H_{21}ClFN_9O_2$: 521.15, measured (ES, m/z): 522.3 $[M+H]^+$. $^1H$ NMR (400 MHz, DMSO-$d_6$): δ 9.69 (s, 1H), 8.54 (s, 1H), 8.42 (d, J=1.6 Hz, 1H), 8.33 (d, J=0.7 Hz, 1H), 8.05-8.11 (m, 1H), 7.90 (s, 1H), 7.75-7.80 (m, 1H), 7.28 (d, J=8.3 Hz, 1H), 7.15-7.20 (m, 1H), 7.02 (s, 1H), 6.11-6.18 (m, 1H), 3.80 (s, 3H), 2.42-2.30 (m, 1H), 1.97-1.86 (m, 1H), 0.57-0.66 (m, 1H), 0.26-0.41 (m, 2H), 0.17-0.06 (m, 1H), 0.03--0.08 (m, 1H). $^{19}F$-NMR (376 MHz, DMSO-$d_6$): δ −73.40, −112.76.

Example 711: (R)-5-(3-Chloro-2-fluoro-6-(1H-tetrazol-1-yl)phenyl)-2-(3-(difluoromethoxy)-1-(4-(2-(difluoromethyl)-2H-1,2,3-triazol-4-yl)-1H-pyrazol-1-yl)propyl)pyridine 1-oxide

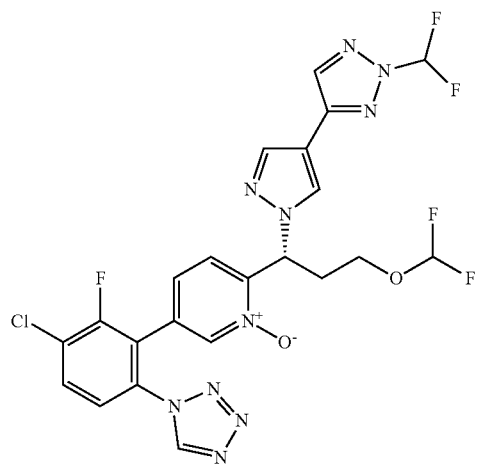 [SMILES: [O-][n+]1cc(-c2c(-n3cnnn3)ccc(Cl)c2F)ccc1[C@@H](CCOC(F)F)n1cc(-c2cnn(C(F)F)n2)cn1]

Step 1: 5-Bromo-2-(3-(difluoromethoxy)-1-(4-(2-(difluoromethyl)-2H-1,2,3-triazol-4-yl)-1H-pyrazol-1-yl)propyl)pyridine A mixture of cesium carbonate (436.9 mg, 1.34 mmol, 1.0 equiv.) and 2-(difluoromethyl)-4-(1H-pyrazol-4-yl)-2H-1,2,3-triazole (248.3 mg, 1.34 mmol, 1.0 equiv.) in acetonitrile (5.0 mL) was stirred for 15 min at room temperature. 1-(5-bromopyridin-2-yl)-3-(difluoromethoxy)propyl methanesulfonate (483.0 mg, 1.34 mmol, 1.0 equiv.) was added and the solution was stirred for 2.5 h at 90° C. The resulting mixture was diluted with water, extracted with EA (3×10 mL). Then the organic layers were combined, washed with brine, dried over Na2SO4 and concentrated. The residue was purified by silica gel chromatography (EA/PE, 0%→80%) to yield 5-bromo-2-(3-(difluoromethoxy)-1-(4-(2-(difluoromethyl)-2H-1,2,3-triazol-4-yl)-1H-pyrazol-1-yl)propyl)pyridine as a light yellow oil. LC/MS: mass calculated for $C_{15}H_{13}BrF_4N_6O$: 446.13, measured (ES, m/z): 448.95 $[M+H+2]^+$.

Step 2: 4-Chloro-2-(6-(3-(difluoromethoxy)-1-(4-(2-(difluoromethyl)-2H-1,2,3-triazol-4-yl)-1H-pyrazol-1-yl)propyl)pyridin-3-yl)-3-fluoroaniline A mixture of 5-bromo-2-(3-(difluoromethoxy)-1-(4-(2-(difluoromethyl)-2H-1,2,3-triazol-4-yl)-1H-pyrazol-1-yl)propyl)pyridine (150.0 mg, 0.33 mmol, 1.0 equiv.), 6-amino-3-chloro-2-fluorophenylboronic acid (94.9 mg, 0.50 mmol, 1.5 equiv.), Pd(PPh3)4 (38.6 mg, 0.03 mmol, 0.1 equiv.) and K2CO3 (138.5 mg, 1.00 mmol, 3.0 equiv.) in 1,4-dioxane/water (V/V=5:1, 6 mL) was refluxed at 90° C. under N2 for 3 h. The resulting mixture was diluted with water, and the mixture extracted with EA (3×15 mL). The organic layers were combined, washed with brine (5 mL), dried over Na₂SO₄ and concentrated. The residue was purified by silica gel chromatography (0%→80%, EA/PE) to yield 4-chloro-2-(6-(3-(difluoromethoxy)-1-(4-(2-(difluoromethyl)-2H-1,2,3-triazol-4-yl)-1H-pyrazol-1-yl)propyl)pyridin-3-yl)-3-fluoroaniline as an orange oil. LC/MS: mass calculated for $C_{21}H_{17}ClF_5N_7O$: 513.11, measured (ES, m/z): 514.00 [M+H]⁺.

Step 3: 5-(3-Chloro-2-fluoro-6-(1H-tetrazol-1-yl)phenyl)-2-(3-(difluoromethoxy)-1-(4-(2-(difluoromethyl)-2H-1,2,3-triazol-4-yl)-1H-pyrazol-1-yl)propyl)pyridine A mixture of 4-chloro-2-(6-(3-(difluoromethoxy)-1-(4-(2-(difluoromethyl)-2H-1,2,3-triazol-4-yl)-1H-pyrazol-1-yl)propyl)pyridin-3-yl)-3-fluoroaniline (128.0 mg, 0.25 mmol, 1.0 equiv.), trimethoxymethane (2.0 mL), azidotrimethylsilane (2.0 mL) and acetic acid (2.0 mL) was stirred overnight at 30° C. The reaction was purified by reverse chromatography on C18 (0→55% MeCN/H₂O (0.05% CF₃COOH)) to yield 5-(3-chloro-2-fluoro-6-(1H-tetrazol-1-yl)phenyl)-2-(3-(difluoromethoxy)-1-(4-(2-(difluoromethyl)-2H-1,2,3-triazol-4-yl)-1H-pyrazol-1-yl)propyl)pyridine as a light yellow solid. LC/MS: mass calculated for $C_{22}H_{16}ClF_5N_{10}O$: 566.11, measured (ES, m/z): 567.00 [M+H]⁺.

Step 4: (R)-5-(3-Chloro-2-fluoro-6-(1H-tetrazol-1-yl)phenyl)-2-(3-(difluoromethoxy)-1-(4-(2-(difluoromethyl)-2H-1,2,3-triazol-4-yl)-1H-pyrazol-1-yl)propyl)pyridine 1-oxide A mixture of 5-(3-chloro-2-fluoro-6-(1H-tetrazol-1-yl)phenyl)-2-(3-(difluoromethoxy)-1-(4-(2-(difluoromethyl)-2H-1,2,3-triazol-4-yl)-1H-pyrazol-1-yl)propyl)pyridine (110.0 mg, 0.19 mmol, 1.0 equiv.), methyltrioxorhenium (24.2 mg, 0.10 mmol, 0.5 equiv.) and hydrogen peroxide (0.5 mL, 30 wt %) in CH₃OH (2.0 mL) was stirred for 3 h at room temperature. The resulting mixture was purified by reverse phase chromatography on C18 (MeCN/H₂O (0.05% CF₃COOH)) to yield 5-(3-chloro-2-fluoro-6-(1H-tetrazol-1-yl)phenyl)-2-(3-(difluoromethoxy)-1-(4-(2-(difluoromethyl)-2H-1,2,3-triazol-4-yl)-1H-pyrazol-1-yl)propyl)pyridine 1-oxide as a white solid. The racemic product was separated by chiral-HPLC to yield (R)-5-(3-chloro-2-fluoro-6-(1H-tetrazol-1-yl)phenyl)-2-(3-(difluoromethoxy)-1-(4-(2-(difluoromethyl)-2H-1,2,3-triazol-4-yl)-1H-pyrazol-1-yl)propyl)pyridine 1-oxide as a white solid.

LC/MS: mass calculated for $C_{22}H_{16}ClF_5N_{10}O_2$: 582.11, measured (ES, m/z): 605.00 [M+Na]⁺. ¹H NMR (300 MHz, DMSO-d₆) δ 9.68 (s, 1H), 8.56 (s, 1H), 8.42 (d, J=3.0 Hz, 2H), 7.90-8.32 (m, 3H), 7.70-7.79 (m, 1H), 7.27 (d, J=8.3 Hz, 1H), 7.14-7.20 (m, 1H), 6.32-6.90 (m, 1H), 6.12-6.23 (m, 1H), 3.58-3.87 (m, 2H), 2.54-2.71 (m, 2H). ¹⁹F-NMR (282 MHz, DMSO-d₆) δ −83.28, −96.72, −112.68.

Example 712: (R)-5-(3-Chloro-2-fluoro-6-(1H-tetrazol-1-yl)phenyl)-2-(1-(4-(1-(difluoromethyl)-1H-1,2,3-triazol-5-yl)-1H-pyrazol-1-yl)-3-methoxypropyl)pyridine 1-oxide

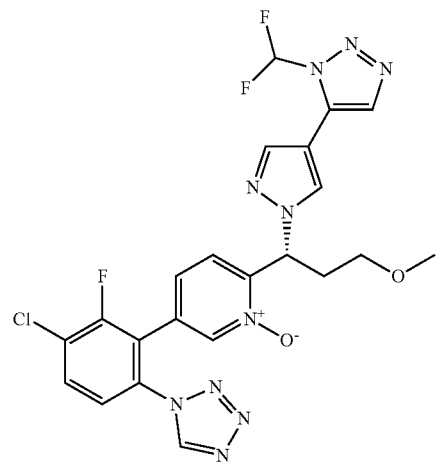 [SMILES: COCC[C@H](c1ccc(-c2c(-n3cnnn3)ccc(Cl)c2F)c[n+]1[O-])n1cc(-c2cnnn2C(F)F)cn1]

Step 1: 5-Bromo-2-(1-(4-(1-(difluoromethyl)-1H-1,2,3-triazol-5-yl)-1H-pyrazol-1-yl)-3-methoxypropyl)pyridine The mixture of 1-(5-bromopyridin-2-yl)-3-methoxypropyl methanesulfonate (260 mg, 0.80 mmol, 1.0 equiv), 1-(difluoromethyl)-5-(1H-pyrazol-4-yl)-1H-1,2,3-triazole (178 mg, 0.96 mmol, 1.2 equiv) and Cs₂CO₃ (523 mg, 1.60 mmol, 2.0 equiv) in acetonitrile (5 mL) was stirred at 90° C. for 2 h. To the reaction mixture was added water, and the mixture extracted with ethyl acetate. The combined organic layers were washed with brine, dried over Na₂SO₄ and concentrated. The residue was purified by silica gel chromatography (0→40% EA/PE) to yield 5-bromo-2-(1-(4-(1-(difluoromethyl)-1H-1,2,3-triazol-5-yl)-1H-pyrazol-1-yl)-3-methoxypropyl)pyridine as a yellow solid. LC/MS: mass calculated for $C_{15}H_{15}BrF_2N_6O$: 412.05, measured (ES, m/z): 413.23 [M+H]⁺.

Step 2: 4-Chloro-2-(6-(1-(4-(1-(difluoromethyl)-1H-1,2,3-triazol-5-yl)-1H-pyrazol-1-yl)-3-methoxypropyl)pyridin-3-yl)-3-fluoroaniline The mixture of 5-bromo-2-(1-(4-(1-(difluoromethyl)-1H-1,2,3-triazol-5-yl)-1H-pyrazol-1-yl)-3-methoxypropyl)pyridine (150 mg, 0.36 mmol, 1.0 equiv), (6-amino-3-chloro-2-fluorophenyl)boronic acid (137 mg, 0.73 mmol, 2.0 equiv), K₂CO₃ (251 mg, 1.82 mmol, 5.0 equiv) and Pd(PPh₃)₄ (42 mg, 0.04 mmol, 0.1 equiv) in 1,4-dioxane (4 mL) and water (1 mL) was stirred at 90° C. under N₂ overnight. To the reaction mixture was added water, and the mixture extracted with ethyl acetate. The combined organic layers were washed with brine, dried over Na₂SO₄ and concentrated. The residue was purified by silica gel chromatography (0→40% EA/PE) to yield 4-chloro-2-(6-(1-(4-(1-(difluoromethyl)-1H-1,2,3-triazol-5-yl)-1H-pyrazol-1-yl)-3-methoxypropyl)pyridin-3-yl)-3-fluoroaniline as a yellow solid. LC/MS: mass calculated for $C_{21}H_{19}ClF_3N_7O$: 477.13, measured (ES, m/z): 478.13 [M+H]⁺.

Step 3: 5-(3-Chloro-2-fluoro-6-(1H-tetrazol-1-yl)phenyl)-2-(1-(4-(1-(difluoromethyl)-1H-1,2,3-triazol-5-yl)-1H-pyrazol-1-yl)-3-methoxypropyl)pyridine The mixture of 4-chloro-2-(6-(1-(4-(1-(difluoromethyl)-1H-1,2,3-triazol-5-yl)-1H-pyrazol-1-yl)-3-methoxypropyl)pyridin-3-yl)-3-fluoroaniline (180 mg, 0.38 mmol, 1.0 equiv), azidotrimethylsilane (2 mL) and trimethoxymethane (2 mL) in acetic acid (3 mL) was stirred at room temperature overnight. The reaction was concentrated and the resulting residue was purified by reverse phase chromatography on C18 (80 g, MeCN/H$_2$O (0.05% CF$_3$COOH): 0→55%) to yield 5-(3-chloro-2-fluoro-6-(1H-tetrazol-1-yl)phenyl)-2-(1-(4-(1-(difluoromethyl)-1H-1,2,3-triazol-5-yl)-1H-pyrazol-1-yl)-3-methoxypropyl)pyridine as a yellow solid. LC/MS: mass calculated for $C_{22}H_{18}ClF_3N_{10}O$: 530.13, measured (ES, m/z): 531.13 [M+H]$^+$.

Step 4: (R)-5-(3-Chloro-2-fluoro-6-(1H-tetrazol-1-yl)phenyl)-2-(1-(4-(1-(difluoromethyl)-1H-1,2,3-triazol-5-yl)-1H-pyrazol-1-yl)-3-methoxypropyl)pyridine 1-oxide The mixture of 5-(3-chloro-2-fluoro-6-(1H-tetrazol-1-yl)phenyl)-2-(1-(4-(1-(difluoromethyl)-1H-1,2,3-triazol-5-yl)-1H-pyrazol-1-yl)-3-methoxypropyl)pyridine (120 mg, 0.23 mmol, 1.0 equiv), methyltrioxorhenium (28 mg, 0.11 mmol, 0.5 equiv) and hydrogen peroxide (128 mg, 1.13 mmol, 5.0 equiv, 30%) in CH$_3$OH (2 mL) was stirred at room temperature for 2 h. The reaction was purified by reverse phase chromatography on C18 (80 g, MeCN/H$_2$O (0.05% CF$_3$COOH): 0→55%) to yield 5-(3-chloro-2-fluoro-6-(1H-tetrazol-1-yl)phenyl)-2-(1-(4-(1-(difluoromethyl)-1H-1,2,3-triazol-5-yl)-1H-pyrazol-1-yl)-3-methoxypropyl)pyridine 1-oxide. The compound, 5-(3-chloro-2-fluoro-6-(1H-tetrazol-1-yl)phenyl)-2-(1-(4-(1-(difluoromethyl)-1H-1,2,3-triazol-5-yl)-1H-pyrazol-1-yl)-3-methoxypropyl)pyridine 1-oxide (80 mg) was separated by Prep-Chiral-HPLC to yield (R)-5-(3-chloro-2-fluoro-6-(1H-tetrazol-1-yl)phenyl)-2-(1-(4-(1-(difluoromethyl)-1H-1,2,3-triazol-5-yl)-1H-pyrazol-1-yl)-3-methoxypropyl)pyridine 1-oxide as a white solid.

LC/MS: mass calculated for $C_{22}H_{18}ClF_3N_{10}O_2$: 546.13, measured (ES, m/z): 547.05 [M+H]$^+$. $^1$H NMR (300 MHz, DMSO-d$_6$) δ 9.69 (s, 1H), 8.58 (s, 1H), 8.44 (s, 1H), 8.43 (s, 1H), 8.13 (t, J=57.0 Hz, 1H), 8.02-8.10 (m, 2H), 7.76 (d, J=8.7 Hz, 1H), 7.33 (d, J=8.3 Hz, 1H), 7.17 (d, J=8.3 Hz, 1H), 6.20 (t, J=7.3 Hz, 1H), 3.27-3.32 (m, 1H), 3.13-3.18 (m, 4H), 2.46-2.52 (m, 2H). $^{19}$F NMR (282 MHz, DMSO-d$_6$) δ −96.69, −112.70.

Example 713: (R)-5-(3-Chloro-2-fluoro-6-(1H-tetrazol-1-yl)phenyl)-2-(3-(difluoromethoxy)-1-(4-(1-(difluoromethyl)-1H-1,2,3-triazol-5-yl)-1H-pyrazol-1-yl)propyl)pyridine 1-oxide

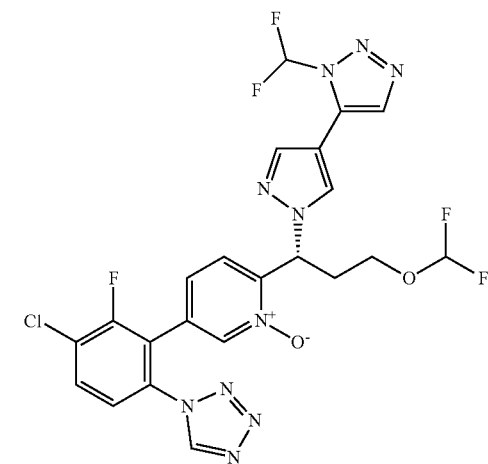 [SMILES: [O-][n+]1cc(-c2c(-n3cnnn3)ccc(Cl)c2F)ccc1[C@@H](CCOC(F)F)n1cc(-c2cnnn2C(F)F)cn1]

Step 1: 5-Bromo-2-(3-(difluoromethoxy)-1-(4-(1-(difluoromethyl)-1H-1,2,3-triazol-5-yl)-1H-pyrazol-1-yl)propyl)pyridine A mixture of cesium carbonate (436.9 mg, 1.34 mmol, 1.0 equiv.) and 1-(difluoromethyl)-5-(1H-pyrazol-4-yl)-1H-1,2,3-triazole (248.3 mg, 1.34 mmol, 1.0 equiv.) in acetonitrile (5.0 mL) was stirred for 15 min at room temperature and then 1-(5-bromopyridin-2-yl)-3-(difluoromethoxy)propyl methanesulfonate (483.0 mg, 1.34 mmol, 1.0 equiv.) was added and the solution was stirred for 2.5 h at 90° C. The resulting mixture was diluted with water, extracted with EA (3×10 mL). Then the organic layers were combined, washed with brine, dried over Na$_2$SO$_4$ and concentrated. The residue was purified by silica gel chromatography (EA/PE, 0%→80%) to yield 5-bromo-2-(3-(difluoromethoxy)-1-(4-(1-(difluoromethyl)-1H-1,2,3-triazol-5-yl)-1H-pyrazol-1-yl)propyl)pyridine as a light yellow oil. LC/MS: mass calculated for $C_{15}H_{13}BrF_4N_6O$: 448.03, measured (ES, m/z): 448.95 [M+H]$^+$.

Step 2: 4-Chloro-2-(6-(3-(difluoromethoxy)-1-(4-(1-(difluoromethyl)-1H-1,2,3-triazol-5-yl)-1H-pyrazol-1-yl)propyl)pyridin-3-yl)-3-fluoroaniline A mixture of 5-bromo-2-(3-(difluoromethoxy)-1-(4-(1-(difluoromethyl)-1H-1,2,3-triazol-5-yl)-1H-pyrazol-1-yl)propyl)pyridine (150.0 mg, 0.33 mmol, 1.0 equiv.), 6-amino-3-chloro-2-fluorophenylboronic acid (94.9 mg, 0.50 mmol, 1.5 equiv.), Pd(PPh$_3$)$_4$ (38.6 mg, 0.03 mmol, 0.1 equiv.) and K$_2$CO$_3$ (138.5 mg, 1.00 mmol, 3.0 equiv.) in 1,4-dioxane/water (V/V=5:1, 6 mL) was refluxed at 90° C. under N$_2$ for 3 h. The resulting mixture was diluted with water, and the mixture extracted with EA (3×15 mL). The organic layers were combined, washed with brine (5 mL), dried over Na$_2$SO$_4$ and concentrated. The residue was purified by silica gel chromatography (0%→80%, EA/PE) to yield 4-chloro-2-(6-(3-(difluoromethoxy)-1-(4-(1-(difluoromethyl)-1H-1,2,3-triazol-5-yl)-1H-pyrazol-1-yl)propyl)

pyridin-3-yl)-3-fluoroaniline as an orange oil. LC/MS: mass calculated for $C_{21}H_{17}ClF_5N_7O$: 513.11, measured (ES, m/z): 514.00 [M+H]$^+$.

Step 3: 5-(3-Chloro-2-fluoro-6-(1H-tetrazol-1-yl)phenyl)-2-(3-(difluoromethoxy)-1-(4-(1-(difluoromethyl)-1H-1,2,3-triazol-5-yl)-1H-pyrazol-1-yl)propyl)pyridine A mixture of 4-chloro-2-(6-(3-(difluoromethoxy)-1-(4-(1-(difluoromethyl)-1H-1,2,3-triazol-5-yl)-1H-pyrazol-1-yl)propyl)pyridin-3-yl)-3-fluoroaniline (100.0 mg, 0.25 mmol, 1.0 equiv.), trimethoxymethane (2.0 mL), azidotrimethylsilane (2.0 mL) and acetic acid (2.0 mL) was stirred overnight at 30° C. The reaction was purified by reverse chromatography on C18 (0→55% MeCN/H$_2$O (0.05% CF$_3$COOH)) to yield 5-(3-chloro-2-fluoro-6-(1H-tetrazol-1-yl)phenyl)-2-(3-(difluoromethoxy)-1-(4-(1-(difluoromethyl)-1H-1,2,3-triazol-5-yl)-1H-pyrazol-1-yl)propyl)pyridine as a light yellow solid. LC/MS: mass calculated for $C_{22}H_{16}ClF_5N_{10}O$: 566.11, measured (ES, m/z): 567.00 [M+H]$^+$.

Step 4: (R)-5-(3-Chloro-2-fluoro-6-(1H-tetrazol-1-yl)phenyl)-2-(3-(difluoromethoxy)-1-(4-(1-(difluoromethyl)-1H-1,2,3-triazol-5-yl)-1H-pyrazol-1-yl)propyl)pyridine 1-oxide A mixture of 5-(3-chloro-2-fluoro-6-(1H-tetrazol-1-yl)phenyl)-2-(3-(difluoromethoxy)-1-(4-(1-(difluoromethyl)-1H-1,2,3-triazol-5-yl)-1H-pyrazol-1-yl)propyl)pyridine (112.0 mg, 0.19 mmol, 1.0 equiv.), methyltrioxorhenium (24.6 mg, 0.10 mmol, 0.5 equiv.) and hydrogen peroxide (0.5 mL, 30 wt %) in CH$_3$OH (2.0 mL) was stirred for 3 h at room temperature. The resulting mixture was purified by reverse phase chromatography on C18 (MeCN/H$_2$O (0.05% CF$_3$COOH)) to yield 5-(3-chloro-2-fluoro-6-(1H-tetrazol-1-yl)phenyl)-2-(3-(difluoromethoxy)-1-(4-(1-(difluoromethyl)-1H-1,2,3-triazol-5-yl)-1H-pyrazol-1-yl)propyl)pyridine 1-oxide as a white solid. The racemic product was separated by chiral-HPLC to yield (R)-5-(3-chloro-2-fluoro-6-(1H-tetrazol-1-yl)phenyl)-2-(3-(difluoromethoxy)-1-(4-(1-(difluoromethyl)-1H-1,2,3-triazol-5-yl)-1H-pyrazol-1-yl)propyl)pyridine 1-oxide as a white solid.

LC/MS: mass calculated for $C_{22}H_{16}ClF_5N_{10}O_2$: 582.11, measured (ES, m/z): 583.05 [M+H]$^+$. $^1$H NMR (300 MHz, DMSO-d$_6$) δ 9.67 (s, 1H), 8.53-7.96 (m, 6H), 7.71-7.80 (m, 1H), 7.36 (d, J=8.3 Hz, 1H), 7.14-7.22 (m, 1H), 6.32-6.90 (m, 1H), 6.18-6.25 (m, 1H), 3.75-3.86 (m, 1H), 3.58-3.72 (m, 1H), 2.51-2.67 (m, 2H). $^{19}$F-NMR (282 MHz, DMSO-d$_6$) δ −83.41, −97.13, −112.66.

Example 714: (S)-5-(3-Chloro-2-fluoro-6-(1H-tetrazol-1-yl)phenyl)-2-(3-(difluoromethoxy)-1-(4-(2-(difluoromethyl)-2H-1,2,3-triazol-4-yl)-1H-pyrazol-1-yl)propyl)pyridine 1-oxide

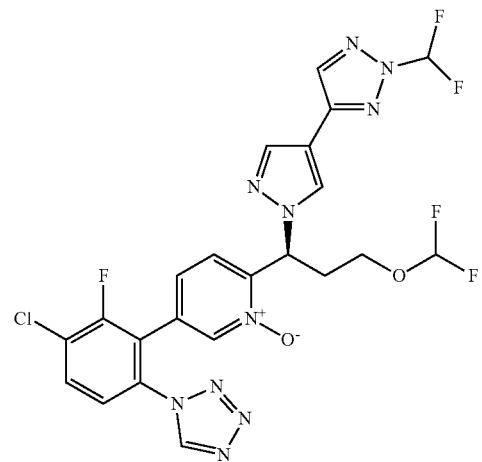 [SMILES: [O-][n+]1cc(-c2c(-n3cnnn3)ccc(Cl)c2F)ccc1[C@H](CCOC(F)F)n1cc(-c2cnn(C(F)F)n2)cn1]

LC/MS: mass calculated for $C_{22}H_{16}ClF_5N_{10}O_2$: 582.11, measured (ES, m/z): 583.05 [M+H]$^+$. $^1$H NMR (300 MHz, DMSO-d$_6$) δ 9.67 (s, 1H), 7.67-8.66 (m, 7H), 7.10-7.32 (m, 2H), 6.61 (t, J=75.7 Hz, 1H), 6.21-6.23 (m, 1H), 3.60-3.88 (m, 2H), 2.53-2.71 (m, 2H). $^{19}$F NMR (282 MHz, DMSO-d$_6$) δ −83.28, −96.71, −112.67.

Example 715: (S)-5-(3-Chloro-6-(4-chloro-1H-1,2,3-triazol-1-yl)-2-fluorophenyl)-2-(3-(difluoromethoxy)-1-(4-(1-(difluoromethyl)-1H-1,2,3-triazol-4-yl)-1H-pyrazol-1-yl)propyl)pyridine 1-oxide

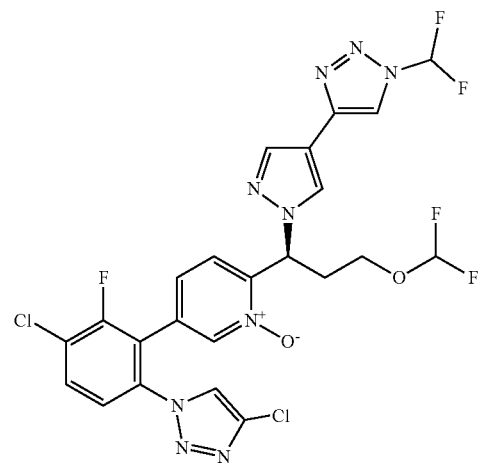 [SMILES: [O-][n+]1cc(-c2c(-n3cc(Cl)nn3)ccc(Cl)c2F)ccc1[C@H](CCOC(F)F)n1cc(-c2cn(C(F)F)nn2)cn1]

LC/MS: mass calculated for $C_{23}H_{16}Cl_2F_5N_9O_2$: 615.07, measured (ES, m/z): 615.95 [M+H]$^+$, $^1$H NMR (300 MHz, DMSO-d$_6$) δ 8.91 (s, 1H), 8.67 (s, 1H), 8.41-8.49 (m, 2H), 7.79-8.32 (m, 3H), 7.69 (dd, J=8.8, 1.5 Hz, 1H), 7.31 (d, J=8.3 Hz, 1H), 7.18 (d, J=8.2 Hz, 1H), 6.64 (t, J=75.7 Hz, 1H), 6.22-6.26 (m, 1H), 3.61-3.90 (m, 2H), 2.56-2.79 (m, 2H). $^{19}$F NMR (282 MHz, DMSO-d$_6$) δ −83.26, −96.25, −112.93.

Example 716: (R)-5-(3-Chloro-6-(4-chloro-1H-1,2,3-triazol-1-yl)-2-fluorophenyl)-2-(3-(difluoromethoxy)-1-(4-(1-(difluoromethyl)-1H-1,2,3-triazol-4-yl)-1H-pyrazol-1-yl)propyl)pyridine 1-oxide

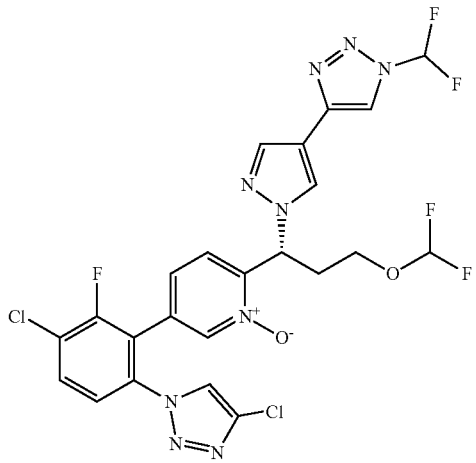 [SMILES: [O-][n+]1cc(-c2c(-n3cc(Cl)nn3)ccc(Cl)c2F)ccc1[C@@H](CCOC(F)F)n1cc(-c2cn(C(F)F)nn2)cn1]

LC/MS: mass calculated for $C_{23}H_{16}Cl_2F_5N_9O_2$: 615.07, measured (ES, m/z): 615.95 [M+H]+, $^1$H NMR (300 MHz, DMSO-$d_6$) δ 8.91 (s, 1H), 8.67 (s, 1H), 8.36-8.52 (m, 2H), 7.95-8.33 (m, 3H), 7.69 (dd, J=8.7, 1.6 Hz, 1H), 7.31 (d, J=8.3 Hz, 1H), 7.18 (dd, J=8.3, 1.7 Hz, 1H), 6.64 (t, J=75.7 Hz, 1H), 6.22-6.26 (m, 1H), 3.65-3.90 (m, 2H), 2.57-2.72 (m, 2 h). $^{19}$F NMR (282 MHz, DMSO-$d_6$) δ −83.26, −96.24, −112.93, −218.14.

Example 717: (R)-5-(3-Chloro-6-(4-chloro-1H-1,2,3-triazol-1-yl)-2-fluorophenyl)-2-(3-(difluoromethoxy)-1-(4-(4-fluoro-1-methyl-1H-1,2,3-triazol-5-yl)-1H-pyrazol-1-yl)propyl)pyridine 1-oxide

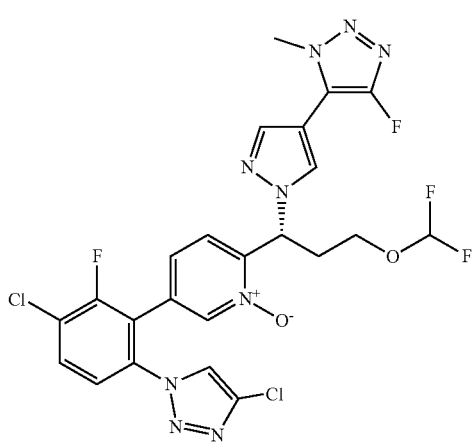 [SMILES: Cn1nnc(F)c1-c1cnn([C@H](CCOC(F)F)c2ccc(-c3c(-n4cc(Cl)nn4)ccc(Cl)c3F)c[n+]2[O-])c1]

Step 1: 5-Bromo-2-(3-(difluoromethoxy)-1-(4-(1-methyl-1H-1,2,3-triazol-5-yl)-1H-pyrazol-1-yl)propyl)pyridine To a mixture of 1-methyl-5-(1H-pyrazol-4-yl)-1H-1,2,3-triazole (145 mg, 0.97 mmol, 1.4 equiv.) in acetonitrile (10 mL) was added cesium carbonate (226 mg, 0.69 mmol, 1.0 equiv.) and 1-(5-bromopyridin-2-yl)-3-(difluoromethoxy)propyl methanesulfonate (250 mg, 0.69 mmol, 1.0 equiv.). The reaction was stirred overnight at 70° C. After cooling to room temperature, water was added, the mixture was extracted with EA. The combined extracts were washed with water, saturated brine and dried over anhydrous Na$_2$SO$_4$ and concentrated. The residue was purified silica gel chromatography (0→5% MeOH/DCM) to yield 5-bromo-2-(3-(difluoromethoxy)-1-(4-(1-methyl-1H-1,2,3-triazol-5-yl)-1H-pyrazol-1-yl)propyl)pyridine as a yellow oil. LC/MS: mass calculated for $C_{15}H_{15}BrF_2N_6O$: 412.05, measured (ES, m/z): 413.95, 414.95 [M+H, M+H+2]+.

Step 2: 5-Bromo-2-(3-(difluoromethoxy)-1-(4-(4-fluoro-1-methyl-1H-1,2,3-triazol-5-yl)-1H-pyrazol-1-yl)propyl)pyridine To a mixture of 5-bromo-2-(3-(difluoromethoxy)-1-(4-(1-methyl-1H-1,2,3-triazol-5-yl)-1H-pyrazol-1-yl)propyl)pyridine (250 mg, 0.61 mmol, 1.0 equiv.) in acetonitrile (5 mL) was added 1-chloromethyl-4-fluoro-1,4-diazoniabicyclo[2.2.2]octane bis(tetrafluoroborate) (Selectfluor™, 429 mg, 1.2 mmol, 2.0 equiv.). The reaction was stirred at 80° C. for 3 h. After cooling to room temperature, water was added, the mixture was extracted with EA. The combined extracts were washed with water, saturated brine and dried over anhydrous Na$_2$SO$_4$ and concentrated. The residue was purified silica gel chromatography (0→10% MeOH/DCM) to yield 5-bromo-2-(3-(difluoromethoxy)-1-(4-(4-fluoro-1-methyl-1H-1,2,3-triazol-5-yl)-1H-pyrazol-1-yl)propyl)pyridine as a yellow oil. LC/MS: mass calculated for $C_{15}H_{14}BrF_3N_6O$: 430.04, measured (ES, m/z): 430.95, 432.95 [M+H, M+H+2]+.

Step 3: (6-(3-(Difluoromethoxy)-1-(4-(4-fluoro-1-methyl-1H-1,2,3-triazol-5-yl)-1H-pyrazol-1-yl)propyl)pyridin-3-yl)boronic acid To a mixture of 5-bromo-2-(3-(difluoromethoxy)-1-(4-(4-fluoro-1-methyl-1H-1,2,3-triazol-5-yl)-1H-pyrazol-1-yl)propyl)pyridine (130 mg, 0.32 mmol, 1.0 equiv.) and 4,4,4',4',5,5,5',5'-octamethyl-2,2'-bi(1,3,2-dioxaborolane) (120 mg, 0.47 mmol, 1.5 equiv.) in 1,4-dioxane (5 mL) was added potassium acetate (62 mg, 0.63 mmol, 2.0 equiv.) and [1,1'-Bis(diphenylphosphino)ferrocene]dichloropalladium (II) (23 mg, 0.03 mmol, 0.1 equiv.) under N$_2$. The reaction was stirred at 100° C. for 1 h. After cooling to room temperature, water was added, the mixture was extracted with EA. The combined extracts were washed with water, saturated brine, and dried over anhydrous Na$_2$SO$_4$. The resulting mixture was then concentration to yield (6-(3-(difluoromethoxy)-1-(4-(4-fluoro-1-methyl-1H-1,2,3-triazol-5-yl)-1H-pyrazol-1-yl)propyl)pyridin-3-yl)boronic acid. LC/MS: mass calculated for $C_{15}H_{16}BF_3N_6O_3$: 396.13, measured (ES, m/z): 397.00 [M+H]+.

Step 4: 5-(3-Chloro-6-(4-chloro-1H-1,2,3-triazol-1-yl)-2-fluorophenyl)-2-(3-(difluoromethoxy)-1-(4-(4-fluoro-1-methyl-1H-1,2,3-triazol-5-yl)-1H-pyrazol-1-yl)propyl)pyridine To a mixture of (6-(3-(difluoromethoxy)-1-(4-(4-fluoro-1-methyl-1H-1,2,3-triazol-5-yl)-1H-pyrazol-1-yl)propyl)pyridin-3-yl)boronic acid (200 mg, resulting) and 4-chloro-1-(4-chloro-3-fluoro-2-iodophenyl)-1H-1,2,3-triazole (108 mg, 0.30 mmol, 1.0 equiv.) in 1,4-dioxane (5 mL) and water (1 mL) was added potassium carbonate (126 mg, 0.91 mmol, 3.0 equiv.) and tetrakis(triphenylphosphine)palladium (35 mg, 0.03 mmol, 0.1 equiv.). After cooling to room temperature, water was added, the mixture was extracted with EA. The combined extracts were washed with water, saturated brine and dried over anhydrous $Na_2SO_4$ and concentrated. The residue was purified silica gel chromatography (0→10% MeOH/DCM) to yield 5-(3-chloro-6-(4-chloro-1H-1,2,3-triazol-1-yl)-2-fluorophenyl)-2-(3-(difluoromethoxy)-1-(4-(4-fluoro-1-methyl-1H-1,2,3-triazol-5-yl)-1H-pyrazol-1-yl)propyl)pyridine as a white solid. LC/MS: mass calculated for $C_{23}H_{17}Cl_2F_4N_9O$: 581.01, measured (ES, m/z): 582.20 $[M+H]^+$.

Step 5: (R)-5-(3-Chloro-6-(4-chloro-1H-1,2,3-triazol-1-yl)-2-fluorophenyl)-2-(3-(difluoromethoxy)-1-(4-(4-fluoro-1-methyl-1H-1,2,3-triazol-5-yl)-1H-pyrazol-1-yl)propyl)pyridine 1-oxide To a solution of 5-(3-chloro-6-(4-chloro-1H-1,2,3-triazol-1-yl)-2-fluorophenyl)-2-(3-(difluoromethoxy)-1-(4-(4-fluoro-1-methyl-1H-1,2,3-triazol-5-yl)-1H-pyrazol-1-yl)propyl)pyridine (90 mg, 0.16 mmol, 1.0 equiv.) in MeOH (3 mL) was added methyltrioxorhenium (12 mg, 0.05 mmol, 0.3 equiv) and $H_2O_2$ (30 wt %, 26 mg, 0.77 mmol, 5.0 equiv.). The resulting mixture was stirred at room temperature. for 2 h. The solution was purified by reverse phase chromatography on C18 (80 g, $MeCN/H_2O$ (0.05% $CF_3COOH$): 0→60%) and Prep-Chiral-HPLC to yield (R)-5-(3-chloro-6-(4-chloro-1H-1,2,3-triazol-1-yl)-2-fluorophenyl)-2-(3-(difluoromethoxy)-1-(4-(4-fluoro-1-methyl-1H-1,2,3-triazol-5-yl)-1H-pyrazol-1-yl)propyl)pyridine 1-oxide as a white solid.

LC/MS: mass calculated for $C_{23}H_{17}Cl_2F_4N_9O_2$: 597.08, measured (ES, m/z): 598.15 $[M+H]^+$. $^1H$ NMR (400 MHz, DMSO-$d_6$): δ 8.67 (s, 1H), 8.53 (s, 1H), 8.42 (d, J=1.7 Hz, 1H), 7.98-8.06 (m, 2H), 7.65-7.72 (m, 1H), 7.36 (d, J=8.3 Hz, 1H), 7.12-7.22 (m, 1H), 6.62 (t, J=75.7 Hz, 1H), 6.22-6.32 (m, 1H), 4.09 (s, 3H), 3.82-3.87 (m, 1H), 3.64-3.75 (m, 1H), 2.54-2.75 (m, 2H). $^{19}F$ NMR (376 MHz, DMSO-$d_6$): δ −83.32, −112.93, −145.13.

Example 718: (S)-5-(3-Chloro-6-(4-chloro-1H-1,2,3-triazol-1-yl)-2-fluorophenyl)-2-(3-(difluoromethoxy)-1-(4-(4-fluoro-1-methyl-1H-1,2,3-triazol-5-yl)-1H-pyrazol-1-yl)propyl)pyridine 1-oxide

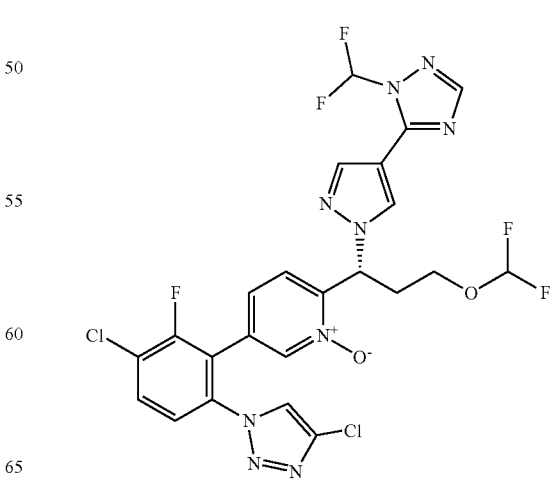

LC/MS: mass calculated for $C_{23}H_{17}Cl_2F_4N_9O_2$: 597.08, measured (ES, m/z): 598.15 $[M+H]^+$. $^1H$ NMR (400 MHz, DMSO-$d_6$) δ 8.67 (s, 1H), 8.53 (s, 1H), 8.40-8.45 (m, 1H), 7.98-8.06 (m, 2H), 7.69 (dd, J=8.7, 1.5 Hz, 1H), 7.36 (d, J=8.3 Hz, 1H), 7.18 (dd, J=8.3, 1.7 Hz, 1H), 6.62 (t, J=75.7 Hz, 1H), 6.26-6.29 (m, 1H), 4.09 (s, 3H), 3.82-3.87 (m, 1H), 3.62-3.66 (m, 1H), 2.56-2.71 (m, 2H). $^{19}F$ NMR (376 MHz, DMSO-$d_6$) δ −83.32, −112.92, −145.10.

Example 719: (S)-5-(3-Chloro-6-(4-chloro-1H-1,2,3-triazol-1-yl)-2-fluorophenyl)-2-(1-(4-(2-(difluoromethyl)-2H-1,2,3-triazol 4-yl)-1H-pyrazol-1-yl).2-(1H-pyrazol-1-yl)ethyl)pyridine 1-oxide

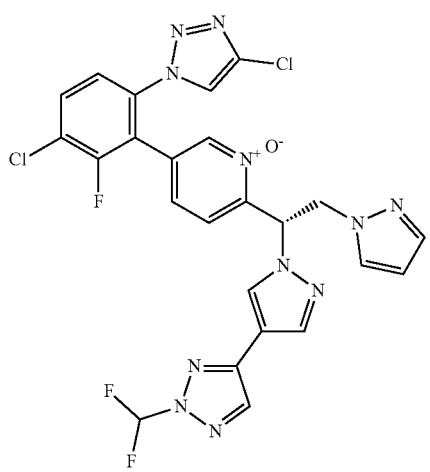

LC/MS: mass calculated for $C_{24}H_{16}Cl_2F_3N_{11}O$: 601.09, measured (ES, m/z): 601.95$[M+H]^+$. $^1H$ NMR (300 MHz, DMSO-$d_6$) δ 8.68 (s, 1H), 8.45-8.52 (m, 1H), 8.39-8.42 (m, 2H), 7.91-8.32 (m, 3H), 7.70 (dd, J=8.7, 1.6 Hz, 1H), 7.39-7.53 (m, 3H), 7.20 (dd, J=8.3, 1.7 Hz, 1H), 6.58-6.62 (m, 1H), 6.13 (t, J=2.1 Hz, 1H), 4.92-5.17 (m, 2H). $^{19}F$ NMR (282 MHz, DMSO-$d_6$) δ −73.51, −96.71, −112.88, −112.93.

Example 720: (R)-5-(3-Chloro-6-(4-chloro-1H-1,2,3-triazol-1-yl)-2-fluorophenyl)-2-(3-(difluoromethoxy)-1-(4-(1-(difluoromethyl)-1H-1,2,4-triazol-5-yl)-1H-pyrazol-1-yl)propyl)pyridine 1-oxide

Step 1: 1-(Difluoromethyl)-5-(1-(tetrahydro-2H-pyran-2-yl)-1H-pyrazol-4-yl)-1H-1,2,4-triazole To a solution of 1-(difluoromethyl)-1H-1,2,4-triazole (3.0 g, 25.20 mmol, 1.0 equiv.) in DMF (40 mL) was added 4-iodo-1-(tetrahydro-2H-pyran-2-yl)-1H-pyrazole (7.0 g, 25.20 mmol, 1.0 equiv.), CuI (2.4 g, 12.60 mmol, 0.5 equiv.), t-BuOLi (2.2 g, 27.71 mmol, 1.1 equiv.) and 3,4,7,8-tetramethyl-1,10-phenanthroline (0.60 g, 2.52 mmol, 0.1 equiv.). The resulting mixture was maintained under nitrogen and stirred at 100° C. for 2 h.

After cooling to room temperature, the reaction was quenched with water (150 mL). The resulting mixture was extracted with ethyl acetate (3×40 mL). The organic layers were combined, dried over anhydrous sodium sulfate, filtered and concentrated. The resulting residue was purified by silica gel chromatography (0→70% EA/PE) to yield 1-(difluoromethyl)-5-(1-(tetrahydro-2H-pyran-2-yl)-1H-pyrazol-4-yl)-1H-1,2,4-triazole as a yellow oil. LC/MS: mass calculated for $C_{11}H_{13}F_2N_5O$: 269.11, measured (ES, m/z): 270.05 $[M+H]^+$.

Step 2: 1-(Difluoromethyl)-5-(1H-pyrazol-4-yl)-1H-1,2,4-triazole

To a solution of 1-(difluoromethyl)-5-(1-(tetrahydro-2H-pyran-2-yl)-1H-pyrazol-4-yl)-1H-1,2,4-triazole (182 mg, 0.68 mmol, 1.0 equiv.) in MeOH (4 mL) and HCl (2 mL) was stirred at room temperature. for 2 h. The resulting mixture was concentrated to yield 1-(difluoromethyl)-5-(1H-pyrazol-4-yl)-1H-1,2,4-triazole as a yellow oil which was used in the next step without further purification. LC/MS: mass calculated for $C_6H_5F_2N_5$: 185.05, measured (ES, m/z): 186.05 $[M+H]^+$.

Step 3: 5-Bromo-2-(3-(difluoromethoxy)-1-(4-(1-(difluoromethyl)-1H-1,2,4-triazol-5-yl)-1H-pyrazol-1-yl)propyl)pyridine To a solution of 4-(difluoromethyl)-3-(1H-pyrazol-4-yl)-4H-1,2,4-triazole (150 mg, 0.81 mmol, 1.0 equiv.) in ACN (20 mL) was added $Cs_2CO_3$ (528 mg, 1.62 mmol, 2.0 equiv.) at room temperature. for 0.5 h. To the resulting mixture was added 1-(5-bromopyridin-2-yl)-3-(difluoromethoxy)propyl methanesulfonate (350 mg, 0.97 mmol, 1.2 equiv.). The resulting mixture was stirred at 80° C. for 2 h. The reaction was quenched with water (50 mL). The resulting mixture was extracted with ethyl acetate (3×20 mL). The organic layers were combined, dried over anhydrous sodium sulfate, filtered and concentrated. The resulting residue was purified by silica gel chromatography (0→50% EA/PE) to yield 5-bromo-2-(3-(difluoromethoxy)-1-(4-(1-(difluoromethyl)-1H-1,2,4-triazol-5-yl)-1H-pyrazol-1-yl)propyl)pyridine as a light yellow oil. LC/MS: mass calculated for $C_{15}H_{13}BrF_4N_6O$: 448.03, measured (ES, m/z): 448.95, 450.95 $[M+H, M+H+2]^+$.

Step 4: (6-(3-(Difluoromethoxy)-1-(4-(1-(difluoromethyl)-1H-1,2,4-triazol-5-yl)-1H-pyrazol-1-yl)propyl)pyridin-3-yl)boronic acid To a solution of 5-bromo-2-(3-(difluoromethoxy)-1-(4-(4-(difluoromethyl)-4H-1,2,4-triazol-3-yl)-1H-pyrazol-1-yl)propyl)pyridine (249 mg, 0.56 mmol, 1.0 equiv.) in 1,4-dioxane (15 mL) was added 4,4,4',4',5,5,5',5'-octamethyl-2,2'-bi(1,3,2-dioxaborolane) (282 mg, 1.11 mmol, 2.0 equiv.), KOAc (163 mg, 1.66 mmol, 3.0 equiv.) and Pd(dppf)Cl$_2$ (47 mg, 0.06 mmol, 0.1 equiv.). The resulting mixture was maintained under nitrogen and stirred at 90° C. for 2 h. After cooling to room temperature, the reaction was quenched with water (50 mL). The resulting mixture was extracted with ethyl acetate (3×20 mL), filtered and concentrated to yield (6-(3-(difluoromethoxy)-1-(4-(1-(difluoromethyl)-1H-1,2,4-triazol-5-yl)-1H-pyrazol-1-yl)propyl)pyridin-3-yl)boronic acid as a black oil for resulting. LC/MS: mass calculated for $C_{15}H_{15}BF_4N_6O_3$: 414.12, measured (ES, m/z): 415.0 $[M+H]^+$.

Step 5: 5-(3-Chloro-6-(4-chloro-1H-1,2,3-triazol-1-yl)-2-fluorophenyl)-2-(3-(difluoromethoxy)-1-(4-(1-(difluoromethyl)-1H-1,2,4-triazol-5-yl)-1H-pyrazol-1-yl)propyl)pyridine To a solution of (6-(3-(difluoromethoxy)-1-(4-(4-(difluoromethyl)-4H-1,2,4-triazol-3-yl)-1H-pyrazol-1-yl)propyl)pyridin-3-yl)boronic acid (250 mg, resulting) in 1,4-dioxane (20 mL) and $H_2O$ (2 mL) was added 4-chloro-1-(4-chloro-3-fluoro-2-iodophenyl)-1H-1,2,3-triazole (432 mg, 1.21 mmol), $K_2CO_3$ (250 mg, 1.81 mmol) and Pd(PPh$_3$)$_4$ (70 mg, 0.06 mmol). The resulting mixture was maintained under nitrogen and stirred at 75° C. for 2 h. After cooling to room temperature, the reaction was quenched with water (50 mL). The resulting mixture was extracted with ethyl acetate (3×20 mL). The organic layers were combined, dried over anhydrous sodium sulfate, filtered and concentrated. The resulting residue was purified by silica gel chromatography (0→5% MeOH/DCM) to yield 5-(3-chloro-6-(4-chloro-1H-1,2,3-triazol-1-yl)-2-fluorophenyl)-2-(3-(difluoromethoxy)-1-(4-(1-(difluoromethyl)-1H-1,2,4-triazol-5-yl)-1H-pyrazol-1-yl)propyl)pyridine as a brown solid. LC/MS: mass calculated for $C_{23}H_{16}Cl_2F_5N_9O$: 599.08, measured (ES, m/z): 621.9 $[M+Na]^+$.

Step 6: (R)-5-(3-Chloro-6-(4-chloro-1H-1,2,3-triazol-1-yl)-2-fluorophenyl)-2-(3-(difluoromethoxy)-1-(4-(1-(difluoromethyl)-1H-1,2,4-triazol-5-yl)-1H-pyrazol-1-yl)propyl)pyridine 1-oxide To a solution of 5-(3-chloro-6-(4-chloro-1H-1,2,3-triazol-1-yl)-2-fluorophenyl)-2-(3-(difluoromethoxy)-1-(4-(1-(difluoromethyl)-1H-1,2,4-triazol-5-yl)-1H-pyrazol-1-yl)propyl)pyridine (100 mg, 0.17 mmol, 1.0 equiv.) in MeOH (4 mL) was added methyltrioxorhenium (20 mg, 0.08 mmol, 0.5 equiv.) and $H_2O_2$ (0.08 mL, 0.83 mmol, 5 equiv.). The resulting mixture was stirred at room temperature. for 6 h. The reaction was purified by reverse phase chromatography on $C_{18}$ (80 g, 5%→55%, MeCN/H$_2$O) and Chiral HPLC to yield (R)-5-(3-chloro-6-(4-chloro-1H-1,2,3-triazol-1-yl)-2-fluorophenyl)-2-(3-(difluoromethoxy)-1-(4-(1-(difluoromethyl)-1H-1,2,4-triazol-5-yl)-1H-pyrazol-1-yl)propyl)pyridine 1-oxide as a white solid.

LC/MS: mass calculated for $C_{23}H_{16}Cl_2F_5N_9O_2$: 615.07, measured (ES, m/z): 616.05 $[M+H]^+$. $^1$H NMR (300 MHz, DMSO-d$_6$) δ 8.67 (s, 1H), 8.66 (s, 1H), 8.43 (s, 1H), 8.26 (s, 1H), 8.12 (s, 1H), 7.98-8.09 (m, 2H), 7.69 (d, J=8.7 Hz, 1H), 7.40 (d, J=8.3 Hz, 1H), 7.20 (d, J=8.2 Hz, 1H), 6.88 (t, J=75.0 Hz, 1H), 6.24-6.41 (m, 1H), 3.80-3.87 (m, 1H), 3.68-3.76 (m, 1H), 2.56-2.70 (m, 2H). $^{19}$F NMR (282 MHz, DMSO-d$_6$) δ −83.36, −96.16, −112.92.

Example 721: (S)-5-(3-Chloro-6-(4-chloro-1H-1,2,3-triazol-1-yl)-2-fluorophenyl)-2-(1-(4-(1-(difluoromethyl)-1H-1,2,3-triazol-5-yl)-1H-pyrazol-1-yl)-2-(1H-pyrazol-1-yl)ethyl)pyridine 1-oxide

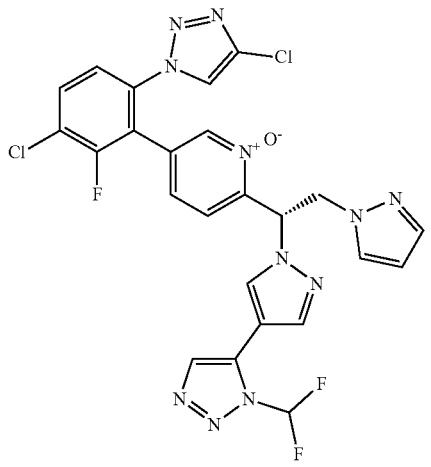

LC/MS: mass calculated for $C_{24}H_{16}Cl_2F_3N_{11}O$: 601.09, measured (ES, m/z): 601.95 [M+H]$^+$. $^1$H NMR (300 MHz, DMSO-d$_6$) δ 8.68 (s, 1H), 8.45-8.52 (m, 1H), 8.37-8.45 (m, 2H), 7.91-8.32 (m, 3H), 7.70 (dd, J=8.7, 1.6 Hz, 1H), 7.39-7.53 (m, 3H), 7.20 (dd, J=8.3, 1.7 Hz, 1H), 6.58-6.63 (m, 1H), 6.13 (t, J=2.1 Hz, 1H), 4.92-5.17 (m, 2H). $^{19}$F NMR (282 MHz, DMSO-d$_6$) δ −73.65, −96.72, −112.88.

Example 722: (R)-5-(3-Chloro-6-(4-chloro-1H-1,2,3-triazol-1-yl)-2-fluorophenyl)-2-(1-(4-(1-(difluoromethyl)-1H-1,2,3-triazol-5-yl)-1H-pyrazol-1-yl)-2-(1H-pyrazol-1-yl)ethyl)pyridine 1-oxide

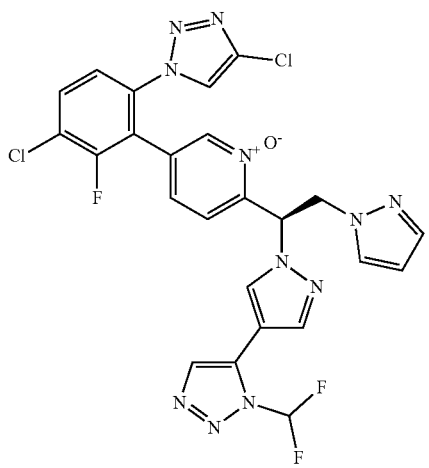

LC/MS: mass calculated for $C_{24}H_{16}Cl_2F_3N_{11}O$: 601.09, measured (ES, m/z): 601.95 [M+H]$^+$. $^1$H NMR (300 MHz, DMSO-d$_6$) δ 8.68 (s, 1H), 8.30-8.58 (m, 3H), 7.91-8.32 (m, 3H), 7.70 (dd, J=8.7, 1.6 Hz, 1H), 7.53-7.39 (m, 3H), 7.20 (dd, J=8.3, 1.7 Hz, 1H), 6.58-6.63 (m, 1H), 6.13 (t, J=2.1 Hz, 1H), 4.95-5.14 (m, 2H). $^{19}$F NMR (282 MHz, DMSO-d$_6$) δ −96.71, −112.88.

Example 723: (S)-5-(3-Chloro-2-fluoro-6-(1H-tetrazol-1-yl)phenyl)-2-(1-(4-(2-(difluoromethyl)-2H-1,2,3-triazol-4-yl)-1H-pyrazol-1-yl)-3-methoxypropyl)pyridine 1-oxide

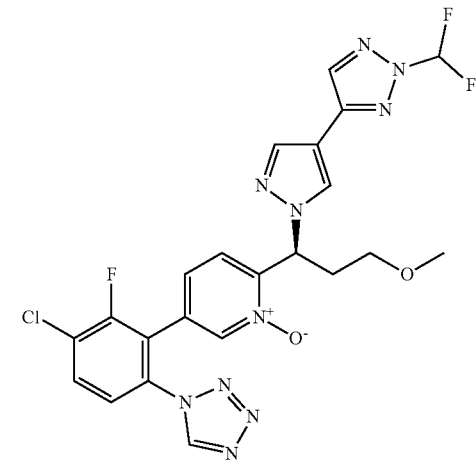 [SMILES: COCC[C@@H](c1ccc(-c2c(-n3cnnn3)ccc(Cl)c2F)c[n+]1[O-])n1cc(-c2cnn(C(F)F)n2)cn1]

LC/MS: mass calculated for $C_{22}H_{18}ClF_3N_{10}O_2$: 546.13, measured (ES, m/z): 547.05 [M+H]$^+$. $^1$H NMR (300 MHz, DMSO-d$_6$) δ 9.70 (s, 1H), 8.33-8.56 (m, 3H), 8.17 (d, J=8.5 Hz, 1H), 7.97-8.12 (m, 2H), 7.76 (dd, J=8.7, 1.6 Hz, 1H), 7.42 (d, J=8.3 Hz, 1H), 7.19 (dd, J=8.3, 1.7 Hz, 1H), 6.20-6.25 (m, 1H), 3.28-3.30 (m, 1H), 3.18-3.20 (m, 4H), 2.48-2.50 (m, 2H). $^{19}$F NMR (282 MHz, DMSO-d$_6$) δ −97.09, −112.68.

Example 724: (S)-5-(3-Chloro-6-(4-chloro-1H-1,2,3-triazol-1-yl)-2-fluorophenyl)-2-(3-(difluoromethoxy)-1-(4-(1-(difluoromethyl)-1H-1,2,4-triazol-5-yl)-1H-pyrazol-1-yl)propyl)pyridine 1-oxide

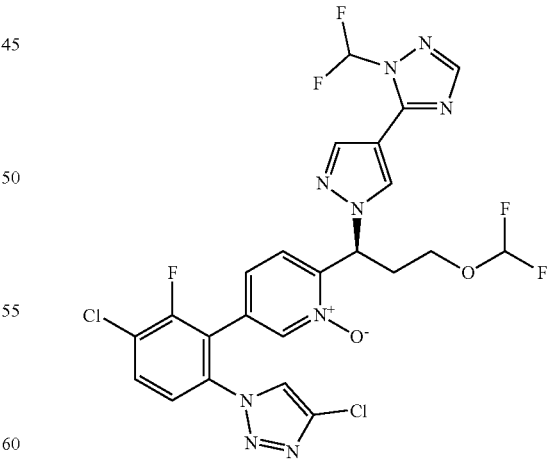

LC/MS: mass calculated for $C_{23}H_{16}Cl_2F_5N_9O_2$: 615.1, measured (ES, m/z): 616.0 [M+H]$^+$. $^1$H NMR (300 MHz, DMSO-d$_6$) δ 8.66-8.68 (m, 2H), 8.39-8.46 (m, 1H), 7.83-8.30 (m, 4H), 7.69 (dd, J=8.7, 1.6 Hz, 1H), 7.40 (d, J=8.3 Hz, 1H), 7.20 (dd, J=8.3, 1.7 Hz, 1H), 6.62 (t, J=100.8 Hz, 1H), 6.28-6.30 (m, 1H), 3.82-3.84 (m, 2H), 2.60-2.71 (m, 2H). $^{19}$F NMR (282 MHz, DMSO-d$_6$) δ −83.36, −96.16, −112.92.

Example 725: (R)-5-(3-Chloro-2-fluoro-6-(1H-tetrazol-1-yl)phenyl)-2-(1-(4-(1-(difluoromethyl)-1H-1,2,3-triazol-4-yl)-1H-pyrazol-1-yl)-3-methoxypropyl)pyridine 1-oxide

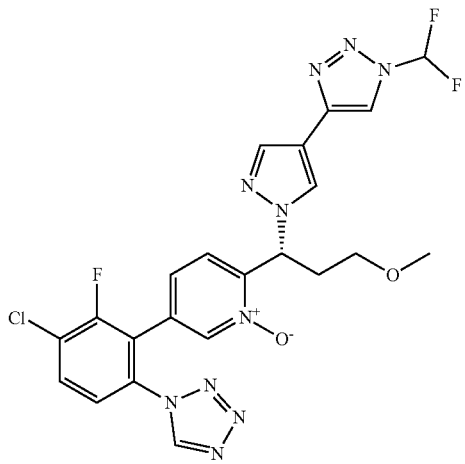 [SMILES: COCC[C@H](c1ccc(-c2c(-n3cnnn3)ccc(Cl)c2F)c[n+]1[O-])n1cc(-c2cn(C(F)F)nn2)cn1]

Step 1: 5-Bromo-2-(1-(4-(1-(difluoromethyl)-1H-1,2,3-triazol-4-yl)-1H-pyrazol-1-yl)-3-methoxypropyl)pyridine The mixture of 1-(5-bromopyridin-2-yl)-3-methoxypropyl methanesulfonate (300 mg, 0.93 mmol, 1.0 equiv), 1-(difluoromethyl)-4-(1H-pyrazol-4-yl)-1H-1,2,3-triazole (206 mg, 1.11 mmol, 1.2 equiv) and Cs$_2$CO$_3$ (603 mg, 1.85 mmol, 2.0 equiv) in acetonitrile (5 mL) was stirred at 90° C. for 2 h. To the reaction mixture was added water, and the mixture extracted with ethyl acetate, the organic layer was washed with brine and dried over anhydrous Na$_2$SO$_4$. Concentrated and purified by silica gel chromatography (0→40% EA/PE) to yield 5-bromo-2-(1-(4-(1-(difluoromethyl)-1H-1,2,3-triazol-4-yl)-1H-pyrazol-1-yl)-3-methoxypropyl)pyridine as a yellow solid. LC/MS: mass calculated for C$_{15}$H$_{15}$BrF$_2$N$_6$O: 412.05, measured (ES, m/z): 413.23 [M+H]$^+$.

Step 2: 4-Chloro-2-(6-(1-(4-(1-(difluoromethyl)-1H-1,2,3-triazol-4-yl)-1H-pyrazol-1-yl)-3-methoxypropyl)pyridin-3-yl)-3-fluoroaniline The mixture of 5-bromo-2-(1-(4-(1-(difluoromethyl)-1H-1,2,3-triazol-4-yl)-1H-pyrazol-1-yl)-3-methoxypropyl)pyridine (400 mg, 0.97 mmol, 1.0 equiv), (6-amino-3-chloro-2-fluorophenyl)boronic acid (367 mg, 1.94 mmol, 2.0 equiv), K$_2$CO$_3$ (669 mg, 4.84 mmol, 5.0 equiv) and Pd(PPh$_3$)$_4$ (112 mg, 0.10 mmol, 0.1 equiv) in 1,4-dioxane (4 mL) and water (1 mL) was stirred at 90° C. under N$_2$ overnight. To the reaction mixture was added water and the mixture extracted with ethyl acetate, the organic layer was washed with brine and dried over anhydrous Na$_2$SO$_4$. The mixture was then concentrated and purified by silica gel chromatography (0→40% EA/PE) to yield 4-chloro-2-(6-(1-(4-(1-(difluoromethyl)-1H-1,2,3-triazol-4-yl)-1H-pyrazol-1-yl)-3-methoxypropyl)pyridin-3-yl)-3-fluoroaniline as a yellow solid. LC/MS: mass calculated for C$_{21}$H$_{19}$ClF$_3$N$_7$O: 477.13, measured (ES, m/z): 478.13 [M+H]$^+$.

Step 3: 5-(3-Chloro-2-fluoro-6-(1H-tetrazol-1-yl)phenyl)-2-(1-(4-(1-(difluoromethyl)-1H-1,2,3-triazol-4-yl)-1H-pyrazol-1-yl)-3-methoxypropyl)pyridine The mixture of 4-chloro-2-(6-(1-(4-(1-(difluoromethyl)-1H-1,2,3-triazol-4-yl)-1H-pyrazol-1-yl)-3-methoxypropyl)pyridin-3-yl)-3-fluoroaniline (400 mg, 0.84 mmol, 1.0 equiv), azidotrimethylsilane (2 mL) and trimethoxymethane (2 mL) in acetic acid (3 mL) was stirred at room temperature overnight. The reaction was concentrated and purified by reverse phase chromatography on C18 (80 g, MeCN/H$_2$O (0.05% CF$_3$COOH): 0→55%) to yield 5-(3-chloro-2-fluoro-6-(1H-tetrazol-1-yl)phenyl)-2-(1-(4-(1-(difluoromethyl)-1H-1,2,3-triazol-4-yl)-1H-pyrazol-1-yl)-3-methoxypropyl)pyridine as a yellow solid. LC/MS: mass calculated for C$_{22}$H$_{18}$ClF$_3$N$_{10}$O: 530.13, measured (ES, m/z): 531.13 [M+H]$^+$.

Step 4: (S*)-5-(3-Chloro-2-fluoro-6-(1H-tetrazol-1-yl)phenyl)-2-(1-(4-(1-(difluoromethyl)-1H-1,2,3-triazol-4-yl)-1H-pyrazol-1-yl)-3-methoxypropyl)pyridine 1-oxide The mixture of 5-(3-chloro-2-fluoro-6-(1H-tetrazol-1-yl)phenyl)-2-(1-(4-(1-(difluoromethyl)-1H-1,2,3-triazol-4-yl)-1H-pyrazol-1-yl)-3-methoxypropyl)pyridine (120 mg, 0.23 mmol, 1.0 equiv), methyltrioxorhenium (28 mg, 0.11 mmol, 0.5 equiv) and hydrogen peroxide (128 mg, 1.13 mmol, 5.0 equiv, 30%) in CH$_3$OH (2 mL) was stirred at room temperature for 2 h. The reaction was purified by reverse phase chromatography on C18 (80 g, MeCN/H$_2$O (0.05% CF$_3$COOH): 0→55%) to yield 5-(3-chloro-2-fluoro-6-(1H-tetrazol-1-yl)phenyl)-2-(1-(4-(1-(difluoromethyl)-1H-1,2,3-triazol-4-yl)-1H-pyrazol-1-yl)-3-methoxypropyl)pyridine 1-oxide. The compound of 5-(3-chloro-2-fluoro-6-(1H-tetrazol-1-yl)phenyl)-2-(1-(4-(1-(difluoromethyl)-1H-1,2,3-triazol-4-yl)-1H-pyrazol-1-yl)-3-methoxypropyl)pyridine 1-oxide was separated by Prep-Chiral-HPLC to yield (R)-5-(3-chloro-2-fluoro-6-(1H-tetrazol-1-yl)phenyl)-2-(1-(4-(1-(difluoromethyl)-1H-1,2,3-triazol-4-yl)-1H-pyrazol-1-yl)-3-methoxypropyl)pyridine 1-oxide as a white solid.

LC/MS: mass calculated for C$_{22}$H$_{18}$ClF$_3$N$_{10}$O$_2$ (ES, m/z): 546.13, measured (ES, m/z): 547.05 [M+H]$^+$. $^1$H NMR (300 MHz, DMSO-d$_6$) δ 9.69 (s, 1H), 8.90 (s, 1H), 8.43-8.45 (m, 2H), 8.30 (t, J=57.0 Hz, 1H), 8.00-8.13 (m, 2H), 7.76 (d, J=8.7 Hz, 1H), 7.31 (d, J=8.3 Hz, 1H), 7.17 (d, J=8.3 Hz, 1H), 6.19 (t, J=7.3 Hz, 1H), 3.26-3.34 (m, 1H), 3.14-3.20 (m, 4H), 2.46-2.49 (m, 2H). $^{19}$F NMR (282 MHz, DMSO-d$_6$) δ −96.23, −112.70.

Example 726: (S)-5-(3-Chloro-2-fluoro-6-(1H-tetra-zol-1-yl)phenyl)-2-(1-(4-(1-(difluoromethyl)-1H-1,2,3-triazol-4-yl)-1H-pyrazol-1-yl)-3-methoxypropyl)pyridine 1-oxide

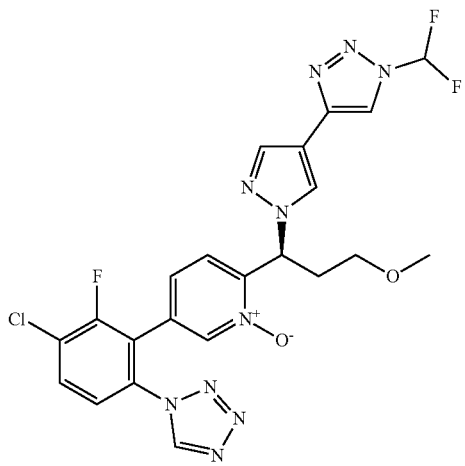 [SMILES: COCC[C@@H](c1ccc(-c2c(-n3cnnn3)ccc(Cl)c2F)c[n+]1[O-])n1cc(-c2cn(C(F)F)nn2)cn1]

LC/MS: mass calculated for $C_{22}H_{18}ClF_3N_{10}O_2$: 546.13, measured (ES, m/z): 547.05 [M+H]$^+$. $^1$H NMR (300 MHz, DMSO-d$_6$) δ 9.69 (s, 1H), 8.90 (s, 1H), 8.28-8.51 (m, 3H), 7.99-8.13 (m, 2H), 7.72-7.88 (m, 1H), 7.29-7.40 (m, 1H), 7.12-7.22 (m, 1H), 6.19 (t, J=7.3 Hz, 1H), 3.28-3.30 (m, 1H), 3.19-3.21 (m, 4H), 2.49-2.51 (m, 2H). $^{19}$F NMR (282 MHz, DMSO-d$_6$) δ −96.23, −112.70.

Example 727: (R)-5-(3-Chloro-2-fluoro-6-(1H-tetra-zol-1-yl)phenyl)-2-(1-(4-(2-(difluoromethyl)-2H-1,2,3-triazol-4-yl)-1H-pyrazol-1-yl)-3-methoxypropyl)pyridine 1-oxide

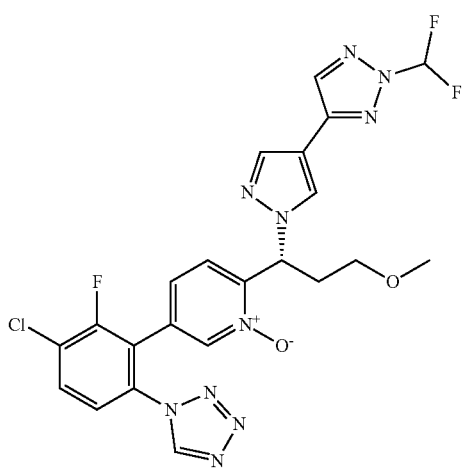 [SMILES: COCC[C@H](c1ccc(-c2c(-n3cnnn3)ccc(Cl)c2F)c[n+]1[O-])n1cc(-c2cnn(C(F)F)n2)cn1]

Step 1: 5-Bromo-2-(1-(4-(2-(difluoromethyl)-2H-1,2,3-triazol-4-yl)-1H-pyrazol-1-yl)-3-methoxypropyl)pyridine The mixture of 1-(5-bromopyridin-2-yl)-3-methoxypropyl methanesulfonate (260 mg, 0.80 mmol, 1.0 equiv), 2-(difluoromethyl)-4-(1H-pyrazol-4-yl)-2H-1,2,3-triazole (178 mg, 0.96 mmol, 1.2 equiv) and Cs$_2$CO$_3$ (523 mg, 1.60 mmol, 2.0 equiv) in acetonitrile (5 mL) was stirred at 90° C. for 2 h. To the reaction mixture was added water, and the mixture extracted with ethyl acetate, the organic layer was washed with brine and dried over anhydrous Na$_2$SO$_4$. The resulting mixture was concentrated and purified by silica gel chromatography (0→40% EA/PE) to yield 5-bromo-2-(1-(4-(2-(difluoromethyl)-2H-1,2,3-triazol-4-yl)-1H-pyrazol-1-yl)-3-methoxypropyl)pyridine as a yellow solid. LC/MS: mass calculated for $C_{15}H_{15}BrF_2N_6O$: 412.05, measured (ES, m/z): 413.23 [M+H]$^+$.

Step 2: 4-Chloro-2-(6-(1-(4-(2-(difluoromethyl)-2H-1,2,3-triazol-4-yl)-1H-pyrazol-1-yl)-3-methoxypropyl)pyridin-3-yl)-3-fluoroaniline The mixture of 5-bromo-2-(1-(4-(2-(difluoromethyl)-2H-1,2,3-triazol-4-yl)-1H-pyrazol-1-yl)-3-methoxypropyl)pyridine (150 mg, 0.36 mmol, 1.0 equiv), (6-amino-3-chloro-2-fluorophenyl)boronic acid (137 mg, 0.73 mmol, 2.0 equiv), K$_2$CO$_3$ (251 mg, 1.82 mmol, 5.0 equiv) and Pd(PPh$_3$)$_4$ (42 mg, 0.04 mmol, 0.1 equiv) in 1,4-dioxane (4 mL) and water (1 mL) was stirred at 90° C. under N$_2$ overnight. To the reaction mixture was added water and then extracted with ethyl acetate, the organic layer was washed with brine and dried over anhydrous Na$_2$SO$_4$. The resulting mixture was concentrated and purified by silica gel chromatography (0→40% EA/PE) to yield 4-chloro-2-(6-(1-(4-(2-(difluoromethyl)-2H-1,2,3-triazol-4-yl)-1H-pyrazol-1-yl)-3-methoxypropyl)pyridin-3-yl)-3-fluoroaniline as a yellow solid. LC/MS: mass calculated for $C_{21}H_{19}ClF_3N_7O$: 477.13, measured (ES, m/z): 478.13 [M+H]$^+$.

Step 3: 5-(3-Chloro-2-fluoro-6-(1H-tetrazol-1-yl)phenyl)-2-(1-(4-(2-(difluoromethyl)-2H-1,2,3-triazol-4-yl)-1H-pyrazol-1-yl)-3-methoxypropyl)pyridine The mixture of 4-chloro-2-(6-(1-(4-(2-(difluoromethyl)-2H-1,2,3-triazol-4-yl)-1H-pyrazol-1-yl)-3-methoxypropyl)pyridin-3-yl)-3-fluoroaniline (180 mg, 0.38 mmol, 1.0 equiv), azidotrimethylsilane (2 mL) and trimethoxymethane (2 mL) in acetic acid (3 mL) was stirred at room temperature overnight. The reaction was concentrated and purified by reverse phase chromatography on C18 (80 g, MeCN/H$_2$O (0.05% CF$_3$COOH): 0→50%) to yield 5-(3-chloro-2-fluoro-6-(1H-tetrazol-1-yl)phenyl)-2-(1-(4-(2-(difluoromethyl)-2H-1,2,3-triazol-4-yl)-1H-pyrazol-1-yl)-3-methoxypropyl)pyridine as a yellow solid. LC/MS: mass calculated for $C_{22}H_{18}ClF_3N_{10}O$: 530.13, measured (ES, m/z): 531.13 [M+H]$^+$.

Step 4: (R)-5-(3-Chloro-2-fluoro-6-(1H-tetrazol-1-yl)phenyl)-2-(1-(4-(2-(difluoromethyl)-2H-1,2,3-triazol-4-yl)-1H-pyrazol-1-yl)-3-methoxypropyl)pyridine 1-oxide The mixture of 5-(3-chloro-2-fluoro-6-(1H-tetrazol-1-yl)phenyl)-2-(1-(4-(2-(difluoromethyl)-2H-1,2,3-triazol-4-yl)-

1H-pyrazol-1-yl)-3-methoxypropyl)pyridine (120 mg, 0.23 mmol, 1.0 equiv), methyltrioxorhenium (28 mg, 0.11 mmol, 0.5 equiv) and hydrogen peroxide (128 mg, 1.13 mmol, 5.0 equiv, 30%) in CH₃OH (2 mL) was stirred at room temperature for 2 h. The solution was purified by reverse phase chromatography on C18 (80 g, MeCN/H₂O (0.05% CF₃COOH): 0→55%) to yield 5-(3-chloro-2-fluoro-6-(1H-tetrazol-1-yl)phenyl)-2-(1-(4-(2-(difluoromethyl)-2H-1,2,3-triazol-4-yl)-1H-pyrazol-1-yl)-3-methoxypropyl)pyridine 1-oxide. The compound of 5-(3-chloro-2-fluoro-6-(1H-tetrazol-1-yl)phenyl)-2-(1-(4-(2-(difluoromethyl)-2H-1,2,3-triazol-4-yl)-1H-pyrazol-1-yl)-3-methoxypropyl)pyridine 1-oxide (80 mg) was separated by Prep-Chiral-HPLC to yield (R)-5-(3-chloro-2-fluoro-6-(1H-tetrazol-1-yl)phenyl)-2-(1-(4-(2-(difluoromethyl)-2H-1,2,3-triazol-4-yl)-1H-pyrazol-1-yl)-3-methoxypropyl)pyridine 1-oxide as a white solid.

LC/MS: mass calculated for $C_{22}H_{18}ClF_3N_{10}O_2$: 546.13, measured (ES, m/z): 547.05 [M+H]⁺. ¹H NMR (300 MHz, DMSO-$d_6$) δ 9.70 (s, 1H), 8.51 (s, 1H), 8.45 (s, 1H), 8.35 (t, J=57.0 Hz, 1H), 8.19 (s, 1H), 8.07 (t, J=8.2 Hz, 1H), 8.00 (s, 1H), 7.76 (d, J=8.7 Hz, 1H), 7.42 (d, J=8.3 Hz, 1H), 7.19 (d, J=8.3 Hz, 1H), 6.23 (t, J=7.3 Hz, 1H), 3.26-3.31 (m, 1H), 3.19 (s, 3H), 3.08-3.15 (m, 1H), 2.47-2.49 (m, 2H). ¹⁹F NMR (282 MHz, DMSO-$d_6$) δ −97.08, −97.11, −112.68.

Example 728: (R)-5-(3-Chloro-6-(4-chloro-1H-1,2,3-triazol-1-yl)-2-fluorophenyl)-2-(1-(4-(2-(difluoromethyl)-2H-1,2,3-triazol-4-yl)-1H-pyrazol-1-yl)-2-(1H-pyrazol-1-yl)ethyl)pyridine 1-oxide

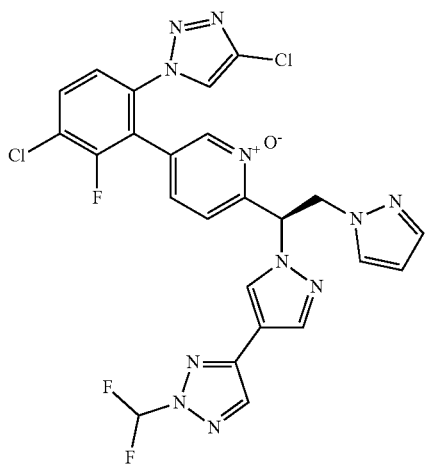

LC/MS: mass calculated for $C_{24}H_{16}Cl_2F_3N_{11}O$: 601.09, measured (ES, m/z): 601.95 [M+H]⁺. ¹H NMR (300 MHz, DMSO-$d_6$) δ 8.68 (s, 1H), 8.48-8.55 (m, 1H), 8.35-8.47 (m, 2H), 7.91-8.33 (m, 3H), 7.65-7.75 (m, 1H), 7.39-7.53 (m, 3H), 7.16-7.29 (m, 1H), 6.55-6.69 (m, 1H), 6.13 (t, J=2.1 Hz, 1H), 5.17-4.92 (m, 2H). ¹⁹F NMR (282 MHz, DMSO-$d_6$) δ −73.51, −96.72, −112.88.

Example 729: (R)-5-(3-Chloro-6-(4-chloro-1H-1,2,3-triazol-1-yl)-2-fluorophenyl)-2-(3-(difluoromethoxy)-1-(4-(4-(difluoromethyl)-4H-1,2,4-triazol-3-yl)-1H-pyrazol-1-yl)propyl)pyridine 1-oxide

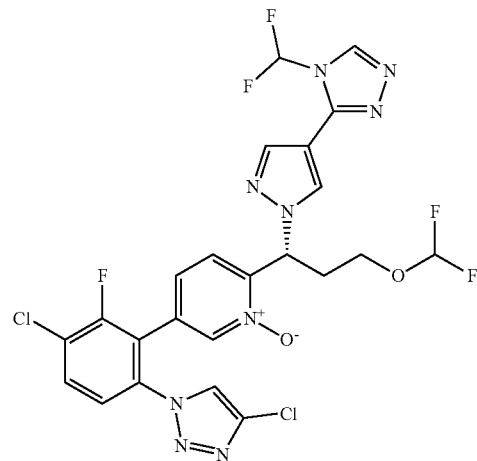 [SMILES: [O-][n+]1cc(-c2c(-n3cc(Cl)nn3)ccc(Cl)c2F)ccc1[C@@H](CCOC(F)F)n1cc(-c2nncn2C(F)F)cn1]

Step 1: 3-(1-(Tetrahydro-2H-pyran-2-yl)-1H-pyrazol-4-yl)-4H-1,2,4-triazole

To a solution of 3-bromo-4H-1,2,4-triazole (15.0 g 101.38 mmol, 1.0 equiv.) in 1,4-dioxane (100 mL) and H₂O (20 mL) was added 1-(tetrahydro-2H-pyran-2-yl)-4-(4,4,5,5-tetramethyl-1,3,2-dioxaborolan-2-yl)-1H-pyrazole (33.8 g, 121.65 mmol, 1.2 equiv.), K₂CO₃ (21.0 g, 152.07 mmol, 1.5 equiv.) and Pd(PPh₃)₄ (5.9 g, 5.07 mmol, 0.05 equiv.). The resulting mixture was maintained under nitrogen and stirred at 75° C. for 2 h.

After cooling to room temperature. The resulting residue was concentrated and purified by silica gel chromatography (0→10% MeOH/DCM) to yield 3-(1-(tetrahydro-2H-pyran-2-yl)-1H-pyrazol-4-yl)-4H-1,2,4-triazole as a white solid. LC/MS: mass calculated for $C_{10}H_{13}N_5O$: 219.11, measured (ES, m/z): 242.05 [M+Na]⁺.

Step 2: 4-(Difluoromethyl)-3-(1-(tetrahydro-2H-pyran-2-yl)-1H-pyrazol-4-yl)-4H-1,2,4-triazole To a solution of 3-(1-(tetrahydro-2H-pyran-2-yl)-1H-pyrazol-4-yl)-4H-1,2,4-triazole (3.4 g, 15.51 mmol, 1.0 equiv.) in DMF (405 mL) was added Cs₂CO₃ (7.6 g, 23.26 mmol, 1.5 equiv.) and sodium 2-chloro-2,2-difluoroacetate (2.8 g, 18.61 mmol, 1.2 equiv.) at 80° C. for 2 h. The reaction was quenched with water (150 mL). The resulting mixture was extracted with ethyl acetate (3×40 mL). The organic layers were combined, dried over anhydrous sodium sulfate, filtered and concentrated. The resulting residue was purified by reverse phase chromatography on C18 (330 g, 5%→60%, MeCN/H₂O) to yield 4-(difluoromethyl)-3-(1-(tetrahydro-2H-pyran-2-yl)-1H-pyrazol-4-yl)-4H-1,2,4-triazole as a yellow solid. LC/MS: mass calculated for $C_{11}H_{13}F_2N_5O$: 269.11, measured (ES, m/z): 270.05 [M+H]⁺.

Step 3: 4-(Difluoromethyl)-3-(1H-pyrazol-4-yl)-4H-1,2,4-triazole

To a solution of 4-(difluoromethyl)-3-(1-(tetrahydro-2H-pyran-2-yl)-1H-pyrazol-4-yl)-4H-1,2,4-triazole (259 mg, 0.96 mmol, 1.0 equiv.) in MeOH (4 mL) and HCl (2 mL) was stirred at room temperature for 2 h. The resulting mixture was concentrated to yield 4-(difluoromethyl)-3-(1H-pyrazol-4-yl)-4H-1,2,4-triazole as a yellow oil which was used in the next step without further purification. LC/MS: mass calculated for $C_6H_5F_2N_5$: 185.05, measured (ES, m/z): 186.05 [M+H]$^+$.

Step 4: 5-Bromo-2-(3-(difluoromethoxy)-1-(4-(4-(difluoromethyl)-4H-1,2,4-triazol-3-yl)-1H-pyrazol-1-yl)propyl)pyridine To a solution of 4-(difluoromethyl)-3-(1H-pyrazol-4-yl)-4H-1,2,4-triazole (230 mg, 1.24 mmol, 1.0 equiv.) in ACN (20 mL) was added Cs$_2$CO$_3$ (810 mg, 2.49 mmol, 2.0 equiv.) at room temperature. for 0.5 h.
To the resulting mixture was added 1-(5-bromopyridin-2-yl)-3-(difluoromethoxy)propyl methanesulfonate (492 mg, 1.37 mmol, 1.1 equiv.). The resulting mixture was stirred at 80° C. for 2 h. The reaction was quenched with water (60 mL). The resulting mixture was extracted with ethyl acetate (3×20 mL). The organic layers were combined, dried over anhydrous sodium sulfate, filtered and concentrated. The resulting residue was purified by silica gel chromatography (0→50% EA/PE) to yield 5-bromo-2-(3-(difluoromethoxy)-1-(4-(4-(difluoromethyl)-4H-1,2,4-triazol-3-yl)-1H-pyrazol-1-yl)propyl)pyridine as a light yellow oil. LC/MS: mass calculated for $C_{15}H_{13}BrF_4N_6O$: 448.03, measured (ES, m/z): 448.90, 450.90 [M+H, M+H+2]$^+$.

Step 5: (6-(3-(Difluoromethoxy)-1-(4-(4-(difluoromethyl)-4H-1,2,4-triazol-3-yl)-1H-pyrazol-1-yl)propyl)pyridin-3-yl)boronic acid To a solution of 5-bromo-2-(3-(difluoromethoxy)-1-(4-(4-(difluoromethyl)-4H-1,2,4-triazol-3-yl)-1H-pyrazol-1-yl)propyl)pyridine (239 mg, 0.53 mmol, 1.0 equiv.) in 1,4-dioxane (15 mL) was added 4,4,4',4',5,5,5',5'-octamethyl-2,2'-bi(1,3,2-dioxaborolane) (270 mg, 1.06 mmol, 2.0 equiv.), KOAc (157 mg, 1.60 mmol, 3.0 equiv.) and Pd(dppf)Cl$_2$ (45 mg, 0.05 mmol, 0.1 equiv.). The resulting mixture was maintained under nitrogen and stirred at 90° C. for 2 h. After cooling to room temperature, the reaction was quenched with water (50 mL). The resulting mixture was extracted with ethyl acetate (3×20 mL), filtered and concentrated to yield (6-(3-(difluoromethoxy)-1-(4-(4-(difluoromethyl)-4H-1,2,4-triazol-3-yl)-1H-pyrazol-1-yl)propyl)pyridin-3-yl)boronic acid as a black oil for resulting. LC/MS: mass calculated for $C_{15}H_{15}BF_4N_6O_3$: 414.12, measured (ES, m/z): 415.00 [M+H]$^+$.

Step 6: 5-(3-Chloro-6-(4-chloro-1H-1,2,3-triazol-1-yl)-2-fluorophenyl)-2-(3-(difluoromethoxy)-1-(4-(4-(difluoromethyl)-4H-1,2,4-triazol-3-yl)-1H-pyrazol-1-yl)propyl)pyridine To a solution of (6-(3-(difluoromethoxy)-1-(4-(4-(difluoromethyl)-4H-1,2,4-triazol-3-yl)-1H-pyrazol-1-yl)propyl)pyridin-3-yl)boronic acid (250 mg, resulting) in 1,4-dioxane (20 mL) and H$_2$O (2 mL) was added 4-chloro-1-(4-chloro-3-fluoro-2-iodophenyl)-1H-1,2,3-triazole (432 mg, 1.21 mmol), K$_2$CO$_3$ (250 mg, 1.81 mmol) and Pd(PPh$_3$)$_4$ (69.76 mg, 0.06 mmol). The resulting mixture was maintained under nitrogen and stirred at 75° C. for 2 h. After cooling to room temperature, the reaction was quenched with water (50 mL). The resulting mixture was extracted with ethyl acetate (3×20 mL). The organic layers were combined, dried over anhydrous sodium sulfate, filtered and concentrated. The resulting residue was purified by silica gel chromatography (0→5% MeOH/DCM) to yield 5-(3-chloro-6-(4-chloro-1H-1,2,3-triazol-1-yl)-2-fluorophenyl)-2-(3-(difluoromethoxy)-1-(4-(4-(difluoromethyl)-4H-1,2,4-triazol-3-yl)-1H-pyrazol-1-yl)propyl)pyridine as a brown solid. LC/MS: mass calculated for $C_{23}H_{16}Cl_2F_5N_9O$: 599.08, measured (ES, m/z): 600.00 [M+H]$^+$.

Step 7: (R)-5-(3-Chloro-6-(4-chloro-1H-1,2,3-triazol-1-yl)-2-fluorophenyl)-2-(3-(difluoromethoxy)-1-(4-(4-(difluoromethyl)-4H-1,2,4-triazol-3-yl)-1H-pyrazol-1-yl)propyl)pyridine 1-oxide To a solution of 5-(3-chloro-6-(4-chloro-1H-1,2,3-triazol-1-yl)-2-fluorophenyl)-2-(3-(difluoromethoxy)-1-(4-(4-(difluoromethyl)-4H-1,2,4-triazol-3-yl)-1H-pyrazol-1-yl)propyl)pyridine (100 mg, 0.17 mmol, 1.0 equiv.) in MeOH (4 mL) was added methyltrioxorhenium (21 mg, 0.08 mmol, 0.5 equiv.) and H$_2$O$_2$ (0.08 mL, 0.83 mmol, 5 equiv.). The resulting mixture was stirred at room temperature for 6 h. The mixture was then purified by reverse phase chromatography on C18 (80 g, 5%→55%, MeCN/H$_2$O) and Chiral HPLC to yield (R)-5-(3-chloro-6-(4-chloro-1H-1,2,3-triazol-1-yl)-2-fluorophenyl)-2-(3-(difluoromethoxy)-1-(4-(4-(difluoromethyl)-4H-1,2,4-triazol-3-yl)-1H-pyrazol-1-yl)propyl)pyridine 1-oxide as a white solid.
LC/MS: mass calculated for $C_{23}H_{16}Cl_2F_5N_9O_2$: 615.1, measured (ES, m/z): 616.0 [M+H]$^+$. $^1$H NMR (300 MHz, DMSO-d$_6$) δ 9.08 (s, 1H), 8.67 (s, 1H), 8.54 (s, 1H), 8.41 (s, 1H), 8.07 (s, 1H), 8.02 (d, J=8.7 Hz, 1H), 7.97 (t, J=57.0 Hz, 1H), 7.69 (d, J=8.7 Hz, 1H), 7.28 (d, J=8.3 Hz, 1H), 7.17 (d, J=8.3 Hz, 1H), 6.63 (t, J=78.0 Hz, 1H), 6.25 (dd, J=9.9, 4.6 Hz, 1H), 3.80-3.87 (m, 1H), 3.66-3.74 (m, 1H), 2.58-2.73 (m, 2H). $^{19}$F NMR (282 MHz, DMSO-d$_6$) δ −83.33, −96.94, −112.93.

Example 730: (S)-5-(3-Chloro-6-(4-chloro-1H-1,2,3-triazol-1-yl)-2-fluorophenyl)-2-(3-(difluoromethoxy)-1-(4-(4-(difluoromethyl)-4H-1,2,4-triazol-3-yl)-1H-pyrazol-1-yl)propyl)pyridine 1-oxide

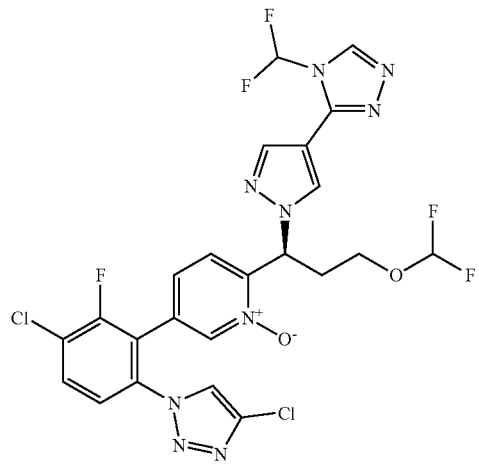 [SMILES: [O-][n+]1cc(-c2c(-n3cc(Cl)nn3)ccc(Cl)c2F)ccc1[C@H](CCOC(F)F)n1cc(-c2nncn2C(F)F)cn1]

LC/MS: mass calculated for $C_{23}H_{16}Cl_2F_5N_9O_2$: 615.1, measured (ES, m/z): 616.0 [M+H]$^+$. $^1$H NMR (300 MHz, DMSO-d$_6$) δ 9.08 (s, 1H), 8.67 (s, 1H), 8.51-8.58 (m, 1H), 8.37-8.45 (m, 1H), 7.74-8.21 (m, 3H), 7.65-7.72 (m, 1H), 7.25-7.32 (m, 1H), 7.13-7.23 (m, 1H), 6.63 (t, J=75.7 Hz, 1H), 6.20-6.31 (m, 1H), 3.77-3.88 (m, 1H), 3.64-3.77 (m, 1H), 2.55-2.80 (m, 2H). $^{19}$F NMR (282 MHz, DMSO-d$_6$) δ −83.33, −96.94, −112.93.

Example 731: 5-(3-Chloro-2-fluoro-6-(1H-tetrazol-1-yl)phenyl)-2-(2-(2-methyl-2H-1,2,3-triazol-4-yl)-1-(4-(2-(trifluoromethyl)pyridin-4-yl)-1H-pyrazol-1-yl)ethyl)pyridine 1-oxide

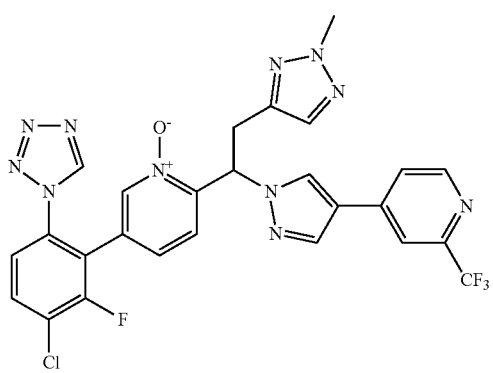 [SMILES: Cn1ncc(CC(c2ccc(-c3c(-n4cnnn4)ccc(Cl)c3F)c[n+]2[O-])n2cc(-c3ccnc(C(F)(F)F)c3)cn2)n1]

LC/MS: mass calculated for C$_{26}$H$_{18}$ClF$_4$N$_{11}$O: 611.1, measured (ES, m/z): 612.2 [M+H]+. $^1$H NMR (400 MHz, CD$_3$OD) δ ppm 3.66-3.92 (m, 1H), 4.06 (s, 1H), 5.51 (s, 1H), 6.48-6.55 (m, 2H), 7.19-7.43 (m, 2H), 7.48-7.70 (m, 1H), 7.71-7.77 (m, 1H), 7.77-7.84 (m, 1H), 7.87-7.97 (m, 1H), 7.97-8.01 (m, 2H), 8.20 (s, 1H), 8.33-8.46 (m, 1H), 8.50-8.56 (m, 1H), 8.59 (d, J=5.4 Hz, 1H), 9.38 (s, 1H).

Example 732: 5-(3-Chloro-2-fluoro-6-(1H-tetrazol-1-yl)phenyl)-2-(2-(1-methyl-1H-1,2,3-triazol-4-yl)-1-(4-(2-(trifluoromethyl)pyridin-4-yl)-1H-pyrazol-1-yl)ethyl)pyridine 1-oxide

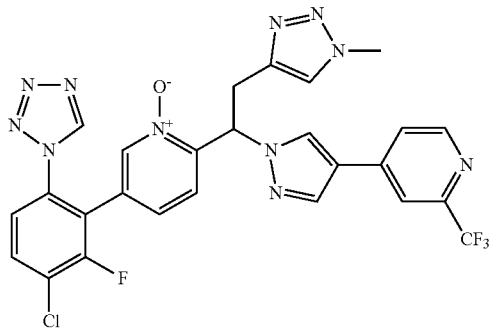 [SMILES: Cn1cc(CC(c2ccc(-c3c(-n4cnnn4)ccc(Cl)c3F)c[n+]2[O-])n2cc(-c3ccnc(C(F)(F)F)c3)cn2)nn1]

LC/MS: mass calculated for C$_{26}$H$_{18}$ClF$_4$N$_{11}$O: 611.1, measured (ES, m/z): 612.3 [M+H]+. $^1$H NMR (400 MHz, CD$_3$OD) δ ppm 3.73-3.96 (m, 2H), 4.02 (s, 3H), 6.43-6.62 (m, 1H), 7.24-7.33 (m, 2H), 7.52-7.58 (m, 1H), 7.61 (dd, J=8.8, 1.5 Hz, 1H), 7.76-7.86 (m, 1H), 7.86-7.97 (m, 1H), 8.00 (s, 1H), 8.11-8.29 (m, 1H), 8.29-8.48 (m, 1H), 8.51-8.56 (m, 1H), 8.59 (d, J=4.9 Hz, 1H), 9.32-9.44 (m, 1H).

Example 733: 5-(3-Chloro-2-fluoro-6-(1H-tetrazol-1-yl)phenyl)-2-(1-(2-(difluoromethyl)-1'H,2H-[3,4'-bipyrazol]-1'-yl)-2-(2-methyl-2H-1,2,3-triazol-4-yl)ethyl)pyridine 1-oxide

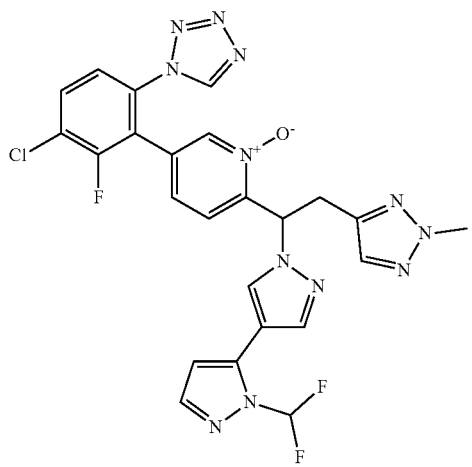 [SMILES: Cn1ncc(CC(c2ccc(-c3c(-n4cnnn4)ccc(Cl)c3F)c[n+]2[O-])n2cc(-c3ccnn3C(F)F)cn2)n1]

LC/MS: mass calculated for C$_{24}$H$_{18}$ClF$_3$N$_{12}$O: 582.1, measured (ES, m/z): 583.2 [M+H]+. $^1$H NMR (400 MHz, CD$_3$OD) δ 9.38 (s, 1H), 8.40 (s, 1H), 8.12 (s, 1H), 7.92 (s, 1H), 7.83 (s, 1H), 7.67 (d, J=1.47 Hz, 1H), 7.54-7.64 (m, 2H), 7.29 (s, 2H), 6.54 (d, J=1.47 Hz, 1H), 6.44-6.52 (m, 1H), 4.06 (s, 3H), 3.73-3.81 (m, 2H).

Example 734: 5-(3-Chloro-2-fluoro-6-(1H-tetrazol-1-yl)phenyl)-2-(1-(2-(difluoromethyl)-1'H,2H-[3,4'-bipyrazol]-1'-yl)-2-(2-phenyl-2H-1,2,3-triazol-4-yl)ethyl)pyridine 1-oxide

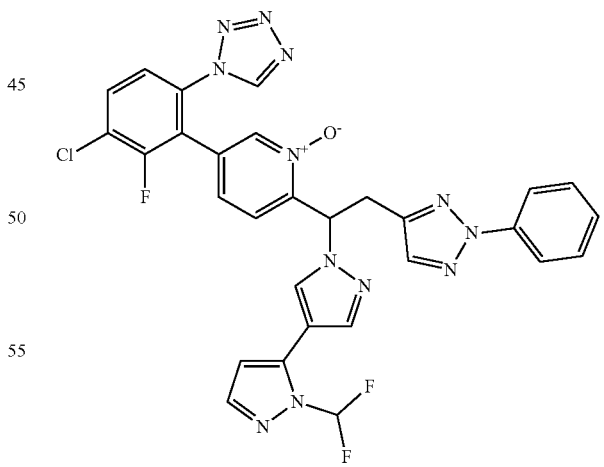

LC/MS calculated for C$_{29}$H$_{20}$ClF$_3$N$_{12}$O: 644.2, measured (ES, m/z): 645.3 [M+H]+. $^1$H NMR (400 MHz, CD$_3$OD) δ ppm 3.86-3.97 (m, 2 h) 6.51-6.53 (m, 1H) 6.56-6.61 (m, 1H) 7.29-7.37 (m, 2 h) 7.43-7.47 (m, 2 h) 7.56 (s, 1H) 7.58-7.67 (m, 3H) 7.86-7.88 (m, 1H) 7.90-7.96 (m, 3H) 8.17 (s, 1H) 8.43 (s, 1H) 9.39 (s, 1H).

Example 735: 5-(3-Chloro-2-fluoro-6-(1H-tetrazol-1-yl)phenyl)-2-(2-(2-phenyl-2H-1,2,3-triazol-4-yl)-1-(4-(2-(trifluoromethyl)pyridin-4-yl)-1H-pyrazol-1-yl)ethyl)pyridine 1-oxide

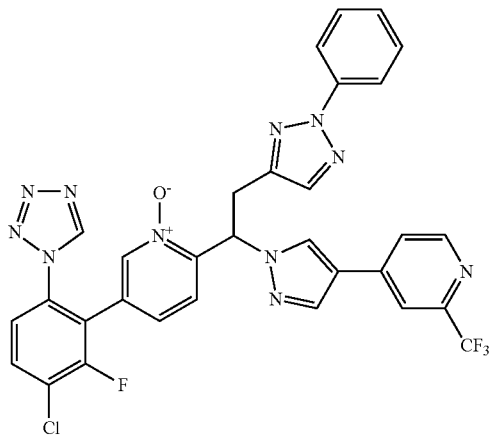 [SMILES: [O-][n+]1cc(-c2c(-n3cnnn3)ccc(Cl)c2F)ccc1C(Cc1cnn(-c2ccccc2)n1)n1cc(-c2ccnc(C(F)(F)F)c2)cn1]

LC/MS: mass calculated for $C_{31}H_{20}ClF_4N_{11}O$: 673.1, measured (ES, m/z): 674.1 [M+H]+. $^1$H NMR (400 MHz, CD$_3$OD) δ ppm 3.80-4.03 (m, 3H), 6.59 (dd, J=9.8, 5.4 Hz, 1H), 7.27-7.38 (m, 1H), 7.44 (t, J=8.1 Hz, 2H), 7.53-7.69 (m, 2H), 7.70-7.88 (m, 2H), 7.89-7.96 (m, 2H), 7.99 (s, 1H), 8.23 (s, 1H), 8.36-8.51 (m, 2H), 8.51-8.63 (m, 2H), 9.39 (s, 1H).

Example 736: (R)-5-(3-Chloro-2-fluoro-6-(1H-tetrazol-1-yl)phenyl)-2-(1-(4-(1-(difluoromethyl)-1H-1,2,3-triazol-4-yl)-1H-pyrazol-1-yl)-4,4,4-trifluorobutyl)pyridine 1-oxide

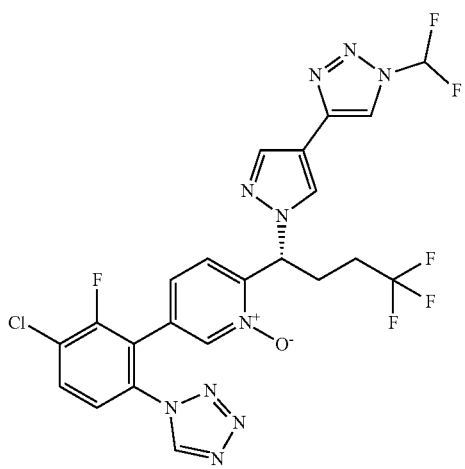 [SMILES: [O-][n+]1cc(-c2c(-n3cnnn3)ccc(Cl)c2F)ccc1[C@@H](CCC(F)(F)F)n1cc(-c2cn(C(F)F)nn2)cn1]

LC/MS: mass calculated for $C_{22}H_{15}ClF_6N_{10}O$: 584.10, measured (ES, m/z): 585.10 [M+H]+. $^1$H NMR (400 MHz, DMSO-d$_6$) δ 9.69 (s, 1H), 8.93 (s, 1H), 8.15-8.49 (m, 3H), 8.03-8.11 (m, 2H), 7.72-7.82 (m, 1H), 7.21-7.30 (m, 1H), 7.12-7.20 (m, 1H), 6.10-6.25 (m, 1H), 2.53-2.64 (m, 1H), 2.36-2.51 (m, 2H), 1.90-2.04 (m, 1H). $^{19}$F NMR (376 MHz, DMSO-d$_6$) δ −64.73, −64.73, −96.24, −112.68.

Example 737: (S)-5-(3-Chloro-2-fluoro-6-(1H-tetrazol-1-yl)phenyl)-2-(1-(4-(1-(difluoromethyl)-1H-1,2,3-triazol-4-yl)-1H-pyrazol-1-yl)-4,4,4-trifluorobutyl)pyridine 1-oxide

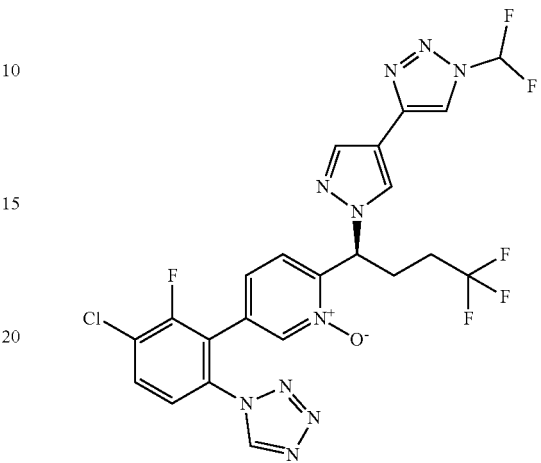

LC/MS: mass calculated for $C_{22}H_{15}ClF_6N_{10}O$: 584.10, measured (ES, m/z): 585.10 [M+H]+. $^1$H NMR (400 MHz, DMSO-d$_6$) δ 9.69 (s, 1H), 8.92 (s, 1H), 8.15-8.50 (m, 3H), 8.03-8.11 (m, 2H), 7.75-7.82 (m, 1H), 7.10-7.31 (m, 2H), 6.10-6.23 (m, 1H), 2.36-2.64 (m, 3H), 1.90-2.04 (m, 1H). $^{19}$F NMR (376 MHz, DMSO-d$_6$) δ −64.73, −64.82, −96.24, −112.68, −218.53.

Example 738: (S)-5-(3-Chloro-2-fluoro-6-(1H-tetrazol-1-yl)phenyl)-2-(3-(difluoromethoxy)-1-(4-(1-(difluoromethyl)-1H-1,2,4-triazol-5-yl)-1H-pyrazol-1-yl)propyl)pyridine 1-oxide

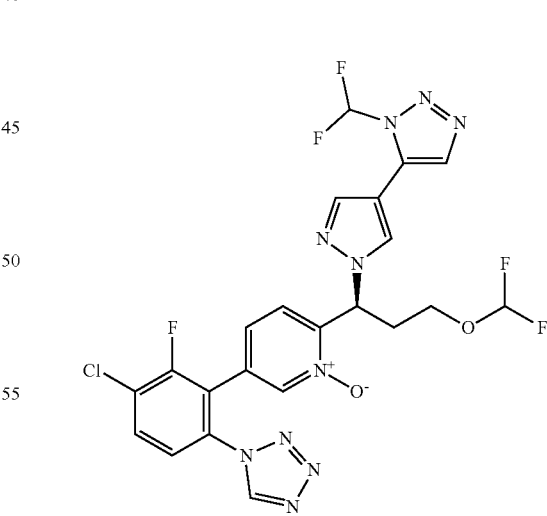

LC/MS: mass calculated for $C_{22}H_{16}ClF_5N_{10}O_2$: 582.11, measured (ES, m/z): 583.10 [M+H]+. $^1$H NMR (400 MHz, DMSO-d$_6$) δ 9.69 (s, 1H), 8.67 (s, 1H), 8.46 (s, 1H), 8.27 (s, 1H), 8.12 (s, 1H), 8.06 (t, J=56.0 Hz 1H), 8.04-8.10 (m, 1H), 7.76 (dd, J=8.7, 1.5 Hz, 1H), 7.38 (d, J=8.3 Hz, 1H), 7.21 (dd, J=8.3, 1.6 Hz, 1H), 6.63 (t, J=75.7 Hz, 1H), 6.25-6.31

(dd, J=10.1, 4.4 Hz, 1H), 3.81-3.88 (m, 1H), 3.68-3.75 (m, 1H), 2.57-2.73 (m, 2H). $^{19}$F NMR (376 MHz, DMSO-$d_6$) δ −83.35, −96.16, −112.65.

Example 739: (R)-5-(3-Chloro-2-fluoro-6-(1H-tetrazol-1-yl)phenyl)-2-(3-(difluoromethoxy)-1-(4-(1-(difluoromethyl)-1H-1,2,4-triazol-5-yl)-1H-pyrazol-1-ylpropyl)pyridine 1-oxide

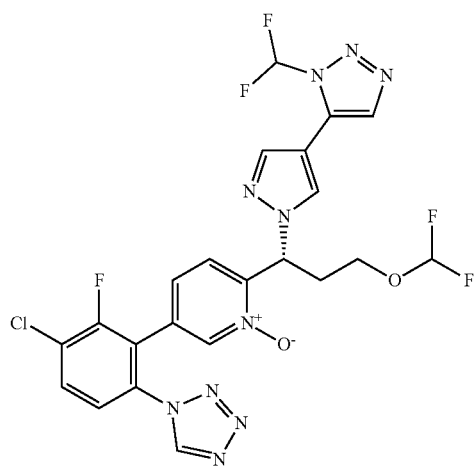 [SMILES: [O-][n+]1cc(-c2c(-n3cnnn3)ccc(Cl)c2F)ccc1[C@@H](CCOC(F)F)n1cc(-c2cnnn2C(F)F)cn1]

Step 1: 5-Bromo-2-(3-(difluoromethoxy)-1-(4-(1-(difluoromethyl)-1H-1,2,4-triazol-5-yl)-1H-pyrazol-1-yl)propyl)pyridine A mixture of 1-(5-bromopyridin-2-yl)-3-(difluoromethoxy)propyl methanesulfonate (283 mg, 0.79 mmol, 1.0 equiv.), 1-(difluoromethyl)-5-(1H-pyrazol-4-yl)-1H-1,2,4-triazole (160 mg, 0.86 mmol, 1.10 equiv.) and cesium carbonate (282 mg, 0.86 mmol, 1.1 equiv.) in acetonitrile (5 mL) was stirred at 90° C. for 4 h. The reaction was diluted with water, and the mixture extracted with ethyl acetate twice. The combined organic layers were washed with brine, dried over Na$_2$SO$_4$ and concentrated. The residue was purified by silica gel chromatography (0→10% MeOH/DCM) to yield 5-bromo-2-(3-(difluoromethoxy)-1-(4-(1-(difluoromethyl)-1H-1,2,4-triazol-5-yl)-1H-pyrazol-1-yl)propyl)pyridine as a light yellow solid. LC/MS: mass calculated for $C_{15}H_{13}BrF_4N_6O$: 448.03, measured (ES, m/z): 449.05, 451.05 [M+H, M+H+2]$^+$.

Step 2: 4-Chloro-2-(6-(3-(difluoromethoxy)-1-(4-(1-(difluoromethyl)-1H-1,2,4-triazol-5-yl)-1H-pyrazol-1-yl)propyl)pyridin-3-yl)-3-fluoroaniline To a mixture of 5-bromo-2-(3-(difluoromethoxy)-1-(4-(1-(difluoromethyl)-1H-1,2,4-triazol-5-yl)-1H-pyrazol-1-yl)propyl)pyridine (190 mg, 0.42 mmol, 1.0 equiv.), 6-amino-3-chloro-2-fluorophenylboronic acid (120 mg, 0.63 mmol, 1.5 equiv.) and potassium carbonate (175 mg, 1.27 mmol, 3.0 equiv.) in 1,4-dioxane (5 mL) and water (1 mL) was added tetrakis(triphenylphosphine)palladium(0) (49 mg, 0.04 mmol, 0.1 equiv.) and the mixture was stirred at 90° C. for 2 h. After cooling to room temperature, the reaction was quenched with water, and the mixture extracted with ethyl acetate twice. The combined organic layers were washed with brine, dried over anhydrous sodium sulfate and concentrated. The residue was purified silica gel chromatography (0→10% MeOH/DCM) to yield 4-chloro-2-(6-(3-(difluoromethoxy)-1-(4-(1-(difluoromethyl)-1H-1,2,4-triazol-5-yl)-1H-pyrazol-1-yl)propyl)pyridin-3-yl)-3-fluoroaniline as a light yellow solid. LC/MS: mass calculated for $C_{21}H_{17}ClF_5N_7O$: 513.11, measured (ES, m/z): 514.10 [M+H]$^+$.

Step 3: 5-(3-Chloro-2-fluoro-6-(1H-tetrazol-1-yl)phenyl)-2-(3-(difluoromethoxy)-1-(4-(1-(difluoromethyl)-1H-1,2,4-triazol-5-yl)-1H-pyrazol-1-yl)propyl)pyridine A mixture of 4-chloro-2-(6-(3-(difluoromethoxy)-1-(4-(1-(difluoromethyl)-1H-1,2,4-triazol-5-yl)-1H-pyrazol-1-yl)propyl)pyridin-3-yl)-3-fluoroaniline (200 mg, 0.39 mmol, 1.0 equiv.), azidotrimethylsilane (1 mL) and trimethoxymethane (1 mL) in acetic acid glacial (1 mL) was stirred at room temperature overnight. The mixture was concentrated and the residue was purified by reverse phase chromatography on C18 (80 g, MeCN/H$_2$O (0.05% CF$_3$COOH): 0→50%) to yield 5-(3-chloro-2-fluoro-6-(1H-tetrazol-1-yl)phenyl)-2-(3-(difluoromethoxy)-1-(4-(1-(difluoromethyl)-1H-1,2,4-triazol-5-yl)-1H-pyrazol-1-yl)propyl)pyridine as a light yellow solid. LC/MS: mass calculated for $C_{22}H_{16}ClF_5N_{10}O$: 566.11, measured (ES, m/z): 567.25 [M+H]$^+$.

Step 4: (R)-5-(3-Chloro-2-fluoro-6-(1H-tetrazol-1-yl)phenyl)-2-(3-(difluoromethoxy)-1-(4-(1-(difluoromethyl)-1H-1,2,4-triazol-5-yl)-1H-pyrazol-1-yl)propyl)pyridine 1-oxide To the mixture of 5-(3-chloro-2-fluoro-6-(1H-tetrazol-1-yl)phenyl)-2-(3-(difluoromethoxy)-1-(4-(1-(difluoromethyl)-1H-1,2,4-triazol-5-yl)-1H-pyrazol-1-yl)propyl)pyridine (180 mg, 0.32 mmol, 1.0 equiv.) in CH$_3$OH (2 mL) was added methyl trioxorhenium (VII) (40 mg, 0.16 mmol, 0.5 equiv.) and hydrogen peroxide (0.16 mL, 1.59 mmol, 30 wt %, 5.0 equiv.) and the solution was stirred at room temperature for 2 h. The solution was purified by reverse phase chromatography on C18 (80 g, MeCN/H$_2$O (0.05% CF$_3$COOH): 0→50%) and Prep-Chiral-HPLC to yield (R)-5-(3-chloro-2-fluoro-6-(1H-tetrazol-1-yl)phenyl)-2-(3-(difluoromethoxy)-1-(4-(1-(difluoromethyl)-1H-1,2,4-triazol-5-yl)-1H-pyrazol-1-yl)propyl)pyridine 1-oxide as a white solid.

LC/MS: mass calculated for $C_{22}H_{16}ClF_5N_{10}O_2$: 582.1, measured (ES, m/z): 583.1 [M+H]$^+$. $^1$H NMR (400 MHz, DMSO-$d_6$)): δ 9.69 (s, 1H), 8.67 (s, 1H), 8.46 (d, J=1.6 Hz, 1H), 8.27 (s, 1H), 7.89-8.22 (m, 3H), 7.72-7.78 (m, 1H), 7.38 (d, J=8.3 Hz, 1H), 7.19-7.23 (m, 1H), 6.62 (t, J=75.7 Hz, 1H), 6.25-6.28 (m, 1H), 3.81-3.89 (m, 1H), 3.67-3.76 (m, 1H), 2.59-2.72 (m, 2H). $^{19}$F-NMR (376 MHz, DMSO-$d_6$)): 6-83.34, −96.16, −112.64.

Example 740: 5-(3-Chloro-2-fluoro-6-(1H-tetrazol-1-yl)phenyl)-2-(2-(1-(difluoromethyl)-1H-pyrazol-3-yl)-1-(4-(2-(trifluoromethyl)pyridin-4-yl)-1H-pyrazol-1-yl)ethyl)pyridine 1-oxide

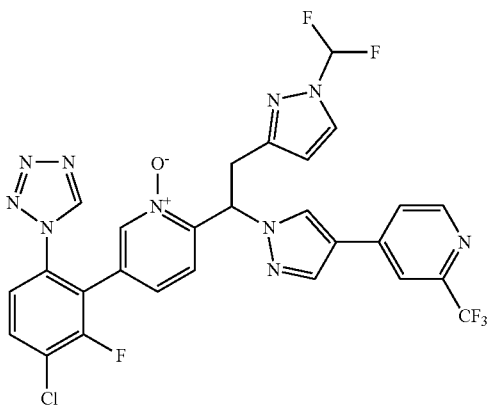 [SMILES: [O-][n+]1cc(-c2c(-n3cnnn3)ccc(Cl)c2F)ccc1C(Cc1ccn(C(F)F)n1)n1cc(-c2ccnc(C(F)(F)F)c2)cn1]

LC/MS: mass calculated for $C_{27}H_{17}ClF_6N_{10}O$: 646.1, measured (ES, m/z): 647.2 [M+H]+. $^1$H NMR (400 MHz, CD$_3$OD) δ ppm 3.72-3.85 (m, 3H), 6.21 (d, J=2.9 Hz, 1H), 6.51-6.62 (m, 1H), 7.15-7.26 (m, 1H), 7.26-7.33 (m, 1H), 7.36 (s, 1H), 7.47-7.54 (m, 1H), 7.54-7.66 (m, 1H), 7.79 (d, J=5.4 Hz, 1H), 7.84-7.95 (m, 1H), 7.98 (s, 1H), 8.18 (s, 1H), 8.31-8.47 (m, 1H), 8.52-8.56 (m, 1H), 8.59 (d, J=5.4 Hz, 1H), 9.38 (s, 1H).

Example 741: (R)-5-(3-Chloro-2-fluoro-6-(1H-tetrazol-1-yl)phenyl)-2-(2-(2-methyl-2H-1,2,3-triazol-4-yl)-1-(4-(2-(trifluoromethyl)pyridin-4-yl)-1H-pyrazol-1-yl)ethyl)pyridine 1-oxide

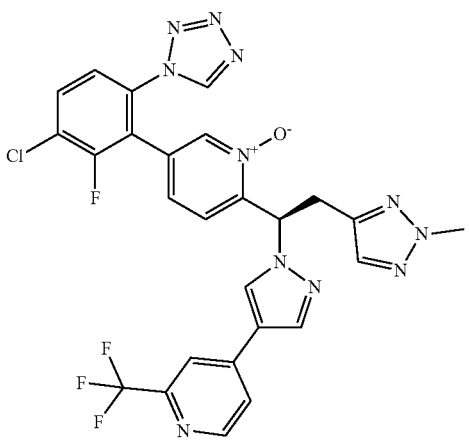 [SMILES: Cn1ncc(C[C@H](c2ccc(-c3c(-n4cnnn4)ccc(Cl)c3F)c[n+]2[O-])n2cc(-c3ccnc(C(F)(F)F)c3)cn2)n1]

LC/MS: mass calculated for $C_{2H}H_{18}ClF_4N_{11}O$: 611.13, measured (ES, m/z): 612.10 [M+H]$^+$. $^1$H NMR (400 MHz, DMSO-d$_6$) δ 9.64 (s, 1H), 8.78 (s, 1H), 8.65 (d, J=5.2 Hz, 1H), 8.42-8.48 (m, 1H), 8.31 (s, 1H), 8.09-8.12 (m, 1H), 8.00-8.08 (m, 1H), 7.85-7.93 (m, 1H), 7.70-7.80 (m, 1H), 7.40 (d, J=8.3 Hz, 1H), 7.33 (s, 1H), 7.16-7.25 (m, 1H), 6.30-6.42 (m, 1H), 4.02 (s, 3H), 3.66-3.71 (m, 2H). $^{19}$F NMR (376 MHz, DMSO-de) δ −66.54, −73.63, −112.77.

Example 742: (R)-5-(3-Chloro-6-(4-chloro-1H-1,2,3-triazol-1-yl)-2-fluorophenyl)-2-(3-(difluoromethoxy)-1-(4-(5-fluoro-1-methyl-1H-1,2,3-triazol-4-yl)-1H-pyrazol-1-yl)propyl)pyridine 1-oxide

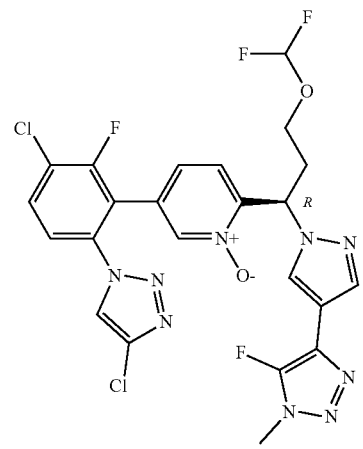

LC/MS: mass calculated for $C_{23}H_{17}Cl_2F_4N_9O_2$: 597.08, measured (ES, m/z): 620.00 [M+Na]$^+$. $^1$H NMR (400 MHz, DMSO-d$_6$) δ 8.68 (s, 1H), 8.41 (d, J=1.6 Hz, 1H), 8.34 (s, 1H), 8.03 (dd, J=8.7, 7.8 Hz, 1H), 7.91 (s, 1H), 7.69 (dd, J=8.7, 1.5 Hz, 1H), 7.26 (d, J=8.3 Hz, 1H), 7.17 (dd, J=8.4, 1.7 Hz, 1H), 6.64 (t, 75.7 Hz, 1H), 6.25 (dd, J=10.1, 4.4 Hz, 1H), 3.97 (s, 3H), 3.83 (ddd, J=10.6, 6.2, 4.7 Hz, 1H), 3.70 (ddd, J=10.1, 8.3, 5.6 Hz, 1H), 2.73-2.56 (m, 2H)./19F NMR (376 MHz, DMSO-d$_6$) d −83.34, −112.93, −153.61, −218.51.

Example 743: (S)-5-(3-Chloro-6-(4-chloro-1H-1,2,3-triazol-1-yl)-2-fluorophenyl)-2-(3-(difluoromethoxy)-1-(4-(5-fluoro-1-methyl-1H-1,2,3-triazol-4-yl)-1H-pyrazol-1-yl)propyl)pyridine 1-oxide

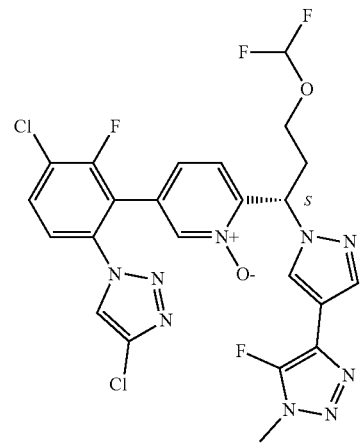

LC/MS: mass calculated for $C_{23}H_{17}Cl_2F_4N_9O_2$: 597.08, measured (ES, m/z): 620.00 [M+Na]$^+$. $^1$H NMR (400 MHz, DMSO-d$_6$) δ 8.68 (s, 1H), 8.41 (d, J=1.6 Hz, 1H), 8.34 (s, 1H), 8.03 (t, J=8.2 Hz, 1H), 7.91 (s, 1H), 7.65-7.75 (m, 1H), 7.21-7.28 (m, 1H), 7.12-7.18 (m, 1H), 6.64 (t, J=75.7 Hz, 1H), 6.17-6.30 (m, 1H), 3.97 (s, 3H), 3.78-3.90 (m, 1H), 3.65-3.75 (m, 1H), 2.52-2.71 (m, 2H). $^{19}$F NMR (376 MHz, DMSO-d$_6$) δ −83.34, −83.36, −112.93, −153.61.

Example 744: (S)-5-(3-Chloro-2-fluoro-6-(1H-tetrazol-1-yl)phenyl)-2-(2-(2-methyl-2H-1,2,3-triazol-4-yl)-1-(4-(2-(trifluoromethyl)pyridin-4-yl)-1H-pyrazol-1-yl)ethyl)pyridine 1-oxide

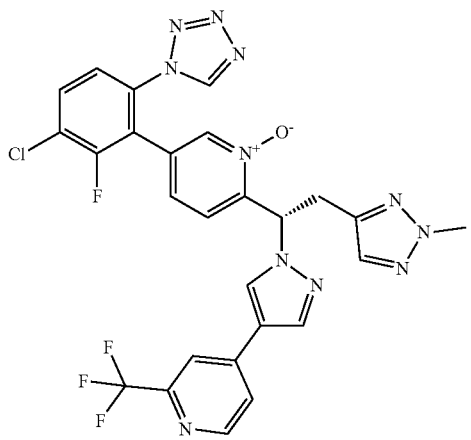 [SMILES: Cn1ncc(C[C@@H](c2ccc(-c3c(-n4cnnn4)ccc(Cl)c3F)c[n+]2[O-])n2cc(-c3ccnc(C(F)(F)F)c3)cn2)n1]

LC/MS: mass calculated for C$_{2H}$H$_{18}$ClF$_4$N$_{11}$O: 611.13, measured (ES, m/z): 612.10 [M+H]$^+$. $^1$H NMR (400 MHz, DMSO-d$_6$) δ 9.69 (s, 1H), 8.85 (s, 1H), 8.68 (d, J=5.2 Hz, 1H), 8.46-8.52 (m, 1H), 8.35 (s, 1H), 8.02-8.13 (m, 2H), 7.85-7.95 (m, 1H), 7.70-7.82 (m, 1H), 7.39 (d, J=8.3 Hz, 1H), 7.33 (s, 1H), 7.16-7.23 (m, 1H), 6.30-6.40 (m, 1H), 4.04 (s, 3H), 3.60-3.73 (m, 2H) $^{19}$F NMR (376 MHz, DMSO-d$_6$) δ −66.53, −112.67.

Example 745: 5-(3-Chloro-2-fluoro-6-(1H-tetrazol-1-yl)phenyl)-2-(2-cyclopropyl-1-(1'-(trifluoromethyl)-1H,1'H-[4,4'-bipyrazol]-1-yl)ethyl)pyridine 1-oxide

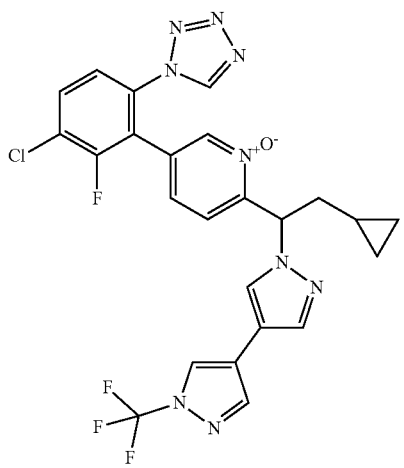

LC/MS: mass calculated for C$_{24}$H$_{18}$ClF$_4$N$_9$O: 599.1, measured 600.2 [M+H]$^+$. $^1$H NMR (400 MHz, METHANOL-d4) δ 9.35-9.42 (m, 1H), 8.42 (s, 1H), 8.35-8.38 (m, 1H), 8.20-8.24 (m, 1H), 8.05-8.09 (m, 1H), 7.90-7.95 (m, 1H), 7.85-7.89 (m, 1H), 7.60 (dd, J=1.47, 8.80 Hz, 1H), 7.41 (d, J=8.31 Hz, 1H), 7.27 (dd, J=1.47, 8.31 Hz, 1H), 6.17-6.24 (m, 1H), 2.41-2.53 (m, 1H), 1.90-2.01 (m, 1H), 0.65-0.74 (m, 1H), 0.36-0.47 (m, 2H), 0.17-0.25 (m, 1H), 0.03-0.10 (m, 1H).

Example 746: 5-(3-Chloro-2-fluoro-6-(1H-tetrazol-1-yl)phenyl)-2-(2-cyclopropyl-1-(1'-(difluoromethyl)-3'-hydroxy-1H,1'H-[4,4'-bipyrazol]-1-yl)ethyl)pyridine 1-oxide

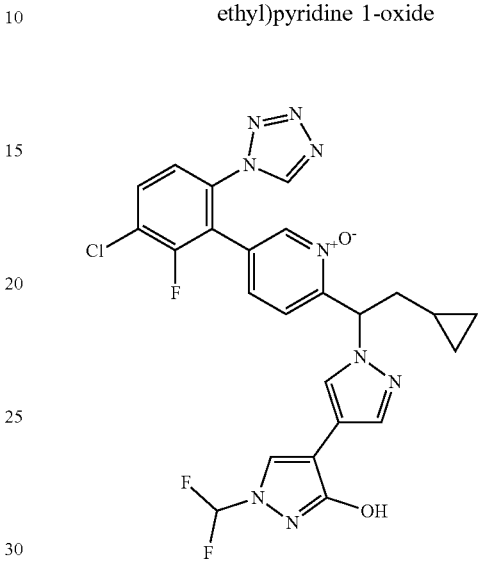

LC/MS: mass calculated for C$_{24}$H$_{19}$ClF$_3$N$_9$O$_2$: 557.1, measured (ES, m/z): 558.2 [M+H]$^+$. $^1$H NMR (400 MHz, CD$_3$OD) Shift 9.40 (s, 1H), 8.42 (s, 1H), 8.19 (s, 1H), 7.92 (dd, J=7.83, 8.80 Hz, 1H), 7.88 (s, 1H), 7.78 (s, 1H), 7.70 (d, J=8.31 Hz, 1H), 7.50 (s, 2H), 7.31-7.35 (m, 1H), 5.99 (dd, J=3.91, 10.27 Hz, 1H), 1.90-2.08 (m, 2H), 0.58-0.68 (m, 1H), 0.36 (br d, J=4.40 Hz, 1H), 0.19-0.27 (m, 1H), 0.07-0.15 (m, 1H), −0.02-0.01 (m, 1H).

Example 747: (S)-5-(3-Chloro-2-fluoro-6-(1H-tetrazol-1-yl)phenyl)-2-(2-(1-(2,2,2-trifluoroethyl)-1H-pyrazol-3-yl)-1-(4-(2-(trifluoromethyl)pyridin-4-yl)-1H-pyrazol-1-yl)ethyl)pyridine 1-oxide

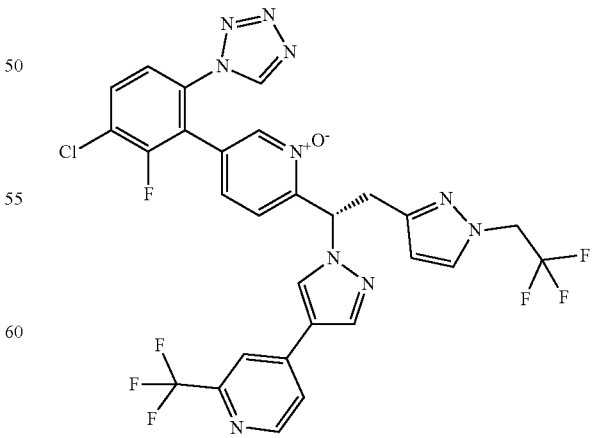

LC/MS: mass calculated for C$_{28}$H$_{18}$ClF$_7$N$_{10}$O: 678.12, measured (ES, m/z): 679.10 [M+H]$^+$. $^1$H NMR (400 MHz, DMSO-d$_6$) δ 9.69 (s, 1H), 8.79 (s, 1H), 8.67 (d, J=5.2 Hz, 1H), 8.47 (d, J=1.6 Hz, 1H), 8.32 (s, 1H), 8.03-8.11 (m, 2H), 7.85-7.90 (m, 1H), 7.72-7.81 (m, 1H), 7.66 (d, J=2.3 Hz, 1H), 7.41 (d, J=8.3 Hz, 1H), 7.15-7.22 (m, 1H), 6.30-6.40 (m, 1H), 5.97 (d, J=2.3 Hz, 1H), 4.90-5.10 (m, 2H), 3.52-3.64 (m, 2H) $^{19}$F NMR (376 MHz, DMSO-d$_6$) δ −66.57, −70.40, −112.68.

Example 748: (R)-5-(3-Chloro-2-fluoro-6-(1H-tetrazol-1-yl)phenyl)-2-(2-(1-(2,2,2-trifluoroethyl)-1H-pyrazol-3-yl)-1-(4-(2-(trifluoromethyl)pyridin-4-yl)-1H-pyrazol-1-yl)ethyl)pyridine 1-oxide

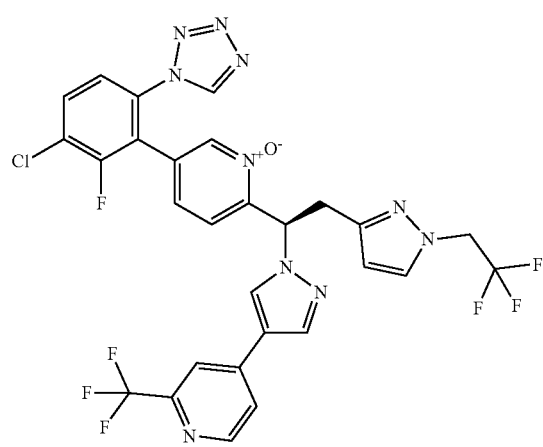

LC/MS: mass calculated for C$_{28}$H$_{18}$ClF$_7$N$_{10}$O: 678.12, measured (ES, m/z): 679.10 [M+H]$^+$. $^1$H NMR (400 MHz, DMSO-d$_6$) δ 9.69 (s, 1H), 8.79 (s, 1H), 8.66 (d, J=5.1 Hz, 1H), 8.46 (d, J=1.6 Hz, 1H), 8.31 (s, 1H), 8.02-8.11 (m, 2H), 7.85-7.90 (m, 1H), 7.72-7.82 (m, 1H), 7.65 (d, J=2.4 Hz, 1H), 7.41 (d, J=8.3 Hz, 1H), 7.15-7.21 (m, 1H), 6.30-6.40 (m, 1H), 5.97 (d, J=2.4 Hz, 1H), 4.90-5.10 (m, 2H), 3.50-3.65 (m, 2H) 15 $^{19}$F NMR (376 MHz, DMSO-d$_6$) δ −66.57, −70.40, −112.69.

Example 749: (S)-5-(6-Amino-3-chloro-2-fluorophenyl)-2-(3-(difluoromethoxy)-1-(4-(1-methyl-1H-1,2,3-triazol-5-yl)-1H-pyrazol-1-yl)propyl)pyridine 1-oxide

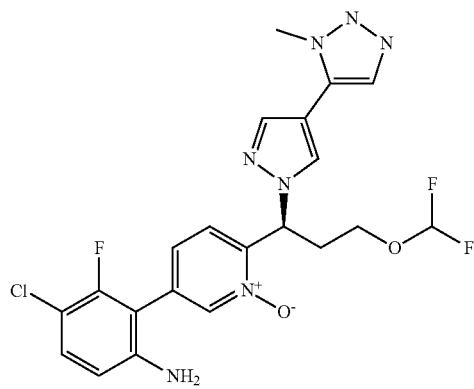 [SMILES: CN1NNC=C1c1cnn([C@@H](CCOC(F)F)c2ccc(-c3c(N)ccc(Cl)c3F)c[n+]2[O-])c1]

LC/MS: mass calculated for C$_{21}$H$_{19}$ClF$_3$N$_7$O$_2$: 493.12, measured (ES, m/z): 494.05 [M+H]$^+$. $^1$H NMR (300 MHz, DMSO-d$_6$) δ 8.57 (s, 1H), 8.33 (s, 1H), 8.09 (s, 1H), 7.92 (s, 1H), 7.30-7.50 (m, 2H), 7.24 (t, J=8.7 Hz, 1H), 6.30-6.97 (m, 3H), 5.51 (s, 2H), 4.12 (s, 3H), 3.85-4.00 (m, 1H), 3.70-3.84 (m, 1H), 2.60-2.90 (m, 2H). $^{19}$F NMR (282 MHz, DMSO-d$_6$) δ −73.46, −83.05, −118.22.

Example 750: (R)-5-(3-Chloro-6-(4-chloro-1H-1,2,3-triazol-1-yl)-2-fluorophenyl)-2-(2-(2-methyl-2H-1,2,3-triazol-4-yl)-1-(4-(2-(trifluoromethyl)pyridin-4-yl)-1H-pyrazol-1-yl)ethyl)pyridine 1-oxide

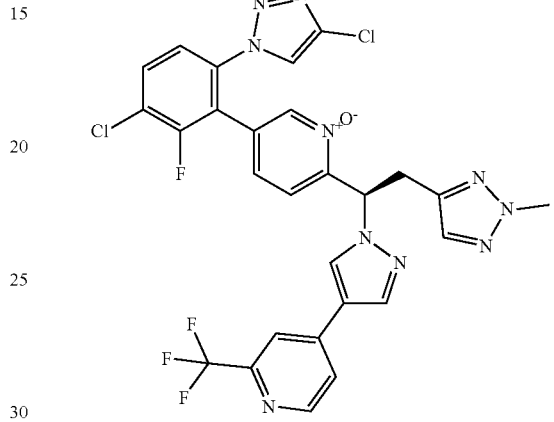

LC/MS: mass calculated for C$_{27}$H$_{18}$Cl$_2$F$_4$N$_{10}$O: 644.10, measured (ES, m/z): 645.05 [M+H]$^+$. $^1$H NMR (400 MHz, DMSO-d$_6$) δ 8.83 (s, 1H), 8.64-8.67 (m, 2H), 8.43 (d, J=1.6 Hz, 1H), 8.33 (s, 1H), 8.09 (d, J=1.6 Hz, 1H), 8.00-8.08 (m, 1H), 7.85-7.92 (m, 1H), 7.65-7.75 (m, 1H), 7.39 (d, J=8.3 Hz, 1H), 7.31 (s, 1H), 7.15-7.22 (m, 1H), 6.31-6.41 (m, 1H), 4.02 (s, 3H), 3.60-3.73 (m, 2H). $^{19}$F NMR (376 MHz, DMSO-d$_6$) δ −66.53, −73.67, −112.93.

Example 751: 5-(3-Chloro-2-fluoro-6-(1H-tetrazol-1-yl)phenyl)-2-((1S,2S)-1-(2-(difluoromethyl)-1'H,2H-[3,4'-bipyrazol]-1'-yl)-2-hydroxy-2-phenylethyl)pyridine 1-oxide

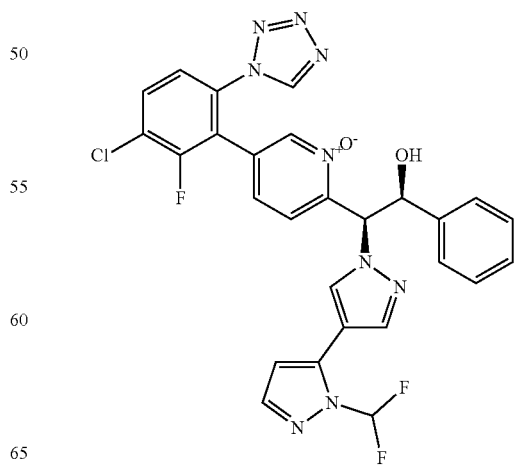

Step 1: 2-(6-(2-((tert-Butyldimethylsilyl)oxy)-1-(2-(difluoromethyl)-1'H,2H-[3,4'-bipyrazol]-1'-yl)-2-phenylethyl)pyridin-3-yl)-4-chloro-3-fluoroaniline The mixture of 1'-(1-(5-bromopyridin-2-yl)-2-((tert-butyldimethylsilyl)oxy)-2-phenylethyl)-2-(difluoromethyl)-1'H,2H-3,4'-bipyrazole (340 mg, 0.59 mmol, 1.0 equiv.), (6-amino-3-chloro-2-fluorophenyl)boronic acid (224 mg, 1.18 mmol, 2.0 equiv.), $K_2CO_3$ (409 mg, 2.96 mmol, 5.0 equiv.) and $Pd(PPh_3)_4$ (68 mg, 0.06 mmol, 0.1 equiv.) in 1,4-dioxane (5 mL) and water (1 mL) was stirred at 90° C. under $N_2$ overnight. To the reaction mixture was added water, and the mixture extracted with ethyl acetate. The organic layer was washed with brine and dried over anhydrous $Na_2SO_4$. The resulting mixture was concentrated and purified by silica gel chromatography (0→40% EA/PE) to yield 2-(6-(2-((tert-butyldimethylsilyl)oxy)-1-(2-(difluoromethyl)-1'H,2H-[3,4'-bipyrazol]-1'-yl)-2-phenylethyl)pyridin-3-yl)-4-chloro-3-fluoroaniline as a yellow solid. LC/MS: mass calculated for $C_{32}H_{34}ClF_3N_6OSi$: 638.22, measured (ES, m/z): 639.30 [M+H]$^+$.

Step 2: 1'-(2-((tert-Butyldimethylsilyl)oxy)-1-(5-(3-chloro-2-fluoro-6-(1H-tetrazol-1-yl)phenyl)pyridin-2-yl)-2-phenylethyl)-2-(difluoromethyl)-1'H,2H-3,4'-bipyrazole The mixture of 2-(6-(2-((tert-butyldimethylsilyl)oxy)-1-(2-(difluoromethyl)-1'H,2H-[3,4'-bipyrazol]-1'-yl)-2-phenylethyl)pyridin-3-yl)-4-chloro-3-fluoroaniline (200 mg, 0.31 mmol, 1.0 equiv.), azidotrimethylsilane (1 mL) and trimethoxymethane (1 mL) in acetic acid (2 mL) was stirred at room temperature overnight. The reaction mixture was concentrated and purified by reverse phase chromatography on C18 (80 g, MeCN/$H_2O$ (0.05% $CF_3COOH$): 0→55%) to yield 1'-(2-((tert-butyldimethylsilyl)oxy)-1-(5-(3-chloro-2-fluoro-6-(1H-tetrazol-1-yl)phenyl)pyridin-2-yl)-2-phenylethyl)-2-(difluoromethyl)-1'H,2H-3,4'-bipyrazole as a yellow solid. LC/MS: mass calculated for $C_{33}H_{33}ClF_3N_9OSi$: 691.22, measured (ES, m/z): 692.30 [M+H]$^+$.

Step 3: 2-(2-((tert-Butyldimethylsilyl)oxy)-1-(2-(difluoromethyl)-1'H,2H-[3,4'-bipyrazol]-1'-yl)-2-phenylethyl)-5-(3-chloro-2-fluoro-6-(1H-tetrazol-1-yl)phenyl)pyridine 1-oxide The mixture of 1'-(2-((tert-butyldimethylsilyl)oxy)-1-(5-(3-chloro-2-fluoro-6-(1H-tetrazol-1-yl)phenyl)pyridin-2-yl)-2-phenylethyl)-2-(difluoromethyl)-1'H,2H-3,4'-bipyrazole (180 mg, 0.26 mmol, 1.0 equiv.), methyltrioxorhenium (32 mg, 0.13 mmol, 0.5 equiv.) and hydrogen peroxide (147 mg, 1.30 mmol, 5.0 equiv, 30%) in $CH_3OH$ (2 mL) was stirred at room temperature for 2 h. The mixture was purified by reverse phase chromatography on C18 (80 g, MeCN/$H_2O$ (0.05% $CF_3COOH$): 0→55%) to yield 2-(2-((tert-butyldimethylsilyl)oxy)-1-(2-(difluoromethyl)-1'H,2H-[3,4'-bipyrazol]-1'-yl)-2-phenylethyl)-5-(3-chloro-2-fluoro-6-(1H-tetrazol-1-yl)phenyl)pyridine 1-oxide as a yellow solid. LC/MS: mass calculated for $C_{33}H_{33}ClF_3N_9O_2Si$: 707.22, measured (ES, m/z): 708.30 [M+H]$^+$.

Step 4: 5-(3-Chloro-2-fluoro-6-(1H-tetrazol-1-yl)phenyl)-2-((1R*,2S*)-1-(2-(difluoromethyl)-1'H,2H-[3,4'-bipyrazol]-1'-yl)-2-hydroxy-2-phenylethyl)pyridine 1-oxide To a solution of 2-(2-((tert-butyldimethylsilyl)oxy)-1-(2-(difluoromethyl)-1'H,2H-[3,4'-bipyrazol]-1'-yl)-2-phenyl-ethyl)-5-(3-chloro-2-fluoro-6-(1H-tetrazol-1-yl)phenyl)pyridine 1-oxide (100 mg, 0.14 mmol, 1.0 equiv.) in DCM (2 mL) was added trifluoroacetic acid (2 mL) at room temperature and stirred for 2 h. The mixture was purified by reverse phase chromatography on C18 (80 g, MeCN/$H_2O$ (0.05% $CF_3COOH$): 0→55%) to yield 5-(3-chloro-2-fluoro-6-(1H-tetrazol-1-yl)phenyl)-2-(1-(2-(difluoromethyl)-1'H,2H-[3,4'-bipyrazol]-1'-yl)-2-hydroxy-2-phenylethyl)pyridine 1-oxide. The compound, 5-(3-chloro-2-fluoro-6-(1H-tetrazol-1-yl)phenyl)-2-(1-(2-(difluoromethyl)-1'H,2H-[3,4'-bipyrazol]-1'-yl)-2-hydroxy-2-phenylethyl)pyridine 1-oxide (70 mg) was separated by Prep-Chiral-HPLC to yield 5-(3-chloro-2-fluoro-6-(1H-tetrazol-1-yl)phenyl)-2-((1S,2S)-1-(2-(difluoromethyl)-1'H,2H-[3,4'-bipyrazol]-1'-yl)-2-hydroxy-2-phenylethyl)pyridine 1-oxide as a white solid.

LC/MS: mass calculated for $C_{27}H_{19}ClF_3N_9O_2$: 593.13, measured (ES, m/z): 594.15 [M+H]$^+$. $^1$H NMR (300 MHz, DMSO-$d_6$) δ 9.62 (s, 1H), 8.53 (s, 1H), 8.37 (s, 1H), 7.98-8.10 (m, 1H), 7.81-7.82 (m, 2H), 7.71-7.79 (m, 2H), 7.54 (d, J=8.3 Hz, 1H), 7.32-7.35 (m, 2H), 7.16-7.31 (m, 3H), 7.13 (d, J=8.3 Hz, 1H), 6.70 (s, 1H), 6.43 (d, J=6.6 Hz, 1H), 6.10 (d, J=5.7 Hz, 1H), 5.60 (t, J=6.1 Hz, 1H). $^{19}$F NMR (282 MHz, DMSO-$d_6$) δ −93.48, −93.74, −112.73.

Example 752: (R)-2-(1-(4-(4-Chloro-1-(difluoromethyl)-1H-1,2,3-triazol-5-yl)-1H-pyrazol-1-yl)-3-(difluoromethoxy)propyl)-5-(3-Chloro-2-fluoro-6-(1H-tetrazol-1-yl)phenyl)pyridine 1-oxide

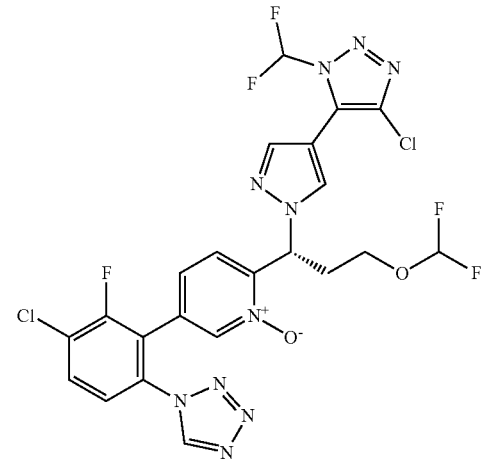 [SMILES: [O-][n+]1cc(-c2c(-n3cnnn3)ccc(Cl)c2F)ccc1[C@@H](CCOC(F)F)n1cc(-c2c(Cl)nnn2C(F)F)cn1]

Step 1: 2-(1-(4-(4-Chloro-1-(difluoromethyl)-1H-1,2,3-triazol-5-yl)-1H-pyrazol-1-yl)-3-(difluoromethoxy)propyl)-5-(3-chloro-2-fluoro-6-(1H-tetrazol-1-yl)phenyl)pyridine To a solution of 5-(3-chloro-2-fluoro-6-(1H-tetrazol-1-yl)phenyl)-2-(3-(difluoromethoxy)-1-(4-(1-(difluoromethyl)-1H-1,2,3-triazol-5-yl)-1H-pyrazol-1-yl)propyl)pyridine (100 mg, 0.18 mmol, 1.0 equiv.) in N,N-dimethylformamide (0.5 mL) was added 2-chloroisoindoline-1,3-dione (32.0 mg, 32.03 mmol, 1.0 equiv.). The resulting mixture was stirred at 60° C. for 2 h. The resulting mixture was purified by reverse phase chromatography on C18 (MeCN/$H_2O$ (0.05% $CF_3COOH$)) to yield 2-(1-(4-(4-chloro-1-(difluoromethyl)-1H-1,2,3-triazol-5-yl)-1H-pyrazol-1-yl)-3-(difluoromethoxy)propyl)-5-(3-chloro-2-fluoro-6-(1H-tetrazol-1-yl)phenyl)pyridine as a white solid. LC/MS: mass calculated for $C_{22}H_{15}Cl_2F_5N_{10}O$: 600.07, measured (ES, m/z): 601.05 [M+H]$^+$.

Step 2: (R)-2-(1-(4-(4-Chloro-1-(difluoromethyl)-1H-1,2,3-triazol-5-yl)-1H-pyrazol-1-yl)-3-(difluoromethoxy)propyl)-5-(3-chloro-2-fluoro-6-(1H-tetrazol-1-yl)phenyl)pyridine 1-oxide A mixture of 2-(1-(4-(4-chloro-1-(difluoromethyl)-1H-1,2,3-triazol-5-yl)-1H-pyrazol-1-yl)-3-(difluoromethoxy)propyl)-5-(3-chloro-2-fluoro-6-(1H-tetrazol-1-yl)phenyl)pyridine (46 mg, 0.08 mmol, 1.0 equiv.), methyltrioxorhenium (9.5 mg, 0.04 mmol, 0.5 equiv.), hydrogen peroxide (0.5 mL, 30 wt %) in $CH_3OH$ (2 mL) was stirred for 1 h at room temperature. The resulting mixture was purified by reverse phase chromatography on C18 (MeCN/$H_2O$ (0.05% $CF_3COOH$)) to yield 2-(1-(4-(4-chloro-1-(difluoromethyl)-1H-1,2,3-triazol-5-yl)-1H-pyrazol-1-yl)-3-(difluoromethoxy)propyl)-5-(3-chloro-2-fluoro-6-(1H-tetrazol-1-yl)phenyl)pyridine 1-oxide as a white solid. The racemic product was separated by chiral-HPLC to yield (R)-2-(1-(4-(4-chloro-1-(difluoromethyl)-1H-1,2,3-triazol-5-yl)-1H-pyrazol-1-yl)-3-(difluoromethoxy)propyl)-5-(3-chloro-2-fluoro-6-(1H-tetrazol-1-yl)phenyl)pyridine 1-oxide as a white solid.

LC/MS: mass calculated for $C_{22}H_{15}Cl_2F_5N_{10}O_2$: 616.07, measured (ES, m/z): 617.00 [M+H]$^+$. $^1$H NMR (400 MHz, DMSO-$d_6$) δ 9.68 (s, 1H), 8.56 (s, 1H), 8.43-8.48 (m, 1H), 8.12-8.38 (m, 1H), 8.00-8.08 (m, 2H), 7.70-7.80 (m, 1H), 7.38 (d, J=8.3 Hz, 1H), 7.17-7.23 (m, 1H), 6.35-6.80 (m, 1H), 6.20-6.31 (m, 1H), 3.78-3.84 (m, 1H), 3.60-3.71 (m, 1H), 2.54-2.69 (m, 2H). $^{19}$F-NMR (376 MHz, DMSO-$d_6$) δ −83.50, −97.56, −112.65.

Example 753: (S)-5-(3-Chloro-6-(4-chloro-1H-1,2,3-triazol-1-yl)-2-fluorophenyl)-2-(2-(2-methyl-2H-1,2,3-triazol-4-yl)-1-(4-(2-(trifluoromethyl)pyridin-4-yl)-1H-pyrazol-1-yl)ethyl)pyridine 1-oxide

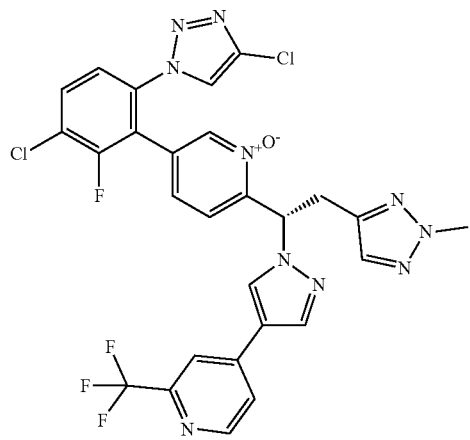

LC/MS: mass calculated for $C_{27}H_{18}Cl_2F_4N_{10}O$: 644.10, measured (ES, m/z): 645.00 [M+H]$^+$. $^1$H NMR (400 MHz, DMSO-$d_6$) δ 8.83 (s, 1H), 8.67-8.64 (m, 2H), 8.43 (d, J=1.6 Hz, 1H), 8.33 (s, 1H), 8.07-8.12 (m, 1H), 8.00-8.08 (m, 1H), 7.84-7.90 (m, 1H), 7.67-7.85 (m, 1H), 7.39 (d, J=8.3 Hz, 1H), 7.31 (s, 1H), 7.15-7.22 (m, 1H), 6.30-6.40 (m, 1H), 4.02 (s, 3H), 3.60-3.73 (m, 2H). $^{19}$F NMR (376 MHz, DMSO-$d_6$) δ −66.53, −112.93.

Example 754: 5-(3-Chloro-2-fluoro-6-(1H-tetrazol-1-yl)phenyl)-2-((1S,2R)-1-(2-(difluoromethyl)-1'H,2H-[3,4'-bipyrazol]-1'-yl)-2-hydroxy-2-phenylethyl)pyridine 1-oxide

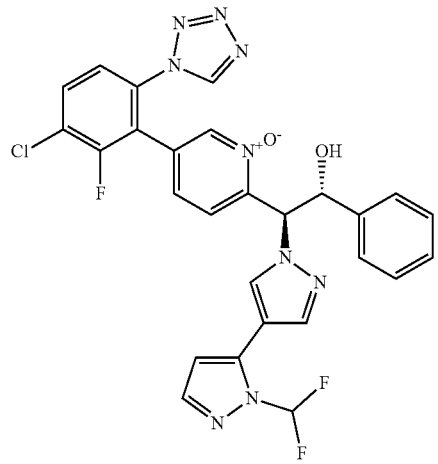

LC/MS: mass calculated for $C_{27}H_{19}ClF_3N_9O_2$: 593.1, measured (ES, m/z): 594.1 [M+H]$^+$. $^1$H NMR (300 MHz, DMSO-$d_6$) δ 9.73 (s, 1H), 8.41 (d, J=1.6 Hz, 1H), 8.01-8.14 (m, 2H), 7.73-7.84 (m, 2H), 7.70 (d, J=1.7 Hz, 2H), 7.07-7.45 (m, 7H), 6.49 (d, J=1.7 Hz, 1H), 6.18 (t, J=11.4 Hz, 2H), 5.47 (d, J=9.6 Hz, 1H). 19F NMR (282 MHz, DMSO-$d_6$) d −71.03-−76.08 (m), −93.75 (d, J=34.7 Hz), −112.69.

Example 755: (S)-2-(1-(4-(4-Chloro-1-(difluoromethyl)-1H-1,2,3-triazol-5-yl)-1H-pyrazol-1-yl)-3-(difluoromethoxy)propyl)-5-(3-chloro-2-fluoro-6-(1H-tetrazol-1-yl)phenyl)pyridine 1-oxide

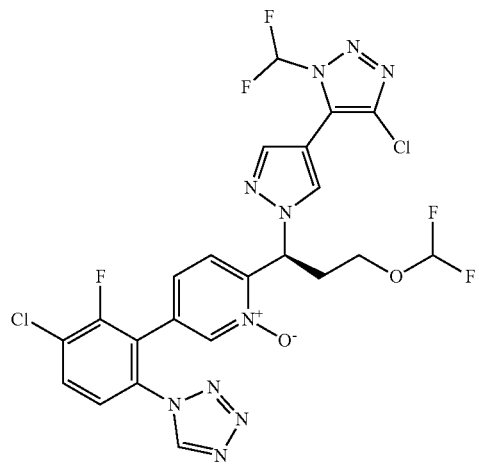 [SMILES: [O-][n+]1cc(-c2c(-n3cnnn3)ccc(Cl)c2F)ccc1[C@H](CCOC(F)F)n1cc(-c2c(Cl)nnn2C(F)F)cn1]

LC/MS: mass calculated for $C_{22}H_{15}Cl_2F_5N_{10}O_2$: 616.07, measured (ES, m/z): 617.00 [M+H]$^+$. $^1$H NMR (400 MHz, DMSO-$d_6$) δ 9.67 (s, 1H), 8.56 (s, 1H), 8.43-8.48 (m, 1H), 8.27 (t, J=56.5 Hz, 1H), 7.99-8.09 (m, 2H), 7.74 (dd, J=8.7, 1.5 Hz, 1H), 7.38 (d, J=8.3 Hz, 1H), 7.20 (dd, J=8.4, 1.7 Hz, 1H), 6.60 (t, J=75.6 Hz, 1H), 6.24-6.31 (m, 1H), 3.78-3.84 (m, 1H), 3.62-3.68 (m, 1H), 2.61 (m, 2H). $^{19}$F NMR (376 MHz, DMSO-d$_6$) δ −83.34, −97.16, −112.65.

Example 756: (R)-5-(3-Chloro-2-fluoro-6-(1H-tetrazol-1-yl)phenyl)-2-(1-(2-(difluoromethyl)-1'H,2H-[3,4'-bipyrazol]-1'-yl)-2-(thiazol-2-yl)ethyl)pyridine 1-oxide

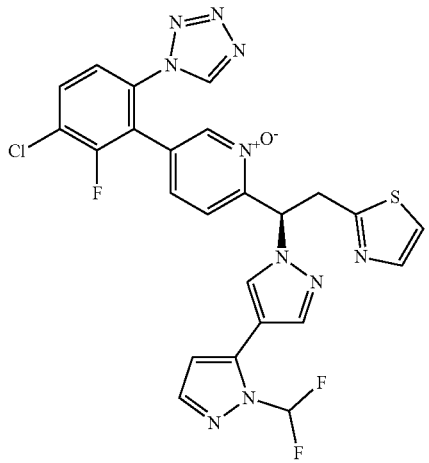

LC/MS: mass calculated for C$_{24}$H$_{16}$ClF$_3$N$_{10}$OS: 584.09, measured (ES, m/z): 585.05 [M+H]$^+$. $^1$H NMR (300 MHz, DMSO-d$_6$) δ 9.69 (s, 1H), 8.50 (d, J=1.4 Hz, 1H), 8.38 (s, 1H), 8.07 (dd, J=8.7, 7.7 Hz, 1H), 7.72-7.99 (m, 4H), 7.68 (d, J=3.3 Hz, 1H), 7.56 (t, J=3.0 Hz, 1H), 7.31 (d, J=8.3 Hz, 1H), 7.21 (dd, J=8.2, 1.7 Hz, 1H), 6.65 (d, J=1.8 Hz, 1H), 6.54 (dd, J=9.3, 5.1 Hz, 1H), 3.95-4.16 (m, 2H). $^{19}$F NMR (282 MHz, DMSO-d$_6$) d −93.63, −112.62, −218.39.

Example 757: 5-(3-Chloro-2-fluoro-6-(1H-tetrazol-1-yl)phenyl)-2-((1R*,2R*)-1-(2-(difluoromethyl)-1'H,2H-[3,4'-bipyrazol]-1'-yl)-2-hydroxy-2-phenylethyl)pyridine 1-oxide

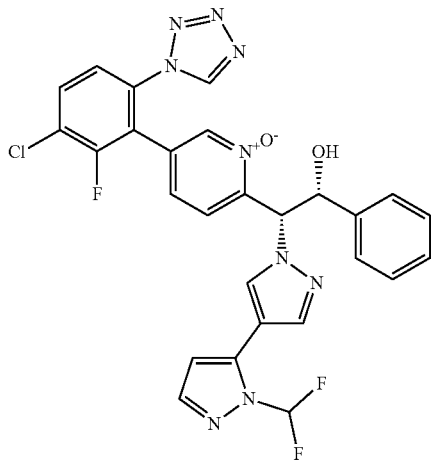

LC/MS: mass calculated for C$_{27}$H$_{19}$ClF$_3$N$_9$O$_2$: 593.13, measured (ES, m/z): 594.15 [M+H]$^+$. $^1$H NMR (300 MHz, DMSO-d$_6$) δ 9.73 (s, 1H), 8.41 (s, 1H), 8.01-8.14 (m, 2H), 7.73-7.84 (m, 2H), 7.67-7.73 (m, 2H), 7.08-7.45 (m, 7H), 6.49 (d, J=1.7 Hz, 1H), 6.20 (d, J=9.6 Hz, 1H), 6.14 (s, 1H), 5.47 (d, J=9.6 Hz, 1H). $^{19}$F NMR (282 MHz, DMSO-d$_6$) δ −73.56, −92.88, −112.69.

Example 758: (S)-5-(3-Chloro-6-(4-chloro-1H-1,2,3-triazol-1-yl)-2-fluorophenyl)-2-(3-(difluoromethoxy)-1-(4-(1-methyl-1H-1,2,4-triazol-5-yl)-1H-pyrazol-1-yl)propyl)pyridine 1-oxide

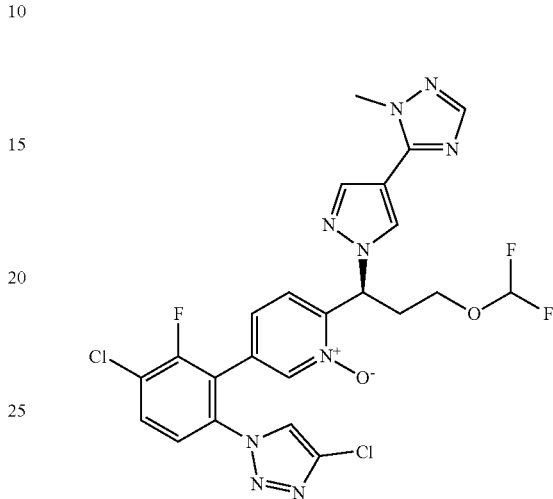

LC/MS: mass calculated for C$_{23}$H$_{18}$Cl$_2$F$_3$N$_9$O$_2$: 579.09, measured (ES, m/z): 580.05 [M+H]$^+$. $^1$H NMR (300 MHz, DMSO-d$_6$) δ 8.67 (s, 1H), 8.62 (s, 1H), 8.42 (s, 1H), 8.10 (s, 1H), 8.03 (dd, J=8.7, 7.8 Hz, 1H), 7.90 (s, 1H), 7.69 (dd, J=8.7, 1.6 Hz, 1H), 7.33 (d, J=8.3 Hz, 1H), 7.19 (dd, J=8.2, 1.7 Hz, 1H), 6.51 (d, J=75.7 Hz, 1H), 6.23-6.32 (m, 1H), 3.97 (s, 3H), 3.80-3.90 (m, 1H), 3.65-3.79 (m, 1H), 2.57-2.73 (m, 2H). $^{19}$F NMR (282 MHz, DMSO-d$_6$) δ −73.50, −83.28, −112.92.

Example 759: 5-(3-Chloro-2-fluoro-6-(1H-tetrazol-1-yl)phenyl)-2-((1R*,2S*)-1-(2-(difluoromethyl)-1'H,2H-[3,4'-bipyrazol]-1'-yl)-2-hydroxy-2-phenylethyl)pyridine 1-oxide

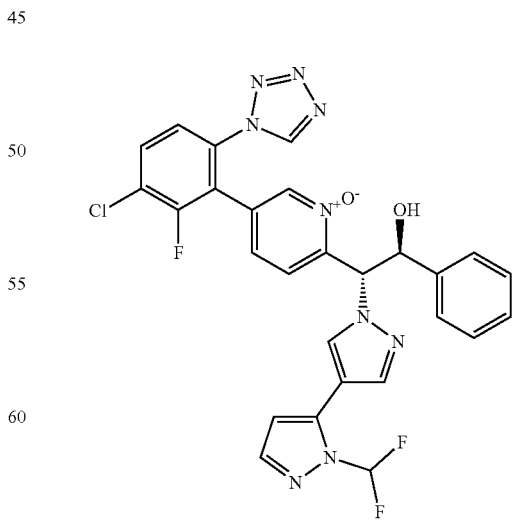

LC/MS: mass calculated for C$_{27}$H$_{19}$ClF$_3$N$_9$O$_2$: 593.13, measured (ES, m/z): 594.10 [M+H]$^+$. $^1$H NMR (300 MHz, DMSO-d$_6$) δ 9.62 (s, 1H), 8.53 (s, 1H), 8.37 (s, 1H), 7.98-8.10 (m, 1H), 7.79-7.84 (m, 2H), 7.70-7.78 (m, 2H), 7.54 (d, J=8.3 Hz, 1H), 7.30-7.38 (m, 2H), 7.19-7.30 (m, 3H), 7.09-7.15 (m, 1H), 6.70 (d, J=1.7 Hz, 1H), 6.43 (d, J=6.6 Hz, 1H), 6.10 (s, 1H), 5.60 (s, 1H). $^{19}$F NMR (282 MHz, DMSO-d$_6$) δ −73.57, −93.47, −93.74, −112.73.

Example 760: (R)-5-(3-Chloro-6-(4-chloro-1H-1,2,3-triazol-1-yl)-2-fluorophenyl)-2-(3-(difluoromethoxy)-1-(4-(1-methyl-1H-1,24-triazol-5-yl)-1H-pyrazo-1-yl)propyl)pyridine 1-oxide

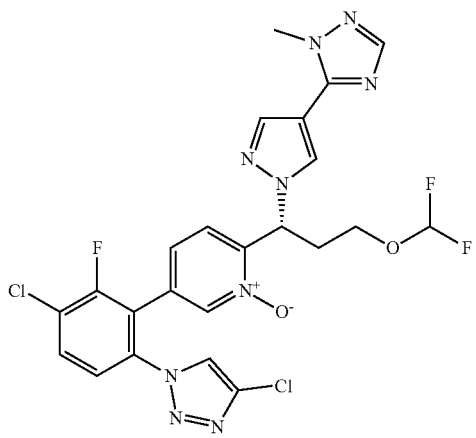

Step 1: 5-Bromo-2-(3-(difluoromethoxy)-1-(4-(1-methyl-1H-1,2,4-triazol-5-yl)-1H-pyrazol-1-yl)propyl)pyridine A mixture of 1-methyl-5-(1H-pyrazol-4-yl)-1H-1,2,4-triazole (830 mg, 5.55 mmol, 1.0 equiv.) and cesium carbonate (2.0 g, 6.11 mmol, 1.1 equiv.) in acetonitrile (20 mL) was stirred for 15 min at room temperature. 1-(5-Bromopyridin-2-yl)-3-(difluoromethoxy)propyl methanesulfonate (2.0 g, 5.55 mmol, 1.0 equiv.) was added and the solution was stirred for 2 h at 80° C. The solution was diluted with H$_2$O, extracted with ethyl acetate twice. The combined organic layers were washed with brine, dried over Na$_2$SO$_4$, concentrated and purified by silica gel chromatography (0→50% EA/PE) to yield 5-bromo-2-(3-(difluoromethoxy)-1-(4-(1-methyl-1H-1,2,4-triazol-5-yl)-1H-pyrazol-1-yl)propyl)pyridine as a light yellow oil. LC/MS: mass calculated for C$_{15}$H$_{15}$BrF$_2$N$_6$O: 412.05, measured (ES, m/z): 414.95 [M+H+2]$^+$.

Step 2: (6-(3-(Difluoromethoxy)-1-(4-(1-methyl-1H-1,2,4-triazol-5-yl)-1H-pyrazol-1-yl)propyl)pyridin-3-yl)boronic acid A mixture of 5-bromo-2-(3-(difluoromethoxy)-1-(4-(1-methyl-1H-1,2,4-triazol-5-yl)-1H-pyrazol-1-yl)propyl)pyridine (1.8 g, 4.4 mmol, 1.0 equiv.), 4,4,4',4',5,5,5',5'-octamethyl-2,2'-bi(1,3,2-dioxaborolane) (2.2 g, 8.7 mmol, 2.0 equiv.), Pd(dppf)Cl$_2$ (0.32 g, 0.44 mmol, 0.1 equiv.) and KOAc (1.3 g, 13.1 mmol, 3.0 equiv.) in 1,4-dioxane (20 mL) was stirred for 2 h at 90° C. in a nitrogen atmosphere. The mixture was diluted with water, extracted with ethyl acetate twice. The combined organic layers were washed with brine, dried over Na$_2$SO$_4$ and concentrated to yield (6-(3-(difluoromethoxy)-1-(4-(1-methyl-1H-1,2,4-triazol-5-yl)-1H-pyrazol-1-yl)propyl)pyridin-3-yl)boronic acid as deep yellow oil. LC/MS: mass calculated for C$_{15}$H$_{17}$BF$_2$N$_6$O$_3$: 378.14, measured (ES, m/z): 379.05 [M+H]$^+$.

Step 3: 5-(3-Chloro-6-(4-chloro-1H-1,2,3-triazol-1-yl)-2-fluorophenyl)-2-(3-(difluoromethoxy)-1-(4-(1-methyl-1H-1,2,4-triazol-5-yl)-1H-pyrazol-1-yl)propyl)pyridine A mixture of (6-(3-(difluoromethoxy)-1-(4-(1-methyl-1H-1,2,4-triazol-5-yl)-1H-pyrazol-1-yl)propyl)pyridin-3-yl)boronic acid (3.6 g, resulting), 4-chloro-1-(4-chloro-3-fluoro-2-iodophenyl)-1H-1,2,3-triazole (1.8 g, 5.1 mmol), Pd(PPh$_3$)$_4$ (0.98 g, 0.85 mmol, 0.2 equiv.), K$_2$CO$_3$ (3.51 g, 25.4 mmol, 6.0 equiv.) in 1,4-dioxane (16 mL) and water (4 mL) was refluxed at 90° C. under N$_2$ for 2 h. The mixture was diluted with H$_2$O, extracted with ethyl acetate twice. The combined organic layers were washed with brine, dried over Na$_2$SO$_4$, concentrated and purified by silica gel chromatography (0→10% MeOH/DCM) to yield 5-(3-chloro-6-(4-chloro-1H-1,2,3-triazol-1-yl)-2-fluorophenyl)-2-(3-(difluoromethoxy)-1-(4-(1-methyl-1H-1,2,4-triazol-5-yl)-1H-pyrazol-1-yl)propyl)pyridine as a light yellow solid. LC/MS: mass calculated for C$_{23}$H$_{18}$Cl$_2$F$_3$N$_9$O: 563.10, measured (ES, m/z): 564.00 [M+H]$^+$.

Step 4: (R)-5-(3-Chloro-6-(4-chloro-1H-1,2,3-triazol-1-yl)-2-fluorophenyl)-2-(3-(difluoromethoxy)-1-(4-(1-methyl-1H-1,2,4-triazol-5-yl)-1H-pyrazol-1-yl)propyl)pyridine 1-oxide A mixture of 5-(3-chloro-6-(4-chloro-1H-1,2,3-triazol-1-yl)-2-fluorophenyl)-2-(3-(difluoromethoxy)-1-(4-(1-methyl-1H-1,2,4-triazol-5-yl)-1H-pyrazol-1-yl)propyl)pyridine (1.8 g, 3.20 mmol, 1.0 equiv.), hydrogen peroxide (3.6 mL, 31.90 mmol, 10.0 equiv.) and methyltrioxorhenium (0.16 g, 0.64 mmol, 0.2 equiv.) in CH$_3$OH (10 mL) was stirred for 1 h at room temperature. The mixture was purified by reverse phase chromatography on C18 (80 g, MeCN/H$_2$O (0.05% CF$_3$COOH): 0→45%) to yield 5-(3-chloro-6-(4-chloro-1H-1,2,3-triazol-1-yl)-2-fluorophenyl)-2-(3-(difluoromethoxy)-1-(4-(1-methyl-1H-1,2,4-triazol-5-yl)-1H-pyrazol-1-yl)propyl)pyridine 1-oxide. The racemic product was separated by chiral-HPLC to yield (R)-5-(3-chloro-6-(4-chloro-1H-1,2,3-triazol-1-yl)-2-fluorophenyl)-2-(3-(difluoromethoxy)-1-(4-(1-methyl-1H-1,2,4-triazol-5-yl)-1H-pyrazol-1-yl)propyl)pyridine 1-oxide as a light yellow solid. LC/MS: mass calculated for C$_{23}$H$_{18}$Cl$_2$F$_3$N$_9$O$_2$: 579.09, measured (ES, m/z): 580.05 [M+H]$^+$. $^1$H NMR (400 MHz, DMSO-d$_6$): δ 8.68 (s, 1H), 8.63 (s, 1H), 8.41-8.46 (m, 1H), 8.10 (s, 1H), 8.00-8.09 (m, 1H), 7.91 (s, 1H), 7.66-7.72 (m, 1H), 7.33 (d, J=8.3 Hz, 1H), 7.15-7.22 (m, 1H), 6.64 (t, J=75.7 Hz, 1H), 6.23-6.32 (m, 1H), 3.97 (s, 3H), 3.81-3.91 (m, 1H), 3.66-3.76 (m, 1H), 2.55-2.74 (m, 2H). $^{19}$F NMR (376 MHz, DMSO-d$_6$): δ −83.32, −112.94.

Example 761: (S)-5-(3-Chloro-2-fluoro-6-(1H-tetrazol-1-yl)phenyl)-2-(1-(2-(difluoromethyl)-1'H,2H-[3,4'-bipyrazol]-1'-yl)-2-(thiazol-2-yl)ethyl)pyridine 1-oxide

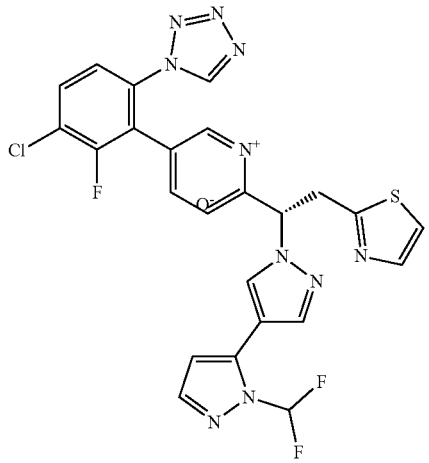

LC/MS: mass calculated for $C_{24}H_{16}ClF_3N_{10}OS$: 584.09, measured (ES, m/z): 585.10 [M+H]$^+$. $^1$H NMR (300 MHz, DMSO-$d_6$) δ 9.69 (s, 1H), 8.50 (s, 1H), 8.38 (s, 1H), 8.02-8.15 (m, 1H), 7.72-7.99 (m, 4H), 7.69 (d, J=3.3 Hz, 1H), 7.52-7.65 (m, 1H), 7.32 (d, J=8.3 Hz, 1H), 7.15-7.25 (m, 1H), 6.65 (d, J=1.7 Hz, 1H), 6.48-6.62 (m, 1H), 3.95-4.16 (m, 2H). $^{19}$F NMR (282 MHz, DMSO-$d_6$) δ −93.62, −112.62.

Example 762: (R)-5-(3-Chloro-2-fluoro-6-(1H-tetrazol-1-yl)phenyl)-2-(3-(difluoromethoxy)-1-(4-(5-fluoro-3-methyl-3H-1,2,3-triazol-4-yl)-1H-pyrazol-1-yl)propyl)pyridine 1-oxide

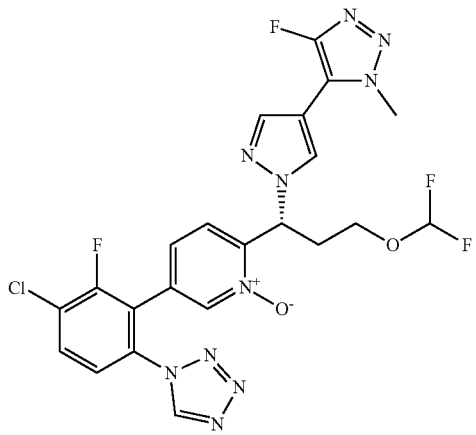 [SMILES: Cn1nnc(F)c1-c1cnn([C@H](CCOC(F)F)c2ccc(-c3c(-n4cnnn4)ccc(Cl)c3F)c[n+]2[O-])c1]

Step 1: 4-Chloro-2-(6-(3-(difluoromethoxy)-1-(4-(5-fluoro-3-methyl-3H-1,2,3-triazol-4-yl)-1H-pyrazol-1-yl)propyl)pyridin-3-yl)-3-fluorobenzenamine To a mixture of 5-bromo-2-(3-(difluoromethoxy)-1-(4-(4-fluoro-1-methyl-1H-1,2,3-triazol-5-yl)-1H-pyrazol-1-yl)propyl)pyridine (160 mg, 0.37 mmol, 1.0 equiv.) and 6-amino-3-chloro-2-fluorophenylboronic acid (105 mg, 0.56 mmol, 1.5 equiv.) in 1,4-dioxane (10 mL) and water (2 mL) was added potassium carbonate (154 mg, 1.11 mmol, 3.0 equiv.) and tetrakis(triphenylphosphine)palladium (43 mg, 0.04 mmol, 0.1 equiv.). The reaction was stirred at 100° C. for 3H under $N_2$. After cooling to room temperature, the reaction was quenched with water, and the mixture extracted with EA. The combined extracts were washed with water, saturated brine and dried over anhydrous $Na_2SO_4$ and concentrated. The residue was purified silica gel chromatography (0→10% MeOH/DCM) to yield 4-chloro-2-(6-(3-(difluoromethoxy)-1-(4-(5-fluoro-3-methyl-3H-1,2,3-triazol-4-yl)-1H-pyrazol-1-yl)propyl)pyridin-3-yl)-3-fluorobenzenamine as a yellow solid. LC/MS: mass calculated for $C_{21}H_{18}ClF_4N_7O$: 495.12, measured (ES, m/z): 496.10 [M+H]$^+$.

Step 2: 5-(3-Chloro-2-fluoro-6-(1H-tetrazol-1-yl)phenyl)-2-(3-(difluoromethoxy)-1-(4-(4-fluoro-1-methyl-1H-1,2,3-triazol-5-yl)-1H-pyrazol-1-yl)propyl)pyridine The mixture of 4-chloro-2-(6-(3-(difluoromethoxy)-1-(4-(5-fluoro-3-methyl-3H-1,2,3-triazol-4-yl)-1H-pyrazol-1-yl)propyl)pyridin-3-yl)-3-fluorobenzenamine (80 mg, 0.16 mmol, 1.0 equiv.), azidotrimethylsilane (93 mg, 0.81 mmol, 5.0 equiv.) and trimethoxymethane (171 mg, 1.61 mmol, 10.0 equiv.) in acetic acid (5 mL) was stirred overnight at room temperature. The mixture was concentrated and the resulting residue was purified by reverse phase chromatography on C18 (80 g, $CH_3CN/H_2O$ (0.05% $CF_3COOH$): 0→60%) to yield 5-(3-chloro-2-fluoro-6-(1H-tetrazol-1-yl)phenyl)-2-(3-(difluoromethoxy)-1-(4-(4-fluoro-1-methyl-1H-1,2,3-triazol-5-yl)-1H-pyrazol-1-yl)propyl)pyridine as an off-white solid. LC/MS: mass calculated for $C_{22}H_{17}ClF_4N_{10}O$: 548.12, measured (ES, m/z): 549.05 [M+H]$^+$.

Step 3: (R)-5-(3-Chloro-2-fluoro-6-(2H-tetrazol-2-yl)phenyl)-2-(3-(difluoromethoxy)-1-(4-(4-fluoro-1-methyl-1H-1,2,3-triazol-5-yl)-1H-pyrazol-1-yl)propyl)pyridine 1-oxide To a solution of 5-(3-chloro-2-fluoro-6-(1H-tetrazol-1-yl)phenyl)-2-(3-(difluoromethoxy)-1-(4-(4-fluoro-1-methyl-1H-1,2,3-triazol-5-yl)-1H-pyrazol-1-yl)propyl)pyridine (60 mg, 0.11 mmol, 1.0 equiv.) in MeOH (3 mL) was added methyltrioxorhenium (8 mg, 0.03 mmol, 0.3 equiv.) and $H_2O_2$ (30 wt %, 18 mg, 0.55 mmol, 5.0 equiv.). The resulting mixture was stirred at room temperature. for 2 h. The mixture was purified by reverse phase chromatography on C18 (80 g, $CH_3CN/H_2O$ (0.05% $CF_3COOH$)): 0→60%) and Prep-Chiral-HPLC to yield (R)-5-(3-chloro-2-fluoro-6-(2H-tetrazol-2-yl)phenyl)-2-(3-(difluoromethoxy)-1-(4-(4-fluoro-1-methyl-1H-1,2,3-triazol-5-yl)-1H-pyrazol-1-yl)propyl)pyridine 1-oxide as a white solid.

LC/MS: mass calculated for $C_{22}H_{17}ClF_4N_{10}O_2$: 564.12, measured (ES, m/z): 565.10 [M+H]$^+$. $^1$H NMR (400 MHz, DMSO-$d_6$): δ 9.68 (s, 1H), 8.53 (s, 1H), 8.45 (d, J=1.6 Hz, 1H), 8.02-8.10 (m, 1H), 8.01 (s, 1H), 7.70-7.80 (m, 1H), 7.33 (d, J=8.3 Hz, 1H), 7.15-7.22 (m, 1H), 6.62 (t, J=75.7 Hz, 1H), 6.22-6.30 (m, 1H), 4.09 (s, 3H), 3.82-3.87 (m, 1H), 3.65-3.71 (m, 1H), 2.57-2.69 (m, 2H). $^{19}$F NMR (376 MHz, DMSO-$d_6$): δ −83.31, −112.65, −145.08.

Example 763: (S)-5-(3-Chloro-2-fluoro-6-(1H-tetrazol-1-yl)phenyl)-2-(1-(4-(5-chloro-3-methyl-3H-1,2,3-triazol-4-yl)-1H-pyrazol-1-yl)-3-(difluoromethoxy)propyl)pyridine 1-oxide

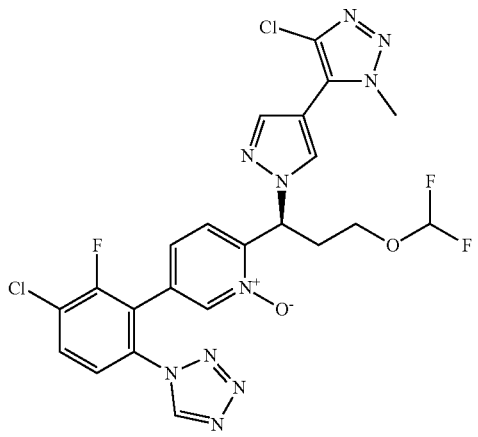 [SMILES: Cn1nnc(Cl)c1-c1cnn([C@@H](CCOC(F)F)c2ccc(-c3c(-n4cnnn4)ccc(Cl)c3F)c[n+]2[O-])c1]

LC/MS: mass calculated for $C_{22}H_{17}Cl_2F_3N_{10}O_2$: 580.09, measured (ES, m/z): 581.05 [M+H]$^+$. $^1$H NMR (400 MHz, DMSO-d$_6$) δ 9.68 (s, 1H), 8.59 (s, 1H), 8.46 (s, 1H), 8.09 (s, 1H), 8.06 (t, J=8.2 Hz, 1H), 7.75 (dd, J=8.7, 1.5 Hz, 1H), 7.36 (d, J=8.3 Hz, 1H), 7.20 (dd, J=8.2, 1.7 Hz, 1H), 6.62 (t, J=75.7 Hz, 1H), 6.24-6.31 (m, 1H), 4.11 (s, 3H), 3.82-3.88 (m, 1H), 3.65-3.71 (m, 1H), 2.55-2.74 (m, 2H). $^{19}$F NMR (376 MHz, DMSO-d$_6$) δ −83.30, −112.64.

Example 764: (R)-2-(1-(4-(4-Chloro-1-methyl-1H-1,2,3-triazol-5-yl)-1H-pyrazol-1-yl)-3-(difluoromethoxy)propyl)-5-(3-Chloro-2-fluoro-6-(1H-tetrazol-1-yl)phenyl)pyridine 1-oxide

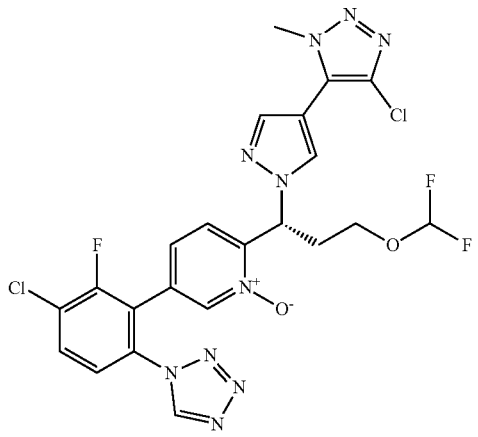 [SMILES: Cn1nnc(Cl)c1-c1cnn([C@H](CCOC(F)F)c2ccc(-c3c(-n4cnnn4)ccc(Cl)c3F)c[n+]2[O-])c1]

LC/MS: mass calculated for $C_{22}H_{17}Cl_2F_3N_{10}O_2$: 580.09, measured (ES, m/z): 581.05 [M+H]$^+$. $^1$H NMR (300 MHz, DMSO-d$_6$) δ 9.59 (s, 1H), 8.48 (s, 1H), 8.38 (s, 1H), 8.05 (s, 1H), 7.90-8.00 (m, 1H), 7.62-7.72 (m, 1H), 7.42 (d, J=8.3 Hz, 1H), 7.15-7.27 (m, 1H), 6.20-6.80 (m, 2H), 4.06 (s, 3H), 3.86-3.88 (m, 1H), 3.58-3.72 (m, 1H), 2.51-2.71 (m, 2H)$^{19}$F NMR (282 MHz, DMSO-d$_6$) δ −73.80, −83.20, −112.76.

Example 765: (S)-5-(3-Chloro-2-fluoro-6-(1H-tetrazol-1-yl)phenyl)-2-(3-(difluoromethoxy)-1-(4-(5-fluoro-3-methyl-3H-1,2,3-triazol-4-yl)-1H-pyrazol-1-yl)propyl)pyridine 1-oxide

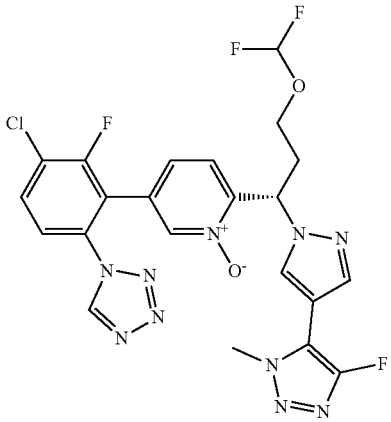 [SMILES: Cn1nnc(F)c1-c1cnn([C@@H](CCOC(F)F)c2ccc(-c3c(-n4cnnn4)ccc(Cl)c3F)c[n+]2[O-])c1]

LC/MS: mass calculated for $C_{22}H_{17}ClF_4N_{10}O_2$: 564.12, measured (ES, m/z): 565.10 [M+H]$^+$. $^1$H NMR (400 MHz, DMSO-d$_6$) δ 9.68 (s, 1H), 8.53 (s, 1H), 8.45 (s, 1H), 8.10-8.02 (m, 1H), 8.01 (s, 1H), 7.70-7.80 (m, 1H), 7.33 (d, J=8.3 Hz, 1H), 7.15-7.23 (m, 1H), 6.62 (t, J=75.7 Hz, 1H), 6.20-6.30 (m, 1H), 4.09 (s, 3H), 3.87-3.82 (m, J=10.7, 5.5 Hz, 1H), 3.77-3.63 (m, 1H), 2.75-2.53 (m, 2H). $^{19}$F NMR (376 MHz, DMSO-d$_6$) δ −83.31, −112.66, −145.08.

Example 766: 5-(3-Chloro-6-(4-chloro-1H-1,2,3-triazol-1-yl)-2-fluorophenyl)-2-((1R*,2S*)-1-(2-(difluoromethyl)-1'H,2H-[3,4'-bipyrazol]-1'-yl)-2-hydroxy-2-phenylethyl)pyridine 1-oxide

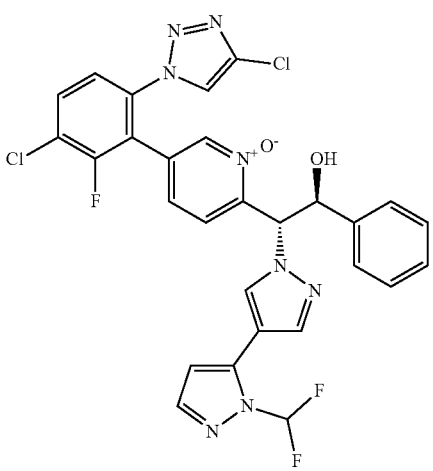

LC/MS: mass calculated for $C_{28}H_{19}Cl_2F_3N_8O_2$: 626.10, measured (ES, m/z): 627.1 [M+H]$^+$. $^1$H NMR (300 MHz, DMSO-d$_6$) δ 8.61 (s, 1H), 8.53 (s, 1H), 8.33 (s, 1H), 7.97-8.04 (m, 1H), 7.82 (t, J=57 Hz, 1H), 7.81 (s, 1H), 7.77 (d, J=1.7 Hz, 1H), 7.66 (dd, J=8.7, 1.6 Hz, 1H), 7.57 (d, J=8.3 Hz, 1H), 7.31-7.40 (m, 2H), 7.16-7.31 (m, 3H), 7.12 (dd, J=8.2, 1.6 Hz, 1H), 6.70 (d, J=1.7 Hz, 1H), 6.44 (d, J=6.8 Hz, 1H), 5.61 (d, J=6.9 Hz, 1H). $^{19}$F NMR (282 MHz, DMSO-d$_6$) δ −74.70, −93.48, −93.73, −112.98.

Example 767: 5-(3-Chloro-6-(4-chloro-1H-1,2,3-triazol-1-yl)-2-fluorophenyl)-2-((1S*,2R*)-1-(2-(difluoromethyl)-1'H,2H-[3,4'-bipyrazol]-1'-yl)-2-hydroxy-2-phenylethyl)pyridine 1-oxide

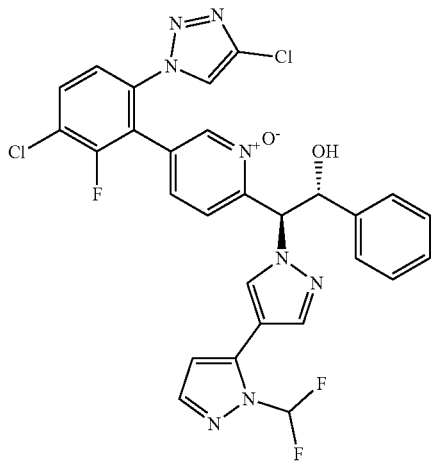

Step 1: 5-Bromo-2-(bromomethyl)pyridine

The mixture of 5-bromo-2-methylpyridine (20 g, 116.26 mmol, 1.0 equiv), NBS (24.8 g, 139.5 mmol, 1.2 equiv) and BPO (2.8 g, 11.63 mmol, 0.1 equiv) in CCl$_4$ (200 mL) was stirred at 70° C. under N$_2$ overnight.

To the reaction mixture was added water, and the mixture extracted with CH$_2$Cl$_2$, the organic layer was washed with brine and dried over anhydrous Na$_2$SO$_4$. The resulting mixture was concentrated and purified silica gel chromatography (0→50% EA/PE) to yield 5-bromo-2-(bromomethyl)pyridine as a yellow solid.

Step 2: 1'-((5-Bromopyridin-2-yl)methyl)-2-(difluoromethyl)-1'H,2H-3,4'-bipyrazole The mixture of 5-bromo-2-(bromomethyl)pyridine (1.0 g, 3.99 mmol, 1.0 equiv), 2-(difluoromethyl)-1'H,2H-3,4'-bipyrazole (881 mg, 4.78 mmol, 1.2 equiv) and Cs$_2$CO$_3$ (2.6 g, 7.97 mmol, 2.0 equiv) in acetonitrile (12 mL) was stirred at 90° C. for 3 h. To the reaction mixture was added water, and the mixture extracted with ethyl acetate, the organic layer was washed with brine and dried over anhydrous Na$_2$SO$_4$. The resulting mixture was concentrated and purified silica gel chromatography (0→50% EA/PE) to yield 1'-((5-bromopyridin-2-yl)methyl)-2-(difluoromethyl)-1'H,2H-3,4'-bipyrazole as a yellow solid. LC/MS: mass calculated for C$_{13}$H$_{10}$BrF$_2$N$_5$: 353.01, measured (ES, m/z): 354.16 [M+H]$^+$.

Step 3: 2-(5-Bromopyridin-2-yl)-2-(2-(difluoromethyl)-1'H,2H-[3,4'-bipyrazol]-1'-yl)-1-phenylethan-1-ol To a solution of 1'-((5-bromopyridin-2-yl)methyl)-2-(difluoromethyl)-1'H,2H-3,4'-bipyrazole (520 mg, 1.47 mmol, 1.0 equiv) and benzaldehyde (467 mg, 4.41 mmol, 3 equiv) in THF (8 mL) was added LiHMDS (8.8 mL, 8.8 mmol, 6 equiv) at −78° C. under N$_2$, and the reaction mixture stirred 2 h at −78° C. under N$_2$. To the reaction mixture was added NH$_4$Cl (aq.) and extracted with ethyl acetate, the organic layer was washed with brine and dried over anhydrous Na$_2$SO$_4$. The resulting mixture was concentrated and purified silica gel chromatography (0→40% EA/PE) to yield 2-(5-bromopyridin-2-yl)-2-(2-(difluoromethyl)-1'H,2H-[3,4'-bipyrazol]-1'-yl)-1-phenylethan-1-ol as a yellow solid. LC/MS: mass calculated for C$_{20}$H$_{16}$BrF$_2$N$_5$O: 459.05, measured (ES, m/z): 460.28 [M+H]$^+$.

Step 4: 1'-(1-(5-Bromopyridin-2-yl)-2-((tert-butyldimethylsilyl)oxy)-2-phenylethyl)-2-(difluoromethyl)-1'H,2H-3,4'-bipyrazole The mixture of 2-(5-bromopyridin-2-yl)-2-(2-(difluoromethyl)-1'H,2H-[3,4'-bipyrazol]-1'-yl)-1-phenylethan-1-ol (540 mg, 1.17 mmol, 1.0 equiv), imidazole (200 mg, 2.93 mmol, 2.5 equiv) and TBSCl (212 mg, 1.41 mmol, 1.2 equiv) in DMF (8 mL) was stirred at room temperature for 4 h. To the reaction mixture was added water and the mixture extracted with ethyl acetate, the organic layer was washed with brine and dried over anhydrous Na$_2$SO$_4$. The resulting mixture was concentrated and purified silica gel chromatography (0→40% EA/PE) to yield 1'-(1-(5-bromopyridin-2-yl)-2-((tert-butyldimethylsilyl)oxy)-2-phenylethyl)-2-(difluoromethyl)-1'H,2H-3,4'-bipyrazole as a yellow solid. LC/MS: mass calculated for C$_{26}$H$_{30}$BrF$_2$N$_5$OSi: 573.14, measured (ES, m/z): 574.55 [M+H]$^+$.

Step 5: (6-(2-((tert-Butyldimethylsilyl)oxy)-1-(2-(difluoromethyl)-1'H,2H-[3,4'-bipyrazol]-1'-yl)-2-phenylethyl)pyridin-3-yl)boronic acid The mixture of 1'-(1-(5-bromopyridin-2-yl)-2-((tert-butyldimethylsilyl)oxy)-2-phenylethyl)-2-(difluoromethyl)-1'H,2H-3,4'-bipyrazole (340 mg, 0.59 mmol, 1.0 equiv), KOAc (145 mg, 1.48 mmol, 2.5 equiv), 4,4,4',4',5,5,5',5'-octamethyl-2,2'-bi(1,3,2-dioxaborolane) (301 mg, 1.18 mmol, 2.0 equiv) and Pd(dppf)Cl$_2$ (43 mg, 0.06 mmol, 0.1 equiv) in 1,4-dioxane (5 mL) was stirred at 90° C. for 2 h under N$_2$(g). To the reaction mixture was added water, and the mixture extracted with ethyl acetate, the organic layer was washed with brine and dried over anhydrous Na$_2$SO$_4$. Concentrated to yield (6-(2-((tert-butyldimethylsilyl)oxy)-1-(2-(difluoromethyl)-1'H,2H-[3,4'-bipyrazol]-1'-yl)-2-phenylethyl)pyridin-3-yl)boronic acid as a yellow solid. LC/MS: mass calculated for C$_{26}$H$_{32}$BF$_2$N$_5$O$_3$Si: 539.23, measured (ES, m/z): 540.24 [M+H]$^+$.

Step 6: 1'-(2-((tert-butyldimethylsilyl)oxy)-1-(5-(3-chloro-6-(4-chloro-1H-1,2,3-triazol-1-yl)-2-fluorophenyl)pyridin-2-yl)-2-phenylethyl)-2-(difluoromethyl)-1'H,2H-3,4'-bipyrazole The mixture of (6-(2-((tert-butyldimethylsilyl)oxy)-1-(2-(difluoromethyl)-1'H,2H-[3,4'-bipyrazol]-1'-yl)-2-phenylethyl)pyridin-3-yl)boronic acid (300 mg, 0.56 mmol, 1.0 equiv), 4-chloro-1-(4-chloro-3-fluoro-2-iodophenyl)-1H-1,2,3-triazole (199 mg, 0.56 mmol, 1.0 equiv), K$_2$CO$_3$ (384 mg, 2.78 mmol, 5.0 equiv) and Pd(PPh$_3$)$_4$ (64 mg, 0.06 mmol, 0.1 equiv) in 1,4-dioxane (5 mL) and water (1 mL) was stirred at 90° C. for 2 h under N$_2$. To the reaction mixture was added water, and the mixture extracted with ethyl acetate, the organic layer was washed with brine and dried over anhydrous Na$_2$SO$_4$. The resulting mixture was concentrated and chromatography on EA/PE (1-40%) to yield 1'-(2-((tert-butyldimethylsilyl)oxy)-1-(5-(3-chloro-6-(4-chloro-1H-1,2,3-triazol-1-yl)-2-fluorophenyl)pyridin-2-yl)-2-phenylethyl)-2-(difluoromethyl)-1'H,2H-3,4'-bipyrazole as a yellow solid. LC/MS: mass calculated for $C_{34}H_{33}Cl_2F_3N_8OSi$: 724.19, measured (ES, m/z): 725.67 $[M+H]^+$.

Step 7: 2-(2-((tert-Butyldimethylsilyl)oxy)-1-(2-(difluoromethyl)-1'H,2H-[3,4'-bipyrazol]-1'-yl)-2-phenylethyl)-5-(3-chloro-6-(4-chloro-1H-1,2,3-triazol-1-yl)-2-fluorophenyl)pyridine 1-oxide The mixture of 1'-(2-((tert-butyldimethylsilyl)oxy)-1-(5-(3-chloro-6-(4-chloro-1H-1,2,3-triazol-1-yl)-2-fluorophenyl)pyridin-2-yl)-2-phenylethyl)-2-(difluoromethyl)-1'H,2H-3,4'-bipyrazole (250 mg, 0.35 mmol, 1.0 equiv), methyltrioxorhenium (43 mg, 0.17 mmol, 0.5 equiv) and hydrogen peroxide (195 mg, 1.72 mmol, 5.0 equiv, 30%) in $CH_3OH$ (2 mL) was stirred at room temperature for 2 h. The residue was purified by reverse phase chromatography on C18 (80 g, $MeCN/H_2O$ (0.05% $CF_3COOH$): 0→55%) to yield 2-(2-((tert-butyldimethylsilyl)oxy)-1-(2-(difluoromethyl)-1'H,2H-[3,4'-bipyrazol]-1'-yl)-2-phenylethyl)-5-(3-chloro-6-(4-chloro-1H-1,2,3-triazol-1-yl)-2-fluorophenyl)pyridine 1-oxide as a white solid. LC/MS: mass calculated for $C_{34}H_{33}Cl_2F_3N_8O_2Si$: 740.18, measured (ES, m/z): 741.67 $[M+H]^+$.

Step 8: 5-(3-Chloro-6-(4-chloro-1H-1,2,3-triazol-1-yl)-2-fluorophenyl)-2-((1S*,2R*)-1-(2-(difluoromethyl)-1'H,2H-[3,4'-bipyrazol]-1'-yl)-2-hydroxy-2-phenylethyl)pyridine 1-oxide To a solution of 2-(2-((tert-butyldimethylsilyl)oxy)-1-(2-(difluoromethyl)-1'H,2H-[3,4'-bipyrazol]-1'-yl)-2-phenylethyl)-5-(3-chloro-6-(4-chloro-1H-1,2,3-triazol-1-yl)-2-fluorophenyl)pyridine 1-oxide (100 mg, 0.14 mmol, 1.0 equiv) in $CH_2Cl_2$ (3 mL) was added trifluoroacetic acid (3 mL) at room temperature and stirred for 2 h. The residue was purified by reverse phase chromatography on C18 (80 g, $MeCN/H_2O$ (0.05% $CF_3COOH$): 0→55%) to yield 5-(3-chloro-6-(4-chloro-1H-1,2,3-triazol-1-yl)-2-fluorophenyl)-2-(1-(2-(difluoromethyl)-1'H,2H-[3,4'-bipyrazol]-1'-yl)-2-hydroxy-2-phenylethyl)pyridine 1-oxide, which was separated by Prep-Chiral-HPLC to yield 5-(3-chloro-6-(4-chloro-1H-1,2,3-triazol-1-yl)-2-fluorophenyl)-2-((1S*,2R*)-1-(2-(difluoromethyl)-1'H,2H-[3,4'-bipyrazol]-1'-yl)-2-hydroxy-2-phenylethyl)pyridine 1-oxide as a white solid.

LC/MS: mass calculated for $C_{28}H_{19}Cl_2F_3N_8O_2$: 626.10, measured (ES, m/z): 627.10 $[M+H]^+$. $^1H$ NMR (300 MHz, DMSO-$d_6$) δ 8.61 (s, 1H), 8.53 (s, 1H), 8.33 (s, 1H), 8.00 (t, J=8.7 Hz, 1H), 7.82 (s, 2H), 7.77 (s, 1H), 7.62-7.69 (m, 1H), 7.57 (d, J=8.3 Hz, 1H), 7.32-7.40 (m, 2H), 7.16-7.31 (m, 3H), 7.12 (d, J=8.3 Hz, 1H), 6.70 (s, 1H), 6.44 (d, J=6.9 Hz, 1H), 6.08 (d, J=5.7 Hz, 1H), 5.61 (t, J=6.3 Hz, 1H). $^{19}F$ NMR (282 MHz, DMSO-$d_6$) δ −93.48, −93.73, −112.98.

Example 768: (S)-5-(3-Chloro-2-fluoro-6-(1H-tetrazol-1-yl)phenyl)-2-(1-(4-(1-(difluoromethyl)-1H-1,2,3-triazol-5-yl)-1H-pyrazol-1-yl)-2-(4-(difluoromethyl)phenyl)ethyl)pyridine 1-oxide

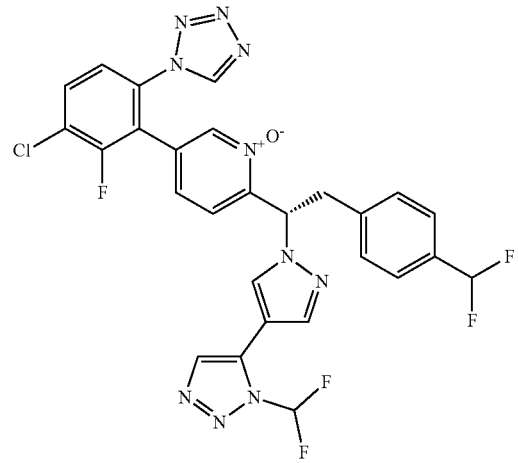

LC/MS: mass calculated for $C_{27}H_{18}ClF_5N_{10}O$: 628.1, measured (ES, m/z): 629.1 $[M+H]^+$. $^1H$ NMR (300 MHz, DMSO-$d_6$) δ 9.70 (s, 1H), 8.83 (s, 1H), 8.49 (d, J=1.6 Hz, 1H), 8.36 (s, 1H), 8.27 (t, J=57.0 Hz, 1H), 8.00-8.07 (m, 2H), 7.77 (dd, J=8.7, 1.6 Hz, 1H), 7.41-7.48 (d, J=8.0 Hz, 2H), 7.30-7.36 (m, 3H), 7.21 (dd, J=8.3, 1.7 Hz, 1H), 6.94 (t, J=54.0 Hz, 1H), 6.26-6.37 (m, 1H), 3.56-3.76 (m, 2H). $^{19}F$ NMR (282 MHz, DMSO-$d_6$) δ −73.50, −96.27, −109.28, −112.68.

Example 769: (R)-5-(3-Chloro-2-fluoro-6-(1H-tetrazol-1-yl)phenyl)-2-(1-(4-(1-(difluoromethyl)-1H-1,2,3-triazol-5-yl)-1H-pyrazol-1-yl)-2-(4-(difluoromethyl)phenyl)ethyl)pyridine 1-oxide

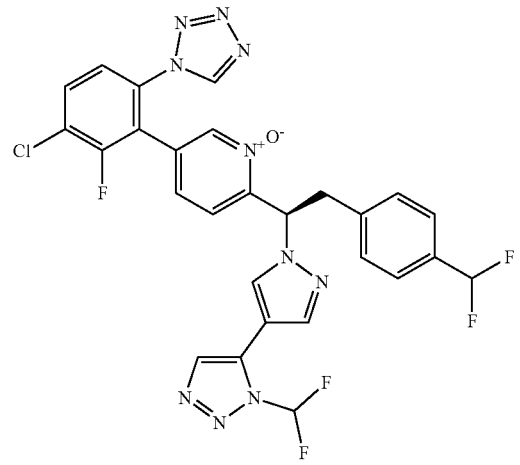

Step 1: Ethyl 2-(4-(difluoromethyl)phenyl)acetate

To a solution of ethyl (4-forMylphenyl)acetate (1.9 g, 9.89 mmol, 1.0 equiv) in $CH_2Cl_2$ (20 mL) was add DAST (7.8 mL, 59.31 mmol, 6 equiv) at −78° C. under $N_2$, then the reaction mixture was stirred 2 hours at −78° C. under N$_2$. To the reaction mixture was added NaHCO$_3$ (aq.), and the mixture extracted with ethyl acetate, the organic layer was washed with brine and dried over anhydrous Na$_2$SO$_4$, The resulting mixture was concentrated and chromatography on EA/PE (1-40%) to yield ethyl 2-(4-(difluoromethyl)phenyl) acetate as a yellow solid. LC/MS: mass calculated for C$_{11}$H$_{12}$F$_2$O$_2$: 214.08, measured (ES, m/z): 215.08 [M+H]$^+$.

Step 2: 2-(4-(Difluoromethyl)phenyl)acetic acid

To a solution of ethyl 2-(4-(difluoromethyl)phenyl)acetate (1.2 g, 5.60 mmol, 1.0 equiv) in ethanol (12 mL) was added LiOH (7.5 ml, 22.41 mmol, 4.0 equiv) at 0° C. The mixture was then warmed to room temperature and stirred for 4 h. To the reaction mixture was added HCl (1 N) to adjust to pH=5. The mixture wasnd extracted with ethyl acetate, the organic layer was washed with brine and dried over anhydrous Na$_2$SO$_4$ and concentrated to yield 2-(4-(difluoromethyl) phenyl)acetic acid as a yellow solid.

Step 3: 2-(4-(Difluoromethyl)phenyl)-N-methoxy-N-methylacetamide

To a solution of 2-(4-(difluoromethyl)phenyl)acetic acid (950 mg, 5.10 mmol, 1.0 equiv) in DCM (12 mL) was added CDI (1.2 g, 7.66 mmol, 1.5 equiv) at room temperature under N$_2$. The mixture was stirred at room temperature for 1 h. Then N-methoxymethanamine hydrochloride (548 mg, 5.61 mmol, 1.1 equiv) was added. The mixture was stirred at room temperature overnight. To the reaction mixture was added water, and the mixture extracted with CH$_2$Cl$_2$, the organic layer was washed with NaHCO$_3$ (aq.), 2 N HCl and brine and dried over anhydrous Na$_2$SO$_4$, and concentrated to yield 2-(4-(difluoromethyl)phenyl)-N-methoxy-N-methyl-acetamide as a yellow liquid. LC/MS: mass calculated for C$_{11}$H$_{13}$F$_2$NO$_2$: 229.09, measured (ES, m/z): 230.09 [M+H]$^+$.

Step 4: 1-(5-Bromopyridin-2-yl)-2-(4-(difluoromethyl)phenyl)ethan-1-one

To a solution of 2,5-dibromopyridine (353 mg, 1.49 mmol, 1.0 equiv) in toluene (5 mL) was add n-BuLi (0.66 ml, 1.64 mmol, 1.1 equiv) at −78° C. under N$_2$. After 1 hour 2-(4-(difluoromethyl)phenyl)-N-methoxy-N-methylacet-amide (410 mg, 1.79 mmol, 1.2 equiv) in toluene (1 mL) was added to the mixture slowly at −78° C. The reaction mixture was stirred 2 hours at −78° C. To the reaction mixture was added NH$_4$Cl (aq.) and the mixture extracted with ethyl acetate, the organic layer was washed with brine and dried over anhydrous Na$_2$SO$_4$, then concentrated and purified by silica gel chromatography (0→40% EA/PE) to yield 1-(5-bromopyridin-2-yl)-2-(4-(difluoromethyl)phenyl)ethan-1-one as a yellow solid. LC/MS: mass calculated for C$_{14}$H$_{10}$BrF$_2$NO: 324.99, measured (ES, m/z): 326.14 [M+H]$^+$.

Step 5: 1-(5-Bromopyridin-2-yl)-2-(4-(difluoromethyl)phenyl)ethan-1-ol

To a solution of 1-(5-bromopyridin-2-yl)-2-(4-(difluoromethyl)phenyl)ethan-1-one (280 mg, 0.86 mmol, 1.0 equiv) in CH$_3$OH (5 mL) was added NaBH$_4$ (39 mg, 1.03 mmol, 1.2 equiv) slowly at 0° C., then warmed to room temperature and stirred for 1 h. To the reaction mixture was added water, and the mixture extracted with ethyl acetate, the organic layer was washed with brine and dried over anhydrous Na$_2$SO$_4$, then concentrated to yield 1-(5-bromopyridin-2-yl)-2-(4-(difluoromethyl)phenyl)ethan-1-ol as a yellow solid. LC/MS: mass calculated for C$_{14}$H$_{12}$BrF$_2$NO: 327.01, measured (ES, m/z): 328.16 [M+H]$^+$.

Step 6: 1-(5-Bromopyridin-2-yl)-2-(4-(difluoromethyl)phenyl)ethyl methanesulfonate To a solution of 1-(5-bromopyridin-2-yl)-2-(4-(difluoromethyl)phenyl)ethan-1-ol (370 mg, 1.13 mmol, 1.0 equiv) in CH$_2$Cl$_2$ (6 mL) was added triethylamine (0.31 ml, 2.26 mmol, 2.0 equiv) and methanesulfonic anhydride (294 mg, 1.69 mmol, 1.5 equiv) at 0° C., then warmed to room temperature and stirred for 4 h. To the reaction was added water, and the mixture extracted with CH$_2$Cl$_2$, the organic layer was washed with brine and dried over anhydrous Na$_2$SO$_4$. The resulting mixture was concentrated and purified by silica gel chromatography (0→40% EA/PE) to yield 1-(5-bromopyridin-2-yl)-2-(4-(difluoromethyl)phenyl)ethyl methanesulfonate as a yellow solid. LC/MS: mass calculated for C$_{15}$H$_{14}$BrF$_2$NO$_3$S: 404.98, measured (ES, m/z): 406.24 [M+H]$^+$.

Step 7: 5-Bromo-2-(1-(4-(1-(difluoromethyl)-1H-1,2,3-triazol-4-yl)-1H-pyrazol-1-yl)-2-(4-(difluoromethyl)phenyl)ethyl)pyridine A mixture of 1-(5-bromopyridin-2-yl)-2-(4-(difluoromethyl)phenyl)ethyl methanesulfonate (274 mg, 0.68 mmol, 1.0 equiv), 1-(difluoromethyl)-5-(1H-pyrazol-4-yl)-1H-1,2,3-triazole (150 mg, 0.81 mmol, 1.2 equiv) and Cs$_2$CO$_3$ (440 mg, 1.35 mmol, 2.0 equiv) in acetonitrile (5 mL) was stirred at 90° C. for 2 h. To the reaction mixture was added water, and the mixture extracted with ethyl acetate, the organic layer was washed with brine and dried over anhydrous Na$_2$SO$_4$. The resulting mixture was concentrated and purified by silica gel chromatography (0→40% EA/PE) to yield 5-bromo-2-(1-(4-(1-(difluoromethyl)-1H-1,2,3-triazol-5-yl)-1H-pyrazol-1-yl)-2-(4-(difluoromethyl)phenyl)ethyl) pyridine as a yellow solid. LC/MS: mass calculated for C$_{20}$H$_{15}$BrF$_4$N$_6$: 494.05, measured (ES, m/z): 495.28 [M+H]$^+$.

Step 8: 4-Chloro-2-(6-(1-(4-(1-(difluoromethyl)-1H-1,2,3-triazol-4-yl)-1H-pyrazol-1-yl)-2-(4-(difluoromethyl)phenyl)ethyl)pyridin-3-yl)-3-fluoroaniline A mixture of 5-bromo-2-(1-(4-(1-(difluoromethyl)-1H-1,2,3-triazol-5-yl)-1H-pyrazol-1-yl)-2-(4-(difluoromethyl) phenyl)ethyl)pyridine (110 mg, 0.22 mmol, 1.0 equiv), (6-amino-3-chloro-2-fluorophenyl)boronic acid (84 mg, 0.44 mmol, 2.0 equiv), K$_2$CO$_3$ (153 mg, 1.11 mmol, 5.0 equiv) and Pd(PPh$_3$)$_4$ (26 mg, 0.02 mmol, 0.1 equiv) in 1,4-dioxane (4 mL) and water (1 mL) was stirred at 90° C. under $N_2$ overnight. To the reaction mixture was added water, and the mixture extracted with ethyl acetate, the organic layer was washed with brine and dried over anhydrous $Na_2SO_4$. The resulting mixture was concentrated and purified by silica gel chromatography (0→40% EA/PE) to yield 4-chloro-2-(6-(1-(4-(1-(difluoromethyl)-1H-1,2,3-triazol-5-yl)-1H-pyrazol-1-yl)-2-(4-(difluoromethyl)phenyl) ethyl)pyridin-3-yl)-3-fluoroaniline as a yellow solid. LC/MS: mass calculated for $C_{26}H_{19}ClF_5N_7$: 559.13, measured (ES, m/z): 560.13 $[M+H]^+$.

Step 9: 5-(3-Chloro-2-fluoro-6-(1H-tetrazol-1-yl) phenyl)-2-(1-(4-(1-(difluoromethyl)-1H-1,2,3-triazol-4-yl)-1H-pyrazol-1-yl)-2-(4-(difluoromethyl) phenyl)ethyl)pyridine A mixture of 4-chloro-2-(6-(1-(4-(1-(difluoromethyl)-1H-1,2,3-triazol-5-yl)-1H-pyrazol-1-yl)-2-(4-(difluoromethyl) phenyl)ethyl)pyridin-3-yl)-3-fluoroaniline (100 mg, 0.18 mmol, 1.0 equiv), azidotrimethylsilane (2 mL) and trimethoxymethane (2 mL) in acetic acid (3 mL) was stirred at room temperature overnight. The reaction was concentrated and the resulting residue was purified by reverse phase chromatography on C18 (80 g, $MeCN/H_2O$ (0.05% $CF_3COOH$): 0→55%) to yield 5-(3-chloro-2-fluoro-6-(1H-tetrazol-1-yl)phenyl)-2-(1-(4-(1-(difluoromethyl)-1H-1,2,3-triazol-5-yl)-1H-pyrazol-1-yl)-2-(4-(difluoromethyl)phenyl)ethyl)pyridine as a yellow solid. LC/MS: mass calculated for $C_{27}H_{18}ClF_5N_1O$: 612.13, measured (ES, m/z): 613.14 $[M+H]^+$ Step 10: (R)-5-(3-Chloro-2-fluoro-6-(1H-tetrazol-1-yl)phenyl)-2-(1-(4-(1-(difluoromethyl)-1H-1,2,3-triazol-5-yl)-1H-pyrazol-1-yl)-2-(4-(difluoromethyl) phenyl)ethyl)pyridine 1-oxide A mixture of 5-(3-chloro-2-fluoro-6-(1H-tetrazol-1-yl) phenyl)-2-(1-(4-(1-(difluoromethyl)-1H-1,2,3-triazol-5-yl)-1H-pyrazol-1-yl)-2-(4-(difluoromethyl)phenyl)ethyl)pyridine (100 mg, 0.16 mmol, 1.0 equiv), methyltrioxorhenium (20 mg, 0.08 mmol, 0.5 equiv) and hydrogen peroxide (92 mg, 0.82 mmol, 5.0 equiv, 30%) in $CH_3OH$ (2 mL) was stirred at room temperature for 2 h. The reaction was purified by reverse phase chromatography on C18 (80 g, $MeCN/H_2O$ (0.05% $CF_3COOH$): 0→55%) to yield 5-(3-chloro-2-fluoro-6-(1H-tetrazol-1-yl)phenyl)-2-(1-(4-(1-(difluoromethyl)-1H-1,2,3-triazol-5-yl)-1H-pyrazol-1-yl)-2-(4-(difluoromethyl)phenyl)ethyl)pyridine 1-oxide, which was separated by Prep-Chiral-HPLC to yield (R)-5-(3-chloro-2-fluoro-6-(1H-tetrazol-1-yl)phenyl)-2-(1-(4-(1-(difluoromethyl)-1H-1,2,3-triazol-5-yl)-1H-pyrazol-1-yl)-2-(4-(difluoromethyl) phenyl)ethyl)pyridine 1-oxide as a white solid.

LC/MS: mass calculated for $C_{27}H_1ClF_5N_{10}O$: 628.1, measured (ES, m/z): 629.1 $[M+H]^+$. $^1H$ NMR (300 MHz, DMSO-$d_6$) δ 9.70 (s, 1H), 8.83 (s, 1H), 8.49 (s, 1H), 8.36 (s, 1H), 8.27 (t, J=75.0 Hz, 1H), 8.07 (s, 1H), 8.02 (s, 1H), 7.77 (d, J=8.7 Hz, 1H), 7.43-7.46 (m, 2H), 7.31-7.35 (m, 3H), 7.21 (d, J=8.3 Hz, 1H), 6.94 (t, J=57.0 Hz, 1H), 6.32 (dd, J=9.6, 4.8 Hz, 1H), 3.56-3.76 (m, 2H). $^{19}F$ NMR (282 MHz, DMSO-$d_6$) δ −95.95, −96.27, −108.99, 1109.27, −112.67.

Example 770: 5-(3-Chloro-6-(4-chloro-1H-1,2,3-triazol-1-yl)-2-fluorophenyl)-2-((1S*,2S*)-1-(2-(difluoromethyl)-1'H,2H-[3,4'-bipyrazol]-1'-yl)-2-hydroxy-2-phenylethyl)pyridine 1-oxide

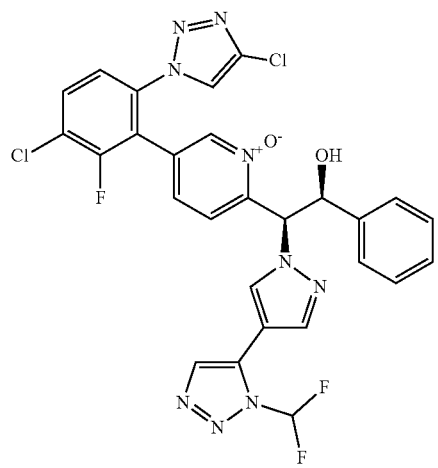

Step 1: 5-Bromo-2-(bromomethyl)pyridine

A mixture of 5-bromo-2-methylpyridine (20 g, 116.26 mmol, 1.0 equiv), NBS (24.8 g, 139.52 mmol, 1.2 equiv) and BPO (2.8 g, 11.63 mmol, 0.1 equiv) in $CCl_4$ (200 mL) was stirred at 70° C. under $N_2$ overnight.

To the reaction mixture was added water, and the mixture extracted with $CH_2Cl_2$, the organic layer was washed with brine and dried over anhydrous $Na_2SO_4$. The resulting mixture was concentrated and purified by silica gel chromatography (0→50% EA/PE) to yield 5-bromo-2-(bromomethyl)pyridine as a yellow solid.

Step 2: 1'-((5-Bromopyridin-2-yl)methyl)-2-(difluoromethyl)-1'H,2H-3,4'-bipyrazole A mixture of 5-bromo-2-(bromomethyl)pyridine (1 g, 3.99 mmol, 1.0 equiv), 2-(difluoromethyl)-1'H,2H-3,4'-bipyrazole (881 mg, 4.78 mmol, 1.2 equiv) and $Cs_2CO_3$ (2.6 g, 7.97 mmol, 2.0 equiv) in acetonitrile (12 mL) was stirred at 90° C. for 3 h. To the reaction mixture was added water, and the mixture extracted with ethyl acetate, the organic layer was washed with brine and dried over anhydrous $Na_2SO_4$. The resulting mixture was concentrated and purified by silica gel chromatography (0→50% EA/PE) to yield 1'-((5-bromopyridin-2-yl)methyl)-2-(difluoromethyl)-1'H, 2H-3,4'-bipyrazole as a yellow solid. LC/MS: mass calculated for $C_{13}H_{10}BrF_2N_5$: 353.01, measured (ES, m/z): 354.16 $[M+H]^+$.

Step 3: 2-(5-Bromopyridin-2-yl)-2-(2-(difluoromethyl)-1'H,2H-[3,4'-bipyrazol]-1'-yl)-1-phenylethan-1-ol To a solution of 1'-((5-bromopyridin-2-yl)methyl)-2-(difluoromethyl)-1'H,2H-3,4'-bipyrazole (520 mg, 1.47 mmol, 1.0 equiv) and benzaldehyde (467 mg, 4.41 mmol, 3 equiv) in THF (8 mL) was added LiHMDS (8.81 ml, 8.81 mmol, 6 equiv) at −78° C. under $N_2$, and the reaction mixture was stirred 2 hours at −78° C. under $N_2$. To the reaction mixture was added NH₄Cl, and the mixture extracted with ethyl acetate, the organic layer was washed with brine and dried over anhydrous Na₂SO₄. The resulting mixture was concentrated and purified by silica gel chromatography (0→40% EA/PE) to yield 2-(5-bromopyridin-2-yl)-2-(2-(difluoromethyl)-1'H,2H-[3,4'-bipyrazol]-1'-yl)-1-phenylethan-1-ol as a yellow solid. LC/MS: mass calculated for $C_{20}H_{16}BrF_2N_5O$: 459.05, measured (ES, m/z): 460.28 [M+H]⁺.

Step 4: 1'-(1-(5-Bromopyridin-2-yl)-2-((tert-butyldimethylsilyl)oxy)-2-phenylethyl)-2-(difluoromethyl)-1'H,2H-3,4'-bipyrazole A mixture of 2-(5-bromopyridin-2-yl)-2-(2-(difluoromethyl)-1'H,2H-[3,4'-bipyrazol]-1'-yl)-1-phenylethan-1-ol (540 mg, 1.17 mmol, 1.0 equiv), imidazole (200 mg, 2.93 mmol, 2.5 equiv) and TBSCl (212 mg, 1.41 mmol, 1.2 equiv) in DMF (8 mL) was stirred at room temperature for 4 h. To the reaction mixture was added water, and the mixture extracted with ethyl acetate, the organic layer was washed with brine and dried over anhydrous Na₂SO₄. The resulting mixture was concentrated and purified by silica gel chromatography (0→40% EA/PE) to yield 1'-(1-(5-bromopyridin-2-yl)-2-((tert-butyldimethylsilyl)oxy)-2-phenylethyl)-2-(difluoromethyl)-1'H,2H-3,4'-bipyrazole as a yellow solid. LC/MS: mass calculated for $C_{26}H_{30}BrF_2N_5OSi$: 573.14, measured (ES, m/z): 574.55 [M+H]⁺.

Step 5: (6-(2-((tert-Butyldimethylsilyl)oxy)-1-(2-(difluoromethyl)-1'H,2H-[3,4'-bipyrazol]-1'-yl)-2-phenylethyl)pyridin-3-yl)boronic acid A mixture of 1'-(1-(5-bromopyridin-2-yl)-2-((tert-butyldimethylsilyl)oxy)-2-phenylethyl)-2-(difluoromethyl)-1'H,2H-3,4'-bipyrazole (340 mg, 0.59 mmol, 1.0 equiv), KOAc (145 mg, 1.48 mmol, 2.5 equiv), 4,4,4',4',5,5,5',5'-octamethyl-2,2'-bi(1,3,2-dioxaborolane) (301 mg, 1.18 mmol, 2.0 equiv) and Pd(dppf)Cl₂ (43 mg, 0.06 mmol, 0.1 equiv) in 1,4-dioxane (5 mL) was stirred at 90° C. for 2 h under N₂. To the reaction mixture was added water, and the mixture extracted with ethyl acetate, the organic layer was washed with brine and dried over anhydrous Na₂SO₄. The resulting mixture was concentrated to yield (6-(2-((tert-butyldimethylsilyl)oxy)-1-(2-(difluoromethyl)-1'H,2H-[3,4'-bipyrazol]-1'-yl)-2-phenylethyl)pyridin-3-yl)boronic acid as a yellow solid. LC/MS: mass calculated for $C_{26}H_{32}BF_2N_5O_3Si$: 539.23, measured (ES, m/z): 540.24 [M+H]⁺.

Step 6: 1'-(2-((tert-butyldimethylsilyl)oxy)-1-(5-(3-chloro-6-(4-chloro-1H-1,2,3-triazol-1-yl)-2-fluorophenyl)pyridin-2-yl)-2-phenylethyl)-2-(difluoromethyl)-1'H,2H-3,4'-bipyrazole A mixture of (6-(2-((tert-butyldimethylsilyl)oxy)-1-(2-(difluoromethyl)-1'H,2H-[3,4'-bipyrazol]-1'-yl)-2-phenylethyl)pyridin-3-yl)boronic acid (300 mg, 0.56 mmol, 1.0 equiv), 4-chloro-1-(4-chloro-3-fluoro-2-iodophenyl)-1H-1,2,3-triazole (199 mg, 0.56 mmol, 1.0 equiv), K₂CO₃ (384 mg, 2.78 mmol, 5.0 equiv) and Pd(PPh₃)₄ (64 mg, 0.06 mmol, 0.1 equiv) in 1,4-dioxane (5 mL) and water (1 mL) was stirred at 90° C. for 2 h under N₂. To the reaction mixture was added water, and the mixture extracted with ethyl acetate, the organic layer was washed with brine and dried over anhydrous Na₂SO₄. The resulting mixture was concentrated and purified by silica gel chromatography (0→40% EA/PE) to yield 1'-(2-((tert-butyldimethylsilyl)oxy)-1-(5-(3-chloro-6-(4-chloro-1H-1,2,3-triazol-1-yl)-2-fluorophenyl)pyridin-2-yl)-2-phenylethyl)-2-(difluoromethyl)-1'H,2H-3,4'-bipyrazole as a yellow solid. LC/MS: mass calculated for $C_{34}H_{33}Cl_2F_3N_8OSi$: 724.19, measured (ES, m/z): 725.67 [M+H]⁺.

Step 7: 2-(2-((tert-Butyldimethylsilyl)oxy)-1-(2-(difluoromethyl)-1'H,2H-[3,4'-bipyrazol]-1'-yl)-2-phenylethyl)-5-(3-chloro-6-(4-chloro-1H-1,2,3-triazol-1-yl)-2-fluorophenyl)pyridine 1-oxide A mixture of 1'-(2-((tert-butyldimethylsilyl)oxy)-1-(5-(3-chloro-6-(4-chloro-1H-1,2,3-triazol-1-yl)-2-fluorophenyl)pyridin-2-yl)-2-phenylethyl)-2-(difluoromethyl)-1'H,2H-3,4'-bipyrazole (250 mg, 0.35 mmol, 1.0 equiv), methyltrioxorhenium (43 mg, 0.17 mmol, 0.5 equiv) and hydrogen peroxide (195 mg, 1.72 mmol, 5.0 equiv, 30%) in CH₃OH (2 mL) was stirred at room temperature for 2 h. The mixture was concentrated and the residue was purified by reverse phase chromatography on C18 (80 g, MeCN/H₂O (0.05% CF₃COOH): 0→55%) to yield 2-(2-((tert-butyldimethylsilyl)oxy)-1-(2-(difluoromethyl)-1'H,2H-[3,4'-bipyrazol]-1'-yl)-2-phenylethyl)-5-(3-chloro-6-(4-chloro-1H-1,2,3-triazol-1-yl)-2-fluorophenyl)pyridine 1-oxide as a white solid.

LC/MS: mass calculated for $C_{34}H_{33}Cl_2F_3N_8O_2Si$: 740.18, measured (ES, m/z): 741.67 [M+H]⁺.

Step 8: 5-(3-Chloro-6-(4-chloro-1H-1,2,3-triazol-1-yl)-2-fluorophenyl)-2-((1S,2S)-1-(2-(difluoromethyl)-1'H,2H-[3,4'-bipyrazol]-1-ium-1'-yl)-2-hydroxy-2-phenylethyl)pyridine 1-oxide To a solution of 2-(2-((tert-butyldimethylsilyl)oxy)-1-(2-(difluoromethyl)-1'H,2H-[3,4'-bipyrazol]-1'-yl)-2-phenylethyl)-5-(3-chloro-6-(4-chloro-1H-1,2,3-triazol-1-yl)-2-fluorophenyl)pyridine 1-oxide (100 mg, 0.14 mmol, 1.0 equiv) in CH₂Cl₂ (3 mL) was added trifluoroacetic acid (3 mL) at room temperature and stirred for 2 h. The mixture was concentrated and the residue was purified by reverse phase chromatography on C18 (80 g, MeCN/H₂O (0.05% CF₃COOH): 0→55%) to yield 5-(3-chloro-6-(4-chloro-1H-1,2,3-triazol-1-yl)-2-fluorophenyl)-2-(1-(2-(difluoromethyl)-1'H,2H-[3,4'-bipyrazol]-1'-yl)-2-hydroxy-2-phenylethyl)pyridine 1-oxide, which was separated by Prep-Chiral-HPLC to yield 5-(3-chloro-6-(4-chloro-1H-1,2,3-triazol-1-yl)-2-fluorophenyl)-2-((1S*,2S*)-1-(2-(difluoromethyl)-1'H,2H-[3,4'-bipyrazol]-1'-yl)-2-hydroxy-2-phenylethyl)pyridine 1-oxide as a white solid.

LC/MS: mass calculated for $C_{28}H_{19}Cl_2F_3N_8O_2$: 626.10, measured (ES, m/z): 627.10 [M+H]⁺. ¹H NMR (300 MHz, DMSO-d₆) δ 8.70 (s, 1H), 8.39 (s, 1H), 7.98-8.11 (m, 2H), 7.82 (s, 1H), 7.61-7.75 (m, 3H), 7.44 (t, J=57.0 Hz, 1H), 7.15-7.33 (m, 6H), 6.49 (s, 1H), 6.22 (d, J=9.6 Hz, 1H), 6.15 (s, 1H), 5.49 (d, J=9.6 Hz, 1H). ¹⁹F NMR (282 MHz, DMSO-d₆) δ −73.58, −93.69, −93.80, −112.95.

Example 771: 5-(3-Chloro-6-(4-chloro-1H-1,2,3-triazol-1-yl)-2-fluorophenyl)-2-((1R*,2R*)-1-(2-(difluoromethyl)-1'H,2H-[3,4'-bipyrazol]-1'-yl)-2-hydroxy-2-phenylethyl)pyridine 1-oxide

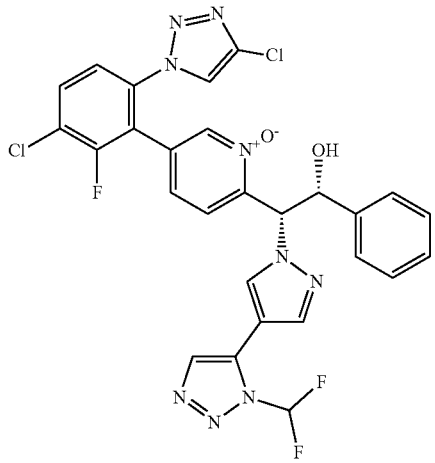

LC/MS: mass calculated for $C_{28}H_{19}Cl_2F_3N_8O_2$: 626.10, measured (ES, m/z): 627.10 [M+H]$^+$. $^1$H NMR (300 MHz, DMSO-d$_6$) δ 8.70 (s, 1H), 8.38 (d, J=1.5 Hz, 1H), 7.98-8.11 (m, 2H), 7.82 (s, 1H), 7.62-7.75 (m, 3H), 7.14-7.46 (m, 7H), 6.49 (d, J=1.7 Hz, 1H), 6.22 (d, J=9.5 Hz, 1H), 6.15 (d, J=5.4 Hz, 1H), 5.45-5.55 (m, 1H). $^{19}$F NMR (282 MHz, DMSO-d$_6$) δ −93.74, −112.95.

Example 772: (R)-5-(3-Chloro-2-fluoro-6-(1H-tetrazol-1-yl)phenyl)-2-(1-(2-(difluoromethyl)-1'H,2H-[3,4'-bipyrazol]-1'-yl)-2-(1-(difluoromethyl)-1H-pyrazol-4-yl)ethyl)pyridine 1-oxide

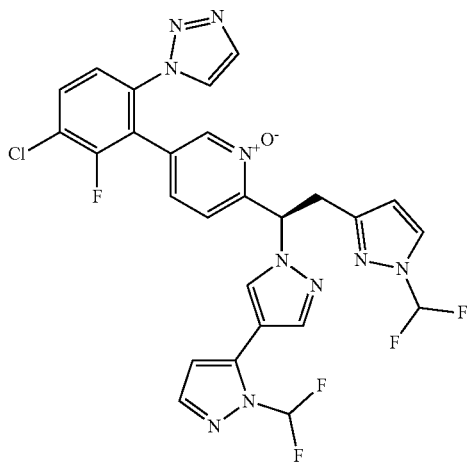

LC/MS: mass calculated for $C_{25}H_{17}ClF_5N_{11}O$: 617.12, measured (ES, m/z): 618.10 [M+H]$^+$. $^1$H NMR (300 MHz, DMSO-d$_6$) δ 9.68 (s, 1H), 8.47 (s, 1H), 8.33 (s, 1H), 8.00-8.12 (m, 2H), 7.72-7.99 (m, 4H), 7.45-7.69 (m, 1H), 7.38 (d, J=8.3 Hz, 1H), 7.20 (dd, J=8.2, 1.7 Hz, 1H), 6.63 (d, J=1.7 Hz, 1H), 6.35-6.46 (m, 1H), 6.11 (d, J=2.7 Hz, 1H), 3.59-3.73 (m, 2H)/19F NMR (282 MHz, DMSO-d$_6$) d −93.68 (d, J=2.1 Hz), −93.89, −112.64.

Example 773: (S)-5-(3-Chloro-2-fluoro-6-(1H-tetrazol-1-yl)phenyl)-2-(1-(2-(difluoromethyl)-1'H,2H-[3,4'-bipyrazol]-1'-yl)-2-(1-(difluoromethyl)-1H-pyrazol-4-yl)ethyl)pyridine 1-oxide

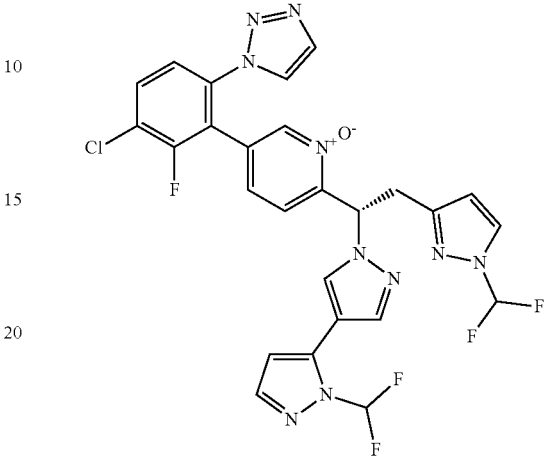

LC/MS: mass calculated for $C_{25}H_{17}ClF_5N_{11}O$: 617.12, measured (ES, m/z): 618.10 [M+H]$^+$. $^1$H NMR (300 MHz, DMSO-d$_6$) δ 9.68 (s, 1H), 8.47 (d, J=1.6 Hz, 1H), 8.33 (s, 1H), 8.00-8.12 (m, 2H), 7.70-7.98 (m, 4H), 7.45-7.69 (m, 1H), 7.38 (d, J=8.3 Hz, 1H), 7.20 (dd, J=8.2, 1.6 Hz, 1H), 6.63 (d, J=1.8 Hz, 1H), 6.35-6.46 (m, 1H), 6.11 (d, J=2.6 Hz, 1H), 3.56-3.73 (m, 2H). $^{19}$F NMR (282 MHz, DMSO-d$_6$) δ −93.68 (d, J=2.3 Hz), −93.89, −112.64.

Example 774: (R)-5-(6-Amino-3-chloro-2-fluorophenyl)-2-(3-(difluoromethoxy)-1-(4-(1-methyl-1H-1,2,3-triazol-5-yl)-1H-pyrazol-1-yl)propyl)pyridine 1-oxide

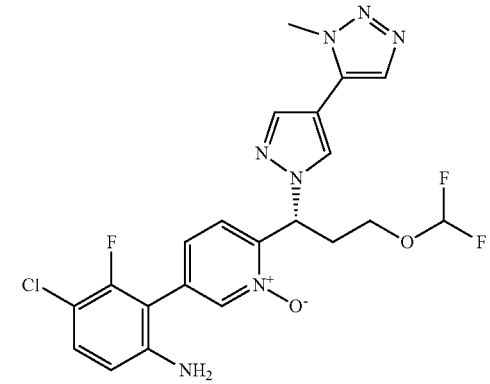 [SMILES: Cn1nncc1-c1cnn([C@H](CCOC(F)F)c2ccc(-c3c(N)ccc(Cl)c3F)c[n+]2[O-])c1]

LC/MS: mass calculated for $C_{21}H_{19}ClF_3N_7O_2$: 493.12, measured (ES, m/z): 494.05 [M+H]$^+$. $^1$H NMR (300 MHz, DMSO-d$_6$) δ 8.58 (s, 1H), 8.33 (s, 1H), 8.09 (s, 1H), 7.92 (s, 1H), 7.44 (d, J=8.2 Hz, 1H), 7.35 (d, J=8.3 Hz, 1H), 7.24 (t, J=8.6 Hz, 1H), 6.68 (t, J=75.8 Hz, 1H), 6.59 (d, J=8.9 Hz, 1H), 6.29-6.39 (m, 1H), 5.51 (s, 2H), 4.12 (s, 3H), 3.87-3.98 (m, 1H), 3.67-3.81 (m, 1H), 2.59-2.81 (m, 2H). $^{19}$F NMR (282 MHz, DMSO-d$_6$) δ −83.05, −118.21, −218.51.

Example 775: (R)-5-(3-Chloro-2-fluoro-6-(1H-tetrazol-1-yl)phenyl)-2-(2-(1-methyl-1H-1,2,3-triazol-4-yl)-1-(4-(2-(trifluoromethyl)pyridin-4-yl)-1H-pyrazol-1-yl)ethyl)pyridine 1-oxide

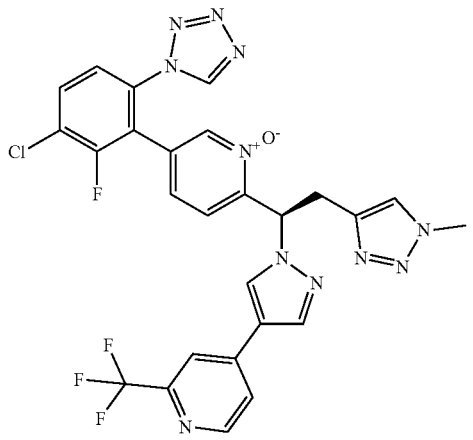

LC/MS: mass calculated for $C_{27}H_{18}ClF_4N_{11}O$: 611.13, measured (ES, m/z): 612.10 [M+H]+. 1H NMR (400 MHz, DMSO-$d_6$) δ 9.67 (s, 1H), 8.84 (s, 1H), 8.65 (d, J=5.2 Hz, 1H), 8.46 (d, J=1.6 Hz, 1H), 8.32 (s, 1H), 7.98-8.14 (m, 2H), 7.85-7.95 (m, 1H), 7.75-7.82 (m, 1H), 7.61 (s, 1H), 7.35 (d, J=8.4 Hz, 1H), 7.13-7.22 (m, 1H), 6.33-6.40 (m, 1H), 3.92 (s, 3H), 3.57-3.72 (m, 2H). 19F NMR (376 MHz, DMSO-$d_6$) δ −66.52, −112.66.

Example 776: (S)-5-(3-Chloro-2-fluoro-6-(1H-tetrazol-1-yl)phenyl)-2-(2-(1-methyl-1H-1,2,3-triazol-4-yl)-1-(4-(2-(trifluoromethyl)pyridin-4-yl)-1H-pyrazol-1-yl)ethyl)pyridine 1-oxide

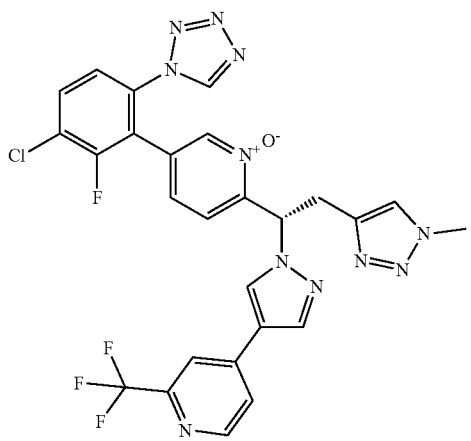

LC/MS: mass calculated for $C_{27}H_{18}ClF_4N_{11}O$: 611.13, measured (ES, m/z): 612.10 [M+H]+. 1H NMR (400 MHz, DMSO-$d_6$) δ 9.67 (s, 1H), 8.84 (s, 1H), 8.65 (d, J=5.2 Hz, 1H), 8.46 (s, 1H), 8.32 (s, 1H), 7.99-8.13 (m, 2H), 7.85-7.95 (m, 1H), 7.72-7.80 (m, 1H), 7.61 (s, 1H), 7.35 (d, J=8.3 Hz, 1H), 7.12-7.20 (m, 1H), 6.33-6.38 (m, 1H), 3.92 (s, 3H), 3.57-3.72 (m, 2H). 19F NMR (376 MHz, DMSO-$d_6$) δ −66.52, −112.66.

Example 777: (S)-5-(3-Chloro-6-(4-chloro-1H-1,2,3-triazol-1-yl)-2-fluorophenyl)-2-(2-(1-methyl-1H-1,2,3-triazol-4-yl)-1-(4-(2-(trifluoromethyl)pyridin-4-yl)-1H-pyrazol-1-yl)ethyl)pyridine 1-oxide

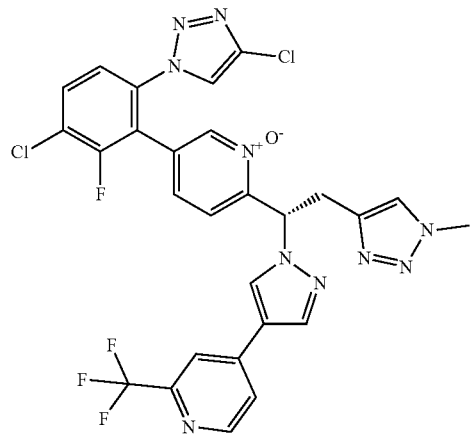

LC/MS: mass calculated for $C_{27}H_{18}Cl_2F_4N_{10}O$; 644.10, measured (ES, m/z): 645.10 [M+H]+. 1H NMR (400 MHz, DMSO-$d_6$) δ 8.84 (s, 1H), 8.62-8.70 (m, 2H), 8.43 (d, J=1.6 Hz, 1H), 8.32 (s, 1H), 8.10 (d, J=1.6 Hz, 1H), 7.97-8.05 (m, 1H), 7.85-7.95 (m, 1H), 7.57-7.70 (m, 2H), 7.37 (d, J=8.3 Hz, 1H), 7.12-7.22 (m, 1H), 6.35-6.42 (m, 1H), 3.92 (s, 3H), 3.58-3.73 (m, 2H). 19F NMR (376 MHz, DMSO-$d_6$) δ −66.52, −112.91.

Example 778: (R)-5-(3-Chloro-6-(4-chloro-1H-1,2,3-triazol-1-yl)-2-fluorophenyl)-2-(2-(1-methyl-1H-1,2,3-triazol-4-yl)-1-(4-(2-(trifluoromethyl)pyridin-4-yl)-1H-pyrazol-1-yl)ethyl)pyridine 1-oxide LC/MS: mass calculated for $C_{27}H_{18}Cl_2F_4N_{10}O$; 644.10, measured (ES, m/z): 645.10 [M+H]+. 1H NMR (400 MHz, DMSO-$d_6$) δ 8.84 (s, 1H), 8.62-8.69 (m, 2H), 8.41-8.46 (m, 1H), 8.32 (s, 1H), 8.10 (d, J=1.6 Hz, 1H), 8.00-8.07 (m, 1H), 7.85-7.95 (m, 1H), 7.65-7.73 (m, 2H), 7.37 (d, J=8.3 Hz, 1H), 7.13-7.20 (m, 1H), 6.35-6.42 (m, 1H), 3.92 (s, 3H), 3.59-3.72 (m, 2H) 19F NMR (376 MHz, DMSO-$d_6$) δ −66.52, −112.91.

Example 779: (S)-5-(3-Chloro-2-fluoro-6-(1H-tetrazol-1-yl)phenyl)-2-(2-(2-(difluoromethyl)-2H-1,2,3-triazol-4-yl)-1-(4-(2-(trifluoromethyl)pyridin-4-yl)-1H-pyrazol-1-yl)ethyl)pyridine 1-oxide

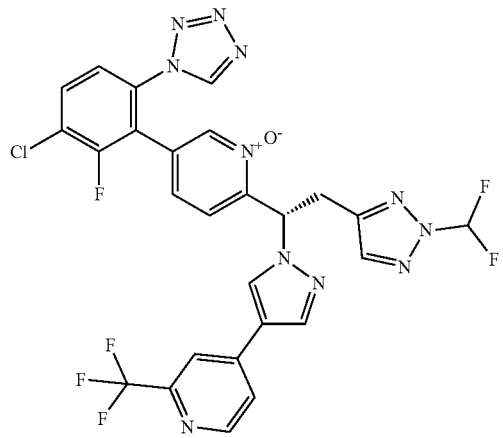

LC/MS: mass calculated for C$_{2H}$H$_{16}$ClF$_6$N$_{11}$O: 647.11, measured (ES, m/z): 648.15 [M+H]$^+$. $^1$H NMR (400 MHz, DMSO-d$_6$) δ 9.69 (s, 1H), 8.84 (s, 1H), 8.67 (d, J=5.2 Hz, 1H), 8.50 (s, 1H), 8.32-8.38 (m, 2H), 7.96-8.30 (m, 3H), 7.85-7.95 (m, 1H), 7.73-7.80 (m, 1H), 7.40 (d, J=8.3 Hz, 1H), 7.15-7.25 (m, 1H), 6.40-6.50 (m, 1H), 3.70-3.85 (m, 2H)$^{19}$F NMR (376 MHz, DMSO-d$_6$) δ −66.55, −96.10-112.66.

Example 780: 5-(3-Chloro-2-fluoro-6-(1H-tetrazol-1-yl)phenyl)-2-(2-(4-fluoro-1-(2,2,2-trifluoroethyl)-1H-pyrazol-3-yl)-1-(4-(2-(trifluoromethyl)pyridin-4-yl)-1H-pyrazol-1-yl)ethyl)pyridine 1-oxide

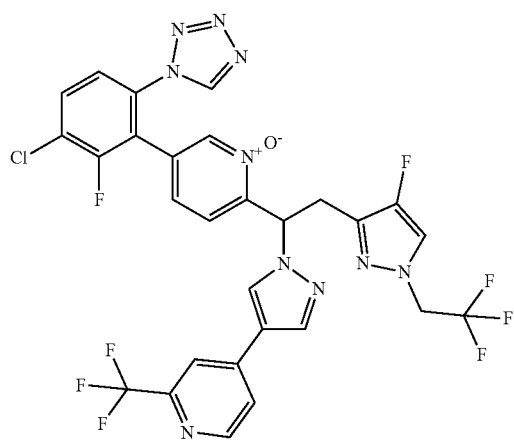

LC/MS: mass calculated for C$_{28}$H$_{17}$ClF$_8$N$_{10}$: 696.11, measured (ES, m/z): 697.10 [M+H]$^+$. $^1$H NMR (400 MHz, CD$_3$OD) δ 9.37 (s, 1H), 8.59 (d, J=5.2 Hz, 1H), 8.51 (s, 1H), 8.38 (s, 1H), 8.14 (s, 1H), 7.88-7.98 (m, 2H), 7.75-7.82 (m, 1H), 7.59-7.64 (m, 3H), 7.26-7.32 (m, 1H), 6.63 (t, J=7.6 Hz, 1H), 4.69-4.82 (m, 2H), 3.74 (d, J=7.7 Hz, 2H). $^{19}$F NMR (376 MHz, CD$_3$OD) δ −69.57, −73.50, −113.69, −178.77.

Example 781: (R)-5-(3-Chloro-2-fluoro-6-(1H-tetrazol-1-yl)phenyl)-2-(2-(2-(difluoromethyl)-2H-1,2,3-triazol-4-yl)-1-(4-(2-(trifluoromethyl)pyridin-4-yl)-1H-pyrazol-1-yl)ethyl)pyridine 1-oxide

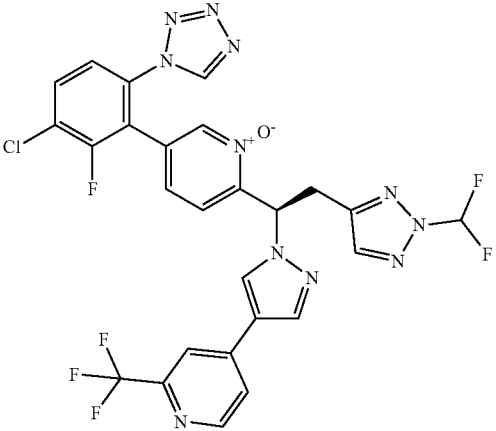

LC/MS: mass calculated for C$_{2H}$H$_{16}$ClF$_6$N$_{11}$O: 647.11, measured (ES, m/z): 648.1 [M+H]$^+$. $^1$H NMR (400 MHz, DMSO-d$_6$) δ 9.69 (s, 1H), 8.83 (s, 1H), 8.66 (d, J=5.2 Hz, 1H), 8.50 (s, 1H), 8.31-8.37 (m, 2H), 7.97-8.30 (m, 3H), 7.83-7.91 (m, 1H), 7.72-7.80 (m, 1H), 7.39 (d, J=8.3 Hz, 1H), 7.15-7.25 (m, 1H), 6.40-6.50 (m, 1H), 3.69-3.85 (m, 2H). $^{19}$F NMR (376 MHz, DMSO-d$_6$) δ −66.55, −96.10-112.66.

Example 782A: (S)-5-(3-Chloro-2-fluoro-6-(1H-tetrazol-1-yl)phenyl)-2-(2-cyclopropyl-1-(4-(4-fluoro-1-methyl-1H-1,2,3-triazol-5-yl)-1H-pyrazol-1-yl)ethyl)pyridine 1-oxide

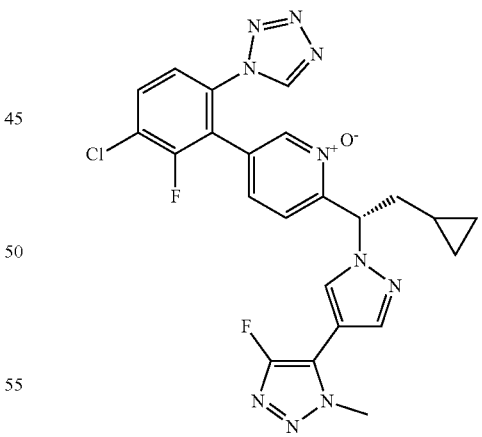

LC/MS: mass calculated for C$_{23}$H$_{19}$ClF$_2$N$_{10}$O: 524.14, measured (ES, m/z): 525.25 [M+H]$^+$. $^1$H NMR (300 MHz, DMSO-d$_6$) δ 9.70 (s, 1H), 8.60 (s, 1H), 8.44 (s, 1H), 8.07 (t, J=7.8, 1H), 7.98 (s, 1H), 7.76 (dd, J=8.7, 1.6 Hz, 1H), 7.37 (d, J=8.3 Hz, 1H), 7.17 (dd, J=8.4, 1.6 Hz, 1H), 6.21-6.16 (m, 1H), 4.11 (s, 3H), 2.39-2.28 (m, 1H), 2.01-1.92 (m, 1H), 0.62-0.57 (m, 1H), 0.38-0.35 (m, 2H), 0.18-0.11 (m, 1H), −0.02--0.08 (m, 1H). $^{19}$F NMR (282 MHz, DMSO-d$_6$) δ −112.80, 145.24.

Example 782B (S*)-5-(3-Chloro-2-fluoro-6-(1H-tetrazol-1-yl)phenyl)-2-(2-cyclopropyl-1-(4-(4-fluoro-1-methyl-1H-1,2,3-triazol-5-yl)-1H-pyrazol-1-yl)ethyl)pyridine 1-oxide

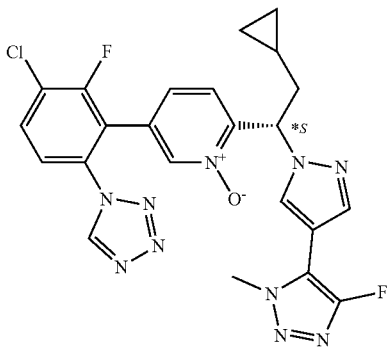

Step 1: 5-Bromo-2-(2-cyclopropyl-1-(4-(1-methyl-1H-1,2,3-triazol-5-yl)-1H-pyrazol-1-yl)ethyl)pyridine A mixture of 1-(5-bromopyridin-2-yl)-2-cyclopropylethyl methanesulfonate (301 mg, 0.94 mmol, 1.0 equiv.), 1-methyl-5-(1H-pyrazol-4-yl)-1H-1,2,3-triazole (140 mg, 0.94 mmol, 1.0 equiv.) and cesium carbonate (306 mg, 0.94 mmol, 1.0 equiv.) in acetonitrile (5 mL) was stirred for 2 h at 80° C., diluted with H$_2$O, and extracted with EA twice. The combined organic layers was washed with brine, dried over Na$_2$SO$_4$, concentrated and purified by silica gel chromatography (0→10% CH$_3$OH/DCM) to yield 5-bromo-2-(2-cyclopropyl-1-(4-(1-methyl-1H-1,2,3-triazol-5-yl)-1H-pyrazol-1-yl)ethyl)pyridine as brown oil. LC/MS: mass calculated for C$_{16}$H$_{17}$BrN$_6$: 372.07, measured (ES, m/z): 373.00, 375.00 [M+H, M+H+2]$^+$.

Step 2: 5-Bromo-2-(2-cyclopropyl-1-(4-(4-fluoro-1-methyl-1H-1,2,3-triazol-5-yl)-1H-pyrazol-1-yl)ethyl)pyridine To a mixture of 5-bromo-2-(2-cyclopropyl-1-(4-(1-methyl-1H-1,2,3-triazol-5-yl)-1H-pyrazol-1-yl)ethyl)pyridine (310 mg, 0.83 mmol, 1.0 equiv.) in acetonitrile (5 mL) was added 1-chloromethyl-4-fluoro-1,4-diazoniabicyclo[2.2.2]octane bis(tetrafluoroborate) (883 mg, 2.49 mmol, 3.0 equiv.). The solution was stirred at 80° C. for 2 h. The mixture was diluted with H$_2$O, extracted with EA twice. The combined organic layers was washed with brine, dried over Na$_2$SO$_4$, concentrated and purified by silica gel chromatography (0→50% EtOAc/petroleum ether) to yield 5-bromo-2-(2-cyclopropyl-1-(4-(4-fluoro-1-methyl-1H-1,2,3-triazol-5-yl)-1H-pyrazol-1-yl)ethyl)pyridine as brown oil. LC/MS: mass calculated for C$_{16}$H$_{16}$BrFN$_6$: 390.06, measured (ES, m/z): 391.00, 393.00 [M+H, M+H+2]$^+$.

Step 3: 4-Chloro-2-(6-(2-cyclopropyl-1-(4-(4-fluoro-1-methyl-1H-1,2,3-triazol-5-yl)-1H-pyrazol-1-yl)ethyl)pyridin-3-yl)-3-fluoroaniline To a mixture of 5-bromo-2-(2-cyclopropyl-1-(4-(4-fluoro-1-methyl-1H-1,2,3-triazol-5-yl)-1H-pyrazol-1-yl)ethyl)pyridine (60 mg, 0.15 mmol, 1.0 equiv.) and (6-amino-3-chloro-2-fluorophenyl)boronic acid (44 mg, 0.23 mmol, 1.5 equiv.) in a mixed solution of 1,4-dioxane (2 mL) and water (0.5 mL) was added potassium carbonate (64 mg, 0.46 mmol, 3.0 equiv.) and tetrakis(triphenylphosphine)Palladium(18 mg, 0.02 mmol, 0.1 equiv.). The flask was evacuated, then purged with nitrogen. This was repeated 2×. The reaction mixture was stirred at 90° C. for 2 h under N$_2$. The mixture was diluted with H$_2$O, extracted with EA twice. The combined organic layers was washed with brine, dried over Na$_2$SO$_4$, concentrated and purified by silica gel chromatography CH$_3$OH/DCM (0→10%) to yield 4-chloro-2-(6-(2-cyclopropyl-1-(4-(4-fluoro-1-methyl-1H-1,2,3-triazol-5-yl)-1H-pyrazol-1-yl)ethyl)pyridin-3-yl)-3-fluoroaniline as a brown oil. LC/MS: mass calculated for C$_{22}$H$_{20}$ClF$_2$N$_7$: 455.14, measured (ES, m/z): 456.10 [M+H]$^+$.

Step 4: 5-(3-Chloro-2-fluoro-6-(1H-tetrazol-1-yl)phenyl)-2-(2-cyclopropyl-1-(4-(4-fluoro-1-methyl-1H-1,2,3-triazol-5-yl)-1H-pyrazol-1-yl)ethyl)pyridine To a solution of 4-chloro-2-(6-(2-cyclopropyl-1-(4-(4-fluoro-1-methyl-1H-1,2,3-triazol-5-yl)-1H-pyrazol-1-yl)ethyl)pyridin-3-yl)-3-fluoroaniline (60 mg, 0.13 mmol, 1.0 equiv.) in Acetic acid (0.5 mL) was added azidotrimethylsilane (0.5 mL, 3.80 mmol, 28.9 equiv) and trimethoxymethane (0.5 mL, 4.57 mmol, 34.7 equiv.). The reaction mixture was stirred at room temperature overnight. The reaction mixture was concentrated under vacuum. The reaction mixture was purified by reverse phase chromatography on C18 (40 g, MeCN/H$_2$O (0.05% CF$_3$COOH): 0→28%). To yield 5-(3-chloro-2-fluoro-6-(1H-tetrazol-1-yl)phenyl)-2-(2-cyclopropyl-1-(4-(4-fluoro-1-methyl-1H-1,2,3-triazol-5-yl)-1H-pyrazol-1-yl)ethyl)pyridine as a pink solid. LC/MS: mass calculated for C$_{23}$H$_{19}$ClF$_2$N$_{10}$: 508.15, measured (ES, m/z): 509.10 [M+H]$^+$.

Step 5: (S*)-5-(3-Chloro-2-fluoro-6-(1H-tetrazol-1-yl)phenyl)-2-(2-cyclopropyl-1-(4-(4-fluoro-1-methyl-1H-1,2,3-triazol-5-yl)-1H-pyrazol-1-yl)ethyl)pyridine 1-oxide To a solution of 5-(3-chloro-2-fluoro-6-(1H-tetrazol-1-yl)phenyl)-2-(2-cyclopropyl-1-(4-(4-fluoro-1-methyl-1H-1,2,3-triazol-5-yl)-1H-pyrazol-1-yl)ethyl)pyridine (45 mg, 0.09 mmol, 1.0 equiv.) and methyltrioxorhenium (VII) (4 mg, 0.02 mmol, 0.2 equiv.) in CH$_3$OH (1 mL) was added hydrogen peroxide (0.09 mL, 0.88 mmol, 10.0 equiv.). The reaction mixture was stirred at room temperature for 2.5 h. The reaction mixture was purified by reverse phase chromatography on C18 (80 g, MeCN/H$_2$O (0.05% CF$_3$COOH): 0→60%). The resulting residue was purified by Prep-Chiral-HPLC to yield (S*)-5-(3-chloro-2-fluoro-6-(1H-tetrazol-1-yl)phenyl)-2-(2-cyclopropyl-1-(4-(4-fluoro-1-methyl-1H-1,2,3-triazol-5-yl)-1H-pyrazol-1-yl)ethyl)pyridine 1-oxide as a white solid.

LC/MS: mass calculated for C$_{23}$H$_{19}$ClF$_2$N$_{10}$O: 524.14, measured (ES, m/z): 525.25 [M+H]$^+$. $^1$H NMR (300 MHz, DMSO-d$_6$): δ 9.70 (s, 1H), 8.60 (s, 1H), 8.43 (s, 1H), 8.07 (t, J=8.3 Hz, 1H), 7.98 (s, 1H), 7.76 (dd, J=8.7, 1.6 Hz, 1H), 7.37 (d, J=8.3 Hz, 1H), 7.18 (d, J=8.1 Hz, 1H), 6.17-6.19 (m, 1H), 4.11 (s, 3H), 2.25-2.42 (m, 1H), 1.95-2.01 (m, 1H), 0.58-0.65 (m, 1H), 0.29-0.40 (m, 2H), 0.08-0.14 (m, 1H), −0.08-0.02 (m, 1H). $^{19}$F-NMR (282 MHz, DMSO-d$_6$): δ −112.75, −145.15.

Example 783: (R*)-5-(3-Chloro-6-(4-chloro-1H-1,2,3-triazol-1-yl)-2-fluorophenyl)-2-(3-(difluoromethoxy)-1-(4-hydroxy-2-methyl-1'H,2H-[3,4'-bipyrazol]-1'-yl)propyl)pyridine 1-oxide

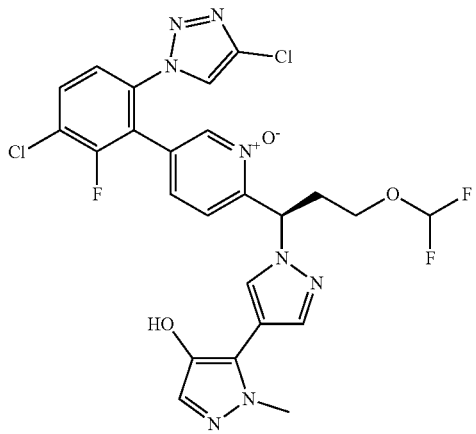

LC/MS: mass calculated for $C_{24}H_{19}Cl_2F_3N_8O_3$: 594.10, measured (ES, m/z): 595.05 [M+H]$^+$. $^1$H NMR (400 MHz, DMSO-d$_6$) δ 8.67 (s, 1H), 8.54 (s, 1H), 8.41 (s, 1H), 8.28 (s, 1H), 7.97-8.03 (m, 1H), 7.93 (s, 1H), 7.65-7.77 (m, 1H), 7.28 (d, J=8.3 Hz, 1H), 7.13-7.22 (m, 1H), 7.02 (s, 1H), 6.36-6.87 (m, 1H), 6.20-6.30 (m, 1H), 3.80-3.88 (m, 1H), 3.79 (s, 3H), 3.63-3.81 (m, 1H), 2.52-2.73 (m, 2H). $^{19}$F NMR (376 MHz, DMSO-d$_6$) δ −73.41, −83.20, −112.92.

Example 784: (S)-5-(3-Chloro-2-fluoro-6-(1H-tetrazol-1-yl)phenyl)-2-(2-(1-(difluoromethyl)-1H-1,2,3-triazol-4-yl)-1-(4-(2-(trifluoromethyl)pyridin-4-yl)-1H-pyrazol-1-yl)ethyl)pyridine 1-oxide

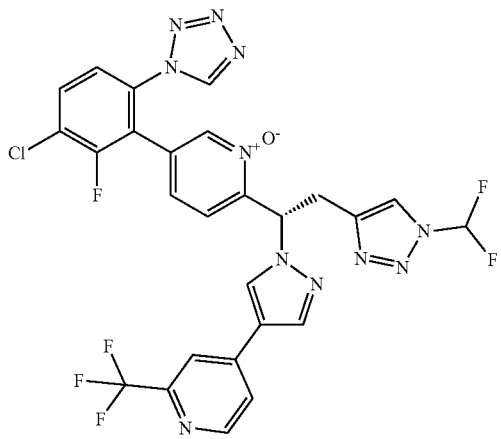

LC/MS: mass calculated for $C_{27}H_{16}ClF_6N_{11}O$: 647.11, measured (ES, m/z): 648.05 [M+H]$^+$. $^1$H NMR (400 MHz, DMSO-d$_6$) δ 9.66 (s, 1H), 8.76 (s, 1H), 8.67 (d, J=5.2 Hz, 1H), 8.47 (s, 1H), 8.33 (s, 1H), 7.80-8.12 (m, 5H), 7.70-7.76 (m, 1H), 7.44 (d, J=8.3 Hz, 1H), 7.20-7.30 (m, 1H), 6.40-6.50 (m, 1H), 3.76-3.90 (m, 2H). $^{19}$F NMR (376 MHz, DMSO-d$_6$) δ −66.55, −73.48, −96.74, −112.67.

Example 785: (R)-5-(3-Chloro-6-(4-chloro-1H-1,2,3-triazol-1-yl)-2-fluorophenyl)-2-(3-(difluoromethoxy)-1-(4-hydroxy-2-methyl-1'H,2H-[3,4'-bipyrazol]-1'-yl)propyl)pyridine 1-oxide

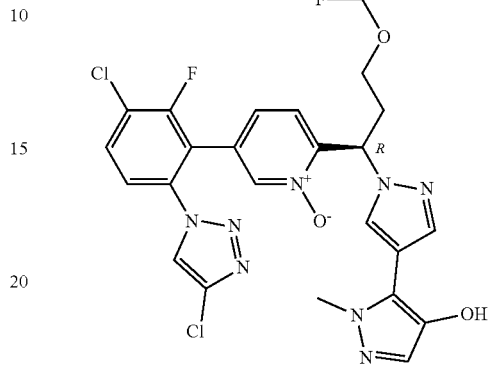

Step 1: 4-(Methoxymethoxy)-1-methyl-1H-pyrazole

To a solution of 1-methyl-1H-pyrazol-4-ol (5.0 g, 50.97 mmol, 1.0 equiv.) in DMF (25 mL) was added NaH (1.6 g, 66.26 mmol, 1.3 equiv.) at 0° C. and the mixture was stirred for 0.5 h. To the solution was then added a solution of bromo(methoxy)methane (5.0 mL, 61.16 mmol, 1.2 equiv.) in DMF (5.0 mL) at 0° C. and the solution was allowed to stir for 1 h at room temperature. The solution was poured into ice/water, and the mixture extracted with ethyl acetate twice. The combined organic layer was washed with water and then brine, dried over Na$_2$SO$_4$ and concentrated. The residue was purified by silica gel chromatography (0→50% EtOAc/petroleum ether) to yield 4-(methoxymethoxy)-1-methyl-1H-pyrazole as a yellow liquid.

Step 2: 5-Iodo-4-(methoxymethoxy)-1-methyl-1H-pyrazole

To a solution of 4-(methoxymethoxy)-1-methyl-1H-pyrazole (500 mg, 3.52 mmol, 1.0 equiv.) in THF (15 mL) was added n-butyllithium (1.55 mL, 3.87 mmol, 2.5 M, 1.1 equiv.) under nitrogen and stirred at −78° C. for 1H. To the resulting mixture was added I$_2$ (1.1 g, 4.22 mmol, 1.0 equiv.) in THF (5 mL). The resulting mixture was maintained under nitrogen and stirred at −78° C. for 2 h. The reaction was quenched with aqueous NH$_4$Cl (40 mL). The resulting mixture was extracted with ethyl acetate (3×20 mL). The organic layers were combined, dried over anhydrous sodium sulfate, filtered and concentrated. The resulting residue was purified by silica gel chromatography (0→50% EA/PE) to yield 5-iodo-4-(methoxymethoxy)-1-methyl-1H-pyrazole as a yellow solid. LC/MS: mass calculated for $C_6H_9IN_2O_2$: 267.97, measured (ES, m/z): 268.95 [M+H]$^+$.

Step 3: 4-(Methoxymethoxy)-2-methyl-1'H,2H-3,4'-bipyrazole

To a solution of 5-iodo-4-(methoxymethoxy)-1-methyl-1H-pyrazole (0.85 g, 3.16 mmol, 1.0 equiv.) in DMF (25 mL) and H$_2$O (5 mL) was added tert-butyl 4-(4,4,5,5-tetramethyl-1,3,2-dioxaborolan-2-yl)-1H-pyrazole-1-carboxylate (1.86 g, 6.32 mmol, 2.0 equiv.), K₂CO₃ (1.3 g, 9.48 mmol, 3.0 equiv.) and Pd(PPh₃)₄ (0.37 g, 0.32 mmol, 0.1 equiv.). The resulting mixture was maintained under nitrogen and stirred at 90° C. for 2 h. After cooling to room temperature, the reaction was quenched with water (60 mL). The resulting mixture was extracted with ethyl acetate (3×20 mL). The organic layers were combined, dried over anhydrous sodium sulfate, filtered and concentrated. The resulting residue was purified by silica gel chromatography (0→7% MeOH/DCM) to yield 4-(methoxymethoxy)-2-methyl-1'H,2H-3,4'-bipyrazole as a yellow solid. LC/MS: mass calculated for $C_9H_{12}N_4O_2$: 208.10, measured (ES, m/z): 209.10 [M+H]⁺.

Step 4: 1'-(1-(5-Bromopyridin-2-yl)-3-(difluoromethoxy)propyl)-4-(methoxymethoxy)-2-methyl-1'H,2H-3,4'-bipyrazole To a solution of 4-(methoxymethoxy)-2-methyl-1'H,2H-3,4'-bipyrazole (150 mg, 0.72 mmol, 1.0 equiv.) in ACN (20 mL) was added Cs₂CO₃ (469 mg, 1.44 mmol, 2.0 equiv.) at room temperature over 0.5 h.

To the resulting mixture was added 1-(5-bromopyridin-2-yl)-3-(difluoromethoxy)propyl methanesulfonate (311 mg, 0.86 mmol, 1.2 equiv.). The resulting mixture was stirred at 80° C. for 2 h. The reaction was quenched with water (50 mL). The resulting mixture was extracted with ethyl acetate (3×20 mL). The organic layers were combined, dried over anhydrous sodium sulfate, filtered and concentrated. The resulting residue was purified by silica gel chromatography (0→80% EA/PE) to yield 1'-(1-(5-bromopyridin-2-yl)-3-(difluoromethoxy)propyl)-4-(methoxymethoxy)-2-methyl-1'H,2H-3,4'-bipyrazole as a yellow oil. LC/MS: mass calculated for $C_{18}H_{20}BrF_2N_5O_3$: 471.07, measured (ES, m/z): 472.05, 474.05 [M+H, M+H+2]⁺.

Step 5: (6-(3-(Difluoromethoxy)-1-(4-(methoxymethoxy)-2-methyl-1'H,2H-[3,4'-bipyrazol]-1'-yl)propyl)pyridin-3-yl)boronic acid To a solution of 1'-(1-(5-bromopyridin-2-yl)-3-(difluoromethoxy)propyl)-4-(methoxymethoxy)-2-methyl-1'H,2H-3,4'-bipyrazole (150 mg, 0.32 mmol, 1.0 equiv.) in 1,4-dioxane (15 mL) was added 4,4,4',4',5,5,5',5'-octamethyl-2,2'-bi(1,3,2-dioxaborolane) (161 mg, 0.64 mmol, 2.0 equiv.), KOAc (94 mg, 0.95 mmol, 3.0 equiv.) and Pd(dppf)Cl₂ (27 mg, 0.03 mmol, 0.1 equiv.). The resulting mixture was maintained under nitrogen and stirred at 90° C. for 2 h. After cooling to room temperature, the reaction was quenched with water (50 mL).

The resulting mixture was extracted with ethyl acetate (3×20 mL). The resulting mixture was filtered and concentrated to yield (6-(3-(difluoromethoxy)-1-(4-(methoxymethoxy)-2-methyl-1'H,2H-[3,4'-bipyrazol]-1'-yl)propyl)pyridin-3-yl)boronic acid as a black oil for resulting. LC/MS: mass calculated for $C_{18}H_{22}BF_2N_5O_5$: 437.17, measured (ES, m/z): 438.05 [M+H]⁺.

Step 6: 1'-(1-(5-(3-Chloro-6-(4-chloro-1H-1,2,3-triazol-1-yl)-2-fluorophenyl)pyridin-2-yl)-3-(difluoromethoxy)propyl)-4-(methoxymethoxy)-2-methyl-1'H,2H-3,4'-bipyrazole To a solution of (6-(3-(difluoromethoxy)-1-(4-(methoxymethoxy)-2-methyl-1'H,2H-[3,4'-bipyrazol]-1'-yl)propyl)pyridin-3-yl)boronic acid (140 mg, 0.32 mmol, 1.0 equiv.) in 1,4-dioxane (20 mL) and H₂O (2 mL) was added 4-chloro-1-(4-chloro-3-fluoro-2-iodophenyl)-1H-1,2,3-triazole (229 mg, 0.64 mmol, 2.0 equiv.), K₂CO₃ (133 mg, 0.96 mmol, 3.0 equiv.) and Pd(PPh₃)₄ (37 mg, 0.03 mmol, 0.1 equiv.). The resulting mixture was maintained under nitrogen and stirred at 90° C. for 2 h. After cooling to room temperature, the reaction was quenched with water (50 mL). The resulting mixture was extracted with ethyl acetate (3×20 mL). The organic layers were combined, dried over anhydrous sodium sulfate, filtered and concentrated. The resulting residue was purified by silica gel chromatography (0→5% MeOH/DCM) to yield 1'-(1-(5-(3-chloro-6-(4-chloro-1H-1,2,3-triazol-1-yl)-2-fluorophenyl)pyridin-2-yl)-3-(difluoromethoxy)propyl)-4-(methoxymethoxy)-2-methyl-1'H,2H-3,4'-bipyrazole as a yellow solid. LC/MS: mass calculated for $C_{26}H_{23}Cl_2F_3N_8O_3$: 622.12, measured (ES, m/z): 623.05 [M+H]⁺.

Step 7: 5-(3-Chloro-6-(4-chloro-1H-1,2,3-triazol-1-yl)-2-fluorophenyl)-2-(3-(difluoromethoxy)-1-(4-(methoxymethoxy)-2-methyl-1'H,2H-[3,4'-bipyrazol]-1'-yl)propyl)pyridine 1-oxide To a solution of 1'-(1-(5-(3-chloro-6-(4-chloro-1H-1,2,3-triazol-1-yl)-2-fluorophenyl)pyridin-2-yl)-3-(difluoromethoxy)propyl)-4-(methoxymethoxy)-2-methyl-1'H,2H-3,4'-bipyrazole (176 mg, 0.28 mmol, 1.0 equiv.) in MeOH (1 mL) was added methyltrioxorhenium (35 mg, 0.14 mmol, 0.5 equiv.) and H₂O₂ (0.14 mL, 1.41 mmol, 5.0 equiv.). The resulting mixture was stirred at room temperature. for 4 h. The reaction mixture was purified by reverse phase chromatography on C₁₈ (80 g, 5%→55%, MeCN/H₂O) to yield 5-(3-chloro-6-(4-chloro-1H-1,2,3-triazol-1-yl)-2-fluorophenyl)-2-(3-(difluoromethoxy)-1-(4-(methoxymethoxy)-2-methyl-1'H,2H-[3,4'-bipyrazol]-1'-yl)propyl)pyridine 1-oxide as a yellow solid. LC/MS: mass calculated for $C_{26}H_{23}Cl_2F_3N_8O_4$: 638.12, measured (ES, m/z): 639.10 [M+H]⁺.

Step 8: (R)-5-(3-Chloro-6-(4-chloro-1H-1,2,3-triazol-1-yl)-2-fluorophenyl)-2-(3-(difluoromethoxy)-1-(4-hydroxy-2-methyl-1'H,2H-[3,4'-bipyrazol]-1'-yl)propyl)pyridine 1-oxide A solution of 5-(3-chloro-6-(4-chloro-1H-1,2,3-triazol-1-yl)-2-fluorophenyl)-2-(3-(difluoromethoxy)-1-(4-(methoxymethoxy)-2-methyl-1'H,2H-[3,4'-bipyrazol]-1'-yl)propyl)pyridine 1-oxide (81 mg, 0.13 mmol, 1.0 equiv.) in DCM (3 mL) and TFA (1 mL) was stirred at room temperature. for 14 h. The resulting mixture was concentrated and purified by reverse phase chromatography on C₁₈ (80 g, 5%→55%, MeCN/H₂O) and Chiral HPLC to yield (R)-5-(3-chloro-6-(4-chloro-1H-1,2,3-triazol-1-yl)-2-fluorophenyl)-2-(3-(difluoromethoxy)-1-(4-hydroxy-2-methyl-1'H,2H-[3,4'-bipyrazol]-1'-yl)propyl)pyridine 1-oxide as a white solid.

LC/MS: mass calculated for $C_{24}H_{19}Cl_2F_3N_8O_3$: 594.10, measured (ES, m/z): 595.05 [M+H]⁺. ¹H NMR (400 MHz, DMSO-d₆) δ 8.66 (s, 1H), 8.53 (s, 1H), 8.41 (s, 1H), 8.27 (s, 1H), 8.02 (t, J=8.2 Hz, 1H), 7.93 (s, 1H), 7.68 (d, J=8.6 Hz, 1H), 7.28 (d, J=8.3 Hz, 1H), 7.16 (d, J=8.3 Hz, 1H), 7.02 (s, 1H), 6.63 (t, J=57.0 Hz, 1H), 6.21-6.25 (m, 1H), 3.81-3.86 (m, 1H), 3.79 (s, 3H), 3.65-3.73 (m, 1H), 2.57-2.68 (m, 2H). ¹⁹F NMR (376 MHz, DMSO-d₆) δ −83.20, −112.92.

Example 786: (R)-5-(3-Chloro-2-fluoro-6-(1H-tetrazol-1-yl)phenyl)-2-(2-(1-(difluoromethyl)-1H-1,2,3-triazol-4-yl)-1-(4-(2-(trifluoromethyl)pyridin-4-yl)-1H-pyrazol-1-yl)ethyl)pyridine 1-oxide

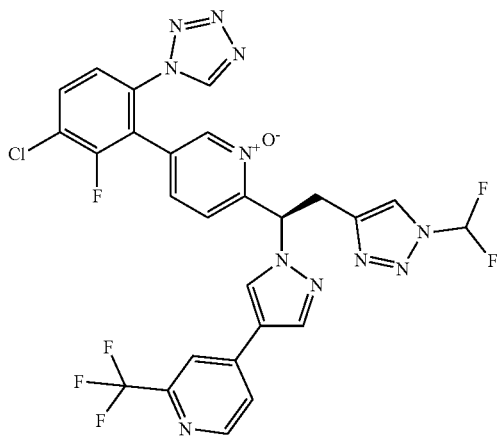

LC/MS: mass calculated for $C_{26}H_{16}ClF_6N_{11}O$: 647.11, measured (ES, m/z): 648.05 [M+H]$^+$. $^1$H NMR (400 MHz, DMSO-d$_6$) δ 9.61 (s, 1H), 8.63-8.71 (m, 2H), 8.44 (s, 1H), 8.29 (s, 1H), 8.07 (d, J=1.7 Hz, 1H), 8.01 (d, J=8.7 Hz, 1H), 7.72-7.99 (m, 3H), 7.65-7.75 (m, 1H), 7.50 (d, J=8.3 Hz, 1H), 7.25-7.35 (m, 1H), 6.40-6.51 (m, 1H), 3.73-3.91 (m, 2H). $^{19}$F NMR (376 MHz, DMSO-d$_6$) δ −66.58, −73.83, −96.50, −112.78.

Example 787: (R)-5-(3-Chloro-2-fluoro-6-(1H-tetrazol-1-yl)phenyl)-2-(3-(difluoromethoxy)-1-(4-(1-(difluoromethyl)-4-fluoro-1H-1,2,3-triazol-5-yl)-1H-pyrazol-1-yl)propyl)pyridine 1-oxide

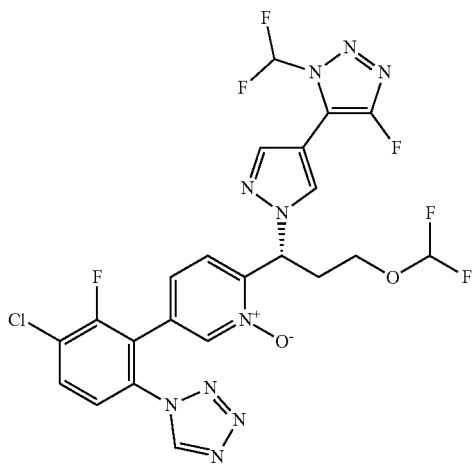 [SMILES: [O-][n+]1cc(-c2c(-n3cnnn3)ccc(Cl)c2F)ccc1[C@@H](CCOC(F)F)n1cc(-c2c(F)nnn2C(F)F)cn1]

Step 1: 4-Iodo-1-(4-methoxybenzyl)-5-(1-(tetrahydro-2H-pyran-2-yl)-1H-pyrazol-4-yl)-1H-1,2,3-triazole To a solution of 1-(azidomethyl)-4-methoxybenzene (1.0 g, 5.96 mmol, 1.5 equiv.) in THF (10 mL) was added cuprous iodide (0.76 g, 3.97 mmol, 1.0 equiv.), iodine monochloride (0.77 g, 4.77 mmol, 1.2 equiv.), triethylamine (0.66 mL, 4.77 mmol, 1.2 equiv.) and 4-ethynyl-1-(tetrahydro-2H-pyran-2-yl)-1H-pyrazole (0.70 g, 3.97 mmol, 1.0 equiv.). The solution was stirred for 3 h at room temperature. The reaction mixture was filtered, the filtrate was diluted with H$_2$O, extracted with ethyl acetate twice. The combined organic layers were washed with brine, dried over Na$_2$SO$_4$, concentrated and purified by silica gel chromatography (0→60%, EA/PE) to yield 4-iodo-1-(4-methoxybenzyl)-5-(1-(tetrahydro-2H-pyran-2-yl)-1H-pyrazol-4-yl)-1H-1,2,3-triazole as a yellow solid. LC/MS: mass calculated for $C_{18}H_{20}IN_5O_2$: 465.07, measured (ES, m/z): 466.00 [M+H]$^+$.

Step 2: 4-Fluoro-1-(4-methoxybenzyl)-5-(1-(tetrahydro-2H-pyran-2-yl)-1H-pyrazol-4-yl)-1H-1,2,3-triazole A mixture of 4-iodo-1-(4-methoxybenzyl)-5-(1-(tetrahydro-2H-pyran-2-yl)-1H-pyrazol-4-yl)-1H-1,2,3-triazole (0.90 g, 1.93 mmol, 1.0 equiv.), potassium fluoride (1.1 g, 19.34 mmol, 10.0 equiv.) in acetonitrile (5 mL) and water (5 mL) was stirred for 10 min at 180° C. The mixture was diluted with water, extracted with ethyl acetate twice. The combined organic layers were washed with brine, dried over Na$_2$SO$_4$, concentrated and purified by silica gel chromatography (0→80%, EA/PE) to yield 4-fluoro-1-(4-methoxybenzyl)-5-(1-(tetrahydro-2H-pyran-2-yl)-1H-pyrazol-4-yl)-1H-1,2,3-triazole as a light yellow oil. LC/MS: mass calculated for $C_{18}H_{20}FN_5O_2$: 357.16, measured (ES, m/z): 358.15 [M+H]$^+$.

Step 3: 4-Fluoro-5-(1-(tetrahydro-2H-pyran-2-yl)-1H-pyrazol-4-yl)-1H-1,2,3-triazole. 4-Fluoro-1-(4-methoxybenzyl)-5-(1-(tetrahydro-2H-pyran-2-yl)-1H-pyrazol-4-yl)-1H-1,2,3-triazole (0.50 g, 1.40 mmol, 1.0 equiv.) was dissolved in CH$_3$OH (10 mL), and 10% palladium-carbon (0.12 g) was added for hydrogenation with H$_2$ under atmospheric pressure. After 24 h stirring at 50° C., the reaction was stopped, and the catalyst was removed by filtration. The filtrate was concentrated under vacuum to yield 4-fluoro-5-(1-(tetrahydro-2H-pyran-2-yl)-1H-pyrazol-4-yl)-1H-1,2,3-triazole as yellow oil. LC/MS: mass calculated for $C_{10}H_{12}FN_5O$: 237.10, measured (ES, m/z): 238.15 [M+H]$^+$ Step 4: 1-(Difluoromethyl)-4-fluoro-5-(1-(tetrahydro-2H-pyran-2-yl)-1H-pyrazol-4-yl)-1H-1,2,3-triazole A mixture of 4-fluoro-5-(1-(tetrahydro-2H-pyran-2-yl)-1H-pyrazol-4-yl)-1H-1,2,3-triazole (0.42 g, 1.77 mmol, 1.0 equiv.), sodium chlorodifluoroacetate (0.54 g, 3.54 mmol, 2.0 equiv.) and cesium carbonate (1.7 g, 5.31 mmol, 3.0 equiv.) in DMF (5 mL) was stirred for 4 h at 90° C. under N$_2$. The solution was diluted with water, extracted with ethyl acetate twice. The combined organic layers were washed with brine, dried over Na$_2$SO$_4$, concentrated and purified by silica gel chromatography (0→50% EtOAc/petroleum ether) to yield 1-(difluoromethyl)-4-fluoro-5-(1-(tetrahydro-2H-pyran-2-yl)-1H-pyrazol-4-yl)-1H-1,2,3-triazole as an yellow oil. LC/MS: mass calculated for $C_{11}H_{12}F_3N_5O$: 287.10, measured (ES, m/z): 288.10 [M+H]$^+$.

Step 5: 1-(Difluoromethyl)-4-fluoro-5-(1H-pyrazol-4-yl)-1H-1,2,3-triazole

A mixture of 1-(difluoromethyl)-4-fluoro-5-(1-(tetrahydro-2H-pyran-2-yl)-1H-pyrazol-4-yl)-1H-1,2,3-triazole (0.19 g, 0.66 mmol, 1.0 equiv.) and HCl in 1,4-dioxane (1 mL) was stirred for 1 h at room temperature. The reaction solution was concentrated under vacuum to yield 1-(difluoromethyl)-4-fluoro-5-(1H-pyrazol-4-yl)-1H-1,2,3-triazole as yellow oil. LC/MS: mass calculated for $C_6H_4F_3N_5$: 203.04, measured (ES, m/z): 204.05 [M+H]$^+$.

Step 6: 5-Bromo-2-(3-(difluoromethoxy)-1-(4-(1-(difluoromethyl)-4-fluoro-1H-1,2,3-triazol-5-yl)-1H-pyrazol-1-yl)propyl)pyridine A mixture of 1-(difluoromethyl)-4-fluoro-5-(1H-pyrazol-4-yl)-1H-1,2,3-triazole (0.10 g, 0.49 mmol, 1.0 equiv.) and cesium carbonate (0.18 g, 0.54 mmol, 1.1 equiv.) in acetonitrile (2 mL) was stirred for 15 min at room temperature. 1-(5-Bromopyridin-2-yl)-3-(difluoromethoxy)propyl methanesulfonate (0.18 g, 0.49 mmol, 1.0 equiv.) was added and the solution was stirred for 3 h at 90° C. The solution was diluted with H$_2$O, extracted with ethyl acetate twice. The combined organic layers were washed with brine, dried over Na$_2$SO$_4$, concentrated and purified by silica gel chromatography (0→60% EtOAc/petroleum ether) to yield 5-bromo-2-(3-(difluoromethoxy)-1-(4-(1-(difluoromethyl)-4-fluoro-1H-1,2,3-triazol-5-yl)-1H-pyrazol-1-yl)propyl)pyridine as a light yellow oil. LC/MS: mass calculated for $C_{15}H_{12}BrF_5N_6O$: 466.02, measured (ES, m/z): 466.98, 468.95 [M+H, M+H+2]$^+$.

Step 7: 4-Chloro-2-(6-(3-(difluoromethoxy)-1-(4-(1-(difluoromethyl)-4-fluoro-1H-1,2,3-triazol-5-yl)-1H-pyrazol-1-yl)propyl)pyridin-3-yl)-3-fluoroaniline A mixture of 5-bromo-2-(3-(difluoromethoxy)-1-(4-(1-(difluoromethyl)-4-fluoro-1H-1,2,3-triazol-5-yl)-1H-pyrazol-1-yl)propyl)pyridine (67 mg, 0.14 mmol, 1.0 equiv.), (6-amino-3-chloro-2-fluorophenyl)boronic acid (54 mg, 0.29 mmol, 2.0 equiv.), Pd(PPh$_3$)$_4$ (33 mg, 0.03 mmol, 0.2 equiv.), K$_2$CO$_3$ (120 mg, 0.86 mmol, 6.0 equiv.) in 1,4-dioxane (2 mL) and water (0.5 mL) was refluxed at 90° C. under N$_2$ for 2 h. The mixture was diluted with water, extracted with ethyl acetate twice. The combined organic layers were washed with brine, dried over Na$_2$SO$_4$, concentrated and purified by silica gel chromatography (0→60% EA/PE) to yield 4-chloro-2-(6-(3-(difluoromethoxy)-1-(4-(1-(difluoromethyl)-4-fluoro-1H-1,2,3-triazol-5-yl)-1H-pyrazol-1-yl)propyl)pyridin-3-yl)-3-fluoroaniline as a light yellow oil. LC/MS: mass calculated for $C_{21}H_{16}ClF_6N_7O$: 531.10, measured (ES, m/z): 532.00 [M+H]$^+$.

Step 8: 5-(3-Chloro-2-fluoro-6-(1H-tetrazol-1-yl)phenyl)-2-(3-(difluoromethoxy)-1-(4-(1-(difluoromethyl)-4-fluoro-1H-1,2,3-triazol-5-yl)-1H-pyrazol-1-yl)propyl)pyridine A mixture of 4-chloro-2-(6-(3-(difluoromethoxy)-1-(4-(1-(difluoromethyl)-4-fluoro-1H-1,2,3-triazol-5-yl)-1H-pyrazol-1-yl)propyl)pyridin-3-yl)-3-fluoroaniline (67 mg, 0.13 mmol, 1.0 equiv.), trimethoxymethane (1 mL), azidotrimethylsilane (1 mL) and acetic acid (1 mL) was stirred overnight at room temperature. The reaction was purified by reverse phase chromatography on C18 (80 g, MeCN/H$_2$O (0.05% CF$_3$COOH): 0→45%) to yield 5-(3-chloro-2-fluoro-6-(1H-tetrazol-1-yl)phenyl)-2-(3-(difluoromethoxy)-1-(4-(1-(difluoromethyl)-4-fluoro-1H-1,2,3-triazol-5-yl)-1H-pyrazol-1-yl)propyl)pyridine as a light yellow solid. LC/MS: mass calculated for $C_{22}H_{15}ClF_6N_{10}O$: 584.10, measured (ES, m/z): 585.10 [M+H]$^+$.

Step 9: (R)-5-(3-chloro-2-fluoro-6-(1H-tetrazol-1-yl)phenyl)-2-(3-(difluoromethoxy)-1-(4-(1-(difluoromethyl)-4-fluoro-1H-1,2,3-triazol-5-yl)-1H-pyrazol-1-yl)propyl)pyridine 1-oxide A mixture of 5-(3-chloro-2-fluoro-6-(1H-tetrazol-1-yl)phenyl)-2-(3-(difluoromethoxy)-1-(4-(1-(difluoromethyl)-4-fluoro-1H-1,2,3-triazol-5-yl)-1H-pyrazol-1-yl)propyl)pyridine (40 mg, 0.07 mmol, 1.0 equiv.), hydrogen peroxide (30 wt %, 0.078 mL, 0.68 mmol, 10.0 equiv.) and methyltrioxorhenium (30 mg, 0.014 mmol, 0.2 equiv.) in CH$_3$OH (1 mL) was stirred for 1 h at room temperature. The mixture was purified by reverse phase chromatography on C18 (80 g, MeCN/H$_2$O (0.05% CF$_3$COOH): 0→45%) to yield and Prep-Chiral-HPLC to yield (R)-5-(3-chloro-2-fluoro-6-(1H-tetrazol-1-yl)phenyl)-2-(3-(difluoromethoxy)-1-(4-(1-(difluoromethyl)-4-fluoro-1H-1,2,3-triazol-5-yl)-1H-pyrazol-1-yl)propyl)pyridine 1-oxide as a white solid.

LC/MS: mass calculated for $C_{22}H_{15}ClF_6N_{10}O_2$: 600.1, measured (ES, m/z): 623.00 [M+Na]$^+$. $^1$H NMR (400 MHz, DMSO-d$_6$): δ9.69 (s, 1H), 8.52 (s, 1H), 8.12-8.50 (m, 2H), 8.05 (t, J=8.2 Hz, 1H), 7.97 (s, 1H), 7.70-7.80 (m, 1H), 7.37 (d, J=8.3 Hz, 1H), 7.15-7.25 (m, 1H), 6.60 (t, J=75.6 Hz, 1H), 6.20-6.34 (m, 1H), 3.79-3.90 (m, 1H), 3.60-3.71 (m, 1H), 2.53-2.68 (m, 2H). $^{19}$F NMR (376 MHz, DMSO-d$_6$): δ −83.51, −98.14, −112.66, −142.95.

Example 788: (R)-5-(3-Chloro-2-fluoro-6-(1H-tetrazol-1-yl)phenyl)-2-(3-(difluoromethoxy)-1-(4-(2-(difluoromethyl)-5-fluoro-2H-1,2,3-triazol-4-yl)-1H-pyrazol-1-yl)propyl)pyridine 1-oxide

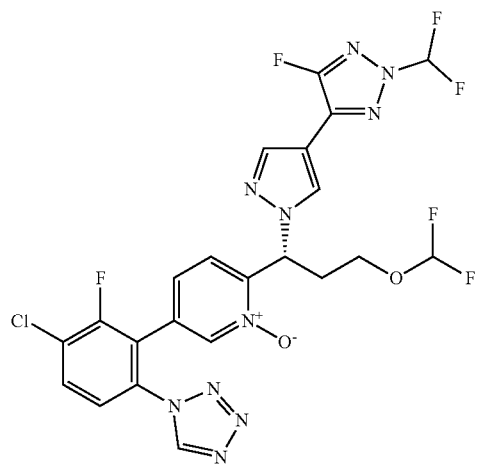 [SMILES: [O-][n+]1cc(-c2c(-n3cnnn3)ccc(Cl)c2F)ccc1[C@@H](CCOC(F)F)n1cc(-c2nn(C(F)F)nc2F)cn1]

A mixture of 5-(3-chloro-2-fluoro-6-(1H-tetrazol-1-yl)phenyl)-2-(3-(difluoromethoxy)-1-(4-(2-(difluoromethyl)-5-fluoro-2H-1,2,3-triazol-4-yl)-1H-pyrazol-1-yl)propyl)pyridine (40 mg, 0.07 mmol, 1.0 equiv.), hydrogen peroxide (30 wt %, 0.078 mL, 0.68 mmol, 10.0 equiv.) and methyltrioxorhenium (3 mg, 0.014 mmol, 0.2 equiv.) in CH$_3$OH (1 mL) was stirred for 1 h at room temperature. The mixture was purified by reverse phase chromatography on C18 (80 g, MeCN/H$_2$O (0.05% CF$_3$COOH): 0→45%) and Prep-Chiral-HPLC to yield (R)-5-(3-chloro-2-fluoro-6-(1H-tetrazol-1-yl)phenyl)-2-(3-(difluoromethoxy)-1-(4-(2-(difluoromethyl)-5-fluoro-2H-1,2,3-triazol-4-yl)-1H-pyrazol-1-yl)propyl)pyridine 1-oxide as a white solid.

LC/MS: mass calculated for C$_{22}$H$_{15}$ClF$_6$N$_{10}$O$_2$: 600.1, measured (ES, m/z): 623.00 [M+Na]$^+$. $^1$H NMR (400 MHz, DMSO-d$_6$): δ9.67 (s, 1H), 8.55 (s, 1H), 8.42-8.47 (m, 1H), 7.87-8.20 (m, 3H), 7.70-7.80 (m, 1H), 7.27 (d, J=8.3 Hz, 1H), 7.13-7.23 (m, 1H), 6.61 (t, J=75.7 Hz, 1H), 6.20-6.30 (m, 1H), 3.79-3.89 (m, 1H), 3.63-3.76 (m, 1H), 2.51-2.71 (m, 2H). $^{19}$F NMR (376 MHz, DMSO-d$_6$): 5-83.38, −97.31, −112.68, −139.72.

Example 789: (S)-5-(3-Chloro-2-fluoro-6-(1H-tetrazol-1-yl)phenyl)-2-(3-(difluoromethoxy)-1-(4-(1-(difluoromethyl)-4-fluoro-1H-1,2,3-triazol-5-yl)-1H-pyrazol-1-yl)propyl)pyridine 1-oxide

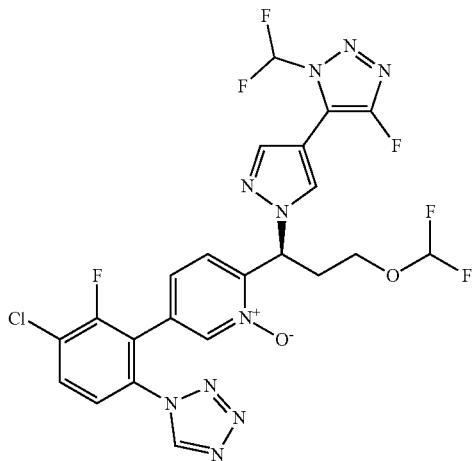 [SMILES: [O-][n+]1cc(-c2c(-n3cnnn3)ccc(Cl)c2F)ccc1[C@H](CCOC(F)F)n1cc(-c2c(F)nnn2C(F)F)cn1]

LC/MS: mass calculated for C$_{22}$H$_{15}$ClF$_6$N$_{10}$O$_2$: 600.10, measured (ES, m/z): 623.00 [M+Na]. $^1$H NMR (400 MHz, DMSO-d$_6$) δ 9.67 (s, 1H), 8.53-8.14 (m, 3H), 8.01-8.10 (m, 1H), 7.97 (s, 1H), 7.72-7.80 (m, 1H), 7.37 (d, J=8.3 Hz, 1H), 7.15-7.25 (m, 1H), 6.60 (t, J=75.6 Hz, 1H), 6.20-6.30 (m, 1H), 3.80-3.90 (m, 1H), 3.60-3.70 (m, 1H), 2.53-2.70 (m, 2H). $^{19}$F NMR (376 MHz, DMSO-d$_6$) δ −83.51, −98.16, −112.66, −142.96.

Example 790: (R*)-5-(3-Chloro-2-fluoro-6-(1H-tetrazol-1-yl)phenyl)-2-(3-(difluoromethoxy)-1-(4-(1-(difluoromethyl)-4-fluoro-1H-1,2,3-triazol-5-yl)-1H-pyrazol-1-yl)propyl)pyridine 1-oxide

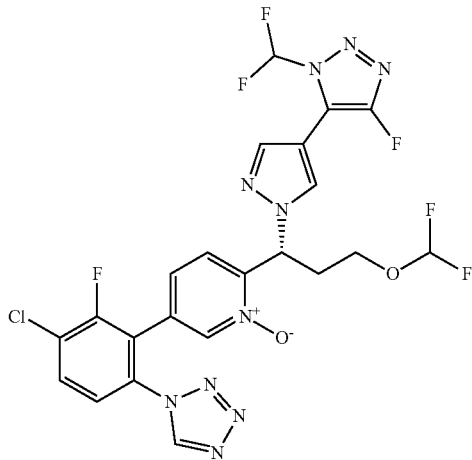

LC/MS: mass calculated for C$_{22}$H$_{15}$ClF$_6$N$_{10}$O$_2$: 600.10, measured (ES, m/z): 623.00 [M+Na]$^+$. $^1$H NMR (400 MHz, DMSO-d$_6$) δ 9.67 (s, 1H), 8.55 (s, 1H), 8.44 (d, J=1.6 Hz, 1H), 7.88-8.20 (m, 3H), 7.73-7.81 (m, 1H), 7.27 (d, J=8.3 Hz, 1H), 7.15-7.21 (m, 1H), 6.61 (t, J=75.7 Hz, 1H), 6.20-6.30 (m, 1H), 3.80-3.90 (m, 1H), 3.63-3.75 (m, 1H), 2.52-2.71 (m, 2H). $^{19}$F NMR (376 MHz, DMSO-d$_6$) δ −83.39, −97.29, −112.68, −139.71.

Example 791: 5-(3-Chloro-2-fluoro-6-(1H-tetrazol-1-yl)phenyl)-2-(1-(1'-(difluoromethyl)-1H,1'H-[4,4'-bipyrazol]-1-yl)-2-(6-(trifluoromethyl)pyridin-3-yl)ethyl)pyridine 1-oxide

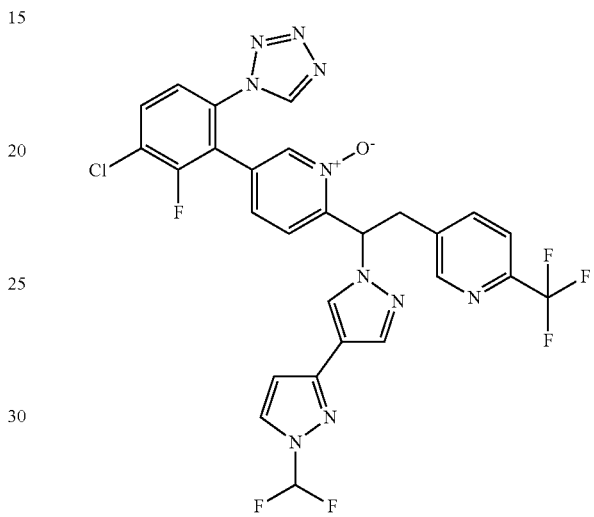

LC/MS: mass calculated for C$_{27}$H$_{17}$ClF$_6$N$_{10}$O: 600.1, measured (ES, m/z 647.2 [M+H]$^+$. $^1$H NMR (400 MHz, CD$_3$OD) δ ppm 3.71-3.92 (m, 2 h) 6.25-6.37 (m, 1H) 7.28-7.35 (m, 1H) 7.41-7.48 (m, 1H) 7.56-7.65 (m, 1H) 7.67-7.74 (m, 1H) 7.79-7.87 (m, 2 h) 7.89-7.96 (m, 3H) 8.18 (s, 1H) 8.43 (s, 1H) 8.53 (s, 1H) 9.40 (s, 1H).

Example 792: (R)-5-(3-Chloro-2-fluoro-6-(4-(trifluoromethyl)-1H-1,2,3-triazol-1-yl)phenyl)-2-(3-(difluoromethoxy)-1-(4-(4-fluoro-1-methyl-1H-1,2,3-triazol-5-yl)-1H-pyrazol-1-yl)propyl)pyridine 1-oxide

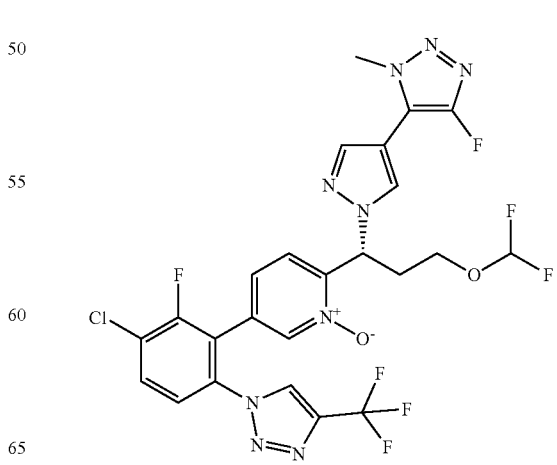

LC/MS: mass calculated for $C_{24}H_{17}ClF_7N_9O_2$: 631.11, measured (ES, m/z): 632.10 [M+H]$^+$. $^1$H NMR (300 MHz, DMSO-d$_6$) δ 9.16 (s, 1H), 8.52 (s, 1H), 8.44 (s, 1H), 8.07 (t, J=8.2 Hz, 1H), 8.00 (s, 1H), 7.73-7.83 (m, 1H), 7.35 (d, J=8.3 Hz, 1H), 7.07-7.21 (m, 1H), 6.62 (t, J=75.7 Hz, 1H), 6.29 (dd, J=9.7, 4.8 Hz, 1H), 4.09 (s, 3H), 3.83-3.85 (m, 1H), 3.70-3.72 (m, 1H), 2.61-2.63 (m, 2 h)/19F NMR (282 MHz, DMSO-d$_6$) d −59.83, −83.37, −112.84, −145.20.

Example 793: (S)-5-(3-Chloro-2-fluoro-6-(4-(trifluoromethyl)-1H-1,2,3-triazol-1-yl)phenyl)-2-(3-(difluoromethoxy)-1-(4-(4-fluoro-1-methyl-1H-1,2,3-triazol-5-yl)-1H-pyrazol-1-yl)propyl)pyridine 1-oxide

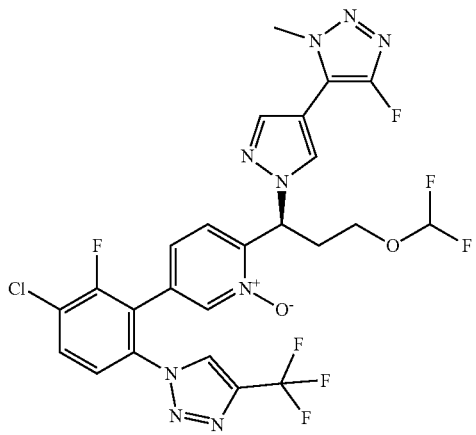 [SMILES: Cn1nnc(F)c1-c1cnn([C@@H](CCOC(F)F)c2ccc(-c3c(-n4cc(C(F)(F)F)nn4)ccc(Cl)c3F)c[n+]2[O-])c1]

LC/MS: mass calculated for $C_{24}H_{17}ClF_7N_9O_2$: 631.11, measured (ES, m/z): 632.10 [M+H]$^+$. $^1$H NMR (300 MHz, DMSO-d$_6$) δ 9.16 (s, 1H), 8.52 (s, 1H), 8.44 (s, 1H), 8.03-8.13 (m, 1H), 8.00 (s, 1H), 7.78 (d, J=8.4 Hz, 1H), 7.35 (d, J=8.1 Hz, 1H), 7.17 (d, J=8.4 Hz, 1H), 6.36-6.89 (m, 1H), 6.26-6.33 (m, 1H), 4.09 (s, 3H), 3.82-3.84 (m, 1H), 3.69-3.71 (m, 1H), 2.62-2.64 (m, 2H). $^{19}$F NMR (282 MHz, DMSO-d$_6$) δ −59.83, −83.37, −112.84, −145.20.

Example 794: (S)-5-(3-Chloro-2-fluoro-6-(4-(trifluoromethyl)-1H-1,2,3-triazol-1-yl)phenyl)-2-(3-(difluoromethoxy)-1-(4-(1-methyl-1H-1,2,3-triazol-5-yl)-1H-pyrazol-1-yl)propyl)pyridine 1-oxide

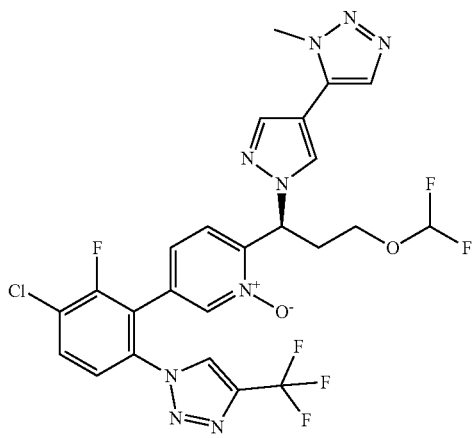 [SMILES: Cn1nncc1-c1cnn([C@@H](CCOC(F)F)c2ccc(-c3c(-n4cc(C(F)(F)F)nn4)ccc(Cl)c3F)c[n+]2[O-])c1]

LC/MS: mass calculated for $C_{24}H_{18}ClF_6N_9O_2$: 613.12, measured (ES, m/z): 614.10 [M+H]$^+$. $^1$H NMR (300 MHz, DMSO-d$_6$) δ 9.17 (s, 1H), 8.52 (s, 1H), 8.44 (s, 1H), 8.00-8.12 (m, 2H), 7.89 (s, 1H), 7.76-7.80 (m, 1H), 7.24-7.37 (m, 1H), 6.91-7.20 (m, 1H), 6.63 (t, J=75.7 Hz, 1H), 6.20-6.30 (m, 1H), 4.09 (s, 3H), 3.80-3.90 (m, 1H), 3.67-3.78 (m, 1H), 2.55-2.70 (m, 2H). $^{19}$F NMR (282 MHz, DMSO-d$_6$) δ −59.80, −73.54, −83.31, −112.84.

Example 795: (R)-5-(3-chloro-2-fluoro-6-(4-(trifluoromethyl)-1H-1,2,3-triazol-1-yl)phenyl)-2-(3-(difluoromethoxy)-1-(4-(1-methyl-1H-1,2,4-triazol-5-yl)-1H-pyrazol-1-yl)propyl)pyridine 1-oxide

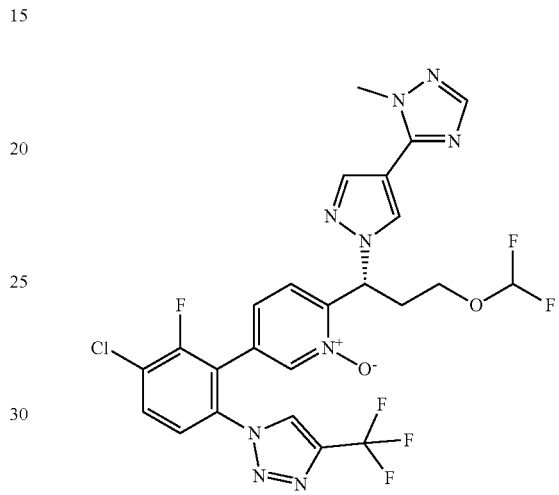

Step 1: (R)-5-Bromo-2-(3-(difluoromethoxy)-1-(4-(1-methyl-1H-1,2,4-triazol-5-yl)-1H-pyrazol-1-yl)propyl)pyridine Methyl-5-(1H-pyrazol-4-yl)-1H-1,2,4-triazole (31.9 g, 213.79 mmol, 1.1 equiv.) and Cs$_2$CO$_3$ (63.3 g, 194.35 mmol, 1.0 equiv.) were suspended in CH$_3$CN (100 mL) and stirred at room temperature for 30 min, after which a solution of 1-(5-bromopyridin-2-yl)-3-(difluoromethoxy)propyl methanesulfonate (70.0 g, 194.35 mmol, 1.0 equiv.) in CH$_3$CN (40 mL) was added. The resulting mixture was stirred at 80° C. for 2 hours.

Following this, EA (2000 mL) was added after the mixture cooled to room temperature and washed by H$_2$O (300 mL), then dried over anhydrous Na$_2$SO$_4$, filtered, and concentrated under reduced pressure. The residue was purified by normal phase chromatography (mobile phase: PE/EA 0→100%) to yield 73.0 g (44.8% yield) yellow oil which was further separated by chiral SFC to yield (R)-5-bromo-2-(3-(difluoromethoxy)-1-(4-(1-methyl-1H-1,2,4-triazol-5-yl)-1H-pyrazol-1-yl)propyl)pyridine. LC/MS: mass calculated for $C_{15}H_{15}BrF_2N_6O$: 412.05, measured (ES, m/z): 413.10 [M+H]$^+$.

Step 2: (R)-(6-(3-(Difluoromethoxy)-1-(4-(1-methyl-1H-1,2,4-triazol-5-yl)-1H-pyrazol-1-yl)propyl)pyridin-3-yl)boronic acid (R)-5-Bromo-2-(3-(difluoromethoxy)-1-(4-(1-methyl-1H-1,2,4-triazol-5-yl)-1H-pyrazol-1-yl)propyl)pyridine (15.3 g, 36.90 mmol, 1.0 equiv.), 4,4,4',4',5,5,5',5'-octamethyl-2,2'-bi(1,3,2-dioxaborolane) (14.1 g, 55.36 mmol, 1.5 equiv.), KOAc (10.9 g, 110.72 mmol, 3.0 equiv.) and Pd(dppf)Cl$_2$ (2.7 g, 3.69 mmol, 0.1 equiv.) were dissolved in 1,4-dioxane (150.0 mL). The mixture was charged with N$_2$ and then heated to 100° C. for 2.0 h. The resulting solution was diluted with 200 mL of water, then extracted with EA (600 mL×3). The organic layers were combined, washed with brine (200 mL), dried and concentrated under vacuum to yield (R)-(6-(3-(difluoromethoxy)-1-(4-(1-methyl-1H-1,2,4-triazol-5-yl)-1H-pyrazol-1-yl)propyl)pyridin-3-yl)boronic acid as a residue, which was used for the next step without further purification. LC/MS: mass calculated for C$_{15}$H$_{17}$BF$_2$N$_6$O$_3$: 378.14, measured (ES, m/z): 379.05 [M+H]$^+$.

Step 3: (R)-5-(3-Chloro-2-fluoro-6-(4-(trifluoromethyl)-1H-1,2,3-triazol-1-yl)phenyl)-2-(3-(difluoromethoxy)-1-(4-(1-methyl-1H-1,2,4-triazol-5-yl)-1H-pyrazol-1-yl)propyl)pyridine (R)-(6-(3-(Difluoromethoxy)-1-(4-(1-methyl-1H-1,2,4-triazol-5-yl)-1H-pyrazol-1-yl)propyl)pyridin-3-yl)boronic acid (13.9 g, 36.90 mmol, 1.0 equiv.), 1-(4-chloro-3-fluoro-2-iodophenyl)-4-(trifluoromethyl)-1H-1,2,3-triazole (17.3 g, 44.29 mmol, 1.2 equiv.), K$_2$CO$_3$ (15.3 g, 110.71 mmol, 3.0 equiv.) and Pd(PPh$_3$)$_4$ (4.3 g, 3.69 mmol, 0.1 equiv.) were dissolved in 1,4-dioxane (140.0 mL) and H$_2$O (28.0 mL). The flask was evacuated and flushed three times with nitrogen and the mixture was stirred 2.0 h at 100° C. under an atmosphere of nitrogen. EA (1000 mL) was added after the mixture cooled to room temperature and washed by water (300 mL), then dried over anhydrous Na$_2$SO$_4$, filtered, and concentrated under reduced pressure. The residue was purified by normal phase chromatography (mobile phase: PE/EA, 0→90%) to yield (R)-5-(3-chloro-2-fluoro-6-(4-(trifluoromethyl)-1H-1,2,3-triazol-1-yl)phenyl)-2-(3-(difluoromethoxy)-1-(4-(1-methyl-1H-1,2,4-triazol-5-yl)-1H-pyrazol-1-yl)propyl)pyridine as a yellow solid. LC/MS: mass calculated for C$_{24}$H$_{18}$ClF$_6$N$_9$O: 597.12, measured (ES, m/z): 598.25 [M+H]$^+$.

Step 4: (R)-5-(3-Chloro-2-fluoro-6-(4-(trifluoromethyl)-1H-1,2,3-triazol-1-yl)phenyl)-2-(3-(difluoromethoxy)-1-(4-(1-methyl-1H-1,2,4-triazol-5-yl)-1H-pyrazol-1-yl)propyl)pyridine 1-oxide H$_2$O$_2$ (32.0 mL, 30 wt %) was added to the solution of (R)-5-(3-chloro-2-fluoro-6-(4-(trifluoromethyl)-1H-1,2,3-triazol-1-yl)phenyl)-2-(3-(difluoromethoxy)-1-(4-(1-methyl-1H-1,2,4-triazol-5-yl)-1H-pyrazol-1-yl)propyl)pyridine (13.0 g, 21.74 mmol, 1.0 equiv.) and ReMeO$_3$ (5.4 g, 21.74 mmol, 1.0 equiv.) in MeOH (320 mL) and the mixture stirred at room temperature for 3 hours. Following this, EA (600 mL) was added and washed by water (100 mL), then dried over anhydrous Na$_2$SO$_4$, filtered, and concentrated under reduced pressure. The residue was purified by normal phase chromatography (mobile phase: PE/EA, 0→100%) to yield yellow resulting residue which was further purified by chiral SFC to yield (R)-5-(3-chloro-2-fluoro-6-(4-(trifluoromethyl)-1H-1,2,3-triazol-1-yl)phenyl)-2-(3-(difluoromethoxy)-1-(4-(1-methyl-1H-1,2,4-triazol-5-yl)-1H-pyrazol-1-yl)propyl)pyridine 1-oxide as a light yellow solid.
LC/MS: mass calculated for C$_{24}$H$_{18}$ClF$_6$N$_9$O$_2$: 613.12, measured (ES, m/z): 614.00 [M+H]$^+$. $^1$H NMR (400 MHz, DMSO-d$_6$) δ 9.17 (s, 1H), 8.61 (s, 1H), 8.43 (s, 1H), 8.01-8.10 (m, 2H), 7.89 (s, 1H), 7.70-7.80 (m, 1H), 7.32 (d, J=8.3 Hz, 1H), 7.10-7.20 (m, 1H), 6.43-6.84 (m, 1H), 6.21-6.31 (m, 1H), 3.96 (s, 3H), 3.79-3.88 (m, 1H), 3.66-3.76 (m, 1H), 2.52-2.72 (m, 2H). $^{19}$F NMR (376 MHz, DMSO-d$_6$) δ −59.80, −83.37, −112.84.

Example 797: (S)-5-(3-Chloro-2-fluoro-6-(4-(trifluoromethyl)-1H-1,2,3-triazol-1-yl)phenyl)-2-(3-(difluoromethoxy)-1-(4-(1-methyl-1H-1,2,3-triazol-4-yl)-1H-pyrazol-1-yl)propyl)pyridine 1-oxide

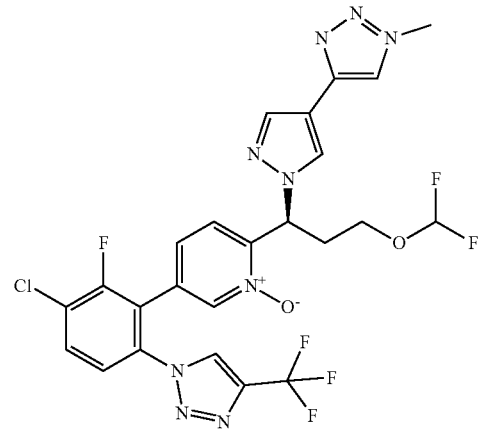

LC/MS: mass calculated for C$_{24}$H$_{18}$ClF$_6$N$_9$O$_2$: 613.12, measured (ES, m/z): 614.00 [M+H]$^+$. $^1$H NMR (300 MHz, DMSO-d$_6$) δ 9.17 (s, 1H), 8.61 (s, 1H), 8.44 (s, 1H), 8.21 (s, 1H), 8.01-8.10 (m, 1H), 7.90 (s, 1H), 7.73-7.80 (m, 1H), 7.32 (d, J=8.3 Hz, 1H), 7.13-7.21 (m, 1H), 6.63 (t, J=75.7 Hz, 1H), 6.15-6.27 (m, 1H), 3.96 (s, 3H), 3.80-3.90 (m, 1H), 3.60-3.77 (m, 1H), 2.56-2.74 (m, 2H). $^{19}$F NMR (282 MHz, DMSO-d$_6$) δ −59.80, −73.66, −83.34, −112.83.

Example 798: (S)-5-(3-Chloro-2-fluoro-6-(4-(trifluoromethyl)-1H-1,2,3-triazol-1-yl)phenyl)-2-(3-(difluoromethoxy)-1-(4-(1-methyl-1H-1,2,4-triazol-5-yl)-1H-pyrazol-1-yl)propyl)pyridine 1-oxide

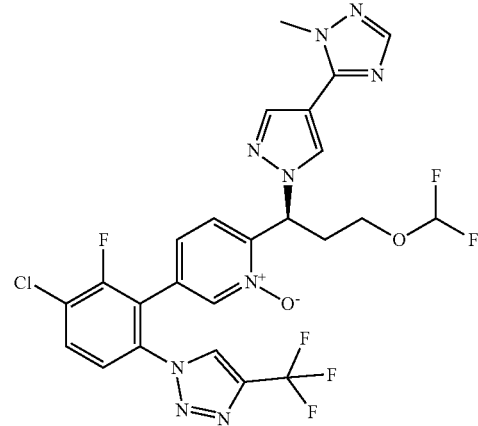 [SMILES: Cn1ncnc1-c1cnn([C@@H](CCOC(F)F)c2ccc(-c3c(-n4cc(C(F)(F)F)nn4)ccc(Cl)c3F)c[n+]2[O-])c1]

LC/MS: mass calculated for C$_{24}$H$_{18}$ClF$_6$N$_9$O$_2$: 613.12, measured (ES, m/z): 614.10 [M+H]$^+$. $^1$H NMR (300 MHz, DMSO-d$_6$) δ 9.17 (s, 1H), 8.61 (s, 1H), 8.44 (s, 1H), 8.01-8.12 (m, 2H), 7.90 (s, 1H), 7.75-7.82 (m, 1H), 7.32 (d, J=8.3 Hz, 1H), 7.13-7.21 (m, 1H), 6.63 (t, J=75.7 Hz, 1H), 6.25-6.33 (m, 1H), 3.96 (s, 3H), 3.80-3.90 (m, 1H), 3.65-

3.79 (m, 1H), 2.56-2.74 (m, 2H) $^{19}$F NMR (282 MHz, DMSO-d$_6$) δ -59.80, -83.34, -112.83.

Example 799: (R)-5-(3-Chloro-2-fluoro-6-(4-(trifluoromethyl)-1H-1,2,3-triazol-1-yl)phenyl)-2-(3-(difluoromethoxy)-1-(4-(1-methyl-1H-1,2,3-triazol-4-yl)-1H-pyrazol-1-yl)propyl)pyridine 1-oxide

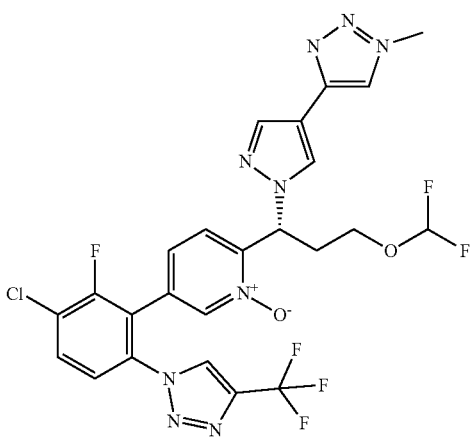

LC/MS: mass calculated for C$_{24}$H$_{18}$ClF$_6$N$_9$O$_2$: 613.12, measured (ES, m/z): 614.00 [M+H]$^+$. $^1$H NMR (300 MHz, DMSO-d$_6$) δ 9.19 (s, 1H), 8.43 (s, 1H), 8.31 (s, 1H), 8.20 (s, 1H), 8.04-8.11 (m, 1H), 7.92 (s, 1H), 7.76-7.82 (m, 1H), 7.23-7.30 (m, 1H), 7.13-7.19 (m, 1H), 6.63 (t, J=75.0 Hz, 1H), 6.18-6.26 (m, 1H), 4.06 (s, 3H), 3.81-3.88 (m, 1H), 3.66-3.74 (m, 1H), 2.56-2.64 (m, 2H). $^{19}$F NMR (282 MHz, DMSO) δ -59.78, -83.33, -112.84.

Example 800: (R)-5-(3-Chloro-2-fluoro-6-(4-(trifluoromethyl)-1H-1,2,3-triazol-1-yl)phenyl)-2-(3-(difluoromethoxy)-1-(4-(1-methyl-1H-1,2,3-triazol-5-yl)-1H-pyrazol-1-yl)propyl)pyridine 1-oxide

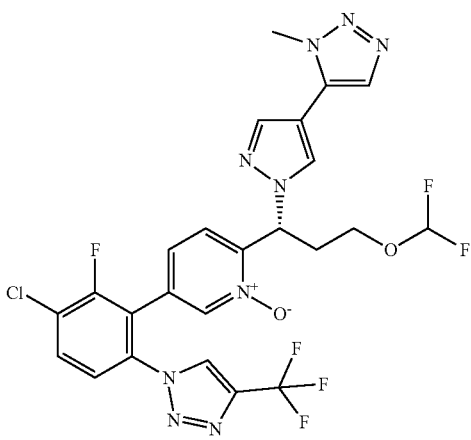 [SMILES: Cn1nncc1-c1cnn([C@H](CCOC(F)F)c2ccc(-c3c(-n4cc(C(F)(F)F)nn4)ccc(Cl)c3F)c[n+]2[O-])c1]

Step 1: 5-(3-Chloro-2-fluoro-6-(4-(trifluoromethyl)-1H-1,2,3-triazol-1-yl)phenyl)-2-(3-(difluoromethoxy)-1-(4-(1-methyl-1H-1,2,3-triazol-5-yl)-1H-pyrazol-1-yl)propyl)pyridine A mixture of (6-(3-(difluoromethoxy)-1-(4-(1-methyl-1H-1,2,3-triazol-5-yl)-1H-pyrazol-1-yl)propyl)pyridin-3-yl)boronic acid (2 g, 5.3 mmol, 1 eq), 1-(4-chloro-3-fluoro-2-iodophenyl)-4-(trifluoromethyl)-1H-1,2,3-triazole (2.5 g, 6.3 mmol, 1.2 eq), Pd(PPh$_3$)$_4$ (1.2 g, 1.06 mmol, 0.2 eq.), K$_2$CO$_3$ (4.4 g, 31.7 mmol, 6 eq.) in 1,4-dioxane (20 mL) and water (5 mL) was heated at reflux at 90° C. under N$_2$ for 2 h. The mixture was diluted with H$_2$O, extracted with ethyl acetate twice. The combined organic layers was washed with brine, dried over Na$_2$SO$_4$, concentrated and purified by silica gel chromatography (0-8%, MeOH/DCM) to yield 5-(3-chloro-2-fluoro-6-(4-(trifluoromethyl)-1H-1,2,3-triazol-1-yl)phenyl)-2-(3-(difluoromethoxy)-1-(4-(1-methyl-1H-1,2,3-triazol-5-yl)-1H-pyrazol-1-yl)propyl)pyridine as a yellow solid. LC/MS: mass calculated for C$_{24}$H$_{18}$ClF$_6$N$_9$O: 597, measured: 598.05 [M+H]$^+$.

Step 2: (R)-5-(3-chloro-2-fluoro-6-(4-(trifluoromethyl)-1H-1,2,3-triazol-1-yl)phenyl)-2-(3-(difluoromethoxy)-1-(4-(1-methyl-1H-1,2,3-triazol-5-yl)-1H-pyrazol-1-yl)propyl)pyridine 1-oxide A mixture of 5-(3-chloro-2-fluoro-6-(4-(trifluoromethyl)-1H-1,2,3-triazol-1-yl)phenyl)-2-(3-(difluoromethoxy)-1-(4-(1-methyl-1H-1,2,3-triazol-5-yl)-1H-pyrazol-1-yl)propyl)pyridine (120 mg, 0.20 mmol, 1.0 eq.), methyltrioxorhenium (25.0 mg, 0.10 mmol, 0.5 eq.) and hydrogen peroxide (113.8 mg, 1.0 mmol, 5.0 eq, 30%) in methanol (2 mL) was stirred at room temperature for 2 h. The reaction was purified by reverse phase chromatography on C18 (80 g, MeCN/H$_2$O (0.05% CF$_3$COOH): 0>>>55%) to yield 5-(3-chloro-2-fluoro-6-(4-(trifluoromethyl)-1H-1,2,3-triazol-1-yl)phenyl)-2-(3-(difluoromethoxy)-1-(4-(1-methyl-1H-1,2,3-triazol-5-yl)-1H-pyrazol-1-yl)propyl)pyridine 1-oxide, which was further separated by prep-chiral-HPLC to yield (R)-5-(3-chloro-2-fluoro-6-(4-(trifluoromethyl)-1H-1,2,3-triazol-1-yl)phenyl)-2-(3-(difluoromethoxy)-1-(4-(1-methyl-1H-1,2,3-triazol-5-yl)-1H-pyrazol-1-yl)propyl)pyridine 1-oxide as a white solid.

HPLC purity (method A): 99.9%, retention time=1.390 min. LC/MS: mass calculated for C$_{24}$H$_{18}$ClF$_6$N$_9$O$_2$: 613.12, measured (ES, m/z): 614.10 [M+H]$^+$. $^1$H NMR (300 MHz, DMSO-d$_6$) δ 9.17 (s, 1H), 8.53 (s, 1H), 8.44 (d, J=1.4 Hz, 1H), 8.00-8.12 (m, 2H), 7.89 (s, 1H), 7.78 (dd, J=8.7, 1.5 Hz, 1H), 7.24-7.37 (m, 1H), 6.91-7.21 (m, 1H), 6.63 (t, J=75.7 Hz, 1H), 6.26 (dd, J=9.7, 4.9 Hz, 1H), 4.09 (s, 3H), 3.65-3.91 (m, 2H), 2.61 (td, J=14.7, 12.2, 5.9 Hz, 2H)/19F NMR (282 MHz, DMSO-d$_6$) d -59.80, -73.57, -83.32, -112.83.

Example 801: (R)-5-(3-Chloro-2-fluoro-6-(1H-tetrazol-1-yl)phenyl)-2-(2-cyclopropyl-1-(4-(1-(difluoromethyl)-1H-1,2,4-triazol-5-yl)-1H-pyrazol-1-yl)ethyl)pyridine 1-oxide

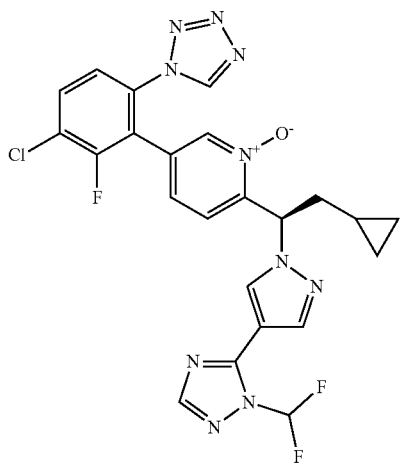 [SMILES: [O-][n+]1cc(-c2c(-n3cnnn3)ccc(Cl)c2F)ccc1[C@@H](CC1CC1)n1cc(-c2ncnn2C(F)F)cn1]

Step 1: 5-Bromo-2-(2-cyclopropyl-1-(4-(1-(difluoromethyl)-1H-1,2,4-triazol-5-yl)-1H-pyrazol-1-yl)ethyl)pyridine A mixture of cesium carbonate (365.6 mg, 1.12 mmol, 1.0 equiv.) and 4-chloro-5-(1H-imidazol-4-yl)-1-methyl-1H-1,2,3-triazole (206 mg, 1.12 mmol, 1.0 equiv.) in acetonitrile (5 mL) was stirred for 15 min at room temperature. 1-(5-bromopyridin-2-yl)-3-(difluoromethoxy)propyl methanesulfonate (323.3 mg, 0.90 mmol, 0.8 equiv.) was added and the solution was stirred for 2.5 h at 90° C. The resulting mixture was diluted with water, and the mixture extracted with EA (3×15 mL). The organic layers were combined, washed with brine (5 mL), dried over Na$_2$SO$_4$ and concentrated. The residue was purified by silica gel chromatography (0%→80%, EA/PE) to yield 5-bromo-2-(2-cyclopropyl-1-(4-(1-(difluoromethyl)-1H-1,2,4-triazol-5-yl)-1H-pyrazol-1-yl)ethyl)pyridine as a light yellow solid. LC/MS: mass calculated for C$_{16}$H$_{15}$BrF$_2$N$_6$: 408.05, measured (ES, m/z): 409.00 [M+H]$^+$.

Step 2: 4-Chloro-2-(6-(2-cyclopropyl-1-(4-(1-(difluoromethyl)-1H-1,2,4-triazol-5-yl)-1H-pyrazol-1-yl)ethyl)pyridin-3-yl)-3-fluoroaniline A mixture of 5-bromo-2-(2-cyclopropyl-1-(4-(1-(difluoromethyl)-1H-1,2,4-triazol-5-yl)-1H-pyrazol-1-yl)ethyl)pyridine (150 mg, 0.37 mmol, 1.0 equiv.), 6-amino-3-chloro-2-fluorophenylboronic acid (104 mg, 0.55 mmol, 1.5 equiv.), Pd(PPh$_3$)$_4$ (42 mg, 0.04 mmol, 0.1 equiv.) and K$_2$CO$_3$ (152 mg, 1.10 mmol, 3.0 equiv.) in 1,4-dioxane/water (V/V=5:1, 1.2 mL) was refluxed at 90° C. under N$_2$ for 3 h. The resulting mixture was diluted with water, and the mixture extracted with EA (3×15 mL). The organic layers were combined, washed with brine (5 mL), dried over Na$_2$SO$_4$ and concentrated. The residue was purified by silica gel chromatography (0%→80%, EA/PE) to yield 4-chloro-2-(6-(2-cyclopropyl-1-(4-(1-(difluoromethyl)-1H-1,2,4-triazol-5-yl)-1H-pyrazol-1-yl)ethyl)pyridin-3-yl)-3-fluoroaniline as an orange solid. LC/MS: mass calculated for C$_{22}$H$_{19}$ClF$_3$N$_7$: 473.13, measured (ES, m/z): 474.25 [M+H]$^+$.

Step 3: 5-(3-Chloro-2-fluoro-6-(1H-tetrazol-1-yl)phenyl)-2-(2-cyclopropyl-1-(4-(1-(difluoromethyl)-1H-1,2,4-triazol-5-yl)-1H-pyrazol-1-yl)ethyl)pyridine A mixture of 4-chloro-2-(6-(2-cyclopropyl-1-(4-(1-(difluoromethyl)-1H-1,2,4-triazol-5-yl)-1H-pyrazol-1-yl)ethyl)pyridin-3-yl)-3-fluoroaniline (138 mg, 0.29 mmol, 1.0 equiv.), trimethoxymethane (2 mL), azidotrimethylsilane (2 mL) and acetic acid (2 mL) was stirred overnight at room temperature. The reaction was purified by reverse chromatography on C18 (0→55% MeCN/H$_2$O (0.05% CF$_3$COOH)) to yield 5-(3-chloro-2-fluoro-6-(1H-tetrazol-1-yl)phenyl)-2-(2-cyclopropyl-1-(4-(1-(difluoromethyl)-1H-1,2,4-triazol-5-yl)-1H-pyrazol-1-yl)ethyl)pyridine as a white solid. LC/MS: mass calculated for C$_{23}$H$_{18}$ClF$_3$N$_{10}$: 526.14, measured (ES, m/z): 527.05 [M+H]$^+$.

Step 4: (R)-5-(3-Chloro-2-fluoro-6-(1H-tetrazol-1-yl)phenyl)-2-(2-cyclopropyl-1-(4-(1-(difluoromethyl)-1H-1,2,4-triazol-5-yl)-1H-pyrazol-1-yl)ethyl)pyridine 1-oxide A mixture of 5-(3-chloro-2-fluoro-6-(1H-tetrazol-1-yl)phenyl)-2-(2-cyclopropyl-1-(4-(1-(difluoromethyl)-1H-1,2,4-triazol-5-yl)-1H-pyrazol-1-yl)ethyl)pyridine (110 mg, 0.21 mmol, 1.0 equiv.), methyltrioxorhenium (26 mg, 0.10 mmol, 0.5 equiv.), hydrogen peroxide (0.5 mL, 30 wt %) in CH$_3$OH (2 mL) was stirred for 1 h at room temperature. The resulting mixture was purified by reverse phase chromatography on C18 (MeCN/H$_2$O (0.05% CF$_3$COOH)) to yield 5-(3-chloro-2-fluoro-6-(1H-tetrazol-1-yl)phenyl)-2-(2-cyclopropyl-1-(4-(1-(difluoromethyl)-1H-1,2,4-triazol-5-yl)-1H-pyrazol-1-yl)ethyl)pyridine 1-oxide as a white solid. The racemic product was separated by chiral-HPLC to yield (R)-5-(3-chloro-2-fluoro-6-(1H-tetrazol-1-yl)phenyl)-2-(2-cyclopropyl-1-(4-(1-(difluoromethyl)-1H-1,2,4-triazol-5-yl)-1H-pyrazol-1-yl)ethyl)pyridine 1-oxide as a white solid.

LC/MS: mass calculated for C$_{23}$H$_{18}$ClF$_3$N$_{10}$O: 542.13, measured (ES, m/z): 565.05 [M+Na]$^+$. $^1$H NMR (300 MHz, DMSO-d$_6$) δ 9.70 (s, 1H), 8.73 (s, 1H), 8.44-8.47 (m, 1H), 7.86-8.29 (m, 4H), 7.70-7.80 (m, 1H), 7.41 (d, J=8.3 Hz, 1H), 7.15-7.23 (m, 1H), 6.10-6.20 (m, 1H), 2.27-2.38 (m, 1H), 1.92-2.07 (m, 1H), 0.55-0.64 (m, 1H), 0.27-0.38 (m, 2H), 0.06-0.17 (m, 1H), −0.01--0.10 (m, 1H). $^{19}$F-NMR (282 MHz, DMSO-d$_6$) δ −96.12, −112.75.

Example 802: (S)-5-(3-Chloro-2-fluoro-6-(1H-tetrazol-1-yl)phenyl)-2-(2-cyclopropyl-1-(4-(1-(difluoromethyl)-1H-1,2,4-triazol-5-yl)-1H-pyrazol-1-yl)ethyl)pyridine 1-oxide

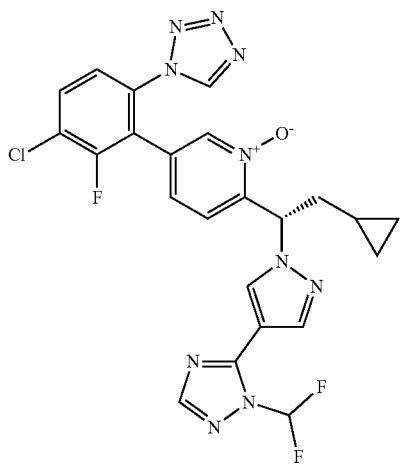 [SMILES: [O-][n+]1cc(-c2c(-n3cnnn3)ccc(Cl)c2F)ccc1[C@H](CC1CC1)n1cc(-c2ncnn2C(F)F)cn1]

LC/MS: mass calculated for $C_{23}H_{18}ClF_3N_{10}O$: 542.13, measured (ES, m/z): 543.05[M+H]$^+$. $^1$H NMR (300 MHz, DMSO-$d_6$) δ 9.70 (s, 1H), 8.73 (s, 1H), 8.44 (s, 1H), 8.27 (s, 1H), 8.02-8.11 (m, 2H), 8.07 (t, J=54.0 Hz, 1H), 7.76 (dd, J=8.7, 1.6 Hz, 1H), 7.41 (d, J=8.3 Hz, 1H), 7.19 (dd, J=8.3, 1.7 Hz, 1H), 6.15-6.22 (m, 1H), 2.38-2.27 (m, 1H), 2.07-1.92 (m, 1H), 0.64-0.55 (m, 1H), 0.41-0.21 (m, 2H), 0.17-0.06 (m, 1H), −0.01--0.10 (m, 1H). $^{19}$F NMR (282 MHz, DMSO-$d_6$) δ −96.12 (d, J=4.7 Hz), −112.75.

Example 803: 5-(3-Chloro-2-fluoro-6-(1H-tetrazol-1-yl)phenyl)-2-((1S*)-1-(4-(1-(difluoromethyl)-1H-1,2,4-triazol-5-yl)-1H-pyrazol-1-yl)-2-((1S*)-2-methylcyclopropyl)ethyl)pyridine 1-oxide

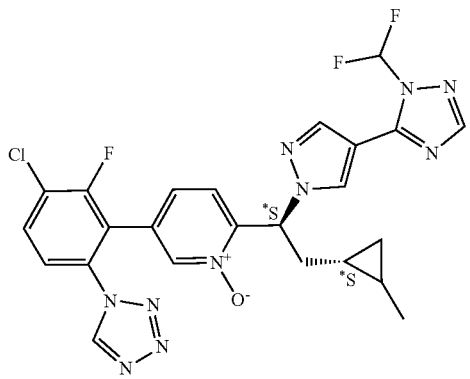 [SMILES: CC1C[C@H]1C[C@@H](c1ccc(-c2c(-n3cnnn3)ccc(Cl)c2F)c[n+]1[O-])n1cc(-c2ncnn2C(F)F)cn1]

Step 1: N-Methoxy-N-methyl-2-(2-methylcyclopropyl)acetamide

To a solution of 2-(2-methylcyclopropyl)acetic acid (1.0 g, 8.8 mmol, 1.0 equiv.) in DCM (15 mL) was added di(1H-imidazol-1-yl)methanone (2.8 g, 17.5 mmol, 2.0 equiv.) at room temperature and the solution was stirred for 0.5 h. To the solution was then added N,O-dimethylhydroxylamine hydrochloride (1.7 g, 17.5 mmol, 2.0 equiv.) and the solution was stirred at room temperature overnight. The reaction was quenched with water, and the mixture extracted with DCM twice. The combined organic layer was washed with 1N HCl, saturated aqueous NaHCO$_3$ and brine, dried over anhydrous Na$_2$SO$_4$ and concentrated to yield N-methoxy-N-methyl-2-(2-methylcyclopropyl)acetamide as a colorless oil. $^1$H NMR (400 MHz, Chloroform-d): δ 3.68 (s, 3H), 3.20 (s, 3H), 2.32-2.40 (m, 2H), 1.07 (d, J=6.0 Hz, 3H), 0.75-0.80 (m, 1H), 0.64-0.51 (m, 1H), 0.30-0.34 (m, 2 h).

Step 2: 1-(5-Bromopyridin-2-yl)-2-(2-methylcyclopropyl)ethan-1-one

To a solution of 2,5-dibromopyridine (1.1 g, 4.6 mmol, 1.2 equiv.) in toluene (15 mL) under nitrogen was added n-butyllithium (1.8 mL, 4.6 mmol, 2.5 M in THF, 1.1 equiv.) at −78° C. and the solution was stirred for 1 h at this temperature. To the solution was then added the solution of N-methoxy-N-methyl-2-(2-methylcyclopropyl)acetamide (0.6 g, 3.8 mmol, 1.0 equiv.) in toluene (2 mL) at −78° C. and the solution was allowed to stirred at −78° C. for 2 h. The reaction was quenched with saturated NH$_4$Cl solution and extracted with ethyl acetate twice. The combined organic layer was washed with brine, dried over Na$_2$SO$_4$ and concentrated. The residue was purified by silica gel chromatography (0→50% ethyl acetate/petroleum ether) to yield 1-(5-bromopyridin-2-yl)-2-(2-methylcyclopropyl)ethan-1-one as a colorless oil. LC/MS: mass calculated for $C_{11}H_{12}BrNO$: 253.01, measured (ES, m/z): 254.00, 256.00 [M+H, M+H+2]$^+$.

Step 3: 1-(5-Bromopyridin-2-yl)-2-(2-methylcyclopropyl)ethan-1-ol

To a solution of 1-(5-bromopyridin-2-yl)-2-(2-methylcyclopropyl)ethan-1-one (750 mg, 2.95 mmol, 1.0 equiv.) in CH$_3$OH (10 mL) was added NaBH$_4$ (167 mg, 4.43 mmol, 1.5 equiv.) and the solution was stirred at room temperature for 2 h. The reaction was diluted with water, and the mixture extracted with ethyl acetate twice. The combined organic layers were washed with brine, dried over Na$_2$SO$_4$ and concentrated to yield 1-(5-bromopyridin-2-yl)-2-(2-methylcyclopropyl)ethan-1-ol as a colorless oil. LC/MS: mass calculated for $C_{11}H_{14}BrNO$: 255.03, measured (ES, m/z): 255.95, 257.95 [M+H, M+H+2]$^+$.

Step 4: 1-(5-Bromopyridin-2-yl)-2-(2-methylcyclopropyl)ethyl methanesulfonate

To a mixture of 1-(5-bromopyridin-2-yl)-2-(2-methylcyclopropyl)ethan-1-ol (750 mg, 2.93 mmol, 1.0 equiv.) and triethylamine (1.63 g, 11.71 mmol, 4.0 equiv.) in DCM (10 mL) was added methanesulfonic anhydride (1.02 g, 5.86 mmol, 2.0 equiv.) at 0° C. and the solution was stirred at room temperature for 1 h. The reaction was diluted with water, and the mixture extracted with DCM twice. The combined organic layers were washed with brine, dried over Na$_2$SO$_4$ and concentrated. The residue was purified by silica gel chromatography (0→40% ethyl acetate/petroleum ether) to yield 1-(5-bromopyridin-2-yl)-2-(2-methylcyclopropyl) ethyl methanesulfonate as a colorless oil. LC/MS: mass calculated for $C_{12}H_{16}BrNO_3S$: 333.00, measured (ES, m/z): 333.95, 335.95 [M+H, M+H+2]$^+$.

Step 5: 5-Bromo-2-(1-(4-(1-(difluoromethyl)-1H-1,2,4-triazol-5-yl)-1H-pyrazol-1-yl)-2-(2-methylcyclopropyl)ethyl)pyridine A mixture of 1-(5-bromopyridin-2-yl)-2-(2-methylcyclopropyl)ethyl methanesulfonate (200 mg, 0.60 mmol, 1.0 equiv.), 1-(difluoromethyl)-5-(1H-pyrazol-4-yl)-1H-1,2,3-triazole (166 mg, 0.90 mmol, 1.5 equiv.) and cesium carbonate (390 mg, 1.20 mmol, 2.0 equiv.) in acetonitrile (4 mL) was stirred at 90° C. for 2 h. The reaction was diluted with water, and the mixture extracted with ethyl acetate twice. The combined organic layers were washed with brine, dried over $Na_2SO_4$ and concentrated. The residue was purified by silica gel chromatography (0→50% ethyl acetate/petroleum ether) to yield 5-bromo-2-(1-(4-(1-(difluoromethyl)-1H-1,2,4-triazol-5-yl)-1H-pyrazol-1-yl)-2-(2-methylcyclopropyl)ethyl)pyridine as a colorless oil. LC/MS: mass calculated for $C_{17}H_{17}BrF_2N_6$: 422.07, measured (ES, m/z): 423.05, 425.05 [M+H, M+H+2]$^+$.

Step 6: 4-Chloro-2-(6-(1-(4-(1-(difluoromethyl)-1H-1,2,4-triazol-5-yl)-1H-pyrazol-1-yl)-2-(2-methylcyclopropyl)ethyl)pyridin-3-yl)-3-fluoroaniline To a mixture of 5-bromo-2-(1-(4-(1-(difluoromethyl)-1H-1,2,4-triazol-5-yl)-1H-pyrazol-1-yl)-2-(2-methylcyclopropyl)ethyl)pyridine (150 mg, 0.35 mmol, 1.0 equiv.), 6-amino-3-chloro-2-fluorophenylboronic acid (87 mg, 0.46 mmol, 1.3 equiv.) and potassium carbonate (147 mg, 1.06 mmol, 3.0 equiv.) in 1,4-dioxane (5 mL) and water (1 mL) was added tetrakis(triphenylphosphine)palladium(0) (41 mg, 0.035 mmol, 0.1 equiv.) and the mixture was stirred at 90° C. for 2 h. After cooling to room temperature, the reaction was quenched with water, and the mixture extracted with ethyl acetate twice. The combined organic layers were washed with brine, dried over anhydrous sodium sulfate and concentrated. The residue was purified silica gel chromatography (0→10% MeOH/DCM) to yield 4-chloro-2-(6-(1-(4-(1-(difluoromethyl)-1H-1,2,4-triazol-5-yl)-1H-pyrazol-1-yl)-2-(2-methylcyclopropyl)ethyl)pyridin-3-yl)-3-fluoroaniline as a light yellow solid. LC/MS: mass calculated for $C_{23}H_{21}ClF_3N_7$: 487.15, measured (ES, m/z): 488.20 [M+H]$^+$.

Step 7: 5-(3-Chloro-2-fluoro-6-(1H-tetrazol-1-yl)phenyl)-2-(1-(4-(1-(difluoromethyl)-1H-1,2,4-triazol-5-yl)-1H-pyrazol-1-yl)-2-(2-methylcyclopropyl)ethyl)pyridine A mixture of 4-chloro-2-(6-(1-(4-(1-(difluoromethyl)-1H-1,2,4-triazol-5-yl)-1H-pyrazol-1-yl)-2-(2-methylcyclopropyl)ethyl)pyridin-3-yl)-3-fluoroaniline (160 mg, 0.33 mmol, 1.0 equiv.), azidotrimethylsilane (1 mL) and trimethoxymethane (1 mL) in acetic acid glacial (1 mL) was stirred at room temperature overnight.

The mixture was concentrated and the residue was purified by reverse phase chromatography on C18 (80 g, MeCN/$H_2O$ (0.05% $CF_3COOH$): 0→50%) to yield 5-(3-chloro-2-fluoro-6-(1H-tetrazol-1-yl)phenyl)-2-(1-(4-(1-(difluoromethyl)-1H-1,2,4-triazol-5-yl)-1H-pyrazol-1-yl)-2-(2-methylcyclopropyl)ethyl)pyridine as a light yellow solid. LC/MS: mass calculated for $C_{24}H_{20}ClF_3N_{10}$: 540.15, measured (ES, m/z): 541.15 [M+H]$^+$.

Step 8: 5-(3-Chloro-2-fluoro-6-(1H-tetrazol-1-yl)phenyl)-2-((1S*)-1-(4-(1-(difluoromethyl)-1H-1,2,4-triazol-5-yl)-1H-pyrazol-1-yl)-2-((1S*)-2-methylcyclopropyl)ethyl)pyridine 1-oxide A mixture of 5-(3-chloro-2-fluoro-6-(1H-tetrazol-1-yl)phenyl)-2-(1-(4-(1-(difluoromethyl)-1H-1,2,4-triazol-5-yl)-1H-pyrazol-1-yl)-2-(2-methylcyclopropyl)ethyl)pyridine (120 mg, 0.22 mmol, 1.0 equiv.), methyl trioxorhenium (VII) (41 mg, 0.17 mmol, 0.5 equiv.) and hydrogen peroxide (0.17 mL, 1.66 mmol, 30 wt %, 5.0 equiv.) in $CH_3OH$ (2.0 mL) was stirred at room temperature for 1H. The solution was purified by reverse phase chromatography on C18 (80 g, MeCN/$H_2O$ (0.05% $CF_3COOH$): 0→50%) and Prep-Chiral-HPLC to yield 5-(3-chloro-2-fluoro-6-(1H-tetrazol-1-yl)phenyl)-2-((1S*)-1-(4-(1-(difluoromethyl)-1H-1,2,4-triazol-5-yl)-1H-pyrazol-1-yl)-2-((1S*)-2-methylcyclopropyl)ethyl)pyridine 1-oxide as a white solid. LC/MS: mass calculated for $C_{24}H_{20}ClF_3N_{10}O$: 556.2, measured (ES, m/z): 557.2 [M+H]$^+$. $^1$H NMR (400 MHz, DMSO-$d_6$): δ 9.68 (s, 1H), 8.71 (s, 1H), 8.41 (s, 1H), 8.25 (s, 1H), 8.22-7.91 (m, 3H), 7.72-7.78 (m, 1H), 7.43 (d, J=8.3 Hz, 1H), 7.15-7.22 (m, 1H), 6.15-6.18 (m, 1H), 2.15-2.24 (m, 1H), 2.08-2.12 (m, 1H), 0.76 (d, J=4.6 Hz, 3H), 0.31-0.36 (m, 1H), 0.22-0.27 (m, 2H), 0.08-0.12 (m, 1H). $^{19}$F-NMR (376 MHz, DMSO-$d_6$): 5-96.12, -112.73.

Example 804: 5-(3-Chloro-2-fluoro-6-(1H-tetrazol-1-yl)phenyl)-2-((1R*)-1-(4-(1-(difluoromethyl)-1H-1,2,4-triazol-5-yl)-1H-pyrazol-1-yl)-2-((1S*)-2-methylcyclopropyl)ethyl)pyridine 1-oxide

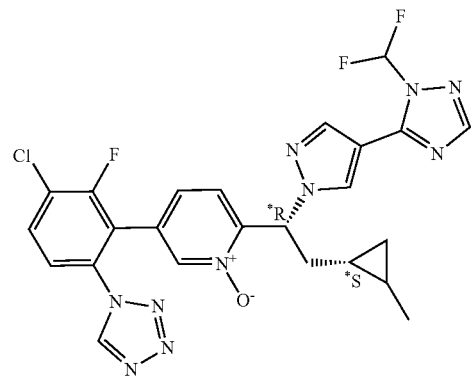 [SMILES: CC1C[C@H]1C[C@H](c1ccc(-c2c(-n3cnnn3)ccc(Cl)c2F)c[n+]1[O-])n1cc(-c2ncnn2C(F)F)cn1]

LC/MS: mass calculated for $C_{24}H_{20}ClF_3N_{10}O$: 556.15, measured (ES, m/z): 557.15 [M+H]$^+$. $^1$H NMR (400 MHz, DMSO-$d_6$) δ 9.68 (s, 1H), 8.71 (s, 1H), 8.41 (d, J=1.7 Hz, 1H), 8.25 (s, 1H), 7.91-8.22 (m, 3H), 7.73-7.79 (m, 1H), 7.43 (d, J=8.3 Hz, 1H), 7.16-7.82 (m, 1H), 6.15-6.22 (m, 1H), 2.15-2.25 (m, 1H), 2.06-2.14 (m, 1H), 0.70-0.82 (m, 3H), 0.31-0.37 (m, 1H), 0.23-0.28 (m, 2H), 0.10 (d, J=8.2 Hz, 1H). $^{19}$F NMR (376 MHz, DMSO-$d_6$) δ -96.12, -112.73.

Example 805: 5-(3-Chloro-2-fluoro-6-(1H-tetrazol-1-yl)phenyl)-2-((1R*)-1-(4-(1-(difluoromethyl)-1H-1,2,4-triazol-5-yl)-1H-pyrazol-1-yl)-2-((1R*)-2-methylcyclopropyl)ethyl)pyridine 1-oxide

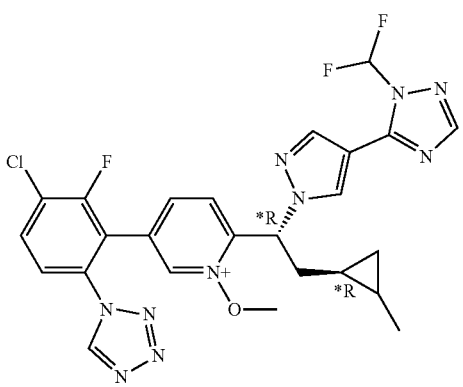 [SMILES: CO[n+]1cc(-c2c(-n3cnnn3)ccc(Cl)c2F)ccc1[C@@H](C[C@H]1CC1C)n1cc(-c2ncnn2C(F)F)cn1]

LC/MS: mass calculated for $C_{24}H_{20}ClF_3N_{10}O$: 556.15, measured (ES, m/z): 557.10 [M+H]$^+$. $^1$H NMR (400 MHz, DMSO-d$_6$) δ 9.68 (s, 1H), 8.69 (s, 1H), 8.42 (d, J=1.6 Hz, 1H), 8.25 (s, 1H), 7.90-8.21 (m, 3H), 7.72-7.78 (m, 1H), 7.46 (d, J=8.2 Hz, 1H), 7.15-7.22 (m, 1H), 6.15-6.25 (m, 1H), 2.30-2.41 (m, 1H), 1.92-2.03 (m, 1H), 0.87 (d, J=5.9 Hz, 3H), 0.46-0.53 (m, 1H), 0.21-0.28 (m, 1H), 0.12-0.18 (m, 1H), 0.03-0.09 (m, 1H). $^{19}$F NMR (376 MHz, DMSO-d$_6$) δ −96.14, −112.73.

Example 806: 5-(3-Chloro-2-fluoro-6-(1H-tetrazol-1-yl)phenyl)-2-((1R)-1-(4-(1-(difluoromethyl)-1H-1,2,4-triazol-5-yl)-1H-pyrazol-1-yl)-2-((1R*)-2-methylcyclopropyl)ethyl)pyridine 1-oxide

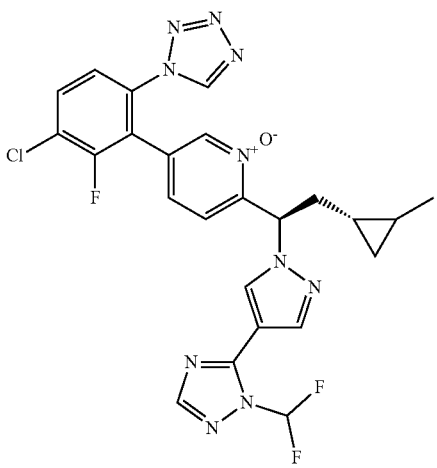

Step 1: N-Methoxy-N-methyl-2-(2-methylcyclopropyl)acetamide

To a solution of 2-(2-methylcyclopropyl)acetic acid (1.0 g, 8.8 mmol, 1.0 equiv.) in DCM (15 mL) was added di(1H-imidazol-1-yl)methanone (2.8 g, 17.5 mmol, 2.0 equiv.) at room temperature and the solution was stirred for 0.5 h. To the solution was then added N,O-dimethylhydroxylamine hydrochloride (1.7 g, 17.5 mmol, 2.0 equiv.) and the solution was stirred at room temperature overnight. The reaction was quenched with water, and the mixture extracted with DCM twice. The combined organic layer was washed with 1N HCl, saturated aqueous NaHCO$_3$ and brine, dried over anhydrous Na$_2$SO$_4$ and concentrated to yield N-methoxy-N-methyl-2-(2-methylcyclopropyl)acetamide as a colorless oil. $^1$H NMR (400 MHz, Chloroform-d): δ 3.68 (s, 3H), 3.20 (s, 3H), 2.32-2.40 (m, 2H), 1.07 (d, J=6.0 Hz, 3H), 0.75-0.80 (m, 1H), 0.64-0.51 (m, 1H), 0.30-0.34 (m, 2 h).

Step 2: 1-(5-Bromopyridin-2-yl)-2-(2-methylcyclopropyl)ethan-1-one

To a solution of 2,5-dibromopyridine (1.1 g, 4.6 mmol, 1.2 equiv.) in toluene (15 mL) under nitrogen was added n-butyllithium (1.8 mL, 4.6 mmol, 2.5 M in THF, 1.1 equiv.) at −78° C. and the solution was stirred for 1 h at this temperature. To the solution was then added the solution of N-methoxy-N-methyl-2-(2-methylcyclopropyl)acetamide (0.6 g, 3.8 mmol, 1.0 equiv.) in toluene (2 mL) at −78° C. and the solution was allowed to stirred at −78° C. for 2 h. The reaction was quenched with saturated NH$_4$Cl solution and extracted with ethyl acetate twice. The combined organic layer was washed with brine, dried over Na$_2$SO$_4$ and concentrated. The residue was purified by silica gel chromatography (0→50% ethyl acetate/petroleum ether) to yield 1-(5-bromopyridin-2-yl)-2-(2-methylcyclopropyl)ethan-1-one as a colorless oil. LC/MS: mass calculated for $C_{11}H_{12}BrNO$: 253.01, measured (ES, m/z): 254.00, 256.00 [M+H, M+H+2]$^+$.

Step 3: 1-(5-Bromopyridin-2-yl)-2-(2-methylcyclopropyl)ethan-1-ol

To a solution of 1-(5-bromopyridin-2-yl)-2-(2-methylcyclopropyl)ethan-1-one (750 mg, 2.95 mmol, 1.0 equiv.) in CH$_3$OH (10 mL) was added NaBH$_4$ (167 mg, 4.43 mmol, 1.5 equiv.) and the solution was stirred at room temperature for 2 h. The reaction was diluted with water, and the mixture extracted with ethyl acetate twice. The combined organic layers were washed with brine, dried over Na$_2$SO$_4$ and concentrated to yield 1-(5-bromopyridin-2-yl)-2-(2-methylcyclopropyl)ethan-1-ol as a colorless oil. LC/MS: mass calculated for $C_{11}H_{14}BrNO$: 255.03, measured (ES, m/z): 255.95, 257.95 [M+H, M+H+2]$^+$.

Step 4: 1-(5-Bromopyridin-2-yl)-2-(2-methylcyclopropyl)ethyl methanesulfonate

To a mixture of 1-(5-bromopyridin-2-yl)-2-(2-methylcyclopropyl)ethan-1-ol (750 mg, 2.93 mmol, 1.0 equiv.) and triethylamine (1.63 g, 11.71 mmol, 4.0 equiv.) in DCM (10 mL) was added methanesulfonic anhydride (1.02 g, 5.86 mmol, 2.0 equiv.) at 0° C. and the solution was stirred at room temperature for 1 h. The reaction was diluted with water, and the mixture extracted with DCM twice. The combined organic layers were washed with brine, dried over Na$_2$SO$_4$ and concentrated. The residue was purified by silica gel chromatography (0→40% ethyl acetate/petroleum ether) to yield 1-(5-bromopyridin-2-yl)-2-(2-methylcyclopropyl) ethyl methanesulfonate as a colorless oil. LC/MS: mass calculated for $C_{12}H_{16}BrNO_3S$: 333.00, measured (ES, m/z): 333.95, 335.95 [M+H, M+H+2]$^+$.

Step 5: 5-Bromo-2-(1-(4-(1-(difluoromethyl)-1H-1,2,4-triazol-5-yl)-1H-pyrazol-1-yl)-2-(2-methylcyclopropyl)ethyl)pyridine A mixture of 1-(5-bromopyridin-2-yl)-2-(2-methylcyclopropyl)ethyl methanesulfonate (200 mg, 0.60 mmol, 1.0 equiv.), 1-(difluoromethyl)-5-(1H-pyrazol-4-yl)-1H-1,2,3-triazole (166 mg, 0.90 mmol, 1.5 equiv.) and cesium carbonate (390 mg, 1.20 mmol, 2.0 equiv.) in acetonitrile (4 mL) was stirred at 90° C. for 2 h. The reaction was diluted with water, and the mixture extracted with ethyl acetate twice. The combined organic layers were washed with brine, dried over $Na_2SO_4$ and concentrated. The residue was purified by silica gel chromatography (0→50% ethyl acetate/petroleum ether) to yield 5-bromo-2-(1-(4-(1-(difluoromethyl)-1H-1,2,4-triazol-5-yl)-1H-pyrazol-1-yl)-2-(2-methylcyclopropyl)ethyl)pyridine as a colorless oil. LC/MS: mass calculated for $C_{17}H_{17}BrF_2N_6$: 422.07, measured (ES, m/z): 423.05, 425.05 [M+H, M+H+2]$^+$.

Step 6: 4-Chloro-2-(6-(1-(4-(1-(difluoromethyl)-1H-1,2,4-triazol-5-yl)-1H-pyrazol-1-yl)-2-(2-methylcyclopropyl)ethyl)pyridin-3-yl)-3-fluoroaniline To a mixture of 5-bromo-2-(1-(4-(1-(difluoromethyl)-1H-1,2,4-triazol-5-yl)-1H-pyrazol-1-yl)-2-(2-methylcyclopropyl)ethyl)pyridine (150 mg, 0.35 mmol, 1.0 equiv.), 6-amino-3-chloro-2-fluorophenylboronic acid (87 mg, 0.46 mmol, 1.3 equiv.) and potassium carbonate (147 mg, 1.06 mmol, 3.0 equiv.) in 1,4-dioxane (5 mL) and water (1 mL) was added tetrakis(triphenylphosphine)palladium(0) (41 mg, 0.035 mmol, 0.1 equiv.) and the mixture was stirred at 90° C. for 2 h. After cooling to room temperature, the reaction was quenched with water, and the mixture extracted with ethyl acetate twice. The combined organic layers were washed with brine, dried over anhydrous sodium sulfate and concentrated. The residue was purified silica gel chromatography (0→10% MeOH/DCM) to yield 4-chloro-2-(6-(1-(4-(1-(difluoromethyl)-1H-1,2,4-triazol-5-yl)-1H-pyrazol-1-yl)-2-(2-methylcyclopropyl)ethyl)pyridin-3-yl)-3-fluoroaniline as a light yellow solid. LC/MS: mass calculated for $C_{23}H_{21}ClF_3N_7$: 487.15, measured (ES, m/z): 488.20 [M+H]$^+$.

Step 7: 5-(3-Chloro-2-fluoro-6-(1H-tetrazol-1-yl)phenyl)-2-(1-(4-(1-(difluoromethyl)-1H-1,2,4-triazol-5-yl)-1H-pyrazol-1-yl)-2-(2-methylcyclopropyl)ethyl)pyridine A mixture of 4-chloro-2-(6-(1-(4-(1-(difluoromethyl)-1H-1,2,4-triazol-5-yl)-1H-pyrazol-1-yl)-2-(2-methylcyclopropyl)ethyl)pyridin-3-yl)-3-fluoroaniline (160 mg, 0.33 mmol, 1.0 equiv.), azidotrimethylsilane (1 mL) and trimethoxymethane (1 mL) in acetic acid glacial (1 mL) was stirred at room temperature overnight.

The mixture was concentrated and the residue was purified by reverse phase chromatography on C18 (80 g, MeCN/$H_2O$ (0.05% $CF_3COOH$): 0→50%) to yield 5-(3-chloro-2-fluoro-6-(1H-tetrazol-1-yl)phenyl)-2-(1-(4-(1-(difluoromethyl)-1H-1,2,4-triazol-5-yl)-1H-pyrazol-1-yl)-2-(2-methylcyclopropyl)ethyl)pyridine as a light yellow solid. LC/MS: mass calculated for $C_{24}H_{20}ClF_3N_{10}$: 540.15, measured (ES, m/z): 541.15 [M+H]$^+$.

Step 8: 5-(3-Chloro-2-fluoro-6-(1H-tetrazol-1-yl)phenyl)-2-((1S*)-1-(4-(1-(difluoromethyl)-1H-1,2,4-triazol-5-yl)-1H-pyrazol-1-yl)-2-((1R*)-2-methylcyclopropyl)ethyl)pyridine 1-oxide A mixture of 5-(3-chloro-2-fluoro-6-(1H-tetrazol-1-yl)phenyl)-2-(1-(4-(1-(difluoromethyl)-1H-1,2,4-triazol-5-yl)-1H-pyrazol-1-yl)-2-(2-methylcyclopropyl)ethyl)pyridine (120 mg, 0.22 mmol, 1.0 equiv.), methyl trioxorhenium (VII) (41 mg, 0.17 mmol, 0.5 equiv.) and hydrogen peroxide (0.17 mL, 1.66 mmol, 30 wt %, 5.0 equiv.) in $CH_3OH$ (2.0 mL) was stirred at room temperature for 1 h. The solution was purified by reverse phase chromatography on C18 (80 g, MeCN/$H_2O$ (0.05% $CF_3COOH$): 0→50%) and Prep-Chiral-HPLC to yield 5-(3-chloro-2-fluoro-6-(1H-tetrazol-1-yl)phenyl)-2-((1R)-1-(4-(1-(difluoromethyl)-1H-1,2,4-triazol-5-yl)-1H-pyrazol-1-yl)-2-((1R*)-2-methylcyclopropyl)ethyl)pyridine 1-oxide as a white solid.

LC/MS: mass calculated for $C_{24}H_{20}ClF_3N_{10}O$: 556.2, measured (ES, m/z): 557.1 [M+H]$^+$. $^1$H NMR (400 MHz, DMSO-$d_6$): δ 9.68 (s, 1H), 8.69 (s, 1H), 8.42 (s, 1H), 8.25 (s, 1H), 7.89-8.22 (m, 3H), 7.72-7.78 (m, 1H), 7.46 (d, J=8.3 Hz, 1H), 7.17-7.20 (m, 1H), 6.18-6.21 (m, 1H), 2.22-2.41 (m, 1H), 1.94-2.01 (m, 1H), 0.87 (d, J=6.0 Hz, 3H), 0.44-0.52 (m, 1H), 0.21-0.29 (m, 1H), 0.13-0.18 (m, 1H), 0.02-0.09 (m, 1H). $^{19}$F-NMR (376 MHz, DMSO-$d_6$): δ −96.13, −112.72.

Example 807: 5-(3-Chloro-2-fluoro-6-(1H-tetrazol-1-yl)phenyl)-2-((1R)-1-(4-(4-fluoro-1-methyl-1H-1,2,3-triazol-5-yl)-1H-pyrazol-1-yl)-2-(2-methylcyclopropyl)ethyl)pyridine 1-oxide

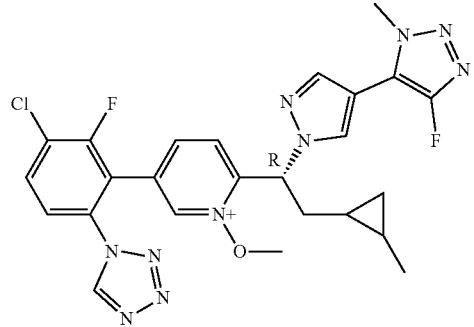

Step 1: 5-Bromo-2-(1-(4-(1-methyl-1H-1,2,3-triazol-5-yl)-1H-pyrazol-1-yl)-2-(2-methylcyclopropyl)ethyl)pyridine A mixture of 1-(5-bromopyridin-2-yl)-2-(2-methylcyclopropyl)ethyl methanesulfonate (0.3 g, 0.90 mmol, 1.0 equiv.), 1-methyl-5-(1H-pyrazol-4-yl)-1H-1,2,3-triazole (0.16 g, 1.08 mmol, 1.2 equiv.) and cesium carbonate (0.35 g, 1.08 mmol, 1.20 equiv.) in acetonitrile (5 mL) was stirred at 90° C. for 4 h. The reaction was diluted with water, and the mixture extracted with EtOAc twice. The combined organic layers were washed with brine, dried over $Na_2SO_4$ and concentrated. The residue was purified by silica gel chromatography (0→10% MeOH/DCM) to yield 5-bromo-2-(1-(4-(1-methyl-1H-1,2,3-triazol-5-yl)-1H-pyrazol-1-yl)-2-(2-methylcyclopropyl)ethyl)pyridine as a colorless oil. LC/MS: mass calculated for $C_{17}H_{19}BrN_6$: 386.09, measured (ES, m/z): 387.10 [M+H]$^+$.

Step 2: 5-Bromo-2-(1-(4-(4-fluoro-1-methyl-1H-1,2,3-triazol-5-yl)-1H-pyrazol-1-yl)-2-(2-methylcyclopropyl)ethyl)pyridine A mixture of 5-bromo-2-(1-(4-(1-methyl-1H-1,2,3-triazol-5-yl)-1H-pyrazol-1-yl)-2-(2-methylcyclopropyl)ethyl)

pyridine (0.32 g, 0.83 mmol, 1.0 equiv.) and Selectfluor™ (0.88 g, 2.48 mmol, 3.0 equiv.) in acetonitrile (5 mL) was stirred for 2 h at 60° C. The reaction was quenched with water, and the mixture extracted with EtOAc twice. The combined organic layers were washed with brine, dried over anhydrous sodium sulfate and concentrated. The residue was purified silica gel chromatography (0→50% EtOAc/petroleum ether) to yield 5-bromo-2-(1-(4-(4-fluoro-1-methyl-1H-1,2,3-triazol-5-yl)-1H-pyrazol-1-yl)-2-(2-methylcyclopropyl)ethyl)pyridine as a light yellow solid. LC/MS: mass calculated for $C_{17}H_{18}BrFN_6$: 404.08, measured (ES, m/z): 407.05 $[M+H+2]^+$.

Step 3: 4-Chloro-3-fluoro-2-(6-(1-(4-(4-fluoro-1-methyl-1H-1,2,3-triazol-5-yl)-1H-pyrazol-1-yl)-2-(2-methylcyclopropyl)ethyl)pyridin-3-yl)aniline A mixture of 5-bromo-2-(1-(4-(4-fluoro-1-methyl-1H-1,2,3-triazol-5-yl)-1H-pyrazol-1-yl)-2-(2-methylcyclopropyl)ethyl)pyridine (90 mg, 0.22 mmol, 1.0 equiv.), (6-amino-3-chloro-2-fluorophenyl)boronic acid (84 mg, 0.44 mmol, 2 equiv.), Pd(PPh₃)₄ (51 mg, 0.04 mmol, 0.2 equiv.), $K_2CO_3$ (184 mg, 1.33 mmol, 6.0 equiv.) in 1,4-dioxane (2 mL) and water (0.5 mL) was refluxed at 90° C. under $N_2$ for 2 h. The mixture was diluted with $H_2O$, extracted with ethyl acetate twice. The combined organic layers were washed with brine, dried over $Na_2SO_4$, concentrated and purified by silica gel chromatography (0→80% EA/PE) to yield 4-chloro-3-fluoro-2-(6-(1-(4-(4-fluoro-1-methyl-1H-1,2,3-triazol-5-yl)-1H-pyrazol-1-yl)-2-(2-methylcyclopropyl)ethyl)pyridin-3-yl)aniline as a light yellow oil. LC/MS: mass calculated for $C_{23}H_{22}ClF_2N_7$: 469.16, measured (ES, m/z): 470.15 $[M+H]^+$.

Step 4: 5-(3-Chloro-2-fluoro-6-(1H-tetrazol-1-yl)phenyl)-2-(1-(4-(4-fluoro-1-methyl-1H-1,2,3-triazol-5-yl)-1H-pyrazol-1-yl)-2-(2-methylcyclopropyl)ethyl)pyridine A mixture of 4-chloro-3-fluoro-2-(6-(1-(4-(4-fluoro-1-methyl-1H-1,2,3-triazol-5-yl)-1H-pyrazol-1-yl)-2-(2-methylcyclopropyl)ethyl)pyridin-3-yl)aniline (100 mg, 0.20 mmol, 1.0 equiv.), trimethoxymethane (0.2 mL), azidotrimethylsilane (0.2 mL) and acetic acid (0.2 mL) was stirred overnight at room temperature. The reaction was purified by reverse phase chromatography on C18 (80 g, MeCN/H₂O (0.05% CF₃COOH): 0→45%) to yield 5-(3-chloro-2-fluoro-6-(1H-tetrazol-1-yl)phenyl)-2-(1-(4-(4-fluoro-1-methyl-1H-1,2,3-triazol-5-yl)-1H-pyrazol-1-yl)-2-(2-methylcyclopropyl)ethyl)pyridine as a light yellow solid. LC/MS: mass calculated for $C_{24}H_{21}ClF_2N_{10}$: 522.16, measured (ES, m/z): 523.15 $[M+H]^+$.

Step 5: 5-(3-Chloro-2-fluoro-6-(1H-tetrazol-1-yl)phenyl)-2-((1S*)-1-(4-(4-fluoro-1-methyl-1H-1,2,3-triazol-5-yl)-1H-pyrazol-1-yl)-2-(2-methylcyclopropyl)ethyl)pyridine 1-oxide A mixture of 5-(3-chloro-2-fluoro-6-(1H-tetrazol-1-yl)phenyl)-2-(1-(4-(4-fluoro-1-methyl-1H-1,2,3-triazol-5-yl)-1H-pyrazol-1-yl)-2-(2-methylcyclopropyl)ethyl)pyridine (45 mg, 0.09 mmol, 1.0 equiv.), hydrogen peroxide (30 wt %, 0.1 mL, 0.86 mmol, 10.0 equiv.) and methyltrioxorhenium (4 mg, 0.02 mmol, 0.2 equiv.) in CH₃OH (0.5 mL) was stirred for 1H at room temperature. The mixture was purified by reverse phase chromatography on C18 (80 g, MeCN/H₂O (0.05% CF₃COOH): 0→45%) to yield 5-(3-chloro-2-fluoro-6-(1H-tetrazol-1-yl)phenyl)-2-(1-(4-(4-fluoro-1-methyl-1H-1,2,3-triazol-5-yl)-1H-pyrazol-1-yl)-2-(2-methylcyclopropyl)ethyl)pyridine 1-oxide. The racemic product was separated by Chiral-HPLC to yield 5-(3-chloro-2-fluoro-6-(1H-tetrazol-1-yl)phenyl)-2-((1R)-1-(4-(4-fluoro-1-methyl-1H-1,2,3-triazol-5-yl)-1H-pyrazol-1-yl)-2-(2-methylcyclopropyl)ethyl)pyridine 1-oxide as a white solid.

LC/MS: mass calculated for $C_{24}H_{21}ClF_2N_{10}O$: 538.16, measured (ES, m/z): 539.10 $[M+H]^+$. ¹H NMR (400 MHz, DMSO-d₆): δ 9.67 (d, J=1.6 Hz, 1H), 8.57 (d, J=7.7 Hz, 1H), 8.40-8.44 (m, 1H), 8.01-8.08 (m, 1H), 7.96 (d, J=10.0 Hz, 1H), 7.70-7.76 (m, 1H), 7.36-7.45 (m, 1H), 7.13-7.20 (m, 1H), 6.10-6.23 (m, 1H), 4.09 (d, J=4.0 Hz, 3H), 2.14-2.40 (m, 1H), 1.88-2.11 (m, 1H), 0.74-0.90 (m, 3H), 0.05-0.55 (m, 4H). ¹⁹F NMR (376 MHz, DMSO-d₆): δ −112.74, −145.19.

Example 808: 5-(3-Chloro-2-fluoro-6-(1H-tetrazol-1-yl)phenyl)-2-((1S)-1-(4-(4-fluoro-1-methyl-1H-1,2,3-triazol-5-yl)-1H-pyrazol-1-yl)-2-(2-methylcyclopropyl)ethyl)pyridine 1-oxide

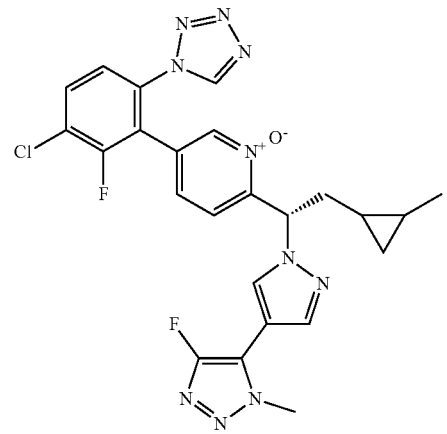

LC/MS: mass calculated for $C_{24}H_{21}ClF_2N_{10}O$: 538.16, measured (ES, m/z): 539.15 $[M+H]^+$. ¹H NMR (400 MHz, DMSO-d₆) δ 9.67 (s, 1H), 8.54-8.64 (m, 1H), 8.41 (d, J=4.8 Hz, 1H), 8.04 (t, J=8.7 Hz, 1H), 7.96 (d, J=9.8 Hz, 1H), 7.74 (t, J=8.7 Hz, 1H), 7.30-7.47 (m, 1H), 7.16 (d, J=8.6 Hz, 1H), 6.12-6.18 (m, 1H), 4.09 (s, 3H), 2.14-2.41 (m, 1H), 1.88-2.12 (m, 1H), 0.81-0.90 (m, 3H), 0.21-0.58 (m, 2H), 0.11-0.18 (m, 2H). ¹⁹F NMR (376 MHz, DMSO-d₆) δ −73.70, −112.72, −145.11.

Example 809: (S)-5-(3-Chloro-2-fluoro-6-(1H-tetra-zol-1-yl)phenyl)-2-(3-(difluoromethoxy)-1-(4-(1-(difluoromethyl)-1H-imidazol-5-yl)-1H-pyrazol-1-yl)propyl)pyridine 1-oxide

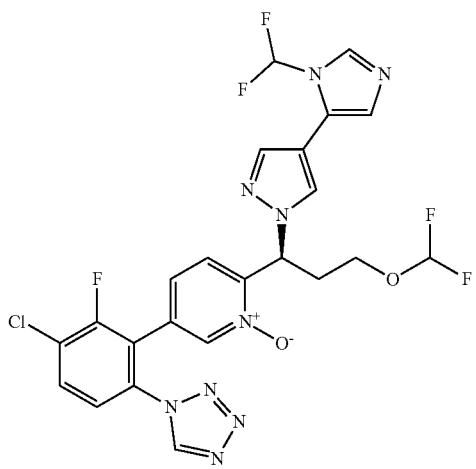 [SMILES: [O-][n+]1cc(-c2c(-n3cnnn3)ccc(Cl)c2F)ccc1[C@H](CCOC(F)F)n1cc(-c2cncn2C(F)F)cn1]

LC/MS: mass calculated for $C_{23}H_{17}ClF_5N_9O_2$: 581.11, measured (ES, m/z): 582.05 [M+H]$^+$. $^1$H NMR (400 MHz, DMSO-d$_6$) δ 9.67 (s, 1H), 8.40-8.47 (m, 2H), 8.01-8.09 (m, 1H), 7.64-7.97 (m, 3H), 7.61 (d, J=1.6 Hz, 1H), 7.29 (d, J=8.3 Hz, 1H), 7.11-7.22 (m, 2H), 6.61 (t, J=75.7 Hz, 1H), 6.18-6.27 (m, 1H), 3.80-3.90 (m, 1H), 3.62-3.78 (m, 1H), 2.57-2.65 (m, 1H), 1.95-2.05 (m, 1H). $^{19}$F NMR (376 MHz, DMSO-d$_6$) δ −73.92, −83.32, −91.96, −112.67.

Example 810: (R)-5-(3-Chloro-2-fluoro-6-(1H-tetra-zol-1-yl)phenyl)-2-(3-(difluoromethoxy)-1-(4-(1-(difluoromethyl)-1H-imidazol-5-yl)-1H-pyrazol-1-yl)propyl)pyridine 1-oxide

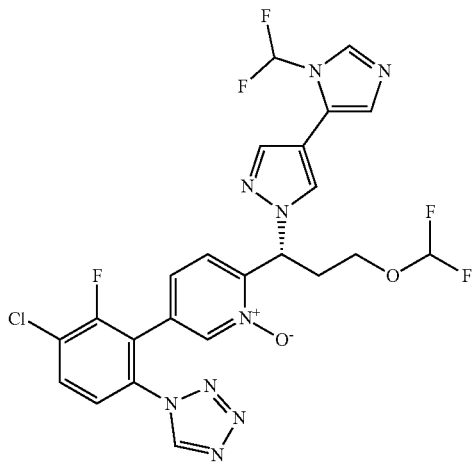

Step 1: 1-(Difluoromethyl)-1H-imidazole

Imidazole 1H-pyrazole (40.0 g, 587.6 mmol, 1.0 equiv.), dibenzo-18-crown-6 (4.2 g, 11.8 mmol, 0.02 equiv.) and DME (500 mL) were placed into a 2-L flask equipped with a condenser, a mechanical stirrer, a gas bubble inlet and a dropping funnel and heated to 65-70° C. CHClF$_2$ was bubbled through and KOH (35% aqueous) was gradually added to the reaction mixture until disappearance of the starting imidazole by TLC (approx. 3 mol of the alkali). The consumption of the KOH was monitored by pH control (indicator paper, pH=9-11). After the reaction was complete, the mixture was cooled, the aqueous salt layers were separated, and the organic layers were concentrated under reduced pressure at room temperature. The residue was distilled under reduced pressure. The first fraction with bp=40° C./12 mmHg was 1-(difluoromethyl)-1H-imidazole as a colorless oil. $^1$H NMR (400 MHz, DMSO-d$_6$) δ 8.13 (d, J=1.1 Hz, 1H), 7.79 (t, J=59.9 Hz, 1H), 7.58 (t, J=1.4 Hz, 1H), 6.97-7.18 (m, 1H)

Step 2: 4-(1-(Difluoromethyl)-1H-imidazol-5-yl)-1-(tetrahydro-2H-pyran-2-yl)-1H-pyrazole A mixture of 1-(difluoromethyl)-1H-imidazole (1.5 g, 12.7 mmol, 1.0 equiv.), 4-iodo-1-(tetrahydro-2H-pyran-2-yl)-1H-pyrazole (3.5 g, 12.7 mmol, 1.0 equiv.), CuI (1.2 g, 6.4 mmol, 0.5 equiv.), lithium tert-butoxide (1.4 g, 17.8 mmol, 1.4 equiv.) and 3,4,7,8-tetramethyl-1,10-phenanthroline (0.30 g, 1.27 mmol, 0.1 equiv.) in DMF (15 mL) was stirred for 1 h at room temperature. The solution was diluted with water, extracted with ethyl acetate twice. The combined organic layers were washed with brine, dried over Na$_2$SO$_4$, concentrated and purified by silica gel chromatography (0→10% MeOH/DCM) to yield 4-(1-(difluoromethyl)-1H-imidazol-5-yl)-1-(tetrahydro-2H-pyran-2-yl)-1H-pyrazole as yellow solid. LC/MS: mass calculated for $Cl_2H_{14}F_2N_4O$: 268.11, measured (ES, m/z): 269.05 [M+H]$^+$.

Step 3: 4-(1-(Difluoromethyl)-1H-imidazol-5-yl)-1H-pyrazole

A mixture of 4-(1-(difluoromethyl)-1H-imidazol-5-yl)-1-(tetrahydro-2H-pyran-2-yl)-1H-pyrazole (0.42 g, 1.57 mmol, 1.0 equiv.) in MeOH was added HCl (4 M in dioxane). The resulting mixture was stirred for 1 h at room temperature. The reaction solution was concentrated under vacuum to yield 4-(1-(difluoromethyl)-1H-imidazol-5-yl)-1H-pyrazole as yellow oil. LC/MS: mass calculated for $C_7H_6F_2N_4$: 184.06, measured (ES, m/z): 185.10 [M+H]$^+$.

Step 4: 5-Bromo-2-(3-(difluoromethoxy)-1-(4-(1-(difluoromethyl)-1H-imidazol-5-yl)-1H-pyrazol-1-yl)propyl)pyridine A mixture of 4-(1-(difluoromethyl)-1H-imidazol-5-yl)-1H-pyrazole (0.14 g, 0.76 mmol, 1.0 equiv.) and cesium carbonate (0.27 g, 0.84 mmol, 1.1 equiv.) in acetonitrile (2 mL) was stirred for 15 min at room temperature. 1-(5-Bromopyridin-2-yl)-3-(difluoromethoxy)propyl methanesulfonate (0.30 g, 0.84 mmol, 1.1 equiv.) was added and the solution was stirred for 3 h at 90° C. The solution was diluted with H$_2$O, extracted with ethyl acetate twice. The combined organic layers were washed with brine, dried over Na$_2$SO$_4$, concentrated and purified by silica gel chromatography (0→80% EtOAc/petroleum ether) to yield 5-bromo-2-(3-(difluoromethoxy)-1-(4-(1-(difluoromethyl)-1H-imidazol-5-yl)-1H-pyrazol-1-yl)propyl)pyridine as a light yellow oil. LC/MS: mass calculated for $C_{16}H_{14}BrF_4N_5O$: 447.03, measured (ES, m/z): 447.95, 449.95 [M+H, M+H+2]$^+$.

Step 5: 4-Chloro-2-(6-(3-(difluoromethoxy)-1-(4-(1-(difluoromethyl)-1H-imidazol-5-yl)-1H-pyrazol-1-yl)propyl)pyridin-3-yl)-3-fluoroaniline A mixture of 5-bromo-2-(3-(difluoromethoxy)-1-(4-(1-(difluoromethyl)-1H-imidazol-5-yl)-1H-pyrazol-1-yl)propyl)pyridine (66 mg, 0.15 mmol, 1.0 equiv.), (6-amino-3-chloro-2-fluorophenyl)boronic acid (56 mg, 0.30 mmol, 2.0 equiv.), Pd(PPh$_3$)$_4$ (34 mg, 0.03 mmol, 0.2 equiv.), K$_2$CO$_3$ (120 mg, 0.88 mmol, 6.0 equiv.) in 1,4-dioxane (2 mL) and water (0.5 mL) was refluxed at 90° C. under N$_2$ for 2 h. The mixture was diluted with H$_2$O, extracted with ethyl acetate twice. The combined organic layers were washed with brine, dried over Na$_2$SO$_4$, concentrated and purified by silica gel chromatography (0→5% MeOH/DCM) to yield 4-chloro-2-(6-(3-(difluoromethoxy)-1-(4-(1-(difluoromethyl)-1H-imidazol-5-yl)-1H-pyrazol-1-yl)propyl)pyridin-3-yl)-3-fluoroaniline as a light yellow oil. LC/MS: mass calculated for C$_{22}$H$_{18}$ClF$_5$N$_6$O: 512.12, measured (ES, m/z): 513.00 [M+H]$^+$.

Step 6: 5-(3-Chloro-2-fluoro-6-(1H-tetrazol-1-yl)phenyl)-2-(3-(difluoromethoxy)-1-(4-(1-(difluoromethyl)-1H-imidazol-5-yl)-1H-pyrazol-1-yl)propyl)pyridine A mixture of 4-chloro-2-(6-(3-(difluoromethoxy)-1-(4-(1-(difluoromethyl)-1H-imidazol-5-yl)-1H-pyrazol-1-yl)propyl)pyridin-3-yl)-3-fluoroaniline (46 mg, 0.09 mmol, 1.0 equiv.), trimethoxymethane (0.5 mL), azidotrimethylsilane (0.5 mL) and acetic acid (0.5 mL) was stirred at room temperature overnight. The reaction was purified by reverse phase chromatography on C18 (80 g, MeCN/H$_2$O (0.05% CF$_3$COOH): 0→45%) to yield 5-(3-chloro-2-fluoro-6-(1H-tetrazol-1-yl)phenyl)-2-(3-(difluoromethoxy)-1-(4-(1-(difluoromethyl)-1H-imidazol-5-yl)-1H-pyrazol-1-yl)propyl)pyridine as a light yellow solid. LC/MS: mass calculated for C$_{23}$H$_{17}$ClF$_5$N$_9$O: 565.12, measured (ES, m/z): 566.05 [M+H]$^+$.

Step 7: (R)-5-(3-Chloro-2-fluoro-6-(1H-tetrazol-1-yl)phenyl)-2-(3-(difluoromethoxy)-1-(4-(1-(difluoromethyl)-1H-imidazol-5-yl)-1H-pyrazol-1-yl)propyl)pyridine 1-oxide A mixture of 5-(3-chloro-2-fluoro-6-(1H-tetrazol-1-yl)phenyl)-2-(3-(difluoromethoxy)-1-(4-(1-(difluoromethyl)-1H-imidazol-5-yl)-1H-pyrazol-1-yl)propyl)pyridine (40 mg, 0.07 mmol, 1 equiv.) and 3-chlorobenzoperoxoic acid (61 mg, 0.35 mmol, 5 equiv.) in ethyl acetate (0.5 mL) was stirred for 1 h at room temperature. The mixture was purified by reverse phase chromatography on C18 (80 g, MeCN/H$_2$O (0.05% CF$_3$COOH): 0>>>45%) to yield 5-(3-chloro-2-fluoro-6-(1H-tetrazol-1-yl)phenyl)-2-(3-(difluoromethoxy)-1-(4-(1-(difluoromethyl)-1H-imidazol-5-yl)-1H-pyrazol-1-yl)propyl)pyridine 1-oxide. The racemic product was separated by Chiral-HPLC to yield (R)-5-(3-chloro-2-fluoro-6-(1H-tetrazol-1-yl)phenyl)-2-(3-(difluoromethoxy)-1-(4-(1-(difluoromethyl)-1H-imidazol-5-yl)-1H-pyrazol-1-yl)propyl)pyridine 1-oxide as a white solid.

LC/MS: mass calculated for C$_{23}$H$_{17}$ClF$_5$N$_9$O$_2$: 581.11, measured (ES, m/z): 582.05 [M+H]$^+$. $^1$H NMR (400 MHz, DMSO-d$_6$): δ 9.67 (s, 1H), 8.46 (s, 1H), 8.42 (s, 1H), 8.01-8.10 (m, 1H), 7.63-7.96 (m, 3H), 7.59 (d, J=1.6 Hz, 1H), 7.29 (d, J=8.3 Hz, 1H), 7.15-7.23 (m, 1H), 7.10 (d, J=1.6 Hz, 1H), 6.61 (t, J=75.7 Hz, 1H), 6.17-6.27 (m, 1H), 3.79-3.88 (m, 1H), 3.62-3.73 (m, 1H), 2.53-2.65 (m, 1H), 1.94-2.05 (m, 1H). $^{19}$F NMR (376 MHz, DMSO-d$_6$): δ −73.44, −83.32, −91.80, −112.67.

Example 811: (R)-5-(3-Chloro-6-(4-chloro-1H-1,2,3-triazol-1-yl)-2-fluorophenyl)-2-(1-(4-(1-methyl-1H-1,2,3-triazol-5-yl)-1H-pyrazol-1-yl)-2-(6-(trifluoromethyl)pyridin-3-yl)ethyl)pyridine 1-oxide

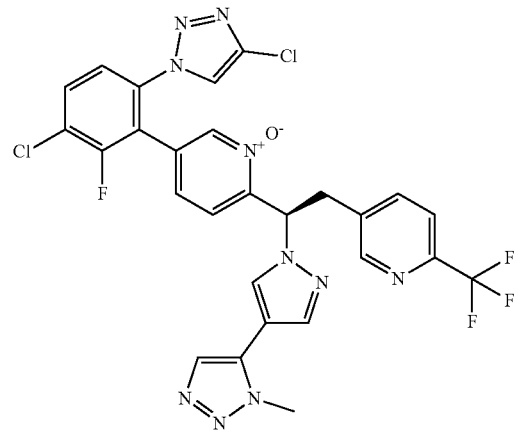

Step 1: 5-Bromo-2-((4-(1-methyl-1H-1,2,3-triazol-5-yl)-1H-pyrazol-1-yl)methyl)pyridine To a solution of 1-methyl-5-(1H-pyrazol-4-yl)-1H-1,2,3-triazole (770.0 mg, 5.16 mmol, 1.0 equiv.) in CH$_3$CN (10 mL) was added 5-bromo-2-(bromomethyl)pyridine (1.5 g, 6.20 mmol, 1.2 equiv.), Cs$_2$CO$_3$ (2.5 g, 7.74 mmol, 1.5 equiv.). The resulting mixture was maintained under nitrogen and stirred at 90° C. for 3H. After cooling to room temperature, the reaction was quenched with water (20 mL). The resulting mixture was extracted with ethyl acetate (3×20 mL). The organic layers were combined, dried over anhydrous sodium sulfate, filtered and concentrated. The resulting residue was purified by silica gel chromatography (0→10% MeOH/DCM) to yield the 5-bromo-2-((4-(1-methyl-1H-1,2,3-triazol-5-yl)-1H-pyrazol-1-yl)methyl)pyridine as a brown solid. LC/MS: mass calculated for C$_{12}$H$_{11}$BrN$_6$: 318.02, measured (ES, m/z): 319.05 [M+H]$^+$.

Step 2: 5-Bromo-2-(1-(4-(1-methyl-1H-1,2,3-triazol-5-yl)-1H-pyrazol-1-yl)-2-(6-(trifluoromethyl)pyridin-3-yl)ethyl)pyridine To a solution of 5-bromo-2-((4-(1-methyl-1H-1,2,3-triazol-5-yl)-1H-pyrazol-1-yl)methyl)pyridine (500.0 mg, 1.57 mmol, 1.0 equiv.) in THF (15 mL) was added LiHMDS (1.5 mL, 1.57 mmol, 1M in THF, 1.0 equiv.) at −78° C. After 1 h, the 5-(bromomethyl)-2-(trifluoromethyl)pyridine (564.0 mg, 2.35 mmol, 1.5 equiv.) was added (−78° C.) with THF (3 mL). The resulting mixture was maintained under nitrogen and stirred at −78° C. for 2 h.

The resulting mixture was maintained under nitrogen and stirred at −78° C. for 2 h. The reaction was quenched with NH$_4$Cl solution (20 mL). The resulting mixture was extracted with ethyl acetate (3×20 mL). The organic layers were combined, dried over anhydrous sodium sulfate, filtered and concentrated. The resulting residue was purified by silica gel chromatography (0→60% ethyl acetate/petroleum ether) to yield the 5-bromo-2-(1-(4-(1-methyl-1H-1,2,3-triazol-5-yl)-1H-pyrazol-1-yl)-2-(6-(trifluoromethyl)pyridin-3-yl)ethyl)pyridine as a yellow oil. LC/MS: mass calculated for $C_{19}H_{15}BrF_3N_7$: 477.05, measured (ES, m/z): 480.10 [M+H+2]+.

Step 3: (6-(1-(4-(1-Methyl-1H-1,2,3-triazol-5-yl)-1H-pyrazol-1-yl)-2-(6-(trifluoromethyl)pyridin-3-yl)ethyl)pyridin-3-yl)boronic acid To a solution of 5-bromo-2-(1-(4-(1-methyl-1H-1,2,3-triazol-5-yl)-1H-pyrazol-1-yl)-2-(6-(trifluoromethyl)pyridin-3-yl)ethyl)pyridine (540.0 mg, 1.13 mmol, 1.0 equiv.) in 1,4-dioxane (10 mL) was added 4,4,4',4',5,5,5',5'-octamethyl-2,2'-bi(1,3,2-dioxaborolane) (860.1 mg, 3.39 mmol, 3.0 equiv.), KOAc (332.4 mg, 3.39 mmol, 3.0 equiv.), Pd(dppf)Cl$_2$ (82.6 mg, 0.11 mmol, 0.1 equiv.). The resulting mixture was maintained under nitrogen and stirred at 100° C. for 2 h. The reaction was quenched with H$_2$O (20 mL). The resulting mixture was extracted with ethyl acetate (3×20 mL). The organic layers were combined, dried over anhydrous sodium sulfate, filtered and concentrated to yield the (6-(1-(4-(1-methyl-1H-1,2,3-triazol-5-yl)-1H-pyrazol-1-yl)-2-(6-(trifluoromethyl)pyridin-3-yl)ethyl)pyridin-3-yl)boronic acid as a black solid. LC/MS: mass calculated for $C_{19}H_{17}BF_3N_7O_2$: 443.15, measured (ES, m/z): 444.05 [M+H]+.

Step 4: 5-(3-Chloro-6-(4-chloro-1H-1,2,3-triazol-1-yl)-2-fluorophenyl)-2-(1-(4-(1-methyl-1H-1,2,3-triazol-5-yl)-1H-pyrazol-1-yl)-2-(6-(trifluoromethyl)pyridin-3-yl)ethyl)pyridine To a solution of 4-chloro-1-(4-chloro-3-fluoro-2-iodophenyl)-1H-1,2,3-triazole (300.0 mg, 0.84 mmol, 1.0 equiv.) in 1,4-dioxane (10 mL) and H$_2$O (1 mL) was added (6-(1-(4-(1-methyl-1H-1,2,3-triazol-5-yl)-1H-pyrazol-1-yl)-2-(6-(trifluoromethyl)pyridin-3-yl)ethyl)pyridin-3-yl)boronic acid (557.1 mg, 1.26 mmol, 1.5 equiv.), K$_2$CO$_3$ (173.7 mg, 1.26 mmol, 1.5 equiv.), Pd(pph$_3$)$_4$ (96.8 mg, 0.08 mmol, 0.1 equiv.). The resulting mixture was maintained under nitrogen and stirred at 90° C. for 3 h. The reaction was quenched with water (20 mL).

The resulting mixture was extracted with ethyl acetate (3×50 mL). The organic layers were combined, dried over anhydrous sodium sulfate, filtered and concentrated. The resulting residue was purified by silica gel chromatography (0→100% ethyl acetate/petroleum ether) to yield the 5-(3-chloro-6-(4-chloro-1H-1,2,3-triazol-1-yl)-2-fluorophenyl)-2-(1-(4-(1-methyl-1H-1,2,3-triazol-5-yl)-1H-pyrazol-1-yl)-2-(6-(trifluoromethyl)pyridin-3-yl)ethyl)pyridine as a yellow oil. LC/MS: mass calculated for $C_{27}H_{18}Cl_2F_4N_{10}$: 528.10, measured (ES, m/z): 529.10 [M+H]+.

Step 5: (R)-5-(3-Chloro-6-(4-chloro-1H-1,2,3-triazol-1-yl)-2-fluorophenyl)-2-(1-(4-(1-methyl-1H-1,2,3-triazol-5-yl)-1H-pyrazol-1-yl)-2-(6-(trifluoromethyl)pyridin-3-yl)ethyl)pyridine 1-oxide To a solution of 5-(3-chloro-6-(4-chloro-1H-1,2,3-triazol-1-yl)-2-fluorophenyl)-2-(1-(4-(1-methyl-1H-1,2,3-triazol-5-yl)-1H-pyrazol-1-yl)-2-(6-(trifluoromethyl)pyridin-3-yl)ethyl)pyridine (240.0 mg, 0.38 mmol, 1.0 equiv.) in MeOH (4 mL) and H$_2$O$_2$ (0.4 mL) was added methyltrioxorhenium (VII) (9.5 mg, 0.04 mmol, 0.1 equiv.). The mixture stirred at room temperature for 5 h. The residue was purified by silica gel chromatography with CH$_3$CN/0.05% TFA water (5%460%) to yield the resulting residue, which was purified by chiral-HPLC with MtBE(0.1% DEA):EtOH=50:50 to yield (R)-5-(3-chloro-6-(4-chloro-1H-1,2,3-triazol-1-yl)-2-fluorophenyl)-2-(1-(4-(1-methyl-1H-1,2,3-triazol-5-yl)-1H-pyrazol-1-yl)-2-(6-(trifluoromethyl)pyridin-3-yl)ethyl)pyridine 1-oxide as off-white solid.

LC/MS: mass calculated for $C_{27}H_{18}Cl_2F_4N_{10}O$: 644.1, measured (ES, m/z): 645.1 [M+H]+. $^1$H NMR (300 MHz, DMSO-d$_6$) δ 8.69 (s, 1H), 8.32-8.58 (m, 3H), 7.94-8.08 (m, 2H), 7.72-7.87 (m, 3H), 7.61-7.71 (m, 1H), 7.42-7.56 (m, 1H), 7.15-7.27 (m, 1H), 6.30-6.45 (m, 1H), 3.96 (s, 3H), 3.64-3.84 (m, 2H). $^{19}$F NMR (282 MHz, DMSO-d$_6$) δ −66.29, −112.92.

Example 812: (S)-5-(3-Chloro-6-(4-chloro-1H-1,2,3-triazol-1-yl)-2-fluorophenyl)-2-(1-(4-(1-methyl-1H-1,2,3-triazol-5-yl)-1H-pyrazol-1-yl)-2-(6-(trifluoromethyl)pyridin-3-yl)ethyl)pyridine 1-oxide

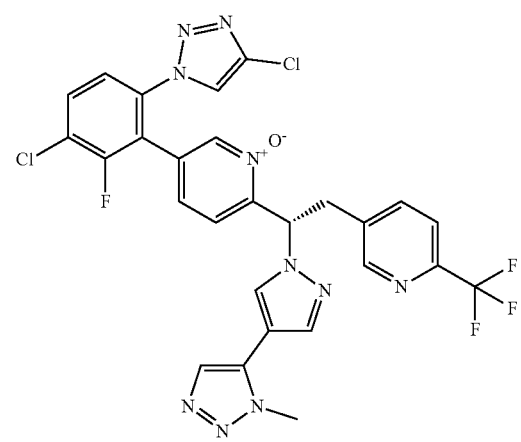

LC/MS: mass calculated for $C_{27}H_{18}Cl_2F_4N_{10}O$: 644.10, measured (ES, m/z): 645.10 [M+H]+. $^1$H NMR (300 MHz, DMSO-d$_6$) δ 8.69 (s, 1H), 8.52 (s, 1H), 8.45 (s, 1H), 8.37 (s, 1H), 7.94-8.08 (m, 2H), 7.72-7.87 (m, 3H), 7.61-7.71 (m, 1H), 7.42-7.56 (m, 1H), 7.15-7.27 (m, 1H), 6.26-6.45 (m, 1H), 3.85-4.01 (m, 3H), 3.60-3.84 (m, 2H). $^{19}$F NMR (282 MHz, DMSO-d$_6$) δ −66.30, −73.49, −112.92.

Example 813: 5-(3-Chloro-2-fluoro-6-(1H-tetrazol-1-yl)phenyl)-2-(1-(2-methyl-1'H,2H-[3,4'-bipyrazol]-1'-yl)-2-(6-(trifluoromethyl)pyridin-2-yl)ethyl)pyridine 1-oxide

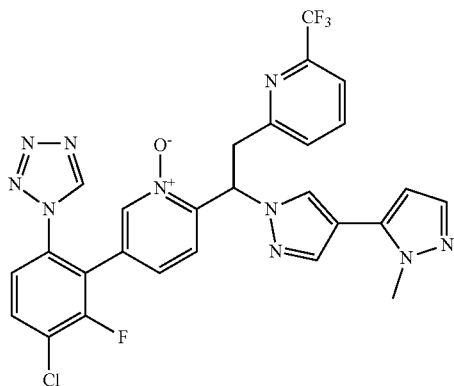 [SMILES: Cn1nccc1-c1cnn(C(Cc2cccc(C(F)(F)F)n2)c2ccc(-c3c(-n4cnnn4)ccc(Cl)c3F)c[n+]2[O-])c1]

LC/MS: mass calculated for $C_{27}H_{19}ClF_4N_{10}O$: 610.1, measured (ES, m/z): 674.2 [M+H]+. $^1$H NMR (400 MHz, CD$_3$OD) δ ppm 3.76 (s, 1H), 3.89-4.07 (m, 3H), 6.75-6.97 (m, 3H), 7.20-7.42 (m, 3H), 7.42-7.55 (m, 2H), 7.56-7.63 (m, 4H), 7.67 (d, J=8.3 Hz, 1H), 7.83-7.96 (m, 4H), 8.09 (s, 1H), 8.28 (s, 1H), 8.36-8.44 (m, 2H), 8.62 (s, 1H), 9.37 (s, 1H).

Example 814: (S)-5-(3-Chloro-2-fluoro-6-(1H-tetrazol-1-yl)phenyl)-2-(2-(1-(difluoromethyl)-1H-pyrazol-3-yl)-1-(4-(2-(trifluoromethyl)pyridin-4-yl)-1H-pyrazol-1-yl)ethyl)pyridine 1-oxide

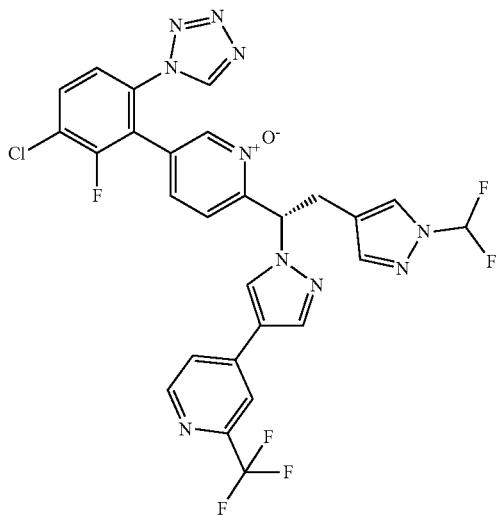

LC/MS: mass calculated for $C_{27}H_{17}ClF_6N_{10}O$: 646.12, measured (ES, m/z): 647.1 [M+H]$^+$. $^1$H NMR (300 MHz, DMSO-d$_6$) δ 9.67 (s, 1H), 8.83 (s, 1H), 8.66 (d, J=5.2 Hz, 1H), 8.47 (s, 1H), 8.33 (s, 1H), 7.99-8.12 (m, 3H), 7.83-7.91 (m, 1H), 7.66 (t, J=57.0 Hz, 1H), 7.38 (d, J=8.3 Hz, 1H), 7.21 (d, J=8.3 Hz, 1H), 6.39 (dd, J=9.4, 5.4 Hz, 1H), 6.14 (d, J=2.6 Hz, 1H), 3.55-3.76 (m, 2H). $^{19}$F NMR (282 MHz, DMSO-d$_6$) δ −66.56, −73.70, −93.84, −112.69.

Example 815: (R)-5-(3-Chloro-2-fluoro-6-(1H-tetrazol-1-yl)phenyl)-2-(2-(1-(difluoromethyl)-1H-pyrazol-3-yl)-1-(4-(2-(trifluoromethyl)pyridin-4-yl)-1H-pyrazol-1-yl)ethyl)pyridine 1-oxide

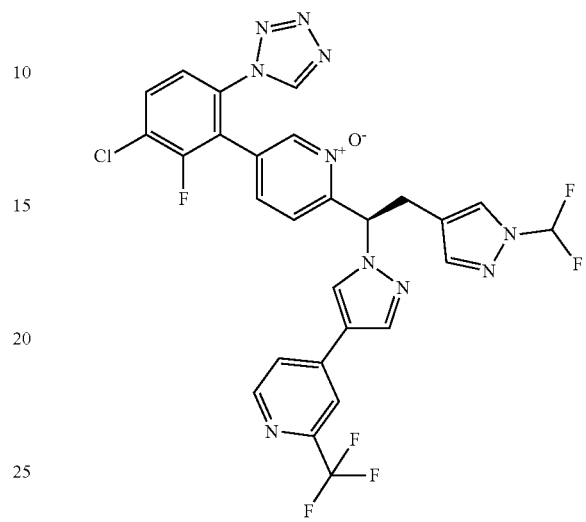

Step 1:
(1-(Difluoromethyl)-1H-pyrazol-3-yl)methanol

To a solution of 1-(difluoromethyl)-1H-pyrazole-3-carboxylic acid (3.0 g, 18.51 mmol, 1.0 equiv.) in THF (20 mL) was added BH$_3$ (30 mL, 2M in THF, 3.2 equiv.). The mixture stirred at room temperature overnight. The reaction was quenched with HCl (2M, 20 mL). The resulting mixture was extracted with ethyl acetate (3×20 mL). The organic layers were combined, dried over anhydrous sodium sulfate, filtered and concentrated to yield the (1-(difluoromethyl)-1H-pyrazol-3-yl)methanol as a yellow oil. LC/MS: mass calculated for $C_5H_6F_2N_2O$: 148.04, measured (ES, m/z): 149.00 [M+H]$^+$.

Step 2:
3-(Bromomethyl)-1-(difluoromethyl)-1H-pyrazole

To a solution of (1-(difluoromethyl)-1H-pyrazol-3-yl)methanol (2.0 g, 13.50 mmol, 1.0 equiv.) in THF (10 mL) was added PBr$_3$ (4.3 g, 16.20 mmol, 1.2 equiv.) at 0° C. The mixture stirred at room temperature for 2 h. The reaction was quenched with water (20 mL). The resulting mixture was extracted with ethyl acetate (3×20 mL). The organic layers were combined, dried over anhydrous sodium sulfate, filtered and concentrated to yield the 3-(bromomethyl)-1-(difluoromethyl)-1H-pyrazole as a yellow oil. LC/MS: mass calculated for $C_5H_5BrF_2N_2$: 209.96, measured (ES, m/z): 210.95 [M+H]$^+$.

Step 3: 4-(1-(1-(5-Bromopyridin-2-yl)-2-(1-(difluoromethyl)-1H-pyrazol-3-yl)ethyl)-1H-pyrazol-4-yl)-2-(trifluoromethyl)pyridine To a solution of 4-(1-((5-bromopyridin-2-yl)methyl)-1H-pyrazol-4-yl)-2-(trifluoromethyl)pyridine (500 mg, 1.31 mmol, 1.0 equiv.) in THF (10 mL) was added LiHMDS (1.3 mL, 1.31 mmol, 1.0 equiv. 1M in THF) at −78° C. After 1H, the solution of 3-(bromomethyl)-1-(difluoromethyl)-1H-pyrazole (413 mg, 1.96 mmol) in THF (3 mL) was added (−78° C.). The resulting mixture was maintained under nitrogen and stirred at room temperature for 2 h. The reaction was quenched with water (20 mL). The resulting mixture was extracted with ethyl acetate (3×20 mL). The organic layers were combined, dried over anhydrous sodium sulfate, filtered and concentrated. The resulting residue was purified by silica gel chromatography (0→30% ethyl acetate/petroleum ether) to yield the 4-(1-(1-(5-bromopyridin-2-yl)-2-(1-(difluoromethyl)-1H-pyrazol-3-yl)ethyl)-1H-pyrazol-4-yl)-2-(trifluoromethyl)pyridine as a yellow oil. LC/MS: mass calculated for $C_{20}H_{14}BrF_5N_6$: 512.04, measured (ES, m/z): 513.15 [M+H]$^+$.

Step 4: 4-Chloro-2-(6-(2-(1-(difluoromethyl)-1H-pyrazol-3-yl)-1-(4-(2-(trifluoromethyl)pyridin-4-yl)-1H-pyrazol-1-yl)ethyl)pyridin-3-yl)-3-fluoroaniline To a solution of 4-(1-(1-(5-bromopyridin-2-yl)-2-(1-(difluoromethyl)-1H-pyrazol-3-yl)ethyl)-1H-pyrazol-4-yl)-2-(trifluoromethyl)pyridine (530 mg, 1.03 mmol, 1.0 equiv.) in 1,4-dioxane (10 mL) and H$_2$O (1 mL) was added (6-amino-3-chloro-2-fluorophenyl)boronic acid (234.6 mg, 1.24 mmol, 1.2 equiv.), K$_2$CO$_3$ (214 mg, 1.55 mmol, 1.5 equiv.), Pd(pph$_3$)$_4$ (119 mg, 0.10 mmol, 0.1 equiv.). The resulting mixture was maintained under nitrogen and stirred at 90° C. for 3 h. The reaction was quenched with water (20 mL). The resulting mixture was extracted with ethyl acetate (3×20 mL). The organic layers were combined, dried over anhydrous sodium sulfate, filtered and concentrated. The resulting residue was purified by silica gel chromatography (0→100% ethyl acetate/petroleum ether) to yield the 4-chloro-2-(6-(2-(1-(difluoromethyl)-1H-pyrazol-3-yl)-1-(4-(2-(trifluoromethyl)pyridin-4-yl)-1H-pyrazol-1-yl)ethyl)pyridin-3-yl)-3-fluoroaniline as a yellow oil. LC/MS: mass calculated for $C_{26}H_{18}ClF_6N_7$: 477.12, measured (ES, m/z): 478.20 [M+H]$^+$.

Step 5: 4-(1-(1-(5-(3-Chloro-2-fluoro-6-(1H-tetrazol-1-yl)phenyl)pyridin-2-yl)-2-(1-(difluoromethyl)-1H-pyrazol-3-yl)ethyl)-1H-pyrazol-4-yl)-2-(trifluoromethyl)pyridine To a solution of 4-chloro-2-(6-(2-(1-(difluoromethyl)-1H-pyrazol-3-yl)-1-(4-(2-(trifluoromethyl)pyridin-4-yl)-1H-pyrazol-1-yl)ethyl)pyridin-3-yl)-3-fluoroaniline (500 mg, 0.87 mmol, 1.0 equiv.) in AcOH (5 mL) was added TMSN$_3$ (2.5 mL) and trimethoxymethane (2.5 mL). The mixture stirred at room temperature overnight. The residue was purified by C18 column with CH$_3$CN/0.05% TFA water (5%460%) to yield the 4-(1-(1-(5-(3-chloro-2-fluoro-6-(1H-tetrazol-1-yl)phenyl)pyridin-2-yl)-2-(1-(difluoromethyl)-1H-pyrazol-3-yl)ethyl)-1H-pyrazol-4-yl)-2-(trifluoromethyl)pyridine as a yellow oil. LC/MS: mass calculated for $C_{27}H_{17}ClF_6N_{10}$: 630.12, measured (ES, m/z): 631.20 [M+H]$^+$.

Step 6: (R)-5-(3-chloro-2-fluoro-6-(1H-tetrazol-1-yl)phenyl)-2-(2-(1-(difluoromethyl)-1H-pyrazol-3-yl)-1-(4-(2-(trifluoromethyl)pyridin-4-yl)-1H-pyrazol-1-yl)ethyl)pyridine 1-oxide To a solution of 4-(1-(1-(5-(3-chloro-2-fluoro-6-(1H-tetrazol-1-yl)phenyl)pyridin-2-yl)-2-(1-(difluoromethyl)-1H-pyrazol-3-yl)ethyl)-1H-pyrazol-4-yl)-2-(trifluoromethyl)pyridine (490 mg, 0.77 mmol, 1.0 equiv.) in MeOH (4 mL) and H$_2$O$_2$ (0.4 mL, 30 wt %) was added methyltrioxorhenium (VII) (19.3 mg, 0.08 mmol, 0.1 equiv.). The mixture stirred at room temperature for 6 h. The residue was purified by silica gel chromatography with CH$_3$CN/0.05% TFA water (5%460%) to yield the resulting residue, which was purified by Chiral-HPLC with (Hex:DCM=3:1) (0.1% DEA):EtOH=50:50 to yield (R)-5-(3-chloro-2-fluoro-6-(1H-tetrazol-1-yl)phenyl)-2-(2-(1-(difluoromethyl)-1H-pyrazol-3-yl)-1-(4-(2-(trifluoromethyl)pyridin-4-yl)-1H-pyrazol-1-yl)ethyl)pyridine 1-oxide as off-white solid.

LC/MS: mass calculated for $C_{27}H_{17}ClF_6N_{10}O$: 646.12, measured (ES, m/z): 647.1 [M+H]$^+$. $^1$H NMR (300 MHz, DMSO-d$_6$) δ 9.67 (s, 1H), 8.83 (s, 1H), 8.65-8.71 (m, 1H), 8.46 (s, 1H), 8.32 (s, 1H), 7.99-8.20 (m, 3H), 7.48-7.95 (m, 3H), 7.15-7.40 (m, 2H), 6.30-6.50 (m, 1H), 6.07-6.15 (m, 1H), 3.60-3.89 (m, 2H). $^{19}$F NMR (282 MHz, DMSO-d$_6$) δ −66.57, −93.87, −112.64.

Example 816: (R)-5-(3-Chloro-2-fluoro-6-(1H-tetrazol-1-yl)phenyl)-2-(1-(2-(difluoromethyl)-1'H,2H-[3,4'-bipyrazol]-1'-yl)-2-(6-(trifluoromethyl)pyridin-3-yl)ethyl)pyridine 1-oxide

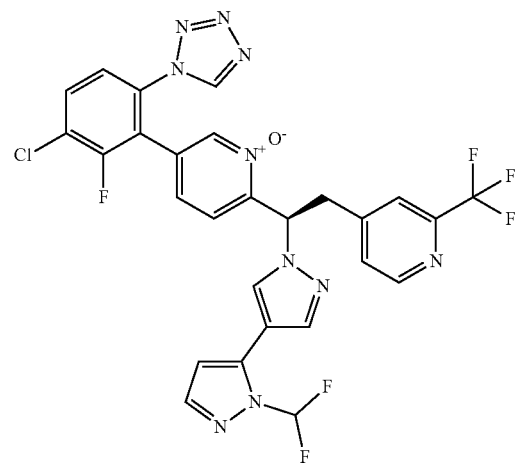

LC/MS: mass calculated for $C_{27}H_{17}ClF_6N_{10}O$: 646.12, measured (ES, m/z): 647.10 [M+H]$^+$. $^1$H NMR (300 MHz, DMSO-d$_6$) δ 9.71 (s, 1H), 8.52 (dt, J=10.9, 1.4 Hz, 2H), 8.22 (s, 1H), 8.08 (dd, J=8.7, 7.8 Hz, 1H), 7.49-7.95 (m, 7H), 7.26 (dd, J=8.3, 1.7 Hz, 1H), 6.61 (d, J=1.7 Hz, 1H), 6.38 (dd, J=9.9, 4.8 Hz, 1H), 3.75 (td, J=14.2, 9.5 Hz, 2H). $^{19}$F NMR (282 MHz, DMSO-d$_6$) d −66.35, −93.63, −93.83, −112.67.

Example 817: (S)-5-(3-Chloro-2-fluoro-6-(1H-tetrazol-1-yl)phenyl)-2-(1-(2-(difluoromethyl)-1'H,2H-[3,4'-bipyrazol]-1'-yl)-2-(6-(trifluoromethyl)pyridin-3-yl)ethyl)pyridine 1-oxide

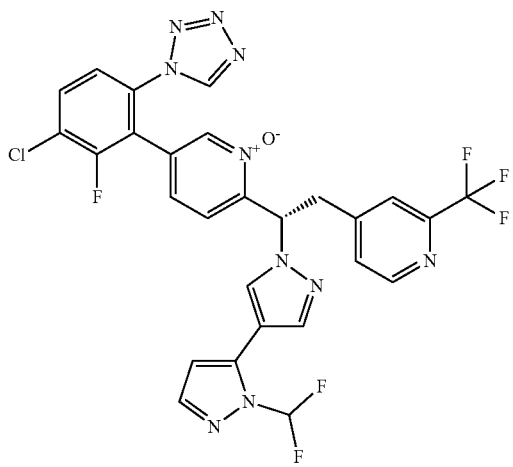

LC/MS: mass calculated for $C_{27}H_{17}ClF_6N_{10}O$: 646.12, measured (ES, m/z): 647.10 [M+H]$^+$. $^1$H NMR (300 MHz, DMSO-d$_6$) δ 9.71 (s, 1H), 8.47-8.57 (m, 2H), 8.22 (s, 1H), 8.02-8.11 (m, 1H), 7.92 (s, 1H), 7.48-7.90 (m, 6H), 7.20-7.30 (m, 1H), 6.61 (d, J=1.7 Hz, 1H), 6.34-6.40 (m, 1H), 3.65-3.84 (m, 2H). $^{19}$F NMR (282 MHz, DMSO-d$_6$) δ −66.34, −93.73, −112.68.

Example 818: (S)-5-(3-Chloro-2-fluoro-6-(1H-tetrazol-1-yl)phenyl)-2-(1-(4-(4-fluoro-1-methyl-1H-1,2,3-triazol-5-yl)-1H-pyrazol-1-yl)-2-(6-(trifluoromethyl)pyridin-3-yl)ethyl)pyridine 1-oxide

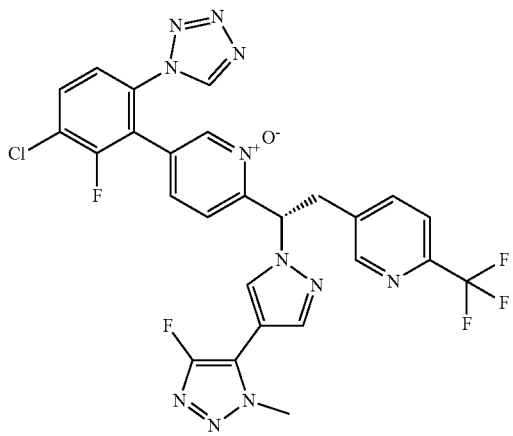

Step 1: 5-Bromo-2-((4-(1-methyl-1H-1,2,3-triazol-5-yl)-1H-pyrazol-1-yl)methyl)pyridine A mixture of cesium carbonate (2.2 g, 6.71 mmol, 1.0 equiv.) and 1-methyl-5-(1H-pyrazol-4-yl)-1H-1,2,3-triazole (1.0 g, 6.71 mmol, 1.0 equiv.) in acetonitrile (15 mL) was stirred for 15 min at room temperature. 5-bromo-2-(bromomethyl)pyridine (1.7 g, 6.71 mmol, 1.0 equiv.) was added and the solution was stirred for 2.5 h at 80° C. The resulting mixture was diluted with water, and the mixture extracted with EA (3×20 mL).

The organic layers were combined, washed with brine (10 mL), dried over Na$_2$SO$_4$ and concentrated. The residue was purified by silica gel chromatography (0%→5%, MeOH/DCM) to yield 5-bromo-2-((4-(1-methyl-1H-1,2,3-triazol-5-yl)-1H-pyrazol-1-yl)methyl)pyridine as a pink solid. LC/MS: mass calculated for $C_{12}H_{11}BrN_6$: 318.02, measured (ES, m/z): 320.95 [M+H+2]$^+$.

Step 2: 5-Bromo-2-(1-(4-(1-methyl-1H-1,2,3-triazol-5-yl)-1H-pyrazol-1-yl)-2-(6-(trifluoromethyl)pyridin-3-yl)ethyl)pyridine To a solution of 5-bromo-2-((4-(1-methyl-1H-1,2,3-triazol-5-yl)-1H-pyrazol-1-yl)methyl)pyridine (500 mg, 1.57 mmol, 1.0 equiv.) in tetrahydrofuran (10 mL) under −80° C. was added Lithium bis(trimethylsilyl)amide (1.6 mL, 1.57 mmol, 1.0 equiv, 1M in THF) by drops. The resulting mixture was then stirred at that temperature for 1 h and 5-(bromomethyl)-2-(trifluoromethyl)pyridine (451 mg, 1.88 mmol, 1.2 equiv.) was added. The resulting mixture was stirred under −80° C. for 1 h. The resulting mixture was diluted with water, and the mixture extracted with EA (3×10 mL). The organic layers were combined, washed with water (5×10 mL), then washed with brine (10 mL), dried over Na$_2$SO$_4$ and concentrated. The residue was purified by silica gel chromatography (0%→5%, MeOH/DCM) to yield 5-bromo-2-(1-(4-(1-methyl-1H-1,2,3-triazol-5-yl)-1H-pyrazol-1-yl)-2-(6-(trifluoromethyl)pyridin-3-yl)ethyl)pyridine as a brown solid. LC/MS: mass calculated for $C_{19}H_{15}BrF_3N_7$: 477.05, measured (ES, m/z): 478.00 [M+H]$^+$ Step 3: 5-Bromo-2-(1-(4-(4-fluoro-1-methyl-1H-1,2,3-triazol-5-yl)-1H-pyrazol-1-yl)-2-(6-(trifluoromethyl)pyridin-3-yl)ethyl)pyridine A mixture of 5-bromo-2-(1-(4-(1-methyl-1H-1,2,3-triazol-5-yl)-1H-pyrazol-1-yl)-2-(6-(trifluoromethyl)pyridin-3-yl)ethyl)pyridine (512 mg, 1.07 mmol, 1.0 equiv.) and 1-chloromethyl-4-fluoro-1,4-diazoniabicyclo[2.2.2]octane bis(tetrafluoroborate) (569 mg, 1.61 mmol, 1.5 equiv.) in acetonitrile (6 mL) was stirred at 80° C. for 2.5 h. The resulting mixture was diluted with water, and the mixture extracted with EA (3×10 mL). The organic layers were combined, washed with water (5×10 mL), then washed with brine (10 mL), dried over Na$_2$SO$_4$ and concentrated. The residue was purified by silica gel column (0%→5%, MeOH/DCM) to yield 5-bromo-2-(1-(4-(4-fluoro-1-methyl-1H-1,2,3-triazol-5-yl)-1H-pyrazol-1-yl)-2-(6-(trifluoromethyl)pyridin-3-yl)ethyl)pyridine as a light yellow oil. LC/MS: mass calculated for $C_{19}H_{14}BrF_4N_7$: 495.04, measured (ES, m/z): 498.05 [M+H+2]$^+$.

Step 4: 4-Chloro-3-fluoro-2-(6-(1-(4-(4-fluoro-1-methyl-1H-1,2,3-triazol-5-yl)-1H-pyrazol-1-yl)-2-(6-(trifluoromethyl)pyridin-3-yl)ethyl)pyridin-3-yl)aniline A mixture of 5-bromo-2-(1-(4-(4-fluoro-1-methyl-1H-1,2,3-triazol-5-yl)-1H-pyrazol-1-yl)-2-(6-(trifluoromethyl)pyridin-3-yl)ethyl)pyridine (558 mg, 1.12 mmol, 1.0 equiv.), 6-amino-3-chloro-2-fluorophenylboronic acid (319 mg, 319.41 mmol, 1.5 equiv.), Pd(PPh$_3$)$_4$ (130 mg, 0.11 mmol, 0.1 equiv.) and K$_2$CO$_3$ (466 mg, 3.37 mmol, 3.0 equiv.) in 1,4-dioxane/water (V/V=5:1, 2.4 mL) was refluxed at 90° C. under N$_2$ for 3 h. The resulting mixture was diluted with water, and the mixture extracted with EA (3×10 mL). The organic layers were combined, washed with water (5×10 mL), then washed with brine (10 mL), dried over Na$_2$SO$_4$ and concentrated. The residue was purified by silica gel column (0%→5%, MeOH/DCM) to yield 4-chloro-3-fluoro-2-(6-(1-(4-(4-fluoro-1-methyl-1H-1,2,3-triazol-5-yl)-1H-pyrazol-1-yl)-2-(6-(trifluoromethyl)pyridin-3-yl)ethyl)pyridin-3-yl)aniline as a light yellow oil. LC/MS: mass calculated for C$_{25}$H$_{18}$ClF$_5$N$_8$: 560.13, measured (ES, m/z): 560.91 [M+H]$^+$.

Step 5: 5-(3-Chloro-2-fluoro-6-(1H-tetrazol-1-yl)phenyl)-2-(1-(4-(4-fluoro-1-methyl-1H-1,2,3-triazol-5-yl)-1H-pyrazol-1-yl)-2-(6-(trifluoromethyl)pyridin-3-yl)ethyl)pyridine A mixture of 4-chloro-3-fluoro-2-(6-(1-(4-(4-fluoro-1-methyl-1H-1,2,3-triazol-5-yl)-1H-pyrazol-1-yl)-2-(6-(trifluoromethyl)pyridin-3-yl)ethyl)pyridin-3-yl)aniline (319 mg, 0.57 mmol, 1.0 equiv.), trimethoxymethane (2 mL), azidotrimethylsilane (2 mL) and acetic acid (2 mL) was stirred overnight at room temperature. The reaction was purified by reverse chromatography on C18 (0%→55% MeCN/H$_2$O (0.05% CF$_3$COOH)) to yield 5-(3-chloro-2-fluoro-6-(1H-tetrazol-1-yl)phenyl)-2-(1-(4-(4-fluoro-1-methyl-1H-1,2,3-triazol-5-yl)-1H-pyrazol-1-yl)-2-(6-(trifluoromethyl)pyridin-3-yl)ethyl)pyridine as a yellow solid. LC/MS: mass calculated for C$_2$H$_{17}$ClF$_5$N$_{11}$: 613.13, measured (ES, m/z): 614.05 [M+H]$^+$.

Step 6: (S)-5-(3-Chloro-2-fluoro-6-(1H-tetrazol-1-yl)phenyl)-2-(1-(4-(4-fluoro-1-methyl-1H-1,2,3-triazol-5-yl)-1H-pyrazol-1-yl)-2-(6-(trifluoromethyl)pyridin-3-yl)ethyl)pyridine 1-oxide A mixture of 5-(3-chloro-2-fluoro-6-(1H-tetrazol-1-yl)phenyl)-2-(1-(4-(4-fluoro-1-methyl-1H-1,2,3-triazol-5-yl)-1H-pyrazol-1-yl)-2-(6-(trifluoromethyl)pyridin-3-yl)ethyl)pyridine (280 mg, 0.46 mmol, 1.0 equiv.), methyltrioxorhenium (57 mg, 0.23 mmol, 0.5 equiv.), hydrogen peroxide (0.9 mL, 30 wt %) in CH$_3$OH (3 mL) was stirred for 3 h at room temperature. The resulting mixture was purified by reverse phase chromatography on C18 (MeCN/H$_2$O (0.05% CF$_3$COOH)) to yield 5-(3-chloro-2-fluoro-6-(1H-tetrazol-1-yl)phenyl)-2-(1-(4-(4-fluoro-1-methyl-1H-1,2,3-triazol-5-yl)-1H-pyrazol-1-yl)-2-(6-(trifluoromethyl)pyridin-3-yl)ethyl)pyridine 1-oxide as a white solid. The racemic product was separated by chiral-HPLC to yield (S)-5-(3-chloro-2-fluoro-6-(1H-tetrazol-1-yl)phenyl)-2-(1-(4-(4-fluoro-1-methyl-1H-1,2,3-triazol-5-yl)-1H-pyrazol-1-yl)-2-(6-(trifluoromethyl)pyridin-3-yl)ethyl)pyridine 1-oxide as a white solid.

LC/MS: mass calculated for C$_{27}$H$_{17}$ClF$_5$N$_{11}$O: 629.12, measured (ES, m/z): 630.10 [M+H]$^+$. $^1$H NMR (300 MHz, DMSO-d$_6$) δ 9.72 (s, 1H), 8.52 (d, J=5.2 Hz, 2H), 8.37 (s, 1H), 8.00-8.10 (m, 1H), 7.99 (s, 1H), 7.73-7.86 (m, 3H), 7.53 (d, J=8.3 Hz, 1H), 7.24-7.26 (m, 1H), 6.37-6.42 (m, 1H), 3.98 (s, 3H), 3.68-3.84 (m, 2H). $^{19}$F-NMR (282 MHz, DMSO-d$_6$) δ −66.31, −112.68, −145.24.

Example 819: (R)-5-(3-Chloro-2-fluoro-6-(1H-tetrazol-1-yl)phenyl)-2-(1-(4-(4-fluoro-1-methyl-1H-1,2,3-triazol-5-yl)-1H-pyrazol-1-yl)-2-(6-(trifluoromethyl)pyridin-3-yl)ethyl)pyridine 1-oxide

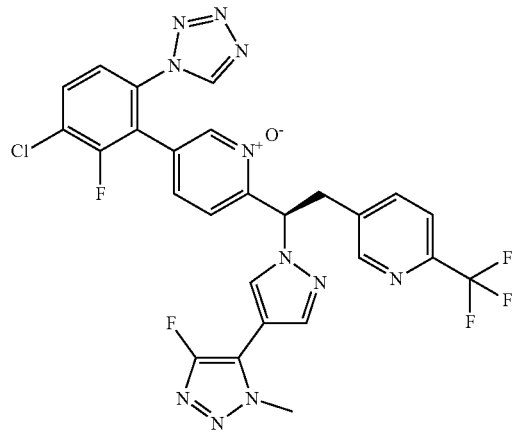

Step 1: 5-Bromo-2-((4-(1-methyl-1H-1,2,3-triazol-5-yl)-1H-pyrazol-1-yl)methyl)pyridine A mixture of cesium carbonate (2.2 g, 6.71 mmol, 1.0 equiv.) and 1-methyl-5-(1H-pyrazol-4-yl)-1H-1,2,3-triazole (1.0 g, 6.71 mmol, 1.0 equiv.) in acetonitrile (15 mL) was stirred for 15 min at room temperature.

5-Bromo-2-(bromomethyl)pyridine (1.7 g, 6.71 mmol, 1.0 equiv.) was added and the solution was stirred for 2.5 h at 80° C. The resulting mixture was diluted with water, and the mixture extracted with EA (3×20 mL). The organic layers were combined, washed with brine (10 mL), dried over Na$_2$SO$_4$ and concentrated. The residue was purified by silica gel chromatography (0%→5%, MeOH/DCM) to yield 5-bromo-2-((4-(1-methyl-1H-1,2,3-triazol-5-yl)-1H-pyrazol-1-yl)methyl)pyridine (707 mg, 33.0% yield) s a pink solid. LC/MS: mass calculated for C$_{12}$H$_{11}$BrN$_6$: 318.02, measured (ES, m/z): 320.95 [M+H+2]$^+$.

Step 2: 5-Bromo-2-(1-(4-(1-methyl-1H-1,2,3-triazol-5-yl)-1H-pyrazol-1-yl)-2-(6-(trifluoromethyl)pyridin-3-yl)ethyl)pyridine To a solution of 5-bromo-2-((4-(1-methyl-1H-1,2,3-triazol-5-yl)-1H-pyrazol-1-yl)methyl)pyridine (500 mg, 1.57 mmol, 1.0 equiv.) in tetrahydrofuran (10 mL) at −80° C. was added lithium bis(trimethylsilyl)amide (1.6 mL, 1.57 mmol, 1.0 equiv, 1 M in THF) by drops. The resulting mixture was then stirred at that temperature for 1 h and 5-(bromomethyl)-2-(trifluoromethyl)pyridine (451 mg, 1.88 mmol, 1.2 equiv.) was added. The resulting mixture was slowly warmed to room temperature and stirred for 1 h. The resulting mixture was diluted with water, and the mixture extracted with EA (3×10 mL). The organic layers were combined, washed with water (5×10 mL), then washed with brine (10 mL), dried over Na$_2$SO$_4$ and concentrated. The residue was purified by silica gel chromatography (0%→5%, MeOH/DCM) to yield 5-bromo-2-(1-(4-(1-methyl-1H-1,2,3-triazol-5-yl)-1H-pyrazol-1-yl)-2-(6-(trifluoromethyl)pyridin-3-yl)ethyl)pyridine as a brown solid. LC/MS: mass calculated for C$_{19}$H$_{15}$BrF$_3$N$_7$: 477.05, measured (ES, m/z): 478.00 [M+H]$^+$.

Step 3: 5-Bromo-2-(1-(4-(4-fluoro-1-methyl-1H-1,2,3-triazol-5-yl)-1H-pyrazol-1-yl)-2-(6-(trifluoromethyl)pyridin-3-yl)ethyl)pyridine A mixture of 5-bromo-2-(1-(4-(1-methyl-1H-1,2,3-triazol-5-yl)-1H-pyrazol-1-yl)-2-(6-(trifluoromethyl)pyridin-3-yl)ethyl)pyridine (512 mg, 1.07 mmol, 1.0 equiv.) and 1-chloromethyl-4-fluoro-1,4-diazoniabicyclo[2.2.2]octane bis(tetrafluoroborate) (569 mg, 1.61 mmol, 1.5 equiv.) in acetonitrile (6 mL) was stirred at 80° C. for 2.5 h. The resulting mixture was diluted with water, and the mixture extracted with EA (3×10 mL). The organic layers were combined, washed with water (5×10 mL), then washed with brine (10 mL), dried over $Na_2SO_4$ and concentrated. The residue was purified by silica gel column (0%→5%, MeOH/DCM) to yield 5-bromo-2-(1-(4-(4-fluoro-1-methyl-1H-1,2,3-triazol-5-yl)-1H-pyrazol-1-yl)-2-(6-(trifluoromethyl)pyridin-3-yl)ethyl)pyridine as a light yellow oil. LC/MS: mass calculated for $C_{19}H_{14}BrF_4N_7$: 495.04, measured (ES, m/z): 498.05 $[M+H+2]^+$.

Step 4: 4-Chloro-3-fluoro-2-(6-(1-(4-(4-fluoro-1-methyl-1H-1,2,3-triazol-5-yl)-1H-pyrazol-1-yl)-2-(6-(trifluoromethyl)pyridin-3-yl)ethyl)pyridin-3-yl)aniline A mixture of 5-bromo-2-(1-(4-(4-fluoro-1-methyl-1H-1,2,3-triazol-5-yl)-1H-pyrazol-1-yl)-2-(6-(trifluoromethyl)pyridin-3-yl)ethyl)pyridine (558 mg, 1.12 mmol, 1.0 equiv.), 6-amino-3-chloro-2-fluorophenylboronic acid (319 mg, 319.41 mmol, 1.5 equiv.), $Pd(PPh_3)_4$ (130 mg, 0.11 mmol, 0.1 equiv.) and $K_2CO_3$ (466 mg, 3.37 mmol, 3.0 equiv.) in 1,4-dioxane/water (V/V=5:1, 2.4 mL) was refluxed at 90° C. under $N_2$ for 3 h. The resulting mixture was diluted with water, and the mixture extracted with EA (3×10 mL). The organic layers were combined, washed with water (5×10 mL), then washed with brine (10 mL), dried over $Na_2SO_4$ and concentrated. The residue was purified by silica gel column (0%→5%, MeOH/DCM) to yield 4-chloro-3-fluoro-2-(6-(1-(4-(4-fluoro-1-methyl-1H-1,2,3-triazol-5-yl)-1H-pyrazol-1-yl)-2-(6-(trifluoromethyl)pyridin-3-yl)ethyl)pyridin-3-yl)aniline as a light yellow oil. LC/MS: mass calculated for $C_{25}H_{18}ClF_5N_8$: 560.13, measured (ES, m/z): 560.91 $[M+H]^+$.

Step 5: 5-(3-Chloro-2-fluoro-6-(1H-tetrazol-1-yl)phenyl)-2-(1-(4-(4-fluoro-1-methyl-1H-1,2,3-triazol-5-yl)-1H-pyrazol-1-yl)-2-(6-(trifluoromethyl)pyridin-3-yl)ethyl)pyridine A mixture of 4-chloro-3-fluoro-2-(6-(1-(4-(4-fluoro-1-methyl-1H-1,2,3-triazol-5-yl)-1H-pyrazol-1-yl)-2-(6-(trifluoromethyl)pyridin-3-yl)ethyl)pyridin-3-yl)aniline (319 mg, 0.57 mmol, 1.0 equiv.), trimethoxymethane (2 mL), azidotrimethylsilane (2 mL) and acetic acid (2 mL) was stirred overnight at room temperature. The reaction was purified by reverse chromatography on C18 (0%→55% MeCN/$H_2O$ (0.05% $CF_3COOH$)) to yield 5-(3-chloro-2-fluoro-6-(1H-tetrazol-1-yl)phenyl)-2-(1-(4-(4-fluoro-1-methyl-1H-1,2,3-triazol-5-yl)-1H-pyrazol-1-yl)-2-(6-(trifluoromethyl)pyridin-3-yl)ethyl)pyridine as a yellow solid. LC/MS: mass calculated for $C_{26}H_{17}ClF_5N_{11}$: 613.13, measured (ES, m/z): 614.05 $[M+H]^+$.

Step 6: (R)-5-(3-Chloro-2-fluoro-6-(1H-tetrazol-1-yl)phenyl)-2-(1-(4-(4-fluoro-1-methyl-1H-1,2,3-triazol-5-yl)-1H-pyrazol-1-yl)-2-(6-(trifluoromethyl)pyridin-3-yl)ethyl)pyridine 1-oxide A mixture of 5-(3-chloro-2-fluoro-6-(1H-tetrazol-1-yl)phenyl)-2-(1-(4-(4-fluoro-1-methyl-1H-1,2,3-triazol-5-yl)-1H-pyrazol-1-yl)-2-(6-(trifluoromethyl)pyridin-3-yl)ethyl)pyridine (280 mg, 0.46 mmol, 1.0 equiv.), methyltrioxorhenium (57 mg, 0.23 mmol, 0.5 equiv.), hydrogen peroxide (0.9 mL, 30 wt %) in $CH_3OH$ (3 mL) was stirred for 3 h at room temperature. The resulting mixture was purified by reverse phase chromatography on C18 (MeCN/$H_2O$ (0.05% $CF_3COOH$)) to yield 5-(3-chloro-2-fluoro-6-(1H-tetrazol-1-yl)phenyl)-2-(1-(4-(4-fluoro-1-methyl-1H-1,2,3-triazol-5-yl)-1H-pyrazol-1-yl)-2-(6-(trifluoromethyl)pyridin-3-yl)ethyl)pyridine 1-oxide as a white solid. The racemic product was separated by chiral-HPLC to yield (R)-5-(3-chloro-2-fluoro-6-(1H-tetrazol-1-yl)phenyl)-2-(1-(4-(4-fluoro-1-methyl-1H-1,2,3-triazol-5-yl)-1H-pyrazol-1-yl)-2-(6-(trifluoromethyl)pyridin-3-yl)ethyl)pyridine 1-oxide as a white solid.

LC/MS: mass calculated for $C_{26}H_{17}ClF_5N_{11}O$: 629.12, measured (ES, m/z): 630.10 $[M+H]^+$. $^1H$ NMR (300 MHz, DMSO-$d_6$) δ 9.72 (s, 1H), 8.52 (d, J=5.3 Hz, 2H), 8.37 (s, 1H), 8.03-8.14 (m, 1H), 8.00 (s, 1H), 7.73-7.86 (m, 3H), 7.53 (d, J=8.3 Hz, 1H), 7.24-7.26 (m, 1H), 6.38-6.42 (m, 1H), 3.98 (s, 3H), 3.65-3.87 (m, 2H). $^{19}$F-NMR (282 MHz, DMSO-$d_6$) δ −66.31, −112.68, −145.24.

Example 820: (R)-5-(3-Chloro-6-(4-cyclopropyl-1H-1,2,3-triazol-1-yl)-2-fluorophenyl)-2-(3-(difluoromethoxy)-1-(4-(1-methyl-1H-1,2,4-triazol-5-yl)-1H-pyrazol-1-yl)propyl)pyridine 1-oxide

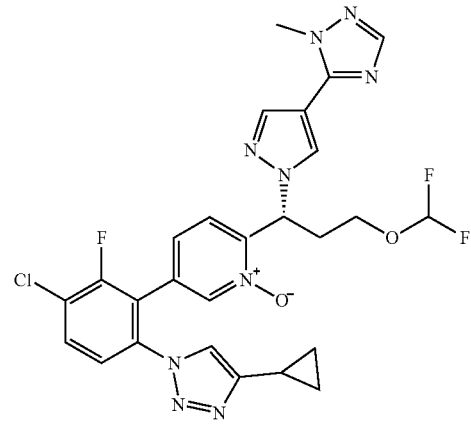

Step 1: 5-Bromo-2-(3-(difluoromethoxy)-1-(4-(1-methyl-1H-1,2,4-triazol-5-yl)-1H-pyrazol-1-yl)propyl)pyridine To a solution of 1-methyl-5-(1H-pyrazol-4-yl)-1H-1,2,4-triazole (80 mg, 0.54 mmol, 1.0 equiv.) and cesium carbonate (0.52 g, 1.61 mmol, 3.0 equiv.) in acetonitrile (2 mL) was added 1-(5-bromopyridin-2-yl)-3-(difluoromethoxy)propyl methanesulfonate (193 mg, 0.54 mmol, 1.0 equiv.) 10 minutes later. The reaction mixture was stirred at 80° C. for 3.5 h. The reaction was added water, and the mixture extracted with EA three times. The combined organic layers were washed with brine, dried over $Na_2SO_4$, and concentrated under vacuum. The residue was purified by silica gel chromatography with $CH_3OH$/DCM (0→10%) to yield 5-bromo-2-(3-(difluoromethoxy)-1-(4-(1-methyl-1H-1,2,4-triazol-5-yl)-1H-pyrazol-1-yl)propyl)pyridine as off-white solid. LC/MS: mass calculated for $C_{15}H_{15}BrF_2N_6O$: 412.05, measured (ES, m/z): 413.00, 414.95 $[M+H, M+H+2]^+$.

Step 2: (6-(3-(Difluoromethoxy)-1-(4-(1-methyl-1H-1,2,4-triazol-5-yl)-1H-pyrazol-1-yl)propyl)pyridin-3-yl)boronic acid To a mixture of 5-bromo-2-(3-(difluoromethoxy)-1-(4-(1-methyl-1H-1,2,4-triazol-5-yl)-1H-pyrazol-1-yl)propyl)pyridine (190 mg, 0.46 mmol, 1.0 equiv.) and 4,4,4',4',5,5,5',5'-octamethyl-2,2'-bi(1,3,2-dioxaborolane) (234 mg, 0.92 mmol, 2.0 equiv.) in 1,4-dioxane (3 mL) was added potassium acetate (226 mg, 2.30 mmol, 5.0 equiv.) and Pd(dppf)Cl$_2$ (39 mg, 0.05 mmol, 0.1 equiv.) under N$_2$. The solution was stirred at 100° C. for 2 h. The mixture was diluted with H$_2$O, extracted with DCM twice. The combined organic layers were washed with brine, dried over Na$_2$SO$_4$ concentrated under vacuum to yield (6-(3-(difluoromethoxy)-1-(4-(1-methyl-1H-1,2,4-triazol-5-yl)-1H-pyrazol-1-yl)propyl)pyridin-3-yl)boronic acid as a brown solid. LC/MS: mass calculated for C$_{15}$H$_{17}$BF$_2$N$_6$O$_3$: 378.14, measured (ES, m/z): 379.15 [M+H]$^+$.

Step 3: 5-(3-Chloro-6-(4-cyclopropyl-1H-1,2,3-triazol-1-yl)-2-fluorophenyl)-2-(3-(difluoromethoxy)-1-(4-(1-methyl-1H-1,2,4-triazol-5-yl)-1H-pyrazol-1-yl)propyl)pyridine To a mixture of (6-(3-(difluoromethoxy)-1-(4-(1-methyl-1H-1,2,4-triazol-5-yl)-1H-pyrazol-1-yl)propyl)pyridin-3-yl) boronic acid (100 mg, 0.26 mmol, 1.2 equiv.) and 1-(4-chloro-3-fluoro-2-iodophenyl)-4-cyclopropyl-1H-1,2,3-triazole (80 mg, 0.22 mmol, 1.0 equiv.) in the mixed solution of 1,4-dioxane (2 mL) and water (0.5 mL) was added potassium carbonate (122 mg, 0.88 mmol, 4.0 equiv.) and tetrakis(triphenylphosphine) palladium(25 mg, 0.02 mmol, 0.1 equiv.). The reaction vessel was evacuated, then purged with nitrogen. This was repeated 2×. The reaction mixture was stirred at 100° C. for 2 h under N$_2$.

Water was added, the mixture was extracted with EA. The combined organic layers were washed with brine, dried over Na$_2$SO$_4$, and concentrated under vacuum. Than the mixture solid was purified by silica gel chromatography with EtOAc/petroleum (0→90%) to yield 5-(3-chloro-6-(4-cyclopropyl-1H-1,2,3-triazol-1-yl)-2-fluorophenyl)-2-(3-(difluoromethoxy)-1-(4-(1-methyl-1H-1,2,4-triazol-5-yl)-1H-pyrazol-1-yl)propyl) pyridine as off-white solid. LC/MS: mass calculated for C$_{26}$H$_{23}$ClF$_3$N$_9$O: 569.17, measured (ES, m/z): 570.25 [M+H]$^+$.

Step 4: (R)-5-(3-Chloro-6-(4-cyclopropyl-1H-1,2,3-triazol-1-yl)-2-fluorophenyl)-2-(3-(difluoromethoxy)-1-(4-(1-methyl-1H-1,2,4-triazol-5-yl)-1H-pyrazol-1-yl)propyl)pyridine 1-oxide To a solution of 5-(3-chloro-6-(4-cyclopropyl-1H-1,2,3-triazol-1-yl)-2-fluorophenyl)-2-(3-(difluoromethoxy)-1-(4-(1-methyl-1H-1,2,4-triazol-5-yl)-1H-pyrazol-1-yl)propyl) pyridine (55 mg, 0.10 mmol, 1.0 equiv.) and methyltrioxorhenium (VII) (5 mg, 0.02 mmol, 0.2 equiv.) in CH$_3$OH (0.5 mL) was added hydrogen peroxide (0.10 mL, 0.97 mmol, 10.0 equiv.). The reaction mixture was stirred at room temperature for 2 h. The reaction was purified by reverse phase chromatography on C18 (80 g, MeCN/H$_2$O (0.05% CF$_3$COOH: 0-50%). The resulting residue was purified by Prep-Chiral-HPLC to yield (R)-5-(3-chloro-6-(4-cyclopropyl-1H-1,2,3-triazol-1-yl)-2-fluorophenyl)-2-(3-(difluoromethoxy)-1-(4-(1-methyl-1H-1,2,4-triazol-5-yl)-1H-pyrazol-1-yl)propyl)pyridine 1-oxide as a white solid.

LC/MS: mass calculated for C$_{26}$H$_{23}$ClF$_3$N$_9$O$_2$: 585.16, measured (ES, m/z): 586.15 [M+H]$^+$. $^1$H NMR (300 MHz, DMSO-d$_6$): b 8.60 (s, 1H), 8.33 (s, 1H), 8.09 (s, 1H), 7.91-8.01 (m, 2H), 7.89 (s, 1H), 7.59 (dd, J=8.7, 1.5 Hz, 1H), 7.31 (d, J=8.3 Hz, 1H), 7.10 (d, J=8.2 Hz, 1H), 6.63 (t, J=75.7 Hz, 1H), 6.24-6.35 (m, 1H), 3.96 (s, 3H), 3.79-3.90 (m, 1H), 3.68-3.80 (m, 1H), 2.58-2.78 (m, 2H), 1.85-1.95 (m, 1H), 0.80-0.92 (m, 2H), 0.53-0.64 (m, 2H). $^{19}$F-NMR (282 MHz, DMSO-d$_6$): δ −83.91, −113.37.

Example 821: (S)-5-(3-Chloro-6-(4-cyclopropyl-1H-1,2,3-triazol-1-yl)-2-fluorophenyl)-2-(3-(difluoromethoxy)-1-(4-(1-methyl-1H-1,2,4-triazol-5-yl)-1H-pyrazol-1-yl)propyl)pyridine 1-oxide

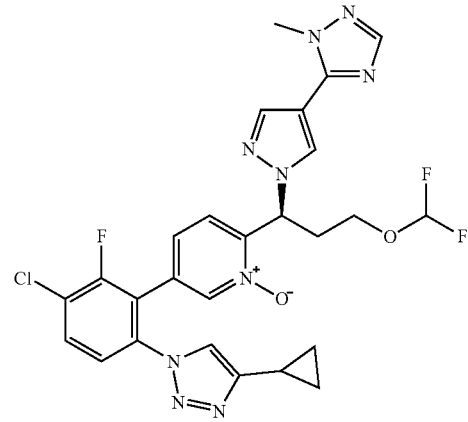 [SMILES: Cn1ncnc1-c1cnn([C@@H](CCOC(F)F)c2ccc(-c3c(-n4cc(C5CC5)nn4)ccc(Cl)c3F)c[n+]2[O-])c1]

LC/MS: mass calculated for C$_{26}$H$_{23}$ClF$_3$N$_9$O$_2$: 585.16, measured (ES, m/z): 586.15 [M+H]$^+$. $^1$H NMR (300 MHz, DMSO-d$_6$) δ 8.60 (s, 1H), 8.33 (s, 1H), 8.09 (s, 1H), 7.91-8.01 (m, 2H), 7.89 (s, 1H), 7.56-7.74 (m, 1H), 7.31 (d, J=8.3 Hz, 1H), 7.10 (d, J=8.2 Hz, 1H), 6.63 (t, J=75.8 Hz, 1H), 6.25-6.34 (m, 1H), 3.96 (s, 3H), 3.81-3.90 (m, 1H), 3.65-3.75 (m, 1H), 2.60-2.72 (m, 2H), 1.85-1.95 (m, 1H), 0.80-0.92 (m, 2H), 0.53-0.64 (m, 2H). $^{19}$F NMR (282 MHz, DMSO) δ −83.25, −112.37.

Example 822: (R)-5-(3-Chloro-2-fluoro-6-(1H-tetrazol-1-yl)phenyl)-2-(1-(4-(1-(difluoromethyl)-1H-1,2,4-triazol-5-yl)-1H-pyrazol-1-yl)-2-(6-(trifluoromethyl)pyridin-3-yl)ethyl)pyridine 1-oxide

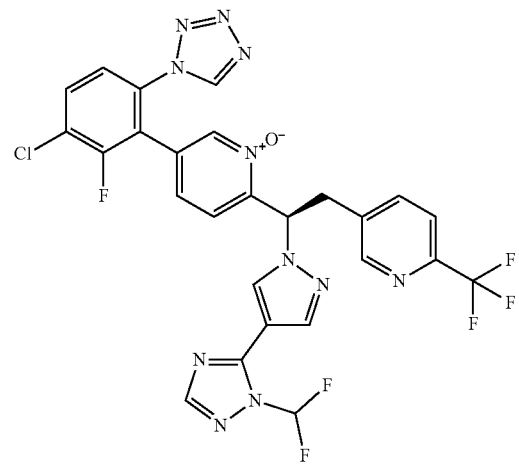

Step 1: N-Methoxy-N-methyl-2-(6-(trifluoromethyl) pyridin-3-yl)acetamide

To a solution of (6-trifluoromethyl-pyridin-3-yl)-acetic acid (1.0 g, 4.88 mmol, 1.0 equiv.) in DCM (30 mL) was added CDI (1.0 g, 6.34 mmol, 1.3 equiv.). The above mixture was stirred for 0.5 hour at room temperature. Then added N,O-dimethylhydroxylamine hydrochloride (0.57 g, 5.85 mmol, 1.2 equiv.). The resulting mixture was stirred at room temperature. for 14 h. The reaction was quenched with water (30 mL).

The resulting mixture was extracted with DCM (3×25 mL). The organic layers were combined and washed with 0.5 M HCl (30 mL) NaHCO$_3$ (aq.) (30 mL). The organic layers were dried over anhydrous sodium sulfate, filtered and concentrated. The resulting residue was N-methoxy-N-methyl-2-(6-(trifluoromethyl)pyridin-3-yl)acetamide as a brown oil. LC/MS: mass calculated for $C_{10}H_{11}F_3N_2O_2$: 248.08, measured (ES, m/z): 249.05 [M+H]$^+$.

Step 2: 1-(5-Bromopyridin-2-yl)-2-(6-(trifluoromethyl)pyridin-3-yl)ethan-1-one To a solution of 2,5-dibromopyridine (1.7 g, 7.25 mmol, 1.5 equiv.) in toluene (20 mL) was added n-butyllithium (2.5 mL, 6.28 mmol, 2.5 M, 1.3 equiv.) under nitrogen and stirred at −78° C. for 1 h. To the resulting mixture was added N-methoxy-N-methyl-2-(6-(trifluoromethyl)pyridin-3-yl) acetamide (1.2 g, 4.83 mmol, 1.0 equiv.) in toluene (5 mL). The resulting mixture was maintained under nitrogen and stirred at −78° C. for 2 h. The reaction was quenched with aqueous NH$_4$Cl (40 mL). The resulting mixture was extracted with ethyl acetate (3×20 mL). The organic layers were combined, dried over anhydrous sodium sulfate, filtered and concentrated. The resulting residue was purified by silica gel chromatography (0→50% EA/PE) to yield 1-(5-bromopyridin-2-yl)-2-(6-(trifluoromethyl)pyridin-3-yl)ethan-1-one as a brown solid. LC/MS: mass calculated for $C_{13}H_8BrF_3N_2O$: 343.98, measured (ES, m/z): 345.00, 347.00 [M+H, M+H+2]$^+$.

Step 3: 1-(5-Bromopyridin-2-yl)-2-(6-(trifluoromethyl)pyridin-3-yl)ethan-1-ol To a solution of 1-(5-bromopyridin-2-yl)-2-(6-(trifluoromethyl)pyridin-3-yl)ethan-1-one (1.2 g, 3.33 mmol, 1.0 equiv.) in MeOH (20 mL) was added NaBH$_4$ (126 mg, 3.33 mmol, 1.0 equiv.) at 0° C. The resulting mixture was stirred at room temperature for 2 h. The reaction was quenched with water (40 mL). The resulting mixture was extracted with ethyl acetate (3×20 mL). The organic layers were combined, dried over anhydrous sodium sulfate, filtered and concentrated. The resulting residue was purified by silica gel chromatography (0→50% EA/PE) to yield 1-(5-bromopyridin-2-yl)-2-(6-(trifluoromethyl)pyridin-3-yl)ethan-1-ol as a light yellow solid. LC/MS: mass calculated for $C_{13}H_{10}BrF_3N_2O$: 345.99, measured (ES, m/z): 346.90, 348.90 [M+H, M+H+2]$^+$.

Step 4: 1-(5-Bromopyridin-2-yl)-2-(6-(trifluoromethyl)pyridin-3-yl)ethyl methanesulfonate To a solution of 1-(5-bromopyridin-2-yl)-2-(6-(trifluoromethyl)pyridin-3-yl)ethan-1-ol (589 mg, 1.70 mmol, 1.0 equiv.) and triethylamine (0.59 mL, 4.24 mmol, 2.5 equiv.) in DCM (20 mL) was added methanesulfonic anhydride (591 mg, 3.39 mmol, 2.0 equiv.) at 0° C. The resulting mixture was stirred at room temperature. for 2 h. The reaction was quenched with water (40 mL). The resulting mixture was extracted with DCM (3×20 mL). The organic layers were combined, dried over anhydrous sodium sulfate, filtered and concentrated. The resulting residue was purified by silica gel chromatography (0→50% EA/PE) to yield 1-(5-bromopyridin-2-yl)-2-(6-(trifluoromethyl)pyridin-3-yl)ethyl methanesulfonate as a light yellow solid. LC/MS: mass calculated for $C_{14}H_{12}BrF_3N_2O_3S$: 423.97, measured (ES, m/z): 424.85, 426.85 [M+H, M+H+2]$^+$.

Step 5: 5-Bromo-2-(1-(4-(1-(difluoromethyl)-1H-1,2,4-triazol-5-yl)-1H-pyrazol-1-yl)-2-(6-(trifluoromethyl)pyridin-3-yl)ethyl)pyridine To a solution of 1-(difluoromethyl)-5-(1H-pyrazol-4-yl)-1H-1,2,4-triazole (181 mg, 0.980 mmol, 1.0 equiv.) in ACN (15 mL) was added Cs$_2$CO$_3$ (223 mg, 0.69 mmol, 0.7 equiv.) at room temperature for 0.5 h. To the resulting mixture was added 1-(5-bromopyridin-2-yl)-2-(6-(trifluoromethyl)pyridin-3-yl)ethyl methanesulfonate (500 mg, 1.18 mmol, 1.2 equiv.). The resulting mixture was stirred at 80° C. for 2 h. The reaction was quenched with water (50 mL). The resulting mixture was extracted with ethyl acetate (3×20 mL). The organic layers were combined, dried over anhydrous sodium sulfate, filtered and concentrated. The resulting residue was purified by silica gel chromatography (0→50% EA/PE) to yield 5-bromo-2-(1-(4-(1-(difluoromethyl)-1H-1,2,4-triazol-5-yl)-1H-pyrazol-1-yl)-2-(6-(trifluoromethyl)pyridin-3-yl)ethyl)pyridine as a yellow oil. LC/MS: mass calculated for $C_{19}H_{13}BrF_5N_7$: 513.03, measured (ES, m/z): 514.10, 516.10 [M+H, M+H+2]$^+$.

Step 6: 4-Chloro-2-(6-(1-(4-(1-(difluoromethyl)-1H-1,2,4-triazol-5-yl)-1H-pyrazol-1-yl)-2-(6-(trifluoromethyl)pyridin-3-yl)ethyl)pyridin-3-yl)-3-fluoroaniline To a solution of 5-bromo-2-(1-(4-(1-(difluoromethyl)-1H-1,2,4-triazol-5-yl)-1H-pyrazol-1-yl)-2-(6-(trifluoromethyl)pyridin-3-yl)ethyl)pyridine (367 mg, 0.71 mmol, 1.0 equiv.) in 1,4-dioxane (20 mL) and H$_2$O (2 mL) was added (6-amino-3-chloro-2-fluorophenyl)boronic acid (189 mg, 1.00 mmol, 1.4 equiv.), K$_2$CO$_3$ (296 mg, 2.14 mmol, 3.0 equiv.) and Pd(PPh$_3$)$_4$ (82 mg, 0.07 mmol, 0.1 equiv.). The resulting mixture was maintained under nitrogen and stirred at 75° C. for 2 h. After cooling to room temperature, the reaction was quenched with water (50 mL). The resulting mixture was extracted with ethyl acetate (3×20 mL). The organic layers were combined, dried over anhydrous sodium sulfate, filtered and concentrated. The resulting residue was purified by silica gel chromatography (0→5% MeOH/DCM) to yield 4-chloro-2-(6-(1-(4-(1-(difluoromethyl)-1H-1,2,4-triazol-5-yl)-1H-pyrazol-1-yl)-2-(6-(trifluoromethyl)pyridin-3-yl)ethyl)pyridin-3-yl)-3-fluoroaniline as a yellow solid. LC/MS: mass calculated for $C_{25}H_{17}ClF_6N_8$: 578.12, measured (ES, m/z): 579.05 [M+H]$^+$.

Step 7: 5-(3-Chloro-2-fluoro-6-(1H-tetrazol-1-yl)phenyl)-2-(1-(4-(1-(difluoromethyl)-1H-1,2,4-triazol-5-yl)-1H-pyrazol-1-yl)-2-(6-(trifluoromethyl)pyridin-3-yl)ethyl)pyridine To a solution of 4-chloro-2-(6-(1-(4-(1-(difluoromethyl)-1H-1,2,4-triazol-5-yl)-1H-pyrazol-1-yl)-2-(6-(trifluoromethyl)pyridin-3-yl)ethyl)pyridin-3-yl)-3-fluoroaniline (350 mg, 0.61 mmol, 1.0 equiv.) in AcOH (3 mL) was added trimethoxymethane (2 mL) and TMSN₃ (2 mL). The resulting mixture was stirred at room temperature. for 14 h. The reaction was purified by reverse phase chromatography on C$_{18}$ (120 g, 5%→90%, MeCN/H$_2$O) to yield 5-(3-chloro-2-fluoro-6-(1H-tetrazol-1-yl)phenyl)-2-(1-(4-(1-(difluoromethyl)-1H-1,2,4-triazol-5-yl)-1H-pyrazol-1-yl)-2-(6-(trifluoromethyl)pyridin-3-yl)ethyl)pyridine as a yellow oil. LC/MS: mass calculated for $C_{26}H_{16}ClF_6N_{11}$: 631.12, measured (ES, m/z): 653.95 [M+Na]⁺.

Step 8: (R)-5-(3-Chloro-2-fluoro-6-(1H-tetrazol-1-yl)phenyl)-2-(1-(4-(1-(difluoromethyl)-1H-1,2,4-triazol-5-yl)-1H-pyrazol-1-yl)-2-(6-(trifluoromethyl)pyridin-3-yl)ethyl)pyridine 1-oxide To a solution of 5-(3-chloro-2-fluoro-6-(1H-tetrazol-1-yl)phenyl)-2-(1-(4-(1-(difluoromethyl)-1H-1,2,4-triazol-5-yl)-1H-pyrazol-1-yl)-2-(6-(trifluoromethyl)pyridin-3-yl)ethyl)pyridine (300 mg, 0.48 mmol, 1.0 equiv.) in MeOH (8 mL) was added Methyltrioxorhenium (59 mg, 0.24 mmol, 0.5 equiv.) and H$_2$O$_2$ (0.24 mL, 2.37 mmol, 5.0 equiv.). The resulting mixture was stirred at room temperature. for 14 h. The reaction was purified by reverse phase chromatography on C18 (120 g, 5%→60%, MeCN/H$_2$O) and Chiral HPLC to yield (R)-5-(3-chloro-2-fluoro-6-(1H-tetrazol-1-yl)phenyl)-2-(1-(4-(1-(difluoromethyl)-1H-1,2,4-triazol-5-yl)-1H-pyrazol-1-yl)-2-(6-(trifluoromethyl)pyridin-3-yl)ethyl)pyridine 1-oxide as a white solid.

LC/MS: mass calculated for $C_{2H}H_{16}ClF_6N_{11}O$: 647.12, measured (ES, m/z): 648.05 [M+H]⁺. ¹H NMR (400 MHz, DMSO-d$_6$) δ 9.69 (s, 1H), 8.55 (s, 1H), 8.51 (s, 1H), 8.49 (s, 1H), 8.22 (s, 1H), 8.07-8.10 (m, 2H), 7.95 (t, J=57.0 Hz, 1H), 7.75-7.78 (m, 3H), 7.53 (d, J=8.3 Hz, 1H), 7.25 (d, J=8.3 Hz, 1H), 6.41-6.48 (m, 1H), 3.68-3.84 (m, 2H). ¹⁹F NMR (376 MHz, DMSO-d$_6$) δ −66.34, −96.18, −112.67.

Example 823: (S)-5-(3-Chloro-2-fluoro-6-(1H-tetrazol-1-yl)phenyl)-2-(1-(4-(1-(difluoromethyl)-1H-1,2,4-triazol-5-yl)-1H-pyrazol-1-yl)-2-(6-(trifluoromethyl)pyridin-3-yl)ethyl)pyridine 1-oxide

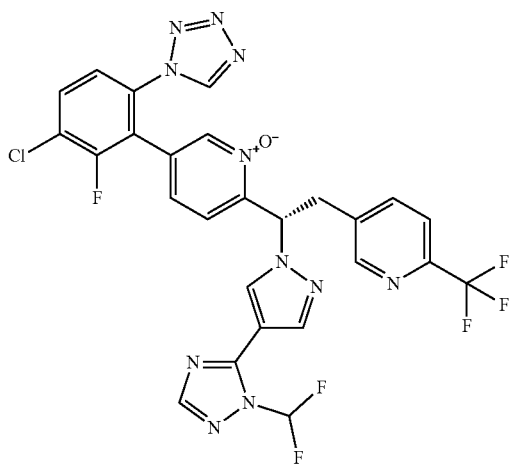

LC/MS: mass calculated for $C_{2H}H_{16}ClF_6N_{11}O$: 647.12, measured (ES, m/z): 648.05 [M+H]⁺. ¹H NMR (400 MHz, DMSO-d$_6$) δ 9.65 (s, 1H), 8.52 (s, 1H), 8.40-8.50 (m, 2H), 8.20 (s, 1H), 8.08 (s, 1H), 8.00-8.06 (m, 1H), 7.92 (s, 1H), 7.67-7.82 (m, 3H), 7.56 (d, J=8.3 Hz, 1H), 7.20-7.30 (m, 1H), 6.38-6.46 (m, 1H), 3.70-3.86 (m, 2H). ¹⁹F NMR (376 MHz, DMSO-d$_6$) δ −66.34, −97.28, −112.67.

Example 824: (R)-5-(3-Chloro-2-fluoro-6-(1H-tetrazol-1-yl)phenyl)-2-(1-(4-(1-(difluoromethyl)-1H-imidazol-5-yl)-1H-pyrazol-1-yl)-2-(6-(trifluoromethyl)pyridin-3-yl)ethyl)pyridine 1-oxide

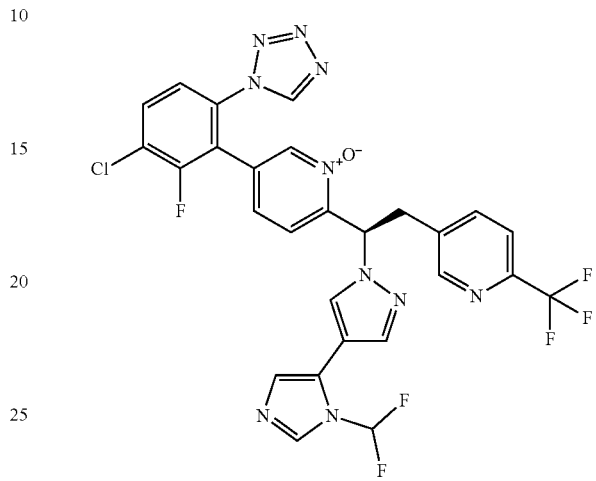

LC/MS: mass calculated for $C_{27}H_{17}ClF_6N_{10}O$: 646.12, measured (ES, m/z): 647.10 [M+H]⁺. ¹H NMR (300 MHz, DMSO-d$_6$) δ 9.71 (s, 1H), 8.55 (s, 1H), 8.50 (s, 1H), 8.31 (s, 1H), 8.08 (t, J=8.7 Hz, 1H), 7.95 (s, 1H), 7.79 (s, 3H), 7.69 (t, J=57.0 Hz, 1H), 7.58 (s, 1H), 7.47 (d, J=8.3 Hz, 1H), 7.25 (d, J=8.2 Hz, 1H), 7.11 (s, 1H), 6.40 (dd, J=9.8, 4.7 Hz, 1H), 3.65-3.86 (m, 2H). ¹⁹F NMR (282 MHz, DMSO-d$_6$) δ −66.32, −73.79, −92.02, −92.10, −112.68.

Example 825: (S)-5-(3-Chloro-2-fluoro-6-(1H-tetrazol-1-yl)phenyl)-2-(1-(4-(1-(difluoromethyl)-1H-imidazol-5-yl)-1H-pyrazol-1-yl)-2-(6-(trifluoromethyl)pyridin-3-yl)ethyl)pyridine 1-oxide

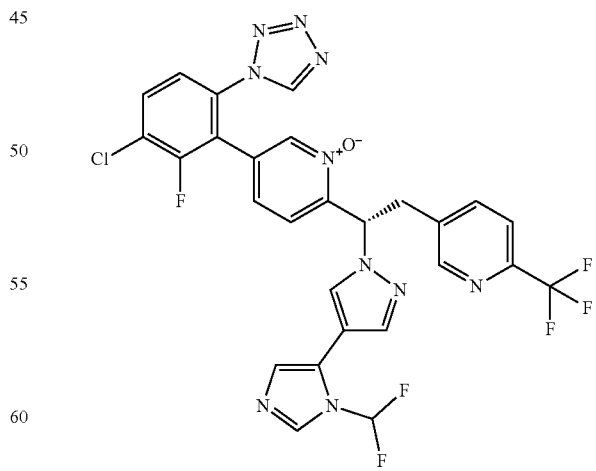

LC/MS: mass calculated for $C_{27}H_{17}ClF_6N_{10}O$: 646.12, measured (ES, m/z): 647.10 [M+H]⁺. ¹H NMR (300 MHz, DMSO-d$_6$) δ 9.71 (s, 1H), 8.50-8.60 (m, 2H), 8.31 (s, 1H), 8.02-8.12 (m, 1H), 7.95 (s, 1H), 7.89-7.44 (m, 6H), 7.20-

7.30 (m, 1H), 7.06-7.14 (m, 1H), 6.35-6.45 (m, 1H), 3.65-3.86 (m, 2H). $^{19}$F NMR (282 MHz, DMSO-d$_6$) δ −66.32, −73.79, −92.06, −112.68.

Example 826: (S)-5-(6-(4-Bromo-1H-1,2,3-triazol-1-yl)-3-chloro-2-fluorophenyl)-2-(3-(difluoromethoxy)-1-(4-(1-(difluoromethyl)-1H-1,2,4-triazol-5-yl)-1H-pyrazol-1-yl)propyl)pyridine 1-oxide

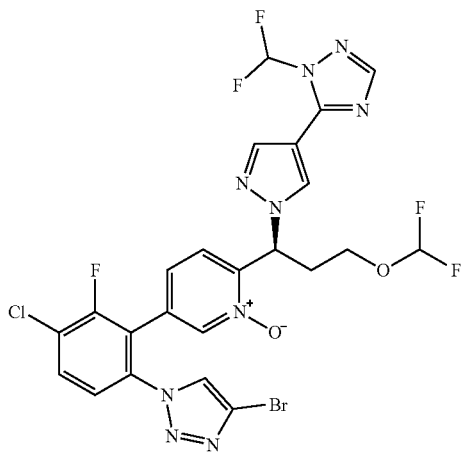

LC/MS: mass calculated for C$_{23}$H$_{16}$BrClF$_5$N$_9$O$_2$: 659.02, measured (ES, m/z): 659.95 [M+H+2]$^+$. $^1$H NMR (300 MHz, DMSO-d$_6$) δ 8.69 (s, 1H), 8.67 (s, 1H), 8.42 (s, 1H), 8.30 (s, 1H), 8.11 (s, 1H), 7.86-8.07 (m, 2H), 7.69 (d, J=8.7 Hz, 1H), 7.40 (d, J=8.3 Hz, 1H), 7.19 (d, J=8.1 Hz, 1H), 6.63 (t, J=75.7 Hz, 1H), 6.29 (dd, J=9.8, 4.7 Hz, 1H), 3.78-3.89 (m, 1H), 3.66-3.71 (m, 1H), 2.59-2.70 (m, 2H). $^{19}$F NMR (282 MHz, DMSO-d$_6$) δ −83.36, −96.15, −112.95.

Example 827: (R)-5-(6-(4-Bromo-1H-1,2,3-triazol-1-yl)-3-chloro-2-fluorophenyl)-2-(3-(difluoromethoxy)-1-(4-(1-(difluoromethyl)-1H-1,2,4-triazol-5-yl)-1H-pyrazol-1-yl)propyl)pyridine 1-oxide

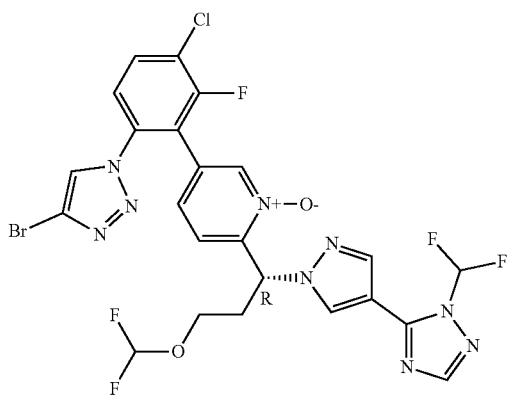

Step 1: (6-(3-(Difluoromethoxy)-1-(4-(1-(difluoromethyl)-1H-1,2,4-triazol-5-yl)-1H-pyrazol-1-yl)propyl)pyridin-3-yl)boronic acid A mixture of 5-bromo-2-(3-(difluoromethoxy)-1-(4-(1-(difluoromethyl)-1H-1,2,4-triazol-5-yl)-1H-pyrazol-1-yl)propyl)pyridine (452.0 mg, 1.01 mmol, 1.0 equiv.), 4,4,4',4',5,5,5',5'-octamethyl-2,2'-bi(1,3,2-dioxaborolane) (511.0 mg, 2.01 mmol, 2.0 equiv.), Pd(dppf)Cl$_2$ (73.6 mg, 0.10 mmol, 0.1 equiv.) and KOAc (296.2 mg, 3.02 mmol, 3.0 equiv.) in 1,4-dioxane (5 mL) was stirred for 2 h at 90° C. The resulting mixture was diluted with water (10 mL), extracted with EA (3×10 mL). The organic layers were combined, washed with brine, dried over Na$_2$SO$_4$ and concentrated to yield (6-(3-(difluoromethoxy)-1-(4-(1-(difluoromethyl)-1H-1,2,4-triazol-5-yl)-1H-pyrazol-1-yl)propyl)pyridin-3-yl)boronic acid as a black oil. LC/MS: mass calculated for C$_{15}$H$_{15}$BF$_4$N$_6$O$_3$: 414.12, measured (ES, m/z): 414.95 [M+H]$^+$.

Step 2: 5-(6-(4-Bromo-1H-1,2,3-triazol-1-yl)-3-chloro-2-fluorophenyl)-2-(3-(difluoromethoxy)-1-(4-(1-(difluoromethyl)-1H-1,2,4-triazol-5-yl)-1H-pyrazol-1-yl)propyl)pyridine A mixture of 4-bromo-1-(4-chloro-3-fluoro-2-iodophenyl)-1H-1,2,3-triazole (233.200 mg, 0.58 mmol, 1.0 equiv.), (6-(3-(difluoromethoxy)-1-(4-(1-(difluoromethyl)-1H-1,2,4-triazol-5-yl)-1H-pyrazol-1-yl)propyl)pyridin-3-yl)boronic acid (200.0 mg, 0.48 mmol, 1.0 equiv.), Pd(PPh$_3$)$_4$ (55.8 mg, 0.05 mmol, 0.1 equiv.) and K$_2$CO$_3$ (200.2 mg, 1.45 mmol, 3.0 equiv.) in 1,4-dioxane/water (V/V=4:1, 1.2 mL) was refluxed at 90° C. under N$_2$ for 3 h. The resulting mixture was diluted with water (10 mL), extracted with EA (3×10 mL).

The organic layers were combined, washed with brine, dried over Na$_2$SO$_4$ and concentrated to yield 5-(6-(4-bromo-1H-1,2,3-triazol-1-yl)-3-chloro-2-fluorophenyl)-2-(3-(difluoromethoxy)-1-(4-(1-(difluoromethyl)-1H-1,2,4-triazol-5-yl)-1H-pyrazol-1-yl)propyl)pyridine as a black oil. LC/MS: mass calculated for C$_{23}$H$_{16}$BrClF$_5$N$_9$O: 643.03, measured (ES, m/z): 646.10 [M+H+2]$^+$.

Step 3: (R)-5-(6-(4-Bromo-1H-1,2,3-triazol-1-yl)-3-chloro-2-fluorophenyl)-2-(3-(difluoromethoxy)-1-(4-(1-(difluoromethyl)-1H-1,2,4-triazol-5-yl)-1H-pyrazol-1-yl)propyl)pyridine 1-oxide A mixture of 5-(6-(4-bromo-1H-1,2,3-triazol-1-yl)-3-chloro-2-fluorophenyl)-2-(3-(difluoromethoxy)-1-(4-(1-(difluoromethyl)-1H-1,2,4-triazol-5-yl)-1H-pyrazol-1-yl)propyl)pyridine (200.0 mg, 0.31 mmol, 1.0 equiv.), methyltrioxorhenium (38.7 mg, 0.16 mmol, 0.5 equiv.), hydrogen peroxide (0.8 mL, 30 wt %) in CH$_3$OH (2 mL) was stirred for 3 h at room temperature. The resulting mixture was purified by reverse phase chromatography on C18 (MeCN/H$_2$O (0.05% CF$_3$COOH)) to yield 5-(6-(4-bromo-1H-1,2,3-triazol-1-yl)-3-chloro-2-fluorophenyl)-2-(3-(difluoromethoxy)-1-(4-(1-(difluoromethyl)-1H-1,2,4-triazol-5-yl)-1H-pyrazol-1-yl)propyl)pyridine 1-oxide as a white solid. The racemic product was separated by chiral-HPLC to yield (R)-5-(6-(4-bromo-1H-1,2,3-triazol-1-yl)-3-chloro-2-fluorophenyl)-2-(3-(difluoromethoxy)-1-(4-(1-(difluoromethyl)-1H-1,2,4-triazol-5-yl)-1H-pyrazol-1-yl)propyl)pyridine 1-oxide as a white solid.

LC/MS: mass calculated for C$_{23}$H$_{16}$BrClF$_5$N$_9$O$_2$: 659.02, measured (ES, m/z): 683.95 [M+Na+2]$^+$. $^1$H NMR (300 MHz, DMSO-d$_6$) δ 8.62-8.70 (m, 2H), 8.42 (d, J=1.4 Hz, 1H), 7.85-8.31 (m, 4H), 7.65-7.72 (m, 1H), 7.40 (d, J=8.3 Hz, 1H), 7.19 (d, J=8.3 Hz, 1H), 6.30-6.90 (m, 1H), 6.20-6.31 (m, 1H), 3.78-3.89 (m, 1H), 3.62-3.72 (m, 1H), 2.59-2.70 (m, 2H). $^{19}$F-NMR (282 MHz, DMSO-d$_6$) δ −83.36, −96.15, −112.95.

Example 828: (S)-5-(3-Chloro-6-(4-cyano-1H-1,2,3-triazol-1-yl)-2-fluorophenyl)-2-(3-(difluoromethoxy)-1-(4-(1-(difluoromethyl)-1H-1,2,4-triazol-5-yl)-1H-pyrazol-1-yl)propyl)pyridine 1-oxide

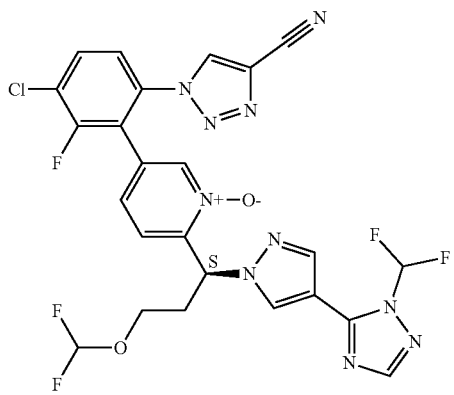

LC/MS: mass calculated for $C_{24}H_{16}ClF_5N_{10}O_2$: 606.11, measured (ES, m/z): 607.05 [M+H]$^+$. $^1$H NMR (300 MHz, DMSO-d$_6$) δ 9.33 (s, 1H), 8.66 (s, 1H), 8.46 (d, J=1.5 Hz, 1H), 8.26 (d, J=6.3 Hz, 1H), 7.89-8.15 (m, 3H), 7.70-7.78 (m, 1H), 7.40 (d, J=8.3 Hz, 1H), 7.15-7.21 (m, 1H), 6.62 (t, J=78.3 Hz, 1H), 6.20-6.28 (m, 1H), 3.82-3.92 (m, 1H), 3.62-3.73 (m, 1H), 2.56-2.72 (m, 2H). $^{19}$F NMR (282 MHz, DMSO-d$_6$) δ --73.43, -83.37, -96.16, 112.82.

Example 829: (R)-5-(3-Chloro-6-(4-cyano-1H-1,2,3-triazol-1-yl)-2-fluorophenyl)-2-(3-(difluoromethoxy)-1-(4-(1-(difluoromethyl)-1H-1,2,4-triazol-5-yl)-1H-pyrazol-1-yl)propyl)pyridine 1-oxide

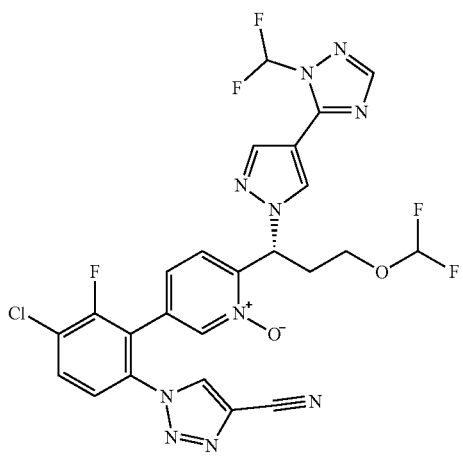 [SMILES: N#Cc1cn(-c2ccc(Cl)c(F)c2-c2ccc([C@@H](CCOC(F)F)n3cc(-c4ncnn4C(F)F)cn3)[n+]([O-])c2)nn1]

Step 1: 1-(Difluoromethyl)-5-(1H-pyrazol-3-yl)-1H-1,2,4-triazole

To a solution of tert-butyl 3-(4,4,5,5-tetramethyl-1,3,2-dioxaborolan-2-yl)-1H-pyrazole-1-carboxylate (998.4 mg, 2.86 mmol, 1.0 equiv.) in 1,4-dioxane (30.0 mL) was added 1-(difluoromethyl)-5-iodo-1H-1,2,4-triazole (700.0 mg, 2.86 mmol, 1.0 equiv.) and potassium carbonate (592.4 mg, 4.29 mmol, 1.5 equiv.) and tetrakis(triphenylphosphine) platinum (209.1 mg, 0.29 mmol, 0.1 equiv.). The resulting mixture was stirred at 90° C. for 3 h. The reaction was quenched with water (50 mL). The resulting mixture was extracted with ethyl acetate (3×50 mL). The organic layers were combined, dried over anhydrous sodium sulfate, filtered and concentrated. The resulting residue was purified by silica gel chromatography (0→10% DCM:MeOH) to yield the 1-(difluoromethyl)-5-(1H-pyrrol-3-yl)-1H-1,2,4-triazole as a yellow oil. LC/MS: mass calculated for $C_7H_6F_2N_4$: 185.05, measured (ES, m/z): 186.20 [M+H]$^+$.

Step 2: 5-Bromo-2-(3-(difluoromethoxy)-1-(3-(1-(difluoromethyl)-1H-1,2,4-triazol-5-yl)-1H-pyrazol-1-yl)propyl)pyridine To a solution of 1-(difluoromethyl)-5-(1H-pyrrol-3-yl)-1H-1,2,4-triazole (130.0 mg, 0.71 mmol, 1.0 equiv.) and cesium carbonate (207.0 mg, 0.64 mmol, 0.9 equiv.) in acetonitrile (10.0 mL) was added 1-(5-bromopyridin-2-yl)-3-(difluoromethoxy)propyl methanesulfonate (177.9 mg, 0.49 mmol, 0.7 equiv.). The resulting mixture was stirred at 90° C. for 16 h. The reaction was quenched with water (50 mL). The resulting mixture was extracted with ethyl acetate (3×50 mL). The organic layers were combined, dried over anhydrous sodium sulfate, filtered and concentrated. The resulting residue was purified by silica gel chromatography (0→20% ethyl acetate/petroleum ether) to yield the 5-bromo-2-(3-(difluoromethoxy)-1-(3-(1-(difluoromethyl)-1H-1,2,4-triazol-5-yl)-1H-pyrrol-1-yl)propyl)pyridine as a yellow solid. LC/MS: mass calculated for $C_{16}H_{14}BrF_4N_5O$: 448.03, measured (ES, m/z): 449.15 [M+H]$^+$.

Step 3: (6-(3-(Difluoromethoxy)-1-(3-(1-(difluoromethyl)-1H-1,2,4-triazol-5-yl)-1H-pyrazol-1-yl)propyl)pyridin-3-yl)boronic acid To a solution of 5-bromo-2-(3-(difluoromethoxy)-1-(3-(1-(difluoromethyl)-1H-1,2,4-triazol-5-yl)-1H-pyrazol-1-yl)propyl)pyridine (300.0 mg, 0.67 mmol, 1.0 equiv.) in 1,4-dioxane (25.0 mL) was added 4,4,4',4',5,5,5',5'-octamethyl-2,2'-bi(1,3,2-dioxaborolane) (254.4 mg, 1.00 mmol, 1.5 equiv.) [1,1'-bis(diphenylphosphino)ferrocene]dichloropalladium(II) (48.9 mg, 0.06 mmol, 0.1 equiv.) and potassium acetate (98.3 mg, 1.00 mmol, 1.5 equiv.). The resulting mixture was maintained under nitrogen and stirred at 90° C. for 16 h. The reaction was quenched with water (50 mL). The resulting mixture was extracted with ethyl acetate (3×50 mL). The organic layers were combined, dried over anhydrous sodium sulfate, filtered and concentrated to yield (6-(3-(difluoromethoxy)-1-(3-(1-(difluoromethyl)-1H-1,2,4-triazol-5-yl)-1H-pyrazol-1-yl)propyl)pyridin-3-yl)boronic acid as a yellow oil. LC/MS: mass calculated for $C_{15}H_{15}BF_4N_6O_3$: 414.12, measured (ES, m/z): 415.15[M+H]$^+$.

Step 4: 1-(4-Chloro-2-(6-(3-(difluoromethoxy)-1-(3-(1-(difluoromethyl)-1H-1,2,4-triazol-5-yl)-1H-pyrrol-1-yl)propyl)pyridin-3-yl)-3-fluorophenyl)-1H-1,2,3-triazole-4-carbonitrile To a solution of (6-(3-(difluoromethoxy)-1-(3-(1-(difluoromethyl)-1H-1,2,4-triazol-5-yl)-1H-pyrrol-1-yl)propyl)pyridin-3-yl)boronic acid (178.0 mg, 0.43 mmol, 1.0 equiv.) in 1,4-dioxane (12.0 mL) was added 1-(4-chloro-3-fluoro-2-iodophenyl)-1H-1,2,3-triazole-4-carbonitrile (150.2 mg, 0.43 mmol, 1.0 equiv.), tetrakis(triphenylphosphine)palladium (49.8 mg, 0.043 mmol, 0.1 equiv.), potassium phosphate (137.2 mg, 0.65 mmol, 1.5 equiv.) and water (1.2 mL). The resulting mixture was maintained under nitrogen and stirred at 90° C. for 3 h. The reaction was quenched with water (50 mL). The resulting mixture was extracted with ethyl acetate (3×50 mL). The organic layers were combined, dried over anhydrous sodium sulfate, filtered and concentrated. The resulting residue was purified by silica gel chromatography (0→40% ethyl acetate/petroleum ether) to yield the 1-(4-chloro-2-(6-(3-(difluoromethoxy)-1-(3-(1-(difluoromethyl)-1H-1,2,4-triazol-5-yl)-1H-pyrrol-1-yl)propyl)pyridin-3-yl)-3-fluorophenyl)-1H-1,2,3-triazole-4-carbonitrile as a yellow oil. LC/MS: mass calculated for $C_{25}H_{17}ClF_5N_9O$: 589.12, measured (ES, m/z): 593.15 $[M+H+2]^+$.

Step 5: (R)-5-(3-Chloro-6-(4-cyano-1H-1,2,3-triazol-1-yl)-2-fluorophenyl)-2-(3-(difluoromethoxy)-1-(4-(1-(difluoromethyl)-1H-1,2,4-triazol-5-yl)-1H-pyrazol-1-yl)propyl)pyridine 1-oxide To a solution of 1-(4-chloro-2-(6-(3-(difluoromethoxy)-1-(4-(1-(difluoromethyl)-1H-1,2,4-triazol-5-yl)-1H-pyrazol-1-yl)propyl)pyridin-3-yl)-3-fluorophenyl)-1H-1,2,3-triazole-4-carbonitrile (120.0 mg, 0.20 mmol, 1.0 equiv.) in $CH_3OH$ (5.0 mL) was added hydrogen peroxide (1.2 mL, 30 wt %) and methyltrioxorhenium (VII) (25.3 mg, 0.10 mmol, 0.5 equiv.). The resulting mixture was stirred at room temperature for 2 h. The mixture was purified by silica gel chromatography with MeOH/DCM (0→10%) to yield the resulting residue, which was purified by chiral-HPLC with (Hex:DCM=3:1) (0.1% DEA):EtOH=70:30 to yield (R)-5-(3-chloro-6-(4-cyano-1H-1,2,3-triazol-1-yl)-2-fluorophenyl)-2-(3-(difluoromethoxy)-1-(4-(1-(difluoromethyl)-1H-1,2,4-triazol-5-yl)-1H-pyrazol-1-yl)propyl)pyridine 1-oxide as a white solid.

LC/MS: mass calculated for $C_{24}H_{16}ClF_5N_{10}O_2$: 606.11, measured (ES, m/z): 607.05 $[M+H]^+$. $^1H$ NMR (300 MHz, DMSO-$d_6$) δ 9.34 (s, 1H), 8.67 (s, 1H), 8.47 (s, 1H), 8.26 (d, J=5.9 Hz, 1H), 7.82-8.15 (m, 3H), 7.70-7.77 (m, 1H), 7.40 (d, J=8.3 Hz, 1H), 7.14-7.21 (m, 1H), 6.41-6.92 (m, 1H), 6.21-6.29 (m, 1H), 3.85-3.91 (m, 1H), 3.62-3.71 (m, 1H), 2.61-2.73 (m, 2H). $^{19}F$ NMR (282 MHz, DMSO-$d_6$) δ -83.39, -96.60, -112.66.

Example 830: (S)-5-(3-Chloro-2-fluoro-6-(4-(trifluoromethyl)-1H-1,2,3-triazol-1-yl)phenyl)-2-(2-(1-(difluoromethyl)-1H-pyrazol-3-yl)-1-(4-(1-methyl-1H-1,2,3-triazol-5-yl)-1H-pyrazol-1-yl)ethyl)pyridine 1-oxide

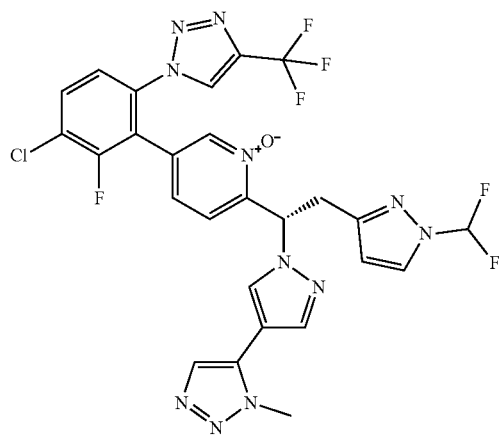

LC/MS: mass calculated for $C_{27}H_{18}ClF_6N_{11}O$: 649.13, measured (ES, m/z): 650.10 $[M+H]^+$. $^1H$ NMR (300 MHz, DMSO-$d_6$) δ 9.18 (s, 1H), 8.40-8.60 (m, 2H), 7.99-8.10 (m, 2H), 7.96 (s, 1H), 7.44-7.90 (m, 3H), 6.90-7.45 (m, 2H), 6.38-6.48 (m, 1H), 6.12 (s, 1H), 4.02 (s, 3H), 3.63 (d, J=8.2 Hz, 2H). $^{19}F$ NMR (282 MHz, DMSO) δ -59.77, -73.54, -93.88, -112.82.

Example 831: (R)-5-(3-Chloro-2-fluoro-6-(4-(trifluoromethyl)-1H-1,2,3-triazol-1-yl)phenyl)-2-(2-(1-(difluoromethyl)-1H-pyrazol-3-yl)-1-(4-(1-methyl-1H-1,2,3-triazol-5-yl)-1H-pyrazol-1-yl)ethyl) pyridine 1-oxide

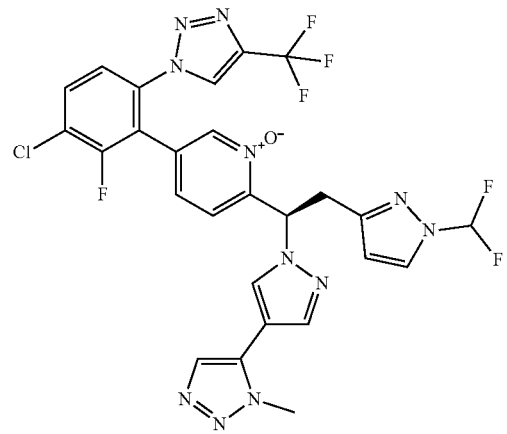

Step 1: 5-Bromo-2-((4-(1-methyl-1H-1,2,3-triazol-5-yl)-1H-pyrazol-1-yl)methyl)pyridine A mixture of 1-methyl-5-(1H-pyrazol-4-yl)-1H-1,2,3-triazole (4.0 g, 26.8 mmol, 1.0 eq.) and cesium carbonate (8.7 g, 26.8 mmol, 1.0 eq.) in acetonitrile (50 mL) was stirred at room temperature for 30 minutes.

Then (5-bromopyridin-2-yl)methyl methanesulfonate (9.3 g, 34.9 mmol, 1.3 eq.) was added the reaction mixture and the solution was stirred at 90° C. for 3 h. The mixture was added $H_2O$, extracted with EtOAc three times. The combined organic layers was washed with brine, dried over $Na_2SO_4$, concentrated and purified by silica gel chromatography (0-20% MeOH:DCM) to yield 5-bromo-2-((4-(1-methyl-1H-1,2,3-triazol-5-yl)-1H-pyrazol-1-yl)methyl) pyridine as a yellow solid. LC/MS: mass calculated for $C_{12}H_{11}BrN_6$: 318, measured: 319 $[M+H]^+$.

Step 2: 5-Bromo-2-(2-(1-(difluoromethyl)-1H-pyrazol-3-yl)-1-(4-(1-methyl-1H-1,2,3-triazol-5-yl)-1H-pyrazol-1-yl)ethyl)pyridine To a solution of 5-bromo-2-((4-(1-methyl-1H-1,2,3-triazol-5-yl)-1H-pyrazol-1-yl)methyl)pyridine (4.2 g, 13.2 mmol, 1 eq.) in tetrahydrofuran (80 mL) under nitrogen was added lithium bis(trimethylsilyl)amide (19.7 mL, 19.7 mmol, 1.0 M in THF, 1.5 eq.) in portions at -78° C. and the solution was stirred for 30 min at this temperature. 3-(Bromomethyl)-1-(difluoromethyl)-1H-pyrazole (4.2 g, 19.7 mmol, 1.5 eq.) in tetrahydrofuran (2 mL) under nitrogen was added the solution. The reaction mixture was stirred at -70° C. for 2 h. The solution was quenched with sat. $NH_4Cl$ (aq.)

and extracted with ethyl acetate twice. The combined organic layer was washed with brine, dried over Na$_2$SO$_4$ and concentrated. The residue was purified by silica gel chromatography (0-100% EtOAc/petroleum ether) to yield 5-bromo-2-(2-(1-(difluoromethyl)-1H-pyrazol-3-yl)-1-(4-(1-methyl-1H-1,2,3-triazol-5-yl)-1H-pyrazol-1-yl)ethyl)pyridine as a yellow solid. LC/MS: mass calculated for C$_{17}$H$_{15}$BrF$_2$N$_8$: 448, measured: 449, 451 [M+H, M+H+2]$^+$.

Step 3: (6-(2-(1-(Difluoromethyl)-1H-pyrazol-3-yl)-1-(4-(1-methyl-1H-1,2,3-triazol-5-yl)-1H-pyrazol-1-yl)ethyl)pyridin-3-yl)boronic acid A mixture of 5-bromo-2-(2-(1-(difluoromethyl)-1H-pyrazol-3-yl)-1-(4-(1-methyl-1H-1,2,3-triazol-5-yl)-1H-pyrazol-1-yl)ethyl)pyridine (350 mg, 0.75 mmol, 1.0 equiv.) and 4,4,4',4',5,5,5',5'-octamethyl-2,2'-bi(1,3,2-dioxaborolane) (380 mg, 1.50 mmol, 2.0 equiv.) in 1,4-dioxane (10 mL) was added potassium acetate (294 mg, 2.99 mmol, 4.0 equiv.) and Pd(dppf)Cl$_2$ (55 mg, 0.08 mmol, 0.1 equiv.) under N$_2$. The solution was stirred at 90° C. for 2 h. Water was added, the mixture was extracted with ethyl acetate. The combined organic layers were washed with brine, dried over Na$_2$SO$_4$ and concentrated under vacuum to yield (6-(2-(1-(difluoromethyl)-1H-pyrazol-3-yl)-1-(4-(1-methyl-1H-1, 2, 3-triazol-5-yl)-1H-pyrazol-1-yl)ethyl)pyridin-3-yl)boronic acid as a brown solid. LC/MS: mass calculated for C$_{17}$H$_{17}$BF$_2$N$_8$O$_2$: 414.15, measured (ESI, m/z): 415.05 [M+H]$^+$.

Step 4: 5-(3-Chloro-2-fluoro-6-(4-(trifluoromethyl)-1H-1,2,3-triazol-1-yl)phenyl)-2-(2-(1-(difluoromethyl)-1H-pyrazol-3-yl)-1-(4-(1-methyl-1H-1,2,3-triazol-5-yl)-1H-pyrazol-1-yl)ethyl)pyridine A mixture of (6-(2-(1-(difluoromethyl)-1H-pyrazol-3-yl)-1-(4-(1-methyl-1H-1,2,3-triazol-5-yl)-1H-pyrazol-1-yl)ethyl)pyridin-3-yl)boronic acid (300 mg, 0.72 mmol, 1.0 eq.) and 1-(4-chloro-3-fluoro-2-iodophenyl)-4-(trifluoromethyl)-1H-1,2,3-triazole (425 mg, 1.1 mmol, 1.5 eq.) in a mixed solution of 1,4-dioxane (4 mL) and water (1 mL) was added potassium carbonate (400 mg, 2.90 mmol, 4.0 eq.) and tetrakis(triphenylphosphine) palladium(0) (167 mg, 0.15 mmol, 0.1 eq.). The flask was evacuated flask, then purged with nitrogen. This was repeated twice. The reaction mixture was stirred at 100° C. for 3 h under N$_2$.

Water was added, the mixture was extracted with EtOAc. The combined organic layer was washed with brine, dried over Na$_2$SO$_4$ and concentrated under vacuum. The resulting solid was purified by silica gel chromatography with EtOAc/petroleum ether (0→90%) to yield 5-(3-chloro-2-fluoro-6-(4-(trifluoromethyl)-1H-1,2,3-triazol-1-yl)phenyl)-2-(2-(1-(difluoromethyl)-1H-pyrazol-3-yl)-1-(4-(1-methyl-1H-1,2,3-triazol-5-yl)-1H-pyrazol-1-yl)ethyl)pyridine as a yellow solid. LC/MS: mass calculated for C$_{27}$H$_{18}$ClF$_6$N$_{11}$: 633.13, measured (ES, m/z): 634.25 [M+H]$^+$.

Step 5: (R)-5-(3-Chloro-2-fluoro-6-(4-(trifluoromethyl)-1H-1,2,3-triazol-1-yl)phenyl)-2-(2-(1-(difluoromethyl)-1H-pyrazol-3-yl)-1-(4-(1-methyl-1H-1,2,3-triazol-5-yl)-1H-pyrazol-1-yl)ethyl)pyridine 1-oxide To a solution of 5-(3-chloro-2-fluoro-6-(4-(trifluoromethyl)-1H-1,2,3-triazol-1-yl)phenyl)-2-(2-(1-(difluoromethyl)-1H-pyrazol-3-yl)-1-(4-(1-methyl-1H-1,2,3-triazol-5-yl)-1H-pyrazol-1-yl)ethyl)pyridine (200 mg, 0.32 mmol, 1.0 eq.) and methyltrioxorhenium (VII) (16 mg, 0.06 mmol, 0.2 eq.) in CH$_3$OH (2 mL) was added hydrogen peroxide (0.32 mL, 3.2 mmol, 10.0 eq.). The reaction mixture was stirred at room temperature for 3 h. The reaction mixture was purified by reverse phase chromatography on C18 (120 g, ACN/H$_2$O (0.05% CF$_3$COOH: 0→50%). The resulting residue was purified by prep-chiral-HPLC to yield (R)-5-(3-chloro-2-fluoro-6-(4-(trifluoromethyl)-1H-1,2,3-triazol-1-yl)phenyl)-2-(2-(1-(difluoromethyl)-1H-pyrazol-3-yl)-1-(4-(1-methyl-1H-1,2,3-triazol-5-yl)-1H-pyrazol-1-yl)ethyl)pyridine 1-oxide as an off-white solid.

HPLC purity (method A): 99.8%, retention time=1.392 min. LC/MS: mass calculated for C$_{28}$H$_{18}$ClF$_6$N$_{11}$O:649.13, measured (ES, m/z): 650.10 [M+H]$^+$. $^1$H NMR (300 MHz, DMSO-d$_6$): δ 9.17 (s, 1H), 8.47 (s, 1H), 8.45 (s, 1H), 7.99-8.10 (m, 2H), 7.95 (s, 1H), 7.47-7.90 (m, 3H), 7.38 (d, J=8.3 Hz, 1H), 7.19 (d, J=8.3 Hz, 1H), 6.38-6.51 (m, 1H), 6.12 (d, J=2.7 Hz, 1H), 4.02 (s, 3H), 3.53-3.73 (m, 2H). $^{19}$F-NMR (282 MHz, DMSO-d$_6$): δ −59.85, −93.88, −112.81.

Example 832: (S)-5-(3-Chloro-6-(4-chloro-1H-1,2,3-triazol-1-yl)-2-fluorophenyl)-2-(2-(1-(difluoromethyl)-1H-pyrazol-3-yl)-1-(4-(1-methyl-1H-1,2,4-triazol-5-yl)-1H-pyrazol-1-yl)ethyl)pyridine 1-oxide

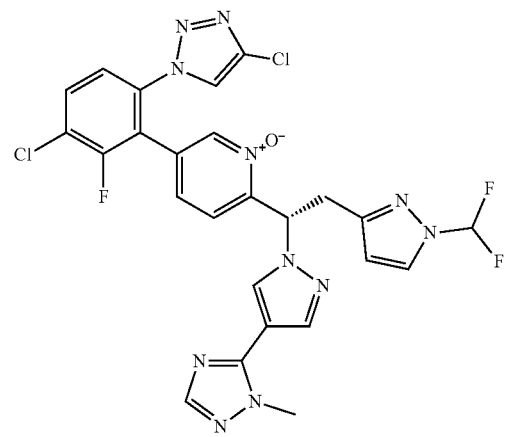

LC/MS: mass calculated for C$_{25}$H$_{18}$Cl$_2$F$_3$N$_{11}$O: 615.1, measured (ES, m/z): 616.1 [M+H]$^+$. $^1$H NMR (300 MHz, CD$_3$OD) δ 8.45 (s, 1H), 8.39 (s, 1H), 8.33 (s, 1H), 8.07 (s, 1H), 7.85-7.97 (m, 3H), 7.15-7.72 (m, 4H), 6.61-6.68 (m, 1H), 6.25 (d, J=2.7 Hz, 1H), 3.99 (s, 3H), 3.72-3.93 (m, 2H). $^{19}$F NMR (282 MHz, CD$_3$OD) δ −95.99, −114.15.

Example 833: (R)-5-(3-Chloro-6-(4-chloro-1H-1,2,3-triazol-1-yl)-2-fluorophenyl)-2-(2-(1-(difluoromethyl)-1H-pyrazol-3-yl)-1-(4-(1-methyl-1H-1,2,4-triazol-5-yl)-1H-pyrazol-1-yl)ethyl)pyridine 1-oxide

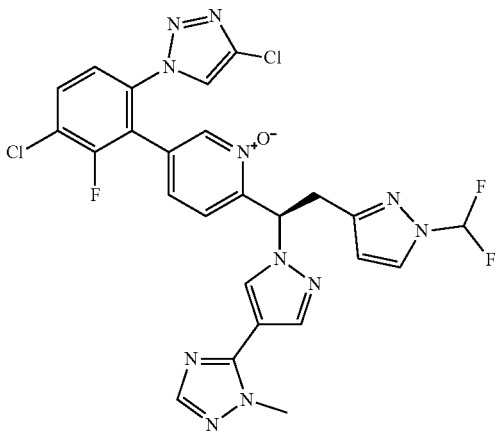

Step 1:
(1-(Difluoromethyl)-1H-pyrazol-3-yl)methanol

To a solution of 1-(difluoromethyl)-1H-pyrazole-3-carboxylic acid (3.0 g, 18.51 mmol, 1.0 equiv.) in tetrahydrofuran (30 mL) was added brane-tetrahydrofuran complex (92.5 mL, 92.54 mmol, 1M in THF, 5.0 equiv.) at 0° C. The resulting mixture was stirred at room temperature overnight. The reaction was quenched with water (20 mL) and 2M HCl. The resulting mixture was extracted with ethyl acetate (3×20 mL). The organic layers were combined, dried over anhydrous sodium sulfate, filtered and concentrated to yield (1-(difluoromethyl)-1H-pyrazol-3-yl)methanol as a white solid without any purifications. LC/MS: mass calculated for $C_5H_6F_2N_2O$: 148.04, measured (ES, m/z): 149.10 [M+H]$^+$.

Step 2:
3-(Bromomethyl)-1-(difluoromethyl)-1H-pyrazole

To a solution of (1-(difluoromethyl)-1H-pyrazol-3-yl)methanol (2.0 g, 18.23 mmol, 1.0 equiv.) in dichloromethane (30 mL) was added phosphorus tribromide (18.6 mL, 18.6 mmol, 1M in THF, 1.02 equiv.).

The resulting mixture was maintained under nitrogen and stirred at room temperature. for 2 h. The reaction was quenched with water (50 mL). The resulting mixture was extracted with dichloromethane (3×50 mL). The pH value of the organic layers was adjusted to 8 used saturated sodium bicarbonate solution. The organic layers were combined, dried over anhydrous sodium sulfate, filtered and concentrated to yield the 3-(bromomethyl)-1-(difluoromethyl)-1H-pyrazole as a colorless oil. LC/MS: mass calculated for $C_5H_5BrF_2N_2$: 209.96, measured (ES, m/z): 211.0, 213.0 [M+H, M+H+2]$^+$.

Step 3: 5-Bromo-2-(2-(1-(difluoromethyl)-1H-pyrazol-3-yl)-1-(4-(1-methyl-1H-1,2,4-triazol-5-yl)-1H-pyrazol-1-yl)ethyl)pyridine To a solution of 5-bromo-2-((4-(1-methyl-1H-1,2,4-triazol-5-yl)-1H-pyrazol-1-yl)methyl)pyridine (245 mg, 0.77 mmol, 1.0 equiv.) in THF (50 mL) was added LiHMDS (1.2 mL, 1.2 mmol, 1M in THF, 1.5 equiv.) under $N_2$ at −78° C. After stirring for 30 min, 3-(bromomethyl)-1-(difluoromethyl)-1H-pyrazole (194 mg, 0.92 mmol, 1.2 equiv.) was added at −78° C. The resulting mixture was maintained under nitrogen and stirred at −78° C. for 2 h. The reaction was quenched with $NH_4Cl$. The resulting mixture was extracted with ethyl acetate.

The organic layers were combined, dried over anhydrous sodium sulfate, filtered and concentrated. The resulting residue was purified by silica gel chromatography (0→80% ethyl acetate/petroleum ether) to yield the 5-bromo-2-(2-(1-(difluoromethyl)-1H-pyrazol-3-yl)-1-(4-(1-methyl-1H-1,2,4-triazol-5-yl)-1H-pyrazol-1-yl)ethyl)pyridine as an yellow oil. LC/MS: mass calculated for $C_{17}H_{15}BrF_2N_8$: 448.06, measured (ES, m/z): 449.00, 451.00 [M+H, M+H+2]$^+$.

Step 4: (6-(2-(1-(Difluoromethyl)-1H-pyrazol-3-yl)-1-(4-(1-methyl-1H-1,2,4-triazol-5-yl)-1H-pyrazol-1-yl)ethyl)pyridin-3-yl)boronic acid To a solution of 5-bromo-2-(2-(1-(difluoromethyl)-1H-pyrazol-3-yl)-1-(4-(1-methyl-1H-1,2,4-triazol-5-yl)-1H-pyrazol-1-yl)ethyl)pyridine (142 mg, 0.32 mmol, 1.0 equiv.) in 1,4-dioxane (1 mL) was added bis(pinacolato)diboron (160.529 mg, 0.632 mmol, 2.0 equiv.), potassium acetate (93 mg, 0.95 mmol, 3.0 equiv.), Pd(dppf)$Cl_2 \cdot CH_2Cl_2$ (26 mg, 0.03 mmol, 0.1 equiv.). The resulting mixture was maintained under nitrogen and stirred at 90° C. for 3H. After cooling to room temperature, the reaction was quenched with water. The resulting mixture was extracted with ethyl acetate. The organic layers were combined, dried over anhydrous sodium sulfate, filtered and concentrated to yield the (6-(2-(1-(difluoromethyl)-1H-pyrazol-3-yl)-1-(4-(1-methyl-1H-1,2,4-triazol-5-yl)-1H-pyrazol-1-yl)ethyl)pyridin-3-yl)boronic acid without any purifications.

LC/MS: mass calculated for $C_{17}H_{17}BF_2N_8O_2$: 414.15, measured (ES, m/z): 415.10 [M+H]$^+$.

Step 5: 5-(3-Chloro-6-(4-chloro-1H-1,2,3-triazol-1-yl)-2-fluorophenyl)-2-(2-(1-(difluoromethyl)-1H-pyrazol-3-yl)-1-(4-(1-methyl-1H-1,2,4-triazol-5-yl)-1H-pyrazol-1-yl)ethyl)pyridine To a solution of (6-(2-(1-(difluoromethyl)-1H-pyrazol-3-yl)-1-(4-(1-methyl-1H-1,2,4-triazol-5-yl)-1H-pyrazol-1-yl)ethyl)pyridin-3-yl)boronic acid (290 mg, 0.70 mmol, 1.0 equiv.) in 1,4-dioxane (15 mL) and $H_2O$ (3 mL) was added 4-chloro-1-(4-chloro-3-fluoro-2-iodophenyl)-1H-1,2,3-triazole (125 mg, 0.350 mmol, 0.5 equiv.), Pd(PPh$_3$)$_4$ (40 mg, 0.035 mmol, 0.05 equiv.), $K_2CO_3$ (73 mg, 0.53 mmol, 0.8 equiv.). The resulting mixture was maintained under nitrogen and stirred at 90° C. for 3H. After cooling to room temperature, the reaction was quenched with water. The resulting mixture was extracted with ethyl acetate. The organic layers were combined, dried over anhydrous sodium sulfate, filtered and concentrated. The resulting residue was purified by silica gel chromatography (0→75% ethyl acetate/petroleum ether) to yield the 5-(3-chloro-6-(4-chloro-1H-1,2,3-triazol-1-yl)-2-fluorophenyl)-2-(2-(1-(difluoromethyl)-1H-pyrazol-3-yl)-1-(4-(1-methyl-1H-1,2,4-triazol-5-yl)-1H-pyrazol-1-yl)ethyl)pyridine as an yellow oil. LC/MS: mass calculated for $C_{25}H_{18}Cl_2F_3N_{11}$: 599.11, measured (ES, m/z): 600.10 $[M+H]^+$.

Step 6: (R)-5-(3-Chloro-6-(4-chloro-1H-1,2,3-triazol-1-yl)-2-fluorophenyl)-2-(2-(1-(difluoromethyl)-1H-pyrazol-3-yl)-1-(4-(1-methyl-1H-1,2,4-triazol-5-yl)-1H-pyrazol-1-yl)ethyl)pyridine 1-oxide To a solution of 5-(3-chloro-6-(4-chloro-1H-1,2,3-triazol-1-yl)-2-fluorophenyl)-2-(2-(1-(difluoromethyl)-1H-pyrazol-3-yl)-1-(4-(1-methyl-1H-1,2,4-triazol-5-yl)-1H-pyrazol-1-yl)ethyl)pyridine (85 mg, 0.14 mmol, 1.0 equiv.) in MeOH (2 mL) was added $ReMeO_3$ (4 mg, 0.014 mmol, 0.1 equiv.), $H_2O_2$ (86 mg, 0.71 mmol, 1.0 equiv.). The resulting mixture was stirred at room temperature. for 3H. The resulting residue was purified by reverse-phase flash. The resulting residue was further purified by Chiral-HPLC with (Hex: DCM=3:1) (0.1% DEA):EtOH=50:50 to yield the (R)-5-(3-chloro-6-(4-chloro-1H-1,2,3-triazol-1-yl)-2-fluorophenyl)-2-(2-(1-(difluoromethyl)-1H-pyrazol-3-yl)-1-(4-(1-methyl-1H-1,2,4-triazol-5-yl)-1H-pyrazol-1-yl)ethyl)pyridine 1-oxide as a white solid.

LC/MS: mass calculated for $C_{25}H_{18}Cl_2F_3N_{11}O$: 615.10, measured (ES, m/z): 616.05 $[M+H]^+$. $^1H$ NMR (400 MHz, DMSO-$d_6$) δ 8.68 (s, 1H), 8.58 (s, 1H), 8.45 (s, 1H), 8.00-8.05 (m, 3H), 7.87 (s, 1H), 7.70 (t, J=57.0 Hz, 1H), 7.68 (s, 1H), 7.38 (d, J=8.3 Hz, 1H), 7.19 (d, J=8.3 Hz, 1H), 6.47 (dd, J=9.4, 5.5 Hz, 1H), 6.14 (d, J=2.7 Hz, 1H), 3.91 (s, 3H), 3.60-3.75 (m, 2H). $^{19}F$ NMR (376 MHz, DMSO-$d_6$) δ −93.82, −112.92.

Example 834: (R)-5-(3-Chloro-6-(4-chloro-1H-1,2,3-triazol-1-yl)-2-fluorophenyl)-2-(2-(1-(difluoromethyl)-1H-pyrazol-4-yl)-1-(4-(4-fluoro-1-methyl-1H-1,2,3-triazol-5-yl)-1H-pyrazol-1-yl)ethyl)pyridine 1-oxide

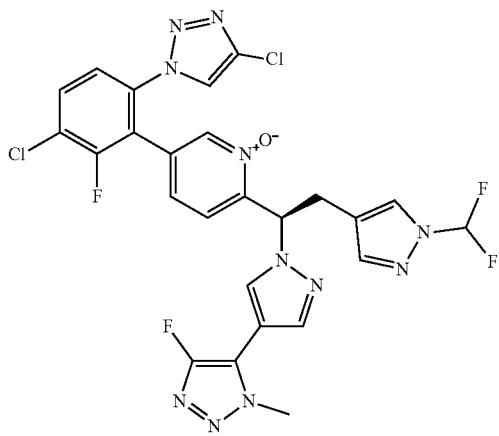

Step 1: 2-(1-(Difluoromethyl)-1H-pyrazol-4-yl)-N-methoxy-N-methylacetamide

To a solution of 1-(difluoromethyl)-1H-pyrazole-4-carboxylic acid (1.0 g, 5.68 mmol, 1.0 equiv.) in dichloromethane (10 mL) was added 1,1'-carbonyldiimidazole (1.4 g, 8.52 mmol, 1.5 equiv.) and N,O-dimethylhydroxylamine (831 mg, 8.52 mmol, 1.5 equiv.). The reaction mixture was stirred at room temperature overnight. The reaction was added water, and the mixture extracted with EA twice. The combined layers were washed with hydrochloric acid (pH=3~4), saturated sodium bicarbonate and brine twice respectively, dried over $Na_2SO_4$ and concentrated to yield 2-(1-(difluoromethyl)-1H-pyrazol-4-yl)-N-methoxy-N-methylacetamide as an off-white solid. LC/MS: mass calculated for $C_8H_{11}F_2N_3O_2$: 219.08, measured (ES, m/z): 220.00 $[M+H]^+$.

Step 2: 1-(5-Bromopyridin-2-yl)-2-(1-(difluoromethyl)-1H-pyrazol-4-yl)ethan-1-one To a solution of 2,5-dibromopyridine (1.1 g, 5.02 mmol, 1.0 equiv.) in dry toluene (10 mL) added butyllithium (2.1 mL, 5.27 mmol, 1.05 equiv.) after the temperature was dropped to −78° C. and stirred for 1 h under $N_2$. A solution of 2-(1-(difluoromethyl)-1H-pyrazol-4-yl)-N-methoxy-N-methylacetamide (1.0 g, 5.02 mol, 1.0 equiv.) in dry toluene (5 mL) was then added and stirred for additional 1 h. The reaction was then quenched by the addition of saturated ammonium chloride aqueous solution and extracted with ethyl acetate twice. The combined organic layers was washed with brine, dried over $Na_2SO_4$, concentrated and purified by silica gel chromatography (0→30% EtOAc/petroleum ether) to yield 1-(5-bromopyridin-2-yl)-2-(1-(difluoromethyl)-1H-pyrazol-4-yl)ethan-1-one as white solid. LC/MS: mass calculated for $C_{11}H_8BrF_2N_3O$: 314.98, measured (ES, m/z): 316.00, 317.95 $[M+H, M+H+2]^+$.

Step 3: 1-(5-Bromopyridin-2-yl)-2-(1-(difluoromethyl)-1H-pyrazol-4-yl)ethan-1-ol To a solution of 1-(5-bromopyridin-2-yl)-2-(1-(difluoromethyl)-1H-pyrazol-4-yl)ethan-1-one (390 mg, 1.23 mmol, 1.0 equiv.) in $CH_3OH$ (4 mL) at 0° C. To the reaction mixture was then added sodium borohydride in portions (70 mg, 1.85 mmol, 1.5 equiv.). The reaction mixture was stirred at room temperature for 1 h. The reaction was quenched with water, and the mixture extracted with EA twice. The combined organic layers were washed with brine, dried over $Na_2SO_4$ and concentrated under vacuum to yield 1-(5-bromopyridin-2-yl)-2-(1-(difluoromethyl)-1H-pyrazol-4-yl)ethan-1-ol as a yellow oil. LC/MS: mass calculated for $C_{11}H_{10}BrF_2N_3O$: 317.00, measured (ES, m/z): 318.00, 319.90 $[M+H, M+H+2]^+$.

Step 4: 1-(5-Bromopyridin-2-yl)-2-(1-(difluoromethyl)-1H-pyrazol-4-yl)ethyl methanesulfonate To a solution of 1-(5-bromopyridin-2-yl)-3-(difluoromethoxy)propan-1-ol (370 mg, 1.16 mmol, 1.0 equiv.) and triethylamine (0.5 mL, 3.49 mmol, 3.0 equiv.) in DCM (4 mL) was added methanesulfonic anhydride (304 mg, 1.75 mmol, 1.5 equiv.) at 0° C. and the solution was stirred for 2 h at room temperature. The mixture was added $H_2O$, extracted with DCM twice. The combined organic layers was washed with brine, dried over $Na_2SO_4$, concentrated and purified by silica gel chromatography (0→50% EtOAc/petroleum ether) to yield 1-(5-bromopyridin-2-yl)-2-(1-(difluoromethyl)-1H-pyrazol-4-yl)ethyl methanesulfonate as a yellow oil. LC/MS: mass calculated for $C_{12}H_{12}BrF_2N_3O_3S$: 394.98, measured (ES, m/z): 396.00, 397.85 $[M+H, M+H+2]^+$.

Step 5: 5-Bromo-2-(2-(1-(difluoromethyl)-1H-pyrazol-4-yl)-1-(4-(1-methyl-1H-1,2,3-triazol-5-yl)-1H-pyrazol-1-yl)ethyl)pyridine To a mixture of 1-methyl-5-(1H-pyrazol-4-yl)-1H-1,2,3-triazole (145 mg, 0.97 mmol, 1.1 equiv.) and cesium carbonate (317 mg, 0.97 mmol, 1.1 equiv.) in acetonitrile (4 mL) was added 1-(5-bromopyridin-2-yl)-2-(1-(difluoromethyl)-1H-pyrazol-4-yl)ethyl methanesulfonate (350 mg, 0.88 mmol, 1.0 equiv.) at room temperature and the solution was stirred for 2 h at 80° C. The mixture was diluted with H$_2$O, extracted with DCM twice. The combined organic layers was washed with brine, dried over Na$_2$SO$_4$, concentrated and purified by silica gel chromatography (0→10% CH$_3$OH/DCM) to yield 5-bromo-2-(2-(1-(difluoromethyl)-1H-pyrazol-4-yl)-1-(4-(1-methyl-1H-1,2,3-triazol-5-yl)-1H-pyrazol-1-yl)ethyl)pyridine as a yellow solid. LC/MS: mass calculated for C$_{17}$H$_{15}$BrF$_2$N$_8$: 448.06, measured (ES, m/z): 449.00, 450.95 [M+H, M+H+2]$^+$.

Step 6: 5-Bromo-2-(2-(1-(difluoromethyl)-1H-pyrazol-4-yl)-1-(4-(4-fluoro-1-methyl-1H-1,2,3-triazol-5-yl)-1H-pyrazol-1-yl)ethyl)pyridine To a mixture of 5-bromo-2-(2-(1-(difluoromethyl)-1H-pyrazol-4-yl)-1-(4-(1-methyl-1H-1,2,3-triazol-5-yl)-1H-pyrazol-1-yl)ethyl)pyridine (320 mg, 0.71 mmol, 1.0 equiv.) in acetonitrile (4 mL) was added Selectfluor™ (505 mg, 1.43 mmol, 2.0 equiv.). The reaction mixture was stirred at 60° C. for 6 h. To the reaction was added water, and the mixture extracted with EtOAc twice. The combined organic layers were washed with brine, dried over sodium sulfate, and concentrated. The residue was purified by silica gel chromatography (0→60% EtOAc/petroleum ether) to yield 5-bromo-2-(2-(1-(difluoromethyl)-1H-pyrazol-4-yl)-1-(4-(4-fluoro-1-methyl-1H-1,2,3-triazol-5-yl)-1H-pyrazol-1-yl)ethyl)pyridine as a light yellow oil. LC/MS: mass calculated for C$_{17}$H$_{14}$BrF$_3$N$_8$: 466.05, measured (ES, m/z): 467.00, 468.95 [M+H, M+H+2]$^+$.

Step 7: (6-(2-(1-(Difluoromethyl)-1H-pyrazol-4-yl)-1-(4-(4-fluoro-1-methyl-1H-1,2,3-triazol-5-yl)-1H-pyrazol-1-yl)ethyl)pyridin-3-yl)boronic acid To a mixture of 5-bromo-2-(2-(1-(difluoromethyl)-1H-pyrazol-4-yl)-1-(4-(4-fluoro-1-methyl-1H-1,2,3-triazol-5-yl)-1H-pyrazol-1-yl)ethyl)pyridine (150 mg, 0.32 mmol, 1.0 equiv.) and 4,4,4',4',5,5,5',5'-octamethyl-2,2'-bi(1,3,2-dioxaborolane) (163 mg, 0.64 mmol, 2.0 equiv.) in 1,4-dioxane (5 mL) was added potassium acetate (126 mg, 1.28 mmol, 4.0 equiv.) and Pd(dppf)Cl$_2$ (23 mg, 0.03 mmol, 0.1 equiv.) under N$_2$. The solution was stirred at 90° C. for 2 h. To the reaction was added water, and the mixture extracted with EA twice. The combined organic layers were washed with brine, dried over Na$_2$SO$_4$ and concentrated under vacuum to yield (6-(2-(1-(difluoromethyl)-1H-pyrazol-4-yl)-1-(4-(4-fluoro-1-methyl-1H-1,2,3-triazol-5-yl)-1H-pyrazol-1-yl)ethyl)pyridin-3-yl)boronic acid as brown oil. LC/MS: mass calculated for C$_{17}$H$_{16}$BF$_3$N$_8$O$_2$: 432.14, measured (ES, m/z): 433.15[M+H]$^+$.

Step 8: 5-(3-Chloro-6-(4-chloro-1H-1,2,3-triazol-1-yl)-2-fluorophenyl)-2-(2-(1-(difluoromethyl)-1H-pyrazol-4-yl)-1-(4-(4-fluoro-1-methyl-1H-1,2,3-triazol-5-yl)-1H-pyrazol-1-yl)ethyl)pyridine To a mixture of (6-(2-(1-(difluoromethyl)-1H-pyrazol-4-yl)-1-(4-(4-fluoro-1-methyl-1H-1,2,3-triazol-5-yl)-1H-pyrazol-1-yl)ethyl)pyridin-3-yl)boronic acid (130 mg, 0.30 mmol, 1.0 equiv.) and 4-chloro-1-(4-chloro-3-fluoro-2-iodophenyl)-1H-1,2,3-triazole (129 mg, 0.36 mmol, 1.2 equiv.) in the mixed solution of 1,4-dioxane (2 mL) and water (0.5 mL) was added potassium carbonate (166 mg, 4.81 mmol, 4.0 equiv.) and tetrakis(triphenylphosphine)Palladium(0) (35 mg, 0.03 mmol, 0.1 equiv.). The reaction mixture was evacuated and purged with nitrogen. This was repeated 2×. The reaction mixture was then stirred at 100° C. for 2 h under N$_2$. Water was added, the mixture was extracted with EA. The combined organic layers were washed with brine, dried over Na$_2$SO$_4$ and concentrated under vacuum. The resulting residue was purified by silica gel chromatography with EtOAc/petroleum (0→90%) to yield 5-(3-chloro-6-(4-chloro-1H-1,2,3-triazol-1-yl)-2-fluorophenyl)-2-(2-(1-(difluoromethyl)-1H-pyrazol-4-yl)-1-(4-(4-fluoro-1-methyl-1H-1,2,3-triazol-5-yl)-1H-pyrazol-1-yl)ethyl)pyridine as a light yellow solid. LC/MS: mass calculated for C$_{25}$H$_{17}$Cl$_2$F$_4$N$_{11}$: 617.10, measured (ES, m/z): 618.15[M+H]$^+$.

Step 9: (R)-5-(3-Chloro-6-(4-chloro-1H-1,2,3-triazol-1-yl)-2-fluorophenyl)-2-(2-(1-(difluoromethyl)-1H-pyrazol-4-yl)-1-(4-(4-fluoro-1-methyl-1H-1,2,3-triazol-5-yl)-1H-pyrazol-1-yl)ethyl)pyridine 1-oxide To a solution of 5-(3-chloro-6-(4-chloro-1H-1,2,3-triazol-1-yl)-2-fluorophenyl)-2-(2-(1-(difluoromethyl)-1H-pyrazol-4-yl)-1-(4-(4-fluoro-1-methyl-1H-1,2,3-triazol-5-yl)-1H-pyrazol-1-yl)ethyl)pyridine (130 mg, 0.21 mmol, 1.0 equiv.) and methyl trioxorhenium (VII) (10 mg, 0.04 mmol, 0.2 equiv.) in CH$_3$OH (1.5 mL) was added hydrogen peroxide (0.2 mL, 2.10 mmol, 10.0 equiv.). The reaction mixture was stirred at room temperature for 1 h. The reaction was purified by reverse phase chromatography on C18 (80 g, CH$_3$CN/H$_2$O (0.05% CF$_3$COOH: 0→50%). The resulting residue was purified Prep-Chiral-HPLC to yield (R)-5-(3-chloro-6-(4-chloro-1H-1,2,3-triazol-1-yl)-2-fluorophenyl)-2-(2-(1-(difluoromethyl)-1H-pyrazol-4-yl)-1-(4-(4-fluoro-1-methyl-1H-1,2,3-triazol-5-yl)-1H-pyrazol-1-yl)ethyl)pyridine 1-oxide as an off-white solid.

LC/MS: mass calculated for C$_{25}$H$_{17}$Cl$_2$F$_4$N$_{11}$O: 633.09, measured (ES, m/z): 634.20 [M+H]$^+$. $^1$H NMR (300 MHz, DMSO-d$_6$): b 8.68 (s, 1H), 8.43 (s, 2H), 8.05-7.98 (m, 1H), 7.97 (s, 1H), 7.82 (s, 1H), 7.72-7.63 (m, 2H), 7.54-7.44 (m, 1H), 7.41 (s, 1H), 7.24-7.14 (m, 1H), 6.24-6.29 (m, 1H), 4.02 (s, 3H), 3.59-3.38 (m, 2H). $^{19}$F-NMR (282 MHz, DMSO-d$_6$): δ −93.85, −112.93, −145.25.

Example 835: (S)-5-(3-Chloro-6-(4-chloro-1H-1,2,3-triazol-1-yl)-2-fluorophenyl)-2-(2-(1-(difluoromethyl)-1H-pyrazol-4-yl)-1-(4-(4-fluoro-1-methyl-1H-1,2,3-triazol-5-yl)-1H-pyrazol-1-yl)ethyl)pyridine 1-oxide

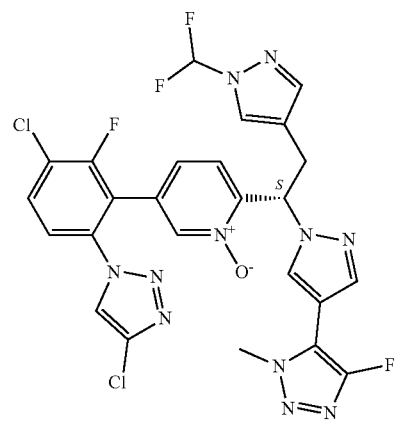

LC/MS: mass calculated for $C_{25}H_{17}Cl_2F_4N_{11}O$: 633.09, measured (ES, m/z): 634.05 [M+H]$^+$, $^1$H NMR (300 MHz, DMSO-$d_6$) δ 8.68 (s, 1H), 8.43-8.48 (m, 2H), 7.94-8.07 (m, 2H), 7.46-7.88 (m, 4H), 7.41 (s, 1H), 7.19-7.25 (m, 1H), 6.23-6.31 (m, 1H), 4.02 (s, 3H), 3.38-3.59 (m, 2H). $^{19}$F NMR (282 MHz, DMSO-$d_6$) δ −93.82, −93.85, −112.93, −145.25.

Example 836: (R)-5-(3-Chloro-6-(4-chloro-1H-1,2,3-triazol-1-yl)-2-fluorophenyl)-2-(2-(1-(difluoromethyl)-1H-pyrazol-3-yl)-1-(4-(4-fluoro-1-methyl-1H-1,2,3-triazol-5-yl)-1H-pyrazol-1-yl)ethyl)pyridine 1-oxide

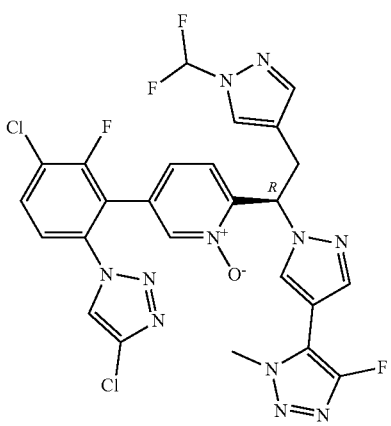

Step 1: 2-(1-(Difluoromethyl)-1H-pyrazol-3-yl)-N-methoxy-N-methylacetamide

To a solution of 1-(difluoromethyl)-1H-pyrazole-3-carboxylic acid (4.0 g, 22.71 mmol, 1.0 equiv.) in dichloromethane (40 mL) was added 1,1'-carbonyldiimidazole (5.5 g, 34.07 mmol, 1.5 equiv.) and N,O-dimethylhydroxylamine (3.3 g, 34.07 mol, 1.5 equiv). The reaction mixture was stirred at room temperature overnight. The reaction was added water, and the mixture extracted with EA twice. The combined layers were washed with hydrochloric acid (pH=3~4), saturated sodium bicarbonate and brine twice respectively, dried over $Na_2SO_4$ and concentrated to yield 2-(1-(difluoromethyl)-1H-pyrazol-3-yl)-N-methoxy-N-methylacetamide as white solid. LC/MS: mass calculated for $C_8H_{11}F_2N_3O_2$: 219.08, measured (ES, m/z): 220.05 [M+H]$^+$.

Step 2: 1-(5-Bromopyridin-2-yl)-2-(1-(difluoromethyl)-1H-pyrazol-3-yl)ethan-1-one A solution of 2, 5-dibromopyridine (4.5 g, 0.02 mol, 1.0 equiv) in dry toluene (40 mL) was added butyllithium (8 mL, 0.020 mol, 1.05 equiv.) after the temperature was dropped to −78° C. and stirred for 1 h under $N_2$. Then, a solution of 2-(1-(difluoromethyl)-1H-pyrazol-3-yl)-N-methoxy-N-methylacetamide (4.2 g, 0.02 mol, 1.0 equiv.) in dry toluene (10 mL) was added and the mixture stirred for additional 1 h. The reaction was then quenched by the addition of saturated ammonium chloride aqueous solution and extracted with ethyl acetate twice. The combined organic layers was washed with brine, dried over $Na_2SO_4$, concentrated and purified by silica gel chromatography (0→30% EA/petroleum ether) to yield 1-(5-bromopyridin-2-yl)-2-(1-(difluoromethyl)-1H-pyrazol-3-yl)ethan-1-one as yellow solid. LC/MS: mass calculated for $C_{11}H_8BrF_2N_3O$: 314.98, measured (ES, m/z): 315.95, 318.00[M+H, M+H+2]$^+$.

Step 3: 1-(5-Bromopyridin-2-yl)-2-(1-(difluoromethyl)-1H-pyrazol-3-yl)ethan-1-ol To a solution of 1-(5-bromopyridin-2-yl)-2-(1-(difluoromethyl)-1H-pyrazol-3-yl)ethan-1-one (850 mg, 2.69 mmol, 1.0 equiv.) in $CH_3OH$ (9 mL) at 0° C. was added sodium borohydride in portions (153 mg, 4.03 mmol, 1.5 equiv.). The reaction mixture was stirred at room temperature for 1 h. The reaction was quenched with water, and the mixture extracted with EA twice. The combined organic layers were washed with brine, dried over $Na_2SO_4$ and concentrated under vacuum. The resulting residue 1-(5-bromopyridin-2-yl)-2-(1-(difluoromethyl)-1H-pyrazol-3-yl)ethan-1-ol as a yellow oil. LC/MS: mass calculated for $C_{11}H_{10}BrF_2N_3O$: 317.00, measured (ES, m/z): 318.00, 319.95 [M+H, M+H+2]$^+$.

Step 4: 1-(5-Bromopyridin-2-yl)-2-(1-(difluoromethyl)-1H-pyrazol-3-yl)ethyl methanesulfonate To a mixture of 1-(5-bromopyridin-2-yl)-2-(1-(difluoromethyl)-1H-pyrazol-3-yl)ethan-1-ol (850 mg, 2.67 mmol, 1.0 equiv.) and triethylamine (1 mL, 8.02 mmol, 3.0 equiv.) in DCM (9 mL) was added methanesulfonic anhydride (0.70 mg, 4.01 mmol, 2.0 equiv.) at 0° C. and the solution was stirred for 1 h at room temperature. The mixture was added $H_2O$, extracted with DCM twice. The combined organic layers was washed with brine, dried over $Na_2SO_4$, concentrated and purified by silica gel chromatography (0→50% EA/petroleum ether) to yield 1-(5-bromopyridin-2-yl)-2-(1-(difluoromethyl)-1H-pyrazol-3-yl)ethyl methanesulfonate as a yellow oil. LC/MS: mass calculated for $C_{12}H_{12}BrF_2N_3O_3S$: 394.98, measured (ES, m/z):396.00, 397.85 [M+H, M+H+2]$^+$.

Step 5: 5-Bromo-2-(2-(1-(difluoromethyl)-1H-pyrazol-3-yl)-1-(4-(1-methyl-1H-1,2,3-triazol-5-yl)-1H-pyrazol-1-yl)ethyl)pyridine To a mixture of 1-methyl-5-(1H-pyrazol-4-yl)-1H-1,2,3-triazole (219 mg, 1.47 mmol, 1.1 equiv.) and cesium carbonate (479 mg, 1.47 mmol, 1.1 equiv.) in acetonitrile (6 mL) was stirred at room temperature for 10 minutes. To the reaction mixture was then added 1-(5-bromopyridin-2-yl)-2-(1-(difluoromethyl)-1H-pyrazol-3-yl)ethyl methanesulfonate (530 mg, 1.34 mmol, 1.0 equiv.) at room temperature and the solution was stirred for 2 h at room temperature. The mixture was diluted with $H_2O$, extracted with DCM twice. The combined organic layers was washed with brine, dried over $Na_2SO_4$, concentrated and purified by silica gel chromatography (0→10% $CH_3OH$/DCM) to yield 5-bromo-2-(2-(1-(difluoromethyl)-1H-pyrazol-3-yl)-1-(4-(1-methyl-1H-1,2,3-triazol-5-yl)-1H-pyrazol-1-yl)ethyl)pyridine as a yellow oil. LC/MS: mass calculated for $C_{17}H_{15}BrF_2N_8$: 448.06, measured (ES, m/z):449.00, 450.95 [M+H, M+H+2]$^+$.

Step 6: 5-Bromo-2-(2-(1-(difluoromethyl)-1H-pyrazol-3-yl)-1-(4-(4-fluoro-1-methyl-1H-1,2,3-triazol-5-yl)-1H-pyrazol-1-yl)ethyl)pyridine The mixture of 5-bromo-2-(2-(1-(difluoromethyl)-1H-pyrazol-3-yl)-1-(4-(1-methyl-1H-1, 2, 3-triazol-5-yl)-1H- pyrazol-1-yl)ethyl)pyridine (320 mg, 0.71 mmol, 1.0 equiv.) in Acetonitrile (3.5 mL) was added Selectfluor™ (505 mg, 1.43 mmol, 2.0 equiv.). The reaction mixture was stirred at 60° C. for 6 h. To the reaction was added water, and the mixture extracted with EA twice. The combined organic layers were washed with brine, dried over sodium sulfate and concentrated. The residue was purified by silica gel chromatography (0→60% EA/petroleum ether) to yield 5-bromo-2-(2-(1-(difluoromethyl)-1H-pyrazol-3-yl)-1-(4-(4-fluoro-1-methyl-1H-1,2,3-triazol-5-yl)-1H-pyrazol-1-yl)ethyl)pyridine as a light yellow solid. LC/MS: mass calculated for $C_{17}H_{14}BrF_3N_8$: 466.05, measured (ES, m/z): 467.00 468.95 [M+H, M+H+2]$^+$.

Step 7: (6-(2-(1-(Difluoromethyl)-1H-pyrazol-3-yl)-1-(4-(4-fluoro-1-methyl-1H-1,2,3-triazol-5-yl)-1H-pyrazol-1-yl)ethyl)pyridin-3-yl)boronic acid To a mixture of 5-bromo-2-(2-(1-(difluoromethyl)-1H-pyrazol-4-yl)-1-(4-(4-fluoro-1-methyl-1H-1,2,3-triazol-5-yl)-1H-pyrazol-1-yl)ethyl)pyridine (160 mg, 0.34 mmol, 1.0 equiv.) and 4,4,4',4',5,5,5',5'-octamethyl-2,2'-bi(1,3,2-dioxaborolane) (174 mg, 0.69 mmol, 2.0 equiv.) in 1,4-dioxane (2 mL) was added potassium acetate (168 mg, 1.72 mmol, 5.0 equiv.) and Pd(dppf)Cl$_2$ (25 mg, 0.03 mmol, 0.1 equiv.) under N$_2$. The solution was stirred at 90° C. for 2 h. Water was added, the mixture was extracted with EA. The combined organic layers were washed with brine, dried over Na$_2$SO$_4$ and concentrated under vacuum to yield (6-(2-(1-(difluoromethyl)-1H-pyrazol-3-yl)-1-(4-(4-fluoro-1-methyl-1H-1, 2, 3-triazol-5-yl)-1H-pyrazol-1-yl)ethyl)pyridin-3-yl)boronic acid as a brown oil. LC/MS: mass calculated for $C_{17}H_{16}BF_3N_8O_2$: 432.14, measured (ES, m/z): 433.00 [M+H]$^+$.

Step 8: 5-(3-Chloro-6-(4-chloro-1H-1,2,3-triazol-1-yl)-2-fluorophenyl)-2-(2-(1-(difluoromethyl)-1H-pyrazol-3-yl)-1-(4-(4-fluoro-1-methyl-1H-1,2,3-triazol-5-yl)-1H-pyrazol-1-yl)ethyl)pyridine To a mixture of (6-(2-(1-(difluoromethyl)-1H-pyrazol-4-yl)-1-(4-(4-fluoro-1-methyl-1H-1,2,3-triazol-5-yl)-1H-pyrazol-1-yl)ethyl)pyridin-3-yl)boronic acid (130 mg, 0.30 mmol, 1.0 equiv.) and 4-chloro-1-(4-chloro-3-fluoro-2-iodophenyl)-1H-1,2,3-triazole (162 mg, 0.45 mmol, 1.5 equiv.) in the mixed solution of 1,4-dioxane (2 mL) and water (0.5 mL) was added potassium carbonate (166 mg, 1.20 mmol, 4.0 equiv.) and tetrakis(triphenylphosphine)Palladium(0) (35 mg, 0.03 mmol, 0.1 equiv.). The reaction flask was evacuated, purged with nitrogen. This was repeated 2×. The reaction mixture was stirred at 100° C. for 2 h under N$_2$.

Water was added, the mixture was extracted with EA. The combined organic layers were washed with brine, dried over Na$_2$SO$_4$ and concentrated under vacuum. The resulting residue was purified by silica gel chromatography with EA/PE (0→90%) to yield 5-(3-chloro-6-(4-chloro-1H-1,2,3-triazol-1-yl)-2-fluorophenyl)-2-(2-(1-(difluoromethyl)-1H-pyrazol-3-yl)-1-(4-(4-fluoro-1-methyl-1H-1,2,3-triazol-5-yl)-1H-pyrazol-1-yl)ethyl)pyridine as off-white solid. LC/MS: mass calculated for $C_{25}H_{17}Cl_2F_4N_{11}$: 617.10, measured (ES, m/z): 618.05 [M+H]$^+$.

Step 9: (R)-5-(3-Chloro-6-(4-chloro-1H-1,2,3-triazol-1-yl)-2-fluorophenyl)-2-(2-(1-(difluoromethyl)-1H-pyrazol-3-yl)-1-(4-(4-fluoro-1-methyl-1H-1,2,3-triazol-5-yl)-1H-pyrazol-1-yl)ethyl)pyridine 1-oxide To a solution of 5-(3-chloro-6-(4-chloro-1H-1,2,3-triazol-1-yl)-2-fluorophenyl)-2-(2-(1-(difluoromethyl)-1H-pyrazol-3-yl)-1-(4-(4-fluoro-1-methyl-1H-1,2,3-triazol-5-yl)-1H-pyrazol-1-yl)ethyl)pyridine (120 mg, 0.19 mmol, 1.0 equiv.) and methyl trioxorhenium (VII) (10 mg, 0.04 mmol, 0.2 equiv.) in CH$_3$OH (3 mL) was added hydrogen peroxide (0.2 mL, 1.94 mmol, 10.0 equiv.). The reaction mixture was stirred at room temperature for 1 h. The reaction was purified by reverse phase chromatography on C18 (80 g, ACN/H$_2$O (0.05% CF$_3$COOH: 0→50%). The resulting residue was purified by Prep-Chiral-HPLC to yield (R)-5-(3-chloro-6-(4-chloro-1H-1,2,3-triazol-1-yl)-2-fluorophenyl)-2-(2-(1-(difluoromethyl)-1H-pyrazol-3-yl)-1-(4-(4-fluoro-1-methyl-1H-1,2,3-triazol-5-yl)-1H-pyrazol-1-yl)ethyl) pyridine 1-oxide as a white solid.

LC/MS: mass calculated for $C_{25}H_{17}Cl_2F_4N_{11}O$: 633.09, measured (ES, m/z): 634.05 [M+H]$^+$. $^1$H NMR (300 MHz, DMSO-d$_6$): b 8.66 (s, 1H), 8.47 (s, 1H), 8.43 (s, 1H), 7.96-8.07 (m, 2H), 7.93 (s, 1H), 7.70 (s, 1H), 7.68 (t, J=59.1 Hz, 1H), 7.41 (d, J=8.3 Hz, 1H), 7.18 (dd, J=8.2, 1.6 Hz, 1H), 6.45-6.50 (m, 1H), 6.13 (d, J=2.6 Hz, 1H), 4.02 (s, 3H), 3.74-3.57 (m, 2H). $^{19}$F NMR (282 MHz, DMSO-d$_6$): b −93.85, −112.92, −145.18.

Example 837: (S)-5-(3-Chloro-6-(4-chloro-1H-1,2,3-triazol-1-yl)-2-fluorophenyl)-2-(2-(1-(difluoromethyl)-1H-pyrazol-3-yl)-1-(4-(4-fluoro-1-methyl-1H-1,2,3-triazol-5-yl)-1H-pyrazol-1-yl)ethyl)pyridine 1-oxide

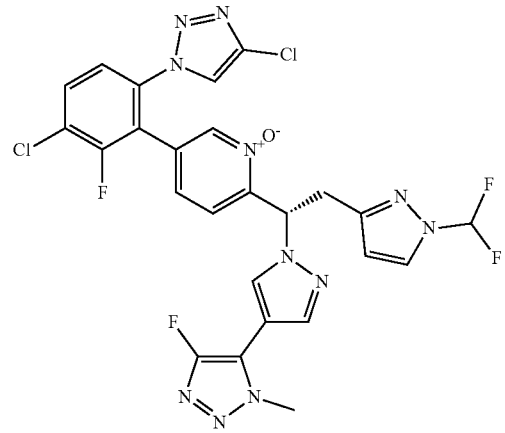

LC/MS: mass calculated for $C_{25}H_{17}Cl_2F_4N_{11}O$: 633.09, measured (ES, m/z): 634.05 [M+H]$^+$, $^1$H NMR (300 MHz, DMSO-d$_6$) δ 8.67 (s, 1H), 8.46 (s, 1H), 8.44 (s, 1H), 7.96-8.07 (m, 2H), 7.94 (s, 1H), 7.88 (s, 1H), 7.86 (d, J=57.0 Hz, 1H), 7.41 (d, J=8.3 Hz, 1H), 7.18 (d, J=8.4 Hz, 1H), 6.45-6.50 (m, 1H), 6.14 (d, J=2.6 Hz, 1H), 4.03 (s, 3H), 3.57-3.75 (m, 2H). $^{19}$F NMR (282 MHz, DMSO) δ −93.85, −94.42, −112.91, −145.17.

Example 838: (S)-5-(3-Chloro-6-(5-(difluoromethyl)-1H-1,2,3-triazol-1-yl)-2-fluorophenyl)-2-(3-(difluoromethoxy)-1-(4-(1-methyl-1H-1,2,4-triazol-5-yl)-1H-pyrazol-1-yl)propyl)pyridine 1-oxide

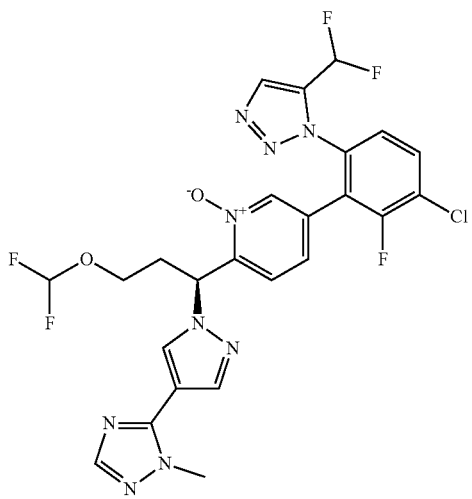

LC/MS: mass calculated for $C_{24}H_{19}ClF_5N_9O_2$: 595.13, measured (ES, m/z): 596.10 $[M+H]^+$. $^1$H NMR (300 MHz, CD$_3$OD) δ 8.39-8.55 (m, 2H), 8.35 (s, 1H), 8.11 (s, 1H), 7.84-7.96 (m, 2H), 7.51-7.64 (m, 2H), 7.29-7.33 (m, 1H), 6.72-7.15 (t, J=6.0 Hz, 1H), 6.11-6.55 (m, 2H), 3.90-4.03 (m, 4H), 3.68-3.74 (m, 1H), 2.65-2.92 (m, 2H). $^{19}$F NMR (300 MHz, CD$_3$OD) δ −85.54, −113.83, −114.53.

Example 839: (S*)-5-(3-Chloro-6-(5-(difluoromethyl)-1H-1,2,3-triazol-1-yl)-2-fluorophenyl)-2-(3-(difluoromethoxy)-1-(4-(1-methyl-1H-1,2,4-triazol-5-yl)-1H-pyrazol-1-yl)propyl)pyridine 1-oxide

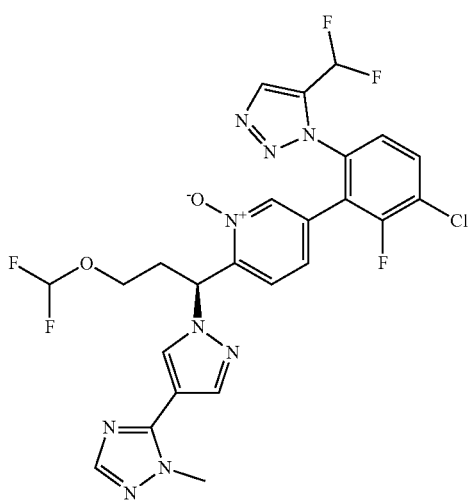

Step 1: 5-Bromo-2-(3-(difluoromethoxy)-1-(4-(1-methyl-1H-1,2,4-triazol-5-yl)-1H-pyrazol-1-yl)propyl)pyridine To a solution of 1-methyl-5-(1H-pyrazol-4-yl)-1H-1,2,4-triazole (360.0 mg, 2.41 mmol, 1.0 equiv.) and cesium carbonate (629.1 mg, 1.93 mmol, 0.8 equiv.) in acetonitrile (15.0 mL) was added 1-(5-bromopyridin-2-yl)-3-(difluoromethoxy)propyl methanesulfonate (869.3 mg, 2.41 mmol, 1.0 equiv.). The resulting mixture was stirred at 70° C. for 2 h. The reaction was quenched with water (50 mL). The resulting mixture was extracted with ethyl acetate (3×50 mL). The organic layers were combined, dried over anhydrous sodium sulfate, filtered and concentrated. The resulting residue was purified by silica gel chromatography (0→10% DCM:MeOH) to yield the 5-bromo-2-(3-(difluoromethoxy)-1-(4-(1-methyl-1H-1,2,4-triazol-5-yl)-1H-pyrazol-1-yl)propyl)pyridine as a yellow oil. LC/MS: mass calculated for $C_{15}H_{15}BrF_2N_6O$: 412.05, measured (ES, m/z): 413.10 $[M+H]^+$.

Step 2: (6-(3-(Difluoromethoxy)-1-(4-(1-methyl-1H-1,2,4-triazol-5-yl)-1H-pyrazol-1-yl)propyl)pyridin-3-yl)boronic acid To a solution of 5-bromo-2-(3-(difluoromethoxy)-1-(4-(1-methyl-1H-1,2,4-triazol-5-yl)-1H-pyrazol-1-yl)propyl)pyridine (900.0 mg, 2.18 mmol, 1.0 equiv.) in 1,4-dioxane (25.0 mL) was added 4,4,4',4',5,5,5',5'-octamethyl-2,2'-bi(1,3,2-dioxaborolane) (829.6 mg, 3.27 mmol, 1.5 equiv.) [1,1'-bis(diphenylphosphino)ferrocene]dichloropalladium(II) (160 mg, 0.22 mmol, 0.2 equiv.) and potassium acetate (320.6 mg, 3.27 mmol, 1.5 equiv.). The resulting mixture was maintained under nitrogen and stirred at 90° C. for 16 h. The reaction was quenched with water (50 mL). The resulting mixture was extracted with ethyl acetate (3×100 mL). The organic layers were combined, dried over anhydrous sodium sulfate, filtered and concentrated to yield (6-(3-(difluoromethoxy)-1-(4-(1-methyl-1H-1,2,4-triazol-5-yl)-1H-pyrazol-1-yl)propyl)pyridin-3-yl)boronic acid as a dark oil. LC/MS: mass calculated for $C_{15}H_{17}BF_2N_6O_3$: 378.14, measured (ES, m/z): 379.15 $[M+H]^+$.

Step 3: (1-(4-Chloro-3-fluoro-2-iodophenyl)-1H-1,2,3-triazol-4-yl) methanol

To a solution of 1-azido-4-chloro-3-fluoro-2-iodobenzene (1.0 g, 3.36 mmol, 1.0 equiv.) in toluene (20.0 mL) was added prop-2-yn-1-ol (565.4 mg, 10.09 mmol, 10.0 equiv.). The resulting mixture was stirred at 100° C. for 16 h. The mixture was then concentrated under reduced pressure to yield 1-(4-Chloro-3-fluoro-2-iodophenyl)-1H-1,2,3-triazol-4-yl) methanol as a black solid. LCMS: mass calculated for $C_9H_6ClFIN_3O$: 352.92, measured (ES, m/z): 353.9 $[M+H]^+$.

Step 4: 1-(4-Chloro-3-fluoro-2-iodophenyl)-1H-1,2,3-triazole-4-carbaldehyde

To a solution of (1-(4-chloro-3-fluoro-2-iodophenyl)-1H-1,2,3-triazol-4-yl) methanol (400.0 mg, 1.13 mmol, 1.0 equiv.) in dichloromethane (20.0 mL) was added Dess Martin reagent (719.9 mg, 1.70 mmol, 1.5 equiv.). The resulting mixture was stirred at room temperature for 2 h. The reaction was quenched with water (50 mL). The resulting mixture was extracted with DCM (3×50 mL). The organic layers were combined, dried over anhydrous sodium sulfate, filtered and concentrated. The resulting residue was purified by silica gel chromatography (0→40% ethyl acetate/petroleum ether) to yield 1-(4-chloro-3-fluoro-2-iodophenyl)-1H-1,2,3-triazole-4-carbaldehyde as a yellow oil. LCMS: mass calculated for $C_9H_4ClFIN_3O$: 350.91, measured (ES, m/z): 351.90 $[M+H]^+$.

Step 5: 1-(4-Chloro-3-fluoro-2-iodophenyl)-4-(difluoromethyl)-1H-1,2,3-triazole To a solution of 1-(4-chloro-3-fluoro-2-iodophenyl)-1H-1,2,3-triazole-4-carbaldehyde (160.0 mg, 0.46 mmol, 1.0 equiv.) in dichloromethane (20 mL) maintained under nitrogen at 0° C. was added diethylaminosulfur trifluoride (110 mg, 0.68 mmol, 1.5 equiv.). The resulting mixture was stirred at room temperature. for 2 h. The reaction was quenched with water (50 mL). The resulting mixture was extracted with DCM (3×50 mL). The organic layers were combined, dried over anhydrous sodium sulfate, filtered and concentrated. The resulting residue was purified by silica gel chromatography (0→35% ethyl acetate/petroleum ether) to yield the 1-(4-Chloro-3-fluoro-2-iodophenyl)-4-(difluoromethyl)-1H-1,2,3-triazole as a yellow solid. LCMS: mass calculated for $C_9H_4ClF_3IN_3$: 372.91, measured (ES, m/z): 374.00 $[M+H]^+$.

Step 6: 5-(3-Chloro-6-(4-(difluoromethyl)-1H-1,2,3-triazol-1-yl)-2-fluorophenyl)-2-(3-(difluoromethoxy)-1-(4-(1-methyl-1H-1,2,4-triazol-5-yl)-1H-pyrazol-1-yl)propyl)pyridine To a solution of (6-(3-(difluoromethoxy)-1-(4-(1-methyl-1H-1,2,4-triazol-5-yl)-1H-pyrazol-1-yl)propyl)pyridin-3-yl)boronic acid (200.0 mg, 0.53 mmol, 1.0 equiv.) in 1,4-dioxane (15.0 mL) was added 1-(4-chloro-3-fluoro-2-iodophenyl)-4-(difluoromethyl)-1H-1,2,3-triazole (197.5 mg, 0.53 mmol, 1.0 equiv.), tetrakis(triphenylphosphine)palladium (61.1 mg, 0.053 mmol, 0.1 equiv.) and potassium carbonate (109.6 mg, 0.79 mmol, 1.5 equiv.) and water (1.5 mL). The resulting mixture was maintained under nitrogen and stirred at 90° C. for 3 h. The reaction was quenched with water (50 mL). The resulting mixture was extracted with ethyl acetate (3×50 mL). The organic layers were combined, dried over anhydrous sodium sulfate, filtered and concentrated. The resulting residue was purified by silica gel chromatography (0→35% ethyl acetate/petroleum ether) to yield the 5-(3-chloro-6-(4-(difluoromethyl)-1H-1,2,3-triazol-1-yl)-2-fluorophenyl)-2-(3-(difluoromethoxy)-1-(4-(1-methyl-1H-1,2,4-triazol-5-yl)-1H-pyrazol-1-yl)propyl)pyridine as a yellow oil. LCMS: mass calculated for $C_{24}H_{19}ClF_5N_9O$: 579.13, measured (ES, m/z): 580.25 $[M+H]^+$.

Step 7: (S*)-5-(3-Chloro-6-(5-(difluoromethyl)-1H-1,2,3-triazol-1-yl)-2-fluorophenyl)-2-(3-(difluoromethoxy)-1-(4-(1-methyl-1H-1,2,4-triazol-5-yl)-1H-pyrazol-1-yl)propyl)pyridine 1-oxide To a solution of (5-(3-chloro-6-(4-(difluoromethyl)-1H-1,2,3-triazol-1-yl)-2-fluorophenyl)-2-(3-(difluoromethoxy)-1-(4-(1-methyl-1H-1,2,4-triazol-5-yl)-1H-pyrazol-1-yl)propyl)pyridine (180.0 mg, 0.31 mmol, 1.0 equiv.) in $CH_3OH$ (15.0 mL) was added hydrogen peroxide (2.0 mL, 30 wt %) and methyltrioxorhenium (VII) (7.7 mg, 0.031 mmol, 0.1 equiv.). The mixture was stirred at room temperature. for 1 h. The mixture was purified by silica gel chromatography with MeOH/DCM (0→10%) to yield the resulting residue, which was purified by chiral-HPLC with (mobile phase: MtBE(0.1% DEA):EtOH=70:30 to yield (S*)-5-(3-Chloro-6-(5-(difluoromethyl)-1H-1,2,3-triazol-1-yl)-2-fluorophenyl)-2-(3-(difluoromethoxy)-1-(4-(1-methyl-1H-1,2,4-triazol-5-yl)-1H-pyrazol-1-yl)propyl)pyridine 1-oxide as a white solid.

LC/MS: mass calculated for $C_{24}H_{19}ClF_5N_9O_2$: 595.13, measured (ES, m/z): 596.10 $[M+H]^+$. $^1H$ NMR (300 MHz, $CD_3OD$) δ 8.50 (t, J=1.5 Hz, 1H), 8.29-8.37 (m, 2H), 7.96 (s, 1H), 7.84-7.90 (m, 1H), 7.82 (s, 1H), 7.49-7.62 (m, 2H), 7.24-7.32 (m, 1H), 6.75-7.12 (m, 1H), 6.05-6.66 (m, 2H), 4.13 (s, 3H), 3.90-4.00 (m, 1H), 3.63-3.80 (m, 1H), 2.54-2.83 (m, 2H). $^{19}F$ NMR (282 MHz, $CD_3OD$) δ −86.14, −114.19, −114.78.

Example 840: (R)-5-(3-Chloro-6-(5-(difluoromethyl)-1H-1,2,3-triazol-1-yl)-2-fluorophenyl)-2-(3-(difluoromethoxy)-1-(4-(1-methyl-1H-1,2,4-triazol-5-yl)-1H-pyrazol-1-yl)propyl)pyridine 1-oxide

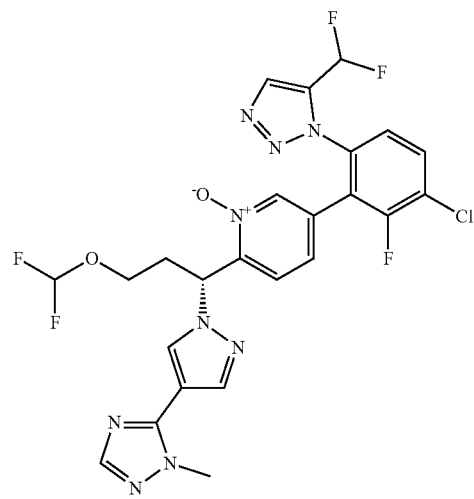

Step 1: 5-Bromo-2-(3-(difluoromethoxy)-1-(4-(1-methyl-1H-1,2,4-triazol-5-yl)-1H-pyrazol-1-yl)propyl)pyridine To a solution of 1-methyl-5-(1H-pyrazol-4-yl)-1H-1,2,4-triazole (360.0 mg, 2.41 mmol, 1.0 equiv.) and cesium carbonate (629.1 mg, 1.93 mmol, 0.8 equiv) in acetonitrile (15.0 mL) was added 1-(5-bromopyridin-2-yl)-3-(difluoromethoxy)propyl methanesulfonate (869.3 mg, 2.41 mmol, 1.0 equiv.). The resulting mixture was stirred at 70° C. for 2 h. The reaction was quenched with water (50 mL). The resulting mixture was extracted with ethyl acetate (3×50 mL). The organic layers were combined, dried over anhydrous sodium sulfate, filtered, and concentrated under reduced pressure. The resulting residue was purified by silica gel chromatography (0→10% DCM/MeOH) to yield the 5-bromo-2-(3-(difluoromethoxy)-1-(4-(1-methyl-1H-1,2,4-triazol-5-yl)-1H-pyrazol-1-yl)propyl)pyridine as a yellow oil. LCMS: mass calculated for $C_{15}H_{15}BrF_2N_6O$: 412.05, measured (ES, m/z): 413.10 $[M+H]^+$.

Step 2: (6-(3-(Difluoromethoxy)-1-(4-(1-methyl-1H-1,2,4-triazol-5-yl)-1H-pyrazol-1-yl)propyl)pyridin-3-yl)boronic acid To a solution of 5-bromo-2-(3-(difluoromethoxy)-1-(4-(1-methyl-1H-1,2,4-triazol-5-yl)-1H-pyrazol-1-yl)propyl)pyridine (900.0 mg, 2.18 mmol, 1.0 equiv.) in 1,4-dioxane (25.0 mL) was added 4,4,4',4',5,5,5',5'-octamethyl-2,2'-bi(1,3,2-dioxaborolane) (829.6 mg, 3.27 mmol, 1.5 equiv.) [1,1'-bis (diphenylphosphino)ferrocene]dichloropalladium(II) (160 mg, 0.22 mmol, 0.2 equiv.) and potassium acetate (320.6 mg, 3.27 mmol, 1.5 equiv.). The resulting mixture was maintained under nitrogen and stirred at 90° C. for 16 h. The reaction was quenched with water (50 mL). The resulting mixture was extracted with ethyl acetate (3×100 mL). The organic layers were combined, dried over anhydrous sodium sulfate, filtered, and concentrated to yield 800 mg dark oil. LCMS: mass calculated for $C_{15}H_{17}BF_2N_6O_3$: 378.14, measured (ES, m/z): 379.15 [M+H]$^+$.

Step 3: (1-(4-Chloro-3-fluoro-2-iodophenyl)-1H-1,2,3-triazol-4-yl)methanol

To a solution of 1-azido-4-chloro-3-fluoro-2-iodobenzene (1.0 g, 3.36 mmol, 1.0 equiv.) in toluene (20.0 mL) was added prop-2-yn-1-ol (565.4 mg, 10.09 mmol, 10.0 equiv.). The resulting mixture was stirred at 100° C. for 16 h. The mixture was concentrated under reduced pressure to yield ethyl 1-(4-Chloro-3-fluoro-2-iodophenyl)-1H-1,2,3-triazol-4-yl) methanol as a black solid. LC/MS: mass calculated For $C_9H_6ClFIN_3O$: 352.92, measured (ES, m/z): 353.9 [M+H]$^+$.

Step 4: 1-(4-Chloro-3-fluoro-2-iodophenyl)-1H-1,2,3-triazole-4-carbaldehyde

To a solution of (1-(4-chloro-3-fluoro-2-iodophenyl)-1H-1,2,3-triazol-4-yl)methanol (400.0 mg, 1.13 mmol, 1.0 equiv.) in dichloromethane (20.0 mL) was added Dess Martin reagent (719.9 mg, 1.70 mmol, 1.5 equiv.). The resulting mixture was stirred at room temperature for 2 h. The reaction was quenched with water (50 mL). The resulting mixture was extracted with DCM (3×50 mL). The organic layers were combined, dried over anhydrous sodium sulfate, filtered, and concentrated. The resulting residue was purified by silica gel chromatography (0→40% ethyl acetate/petroleum ether) to yield the 1-(4-chloro-3-fluoro-2-iodophenyl)-1H-1,2,3-triazole-4-carbaldehyde as a yellow oil. LCMS: mass calculated for $C_9H_4ClFIN_3O$: 350.91, measured (ES, m/z): 351.90 [M+H]$^+$.

Step 5: 1-(4-Chloro-3-fluoro-2-iodophenyl)-4-(difluoromethyl)-1H-1,2,3-triazole To a solution of 1-(4-chloro-3-fluoro-2-iodophenyl)-1H-1,2,3-triazole-4-carbaldehyde (160.0 mg, 0.46 mmol, 1.0 equiv.) in dichloromethane (20 mL) maintained under nitrogen at 0° C. was added diethylaminosulfur trifluoride (110 mg, 0.68 mmol, 1.5 equiv.). The resulting mixture was stirred at room temperature. for 2 h. The reaction was quenched with water (50 mL). The resulting mixture was extracted with DCM (3×50 mL). The organic layers were combined, dried over anhydrous sodium sulfate, filtered, and concentrated. The resulting residue was purified by silica gel chromatography (0→35% ethyl acetate/petroleum ether) to yield the 1-(4-Chloro-3-fluoro-2-iodophenyl)-4-(difluoromethyl)-1H-1,2,3-triazole as a yellow solid. LC/MS: mass calculated for $C_9H_4ClF_3IN_3$: 372.91, measured (ES, m/z): 374.00 [M+H]$^+$.

Step 6: 5-(3-Chloro-6-(4-(difluoromethyl)-1H-1,2,3-triazol-1-yl)-2-fluorophenyl)-2-(3-(difluoromethoxy)-1-(4-(1-methyl-1H-1,2,4-triazol-5-yl)-1H-pyrazol-1-yl)propyl)pyridine To a solution of (6-(3-(difluoromethoxy)-1-(4-(1-methyl-1H-1,2,4-triazol-5-yl)-1H-pyrazol-1-yl)propyl)pyridin-3-yl) boronic acid (200.0 mg, 0.53 mmol, 1.0 equiv.) in 1,4-dioxane (15.0 mL) was added 1-(4-chloro-3-fluoro-2-iodophenyl)-4-(difluoromethyl)-1H-1,2,3-triazole (197.5 mg, 0.53 mmol, 1.0 equiv.), tetrakis(triphenylphosphine) palladium (61 mg, 0.05 mmol, 0.1 equiv.) and potassium carbonate (109.6 mg, 0.79 mmol, 1.5 equiv.) and water (1.5 mL). The resulting mixture was maintained under nitrogen and stirred at 90° C. for 3 h. The reaction was quenched with water (50 mL). The resulting mixture was extracted with ethyl acetate (3×50 mL). The organic layers were combined, dried over anhydrous sodium sulfate, filtered, and concentrated under reduced pressure. The resulting residue was purified by silica gel chromatography (0→65% ethyl acetate/petroleum ether) to yield the 5-(3-chloro-6-(4-(difluoromethyl)-1H-1,2,3-triazol-1-yl)-2-fluorophenyl)-2-(3-(difluoromethoxy)-1-(4-(1-methyl-1H-1,2,4-triazol-5-yl)-1H-pyrazol-1-yl)propyl)pyridine as a yellow oil. LC/MS: mass calculated for $C_{24}H_{19}ClF_5N_9O$: 579.13, measured (ES, m/z): 580.25 [M+H]$^+$.

Step 7: (R)-5-(3-Chloro-6-(5-(difluoromethyl)-1H-1,2,3-triazol-1-yl)-2-fluorophenyl)-2-(3-(difluoromethoxy)-1-(4-(1-methyl-1H-1,2,4-triazol-5-yl)-1H-pyrazol-1-yl)propyl)pyridine 1-oxide To a solution of (5-(3-chloro-6-(4-(difluoromethyl)-1H-1,2,3-triazol-1-yl)-2-fluorophenyl)-2-(3-(difluoromethoxy)-1-(4-(1-methyl-1H-1,2,4-triazol-5-yl)-1H-pyrazol-1-yl)propyl)pyridine (180.0 mg, 0.31 mmol, 1.0 equiv.) in $CH_3OH$ (15.0 mL) was added hydrogen peroxide (2.0 mL, 30 wt %) and methyltrioxorhenium (VII) (7.7 mg, 0.031 mmol, 0.1 equiv.). The mixture was stirred at room temperature for 1 h. The mixture was purified by silica gel chromatography with MeOH/DCM (0→10%) to yield the resulting residue, which was purified by chiral-HPLC with (mobile phase: MtBE(0.1% DEA):EtOH=70:30 to yield (R)-5-(3-Chloro-6-(5-(difluoromethyl)-1H-1,2,3-triazol-1-yl)-2-fluorophenyl)-2-(3-(difluoromethoxy)-1-(4-(1-methyl-1H-1,2,4-triazol-5-yl)-1H-pyrazol-1-yl)propyl)pyridine 1-oxide as a white solid.

LC/MS: mass calculated for $C_{24}H_{19}ClF_5N_9O_2$: 595.13, measured (ES, m/z): 596.10 [M+H]$^+$. $^1$H NMR (300 MHz, $CD_3OD$) δ 8.50 (t, J=1.5 Hz, 1H), 8.29-8.37 (m, 2H), 7.96 (s, 1H), 7.84-7.90 (m, 1H), 7.82 (s, 1H), 7.49-7.62 (m, 2H), 7.24-7.32 (m, 1H), 6.75-7.12 (m, 1H), 6.05-6.66 (m, 2H), 4.13 (s, 3H), 3.90-4.00 (m, 1H), 3.63-3.80 (m, 1H), 2.54-2.83 (m, 2H). $^{19}$F NMR (282 MHz, $CD_3OD$) δ −86.14, −114.19, −114.78.

Example 841: (R*)-5-(3-Chloro-6-(4-(difluoromethyl)-1H-1,2,3-triazol-1-yl)-2-fluorophenyl)-2-(3-(difluoromethoxy)-1-(4-(1-methyl-1H-1,2,4-triazol-5-yl)-1H-pyrazol-1-yl)propyl)pyridine 1-oxide

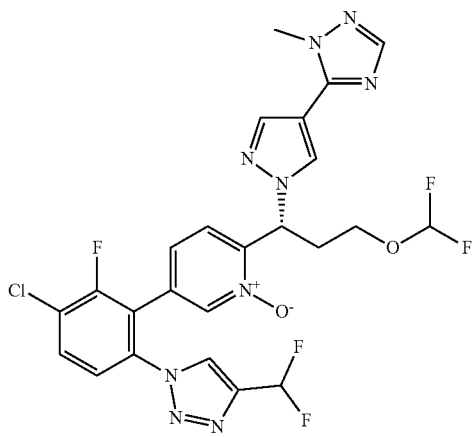 [SMILES: Cn1ncnc1-c1cnn([C@H](CCOC(F)F)c2ccc(-c3c(-n4cc(C(F)F)nn4)ccc(Cl)c3F)c[n+]2[O-])c1]

LC/MS: mass calculated for $C_{24}H_{19}ClF_5N_9O_2$: 595.13, measured (ES, m/z): 596.10 [M+H]$^+$. $^1$H NMR (300 MHz, CD$_3$OD) δ 8.52 (s, 1H), 8.30-8.38 (m, 2H), 7.80-7.98 (m, 3H), 7.58-7.64 (m, 2H), 7.22-7.31 (m, 1H), 6.70-7.10 (m, 1H), 6.10-6.60 (m, 2H), 4.15 (s, 3H), 3.92-4.03 (m, 1H), 3.72-3.81 (m, 1H), 2.65-2.84 (m, 2H). $^{19}$F NMR (300 MHz, CD$_3$OD) δ −76.95, −86.17, −114.20, −114.80.

Example 842: 5-(3-Chloro-2-fluoro-6-(4-(trifluoromethyl)-1H-1,2,3-triazol-1-yl)phenyl)-2-(3-(difluoromethoxy)-1-(4-(1-isopropyl-1H-1,2,3-triazol-5-yl)-1H-pyrazol-1-yl)propyl)pyridine 1-oxide

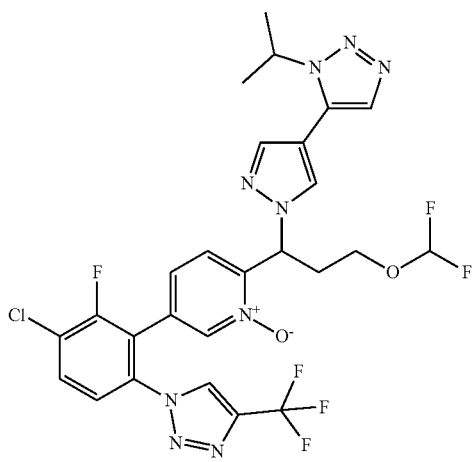 [SMILES: CC(C)n1nncc1-c1cnn(C(CCOC(F)F)c2ccc(-c3c(-n4cc(C(F)(F)F)nn4)ccc(Cl)c3F)c[n+]2[O-])c1]

LC/MS: mass calculated for $C_{26}H_{22}ClF_6N_9O_2$: 641.2, measured (ES, m/z): 642.1 [M+H]$^+$. $^1$H NMR (400 MHz, CD$_3$OD) δ ppm 1.55-1.62 (m, 6H) 2.64-2.72 (m, 1H) 2.74-2.86 (m, 1H) 3.64-3.79 (m, 1H) 3.93-4.05 (m, 1H) 4.84-4.88 (m, 1H) 6.15-6.58 (m, 2 h) 7.29-7.34 (m, 1H) 7.54-7.64 (m, 2 h) 7.81-7.95 (m, 3H) 8.26 (s, 1H) 8.38 (s, 1H) 8.80 (s, 1H).

Example 843: (S*)-5-(3-Chloro-2-fluoro-6-(1H-1,2,3-triazol-1-yl)phenyl)-2-(3-(difluoromethoxy)-1-(4-(1-(difluoromethyl)-1H-1,2,4-triazol-5-yl)-1H-pyrazol-1-yl)propyl)pyridine 1-oxide

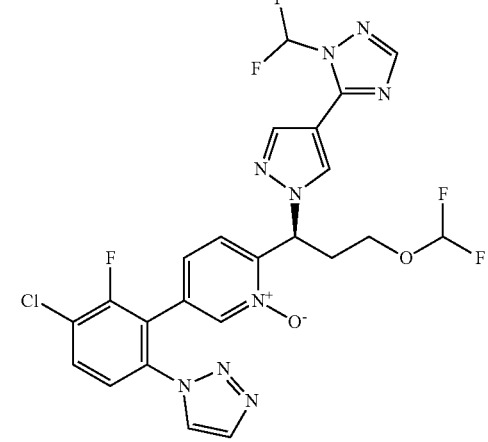

LC/MS: mass calculated for $C_{23}H_{17}ClF_5N_9O_2$: 581.11, measured (ES, m/z): 582.05 [M+H]$^+$. $^1$H NMR (300 MHz, CD$_3$OD) δ 9.21 (s, 1H), 8.94 (s, 1H), 8.55 (s, 1H), 8.01-8.31 (m, 3H), 7.60-8.01 (m, 5H), 6.15-6.65 (m, 2H), 3.97-4.13 (m, 1H), 3.72-3.87 (m, 1H), 2.67-3.01 (m, 2 h) $^{19}$F NMR (282 MHz, CD$_3$OD) δ −86.12, −97.82, −97.99, −113.74.

Example 844: (R)-5-(5-Chloro-2-(4-(trifluoromethyl)-1H-1,2,3-triazol-1-yl)phenyl)-2-(3-(difluoromethoxy)-1-(4-(1-methyl-1H-1,2,4-triazol-5-yl)-1H-pyrazol-1-yl)propyl)pyridine 1-oxide

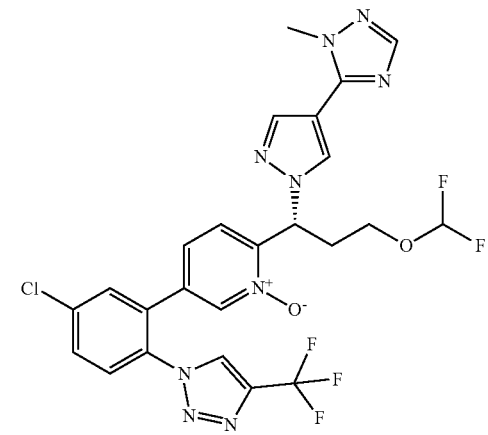 [SMILES: Cn1ncnc1-c1cnn([C@H](CCOC(F)F)c2ccc(-c3cc(Cl)ccc3-n3cc(C(F)(F)F)nn3)c[n+]2[O-])c1]

Step 1: 5-Bromo-2-(3-(difluoromethoxy)-1-(4-(1-methyl-1H-1,2,4-triazol-5-yl)-1H-pyrazol-1-yl)propyl)pyridine To a solution of 1-methyl-5-(1H-pyrazol-4-yl)-1H-1,2,4-triazole (1.4 g, 9.16 mmol, 1.1 equiv.) in acetonitrile (20 mL) was added cesium carbonate (3.0 g, 9.16 mmol, 1.1 equiv.). After the reaction mixture was stirred for 30 min, 1-(5-bromopyridin-2-yl)-3-(difluoromethoxy)propyl methanesulfonate (3.0 g, 8.33 mmol, 1.0 equiv.) was added. The reaction mixture was stirred at 80° C. for 2 h. The reaction mixture was cooled to room temperature and filtered. The filtrate was concentrated under vacuum. The residue was purified by silica gel chromatography (0→80% EA/PE) to yield 5-bromo-2-(3-(difluoromethoxy)-1-(4-(1-methyl-1H-1,2,4-triazol-5-yl)-1H-pyrazol-1-yl)propyl)pyridine as yellow solid. LC/MS: mass calculated for $C_{15}H_{15}BrF_2N_6O$: 412.05, measured (ES, m/z): 413.10 [M+H]$^+$.

Step 2: (6-(3-(Difluoromethoxy)-1-(4-(1-methyl-1H-1,2,4-triazol-5-yl)-1H-pyrazol-1-yl)propyl)pyridin-3-yl)boronic acid To a solution of 5-bromo-2-(3-(difluoromethoxy)-1-(4-(1-methyl-1H-1,2,4-triazol-5-yl)-1H-pyrazol-1-yl)propyl)pyridine (600 mg, 1.45 mmol, 1.0 equiv.) in 1,4-dioxane (30 mL) was added 4,4,4',4',5,5,5',5'-octamethyl-2,2'-bi(1,3,2-dioxaborolane) (664 mg, 2.61 mmol, 1.8 equiv.), potassium acetate (410 mg, 4.12 mmol, 3.0 equiv.) and Pd(dppf)Cl$_2$ (0.1 g, 0.14 mmol, 0.1 equiv.) under N$_2$. The mixture was stirred for 3 h at 100° C. The reaction was quenched with H$_2$O. The resulting mixture was extracted with EA twice. The organic layers were combined, dried over Na$_2$SO$_4$, filtered and concentrated to yield (6-(3-(difluoromethoxy)-1-(4-(1-methyl-1H-1,2,4-triazol-5-yl)-1H-pyrazol-1-yl)propyl)pyridin-3-yl)boronic acid as black oil. LC/MS: mass calculated for $C_{15}H_{17}BF_2N_6O_3$: 378.14, measured (ES, m/z): 379.20 [M+H]$^+$.

Step 3: 5-(5-Chloro-2-(4-(trifluoromethyl)-1H-1,2,3-triazol-1-yl)phenyl)-2-(3-(difluoromethoxy)-1-(4-(1-methyl-1H-1,2,4-triazol-5-yl)-1H-pyrazol-1-yl)propyl)pyridine To a solution of (6-(3-(difluoromethoxy)-1-(4-(1-methyl-1H-1,2,4-triazol-5-yl)-1H-pyrazol-1-yl)propyl)pyridin-3-yl)boronic acid (546 mg, resulting) in 1,4-dioxane (10 mL) and water (2 mL) was added 1-(2-bromo-4-chlorophenyl)-4-(trifluoromethyl)-1H-1,2,3-triazole (200 mg, 0.43 mmol, 1.0 equiv.), tetrakis(triphenylphosphine)palladium (58 mg, 0.05 mmol, 0.1 equiv.) and potassium carbonate (200 mg, 1.28 mmol, 3.0 equiv.) under N$_2$. The reaction mixture was stirred at 100° C. for 2 h. The reaction mixture was cooled to room temperature, water added, and the resulting mixture was extracted with ethyl acetate twice. The combined organic layers were dried over Na$_2$SO$_4$ and concentrated under vacuum. The residue was applied onto a silica gel column (20→80% EA/PE) to yield 5-(5-chloro-2-(4-(trifluoromethyl)-1H-1,2,3-triazol-1-yl)phenyl)-2-(3-(difluoromethoxy)-1-(4-(1-methyl-1H-1,2,4-triazol-5-yl)-1H-pyrazol-1-yl)propyl)pyridine as a brown solid. LC/MS: mass calculated for $C_{24}H_{19}ClF_5N_9O$: 579.13, measured (ES, m/z): 580.10 [M+H]$^+$.

Step 4: (R)-5-(5-Chloro-2-(4-(trifluoromethyl)-1H-1,2,3-triazol-1-yl)phenyl)-2-(3-(difluoromethoxy)-1-(4-(1-methyl-1H-1,2,4-triazol-5-yl)-1H-pyrazol-1-yl)propyl)pyridine 1-oxide To a solution of 5-(5-chloro-2-(4-(trifluoromethyl)-1H-1,2,3-triazol-1-yl)phenyl)-2-(3-(difluoromethoxy)-1-(4-(1-methyl-1H-1,2,4-triazol-5-yl)-1H-pyrazol-1-yl)propyl)pyridine (130 mg, 0.22 mmol, 1.0 equiv.) in MeOH (5 mL) was add methylrhenium (VII) trioxide (6 mg, 0.02 mmol, 0.1 equiv.) and hydrogen peroxide (30 wt %, 38 mg, 1.12 mmol, 5.0 equiv.). The reaction mixture was stirred 1 at room temperature, then purified by reverse column chromatography on C18 (80 g, MeCN/H$_2$O (0.05% CF$_3$COOH): 0→50%) to yield 5-(5-chloro-2-(4-(trifluoromethyl)-1H-1,2,3-triazol-1-yl)phenyl)-2-(3-(difluoromethoxy)-1-(4-(1-methyl-1H-1,2,4-triazol-5-yl)-1H-pyrazol-1-yl)propyl)pyridine 1-oxide as a white solid. The racemic mixture was purified by Prep-Chiral-HPLC with (Hex:DCM=3:1)(0.1% DEA):EtOH=50:50 to yield (R)-5-(5-chloro-2-(4-(trifluoromethyl)-1H-1,2,3-triazol-1-yl)phenyl)-2-(3-(difluoromethoxy)-1-(4-(1-methyl-1H-1,2,4-triazol-5-yl)-1H-pyrazol-1-yl)propyl)pyridine 1-oxide as a white solid.

LC/MS: mass calculated for $C_{24}H_{19}ClF_5N_9O_2$: 595.13, measured (ES, m/z): 618.00 [M+Na]$^+$. $^1$H NMR (300 MHz, CD$_3$OD) δ 8.80 (s, 1H), 8.48 (s, 1H), 8.29 (s, 1H), 8.10 (s, 1H), 7.93 (s, 1H), 7.68-7.85 (m, 3H), 7.53 (d, J=8.3 Hz, 1H), 7.15-7.27 (m, 1H), 6.08-6.72 (m, 2H), 3.95-4.03 (m, 4H), 3.76-3.85 (m, 1H), 2.61-2.91 (m, 2H). $^{19}$F NMR (282 MHz, CD$_3$OD) δ −62.66, −86.10.

Example 845: (R*)-5-(3-Chloro-2-fluoro-6-(1H-1,2,3-triazol-1-yl)phenyl)-2-(3-(difluoromethoxy)-1-(4-(1-(difluoromethyl)-1H-1,2,4-triazol-5-yl)-1H-pyrazol-1-yl)propyl)pyridine 1-oxide

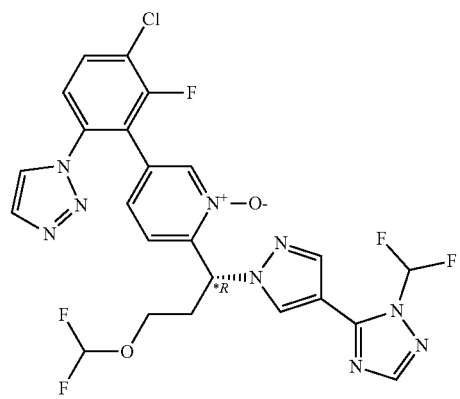 [SMILES: [O-][n+]1cc(-c2c(-n3ccnn3)ccc(Cl)c2F)ccc1[C@@H](CCOC(F)F)n1cc(-c2ncnn2C(F)F)cn1]

LC/MS: mass calculated for $C_{23}H_{17}ClF_5N_9O_2$: 581.1, measured (ES, m/z): 582.1 [M+H]$^+$. $^1$H NMR (300 MHz, CD$_3$OD) δ 9.20 (s, 1H), 8.96 (s, 1H), 8.55 (s, 1H), 8.06-8.16 (m, 3H), 7.92-7.99 (m, 1H), 7.56-7.85 (m, 4H), 6.13-6.71 (m, 2H), 3.98-4.13 (m, 1H), 3.65-3.87 (m, 1H), 3.00-3.68 (m, 2H)$^{19}$F NMR (282 MHz, CD$_3$OD) δ −86.12, −97.82, −97.99, −113.74.

Example 846: (S)-5-(5-Chloro-2-(4-(trifluoromethyl)-1H-1,2,3-triazol-1-yl)phenyl)-2-(3-(difluoromethoxy)-1-(4-(1-methyl-1H-1,2,4-triazol-5-yl)-1H-pyrazol-1-yl)propyl)pyridine 1-oxide

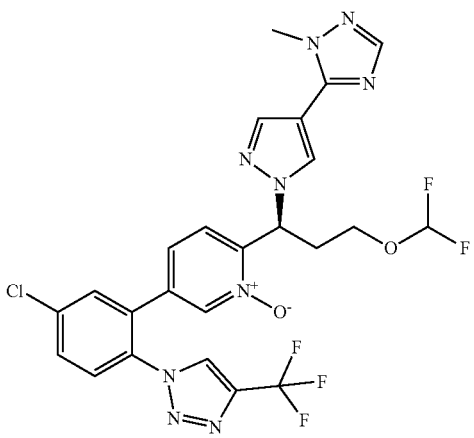 [SMILES: Cn1ncnc1-c1cnn([C@@H](CCOC(F)F)c2ccc(-c3cc(Cl)ccc3-n3cc(C(F)(F)F)nn3)c[n+]2[O-])c1]

LC/MS: mass calculated for $C_{24}H_{19}ClF_5N_9O_2$: 595.13, measured (ES, m/z): 618.00 [M+Na]$^+$. $^1$H NMR (300 MHz, CD$_3$OD) δ 8.77-8.83 (m, 1H), 8.49 (d, J=0.8 Hz, 1H), 8.29 (d, J=1.7 Hz, 1H), 8.10 (s, 1H), 7.93 (s, 1H), 7.70-8.83 (m, 3H), 7.51-7.57 (m, 1H), 7.20-7.25 (m, 1H), 6.10-6.65 (m, 2H), 3.94-4.08 (m, 4H), 3.68-3.82 (m, 1H), 2.62-2.91 (m, 2H). $^{19}$F NMR (282 MHz, CD$_3$OD) δ −62.67, −86.10, −86.14.

Example 847: (S*)-5-(3-chloro-2-fluoro-6-(1H-tetrazol-1-yl)phenyl)-2-(3-(difluoromethoxy)-1-(4-(1-(difluoromethyl)-1H-imidazol-5-yl)-1H-pyrazol-1-yl)propyl)pyridine 1-oxide

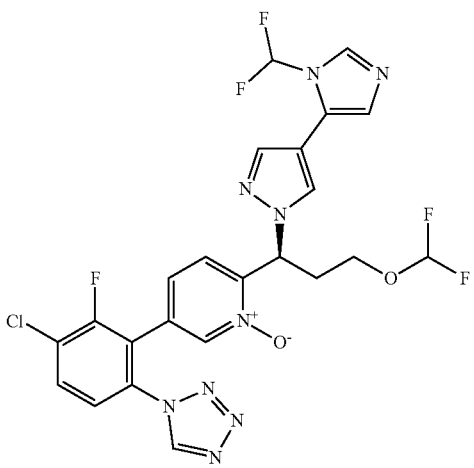 [SMILES: [O-][n+]1cc(-c2c(-n3cnnn3)ccc(Cl)c2F)ccc1[C@H](CCOC(F)F)n1cc(-c2cncn2C(F)F)cn1]

Step 1: 5-Bromo-2-(3-(difluoromethoxy)-1-(4-(1-(difluoromethyl)-1H-imidazol-5-yl)-1H-pyrazol-1-yl)propyl)pyridine To a solution of 4-(1-(difluoromethyl)-1H-imidazol-5-yl)-1H-pyrazole (320 mg, 1.74 mmol, 1.0 equiv.) in CH$_3$CN (5 mL) was added cesium carbonate (566.2 mg, 1.74 mmol, 1.0 equiv.). The resulting mixture was stirred at 25° C. for 0.5 h. To the reaction was added 1-(5-bromopyridin-2-yl)-3-(difluoromethoxy)propyl methanesulfonate (668.5 mg, 1.91 mmol, 1.1 equiv.). The resulting mixture was stirred at 80° C. for 2 hrs. The mixture was filtered and concentrated under vacuum. The resulting residue was purified by silica gel chromatography (40450% ethyl acetate/petroleum ether) to yield 5-bromo-2-(3-(difluoromethoxy)-1-(4-(1-(difluoromethyl)-1H-imidazol-5-yl)-1H-pyrazol-1-yl)propyl)pyridine as a yellow oil. LC/MS: mass calculated for $C_{16}H_{14}BrF_4N_5O$: 447.03, measured (ES, m/z): 450.05 [M+H+2]$^+$.

Step 2: 4-Chloro-2-(6-(3-(difluoromethoxy)-1-(4-(1-(difluoromethyl)-1H-imidazol-5-yl)-1H-pyrazol-1-yl)propyl)pyridin-3-yl)-3-fluoroaniline To a solution of 5-bromo-2-(3-(difluoromethoxy)-1-(4-(1-(difluoromethyl)-1H-imidazol-5-yl)-1H-pyrazol-1-yl)propyl)pyridine (470 mg, 1.05 mmol, 1.0 equiv.) in 1,4-dioxane (5 mL) and water (0.5 mL) was added (6-amino-3-chloro-2-fluorophenyl)boronic acid (238.3 mg, 1.26 mmol, 1.2 equiv.), potassium carbonate (434.8 mg, 3.15 mmol, 3.0 equiv) and tetrakis(triphenylphosphine)palladium (60.6 mg, 0.05 mmol, 0.05 equiv.). The resulting mixture was maintained under nitrogen and stirred at 100° C. for 2 hrs. The mixture was filtered and concentrated. The resulting residue was purified by silica gel chromatography (60470% ethyl acetate/petroleum ether) to yield 4-chloro-2-(6-(3-(difluoromethoxy)-1-(4-(1-(difluoromethyl)-1H-imidazol-5-yl)-1H-pyrazol-1-yl)propyl)pyridin-3-yl)-3-fluoroaniline. LC/MS: mass calculated for $C_{22}H_{18}ClF_5N_6O$: 512.12, measured (ES, m/z): 513.20 [M+H]$^+$.

Step 3: 5-(3-Chloro-2-fluoro-6-(1H-tetrazol-1-yl)phenyl)-2-(3-(difluoromethoxy)-1-(4-(1-(difluoromethyl)-1H-imidazol-5-yl)-1H-pyrazol-1-yl)propyl)pyridine To a solution of 4-chloro-2-(6-(3-(difluoromethoxy)-1-(4-(1-(difluoromethyl)-1H-imidazol-5-yl)-1H-pyrazol-1-yl)propyl)pyridin-3-yl)-3-fluoroaniline (530 mg, 1.03 mmol, 1.0 equiv.) in acetic acid (2 mL) was added azidotrimethylsilane (1 mL) and trimethoxymethane (1 mL). The resulting mixture was stirred overnight at 25° C. The mixture was concentrated under vacuum. The resulting residue was purified by reverse-phase chromatography with CH$_3$CN/H$_2$O (0.05% TFA) (40450%) to yield 5-(3-chloro-2-fluoro-6-(1H-tetrazol-1-yl)phenyl)-2-(3-(difluoromethoxy)-1-(4-(1-(difluoromethyl)-1H-imidazol-5-yl)-1H-pyrazol-1-yl)propyl)pyridine as a yellow solid. LC/MS: mass calculated for $C_{23}H_{17}ClF_5N_9O$: 565.12, measured (ES, m/z): 566.20 [M+H]$^+$.

Step 4: (S*)-5-(3-Chloro-2-fluoro-6-(1H-tetrazol-1-yl)phenyl)-2-(3-(difluoromethoxy)-1-(4-(1-(difluoromethyl)-1H-imidazol-5-yl)-1H-pyrazol-1-yl)propyl)pyridine 1-oxide To a solution of 5-(3-chloro-2-fluoro-6-(1H-tetrazol-1-yl)phenyl)-2-(3-(difluoromethoxy)-1-(4-(1-(difluoromethyl)-1H-imidazol-5-yl)-1H-pyrazol-1-yl)propyl)pyridine (480 mg, 0.85 mmol, 1.0 equiv.) in DCM (5 mL) was added 3-chloroperoxybenzoic acid (585.5 mg, 3.39 mmol, 4.0 equiv.). The resulting mixture was stirred at 25° C. for 2 h, then concentrated under vacuum. The residue was purified by reverse-phase chromatography with CH$_3$CN/H$_2$O (0.05% TFA)(35→40%) to yield the resulting residue which was purified by chiral-HPLC with (Hex:DCM=3:1)(0.1% DEA):EtOH=50:50 to yield (S*)-5-(3-chloro-2-fluoro-6-(1H-tetrazol-1-yl)phenyl)-2-(3-(difluoromethoxy)-1-(4-(1-(difluoromethyl)-1H-imidazol-5-yl)-1H-pyrazol-1-yl)propyl)pyridine 1-oxide as a white solid.

LC/MS: mass calculated for C$_{23}$H$_{17}$ClF$_5$N$_9$O$_2$: 581.11, measured (ES, m/z): 582.05 [M+H]$^+$. $^1$H NMR (400 MHz, CD$_3$OD) δ 9.39 (s, 1H), 8.40 (s, 1H), 8.29 (s, 1H), 7.91-7.97 (m, 2H), 7.53-7.70 (m, 4H), 7.30-7.32 (m, 1H), 7.15 (s, 1H), 6.15-6.55 (m, 2H), 3.96-4.01 (m, 1H), 3.71-3.77 (m, 1H), 2.76-2.85 (m, 1H), 2.65-2.73 (m, 1H). $^{19}$F NMR (376 MHz, CD$_3$OD) δ −86.16, −94.12, −113.68.

Example 848: (R)-5-(6-amino-3-chloro-2-fluorophenyl)-2-(3-(difluoromethoxy)-1-(4-(1-methyl-1H-1,2,4-triazol-5-yl)-1H-pyrazol-1-yl)propyl)pyridine 1-oxide

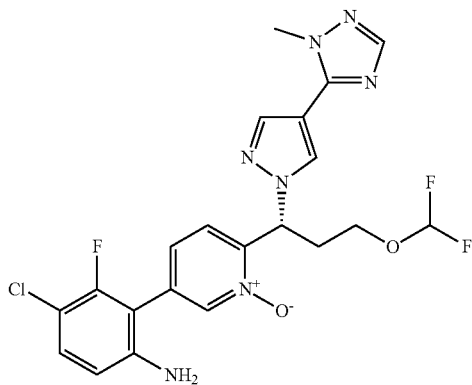 [SMILES: Cn1ncnc1-c1cnn([C@H](CCOC(F)F)c2ccc(-c3c(N)ccc(Cl)c3F)c[n+]2[O-])c1]

LC/MS: mass calculated for C$_{21}$H$_{19}$ClF$_3$N$_7$O$_2$: 493.12, measured (ES, m/z): 494.05 [M+H]$^+$. $^1$H NMR (400 MHz, DMSO-d$_6$) δ 8.64 (s, 1H), 8.32 (s, 1H), 8.14 (s, 1H), 7.91 (s, 1H), 7.41 (d, J=8.2 Hz, 1H), 7.34 (d, J=8.3 Hz, 1H), 7.24 (t, J=8.7 Hz, 1H), 6.86 (t, J=76.0 Hz, 1H), 6.58 (d, J=8.3 Hz, 1H), 6.34-6.37 (m, 1H), 5.50 (s, 2H), 3.98 (s, 3H), 3.86-3.96 (m, 1H), 3.73-3.79 (m, 1H), 2.58-2.82 (m, 2H). $^{19}$F NMR (376 MHz, DMSO-d$_6$) δ −83.10, −83.12, −118.24, −218.26.

Example 849: (S)-5-(3-Chloro-6-(4-chloro-1H-1,2,3-triazol-1-yl)-2-fluorophenyl)-2-(1-(4-(cyclopropanecarboxamido)-2-(methyl-d3)-1'H,2H-[3,4'-bipyrazol]-1'-yl)-3-(difluoromethoxy)propyl)pyridine 1-oxide

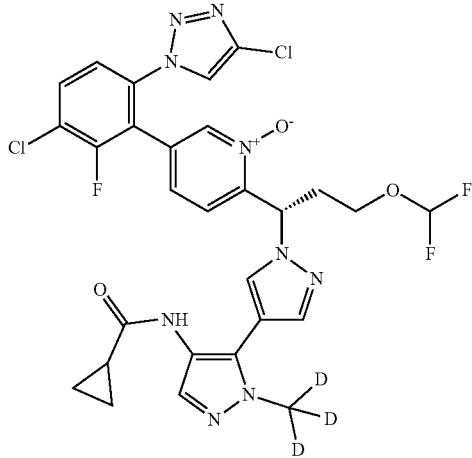 [SMILES: [2H]C([2H])([2H])n1ncc(NC(=O)C2CC2)c1-c1cnn([C@@H](CCOC(F)F)c2ccc(-c3c(-n4cc(Cl)nn4)ccc(Cl)c3F)c[n+]2[O-])c1]

LC/MS: mass calculated for C$_{28}$H$_{21}$Cl$_2$D$_3$F$_3$N$_9$O$_3$: 664.15, measured (ES, m/z): 665.05 [M+H]$^+$. $^1$H NMR (400 MHz, DMSO-d$_6$) δ 9.36 (s, 1H), 8.68 (s, 1H), 8.43 (d, J=1.7 Hz, 1H), 8.32 (s, 1H), 7.98-8.07 (m, 1H), 7.84 (s, 1H), 7.68-7.71 (m, 1H), 7.50 (s, 1H), 7.34-7.39 (m, 1H), 7.18-7.21 (m, 1H), 6.63 (t, J=75.7 Hz, 1H), 6.22-6.28 (m, 1H), 3.82-3.90 (m, 1H), 3.63-3.74 (m, 1H), 2.56-2.70 (m, 2H), 1.72-1.80 (m, 1H), 0.69-0.78 (m, 4H). $^{19}$F NMR (376 MHz, DMSO-d$_6$) δ −83.19, −112.92.

Example 850: (S*)-5-(3-Chloro-6-(4-chloro-1H-1,2,3-triazol-1-yl)-2-fluorophenyl)-2-(1-(4-(cyclopropanecarboxamido)-2-(methyl-d3)-1'H,2H-[3,4'-bipyrazol]-1'-yl)-3-(difluoromethoxy)propyl)pyridine 1-oxide

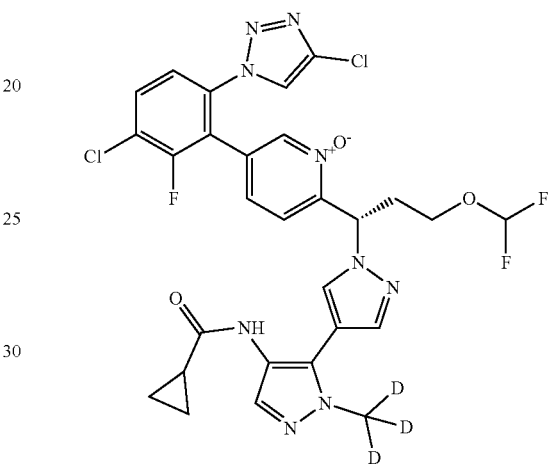

LC/MS: mass calculated for C$_{28}$H$_{21}$Cl$_2$D$_3$F$_3$N$_9$O$_3$: 664.15, measured (ES, m/z): 665.05 [M+H]$^+$. $^1$H NMR (400 MHz, DMSO-d$_6$) δ 9.36 (s, 1H), 8.68 (s, 1H), 8.43 (d, J=1.6 Hz, 1H), 8.32 (s, 1H), 8.00-8.07 (m, 1H), 7.84 (s, 1H), 7.67-7.71 (m, 1H), 7.50 (s, 1H), 7.34-7.39 (m, 1H), 7.16-7.22 (m, 1H), 6.63 (t, J=75.7 Hz, 1H), 6.21-6.29 (m, 1H), 3.81-3.90 (m, 1H), 3.64-3.74 (m, 1H), 2.55-2.70 (m, 2H), 1.71-1.80 (m, 1H), 0.66-0.78 (m, 4H). $^{19}$F NMR (376 MHz, DMSO-d$_6$) δ −73.43, −83.19, −112.92.

Example 851: (R*)-5-(3-Chloro-2-fluoro-6-(4-(trifluoromethyl)-1H-1,2,3-triazol-1-yl)phenyl)-2-(3-hydroxy-1-(4-(1-methyl-1H-1,2,4-triazol-5-yl)-1H-pyrazol-1-yl)propyl)pyridine 1-oxide

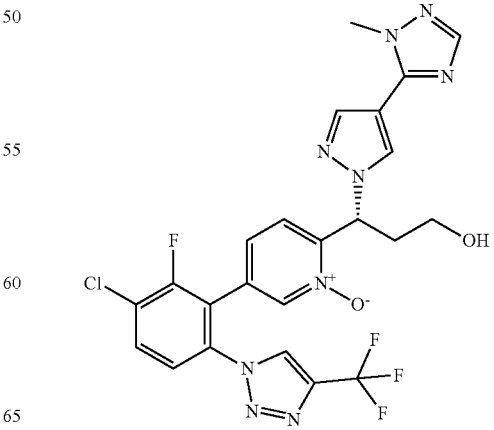

LC/MS: mass calculated for $C_{23}H_{18}ClF_4N_9O_2$: 563.12, measured (ES, m/z): 564.10 [M+H]$^+$. $^1$H NMR (400 MHz, DMSO-d$_6$) δ 9.12 (d, J=1.0 Hz, 1H), 8.53 (d, J=0.8 Hz, 1H), 8.39 (d, J=1.6 Hz, 1H), 7.98-8.07 (m, 2H), 7.89 (s, 1H), 7.73-7.78 (m, 1H), 7.40-7.45 (m, 1H), 7.15-7.20 (m, 1H), 6.28-6.32 (m, 1H), 3.95 (s, 3H), 3.33-3.43 (m, 1H), 3.18-3.29 (m, 1H), 2.39-2.51 (m, 1H), 2.25-2.37 (m, 1H). $^{19}$F NMR (376 MHz, DMSO-d$_6$) δ −59.77, −59.80, −73.61, −73.67, −112.97.

Example 852: (S*)-5-(6-amino-3-chloro-2-fluorophenyl)-2-(3-(difluoromethoxy)-1-(4-(1-methyl-1H-1,2,4-triazol-5-yl)-1H-pyrazol-1-yl)propyl)pyridine 1-oxide

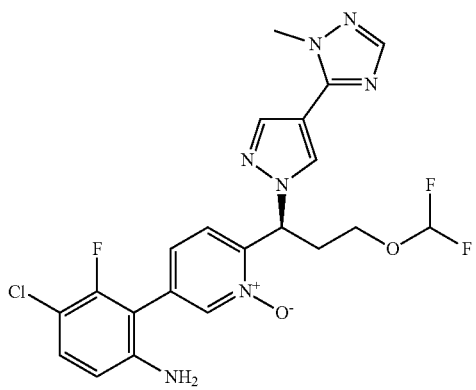

LC/MS: mass calculated for $C_{21}H_{19}ClF_3N_7O_2$: 493.12, measured (ES, m/z): 494.05 [M+H]$^+$. $^1$H NMR (400 MHz, DMSO-d$_6$) δ 8.64 (s, 1H), 8.32 (s, 1H), 8.14 (s, 1H), 7.91 (s, 1H), 7.41 (d, J=8.2 Hz, 1H), 7.34 (d, J=8.3 Hz, 1H), 7.24 (t, J=8.7 Hz, 1H), 6.86 (t, J=76.0 Hz, 1H), 6.58 (d, J=8.3 Hz, 1H), 6.34-6.37 (m, 1H), 5.50 (s, 2H), 3.98 (s, 3H), 3.86-3.96 (m, 1H), 3.73-3.79 (m, 1H), 2.58-2.82 (m, 2H). $^{19}$F NMR (376 MHz, DMSO-d$_6$) δ −83.10, −83.12, −118.24, −218.26.

Example 853: (S*)-5-(3-Chloro-2-fluoro-6-(4-(trifluoromethyl)-1H-1,2,3-triazol-1-yl)phenyl)-2-(3-(difluoromethoxy)-1-(3-(1-methyl-1H-1,2,4-triazol-5-yl)-1H-pyrazol-1-yl)propyl)pyridine 1-oxide

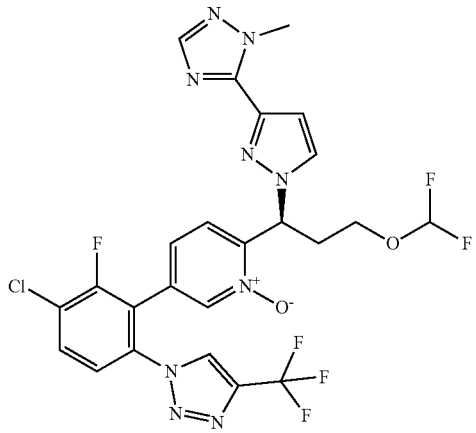 [SMILES: Cn1ncnc1-c1ccn([C@@H](CCOC(F)F)c2ccc(-c3c(-n4cc(C(F)(F)F)nn4)ccc(Cl)c3F)c[n+]2[O-])n1]

LC/MS: mass calculated for $C_{24}H_{18}ClF_6N_9O_2$: 613.1, measured (ES, m/z): 614.1 [M+H]$^+$. $^1$H NMR (400 MHz, DMSO-d$_6$) δ 9.15-9.20 (m, 1H), 8.46 (s, 1H), 8.14 (d, J=2.4 Hz, 1H), 8.02-8.10 (m, 1H), 7.96 (s, 1H), 7.75-7.80 (m, 1H), 7.32-7.37 (m, 1H), 7.10-7.15 (m, 1H), 6.43-6.83 (m, 2H), 6.26-6.32 (m, 1H), 4.09 (s, 3H), 3.82-3.90 (m, 1H), 3.68-3.78 (m, 1H), 2.61-2.74 (m, 2H). $^{19}$F NMR (376 MHz, DMSO-d$_6$) δ −59.88, −83.32, −112.87.

Example 854: (R*)-5-(3-Chloro-2-fluoro-6-(4-(trifluoromethyl)-1H-1,2,3-triazol-1-yl)phenyl)-2-(3-(difluoromethoxy)-1-(3-(1-methyl-1H-1,2,4-triazol-5-yl)-1H-pyrazol-1-yl)propyl)pyridine 1-oxide

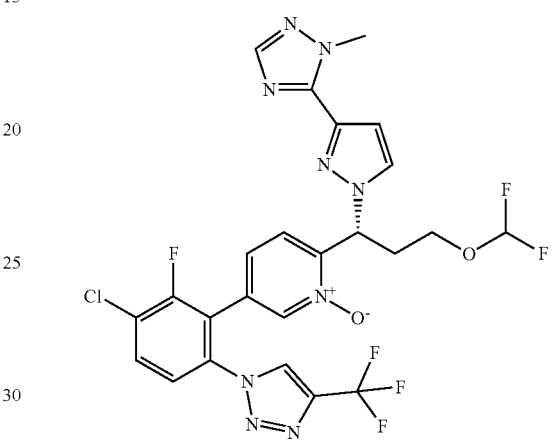

LC/MS: mass calculated for $C_{24}H_{18}ClF_6N_9O_2$: 613.12, measured (ES, m/z): 614.15 [M+H]$^+$. $^1$H NMR (400 MHz, DMSO-d$_6$) δ 9.18 (d, J=1.0 Hz, 1H), 8.46 (d, J=1.6 Hz, 1H), 8.14 (d, J=2.4 Hz, 1H), 8.02-8.10 (m, 1H), 7.97 (s, 1H), 7.75-7.80 (m, 1H), 7.30-7.38 (m, 1H), 7.10-7.15 (m, 1H), 6.43-6.83 (m, 2H), 6.27-6.31 (m, 1H), 4.09 (s, 3H), 3.81-3.90 (m, 1H), 3.69-3.77 (m, 1H), 2.55-2.74 (m, 2H). $^{19}$F NMR (376 MHz, DMSO-d$_6$) δ −59.88, −83.32, −112.86.

Example 855: (S)-5-(3-Chloro-2-fluoro-6-(4-(trifluoromethyl)-1H-1,2,3-triazol-1-yl)phenyl)-2-(2-(1-(difluoromethyl)-1H-pyrazol-3-yl)-1-(4-(1-methyl-1H-1,2,4-triazol-5-yl)-1H-pyrazol-1-yl)ethyl)pyridine 1-oxide

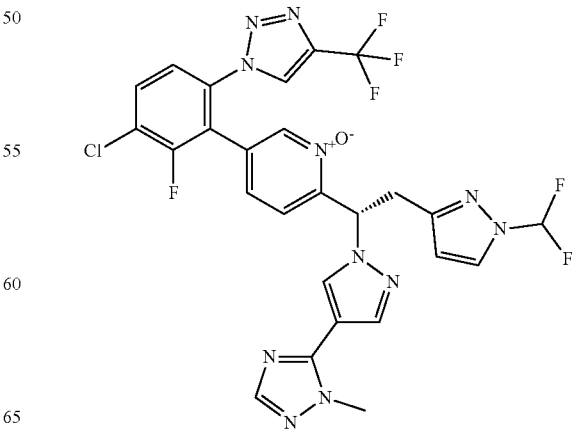

LC/MS: mass calculated for $C_{2H}H_{18}ClF_6N_{11}O$: 649.13, measured (ES, m/z): 650.10 [M+H]⁺. ¹H NMR (300 MHz, CD₃OD) δ 8.82 (s, 1H), 8.31-8.51 (m, 2H), 8.05 (s, 1H), 7.85-7.98 (m, 3H), 7.59-7.68 (m, 2H), 7.29-7.58 (m, 2H), 6.60-6.69 (m, 1H), 6.24 (d, J=2.7 Hz, 1H), 3.98 (s, 3H), 3.71-3.92 (m, 2H). ¹⁹F NMR (282 MHz, CD₃OD) δ −62.69, −96.05, −113.93.

Example 856: (R)-5-(3-Chloro-2-fluoro-6-(4-(trifluoromethyl)-1H-1,2,3-triazol-1-yl) phenyl)-2-(2-(1-(difluoromethyl)-1H-pyrazol-3-yl)-1-(4-(1-methyl-1H-1,2,4-triazol-5-yl)-1H-pyrazol-1-yl)ethyl) pyridine 1-oxide

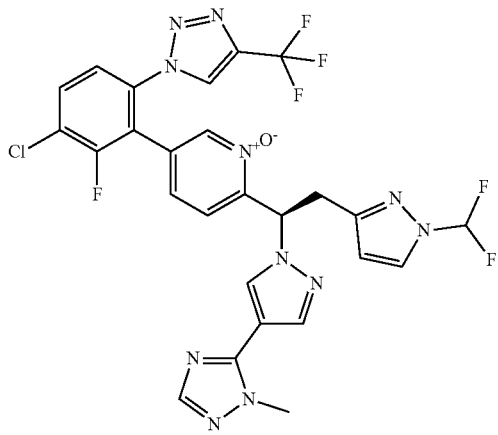

Step 1: 5-Bromo-2-((4-(1-methyl-1H-1,2,4-triazol-5-yl)-1H-pyrazol-1-yl)methyl)pyridine To a solution of 1-methyl-5-(1H-pyrazol-4-yl)-1H-1,2,4-triazole (1.0 g, 6.7 mmol, 1.0 equiv.) in ACN (20 mL) was added cesium carbonate (3.2 g, 10.1 mmol, 1.5 equiv.). The mixture was stirred for 0.5 h at room temperature. 5-Bromo-2-(bromomethyl)pyridine (2.0 g, 8.1 mmol, 1.2 equiv.) was added. The mixture was stirred for 2 h at 70° C., then concentrated under vacuum. The residue was purified by silica gel chromatography (0→20% MeOH/DCM) to yield 5-bromo-2-((4-(1-methyl-1H-1,2,4-triazol-5-yl)-1H-pyrazol-1-yl)methyl)pyridine as a yellow solid. LC/MS: mass calculated for $C_{12}H_{11}BrN_6$: 318.02, measured (ES, m/z): 319.05 [M+H]⁺.

Step 2: 5-Bromo-2-(2-(1-(difluoromethyl)-1H-pyrazol-3-yl)-1-(4-(1-methyl-1H-1,2,4-triazol-5-yl)-1H-pyrazol-1-yl)ethyl)pyridine To a solution of 5-bromo-2-((4-(1-methyl-1H-1,2,4-triazol-5-yl)-1H-pyrazol-1-yl)methyl)pyridine (800 mg, 2.51 mmol, 1.0 equiv.) in THF (15 mL) was added LDA (2M in THF, 1.32 ml, 2.64 mmol, 1.05 equiv.) under nitrogen at −78° C. The mixture was stirred for 0.5 h, then 3-(bromomethyl)-1-(difluoromethyl)-1H-pyrazole (634 mg, 3.01 mmol, 1.2 equiv.) was added. The mixture was stirred at −78° C. for 1 h, then quenched with saturated NH₄Cl, extracted with EA twice. The combined organic layers were dried over Na₂SO₄ and concentrated under vacuum. The residue was purified by silica gel chromatography with (0→30% PE/EA) to yield 5-bromo-2-(2-(1-(difluoromethyl)-1H-pyrazol-3-yl)-1-(4-(1-methyl-1H-1,2,4-triazol-5-yl)-1H-pyrazol-1-yl)ethyl) pyridine as a yellow solid. LC/MS: mass calculated for $C_{17}H_{15}BrF_2N_8$: 448.06, measured (ES, m/z):449.10 [M+H]⁺.

Step 3: 2-(2-(1-(Difluoromethyl)-1H-pyrazol-3-yl)-1-(4-(1-methyl-1H-1,2,4-triazol-5-yl)-1H-pyrazol-1-yl)ethyl)-5-(4,4,5,5-tetramethyl-1,3,2-dioxaborolan-2-yl)pyridine To a solution of 5-bromo-2-(2-(1-(difluoromethyl)-1H-pyrazol-3-yl)-1-(4-(1-methyl-1H-1,2,4-triazol-5-yl)-1H-pyrazol-1-yl)ethyl)pyridine (300 mg, 0.60 mmol, 1.0 equiv.) in 1,4-dioxane (10 mL) was added 4,4,4',4',5,5,5',5'-octamethyl-2,2'-bi(1,3,2-dioxaborolane) (300 mg, 1.20 mmol, 2.0 equiv.), KOAc (180 mg, 1.80 mmol, 3.0 equiv.) and Pd(dppf)Cl₂ (44 mg, 0.06 mmol, 0.1 equiv.) under N₂. The mixture was stirred for 3 h at 100° C. The reaction was quenched with H₂O. The resulting mixture was extracted with EA. The organic layers were combined, dried over Na₂SO₄, filtered and concentrated. To yield 2-(2-(1-(difluoromethyl)-1H-pyrazol-3-yl)-1-(4-(1-methyl-1H-1,2,4-triazol-5-yl)-1H-pyrazol-1-yl)ethyl)-5-(4,4,5,5-tetramethyl-1,3,2-dioxaborolan-2-yl)pyridine as a brown solid. LC/MS: mass calculated for $C_{23}H_{27}BF_2N_8O_2$: 496.23, measured (ES, m/z): 496.25 [M+H]⁺.

Step 4: 5-(3-Chloro-2-fluoro-6-(4-(trifluoromethyl)-1H-1,2,3-triazol-1-yl) phenyl)-2-(2-(1-(difluoromethyl)-1H-pyrazol-3-yl)-1-(4-(1-methyl-1H-1,2,4-triazol-5-yl)-1H-pyrazol-1-yl)ethyl)pyridine To a solution of 4-chloro-1-(4-chloro-3-fluoro-2-iodophenyl)-1H-1,2,3-triazole (200 mg, 0.51 mmol, 1.0 equiv.) in 1,4-dioxane (20 mL) and water (4 mL) was added 2-(2-(1-(difluoromethyl)-1H-pyrazol-3-yl)-1-(4-(1-methyl-1H-1,2,4-triazol-5-yl)-1H-pyrazol-1-yl)ethyl)-5-(4,4,5,5-tetramethyl-1,3,2-dioxaborolan-2-yl)pyridine (585 mg, resulting) and potassium carbonate (211 mg, 1.53 mmol, 3.0 equiv.) and tetrakis(triphenylphosphine)palladium(0) (59 mg, 0.05 mmol, 0.1 equiv.). The reaction mixture was maintained under nitrogen and stirred at 100° C. for 2 h. The reaction was quenched with H₂O. The resulting mixture was extracted with EA. The organic layers were combined, dried over Na₂SO₄, filtered and concentrated. The residue was purified by silica gel chromatography (10→80% EA/PE) to yield 5-(3-chloro-2-fluoro-6-(4-(trifluoromethyl)-1H-1,2,3-triazol-1-yl)phenyl)-2-(2-(1-(difluoromethyl)-1H-pyrazol-3-yl)-1-(4-(1-methyl-1H-1,2,4-triazol-5-yl)-1H-pyrazol-1-yl)ethyl)pyridine as a brown solid. LC/MS: mass calculated for $C_{2H}H_{18}ClF_6N_{11}$: 633.13, measured (ES, m/z): 634.30 [M+H]⁺.

Step 5: (R)-5-(3-Chloro-2-fluoro-6-(4-(trifluoromethyl)-1H-1,2,3-triazol-1-yl)phenyl)-2-(2-(1-(difluoromethyl)-1H-pyrazol-3-yl)-1-(4-(1-methyl-1H-1,2,4-triazol-5-yl)-1H-pyrazol-1-yl)ethyl)pyridine 1-oxide To a solution of 5-(3-chloro-2-fluoro-6-(4-(trifluoromethyl)-1H-1,2,3-triazol-1-yl)phenyl)-2-(2-(1-(difluoromethyl)-1H-pyrazol-3-yl)-1-(4-(1-methyl-1H-1,2,4-triazol-5-yl)-1H-pyrazol-1-yl)ethyl)pyridine (110 mg, 0.19 mmol, 1.0 equiv.) in MeOH (5 mL) was add methylrhenium (VII) trioxide (5 mg, 0.02 mmol, 0.1 equiv.) and hydrogen peroxide (30 wt %, 33 mg, 0.97 mmol, 5.0 equiv.). The reaction mixture was stirred 1 h at room temperature, then purified by reverse phase chromatography on C18 (80 g, MeCN/H$_2$O (0.05% CF$_3$COOH): 0→50%) to yield a residue, which was purified by Prep-Chiral-HPLC to yield (R)-5-(3-chloro-2-fluoro-6-(4-(trifluoromethyl)-1H-1,2,3-triazol-1-yl)phenyl)-2-(2-(1-(difluoromethyl)-1H-pyrazol-3-yl)-1-(4-(1-methyl-1H-1,2,4-triazol-5-yl)-1H-pyrazol-1-yl)ethyl)pyridine 1-oxide as an white solid.

LC/MS: mass calculated for C$_{2H}$H$_{18}$ClF$_6$N$_{11}$O: 649.13, measured (ES, m/z): 650.15 [M+H]$^+$. $^1$H NMR (300 MHz, CD$_3$OD) δ 8.82 (s, 1H), 8.37-8.46 (m, 2H), 8.05 (s, 1H), 7.85-7.98 (m, 3H), 7.58-7.68 (m, 2H), 7.11-7.57 (m, 2H), 6.60-6.70 (m, 1H), 6.24 (d, J=2.7 Hz, 1H), 3.98 (s, 3H), 3.71-3.92 (m, 2H). $^{19}$F NMR (282 MHz, CD$_3$OD) δ −62.69, −96.06, −113.94.

Example 857: (R)-5-(3-Chloro-6-(4-cyano-1H-1,2,3-triazol-1-yl)-2-fluorophenyl)-2-(3-(difluoromethoxy)-1-(4-(3-(difluoromethyl)-3H-1,2,3-triazol-4-yl)-1H-pyrazol-1-yl)propyl)pyridine 1-oxide

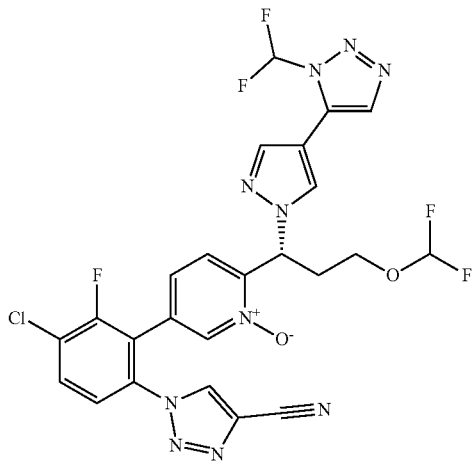 [SMILES: N#Cc1cn(-c2ccc(Cl)c(F)c2-c2ccc([C@@H](CCOC(F)F)n3cc(-c4cnnn4C(F)F)cn3)[n+]([O-])c2)nn1]

Step 1: 1-(Difluoromethyl)-5-(1H-pyrazol-4-yl)-1H-1,2,3-triazole

To a solution of 1-(difluoromethyl)-5-iodo-1H-1,2,3-triazole (1.0 g, 4.1 mmol, 1.0 equiv.) and tert-butyl 4-(4,4,5,5-tetramethyl-1,3,2-dioxaborolan-2-yl)-1H-pyrazole-1-carboxylate (1.8 g, 6.1 mmol, 1.5 equiv.) in 1,4-dioxane (15 mL) and water (3 mL) was added potassium carbonate (2.3 g, 16.3 mmol, 4.0 equiv.) and Pd(PPh$_3$)$_4$ (236 mg, 0.20 mmol, 0.05 equiv.) under N$_2$. The reaction mixture was stirred for 2 h at 90° C., then quenched with water, extracted with EA twice. The combined organic layers were dried over Na$_2$SO$_4$ and concentrated under vacuum. The residue was purified by silica gel chromatography (0→10% MeOH/DCM) to yield 1-(difluoromethyl)-5-(1H-pyrazol-4-yl)-1H-1,2,3-triazole as light yellow oil. LC/MS: mass calculated for C$_6$H$_5$F$_2$N$_5$: 185.05, measured (ES, m/z): 186.05 [M+H]$^+$.

Step 2: 5-Bromo-2-(3-(difluoromethoxy)-1-(4-(1-(difluoromethyl)-1H-1,2,3-triazol-5-yl)-1H-pyrazol-1-yl)propyl)pyridine To a solution of 1-(difluoromethyl)-5-(1H-pyrazol-4-yl)-1H-1,2,3-triazole (140. mg, 0.76 mmol, 1.0 equiv.) in acetonitrile (10 mL) was added cesium carbonate (246 mg, 0.76 mmol, 1.0 equiv.). After the reaction mixture was stirred for 1H at room temperature, 1-(5-bromopyridin-2-yl)-3-(difluoromethoxy)propyl methanesulfonate (300 mg, 0.83 mmol, 1.1 equiv.) was added. The reaction mixture was stirred for 2 h at 80° C., then cooled to room temperature. and filtered, washed with EA. The filtrate was concentrated under vacuum. The residue was purified by silica gel chromatography (0→60% EA-PE) to yield 5-bromo-2-(3-(difluoromethoxy)-1-(4-(1-(difluoromethyl)-1H-1,2,3-triazol-5-yl)-1H-pyrazol-1-yl)propyl)pyridine as light brown oil. LC/MS: mass calculated for C$_{15}$H$_{13}$BrF$_4$N$_6$O: 448.03, measured (ES, m/z): 448.95, 450.95 [M+H, M+H+2]$^+$.

Step 3: (6-(3-(Difluoromethoxy)-1-(4-(1-(difluoromethyl)-1H-1,2,3-triazol-5-yl)-1H-pyrazol-1-yl)propyl)pyridin-3-yl)boronic acid To a solution of 5-bromo-2-(3-(difluoromethoxy)-1-(4-(1-(difluoromethyl)-1H-1,2,3-triazol-5-yl)-1H-pyrazol-1-yl)propyl)pyridine (310 mg, 0.69 mmol, 1.0 equiv.) in 1,4-dioxane (15 mL) was added 4,4,4',4',5,5,5',5'-octamethyl-2,2'-bi(1,3,2-dioxaborolane) (350 mg, 1.38 mmol, 2.0 equiv.), potassium acetate (203 mg, 2.07 mmol, 3.0 equiv.) and Pd(dppf)Cl$_2$·CH$_2$Cl$_2$ (56 mg, 0.07 mmol, 0.1 equiv.) under N$_2$. The reaction mixture was stirred for 2 h at 90° C., then cooled to room temperature. and quenched with water, extracted with EA twice. The combined organic layers were washed with brine, dried over Na$_2$SO$_4$ and concentrated under vacuum to yield (6-(3-(difluoromethoxy)-1-(4-(1-(difluoromethyl)-1H-1,2,3-triazol-5-yl)-1H-pyrazol-1-yl)propyl)pyridin-3-yl)boronic acid as black oil. LC/MS: mass calculated for C$_{15}$H$_{15}$BF$_4$N$_6$O$_3$: 414.12, measured (ES, m/z): 415.05 [M+H]$^+$.

Step 4: 1-(4-Chloro-2-(6-(3-(difluoromethoxy)-1-(4-(1-(difluoromethyl)-1H-1,2,3-triazol-5-yl)-1H-pyrazol-1-yl)propyl)pyridin-3-yl)-3-fluorophenyl)-1H-1,2,3-triazole-4-carbonitrile To a solution of 1-(4-chloro-3-fluoro-2-iodophenyl)-1H-1,2,3-triazole-4-carbonitrile (200 mg, 0.57 mmol, 1.0 equiv.) and (6-(3-(difluoromethoxy)-1-(4-(1-(difluoromethyl)-1H-1,2,3-triazol-5-yl)-1H-pyrazol-1-yl)propyl)pyridin-3-yl)boronic acid (523 mg, resulting) in 1,4-dioxane (15 mL) and water (3 mL) was added potassium carbonate (238 g, 1.72 mmol, 3.0 equiv.) and Pd(PPh$_3$)$_4$ (66 mg, 0.06 mmol, 0.1 equiv.) under N$_2$. The reaction mixture was stirred for 2 h at 90° C., then quenched with water, extracted with EA twice. The combined organic layers were dried over Na$_2$SO$_4$ and concentrated under vacuum. The residue was purified by silica gel chromatography with EA/PE (0→80% EA-PE) to yield 1-(4-chloro-2-(6-(3-(difluoromethoxy)-1-(4-(1-(difluoromethyl)-1H-1,2,3-triazol-5-yl)-1H-pyrazol-1-yl)propyl)pyridin-3-yl)-3-fluorophenyl)-1H-1,2,3-triazole-4-carbonitrile as light yellow oil. LC/MS: mass calculated for C$_{24}$H$_{16}$ClF$_5$N$_{10}$O: 590.11, measured (ES, m/z): 591.05 [M+H]$^+$.

Step 5: (R)-5-(3-Chloro-6-(4-cyano-1H-1,2,3-triazol-1-yl)-2-fluorophenyl)-2-(3-(difluoromethoxy)-1-(4-(1-(difluoromethyl)-1H-1,2,3-triazol-5-yl)-1H-pyrazol-1-yl)propyl)pyridine 1-oxide To a solution of 1-(4-chloro-2-(6-(3-(difluoromethoxy)-1-(4-(1-(difluoromethyl)-1H-1,2,3-triazol-5-yl)-1H-pyrazol-1-yl)propyl)pyridin-3-yl)-3-fluorophenyl)-1H-1,2,3-triazole-4-carbonitrile (240 mg, 0.41 mmol, 1.0 equiv.) in MeOH (10 mL) was added hydrogen peroxide solution (30 wt %, 921 mg, 8.12 mmol, 20.0 equiv.) followed by the addition of methyltrioxorhenium (20 mg, 0.08 mmol, 0.2 equiv.). The reaction mixture was stirred for 2 h at room temperature, then purified by reverse column chromatography on C18 (0→70% MeCN/H$_2$O) to yield the resulting residue, which was purified by Chiral-HPLC with (Hex:DCM=3:1)(0.1% DEA):EtOH=50:50 to yield (R)-5-(3-chloro-6-(4-cyano-1H-1,2,3-triazol-1-yl)-2-fluorophenyl)-2-(3-(difluoromethoxy)-1-(4-(1-(difluoromethyl)-1H-1,2,3-triazol-5-yl)-1H-pyrazol-1-yl)propyl)pyridine 1-oxide as a white solid.

LC/MS: mass calculated for C$_{24}$H$_{16}$ClF$_5$N$_{10}$O$_2$: 606.11, measured (ES, m/z): 607.05 [M+H]$^+$. $^1$H NMR (400 MHz, CD$_3$OD): δ 8.90 (s, 1H), 8.34 (s, 2H), 7.86-8.19 (m, 4H), 7.55-7.63 (m, 2H), 7.25-7.35 (m, 1H), 6.15-6.55 (m, 2H), 3.93-4.02 (m, 1H), 3.65-3.75 (m, 1H), 2.74-2.84 (m, 1H), 2.62-2.74 (m, 1H). $^{19}$F-NMR (376 MHz, CD$_3$OD): δ −86.26, −98.33, −113.83.

Example 858: (S)-5-(3-Chloro-6-(4-cyano-1H-1,2,3-triazol-1-yl)-2-fluorophenyl)-2-(3-(difluoromethoxy)-1-(4-(1-(difluoromethyl)-1H-1,2,3-triazol-5-yl)-1H-pyrazol-1-yl)propyl)pyridine 1-oxide

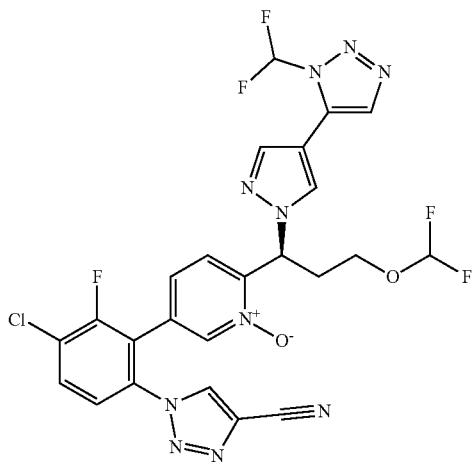 [SMILES: N#Cc1cn(-c2ccc(Cl)c(F)c2-c2ccc([C@H](CCOC(F)F)n3cc(-c4cnnn4C(F)F)cn3)[n+]([O-])c2)nn1]

LC/MS: mass calculated for C$_{24}$H$_{16}$ClF$_5$N$_{10}$O$_2$: 606.11, measured (ES, m/z): 607.1 [M+H]$^+$. $^1$H NMR (400 MHz, CD$_3$OD) d 8.90 (s, 1H), 8.34 (d, J=1.9 Hz, 2H), 7.85-8.91 (m, 4H), 7.56-7.64 (m, 2H), 7.32 (dd, J=8.4, 1.7 Hz, 1H), 6.14-6.56 (m, 2H), 3.90-4.02 (m, 1H), 3.66-3.78 (m, 1H), 2.74-2.85 (m, 1H), 2.61-2.74 (m, 1H). $^{19}$F NMR (376 MHz, CD$_3$OD) d −86.21, −98.33, −113.83.

Example 859: (S)-5-(3-Chloro-2-fluoro-6-(4-(trifluoromethyl)-1H-1,2,3-triazol-1-yl)phenyl)-2-(3-(difluoromethoxy)-1-(4-(1-methyl-1H-1,2,4-triazol-5-yl)-1H-pyrazol-1-yl)propyl-3,3-d2)pyridine 1-oxide

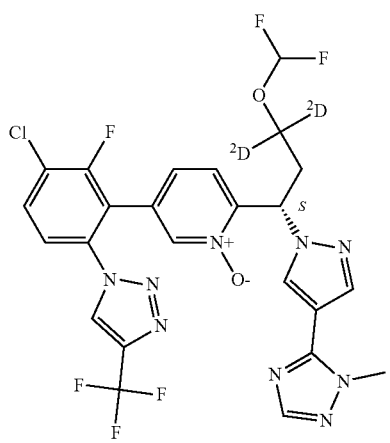

LC/MS: mass calculated for C$_{24}$H$_{16}$ClD$_2$F$_6$N$_9$O$_2$: 615.13, measured (ES, m/z): 616.05 [M+H]$^+$. $^1$H NMR (400 MHz, DMSO-d$_6$) δ 9.18 (d, J=1.0 Hz, 1H), 8.61 (d, J=0.8 Hz, 1H), 8.44 (d, J=1.6 Hz, 1H), 8.02-8.11 (m, 2H), 7.90 (s, 1H), 7.75-7.80 (m, 1H), 7.30-7.35 (m, 1H), 7.15-7.20 (m, 1H), 6.63 (t, J=75.7 Hz, 1H), 6.25-6.31 (m, 1H), 3.96 (s, 3H), 2.55-2.70 (m, 2H). $^{19}$F NMR (376 MHz, DMSO-d$_6$) δ −59.79, −73.94, −83.33, −83.35, −112.84.

Example 860: (R)-5-(3-Chloro-2-fluoro-6-(4-(trifluoromethyl)-1H-1,2,3-triazol-1-yl)phenyl)-2-(3-(difluoromethoxy)-1-(4-(1-methyl-1H-1,2,4-triazol-5-yl)-1H-pyrazol-1-yl)propyl-3,3-d2)pyridine 1-oxide

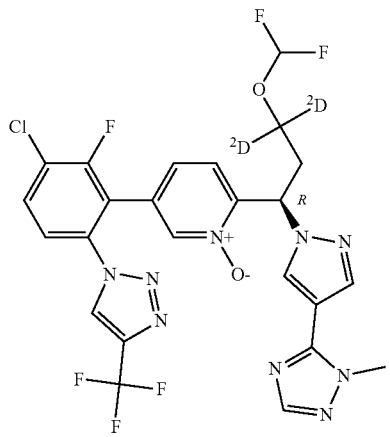

Step 1: 1-(5-Bromopyridin-2-yl)propane-1,3,3-d3-1,3-diol

To a solution of ethyl 3-(5-bromopyridin-2-yl)-3-oxopropanoate (3.0 g, 11.03 mmol, 1.0 equiv.) in CH$_3$OH (30 mL) was added sodium tetrahydroborate-d$_4$ (3.7 g, 88.20 mmol, 8.0 equiv.) at room temperature. The mixture was stirred at room temperature for 30 min. then stirred at 60° C. for 1 h. The resulting mixture was quenched by water (30 mL) and extract with EA (3×30 mL). Then the organic layers were combined, washed with brine, dried over $Na_2SO_4$ and concentrated to yield 1-(5-bromopyridin-2-yl)propane-1,3,3-d3-1,3-diol as a light yellow oil. LCMS: mass calculated for $C_8H_7D_3BrNO_2$: 234.01, measured (ES, m/z): 235.00 $[M+H]^+$.

Step 2: 1-(5-Bromopyridin-2-yl)-3-hydroxypropan-1-one-3,3-d2

To a solution of 1-(5-bromopyridin-2-yl)propane-1,3,3-d3-1,3-diol (1.3 g, 5.32 mmol, 1.0 equiv.) in DCM (15 mL) was added manganese dioxide (9.2 g, 106.34 mmol, 20.0 equiv.). The resulting mixture was stirred at 50° C. for 48 h. The catalyst was filtered out. The filtrate was concentrated and purified by silica gel column (EA/PE, 0%→50%) to yield 1-(5-bromopyridin-2-yl)-3-hydroxypropan-1-one-3,3-d2 as a brown solid.
LCMS: mass calculated for $C_8H_6D_2BrNO_2$: 230.99, measured (ES, m/z): 232.05 $[M+H]^+$.

Step 3: 1-(5-Bromopyridin-2-yl)-3-(difluoromethoxy)propan-1-one-3,3-d2

To a solution of 1-(5-bromopyridin-2-yl)-3-hydroxypropan-1-one-3,3-d2 (820 mg, 3.53 mmol, 1.0 equiv.) in acetonitrile (4 mL) was added CuI (135 mg, 0.71 mmol, 0.2 equiv.). The resulting mixture was stirred at 50° C. Then 2,2-difluoro-2-(fluorosulfonyl)acetic acid (0.4 mL) in acetonitrile (4 mL) was added to the mixture by drops. The reaction mixture was stirred at 50° C. for 2 h. The resulting mixture was quenched by water, extracted with EA (10 mL×3). Then the organic layers were combined, washed with brine, dried over $Na_2SO_4$ and concentrated to yield 1-(5-bromopyridin-2-yl)-3-(difluoromethoxy)propan-1-one-3,3-d2 as a light yellow oil. LC/MS: mass calculated for $C_9H_6D_2BrF_2NO_2$: 280.98, measured (ES, m/z): 283.95 $[M+H+2]^+$.

Step 4: 1-(5-Bromopyridin-2-yl)-3-(difluoromethoxy)propan-3,3-d2-1-ol

To a solution of 1-(5-bromopyridin-2-yl)-3-(difluoromethoxy)propan-1-one-3,3-d2 (294 mg, 1.0 mmol, 1.0 equiv.) in $CH_3OH$ (3.0 mL) was added sodium borohydride (79 mg, 2.09 mmol, 2.0 equiv.) at 0° C. Then the mixture was stirred at room temperature for 2 h. The resulting mixture was quenched by water (10 mL) and extract with EA (3×10 mL). The organic layers were combined, washed with brine, dried over $Na_2SO_4$, and concentrated to yield 1-(5-bromopyridin-2-yl)-3-(difluoromethoxy)propan-3,3-d2-1-ol as a light yellow oil. LCMS: mass calculated for $C_9H_8D_2BrF_2NO_2$: 283.00, measured (ES, m/z): 283.95 $[M+H]^+$.

Step 5: 1-(5-Bromopyridin-2-yl)-3-(difluoromethoxy)propyl-3,3-d2 methanesulfonate To a solution of 1-(5-bromopyridin-2-yl)-3-(difluoromethoxy)propan-3,3-d2-1-ol (296 mg, 1.04 mmol, 1.0 equiv.) in chloromethane (3 mL) was added triethylamine (422 mg, 4.17 mmol, 4.0 equiv.) under 0° C., followed by methanesulfonic anhydride (363 mg, 2.08 mmol, 2.0 equiv.) The resulting mixture was stirred at room temperature for 2 h. The reaction was quenched by water (10 mL), extracted with EA (3×20 mL). The organic layers were combined, washed with brine, dried over $Na_2SO_4$ and concentrated. The residue was purified by silica gel chromatography (EA/PE, 0%460%) to yield 1-(5-bromopyridin-2-yl)-3-(difluoromethoxy)propyl-3,3-d2 methanesulfonate as a yellow solid. LCMS: mass calculated for $C_{10}H_{10}D_2BrF_2NO_4S$: 360.98, measured (ES, m/z): 363.95 $[M+H+2]^+$.

Step 6: 5-Bromo-2-(3-(difluoromethoxy)-1-(4-(1-methyl-1H-1,2,4-triazol-5-yl)-1H-pyrazol-1-yl)propyl-3,3-d2)pyridine A mixture of cesium carbonate (210 mg, 0.65 mmol, 1.0 equiv.) and 4-methyl-3-(1H-pyrazol-4-yl)-4H-1,2,4-triazole (96 mg, 0.65 mmol, 1.0 equiv.) in acetonitrile (3 mL) was stirred for 15 min at room temperature.
1-(5-Bromopyridin-2-yl)-3-(difluoromethoxy)propyl-3,3-d2 methanesulfonate (234 mg, 0.65 mmol, 1.0 equiv.) was added and the solution was stirred for 2.5 h at 90° C. The resulting mixture was diluted with water (20 mL), extracted with EA (3×20 mL). Then the organic layers were combined, washed with brine, dried over $Na_2SO_4$ and concentrated. The resulting mixture was purified by silica gel column (EA/PE, 0%480%) to yield 5-bromo-2-(3-(difluoromethoxy)-1-(4-(1-methyl-1H-1,2,4-triazol-5-yl)-1H-pyrazol-1-yl)propyl-3,3-d2)pyridine as a yellow oil. LCMS: mass calculated for $C_{15}H_{13}D_2BrF_2N_6O$: 414.06, measured (ES, m/z): 416.95 $[M+H+2]^+$.

Step 7: (6-(3-(Difluoromethoxy)-1-(4-(1-methyl-1H-1,2,4-triazol-5-yl)-1H-pyrazol-1-yl)propyl-3,3-d2)pyridin-3-yl)boronic acid A mixture of 5-bromo-2-(3-(difluoromethoxy)-1-(4-(1-methyl-1H-1,2,4-triazol-5-yl)-1H-pyrazol-1-yl)propyl-3,3-d2)pyridine (240 mg, 0.58 mmol, 1.0 equiv.), 4,4,4',4',5,5,5',5'-octamethyl-2,2'-bi(1,3,2-dioxaborolane) (220 mg, 0.87 mmol, 1.5 equiv.), $Pd(dppf)Cl_2$ (42 mg, 0.06 mmol, 0.1 equiv.) and KOAc (170 mg, 1.70 mmol, 3.0 equiv.) in 1,4-dioxane (2.4 mL) was stirred for 2 h at 90° C. The resulting mixture was diluted with water, extracted with EA (3×15 mL). The organic layers were combined, washed with brine, dried over $Na_2SO_4$ and concentrated to yield (6-(3-(difluoromethoxy)-1-(4-(1-methyl-1H-1,2,4-triazol-5-yl)-1H-pyrazol-1-yl)propyl-3,3-d2)pyridin-3-yl)boronic acid as a black oil. LCMS: mass calculated for $C_{15}H_{15}D_2BF_2N_6O_3$: 380.15, measured (ES, m/z): 381.10 $[M+H]^+$.

Step 8: 5-(3-Chloro-2-fluoro-6-(4-(trifluoromethyl)-1H-1,2,3-triazol-1-yl)phenyl)-2-(3-(difluoromethoxy)-1-(4-(1-methyl-1H-1,2,4-triazol-5-yl)-1H-pyrazol-1-yl)propyl-3,3-d2)pyridine A mixture of 1-(4-chloro-3-fluoro-2-iodophenyl)-4-(trifluoromethyl)-1H-1,2,3-triazole (330 mg, 0.8 mmol, 1.2 equiv.), (6-(3-(difluoromethoxy)-1-(4-(1-methyl-1H-1,2,4-triazol-5-yl)-1H-pyrazol-1-yl)propyl-3,3-d2)pyridin-3-yl)boronic acid (267 mg, 0.7 mmol, 1.0 equiv.), $Pd(PPh_3)_4$ (66 mg, 0.06 mmol, 0.1 equiv.) and $K_2CO_3$ (236 mg, 1.71 mmol, 3.0 equiv.) in 1,4-dioxane/water (V/V=4:1, 2.4 mL) was refluxed at 90° C. under $N_2$ for 3 h. The resulting mixture was diluted with water (10 mL), extracted with EA (3×10 mL). The organic layers were combined, washed with brine, dried over $Na_2SO_4$ and concentrated. The residue was purified by silica gel chromatography to yield 5-(3-chloro-2-fluoro-6-(4-(trifluoromethyl)-1H-1,2,3-triazol-1-yl)phenyl)-

2-(3-(difluoromethoxy)-1-(4-(1-methyl-1H-1,2,4-triazol-5-yl)-1H-pyrazol-1-yl)propyl-3,3-d2)pyridine as a light yellow oil. LCMS: mass calculated for C₂₄H₁₆D₂ClF₆N₉O: 599.14, measured (ES, m/z): 600.25 [M+H]⁺.

Step 9: (R)-5-(3-Chloro-2-fluoro-6-(4-(trifluoromethyl)-1H-1,2,3-triazol-1-yl)phenyl)-2-(3-(difluoromethoxy)-1-(4-(1-methyl-1H-1,2,4-triazol-5-yl)-1H-pyrazol-1-yl)propyl-3,3-d2)pyridine 1-oxide A mixture of 5-(3-chloro-2-fluoro-6-(4-(trifluoromethyl)-1H-1,2,3-triazol-1-yl)phenyl)-2-(3-(difluoromethoxy)-1-(4-(1-methyl-1H-1,2,4-triazol-5-yl)-1H-pyrazol-1-yl)propyl-3,3-d2)pyridine (219 mg, 0.37 mmol, 1.0 equiv.), methyltrioxorhenium (27 mg, 0.11 mmol, 0.5 equiv.), hydrogen peroxide (0.06 mL, 30 wt %) in CH₃OH (2 mL) was stirred for 3 h at room temperature. The resulting mixture was purified by reverse phase chromatography on C18 (MeCN/H₂O (0.05% CF₃COOH)) to yield 5-(3-chloro-2-fluoro-6-(4-(trifluoromethyl)-1H-1,2,3-triazol-1-yl)phenyl)-2-(3-(difluoromethoxy)-1-(4-(1-methyl-1H-1,2,4-triazol-5-yl)-1H-pyrazol-1-yl)propyl-3,3-d2)pyridine 1-oxide as a white solid. The racemic product was separated by chiral-HPLC to yield (R)-5-(3-chloro-2-fluoro-6-(4-(trifluoromethyl)-1H-1,2,3-triazol-1-yl)phenyl)-2-(3-(difluoromethoxy)-1-(4-(1-methyl-1H-1,2,4-triazol-5-yl)-1H-pyrazol-1-yl)propyl-3,3-d2)pyridine 1-oxide as a white solid.

LC/MS: mass calculated for C₂₄H₁₆ClD₂F₆N₉O₂: 615.13, measured (ES, m/z): 616.05 ¹H NMR (400 MHz, DMSO-d₆) δ 9.18 (s, 1H), 8.61 (s, 1H), 8.44 (s, 1H), 8.02-8.11 (m, 2H), 7.90 (s, 1H), 7.75-7.82 (m, 1H), 7.32 (d, J=8.3 Hz, 1H), 7.15-7.22 (m, 1H), 6.40-6.80 (m, 1H), 6.20-6.32 (m, 1H), 3.96 (s, 3H), 2.53-2.68 (m, 2H). ¹⁹F-NMR (376 MHz, DMSO-d₆) δ −59.79, −83.34, −112.84.

Example 861: (R)-5-(3-chloro-2-fluoro-6-(4-(trifluoromethyl)-1H-1,2,3-triazol-1-yl)phenyl)-2-(3-(difluoromethoxy)-1-(4-(3-methyl-4H-1,2,4-triazol-4-yl)-1H-pyrazol-1-yl)propyl)pyridine 1-oxide 0.07 TFA salt

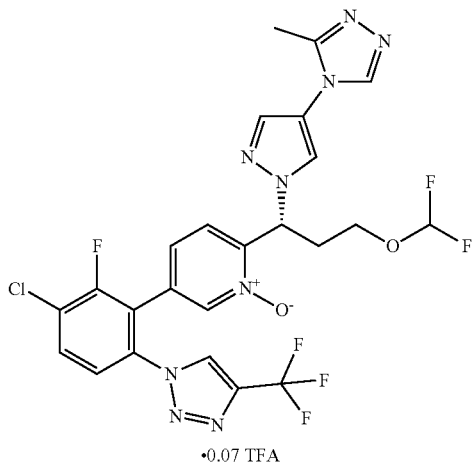 [SMILES: Cc1nncn1-c1cnn([C@H](CCOC(F)F)c2ccc(-c3c(-n4cc(C(F)(F)F)nn4)ccc(Cl)c3F)c[n+]2[O-])c1]

•0.07 TFA

Step 1: 5-(3-Chloro-2-fluoro-6-(4-(trifluoromethyl)-1H-1,2,3-triazol-1-yl)phenyl)-2-(3-(difluoromethoxy)-1-(4-(3-methyl-4H-1,2,4-triazol-4-yl)-1H-pyrazol-1-yl)propyl)pyridine To a solution of (6-(3-(difluoromethoxy)-1-(4-(3-methyl-4H-1,2,4-triazol-4-yl)-1H-pyrazol-1-yl)propyl)pyridin-3-yl) boronic acid (200 mg, 0.53 mmol, 1.0 equiv.) in 1,4-dioxane (10 mL) and H₂O (1 mL) was added 1-(4-chloro-3-fluoro-2-iodophenyl)-4-(trifluoromethyl)-1H-1,2,3-triazole (248 mg, 0.64 mmol, 1.2 equiv.), K₂CO₃ (110 mg, 0.79 mmol, 1.5 equiv.), Pd(pph₃)₄ (61 mg, 0.05 mmol, 0.1 equiv.). The resulting mixture was maintained under nitrogen and stirred at 90° C. for 3H. After cooling to room temperature, the reaction was quenched with water (20 mL). The resulting mixture was extracted with ethyl acetate (3×20 mL). The organic layers were combined, dried over anhydrous sodium sulfate, filtered and concentrated. The resulting residue was purified by silica gel chromatography (0→80% ethyl acetate/petroleum ether) to yield the 5-(3-chloro-2-fluoro-6-(4-(trifluoromethyl)-1H-1,2,3-triazol-1-yl)phenyl)-2-(3-(difluoromethoxy)-1-(4-(3-methyl-4H-1,2,4-triazol-4-yl)-1H-pyrazol-1-yl)propyl)pyridine as a yellow solid. LC/MS: mass calculated for C₂₄H₁₈ClF₆N₉O: 597.12, measured (ES, m/z): 598.10 [M+H]⁺.

Step 2: (R)-5-(3-chloro-2-fluoro-6-(4-(trifluoromethyl)-1H-1,2,3-triazol-1-yl)phenyl)-2-(3-(difluoromethoxy)-1-(4-(3-methyl-4H-1,2,4-triazol-4-yl)-1H-pyrazol-1-yl)propyl)pyridine 1-oxide (0.07 TFA salt)

To a solution of 5-(3-chloro-2-fluoro-6-(4-(trifluoromethyl)-1H-1,2,3-triazol-1-yl)phenyl)-2-(3-(difluoromethoxy)-1-(4-(3-methyl-4H-1,2,4-triazol-4-yl)-1H-pyrazol-1-yl)propyl)pyridine (300.0 mg, 0.50 mmol, 1.0 equiv.) in MeOH (10 mL) and H₂O₂ (0.3 mL, 30 wt %) was added methyltelioxorioxorhenium (VII) (125.0 mg, 0.50 mmol, 1.0 equiv.). The mixture stirred at room temperature for 2 h. The residue was purified by C18 column with CH₃CN/0.05% TFA water (5%→40%), and then purified by chiral-HPLC with (Hex(0.1% DEA):EtOH=55:45) to yield (R)-5-(3-chloro-2-fluoro-6-(4-(trifluoromethyl)-1H-1,2,3-triazol-1-yl)phenyl)-2-(3-(difluoromethoxy)-1-(4-(3-methyl-4H-1,2,4-triazol-4-yl)-1H-pyrazol-1-yl)propyl)pyridine 1-oxide (0.07 TFA salt) as off-white solid.

LC/MS: mass calculated for C₂₄H₁₈ClF₆N₉O₂: 613.1, measured (ES, m/z): 614.1 [M+H]⁺. ¹H NMR (300 MHz, DMSO-d₆) δ 9.17 (s, 1H), 8.38-8.55 (m, 2H), 7.92-8.15 (m, 3H), 7.71-7.89 (m, 1H), 7.30-7.38 (m, 1H), 7.09-7.20 (m, 1H), 6.35-6.90 (m, 1H), 6.15-6.29 (m, 1H), 3.61-3.91 (m, 2H), 2.60-2.75 (m, 2H), 2.43 (s, 3H). ¹⁹F NMR (282 MHz, DMSO-d₆) δ −59.80, −73.71, −83.41, −112.83.

Example 862: (S)-5-(3-Chloro-2-fluoro-6-(4-(trifluoromethyl)-1H-1,2,3-triazol-1-yl)phenyl)-2-(3-(difluoromethoxy)-1-(4-(3-methyl-1H-1,2,4-triazol-1-yl)-1H-pyrazol-1-yl)propyl)pyridine 1-oxide

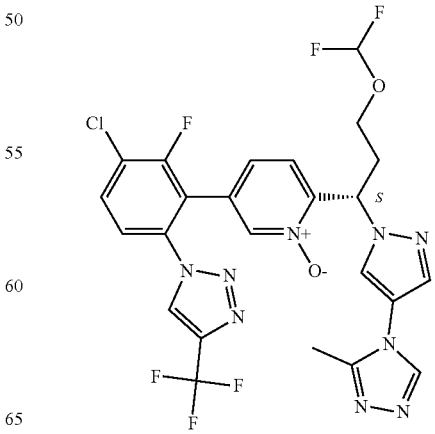

LC/MS: mass calculated for $C_{24}H_{18}ClF_6N_9O_2$: 613.1, measured (ES, m/z): 614.1 [M+H]⁺. ¹H NMR (300 MHz, DMSO-$d_6$) δ 9.11-9.25 (m, 1H), 8.38-8.55 (m, 2H), 8.01-8.15 (m, 1H), 7.94-8.00 (m, 2H), 7.71-7.89 (m, 1H), 7.30-7.38 (m, 1H), 7.09-7.20 (m, 1H), 6.35-6.90 (m, 1H), 6.15-6.29 (m, 1H), 3.61-3.91 (m, 2H), 2.55-2.75 (m, 2H), 2.43 (s, 3H). ¹⁹F NMR (282 MHz, DMSO-$d_6$) δ −59.80, −73.83, −83.42, −112.83.

Example 863: (R)-2-(1-(4-(1H-1,2,4-triazol-1-yl)-1H-pyrazol-1-yl)-3-(difluoromethoxy)propyl)-5-(3-chloro-2-fluoro-6-(4-(trifluoromethyl)-1H-1,2,3-triazol-1-yl)phenyl)pyridine 1-oxide

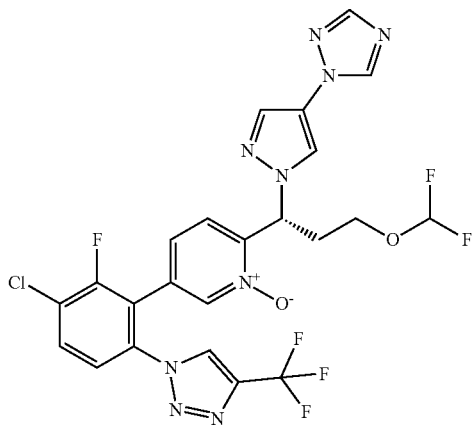 [SMILES: [O-][n+]1cc(-c2c(-n3cc(C(F)(F)F)nn3)ccc(Cl)c2F)ccc1[C@@H](CCOC(F)F)n1cc(-n2cncn2)cn1]

Step 1: (R)-2-(1-(4-(1H-1,2,4-triazol-1-yl)-1H-pyrazol-1-yl)-3-(difluoromethoxy)propyl)-5-(3-chloro-2-fluoro-6-(4-(trifluoromethyl)-1H-1,2,3-triazol-1-yl)phenyl)pyridine To a solution of (6-(3-(difluoromethoxy)-1-(4-(3-methyl-4H-1,2,4-triazol-4-yl)-1H-pyrazol-1-yl)propyl)pyridin-3-yl)boronic acid (200 mg, 0.53 mmol, 1.0 equiv.) in 1,4-dioxane (10 mL) and H₂O (1 mL) was added 1-(4-chloro-3-fluoro-2-iodophenyl)-4-(trifluoromethyl)-1H-1,2,3-triazole (248 mg, 0.64 mmol, 1.2 equiv.), K₂CO₃ (110 mg, 0.79 mmol, 1.5 equiv.), Pd(pph₃)₄ (61 mg, 0.05 mmol, 0.1 equiv.). The resulting mixture was maintained under nitrogen and stirred at 90° C. for 3 h. After cooling to room temperature, the reaction was quenched with water (20 mL). The resulting mixture was extracted with ethyl acetate (3×20 mL). The organic layers were combined, dried over anhydrous sodium sulfate, filtered and concentrated. The resulting residue was purified by silica gel chromatography (0→80% ethyl acetate/petroleum ether) to yield the 5-(3-chloro-2-fluoro-6-(4-(trifluoromethyl)-1H-1,2,3-triazol-1-yl)phenyl)-2-(3-(difluoromethoxy)-1-(4-(3-methyl-4H-1,2,4-triazol-4-yl)-1H-pyrazol-1-yl)propyl)pyridine as a yellow solid. LC/MS: mass calculated for $C_{24}H_{18}ClF_6N_9O$: 597.12, measured (ES, m/z): 598.10 [M+H]⁺.

Step 2: (R)-2-(1-(4-(1H-1,2,4-triazol-1-yl)-1H-pyrazol-1-yl)-3-(difluoromethoxy)propyl)-5-(3-chloro-2-fluoro-6-(4-(trifluoromethyl)-1H-1,2,3-triazol-1-yl)phenyl)pyridine 1-oxide To a solution of 5-(3-chloro-2-fluoro-6-(4-(trifluoromethyl)-1H-1,2,3-triazol-1-yl)phenyl)-2-(3-(difluoromethoxy)-1-(4-(3-methyl-4H-1,2,4-triazol-4-yl)-1H-pyrazol-1-yl)propyl)pyridine (300 mg, 0.50 mmol, 1.0 equiv.) in MeOH (10 mL) and H₂O₂ (0.3 mL, 30 wt %) was added methylteioxorioxorhenium (VII) (125 mg, 0.50 mmol, 1.0 equiv.). The mixture stirred at room temperature for 2 h. The residue was purified by C18 column with CH₃CN/0.05% TFA water (5%440%) to yield a residue, which was purified by chiral-HPLC with (Hex(0.1% DEA):EtOH=55:45) to yield (R)-5-(3-chloro-2-fluoro-6-(4-(trifluoromethyl)-1H-1,2,3-triazol-1-yl)phenyl)-2-(3-(difluoromethoxy)-1-(4-(3-methyl-4H-1,2,4-triazol-4-yl)-1H-pyrazol-1-yl)propyl)pyridine 1-oxide as off-white solid.

LC/MS: mass calculated for $C_{24}H_{18}ClF_6N_9O_2$: 613.1, measured (ES, m/z): 614.1 [M+H]⁺. ¹H NMR (300 MHz, DMSO-$d_6$) δ 9.17 (s, 1H), 8.81 (s, 1H), 8.39-8.56 (m, 2H), 7.99-8.19 (m, 2H), 7.72-7.89 (m, 1H), 7.25-7.36 (m, 1H), 7.05-7.19 (m, 1H), 6.35-6.98 (m, 1H), 6.10-6.29 (m, 1H), 3.61-3.91 (m, 2H), 2.60-2.75 (m, 2H), 2.25 (s, 3H). ¹⁹F NMR (282 MHz, DMSO-$d_6$) δ −59.79, −83.33, −112.83.

Example 864: (S)-5-(3-Chloro-2-fluoro-6-(4-(trifluoromethyl)-1H-1,2,3-triazol-1-yl)phenyl)-2-(3-(difluoromethoxy)-1-(4-(3-methyl-4H-1,2,4-triazol-4-yl)-1H-pyrazol-1-yl)propyl)pyridine 1-oxide

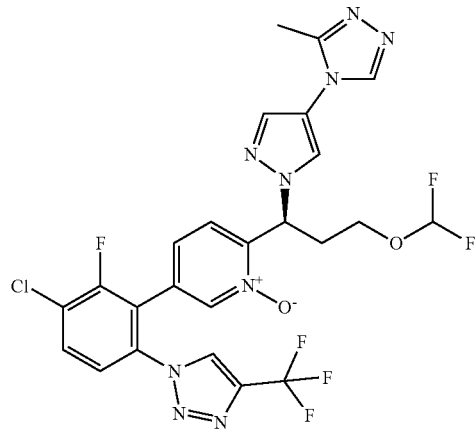 [SMILES: Cc1nncn1-c1cnn([C@@H](CCOC(F)F)c2ccc(-c3c(-n4cc(C(F)(F)F)nn4)ccc(Cl)c3F)c[n+]2[O-])c1]

LC/MS: mass calculated for $C_{24}H_{18}ClF_6N_9O_2$: 613.1, measured (ES, m/z): 614.1 [M+H]⁺. ¹H NMR (300 MHz, DMSO-$d_6$) δ 9.11-9.25 (m, 1H), 8.81 (s, 1H), 8.39-8.56 (m, 2H), 7.99-8.19 (m, 2H), 7.72-7.89 (m, 1H), 7.25-7.36 (m, 1H), 6.99-7.19 (m, 1H), 6.63 (t, J=75.6 Hz, 1H), 6.35-6.98 (m, 1H), 6.10-6.29 (m, 1H), 3.61-3.91 (m, 2H), 2.60-2.75 (m, 2H), 2.35 (s, 3H). ¹⁹F NMR (282 MHz, DMSO-$d_6$) δ −59.79, −73.63, −83.33, −112.83.

Example 865: (S*)-5-(3-chloro-6-(4-(difluoromethyl)-1H-1,2,3-triazol-1-yl)-2-fluorophenyl)-2-(3-(difluoromethoxy)-1-(4-(3-methyl-1H-1,2,4-triazol-1-yl)-1H-pyrazol-1-yl)propyl)pyridine 1-oxide

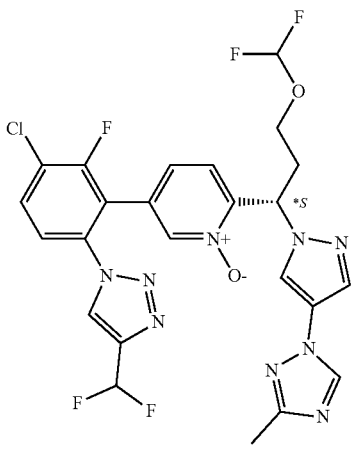 [SMILES: Cc1ncn(-c2cnn([C@@H](CCOC(F)F)c3ccc(-c4c(-n5cc(C(F)F)nn5)ccc(Cl)c4F)c[n+]3[O-])c2)n1]

Step 1: 3-Methyl-4-(1-(tetrahydro-2H-pyran-2-yl)-1H-pyrazol-4-yl)-4H-1,2,4-triazole To a solution of 4-iodo-1-(tetrahydro-2H-pyran-2-yl)-1H-pyrazole (4.0 g, 14.38 mmol, 1.0 equiv.) in N,N-dimethylformamide (100.0 mL) was added 3-methyl-4H-1,2,4-triazole (4.8 g, 57.53 mmol, 4.0 equiv.), cupric acetate (261.3 mg, 1.44 mmol, 0.1 equiv.) and cesium carbonate (14.1 g, 43.15 mmol, 3.0 equiv.). The resulting mixture was maintained under nitrogen and stirred at 130° C. for 16 h. The reaction was quenched with water (250 mL). The resulting mixture was extracted with DCM (3×250 mL). The organic layers were combined, dried over anhydrous sodium sulfate, filtered, and concentrated. The resulting residue was purified by silica gel chromatography (0→20% ethyl acetate/petroleum ether) to yield 3-methyl-4-(1-(tetrahydro-2H-pyran-2-yl)-1H-pyrazol-4-yl)-4H-1,2,4-triazole as a yellow oil. LC/MS: mass calculated For $C_{11}H_{15}N_5O$: 233.13, measured (ES, m/z): 234.25 $[M+H]^+$.

Step 2: 3-Methyl-4-(1H-pyrazol-4-yl)-4H-1,2,4-triazole

To a solution of 4-(2-methyl-1H-imidazol-1-yl)-1-(tetrahydro-2H-pyran-2-yl)-1H-pyrazole (1.0 g, 4.29 mmol, 1.0 equiv.) in $CH_3OH$ (20.0 mL) and 4M HCl in 1,4-dioxane (5.0 mL) was added slowly. The resulting mixture was stirred at room temperature. for 3 hours, then concentrated under reduced pressure to yield 3-methyl-4-(1H-pyrazol-4-yl)-4H-1,2,4-triazole a as a residue. LC/MS: mass calculated for $C_6H_7N_5$: 149.07, measured (ES, m/z): 150.25 $[M+H]^+$.

Step 3: 5-Bromo-2-(3-(difluoromethoxy)-1-(4-(3-methyl-4H-1,2,4-triazol-4-yl)-1H-pyrazol-1-yl)propyl)pyridine To a solution of 3-methyl-4-(1H-pyrazol-4-yl)-4H-1,2,4-triazole (500.0 mg, 3.33 mmol, 1.0 equiv.) in acetonitrile (20.0 mL) was added cesium carbonate (873.8 mg, 2.68 mmol, 0.8 equiv.), and then stirred at room temperature for 0.5 h. 1-(5-Bromopyridin-2-yl)-3-(difluoromethoxy)propyl methanesulfonate (1.2 g, 3.33 mmol, 1.0 equiv.) was added and the resulting mixture was stirred at 70° C. for 2 h. The reaction mixture was diluted with water, and the mixture extracted with ethyl acetate (3×50 mL). The organic layers were combined, dried over anhydrous sodium sulfate, filtered and concentrated. The resulting residue was purified by silica gel chromatography (0→60% ethyl acetate/petroleum ether) to yield the 5-bromo-2-(3-(difluoromethoxy)-1-(4-(3-methyl-4H-1,2,4-triazol-4-yl)-1H-pyrazol-1-yl)propyl)pyridine as a yellow oil. LC/MS: mass calculated for $C_{15}H_{15}BrF_2N_6O$: 412.05, measured (ES, m/z): 413.05 $[M+H]^+$.

Step 4: (6-(3-(Difluoromethoxy)-1-(4-(3-methyl-4H-1,2,4-triazol-4-yl)-1H-pyrazol-1-yl)propyl)pyridin-3-yl)boronic acid To a solution of 5-bromo-2-(3-(difluoromethoxy)-1-(4-(3-methyl-4H-1,2,4-triazol-4-yl)-1H-pyrazol-1-yl)propyl)pyridine (590.0 mg, 1.43 mmol, 1.0 equiv.) in 1,4-dioxane (20.0 mL) was added 4,4,4',4',5,5,5',5'-octamethyl-2,2'-bi(1,3,2-dioxaborolane) (543.8 mg, 2.14 mmol, 1.5 equiv.) [1,1'-bis(diphenylphosphino)ferrocene]dichloropalladium(II) (104.5 mg, 0.14 mmol, 0.1 equiv.) and potassium acetate (210.2 mg, 2.14 mmol, 1.5 equiv.). The resulting mixture was maintained under nitrogen and stirred at 90° C. for 16 h. The resulting mixture was extracted with ethyl acetate (3×50 mL). The organic layers were combined, dried over anhydrous sodium sulfate, filtered and concentrated under reduced pressure to yield a resulting residue. LC/MS: mass calculated for $C_{15}H_{17}BF_2N_6O_3$: 378.14, measured (ES, m/z): 379.20 $[M+H]^+$.

Step 5: 5-(3-chloro-6-(4-(difluoromethyl)-1H-1,2,3-triazol-1-yl)-2-fluorophenyl)-2-(3-(difluoromethoxy)-1-(4-(3-methyl-1H-1,2,4-triazol-1-yl)-1H-pyrazol-1-yl)propyl)pyridine To a solution of (6-(3-(difluoromethoxy)-1-(4-(3-methyl-4H-1,2,4-triazol-4-yl)-1H-pyrazol-1-yl)propyl)pyridin-3-yl)boronic acid (300.0 mg, 0.79 mmol, 1.0 equiv.) in 1,4-dioxane (20.0 mL) and water (2.0 mL) was added 1-(4-chloro-3-fluoro-2-iodophenyl)-4-(difluoromethyl)-1H-1,2,3-triazole (296.3 mg, 0.79 mmol, 1.0 equiv.), tetrakis(triphenylphosphine)palladium (91.7 mg, 0.08 mmol, 0.1 equiv.) and potassium carbonate (164.5 mg, 1.19 mmol, 1.5 equiv.). The resulting mixture was maintained under nitrogen and stirred at 90° C. for 2 h. The reaction was quenched with water (50 mL). The resulting mixture was extracted with ethyl acetate (3×50 mL). The organic layers were combined, dried over anhydrous sodium sulfate, filtered and concentrated. The resulting residue was purified by silica gel chromatography (0→80% ethyl acetate/petroleum ether) to yield 5-(3-chloro-6-(4-(difluoromethyl)-1H-1,2,3-triazol-1-yl)-2-fluorophenyl)-2-(3-(difluoromethoxy)-1-(4-(3-methyl-4H-1,2,4-triazol-4-yl)-1H-pyrazol-1-yl)propyl)pyridine as a yellow oil. LC/MS: mass calculated for $C_{24}H_{19}ClF_5N_9O$: 579.13, measured (ES, m/z): 580.10 $[M+H]^+$.

Step 6: (S*)-5-(3-chloro-6-(4-(difluoromethyl)-1H-1,2,3-triazol-1-yl)-2-fluorophenyl)-2-(3-(difluoromethoxy)-1-(4-(3-methyl-1H-1,2,4-triazol-1-yl)-1H-pyrazol-1-yl)propyl)pyridine 1-oxide To a solution of 5-(3-chloro-6-(4-(difluoromethyl)-1H-1,2,3-triazol-1-yl)-2-fluorophenyl)-2-(3-(difluoromethoxy)-1-

(4-(3-methyl-4H-1,2,4-triazol-4-yl)-1H-pyrazol-1-yl)propyl)pyridine (140.0 mg, 0.24 mmol, 1.0 equiv.) in CH$_3$OH (5.0 mL) was added methyltrioxorhenium (VII) (6.0 mg, 0.024 mmol, 0.1 equiv.) and hydrogen peroxide (0.5 mL, 30 wt. %). The mixture was stirred at room temperature for 1 h. The resulting mixture was purified by silica gel chromatography with MeOH/DCM (0→10%) to yield a residue, which was purified by Chiral-HPLC with mobile phase: (Hex:DCM=3:1) (0.1% DEA):EtOH=70:30 to yield (S*)-5-(3-Chloro-6-(4-(difluoromethyl)-1H-1,2,3-triazol-1-yl)-2-fluorophenyl)-2-(3-(difluoromethoxy)-1-(4-(3-methyl-1H-1,2,4-triazol-1-yl)-1H-pyrazol-1-yl)propyl)pyridine 1-oxide as a white solid.

LC/MS: mass calculated for C$_{24}$H$_{19}$ClF$_5$N$_9$O$_2$: 595.13, measured (ES, m/z): 596.10 [M+H]$^+$. $^1$H NMR (400 MHz, CD$_3$OD) δ 8.71 (s, 1H), 8.52 (s, 1H), 8.32-8.39 (m, 2H), 7.99 (s, 1H), 7.88-7.93 (m, 1H), 7.58-7.64 (m, 1H), 7.51 (d, J=8.3 Hz, 1H), 7.28-7.34 (m, 1H), 6.80-7.10 (m, 1H), 6.15-6.56 (m, 2H), 3.96-4.10 (m, 1H), 3.75-3.88 (m, 1H), 2.76-2.89 (m, 1H), 2.61-2.75 (m, 1H), 2.42 (s, 3H). $^{19}$F NMR (376 MHz, CD$_3$OD) δ −86.14, −114.82.

Example 866: (S*)-5-(3-Chloro-6-(4-(difluoromethyl)-1H-1,2,3-triazol-1-yl)-2-fluorophenyl)-2-(3-(difluoromethoxy)-1-(4-(2-methyl-1H-imidazol-1-yl)-1H-pyrazol-1-yl)propyl)pyridine 1-oxide

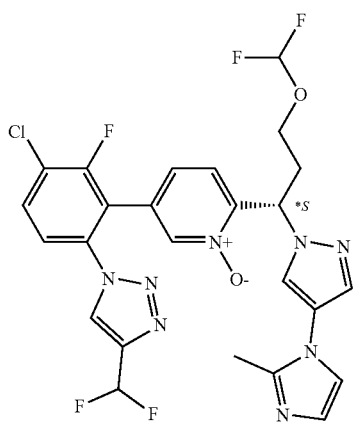 [SMILES: Cc1nccn1-c1cnn([C@@H](CCOC(F)F)c2ccc(-c3c(-n4cc(C(F)F)nn4)ccc(Cl)c3F)c[n+]2[O-])c1]

Step 1: 4-(2-Methyl-1H-imidazol-1-yl)-1-(tetrahydro-2H-pyran-2-yl)-1H-pyrazole

To a solution of 4-iodo-1-(tetrahydro-2H-pyran-2-yl)-1H-pyrazole (2.0 g, 7.19 mmol, 1.0 equiv.) in N,N-dimethylformamide (100.0 mL) was added 2-methyl-1H-imidazole (2.4 g, 28.77 mmol, 4.0 equiv.), cupric acetate (130.6 mg, 0.72 mmol, 0.1 equiv.) and cesium carbonate (7.0 g, 21.58 mmol, 3.0 equiv.). The resulting mixture was maintained under nitrogen and stirred at 130° C. for 3 h. The reaction was quenched with water (50.0 mL). The resulting mixture was extracted with DCM (3×100 mL). The organic layers were combined, dried over anhydrous sodium sulfate, filtered, and concentrated. The resulting residue was purified by silica gel chromatography (0→20% ethyl acetate/petroleum ether) to yield 4-(2-methyl-1H-imidazol-1-yl)-1-(tetrahydro-2H-pyran-2-yl)-1H-pyrazole as a yellow oil. LC/MS: mass calculated for C$_{12}$H$_{16}$N$_4$O: 232.13, measured (ES, m/z): 233.20 [M+H]$^+$.

Step 2: 4-(2-Methyl-1H-imidazol-1-yl)-1H-pyrazole

To a solution of 4-(2-methyl-1H-imidazol-1-yl)-1-(tetrahydro-2H-pyran-2-yl)-1H-pyrazole (1.0 g, 4.31 mmol, 1.0 equiv.) in CH$_3$OH (20.0 mL) was added 4M HCl in 1,4-dioxane (5.0 mL). The resulting mixture was stirred at room temperature for 3 h. The resulting mixture was concentrated under reduced pressure to yield 4-(2-methyl-1H-imidazol-1-yl)-1H-pyrazole. LC/MS: mass calculated for C$_7$H$_8$N$_4$: 148.07, measured (ES, m/z): 149.25 [M+H]$^+$.

Step 3: 5-Bromo-2-(3-(difluoromethoxy)-1-(4-(2-methyl-1H-imidazol-1-yl)-1H-pyrazol-1-yl)propyl)pyridine To a solution of 4-(2-methyl-1H-imidazol-1-yl)-1H-pyrazole (130.0 mg, 0.88 mmol, 1.0 equiv.) in acetonitrile (15.0 mL) was added cesium carbonate (228.7 mg, 0.70 mmol, 0.8 equiv.) and the resulting mixture stirred at room temperature for 0.5 h. 1-(5-Bromopyridin-2-yl)-3-(difluoromethoxy)propyl methanesulfonate (316.0 mg, 0.88 mmol, 1.0 equiv.) was added. The resulting mixture was heated at 70° C. for 2 h. The reaction was quenched with water (50 mL). The resulting mixture was extracted with ethyl acetate (3×50 mL). The organic layers were combined, dried over anhydrous sodium sulfate, filtered and concentrated. The resulting residue was purified by silica gel chromatography (0→20% DCM/MeOH) to yield 5-bromo-2-(3-(difluoromethoxy)-1-(4-(2-methyl-1H-imidazol-1-yl)-1H-pyrazol-1-yl)propyl)pyridine as a yellow oil. LC/MS: mass calculated for C$_{16}$H$_{16}$BrF$_2$N$_5$O: 411.05, measured (ES, m/z): 412.00 [M+H]$^+$.

Step 4: (6-(3-(Difluoromethoxy)-1-(4-(2-methyl-1H-imidazol-1-yl)-1H-pyrazol-1-yl)propyl)pyridin-3-yl)boronic acid To a solution of 5-bromo-2-(3-(difluoromethoxy)-1-(4-(2-methyl-1H-imidazol-1-yl)-1H-pyrazol-1-yl)propyl)pyridine (290.0 mg, 0.70 mmol, 1.0 equiv.) in 1,4-dioxane (15.0 mL) was added 4,4,4',4',5,5,5',5'-octamethyl-2,2'-bi(1,3,2-dioxaborolane) (267.9 mg, 1.06 mmol, 1.5 equiv.) [1,1'-bis(diphenylphosphino)ferrocene]dichloropalladium(II) (51 mg, 0.07 mmol, 0.1 equiv.) and potassium acetate (103.6 mg, 1.06 mmol, 1.5 equiv.). The resulting mixture was maintained under nitrogen and stirred at 90° C. for 16 h. The reaction was quenched with water (50 mL). The resulting mixture was extracted with ethyl acetate (3×50 mL). The organic layers were combined, dried over anhydrous sodium sulfate, filtered and concentrated to yield the (6-(3-(difluoromethoxy)-1-(4-(2-methyl-1H-imidazol-1-yl)-1H-pyrazol-1-yl)propyl)pyridin-3-yl)boronic acid as a yellow oil. LC/MS: mass calculated for C$_{16}$H$_{18}$BF$_2$N$_5$O$_3$: 377.15, measured (ES, m/z): 378.10 [M+H]$^+$.

Step 5: 5-(3-Chloro-6-(4-(difluoromethyl)-1H-1,2,3-triazol-1-yl)-2-fluorophenyl)-2-(3-(difluoromethoxy)-1-(4-(2-methyl-1H-imidazol-1-yl)-1H-pyrazol-1-yl)propyl)pyridine To a solution of (6-(3-(difluoromethoxy)-1-(4-(2-methyl-1H-imidazol-1-yl)-1H-pyrazol-1-yl)propyl)pyridin-3-yl)boronic acid (250.0 mg, 0.66 mmol, 1.0 equiv.) in 1,4-dioxane (20.0 mL) and water (2.0 mL) was added 1-(4-chloro-3-fluoro-2-iodophenyl)-4-(difluoromethyl)-1H-1,2,3-triazole (297.1 mg, 0.80 mmol, 1.1 equiv.), tetrakis(triphenylphosphine)palladium (91.9 mg, 0.06 mmol, 0.1 equiv.) and potassium carbonate (165 mg, 1.19 mmol, 1.7 equiv.). The resulting mixture was maintained under nitrogen and stirred at 90° C. for 3 h. The resulting mixture was extracted with ethyl acetate (3×50 mL). The organic layers were combined, dried over anhydrous sodium sulfate, filtered and concentrated. The resulting residue was purified by silica gel chromatography (0→80% ethyl acetate/petroleum ether) to yield the 5-(3-chloro-6-(4-(difluoromethyl)-1H-1,2,3-triazol-1-yl)-2-fluorophenyl)-2-(3-(difluoromethoxy)-1-(4-(2-methyl-1H-imidazol-1-yl)-1H-pyrazol-1-yl)propyl)pyridine as a yellow oil. LC/MS: mass calculated for $C_{25}H_{20}ClF_5N_8O$: 578.14, measured (ES, m/z): 579.30 $[M+H]^+$.

Step 6: (S*)-5-(3-Chloro-6-(4-(difluoromethyl)-1H-1,2,3-triazol-1-yl)-2-fluorophenyl)-2-(3-(difluoromethoxy)-1-(4-(2-methyl-1H-imidazol-1-yl)-1H-pyrazol-1-yl)propyl)pyridine 1-oxide To a solution of 5-(3-chloro-6-(4-(difluoromethyl)-1H-1,2,3-triazol-1-yl)-2-fluorophenyl)-2-(3-(difluoromethoxy)-1-(4-(2-methyl-1H-imidazol-1-yl)-1H-pyrazol-1-yl)propyl)pyridine (100.0 mg, 0.17 mmol, 1.0 equiv.) in DCM was added peroxyacetic acid (2 mL). The resulting mixture was stirred for 3 h. The mixture was diluted with water, and the mixture extracted with ethyl acetate (50 mL×3), the combined extracts were evaporated and then purified by silica gel chromatography with MeOH/DCM (0→10%) to yield the resulting residue, which was purified by chiral-HPLC with mobile phase: MtBE(0.1% DEA):EtOH=85:15 to yield (S*)-5-(3-chloro-6-(4-(difluoromethyl)-1H-1,2,3-triazol-1-yl)-2-fluorophenyl)-2-(3-(difluoromethoxy)-1-(4-(2-methyl-1H-imidazol-1-yl)-1H-pyrazol-1-yl)propyl)pyridine 1-oxide as a yellow solid.

LC/MS: mass calculated for $C_{25}H_{20}ClF_5N_8O_2$: 594.13, measured (ES, m/z): 595.05$[M+H]^+$. $^1H$ NMR (400 MHz, $CD_3OD$) δ 8.55 (s, 1H), 8.45 (s, 1H), 8.35 (s, 1H), 7.81-7.98 (m, 2H), 7.68 (d, J=8.3 Hz, 1H), 7.65-7.67 (m, 1H), 7.55-7.64 (m, 1H), 7.45 (s, 1H), 7.31-7.42 (m, 1H), 6.80-7.10 (m, 1H), 6.18-6.58 (m, 2H), 3.99-4.08 (m, 1H), 3.71-3.78 (m, 1H), 2.80-2.95 (m, 1H), 2.63-2.77 (m, 1H), 2.55 (s, 3H). $^{19}F$ NMR (376 MHz, $CD_3OD$) δ −76.92, −86.13, −114.76.

Example 867: (R*)-5-(3-Chloro-6-(4-(difluoromethyl)-1H-1,2,3-triazol-1-yl)-2-fluorophenyl)-2-(3-(difluoromethoxy)-1-(4-(3-methyl-4H-1,2,4-triazol-4-yl)-1H-pyrazol-1-yl)propyl)pyridine 1-oxide

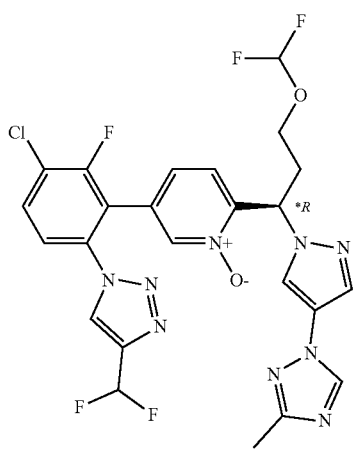 [SMILES: Cc1ncn(-c2cnn([C@H](CCOC(F)F)c3ccc(-c4c(-n5cc(C(F)F)nn5)ccc(Cl)c4F)c[n+]3[O-])c2)n1]

LC/MS: mass calculated for $C_{24}H_{19}ClF_5N_9O_2$: 595.13, measured (ES, m/z): 596.05 $[M+H]^+$. $^1H$ NMR (400 MHz, $CD_3OD$) δ 8.71 (s, 1H), 8.55 (s, 1H), 8.32-8.38 (m, 2H), 7.99 (s, 1H), 7.89-7.94 (m, 1H), 7.58-7.62 (m, 1H), 7.50-7.53 (m, 1H), 7.30-7.33 (m, 1H), 6.95 (t, J=54.4 Hz, 1H), 6.15-6.59 (m, 2H), 3.95-4.05 (m, 1H), 3.70-3.89 (m, 1H), 2.78-2.89 (m, 1H), 2.61-2.77 (m, 1H), 2.43 (s, 3H). $^{19}F$ NMR (376 MHz, $CD_3OD$) δ −76.97, −86.14, −114.17, −114.83.

Example 868: (R*)-5-(3-Chloro-6-(4-(difluoromethyl)-1H-1,2,3-triazol-1-yl)-2-fluorophenyl)-2-(3-(difluoromethoxy)-1-(4-(2-methyl-1H-imidazol-1-yl)-1H-pyrazol-1-yl)propyl)pyridine 1-oxide

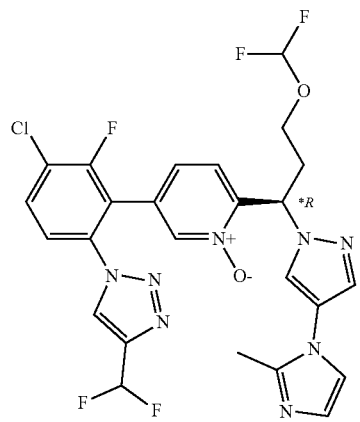 [SMILES: Cc1nccn1-c1cnn([C@H](CCOC(F)F)c2ccc(-c3c(-n4cc(C(F)F)nn4)ccc(Cl)c3F)c[n+]2[O-])c1]

LC/MS: mass calculated for $C_{25}H_{20}ClF_5N_8O_2$: 594.13, measured (ES, m/z): 595.05 $[M+H]^+$. $^1H$ NMR (400 MHz, $CD_3OD$) δ 8.55 (s, 1H), 8.45 (s, 1H), 8.36 (s, 1H), 7.88-7.97 (m, 2H), 7.67-7.70 (m, 1H), 7.59-7.63 (m, 2H), 7.52-7.56 (m, 1H), 7.34-7.39 (m, 1H), 6.96 (t, J=54.4 Hz, 1H), 6.18-6.62 (m, 2H), 4.01-4.08 (m, 1H), 3.71-3.87 (m, 1H), 2.79-2.88 (m, 1H), 2.67-2.75 (m, 1H), 2.60 (s, 3H). $^{19}F$ NMR (376 MHz, $CD_3OD$) δ −76.93, −86.13, −114.23, −114.77.

Example 869: (R*)-5-(3-Chloro-6-(4-(difluoromethyl)-1H-1,2,3-triazol-1-yl)-2-fluorophenyl)-2-(3-(difluoromethoxy)-1-(4-(3-methyl-1H-1,24-triazol-1-yl)-1H-pyrazol-1-yl)propyl)pyridine 1-oxide

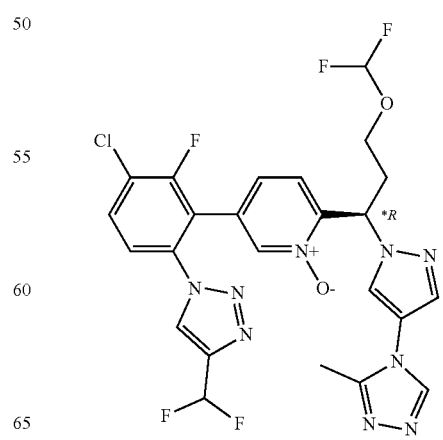

LC/MS: mass calculated for $C_{24}H_{19}ClF_5N_9O_2$: 595.13, measured (ES, m/z): 596.10 [M+H]$^+$. $^1$H NMR (400 MHz, CD$_3$OD) 8.55 (s, 1H), 8.39 (s, 1H), 8.34 (s, 1H), 7.82-8.01 (m, 3H), 7.61 (dd, J=8.7, 1.6 Hz, 1H), 7.55 (d, J=8.3 Hz, 1H), 7.30 (dd, J=8.4, 1.7 Hz, 1H), 6.79-7.10 (t, J=8.4 Hz, 1H), 6.15-6.65 (m, 2H), 3.95-4.02 (m, 1H), 3.71-3.89 (m, 1H), 2.79-2.90 (m, 1H), 2.60-2.75 (m, 1H), 2.51 (s, 3H)./19F NMR (376 MHz, CD$_3$OD) d −114.793, −86.160, −76.933.

Example 870: (S*)-5-(3-Chloro-6-(4-(difluoromethyl)-1H-1,2,3-triazol-1-yl)-2-fluorophenyl)-2-(3-(difluoromethoxy)-1-(4-(3-methyl-1H-1,2,4-triazol-1-yl)-1H-pyrazol-1-yl)propyl)pyridine 1-oxide

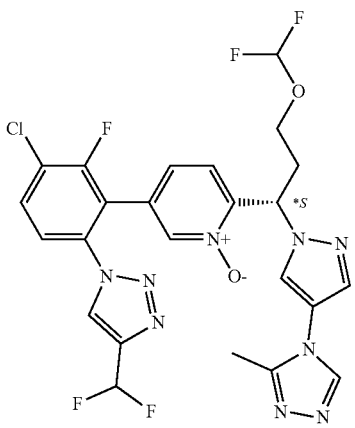 [SMILES: Cc1nncn1-c1cnn([C@@H](CCOC(F)F)c2ccc(-c3c(-n4cc(C(F)F)nn4)ccc(Cl)c3F)c[n+]2[O-])c1]

Step 1: 3-Methyl-4-(1-(tetrahydro-2H-pyran-2-yl)-1H-pyrazol-4-yl)-4H-1,2,4-triazole To a solution of 4-iodo-1-(tetrahydro-2H-pyran-2-yl)-1H-pyrazole (4.0 g, 14.38 mmol, 1.0 equiv.) in N,N-dimethylformamide (100 mL) was added 3-methyl-4H-1,2,4-triazole (4.8 g, 57.53 mmol, 4.0 equiv.), cupric acetate (261.3 mg, 1.44 mmol, 0.1 equiv.) and cesium carbonate (14.1 g, 43.15 mmol, 3.0 equiv.). The resulting mixture was maintained under nitrogen and stirred at 130° C. for 16 h. The reaction was quenched with water (250 mL). The resulting mixture was extracted with DCM (3×250 mL). The organic layers were combined, dried over anhydrous sodium sulfate, filtered and concentrated. The resulting residue was purified by silica gel chromatography (0→20% ethyl acetate/petroleum ether) to yield 3-methyl-4-(1-(tetrahydro-2H-pyran-2-yl)-1H-pyrazol-4-yl)-4H-1,2,4-triazole as a yellow oil. LC/MS: mass calculated for $C_{11}H_{15}N_5O$: 233.13, measured (ES, m/z): 234.25 [M+H]$^+$.

Step 2: 3-Methyl-4-(1H-pyrazol-4-yl)-4H-1,2,4-triazole

To a solution of 4-(2-methyl-1H-imidazol-1-yl)-1-(tetrahydro-2H-pyran-2-yl)-1H-pyrazole (1.0 g, 4.29 mmol, 1.0 equiv.) in CH$_3$OH (20.0 mL) was added 4M HCl in 1,4-dioxane (5.0 mL). The resulting mixture was stirred at room temperature for 3H. The resulting mixture was concentrated under reduced pressure to yield 3-methyl-4-(1H-pyrazol-4-yl)-4H-1,2,4-triazole as a residue. (300.0 mg resulting). LC/MS: mass calculated For $C_6H_7N_5$: 149.07, measured (ES, m/z): 150.25 [M+H]$^+$.

Step 3: 5-Bromo-2-(3-(difluoromethoxy)-1-(4-(3-methyl-4H-1,2,4-triazol-4-yl)-1H-pyrazol-1-yl)propyl)pyridine To a solution of 3-methyl-4-(1H-pyrazol-4-yl)-4H-1,2,4-triazole (500.0 mg, 3.33 mmol, 1.0 equiv.) in acetonitrile (20.0 mL) was added cesium carbonate (873.8 mg, 2.68 mmol, 0.8 equiv.), after stirred at room temperature for 0.5 h. 1-(5-Bromopyridin-2-yl)-3-(difluoromethoxy)propyl methanesulfonate (1.2 g, 3.33 mmol, 1.0 equiv.) was then added. The resulting mixture was heated at 70° C. for 2 h. The resulting mixture was extracted with ethyl acetate (3×50 mL). The organic layers were combined, dried over anhydrous sodium sulfate, filtered and concentrated. The resulting residue was purified by silica gel chromatography (0→60% ethyl acetate/petroleum ether) to yield the 5-bromo-2-(3-(difluoromethoxy)-1-(4-(3-methyl-4H-1,2,4-triazol-4-yl)-1H-pyrazol-1-yl)propyl)pyridine as a yellow oil. LC/MS: mass calculated for $C_{15}H_{15}BrF_2N_6O$: 412.05, measured (ES, m/z): 413.05 [M+H]$^+$.

Step 4: (6-(3-(Difluoromethoxy)-1-(4-(3-methyl-4H-1,2,4-triazol-4-yl)-1H-pyrazol-1-yl)propyl)pyridin-3-yl)boronic acid To a solution of 5-bromo-2-(3-(difluoromethoxy)-1-(4-(3-methyl-4H-1,2,4-triazol-4-yl)-1H-pyrazol-1-yl)propyl)pyridine (590.0 mg, 1.43 mmol, 1.0 equiv.) in 1,4-dioxane (20.0 mL) was added 4,4,4',4',5,5,5',5'-octamethyl-2,2'-bi(1,3,2-dioxaborolane) (543.8 mg, 2.14 mmol, 1.5 equiv.) [1,1'-bis(diphenylphosphino)ferrocene]dichloropalladium(II) (104.5 mg, 0.14 mmol, 0.1 equiv.) and potassium acetate (210.2 mg, 2.14 mmol, 1.5 equiv.). The resulting mixture was maintained under nitrogen and stirred at 90° C. for 16 h. The resulting mixture was extracted with ethyl acetate (3×50 mL). The organic layers were combined, dried over anhydrous sodium sulfate, filtered and concentrated under reduced pressure to yield (6-(3-(difluoromethoxy)-1-(4-(3-methyl-4H-1,2,4-triazol-4-yl)-1H-pyrazol-1-yl)propyl)pyridin-3-yl)boronic acid as a dark oil. LC/MS: mass calculated for $C_{15}H_{17}BF_2N_6O_3$: 378.14, measured (ES, m/z): 379.20 [M+H]$^+$.

Step 5: 5-(3-Chloro-6-(4-(difluoromethyl)-1H-1,2,3-triazol-1-yl)-2-fluorophenyl)-2-(3-(difluoromethoxy)-1-(4-(3-methyl-4H-1,2,4-triazol-4-yl)-1H-pyrazol-1-yl)propyl)pyridine To a solution of (6-(3-(difluoromethoxy)-1-(4-(3-methyl-4H-1,2,4-triazol-4-yl)-1H-pyrazol-1-yl)propyl)pyridin-3-yl) boronic acid (300.0 mg, 0.79 mmol, 1.0 equiv.) in 1,4-dioxane (10.0 mL) and water (1.0 mL) was added 1-(4-chloro-3-fluoro-2-iodophenyl)-4-(difluoromethyl)-1H-1,2,3-triazole (296.3 mg, 0.79 mmol, 1.0 equiv.), tetrakis(triphenylphosphine)palladium (92 mg, 0.08 mmol, 0.1 equiv.) and potassium carbonate (164.5 mg, 1.19 mmol, 1.5 equiv.). The resulting mixture was maintained under nitrogen and stirred at 90° C. for 2 h. The reaction was quenched with water (50 mL). The resulting mixture was extracted with ethyl acetate (3×50 mL). The organic layers were combined, dried over anhydrous sodium sulfate, filtered and concentrated. The resulting residue was purified by silica gel chromatography (0→80% ethyl acetate/petroleum ether) to yield 5-(3-chloro-6-(4-(difluoromethyl)-1H-1,2,3-triazol-1-yl)-2-fluorophenyl)-2-(3-(difluoromethoxy)-1-(4-(3-methyl-4H-1,2,4-triazol-4-yl)-1H-pyrazol-1-yl)propyl)pyri- Step 6: (S*)-5-(3-Chloro-6-(4-(difluoromethyl)-1H-1,2,3-triazol-1-yl)-2-fluorophenyl)-2-(3-(difluoromethoxy)-1-(4-(3-methyl-4H-1,2,4-triazol-4-yl)-1H-pyrazol-1-yl)propyl)pyridine 1-oxide To a solution of 5-(3-chloro-6-(4-(difluoromethyl)-1H-1,2,3-triazol-1-yl)-2-fluorophenyl)-2-(3-(difluoromethoxy)-1-(4-(3-methyl-4H-1,2,4-triazol-4-yl)-1H-pyrazol-1-yl)propyl)pyridine (140.0 mg, 0.24 mmol, 1.0 equiv.) in $CH_3OH$ (5.0 mL) was added methyltrioxorhenium (VII) (6 mg, 0.02 mmol, 0.1 equiv.) and hydrogen peroxide (0.5 mL, 30 wt. %). The mixture was stirred at room temperature for 1 h. The mixture was purified by silica gel chromatography with MeOH/DCM (0→10%) to yield a residue, which was purified by chiral-HPLC with mobile phase: MtBE(0.1% DEA):EtOH=60:40 to yield (S*)-5-(3-chloro-6-(4-(difluoromethyl)-1H-1,2,3-triazol-1-yl)-2-fluorophenyl)-2-(3-(difluoromethoxy)-1-(4-(3-methyl-4H-1,2,4-triazol-4-yl)-1H-pyrazol-1-yl)propyl)pyridine 1-oxide as a white solid. LC/MS: mass calculated for $C_{24}H_{19}ClF_5N_9O_2$: 595.13, measured (ES, m/z): 596.10 [M+H]+. $^1$H NMR (400 MHz, $CD_3OD$) δ 8.55 (s, 1H), 8.38 (d, J=4.4 Hz, 2H), 7.85-8.01 (m, 3H), 7.60-7.63 (m, 1H), 7.55 (d, J=8.3 Hz, 1H), 7.30-7.37 (m, 1H), 6.76-7.11 (m, 1H), 6.13-6.61 (m, 2H), 3.98-4.10 (m, 1H), 3.72-3.85 (m, 1H), 2.79-2.90 (m, 1H), 2.61-2.78 (m, 1H), 2.51 (s, 3H). $^{19}$F NMR (376 MHz, $CD_3OD$) δ −86.12, −114.18, −114.80.

Example 871: (R*)-5-(3-Chloro-2-fluoro-6-(4-(trifluoromethyl)-1H-1,2,3-triazol-1-yl)phenyl)-2-(1-(4-(cyclopropanecarboxamido)-2-(methyl-d3)-1'H,2H-[3,4'-bipyrazol]-1'-yl)-3-(difluoromethoxy)propyl)pyridine 1-oxide

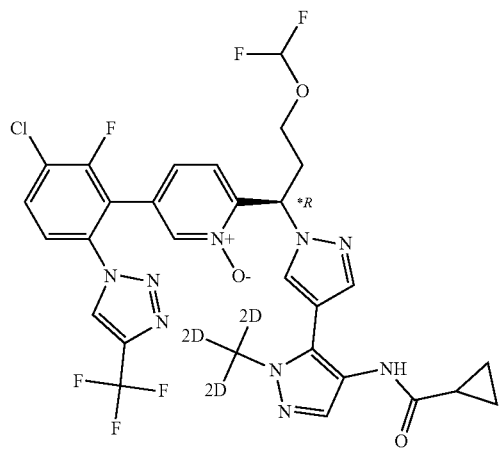

LC/MS: mass calculated for $C_{29}H_{21}ClD_3F_6N_9O_3$: 698.2, measured (ES, m/z): 699.2 [M+H]+. $^1$H NMR (400 MHz, DMSO-$d_6$) δ 9.35 (s, 1H), 9.18 (s, 1H), 8.44 (d, J=1.6 Hz, 1H), 8.32 (s, 1H), 8.02-8.10 (m, 1H), 7.83 (s, 1H), 7.74-7.80 (m, 1H), 7.49 (s, 1H), 7.32-7.38 (m, 1H), 7.15-7.20 (m, 1H), 6.62 (t, J=75.7 Hz, 1H), 6.21-6.29 (m, 1H), 3.80-3.89 (m, 1H), 3.65-3.73 (m, 1H), 2.52-2.69 (m, 2H), 1.70-1.81 (m, 1H), 0.66-0.76 (m, 4H). $^{19}$F NMR (376 MHz, DMSO-$d_6$) δ −59.78, −83.25, −112.82.

Example 872: (S*)-5-(3-Chloro-2-fluoro-6-(4-(trifluoromethyl)-1H-1,2,3-triazol-1-yl)phenyl)-2-(1-(4-(cyclopropanecarboxamido)-2-(methyl-d3)-1'H,2H-[3,4'-bipyrazol]-1'-yl)-3-(difluoromethoxy)propyl)pyridine 1-oxide

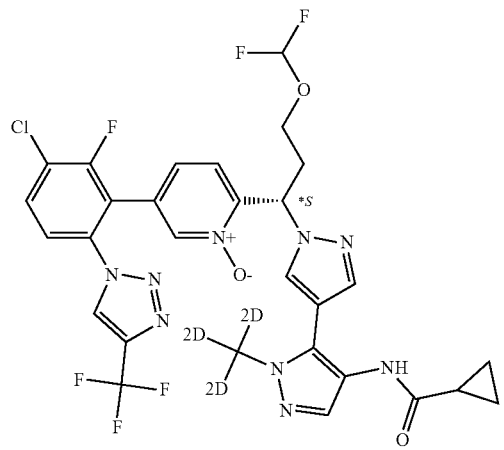

LC/MS: mass calculated for $C_{29}H_{21}ClD_3F_6N_9O_3$: 698.2, measured (ES, m/z): 699.2 [M+H]+. $^1$H NMR (400 MHz, DMSO-$d_6$) δ 9.35 (s, 1H), 9.18 (s, 1H), 8.44 (s, 1H), 8.31 (s, 1H), 8.02-8.10 (m, 1H), 7.83 (s, 1H), 7.74-7.80 (m, 1H), 7.49 (s, 1H), 7.32-7.38 (m, 1H), 7.15-7.20 (m, 1H), 6.62 (t, J=75.7 Hz, 1H), 6.21-6.29 (m, 1H), 3.80-3.89 (m, 1H), 3.65-3.73 (m, 1H), 2.48-2.70 (m, 2H), 1.73-1.79 (m, 1H), 0.66-0.76 (m, 4H). $^{19}$F NMR (376 MHz, DMSO-$d_6$) δ −59.78, −83.26, −112.82.

Example 873: (S*)-2-(1-(4-(5-Amino-3-fluoropyrazin-2-yl)-1H-pyrazol-1-yl)-3-(difluoromethoxy)propyl)-5-(3-chloro-2-fluoro-6-(4-(trifluoromethyl)-1H-1,2,3-triazol-1-ylphenyl)pyridine 1-oxide

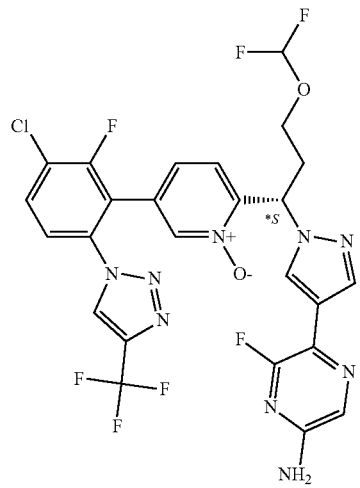 [SMILES: Nc1cnc(-c2cnn([C@@H](CCOC(F)F)c3ccc(-c4c(-n5cc(C(F)(F)F)nn5)ccc(Cl)c4F)c[n+]3[O-])c2)c(F)n1]

LC/MS: mass calculated for $C_{25}H_{17}ClF_7N_9O_2$: 643.11, measured (ES, m/z): 644.00 [M+H]+. $^1$H NMR (300 MHz, DMSO-$d_6$) δ 9.15 (d, J=1.0 Hz, 1H), 8.41-8.44 (m, 1H), 8.23 (d, J=1.9 Hz, 1H), 8.05 (dd, J=8.7, 7.7 Hz, 1H), 7.93 (d, J=1.5 Hz, 1H), 7.72-7.85 (m, 2H), 7.24 (d, J=8.3 Hz, 1H), 7.13 (dd, J=8.3, 1.6 Hz, 1H), 6.37-6.91 (m, 3H), 6.21 (dd, J=10.1, 4.5 Hz, 1H), 3.58-3.93 (m, 2H), 2.56-2.61 (m, 2H). $^{19}$F NMR (282 MHz, DMSO) d −59.47, −80.64, −83.31, −112.91.

Example 874: (R)-5-(3-Chloro-2-fluoro-6-(4-(trifluoromethyl)-1H-1,2,3-triazol-1-yl)phenyl)-2-(3-(difluoromethoxy)-1-(4-(1-methyl-1H-1,2,4-triazol-5-yl)-1H-pyrazol-1-yl)propyl-1,3,3-d$_3$)pyridine 1-oxide

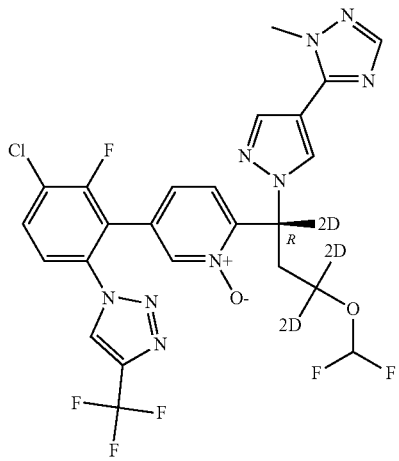

Step 1:
1-(5-Bromopyridin-2-yl)propane-1,3,3-d3-1,3-diol

To a solution of ethyl 3-(5-bromopyridin-2-yl)-3-oxopropanoate (2 g, 7.35 mmol, 1 equiv.) in CH$_3$OH (20 mL) was added sodium tetrahydroborate-d$_4$ (2.5 g, 58.80 mmol, 8 equiv.) at 0° C. The mixture was stirred at room temperature for 30 min., then heated at 60° C. for 1 h. The resulting mixture was quenched by water (30 mL) and extract with EA (3×30 mL). Then the organic layers were combined, washed with brine, dried over Na$_2$SO$_4$ and concentrated to yield 1-(5-bromopyridin-2-yl)propane-1,3,3-d3-1,3-diol as a light yellow oil. LC/MS: mass calculated for C$_8$H$_7$D$_3$BrNO$_2$: 234.01, measured (ES, m/z): 237.00 [M+H+2]$^+$.

Step 2: 1-(5-Bromopyridin-2-yl)-3-hydroxypropan-1-one-3,3-d2

To a solution of 1-(5-bromopyridin-2-yl)propane-1,3,3-d3-1,3-diol (1.7 g, 7.02 mmol, 1 equiv.) in DCM (20 mL) was added manganese dioxide (12.2 g, 140.40 mmol, 20 equiv.). The resulting mixture was stirred at 50° C. for 48 h. The catalyst was filtered out. The filtrate was concentrated under reduced pressure and the residue was purified by silica gel column chromatography (EA/PE, 0%→50%) to yield 1-(5-bromopyridin-2-yl)-3-hydroxypropan-1-one-3,3-d$_2$ as a brown solid. LC/MS: mass calculated for C$_8$H$_6$D$_2$BrNO$_2$: 230.99, measured (ES, m/z): 231.95 [M+H]$^+$.

Step 3: 1-(5-Bromopyridin-2-yl)-3-(difluoromethoxy)propan-1-one-3,3-d2

To a solution of 1-(5-bromopyridin-2-yl)-3-hydroxypropan-1-one-3,3-d$_2$ (650 mg, 2.80 mmol, 1.0 equiv.) in DCM/ H$_2$O (6 mL) were added potassium acetate (1.1 g, 11.20 mmol, 4.0 equiv.) and TMSCF$_2$Br (1.4 ml, 2.80 mmol, 1.0 equiv.) dropwise over 30 min at 0~10° C. The resulting mixture was stirred for 2 h, then diluted with water, extracted with DCM (3×15 mL) and the organic layers were separated, combined, washed with brine, dried over Na$_2$SO$_4$ and concentrated to yield 1-(5-bromopyridin-2-yl)-3-(difluoromethoxy)propan-1-one-3,3-d$_2$ as a black oil. LC/MS: mass calculated for C$_9$H$_6$D$_2$BrF$_2$NO$_2$: 280.98, measured (ES, m/z): 283.95 [M+H+2]$^+$.

Step 4: 1-(5-Bromopyridin-2-yl)-3-(difluoromethoxy)propan-1,3,3-d3-1-ol

To a solution of ethyl 3-(5-bromopyridin-2-yl)-3-oxopropanoate (639 mg, 2.27 mmol, 1.0 equiv.) in CH$_3$OH (10 mL) was added sodium tetrahydroborate-d$_4$ (759 mg, 18.12 mmol, 8.0 equiv.) at room temperature. The mixture was stirred at room temperature for 30 min, then stirred at 60° C. for 1 h. The resulting mixture was quenched by water (20 mL) and extract with EA (3×20 mL). Then the organic layers were combined, washed with brine, dried over Na$_2$SO$_4$ and concentrated to yield 1-(5-bromopyridin-2-yl)-3-(difluoromethoxy)propan-1,3,3-d3-1-ol as black oil. LC/MS: mass calculated for C$_9$H$_7$D$_3$BrF$_2$NO$_2$: 284.01, measured (ES, m/z): 284.95 [M+H]$^+$.

Step 5: 1-(5-Bromopyridin-2-yl)-3-(difluoromethoxy)propyl-1,3,3-d3 methanesulfonate To a solution of 1-(5-bromopyridin-2-yl)-3-(difluoromethoxy)propan-1,3,3-d3-1-ol (640 mg, 2.25 mmol, 1.0 equiv.) in dichloromethane (7 mL) was added triethylamine (909 mg, 8.98 mmol, 4.0 equiv.) at 0° C. Then methanesulfonic anhydride (782 mg, 4.49 mmol, 2.0 equiv.) was added. The resulting mixture was stirred at room temperature for 2 h. The reaction was quenched by water (10 mL), extracted with EA (3×20 mL). The organic layers were combined, washed with brine, dried over Na$_2$SO$_4$ and concentrated. The residue was purified by silica gel chromatography (EA/PE, 0%→60%) to yield 1-(5-bromopyridin-2-yl)-3-(difluoromethoxy)propyl-1,3,3-d3 methanesulfonate as a yellow solid. LC/MS: mass calculated for C$_{10}$H$_9$D$_3$BrF$_2$NO$_4$S: 361.98, measured (ES, m/z): 364.90 [M+H+2]$^+$.

Step 6: 5-Bromo-2-(3-(difluoromethoxy)-1-(4-(1-methyl-1H-1,2,4-triazol-5-yl)-1H-pyrazol-1-yl)propyl-1,3,3-d3)pyridine A mixture of cesium carbonate (287 mg, 0.88 mmol, 1.0 equiv.) and 4-methyl-3-(1H-pyrazol-4-yl)-4H-1,2,4-triazole (131 mg, 0.88 mmol, 1.0 equiv.) in acetonitrile (3 mL) was stirred for 15 min at room temperature. 1-(5-Bromopyridin-2-yl)-3-(difluoromethoxy)propyl-1,3,3-d$_3$ methanesulfonate (320 mg, 0.88 mmol, 1.0 equiv.) was added and the solution was stirred for 2.5 h at 90° C. The resulting mixture was diluted with water (20 mL), extracted with EA (3×20 mL). Then the organic layers were combined, washed with brine, dried over Na$_2$SO$_4$ and concentrated. The resulting mixture was purified by silica gel column (EA/PE, 0%→80%) to yield 5-bromo-2-(3-(difluoromethoxy)-1-(4-(1-methyl-1H-1,2,4-triazol-5-yl)-1H-pyrazol-1-yl)propyl-1,3,3-d$_3$)pyridine as a yellow oil. LC/MS: mass calculated for C$_{15}$H$_{12}$D$_3$BrF$_2$N$_6$O: 415.06, measured (ES, m/z): 415.95 [M+H]$^+$.

Step 7: (6-(3-(Difluoromethoxy)-1-(4-(1-methyl-1H-1,2,4-triazol-5-yl)-1H-pyrazol-1-yl)propyl-1,3,3-d3) pyridin-3-yl)boronic acid A mixture of 5-bromo-2-(3-(difluoromethoxy-d)-1-(4-(1-methyl-1H-1,2,4-triazol-5-yl)-1H-pyrazol-1-yl)propyl-3,3-d2)pyridine (369 mg, 0.88 mmol, 1.0 equiv.), 4,4,4',4',5,5,5',5'-octamethyl-2,2'-bi(1,3,2-dioxaborolane) (338 mg, 1.33 mmol, 1.5 equiv.), Pd(dppf)Cl$_2$ (65 mg, 0.09 mmol, 0.1 equiv.) and KOAc (261 mg, 2.66 mmol, 3.0 equiv.) in 1,4-dioxane (5 mL) was stirred for 2 h at 90° C. The resulting mixture was diluted with water (10 mL), extracted with EA (3×10 mL). The organic layers were combined, washed with brine, dried over Na$_2$SO$_4$ and concentrated. The residue was purified by silica gel chromatography to yield (6-(3-(difluoromethoxy-d)-1-(4-(1-methyl-1H-1,2,4-triazol-5-yl)-1H-pyrazol-1-yl)propyl-3,3-d2)pyridin-3-yl)boronic acid as a black oil. LC/MS: mass calculated for C$_{15}$H$_{14}$D$_3$BF$_2$N$_6$O$_3$: 381.16, measured (ES, m/z): 382.05 [M+H]$^+$.

Step 8: 5-(3-Chloro-2-fluoro-6-(4-(trifluoromethyl)-1H-1,2,3-triazol-1-yl)phenyl)-2-(3-(difluoromethoxy)-1-(4-(1-methyl-1H-1,2,4-triazol-5-yl)-1H-pyrazol-1-yl)propyl-1,3,3-d3)pyridine A mixture of 1-(4-chloro-3-fluoro-2-iodophenyl)-4-(trifluoromethyl)-1H-1,2,3-triazole (279 mg, 0.71 mmol, 1.2 equiv.), (6-(3-(difluoromethoxy)-1-(4-(1-methyl-1H-1,2,4-triazol-5-yl)-1H-pyrazol-1-yl)propyl-1,3,3-d3)pyridin-3-yl) boronic acid (226 mg, 0.59 mmol, 1.0 equiv.), Pd(PPh$_3$)$_4$ (69 mg, 0.06 mmol, 0.1 equiv.) and K$_2$CO$_3$ (246 mg, 1.78 mmol, 3.0 equiv.) in 1,4-dioxane/water (V/V=4:1, 2.4 mL) was refluxed at 90° C. under N$_2$ for 3 h. The resulting mixture was diluted with water (10 mL), extracted with EA (3×10 mL). The organic layers were combined, washed with brine, dried over Na$_2$SO$_4$ and concentrated. The resulting residue was purified by silica gel chromatography to yield 5-(3-chloro-2-fluoro-6-(4-(trifluoromethyl)-1H-1,2,3-triazol-1-yl)phenyl)-2-(3-(difluoromethoxy)-1-(4-(1-methyl-1H-1,2,4-triazol-5-yl)-1H-pyrazol-1-yl)propyl-1,3,3-d3)pyridine as a light yellow oil. LC/MS: mass calculated for C$_{24}$H$_{15}$D$_3$ClF$_6$N$_9$O: 600.14, measured (ES, m/z): 601.05 [M+H]$^+$.

Step 9: (R)-5-(3-Chloro-2-fluoro-6-(4-(trifluoromethyl)-1H-1,2,3-triazol-1-yl)phenyl)-2-(3-(difluoromethoxy)-1-(4-(1-methyl-1H-1,2,4-triazol-5-yl)-1H-pyrazol-1-yl)propyl-1,3,3-d3)pyridine 1-oxide A mixture of 5-(3-chloro-2-fluoro-6-(4-(trifluoromethyl)-1H-1,2,3-triazol-1-yl)phenyl)-2-(3-(difluoromethoxy)-1-(4-(1-methyl-1H-1,2,4-triazol-5-yl)-1H-pyrazol-1-yl)propyl-1,3,3-d3)pyridine (264 mg, 0.44 mmol, 1.0 equiv.), methyltrioxorhenium (55 mg, 0.22 mmol, 0.5 equiv.), hydrogen peroxide (0.07 mL, 30 wt %) in CH$_3$OH (2 mL) was stirred for 3 h at room temperature. The resulting mixture was purified by reverse phase chromatography on C18 (MeCN/H$_2$O (0.05% CF$_3$COOH)) to yield product which was separated by chiral-HPLC to yield (R)-5-(3-chloro-2-fluoro-6-(4-(trifluoromethyl)-1H-1,2,3-triazol-1-yl)phenyl)-2-(3-(difluoromethoxy)-1-(4-(1-methyl-1H-1,2,4-triazol-5-yl)-1H-pyrazol-1-yl)propyl-1,3,3-d3)pyridine 1-oxide as a white solid.

LC/MS: mass calculated for C$_{24}$H$_{15}$ClD$_3$F$_6$N$_9$O$_2$: 616.14, measured (ES, m/z): 617.10 [M+H]$^+$. $^1$H NMR (300 MHz, DMSO-d$_6$) δ 9.19 (s, 1H), 8.62 (s, 1H), 8.45 (s, 1H), 8.02-8.13 (m, 2H), 7.91 (d, J=1.1 Hz, 1H), 7.79 (d, J=8.5 Hz, 1H), 7.34 (d, J=8.0 Hz, 1H), 7.18 (d, J=8.2 Hz, 1H), 6.35-6.93 (m, 1H), 3.94-4.01 (m, 3H), 2.59-2.64 (m, 2H). $^{19}$F-NMR (282 MHz, DMSO-d$_6$) δ −59.78, −83.32, −112.83.

Example 875: (S)-5-(3-Chloro-2-fluoro-6-(4-(trifluoromethyl)-1H-1,2,3-triazol-1-yl)phenyl)-2-(3-(difluoromethoxy)-1-(4-(1-methyl-1H-1,2,4-triazol-5-yl)-1H-pyrazol-1-yl)propyl-1,3,3-d3)pyridine 1-oxide

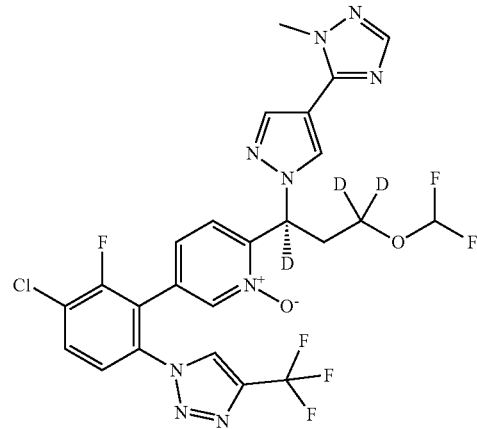 [SMILES: [2H]C([2H])(C[C@@]([2H])(c1ccc(-c2c(-n3cc(C(F)(F)F)nn3)ccc(Cl)c2F)c[n+]1[O-])n1cc(-c2ncnn2C)cn1)OC(F)F]

LC/MS: mass calculated for C$_{24}$H$_{15}$ClD$_3$F$_6$N$_9$O$_2$: 616.14, measured (ES, m/z): 617.10 [M+H]$^+$. $^1$H NMR (300 MHz, DMSO-d$_6$) δ 9.19 (s, 1H), 8.62 (s, 1H), 8.45 (s, 1H), 8.02-8.13 (m, 2H), 7.91 (d, J=1.1 Hz, 1H), 7.77-7.82 (m, 1H), 7.30-7.38 (m, 1H), 7.15-7.21 (m, 1H), 6.64 (t, J=75.7 Hz, 1H), 3.97 (d, J=1.1 Hz, 3H), 2.57-2.71 (m, 2H). $^{19}$F NMR (282 MHz, DMSO-d$_6$) δ −59.78, −73.60, −83.33, −112.83.

Example 876: (S)-5-(3-Chloro-2-fluoro-6-(4-(trifluoromethyl)-1H-1,2,3-triazol-1-yl)phenyl)-2-(1-(4-(1-(difluoromethyl)-1H-1,2,4-triazol-5-yl)-1H-pyrazol-1-yl)-2-(1-(difluoromethyl)-1H-pyrazol-3-yl)ethyl)pyridine 1-oxide

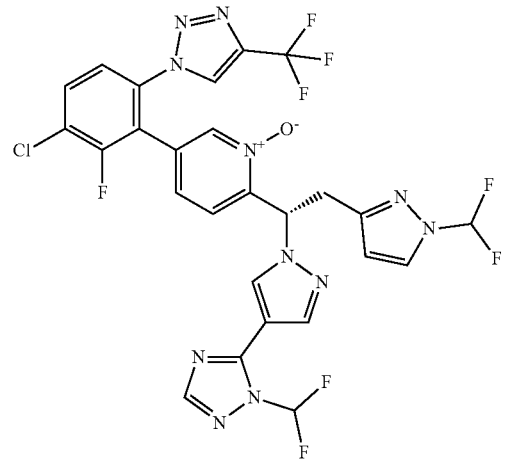 [SMILES: [O-][n+]1cc(-c2c(-n3cc(C(F)(F)F)nn3)ccc(Cl)c2F)ccc1[C@H](Cc1ccn(C(F)F)n1)n1cc(-c2ncnn2C(F)F)cn1]

LC/MS: mass calculated for $C_{2H}H_{16}ClF_8N_{11}O$: 685.11, measured (ES, m/z): 685.95 [M+H]$^+$. $^1$H NMR (300 MHz, DMSO-d$_6$) δ 9.17 (d, J=1.0 Hz, 1H), 8.61 (s, 1H), 8.45 (d, J=1.6 Hz, 1H), 8.24 (s, 1H), 7.40-8.20 (m, 7H), 7.18-7.21 (m, 1H), 6.53 (t, J=7.5 Hz, 1H), 6.17 (d, J=2.6 Hz, 1H), 3.62-3.70 (m, 2H). $^{19}$F NMR (282 MHz, DMSO-d$_6$) δ −59.80, −93.93, −93.95, −96.28, −112.83.

Example 877: (R)-5-(3-Chloro-2-fluoro-6-(4-(trifluoromethyl)-1H-1,2,3-triazol-1-yl)phenyl)-2-(1-(4-(1-(difluoromethyl)-1H-1,2,4-triazol-5-yl)-1H-pyrazol-1-yl)-2-(1-(difluoromethyl)-1H-pyrazol-3-yl)ethyl)pyridine 1-oxide

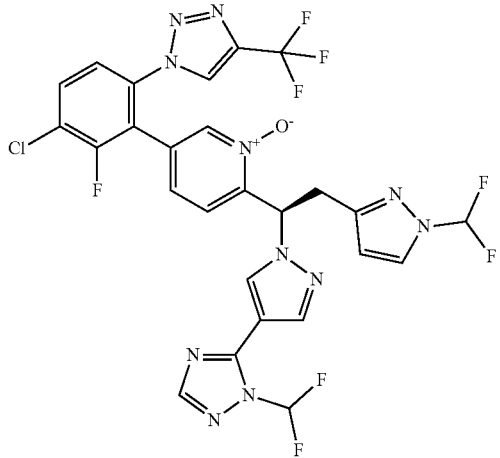 [SMILES: [O-][n+]1cc(-c2c(-n3cc(C(F)(F)F)nn3)ccc(Cl)c2F)ccc1[C@@H](Cc1ccn(C(F)F)n1)n1cc(-c2ncnn2C(F)F)cn1]

Step 1: 5-Bromo-2-(1-(4-(1-(difluoromethyl)-1H-1,2,4-triazol-5-yl)-1H-pyrazol-1-yl)-2-(1-(difluoromethyl)-1H-pyrazol-3-yl)ethyl)pyridine A mixture of 1-(difluoromethyl)-5-(1H-pyrazol-4-yl)-1H-1,2,4-triazole (128 mg, 0.69 mmol, 1.1 equiv.) and cesium carbonate (226 mg, 0.69 mmol, 1.1 equiv.) in Acetonitrile (3 mL) was stirred at room temperature for 10 minutes. Then 1-(5-bromopyridin-2-yl)-2-(1-(difluoromethyl)-1H-pyrazol-3-yl)ethyl methanesulfonate (250 mg, 0.63 mmol, 1.0 equiv.) was added to the reaction mixture and the mixture was stirred at 85° C. for 2 h.

To the mixture was added H$_2$O, the mixture was then extracted with EA three times. The combined organic layers was washed with brine, dried over Na$_2$SO$_4$, concentrated and purified by silica gel chromatography (0→80% EA/PE) to yield 5-bromo-2-(1-(4-(1-(difluoromethyl)-1H-1,2,4-triazol-5-yl)-1H-pyrazol-1-yl)-2-(1-(difluoromethyl)-1H-pyrazol-3-yl)ethyl)pyridine as a yellow solid. LC/MS: mass calculated for $C_{17}H_{13}BrF_4N_8$: 484.04, measured (ES, m/z): 485.00, 486.95 [M+H, M+H+2]$^+$.

Step 2: (6-(1-(4-(1-(Difluoromethyl)-1H-1,2,4-triazol-5-yl)-1H-pyrazol-1-yl)-2-(1-(difluoromethyl)-1H-pyrazol-3-yl)ethyl)pyridin-3-yl)boronic acid A mixture of 5-bromo-2-(1-(4-(1-(difluoromethyl)-1H-1,2,4-triazol-5-yl)-1H-pyrazol-1-yl)-2-(1-(difluoromethyl)-1H-pyrazol-3-yl)ethyl)pyridine (250 mg, 0.51 mmol, 1.0 equiv.) and 4,4,4',4',5,5,5',5'-octamethyl-2,2'-bi(1,3,2-dioxaborolane) (262 mg, 1.03 mmol, 2.0 equiv.) in 1,4-dioxane (4 mL) was added potassium acetate (202 mg, 2.06 mmol, 4.0 equiv.) and Pd(dppf)Cl$_2$ (38 mg, 0.05 mmol, 0.1 equiv.) under N$_2$.

The flask was evacuated, then purged with nitrogen. This was repeated 2×. The mixture was then stirred at 90° C. for 2 h. To the reaction was added water, and the mixture extracted with EA twice. The combined organic layers were washed with brine, dried over Na$_2$SO$_4$, and concentrated under vacuum. To yield (6-(1-(4-(1-(difluoromethyl)-1H-1,2,4-triazol-5-yl)-1H-pyrazol-1-yl)-2-(1-(difluoromethyl)-1H-pyrazol-3-yl)ethyl)pyridin-3-yl)boronic acid as brown oil. LC/MS: mass calculated for $C_{17}H_{15}BF_4N_8O_2$: 450.13, measured (ES, m/z): 451.15 [M+H]$^+$.

Step 3: 5-(3-Chloro-2-fluoro-6-(4-(trifluoromethyl)-1H-1,2,3-triazol-1-yl)phenyl)-2-(1-(4-(1-(difluoromethyl)-1H-1,2,4-triazol-5-yl)-1H-pyrazol-1-yl)-2-(1-(difluoromethyl)-1H-pyrazol-3-yl)ethyl)pyridine A mixture of (6-(1-(4-(1-(difluoromethyl)-1H-1,2,4-triazol-5-yl)-1H-pyrazol-1-yl)-2-(1-(difluoromethyl)-1H-pyrazol-3-yl)ethyl)pyridin-3-yl)boronic acid (200 mg, 0.44 mmol, 1.0 equiv.) and 1-(4-chloro-3-fluoro-2-iodophenyl)-4-(trifluoromethyl)-1H-1,2,3-triazole (261 mg, 0.67 mmol, 1.5 equiv.) in the mixed solution of 1,4-dioxane (4 mL) and water (1 mL) was added potassium carbonate (246 mg, 1.78 mmol, 4.0 equiv.) and tetrakis(triphenylphosphine) palladium(0) (103 mg, 0.09 mmol, 0.2 equiv.). The flask was evacuated, then purged with nitrogen. This was repeated 2×. The reaction mixture was stirred at 100° C. overnight under N$_2$.

Water was added, and the mixture was extracted with EA. The combined organic layers were washed with brine, dried over Na$_2$SO$_4$ and concentrated under vacuum to yield a residue which was purified by silica gel chromatography with EA/petroleum (0→60%) to yield 5-(3-chloro-2-fluoro-6-(4-(trifluoromethyl)-1H-1,2,3-triazol-1-yl)phenyl)-2-(1-(4-(1-(difluoromethyl)-1H-1,2,4-triazol-5-yl)-1H-pyrazol-1-yl)-2-(1-(difluoromethyl)-1H-pyrazol-3-yl)ethyl)pyridine as a yellow solid. LC/MS: mass calculated for $C_{26}H_{16}ClF_8N_{11}$: 669.12, measured (ES, m/z): 670.25 [M+H]$^+$.

Step 4: (R)-5-(3-Chloro-2-fluoro-6-(4-(trifluoromethyl)-1H-1,2,3-triazol-1-yl)phenyl)-2-(1-(4-(1-(difluoromethyl)-1H-1,2,4-triazol-5-yl)-1H-pyrazol-1-yl)-2-(1-(difluoromethyl)-1H-pyrazol-3-yl)ethyl)pyridine 1-oxide A solution of 5-(3-chloro-2-fluoro-6-(4-(trifluoromethyl)-1H-1,2,3-triazol-1-yl)phenyl)-2-(1-(4-(1-(difluoromethyl)-1H-1,2,4-triazol-5-yl)-1H-pyrazol-1-yl)-2-(1-(difluoromethyl)-1H-pyrazol-3-yl)ethyl)pyridine (180 mg, 0.27 mmol, 1.0 equiv.) and methyl trioxorhenium (VII) (13 mg, 0.05 mmol, 0.2 equiv.) in CH$_3$OH (3 mL) was added hydrogen peroxide (0.3 mL, 2.69 mmol, 10.0 equiv.). The reaction mixture was stirred at room temperature for 2.5 h. The reaction mixture was purified by reverse phase chromatography on C18 (80 g, ACN/H$_2$O (0.05% CF$_3$COOH: 0→60%) to yield a residue which was further purified by Prep-Chiral-HPLC to yield (R)-5-(3-chloro-2-fluoro-6-(4-(trifluoromethyl)-1H-1,2,3-triazol-1-yl)phenyl)-2-(1-(4-(1-(difluoromethyl)-1H-1,2,4-triazol-5-yl)-1H-pyrazol-1-yl)-2-(1-(difluoromethyl)-1H-pyrazol-3-yl)ethyl)pyridine 1-oxide as a white solid.

LC/MS: mass calculated for $C_{26}H_{16}ClF_8N_{11}O$: 685.11, measured (ES, m/z): 686.00 [M+H]$^+$. $^1$H NMR (300 MHz, DMSO-d$_6$): 39.17 (d, J=1.0 Hz, 1H), 8.61 (s, 1H), 8.45 (s, 1H), 8.24 (s, 1H), 8.08-8.01 (m, 3H), 8.00 (t, J=57.3 Hz, 1H), 7.75 (dd, J=8.7, 1.5 Hz, 1H), 7.67 (t, J=59.4 Hz, 1H), 7.45 (d, J=8.3 Hz, 1H), 7.17 (dd, J=8.3, 1.7 Hz, 1H), 6.51 (t, J=7.5 Hz, 1H), 6.17 (d, J=2.6 Hz, 1H), 3.65 (d, J=7.5 Hz, 2H). $^{19}$F NMR (282 MHz, DMSO-d$_6$): δ −59.81, −93.93, −96.28, −112.83.

Example 878: 2-(1-(4-(4-Carboxyphenyl)-1H-pyrazol-1-yl)-3-(difluoromethoxy)propyl)-5-(3-chloro-2-fluoro-6-(4-(trifluoromethyl)-1H-1,2,3-triazol-1-yl)phenyl)pyridine 1-oxide

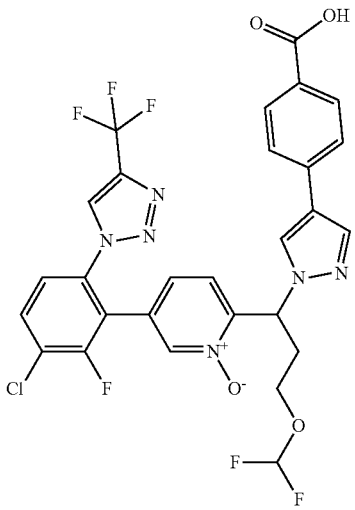 [SMILES: O=C(O)c1ccc(-c2cnn(C(CCOC(F)F)c3ccc(-c4c(-n5cc(C(F)(F)F)nn5)ccc(Cl)c4F)c[n+]3[O-])c2)cc1]

To a solution of 4-(1-(1-(5-(3-chloro-2-fluoro-6-(4-(trifluoromethyl)-1H-1,2,3-triazol-1-yl)phenyl)pyridin-2-yl)-3-(difluoromethoxy)propyl)-1H-pyrazol-4-yl)benzoic acid (55 mg, 0.09 mmol) in MeOH (2 mL) was added methyltrioxorhenium (6.4 mg, 0.02 mmol), followed by $H_2O_2$ (30%, 293.7 mg, 2.6 mmol) and the reaction mixture was stirred at room temperature for 2 h. The resulting mixture was subjected to Gilson HPLC purification to yield 2-(1-(4-(4-Carboxyphenyl)-1H-pyrazol-1-yl)-3-(difluoromethoxy)propyl)-5-(3-chloro-2-fluoro-6-(4-(trifluoromethyl)-1H-1,2,3-triazol-1-yl)phenyl)pyridine 1-oxide as a light orange film.

LC/MS: mass calculated for $C_{28}H_{19}ClF_6N_6O_4$: 652.1, measured (ES, m/z): 653.0 [M+H]$^+$. $^1$H NMR (400 MHz, CD$_3$OD) δ ppm 2.68-2.81 (m, 2H) 3.71-3.81 (m, 1H) 3.97 (dt, J=10.15, 4.95 Hz, 1H) 6.15-6.57 (m, 2H) 7.24-7.34 (m, 1H) 7.44-7.48 (m, 1H) 7.57-7.63 (m, 1H) 7.66-7.73 (m, 2H), 7.89 (dd, J=8.80, 7.83 Hz, 1H) 7.99-8.04 (m, 2H) 8.07 (s, 1H) 8.35 (d, J=11.74 Hz, 2H), 8.76-8.81 (m, 1H).

Example 879: (S)-5-(3-Chloro-2-fluoro-6-(4-(trifluoromethyl)-1H-1,2,3-triazol-1-yl) phenyl)-2-(1-(4-(1-methyl-1H-1,2,4-triazol-5-yl)-1H-pyrazol-1-yl)-3-(trifluoromethoxy)propyl)pyridine 1-oxide

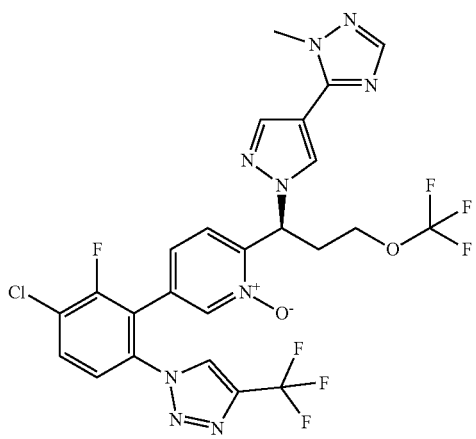 [SMILES: Cn1ncnc1-c1cnn([C@@H](CCOC(F)(F)F)c2ccc(-c3c(-n4cc(C(F)(F)F)nn4)ccc(Cl)c3F)c[n+]2[O-])c1]

LC/MS: mass calculated for $C_{24}H_{17}ClF_7N_9O_2$: 631.11, measured (ES, m/z): 631.95 [M+H]$^+$. $^1$H NMR (400 MHz, DMSO-d$_6$) δ 9.18 (s, 1H), 8.65 (s, 1H), 8.46 (d, J=1.6 Hz, 1H), 8.13-8.02 (m, 2H), 7.90 (s, 1H), 7.78 (dd, J=8.7, 1.5 Hz, 1H), 7.31 (d, J=8.3 Hz, 1H), 7.18 (dd, J=8.3, 1.6 Hz, 1H), 6.31 (dd, J=9.0, 5.5 Hz, 1H), 4.11 (dt, J=10.6, 5.5 Hz, 1H), 4.03-3.91 (m, 1H), 3.96 (s, 3H), 2.72 (dq, J=9.6, 5.6 Hz, 2H). $^{19}$F NMR (376 MHz, DMSO-d$_6$) d −59.30, −59.57 (d, J=185.3 Hz), −73.46 (d, J=2.2 Hz), −112.87, −218.40.

Example 880: (R)-5-(3-Chloro-2-fluoro-6-(4-(trifluoromethyl)-1H-1,2,3-triazol-1-yl) phenyl)-2-(1-(4-(1-methyl-1H-1,2,4-triazol-5-yl)-1H-pyrazol-1-yl)-3-(trifluoromethoxy)propyl)pyridine 1-oxide

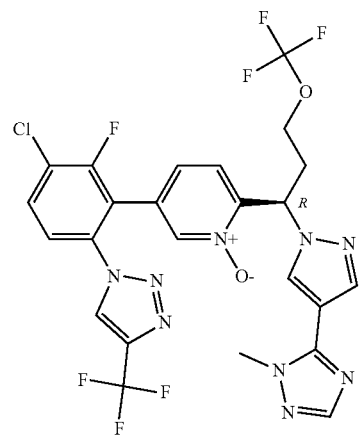

Step 1: (6-(3-((tert-Butyldimethylsilyl)oxy)-1-(4-(1-methyl-1H-1,2,4-triazol-5-yl)-1H-pyrazol-1-yl)propyl)pyridin-3-yl)boronic acid A mixture of 5-bromo-2-(3-((tert-butyldimethylsilyl)oxy)-1-(4-(1-methyl-1H-1,2,4-triazol-5-yl)-1H-pyrazol-1-yl)propyl)pyridine (0.65 g, 1.36 mmol, 1.0 equiv.), 4,4,4',4',5,5,5',5'-octamethyl-2,2'-bi(1,3,2-dioxaborolane) (0.69 g, 2.72 mmol, 2.0 equiv.), Pd(dppf)Cl$_2$ (0.10 g, 0.14 mmol, 0.1 equiv.) and KOAc (0.40 g, 4.08 mmol, 3.0 equiv.) in 1,4-dioxane (6 mL) was stirred for 2 h at 90° C. in a nitrogen atmosphere. The mixture was diluted with H$_2$O, extracted with ethyl acetate twice. The combined organic layers was washed with brine, dried over Na$_2$SO$_4$ and concentrated to yield (6-(3-((tert-butyldimethylsilyl)oxy)-1-(4-(1-methyl-1H-1,2,4-triazol-5-yl)-1H-pyrazol-1-yl)propyl)pyridin-3-yl) boronic acid as deep yellow oil. LC/MS: mass calculated for $C_{20}H_{31}BN_6O_3Si$: 442.23, measured (ES, m/z): 443.15 [M+H]$^+$.

Step 2: 2-(3-((tert-Butyldimethylsilyl)oxy)-1-(4-(1-methyl-1H-1,2,4-triazol-5-yl)-1H-pyrazol-1-yl)propyl)-5-(3-chloro-2-fluoro-6-(4-(trifluoromethyl)-1H-1,2,3-triazol-1-yl)phenyl)pyridine A mixture of (6-(3-((tert-butyldimethylsilyl)oxy)-1-(4-(1-methyl-1H-1,2,4-triazol-5-yl)-1H-pyrazol-1-yl)propyl)pyridin-3-yl)boronic acid (0.6 g, resulting), 1-(4-chloro-3-fluoro-2-iodophenyl)-4-(trifluoromethyl)-1H-1,2,3-triazole (0.64 g, 1.63 mmol), Pd(PPh$_3$)$_4$ (0.31 g, 0.27 mmol), K$_2$CO$_3$ (1.1 g, 8.14 mmol) in 1,4-dioxane (5 mL) and water (1 mL)

was refluxed at 90° C. under N₂ for 2 h. The mixture was diluted with H₂O, extracted with ethyl acetate twice. The combined organic layers were washed with brine, dried over Na₂SO₄, concentrated and purified by silica gel chromatography (0→3%, MeOH/DCM) to yield 2-(3-((tert-butyldimethylsilyl)oxy)-1-(4-(1-methyl-1H-1,2,4-triazol-5-yl)-1H-pyrazol-1-yl)propyl)-5-(3-chloro-2-fluoro-6-(4-(trifluoromethyl)-1H-1,2,3-triazol-1-yl)phenyl)pyridine as a yellow oil. LC/MS: mass calculated for $C_{29}H_{32}ClF_4N_9OSi$: 661.21, measured (ES, m/z): 662.15 [M+H]⁺.

Step 3: 3-(5-(3-Chloro-2-fluoro-6-(4-(trifluoromethyl)-1H-1,2,3-triazol-1-yl) phenyl)pyridin-2-yl)-3-(4-(1-methyl-1H-1,2,4-triazol-5-yl)-1H-pyrazol-1-yl) propan-1-ol A mixture of 2-(3-((tert-butyldimethylsilyl)oxy)-1-(4-(1-methyl-1H-1,2,4-triazol-5-yl)-1H-pyrazol-1-yl)propyl)-5-(3-chloro-2-fluoro-6-(4-(trifluoromethyl)-1H-1,2,3-triazol-1-yl)phenyl)pyridine (0.45 g, 0.68 mmol, 1.0 equiv) and triethylamine trihydrofluoride (0.22 g, 1.36 mmol, 2.0 equiv) in THF (5 mL) was stirred for 1 h at 70° C. The mixture was diluted with H₂O, extracted with ethyl acetate twice. The combined organic layers were washed with brine, dried over Na₂SO₄, concentrated and purified by silica gel chromatography (0→5%, MeOH/DCM) to yield 3-(5-(3-chloro-2-fluoro-6-(4-(trifluoromethyl)-1H-1,2,3-triazol-1-yl)phenyl)pyridin-2-yl)-3-(4-(1-methyl-1H-1,2,4-triazol-5-yl)-1H-pyrazol-1-yl)propan-1-ol as a light yellow solid. LC/MS: mass calculated for $C_{23}H_{18}ClF_4N_9O$: 547.13, measured (ES, m/z): 548.25 [M+H]⁺.

Step 4: 5-(3-Chloro-2-fluoro-6-(4-(trifluoromethyl)-1H-1,2,3-triazol-1-yl)phenyl)-2-(1-(4-(1-methyl-1H-1,2,4-triazol-5-yl)-1H-pyrazol-1-yl)-3-(trifluoromethoxy)propyl)pyridine To a mixture of 3-(5-(3-chloro-2-fluoro-6-(4-(trifluoromethyl)-1H-1,2,3-triazol-1-yl)phenyl)pyridin-2-yl)-3-(4-(1-methyl-1H-1,2,4-triazol-5-yl)-1H-pyrazol-1-yl)propan-1-ol (150 mg, 0.27 mmol, 1.0 equiv.), KF (64 mg, 1.10 mmol, 4.0 equiv.), silver trifluoromethanesulfonete (210 mg, 0.82 mmol, 3.0 equiv.), Selectfluor™ (145 mg, 0.41 mmol, 1.5 equiv.) in EA (10 mL) was added 2-fluoropyridine (0.080 g, 0.82 mmol, 3 equiv.) under N₂.

Then trimethyl(trifluoromethyl)silane (117 mg, 0.82 mmol, 3.0 equiv.) was added the above mixture at 0° C. and stirred 2 h at room temperature. The reaction was quenched by the addition water, extracted with ethyl acetate three times. The combined organic layers were washed with brine, dried over Na₂SO₄, concentrated and purified by silica gel chromatography (0→5%, MeOH/DCM) to yield 5-(3-chloro-2-fluoro-6-(4-(trifluoromethyl)-1H-1,2,3-triazol-1-yl)phenyl)-2-(1-(4-(1-methyl-1H-1,2,4-triazol-5-yl)-1H-pyrazol-1-yl)-3-(trifluoromethoxy)propyl)pyridine as a light yellow oil. LC/MS: mass calculated for $C_{24}H_{17}ClF_7N_9O$: 615.11, measured (ES, m/z): 616.00 [M+H]⁺.

Step 5: (R)-5-(3-Chloro-2-fluoro-6-(4-(trifluoromethyl)-1H-1,2,3-triazol-1-yl) phenyl)-2-(1-(4-(1-methyl-1H-1,2,4-triazol-5-yl)-1H-pyrazol-1-yl)-3-(trifluoromethoxy)propyl)pyridine 1-oxide A mixture of 5-(3-chloro-2-fluoro-6-(4-(trifluoromethyl)-1H-1,2,3-triazol-1-yl) phenyl)-2-(1-(4-(1-methyl-1H-1,2,4-triazol-5-yl)-1H-pyrazol-1-yl)-3-(trifluoromethoxy)propyl)pyridine (100 mg, 0.16 mmol, 1.0 equiv.), hydrogen peroxide (30 wt %, 0.18 mL, 1.62 mmol, 10.0 equiv.) and methyltrioxorhenium (8 mg, 0.03 mmol, 0.2 equiv.) in CH₃OH (1 mL) was stirred for 1 h at room temperature. The solution was purified by reverse phase chromatography on C18 (0→60% ACN/H₂O) to yield 5-(3-chloro-2-fluoro-6-(4-(trifluoromethyl)-1H-1,2,3-triazol-1-yl)phenyl)-2-(1-(4-(1-methyl-1H-1,2,4-triazol-5-yl)-1H-pyrazol-1-yl)-3-(trifluoromethoxy)propyl)pyridine 1-oxide. The racemic product was separated by Chiral-HPLC to yield (R)-5-(3-chloro-2-fluoro-6-(4-(trifluoromethyl)-1H-1,2,3-triazol-1-yl)phenyl)-2-(1-(4-(1-methyl-1H-1,2,4-triazol-5-yl)-1H-pyrazol-1-yl)-3-(trifluoromethoxy)propyl)pyridine 1-oxide as a white solid.

LC/MS: mass calculated for $C_{24}H_{17}ClF_7N_9O_2$: 631.11, measured (ES, m/z): 631.95 [M+H]⁺. ¹H NMR (400 MHz, DMSO-d₆): δ 9.18 (s, 1H), 8.65 (s, 1H), 8.46 (d, J=1.7 Hz, 1H), 8.03-8.13 (m, 2H), 7.90 (s, 1H), 7.75-7.85 (m, 1H), 7.31 (d, J=8.3 Hz, 1H), 7.15-7.22 (m, 1H), 6.27-6.36 (m, 1H), 4.06-4.15 (m, 1H), 3.92-4.03 (m, 4H), 2.65-2.82 (m, 2H). ¹⁹F NMR (376 MHz, DMSO-d₆): δ −59.32, −59.81, −112.86.

Example 881: (S)-2-(1-(4-(5-Acetamido-2-(trifluoromethyl)pyridin-4-yl)-1H-pyrazol-1-yl)-2-cyclopropylethyl)-5-(3-chloro-2-fluoro-6-(1H-tetrazol-1-yl) phenyl)pyridine 1-oxide

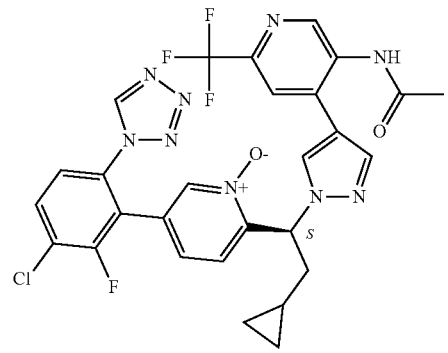

LC/MS: mass calculated for $C_{28}H_{22}ClF_4N_9O_2$: 627.15, measured (ES, m/z): 628.20 [M+H]⁺. ¹H NMR (300 MHz, DMSO-d₆) δ 9.90 (s, 1H), 9.69 (s, 1H), 8.77 (s, 1H), 8.68 (s, 1H), 8.43 (d, J=1.5 Hz, 1H), 8.16 (s, 1H), 8.00-8.14 (m, 2H), 7.72-7.79 (m, 1H), 7.34-7.39 (m, 1H), 7.14-7.20 (m, 1H), 6.11-6.19 (m, 1H), 3.42-3.50 (m, 1H), 2.31-2.42 (m, 1H), 2.12 (s, 3H), 1.81-1.95 (m, 1H), 0.55-0.68 (m, 1H), 0.26-0.39 (m, 2H), 0.08-0.17 (m, 1H). ¹⁹F NMR (283 MHz, DMSO-d₆) δ −65.94, −112.77.

Example 882: (R)-2-(1-(4-(5-Acetamido-2-(trifluoromethyl)pyridin-4-yl)-1H-pyrazol-1-yl)-2-cyclopropylethyl)-5-(3-chloro-2-fluoro-6-(1H-tetrazol-1-yl)phenyl)pyridine 1-oxide

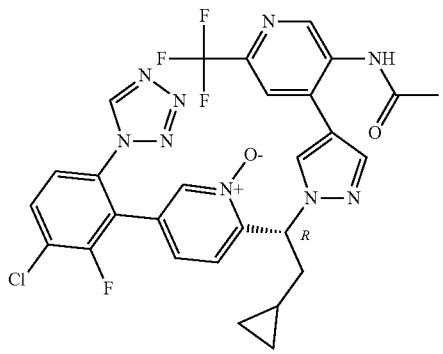

LC/MS: mass calculated for $C_{28}H_{22}ClF_4N_9O_2$: 627.15, measured (ES, m/z): 628.15 [M+H]$^+$. $^1$H NMR (300 MHz, DMSO-d$_6$) δ 9.90 (s, 1H), 9.69 (s, 1H), 8.77 (s, 1H), 8.68 (s, 1H), 8.43 (s, 1H), 8.16 (s, 1H), 8.00-8.14 (m, 2H), 7.72-7.79 (m, 1H), 7.34-7.39 (m, 1H), 7.14-7.20 (m, 1H), 6.11-6.19 (m, 1H), 3.42-3.50 (m, 1H), 2.38-2.41 (m, 1H), 2.12 (s, 3H), 1.81-1.95 (m, 1H), 0.52-0.68 (m, 1H), 0.28-0.39 (m, 2H), 0.08-0.17 (m, 1H). $^{19}$F NMR (283 MHz, DMSO-d$_6$) δ −65.94, −112.77.

Example 883: (R)-2-(1-(4-(4-Chloro-1-(difluoromethyl)-1H-imidazol-5-yl)-1H-pyrazol-1-yl)-3-(difluoromethoxy)propyl)-5-(3-chloro-2-fluoro-6-(1H-tetrazol-1-yl)phenyl)pyridine 1-oxide

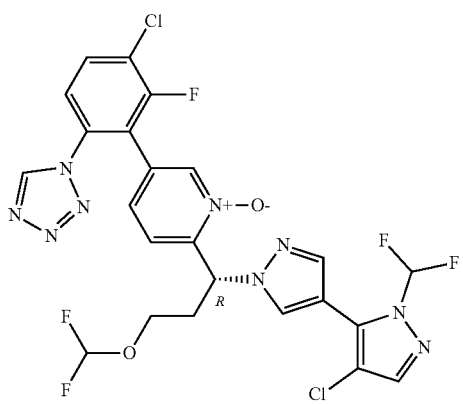

LC/MS: mass calculated for $C_{23}H_{16}Cl_2F_5N_9O_2$: 615.07, measured (ES, m/z): 615.95 [M+H]$^+$. $^1$H NMR (300 MHz, CD$_3$OD) δ 9.39 (s, 1H), 8.40 (s, 1H), 8.30 (s, 1H), 7.87-8.00 (m, 2H), 7.36-7.79 (m, 3H), 7.29-7.33 (m, 1H), 7.12 (s, 1H), 6.09-6.64 (m, 2H), 3.94-4.04 (m, 1H), 3.66-3.77 (m, 1H), 2.68-2.80 (m, 2H). $^{19}$F NMR (282 MHz, CD$_3$OD) δ −86.16, −96.57, −113.67.

Example 884: (S)-2-(1-(4-(4-Carboxyphenyl)-1H-pyrazol-1-yl)-2-(1-methyl-1H-pyrazol-3-yl)ethyl)-5-(5-chloro-2-cyanophenyl)pyridine 1-oxide

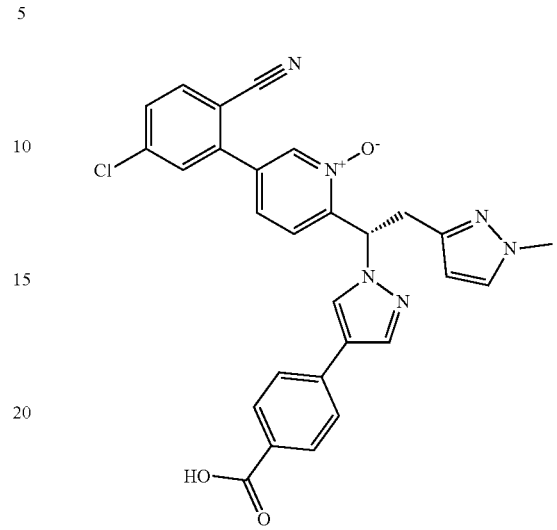

LC/MS: mass calculated for $C_{28}H_{21}ClN_8O_3$: 524.14, measured (ES, m/z): 525.05[M+H]$^+$. $^1$H NMR (400 MHz, DMSO-d$_6$) δ 8.69 (d, J=1.7 Hz, 1H), 8.61 (s, 1H), 8.12 (s, 1H), 8.05 (d, J=8.4 Hz, 1H), 7.88-7.94 (m, 3H), 7.68-7.80 (m, 3H), 7.59-7.65 (m, 1H), 7.46-7.52 (m, 2H), 6.40-6.47 (m, 1H), 5.87 (d, J=2.2 Hz, 1H), 3.73 (s, 3H), 3.57-3.64 (m, 2H).

Example 885: (R)-2-(1-(4-(4-Carboxyphenyl)-1H-pyrazol-1-yl)-2-(1-methyl-1H-pyrazol-3-yl)ethyl)-5-(5-chloro-2-cyanophenyl)pyridine 1-oxide

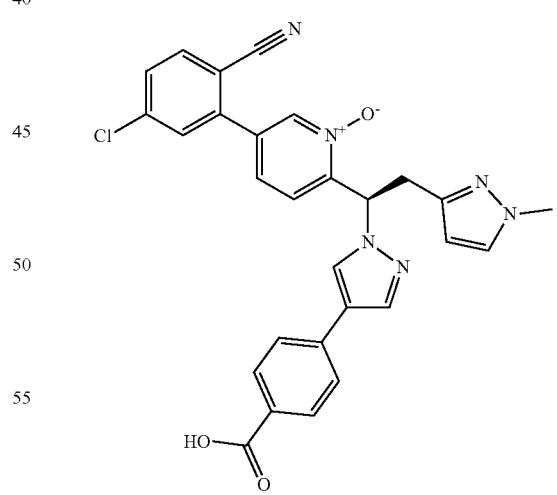

LC/MS: mass calculated for $C_{28}H_{21}ClN_6O_3$: 524.14, measured (ES, m/z): 525.05[M+H]$^+$. $^1$H NMR (400 MHz, DMSO-d$_6$) δ 8.69 (d, J=1.7 Hz, 1H), 8.61 (s, 1H), 8.12 (s, 1H), 8.05 (d, J=8.4 Hz, 1H), 7.88-7.94 (m, 3H), 7.68-7.80 (m, 3H), 7.58-7.65 (m, 1H), 7.46-7.52 (m, 2H), 6.40-6.47 (m, 1H), 5.87 (d, J=2.2 Hz, 1H), 3.73 (s, 3H), 3.57-3.64 (m, 2H).

Example 886: (S)-2-(1-(4-(4-Carboxyphenyl)-1H-pyrazol-1-yl)-2-(1-methyl-1H-pyrazol-3-yl)ethyl)-5-(3-Chloro-6-(difluoromethyl)-2-fluorophenyl)pyridine 1-oxide

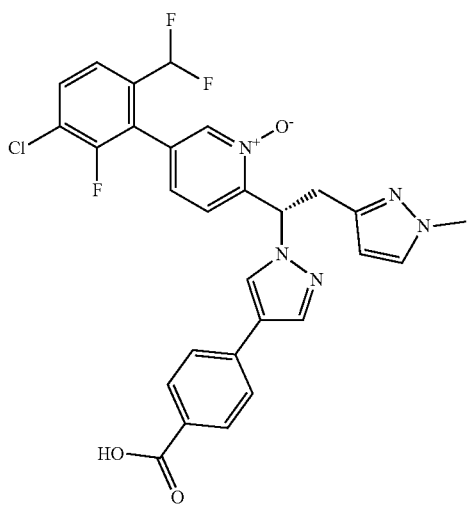 [SMILES: Cn1ccc(C[C@@H](c2ccc(-c3c(C(F)F)ccc(Cl)c3F)c[n+]2[O-])n2cc(-c3ccc(C(=O)O)cc3)cn2)n1]

LC/MS: mass calculated for C$_{28}$H$_{21}$ClF$_3$N$_5$O$_3$: 567.13, measured (ES, m/z): 568.05 [M+H]$^+$. $^1$H NMR (400 MHz, DMSO-d$_6$) δ 8.61 (s, 1H), 8.52 (s, 1H), 8.14 (s, 1H), 7.85-7.95 (m, 3H), 7.72 (d, J=8.3 Hz, 2H), 7.61 (d, J=8.7 Hz, 1H), 7.48 (d, J=2.1 Hz, 1H), 7.38-7.43 (m, 2H), 6.90 (t, J=53.9 Hz, 1H), 6.38-6.42 (m, 1H), 5.83 (d, J=2.2 Hz, 1H), 3.73 (s, 3H), 3.52-3.68 (m, 2H).

Example 887: (R)-2-(1-(4-(4-Carboxyphenyl)-1H-pyrazol-1-yl)-2-(1-methyl-1H-pyrazol-3-yl)ethyl)-5-(3-Chloro-6-(difluoromethyl)-2-fluorophenyl)pyridine 1-oxide

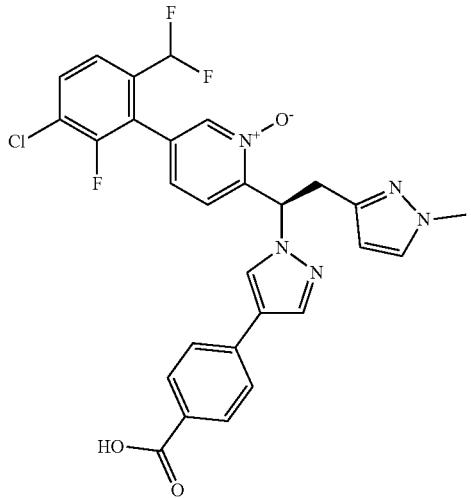 [SMILES: Cn1ccc(C[C@H](c2ccc(-c3c(C(F)F)ccc(Cl)c3F)c[n+]2[O-])n2cc(-c3ccc(C(=O)O)cc3)cn2)n1]

LC/MS: mass calculated for C$_{28}$H$_{21}$ClF$_3$N$_5$O$_3$: 567.13, measured (ES, m/z): 568.05 [M+H]$^+$. $^1$H NMR (400 MHz, DMSO-d$_6$) δ 8.61 (s, 1H), 8.52 (s, 1H), 8.14 (s, 1H), 7.85-7.95 (m, 3H), 7.72 (d, J=8.3 Hz, 2H), 7.61 (d, J=8.5 Hz, 1H), 7.48 (d, J=2.2 Hz, 1H), 7.38-7.43 (m, 2H), 6.90 (t, J=53.9 Hz, 1H), 6.38-6.42 (m, 1H), 5.83 (d, J=2.2 Hz, 1H), 3.73 (s, 3H), 3.54-3.68 (m, 2H).

Example 888: (S)-2-(1-(4-(4-Carboxyphenyl)-1H-pyrazol-1-yl)-2-cyclopropylethyl)-5-(5-chloro-2-cyanophenyl)-4-methoxypyridine 1-oxide

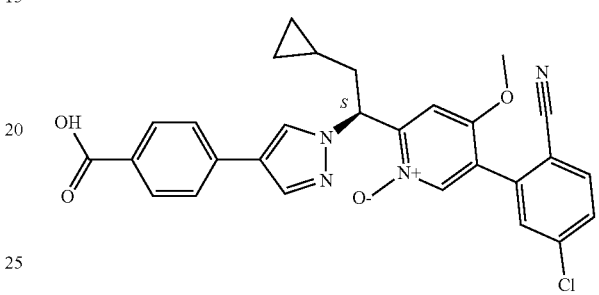

LC/MS: mass calculated for C$_{28}$H$_{23}$ClN$_4$O$_4$: 514.14, measured (ES, m/z): 515.10 [M+H]$^+$. $^1$H NMR (400 MHz, DMSO-d$_6$) δ 8.66 (s, 1H), 8.39 (s, 1H), 8.14 (s, 1H), 7.99 (d, J=8.4 Hz, 1H), 7.90 (d, J=8.4 Hz, 2H), 7.78 (d, J=2.2 Hz, 1H), 7.76-7.68 (m, 3H), 7.19 (s, 1H), 6.21 (dd, J=10.2, 4.5 Hz, 1H), 3.78 (s, 3H), 2.46-2.35 (m, 1H), 2.10-1.91 (m, 1H), 0.64-0.60 (m, 1H), 0.42-0.38 (m, 1H), 0.36-0.31 (m, 1H), 0.21-0.14 (m, 1H), 0.07-0.00 (m, 1H).

Example 889: (R)-2-(1-(4-(4-Carboxyphenyl)-1H-pyrazol-1-yl)-2-cyclopropylethyl)-5-(5-chloro-2-cyanophenyl)-4-methoxypyridine 1-oxide

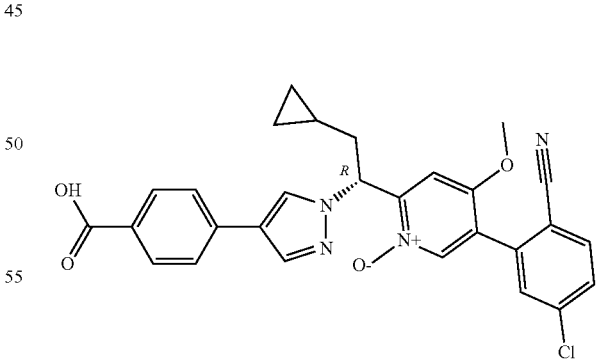

LC/MS: mass calculated for C$_{28}$H$_{23}$ClN$_4$O$_4$: 514.14, measured (ES, m/z): 515.10 [M+H]$^+$. $^1$H NMR (400 MHz, DMSO-d$_6$) δ 12.71 (s, 1H), 8.67 (s, 1H), 8.39 (s, 1H), 8.15 (s, 1H), 7.99-8.02 (m, 1H), 7.89-7.95 (m, 2H), 7.68-7.81 (m, 4H), 7.20 (s, 1H), 6.20-6.26 (m, 1H), 3.78 (s, 3H), 2.35-2.45 (m, 1H), 1.94-2.05 (m, 1H), 0.58-0.66 (m, 1H), 0.27-0.46 (m, 2H), 0.14-0.22 (m, 1H), 0.00-0.06 (m, 1H).

Example 890: 2-(1-(4-(4-Carbamoyl-3-fluorophenyl)-1H-pyrazol-1-yl)-3-(difluoromethoxy)propyl)-5-(3-Chloro-2-fluoro-6-(4-(trifluoromethyl)-1H-1,2,3-triazol-1-yl)phenyl)pyridine 1-oxide

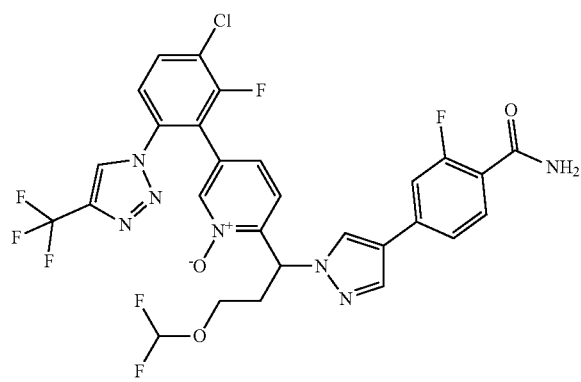

To a solution of 4-(1-(1-(5-(3-Chloro-2-fluoro-6-(4-(trifluoromethyl)-1H-1,2,3-triazol-1-yl)phenyl)pyridin-2-yl)-3-(difluoromethoxy)propyl)-1H-pyrazol-4-yl)-2-fluorobenzamide (190 mg, 0.29 mmol) in MeOH (3.5 mL) was added MeReO$_3$ (18.1 mg, 0.07 mmol), followed by 30% H$_2$O$_2$ (329.4 mg, 2.9 mmol). The reaction mixture was stirred at room temperature for 2 h. The resulting mixture was subjected to Gilson HPLC purification to yield 2-(1-(4-(4-Carbamoyl-3-fluorophenyl)-1H-pyrazol-1-yl)-3-(difluoromethoxy)propyl)-5-(3-Chloro-2-fluoro-6-(4-(trifluoromethyl)-1H-1,2,3-triazol-1-yl)phenyl)pyridine 1-oxide as a white solid.

LC/MS: mass calculated for C$_{28}$H$_{19}$ClF$_7$N$_7$O$_3$: 669.1, measured (ES, m/z): 670.2 [M+H]$^+$. $^1$H NMR (400 MHz, CD$_3$OD) δ ppm 2.69-2.82 (m, 2H), 3.72-3.81 (m, 1H), 3.96-4.02 (m, 1H), 6.17-6.58 (m, 2H), 7.30-7.34 (m, 1H), 7.46-7.55 (m, 3H), 7.62 (dd, J=8.56, 1.71 Hz, 1H), 7.86 (t, J=8.07 Hz, 1H), 7.89-7.95 (m, 1H), 8.09 (s, 1H), 8.39 (s, 2H), 8.79-8.84 (m, 1H).

Example 891: (R*)-5-(3-Chloro-2-fluoro-6-(oxazol-5-yl)phenyl)-2-(3-(difluoromethoxy)-1-(4-(4-fluoro-1-methyl-1H-1,2,3-triazol-5-yl)-1H-pyrazol-1-yl)propyl)pyridine 1-oxide

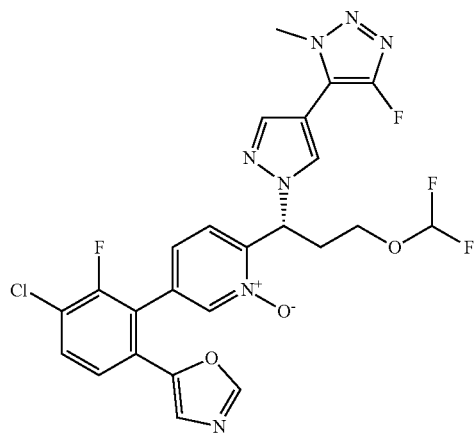 [SMILES: Cn1nnc(F)c1-c1cnn([C@H](CCOC(F)F)c2ccc(-c3c(-c4cnco4)ccc(Cl)c3F)c[n+]2[O-])c1]

LC/MS: mass calculated for C$_{24}$H$_{18}$ClF$_4$N$_7$O$_3$: 563.11, measured (ES, m/z): 564.05 [M+H]$^+$. $^1$H NMR (400 MHz, DMSO-d$_6$) δ 8.59 (s, 1H), 8.53 (d, J=1.6 Hz, 1H), 8.40 (s, 1H), 8.05 (s, 1H), 7.82-7.89 (m, 1H), 7.68-7.71 (m, 1H), 7.38-7.50 (m, 2H), 6.47-6.87 (m, 2H), 6.32-6.40 (m, 1H), 4.12 (s, 3H), 3.87-3.95 (m, 1H), 3.71-3.79 (m, 1H), 2.65-2.80 (m, 2H). $^{19}$F NMR (376 MHz, DMSO-d$_6$) δ −73.45, −83.29, −114.98, −145.05.

Example 892: (S*)-5-(3-Chloro-2-fluoro-6-(oxazol-5-yl)phenyl)-2-(3-(difluoromethoxy)-1-(4-(4-fluoro-1-methyl-1H-1,2,3-triazol-5-yl)-1H-pyrazol-1-yl)propyl)pyridine 1-oxide

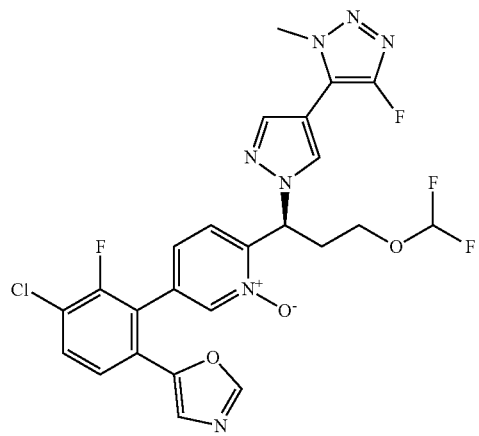 [SMILES: Cn1nnc(F)c1-c1cnn([C@@H](CCOC(F)F)c2ccc(-c3c(-c4cnco4)ccc(Cl)c3F)c[n+]2[O-])c1]

LC/MS: mass calculated for C$_{24}$H$_{18}$ClF$_4$N$_7$O$_3$: 563.11, measured (ES, m/z): 564.05 [M+H]$^+$. $^1$H NMR (400 MHz, DMSO-d$_6$) δ 8.59 (s, 1H), 8.53 (s, 1H), 8.40 (s, 1H), 8.05 (s, 1H), 7.85 (t, J=8.6 Hz, 1H), 7.69 (d, J=8.6 Hz, 1H), 7.48 (d, J=8.2 Hz, 1H), 7.39 (d, J=8.3 Hz, 1H), 6.74 (s, 1H), 6.67 (t, J=76.0 Hz, 1H), 6.36 (dd, J=9.8, 4.8 Hz, 1H), 4.12 (s, 3H), 3.87-3.95 (m, 1H), 3.70-3.77 (m, 1H), 2.67-2.77 (m, 2H). $^{19}$F NMR (376 MHz, DMSO-d$_6$) δ 73.47, −83.29, −114.98, −145.04.

Example 893: (R*)-5-(5-Chloro-2-cyanophenyl)-2-(3-(difluoromethoxy)-1-(4-(1-(difluoromethyl)-1H-1,2,4-triazol-5-yl)-1H-pyrazol-1-yl)propyl-3,3-d2)pyridine 1-oxide

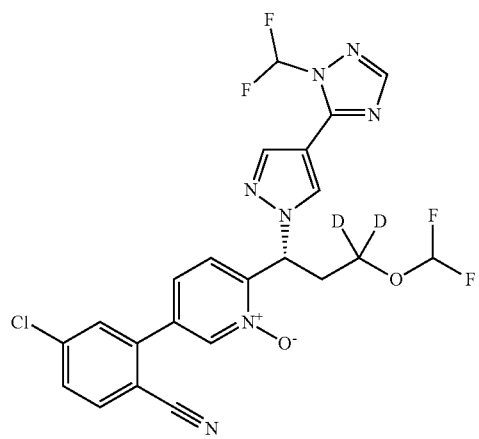 [SMILES: [2H]C([2H])(C[C@H](c1ccc(-c2cc(Cl)ccc2C#N)c[n+]1[O-])n1cc(-c2ncnn2C(F)F)cn1)OC(F)F]

LC/MS: mass calculated for $C_{24}H_{18}ClF_4N_7O_3$: 523.11, measured (ES, m/z): 524.05 [M+H]$^+$. $^1$H NMR (400 MHz, DMSO-d$_6$) δ 8.66-8.72 (m, 2H), 8.26 (s, 1H), 8.13 (s, 1H), 8.04-8.08 (m, 1H), 8.03 (t, J=68.0 Hz, 1H), 7.88 (d, J=2.1 Hz, 1H), 7.76 (d, J=8.4 Hz, 1H), 7.64 (d, J=8.3 Hz, 1H), 7.56 (d, J=8.3 Hz, 1H), 6.64 (t, J=76.0 Hz, 1H), 6.36 (dd, J=10.3, 4.4 Hz, 1H), 2.71-2.77 (m, 1H), 2.61-2.65 (m, 1H). $^{19}$F NMR (376 MHz, DMSO-d$_6$) δ −83.29, −96.13.

Example 894: (S*)-5-(5-Chloro-2-cyanophenyl)-2-(3-(difluoromethoxy)-1-(4-(1-(difluoromethyl)-1H-1,2,4-triazol-5-yl)-1H-pyrazol-1-yl)propyl-3,3-d2) pyridine 1-oxide

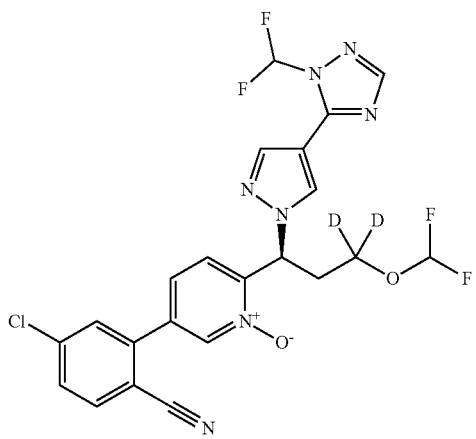 [SMILES: [2H]C([2H])(C[C@@H](c1ccc(-c2cc(Cl)ccc2C#N)c[n+]1[O-])n1cc(-c2ncnn2C(F)F)cn1)OC(F)F]

LC/MS: mass calculated for $C_{22}H_{14}D_2ClF_4N_7O_2$: 523.11, measured (ES, m/z): 524.05 [M+H]$^+$. $^1$H NMR (400 MHz, DMSO-d$_6$) δ 8.71-8.72 (m, 2H), 8.22-8.28 (m, 1H), 8.22-7.86 (m, 4H), 7.76 (d, J=8.5 Hz, 1H), 7.58-7.64 (m, 2H), 6.66 (t, J=76.0 Hz, 1H), 6.37-6.39 (m, 1H), 2.65-2.79 (m, 2H). $^{19}$F NMR (376 MHz, DMSO-d$_6$) δ −83.28, −96.13.

Example 895: (S)-2-(1-(4-(4-Chloro-1-methyl-1H-imidazol-5-yl)-1H-pyrazol-1-yl)-2-cyclopropylethyl)-5-(3-chloro-2-fluoro-6-(1H-tetrazol-1-yl)phenyl)pyridine 1-oxide

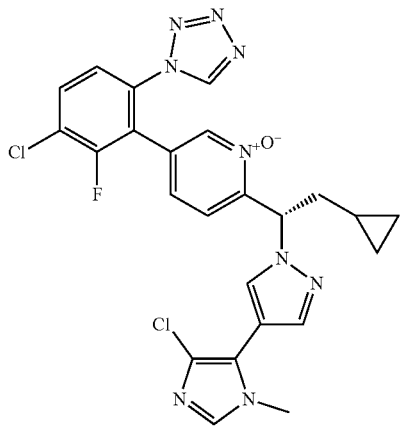

LC/MS: mass calculated for $C_{24}H_{20}Cl_2FN_9O$: 539.12, measured (ES, m/z): 540.10 [M+H]$^+$. $^1$H NMR (400 MHz, CD$_3$OD) δ 9.41 (s, 1H), 8.35 (s, 1H), 8.26 (s, 1H), 7.88-7.98 (m, 2H), 7.59-7.67 (m, 2H), 7.55 (d, J=8.3 Hz, 1H), 7.32 (dd, J=8.3, 1.7 Hz, 1H), 6.26-6.30 (m, 1H), 3.73 (s, 3H), 2.03-2.47 (m, 1H), 2.03-2.08 (m, 1H), 0.62-0.71 (m, 1H), 0.35-0.49 (m, 2H), 0.18-0.22 (m, 1H), −0.09-1.02 (m, 1H). $^{19}$F NMR (376 MHz, CD$_3$OD) δ −113.724, −76.947.

Example 896: (R)-2-(1-(4-(4-Chloro-1-methyl-1H-imidazol-5-yl)-1H-pyrazol-1-yl)-2-cyclopropylethyl)-5-(3-chloro-2-fluoro-6-(1H-tetrazol-1-yl)phenyl)pyridine 1-oxide

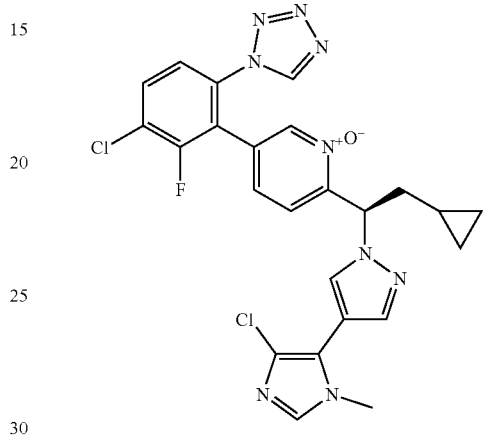

LC/MS: mass calculated for $C_{24}H_2O Cl_2FN_9O$: 539.12, measured (ES, m/z): 540.10 [M+H]$^+$. $^1$H NMR (400 MHz, CD$_3$OD) 9.41 (s, 1H), 8.41 (s, 1H), 8.27 (s, 1H), 7.88-8.00 (m, 2H), 7.60-7.67 (m, 2H), 7.55 (d, J=8.3 Hz, 1H), 7.32 (dd, J=8.3, 1.7 Hz, 1H), 6.28 (dd, J=10.1, 4.3 Hz, 1H), 3.73 (s, 3H), 2.47 (ddd, J=13.9, 10.1, 6.3 Hz, 1H), 2.07 (ddd, J=14.1, 7.9, 4.4 Hz, 1H), 0.65-0.77 (m, 1H), 0.35-0.50 (m, 2H), 0.12-0.21 (m, 1H), −0.09-1.03 (m, 1H). $^{19}$F NMR (376 MHz, CD$_3$OD) d −113.722, −76.940.

Example 897: (S)-2-(1-(3'-Chloro-1'-methyl-1H,1'H-[4,4'-bipyrazol]-1-yl)-3-(difluoromethoxy)propyl-3,3-d2)-5-(3-chloro-2-fluoro-6-(1H-tetrazol-1-yl)phenyl)pyridine 1-oxide

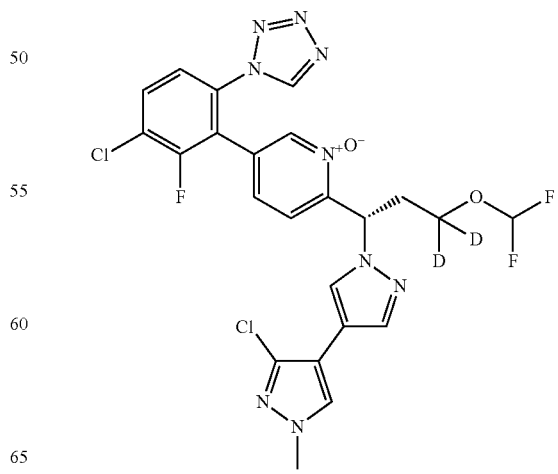

LC/MS: mass calculated for $C_{23}H_{16}Cl_2D_2F_3N_9O_2$: 581.1, measured (ES, m/z): 582.0 [M+H]$^+$. $^1$H NMR (300 MHz, CD$_3$OD) δ 9.39 (s, 1H), 8.40 (s, 1H), 8.13 (s, 1H), 7.88-7.98 (m, 2H), 7.85 (s, 1H), 7.60-7.64 (m, 1H), 7.40-7.47 (m, 1H), 7.26-7.32 (m, 1H), 6.10-6.64 (m, 2H), 3.87 (s, 3H), 2.64-2.80 (m, 2H). $^{19}$F NMR (282 MHz, CD$_3$OD) δ −86.00, −113.67.

Example 898: (R)-2-(1-(3'-Chloro-1'-methyl-1H, 1'H-[4,4'-bipyrazol]-1-yl)-3-(difluoromethoxy)propyl-3,3-d2)-5-(3-chloro-2-fluoro-6-(1H-tetrazol-1-yl)phenyl)pyridine 1-oxide

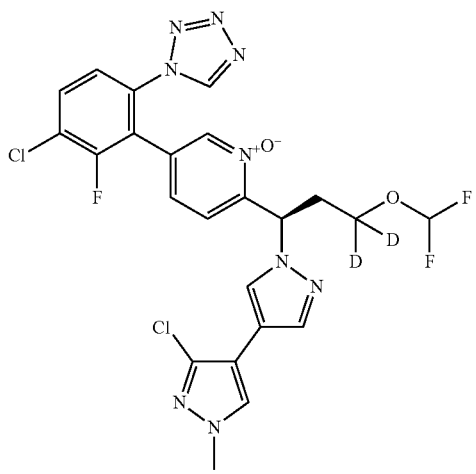

LC/MS: mass calculated for $C_{23}H_{16}Cl_2D_2F_3N_9O_2$: 581.1, measured (ES, m/z): 582.0 [M+H]$^+$. $^1$H NMR (300 MHz, CD$_3$OD) δ 9.39 (s, 1H), 8.40 (s, 1H), 8.13 (s, 1H), 7.88-7.99 (m, 2H), 7.85 (s, 1H), 7.60-7.64 (m, 1H), 7.40-7.47 (m, 1H), 7.26-7.32 (m, 1H), 6.10-6.64 (m, 2H), 3.87 (s, 3H), 2.63-2.80 (m, 2H). $^{19}$F NMR (282 MHz, CD$_3$OD) δ −86.00, −113.6.

Example 899: 5-(5-Chloro-2-cyanophenyl)-2-(1-(4-(1-(difluoromethyl)-1H-1,2,4-triazol-5-yl)-1H-pyrazol-1-yl)propyl)-4-methoxypyridine 1-oxide

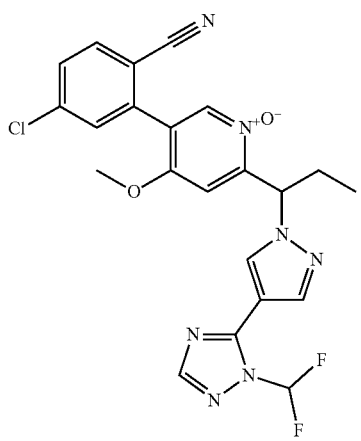

LC/MS: mass calculated for $C_{22}H_{18}ClF_2N_7O_2$: 485.12, measured (ES, m/z): 486.10 [M+H]$^+$. $^1$H NMR (400 MHz, CD$_3$OD) δ 8.60 (s, 1H), 8.42 (s, 1H), 8.17 (s, 1H), 8.13 (s, 1H), 7.81-7.91 (m, 2H), 7.66-7.73 (m, 2H), 7.44 (s, 1H), 6.23-6.29 (m, 1H), 3.97 (s, 3H), 2.52-2.66 (m, 1H), 2.38-2.50 (m, 1H), 1.03 (t, J=7.3 Hz, 3H). $^{19}$F NMR (376 MHz, CD$_3$OD) δ −77.49, −97.70, −97.97.

Example 900: 5-(3-Chloro-6-cyano-2-fluorophenyl)-2-((S)-2-cyclopropyl-1-(4-(1-(difluoromethyl)-1H-1,2,4-triazol-5-yl)-1H-pyrazol-1-yl)ethyl)-4-methoxypyridine 1-oxide

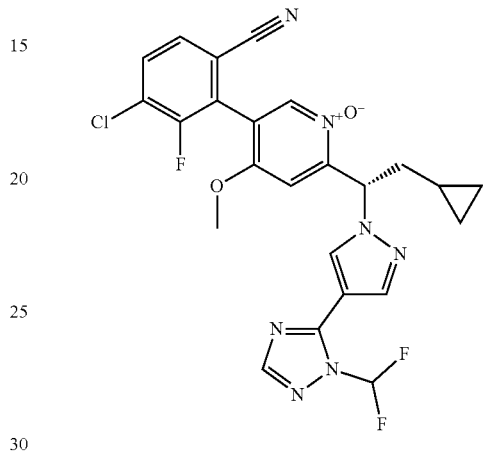

LC/MS: mass calculated for $C_{24}H_{19}ClF_3N_7O_2$: 529.12, measured (ES, m/z): 530.05 [M+H]$^+$. $^1$H NMR (300 MHz, DMSO-d$_6$) δ 8.78 (d, J=5.8 Hz, 1H), 8.59 (s, 1H), 8.28 (s, 1H), 8.06-8.15 (m, 2H), 7.87-8.02 (m, 2H), 7.32 (d, J=4.8 Hz, 1H), 6.28-6.35 (m, 1H), 3.85 (s, 3H), 2.41-2.48 (m, 1H), 2.08-2.22 (m, 1H), 0.63-0.69 (m, 1H), 0.28-0.44 (m, 2H), 0.14-0.25 (m, 1H), 0-0.02 (m, 1H). $^{19}$F NMR (282 MHz, DMSO-d$_6$) δ −96.10, −112.62.

Example 901: (R)-5-(3-Chloro-6-cyano-2-fluorophenyl)-2-((S*)-2-cyclopropyl-1-(4-(1-(difluoromethyl)-1H-1,2,4-triazol-5-yl)-1H-pyrazol-1-yl)ethyl)-4-methoxypyridine 1-oxide

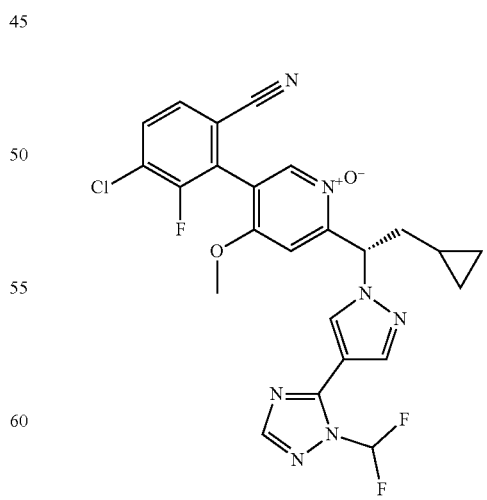

LC/MS: mass calculated for $C_{24}H_{19}ClF_3N_7O_2$: 529.12, measured (ES, m/z): 530.05 [M+H]$^+$. $^1$H NMR (300 MHz, DMSO-d$_6$) δ 8.78 (d, J=5.7 Hz, 1H), 8.59 (s, 1H), 8.27 (s, 1H), 8.06-8.15 (m, 2H), 7.87-8.02 (m, 2H), 7.32 (d, J=4.8 Hz, 1H), 6.28-6.35 (m, 1H), 3.85 (s, 3H), 2.38-2.46 (m, 1H), 2.05-2.22 (m, 1H), 0.61-0.69 (m, 1H), 0.28-0.45 (m, 2H), 0.14-0.24 (m, 1H), −0.04-0.04 (m, 1H). $^{19}$F NMR (282 MHz, DMSO-d$_6$) δ −96.10, −112.62.

Example 902: (S)-2-(1-(3'-Chloro-1'-methyl-1H,1'H-[4,4'-bipyrazol]-1-yl)-2-(1-(difluoromethyl)-1H-pyrazol-3-yl)ethyl)-5-(3-chloro-6-4-cyano-1H-1,2,3-triazol-1-yl)-2-fluorophenyl)pyridine 1-oxide

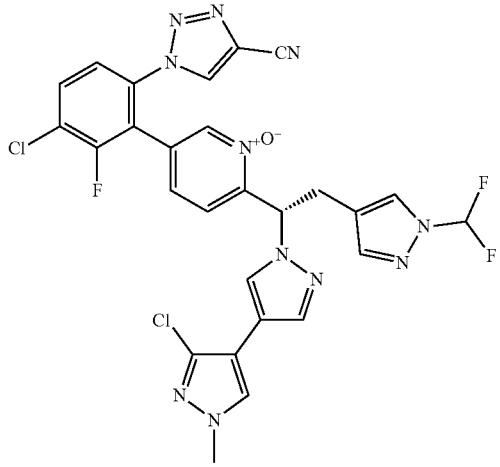

LC/MS: mass calculated for $C_{27}H_{18}Cl_2F_3N_{11}O$: 639.1, measured (ES, m/z): 640.2 [M+H]$^+$. $^1$H NMR (400 MHz, CD$_3$OD) δ 8.90 (s, 1H), 8.34 (s, 1H), 8.07 (s, 1H), 7.85-7.94 (m, 2H), 7.76-7.85 (m, 2H), 7.56-7.62 (m, 1H), 7.20-7.52 (m, 3H), 6.51 (t, J=7.5 Hz, 1H), 6.17 (d, J=2.7 Hz, 1H), 3.83 (s, 3H), 3.72-3.80 (m, 2H). $^{19}$F NMR (376 MHz, CD$_3$OD) δ −76.97, −95.78, −113.80.

Example 903: (R)-2-(1-(3'-Chloro-1'-methyl-1H,1'H-[4,4'-bipyrazol]-1-yl)-2-(1-(difluoromethyl)-1H-pyrazol-3-yl)ethyl)-5-(3-chloro-6-(4-cyano-1H-1,2,3-triazol-1-yl)-2-fluorophenyl)pyridine 1-oxide

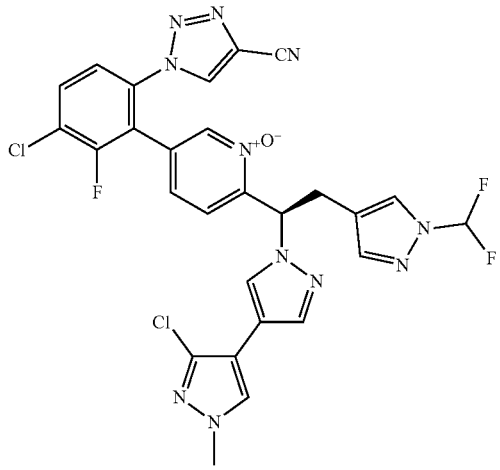

LC/MS: mass calculated for $C_{27}H_{18}Cl_2F_3N_{11}O$: 639.1, measured (ES, m/z): 640.1 [M+H]$^+$. $^1$H NMR (400 MHz, CD$_3$OD) δ 8.90 (s, 1H), 8.34 (s, 1H), 8.07 (s, 1H), 7.86-7.94 (m, 2H), 7.82 (s, 1H), 7.78 (s, 1H), 7.56-7.62 (m, 1H), 7.19-7.52 (m, 3H), 6.51 (t, J=7.5 Hz, 1H), 6.17 (d, J=2.7 Hz, 1H), 3.83 (s, 3H), 3.76 (d, J=7.5 Hz, 2H). $^{19}$F NMR (376 MHz, CD$_3$OD) δ −95.91, −113.80.

Example 904: 5-(3-Chloro-2-fluoro-6-(4-(trifluoromethyl)-1H-1,2,3-triazol-1-yl)phenyl)-2-(1-(2-(difluoromethyl)-1'H,2H-[3,4'-bipyrazol]-1'-yl)-3-(methoxy-d3)propyl-1,3,3-d3)pyridine 1-oxide TFA

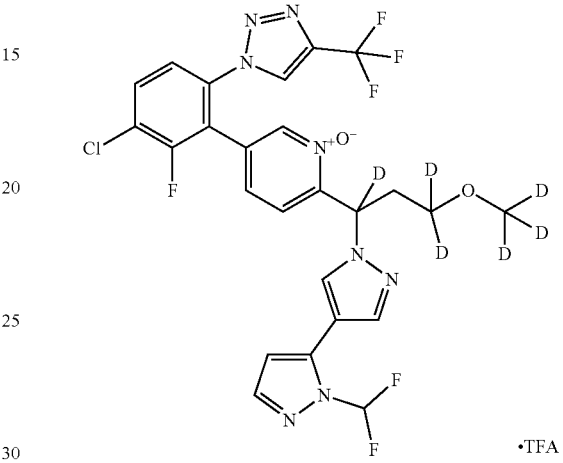

LC-MS: calculated mass for $C_{25}H_{13}D_6ClF_6N_8O_2$: 618.2, measured (ES, m/z): 619.0 [M+H]$^+$. $^1$H NMR (CD$_3$OD, 400 MHz) δ-8.79 (s, 1H), 8.36 (s, 1H), 8.20 (s, 1H), 7.90 (t, J=8.3 Hz, 1H), 7.84 (s, 1H), 7.73-7.55 (m, 3H), 7.53 (t, J=58.2 Hz, 1H), 7.30 (d, J=8.3 Hz, 1H), 6.58 (s, 1H), 2.65-2.50 (m, 2H). $^{19}$F NMR (CD$_3$OD, 377 MHz) δ--114.0 (s), −95.3 (s), −62.7 (s).

Example 905: (S)-2-(1-(4-(4-Carboxyphenyl)-1H-pyrazol-1-yl)-2-(1-methyl-1H-pyrazol-3-yl)ethyl)-5-(3-chloro-2-fluoro-6-(4-(trifluoromethyl)-1H-1,2,3-triazol-1-yl)phenyl)pyridine 1-oxide

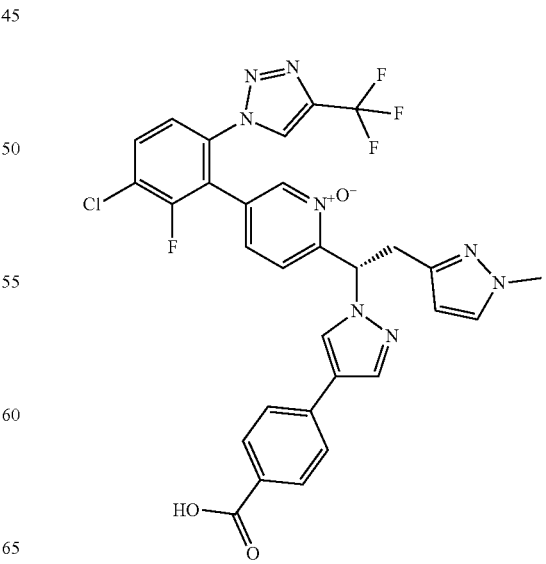

LC/MS: mass calculated for C₃₀H₂₁ClF₄N₈O₃: 652.14, measured (ES, m/z): 653.05 [M+H]⁺. ¹H NMR (400 MHz, DMSO-d₆) δ 9.16 (s, 1H), 8.53 (s, 1H), 8.42 (d, J=1.6 Hz, 1H), 8.00-8.09 (m, 2H), 7.89-7.93 (m, 2H), 7.73-7.79 (m, 1H), 7.68-7.72 (m, 2H), 7.44 (d, J=2.1 Hz, 1H), 7.30-7.35 (m, 1H), 7.12-7.18 (m, 1H), 6.33 (t, J=7.4 Hz, 1H), 5.79 (d, J=2.2 Hz, 1H), 3.72 (s, 3H), 3.51 (d, J=7.4 Hz, 2H).

Example 906: (R)-2-(1-(4-(4-Carboxyphenyl)-1H-pyrazol-1-yl)-2-(1-methyl-1H-pyrazol-3-yl)ethyl)-5-(3-chloro-2-fluoro-6-(4-(trifluoromethyl)-1H-1,2,3-triazol-1-yl)phenyl)pyridine 1-oxide

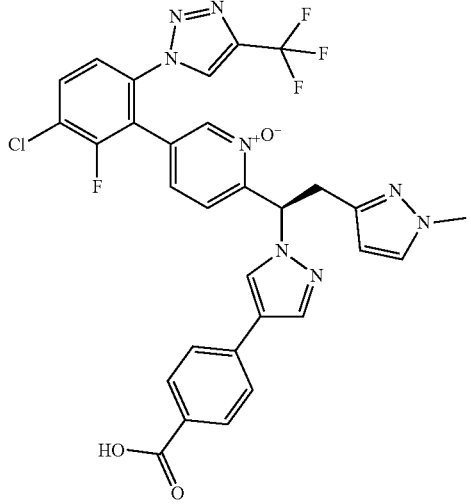

LC/MS: mass calculated for C₃₀H₂₁ClF₄N₈O₃: 652.14, measured (ES, m/z): 653.05 [M+H]⁺. ¹H NMR (400 MHz, DMSO-d₆) δ 12.67 (s, 1H), 9.16 (s, 1H), 8.53 (s, 1H), 8.42 (d, J=1.6 Hz, 1H), 8.00-8.09 (m, 2H), 7.87-7.94 (m, 2H), 7.66-7.79 (m, 3H), 7.45 (d, J=2.2 Hz, 1H), 7.30-7.34 (m, 1H), 7.11-7.17 (m, 1H), 6.33 (t, J=7.4 Hz, 1H), 5.79 (d, J=2.2 Hz, 1H), 3.72 (s, 3H), 3.51 (d, J=7.4 Hz, 2H).

Example 907: (S)-2-(1-(4-(4-Carboxyphenyl)-1H-pyrazol-1-yl)-2-(1-methyl-1H-pyrazol-3-yl)ethyl)-5-(5-chloro-2-(2,2,2-trifluoroethoxy)phenyl)pyridine 1-oxide

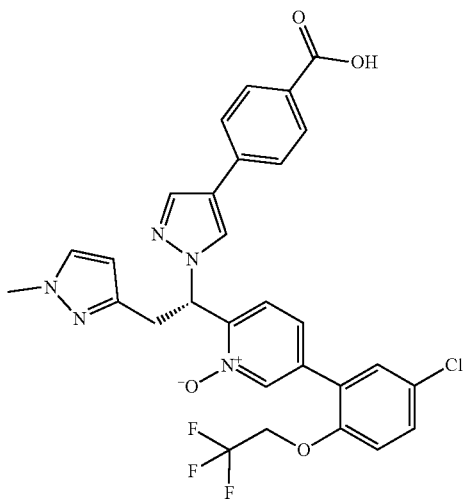

LC/MS: mass calculated for C₂₉H₂₃ClF₃N₅O₄:597.1, measured (ES, m/z): 598.1 [M+H]⁺. ¹H NMR (400 MHz, DMSO-d₆) δ 8.59 (s, 1H), 8.50 (d, J=1.7 Hz, 1H), 8.11 (s, 1H), 7.88-7.94 (m, 2H), 7.69-7.74 (m, 2H), 7.44-7.60 (m, 4H), 7.38-7.42 (m, 1H), 7.30-7.34 (m, 1H), 6.41 (t, J=7.4 Hz, 1H), 5.85 (d, J=2.2 Hz, 1H), 4.85 (q, J=8.8 Hz, 2H), 3.73 (s, 3H), 3.59 (d, J=7.6 Hz, 2H).

Example 908: (R)-2-(1-(4-(4-Carboxyphenyl)-1H-pyrazol-1-yl)-2-(1-methyl-1H-pyrazol-3-yl)ethyl)-5-(5-chloro-2-(2,2,2-trifluoroethoxy)phenyl)pyridine 1-oxide

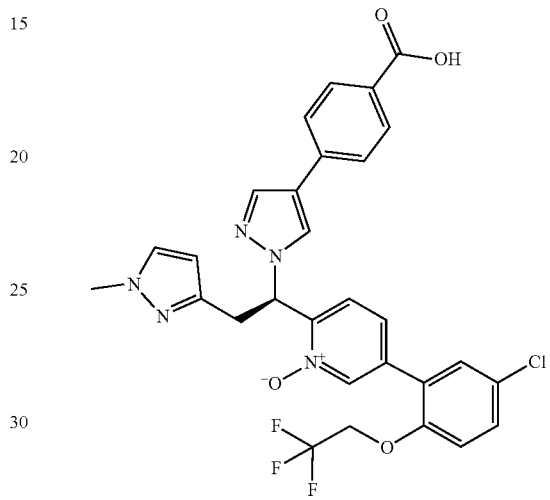

LC/MS: mass calculated for C₂₉H₂₃ClF₃N₅O₄:597.14, measured (ES, m/z): 598.25 [M+H]⁺. ¹H NMR (400 MHz, DMSO-d₆) δ 8.59 (s, 1H), 8.50 (d, J=1.7 Hz, 1H), 8.11 (s, 1H), 7.88-7.94 (m, 2H), 7.68-7.75 (m, 2H), 7.45-7.60 (m, 4H), 7.38-7.42 (m, 1H), 7.30-7.34 (m, 1H), 6.39-6.46 (m, 1H), 5.85 (d, J=2.2 Hz, 1H), 4.85 (q, J=8.8 Hz, 2H), 3.73 (s, 3H), 3.53-3.62 (m, 2H).

Example 909: (R)-5-(3-Chloro-6-(4-cyano-1H-1,2,3-triazol-1-yl)-2-fluorophenyl)-2-(1-(4-(1-(difluoromethyl)-1H-1,2,4-triazol-5-yl)-1H-pyrazol-1-yl)-3-hydroxypropyl-3,3-d2)pyridine 1-oxide

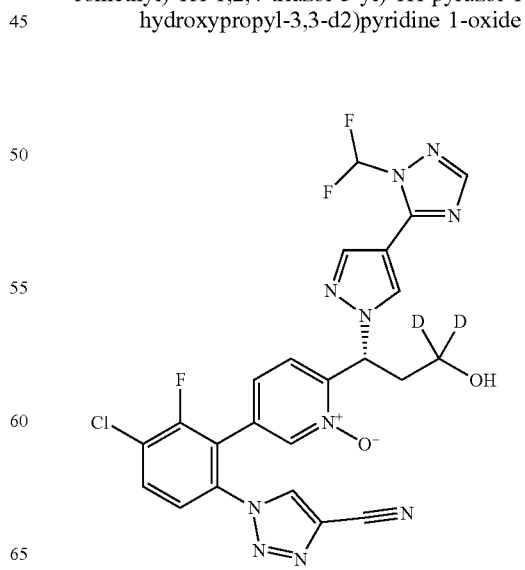

LC/MS: mass calculated for $C_{23}H_{14}ClD_2F_3N_{10}O_2$: 558.12, measured (ES, m/z): 559.05 [M+H]$^+$. $^1$H NMR (400 MHz, DMSO-d$_6$) δ 9.32 (s, 1H), 8.60 (s, 1H), 8.42 (d, J=1.6 Hz, 1H), 8.24 (s, 1H), 8.21-7.88 (m, 3H), 7.72 (dd, J=8.8, 1.5 Hz, 1H), 7.44 (d, J=8.3 Hz, 1H), 7.50-7.65 (m, 1H), 7.14-7.18 (m, 1H), 6.28-6.35 (m, 1H), 2.40-2.50 (m, 1H), 2.25-2.40 (m, 1H). $^{19}$F NMR (376 MHz, DMSO-d$_6$) δ −95.48, −96.10, −96.13, −96.78, −112.66.

Example 910: (S)-5-(3-Chloro-6-(4-cyano-1H-1,2,3-triazol-1-yl)-2-fluorophenyl)-2-(1-(4-(1-(difluoromethyl)-1H-1,2,4-triazol-5-yl)-1H-pyrazol-1-yl)-3-hydroxypropyl-3,3-d$_2$)pyridine 1-oxide

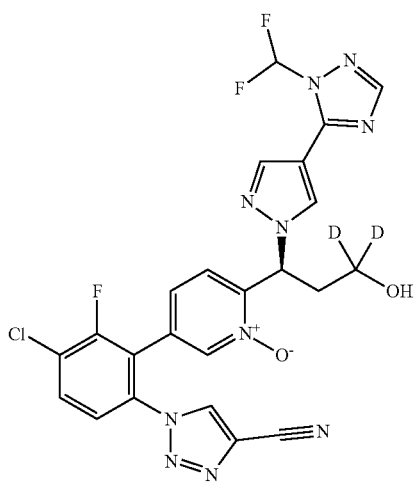 [SMILES: [2H]C([2H])(O)C[C@@H](c1ccc(-c2c(-n3cc(C#N)nn3)ccc(Cl)c2F)c[n+]1[O-])n1cc(-c2ncnn2C(F)F)cn1]

LC/MS: mass calculated for $C_{23}H_{14}ClD_2F_3N_{10}O_2$: 558.12, measured (ES, m/z): 559.05 [M+H]$^+$. $^1$H NMR (400 MHz, DMSO-d$_6$) δ 9.32 (s, 1H), 8.60 (s, 1H), 8.42 (d, J=1.7 Hz, 1H), 8.24 (s, 1H), 8.21-7.87 (m, 3H), 7.70-7.75 (m, 1H), 7.48-7.52 (m, 1H), 7.18-7.22 (m, 1H), 6.28-6.32 (m, 1H), 2.40-2.50 (m, 1H), 2.29-2.37 (m, 1H). $^{19}$F NMR (376 MHz, DMSO-d$_6$) δ −96.03, −96.14, −112.75.

Example 911: 5-(3-Chloro-6-(4-cyano-1H-1,2,3-triazol-1-yl)-2-fluorophenyl)-2-(1-(4-(1-(difluoromethyl)-1H-1,2,4-triazol-5-yl)-1H-pyrazol-1-yl)-3-hydroxypropyl-3,3-d$_2$)pyridine 1-oxide

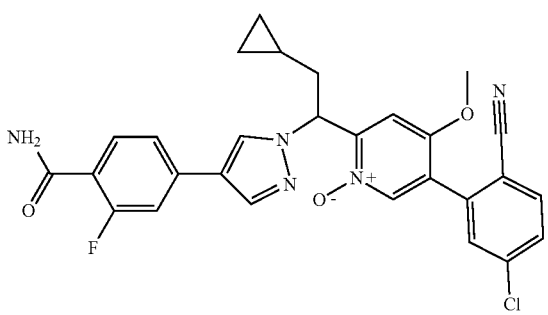

LC/MS: mass calculated for $C_{28}H_{23}ClFN_5O_3$: 531.15, measured (ES, m/z): 532.15 [M+H]$^+$. $^1$H NMR (400 MHz, DMSO-d$_6$) δ 8.69 (s, 1H), 8.39 (s, 1H), 8.16 (s, 1H), 7.98-8.02 (m, 1H), 7.78-7.83 (m, 1H), 7.74-7.52 (m, 6H), 7.20 (s, 1H), 6.18-6.24 (m, 1H), 3.78 (s, 3H), 2.40-2.48 (m, 1H), 1.90-2.09 (m, 1H), 0.54-0.67 (m, 1H), 0.24-0.47 (m, 2H), 0.10-0.22 (m, 1H), 0.00-0.09 (m, 1H). $^{19}$F NMR (376 MHz, DMSO-d$_6$) δ −112.98.

Example 912: (R*)-5-(5-Chloro-2-cyanophenyl)-2-(2-cyclopropyl-1-(4-(1-methyl-1H-1,2,4-triazol-5-yl)-1H-pyrazol-1-yl)ethyl)-4-methoxypyridine 1-oxide

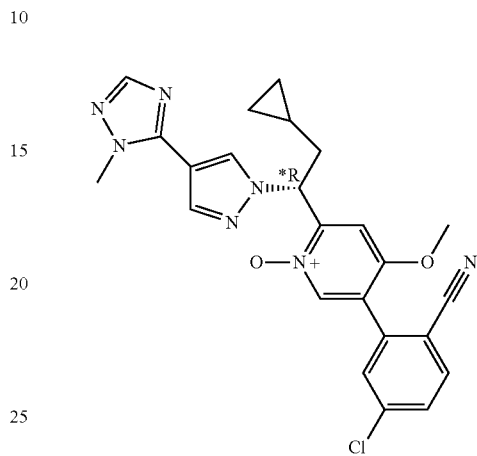

LC/MS: mass calculated for $C_{24}H_{22}ClN_7O_2$: 475.15, measured (ES, m/z): 498.10 [M+Na]$^+$. $^1$H NMR (400 MHz, DMSO-d$_6$) δ 8.70 (s, 1H), 8.40 (s, 1H), 8.08 (s, 1H), 7.97-8.03 (m, 1H), 7.88 (s, 1H), 7.79 (d, J=2.2 Hz, 1H), 7.71-7.78 (m, 1H), 7.24 (s, 1H), 6.28-6.33 (m, 1H), 3.97 (s, 3H), 3.80 (s, 3H), 2.36-2.45 (m, 1H), 2.02-2.14 (m, 1H), 0.56-0.66 (m, 1H), 0.37-0.43 (m, 1H), 0.26-0.36 (m, 1H), 0.14-0.22 (m, 1H), −0.06-0.03 (m, 1H).

Example 913: (S*)-5-(5-Chloro-2-cyanophenyl)-2-(2-cyclopropyl-1-(4-(1-methyl-1H-1,2,4-triazol-5-yl)-1H-pyrazol-1-yl)ethyl)-4-methoxypyridine 1-oxide

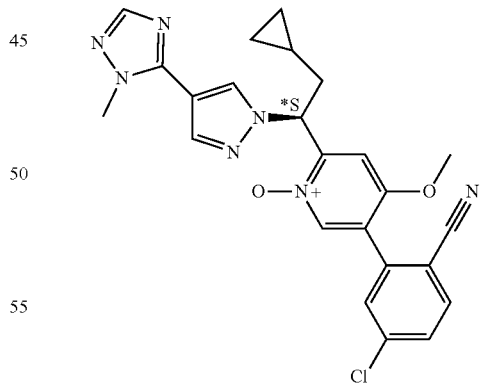

LC/MS: mass calculated for $C_{24}H_{22}ClN_7O_2$: 475.15, measured (ES, m/z): 498.05 [M+Na]$^+$. $^1$H NMR (400 MHz, DMSO-d$_6$) δ 8.70 (s, 1H), 8.40 (s, 1H), 8.08 (s, 1H), 7.99 (d, J=8.3 Hz, 1H), 7.88 (s, 1H), 7.79 (s, 1H), 7.72 (d, J=8.5 Hz, 1H), 7.24 (s, 1H), 6.28-6.32 (m, 1H), 3.97 (s, 3H), 3.80 (s, 3H), 2.32-2.44 (m, 1H), 2.02-2.14 (m, 1H), 0.56-0.66 (m, 1H), 0.37-0.44 (m, 1H), 0.26-0.36 (m, 1H), 0.15-0.21 (m, 1H), −0.05-0.03 (m, 1H).

Example 914: (R)-2-(1-(4-(4-Carboxyphenyl)-1H-pyrazol-1-yl)-3-(difluoromethoxy)propyl)-5-(3-chloro-2-fluoro-6-(4-(trifluoromethyl)-1H-1,2,3-triazol-1-yl)phenyl)pyridine 1-oxide

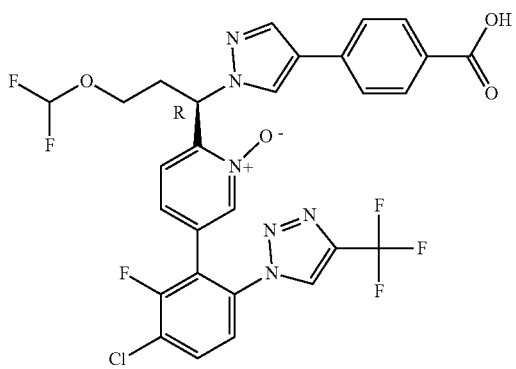

Step 1: tert-Butyl 4-(1-(1-(6-bromopyridin-3-yl)-3-(difluoromethoxy)propyl)-1H-pyrazol-4-yl)benzoate A mixture of tert-butyl 4-(1H-pyrazol-4-yl)benzoate (339 mg, 1.39 mmol, 1.0 equiv.) and t-BuONa (500 mg, 1.39 mmol, 0.9 equiv.) in DMF was stirred at ice bath for 30 min. To the solution was then added 1-(6-bromopyridin-3-yl)-3-(difluoromethoxy)propyl methanesulfonate (120 mg, 1.25 mmol, 1.0 equiv.). The resulting mixture was stirred at room temperature for 2 h. The reaction was diluted with water, extracted with EA (3×10 mL). The organic layers were combined, washed with brine, dried over $Na_2SO_4$ and concentrated. The residue was purified by silica gel column to yield tert-butyl 4-(1-(1-(6-bromopyridin-3-yl)-3-(difluoromethoxy)propyl)-1H-pyrazol-4-yl)benzoate as a colorless oil. LC/MS: mass calculated for $C_{23}H_{24}BrF_2N_3O_3$: 507.10, measured (ES, m/z): 508.20 $[M+H]^+$.

Step 2: (5-(1-(4-(4-(tert-Butoxycarbonyl)phenyl)-1H-pyrazol-1-yl)-3-(difluoromethoxy)propyl)pyridin-2-yl)boronic acid A mixture of tert-butyl 4-(1-(1-(6-bromopyridin-3-yl)-3-(difluoromethoxy)propyl)-1H-pyrazol-4-yl)benzoate (600 mg, 1.18 mmol, 1.0 equiv.), 4,4,4',4',5,5,5',5'-octamethyl-2,2'-bi(1,3,2-dioxaborolane) (450 mg, 1.77 mmol, 1.5 equiv.), Pd(dppf)Cl$_2$ (86 mg, 0.12 mmol, 0.1 equiv.) and KOAc (348 mg, 3.54 mmol, 3.0 equiv.) in 1,4-dioxane (6 mL) was stirred for 2 h at 90° C. The reaction was diluted with water, extracted with EA (3×20 mL). The organic layers were combined and washed with brine, dried over $Na_2SO_4$ and concentrated to yield (5-(1-(4-(4-(tert-butoxycarbonyl)phenyl)-1H-pyrazol-1-yl)-3-(difluoromethoxy)propyl)pyridin-2-yl)boronic acid as a black oil. LC/MS: mass calculated for $C_{23}H_{26}BF_2N_3O_5$: 473.19, measured (ES, m/z): 474.10 $[M+H]^+$.

Step 3: tert-butyl 4-(1-(1-(6-(3-chloro-2-fluoro-6-(4-(trifluoromethyl)-1H-1,2,3-triazol-1-yl)phenyl)pyridin-3-yl)-3-(difluoromethoxy)propyl)-1H-pyrazol-4-yl)benzoate A mixture of 1-(4-chloro-3-fluoro-2-iodophenyl)-4-(trifluoromethyl)-1H-1,2,3-triazole (538 mg, 1.37 mmol, 1.3 equiv.), (5-(1-(4-(4-(tert-butoxycarbonyl)phenyl)-1H-pyrazol-1-yl)-3-(difluoromethoxy)propyl)pyridin-2-yl)boronic acid (500 mg, 1.06 mmol, 1.0 equiv.), Pd(PPh$_3$)$_4$ (122.1 mg, 0.11 mmol, 0.1 equiv.) and K$_2$CO$_3$ (438 mg, 3.17 mmol, 3.0 equiv.) in 1,4-dioxane/water (V/V=5:1, 6 mL) was refluxed at 90° C. under N$_2$ for 3 h.

The resulting mixture was diluted with water (20 mL), extracted with EA (3×20 mL). The organic layers were combined, washed with brine, dried over Na$_2$SO$_4$ and concentrated. The residue was purified by silica gel chromatography to yield tert-butyl 4-(1-(1-(6-(3-chloro-2-fluoro-6-(4-(trifluoromethyl)-1H-1,2,3-triazol-1-yl)phenyl)pyridin-3-yl)-3-(difluoromethoxy)propyl)-1H-pyrazol-4-yl)benzoate as a light yellow oil. LC/MS: mass calculated for $C_{32}H_{27}ClF_6N_6O_3$: 692.17, measured (ES, m/z): 693.35 $[M+H]^+$.

Step 4: 4-(1-(1-(6-(3-Chloro-2-fluoro-6-(4-(trifluoromethyl)-1H-1,2,3-triazol-1-yl)phenyl)pyridin-3-yl)-3-(difluoromethoxy)propyl)-1H-pyrazol-4-yl)benzoic acid To a solution of tert-butyl 4-(1-(1-(6-(3-chloro-2-fluoro-6-(4-(trifluoromethyl)-1H-1,2,3-triazol-1-yl)phenyl)pyridin-3-yl)-3-(difluoromethoxy)propyl)-1H-pyrazol-4-yl)benzoate (550 mg, 0.79 mmol, 1.0 equiv.) in DCM (6 mL) was added 2,2,2-trifluoroacetic acid (6 mL). The resulting mixture was stirred at room temperature for 2 h. The resulting mixture was concentrated to yield 4-(1-(1-(6-(3-chloro-2-fluoro-6-(4-(trifluoromethyl)-1H-1,2,3-triazol-1-yl)phenyl)pyridin-3-yl)-3-(difluoromethoxy)propyl)-1H-pyrazol-4-yl)benzoic acid as a light yellow oil which was used in the next step without purification. LC/MS: mass calculated for $C_{28}H_{19}ClF_6N_6O_3$: 636.11, measured (ES, m/z): 637.05 $[M+H]^+$.

Step 5: 5-((R)-1-(4-(4-Carboxyphenyl)-1H-pyrazol-1-yl)-3-(difluoromethoxy)propyl)-2-(3-chloro-2-fluoro-6-(4-(trifluoromethyl)-1H-1,2,3-triazol-1-yl)phenyl)pyridine 1-oxide To a solution of 4-(1-(1-(6-(3-chloro-2-fluoro-6-(4-(trifluoromethyl)-1H-1,2,3-triazol-1-yl)phenyl)pyridin-3-yl)-3-(difluoromethoxy)propyl)-1H-pyrazol-4-yl)benzoic acid (250 mg, 0.39 mmol, 1.0 equiv.) in CH$_3$OH (2 mL) was added methyltrioxorhenium (73.3 mg, 0.29 mmol, 0.75 equiv.) and hydrogen peroxide (0.7 mL, 30 wt %). The resulting mixture stirred at room temperature for 1 h. The resulting mixture was purified by reverse phase chromatography on C18 (MeCN/H$_2$O (0.05% CF$_3$COOH)) to yield racemic product (135 mg), which was separated by chiral-HPLC to yield 5-((R)-1-(4-(4-carboxyphenyl)-1H-pyrazol-1-yl)-3-(difluoromethoxy)propyl)-2-(3-chloro-2-fluoro-6-(4-(trifluoromethyl)-1H-1,2,3-triazol-1-yl)phenyl)pyridine 1-oxide as an off-white solid.

LC/MS: mass calculated for $C_{28}H_{19}ClF_6N_8O_4$: 652.11, measured (ES, m/z): 653.10 $[M+H]^+$. $^1$H NMR (400 MHz, DMSO-d$_6$) δ 12.78-12.88 (m, 1H), 9.15 (d, J=1.1 Hz, 1H), 8.55 (s, 1H), 8.41 (d, J=1.6 Hz, 1H), 8.13 (s, 1H), 8.00-8.05 m, 1H), 7.87-7.94 (m, 2H), 7.68-7.79 (m, 3H), 7.24 (d, J=8.3 Hz, 1H), 7.10-7.15 (m, 1H), 6.40-6.82 (m, 1H), 6.10-6.21 (m, 1H), 3.80-3.86 (m, 1H), 3.66-3.72 (m, 1H), 2.53-2.64 (m, 2H). $^{19}$F-NMR (282 MHz, DMSO-d$_6$) δ −59.78, −83.29, −112.84.

Example 915: ((R)-5-(1-(4-(4-Carbamoyl-3-fluoro-phenyl)-1H-pyrazol-1-yl)-3-(difluoromethoxy)pro-pyl)-2-(5-chloro-2-(4-(trifluoromethyl)-1H-1,2,3-triazol-1-yl)phenyl)pyridine 1-oxide

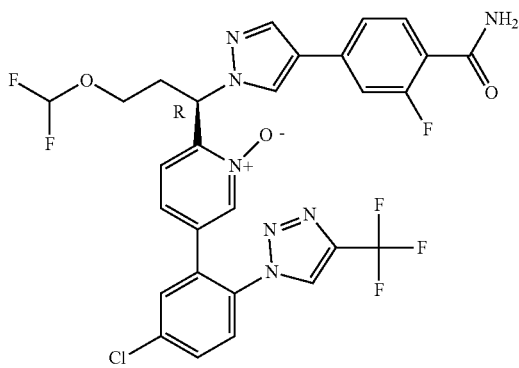

Step 1: 4-(1-(1-(6-Bromopyridin-3-yl)-3-(difluo-romethoxy)propyl)-1H-pyrazol-4-yl)-2-fluorobenz-amide A mixture of 2-fluoro-4-(1H-pyrazol-4-yl)benzamide (684 mg, 3.33 mmol, 1.2 equiv.) and t-BuONa (240 mg, 2.49 mmol, 0.9 equiv.) in DMF was stirred at ice bath for 30 min. To the solution was then added 1-(6-bromopyridin-3-yl)-3-(difluoromethoxy)propyl methanesulfonate (1.0 g, 2.78 mmol, 1.0 equiv.). The resulting mixture was stirred at room temperature for 2 h. The resulting mixture was diluted with water (20 mL), extracted with EA (3×20 mL). Then the organic layers were combined, washed with water and brine, dried over $Na_2SO_4$ and concentrated. The residue was purified by silica gel chromatography to yield 4-(1-(1-(5-bro-mopyridin-2-yl)-3-(difluoromethoxy)propyl)-1H-pyrazol-4-yl)-2-fluorobenzamide as a light yellow oil. LC/MS: mass calculated for $C_{19}H_{16}BrF_3N_4O_2$: 468.04, measured (ES, m/z): 469.00 $[M+H]^+$.

Step 2: (5-(1-(4-(4-Carbamoyl-3-fluorophenyl)-1H-pyrazol-1-yl)-3-(difluoromethoxy)propyl)pyridin-2-yl)boronic acid A mixture of 4-(1-(1-(5-bromopyridin-2-yl)-3-(difluo-romethoxy)propyl)-1H-pyrazol-4-yl)-2-fluorobenzamide (509 mg, 1.09 mmol, 1.0 equiv.), 4,4,4',4',5,5,5',5'-octam-ethyl-2,2'-bi(1,3,2-dioxaborolane) (413 mg, 1.63 mmol, 1.5 equiv.), Pd(dppf)Cl$_2$ (79 mg, 0.11 mmol, 0.1 equiv.) and KOAc (319 mg, 3.25 mmol, 3.0 equiv.) in 1,4-dioxane (6 mL) was stirred for 2 h at 90° C. The resulting mixture was diluted with water (10 mL), extracted with EA (3×10 mL). Then the organic layers were combined, washed with brine, dried over $Na_2SO_4$ and concentrated to yield (5-(1-(4-(4-carbamoyl-3-fluorophenyl)-1H-pyrazol-1-yl)-3-(difluo-romethoxy)propyl)pyridin-2-yl)boronic acid (470 mg) as a black oil. LC/MS: mass calculated for $C_{19}H_{18}BF_3N_4O_4$: 434.14, measured (ES, m/z): 435.25 $[M+H]^+$.

Step 3: 4-(1-(1-(6-(5-Chloro-2-(4-(trifluoromethyl)-1H-1,2,3-triazol-1-yl)phenyl)pyridin-3-yl)-3-(difluo-romethoxy)propyl)-1H-pyrazol-4-yl)-2-fluorobenz-amide A mixture of 1-(4-chloro-3-fluoro-2-iodophenyl)-4-(trif-luoromethyl)-1H-1,2,3-triazole (224 mg, 0.59 mmol, 1.2 equiv.), (5-(1-(4-(4-carbamoyl-3-fluorophenyl)-1H-pyrazol-1-yl)-3-(difluoromethoxy)propyl)pyridin-2-yl)boronic acid (200 mg, 0.46 mmol, 1.0 equiv.), Pd(PPh$_3$)$_4$ (53 mg, 0.05 mmol, 0.1 equiv.) and K$_2$CO$_3$ (191 mg, 1.38 mmol, 3.0 equiv.) in 1,4-dioxane/water (V/V=5:1, 3.6 mL) was refluxed at 90° C. under N$_2$ for 3 h.

The resulting mixture was diluted with water (10 mL), extracted with EA (3×10 mL). The organic layers were combined, washed with brine, dried over Na$_2$SO$_4$ and concentrated. The residue was purified by silica gel chromatography to yield 4-(1-(1-(6-(5-chloro-2-(4-(trifluoromethyl)-1H-1,2,3-triazol-1-yl)phenyl)pyridin-3-yl)-3-(difluoromethoxy)propyl)-1H-pyrazol-4-yl)-2-fluorobenzamide as a light yellow oil. LC/MS: mass calculated for $C_{28}H_{20}ClF_6N_7O_2$: 635.13, measured (ES, m/z): 636.30 $[M+H]^+$.

Step 4: (R)-5-(1-(4-(4-carbamoyl-3-fluorophenyl)-1H-pyrazol-1-yl)-3-(difluoromethoxy)propyl)-2-(5-chloro-2-(4-(trifluoromethyl)-1H-1,2,3-triazol-1-yl)phenyl)pyridine 1-oxide A mixture of 4-(1-(1-(6-(5-chloro-2-(4-(trifluoromethyl)-1H-1,2,3-triazol-1-yl)phenyl)pyridin-3-yl)-3-(difluo-romethoxy)propyl)-1H-pyrazol-4-yl)-2-fluorobenzamide (300 mg, 0.47 mmol, 1.0 equiv.), methyltrioxorhenium (118 mg, 0.47 mmol, 1.0 equiv.), hydrogen peroxide (0.2 mL, 30 wt %) in CH$_3$OH (3 mL) was stirred for 3 h at room temperature. The resulting mixture was purified by reverse phase chromatography on C$_{18}$ (MeCN/H$_2$O (0.05% CF$_3$COOH)) to yield a residue which was separated by chiral-HPLC to yield (R)-5-(1-(4-(4-carbamoyl-3-fluoro-phenyl)-1H-pyrazol-1-yl)-3-(difluoromethoxy)propyl)-2-(5-chloro-2-(4-(trifluoromethyl)-1H-1,2,3-triazol-1-yl)phe-nyl)pyridine 1-oxide as a white solid.

LC/MS: mass calculated for $C_{28}H_{20}ClF_6N_7O_3$: 651.12, measured (ES, m/z): 652.10 $[M+H]^+$. $^1$H NMR (300 MHz, DMSO-d$_6$) δ 9.17 (d, J=1.2 Hz, 1H), 8.58 (s, 1H), 8.30 (d, J=1.7 Hz, 1H), 8.16 (s, 1H), 7.87-7.90 (m, 1H), 7.84 (d, J=1.4 Hz, 2H), 7.47-7.73 (m, 5H), 7.24 (d, J=8.3 Hz, 1H), 6.92-6.98 (m, 1H), 6.30-6.90 (m, 1H), 6.18-6.23 (m, 1H), 3.79-3.89 (m, 1H), 3.66-3.74 (m, 1H), 2.52-2.67 (m, 2H). $^{19}$F-NMR (282 MHz, DMSO-d$_6$) δ −59.71, −83.26, −112.97.

Example 916: (R)-2-(1-(4-(4-Carbamoyl-3-fluoro-phenyl)-1H-pyrazol-1-yl)-3-(difluoromethoxy)pro-pyl)-5-(3-chloro-2-fluoro-6-(4-(trifluoromethyl)-1H-1,2,3-triazol-1-yl)phenyl)pyridine 1-oxide

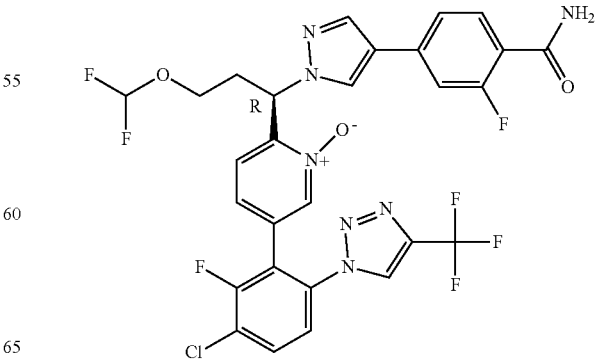

Step 1: 4-(1-(1-(6-(3-Chloro-2-fluoro-6-(4-(trifluoromethyl)-1H-1,2,3-triazol-1-yl)phenyl)pyridin-3-yl)-3-(difluoromethoxy)propyl)-1H-pyrazol-4-yl)-2-fluorobenzamide A mixture of (6-(1-(4-(4-carbamoyl-3-fluorophenyl)-1H-pyrazol-1-yl)-3-(difluoromethoxy)propyl)pyridin-3-yl)boronic acid (300 mg, 0.69 mmol, 1.0 equiv.), 1-(4-chloro-3-fluoro-2-iodophenyl)-4-(trifluoromethyl)-1H-1,2,3-triazole (325 mg, 0.83 mmol, 1.2 equiv.), Pd(PPh$_3$)$_4$ (80 mg, 0.07 mmol, 0.1 equiv.) and K$_2$CO$_3$ (287 mg, 2.07 mmol, 3.0 equiv.) in 1,4-dioxane/water (V/V=5:1, 2.4 mL) was refluxed at 90° C. under N$_2$ for 3 h. The resulting mixture was diluted with water (10 mL), extracted with EA (3×10 mL). The organic layers were combined, washed with brine, dried over Na$_2$SO$_4$ and concentrated. The resulting residue was purified by silica gel chromatography to yield 4-(1-(1-(5-(3-chloro-2-fluoro-6-(4-(trifluoromethyl)-1H-1,2,3-triazol-1-yl)phenyl)pyridin-2-yl)-3-(difluoromethoxy)propyl)-1H-pyrazol-4-yl)-2-fluorobenzamide (as a light yellow oil. LC/MS: mass calculated for C$_{28}$H$_{19}$ClF$_7$N$_7$O$_2$: 653.12, measured (ES, m/z): 653.93 [M+H]$^+$.

Step 2: 5-((R)-1-(4-(4-Carbamoyl-3-fluorophenyl)-1H-pyrazol-1-yl)-3-(difluoromethoxy)propyl)-2-(3-chloro-2-fluoro-6-(4-(trifluoromethyl)-1H-1,2,3-triazol-1-yl)phenyl)pyridine 1-oxide 4-(1-(1-(6-(3-Chloro-2-fluoro-6-(4-(trifluoromethyl)-1H-1,2,3-triazol-1-yl)phenyl)pyridin-3-yl)-3-(difluoromethoxy)propyl)-1H-pyrazol-4-yl)-2-fluorobenzamide (250 mg, 0.38 mmol, 1.0 equiv.), methyltrioxorhenium (95 mg, 0.38 mmol, 1.0 equiv.), hydrogen peroxide (0.12 mL, 30 wt %) in CH$_3$OH (3 mL) was stirred for 3 h at room temperature. The resulting mixture was purified by reverse phase chromatography on C18 (MeCN/H$_2$O (0.05% CF$_3$COOH)) to yield the racemic product, which was separated by chiral-HPLC to yield 5-((R)-1-(4-(4-carbamoyl-3-fluorophenyl)-1H-pyrazol-1-yl)-3-(difluoromethoxy)propyl)-2-(3-chloro-2-fluoro-6-(4-(trifluoromethyl)-1H-1,2,3-triazol-1-yl)phenyl)pyridine 1-oxide as a white solid.

LC/MS: mass calculated for C$_{28}$H$_{19}$ClF$_7$N$_7$O$_3$: 669.11, measured (ES, m/z): 670.05 [M+H]$^+$. $^1$H NMR (300 MHz, DMSO-d$_6$) δ 9.16 (s, 1H), 8.58 (s, 1H), 8.43 (s, 1H), 8.17 (s, 1H), 8.06 (t, J=8.2 Hz, 1H), 7.70-7.77 (m, 1H), 7.68 (t, J=8.0 Hz, 1H), 7.48-7.62 (m, 4H), 7.28 (d, J=8.3 Hz, 1H), 7.10-7.17 (m, 1H), 6.32-6.84 (m, 1H), 6.10-6.20 (m, 1H), 3.80-3.89 (m, 1H), 3.66-3.74 (m, 1H), 2.49-2.60 (m, 2H). $^{19}$F-NMR (282 MHz, DMSO-d$_6$) δ −59.78, −83.30, −112.84.

Example 917: (R*)3-Chloro-4-(1-(1-(5-(3-chloro-2-fluoro-6-(1H-tetrazol-1-yl)phenyl)-1-oxidopyridin-2-yl)-2-cyclopropylethyl)-1H-pyrazol-4-yl)-5-fluoropyridine 1-oxide

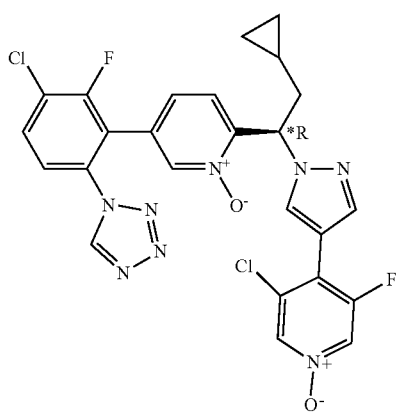

LC/MS: mass calculated for C$_{25}$H$_{18}$Cl$_2$F$_2$N$_8$O$_2$: 570.09, measured (ES, m/z): 571.10 [M+H]$^+$. $^1$H NMR (400 MHz, CD$_3$OD) δ 9.40 (s, 1H), 8.50-8.60 (m, 3H), 8.38 (s, 1H), 8.11 (d, J=2.2 Hz, 1H), 7.91-7.98 (m, 1H), 7.55-7.66 (m, 2H), 7.30-7.34 (m, 1H), 6.28-6.34 (m, 1H), 2.42-2.55 (m, 1H), 2.02-2.13 (m, 1H), 0.62-0.70 (m, 1H), 0.31-0.49 (m, 2H), 0.15-0.22 (m, 1H), 0.00-0.07 (m, 1H). $^{19}$F NMR (376 MHz, CD$_3$OD) δ −77.01, −113.73-, 121.94.

Example 918: (S*)-3-Chloro-4-(1-(1-(5-(3-chloro-2-fluoro-6-(1H-tetrazol-1-yl)phenyl)-1-oxidopyridin-2-yl)-2-cyclopropylethyl)-1H-pyrazol-4-yl)-5-fluoropyridine 1-oxide

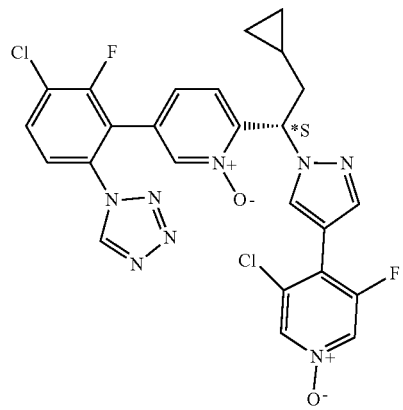

LC/MS: mass calculated for C$_{25}$H$_{18}$Cl$_2$F$_2$N$_8$O$_2$: 570.09, measured (ES, m/z): 571.10 [M+H]$^+$. $^1$H NMR (400 MHz, CD$_3$OD) δ 9.40 (s, 1H), 8.49-8.62 (m, 3H), 8.40 (s, 1H), 8.11 (d, J=2.2 Hz, 1H), 7.89-7.97 (m, 1H), 7.55-7.66 (m, 2H), 7.30-7.34 (m, 1H), 6.28-6.34 (m, 1H), 2.40-2.51 (m, 1H), 2.03-2.13 (m, 1H), 0.65-0.75 (m, 1H), 0.34-0.52 (m, 2H), 0.19-0.25 (m, 1H), 0.00-0.07 (m, 1H). $^{19}$F NMR (376 MHz, CD$_3$OD) δ −113.73, −121.94.

Example 919: (S*)-5-(3-Chloro-2-fluoro-6-(4-(trifluoromethyl)-1H-1,2,3-triazol-1-yl)phenyl)-2-(3-(methoxy-d$_3$)-1-(4-(1-methyl-1H-1,2,4-triazol-5-yl)-1H-pyrazol-1-yl)propyl-3,3-d2)pyridine 1-oxide

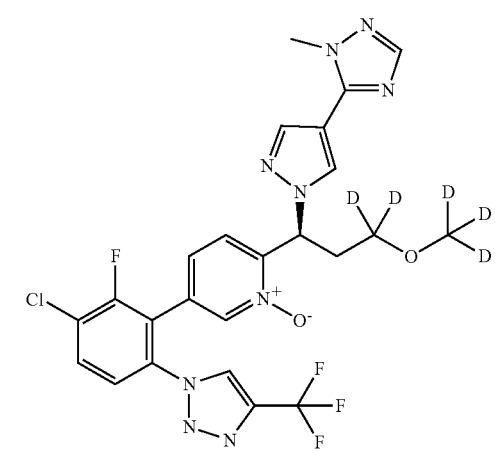

LC/MS: mass calculated for $C_{24}H_{15}ClD_5F_4N_9O_2$: 582.2, measured (ES, m/z): 583.2 [M+H]+. $^1$H NMR (400 MHz, DMSO-d$_6$) δ 9.13 (d, J=1.0 Hz, 1H), 8.56 (s, 1H), 8.36-8.42 (m, 1H), 8.00-8.09 (m, 2H), 7.91 (s, 1H), 7.73-7.77 (m, 1H), 7.37-7.41 (m, 1H), 7.15-7.20 (m, 1H), 6.25 (t, J=7.4 Hz, 1H), 3.96 (s, 3H), 2.45-2.52 (m, 2H). $^{19}$F NMR (376 MHz, DMSO-d$_6$) δ −59.73, −73.69, −112.89.

Example 920: (R*)-5-(3-Chloro-2-fluoro-6-(4-(trifluoromethyl)-1H-1,2,3-triazol-1-yl)phenyl)-2-(3-(methoxy-d3)-1-(4-(1-methyl-1H-1,2,4-triazol-5-yl)-1H-pyrazol-1-yl)propyl-3,3-d2)pyridine 1-oxide

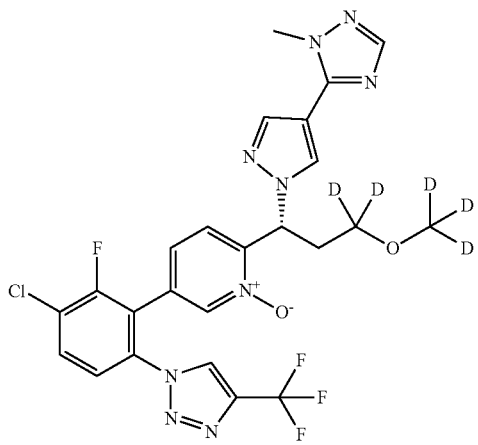 [SMILES: [2H]C([2H])([2H])OC([2H])([2H])C[C@H](c1ccc(-c2c(-n3cc(C(F)(F)F)nn3)ccc(Cl)c2F)c[n+]1[O-])n1cc(-c2ncnn2C)cn1]

LC/MS: mass calculated for $C_{24}H_{15}ClD_5F_4N_9O_2$: 582.2, measured (ES, m/z): 583.2 [M+H]+. $^1$H NMR (400 MHz, DMSO-d$_6$) δ 9.17 (d, J=1.1 Hz, 1H), 8.59 (s, 1H), 8.42 (d, J=1.6 Hz, 1H), 8.01-8.10 (m, 2H), 7.89 (s, 1H), 7.77 (dd, J=8.7, 1.5 Hz, 1H), 7.34 (d, J=8.3 Hz, 1H), 7.14 (dd, J=8.3, 1.7 Hz, 1H), 6.22-6.26 (m, 1H), 3.96 (s, 3H), 2.48 (d, J=5.9 Hz, 2H). $^{19}$F NMR (376 MHz, DMSO-d$_6$) δ −59.77, −112.88.

Example 921: (S*)-5-(3-Chloro-2-fluoro-6-(4-(trifluoromethyl)-1H-1,2,3-triazol-1-yl)phenyl)-2-(3-(difluoromethoxy)-1-(4-(3-fluoro-1-oxidopyridin-4-yl)-1H-pyrazol-1-yl)propyl-3,3-d$_2$)pyridine 1-oxide

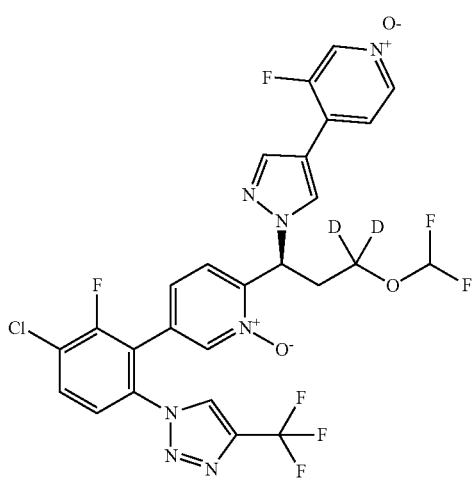

LC/MS: mass calculated for $C_{2H}H_{15}ClD_2F_7N_7O_3$: 645.11, measured (ES, m/z): 646.05 [M+H]+. $^1$H NMR (400 MHz, DMSO-d$_6$) δ 9.15 (s, 1H), 8.51-8.59 (m, 2H), 8.42 (d, J=1.6 Hz, 1H), 8.12-8.19 (m, 2H), 8.04-8.10 (m, 1H), 7.73-7.85 (m, 2H), 7.29-7.33 (m, 1H), 7.12-7.18 (m, 1H), 6.62 (t, J=75.7 Hz, 1H), 6.21-6.29 (m, 1H), 2.51-2.68 (m, 2H). $^{19}$F NMR (376 MHz, DMSO-d$_6$) δ −59.81, −83.31, −112.85, −124.12.

Example 922: (R*)-5-(3-Chloro-2-fluoro-6-(4-(trifluoromethyl)-1H-1,2,3-triazol-1-yl)phenyl)-2-(3-(difluoromethoxy)-1-(4-(3-fluoro-1-oxidopyridin-4-yl)-1H-pyrazol-1-yl)propyl-3,3-d$_2$)pyridine 1-oxide

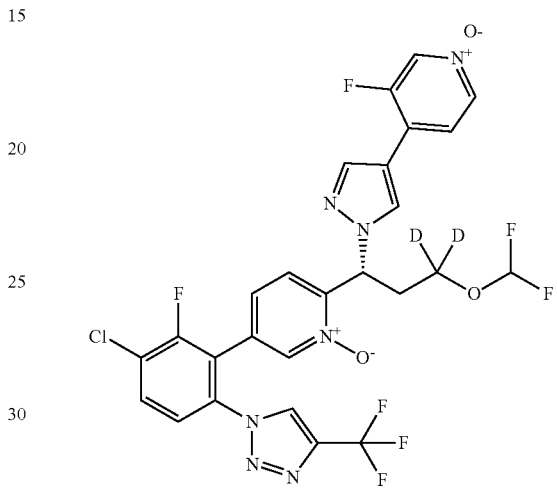

LC/MS: mass calculated for $C_{26}H_{15}ClD_2F_7N_7O_3$: 645.11, measured (ES, m/z): 646.05 [M+H]+. $^1$H NMR (400 MHz, DMSO-d$_6$) δ 9.15 (s, 1H), 8.51-8.59 (m, 2H), 8.42 (d, J=1.6 Hz, 1H), 8.11-8.18 (m, 2H), 8.04-8.10 (m, 1H), 7.73-7.85 (m, 2H), 7.29-7.33 (m, 1H), 7.12-7.18 (m, 1H), 6.62 (t, J=75.7 Hz, 1H), 6.21-6.29 (m, 1H), 2.51-2.66 (m, 2H). $^{19}$F NMR (376 MHz, DMSO-d$_6$) δ −59.81, −83.32, −112.85, −124.12.

Example 923: 2-(S*)-1-(4-(4-Carbamoyl-3-fluorophenyl)-1H-pyrazol-1-yl)propyl)-5-(3-chloro-2-fluoro-6-(4-(trifluoromethyl)-1H-1,2,3-triazol-1-yl)phenyl)-4-methoxypyridine 1-oxide

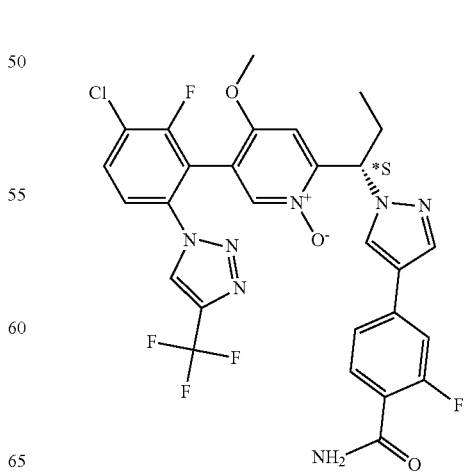

LC/MS: mass calculated for $C_{28}H_{21}ClF_5N_7O_3$: 633.1, measured (ES, m/z): 634.1 [M+H]$^+$. $^1$H NMR (300 MHz, DMSO-d$_6$) δ 9.20-9.26 (m, 1H), 8.57-8.62 (m, 1H), 8.42 (d, J=1.2 Hz, 1H), 8.15 (s, 1H), 8.01-8.10 (m, 1H), 7.76-7.82 (m, 1H), 7.65-7.74 (m, 1H), 7.50-7.64 (m, 4H), 7.00-7.06 (m, 1H), 5.92-6.08 (m, 1H), 3.50-3.56 (m, 3H), 2.18-2.30 (m, 2H), 0.79-0.89 (m, 3H). $^{19}$F NMR (282 MHz, DMSO-d$_6$) δ −59.71, −59.75, −111.77, −111.91, −113.01.

Example 924: 2-((R*)-1-(4-(4-Carbamoyl-3-fluorophenyl)-1H-pyrazol-1-yl)propyl)-5-(3-chloro-2-fluoro-6-(4-(trifluoromethyl)-1H-1,2,3-triazol-1-yl)phenyl)-4-methoxypyridine 1-oxide

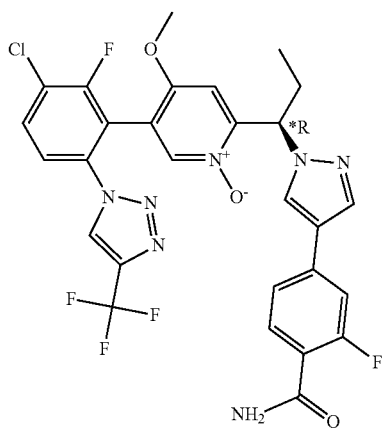 [SMILES: CC[C@H](c1cc(OC)c(-c2c(-n3cc(C(F)(F)F)nn3)ccc(Cl)c2F)c[n+]1[O-])n1cc(-c2ccc(C(N)=O)c(F)c2)cn1]

LC/MS: mass calculated for $C_{28}H_{21}ClF_5N_7O_3$: 633.1, measured (ES, m/z): 634.1 [M+H]$^+$. $^1$H NMR (300 MHz, DMSO-d$_6$) δ 9.20-9.26 (m, 1H), 8.57-8.62 (m, 1H), 8.42 (s, 1H), 8.16 (s, 1H), 8.01-8.10 (m, 1H), 7.76-7.84 (m, 1H), 7.66-7.74 (m, 1H), 7.48-7.65 (m, 4H), 7.00-7.06 (m, 1H), 5.94-6.08 (m, 1H), 3.50-3.56 (m, 3H), 2.20-2.37 (m, 2H), 0.81-0.90 (m, 3H) $^{19}$F NMR (282 MHz, DMSO-d$_6$) δ −59.72, −111.77, −111.90, −113.02.

Example 925: (S*)-5-(3-Chloro-2-fluoro-6-(1H-tetrazol-1-yl)phenyl)-2-(1-(2-(difluoromethyl)-1'H,2H-[3,4'-bipyrazol]-1'-yl)-3-(methoxy-d3)propyl-3,3-d2)pyridine 1-oxide

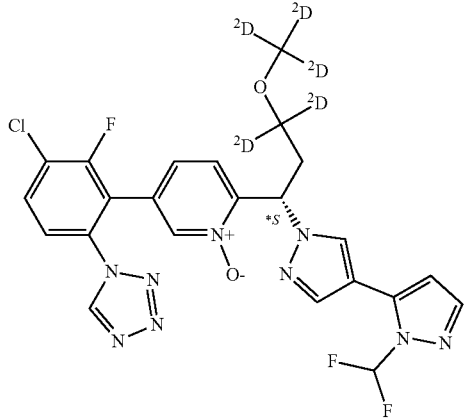

LC/MS: mass calculated for $C_{23}H_{14}ClD_5F_3N_9O_2$: 550.2, measured (ES, m/z): 551.1 [M+H]$^+$. $^1$H NMR (400 MHz, DMSO-d$_6$) δ 9.69 (s, 1H), 8.34-8.47 (m, 2H), 8.06 (dd, J=8.7, 7.7 Hz, 1H), 7.66-8.01 (m, 4H), 7.36 (d, J=8.3 Hz, 1H), 7.18 (dd, J=8.3, 1.7 Hz, 1H), 6.69 (d, J=1.7 Hz, 1H), 6.19-6.22 (m, 1H), 2.38-2.48 (m, 2H). $^{19}$F NMR (376 MHz, DMSO-d$_6$) δ −73.40, −93.55, −112.70.

Example 926: (S*)-5-(3-Chloro-2-fluoro-6-(1H-tetrazol-1-yl)phenyl)-2-(1-(2-(difluoromethyl)-1'H,2H-[3,4'-bipyrazol]-1'-yl)-3-(methoxy-d$_3$)propyl-3,3-d2)pyridine 1-oxide

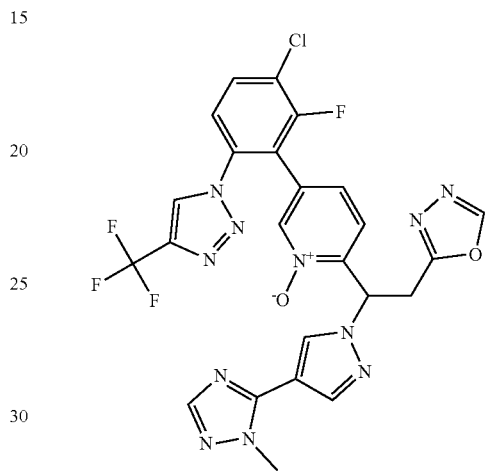

Step 1: 1'-(1-(5-Bromopyridin-2-yl)-3-(methoxy-d3)propyl-3,3-d2)-2-(difluoromethyl)-1'H,2H-3,4'-bipyrazole To a solution of 2-(difluoromethyl)-1'H,2H-3,4'-bipyrazole (111 mg, 0.60 mmol, 1.1 equiv.) in ACN (10 mL) was added cesium carbonate (196 mg, 0.60 mmol, 1.1 equiv.). After the reaction mixture was stirred at room temperature for 1 h, 1-(5-bromopyridin-2-yl)-3-(methoxy-d$_3$)propyl-3,3-d2 methanesulfonate (180 mg, 0.55 mmol, 1.0 equiv.) was added. The reaction mixture was stirred for 2 h at 80° C., then cooled to room temperature. and filtrated, then washed with EA. The filtrate was concentrated under vacuum. The residue was purified by silica gel chromatography (0→60% EA/PE) to yield 1'-(1-(5-bromopyridin-2-yl)-3-(methoxy-d3)propyl-3,3-d2)-2-(difluoromethyl)-1'H,2H-3,4'-bipyrazole as light yellow oil. LC/MS: mass calculated for $C_{16}H_{11}BrD_5F_2N_5O$: 416.08, measured (ES, m/z): 417.05, 419.05 [M+H, M+H+2]$^+$.

Step 2: 4-Chloro-2-(6-(1-(2-(difluoromethyl)-1'H,2H-[3,4'-bipyrazol]-1'-yl)-3-(methoxy-d3)propyl-3,3-d2)pyridin-3-yl)-3-fluoroaniline To a mixture of 1'-(1-(5-bromopyridin-2-yl)-3-(methoxy-d3)propyl-3,3-d2)-2-(difluoromethyl)-1'H,2H-3,4'-bipyrazole (200 mg, 0.48 mmol, 1.0 equiv.) in 1,4-dioxane (10 mL) and water (2 mL) was added (6-amino-3-chloro-2-fluorophenyl)boronic acid (182 mg, 0.96 mmol, 2.0 equiv.) and potassium carbonate (199 mg, 1.44 mmol, 3.0 equiv.) and tetrakis(triphenylphosphine)palladium (55 mg, 0.05 mmol, 0.1 equiv.). The reaction was stirred at 100° C. for 3 h under N$_2$. After cooling to room temperature, the reaction was quenched with water, and the mixture extracted with ethyl acetate twice. The combined organic layers were dried over anhydrous sodium sulfate and concentrated. The residue was purified silica gel chromatography (0→80% EA/PE) to yield 4-chloro-2-(6-(1-(2-(difluoromethyl)-1'H,2H-[3,4'-bipyrazol]-1'-yl)-3-(methoxy-d$_3$)propyl-3,3-d2)pyridin-3-yl)-3-fluoroaniline as a brown solid. LC/MS: mass calculated for $C_{22}H_{15}ClD_5F_3N_6O$: 481.17, measured (ES, m/z): 482.10 [M+H]$^+$.

Step 3: 1'-(1-(5-(3-Chloro-2-fluoro-6-(1H-tetrazol-1-yl)phenyl)pyridin-2-yl)-3-(methoxy-d3)propyl-3,3-d2)-2-(difluoromethyl)-1'H,2H-3,4'-bipyrazole The mixture of 4-chloro-2-(6-(1-(2-(difluoromethyl)-1'H,2H-[3,4'-bipyrazol]-1'-yl)-3-(methoxy-d3)propyl-3,3-d2)pyridin-3-yl)-3-fluoroaniline (180 mg, 0.37 mmol, 1.0 equiv.), azidotrimethylsilane (430 mg, 3.73 mmol, 10.0 equiv.) and trimethoxymethane (396 mg, 3.73 mmol, 10.0 equiv.) in acetic acid (10 mL) was stirred at room temperature overnight. The mixture was concentrated and the resulting residue was purified by reverse phase chromatography on C18 (120 g, MeCN/H$_2$O (0.05% CF$_3$COOH): 0→60%) to yield 1'-(1-(5-(3-chloro-2-fluoro-6-(1H-tetrazol-1-yl)phenyl)pyridin-2-yl)-3-(methoxy-d$_3$)propyl-3,3-d2)-2-(difluoromethyl)-1'H,2H-3,4'-bipyrazole as a yellow oil. LC/MS: mass calculated for $C_{23}H_{14}ClD_5F_3N_9O$: 534.17, measured (ES, m/z): 535.10 [M+H]$^+$.

Step 4: (S*)-5-(3-Chloro-2-fluoro-6-(1H-tetrazol-1-yl)phenyl)-2-(1-(2-(difluoromethyl)-1'H,2H-[3,4'-bipyrazol]-1'-yl)-3-(methoxy-d3)propyl-3,3-d2)pyridine 1-oxide To a solution of 1'-(1-(5-(3-chloro-2-fluoro-6-(1H-tetrazol-1-yl) phenyl)pyridin-2-yl)-3-(methoxy-d3)propyl-3,3-d2)-2-(difluoromethyl)-1'H,2H-3,4'-bipyrazole (150 mg, 0.28 mmol, 1.0 equiv.) in CH$_3$OH (10 mL) was added hydrogen peroxide (30 wt %, 636 mg, 5.61 mmol, 20.0 equiv.) and methyltrioxorhenium (35 mg, 0.14 mmol, 0.5 equiv.). The reaction was stirred at room temperature for 4 h. The mixture was purified by reverse phase chromatography on C18 (120 g, MeCN/H$_2$O (0.05% CF$_3$COOH): 0→60%) and Prep-Chiral-HPLC with MtBE(0.1% DEA):EtOH=85:15 to yield (S*)-5-(3-chloro-2-fluoro-6-(1H-tetrazol-1-yl)phenyl)-2-(1-(2-(difluoromethyl)-1'H,2H-[3,4'-bipyrazol]-1'-yl)-3-(methoxy-d3)propyl-3,3-d$_2$)pyridine 1-oxide as a white solid.

LC/MS: mass calculated for $C_{23}H_{14}ClD_5F_3N_9O_2$: 550.16, measured (ES, m/z): 551.10 [M+H]$^+$. $^1$H NMR (400 MHz, DMSO-d$_6$): δ 9.69 (s, 1H), 8.44 (s, 1H), 8.37 (s, 1H), 8.01-8.10 (m, 1H), 7.68-7.99 (m, 4H), 7.36 (d, J=8.3 Hz, 1H), 7.12-7.21 (m, 1H), 6.69 (d, J=1.8 Hz, 1H), 6.12-6.25 (m, 1H), 2.41-2.48 (m, 2H). $^{19}$F NMR (376 MHz, DMSO-d$_6$): 5-73.40, −93.55, −112.70.

Example 927: 2-(1-(4-(4-Carboxy-3-fluorophenyl)-1H-pyrazol-1-yl)-3-(difluoromethoxy)propyl)-5-(3-chloro-2-fluoro-6-(4-(trifluoromethyl)-1H-1,2,3-triazol-1-yl)phenyl)pyridine 1-oxide

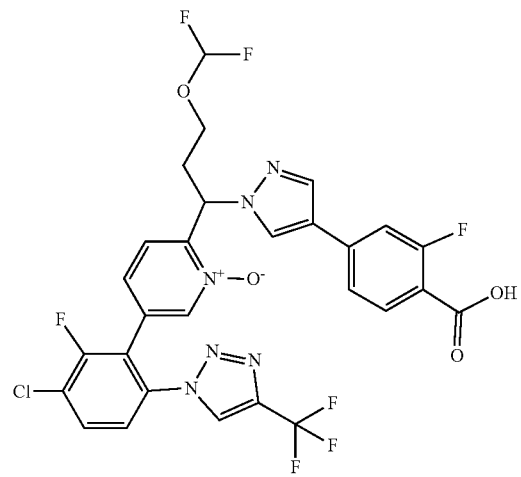 [SMILES: O=C(O)c1ccc(-c2cnn(C(CCOC(F)F)c3ccc(-c4c(-n5cc(C(F)(F)F)nn5)ccc(Cl)c4F)c[n+]3[O-])c2)cc1F]

LC/MS: mass calculated for $C_{28}H_{18}ClF_7N_6O_4$: 670.10, measured (ES, m/z): 671.0 [M+H]$^+$. $^1$H NMR (400 MHz, CD$_3$OD) δ ppm 2.69-2.85 (m, 2H) 3.71-3.83 (m, 1H) 3.95-4.06 (m, 1H) 6.16-6.60 (m, 2H), 7.28-7.34 (m, 1H) 7.44-7.54 (m, 3H) 7.62 (dd, J=8.80, 1.47 Hz, 1H) 7.89-7.98 (m, 2H), 8.10 (s, 1H) 8.40 (d, J=4.89 Hz, 2H), 8.81 (s, 1H).

Example 928: 2-(1-(4-(4-Carboxy-3-fluorophenyl)-1H-pyrazol-1-yl)-2-(1-(difluoromethyl)-1H-pyrazol-3-yl)ethyl)-5-(3-chloro-2-fluoro-6-(4-(trifluoromethyl)-1H-1,2,3-triazol-1-yl)phenyl)pyridine 1-oxide

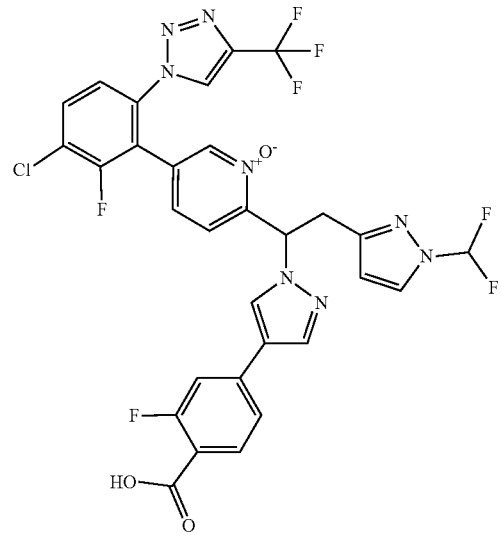

Step 1: (5-Bromopyridin-2-yl)methyl methanesulfonate

To a solution of (5-bromopyridin-2-yl)methanol (1.8 g, 9.573 mmole) in DCM (20 mL), DIPEA (1.65 mL, 9.573 mmole) was added at room temperature under $N_2$. Methanesulfonic anhydride (2.501 g, 14.36 mmole) was added portion wise at 0° Celsius. The reaction was stirred at room temperature for 4 hours. The reaction was partitioned with water and DCM. The organic was separated washed with brine and dried over $Na_2SO_4$.

The solid was filtered and washed with EA. The filtrate was adsorbed onto silica gel and purified via ISCO normal phase chromatography with heptane and EA as eluent (5% to 20% gradient) to yield (5-bromopyridin-2-yl)methyl methanesulfonate as an off white solid. $^1H$ NMR ($CDCl_3$, 400 MHz) 5-8.68 (s, 1H), 7.90 (d, 1H, J=8.3 Hz), 7.38 (d, J=8.3 Hz, 1H), 5.29 (s, 2H), 3.12 (s, 3H).

Step 2: tert-Butyl 4-(1-((5-bromopyridin-2-yl)methyl)-1H-pyrazol-4-yl)-2-fluorobenzoate To a solution of tert-butyl 2-fluoro-4-(1H-pyrazol-4-yl)benzoate (0.295 g, 1.109 mmole) in acetonitrile (12 mL), (5-bromopyridin-2-yl)methyl methanesulfonate (0.291 g, 1.109 mmole) and $Cs_2CO_3$ (0.722 g, 2.217 mmole) were added. The reaction mixture was heated at 70° C. overnight. The sold was filtered thru CELITE® and washed with EA. The filtrate was concentrated to yield an oil. The oil was purified via ISCO normal phase column chromatography with heptane and EA as eluent (5% to 60% EA gradient) to yield tert-butyl 4-(1-(1-(5-bromopyridin-2-yl)-2-(1-(difluoromethyl)-1H-pyrazol-3-yl)ethyl)-1H-pyrazol-4-yl)-2-fluorobenzoate as a white solid. LC-MS: calculated mass for $C_{20}H_{19}BrFN_3O_2$: 431.1, measured (ES, m/z): 432.1 $[M+H]^+$.

Step 3: tert-Butyl 4-(1-(1-(5-bromopyridin-2-yl)-2-(1-(difluoromethyl)-1H-pyrazol-3-yl)ethyl)-1H-pyrazol-4-yl)-2-fluorobenzoate To a solution of tert-butyl 4-(1-((5-bromopyridin-2-yl)methyl)-1H-pyrazol-4-yl)-2-fluorobenzoate (0.24 g, 0.555 mmole) in tetrahydrofuran (8 mL), 1.0M Lithium bis(trimethylsilyl)amide in THF (0.67 mL, 0.67 mmole) was added dropwise at −78° C. under $N_2$. The reaction mixture was stirred at −78° C. for 15 minutes. 3-(Bromomethyl)-1-(difluoromethyl)-1H-pyrazole (117 mg, 0.555 mmole) in THF (3 mL) was added. The reaction was slowly warmed to room temperature and stirred for 2 hours. The reaction was quenched with saturated $NH_4Cl$. The aqueous was extracted with EA (2×50 mL). The organic was washed with brine and dried over $Na_2SO_4$. The solid was filtered and washed with EA. The solvent was removed under vacuum to yield an oil. The residue was purified via normal phase ISCO column chromatography with heptane and EA as eluent (5 to 45% EA gradient) to yield tert-butyl 4-(1-(1-(5-bromopyridin-2-yl)-2-(1-(difluoromethyl)-1H-pyrazol-3-yl)ethyl)-1H-pyrazol-4-yl)-2-fluorobenzoate as a solid. LC-MS: calculated mass for $C_{25}H_{23}BrF_3N_5O_2$: 561.1, measured (ES, m/z): 562.2 $[M+H]^+$.

Step 4: (6-(1-(4-(4-(tert-Butoxycarbonyl)-3-fluorophenyl)-1H-pyrazol-1-yl)-2-(1-(difluoromethyl)-1H-pyrazol-3-yl)ethyl)pyridin-3-yl)boronic acid To a solution of tert-butyl 4-(1-(1-(5-bromopyridin-2-yl)-2-(1-(difluoromethyl)-1H-pyrazol-3-yl)ethyl)-1H-pyrazol-4-yl)-2-fluorobenzoate (0.100 g, 0.178 mmole) in dioxane (3 mL) in a microwave vial, bis-(pinacolato) diborane (0.054 g, 0.213 mmole), Pd(dppf)$Cl_2 \cdot CH_2Cl_2$ (0.015 g, 0.178 mmole), and KOAc (0.035 g, 0.356 mmole) were added. The reaction mixture was purged with $N_2$ via needle inlet for 5 minutes. The reaction was capped and heated in the microwave at 130° C. for 3 hours to yield (6-(1-(4-(4-(tert-butoxycarbonyl)-3-fluorophenyl)-1H-pyrazol-1-yl)-2-(1-(difluoromethyl)-1H-pyrazol-3-yl)ethyl)pyridin-3-yl)boronic acid which was used in-situ in the next reaction without further purification. LC-MS: calculated mass for $C_{25}H_{25}BF_3N_5O_4$: 527.2, measured (ES, m/z): 528.3 $[M+H]^+$.

Step 5: tert-Butyl 4-(1-(1-(5-(3-chloro-2-fluoro-6-(4-(trifluoromethyl)-1H-1,2,3-triazol-1-yl)phenyl)pyridin-2-yl)-2-(1-(difluoromethyl)-1H-pyrazol-3-yl)ethyl)-1H-pyrazol-4-yl)-2-fluorobenzoate To a solution of (6-(1-(4-(4-(tert-butoxycarbonyl)-3-fluorophenyl)-1H-pyrazol-1-yl)-2-(1-(difluoromethyl)-1H-pyrazol-3-yl)ethyl)pyridin-3-yl)boronic acid (0.092 g, 0.174 mmole) in dioxane (3 mL), 1-(4-chloro-3-fluoro-2-iodophenyl)-4-(trifluoromethyl)-1H-1,2,3-triazole (0.068 g, 0.17 mmole), tetrakis triphenylphosphine palladium (0.020 g, 0.017 mmole), and 2M $K_2CO_3$ (0.19 mL, 0.38 mmole) were added. The reaction mixture was purged with $N_2$ via a needle inlet for 5 minutes. The reaction was capped and heated in microwave for 2 hours at 120° C. The reaction was partitioned with water and EA. The organic was separated.

The aqueous was extracted with EA. The combined organic was washed with brine and dried over $Na_2SO_4$.

The solid was filtered and washed with EA. The filtrate was adsorbed onto silica gel and purified via ISCO normal phase column chromatography with heptane and EA as eluent (10% to 90% EA) to yield tert-butyl 4-(1-(1-(5-(3-chloro-2-fluoro-6-(4-(trifluoromethyl)-1H-1,2,3-triazol-1-yl)phenyl)pyridin-2-yl)-2-(1-(difluoromethyl)-1H-pyrazol-3-yl)ethyl)-1H-pyrazol-4-yl)-2-fluorobenzoate a yellow solid. LC-MS: calculated mass for $C_{34}H_{26}ClF_7N_8O_2$: 746.2, measured (ES, m/z): 747.3 $[M+H]^+$.

Step 6: 4-(1-(1-(5-(3-Chloro-2-fluoro-6-(4-(trifluoromethyl)-1H-1,2,3-triazol-1-yl)phenyl)pyridin-2-yl)-2-(1-(difluoromethyl)-1H-pyrazol-3-yl)ethyl)-1H-pyrazol-4-yl)-2-fluorobenzoic acid To a solution of tert-butyl 4-(1-(1-(5-(3-chloro-2-fluoro-6-(4-(trifluoromethyl)-1H-1,2,3-triazol-1-yl)phenyl)pyridin-2-yl)-2-(1-(difluoromethyl)-1H-pyrazol-3-yl)ethyl)-1H-pyrazol-4-yl)-2-fluorobenzoate (0.095 g, 0.127 mmole) in DCM (2 mL), TFA (2 mL) was added. The reaction was stirred at room temperature for 2 hours.

The solvent was removed under vacuum to yield an oil. The oil was co-evaporated with DCM (2×) to yield 4-(1-(1-(5-(3-chloro-2-fluoro-6-(4-(trifluoromethyl)-1H-1,2,3-triazol-1-yl)phenyl)pyridin-2-yl)-2-(1-(difluoromethyl)-1H-pyrazol-3-yl)ethyl)-1H-pyrazol-4-yl)-2-fluorobenzoic acid as a gummy solid. LC-MS: calculated mass for $C_{30}H_{18}ClF_7N_8O_2$: 690.1, measured (ES, m/z): 691.2 $[M+H]^+$.

Step 7: 2-(1-(4-(4-Carboxy-3-fluorophenyl)-1H-pyrazol-1-yl)-2-(1-(difluoromethyl)-1H-pyrazol-3-yl)ethyl)-5-(3-chloro-2-fluoro-6-(4-(trifluoromethyl)-1H-1,2,3-triazol-1-yl)phenyl)pyridine 1-oxide Into a 20 mL scintillation vial were added 4-(1-(1-(5-(3-chloro-2-fluoro-6-(4-(trifluoromethyl)-1H-1,2,3-triazol-1-yl)phenyl)pyridin-2-yl)-2-(1-(difluoromethyl)-1H-pyrazol-3-yl)ethyl)-1H-pyrazol-4-yl)-2-fluorobenzoic acid (84 mg, 0.12 mmol), MeReO$_3$ (15.2 mg, 0.16 mmol), 30% $H_2O_2$ (0.13 mL, 1.22 mmol), and MeOH (2 ml). The reaction mixture was stirred at room temperature for 3 hours. The solution was purified via ISCO reverse phase column chromatography with 0.1% TFA in water and 0.1% TFA in ACN (35% to 60% 0.1% TFA in ACN gradient) to give 2-(1-(4-(4-carboxy-3-fluorophenyl)-1H-pyrazol-1-yl)-2-(1-(difluoromethyl)-1H-pyrazol-3-yl)ethyl)-5-(3-chloro-2-fluoro-6-(4-(trifluoromethyl)-1H-1,2,3-triazol-1-yl)phenyl)pyridine 1-oxide as a white solid.

LC-MS: calculated mass for $C_{30}H_{18}ClF_7N_8O_3$: 706.1, measured (ES, m/z): 707.3 [M+H]+. $^1$H NMR (CD$_3$OD, 400 MHz) δ 13.11 (s, 1H), 9.19 (s, 1H), 8.61 (s, 1H), 8.46 (s, 1H), 8.16 (s, 1H), 8.11-7.90 (m, 2H), 7.88-7.45 (m, 5H), 7.33 (d, J=8.3 Hz, 1H), 7.17 (d, J=8.8 Hz, 1H), 6.41-6.35 (m, 1H), 6.12 (s, 1H), 3.82-3.25 (m, 2H). $^{19}$F NMR (CD$_3$OD, 377 MHz) δ −113.9, −110.9, −86.5, 62.7.

Example 929: 2-((R)-1-(4-(4-Carbamoyl-3-fluorophenyl)-1H-pyrazol-1-yl)-2-cyclopropylethyl)-5-(3-chloro-2-fluoro-6-(4-(trifluoromethyl)-1H-1,2,3-triazol-1-yl)phenyl)-4-methoxypyridine 1-oxide

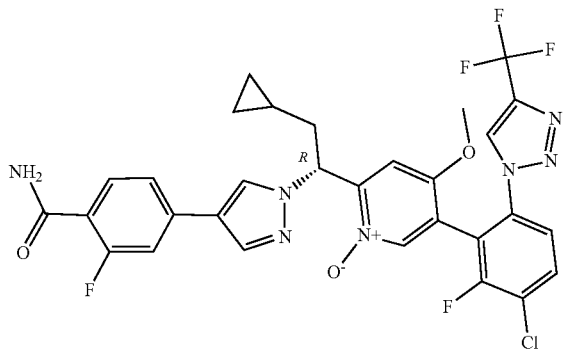

LC/MS: mass calculated for $C_{30}H_{23}ClF_5N_7O_3$: 659.15, measured (ES, m/z): 660.15 [M+H]+. $^1$H NMR (300 MHz, CD$_3$OD) δ 8.82-8.91 (m, 1H), 8.45 (d, J=4.2 Hz, 1H), 8.34-8.39 (m, 1H), 8.12 (d, J=2.2 Hz, 1H), 7.82-7.97 (m, 2H), 7.41-7.67 (m, 3H), 7.20 (d, J=4.8 Hz, 1H), 6.20-6.41 (m, 1H), 3.70 (s, 3H), 2.42-2.62 (m, 1H), 1.90-2.25 (m, 1H), 0.65-0.76 (m, 1H), 0.4-0.52 (m, 2H), 0.18-0.21 (m, 1H), 0.08-0.11 (m, 1H). $^{19}$F NMR (300 MHz, CD$_3$OD) δ −114.627, −112.785, −77.525, −62.663.

Example 930: (R*) 5-(5-Chloro-2-cyanophenyl)-2-(2-cyclopropyl-1-(4-(4-fluoro-1-methyl-1H-1,2,3-triazol-5-yl)-1H-pyrazol-1-yl)ethyl)-4-methoxypyridine 1-oxide

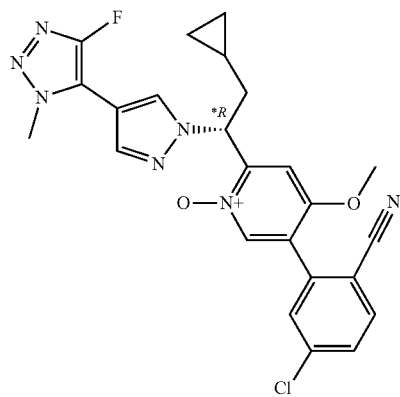 [SMILES: COc1cc([C@@H](CC2CC2)n2cc(-c3c(F)nnn3C)cn2)[n+](O)cc1-c1cc(Cl)ccc1C#N]

LC/MS: mass calculated for $C_{24}H_{21}ClFN_7O_2$: 493.14, measured (ES, m/z): 494.10 [M+H]+. $^1$H NMR (400 MHz, DMSO-d$_6$) δ 8.66 (s, 1H), 8.42 (s, 1H), 7.98-8.05 (m, 2H), 7.71-7.81 (m, 2H), 7.25 (s, 1H), 6.29-6.33 (m, 1H), 4.12 (s, 3H), 3.83 (s, 3H), 2.37-2.45 (m, 1H), 2.06-2.17 (m, 1H), 0.60-0.69 (m, 1H), 0.39-0.45 (m, 1H), 0.30-0.37 (m, 1H), 0.17-0.24 (m, 1H), −0.09-0.02 (m, 1H). $^{19}$F NMR (376 MHz, DMSO-d$_6$) δ −145.28.

Example 931: (S*)-5-(5-Chloro-2-cyanophenyl)-2-(2-cyclopropyl-1-(4-(4-fluoro-1-methyl-1H-1,2,3-triazol-5-yl)-1H-pyrazol-1-yl)ethyl)-4-methoxypyridine 1-oxide

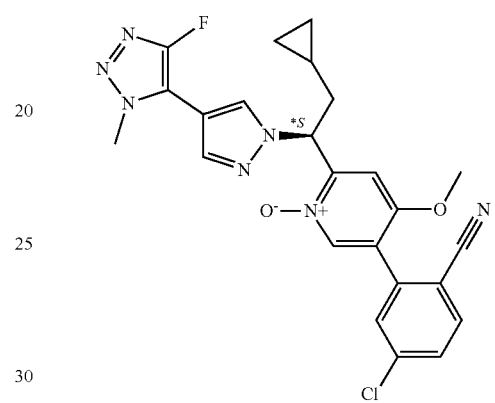

LC/MS: mass calculated for $C_{24}H_{21}ClFN_7O_2$: 493.14, measured (ES, m/z): 494.10 [M+H]+. $^1$H NMR (400 MHz, DMSO-d$_6$) δ 8.66 (s, 1H), 8.42 (s, 1H), 7.98-8.05 (m, 2H), 7.71-7.81 (m, 2H), 7.25 (s, 1H), 6.29-6.33 (m, 1H), 4.12 (s, 3H), 3.83 (s, 3H), 2.38-2.52 (m, 1H), 2.08-2.16 (m, 1H), 0.60-0.69 (m, 1H), 0.39-0.45 (m, 1H), 0.30-0.37 (m, 1H), 0.16-0.23 (m, 1H), −0.09-0.02 (m, 1H).

Example 932: 5-(3-Chloro-2-fluoro-6-(4-(trifluoromethyl)-1H-1,2,3-triazol-1-yl)phenyl)-2-(2-cyclopropyl-1-(4-(1-methyl-1H-1,2,4-triazol-5-yl)-1H-pyrazol-1-yl)ethyl)-4-methoxypyridine 1-oxide

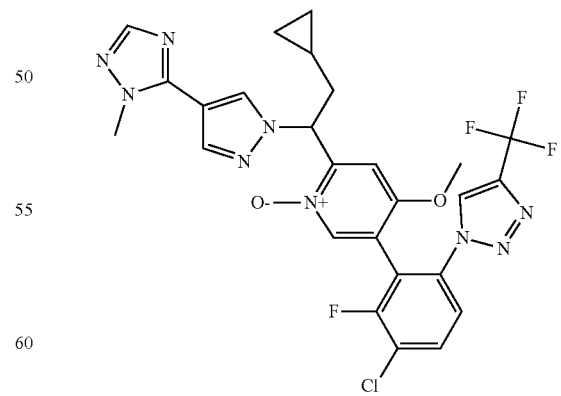

LC/MS: mass calculated for $C_{26}H_{22}ClF_4N_9O_2$: 603.15, measured (ES, m/z): 604.10 [M+H]+. $^1$H NMR (400 MHz, DMSO-d$_6$) δ 8.84-8.92 (m, 1H), 8.57 (d, J=0.9 Hz, 1H), 8.37 (d, J=2.1 Hz, 1H), 8.14 (d, J=4.9 Hz, 1H), 7.88-7.97 (m, 2H), 7.60-7.68 (m, 1H), 7.26 (d, J=3.4 Hz, 1H), 6.30-6.35 (m, 1H), 4.06 (s, 3H), 3.72 (s, 3H), 2.48-2.60 (m, 1H), 2.08-2.18 (m, 1H), 0.68-0.75 (m, 1H), 0.39-0.52 (m, 2H), 0.19-0.29 (m, 1H), 0.01-0.11 (m, 1H). $^{19}$F NMR (282 MHz, DMSO-$d_6$) δ −59.71, −59.76, −111.83, −111.91.

Example 933: (R*)-2-(1-(4-(4-Carbamoyl-3-fluorophenyl)-1H-pyrazol-1-yl)-3-(difluoromethoxy)propyl)-5-(3-chloro-6-(4-chloro-1H-1,2,3-triazol-1-yl)-2-fluorophenyl)pyridine 1-oxide

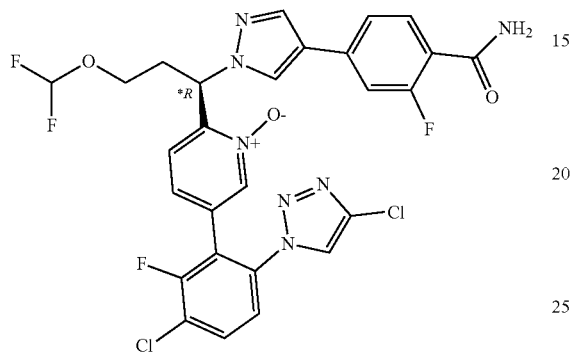

LC/MS: mass calculated for $C_{27}H_{19}Cl_2F_4N_7O_3$: 635.09, measured (ES, m/z): 636.05 [M+H]$^+$. $^1$H NMR (400 MHz, DMSO-$d_6$) δ 8.68 (s, 1H), 8.61 (s, 1H), 8.43 (s, 1H), 8.20 (s, 1H), 8.01-8.10 (m, 1H), 7.67-7.71 (m, 2H), 7.51-7.65 (m, 4H), 7.31-7.33 (m, 1H), 7.18-7.22 (m, 1H), 6.65 (t, J=75.6 Hz, 1H), 6.16-6.22 (m, 1H), 3.83-3.92 (m, 1H), 3.63-3.76 (m, 1H), 2.52-2.74 (m, 2H). $^{19}$F NMR (400 MHz, DMSO-$d_6$) δ −83.22, −112.97.

Example 934: (S*)-2-(1-(4-(4-Carbamoyl-3-fluorophenyl)-1H-pyrazol-1-yl)-3-(difluoromethoxy)propyl)-5-(3-chloro-6-(4-chloro-1H-1,2,3-triazol-1-yl)-2-fluorophenyl)pyridine 1-oxide

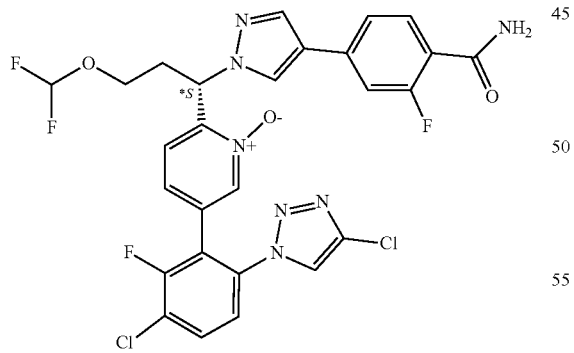

LC/MS: mass calculated for $C_{27}H_{19}Cl_2F_4N_7O_3$: 635.09, measured (ES, m/z): 636.05 [M+H]$^+$. 1H NMR (400 MHz, DMSO-$d_6$) δ 8.67 (s, 1H), 8.60 (s, 1H), 8.42 (s, 1H), 8.19 (s, 1H), 8.00-8.05 (m, 1H), 7.70-7.72 (m, 2H), 7.52-7.68 (m, 4H), 7.31-7.33 (m, 1H), 7.18-7.22 (m, 1H), 6.65 (t, J=75.6 Hz, 1H), 6.19-6.23 (m, 1H), 3.83-3.91 (m, 1H), 3.62-3.75 (m, 1H), 2.52-2.74 (m, 2H). $^{19}$F NMR (400 MHz, DMSO-$d_6$) δ −83.22, −112.97.

Example 935: (R*)-2-(1-(4-(4-Carbamoyl-3-fluorophenyl)-1H-pyrazol-1-yl)propyl)-5-(5-chloro-2-(4-(trifluoromethyl)-1H-1,2,3-triazol-1-yl)phenyl)-4-methoxypyridine 1-oxide

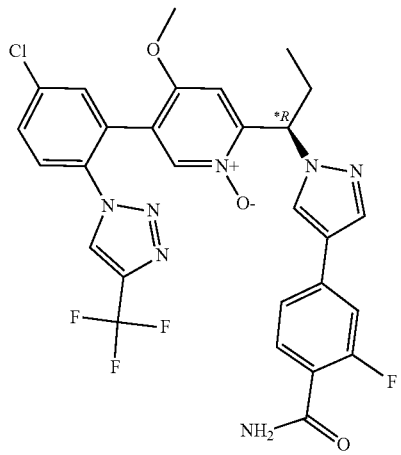

LC/MS: mass calculated for $C_{28}H_{22}ClF_4N_7O_3$: 615.14, measured (ES, m/z): 616.2 [M+H]$^+$. $^1$H NMR (400 MHz, DMSO-$d_6$) δ 9.19 (s, 1H), 8.58 (s, 1H), 8.35 (s, 1H), 8.12 (s, 1H), 7.77-7.88 (m, 3H), 7.62-7.72 (m, 1H), 7.46-7.61 (m, 4H), 6.92 (s, 1H), 5.95-6.06 (m, 1H), 3.35-3.49 (m, 3H), 2.19-2.36 (m, 2H), 0.79-0.91 (m, 3H). $^{19}$F NMR (376 MHz, DMSO-$d_6$) δ −59.71, −113.02.

Example 936: (S*)-2-(1-(4-(4-Carbamoyl-3-fluorophenyl)-1H-pyrazol-1-yl)propyl)-5-(5-chloro-2-(4-(trifluoromethyl)-1H-1,2,3-triazol-1-yl)phenyl)-4-methoxypyridine 1-oxide

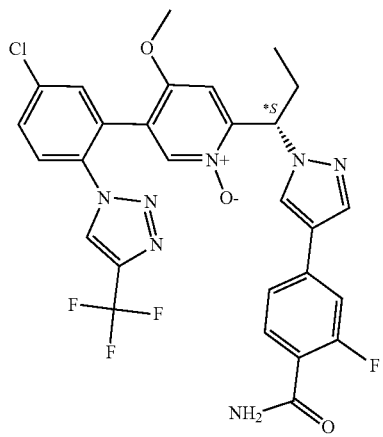 [SMILES: CC[C@@H](c1cc(OC)c(-c2cc(Cl)ccc2-n2cc(C(F)(F)F)nn2)c[n+]1[O-])n1cc(-c2ccc(C(N)=O)c(F)c2)cn1]

LC/MS: mass calculated for $C_{28}H_{22}ClF_4N_7O_3$: 615.14, measured (ES, m/z): 616.1 [M+H]$^+$. $^1$H NMR (400 MHz, DMSO-$d_6$) δ 9.19 (s, 1H), 8.58 (s, 1H), 8.34 (s, 1H), 8.12 (s, 1H), 7.75-7.88 (m, 3H), 7.62-7.72 (m, 1H), 7.46-7.61 (m, 4H), 6.90 (s, 1H), 5.95-6.06 (m, 1H), 3.35-3.49 (m, 3H), 2.19-2.36 (m, 2H), 0.75-0.91 (m, 3H). $^{19}$F NMR (376 MHz, DMSO-$d_6$) δ −59.71, −113.02.

Example 937: 2-(1-4-(4-Carboxy-3-fluorophenyl)-
1H-pyrazol-1-yl)-3-(dimethylamino)-3-oxopropyl)-
5-(3-chloro-2-fluoro-6-(4-(trifluoromethyl)-1H-1,2,
3-triazol-1-yl)phenyl)pyridine 1-oxide TFA

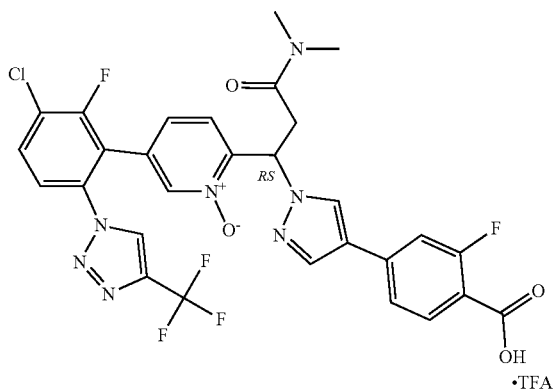 [SMILES: CN(C)C(=O)CC(c1ccc(-c2c(-n3cc(C(F)(F)F)nn3)ccc(Cl)c2F)c[n+]1[O-])n1cc(-c2ccc(C(=O)O)c(F)c2)cn1]

Step 1: (5-Bromopyridin-2-yl)methyl methanesulfonate

To a solution of (5-bromopyridin-2-yl)CH₃OH (2.0 g, 10.67 mmol) in DCM (50 mL) at 0° C. was added TEA (4.44 mL, 31.9 mmol). Then methanesulfonyl chloride (1.65 mL, 21.3 mmol) was added dropwise. The resulting mixture was stirred at 0° C. for 2 h. To the reaction mixture was added saturated NaHCO₃ solution (50 mL). The organic phase was separated and the aqueous phase was extracted further with DCM (2×50 mL). The combined organic phase was washed with brine, dried over sodium sulfate and concentrated to yield (5-bromopyridin-2-yl)methyl methanesulfonate as a pale brown oil. LC/MS: mass calculated for $C_7H_8BrNO_3S$: 264.9, measured (ES, m/z): 265.9 [M+H]⁺

Step 2: tert-Butyl 2-fluoro-4-(1H-pyrazol-4-yl)benzoate

To a mixture of tert-butyl 4-bromo-2-fluorobenzoate (1.2 g, 4.36 mmol) in 1,4-dioxane (30 mL) was added tert-butyl 4-(4,4,5,5-tetramethyl-1,3,2-dioxaborolan-2-yl)-1H-pyrazol-1-carboxylate (1.92 g, 6.54 mmol) and potassium carbonate (6.54 mL, 2 M, 13.1 mmol). The reaction mixture was bubbled with argon for 10 minutes. Then [1,1'-bis(diphenylphosphino)ferrocene] dichloropalladium(II) (0.504 g, 0.436 mmol) was added. The reaction was stirred at 100° C. for 2 h. Water was added, the mixture was extracted with EtOAc three times. The combined extracts were washed with water, saturated brine and dried over anhydrous Na₂SO₄, then concentrated and purified by chromatography on Heptane/EtOAc (10-90%) to yield tert-butyl 2-fluoro-4-(1H-pyrazol-4-yl) benzoate as a light yellow solid. LC/MS: mass calculated for $C_{14}H_{15}FN_2O_2$: 262.1, measured (ES, m/z): 263.0 [M+H]⁺

Step 3: tert-Butyl 4-(1-((5-bromopyridin-2-yl)methyl)-1H-pyrazol-4-yl)-2-fluorobenzoate To a solution of tert-butyl 2-fluoro-4-(1H-pyrazol-4-yl) benzoate (0.850 g, 3.24 mmol) in CH₃CN (35 mL) was added (5-bromopyridin-2-yl)methyl methanesulfonate (0.862 g, 3.24 mmol) and cesium carbonate (2.11 g, 6.48 mmol). The resulting mixture was stirred at 70° C. for 2 h. After cooling to room temperature, the solid was filtered off and the mother liquor was concentrated. The resulting residue was purified by silica gel chromatography (0-100% EtOAc/DCM) to yield tert-butyl 4-(1-((5-bromopyridin-2-yl)methyl)-1H-pyrazol-4-yl)-2-fluorobenzoate as a white solid. LC/MS: mass calculated for: $C_{20}H_{19}BrFN_3O_2$: 431.1, measured (ES, m/z): 432.1, 434.1 [M+H, M+H+2]⁺

Step 4: tert-Butyl 4-(1-(1-(5-bromopyridin-2-yl)-3-(dimethylamino)-3-oxopropyl)-1H-pyrazol-4-yl)-2-fluorobenzoate To a solution of tert-butyl 4-(1-((5-bromopyridin-2-yl) methyl)-1H-pyrazol-4-yl)-2-fluorobenzoate (0.25 g, 0.555 mmol) in THF (8 mL) was added lithium bis(trimethylsilyl) amide (0.867 mL, 1 M, 0.867 mmol) under Argon at −78° C. dropwise. After the addition, the reaction mixture was stirred at −78° C. for 15 min. 2-Bromo-N, N-dimethylacetamide (0.124 mL, 1.041 mmol) was added. The resulting mixture was warmed up to room temperature and stirred for 2 h. The reaction was then quenched by sat. NH₄Cl solution. The aqueous was extracted with EtOAc (2×50 mL). The organic layers were combined, washed with water, brine, dried over anhydrous sodium sulfate, filtered and concentrated. The resulting residue was purified by silica gel chromatography (5-45% EtOAc/heptane) to yield the tert-butyl 4-(1-(1-(5-bromopyridin-2-yl)-3-(dimethylamino)-3-oxopropyl)-1H-pyrazol-4-yl)-2-fluorobenzoate as a light yellow solid. LC/MS: mass calculated for $C_{24}H_{26}BrFN_4O_3$: 516.1, measured (ES, m/z): 517.0 [M+H]⁺

Step 5: ((6-(1-(4-(4-(tert-Butoxycarbonyl)-3-fluorophenyl)-1H-pyrazol-1-yl)-3-(dimethylamino)-3-oxopropyl)pyridin-3-yl)boronic acid To a mixture of tert-butyl 4-(1-(1-(5-bromopyridin-2-yl)-3-(dimethylamino)-3-oxopropyl)-1H-pyrazol-4-yl)-2-fluorobenzoate (200 mg, 0.387 mmol) in 1,4-dioxane (5 mL) was added 4,4,5,5-tetramethyl-2-(4,4,5,5-tetramethyl-1,3,2-dioxaborolan-2-yl)-1,3,2-dioxaborolane (118 mg, 0.464 mmol) and potassium acetate (75.8 mg, 0.773 mmol). The reaction mixture was bubbled with argon for 10 minutes. Then [1,1'-bis(diphenylphosphino)ferrocene] dichloropalladium(II) (32.7 mg, 0.0387 mmol) was added. The reaction was stirred at 130° C. for 1 h. LC-MS suggested the formation of ((6-(1-(4-(4-(tert-butoxycarbonyl)-3-fluorophenyl)-1H-pyrazol-1-yl)-3-(dimethylamino)-3-oxopropyl) pyridin-3-yl)boronic acid. LC/MS: mass calculated for $C_{24}H_{28}BFN_4O_5$: 482.2, measured (ES, m/z): 483.1 [M+H]⁺. The reaction mixture was then used in the next step without workup and purification.

Step 6: tert-Butyl 4-(1-(1-(5-(3-chloro-2-fluoro-6-(4-(trifluoromethyl)-1H-1,2,3-triazol-1-yl)phenyl) pyridin-2-yl)-3-(dimethylamino)-3-oxopropyl-1H-pyrazol-4-yl)-2-fluorobenzoate To a solution of (6-(1-(4-(4-(tert-butoxycarbonyl)-3-fluorophenyl)-1H-pyrazol-1-yl)-3-(dimethylamino)-3-oxopropyl)pyridin-3-yl)boronic acid (0.18 g, 0.373 mmol) in 1,4-dioxane (3 mL) was added 1-(4-chloro-3-fluoro-2-iodophenyl)-4-trifluoromethyl)-1H-1,2,3-triazole (0.146 g, 0.343 mmol) and potassium carbonate (0.411 mL, 2 M, 0.821 mmol). The reaction mixture was bubbled with argon for 10 minutes. Then tetrakis(triphenylphosphine)palladium (0) (0.0431 g, 0.0343 mmol) was added. The reaction was heated in Biotage microwave for 2.5 hours at 108° C. The reaction was cooled down to room temperature. Water was added, the mixture was extracted with EtOAc twice. The combined extracts were washed with water, brine and dried over anhydrous $Na_2SO_4$. Concentration and chromatography on EtOAc/DCM (10-90%) to yield tert-butyl 4-(1-(1-(5-(3-chloro-2-fluoro-6-(4-(trifluoromethyl)-1H-1,2,3-triazol-1-yl)phenyl)pyridin-2-yl)-3-(dimethylamino)-3-oxopropyl-1H-pyrazol-4-yl)-2-fluorobenzoate as a yellow solid. LC/MS: mass calculated for $C_{33}H_{29}ClF_5N_7O_3$: 701.2, measured (ES, m/z): 702.2 [M+H]$^+$.

Step 7: 4-(1-(1-(5-(3-Chloro-2-fluoro-6-(4-(trifluoromethyl)-1H-1,2,3-triazol-1-yl)phenyl)pyridin-2-yl)-3-(dimethylamino)-3-oxopropyl-1H-pyrazol-4-yl)-2-fluorobenzoic acid To a solution of tert-butyl 4-(1-(1-(5-(3-chloro-2-fluoro-6-(4-(trifluoromethyl)-1H-1,2,3-triazol-1-yl)phenyl)pyridin-2-yl)-3-(dimethylamino)-3-oxopropyl-1H-pyrazol-4-yl)-2-fluorobenzoate (100 mg, 0.142 mmol) in DCM (2 mL) was added TFA (2 mL). The resulting mixture was stirred at room temperature for 2 h. The reaction mixture was concentrated to yield 4-(1-(1-(5-(3-chloro-2-fluoro-6-(4-(trifluoromethyl)-1H-1,2,3-triazol-1-yl)phenyl)pyridin-2-yl)-3-(dimethylamino)-3-oxopropyl-1H-pyrazol-4-yl)-2-fluorobenzoic acid as a gummy solid, which was used in the next step without further purification. LC/MS: mass calculated for $C_{29}H_{21}ClF_5N_7O_3$: 645.1, measured (ES, m/z): 646.1 [M+H]$^+$.

Step 8: 2-(1-4-(4-Carboxy-3-fluorophenyl)-1H-pyrazol-1-yl)-3-(dimethylamino)-3-oxopropyl)-5-(3-chloro-2-fluoro-6-(4-(trifluoromethyl)-1H-1,2,3-triazol-1-yl)phenyl)pyridine 1-oxide TFA To a solution of 4-(1-(1-(5-(3-chloro-2-fluoro-6-(4-(trifluoromethyl)-1H-1,2,3-triazol-1-yl)phenyl)pyridin-2-yl)-3-(dimethylamino)-3-oxopropyl-1H-pyrazol-4-yl)-2-fluorobenzoic acid (45 mg, 0.069 mmol) in $CH_3OH$ (1 mL) was added methyltrioxorhenium (8.68 mg, 0.0348 mmol) and $H_2O_2$ (0.0718 mL, 0.697 mmol, 30%). The resulting mixture was stirred at room temperature for 1.5 h. The solvent was removed and the residue was purified by via ISCO reverse phase column 0.1% TFA in water and 0.1% TFA in ACN (35% to 60% 0.1% TFA in ACN gradient) to yield 2-(1-4-(4-carboxy-3-fluorophenyl)-1H-pyrazol-1-yl)-3-(dimethylamino)-3-oxopropyl)-5-(3-chloro-2-fluoro-6-(4-(trifluoromethyl)-1H-1,2,3-triazol-1-yl)phenyl)pyridine 1-oxide TFA salt as an off-white solid.

LC/MS: mass calculated for $C_{29}H_{21}ClF_5N_7O_4$: 661.1, measured (ES, m/z): 662.3 [M+H]$^+$. $^1$H NMR: (CD$_3$OD, 400 MHz) δ 8.79 (s, 1H), 8.37 (d, J=7.34 Hz, 2H), 8.04 (s, 1H), 7.91 (dt, J=9.78, 8.07 Hz, 2H), 7.60 (dd, J=8.80, 1.47 Hz, 1H), 7.38-7.49 (m, 2H), 7.14-7.33 (m, 2H), 6.64 (d, J=5.38 Hz, 1H), 3.63 (m, 1H), 3.43 (m, 1H), 3.13 (s, 3H), 2.89 (s, 3H). $^{19}$F-NMR: (CD$_3$OD, 377 MHz) δ −126.34, −123.64, −89.95, −75.05.

Example 938: (R*)-2-(1-(4-(4-Carboxyphenyl)-1H-pyrazol-1-yl)-3-(difluoromethoxy)propyl)-5-(3-chloro-6-(4-chloro-1H-1,2,3-triazol-1-yl)-2-fluorophenyl)pyridine 1-oxide

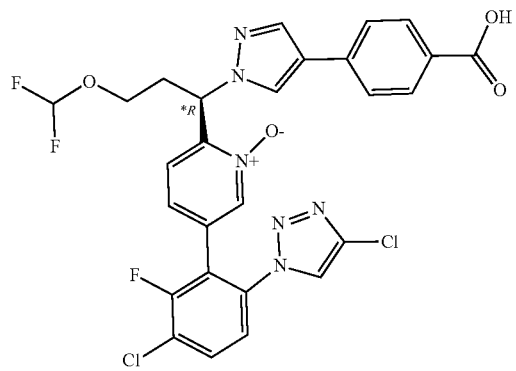 [SMILES: O=C(O)c1ccc(-c2cnn([C@H](CCOC(F)F)c3ccc(-c4c(-n5cc(Cl)nn5)ccc(Cl)c4F)c[n+]3[O-])c2)cc1]

LC/MS: mass calculated for $C_{27}H_{19}Cl_2F_3N_6O_4$: 618.08, measured (ES, m/z): 619.1 [M+H]$^+$. $^1$H NMR (400 MHz, DMSO-d$_6$) δ 12.85 (s, 1H), 8.68 (s, 1H), 8.58 (s, 1H), 8.42 (s, 1H), 8.17 (s, 1H), 8.02 (dd, J=8.7, 7.8 Hz, 1H), 7.89-7.96 (m, 2H), 7.65-7.79 (m, 3H), 7.27 (d, J=8.3 Hz, 1H), 7.17 (dd, J=8.3, 1.7 Hz, 1H), 6.64 (t, J=75.8 Hz, 1H), 6.20-6.28 (m, 1H), 3.64-3.90 (m, 2H), 2.52-2.69 (m, 2H). $^{19}$F NMR (376 MHz, DMSO-d$_6$) δ −83.25, −112.94.

Example 939: (S*)-2-(1-(4-(4-Carboxyphenyl)-1H-pyrazol-1-yl)-3-(difluoromethoxy)propyl)-5-(3-chloro-6-(4-chloro-1H-1,2,3-triazol-1-yl)-2-fluorophenyl)pyridine 1-oxide

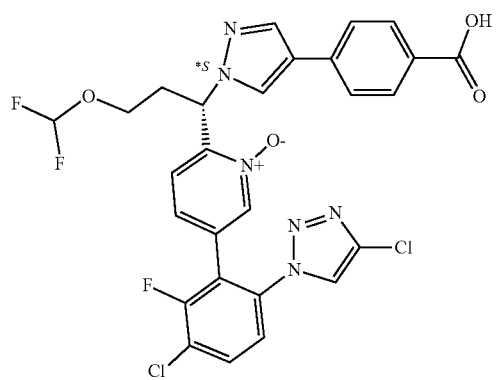 [SMILES: O=C(O)c1ccc(-c2cnn([C@@H](CCOC(F)F)c3ccc(-c4c(-n5cc(Cl)nn5)ccc(Cl)c4F)c[n+]3[O-])c2)cc1]

Step 1: tert-Butyl 4-(1-(1-(5-bromopyridin-2-yl)-3-(difluoromethoxy)propyl)-1H-pyrazol-4-yl)benzoate To a solution of tert-butyl 4-(1H-pyrazol-4-yl)benzoate (271 mg, 1.11 mmol, 1.0 equiv.) in N,N-dimethylformamide (10 mL) was added sodium tert-butoxide (101 mg, 1.05 mmol, 0.9 equiv.). The reaction was stirred at room temperature for 30 min. 1-(5-Bromopyridin-2-yl)-3-(difluoromethoxy)propyl methanesulfonate (400 mg, 1.11 mmol, 1.0 equiv.) was added and the reaction was stirred at room temperature. for 4 h. Water was added, the mixture was extracted with ethyl acetate. The combined extracts were washed with water, saturated brine and dried over anhydrous Na$_2$SO$_4$ and concentrated. The residue was purified silica gel chromatography (0→75% EA/PE) to yield tert-butyl 4-(1-(1-(5-bromopyridin-2-yl)-3-(difluoromethoxy)propyl)-1H-pyrazol-4-yl)benzoate as yellow oil. LC/MS: mass calculated for C$_{23}$H$_{24}$BrF$_2$N$_3$O$_3$: 507.10, measured (ES, m/z): 508.05, 510.05 [M+H, M+H+2]$^+$.

Step 2: (6-(1-(4-(4-(tert-Butoxycarbonyl)phenyl)-1H-pyrazol-1-yl)-3-(difluoromethoxy)propyl)pyridin-3-yl)boronic acid To a mixture of tert-butyl 4-(1-(1-(5-bromopyridin-2-yl)-3-(difluoromethoxy)propyl)-1H-pyrazol-4-yl)benzoate (550 mg, 1.08 mmol, 1.0 equiv.) and 4,4,4',4',5,5,5',5'-octamethyl-2,2'-bi(1,3,2-dioxaborolane) (549 mg, 2.16 mmol, 2.0 equiv.) in 1,4-dioxane (15 mL) was added potassium acetate (318 mg, 3.25 mmol, 3.0 equiv.) and [1,1'-bis(diphenylphosphino)ferrocene]dichloropalladium(II) (79 mg, 0.11 mmol, 0.1 equiv.). The reaction was stirred at 100° C. for 3H under N$_2$. After cooling to room temperature, the reaction was quenched with water, and the mixture extracted with EA. The combined extracts were washed with water, saturated brine and dried over anhydrous Na$_2$SO$_4$. Concentration to yield (6-(1-(4-(4-(tert-butoxycarbonyl)phenyl)-1H-pyrazol-1-yl)-3-(difluoromethoxy)propyl)pyridin-3-yl)boronic acid as a black solid. LC/MS: mass calculated for C$_{23}$H$_{26}$BF$_2$N$_3$O$_5$: 473.19, measured (ES, m/z): 474.35 [M+H]$^+$.

Step 3: tert-Butyl 4-(1-(1-(5-(3-chloro-6-(4-chloro-1H-1,2,3-triazol-1-yl)-2-fluorophenyl)pyridin-2-yl)-3-(difluoromethoxy)propyl)-1H-pyrazol-4-yl)benzoate To a mixture of (6-(1-(4-(4-(tert-butoxycarbonyl)phenyl)-1H-pyrazol-1-yl)-3-(difluoromethoxy)propyl)pyridin-3-yl)boronic acid (850 mg, resulting) and 4-chloro-1-(4-chloro-3-fluoro-2-iodophenyl)-1H-1,2,3-triazole (295 mg, 0.82 mmol, 1.0 equiv.) in 1,4-dioxane (10 mL) and water (2 mL) was added potassium acetate (341 mg, 2.45 mmol, 3.0 equiv.) and tetrakis(triphenylphosphine)palladium (100 mg, 0.08 mmol, 0.1 equiv.). The reaction was stirred at 100° C. for 4 h under N$_2$. After cooling to room temperature, the reaction was quenched with water, and the mixture extracted with EA. The combined extracts were dried over anhydrous Na$_2$SO$_4$ and concentrated. The residue was purified silica gel chromatography (0→65% EA/PE) to yield tert-butyl 4-(1-(1-(5-(3-chloro-6-(4-chloro-1H-1,2,3-triazol-1-yl)-2-fluorophenyl)pyridin-2-yl)-3-(difluoromethoxy)propyl)-1H-pyrazol-4-yl)benzoate as a yellow solid. LC/MS: mass calculated for C$_{31}$H$_{27}$Cl$_2$F$_3$N$_6$O$_3$: 658.15, measured (ES, m/z): 659.20 [M+H]$^+$.

Step 4: 4-(1-(1-(5-(3-Chloro-6-(4-chloro-1H-1,2,3-triazol-1-yl)-2-fluorophenyl)pyridin-2-yl)-3-(difluoromethoxy)propyl)-1H-pyrazol-4-yl)benzoic acid To a solution of tert-butyl 4-(1-(1-(5-(3-chloro-6-(4-chloro-1H-1,2,3-triazol-1-yl)-2-fluorophenyl)pyridin-2-yl)-3-(difluoromethoxy)propyl)-1H-pyrazol-4-yl)benzoate (470 mg, 0.71 mmol, 1.0 equiv.) in dichloromethane (15 mL) was added trifluoroacetic acid (5 mL). The reaction was stirred at room temperature. for 6 h. The mixture was concentrated under vacuum. The residue was purified by reverse phase chromatography on C18 (120 g, MeCN/H$_2$O (0.05% CF$_3$COOH): 5→50%) to yield 4-(1-(1-(5-(3-chloro-6-(4-chloro-1H-1,2,3-triazol-1-yl)-2-fluorophenyl)pyridin-2-yl)-3-(difluoromethoxy)propyl)-1H-pyrazol-4-yl)benzoic acid as yellow solid. LC/MS: mass calculated for C$_{27}$H$_{19}$Cl$_2$F$_3$N$_6$O$_3$: 602.08, measured (ES, m/z): 603.25 [M+H]$^+$ Step 5: (S*)-2-(1-(4-(4-Carboxyphenyl)-1H-pyrazol-1-yl)-3-(difluoromethoxy)propyl)-5-(3-chloro-6-(4-chloro-1H-1,2,3-triazol-1-yl)-2-fluorophenyl)pyridine 1-oxide To a mixture of 4-(1-(1-(5-(3-chloro-6-(4-chloro-1H-1,2,3-triazol-1-yl)-2-fluorophenyl)pyridin-2-yl)-3-(difluoromethoxy)propyl)-1H-pyrazol-4-yl)benzoic acid (370 mg, 0.61 mmol, 1.0 equiv.) and methyltrioxorhenium (46 mg, 0.18 mmol, 0.3 equiv) in CH$_3$OH (10 mL) was added hydrogen peroxide (30 wt %, 695 mg, 6.13 mmol, 10.0 equiv.). The reaction was stirred at room temperature for 5 h. The resulting mixture was purified by reverse phase chromatography on C18 (120 g, MeCN/H$_2$O (0.05% CF$_3$COOH): 5→65%) and Prep-Chiral-HPLC to yield (S*)-2-(1-(4-(4-carboxyphenyl)-1H-pyrazol-1-yl)-3-(difluoromethoxy)propyl)-5-(3-chloro-6-(4-chloro-1H-1,2,3-triazol-1-yl)-2-fluorophenyl)pyridine 1-oxide as a white solid.

LC/MS: mass calculated for C$_{27}$H$_{19}$Cl$_2$F$_3$N$_6$O$_4$: 618.08, measured (ES, m/z): 619.05 [M+H]$^+$. $^1$H NMR (400 MHz, DMSO-d$_6$): δ 8.67 (s, 1H), 8.58 (s, 1H), 8.42 (s, 1H), 8.17 (s, 1H), 7.98-8.08 (m, 1H), 7.87-7.95 (m, 2H), 7.64-7.79 (m, 3H), 7.27 (d, J=8.3 Hz, 1H), 7.11-7.21 (m, 1H), 6.64 (t, J=75.7 Hz, 1H), 6.15-6.25 (m, 1H), 3.81-3.91 (m, 1H), 3.66-3.75 (m, 1H), 2.54-2.70 (m, 2H). $^{19}$F NMR (376 MHz, DMSO-d$_6$): δ −83.25, −112.94.

Example 940: (R*)-2-(1-(4-(4-Carbamoyl-3-fluorophenyl)-1H-pyrazol-1-yl)propyl)-5-(5-chloro-2-(4-(trifluoromethyl)-1H-1,2,3-triazol-1-yl)phenyl)pyridine 1-oxide

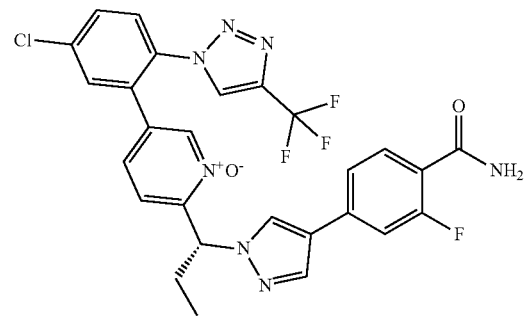

LC/MS: mass calculated for C$_{27}$H$_{19}$ClF$_5$N$_7$O$_2$: 603.12, measured (ES, m/z): 604.05 [M+H]$^+$. $^1$H NMR (400 MHz, DMSO-d$_6$) δ 9.16-9.17 (m, 1H), 8.60 (s, 1H), 8.40-8.41 (m, 1H), 8.13 (s, 1H), 8.02-8.06 (m, 1H), 7.78-7.80 (m, 1H), 7.62-7.71 (m, 1H), 7.51-7.60 (m, 4H), 7.29-7.31 (m, 1H), 7.15-7.18 (m, 1H), 5.89-5.94 (m, 1H), 2.17-2.31 (m, 2H), 0.84-0.86 (m, 3H). $^{19}$F NMR (400 MHz, DMSO-d$_6$) δ −59.77, 113.00.

Example 941: (R*)-2-(1-(4-(4-Carbamoyl-3-fluoro-phenyl)-1H-pyrazol-1-yl)propyl)-5-(3-chloro-2-fluoro-6-(4-(trifluoromethyl)-1H-1,2,3-triazol-1-yl)phenyl)pyridine 1-oxide

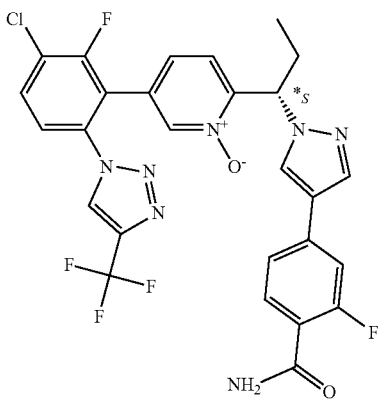 [SMILES: CC[C@@H](c1ccc(-c2c(-n3cc(C(F)(F)F)nn3)ccc(Cl)c2F)c[n+]1[O-])n1cc(-c2ccc(C(N)=O)c(F)c2)cn1]

LC/MS: mass calculated for $C_{27}H_{19}ClF_5N_7O_2$: 603.12, measured (ES, m/z): 604.05 [M+H]$^+$. $^1$H NMR (400 MHz, DMSO-d$_6$) δ 9.17 (d, J=1.1 Hz, 1H), 8.60 (s, 1H), 8.41 (d, J=1.6 Hz, 1H), 8.13 (s, 1H), 8.06 (dd, J=8.7, 7.7 Hz, 1H), 7.78 (dd, J=8.7, 1.5 Hz, 1H), 7.68 (t, J=8.0 Hz, 1H), 7.58-7.63 (m, 2H), 7.50-7.58 (m, 2H), 7.30 (d, J=8.3 Hz, 1H), 7.14 (dd, J=8.3, 1.7 Hz, 1H), 5.89-5.93 (m, 1H), 2.13-2.31 (m, 2H), 0.84 (t, J=7.2 Hz, 3H). $^{19}$F NMR (400 MHz, DMSO-d$_6$) δ −59.77, 113.00.

Example 942: 2-(1-4-(4-Carbamoyl-3-fluorophe-nyl)-1H-pyrazol-1-yl)-3-(dimethylamino)-3-oxopro-pyl)-5-(3-chloro-2-fluoro-6-(4-(trifluoromethyl)-1H-1,2,3-triazol-1-yl)phenyl)pyridine 1-oxide TFA

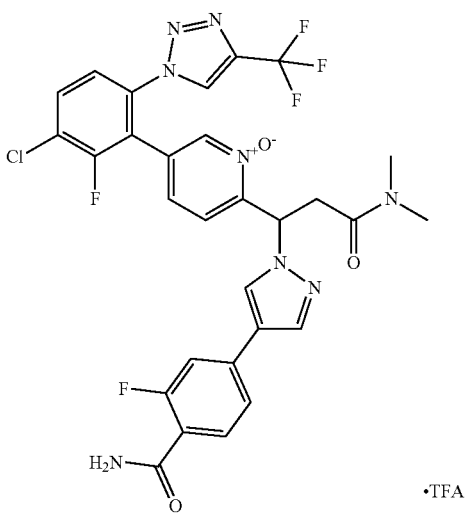

Step 1: (5-Bromopyridin-2-yl)methyl methanesulfonate

To a solution of (5-bromopyridin-2-yl)methanol (2.0 g, 10.67 mmol) in DCM (50 mL) at 0° C. was added TEA (4.44 mL, 31.9 mmol). Then methanesulfonyl chloride (1.65 mL, 21.3 mmol) was added dropwise.

The resulting mixture was stirred at 0° C. for 2 h. To the reaction mixture was added saturated NaHCO$_3$ solution (50 mL). The organic phase was separated and the aqueous phase was extracted further with DCM (2×50 mL). The combined organic phase was washed with brine, dried over sodium sulfate and concentrated to yield (5-bromopyridin-2-yl)methyl methanesulfonate as a pale brown oil. LC/MS: mass calculated for $C_7H_8BrNO_3S$: 264.9, measured (ES, m/z): 265.9 [M+H]$^+$ Step 2: tert-Butyl 2-fluoro-4-(1H-pyrazol-4-yl)benzoate To a mixture of tert-butyl 4-bromo-2-fluorobenzoate (1.2 g, 4.36 mmol) in 1,4-dioxane (30 mL) was added tert-butyl 4-(4,4,5,5-tetramethyl-1,3,2-dioxaborolan-2-yl)-1H-pyra-zol-1-carboxylate (1.92 g, 6.54 mmol) and potassium carbonate (6.54 mL, 2 M, 13.1 mmol). The reaction mixture was bubbled with argon for 10 minutes. Then [1,1'-bis(diphenylphosphino)ferrocene] dichloropalladium(II) (0.504 g, 0.436 mmol) was added. The reaction was stirred at 100° C. for 2 h. Water was added, the mixture was extracted with EtOAc three times. The combined extracts were washed with water, saturated brine and dried over anhydrous Na$_2$SO$_4$, then concentrated and purified by chromatography on Heptane/EtOAc (10-90%) to yield tert-butyl 2-fluoro-4-(1H-pyrazol-4-yl) benzoate as a light yellow solid. LC/MS: mass calculated for $C_{14}H_{15}FN_2O_2$: 262.1, measured (ES, m/z): 263.0 [M+H]$^+$.

Step 3: tert-Butyl 4-(1-((5-bromopyridin-2-yl)methyl)-1H-pyrazol-4-yl)-2-fluorobenzoate To a solution of tert-butyl 2-fluoro-4-(1H-pyrazol-4-yl)benzoate (0.850 g, 3.24 mmol) in CH$_3$CN (35 mL) was added (5-bromopyridin-2-yl)methyl methanesulfonate (0.862 g, 3.24 mmol) and cesium carbonate (2.11 g, 6.48 mmol). The resulting mixture was stirred at 70° C. for 2 h. After cooling to room temperature, the solid was filtered off and the mother liquor was concentrated. The resulting residue was purified by silica gel chromatography (0-100% EtOAc/DCM) to yield tert-butyl 4-(1-((5-bromopyridin-2-yl)methyl)-1H-pyrazol-4-yl)-2-fluorobenzoate as a white solid. LC/MS: mass calculated for: $C_{20}H_1BrFN_3O_2$: 431.1, measured (ES, m/z): 432.1, 434.1 [M+H, M+H+2]$^+$ Step 4: tert-Butyl 4-(1-(1-(5-bromopyridin-2-yl)-3-(dimethylamino)-3-oxopropyl)-1H-pyrazol-4-yl)-2-fluorobenzoate To a solution of tert-butyl 4-(1-((5-bromopyridin-2-yl)methyl)-1H-pyrazol-4-yl)-2-fluorobenzoate (0.25 g, 0.555 mmol) in THF (8 mL) was added lithium bis(trimethylsilyl)amide (0.867 mL, 1 M, 0.867 mmol) under Argon at −78° C. dropwise. After the addition, the reaction mixture was stirred at −78° C. for 15 min. 2-bromo-N, N-dimethylacetamide (0.124 mL, 1.041 mmol) was added. The resulting mixture was warmed up to room temperature and stirred for 2 h. The reaction was then quenched by sat. NH$_4$Cl solution. The aqueous was extracted with EtOAc (2×50 mL). The organic layers were combined, washed with water, brine, dried over anhydrous sodium sulfate, filtered and concentrated. The resulting residue was purified by silica gel chromatography (5-45% EtOAc/heptane) to yield the tert-butyl 4-(1-(1-(5-bromopyridin-2-yl)-3-(dimethylamino)-3-oxopropyl)-1H- pyrazol-4-yl)-2-fluorobenzoate as a light yellow solid. LC/MS: mass calculated for $C_{24}H_{26}BrFN_4O_3$: 516.1, measured (ES, m/z): 517.0 [M+H]$^+$ Step 5: ((6-(1-(4-(4-(tert-Butoxycarbonyl)-3-fluorophenyl)-1H-pyrazol-1-yl)-3-(dimethylamino)-3-oxopropyl)pyridin-3-yl)boronic acid To a mixture of tert-butyl 4-(1-(1-(5-bromopyridin-2-yl)-3-(dimethylamino)-3-oxopropyl)-1H-pyrazol-4-yl)-2-fluorobenzoate (200 mg, 0.387 mmol) in 1,4-dioxane (5 mL) was added 4,4,5,5-tetramethyl-2-(4,4,5,5-tetramethyl-1,3,2-dioxaborolan-2-yl)-1,3,2-dioxaborolane (118 mg, 0.464 mmol) and potassium acetate (75.8 mg, 0.773 mmol). The reaction mixture was bubbled with argon for 10 minutes. Then [1,1'-bis(diphenylphosphino)ferrocene] dichloropalladium(II) (32.7 mg, 0.0387 mmol) was added. The reaction was stirred at 130° C. for 1H. LC-MS suggested the formation of ((6-(1-(4-(4-(tert-butoxycarbonyl)-3-fluorophenyl)-1H-pyrazol-1-yl)-3-(dimethylamino)-3-oxopropyl)pyridin-3-yl)boronic acid. LC/MS: mass calculated for $C_{24}H_{28}BFN_4O_5$: 482.2, measured (ES, m/z): 483.1 [M+H]$^+$. The reaction mixture was then used in the next step without workup and purification.

Step 6: tert-Butyl 4-(1-(1-(5-(3-chloro-2-fluoro-6-(4-(trifluoromethyl)-1H-1,2,3-triazol-1-yl)phenyl) pyridin-2-yl)-3-(dimethylamino)-3-oxopropyl-1H-pyrazol-4-yl)-2-fluorobenzoate To a solution of (6-(1-(4-(4-(tert-butoxycarbonyl)-3-fluorophenyl)-1H-pyrazol-1-yl)-3-(dimethylamino)-3-oxopropyl)pyridin-3-yl)boronic acid (0.18 g, 0.373 mmol) in 1,4-dioxane (3 mL) was added 1-(4-chloro-3-fluoro-2-iodophenyl)-4-trifluoromethyl)-1H-1,2,3-triazole (0.146 g, 0.343 mmol) and potassium carbonate (0.411 mL, 2 M, 0.821 mmol). The reaction mixture was bubbled with argon for 10 minutes. Then tetrakis(triphenylphosphine)palladium (0) (0.0431 g, 0.0343 mmol) was added. The reaction was heated in Biotage microwave for 2.5 hours at 108° C. The reaction was cooled down to room temperature. Water was added, the mixture was extracted with EtOAc twice. The combined extracts were washed with water, brine and dried over anhydrous $Na_2SO_4$, then concentrated and purified by chromatography on EtOAc/DCM (10-90%) to yield tert-butyl 4-(1-(1-(5-(3-chloro-2-fluoro-6-(4-(trifluoromethyl)-1H-1,2,3-triazol-1-yl)phenyl)pyridin-2-yl)-3-(dimethylamino)-3-oxopropyl-1H-pyrazol-4-yl)-2-fluorobenzoate as a yellow solid. LC/MS: mass calculated for $C_{33}H_{29}ClF_5N_7O_3$: 701.2, measured (ES, m/z): 702.2 [M+H]$^+$.

Step 7: 4-(1-(1-(5-(3-Chloro-2-fluoro-6-(4-(trifluoromethyl)-1H-1,2,3-triazol-1-yl)phenyl)pyridin-2-yl)-3-(dimethylamino)-3-oxopropyl-1H-pyrazol-4-yl)-2-fluorobenzoic acid To a solution of tert-butyl 4-(1-(1-(5-(3-chloro-2-fluoro-6-(4-(trifluoromethyl)-1H-1,2,3-triazol-1-yl)phenyl)pyridin-2-yl)-3-(dimethylamino)-3-oxopropyl-1H-pyrazol-4-yl)-2-fluorobenzoate (100 mg, 0.142 mmol) in DCM (2 mL) was added TFA (2 mL). The resulting mixture was stirred at room temperature for 2 h. The reaction mixture was concentrated to yield 4-(1-(1-(5-(3-chloro-2-fluoro-6-(4-(trifluoromethyl)-1H-1,2,3-triazol-1-yl)phenyl)pyridin-2-yl)-3-(dimethylamino)-3-oxopropyl-1H-pyrazol-4-yl)-2-fluorobenzoic acid as a gummy solid, which was used for the next step without further purification. LC/MS: mass calculated for $C_{29}H_{21}ClF_5N_7O_3$: 645.1, measured (ES, m/z): 646.1 [M+H]$^+$.

Step 8: 2-(1-4-(4-Carbamoyl-3-fluorophenyl)-1H-pyrazol-1-yl)-3-(dimethylamino)-3-oxopropyl)-5-(3-chloro-2-fluoro-6-(4-(trifluoromethyl)-1H-1,2,3-triazol-1-yl)phenyl)pyridine 1-oxide TFA To a solution of 4-(1-(1-(5-(3-chloro-2-fluoro-6-(4-(trifluoromethyl)-1H-1,2,3-triazol-1-yl)phenyl)pyridin-2-yl)-3-(dimethylamino)-3-oxopropyl-1H-pyrazol-4-yl)-2-fluorobenzoic acid (45 mg, 0.069 mmol) in $CH_3OH$ (1 mL) was added methyltrioxorhenium (8.68 mg, 0.0348 mmol) and $H_2O_2$ (0.0718 mL, 0.697 mmol, 30%). The resulting mixture was stirred at room temperature for 0.5 h. The solvent was removed and the residue was re-dissolved in DMF (0.5 mL), followed by the addition of hydroxybenzotriazole hydrate (11.3 mg, 0.0836 mmol), 1-ethyl-3-(3-dimethylaminopropyl)carbodiimide (16.0 mg, 0.0836 mmol), ammonium chloride (37.6 mg, 0.697 mmol) and Hunig's base (0.024 mL, 0.75 g/mL, 0.139 mmol). The reaction mixture was then heated at 60° C. for 2 h. The reaction mixture was cooled to room temperature, then partitioned between water and EtOAc. The organic layer was collected, washed with water and brine, dried over $MgSO_4$, filtered and concentrated. The residue was purified by via ISCO reverse phase column 0.1% TFA in water and 0.1% TFA in ACN (35% to 60% 0.1% TFA in ACN gradient) to yield 2-(1-4-(4-carbamoyl-3-fluorophenyl)-1H-pyrazol-1-yl)-3-(dimethylamino)-3-oxopropyl)-5-(3-chloro-2-fluoro-6-(4-(trifluoromethyl)-1H-1,2,3-triazol-1-yl)phenyl)pyridine 1-oxide TFA salt as a white solid.

LC/MS: mass calculated for $C_{29}H_{22}ClF_5N_8O_3$: 660.1, measured (ES, m/z): 661.1. $^1$H NMR: (CD$_3$OD, 400 MHz) δ 8.79 (s, 1H), 8.35 (m, 2H), 8.10 (s, 1H), 7.79-7.96 (m, 2H), 7.56 (m, 1H), 7.30-7.49 (m, 2H), 7.23 (bs, 2H), 6.63 (m, 1H), 3.65 (m, 1H), 3.43 (m, 1H), 3.10 (m, 3H), 2.89 (s, 3H). $^{19}$F-NMR: (CD$_3$OD, 377 MHz) δ −127.08, −126.30, −89.98, −75.05.

Example 943: 5-(3-Chloro-2-fluoro-6-(4-(trifluoromethyl)-1H-1,2,3-triazol-1-yl)phenyl)-2-(3-(difluoromethoxy)-1-(4-(3-oxoisoindolin-5-yl)-1H-pyrazol-1-yl)propyl)pyridine 1-oxide

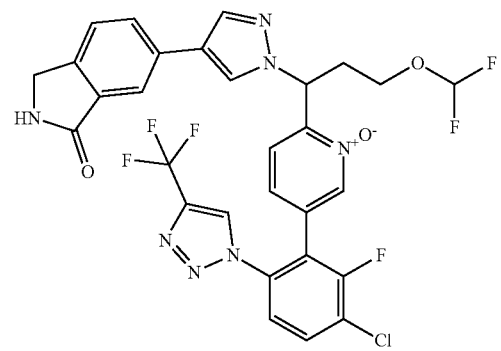

LC/MS: mass calculated for $C_{29}H_{20}ClF_6N_7O_3$: 663.1, measured (ES, m/z): 664.1 [M+H]$^+$. $^1$H NMR (400 MHz, CD$_3$OD) δ ppm 2.68-2.85 (m, 2H), 3.78 (td, J=9.54, 4.40 Hz, 1H), 3.97-4.05 (m, 1H), 4.49 (s, 2H), 6.11-6.62 (m, 2H), 7.22-7.34 (m, 1H), 7.44-7.52 (m, 1H), 7.57-7.65 (m, 2H), 7.84-7.95 (m, 2H), 7.97 (s, 1H), 8.07-8.21 (m, 1H), 8.35-8.47 (m, 1H), 8.78-8.84 (m, 1H).

Example 944: (S*)-2-(1-(4-(4-Carboxy-3-fluorophenyl)-1H-pyrazol-1-yl)-3-(difluoromethoxy)propyl)-5-(3-chloro-2-fluoro-6-(4-(trifluoromethyl)-1H-1,2,3-triazol-1-yl)phenyl)pyridine 1-oxide

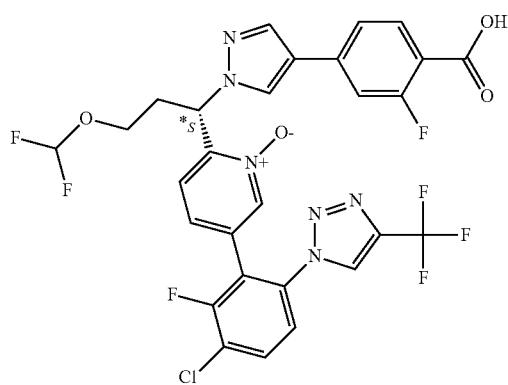 [SMILES: O=C(O)c1ccc(-c2cnn([C@@H](CCOC(F)F)c3ccc(-c4c(-n5cc(C(F)(F)F)nn5)ccc(Cl)c4F)c[n+]3[O-])c2)cc1F]

LC/MS: mass calculated for $C_{28}H_{18}ClF_7N_6O_4$: 670.10, measured (ES, m/z): 671.15 [M+H]$^+$. $^1$H NMR (400 MHz, CD$_3$OD) δ 8.78 (s, 1H), 8.34-8.40 (m, 2H), 8.08 (s, 1H), 7.85-7.97 (m, 2H), 7.60 (dd, J=8.6, 1.6 Hz, 1H), 7.40-7.51 (m, 3H), 7.29 (dd, J=8.4, 1.7 Hz, 1H), 6.36-6.40 (m, 1H), 6.36 (t, J=75.2 Hz, 1H), 3.92-4.00 (m, 1H), 3.69-3.78 (m, 1H), 2.62-2.83 (m, 2H). $^{19}$F NMR (376 MHz, CD$_3$OD) δ −62.72, −86.13, −111.22, −113.94.

Example 945: (R*)-2-(1-(4-(4-Carboxy-3-fluorophenyl)-1H-pyrazol-1-yl)-3-(difluoromethoxy)propyl)-5-(3-chloro-2-fluoro-6-(4-(trifluoromethyl)-1H-1,2,3-triazol-1-yl)phenyl)pyridine 1-oxide

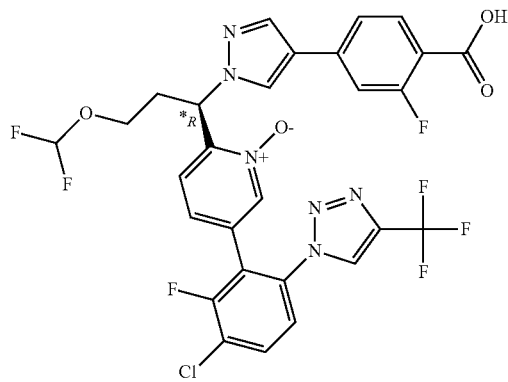 [SMILES: O=C(O)c1ccc(-c2cnn([C@H](CCOC(F)F)c3ccc(-c4c(-n5cc(C(F)(F)F)nn5)ccc(Cl)c4F)c[n+]3[O-])c2)cc1F]

Step 1: tert-Butyl 4-(1-(1-(5-bromopyridin-2-yl)-3-(difluoromethoxy)propyl)-1H-pyrazol-4-yl)-2-fluorobenzoate To a solution of tert-butyl 2-fluoro-4-(1H-pyrazol-4-yl)benzoate (300 mg, 1.14 mmol, 1.0 equiv.) in N,N-dimethylformamide (30 mL) was added sodium tert-butoxide (100 mg, 1.09 mmol, 0.95 equiv.). The resulting mixture was stirred at 0° C. for 0.5 h. Then 1-(5-bromopyridin-2-yl)-3-(difluoromethoxy)propyl methanesulfonate (410 mg, 1.14 mmol, 1.0 equiv.) was added and the mixture was stirred at room temperature for 2 hours. The reaction was quenched with water, extracted with ethyl acetate twice. The organic layers were combined, washed with brine, dried over anhydrous sodium sulfate, filtered and concentrated. The resulting residue was purified by silica gel chromatography (0→20% EA/PE) to yield tert-butyl 4-(1-(1-(5-bromopyridin-2-yl)-3-(difluoromethoxy)propyl)-1H-pyrazol-4-yl)-2-fluorobenzoate as a yellow solid. LC/MS: mass calculated for $C_{23}H_{23}BrF_3N_3O_3$: 525.09, measured (ES, m/z): 428.05 [M+H+2]$^+$.

Step 2: (6-(1-(4-(4-(tert-Butoxycarbonyl)-3-fluorophenyl)-1H-pyrazol-1-yl)-3-(difluoromethoxy)propyl)pyridin-3-yl)boronic acid To a solution of tert-butyl 4-(1-(1-(5-bromopyridin-2-yl)-3-(difluoromethoxy)propyl)-1H-pyrazol-4-yl)-2-fluorobenzoate (340 mg, 0.65 mmol, 1.0 equiv.) in 1,4-dioxane (40 mL) was added 4,4,4',4',5,5,5',5'-octamethyl-2,2'-bi(1,3,2-dioxaborolane) (328 mg, 1.29 mmol, 2.0 equiv), potassium acetate (190 mg, 1.94 mmol, 3.0 equiv.) and Pd(dppf)Cl$_2$ (53 mg, 0.07 mmol, 0.1 equiv.) under N$_2$. The mixture was stirred for 3 h at 100° C. The reaction was quenched with H$_2$O. The resulting mixture was extracted with EA. The organic layers were combined, dried over Na$_2$SO$_4$, filtered and concentrated to yield (6-(1-(4-(4-(tert-butoxycarbonyl)-3-fluorophenyl)-1H-pyrazol-1-yl)-3-(difluoromethoxy)propyl)pyridin-3-yl)boronic acid as brown solid.

Step 3: tert-Butyl 4-(1-(1-(5-(3-chloro-2-fluoro-6-(4-(trifluoromethyl)-1H-1,2,3-triazol-1-yl)phenyl)pyridin-2-yl)-3-(difluoromethoxy)propyl)-1H-pyrazol-4-yl)-2-fluorobenzoate To a solution of (6-(1-(4-(4-(tert-butoxycarbonyl)-3-fluorophenyl)-1H-pyrazol-1-yl)-3-(difluoromethoxy)propyl)pyridin-3-yl)boronic acid (320 mg, resulting) in 1,4-dioxane (20 mL) and water (4 mL) was added 1-(2-bromo-4-chlorophenyl)-4-(trifluoromethyl)-1H-1,2,3-triazole (0.1 g, 0.26 mmol, 1.0 equiv.), tetrakis(triphenylphosphine)palladium (30 mg, 0.03 mmol, 0.1 equiv.) and potassium carbonate (106 mg, 0.77 mmol, 3.0 equiv.) under N$_2$. The reaction mixture was stirred at 100° C. for 2 h. The reaction mixture was cooled to room temperature, water added, and the resulting mixture was extracted with ethyl acetate. The combined organic layers were dried over anhydrous sodium sulfate and concentrated under vacuum. The residue was applied onto a silica gel column (0→80% PE/EA) to yield tert-butyl 4-(1-(1-(5-(3-chloro-2-fluoro-6-(4-(trifluoromethyl)-1H-1,2,3-triazol-1-yl)phenyl)pyridin-2-yl)-3-(difluoromethoxy)propyl)-1H-pyrazol-4-yl)-2-fluorobenzoate as yellow oil. LC/MS: mass calculated for $C_{32}H_{26}ClF_7N_6O_3$: 710.16, measured (ES, m/z): 711.15 [M+H]$^+$.

Step 4: 4-(1-(1-(5-(3-Chloro-2-fluoro-6-(4-(trifluoromethyl)-1H-1,2,3-triazol-1-yl)phenyl)pyridin-2-yl)-3-(difluoromethoxy)propyl)-1H-pyrazol-4-yl)-2-fluorobenzoic acid To a solution of tert-butyl 4-(1-(1-(5-(3-chloro-2-fluoro-6-(4-(trifluoromethyl)-1H-1,2,3-triazol-1-yl)phenyl)pyridin-2-yl)-3-(difluoromethoxy)propyl)-1H-pyrazol-4-yl)-2-fluorobenzoate (150 mg, 0.21 mmol, 1.0 equiv.) in dichloromethane (18 mL) was added trifluoroacetic acid (6 mL). The resulting mixture was stirred at room temperature for 2 h, then concentrated under vacuum, then purified by reverse phase chromatography on C18 (80 g, MeCN/H₂O (0.05% CF₃COOH): 0→50%) to yield 4-(1-(1-(5-(3-chloro-2-fluoro-6-(4-(trifluoromethyl)-1H-1,2,3-triazol-1-yl)phenyl)pyridin-2-yl)-3-(difluoromethoxy)propyl)-1H-pyrazol-4-yl)-2-fluorobenzoic acid as yellow oil. LC/MS: mass calculated for $C_{28}H_{18}ClF_7N_8O_3$: 654.10, measured (ES, m/z): 655.05 [M+H]⁺.

Step 5: (R)-2-(1-(4-(4-Carboxy-3-fluorophenyl)-1H-pyrazol-1-yl)-3-(difluoromethoxy)propyl)-5-(3-chloro-2-fluoro-6-(4-(trifluoromethyl)-1H-1,2,3-triazol-1-yl)phenyl)pyridine 1-oxide To a solution of 4-(1-(1-(5-(3-chloro-2-fluoro-6-(4-(trifluoromethyl)-1H-1,2,3-triazol-1-yl)phenyl)pyridin-2-yl)-3-(difluoromethoxy)propyl)-1H-pyrazol-4-yl)-2-fluorobenzoic acid (130 mg, 0.20 mmol, 1.0 equiv.) in CH₃OH (5 mL) was added hydrogen peroxide (30 wt %, 181 mg, 1.07 mmol, 5.0 equiv.) and methylrhenium (VII) trioxide (5 mg, 0.02 mmol, 0.1 equiv.). The reaction mixture was stirred for 2.0 h at room temperature, then purified by reverse phase chromatography on C18 (80 g, MeCN/H₂O (0.05% CF₃COOH): 0→50%) to yield the a residue, which was purified by Prep-Chiral-HPLC to yield (R)-2-(1-(4-(4-carboxy-3-fluorophenyl)-1H-pyrazol-1-yl)-3-(difluoromethoxy)propyl)-5-(3-chloro-2-fluoro-6-(4-(trifluoromethyl)-1H-1,2,3-triazol-1-yl)phenyl)pyridine 1-oxide as a white solid.

LC/MS: mass calculated for $C_{28}H_{18}ClF_7N_8O_4$: 670.10, measured (ES, m/z): 671.10 [M+H]⁺. ¹H NMR (400 MHz, CD₃OD) δ 8.78 (d, J=1.0 Hz, 1H), 8.34-8.40 (m, 2H), 8.08 (s, 1H), 7.85-7.97 (m, 2H), 7.57-7.68 (m, 1H), 7.39-7.50 (m, 3H), 7.23-7.33 (m, 1H), 6.33-6.41 (m, 2H), 3.92-4.01 (m, 1H), 3.64-3.87 (m, 1H), 2.65-2.87 (m, 2H). ¹⁹F NMR (376 MHz, CD₃OD) δ −62.72, −86.13, −111.19, −113.93.

Example 946: (R*)-2-(1-(4-(4-Carbamoyl-3-fluorophenyl)-1H-pyrazol-1-yl)-2-cyclopropylethyl)-5-(3-chloro-2-fluoro-6-(4-(trifluoromethyl)-1H-1,2,3-triazol-1-yl)phenyl)pyridine 1-oxide

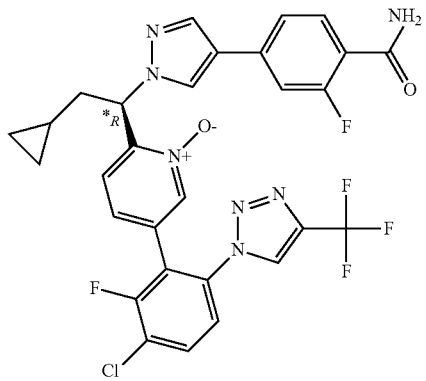 [SMILES: NC(=O)c1ccc(-c2cnn([C@H](CC3CC3)c3ccc(-c4c(-n5cc(C(F)(F)F)nn5)ccc(Cl)c4F)c[n+]3[O-])c2)cc1F]

LC/MS: mass calculated for $C_{29}H_{21}ClF_5N_7O_2$: 629.14, measured (ES, m/z): 630.15 [M+H]⁺. ¹H NMR (300 MHz, DMSO-d₆) δ 9.18 (d, J=1.1 Hz, 1H), 8.65 (s, 1H), 8.40 (s, 1H), 8.13 (s, 1H), 8.06 (dd, J=8.7, 7.8 Hz, 1H), 7.77 (dd, J=8.8, 1.5 Hz, 1H), 7.68 (t, J=8.0 Hz, 1H), 7.58-7.63 (m, 2H), 7.50-7.56 (m, 2H), 7.30 (d, J=8.3 Hz, 1H), 7.14 (dd, J=8.3, 1.6 Hz, 1H), 6.08-6.13 (m, 1H), 2.28-2.50 (m, 1H), 1.89-1.96 (m, 1H), 0.51-0.69 (m, 1H), 0.28-0.42 (m, 2H), 0.05-0.15 (m, 1H), −0.05-0.03 (m, 1H). ¹⁹F NMR (282 MHz, DMSO-d₆) δ: −59.77, −112.93, −113.01.

Example 947: (S*)-2-(1-(4-(4-Carbamoyl-3-fluorophenyl)-1H-pyrazol-1-yl)-2-cyclopropylethyl)-5-(3-chloro-2-fluoro-6-(4-(trifluoromethyl)-1H-1,2,3-triazol-1-yl)phenyl)pyridine 1-oxide

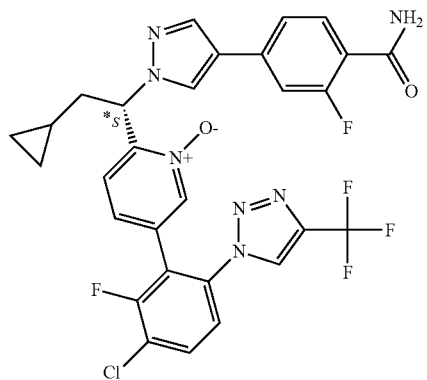 [SMILES: NC(=O)c1ccc(-c2cnn([C@@H](CC3CC3)c3ccc(-c4c(-n5cc(C(F)(F)F)nn5)ccc(Cl)c4F)c[n+]3[O-])c2)cc1F]

LC/MS: mass calculated for $C_{29}H_{21}ClF_5N_7O_2$: 629.14, measured (ES, m/z): 630.15 [M+H]⁺. ¹H NMR (300 MHz, DMSO-d₆) δ 9.16 (d, J=1.1 Hz, 1H), 8.64 (s, 1H), 8.39 (s, 1H), 8.12 (s, 1H), 8.05 (dd, J=8.7, 7.8 Hz, 1H), 7.76 (dd, J=8.7, 1.5 Hz, 1H), 7.68 (t, J=8.0 Hz, 1H), 7.47-7.62 (m, 4H), 7.29 (d, J=8.3 Hz, 1H), 7.13 (dd, J=8.2, 1.7 Hz, 1H), 6.06-6.11 (m, 1H), 2.30-2.50 (m, 1H), 1.86-1.93 (m, 1H), 0.57-0.69 (m, 1H), 0.27-0.35 (m, 2H), 0.04-0.15 (m, 1H), −0.06-0.03 (m, 1H). ¹⁹F NMR (282 MHz, DMSO-d₆) δ −59.77, −112.93, −113.01.

Example 948: 2-(1-(4-(4-Carboxy-3-fluorophenyl)-1H-pyrazol-1-yl)-3-methoxy-3-oxopropyl)-5-(3-chloro-2-fluoro-6-(4-(trifluoromethyl)-1H-1,2,3-triazol-1-yl)phenyl)pyridine 1-oxide

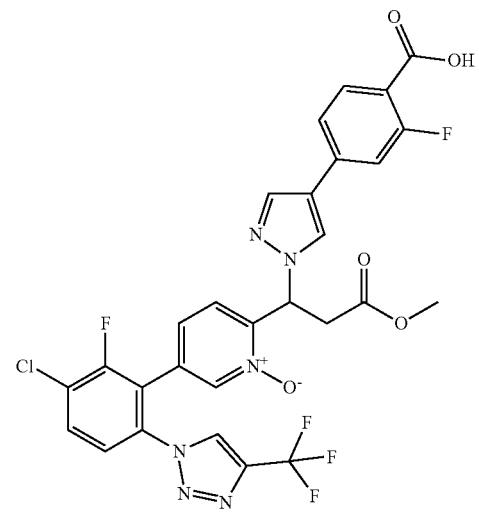 [SMILES: COC(=O)CC(c1ccc(-c2c(-n3cc(C(F)(F)F)nn3)ccc(Cl)c2F)c[n+]1[O-])n1cc(-c2ccc(C(=O)O)c(F)c2)cn1]

Step 1: 4-(1-(1-(5-(3-Chloro-2-fluoro-6-(4-(trifluoromethyl)-1H-1,2,3-triazol-1-yl)phenyl)pyridin-2-yl)-3-methoxy-3-oxopropyl)-1H-pyrazol-4-yl)-2-fluorobenzoic acid To a solution of tert-butyl 4-(1-(1-(5-(3-chloro-2-fluoro-6-(4-(trifluoromethyl)-1H-1,2,3-triazol-1-yl)phenyl)pyridin-2-yl)-2-cyanoethyl)-1H-pyrazol-4-yl)-2-fluorobenzoate (0.125 g, 0.191 mmole) in DCM (2 mL) was added TFA (0.5 mL). The reaction was stirred at room temperature for 2 hours. The solvent was removed to yield a mixture of 4-(1-(1-(5-(3-chloro-2-fluoro-6-(4-(trifluoromethyl)-1H-1,2,3-triazol-1-yl)phenyl)pyridin-2-yl)-3-methoxy-3-oxopropyl)-1H-pyrazol-4-yl)-2-fluorobenzoic acid as a gummy solid which was used as is in the next reaction without purification.

Step 2: 2-(1-(4-(4-Carboxy-3-fluorophenyl)-1H-pyrazol-1-yl)-3-methoxy-3-oxopropyl)-5-(3-chloro-2-fluoro-6-(4-(trifluoromethyl)-1H-1,2,3-triazol-1-yl)phenyl)pyridine 1-oxide To the gummy solid solution in $CH_3OH$, methyl trioxorhenium (VII) (24 mg, 0.0948 mmole), and 30% hydrogen peroxide (0.147 mL, 1.422 mmole) were added. The reaction mixture was stirred at room temperature for 1.5 hour. The solid was filtered and washed with DCM. The organic solvent was removed under vacuum. The residue was purified via reverse phase column chromatography with 0.1% TFA in water and 0.1% TFA in acetonitrile as eluent (20% to 55% 0.1% TFA in ACN gradient) to yield 2-(1-(4-(4-carboxy-3-fluorophenyl)-1H-pyrazol-1-yl)-3-methoxy-3-oxopropyl)-5-(3-chloro-2-fluoro-6-(4-(trifluoromethyl)-1H-1,2,3-triazol-1-yl)phenyl)pyridine 1-oxide as a white solid. LC-MS: calculated mass for $C_{28}H_{18}ClF_5N_8O_5$: 648.1, measured (ES, m/z): 649.2 [M+H]$^+$. $^1$H NMR (DMSO-d$_6$, 400 MHz) 5-13.12 (bs, 1H), 9.17 (s, 1H), 8.64 (s, 1H), 8.46 (bs, 1H), 8.18 (s, 1H), 8.06 (t, J=7.8 Hz, 1H), 7.85 (t, J=7.8 Hz, 1H), 7.77 (dd, JJ=8.6, 1.2 Hz, 1H), 7.61-7.56 (m, 1H), 7.53 (dd, JJ=8.3, 1.5 Hz, 1H), 7.14 (dd, JJ=8.3, 1.5 Hz, 1H), 7.03 (d, J=8.3 Hz, 1H), 6.38 (t, J=7.1 Hz, 1H), 3.57 (s, 3H), 3.44-3.39 (m, 2H). $^{19}$F NMR (DMSO-d$_6$, 377 MHz) 5--125.2 (s), -122.3 (s), -85.8 (s).

Example 949: (S*)-2-(1-(4-(4-Carbamoyl-3-fluorophenyl)-1H-pyrazol-1-yl)-2-(1-(difluoromethyl)-1H-pyrazol-3-yl)ethyl)-5-(3-Chloro-2-fluoro-6-(4-(trifluoromethyl)-1H-1,2,3-triazol-1-yl)phenyl)pyridine 1-oxide

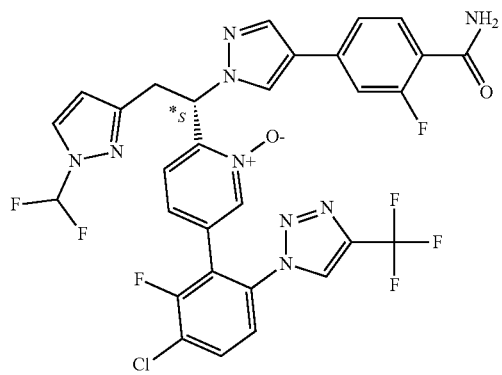 [SMILES: NC(=O)c1ccc(-c2cnn([C@@H](Cc3ccn(C(F)F)n3)c3ccc(-c4c(-n5cc(C(F)(F)F)nn5)ccc(Cl)c4F)c[n+]3[O-])c2)cc1F]

LC/MS: mass calculated for $C_{30}H_{19}ClF_7N_9O_2$: 705.12, measured (ES, m/z): 706.10 [M+H]$^+$. $^1$H NMR (300 MHz, DMSO-d$_6$) δ 9.19 (d, J=1.0 Hz, 1H), 8.57 (s, 1H), 8.46 (s, 1H), 8.13 (s, 1H), 8.02-8.07 (m, 2H), 7.89 (t, J=60.0 Hz 1H), 7.77 (dd, J=8.7, 1.5 Hz, 1H), 7.63-7.69 (m, 1H), 7.56-7.62 (m, 2H), 7.45-7.54 (m, 2H), 7.34 (d, J=8.3 Hz, 1H), 7.15-7.19 (m, 1H), 6.34-6.42 (m, 1H), 6.12 (d, J=2.6 Hz, 1H), 3.54-3.78 (m, 2H). $^{19}$F NMR (282 MHz, DMSO) δ -59.74, -93.85, -112.83.

Example 950: (R)-2-(1-(4-(4-Carbamoyl-3-fluorophenyl)-1H-pyrazol-1-yl)-2-(1-(difluoromethyl)-1H-pyrazol-3-yl)ethyl)-5-(3-chloro-2-fluoro-6-(4-(trifluoromethyl)-1H-1,2,3-triazol-1-yl)phenyl)pyridine 1-oxide

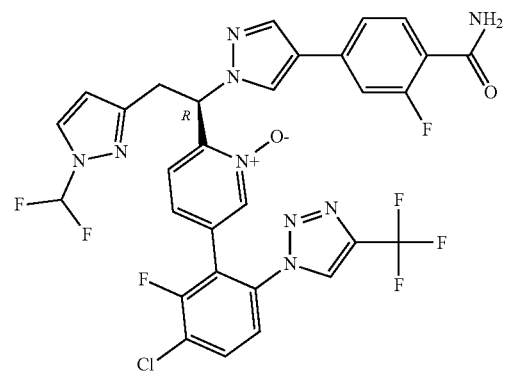

Step 1: tert-Butyl 4-(1-(1-(5-bromopyridin-2-yl)-2-(1-(difluoromethyl)-1H-pyrazol-3-yl)ethyl)-1H-pyrazol-4-yl)-2-fluorobenzoate To a solution of tert-butyl 4-(1-((5-bromopyridin-2-yl)methyl)-1H-pyrazol-4-yl)-2-fluorobenzoate (3.0 g, 6.9 mmol, 1.0 equiv.) in THF (50 mL) was added LiHMDS (1 M in THF, 8.3 mL, 8.28 mmol, 1.2 equiv.) under $N_2$ at -70° C. After the mixture was stirred for 30 min, 3-(bromomethyl)-1-(difluoromethyl)-1H-pyrazole (2.2 g, 10.4 mmol, 1.5 equiv.) was added. The reaction mixture was stirred for 2 h at -70° C., then quenched with $NH_4Cl$ (aq.), extracted with EA twice. The combined organic layers were washed with brine, dried over $Na_2SO_4$, and concentrated under vacuum. The residue was purified by silica gel chromatography (0→50% EA/PE) to yield tert-butyl 4-(1-(1-(5-bromopyridin-2-yl)-2-(1-(difluoromethyl)-1H-pyrazol-3-yl)ethyl)-1H-pyrazol-4-yl)-2-fluorobenzoate as a light yellow solid. LC/MS: mass calculated for $C_{25}H_{23}BrF_3N_5O_2$: 561.10, measured (ES, m/z): 562.00, 564.00 [M+H, M+H+2]$^+$.

Step 2: 4-(1-(1-(5-Bromopyridin-2-yl)-2-(1-(difluoromethyl)-1H-pyrazol-3-yl)ethyl)-1H-pyrazol-4-yl)-2-fluorobenzoic acid To a solution of tert-butyl 4-(1-(1-(5-bromopyridin-2-yl)-2-(1-(difluoromethyl)-1H-pyrazol-3-yl)ethyl)-1H-pyrazol-4-yl)-2-fluorobenzoate (2.2 g, 3.9 mmol, 1.0 equiv.) in DCM (30 mL) was added TFA (10 mL). The reaction mixture was stirred for 2 hours at room temperature, then concentrated under vacuum to yield 4-(1-(1-(5-bromopyridin-2-yl)-2-(1-(difluoromethyl)-1H-pyrazol-3-yl)ethyl)-1H-pyrazol-4-yl)-

2-fluorobenzoic acid as a light yellow solid. LC/MS: mass calculated for $C_{21}H_{15}BrF_3N_5O_2$: 505.04, measured (ES, m/z): 506.15, 508.15 [M+H, M+H+2]⁺.

Step 3: 4-(1-(1-(5-Bromopyridin-2-yl)-2-(1-(difluoromethyl)-1H-pyrazol-3-yl)ethyl)-1H-pyrazol-4-yl)-2-fluorobenzamide To a solution of 4-(1-(1-(5-bromopyridin-2-yl)-2-(1-(difluoromethyl)-1H-pyrazol-3-yl)ethyl)-1H-pyrazol-4-yl)-2-fluorobenzoic acid (2.1 g, resulting) in DMF (30 mL) was added HATU (3.2 g, 8.3 mmol, 2.0 equiv.), DIEA (2.7 g, 20.7 mmol, 5.0 equiv.) and ammonium chloride (1.9 g, 20.7 mmol, 5.0 equiv.). The reaction mixture was stirred for 2 hours at room temperature, then quenched with water, extracted with EA twice. The combined organic layers were washed with brine, dried over $Na_2SO_4$, and concentrated under vacuum. The residue was purified by silica gel chromatography (0→8% MeOH/DCM) to yield 4-(1-(1-(5-bromopyridin-2-yl)-2-(1-(difluoromethyl)-1H-pyrazol-3-yl)ethyl)-1H-pyrazol-4-yl)-2-fluorobenzamide as a white solid. LC/MS: mass calculated for $C_{21}H_{16}BrF_3N_6O$: 504.05, measured (ES, m/z): 505.15, 507.15 [M+H, M+H+2]⁺.

Step 4: (6-(1-(4-(4-Carbamoyl-3-fluorophenyl)-1H-pyrazol-1-yl)-2-(1-(difluoromethyl)-1H-pyrazol-3-yl)ethyl)pyridin-3-yl)boronic acid To a solution of 4-(1-(1-(5-bromopyridin-2-yl)-2-(1-(difluoromethyl)-1H-pyrazol-3-yl)ethyl)-1H-pyrazol-4-yl)-2-fluorobenzamide (4.5 g, 8.9 mmol, 1.0 equiv.) in 1,4-dioxane (80 mL) was added 4,4,4',4',5,5,5',5'-octamethyl-2,2'-bi(1,3,2-dioxaborolane) (4.5 g, 17.8 mmol, 2.0 equiv.), potassium acetate (2.6 g, 26.7 mmol, 3.0 equiv.) and Pd(dppf)Cl₂·CH₂Cl₂ (0.73 g, 0.89 mmol, 0.1 equiv.) under $N_2$. The reaction mixture was stirred for 2 h at 90° C., then cooled to room temperature. and quenched with water, extracted with EA twice. The combined organic layers were washed with brine, dried over $Na_2SO_4$ and concentrated under vacuum to yield (6-(1-(4-(4-carbamoyl-3-fluorophenyl)-1H-pyrazol-1-yl)-2-(1-(difluoromethyl)-1H-pyrazol-3-yl)ethyl)pyridin-3-yl)boronic acid as black oil. LC/MS: mass calculated for $C_{21}H_{18}BF_3N_8O_3$: 470.15, measured (ES, m/z): 471.10 [M+H]⁺.

Step 5: 4-(1-(1-(5-(3-Chloro-2-fluoro-6-(4-(trifluoromethyl)-1H-1,2,3-triazol-1-yl) phenyl)pyridin-2-yl)-2-(1-(difluoromethyl)-1H-pyrazol-3-yl)ethyl)-1H-pyrazol-4-yl)-2-fluorobenzamide To a solution of 1-(4-chloro-3-fluoro-2-iodophenyl)-4-(trifluoromethyl)-1H-1,2,3-triazole (2.8 g, 7.2 mmol, 1.0 equiv.) and (6-(1-(4-(4-carbamoyl-3-fluorophenyl)-1H-pyrazol-1-yl)-2-(1-(difluoromethyl)-1H-pyrazol-3-yl)ethyl)pyridin-3-yl)boronic acid (7.4 g, resulting) in 1,4-dioxane (100 mL) and water (20 mL) was added potassium carbonate (3.0 g, 21.5 mmol, 3.0 equiv.) and Pd(PPh₃)₄ (0.83 g, 0.72 mmol, 0.1 equiv.) under $N_2$. The reaction mixture was stirred overnight at 90° C., then quenched with water, extracted with EA twice. The combined organic layers were dried over $Na_2SO_4$ and concentrated under vacuum. The residue was purified by silica gel chromatography (0→100% EA/PE) to yield 4-(1-(1-(5-(3-chloro-2-fluoro-6-(4-(trifluoromethyl)-1H-1,2,3-triazol-1-yl)phenyl)pyridin-2-yl)-2-(1-(difluoromethyl)-1H-pyrazol-3-yl)ethyl)-1H-pyrazol-4-yl)-2-fluorobenzamide as a light yellow solid. LC/MS: mass calculated for $C_{30}H_{19}ClF_6N_8O_2$: 672.12, measured (ES, m/z): 673.15 [M+H]⁺.

Step 6: (R)-2-(1-(4-(4-carbamoyl-3-fluorophenyl)-1H-pyrazol-1-yl)-2-(1-(difluoromethyl)-1H-pyrazol-3-yl)ethyl)-5-(3-chloro-2-fluoro-6-(4-(trifluoromethyl)-1H-1,2,3-triazol-1-yl)phenyl)pyridine 1-oxide To a solution of 4-(1-(1-(5-(3-chloro-2-fluoro-6-(4-(trifluoromethyl)-1H-1,2,3-triazol-1-yl)phenyl)pyridin-2-yl)-2-(1-(difluoromethyl)-1H-pyrazol-3-yl)ethyl)-1H-pyrazol-4-yl)-2-fluorobenzamide (1.1 g, 1.6 mmol, 1.0 equiv.) in $CH_3OH$ (15 mL) was added hydrogen peroxide solution (30 wt %, 1.8 g, 15.9 mmol, 10.0 equiv.) followed by the addition of methyl trioxorhenium (0.2 g, 0.8 mmol, 0.5 equiv.). The reaction mixture was stirred for 5 h at room temperature, then purified by reverse column chromatography on C18 (5→50%, MeCN/H₂O) to yield the resulting residue, which was purified by Prep-Chiral-HPLC with MtBE (0.1% DEA):EtOH=90:10 to yield (R)-2-(1-(4-(4-carbamoyl-3-fluorophenyl)-1H-pyrazol-1-yl)-2-(1-(difluoromethyl)-1H-pyrazol-3-yl)ethyl)-5-(3-chloro-2-fluoro-6-(4-(trifluoromethyl)-1H-1,2,3-triazol-1-yl)phenyl)pyridine 1-oxide as a white solid.

LC/MS: mass calculated for $C_{30}H_{19}ClF_7N_9O_2$: 705.12, measured (ES, m/z): 706.10 [M+H]⁺. ¹H NMR (400 MHz, DMSO-d₆): δ 9.18 (d, J=1.0 Hz, 1H), 8.56 (s, 1H), 8.45 (d, J=1.6 Hz, 1H), 8.13 (s, 1H), 8.01-8.10 (m, 2H), 7.44-7.86 (m, 7H), 7.33 (d, J=8.3 Hz, 1H), 7.12-7.20 (m, 1H), 6.34-6.41 (m, 1H), 6.11 (d, J=2.6 Hz, 1H), 3.54-3.70 (m, 2H). ¹⁹F-NMR (376 MHz, DMSO-d₆): δ −59.74, −93.85, −113.00, −113.04.

Example 951: (R*)-2-(1-(4-(4-Carbamoyl-3-fluorophenyl)-1H-pyrazol-1-yl)-2-(1-(difluoromethyl)-1H-pyrazol-3-yl)ethyl)-5-(3-chloro-6-(4-chloro-1H-1,2,3-triazol-1-yl)-2-fluorophenyl)pyridine 1-oxide

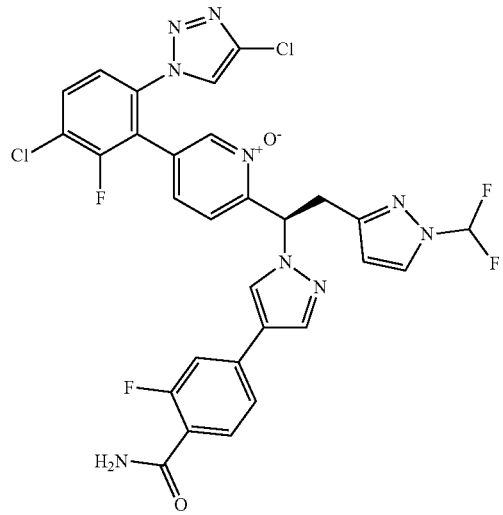

Step 1: (5-Bromopyridin-2-yl)methyl methanesulfonate

A mixture of (5-bromopyridin-2-yl)CH₃OH (2.0 g, 10.64 mmol, 1.0 equiv.) and triethylamine (1.5 mL, 10.6 mmol, 1.0 equiv.) in DCM (20 mL) was stirred for 5 min at 0° C. Then methanesulfonic anhydride (2.8 g, 15.96 mmol, 1.5 equiv.) was added the mixture solution at 0° C. and the solution was stirred for 1 h at room temperature. The mixture was added $H_2O$, extracted with DCM twice. The combined organic layers was washed with brine, dried over $Na_2SO_4$, concentrated under vacuum to yield (5-bromopyridin-2-yl)methyl methanesulfonate as a red solid. LC/MS: mass calculated for $C_7H_8BrNO_3S$: 264.94, measured (ES, m/z):266.00, 267.90 [M+H, M+H+2]$^+$.

Step 2: tert-Butyl-4-(1-((5-bromopyridin-2-yl) methyl)-1H-pyrazol-4-yl)-2-fluorobenzoate A mixture of tert-butyl 2-fluoro-4-(1H-pyrazol-4-yl)benzoate (500 mg, 1.91 mmol, 1.0 equiv.) and cesium carbonate (621 mg, 1.91 mmol, 1.0 equiv.) in acetonitrile (5 mL) was stirred at room temperature for 10 minutes. Then (5-bromopyridin-2-yl) methyl methanesulfonate (659 mg, 2.48 mmol, 1.3 equiv.) was added the reaction mixture and the solution was stirred at 90° C. overnight. The mixture was added $H_2O$, extracted with EA three times. The combined organic layers was washed with brine, dried over $Na_2SO_4$, concentrated and purified by silica gel chromatography (0→60% EA/PE) to yield tert-butyl 4-(1-((5-bromopyridin-2-yl)methyl)-1H-pyrazol-4-yl)-2-fluorobenzoate as a yellow solid. LC/MS: mass calculated for $C_{20}H_{19}BrFN_3O_2$: 431.06, measured (ES, m/z): 432.05, 433.95 [M+H, M+H+2]$^+$.

Step 3: tert-Butyl 4-(1-(1-(5-bromopyridin-2-yl)-2-(1-(difluoromethyl)-1H-pyrazol-3-yl)ethyl)-1H-pyrazol-4-yl)-2-fluorobenzoate To a solution of tert-butyl 4-(1-((5-bromopyridin-2-yl) methyl)-1H-pyrazol-4-yl)-2-fluorobenzoate (500 mg, 1.20 mmol, 1.0 equiv.) in tetrahydrofuran (8 mL) under nitrogen was added lithium bis(trimethylsilyl)amide (1.44 mL, 1.44 mmol, 1.0 M in THF, 1.2 equiv.) in portions at −70° C. and the solution was stirred for 30 min at this temperature. 3-(Bromomethyl)-1-(difluoromethyl)-1H-pyrazole (254 mg, 1.20 mmol, 1.0 equiv.) in tetrahydrofuran (2 mL) under nitrogen was added the solution. The reaction mixture was stirred at −70° C. for 1 h. The reaction was quenched with sat. $NH_4Cl$ (aq.) and extracted with ethyl acetate twice. The combined organic layer was washed with brine, dried over $Na_2SO_4$ and concentrated. The residue was purified by silica gel chromatography (0→50% EtOAc/petroleum ether) to yield tert-butyl 4-(1-(1-(5-bromopyridin-2-yl)-2-(1-(difluoromethyl)-1H-pyrazol-3-yl)ethyl)-1H-pyrazol-4-yl)-2-fluorobenzoate as a light yellow oil. LC/MS: mass calculated for $C_{25}H_{23}BrF_3N_5O_2$: 561.10, measured (ES, m/z): 562.10, 564.00 [M+H, M+H+2]$^+$.

Step 4: 4-(1-(1-(5-Bromopyridin-2-yl)-2-(1-(difluoromethyl)-1H-pyrazol-3-yl)ethyl)-1H-pyrazol-4-yl)-2-fluorobenzoic acid A mixture of tert-butyl 4-(1-(1-(5-bromopyridin-2-yl)-2-(1-(difluoromethyl)-1H-pyrazol-3-yl) ethyl)-1H-pyrazol-4-yl)-2-fluorobenzoate (500 mg, 0.89 mmol, 1.0 equiv.) in dichloromethane (5 mL) was added 2, 2, 2-trifluoroacetic acid (2 mL) was stirred for 1 h. The reaction was concentrated under vacuum to yield 4-(1-(1-(5-bromopyridin-2-yl)-2-(1-(difluoromethyl)-1H-pyrazol-3-yl) ethyl)-1H-pyrazol-4-yl)-2-fluorobenzoic acid as a yellow oil. LC/MS: mass calculated for $C_{21}H_{15}BrF_3N_5O_2$: 505.04, measured (ES, m/z): 506.15, 508.15 [M+H, M+H+2]$^+$.

Step 5: 4-(1-(1-(5-Bromopyridin-2-yl)-2-(1-(difluoromethyl)-1H-pyrazol-3-yl)ethyl)-1H-pyrazol-4-yl)-2-fluorobenzamide A mixture of 4-(1-(1-(5-bromopyridin-2-yl)-2-(1-(difluoromethyl)-1H-pyrazol-3-yl)ethyl)-1H-pyrazol-4-yl)-2-fluorobenzoic acid (1.0 g, 1.98 mmol, 1.0 equiv.) and HATU (1.5 g, 3.95 mmol, 2.0 equiv.) in N,N-dimethylformamide (10 mL) was added N,N-Diisopropylethylamine (1.3 mL, 7.90 mmol, 4.0 equiv.) and ammonium chloride (211 mg, 3.95 mmol, 2.0 equiv.). The solution was stirred at room temperature for 1 h.

Water was added, the mixture was extracted with EA. The combined organic layers were washed with brine, dried over $Na_2SO_4$ and concentrated under vacuum. The resulting residue was purified by reverse phase chromatography on C18 (80 g, ACN/$H_2O$ (0.05% $CF_3COOH$): 0→40%) to yield 4-(1-(1-(5-bromopyridin-2-yl)-2-(1-(difluoromethyl)-1H-pyrazol-3-yl)ethyl)-1H-pyrazol-4-yl)-2-fluorobenzamide as white solid. LC/MS: mass calculated for $C_{21}H_{16}BrF_3N_6O$: 504.05, measured (ES, m/z): 505.15, 507.15 [M+H, M+H+2]$^+$.

Step 6: (6-(1-(4-(4-Carbamoyl-3-fluorophenyl)-1H-pyrazol-1-yl)-2-(1-(difluoromethyl)-1H-pyrazol-3-yl)ethyl)pyridin-3-yl)boronic acid A mixture of 4-(1-(1-(5-bromopyridin-2-yl)-2-(1-(difluoromethyl)-1H-pyrazol-3-yl)ethyl)-1H-pyrazol-4-yl)-2-fluorobenzamide (200 mg, 0.40 mmol, 1.0 equiv.) and 4,4,4',4',5,5,5',5'-octamethyl-2,2'-bi(1,3,2-dioxaborolane) (302 mg, 1.18 mmol, 3.0 equiv.) in 1,4-dioxane (5 mL) was added potassium acetate (155 mg, 1.58 mmol, 4.0 equiv.) and Pd(dppf)$Cl_2$ (58 mg, 0.08 mmol, 0.2 equiv.) under $N_2$. The flask was evacuated, then purged with nitrogen. This was repeated 2×. The solution was stirred at 90° C. for 2 h. The mixture was added $H_2O$, extracted with EA twice. The combined organic layers was washed with brine, dried over $Na_2SO_4$, concentrated to yield (6-(1-(4-(4-carbamoyl-3-fluorophenyl)-1H-pyrazol-1-yl)-2-(1-(difluoromethyl)-1H-pyrazol-3-yl) ethyl) pyridin-3-yl)boronic acid as brown oil. LC/MS: mass calculated for $C_{21}H_{18}BF_3N_6O_3$: 470.15, measured (ES, m/z): 471.10 [M+H]$^+$ Step 7: 4-(1-(1-(5-(3-Chloro-6-(4-chloro-1H-1,2,3-triazol-1-yl)-2-fluorophenyl)pyridin-2-yl)-2-(1-(difluoromethyl)-1H-pyrazol-3-yl)ethyl)-1H-pyrazol-4-yl)-2-fluorobenzamide To a mixture of (6-(1-(4-(4-carbamoyl-3-fluorophenyl)-1H-pyrazol-1-yl)-2-(1-(difluoromethyl)-1H-pyrazol-3-yl) ethyl)pyridin-3-yl)boronic acid (180 mg, 0.38 mmol, 1.0 equiv.), potassium carbonate (212 mg, 1.53 mmol, 3.0 equiv.) and 4-chloro-1-(4-chloro-3-fluoro-2-iodophenyl)-1H-1,2,3-triazole (206 mg, 0.57 mmol, 1.5 equiv.) in the mixed solution 1,4-dioxane (4 mL) and water (1 mL) was added tetrakis(triphenylphosphine)palladium(0) (44 mg, 0.04 mmol, 0.1 equiv.) under $N_2$. The solution was stirred for at 100° C. for 2 h. Water was added and the mixture was extracted with EA. The combined organic layers were washed with brine, dried over $Na_2SO_4$ and concentrated and purified by silica gel chromatography (0→10% $CH_3OH$/DCM) to yield 4-(1-(1-(5-(3-chloro-6-(4-chloro-1H-1,2,3-triazol-1-yl)-2-fluorophenyl)pyridin-2-yl)-2-(1-(difluoromethyl)-1H-pyrazol-3-yl)ethyl)-1H-pyrazol-4-yl)-2-fluorobenzamide as a yellow solid. LC/MS: mass calculated for $C_{29}H_{19}Cl_2F_4N_9O$: 655.10, measured (ES, m/z): 656.05 $[M+H]^+$ Step 8: (R*)-2-(1-(4-(4-Carbamoyl-3-fluorophenyl)-1H-pyrazol-1-yl)-2-(1-(difluoromethyl)-1H-pyrazol-3-yl)ethyl)-5-(3-chloro-6-(4-chloro-1H-1,2,3-triazol-1-yl)-2-fluorophenyl)pyridine 1-oxide A solution of 4-(1-(1-(5-(3-chloro-6-(4-chloro-1H-1,2,3-triazol-1-yl)-2-fluorophenyl)pyridin-2-yl)-2-(1-(difluoromethyl)-1H-pyrazol-3-yl)ethyl)-1H-pyrazol-4-yl)-2-fluorobenzamide (180 mg, 0.27 mmol, 1.0 equiv) and methyltrioxorhenium (VII) (13.7 mg, 0.06 mmol, 0.2 equiv.) in $CH_3OH$ (3 mL) was added hydrogen peroxide (0.3 mL, 2.74 mmol, 10.0 equiv.). The reaction mixture was stirred at room temperature for 4 h. The reaction mixture was purified by reverse phase chromatography on C18 (120 g, $ACN/H_2O$ (0.05% $CF_3COOH$): 0→35%). The resulting residue was purified by Prep-Chiral-HPLC to yield (R*)-2-(1-(4-(4-carbamoyl-3-fluorophenyl)-1H-pyrazol-1-yl)-2-(1-(difluoromethyl)-1H-pyrazol-3-yl)ethyl)-5-(3-chloro-6-(4-chloro-1H-1,2,3-triazol-1-yl)-2-fluorophenyl)pyridine 1-oxide as a white solid.

LC/MS: mass calculated for $C_{29}H_{19}Cl_2F_4N_9O_2$: 671.10, measured (ES, m/z): 672.05 $[M+H]^+$. $^1H$ NMR (300 MHz, DMSO-$d_6$): b 8.68 (s, 1H), 8.57 (s, 1H), 8.44 (s, 1H), 8.14 (s, 1H), 7.95-8.06 (m, 2H), 7.60-7.90 (m, 3H), 7.40-7.60 (m, 4H), 7.33 (d, J=8.3 Hz, 1H), 7.17 (d, J=8.4 Hz, 1H), 6.28-6.45 (m, 1H), 6.09 (d, J=2.7 Hz, 1H), 3.60-3.70 (m, 2H). $^{19}F$ NMR (282 MHz, DMSO-$d_6$): b -93.80, -112.92.

Example 952: (R)-2-(1-(4-(4-Carbamoyl-3-fluorophenyl)-1H-pyrazol-1-yl)-2-(1-(difluoromethyl)-1H-pyrazol-3-yl)ethyl)-5-(3-chloro-6-(4-chloro-1H-1,2,3-triazol-1-yl)-2-fluorophenyl)pyridine 1-oxide

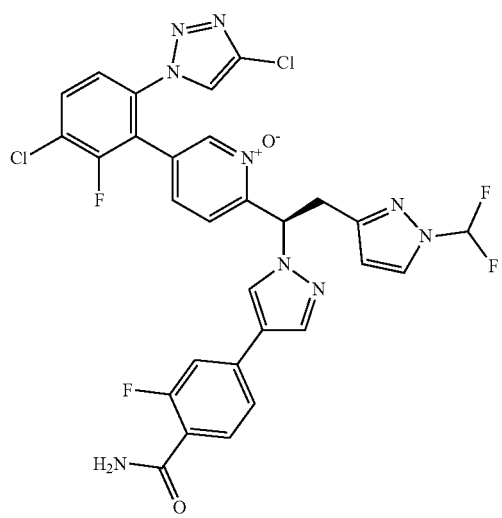

Step 1: (5-Bromopyridin-2-yl)methyl methanesulfonate

A mixture of (5-bromopyridin-2-yl)methanol (2.0 g, 10.64 mmol, 1.0 equiv.) and triethylamine (1.48 mL, 10.64 mmol, 1.0 equiv.) in DCM (20 mL) was stirred for 5 min at 0° C. Then methanesulfonic anhydride (2.78 g, 15.96 mmol, 1.5 equiv.) was added the mixture solution at 0° C. and the solution was stirred for 1 h at room temperature. The mixture was added $H_2O$, extracted with DCM twice. The combined organic layer was washed with brine, dried over $Na_2SO_4$, concentrated under vacuum to yield (5-bromopyridin-2-yl) methyl methanesulfonate as a red solid. LC/MS: mass calculated for $C_7H_8BrNO_3S$: 264.94, measured (ES, m/z): 265.90, 267.90 $[M+H, M+H+2]^+$.

Step 2: tert-Butyl 4-(1-((5-bromopyridin-2-yl)methyl)-1H-pyrazol-4-yl)-2-fluorobenzoate A mixture of tert-butyl 2-fluoro-4-(1H-pyrazol-4-yl)benzoate (500 mg, 1.91 mmol, 1.0 equiv.) and cesium carbonate (621 mg, 1.91 mmol, 1.0 equiv.) in acetonitrile (5 mL) was stirred at room temperature for 10 minutes. Then (5-bromopyridin-2-yl) methyl methanesulfonate (659 mg, 2.48 mmol, 1.3 equiv.) was added the reaction mixture and the solution was stirred at 90° C. overnight. The mixture was added $H_2O$, extracted with EA three times. The combined organic layer was washed with brine, dried over $Na_2SO_4$, concentrated and purified by silica gel chromatography (0→60% EA:PE) to yield tert-butyl 4-(1-((5-bromopyridin-2-yl)methyl)-1H-pyrazol-4-yl)-2-fluorobenzoate as a yellow solid. LC/MS: mass calculated for $C_{20}H_1BrFN_3O_2$: 431.06, measured (ES, m/z): 432.05, 435.05 $[M+H, M+H+2]^+$.

Step 3: tert-Butyl 4-(1-(1-(5-bromopyridin-2-yl)-2-(1-(difluoromethyl)-1H-pyrazol-3-yl)ethyl)-1H-pyrazol-4-yl)-2-fluorobenzoate To a solution of tert-butyl 4-(1-((5-bromopyridin-2-yl)methyl)-1H-pyrazol-4-yl)-2-fluorobenzoate (500 mg, 1.20 mmol, 1.0 equiv.) in tetrahydrofuran (8 mL) under nitrogen was added lithium bis(trimethylsilyl)amide (1.44 mL, 1.44 mol, 1.0 M in THF, 1.2 equiv.) in portions at -78° C. and the solution was stirred for 30 min at this temperature. 3-(Bromomethyl)-1-(difluoromethyl)-1H-pyrazole (254 mg, 1.20 mmol, 1.0 equiv.) in tetrahydrofuran (2 mL) under nitrogen was added the solution. The reaction mixture was stirred at -70° C. for 1 h. The reaction was quenched with sat. $NH_4Cl$ (aq.) and extracted with ethyl acetate twice. The combined organic layer was washed with brine, dried over $Na_2SO_4$ and concentrated. The residue was purified by silica gel chromatography (0→50% EtOAc/petroleum ether) to yield tert-butyl 4-(1-(1-(5-bromopyridin-2-yl)-2-(1-(difluoromethyl)-1H-pyrazol-3-yl)ethyl)-1H-pyrazol-4-yl)-2-fluorobenzoate as a light yellow oil. LC/MS: mass calculated for $C_{25}H_{23}BrF_3N_5O_2$: 561.10, measured (ES, m/z): 562.00, 564.00 $[M+H, M+H+2]^+$.

Step 4: 4-(1-(1-(5-Bromopyridin-2-yl)-2-(1-(difluoromethyl)-1H-pyrazol-3-yl) ethyl)-1H-pyrazol-4-yl)-2-fluorobenzoic acid To a mixture of tert-butyl 4-(1-(1-(5-bromopyridin-2-yl)-2-(1-(difluoromethyl)-1H-pyrazol-3-yl) ethyl)-1H-pyrazol-4-yl)-2-fluorobenzoate (500 mg, 0.89 mmol, 1.0 equiv.) in dichloromethane (5 mL) was added 2, 2, 2-trifluoroacetic acid (2 mL) was stirred for 1 h. The reaction was concentrated under vacuum to yield 4-(1-(1-(5-bromopyridin-2-yl)-2-(1-(difluoromethyl)-1H-pyrazol-3-yl) ethyl)-1H-pyrazol-4-yl)-2-fluorobenzoic acid as a yellow oil. LC/MS: mass calculated for $C_{21}H_{15}BrF_3N_5O_2$: 505.04, measured (ES, m/z): 506.15, 508.15 [M+H, M+H+2]$^+$.

Step 5: 4-(1-(1-(5-Bromopyridin-2-yl)-2-(1-(difluoromethyl)-1H-pyrazol-3-yl)ethyl)-1H-pyrazol-4-yl)-2-fluorobenzamide To a mixture of 4-(1-(1-(5-bromopyridin-2-yl)-2-(1-(difluoromethyl)-1H-pyrazol-3-yl)ethyl)-1H-pyrazol-4-yl)-2-fluorobenzoic acid (1.0 g, 1.98 mmol, 1.0 equiv.) and HATU (1.5 g, 3.95 mmol, 2.0 equiv.) in N,N-dimethylformamide (10.0 mL) was added N,N-diisopropylethylamine (1.29 mL, 7.90 mmol, 4.0 equiv.) and ammonium chloride (211 mg, 3.95 mmol, 2.0 equiv.). The solution was stirred at room temperature for 1 h.

Water was added, the mixture was extracted with EA. The combined organic layers were washed with brine, dried over $Na_2SO_4$ and concentrated under vacuum. The resulting residue was purified by reverse phase chromatography on C18 (80 g, ACN/$H_2O$ (0.05% $CF_3COOH$): 0→40%) to yield 4-(1-(1-(5-bromopyridin-2-yl)-2-(1-(difluoromethyl)-1H-pyrazol-3-yl)ethyl)-1H-pyrazol-4-yl)-2-fluorobenzamide as white solid. LC/MS: mass calculated for $C_{21}H_{16}BrF_3N_6O$: 504.05, measured (ES, m/z): 505.15, 507.15 [M+H, M+H+2]$^+$.

Step 6: (6-(1-(4-(4-Carbamoyl-3-fluorophenyl)-1H-pyrazol-1-yl)-2-(1-(difluoromethyl)-1H-pyrazol-3-yl) ethyl) pyridin-3-yl)boronic acid To a mixture of 4-(1-(1-(5-bromopyridin-2-yl)-2-(1-(difluoromethyl)-1H-pyrazol-3-yl)ethyl)-1H-pyrazol-4-yl)-2-fluorobenzamide (200 mg, 0.40 mmol, 1.0 equiv.) and 4,4,4',4',5,5,5',5'-octamethyl-2,2'-bi(1,3,2-dioxaborolane) (302 mg, 1.19 mmol, 3.0 equiv.) in 1,4-dioxane (5 mL) was added potassium acetate (155 mg, 1.6 mmol, 4.0 equiv.) and Pd(dppf)Cl$_2$ (58 mg, 0.08 mmol, 0.2 equiv.) under N$_2$. The flask was evacuated and purged with nitrogen. This was repeated twice. The solution was stirred at 90° C. for 2 h. The mixture was added H$_2$O, extracted with EA twice. The combined organic layers was washed with brine, dried over Na$_2$SO$_4$, concentrated to yield (6-(1-(4-(4-carbamoyl-3-fluorophenyl)-1H-pyrazol-1-yl)-2-(1-(difluoromethyl)-1H-pyrazol-3-yl) ethyl) pyridin-3-yl)boronic acid as brown oil. LC/MS: mass calculated for $C_{21}H_{18}BF_3N_6O_3$: 470.15, measured (ES, m/z): 471.10 [M+H]$^+$.

Step 7: 4-(1-(1-(5-(3-Chloro-6-(4-chloro-1H-1,2,3-triazol-1-yl)-2-fluorophenyl)pyridin-2-yl)-2-(1-(difluoromethyl)-1H-pyrazol-3-yl)ethyl)-1H-pyrazol-4-yl)-2-fluorobenzamide To a mixture of (6-(1-(4-(4-carbamoyl-3-fluorophenyl)-1H-pyrazol-1-yl)-2-(1-(difluoromethyl)-1H-pyrazol-3-yl) ethyl)pyridin-3-yl)boronic acid (180 mg, 0.38 mmol, 1.0 equiv.), potassium carbonate (212 mg, 1.53 mmol, 3.0 equiv.) and 4-chloro-1-(4-chloro-3-fluoro-2-iodophenyl)-1H-1,2,3-triazole (206 mg, 0.57 mmol, 1.5 equiv.) in solution 1,4-dioxane (4 mL) and water (1 mL) was added tetrakis(triphenylphosphine)Palladium(0) (44 mg, 0.04 mmol, 0.1 equiv.). The solution was stirred for at 100° C. for 2 h under N$_2$. Water was added, the mixture was extracted with EA. The combined organic layers were washed with brine, dried over Na$_2$SO$_4$ and concentrated and purified by silica gel chromatography (0→10% CH$_3$OH/DCM) to yield 4-(1-(1-(5-(3-chloro-6-(4-chloro-1H-1,2,3-triazol-1-yl)-2-fluorophenyl)pyridin-2-yl)-2-(1-(difluoromethyl)-1H-pyrazol-3-yl)ethyl)-1H-pyrazol-4-yl)-2-fluorobenzamide as a yellow solid. LC/MS: mass calculated for $C_{29}H_{19}Cl_2F_4N_9O$: 655.10, measured (ES, m/z): 656.05 [M+H]$^+$.

Step 8: (R)-2-(1-(4-(4-Carbamoyl-3-fluorophenyl)-1H-pyrazol-1-yl)-2-(1-(difluoromethyl)-1H-pyrazol-3-yl)ethyl)-5-(3-chloro-6-(4-chloro-1H-1,2,3-triazol-1-yl)-2-fluorophenyl)pyridine 1-oxide To a solution of 4-(1-(1-(5-(3-chloro-6-(4-chloro-1H-1,2,3-triazol-1-yl)-2-fluorophenyl)pyridin-2-yl)-2-(1-(difluoromethyl)-1H-pyrazol-3-yl)ethyl)-1H-pyrazol-4-yl)-2-fluorobenzamide (20 g, 30.47 mmol, 1.0 equiv.) and ReMeO$_3$ (3.8 g, 15.2 mmol, 0.5 equiv.) in CH$_3$OH (200 mL) was added hydrogen peroxide (30.5 mL, 304.7 mmol, 30 wt %, 10.0 equiv.). The reaction mixture was stirred at room temperature for 4 h. The reaction was added water, and the mixture extracted with EA twice. The combined organic layers were washed with brine, dried over Na$_2$SO$_4$, concentrated under vacuum and purified by silica gel chromatography (0→100% EA/PE) to yield a residue which was further purified by Prep-Chiral-HPLC to yield (R)-2-(1-(4-(4-carbamoyl-3-fluorophenyl)-1H-pyrazol-1-yl)-2-(1-(difluoromethyl)-1H-pyrazol-3-yl)ethyl)-5-(3-chloro-6-(4-chloro-1H-1,2,3-triazol-1-yl)-2-fluorophenyl)pyridine 1-oxide as yellow solid.

LC/MS: mass calculated for $C_{29}H_{19}Cl_2F_4N_9O_2$: 671.10, measured (ES, m/z): 672.05 [M+H]$^+$. $^1$H NMR (300 MHz, DMSO-d$_6$) δ 8.68 (s, 1H), 8.58 (s, 1H), 8.44 (s, 1H), 8.14 (s, 1H), 7.97-8.09 (m, 2H), 7.45-7.92 (m, 7H), 7.33-7.38 (m, 1H), 7.18-7.21 (m, 1H), 6.36-6.42 (m, 1H), 6.12 (d, J=2.6 Hz, 1H), 3.57-3.75 (m, 2H). $^{19}$F-NMR (282 MHz, DMSO) δ −93.82, −112.91.

Example 953: (R*)-2-(1-(4-(4-Carbamoylphenyl)-1H-pyrazol-1-yl)-3-(difluoromethoxy)propyl)-5-(3-chloro-6-(4-chloro-1H-1,2,3-triazol-1-yl)-2-fluorophenyl)pyridine 1-oxide

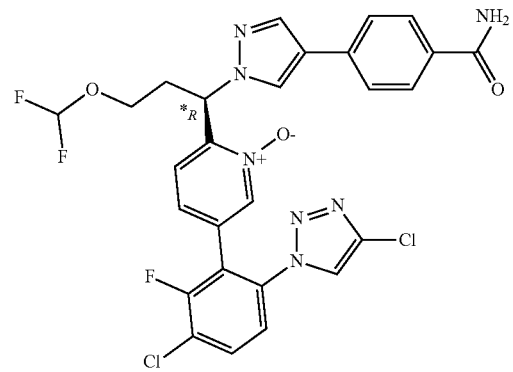 [SMILES: NC(=O)c1ccc(-c2cnn([C@H](CCOC(F)F)c3ccc(-c4c(-n5cc(Cl)nn5)ccc(Cl)c4F)c[n+]3[O-])c2)cc1]

LC/MS: mass calculated for $C_{27}H_{20}Cl_2F_3N_7O_3$: 617.10, measured (ES, m/z): 618.10 [M+H]$^+$. $^1$H NMR (400 MHz, DMSO-d$_6$) δ 8.68 (s, 1H), 8.54 (s, 1H), 8.42 (s, 1H), 8.15 (s, 1H), 8.02 (dd, J=8.7, 7.8 Hz, 1H), 7.96 (s, 1H), 7.86-7.90 (m, 2H), 7.65-7.73 (m, 3H), 7.32 (s, 1H), 7.27 (d, J=8.3 Hz, 1H), 7.17 (dd, J=8.3, 1.7 Hz, 1H), 6.65 (t, J=75.8 Hz, 1H), 6.20 (dd, J=10.0, 4.6 Hz, 1H), 3.81-3.90 (m, 1H), 3.63-3.75 (m, 1H), 2.53-2.70 (m, 2H). $^{19}$F NMR (376 MHz, DMSO-d$_6$) δ −74.70, −83.24, −112.94.

Example 954: (S*)-2-(1-(4-(4-Carbamoylphenyl)-1H-pyrazol-1-yl)-3-(difluoromethoxy)propyl)-5-(3-chloro-6-(4-chloro-1H-1,2,3-triazol-1-yl)-2-fluorophenyl)pyridine 1-oxide

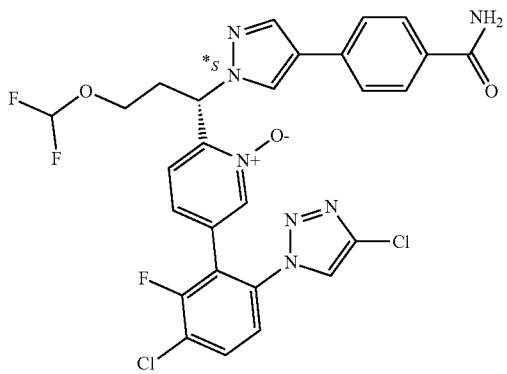 [SMILES: NC(=O)c1ccc(-c2cnn([C@@H](CCOC(F)F)c3ccc(-c4c(-n5cc(Cl)nn5)ccc(Cl)c4F)c[n+]3[O-])c2)cc1]

To a mixture of (S*)-2-(1-(4-(4-carboxyphenyl)-1H-pyrazol-1-yl)-3-(difluoromethoxy)propyl)-5-(3-chloro-6-(4-chloro-1H-1,2,3-triazol-1-yl)-2-fluorophenyl)pyridine 1-oxide (98 mg, 0.16 mmol, 1.0 equiv.), ammonium chloride (42 mg, 0.79 mmol, 5.0 equiv.) and 2-(3H-[1,2,3]triazolo[4,5-b]pyridin-3-yl)-1,1,3,3-tetramethylisouronium (90 mg, 0.24 mmol, 1.5 equiv.) in N,N-dimethylformamide (10 mL) was added N-ethyl-N-isopropylpropan-2-amine (61 mg, 0.47 mmol, 3.0 equiv.). The reaction was stirred at room temperature. for 4 h, then purified by reverse phase chromatography on C18 (120 g, MeCN/H$_2$O (0.05% CF$_3$COOH): 5→60%) to yield (S*)-2-(1-(4-(4-carbamoylphenyl)-1H-pyrazol-1-yl)-3-(difluoromethoxy)propyl)-5-(3-chloro-6-(4-chloro-1H-1,2,3-triazol-1-yl)-2-fluorophenyl)pyridine 1-oxide as white solid.

LC/MS: mass calculated for C$_{27}$H$_{20}$Cl$_2$F$_3$N$_7$O$_3$: 617.10, measured (ES, m/z): 618.10 [M+H]$^+$. $^1$H NMR (400 MHz, DMSO-d$_6$): δ 8.68 (s, 1H), 8.55 (s, 1H), 8.39-8.44 (m, 1H), 8.15 (s, 1H), 7.98-8.06 (m, 1H), 7.95 (s, 1H), 7.85-7.91 (m, 2H), 7.65-7.75 (m, 3H), 7.32 (s, 1H), 7.27 (d, J=8.3 Hz, 1H), 7.11-7.20 (m, 1H), 6.65 (t, J=75.7 Hz, 1H), 6.15-6.25 (m, 1H), 3.80-3.91 (m, 1H), 3.65-3.71 (m, 1H), 2.54-2.71 (m, 2H). $^{19}$F NMR (376 MHz, DMSO-d$_6$): d −74.69, −83.24, −112.94.

Example 955: (R*)-2-(1-(4-(4-Carboxyphenyl)-1H-pyrazol-1-yl)-2-(1-(difluoromethyl)-1H-pyrazol-3-yl)ethyl)-5-(3-chloro-6-(4-chloro-1H-1,2,3-triazol-1-yl)-2-fluorophenyl)pyridine 1-oxide

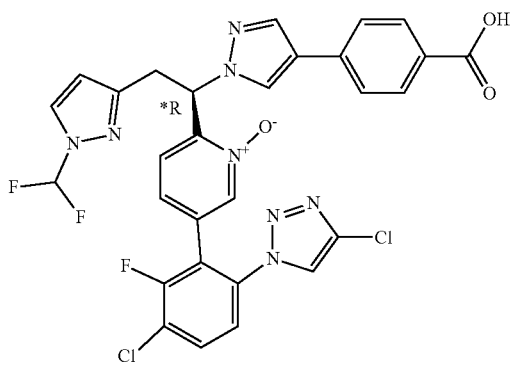 [SMILES: O=C(O)c1ccc(-c2cnn([C@H](Cc3ccn(C(F)F)n3)c3ccc(-c4c(-n5cc(Cl)nn5)ccc(Cl)c4F)c[n+]3[O-])c2)cc1]

LC/MS: mass calculated for C$_{29}$H$_{19}$Cl$_2$F$_3$N$_8$O$_3$: 654.09, measured (ES, m/z): 655.10[M+H]$^+$. $^1$H NMR (400 MHz, CD$_3$OD) δ 8.36 (s, 1H), 8.29-8.31 (m, 2H), 8.02 (s, 1H), 7.99-8.01 (m, 1H), 7.97-7.99 (m, 1H), 7.83-7.91 (m, 2H), 7.61-7.67 (m, 2H), 7.55 (dd, J=8.7, 1.6 Hz, 1H), 7.51 (s, 1H), 7.37 (t, J=64.0 Hz, 1H), 7.31 (dd, J=8.4, 1.7 Hz, 1H), 6.54 (dd, J=8.4, 6.4 Hz, 1H), 6.19 (d, J=2.7 Hz, 1H), 3.75-3.81 (m, 2 h). $^{19}$F NMR (376 MHz, CD$_3$OD) δ −95.97, −114.10.

Example 956: (S*)-2-(1-(4-(4-Carboxyphenyl)-1H-pyrazol-1-yl)-2-(1-(difluoromethyl)-1H-pyrazol-3-yl)ethyl)-5-(3-chloro-6-(4-chloro-1H-1,2,3-triazol-1-yl)-2-fluorophenyl)pyridine 1-oxide

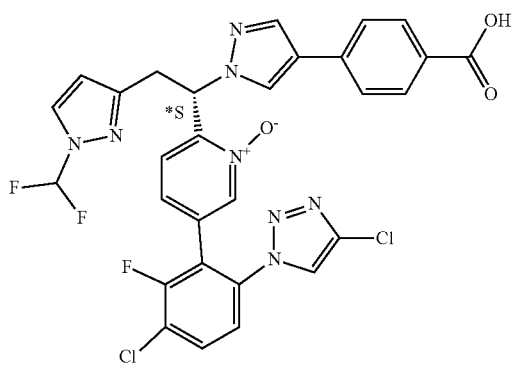 [SMILES: O=C(O)c1ccc(-c2cnn([C@@H](Cc3ccn(C(F)F)n3)c3ccc(-c4c(-n5cc(Cl)nn5)ccc(Cl)c4F)c[n+]3[O-])c2)cc1]

LC/MS: mass calculated for C$_{29}$H$_{19}$Cl$_2$F$_3$N$_8$O$_3$: 654.09, measured (ES, m/z): 655.25 [M+H]$^+$. $^1$H NMR (400 MHz, CD$_3$OD) δ 8.36 (s, 1H), 8.29-8.31 (m, 2H), 8.03 (s, 1H), 8.00-8.02 (m, 1H), 7.98-8.00 (m, 1H), 7.84-7.91 (m, 2H), 7.65-7.67 (m, 1H), 7.63-7.65 (m, 1H), 7.56 (dd, J=8.7, 1.6 Hz, 1H), 7.52 (d, J=1.5 Hz, 1H), 7.38 (t, J=64.0 Hz, 1H), 7.32 (dd, J=8.4, 1.7 Hz, 1H), 6.54 (dd, J=8.4, 6.5 Hz, 1H), 6.19 (d, J=2.7 Hz, 1H), 3.73-3.82 (m, 2H). $^{19}$F NMR (376 MHz, CD$_3$OD) δ −95.97, −114.10.

Example 957: (R*)-2-(1-(4-(4-Carboxyphenyl)-1H-pyrazol-1-yl)-2-(1-(difluoromethyl)-1H-pyrazol-3-yl)ethyl)-5-(3-chloro-6-(4-trifluoromethyl-1H-1,2,3-triazol-1-yl)-2-fluorophenyl)pyridine 1-oxide

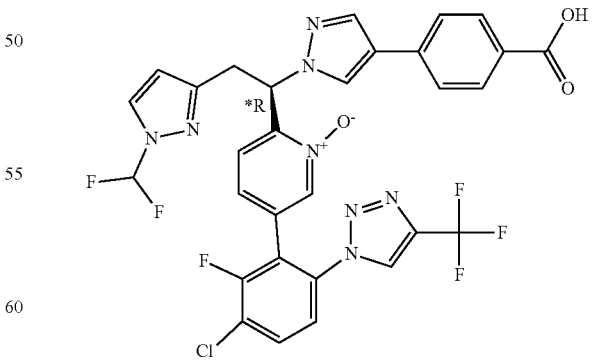

LC/MS: mass calculated for C$_{30}$H$_{19}$ClF$_6$N$_8$O$_3$: 688.12, measured (ES, m/z): 689.15 [M+H]$^+$. $^1$H NMR (400 MHz, CD$_3$OD) δ 8.80 (d, J=0.8 Hz, 1H), 8.38 (s, 1H), 8.28 (s, 1H), 8.01 (s, 1H), 7.99-8.01 (m, 1H), 7.97-7.99 (m, 1H), 7.90 (dd, J=8.7, 7.6 Hz, 1H), 7.86 (d, J=2.7 Hz, 1H), 7.64-7.66 (m, 1H), 7.62-7.64 (m, 1H), 7.60 (dd, J=8.7, 1.6 Hz, 1H), 7.51 (d, J=8.4 Hz, 1H), 7.35 (t, J=60 Hz, 1H), 7.30 (dd, J=8.3, 1.7 Hz, 1H), 6.54 (dd, J=8.5, 6.4 Hz, 1H), 6.19 (d, J=2.7 Hz, 1H), 3.73-3.81 (m, 2H). $^{19}$F NMR (376 MHz, CD$_3$OD) δ −62.68, −96.00, −113.90.

Example 958: (S*)-2-(1-(4-(4-Carboxyphenyl)-1H-pyrazol-1-yl)-2-(1-(difluoromethyl)-1H-pyrazol-3-yl)ethyl)-5-(3-chloro-2-fluoro-6-(4-(trifluoromethyl)-1H-1,2,3-triazol-1-yl)phenyl)pyridine 1-oxide

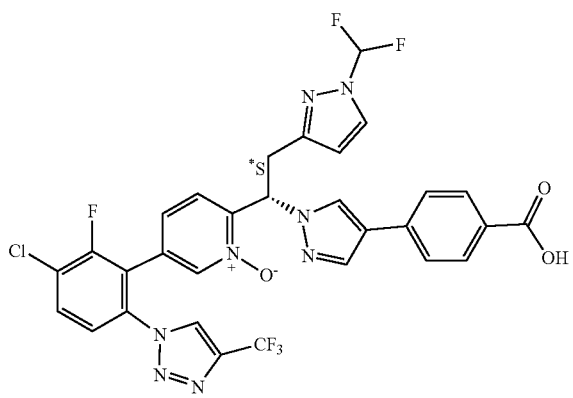

Step 1: tert-butyl 4-(1-(1-(5-(3-chloro-2-fluoro-6-(4-(trifluoromethyl)-1H-1,2,3-triazol-1-yl)phenyl)pyridin-2-yl)-2-(1-(difluoromethyl)-1H-pyrazol-3-yl)ethyl)-1H-pyrazol-4-yl)benzoate To a solution of 1-(4-chloro-3-fluoro-2-iodophenyl)-4-(trifluoromethyl)-1H-1,2,3-triazole (0.31 g, 0.79 mmol, 1.0 equiv.) and (6-(1-(4-(4-(tert-butoxycarbonyl)phenyl)-1H-pyrazol-1-yl)-2-(1-(difluoromethyl)-1H-pyrazol-3-yl)ethyl)pyridin-3-yl)boronic acid (0.99 g, resulting) in 1,4-dioxane (20 mL) and water (4 mL) was added potassium carbonate (0.33 g, 2.4 mmol, 3.0 equiv.) and Pd(PPh$_3$)$_4$ (92 mg, 0.08 mmol, 0.1 equiv.) under N$_2$. The reaction mixture was stirred for 2 h at 95° C., then quenched with water, extracted with EA twice. The combined organic layers were dried over Na$_2$SO$_4$ and concentrated under vacuum. The residue was purified by silica gel chromatography (0→100% EA/PE) to yield tert-butyl 4-(1-(1-(5-(3-chloro-2-fluoro-6-(4-(trifluoromethyl)-1H-1,2,3-triazol-1-yl)phenyl)pyridin-2-yl)-2-(1-(difluoromethyl)-1H-pyrazol-3-yl)ethyl)-1H-pyrazol-4-yl)benzoate as a light brown solid. LC/MS: mass calculated for C$_{34}$H$_{27}$ClF$_6$N$_8$O$_2$: 728.18, measured (ES, m/z): 729.20 [M+H]$^+$.

Step 2: 4-(1-(1-(5-(3-Chloro-2-fluoro-6-(4-(trifluoromethyl)-1H-1,2,3-triazol-1-yl)phenyl)pyridin-2-yl)-2-(1-(difluoromethyl)-1H-pyrazol-3-yl)ethyl)-1H-pyrazol-4-yl)benzoic acid To a solution of tert-butyl 4-(1-(1-(5-(3-chloro-2-fluoro-6-(4-(trifluoromethyl)-1H-1,2,3-triazol-1-yl)phenyl)pyridin-2-yl)-2-(1-(difluoromethyl)-1H-pyrazol-3-yl)ethyl)-1H-pyrazol-4-yl)benzoate (0.35 g, 0.48 mmol, 1.0 equiv.) in DCM (10 mL) was added TFA (3 mL). The reaction mixture was stirred for 2 h at room temperature, then concentrated under vacuum. The residue was purified by reverse column chromatography on C18 (0→70% MeCN/H$_2$O) to yield 4-(1-(1-(5-(3-chloro-2-fluoro-6-(4-(trifluoromethyl)-1H-1,2,3-triazol-1-yl)phenyl)pyridin-2-yl)-2-(1-(difluoromethyl)-1H-pyrazol-3-yl)ethyl)-1H-pyrazol-4-yl)benzoic acid as an off-white solid. LC/MS: mass calculated for C$_{30}$H$_{19}$ClF$_6$N$_8$O$_2$: 672.12, measured (ES, m/z): 673.15 [M+H]$^+$.

Step 3: (S*)-2-(1-(4-(4-Carboxyphenyl)-1H-pyrazol-1-yl)-2-(1-(difluoromethyl)-1H-pyrazol-3-yl)ethyl)-5-(3-chloro-2-fluoro-6-(4-(trifluoromethyl)-1H-1,2,3-triazol-1-yl)phenyl)pyridine 1-oxide To a solution of 4-(1-(1-(5-(3-chloro-2-fluoro-6-(4-(trifluoromethyl)-1H-1,2,3-triazol-1-yl)phenyl)pyridin-2-yl)-2-(1-(difluoromethyl)-1H-pyrazol-3-yl)ethyl)-1H-pyrazol-4-yl)benzoic acid (0.29 g, 0.43 mmol, 1.0 equiv.) in CH$_3$OH (8 mL) was added hydrogen peroxide solution (30 wt %, 0.49 g, 4.3 mmol, 10.0 equiv.) followed by the addition of methyl trioxorhenium (32 mg, 0.13 mmol, 0.3 equiv.). The reaction mixture was stirred for 2 hours at room temperature, then purified by reverse phase column chromatography on C18 (0→70% MeCN/H$_2$O) to yield a residue, which was purified by Prep-Chiral-HPLC with (Hex:DCM=3:1)(0.1% TFA):EtOH=50:50 to yield (R)-2-(1-(4-(4-carboxyphenyl)-1H-pyrazol-1-yl)-2-(1-(difluoromethyl)-1H-pyrazol-3-yl)ethyl)-5-(3-chloro-2-fluoro-6-(4-(trifluoromethyl)-1H-1,2,3-triazol-1-yl)phenyl)pyridine 1-oxide as a white solid and (S*)-2-(1-(4-(4-carboxyphenyl)-1H-pyrazol-1-yl)-2-(1-(difluoromethyl)-1H-pyrazol-3-yl)ethyl)-5-(3-chloro-2-fluoro-6-(4-(trifluoromethyl)-1H-1,2,3-triazol-1-yl)phenyl)pyridine 1-oxide as a white solid.

LC/MS: mass calculated for C$_{30}$H$^{19}$ClF$_6$N$_8$O$_3$: 688.12, measured (ES, m/z): 689.25 [M+H]$^+$. $^1$H NMR (400 MHz, CD$_3$OD): δ 8.80 (d, J=1.0 Hz, 1H), 8.38 (s, 1H), 8.28 (s, 1H), 7.96-8.03 (m, 3H), 7.84-7.93 (m, 2H), 7.57-7.67 (m, 3H), 7.19-7.54 (m, 3H), 6.50-6.57 (m, 1H), 6.19 (d, J=2.7 Hz, 1H), 3.73-3.83 (m, 2H). $^{19}$F-NMR (376 MHz, CD$_3$OD): (376 MHz, CD$_3$OD): δ −62.68, −96.00, −113.90.

Example 959: 2-(1-4-(4-Carboxyl-3-fluorophenyl)-1H-pyrazol-1-yl)-3-oxo-3-(pyrrolidin-1-yl)propyl)-5-(3-chloro-2-fluoro-6-(4-(trifluoromethyl)-1H-1,2,3-triazol-1-yl)phenyl)pyridine 1-oxide TFA

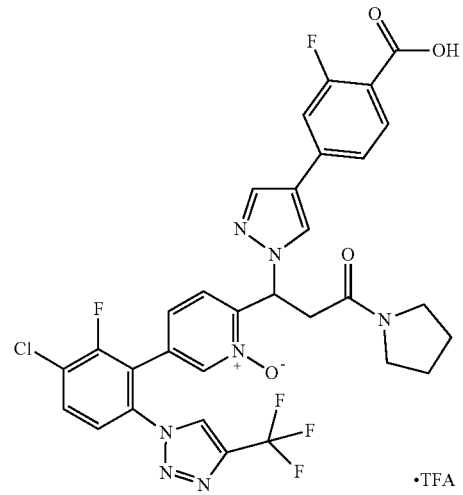

To a solution of 4-(1-(1-(5-(3-chloro-2-fluoro-6-(4-(trifluoromethyl)-1H-1,2,3-triazol-1-yl)phenyl)pyridin-2-yl)-3-oxo-3-(pyrrolidin-1-yl) propyl)-1H-pyrazol-4-yl)-2-fluorobenzoic acid (60 mg, 0.089 mmol) in CH$_3$OH (1 mL) was added methyltrioxorhenium (11.1 mg, 0.0446 mmol) and H$_2$O$_2$ (0.092 mL, 0.893 mmol, 30%). The resulting mixture was stirred at room temperature for 1.5 h. The solvent was removed and the residue was purified by via ISCO reverse phase column 0.1% TFA in water and 0.1% TFA in ACN (35% to 65% 0.1% TFA in ACN gradient) to yield 2-(1-4-(4-carboxyl-3-fluorophenyl)-1H-pyrazol-1-yl)-3-oxo-3-(pyrrolidin-1-yl)propyl)-5-(3-chloro-2-fluoro-6-(4-(trifluoromethyl)-1H-1,2,3-triazol-1-yl)phenyl)pyridine 1-oxide TFA as an off-white solid.

LC/MS: mass calculated for C$_{31}$H$_{23}$ClF$_5$N$_7$O$_4$: 687.1, measured (ES, m/z): 688.2 [M+H]$^+$. $^1$H NMR: (CD$_3$OD, 400 MHz) δ 8.79 (s, 1H), 8.37 (br d, J=6.36 Hz, 2H), 8.04 (s, 1H), 7.87-7.94 (m, 2H), 7.60 (dd, J=8.56, 1.22 Hz, 1H), 7.41-7.49 (m, 2H), 7.20-7.23 (m, 2H), 6.65 (br d, J=5.87 Hz, 1H), 3.47-3.64 (m, 3H) 3.32-3.42 (m, 3H), 1.80-2.01 (m, 4H). $^{19}$F-NMR: (CD$_3$OD, 377 MHz) δ −126.35, −123.60, −89.95, −75.05.

Example 960: 2-(1-4-(4-Carbamoyl-3-fluorophenyl)-1H-pyrazol-1-yl)-3-oxo-3-(pyrrolidin-1-yl)propyl)-5-(3-chloro-2-fluoro-6-(4-(trifluoromethyl)-1H-1,2,3-triazol-1-yl)phenyl)pyridine 1-oxide TFA

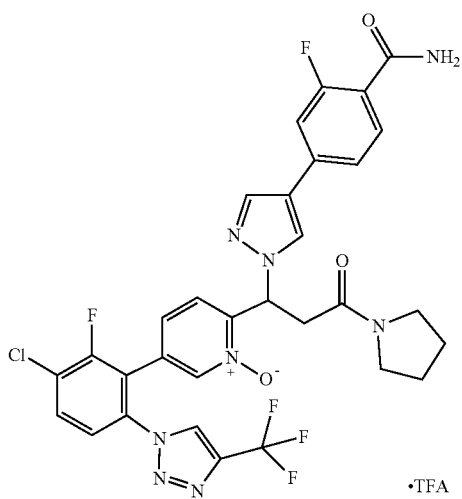

To a solution of 4-(1-(1-(5-(3-chloro-2-fluoro-6-(4-(trifluoromethyl)-1H-1,2,3-triazol-1-yl)phenyl)pyridin-2-yl)-3-oxo-3-(pyrrolidin-1-yl) propyl)-1H-pyrazol-4-yl)-2-fluorobenzamide (100 mg, 0.149 mmol) in CH$_3$OH (1 mL) was added methyltrioxorhenium (18.6 mg, 0.0745 mmol) and H$_2$O$_2$ (0.154 mL, 1.49 mmol, 30%). The resulting mixture was stirred at room temperature for 1.5 h. The solvent was removed, and the residue was purified by via ISCO reverse phase column 0.1% TFA in water and 0.1% TFA in ACN (35% to 60% 0.1% TFA in ACN gradient) to yield 2-(1-4-(4-carbamoyl-3-fluorophenyl)-1H-pyrazol-1-yl)-3-oxo-3-(pyrrolidin-1-yl)propyl)-5-(3-chloro-2-fluoro-6-(4-(trifluoromethyl)-1H-1,2,3-triazol-1-yl)phenyl)pyridine 1-oxide TFA as an off-white solid.

LC/MS: mass calculated for C$_{31}$H$_{24}$ClF$_5$N$_8$O$_3$: 686.1, measured (ES, m/z): 687.3 [M+H]$^+$. $^1$H NMR: (CD$_3$OD, 400 MHz) δ 8.79 (s, 1H), 8.37 (br s, 2H), 8.04 (s, 1H), 7.90 (t, J=7.67 Hz, 1H), 7.83 (t, J=8.07 Hz, 1H), 7.60 (dd, J=8.80, 1.47 Hz, 1H), 7.42-7.52 (m, 2H), 7.23 (s, 2H), 6.65 (br s, 1H), 3.47-3.63 (m, 3H), 3.32-3.42 (m, 3H), 1.79-2.01 (m, 4H). $^{19}$F-NMR: (CD$_3$OD, 377 MHz) δ −127.08, −126.34, −90.03, −75.04.

Example 961: 5-(3-Chloro-2-fluoro-6-(4-(trifluoromethyl)-1H-1,2,3-triazol-1-yl)phenyl)-2-(3-(difluoromethoxy)-1-(4-(4-(5-oxo-2,5-dihydro-1,2,4-oxadiazol-3-yl)phenyl)-1H-pyrazol-1-yl)propyl) pyridine 1-oxide TFA

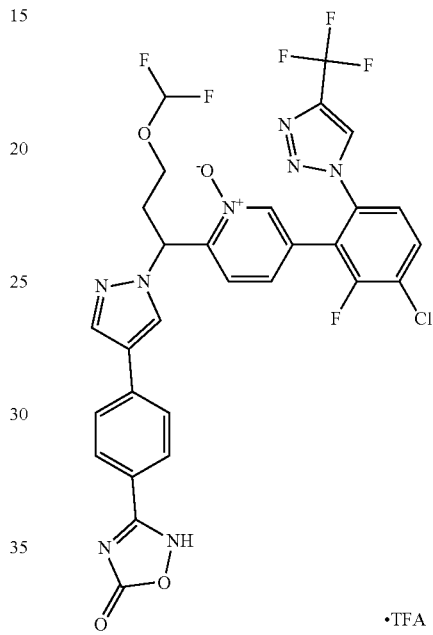

To a solution of 3-(4-(1-(1-(5-(3-chloro-2-fluoro-6-(4-(trifluoromethyl)-1H-1,2,3-triazol-1-yl)phenyl)pyridin-2-yl)-3-(difluoromethoxy)propyl)-1H-pyrazol-4-yl)phenyl)-1,2,4-oxadiazol-5 (2H)-one (0.055 g, 0.0812 mmole) in MeOH (2 mL), methyl trioxorhenium (VII) (0.015 g, 0.061 mmole), and 30% hydrogen peroxide (0.094 mL, 0.92 mmole) were added. The reaction mixture was stirred at room temperature for 1.5 hour. The solid was filtered and washed with DCM. The organic solvent was removed under vacuum. The residue was purified via reverse phase column chromatography with 0.1% TFA in water and 0.1% TFA in ACN as eluent (20% to 55% 0.1% TFA in ACN gradient) to yield 5-(3-chloro-2-fluoro-6-(4-(trifluoromethyl)-1H-1,2,3-triazol-1-yl)phenyl)-2-(3-(difluoromethoxy)-1-(4-(4-(5-oxo-2,5-dihydro-1,2,4-oxadiazol-3-yl)phenyl)-1H-pyrazol-1-yl)propyl)pyridine 1-oxide TFA as a white solid.

LC-MS: calculated mass for C$_{29}$H$_{19}$ClF$_6$N$_8$O$_4$: 692.11, measured (ES, m/z): 693.2 [M+H]$^+$. $^1$H NMR (DMSO-d$_6$, 400 MHz) 5-12.93 (bs, 1H), 9.18 (s, 1H), 8.59 (s, 1H), 8.44 (s, 1H), 8.18 (s, 1H), 8.06 (t, J=8.3 Hz, 1H), 7.87-7.73 (m, 5H), 7.28 (d, J=8.3 Hz, 1H), 7.16 (dd, JJ=8.3, 1.0 Hz, 1H), 6.64 (t, J=76.2 Hz, 1H), 6.24-6.17 (m, 1H), 3.90-3.63 (m, 2H), 2.69-2.53 (m, 2H). $^{19}$F NMR (DMSO-d$_6$, 377 MHz) 5--125.2 (s), −95.8 (s), −95.6 (s), −86.8 (s).

Example 962: 2-(1-(4-(5-Carbamoylthiophen-2-yl)-1H-pyrazol-1-yl)-2-cyclopropylethyl)-5-(3-chloro-2-fluoro-6-(4-(trifluoromethyl)-1H-1,2,3-triazol-1-yl)phenyl)pyridine 1-oxide

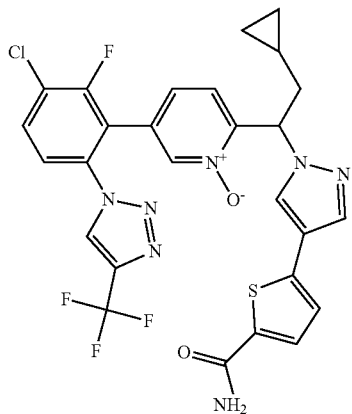 [SMILES: NC(=O)c1ccc(-c2cnn(C(CC3CC3)c3ccc(-c4c(-n5cc(C(F)(F)F)nn5)ccc(Cl)c4F)c[n+]3[O-])c2)s1]

LC/MS: mass calculated for $C_{27}H_{20}ClF_4N_7O_2S$: 617.10, measured (ES, m/z): 618.05 [M+H]⁺. ¹H NMR (400 MHz, DMSO-$d_6$) δ 9.18 (s, 1H), 8.46 (s, 1H), 8.40 (d, J=1.6 Hz, 1H), 8.02-8.10 (m, 1H), 7.85-8.00 (m, 2H), 7.73-7.83 (m, 1H), 7.67 (d, J=3.9 Hz, 1H), 7.28-7.37 (m, 2H), 7.23 (d, J=3.8 Hz, 1H), 7.10-7.18 (m, 1H), 6.08-6.15 (m, 1H), 2.26-2.34 (m, 1H), 1.90-2.00 (m, 1H), 0.55-0.63 (m, 1H), 0.29-0.39 (m, 2H), 0.08-0.12 (m, 1H), 0.01-0.04 (m, 1H). ¹⁹F NMR (376 MHz, DMSO-$d_6$) δ −59.76, −112.88.

Example 963: (S*)-2-(1-(4-(4-Carbamoyl-3-fluorophenyl)-1H-pyrazol-1-yl)-2-(1-(difluoromethyl)-1H-pyrazol-3-yl)ethyl)-5-(5-chloro-2-(4-(trifluoromethyl)-1H-1,2,3-triazol-1-yl)phenyl)pyridine 1-oxide

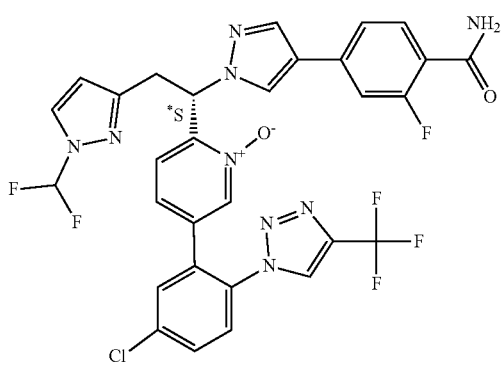 [SMILES: NC(=O)c1ccc(-c2cnn([C@@H](Cc3ccn(C(F)F)n3)c3ccc(-c4cc(Cl)ccc4-n4cc(C(F)(F)F)nn4)c[n+]3[O-])c2)cc1F]

Step 1: (6-(1-(4-(4-Carbamoyl-3-fluorophenyl)-1H-pyrazol-1-yl)-2-(1-(difluoromethyl)-1H-pyrazol-3-yl) ethyl) pyridin-3-yl) boronic acid To a mixture of 4-(1-(1-(5-bromopyridin-2-yl)-2-(1-(difluoromethyl)-1H-pyrazol-3-yl) ethyl)-1H-pyrazol-4-yl)-2-fluorobenzamide (150 mg, 0.30 mmol, 1.0 equiv.) and 4,4,4',4',5,5,5',5'-octamethyl-2,2'-bi(1,3,2-dioxaborolane) (226 mg, 0.89 mmol, 3.0 equiv.) in 1,4-dioxane (5 mL) was added potassium acetate (117 mg, 1.19 mmol, 4.0 equiv.) and Pd(dppf)Cl₂ (43 mg, 0.06 mmol, 0.2 equiv.). The solution was stirred at 90° C. for 2 h under N₂. The reaction was added water, and the mixture extracted with EA twice. The combined organic layers were washed with brine, dried over Na₂SO₄ and concentrated under vacuum to yield (6-(1-(4-(4-carbamoyl-3-fluorophenyl)-1H-pyrazol-1-yl)-2-(1-(difluoromethyl)-1H-pyrazol-3-yl) ethyl) pyridin-3-yl) boronic acid as yellow solid. LC/MS: mass calculated for $C_{21}H_{18}BF_3N_6O_3$: 470.15, measured (ES, m/z): 471.05 [M+H]⁺.

Step 2: 4-(1-(1-(5-(5-Chloro-2-(4-(trifluoromethyl)-1H-1, 2, 3-triazol-1-yl) phenyl)pyridin-2-yl)-2-(1-(difluoromethyl)-1H-pyrazol-3-yl)ethyl)-1H-pyrazol-4-yl)-2-fluorobenzamide To a mixture of (6-(1-(4-(4-carbamoyl-3-fluorophenyl)-1H-pyrazol-1-yl)-2-(1-(difluoromethyl)-1H-pyrazol-3-yl) ethyl)pyridin-3-yl)boronic acid (150 mg, 0.32 mmol, 1.0 equiv.), potassium carbonate (132 mg, 0.96 mmol, 3.0 equiv.) and 1-(4-chloro-2-iodophenyl)-4-(trifluoromethyl)-1H-1,2,3-triazole (143 mg, 0.38 mmol, 1.2 equiv.) in 1,4-dioxane (4 mL) and water (1 mL) added tetrakis(triphenylphosphine)Palladium(0) (37 mg, 0.03 mmol, 0.1 equiv.) and the mixture was stirred at 100° C. for 2 h under N₂. Water was added, the mixture was extracted with EA. The combined organic layers were washed with brine, dried over Na₂SO₄ and concentrated. The residue was purified by silica gel chromatography (0→10% CH₃OH/dichloromethane) to yield 4-(1-(1-(5-(5-chloro-2-(4-(trifluoromethyl)-1H-1, 2, 3-triazol-1-yl) phenyl)pyridin-2-yl)-2-(1-(difluoromethyl)-1H-pyrazol-3-yl)ethyl)-1H-pyrazol-4-yl)-2-fluorobenzamide as yellow solid. LC/MS: mass calculated for $C_{30}H_{20}ClF_3N_9O$: 671.14, measured (ES, m/z): 672.30 [M+H]⁺.

Step 3: (S*)-2-(1-(4-(4-Carbamoyl-3-fluorophenyl)-1H-pyrazol-1-yl)-2-(1-(difluoromethyl)-1H-pyrazol-3-yl) ethyl)-5-(5-chloro-2-(4-(trifluoromethyl)-1H-1, 2,3-triazol-1-yl)phenyl)pyridine 1-oxide To a solution of 4-(1-(1-(5-(5-chloro-2-(4-(trifluoromethyl)-1H-1,2,3-triazol-1-yl)phenyl)pyridin-2-yl)-2-(1-(difluoromethyl)-1H-pyrazol-3-yl)ethyl)-1H-pyrazol-4-yl)-2-fluorobenzamide (170 mg, 0.25 mmol, 1.0 equiv.) and ReMeO₃ (13 mg, 0.05 mmol, 0.2 equiv.) in CH₃OH (3 mL) was added hydrogen peroxide (0.25 mL, 2.53 mmol, 30 wt %, 10.0 equiv.). The reaction mixture was stirred at room temperature for 5 h. The reaction mixture was purified by reverse phase chromatography on C18 (120 g, ACN/H₂O (0.05% CF₃COOH): 0→35%) to yield (S*)-2-(1-(4-(4-carbamoyl-3-fluorophenyl)-1H-pyrazol-1-yl)-2-(1-(difluoromethyl)-1H-pyrazol-3-yl) ethyl)-5-(5-chloro-2-(4-(trifluoromethyl)-1H-1,2,3-triazol-1-yl)phenyl)pyridine 1-oxide as white solid.

LC/MS: mass calculated for $C_{30}H_{20}ClF_6N_9O_2$: 687.13, measured (ES, m/z): 688.10[M+H]⁺. ¹H NMR (300 MHz, DMSO-$d_6$) δ 9.19 (d, J=1.1 Hz, 1H), 8.57 (s, 1H), 8.34 (d, J=1.7 Hz, 1H), 8.13 (s, 1H), 8.04 (d, J=2.6 Hz, 1H), 7.92 (s, 1H), 7.45-7.90 (m, 8H), 7.28-7.31 (m, 1H), 6.95-7.00 (m, 1H), 6.33-6.44 (m, 1H), 6.12 (d, J=2.6 Hz, 1H), 3.56-3.68 (m, 2H). ¹⁹F-NMR (282 MHz, DMSO-$d_6$) δ −59.68, −93.83, −113.03.

Example 964: (R*)-2-(1-(4-(4-Carbamoyl-3-fluoro-phenyl)-1H-pyrazol-1-yl)-2-(1-(difluoromethyl)-1H-pyrazol-3-yl)ethyl)-5-(5-chloro-2-(4-(trifluoromethyl)-1H-1,2,3-triazol-1-yl)phenyl)pyridine 1-oxide

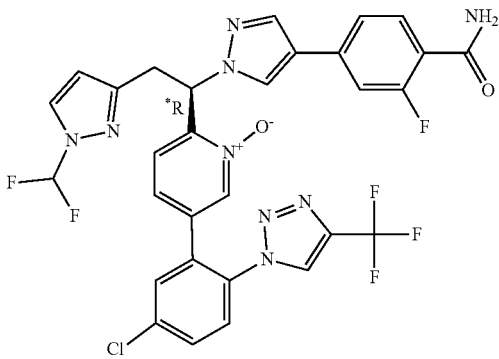 [SMILES: NC(=O)c1ccc(-c2cnn([C@H](Cc3ccn(C(F)F)n3)c3ccc(-c4cc(Cl)ccc4-n4cc(C(F)(F)F)nn4)c[n+]3[O-])c2)cc1F]

Step 1: (6-(1-(4-(4-Carbamoyl-3-fluorophenyl)-1H-pyrazol-1-yl)-2-(1-(difluoromethyl)-1H-pyrazol-3-yl) ethyl) pyridin-3-yl) boronic acid To a mixture of 4-(1-(1-(5-bromopyridin-2-yl)-2-(1-(difluoromethyl)-1H-pyrazol-3-yl) ethyl)-1H-pyrazol-4-yl)-2-fluorobenzamide (150 mg, 0.30 mmol, 1.0 equiv.) and 4,4,4',4',5,5,5',5'-octamethyl-2,2'-bi(1,3,2-dioxaborolane) (226 mg, 0.89 mmol, 3.0 equiv.) in 1,4-dioxane (5 mL) was added potassium acetate (117 mg, 1.19 mmol, 4.0 equiv.) and Pd(dppf)Cl$_2$ (43 mg, 0.06 mmol, 0.2 equiv.). The solution was stirred at 90° C. for 2 h under N$_2$. The reaction was added water, and the mixture extracted with EA twice. The combined organic layers were washed with brine, dried over Na$_2$SO$_4$ and concentrated under vacuum to yield (6-(1-(4-(4-carbamoyl-3-fluorophenyl)-1H-pyrazol-1-yl)-2-(1-(difluoromethyl)-1H-pyrazol-3-yl) ethyl) pyridin-3-yl) boronic acid as yellow solid. LC/MS: mass calculated for C$_{21}$H$_{18}$BF$_3$N$_6$O$_3$: 470.15, measured (ES, m/z): 471.05 [M+H]$^+$.

Step 2: 4-(1-(1-(5-(5-Chloro-2-(4-(trifluoromethyl)-1H-1, 2, 3-triazol-1-yl) phenyl)pyridin-2-yl)-2-(1-(difluoromethyl)-1H-pyrazol-3-yl)ethyl)-1H-pyrazol-4-yl)-2-fluorobenzamide To a mixture of (6-(1-(4-(4-carbamoyl-3-fluorophenyl)-1H-pyrazol-1-yl)-2-(1-(difluoromethyl)-1H-pyrazol-3-yl) ethyl)pyridin-3-yl)boronic acid (150 mg, 0.32 mmol, 1.0 equiv.), potassium carbonate (132 mg, 0.96 mmol, 3.0 equiv.) and 1-(4-chloro-2-iodophenyl)-4-(trifluoromethyl)-1H-1,2,3-triazole (143 mg, 0.38 mmol, 1.2 equiv.) in 1,4-dioxane (4 mL) and water (1 mL) added tetrakis(triphenylphosphine)Palladium(0) (37 mg, 0.03 mmol, 0.1 equiv.) was stirred at 100° C. for 2 h under N$_2$. Water was added, the mixture was extracted with EA. The combined organic layers were washed with brine, dried over Na$_2$SO$_4$ and concentrated. The residue was purified by silica gel chromatography (0→10% CH$_3$OH/dichloromethane) to yield 4-(1-(1-(5-(5-chloro-2-(4-(trifluoromethyl)-1H-1, 2, 3-triazol-1-yl) phenyl)pyridin-2-yl)-2-(1-(difluoromethyl)-1H-pyrazol-3-yl)ethyl)-1H-pyrazol-4-yl)-2-fluorobenzamide as yellow solid. LC/MS: mass calculated for C$_{30}$H$_{20}$ClF$_6$N$_9$O: 671.14, measured (ES, m/z): 672.30 [M+H]$^+$.

Step 3: (R*)-2-(1-(4-(4-Carbamoyl-3-fluorophenyl)-1H-pyrazol-1-yl)-2-(1-(difluoromethyl)-1H-pyrazol-3-yl)ethyl)-5-(5-chloro-2-(4-(trifluoromethyl)-1H-1, 2,3-triazol-1-yl)phenyl)pyridine 1-oxide To a solution of 4-(1-(1-(5-(5-chloro-2-(4-(trifluoromethyl)-1H-1,2,3-triazol-1-yl)phenyl)pyridin-2-yl)-2-(1-(difluoromethyl)-1H-pyrazol-3-yl)ethyl)-1H-pyrazol-4-yl)-2-fluorobenzamide (170 mg, 0.25 mmol, 1.0 equiv) and ReMeO$_3$ (13 mg, 0.05 mmol, 0.2 equiv.) in CH$_3$OH (3 mL) was added hydrogen peroxide (0.25 mL, 2.53 mmol, 30 wt %, 10.0 equiv.). The reaction mixture was stirred at room temperature for 5 h. The reaction mixture was purified by reverse phase chromatography on C18 (120 g, ACN/H$_2$O (0.05% CF$_3$COOH): 0→35%). To yield (R*)-2-(1-(4-(4-carbamoyl-3-fluorophenyl)-1H-pyrazol-1-yl)-2-(1-(difluoromethyl)-1H-pyrazol-3-yl)ethyl)-5-(5-chloro-2-(4-(trifluoromethyl)-1H-1,2,3-triazol-1-yl)phenyl)pyridine 1-oxide as white solid.

LC/MS: mass calculated for C$_{30}$H$_{20}$ClF$_6$N$_9$O$_2$: 687.13, measured (ES, m/z): 688.15 [M+H]$^+$. $^1$H NMR (300 MHz, DMSO-d$_6$) δ 9.19 (d, J=1.1 Hz, 1H), 8.57 (s, 1H), 8.34 (d, J=1.7 Hz, 1H), 8.13 (s, 1H), 8.04 (d, J=2.6 Hz, 1H), 7.92 (s, 1H), 7.45-7.90 (m, 8H), 7.28-7.31 (m, 1H), 6.94-7.00 (m, 1H), 6.33-6.44 (m, 1H), 6.12 (d, J=2.6 Hz, 1H), 3.56-3.68 (m, 2H). $^{19}$F-NMR (282 MHz, DMSO-d$_6$) δ −59.47, −93.83, −113.02.

Example 965: (R*)-2-(1-(4-(4-Carbamoylphenyl)-1H-pyrazol-1-yl)-2-(1-(difluoromethyl)-1H-pyrazol-3-yl)ethyl)-5-(3-chloro-2-fluoro-6-(4-(trifluoromethyl)-1H-1,2,3-triazol-1-yl)phenyl)pyridine 1-oxide

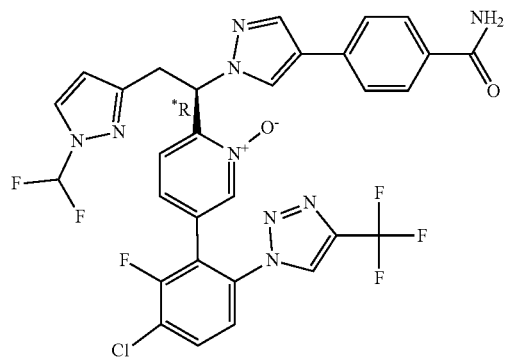 [SMILES: NC(=O)c1ccc(-c2cnn([C@H](Cc3ccn(C(F)F)n3)c3ccc(-c4c(-n5cc(C(F)(F)F)nn5)ccc(Cl)c4F)c[n+]3[O-])c2)cc1]

LC/MS: mass calculated for C$_{30}$H$_{20}$ClF$_6$N$_9$O$_2$: 687.13, measured (ES, m/z): 688.10 [M+H]$^+$. $^1$H NMR (400 MHz, CD$_3$OD) δ 8.80 (s, 1H), 8.37 (s, 1H), 8.27 (s, 1H), 8.00 (s, 1H), 7.73-7.93 (m, 4H), 7.57-7.66 (m, 3H), 7.18-7.53 (m, 3H), 6.54 (t, J=7.5 Hz, 1H), 6.19 (d, J=2.6 Hz, 1H), 3.72-3.84 (m, 2H). $^{19}$F NMR (376 MHz, CD$_3$OD) δ −62.68, −77.23, −99.01, −113.91.

Example 966: (S*)-2-(1-(4-(4-Carbamoylphenyl)-1H-pyrazol-1-yl)-2-(1-(difluoromethyl)-1H-pyrazol-3-yl)ethyl)-5-(3-chloro-2-fluoro-6-(4-(trifluoromethyl)-1H-1,2,3-triazol-1-yl)phenyl)pyridine 1-oxide

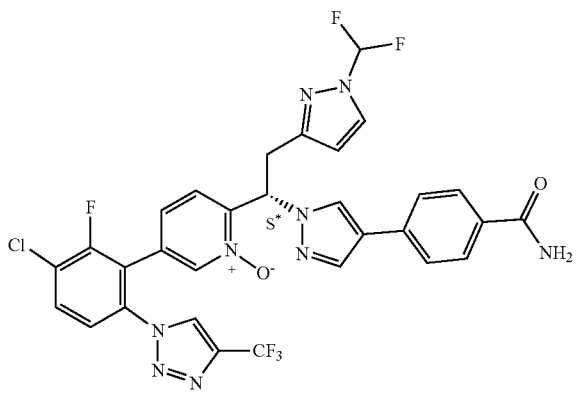

To a solution of 2-(1-(4-(4-carboxyphenyl)-1H-pyrazol-1-yl)-2-(1-(difluoromethyl)-1H-pyrazol-3-yl)ethyl)-5-(3-chloro-2-fluoro-6-(4-(trifluoromethyl)-1H-1,2,3-triazol-1-yl)phenyl)pyridine 1-oxide (1.9 g, 2.8 mmol, 1.0 equiv) in DMF (20 mL) was added HATU (2.1 g, 5.5 mmol, 2.0 equiv.), N-ethyl-N-isopropylpropan-2-amine (1.8 g, 13.8 mmol, 5.0 equiv.) and ammonium chloride (1.2 g, 13.8 mmol, 5.0 equiv.). The reaction mixture was stirred for 2 h at room temperature, then purified by reverse column chromatography on C18 (5→50% MeCN/H$_2$O (0.05% CF3COOH)) to yield a residue, which was purified by SFC with IPA (0.1% DEA) to yield (S*)-2-(1-(4-(4-carbamoylphenyl)-1H-pyrazol-1-yl)-2-(1-(difluoromethyl)-1H-pyrazol-3-yl)ethyl)-5-(3-chloro-2-fluoro-6-(4-(trifluoromethyl)-1H-1,2,3-triazol-1-yl)phenyl)pyridine 1-oxide as a white solid.

LC/MS: mass calculated for $C_{30}H_{20}ClF_6N_9O_2$: 687.13, measured (ES, m/z): 688.10 [M+H]$^+$. $^1$H NMR (400 MHz, CD$_3$OD): δ 8.80 (d, J=1.0 Hz, 1H), 8.37 (s, 1H), 8.26 (s, 1H), 7.99 (s, 1H), 7.82-7.93 (m, 4H), 7.56-7.66 (m, 3H), 7.18-7.53 (m, 3H), 6.49-6.60 (m, 1H), 6.18 (d, J=2.7 Hz, 1H), 3.74-3.81 (m, 2H). $^{19}$F-NMR (376 MHz, CD$_3$OD): δ −62.66, −76.97, −95.99, −113.88.

Example 967: 2-(1-4-(4-Carbamoyl-3-fluorophenyl)-1H-pyrazol-1-yl)-2-(oxazol-2-yl)ethyl)-5-(3-chloro-2-fluoro-6-(4-(trifluoromethyl)-1H-1,2,3-triazol-1-yl)phenyl)pyridine 1-oxide TFA

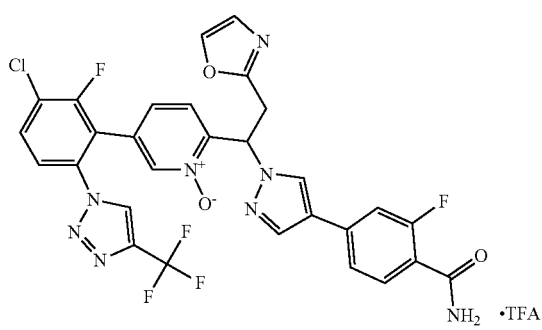 [SMILES: NC(=O)c1ccc(-c2cnn(C(Cc3ncco3)c3ccc(-c4c(-n5cc(C(F)(F)F)nn5)ccc(Cl)c4F)c[n+]3[O-])c2)cc1F]

To a solution of 4-(1-(1-(5-(3-chloro-2-fluoro-6-(4-(trifluoromethyl)-1H-1,2,3-triazol-1-yl)phenyl)pyridin-2-yl)-2-(oxazol-2-yl)ethyl)-1H-pyrazol-4-yl)-2-fluorobenzamide (80 mg, 0.125 mmol) in CH$_3$OH (3 mL) was added methyltrioxorhenium (15.5 mg, 0.0624 mmol) and H$_2$O$_2$ (0.129 mL, 1.23 mmol, 30%). The resulting mixture was stirred at room temperature for 1.5 h. The solvent was removed, and the residue was purified by via SCO reverse phase column 0.1% TFA in water and 0.1% TFA in ACN (35% to 65% 0.1% TFA in ACN gradient) to yield the title compound as a white solid.

LC/MS: mass calculated for $C_{29}H_{18}ClF_5N_8O_3$: 656.1, measured (ES, m/z): 657.2 [M+H]$^+$. $^1$H NMR: (DMSO-d$_6$, 400 MHz) δ 9.19 (s, 1H), 8.59 (s, 1H), 8.48 (s, 1H), 8.04-8.16 (m, 2H), 7.97 (s, 1H), 7.77 (d, J=8.80 Hz, 1H), 7.58-7.70 (m, 3H), 7.46-7.55 (m, 2H), 7.26 (d, J=8.31 Hz, 1H), 7.17 (d, J=8.31 Hz, 1H), 7.06 (s, 1H), 6.54 (dd, J=9.54, 5.14 Hz, 1H), 4.10 (m, 2H). $^{19}$F-NMR: (DMSO-d$_6$, 377 MHz) δ −125.39, −125.19, −86.96, −72.09.

Example 968: (R*)-2-(1-(4-(4-Carbamoylphenyl)-1H-pyrazol-1-yl)-2-(1-(difluoromethyl)-1H-pyrazol-3-yl)ethyl)-5-(3-Chloro-2-fluoro-6-(4-chloro-1H-1,2,3-triazol-1-yl)phenyl)pyridine 1-oxide

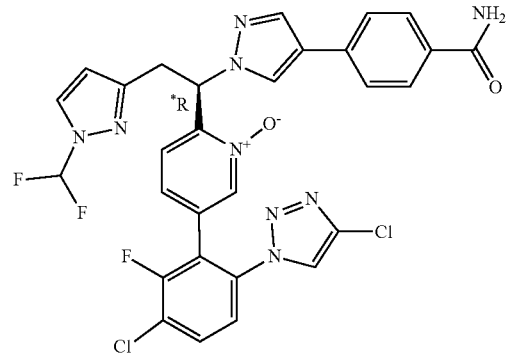 [SMILES: NC(=O)c1ccc(-c2cnn([C@H](Cc3ccn(C(F)F)n3)c3ccc(-c4c(-n5cc(Cl)nn5)ccc(Cl)c4F)c[n+]3[O-])c2)cc1]

LC/MS: mass calculated for $C_{29}H_{20}Cl_2F_3N_9O_2$: 653.11, measured (ES, m/z): 654.05[M+H]$^+$. $^1$H NMR (300 MHz, DMSO-d$_6$) δ 8.69 (s, 1H), 8.54 (s, 1H), 8.45 (s, 1H), 8.12 (s, 1H), 8.03-8.07 (m, 2H), 7.94 (s, 1H), 7.87-7.89 (m, 1H), 7.84-7.87 (m, 1H), 7.70 (t, J=60 Hz, 1H), 7.63-7.72 (m, 4H), 7.29-7.34 (m, 1H), 7.19 (dd, J=8.3, 1.7 Hz, 1H). 6.34-6.43 (m, 1H), 6.16 (d, J=2.6 Hz, 1H), 3.65-3.77 (m, 2H). $^{19}$F NMR (282 MHz, DMSO-d$_6$) δ −74.14, −93.78, −112.93.

Example 969: (S*)-2-(1-(4-(4-Carbamoylphenyl)-1H-pyrazol-1-yl)-2-(1-(difluoromethyl)-1H-pyrazol-3-yl)ethyl)-5-(3-chloro-2-fluoro-6-(4-chloro-1H-1,2,3-triazol-1-yl)phenyl)pyridine 1-oxide

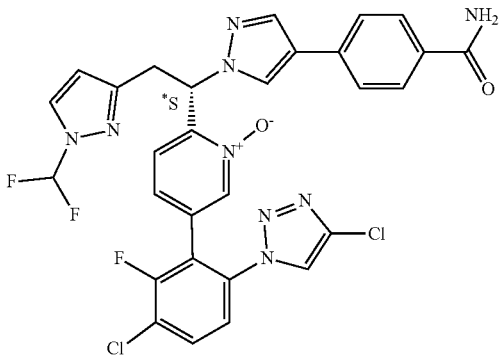 [SMILES: NC(=O)c1ccc(-c2cnn([C@@H](Cc3ccn(C(F)F)n3)c3ccc(-c4c(-n5cc(Cl)nn5)ccc(Cl)c4F)c[n+]3[O-])c2)cc1]

Step 1: tert-Butyl 4-(1-((5-bromopyridin-2-yl)methyl)-1H-pyrazol-4-yl)benzoate To a solution of tert-butyl 4-(1H-pyrazol-4-yl)benzoate (1.3 g, 5.2 mmol, 1.0 equiv.) in MeCN (30 mL) was added cesium carbonate (2.5 g, 7.7 mmol, 1.5 equiv.). After the reaction mixture was stirred for 30 min at room temperature, (5-bromopyridin-2-yl)methyl methanesulfonate (1.5 g, 5.6 mmol, 1.1 equiv.) was added. The reaction mixture was stirred for 2 h at 80° C., then cooled to room temperature. and filtered, washed with EA. The filtrate was concentrated under vacuum. The residue was purified by silica gel chromatography (0→80% EA/PE) to yield tert-butyl 4-(1-((5-bromopyridin-2-yl)methyl)-1H-pyrazol-4-yl)benzoate as a white solid. LC/MS: mass calculated for $C_{20}H_{20}BrN_3O_2$: 413.07, measured (ES, m/z): 414.05, 416.05 [M+H, M+H+2]$^+$.

Step 2: tert-Butyl 4-(1-(1-(5-bromopyridin-2-yl)-2-(1-(difluoromethyl)-1H-pyrazol-3-yl)ethyl)-1H-pyrazol-4-yl)benzoate To a solution of tert-butyl 4-(1-((5-bromopyridin-2-yl)methyl)-1H-pyrazol-4-yl)benzoate (1.8 g, 4.3 mmol, 1.0 equiv.) in THF (30 mL) was added LiHMDS (1 M in THF, 5.2 mL, 5.2 mmol, 1.2 equiv.) under $N_2$ at −70° C. After the mixture was stirred for 30 min, 3-(bromomethyl)-1-(difluoromethyl)-1H-pyrazole (1.2 g, 5.6 mmol, 1.3 equiv.) was added. The reaction mixture was stirred for 2 h at −70° C., then quenched with $NH_4Cl$ (aq.), extracted with EA twice. The combined organic layers were washed with brine, dried over $Na_2SO_4$ and concentrated under vacuum. The residue was purified with silica gel chromatography (0→50% EA/PE) to yield tert-butyl 4-(1-(1-(5-bromopyridin-2-yl)-2-(1-(difluoromethyl)-1H-pyrazol-3-yl)ethyl)-1H-pyrazol-4-yl)benzoate as light yellow oil. LC/MS: mass calculated for $C_{25}H_{24}BrF_2N_5O_2$: 543.11, measured (ES, m/z): 566.10, 568.10 [M+Na, M+Na+2]$^+$.

Step 3: (6-(1-(4-(4-(tert-Butoxycarbonyl)phenyl)-1H-pyrazol-1-yl)-2-(1-(difluoromethyl)-1H-pyrazol-3-yl)ethyl)pyridin-3-yl)boronic acid To a solution of tert-butyl 4-(1-(1-(5-bromopyridin-2-yl)-2-(1-(difluoromethyl)-1H-pyrazol-3-yl)ethyl)-1H-pyrazol-4-yl)benzoate (1.6 g, 2.9 mmol, 1.0 equiv.) in 1,4-dioxane (30 mL) was added 4,4,4',4',5,5,5',5'-octamethyl-2,2'-bi(1,3,2-dioxaborolane) (1.5 g, 5.9 mmol, 2.0 equiv.), potassium acetate (0.87 g, 8.8 mmol, 3.0 equiv.) and Pd(dppf)$Cl_2 \cdot CH_2Cl_2$ (0.24 g, 0.3 mmol, 0.1 equiv.) under $N_2$. The reaction mixture was stirred for 2 h at 90° C., then cooled to room temperature. and quenched with water, extracted with EA twice. The combined organic layers were washed with brine, dried over $Na_2SO_4$ and concentrated under vacuum to yield (6-(1-(4-(4-(Tert-butoxycarbonyl)phenyl)-1H-pyrazol-1-yl)-2-(1-(difluoromethyl)-1H-pyrazol-3-yl)ethyl)pyridin-3-yl)boronic acid as black oil. LC/MS: mass calculated for $C_{25}H_{26}BF_2N_5O_4$: 509.20, measured (ES, m/z): 510.15 [M+H]$^+$.

Step 4: tert-Butyl 4-(1-(1-(5-(3-chloro-6-(4-chloro-1H-1,2,3-triazol-1-yl)-2-fluorophenyl)pyridin-2-yl)-2-(1-(difluoromethyl)-1H-pyrazol-3-yl)ethyl)-1H-pyrazol-4-yl)benzoate To a solution of 4-chloro-1-(4-chloro-3-fluoro-2-iodophenyl)-1H-1,2,3-triazole (0.3 g, 0.84 mmol, 1.0 equiv.) and (6-(1-(4-(4-(tert-butoxycarbonyl)phenyl)-1H-pyrazol-1-yl)-2-(1-(difluoromethyl)-1H-pyrazol-3-yl)ethyl)pyridin-3-yl) boronic acid (1.0 g, resulting) in 1,4-dioxane (20 mL) and water (4 mL) was added potassium carbonate (0.35 g, 2.5 mmol, 3.0 equiv.) and Pd(PPh$_3$)$_4$ (100 mg, 0.08 mmol, 0.1 equiv.) under $N_2$. The reaction mixture was stirred for 2 h at 95° C., then quenched with water, extracted with EA, dried over $Na_2SO_4$ and concentrated under vacuum. The residue was purified by silica gel chromatography (0→100% EA/PE) to yield tert-butyl 4-(1-(1-(5-(3-chloro-6-(4-chloro-1H-1,2,3-triazol-1-yl)-2-fluorophenyl)pyridin-2-yl)-2-(1-(difluoromethyl)-1H-pyrazol-3-yl)ethyl)-1H-pyrazol-4-yl) benzoate as a light brown solid. LC/MS: mass calculated for $C_{33}H_{27}Cl_2F_3N_8O_2$: 694.16, measured (ES, m/z): 695.15 [M+H]$^+$.

Step 5: 4-(1-(1-(5-(3-Chloro-6-(4-chloro-1H-1,2,3-triazol-1-yl)-2-fluorophenyl)pyridin-2-yl)-2-(1-(difluoromethyl)-1H-pyrazol-3-yl)ethyl)-1H-pyrazol-4-yl)benzoic acid To a solution of tert-butyl 4-(1-(1-(5-(3-chloro-6-(4-chloro-1H-1,2,3-triazol-1-yl)-2-fluorophenyl)pyridin-2-yl)-2-(1-(difluoromethyl)-1H-pyrazol-3-yl)ethyl)-1H-pyrazol-4-yl)benzoate (0.5 g, 0.72 mmol, 1.0 equiv.) in DCM (15 mL) was added TFA (5 mL). The reaction mixture was stirred at room temperature. for 2 h, then concentrated under vacuum. The residue was purified by reverse column chromatography on C18 (CH$_3$CN/H$_2$O (0.05% CF$_3$COOH): 5→70%) to yield 4-(1-(1-(5-(3-chloro-6-(4-chloro-1H-1,2,3-triazol-1-yl)-2-fluorophenyl)pyridin-2-yl)-2-(1-(difluoromethyl)-1H-pyrazol-3-yl)ethyl)-1H-pyrazol-4-yl)benzoic acid as an off-white solid. LC/MS: mass calculated for $C_{29}H_{19}Cl_2F_3N_8O_2$: 638.10, measured (ES, m/z): 639.10 [M+H]$^+$.

Step 6: (S*)-2-(1-(4-(4-Carboxyphenyl)-1H-pyrazol-1-yl)-2-(1-(difluoromethyl)-1H-pyrazol-3-yl)ethyl)-5-(3-chloro-6-(4-chloro-1H-1,2,3-triazol-1-yl)-2-fluorophenyl)pyridine 1-oxide To a solution of 4-(1-(1-(5-(3-chloro-6-(4-chloro-1H-1,2,3-triazol-1-yl)-2-fluorophenyl)pyridin-2-yl)-2-(1-(difluoromethyl)-1H-pyrazol-3-yl)ethyl)-1H-pyrazol-4-yl)benzoic acid (390 mg, 0.61 mmol, 1.0 equiv.) in MeOH (10 mL) was added 30 wt % hydrogen peroxide solution (690 mg, 6.10 mmol, 10.0 equiv.) followed by the addition of methyltrioxorhenium (46 mg, 0.18 mmol, 0.3 equiv.). The reaction mixture was stirred at room temperature for 2 h, then purified by reverse column chromatography on C18 (330 g, MeCN/H$_2$O (0.05% CF$_3$COOH): 5→70%) and then by Prep-Chiral-HPLC to yield (S*)-2-(1-(4-(4-carboxyphenyl)-1H-pyrazol-1-yl)-2-(1-(difluoromethyl)-1H-pyrazol-3-yl)ethyl)-5-(3-chloro-6-(4-chloro-1H-1,2,3-triazol-1-yl)-2-fluorophenyl)pyridine 1-oxide as a white solid. LC/MS: mass calculated for C$_{29}$H$_{19}$Cl$_2$F$_3$N$_8$O$_3$: 654.09, measured (ES, m/z): 655.10 [M+H]$^+$ Step 7: (S*)-2-(1-(4-(4-Carbamoylphenyl)-1H-pyrazol-1-yl)-2-(1-(difluoromethyl)-1H-pyrazol-3-yl)ethyl)-5-(3-chloro-6-(4-chloro-1H-1,2,3-triazol-1-yl)-2-fluorophenyl)pyridine 1-oxide To a mixture of (S*)-2-(1-(4-(4-carboxyphenyl)-1H-pyrazol-1-yl)-2-(1-(difluoromethyl)-1H-pyrazol-3-yl)ethyl)-5-(3-chloro-6-(4-chloro-1H-1,2,3-triazol-1-yl)-2-fluorophenyl)pyridine 1-oxide (95 mg, 0.14 mmol, 1.0 equiv.) and ammonium chloride (39 mg, 0.72 mmol, 5.0 equiv.) and 2-(3H-[1,2,3]triazolo[4,5-b]pyridin-3-yl)-1,1,3,3-tetramethylisouronium (82 mg, 0.22 mmol, 1.5 equiv.) in N,N-dimethylformamide (5 mL) was added N-ethyl-N-isopropylpropan-2-amine (56 mg, 0.43 mmol, 3.0 equiv.). The reaction was stirred at room temperature. for 4 h, then purified by reverse phase chromatography on C18 (120 g, MeCN/H$_2$O (0.05% CF$_3$COOH): 5→50%) to yield (S*)-2-(1-(4-(4-carbamoylphenyl)-1H-pyrazol-1-yl)-2-(1-(difluoromethyl)-1H-pyrazol-3-yl)ethyl)-5-(3-chloro-6-(4-chloro-1H-1,2,3-triazol-1-yl)-2-fluorophenyl)pyridine 1-oxide as white solid.

LC/MS: mass calculated for C$_{29}$H$_{20}$Cl$_2$F$_3$N$_9$O$_2$: 653.11, measured (ES, m/z): 654.05 [M+H]$^+$. $^1$H NMR (300 MHz, DMSO-d$_6$): δ 8.69 (s, 1H), 8.53 (s, 1H), 8.45 (s, 1H), 8.11 (s, 1H), 7.98-8.08 (m, 2H), 7.95 (s, 1H), 7.83-7.92 (m, 2H), 7.62-7.74 (m, 3H), 7.12-7.56 (m, 3H), 6.33-6.43 (m, 1H), 6.11 (d, J=2.6 Hz, 1H), 3.64-3.81 (m, 2H). $^{19}$F NMR (282 MHz, DMSO-d$_6$): δ −74.30, −93.79, −112.93.

Example 970: 2-(1-4-(4-Carboxy-3-fluorophenyl)-1H-pyrazol-1-yl)-2-(oxazol-2-yl)ethyl)-5-(3-chloro-2-fluoro-6-(4-(trifluoromethyl)-1H-1,2,3-triazol-1-yl)phenyl)pyridine 1-oxide TFA

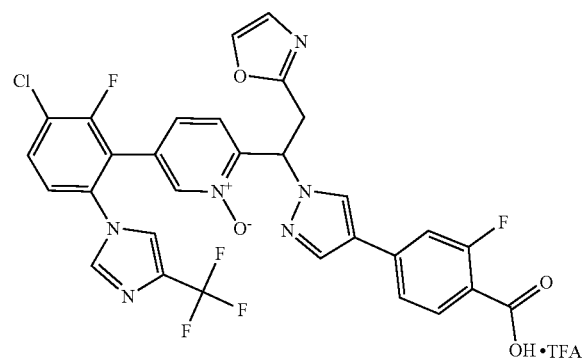 [SMILES: O=C(O)c1ccc(-c2cnn(C(Cc3ncco3)c3ccc(-c4c(-n5cnc(C(F)(F)F)c5)ccc(Cl)c4F)c[n+]3[O-])c2)cc1F]

To a solution of 4-(1-(1-(5-(3-chloro-2-fluoro-6-(4-(trifluoromethyl)-1H-1,2,3-triazol-1-yl)phenyl)pyridin-2-yl)-2-(oxazol-2-yl)ethyl)-1H-pyrazol-4-yl)-2-fluorobenzoic acid (30 mg, 0.0467 mmol) in CH$_3$OH (3 mL) was added methyltrioxorhenium (5.82 mg, 0.0234 mmol) and H$_2$O$_2$ (0.0481 mL, 0.467 mmol, 30%). The resulting mixture was stirred at room temperature for 1.5 h. The solvent was removed, and the residue was purified by via ISCO reverse phase column 0.1% TFA in water and 0.1% TFA in ACN (35% to 65% 0.1% TFA in ACN gradient) to yield: 2-(1-4-(4-carboxy-3-fluorophenyl)-1H-pyrazol-1-yl)-2-(oxazol-2-yl)ethyl)-5-(3-chloro-2-fluoro-6-(4-(trifluoromethyl)-1H-1,2,3-triazol-1-yl)phenyl)pyridine 1-oxide TFA as a white solid.

LC/MS: mass calculated for C$_{29}$H$_{17}$ClF$_5$N$_7$O$_4$: 657.1, measured (ES, m/z): 658.7 [M+H]$^+$. $^1$H NMR: (DMSO-d$_6$, 400 MHz) δ 13.15 (br s, 1H), 9.18 (s, 1H), 8.64 (s, 1H), 8.48 (s, 1H), 8.14 (s, 1H), 8.07 (br t, J=8.07 Hz, 1H), 7.97 (s, 1H), 7.68-7.92 (m, 2H), 7.39-7.67 (m, 2H), 7.26 (d, J=8.31 Hz, 1H), 7.17 (d, J=8.31 Hz, 1H), 7.06 (s, 1H), 6.55 (dd, J=9.54, 5.14 Hz, 1H) 3.64-3.93 (m, 2H). $^{19}$F-NMR: (DMSO-d$_6$, 377 MHz) δ −125.19, −122.35, −86.68, −72.09.

Example 971: (S*)-2-(1-(4-(4-Carbamoyl-3-fluorophenyl)-1H-pyrazol-1-yl)-3-(methoxy-d3)propyl-3,3-d2)-5-(3-chloro-2-fluoro-6-(4-(trifluoromethyl)-1H-1,2,3-triazol-1-yl)phenyl)pyridine 1-oxide

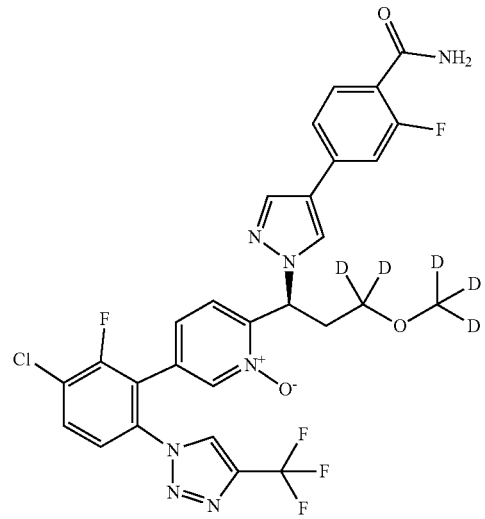 [SMILES: [2H]C([2H])([2H])OC([2H])([2H])C[C@@H](c1ccc(-c2c(-n3cc(C(F)(F)F)nn3)ccc(Cl)c2F)c[n+]1[O-])n1cc(-c2ccc(C(N)=O)c(F)c2)cn1]

Step 1: Ethyl 3-(5-bromopyridin-2-yl)-3-oxopropanoate

To the solution of methyl 5-bromopicolinate (30.0 g, 138.9 mmol, 1.0 equiv.) in EA (122.4 g, 1.39 mol, 10.0 equiv.) and THF (300 mL) was added LiHMDS (166.6 ml, 166.64 mmol, 1.2 equiv.) at −30° C. at N$_2$ atmosphere and stirred for 2 h. The reaction was quenched by saturated NH$_4$Cl aqueous and extracted by EA. The organic layer was washed by H$_2$O and brine, dried by anhydrous Na$_2$SO$_4$ and concentrated to yield yellow oil. The resulting residue was purified by silica gel column chromatography with PE:EA=5:1 to yield ethyl 3-(5-bromopyridin-2-yl)-3-oxopropanoate as a yellow oil. LC/MS: mass calculated for C$_{10}$H$_{10}$BrNO$_3$: 270.98, measured (ES, m/z): 271.95, 273.95 [M+H, M+H+2]$^+$.

Step 2: 1-(5-Bromopyridin-2-yl)propane-1,3,3-d$_3$-1,3-diol

To the solution of ethyl 3-(5-bromopyridin-2-yl)-3-oxopropanoate (20.0 g, 73.50 mmol, 1.0 equiv.) in MeOH (250 mL) was added NaBD$_4$ (2.5 g, 588.03 mmol, 8.0 equiv.) at 0° C. and stirred for 3 h at 80° C. MeOH was removed by rotary evaporate and the residue was dispersed with EA, then the mixture was filtered. The filtrate was concentrated, and the resulting residue was purified by silica gel column chromatography to yield 1-(5-bromopyridin-2-yl)propane-1,3,3-d$_3$-1,3-diol as a white solid. LC/MS: mass calculated for C$_8$H$_7$D$_3$BrNO$_2$: 234.01, measured (ES, m/z): 235.15, 237.10 [M+H, M+H+2]$^+$.

Step 3: 1-(5-Bromopyridin-2-yl)-3-hydroxypropan-1-one-3,3-d$_2$

To the solution of 1-(5-bromopyridin-2-yl)propane-1,3,3-d$_3$-1,3-diol (5.0 g, 21.27 mmol, 1.0 equiv.) in DCM (75 mL) was added manganese (IV) oxide (2.8 g, 319.02 mmol, 15.0 equiv.) and stirred overnight at 50° C. The reaction was monitored by LCMS. The mixture was filtered. The filtrate was concentrated, and the resulting residue was purified by silica gel column chromatography to yield 1-(5-bromopyridin-2-yl)-3-hydroxypropan-1-one-3,3-d$_2$ as a light yellow oil. LC/MS: mass calculated for C$_8$H$_6$D$_2$BrNO$_2$: 230.99, measured (ES, m/z): 232.10, 234.10 [M+H, M+H+2]$^+$.

Step 4: 1-(5-Bromopyridin-2-yl)-3-(methoxy-d3) propan-1-one-3,3-d$_2$

To the solution of 1-(5-bromopyridin-2-yl)-3-hydroxypropan-1-one-3,3-d$_2$ (4.0 g, 17.24 mmol, 1.0 equiv.) in DCM (150 mL) was added Ag$_2$O (2.4 g, 103.42 mmol, 6.0 equiv.) and the mixture stirred for 30 min.
Then iodomethane-d$_3$ (2.0 g, 137.92 mmol, 8.0 equiv.) was added. The reaction was monitored by LCMS. The mixture was filtered. The filtrate was concentrated, and the resulting residue was purified by silica gel column chromatography to yield 1-(5-bromopyridin-2-yl)-3-(methoxy-d$_3$) propan-1-one-3,3-d$_2$ as a light yellow oil. LC/MS: mass calculated for C$_9$H$_5$D$_5$BrNO$_2$: 248.02, measured (ES, m/z): 249.15, 251.15 [M+H, M+H+2]$^+$.

Step 5: 1-(5-Bromopyridin-2-yl)-3-(methoxy-d3) propan-3,3-d$_2$-1-ol

To the solution of 1-(5-bromopyridin-2-yl)-3-(methoxy-d$_3$)propan-1-one-3,3-d$_2$ (2.0 g, 8.03 mmol, 1.0 equiv.) in MeOH (50 mL) was added NaBH$_4$ (334 mg, 8.83 mmol, 1.1 equiv.) at 0° C. and stirred for 3 h. MeOH was removed by rotary evaporate and the residue was dispersed with EA, then the mixture was filtered. The filtrate was concentrated, and the resulting residue was purified by silica gel column chromatography to yield 1-(5-bromopyridin-2-yl)-3-(methoxy-d$_3$)propan-3,3-d$_2$-1-ol as a light yellow oil. LC/MS: mass calculated for C$_9$H$_7$D$_5$BrNO$_2$: 250.04, measured (ES, m/z): 251.05, 253.05 [M+H, M+H+2]$^+$.

Step 6: 1-(5-bromopyridin-2-yl)-3-(methoxy-d$_3$) propyl-3,3-d2 methanesulfonate To the solution of 1-(5-bromopyridin-2-yl)-3-(methoxy-d$_3$)propan-3,3-d$_2$-1-ol (1.2 g, 4.78 mmol, 1.0 equiv.) and methanesulfonic anhydride (1.2 g, 7.17 mmol, 1.5 equiv.) in DCM (50 mL) was added Et$_3$N (1.5 g, 14.34 mmol, 3.0 equiv.) and the mixture stirred for 4 h at room temperature. The mixture was extracted by DCM and washed by H$_2$O, dried by anhydrous Na$_2$SO$_4$ and concentrated to yield a light yellow solid. The light yellow solid was purified by silica gel column chromatography with PE:EA=3:1 to yield 1-(5-bromopyridin-2-yl)-3-(methoxy-d$_3$)propyl-3,3-d$_2$ methanesulfonate as a light yellow solid. LC/MS: mass calculated for C$_{10}$H$_9$D$_5$BrNO$_4$S: 328.01, measured (ES, m/z): 329.10, 331.10 [M+H, M+H+2]$^+$.

Step 7: (R)-4-(1-(1-(5-Bromopyridin-2-yl)-3-(methoxy-d$_3$)propyl-3,3-d$_2$)-1H-pyrazol-4-yl)-2-fluorobenzamide To the solution of 1-(5-bromopyridin-2-yl)-3-(methoxy-d$_3$)propyl-3,3-d$_2$ methanesulfonate (0.42 g, 1.22 mmol, 1.0 equiv.) and 2-fluoro-4-(1H-pyrazol-4-yl)benzamide (249 mg, 1.22 mmol, 1.0 equiv.) in DMF (20 mL) was added sodium 2-methylpropan-2-olate (111 mg, 1.15 mmol, 0.9 equiv.) and the mixture stirred for 4 h at room temperature. The mixture solution was extracted by EA and washed by H$_2$O, dried by anhydrous Na$_2$SO$_4$ and concentrated to yield white solid, which was further purified by silica gel column chromatography with PE:EA=1:3 to yield (R)-4-(1-(1-(5-bromopyridin-2-yl)-3-(methoxy-d$_3$)propyl-3,3-d$_2$)-1H-pyrazol-4-yl)-2-fluorobenzamide as a light yellow solid. LC/MS: mass calculated for C$_{19}$H$_{13}$D$_5$BrFN$_4$O$_2$: 437.09, measured (ES, m/z): 438.15, 440.10 [M+H, M+H+2]$^+$.

Step 8: (R)-(6-(1-(4-(4-Carbamoyl-3-fluorophenyl)-1H-pyrazol-1-yl)-3-(methoxy-d$_3$)propyl-3,3-d$_2$)pyridin-3-yl)boronic acid To the solution of (R)-4-(1-(1-(5-bromopyridin-2-yl)-3-(methoxy-d$_3$)propyl-3,3-d$_2$)-1H-pyrazol-4-yl)-2-fluorobenzamide (530 mg, 1.21 mmol, 1.0 equiv.) and 4,4,4',4',5,5,5',5'-octamethyl-2,2'-bi(1,3,2-dioxaborolane) (614 mg, 2.42 mmol, 2.0 equiv.) in 1,4-dioxane (20 mL) was added Pd(dppf)Cl$_2$ (88 mg, 0.12 mmol, 0.1 equiv.) and KOAc (356 mg, 3.63 mmol, 3.0 equiv.) the mixture stirring overnight at 90° C. The resulting mixture was used in the next step without further purification. LC/MS: mass calculated for C$_{19}$H$_{15}$D$_5$BFN$_4$O$_4$: 403.19, measured (ES, m/z): 404.20 [M+H]$^+$.

Step 9: (R)-4-(1-(1-(5-(3-Chloro-2-fluoro-6-(4-(trifluoromethyl)-1H-1,2,3-triazol-1-yl)phenyl)pyridin-2-yl)-3-(methoxy-d$_3$)propyl-3,3-d$_2$)-1H-pyrazol-4-yl)-2-fluorobenzamide To the solution of (R)-(6-(1-(4-(4-carbamoyl-3-fluorophenyl)-1H-pyrazol-1-yl)-3-(methoxy-d$_3$)propyl-3,3-d$_2$) pyridin-3-yl)boronic acid (0.30 g, 0.74 mmol, 1.0 equiv.) and 1-(4-chloro-3-fluoro-2-iodophenyl)-4-(trifluoromethyl)-1H-1,2,3-triazole (437 mg, 1.12 mmol, 1.5 equiv.) in 1,4-dioxane (30 mL) and H$_2$O (3 mL) was added Pd(PPh$_3$)$_4$ (86 mg, 0.07 mmol, 0.1 equiv.) and K$_2$CO$_3$ (205 mg, 1.49 mmol, 2.0 equiv.) and the mixture stirring overnight at 90° C. The mixture was extracted by EA and washed by H$_2$O, dried by anhydrous Na$_2$SO$_4$ and concentrated to yield a light yellow solid, which was further purified by silica gel column chromatography with PE:EA=1:4 to yield (R)-4-(1-(1-(5-(3-chloro-2-fluoro-6-(4-(trifluoromethyl)-1H-1,2,3-triazol-1-yl)phenyl)pyridin-2-yl)-3-(methoxy-d$_3$)propyl-3,3-d$_2$)-1H-pyrazol-4-yl)-2-fluorobenzamide as a light yellow solid. LC/MS: mass calculated for C$_{28}$H$_{16}$D$_5$ClF$_5$N$_7$O$_2$: 622.17, measured (ES, m/z): 623.30 [M+H]$^+$.

Step 10: (S*)-2-(1-(4-(4-Carbamoyl-3-fluorophenyl)-1H-pyrazol-1-yl)-3-(methoxy-d$_3$)propyl-3,3-d$_2$)-5-(3-chloro-2-fluoro-6-(4-(trifluoromethyl)-1H-1,2,3-triazol-1-yl)phenyl)pyridine 1-oxide A mixture of (R)-4-(1-(1-(5-(3-chloro-2-fluoro-6-(4-(trifluoromethyl)-1H-1,2,3-triazol-1-yl)phenyl)pyridin-2-yl)-3-

(methoxy-d₃)propyl-3,3-d₂)-1H-pyrazol-4-yl)-2-fluorobenzamide (0.20 g, 0.32 mmol, 1.0 equiv.), methyltrioxorhenium (80 mg, 0.32 mmol, 1.0 equiv.), hydrogen peroxide (109 mg, 3.21 mmol, 10.0 equiv.) in CH₃OH (10 mL) was stirred for 3 h at room temperature. The resulting mixture was purified by reverse phase chromatography on C₁₈ (MeCN/H₂O (0.05% CF₃COOH)) to yield 2-(1-(4-(4-carbamoyl-3-fluorophenyl)-1H-pyrazol-1-yl)-3-(methoxy-d₃)propyl-3,3-d₂)-5-(3-chloro-2-fluoro-6-(4-(trifluoromethyl)-1H-1,2,3-triazol-1-yl)phenyl)pyridine 1-oxide as a white solid. The racemic product was separated by Chiral-HPLC to yield (S*)-2-(1-(4-(4-carbamoyl-3-fluorophenyl)-1H-pyrazol-1-yl)-3-(methoxy-d₃)propyl-3,3-d₂)-5-(3-chloro-2-fluoro-6-(4-(trifluoromethyl)-1H-1,2,3-triazol-1-yl)phenyl)pyridine 1-oxide as a white solid.

LC/MS: mass calculated for $C_{28}H_{16}ClD_5F_5N_7O_3$: 638.16, measured (ES, m/z): 639.15 [M+H]⁺. ¹H NMR (400 MHz, DMSO-d₆) δ 9.16 (d, J=1.2 Hz, 1H), 8.58 (s, 1H), 8.40 (d, J=1.6 Hz, 1H), 8.13 (s, 1H), 8.11-8.02 (m, 1H), 7.76-7.81 (m, 1H), 7.66-7.72 (m, 1H), 7.51-7.66 (m, 4H), 7.33 (d, J=8.3 Hz, 1H), 7.13-7.15 (m, 1H), 6.13-6.19 (m, 1H), 2.43-2.44 (m, 2H). ¹⁹F-NMR (376 MHz, DMSO-d₆): δ −59.76, −112.87, −112.99.

Example 972: (R*)-2-(1-(4-(4-Carbamoyl-3-fluorophenyl)-1H-pyrazol-1-yl)-3-(methoxy-d3)propyl-3,3-d2)-5-(3-chloro-2-fluoro-6-(4-(trifluoromethyl)-1H-1,2,3-triazol-1-yl)phenyl)pyridine 1-oxide

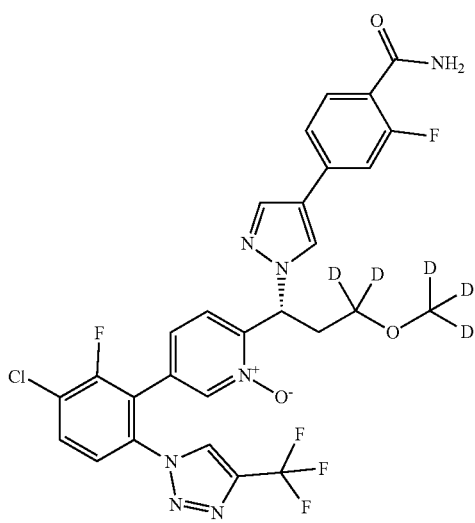 [SMILES: [2H]C([2H])([2H])OC([2H])([2H])C[C@H](c1ccc(-c2c(-n3cc(C(F)(F)F)nn3)ccc(Cl)c2F)c[n+]1[O-])n1cc(-c2ccc(C(N)=O)c(F)c2)cn1]

LC/MS: mass calculated for $C_{28}H_{16}ClD_5F_5N_7O_3$: 638.16, measured (ES, m/z): 639.15 [M+H]⁺. ¹H NMR (400 MHz, DMSO-d₆) δ: 9.18 (s, 1H), 8.59 (s, 1H), 8.42 (s, 1H), 8.14 (s, 1H), 8.04-8.08 (m, 1H), 7.77-7.79 (m, 1H), 7.69-7.71 (m, 1H), 7.52-7.56 (m, 4H), 7.31-7.33 (m, 1H), 7.14-7.16 (m, 1H), 6.17-6.21 (m, 1H), 2.47-2.51 (m, 2H). 19FNMR (400 MHz, DMSO-d₆) d: −59.76, −112.87, −113.00.

Example 973: 2-(1-(4-(4-Carbamoyl-3-fluorophenyl)-1H-pyrazol-1-yl)-2-(1,2,4-oxadiazol-3-yl)ethyl)-5-(3-chloro-2-fluoro-6-(4-(trifluoromethyl)-1H-1,2,3-triazol-1-yl)phenyl)pyridin 1-oxide

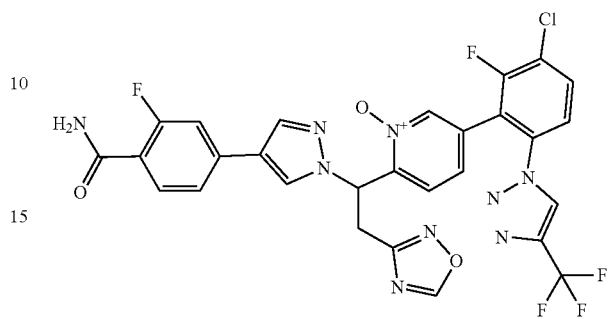

To a solution of 4-(1-(1-(5-(3-chloro-2-fluoro-6-(4-(trifluoromethyl)-1H-1,2,3-triazol-1-yl)phenyl)pyridin-2-yl)-2-(1,2,4-oxadiazol-3-yl)ethyl)-1H-pyrazol-4-yl)-2-fluorobenzamide (0.022 g, 0.0343 mmole) in CH₃OH (2 mL) were added methyl trioxorhenium (VII) (6.5 mg, 0.0259 mmole), and 30% hydrogen peroxide (0.04 mL, 0.388 mmole). The reaction mixture was stirred at room temperature for 3 Hours. The solid was filtered and washed with DCM. The organic solvent was removed under vacuum. The filtrate was concentrated and purified via mass directed reverse phase column chromatography with 0.1% TFA in water and 0.1% TFA in ACN as eluent. The selected fraction was concentrated to yield 2-(1-(4-(4-carbamoyl-3-fluorophenyl)-1H-pyrazol-1-yl)-2-(1,2,4-oxadiazol-3-yl)ethyl)-5-(3-chloro-2-fluoro-6-(4-(trifluoromethyl)-1H-1,2,3-triazol-1-yl)phenyl) pyridine 1-oxide as a white solid.

LC-MS: calculated mass for $C_{28}H_{17}ClF_5N_9O_3$: 657.1, measured (ES, m/z): 658.2 [M+H]⁺. ¹H NMR (DMSO-d₆, 400 MHz) δ 9.51 (s, 1H), 9.18 (s, 1H), 8.58 (s, 1H), 8.49 (s, 1H), 8.11 (s, 1H), 8.07 (t, J=7.9 Hz, 1H), 7.78 (dd, J=8.8, 1.5 Hz, 1H), 7.69-7.44 (m, 4H), 7.30 (d, J=8.3 Hz, 1H), 7.23-7.18 (m, 1H), 6.58-6.52 (m, 1H), 3.95-3.76 (m, 3H). ¹⁹F NMR (DMSO-d₆, 373 MHz) δ −125.3 (s), −125.2 (s), −86.6 (s).

Example 974: (R*)-5-(5-Chloro-2-(1H-tetrazol-1-yl)phenyl)-2-(2-cyclopropyl-1-(4-(1-(difluoromethyl)-1H-1,2,4-triazol-5-yl)-1H-pyrazol-1-yl)ethyl)-4-methoxypyridine 1-oxide

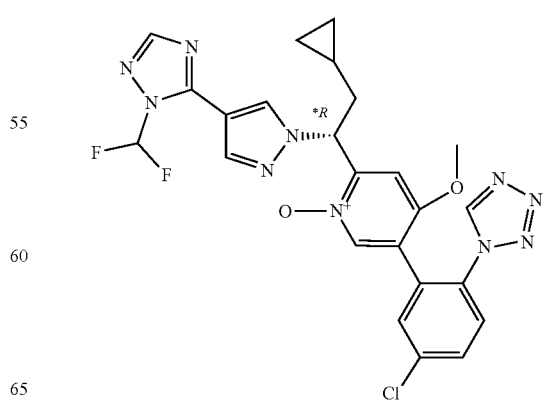

LC/MS: mass calculated for $C_{24}H_{21}ClF_2N_{10}O_2$: 554.15, measured (ES, m/z): 555.15 [M+H]$^+$. $^1$H NMR (300 MHz, CD$_3$OD) δ 9.45 (s, 1H), 8.59 (s, 1H), 8.38 (s, 1H), 7.11-8.14 (m, 2H), 7.82 (t, J=57.7 Hz, 1H), 7.77-7.81 (m, 1H), 7.76 (s, 1H), 7.72-7.75 (m, 1H), 7.17 (s, 1H), 6.42-6.31 (m, 1H), 3.59 (s, 3H), 2.42-2.58 (m, 1H), 2.02-2.18 (m, 1H), 0.64-0.73 (m, 1H), 0.34-0.56 (m, 2H), 0.17-0.28 (m, 1H), 0.03-0.12 (m, 1H). $^{19}$F NMR (282 MHz, CD$_3$OD) δ −96.88, −98.77.

Example 975: (S*)-5-(5-Chloro-2-(1H-tetrazol-1-yl)phenyl)-2-(2-cyclopropyl-1-(4-(1-(difluoromethyl)-1H-1,2,4-triazol-5-yl)-1H-pyrazol-1-yl)ethyl)-4-methoxypyridine 1-oxide

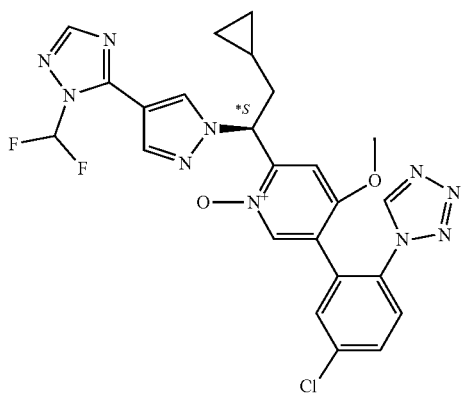

LC/MS: mass calculated for $C_{24}H_{21}ClF_2N_{10}O_2$: 554.15, measured (ES, m/z): 555.15 [M+H]$^+$. $^1$H NMR (400 MHz, CD$_3$OD) δ 9.45 (s, 1H), 8.59 (s, 1H), 8.38 (s, 1H), 8.08-8.12 (m, 2H), 7.80 (t, J=57.8 Hz, 1H), 7.77 (dd, J=8.6, 2.2 Hz, 1H), 7.74 (s, 1H), 7.71 (d, J=2.2 Hz, 1H), 7.17 (s, 1H), 6.31-6.42 (m, 1H), 3.59 (s, 3H), 2.42-2.58 (m, 1H), 2.02-2.18 (m, 1H), 0.64-0.73 (m, 1H), 0.34-0.56 (m, 2H), 0.15-0.25 (m, 1H), 0.03-0.12 (m, 1H). $^{19}$F NMR (282 MHz, CD$_3$OD) δ −95.72, −98.77.

Example 976: (R*)-5-(5-Chloro-2-(4-(trifluoromethyl)-1H-1,2,3-triazol-1-yl)phenyl)-2-(2-cyclopropyl-1-(4-(1-methyl-1H-1,2,4-triazol-5-yl)-1H-pyrazol-1-yl)ethyl)-4-methoxypyridine 1-oxide

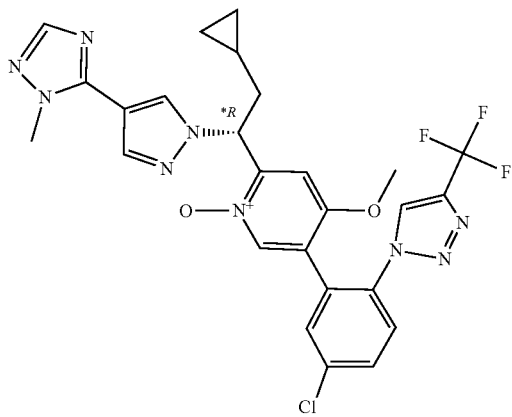

LC/MS: mass calculated for $C_{26}H_{23}ClF_3N_9O_2$: 585.16, measured (ES, m/z): 586.20 [M+H]$^+$. $^1$H NMR (300 MHz, CD$_3$OD) δ 8.86 (s, 1H), 8.57 (s, 1H), 8.36 (s, 1H), 8.12 (s, 1H), 7.94 (s, 1H), 7.81-7.75 (m, 2H), 7.72 (d, J=2.2 Hz, 1H), 7.16 (s, 1H), 6.33-6.44 (m, 1H), 4.06 (s, 3H), 3.58 (s, 3H), 2.43-2.59 (m, 1H), 2.03-2.20 (m, 1H), 0.63-0.73 (m, 1H), 0.38-0.53 (m, 2H), 0.19-0.30 (m, 1H), 0.04-0.14 (m, 1H). $^{19}$F NMR (282 MHz, CD$_3$OD). δ −62.601.

2-(2-cyclopropyl-1-(4-(1-methyl-1H-1,2,4-triazol-5-yl)-1H-pyrazol-1-yl)ethyl)-4-methoxypyridine 1-oxide

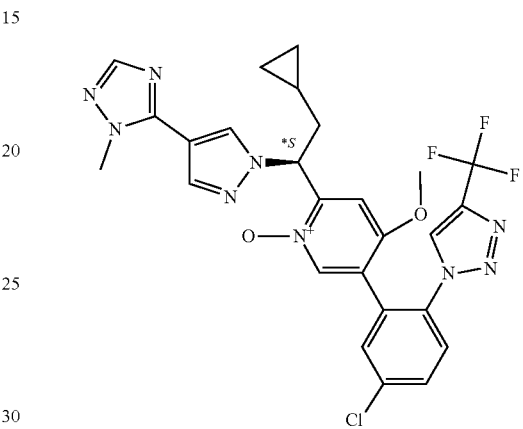

LC/MS: mass calculated for $C_{26}H_{23}ClF_3N_9O_2$: 585.16, measured (ES, m/z): 586.20 [M+H]$^+$. $^1$H NMR (300 MHz, CD$_3$OD) δ 8.86 (s, 1H), 8.57 (s, 1H), 8.36 (s, 1H), 8.12 (s, 1H), 7.94 (s, 1H), 7.69-7.83 (m, 3H), 7.16 (s, 1H), 6.33-6.44 (m, 1H), 4.06 (s, 3H), 3.58 (s, 3H), 2.43-2.59 (m, 1H), 2.03-2.20 (m, 1H), 0.63-0.73 (m, 1H), 0.38-0.53 (m, 2H), 0.19-0.30 (m, 1H), 0.04-0.14 (m, 1H)./19F NMR (282 MHz, CD$_3$OD) δ −62.60.

Example 978: (S*)-5-(3-Chloro-6-(4-chloro-1H-1,2,3-triazol-1-yl)-2-fluorophenyl)-2-(2-(1-(difluoromethyl)-1H-pyrazol-3-yl)-1-(4-(4-fluoro-1-methyl-1H-1,2,3-triazol-5-yl)-1H-pyrazol-1-yl)ethyl)pyridine 1-oxide

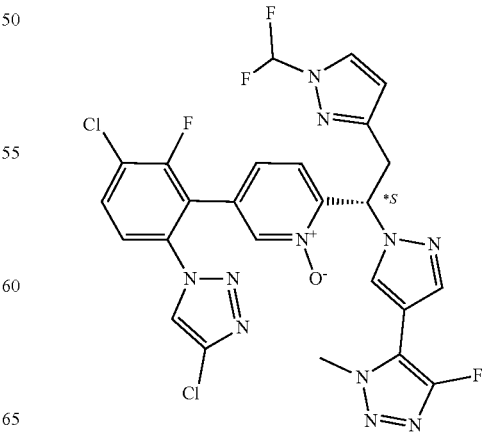

Step 1: 2-(1-(Difluoromethyl)-1H-pyrazol-3-yl)-N-methoxy-N-methylacetamide

To a solution of 1-(difluoromethyl)-1H-pyrazole-3-carboxylic acid (4.0 g, 22.7 mmol, 1.0 equiv.) in dichloromethane (40 mL) was added 1,1'-carbonyldiimidazole (5.5 g, 34.1 mmol, 1.5 equiv.) and N,O-dimethylhydroxylamine (3.3 g, 34.1 mmol, 1.5 equiv.). The reaction mixture was stirred at room temperature overnight. The reaction was added water, and the mixture extracted with EA twice. The combined layers were washed with hydrochloric acid (pH=3~4), saturated sodium bicarbonate and brine twice respectively, dried over $Na_2SO_4$ and concentrated to yield 2-(1-(difluoromethyl)-1H-pyrazol-3-yl)-N-methoxy-N-methylacetamide as white solid. LC/MS: mass calculated for $C_8H_{11}F_2N_3O_2$: 219.08, measured (ES, m/z): 220.05 $[M+H]^+$.

Step 2: 1-(5-Bromopyridin-2-yl)-2-(1-(difluoromethyl)-1H-pyrazol-3-yl)ethan-1-one To a solution of 2, 5-dibromopyridine (4.5 g, 19.2 mmol, 1.0 equiv.) in dry toluene (40 mL) was added butyllithium (8.05 mL, 20.1 mmol, 1.05 equiv. 2.5 M in THF) at −70° C. and the solution was stirred for 1 h under $N_2$. The solution of 2-(1-(difluoromethyl)-1H-pyrazol-3-yl)-N-methoxy-N-methylacetamide (4.2 g, 19.17 mmol, 1.0 equiv.) in dry toluene (10 mL) was added the above solution and the solution was stirred for 1 h. The reaction was then quenched by the addition of saturated ammonium chloride aqueous solution and extracted with ethyl acetate twice. The combined organic layers was washed with brine, dried over $Na_2SO_4$, concentrated and purified by silica gel chromatography (0→30% EA/petroleum ether) to yield 1-(5-bromopyridin-2-yl)-2-(1-(difluoromethyl)-1H-pyrazol-3-yl)ethan-1-one as yellow solid. LC/MS: mass calculated for $C_{11}H_8BrF_2N_3O$: 314.98, measured (ES, m/z): 315.95, 317.95 $[M+H, M+H+2]^+$.

Step 3: 1-(5-Bromopyridin-2-yl)-2-(1-(difluoromethyl)-1H-pyrazol-3-yl)ethan-1-ol To a solution of 1-(5-bromopyridin-2-yl)-2-(1-(difluoromethyl)-1H-pyrazol-3-yl)ethan-1-one (850 mg, 2.69 mmol, 1.0 equiv.) in $CH_3OH$ (9.0 mL) was added sodium borohydride in portions (153 mg, 4.03 mmol, 1.5 equiv.) at 0° C. The reaction mixture was stirred at room temperature for 1 h. The reaction was quenched with water, and the mixture extracted with EA twice. The combined organic layers was washed with brine, dried over $Na_2SO_4$ and concentrated under vacuum to yield 1-(5-bromopyridin-2-yl)-2-(1-(difluoromethyl)-1H-pyrazol-3-yl)ethan-1-ol as a yellow oil. LC/MS: mass calculated for $C_{11}H_{10}BrF_2N_3O$: 317.00, measured (ES, m/z): 317.95, 319.95 $[M+H, M+H+2]^+$.

Step 4: 1-(5-Bromopyridin-2-yl)-2-(1-(difluoromethyl)-1H-pyrazol-3-yl)ethyl methanesulfonate To a mixture of 1-(5-bromopyridin-2-yl)-2-(1-(difluoromethyl)-1H-pyrazol-3-yl)ethan-1-ol (850 mg, 2.67 mmol, 1.0 equiv.) and triethylamine (1.11 mL, 8.02 mmol, 3.0 equiv.) in DCM (9 mL) was added methanesulfonic anhydride (698 mg, 4.01 mmol, 2.0 equiv.) at 0° C. and the solution was stirred for 1 h at room temperature. The mixture was added $H_2O$, extracted with DCM twice. The combined organic layers was washed with brine, dried over $Na_2SO_4$, concentrated and purified by silica gel chromatography (0→50% EA/petroleum ether) to yield 1-(5-bromopyridin-2-yl)-2-(1-(difluoromethyl)-1H-pyrazol-3-yl)ethyl methanesulfonate as a yellow oil. LC/MS: mass calculated for $C_{12}H_{12}BrF_2N_3O_3S$: 394.98, measured (ES, m/z): 395.85, 397.85 $[M+H, M+H+2]^+$.

Step 5: 5-Bromo-2-(2-(1-(difluoromethyl)-1H-pyrazol-3-yl)-1-(4-(1-methyl-1H-1,2,3-triazol-5-yl)-1H-pyrazol-1-yl)ethyl)pyridine A mixture of 1-methyl-5-(1H-pyrazol-4-yl)-1H-1,2,3-triazole (219 mg, 1.47 mmol, 1.1 equiv.) and cesium carbonate (479 mg, 1.47 mmol, 1.1 equiv.) in acetonitrile (6 mL) was stirred at room temperature for 10 minutes. To the reaction mixture was then added 1-(5-bromopyridin-2-yl)-2-(1-(difluoromethyl)-1H-pyrazol-3-yl)ethyl methanesulfonate (530 mg, 1.34 mmol, 1.0 equiv.) at room temperature and the solution was stirred for 2 h at room temperature. The mixture was diluted with $H_2O$, extracted with DCM twice. The combined organic layer was washed with brine, dried over $Na_2SO_4$, concentrated and purified by silica gel chromatography (0→10% $CH_3OH$/DCM) to yield 5-bromo-2-(2-(1-(difluoromethyl)-1H-pyrazol-3-yl)-1-(4-(1-methyl-1H-1,2,3-triazol-5-yl)-1H-pyrazol-1-yl)ethyl)pyridine as a yellow oil. LC/MS: mass calculated for $C_{17}H_{15}BrF_2N_8$: 448.06, measured (ES, m/z): 448.95, 450.95 $[M+H, M+H+2]^+$.

Step 6: 5-Bromo-2-(2-(1-(difluoromethyl)-1H-pyrazol-3-yl)-1-(4-(4-fluoro-1-methyl-1H-1,2,3-triazol-5-yl)-1H-pyrazol-1-yl)ethyl)pyridine To a mixture of 5-bromo-2-(2-(1-(difluoromethyl)-1H-pyrazol-3-yl)-1-(4-(1-methyl-1H-1,2,3-triazol-5-yl)-1H-pyrazol-1-yl)ethyl)pyridine (320 mg, 0.71 mmol, 1.0 equiv.) in acetonitrile (3.5 mL) was added Selectfluor™ (505 mg, 1.43 mmol, 2.0 equiv.). The reaction mixture was stirred at 60° C. for 6 h. The reaction was quenched with water, and the mixture extracted with EA twice. The combined organic layers were washed with brine, dried over sodium sulfate and concentrated. The residue was purified by silica gel chromatography (0→60% EA/petroleum ether) to yield 5-bromo-2-(2-(1-(difluoromethyl)-1H-pyrazol-3-yl)-1-(4-(4-fluoro-1-methyl-1H-1,2,3-triazol-5-yl)-1H-pyrazol-1-yl)ethyl)pyridine as a light yellow solid. LC/MS: mass calculated for $C_{17}H_{14}BrF_3N_8$: 466.05, measured (ES, m/z): 466.95, 468.95 $[M+H, M+H+2]^+$.

Step 7: (6-(2-(1-(Difluoromethyl)-1H-pyrazol-3-yl)-1-(4-(4-fluoro-1-methyl-1H-1, 2, 3-triazol-5-yl)-1H-pyrazol-1-yl)ethyl)pyridin-3-yl)boronic acid To a mixture of 5-bromo-2-(2-(1-(difluoromethyl)-1H-pyrazol-3-yl)-1-(4-(4-fluoro-1-methyl-1H-1,2,3-triazol-5-yl)-1H-pyrazol-1-yl)ethyl)pyridine (160 mg, 0.34 mmol, 1.0 equiv.) and 4,4,4',4',5,5,5',5'-octamethyl-2,2'-bi(1,3,2-dioxaborolane) (174 mg, 0.69 mmol, 2.0 equiv.) in 1,4-dioxane (2.0 mL) was added potassium acetate (134 mg, 1.70 mmol, 5.0 equiv.) and $Pd(dppf)Cl_2$ (25 mg, 0.03 mmol, 0.1 equiv.) under $N_2$. The solution was stirred at 90° C. for 2 h. Water was added, the mixture was extracted with EA. The combined organic layers were washed with brine, dried over $Na_2SO_4$ and concentrated under vacuum to yield (6-(2-(1-(difluoromethyl)-1H-pyrazol-3-yl)-1-(4-(4-fluoro-1-methyl-1H-1, 2, 3-triazol-5-yl)-1H-pyrazol-1-yl)ethyl)pyridin-3-yl)boronic acid as a brown oil. LC/MS: mass calculated for $C_{17}H_{16}BF_3N_8O_2$: 432.14, measured (ES, m/z): 433.00 [M+H]⁺.

Step 8: 5-(3-Chloro-6-(4-chloro-1H-1,2,3-triazol-1-yl)-2-fluorophenyl)-2-(2-(1-(difluoromethyl)-1H-pyrazol-3-yl)-1-(4-(4-fluoro-1-methyl-1H-1,2,3-triazol-5-yl)-1H-pyrazol-1-yl)ethyl)pyridine To a mixture of (6-(2-(1-(difluoromethyl)-1H-pyrazol-3-yl)-1-(4-(4-fluoro-1-methyl-1H-1, 2, 3-triazol-5-yl)-1H-pyrazol-1-yl)ethyl)pyridin-3-yl)boronic acid (130 mg, resulting, 0.30 mmol, 1.0 equiv.) and 4-chloro-1-(4-chloro-3-fluoro-2-iodophenyl)-1H-1,2,3-triazole (162 mg, 0.45 mmol, 1.5 equiv.) in 1,4-dioxane (2 mL) and water (0.5 mL) was added potassium carbonate (166 mg, 1.20 mmol, 4.0 equiv.) and tetrakis(triphenylphosphine)Palladium(0) (35 mg, 0.03 mmol, 0.1 equiv.). The flask was evacuated, then purged with nitrogen. This was repeated 2×. The reaction mixture was stirred at 100° C. for 2 h under $N_2$.

Water was added, the mixture was extracted with EA. The combined organic layers were washed with brine, dried over $Na_2SO_4$ and concentrated under vacuum. The resulting solid was purified by silica gel chromatography with EA/PE (0→90%) to yield 5-(3-chloro-6-(4-chloro-1H-1,2,3-triazol-1-yl)-2-fluorophenyl)-2-(2-(1-(difluoromethyl)-1H-pyrazol-3-yl)-1-(4-(4-fluoro-1-methyl-1H-1,2,3-triazol-5-yl)-1H-pyrazol-1-yl)ethyl)pyridine as off-white solid. LC/MS: mass calculated for $C_{25}H_{17}Cl_2F_4N_{11}$: 617.10, measured (ES, m/z): 618.05 [M+H]⁺.

Step 9: (S*)-5-(3-Chloro-6-(4-chloro-1H-1,2,3-triazol-1-yl)-2-fluorophenyl)-2-(2-(1-(difluoromethyl)-1H-pyrazol-3-yl)-1-(4-(4-fluoro-1-methyl-1H-1,2,3-triazol-5-yl)-1H-pyrazol-1-yl)ethyl)pyridine 1-oxide To a solution of 5-(3-chloro-6-(4-chloro-1H-1,2,3-triazol-1-yl)-2-fluorophenyl)-2-(2-(1-(difluoromethyl)-1H-pyrazol-3-yl)-1-(4-(4-fluoro-1-methyl-1H-1,2,3-triazol-5-yl)-1H-pyrazol-1-yl)ethyl)pyridine (1.7 g, 2.75 mmol, 1.0 equiv.) and ReMeO₃ (343 mg, 1.38 mmol, 0.5 equiv.) in CH₃OH (20 mL) was added hydrogen peroxide (2.8 mL, 27.49 mmol, 30 wt %, 10.0 equiv.). The reaction mixture was stirred at room temperature for 1.0 h. The reaction was purified by reverse phase chromatography on C18 (330 g, ACN/H₂O (0.05% CF₃COOH): 0→50%) to yield a residue which was further purified by Prep-Chiral-HPLC to yield (S*)-5-(3-chloro-6-(4-chloro-1H-1,2,3-triazol-1-yl)-2-fluorophenyl)-2-(2-(1-(difluoromethyl)-1H-pyrazol-3-yl)-1-(4-(4-fluoro-1-methyl-1H-1,2,3-triazol-5-yl)-1H-pyrazol-1-yl)ethyl) pyridine 1-oxide as a white solid.

LC/MS: mass calculated for $C_{25}H_{17}Cl_2F_4N_{11}O$: 633.09, measured (ES, m/z): 634.10 [M+H]⁺. ¹H NMR (300 MHz, DMSO-d₆) δ 8.68 (s, 1H), 8.44-8.48 (m, 2H), 7.62-8.12 (m, 5H), 7.38-7.53 (m, 1H), 7.19-7.22 (m, 1H), 6.43-6.52 (m, 1H), 6.13 (d, J=2.6 Hz, 1H), 4.02 (s, 3H), 3.55-3.79 (m, 2H). ¹⁹F-NMR (282 MHz, DMSO-d₆) δ −93.55, −112.91, −145.20.

Example 979: (R*)-5-(5-Chloro-2-(4-(trifluoromethyl)-1H-1,2,3-triazol-1-yl)phenyl)-4-methoxy-2-(1-(4-(1-methyl-1H-1,2,4-triazol-5-yl)-1H-pyrazol-1-yl)propyl)pyridine 1-oxide

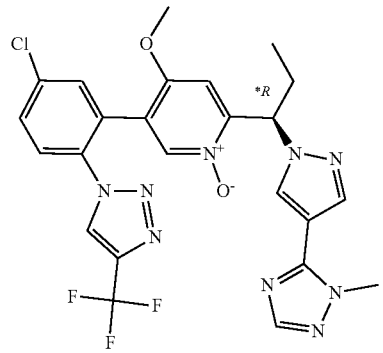 [SMILES: CC[C@H](c1cc(OC)c(-c2cc(Cl)ccc2-n2cc(C(F)(F)F)nn2)c[n+]1[O-])n1cc(-c2ncnn2C)cn1]

LC/MS: mass calculated for $C_{24}H_{21}ClF_3N_9O_2$: 559.15, measured (ES, m/z): 560.10 [M+H]⁺. ¹H NMR (400 MHz, DMSO-d₆) δ 9.21 (s, 1H), 8.62 (s, 1H), 8.35 (s, 1H), 8.04 (s, 1H), 7.89 (s, 1H), 7.83-7.84 (m, 3H), 6.92 (s, 1H), 6.08-6.13 (m, 1H), 3.96 (s, 3H), 3.38 (s, 3H), 2.21-2.37 (m, 2H), 0.85 (t, J=7.2 Hz, 3H). ¹⁹F NMR (400 MHz, DMSO-d₆). δ −59.72.

Example 980: (S*)-5-(5-Chloro-2-(4-(trifluoromethyl)-1H-1,2,3-triazol-1-yl)phenyl)-4-methoxy-2-(1-(4-(1-methyl-1H-1,2,4-triazol-5-yl)-1H-pyrazol-1-yl)propyl)pyridine 1-oxide

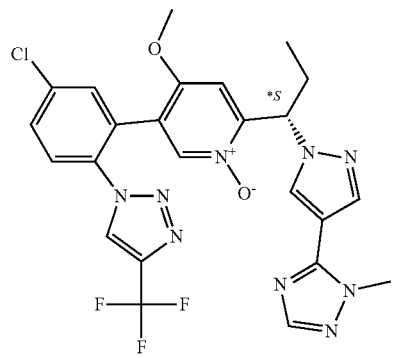 [SMILES: CC[C@@H](c1cc(OC)c(-c2cc(Cl)ccc2-n2cc(C(F)(F)F)nn2)c[n+]1[O-])n1cc(-c2ncnn2C)cn1]

LC/MS: mass calculated for $C_{24}H_{21}ClF_3N_9O_2$: 559.15, measured (ES, m/z): 560.05 [M+H]⁺. ¹H NMR (400 MHz, DMSO-d₆) δ 9.20 (s, 1H), 8.62 (s, 1H), 8.36 (s, 1H), 8.04 (s, 1H), 7.88 (s, 1H), 7.81-7.85 (m, 3H), 6.95 (s, 1H), 6.08-6.16 (m, 1H), 3.96 (s, 3H), 3.36 (s, 3H), 2.23-2.37 (m, 2H), 0.83 (t, J=7.2 Hz, 3H). ¹⁹F NMR (400 MHz, DMSO-d₆) δ −59.78.

Example 981: (R*)-5-(5-Chloro-2-(4-(trifluoromethyl)-1H-1,2,3-triazol-1-yl)phenyl)-2-(1-(4-(1-(difluoromethyl)-1H-1,2,4-triazol-5-yl)-1H-pyrazol-1-yl)propyl)-4-methoxypyridine 1-oxide

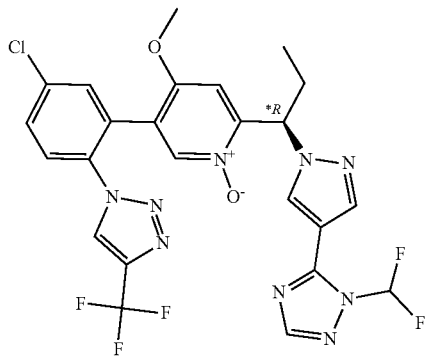 [SMILES: CC[C@H](c1cc(OC)c(-c2cc(Cl)ccc2-n2cc(C(F)(F)F)nn2)c[n+]1[O-])n1cc(-c2ncnn2C(F)F)cn1]

LC/MS: mass calculated for $C_{24}H_{19}ClF_5N_9O_2$: 595.13, measured (ES, m/z): 596.05 [M+H]⁺. ¹H NMR (400 MHz, DMSO-$d_6$) δ 9.18 (s, 1H), 8.67 (s, 1H), 8.35 (s, 1H), 8.26 (s, 1H), 8.06 (t, J=57.2 Hz, 1H), 8.05 (s, 1H), 7.84-7.86 (m, 3H), 6.97 (s, 1H), 6.11-6.13 (m, 1H), 3.39 (s, 3H), 2.29-2.35 (m, 2H), 0.82 (t, J=7.2 Hz, 3H). ¹⁹F NMR (400 MHz, DMSO-$d_6$). δ −96.16, −73.91, −59.76.

Example 982: (S*)-5-(5-Chloro-2-(4-(trifluoromethyl)-1H-1,2,3-triazol-1-yl)phenyl)-2-(1-(4-(1-(difluoromethyl)-1H-1,2,4-triazol-5-yl)-1H-pyrazol-1-yl)propyl)-4-methoxypyridine 1-oxide

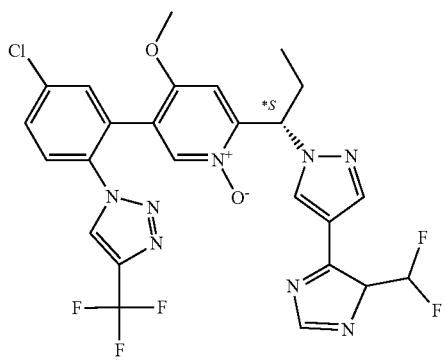

LC/MS: mass calculated for $C_{24}H_{19}ClF_5N_9O_2$: 595.13, measured (ES, m/z): 596.05 [M+H]⁺. ¹H NMR (400 MHz, DMSO-$d_6$) δ 9.19 (s, 1H), 8.67 (s, 1H), 8.36 (s, 1H), 8.26 (s, 1H), 8.06-8.07 (m, 2H), 7.82-7.87 (m, 3H), 6.97-6.98 (m, 1H), 6.11-6.15 (m, 1H), 3.43-3.58 (m, 3H), 2.23-2.42 (m, 2H), 0.83-0.86 (m, 3H). ¹⁹F NMR (400 MHz, DMSO-$d_6$) δ −96.61, −74.09, −59.81.

Example 983: 5-(3-Chloro-2-fluoro-6-(4-(trifluoromethyl)-1H-1,2,3-triazol-1-yl)phenyl)-2-(1-(4-(1-methyl-1H-1,2,3-triazol-5-yl)-1H-pyrazol-1-yl)-2-(oxazol-2-yl)ethyl)pyridine 1-oxide TFA

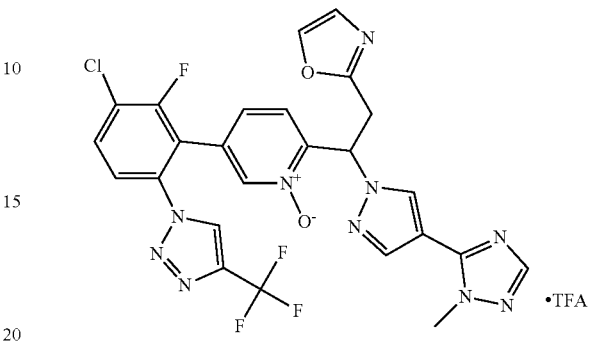

Step 1: 2-(2-(5-Bromopyridin-2-yl)-2-(4-(1-methyl-1H-1,2,3-triazo-5-yl)-1H-pyrazol-1-yl)ethyl)oxazole To a solution of 5-bromo-2-((4-(1-methyl-1H-1,2,3-triazo-5-yl)-1H-pyrazol-1-yl)methyl)pyridine (214 mg, 0.671 mmol) in THF (5 mL) was added lithium bis(trimethylsilyl) amide (0.805 mL, 1 M, 0.805 mmol) under Argon at −78° C. dropwise. After the addition, the reaction mixture was stirred at −78° C. for 15 min. A solution of 2-(iodomethyl) oxazole (168 mg, 0.805 mmol) in THF (1 mL) was added. The resulting mixture was warmed up to room temperature and stirred for 0.5 h. The reaction was then quenched by sat. NH₄Cl solution. The aqueous was extracted with EtOAc twice. The organic layers were combined, washed with water, brine, dried over anhydrous sodium sulfate, filtered and concentrated. The resulting residue was purified by silica gel chromatography (0→10% MeOH/DCM) to yield 2-(2-(5-bromopyridin-2-yl)-2-(4-(1-methyl-1H-1,2,3-triazo-5-yl)-1H-pyrazol-1-yl)ethyl)oxazole as a light yellow solid. LC/MS: mass calculated for $C_{16}H_{14}BrN_7O$: 399.0, measured (ES, m/z): 400.0 [M+H]⁺

Step 2: (6-(1-(4-(1-Methyl-1H-1,2,3-triazo-5-yl)-1H-pyrazol-1-yl)-2-(oxazol-2-yl)ethyl)pyridin-3-yl)boronic acid To a solution of 2-(2-(5-bromopyridin-2-yl)-2-(4-(1-methyl-1H-1,2,3-triazo-5-yl)-1H-pyrazol-1-yl)ethyl)oxazole (120 mg, 0.228 mmol) in 1,4-dioxane (1.86 mL) was added 4,4,5,5-tetramethyl-2-(4,4,5,5-tetramethyl-1,3,2-dioxaborolan-2-yl)-1,3,2-dioxaborolane (69.4 mg, 0.273 mmol) and potassium acetate (44.7 mg, 0.456 mmol). The reaction mixture was bubbled with argon for 10 minutes. Then [1,1'-bis(diphenylphosphino)ferrocene] dichloropalladium(II) (19.3 mg, 0.0228 mmol) was added. The reaction was stirred at 130° C. for 1 h. LC-MS suggested the formation of (6-(1-(4-(1-methyl-1H-1,2,3-triazo-5-yl)-1H-pyrazol-1-yl)-2-(oxazol-2-yl)ethyl)pyridin-3-yl)boronic acid. LC/MS: mass calculated for C$_{16}$H$_{16}$BN$_7$O$_3$: 365.1, measured (ES, m/z): 366.1 [M+H]$^+$. The reaction mixture was then used for the next step without further workup and purification.

Step 3: 2-(2-(5-(3-Chloro-2-fluoro-6-(4-(trifluoromethyl)-1H-1,2,3-triazol-1-yl)phenyl)pyridin-2-yl)-2-(4-(1-methyl-1H-1,2,3-triazo-5-yl)-1H-pyrazol)-1-yl) ethyl)oxazole To a solution of (6-(1-(4-(1-methyl-1H-1,2,3-triazo-5-yl)-1H-pyrazol-1-yl)-2-(oxazol-2-yl)ethyl)pyridin-3-yl)boronic acid (83 mg, 0.227 mmol) in 1,4-dioxane (3 mL) was added 1-(4-chloro-3-fluoro-2-iodophenyl)-4-trifluoromethyl)-1H-1,2,3-triazole (89 mg, 0.227 mmol) and potassium carbonate (0.25 mL, 2 M, 0.5 mmol). The reaction mixture was bubbled with argon for 10 minutes. Then tetrakis(triphenylphosphine)palladium(0) (0.0263 g, 0.0227 mmol) was added. The reaction was heated in Biotage microwave for 2.5 hours at 110° C. The reaction was cooled down to room temperature. Water was added, the mixture was extracted with EtOAc twice. The combined extracts were washed with water, brine and dried over anhydrous Na$_2$SO$_4$, then concentrated and purified by chromatography on EtOAc/DCM (10-90%) to yield 2-(2-(5-(3-chloro-2-fluoro-6-(4-(trifluoromethyl)-1H-1,2,3-triazol-1-yl)phenyl)pyridin-2-yl)-2-(4-(1-methyl-1H-1,2,3-triazo-5-yl)-1H-pyrazol)-1-yl) ethyl)oxazole as a yellow solid. LC/MS: mass calculated for C$_{25}$H$_{17}$ClF$_4$N$_{10}$O: 584.1, measured (ES, m/z): 585.2 [M+H]$^+$.

Step 4: 5-(3-Chloro-2-fluoro-6-(4-(trifluoromethyl)-1H-1,2,3-triazol-1-yl)phenyl)-2-(1-(4-(1-methyl-1H-1,2,3-triazol-5-yl)-1H-pyrazol-1-yl)-2-(oxazol-2-yl) ethyl)pyridine 1-oxide TFA To a solution of 2-(2-(5-(3-chloro-2-fluoro-6-(4-(trifluoromethyl)-1H-1,2,3-triazol-1-yl)phenyl)pyridin-2-yl)-2-(4-(1-methyl-1H-1,2,3-triazo-5-yl)-1H-pyrazol)-1-yl) ethyl)oxazole (45 mg, 0.0769 mmol) in CH$_3$OH (3 mL) was added methyltrioxorhenium (9.59 mg, 0.0385 mmol) and H$_2$O$_2$ (0.0793 mL, 0.769 mmol, 30%). The resulting mixture was stirred at room temperature for 1.5 h. The solvent was removed under reduced pressure and the residue was purified by via SCO reverse phase column 0.1% TFA in water and 0.1% TFA in ACN (35% to 65% 0.1% TFA in ACN gradient) to yield the title compound as a white solid.

LC/MS: mass calculated for C$_{25}$H$_{17}$ClF$_4$N$_{10}$O$_2$: 600.1, measured (ES, m/z): 601.2 [M+H]$^+$. $^1$H NMR: (CD$_3$OD, 400 MHz) δ 8.82 (s, 1H), 8.57 (s, 1H), 8.40 (s, 1H), 8.16 (s, 1H), 8.07 (s, 1H), 7.91 (t, J=8.19 Hz, 1H), 7.79 (s, 1H), 7.54-7.62 (m, 2H), 7.32 (d, J=8.31 Hz, 1H), 7.03 (s, 1H), 6.80 (dd, J=9.54, 5.14 Hz, 1H), 3.90-4.08 (m, 5H). $^{19}$F-NMR: (CD$_3$OD, 377 MHz) δ −126.36, −89.97, −75.05.

Example 984: 2-(1-(4-(4-Carbamoyl-3-fluorophenyl)-1H-pyrazol-1-yl)-3-(methoxy-d$_3$)propyl-3,3-d2)-5-(3-chloro-6-(4-chloro-1H-1,2,3-triazol-1-yl)-2-fluorophenyl)pyridine 1-oxide

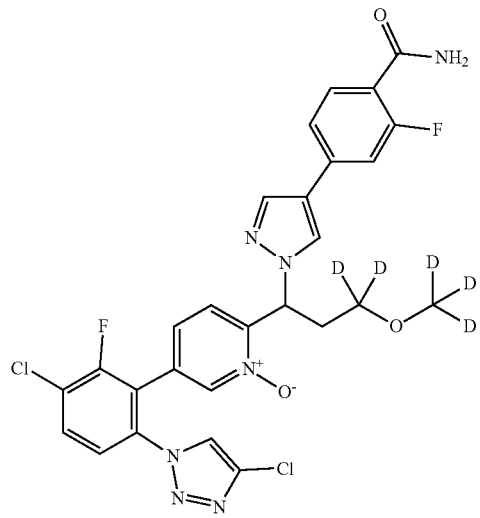 [SMILES: [2H]C([2H])([2H])OC([2H])([2H])CC(c1ccc(-c2c(-n3cc(Cl)nn3)ccc(Cl)c2F)c[n+]1[O-])n1cc(-c2ccc(C(N)=O)c(F)c2)cn1]

LC/MS: mass calculated for C$_{27}$H$_{16}$Cl$_2$D$_5$F$_2$N$_7$O$_3$: 604.14, measured (ES, m/z): 605.15 [M+H]+. 1H NMR (400 MHz, DMSO-d$_6$) δ 8.67 (s, 1H), 8.60 (s, 1H), 8.40 (s, 1H), 8.15 (s, 1H), 8.02 (t, J=8.8 Hz, 1H), 7.63-7.73 (m, 2H), 7.55-7.60 (m, 2H), 7.49-7.55 (m, 2H), 7.33 (d, J=8.3 Hz, 1H), 7.16 (dd, J=8.3, 1.7 Hz, 1H), 6.12-6.23 (m, 1H), 2.40-2.48 (m, 2 h). 19F NMR (376 MHz, DMSO-d$_6$) δ −74.53, −112.98.

Example 985: 2-(1-4-(4-Carbamoyl-3-fluorophenyl)-1H-pyrazol-1-yl)-2-(5-methyl-1,3,4-oxadizol-2-yl)ethyl-5-(3-chloro-2-fluoro-6-(4-(trifluoromethyl)-1H-1,2,3-triazol-1-yl)phenyl)pyridine 1-oxide TFA

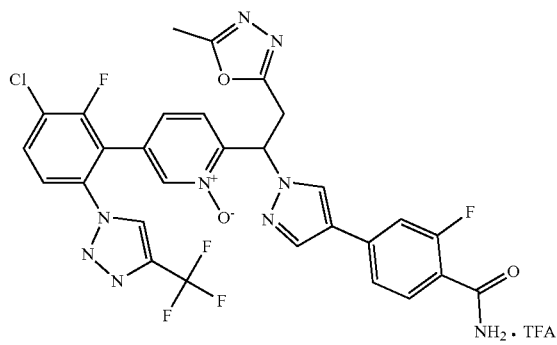

Step 1: (5-Methyl-1,3,4-oxadizol-2-yl)methyl methanesulfonate

To a solution of (5-methyl-1,3,4-oxadizol-2-yl)methanol (1.0 g, 8.76 mmol) in DCM (25 mL) at 0° C. was added TEA (1.47 mL, 10.5 mmol). Then methanesulfonyl chloride (1.02 mL, 13.1 mmol) was added dropwise. The resulting mixture was stirred at 0° C. for 2 h. To the reaction mixture was added dilute HCl solution (0.1 N, 50 mL). The organic phase was separated and the aqueous phase was extracted further with DCM (2×50 mL). The combined organic phase was washed with brine, dried over sodium sulfate and concentrated to yield (5-methyl-1,3,4-oxadizol-2-yl)methyl methanesulfonate as a light yellow oil, which was used in the next step without further purification. LC/MS: mass calculated for $C_5H_8N_2O_4S$: 192.0, measured (ES, m/z): 193.0 $[M+H]^+$.

Step 2: 2-(Iodomethyl)-5-methyl-1,3,4-oxadizol

A mixture of (5-methyl-1,3,4-oxadizol-2-yl)methyl methanesulfonate (1.4 g, 7.28 mmol) and NaI (1.09 g, 7.28 mmol) in acetone (50 mL) was refluxing for 1 h, then cooled to room temperature. The solid was filtered off and the mother liquor was concentrated. The residue was then partitioned between DCM and water. The organic phase was separated and washed with brine, dried over sodium sulfate, and concentrated. The residue was purified with ISCO column (40 g, eluting with EtOAc/Heptane) to yield 2-(iodomethyl)-5-methyl-1,3,4-oxadizol as a yellow oil. LC/MS: mass calculated for $C_4H_5IN_2O$: 223.9, measured (ES, m/z): 224.9 $[M+H]^+$.

Step 3: tert-Butyl 4-(1-(1-(5-bromopyridin-2-yl)-2-(5-methyl-1,3,4-oxadizol-2-yl)ethyl)-1H-pyrazol-4-yl)-2-fluorobenzoate To a solution of tert-butyl 4-(1-((5-bromopyridin-2-yl)methyl)-1H-pyrazol-4-yl)-2-fluorobenzoate (290 mg, 0.671 mmol) in THF (8 mL) was added lithium bis(trimethylsilyl)amide (0.738 mL, 1 M, 0.738 mmol) under argon at −78° C. dropwise. After the addition, the reaction mixture was stirred at −78° C. for 15 min. A solution of 2-(iodomethyl)-5-methyl-1,3,4-oxadizol (180 mg, 0.805 mmol) in THF (1 mL) was added. The resulting mixture was warmed up to room temperature and stirred for 0.5 h. The reaction was then quenched by sat. NH$_4$Cl solution. The aqueous was extracted with EtOAc twice. The organic layers were combined, washed with water, brine, dried over anhydrous sodium sulfate, filtered and concentrated. The resulting residue was purified by silica gel chromatography (0-100% EtOAc/heptane) to yield the tert-butyl 4-(1-(1-(5-bromopyridin-2-yl)-2-(5-methyl-1,3,4-oxadizol-2-yl)ethyl)-1H-pyrazol-4-yl)-2-fluorobenzoate as a light yellow solid. LC/MS: mass calculated for $C_{24}H_{23}BrFN_5O_3$: 527.1, measured (ES, m/z): 528.1.1 $[M+H]^+$ Step 4: (6-(1-(4-(4-(tert-Butoxycarbonyl)-3-fluorophenyl)-1H-pyrazol-1-yl)-2-(5-methyl-1,3,4-oxadizol-2-yl)ethyl)pyridin-3-yl)boronic acid To a solution of tert-butyl 4-(1-(1-(5-bromopyridin-2-yl)-2-(5-methyl-1,3,4-oxadizol-2-yl)ethyl)-1H-pyrazol-4-yl)-2-fluorobenzoate (150 mg, 0.284 mmol) in 1,4-dioxane (2 mL) was added 4,4,5,5-tetramethyl-2-(4,4,5,5-tetramethyl-1,3,2-dioxaborolan-2-yl)-1,3,2-dioxaborolane (86.5 mg, 0.341 mmol) and potassium acetate (55.6 mg, 0.568 mmol). The reaction mixture was bubbled with argon for 10 minutes. Then [1,1'-bis(diphenylphosphino)ferrocene] dichloropalladium(II) (24.0 mg, 0.0284 mmol) was added. The reaction was stirred at 130° C. for 1 h. LC-MS suggested the formation of (6-(1-(4-(4-(tert-butoxycarbonyl)-3-fluorophenyl)-1H-pyrazol-1-yl)-2-(5-methyl-1,3,4-oxadizol-2-yl)ethyl)pyridin-3-yl)boronic acid. LC/MS: mass calculated for $C_{24}H_{25}BFN_5O_5$: 493.2, measured (ES, m/z): 494.2 $[M+H]^+$. The reaction mixture was then used for the next step without workup and purification.

Step 5: tert-Butyl 4-(1-(1-(5-(3-chloro-2-fluoro-6-(4-(trifluoromethyl)-1H-1,2,3-triazol-1-yl)phenyl)pyridin-2-yl)-2-(5-methyl-1,3,4-oxadizol-2-yl)ethyl-1H-pyrazol-4-yl)-2-fluorobenzoate To a solution of (6-(1-(4-(4-(tert-butoxycarbonyl)-3-fluorophenyl)-1H-pyrazol-1-yl)-2-(5-methyl-1,3,4-oxadizol-2-yl)ethyl)pyridin-3-yl)boronic acid (0.14 g, 0.284 mmol) in 1,4-dioxane (3 mL) was added 1-(4-chloro-3-fluoro-2-iodophenyl)-4-trifluoromethyl)-1H-1,2,3-triazole (0.111 g, 0.284 mmol) and potassium carbonate (0.312 mL, 2 M, 0.624 mmol). The reaction mixture was bubbled with argon for 10 minutes. Then tetrakis(triphenylphosphine)palladium(0) (0.0328 g, 0.0284 mmol) was added. The reaction was heated in Biotage microwave for 2.5 hours at 110° C. The reaction was cooled down to room temperature. Water was added, the mixture was extracted with EtOAc twice. The combined extracts were washed with water, brine and dried over anhydrous Na$_2$SO$_4$, then concentrated and purified by chromatography on EtOAc/DCM (10-90%) to yield tert-butyl 4-(1-(1-(5-(3-chloro-2-fluoro-6-(4-(trifluoromethyl)-1H-1,2,3-triazol-1-yl)phenyl)pyridin-2-yl)-2-(5-methyl-1,3,4-oxadizol-2-yl)ethyl-1H-pyrazol-4-yl)-2-fluorobenzoate as a yellow solid. LC/MS: mass calculated for $C_{33}H_{26}ClF_5N_8O_3$: 712.2, measured (ES, m/z): 713.1 $[M+H]^+$ Step 6: 4-(1-(1-(5-(3-Chloro-2-fluoro-6-(4-(trifluoromethyl)-1H-1,2,3-triazol-1-yl)phenyl)pyridin-2-yl)-2-(5-methyl-1,3,4-oxadizol-2-yl)ethyl-1H-pyrazol-4-yl)-2-fluorobenzoic acid To a solution of tert-butyl 4-(1-(1-(5-(3-chloro-2-fluoro-6-(4-(trifluoromethyl)-1H-1,2,3-triazol-1-yl)phenyl)pyridin-2-yl)-2-(5-methyl-1,3,4-oxadizol-2-yl)ethyl-1H-pyrazol-4-yl)-2-fluorobenzoate (110 mg, 0.154 mmol) in DCM (2.17 mL) was added TFA (2.17 mL). The resulting mixture was stirred at room temperature for 2 h. The reaction mixture was concentrated to yield 4-(1-(1-(5-(3-chloro-2-fluoro-6-(4-(trifluoromethyl)-1H-1,2,3-triazol-1-yl)phenyl)pyridin-2-yl)-2-(5-methyl-1,3,4-oxadizol-2-yl)ethyl-1H-pyrazol-4-yl)-2-fluorobenzoic acid (101 mg, 99.8%) as a gummy solid, which was used in the next step without further purification. LC/MS: mass calculated for $C_{29}H_{18}ClF_5N_8O_3$: 656.1, measured (ES, m/z): 657.2 $[M+H]^+$.

Step 7: 4-(1-(1-(5-(3-Chloro-2-fluoro-6-(4-(trifluoromethyl)-1H-1,2,3-triazol-1-yl)phenyl)pyridin-2-yl)-2-(5-methyl-1,3,4-oxadizol-2-yl)ethyl-1H-pyrazol-4-yl)-2-fluorobenzamide To a solution of 4-(1-(1-(5-(3-chloro-2-fluoro-6-(4-(trifluoromethyl)-1H-1,2,3-triazol-1-yl)phenyl)pyridin-2-yl)-2-(5-methyl-1,3,4-oxadizol-2-yl)ethyl-1H-pyrazol-4-yl)-2-fluorobenzoic acid (101 mg, 0.154 mmol) in DMF (2.15 mL) was added hydroxybenzotriazole hydrate (24.9 mg, 0.184 mmol), 1-ethyl-3-(3-dimethylaminopropyl)carbodiimide (30.1 mg, 0.184 mmol), ammonium chloride (83.1 mg, 1.54 mmol) and N,N-diisopropylethylamine (0.0552 mL, 0.32 mmol). The reaction mixture was stirred at 60° C. for 1 h, then cooled to room temperature. To the reaction was added water, extracted with EtOAc. The organic layers were combined, dried over anhydrous sodium sulfate, filtered, and concentrated. The resulting residue was purified by silica gel chromatography (0-5% MeOH/EtOAc) to yield 4-(1-(1-(5-(3-chloro-2-fluoro-6-(4-(trifluoromethyl)-1H-1,2,3-triazol-1-yl)phenyl)pyridin-2-yl)-2-(5-methyl-1,3,4-oxadizol-2-yl)ethyl-1H-pyrazol-4-yl)-2-fluorobenzamide as a light yellow solid. LC/MS: mass calculated for $C_{29}H_{19}ClF_5N_9O_2$: 655.1, measured (ES, m/z): 656.1 $[M+H]^+$.

Step 8: 2-(1-4-(4-Carbamoyl-3-fluorophenyl)-1H-pyrazol-1-yl)-2-(5-methyl-1,3,4-oxadizol-2-yl)ethyl-5-(3-chloro-2-fluoro-6-(4-(trifluoromethyl)-1H-1,2,3-triazol-1-yl)phenyl)pyridine 1-oxide TFA To a solution of 4-(1-(1-(5-(3-chloro-2-fluoro-6-(4-(trifluoromethyl)-1H-1,2,3-triazol-1-yl)phenyl)pyridin-2-yl)-2-(5-methyl-1,3,4-oxadizol-2-yl)ethyl-1H-pyrazol-4-yl)-2-fluorobenzamide (55 mg, 0.0838 mmol) in $CH_3OH$ (3 mL) was added methyltrioxorhenium (20.9 mg, 0.0838 mmol) and $H_2O_2$ (0.173 mL, 1.68 mmol, 30%). The resulting mixture was stirred at room temperature for 1.5 h. The solvent was removed under reduced pressure and the residue was purified by via ISCO reverse phase column 0.1% TFA in water and 0.1% TFA in ACN (35% to 65% 0.1% TFA in ACN gradient) to yield the title compound as a white solid. LC/MS: mass calculated for $C_{29}H_{19}ClF_5N_9O_3$: 671.1, measured (ES, m/z): 672.2 $[M+H]^+$. $^1H$ NMR: (DMSO-$d_6$, 400 MHz) δ 9.19 (s, 1H), 8.60 (s, 1H), 8.50 (s, 1H), 8.14 (s, 1H), 8.07 (t, J=8.07 Hz, 1H), 7.77 (dd, J=8.56, 1.22 Hz, 1H), 7.57-7.69 (m, 3H), 7.46-7.55 (m, 2H), 7.24-7.30 (m, 1H), 7.18-7.23 (m, 1H), 6.52 (dd, J=9.78, 4.89 Hz, 1H), 3.93-3.95 (m, 2H), 2.42 (s, 3H). $^{19}F$-NMR: (DMSO-$d_6$, 377 MHz) δ −125.17, −87.00, −72.09.

Example 986: (R*)-2-(1-(4-(4-Carbamoyl-3-fluorophenyl)-1H-pyrazol-1-yl)-3-(difluoromethoxy)propyl)-5-(3-chloro-2-fluoro-6-(1H-tetrazol-1-yl)phenyl)pyridine 1-oxide

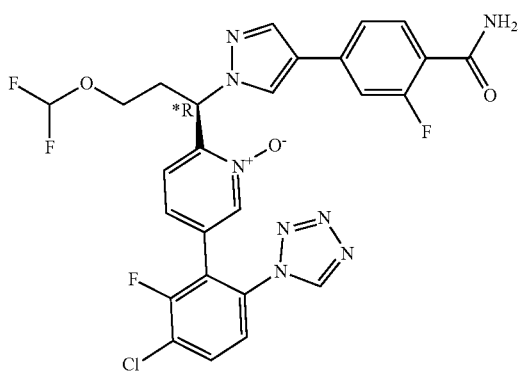

Step 1: 4-(1-(1-(5-Bromopyridin-2-yl)-3-(difluoromethoxy)propyl)-1H-pyrazol-4-yl)-2-fluorobenzamide To a solution of 2-fluoro-4-(1H-pyrazol-4-yl)benzamide (320 mg, 1.56 mmol, 1.0 equiv.) in N,N-dimethylformamide (10 mL) was added sodium tert-butoxide (142 mg, 1.48 mmol, 0.95 equiv.). The reaction mixture was stirred 0.5 h at 0° C. 1-(5-bromopyridin-2-yl)-3-(difluoromethoxy)propyl methanesulfonate (562 mg, 1.56 mmol, 1 equiv.) was added. The reaction mixture was stirred for 2 h at room temperature, then quenched with water. The resulting mixture was extracted with ethyl acetate twice. The combined organic layers were washed with brine, dried over anhydrous sodium sulfate and concentrated under vacuum. The residue was purified by silica gel chromatography (0→10% MeOH/DCM) to yield 4-(1-(1-(5-bromopyridin-2-yl)-3-(difluoromethoxy)propyl)-1H-pyrazol-4-yl)-2-fluorobenzamide as a yellow solid. LC/MS: mass calculated for $C_{19}H_{16}BrF_3N_4O_2$: 468.04, measured (ES, m/z): 469.00 $[M+H]^+$.

Step 2: 4-(1-(1-(5-(6-Amino-3-chloro-2-fluorophenyl)pyridin-2-yl)-3-(difluoromethoxy)propyl)-1H-pyrazol-4-yl)-2-fluorobenzamide To a solution of 4-(1-(1-(5-bromopyridin-2-yl)-3-(difluoromethoxy)propyl)-1H-pyrazol-4-yl)-2-fluorobenzamide (400 mg, 0.85 mmol, 1.0 equiv.) in 1,4-dioxane (50 mL) and water (10 mL) was added (6-amino-3-chloro-2-fluorophenyl)boronic acid (323 mg, resulting), tetrakis(triphenylphosphine)palladium (99 mg, 0.09 mmol, 0.1 equiv.) and potassium carbonate (353 mg, 2.56 mmol, 3.0 equiv.) under $N_2$. The reaction mixture was stirred at 100° C. for 2 h, cooled to room temperature, and then water was added. The resulting mixture was extracted with ethyl acetate twice. The combined organic layers were dried over anhydrous sodium sulfate and concentrated under vacuum. The residue was purified by silica gel chromatography with (0→100% EA/PE) to yield 4-(1-(1-(5-(6-amino-3-chloro-2-fluorophenyl)pyridin-2-yl)-3-(difluoromethoxy)propyl)-1H-pyrazol-4-yl)-2-fluorobenzamide as a brown solid. LC/MS: mass calculated for $C_{25}H_{20}ClF_4N_5O_2$: 533.12, measured (ES, m/z): 534.05 $[M+H]^+$.

Step 3: 4-(1-(1-(5-(3-Chloro-2-fluoro-6-(1H-tetrazol-1-yl)phenyl)pyridin-2-yl)-3-(difluoromethoxy)propyl)-1H-pyrazol-4-yl)-2-fluorobenzamide To a solution of 4-(1-(1-(5-(6-amino-3-chloro-2-fluorophenyl)pyridin-2-yl)-3-(difluoromethoxy)propyl)-1H-pyrazol-4-yl)-2-fluorobenzamide (340 mg, 0.64 mmol, 1.0 equiv.) in acetic acid (10 mL) was added azidotrimethylsilane (734 mg, 6.37 mmol, 10.0 equiv.) and trimethoxymethane (676 mg, 6.37 mmol, 10.0 equiv.). The reaction mixture was stirred overnight at room temperature, concentrated under vacuum. The residue was purified by reverse column chromatography (80 g, MeCN/$H_2O$ (0.05% $CF_3COOH$): 0→50%) to yield 4-(1-(1-(5-(3-chloro-2-fluoro-6-(1H-tetrazol-1-yl)phenyl)pyridin-2-yl)-3-(difluoromethoxy)propyl)-1H-pyrazol-4-yl)-2-fluorobenzamide as a brown solid. LC/MS: mass calculated for $C_{26}H_{19}ClF_4N_8O_2$: 586.13, measured (ES, m/z): 587.15 $[M+H]^+$.

Step 4: (R*)-2-(1-(4-(4-Carbamoyl-3-fluorophenyl)-1H-pyrazol-1-yl)-3-(difluoromethoxy)propyl)-5-(3-chloro-2-fluoro-6-(1H-tetrazol-1-yl)phenyl)pyridine 1-oxide To a solution of 4-(1-(1-(5-(3-chloro-2-fluoro-6-(1H-tetrazol-1-yl)phenyl)pyridin-2-yl)-3-(difluoromethoxy)propyl)-1H-pyrazol-4-yl)-2-fluorobenzamide (200 mg, 0.34 mmol, 1.0 equiv.) in $CH_3OH$ (5 mL) was added methylrhenium (VII) trioxide (8.0 mg, 0.04 mmol, 0.1 equiv.), hydrogen peroxide (30 wt %, 290 mg, 1.71 mmol, 5.0 equiv.). The mixture was stirred for 0.5 h at room temperature. The residue was purified by reverse column chromatography (80 g, MeCN/$H_2O$ (0.05% $CF_3COOH$): 0→50%) to yield 2-(1-

(4-(4-carbamoyl-3-fluorophenyl)-1H-pyrazol-1-yl)-3-(difluoromethoxy)propyl)-5-(3-chloro-2-fluoro-6-(1H-tetrazol-1-yl)phenyl)pyridine 1-oxide as a solid. The racemic solid was purified by Prep-Chiral-HPLC with MTBE (0.1% DEA):MeOH=70:30 to yield (R*)-2-(1-(4-(4-carbamoyl-3-fluorophenyl)-1H-pyrazol-1-yl)-3-(difluoromethoxy)propyl)-5-(3-chloro-2-fluoro-6-(1H-tetrazol-1-yl)phenyl)pyridine 1-oxide as a white solid.

LC/MS: mass calculated for $C_{26}H_{19}ClF_4N_8O_3$: 602.12, measured (ES, m/z): 603.10 [M+H]$^+$. $^1$H NMR (400 MHz, DMSO-d$_6$) 59.69 (s, 1H), 8.48 (d, J=1.6 Hz, 1H), 8.02-8.29 (m, 3H), 7.55-7.85 (m, 6H), 7.45 (d, J=8.3 Hz, 1H), 7.22-7.30 (m, 1H), 6.65 (t, J=75.7 Hz, 1H), 6.04-6.15 (m, 1H), 3.82-3.92 (m, 1H), 3.70-3.80 (m, 1H), 2.57-2.63 (m, 2H). $^{19}$F NMR (376 MHz, DMSO-d$_6$): δ −73.82, −83.26, −113.16.

Example 987: (S*)-2-(1-(4-(4-Carbamoyl-3-fluorophenyl)-1H-pyrazol-1-yl)-3-(difluoromethoxy)propyl)-5-(3-chloro-2-fluoro-6-(1H-tetrazol-1-yl)phenyl)pyridine 1-oxide

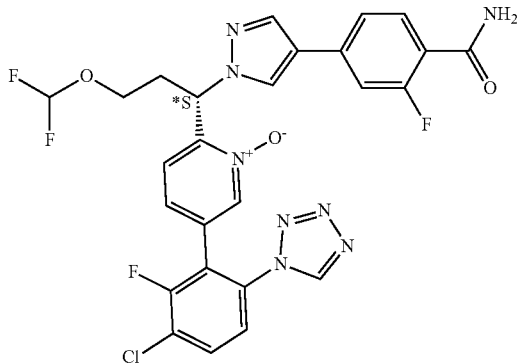 [SMILES: NC(=O)c1ccc(-c2cnn([C@@H](CCOC(F)F)c3ccc(-c4c(-n5cnnn5)ccc(Cl)c4F)c[n+]3[O-])c2)cc1F]

Step 1: 4-(1-(1-(5-Bromopyridin-2-yl)-3-(difluoromethoxy)propyl)-1H-pyrazol-4-yl)-2-fluorobenzamide To a solution of 2-fluoro-4-(1H-pyrazol-4-yl)benzamide (320 mg, 1.56 mmol, 1.0 equiv.) in N,N-dimethylformamide (10 mL) was added sodium tert-butoxide (142 mg, 1.48 mmol, 0.95 equiv.). The reaction mixture was stirred 0.5 h at 0° C. 1-(5-Bromopyridin-2-yl)-3-(difluoromethoxy)propyl methanesulfonate (562 mg, 1.56 mmol, 1 equiv.) was added. The reaction mixture was stirred for 2 h at room temperature, then quenched with water. The resulting mixture was extracted with ethyl acetate twice. The combined organic layers were washed with brine, dried over anhydrous sodium sulfate and concentrated under vacuum. The residue was purified by silica gel chromatography (0→10% MeOH/DCM) to yield 4-(1-(1-(5-bromopyridin-2-yl)-3-(difluoromethoxy)propyl)-1H-pyrazol-4-yl)-2-fluorobenzamide as a yellow solid. LC/MS: mass calculated for $C_{19}H_{16}BrF_3N_4O_2$: 468.04, measured (ES, m/z): 469.00 [M+H]$^+$.

Step 2: 4-(1-(1-(5-(6-Amino-3-chloro-2-fluorophenyl)pyridin-2-yl)-3-(difluoromethoxy)propyl)-1H-pyrazol-4-yl)-2-fluorobenzamide To a solution of 4-(1-(1-(5-bromopyridin-2-yl)-3-(difluoromethoxy)propyl)-1H-pyrazol-4-yl)-2-fluorobenzamide (400 mg, 0.85 mmol, 1.0 equiv.) in 1,4-dioxane (50 mL) and water (10 mL) was added (6-amino-3-chloro-2-fluorophenyl)boronic acid (323 mg, resulting), tetrakis(triphenylphosphine)palladium (99 mg, 0.09 mmol, 0.1 equiv.) and potassium carbonate (353 mg, 2.56 mmol, 3.0 equiv.) under N$_2$. The reaction mixture was stirred at 100° C. for 2 h, then cooled to room temperature, water was added. The resulting mixture was extracted with ethyl acetate twice. The combined organic layers were dried over anhydrous sodium sulfate and concentrated under vacuum. The residue was purified by silica gel chromatography with (0→100% EA/PE) to yield 4-(1-(1-(5-(6-amino-3-chloro-2-fluorophenyl)pyridin-2-yl)-3-(difluoromethoxy)propyl)-1H-pyrazol-4-yl)-2-fluorobenzamide as a brown solid. LC/MS: mass calculated for $C_{25}H_{20}ClF_4N_5O_2$: 533.12, measured (ES, m/z): 534.05 [M+H]$^+$.

Step 3: 4-(1-(1-(5-(3-Chloro-2-fluoro-6-(1H-tetrazol-1-yl)phenyl)pyridin-2-yl)-3-(difluoromethoxy)propyl)-1H-pyrazol-4-yl)-2-fluorobenzamide To a solution of 4-(1-(1-(5-(6-amino-3-chloro-2-fluorophenyl)pyridin-2-yl)-3-(difluoromethoxy)propyl)-1H-pyrazol-4-yl)-2-fluorobenzamide (340 mg, 0.64 mmol, 1.0 equiv.) in acetic acid (10 mL) was added azidotrimethylsilane (734 mg, 6.37 mmol, 10.0 equiv.) and trimethoxymethane (676 mg, 6.37 mmol, 10.0 equiv.). The reaction mixture was stirred overnight at room temperature, then concentrated under vacuum. The residue was purified by reverse column chromatography (80 g, MeCN/H$_2$O (0.05% CF$_3$COOH): 0→50%) to yield 4-(1-(1-(5-(3-chloro-2-fluoro-6-(1H-tetrazol-1-yl)phenyl)pyridin-2-yl)-3-(difluoromethoxy)propyl)-1H-pyrazol-4-yl)-2-fluorobenzamide as a brown solid. LC/MS: mass calculated for $C_{26}H_{19}ClF_4N_8O_2$: 586.13, measured (ES, m/z): 587.15 [M+H]$^+$.

Step 4: (S*)-2-(1-(4-(4-Carbamoyl-3-fluorophenyl)-1H-pyrazol-1-yl)-3-(difluoromethoxy)propyl)-5-(3-chloro-2-fluoro-6-(1H-tetrazol-1-yl)phenyl)pyridine 1-oxide To a solution of 4-(1-(1-(5-(3-chloro-2-fluoro-6-(1H-tetrazol-1-yl)phenyl)pyridin-2-yl)-3-(difluoromethoxy)propyl)-1H-pyrazol-4-yl)-2-fluorobenzamide (200 mg, 0.34 mmol, 1.0 equiv) in CH$_3$OH (5 mL) was added methylrhenium (VII) trioxide (8 mg, 0.04 mmol, 0.1 equiv.), hydrogen peroxide (30 wt %, 290 mg, 1.71 mmol, 5.0 equiv.). The mixture was stirred for 0.5 h at room temperature. The residue was purified by reverse column chromatography (80 g, MeCN/H$_2$O (0.05% CF$_3$COOH): 0→50%) to yield 2-(1-(4-(4-carbamoyl-3-fluorophenyl)-1H-pyrazol-1-yl)-3-(difluoromethoxy)propyl)-5-(3-chloro-2-fluoro-6-(1H-tetrazol-1-yl)phenyl)pyridine 1-oxide as a solid. The racemic solid was purified by Prep-Chiral-HPLC with MTBE (0.1% DEA):MeOH=70:30 to yield (S*)-2-(1-(4-(4-carbamoyl-3-fluorophenyl)-1H-pyrazol-1-yl)-3-(difluoromethoxy)propyl)-5-(3-chloro-2-fluoro-6-(1H-tetrazol-1-yl)phenyl)pyridine 1-oxide as a solid.

LC/MS: mass calculated for $C_{26}H_{19}ClF_4N_8O_3$: 602.12, measured (ES, m/z): 603.10 [M+H]$^+$. $^1$H NMR (400 MHz, DMSO-d$_6$): δ 9.69 (s, 1H), 8.48 (d, J=1.6 Hz, 1H), 8.02-8.17 (m, 2H), 7.97 (d, J=1.2 Hz, 1H), 7.53-7.81 (m, 6H), 7.43 (d, J=8.3 Hz, 1H), 7.20-7.30 (m, 1H), 6.65 (t, J=75.7 Hz, 1H), 6.02-6.12 (m, 1H), 3.81-3.92 (m, 1H), 3.69-3.80 (m, 1H), 2.56-2.70 (m, 2H). $^{19}$F NMR (376 MHz, DMSO-d$_6$): δ −83.25, −112.63, −113.28.

Example 988: (R*)-2-(1-(4-(4-Carboxy-3-fluorophenyl)-1H-pyrazol-1-yl)-2-(1-(difluoromethyl)-1H-pyrazol-3-yl)ethyl)-5-(3-chloro-2-fluoro-6-(4-(trifluoromethyl)-1H-1,2,3-triazol-1-yl)phenyl)pyridine 1-oxide

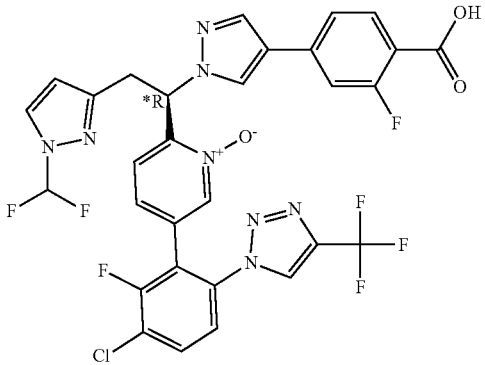 [SMILES: O=C(O)c1ccc(-c2cnn([C@H](Cc3ccn(C(F)F)n3)c3ccc(-c4c(-n5cc(C(F)(F)F)nn5)ccc(Cl)c4F)c[n+]3[O-])c2)cc1F]

Step 1: tert-Butyl 4-(1-(1-(5-bromopyridin-2-yl)-2-(1-(difluoromethyl)-1H-pyrazol-3-yl) ethyl)-1H-pyrazol-4-yl)-2-fluorobenzoate To a solution of tert-butyl 4-(1-((5-bromopyridin-2-yl)methyl)-1H-pyrazol-4-yl)-2-fluorobenzoate (520 mg, 1.20 mmol, 1 equiv.) in tetrahydrofuran (6 mL) under nitrogen was added lithium bis(trimethylsilyl)amide (1.4 mL, 1.40 mmol, 1.0 M in THF, 1.2 equiv.) dropwise at −78° C. and the solution was stirred for 30 min at this temperature. 3-(Bromomethyl)-1-(difluoromethyl)-1H-pyrazole (305 mg, 1.44 mmol, 1.2 equiv.) in tetrahydrofuran (2 mL) was added the solution. The reaction mixture was stirred at −70° C. for 2 h under N$_2$. The reaction was quenched with sat. NH$_4$Cl (aq.) and extracted with EA twice. The combined organic layers were washed with brine, dried over Na$_2$SO$_4$, and concentrated under vacuum. The resulting residue was purified by silica gel chromatography (0→50% EA/PE) to yield tert-butyl 4-(1-(1-(5-bromopyridin-2-yl)-2-(1-(difluoromethyl)-1H-pyrazol-3-yl) ethyl)-1H-pyrazol-4-yl)-2-fluorobenzoate as light yellow oil. LC/MS: mass calculated for C$_{25}$H$_{23}$BrF$_3$N$_5$O$_2$: 561.10, measured (ES, m/z): 562.20, 564.20 [M+H, M+H+2]$^+$.

Step 2: (6-(1-(4-(4-(tert-Butoxycarbonyl)-3-fluorophenyl)-1H-pyrazol-1-yl)-2-(1-(difluoromethyl)-1H-pyrazol-3-yl) ethyl) pyridin-3-yl)boronic acid To a mixture of tert-butyl 4-(1-(1-(5-bromopyridin-2-yl)-2-(1-(difluoromethyl)-1H-pyrazol-3-yl)ethyl)-1H-pyrazol-4-yl)-2-fluorobenzoate (230 mg, 0.41 mmol, 1.0 equiv.) and 4,4,4',4',5,5,5',5'-octamethyl-2,2'-bi(1,3,2-dioxaborolane) (312 mg, 1.23 mmol, 3.0 equiv.) in 1,4-dioxane (5 mL) was added potassium acetate (161 mg, 1.64 mmol, 4.0 equiv.) and Pd(dppf)Cl$_2$ (60 mg, 0.08 mmol, 0.2 equiv.). The solution was stirred at 90° C. for 2 h under N$_2$. The mixture was quenched with H$_2$O, extracted with EA twice. The combined organic layer was washed with brine, dried over Na$_2$SO$_4$ and concentrated to yield (6-(1-(4-(4-(tert-butoxycarbonyl)-3-fluorophenyl)-1H-pyrazol-1-yl)-2-(1-(difluoromethyl)-1H-pyrazol-3-yl) ethyl) pyridin-3-yl)boronic acid as brown oil. LC/MS: mass calculated for C$_{25}$H$_{25}$BF$_3$N$_5$O$_4$: 527.20, measured (ES, m/z): 528.10 [M+H]$^+$.

Step 3: tert-Butyl 4-(1-(1-(5-(3-chloro-2-fluoro-6-(4-(trifluoromethyl)-1H-1, 2, 3-triazol-1-yl)phenyl) pyridin-2-yl)-2-(1-(difluoromethyl)-1H-pyrazol-3-yl) ethyl)-1H-pyrazol-4-yl)-2-fluorobenzoate To a mixture of (6-(1-(4-(4-(tert-butoxycarbonyl)-3-fluorophenyl)-1H-pyrazol-1-yl)-2-(1-(difluoromethyl)-1H-pyrazol-3-yl)ethyl)pyridin-3-yl)boronic acid (200 mg, 0.38 mmol, 1.0 equiv.), potassium carbonate (157 mg, 1.14 mmol, 3.0 equiv.) and tert-butyl 4-(4,4,5,5-tetramethyl-1,3,2-dioxaborolan-2-yl)-1H-pyrazole-1-carboxylate (178 mg, 0.45 mmol, 1.2 equiv.) in 1,4-dioxane (4 mL) and water (1 mL) was added tetrakis(triphenylphosphine)Palladium(0) (44 mg, 0.04 mmol, 0.1 equiv.). The solution was stirred at 100° C. for 2 h under N$_2$. Water was added, the mixture was extracted with EA. The combined organic layers were washed with brine, dried over Na$_2$SO$_4$ and concentrated. The residue was purified by silica gel chromatography (0→100% EA:PE) to yield tert-butyl 4-(1-(1-(5-(3-chloro-2-fluoro-6-(4-(trifluoromethyl)-1H-1, 2, 3-triazol-1-yl)phenyl)pyridin-2-yl)-2-(1-(difluoromethyl)-1H-pyrazol-3-yl) ethyl)-1H-pyrazol-4-yl)-2-fluorobenzoate as yellow solid. LC/MS: mass calculated for C$_{34}$H$_{26}$ClF$_7$N$_8$O$_2$: 746.18, measured (ES, m/z): 747.15 [M+H]$^+$.

Step 4: 4-(1-(1-(5-(3-Chloro-2-fluoro-6-(4-(trifluoromethyl)-1H-1, 2, 3-triazol-1-yl) phenyl) pyridin-2-yl)-2-(1-(difluoromethyl)-1H-pyrazol-3-yl)ethyl)-1H-pyrazol-4-yl)-2-fluorobenzoic acid To a mixture of tert-butyl 4-(1-(1-(5-(3-chloro-2-fluoro-6-(4-(trifluoromethyl)-1H-1,2,3-triazol-1-yl)phenyl)pyridin-2-yl)-2-(1-(difluoromethyl)-1H-pyrazol-3-yl)ethyl)-1H-pyrazol-4-yl)-2-fluorobenzoate (190 mg, 0.25 mmol, 1.0 equiv.) in dichloromethane (3 mL) was added 2, 2, 2-trifluoroacetic acid (2 mL). The reaction mixture was stirred at room temperature for 1 h. The reaction mixture was concentrated under vacuum to yield 4-(1-(1-(5-(3-Chloro-2-fluoro-6-(4-(trifluoromethyl)-1H-1, 2, 3-triazol-1-yl) phenyl) pyridin-2-yl)-2-(1-(difluoromethyl)-1H-pyrazol-3-yl) ethyl)-1H-pyrazol-4-yl)-2-fluorobenzoic acid as yellow oil. LC/MS: mass calculated for C$_{30}$H$_{18}$ClF$_7$N$_8$O$_2$: 690.11, measured (ES, m/z): 691.10 [M+H]$^+$.

Step 5: (R*)-2-(1-(4-(4-Carboxy-3-fluorophenyl)-1H-pyrazol-1-yl)-2-(1-(difluoromethyl)-1H-pyrazol-3-yl)ethyl)-5-(3-chloro-2-fluoro-6-(4-(trifluoromethyl)-1H-1,2,3-triazol-1-yl)phenyl)pyridine 1-oxide To a solution of 4-(1-(1-(5-(3-chloro-2-fluoro-6-(4-(trifluoromethyl)-1H-1,2,3-triazol-1-yl)phenyl)pyridin-2-yl)-2-(1-(difluoromethyl)-1H-pyrazol-3-yl)ethyl)-1H-pyrazol-4-yl)-2-fluorobenzoic acid (160 mg, 0.23 mmol, 1 equiv.) and ReMeO$_3$ (12 mg, 0.05 mmol, 0.2 equiv.) in CH$_3$OH (3.0 mL) was added hydrogen peroxide (0.2 mL, 2.32 mmol, 30 wt %, 10.0 equiv.). The reaction mixture was stirred at room temperature for 1 h. The reaction mixture was purified by reverse phase chromatography on C18 (120 g, ACN/H$_2$O (0.05% CF$_3$COOH): 0→50%). 90 mg of resulting residue was purified by Prep-Chiral-HPLC to yield (R*)-2-(1-(4-(4-carboxy-3-fluorophenyl)-1H-pyrazol-1-yl)-2-(1-(difluoromethyl)-1H-pyrazol-3-yl)ethyl)-5-(3-chloro-2-fluoro-6-(4-(trifluoromethyl)-1H-1,2,3-triazol-1-yl)phenyl)pyridine 1-oxide as white solid.

LC/MS: mass calculated for $C_{30}H_{18}ClF_7N_8O_3$: 706.11, measured (ES, m/z): 707.00[M+H]$^+$. $^1$H NMR (300 MHz, DMSO-$d_6$) δ 9.18 (d, J=1.1 Hz, 1H), 8.61 (s, 1H), 8.46 (d, J=1.5 Hz, 1H), 8.16 (s, 1H), 8.11-8.02 (m, 2H), 7.90-7.75 (m, 2H), 7.71-7.47 (m, 3H), 7.30-7.36 (m, 1H), 7.15-7.20 (m, 1H), 6.35-6.41 (m, 1H), 6.12 (d, J=2.7 Hz, 1H), 3.71-3.57 (m, 2H). $^{19}$F-NMR (282 MHz, DMSO-$d_6$) δ −59.75, −93.86, −109.97, −112.82.

Example 989: (S*)-2-(1-(4-(4-Carboxy-3-fluorophenyl)-1H-pyrazol-1-yl)-2-(1-(difluoromethyl)-1H-pyrazol-3-yl)ethyl)-5-(3-chloro-2-fluoro-6-(4-(trifluoromethyl)-1H-1,2,3-triazol-1-yl)phenyl)pyridine 1-oxide

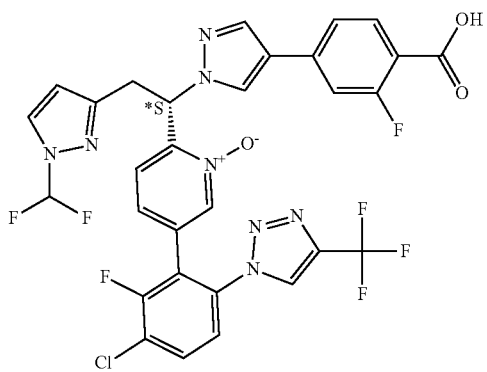 [SMILES: O=C(O)c1ccc(-c2cnn([C@@H](Cc3ccn(C(F)F)n3)c3ccc(-c4c(-n5cc(C(F)(F)F)nn5)ccc(Cl)c4F)c[n+]3[O-])c2)cc1F]

Step 1: tert-Butyl 4-(1-(1-(5-bromopyridin-2-yl)-2-(1-(difluoromethyl)-1H-pyrazol-3-yl) ethyl)-1H-pyrazol-4-yl)-2-fluorobenzoate To a solution of tert-butyl 4-(1-((5-bromopyridin-2-yl)methyl)-1H-pyrazol-4-yl)-2-fluorobenzoate (520 mg, 1.20 mmol, 1 equiv.) in tetrahydrofuran (6 mL) under nitrogen was added lithium bis(trimethylsilyl)amide (1.4 mL, 1.40 mmol, 1.0 M in THF, 1.2 equiv.) dropwise at −78° C. and the solution was stirred for 30 min at this temperature. 3-(Bromomethyl)-1-(difluoromethyl)-1H-pyrazole (305 mg, 1.44 mmol, 1.2 equiv.) in tetrahydrofuran (2 mL) was added the solution. The reaction mixture was stirred at −70° C. for 2 h under N$_2$. The reaction was quenched with sat. NH$_4$Cl (aq.) and extracted with EA twice. The combined organic layers were washed with brine, dried over Na$_2$SO$_4$, and concentrated under vacuum. The resulting residue was purified by silica gel chromatography (0→50% EA/PE) to yield tert-butyl 4-(1-(1-(5-bromopyridin-2-yl)-2-(1-(difluoromethyl)-1H-pyrazol-3-yl) ethyl)-1H-pyrazol-4-yl)-2-fluorobenzoate as light yellow oil. LC/MS: mass calculated for $C_{25}H_{23}BrF_3N_5O_2$: 561.10, measured (ES, m/z): 562.20, 564.20 [M+H, M+H+2]$^+$.

Step 2: (6-(1-(4-(4-(tert-Butoxycarbonyl)-3-fluorophenyl)-1H-pyrazol-1-yl)-2-(1-(difluoromethyl)-1H-pyrazol-3-yl) ethyl) pyridin-3-yl)boronic acid To a mixture of tert-butyl 4-(1-(1-(5-bromopyridin-2-yl)-2-(1-(difluoromethyl)-1H-pyrazol-3-yl)ethyl)-1H-pyrazol-4-yl)-2-fluorobenzoate (230 mg, 0.41 mmol, 1.0 equiv.) and 4,4,4',4',5,5,5',5'-octamethyl-2,2'-bi(1,3,2-dioxaborolane) (312 mg, 1.23 mmol, 3.0 equiv.) in 1,4-dioxane (5 mL) was added potassium acetate (161 mg, 1.64 mmol, 4.0 equiv.) and Pd(dppf)Cl$_2$ (60 mg, 0.08 mmol, 0.2 equiv.). The solution was stirred at 90° C. for 2 h under N$_2$. The mixture was quenched with H$_2$O, extracted with EA twice. The combined organic layer was washed with brine, dried over Na$_2$SO$_4$ and concentrated to yield (6-(1-(4-(4-(tert-butoxycarbonyl)-3-fluorophenyl)-1H-pyrazol-1-yl)-2-(1-(difluoromethyl)-1H-pyrazol-3-yl) ethyl) pyridin-3-yl)boronic acid as brown oil. LC/MS: mass calculated for $C_{25}H_{25}BF_3N_5O_4$: 527.20, measured (ES, m/z): 528.10 [M+H]$^+$.

Step 3: tert-Butyl 4-(1-(1-(5-(3-chloro-2-fluoro-6-(4-(trifluoromethyl)-1H-1, 2, 3-triazol-1-yl)phenyl) pyridin-2-yl)-2-(1-(difluoromethyl)-1H-pyrazol-3-yl) ethyl)-1H-pyrazol-4-yl)-2-fluorobenzoate To a mixture of (6-(1-(4-(4-(tert-butoxycarbonyl)-3-fluorophenyl)-1H-pyrazol-1-yl)-2-(1-(difluoromethyl)-1H-pyrazol-3-yl)ethyl)pyridin-3-yl)boronic acid (200 mg, 0.38 mmol, 1.0 equiv.), potassium carbonate (157 mg, 1.14 mmol, 3.0 equiv.) and tert-butyl 4-(4,4,5,5-tetramethyl-1,3,2-dioxaborolan-2-yl)-1H-pyrazole-1-carboxylate (178 mg, 0.45 mmol, 1.2 equiv.) in 1,4-dioxane (4 mL) and water (1 mL) was added tetrakis(triphenylphosphine)Palladium(0) (44 mg, 0.04 mmol, 0.1 equiv.). The solution was stirred at 100° C. for 2 h under N$_2$. Water was added, the mixture was extracted with EA. The combined organic layers were washed with brine, dried over Na$_2$SO$_4$ and concentrated. The residue was purified by silica gel chromatography (0→100% EA:PE) to yield tert-butyl 4-(1-(1-(5-(3-chloro-2-fluoro-6-(4-(trifluoromethyl)-1H-1, 2, 3-triazol-1-yl)phenyl)pyridin-2-yl)-2-(1-(difluoromethyl)-1H-pyrazol-3-yl) ethyl)-1H-pyrazol-4-yl)-2-fluorobenzoate as yellow solid. LC/MS: mass calculated for $C_{34}H_{26}ClF_7N_8O_2$: 746.18, measured (ES, m/z): 747.15 [M+H]$^+$.

Step 4: 4-(1-(1-(5-(3-Chloro-2-fluoro-6-(4-(trifluoromethyl)-1H-1, 2, 3-triazol-1-yl) phenyl) pyridin-2-yl)-2-(1-(difluoromethyl)-1H-pyrazol-3-yl)ethyl)-1H-pyrazol-4-yl)-2-fluorobenzoic acid To a mixture of tert-butyl 4-(1-(1-(5-(3-chloro-2-fluoro-6-(4-(trifluoromethyl)-1H-1,2,3-triazol-1-yl)phenyl)pyridin-2-yl)-2-(1-(difluoromethyl)-1H-pyrazol-3-yl)ethyl)-1H-pyrazol-4-yl)-2-fluorobenzoate (190 mg, 0.25 mmol, 1.0 equiv.) in dichloromethane (3 mL) was added 2, 2, 2-trifluoroacetic acid (2 mL). The reaction mixture was stirred at room temperature for 1 h. The reaction was concentrated under vacuum to yield 4-(1-(1-(5-(3-Chloro-2-fluoro-6-(4-(trifluoromethyl)-1H-1, 2, 3-triazol-1-yl) phenyl) pyridin-2-yl)-2-(1-(difluoromethyl)-1H-pyrazol-3-yl)ethyl)-1H-pyrazol-4-yl)-2-fluorobenzoic acid as yellow oil. LC/MS: mass calculated for $C_{30}H_{18}ClF_7N_8O_2$: 690.11, measured (ES, m/z): 691.10 [M+H]$^+$.

Step 5: (S*)-2-(1-(4-(4-Carboxy-3-fluorophenyl)-1H-pyrazol-1-yl)-2-(1-(difluoromethyl)-1H-pyrazol-3-yl)ethyl)-5-(3-chloro-2-fluoro-6-(4-(trifluoromethyl)-1H-1,2,3-triazol-1-yl)phenyl)pyridine 1-oxide To a solution of 4-(1-(1-(5-(3-chloro-2-fluoro-6-(4-(trifluoromethyl)-1H-1,2,3-triazol-1-yl)phenyl)pyridin-2-yl)-2-(1-(difluoromethyl)-1H-pyrazol-3-yl)ethyl)-1H-pyrazol-4-yl)-2-fluorobenzoic acid (160 mg, 0.23 mmol, 1 equiv.) and ReMeO$_3$ (12 mg, 0.05 mmol, 0.2 equiv.) in CH$_3$OH (3.0 mL) was added hydrogen peroxide (0.2 mL, 2.32 mmol, 30 wt %, 10.0 equiv.). The reaction mixture was stirred at room temperature for 1 h. The reaction mixture was purified by reverse phase chromatography on C18 (120 g, ACN/H$_2$O (0.05% CF$_3$COOH): 0→50%). The resulting residue was purified by Prep-Chiral-HPLC to yield (S*)-2-(1-(4-(4-carboxy-3-fluorophenyl)-1H-pyrazol-1-yl)-2-(1-(difluoromethyl)-1H-pyrazol-3-yl)ethyl)-5-(3-chloro-2-fluoro-6-(4-(trifluoromethyl)-1H-1,2,3-triazol-1-yl)phenyl)pyridine 1-oxide as white solid.

LC/MS: mass calculated for C$_{30}$H$_{18}$ClF$_7$N$_8$O$_3$: 706.11, measured (ES, m/z): 707.00[M+H]$^+$. $^1$H NMR (300 MHz, DMSO-d$_6$) δ 9.18 (s, 1H), 8.60 (s, 1H), 8.46 (s, 1H), 8.16 (s, 1H), 8.11-8.02 (m, 2H), 7.90-7.74 (m, 2H), 7.71-7.46 (m, 3H), 7.30-7.37 (m, 1H), 7.15-7.20 (m, 1H), 6.32-6.42 (m, 1H), 6.12 (d, J=2.6 Hz, 1H), 3.68-3.58 (m, 2H). $^{19}$F-NMR (282 MHz, DMSO-d$_6$) δ −59.75, −93.86, −110.02, −112.82.

Example 990: (S*)-2-(1-(4-(4-Carbamoyl-3-fluorophenyl)-1H-pyrazol-1-yl)-2-(1-(difluoromethyl)-1H-pyrazol-3-yl)ethyl)-5-(3-chloro-2-fluoro-6-(1H-tetrazol-1-yl)phenyl)pyridine 1-oxide

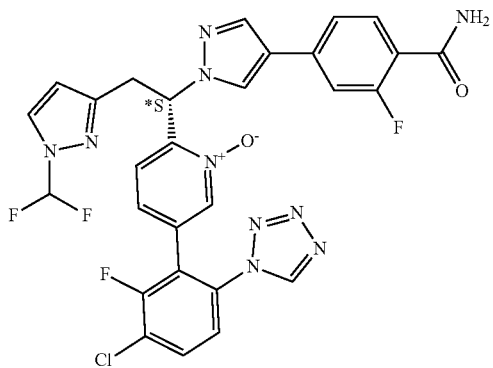 [SMILES: NC(=O)c1ccc(-c2cnn([C@@H](Cc3ccn(C(F)F)n3)c3ccc(-c4c(-n5cnnn5)ccc(Cl)c4F)c[n+]3[O-])c2)cc1F]

LC/MS: mass calculated for C$_{28}$H$_{19}$ClF$_4$N$_{10}$O$_2$: 638.13, measured (ES, m/z): 639.10 [M+H]$^+$. $^1$H NMR (300 MHz, DMSO-d$_6$) δ 9.69 (s, 1H), 8.57 (s, 1H), 8.48 (s, 1H), 8.15 (s, 1H), 8.03-8.12 (m, 2H), 7.89 (t, J=54.0 Hz, 1H), 7.76 (dd, J=8.7, 1.6 Hz, 1H), 7.64-7.69 (m, 1H), 7.55-7.60 (m, 2H), 7.45-7.51 (m, 2H), 7.32 (d, J=8.4 Hz, 1H), 7.18-7.22 (m, 1H), 6.30-6.41 (m, 1H), 6.11 (d, J=2.6 Hz, 1H), 3.69-3.59 (m, 2H) $^{19}$F NMR (282 MHz, DMSO-d$_6$) δ −93.80, −112.66.

Example 991: (R*)-2-(1-(4-(4-Carbamoyl-3-fluorophenyl)-1H-pyrazol-1-yl)-2-(1-(difluoromethyl)-1H-pyrazol-3-yl)ethyl)-5-(3-chloro-2-fluoro-6-(1H-tetrazol-1-yl)phenyl)pyridine 1-oxide

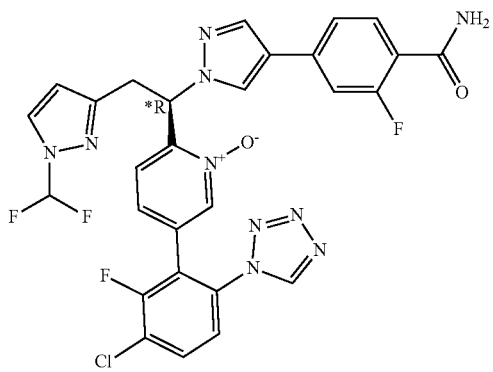 [SMILES: NC(=O)c1ccc(-c2cnn([C@H](Cc3ccn(C(F)F)n3)c3ccc(-c4c(-n5cnnn5)ccc(Cl)c4F)c[n+]3[O-])c2)cc1F]

Step 1: tert-Butyl 4-(1-(1-(5-(6-amino-3-chloro-2-fluorophenyl)pyridin-2-yl)-2-(1-(difluoromethyl)-1H-pyrazol-3-yl)ethyl)-1H-pyrazol-4-yl)-2-fluorobenzoate To a mixture of tert-butyl 4-(1-(1-(5-bromopyridin-2-yl)-2-(1-(difluoromethyl)-1H-pyrazol-3-yl) ethyl)-1H-pyrazol-4-yl)-2-fluorobenzoate (270 mg, 0.48 mmol, 1.0 equiv.), potassium carbonate (199 mg, 1.44 mmol, 3.0 equiv.) and (6-amino-3-chloro-2-fluorophenyl)boronic acid (136 mg, 0.72 mmol, 1.5 equiv.) in 1,4-dioxane (4 mL) and water (1 mL) was added tetrakis(triphenylphosphine) palladium(0) (55 mg, 0.05 mmol, 0.1 equiv.). The solution was stirred at 90° C. for 2 h under N$_2$. Water was added, the mixture was extracted with EA. The combined organic layers were washed with brine, dried over Na$_2$SO$_4$ and concentrated and purified by silica gel chromatography (0→60% EA/PE) to yield tert-butyl 4-(1-(1-(5-(6-amino-3-chloro-2-fluorophenyl)pyridin-2-yl)-2-(1-(difluoromethyl)-1H-pyrazol-3-yl) ethyl)-1H-pyrazol-4-yl)-2-fluorobenzoate as yellow solid. LC/MS: mass calculated for C$_{31}$H$_{27}$ClF$_4$N$_6$O$_2$: 626.18, measured (ES, m/z): 627.15 [M+H]$^+$.

Step 2: 4-(1-(1-(5-(6-Amino-3-chloro-2-fluorophenyl) pyridin-2-yl)-2-(1-(difluoromethyl)-1H-pyrazol-3-yl) ethyl)-1H-pyrazol-4-yl)-2-fluorobenzoic acid To a mixture of tert-butyl 4-(1-(1-(5-(6-amino-3-chloro-2-fluorophenyl)pyridin-2-yl)-2-(1-(difluoromethyl)-1H-pyrazol-3-yl)ethyl)-1H-pyrazol-4-yl)-2-fluorobenzoate (270 mg, 0.43 mmol, 1.0 equiv.) in dichloromethane (3 mL) was added 2, 2, 2-trifluoroacetic acid (2 mL). The reaction mixture was stirred at room temperature for 1 h. The reaction was concentrated under vacuum to yield 4-(1-(1-(5-(6-amino-3-chloro-2-fluorophenyl) pyridin-2-yl)-2-(1-(difluoromethyl)-1H-pyrazol-3-yl) ethyl)-1H-pyrazol-4-yl)-2-fluorobenzoic acid as a yellow oil. LC/MS: mass calculated for C$_{27}$H$_{19}$ClF$_4$N$_6$O$_2$: 570.12, measured (ES, m/z): 571.00 [M+H]$^+$.

Step 3: 4-(1-(1-(5-(3-Chloro-2-fluoro-6-(1H-tetrazol-1-yl) phenyl) pyridin-2-yl)-2-(1-(difluoromethyl)-1H-pyrazol-3-yl) ethyl)-1H-pyrazol-4-yl)-2-fluorobenzoic acid To a solution of 4-(1-(1-(5-(6-amino-3-chloro-2-fluorophenyl) pyridin-2-yl)-2-(1-(difluoromethyl)-1H-pyrazol-3-yl) ethyl)-1H-pyrazol-4-yl)-2-fluorobenzoic acid (220 mg, 0.39 mmol, 1.0 equiv.) in acetonitrile (3.0 mL) was added azidotrimethylsilane (2.0 mL) and trimethoxymethane (2.0 mL). The reaction mixture was stirred at room temperature for 1.5 h. The reaction mixture was concentrated under vacuum. The residue was purified by reverse phase chromatography on C18 (120 g, ACN/H$_2$O (0.05% CF$_3$COOH): 0→70%) to yield 4-(1-(1-(5-(3-chloro-2-fluoro-6-(1H-tetrazol-1-yl) phenyl) pyridin-2-yl)-2-(1-(difluoromethyl)-1H-pyrazol-3-yl) ethyl)-1H-pyrazol-4-yl)-2-fluorobenzoic acid as brown solid. LC/MS: mass calculated for C$_{28}$H$_{18}$ClF$_4$N$_9$O$_2$: 623.12, measured (ES, m/z): 624.15 [M+H]$^+$.

Step 4: 2-(1-(4-(4-Carboxy-3-fluorophenyl)-1H-pyrazol-1-yl)-2-(1-(difluoromethyl)-1H-pyrazol-3-yl) ethyl)-5-(3-chloro-2-fluoro-6-(1H-tetrazol-1-yl) phenyl) pyridine 1-oxide To a solution of 4-(1-(1-(5-(3-chloro-2-fluoro-6-(1H-tetrazol-1-yl) phenyl) pyridin-2-yl)-2-(1-(difluoromethyl)-1H- pyrazol-3-yl) ethyl)-1H-pyrazol-4-yl)-2-fluorobenzoic acid (200 mg, 0.32 mmol, 1.0 equiv.) and MeReO₃ (16 mg, 0.06 mmol, 0.2 equiv.) in CH₃OH (4.0 mL) was added hydrogen peroxide (0.3 mL, 3.20 mmol, 30 wt %, 10.0 equiv.). The reaction mixture was stirred at room temperature for 3 h. The reaction was purified by reverse phase chromatography on C18 (120 g, ACN/H₂O (0.05% CF₃COOH: 0→50%) to yield 2-(1-(4-(4-carboxy-3-fluorophenyl)-1H-pyrazol-1-yl)-2-(1-(difluoromethyl)-1H-pyrazol-3-yl) ethyl)-5-(3-chloro-2-fluoro-6-(1H-tetrazol-1-yl) phenyl) pyridine 1-oxide as white solid. LC/MS: mass calculated for C₂₈H₁₈ClF₄N₉O₃: 639.12, measured (ES, m/z): 640.05 [M+H]⁺.

Step 5: (R*)-2-(1-(4-(4-Carbamoyl-3-fluorophenyl)-1H-pyrazol-1-yl)-2-(1-(difluoromethyl)-1H-pyrazol-3-yl) ethyl)-5-(3-chloro-2-fluoro-6-(1H-tetrazol-1-yl) phenyl) pyridine 1-oxide To a mixture of 2-(1-(4-(4-carboxy-3-fluorophenyl)-1H-pyrazol-1-yl)-2-(1-(difluoromethyl)-1H-pyrazol-3-yl) ethyl)-5-(3-chloro-2-fluoro-6-(1H-tetrazol-1-yl) phenyl) pyridine 1-oxide (130 mg, 0.20 mmol, 1.0 equiv.) and HATU (155 mg, 0.41 mmol, 2.0 equiv.) in N, N-dimethylformamide (3.0 mL) was added N, N-diisopropylethylamine (103 mg, 0.81 mmol, 4.0 equiv.) and ammonium chloride (22 mg, 0.41 mmol, 2.0 equiv.). The solution was stirred at room temperature for 1 h. The reaction mixture was purified by reverse phase chromatography on C18 (120 g, ACN/H₂O (0.05% CF₃COOH): 0→50%). 110 mg of resulting residue was purified by Prep-Chiral-HPLC to yield (R*)-2-(1-(4-(4-carbamoyl-3-fluorophenyl)-1H-pyrazol-1-yl)-2-(1-(difluoromethyl)-1H-pyrazol-3-yl) ethyl)-5-(3-chloro-2-fluoro-6-(1H-tetrazol-1-yl) phenyl) pyridine 1-oxide as a white solid. LC/MS: mass calculated for C₂₈H₁₉ClF₄N₁₀O₂: 638.13, measured (ES, m/z): 639.10 [M+H]⁺. ¹H NMR (300 MHz, DMSO-d₆) δ 9.69 (s, 1H), 8.58 (s, 1H), 8.48 (d, J=1.6 Hz, 1H), 8.15 (s, 1H), 8.02-8.11 (m, 2H), 7.45-7.90 (m, 7H), 7.30-7.35 (m, 1H), 7.17-7.23 (m, 1H), 6.33-6.40 (m, 1H), 6.11 (d, J=2.7 Hz, 1H), 3.54-3.75 (m, 2H). ¹⁹F-NMR (282 MHz, DMSO-d₆) δ −93.80, −112.66, −112.96.

Example 992: 5-(3-Chloro-2-fluoro-6-(4-(trifluoromethyl)-1H-1,2,3-triazol-1-yl)phenyl)-2-(1-(4-(1-methyl-1H-1,2,4-triazol-5-yl)-1H-pyrazol-1-yl)-2-(morpholin-2-yl)ethyl)pyridine 1-oxide TFA

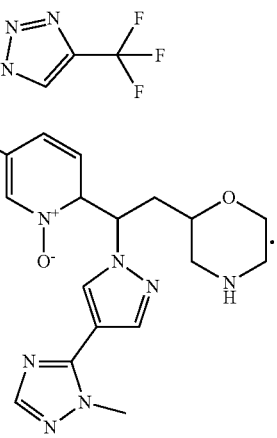

5-(3-Chloro-2-fluoro-6-(4-(trifluoromethyl)-1H-1,2,3-triazol-1-yl)phenyl)-2-(1-(4-(1-methyl-1H-1,2,4-triazol-5-yl)-1H-pyrazol-1-yl)-2-(morpholin-2-yl)ethyl)pyridine 1-oxide TFA was prepared as described herein. The resulting reaction residue was purified via ISCO reverse phase chromatography with 0.1% TFA in water and 0.1% TFA in ACN as eluent (35% to 60% 0.1% TFA in ACN gradient) to yield a white solid.

LC-MS: calculated mass for C₂₆H₂₃ClF₄N₁₀O₂: 618.2, measured (ES, m/z): 619.2 [M+H]⁺. ¹H NMR (DMSO-d₆, 400 MHz) δ-9.20-9.18 (m, 1H), 8.97-8.70 (bs, 1H), 8.68-8.63 (m, 1H), 8.48-8.40 (m, 1H), 8.10-8.03 (m, 1H), 7.95-7.89 (m, 1H), 7.81-7.74 (m, 2H), 7.37-7.13 (m, 1H), 6.40-6.22 (m, 1H), 4.05-3.81 (m, 1H), 3.67-3.42 (m, 2H), 3.35-3.06 (m, 2H), 3.05-2.26 (m, 5H). ¹⁹F NMR (DMSO-d₆, 377 MHz) δ −125.3, −86.5.

Example 993: 5-(3-Chloro-2-fluoro-6-(4-(trifluoromethyl)-1H-1,2,3-triazol-1-yl)phenyl)-2-(1-(4-(1-methyl-1H-1,2,4-triazol-5-yl)-1H-pyrazol-1-yl)-2-(1,3,4-oxadiazol-2-yl)ethyl)pyridine 1-oxide TFA

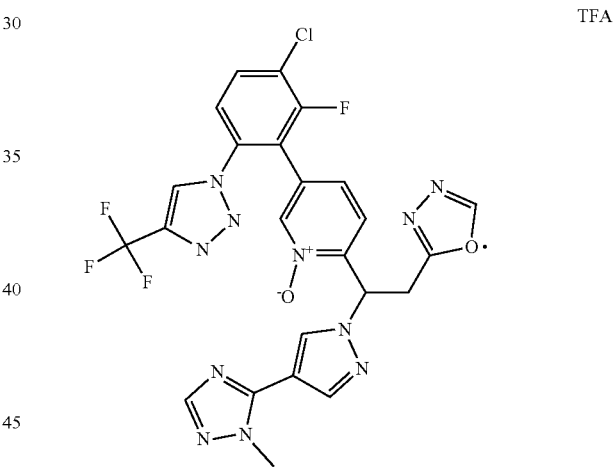

5-(3-Chloro-2-fluoro-6-(4-(trifluoromethyl)-1H-1,2,3-triazol-1-yl)phenyl)-2-(1-(4-(1-methyl-1H-1,2,4-triazol-5-yl)-1H-pyrazol-1-yl)-2-(1,3,4-oxadiazol-2-yl)ethyl)pyridine 1-oxide TFA was prepared according to the procedure as described herein. The resulting residue was purified via ISCO reverse phase chromatography with 0.1% TFA in water and 0.1% TFA in ACN as eluent (35% to 60% 0.1% TFA in ACN gradient) to yield a white solid.

LC-MS: calculated mass for C₂₄H₁₆ClF₄N₁₁O₂: 601.1, measured (ES, m/z): 602.3 [M+H]⁺. ¹H NMR (DMSO-d₆, 400 MHz) δ-9.19 (s, 1H), 9.13 (s, 1H), 8.65 (s, 1H), 8.51 (s, 1H), 8.08 (d, J=8.8 Hz, 1H), 8.05 (s, 1H), 7.89 (s, 1H), 7.78 (dd, JJ=8.8, 1.4 Hz, 1H), 7.28 (d, J=8.3 Hz, 1H), 7.21 (dd, JJ=8.3, 1.5 Hz, 1H), 6.63-6.60 (m, 1H), 4.05-3.99 (m, 2H), 3.93 (s, 3H).

Example 994: (R*)-2-(1-(4-(4-Carbamoyl-3-fluorophenyl)-1H-pyrazol-1-yl)-2-(2-oxopyrrolidin-1-yl)ethyl)-5-(3-chloro-2-fluoro-6-(4-(trifluoromethyl)-1H-1,2,3-triazol-1-yl)phenyl)pyridine 1-oxide

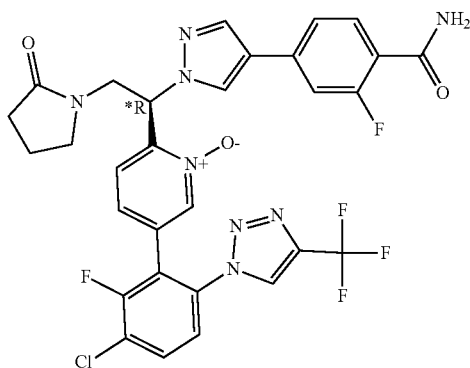 [SMILES: NC(=O)c1ccc(-c2cnn([C@H](CN3CCCC3=O)c3ccc(-c4c(-n5cc(C(F)(F)F)nn5)ccc(Cl)c4F)c[n+]3[O-])c2)cc1F]

LC/MS: mass calculated for $C_{30}H_{22}ClF_5N_8O_3$: 672.14, measured (ES, m/z): 673.10 [M+H]+. $^1$H NMR (300 MHz, DMSO-$d_6$) δ 9.20 (d, J=1.1 Hz, 1H), 8.61 (s, 1H), 8.45 (d, J=1.6 Hz, 1H), 8.12 (s, 1H), 8.07 (dd, J=8.7, 7.8 Hz, 1H), 7.79 (dd, J=8.7, 1.5 Hz, 1H), 7.69 (t, J=8.0 Hz, 1H), 7.48-7.65 (m, 5H), 7.20 (dd, J=8.3, 1.7 Hz, 1H), 6.36 (t, J=7.3 Hz, 1H), 4.03 (d, J=7.4 Hz, 2H), 3.24-3.33 (m, 1H), 2.89-3.03 (m, 1H), 2.08-2.19 (m, 2H), 1.72-1.89 (m, 2H). $^{19}$F NMR (282 MHz, DMSO-$d_6$) δ −59.72, −112.78, −113.01.

Example 995: (S*)-2-(1-(4-(4-Carbamoyl-3-fluorophenyl)-1H-pyrazol-1-yl)-2-(2-oxopyrrolidin-1-yl)ethyl)-5-(3-chloro-2-fluoro-6-(4-(trifluoromethyl)-1H-1,2,3-triazol-1-yl)phenyl)pyridine 1-oxide

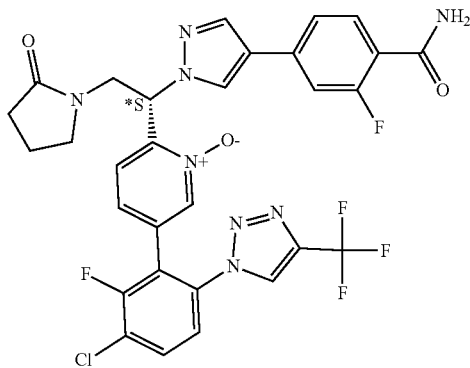 [SMILES: NC(=O)c1ccc(-c2cnn([C@@H](CN3CCCC3=O)c3ccc(-c4c(-n5cc(C(F)(F)F)nn5)ccc(Cl)c4F)c[n+]3[O-])c2)cc1F]

LC/MS: mass calculated for $C_{30}H_{22}ClF_5N_8O_3$: 672.14, measured (ES, m/z): 673.15 [M+H]+. $^1$H NMR (300 MHz, DMSO-$d_6$) δ 9.20 (s, 1H), 8.61 (s, 1H), 8.46 (s, 1H), 8.12 (s, 1H), 8.08 (t, J=8.2 Hz, 1H), 8.04-8.11 (m, 1H), 7.76-7.82 (m, 1H), 7.66-7.74 (m, 1H), 7.48-7.67 (m, 5H), 7.21 (d, J=8.4 Hz, 1H), 6.36 (t, J=7.3 Hz, 1H), 4.04 (d, J=7.4 Hz, 2H), 3.25-3.35 (m, 1H), 2.93-3.04 (m, 1H), 2.06-2.20 (m, 2H), 1.72-1.91 (m, 2H). $^{19}$F NMR (282 MHz, DMSO-$d_6$) δ −59.72, −112.77, −113.00.

Example 996: 2-(1-(3'-Chloro-1H,1'H-[4,4'-bipyrazol]-1-yl)-2-cyclopropylethyl)-5-(3-chloro-2-fluoro-6-(1H-tetrazol-1-yl)phenyl)pyridine 1-oxide

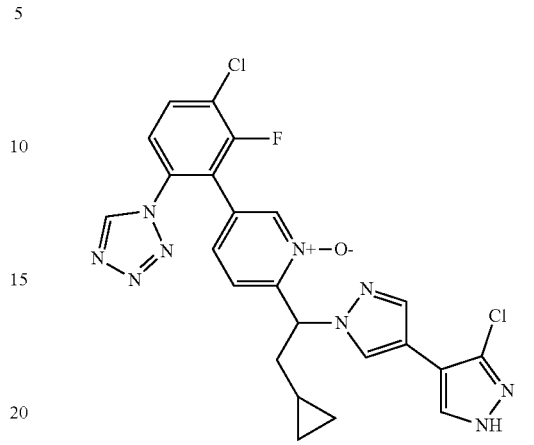

LC/MS: mass calculated for $C_{23}H_{18}Cl_2FN_9$: 525.10, measured (ES, m/z): 526.00 [M+H]+. $^1$H NMR (400 MHz, DMSO-$d_6$) δ 13.11 (br, 1H), 9.68 (s, 1H), 8.41 (s, 1H), 8.27 (s, 1H), 8.07 (s, 1H), 8.04 (d, J=8.2 Hz, 1H), 7.85 (s, 1H), 7.75 (d, J=8.7 Hz, 1H), 7.24 (d, J=8.3 Hz, 1H), 7.10-7.20 (m, 1H), 6.05-6.11 (m, 1H), 2.25-2.43 (m, 1H), 1.80-1.97 (m, 1H), 0.52-0.68 (m, 1H), 0.22-0.42 (m, 2H), 0.06-0.18 (m, 1H), 0.01-0.05 (m, 1H). $^{19}$F NMR (376 MHz, DMSO-$d_6$) δ −74.69, −112.77.

Example 997: (R*)-5-(5-Chloro-2-(4-(trifluoromethyl)-1H-1,2,3-triazol-1-yl)phenyl)-2-(2-cyclopropyl-1-(4-(1-(difluoromethyl)-1H-1,2,4-triazol-5-yl)-1H-pyrazol-1-yl)ethyl)-4-methoxypyridine 1-oxide

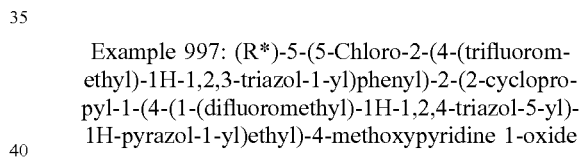
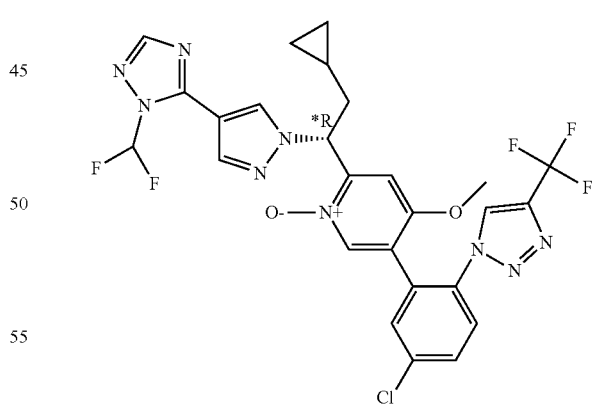

LC/MS: mass calculated for $C_{26}H_{21}ClF_5N_9O_2$: 621.14, measured (ES, m/z): 622.00 [M+H]+. $^1$H NMR (300 MHz, CD$_3$OD) δ 8.83 (s, 1H), 8.57 (s, 1H), 8.35 (s, 1H), 8.10-8.14 (m, 2H), 7.81 (t, J=57.7 Hz, 1H), 7.74-7.80 (m, 2H), 7.72 (d, J=2.2 Hz, 1H), 7.17 (s, 1H), 6.33-6.42 (m, 1H), 3.59 (s, 3H), 2.41-2.57 (m, 1H), 2.06-2.21 (m, 1H), 0.60-0.75 (m, 1H), 0.34-0.57 (m, 2H), 0.16-0.30 (m, 1H), 0.03-0.12 (m, 1H). $^{19}$F NMR (282 MHz, CD$_3$OD) δ −62.60, −97.68, 97.97.

Example 998: (S*)-5-(5-Chloro-2-(4-(trifluoromethyl)-1H-1,2,3-triazol-1-yl)phenyl)-2-(2-cyclopropyl-1-(4-(1-(difluoromethyl)-1H-1,2,4-triazol-5-yl)-1H-pyrazol-1-yl)ethyl)-4-methoxypyridine 1-oxide

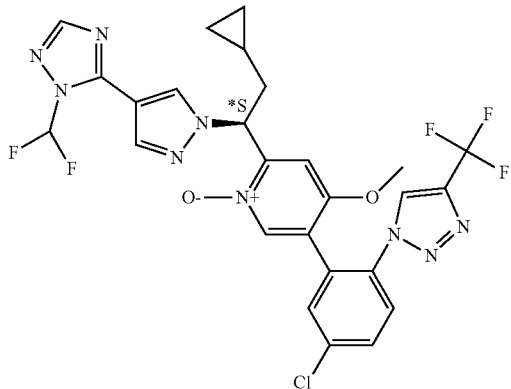 [SMILES: COc1cc([C@H](CC2CC2)n2cc(-c3ncnn3C(F)F)cn2)[n+]([O-])cc1-c1cc(Cl)ccc1-n1cc(C(F)(F)F)nn1]

LC/MS: mass calculated for $C_{26}H_{21}ClF_5N_9O_2$: 621.14, measured (ES, m/z): 622.00 [M+H]$^+$. $^1$H NMR (300 MHz, CD$_3$OD) δ 8.83 (s, 1H), 8.57 (s, 1H), 8.35 (s, 1H), 8.08-8.11 (m, 2H), 7.81 (t, J=57.8 Hz, 1H), 7.74-7.80 (m, 2H), 7.72 (d, J=2.2 Hz, 1H), 7.17 (s, 1H), 6.31-6.39 (m, 1H), 3.59 (s, 3H), 2.41-2.57 (m, 1H), 2.06-2.21 (m, 1H), 0.60-0.75 (m, 1H), 0.34-0.57 (m, 2H), 0.16-0.30 (m, 1H), 0.03-0.12 (m, 1H). $^{19}$F NMR (282 MHz, CD$_3$OD). δ −62.60, −97.68, 97.97.

Example 999: 2-(1-(4-(4-Carboxy-3-fluorophenyl)-1H-pyrazol-1-yl)-2-(thiazol-2-yl)ethyl)-5-(3-chloro-2-fluoro-6-(4-(trifluoromethyl)-1H-1,2,3-triazo-1-yl)phenyl)pyridine 1-oxide

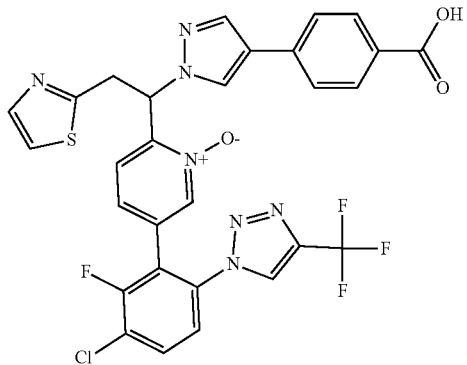 [SMILES: O=C(O)c1ccc(-c2cnn(C(Cc3nccs3)c3ccc(-c4c(-n5cc(C(F)(F)F)nn5)ccc(Cl)c4F)c[n+]3[O-])c2)cc1]

LC/MS: mass calculated for $C_{29}H_{17}ClF_5N_7O_3S$: 673.07, measured (ES, m/z): 673.95 [M+H]$^+$. $^1$H NMR (400 MHz, DMSO-d$_6$) δ 13.10 (brs, 1H), 9.1 (s, 1H), 8.63 (s, 1H), 8.48 (s, 1H), 8.19 (s, 1H), 8.02-8.11 (m, 1H), 7.73-7.89 (m, 2H), 7.61 (s, 1H), 7.42-7.59 (m, 3H), 7.21-7.32 (m, 1H), 7.11-7.21 (m, 1H), 6.51-6.52 (m, 1H), 4.00-4.06 (m, 2H)./19F NMR (400 MHz, DMSO-d$_6$) δ −59.70, −73.79, −109.92, −112.79.

Example 1000: (S*)-2-(1-(4-(4-Carboxy-3-fluorophenyl)-1H-pyrazol-1-yl)-2-(1-(difluoromethyl)-1H-pyrazol-3-yl)ethyl)-5-(3-chloro-6-(difluoromethyl)-2-fluorophenyl)pyridine 1-oxide

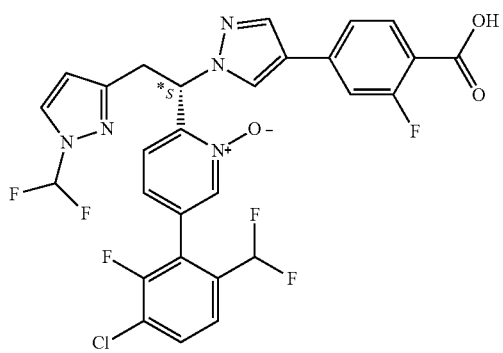

LC/MS: mass calculated for $C_{28}H_{18}ClF_6N_5O_3$: 621.10; measured (ES, m/z): 622.10 [M+H]$^+$. $^1$H NMR (300 MHz, DMSO-d$_6$) δ 8.69 (s, 1H), 8.56 (s, 1H), 8.23 (s, 1H), 8.07 (d, J=2.6 Hz, 1H), 7.89-7.93 (m, 1H), 7.84 (d, J=8.1 Hz, 1H), 7.71 (t, J=51.0 Hz, 1H), 7.50-7.65 (m, 3H), 7.41-7.44 (m, 2H), 6.90 (t, J=53.8 Hz, 1H), 6.42-6.49 (m, 1H), 6.17 (d, J=2.7 Hz, 1H), 3.62-3.78 (m, 2H). $^{19}$F NMR (282 MHz, DMSO-d$_6$) δ −73.54, −93.80, −109.91, −115.22.

Example 1001: (R*)-2-(1-(4-(4-Carboxy-3-fluorophenyl)-1H-pyrazol-1-yl)-2-(1-(difluoromethyl)-1H-pyrazol-3-yl)ethyl)-5-(3-chloro-6-(difluoromethyl)-2-fluorophenyl)pyridine 1-oxide

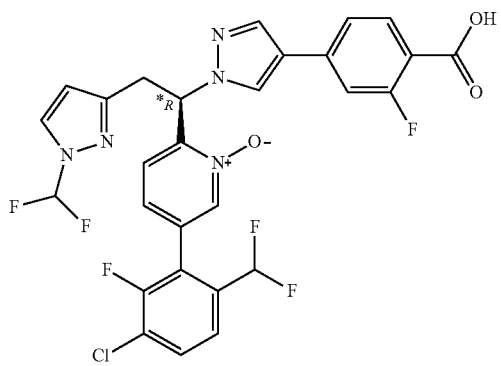

LC/MS: mass calculated for $C_{28}H_{18}ClF_6N_5O_3$: 621.10; measured (ES, m/z): 622.10 [M+H]$^+$. $^1$H NMR (300 MHz, DMSO-d$_6$) δ 8.69 (s, 1H), 8.56 (s, 1H), 8.23 (s, 1H), 8.07 (d, J=2.6 Hz, 1H), 7.90-7.94 (m, 1H), 7.84 (d, J=8.1 Hz, 1H), 7.71 (t, J=51.0 Hz, 1H), 7.66-7.50 (m, 3H), 7.39-7.46 (m, 2H), 6.90 (t, J=53.9 Hz, 1H), 6.41-6.50 (m, 1H), 6.17 (d, J=2.7 Hz, 1H), 3.65-3.83 (m, 2H). $^{19}$F NMR (282 MHz, DMSO-d$_6$) δ −93.80, −109.91, −115.22.

Example 1002: (R*)-2-(1-(4-(4-Carbamoyl-3-fluorophenyl)-1H-pyrazol-1-yl)-2-(1-(difluoromethyl)-1H-pyrazol-3-yl)ethyl)-5-(3-chloro-6-(difluoromethyl)-2-fluorophenyl)pyridine 1-oxide

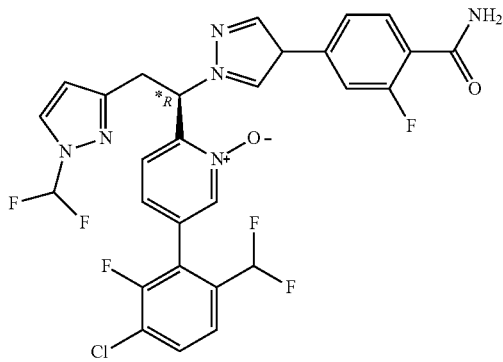

LC/MS: mass calculated for $C_{28}H_{18}ClF_6N_6O_2$: 620.12, measured (ES, m/z): 621.10 [M+H]$^+$. $^1$H NMR (400 MHz, DMSO-d$_6$) δ 8.62 (s, 1H), 8.53 (s, 1H), 8.17 (s, 1H), 8.05 (d, J=2.6 Hz, 1H), 7.82-7.91 (m, 1H), 7.36-7.69 (m, 9H), 6.88 (t, J=53.9 Hz, 1H), 6.39-6.45 (m, 1H), 6.14 (d, J=2.7 Hz, 1H), 3.57-3.80 (m, 2H). $^{19}$F NMR (376 MHz, DMSO-d$_6$) δ −74.76, −93.79, −112.95, −115.23.

Example 1003: (S*)-2-(1-(4-(4-Carbamoyl-3-fluorophenyl)-1H-pyrazol-1-yl)-2-(1-(difluoromethyl)-1H-pyrazol-3-yl)ethyl)-5-(3-chloro-6-(difluoromethyl)-2-fluorophenyl)pyridine 1-oxide

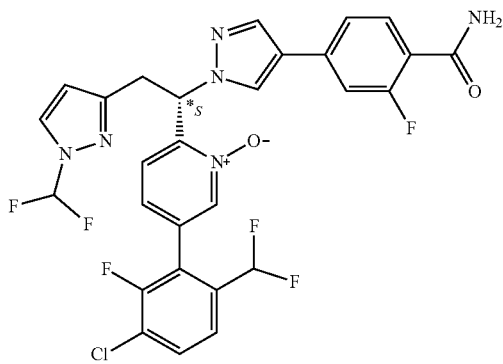 [SMILES: NC(=O)c1ccc(-c2cnn([C@@H](Cc3ccn(C(F)F)n3)c3ccc(-c4c(C(F)F)ccc(Cl)c4F)c[n+]3[O-])c2)cc1F]

LC/MS: mass calculated for $C_{28}H_{19}ClF_6N_6O_2$: 620.12, measured (ES, m/z): 621.10 [M+H]$^+$. $^1$H NMR (400 MHz, DMSO-d$_6$) δ 8.62 (s, 1H), 8.53 (s, 1H), 8.17 (s, 1H), 8.05 (d, J=2.6 Hz, 1H), 7.81-7.94 (m, 1H), 7.36-7.70 (m, 9H), 6.88 (t, J=53.9 Hz, 1H), 6.39-6.45 (m, 1H), 6.13 (d, J=2.7 Hz, 1H), 3.61-3.79 (m, 2H). $^{19}$F NMR (376 MHz, DMSO-d$_6$) δ −74.52, −93.79, −112.95, −115.22.

Example 1004: (R*)-2-(1-(4-(4-Carbamoyl-3-fluorophenyl)-1H-pyrazol-1-yl)-2-(thiazol-2-yl)ethyl)-5-(3-Chloro-2-fluoro-6-(4-(trifluoromethyl)-1H-1,2,3-triazol-1-yl)phenyl)pyridine 1-oxide

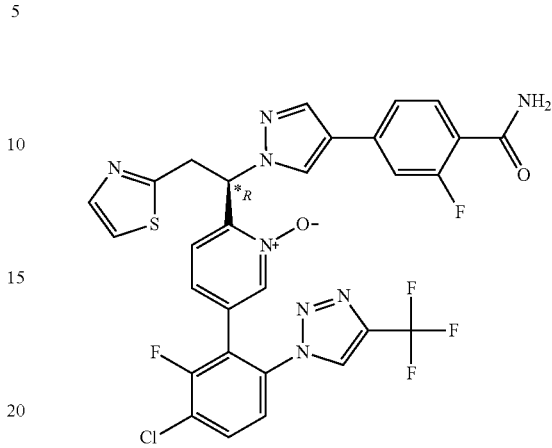

LC/MS: mass calculated for $C_{29}H_{18}ClF_5N_8O_2S$: 672.09; measured (ES, m/z): 672.95 [M+H]$^+$. $^1$H NMR (400 MHz, DMSO-d$_6$) δ 9.11 (d, J=0.8 Hz, 1H), 8.53 (s, 1H), 8.45 (s, 1H), 8.14 (s, 1H), 8.02 (dd, J=8.7, 7.8 Hz, 1H), 7.73 (dd, J=8.7, 1.5 Hz, 1H), 7.65-7.70 (m, 2H), 7.49-7.58 (m, 3H), 7.32 (d, J=8.3 Hz, 1H), 7.21 (dd, J=8.3, 1.7 Hz, 1H), 6.48-6.52 (m, 1H), 3.93-4.18 (m, 2H). $^{19}$F NMR (400 MHz, DMSO-d$_6$) δ −59.76, −73.66, −112.89.

Example 1005: (S*)-2-(1-(4-(4-Carbamoyl-3-fluorophenyl)-1H-pyrazol-1-yl)-2-(thiazol-2-yl)ethyl)-5-(3-chloro-2-fluoro-6-(4-(trifluoromethyl)-1H-1,2,3-triazol-1-yl)phenyl)pyridine 1-oxide

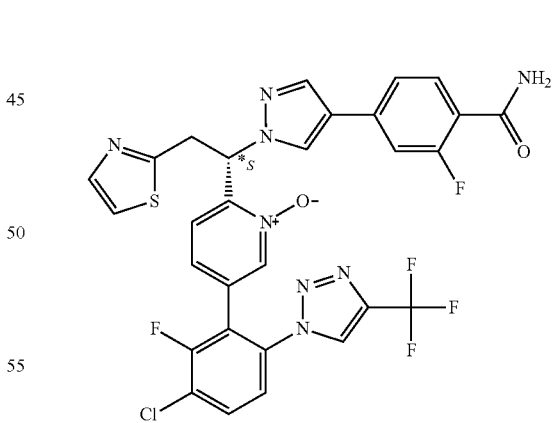

LC/MS: mass calculated for $C_{29}H_{18}ClF_5N_8O_2S$: 672.09; measured (ES, m/z): 672.95 [M+H]$^+$. $^1$H NMR (400 MHz, DMSO-d$_6$) δ 9.11 (d, J=1.0 Hz, 1H), 8.55 (s, 1H), 8.46 (s, 1H), 8.15 (s, 1H), 8.03 (dd, J=8.7, 7.8 Hz, 1H), 7.74 (dd, J=8.7, 1.5 Hz, 1H), 7.64-7.69 (m, 2H), 7.45-7.54 (m, 3H), 7.30 (d, J=8.3 Hz, 1H), 7.18 (dd, J=8.3, 1.7 Hz, 1H), 6.49-6.52 (m, 1H), 3.91-4.12 (m, 2H). $^{19}$F NMR (400 MHz, DMSO-d$_6$) δ −59.73, −73.59, −112.89.

Example 1006: (R*)-5-(5-Chloro-2-(4-(trifluoromethyl)-1H-1,2,3-triazol-1-yl)phenyl)-2-(2-cyclopropyl-1-(4-(1-methyl-1H-1,2,4-triazol-5-yl)-1H-pyrazol-1-yl)ethyl)-4-ethoxypyridine 1-oxide

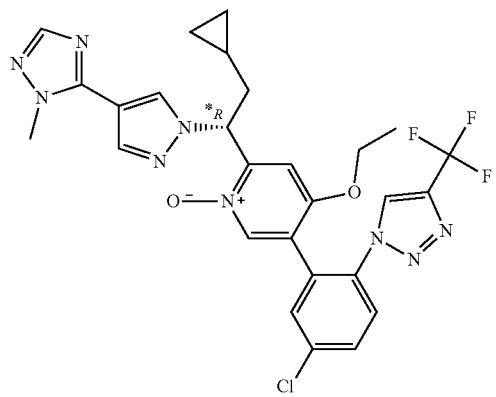

LC/MS: mass calculated for $C_{27}H_{25}ClF_3N_9O_2$: 599.18; measured (ES, m/z): 600.05 [M+H]$^+$. $^1$H NMR (300 MHz, DMSO-d$_6$) δ 9.20 (s, 1H), 8.63 (s, 1H), 8.33 (s, 1H), 8.01 (s, 1H), 7.87 (s, 1H), 7.81 (s, 3H), 6.91 (s, 1H), 6.20-6.29 (m, 1H), 3.94 (s, 3H), 3.51-3.70 (m, 2H), 2.21-2.37 (m, 1H), 2.05-2.15 (m, 1H), 0.95 (t, J=6.9 Hz, 3H), 0.52-0.63 (m, 1H), 0.23-0.42 (m, 2H), 0.07-0.15 (m, 1H), −0.09-0.02 (m, 1H). $^{19}$F NMR (282 MHz, DMSO-d$_6$) δ −59.80.

Example 1007: (S*)-5-(5-Chloro-2-(4-(trifluoromethyl)-1H-1,2,3-triazol-1-yl)phenyl)-2-(2-cyclopropyl-1-(4-(1-methyl-1H-1,2,4-triazol-5-yl)-1H-pyrazol-1-yl)ethyl)-4-ethoxypyridine 1-oxide

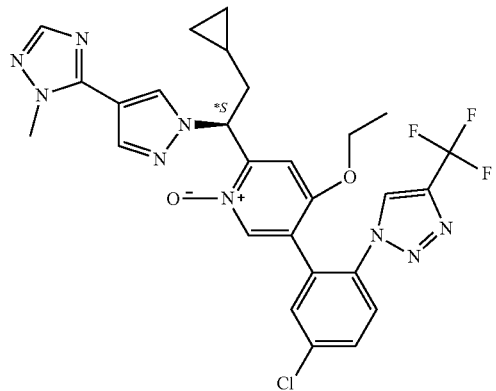

LC/MS: mass calculated for $C_{27}H_{25}ClF_3N_9O_2$: 599.18, measured (ES, m/z): 600.05 [M+H]$^+$. $^1$H NMR (300 MHz, CD$_3$OD) δ 8.82 (s, 1H), 8.53 (s, 1H), 8.34 (s, 1H), 8.10 (s, 1H), 7.92 (s, 1H), 7.75-7.81 (m, 2H), 7.65-7.73 (m, 1H), 7.09 (s, 1H), 6.30-6.42 (m, 1H), 4.03 (s, 3H), 3.72-3.86 (m, 2H), 2.43-2.53 (m, 1H), 2.04-2.13 (m, 1H), 1.11 (t, J=7.0 Hz, 3H), 0.63-0.71 (m, 1H), 0.37-0.50 (m, 2H), 0.16-0.23 (m, 1H), 0.03-0.11 (m, 1H). $^{19}$F NMR (282 MHz, CD$_3$OD) δ −62.64, −77.05.

Example 1008: (R*)-2-(1-(4-(4-Carbamoyl-3-fluorophenyl)-1H-pyrazol-1-yl)-2-cyclopropylethyl)-5-(3-chloro-2-fluoro-6-(1H-tetrazol-1-yl)phenyl)pyridine 1-oxide

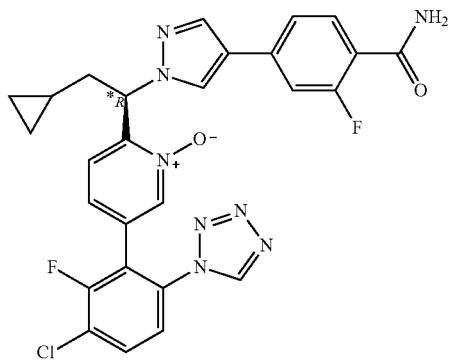 [SMILES: NC(=O)c1ccc(-c2cnn([C@H](CC3CC3)c3ccc(-c4c(-n5cnnn5)ccc(Cl)c4F)c[n+]3[O-])c2)cc1F]

LC/MS: mass calculated for $C_{27}H_{21}ClF_2N_8O_2$: 562.05; measured (ES, m/z): 563.1 [M+H]$^+$. $^1$H NMR (400 MHz, DMSO-d$_6$) δ 9.68 (s, 1H), 8.66 (s, 1H), 8.41 (s, 1H), 8.14 (s, 1H), 8.05 (t, J=8.2 Hz, 1H), 7.75 (d, J=8.7 Hz, 1H), 7.68 (t, J=8.0 Hz, 1H), 7.50-7.61 (m, 4H), 7.28 (d, J=8.3 Hz, 1H), 7.15 (d, J=8.3 Hz, 1H), 6.05-6.11 (m, 1H), 2.32-2.43 (m, 1H), 1.83-1.94 (m, 1H), 0.55-0.65 (m, 1H), 0.25-0.41 (m, 2H), 0.07-0.15 (m, 1H), −0.05-003 (m, 1H). $^{19}$F NMR (376 MHz, DMSO-d$_6$) δ −112.75, −113.00.

Example 1009: (S*)-2-(1-(4-(4-Carbamoyl-3-fluorophenyl)-1H-pyrazol-1-yl)-2-cyclopropylethyl)-5-(3-chloro-2-fluoro-6-(1H-tetrazol-1-yl)phenyl)pyridine 1-oxide

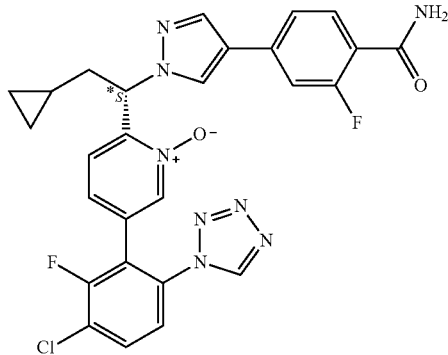 [SMILES: NC(=O)c1ccc(-c2cnn([C@@H](CC3CC3)c3ccc(-c4c(-n5cnnn5)ccc(Cl)c4F)c[n+]3[O-])c2)cc1F]

LC/MS: mass calculated for $C_{27}H_{21}ClF_2N_8O_2$: 562.05, measured (ES, m/z): 563.05 [M+H]$^+$. $^1$H NMR (400 MHz, DMSO-d$_6$) δ 9.68 (s, 1H), 8.66 (s, 1H), 8.41 (s, 1H), 8.14 (s, 1H), 8.05 (t, J=8.2 Hz, 1H), 7.75 (d, J=8.7 Hz, 1H), 7.68 (t, J=8.0 Hz, 1H), 7.55 (m, J=13.8, 7.3 Hz, 4H), 7.28 (d, J=8.3 Hz, 1H), 7.15 (d, J=8.3 Hz, 1H), 6.04-6.11 (m, 1H), 2.31-2.43 (m, 1H), 1.83-1.92 (m, 1H), 0.55-0.66 (m, 1H), 0.26-0.40 (m, 2H), 0.04-0.17 (m, 1H), −0.04-0.03 (m, 1H). $^{19}$F NMR (376 MHz, DMSO-d$_6$) δ −112.75, −113.00.

Example 1010: 2-(1-(4-(4-Carbamoyl-3-fluorophenyl)-1H-pyrazol-1-yl)-2-(1H-pyrazol-1-yl)ethyl)-5-(3-chloro-2-fluoro-6-(4-(trifluoromethyl)-1H-1,2,3-triazol-1-yl)phenyl)pyridine 1-oxide

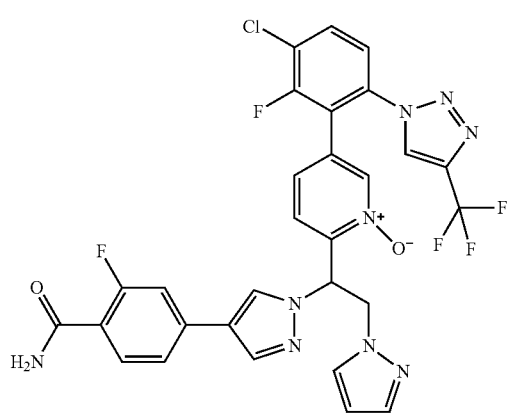 [SMILES: NC(=O)c1ccc(-c2cnn(C(Cn3cccn3)c3ccc(-c4c(-n5cc(C(F)(F)F)nn5)ccc(Cl)c4F)c[n+]3[O-])c2)cc1F]

LC/MS: mass calculated for $C_{29}H_{19}ClF_5N_9O_2$: 655.13; measured (ES, m/z): 656.1 [M+H]$^+$. $^1$H NMR (400 MHz, Chloroform-d) δ 8.28-8.19 (m, 1H), 8.09 (m, 1H), 7.93 (s, 1H), 7.83 (m, 2H), 7.75 (m, 1H), 7.49 (d, J=1.8 Hz, 1H), 7.43-7.35 (m, 2H), 7.32 (m, 1H), 7.22-7.14 (m, 2H), 6.90 (m, 1H), 6.67 (d, J=12.0 Hz, 1H), 6.59 (dd, J=9.1, 4.1 Hz, 1H), 6.11 (m, 1H), 5.75 (s, 1H), 5.17-4.99 (m, 2H).

Example 1011: (S*)-2-(1-(4-(4-Carbamoyl-3-fluorophenyl)-1H-pyrazol-1-yl)propyl)-5-(3-chloro-2-fluoro-6-(1H-tetrazol-1-yl)phenyl)pyridine 1-oxide

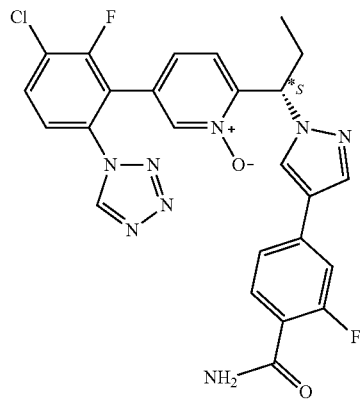

LC/MS: mass calculated for $C_{25}H_{19}ClF_2N_8O_2$: 536.13; measured (ES, m/z): 537.05 [M+H]$^+$. 1H NMR (300 MHz, DMSO-d$_6$) δ 9.69 (s, 1H), 8.62 (s, 1H), 8.43 (s, 1H), 8.15 (s, 1H), 8.06 (dd, J=8.7, 7.8 Hz, 1H), 7.76 (dd, J=8.7, 1.6 Hz, 1H), 7.69 (t, J=8.0 Hz, 1H), 7.61-7.56 (m, 2H), 7.56-7.50 (m, 2H), 7.31 (d, J=8.4 Hz, 1H), 7.17 (dd, J=8.3, 1.7 Hz, 1H), 5.89-5.94 (m, 1H), 2.08-2.32 (m, 2H), 0.86 (t, J=7.2 Hz, 3H). $^{19}$F NMR (282 MHz, DMSO-d$_6$) δ −112.71, −112.98.

Example 1012: (R*)-2-(1-(4-(4-Carbamoyl-3-fluorophenyl)-1H-pyrazol-1-yl)propyl)-5-(3-chloro-2-fluoro-6-(1H-tetrazol-1-yl)phenyl)pyridine 1-oxide

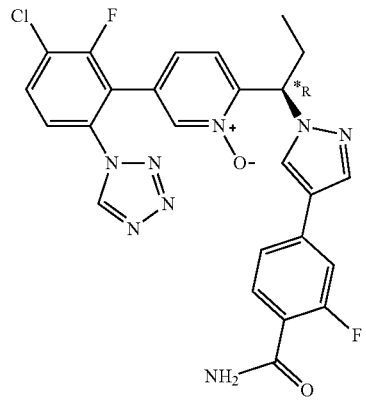

LC/MS: mass calculated for $C_{25}H_{19}ClF_2N_8O$: 536.13; measured (ES, m/z): 537.05 [M+H]$^+$. 1H NMR (300 MHz, DMSO-d$_6$) δ 9.69 (s, 1H), 8.62 (s, 1H), 8.43 (s, 1H), 8.15 (s, 1H), 8.06 (dd, J=8.7, 7.7 Hz, 1H), 7.76 (dd, J=8.7, 1.6 Hz, 1H), 7.69 (t, J=8.0 Hz, 1H), 7.62-7.55 (m, 2H), 7.55-7.48 (m, 2H), 7.31 (d, J=8.4 Hz, 1H), 7.17 (dd, J=8.2, 1.7 Hz, 1H), 5.89-5.94 (m, 1H), 2.08-2.32 (m, 2H), 0.86 (t, J=7.2 Hz, 3H). $^{19}$F NMR (282 MHz, DMSO-d$_6$) δ −112.71, −112.99.

Example 1013: (R*)-2-(1-(4-(4-Carbamoylphenyl)-1H-pyrazol-1-yl)-2-(1-(difluoromethyl)-1H-pyrazol-3-yl)ethyl)-5-(3-chloro-6-difluoromethyl)-2-fluorophenyl)pyridine 1-oxide

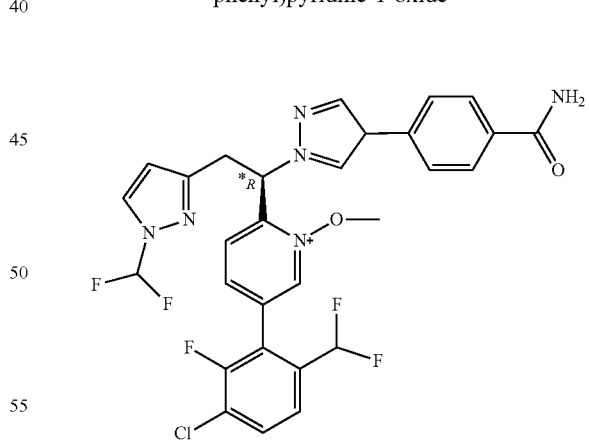

LC/MS: mass calculated for $C_{28}H_{20}ClF_5N_6O_2$: 602.13; measured (ES, m/z): 603.05 [M+H]$^+$. $^1$H NMR (400 MHz, DMSO-d$_6$) δ 8.57 (s, 1H), 8.53 (s, 1H), 8.14 (s, 1H), 8.04 (d, J=2.6 Hz, 1H), 7.93 (s, 1H), 7.90-7.84 (m, 3H), 7.69 (t, J=59.2 Hz, 1H), 7.67-7.63 (m, 2H), 7.60 (d, J=8.5 Hz, 1H), 7.36-7.41 (m, 2H), 7.30 (s, 1H), 6.88 (t, J=52.0 Hz, 1H), 6.40-6.46 (m, 1H), 6.13 (d, J=2.6 Hz, 1H), 3.63-3.78 (m, 2H). $^{19}$F NMR (376 MHz, DMSO-d$_6$) δ −93.77, −109.39, −115.23.

Example 1014: (S*)-2-(1-(4-(4-Carbamoylphenyl)-1H-pyrazol-1-yl)-2-(1-(difluoromethyl)-1H-pyrazol-3-yl)ethyl)-5-(3-chloro-6-(difluoromethyl)-2-fluorophenyl pyridine 1-oxide

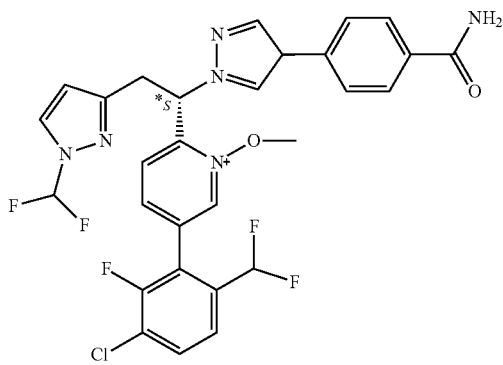

LC/MS: mass calculated for $C_{28}H_{20}ClF_5N_6O_2$: 602.13; measured (ES, m/z): 603.05 [M+H]$^+$. $^1$H NMR (400 MHz, DMSO-d$_6$) δ 8.56 (s, 1H), 8.53 (s, 1H), 8.14 (s, 1H), 8.04 (d, J=2.6 Hz, 1H), 7.93 (s, 1H), 7.90-7.84 (m, 3H), 7.68 (t, J=59.2 Hz, 1H), 7.67-7.63 (m, 2H), 7.60 (d, J=8.5 Hz, 1H), 7.35-7.43 (m, 2H), 7.29 (s, 1H), 6.87 (t, J=52.0 Hz, 1H), 6.40-6.46 (m, 1H), 6.13 (d, J=2.7 Hz, 1H), 3.60-3.76 (m, 2H). $^{19}$F NMR (376 MHz, DMSO-d$_6$) δ −93.77, −108.78, −110.06, −115.23.

Example 1015: (R*)-2-(1-(4-(4-Carboxyphenyl)-1H-pyrazol-1-yl)-2-(1-(difluoromethyl)-1H-pyrazol-3-yl)ethyl)-5-(3-chloro-6-(difluoromethyl)-2-fluorophenyl)pyridine 1-oxide

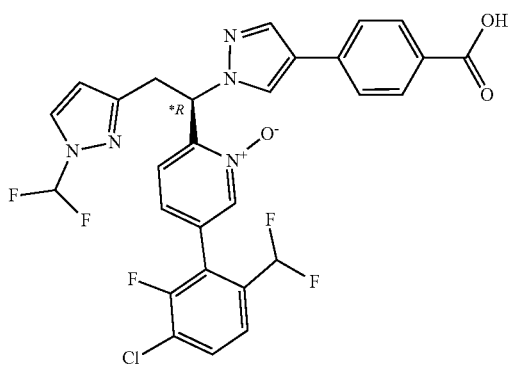 [SMILES: O=C(O)c1ccc(-c2cnn([C@H](Cc3ccn(C(F)F)n3)c3ccc(-c4c(C(F)F)ccc(Cl)c4F)c[n+]3[O-])c2)cc1]

LC/MS: mass calculated for $C_{28}H_{19}ClF_5N_5O_3$: 603.11; measured (ES, m/z): 604.00 [M+H]$^+$. $^1$H NMR (400 MHz, DMSO-d$_6$) δ 12.71 (s, 1H), 8.61 (s, 1H), 8.54 (s, 1H), 8.16 (s, 1H), 8.06 (s, 1H), 7.82-7.98 (m, 3H), 7.72 (t, J=68.0 Hz, 1H), 7.67-7.71 (m, 2H), 7.62 (d, J=8.5 Hz, 1H), 7.38-7.45 (m, 2H), 6.89 (t, J=52.0 Hz, 1H), 6.43-6.49 (m, 1H), 6.16 (s, 1H), 3.66-3.81 (m, 2H). $^{19}$F NMR (376 MHz, DMSO-d$_6$) δ −93.82, −115.21.

Example 1016: (S*)-2-(1-(4-(4-Carboxyphenyl)-1H-pyrazol-1-yl)-2-(1-(difluoromethyl)-1H-pyrazol-3-yl)ethyl)-5-(3-chloro-6-(difluoromethyl)-2-fluorophenyl)pyridine 1-oxide

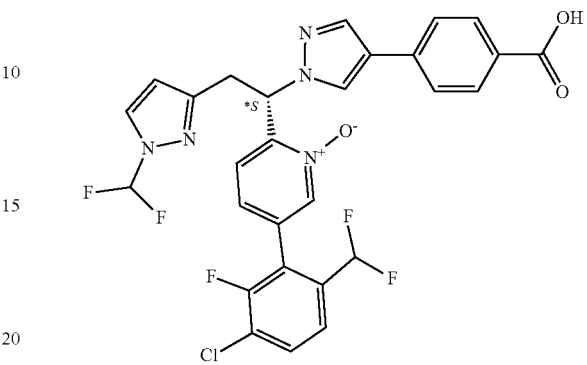

LC/MS: mass calculated for $C_{28}H_{19}ClF_5N_5O_3$: 603.11; measured (ES, m/z): 604.05 [M+H]$^+$. $^1$H NMR (400 MHz, DMSO-d$_6$) δ 12.82 (s, 1H), 8.61 (s, 1H), 8.54 (s, 1H), 8.16 (s, 1H), 8.06 (s, 1H), 7.82-7.95 (m, 3H), 7.72 (t, J=68.0 Hz, 1H), 7.67-7.71 (m, 2H), 7.62 (d, J=8.5 Hz, 1H), 7.38-7.45 (m, 2H), 6.89 (t, J=50.0 Hz, 1H), 6.43-6.49 (m, 1H), 6.15 (s, 1H), 3.62-3.74 (m, 2H). $^{19}$F NMR (376 MHz, DMSO-d$_6$) δ −93.81, −115.21.

Example 1017: (R*)-2-(1-(4-(4-Carbamoyl-3-fluorophenyl)-1H-pyrazol-1-yl)-2-(1-(difluoromethyl)-1H-pyrazol-3-yl)ethyl)-5-(3-chloro-6-(difluoromethoxy)-2-fluorophenyl)pyridine 1-oxide

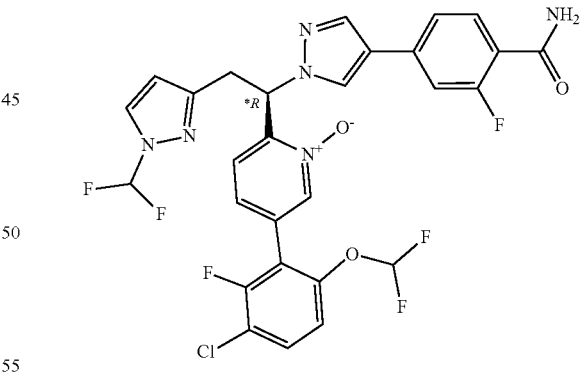

LC/MS: mass calculated for $C_{28}H_{19}ClF_6N_6O_3$: 636.11; measured (ES, m/z): 637.00 [M+H]$^+$. $^1$H NMR (400 MHz, CD$_3$OD) δ 8.49 (s, 1H), 8.36 (s, 1H), 8.05 (s, 1H), 7.87 (d, J=2.7 Hz, 1H), 7.82 (t, J=8.1 Hz, 1H), 7.64-7.72 (m, 2H), 7.58-7.62 (m, 1H), 7.45-7.50 (m, 1H), 7.39-7.44 (m, 1H), 7.35 (t, J=60.0 Hz, 1H), 7.28-7.33 (m, 1H), 6.66 (t, J=72.8 Hz, 1H), 6.60-6.65 (m, 1H), 6.25 (d, J=2.7 Hz, 1H), 3.86-3.80 (m, 2H). $^{19}$F NMR (376 MHz, CD$_3$OD) δ −82.71, −95.94, −114.65, (m), −115.64.

Example 1018: (S*)-2-(1-(4-(4-Carbamoyl-3-fluorophenyl)-1H-pyrazol-1-yl)-2-(1-(difluoromethyl)-1H-pyrazol-3-yl)ethyl)-5-(3-chloro-6-(difluoromethoxy)-2-fluorophenyl)pyridine 1-oxide

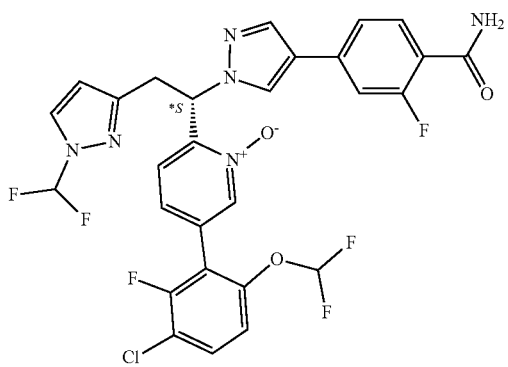 [SMILES: NC(=O)c1ccc(-c2cnn([C@@H](Cc3ccn(C(F)F)n3)c3ccc(-c4c(OC(F)F)ccc(Cl)c4F)c[n+]3[O-])c2)cc1F]

LC/MS: mass calculated for $C_{28}H_{19}ClF_6N_6O_3$: 636.11; measured (ES, m/z): 637.10 [M+H]⁺. ¹H NMR (400 MHz, CD₃OD) δ 8.49 (s, 1H), 8.36 (s, 1H), 8.05 (s, 1H), 7.87 (d, J=2.7 Hz, 1H), 7.82 (t, J=8.1 Hz, 1H), 7.72-7.64 (m, 2H), 7.62-7.59 (m, 1H), 7.40-7.51 (m, 2H), 7.35 (t, J=60.0 Hz, 1H), 7.27-7.34 (m, 1H), 6.65 (t, J=72.8 Hz, 1H), 6.60-6.64 (m, 1H), 6.25 (d, J=2.7 Hz, 1H), 3.86-3.79 (m, 2H). ¹⁹F NMR (376 MHz, CD₃OD) δ −82.49, −95.95, −114.66, −115.24.

Example 1019: 2-(2-(4-(tert-Butyl)-1H-pyrazol-1-yl)-1-(4-(4-carbamoyl-3-fluorophenyl)-1H-pyrazol-1-yl)ethyl)-5-(3-chloro-2-fluoro-6-(4-(trifluoromethyl)-1H-1,2,3-triazol-1-yl)phenyl)pyridine 1-oxide

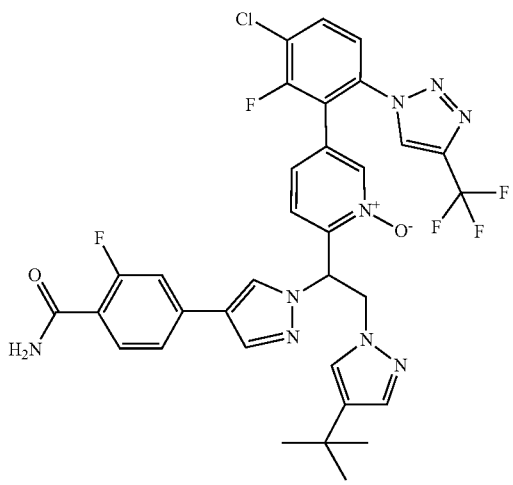 [SMILES: CC(C)(C)c1cnn(CC(c2ccc(-c3c(-n4cc(C(F)(F)F)nn4)ccc(Cl)c3F)c[n+]2[O-])n2cc(-c3ccc(C(N)=O)c(F)c3)cn2)c1]

LC/MS: mass calculated for $C_{33}H_{27}ClF_5N_9O_2$: 711.19, measured (ES, m/z): 712.1 [M+H]⁺. ¹H NMR (400 MHz, Chloroform-d) δ 8.30-8.22 (m, 1H), 7.98 (m, 1H), 7.90 (s, 1H), 7.83-7.70 (m, 3H), 7.49 (d, J=1.8 Hz, 1H), 7.45-7.38 (m, 2H), 7.26 (dt, J=8.1, 1.8 Hz, 1H), 7.22-7.14 (m, 2H), 6.90 (dd, J=8.3, 1.7 Hz, 1H), 6.67 (d, J=12.0 Hz, 1H), 6.24 (t, J=1.6, 1.0 Hz, 1H), 5.86 (s, 1H), 5.24-5.16 (m, 2H), 1.25 (s, 12H).

Example 1020: 2-(1-(4-(4-Carbamoyl-2-fluorophenyl)-1H-pyrazol-1-yl)-2-(1-(difluoromethyl)-1H-pyrazol-3-yl)ethyl)-5-(3-chloro-2-fluoro-6-(4-(trifluoromethyl)-1H-1,2,3-triazol-1-yl)phenyl)pyridine 1-oxide Step 1: tert-Butyl 4-bromo-3-fluorobenzoate To a solution of 4-bromo-3-fluorobenzoic acid (10.0 g, 45.66 mmol, 1.0 equiv) in THF/t-BuOH (50 mL/50 mL) was followed by the addition of DMAP (560 mg, 4.59 mmol, 0.10 equiv) and Boc₂O (14.9 g, 68.27 mmol, 1.50 equiv). The mixture was stirred for 24 h at 50° C. The reaction was then quenched by the addition of H₂O. The resulting solution was extracted with ethyl acetate and the organic layers combined and dried with Na₂SO₄. The solids were filtered out. The resulting organic phase was concentrated under vacuum. The residue was purified by silica gel chromatography (0→30% EA/PE) to yield tert-butyl 4-bromo-3-fluorobenzoate as colorless oil. LC/MS: mass calculated for $C_{11}H_{12}BrFO_2$: 274.00, measured (ES, m/z): 275.12 [M+H]⁺.

Step 2: tert-Butyl 3-fluoro-4-(1H-pyrazol-4-yl)benzoate

To a solution of tert-butyl 4-bromo-3-fluorobenzoate (6.6 g, 23.99 mmol, 1.0 eq.) in 1,4-dioxane (100 mL) and H₂O (20 mL) was added tert-butyl 4-(4,4,5,5-tetramethyl-1,3,2-dioxaborolan-2-yl)-1H-pyrazole-1-carboxylate (9.2 g, 31.19 mmol, 1.3 eq.), K₂CO₃ (6.6 g, 47.98 mmol, 2.0 eq.) and Pd(PPh₃)₄ (2.8 g, 2.40 mmol, 0.1 eq.). The mixture was stirred at 90° C. for 4 h under N₂. After cooling to room temperature, the reaction was quenched with water, extracted with ethyl acetate. The organic layers were combined, dried over anhydrous sodium sulfate, filtered and concentrated. The residue was purified by silica gel chromatography (0→50% EA/PE) to yield the tert-butyl 3-fluoro-4-(1H-pyrazol-4-yl)benzoate as a yellow solid. LC/MS: mass calculated for $C_{14}H_{15}FN_2O_2$: 262.11, measured (ES, m/z): 263.12 [M+H]⁺.

Step 3: tert-Butyl 4-(1-((5-bromopyridin-2-yl)methyl)-1H-pyrazol-4-yl)-3-fluorobenzoate tert-butyl 3-fluoro-4-(1H-pyrazol-4-yl)benzoate (2.0 g, 7.63 mmol, 1.0 eq.) was dissolved in CH₃CN (25 mL). Next added Cs$_2$CO$_3$ (2.0 g, 7.63 mmol, 1.0 eq.), the mixture was stirred 30 min at room temperature. (5-Bromopyridin-2-yl) methyl methanesulfonate (2.5 g, 7.63 mmol, 1.0 eq.) was then added. The resulting mixture was stirred at 80° C. for 3 h. The reaction mixture was concentrated and purified by silica gel chromatography (0→30% EA/PE) to yield tert-butyl 4-(1-((5-bromopyridin-3-yl)methyl)-1H-pyrazol-4-yl)-3-fluorobenzoate. LC/MS: mass calculated for C$_{20}$H$_{1}$BrFN$_3$O$_2$: 431.06, measured (ES, m/z): 432.29 [M+H]$^+$.

Step 4: tert-Butyl 4-(1-(1-(5-bromopyridin-2-yl)-2-(1-(difluoromethyl)-1H-pyrazol-3-yl)ethyl)-1H-pyrazol-4-yl)-3-fluorobenzoate To a solution of tert-butyl 4-(1-((5-bromopyridin-2-yl)methyl)-1H-pyrazol-4-yl)-3-fluorobenzoate (252 mg, 0.58 mmol, 1.0 eq.) in THF (3 mL), the mixture was cooled to −78° C. added LHMDS (0.7 mL, 0.7 mmol, 1.2 eq.) stirred for 30 min. 3-(Bromomethyl)-1-(difluoromethyl)-1H-pyrazole (160 mg, 0.76 mmol, 1.3 eq.) was then added and the mixture was stirred at −78° C. for 2 h. The reaction was quenched with water, extracted with ethyl acetate. The organic layers were combined, dried over anhydrous sodium sulfate, filtered and concentrated to yield tert-butyl 4-(1-(1-(5-bromopyridin-2-yl)-2-(1-(difluoromethyl)-1H-pyrazol-3-yl)ethyl)-1H-pyrazol-4-yl)-3-fluorobenzoate as a yellow solid. LC/MS: mass calculated for C$_{25}$H$_{23}$BrF$_3$N$_5$O$_2$: 561.10, measured (ES, m/z): 562.39 [M+H]$^+$.

Step 5: (6-(1-(4-(4-(tert-Butoxycarbonyl)-2-fluorophenyl)-1H-pyrazol-1-yl)-2-(1-(difluoromethyl)-1H-pyrazol-3-yl)ethyl)pyridin-3-yl)boronic acid To a solution of tert-butyl 4-(1-(1-(5-bromopyridin-2-yl)-2-(1-(difluoromethyl)-1H-pyrazol-3-yl)ethyl)-1H-pyrazol-4-yl)-3-fluorobenzoate (0.2 g, 0.36 mmol, 1.0 eq.), Pd(dppf)Cl$_2$ (26 mg, 0.04 mmol, 0.1 eq.) in 1,4-dioxane (6 mL) was added 4,4,4',4',5,5,5',5'-octamethyl-2,2'-bi(1,3,2-dioxaborolane) (117 mg, 0.46 mmol, 1.3 eq.) and KOAc (70 mg, 0.71 mmol, 2 eq.). The mixture was stirred at 90° C. for 3 h under N$_2$. The residue was concentrated to yield (6-(1-(4-(4-(tert-butoxycarbonyl)-2-fluorophenyl)-1H-pyrazol-1-yl)-2-(1-(difluoromethyl)-1H-pyrazol-3yl)ethyl)pyridin-3-yl)boronic acid as red solid. LC/MS: mass calculated for C$_{25}$H$_{25}$BF$_3$N$_5$O$_4$: 527.20, measured (ES, m/z): 528.20 [M+H]$^+$ Step 6: tert-Butyl 4-(1-(1-(5-(3-chloro-2-fluoro-6-(4-(trifluoromethyl)-1H-1,2,3-triazol-1-yl)phenyl)pyridin-2-yl)-2-(1-(difluoromethyl)-1H-pyrazol-3-yl)ethyl)-1H-pyrazol-4-yl)-3-fluorobenzoate To a solution of (6-(1-(4-(4-(tert-butoxycarbonyl)-2-fluorophenyl)-1H-pyrazol-1-yl)-2-(1-(difluoromethyl)-1H-pyrazol-3-yl)ethyl)pyridin-3-yl)boronic acid (0.4 g, resulting) in 1,4-dioxane (6 mL) and H$_2$O (1 mL) was added 1-(4-chloro-3-fluoro-2-iodophenyl)-4-(trifluoromethyl)-1H-1,2,3-triazole (297 mg), K$_2$CO$_3$ (209 mg) and Pd(PPh$_3$)$_4$ (88 mg). The mixture was stirred at 90° C. for 3 h under N$_2$. After cooling to room temperature, the reaction was quenched with water, extracted with ethyl acetate. The organic layers were combined, dried over anhydrous sodium sulfate, filtered and concentrated. The residue was purified by silica gel chromatography (0→50% EA/PE) to yield the tert-butyl 4-(1-(1-(5-(3-chloro-2-fluoro-6-(4-(trifluoromethyl)-1H-1,2,3-triazol-1-yl)phenyl)pyridin-2-yl)-2-(1-(difluoromethyl)-1H-pyrazol-3-yl)ethyl)-1H-pyrazol-4-yl)-3-fluorobenzoate as a yellow solid. LC/MS: mass calculated for C$_{34}$H$_{26}$ClF$_7$N$_8$O$_2$: 746.18, measured (ES, m/z): 747.07 [M+H]$^+$ Step 7: 4-(1-(1-(5-(3-Chloro-2-fluoro-6-(4-(trifluoromethyl)-1H-1,2,3-triazol-1-yl)phenyl)pyridin-2-yl)-2-(1-(difluoromethyl)-1H-pyrazol-3-yl)ethyl)-1H-pyrazol-4-yl)-3-fluorobenzoic acid To a solution of tert-butyl 4-(1-(1-(5-(3-chloro-2-fluoro-6-(4-(trifluoromethyl)-1H-1,2,3-triazol-1-yl)phenyl)pyridin-2-yl)-2-(1-(difluoromethyl)-1H-pyrazol-3-yl)ethyl)-1H-pyrazol-4-yl)-3-fluorobenzoate (0.1 g, 0.13 mmol, 1.0 eq.) in DCM (3 mL) was added TFA (1 mL). The mixture was stirred at 25° C. for 3 h. The mixture was concentrated and the residue was purified by reverse phase chromatography on C18 (80 g, MeCN/H$_2$O (0.05% CF$_3$COOH): 0→50%) to yield 4-(1-(1-(5-(3-chloro-2-fluoro-6-(4-(trifluoromethyl)-1H-1,2,3-triazol-1-yl)phenyl)pyridin-2-yl)-2-(1-(difluoromethyl)-1H-pyrazol-3-yl)ethyl)-1H-pyrazol-4-yl)-3-fluorobenzoic acid as a yellow solid. LC/MS: mass calculated for C$_{30}$H$_{18}$ClF$_7$N$_8$O$_2$: 690.11, measured (ES, m/z): 691.12 [M+H]$^+$ Step 8: 2-(1-(4-(4-Carboxy-2-fluorophenyl)-1H-pyrazol-1-yl)-2-(1-(difluoromethyl)-1H-pyrazol-3-yl)ethyl)-5-(3-chloro-2-fluoro-6-(4-(trifluoromethyl)-1H-1,2,3-triazol-1-yl)phenyl)pyridine 1-oxide To a solution of 4-(1-(1-(5-(3-chloro-2-fluoro-6-(4-(trifluoromethyl)-1H-1,2,3-triazol-1-yl)phenyl)pyridin-2-yl)-2-(1-(difluoromethyl)-1H-pyrazol-3-yl)ethyl)-1H-pyrazol-4-yl)-3-fluorobenzoic acid (60 mg, 0.09 mmol, 1.0 eq.) in MeOH (3 mL) was added H$_2$O$_2$ (0.1 mL) and ReMeO$_3$ (25 mg, 0.10 mmol, 1.155 equiv). The reaction was stirred at room temperature 2 h. The mixture was concentrated and the residue was purified by reverse phase chromatography on C18 (80 g, MeCN/H$_2$O (0.05% CF$_3$COOH): 0→55%) to yield 2-(1-(4-(4-carboxy-2-fluorophenyl)-1H-pyrazol-1-yl)-2-(1-(difluoromethyl)-1H-pyrazol-3-yl)ethyl)-5-(3-chloro-2-fluoro-6-(4-(trifluoromethyl)-1H-1,2,3-triazol-1-yl)phenyl)pyridine 1-oxide as white solid. LC/MS: mass calculated for C$_{30}$H$_{18}$ClF$_7$N$_8$O$_3$: 706.11, measured (ES, m/z): 707.11 [M+H]$^+$ Step 9: 2-(1-(4-(4-Carbamoyl-2-fluorophenyl)-1H-pyrazol-1-yl)-2-(1-(difluoromethyl)-1H-pyrazol-3-yl)ethyl)-5-(3-chloro-2-fluoro-6-(4-(trifluoromethyl)-1H-1,2,3-triazol-1-yl)phenyl)pyridine 1-oxide To a solution of 2-(1-(4-(4-carboxy-2-fluorophenyl)-1H-pyrazol-1-yl)-2-(1-(difluoromethyl)-1H-pyrazol-3-yl)ethyl)-5-(3-chloro-2-fluoro-6-(4-(trifluoromethyl)-1H-1,2,3-triazol-1-yl)phenyl)pyridine 1-oxide (50 mg, 0.07 mmol, 1.0 equiv) in DMF (3 mL) were added NH$_4$Cl (38 mg, 0.71 mmol, 10 equiv), HATU (40 mg, 0.11 mmol, 1.5 equiv) and DIEA (14 mg, 0.11 mmol, 1.5 equiv). The reaction mixture was stirred overnight at room temperature. The reaction was quenched with water, and the mixture extracted with ethyl acetate. The combined organic layer was washed with brine, dried over Na$_2$SO$_4$ and concentrated. The mixture was concentrated and the residue was purified by reverse phase chromatography on C18 (80 g, MeCN/H$_2$O (0.05% CF$_3$COOH): 0→55%) to yield 2-(1-(4-(4-carbamoyl-2-fluorophenyl)-1H-pyrazol-1-yl)-2-(1-(difluoromethyl)-1H- pyrazol-3-yl)ethyl)-5-(3-chloro-2-fluoro-6-(4-(trifluoromethyl)-1H-1,2,3-triazol-1-yl)phenyl)pyridine 1-oxide as a white solid.

LC/MS: mass calculated for $C_{30}H_{19}ClF_7N_9O_2$: 705.12; measured (ES, m/z): 706.10 [M+H]$^+$. $^1$H NMR (300 MHz, DMSO-$d_6$) δ 9.18 (s, 1H), 8.42-8.50 (m, 2H), 8.00-8.13 (m, 4H), 7.67-7.87 (m, 6H), 7.46-7.48 (m, 1H), 7.34 (d, J=8.4 Hz, 1H), 7.15-7.19 (m, 1H), 6.46 (dd, J=9.0, 5.8 Hz, 1H), 6.13 (d, J=2.7 Hz, 1H), 3.59-3.72 (m, 2H). $^{19}$F NMR (282 MHz, DMSO-$d_6$) δ −59.77, −74.21, −93.87, −112.82, −114.62.

Example 1021: (S*)-2-(1-(4-(5-Carbamoyl-4-fluorothiophen-3-yl)-1H-pyrazol-1-yl)-2-cyclopropylethyl)-5-(3-chloro-2-fluoro-6-(1H-tetrazol-1-yl)phenyl)pyridine 1-oxide

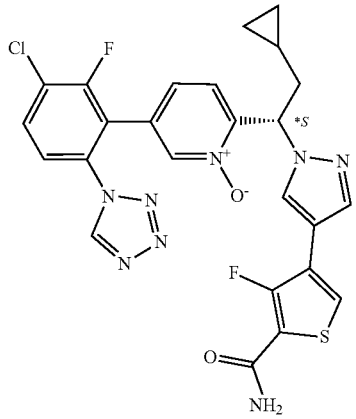 [SMILES: NC(=O)c1scc(-c2cnn([C@@H](CC3CC3)c3ccc(-c4c(-n5cnnn5)ccc(Cl)c4F)c[n+]3[O-])c2)c1F]

LC/MS: mass calculated for $C_{25}H_{19}ClF_2N_8O_2S$: 568.10; measured (ES, m/z): 569.05 [M+H]$^+$. $^1$H NMR (300 MHz, CD$_3$OD) δ 9.37 (s, 1H), 8.35 (s, 1H), 8.25 (s, 1H), 7.94 (s, 1H), 7.86-7.92 (m, 1H), 7.75 (d, J=4.7 Hz, 1H), 7.60 (dd, J=8.7, 1.7 Hz, 1H), 7.44 (d, J=8.3 Hz, 1H), 7.27 (dd, J=8.3, 1.7 Hz, 1H), 6.18-6.25 (m, 1H), 2.40-2.55 (m, 1H), 1.90-2.06 (m, 1H), 0.64-0.72 (m, 1H), 0.32-0.49 (m, 2H), 0.15-0.22 (m, 1H), 0.02-0.10 (m, 1H). $^{19}$F NMR (282 MHz, CD$_3$OD) δ −113.70, −121.76.

Example 1022: (R*)-2-(1-(4-(5-Carbamoyl-4-fluorothiophen-3-yl)-1H-pyrazol-1-yl)-2-cyclopropylethyl)-5-(3-chloro-2-fluoro-6-(1H-tetrazol-1-yl)phenyl)pyridine 1-oxide

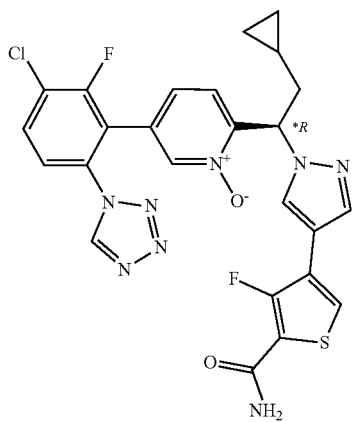 [SMILES: NC(=O)c1scc(-c2cnn([C@H](CC3CC3)c3ccc(-c4c(-n5cnnn5)ccc(Cl)c4F)c[n+]3[O-])c2)c1F]

LC/MS: mass calculated for $C_{25}H_{19}ClF_2N_8O_2S$: 568.10; measured (ES, m/z): 569.10 [M+H]$^+$. $^1$H NMR (300 MHz, CD$_3$OD) δ 9.37 (s, 1H), 8.38 (s, 1H), 8.25 (s, 1H), 7.85-7.98 (m, 2H), 7.75 (d, J=4.8 Hz, 1H), 7.55-7.65 (m, 1H), 7.45 (d, J=8.3 Hz, 1H), 7.22-7.32 (m, 1H), 6.18-6.28 (m, 1H), 2.40-2.55 (m, 1H), 1.90-2.06 (m, 1H), 0.64-0.73 (m, 1H), 0.31-0.50 (m, 2H), 0.13-0.26 (m, 1H), 0.02-0.11 (m, 1H). $^{19}$F NMR (282 MHz, CD$_3$OD) δ −113.69, −121.75.

Example 1023: 2-(1-(4-(4-Carbamoyl-3-fluorophenyl)-1H-pyrazol-1-yl)-2-(4-cyano-1H-pyrazol-1-yl)ethyl)-5-(3-chloro-2-fluoro-6-(4-(trifluoromethyl)-1H-1,2,3-triazol-1-yl)phenyl)pyridine 1-oxide

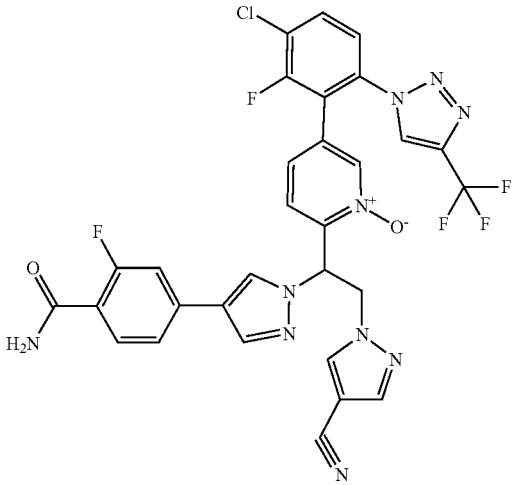 [SMILES: N#Cc1cnn(CC(c2ccc(-c3c(-n4cc(C(F)(F)F)nn4)ccc(Cl)c3F)c[n+]2[O-])n2cc(-c3ccc(C(N)=O)c(F)c3)cn2)c1]

LC/MS: mass calculated for $C_{30}H_{18}ClF_5N_{10}O_2$: 680.12, measured (ES, m/z): 681.0 [M+H]$^+$. $^1$H NMR (400 MHz, Chloroform-d) δ 8.44-8.37 (m, 1H), 8.20 (m, 1H), 8.05 (s, 1H), 7.93-7.80 (m, 3H), 7.49-7.38 (m, 3H), 7.30 (dt, J=8.4, 2.1 Hz, 1H), 7.26-7.18 (m, 2H), 6.99 (dd, J=8.3, 1.7 Hz, 1H), 6.80 (d, J=12.0 Hz, 1H), 6.46 (m, 1H), 5.86 (s, 1H), 5.32-5.26 (m, 2H).

Example 1024: (R*)-2-(1-(4-(5-Carbamoyl-3-methylthiophen-2-yl)-1H-pyrazol-1-yl)-2-cyclopropylethyl)-5-(3-chloro-2-fluoro-6-(4-(trifluoromethyl)-1H-1,2,3-triazol-1-yl)phenyl)pyridine 1-oxide

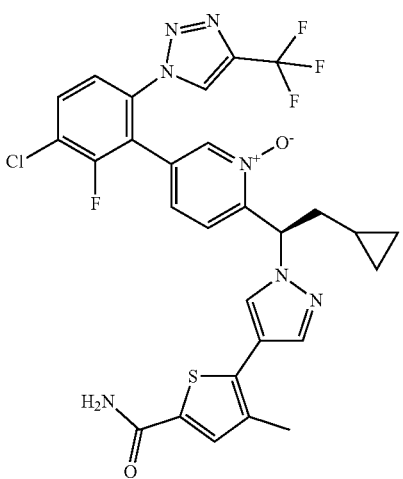 [SMILES: Cc1cc(C(N)=O)sc1-c1cnn([C@H](CC2CC2)c2ccc(-c3c(-n4cc(C(F)(F)F)nn4)ccc(Cl)c3F)c[n+]2[O-])c1]

1013

LC/MS: mass calculated for $C_{28}H_{22}ClF_4N_7O_2S$: 631.12, measured (ES, m/z): 632.10 [M+H]⁺. ¹H NMR (400 MHz, DMSO-d₆) δ 9.18 (d, J=1.1 Hz, 1H), 8.41 (d, J=1.6 Hz, 1H), 8.34 (s, 1H), 8.06 (dd, J=8.7, 7.7 Hz, 1H), 7.85 (m, 1H), 7.80 (s, 1H), 7.78 (dd, J=8.7, 1.5 Hz, 1H), 7.54 (s, 1H), 7.30-7.32 (m, 2H), 7.14 (dd, J=8.3, 1.7 Hz, 1H), 6.13-6.16 (m, 1H), 2.35-2.27 (m, 1H), 2.26 (s, 3H), 1.97-2.07 (m, 1H), 0.58-0.62 (m, 1H), 0.27-0.36 (m, 2H), 0.06-0.11 (m, 1H), −0.06--0.01 (m, 1H). ¹⁹F NMR (400 MHz, DMSO-d₆) δ −59.78, −112.90.

Example 1025: (S*)-2-(1-(4-(5-Carbamoyl-3-methylthiophen-2-yl)-1H-pyrazol-1-yl)-2-cyclopropylethyl)-5-(3-chloro-2-fluoro-6-(4-(trifluoromethyl)-1H-1,2,3-triazol-1-yl)phenyl)pyridine 1-oxide

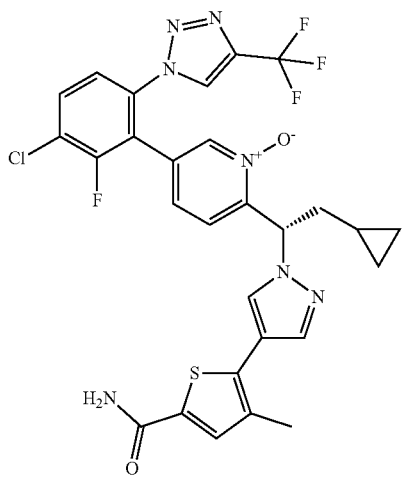 [SMILES: Cc1cc(C(N)=O)sc1-c1cnn([C@@H](CC2CC2)c2ccc(-c3c(-n4cc(C(F)(F)F)nn4)ccc(Cl)c3F)c[n+]2[O-])c1]

LC/MS: mass calculated for $C_{28}H_{22}ClF_4N_7O_2S$: 631.12, measured (ES, m/z): 632.10 [M+H]⁺. ¹H NMR (400 MHz, DMSO-d₆) δ 9.18 (d, J=1.1 Hz, 1H), 8.41 (d, J=1.6 Hz, 1H), 8.35 (s, 1H), 8.06 (dd, J=8.7, 7.7 Hz, 1H), 7.85 (m, 1H), 7.80 (s, 1H), 7.78 (dd, J=8.7, 1.5 Hz, 1H), 7.54 (s, 1H), 7.30-7.32 (m, 2H), 7.14 (dd, J=8.3, 1.7 Hz, 1H), 6.13-6.16 (m, 1H), 2.35-2.27 (m, 1H), 2.26 (s, 3H), 1.95-2.00 (m, 1H), 0.58-0.61 (m, 1H), 0.31-0.35 (m, 2H), 0.06-0.11 (m, 1H), −0.06--0.01 (m, 1H). ¹⁹F NMR (400 MHz, DMSO-d₆) δ −59.78, −112.91.

Example 1026: 2-(1-(4-(4-Carboxy-3-fluorophenyl)-1H-pyrazol-1-yl)-2-(1-(difluoromethyl)-1H-pyrazol-3-yl)ethyl)-5-(3-chloro-6-(difluoromethyl)-2-fluorophenyl)-4-methoxypyridine 1-oxide

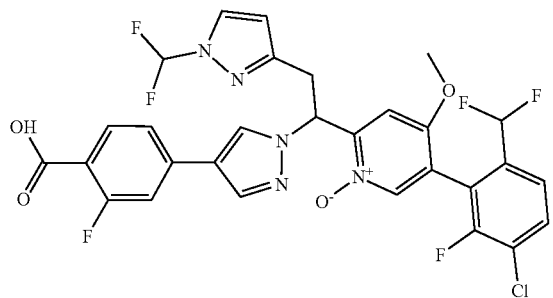 [SMILES: COc1cc(C(Cc2ccn(C(F)F)n2)n2cc(-c3ccc(C(=O)O)c(F)c3)cn2)[n+]([O-])cc1-c1c(C(F)F)ccc(Cl)c1F]

1014

LC/MS: mass calculated for $C_{29}H_{21}ClF_6N_6O_3$: 651.11, measured (ES, m/z): 652.10 [M+H]⁺. ¹H NMR (400 MHz, DMSO-d₆) δ 8.64 (d, J=2.4 Hz, 1H), 8.40 (d, J=2.0 Hz, 1H), 8.22 (d, J=6.1 Hz, 1H), 8.06 (t, J=2.4 Hz, 1H), 7.79-7.92 (m, 2H), 7.50-7.72 (m, 4H), 7.25 (d, J=15.9 Hz, 1H), 6.66-6.99 (m, 1H), 6.44-6.54 (m, 1H), 6.11-6.18 (m, 1H), 3.57-3.92 (m, 5H). ¹⁹F NMR (376 MHz, DMSO-d₆) δ −74.67, −93.87, −109.96, −110.13, −110.74.

Example 1027: 2-(1-(4-(4-Carbamoyl-3-fluorophenyl)-1H-pyrazol-1-yl)-2-(1-(difluoromethyl)-1H-pyrazol-3-yl)ethyl)-5-(3-chloro-6-(difluoromethyl)-2-fluorophenyl)-4-methoxypyridine 1-oxide

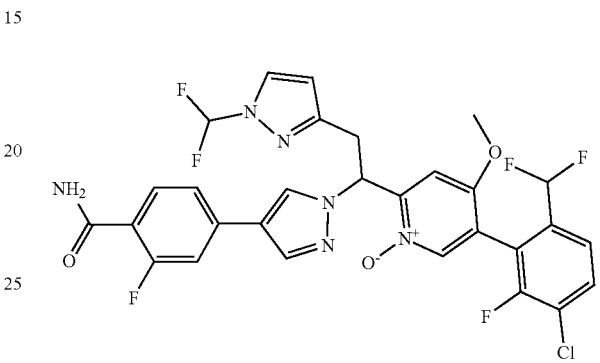

LC/MS: mass calculated for $C_{29}H_{21}ClF_6N_6O_3$: 650.13, measured (ES, m/z): 651.10 [M+H]⁺. ¹H NMR (400 MHz, DMSO-d₆) δ 8.60 (d, J=2.4 Hz, 1H), 8.40 (d, J=1.9 Hz, 1H), 8.19 (d, J=6.0 Hz, 1H), 8.06 (t, J=2.4 Hz, 1H), 7.82-7.91 (m, 1H), 7.62-7.71 (m, 2H), 7.45-7.61 (m, 5H), 7.25 (d, J=17.2 Hz, 1H), 6.68-6.98 (m, 1H), 6.45-6.54 (m, 1H), 6.10-6.20 (m, 1H), 3.65-3.89 (m, 5H). ¹⁹F NMR (376 MHz, DMSO-d₆) δ −74.66, −93.85, −109.74, −110.71, −112.96, −114.64.

Example 1028: 5-(2-Acetyl-5-chlorophenyl)-2-(1-(4-(4-carboxy-3-fluorophenyl)-1H-pyrazol-1-yl)-2-(1-(difluoromethyl)-1H-pyrazol-3-yl)ethyl)-4-methoxypyridine 1-oxide

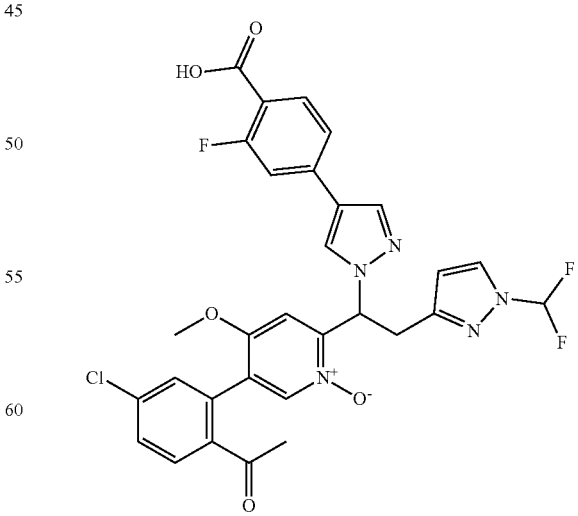

LC/MS: mass calculated for $C_{30}H_{23}ClF_3N_5O_5$: 625.13, measured (ES, m/z): 626.25 [M+H]⁺. ¹H NMR (400 MHz, DMSO-d$_6$) δ 8.49 (s, 1H), 8.27 (s, 1H), 8.01-8.10 (m, 2H), 7.82-7.92 (m, 1H), 7.60-7.79 (m, 4H), 7.25-7.50 (m, 2H), 7.01 (s, 1H), 6.40-6.50 (m, 1H), 6.08-6.20 (m, 1H), 3.67 (s, 3H), 3.45-3.55 (m, 2H), 2.50 (s, 3H). $^{19}$F NMR (376 MHz, DMSO-d$_4$) δ −93.77, −73.40.

Example 1029: (R*)-5-(2-Acetyl-5-chlorophenyl)-2-(1-(4-(4-carbamoyl-3-fluorophenyl)-1H-pyrazol-1-yl)-2-(1-(difluoromethyl)-1H-pyrazol-3-yl)ethyl)-4-methoxypyridine 1-oxide

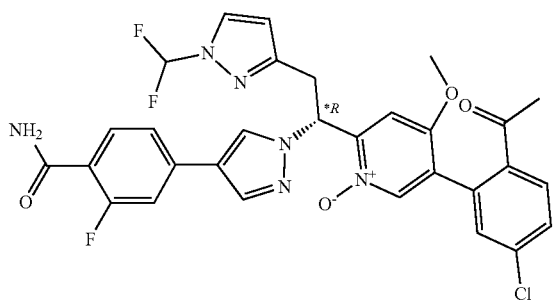 [SMILES: COc1cc([C@@H](Cc2ccn(C(F)F)n2)n2cc(-c3ccc(C(N)=O)c(F)c3)cn2)[n+]([O-])cc1-c1cc(Cl)ccc1C(C)=O]

LC/MS: mass calculated for C$_{30}$H$_{24}$ClF$_3$N$_6$O$_4$: 624.15, measured (ES, m/z): 625.05 [M+H]$^+$. $^1$H NMR (400 MHz, DMSO-d$_6$) δ 8.58 (s, 1H), 8.27 (s, 1H), 8.15 (s, 1H), 8.04 (d, J=2.6 Hz, 1H), 7.89 (d, J=8.4 Hz, 1H), 7.69 (t, J=59.2 Hz, 1H), 7.66 (d, J=8.1 Hz, 1H), 7.62 (dd, J=8.4, 2.0 Hz, 1H), 7.55-7.59 (m, 2H), 7.49-7.54 (m, 2H), 7.46-7.49 (m, 1H), 7.05 (s, 1H), 6.43-6.49 (m, 1H), 6.13 (d, J=2.7 Hz, 1H), 3.62-3.80 (m, 2H), 3.66 (s, 3H). 3.30 (s, 3H). $^{19}$F NMR (376 MHz, DMSO-d$_4$) δ −93.78, −112.98.

Example 1030: (S*)-5-(2-Acetyl-5-chlorophenyl)-2-(1-(4-(4-carbamoyl-3-fluorophenyl)-1H-pyrazol-1-yl)-2-(1-(difluoromethyl)-1H-pyrazol-3-yl)ethyl)-4-methoxypyridine 1-oxide

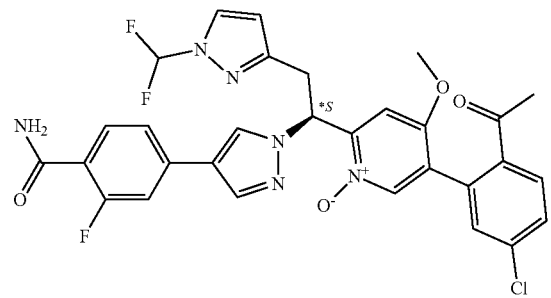 [SMILES: COc1cc([C@H](Cc2ccn(C(F)F)n2)n2cc(-c3ccc(C(N)=O)c(F)c3)cn2)[n+]([O-])cc1-c1cc(Cl)ccc1C(C)=O]

LC/MS: mass calculated for C$_{30}$H$_{24}$ClF$_3$N$_6$O$_4$: 624.15, measured (ES, m/z): 625.05 [M+H]$^+$. $^1$NMR (400 MHz, DMSO-d$_6$) δ 8.58 (s, 1H), 8.27 (s, 1H), 8.15 (s, 1H), 8.04 (d, J=2.6 Hz, 1H), 7.89 (d, J=8.3 Hz, 1H), 7.69 (t, J=59.2 Hz, 1H), 7.66 (d, J=8.1 Hz, 1H), 7.62 (dd, J=8.3, 2.0 Hz, 1H), 7.55-7.59 (m, 2H), 7.54-7.49 (m, 2H), 7.47 (dd, J=8.1, 1.6 Hz, 1H), 7.02 (s, 1H), 6.43-6.49 (m, 1H), 6.13 (d, J=2.7 Hz, 1H), 3.61-3.80 (m, 2H), 3.66 (s, 3H), 3.30 (s, 3H). $^{19}$F NMR (376 MHz, DMSO-d$_4$) δ −93.00, −112.97.

Example 1031: (R*)-2-(1-(4-(5-Carbamoyl-3-methylthiophen-2-yl)-1H-pyrazol-1-yl)-2-cyclopropylethyl)-5-(5-chloro-2-(4-(trifluoromethyl)-1H-1,2,3-triazol-1-yl)phenyl)-4-methoxypyridine 1-oxide

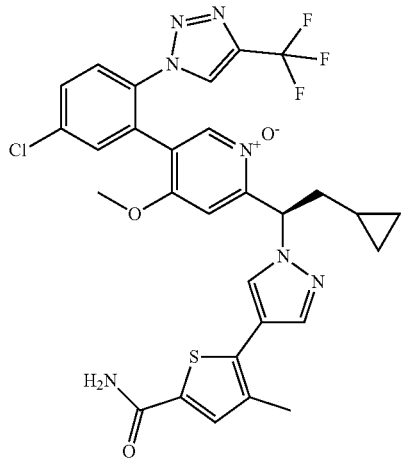

LC/MS: mass calculated for C$_{29}$H$_{25}$ClF$_3$N$_7$O$_3$S: 643.1, measured (ES, m/z): 644.1 [M+H]$^+$, $^1$H NMR (400 MHz, DMSO-d$_6$) δ 9.01 (s, 1H), 8.24-8.29 (m, 2H), 7.76-7.78 (m, 3H), 7.74-7.75 (m, 1H), 7.50 (s, 1H), 6.91 (s, 1H), 6.14-6.22 (m, 1H), 3.35 (s, 3H), 2.24-2.34 (m, 1H), 2.22 (s, 3H), 1.97-2.05 (m, 1H), 0.52-0.61 (m, 1H), 0.22-0.38 (m, 2H), 0.04-0.12 (m, 1H), −0.12-−0.04 (m, 1H). $^{19}$F NMR (376 MHz, DMSO-d$_6$) δ −59.72, −73.69.

Example 1032: (S*)-2-(1-(4-(5-Carbamoyl-3-methylthiophen-2-yl)-1H-pyrazol-1-yl)-2-cyclopropylethyl)-5-(5-chloro-2-(4-(trifluoromethyl)-1H-1,2,3-triazol-1-yl)phenyl)-4-methoxypyridine 1-oxide

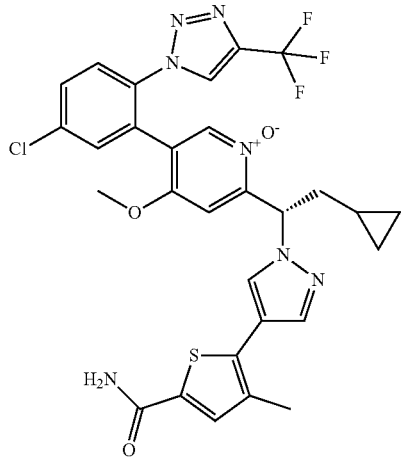

LC/MS: mass calculated for C$_{29}$H$_{25}$ClF$_3$N$_7$O$_3$S: 643.1, measured (ES, m/z): 644.1 [M+H]$^+$, $^1$H NMR (400 MHz, DMSO-d$_6$) δ 9.19 (s, 1H), 8.32-8.36 (m, 2H), 7.80-7.86 (m, 4H), 7.78 (s, 1H), 7.54 (s, 1H), 7.28 (s, 1H), 6.91 (s, 1H), 6.17-6.26 (m, 1H), 3.36 (s, 3H), 2.26-2.34 (m, 1H), 2.24 (s, 3H), 2.0-2.10 (m, 1H), 0.54-0.64 (m, 1H), 0.24-0.42 (m, 2H), 0.07-0.18 (m, 1H), −0.07-0.00 (m, 1H). $^{19}$F NMR (376 MHz, DMSO-$d_6$) δ −59.72.

Example 1033: 2-(1-(4-(5-Carbamoyl-3-methylthiophen-2-yl)-1H-pyrazol-1-yl)-2-cyclopropylethyl)-5-(3-chloro-2-fluoro-6-(1H-tetrazol-1-yl)phenyl)pyridine 1-oxide

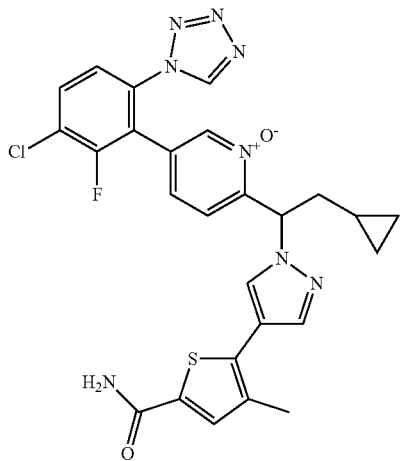

LC/MS: mass calculated for $C_{26}H_{22}ClFN_8O_2S$: 564.13, measured (ES, m/z): 565.05 [M+H]$^+$. $^1$H NMR (400 MHz, DMSO-$d_6$) δ 9.68 (s, 1H), 8.42 (s, 1H), 8.37 (s, 1H), 8.06 (t, J=8.2 Hz, 1H), 7.84-7.89 (m, 1H), 7.82 (s, 1H), 7.76 (dd, J=8.7, 1.5 Hz, 1H), 7.54 (s, 1H), 7.29-7.31 (m, 2H), 7.17 (dd, J=8.3, 1.7 Hz, 1H), 6.10-6.14 (m, 1H), 2.29-2.38 (m, 1H), 2.27 (s, 3H) 1.90-2.07 (m, 1H), 0.58-0.62 (m, 1H), 0.28-0.38 (m, 2H), 0.08-0.13 (m, 1H), −0.06--0.01 (m, 1H). $^{19}$F NMR (400 MHz, DMSO-$d_6$) δ −112.74.

Example 1034: (R*)-5-(3-Chloro-2-fluoro-6-(1H-tetrazol-1-yl)phenyl)-2-(2-cyclopropyl-1-(4-(4-methyl-2-(trifluoromethyl)thiazol-5-yl)-1H-pyrazol-1-yl)ethyl)pyridine 1-oxide

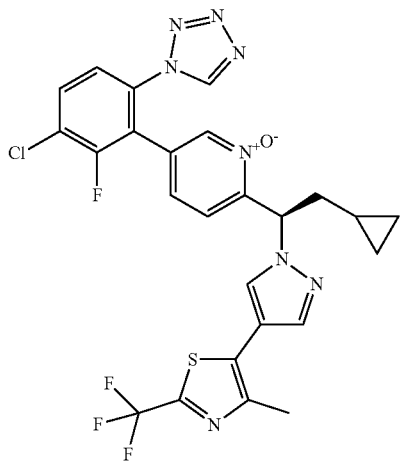

LC/MS: mass calculated for $C_{25}H_{19}ClF_4N_8OS$: 590.10; measured (ES, m/z): 591.00 [M+H]$^+$. $^1$H NMR (300 MHz, DMSO-$d_6$) δ 9.67 (s, 1H), 8.54 (s, 1H), 8.41 (s, 1H), 8.04 (t, J=8.2 Hz, 1H), 7.93 (s, 1H), 7.74 (d, J=8.7 Hz, 1H), 7.34 (d, J=8.2 Hz, 1H), 7.15 (d, J=8.3 Hz, 1H), 6.08-6.18 (m, 1H), 2.49 (s, 3H), 2.38-2.22 (m, 1H), 1.94 (m, 1H), 0.49-0.64 (m, 1H), 0.20-0.40 (m, 2H), 0.02-0.13 (m, 1H), −0.03--0.12 (m, 1H). $^{19}$F NMR (282 MHz, DMSO-$d_6$) δ −59.92, −112.77.

Example 1035: (S*)-5-(3-Chloro-2-fluoro-6-(1H-tetrazol-1-yl)phenyl)-2-(2-cyclopropyl-1-(4-(4-methyl-2-(trifluoromethyl)thiazol-5-yl)-1H-pyrazol-1-yl)ethyl)pyridine 1-oxide

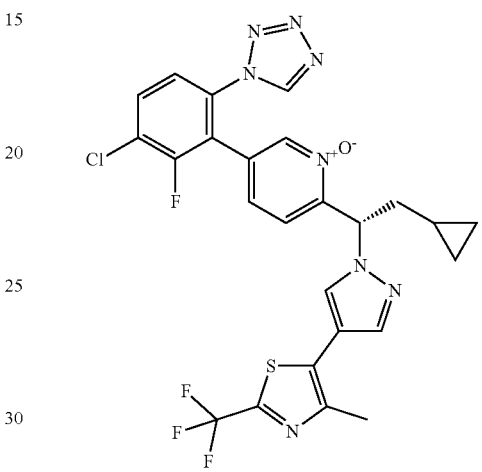

LC/MS: mass calculated for $C_{25}H_{19}ClF_4N_8OS$: 590.10; measured (ES, m/z): 590.95 [M+H]$^+$. $^1$H NMR (300 MHz, DMSO-$d_6$) δ 9.67 (s, 1H), 8.54 (s, 1H), 8.41 (s, 1H), 8.04 (t, J=8.2 Hz, 1H), 7.93 (s, 1H), 7.74 (d, J=8.7 Hz, 1H), 7.34 (d, J=8.3 Hz, 1H), 7.15 (d, J=8.3 Hz, 1H), 6.08-6.18 (m, 1H), 2.48 (s, 3H), 2.23-2.37 (m, 1H), 1.87-1.20 (m, 1H), 0.50-0.64 (m, 1H), 0.19-0.40 (m, 2H), 0.02-0.13 (m, 1H), −0.03--0.13 (m, 1H). $^{19}$F NMR (282 MHz, DMSO-$d_6$) δ −59.92, −112.74.

BIOLOGICAL EXAMPLES

Biological Example 1

Factor XIa inhibition assay utilizing a fluorophore-quencher pair peptide substrate A fluorescence intensity (FLINT) based assay was used to monitor inhibition of Factor XIa. The peptide substrate, 5Fam-KLTRAETV-K5Tamra (purchased from New England Peptide) was chosen based on the FXI sequence. Conversion of zymogen FXI to its activated form, FXIa, occurs by proteolytic cleavage by FXIa at two sites, Arg146 and Arg180. The custom peptide used in this assay was based on the Arg146 cleavage site of FXI. The peptide substrate was designed with a fluorophore-quencher pair, where the fluorescence is quenched until FXIa cleaves the 8-mer peptide after the Arg residue. The substrate $K_M$ was fit to a substrate inhibition model whereby $k_{cat}$=0.86 s$^{-1}$, $K_M$=12.4 μM, $K_i$=61.6 μM with an enzymatic efficiency, and $k_{cat}/K_M$=69523 M$^{-1}$s$^{-1}$.

The Factor XIa FLINT assay was used with the following 5Fam-KLTRAETV-K5Tamra assay buffer: 50 mM Tris, pH 7.5, 100 mM NaCl, 5 mM CaCl$_2$, 0.1 mg/mL BSA, 0.03% CHAPS. Assay buffer was prepared by mixing all ingredients fresh. 5Fam-KLTRAETV-K5Tamra peptide substrate was first prepared at 10 mM in 100% DMSO, then diluted to 3 mM in 100% DMSO. Assay buffer was then added directly to the 3 mM stock of substrate to prepare the 30 μM 2× working concentration (15 μM final concentration). The 2× Factor XIa stock solution was prepared by diluting 6.562 μM stock in 1× assay buffer for a 200 μM working stock solution (100 μM final concentration).

Test compound(s) were run in an 11-point, 3-fold serial dilution with a final top compound concentration of 100 nM. Final DMSO in assay was 2%. FXIa was preincubated with compound for 30-minutes and then substrate was added to initiate the reaction. The assay was run with either end point (EP) reads at 30 min or kinetic (KIN) reads at 5 min intervals over 30 minutes. The time course was linear using 100 μM FXIa greater than 30 minutes. More specifically, the assay was run as follows:

- 100 nL of 0.01 mM test compound was dispensed into black 384-well non-binding Greiner BioOne 784900 plate for 0.1 μM final concentration;
- 5 μL of 1× assay buffer was dispensed to column 24 (low control) and 5 μL 2× Factor XIa solution was dispensed to columns 1-23 (column 23 high control);
- the plate was centrifuged with a "cover" plate at 500 rpm for 1 min
- the plate was pre-incubated for 30 minutes at room temperature with plate covered;
- 5 μL of 2×5Fam-KLTRAETV-K5Tamra peptide substrate was dispensed into the entire plate, columns 1-24;
- the plate was centrifuged with a "cover" plate at 500 rpm for 1 min;
- the plate was read monitoring fluorescence intensity on the BMG PHERAStar at room temperature, using fluorescence module 485 nm/520 nm.

Percent inhibition ($IC_{50}$) curves were generated per compound tested, and data was analyzed using a 4-parameter logistic fit using GeneData Screener. The relative fluorescence unit (RFU) values were normalized to percent inhibition using the following equation:

$$\% \text{ inhibition} = ((HC-LC)-(compound-LC)/(HC-LC))*100$$

where LC—low control=mean signal of no Factor XIa or 100% inhibition of Factor XIa; HC—high control=mean signal of Factor XIa+5Fam-KLTRAETV-K5Tamra peptide substrate with DMSO only.

An 11-point dose response curve for the test compound(s) was generated using GENDATA to determine $IC_{50}$ value based on the following equation:

$$Y=\text{Bottom}+(\text{Top}-\text{Bottom})/(1+10^{\wedge}((\log IC_{50}-X)*\text{HillSlope}))$$

where Y is the % inhibition in the presence of X inhibitor concentration, Top=high control=mean signal of Factor XIa+5Fam-KLTRAETV-K5Tamra peptide substrate with DMSO only; Bottom=low control—mean signal of no Factor XIa or 100% inhibition of Factor XIa; HillSlope—Hill coefficient; and $IC_{50}$=concentration of compound with 50% inhibition in relation to top/high control.

Biological Example 2

Kallikrein Inhibition Assay Utilizing a Quenched AMC Peptide Substrate

A fluorescence intensity (FLINT) based assay was used to monitor inhibition of human plasma kallikrein. The peptide substrate, Z-Gly-Pro-Arg-AMC (Purchased from Bachem; Catalog #1-1150) was chosen based on its relatively low $K_M$ for kallikrein which enables running the assay at lower substrate concentrations to control background fluorescence. The kinetic parameters for this substrate were determined by fitting titration data to the Michaelis-Menten equation yielding a $K_M$=40 μM, $k_{cat}$=0.76 s$^{-1}$, and $k_{cat}/K_M$=18932 M$^{-1}$s$^{-1}$.

The Kallikrein FLINT assay was used with the following Z-Gly-Pro-Arg-AMC assay buffer: 50 mM Tris, pH 7.5, 100 mM NaCl, 5 mM CaCl$_2$, 0.1 mg/mL BSA, 0.03% CHAPS. Assay buffer was prepared by mixing all ingredients fresh. 2× Z-Gly-Pro-Arg-AMC peptide substrate was prepared by diluting 10 mM stock into 1× assay buffer for a 100 μM working concentration (50 μM final concentration). The 2× kallikrein stock solution was prepared by diluting 14.76 μM stock in 1× assay buffer for a 4 nM working stock solution (2 nM final concentration).

Test compound(s) were run in an 11-point, 3-fold serial dilution with a final top compound concentration of 1 μM. Final DMSO in assay was 2%. Plasma kallikrein was pre-incubated for 30-minute with compound and then 50 μM substrate was added to initiate the reaction. The assay was run with either end point (EP) reads at 30 min or kinetic (KIN) reads at 5 min intervals over 30 minutes. The time course was linear using 2 nM kallikrein greater than 30 minutes. More specifically, the assay was run as follows:

- 100 nL of 0.1 mM test compound was dispensed into black 384-well non-binding Greiner BioOne 784900 plate for 1 μM final concentration;
- 5 μL of 1× assay buffer was dispensed to columns 24 (low control) and 5 μL 2× human kallikrein enzyme solution was dispensed to columns 1-23 (column 23 high control);
- the plate was centrifuged with a "cover" plate at 500 rpm for 1 min
- the plate was pre-incubated for 30 minutes at room temperature with plate covered;
- 5 μL of 2× Z-Gly-Pro-Arg-AMC peptide substrate was dispensed into the entire plate, columns 1-24;
- the plate was centrifuged with a "cover" plate at 500 rpm for 1 min;
- the plate was read monitoring fluorescence intensity on the BMG PHERAStar at room temperature, using fluorescence module 340 nm/440 nm.

Percent inhibition ($IC_{50}$) curves were generated per compound tested, and data was analyzed using a 4-parameter logistic fit using GeneData Screener. The relative fluorescence unit (RFU) values were normalized to percent inhibition using the following equation:

$$\% \text{ inhibition} = ((HC-LC)-(compound-LC)/(HC-LC))*100$$

where LC—low control=mean signal of human kallikrein enzyme or 100% inhibition of human kallikrein enzyme; HC—high control=mean signal of Factor XIa+Z-Gly-Pro-Arg-AMC peptide substrate with DMSO only.

An 11-point dose response curve for the test compound(s) was generated using GENDATA to determine $IC_{50}$ value based on the following equation:

$$Y=\text{Bottom}+(\text{Top}-\text{Bottom})/(1+10^{\wedge}((\log IC_{50}-X)*\text{HillSlope}))$$

where Y is the % inhibition in the presence of X inhibitor concentration, Top=high control=mean signal of human kallikrein enzyme+Z-Gly-Pro-Arg-AMC peptide substrate with DMSO only; Bottom=low control—mean signal of no human kallikrein enzyme or 100% inhibition of human kallikrein enzyme; HillSlope—Hill coefficient; and IC$_{50}$=concentration of compound with 50% inhibition in relation to top/high control.

Representative compounds of formula (I) of the present invention were tested according to the procedure described in Biological Example 1 and Biological Example 2 above, with results as listed in Table 8, below. Results listed in columns with (ER) designation were measured using endpoint reads where a single fluorescence reading was measured for each well at a 30 min timepoint. Results listed in columns with (KIN) designation were measured using kinetic reads, where fluorescence readings for each well were collected at 5 min intervals over the course of 30 min, and the resulting linear rate was used to calculate the IC$_{50}$ of inhibition. The notation "NT" indicates that the compound was not tested.

TABLE 8

Biological Activity, Representative Compounds of Formula (I)

| ID No. | FXIa (KIN) IC$_{50}$ (nM) | FXIa (EP) IC$_{50}$ (nM) | Kallikrein (KIN) IC$_{50}$ (nM) | Kallikrein (EP) IC$_{50}$ (nM) |
|---|---|---|---|---|
| P1 | 2.8 | 2.6 | 157.3 | 124.5 |
| P2 | | 15.6 | | 263 |
| P3 | | 9.4 | | 98.2 |
| P4 | | 9.9 | | 517 |
| P5 | | 1.47 μM | | 28.4 μM |
| P6 | 1.9 | 2.1 | 85.2 | 65.8 |
| P7 | 0.1 | 0.8 | 1.3 | 4.1 |
| P8 | | 2.7 | | 328.7 |
| P9 | | 0.29 | | 37.0 |
| P10 | | 2.36 μM | | >100 μM |
| P11 | | 6.9 | | 81.4 |
| P12 | | 71.7 | | 369.5 |
| P13 | 39.5 | | 536.0 | |
| P14 | | 94.4 | | 965.8 |
| P15 | | 55.6 | | 598.1 |
| P16 | | 56.1 | | 401.2 |
| P17 | | 3 | | 81.9 |
| P18 | | 3.1 | | 396.2 |
| P19 | | 3.4 | | 134.9 |
| P20 | | 6.1 | | 77.2 |
| P21 | | 10.1 | | 165.8 |
| P22 | | 10 | | 44.2 |
| P23 | | 4.4 | | 66.1 |
| P24 | | 4.9 | | 114.1 |
| P25 | | 9 | | 749 |
| P26 | | 258.1 | | 2.65 μM |
| P27 | | 121.7 | | 647.9 |
| P28 | 4.1 | 2.7 | 59.8 | 47.5 |
| P29 | | 580.2 | | 1.16 μM |
| P30 | | 3.3 | | 57.3 |
| P31 | | 760.7 | | 4.11 μM |
| P32 | | 717.6 | | 3.45 μM |
| P33 | | 375 | | 2.08 μM |
| P34 | 19.9 | | 256.0 | |
| P35 | | 168.8 | | 800 |
| P36 | | 4.4 | | 47 |
| P37 | | 311.4 | | 1.72 μM |
| P38 | | 3.2 | | 56 |
| P39 | | 3.8 | | 25.8 |
| P40 | | 779.8 | | 2.18 μM |
| P41 | | 1.23 μM | | >10 μM |
| P42 | | 372.3 | | 1.55 μM |
| P43 | | 11 | | 147.1 |
| P44 | | 148.7 | | 1.75 μM |
| P45 | | 2.3 | | 12.6 |
| P46 | | 21.5 | | 341.2 |
| P47 | | 22.2 | | 405.2 |
| P48 | | 317 | | 2.61 μM |
| P49 | | 3.4 | | 79.2 |
| P50 | | 3.5 | | 46.5 |
| P51 | 1.28 μM | | >10 μM | |
| P52 | | 257.3 | | 7707.3 |
| P53 | | 358.8 | | >10 μM |
| P54 | | 92.1 | | 3.37 μM |
| P55 | | 1.5 | | 5.4 |
| P56 | | 2.33 μM | | >10 μM |
| P57 | | 0.4 | | 3.8 |
| P58 | | 6.5 | | 28.5 |
| P59 | | ~0.4 | | 4.4 |
| P60 | | 3.49 μM | | >10 μM |
| P61 | | 6.3 | | 51.9 |
| P62 | | 0.5 | | 7.8 |
| P63 | | 1 | | 7.3 |
| P64 | | 0.3 | | 5.3 |
| P65 | | 24.2 | | 721.4 |
| P66 | | 1.7 | | 20.6 |
| P67 | | 5.1 | | 361.8 |
| P68 | | 4.1 | | 512.9 |
| P69 | | 93.2 | | >10 μM |
| P70 | | 37.2 | | 1.06 μM |
| P71 | | 1.1 | | 7.5 |
| P72 | | 87 | | 4.37 μM |
| P73 | | 15.1 | | 3.41 μM |
| P74 | | 13.3 | | 3.26 μM |
| P75 | | 29.2 | | 248.6 |
| P76 | | 1.4 | | 4.2 |
| P77 | | 1.1 | | 36.2 |
| P78 | | 6.1 | | 6.27 μM |
| P79 | | 11.7 | | 3.37 μM |
| P80 | | 0.6 | | 53.3 |
| P81 | | 7.4 | | 3.85 μM |
| P82 | | 19.2 | | 6.11 μM |
| P83 | | 133.8 | | 1.77 μM |
| P84 | | 0.4 | | 14.5 |
| P85 | | 0.8 | | 4.1 |
| P86 | | 1.6 | | 23 |
| P87 | | 45.6 | | 79.8 |
| P88 | | 622.6 | | 1.14 μM |
| P89 | | 18.7 | | 1.71 uN |
| P90 | | 15.8 | | 80 |
| P91 | | 8.9 | | 1.53 μM |
| P92 | | 3.5 | | 45.5 |
| P93 | | 0.9 | | 4.5 |
| P94 | | 2.9 | | 18.3 |
| P95 | | 10.8 | | 9.37 μM |
| P96 | | 2.3 | | 259.5 |
| P97 | | 47 | | 1.06 μM |
| P98 | | 25.8 | | 4.63 μM |
| P99 | | 1.4 | | 2371.4 |
| P100 | | 10.4 | | 519.9 |
| P101 | | 14.7 | | 625.2 |
| P102 | | 6.9 | | 72.2 |
| P103 | | 464.5 | | >10 μM |
| P104 | | 12.4 | | >10 μM |
| P105 | | 121.6 | | 7.64 μM |
| P106 | | 4.8 | | 634.9 |
| P107 | | 15.7 | | 1.85 μM |
| P108 | | 34.1 | | 648.9 |
| P109 | | 4.1 | | 45.7 |
| P110 | | 5.6 | | 122.5 |
| P111 | | 331.1 | | >10 μM |
| P112 | | 172.1 | | 5.42 μM |
| P113 | | 5.3 | | 291.3 |
| P114 | | 5.2 | | 183.7 |
| P115 | | 0.7 | | 29.1 |
| P116 | | 1 | | 26.2 |
| P117 | | 2.1 | | 9.7 |
| P118 | | 1.9 | | 64.9 |
| P119 | | 2.4 | | 154.7 |
| P120 | | 36.5 | | 2.0 μM |
| P121 | | 3.6 | | 11.3 |
| P122 | | 27.1 | | 260.2 |
| P123 | | 31.6 | | 1.37 μM |
| P124 | | 202.4 | | 7.16 μM |
| P125 | | 1.2 | | 3.3 |
| P126 | | 8.7 | | 247.7 |
| P127 | | 1.3 | | 70.1 |

TABLE 8-continued

Biological Activity, Representative Compounds of Formula (I)

| ID No. | FXIa (KIN) IC$_{50}$ (nM) | FXIa (EP) IC$_{50}$ (nM) | Kallikrein (KIN) IC$_{50}$ (nM) | Kallikrein (EP) IC$_{50}$ (nM) |
|---|---|---|---|---|
| P128 | 3.6 | | 475.1 | |
| P129 | 20.2 | | 135.5 | |
| P130 | 79.6 | | 959.4 | |
| P131 | 16.1 | | 191.6 | |
| P132 | 30.7 | | 1.66 μM | |
| P133 | 483.3 | | 7.86 μM | |
| P134 | 1.1 | | 7.1 | |
| P135 | 3.5 | | 10.8 | |
| P136 | 412.8 | | 189.5 | |
| P137 | 3.8 | | 151.4 | |
| P138 | 0.4 | | 4.1 | |
| P139 | 2.7 | | 57.5 | |
| P140 | 6.8 | | 98.1 | |
| P141 | 3.9 | | 72.8 | |
| P142 | 5.4 | | 107.8 | |
| P143 | 1.7 | | 58.1 | |
| P144 | 255.9 | | 5.54 μM | |
| P145 | 146.3 | | 2.31 μM | |
| P146 | 9 | | 571.3 | |
| P147 | 1.7 | | 12.2 | |
| P148 | 635 | | 349.5 | |
| P149 | 17.6 | | 1.39 μM | |
| P150 | 169.7 | | 397 | |
| P151 | 3.8 | | 80.1 | |
| P152 | 164.4 | | 895.4 | |
| P153 | 4.1 | | 108 | |
| P154 | 497.2 | | 3.28 μM | |
| P155 | 3.7 | | 86.1 | |
| P156 | 6.3 | | 86.7 | |
| P157 | 177.4 | | 2.14 μM | |
| P158 | 3.5 | | 45.1 | |
| P159 | 5.5 | | 214.9 | |
| P160 | 2.8 | | 7 | |
| P161 | 6 | | 76.7 | |
| P162 | 2.3 | | 6.8 | |
| P163 | 0.7 | | 26.9 | |
| P164 | 2.3 | | 28.5 | |
| P165 | 1.2 | | 6 | |
| P166 | 41.5 | | 922.8 | |
| P167 | 36.4 | | 825.8 | |
| P168 | 0.5 | | 772.7 | |
| P169 | 669.4 | | >10 μM | |
| P170 | 3.9 | | 46.8 | |
| P171 | 2.4 | | 15.3 | |
| P172 | 1.1 | | 16.2 | |
| P173 | 8.8 | | 78.4 | |
| P174 | 8.1 | | 50.8 | |
| P175 | <0.2 | | 365 | |
| P176 | 100.9 | | >10 μM | |
| P177 | 119.7 | | 1.39 μM | |
| P178 | 0.5 | | 21.6 | |
| P179 | 14.7 | | 179.3 | |
| P180 | 374.1 | | 1.98 μM | |
| P181 | 5.2 | | 67.7 | |
| P182 | 73.8 | | 55.2 | |
| P183 | 4.8 | | 186.3 | |
| P184 | 7.2 | | 2.0 μM | |
| P185 | 661.3 | | 2.55 μM | |
| P186 | 121.6 | | 319.5 | |
| P187 | 6.4 | | 124.4 | |
| P188 | 82.3 | | 9.78 μM | |
| P189 | >10 μM | | >10 μM | |
| P190 | 2 | | 49.2 | |
| P191 | 146.3 | | 1.92 μM | |
| P192 | 0.6 | | 24 | |
| P193 | 1.16 μM | | ~9.3 μM | |
| P194 | 12.2 | | 227.7 | |
| P195 | 42.9 | | 1.7 μM | |
| P196 | 194.3 | | 994.5 | |
| P197 | 92.2 | | 2.23 μM | |
| P198 | 74.3 | | 1.86 μM | |
| P199 | 71 | | 7.9 μM | |
| P200 | 261.9 | | >10 μM | |
| P201 | 2.7 | | 73.9 | |
| P202 | 3.5 | | 119.2 | |
| P203 | 2.6 | | 63.3 | |
| P204 | 1.5 | | 45.1 | |
| P205 | 616 | | 2.29 μM | |
| P206 | 6.6 | | 137.1 | |
| P207 | 0.8 | | 2.9 | |
| P208 | 69.2 | | 7.1 μM | |
| P209 | 58.3 | | >10 μM | |
| P210 | 3.1 | | 22.8 | |
| P211 | 1.34 μM | | 9.04 μM | |
| P212 | 4 | | 59.3 | |
| P213 | 11.8 | | 491 | |
| P214 | 0.5 | | 6.3 | |
| P215 | 17.1 | | 755.3 | |
| P216 | 32.7 | | 295.9 | |
| P217 | 302.3 | | 4.63 μM | |
| P218 | 2.7 | | 87.2 | |
| P219 | 188.3 | | 3.09 μM | |
| P220 | 0.5 | | 13.9 | |
| P221 | 2.8 | | 376.6 | |
| P222 | 12.7 | | 189.1 | |
| P223 | 11.6 | | 790.9 | |
| P224 | 22.7 | | 591.4 | |
| P225 | 144 | | ~1.4 μM | |
| P226 | 0.4 | | 3 | |
| P227 | 0.5 | | 11.9 | |
| P228 | 98.3 | | 1291.8 | |
| P229 | 8.7 | | 270.7 | |
| P230 | 1.1 | | 24.7 | |
| P231 | 10.5 | | 366.4 | |
| P232 | 256.2 | | 3.78 μM | |
| P233 | 4.19 μM | | >10 μM | |
| P234 | 20.7 | | 298.5 | |
| P235 | 0.4 | | 1.4 | |
| P236 | 14.9 | | 158.2 | |
| P237 | 195.8 | | 2.44 μM | |
| P238 | 0.3 | | 0.7 | |
| P239 | 3.7 | | 180.4 | |
| P240 | 11.1 | | 1.11 μM | |
| P241 | 93.6 | | 1.03 μM | |
| P242 | 0.3 | | 3.9 | |
| P243 | 351 | | 4.37 μM | |
| P244 | 1.1 | | 22.4 | |
| P245 | 25.8 | | 4.28 μM | |
| P246 | 38.3 | | 4.86 μM | |
| P247 | 1.1 | | 5.8 | |
| P248 | 1.4 | | 14.9 | |
| P249 | 34.3 | | 668.2 | |
| P250 | 11.8 | | 45.9 | |
| P251 | 0.3 | | 2.5 | |
| P252 | 12.7 | | 616.5 | |
| P253 | 2.7 | | 159.3 | |
| P254 | 4.2 | | 375.9 | |
| P255 | 9.5 | | 689.6 | |
| P256 | 0.4 | | 3 | |
| P257 | 0.6 | | 7.1 | |
| P258 | 5.8 | | 201 | |
| P259 | 1.49 μM | | 2.89 μM | |
| P260 | 5.8 | | 72.5 | |
| P261 | 401 | | 2.28 μM | |
| P262 | 1.7 | | 31.8 | |
| P263 | 1.01 μM | | 3.75 μM | |
| P264 | 3.9 | | 46.3 | |
| P265 | 7.9 | | 88.1 | |
| P266 | 3.8 | | 197 | |
| P267 | 57.7 | | 1.36 μM | |
| P268 | 36.3 | | 3.02 μM | |
| P269 | 0.5 | | 6.1 | |
| P270 | 410.3 | | 268.2 | |
| P271 | 111.5 | | 252 | |
| P272 | 0.3 | | 3.2 | |
| P273 | 0.5 | | 10.9 | |
| P274 | 10.7 | | 285.8 | |
| P275 | 2.8 | | 19.1 | |

TABLE 8-continued

Biological Activity, Representative Compounds of Formula (I)

| ID No. | FXIa (KIN) IC$_{50}$ (nM) | FXIa (EP) IC$_{50}$ (nM) | Kallikrein (KIN) IC$_{50}$ (nM) | Kallikrein (EP) IC$_{50}$ (nM) |
|---|---|---|---|---|
| P276 | 0.7 | | 8.1 | |
| P277 | 1.3 | | 13.3 | |
| P278 | 6.9 | | 109.9 | |
| P279 | 6.55 μM | | >10 μM | |
| P280 | 3.7 | | 84 | |
| P281 | 0.4 | | 2.6 | |
| P282 | 22.9 | | 775 | |
| P283 | 8.4 | | 74.5 | |
| P284 | 255.9 | | 1.0 μM | |
| P285 | 2.4 | | 16.2 | |
| P286 | 7.1 | | 23 | |
| P287 | 3.3 | | 109.2 | |
| P288 | 16.8 | | 841 | |
| P289 | 0.5 | | 13.8 | |
| P290 | 78.3 | | 1.1 μM | |
| P291 | 1.5 | | 12.5 | |
| P292 | 10.1 | | 51.3 | |
| P293 | 13.1 | | 67.6 | |
| P294 | 44.7 | | 212.4 | |
| P295 | 16.5 | | 384.7 | |
| P296 | 1.9 | | 36.4 | |
| P297 | 0.3 | | 2.2 | |
| P298 | 72.7 | | 1.04 μM | |
| P299 | 1.4 | | 24.9 | |
| P300 | 154.2 | | 1.67 μM | |
| P301 | 112 | | 1.69 μM | |
| P302 | 2.6 | | 54.6 | |
| P303 | 1.5 | | 32.7 | |
| P304 | 116.5 | | 1.15 μM | |
| P305 | 0.4 | | 5.5 | |
| P306 | 0.4 | | 14.8 | |
| P307 | 0.7 | | 7.7 | |
| P308 | 185.7 | | 1.22 μM | |
| P309 | 0.7 | | 9.2 | |
| P310 | 0.8 | | 9 | |
| P311 | 1.2 | | 24.2 | |
| P312 | 0.8 | | 14.3 | |
| P313 | 44.6 | | 150.8 | |
| P314 | 0.2 | | 1.4 | |
| P315 | 2.4 | | 51 | |
| P316 | 530.3 | | 2.78 μM | |
| P317 | 1256.6 | | 5.42 μM | |
| P318 | 0.9 | | 13.9 | |
| P319 | 596.6 | | 1.92 μM | |
| P320 | 2 | | 127.8 | |
| P321 | 16.2 | | 94.9 | |
| P322 | 3.9 | | 83.4 | |
| P323 | 3.6 | | 23 | |
| P324 | 31.0 | | 3.72 μM | |
| P325 | 2.4 | | 125.8 | |
| P326 | 8.8 | | 47.9 | |
| P327 | 1.7 | | 29.1 | |
| P328 | 0.2 | | 0.4 | |
| P329 | 3.1 | | 49.6 | |
| P330 | 0.3 | | 3.3 | |
| P331 | 3.3 | | 28.5 | |
| P332 | 58.5 | | 59.5 | |
| P333 | 2.2 | | 17.2 | |
| P334 | 0.6 | | 29 | |
| P335 | 6.1 | | 39.8 | |
| P336 | 100.4 | | 4.51 μM | |
| P337 | 10.8 | | 556.5 | |
| P338 | 1.3 | | 74.5 | |
| P339 | 25.5 | | 670.2 | |
| P340 | 1.9 | | 39.3 | |
| P341 | 6.7 | | 320.2 | |
| P342 | 0.3 | | 4.3 | |
| P343 | 53.6 | | 767.4 | |
| P344 | 7.9 | | 175.4 | |
| P345 | 9.9 | | 152.5 | |
| P346 | 2.5 | | 11.8 | |
| P347 | 38.3 | | 805.7 | |
| P348 | 0.8 | | 27.2 | |
| P349 | 1.2 | | 30.2 | |
| P350 | 689.6 | | 8.67 μM | |
| P351 | 8.2 | | 131.1 | |
| P352 | 1 | | 13.4 | |
| P353 | 778.4 | | 3.04 μM | |
| P354 | 1.9 | | 38.8 | |
| P355 | 262.1 | | 933.5 | |
| P356 | 2.8 | | 30.7 | |
| P357 | 1.2 | | 23.7 | |
| P358 | 8.9 | | 81.9 | |
| P359 | 0.9 | | 10.2 | |
| P360 | 1.3 | | 36.6 | |
| P361 | 1.95 μM | | >10 μM | |
| P362 | 1.7 | | 38.3 | |
| P363 | 537 | | 2.84 μM | |
| P364 | 1.6 | | 13.5 | |
| P365 | 3.2 | | 30.1 | |
| P366 | 3.3 | | 150.5 | |
| P367 | 1.0 | | 43.9 | |
| P368 | 23.9 | | 621.2 | |
| P369 | 42.8 | | 1.11 μM | |
| P370 | 215.6 | | 2.83 μM | |
| P371 | 198.7 | | 2.29 μM | |
| P372 | 3.53 μM | | 4.07 μM | |
| P373 | 4.2 | | 160.6 | |
| P374 | 163.9 | | 1.86 μM | |
| P375 | 18.8 | | 55.9 | |
| P376 | 1.67 μM | | 2.37 μM | |
| P377 | 0.3 | | 2.1 | |
| P378 | 51.3 | | 139.9 | |
| P379 | 44.6 | | 2.67 μM | |
| P380 | 46.2 | | 1.15 μM | |
| P381 | 4 | | 36.6 | |
| P382 | 0.5 | | 7.3 | |
| P383 | 643.1 | | 1.76 μM | |
| P384 | 206.5 | | 1.79 μM | |
| P385 | 0.6 | | 3.5 | |
| P386 | 4.3 | | 39.8 | |
| P387 | 4.58 μM | | >10 μM | |
| P388 | 13.5 | | 125.5 | |
| P389 | 3.3 | | 517.6 | |
| P390 | 22.6 | | 1.9 μM | |
| P391 | >10 μM | | 5.18 μM | |
| P392 | 2.4 | | 64.1 | |
| P393 | 3.8 | | 36.6 | |
| P394 | 917.7 | | 1.51 μM | |
| P395 | 5.8 | | 25.5 | |
| P396 | 7.73 μM | | >10 μM | |
| P397 | 13.7 | | 397.3 | |
| P398 | 29.2 | | 729.8 | |
| P399 | 447.2 | | 3.85 μM | |
| P400 | 13.4 | | 93.8 | |
| P401 | 0.7 | | 18.6 | |
| P402 | 427.5 | | 5.02 μM | |
| P403 | 964.5 | | 2.18 μM | |
| P404 | 10.6 | | 68.4 | |
| P405 | ~365 | | 3.34 μM | |
| P406 | 0.7 | | 27.6 | |
| P407 | 7.1 | | 109.3 | |
| P408 | 1.3 | | 17.4 | |
| P409 | 3.4 | | 32.3 | |
| P410 | 919 | | 1.74 μM | |
| P411 | 3.1 | | 16 | |
| P412 | 368 | | 2.06 μM | |
| P413 | 0.9 | | 19.3 | |
| P414 | 248.5 | | >10 μM | |
| P415 | 2.5 | | 183.6 | |
| P416 | 0.3 | | 3.3 | |
| P417 | 6.3 | | 77.1 | |
| P418 | 2.2 | | 55.6 | |
| P419 | 3.4 | | 36.3 | |
| P420 | 598.8 | | 4.63 μM | |
| P421 | 1.3 | | 41.1 | |
| P422 | 215.5 | | 2.44 μM | |
| P423 | 1.4 | | 43.9 | |

TABLE 8-continued

Biological Activity, Representative Compounds of Formula (I)

| ID No. | FXIa (KIN) IC$_{50}$ (nM) | FXIa (EP) IC$_{50}$ (nM) | Kallikrein (KIN) IC$_{50}$ (nM) | Kallikrein (EP) IC$_{50}$ (nM) |
|---|---|---|---|---|
| P424 | 2.2 | | 28.6 | |
| P425 | 493.2 | | 572 | |
| P426 | 1.3 | | 53.6 | |
| P427 | 7.6 | | 66.8 | |
| P428 | 5.3 | | 64.1 | |
| P429 | 52.4 | | 3.81 μM | |
| P430 | 4.9 | | 38 | |
| P431 | 211.7 | | 1.79 μM | |
| P432 | 0.6 | | 2.8 | |
| P433 | 28 | | 105.5 | |
| P434 | 199.1 | | 427.1 | |
| P435 | 0.8 | | 9.7 | |
| P436 | 8.3 | | 95.6 | |
| P437 | 4.5 | | 112.8 | |
| P438 | 206.1 | | 2.16 μM | |
| P439 | 4.1 | | 69.8 | |
| P440 | 23.9 | | 70.2 | |
| P441 | 0.5 | | 3.2 | |
| P442 | 2.2 | | ~138 | |
| P443 | 0.4 | | 1.7 | |
| P444 | 0.4 | | 1.8 | |
| P445 | 155.3 | | 4.31 μM | |
| P446 | 283.3 | | 3.08 μM | |
| P447 | 0.5 | | 4.3 | |
| P448 | 6 | | 9.4 | |
| P449 | 2.7 | | 12 | |
| P450 | 368 | | 2.06 μM | |
| P451 | 3.8 | | 17.8 | |
| P452 | 0.7 | | 10.8 | |
| P453 | 20.3 | | 132.2 | |
| P454 | 1 | | 12.6 | |
| P455 | 14.9 | | 495.6 | |
| P456 | 10.7 | | 630.1 | |
| P457 | 3.4 | | 554.2 | |
| P458 | 1.2 | | 19 | |
| P459 | 4.2 | | 104.9 | |
| P460 | 1.9 | | 605.8 | |
| P461 | 3.5 | | 32.5 | |
| P462 | 1.2 | | 14.3 | |
| P463 | 0.5 | | 6.4 | |
| P464 | 12 | | 185.1 | |
| P465 | 5.8 | | 76.5 | |
| P466 | 8 | | 230.5 | |
| P467 | 7.8 | | 779.7 | |
| P468 | 4 | | 158.9 | |
| P469 | 0.8 | | 36.2 | |
| P470 | 8 | | 99.5 | |
| P471 | 0.9 | | 51.7 | |
| P472 | 2.5 | | 40.7 | |
| P473 | 2.7 | | 103.6 | |
| P474 | 1.5 | | 13.2 | |
| P475 | 17.8 | | 324.4 | |
| P476 | 1.1 | | 21.6 | |
| P477 | 10.3 | | 188 | |
| P478 | 1.6 | | 236 | |
| P479 | 196.1 | | 185.1 | |
| P480 | 4.9 | | 31.2 | |
| P481 | 0.8 | | 4.4 | |
| P482 | 1.2 | | 22.9 | |
| P483 | 1.2 | | 9.1 | |
| P484 | 12.8 | | 521.8 | |
| P485 | 233.7 | | 669.9 | |
| P486 | 0.8 | | 10.2 | |
| P487 | 0.5 | | 8.9 | |
| P488 | 0.7 | | 92.5 | |
| P489 | 2.5 | | 57.9 | |
| P490 | 2.4 | | 16.3 | |
| P491 | 0.3 | | 2.1 | |
| P492 | 0.4 | | 2.8 | |
| P493 | 14.4 | | 179.3 | |
| P494 | 2.3 | | 2.67 μM | |
| P495 | 0.8 | | 211.5 | |
| P496 | 4.4 μM | | >10 μM | |
| P497 | 3.3 | | 169.1 | |
| P498 | 1.03 μM | | >10 μM | |
| P499 | 4.96 μM | | >10 μM | |
| P500 | 1.9 | | 3.7 | |
| P501 | 30.1 | | 736.2 | |
| P502 | 0.3 | | 30.1 | |
| P503 | 0.2 | | 13.4 | |
| P504 | 36.5 | | 2.2 μM | |
| P505 | 363.2 | | >10 μM | |
| P506 | 1.5 | | 140.5 | |
| P507 | 841.8 | | >10 μM | |
| P508 | 0.5 | | 137.5 | |
| P509 | 2.8 μM | | >10 μM | |
| P510 | 0.3 | | 74.9 | |
| P511 | >10 μM | | >10 μM | |
| P512 | 7.91 μM | | 6.57 μM | |
| P513 | 0.4 | | 5.3 | |
| P514 | 23.2 | | 72.9 | |
| P515 | 328.7 | | 144.1 | |
| P516 | 912.9 | | 138.6 | |
| P517 | 1.4 | | 93.1 | |
| P518 | 2.3 | | 382.6 | |
| P519 | 6.05 μM | | >10 μM | |
| P520 | 8.4 | | 1.41 μM | |
| P521 | 5.5 | | 1.08 μM | |
| P522 | 114.3 | | 140.9 | |
| P523 | 754.6 | | 258.8 | |
| P524 | 7.3 | | 428 | |
| P525 | 6.2 | | 812.5 | |
| P526 | 6.2 | | 1.42 μM | |
| P527 | 3.5 | | 176.4 | |
| P528 | 3.78 μM | | >10 μM | |
| P529 | 105.2 | | 5006.1 | |
| P530 | 0.2 | | 8 | |
| P531 | 6 | | 174 | |
| P532 | >10 μM | | >10 μM | |
| P533 | 0.8 | | 7.7 | |
| P534 | 26.8 | | 93.1 | |
| P535 | 9 | | 219.9 | |
| P536 | 139.4 | | 8.8 μM | |
| P537 | 0.8 | | 96.7 | |
| P538 | 0.3 | | 1.9 | |
| P539 | 43.3 | | 2.05 μM | |
| P540 | 11.3 | | 471.3 | |
| P541 | 28.5 | | 4.79 μM | |
| P542 | 2.4 | | 302.3 | |
| P543 | 16.5 | | 3.28 μM | |
| P544 | 2.1 | | 354 | |
| P545 | 9.7 | | 942.8 | |
| P546 | 1.67 μM | | >10 μM | |
| P547 | 9.55 μM | | >10 μM | |
| P548 | 22.6 | | 514 | |
| P549 | 596.1 | | >20 μM | |
| P550 | 0.2 | | 18 | |
| P551 | 662.4 | | ~9.2 μM | |
| P552 | 1.5 | | 56 | |
| P553 | 7.40 μM | | >10 μM | |
| P554 | 10.8 | | 3.01 μM | |
| P555 | 5.1 | | 573.5 | |
| P556 | 0.2 | | 2.4 | |
| P557 | 6.5 | | 209.8 | |
| P558 | 2.90 μM | | >10 μM | |
| P559 | 213 | | >10 μM | |
| P560 | 4.4 | | 102.5 | |
| P561 | 0.6 | | 78.3 | |
| P562 | 189.1 | | 4.78 μM | |
| P563 | 0.9 | | 25 | |
| P564 | 0.3 | | 5.6 | |
| P565 | 347.2 | | 6.30 μM | |
| P566 | 15 | | 67.6 | |
| P567 | 326 | | 1.13 μM | |
| P568 | 0.7 | | 3.1 | |
| P569 | 0.7 | | 7.5 | |
| P570 | 2.3 | | 7.2 | |
| P571 | 63.9 | | 133.8 | |

TABLE 8-continued

Biological Activity, Representative Compounds of Formula (I)

| ID No. | FXIa (KIN) IC$_{50}$ (nM) | FXIa (EP) IC$_{50}$ (nM) | Kallikrein (KIN) IC$_{50}$ (nM) | Kallikrein (EP) IC$_{50}$ (nM) |
|---|---|---|---|---|
| P572 | 0.5 | | 24.1 | |
| P573 | 244.2 | | 4.35 μM | |
| P574 | 0.4 | | 7.9 | |
| P575 | 39.1 | | 1.92 μM | |
| P576 | 1.2 | | 62.4 | |
| P577 | 816.2 | | >10 μM | |
| P578 | 1.3 | | 158.4 | |
| P579 | 194.8 | | 5.78 μM | |
| P580 | 0.5 | | 13.5 | |
| P581 | 554.4 | | 3.14 μM | |
| P582 | 0.3 | | 0.9 | |
| P583 | 0.3 | | 1.5 | |
| P584 | 601.6 | | 6.0 μM | |
| P585 | 962.5 | | >10 μM | |
| P586 | 7.3 | | 626.6 | |
| P587 | 5.49 μM | | >10 μM | |
| P588 | 133.8 | | 2.85 μM | |
| P589 | 55.8 | | 520.5 | |
| P590 | | | | |
| P591 | 381.5 | | 2.53 μM | |
| P592 | 102.2 | | 396 | |
| P593 | ~4.7 μM | | >10 μM | |
| P594 | 3.1 | | 247 | |
| P595 | 4 | | 2.41 μM | |
| P596 | 1.3 | | 27.7 | |
| P597 | 1.17 μM | | >10 μM | |
| P598 | 52 | | 862 | |
| P599 | 0.5 | | 4 | |
| P600 | 0.3 | | 43.8 | |
| P601 | >10 μM | | >10 μM | |
| P602 | 340.3 | | 7.51 μM | |
| P603 | ~3.9 μM | | >10 μM | |
| P604 | 1.3 | | 290.2 | |
| P605 | 1.1 | | 10.7 | |
| P606 | 15.2 | | 660.1 | |
| P607 | 2.84 μM | | >10 μM | |
| P608 | 405.7 | | 8.01 μM | |
| P609 | 2.48 μM | | >10 μM | |
| P610 | 66.6 | | 582 | |
| P611 | 482.9 | | >10 μM | |
| P612 | 37.9 | | 5.06 μM | |
| P613 | 250.7 | | 1.72 μM | |
| P614 | 0.3 | | 8 | |
| P615 | >10 μM | | >10 μM | |
| P616 | 36.8 | | 204.8 | |
| P617 | 202.1 | | 2.77 μM | |
| P618 | 0.4 | | 5.6 | |
| P619 | 1.9 | | 89.3 | |
| P620 | 131.2 | | 5288.1 | |
| P621 | 127.9 | | >10 μM | |
| P622 | 1.47 μM | | >10 μM | |
| P623 | 1.3 | | 216.6 | |
| P624 | 0.5 | | 4.9 | |
| P625 | 247.7 | | >10 μM | |
| P626 | 2.8 | | 321.9 | |
| P627 | 621.2 | | >10 μM | |
| P628 | 1.4 | | 164.8 | |
| P629 | 999.5 | | >10 μM | |
| P630 | 0.9 | | 25 | |
| P631 | 0.5 | | 66.2 | |
| P632 | 3.17 μM | | 3.81 μM | |
| P633 | 20.6 | | 2.01 μM | |
| P634 | 192.2 | | 738.9 | |
| P635 | 1.4 | | 3.4 | |
| P636 | 0.3 | | 22.7 | |
| P637 | 1.28 μM | | >10 μM | |
| P638 | 8.12 μM | | >10 μM | |
| P639 | 1.6 | | 315.7 | |
| P640 | 1.3 | | 179.3 | |
| P641 | 212.6 | | 1.57 μM | |
| P642 | 2.08 μM | | >10 μM | |
| P643 | 0.9 | | 50.5 | |
| P644 | 0.6 | | 14.5 | |
| P645 | 36.6 | | 892.7 | |
| P646 | 3.9 | | 506.1 | |
| P647 | 8.47 μM | | >10 μM | |
| P648 | 6.8 | | 531.7 | |
| P649 | 4.52 μM | | >10 μM | |
| P650 | 3.6 | | 282.5 | |
| P651 | 113.4 | | 306.8 | |
| P652 | 0.4 | | 2.2 | |
| P653 | 8.1 | | 3.08 μM | |
| P654 | 465.9 | | >10 μM | |
| P655 | 16.5 | | 734.3 | |
| P656 | 1.41 μM | | >10 μM | |
| P657 | 1.8 | | 468.1 | |
| P658 | 110.8 | | 5.43 μM | |
| P659 | 1.9 | | 170.3 | |
| P660 | 5.1 | | 287.3 | |
| P661 | 1.26 μM | | >10 μM | |
| P662 | 6.63 μM | | >10 μM | |
| P663 | 7 | | 933 | |
| P664 | 1.7 | | 379.6 | |
| P665 | 184.1 | | >10 μM | |
| P666 | 9.5 | | 212.4 | |
| P667 | 322.6 | | >10 μM | |
| P668 | 0.6 | | 39.2 | |
| P669 | 3.40 μM | | >10 μM | |
| P670 | 3.18 μM | | >10 μM | |
| P671 | 772.1 | | >10 μM | |
| P672 | 1.19 μM | | >10 μM | |
| P673 | | | | |
| P674 | 1.4 | | 54.9 | |
| P675 | 8 | | 321.2 | |
| P676 | 0.3 | | 11.8 | |
| P677 | 6.46 μM | | >10 μM | |
| P678 | 774.3 | | >10 μM | |
| P679 | 3 | | 352.6 | |
| P680 | 0.3 | | 29 | |
| P681 | 209.3 | | >10 μM | |
| P682 | 1.1 μM | | 6.31 μM | |
| P683 | 0.4 | | 29.5 | |
| P684 | 1.06 μM | | 4.43 μM | |
| P685 | 4.9 | | 150.6 | |
| P686 | 8.89 μM | | >10 μM | |
| P687 | 1.33 μM | | >10 μM | |
| P688 | 4 | | 1.03 μM | |
| P689 | 3.01 μM | | >10 μM | |
| P690 | 2.3 | | 180 | |
| P691 | 5.6 | | 133.2 | |
| P692 | 5.6 | | 333.9 | |
| P693 | >10 μM | | >10 μM | |
| P694 | 2.4 | | 36.9 | |
| P695 | 5.3 | | 43.7 | |
| P696 | 1.1 | | 63 | |
| P697 | 6.7 | | 178.7 | |
| P698 | 68.3 | | 213.2 | |
| P699 | 45.5 | | 5.60 μM | |
| P700 | 2.13 μM | | >10 μM | |
| P701 | 536.8 | | >10 μM | |
| P702 | 0.3 | | 8.5 | |
| P703 | 1.2 | | 9.7 | |
| P704 | 0.5 | | 5.2 | |
| P705 | 2.2 | | 209.6 | |
| P706 | 7.13 μM | | >10 μM | |
| P707 | 130.1 | | 464.5 | |
| P708 | 31.5 | | 657.7 | |
| P709 | 397.9 | | >10 μM | |
| P710 | 121.4 | | 175 | |
| P711 | 0.5 | | 2.8 | |
| P712 | 5.7 | | 35.4 | |
| P713 | 0.5 | | 29.9 | |
| P714 | 0.4 | | 28.6 | |
| P715 | 301.8 | | 830.2 | |
| P716 | 0.3 | | 22.1 | |
| P717 | 1.43 μM | | >10 μM | |
| P718 | 0.3 | | 11.1 | |
| P719 | 17.6 | | 516.4 | |

TABLE 8-continued

Biological Activity, Representative Compounds of Formula (I)

| ID No. | FXIa (KIN) IC$_{50}$ (nM) | FXIa (EP) IC$_{50}$ (nM) | Kallikrein (KIN) IC$_{50}$ (nM) | Kallikrein (EP) IC$_{50}$ (nM) |
|---|---|---|---|---|
| P720 | 1.28 μM | | >10 μM | |
| P721 | 685 | | >10 μM | |
| P722 | 0.7 | | 39.6 | |
| P723 | 36.3 | | 1.84 μM | |
| P724 | 0.2 | | 8.5 | |
| P725 | 144.1 | | 6.27 μM | |
| P726 | 0.3 | | 7.7 | |
| P727 | 172.4 | | 7.32 μM | |
| P728 | 192.4 | | >10 μM | |
| P729 | 2.1 | | 58.3 | |
| P730 | 576.1 | | 5.29 μM | |
| P731 | 0.8 | | 64.9 | |
| P732 | 1.1 | | 40 | |
| P733 | 98.7 | | 1.34 μM | |
| P734 | 0.4 | | 6.4 | |
| P735 | 78.9 | | 1.6 μM | |
| P736 | 1.7 | | 8.4 | |
| P737 | 289.3 | | 817.5 | |
| P738 | ~790 | | 1.47 μM | |
| P739 | 5 | | 22.8 | |
| P740 | ~352 | | 626.3 | |
| P741 | 5.8 | | 22.1 | |
| P742 | 4.5 | | 19.1 | |
| P743 | >100 | | >100 | |
| P744 | 1 | | 48.9 | |
| P745 | 481.3 | | >10 μM | |
| P746 | 328.7 | | 588.3 | |
| P747 | 0.6 | | 26.2 | |
| P748 | 1.8 | | 6.4 | |
| P749 | 0.5 | | 19.8 | |
| P750 | 1.4 | | 36.2 | |
| P751 | ~200 | | >10 μM | |
| P752 | 497.7 | | >10 μM | |
| P753 | 9.7 | | 54.3 | |
| P754 | 0.8 | | 74.3 | |
| P755 | >100 | | >20 μM | |
| P756 | >100 | | >20 μM | |
| P757 | 0.5 | | 31.9 | |
| P758 | >100 | | >20 μM | |
| P759 | >100 | | >20 μM | |
| P760 | 4 | | 454.4 | |
| P761 | 0.5 | | 41.6 | |
| P762 | 6.2 | | 249.3 | |
| P763 | >200 | | >20 μM | |
| P764 | 1.1 | | >100 | |
| P765 | >100 | | >100 | |
| P766 | >100 | | >100 | |
| P767 | 2 | | >100 | |
| P768 | 0.6 | | 70.5 | |
| P769 | >100 | | >100 | |
| P770 | >94 | | >20 μM | |
| P771 | 0.7 | | 16.2 | |
| P772 | 2.2 | | 42.3 | |
| P773 | >94 | | 4214.1 | |
| P774 | NT | NT | NT | NT |
| P775 | >200 | | 354.4 | |
| P776 | 0.6 | | 3.2 | |
| P777 | 0.9 | | 6.5 | |
| P778 | >200 | | 3.44 μM | |
| P779 | >200 | | 10.8 μM | |
| P780 | 0.8 | | 17.7 | |
| P781 | 17.4 | | 203.1 | |
| P782 | >200 | | >20 μM | |
| P783 | 1.9 | | 18.9 | |
| P784 | >200 | | >2 μM | |
| P785 | 4.8 | | 32.9 | |
| P786 | >200 | | >2 μM | |
| P787 | >200 | | >2 μM | |
| P788 | 0.4 | | 17.4 | |
| P789 | >200 | | >2 μM | |
| P790 | 0.4 | | 35.8 | |
| P791 | >200 | | >2 μM | |
| P792 | 0.6 | | 76.2 | |
| P793 | >200 | | >2 μM | |
| P794 | 0.6 | | 55.8 | |
| P795 | 0.7 | | 32.6 | |
| P796 | >200 | | >2 μM | |
| P797 | 0.2 | | 23.8 | |
| P798 | >200 | | >2 μM | |
| P799 | >100 | | >1 μM | |
| P800 | 0.8 | | 62.7 | |
| P801 | 1.9 | | 84.1 | |
| P802 | >100 | | >1 μM | |
| P803 | 3.1 | | ~93 | |
| P804 | >100 | | >1 μM | |
| P805 | ~2 | | 255.6 | |
| P806 | >100 | | >1 μM | |
| P807 | >100 | | >1 μM | |
| P808 | NT | NT | NT | NT |
| P809 | >100 | | >1 μM | |
| P810 | 13.9 | | ~383 | |
| P811 | >100 | | >1 μM | |
| P812 | >100 | | >1 μM | |
| P813 | >100 | | >1 μM | |
| P814 | >100 | | >1 μM | |
| P815 | >100 | | >1 μM | |
| P816 | 0.7 | | 86.3 | |
| P817 | 0.5 | | 23.5 | |
| P818 | >100 | | >1 μM | |
| P819 | >100 | | >1 μM | |
| P820 | 0.8 | | 68.8 | |
| P821 | 2 | | 214.3 | |
| P822 | >100 | | >1 μM | |
| P823 | 20.7 | | 565.6 | |
| P824 | >100 | | >1 μM | |
| P825 | 51 | | 587.9 | |
| P826 | 5.1 | | 303.3 | |
| P827 | >100 | | >1 μM | |
| P828 | >100 | | >1 μM | |
| P829 | >100 | | >1 μM | |
| P830 | 6.9 | | 359.5 | |
| P831 | >100 | | >1 μM | |
| P832 | 21.9 | | >1 μM | |
| P833 | 2.6 | | 62.7 | |
| P834 | 0.7 | | 68 | |
| P835 | >100 | | >1 μM | |
| P836 | >100 | | >1 μM | |
| P837 | 0.7 | | 48.3 | |
| P838 | 0.7 | | 30.7 | |
| P839 | >100 | | >1 μM | |
| P840 | 5.3 | | ~423 | |
| P841 | >100 | | >1 μM | |
| P842 | 24.2 | | 346 | |
| P843 | 7 | | ~71 | |
| P844 | 3 | | 31.3 | |
| P845 | >100 | | >1 μM | |
| P846 | 28.7 | | 238.5 | |
| P847 | >100 | | >1 μM | |
| P848 | 2.7 | | 184.6 | |
| P849 | 75.7 | | 417.3 | |
| P850 | 0.2 | | 1.4 | |
| P851 | >100 | | >1 μM | |
| P852 | 0.2 | | 2.2 | |
| P853 | ~5.1 | | 276.5 | |
| P854 | 48.6 | | >1 μM | |
| P855 | 0.2 | | 3.7 | |
| P856 | ~24 | | >1 μM | |
| P857 | >100 | | >1 μM | |
| P858 | 0.3 | | 11.6 | |
| P859 | 4 | | 28.7 | |
| P860 | 0.9 | | 10.2 | |
| P861 | >100 | | >1 μM | |
| P862 | 1.9 | | 147.9 | |
| P863 | >100 | | >1 μM | |
| P864 | 9.2 | | 549.2 | |
| P865 | >100 | | | |
| P866 | 1.7 | | | |
| P867 | >100 | | | |

TABLE 8-continued

Biological Activity, Representative Compounds of Formula (I)

| ID No. | FXIa (KIN) IC$_{50}$ (nM) | FXIa (EP) IC$_{50}$ (nM) | Kallikrein (KIN) IC$_{50}$ (nM) | Kallikrein (EP) IC$_{50}$ (nM) |
|---|---|---|---|---|
| P868 | 1.5 | | | |
| P869 | 1.1 | | | |
| P870 | 80.6 | | | |
| P871 | 0.3 | | | |
| P872 | 1.0 | | | |
| P873 | 1.0 | | | |
| P874 | 2.0 | | 41.4 | |
| P875 | 0.4 | | 2.7 | |
| P876 | >100 | | >1 μM | |
| P877 | >100 | | 219.9 | |
| P878 | 2.8 | | 2.7 | |
| P879 | 9.9 | | | |
| P880 | >100 | | >1 μM | |
| P881 | 0.1 | | 7.3 | |
| P882 | >100 | | >1 μM | |
| P883 | 15.5 | | 102.8 | |
| P884 | 25.8 | | 61.3 | |
| P885 | 5.8 | | 31 | |
| P886 | >100 | | >1 μM | |
| P887 | 0.1 | | 5.8 | |
| P888 | >100 | | >1 μM | |
| P889 | 11.3 | | 77.8 | |
| P890 | 0.3 | | 104.7 | |
| P891 | >100 | | 536 | |
| P892 | 0.4 | | 2.9 | |
| P893 | 6.9 | | 20.5 | |
| P894 | 0.4 | | 2.5 | |
| P895 | 79.2 | | 701.9 | |
| P896 | 0.1 | | 0.2 | |
| P897 | >100 | | >1 μM | |
| P898 | 0.1 | | 2.5 | |
| P899 | >100 | | >1 μM | |
| P900 | 0.1 | | 2.2 | |
| P901 | 5.3 | | 286.9 | |
| P902 | 15.1 | | 87.1 | |
| P903 | 0.3 | | 11.5 | |
| P904 | 11.9 | | 123 | |
| P905 | >100 | | 889 | |
| P906 | 0.5 | | 6.5 | |
| P907 | 32.2 | | 70.4 | |
| P908 | 0.1 | | 0.3 | |
| P909 | 0.3 | | 5.5 | |
| P910 | 19.2 | | 30.7 | |
| P911 | 0.1 | | 0.2 | |
| P912 | 0.2 | | 11.8 | |
| P913 | 1.4 | | 7.2 | |
| P914 | >100 | | >1 μM | |
| P915 | 9.8 | | 20.2 | |
| P916 | >100 | | >1 μM | |
| P917 | 0.4 | | 3.9 | |
| P918 | 1.4 | | 29.5 | |
| P919 | >100 | | >1 μM | |
| P920 | NT | NT | NT | NT |
| P921 | >100 | | >1 μM | |
| P922 | 6.8 | | 54.9 | |
| P923 | 3.2 | | 38.5 | |
| P924 | >100 | | >1 μM | |
| P925 | 1.2 | | 187.2 | |
| P926 | 12.5 | | 19.2 | |
| P927 | 2.7 | | 7.6 | |
| P928 | 0.2 | | 0.9 | |
| P929 | 0.8 | | 5.8 | |
| P930 | 25.8 | | >1 μM | |
| P931 | 0.2 | | 2.5 | |
| P932 | 26.5 | | 27 | |
| P933 | 0.1 | | 0.4 | |
| P934 | 6.5 | | 326.3 | |
| P935 | 6.5 | | 486.6 | |
| P936 | >100 | | 397.2 | |
| P937 | 0.4 | | 2.7 | |
| P938 | 0.3 | | 6.9 | |
| P939 | >100 | | >1 μM | |
| P940 | 1.1 | | 14.2 | |
| P941 | 0.3 | | 12.2 | |
| P942 | 89.8 | | 249.3 | |
| P943 | 0.5 | | 6.2 | |
| P944 | >100 | | >1 μM | |
| P945 | 5.3 | | 324 | |
| P946 | >100 | | 833.9 | |
| P947 | 1.8 | | 14.5 | |
| P948 | 1.2 | | 11.8 | |
| P949 | 3.6 | | 21.6 | |
| P950 | >100 | | >1 μM | |
| P951 | 86.8 | | 316.2 | |
| P952 | 0.8 | | 2.3 | |
| P953 | 3.3 | | 13.4 | |
| P954 | >100 | | 788.3 | |
| P955 | 50.2 | | 613.1 | |
| P956 | >100 | | >1 μM | |
| P957 | 8 | | 221.9 | |
| P958 | 1.2 | | 13.1 | |
| P959 | >100 | | >1 μM | |
| P960 | 2 | | 52.9 | |
| P961 | 4.6 | | 85.6 | |
| P962 | >100 | | >1 μM | |
| P963 | 471.3 | | 5.9 μM | |
| Q1 | | 621.4 | | 355.1 |
| Q2 | | 41 | | 674.4 |
| Q3 | | ~37 μM | | >50 μM |
| Q4 | 3.9 | | 265.5 | |
| Q5 | 154.3 | | >10 μM | |
| Q6 | 2.5 | | 10.4 | |
| Q7 | 331.5 | | >10 μM | |
| Q8 | 364.3 | | >10 μM | |
| Q9 | >10 μM | | >10 μM | |
| Q10 | 326.7 | | 374.7 | |
| Q11 | 4.2 μM | | 1.62 μM | |
| Q12 | ~4.4 μM | | >10 μM | |
| Q13 | 28.4 | | 97.1 | |
| Q14 | 2.9 | | 3.9 | |
| Q15 | 259.7 | | 381.5 | |
| Q16 | 89.3 | | 304.9 | |
| Q17 | ~8.8 μM | | 7818.1 | |
| Q18 | 15.4 | | 5.1 | |
| Q19 | 58.8 | | 48.4 | |
| Q20 | 9.26 μM | | 4.12 μM | |
| Q21 | 233.1 | | 1.41 μM | |
| Q22 | 3.23 μM | | 805.7 | |
| Q23 | 203.8 | | 80.4 | |
| Q24 | 21.5 | | 578.1 | |
| Q25 | 73.2 | | 17.8 | |
| Q26 | 1.05 μM | | 419.9 | |
| Q27 | 57.7 | | 4.7 | |
| Q28 | 356.4 | | 94.6 | |
| Q29 | 283.3 | | 258.9 | |
| Q30 | 41.3 | | 88.1 | |
| Q31 | 1.60 μM | | 1.85 μM | |
| Q32 | 2.1 | | 4.4 | |
| Q33 | >10 μM | | >10 μM | |
| Q34 | 17.1 | | 50.5 | |
| Q35 | 1.0 | | 4.0 | |
| Q36 | 2.45 μM | | 4.95 μM | |
| Q37 | 68.1 | | 99.1 | |
| Q38 | 629.5 | | 2.69 μM | |
| Q39 | 26.8 | | 2.38 μM | |
| Q40 | 1.21 μM | | 1.06 μM | |
| Q41 | 895.4 | | 5.05 μM | |
| Q42 | 10.4 | | 44.3 | |
| Q43 | 7.85 μM | | >10 μM | |
| Q44 | 74.6 | | 80.7 | |
| Q45 | >100 | | 230.8 | |
| Q46 | >100 | | >1 μM | |
| Q47 | 23.7 | | 57.6 | |
| Q48 | >100 | | >1 μM | |
| Q49 | 0.8 | | 2.3 | |
| Q50 | >100 | | >1 μM | |
| Q51 | 24.2 | | 14.5 | |
| Q52 | >100 | | >1 μM | |

TABLE 8-continued

Biological Activity, Representative Compounds of Formula (I)

| ID No. | FXIa (KIN) IC$_{50}$ (nM) | FXIa (EP) IC$_{50}$ (nM) | Kallikrein (KIN) IC$_{50}$ (nM) | Kallikrein (EP) IC$_{50}$ (nM) |
|---|---|---|---|---|
| Q53 | >100 | | 222.4 | |
| Q54 | >100 | | 753.2 | |
| Q55 | >100 | | >1 µM | |
| Q56 | 52.3 | | 58.9 | |
| Q57 | >100 | | >1 µM | |
| Q58 | 15.9 | | 517.1 | |
| Q59 | >100 | | 25.2 | |
| Q60 | >100 | | >1 µM | |
| Q61 | >100 | | 280.8 | |
| Q62 | 63.6 | | 80.9 | |
| Q63 | >100 | | >1 µM | |
| Q64 | 1.0 | | 4.7 | |
| Q65 | >100 | | >1 µM | |
| Q66 | >100 | | 476.9 | |
| Q67 | 13.1 | | 2.9 | |
| Q68 | >100 | | 111.2 | |
| Q69 | 0.7 | | 0.8 | |
| Q70 | >28 | | >274 | |
| Q71 | 2.3 | | 4.9 | |
| Q72 | >100 | | 544.5 | |
| Q73 | >100 | | >1 µM | |
| Q74 | 1.7 | | 11 | |
| Q75 | 11.1 | | 10 | |
| Q76 | 2.2 | | 36 | |
| Q77 | 6.4 | | 9.8 | |
| Q78 | >100 | | 510 | |

Formulation Example 1

Solid, Oral Dosage Form—Prophetic Example

As a specific embodiment of an oral composition, 100 mg of any of Compound ID No. P636, P722, P757, P892 or P984, prepared as described in herein, is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

Throughout this application, various publications are cited. The disclosure of these publications is hereby incorporated by reference into this application to describe more fully the state of the art to which this invention pertains.

What is claimed:
1. A compound of formula (I)

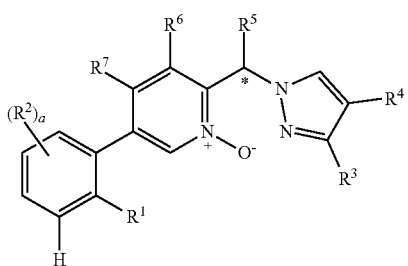

(I)

wherein
$R^1$ is selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, nitro, —NR$^A$R$^B$, —C(O)—$C_{1-4}$alkyl, $C_{3-6}$cycloalkyl, phenyl and 5 to 6 membered heterocyclyl;
wherein the $C_{3-6}$cycloalkyl, phenyl or 5 to 6 membered heterocyclyl is optionally substituted with one or more substituents independently selected from the group consisting of halogen, hydroxy, cyano, $C_{1-4}$alkyl, fluorinated $C_{1-4}$alkyl, $C_{1-4}$alkoxy, fluorinated $C_{1-4}$alkoxy, —C(O)OH, —C(O)O—($C_{1-4}$alkyl), —NR$^A$R$^B$, —($C_{1-4}$ alkyl)-NR$^A$R$^B$, $C_{3-7}$cycloalkyl and 5 to 6 membered heterocyclyl; and
wherein $R^A$ and $R^B$ are each independently selected from the group consisting of hydrogen and $C_{1-4}$alkyl;
a is an integer from 0 to 3;
each $R^2$ is independently selected from the group consisting of chloro, fluoro, methyl and methoxy;
$R^3$ is selected from the group consisting of hydrogen, fluoro, chloro and methyl;
$R^4$ is 5 membered heterocyclyl; wherein the 5 membered heterocyclyl contains at least one heteroatom selected from the group consisting of O, N and S; optionally contains 1 to 3 additional heteroatoms independently selected from the group consisting of O, N and S; wherein the 5 membered heterocyclyl is saturated, partially unsaturated, or aromatic;
and wherein the 5 membered heterocyclyl is optionally substituted with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, $C_{3-7}$cycloalkyl, —C(O)OH, —C(O)—O—$C_{1-4}$alkyl, —$C_{1-2}$alkyl-C(O)—O—$C_{1-4}$alkyl, cyano, —NR$^E$R$^F$, —C(O)—NR$^E$R$^F$, pyrrolidin-2-yl-5-one, pyrrolidin-3-yl-2,5-dione, pyrrol-3-yl-2,5-dione, 1,2,3,4-tetrazol-1-yl, 1,2,3,4-tetrazol-5-yl, 1,2,4-oxadiazol-3-yl-5-one, oxazolidin-5-yl-2,4-dione, 1H-imidazol-5-yl-2,5-dione, thiazol-5-yl-2,4-dione, isoxazol-5-yl-3-ol, isothiazol-5-yl-3-ol, 3-chloro-4-hydroxy-phenyl, —C(O)—NH—CN, —C(O)—NH—SO$_2$—CH$_3$, —SO$_2$—NH—CF$_3$, and —SO$_2$—NH—CF$_2$CF$_3$;
wherein R$^E$ is selected from the group consisting of hydrogen, $C_{1-4}$alkyl, cyclopropyl, 3-hydroxy-cycloprop-1-yl, —C(O)—$C_{1-4}$alkyl, —C(O)-cyclopropyl, —C(O)—O—$C_{1-4}$alkyl and —SO$_2$—$C_{1-4}$alkyl; and
R$^F$ is selected from the group consisting of hydrogen and $C_{1-4}$alkyl;
$R^5$ is selected from the group consisting of
(a) $C_{1-4}$alkyl; wherein the $C_{1-4}$alkyl is optionally substituted with one or more halogen, and further optionally substituted with a substituent selected from the group consisting of hydroxy, $C_{1-4}$alkoxy, fluorinated $C_{1-4}$alkoxy, —C(O)OH, —C(O)—O—($C_{1-4}$alkyl), —C(O)—O-(fluorinated $C_{1-4}$alkyl), —C(O)-(fluorinated $C_{1-4}$alkyl), and —C(O)—NR$^L$R$^M$; wherein R$^L$ and R$^M$ are each independently selected from the group consisting of hydrogen and $C_{1-2}$alkyl;
(b) —CH$_2$—$C_{3-8}$cycloalkyl or —CH$_2$-adamant-1-yl; wherein the $C_{3-8}$cycloalkyl is optionally substituted with one or more halogen or $C_{1-4}$alkyl; and further optionally substituted with a substituent selected from the group consisting of —C(O)OH, —C(O)—O—$C_{1-4}$ alkyl, —C(O)-(5 to 6 membered saturated heterocyclyl), —C(O)-(isoindolin-2-yl), —C(O)-(azaspiro[2.4] heptan-5-yl), —C(O)-(carboxy substituted azaspiro

[2.4]heptan-5-yl), —C(O)—(NR$^P$R$^Q$ substituted azaspiro[2.4]heptan-5-yl), phenyl, 1,1'-biphen-4-yl and —C(O)—NR$^P$R$^Q$;

wherein the —C(O)-(5 to 6 membered saturated heterocyclyl) substituent on the —CH$_2$—C$_{3-8}$cycloalkyl is further optionally substituted on the (5 to 6 membered heterocyclyl) with one or more substituents independently selected from the group consisting of halogen, hydroxy, C$_{1-4}$alkyl, fluorinated C$_{1-4}$alkyl, C$_{1-4}$alkoxy, fluorinated C$_{1-4}$alkoxy, cyano, —C(O)OH, —C(O)—O—C$_{1-4}$alkyl, —NR$^P$R$^Q$, phenyl and C$_{3-8}$cycloalkyl;

wherein the phenyl substituent on the —CH$_2$—C$_{3-8}$cycloalkyl is further optionally substituted with one or more substituents independently selected form the group consisting of halogen, hydroxy, C$_{1-4}$alkyl, fluorinated C$_{1-4}$alkyl, C$_{1-4}$alkoxy, fluorinated C$_{1-4}$alkoxy, cyano, —NR$^P$R$^Q$, and C$_{3-8}$cycloalkyl;

and wherein R$^P$ and R$^Q$ are each independently selected from the group consisting of hydrogen and C$_{1-4}$alkyl;

(c) -L$^1$-(5 to 6 membered saturated heterocyclyl); wherein L$^1$ is selected from the group consisting of —CH$_2$— and —CH$_2$—C(O)—; wherein, when L$^1$ is —CH$_2$—C(O)—, then the (5 to 6 membered saturated heterocyclyl) is bound to the —C(O)— portion of L$^1$; - and wherein the (5 to 6 membered saturated heterocyclyl) is optionally substituted with one to two oxo group;

(d) —C$_{1-2}$alkyl-phenyl; wherein the phenyl is optionally substituted with one or more substituents independently selected from the group consisting of halogen, hydroxy, C$_{1-4}$alkyl, fluorinated C$_{1-4}$alkyl, C$_{1-4}$alkoxy, fluorinated C$_{1-4}$alkoxy, —OCH$_2$—C(O)—NR$^S$R$^T$, phenyl and phenoxy; and wherein R$^S$ and R$^T$ are each independently selected from the group consisting of hydrogen and C$_{1-4}$alkyl;

(e) 1,2,3-triazol-4-yl, 1,2,5-triazol-3-yl, —CH$_2$-1,2,3-triazol-4-yl and —CH$_2$-1,2,5-triazol-3-yl;

wherein the 1,2,3-triazol-4-yl or 1,2,5-triazoly-3-yl, whether alone or as part of the substituent group is optionally substituted with a substituent selected from the group consisting of C$_{1-4}$alkyl, fluorinated C$_{1-4}$alkyl, phenyl and piperidinyl; wherein the piperidinyl is optionally substituted with —C(O)—C$_{1-4}$alkyl;

(f) —CH$_2$-(5 to 6 membered or 9 to 10 membered heterocyclyl); wherein the (5 to 6 membered or 9 to 10 membered heterocyclyl) is other than triazolyl;

wherein the (5 to 6 membered or 9 to 10 membered heterocyclyl) is optionally substituted with one or more substituents independently selected from the group consisting of halogen, hydroxy, oxo, C$_{1-4}$alkyl, fluorinated C$_{1-4}$alkyl, C$_{1-4}$alkoxy, fluorinated C$_{1-4}$alkoxy, cyano, —C(O)OH, —C(O)—O—C$_{1-4}$alkyl, —C$_{1-2}$alkyl-O—C$_{1-4}$alkyl, —C$_{1-2}$alkyl-O-(fluorinated C$_{1-4}$alkyl), —C(O)—NR$^V$R$^W$, —C$_{1-2}$alkyl-C(O)—NR$^V$R$^W$, -(5 to 6 membered saturated heterocyclyl), —C(O)-(5 to 6 membered saturated heterocyclyl), —C(O)-(carboxy substituted 5 to 6 membered saturated heterocyclyl), —C$_{1-2}$alkyl-C(O)-(5 to 6 membered saturated heterocyclyl), phenyl and pyridinyl;

wherein the pyridinyl substituent on the —CH$_2$-(5 to 6 membered or 9 to 10 membered heterocyclyl) is further optionally substituted with one or more substituents independently selected from the group consisting of halogen and fluorinated C$_{1-4}$alkyl;

and wherein R$^V$ and R$^W$ are each independently selected from the group consisting of hydrogen and C$_{1-4}$alkyl;

and (g) —CH$_2$—NR$^8$R$^9$; wherein R$^8$ is selected from the group consisting of hydrogen and C$_{1-4}$alkyl; R$^9$ is selected from the group consisting of C$_{1-4}$alkyl, fluorinated C$_{1-4}$alkyl, C$_{1-4}$alkoxy, fluorinated C$_{1-4}$alkoxy, —C(O)—C$_{1-4}$alkyl, —C(O)—C$_{1-2}$alkyl-O—C$_{1-4}$alkyl, —C(O)-phenyl, —C(O)—C$_{1-2}$alkyl-phenyl, —C(O)—O—C$_{1-4}$alkyl, —C(O)—O-phenyl, —C(O)—O—C$_{1-2}$alkyl-phenyl, —C(O)—C$_{3-7}$cycloalkyl, —C(O)-(1-methyl-cycloprop-1-yl), —C(O)-(5 to 6 membered saturated heterocyclyl), —C(O)—C$_{1-2}$alkyl-C(O)-(5 to 6 membered saturated heterocyclyl), —O—C$_{1-2}$alkyl-C(O)-(5 to 6 membered saturated heterocyclyl), —C(O)-(1-methyl-pyridinyl-one) and —C(O)—NR$^X$R$^Y$; and wherein R$^X$ and R$^Y$ are each independently selected from the group consisting of hydrogen and C$_{1-4}$alkyl;

R$^6$ and R$^7$ are each independently selected from the group consisting of hydrogen, halogen, C$_{1-4}$alkyl and C$_{1-4}$alkoxy;

provided that at least one of R$^6$ or R$^7$ is hydrogen;

or a stereoisomer, isotopologue, isotopomer, or pharmaceutically acceptable salt or solvate thereof.

2. The compound of claim 1, wherein

R$^1$ is selected from the group consisting of halogen, C$_{1-4}$alkyl, fluorinated C$_{1-4}$alkyl, C$_{1-4}$alkoxy, fluorinated C$_{1-4}$alkoxy, cyano, —NR$^A$R$^B$, —C(O)—C$_{1-4}$alkyl, and 5 to 6 membered heterocyclyl;

wherein the 5 to 6 membered heterocyclyl is optionally substituted with one or more substituents independently selected from the group consisting of halogen, cyano, C$_{1-4}$alkyl, fluorinated C$_{1-4}$alkyl, C$_{1-4}$alkoxy, fluorinated C$_{1-4}$alkoxy, and C$_{3-7}$cycloalkyl;

and wherein R$^A$ and R$^B$ are each independently selected from the group consisting of hydrogen and C$_{1-4}$alkyl;

a is an integer from 1 to 2;

each R$^2$ is independently selected from the group consisting of chloro and fluoro;

R$^3$ is selected from the group consisting of hydrogen, and methyl;

R$^4$ is 5 membered heterocyclyl; wherein the 5 membered heterocyclyl contains at least one heteroatom selected from the group consisting of O, N and S; optionally contains 1 to 3 additional heteroatoms independently selected from the group consisting of O, N and S; wherein the 5 membered heterocyclyl is saturated, partially unsaturated, or aromatic;

wherein the 5 membered heterocyclyl is optionally substituted with one to two substituents independently selected from the group consisting of halogen, hydroxy, C$_{1-4}$alkyl, fluorinated C$_{1-4}$alkyl, C$_{1-4}$alkoxy, fluorinated C$_{1-4}$alkoxy, C$_{3-7}$cycloalkyl, —C(O)OH, —C(O)—O—C$_{1-4}$alkyl, —C$_{1-2}$alkyl-C(O)—O—C$_{1-4}$alkyl, cyano, —NR$^E$R$^F$ and —C(O)—NR$^E$R$^F$;

and wherein R$^E$ is selected from the group consisting of hydrogen, C$_{1-4}$alkyl, cyclopropyl, 3-hydroxy-cycloprop-1-yl, —C(O)—C$_{1-4}$alkyl, —C(O)-cyclopropyl, —C(O)—O—C$_{1-4}$alkyl and —SO$_2$—C$_{1-4}$alkyl; and R$^F$ is hydrogen and C$_{1-4}$alkyl;

R$^5$ is selected from the group consisting of (a) C$_{1-4}$alkyl; wherein the C$_{1-4}$alkyl is optionally substituted with one or more halogen, and further optionally substituted with a substituent selected from the group consisting of hydroxy, C$_{1-4}$alkoxy, fluorinated C$_{1-4}$alkoxy, —C(O)OH, —C(O)—O—(C$_{1-4}$alkyl), —C(O)—O-(fluorinated C$_{1-4}$alkyl), —C(O)-(fluorinated C$_{1-4}$alkyl), and —C(O)—NR$^L$R$^M$; wherein R$^L$ and R$^M$ are each independently selected from the group consisting of hydrogen and C$_{1-2}$alkyl;

(b) —CH$_2$—C$_{3-8}$cycloalkyl or —CH$_2$-adamant-1-yl; wherein the C$_{3-8}$cycloalkyl is optionally substituted with one to two halogen or C$_{1-4}$alkyl; and further optionally substituted with a substituent selected from the group consisting of —C(O)OH, —C(O)—O—C$_{1-4}$alkyl, —C(O)-(5 to 6 membered saturated heterocyclyl), —C(O)-(isoindolin-2-yl), —C(O)-(azaspiro[2.4]heptan-5-yl), —C(O)-(carboxy substituted azaspiro[2.4]heptan-5-yl), —C(O)—(NR$^P$R$^Q$ substituted azaspiro[2.4]heptan-5-yl), phenyl, 1,1'-biphen-4-yl and —C(O)—NR$^P$R$^Q$;

wherein the —C(O)-(5 to 6 membered saturated heterocyclyl) substituent on the —CH$_2$—C$_{3-8}$cycloalkyl is further optionally substituted on the (5 to 6 membered heterocyclyl) with one to two substituents independently selected from the group consisting of halogen, C$_{1-4}$alkyl, —C(O)OH, —C(O)—O—C$_{1-4}$alkyl, phenyl and C$_{3-8}$cycloalkyl;

wherein the phenyl substituent on the —CH$_2$—C$_{3-8}$cycloalkyl is further optionally substituted with C$_{1-4}$alkoxy;

and wherein R$^P$ and R$^Q$ are each independently selected from the group consisting of hydrogen and C$_{1-4}$alkyl;

(c) -L$^1$-(5 to 6 membered saturated heterocyclyl); wherein L$^1$ is selected from the group consisting of —CH$_2$— and —CH$_2$—C(O)—; wherein, when L$^1$ is —CH$_2$—C(O)—, then the (5 to 6 membered saturated heterocyclyl) is bound to the —C(O)— portion of L$^1$; and wherein the (5 to 6 membered saturated heterocyclyl) is optionally substituted with one to two oxo group;

(d) —C$_{1-2}$alkyl-phenyl; wherein the phenyl is optionally substituted with one to two substituents independently selected from the group consisting of halogen, hydroxy, C$_{1-4}$alkyl, fluorinated C$_{1-4}$alkyl, C$_{1-4}$alkoxy, fluorinated C$_{1-4}$alkoxy, —OCH$_2$—C(O)—NR$^S$R$^T$, phenyl and phenoxy; and wherein R$^S$ and R$^T$ are each independently selected from the group consisting of hydrogen and C$_{1-2}$alkyl;

(e) 1,2,3-triazol-4-yl, 1,2,5-triazol-3-yl, —CH$_2$-1,2,3-triazol-4-yl and —CH$_2$-1,2,5-triazol-3-yl;

wherein the 1,2,3-triazol-4-yl or 1,2,5-triazoly-3-yl, whether alone or as part of the substituent group is optionally substituted with a substituent selected from the group consisting of C$_{1-4}$alkyl, fluorinated C$_{1-4}$alkyl, phenyl and piperidinyl; wherein the piperidinyl is optionally substituted with —C(O)—C$_{1-4}$alkyl;

(f) —CH$_2$-(5 to 6 membered or 9 to 10 membered heterocyclyl); wherein the (5 to 6 membered or 9 to 10 membered heterocyclyl) is other than triazolyl;

wherein the (5 to 6 membered or 9 to 10 membered heterocyclyl) is optionally substituted with one to two substituents independently selected from the group consisting of halogen, hydroxy, oxo, C$_{1-4}$alkyl, fluorinated C$_{1-4}$alkyl, C$_{1-4}$alkoxy, fluorinated C$_{1-4}$alkoxy, cyano, —C(O)OH, —C(O)—O—C$_{1-4}$alkyl, —C$_{1-2}$alkyl-O—C$_{1-4}$alkyl, —C$_{1-2}$alkyl-O-(fluorinated C$_{1-4}$alkyl), —C(O)—NR$^V$R$^W$, —C$_{1-2}$alkyl-C(O)—NR$^V$R$^W$, -(5 to 6 membered saturated heterocyclyl), —C(O)-(5 to 6 membered saturated heterocyclyl), —C(O)-(carboxy substituted 5 to 6 membered saturated heterocyclyl), —C$_{1-2}$alkyl-C(O)-(5 to 6 membered saturated heterocyclyl), phenyl and pyridinyl;

wherein the pyridinyl substituent on the —CH$_2$-(5 to 6 membered or 9 to 10 membered heterocyclyl) is further optionally substituted with one to two substituents independently selected from the group consisting of halogen and fluorinated C$_{1-4}$alkyl;

and wherein R$^V$ and R$^W$ are each independently selected from the group consisting of hydrogen and C$_{1-4}$alkyl;

and (g) —CH$_2$—NR$^8$R$^9$; wherein R$^8$ is selected from the group consisting of hydrogen and C$_{1-2}$alkyl; R$^9$ is selected from the group consisting of C$_{1-4}$alkyl, fluorinated C$_{1-4}$alkyl, C$_{1-4}$alkoxy, fluorinated C$_{1-4}$alkoxy, —C(O)—C$_{1-4}$alkyl, —C(O)—C$_{1-2}$alkyl-O—C$_{1-4}$alkyl, —C(O)-phenyl, —C(O)—C$_{1-2}$alkyl-phenyl, —C(O)—O—C$_{1-4}$alkyl, —C(O)—O-phenyl, —C(O)—O—C$_{1-2}$alkyl-phenyl, —C(O)—C$_3$-7cycloalkyl, —C(O)-(1-methyl-cycloprop-1-yl), —C(O)-(5 to 6 membered saturated heterocyclyl), —C(O)—C$_{1-2}$alkyl-C(O)-(5 to 6 membered saturated heterocyclyl), —O—C$_{1-2}$alkyl-C(O)-(5 to 6 membered saturated heterocyclyl), —C(O)-(1-methyl-pyridinyl-one) and —C(O)—NR$^X$R$^Y$; and wherein R$^X$ and R$^Y$ are each independently selected from the group consisting of hydrogen and C$_{1-2}$alkyl;

R$^6$ and R$^7$ are each independently selected from the group consisting of hydrogen, halogen, C$_{1-4}$alkyl and C$_{1-4}$alkoxy;

provided that at least one of R$^6$ or R$^7$ is hydrogen;

or a stereoisomer, isotopologue, isotopomer, or pharmaceutically acceptable salt or solvate thereof.

3. The compound of claim 1, wherein

R$^1$ is selected from the group consisting of 5 to 6 membered heterocyclyl; wherein the 5 to 6 membered heterocyclyl is optionally substituted with one or more substituents independently selected from the group consisting of halogen, cyano, fluorinated C$_{1-4}$alkyl, fluorinated C$_{1-4}$alkoxy, and C$_{3-6}$cycloalkyl;

a is an integer from 1 to 2;

each R$^2$ is independently selected from the group consisting of chloro and fluoro;

R$^3$ is hydrogen;

R$^4$ is 5 membered heterocyclyl; wherein the 5 membered heterocyclyl contains at least one heteroatom selected from the group consisting of O, N and S; optionally contains 1 to 3 additional heteroatoms independently selected from the group consisting of O, N and S; wherein the 5 membered heterocyclyl is saturated, partially unsaturated, or aromatic;

and wherein the 5 membered heterocyclyl is optionally substituted with one to two substituents independently selected from the group consisting of halogen, hydroxy, C$_{1-4}$alkyl, fluorinated C$_{1-4}$alkyl, —C$_{1-2}$alkyl-C(O)—O—C$_{1-4}$alkyl, C$_{3-6}$cycloalkyl, cyano, —NR$^E$R$^F$, and —C(O)—NR$^E$R$^F$; wherein R$^E$ is selected from the group consisting of hydrogen and —C(O)-cyclopropyl; and R$^F$ is selected from the group consisting of hydrogen and C$_{1-4}$alkyl;

R$^5$ is selected from the group consisting of (a) C$_{1-4}$alkyl; wherein the C$_{1-4}$alkyl is optionally substituted with one or more halogen, and further optionally substituted with a substituent selected from the group consisting of hydroxy, C$_{1-4}$alkoxy and fluorinated C$_{1-4}$alkoxy;

(b) —CH$_2$—C$_{3-6}$cycloalkyl; wherein the C$_{3-6}$cycloalkyl is optionally substituted with one or more halogen, and further optionally substituted optionally substituted with C$_{1-4}$alkyl;

(c) -L$^1$-(5 to 6 membered saturated heterocyclyl); wherein L$^1$ is —CH$_2$—;

(d) —C$_{1-2}$alkyl-phenyl; wherein the phenyl is optionally substituted with one to two substituents independently selected from the group consisting of halogen and hydroxy;

(e) 1,2,5-triazoly-3-yl; wherein the 1,2,5-triazoly-3-yl, is optionally substituted with a substituent selected from the group consisting of $C_{1-4}$alkyl, and phenyl;

and (f) —$CH_2$-(5 to 6 membered heterocyclyl); wherein the (5 to 6 membered heterocyclyl) is other than triazolyl; wherein the (5 to 6 membered heterocyclyl) is optionally substituted with a substituent selected from the group consisting of halogen, fluorinated $C_{1-4}$alkyl, and fluorinated $C_{1-4}$alkoxy;

$R^6$ is hydrogen;

$R^7$ is selected from the group consisting of hydrogen, halogen and $C_{1-2}$alkoxy;

or a stereoisomer, isotopologue, isotopomer, or pharmaceutically acceptable salt or solvate thereof.

4. The compound of claim 1, wherein $R^1$ is selected from the group consisting of 1,2,3-triazol-1-yl, 4-bromo-1,2,3-triazol-1-yl, 4-chloro-1,2,3-triazol-1-yl, 4-(trifluoro-methyl)-1,2,3-triazol-1-yl, 4-(difluoro-methoxy)-1,2,3-triazol-1-yl, 5-(difluoro-methoxy)-1,2,3-triazol-1-yl, 4-cyano-1,2,3-triazol-1-yl, 4-cyclopropyl-1,2,3-triazol-1-yl, oxazol-5-yl and 1,2,3,4-tetrazol-1-yl;

a is an integer from 1 to 2;

each $R^2$ is independently selected from the group consisting of 5-chloro and 6-fluoro;

$R^3$ is hydrogen;

$R^4$ is selected from the group consisting of 1-(difluoro-methyl)-pyrazol-3-yl, 1-(difluoro-methyl)-4-chloro-pyrazol-3-yl, 1-(difluoro-methyl)-4-cyano-pyrazol-3-yl, 3-chloro-pyrazol-4-yl, 1-methyl-pyrazol-4-yl, 3-methyl-pyrazol-4-yl, 1-methyl-3-chloro-pyrazol-4-yl, 1-(trifluoro-methyl)-pyrazol-4-yl, 1-(difluoro-methyl)-3-hydroxy-pyrazol-4-yl, 1-(methoxy-carbonyl-methyl)-pyrazol-4-yl, pyrazol-5-yl, 1-methyl-4-fluoro-pyrazol-5-yl, 1-methyl-pyrazol-5-yl, 1-methyl-4-cyano-pyrazol-5-yl, 1-(difluoro-methyl)-pyrazol-5-yl, 1-methyl-3-(trifluoro-methyl)-pyrazol-5-yl, 1-methyl-4-chloro-pyrazol-5-yl, 1-(methyl-$d_3$)-pyrazol-5-yl, 1-(difluoro-methyl)-4-chloro-pyrazol-5-yl, 1-(difluoro-methyl)-4-fluoro-pyrazol-5-yl, 1-(difluoro-methyl)-4-cyano-pyrazol-5-yl, 1-methyl-4-hydroxy-pyrazol-5-yl, 1-(difluoro-methyl)-pyrazol-5-yl), 1-(methyl-$d_3$)-4-(cyclopropyl-carbonyl-amino)-pyrazol-5-yl, thiazol-5-yl, 4-methyl-thiazol-5-yl, 4-cyclopropyl-thiazol-5-yl, 2-(difluoro-methyl)-thiazol-5-yl, 4-(trifluoro-methyl)-thiazol-5-yl, 4-chloro-thiazol-5-yl, 2-amino-thaizol-5-yl, 2-amino-4-chloro-thiazol-5-yl, 2-(trifluoro-methyl)-4-methyl-thiazol-5-yl, isothiazol-4-yl, 1,2,4-thiadizol-5-yl, 2-(trifluoro-methyl)-1,3,4-thiadiazol-5-yl, imidazol-1-yl, 2-methyl-imidazol-1-yl, 1-methyl-imidazol-5-yl, 1-(difluoro-methyl)-imidazol-5-yl, 1-(difluoro-methyl)-4-chloro-imidazol-5-yl, 1-methyl-4-chloro-imidazol-5-yl, oxazol-5-yl, 3-methyl-isoxazol-4-yl, 1,3,4-oxadiazol-5-yl, 3-methyl-1,2,4-oxadiazol-5-yl, 1-methyl-1,2,3-triazol-4-yl, 1-(difluoro-methyl)-1,2,3-triazol-4-yl, 1-(difluoro-methyl)-5-chloro-1,2,3-triazol-4-yl, 1-methyl-5-fluoro-1,2,3-triazol-4-yl, 1-methyl-1,2,3-triazol-5-yl, 1-methyl-4-chloro-1,2,3-triazol-5-yl, 1-cyclopropyl-1,2,3-triazol-5-yl, 1-(difluoro-methyl)-1,2,3-triazol-5-yl, 1-(difluoro-methyl)-4-chloro-1,2,3-triazol-5-yl, 1-methyl-4-fluoro-1,2,3-triazol-5-yl, 1-(difluoro-methyl)-4-fluoro-1,2,3-triazol-5-yl, 1-isopropyl-1,2,3-triazol-5-yl, 3-methyl-1,2,4-triazol-1-yl, 1-(difluoro-methyl)-1,2,4-triazol-5-yl, 1-methyl-1,2,4-triazol-5-yl, 1-methyl-1,2,5-triazol-3-yl, 1-(difluoro-methyl)-4-chloro-1,2,5-triazol-3-yl, 1-(difluoro-methyl)-1,2,5-triazol-3-yl, 1-(difluoro-methyl)-4-fluoro-1,2,5-triazol-3-yl, 1-(difluoro-methyl)-1,2,5-triazol-4-yl, 1,3,4-triazol-1-yl, 2-methyl-1,3,4-triazol-1-yl, 1-(difluoro-methyl)-1,3,4-triazol-2-yl, 1-methyl-1,2,3,4-tetrazol-5-yl, 5-(amino-carbonyl)-thien-2-yl, 3-methyl-5-(amino-carbonyl)-thien-2-yl, and 4-fluoro-5-(amino-carbonyl)-thien-3-yl;

$R^5$ is selected from the group consisting of (a) R-ethyl, S-ethyl, S-(2-hydroxy-ethyl-), R-(2-hydroxy-ethyl-), S-(2-methoxy-ethyl-), R-(2-methoxy-ethyl-), 2-(difluoro-methoxy)-ethyl-, S-(2-(difluoro-methoxy)-ethyl-), R-(2-(difluoro-methoxy)-ethyl-), R-(2-trifluoro-methoxy-ethyl-), S-(2-t-butoxy-ethyl-), R-(2-t-butoxy-ethyl-), 2-(methyl-$d_3$)-ethyl-2, 2-$d_2$-, R-(2-hydroxy-ethyl-2,2-$d_2$-), S-(2-hydroxy-ethyl-2,2-$d_2$-), S-(2-(methoxy-$d_3$)-ethyl-2,2-$d_2$-), R-(2-(methoxy-$d_3$)-ethyl-2,2-$d_2$-), S-(2-(difluoro-methoxy)-ethyl-2,2-$d_2$-), R-(2-(difluoro-methoxy)-ethyl-2,2-$d_2$-), S-(2-methoxy-2-methyl-n-propyl-), R-(2-methoxy-2-methyl-n-propyl-), S-(2-hydroxy-2-methyl-n-propyl-), R-(2-hydroxy-2-methyl-n-propyl-), R-(3,3,3-trifluoro-n-propyl), S-(3,3,3-trifluoro-n-propyl);

(b) cyclopropyl-methyl-, S-(cyclopropyl-methyl-), R-(cyclopropyl-methyl-), R-(2,2-difluoro-cyclopropyl-methyl-), S-(2,2-difluoro-cyclopropyl-methyl-), R-(cyclobutyl-methyl-), S-(cyclobutyl-methyl-), R-((2-methyl-cyclopropyl)-methyl-), S-((2-methyl-cyclopropyl)-methyl-), S—(S-(2-methyl-cyclopropyl)-methyl-), R—(S-(2-methyl-cyclopropyl)-methyl-), R—(R-(2-methyl-cyclopropyl)-methyl-);

(c) morpholin-2-yl-methyl-;

(d) R-(4-fluoro-phenyl-methyl-), S-(4-fluoro-phenyl-methyl-), S-(4-(difluoro-methyl)-phenyl-methyl-), R-(4-(difluoro-methyl)-phenyl-methyl-), S—(S-(1-hydroxy-1-phenyl)-methyl-), S—(R-(1-hydroxy-1-phenyl)-methyl-), R—(R-(1-hydroxy-1-phenyl)-methyl-), R—(S-(1-hydroxy-1-phenyl)-methyl-);

(e) 1-methyl-1,2,5-triazol-3-yl, 1-phenyl-1,2,5-triazol-3-yl;

and (f) S-(pyrazol-1-yl-methyl-), R-(pyrazol-1-yl-methyl-), S-(4-fluoro-pyrazol-1-yl-methyl-), R-(4-fluoro-pyrazol-1-yl-methyl-), R-(4-(difluoro-methoxy)-pyrazol-1-yl-methyl-), S-(4-(difluoro-methoxy)-pyrazol-1-yl-methyl-), R-(1-(difluoro-methyl)-pyrazol-3-yl-methyl-), S-(1-(difluoro-methyl)-pyrazol-3-yl-methyl-), R-(thiazol-2-yl-methyl-), S-(thiazol-2-yl-methyl-), 6-(trifluoro-methyl)-pyridin-3-yl-methyl-, R-(6-(trifluoro-methyl)-pyridin-3-yl-methyl-), S-(6-(trifluoro-methyl)-pyridin-3-yl-methyl-), oxazol-2-yl-methyl-, and 1,3,4-oxadiazol-2-yl-methyl-;

$R^6$ is hydrogen;

$R^7$ is selected from the group consisting of hydrogen, chloro, methoxy and ethoxy;

or a pharmaceutically acceptable salt thereof.

5. The compound of claim 4, wherein $R^1$ is selected from the group consisting of 4-bromo-1,2,3-triazol-1-yl, 4-chloro-1,2,3-triazol-1-yl, 4-(trifluoro-methyl)-1,2,3-triazol-1-yl, 4-(difluoro-methoxy)-1,2,3-triazol-1-yl, 5-(difluoro-methoxy)-1,2,3-triazol-1-yl, 4-cyano-1,2,3-triazol-1-yl, 4-cyclopropyl-1,2,3-triazol-1-yl, oxazol-5-yl and 1,2,3,4-tetrazol-1-yl;

a is an integer from 1 to 2;

each $R^2$ is independently selected from the group consisting of 5-chloro and 6-fluoro;

$R^3$ is hydrogen;

$R^4$ is selected from the group consisting of 1-(difluoro-methyl)-pyrazol-3-yl, 1-(difluoro-methyl)-4-chloropyrazol-3-yl, 3-chloro-pyrazol-4-yl, 1-methyl-pyrazol-4-yl, 1-methyl-3-chloro-pyrazol-4-yl, 1-(trifluoro-methyl)-pyrazol-4-yl, 1-(methoxy-carbonyl-methyl)-pyrazol-4-yl, pyrazol-5-yl, 1-methyl-4-fluoro-pyrazol-5-yl, 1-methyl-pyrazol-5-yl, 1-methyl-4-cyano-pyrazol-5-yl, 1-(difluoro-methyl)-pyrazol-5-yl, 1-methyl-3-(trifluoro-methyl)-pyrazol-5-yl, 1-methyl-4-chloro-pyrazol-5-yl, 1-(methyl-$d_3$)-pyrazol-5-yl, 1-(difluoro-methyl)-4-chloro-pyrazol-5-yl, 1-(difluoro-methyl)-4-fluoro-pyrazol-5-yl, 1-(difluoro-methyl)-4-cyano-pyrazol-5-yl, 1-methyl-4-hydroxy-pyrazol-5-yl, 1-(difluoro-methyl)-pyrazol-5-yl), 1-(methyl-$d_3$)-4-(cyclopropyl-carbonyl-amino)-pyrazol-5-yl, thiazol-5-yl, 4-methyl-thiazol-5-yl, 4-cyclopropyl-thiazol-5-yl, 2-(difluoro-methyl)-thiazol-5-yl, 4-(trifluoro-methyl)-thiazol-5-yl, 4-chloro-thiazol-5-yl, 2-amino-thaizol-5-yl, 2-amino-4-chloro-thiazol-5-yl, 2-(trifluoro-methyl)-4-methyl-thiazol-5-yl, isothiazol-4-yl, 1,2,4-thiadizol-5-yl, 2-(trifluoro-methyl)-1,3,4-thiadiazol-5-yl, imidazol-1-yl, 2-methyl-imidazol-1-yl, 1-methyl-imidazol-5-yl, 1-(difluoro-methyl)-imidazol-5-yl, 1-(difluoro-methyl)-4-chloro-imidazol-5-yl, 1-methyl-4-chloro-imidazol-5-yl, oxazol-5-yl, 3-methyl-isoxazol-4-yl, 1,3,4-oxadiazol-5-yl, 3-methyl-1,2,4-oxadiazol-5-yl, 1-methyl-1,2,3-triazol-4-yl, 1-(difluoro-methyl)-1,2,3-triazol-4-yl, 1-(difluoro-methyl)-5-chloro-1,2,3-triazol-4-yl, 1-methyl-5-fluoro-1,2,3-triazol-4-yl, 1-methyl-1,2,3-triazol-5-yl, 1-methyl-4-chloro-1,2,3-triazol-5-yl, 1-cyclopropyl-1,2,3-triazol-5-yl, 1-(difluoro-methyl)-1,2,3-triazol-5-yl, 1-(difluoro-methyl)-4-chloro-1,2,3-triazol-5-yl, 1-methyl-4-fluoro-1,2,3-triazol-5-yl, 1-isopropyl-1,2,3-triazol-5-yl, 3-methyl-1,2,4-triazol-1-yl, 1-(difluoro-methyl)-1,2,4-triazol-5-yl, 1-methyl-1,2,4-triazol-5-yl, 1-methyl-1,2,5-triazol-3-yl, 1-(difluoro-methyl)-1,2,5-triazol-3-yl, 1-(difluoro-methyl)-4-fluoro-1,2,5-triazol-3-yl, 1-(difluoro-methyl)-1,2,5-triazol-4-yl, 1,3,4-triazol-1-yl, 2-methyl-1,3,4-triazol-1-yl, 1-(difluoro-methyl)-1,3,4-triazol-2-yl, 1-methyl-1,2,3,4-tetrazol-5-yl, 5-(amino-carbonyl)-thien-2-yl, 3-methyl-5-(amino-carbonyl)-thien-2-yl, and 4-fluoro-5-(amino-carbonyl)-thien-3-yl;

$R^5$ is selected from the group consisting of (a) R-ethyl, S-ethyl, R-(2-hydroxy-ethyl-), R-(2-methoxy-ethyl-), 2-(difluoro-methoxy)-ethyl-, S-(2-(difluoro-methoxy)-ethyl-), R-(2-(difluoro-methoxy)-ethyl-), R-(2-trifluoro-methoxy-ethyl-), R-(2-t-butoxy-ethyl-), 2-(methyl-$d_3$)-ethyl-2,2-$d_2$-, R-(2-hydroxy-ethyl-2,2-$d_2$) S-(2-(methoxy-$d_3$)-ethyl-2,2-$d_2$-), R-(2-(methoxy-$d_3$)-ethyl-2,2-$d_2$-), S-(2-(difluoro-methoxy)-ethyl-2,2-$d_2$-), R-(2-(difluoro-methoxy)-ethyl-2,2-$d_2$-), R-(2-methoxy-2-methyl-n-propyl-), R-(2-hydroxy-2-methyl-n-propyl-), R-(3,3,3-trifluoro-n-propyl);

(b) cyclopropyl-methyl-, S-(cyclopropyl-methyl-), R-(2,2-difluoro-cyclopropyl-methyl-), R-(cyclobutyl-methyl-), R-((2-methyl-cyclopropyl)-methyl-), S—(S-(2-methyl-cyclopropyl)-methyl-), R—(R-(2-methyl-cyclopropyl)-methyl-);

(c) morpholin-2-yl-methyl-;

(d) R-(4-fluoro-phenyl-methyl-), S-(4-fluoro-phenyl-methyl-), R-(4-(difluoro-methyl)-phenyl-methyl-), S—(S-(1-hydroxy-1-phenyl)-methyl-), S—(R-(1-hydroxy-1-phenyl(methyl-), R—(R-(1-hydroxy-1-phenyl)-methyl-), (e) 1-methyl-1,2,5-triazol-3-yl, 1-phenyl-1,2,5-triazol-3-yl;

and (f) S-(pyrazol-1-yl-methyl-), R-(pyrazol-1-yl-methyl-), S-(4-fluoro-pyrazol-1-yl-methyl-), R-(4-fluoro-pyrazol-1-yl-methyl-), R-(4-(difluoro-methoxy)-pyrazol-1-yl-methyl-), R-(1-(difluoro-methyl)-pyrazol-3-yl-methyl-), S-(1-(difluoro-methyl)-pyrazol-3-yl-methyl-), R-(thiazol-2-yl-methyl-), S-(thiazol-2-yl-methyl-), 6-(trifluoro-methyl)-pyridin-3-yl-methyl-, R-(6-(trifluoro-methyl)-pyridin-3-yl-methyl-), oxazol-2-yl-methyl-, and 1,3,4-oxadiazol-2-yl-methyl-;

$R^6$ is hydrogen;

$R^7$ is selected from the group consisting of hydrogen, methoxy and ethoxy;

or a pharmaceutically acceptable salt thereof.

6. The compound of claim 4, wherein $R^1$ is selected from the group consisting of 4-bromo-1,2,3-triazol-1-yl, 4-chloro-1,2,3-triazol-1-yl, 4-(trifluoro-methyl)-1,2,3-triazol-1-yl, 4-(difluoro-methoxy)-1,2,3-triazol-1-yl, 5-(difluoro-methoxy)-1,2,3-triazol-1-yl, 4-cyano-1,2,3-triazol-1-yl, and 1,2,3,4-tetrazol-1-yl;

a is an integer from 1 to 2;

each $R^2$ is independently selected from the group consisting of 5-chloro and 6-fluoro;

$R^3$ is hydrogen;

$R^4$ is selected from the group consisting of 1-(difluoro-methyl)-pyrazol-3-yl, 1-(difluoro-methyl)-4-chloro-pyrazol-3-yl, 3-chloro-pyrazol-4-yl, 1-methyl-3-chloro-pyrazol-4-yl, pyrazol-5-yl, 1-methyl-4-fluoro-pyrazol-5-yl, 1-methyl-pyrazol-5-yl, 1-methyl-4-cyano-pyrazol-5-yl, 1-(difluoro-methyl)-pyrazol-5-yl, 1-methyl-3-(trifluoro-methyl)-pyrazol-5-yl, 1-methyl-4-chloro-pyrazol-5-yl, 1-(methyl-$d_3$)-pyrazol-5-yl, 1-(difluoro-methyl)-4-chloro-pyrazol-5-yl, 1-(difluoro-methyl)-4-fluoro-pyrazol-5-yl, 1-methyl-4-hydroxy-pyrazol-5-yl, 4-methyl-thiazol-5-yl, 4-cyclopropyl-thiazol-5-yl, 2-(difluoro-methyl)-thiazol-5-yl, 4-(trifluoro-methyl)-thiazol-5-yl, 4-chloro-thiazol-5-yl, 2-amino-thaizol-5-yl, 2-amino-4-chloro-thiazol-5-yl, 2-(trifluoro-methyl)-4-methyl-thiazol-5-yl, 1,2,4-thiadizol-5-yl, imidazol-1-yl, 2-methyl-imidazol-1-yl, 1-methyl-imidazol-5-yl, 1-(difluoro-methyl)-imidazol-5-yl, 1-(difluoro-methyl)-4-chloro-imidazol-5-yl, 1-methyl-4-chloro-imidazol-5-yl, oxazol-5-yl, 3-methyl-isoxazol-4-yl, 1,3,4-oxadiazol-5-yl, 1-methyl-1,2,3-triazol-4-yl, 1-(difluoro-methyl)-1,2,3-triazol-4-yl, 1-(difluoro-methyl)-5-chloro-1,2,3-triazol-4-yl, 1-methyl-5-fluoro-1,2,3-triazol-4-yl, 1-methyl-1,2,3-triazol-5-yl, 1-methyl-4-chloro-1,2,3-triazol-5-yl, 1-cyclopropyl-1,2,3-triazol-5-yl, 1-(difluoro-methyl)-1,2,3-triazol-5-yl, 1-(difluoro-methyl)-4-chloro-1,2,3-triazol-5-yl, 1-methyl-4-fluoro-1,2,3-triazol-5-yl, 1-isopropyl-1,2,3-triazol-5-yl, 1-(difluoro-methyl)-1,2,4-triazol-5-yl, 1-methyl-1,2,4-triazol-5-yl, 1-(difluoro-methyl)-1,2,5-triazol-3-yl, 1-(difluoro-methyl)-4-fluoro-1,2,5-triazol-3-yl, 1-(difluoro-methyl)-1,2,5-triazol-4-yl, 1,3,4-triazol-1-yl, 2-methyl-1,3,4-triazol-1-yl, 1-(difluoro-methyl)-1,3,4-triazol-2-yl, 3-methyl-5-(amino-carbonyl)-thien-2-yl, and 4-fluoro-5-(amino-carbonyl)-thien-3-yl;

$R^5$ is selected from the group consisting of (a) R-ethyl, S-ethyl, R-(2-hydroxy-ethyl-), R-(2-methoxy-ethyl-), 2-(difluoro-methoxy)-ethyl-, S-(2-(difluoro-methoxy)-ethyl-), R-(2-(difluoro-methoxy)-ethyl-), R-(2-trifluoro-methoxy-ethyl-), R-(2-t-butoxy-ethyl-), 2-(methyl-$d_3$)-ethyl-2,2-$d_2$-, S-(2-(methoxy-$d_3$)-ethyl-2,2-$d_2$-), R-(2-(methoxy-$d_3$)-ethyl-2,2-$d_2$-), R-(2-(difluoro-methoxy)-ethyl-2,2-d₂-), R-(2-methoxy-2-methyl-n-propyl-);
(b) cyclopropyl-methyl-, S-(cyclopropyl-methyl-), R-(cyclopropyl-methyl-), R-(2,2-difluoro-cyclopropyl-methyl-), R-(cyclobutyl-methyl-), R-((2-methyl-cyclopropyl)-methyl-), S—(S-(2-methyl-cyclopropyl)-methyl-), R—(R-(2-methyl-cyclopropyl)-methyl-);
(c) morpholin-2-yl-methyl-;
(d) R-(4-fluoro-phenyl-methyl-), R-(4-(difluoro-methyl)-phenyl-methyl-), S—(S-(1-hydroxy-1-phenyl)-methyl-), S—(R-(1-hydroxy-1-phenyl)-methyl-),
(e) 1-methyl-1,2,5-triazol-3-yl, 1-phenyl-1,2,5-triazol-3-yl;
and (f) S-(pyrazol-1-yl-methyl-), R-(pyrazol-1-yl-methyl-), S-(4-fluoro-pyrazol-1-yl-methyl-), R-(4-fluoro-pyrazol-1-yl-methyl-), R-(1-(difluoro-methyl)-pyrazol-3-yl-methyl-), S-(1-(difluoro-methyl)-pyrazol-3-yl-methyl-), R-(thiazol-2-yl-methyl-), 6-(trifluoro-methyl)-pyridin-3-yl-methyl-, R-(6-(trifluoro-methyl)-pyridin-3-yl-methyl-), oxazol-2-yl-methyl-, and 1,3,4-oxadiazol-2-yl-methyl-;
$R^6$ is hydrogen;
$R^7$ is selected from the group consisting of hydrogen, methoxy and ethoxy;
or a pharmaceutically acceptable salt thereof.

7. The compound of claim 4, wherein
$R^1$ is selected from the group consisting of 4-bromo-1,2,3-triazol-1-yl, 4-chloro-1,2,3-triazol-1-yl, 4-(trifluoromethyl)-1,2,3-triazol-1-yl, 4-(difluoro-methoxy)-1,2,3-triazol-1-yl, 5-(difluoro-methoxy)-1,2,3-triazol-1-yl, 4-cyano-1,2,3-triazol-1-yl, and 1,2,3,4-tetrazol-1-yl;
a is an integer from 1 to 2;
each $R^2$ is independently selected from the group consisting of 5-chloro and 6-fluoro;
$R^3$ is hydrogen;
$R^4$ is selected from the group consisting of 1-(difluoro-methyl)-pyrazol-3-yl, 1-(difluoro-methyl)-4-chloro-pyrazol-3-yl, 3-chloro-pyrazol-4-yl, 1-methyl-3-chloro-pyrazol-4-yl, 1-methyl-4-fluoro-pyrazol-5-yl, 1-methyl-pyrazol-5-yl, 1-methyl-4-cyano-pyrazol-5-yl, 1-(difluoro-methyl)-pyrazol-5-yl, 1-methyl-3-(trifluoro-methyl)-pyrazol-5-yl, 1-(methyl-d₃)-pyrazol-5-yl, 1-(difluoro-methyl)-4-chloro-pyrazol-5-yl, 1-(difluoro-methyl)-4-fluoro-pyrazol-5-yl, 1-methyl-4-hydroxy-pyrazol-5-yl, 4-methyl-thiazol-5-yl, 4-(trifluoro-methyl)-thiazol-5-yl, 4-chloro-thiazol-5-yl, 2-amino-thaizol-5-yl, 2-amino-4-chloro-thiazol-5-yl, 1-methyl-imidazol-5-yl, 1-(difluoro-methyl)-imidazol-5-yl, 3-methyl-isoxazol-4-yl, 1-(difluoro-methyl)-1,2,3-triazol-4-yl, 1-(difluoro-methyl)-5-chloro-1,2,3-triazol-4-yl, 1-methyl-1,2,3-triazol-5-yl, 1-methyl-4-chloro-1,2,3-triazol-5-yl, 1-(difluoro-methyl)-1,2,3-triazol-5-yl, 1-methyl-4-fluoro-1,2,3-triazol-5-yl, 1-(difluoro-methyl)-4-chloro-1,2,3-triazol-5-yl, 1-(difluoro-methyl)-1,2,4-triazol-5-yl, 1-methyl-1,2,4-triazol-5-yl, 1-(difluoro-methyl)-1,2,5-triazol-3-yl, 1-(difluoro-methyl)-4-fluoro-1,2,5-triazol-3-yl, and 3-methyl-5-(amino-carbonyl)-thien-2-yl;
$R^5$ is selected from the group consisting of
(a) R-(2-methoxy-ethyl-), 2-(difluoro-methoxy)-ethyl-, R-(2-(difluoro-methoxy)-ethyl-), S-(2-(difluoro-methoxy)-ethyl-), R-(2-t-butoxy-ethyl-), S-(2-(methoxy-d₃)-ethyl-2,2-d₂-), R-(2-(difluoro-methoxy)-ethyl-2,2-d₂-);
(b) cyclopropyl-methyl-, R-(cyclopropyl-methyl-), S-(cyclopropyl-methyl-), R-(cyclobutyl-methyl-), R-((2-methyl-cyclopropyl)-methyl-), S—(S-(2-methyl-cyclopropyl)-methyl-);
(d) R-(4-fluoro-phenyl-methyl-), R-(4-(difluoro-methyl)-phenyl-methyl-), S—(S-(1-hydroxy-1-phenyl)-methyl-), S—(R-(1-hydroxy-1-phenyl)-methyl-);
(e) 1-methyl-1,2,5-triazol-3-yl;
and (f) S-(pyrazol-1-yl-methyl-), S-(4-fluoro-pyrazol-1-yl-methyl-), R-(4-fluoro-pyrazol-1-yl-methyl-), R-(1-(difluoro-methyl)-pyrazol-3-yl-methyl-), S-(1-(difluoro-methyl)-pyrazol-3-yl-methyl-), R-(thiazol-2-yl-methyl-), R-(6-(trifluoro-methyl)-pyridin-3-yl-methyl-) and oxazol-2-yl-methyl-;
$R^6$ is hydrogen;
$R^7$ is selected from the group consisting of hydrogen and methoxy;
or a pharmaceutically acceptable salt thereof.

8. The compound of claim 4, wherein
$R^1$ is selected from the group consisting of 4-bromo-1,2,3-triazol-1-yl, 4-chloro-1,2,3-triazol-1-yl, 4-cyano-1,2,3-triazol-1-yl, and 1,2,3,4-tetrazol-1-yl;
a is an integer from 1 to 2;
each $R^2$ is independently selected from the group consisting of 5-chloro and 6-fluoro;
$R^3$ is hydrogen;
$R^4$ is selected from the group consisting of 3-chloro-pyrazol-4-yl, 1-methyl-3-chloro-pyrazol-4-yl, 1-methyl-4-fluoro-pyrazol-5-yl, 1-methyl-pyrazol-5-yl, 1-(difluoro-methyl)-pyrazol-5-yl, 1-(methyl-d₃)-pyrazol-5-yl, 1-(difluoro-methyl)-4-chloro-pyrazol-5-yl, 4-chloro-thiazol-5-yl, 2-amino-thaizol-5-yl, 1-methyl-imidazol-5-yl, 1-(difluoro-methyl)-1,2,3-triazol-4-yl, 1-methyl-1,2,3-triazol-5-yl, 1-methyl-4-chloro-1,2,3-triazol-5-yl, 1-(difluoro-methyl)-1,2,3-triazol-5-yl, 1-methyl-4-fluoro-1,2,3-triazol-5-yl, 1-(difluoro-methyl)-4-chloro-1,2,3-triazol-5-yl, 1-(difluoro-methyl)-1,2,4-triazol-5-yl, and 1-methyl-1,2,4-triazol-5-yl;
$R^5$ is selected from the group consisting of (a) R-(2-methoxy-ethyl-), R-(2-(difluoro-methoxy)-ethyl-), R-(2-(difluoro-methoxy)-ethyl-2,2-d₂-);
(b) cyclopropyl-methyl-, R-(cyclopropyl-methyl-), S-(cyclopropyl-methyl-);
(d) R-(4-fluoro-phenyl-methyl-), S—(R-(1-hydroxy-1-phenyl)-methyl-);
and (f) R-(4-fluoro-pyrazol-1-yl-methyl-), R-(1-(difluoro-methyl)-pyrazol-3-yl-methyl-), and R-(thiazol-2-yl-methyl-);
$R^6$ is hydrogen;
$R^7$ is selected from the group consisting of hydrogen and methoxy;
or a pharmaceutically acceptable salt thereof.

9. The compound of claim 4, selected from the group consisting of
5-[3-chloro-2-fluoro-6-(tetrazol-1-yl)phenyl]-2-[(1R)-3-(difluoromethoxy)-1-[4-(3-methyltriazol-4-yl)pyrazol-1-yl]propyl]-1-oxido-pyridin-1-ium;
5-[3-chloro-6-(4-chlorotriazol-1-yl)-2-fluoro-phenyl]-2-[(1R)-3-(difluoromethoxy)-1-[4-(3-methyltriazol-4-yl)pyrazol-1-yl]propyl]-1-oxido-pyridin-1-ium;
5-[3-chloro-2-fluoro-6-(tetrazol-1-yl)phenyl]-2-[(1R)-3-(difluoromethoxy)-1-[4-[3-(difluoromethyl)triazol-4-yl]pyrazol-1-yl]propyl]-1-oxido-pyridin-1-ium;

5-[3-chloro-6-(4-chlorotriazol-1-yl)-2-fluoro-phenyl]-2-[(1R)-3-(difluoromethoxy)-1-[4-(5-fluoro-3-methyl-triazol-4-yl)pyrazol-1-yl]propyl]-1-oxido-pyridin-1-ium;

5-[3-chloro-6-(4-chlorotriazol-1-yl)-2-fluoro-phenyl]-2-[(1R)-3-(difluoromethoxy)-1-[4-[2-(difluoromethyl)-1,2,4-triazol-3-yl]pyrazol-1-yl]propyl]-1-oxido-pyridin-1-ium;

5-[3-chloro-6-(4-chlorotriazol-1-yl)-2-fluoro-phenyl]-2-[(1R)-3-(difluoromethoxy)-1-[4-(2-methyl-1,2,4-triazol-3-yl)pyrazol-1-yl]propyl]-1-oxido-pyridin-1-ium;

5-[3-chloro-2-fluoro-6-(tetrazol-1-yl)phenyl]-2-[(1R)-2-cyclopropyl-1-[4-(5-fluoro-3-methyl-triazol-4-yl)pyrazol-1-yl]ethyl]-1-oxido-pyridin-1-ium;

5-[3-chloro-2-fluoro-6-[4-(trifluoromethyl)triazol-1-yl]phenyl]-2-[(1R)-3-(difluoromethoxy)-1-[4-(2-methyl-1,2,4-triazol-3-yl)pyrazol-1-yl]propyl]-1-oxido-pyridin-1-ium;

5-[3-chloro-6-(4-chlorotriazol-1-yl)-2-fluoro-phenyl]-2-[(1R)-2-[1-(difluoromethyl)pyrazol-3-yl]-1-[4-(2-methyl-1,2,4-triazol-3-yl)pyrazol-1-yl]ethyl]-1-oxido-pyridin-1-ium;

5-[3-chloro-6-(4-chlorotriazol-1-yl)-2-fluoro-phenyl]-2-[(1R)-2-[1-(difluoromethyl)pyrazol-3-yl]-1-[4-(5-fluoro-3-methyl-triazol-4-yl)pyrazol-1-yl]ethyl]-1-oxido-pyridin-1-ium;

and pharmaceutically acceptable salts thereof.

10. A pharmaceutical composition comprising a pharmaceutically acceptable carrier and a compound of claim 1.

\* \* \* \* \*